US011708351B2

(12) United States Patent
Wiles et al.

(10) Patent No.: US 11,708,351 B2
(45) Date of Patent: *Jul. 25, 2023

(54) ARYL, HETEROARYL, AND HETEROCYCLIC PHARMACEUTICAL COMPOUNDS FOR TREATMENT OF MEDICAL DISORDERS

(71) Applicant: Achillion Pharmaceuticals, Inc., Boston, MA (US)

(72) Inventors: Jason Allan Wiles, Madison, CT (US); Avinash S. Phadke, Branford, CT (US); Milind Deshpande, Madison, CT (US); Atul Agarwal, Hamden, CT (US); Dawei Chen, Guilford, CT (US); Venkat Rao Gadhachanda, Hamden, CT (US); Akihiro Hashimoto, Branford, CT (US); Godwin Pais, Hamden, CT (US); Qiuping Wang, Bethany, CT (US); Xiangzhu Wang, Branford, CT (US); Joel Charles Barrish, Richboro, CT (US); William Greenlee, Teaneck, NJ (US); Kyle J. Eastman, New Haven, CT (US)

(73) Assignee: Achillion Pharmaceuticals, Inc., Boston, MA (US)

( * ) Notice: Subject to any disclaimer, the term of this patent is extended or adjusted under 35 U.S.C. 154(b) by 46 days.

This patent is subject to a terminal disclaimer.

(21) Appl. No.: 17/366,670

(22) Filed: Jul. 2, 2021

(65) Prior Publication Data
US 2022/0396563 A1    Dec. 15, 2022

Related U.S. Application Data

(63) Continuation of application No. 16/555,914, filed on Aug. 29, 2019, now Pat. No. 11,084,800, which is a continuation of application No. PCT/US2018/020528, filed on Mar. 1, 2018.

(60) Provisional application No. 62/466,301, filed on Mar. 2, 2017, provisional application No. 62/465,782, filed on Mar. 1, 2017.

(51) Int. Cl.
| C07D 401/14 | (2006.01) |
| C07D 403/14 | (2006.01) |
| C07D 409/14 | (2006.01) |
| C07D 471/04 | (2006.01) |
| C07D 471/08 | (2006.01) |
| C07D 491/107 | (2006.01) |
| C07D 498/10 | (2006.01) |
| C07F 5/02 | (2006.01) |

(52) U.S. Cl.
CPC ......... *C07D 401/14* (2013.01); *C07D 403/14* (2013.01); *C07D 409/14* (2013.01); *C07D 471/04* (2013.01); *C07D 471/08* (2013.01); *C07D 491/107* (2013.01); *C07D 498/10* (2013.01); *C07F 5/027* (2013.01)

(58) Field of Classification Search
CPC .. C07D 401/14; C07D 403/14; C07D 409/14; C07D 471/04; C07D 471/08; C07D 491/107; C07D 498/10; C07F 5/027
USPC ..................................................... 514/210.16
See application file for complete search history.

(56) References Cited

U.S. PATENT DOCUMENTS

| 5,628,984 | A  | 5/1997  | Boucher, Jr. |
| 6,319,897 | B1 | 11/2001 | Lambris et al. |
| 6,489,476 | B1 | 12/2002 | Dang et al. |
| 6,492,402 | B1 | 12/2002 | Lee et al. |
| 6,653,340 | B1 | 11/2003 | Babu et al. |
| 7,629,340 | B2 | 12/2009 | Schmitz et al. |
| 7,888,323 | B2 | 2/2011  | Lambris et al. |
| 7,989,589 | B2 | 8/2011  | Lambris |
| 7,999,081 | B2 | 8/2011  | Tedesco et al. |
| 8,168,584 | B2 | 5/2012  | Deschatelets et al. |
| 8,241,628 | B2 | 8/2012  | Diefenbach-Streiber et al. |
| 8,524,716 | B2 | 9/2013  | Raboisson et al. |
| 8,580,735 | B2 | 11/2013 | Francois et al. |
| 8,883,158 | B2 | 11/2014 | Diefenbach-Streiber et al. |
| 8,946,145 | B2 | 2/2015  | Lambris et al. |
| 9,056,076 | B2 | 6/2015  | Deschatelets et al. |
| 9,085,555 | B2 | 7/2015  | Altmann et al. |
| 9,169,307 | B2 | 10/2015 | Lambris et al. |
| 9,291,622 | B2 | 3/2016  | Zhang et al. |
| 9,371,365 | B2 | 6/2016  | Lambris et al. |
| 9,421,240 | B2 | 8/2016  | Francois et al. |
| 9,468,661 | B2 | 10/2016 | Altmann et al. |

(Continued)

FOREIGN PATENT DOCUMENTS

| CN | 103402996 A | 11/2013 |
| EA | 201890594 A1 | 8/2018 |

(Continued)

OTHER PUBLICATIONS

"Are There Any Treatments for ALS?" WebMD, <https://www.webmd.com/brain/understanding-als-treatment#1>, retrieved on May 3, 2019 (8 pages).

(Continued)

*Primary Examiner* — Kristin A Vajda
(74) *Attorney, Agent, or Firm* — Clark & Elbing LLP

(57) ABSTRACT

Complement Factor D inhibitors, pharmaceutical compositions, and uses thereof, as well as processes for their manufacture are provided. The compounds provided include Formula I, Formula II, Formula III, Formula IV, and Formula V, or a pharmaceutically acceptable salt, prodrug, isotopic analog, N-oxide, or isolated isomer thereof, optionally in a pharmaceutically acceptable composition. The inhibitors described herein target Factor D and inhibit or regulate the complement cascade.

17 Claims, 41 Drawing Sheets

(56) References Cited

U.S. PATENT DOCUMENTS

| | | |
|---|---|---|
| 9,598,446 B2 | 3/2017 | Gadhachanda et al. |
| 9,643,986 B2 | 5/2017 | Wiles et al. |
| 9,663,543 B2 | 5/2017 | Wiles et al. |
| 9,695,205 B2 | 7/2017 | Wiles et al. |
| 9,732,103 B2 | 8/2017 | Wiles et al. |
| 9,732,104 B2 | 8/2017 | Gadhachanda et al. |
| 9,758,537 B2 | 9/2017 | Wiles et al. |
| 9,796,741 B2 | 10/2017 | Gadhachanda et al. |
| 9,828,396 B2 | 11/2017 | Wiles et al. |
| 10,000,516 B2 | 6/2018 | Wiles et al. |
| 10,005,802 B2 | 6/2018 | Wiles et al. |
| 10,011,612 B2 | 7/2018 | Wiles et al. |
| 10,081,645 B2 | 9/2018 | Wiles et al. |
| 10,087,203 B2 | 10/2018 | Wiles et al. |
| 10,092,547 B2 | 10/2018 | Wiles et al. |
| 10,092,584 B2 | 10/2018 | Wiles et al. |
| 10,100,072 B2 | 10/2018 | Wiles et al. |
| 10,106,563 B2 | 10/2018 | Wiles et al. |
| 10,138,225 B2 | 11/2018 | Wiles et al. |
| 10,189,869 B2 | 1/2019 | Gadhachanda et al. |
| 10,253,053 B2 | 4/2019 | Wiles et al. |
| 10,287,301 B2 | 5/2019 | Wiles et al. |
| 10,301,336 B2 | 5/2019 | Wiles et al. |
| 10,370,394 B2 | 8/2019 | Wiles et al. |
| 10,385,097 B2 | 8/2019 | Wiles et al. |
| 10,428,094 B2 | 10/2019 | Wiles et al. |
| 10,428,095 B2 | 10/2019 | Wiles et al. |
| 10,464,956 B2 | 11/2019 | Wiles et al. |
| 10,550,140 B2 | 2/2020 | Wiles et al. |
| 10,660,876 B2 | 5/2020 | Wiles et al. |
| 10,662,175 B2 | 5/2020 | Wiles et al. |
| 10,807,952 B2 | 10/2020 | Wiles et al. |
| 10,822,352 B2 | 11/2020 | Wiles et al. |
| 10,906,887 B2 | 2/2021 | Wiles et al. |
| 10,919,884 B2 | 2/2021 | Wiles et al. |
| 11,001,600 B2 | 5/2021 | Wiles et al. |
| 11,053,253 B2 | 7/2021 | Wiles et al. |
| 11,084,800 B2 | 8/2021 | Wiles et al. |
| 11,407,738 B2 | 8/2022 | Wiles et al. |
| 11,447,465 B2 | 9/2022 | Wiles et al. |
| 2002/0133004 A1 | 9/2002 | Sekiyama et al. |
| 2005/0228000 A1 | 10/2005 | Smallheer et al. |
| 2005/0245497 A1 | 11/2005 | Penfold et al. |
| 2005/0267108 A1 | 12/2005 | Hsieh et al. |
| 2006/0004000 A1 | 1/2006 | D'Orchymont et al. |
| 2007/0155712 A1 | 7/2007 | Zahn et al. |
| 2008/0075720 A1 | 3/2008 | Holers et al. |
| 2008/0075728 A1 | 3/2008 | Newman |
| 2008/0108691 A1 | 5/2008 | Hamann et al. |
| 2010/0041628 A1 | 2/2010 | Enomoto et al. |
| 2011/0280808 A1 | 11/2011 | Kroth et al. |
| 2012/0231471 A1 | 9/2012 | Sato et al. |
| 2012/0237515 A1 | 9/2012 | Bell et al. |
| 2012/0295884 A1 | 11/2012 | Altmann et al. |
| 2013/0029912 A1 | 1/2013 | Holers et al. |
| 2013/0035392 A1 | 2/2013 | McGeer et al. |
| 2013/0296377 A1 | 11/2013 | Adams et al. |
| 2013/0324482 A1 | 12/2013 | Francois et al. |
| 2013/0344073 A1 | 12/2013 | Schwaeble et al. |
| 2014/0050739 A1 | 2/2014 | Francois et al. |
| 2014/0323407 A1 | 10/2014 | Francois et al. |
| 2014/0371133 A1 | 12/2014 | Francois et al. |
| 2015/0141455 A1 | 5/2015 | Altmann et al. |
| 2015/0148374 A1 | 5/2015 | Hommel et al. |
| 2015/0158915 A1 | 6/2015 | Lambris et al. |
| 2015/0191462 A1 | 7/2015 | Hommel et al. |
| 2015/0239837 A1 | 8/2015 | Wiles et al. |
| 2015/0239838 A1 | 8/2015 | Phadke et al. |
| 2015/0239868 A1 | 8/2015 | Pais et al. |
| 2015/0239893 A1 | 8/2015 | Wang et al. |
| 2015/0239894 A1 | 8/2015 | Gadhachanda et al. |
| 2015/0239895 A1 | 8/2015 | Gadhachanda et al. |
| 2015/0239919 A1 | 8/2015 | Gadhachanda et al. |
| 2015/0239920 A1 | 8/2015 | Gadhachanda et al. |
| 2015/0239921 A1 | 8/2015 | Wiles et al. |
| 2015/0269868 A1 | 9/2015 | Carney et al. |
| 2015/0322060 A1 | 11/2015 | Flohr et al. |
| 2015/0368271 A1 | 12/2015 | Su et al. |
| 2016/0015810 A1 | 1/2016 | Deschatelets et al. |
| 2016/0024079 A1 | 1/2016 | Adams et al. |
| 2016/0060297 A1 | 3/2016 | Deschatelets et al. |
| 2016/0194359 A1 | 7/2016 | Francois et al. |
| 2016/0215020 A1 | 7/2016 | Francois et al. |
| 2016/0215022 A1 | 7/2016 | Francois et al. |
| 2016/0361329 A1 | 12/2016 | Wiles et al. |
| 2016/0362398 A1 | 12/2016 | Wiles et al. |
| 2016/0362399 A1 | 12/2016 | Wiles et al. |
| 2016/0362432 A1 | 12/2016 | Wiles et al. |
| 2016/0362433 A1 | 12/2016 | Wiles et al. |
| 2017/0056428 A1 | 3/2017 | Wiles et al. |
| 2017/0057950 A1 | 3/2017 | Wiles et al. |
| 2017/0057983 A1 | 3/2017 | Wiles et al. |
| 2017/0057993 A1 | 3/2017 | Wiles et al. |
| 2017/0066783 A1 | 3/2017 | Wiles et al. |
| 2017/0189410 A1 | 7/2017 | Gadhachanda et al. |
| 2017/0202821 A1 | 7/2017 | Bekker |
| 2017/0202935 A1 | 7/2017 | Lambris et al. |
| 2017/0226142 A1 | 8/2017 | Wiles et al. |
| 2017/0260219 A1 | 9/2017 | Wiles et al. |
| 2017/0298084 A1 | 10/2017 | Wiles et al. |
| 2017/0298085 A1 | 10/2017 | Wiles et al. |
| 2018/0022766 A1 | 1/2018 | Wiles et al. |
| 2018/0022767 A1 | 1/2018 | Wiles et al. |
| 2018/0030075 A1 | 2/2018 | Wiles et al. |
| 2018/0072762 A1 | 3/2018 | Wiles et al. |
| 2018/0177761 A1 | 6/2018 | Wiles et al. |
| 2018/0179185 A1 | 6/2018 | Wiles et al. |
| 2018/0179186 A1 | 6/2018 | Wiles et al. |
| 2018/0179236 A1 | 6/2018 | Wiles et al. |
| 2018/0186782 A1 | 7/2018 | Wiles et al. |
| 2018/0201580 A1 | 7/2018 | Wiles et al. |
| 2018/0305375 A1 | 10/2018 | Wiles et al. |
| 2019/0023729 A1 | 1/2019 | Wiles et al. |
| 2019/0031692 A1 | 1/2019 | Wiles et al. |
| 2019/0038623 A1 | 2/2019 | Huang et al. |
| 2019/0048033 A1 | 2/2019 | Wiles et al. |
| 2019/0085005 A1 | 3/2019 | Wiles et al. |
| 2019/0144473 A1 | 5/2019 | Gadhachanda et al. |
| 2019/0211033 A1 | 7/2019 | Wiles et al. |
| 2019/0359645 A1 | 11/2019 | Birkus et al. |
| 2019/0382376 A1 | 12/2019 | Wiles et al. |
| 2020/0002347 A1 | 1/2020 | Wiles et al. |
| 2020/0062790 A1 | 2/2020 | Wiles et al. |
| 2020/0071301 A1 | 3/2020 | Wiles et al. |
| 2020/0101071 A1 | 4/2020 | Huang et al. |
| 2020/0262818 A1 | 8/2020 | Wiles et al. |
| 2021/0332026 A1 | 10/2021 | Phadke et al. |
| 2022/0079943 A1 | 3/2022 | Huang et al. |

FOREIGN PATENT DOCUMENTS

| | | |
|---|---|---|
| JP | 2014-506877 A | 3/2014 |
| JP | 2015-522005 A | 8/2015 |
| JP | 2015-522006 A | 8/2015 |
| JP | 2015-522007 A | 8/2015 |
| JP | 2015-522008 A | 8/2015 |
| JP | 2015-522062 A | 8/2015 |
| JP | 2017-511815 A | 4/2017 |
| JP | 6400738 B2 | 10/2018 |
| JP | 2018-199714 A | 12/2018 |
| JP | 6537532 B2 | 7/2019 |
| JP | 6688352 B2 | 4/2020 |
| JP | 6877406 B2 | 5/2021 |
| RU | 2202344 C2 | 4/2003 |
| RU | 2470918 C2 | 12/2012 |
| WO | WO-93/20099 A2 | 10/1993 |
| WO | WO-95/29697 A1 | 11/1995 |
| WO | WO-99/48492 A1 | 9/1999 |
| WO | WO-2004/007501 A1 | 1/2004 |
| WO | WO-2004/045518 A2 | 6/2004 |
| WO | WO-2004/111041 A1 | 12/2004 |
| WO | WO-2008/047831 A1 | 4/2008 |
| WO | WO-2009/091826 A2 | 7/2009 |
| WO | WO-2011/057158 A1 | 5/2011 |

(56) References Cited

FOREIGN PATENT DOCUMENTS

| | | |
|---|---|---|
| WO | WO-2012/093101 A1 | 7/2012 |
| WO | WO-2012/177782 A1 | 12/2012 |
| WO | WO-2013/166436 A1 | 11/2013 |
| WO | WO-2013/192345 A1 | 12/2013 |
| WO | WO-2014/002051 A2 | 1/2014 |
| WO | WO-2014/002052 A1 | 1/2014 |
| WO | WO-2014/002053 A1 | 1/2014 |
| WO | WO-2014/002054 A1 | 1/2014 |
| WO | WO-2014/002057 A1 | 1/2014 |
| WO | WO-2014/002058 A2 | 1/2014 |
| WO | WO-2014/002059 A1 | 1/2014 |
| WO | WO-2014/002067 A2 | 1/2014 |
| WO | WO-2014/005150 A1 | 1/2014 |
| WO | WO-2014/009833 A2 | 1/2014 |
| WO | WO-2014/037480 A1 | 3/2014 |
| WO | WO-2014/116880 A1 | 7/2014 |
| WO | WO-2015/008861 A1 | 1/2015 |
| WO | WO-2015/021166 A2 | 2/2015 |
| WO | WO-2015/054569 A1 | 4/2015 |
| WO | WO-2015/130784 A1 | 9/2015 |
| WO | WO-2015/130795 A1 | 9/2015 |
| WO | WO-2015/130806 A1 | 9/2015 |
| WO | WO-2015/130830 A1 | 9/2015 |
| WO | WO-2015/130838 A1 | 9/2015 |
| WO | WO-2015/130842 A2 | 9/2015 |
| WO | WO-2015/130845 A1 | 9/2015 |
| WO | WO-2015/130854 A1 | 9/2015 |
| WO | WO-2017/035348 A1 | 3/2017 |
| WO | WO-2017/035349 A1 | 3/2017 |
| WO | WO-2017/035351 A1 | 3/2017 |
| WO | WO-2017/035352 A1 | 3/2017 |
| WO | WO-2017/035353 A1 | 3/2017 |
| WO | WO-2017/035355 A1 | 3/2017 |
| WO | WO-2017/035357 A1 | 3/2017 |
| WO | WO-2017/035360 A1 | 3/2017 |
| WO | WO-2017/035361 A1 | 3/2017 |
| WO | WO-2017/035362 A1 | 3/2017 |
| WO | WO-2017/035401 A1 | 3/2017 |
| WO | WO-2017/035405 A1 | 3/2017 |
| WO | WO-2017/035408 A1 | 3/2017 |
| WO | WO-2017/035409 A1 | 3/2017 |
| WO | WO-2017/035411 A1 | 3/2017 |
| WO | WO-2017/035413 A2 | 3/2017 |
| WO | WO-2017/035415 A1 | 3/2017 |
| WO | WO-2017/035417 A1 | 3/2017 |
| WO | WO-2017/035418 A1 | 3/2017 |
| WO | WO-2017/098328 A2 | 6/2017 |
| WO | WO-2017/127761 A1 | 7/2017 |
| WO | WO-2017/136395 A1 | 8/2017 |
| WO | WO-2018/005552 A1 | 1/2018 |
| WO | WO-2018/026722 A1 | 2/2018 |
| WO | WO-2018/160889 A1 | 9/2018 |
| WO | WO-2018/160891 A1 | 9/2018 |
| WO | WO-2018/160892 A1 | 9/2018 |
| WO | WO-2019/028284 A1 | 2/2019 |
| WO | WO-2019/070714 A1 | 4/2019 |
| WO | WO-2020/069024 A1 | 4/2020 |
| WO | WO-2020/109343 A1 | 6/2020 |
| WO | WO-2021/021909 A1 | 2/2021 |

OTHER PUBLICATIONS

"Arteriosclerosis/atherosclerosis," Mayo Clinic, <https://www.mayoclinic.org/diseases-conditions/arteriosclerosis-atherosclerosis/diagnosis-treatment/drc-20350575>, retrieved on Apr. 24, 2018 (10 pages).
"Cancer," MedLine Plus, <http://www.nlm.nih.gov/medlineplus/cancer.html>, retrieved Jul. 6, 2007 (10 pages).
"Dermatomyositis," Mayo Clinic, <https://www.mayoclinic.org/diseases-conditions/dermatomyositis/diagnosis-treatment/drc-20353192>, retrieved on Aug. 1, 2017 (7 pages).
"History of Changes for Study: NCT03053102—A Treatment Study of ACH-0144471 in Patients With Paroxysmal Nocturnal Hemoglobinuria (PNH)," U.S. National Library of Medicine, available at: <https://clinicaltrials.gov/ct2/history/NCT03053102?V_4=View#StudyPageTop>, submitted Jun. 6, 2017, retrieved Mar. 9, 2021 (3 pages).
"NCT03472885—A Treatment Study of ACH-0144471 in Patients With Paroxysmal Nocturnal Hemoglobinuria (PNH) With Inadequate Response to Eculizumab (PNH)," U.S. National Library of Medicine, available at: <https://clinicaltrials.gov/ct2/show/NCT03472885>, first posted Mar. 21, 2018, last update posted Dec. 3, 2019, retrieved Mar. 27, 2020 (7 pages).
"Reperfusion injury," Wikipedia, <https://en.wikipedia.org/wiki/Reperfusion_injury>, retrieved Apr. 30, 2020 (8 pages).
"Treatment for Multiple Sclerosis," WebMD, <https://www.webmd.com/multiple-sclerosis/ms-treatment#1>, retrieved on May 3, 2019 (24 pages).
"What are the Treatments for Cirrhosis?," WebMD, <https://www.webmd.com/digestive-disorders/understanding-cirrhosis-treatment#1>, retrieved May 3, 2019 (15 pages).
"What is Cardiovascular Disease?" American Heart Association, <https://www.heart.org/en/health-topics/consumer-healthcare/what-is-cardiovascular-disease>, last reviewed May 31, 2017 (4 pages).
"What is Dementia?" Alzheimer's Association, <https://www.alz.org/alzheimers-dementia/what-is-dementia>, retrieved on Nov. 17, 2020 (6 pages).
Airey et al., "A Convenient Preparation of Thieno[3,2-c]pyrazole," Synthesis. 46: 96-100 (2014).
Armand, "Fatty liver disease: What it is and what to do about it," Harvard Health Publishing, <https://www.health.harvard.edu/blog/fatty-liver-disease-what-it-is-and-what-to-do-about-it-2019011015746>, dated Jan. 10, 2019, retrieved May 2, 2019 (3 pages).
Babiker et al., "Transfer of prostasomal CD59 to CD59-deficient red blood cells results in protection against complement-mediated hemolysis," Am J Reprod Immunol. 47(3): 183-92 (2002) (Abstract Only).
Barraclough et al., "Synthesis of (2S,3R)- and (2S,3S)-[3-$^2$H$_1$]-proline via highly selective hydrolysis of a silyl enol ether," Tetrahedron Letters. 46(1): 4653-4655 (2005).
Barraclough et al., "Two separate and distinct syntheses of stereospecifically deuteriated samples of (2S)-proline," Org Biomol Chem. 4(8):1483-1491 (2006).
Borowitz et al., "Guidelines for the Diagnosis and Monitoring of Paroxysmal Nocturnal Hemoglobinuria and Related Disorders by Flow Cytometry," Cytometry B Clin Cytom. 78B(4): 211-230 (2010).
Brodsky, "Eculizumab: another breakthrough," Blood. 129(8):922-3 (2017).
Carter, "Complement Activation: An Emerging Player in the Pathogenesis of Cardiovascular Disease," Scientifica. 2012:402783 (2012) (14 pages).
CAS RN 1236228-05-9, dated Aug. 16, 2010 (1 page).
CAS RN 1236251-51-6, dated Aug. 17, 2010 (2 pages).
CAS RN 1270608-88-2, dated 2019 (1 page).
CAS RN 1277041-86-7, dated Apr. 8, 2011 (2 pages).
Cofiell et al., "Eculizumab reduces complement activation, inflammation, endothelial damage, thrombosis, and renal injury markers in aHUS," Blood. 125(21):3253-62 (2015).
Cole et al. "Structure of 3,4-Dichloroisocoumarin-Inhibited Factor D," Acta Crystallogr D Biol Crystallogr. 54(Pt 5): 711-717 (1998).
Compound Summary for CID 1129904, PubChem. <https://pubchem.ncbi.nlm.nih.gov/compound/1129904> retrieved Jul. 14, 2020, created Jul. 10, 2005 (10 pages).
Compound Summary for CID 118324207, PubChem, <https://pubchem.ncbi.nlm.nih.gov/compound/118324207>, created Feb. 23, 2016, retrieved on Jul. 14, 2020 (8 pages).
Compound Summary for CID 123543544, PubChem, <https://pubchem.ncbi.nlm.nih.gov/compound/123543544>, created on Jan. 25, 2017, retrieved on Jul. 13, 2020 (8 pages).
Compound Summary for CID 134222466, PubChem, <https://pubchem.ncbi.nlm.nih.gov/compound/134222466>, created on Jun. 23, 2018, retrieved on Jul. 14, 2020 (11 pages).

(56) References Cited

OTHER PUBLICATIONS

Compound Summary for CID 59912842, PubChem, <https://pubchem.ncbi.nlm.nih.gov/compound/59912842>, created Aug. 20, 2012, retrieved Jul. 14, 2020 (9 pages).
Damasio, "Alzheimer's disease and related dementias," Cecil Textbook of Medicine, 20th Edition, vol. 2. Bennet and Plum, 1992-6 (1996).
Database Registry Chemical Abstracts Service, Columbus, Ohio, Accession No. RN1236248-20-6, Entered STN: Aug. 16, 2010 (1 page).
Database Registry Chemical Abstracts Service, Columbus, Ohio, Accession No. RN1380849-41-1, Entered STN: Jul. 3, 2012 (2 pages).
De Luca et al., "HIV-1 integrase strand-transfer inhibitors: Design, synthesis and molecular modeling investigation," Eur J Med Chem. 46(2): 756-764 (2011).
DeZern et al., "Paroxysmal nocturnal hemoglobinuria: a complement-mediated hemolytic anemia," available in PMC Dec. 30, 2015, published in final edited form as: Hematol Oncol Clin North Am. 29(3):479-94 (2015) (18 pages).
Donthiri et al., "Copper-Catalyzed C—H Functionalization of Pyridines and Isoquinolines with Vinyl Azides: Synthesis of Imidazo Heterocycles," J Org Chem. 79(22): 11277-11284 (2014).
Dormoy et al., "Synthesis of N-t-Butoxycarbonyl-4,4-dideuterio-L-proline," Synthesis. 1: 81-82 (1986).
Ellis-Pegler et al., "An Orally Administered Small Molecule Factor D Inhibitor (ACH-4471) for Treatment of PNH and Complement Diseases: Preliminary Phase 1 Results In Healthy Volunteers," European Hematology Association. Abstract LB2250, available <https://library.ehaweb.org/eha/2016/21st/135361/roderick.b.ellis-pegler.an.orally.administered.small.molecule.factor.d.html> (2016) (2 pages).
Ellis-Pegler et al., "An Orally Administered Small Molecule Factor D Inhibitor (ACH-4471) for Treatment of PNH, C3G and Complement—Mediated Diseases: Interim Phase 1 Results In Healthy Volunteers," European Hematology Association, Copenhagen 21st Congress, Jun. 9-12, Abstract ID: EHA-4145 (2016).
Extended European Search Report for European Application No. 18761960.6, dated Mar. 1, 2021 (10 pages).
Extended European Search Report for European Application No. 18840849.6, dated Mar. 17, 2021 (11 pages).
Gadhachanda et al., CAplus Database Summary Sheet for Document No. 164:507515, Accession No. 2016:627420, CAplus on STN. (2016) (6 pages).
Gavrillaki et al., "275 Small Molecule Factor D Inhibitors Block Complement Activation in Paroxysmal Nocturnal Hemoglobinuria and Atypical Hemolytic Uremic Syndrome," ASH 57th Annual Meeting & Exposition, Session: 101. Dec. 6, 2015 (2 pages).
Golub et al., "Molecular classification of cancer: class discovery and class prediction by gene expression monitoring," Science. 286(5439):531-537 (1999) (8 pages).
Gura, "Systems for identifying new drugs are often faulty," Science. 278(5340):1041-2 (1997).
Haddrill, "Stargardt's Disease (Fundus Flavimaculatus)," All About Vision, <https://www.allaboutvision.com/conditions/stargardts.htm#article-section-2>, retrieved May 3, 2019 (5 pages).
Harder et al., "Incomplete inhibition by eculizumab: mechanistic evidence for residual C5 activity during strong complement activation," Blood.129(8):970-80 (2017).
Hartmann et al., "Diagnostic Specificity of Sucrose Hemolysis Test for Paroxysmal Nocturnal Hemoglobinuria," Blood. 35(4):462-475 (1970).
Hecker et al., "Liver-Targeted Prodrugs of 2'-C-Methyladenosine for Therapy of Hepatitis C Virus Infection," J Med Chem. 50(16): 3891-3896 (2007).
Hruby et al., "$^{13}$C Nuclear Magnetic Resonance Studies of the Peptide Hormones Oxytocin, Arginine Vasopressin, Isotocin, Mesotocin, Glumitocin, Aspartocin, Related Analogues, and Diastereoisomers. Use of Specifically Deuterated Hormone Derivatives for Assignments and Effects of Structural Changes on $_{13}$C NMR Chemical Shifts in Peptides," J Am Chem Soc. 101(1): 202-212(1979).
Hu et al., "Evidence of complement dysregulation in outer retina of Stargardt disease donor eyes," Redox Biol. 37:101787 (2020) (10 pages).
International Search Report and Written Opinion for International Application No. PCT/US2015/017523, dated May 14, 2015 (7 pages).
International Search Report and Written Opinion for International Application No. PCT/US2015/017538, dated May 14, 2015 (8 pages).
International Search Report and Written Opinion for International Application No. PCT/US2015/017554, dated May 14, 2015 (7 pages).
International Search Report and Written Opinion for International Application No. PCT/US2015/017583, dated May 27, 2015 (12 pages).
International Search Report and Written Opinion for International Application No. PCT/US2015/017593, dated Jun. 16, 2015 (6 pages).
International Search Report and Written Opinion for International Application No. PCT/US2015/017597, dated Jan. 29, 2016 (10 pages).
International Search Report and Written Opinion for International Application No. PCT/US2015/017600, dated May 27, 2015 (12 pages).
International Search Report and Written Opinion for International Application No. PCT/US2015/017609, dated May 29, 2015 (6 pages).
International Search Report and Written Opinion for International Application No. PCT/US2016/048688, dated Dec. 28, 2016 (11 pages).
International Search Report and Written Opinion for International Application No. PCT/US2016/048690, dated Dec. 28, 2016 (11 pages).
International Search Report and Written Opinion for International Application No. PCT/US2016/048693, dated Jan. 13, 2017 (11 pages).
International Search Report and Written Opinion for International Application No. PCT/US2016/048695, dated Dec. 30, 2016 (10 pages).
International Search Report and Written Opinion for International Application No. PCT/US2016/048696, dated Jan. 5, 2017 (10 pages).
International Search Report and Written Opinion for International Application No. PCT/US2016/048701, dated Jan. 10, 2017 (10 pages).
International Search Report and Written Opinion for International Application No. PCT/US2016/048704, dated Dec. 27, 2016 (7 pages).
International Search Report and Written Opinion for International Application No. PCT/US2016/048707, dated Jan. 5, 2017 (10 pages).
International Search Report and Written Opinion for International Application No. PCT/US2016/048709, dated Jan. 17, 2017 (9 pages).
International Search Report and Written Opinion for International Application No. PCT/US2016/048710, dated Jan. 5, 2017 (8 pages).
International Search Report and Written Opinion for International Application No. PCT/US2016/048779, dated Dec. 27, 2016 (8 pages).
International Search Report and Written Opinion for International Application No. PCT/US2016/048783, dated Feb. 3, 2017 (8 pages).
International Search Report and Written Opinion for International Application No. PCT/US2016/048787, dated Jan. 5, 2017 (13 pages).
International Search Report and Written Opinion for International Application No. PCT/US2016/048788, dated Jan. 5, 2017 (12 pages).
International Search Report and Written Opinion for International Application No. PCT/US2016/048793, dated Dec. 28, 2016 (8 pages).

(56) References Cited

OTHER PUBLICATIONS

International Search Report and Written Opinion for International Application No. PCT/US2016/048795, dated Feb. 17, 2017 (12 pages).
International Search Report and Written Opinion for International Application No. PCT/US2016/048797, dated Jan. 5, 2017 (12 pages).
International Search Report and Written Opinion for International Application No. PCT/US2016/048799, dated Nov. 15, 2016 (7 pages).
International Search Report and Written Opinion for International Application No. PCT/US2016/048800, dated Jan. 5, 2017 (12 pages).
International Search Report and Written Opinion for International Application No. PCT/US21/18871, dated May 24, 2021 (24 pages).
International Search Report and Written Opinion for International Application No. PCT/US21/21563, dated May 18, 2021 (15 pages).
International Search Report for International Application No. PCT/US18/20530, dated Jun. 25, 2018 (3 pages).
International Search Report for International Application No. PCT/US20/24017, dated Jun. 26, 2020 (3 pages).
International Search Report for International Application No. PCT/US2018/020528, dated Apr. 24, 2018 (3 pages).
International Search Report for International Application No. PCT/US2018/045057, dated Nov. 15, 2018 (5 pages).
International Search Report for International Application No. PCT/US2018/20531, dated May 15, 2018 (3 pages).
International Search Report for International Application No. PCT/US2019/034210, dated Sep. 13, 2019 (4 pages).
International Search Report for International Application No. PCT/US2019/047252, dated Dec. 17, 2019 (4 pages).
International Search Report for International Application No. PCT/US2019/050065, dated Feb. 25, 2020 (4 pages).
International Search Report for International Application No. PCT/US2019/050073, dated Nov. 21, 2019 (3 pages).
International Search Report for International Application No. PCT/US2019/053012, dated Jan. 28, 2020 (4 pages).
International Search Report for International Application No. PCT/US2019/066999, dated Feb. 12, 2020 (3 pages).
Ishibashi et al., "Four-year outcomes of intravitreal aflibercept treatment for neovascular age-related macular degeneration using a treat-and-extend regimen in Japanese patients," Ther Adv Ophthalmol. 13:1-5 (2021).
Jensen et al., "Associations between the Complement System and Choroidal Neovascularization in Wet Age-Related Macular Degeneration," Int J Mol Sci. 21(24):9752 (2020) (28 pages).
Johnson et al., "Relationships between drug activity in NCI preclinical in vitro and in vivo models and early clinical trials," Br J Cancer. 84(10):1424-31 (2001).
Józsi, "Anti-Complement Autoantibodies in Membranoproliferative Glomerulonephritis and Dense Deposit Disease", *An Update on Glomerulopathies—Etiology and Pathogenesis*. Prof. Sharma Prabhakar, 31-46 (2011) (18 pages).
Kathuria, "Membranoproliferative Glomerulonephritis Medication," Medscape, <https://emedicine.medscape.com/article/240056-medication>, updated Jun. 23, 2016, retrieved May 3, 2019, (1 page).
Kinman, "COPD Drugs: A List of Medications to Help Relieve Your Symptoms," Healthline, <https://www.healthline.com/health/copd/drugs>, retrieved on May 3, 2019 (12 pages).
Komiya et al., CAplus Database Summary Sheet for Document No. 162:229476, Accession No. 2015:126147, CAplus on STN. (2015) (2 pages).
Krauss, "Laboratory Diagnosis of Paroxysmal Nocturnal Hemoglobinuria," Annals of Clinical & Laboratory Science. 33(4):401-406 (2003).
Kuang et al., "Synthesis of (Z)-1-bromo-1-alkenes and terminal alkynes from anti-2,3-dibromoalkanoic acids by microwave-induced reaction," Tetrahedron. 61(16):4043-4052 (2005).

Lala et al., "Role of nitric oxide in tumor progression: lessons from experimental tumors," Cancer Metastasis Rev. 17(1):91-106 (1998).
Lassmann, "What drives disease in multiple sclerosis: Inflammation or neurodegeneration?" Clinical and Experimental Neuroimmunology. 1:2-11 (2010).
Layzer, "Degenerative Diseases of the Nervous System," *Cecil Textbook of Medicine, 20th Edition*, vol. 2. J. Claude Bennett and Fred Plum, p. 2050-2057 (1996).
Le et al., "A mechanistic pharmacokinetic/pharmacodynamic model of factor D inhibition in cynomolgus monkeys by lampalizumab for the treatment of geographic atrophy," J Pharmacol Exp Ther. 355(2):288-96 (2015).
MacKay et al., "Rapid Synthesis of the N-Methylwelwitindolinone Skeleton," Org Lett. 7(16):3421-4 (2005).
Mastellos et al., "Complement in paroxysmal nocturnal hemoglobinuria: exploiting our current knowledge to improve the treatment landscape," available in PMC Apr. 2, 2015, published in final edited form as: Expert Rev Hematol. 7(5):583-98 (2014) (26 pages).
Noris et al., "Overview of Complement Activation and Regulation," Semin Nephrol. 33:479-492 (2013).
Office Action issued for Eurasian Patent Application No. 201992005, dated Oct. 23, 2020 (6 pages).
Okutani et al., "Conversion of Bromoalkenes into Alkynes by Wet Tetra-n-butylammonium Fluoride," J Org Chem. 74(1):442-444 (2009).
Oseini et al., "Therapies in Non-Alcoholic Steatohepatitis (NASH)," available in PMC Jan. 1, 2018, published in final edited form as: Liver Int. 37(Suppl 1):97-103 (2017) (15 pages).
Oshima et al., "Correlation between improvement in visual acuity and QOL after Ranibizumab treatment for age-related macular degeneration patients: QUATRO study," BMC Ophthalmol. 21(1):58 (2021) (11 pages).
Pandya et al., "Complement System in Lung Disease," Am J Respir Cell Mol Biol. 51(4):467-473 (2014).
Parker, "Update on the diagnosis and management of paroxysmal nocturnal hemoglobinuria," Hematology Am Soc Hemtol Educ Program. 2016(1):208-16 (2016).
Partial Supplementary European Search Report for European Application No. 18761960.6, dated Nov. 27, 2020 (12 pages).
Patel et al., "In Vitro Combination Studies of ACH-4471 with Eculizumab to Assess a Potential 'Switch' Treatment Approach for Paroxysmal Nocturnal Hemoglobinuria" 59th American Society of Hematology Annual Meeting and Exposition, Dec. 9-12, Atlanta, Georgia, Poster Abstract 2198 (2017).
Pearce et al., "Failure modes in anticancer drug discovery and development," Cancer Drug Design and Discovery Edited by Stephen Neidle, Chapter 18, pp. 424-435 (2008).
Peifer et al., "Design, Synthesis, and Biological Evaluation of Novel 3-Aryl-4-(1H-indole-3yl)-1,5-dihydro-2H-pyrrole-2-ones as Vascular Endothelial Growth Factor Receptor (VEGF-R) Inhibitors," J Med Chem. 51(13):3814-3824 (2008).
Pugsley et al., "Inhibitors of the complement system currently in development for cardiovascular disease," Cardiovasc Toxicol. 3(1):43-69 (2003).
Qu et al., "Recent Developments in Low Molecular Weight Complement Inhibitors," available in PMC, Dec. 1, 2010, published in final edited form as: Mol Immunol. 47(2-3):185-195 (2009) (25 pages).
Quesada et al., "One-pot conversion of activated alcohols into terminal alkynes using manganese dioxide in combination with the Bestmann--Ohira reagent," Tetrahedron Letters. 46:6473-6476 (2005).
Ricklin et al., "Complement in immune and inflammatory disorders: pathophysiological mechanisms," J Immunol. 190(8):3831-3838 (2013).
Risitano et al., "Complement fraction 3 binding on erythrocytes as additional mechanism of disease in paroxysmal nocturnal hemoglobinuria patients treated by eculizumab," Blood. 113(17):4094-4100 (2009) (25 pages).
Risitano et al., "Peptide inhibitors of C3 activation as a novel strategy of complement inhibition for the treatment of paroxysmal nocturnal hemoglobinuria," Blood. 123(13):2094-101 (2014).
Risitano et al., "Safety and Pharmacokinetics of the Complement Inhibitor TT30 in a Phase I Trial for Untreated PNH Patients" Blood. 126(23): 2137 (2015) (Abstract Only) (7 pages).

(56) References Cited

OTHER PUBLICATIONS

Risitano et al., "Toward complement inhibition 2.0: Next generation anticomplement agents for paroxysmal nocturnal hemoglobinuria," Am J Hematol. 93(4):564-77 (2018).
Risitano, "Anti-Complement Treatment in Paroxysmal Nocturnal Hemoglobinuria: Where we Stand and Where we are Going," Transl Med UniSa. 8:43-52 (2014).
Risitano, "Paroxysmal nocturnal hemoglobinuria in the era of complement inhibition," Am J Hematol. 91(4):359-60 (2016).
Rohrer et al., "Eliminating complement factor D reduces photoreceptor susceptibility to light-induced damage," Invest Ophthalmol Vis Sci. 48(11):5282-9 (2007).
Roth et al., "Further Improvements of the Synthesis of Alkynes from Aldehydes," Synthesis. 1:59-62 (2004).
Ruiz-Gómez et al., "Structure--Activity Relationships for Substrate-Based Inhibitors of Human Complement Factor B," J Med Chem. 52(19):6042-6052 (2009).
Salifu, "Chronic Glomerulonephritis Medication," Medscape, <https://emedicine.medscape.com/article/239392-medication>, updated Feb. 1, 2017, retrieved on May 2, 2019 (1 page).
Segers et al., "Complement Alternative Pathway Activation in Human Nonalcoholic Steatohepatitis," PLOS ONE. 9(10):e110053 (2014) (9 pages).
Sica et al., "Eculizumab treatment: stochastic occurrence of C3 binding to individual PNH erythrocytes," J Hematol Oncol. 10(1):126 (2017) (10 pages).
Simone, "Oncology: Introduction," Cecil Textbook of Medicine, 20th Edition, vol. 1, pp. 1004-1010, (1996).
Stanton et al., "Complement Factor D in Age-Related Macular Degeneration," Invest Ophthalmol Vis Sci. 52(12):8828-8834 (2011) (15 pages).
Steinle et al., "Impact of Baseline Characteristics on Geographic Atrophy Progression in the FILLY Trial Evaluating the Complement C3 Inhibitor Pegcetacoplan," Am J Ophthalmol. DOI: https://doi.org/10.1016/j.ajo.2021.02.031 (Journal Pre-proof version) (2021) (19 pages).
Strobel et al., "Anti-factor B autoantibody in dense deposit disease," Mol Immunol. 47:1476-1483 (2010).
Tandon et al., "Substrate specificity of human prolyl-4-hydroxylase," Bioorg Med Chem Lett. 8(10):1139-1144 (1998).
Tang et al. "Palladium-Catalyzed Carbonylative Sonogashira Coupling of Aryl Bromides via tert-Butyl Isocyanide Insertion," J Org Chem. 78(7):3170-3175 (2013).
Wehling et al., "Monitoring of complement activation biomarkers and eculizumab in complement-mediated renal disorders," Clin Exp Immunol. 187(2):304-15 (2017).
Written Opinion for International Application No. PCT/US18/20528, dated Apr. 24, 2018 (6 pages).
Written Opinion for International Application No. PCT/US18/20530, dated Jun. 25, 2018 (6 pages).
Written Opinion for International Application No. PCT/US18/20531, dated May 15, 2018 (7 pages).
Written Opinion for International Application No. PCT/US19/47252, dated Dec. 17, 2019 (6 pages).
Written Opinion for International Application No. PCT/US19/50065, dated Feb. 25, 2020 (7 pages).
Written Opinion for International Application No. PCT/US19/53012, dated Jan. 28, 2020 (5 pages).
Written Opinion for International Application No. PCT/US19/66999, dated Feb. 12, 2020 (7 pages).
Written Opinion for International Application No. PCT/US20/24017, dated Jun. 26, 2020 (6 pages).
Written Opinion for International Application No. PCT/US2018/045057, dated Nov. 15, 2018 (7 pages).
Written Opinion for International Application No. PCT/US2019/034210, dated Sep. 13, 2019 (17 pages).
Written Opinion for International Application No. PCT/US2019/050073, dated Nov. 21, 2019 (4 pages).
Yonemoto-Kobayashi et al., "Carboxylation of alkynylsilanes with carbon dioxide mediated by cesium fluoride in DMSO," Org Biomol Chem. 11(23):3773-5 (2013).
Yuan et al., "Small-molecule Factor D Inhibitors Selectively Block the Alternative Pathway of Complement in Paroxysmal Nocturnal Hemoglobinuria and Atypical Hemolytic Uremic Syndrome," Haematologica. 102(3):466-75 (2017).
"Patient Information for Tarpeyo (tar-PAY-oh) (budesonide) delayed release capsules," Calliditas Therapeutics AB, 2021 (2 pages).
Andrighetto et al., "Complement and Complement Targeting Therapies in Glomerular Diseases," Int J Mol Sci. 20(24):6336 (Dec. 2019), available <https://www.ncbi.nlm.nih.gov/pmc/articles/PMC6940904/>, retrieved on May 26, 2022 (21 pages).
Gilkeson, "Complement-Targeted Therapies in Lupus," Curr Treat Options in Rheum. 1:10-18 (Jan. 22, 2015).
Harris et al., "Developments in anti-complement therapy; from disease to clinical trial," Mol Immunol. 102:89-119 (Oct. 2018).
Hom et al., "Complement Inhibitors for Treatment of Geographic Atrophy and Advanced Nonexudative AMD," Retinal Physician. 16:28-31 (Mar. 1, 2019) (7 pages).
Iatropoulos et al., "Cluster Analysis Identifies Distinct Pathogenetic Patterns in C3 Glomerulopathies/Immune Complex-Mediated Membranoproliferative GN," J Am Soc Nephrol. 29(1):283-94 (with supplemental material) (Jan. 2018) (36 pages).
Kocinsky et al., "Abstract SaO018: Factor D inhibition with ACH-4471 to reduce complement alternative pathway hyperactivity and proteinuria in C3 glomerulopathy: preliminary proof of concept data," Nephrology Dialysis Transplantation. 33(Supplement 1):i322-3 (May 2018) (1 page).
Mantegazza et al., "Complement Inhibition for the Treatment of Myasthenia Gravis," Immunotargets Ther. 9:317-31 (2020), <https://www.ncbi.nlm.nih.gov/pmc/articles/PMC7751298/>, retrieved on May 26, 2022 (24 pages).
Marinozzi et al., "C5 nephritic factors drive the biological phenotype of C3 glomerulopathies," Kidney Int. 92(5):1232-41 (Nov. 2017).
Michels et al., "Long-term follow-up including extensive complement analysis of a pediatric C3 glomerulopathy cohort," Pediatr Nephrol. 37(3):601-12 (Mar. 2022).
Risitano et al., "Danicopan: an oral complement factor D inhibitor for paroxysmal nocturnal hemoglobinuria," Haematologica. 106(12):3188-97 (2021).
Varelas et al., "Complement in Sickle Cell Disease: Are We Ready for Prime Time?," J Blood Med. 12:177-87 (2021), <https://www.ncbi.nlm.nih.gov/pmc/articles/PMC8001680/>, dated Mar. 23, 2021, retrieved on May 26, 2022 (19 pages).
Willows et al., "The role of complement in kidney disease," Clin Med (Lond). 20(2):156-60 (2020) (9 pages).
Zhang et al., "Defining the complement biomarker profile of C3 glomerulopathy," Clin J Am Soc Nephrol. 9(11):1876-82 (supplemental materials) (Nov. 7, 2014) (10 pages).

Rxn#1: 2.4 g from 2.5 g of 1

ARYL, HETEROARYL, AND HETEROCYCLIC PHARMACEUTICAL COMPOUNDS FOR TREATMENT OF MEDICAL DISORDERS

CROSS-REFERENCE TO RELATED APPLICATIONS

This application is a continuation of U.S. application Ser. No. 16/555,914, filed Aug. 29, 2019, which is a continuation of International Application No. PCT/US2018/020528, filed Mar. 1, 2018, which claims the benefit of priority to U.S. Application No. 62/465,782, filed Mar. 1, 2017; and U.S. Application No. 62/466,301 filed Mar. 2, 2017; each of which are incorporated by reference herein for all purposes.

FIELD OF THE INVENTION

This invention provides aryl, heteroaryl and heterocyclic drugs to treat medical disorders, such as complement-mediated disorders.

BACKGROUND OF THE INVENTION

The complement system is a part of the innate immune system which does not adapt to changes over the course of the host's life, but is recruited and used by the adaptive immune system. For example, it assists, or complements, the ability of antibodies and phagocytic cells to clear pathogens. This sophisticated regulatory pathway allows rapid reaction to pathogenic organisms while protecting host cells from destruction. Over thirty proteins and protein fragments make up the complement system. These proteins act through opsonization (enhancing phagocytosis of antigens), chemotaxis (attracting macrophages and neutrophils), cell lysis (rupturing membranes of foreign cells), and agglutination (clustering and binding of pathogens together).

The complement system has three pathways: classical, alternative, and lectin. Complement Factor D plays an early and central role in activation of the alternative pathway of the complement cascade. Activation of the alternative complement pathway is initiated by spontaneous hydrolysis of a thioester bond within C3 to produce $C3(H_2O)$, which associates with Factor B to form the $C3(H_2O)B$ complex. Complement Factor D acts to cleave Factor B within the $C3(H_2O)B$ complex to form Ba and Bb. The Bb fragment remains associated with $C3(H_2O)$ to form the alternative pathway C3 convertase $C3(H_2O)Bb$. Additionally, C3b generated by any of the C3 convertases also associates with Factor B to form C3bB, which Factor D cleaves to generate the later stage alternative pathway C3 convertase C3bBb. This latter form of the alternative pathway C3 convertase may provide important downstream amplification within all three of the defined complement pathways, leading ultimately to the recruitment and assembly of additional factors in the complement cascade pathway, including the cleavage of C5 to C5a and C5b. C5b acts in the assembly of factors C6, C7, C8, and C9 into the membrane attack complex, which can destroy pathogenic cells by lysing the cell.

The dysfunction of or excessive activation of complement has been linked to certain autoimmune, inflammatory, and neurodegenerative diseases, as well as ischemia-reperfusion injury and cancer. For example, activation of the alternative pathway of the complement cascade contributes to the production of C3a and C5a, both potent anaphylatoxins, which also have roles in a number of inflammatory disorders. Therefore, in some instances, it is desirable to decrease the response of the complement pathway, including the alternative complement pathway. Some examples of disorders mediated by the complement pathway include age-related macular degeneration (AMD), paroxysmal nocturnal hemoglobinuria (PNH), multiple sclerosis, and rheumatoid arthritis.

Age-related macular degeneration (AMD) is a leading cause of vision loss in industrialized countries. Based on a number of genetic studies, there is evidence of the link between the complement cascade and macular degeneration. Individuals with mutations in the gene encoding complement Factor H have a fivefold increased risk of macular degeneration and individuals with mutations in other complement factor genes also have an increased risk of AMD. Individuals with mutant Factor H also have increased levels of C-reactive protein, a marker of inflammation. Without adequate functioning Factor H, the alternative pathway of the complement cascade is overly activated leading to cellular damage.

Paroxysmal nocturnal hemoglobinuria (PNH) is a non-malignant, hematological disorder characterized by the expansion of hematopoietic stem cells and progeny mature blood cells that are deficient in some surface proteins. PNH erythrocytes are not capable of modulating their surface complement activation, which leads to the typical hallmark of PNH—the chronic activation of complement mediated intravascular anemia. Currently, only one product, the anti-C5 monoclonal antibody eculizumab, has been approved in the U.S. for treatment of PNH. However, many of the patients treated with eculizumab remain anemic, and many patients continue to require blood transfusions. In addition, treatment with eculizumab requires life-long intravenous injections.

Additional complement-mediated disorders include those classified under component 3 glomerulopathy (C3G). C3G is a recently defined entity comprised of dense deposit disease (DDD) and C3 glomerulonephritis (C3GN) which encompasses a population of chronic kidney diseases wherein elevated activity of the alternative complement pathway and terminal complement pathway results in glomerular deposits made solely of complement C3 and no immunoglobulin (Ig).

Immune-complex membranoproliferative glomerulonephritis (IC-MPGN) is a renal disease which shares many clinical, pathologic, genetic and laboratory features with C3G, and therefore can be considered a sister disease of C3G. In the majority of patients with IC-MPGN, an underlying disease or disorder—most commonly infections, autoimmune diseases, or monoclonal gammopathies—are identified to which the renal disease is secondary. Patients with idiopathic IC-MPGN can have low C3 and normal C4 levels, similar to those observed in C3G, as well as many of the same genetic or acquired factors that are associated with abnormal alternative pathway activity. Although there are current hypotheses suggesting that the majority of IC-MPGN is attributable to over activity of the classical pathway, those patients with a low C3 and a normal C4 are likely to have significant overactivity of the alternative pathway. IC-MPGN patients with a low C3 and a normal C4 may benefit from alternative pathway inhibition.

Other disorders that have been linked to the complement cascade include atypical hemolytic uremic syndrome (aHUS), hemolytic uremic syndrome (HUS), abdominal aortic aneurysm, hemodialysis complications, hemolytic anemia, or hemodialysis, neuromyelitis optica (NMO), myasthenia gravis (MG), fatty liver, nonalcoholic steatohepatitis (NASH), liver inflammation, cirrhosis, liver failure, dermatomyositis, and amyotrophic lateral sclerosis.

Factor D is an attractive target for inhibition or regulation of the complement cascade due to its early and essential role in the alternative complement pathway, and for its potential role in signal amplification within the classical and lectin complement pathways. Inhibition of Factor D effectively interrupts the pathway and attenuates the formation of the membrane attack complex.

While initial attempts have been made to develop inhibitors of Factor D, there are currently no clinically approved small molecule Factor D inhibitors. Examples of Factor D inhibitor compounds are described in the following disclosures.

Biocryst Pharmaceuticals U.S. Pat. No. 6,653,340 titled "Compounds useful in the complement, coagulate and kallikrein pathways and method for their preparation" describes fused bicyclic ring compounds that are potent inhibitors of Factor D. Development of the Factor D inhibitor BCX1470 was discontinued due to lack of specificity and short half-life of the compound.

Novartis PCT patent publication WO2012/093101 titled "Indole compounds or analogues thereof useful for the treatment of age-related macular degeneration" describes certain Factor D inhibitors. Additional Factor D inhibitors are described in Novartis PCT patent publications WO2013/164802, WO2013/192345, WO2014/002051, WO2014/002052, WO2014/002053, WO2014/002054, WO2014/002057, WO2014/002058, WO2014/002059, WO2014/005150, WO2014/009833, WO2014/143638, WO2015/009616, WO2015/009977, and WO2015/066241.

A paper published by Novartis titled "Structure-Based Library Design and Fragment Screening for the Identification of Reversible Complement Factor D Protease Inhibitors" (Vulpetti et al., J. Med. Chem. 10.1021/acs.jmedchem.6b01684) describes an in silico active site mapping for regions that contribute to a large fraction of binding energy using the Factor D crystal structure and NMR-based screening (structure-based drug design (SBDD) and fragment-based screening (FBD)). Another Novartis paper titled "Small-molecule factor D inhibitors targeting the alternative complement pathway" (Maibaum et al., Nat. Chem. Bio. 2016; 12; 1105) discloses small-molecule inhibitors designed by use of a structure-based design approach in combination with fragment-based screening.

Lifesci Pharmaceuticals PCT patent publication WO2017/098328 titled "Therapeutic Inhibitory Compounds" describes various Factor D inhibitors with variations in the central core ring heterocycle ring. PCT patent publication WO/2018/015818 is also titled "Therapeutic Inhibitory Compounds" and describes Factor D inhibitors without cyclic central core.

Bristol-Myers Squibb PCT patent publication WO2004/045518 titled "Open chain prolyl urea-related modulators of androgen receptor function" describes open chain prolyl urea and thiourea related compounds for the treatment of androgen receptor-associated conditions, such as age-related diseases, for example, sarcopenia.

Japan Tobacco Inc. PCT patent publication WO1999/048492 titled "Amide derivatives and nociceptin antagonists" describes compounds with a proline-like core and aromatic substituents connected to the proline core through amide linkages useful for the treatment of pain.

Ferring B. V. and Yamanouchi Pharmaceutical Co. lTD. PCT patent publication WO1993/020099 titled "CCK and/or gastrin receptor ligands" describes compounds with a proline-like core and heterocyclic substituents connected to the proline core through amide linkages for the treatment of, for example, gastric disorders or pain.

Alexion Pharmaceuticals PCT patent publication WO1995/029697 titled "Methods and compositions for the treatment of glomerulonephritis and other inflammatory diseases" discloses antibodies directed to C5 of the complement pathway for the treatment of glomerulonephritis and inflammatory conditions involving pathologic activation of the complement system. Alexion Pharmaceutical's anti-C5 antibody eculizumab (Soliris®) is currently the only complement-specific antibody on the market, and is the first and only approved treatment for paroxysmal nocturnal hemoglobinuria (PNH).

On Feb. 25, 2015, Achillion Pharmaceuticals filed PCT Patent Application No. PCT/US2015/017523 and U.S. patent application Ser. No. 14/631,090 titled "Alkyne Compounds for Treatment of Complement Mediated Disorders"; PCT Patent Application No. PCT/US2015/017538 and U.S. patent application Ser. No. 14/631,233 titled "Amide Compounds for Treatment of Complement Mediated Disorders"; PCT Patent Application No. PCT/US2015/017554 and U.S. patent application Ser. No. 14/631,312 titled "Amino Compounds for Treatment of Complement Mediated Disorders"; PCT Patent Application No. PCT/US2015/017583 and U.S. patent application Ser. No. 14/631,440 titled "Carbamate, Ester, and Ketone Compounds for Treatment of Complement Mediated Disorders"; PCT Patent Application No. PCT/US2015/017593 and U.S. patent application Ser. No. 14/631,625 titled "Aryl, Heteroaryl, and Heterocyclic Compounds for Treatment of Complement Mediated Disorders"; PCT Patent Application No. PCT/US2015/017597 and U.S. patent application Ser. No. 14/631,683 titled "Ether Compounds for Treatment of Complement Mediated Disorders"; PCT Patent Application No. PCT/US2015/017600 and U.S. patent application Ser. No. 14/631,785 titled "Phosphonate Compounds for Treatment of Complement Mediated Disorders"; and PCT Patent Application No. PCT/US2015/017609 and U.S. patent application Ser. No. 14/631,828 titled "Compounds for Treatment of Complement Mediated Disorders" and U.S. patent application Ser. No. 14/630,959 titled "Factor D Inhibitors Useful for Treating Infectious Disorders."

Additional complement factor D inhibitors are described in U.S. Pat. Nos. 9,828,396; 9,695,205; 9,598,446; 9,732,103; 9,796,741; 9,732,104; 9,663,543; 9,758,537; and 9,643,986; International Publication Nos. WO 2015/130784; WO 2015/130795; WO 2015/130806; WO 2015/130830; WO 2015/130838; WO 2015/130842; WO 2015/130845; and WO 2015/130854; and U.S. Patent Publication Nos. US 2017-0298084; US 2016-0362398; US 2017-0189410; US 2017-0298085; US 2018-0030075; US 2016-0362399; US 2018-0022766; US 2016-0362433; US 2017-0260219; US 2016-0362432; US 2018-0022767; US 2016-0361329; and US 2017-0226142; all owned by Achillion Pharmaceuticals, Inc.

Given the wide variety of medical disorders that are caused by detrimental immune or inflammatory responses, new compounds are needed for medical treatment.

SUMMARY

This invention includes a compound of Formula I, Formula II, Formula III, Formula IV, or Formula V or a pharmaceutically acceptable salt, prodrug, isotopic analog, N-oxide, or isolated isomer thereof, optionally in a pharmaceutically acceptable composition, wherein at least one of $R^{12}$ or $R^{13}$ on the A group is an aryl, heteroaryl or heterocycle substituent, which is $R^{32}$. In one embodiment, the compound or its salt or composition, as described herein is used to treat a medical disorder which is an inflammatory or immune condition, a disorder mediated by the complement cascade (including a dysfunctional cascade), a disorder or abnormality of a cell that adversely affects the ability of the cell to engage in or respond to normal complement activity including the alternative complement pathway, or an undesired complement-mediated response to a medical treatment, such as surgery or other medical procedure or a pharmaceutical or biopharmaceutical drug administration, a blood transfusion, or other allogenic tissue or fluid administration.

In certain aspects of the invention, the compound presented herein has one or more of the following:

a. An A ring of the formula:

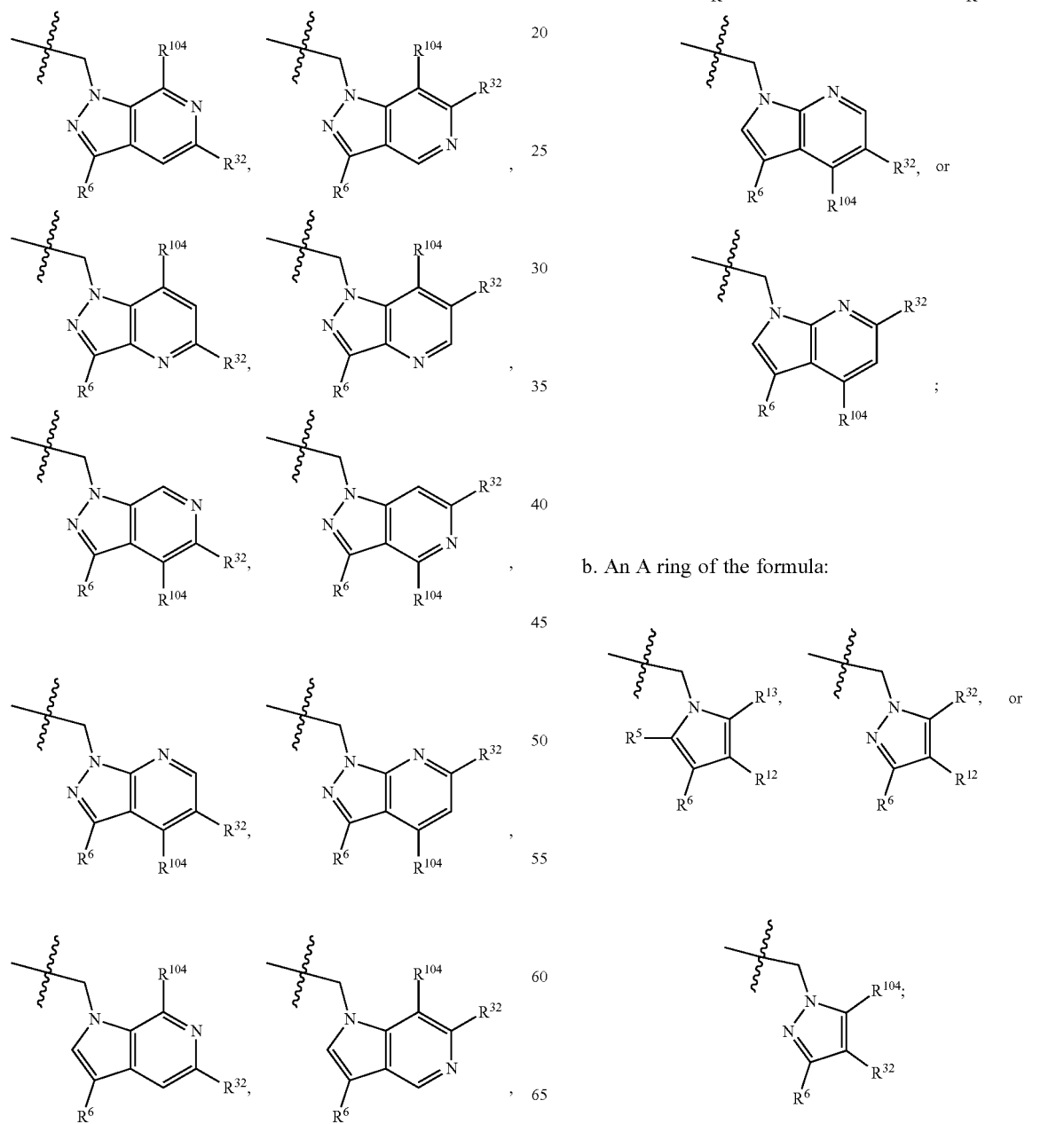

b. An A ring of the formula:

c. An A ring of the formula:

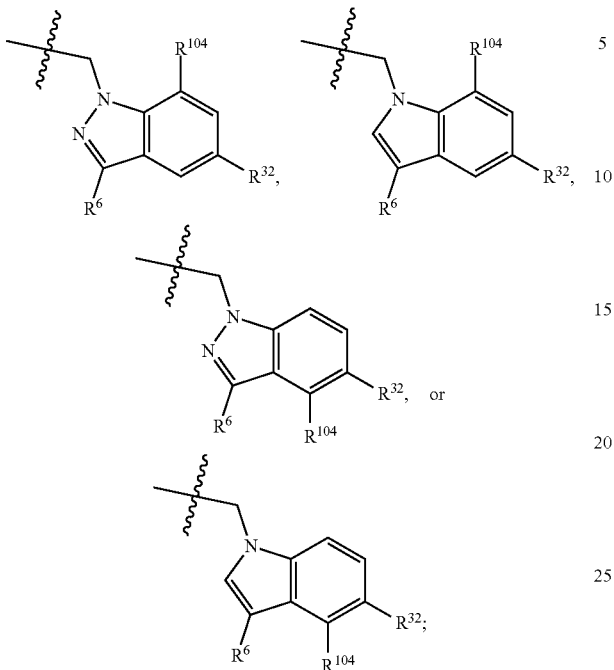

d. A B ring of the formula:

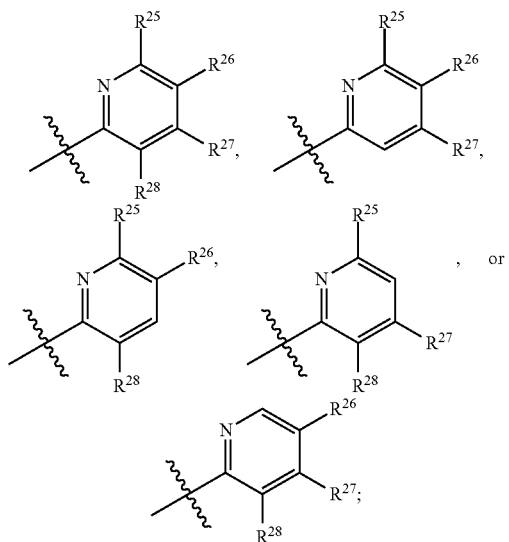

e. A C ring selected from:

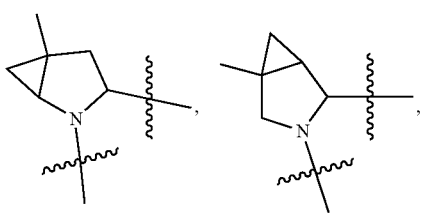

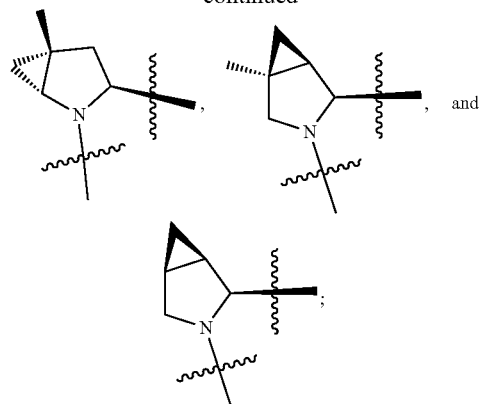

, and f. A C ring of formula:

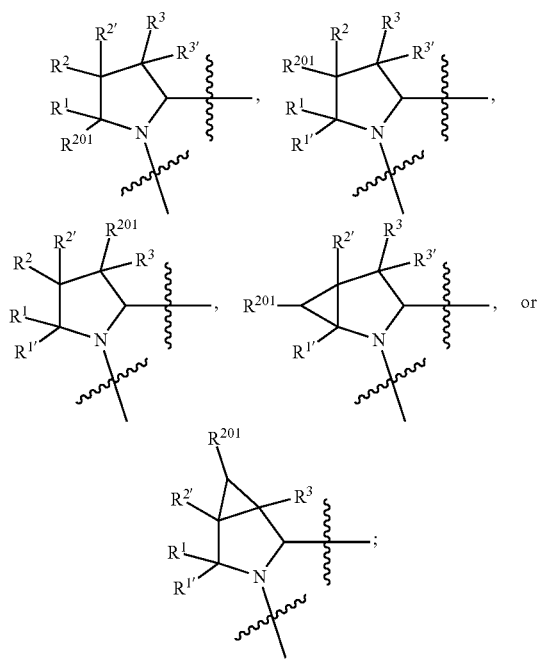

g. A C ring selected from a proline spirocycle (such as those described in the paper published by Litter et al. titled "Development of a Manufacturing Process for an HCV Protease Inhibitor Candidate Molecule" (Organic Process Research & Development 2015, 19, 270-283);

h. An $R^{32}$ selected from a cyclic sulfonimidamide (such as those described in the paper published by Pemberton et al. titled "Synthesis and Functionalization of Cyclic Sulfonimidamides: A Novel Chiral Heterocyclic Carboxylic Acid Biostere" (ACS Med. Chem Letters 2012, 3, 574-578);

i. A compound of the invention with at least one $R^{201}$ substituent selected from aminoalkyl-, alkylaminoalkyl-, heterocycloalkyl-, and hydroxyalkyl; -alkyl-O-alkyl including —CH$_2$OCH$_3$, -alkyl-S-alkyl, -alkyl-N(alkyl)-alkyl, -alkyl-NH-alkyl, -aliphatic-O-aliphatic, -aliphatic-S-aliphatic, -aliphatic-N(aliphatic)-aliphatic, -aliphatic-NH-aliphatic, -aliphatic-O-heterocycle, -aliphatic-S-heterocycle, -aliphatic-N(aliphatic)-heterocycle, -aliphatic-NH-heterocycle, -alkyl-NHC(O)haloalkyl, -alkyl-NR⁹C(O)haloalkyl, -alkyl-C(O)NHhaloalkyl, -alkyl-C(O)NR⁹haloalkyl, -alkyl-NHC(O)haloalkyl, -alkyl-NR⁹C(O)aliphatic, -alkyl-C(O)NHaliphatic, -alkyl-NR⁹C(O)aliphatic, -alkyl-NHC(O)aliphatic, -substituted alkyl-N(R⁹)-substituted alkyl, alkyl-heteroaryl, heteroaryl, heterocycle, alkyl-heterocycle, -alkyl-O-haloalkyl, —N(aliphatic)₂; and wherein each $R^{201}$ can be optionally substituted as defined in the Terminology section below, and wherein each $R^{201}$ can be optionally substituted with $R^{301}$, which can be directly linked to $R^{201}$ or can be linked to $R^{201}$ through an amino, hydroxyl, thio, carboxyl acid, phosphate, phosphonate or sulfonate linkage as desired and appropriate;

j. A compound with at least one $R^{201}$ substituent on the A ring;

k. A compound with at least one $R^{201}$ substituent on the B ring;

l. A compound with at least one $R^{201}$ substituent on the C ring;

m. Certain stable acylated embodiments and acyl prodrugs of the present invention, that include an $R^{301}$ substituent, as further described below.

These compounds can be used to treat medical conditions in a host in need thereof, typically a human. The active compound may act as an inhibitor of the complement factor D cascade. In one embodiment, a method for the treatment of such a disorder is provided that includes the administration of an effective amount of a compound of Formula I, Formula II, Formula III, Formula IV, or Formula V or a pharmaceutically acceptable salt, prodrug, isotopic analog, N-oxide, or isolated isomer thereof, optionally in a pharmaceutically acceptable composition, as described in more detail below.

In certain embodiments, compounds are provided that have minimal effect on BSEP (bile salt export pump protein) (e.g., with an $IC_{50}$ of greater than about 20, 30, 40, 50, 60, 75 or 100 µM or greater), or with a therapeutic index of BSEP relative to complement D inhibition (e.g., $IC_{50}$ inhibition of BSEP/$IC_{50}$ inhibition of complement D inhibitor), of about at least 50, 100, 200, 300, 400, 500, 750 or 1000 or greater). BSEP inhibition correlates with cholestatic drug-induced liver injury. Certain compounds of the present invention with low BSEP inhibition have at least one $R^{201}$.

In some embodiments, the compounds of the present invention exhibit minimal hydrolysis of the amide bond between the C ring and the B ring in vivo, for example, by including a proline that has a cis-substituent relative to the proline-carbonyl bond directed toward the B-ring. In certain embodiments, the cis-substituent is in the Q3 position or the Q2 position or is a group that bridges Q3 and Q2.

It has also been discovered that including a B-ring substituent in the position ortho to the amide (for example 2-(L1)-3-methyl-6-substituted-pyridine or 2-(L1)-3-cyclopropyl-6-substituted-pyridine) may decrease the potential for formation of reactive metabolites.

In one aspect of the invention, an $R^{301}$ acylated embodiment of an active compound of the invention is provided that exhibits extended half-life or other advantageous pharmacokinetic properties, which may be achieved by albumin stabilization in vivo. In certain embodiments, the acylated analogue can include several linking moieties in linear, branched or cyclic manner. In certain embodiments, either one or a series of amino acids is used as a linker to a terminal fatty acid. In one non-limiting example a non-natural amino acid such as one described below, for example 8-amino-3,6-dioxaoctanoic acid (one or several in sequence) is covalently bound to the selected complement D inhibitor of the present invention through a functional group such as a carboxylic acid, sulfonyl, hydroxyl or amino group. See generally Lau, et al., "Discovery of the Once-Weekly Glucagon-Like Peptide-1 (GLP-1) Analogue Semiglutide", *J. Med. Chem.*, 2015, 58, 7370-7380. In this embodiment, the 8-amino-3,6-dioxaoctanoic acid or similar molecule is covalently linked to an aliphatic acid, including but not limited to a $C_{16}$, $C_{18}$, $C_{20}$ aliphatic acid, or a dicarboxylic acid, including but not limited to a $C_8$, $C_{10}$, $C_{12}$, $C_{14}$, $C_{16}$, $C_{18}$ or $C_{20}$ diacid. One or more amino acids can also be used in the selected configuration to add length or functionality. More generally, nonlimiting embodiments include the use of a divalent linker moiety such as a dicarboxylic acid, amino acid, diamine, hydroxycarboxylic acid, hydroxyamine, dihydroxy compound, or other compound that has at least two functional groups that can link the parent molecule with another linking moiety, and which may be albumin stabilized in vivo. In some embodiments, 2, 3, 4 or 5 linking moieties are covalently bound in sequence, branched or cyclic fashion to the parent compound. In some embodiments, an $R^{301}$ acyl group is located in a position of the active compound that does not significantly adversely affect the complement D inhibition of the molecule, for example, as (i) a substituent on the $R^{32}$ group or (ii) a substituent on a C-ring, such as proline, or as a substituent on a substituent on the C-ring, such as on an $R^1$, $R^2$ or $R^3$ substituent, including for example, on a bridged moiety such as a fused cyclopropyl on the proline ring. In certain embodiments, the acyl group has an aliphatic or heteroaliphatic carbon range of $C_{12}$, $C_{14}$, $C_{16}$, $C_{18}$, $C_{20}$, $C_{22}$ or $C_{24}$.

In one embodiment, the disorder is associated with the alternative complement cascade pathway. In yet another embodiment, the disorder is associated with the complement classical pathway. In a further embodiment, the disorder is associated with the complement lectin pathway. Alternatively, the active compound or its salt or prodrug may act through a different mechanism of action than the complement cascade, or in particular as a complement factor D inhibitor, to treat the disorder described herein.

In one embodiment, a method for the treatment of C3 glomerulonephritis (C3G) is provided that includes the administration of an effective amount of a compound to a host of Formula I, Formula II, Formula III, Formula IV, or Formula V or a pharmaceutically acceptable salt, prodrug, isotopic analog, N-oxide, or isolated isomer thereof, optionally in a pharmaceutically acceptable composition. In one embodiment, a method for the treatment of paroxysmal nocturnal hemoglobinuria (PNH) is provided that includes the administration of an effective amount of a compound to a host of Formula I, Formula II, Formula III, Formula IV, or Formula V or a pharmaceutically acceptable salt, prodrug, isotopic analog, N-oxide, or isolated isomer thereof, optionally in a pharmaceutically acceptable composition. In another embodiment, a method for the treatment of wet or dry age-related macular degeneration (AMD) in a host is provided that includes the administration of an effective amount of a compound of Formula I, Formula II, Formula III, Formula IV, or Formula V, or a pharmaceutically acceptable salt, prodrug, isotopic analog, N-oxide, or isolated isomer thereof, optionally in a pharmaceutically acceptable composition. In another embodiment, a method for the treatment of rheumatoid arthritis in a host is provided that includes the administration of an effective amount of a compound of Formula I, Formula II, Formula III, Formula IV, or Formula V or a pharmaceutically acceptable salt, prodrug, isotopic analog, N-oxide, or isolated isomer thereof, optionally in a pharmaceutically acceptable composition. In another embodiment, a method for the treatment of multiple sclerosis in a host is provided that includes the administration of an effective amount of a compound of Formula I, Formula II, Formula III, Formula IV, or Formula V or a pharmaceutically acceptable salt, prodrug, isotopic analog, N-oxide, or isolated isomer thereof, optionally in a pharmaceutically acceptable composition.

In other embodiments, an active compound or its salt or prodrug as described herein can be used to treat fatty liver and conditions stemming from fatty liver, nonalcoholic steatohepatitis (NASH), liver inflammation, cirrhosis, and liver failure, dermatomyositis, or amyotrophic lateral sclerosis.

The active compound or its pharmaceutically acceptable salt, prodrug, isotopic analog, N-oxide, or isolated isomer thereof, optionally in a pharmaceutically acceptable composition, as disclosed herein is also useful for administration in combination (in the same or a different dosage form) or alternation with a second pharmaceutical agent for use in ameliorating or reducing a side effect of the second pharmaceutical agent. For example, in one embodiment, the active compound may be used in combination with an adoptive cell transfer therapy to reduce an inflammatory response associated with such therapy, for example, a cytokine mediated response such as cytokine response syndrome. In one embodiment, the adoptive cell transfer therapy is a chimeric antigen receptor T-Cell (CAR T) or a dendritic cell used to treat a hematologic or solid tumor, for example, a B-cell related hematologic cancer. In one embodiment, the hematologic or solid tumor is acute lymphoblastic leukemia (ALL), acute myeloid leukemia (AML), non-Hodgkin's lymphoma, chronic lymphocytic leukemia (CLL), pancreatic cancer, glioblastoma, or a cancer that expresses CD19. In one embodiment, the associated inflammatory response is a cytokine mediated response.

Another embodiment is provided that includes the administration of an effective amount of an active compound or a pharmaceutically acceptable salt, prodrug, isotopic analog, N-oxide, or isolated isomer thereof, optionally in a pharmaceutically acceptable composition to a host to treat an ocular, pulmonary, gastrointestinal, or other disorder that can benefit from topical or local delivery.

Any of the compounds described herein (e.g. Formula I, Formula II, Formula III, Formula IV, or Formula V) can be administered to the eye in any desired form of administration, including via intravitreal, intrastromal, intracameral, sub-tenon, sub-retinal, retro-bulbar, peribulbar, suprachoroidal, choroidal, subchoroidal, conjunctival, subconjunctival, episcleral, posterior juxtascleral, scleral, circumcorneal, and tear duct injections, or through a mucus, mucin, or a mucosal barrier, in an immediate or controlled release fashion. In certain embodiments, the active compound includes a lipophilic group, such as a lipophilic acyl group, which is delivered to the eye in a polymeric drug delivery system such as polylactic acid, polylactide-co-glycolide, polyglycolide or other erodible polymer, or a combination thereof, or in another type of lipophilic material for ocular delivery. In some embodiments, the lipophilic active molecule is more soluble in the polymeric or other form of delivery system than in ocular fluid.

In other embodiments of the invention, an active compound provided herein can be used to treat or prevent a disorder in a host mediated by complement factor D, or by an excessive or detrimental amount of the complement-C3 amplification loop of the complement pathway. As examples, the invention includes methods to treat or prevent complement associated disorders that are induced by antibody-antigen interactions, a component of an immune or autoimmune disorder or by ischemic injury. The invention also provides methods to decrease inflammation or an immune response, including an autoimmune response, where mediated or affected by factor D.

In another embodiment, a method is provided for treating a host, typically a human, with a disorder mediated by the complement system, that includes administration of a prophylactic antibiotic or vaccine to reduce the possibility of a bacterial infection during the treatment using one of the compounds described herein. In certain embodiments, the host, typically a human, is given a prophylactic vaccine prior to, during or after treatment with one of the compounds described herein. In certain embodiments, the host, typically a human, is given a prophylactic antibiotic prior to, during or after treatment with one of the compounds described herein. In some embodiments, the infection is a meningococcal infection (e.g., septicemia and/or meningitis), an *Aspergillus* infection, or an infection due to an encapsulated organism, for example, *Streptococcus pneumoniae* or *Haemophilus* influenza type b (Hib), especially in children. In other embodiments, the vaccine or antibiotic is administered to the patient after contracting an infection due to, or concommitent with inhibition of the complement system.

The disclosure provides a compound of Formula I, Formula II, or Formula III:

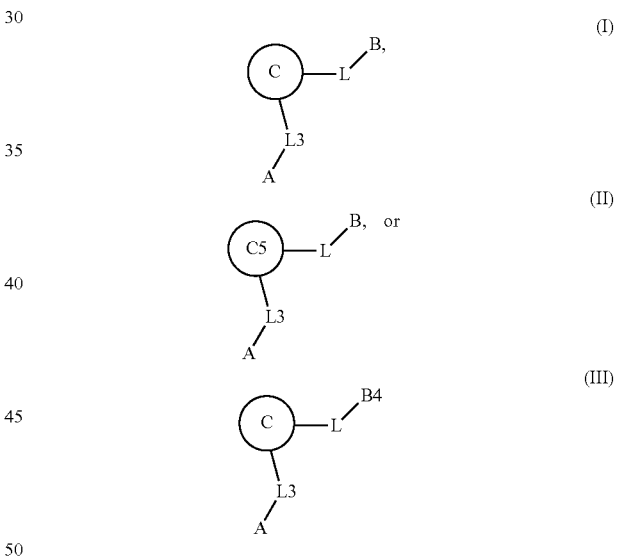

or a pharmaceutically acceptable salt, isotopic analog, prodrug, or isolated isomer thereof optionally in pharmaceutically acceptable carrier;

wherein:

A is selected from A1, A2, and A3;

B is selected from B1, B2, and B3;

or B is B4;

B4 is separately defined below;

C is selected from C1, C2, C3, and C4;

or C is C5;

C5 is separately defined below;

and wherein for compounds of Formula I at least one of the following limitations is present: A is A3, B is B3, or C is C4;

C1 is

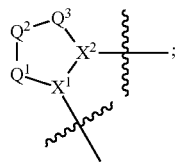

Q$^1$ is N(R$^1$), C(R$^1$R$^{1'}$), C(R$^1$R$^{1'}$)C(R$^1$R$^{1'}$), C(R$^1$R$^{1'}$)C(R$^1$R$^{1'}$)C(R$^1$R$^{1'}$), S or O;

Q$^2$ is C(R$^2$R$^{2'}$), C(R$^2$R$^{2'}$)C(R$^2$R$^{2'}$), C(R$^2$R$^{2'}$)C(R$^2$R$^{2'}$)C(R$^2$R$^{2'}$), N(R$^2$), S, O, or C(R$^2$R$^{2'}$)O;

Q$^3$ is N(R$^3$), S, O, C(R$^3$R$^{3'}$), C(R$^3$R$^{3'}$)C(R$^3$R$^{3'}$), or C(R$^3$R$^{3'}$)C(R$^3$R$^{3'}$)C(R$^3$R$^{3'}$);

X$^1$ and X$^2$ are independently N, CH, or CZ;

or X$^1$ and X$^2$ together are C=C;

wherein X$^1$ is directly bound to L3 and X$^2$ is directly bound to L; and wherein Q$^1$, Q$^2$, Q$^3$, X$^1$, and X$^2$ are selected such that a stable compound results;

Z is F, Cl, NH$_2$, CH$_3$, CH$_2$D, CHD$_2$, or CD$_3$;

R$^1$, R$^{1'}$, R$^2$, R$^{2'}$, R$^3$, and R$^{3'}$ are independently selected at each occurrence, as appropriate, and only where a stable compound results, from hydrogen, R$^{201}$, R$^{301}$, halogen (and specifically fluoro, chloro, bromo), hydroxyl, nitro, cyano, amino, alkyl including C$_1$-C$_6$alkyl, alkenyl including C$_2$-C$_6$alkenyl, alkynyl including C$_2$-C$_6$alkynyl, alkoxy including C$_1$-C$_6$alkoxy, alkanoyl including C$_2$-C$_6$alkanoyl, thioalkyl including C$_1$-C$_6$alkylthio, hydroxyC$_1$-C$_6$alkyl, aminoC$_1$-C$_6$alkyl, —C$_0$-C$_4$alkylNR$^9$R$^{10}$, —C(O)OR$^9$, —OR', —NR'R'', —OC(O)R$^9$, —NR$^9$C(O)R$^{10}$, —C(O)NR$^9$R$^{10}$, —OC(O)NR$^9$R$^{10}$, —NR$^9$C(O)OR$^{10}$, haloalkyl including C$_1$-C$_6$haloalkyl, and C$_1$-C$_6$haloalkoxy;

or R$^1$ and R$^{1'}$ are taken together to form a 3- to 6-membered carbocyclic spiro ring or a 3- to 6-membered heterocyclic spiro ring containing 1 or 2 heteroatoms independently selected from N, O, or S;

or R$^3$ and R$^{3'}$ are taken together to form a 3- to 6-membered carbocyclic spiro ring or a 3- to 6-membered heterocyclic spiro ring containing 1 or 2 heteroatoms independently selected from N, O, or S;

or R$^2$ and R$^{2'}$ are taken together to form a 3- to 6-membered carbocyclic spiro ring or a 3- to 6-membered heterocyclic spiro ring;

wherein, each of the above spiro rings may be optionally substituted with 1 or more substituents independently selected from R$^{201}$, halogen (and in particular F), hydroxyl, cyano, —COOH, alkyl including C$_1$-C$_4$alkyl (and in particular methyl), alkenyl including C$_2$-C$_4$alkenyl, alkynyl including C$_2$-C$_4$alkynyl, alkoxy including C$_1$-C$_6$alkoxy, alkanoyl, including C$_2$-C$_4$alkanoyl, hydroxyC$_1$-C$_4$alkyl, (mono- and di-alkylamino)C$_1$-C$_4$alkyl, —C$_0$-C$_4$alkyl(C$_3$-C$_7$cycloalkyl), —O-alkyl(C$_3$-C$_7$cycloalkyl), haloalkyl including C$_1$-C$_6$haloalkyl, and haloalkoxy including C$_1$-C$_6$haloalkoxy;

or in an alternative embodiment, each of the above spiro rings may be optionally substituted with an aryl ring;

or R$^1$ and R$^2$ are taken together to form a 3-membered carbocyclic ring, a 4- to 6-membered carbocyclic or aryl ring, or a 4- to 6-membered heterocyclic or heteroaryl ring containing 1 or 2 heteroatoms independently selected from N, O, and S;

or R$^2$ and R$^3$ are taken together to form a 3- to 6-membered carbocyclic or aryl ring or a 3- to 6-membered heterocyclic or heteroaryl ring;

wherein each of which fused R$^1$ and R$^2$ or R$^2$ and R$^3$ rings, or generally R$^1$, R$^2$, R$^3$, R$^{1'}$, R$^{2'}$, or R$^{3'}$, are optionally substituted with 1 or more substituents independently selected from R$^{201}$, halogen (and in particular F), hydroxyl, cyano, —COOH, alkyl including C$_1$-C$_4$alkyl (and in particular methyl), alkenyl including C$_2$-C$_4$alkenyl, alkynyl including C$_2$-C$_4$alkynyl, alkoxy including C$_1$-C$_4$alkoxy, alkanoyl including C$_2$-C$_4$alkanoyl, hydroxyC$_1$-C$_4$alkyl, (mono- and di-alkylamino)C$_0$-C$_4$alkyl, alkyl(C$_3$-C$_7$cycloalkyl) including —C$_1$-C$_4$alkyl(C$_3$-C$_7$cycloalkyl), —O—(C$_3$-C$_7$cycloalkyl), haloalkyl including C$_1$-C$_6$haloalkyl, and haloalkoxy including C$_1$-C$_6$haloalkoxy;

or R$^1$ and R$^{1'}$ are taken together to form a carbonyl group;

or R$^2$ and R$^{2'}$ are taken together to form a carbonyl group;

or R$^3$ and R$^{3'}$ are taken together to form a carbonyl group;

or R$^1$ and R$^2$ are taken together to form a carbon-carbon double bond;

or R$^2$ and R$^3$ are taken together to form a carbon-carbon double bond;

R and R' are independently selected from H, R$^{201}$, alkyl, cycloalkyl, cycloalkylalkyl, heterocycle, heterocycloalkyl, aryl, arylalkyl, heteroaryl, and heteroarylalkyl;

or in an alternative embodiment, R, R', and R'' are independently selected from R$^{301}$, heteroalkyl, H, R$^{201}$, alkyl, cycloalkyl, cycloalkylalkyl, heterocycle, heterocycloalkyl, aryl, arylalkyl, heteroaryl, and heteroarylalkyl, and heteroaliphatic;

R$^9$ and R$^{10}$ are independently selected from hydrogen, alkyl including C$_1$-C$_6$alkyl, (C$_3$-C$_7$cycloalkyl)C$_0$-C$_4$alkyl, —C$_0$-C$_4$alkyl(C$_3$-C$_7$cycloalkyl), and —O—C$_0$-C$_4$alkyl(C$_3$-C$_7$cycloalkyl);

C2 is selected from:

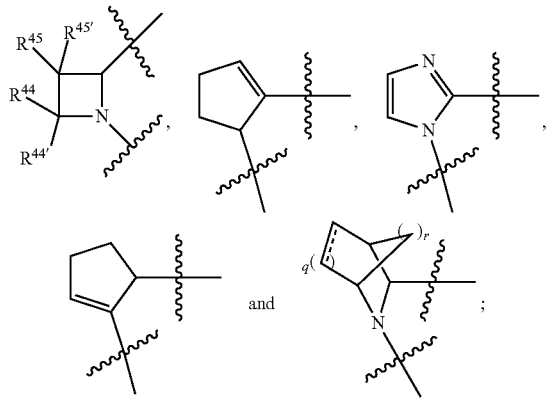

q is 0, 1, 2 or 3;

r is 1, 2 or 3;

R$^{44}$, R$^{44'}$, R$^{45}$, R$^{45'}$ are independently selected at each occurrence, as appropriate, and only where a stable compound results, from hydrogen, R$^{201}$, halogen (and specifically fluoro, chloro, bromo), hydroxyl, nitro, cyano, amino, alkyl including C$_1$-C$_6$alkyl, alkenyl including C$_2$-C$_6$alkenyl, alkynyl including C$_2$-C$_6$alkynyl, alkoxy including C$_1$-C$_6$alkoxy, alkanoyl including C$_2$-C$_6$alkanoyl, thioalkyl including —C$_1$-C$_6$alkylthio, hydroxyC$_1$-C$_6$alkyl, aminoC$_1$-C$_6$alkyl, —C$_0$-C$_4$alkylNR$^9$R$^{10}$, —C(O)OR$^9$, —OC(O)R$^9$, —NR$^9$C(O)R$^{10}$, —C(O)NR$^9$R$^{10}$, —OC(O)NR$^9$R$^{10}$, —NR$^9$C(O)OR$^{10}$, haloalkyl including C$_1$-C$_6$haloalkyl, and C$_1$-C$_6$haloalkoxy;

or $R^{44}$ and $R^{44'}$ or $R^{45}$ and $R^{45'}$, or two $R^{47}$ groups are taken together to form a carbonyl group;

or $R^{44}$ and $R^{44'}$ or $R^{45}$ and $R^{45'}$ substituted 3- to 6-membered carbocyclic spiro ring or a 3- to 6-membered heterocyclic spiro ring containing 1 or 2 heteroatoms independently selected from N, O, or S;

wherein, each of the above spiro rings may be optionally substituted with 1 or more substituents independently selected from $R^{201}$, halogen (and in particular F), hydroxyl, cyano, —COOH; alkyl including $C_1$-$C_4$alkyl (and in particular methyl), alkenyl including $C_2$-$C_4$alkenyl, alkynyl including $C_2$-$C_4$alkynyl, alkoxy including $C_1$-$C_6$alkoxy, alkanoyl including $C_2$-$C_4$alkanoyl, hydroxy$C_1$-$C_4$alkyl, (mono- and di-alkylamino)$C_1$-$C_4$alkyl, —$C_0$-$C_4$alkyl($C_3$-$C_7$cycloalkyl), —O-alkyl($C_3$-$C_7$cycloalkyl), haloalkyl including $C_1$-$C_6$haloalkyl, and haloalkoxy including $C_1$-$C_6$haloalkoxy;

or $R^{44}$ and $R^{45}$ or $R^{44'}$ and $R^{45'}$ are taken together to form a 4- to 6-membered carbocyclic or aryl ring or a 4- to 6-membered heterocyclic or heteroaryl ring; each of which ring may be optionally substituted with 1 or more substituents;

each of which fused rings or generally $R^{44}$, $R^{44'}$, $R^{45}$, or $R^{45'}$ are optionally substituted with 1 or more substituents independently selected from $R^{201}$, halogen (and in particular F), hydroxyl, cyano, —COOH, alkyl including $C_1$-$C_4$alkyl (and in particular methyl), alkenyl including C2-$C_4$alkenyl, alkynyl including $C_2$-$C_4$alkynyl, alkoxy including $C_1$-$C_4$alkoxy, alkanoyl including $C_2$-$C_4$alkanoyl, hydroxy$C_1$-$C_4$alkyl, (mono- and di-alkylamino)$C_0$-$C_4$alkyl, alkyl($C_3$-$C_7$cycloalkyl) including —$C_1$-$C_4$alkyl($C_3$-$C_7$cycloalkyl), —O—($C_3$-$C_7$cycloalkyl), haloalkyl including —$C_1$-$C_6$haloalkyl, and haloalkoxy including $C_1$-$C_6$haloalkoxy;

C3 is selected from:

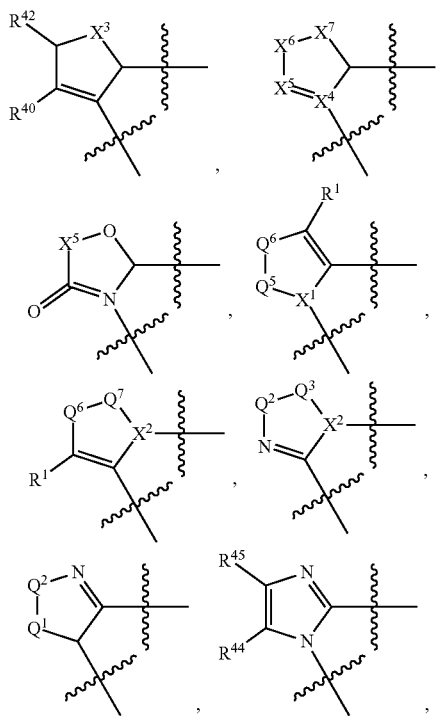

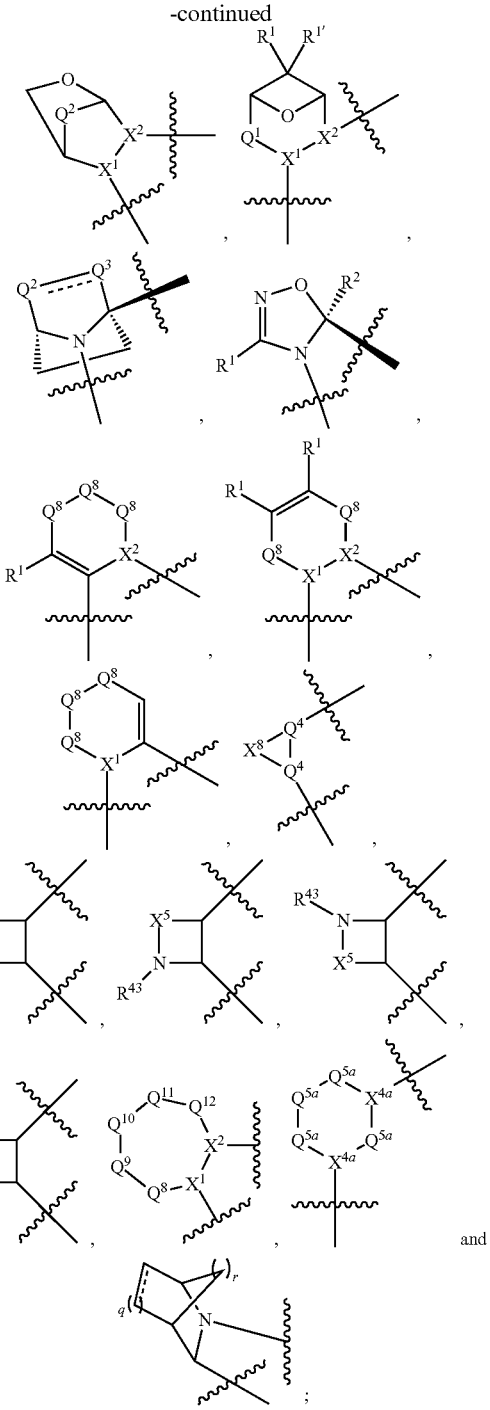

and

;

$X^3$ is $C(R^1R^{1'})$;
$X^4$ is N or CH;
$X^{4a}$ is N, CH or CZ;
$X^5$ and $X^6$ are $C(R^1R^{1'})$;
or $X^4$ and $X^5$ or $X^5$ and $X^6$ together are C=C;
$X^7$ is SO or $SO_2$;
$X^8$ is $C(R^1R^{1'})$ or $N(R^{43})$;
$X^{5a}$ is independently selected from $C(R^1R^{1'})$ and O;
$Q^4$ is N or CH;
$Q^5$ is $N(R^{47})$ or $C(R^{46}R^{46'})$;
$Q^{5a}$ is independently selected from $C(R^{47}R^{47})$, $N(R^{47})$, O, S, SO, and $SO_2$;

$Q^6$ is $N(R^{47})$, $C(R^{46}R^{46'})$, S, or O;

$Q^7$ is $C(R^{46}R^{46'})$, S or $N(R^{47})$;

$Q^8$, $Q^9$, $Q^{10}$, $Q^{11}$ and $Q^{12}$ are each independently $C(R^2R^{2'})$, S, SO, $SO_2$, O, $N(R^2)$, $B(R^{50})$, or $Si(R^{49})_2$;

$R^{40}$ is hydrogen, alkyl, cycloalkyl, cycloalkylalkyl, heterocycle, heterocycloalkyl, aryl, arylalkyl, heteroaryl, or heteroarylalkyl wherein each group can be optionally substituted;

$R^{42}$ is halo, hydroxy, alkoxy including $C_1$-$C_6$alkoxy, haloalkoxy including $C_1$-$C_6$haloalkoxy, —SH, or —S($C_1$-$C_6$alkyl);

$R^{43}$ is hydrogen, acyl, alkyl, cycloalkyl, cycloalkylalkyl, heterocycle, heterocycloalkyl, aryl, arylalkyl, heteroaryl, or heteroarylalkyl wherein each group can be optionally substituted;

$R^{46}$ and $R^{46'}$ are independently hydrogen, alkyl, cycloalkyl, cycloalkylalkyl, heterocycle, heterocycloalkyl, aryl, arylalkyl, heteroaryl, or heteroarylalkyl wherein each group can be optionally substituted;

or $R^{46}$ and $R^{46'}$ are taken together to form an optionally substituted 3- to 6-membered carbocyclic spiro ring or a 3- to 6-membered heterocyclic spiro ring containing 1 or 2 heteroatoms independently selected from N, O, or S;

$R^{47}$ is hydrogen, acyl, alkyl, cycloalkyl, cycloalkylalkyl, heterocycle, heterocycloalkyl, aryl, arylalkyl, heteroaryl, or heteroarylalkyl wherein each group can be optionally substituted;

or two $R^{47}$ groups are taken together to form a carbonyl group;

$R^{49}$ is halo, hydrogen, alkyl, cycloalkyl, cycloalkylalkyl, heterocycle, heterocycloalkyl, aryl, arylalkyl, heteroaryl, or heteroarylalkyl wherein each group can be optionally substituted $R^{50}$ is hydroxy or $C_1$-$C_6$alkoxy;

or $X^1$ and $Q^8$ or $Q^8$ and $Q^9$ or $Q^9$ and $Q^{10}$ or $Q^{10}$ and $Q^{11}$ or $Q^{11}$ and $Q^{12}$ or $Q^{12}$ and $X^2$ can form a carbon-carbon double bond;

or two $Q^{5a}$ groups or a $X^{4a}$ and a $Q^{5a}$ group can form a carbon-carbon double bond;

and where any of these groups may be further optionally substituted as that term is defined in the Terminology Section below, if desired to achieve the target effect, results in a stable compound that makes chemical sense to the skilled artisan, and the group is not redundant (i.e., as known in the art, alkyl substituted with alkyl is redundant; however, for example, alkoxy substituted with alkoxy is not redundant);

or the central core moiety, C3, is a small mimetic of a beta-turn such as a benzodiazepine, a Friedinger lactam, a 2-oxo-1,3-oxazolidine-4-carboxylate or a β-D-glucose scaffold. See, De Marco, R. et al., "In-peptide synthesis of di-oxazolidinone and dehydroamino acid-oxazolidinone motifs as β-turn inducers", J. Org. Biomol. Chem., 2013, 11, 4316-4326, Hirschmann, R. F. et al., The β-D-Glucose Scaffold as a β-Turn Mimetic, Accounts Chem. Res., 2009, 42, 1511-1520 and Smith, A. B, et al., Accounts of Chem. Res., 2011, 44, 180-193. In another embodiment, the central core moiety, C, can comprise a reverse turn mimetic that can include, but is not limited to; a non-peptidic residue, a metal chelation based mimic, or a foldamer. See, Nair, R. V. et al., "Synthetic turn mimetics and hairpin nucleators: Quo Vadimus?", Chem. Comm., 2014, 50, 13874-13884. In some embodiments, the central core moiety, C, can comprise a conformationally constrained cyclic amino acid including but not limited to a (S)- or (R)-α-trifluoromethyl pyroglutamic acid derivative. See, Chaume, G. et al., "Concise access to enantiopure (S)- or (R)-α-trifluoromethyl pyroglutamic acids from ethyl trifluoropyruvate-base chiral CF3-oxazolidines (Fox)", J. Fluor. Chem., 2008, 129, 1104-1109 and Andre, C. et al., "(S)-ABOC: A Rigid Bicyclic β-Amino Acid as Turn Inducer", Org. Lett., 2012, 14, 960-963. In some embodiments, the central core moiety, C, can comprise a monomeric unit of a foldamer such as, but not limited to an oxazolidin-2-one. See, Tomasii, C., Angelicim G. and Castellucci, N., "Foldamers Based on Oxazolidin-2-ones", Eur. J. Org. Chem., 2011, 3648-3669;

C4 is selected from:

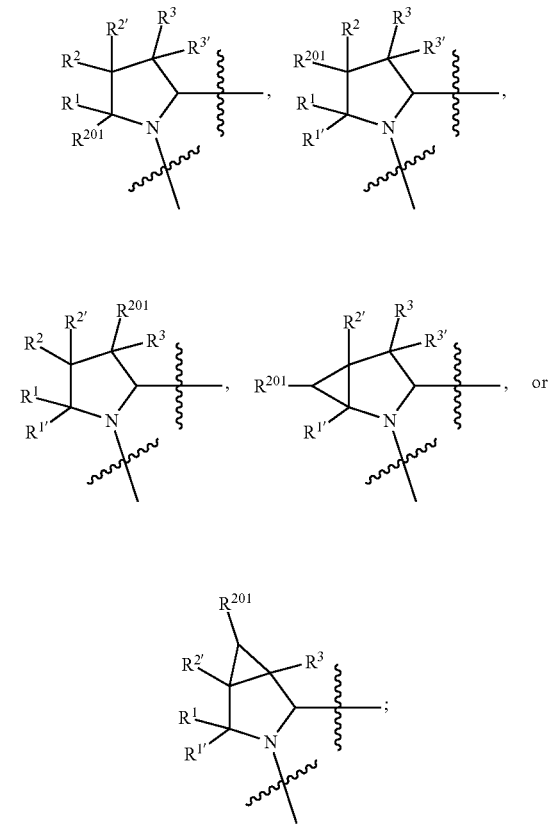

or C4 is selected from:

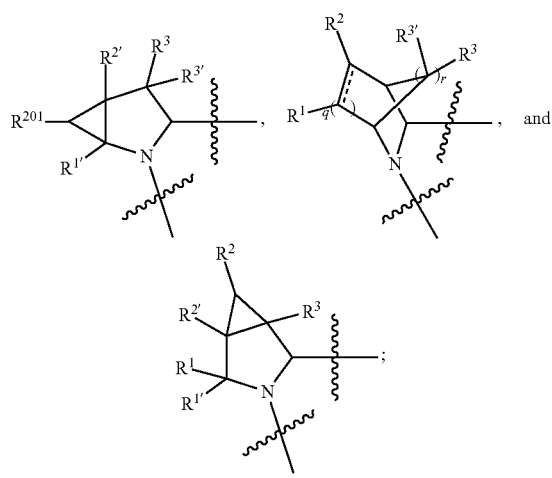

or C4 is selected from:
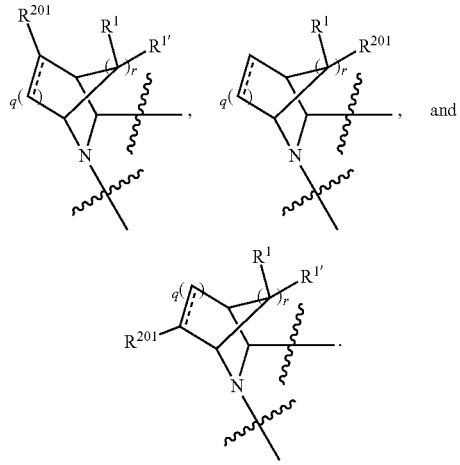
∥ is a single or double bond;
C5 is selected from:
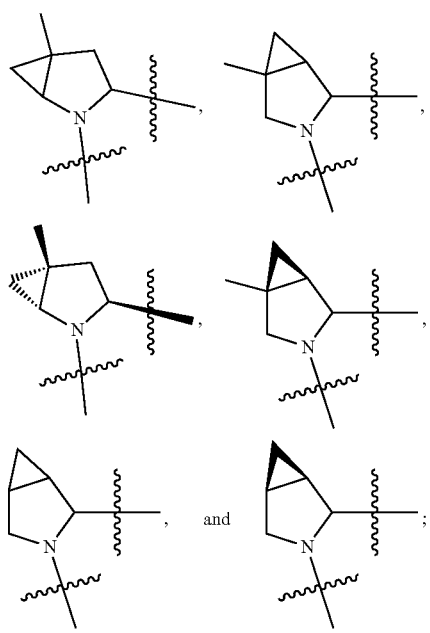
A1 is selected from:
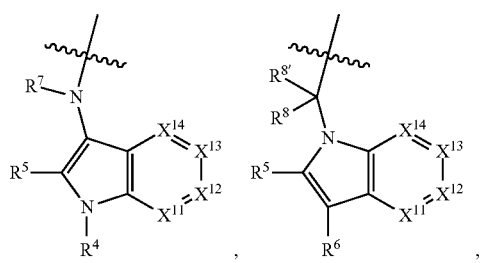
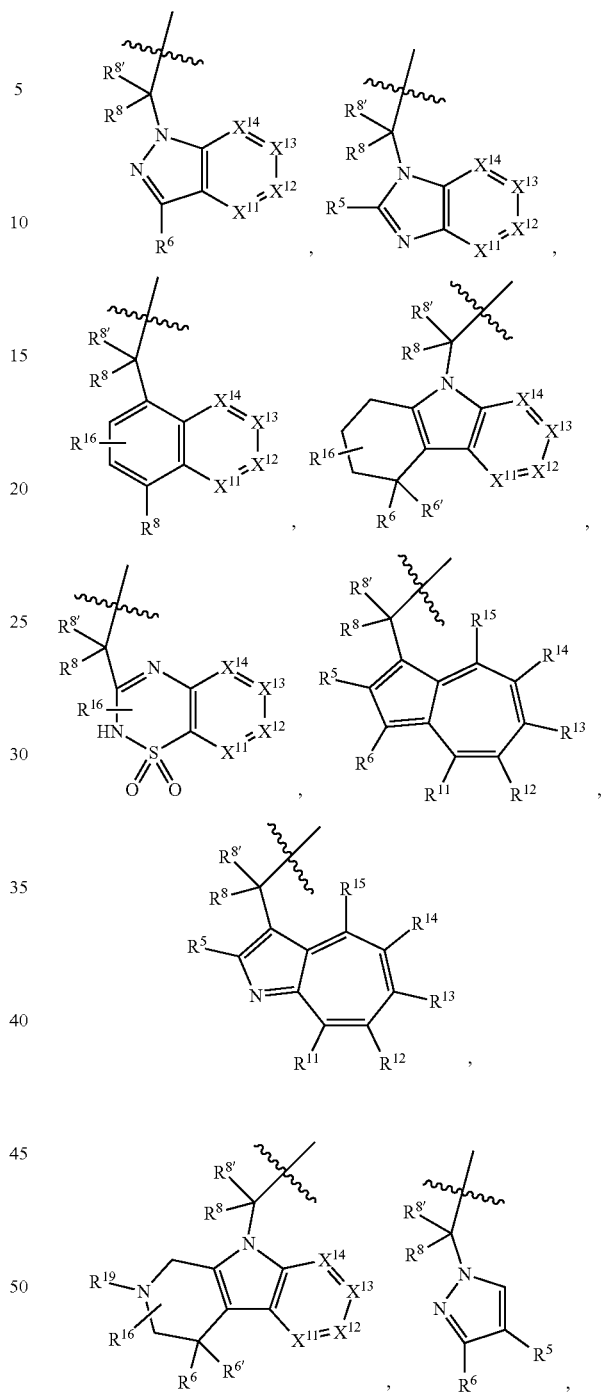
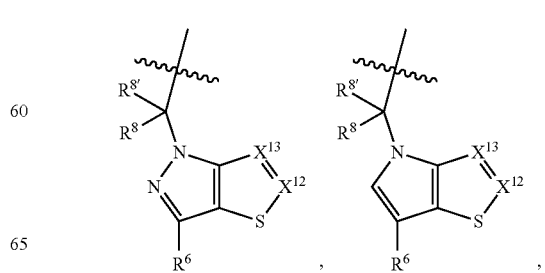

-continued
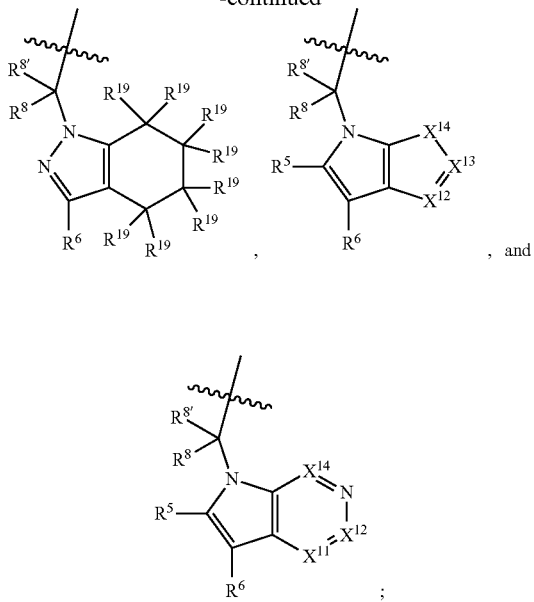
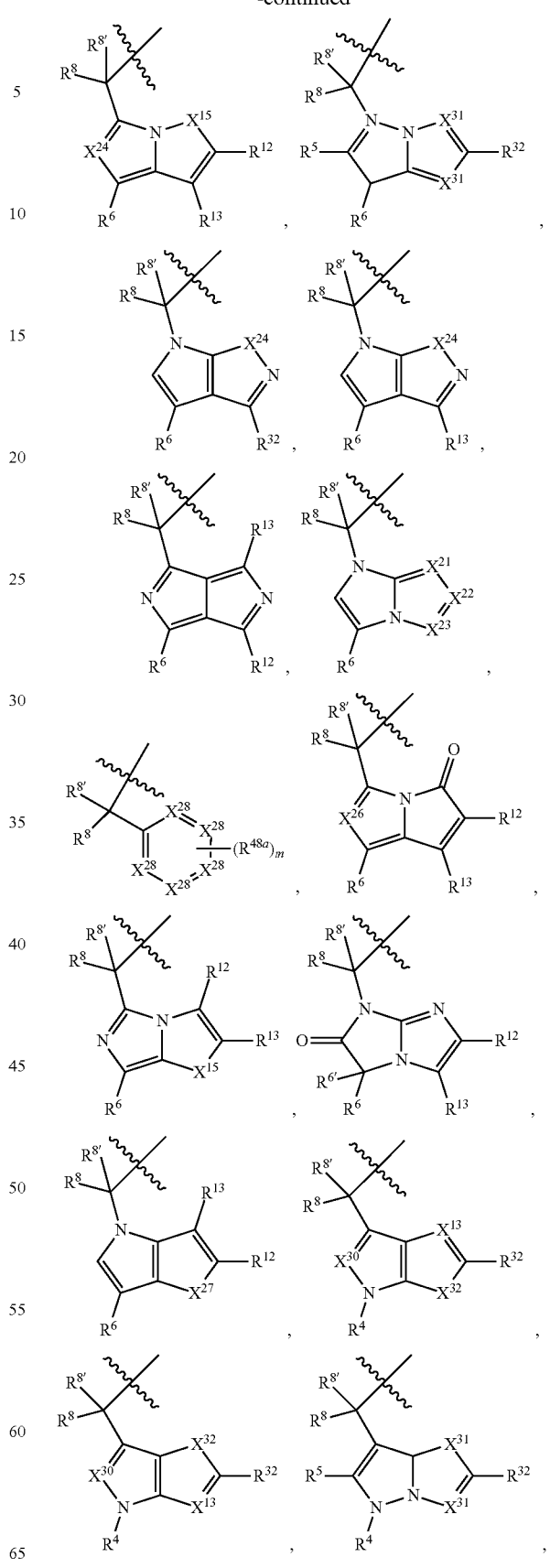
or A1 is selected from:
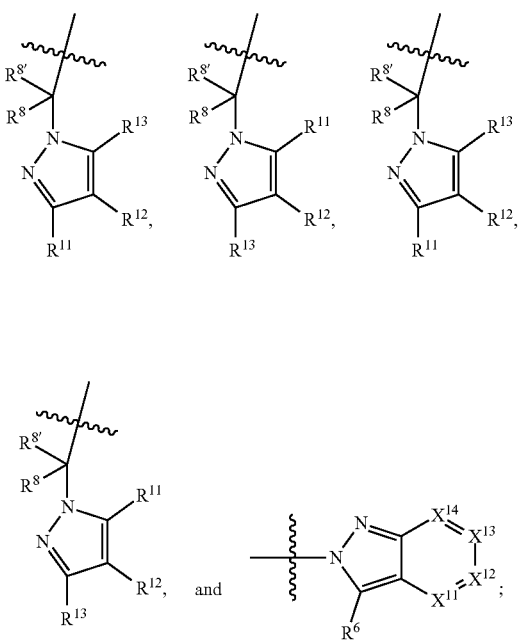
A2 is selected from:
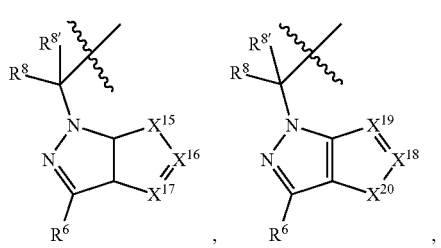

-continued
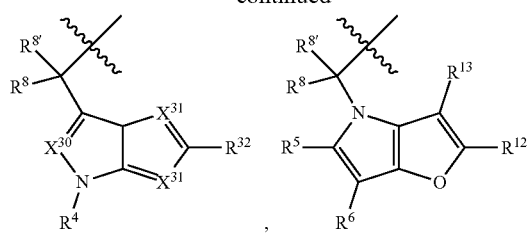
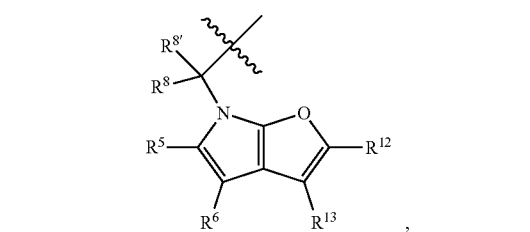
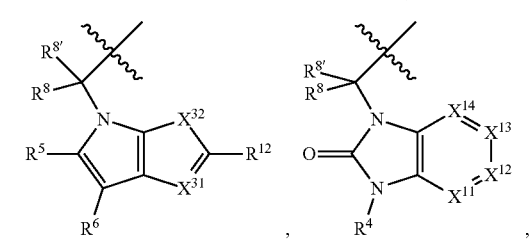

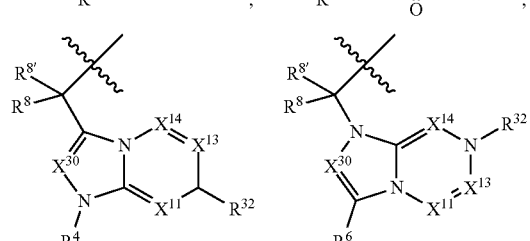
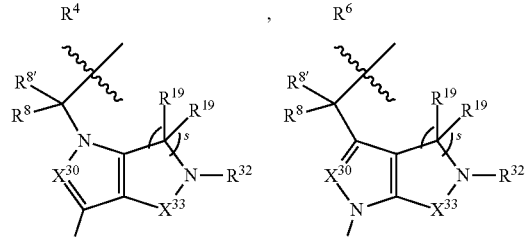
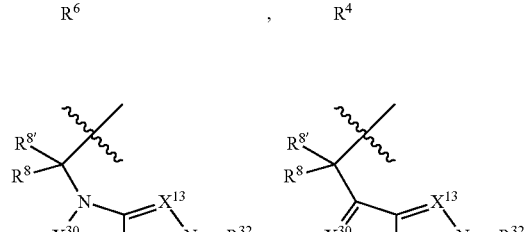
-continued
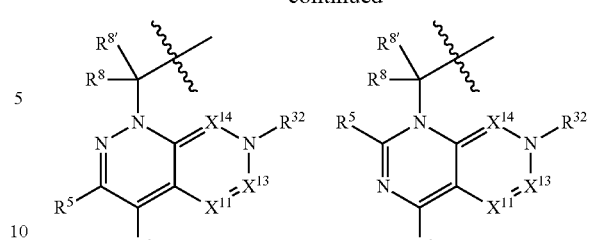
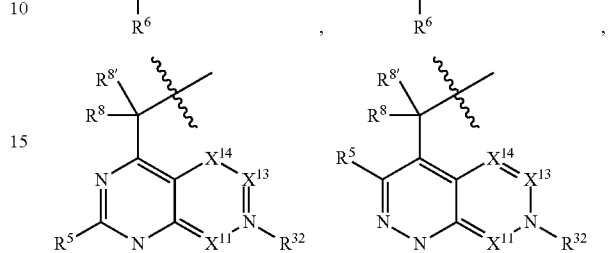
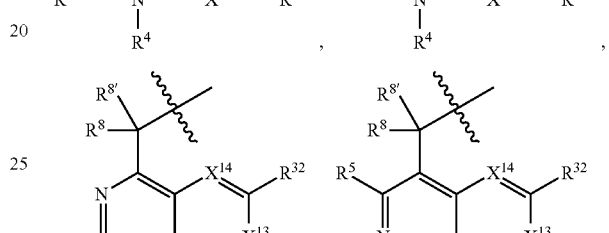
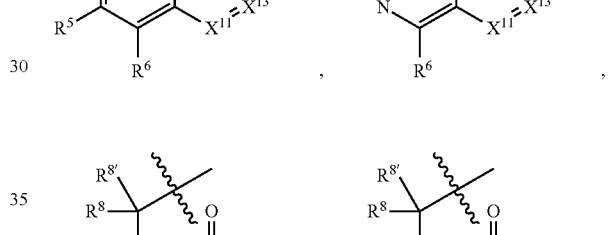

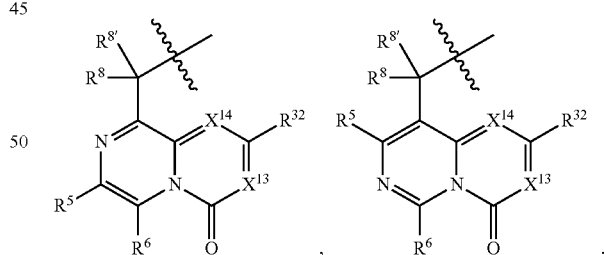
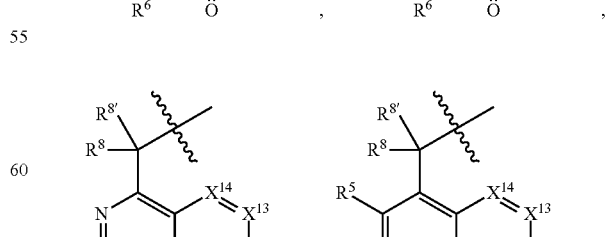

-continued
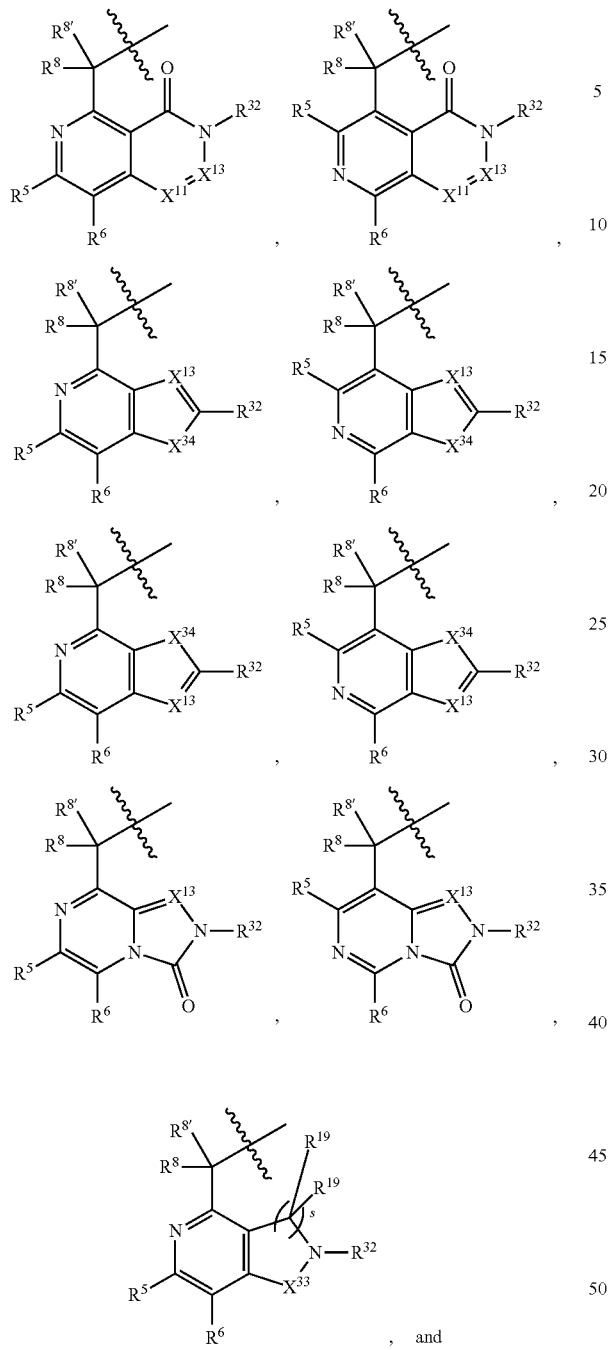
A3 is selected from:
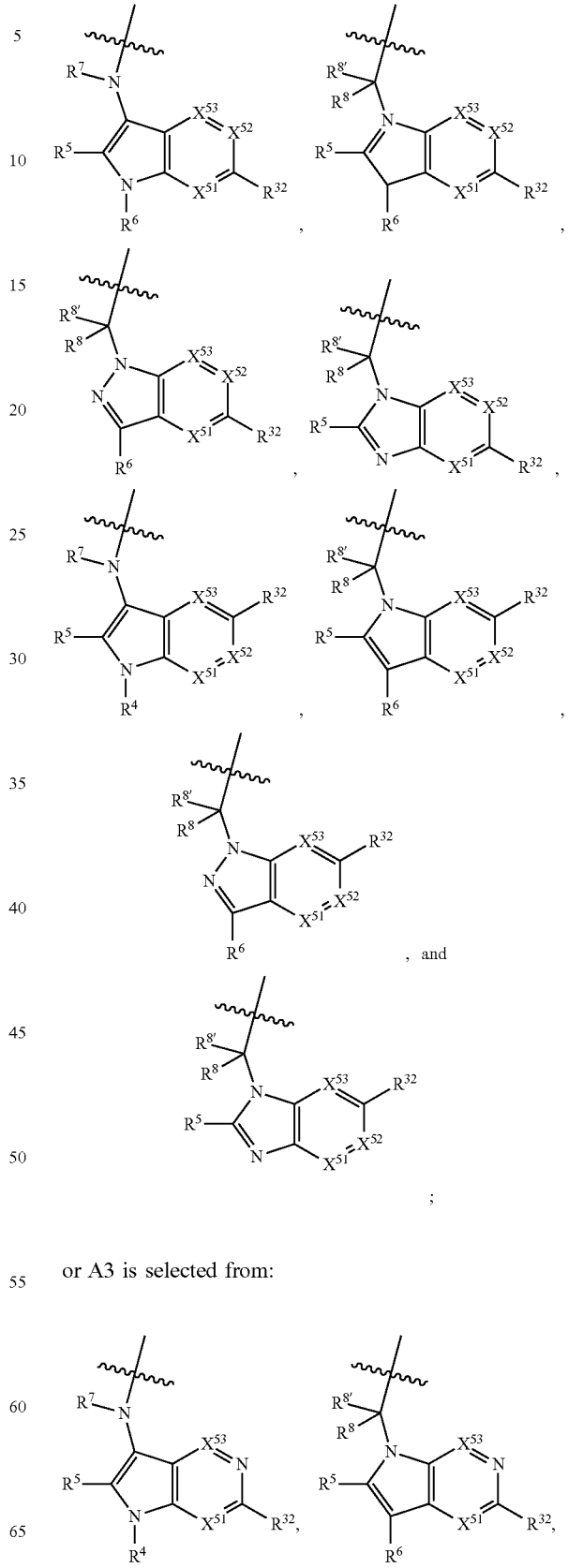
or A3 is selected from:

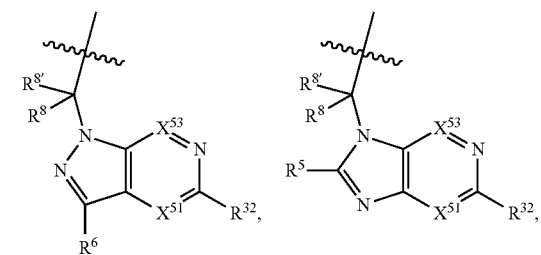
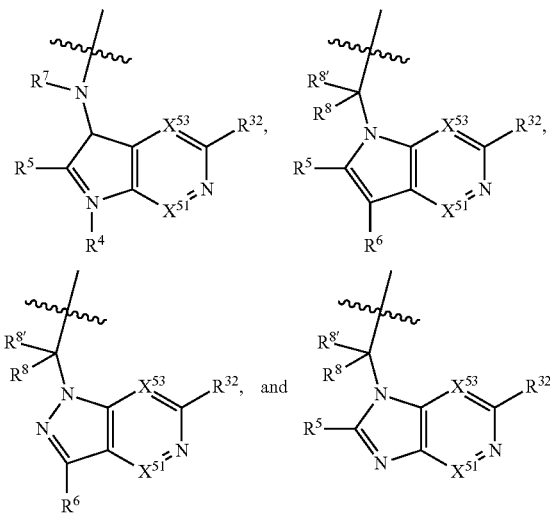
or A3 is selected from:
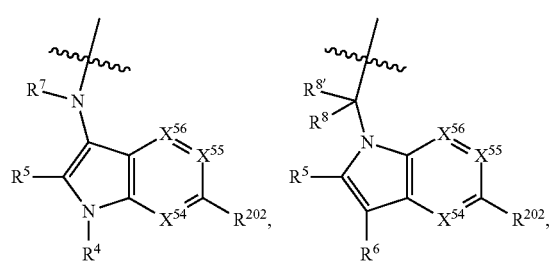
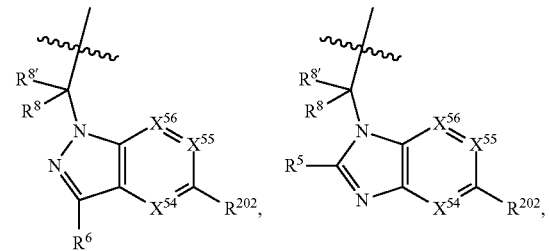
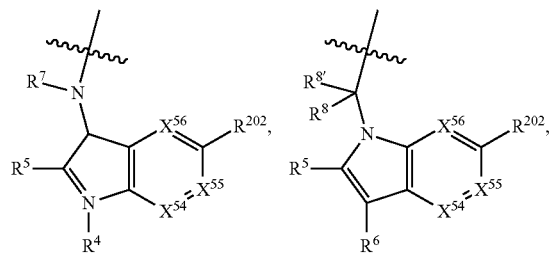
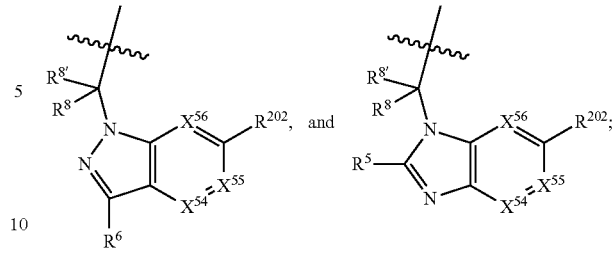
or A3 is selected from:
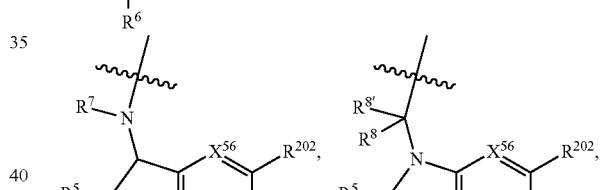
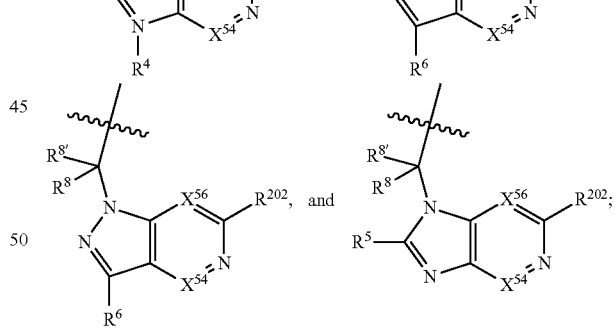
or A3 is selected from:
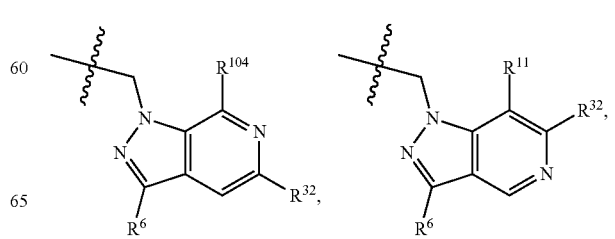

29

-continued

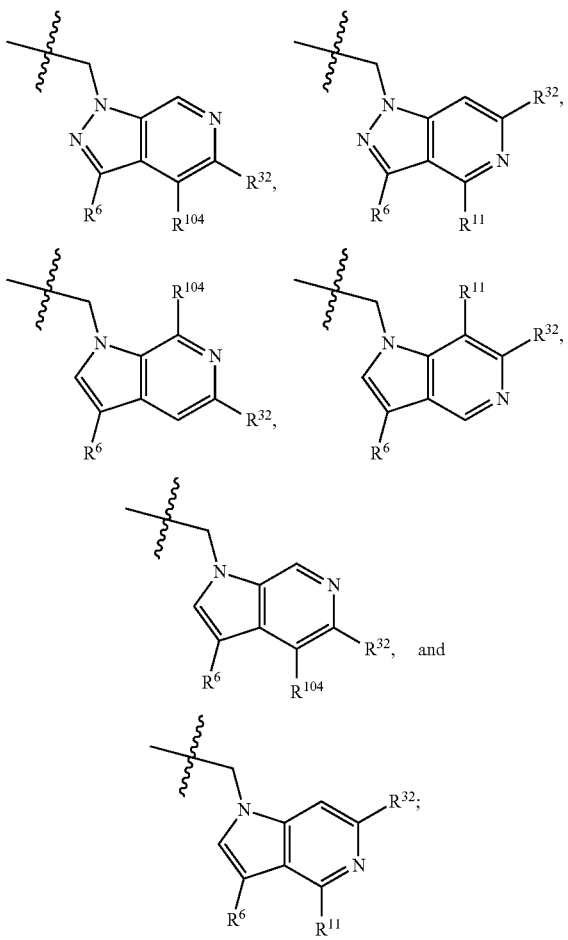

or A3 is selected from:

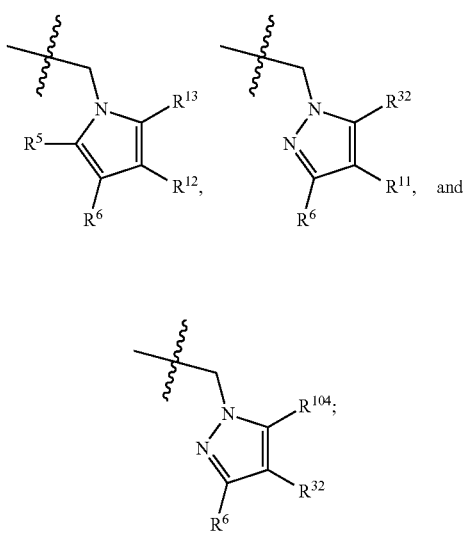

30 or A3 is selected from:

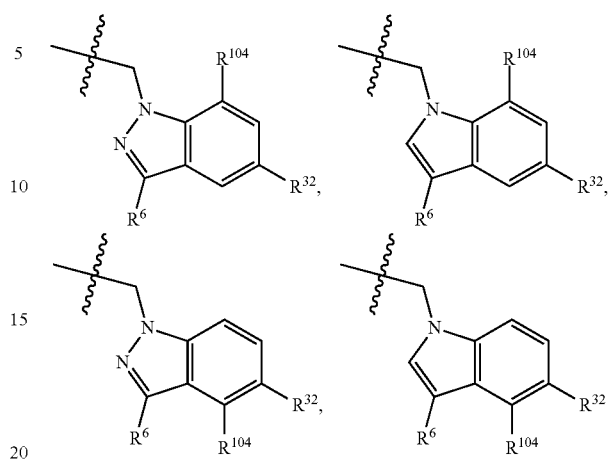

$X^{51}$, $X^{52}$, and $X^{53}$ are independently selected from N, $CR^{31}$, and $CR^{201}$;
wherein at least one of $X^{51}$, $X^{52}$, and $X^{53}$ is selected from $CR^{201}$;
$X^{54}$, $X^{55}$, and $X^{56}$ are independently selected from N, $CR^{31}$, and $CR^{201}$;
$R^{104}$ is selected from $R^{201}$, $C_1$-$C_4$ alkyl, $C_3$-$C_6$ cycloalkyl, $C_1$-$C_4$ haloalkyl, deuterium, —$CO_2H$, $CO_2R^9$, heteroaryl, F, Cl, Br, and cyano;
$R^{201}$ is selected from aminoalkyl-, alkylaminoalkyl-, heterocycloalkyl-, and hydroxyalkyl; -alkyl-O-alkyl including —$CH_2OCH_3$, -alkyl-S-alkyl, -alkyl-N(alkyl)-alkyl, -alkyl-NH-alkyl, -aliphatic-O-aliphatic, -aliphatic-S-aliphatic, -aliphatic-N(aliphatic)-aliphatic, -aliphatic-NH-aliphatic, -aliphatic-O-heterocycle, -aliphatic-S-heterocycle, -aliphatic-N(aliphatic)-heterocycle, -aliphatic-NH-heterocycle, -alkyl-NHC(O)haloalkyl, -alkyl-$NR^9$C(O)haloalkyl, -alkyl-C(O)NHhaloalkyl, -alkyl-C(O)$NR^9$haloalkyl, -alkyl-NHC(O)haloalkyl, -alkyl-$NR^9$C(O)aliphatic, -alkyl-C(O)NHaliphatic, -alkyl-$NR^9$C(O)aliphatic, -alkyl-NHC(O)aliphatic, -substituted alkyl-N($R^9$)-substituted alkyl, alkyl-heteroaryl, -alkyl-O-haloalkyl, heteroaryl, heterocycle, alkyl-heterocycle, —N(aliphatic)$_2$; and wherein each $R^{201}$ can be optionally substituted as defined in the Terminology section below, and wherein $R^{201}$ can be optionally substituted with $R^{301}$, which can be directly linked to $R^{201}$ or can be linked to $R^{201}$ through an amino, hydroxyl, thio, carboxylic acid, phosphate, phosphonate or sulfonate linkage;

In an alternative embodiment, $R^{201}$ is selected from $R^{301}$, -alkyl-CN, -alkyl-$NR^9$C(O)alkenyl, -alkyl-$SO_2$-alkyl; and -alkyl-S(O)$NR^9$-alkyl;

In an alternative embodiment, $R^{201}$ is substituted with an oxime, and —C(O)Oalkyl;

$R^{202}$ is selected from aryl, heteroaryl, and heterocycle, wherein the aryl, heteroaryl, or heterocycle ring is substituted with $R^{201}$;

$R^{301}$ is selected from the following:
i. The residue of a fatty acid. Examples are short chain fatty acids with 3, 4, or 5 aliphatic carbons, medium-chain fatty acids with aliphatic tails of 6, 7, 8, 9, 10, 11 or 12 carbons, long chain fatty acids, which have aliphatic tails of 13, 14, 15, 16, 17, 18, 19, 20, 21 or 22 carbons, or a very long fatty acid, which has 22, 23, 24, 25, 26 27, or 28 or more aliphatic carbons. The aliphatic chain can be saturated, mono-unsaturated, di-unsaturated, tri-unsaturated, polyunsaturated, or alkynyl. Unsaturated fatty acids can be used in a cis or trans configuration, and include, but are not limited to oleic acid, ω6 fatty acid such as linoleic acid, ω3 fatty acid such as α-linolenic acid, docosahexaenoic acid, stearidonic acid, eicosapentaenoic acid, docosapentaenoic acid, eicosatetraenoic acid, myristoleic acid, palmitoleic acid, sapienic acid, elaidic acid, vaccenic acid, gadoleic acid, eicosenoic acid, nervonic acid, eicosadienoic acid, docasadienoic acid, linolenic acid, t-linolenic acid, pinolenic acid, eleosteric acid, β-eleostearic acid, mead acid, eicosatrienoic acid, linoleic acid, linoelaidic acid, α-linolenic acid, arachidonic acid, erucic acid and docosahexaenoic acid. Nonlimiting examples of saturated fatty acids that can be used to provide the prodrugs of the present invention are caprylic acid, capric acid, lauric acid, myristic acid, palmitic, stearic acid, arachidic acid, behenic acid, lignoceric acid and cerotic acid.

ii. The residue of an amino acid that is naturally occurring or synthetic, and includes for example, α, β γ or δ amino acids. Naturally occurring amino acids include those found in proteins, e.g., glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In some embodiments, the amino acid is in the L-configuration. Alternatively, the amino acid can be used in the D-configuration or in a mixture of L- and D-. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. Additional amino acids include selenocysteine, pyrrolysine, N-formylmethionine, γ-aminobutyric acid (GABA), δ-aminolevulinic acid, aminobenzoic acid (including 4-aminobenzoic acid), aminoisobutyric acid, dehydroalanine, cystathionine, lanthionine, djenkolic acid, diaminopimelic acid, norvaline, alloisoleucine, t-leucine, α-amino-heptanoic acid, pipecolic acid, α, β-diaminopropionic acid, α,γ-diaminobutyric acid, ornithine, glutamic acid, allothreonine, homocysteine, β-aminobutyric acid, α-aminoisobutyric acid, isovaline, sarcosine, N-ethylglycine, N-propylglycine, N-isopropyl glycine, N-methyl alanine, N-ethyl alanine, N-methyl-β-alanine, isoserine, norleucine, homoserine, O-methyl-homoserine, O-ethyl-homoserine, homonorleucine, carboxyglutamic acid, hydroxyproline, hypusine, pyroglutamic acid, and α-hydroxy-γ-aminobutyric acid.

iii. The residue of a non-naturally occurring amino acid with an extended length between the amino group and the carboxylic acid, which can be used either alone or as a linker to another prodrug moiety. Examples include amino acids wherein the amino and carboxylic acid are separated by an aliphatic or heteroaliphatic moiety (nonlimiting example is 8-amino-3,6-dioxaoctanoic acid), for example an alkyl, alkenyl, alkynyl, ethylene glycol, propylene glycol, alkylene glycol, or the like, moiety, e.g., with 3, 4, 5, 6, 7, 8, 9, 10, 11 or 12 or more straight, branched or cyclic atoms or moieties (e.g., alkylene glycol moieties), as appropriate to provide the desired properties. In some embodiments, the amino acid has one or more internal amine, carbonyl, carboxy, oxo, thio, phosphate or phosphonate moieties in the heteroaliphatic chain.

iv. The residue of one or a series of amino acids linked to a terminal fatty acid or to an endcap like hydrogen or alkyl. In one non-limiting example, 8-amino-3,6-dioxaoctanoic acid (one or several in sequence) is covalently bound to the selected complement D inhibitor of the present invention through a functional group such as a carboxylic acid, sulfonyl, hydroxyl or amino group. See generally Lau, et al., "Discovery of the Once-Weekly Glucagon-Like Peptide-1 (GLP-1) Analogue Semiglutide", *J. Med. Chem.*, 2015, 58, 7370-7380. The 8-amino-3,6-dioxaoctanoic acid is covalently linked to an aliphatic acid, including but not limited to a C16, C18, C20 aliphatic acid, or a dicarboxylic acid, including but not limited to a C8, C10, C12, C14, C16, C18 or C20 diacid. One or more amino acids can also be used in the selected configuration to add length or functionality.

$R^4$, $R^5$, and $R^6$ are selected from hydrogen, -JCHO, -JC(O)NH$_2$, -JC$_2$-C$_6$alkanoyl, -JC(O)NH(CH$_3$), -J-COOH, -JP(O)(OR$^9$)$_2$, -JOC(O)R$^9$, -JC(O)OR$^9$, -JC(O)N(CH$_2$CH$_2$R$^9$)(R$^{10}$), -JNR$^9$C(O)R$^{10}$, -JSO$_2$NH$_2$, -JS(O)NH$_2$, -JC(CH$_2$)$_2$F, -JCH(CF$_3$)NH$_2$, -JC(O)C$_0$-C$_2$alkyl(C$_3$-C$_7$cycloalkyl), -JNR$^9$(C$_2$-C$_6$alkanoyl), -JNR$^9$C(O)NR$^9$R$^{10}$, -JSO$_2$(C$_1$-C$_6$alkyl), -JSO$_2$(C$_1$-C$_6$haloalkyl), -JSO$_2$NR$^7$R$^7$, -JSO=NH(C$_1$-C$_6$alkyl), -J-nitro, -J-halogen, -J-hydroxyl, -J-phenyl, a 5- to 6-membered heteroaryl, -J-cyano, -J-cyanoimino, -J-amino, -J-imino, —C$_1$-C$_6$alkyl, —C$_0$-C$_4$alkyl(C$_3$-C$_7$heterocycloalkyl), —C$_0$-C$_4$alkyl(C$_3$-C$_7$cycloalkyl),

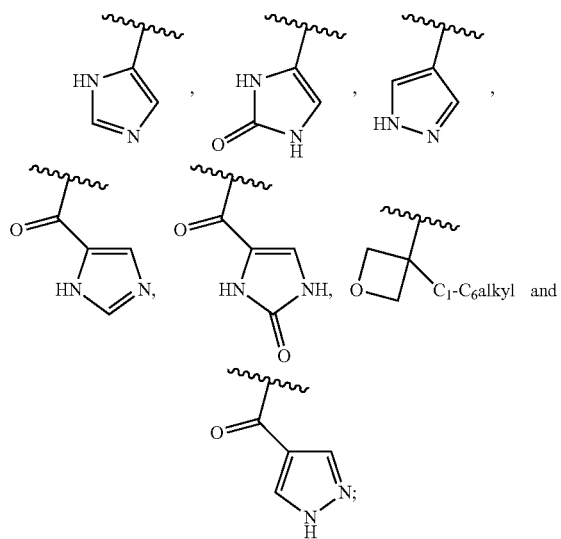

each of which $R^4$, $R^5$ and $R^6$ other than hydrogen, nitro, halogen, cyano, cyanoimino, or —CHO, is optionally substituted with one or more of amino, imino, halogen, hydroxyl, cyano, cyanoimino, alkyl including C$_1$-C$_6$alkyl, alkoxy including C$_1$-C$_6$alkoxy, —C$_0$-C$_2$alkyl(mono- and di-C$_1$-C$_4$alkylamino), —C$_1$-C$_6$haloalkyl, and haloalkoxy including C$_1$-C$_6$haloalkoxy;

J is independently selected from a covalent bond, alkylene including C$_1$-C$_4$alkylene, O-alkylene including —OC$_1$-C$_4$alkylene, alkenylene including C$_2$-C$_4$alkenylene, and alkynylene C$_2$-C$_4$alkynylene;

$R^{6'}$ is hydrogen, halogen, hydroxyl, $C_1$-$C_4$alkyl, —$C_0$-$C_4$alkyl($C_3$-$C_7$cycloalkyl), or $C_1$-$C_4$alkoxy;

or $R^6$ and $R^{6'}$ may be taken together to form an oxo, vinyl, or imino group;

$R^7$ is hydrogen, alkyl including $C_1$-$C_6$alkyl, or —$C_0$-$C_4$alkyl($C_3$-$C_7$cycloalkyl);

$R^8$ and $R^{8'}$ are selected from hydrogen, halogen, hydroxyl, alkyl including $C_1$-$C_6$alkyl, —$C_0$-$C_4$alkyl($C_3$-$C_7$cycloalkyl), alkoxy including $C_1$-$C_6$alkoxy, and ($C_1$-$C_4$alkylamino)$C_0$-$C_2$alkyl;

or $R^8$ and $R^{8'}$ are taken together to form an oxo group;

or $R^8$ and $R^{8'}$ are taken together with the carbon that they are bonded to form a 3-membered carbocyclic ring;

$R^{16}$ is independently selected from hydrogen, halogen, hydroxyl, nitro, cyano, —$C_1$-$C_6$alkyl, alkenyl including $C_2$-$C_6$alkenyl, alkanoyl including $C_2$-$C_6$alkanoyl, alkoxy including $C_1$-$C_6$alkoxy, —$C_0$-$C_4$alkyl(mono- and di-$C_1$-$C_6$alkylamino), —$C_0$-$C_4$alkyl($C_3$-$C_7$cycloalkyl), haloalkyl including $C_1$-$C_6$haloalkyl, and haloalkoxy including $C_1$-$C_6$haloalkoxy;

$R^{19}$ is hydrogen, alkyl including $C_1$-$C_6$alkyl, alkenyl including $C_2$-$C_6$alkenyl, alkanoyl including $C_2$-$C_6$alkanoyl, —$SO_2C_1$-$C_6$alkyl, (mono- and di-$C_1$-$C_6$alkylamino)$C_1$-$C_4$alkyl, —$C_0$-$C_4$alkyl($C_3$-$C_7$cycloalkyl), —$C_0$-$C_4$alkyl($C_3$-$C_7$heterocycloalkyl), —$C_0$-$C_4$alkyl(aryl), or $C_0$-$C_4$alkyl(heteroaryl), wherein each $R^{19}$ other than hydrogen is optionally substituted with one or more substituents independently selected from halogen, hydroxyl, amino, —COOH, and —C(O)O$C_1$-$C_4$alkyl;

$X^{11}$ is N or $CR^{11}$;
$X^{12}$ is N or $CR^{12}$;
$X^{13}$ is N or $CR^{13}$;
$X^{14}$ is N or $CR^{14}$;
wherein no more than 2 of $X^{11}$, $X^{12}$, $X^{13}$, and $X^{14}$ are N;
wherein one of $R^{12}$ and $R^{13}$ is $R^{32}$ and the other is $R^{31}$ or $R^{32}$;

and wherein if there is no $R^{13}$ and no $R^{32}$ on the A ring then $R^{12}$ is $R^{32}$;

and wherein if there is no $R^{12}$ and no $R^{32}$ on the A ring then $R^{13}$ is $R^{32}$;

$R^{31}$ is independently selected from hydrogen, halogen, hydroxyl, nitro, cyano, amino, —COOH, haloalkyl including $C_1$-$C_6$haloalkyl, haloalkoxy including $C_1$-$C_6$haloalkoxy, alkyl including $C_1$-$C_6$alkyl, —$C_0$-$C_4$alkyl($C_3$-$C_7$cycloalkyl), alkenyl including $C_2$-$C_6$alkenyl, alkanoyl including $C_2$-$C_6$alkanoyl, alkoxy including $C_1$-$C_6$alkoxy, alkenyloxy including $C_2$-$C_6$alkenyloxy, —C(O)O$R^9$, thioalkyl including $C_1$-$C_6$thioalkyl, —$C_0$-$C_4$alkyl$NR^9R^{10}$, —C(O)$NR^9R^{10}$, —$SO_2R^9$, —$SO_2NR^9R^{10}$, —OC(O)$R^9$, and —C($NR^9$)$NR^9R^{10}$, each of which $R^{31}$ other than hydrogen, halogen, hydroxyl, nitro, cyano, haloalkyl including $C_1$-$C_6$haloalkyl, and $C_1$-$C_6$haloalkoxy is optionally substituted with one or more substituents independently selected from halogen, hydroxyl, nitro, cyano, amino, —COOH, —C(O)$NR^9R^{10}$, haloalkyl including $C_1$-$C_6$haloalkyl, haloalkoxy including $C_1$-$C_6$haloalkoxy, phenyl, and 4- to 7-membered heterocycle containing 1, 2, or 3 heteroatoms independently selected from N, O, and S; each of which phenyl or 4- to 7-membered heterocycle is optionally substituted with one or more substituents independently selected from halogen, hydroxyl, nitro, cyano, alkyl including $C_1$-$C_6$alkyl, alkenyl including $C_2$-$C_6$alkenyl, alkanoyl including $C_2$-$C_6$alkanoyl, alkoxy including $C_1$-$C_6$alkoxy, (mono- and di-$C_1$-$C_6$alkylamino)$C_0$-$C_4$alkyl, alkylester including $C_1$-$C_6$alkylester, —$C_0$-$C_4$alkyl)($C_3$-$C_7$cycloalkyl), $C_1$-$C_6$haloalkyl, and haloalkoxy including $C_1$-$C_6$haloalkoxy;

$R^{32}$ is selected from aryl, heteroaryl, and heterocycle wherein the aryl, heteroaryl, or heterocycle ring can be optionally substituted;

in one embodiment $R^{32}$ is substituted with $R^{301}$, —$CH_2$—$R^{301}$, or $R^{201}$;

$R^{11}$, $R^{14}$, and $R^{15}$ are independently selected from hydrogen, halogen, hydroxyl, nitro, cyano, —O(PO)(O$R^9$)$_2$, —(PO)(O$R^9$)$_2$, alkyl including $C_1$-$C_6$alkyl, alkenyl including $C_2$-$C_6$alkenyl, alkynyl including $C_2$-$C_6$alkynyl, $C_2$-$C_6$alkenyl(aryl), $C_2$-$C_6$alkenyl(cycloalkyl), $C_2$-$C_6$alkenyl(heterocycle), $C_2$-$C_6$alkenyl(heteroaryl), $C_2$-$C_6$alkynyl(aryl), $C_2$-$C_6$alkynyl(cycloalkyl), $C_2$-$C_6$alkynyl(heterocycle), $C_2$-$C_6$alkynyl(heteroaryl), alkanoyl including $C_2$-$C_6$alkanoyl, alkoxy including $C_1$-$C_6$alkoxy, thioalkyl including $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —$C_0$-$C_4$alkoxy($C_3$-$C_7$cycloalkyl), haloalkyl including $C_1$-$C_6$haloalkyl, and haloalkoxy including $C_1$-$C_6$haloalkoxy;

$X^{15}$ is NH, O, or S;
$X^{16}$ is $CR^{12}$;
$X^{17}$ is N or $CR^{13}$;
$X^{18}$ is $CR^{12}$;
$X^{19}$ is N or $CR^{13}$;
$X^{20}$ is NH or O;
$X^{21}$ is N or $CR^{14}$;
$X^{22}$ is N or $CR^{13}$;
$X^{23}$ is $CR^{12}$;
$X^{24}$ is O or S;
$X^{26}$ is N or $CR^{41}$;
$X^{27}$ is $CR^{12}$, NH, or O;
$X^{28}$ is N or CH;
$X^{30}$ is N or $CR^5$;
$X^{31}$ is N, C($R^{34}$)$_2$, or $CR^{54}$;
$X^{32}$ is NH, C($R^{54}$)$_2$, or $CR^{54}$;
$X^{33}$ is —CO—, —SO—, or —$SO_2$—;
$X^{34}$ is $CHR^{13}$, NH, O, or S;
wherein no more than 2 of $X^{28}$ are N;

$R^{41}$ is hydrogen, alkyl including $C_1$-$C_6$alkyl, or —($C_0$-$C_2$alkyl)($C_3$-$C_5$cycloalkyl);

$R^{48}$ and $R^{48a}$ is selected from hydrogen, halogen, hydroxyl, nitro, cyano, amino, alkyl including $C_1$-$C_6$alkyl, haloalkyl including $C_1$-$C_6$haloalkyl, alkenyl including $C_2$-$C_6$alkenyl, alkynyl including $C_2$-$C_6$alkynyl, thioalkyl including $C_1$-$C_6$thioalkyl, alkoxy including $C_1$-$C_6$alkoxy, -J$C_3$-$C_7$cycloalkyl, —B(OH)$_2$, -JC(O)$NR^9R^{23}$, -JOS$O_2OR^{21}$, —C(O)(CH$_2$)$_{1-4}$S(O)$R^{21}$, —O(CH$_2$)$_{1-4}$S(O)$NR^{21}R^{22}$, -JOP(O)(O$R^{21}$)(O$R^{22}$), -JP(O))(O$R^{21}$)(O$R^{22}$), -JOP(O)(O$R^{21}$)$R^{22}$, -JP(O)(O$R^{21}$)$R^{22}$, -JOP(O)$R^{21}R^{22}$, -JP(O)$R^{21}R^{22}$, -JSP(O)(O$R^{21}$)(O$R^{22}$), -JSP(O)(O$R^{21}$)($R^{22}$), -JSP(O)($R^{21}$))($R^{22}$), -J$NR^9$P(O)(NH$R^{21}$)(NH$R^{22}$), -J$NR^9$P(O)(O$R^{21}$)(NH$R^{22}$), -J$NR^9$P(O)(O$R^{21}$)(O$R^{22}$), -JC(S)$R^{21}$, -J$NR^{21}SO_2R^{22}$, -J$NR^9$S(O)$NR^{10}R^{22}$, -J$NR^9SO_2NR^{10}R^{22}$, -JS$O_2NR^9COR^{22}$, -JS$O_2NR^9CONR^{21}R^{22}$, -J$NR^{21}SO_2R^{22}$, -JC(O)$NR^{21}SO_2R^{22}$, -JC(NH$_2$)=$NR^{22}$, -JCH(NH$_2$)$NR^9$S(O)$_2R^{22}$, -JOC(O)$NR^{21}R^{22}$, -J$NR^{21}$C(O)O$R^{22}$, -J$NR^{21}$OC(O)$R^{22}$, —(CH$_2$)$_{1-4}$C(O)$NR^{21}R^{22}$, -JC(O)$NR^{24}R^{30}$, -J$NR^9$C(O)$R^{21}$, -JC(O)$R^{21}$, -J$NR^9$C(O)$NR^{10}R^{22}$, —CC$R^{21}$, —(CH$_2$)$_{1-4}$OC(O)$R^{21}$, -JC(O)O$R^{23}$, and $R^{103}$; each of which $R^{48}$ may be optionally substituted with one or more substituents selected from halogen, hydroxyl, nitro, cyano, amino, oxo, —B(OH)$_2$, —Si(CH$_3$)$_3$, —COOH, —CON$R^9R^{10}$, —P(O)(OH)$_2$, alkyl including $C_1$-$C_6$alkyl, —$C_0$-$C_4$alkyl($C_3$-$C_7$cycloalkyl), $C_1$-$C_6$alkoxy, —$C_0$-

C$_4$alkyl(mono- and di-C$_1$-C$_4$alkylNR$^9$R$^{10}$), alkylester including C$_1$-C$_6$alkylester, C$_1$-C$_4$alkylamino, C$_1$-C$_4$hydroxylalkyl, haloalkyl including C$_1$-C$_6$haloalkyl, —OC(O)R$^9$, —NR$^9$C(O)R$^{10}$, —C(O)NR$^9$R$^{10}$, —OC(O)NR$^9$R$^{10}$, —NR$^9$C(O)OR$^{10}$, haloalkyl including C$_1$-C$_6$haloalkyl, S(O)=NHR$^{21}$, SF$_5$, JC(R$^9$)=NR$^{21}$, SO$_2$OR$^{21}$, and haloalkoxy including C$_1$-C$_6$haloalkoxy;

R$^{103}$ is independently C$_1$-C$_4$ alkyl, C$_3$-C$_6$ cycloalkyl, fluorine, chlorine, or bromine;

R$^{54}$ is hydrogen, alkyl including C$_1$-C$_6$alkyl, alkenyl including C$_2$-C$_6$alkenyl, alkynyl including C$_2$-C$_6$alkynyl, alkoxy including C$_1$-C$_6$alkoxy, C$_2$-C$_6$alkynyl, alkanoyl including C$_2$-C$_6$alkanoyl, thioalkyl including C$_1$-C$_6$thioalkyl, hydroxyC$_1$-C$_6$alkyl, aminoC$_1$-C$_6$alkyl, —C$_0$-C$_4$alkyl(C$_3$-C$_7$cycloalkyl), (phenyl)C$_0$-C$_4$alkyl-, (heterocycloalkyl)C$_0$-C$_4$alkyl or (heteroaryl)C$_0$-C$_4$alkyl- wherein each R$^{54}$ is optionally substituted;

s is 1 or 2;

L is selected from L1 and L2;

L1 is a bond,

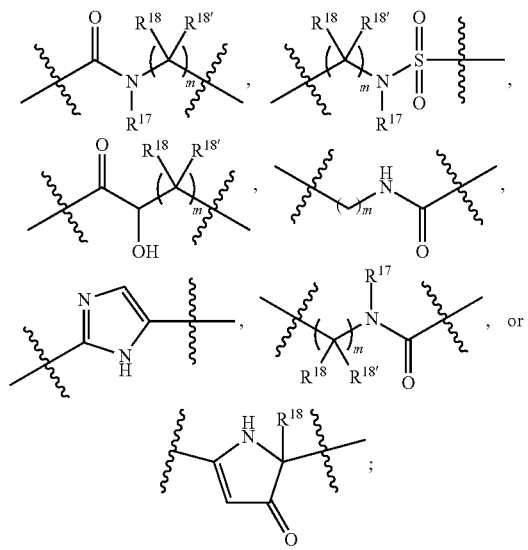

R$^{17}$ is hydrogen, alkyl including C$_1$-C$_6$alkyl, or —C$_0$-C$_4$alkyl(C$_3$-C$_7$cycloalkyl);

R$^{18}$ and R$^{18'}$ are independently selected from hydrogen, halogen, hydroxymethyl, and methyl;

m is 0, 1, 2, or 3;

L2 is selected from:

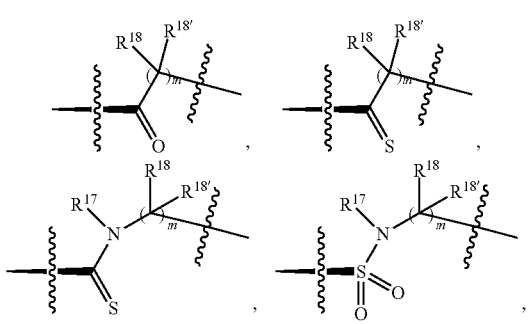

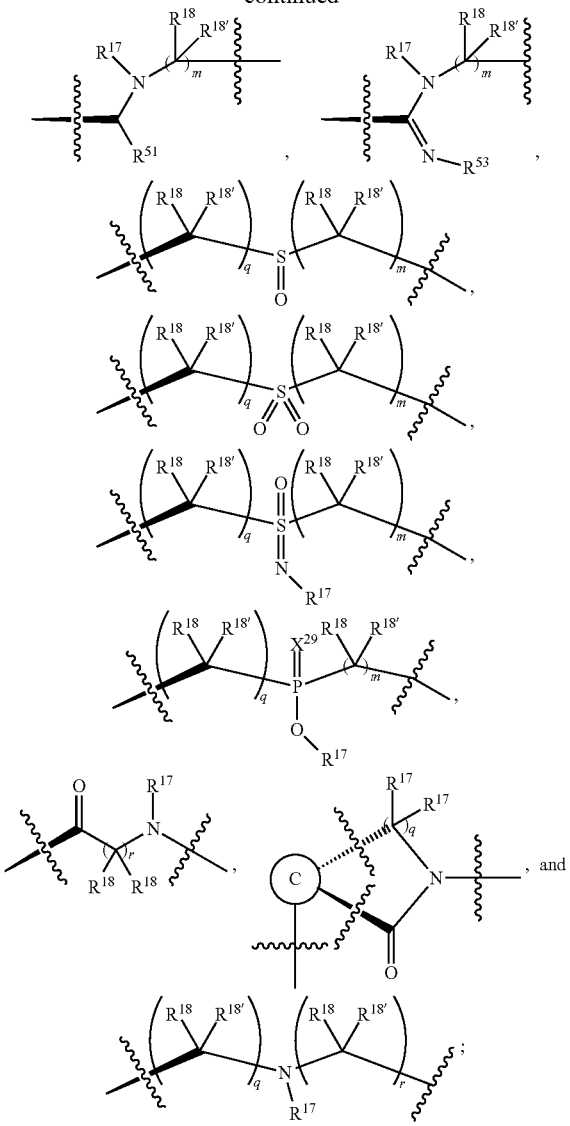

or L2 is selected from an optionally substituted monocyclic or bicyclic carbocyclic; an optionally substituted monocyclic or bicyclic carbocyclic-oxy group; an optionally substituted monocyclic or bicyclic heterocycle group having 1, 2, 3, or 4 heteroatoms independently selected from N, O, and S and from 4 to 7 ring atoms per ring, an optionally substituted —(C$_0$-C$_4$alkyl)(aryl); an optionally substituted —(C$_0$-C$_4$alkyl)(5-membered heteroaryl); an optionally substituted —(C$_0$-C$_4$alkyl)(6-membered heteroaryl); an optionally substituted —(C$_0$-C$_4$alkyl)(8-membered heteroaryl); an optionally substituted —(C$_0$-C$_4$alkyl)(9-membered heteroaryl); and —(C$_0$-C$_4$alkyl)(10-membered heteroaryl);

q is 1, 2 or 3;

R$^{51}$ is CH$_3$, CH$_2$F, CHF$_2$ or CF$_3$;

R$^{53}$ is cyano, nitro, hydroxyl, or alkoxy including C$_1$-C$_6$alkoxy;

X$^{29}$ can be O or S;

L3 is —C(O)—, —C(S)—, —P(O)OH—, —S(O)—, —S(O)$_2$—, or —C(R$^{52}$)$_2$—;

each R$^{52}$ is independently selected from halo, hydrogen, or optionally substituted alkyl including C$_1$-C$_6$alkyl;

or two R$^{52}$ groups are taken together to form a 3- to 6-membered carbocyclic spiro ring or a 3- to 6-membered heterocyclic spiro ring containing 1 or 2 heteroatoms independently selected from N, O, or S;

B1 is heteroaryl; aryl; biphenyl, a monocyclic or bicyclic carbocycle; a monocyclic or bicyclic carbocyclic-oxy group; a monocyclic, bicyclic, or tricyclic heterocycle group having 1, 2, 3, or 4 heteroatoms independently selected from Boron, Si, N, O, and S and from 4 to 8 ring atoms per ring; alkenyl including $C_2$-$C_6$alkenyl; or alkynyl including $C_2$-$C_6$alkynyl; each of which B1 is optionally substituted with one or more substituents independently selected from $R^{33}$, $R^{34}$, $R^{35}$, and $R^{36}$;

$R^{33}$ is independently selected from halogen, hydroxyl, —COOH, cyano, alkyl including $C_1$-$C_6$alkyl, alkanoyl including $C_2$-$C_6$alkanoyl, alkoxy including $C_1$-$C_6$alkoxy, —$C_0$-$C_4$alkyl$NR^9R^{10}$, —$SO_2R^9$, haloalkyl including $C_1$-$C_6$haloalkyl, $S(O)=NHR^{21}$, $SF_5$, and $JC(R^9)=NR^{21}$, and haloalkoxy including $C_1$-$C_6$haloalkoxy;

$R^{34}$ is independently selected from nitro, alkenyl including $C_2$-$C_6$alkenyl, alkynyl including $C_2$-$C_6$alkynyl, thioalkyl including $C_1$-$C_6$thioalkyl, -$JC_3$-$C_7$cycloalkyl, -$JB(OH)_2$, -$JC(O)NR^9R^{23}$, -$JOSO_2OR^{21}$, -$JC(O)(CH_2)_{1-4}S(O)R^{21}$, —$O(CH_2)_{1-4}S(O)NR^{21}R^{22}$, -$JOP(O)(OR^{21})(OR^{22})$, -$JP(O)(OR^{21})(OR^{22})$, -$JOP(O)(OR^{21})R^{22}$, -$JP(O)(OR^{21})R^{22}$, -$JOP(O)R^{21}R^{22}$, -$JP(O)R^{21}R^{22}$, -$JSP(O)(OR^{21})(OR^{22})$, -$JSP(O)(OR^{21})(R^{22})$, -$JSP(O)(R^{21})(R^{22})$, -$JNR^9P(O)(NHR^{21})(NHR^{22})$, -$JNR^9P(O)(OR^{21})(NHR^{22})$, -$JNR^9P(O)(OR^{21})(OR^{22})$, -$JC(S)R^{21}$, -$JNR^{21}SO_2R^{22}$, -$JNR^9S(O)NR^{10}R^{22}$, -$JNR^9SO_2NR^{10}R^{22}$, -$JSO_2NR^9COR^{22}$, -$JSO_2NR^9CONR^{21}R^{22}$, -$JNR^{21}SO_2R^{22}$, -$JC(O)NR^{21}SO_2R^{22}$, -$JC(NH_2)=NR^{22}$, -$JCH(NH_2)NR^9S(O)_2R^{22}$, -$JOC(O)NR^{21}R^{22}$, -$JNR^{21}C(O)OR^{22}$, -$JNR^{21}OC(O)R^{22}$, —$(CH_2)_{1-4}C(O)NR^{21}R^{22}$, -$JC(O)R^{24}R^{30}$, -$JNR^9C(O)R^{21}$, -$JC(O)R^{21}$, -$JNR^9C(O)NR^{10}R^{22}$, —$CCR^{21}$, —$(CH_2)_{1-4}OC(O)R^{21}$, —$S(O)_2OR^{21}$, and -$JC(O)OR^{23}$; each of which $R^{34}$ may be unsubstituted or substituted with one or more substituents independently selected from halogen, hydroxyl, nitro, cyano, amino, oxo, —$B(OH)_2$, —$Si(CH_3)_3$, —COOH, —$CONR^9R^{10}$, —$P(O)(OH)_2$, $C_1$-$C_6$alkyl, —$C_0$-$C_4$alkyl($C_3$-$C_7$cycloalkyl), alkoxy including $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, haloalkyl including $C_1$-$C_6$haloalkyl, and $C_1$-$C_6$haloalkoxy;

$R^{35}$ is independently selected from naphthyl, naphthyloxy, indanyl, (4- to 7-membered heterocycloalkyl)$C_0$-$C_4$alkyl containing 1 or 2 heteroatoms selected from N, O, and S, and bicyclic heterocycle containing 1, 2, or 3 heteroatoms independently selected from N, O, and S, and containing 4- to 8-ring atoms in each ring; each of which $R^{35}$ is optionally substituted with one or more substituents independently selected from halogen, hydroxyl, nitro, cyano, $C_1$-$C_6$alkyl, alkenyl including $C_2$-$C_6$alkenyl, alkanoyl including $C_2$-$C_6$alkanoyl, alkoxy including $C_1$-$C_6$alkoxy, $C_1$-$C_6$alkylester, —$C_0$-$C_4$alkyl($C_3$-$C_7$cycloalkyl), —$SO_2R^9$, haloalkyl including $C_1$-$C_6$haloalkyl, and haloalkoxy including $C_1$-$C_6$haloalkoxy;

$R^{36}$ is independently selected from tetrazolyl, (phenyl)$C_0$-$C_2$alkyl, (phenyl)$C_1$-$C_6$alkoxy, phenoxy, and 5- or 6-membered heteroaryl containing 1, 2, or 3 heteroatoms independently selected from N, O, Boron, Si, and S, each of which $R^{36}$ is optionally substituted with one or more substituents independently selected from halogen, hydroxyl, nitro, cyano, alkyl including $C_1$-$C_6$alkyl, alkenyl including $C_2$-$C_6$alkenyl, alkanoyl including $C_2$-$C_6$alkanoyl, alkoxy including $C_1$-$C_6$alkoxy, $C_1$-$C_6$alkylester, —$C_0$-$C_4$alkyl($C_3$-$C_7$cycloalkyl), —$SO_2R^9$, —$OSi(CH_3)_2C(CH_3)_3$, —$Si(CH_3)_2C(CH_3)_3$, haloalkyl including $C_1$-$C_6$haloalkyl, and haloalkoxy including $C_1$-$C_6$haloalkoxy;

in an alternative embodiment $R^{36}$ is a bicyclic heteroaryl such as a 9-membered heteroaryl;

$R^{21}$ and $R^{22}$ are independently selected from hydrogen, hydroxyl, cyano, amino, $C_1$-$C_6$alkyl, haloalkyl including $C_1$-$C_6$haloalkyl, alkoxy including $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)OC$_1$-$C_6$alkyl, —$C_1$-$C_4$alkylOC(O)C$_1$-$C_6$alkyl, —$C_1$-$C_4$alkylC(O)OC$_1$-$C_6$alkyl, (4- to 8-membered heterocycloalkyl)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S, and each $R^{21}$ and $R^{22}$ can be optionally substituted;

or $R^{21}$ and $R^{22}$ can be taken together to form a carbocyclic or heterocyclic ring;

$R^{23}$ is independently selected at each occurrence from alkyl including $C_1$-$C_6$alkyl, haloalkyl including $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 8-membered heterocycle)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S, wherein each $R^{23}$ can be optionally substituted;

$R^{24}$ and $R^{30}$ are taken together with the nitrogen to which they are attached to form a 4- to 7-membered monocyclic heterocycle, or a 6- to 10-membered bicyclic heterocycle group having fused, spiro, or bridged rings, wherein each ring can be optionally substituted;

B2 is selected from:
a. a 4-membered carbocycle fused to a 5- or 6-membered heteroaryl having 1, 2, or 3 heteroatoms independently selected from N, O, and S; wherein the 4-5 or 4-6 ring system can be optionally substituted;
b. (optionally substituted alkyl)-(optionally substituted cycloalkyl), (optionally substituted alkenyl)-(optionally substituted cycloalkyl), or (optionally substituted alkynyl)-(optionally substituted cycloalkyl);
c. a 4-membered carbocycle fused to a 6-membered aryl ring wherein the 4-6 ring system can be optionally substituted;
d. (cycloalkyl)-(optionally substituted aryl), (cycloalkyl)-(optionally substituted heteroaryl), (cycloalkyl)-(optionally substituted heterocycle), (alkyl)-alkenyl), cycloalkyl-alkenyl;
e. alkyl, alkyl(alkynyl), each of which can be optionally substituted;

wherein B2 can be further substituted 1, 2, 3, or 4 times or more with the substituents independently selected from $R^{33}$, $R^{34}$, $R^{35}$, $R^{36}$, and $R^{48}$;

B3 is a monocyclic or bicyclic carbocycle; a monocyclic or bicyclic carbocyclic-oxy group; a monocyclic, bicyclic, or tricyclic heterocycle group having 1, 2, 3, or 4 heteroatoms independently selected from Boron, Si, N, O, and S and from 4 to 8 ring atoms per ring; alkenyl including $C_2$-$C_6$alkenyl; alkynyl including $C_2$-$C_6$alkynyl; —($C_0$-$C_4$alkyl)(aryl); —($C_0$-$C_4$alkyl)(heteroaryl); or —($C_0$-$C_4$alkyl)(biphenyl), each of which B3 is substituted with at least one $R^{201}$ and optionally substituted with one or more substituents independently selected from $R^{33}$, $R^{34}$, $R^{35}$, and $R^{36}$;

B4 is a six membered heteroaryl ring with at least two substituents selected from $R^{25}$, $R^{26}$, $R^{27}$ and $R^{28}$;

or B4 is a six membered heteroaryl ring with at least three substituents selected from $R^{25}$, $R^{26}$, $R^{27}$ and $R^{28}$;

or B4 is a pyridine with at least two substituents selected from $R^{25}$, $R^{26}$, $R^{27}$ and $R^{28}$;

or B4 is selected from:

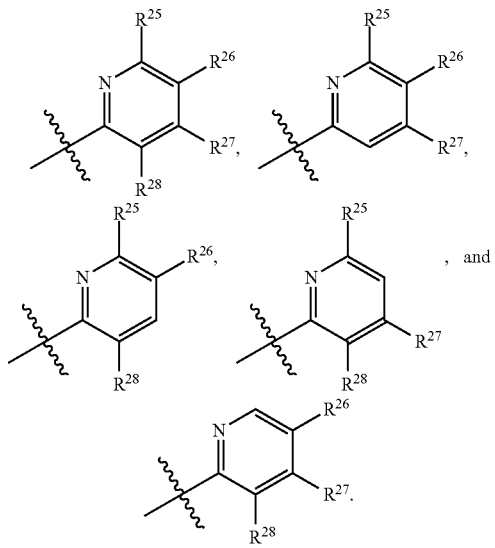

$R^{25}$, $R^{26}$, $R^{27}$, and $R^{28}$ are independently selected from halogen, hydroxyl, nitro, cyano, alkyl including $C_1$-$C_6$alkyl, alkenyl including $C_2$-$C_6$alkenyl, alkanoyl including $C_2$-$C_6$alkanoyl, alkoxy including $C_1$-$C_6$alkoxy, thioalkyl including $C_1$-$C_6$thioalkyl, (mono- and di-$C_1$-$C_6$alkylamino) $C_0$-$C_4$alkyl, ($C_3$-$C_7$cycloalkyl)$C_0$-$C_4$alkyl, (aryl)$C_0$-$C_4$alkyl-, (heteroaryl)$C_0$-$C_4$alkyl-, and —$C_0$-$C_4$alkoxy($C_3$-$C_7$cycloalkyl); each of which $R^{25}$, $R^{26}$, $R^{27}$, and $R^{28}$ other than hydrogen, halogen, hydroxyl, nitro, cyano, is unsubstituted or substituted with one or more substituents independently selected from halogen, hydroxyl, amino, alkoxy including $C_1$-$C_6$alkoxy, haloalkyl including $C_1$-$C_6$haloalkyl, ($C_3$-$C_7$cycloalkyl)$C_0$-$C_4$alkyl-, and haloalkoxy including $C_1$-$C_6$haloalkoxy;

or $R^{25}$, $R^{26}$, $R^{27}$, and $R^{28}$ are independently selected from tetrazole, halogen, hydroxyl, nitro, cyano, alkyl including $C_1$-$C_6$alkyl, alkenyl including $C_2$-$C_6$alkenyl, alkanoyl including $C_2$-$C_6$alkanoyl, alkoxy including $C_1$-$C_6$alkoxy, thioalkyl including $C_1$-$C_6$thioalkyl, (mono- and di-$C_1$-$C_6$alkylamino)$C_0$-$C_4$alkyl, ($C_3$-$C_7$cycloalkyl)$C_0$-$C_4$alkyl, (aryl)$C_0$-$C_4$alkyl-, (heteroaryl)$C_0$-$C_4$alkyl-, and —$C_0$-$C_4$alkoxy($C_3$-$C_7$cycloalkyl); each of which $R^{25}$, $R^{26}$, $R^{27}$, and $R^{28}$ other than hydrogen, halogen, hydroxyl, nitro, cyano, is unsubstituted or substituted with one or more substituents independently selected from halogen, hydroxyl, amino, alkoxy including $C_1$-$C_6$alkoxy, haloalkyl including $C_1$-$C_6$haloalkyl, ($C_3$-$C_7$cycloalkyl)$C_0$-$C_4$alkyl-, and haloalkoxy including $C_1$-$C_6$haloalkoxy;

and wherein any of these groups may be further optionally substituted as that term is defined in the Terminology Section below, if desired to achieve the target effect, results in a stable compound that makes chemical sense to the skilled artisan, and the group is not redundant (i.e., as known in the art, alkyl substituted with alkyl is redundant; however for examples, alkoxy substituted with alkoxy is not redundant); and wherein any of the structures illustrated herein, e.g., A1, A2, A3, B1, B2, B3, B4, C1, C2, C3, C4, C5, L, L3, or any of the R moieties, can be optionally independently substituted with 0, 1, 2, 3, or 4, as appropriate, $R^{48}$ substituents.

In another aspect the invention provides a compound of Formula IV:

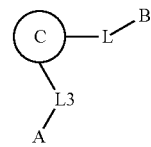

(IV)

or a pharmaceutically acceptable salt, isotopic analog, prodrug, or isolated isomer thereof optionally in pharmaceutically acceptable carrier;

wherein:

the $R^{32}$ group on the A-ring is selected from

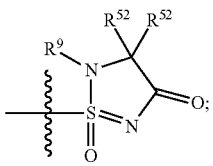

and wherein all other variables are as defined herein.

In another aspect the invention provides a compound of Formula V:

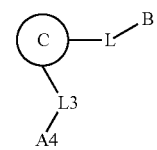

(V)

or a pharmaceutically acceptable salt, isotopic analog, prodrug, N-oxide, or isolated isomer thereof optionally in pharmaceutically acceptable carrier;

wherein:

B is as defined above.

C is as defined above.

L is as defined above.

L3 is as defined above.

A4 is selected from:

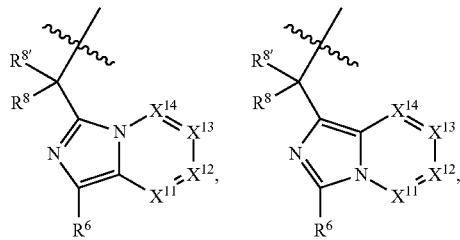

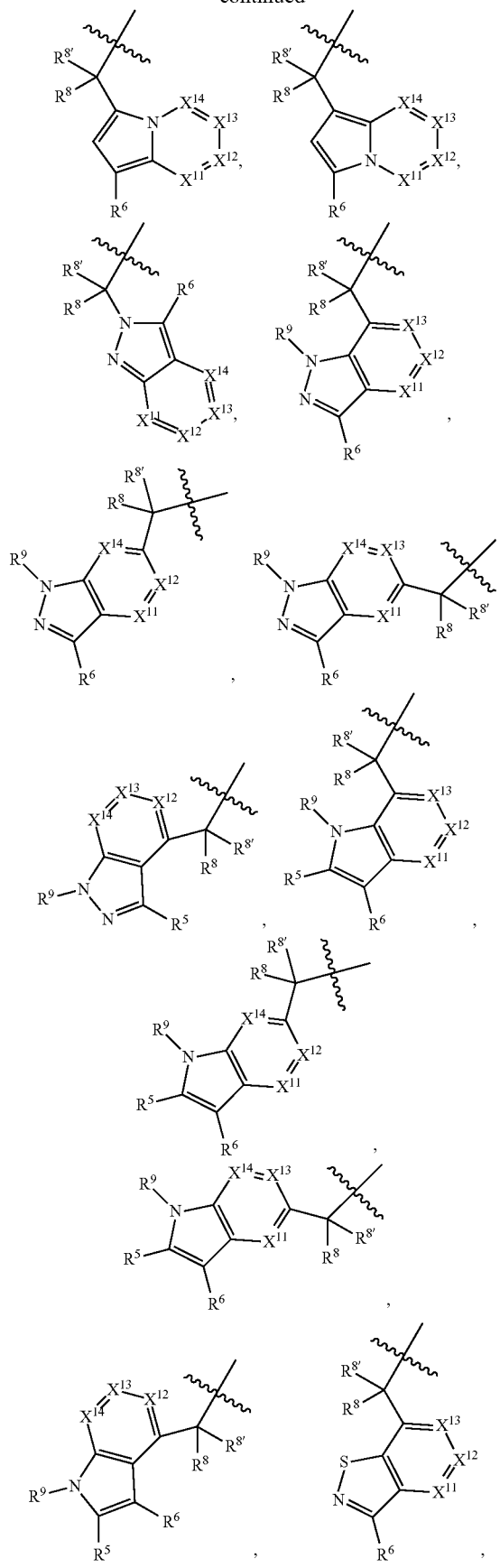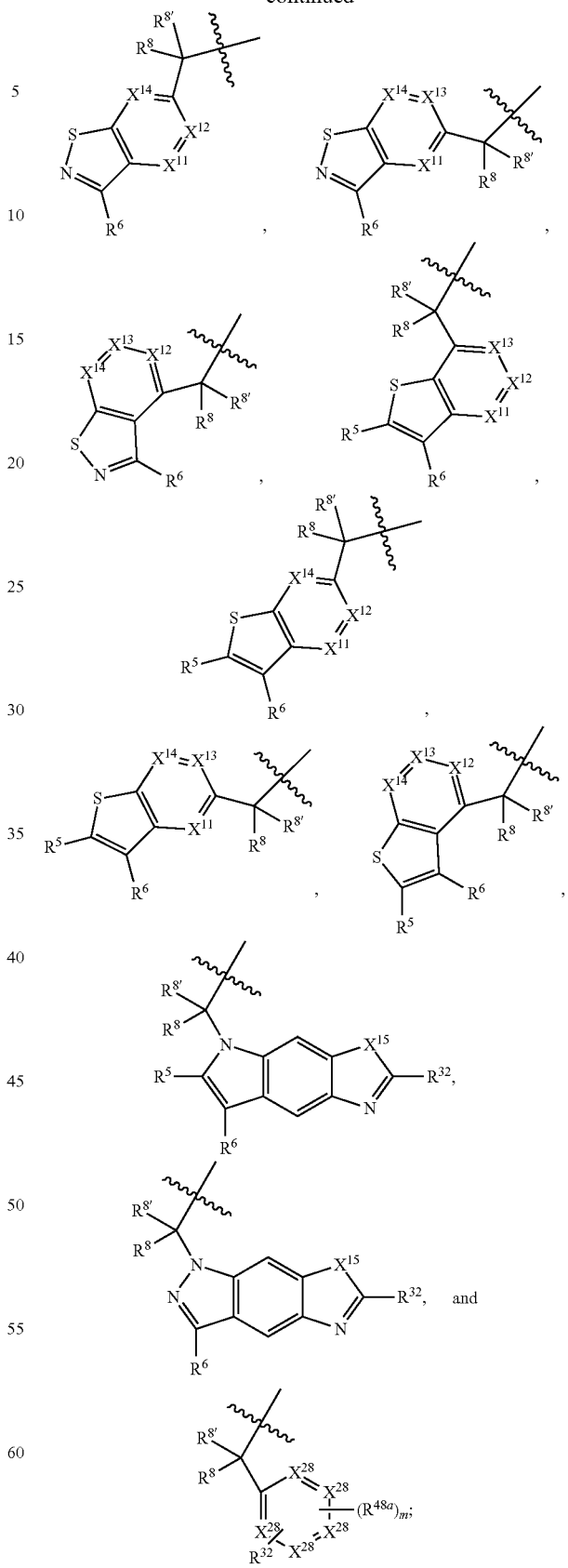
wherein all other variables are as defined herein.

Pharmaceutical compositions comprising a compound or salt of Formula I, Formula II, Formula III, Formula IV, or Formula V together with a pharmaceutically acceptable carrier are also disclosed.

The present invention thus includes at least the following features:

a. a compound of Formula I, Formula II, Formula III, Formula IV, or Formula V or a pharmaceutically acceptable salt, prodrug, isotopic analog, N-oxide, or isolated isomer thereof, optionally in a pharmaceutically acceptable composition, b. a compound of Formula I, Formula II, Formula III, Formula IV, or Formula V or a pharmaceutically acceptable salt, prodrug, isotopic analog, N-oxide, or isolated isomer thereof, optionally in a pharmaceutically acceptable composition, for use in treating or preventing a disorder including but not limited to the development of fatty liver and conditions stemming from fatty liver, such as nonalcoholic steatohepatitis (NASH), liver inflammation, cirrhosis, or liver failure; dermatomyositis; amyotrophic lateral sclerosis; cytokine or inflammatory reactions in response to biotherapeutics (e.g. CAR T-cell therapy); paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease;

c. a pharmaceutically acceptable composition of a compound of Formula I, Formula II, Formula III, Formula IV, or Formula V or its pharmaceutically acceptable salt, prodrug, isotopic analog, N-oxide, or isolated isomer thereof in a pharmaceutically acceptable carrier;

d. a compound selected from Formula I, Formula II, Formula III, Formula IV, or Formula V or a pharmaceutically acceptable salt, prodrug, isotopic analog, N-oxide, or isolated isomer thereof, optionally in a pharmaceutically acceptable composition, for use in treating or preventing a disorder mediated by the complement pathway, and for example, cascade Factor D;

e. use of a compound of Formula I, Formula II, Formula III, Formula IV, or Formula V as described herein, or a pharmaceutically acceptable salt, prodrug, isotopic analog, N-oxide, or isolated isomer thereof, optionally in a pharmaceutically acceptable composition, in the manufacture of a medicament for treating or preventing a disorder, including but not limited to the development of fatty liver and conditions stemming from fatty liver, such as nonalcoholic steatohepatitis (NASH), liver inflammation, cirrhosis, liver failure; dermatomyositis; amyotrophic lateral sclerosis; cytokine or inflammatory reactions in response to biotherapeutics (e.g. CAR T-cell therapy); paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease;

f. a process for manufacturing a medicament intended for the therapeutic use for treating or preventing a disorder, or generally for treating or preventing disorders mediated by complement cascade Factor D, characterized in that a compound selected from Formula I, Formula II, Formula III, Formula IV, or Formula V or an embodiment of the active compound is used in the manufacture;

g. a compound selected from Formula I, Formula II, Formula III, Formula IV, or Formula V or a salt thereof as described herein in substantially pure form (e.g., at least 90 or 95%):

h. a compound of Formula I, Formula II, Formula III, Formula IV, or Formula V as described herein, or a pharmaceutically acceptable salt, prodrug, isotopic analog, N-oxide, or isolated isomer thereof, optionally in a carrier to form a pharmaceutically acceptable composition, for use in treating a medical disorder which is an inflammatory or immune condition, a disorder mediated by the complement cascade (including a dysfunctional cascade), a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration.

i. For each of (a) through (i) above, and otherwise herein, each assembly of moieties in the Figures and each active compound made therefrom or its use is considered and deemed specifically and individually disclosed, as such depiction is for convenience of space only and not intended to describe a only a genus or even a subgenus for such indication.

DETAILED DESCRIPTION

Terminology

Figure 1:
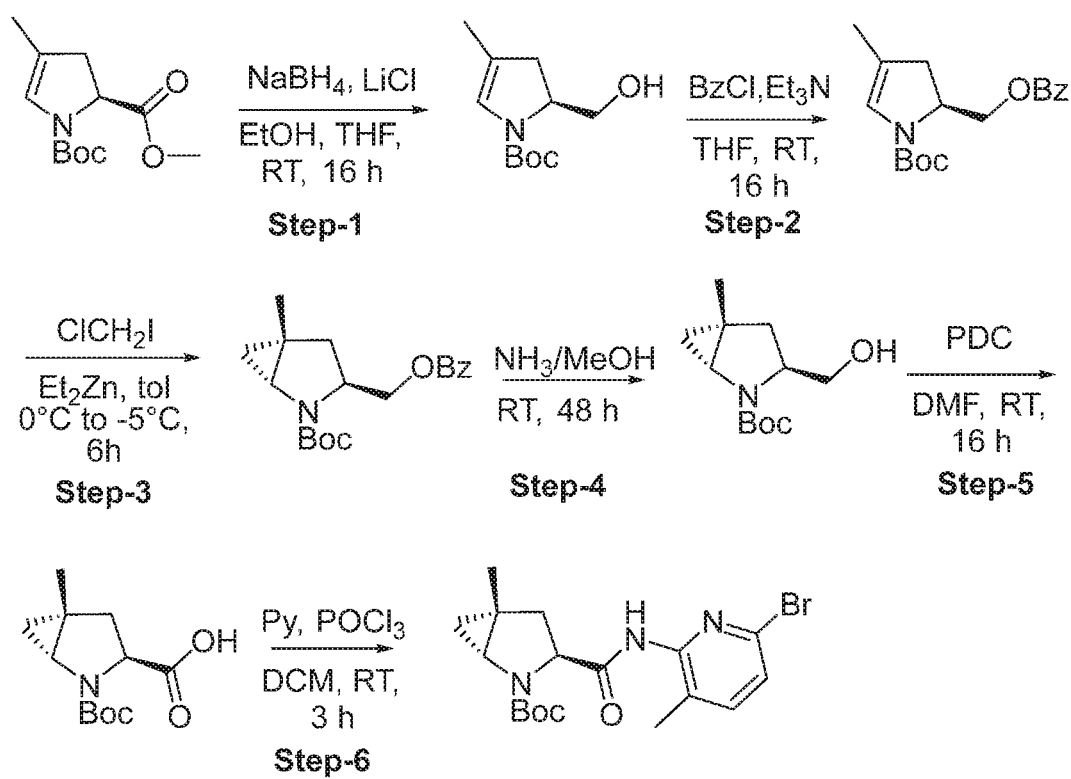
FIG. 1 is the six-step procedure to synthesize intermediate tert-butyl (1R,3S,5R)-3-((6-bromo-3-methylpyridin-2-yl)carbamoyl)-5-methyl-2-azabicyclo[3.1.0]hexane-2-carboxylate.
Figure 2:
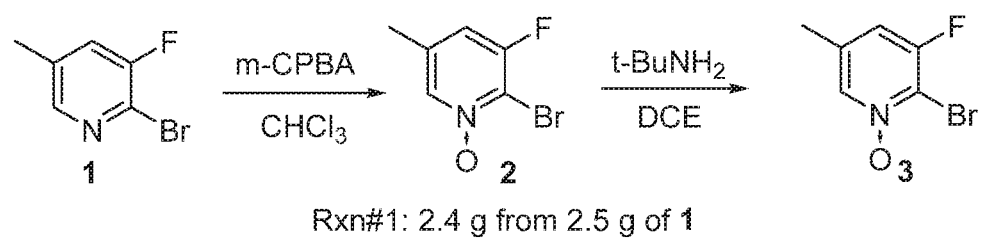
FIG. 2 is the two-step synthesis of intermediate 2-bromo-3-fluoro-5-methylpyridine 1-oxide (Compound 3 in FIG. 2).
Figure 3:
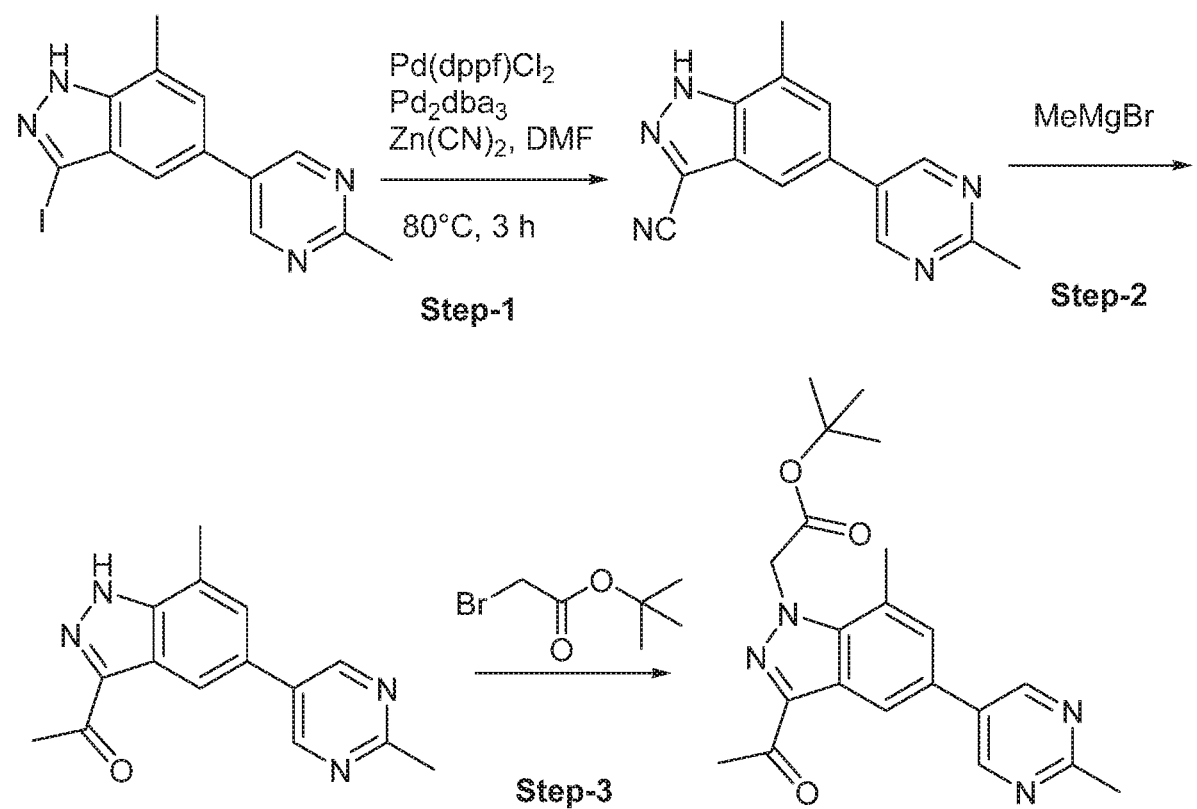
FIG. 3 is the three-step procedure to synthesize the intermediate tert-butyl 2-(3-acetyl-7-methyl-5-(2-methylpyrimidin-5-yl)-1H-indazol-1-yl)acetate.
Figure 4:
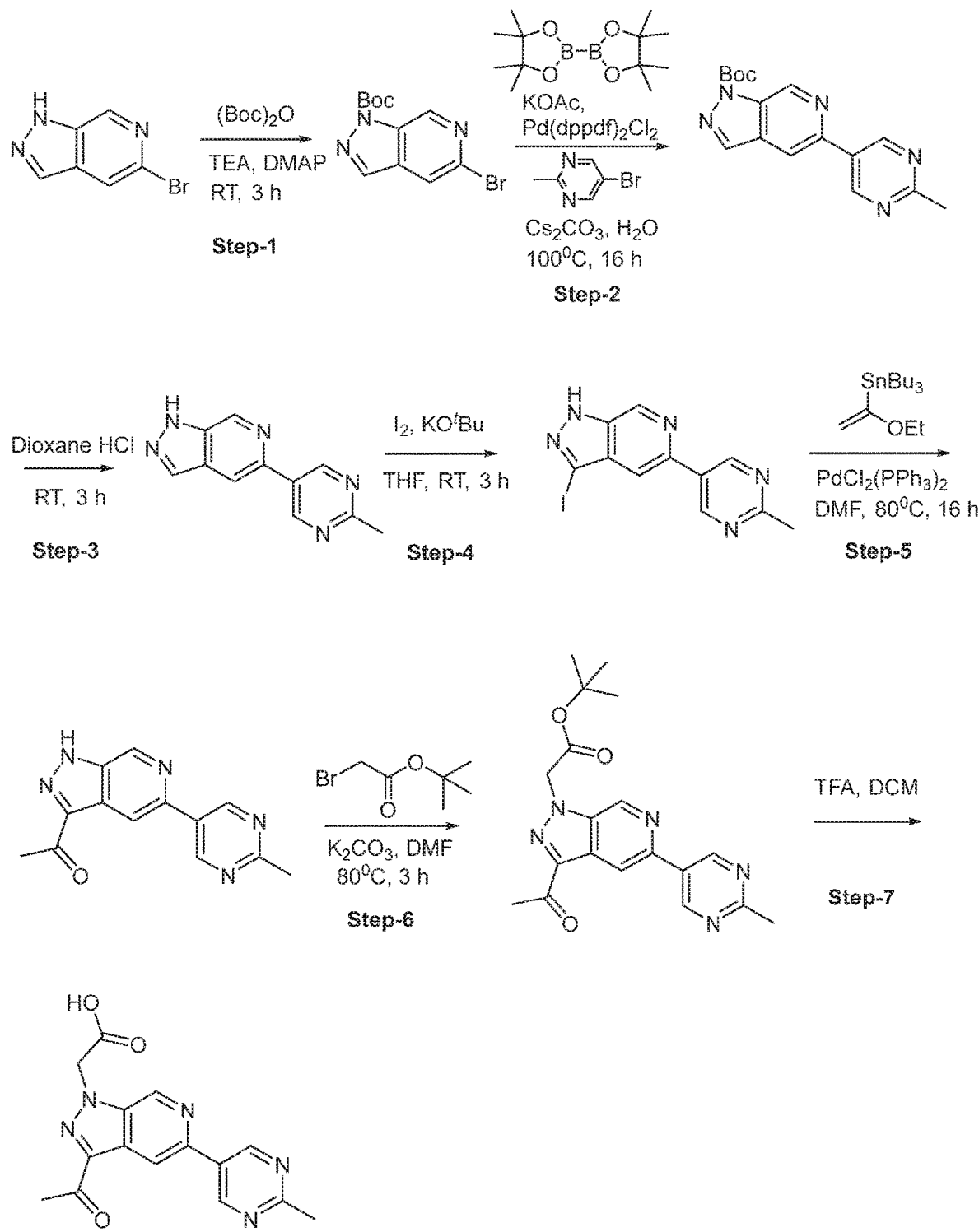
FIG. 4 is a seven-step procedure to synthesize the intermediate 2-(3-acetyl-5-(2-methylpyrimidin-5-yl)-1H-pyrazolo[3,4-c]pyridin-1-yl)acetic acid.
Figure 5:
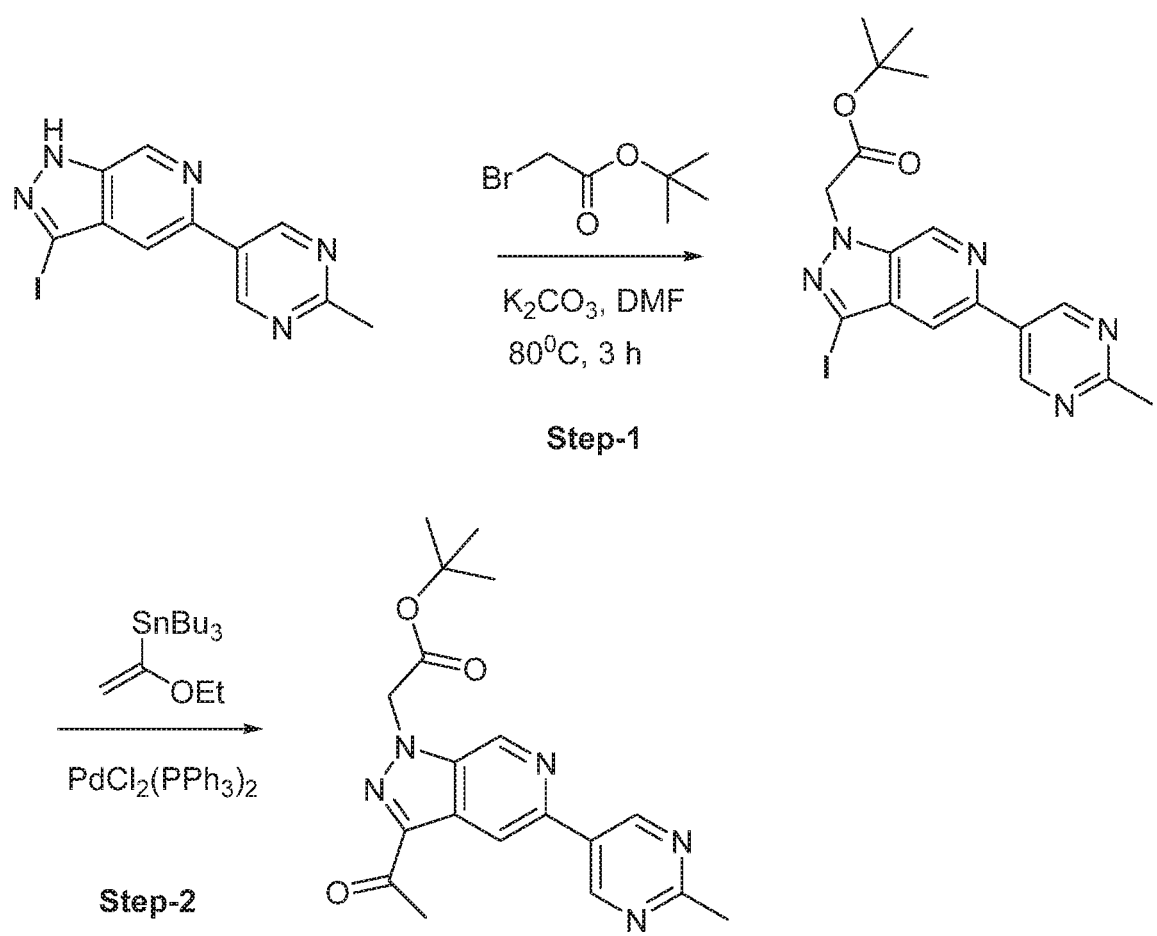
FIG. 5 is the two-step procedure to synthesize the intermediate tert-butyl 2-(3-acetyl-5-(2-methylpyrimidin-5-yl)-1H-pyrazolo[3,4-c]pyridin-1-yl)acetate.
Figure 6:
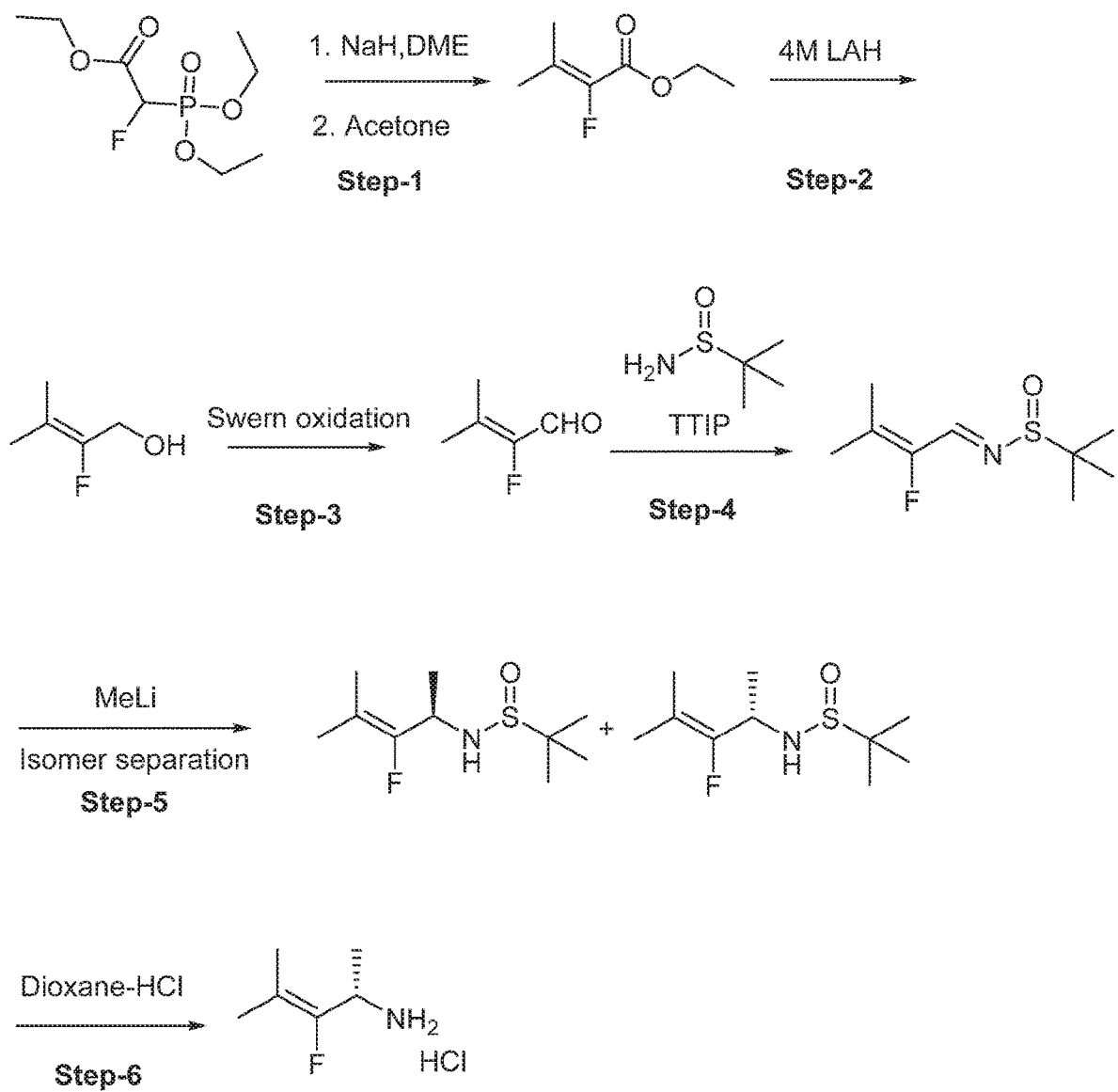
FIG. 6 is the six-step procedure to synthesize intermediate (S)-3-fluoro-4-methylpent-3-en-2-amine hydrochloric acid salt.
Figure 7:
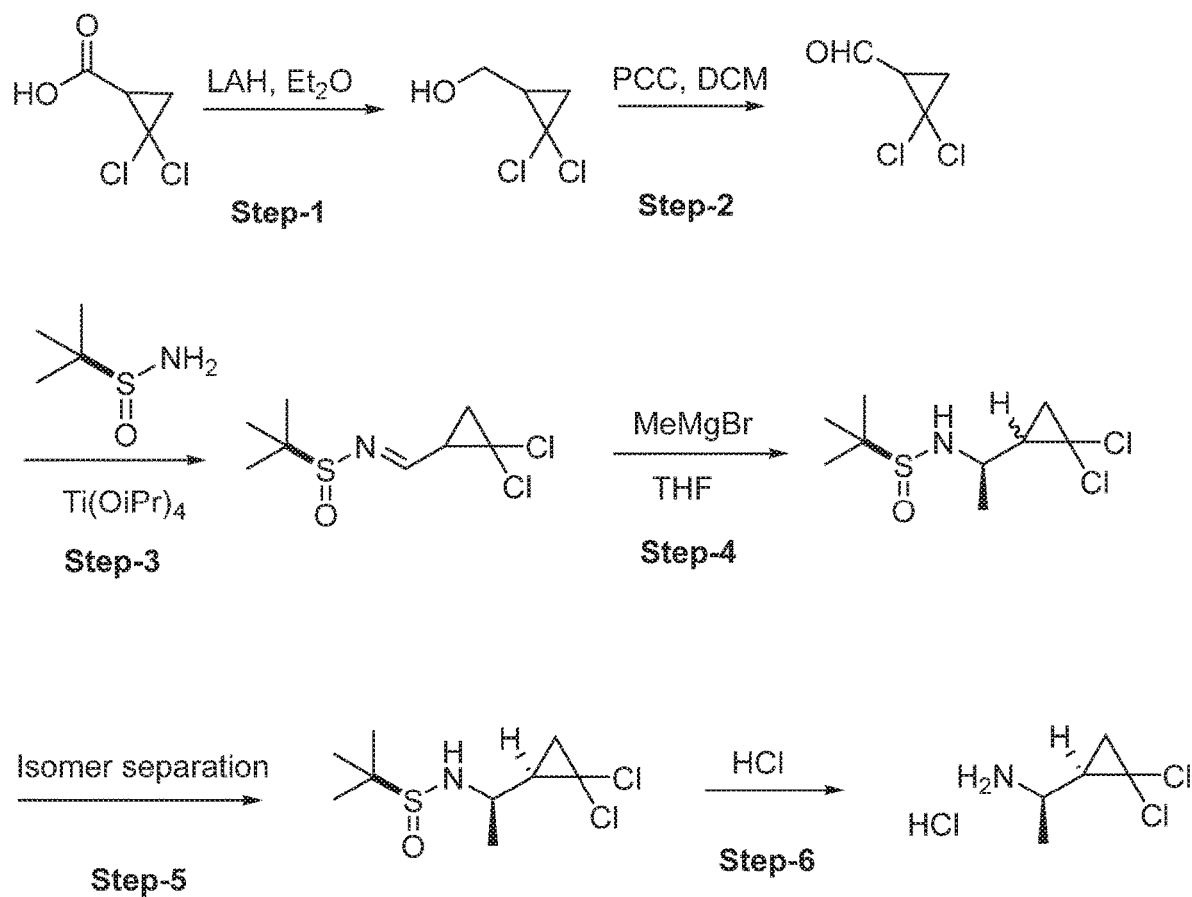
FIG. 7 is the six-step procedure to synthesize intermediate (R)-1-((R)-2,2-dichlorocyclopropyl)ethan-1-amine hydrochloric acid salt.
Figure 8:
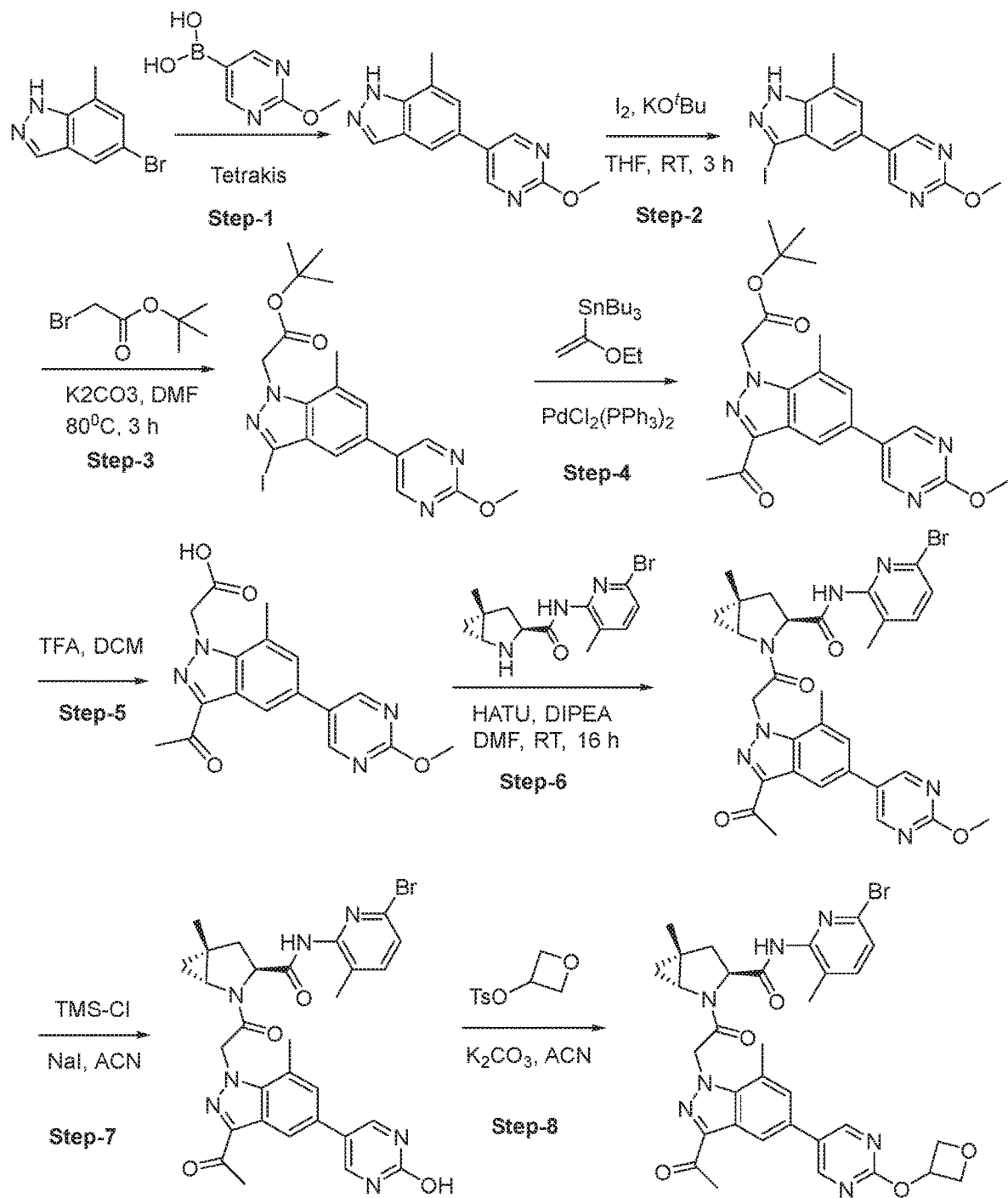
FIG. 8 is the expanded eight-step synthesis of Compound 208 shown in Scheme 153.
Figure 9:
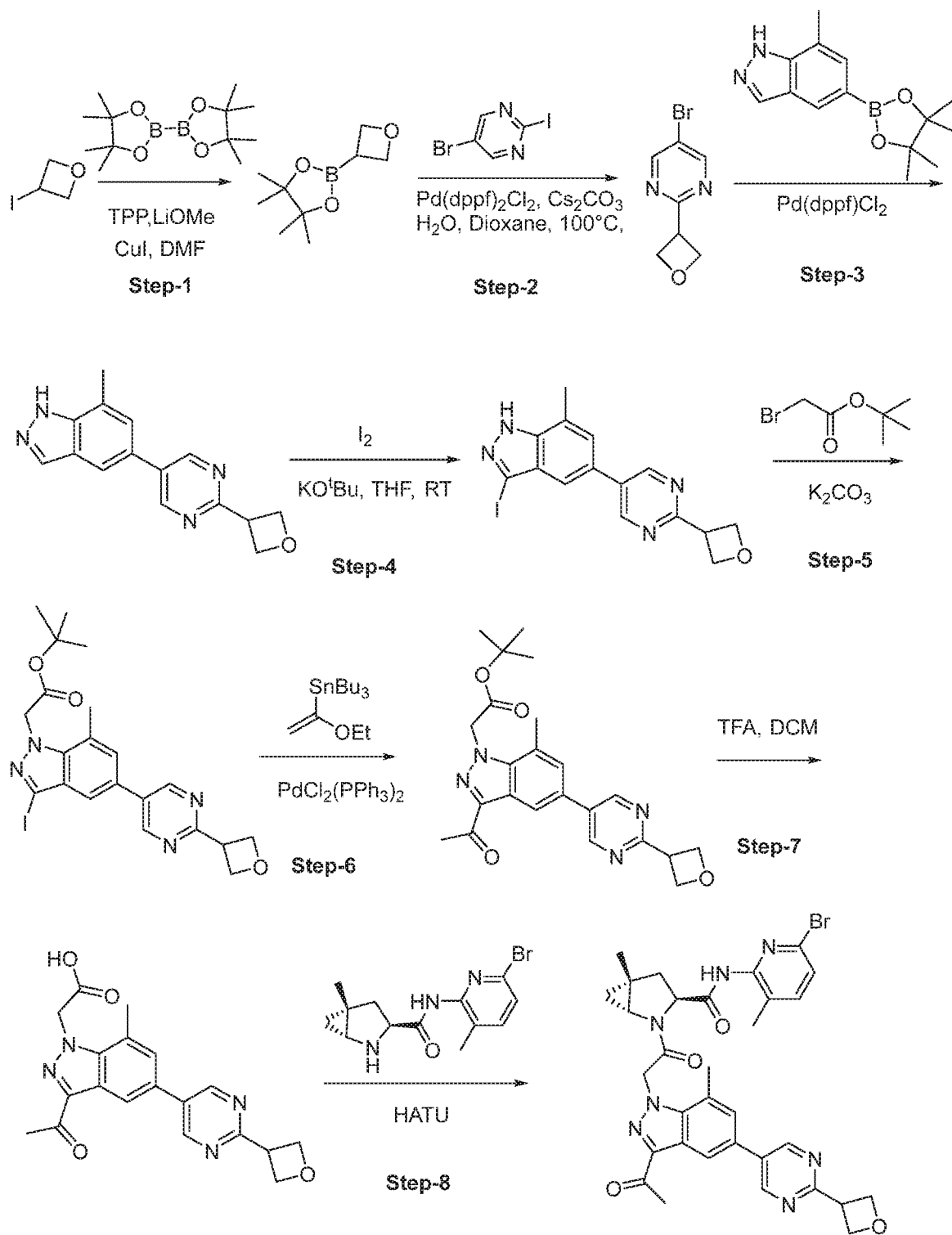
FIG. 9 is the eight-step procedure to synthesize (1R,3S,5R)-2-(2-(3-acetyl-7-methyl-5-(2-(oxetan-3-yl)pyrimidin-5-yl)-1H-indazol-1-yl)acetyl)-N-(6-bromo-3-methylpyridin-2-yl)-5-methyl-2-azabicyclo[3.1.0]hexane-3-carboxamide.
Figure 10:
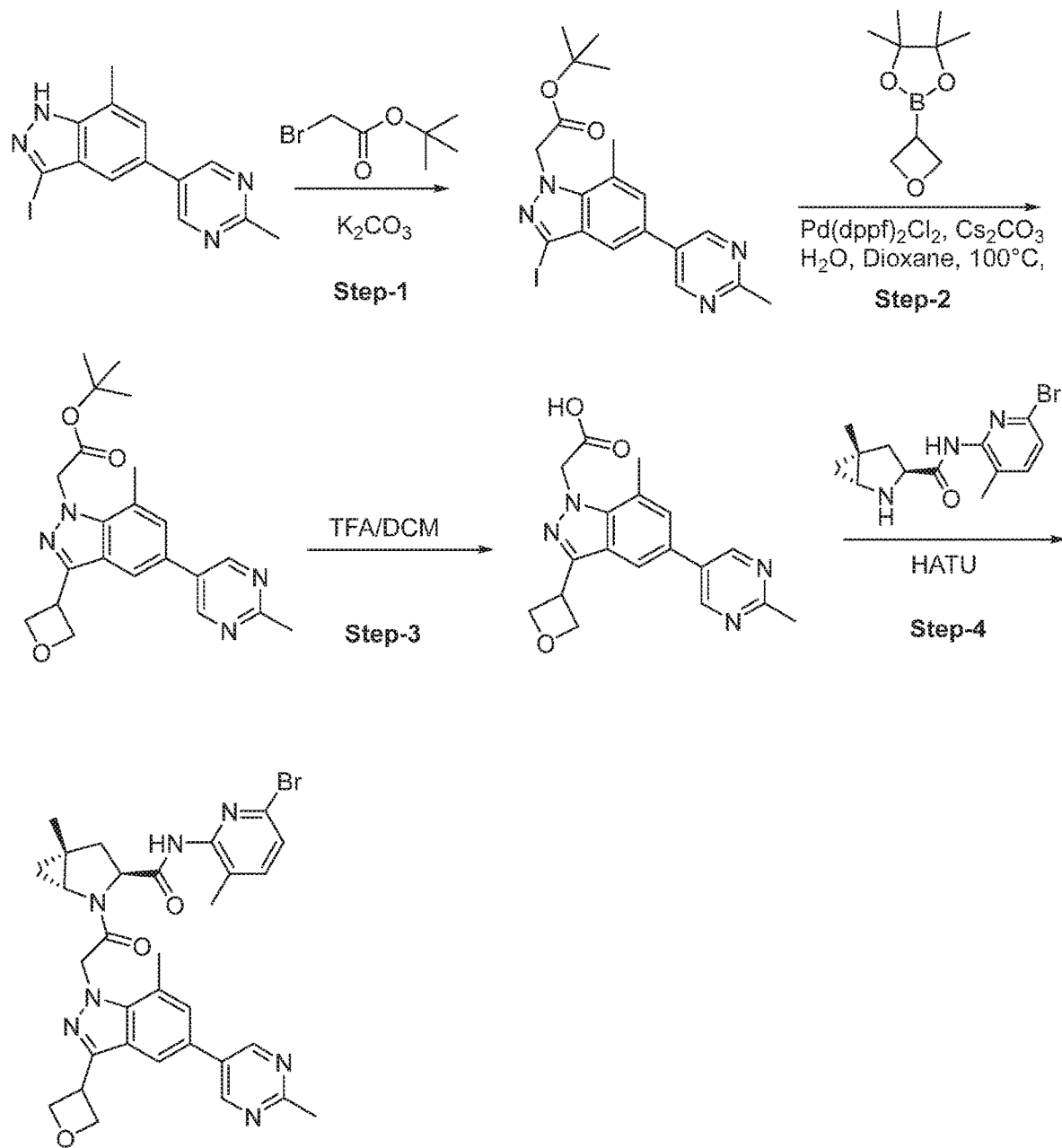
FIG. 10 is a four-step procedure to synthesize (1R,3S,5R)—N-(6-bromo-3-methylpyridin-2-yl)-5-methyl-2-(2-(7-methyl-5-(2-methylpyrimidin-5-yl)-3-(oxetan-3-yl)-1H-indazol-1-yl)acetyl)-2-azabicyclo[3.1.0]hexane-3-carboxamide.
Figure 11:
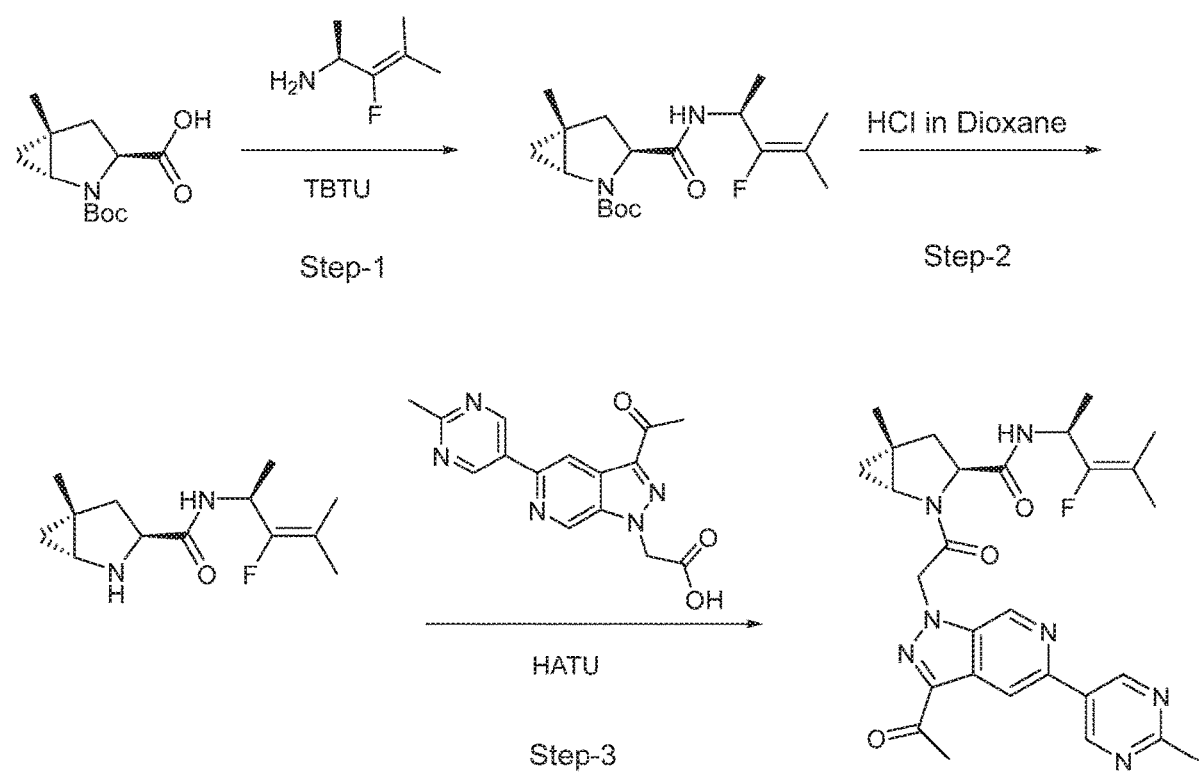
FIG. 11 is a three-step procedure to synthesize (1R,3S,5R)-2-(2-(3-acetyl-5-(2-methylpyrimidin-5-yl)-1H-pyrazolo[3,4-c]pyridin-1-yl)acetyl)-N—((S)-3-fluoro-4-methyl-pent-3-en-2-yl)-5-methyl-2-azabicyclo[3.1.0]hexane-3-carboxamide.
Figure 12:
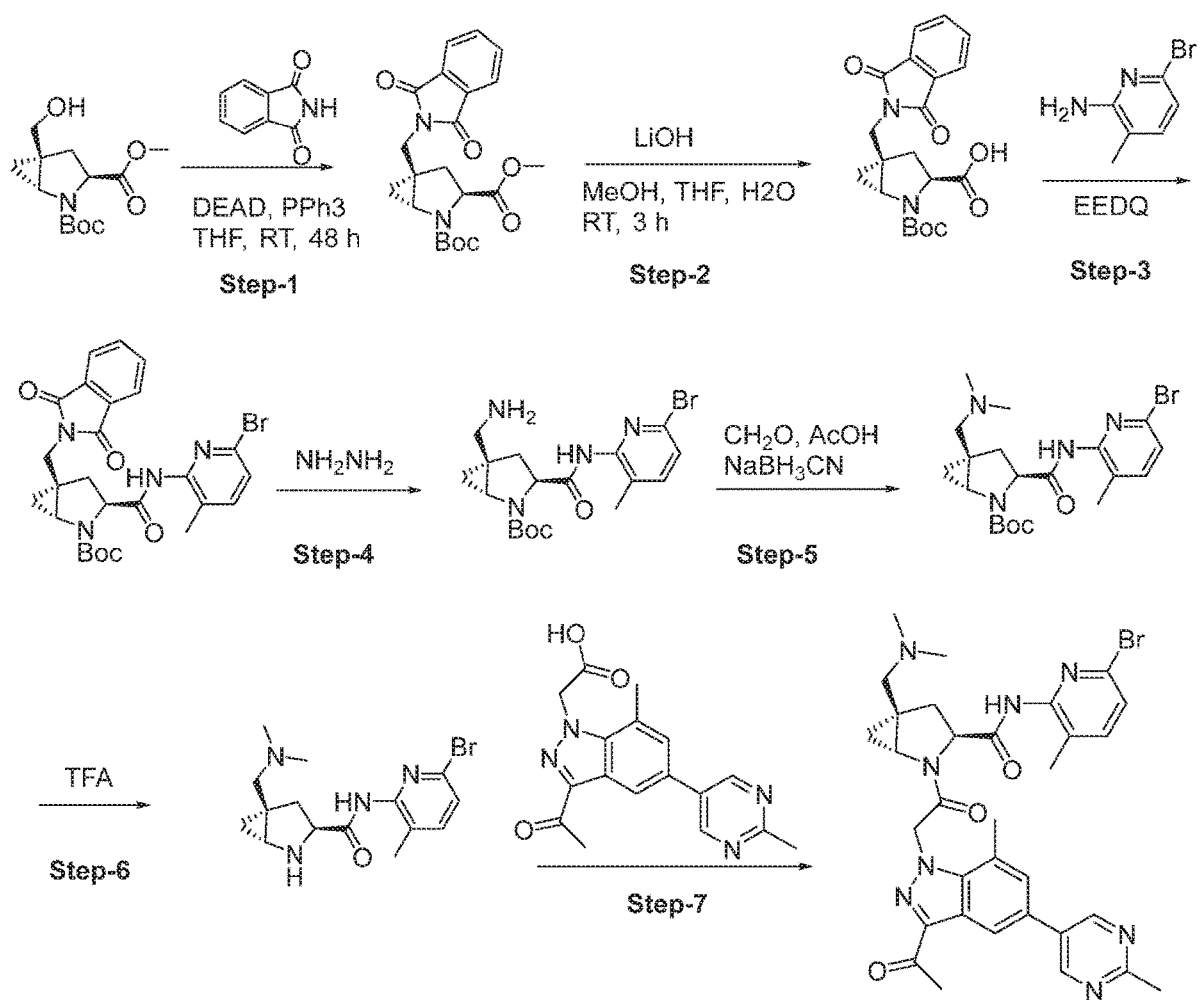
FIG. 12 is a seven-step procedure to synthesize Compound 100.
Figure 13:
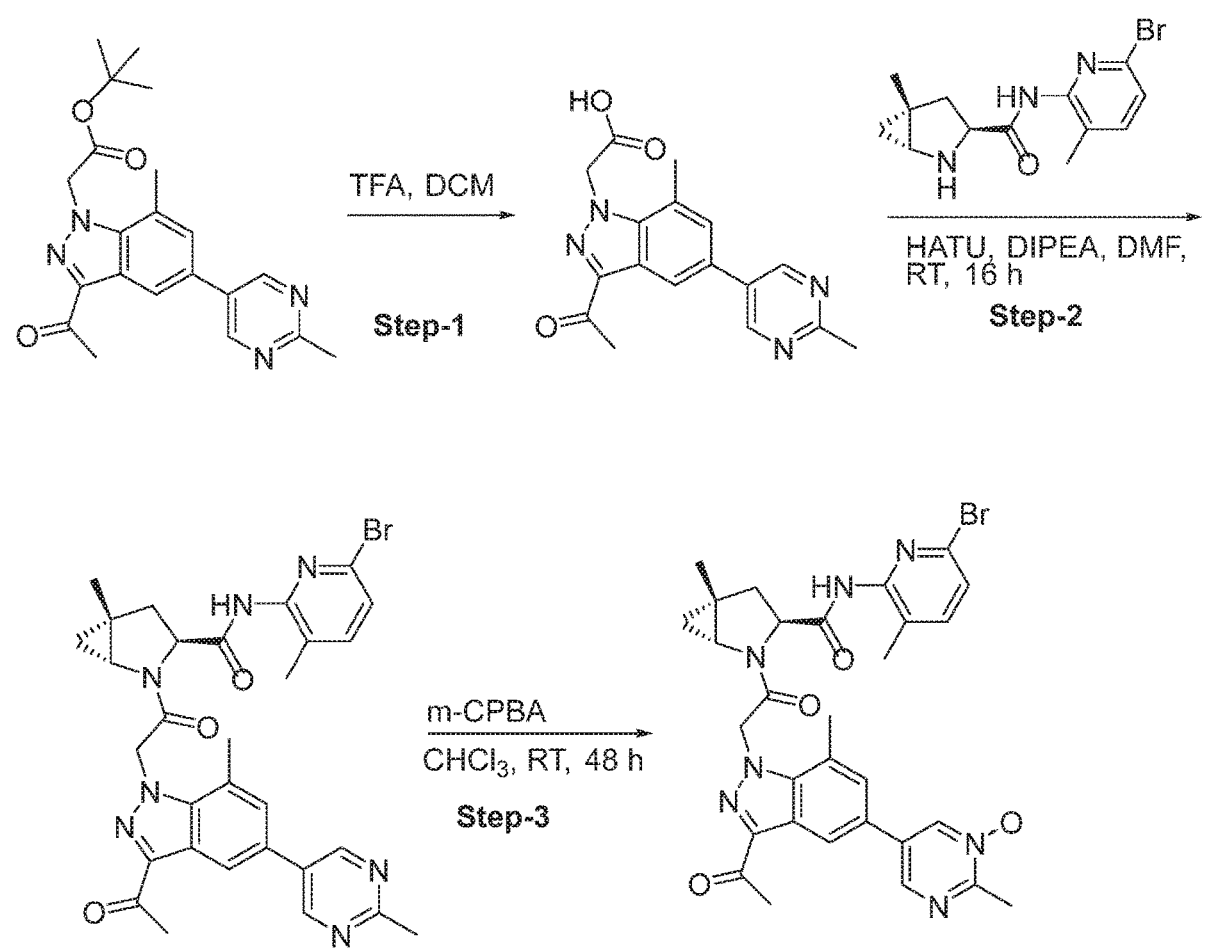
FIG. 13 is a three-step procedure for synthesizing Compound 50 and is an alternative to a synthesis shown in Scheme 45.
Figure 14:
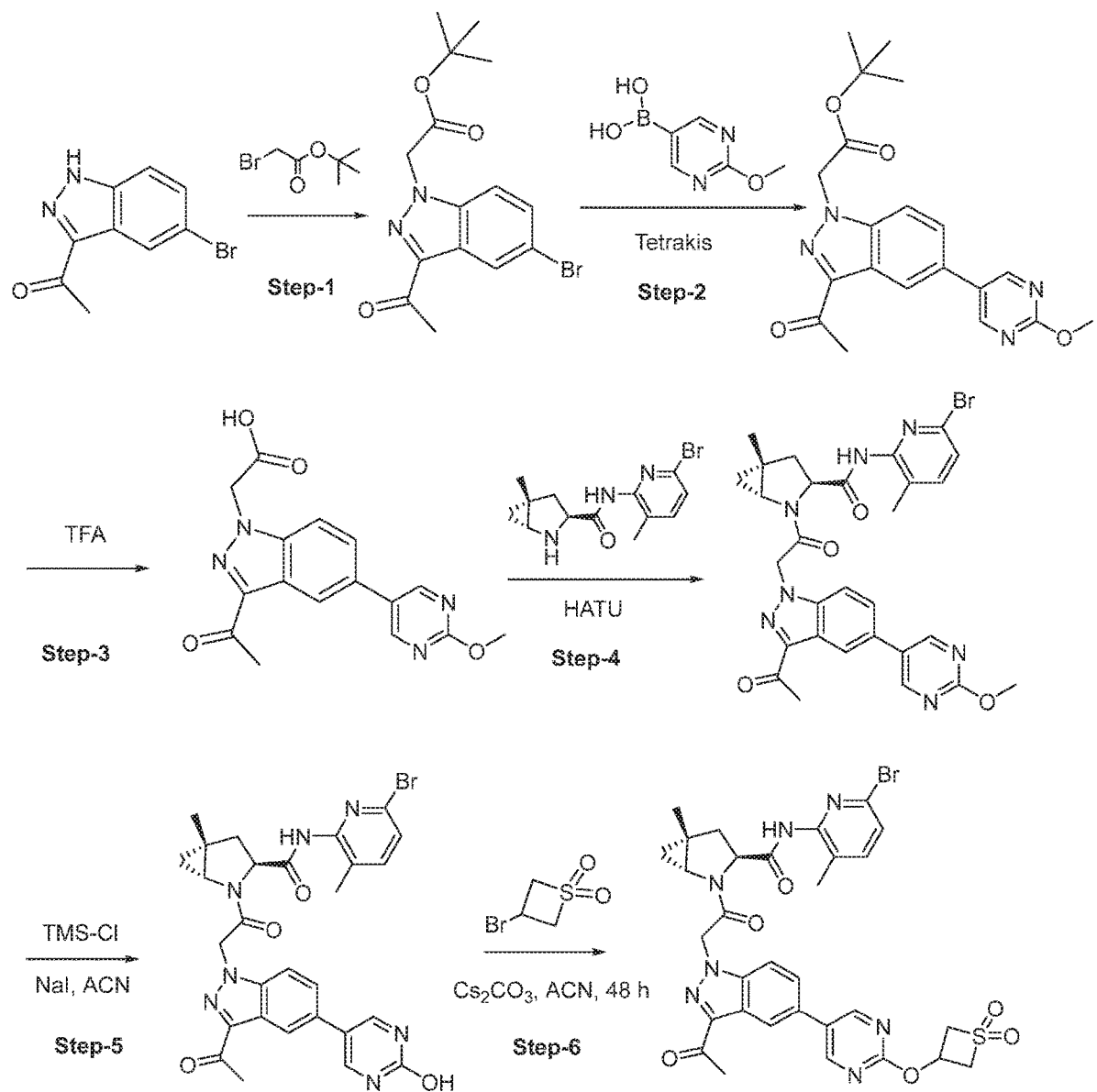
FIG. 14 is the expanded six-step synthesis of Compound 107 shown in Scheme 80.
Figure 15A:
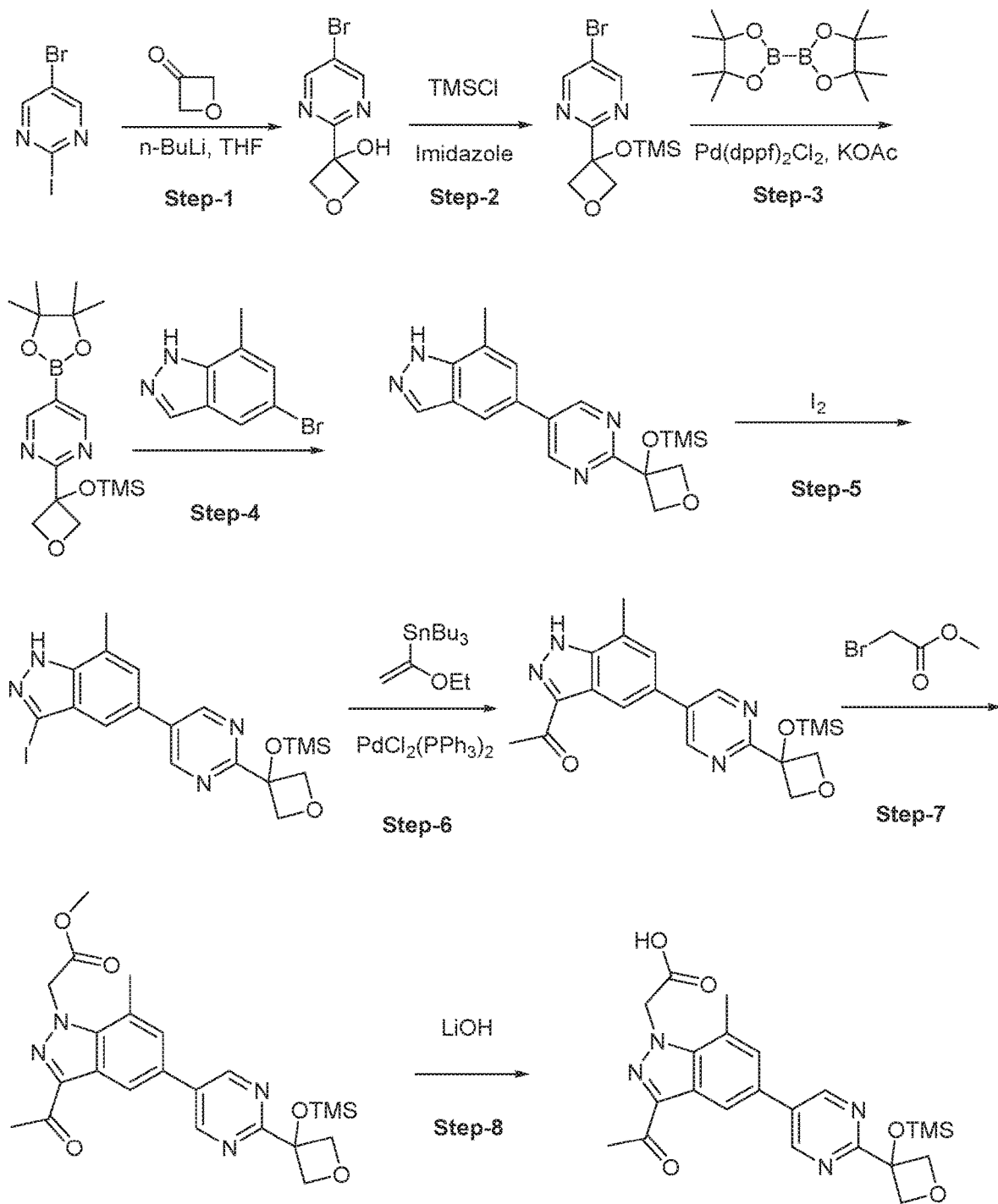
FIG. 15A is the eight-step procedure to synthesize intermediate 2-(3-acetyl-7-methyl-5-(2-(3-((trimethylsilyl)oxy) oxetan-3-yl)pyrimidin-5-yl)-1H-indazol-1-yl)acetic acid.
Figure 15B:
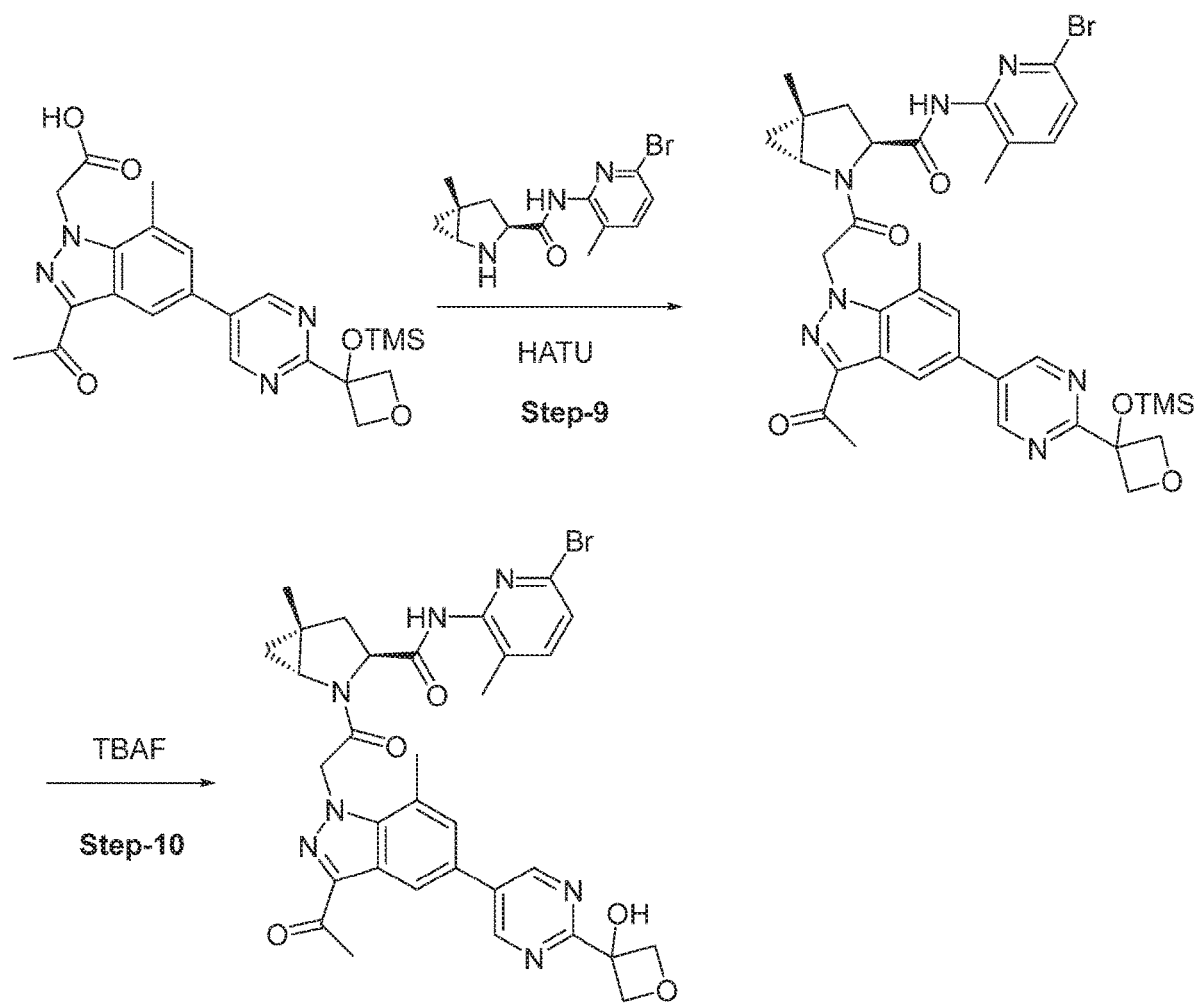
FIG. 15B is the final two steps of a synthesis of (1R,3S,5R)-2-(2-(3-acetyl-5-(2-(3-hydroxyoxetan-3-yl)pyrimidin-5-yl)-7-methyl-1H-indazol-1-yl)acetyl)-N-(6-bromo-3-methylpyridin-2-yl)-5-methyl-2-azabicyclo[3.1.0]hexane-3-carboxamide from the intermediate shown in FIG. 18A.
Figure 16:
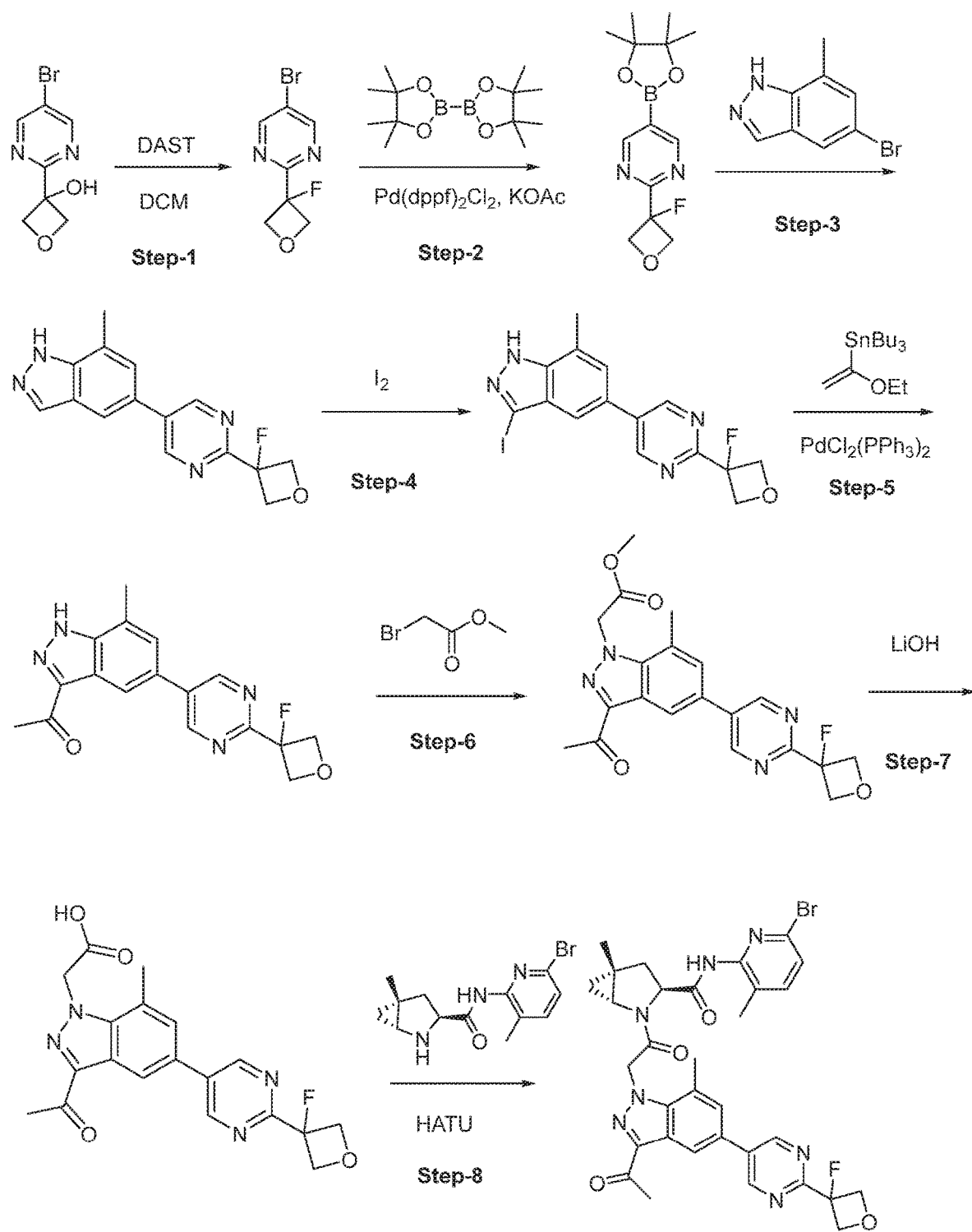
FIG. 16 is the eight-step procedure to synthesize (1R,3S,5R)-2-(2-(3-acetyl-5-(2-(3-fluorooxetan-3-yl)pyrimidin-5-yl)-7-methyl-1H-indazol-1-yl)acetyl)-N-(6-bromo-3-methylpyridin-2-yl)-5-methyl-2-azabicyclo[3.1.0]hexane-3-carboxamide.
Figure 17:
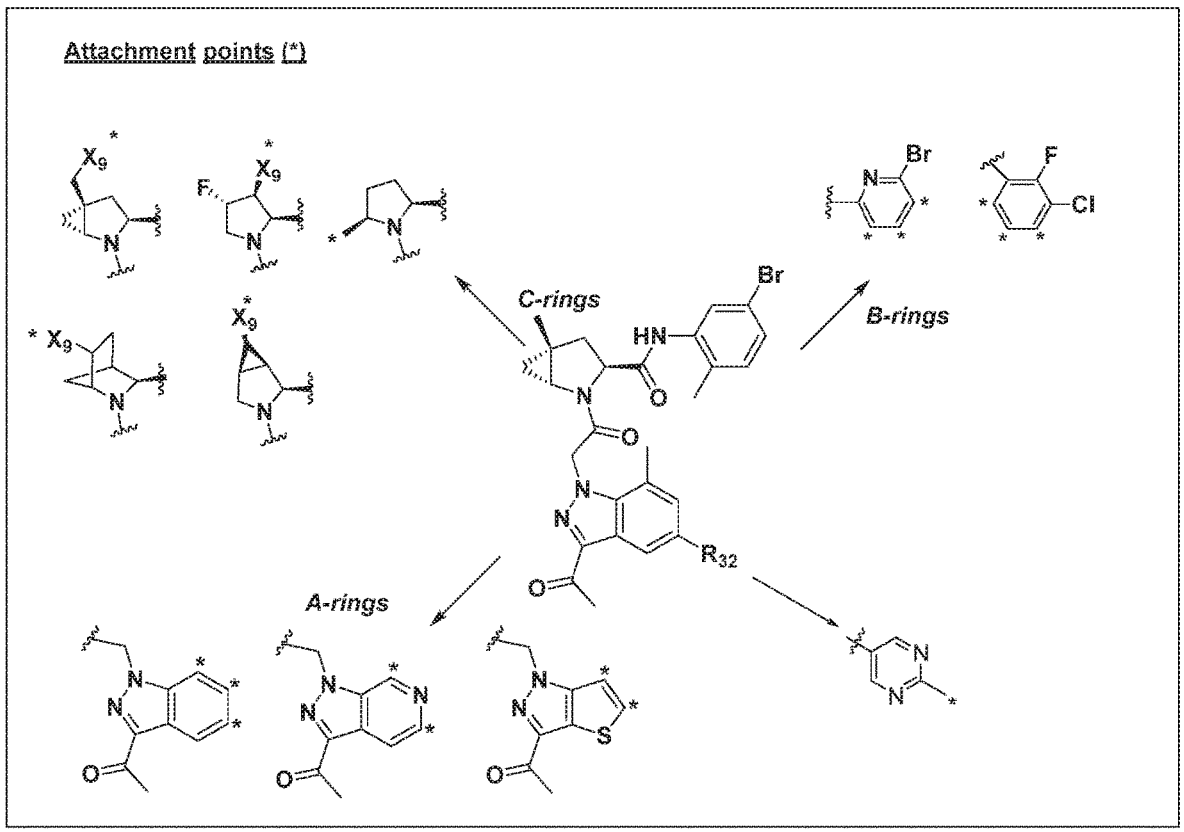
FIG. 17 is a schematic showing the various potential attachment points for $R^{301}$ functionality on the A-ring, B-ring, C-ring, or heteroaryl-containing $R_{32}$ group. $X_9$ as used in FIG. 17 is selected from —$CH_2$—, —O—, —NH—, and —Nalkyl-.
Figure 18A:
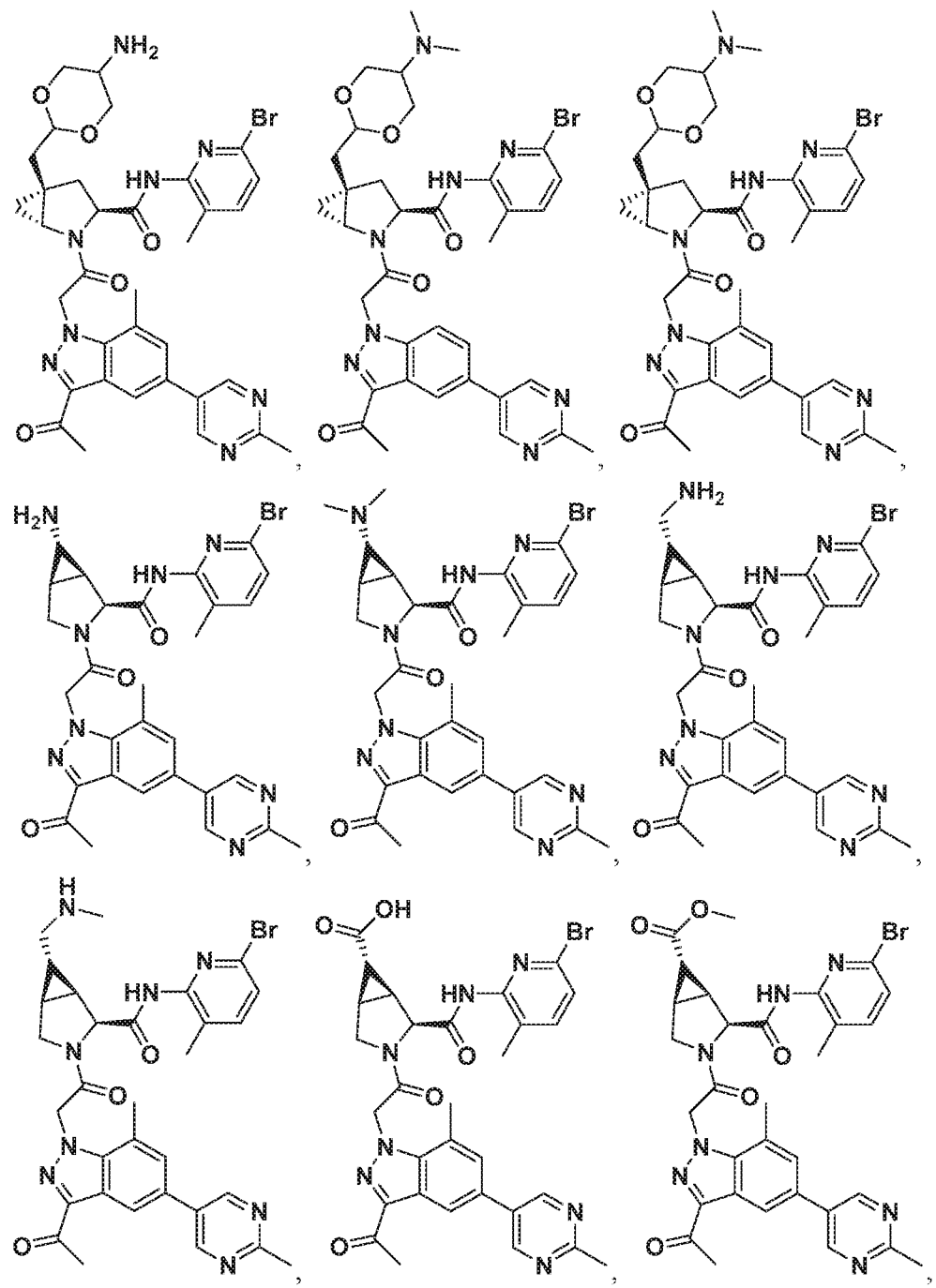
FIGS. 18A, 18B, 18C, 18D, 18E, 18F, 18G, 18H, 18I, 18J, 18K, 18L, 18M, 18N, 18O, 18P, 18Q, 18R, 18S, 18T, 18U, and 18V are examples of compounds that exemplify Formula I, Formula II, or Formula III.
Figure 18B:
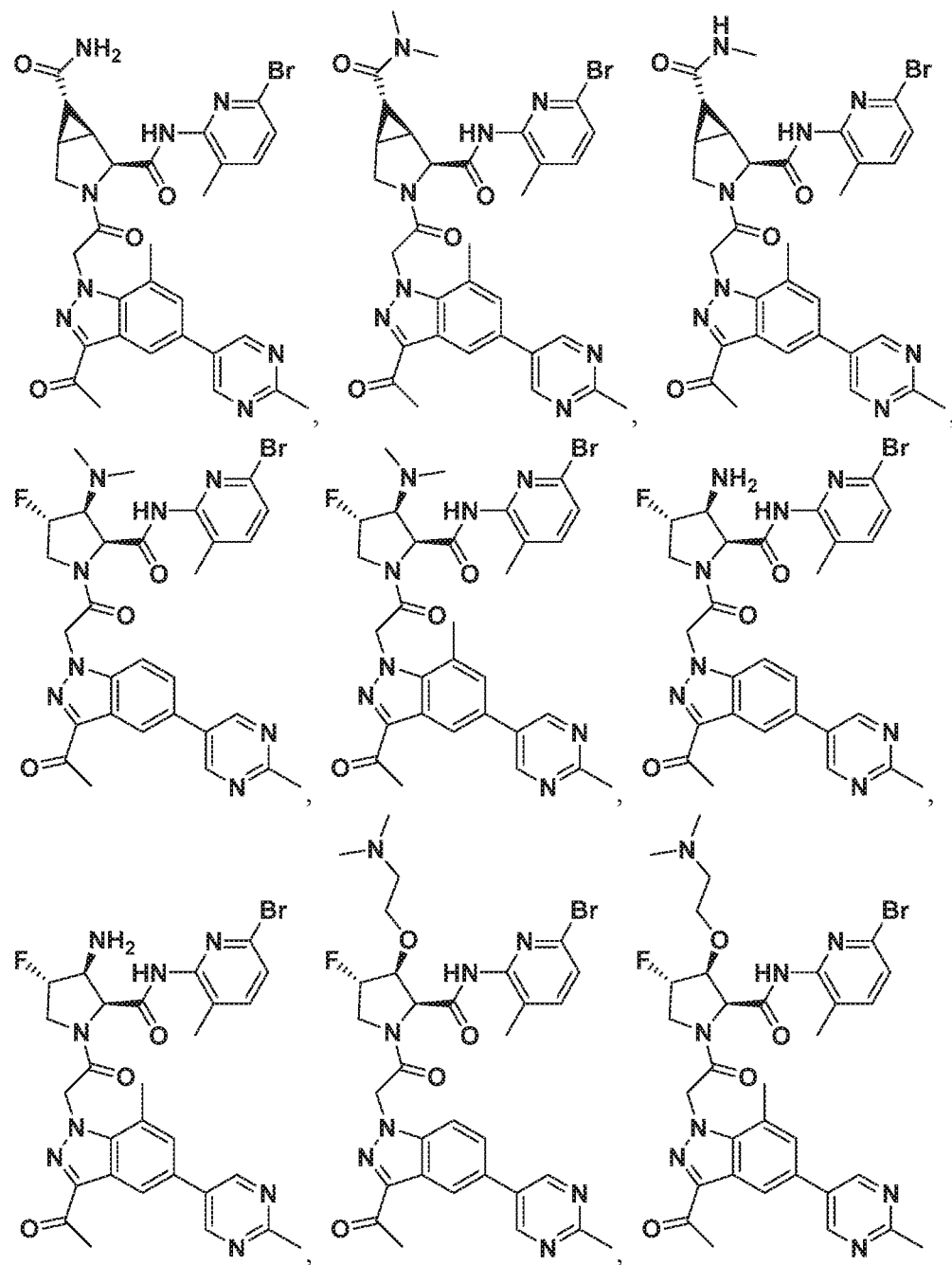
Figure 18C:
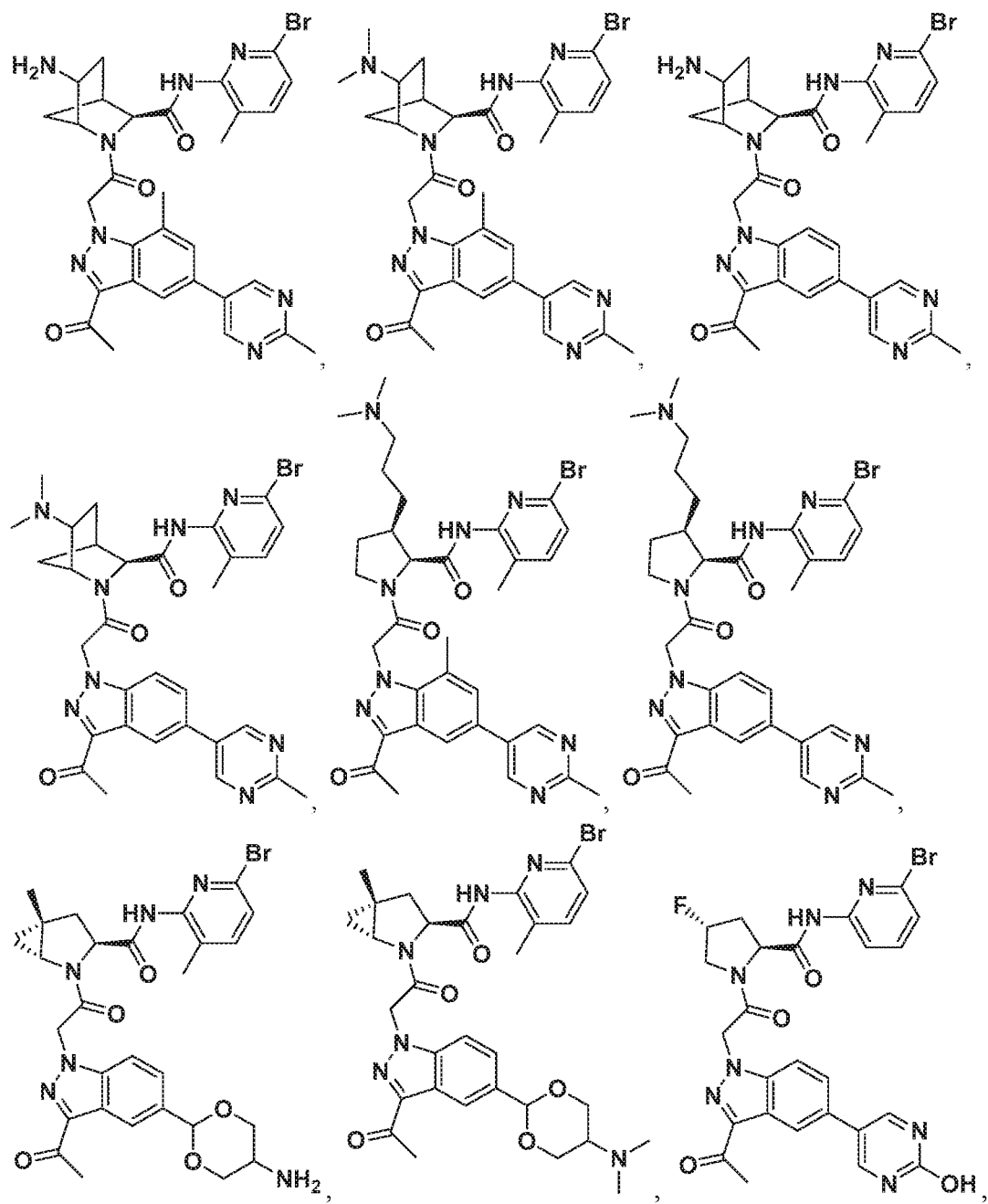
Figure 18D:
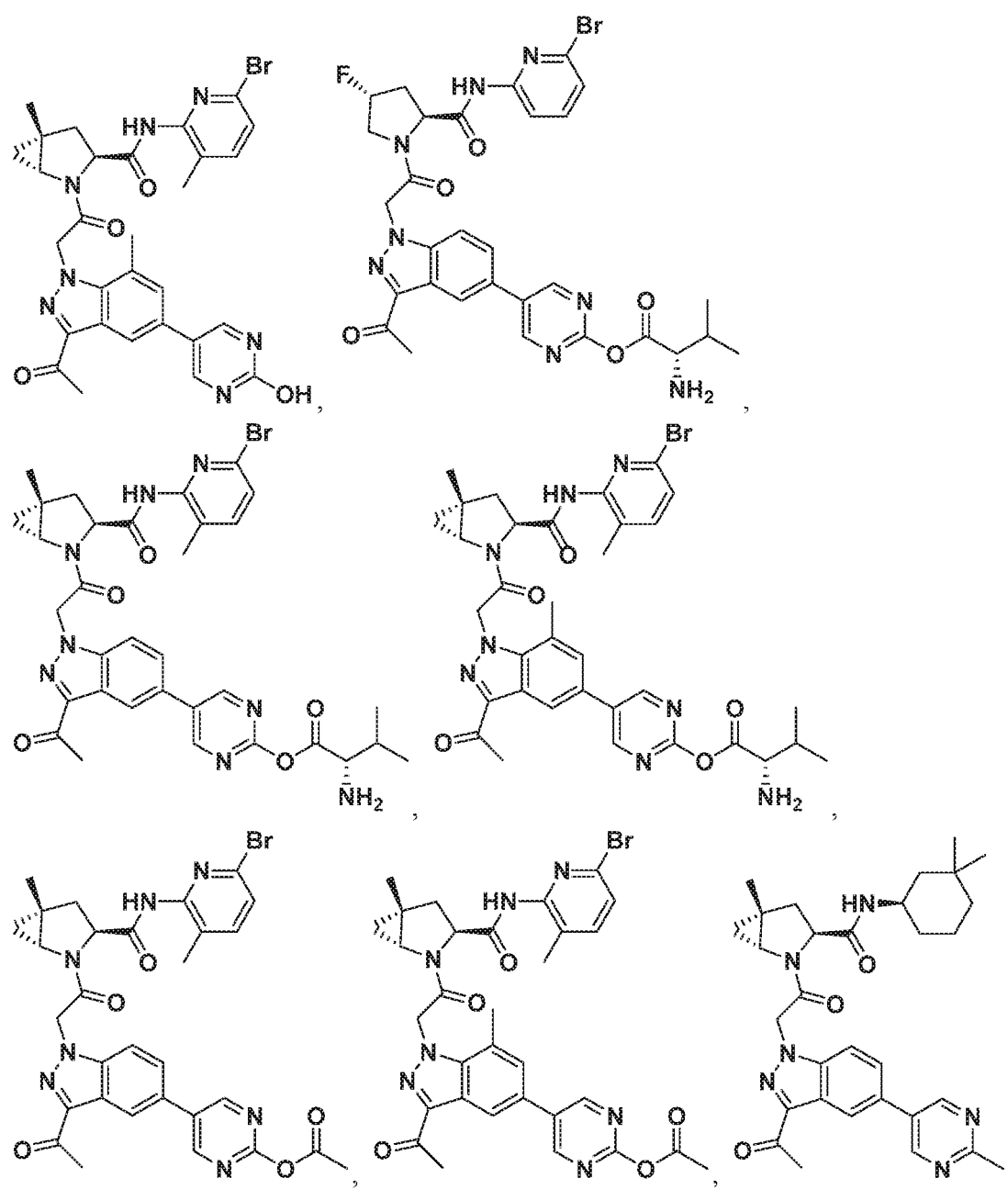
Figure 18E:
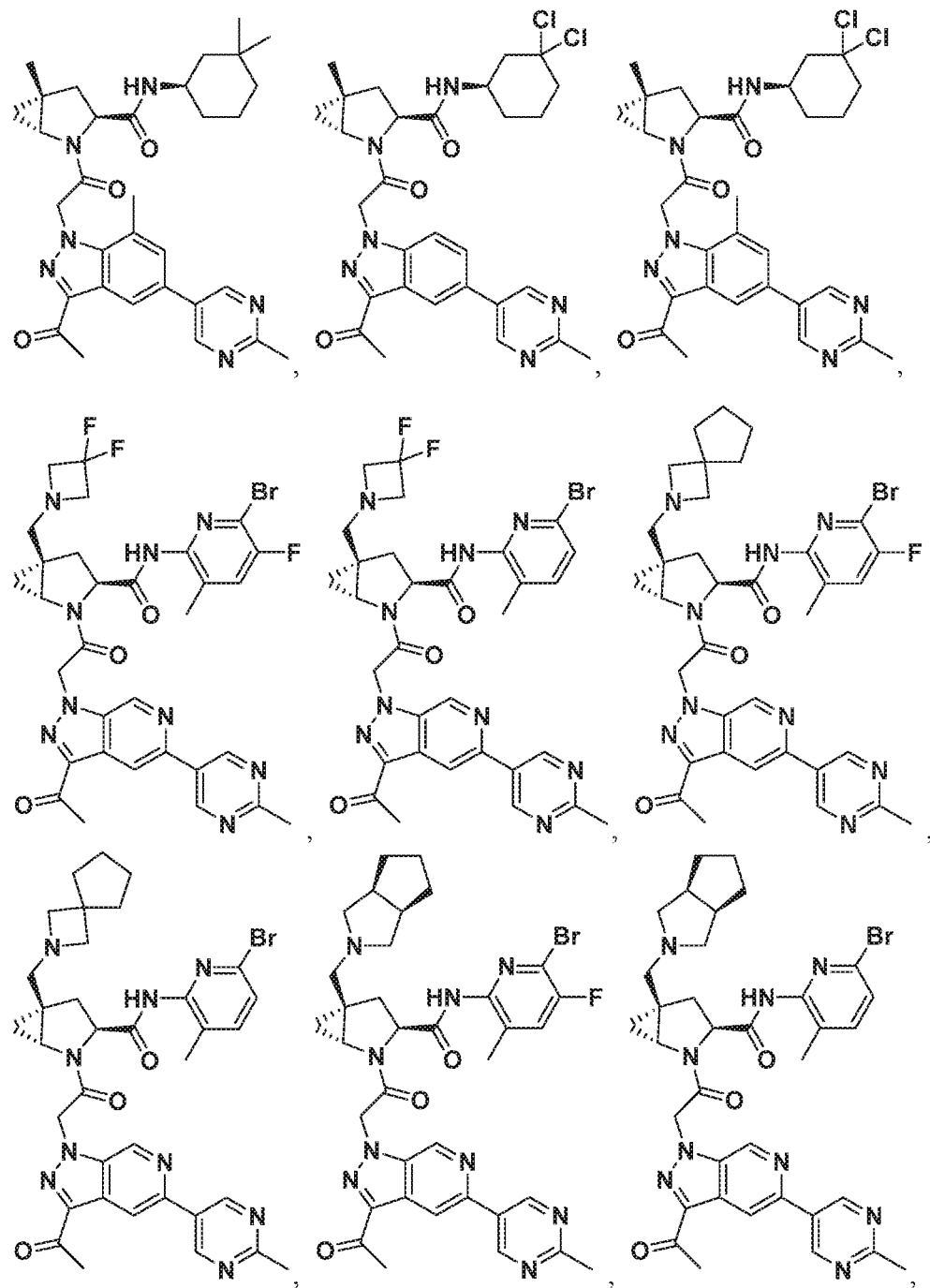
Figure 18F:
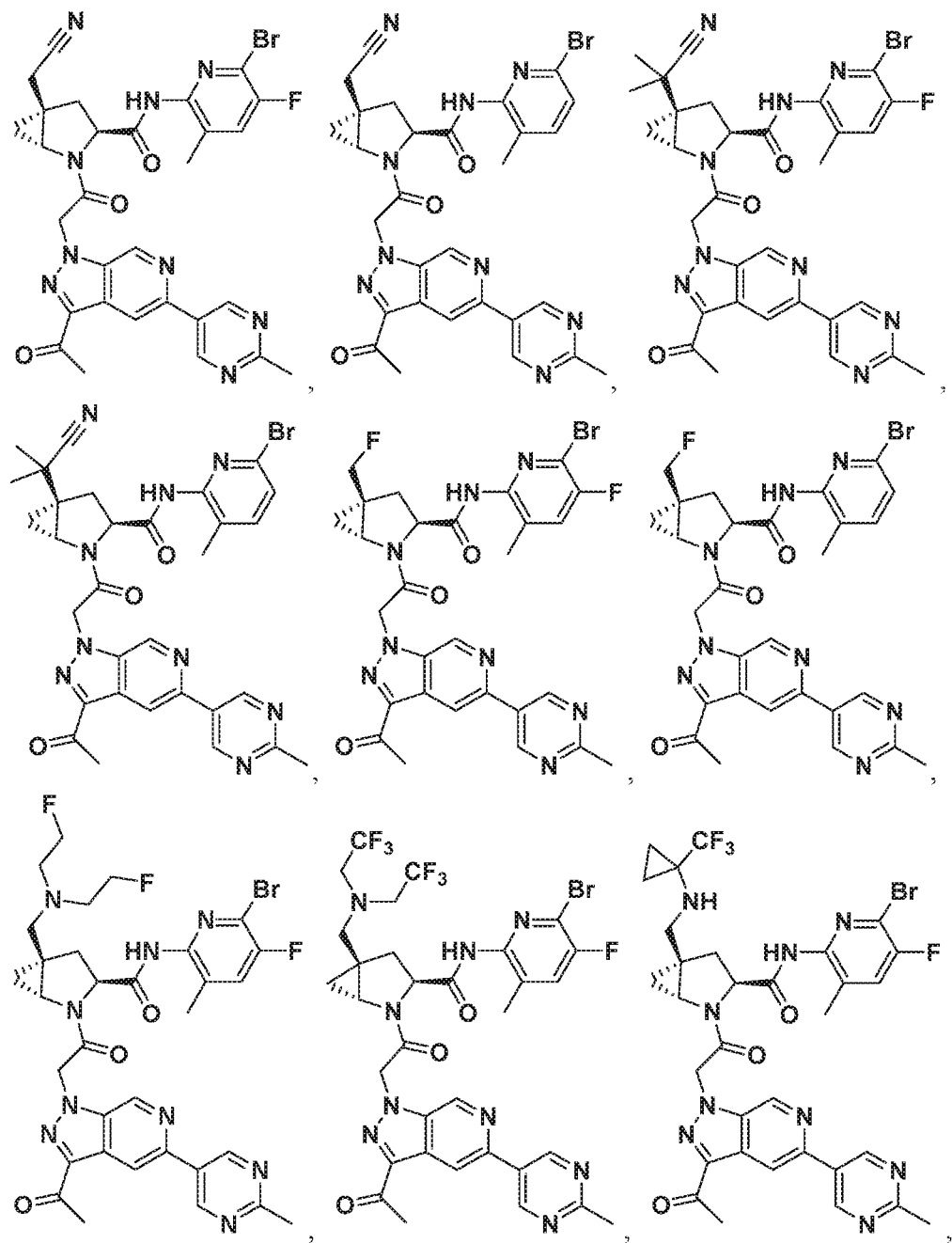
Figure 18G:
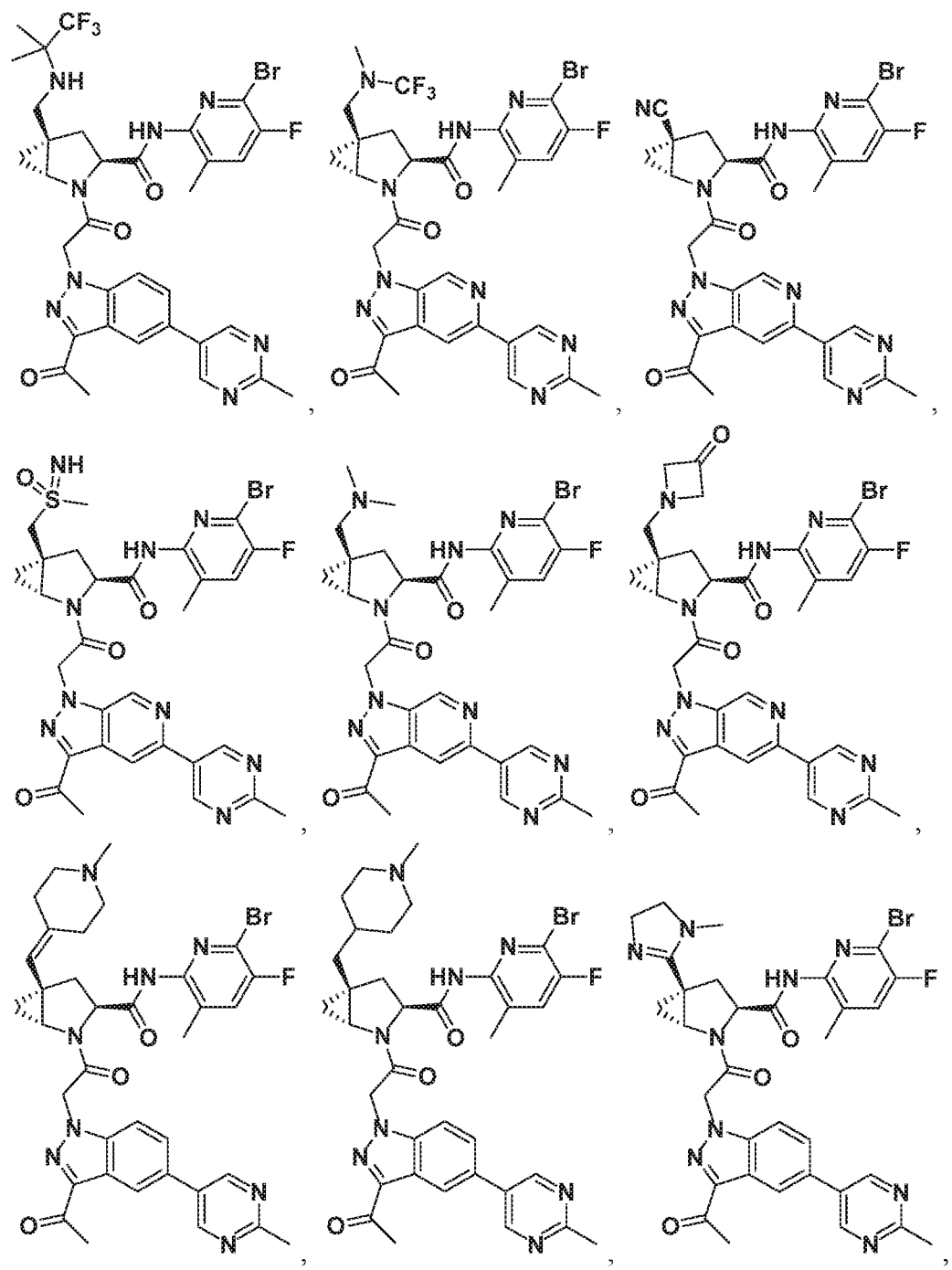
Figure 18H:
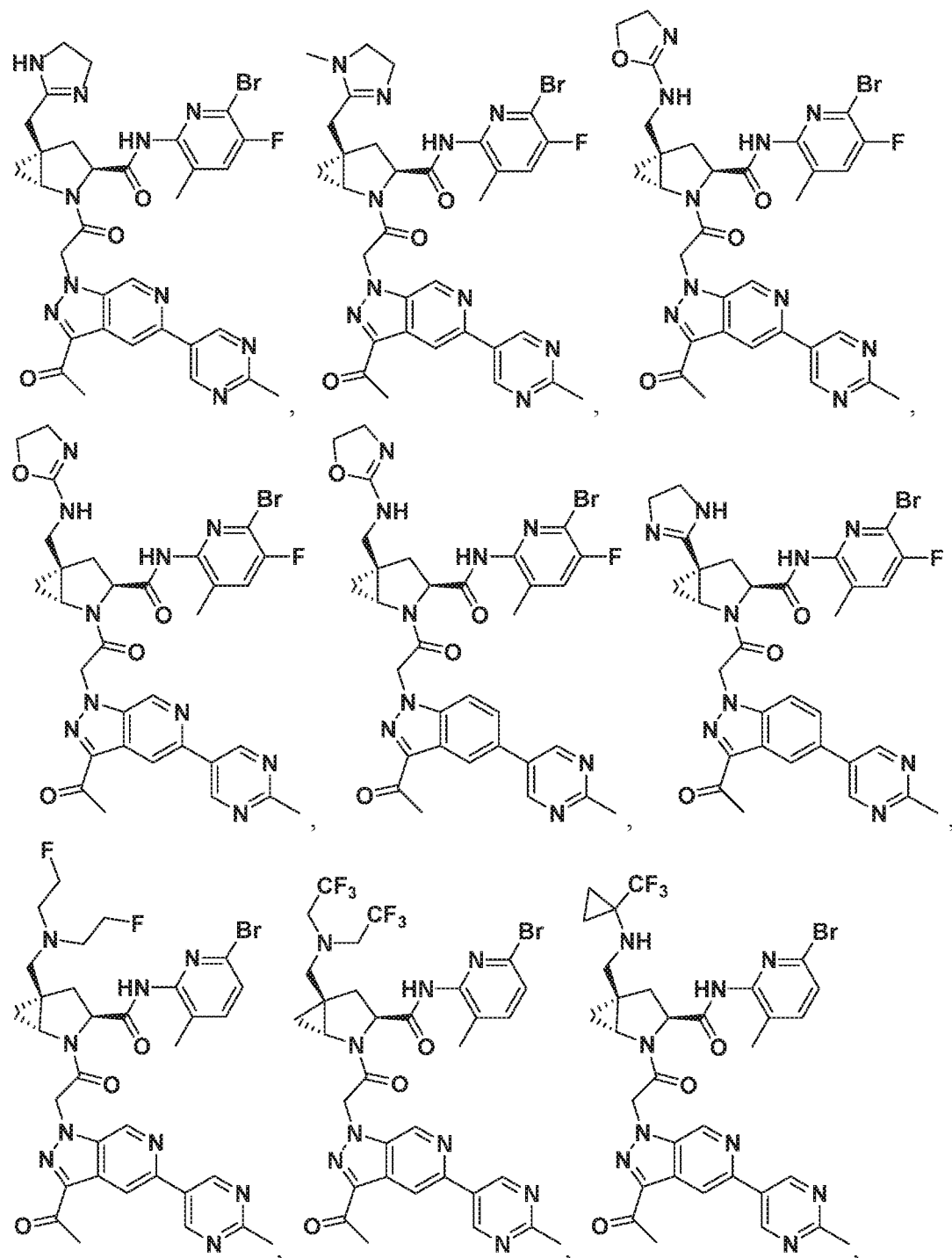
Figure 18I:
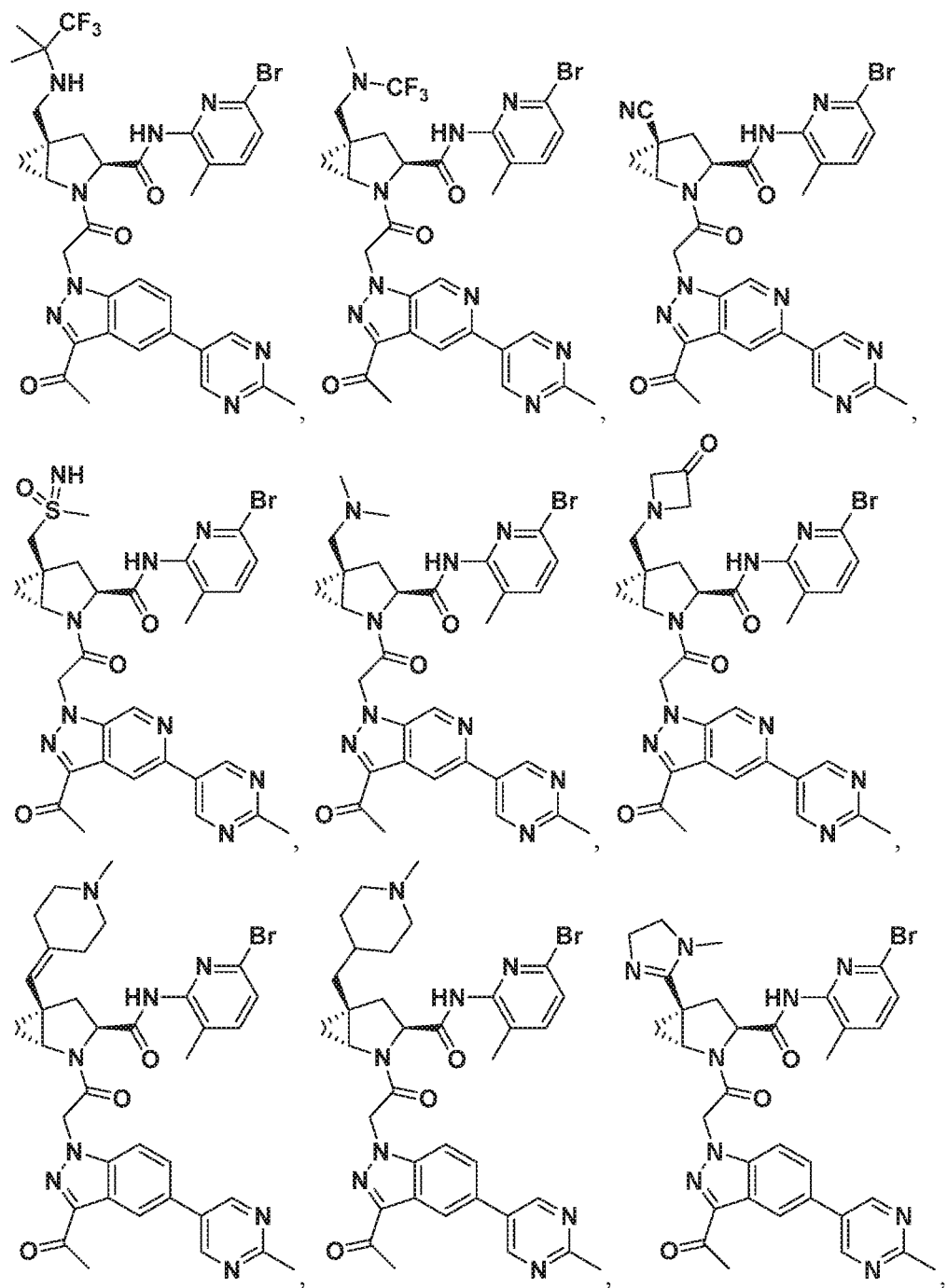
Figure 18J:
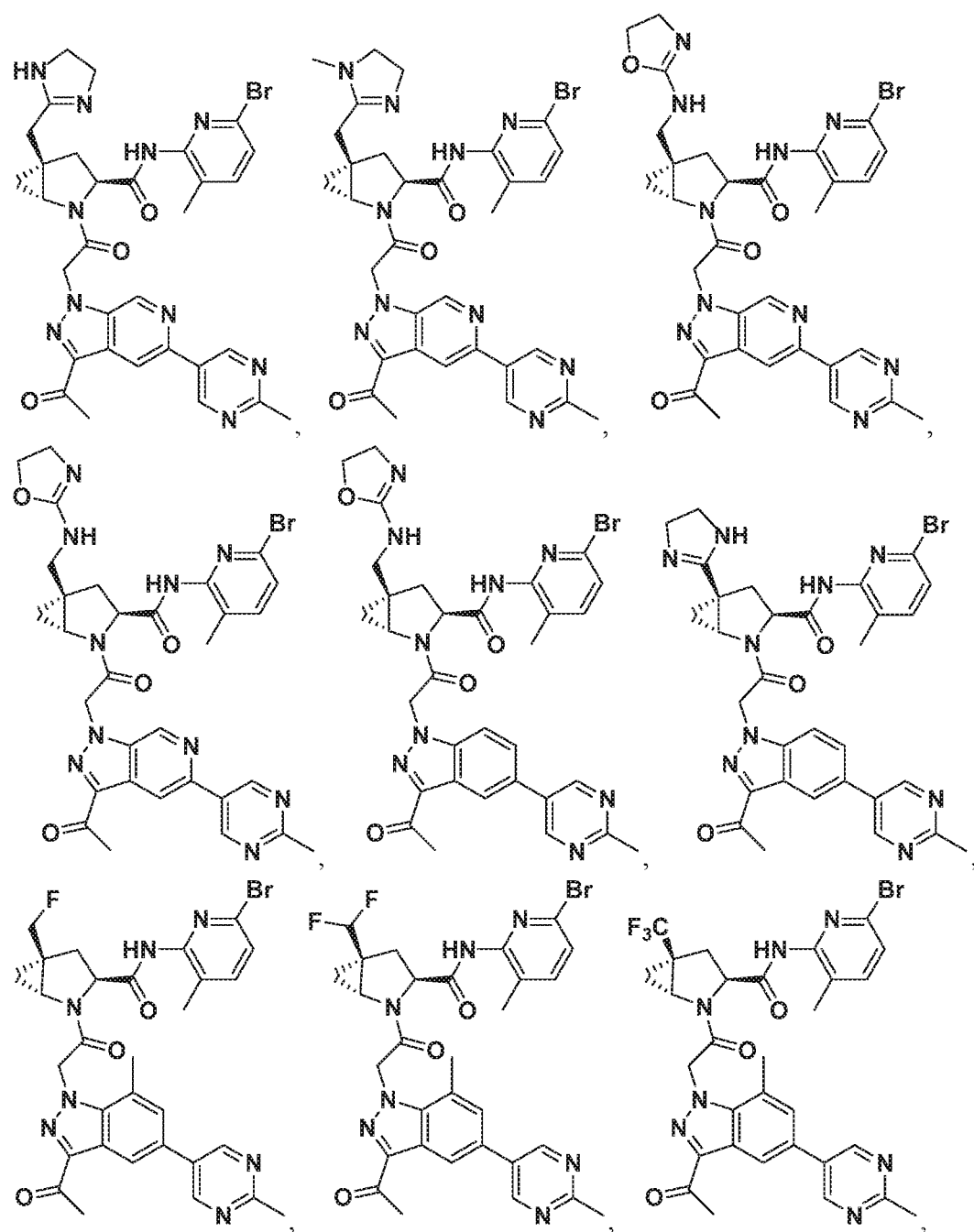
Figure 18K:
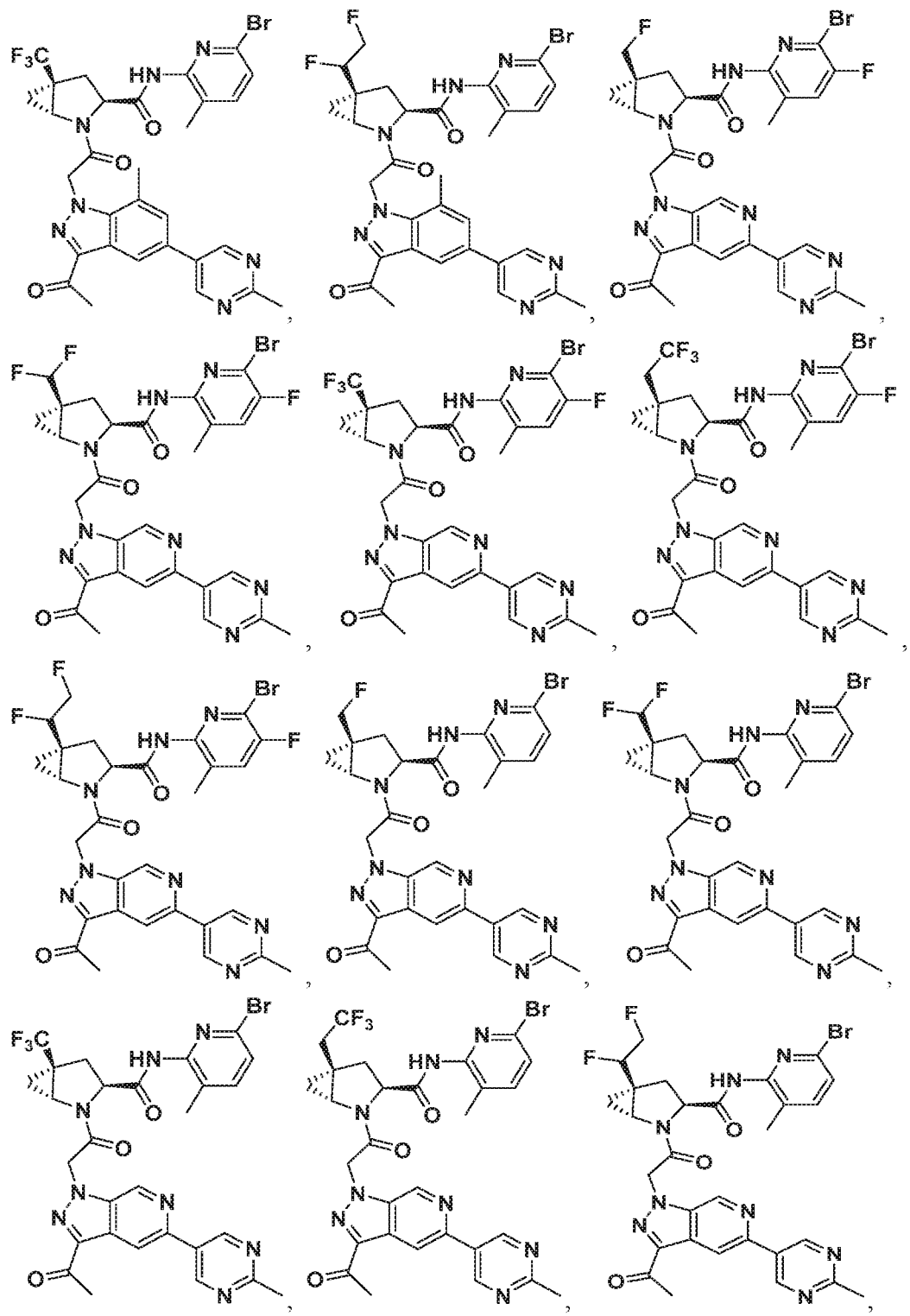
Figure 18L:
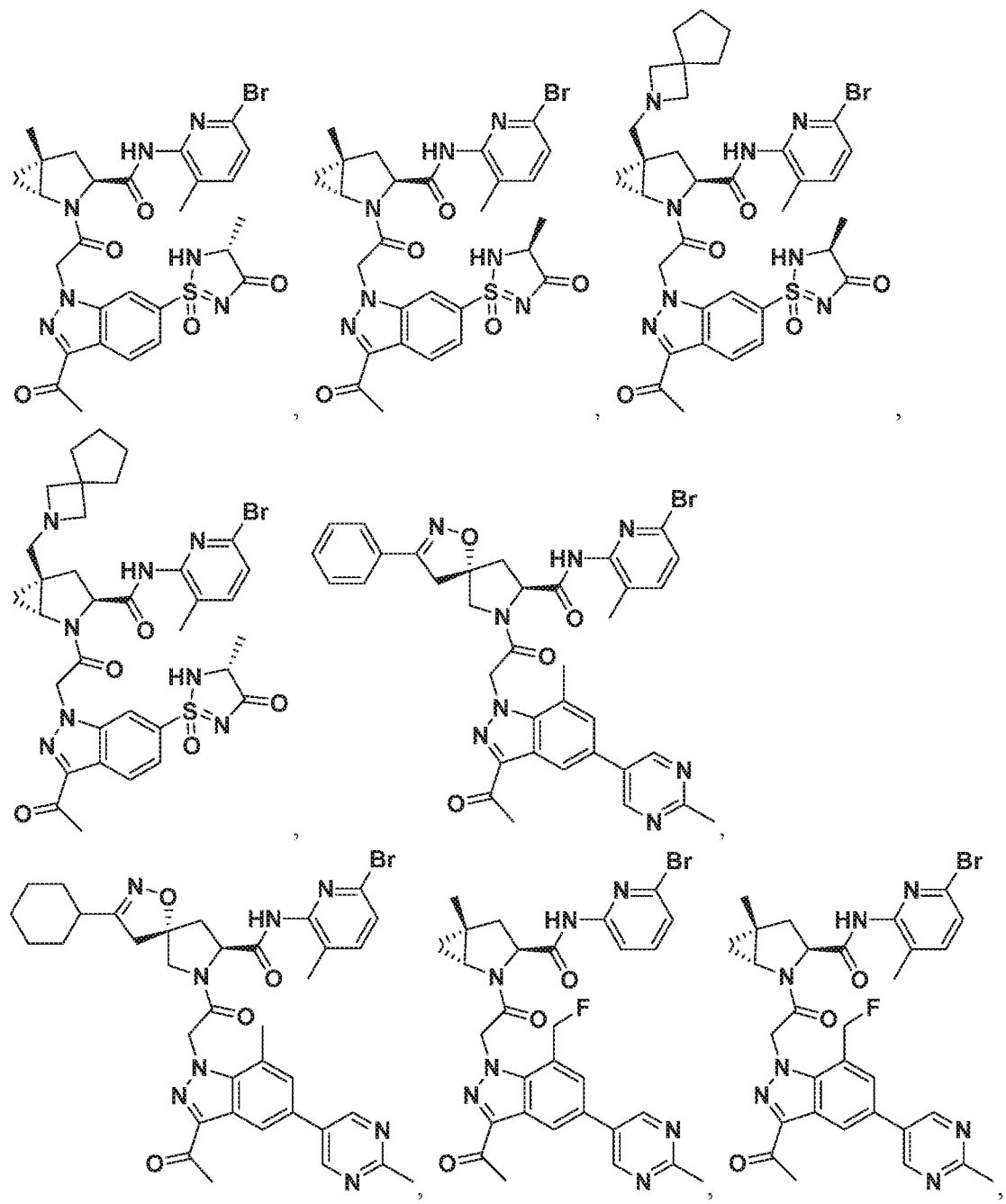
Figure 18M:
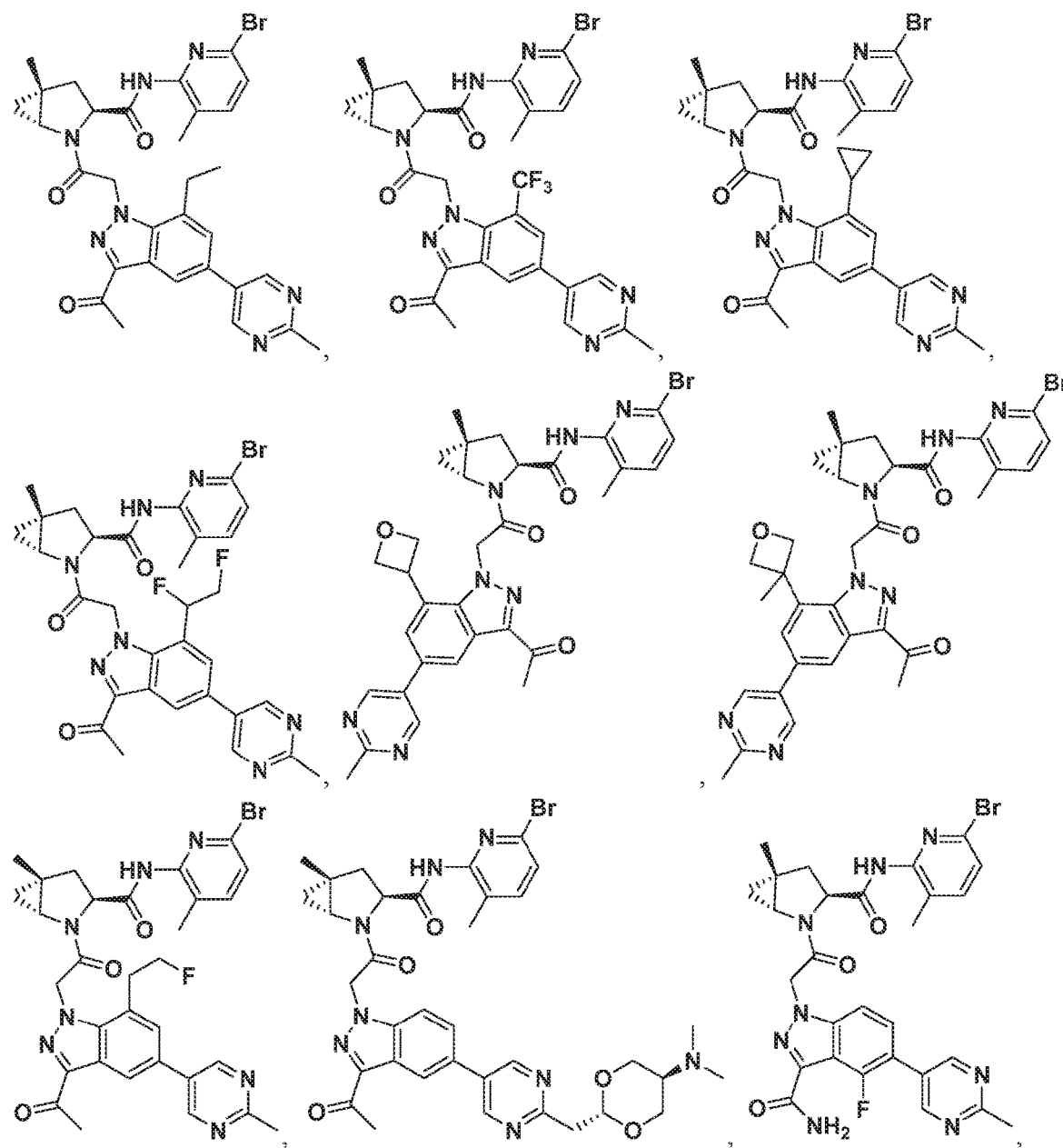
Figure 18N:
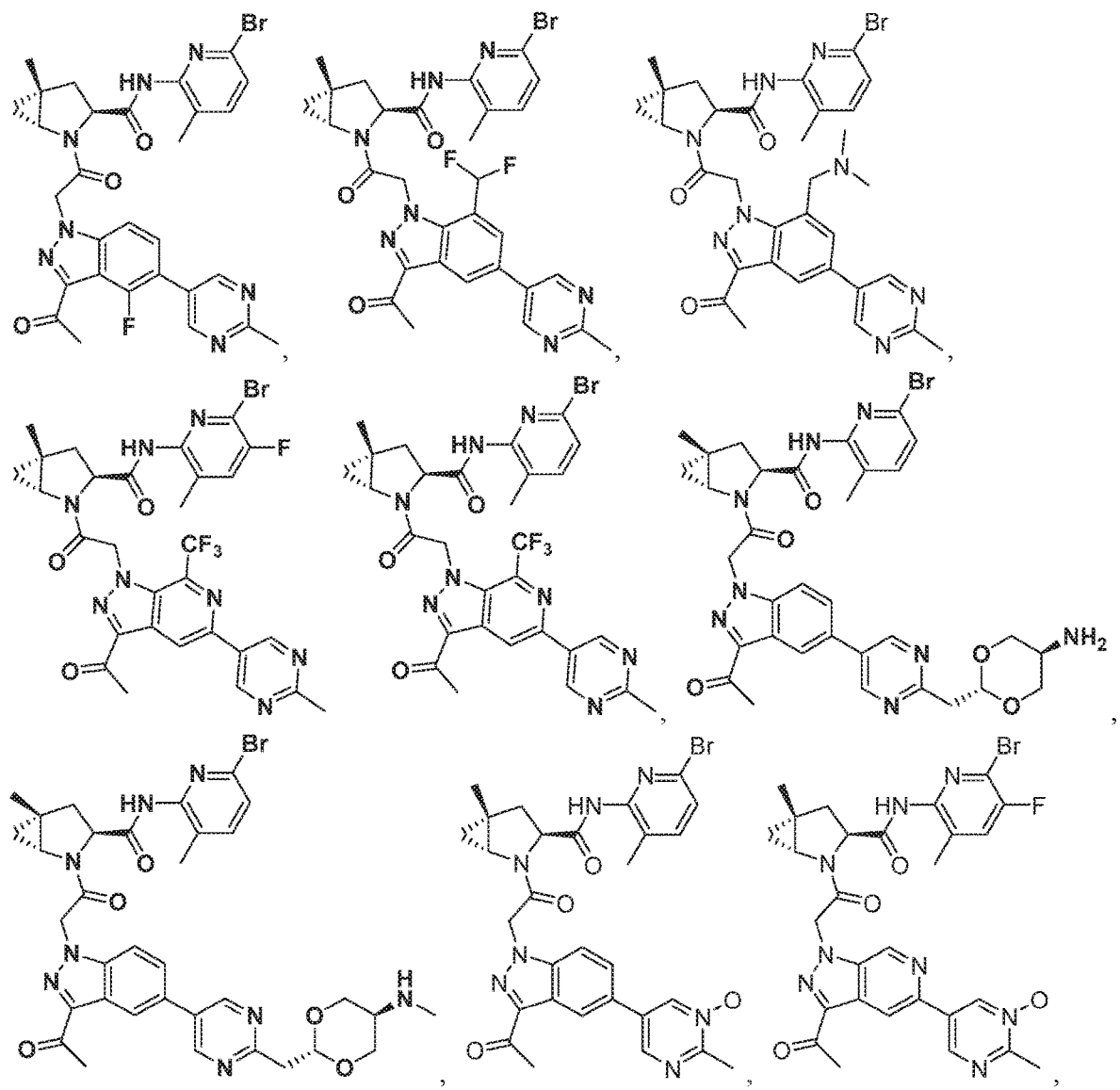
Figure 18O:
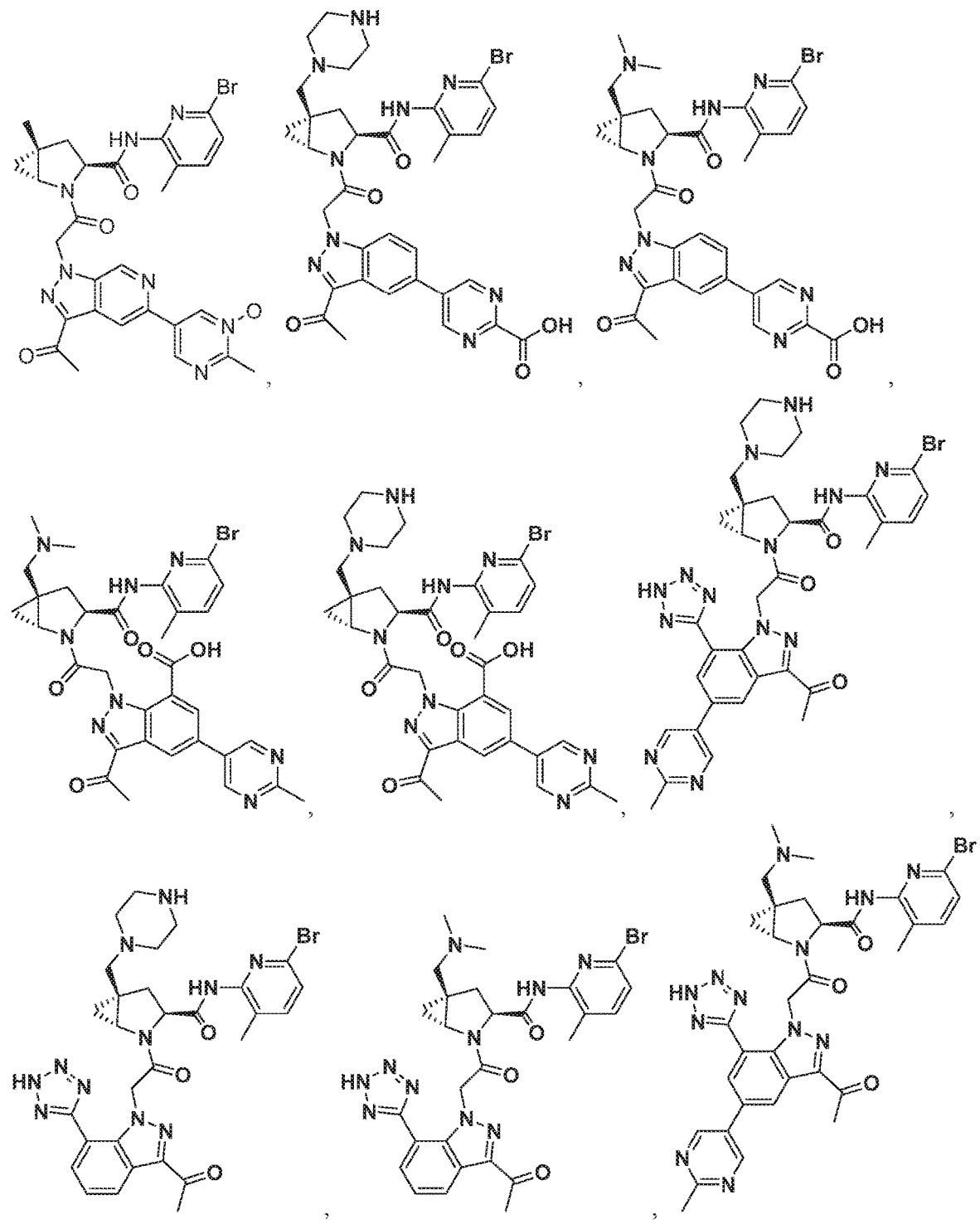
Figure 18P:
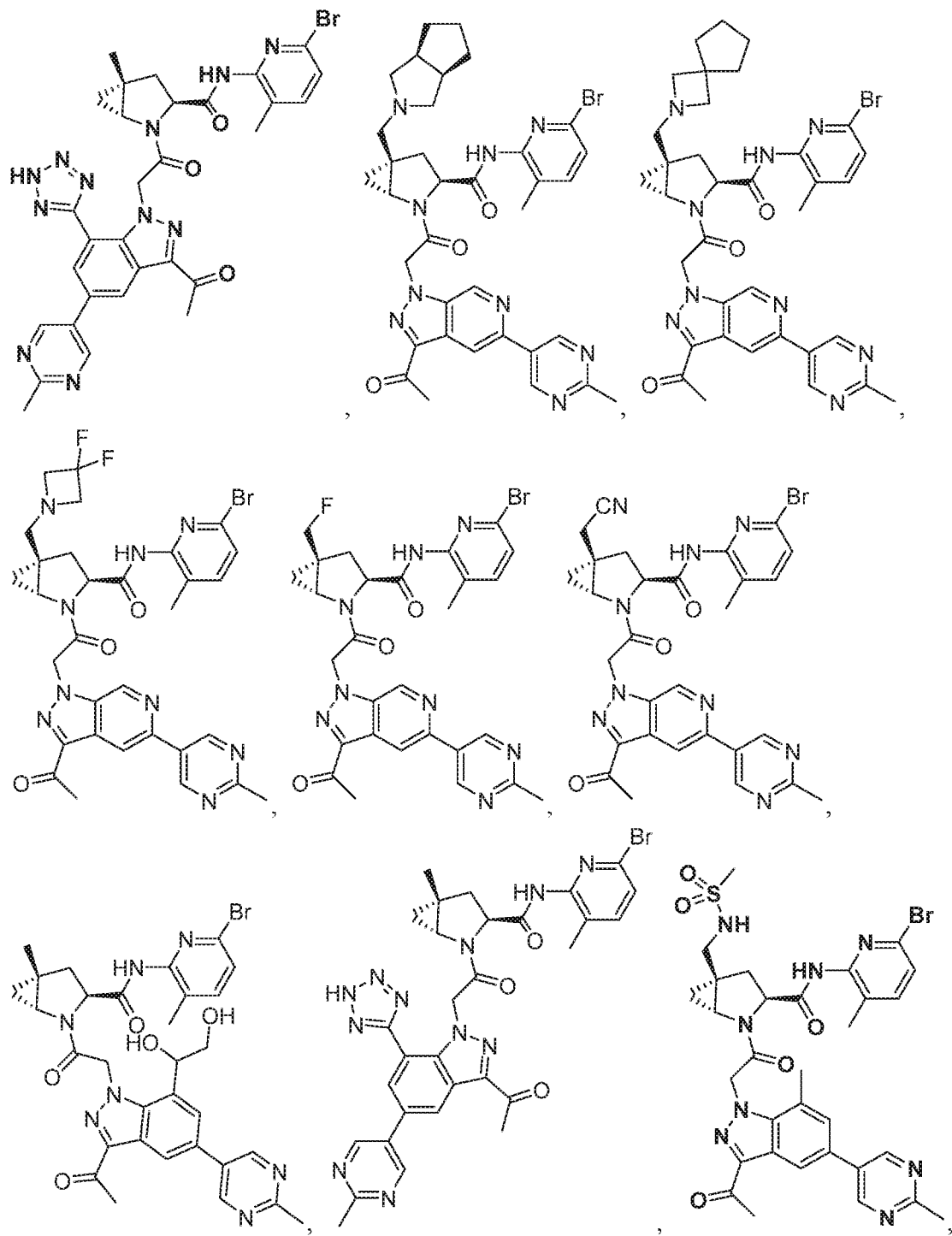
Figure 18Q:
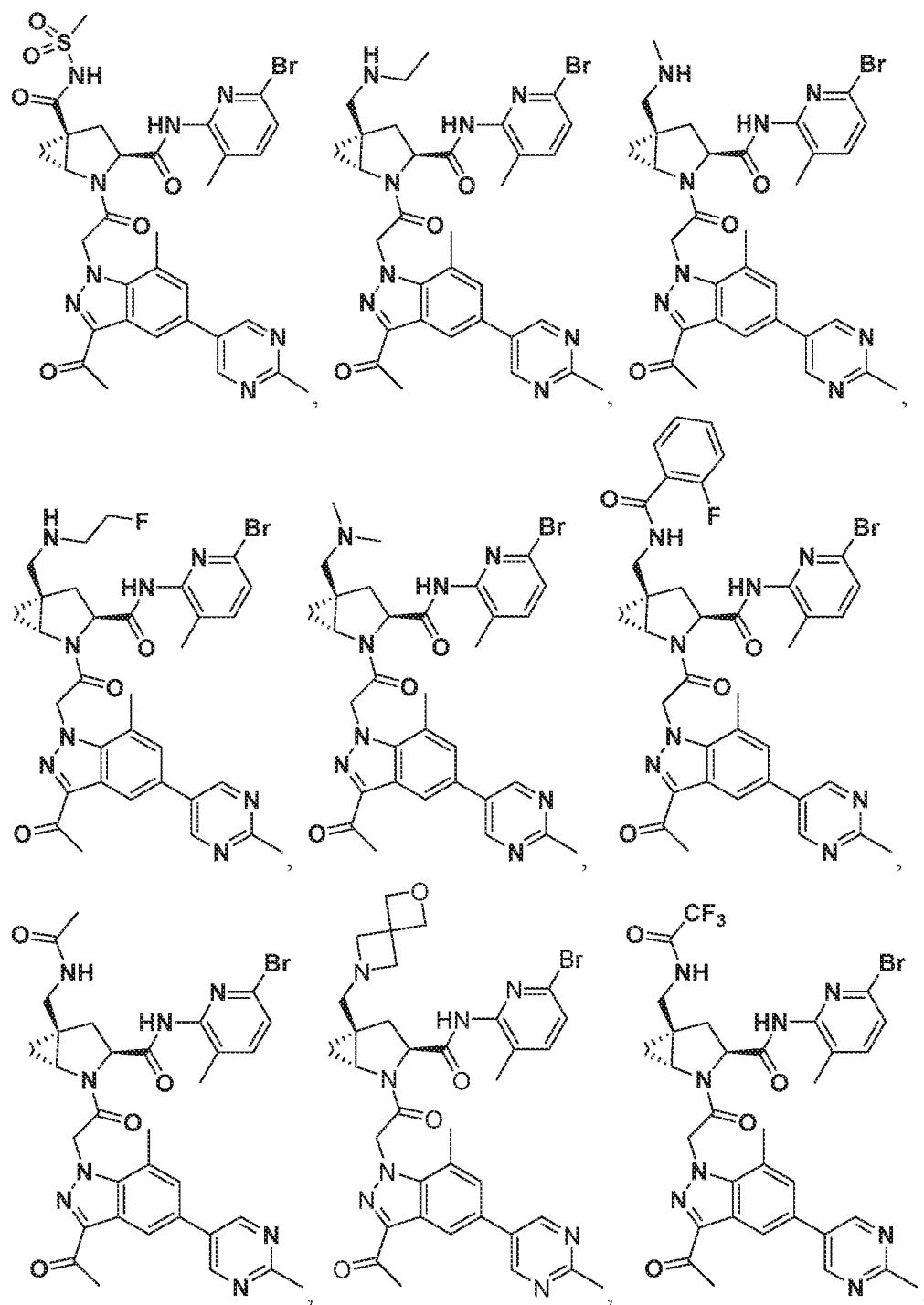
Figure 18R:
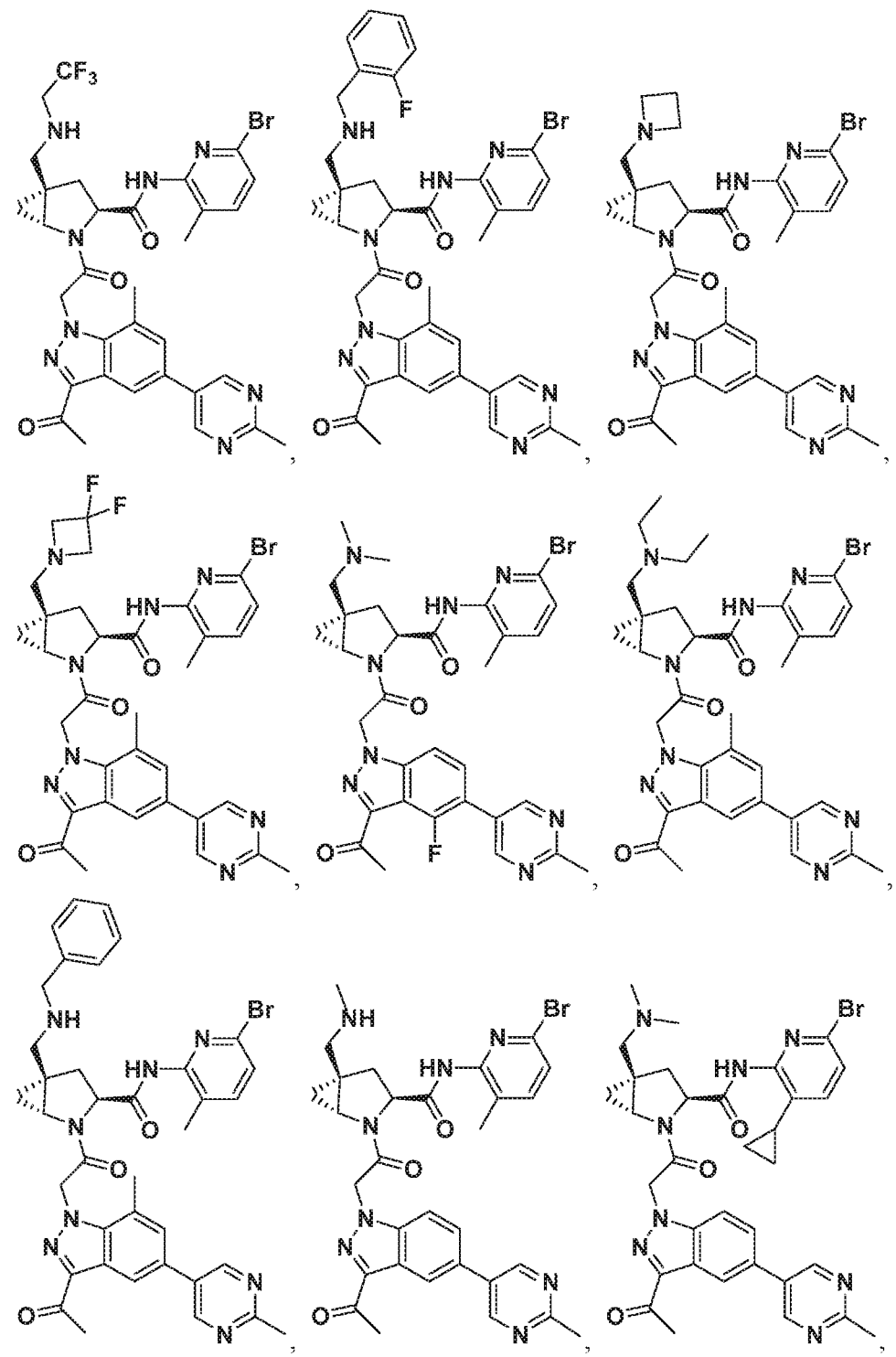
Figure 18S:
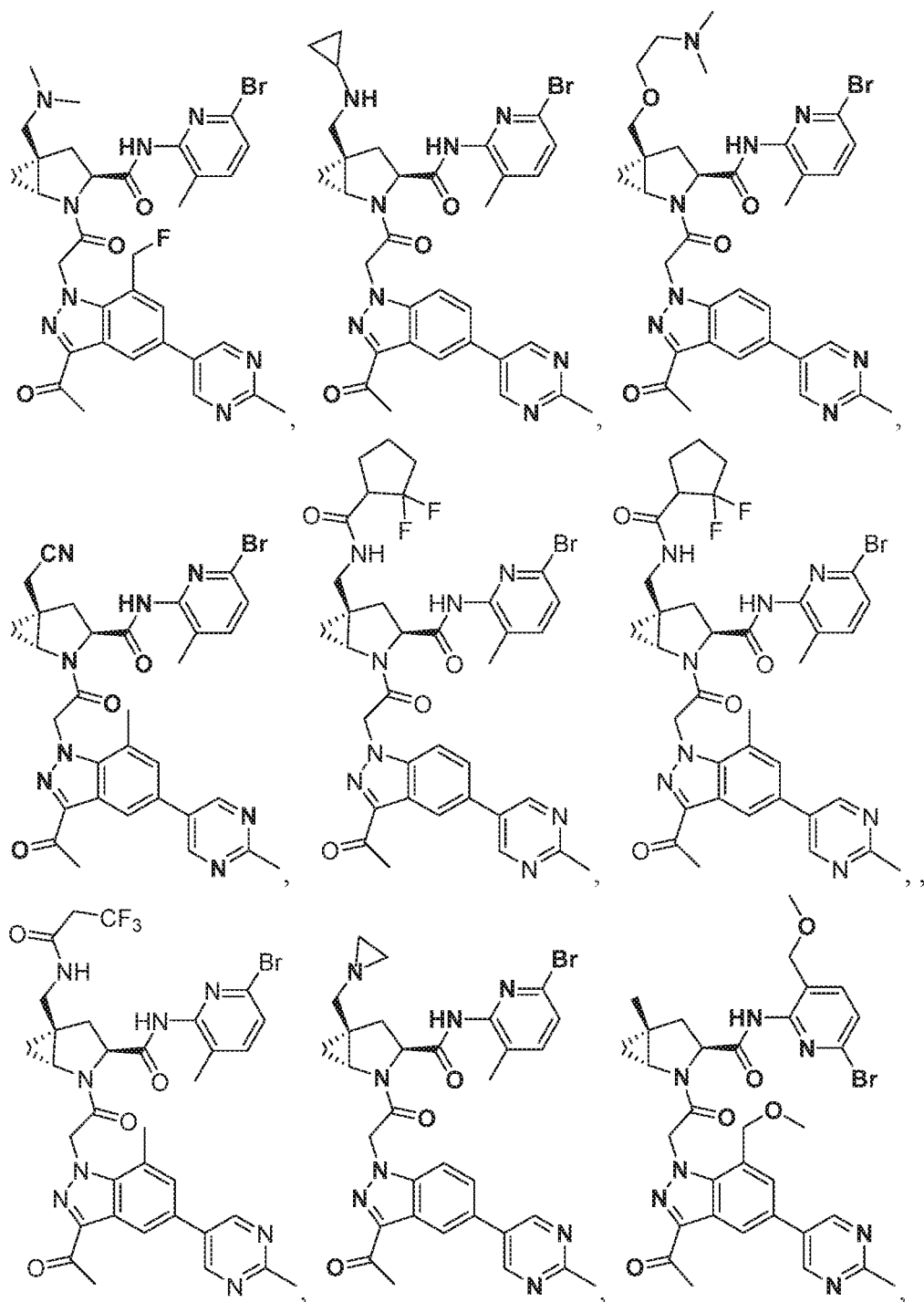
Figure 18T:
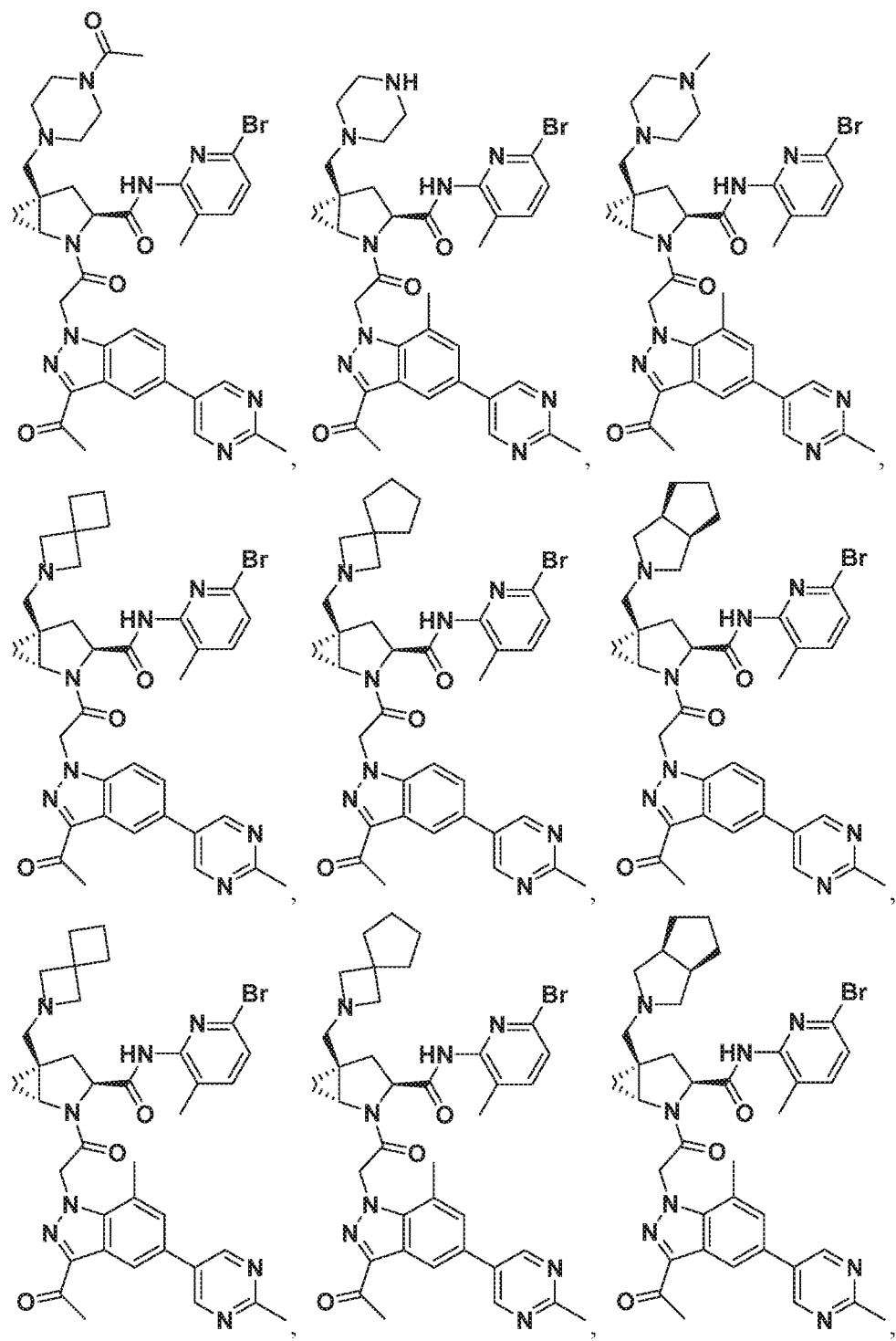
Figure 18U:
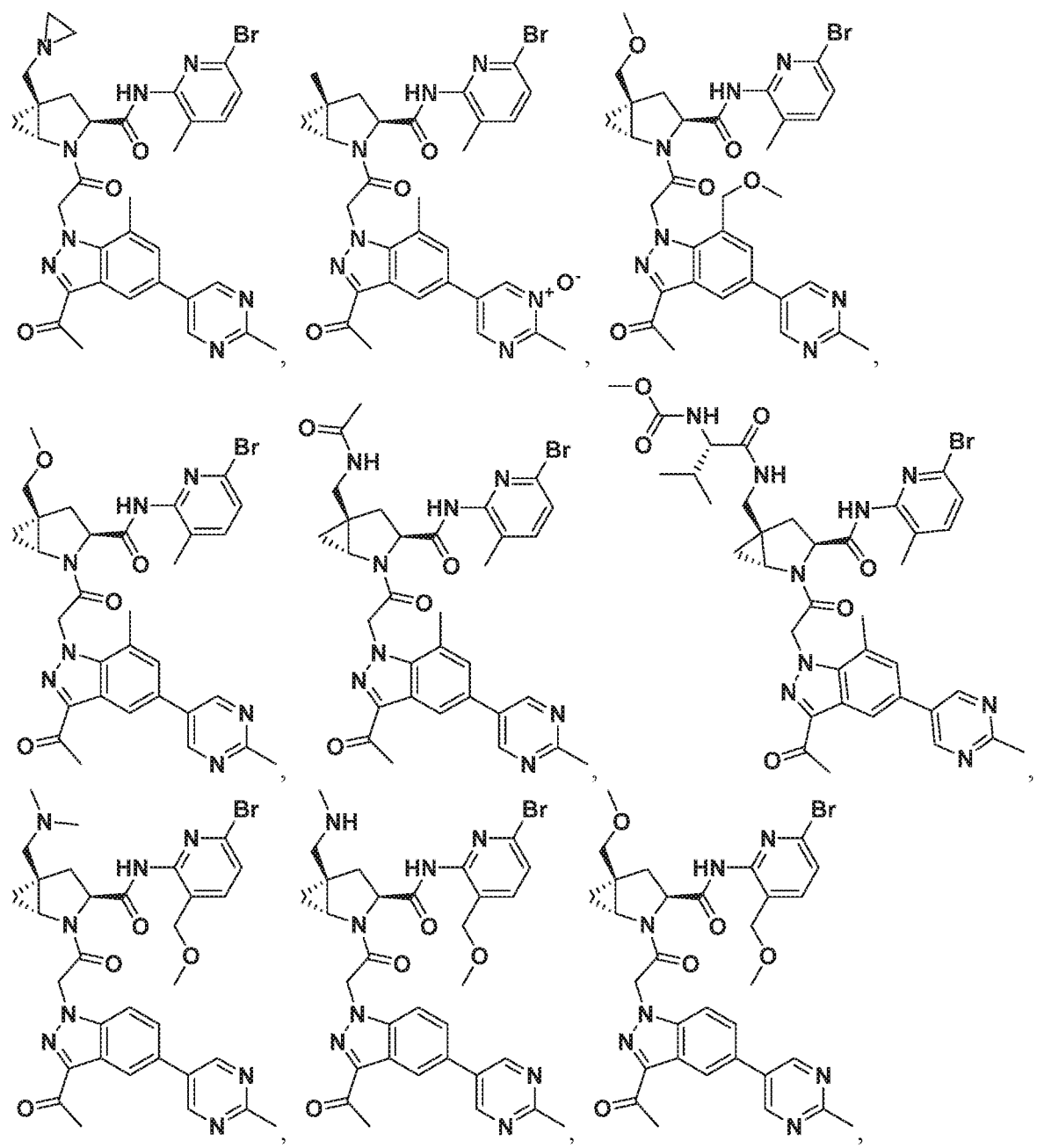
Figure 18V:
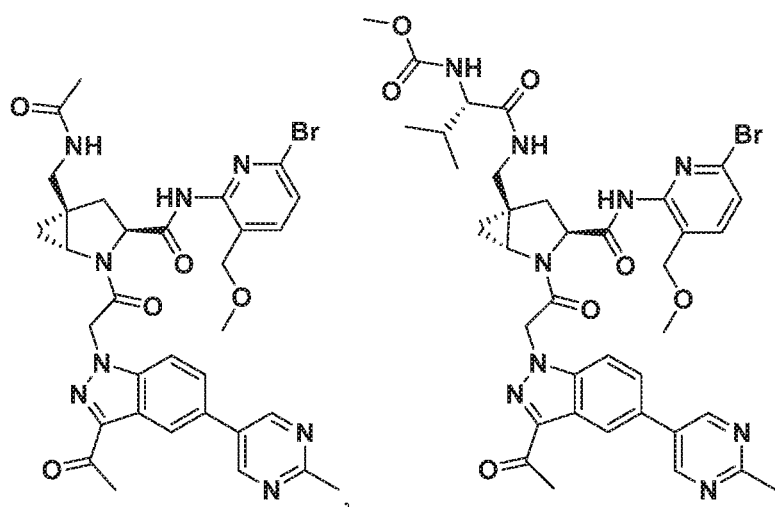
Figure 19:
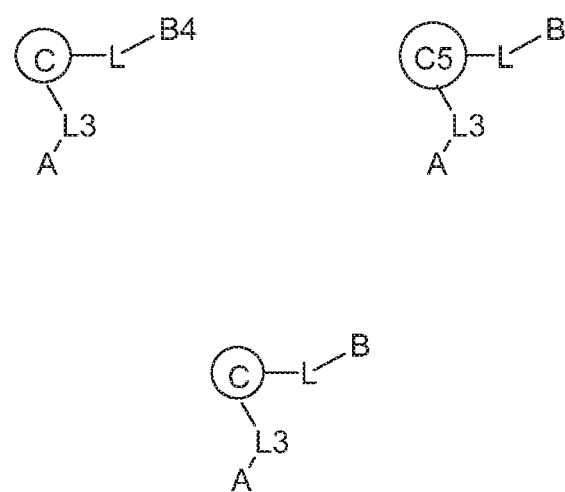
FIG. 19 depicts Formula I, Formula II, and Formula III.

Compounds are described using standard nomenclature. Unless defined otherwise, all technical and scientific terms used herein have the same meaning as is commonly understood by one of skill in the art to which this invention belongs.

The compounds in any of the Formulas described herein include enantiomers, mixtures of enantiomers, diastereomers, tautomers, racemates and other isomers, such as rotamers, as if each is specifically described, unless otherwise indicated or otherwise excluded by context.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

The present invention includes compounds of Formula I, Formula II, Formula III, Formula IV, or Formula V with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. In one embodiment, isotopically labelled compounds can be used in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2H$) and tritium ($^3H$) may optionally be used anywhere in described structures that achieves the desired result. Alternatively or in addition, isotopes of carbon, e.g., $^{13}C$ and $^{14}C$, may be used. In one embodiment, the isotopic substitution is replacing hydrogen with a deuterium at one or more locations on the molecule to improve the performance of the drug, for example, the pharmacodynamics, pharmacokinetics, biodistribution, half-life, stability, AUC, Tmax, Cmax, etc. For example, the deuterium can be bound to carbon in a location of bond breakage during metabolism (an α-deuterium kinetic isotope effect) or next to or near the site of bond breakage (a β-deuterium kinetic isotope effect).

Isotopic substitutions, for example deuterium substitutions, can be partial or complete. Partial deuterium substitution means that at least one hydrogen is substituted with deuterium. In certain embodiments, the isotope is 80, 85, 90, 95 or 99% or more enriched in an isotope at any location of interest. In one embodiments deuterium is 80, 85, 90, 95 or 99% enriched at a desired location. Unless otherwise stated, the enrichment at any point is above natural abundance. And in an embodiment is enough to alter a detectable property of the drug in a human.

In one embodiment, the substitution of a hydrogen atom for a deuterium atom can be provided in any of A1, A1', A2, B1, B1', B2, B3, B4, C1, C1', C2, C3, C4, L1, L1', L2, L2', L4 or L5. In one embodiment, the substitution of a hydrogen atom for a deuterium atom occurs within any R group. In one embodiment the R group is selected from any of $R^1$, $R^{1'}$, $R^2$, $R^{2'}$, $R^3$, $R^{3'}$, $R^4$, $R^{4'}$, $R^5$, $R^6$, $R^{6'}$, $R^7$, $R^8$, $R^{8'}$, $R^9$, $R^{10}$, $R^{11}$, $R^{12}$, $R^{13}$, $R^{14}$, $R^{15}$, $R^{16}$, $R^{17}$, $R^{18}$, $R^{18'}$, $R^{19}$, $R^{21}$, $R^{22}$, $R^{23}$, $R^{25}$, $R^{26}$, $R^{27}$, $R^{28}$, $R^{30}$, $R^{31}$, $R^{32}$, $R^{33}$, $R^{34}$, $R^{35}$, $R^{36}$, $R^{40}$, $R^{41}$, $R^{42}$, $R^{43}$, $R^{44}$, $R^{44'}$, $R^{45}$, $R^{45'}$, $R^{46}$, $R^{46'}$, $R^{47}$, $R^{48}$, $R^{48a}$, $R^{49}$, $R^{50}$, $R^{51}$, $R^{52}$, $R^{53}$, $R^{54}$, $R^{103}$, $R^{104}$, $R^{201}$, $R^{202}$, and $R^{301}$. For example, when any of R groups are, or contain for example through substitution, methyl, ethyl, or methoxy, the alkyl residue may be deuterated (in nonlimiting embodiments, $CD_3$, $CH_2CD_3$, $CD_2CD_3$, $CDH_2$, $CD_2H$, $CD_3$, $CHDCH_2D$, $CH_2CD_3$, $CHDCHD_2$, $OCDH_2$, $OCD_2H$, or $OCD_3$ etc.). In certain other embodiments, an R group has a "'" or an "a" designation, which in one embodiment can be deuterated. In certain other embodiments, when two substituents of the central core ring are combined to form a cyclopropyl ring, the unsubstituted methylene carbon may be deuterated.

The compound of the present invention may form a solvate with solvents (including water). Therefore, in one embodiment, the invention includes a solvated form of the active compound. The term "solvate" refers to a molecular complex of a compound of the present invention (including a salt thereof) with one or more solvent molecules. Non-limiting examples of solvents are water, ethanol, dimethyl sulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO. A solvate can be in a liquid or solid form.

A dash ("-") that is not between two letters or symbols is used to indicate a point of attachment for a substituent. For example, —(C=O)NH$_2$ is attached through carbon of the keto (C=O) group.

The term "substituted", as used herein, means that any one or more hydrogens on the designated atom or group is replaced with a moiety selected from the indicated group, provided that the designated atom's normal valence is not exceeded and the resulting compound is stable. For example, when the substituent is oxo (i.e., =O) then two hydrogens on the atom are replaced. For example a pyridyl group substituted by oxo is a pyridone. Combinations of substituents and/or variables are permissible only if such combinations result in stable compounds or useful synthetic intermediates.

A stable active compound refers to a compound that can be isolated and can be formulated into a dosage form with a shelf life of at least one month. A stable manufacturing intermediate or precursor to an active compound is stable if it does not degrade within the period needed for reaction or other use. A stable moiety or substituent group is one that does not degrade, react or fall apart within the period necessary for use. Nonlimiting examples of unstable moieties are those that combine heteroatoms in an unstable arrangement, as typically known and identifiable to those of skill in the art.

Any suitable group may be present on a "substituted" or "optionally substituted" position that forms a stable molecule and meets the desired purpose of the invention and includes, but is not limited to, e.g., halogen (which can independently be F, Cl, Br or I); cyano; hydroxyl; nitro; azido; alkanoyl (such as a $C_2$-$C_6$ alkanoyl group); carboxamide; alkyl, cycloalkyl, alkenyl, alkynyl, alkoxy, aryloxy such as phenoxy; thioalkyl including those having one or more thioether linkages; alkylsulfinyl; alkylsulfonyl groups including those having one or more sulfonyl linkages; aminoalkyl groups including groups having more than one N atoms; aryl (e.g., phenyl, biphenyl, naphthyl, or the like, each ring either substituted or unsubstituted); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated or partially unsaturated heterocycle having 1 to 3 separate or fused rings with one or more N, O or S atoms, or a heteroaryl having 1 to 3 separate or fused rings with one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such groups may be further substituted, e.g. with hydroxy, alkyl, alkoxy, halogen and amino. In certain embodiments "optionally substituted" includes one or more substituents independently selected from halogen, hydroxyl, amino, cyano, —CHO, —COOH, —CONH$_2$, alkyl including $C_1$-$C_6$alkyl, alkenyl including $C_2$-$C_6$alkenyl, alkynyl including $C_2$-$C_6$alkynyl, —$C_1$-$C_6$alkoxy, alkanoyl including $C_2$-$C_6$alkanoyl, $C_1$-$C_6$alkylester, (mono- and di-$C_1$-$C_6$alkylamino)$C_0$-$C_2$alkyl, haloalkyl including $C_1$-$C_6$haloalkyl, hydroxy$C_1$-$C_6$alkyl, ester, carbamate, urea, sulfonamide, —$C_1$-$C_6$alkyl(heterocyclo), $C_1$-$C_6$alkyl(heteroaryl), —$C_1$-$C_6$alkyl($C_3$-$C_7$cycloalkyl), O—$C_1$-$C_6$alkyl ($C_3$-$C_7$cycloalkyl), B(OH)$_2$, phosphate, phosphonate and haloalkoxy including $C_1$-$C_6$haloalkoxy.

"Alkyl" is a branched or straight chain saturated aliphatic hydrocarbon group. In one embodiment, the alkyl contains from 1 to about 12 carbon atoms, more generally from 1 to about 6 carbon atoms or from 1 to about 4 carbon atoms. In one embodiment, the alkyl contains from 1 to about 8 carbon atoms. In certain embodiments, the alkyl is $C_1$-$C_2$, $C_1$-$C_3$, $C_1$-$C_4$, $C_1$-$C_5$ or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$alkyl as used herein indicates a straight or branched alkyl group having from 1, 2, 3, or 4 carbon atoms and is intended to mean that each of these is described as an independent species. When $C_0$-$C_n$ alkyl is used herein in conjunction with another group, for example, ($C_3$-$C_7$cycloalkyl)$C_0$-$C_4$ alkyl, or —$C_0$-$C_4$alkyl($C_3$-$C_7$cycloalkyl), the indicated group, in this case cycloalkyl, is either directly bound by a single covalent bond ($C_0$alkyl), or attached by an alkyl chain in this case 1, 2, 3, or 4 carbon atoms. Alkyls can also be attached via other groups such as heteroatoms as in —O—$C_0$-$C_4$alkyl ($C_3$-$C_7$cycloalkyl). Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, 2,3-dimethylbutane, and hexyl. In one embodiment, the alkyl group is optionally substituted as described above. In one embodiment, trimethylsilyl can be used instead of t-butyl.

"Aliphatic" refers to a saturated or unsaturated, straight, branched, or cyclic hydrocarbon. "Aliphatic" is intended herein to include, but is not limited to, alkyl, alkenyl, alkynyl, cycloalkyl, cycloalkenyl, and cycloalkynyl moieties, and thus incorporates each of these definitions. In one embodiment, "aliphatic" is used to indicate those aliphatic groups having 1-20 carbon atoms. The aliphatic chain can be, for example, mono-unsaturated, di-unsaturated, tri-unsaturated, polyunsaturated, or alkynyl. Unsaturated aliphatic groups can be in a cis or trans configuration. In one embodiment, the aliphatic group contains from 1 to about 12 carbon atoms, more generally from 1 to about 6 carbon atoms or from 1 to about 4 carbon atoms. In one embodiment, the aliphatic group contains from 1 to about 8 carbon atoms. In certain embodiments, the aliphatic group is $C_1$-$C_2$, $C_1$-$C_3$, $C_1$-$C_4$, $C_1$-$C_5$ or $C_1$-$C_6$. The specified ranges as used herein indicate an aliphatic group having each member of the range described as an independent species. For example, the term $C_1$-$C_6$ aliphatic as used herein indicates a straight or branched alkyl, alkenyl, or alkynyl group having from 1, 2, 3, 4, 5, or 6 carbon atoms and is intended to mean that each of these is described as an independent species. For example, the term $C_1$-$C_4$ aliphatic as used herein indicates a straight or branched alkyl, alkenyl, or alkynyl group having from 1, 2, 3, or 4 carbon atoms and is intended to mean that each of these is described as an independent species. In one embodiment, the aliphatic group is substituted with one or more functional groups that results in the formation of a stable moiety.

The term "heteroaliphatic" refers to an aliphatic moiety that contains at least one heteroatom in the chain, for example, an amine, carbonyl, carboxy, oxo, thio, phosphate, phosphonate, nitrogen, phosphorus, silicon, or boron atoms in place of a carbon atom. In one embodiment, the only heteroatom is nitrogen. In one embodiment, the only heteroatom is oxygen. In one embodiment, the only heteroatom is sulfur. "Heteroaliphatic" is intended herein to include, but is not limited to, heteroalkyl, heteroalkenyl, heteroalkynyl, heterocycloalkyl, heterocycloalkenyl, and heterocycloalkynyl moieties. In one embodiment, "heteroaliphatic" is used to indicate a heteroaliphatic group (cyclic, acyclic, substituted, unsubstituted, branched or unbranched) having 1-20 carbon atoms. In one embodiment, the heteroaliphatic group is optionally substituted in a manner that results in the formation of a stable moiety. Nonlimiting examples of heteroaliphatic moieties are polyethylene glycol, polyalkylene glycol, amide, polyamide, polylactide, polyglycolide, thioether, ether, alkyl-heterocycle-alkyl, —O-alkyl-O-alkyl, alkyl-O-haloalkyl, etc.

In one embodiment, when a term is used that includes "alk" it should be understood that "cycloalkyl" or "carbocyclic" can be considered part of the definition, unless unambiguously excluded by the context. For example and without limitation, the terms alkyl, alkenyl, alkynyl, alkoxy, alkanoyl, alkenyloxy, haloalkyl, aminoalkyl, alkylene, alkenylene, alkynylene, etc. can all be considered to include the cyclic forms of alkyl, unless unambiguously excluded by context.

"Alkenyl" is a branched or straight chain aliphatic hydrocarbon group having one or more carbon-carbon double bonds that may occur at a stable point along the chain. Nonlimiting examples are $C_2$-$C_8$alkenyl, $C_2$-$C_7$alkenyl, $C_2$-$C_6$alkenyl, $C_2$-$C_5$alkenyl and $C_2$-$C_4$alkenyl. The specified ranges as used herein indicate an alkenyl group having each member of the range described as an independent species, as described above for the alkyl moiety. Examples of alkenyl include, but are not limited to, ethenyl and propenyl. In one embodiment, the alkenyl group is optionally substituted as described above.

"Alkynyl" is a branched or straight chain aliphatic hydrocarbon group having one or more carbon-carbon triple bonds that may occur at any stable point along the chain, for example, $C_2$-$C_8$alkynyl or $C_2$-$C_6$alkynyl. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In one embodiment, the alkynyl group is optionally substituted as described above.

"Alkylene" is a bivalent saturated hydrocarbon. Alkylenes, for example, can be a 1, 2, 3, 4, 5, 6, 7 to 8 carbon moiety, 1 to 6 carbon moiety, or an indicated number of carbon atoms, for example $C_1$-$C_2$alkylene, $C_1$-$C_3$alkylene, $C_1$-$C_4$alkylene, $C_1$-$C_5$alkylene, or $C_1$-$C_6$alkylene.

"Alkenylene" is a bivalent hydrocarbon having at least one carbon-carbon double bond. Alkenylenes, for example, can be a 2 to 8 carbon moiety, 2 to 6 carbon moiety, or an indicated number of carbon atoms, for example $C_2$-$C_4$alkenylene.

"Alkynylene" is a bivalent hydrocarbon having at least one carbon-carbon triple bond. Alkynylenes, for example, can be a 2 to 8 carbon moiety, 2 to 6 carbon moiety, or an indicated number of carbon atoms, for example $C_2$-$C_4$alkynylene.

"Alkoxy" is an alkyl group as defined above covalently bound through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "alkylthio" or a "thioalkyl" group is an alkyl group as defined above with the indicated number of carbon atoms covalently bound through a sulfur bridge (—S—). In one embodiment, the alkoxy group is optionally substituted as described above.

"Alkenyloxy" is an alkenyl group as defined covalently bound to the group it substitutes by an oxygen bridge (—O—).

"Alkanoyl" is an alkyl group as defined above covalently bound through a carbonyl (C=O) bridge. The carbonyl carbon is included in the number of carbons, that is $C_2$alkanoyl is a $CH_3(C=O)$— group. In one embodiment, the alkanoyl group is optionally substituted as described above.

"Alkylester" is an alkyl group as defined herein covalently bound through an ester linkage. The ester linkage may be in either orientation, e.g., a group of the formula —O(C=O)alkyl or a group of the formula —(C=O)Oalkyl.

"Amide" or "carboxamide" is —C(O)NR$^a$R$^b$ wherein R$^a$ and R$^b$ are each independently selected from hydrogen, alkyl, for example, alkyl including $C_1$-$C_6$alkyl, alkenyl, for example, $C_2$-$C_6$alkenyl, alkynyl, for example, $C_2$-$C_6$alkynyl, —$C_0$-$C_4$alkyl($C_3$-$C_7$cycloalkyl), —$C_0$-$C_4$alkyl($C_3$-$C_7$heterocycloalkyl), —$C_0$-$C_4$alkyl(aryl), and —$C_0$-$C_4$alkyl(heteroaryl); or together with the nitrogen to which they are bonded, R$^a$ and R$^b$ can form a $C_3$-$C_7$heterocyclic ring. In one embodiment, the R$^a$ and R$^b$ groups are each independently be optionally substituted as described herein.

"Carbocyclic group", "carbocyclic ring", or "cycloalkyl" is a saturated or partially unsaturated (i.e., not aromatic) group containing all carbon ring atoms. A carbocyclic group typically contains 1 ring of 3 to 7 carbon atoms or 2 fused rings each containing 3 to 7 carbon atoms. Cycloalkyl substituents may be pendant from a substituted nitrogen or carbon atom, or a substituted carbon atom that may have two substituents can have a cycloalkyl group, which is attached as a spiro group. Examples of carbocyclic rings include cyclohexenyl, cyclohexyl, cyclopentenyl, cyclopentyl, cyclobutenyl, cyclobutyl and cyclopropyl rings. In one embodiment, the carbocyclic ring is optionally substituted as described above. In one embodiment, the cycloalkyl is a partially unsaturated (i.e., not aromatic) group containing all carbon ring atoms. In another embodiment, the cycloalkyl is a saturated group containing all carbon ring atoms.

"Carbocyclic-oxy group" is a monocyclic carbocyclic ring or a mono- or bi-cyclic carbocyclic group as defined above attached to the group it substitutes via an oxygen, —O—, linker.

"Haloalkyl" indicates both branched and straight-chain alkyl groups substituted with 1 or more halogen atoms, up to the maximum allowable number of halogen atoms. Examples of haloalkyl include, but are not limited to, trifluoromethyl, monofluoromethyl, difluoromethyl, 2-fluoroethyl, and penta-fluoroethyl.

"Haloalkoxy" indicates a haloalkyl group as defined herein attached through an oxygen bridge (oxygen of an alcohol radical).

"Hydroxyalkyl" is an alkyl group as previously described, substituted with at least one hydroxyl substituent.

"Aminoalkyl" is an alkyl group as previously described, substituted with at least one amino substituent.

"Halo" or "halogen" indicates independently, any of fluoro, chloro, bromo or iodo.

"Aryl" indicates an aromatic group containing only carbon in the aromatic ring or rings. In one embodiment, the aryl group contains 1 to 3 separate or fused rings and is 6 to about 14 or 18 ring atoms, without heteroatoms as ring members. When indicated, such aryl groups may be further substituted with carbon or non-carbon atoms or groups. Such substitution may include fusion to a 4 to 7 or a 5 to 7-membered saturated or partially unsaturated cyclic group that optionally contains 1, 2 or 3 heteroatoms independently selected from N, O, B, P, Si and/or S, to form, for example, a 3,4-methylenedioxyphenyl group. Aryl groups include, for example, phenyl and naphthyl, including 1-naphthyl and 2-naphthyl. In one embodiment, aryl groups are pendant. An example of a pendant ring is a phenyl group substituted with a phenyl group. In one embodiment, the aryl group is optionally substituted as described above.

The term "heterocycle," or "heterocyclic ring" as used herein refers to a saturated or a partially unsaturated (i.e., having one or more double and/or triple bonds within the ring without aromaticity) carbocyclic moiety of 3 to about 12, and more typically 3, 4, 5, 6, 7, 8 to 10 ring atoms in which at least one ring atom is a heteroatom selected from nitrogen, oxygen, phosphorus sulfur, silicon and boron, the remaining ring atoms being C, where one or more ring atoms is optionally substituted independently with one or more substituents described above. A heterocycle may be a monocycle having 3 to 7 ring members (2 to 6 carbon atoms and 1 to 4 heteroatoms selected from N, O, P, S, Si and B) or a bicycle having 6 to 10 ring members (4 to 9 carbon atoms and 1 to 6 heteroatoms selected from N, O, P, S, Si and B), for example: a bicyclo [4,5], [5,5], [5,6], or [6,6] system. In one embodiment, the only heteroatom is nitrogen. In one embodiment, the only heteroatom is oxygen. In one embodiment, the only heteroatom is sulfur, boron or silicon. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. Examples of heterocyclic rings include, but are not limited to, pyrrolidinyl, dihydrofuranyl, tetrahydrothienyl, tetrahydropyranyl, dihydropyranyl, tetrahydrothiopyranyl, piperidino, piperidonyl, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, dihydroisoquinolinyl, tetrahydroisoquinolinyl, pyrazolidinylimidazolinyl, imidazolidinyl, 2-oxa-5-azabicyclo[2.2.2]octane, 3-oxa-8-azabicyclo[3.2.1]octane, 8-oxa-3-azabicyclo[3.2.1]octane, 6-oxa-3-azabicyclo[3.1.1]heptane, 2-oxa-5-azabicyclo[2.2.1]heptane, 3-azabicyclo[3.1.0]hexanyl, 3-azabicyclo[4.1.0]heptanyl, azabicyclo[2.2.2]hexanyl, 3H-indolyl, quinolizinyl, N-pyridyl ureas, and pyrrolopyrimidine. Spiro moieties are also included within the scope of this definition. Examples of a heterocyclic group wherein 1 or 2 ring carbon atoms are substituted with oxo (=O) moieties are pyrimidinonyl and 1,1-dioxo-thiomorpholinyl. The heterocycle groups herein are optionally substituted independently with one or more substituents described herein, for example, 1, 2, or 3 substituents.

"Heterocyclicoxy group" is a monocyclic heterocyclic ring or a bicyclic heterocyclic group as described previously linked to the group it substitutes via an oxygen, —O—, linker.

"Heteroaryl" refers to a stable monocyclic, bicyclic, or multicyclic aromatic ring which contains from 1 to 3, or in some embodiments from 1, 2, or 3 heteroatoms selected from N, O, S, B or P with remaining ring atoms being carbon, or a stable bicyclic or tricyclic system containing at least one 5, 6, or 7 membered aromatic ring which contains from 1 to 3, or in some embodiments from 1 to 2, heteroatoms selected from N, O, S, B or P with remaining ring atoms being carbon. In one embodiment, the only heteroatom is nitrogen. In one embodiment, the only heteroatom is oxygen. In one embodiment, the only heteroatom is sulfur. Monocyclic heteroaryl groups typically have from 5, 6, or 7 ring atoms. In some embodiments bicyclic heteroaryl groups are 8- to 10-membered heteroaryl groups, that is, groups containing 8 or 10 ring atoms in which one 5, 6, or 7 member aromatic ring is fused to a second aromatic or non-aromatic ring. When the total number of S and O atoms in the heteroaryl group exceeds 1, these heteroatoms are not adjacent to one another. In one embodiment, the total number of S and O atoms in the heteroaryl group is not more than 2. In another embodiment, the total number of S and O atoms in the aromatic heterocycle is not more than 1. Examples of heteroaryl groups include, but are not limited to, pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, tetrahydrofuranyl, and furopyridinyl. Heteroaryl groups are optionally substituted independently with one or more substituents described herein. "Heteroaryloxy" is a heteroaryl group as described bound to the group it substituted via an oxygen, —O—, linker.

"Heterocycloalkyl" is a fully saturated heterocycle as defined herein. It may have, for example, include 1, 2, 3, or 4 heteroatoms independently selected from N, S, O, Si and B with the remaining ring atoms being carbon. In a typical embodiment, nitrogen is the heteroatom. Monocyclic heterocycloalkyl groups typically have from 3 to about 8 ring atoms or from 4 to 6 ring atoms.

The term "mono- and/or di-alkylamino" indicate a secondary or tertiary alkylamino group, wherein the alkyl groups are independently selected as defined herein. The point of attachment of the alkylamino group is on the nitrogen. Examples of mono- and di-alkylamino groups include ethylamino, dimethylamino, and methyl-propylamino.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

"Pharmaceutical compositions" are compositions comprising at least one active agent, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

A "pharmaceutically acceptable salt" is a derivative of the disclosed compound in which the parent compound is modified by making inorganic and organic, pharmaceutically acceptable, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include salts which are acceptable for human consumption and the quaternary ammonium salts of the parent compound formed, for example, from inorganic or organic acids. Examples, of such salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like, or using a different acid that produces the same counterion. Lists of additional suitable salts may be found, e.g., in *Remington's Pharmaceutical Sciences,* 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, acceptable for human consumption, and neither biologically nor otherwise inappropriate for administration to a host, typically a human. In one embodiment, an excipient is used that is acceptable for veterinary use.

A "patient" or "host" or "subject" is a human or non-human animal in need of treatment or prevention of any of the disorders as specifically described herein, including but not limited to by modulation of the complement Factor D pathway or with a condition that is treatable with one of the compounds described herein. Typically the host is a human. A "patient" or "host" or "subject" also refers to for example, a mammal, primate (e.g., human), cows, sheep, goat, horse, dog, cat, rabbit, rat, mice, bird and the like.

A "prodrug" as used herein, means a compound which when administered to a host in vivo is converted into a parent drug. As used herein, the term "parent drug" means any of the presently described chemical compounds herein. Prodrugs can be used to achieve any desired effect, including to enhance properties of the parent drug or to improve the pharmaceutic or pharmacokinetic properties of the parent, including to increase the half-life of the drug in vivo. Prodrug strategies provide choices in modulating the conditions for in vivo generation of the parent drug. Nonlimiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others. In certain embodiments, the prodrug renders the parent compound more lipophilic. In certain embodiments, a prodrug can be provided that has several prodrug moieties in linear, branched or cyclic manner. For example, nonlimiting embodiments include the use of a divalent linker moiety such as a dicarboxylic acid, amino acid, diamine, hydroxycarboxylic acid, hydroxyamine, di-hydroxy compound, or other compound that has at least two functional groups that can link the parent molecule with another prodrug moiety, and is typically biodegradable in vivo. In some embodiments, 2, 3, 4 or 5 prodrug biodegradable moieties are covalently bound in sequence, branched or cyclic fashion to the parent compound. Nonlimiting examples of prodrugs according to the present invention are formed with:

i. a carboxylic acid on the parent drug and a hydroxylated prodrug moiety to form an ester;
ii. a carboxylic acid on the parent drug and an amine prodrug to form an amide;
iii. an amino on the parent drug and a carboxylic acid prodrug moiety to form an amide,
iv. an amino on the parent drug and a sulfonic acid to form a sulfonamide;
v. a sulfonic acid on the parent drug and an amino on the prodrug moiety to form a sulfonamide;
vi. a hydroxyl group on the parent drug and a carboxylic acid on the prodrug moiety to form an ester;
vii. a hydroxyl on the parent drug and a hydroxylated prodrug moiety to form an ether;
viii. a phosphonate on the parent drug and a hydroxylated prodrug moiety to form a phosphonate ester;
ix. a phosphoric acid on the parent drug and a hydroxylated prodrug moiety to form a phosphate ester;
x. a hydroxyl on the parent drug and a phosphonate on the prodrug to form a phosphonate ester;
xi. a hydroxyl on the parent drug and a phosphoric acid prodrug moiety to form a phosphate ester;

xii. a carboxylic acid on the parent drug and a prodrug of the structure HO—(CH$_2$)$_2$—O—(C$_{2-24}$ aliphatic group), for example, HO—(CH$_2$)$_2$—O—(C$_{2-24}$ alkyl group) to form an ester;

xiii. a carboxylic acid on the parent drug and a prodrug of the structure HO—(CH$_2$)$_2$—S—(C$_{2-24}$ aliphatic group), for example, HO—(CH$_2$)$_2$—S—(C$_{2-24}$ alkyl group) to form a thioester;

xiv. a hydroxyl on the parent drug and a prodrug of the structure HO—(CH$_2$)$_2$—O—(C$_{2-24}$ aliphatic group), for example, HO—(CH$_2$)$_2$—O—(C$_{2-24}$ alkyl group) to form an ether;

xv. a carboxylic acid on the parent drug and a prodrug of the structure HO—(CH$_2$)$_2$—S—(C$_{2-24}$ aliphatic group), for example, HO—(CH$_2$)$_2$—S—(C$_{2-24}$ alkyl group), to form a thioether; and xvi. a carboxylic acid, oxime, hydrazide, hydrazone, amine or hydroxyl on the parent compound and a prodrug moiety that is a biodegradable polymer or oligomer including but not limited to polylactic acid, polylactide-co-glycolide, polyglycolide, polyethylene glycol, polyanhydride, polyester, polyamide or a peptide. An exemplary synthesis of Oxime linkages is provided in the paper published by Jin et. al. titled "Oxime Linkage: A Robust Tool for the Design of PH-Sensitive Polymeric Drug Carriers" in BioMacromolecules, 2011, 12(10), 3460-3468.

In one embodiment, a prodrug is provided by attaching a natural or non-natural amino acid to an appropriate functional moiety on the parent compound, for example, oxygen, nitrogen or sulfur, and typically oxygen or nitrogen, usually in a manner such that the amino acid can be cleaved in vivo to provide the parent drug. The amino acid can be used alone or covalently linked (straight, branched or cyclic) to one or more other prodrug moieties to modify the parent drug to achieve the desired performance, such as increased half-life, lipophilicity, or other drug delivery or pharmacokinetic properties. The amino acid can be any compound with an amino group and a carboxylic acid, which includes an aliphatic amino acid, alkyl amino acid, aromatic amino acid, heteroaliphatic amino acid, heteroalkyl amino acid, or heterocyclic amino acid or heteroaryl amino acid.

"Providing a compound with at least one additional active agent," for example, in one embodiment can mean that the compound and the additional active agent(s) are provided simultaneously in a single dosage form, provided concomitantly in separate dosage forms, or provided in separate dosage forms for administration. In one embodiment, the compound administrations are separated by some amount of time that is within the time in which both the compound and the at least one additional active agent are within the blood stream of a patient. In certain embodiments the compound and the additional active agent need not be prescribed for a patient by the same medical care worker. In certain embodiments the additional active agent or agents need not require a prescription. Administration of the compound or the at least one additional active agent can occur via any appropriate route, for example, oral tablets, oral capsules, oral liquids, inhalation, injection, suppositories, parenteral, sublingual, buccal, intravenous, intraaortal, transdermal, polymeric controlled delivery, non-polymeric controlled delivery, nano or microparticles, liposomes, and/or topical contact. In one embodiment, the instructions for administration in a form of combination therapy is provided in the drug labeling.

A "therapeutically effective amount" of a pharmaceutical composition/combination of this invention means an amount effective, when administered to a host, provides a therapeutic benefit such as an amelioration of symptoms or reduction or diminution of the disease itself. In one embodiment, a therapeutically effective amount is an amount sufficient to prevent a significant increase or will significantly reduce the detectable level of complement Factor D in the patient's blood, serum, or tissues.

Detailed Description of the Active Compounds

N-Oxides

In certain embodiments, any of the active compounds can be provided in its N-oxide form to a patient in need thereof. In one embodiment, an N-oxide of an active compound or a precursor of the active compound is used in a manufacturing scheme. In yet another embodiment, the N-oxide is a metabolite of administration of one of the active compounds herein, and may have independent activity. The N-oxide can be formed by treating the compound of interest with an oxidizing agent, for example a suitable peroxyacid or peroxide, to generate an N-oxide compound. For example, a heteroaryl group, for example a pyridyl group, can be treated with an oxidizing agent such as sodium percarbonate in the presence of a rhenium-based catalyst under mild reaction conditions to generate an N-oxide compound. A person skilled in the art will understand that appropriate protecting groups may be necessary to carry out the chemistry. See, Jain, S. L. et al., "Rhenium-Catalyzed Highly Efficient Oxidations of Tertiary Nitrogen Compounds to N-Oxides Using Sodium Percarbonate as Oxygen Source, Synlett, 2261-2663, 2006.

In one embodiment the N-oxide is in the A-Ring. In one embodiment the N-oxide is in the B-Ring. In one embodiment the N-oxide is on the R$^{32}$ group.

In other embodiments, any of the active compounds with a sulfur can be provided in its sulfoxide or sulfone form to a patient in need thereof. In a different embodiment, a sulfoxide or sulfone of one of the active compounds or a precursor of the active compound is used in a manufacturing scheme. A sulfur atom in a selected compound as described herein can be oxidized to form a sulfoxide

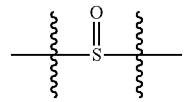 [SMILES: *S(*)=O]

or a sulfon

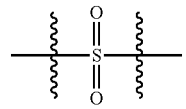 [SMILES: *S(*)(=O)=O]

using known methods. For example, the compound 1,3,5-triazo-2,4,6-triphosphorine-2,2,4,4,6,6-tetrachloride (TAPC) is an efficient promoter for the oxidation of sulfides to sulfoxides. See, Bahrami, M. et al., "TAPC-Promoted Oxidation of sulfides and Deoxygenation of Sulfoxides", J. Org. Chem., 75, 6208-6213 (2010). Oxidation of sulfides with 30% hydrogen peroxide catalyzed by tantalum carbide provides sulfoxides in high yields, see, Kirihara, A., et al., "Tantalum Carbide or Niobium Carbide Catalyzed Oxidation of Sulfides with Hydrogen Peroxide: Highly Efficient and Chemoselective Syntheses of Sulfoxides and Sulfones", Synlett, 1557-1561 (2010). Sulfides can be oxidized to sulfones using, for example, niobium carbide as the catalyst, see, Kirihara, A., et al., "Tantalum Cardide or Niobium Carbide Catalyzed Oxidation of Sulfides with Hydrogen Peroxide: Highly Efficient and Chemoselective Syntheses of Sulfoxides and Sulfones", Synlett, 1557-1561 (2010). Urea-hydrogen peroxide adduct is a stable inexpensive and easily handled reagent for the oxidation of sulfides to sulfones, see Varma, R. S. and Naicker, K. P., "The Urea-Hydrogen Peroxide Complex: Solid-State Oxidative Protocols for Hydroxylated Aldehydes and Ketones (Dakin Reaction), Nitriles, Sulfides, and Nitrogen Heterocycles", Org. Lett., 1, 189-191 (1999). One skilled in the art will appreciate that other heteroatoms, such as nitrogen, may need to be protected and then deprotected while carrying out the oxidation of a sulfur atom to produce the desired compound.

Embodiments of "Alkyl"

In one embodiment "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-$C_4$alkyl, $C_1$-$C_3$alkyl, or $C_1$-$C_2$alkyl.
In one embodiment "alkyl" has one carbon.
In one embodiment "alkyl" has two carbons.
In one embodiment "alkyl" has three carbons.
In one embodiment "alkyl" has four carbons.
In one embodiment "alkyl" has five carbons.
In one embodiment "alkyl" has six carbons.
Non-limiting examples of "alkyl" include: methyl, ethyl, propyl, butyl, pentyl, and hexyl.
Additional non-limiting examples of "alkyl" include: iso-propyl, isobutyl, isopentyl, and isohexyl.
Additional non-limiting examples of "alkyl" include: sec-butyl, sec-pentyl, and sec-hexyl.
Additional non-limiting examples of "alkyl" include: tert-butyl, tert-pentyl, and tert-hexyl.
Additional non-limiting examples of "alkyl" include: neo-pentyl, 3-pentyl, and active pentyl.
In one embodiment "alkyl" is "substituted alkyl"
In one embodiment "alkenyl" is "substituted alkenyl"
In one embodiment "alkynyl" is "substituted alkynyl"

Embodiments of "Haloalkyl"

In one embodiment "haloalkyl" is a $C_1$-$C_{10}$haloalkyl, $C_1$-$C_9$haloalkyl, $C_1$-$C_8$haloalkyl, $C_1$-$C_7$haloalkyl, $C_1$-$C_6$haloalkyl, $C_1$-$C_5$haloalkyl, $C_1$-$C_4$haloalkyl, $C_1$-$C_3$haloalkyl, and $C_1$-$C_2$haloalkyl.
In one embodiment "haloalkyl" has one carbon.
In one embodiment "haloalkyl" has one carbon and one halogen.
In one embodiment "haloalkyl" has one carbon and two halogens.
In one embodiment "haloalkyl" has one carbon and three halogens.
In one embodiment "haloalkyl" has two carbons.
In one embodiment "haloalkyl" has three carbons.
In one embodiment "haloalkyl" has four carbons.
In one embodiment "haloalkyl" has five carbons.
In one embodiment "haloalkyl" has six carbons.
Non-limiting examples of "haloalkyl" include:

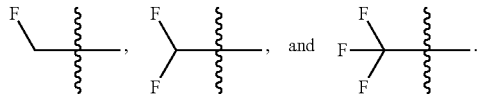

Additional non-limiting examples of "haloalkyl" include:

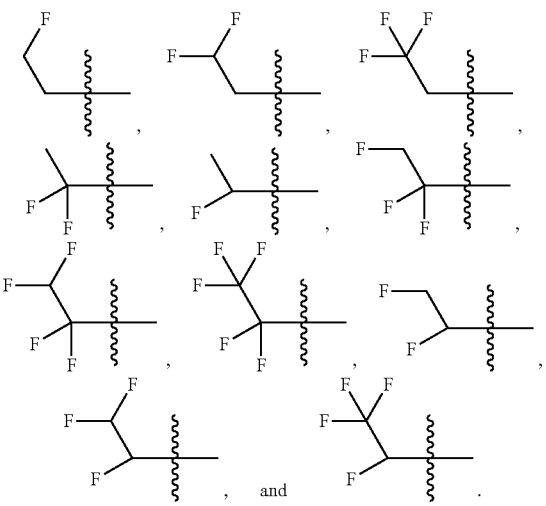

Additional non-limiting examples of "haloalkyl" include:

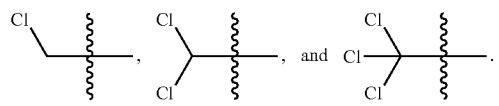

Additional non-limiting examples of "haloalkyl" include:

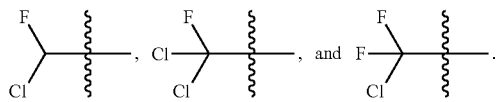

Embodiments of "Aryl"

In one embodiment "aryl" is a 6 carbon aromatic group (phenyl)
In one embodiment "aryl" is a 10 carbon aromatic group (napthyl)
In one embodiment "aryl" is "substituted aryl".

Embodiments of "Heteroaryl"

In one embodiment "heteroaryl" is a 5 membered aromatic group containing 1, 2, or 3, nitrogen atoms.
Non-limiting examples of 5 membered "heteroaryl" groups include pyrrole, furan, thiophene, pyrazole, imidazole, triazole, isoxazole, oxazole, oxadiazole, oxatriazole, isothiazole, thiazole, thiadiazole, and thiatriazole.
Additional non-limiting examples of 5 membered "heteroaryl" groups include:

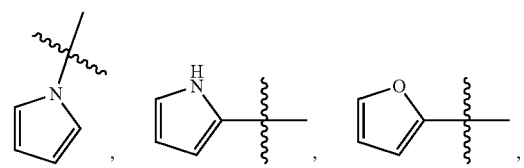

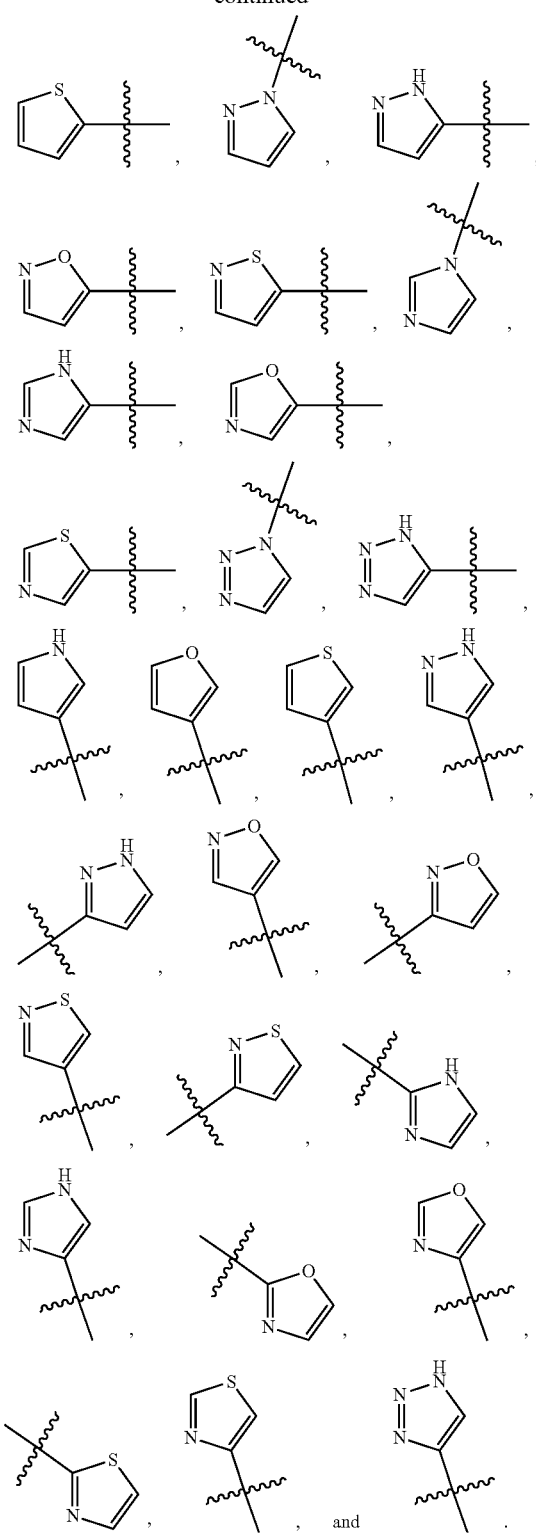

In one embodiment "heteroaryl" is a 6 membered aromatic group containing 1, 2, or 3 nitrogen atoms (i.e. pyridinyl, pyridazinyl, triazinyl, pyrimidinyl, and pyrazinyl).

Non-limiting examples of 6 membered "heteroaryl" groups with 1 or 2 nitrogen atoms include:

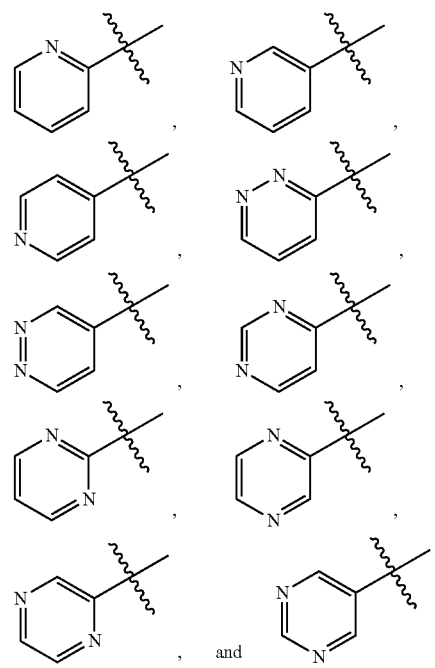

In one embodiment "heteroaryl" is a 9 membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of "heteroaryl" groups that are bicyclic include:

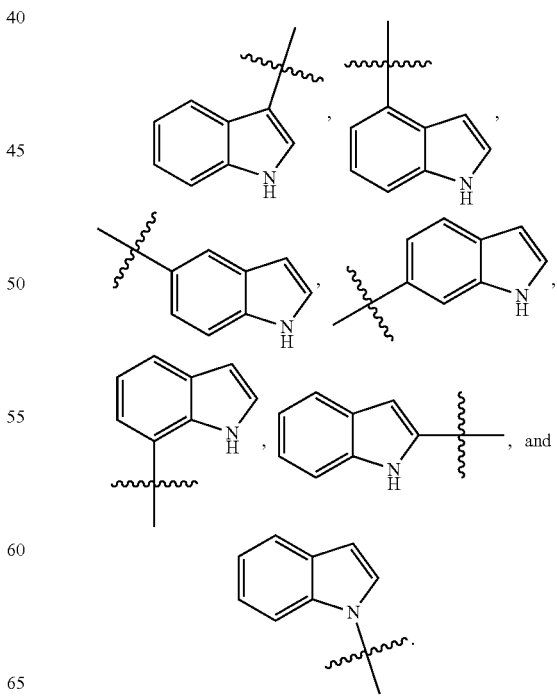

Additional non-limiting examples of "heteroaryl" groups that are bicyclic include:

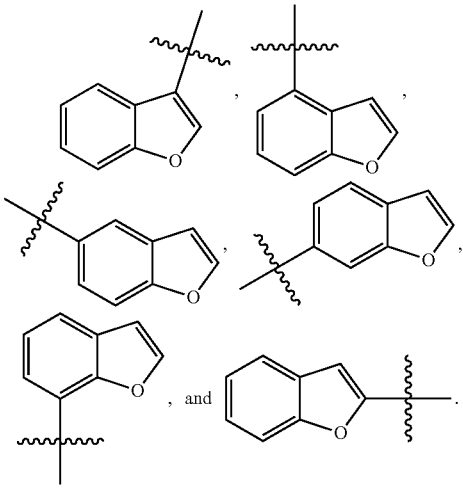

Additional non-limiting examples of "heteroaryl" groups that are bicyclic include:

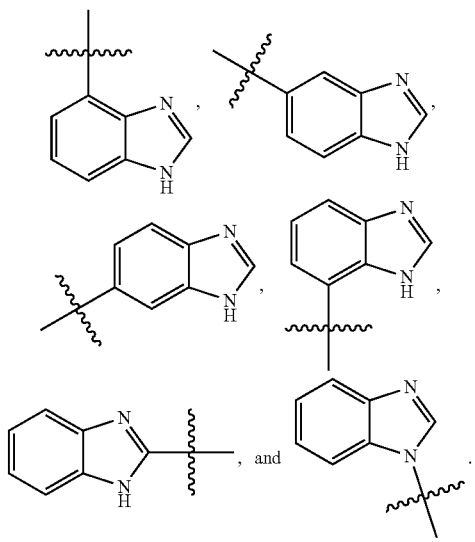

In one embodiment "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

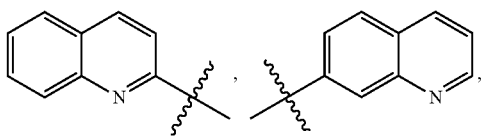

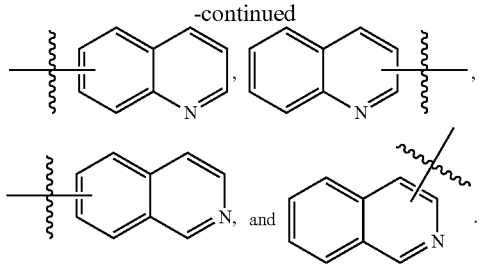

In one embodiment "heteroaryl" is "substituted heteroaryl."

In an alternative embodiment heteroaryl is tetrazole.

Embodiments of "Cycloalkyl"

In one embodiment "cycloalkyl" is a $C_3$-$C_8$cycloalkyl, $C_3$-$C_7$cycloalkyl, $C_3$-$C_6$cycloalkyl, $C_3$-$C_5$cycloalkyl, $C_3$-$C_4$cycloalkyl, $C_4$-$C_8$cycloalkyl, $C_5$-$C_8$cycloalkyl, or $C_6$-$C_8$cycloalkyl.

In one embodiment "cycloalkyl" has three carbons.
In one embodiment "cycloalkyl" has four carbons.
In one embodiment "cycloalkyl" has five carbons.
In one embodiment "cycloalkyl" has six carbons.
In one embodiment "cycloalkyl" has seven carbons.
In one embodiment "cycloalkyl" has eight carbons.
In one embodiment "cycloalkyl" has nine carbons.
In one embodiment "cycloalkyl" has ten carbons.

Non-limiting examples of "cycloalkyl" include: cyclopropyl, cyclobutyl, cyclopentyl, cyclohexyl, cycloheptyl, cyclooctyl, and cyclodecyl.

In one embodiment "cycloalkyl" is a "substituted cycloalkyl"

Embodiments of "Heterocycle"

In one embodiment "heterocycle" refers to a cyclic ring with one nitrogen and 3, 4, 5, 6, 7, or 8 carbon atoms.

In one embodiment "heterocycle" refers to a cyclic ring with one nitrogen and one oxygen and 3, 4, 5, 6, 7, or 8 carbon atoms.

In one embodiment "heterocycle" refers to a cyclic ring with two nitrogens and 3, 4, 5, 6, 7, or 8 carbon atoms.

In one embodiment "heterocycle" refers to a cyclic ring with one oxygen and 3, 4, 5, 6, 7, or 8 carbon atoms.

In one embodiment "heterocycle" refers to a cyclic ring with one sulfur and 3, 4, 5, 6, 7, or 8 carbon atoms.

Non-limiting examples of "heterocycle" include aziridine, oxirane, thiirane, azetidine, 1,3-diazetidine, oxetane, and thietane.

Additional non-limiting examples of "heterocycle" include pyrrolidine, 3-pyrroline, 2-pyrroline, pyrazolidine, and imidazolidine.

Additional non-limiting examples of "heterocycle" include tetrahydrofuran, 1,3-dioxolane, tetrahydrothiophene, 1,2-oxathiolane, and 1,3-oxathiolane.

Additional non-limiting examples of "heterocycle" include piperidine, piperazine, tetrahydropyran, 1,4-dioxane, thiane, 1,3-dithiane, 1,4-dithiane, morpholine, and thiomorpholine.

Non-limiting examples of "heterocycle" also include:

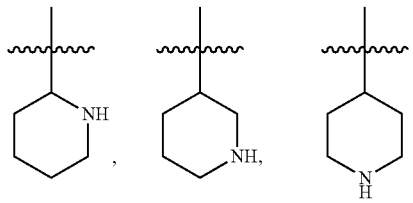

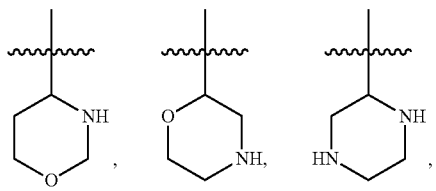

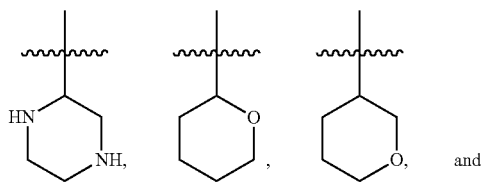

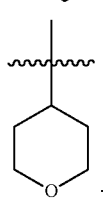

Additional non-limiting examples of "heterocycle" include:

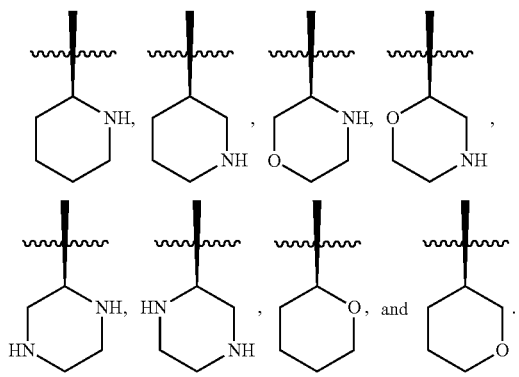

Additional non-limiting examples of "heterocycle" include:

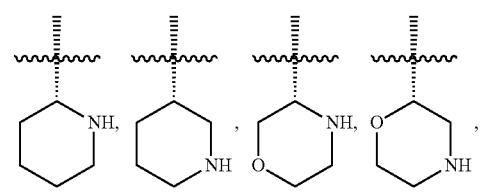

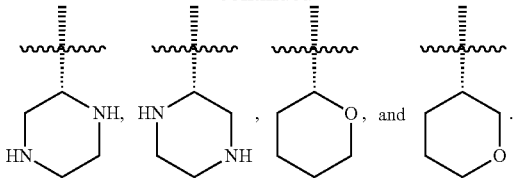

Non-limiting examples of "heterocycle" also include:

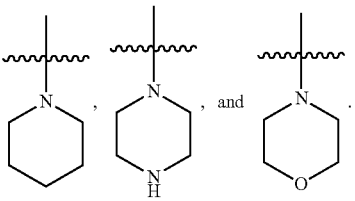

Non-limiting examples of "heterocycle" also include:

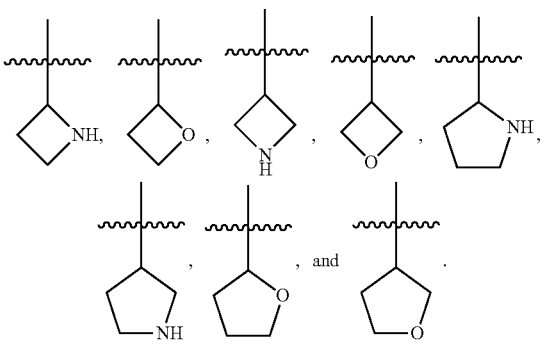

Additional non-limiting examples of "heterocycle" include:

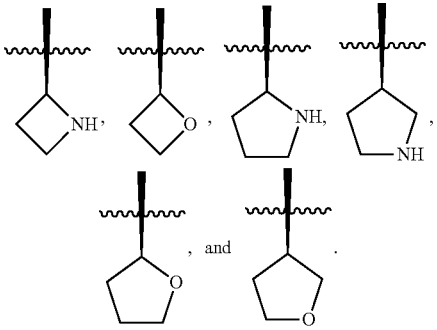

Additional non-limiting examples of "heterocycle" include:

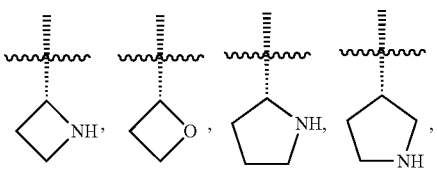

-continued

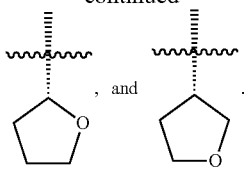, and

In one embodiment "heterocycle" is "substituted heterocycle".

Embodiments of $R^{201}$

In one embodiment $R^{201}$ is selected from $-(CH_2)_m-O$-heterocycle, $-(CH_2)_m-NH$-heterocycle, or $-(CH_2)_m-NR^9$-heterocycle;

In one embodiment $R^{201}$ is selected from $-(CH_2)_m-NR^9R^{10}$, $-(CH_2)_m-OR^9$, or $-(CH_2)_m$-heterocycle;

In one embodiment $R^{201}$ is selected from $-CH_2-O$-heterocycle, $-CH_2-NH$-heterocycle, or $-CH_2-NR^9$-heterocycle;

In one embodiment $R^{201}$ is selected from $-CH_2-NR^9R^{10}$, $-CH_2-OR^9$, or $-CH_2$-heterocycle;

In one embodiment $R^{201}$ is selected from $-(CH_2)_m-NH_2$, $-(CH_2)_m-OH$, or $-(CH_2)_m-OC_1-C_6$alkyl;

In one embodiment m is 1, 2, or 3.
In one embodiment m is 1.
In one embodiment m is 2.
In one embodiment m is 3.
In one embodiment $R^{201}$ is selected from:

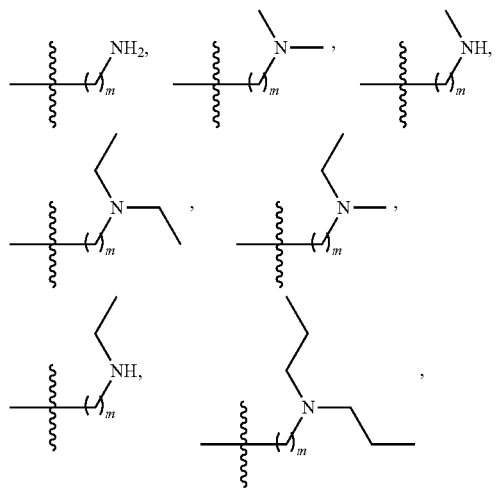

In one embodiment $R^{201}$ is selected from:

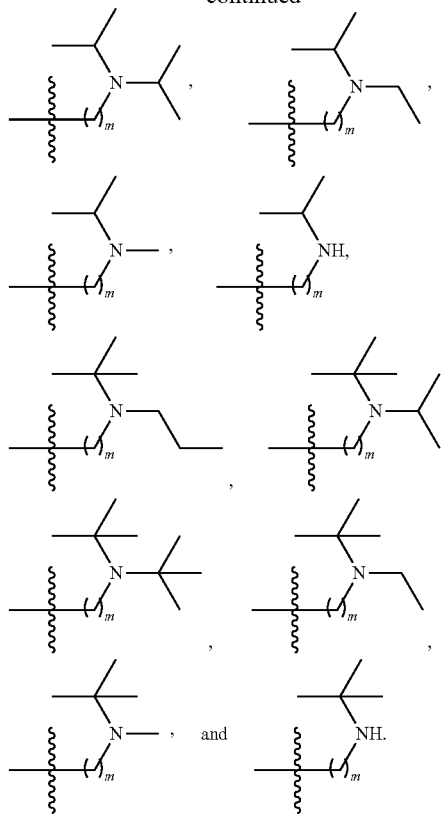

In one embodiment $R^{201}$ is selected from:

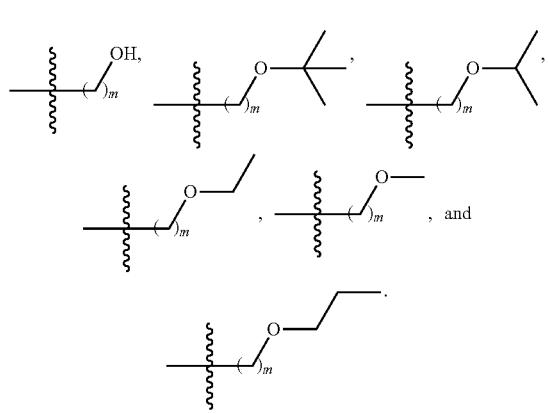

In one embodiment $R^{201}$ is selected from:

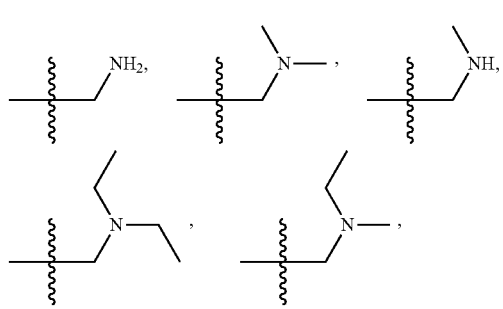

-continued
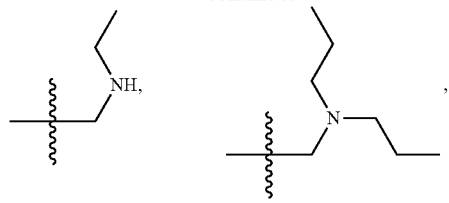
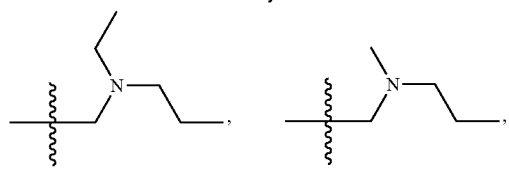
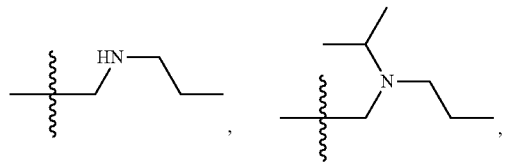
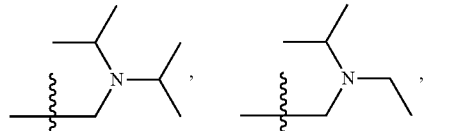
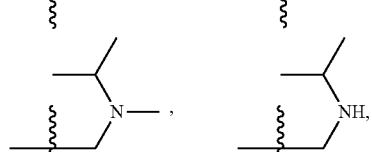
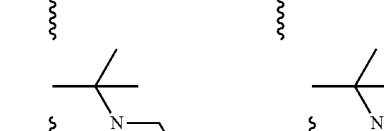
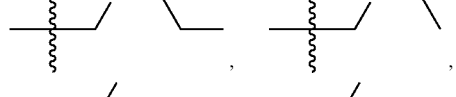
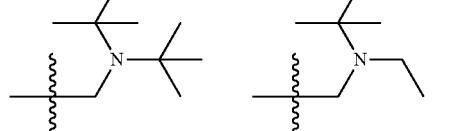
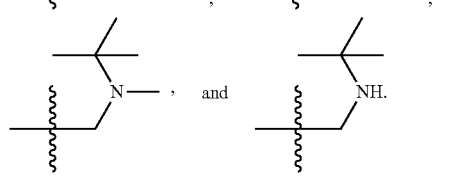
In one embodiment $R^{201}$ is selected from:
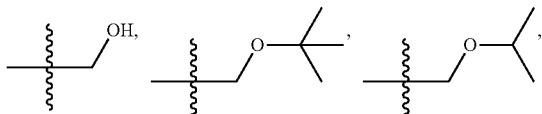
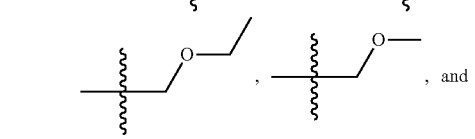, and
-continued
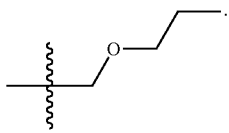
In one embodiment $R^{201}$ is selected from:
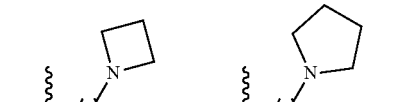
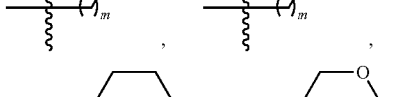
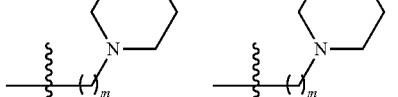
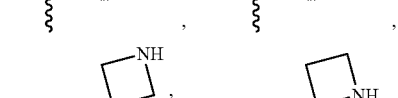
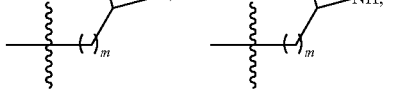
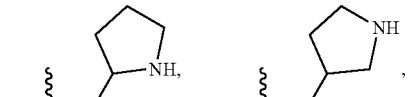
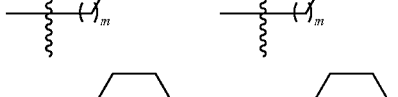
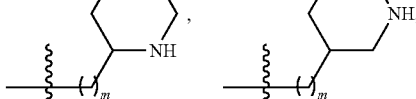
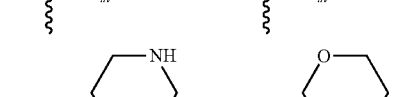
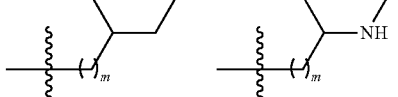
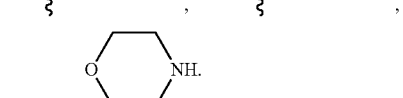, and
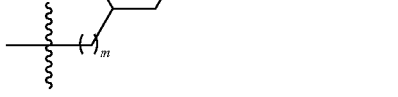
In one embodiment $R^{201}$ is selected from:
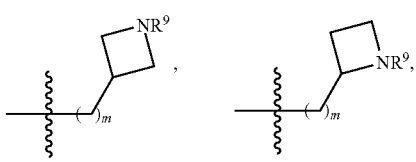

-continued
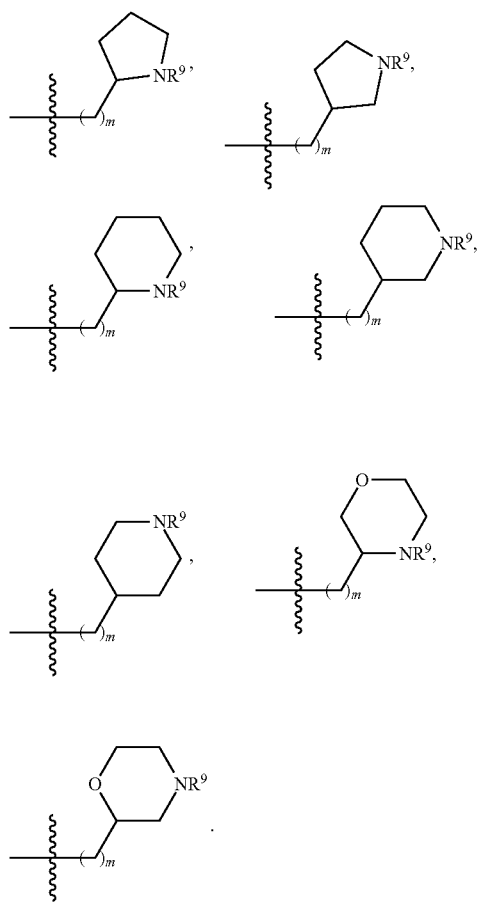
In one embodiment R²⁰¹ is selected from:
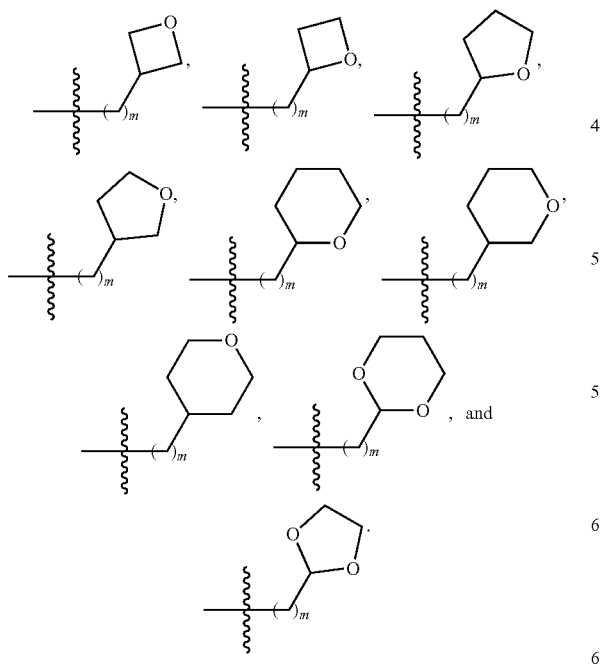
In one embodiment R²⁰¹ is selected from:
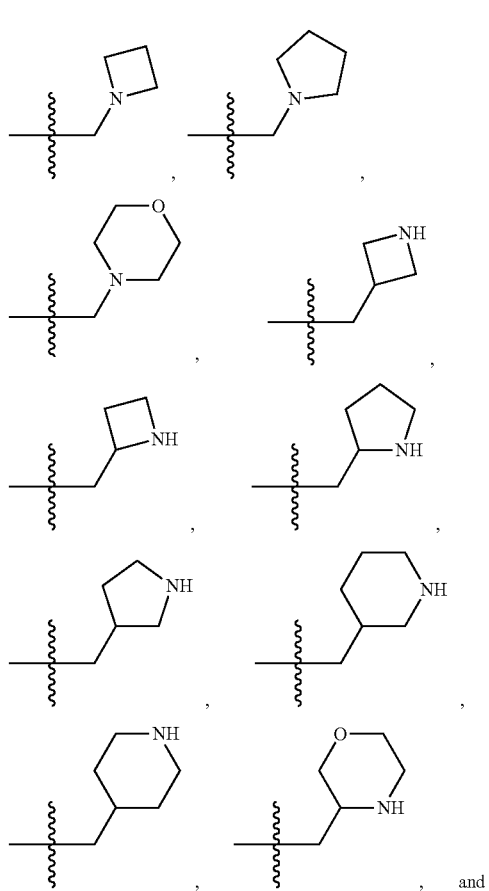
In one embodiment R²⁰¹ is selected from:
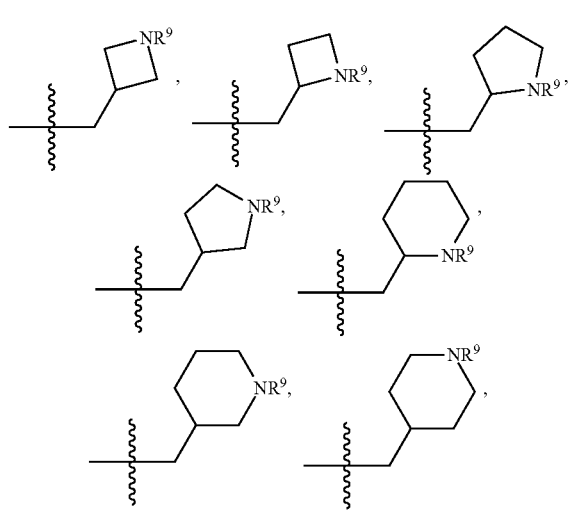

-continued
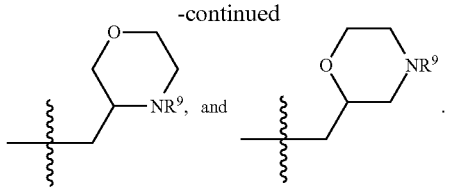
In one embodiment $R^{201}$ is selected from:
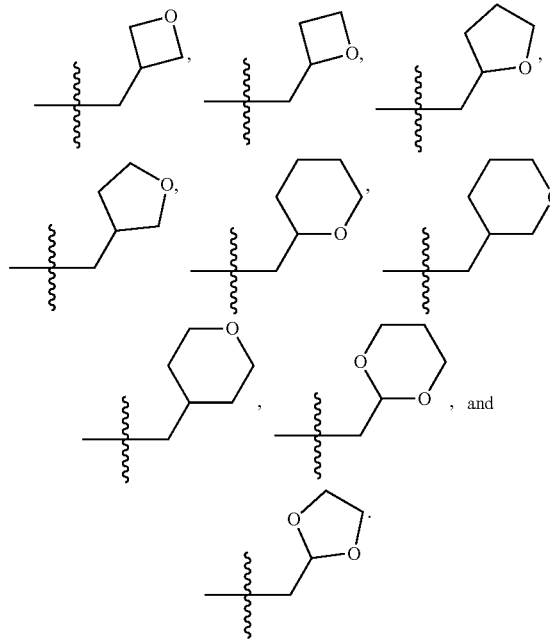
In one embodiment $R^{201}$ is selected from:
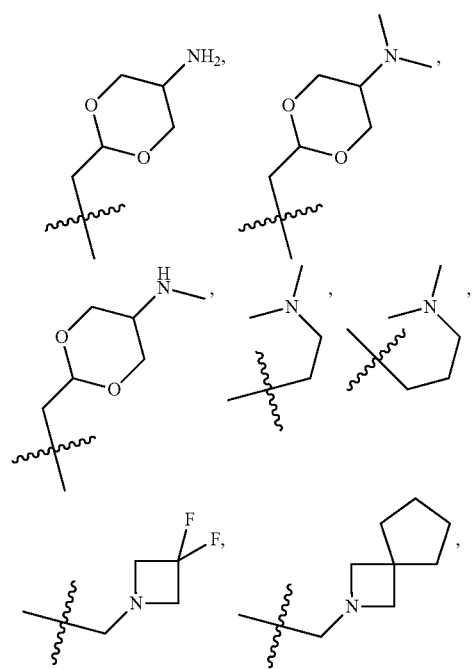
-continued
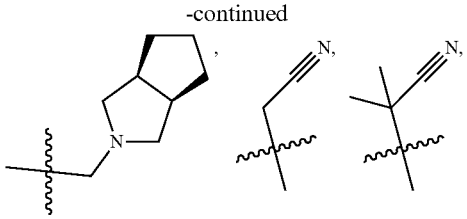
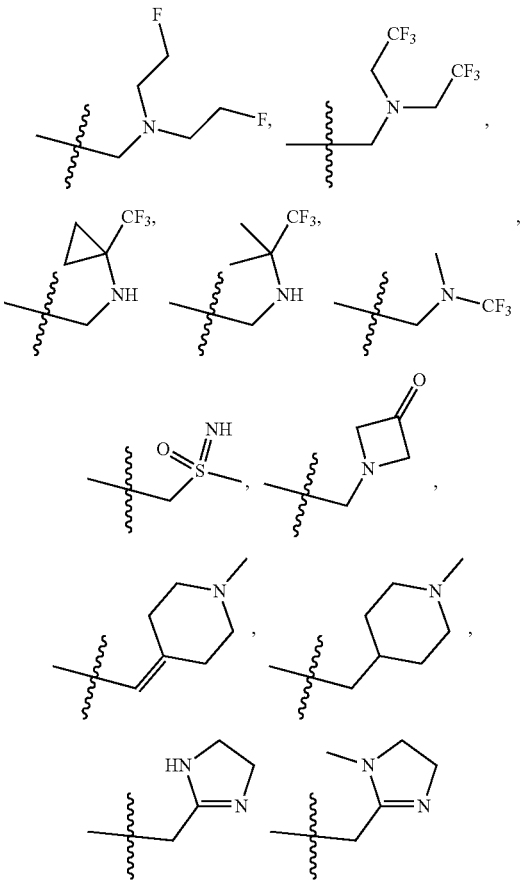
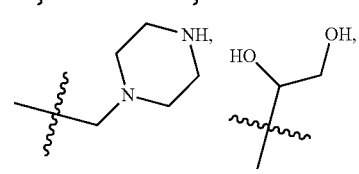

-continued
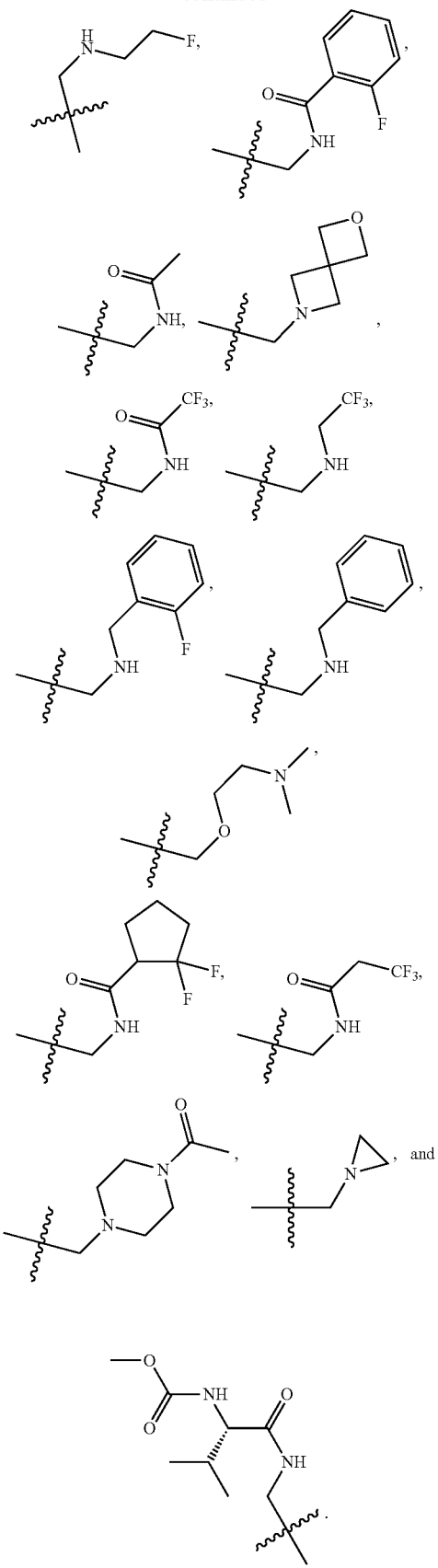
Embodiments of C
In one embodiment C5 is
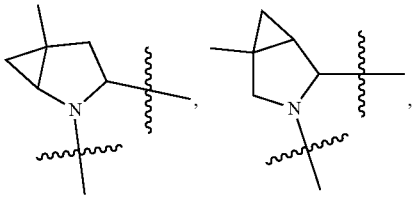
In one embodiment C5 is
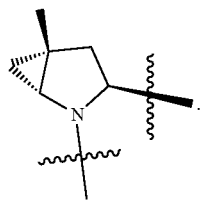 [SMILES: *N1[C@H](C)C[C@@]2(C)C[C@@H]12]
In one embodiment C5 is
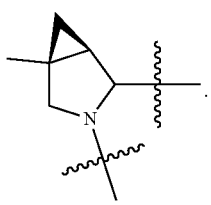 [SMILES: *C1[C@@H]2C[C@]2(C)CN1*]
In one embodiment C5 is
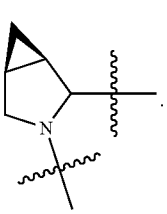 [SMILES: *C1[C@@H]2C[C@@H]2CN1*]

In one embodiment C1 is selected from:
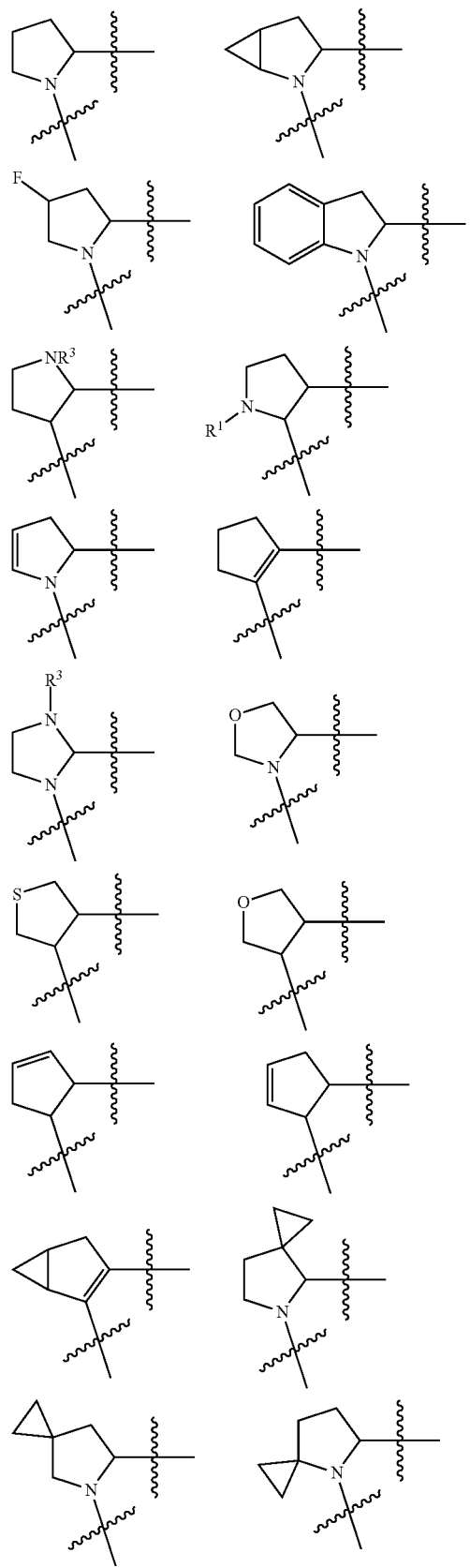
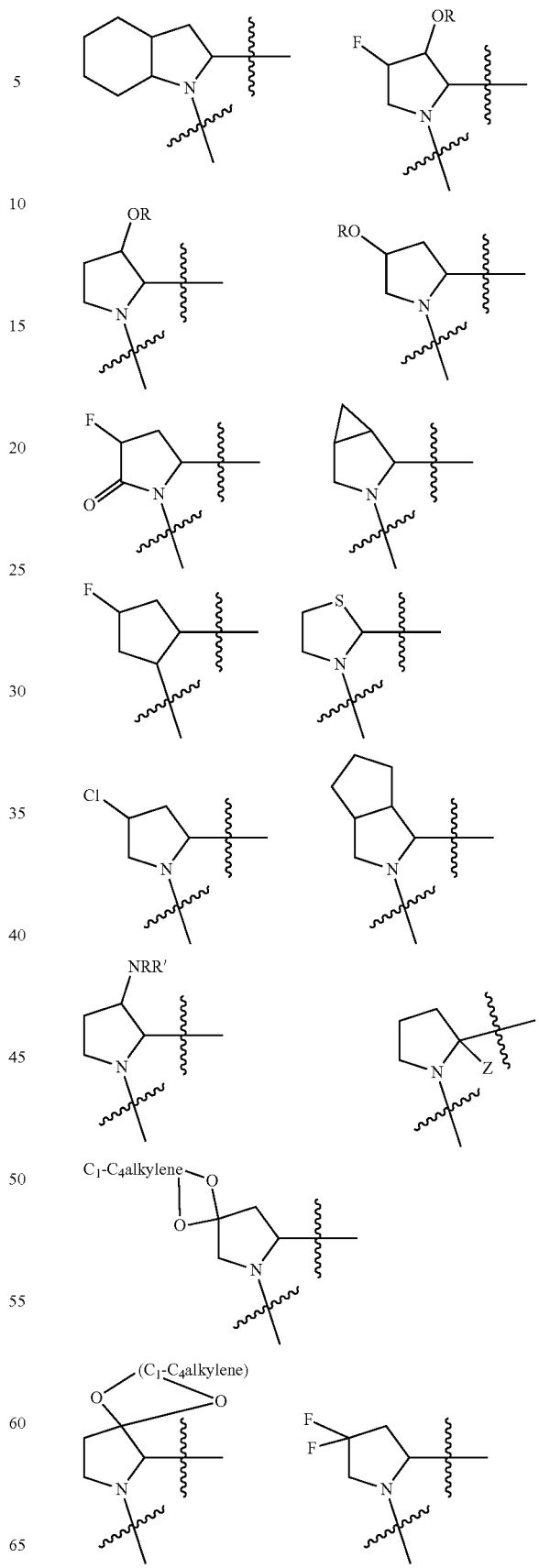
-continued

77
-continued
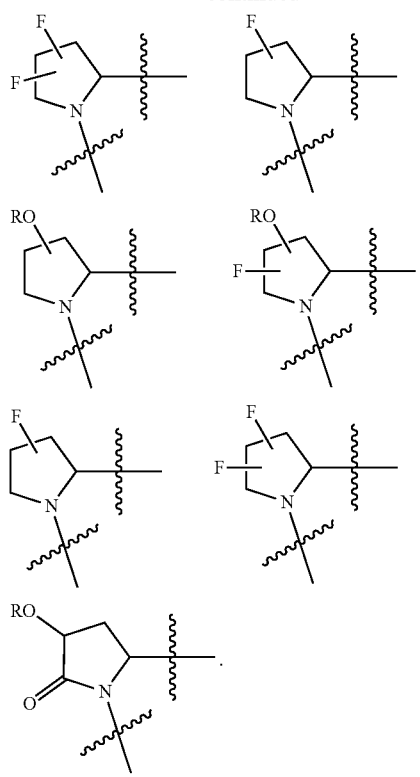
In one embodiment C1 is selected from:
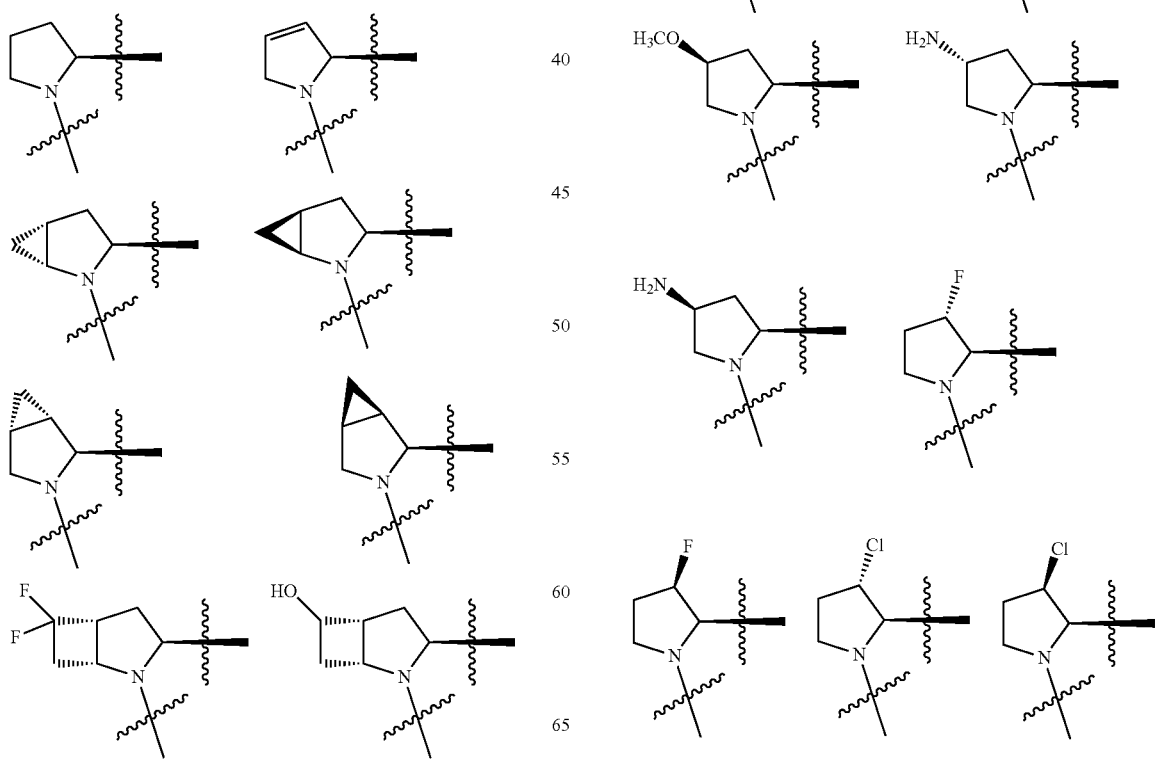
78
-continued
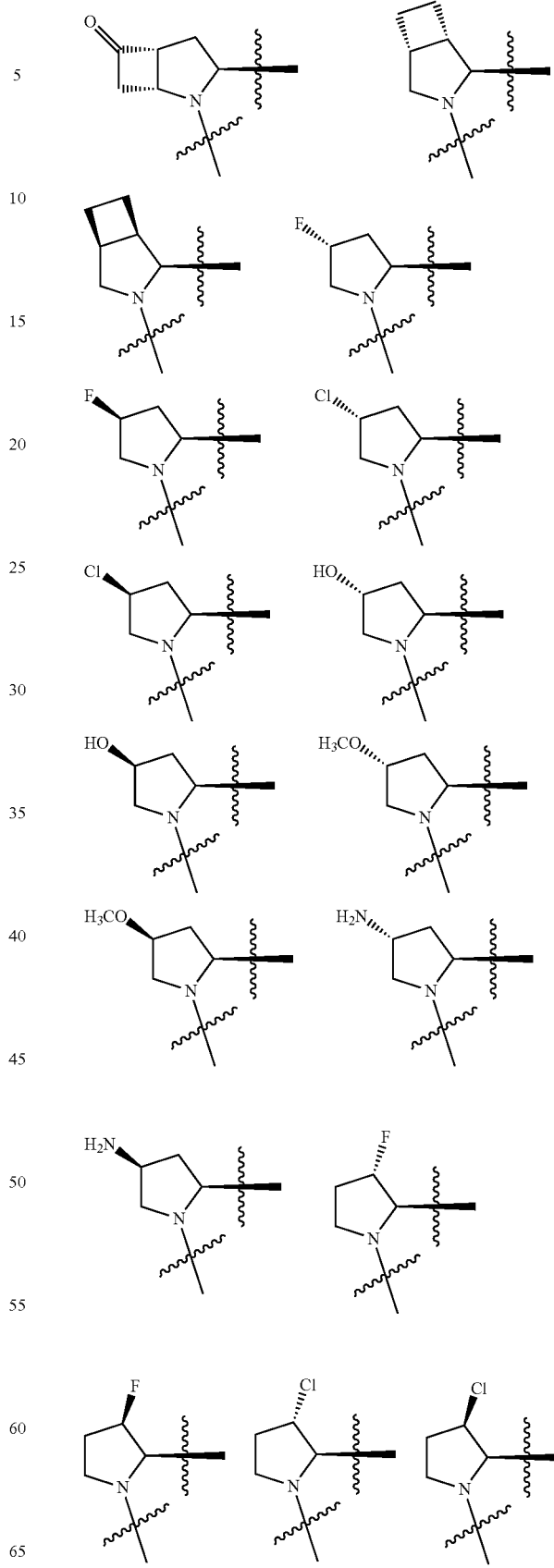
and

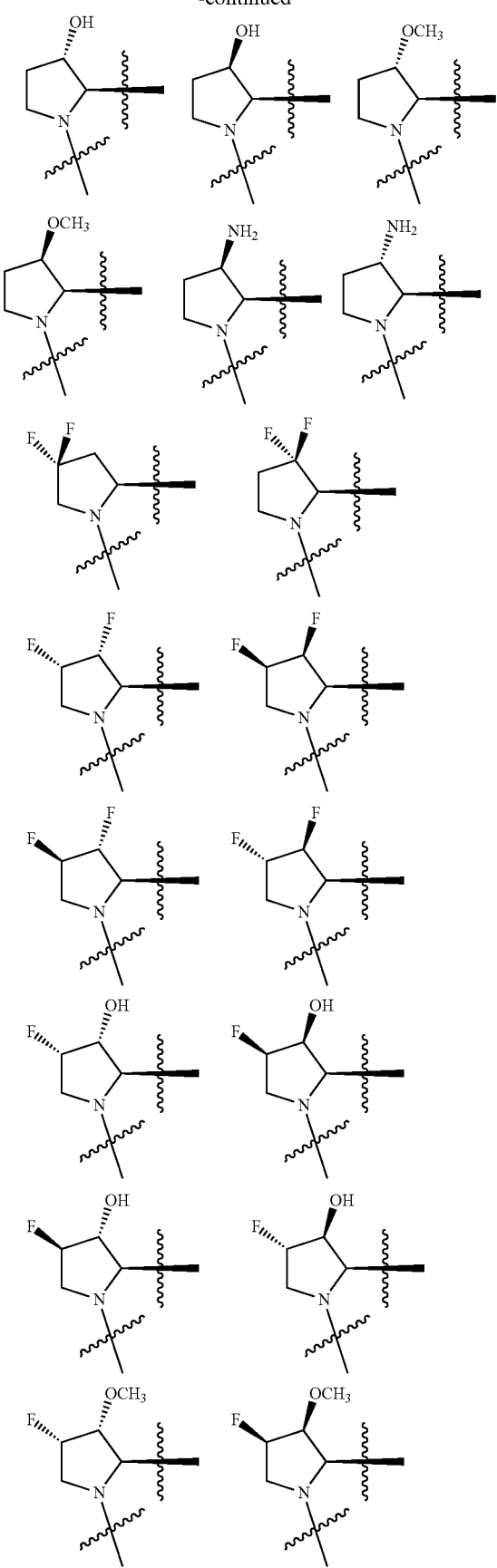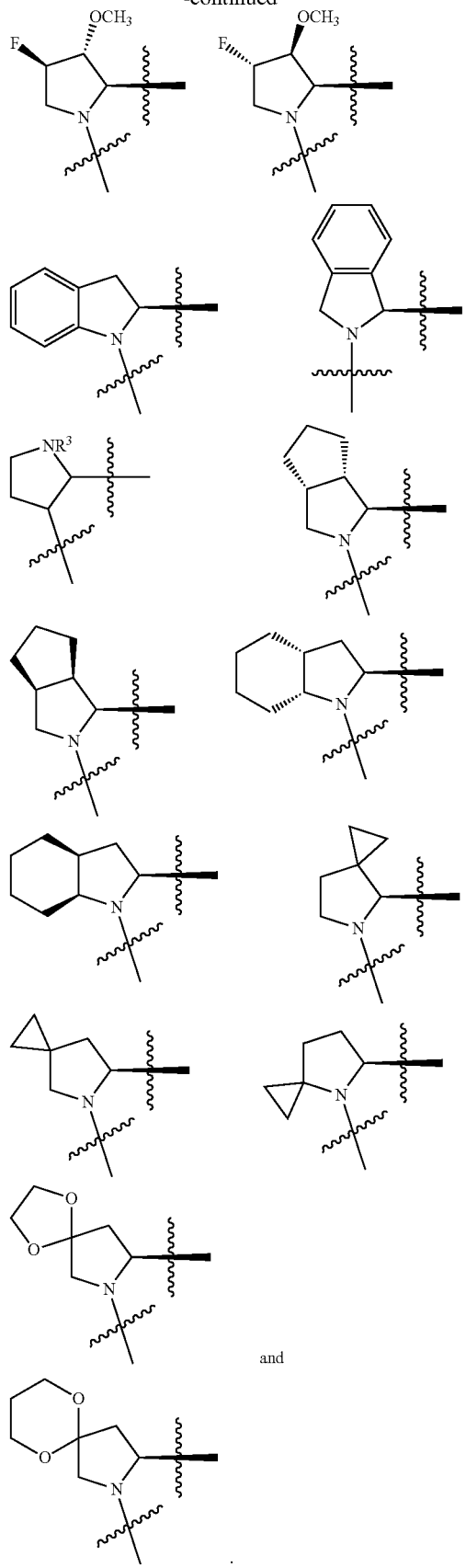

In one embodiment, a methyl group in a structure illustrated above can be replaced with a different alkyl group, as defined herein. In another embodiment, the fluoro atoms in the structures illustrated above can be replaced with any other halogen. Any of the structures illustrated above or otherwise can be optionally substituted with 0, 1, 2, 3, or 4, as appropriate, and independently, with an $R^{48}$ substituent.

Examples of central core small mimetics of a beta-turn, beta turn inducers, reverse turn mimetics and foldamer monomers include:

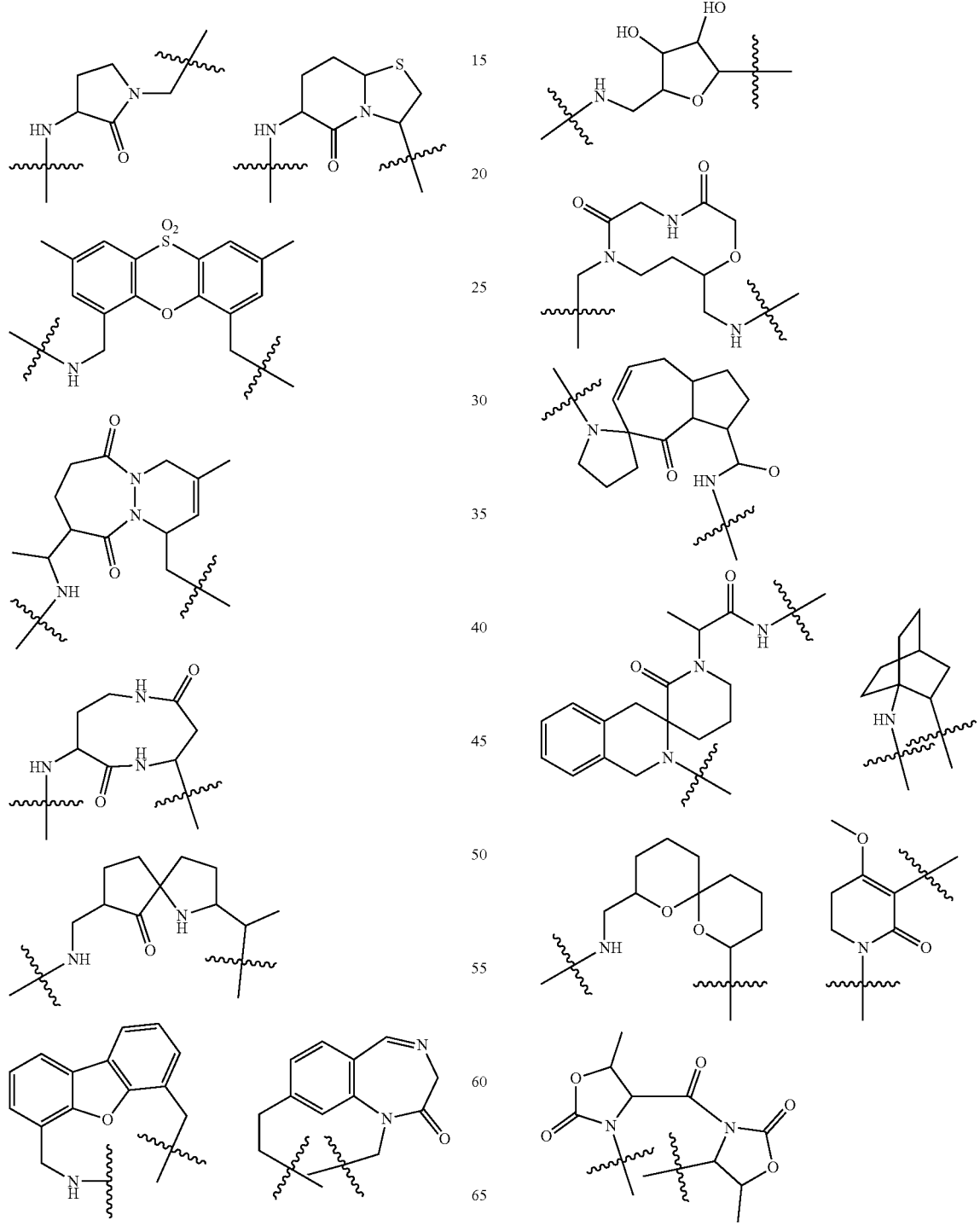

-continued

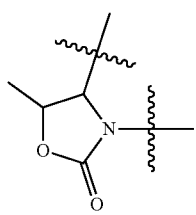
In one embodiment C is selected from:
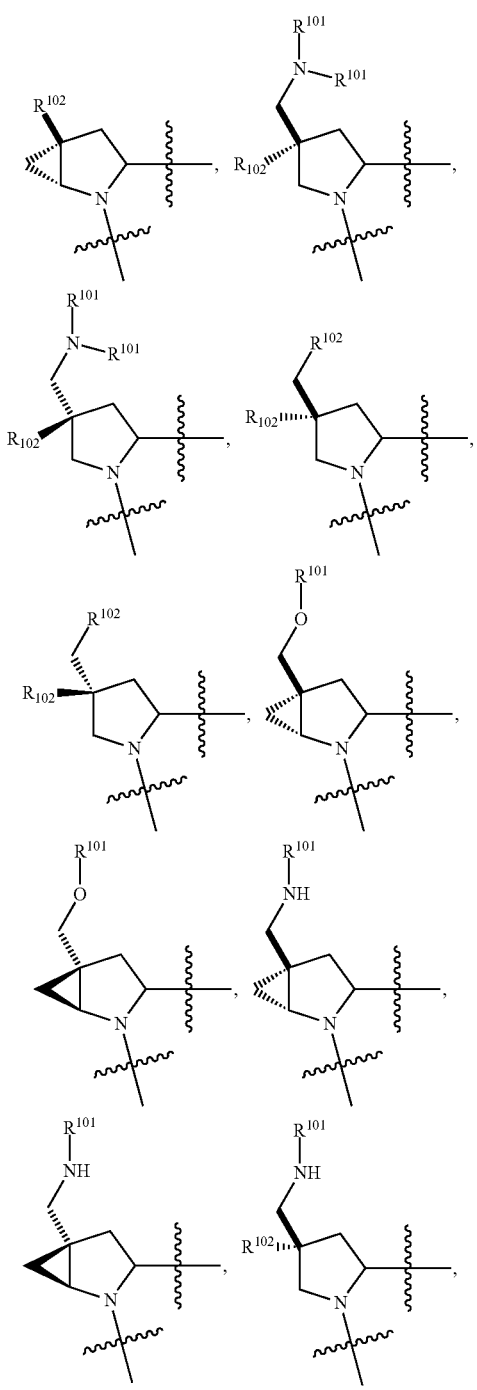

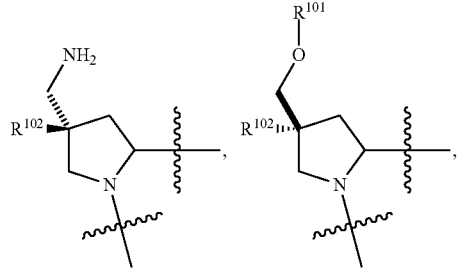
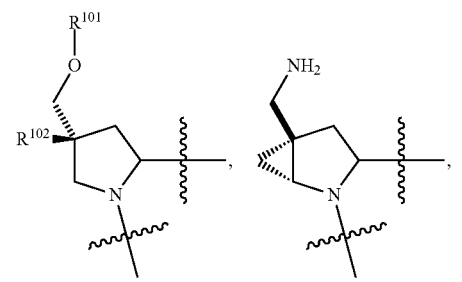
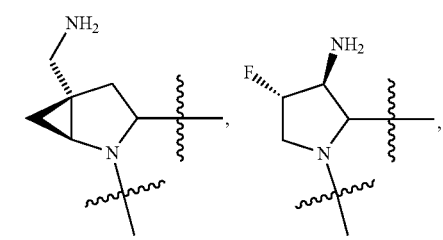
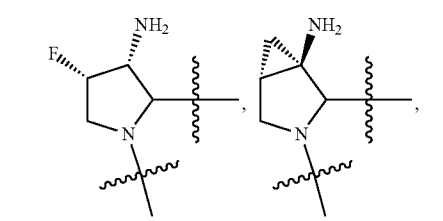
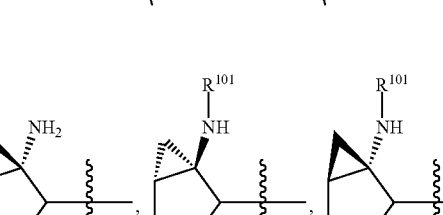

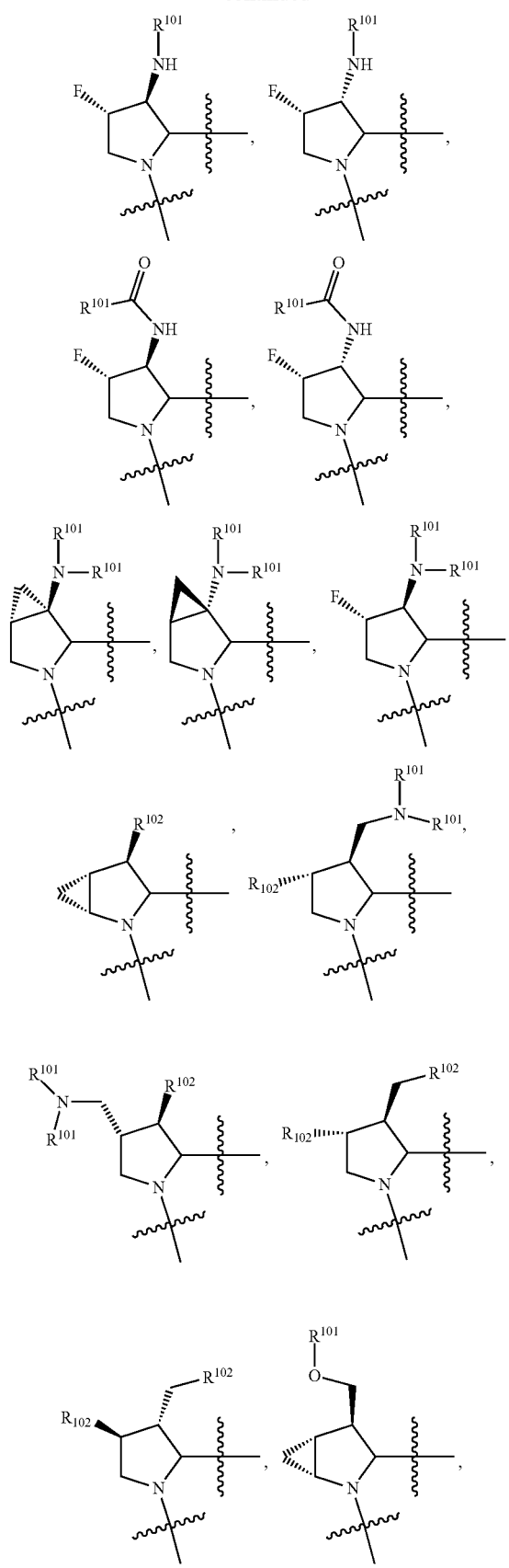
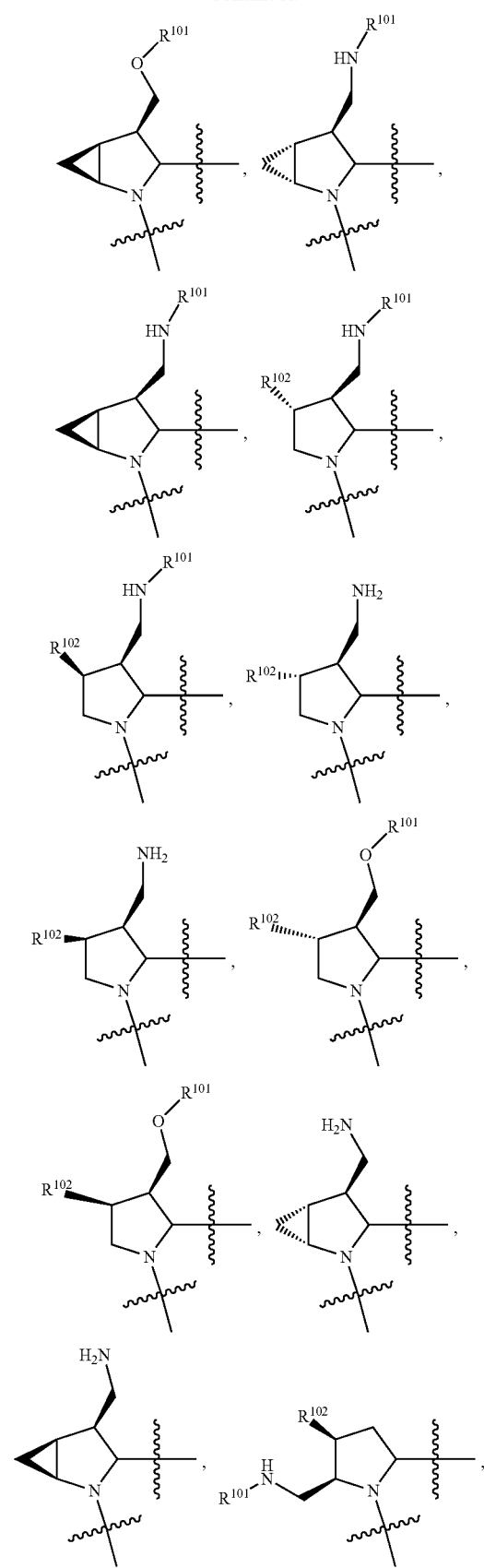

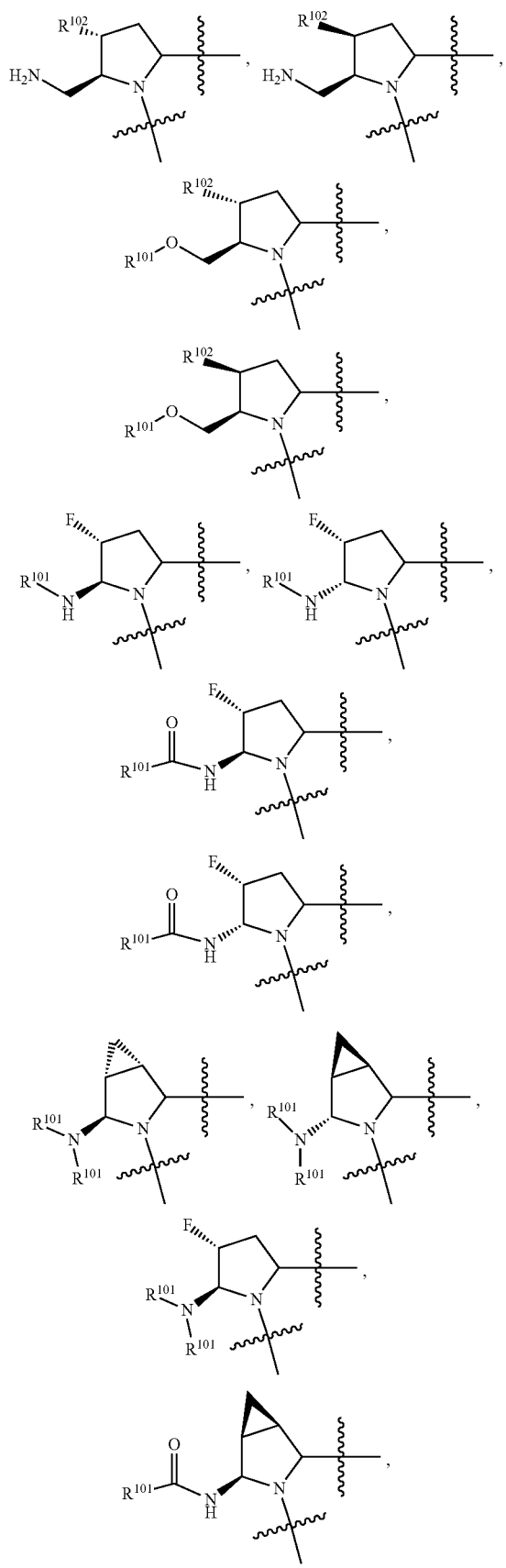
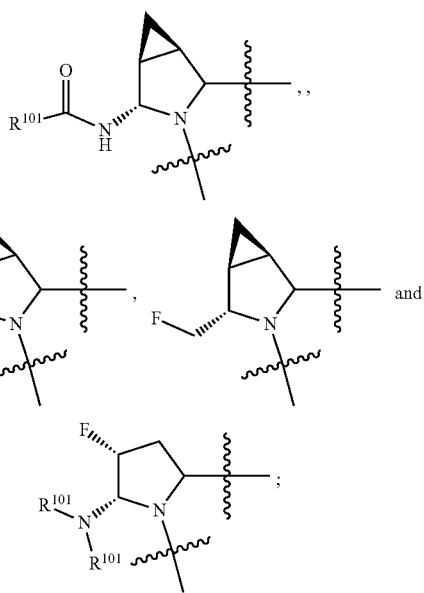
wherein:
$R^{101}$ is $C_1$-$C_4$ alkyl or $C_3$-$C_7$ cycloalkyl; and
$R^{102}$ is $C_1$-$C_4$ alkyl, fluorine, chlorine, or bromine.
In one embodiment C4 is selected from:
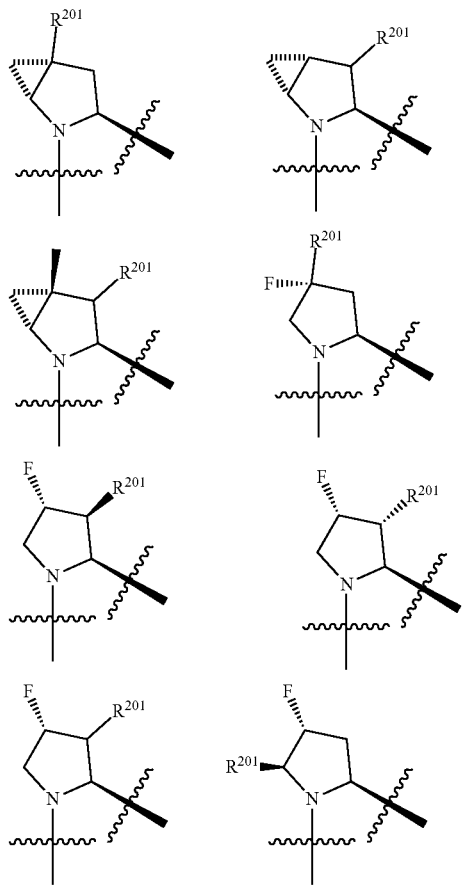

-continued
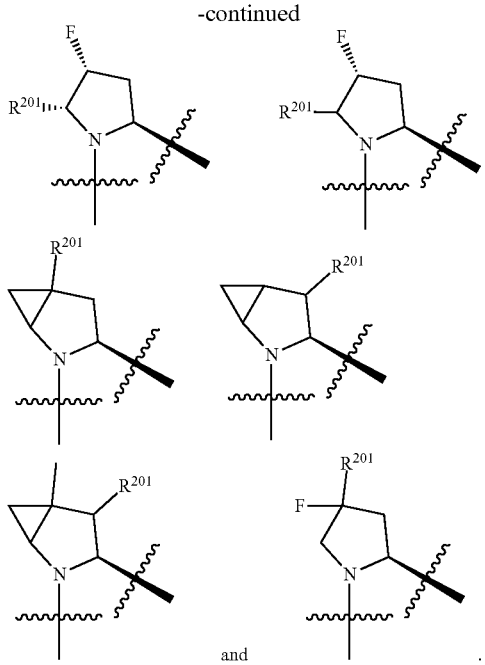
In one embodiment C4 is selected from:
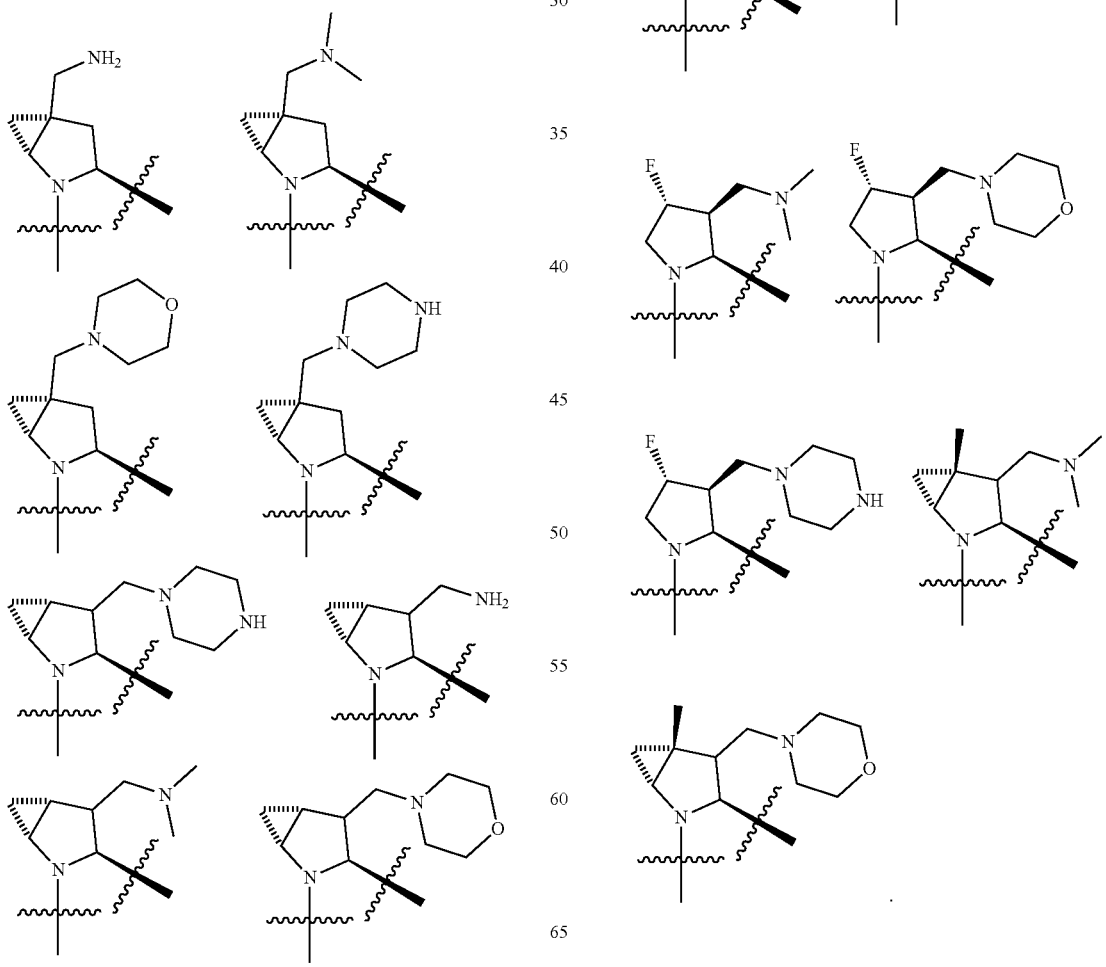
-continued
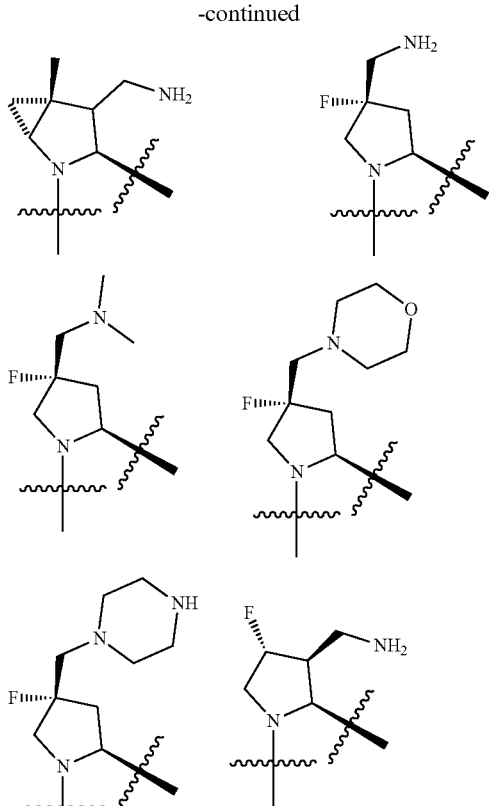

In one embodiment C4 is selected from:
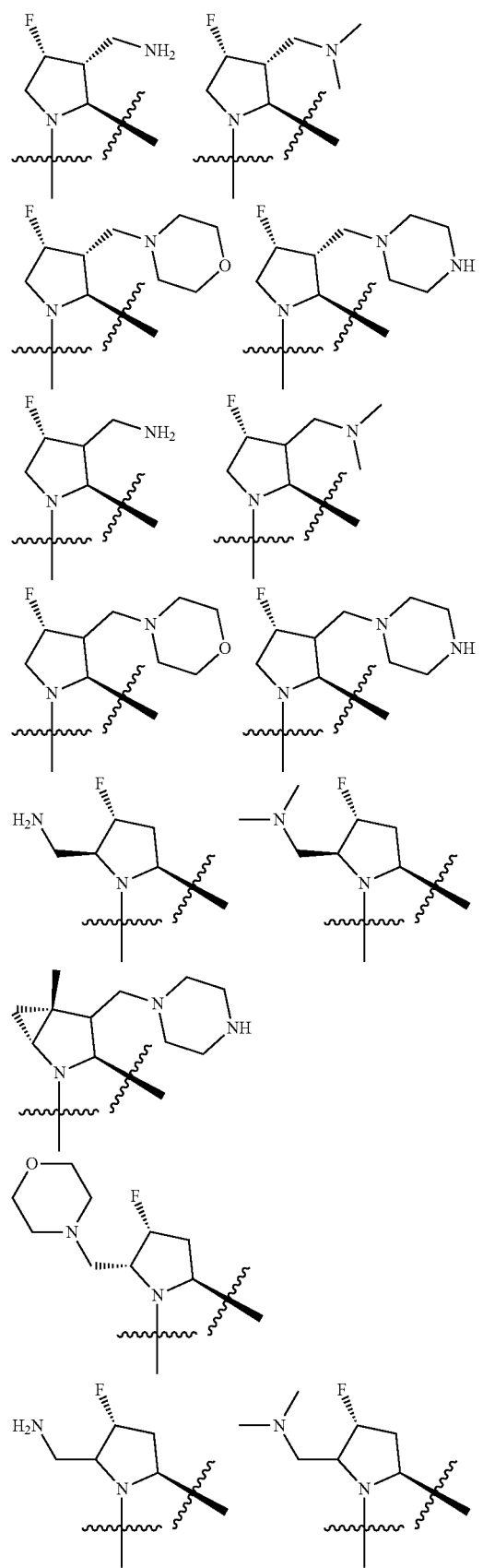
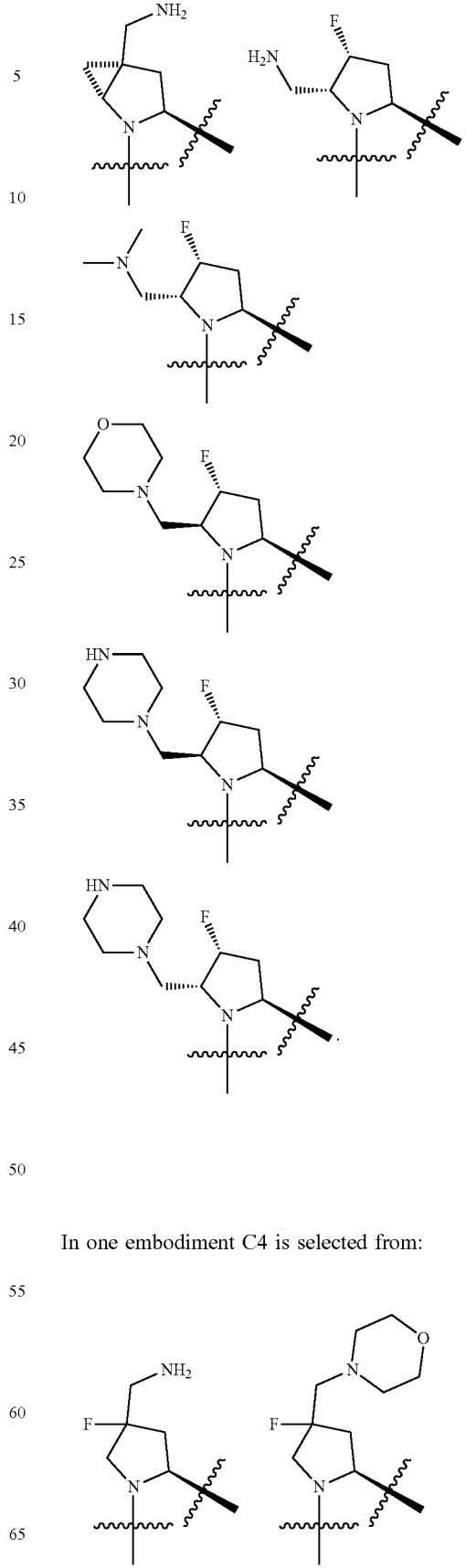
In one embodiment C4 is selected from:

-continued
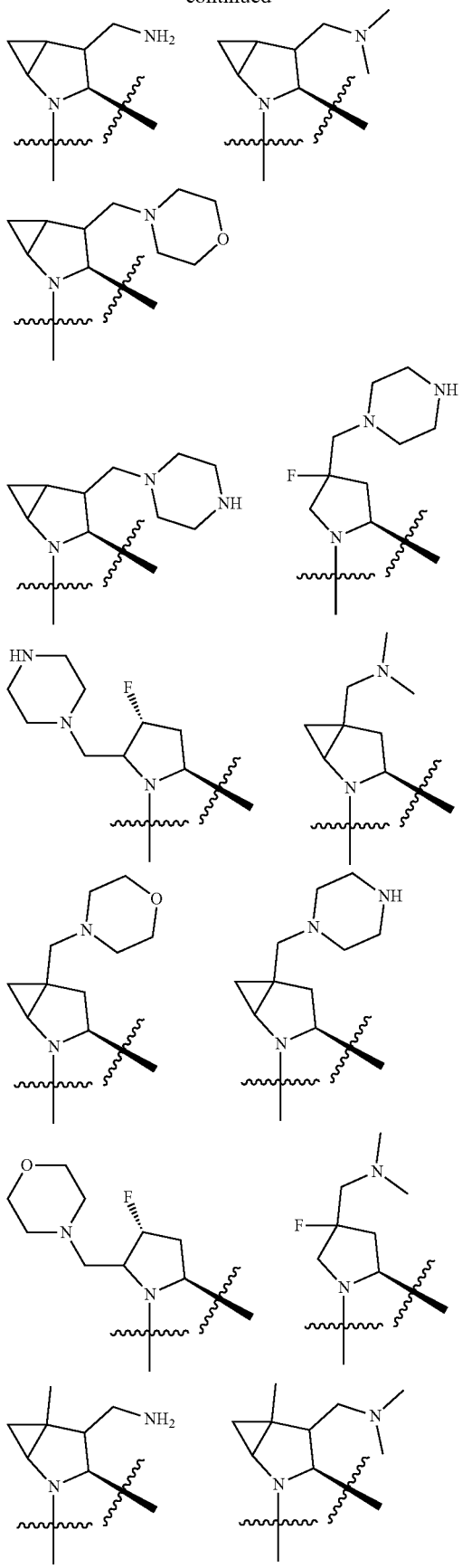
-continued
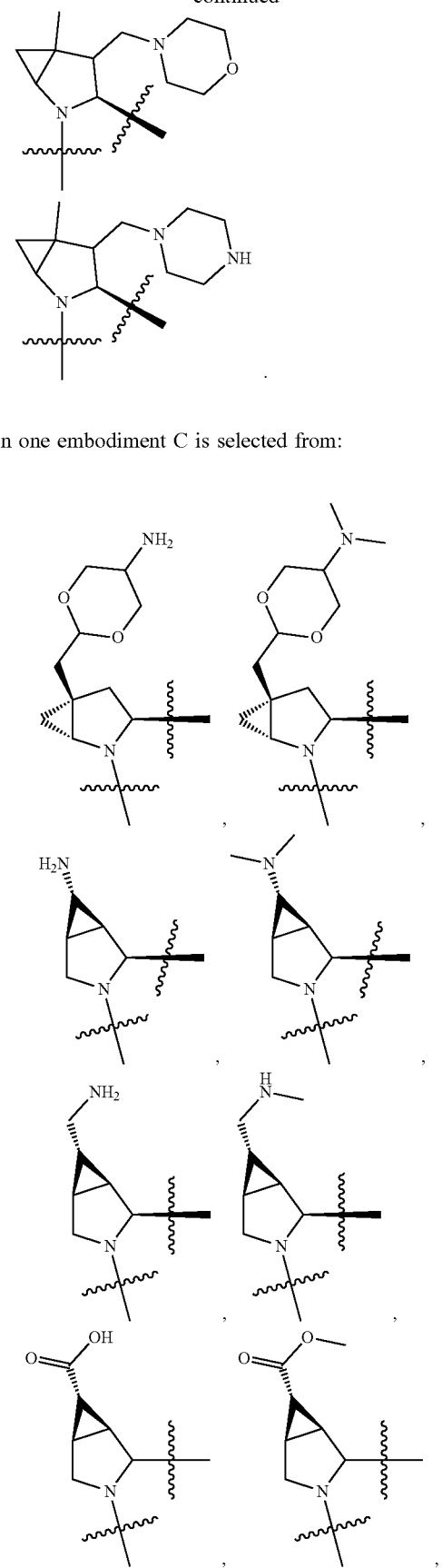
In one embodiment C is selected from:

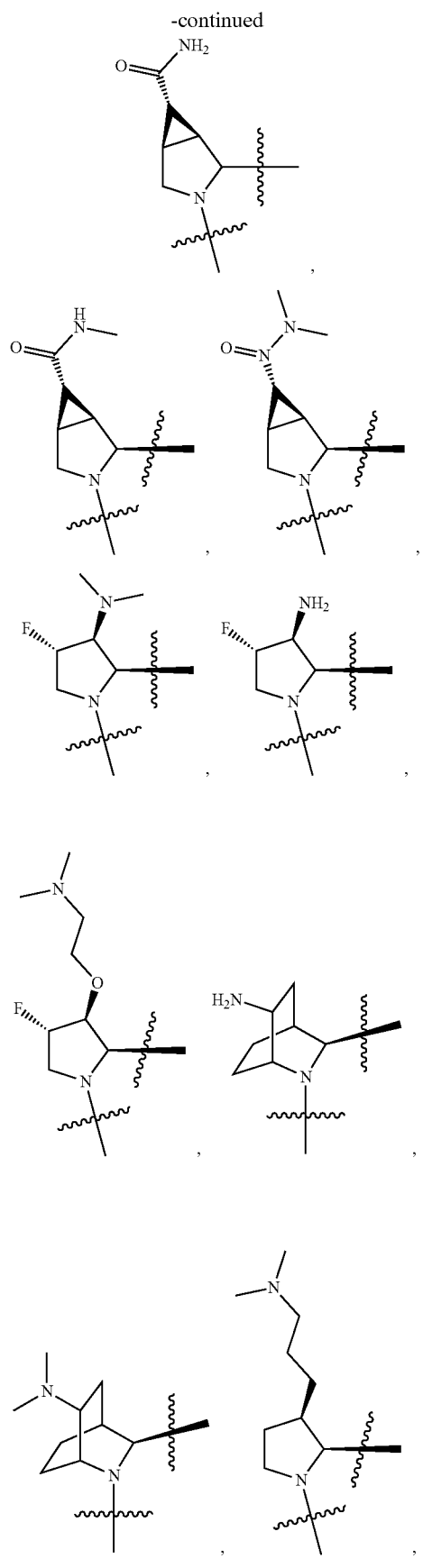
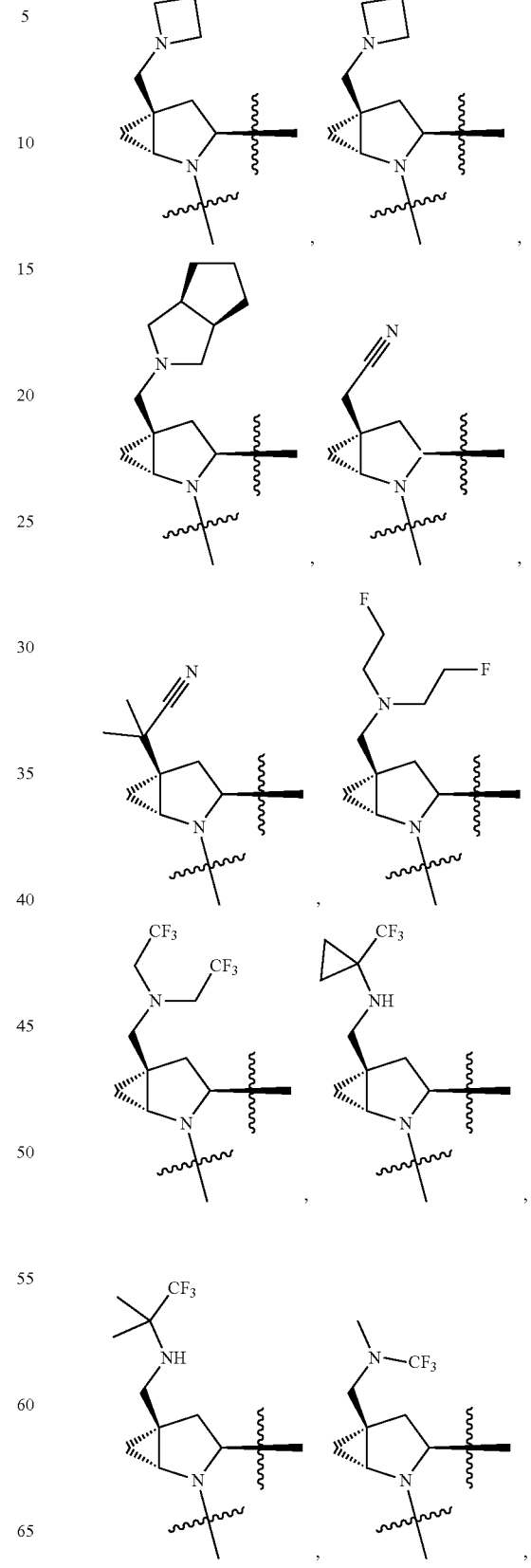

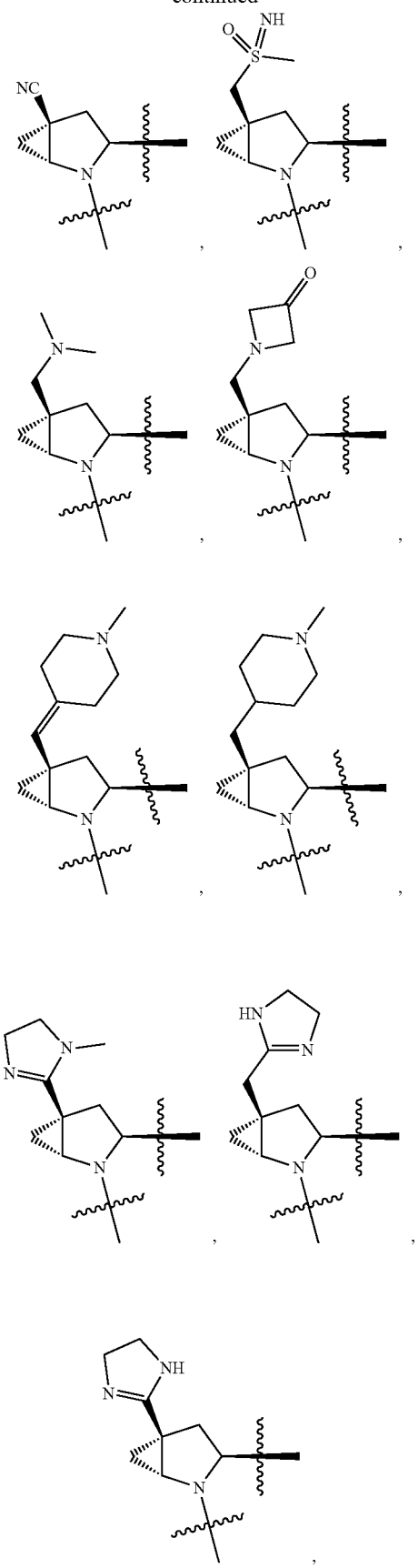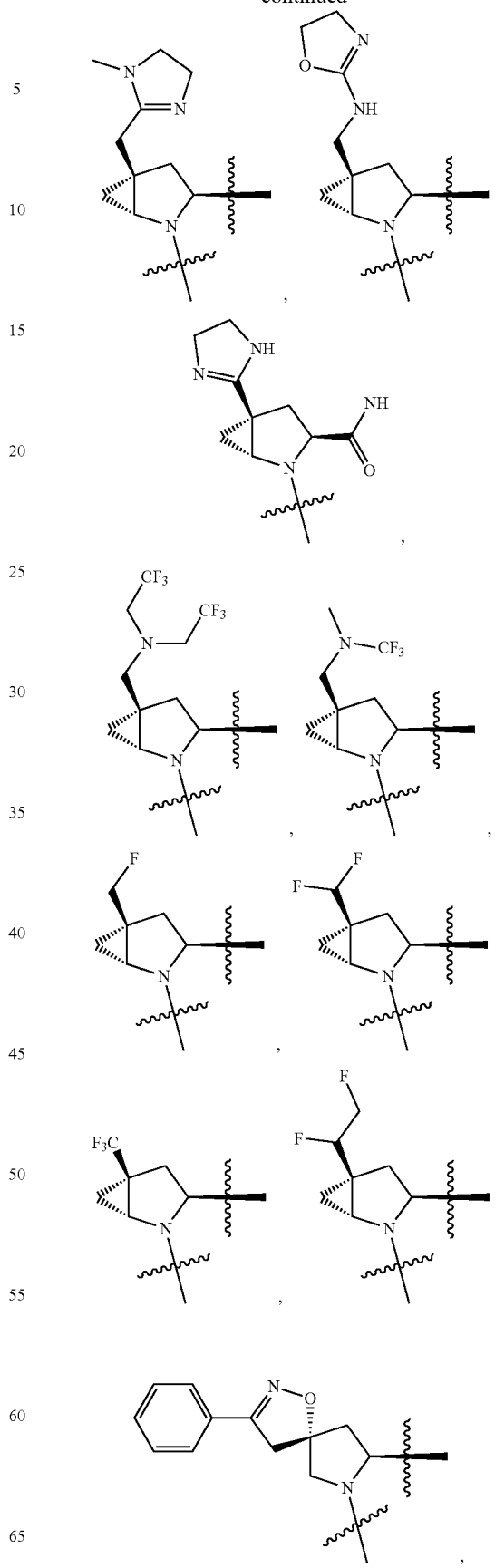

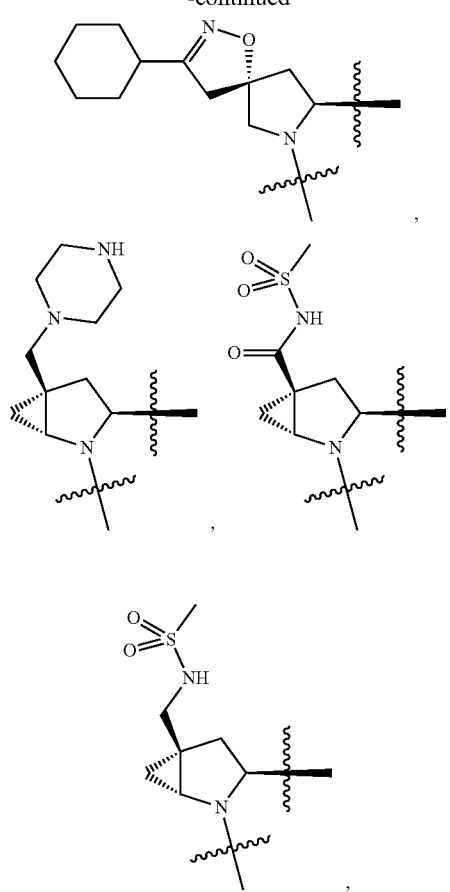
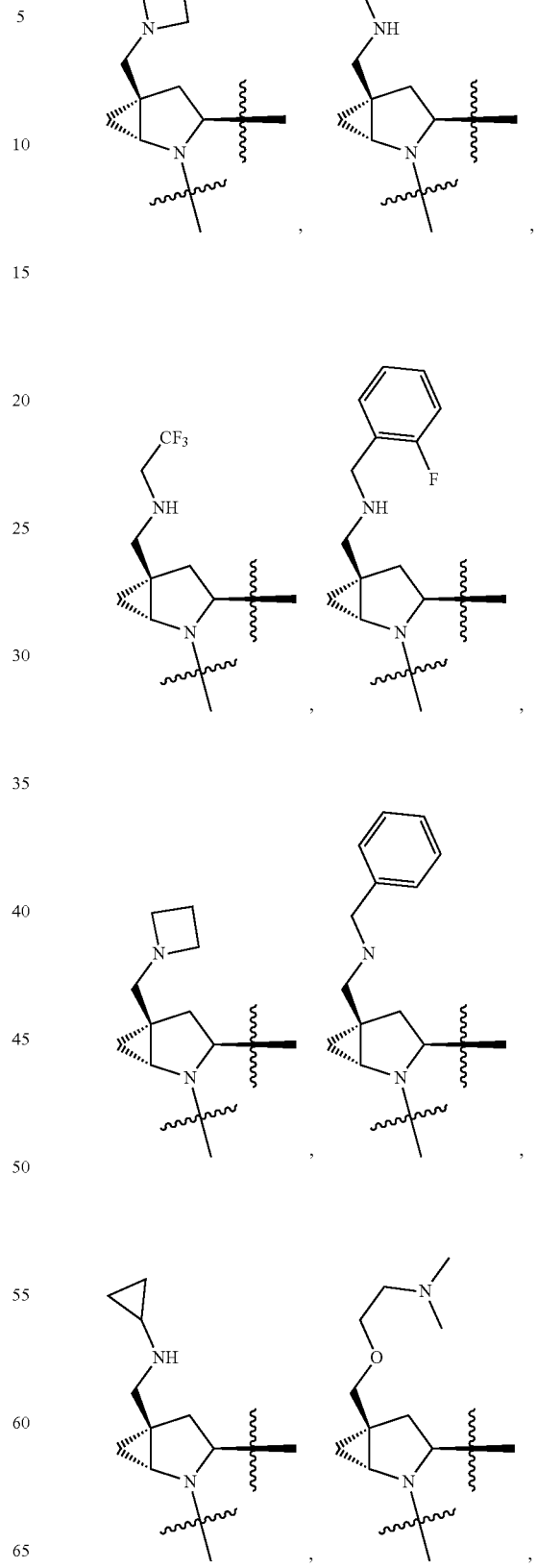

101
-continued
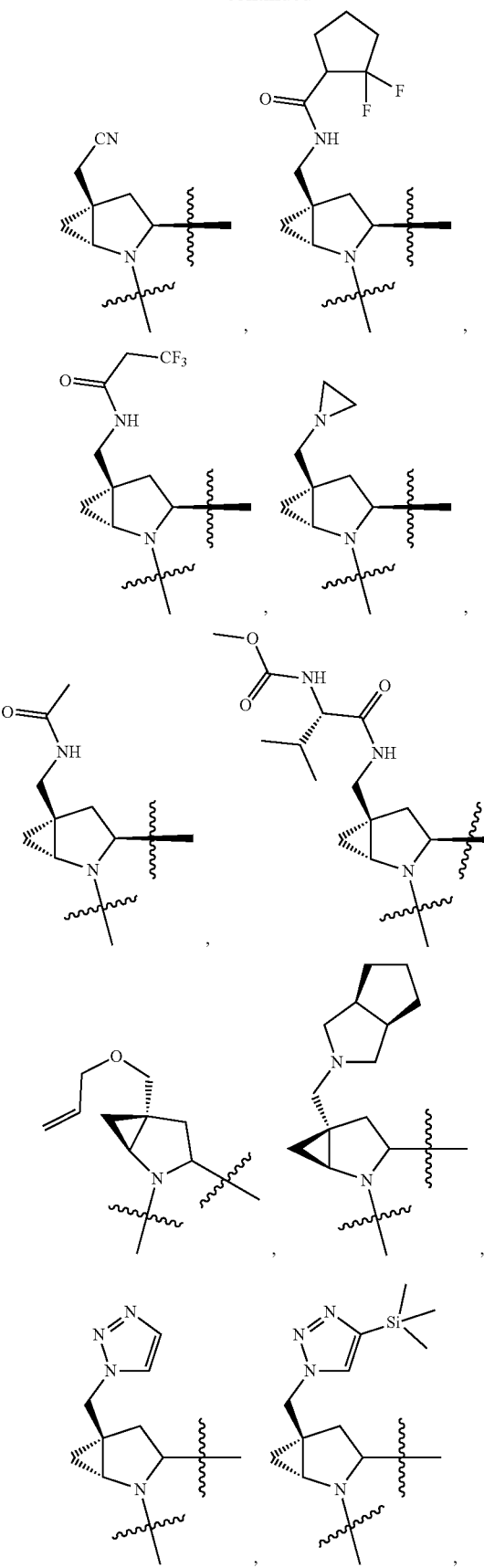
102
-continued
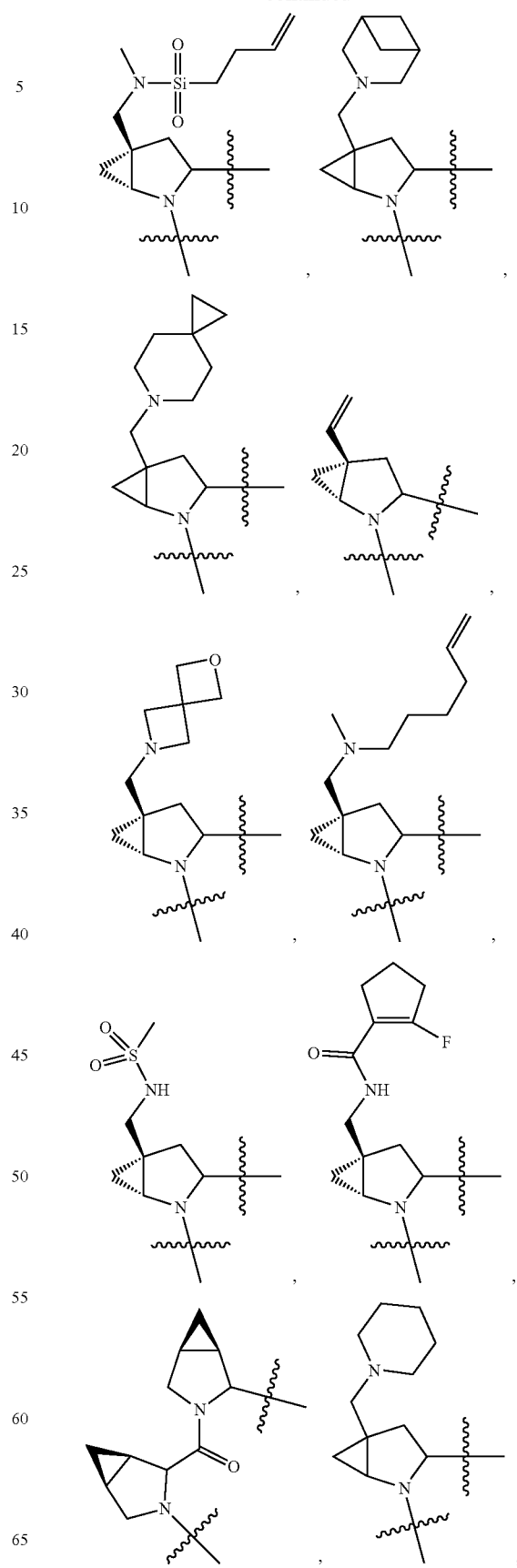

103
-continued

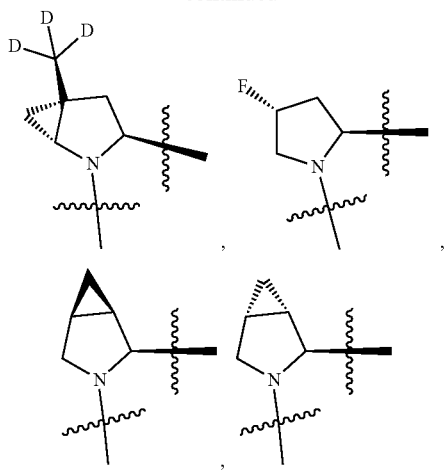

In one embodiment R¹ is selected from F, Cl, Br, and $C_1$-$C_6$alkyl.

In one embodiment R¹ is selected from hydroxyl and $C_1$-$C_6$alkoxy.

In one embodiment R¹ is selected from $C_2$-$C_6$alkynyl, $C_2$-$C_6$alkanoyl, and $C_1$-$C_6$thioalkyl.

In one embodiment R¹ is selected from amino$C_1$-$C_6$alkyl and —$C_0$-$C_4$alkylNR⁹R¹⁰.

In an alternative embodiment, C is selected from

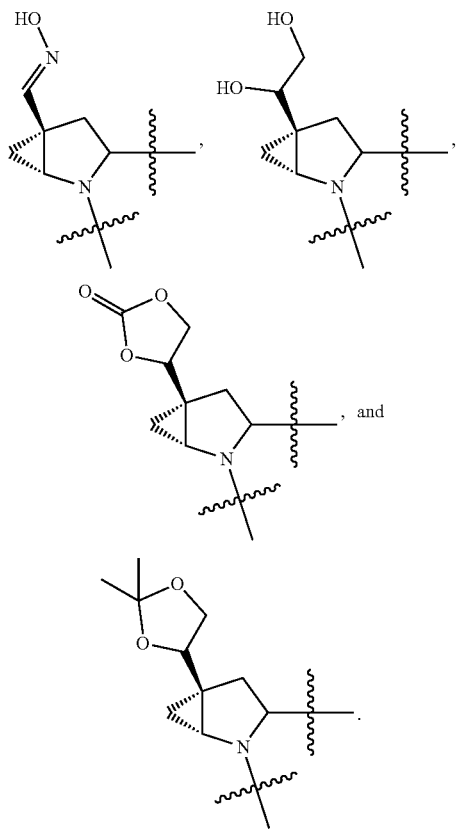

104
Embodiments of A

Non-limiting examples of A1 include:

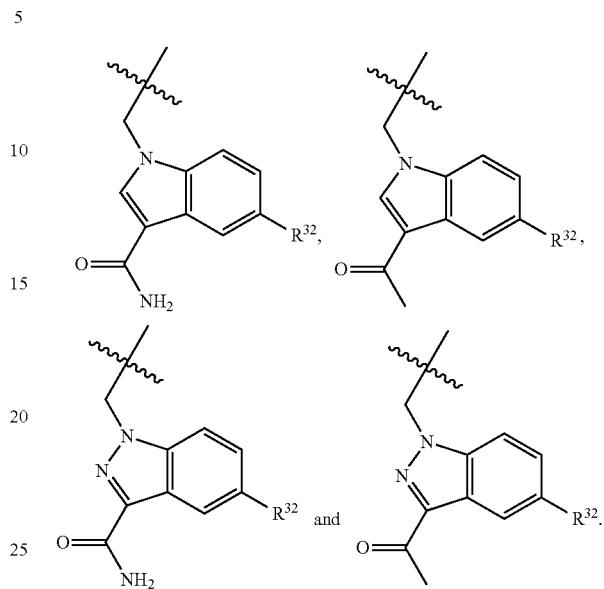

In one embodiment A1 is selected from:

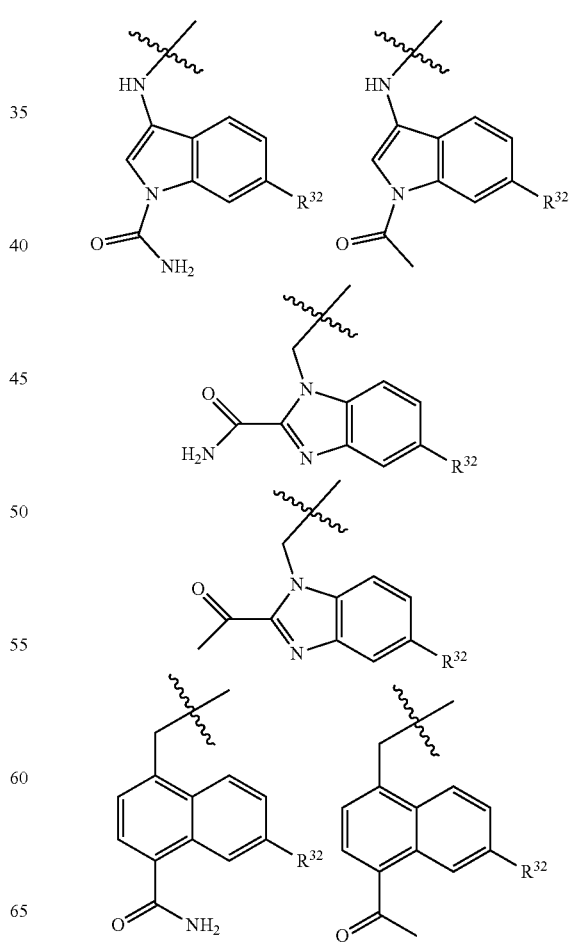

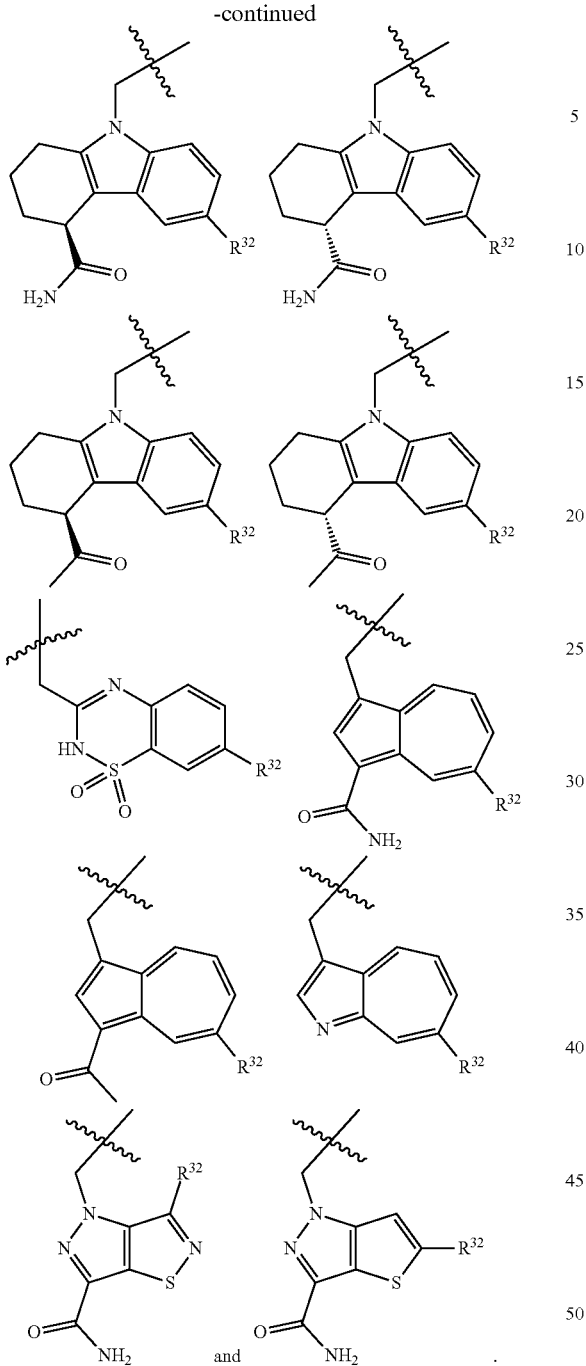
In one embodiment A3 is selected from:
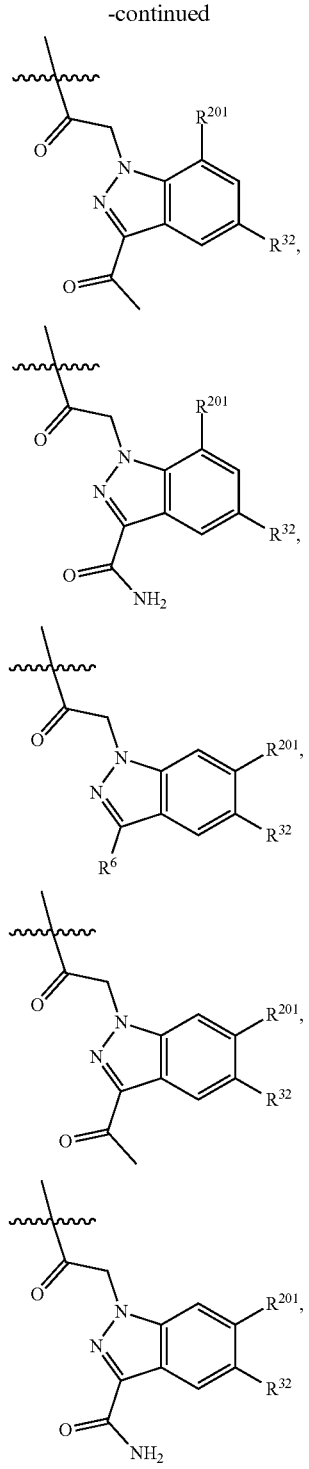
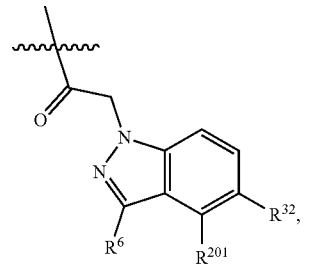

-continued
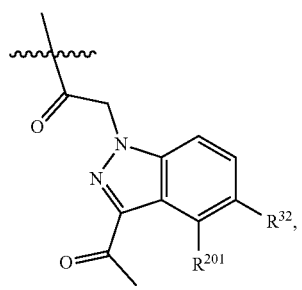
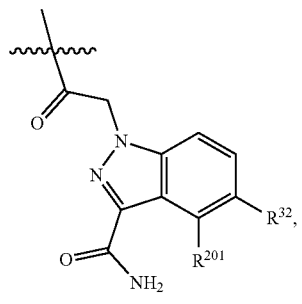
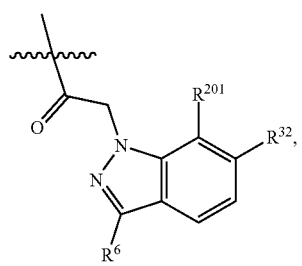
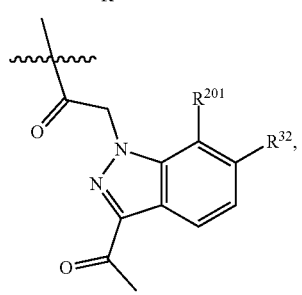
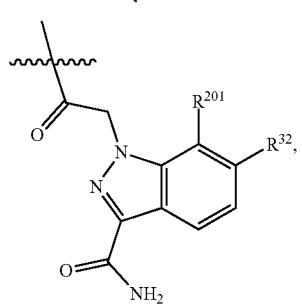
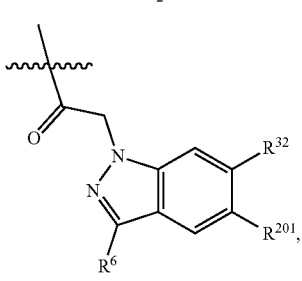
-continued
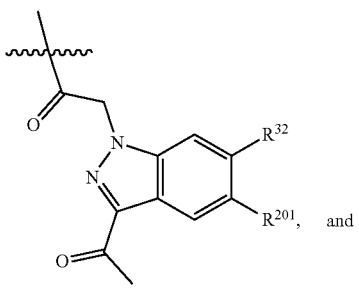
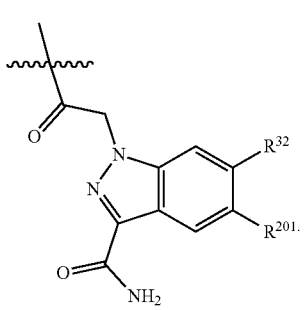
In one embodiment A3 is selected from:
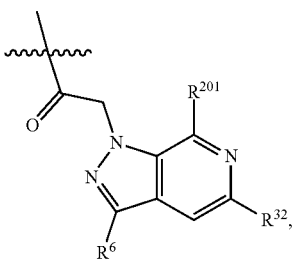
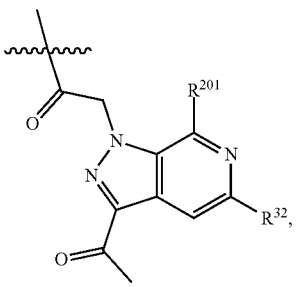
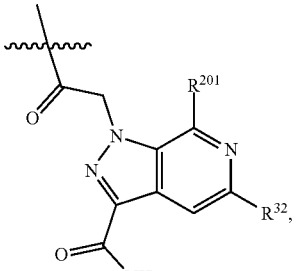

-continued
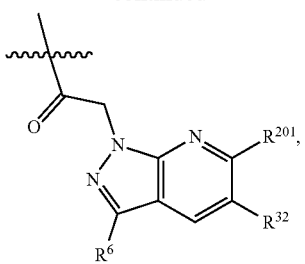
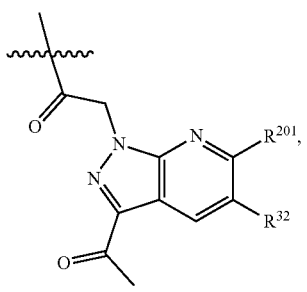
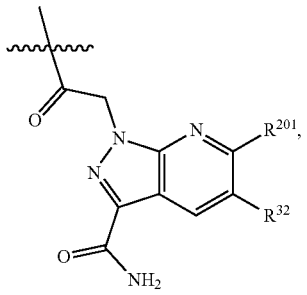
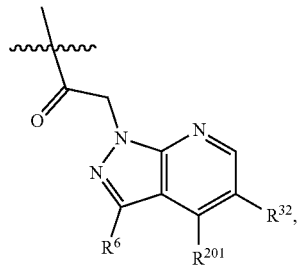
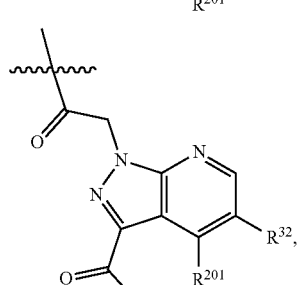
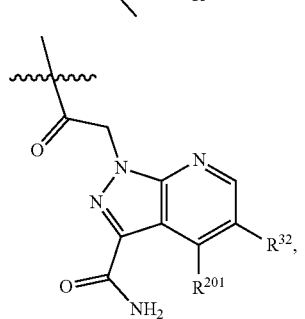
-continued
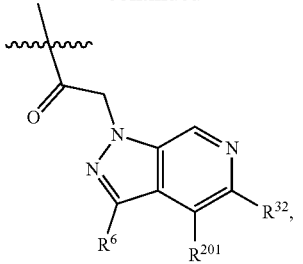
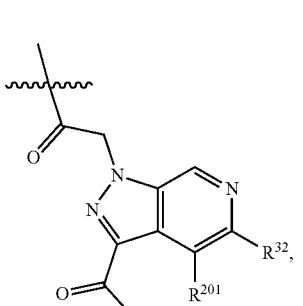
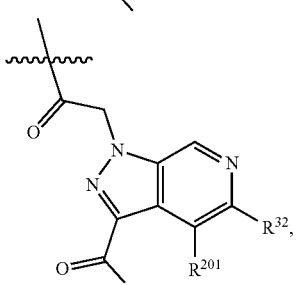
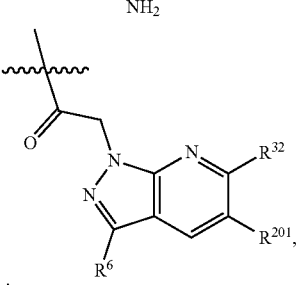
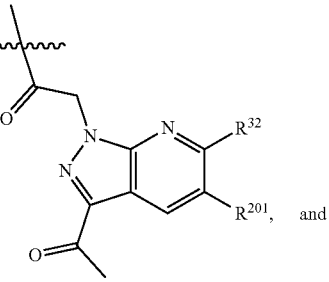, and
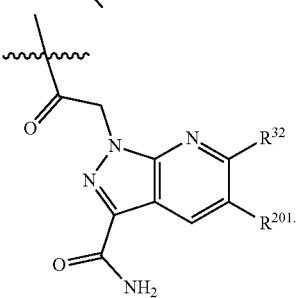.

In one embodiment A3 is selected from:
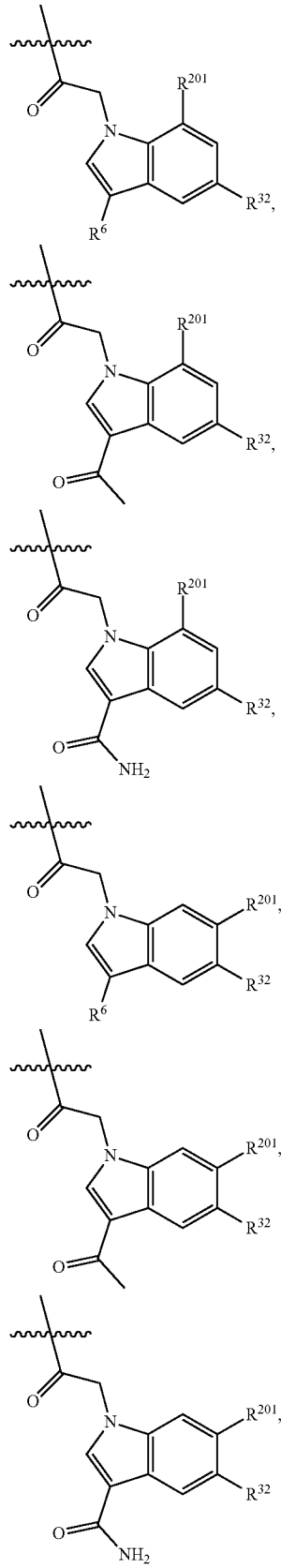
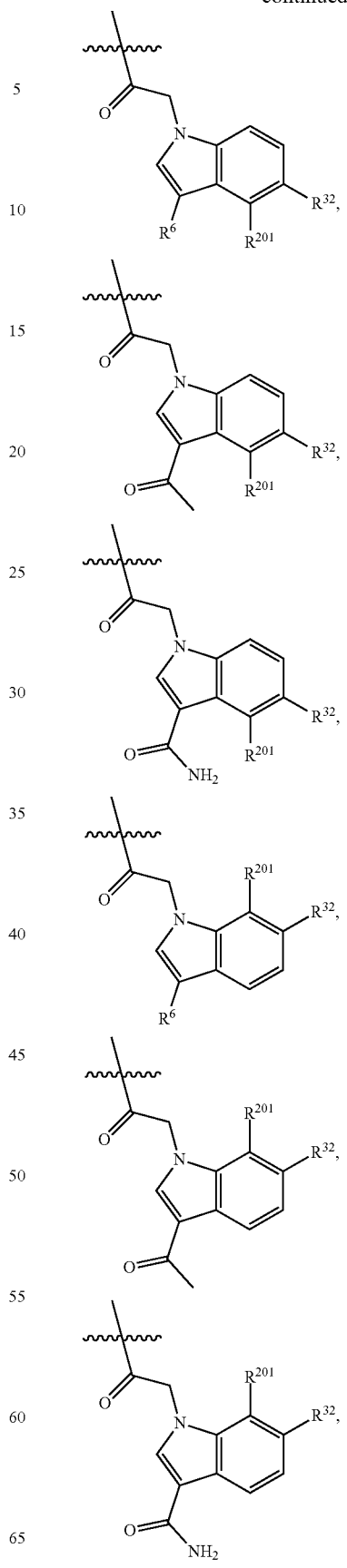

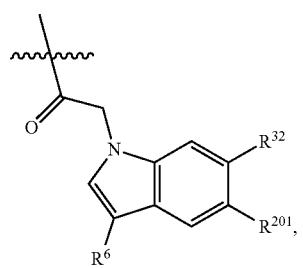
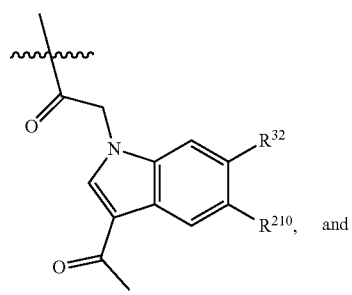 and
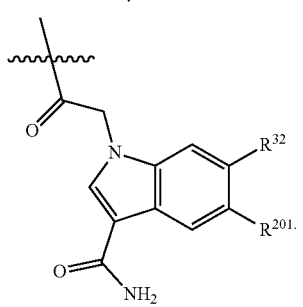
In one embodiment A3 is selected from:
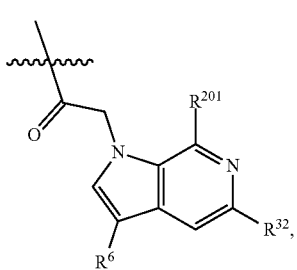
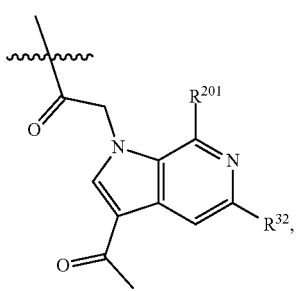
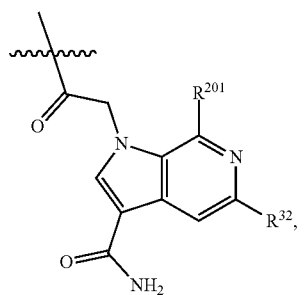
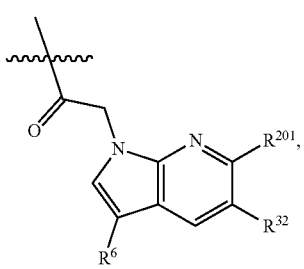
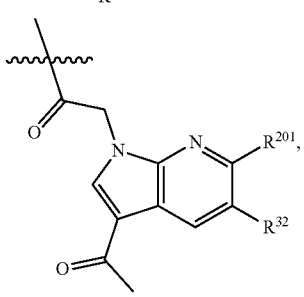
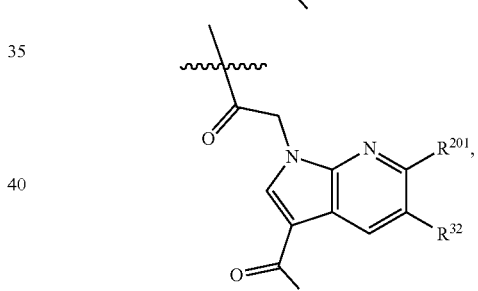
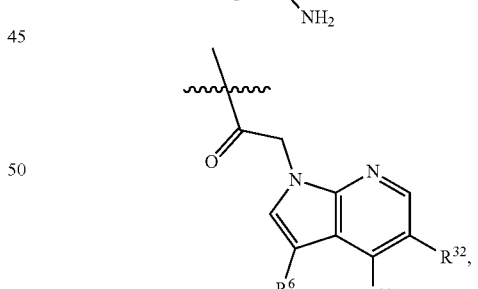
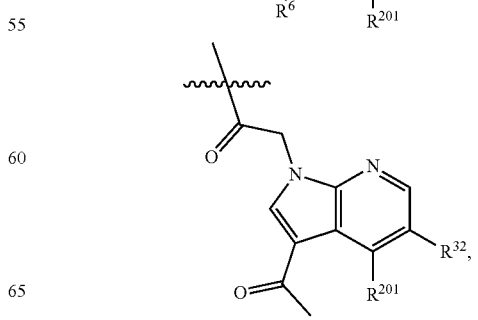

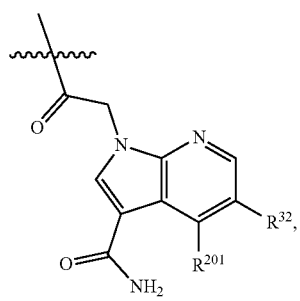
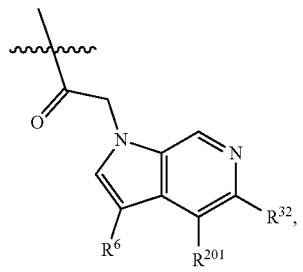
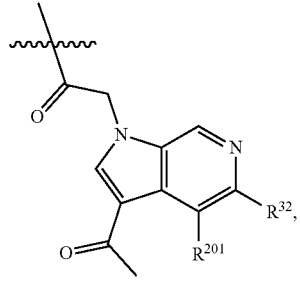
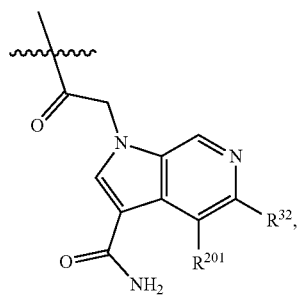
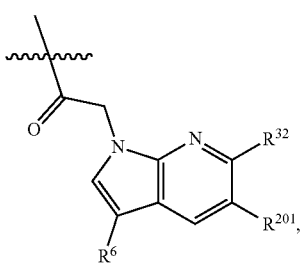
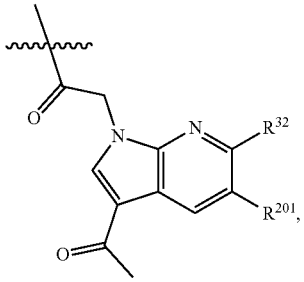
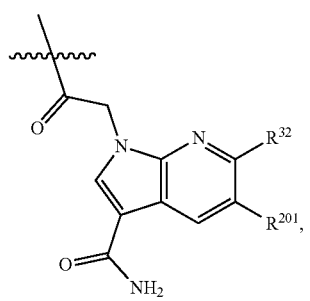
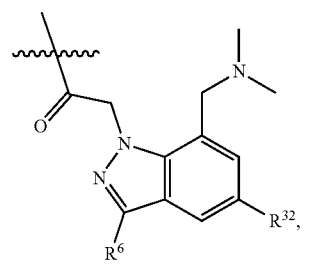
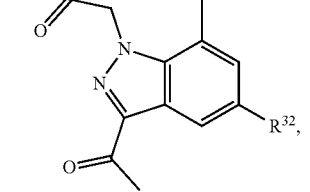
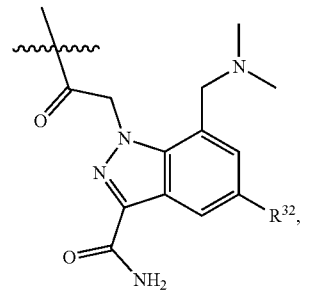
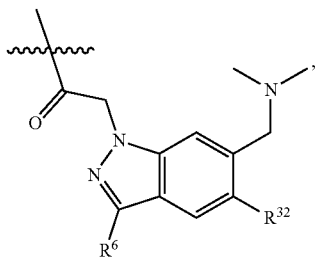
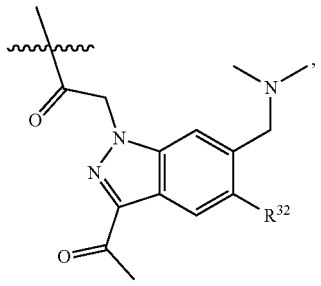

117
-continued
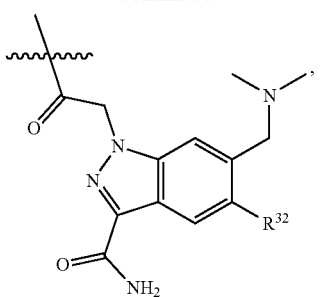
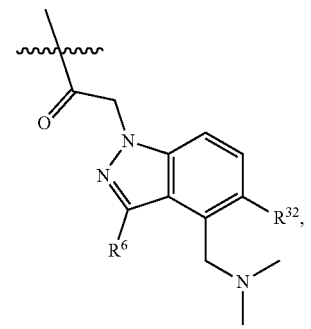
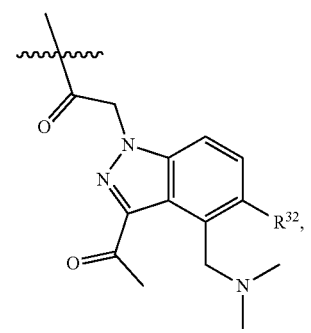
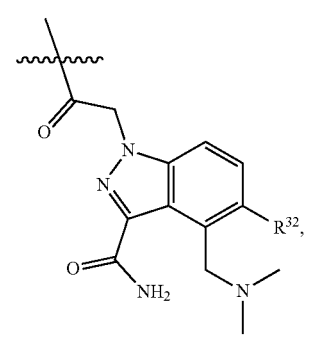
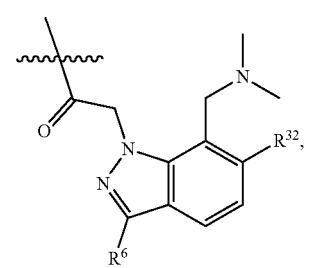
118
-continued
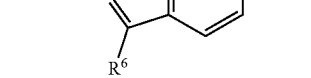
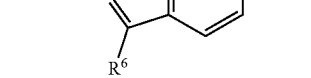
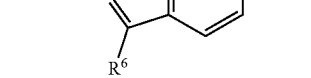
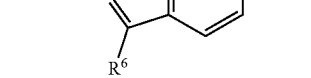, and
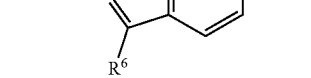

In one embodiment A3 is selected from:
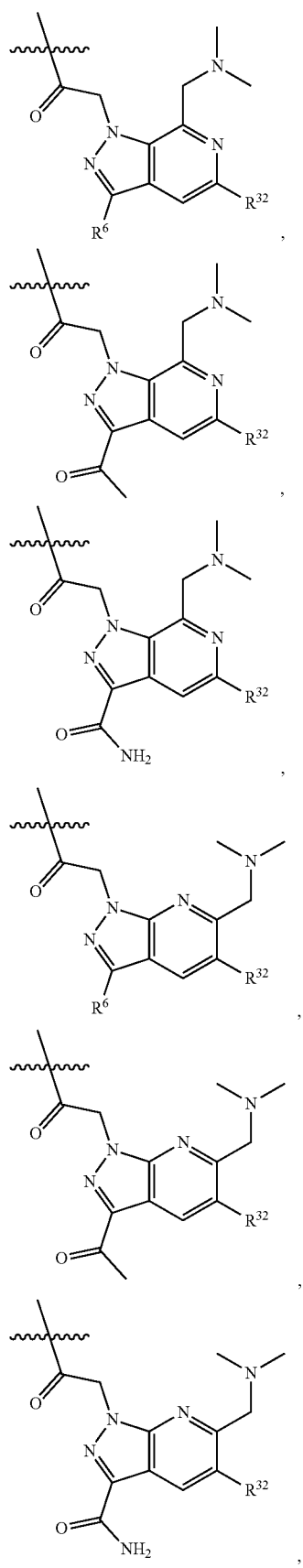
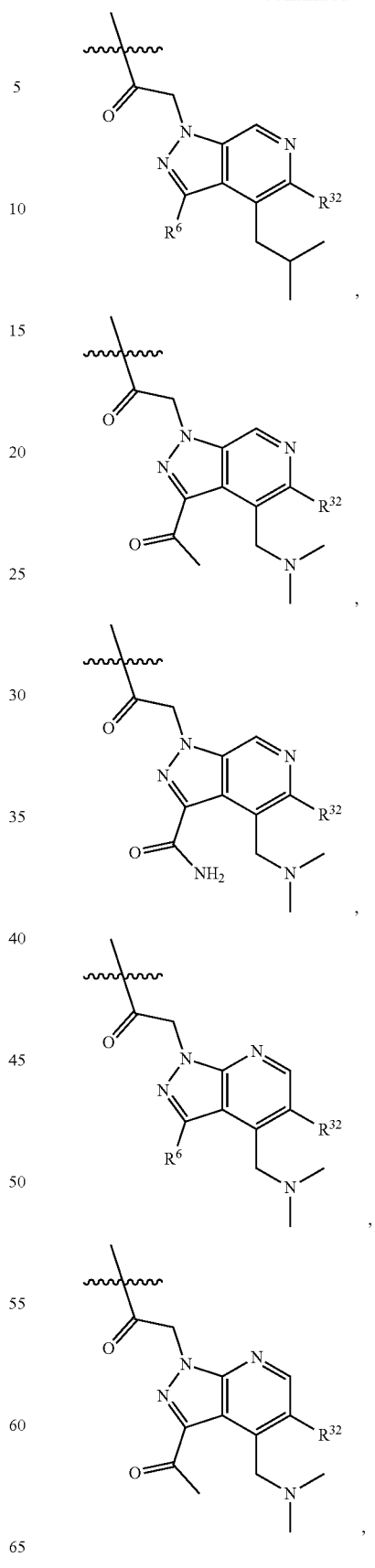

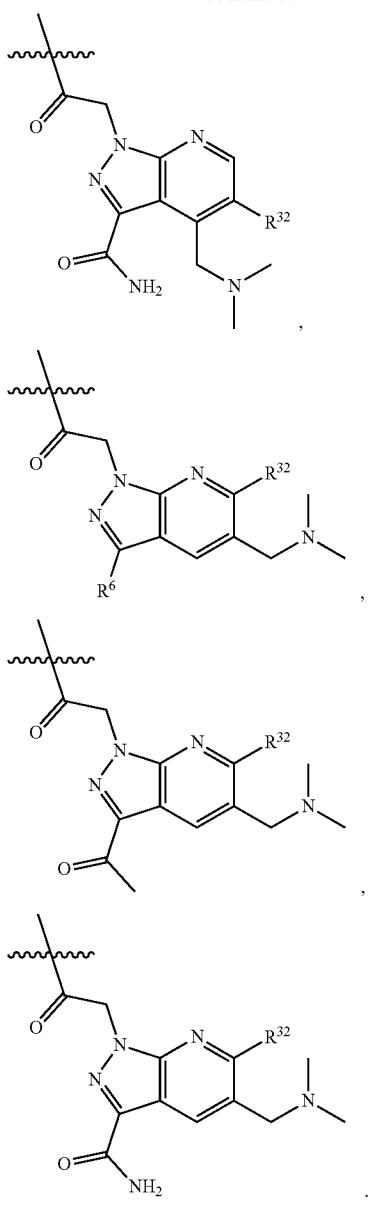
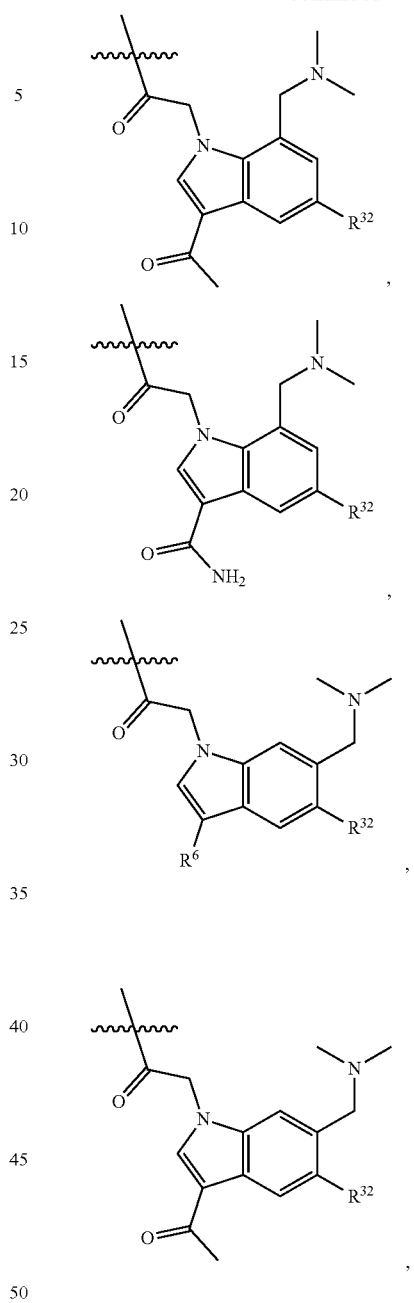
In one embodiment A3 is selected from:
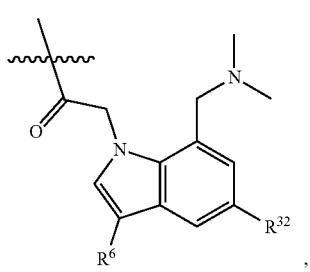
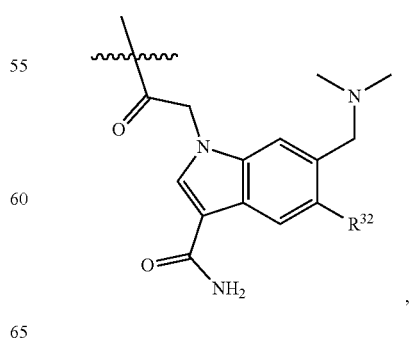

123
-continued
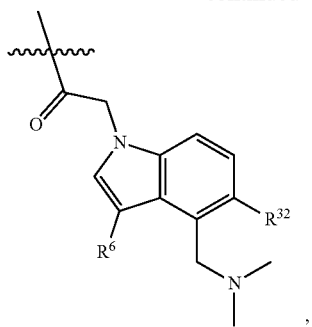
,

,
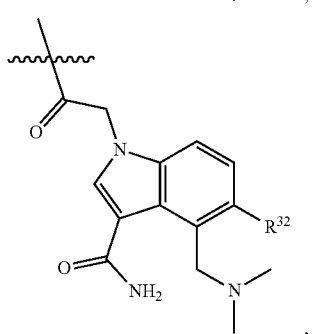
,
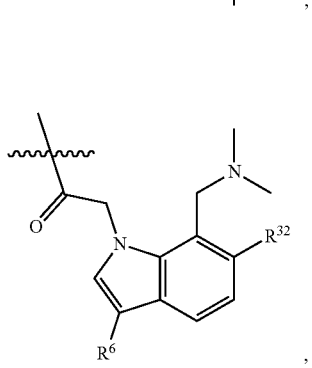
,
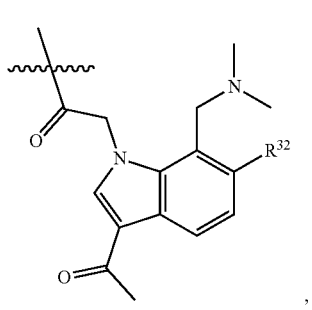
,
124
-continued
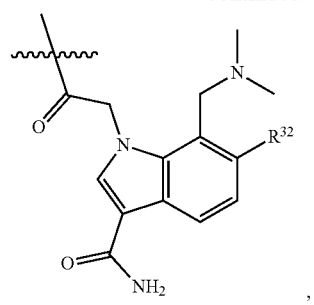
,
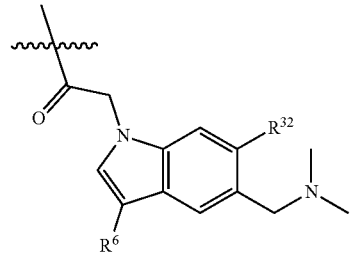
,
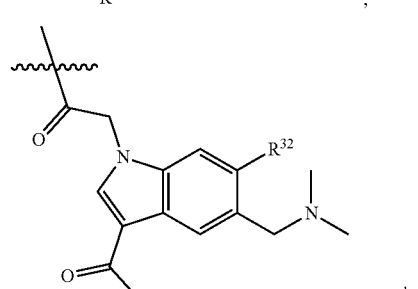
, and
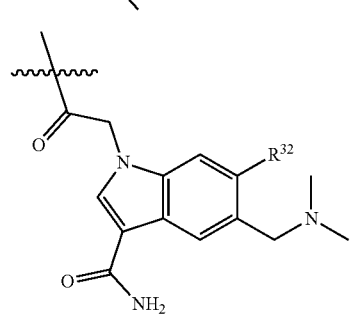
.
In one embodiment A3 is selected from:

125
-continued
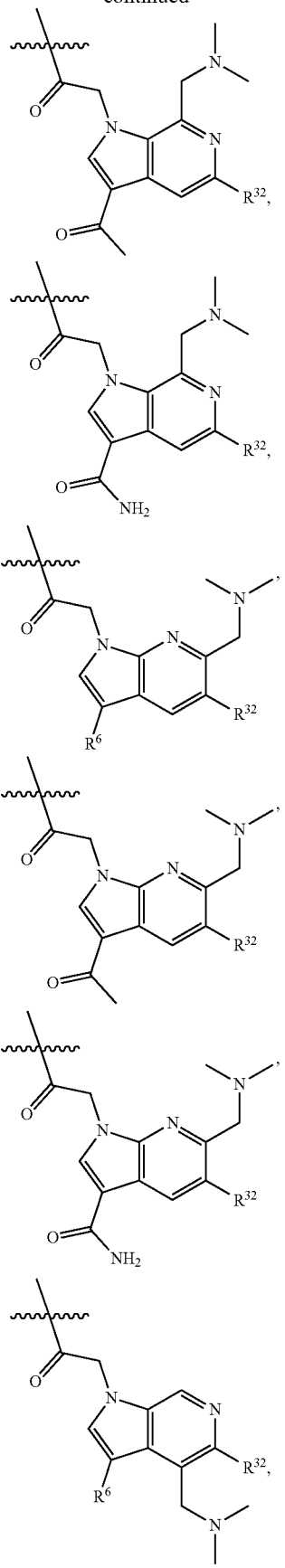
126
-continued
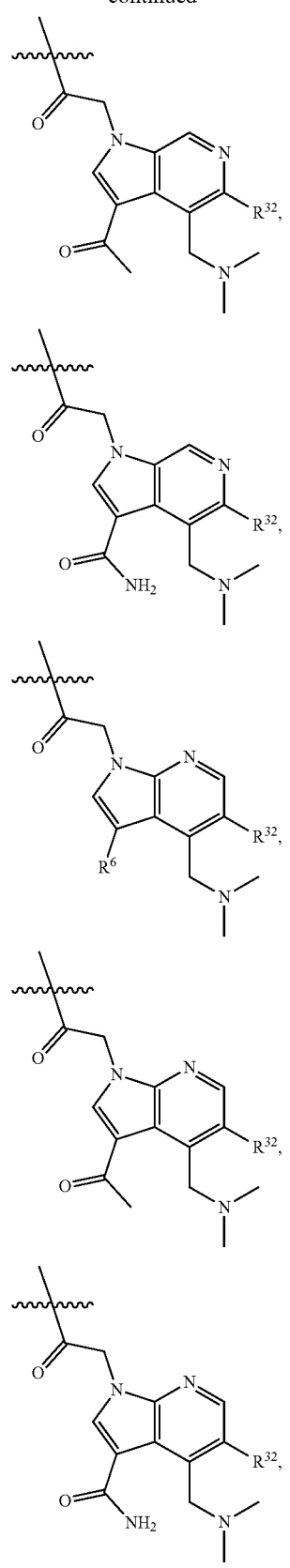

-continued
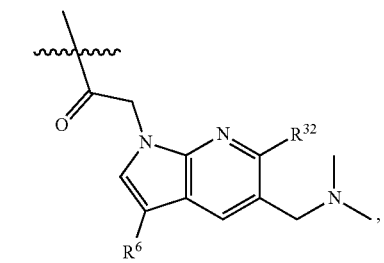
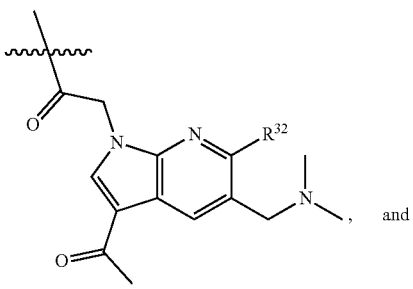, and
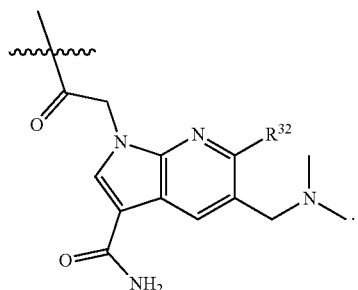
In one embodiment A1 is selected from:
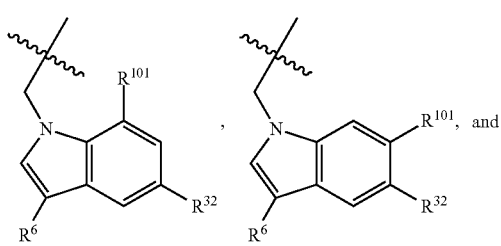
In one embodiment A1 is selected from:
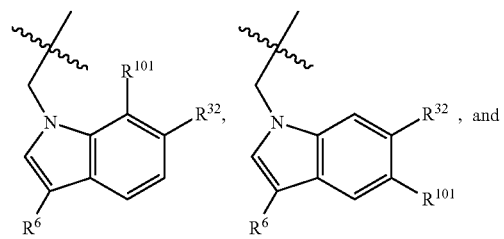
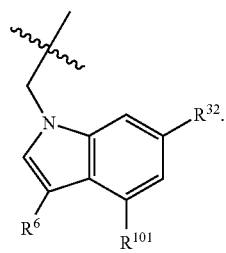
In one embodiment A1 is selected from:
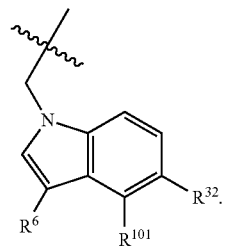
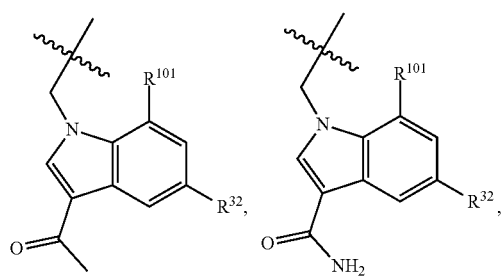
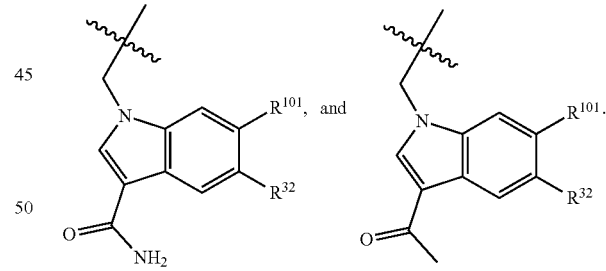
In one embodiment A1 is selected from:
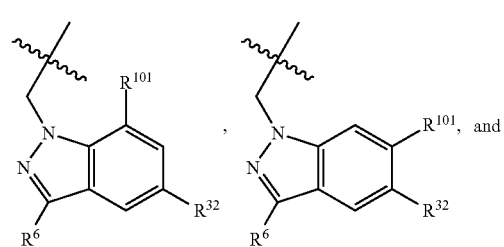

-continued
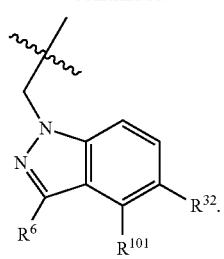
In one embodiment A1 is selected from:
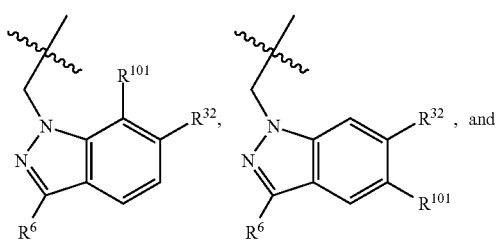
In one embodiment A1 is selected from:
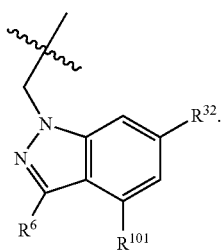
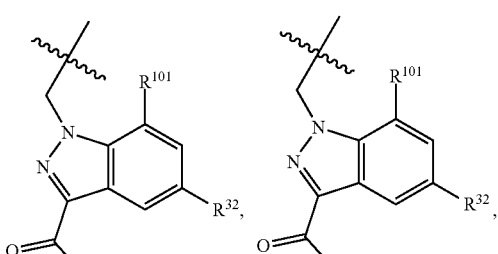
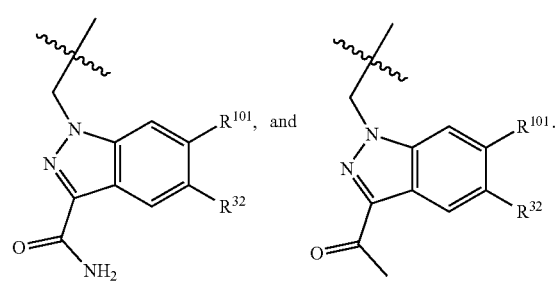
In the above embodiments and throughout this specification $R^{101}$ is $C_1$-$C_4$ alkyl or $C_3$-$C_7$ cycloalkyl.
In another embodiment A1 is selected from:
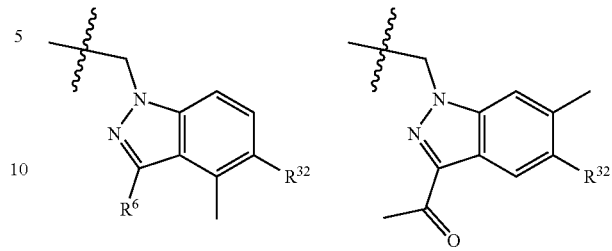
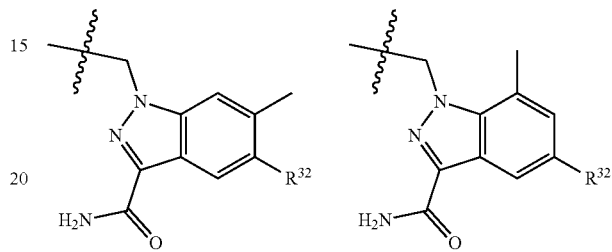
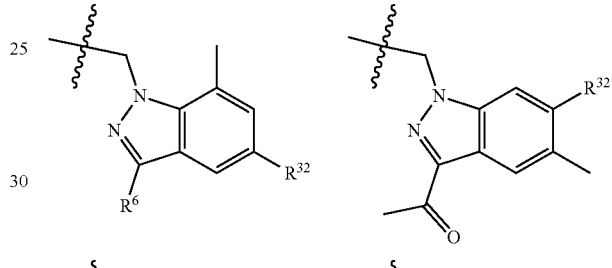
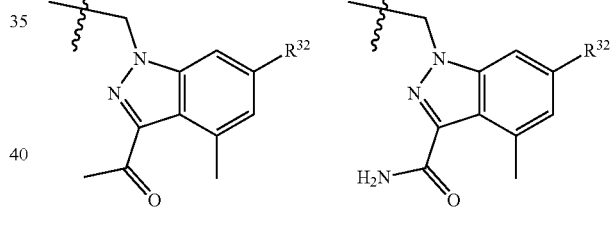
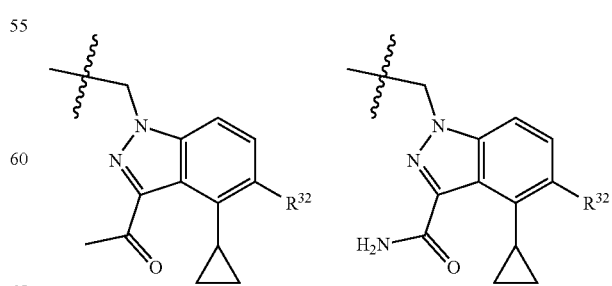

131
-continued
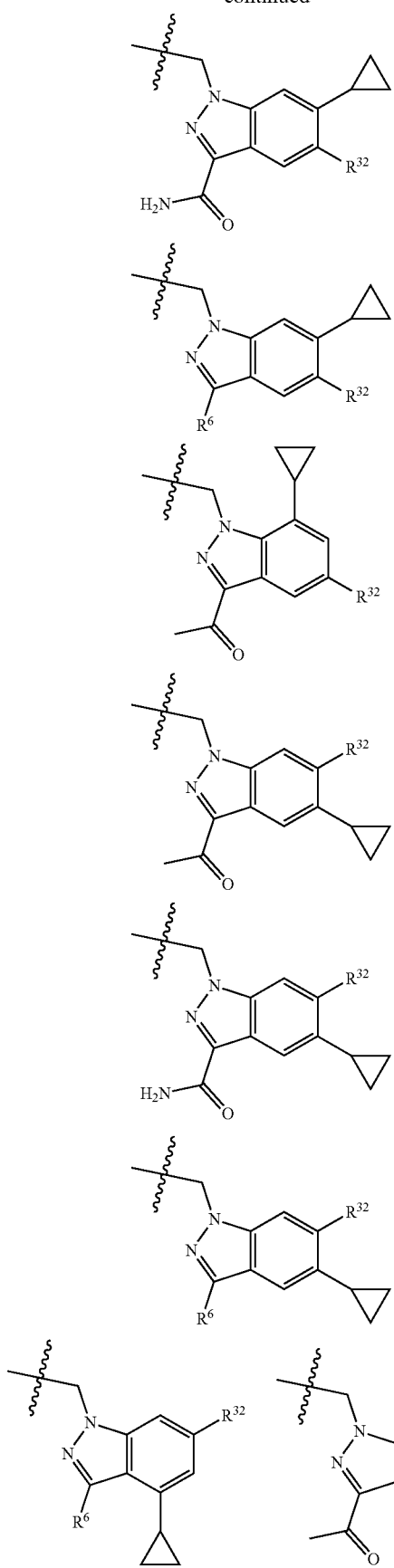
132
-continued
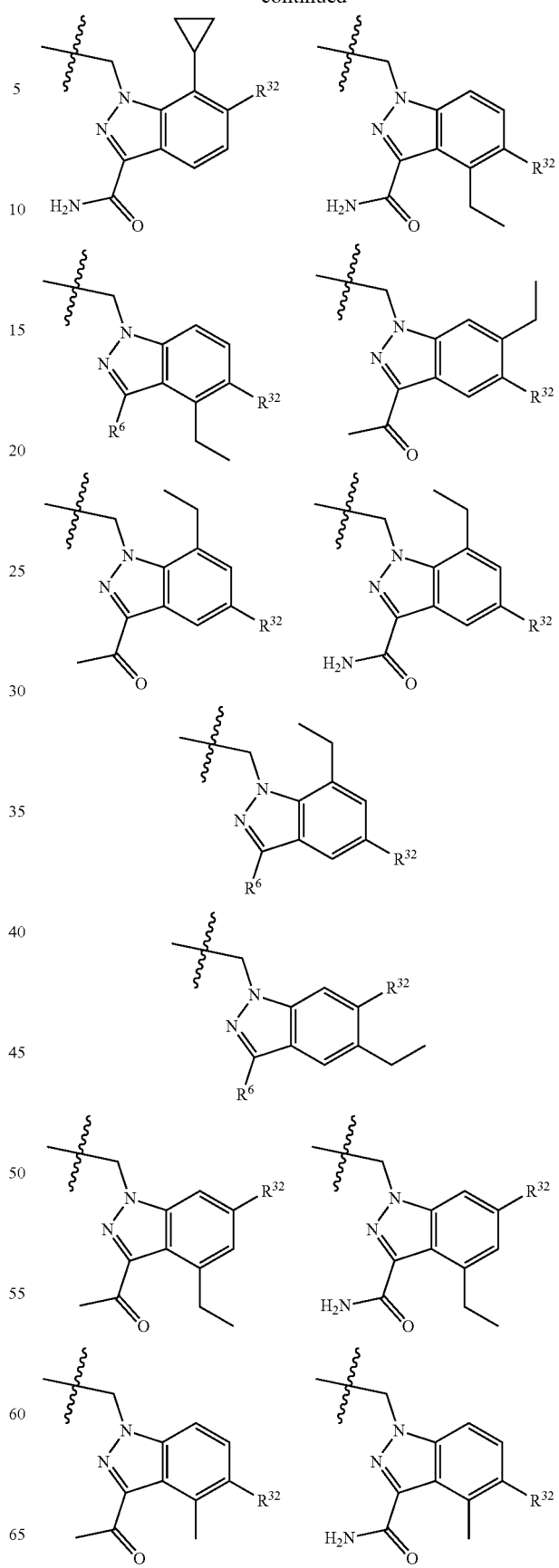

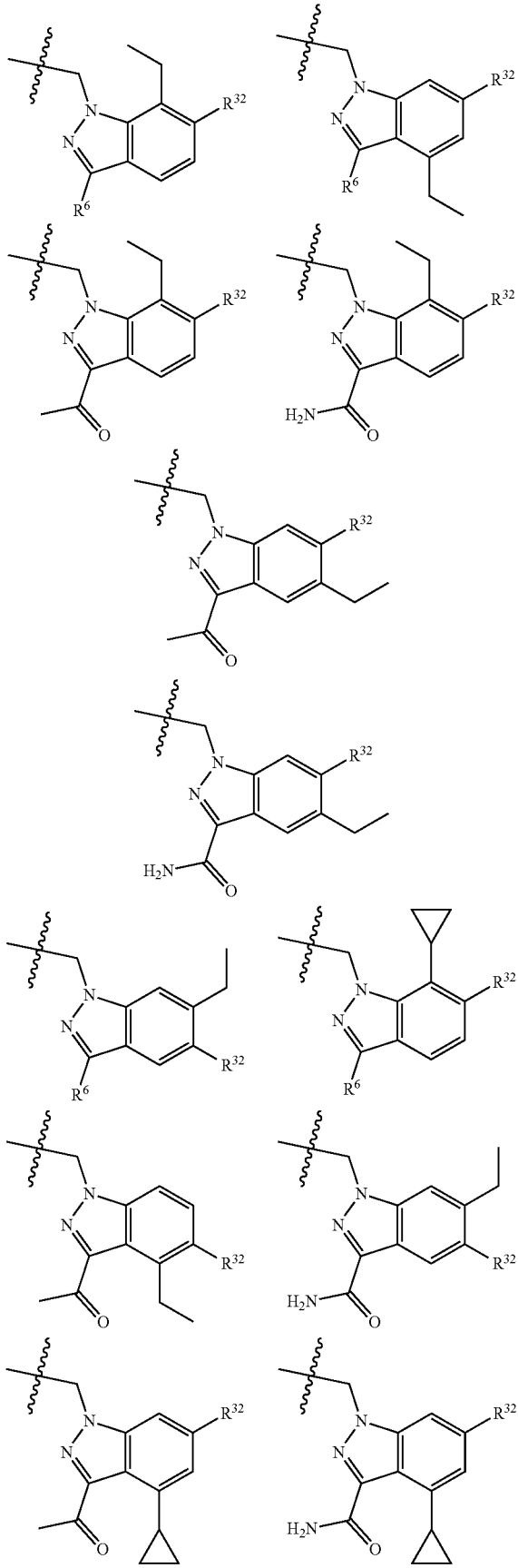
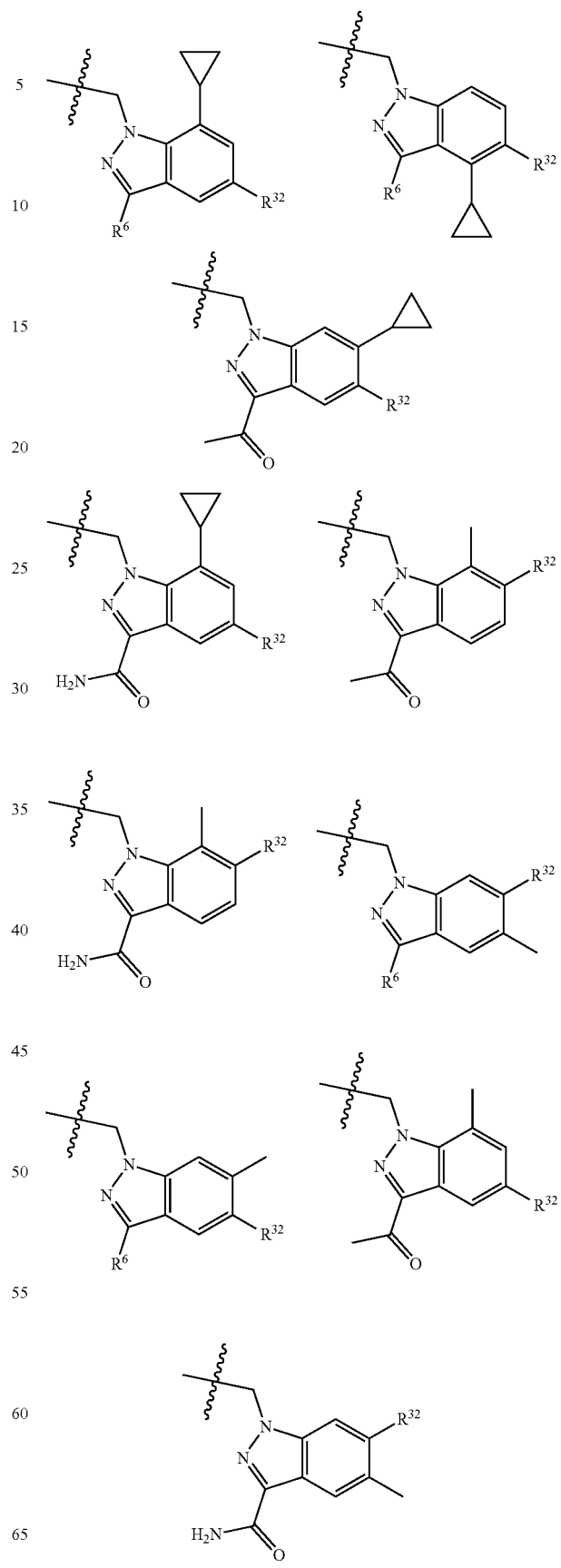

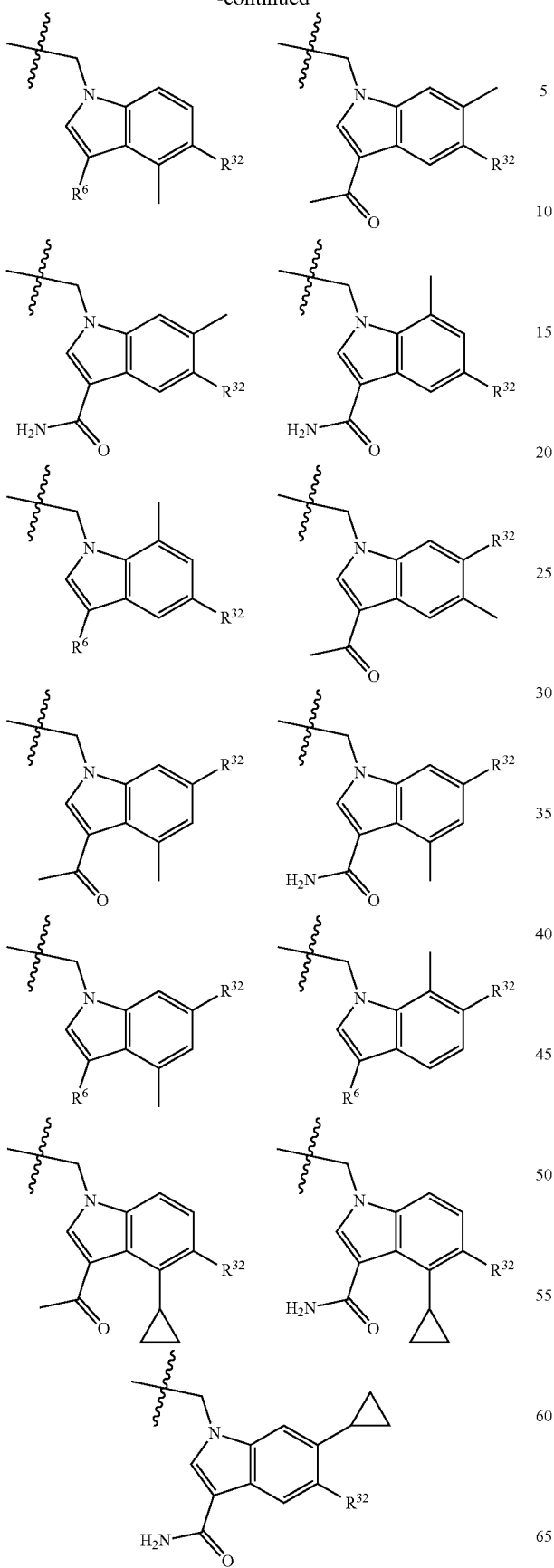
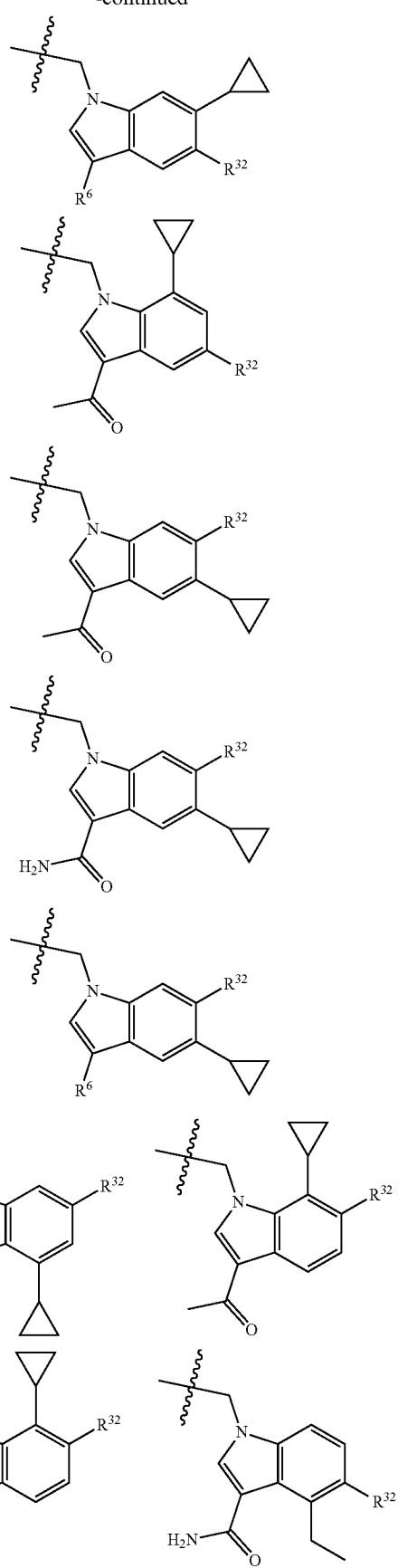

-continued
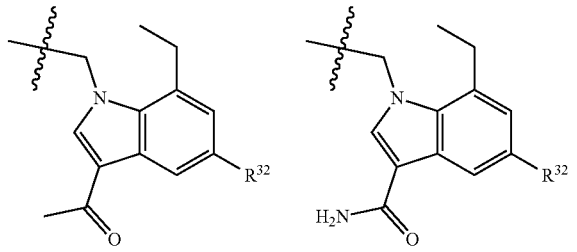
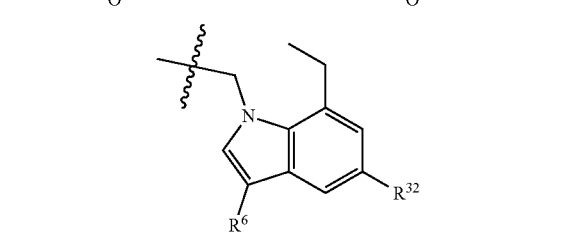
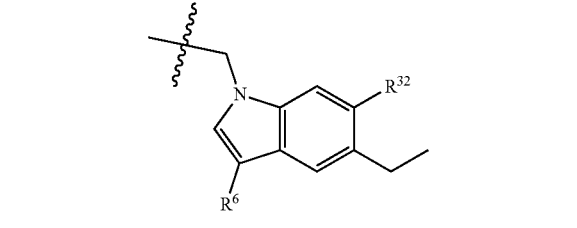
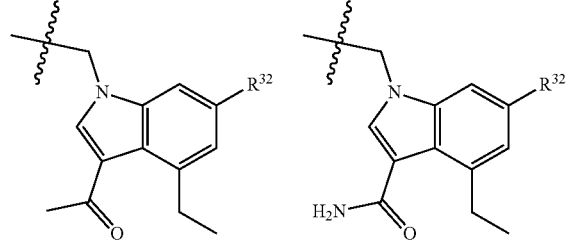
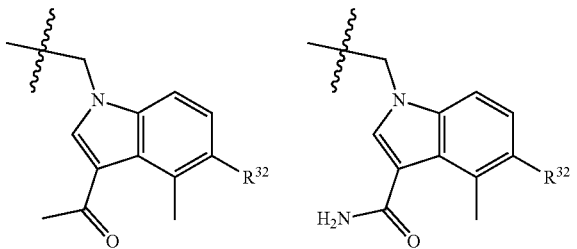
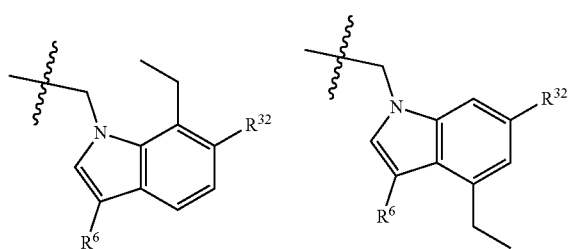
-continued
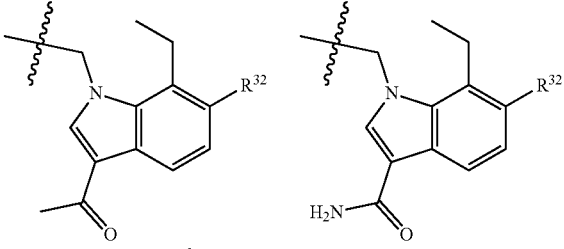
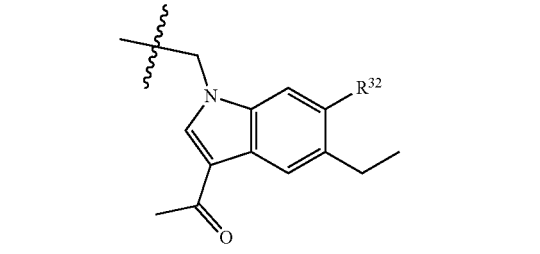
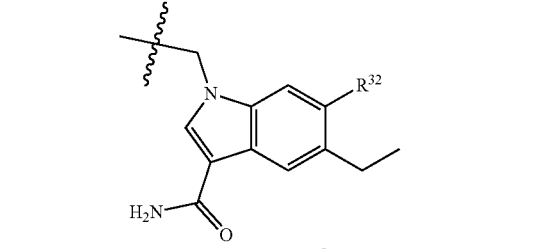
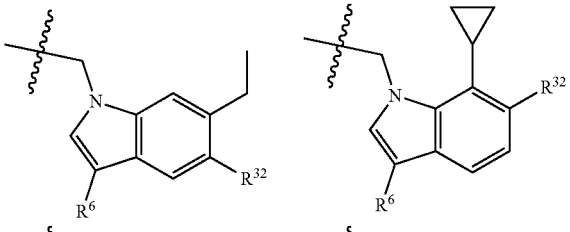
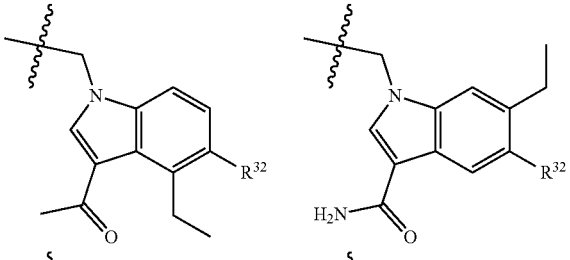
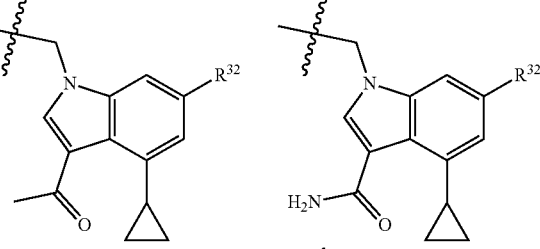
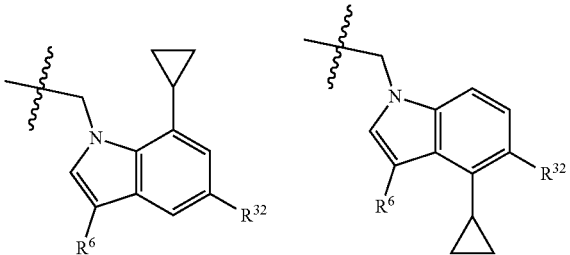

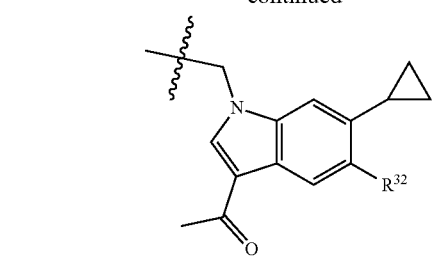
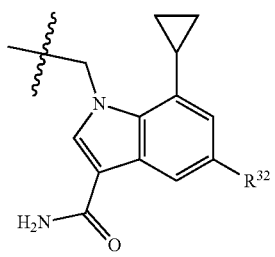
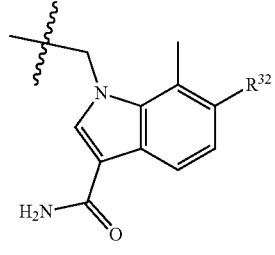
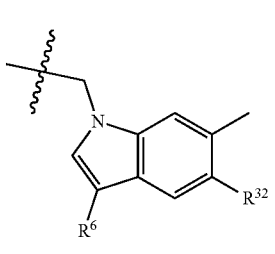
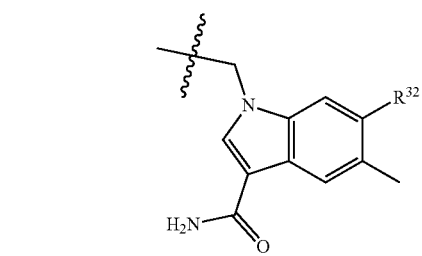
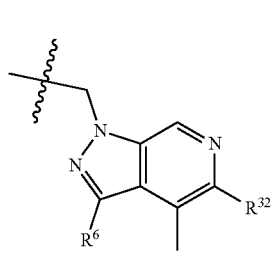
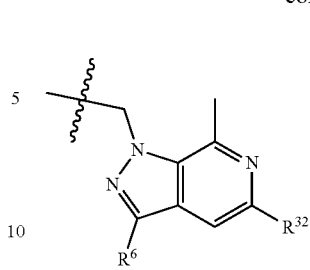
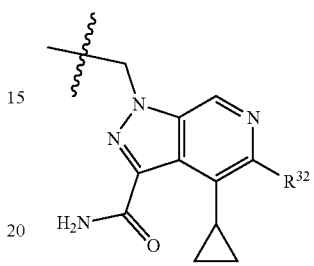
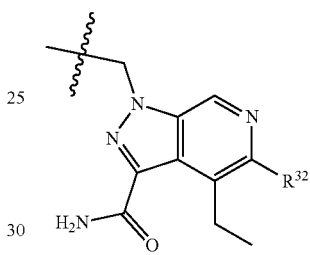
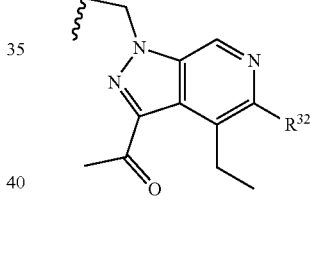
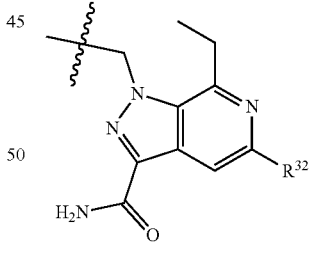
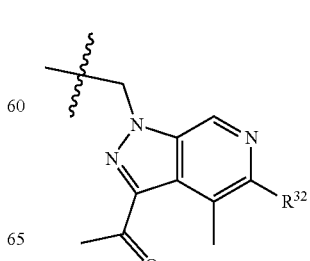

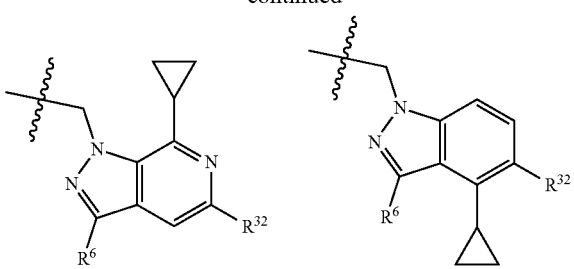
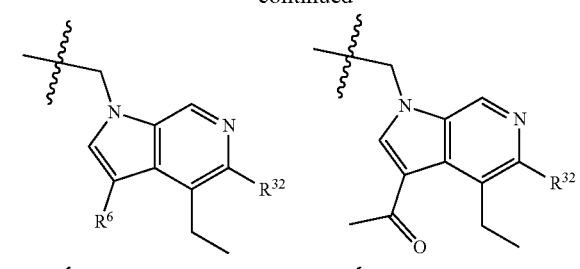
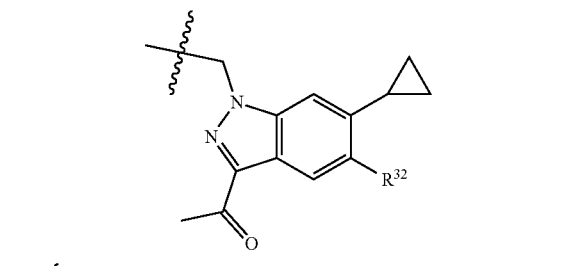
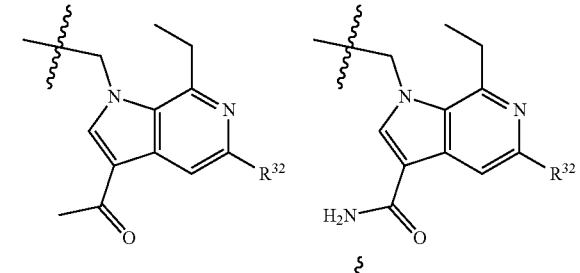
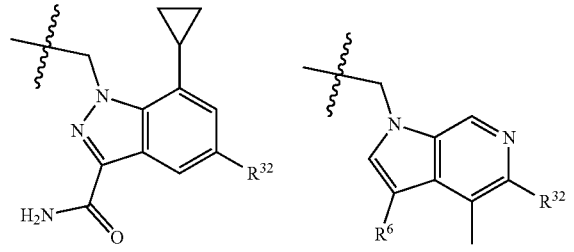
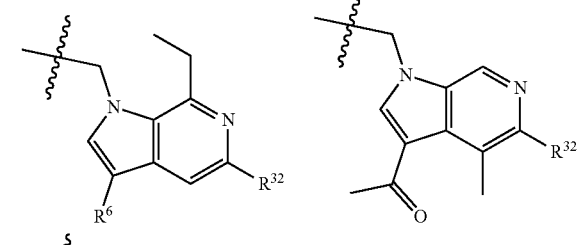
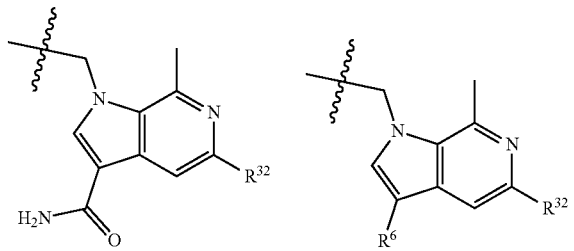
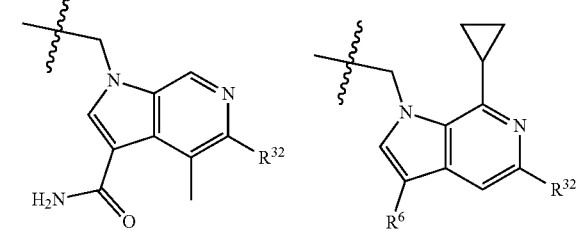
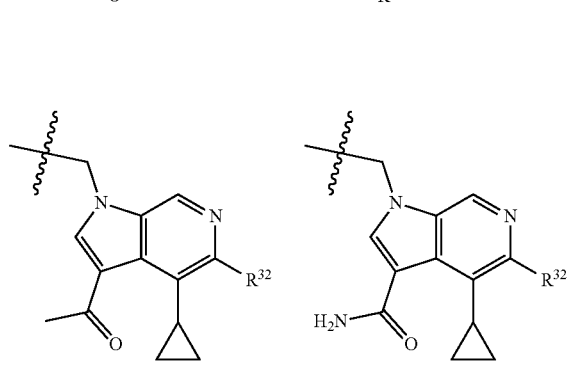
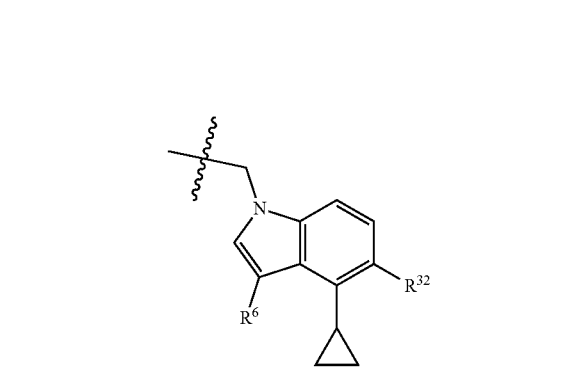

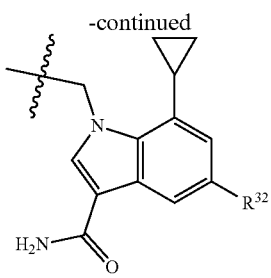
In another embodiment A is selected from:
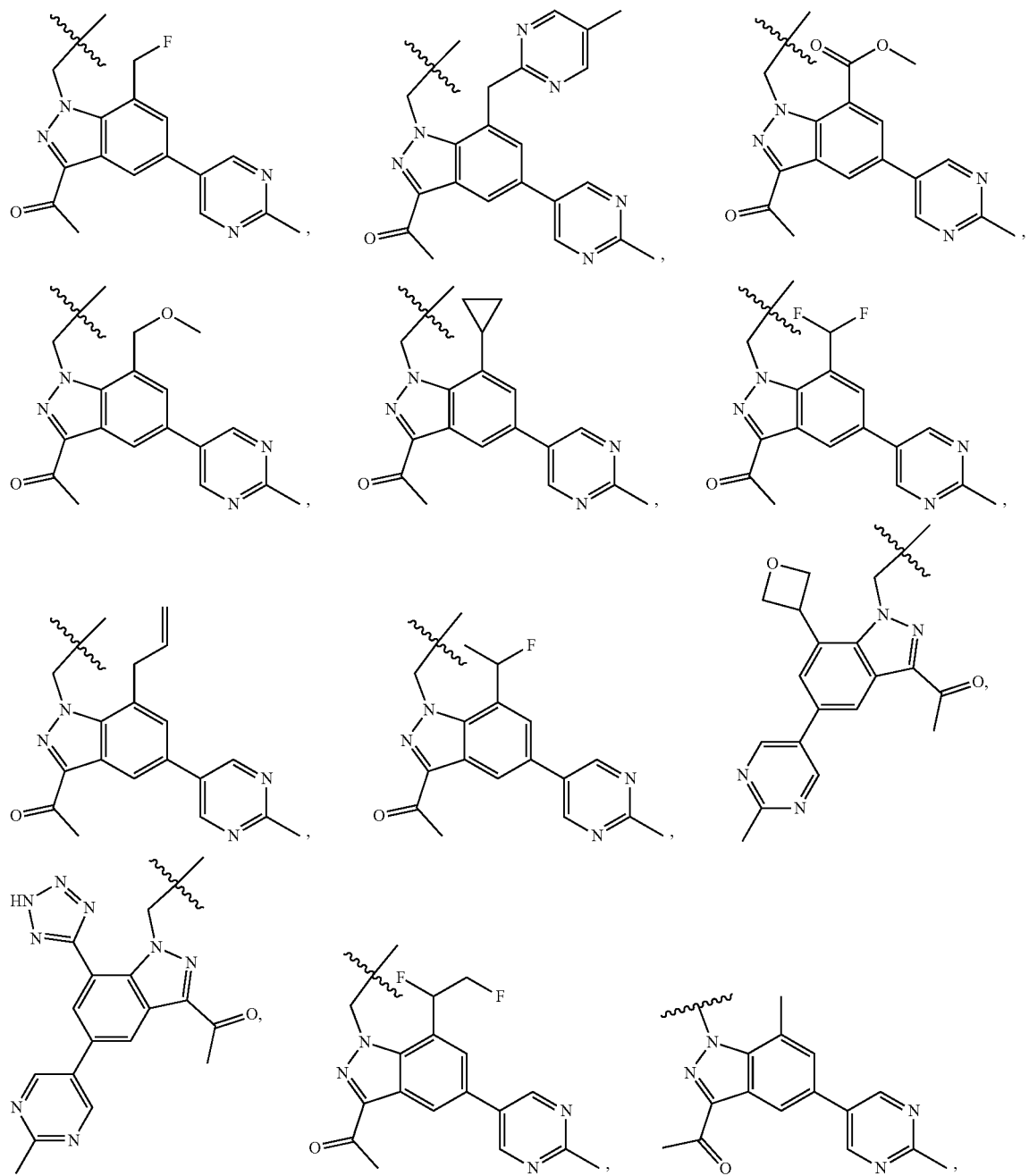

-continued
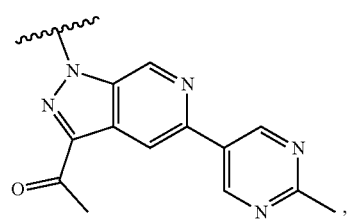
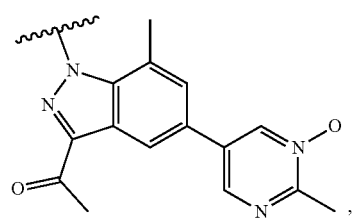
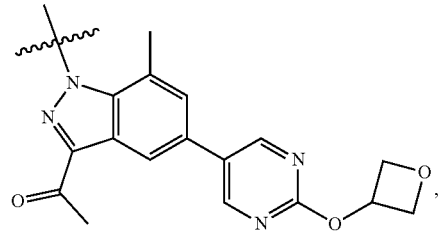
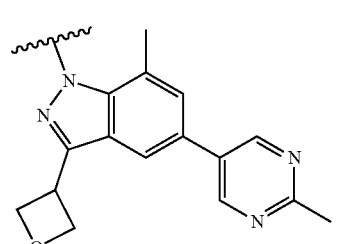
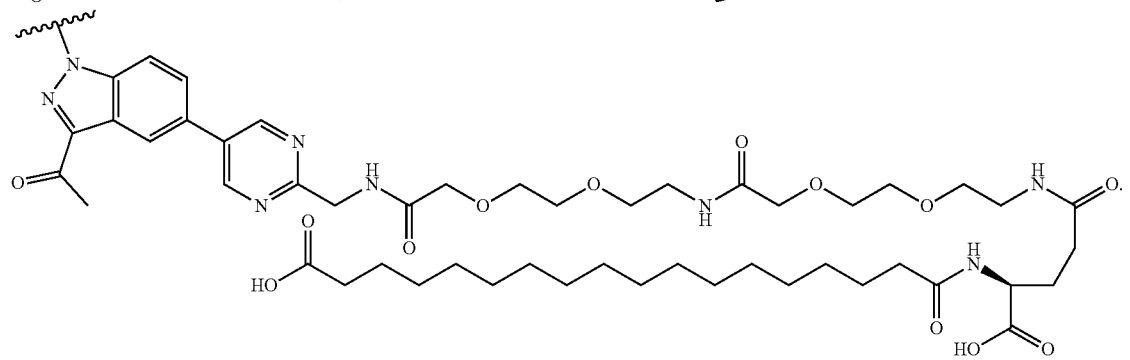
In one embodiment A4 is selected from:
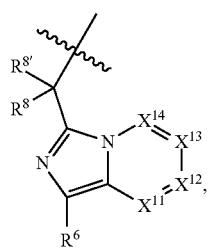 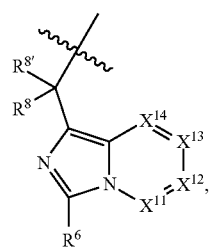
-continued
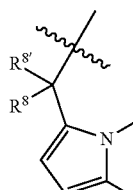 and 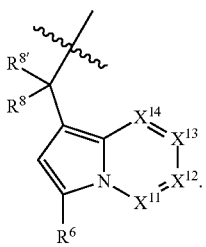

In one embodiment A4 is
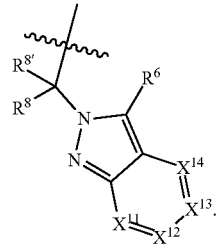
In one embodiment A4 is selected from:
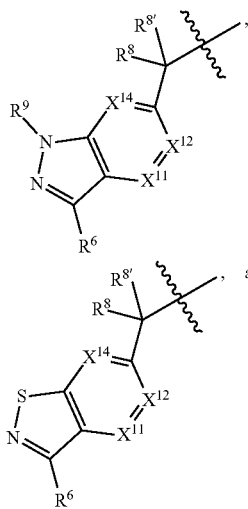
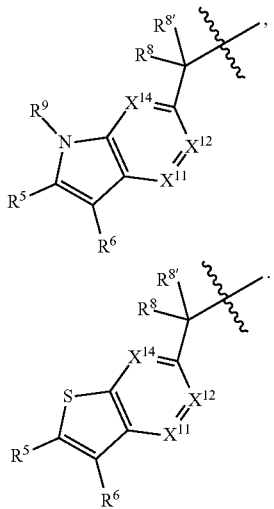
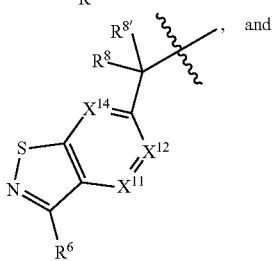
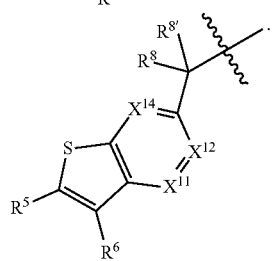
and
In one embodiment A4 is selected from:
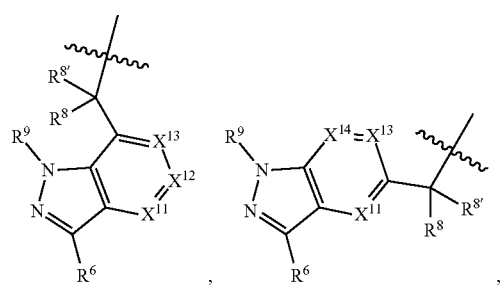
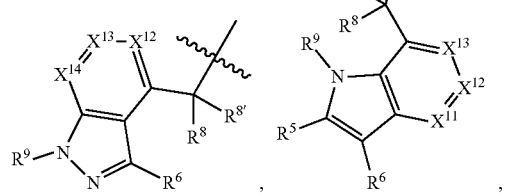
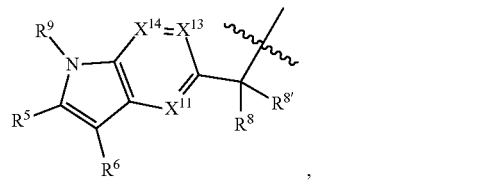
-continued
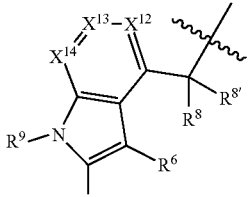
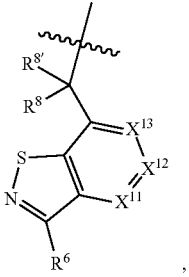
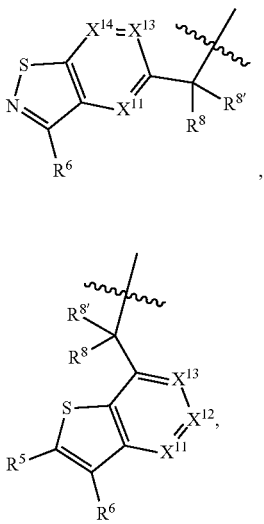
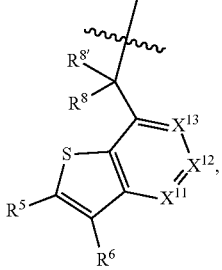
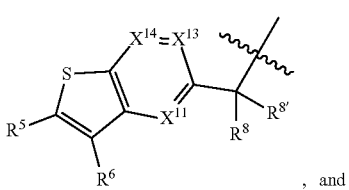
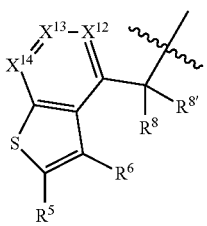
, and
In one embodiment A4 is selected from:
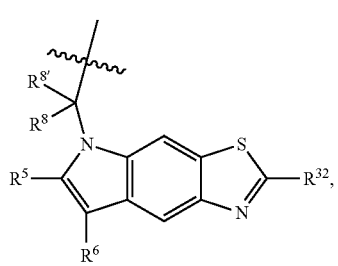

149
-continued
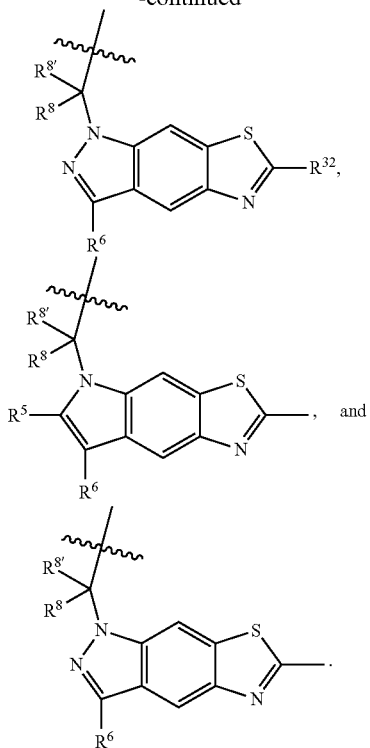
In one embodiment A4 is
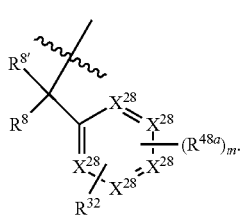
Embodiments of L
In one embodiment L1 is selected from:
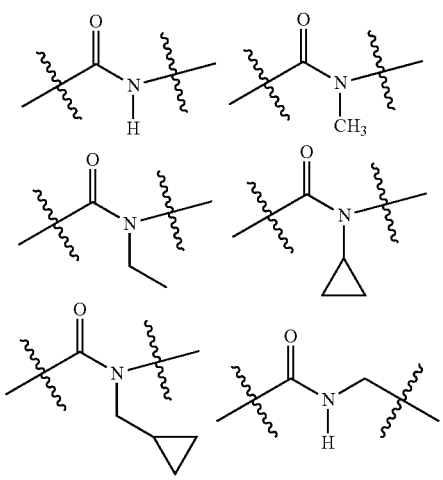
150
-continued
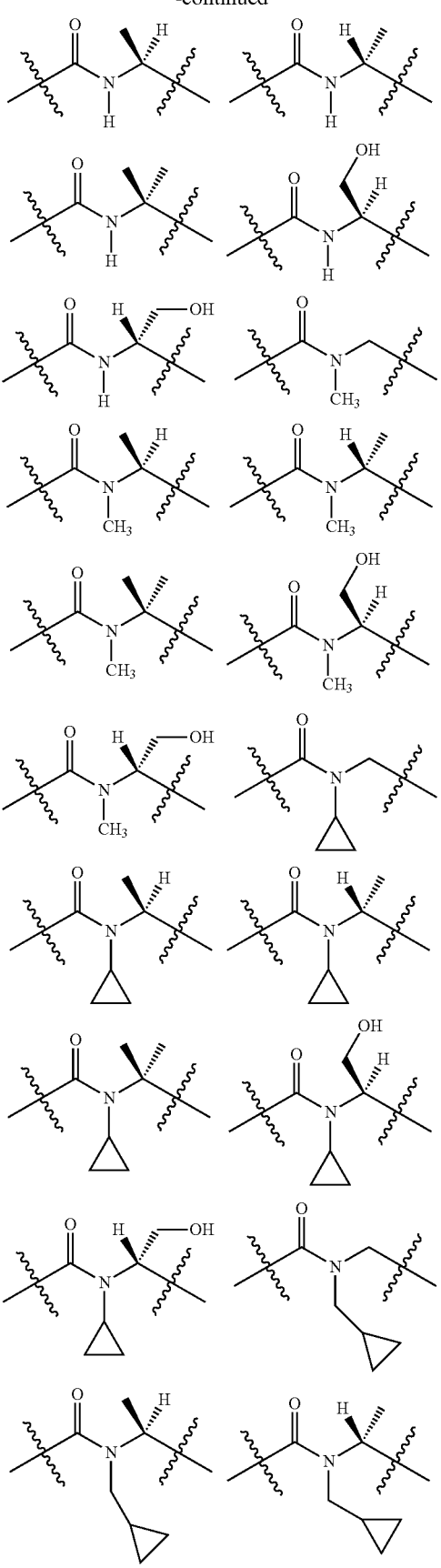

151
-continued
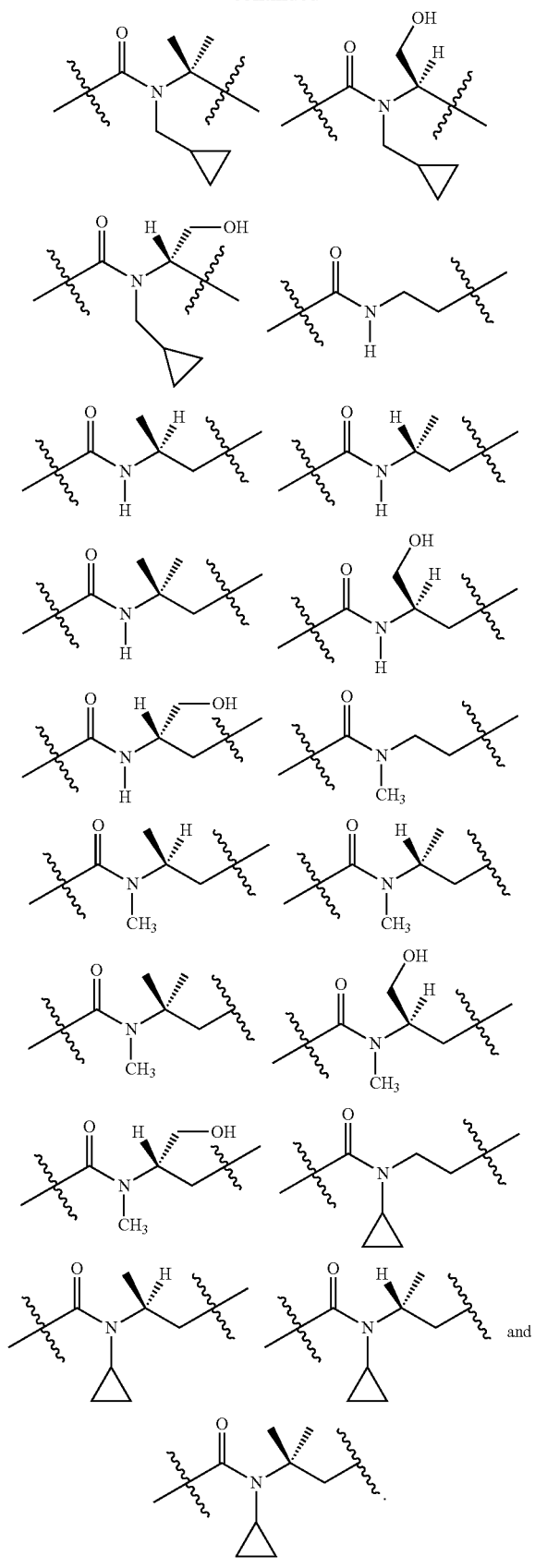
152
In one embodiment L1 is selected from:
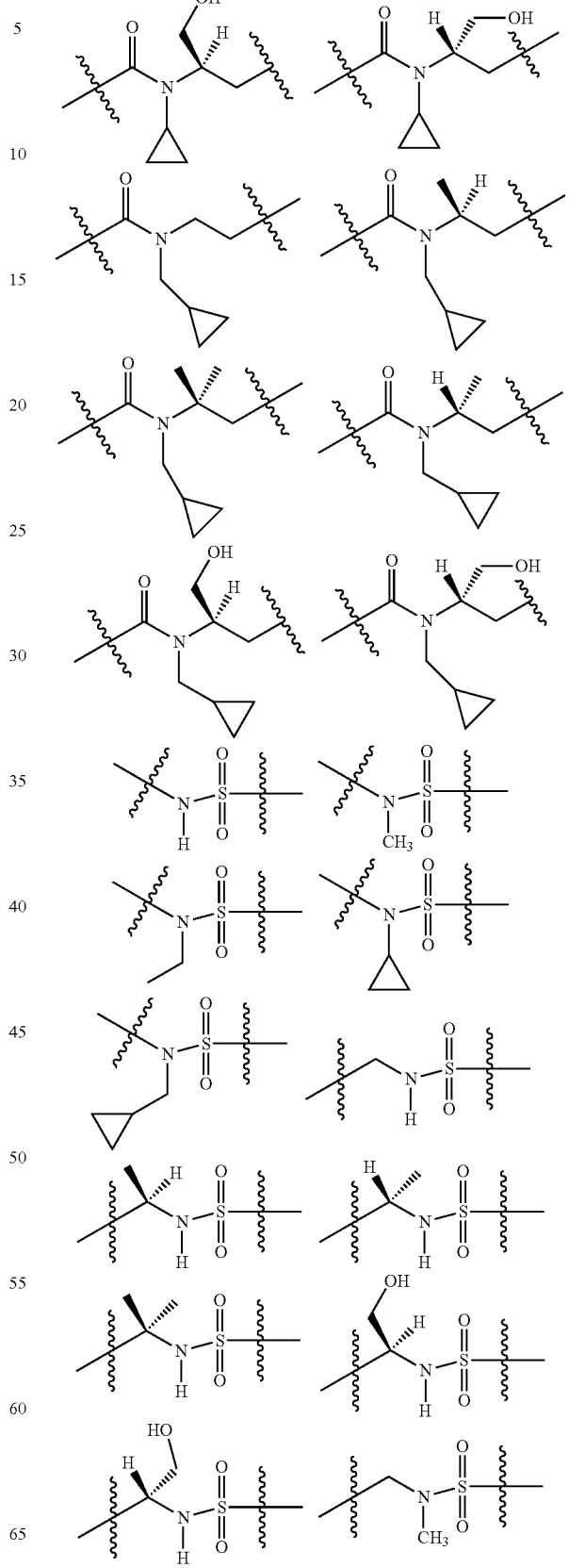

-continued
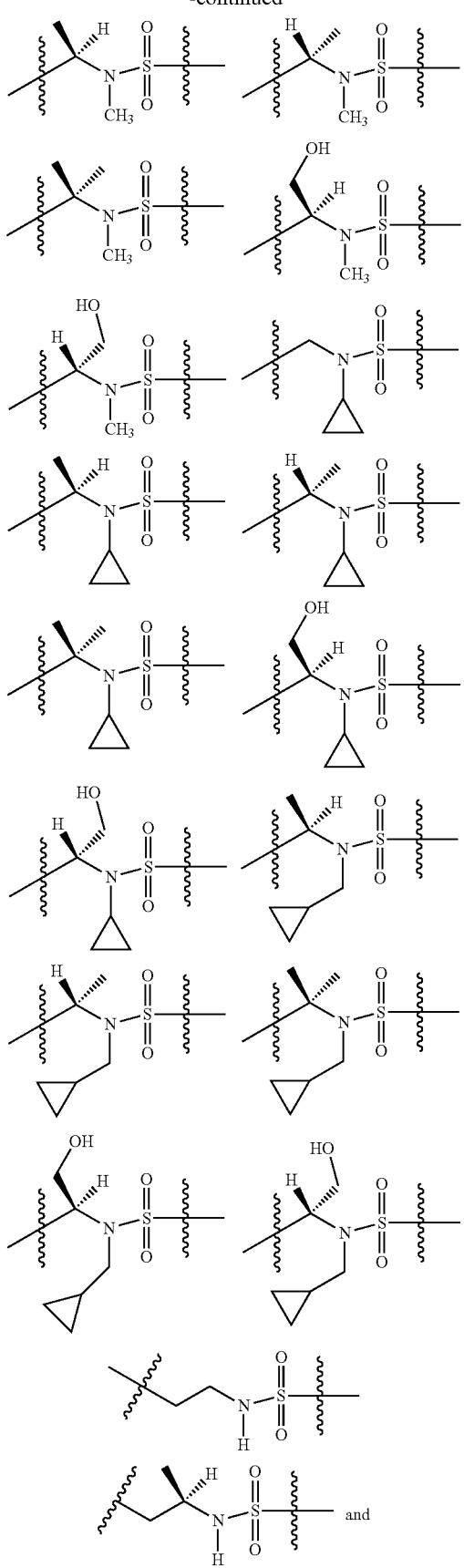
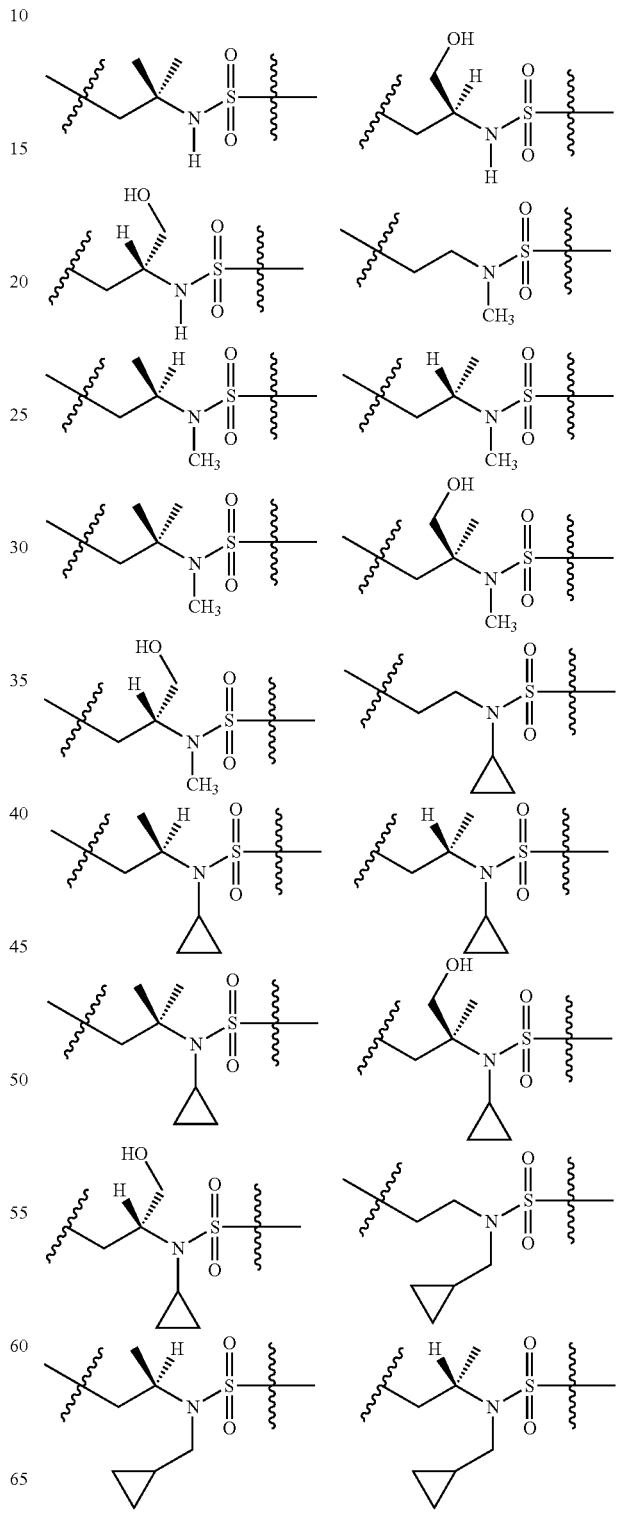
In one embodiment L1 is selected from:

In one embodiment L1 is selected from:

-continued
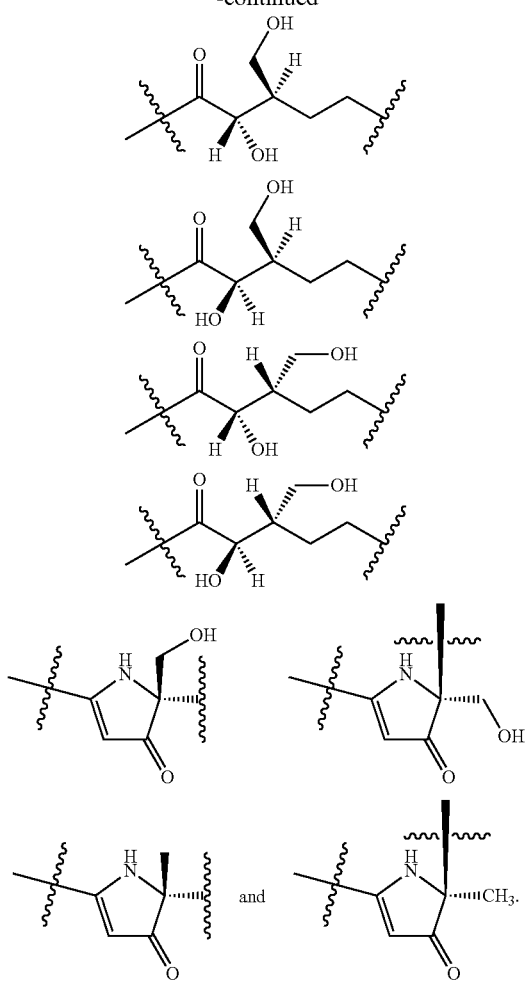
In one embodiment, L1 is selected from:
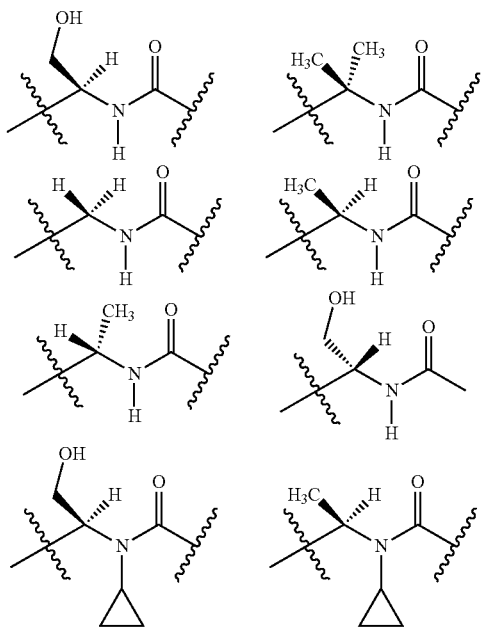
-continued
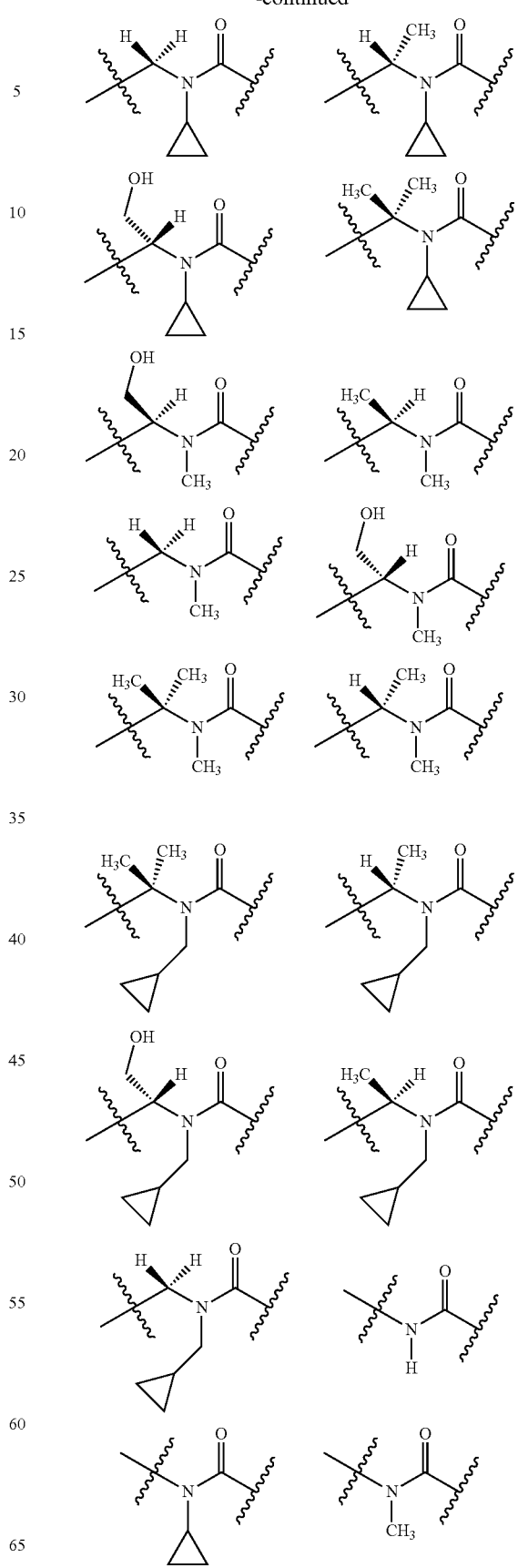

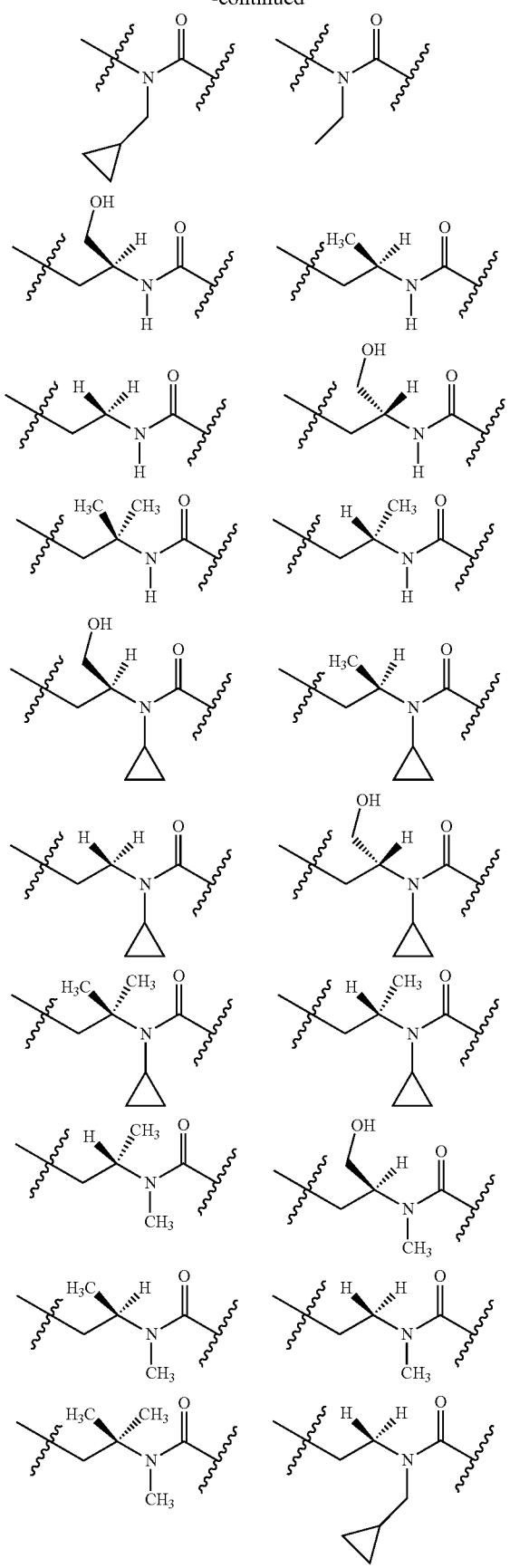
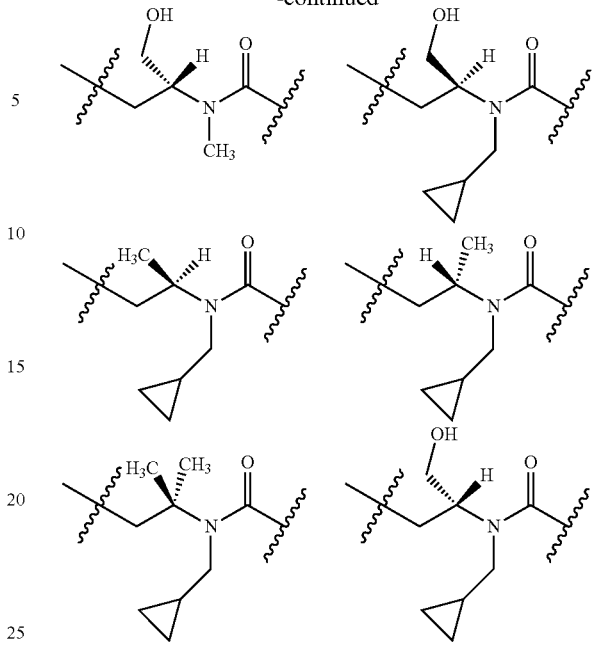
In one embodiment, the methyl groups in the structures illustrated above can be replaced with another alkyl group, as defined herein.
In one embodiment L2 is selected from:
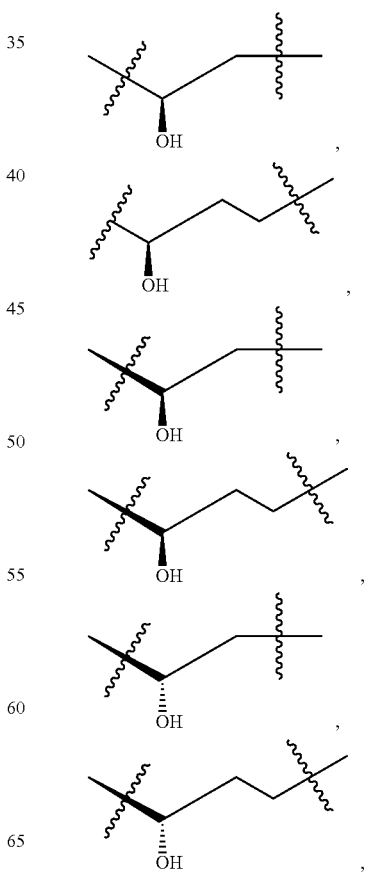

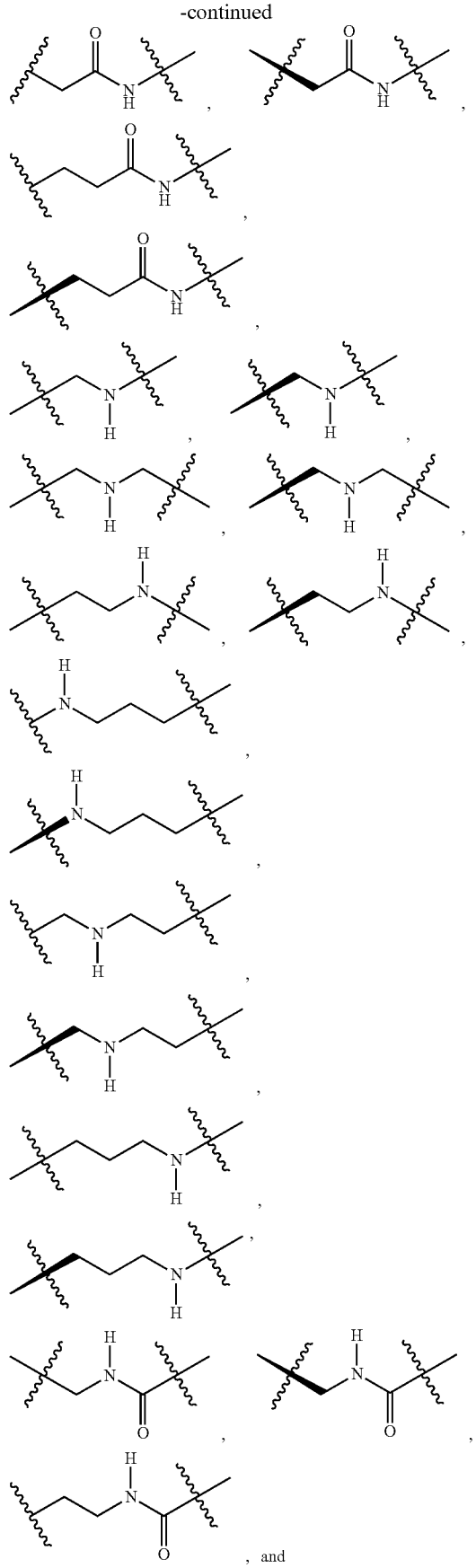
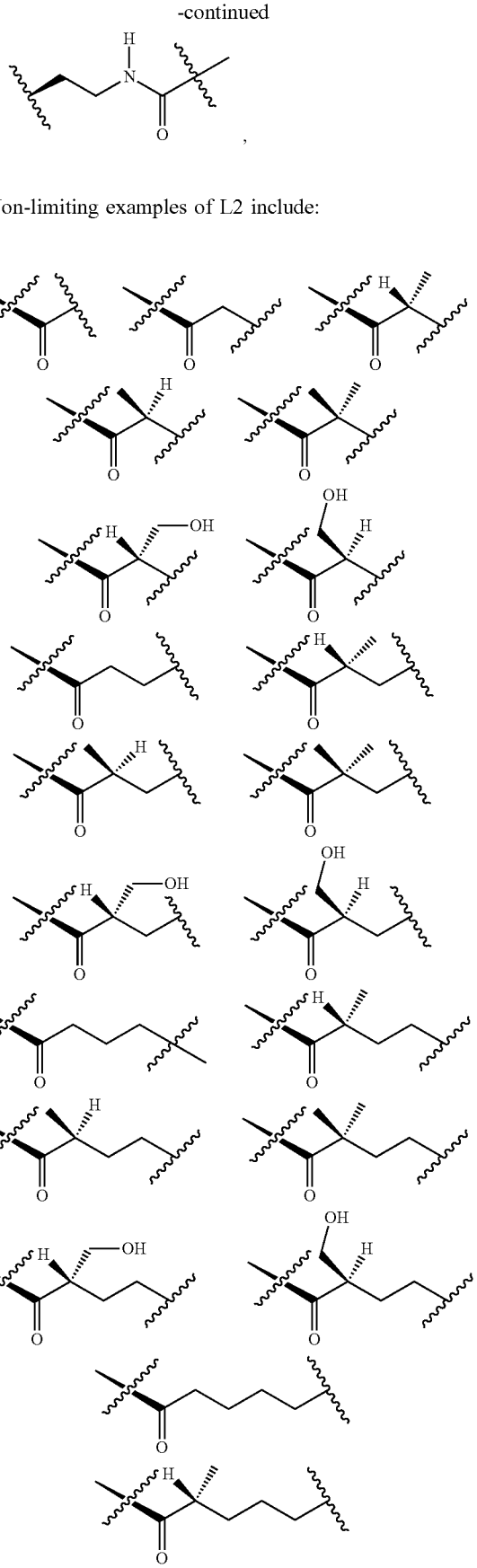
Non-limiting examples of L2 include:

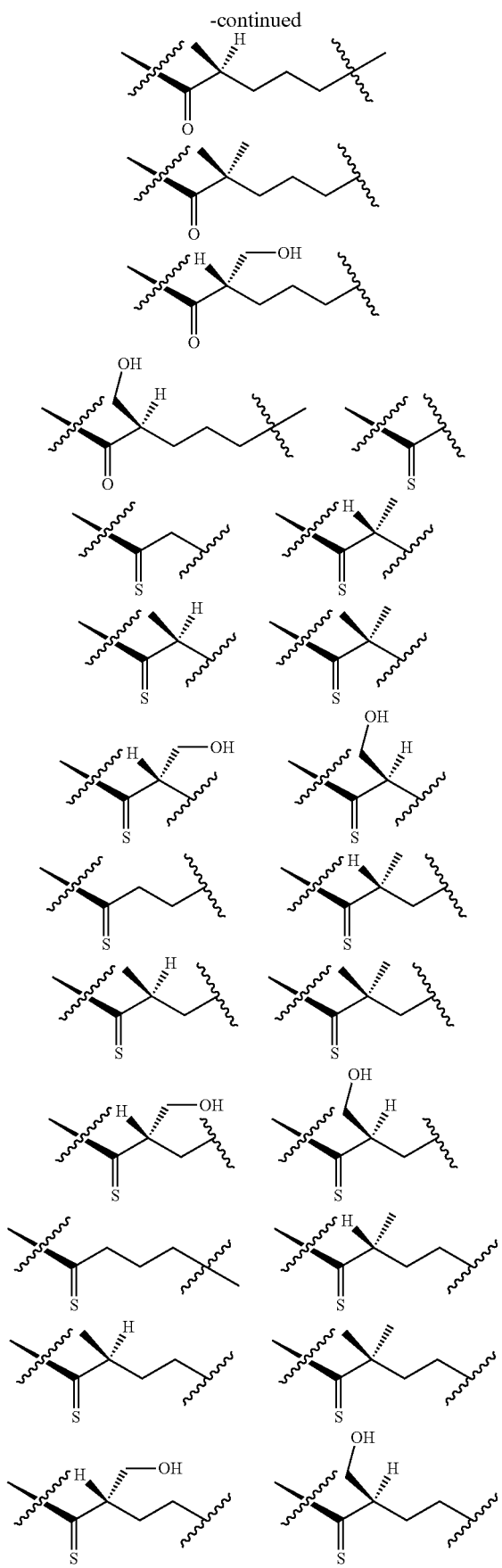
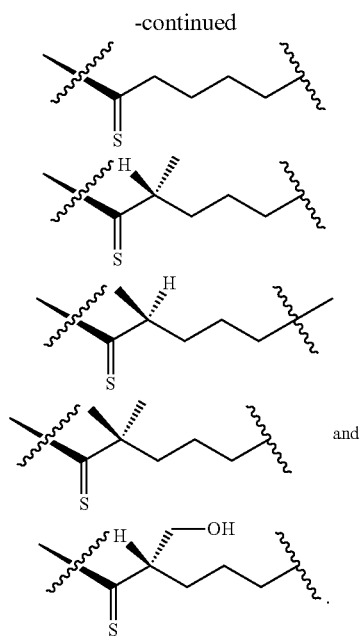
Non-limiting examples of L2 include:
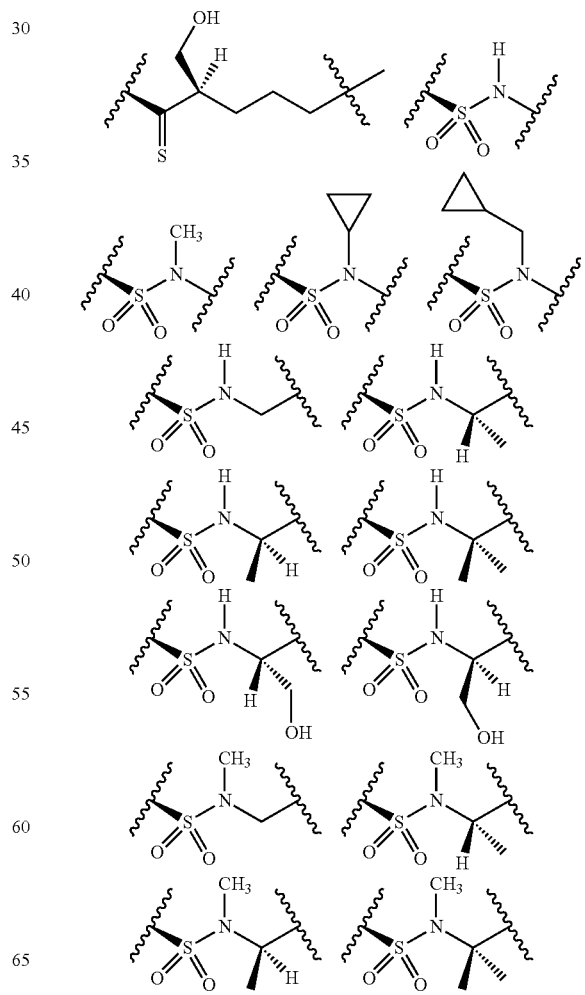

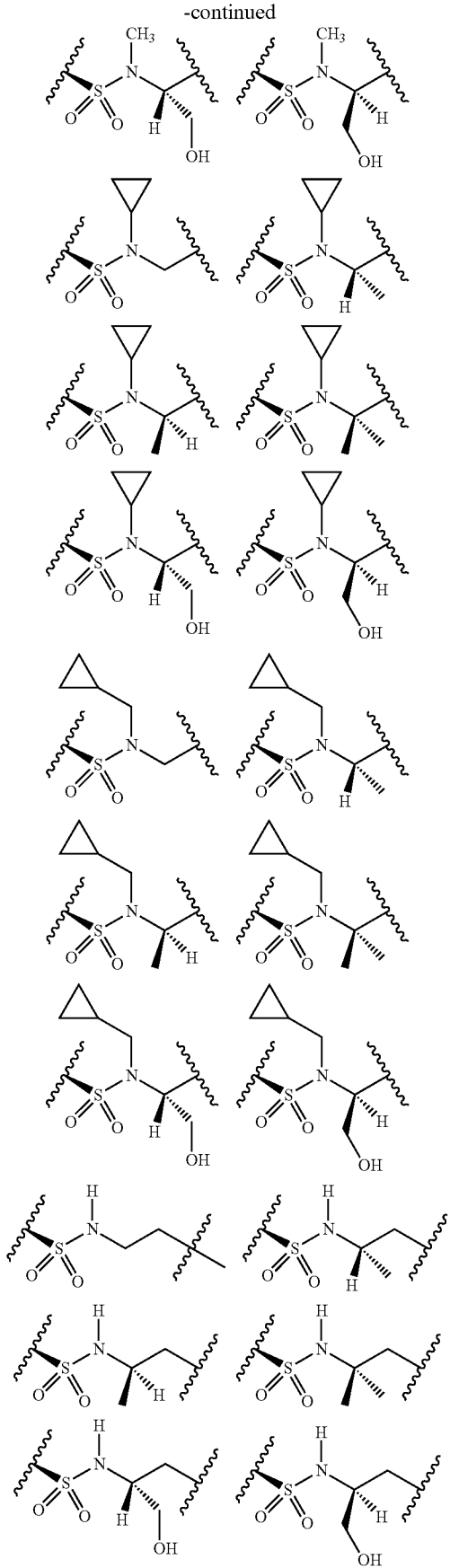
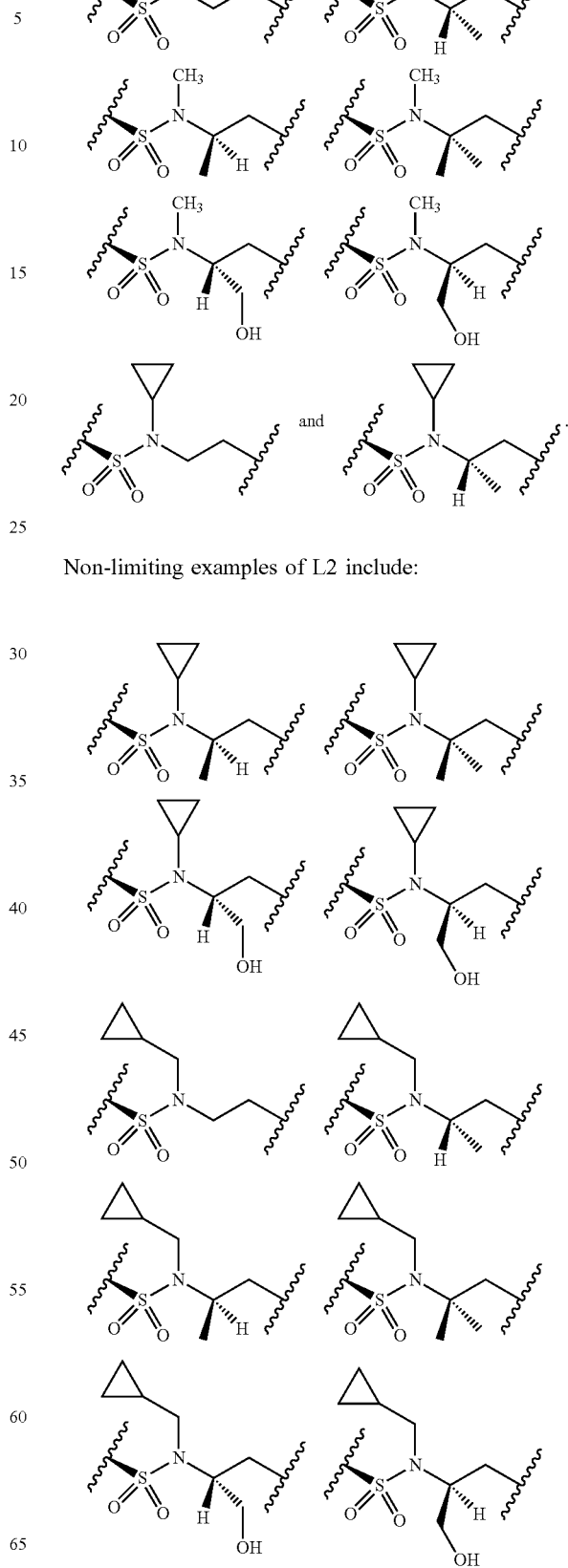
Non-limiting examples of L2 include:

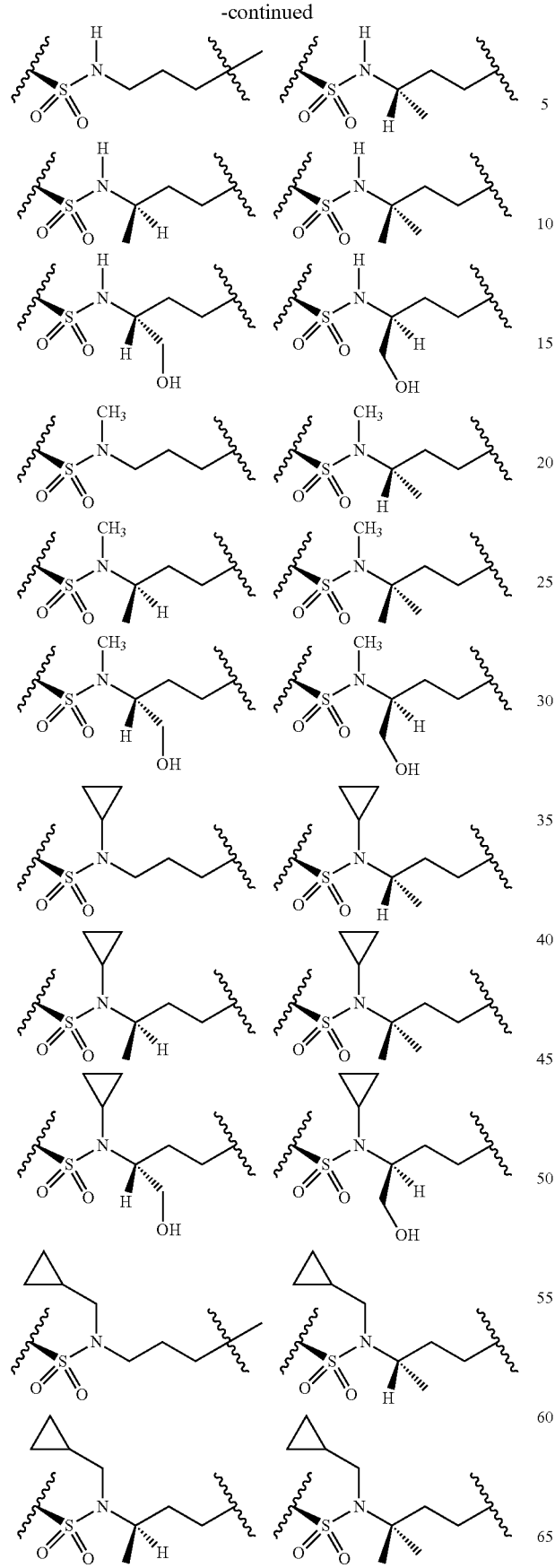
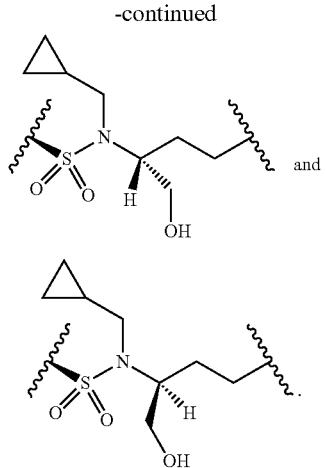
Non-limiting examples of L2 include:
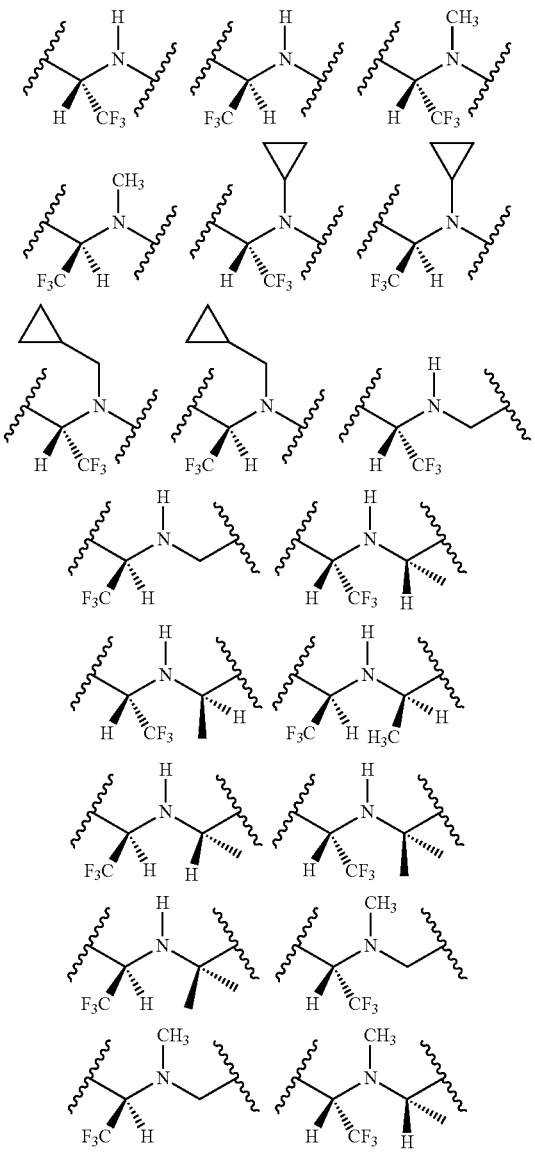

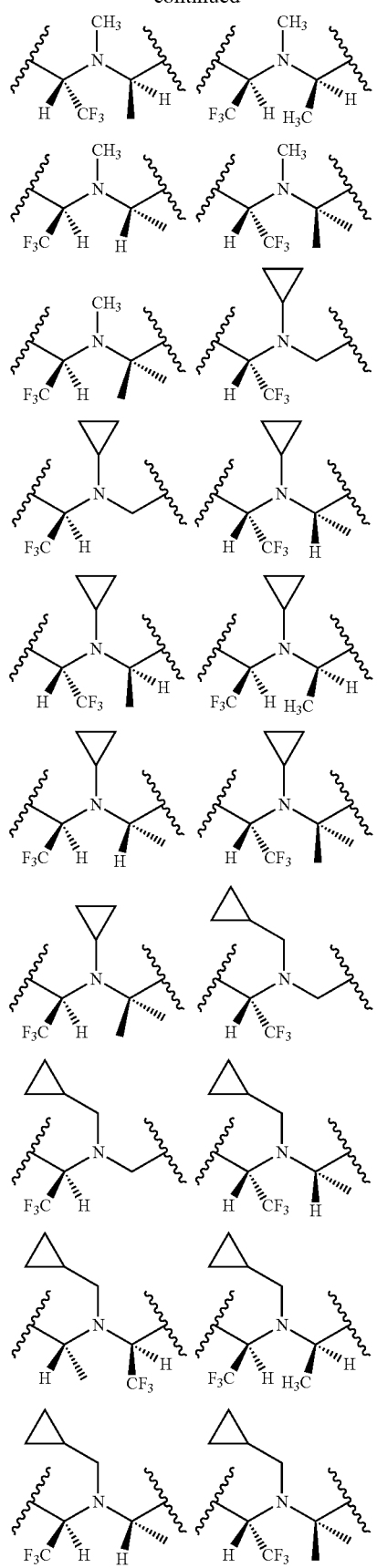
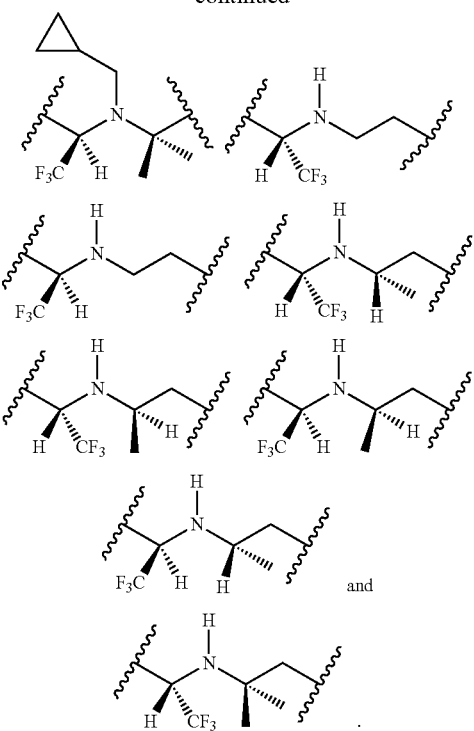
and
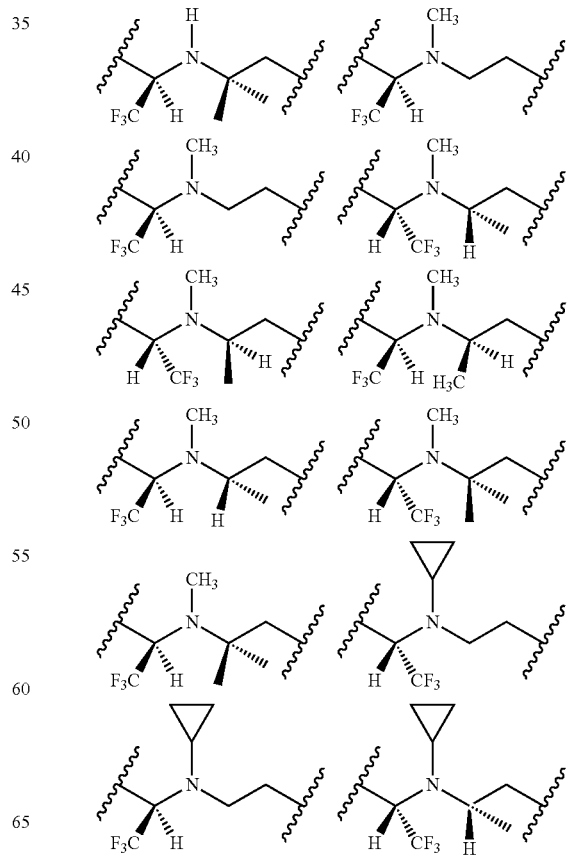
Non-limiting examples of L2 include:

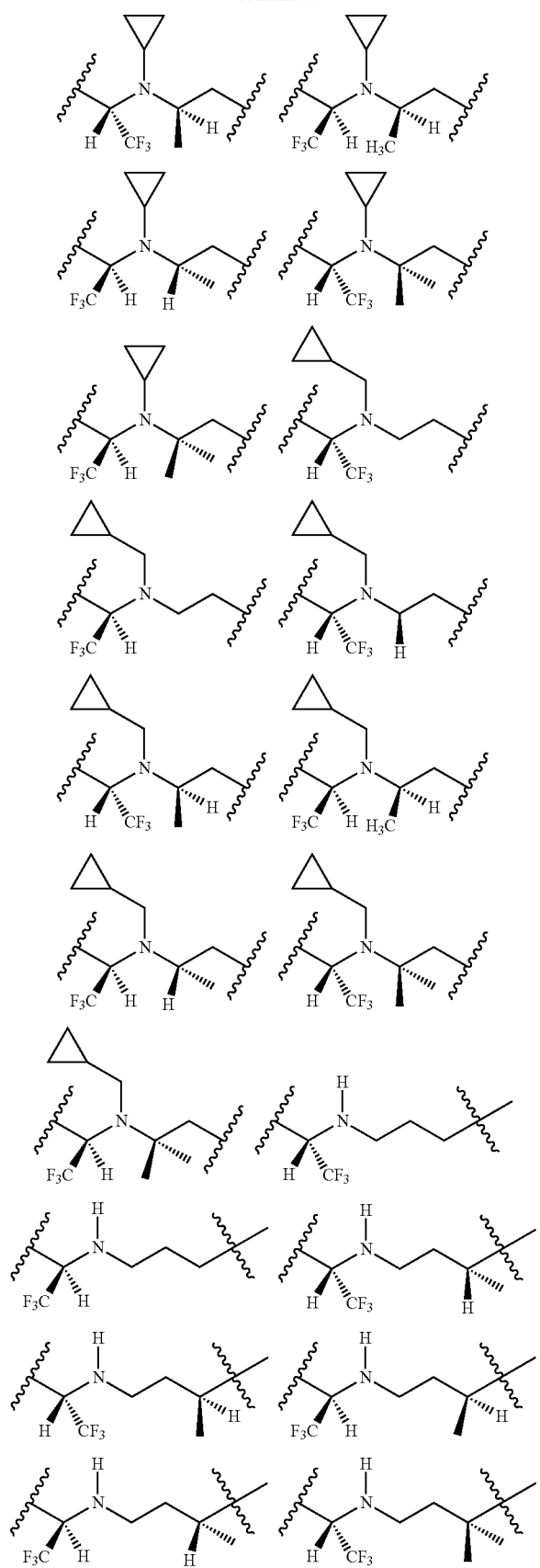

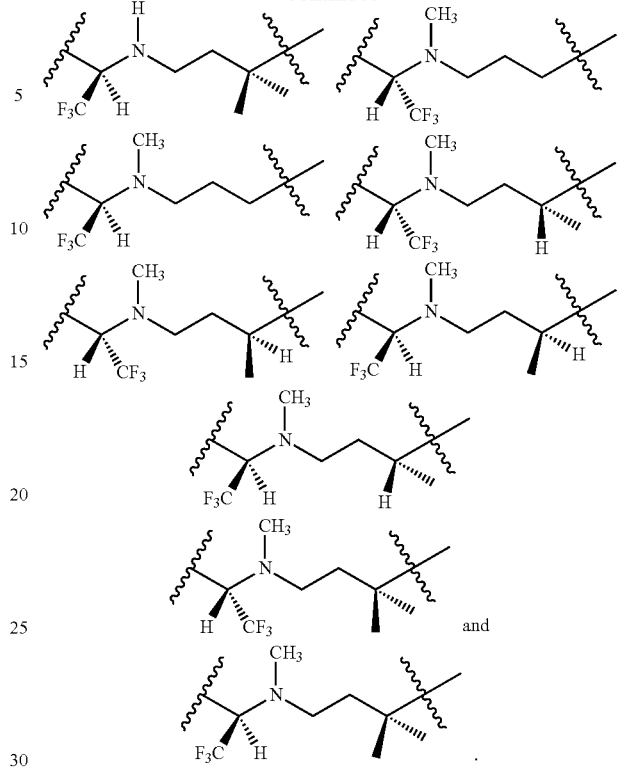

In one embodiment, the methyl groups in the structures illustrated above can be replaced with another alkyl or acyl, as defined herein. In another embodiment, the carbocyclic, heterocyclic, aryl or heteroaryl rings can be optionally substituted. As indicated above, any of the structures illustrated above or below can be optionally substituted with 0, 1, 2, 3, or 4, as appropriate, and independently, of an $R^{48}$ substituent.

In certain embodiment, L2 is a bond. In certain embodiments, if L2 is heterocyclic or heteroaryl, then B can be hydrogen.

Embodiments of B

In one additional alternative embodiment B is selected from:

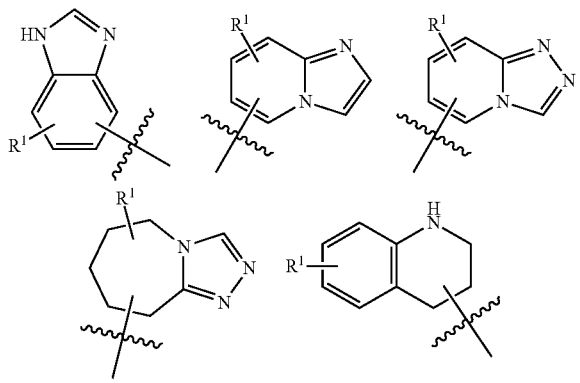

-continued
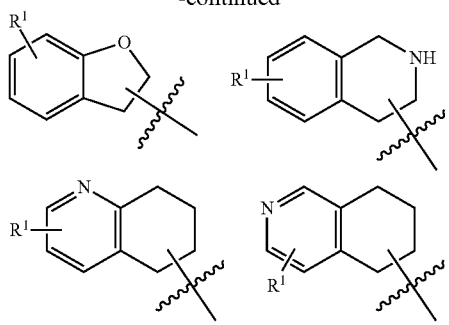
In another embodiment, B1 is selected from:
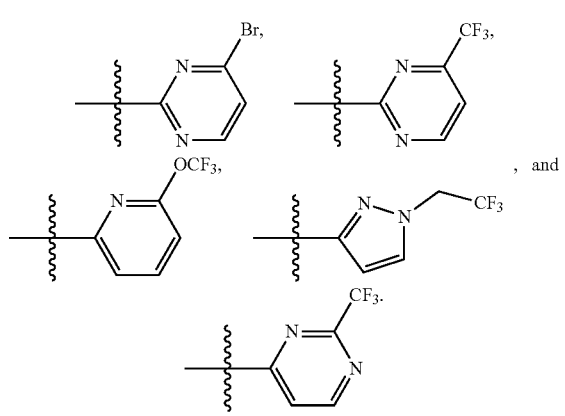
In one additional alternative embodiment R³⁶ is selected from:
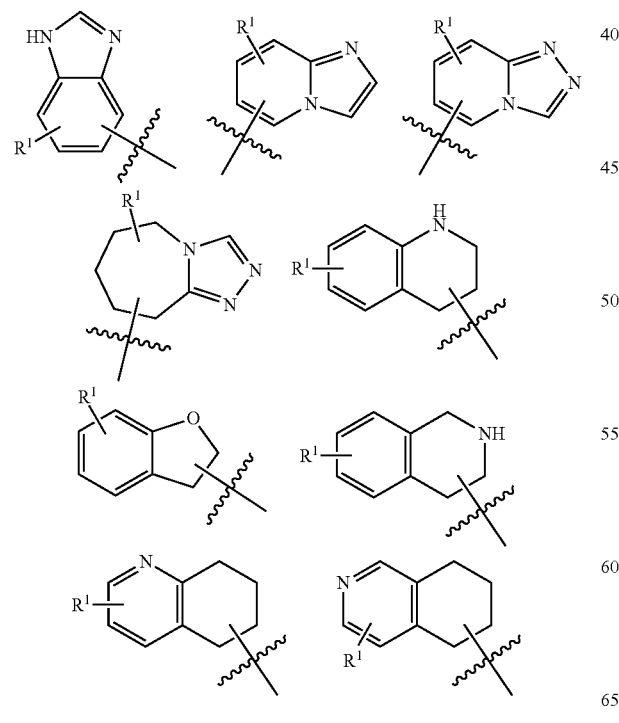
In one embodiment, B is selected from:
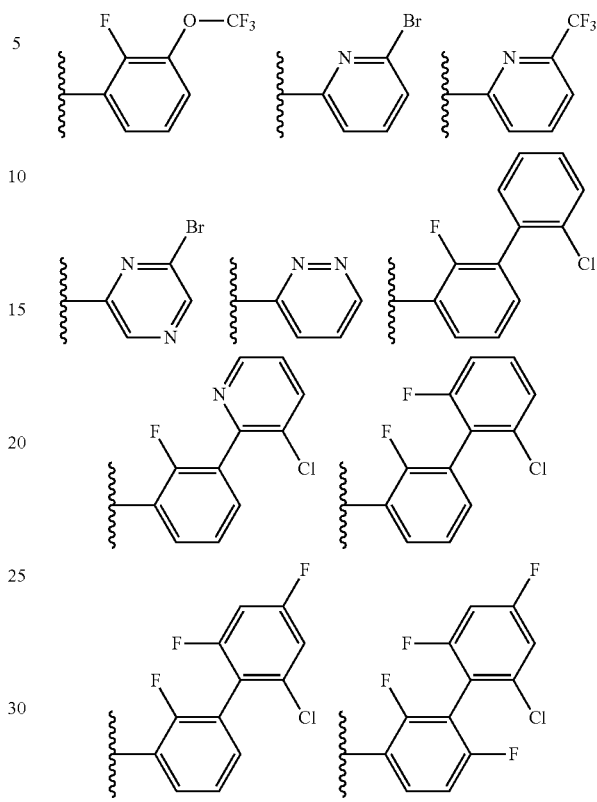
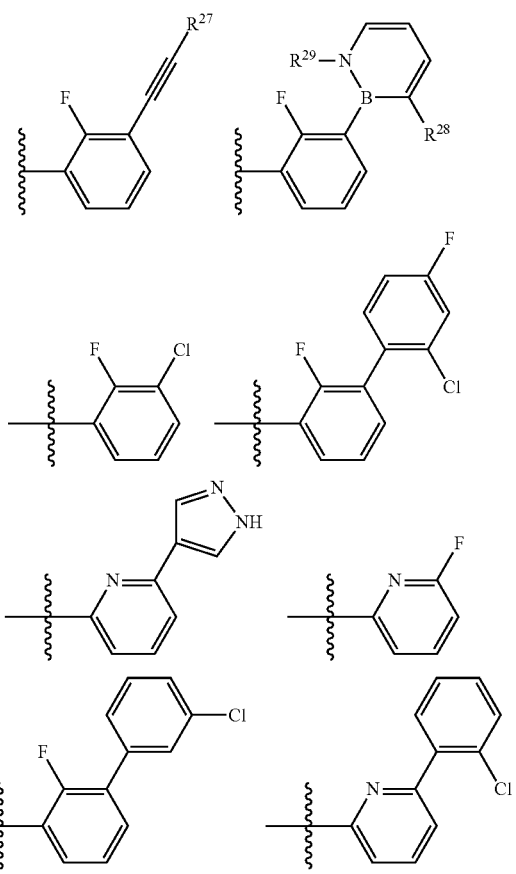

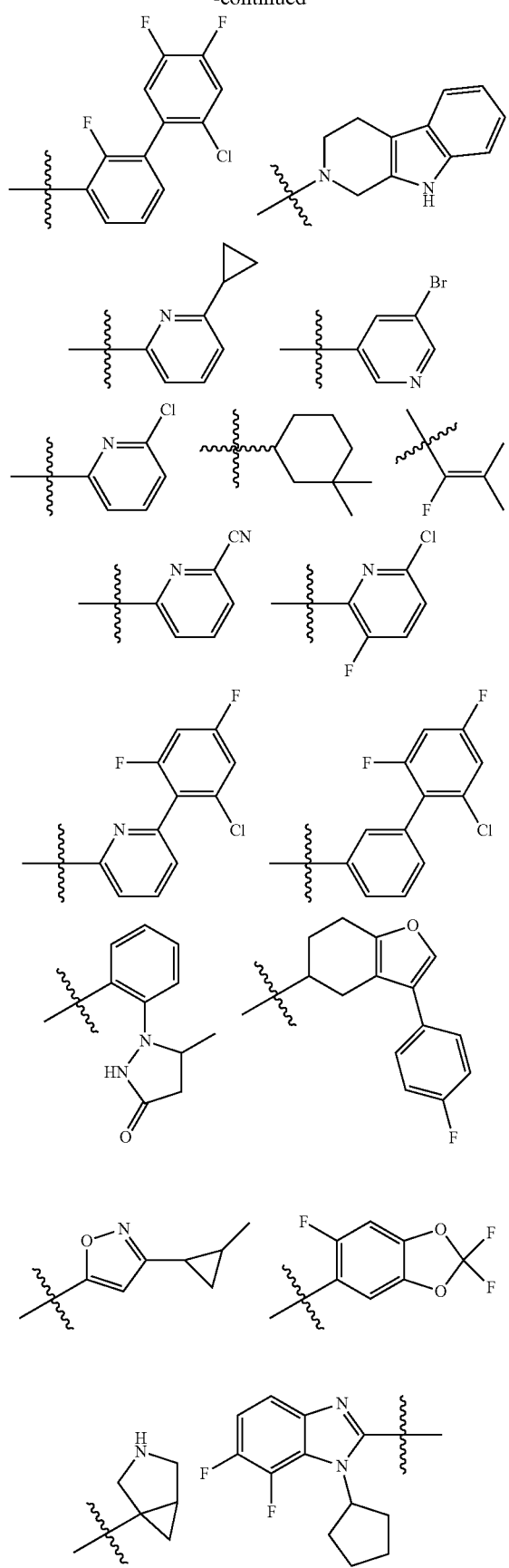
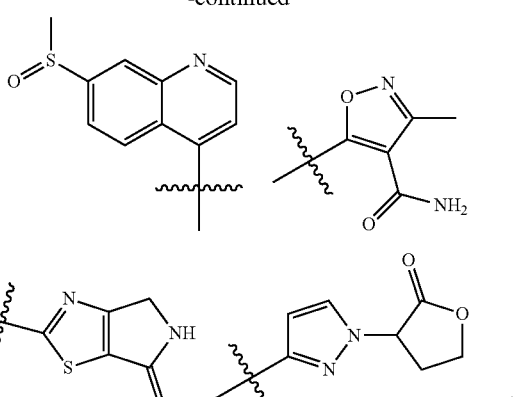
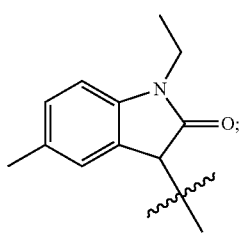
wherein $R^{27}$ is hydrogen, methyl, or trifluoromethyl; $R^{28}$ is hydrogen or halogen; and $R^{29}$ is hydrogen, methyl, trifluoromethyl, or —Si(CH$_3$)$_2$C(CH$_3$)$_3$.
In one embodiment, B is selected from:
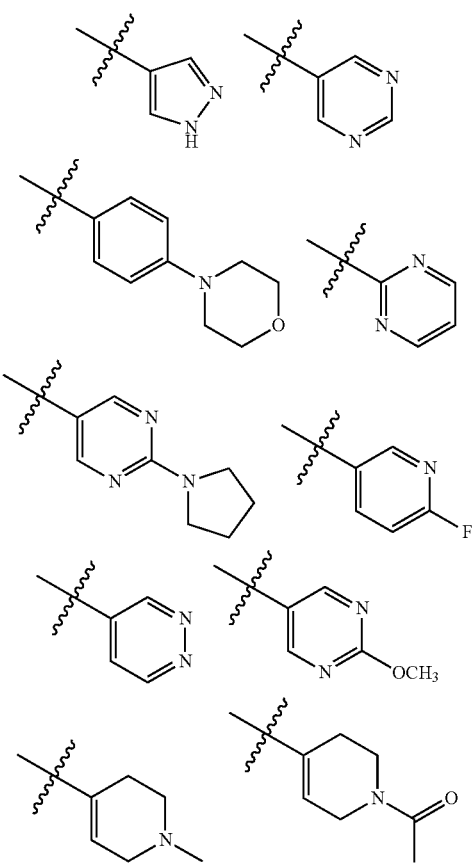

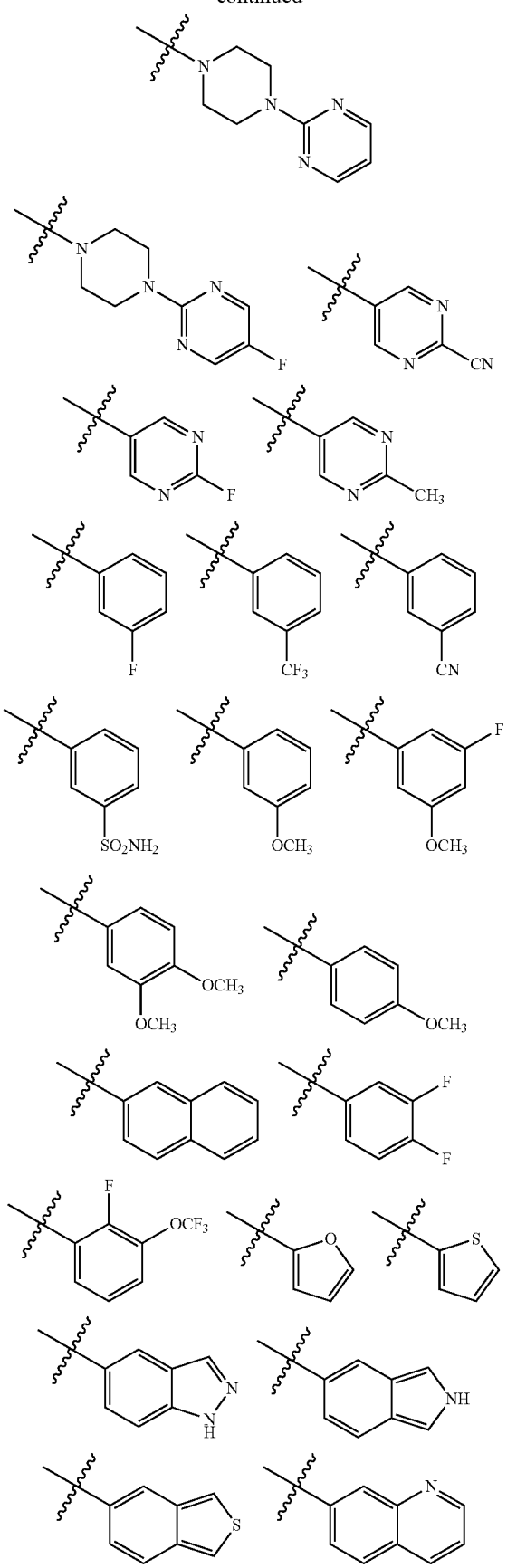
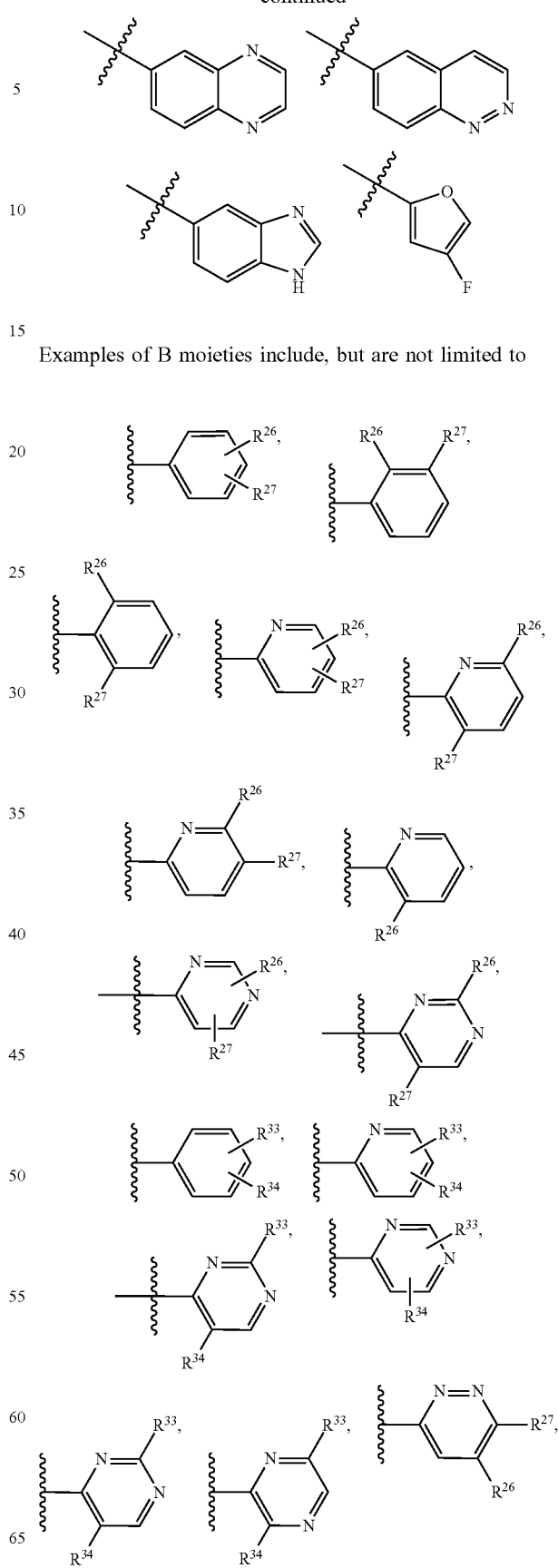
Examples of B moieties include, but are not limited to

-continued
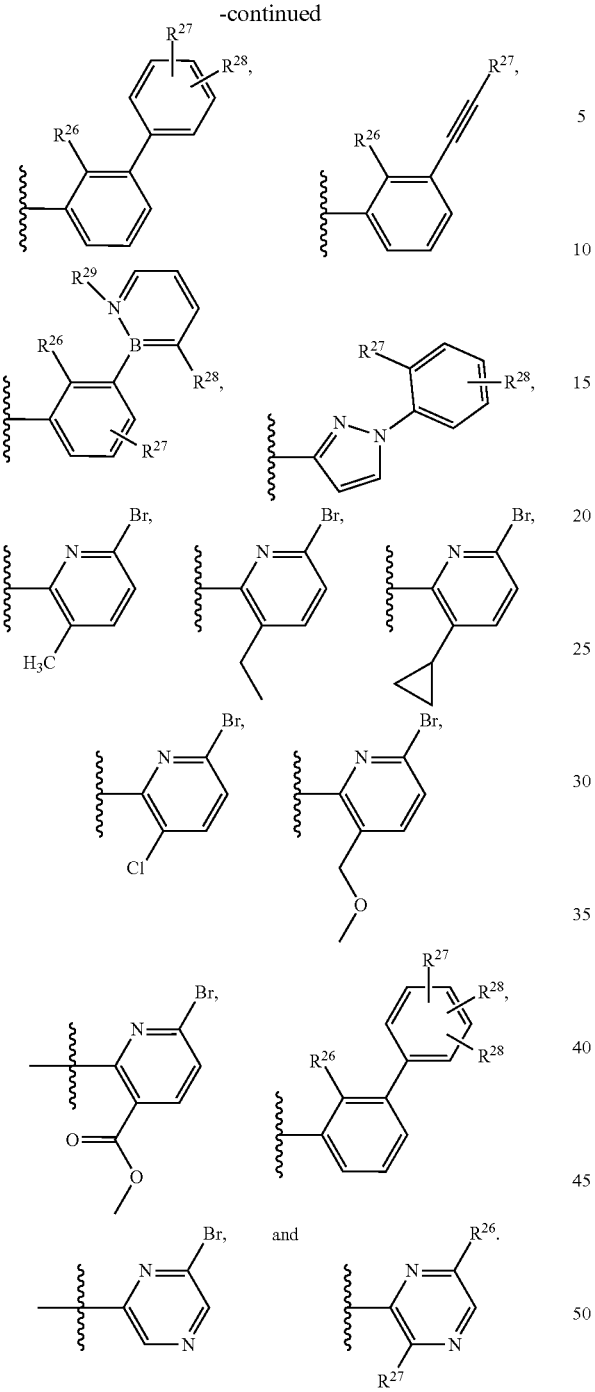
In one embodiment, B4 is
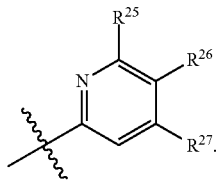
In one embodiment, B4 is
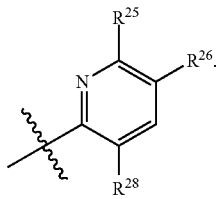
In one embodiment, B4 is
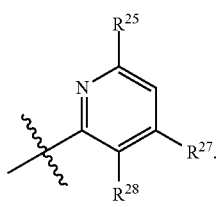
In one embodiment, B4 is
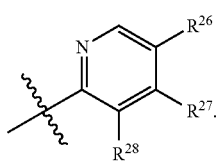
In one embodiment, B4 is selected from:
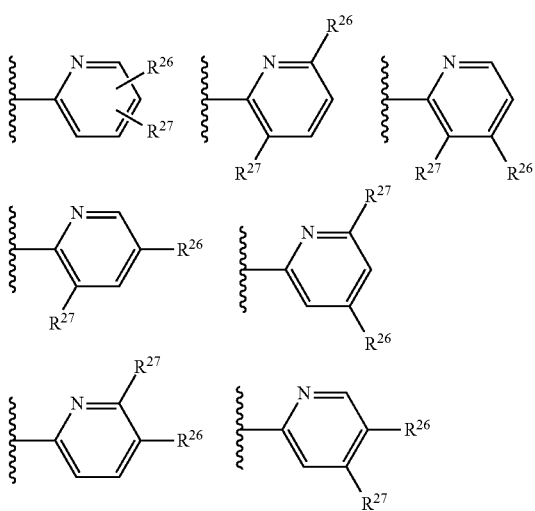
In one embodiment, B4 is
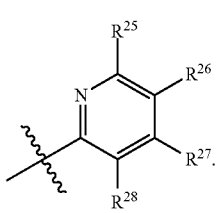

-continued
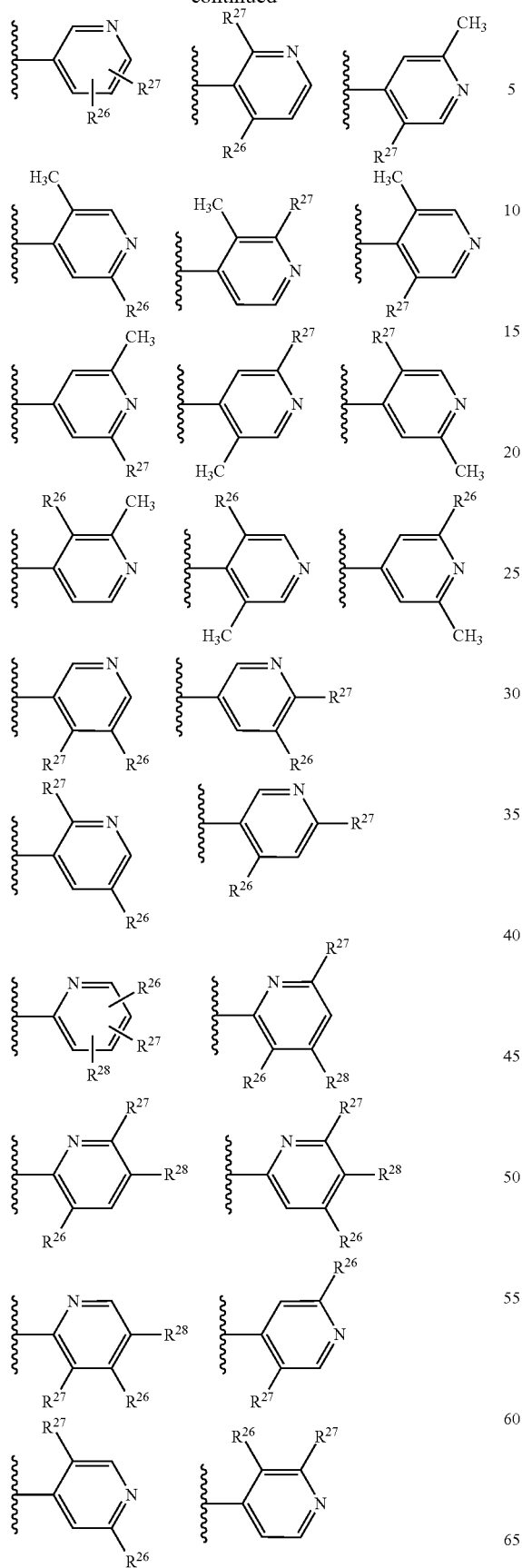
In one embodiment, B4 is selected from:
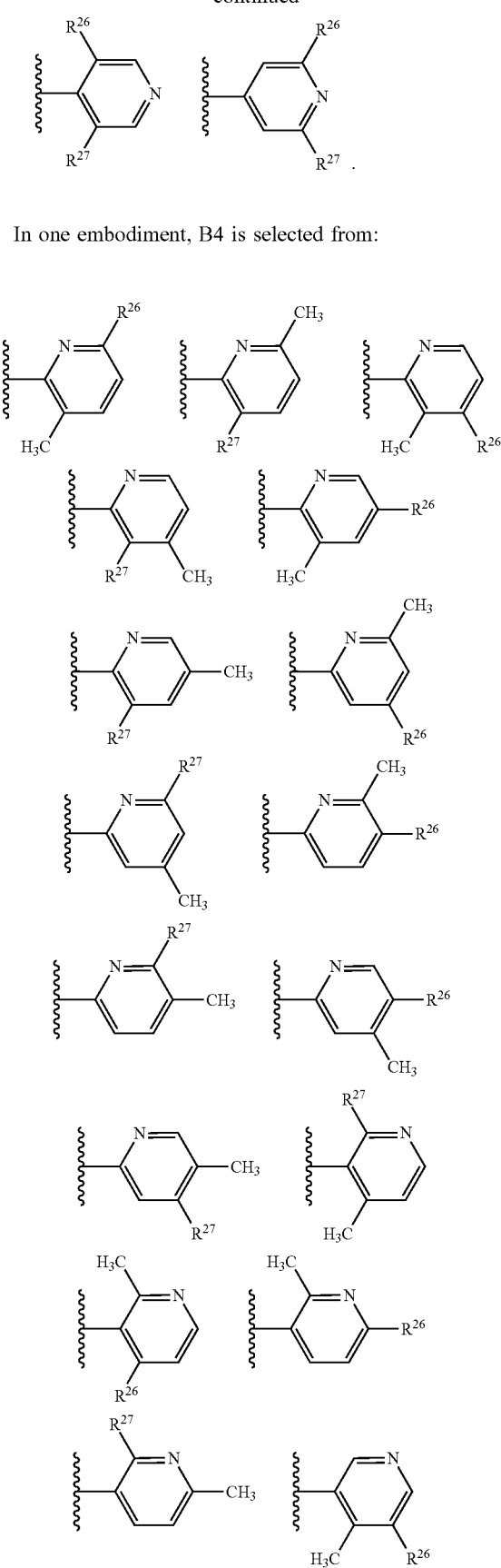

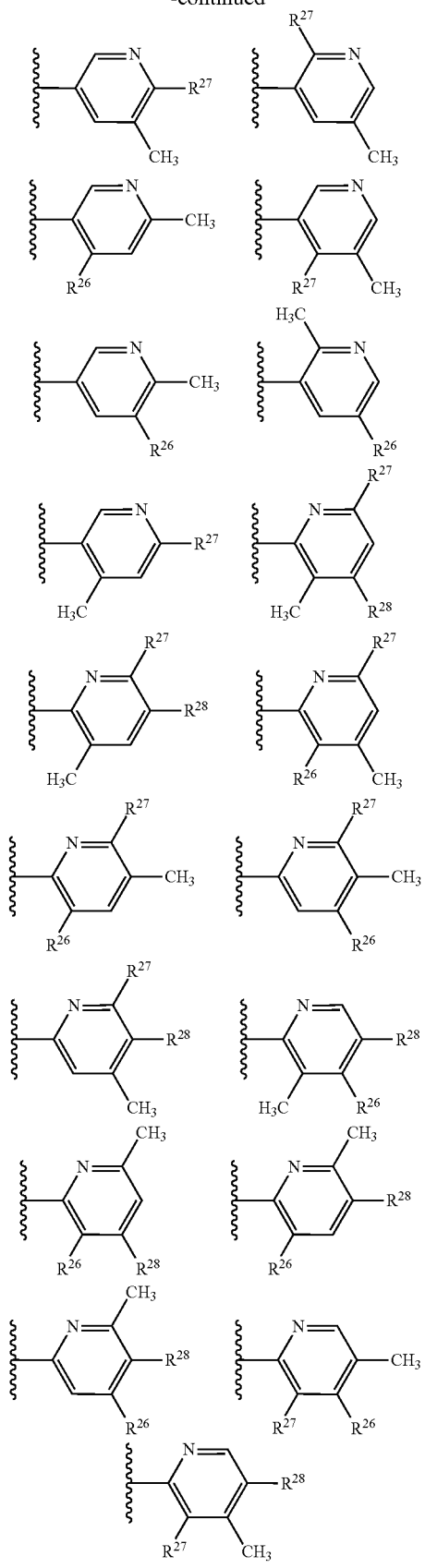
In one embodiment, B4 is selected from:
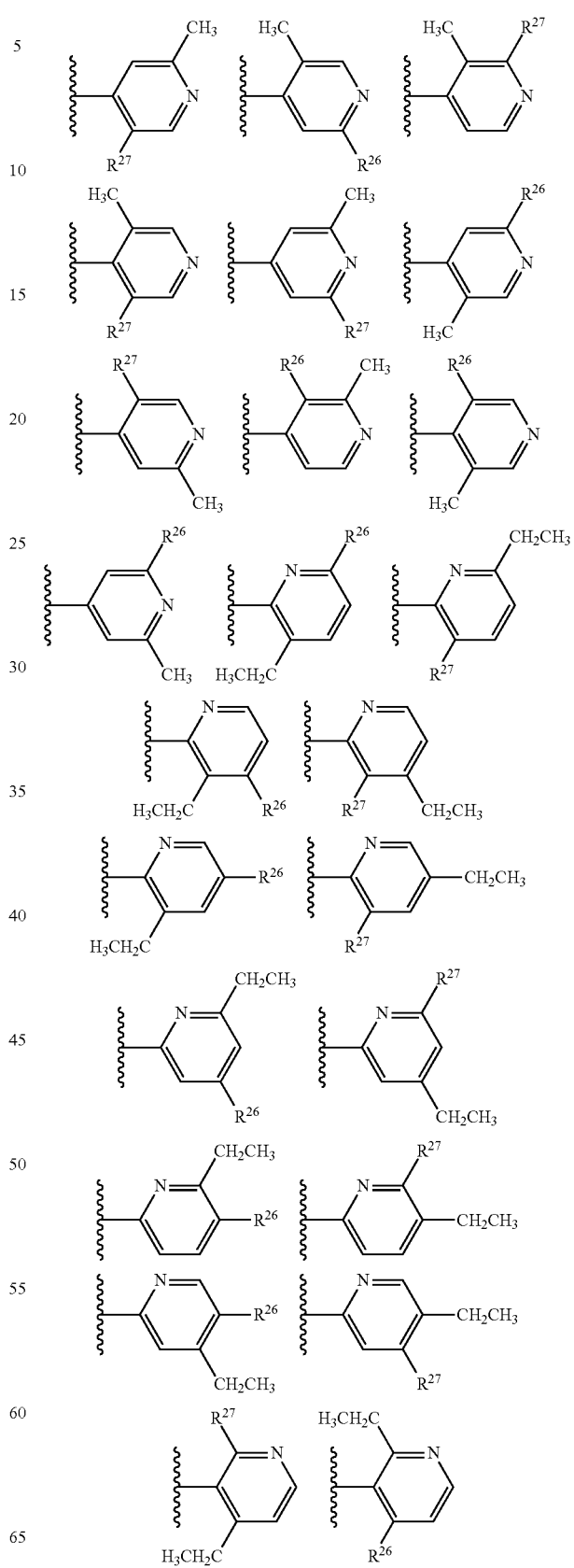

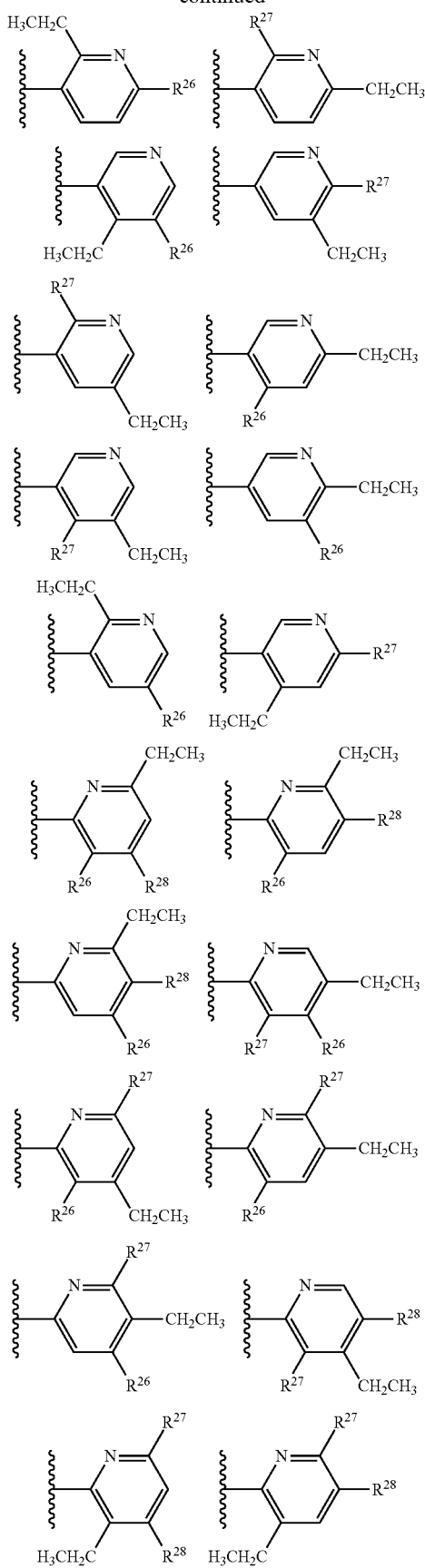
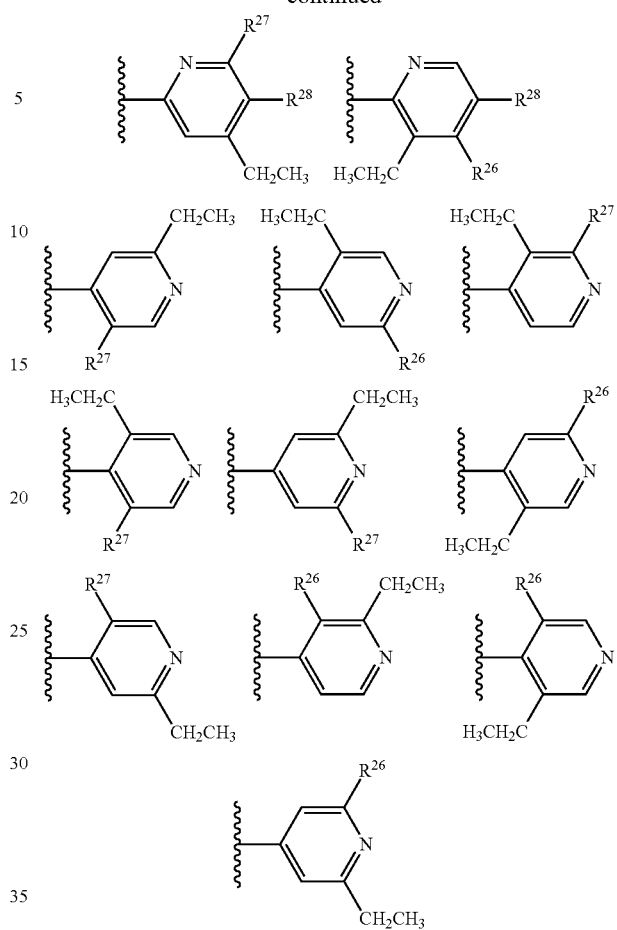
In one embodiment, B4 is selected from:
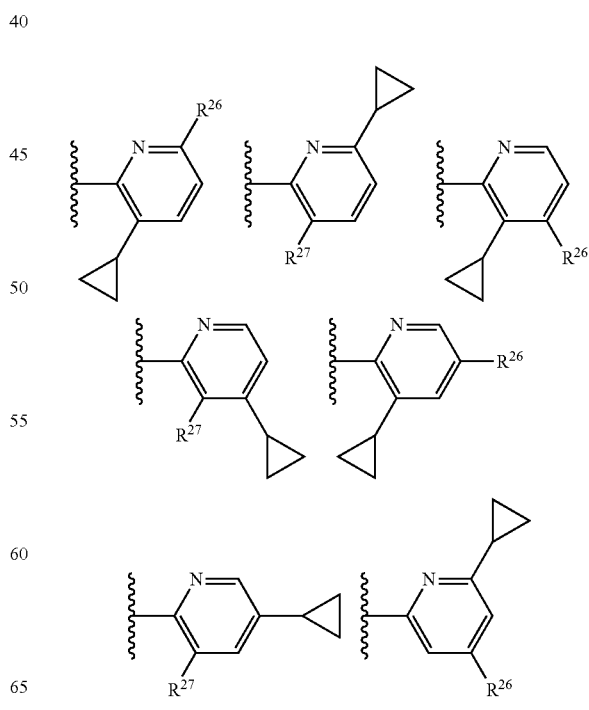

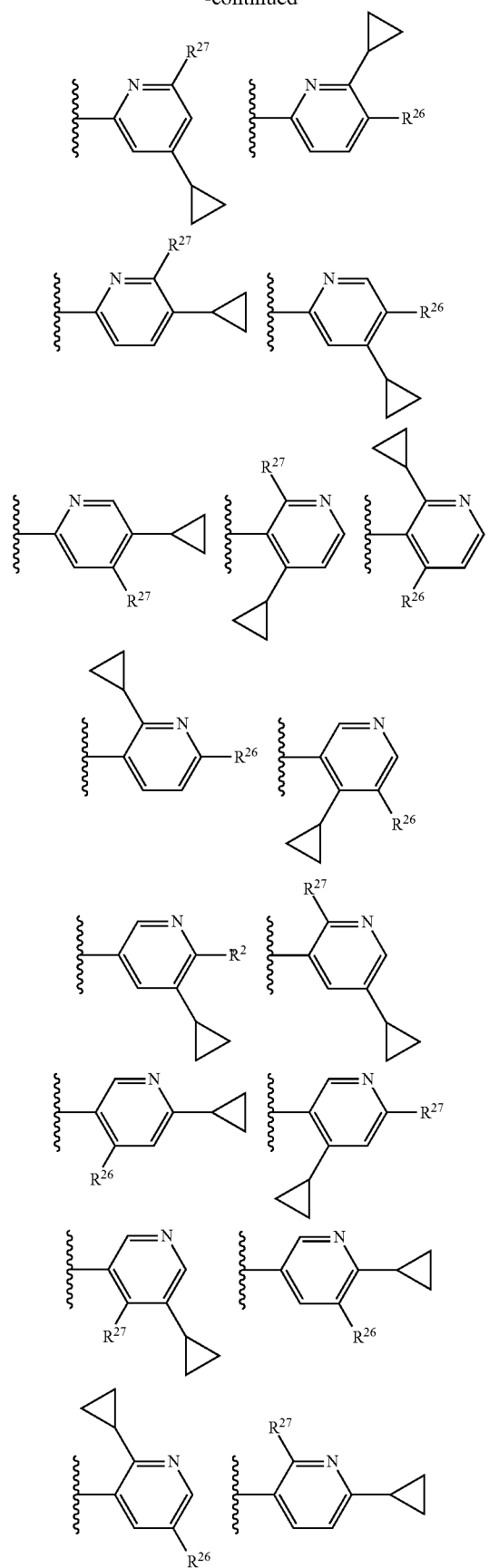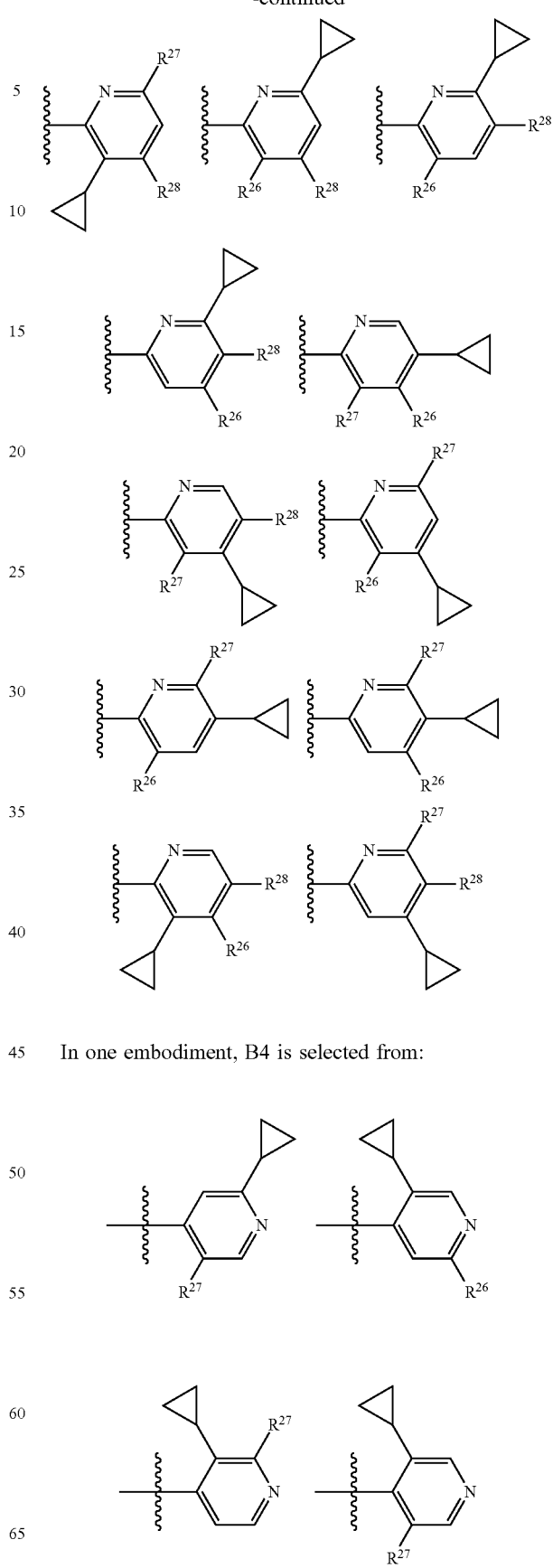
In one embodiment, B4 is selected from:
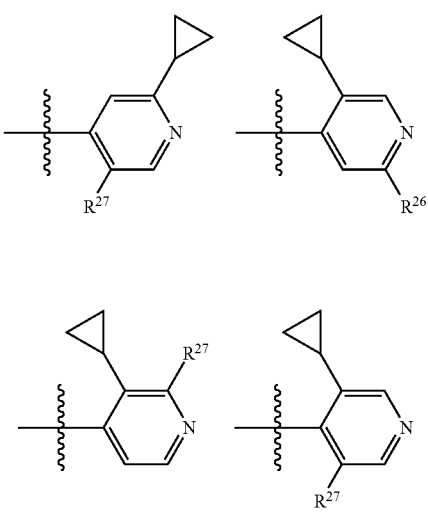

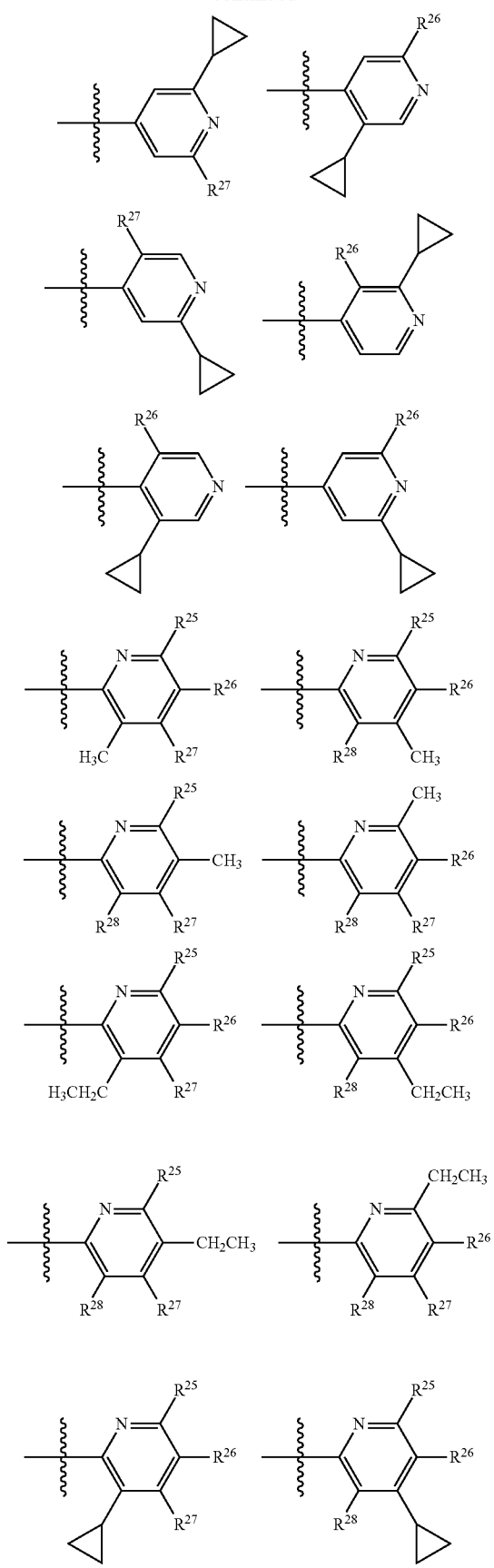
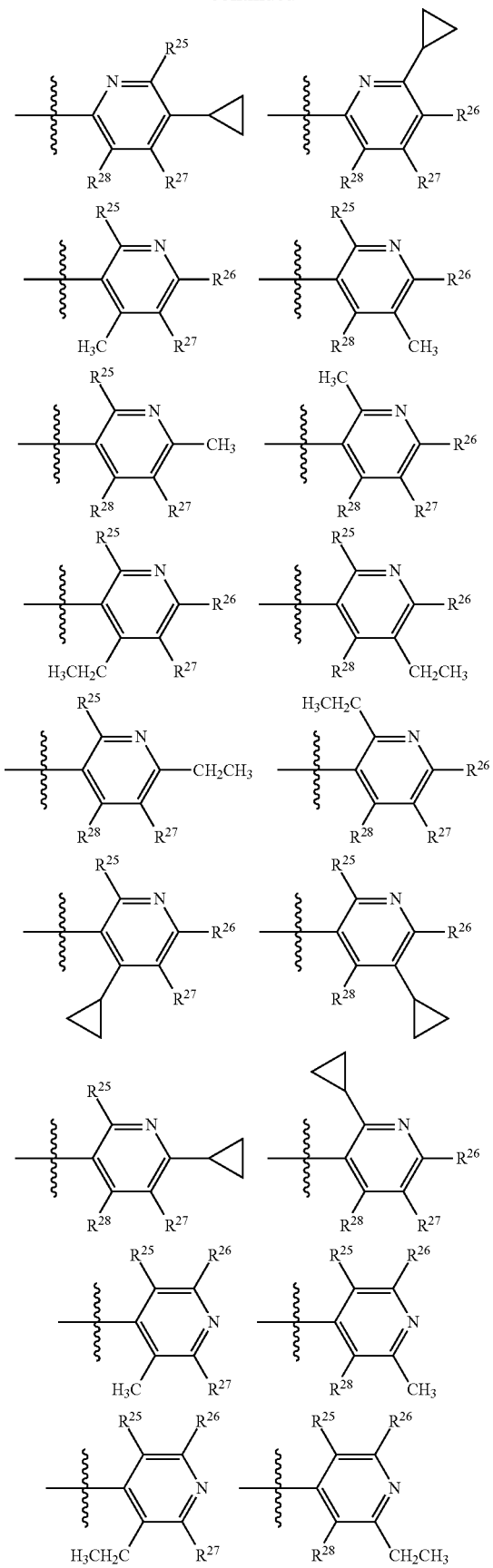

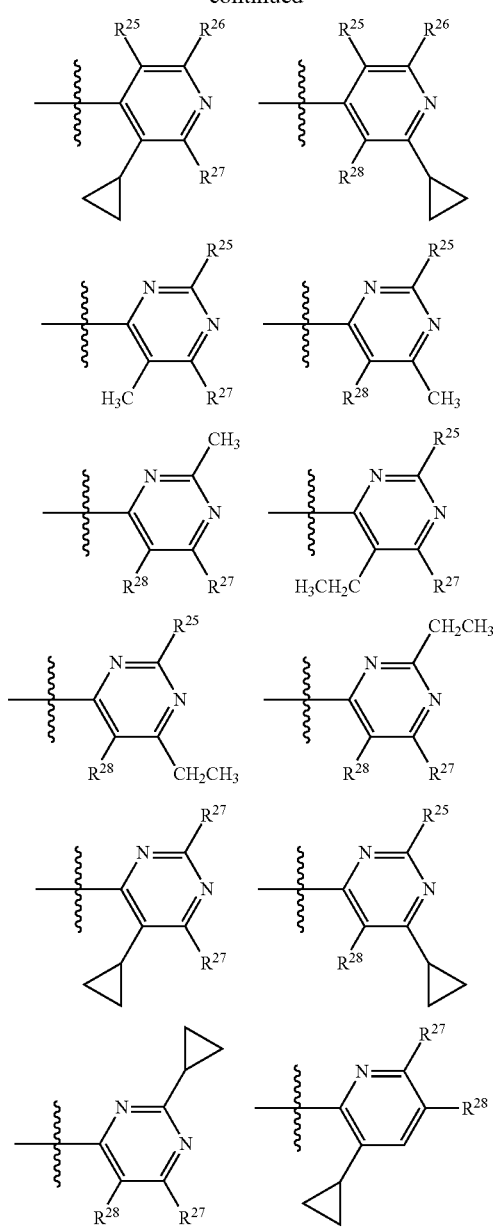
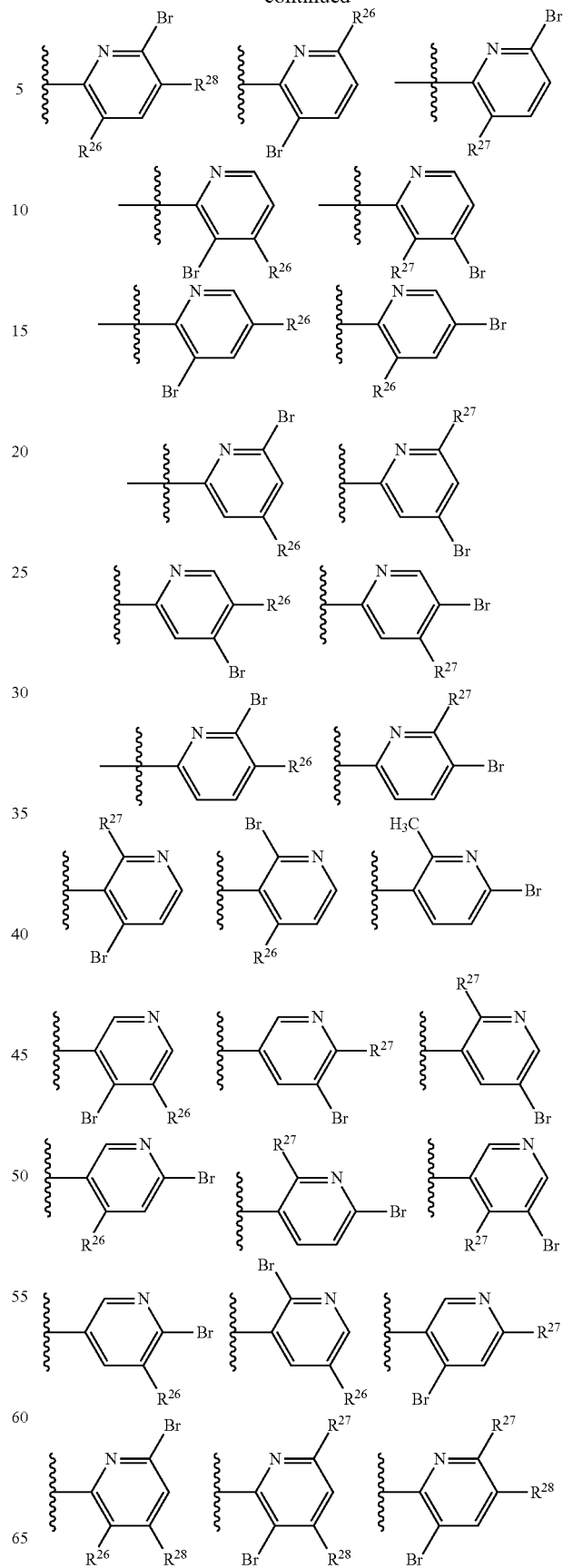
In one embodiment, B4 is selected from:
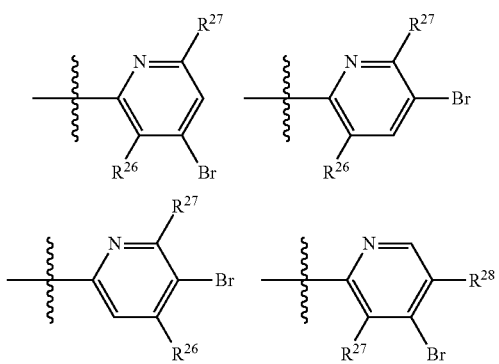

193
-continued
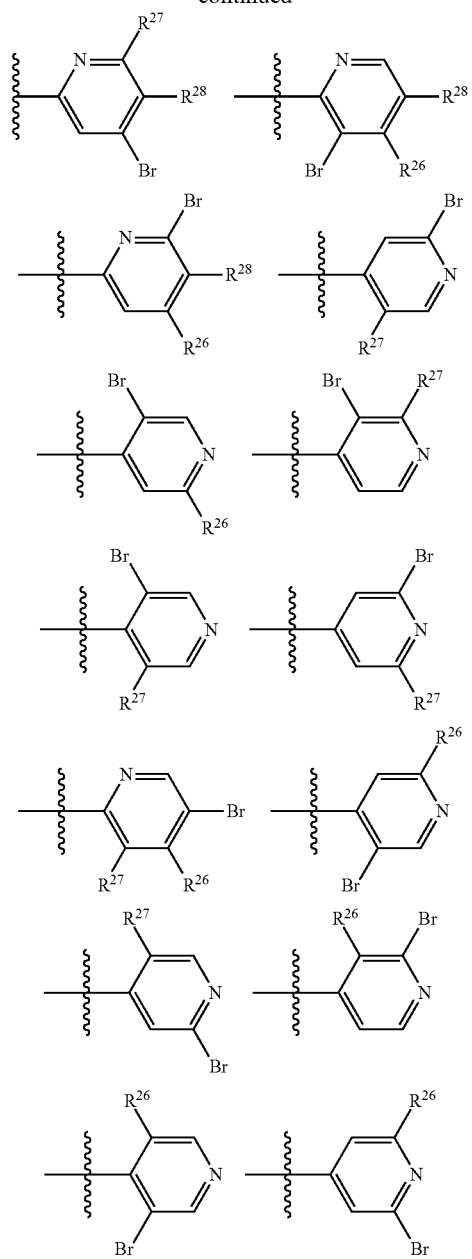
In one embodiment, B4 is selected from:
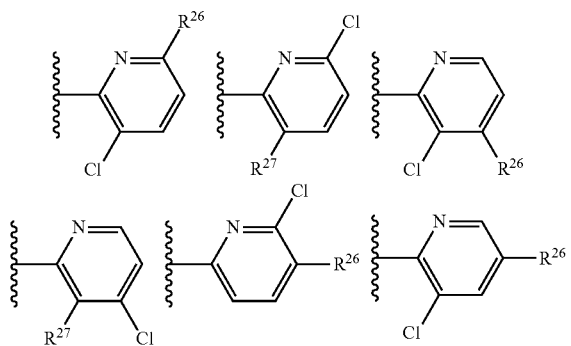
194
-continued
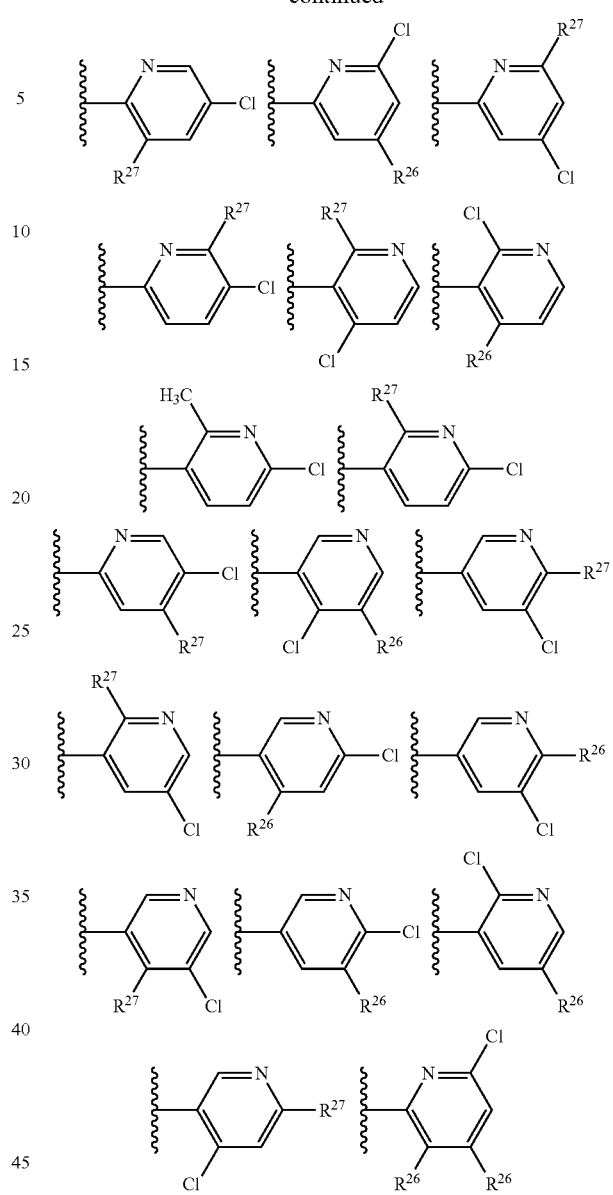
In one embodiment, B4 is selected from:
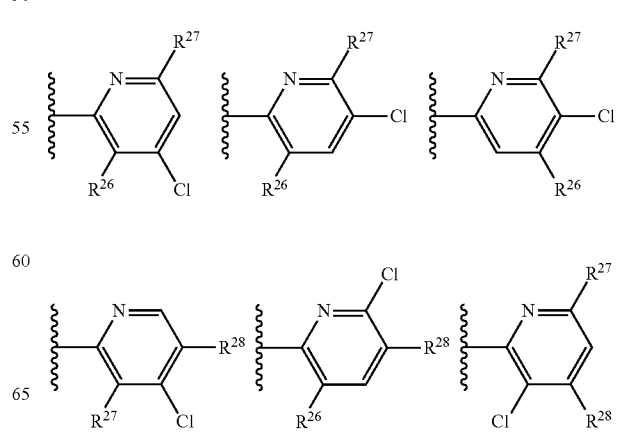

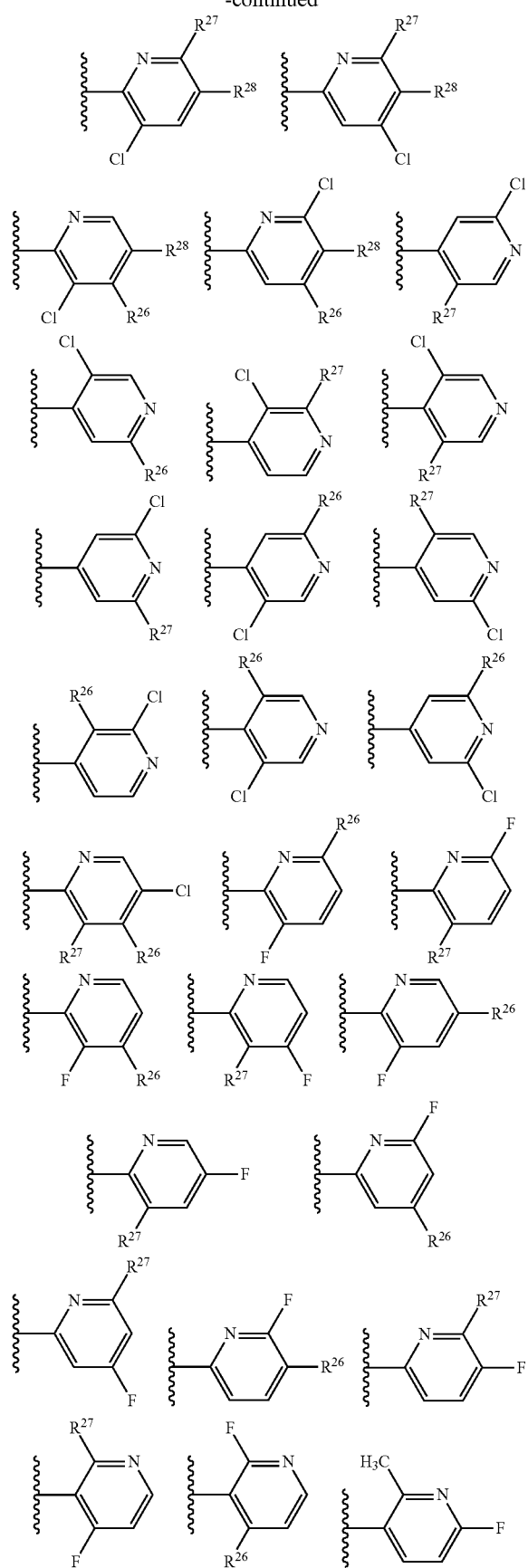
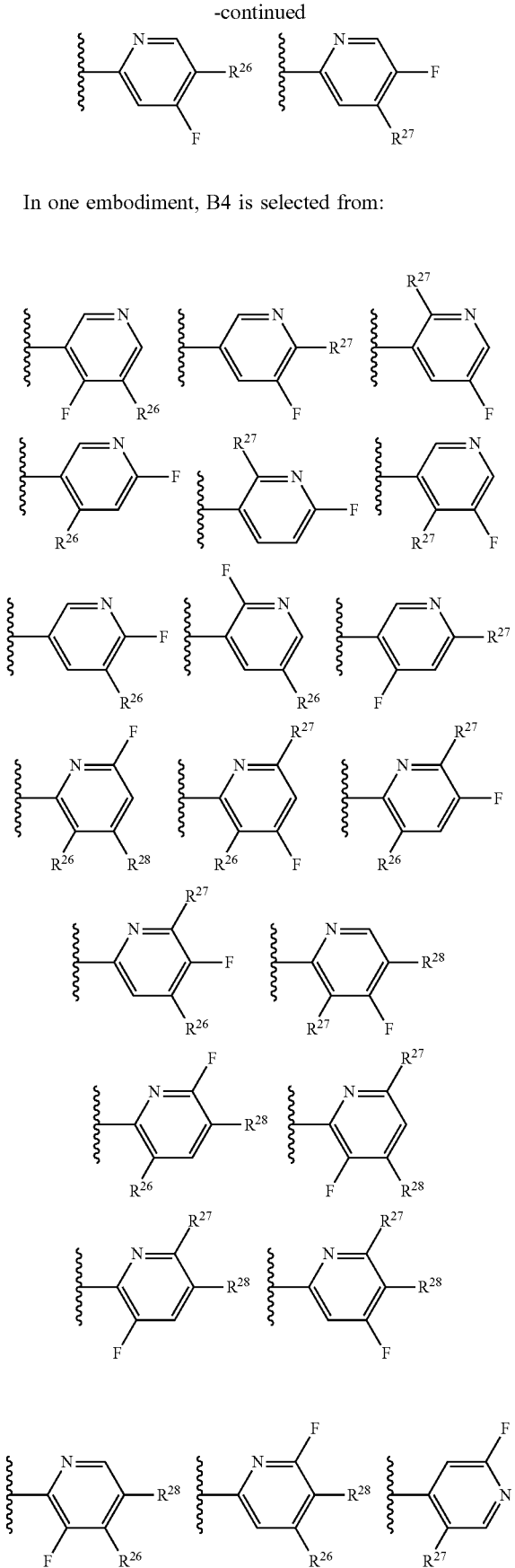
In one embodiment, B4 is selected from:

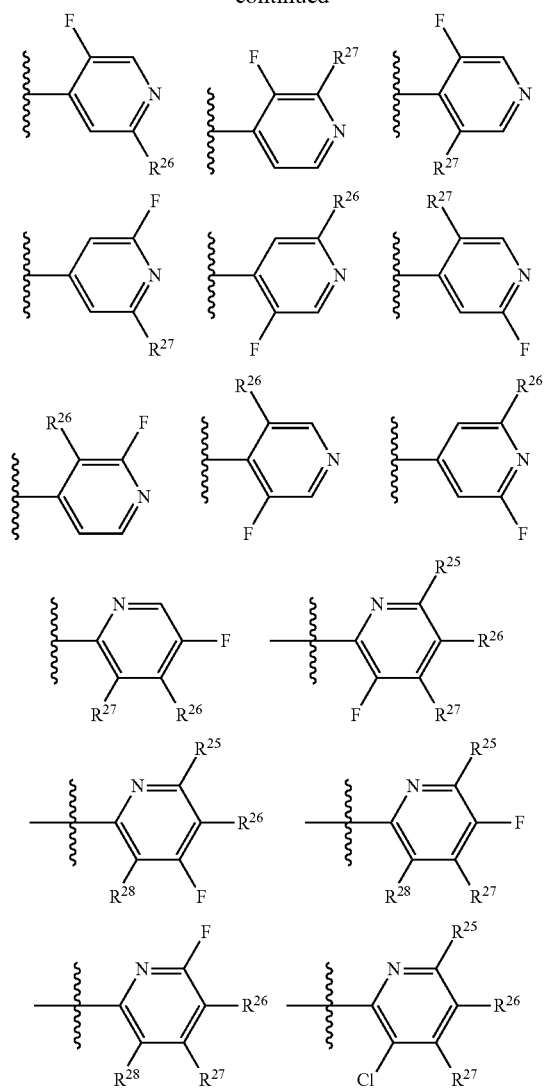
In one embodiment, B4 is selected from:
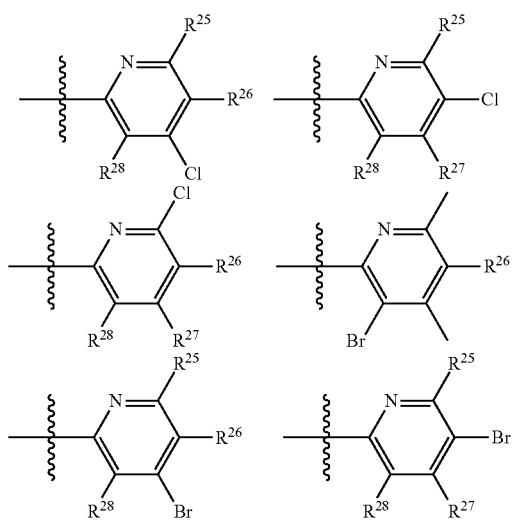
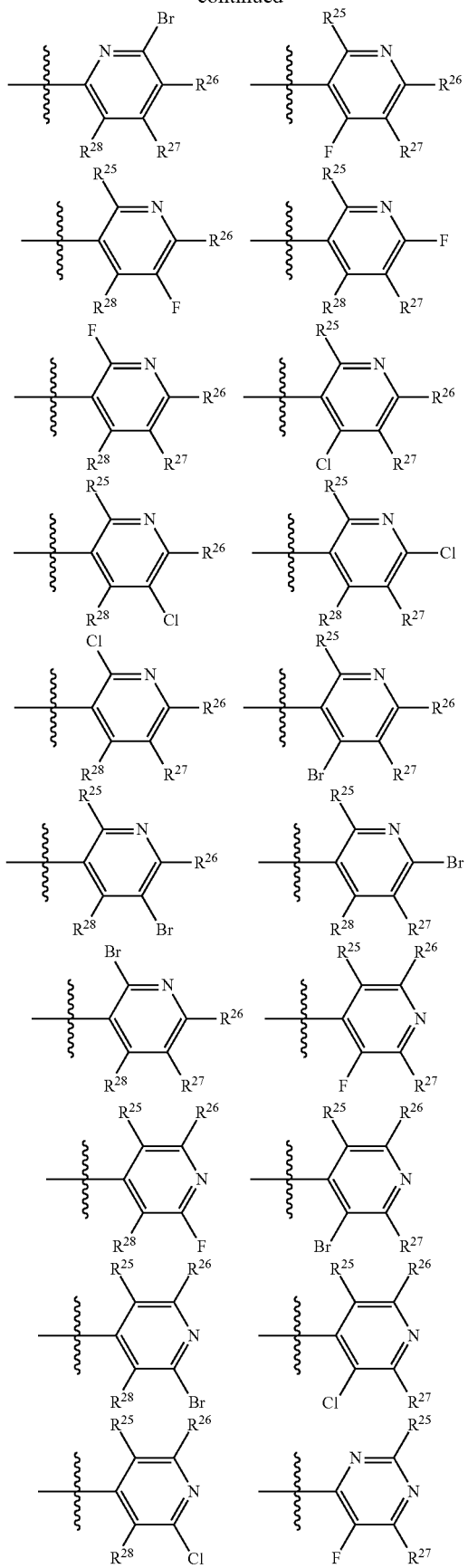

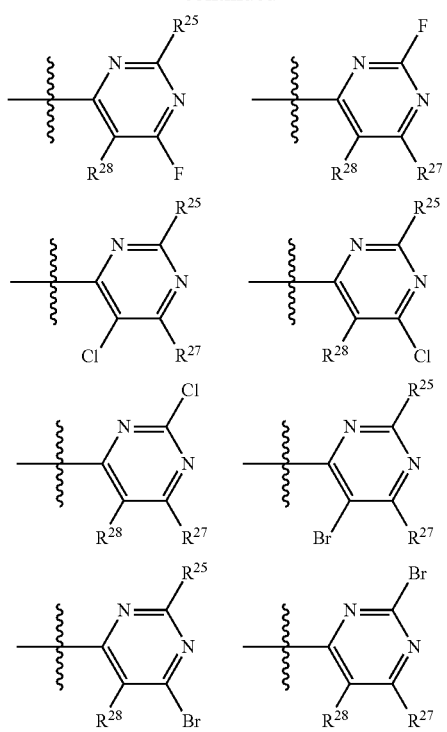
In one embodiment B4 is selected from:
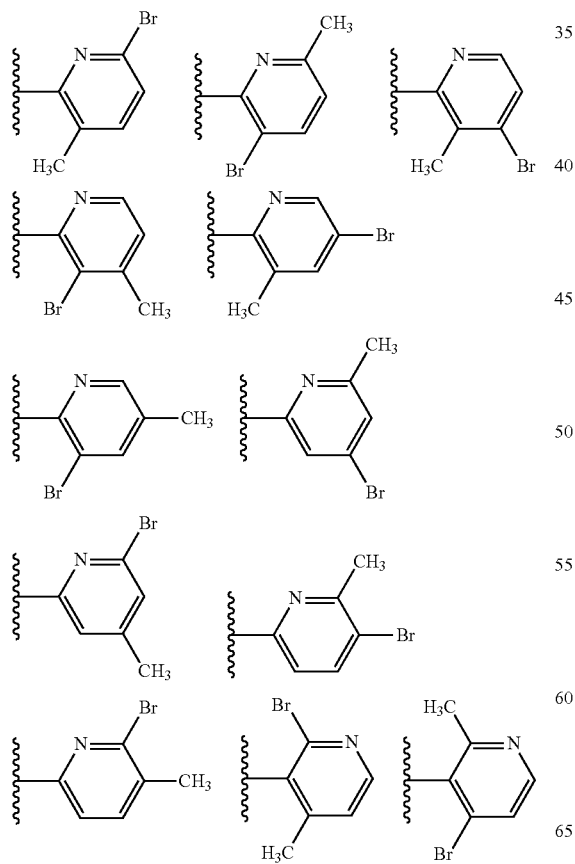
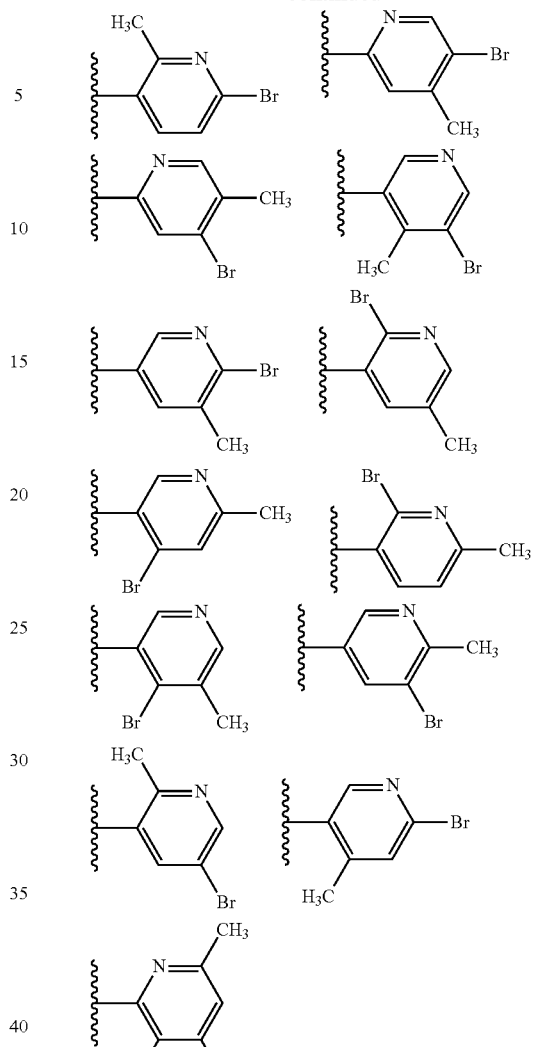
In one embodiment, B4 is selected from:
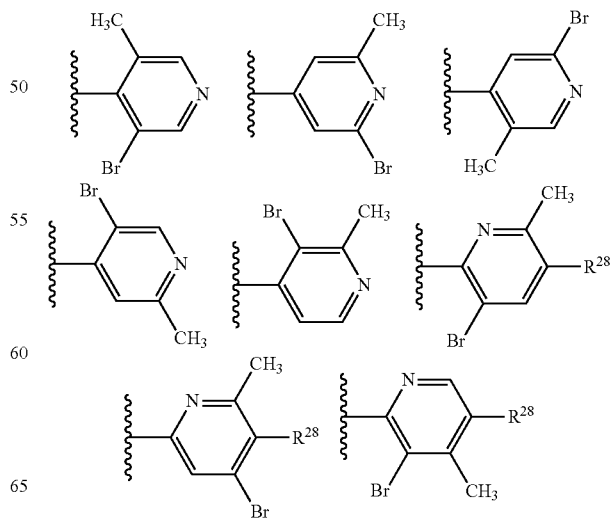

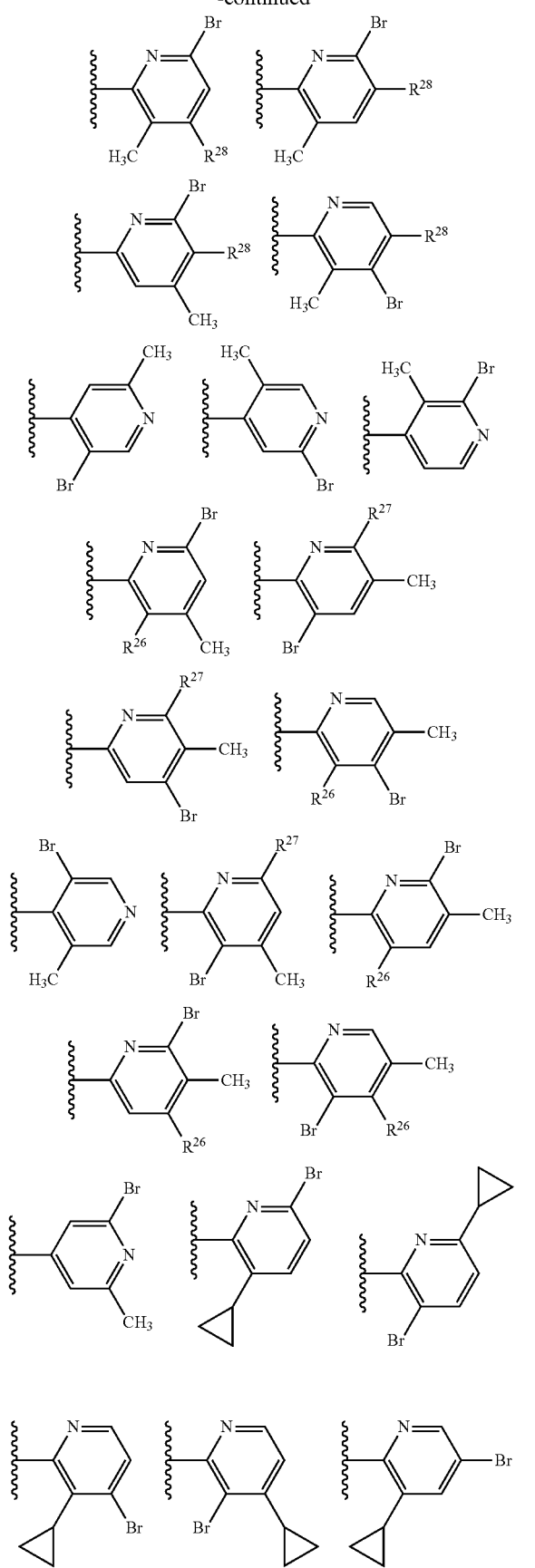
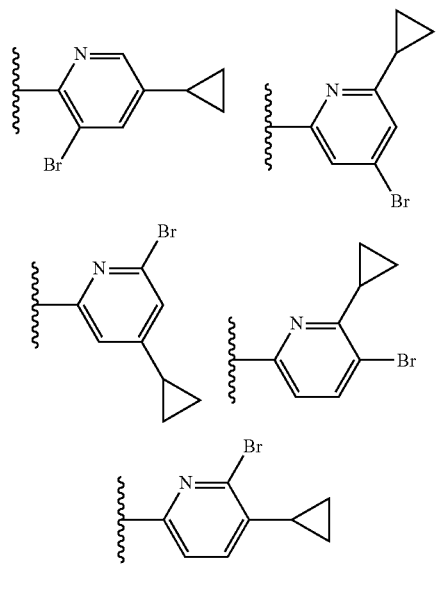
In one embodiment, B4 is selected from:
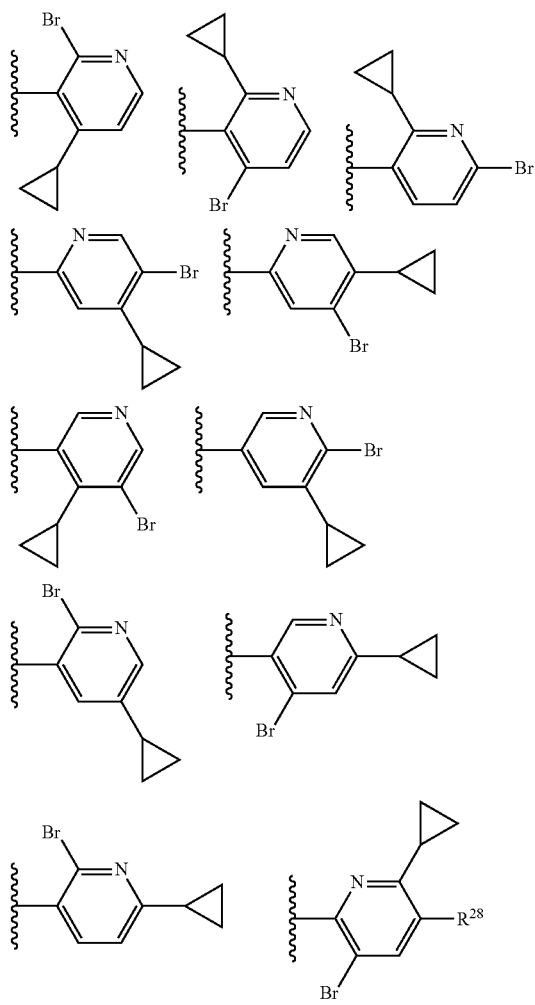

-continued
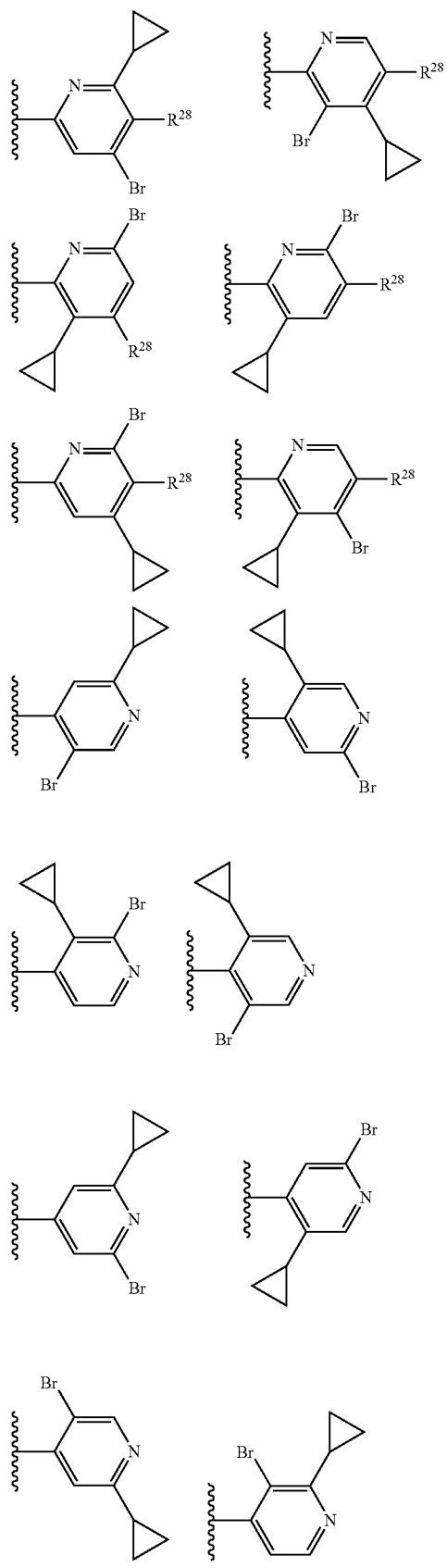
In one embodiment, B4 is selected from:
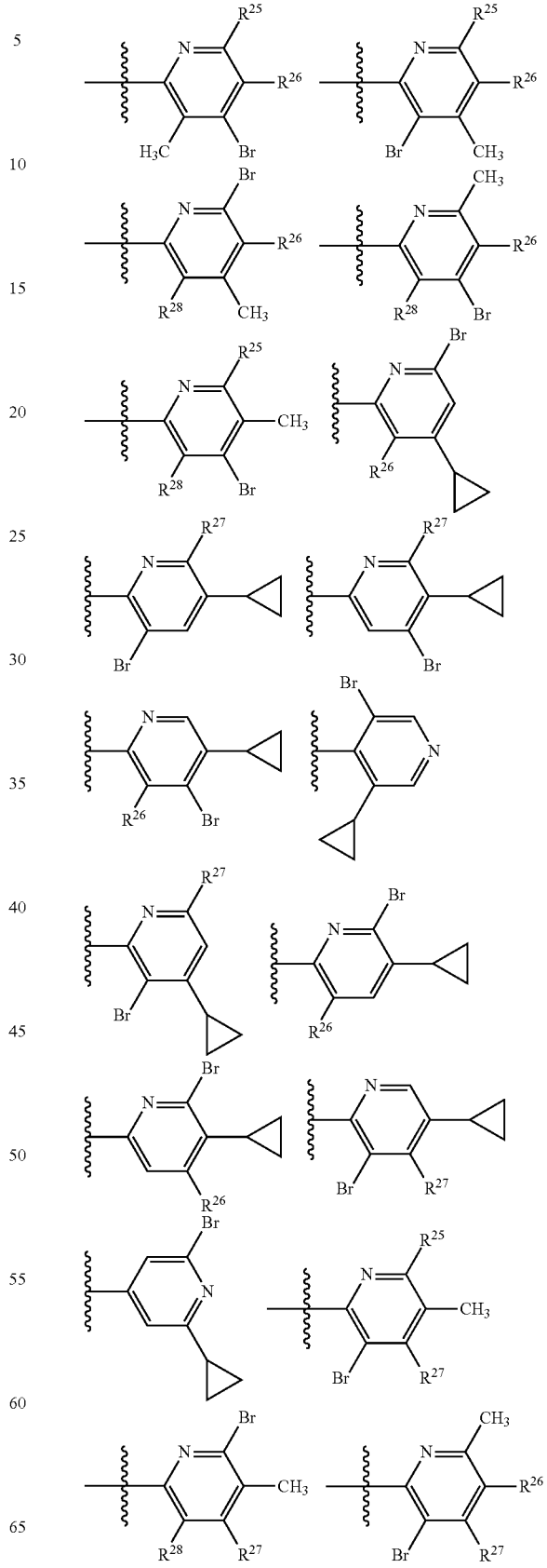

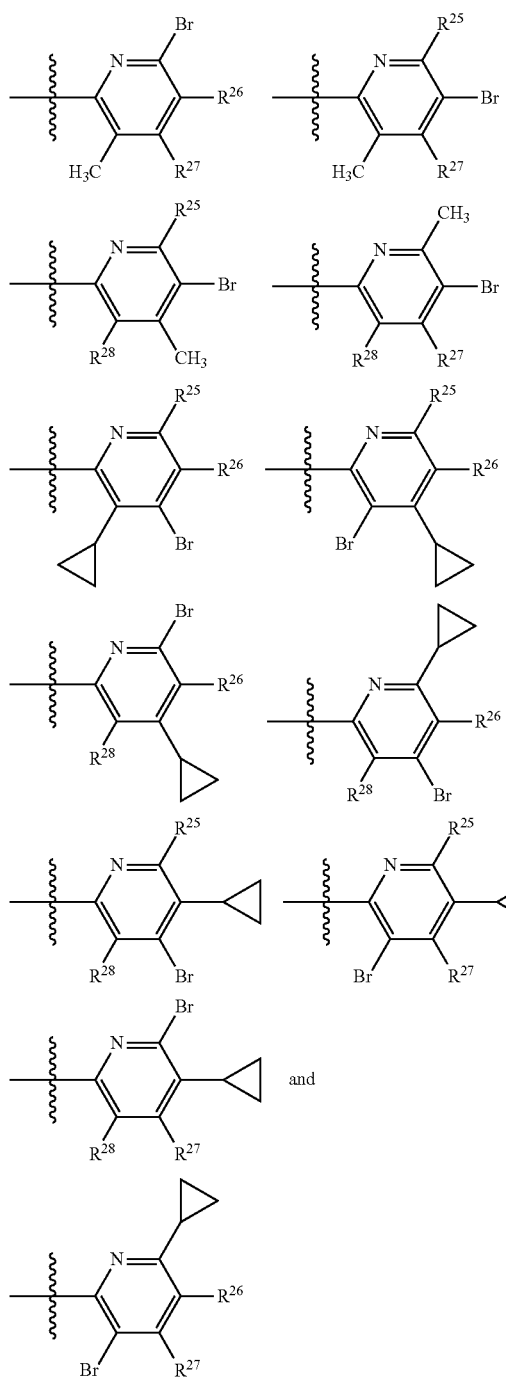
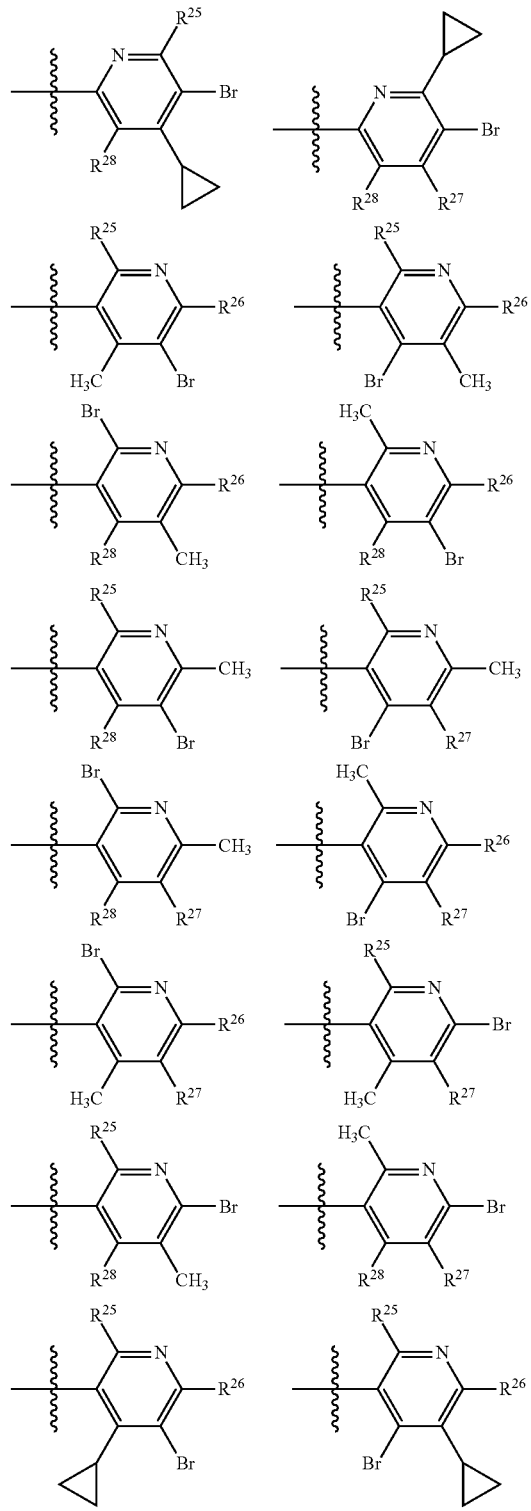
In one embodiment, B4 is selected from:
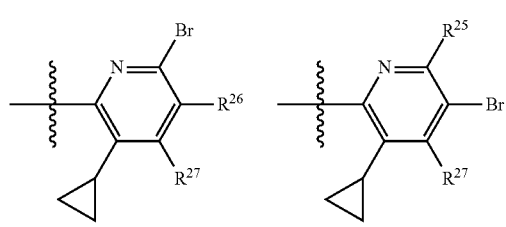
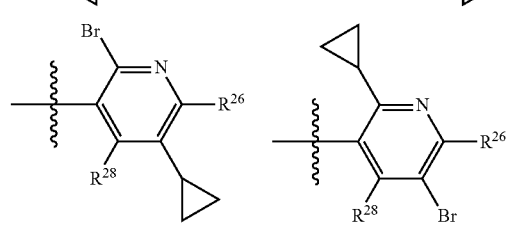

-continued
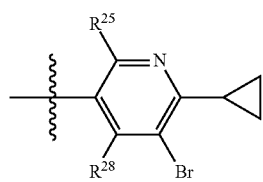
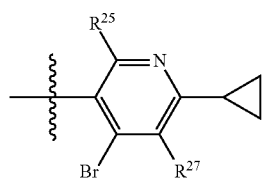
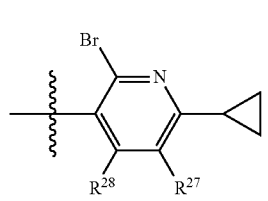
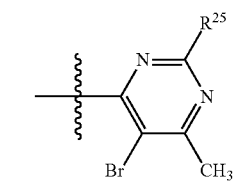
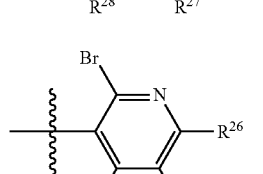
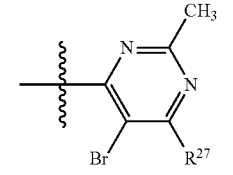

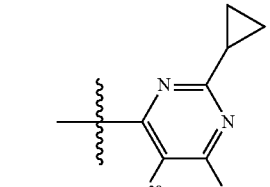

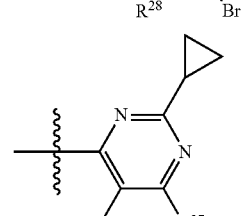
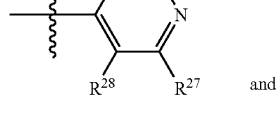
In one embodiment, B4 is selected from:
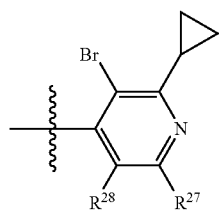
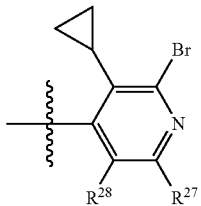
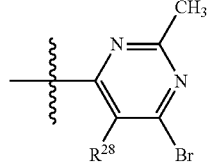
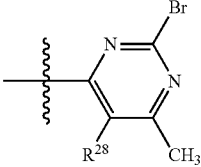
-continued
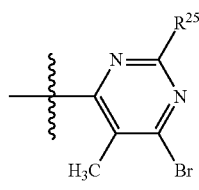
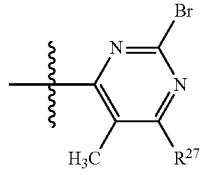
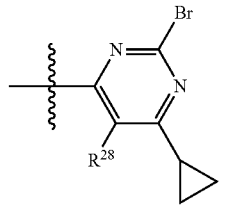
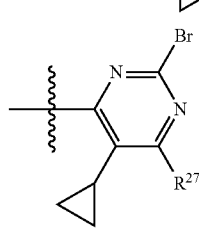
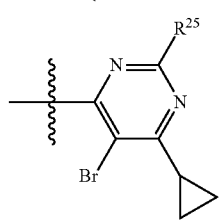
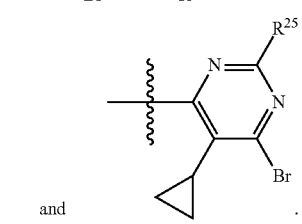
and .
In one embodiment, B4 is selected from:
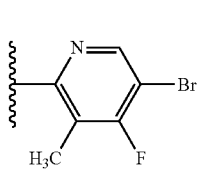
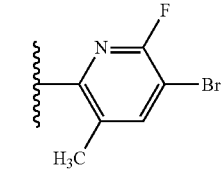
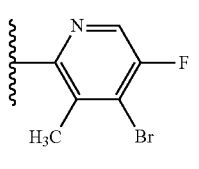
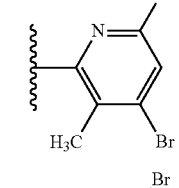
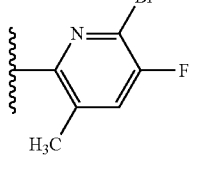
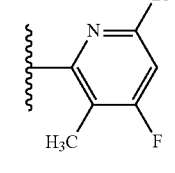

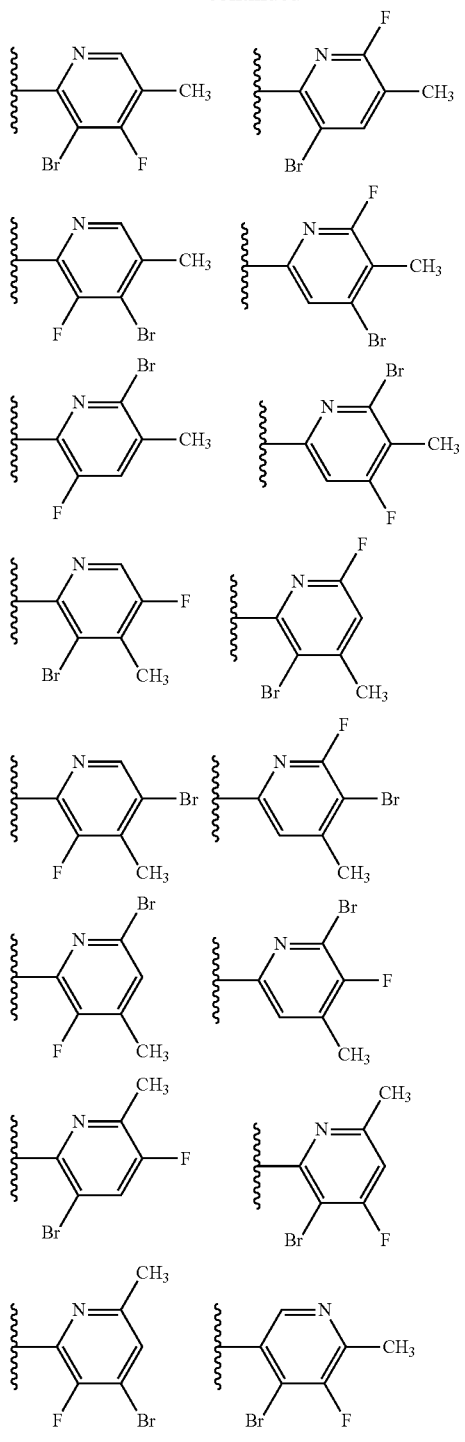
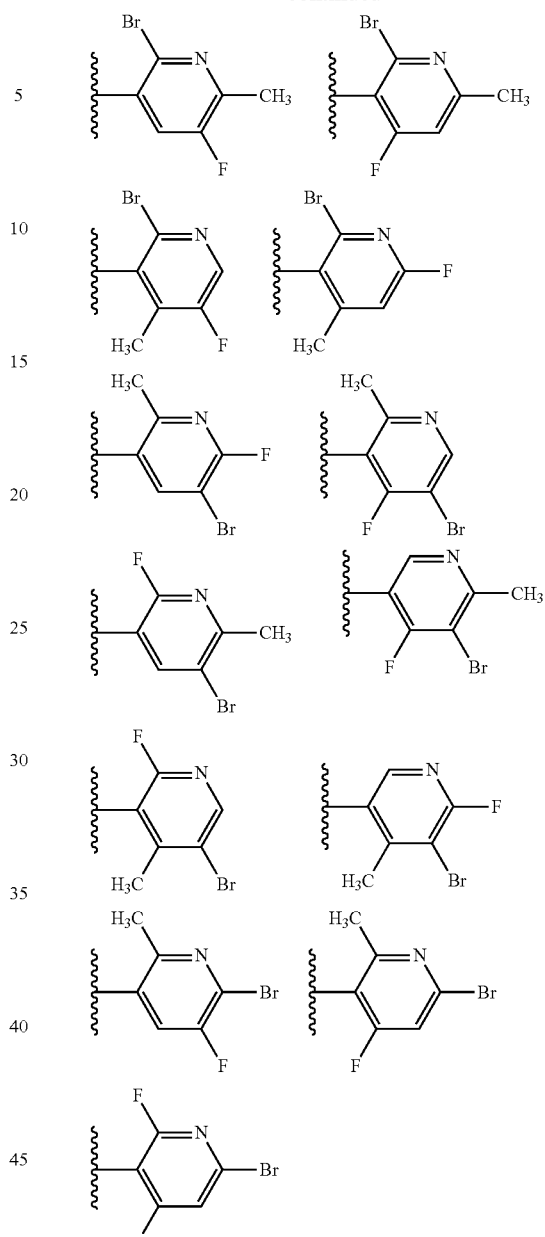
In one embodiment, B4 is selected from:
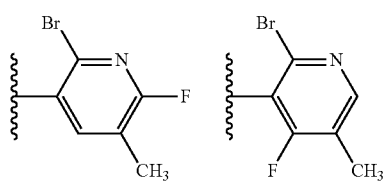
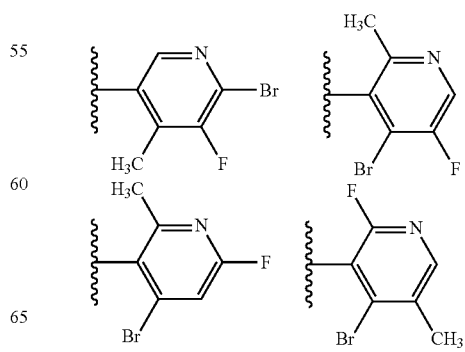

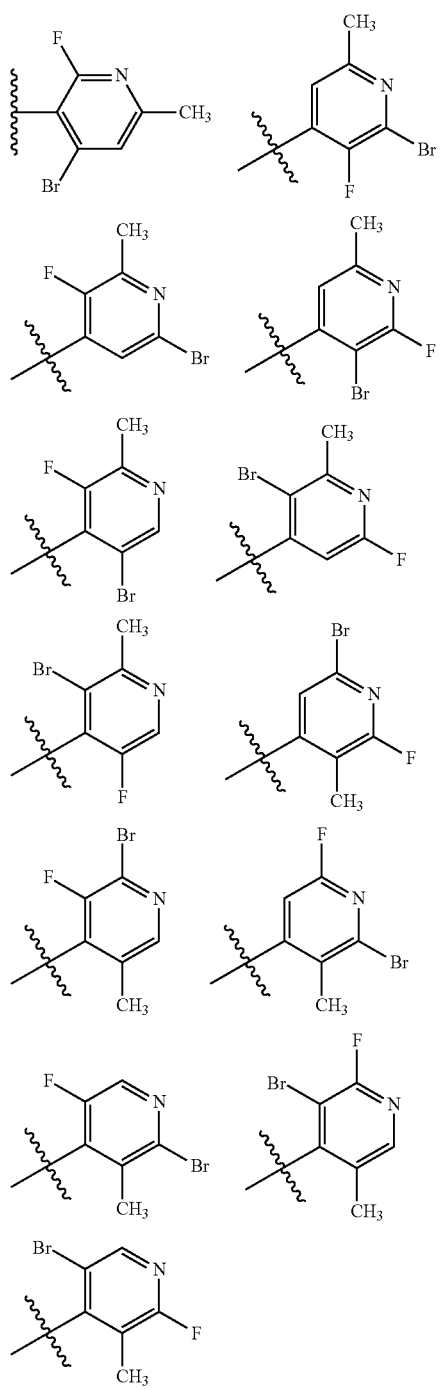
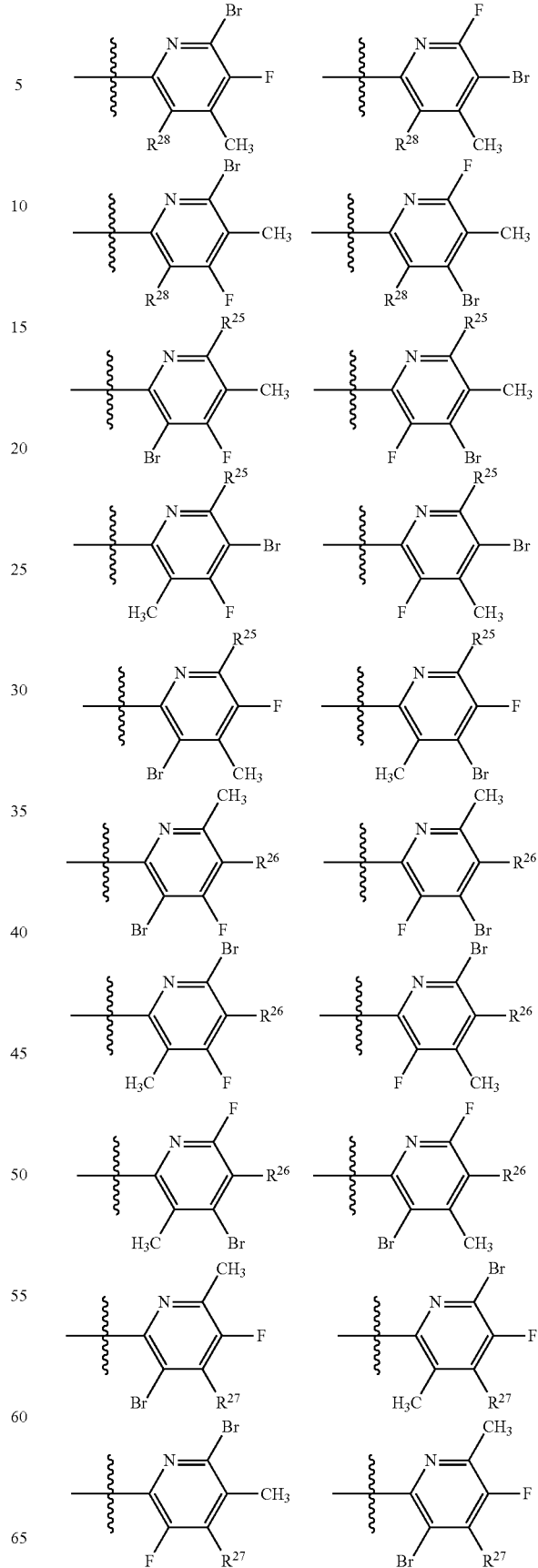
In one embodiment, B4 is selected from:
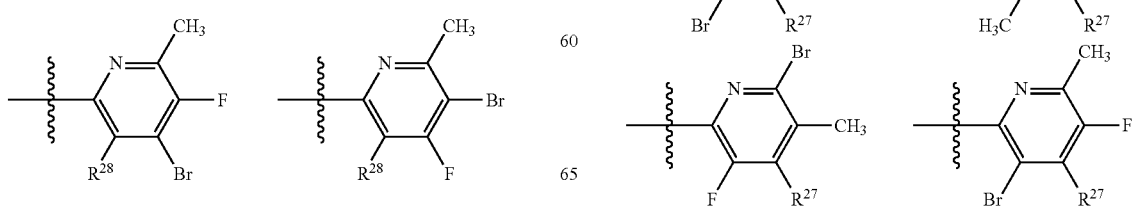

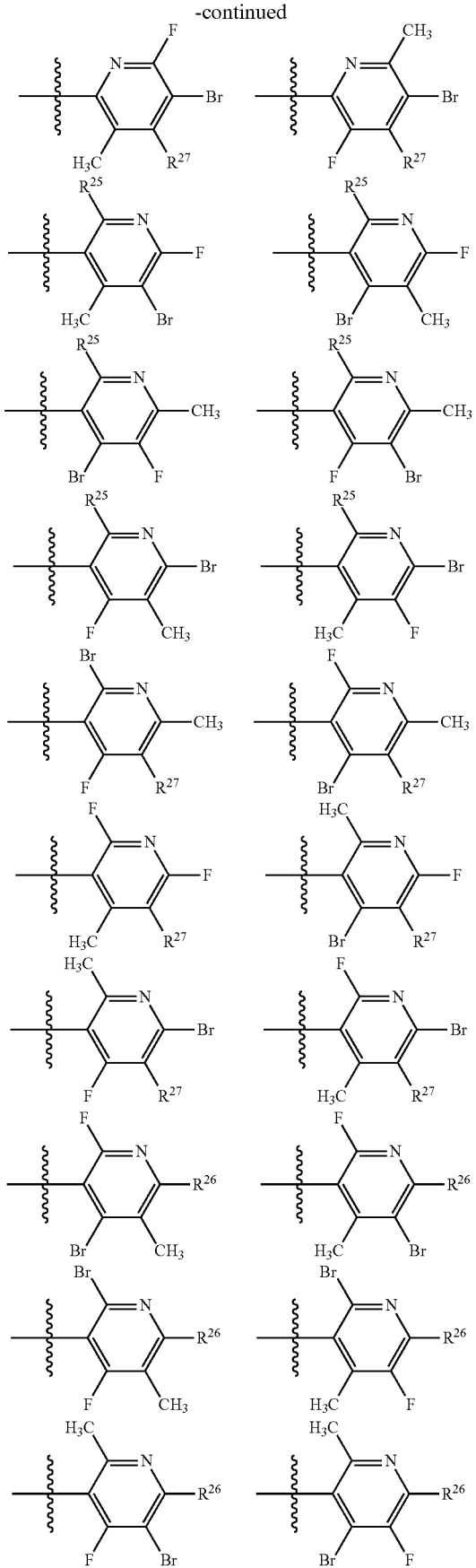
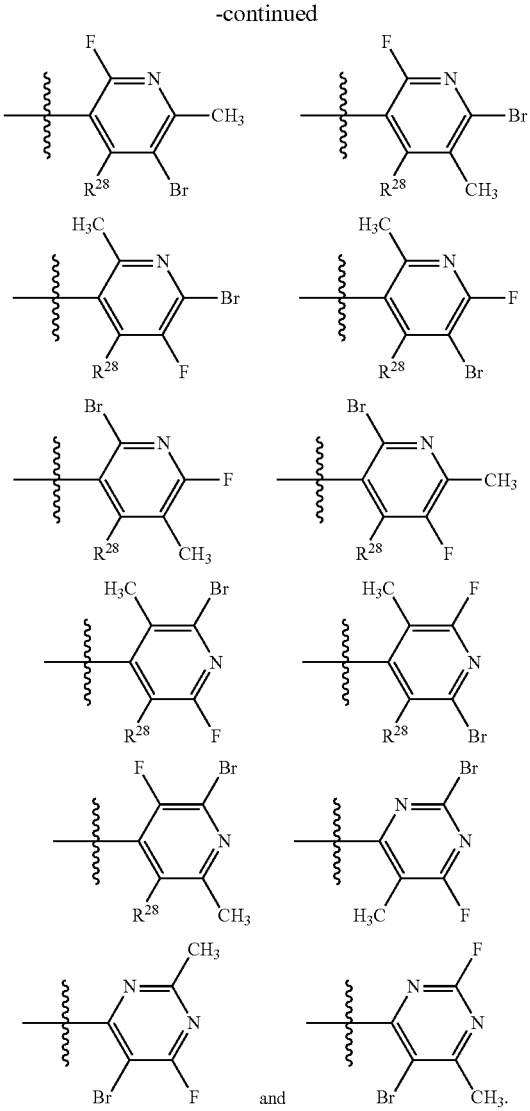
In one embodiment, B4 is selected from:
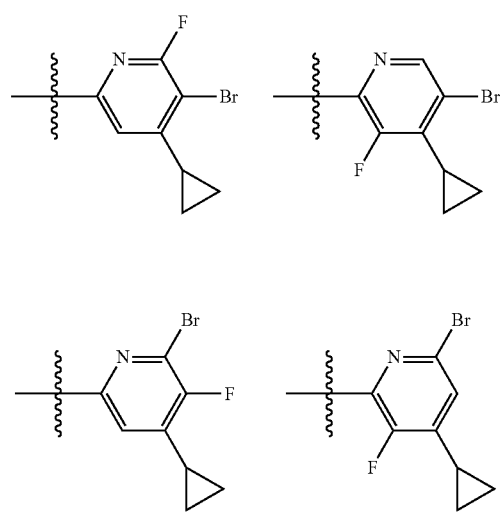

-continued
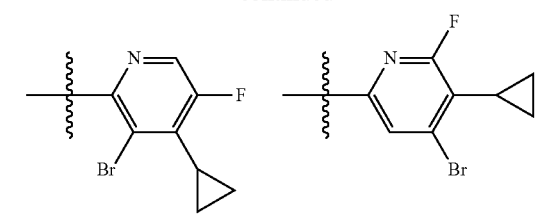
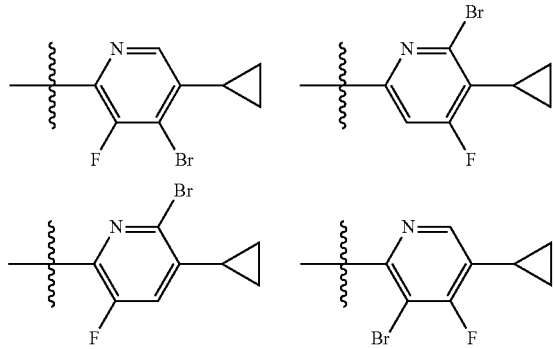
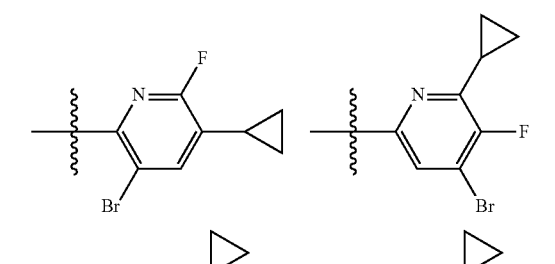
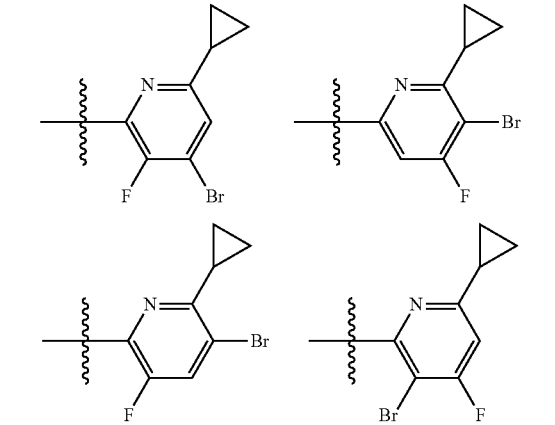
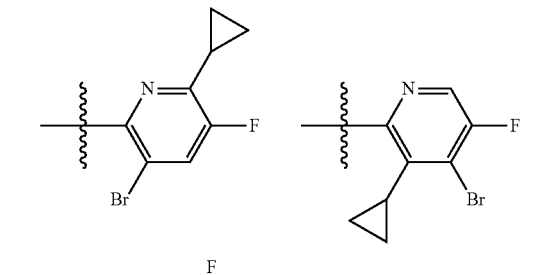
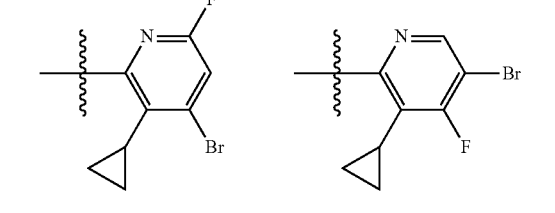
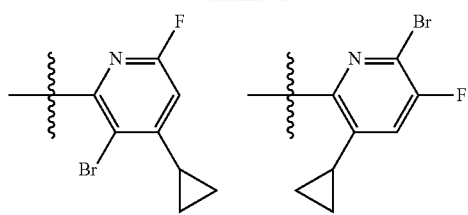
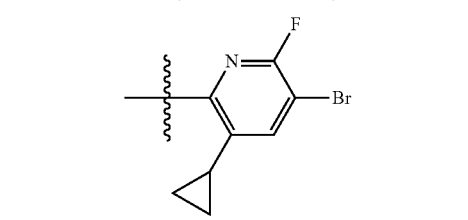
In one embodiment, B4 is selected from:
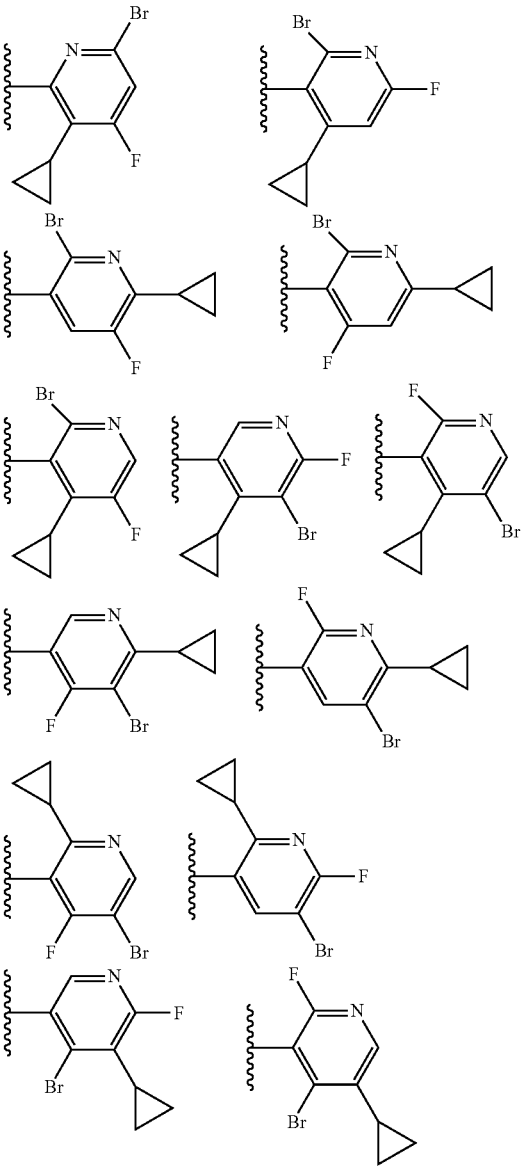

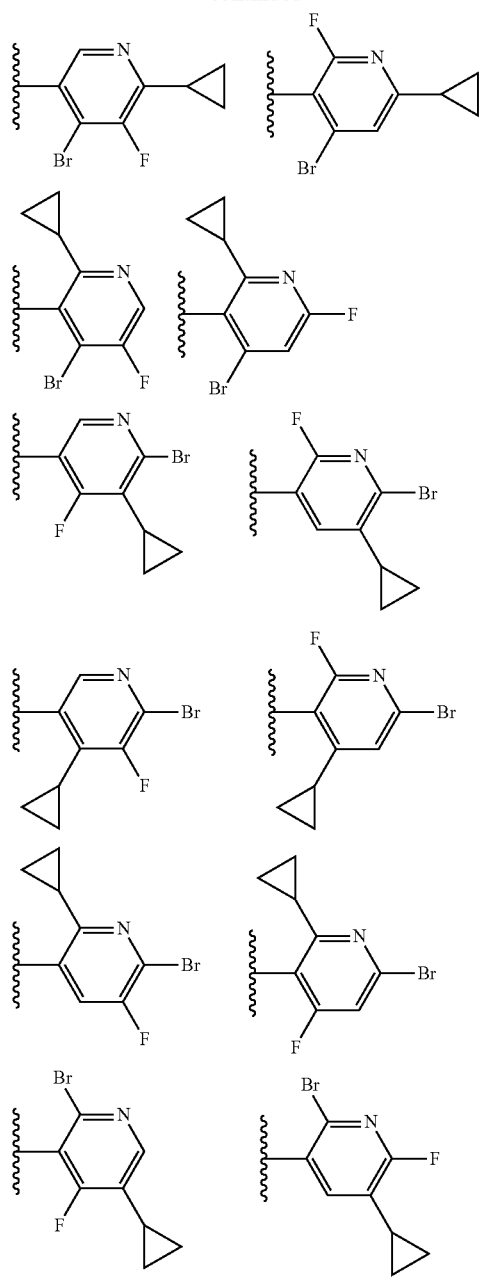
In one embodiment, B4 is selected from:
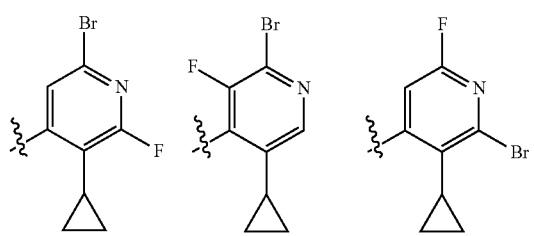
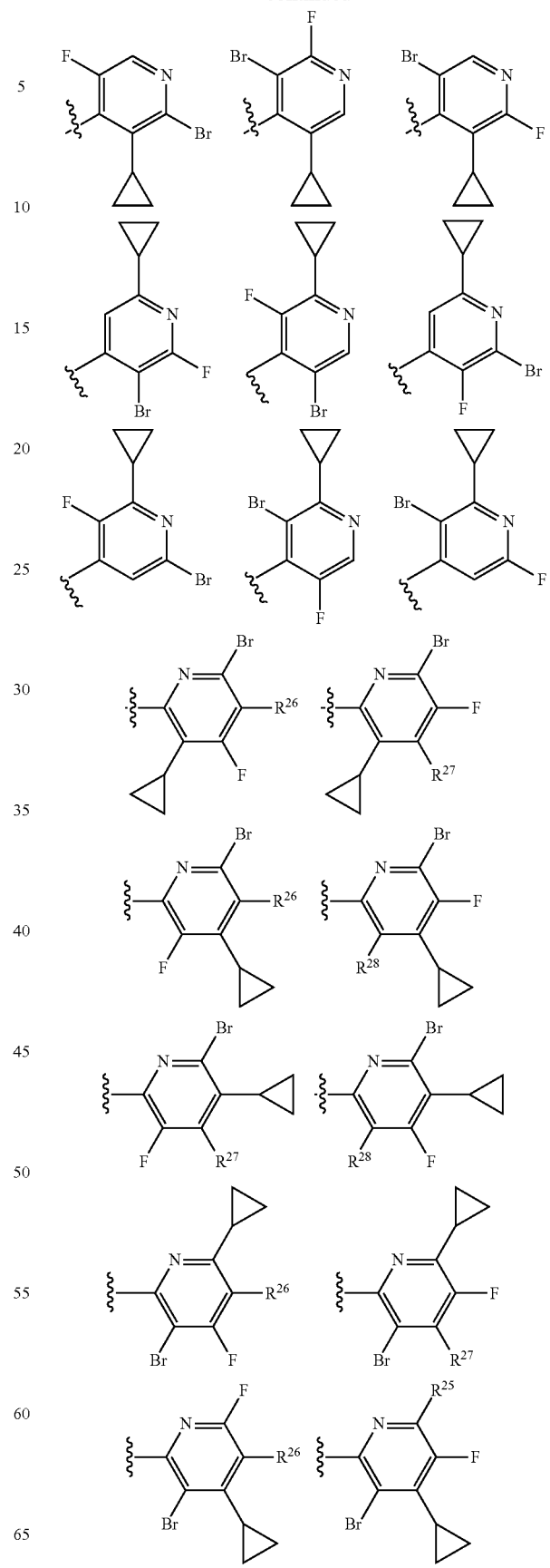

-continued
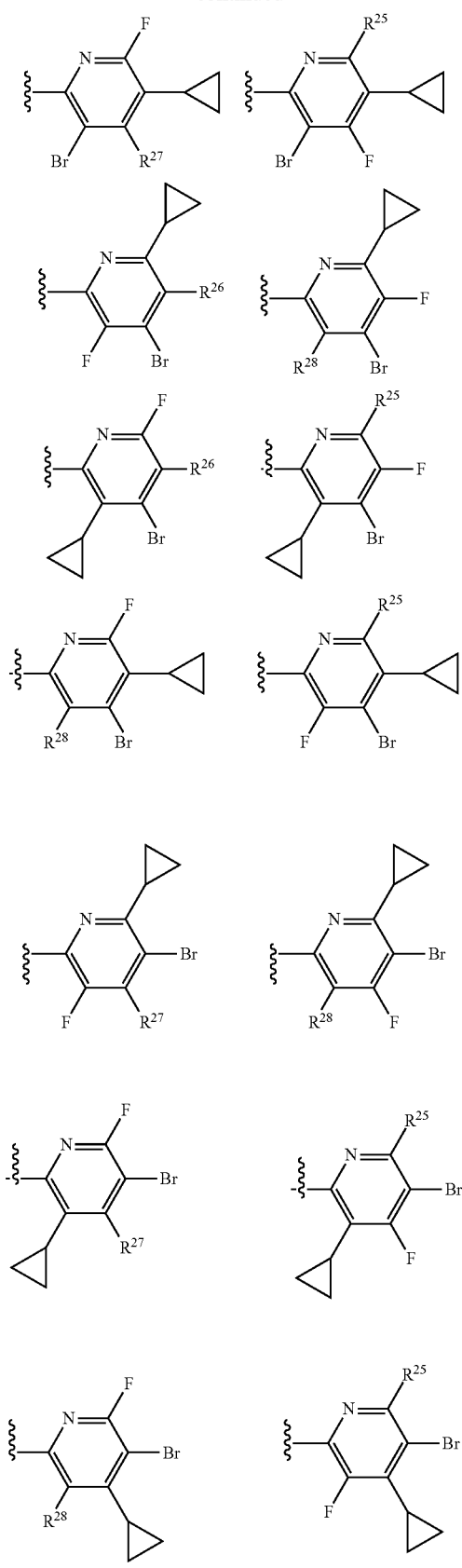
In one embodiment, B4 is selected from:
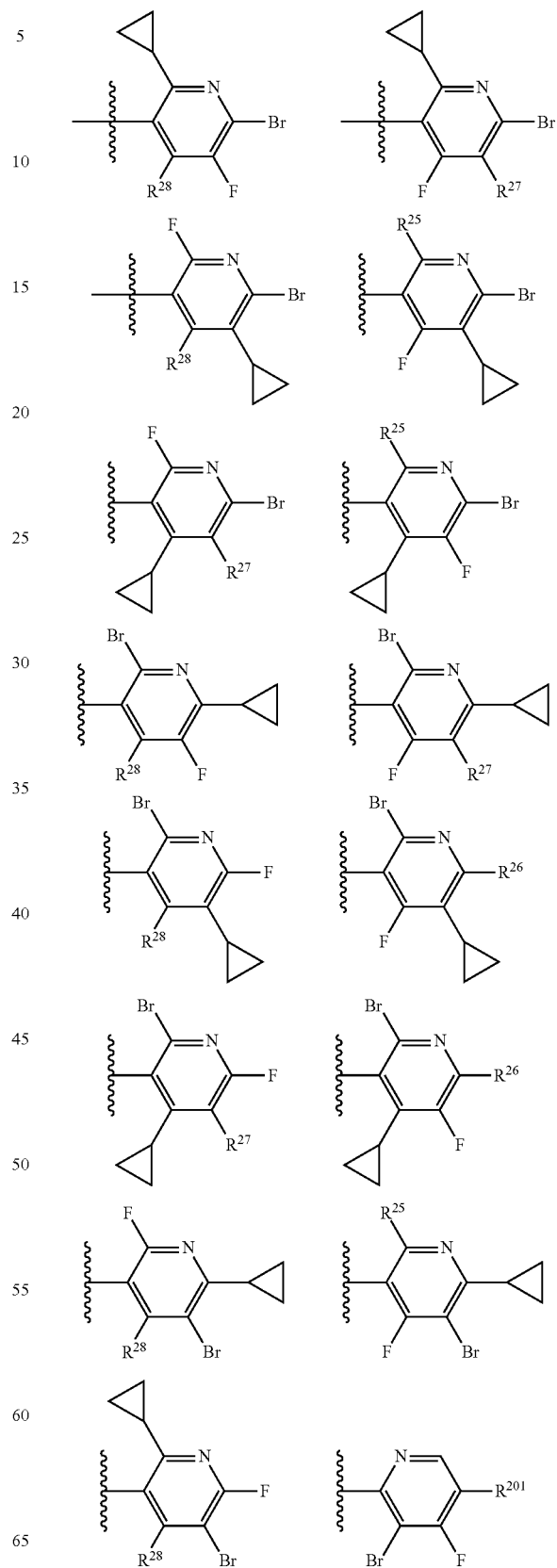

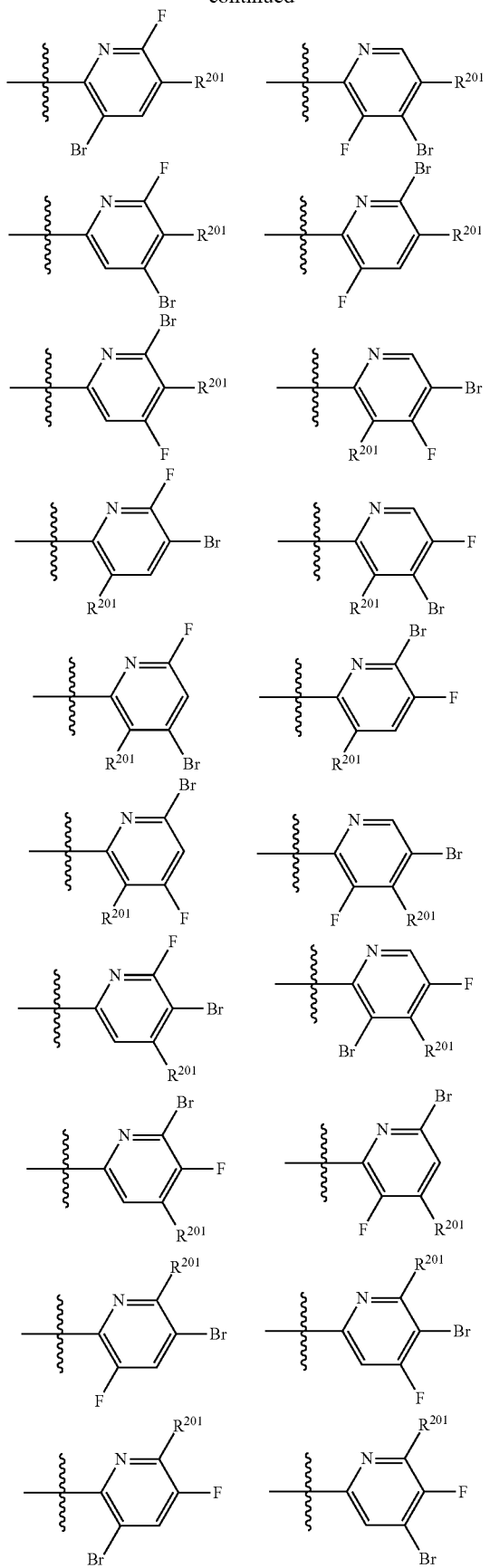
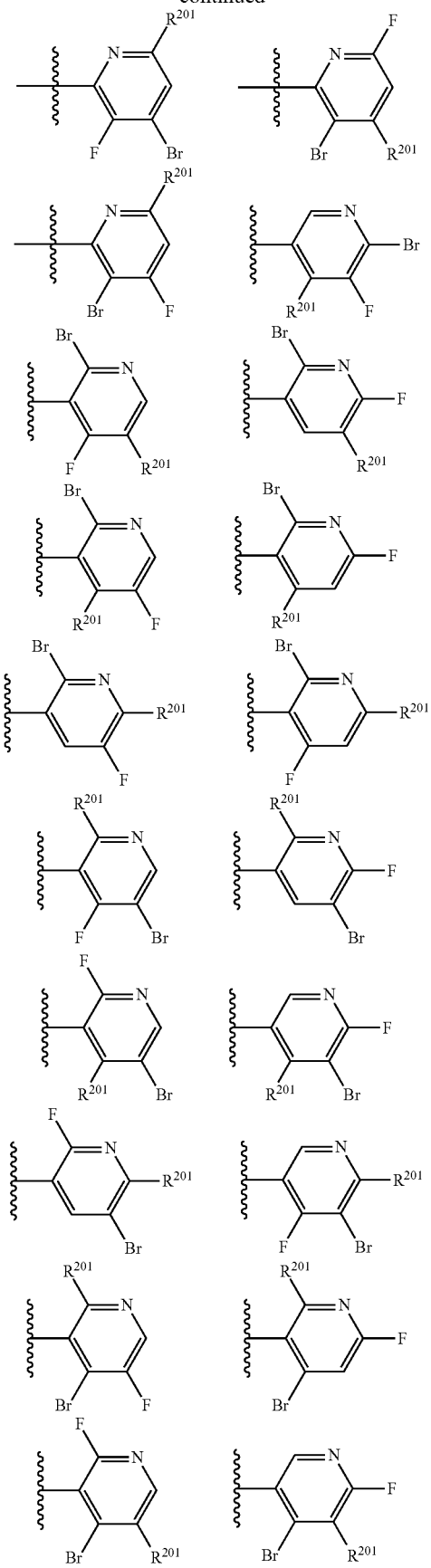

-continued
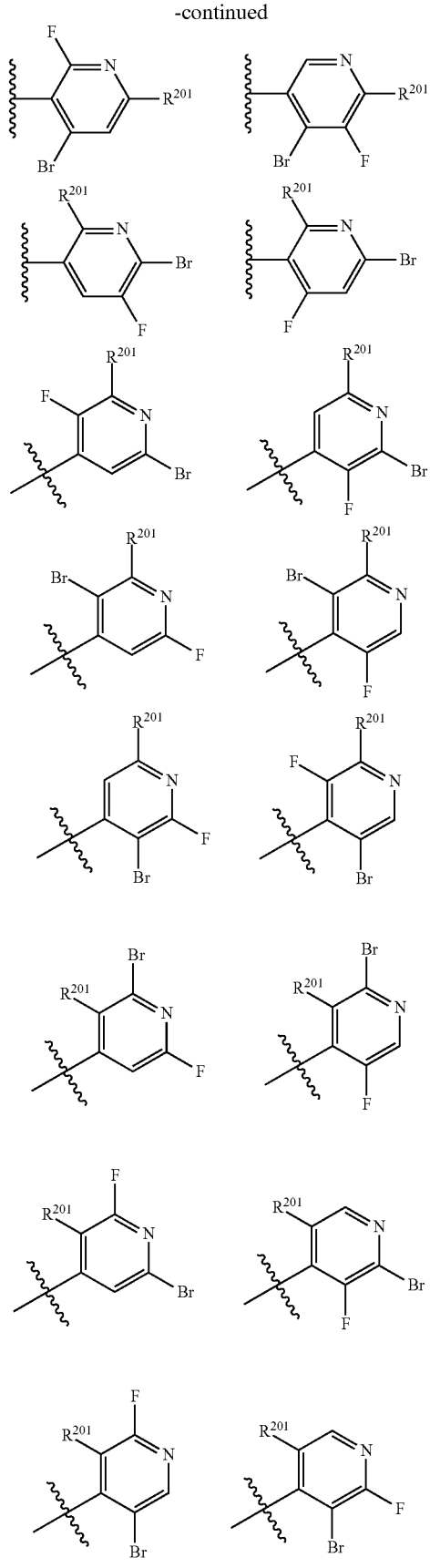
In one embodiment, B4 is selected from:
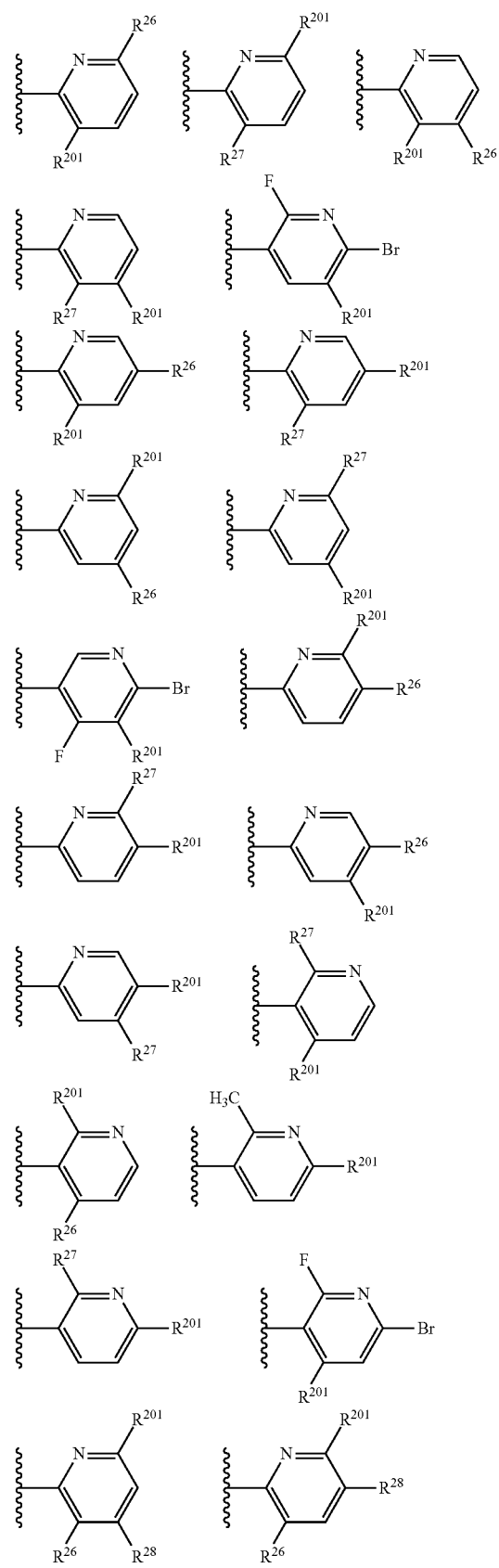

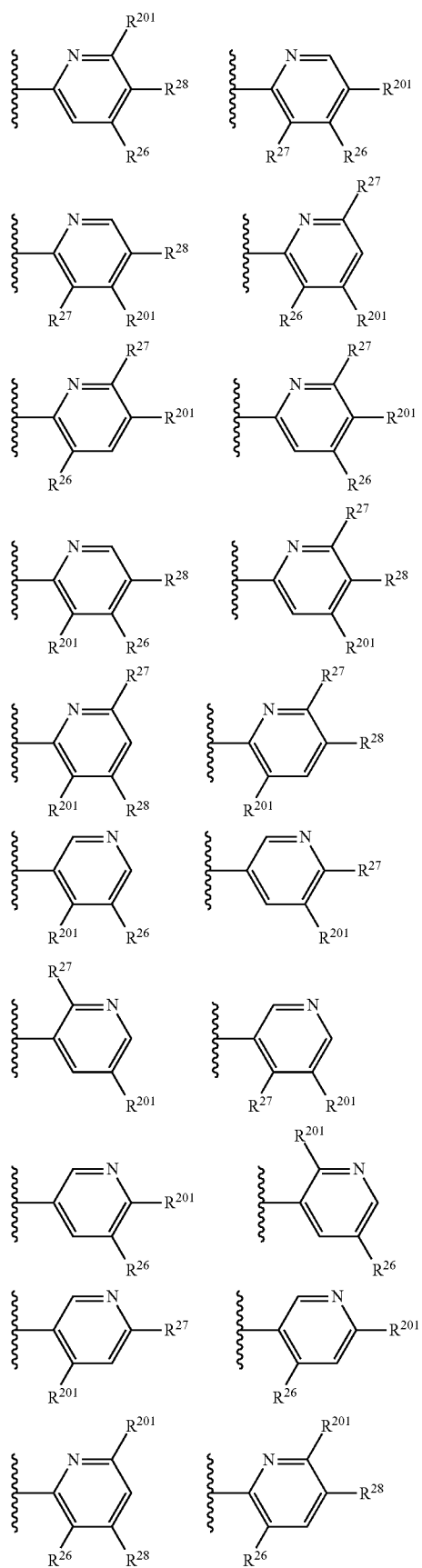
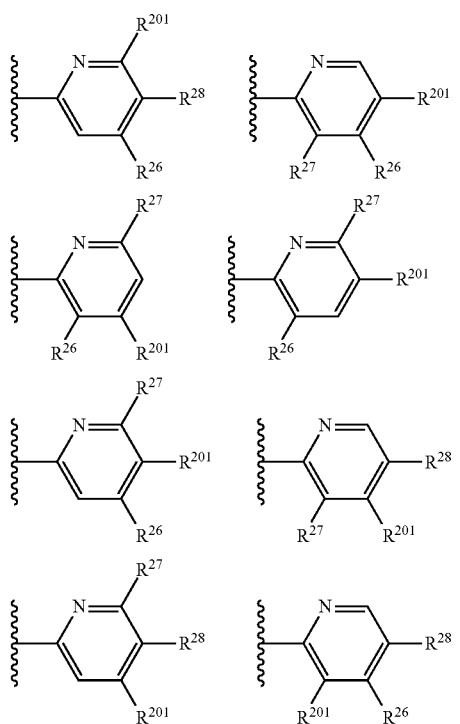
In one embodiment, B4 is selected from:
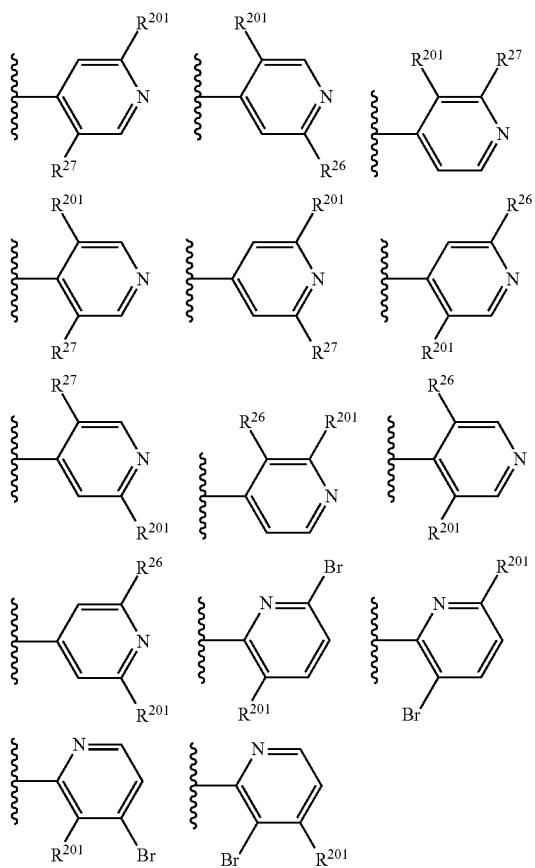

-continued
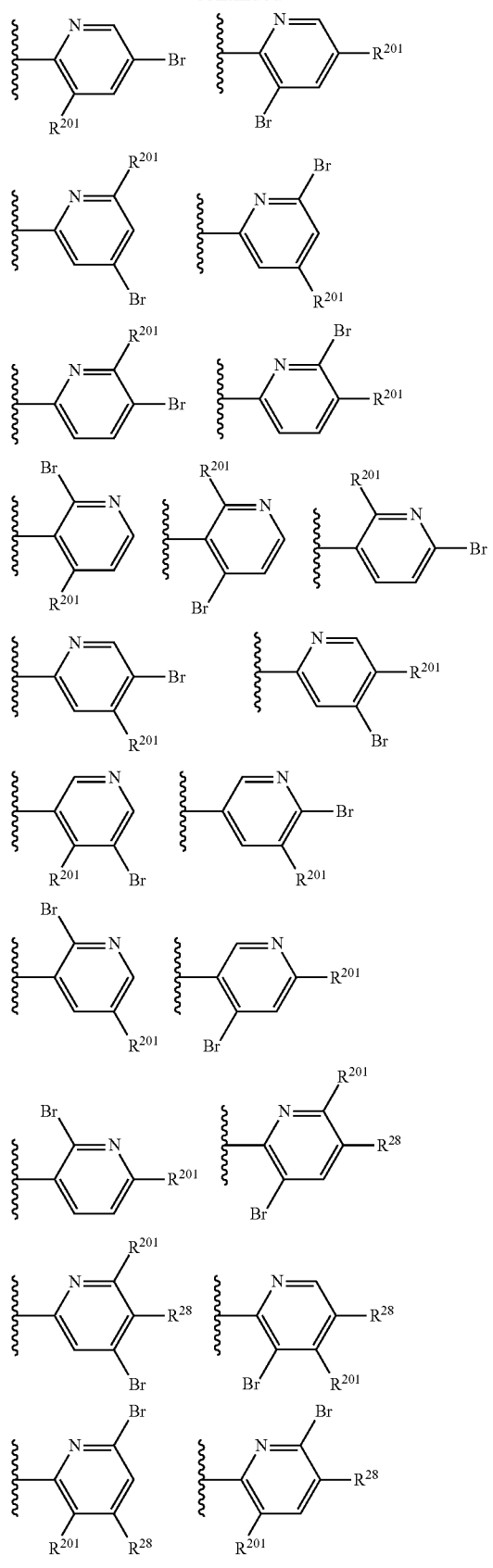
In one embodiment, B4 is selected from:
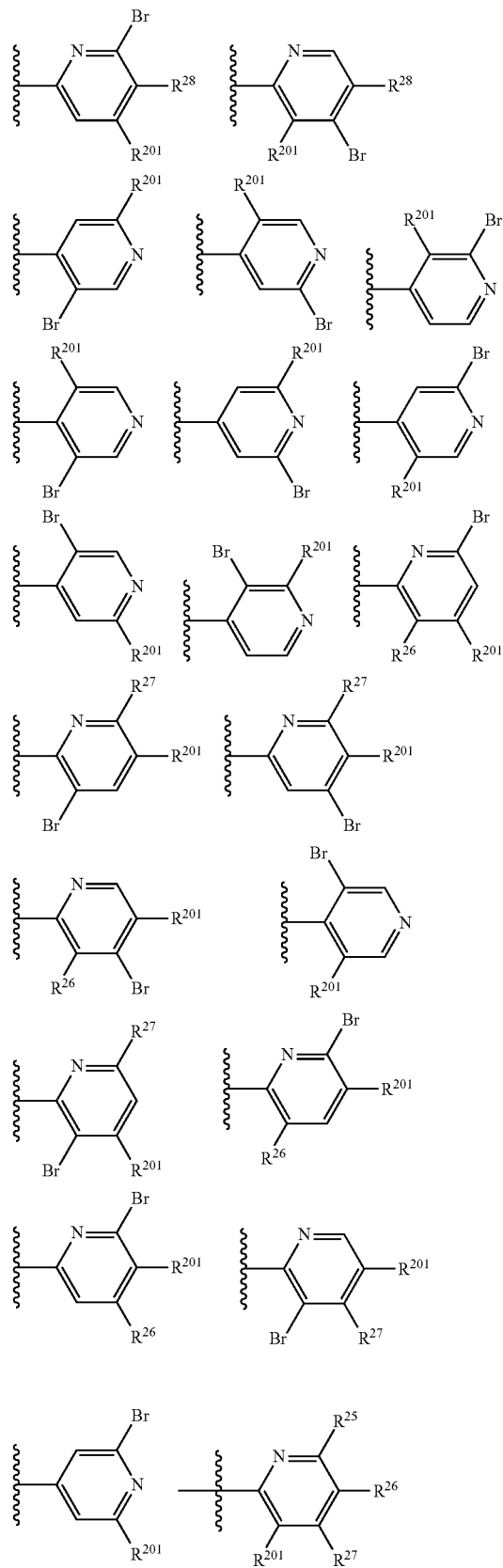

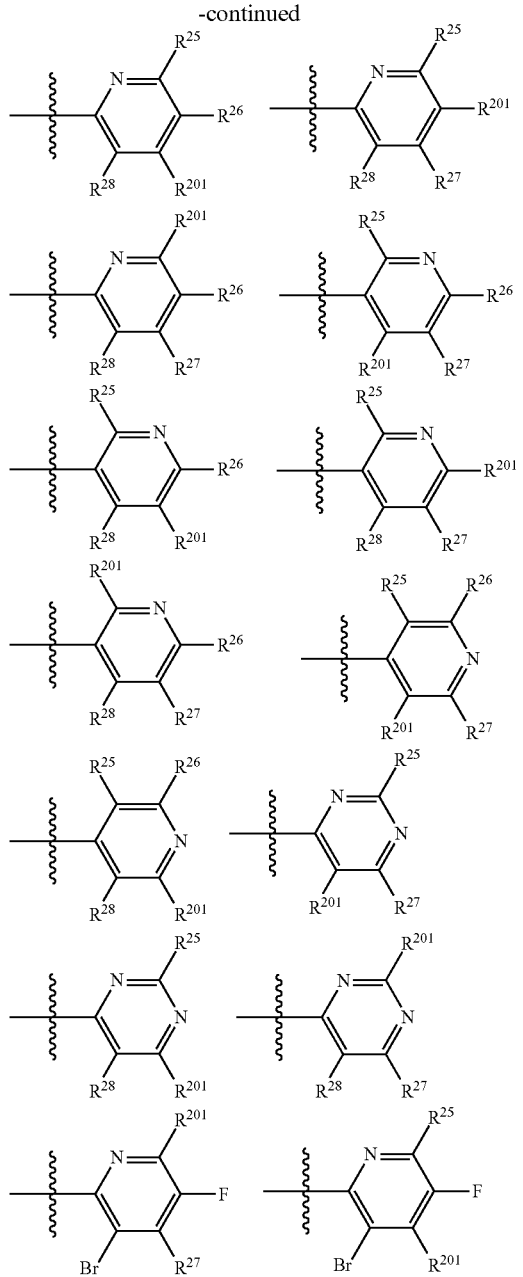
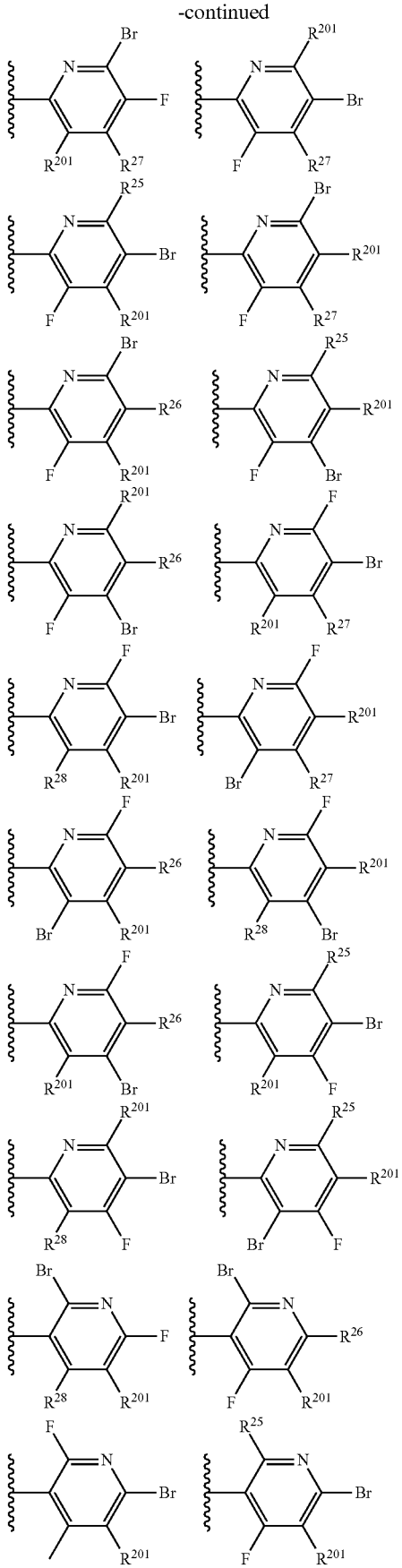
In one embodiment, B4 is selected from:

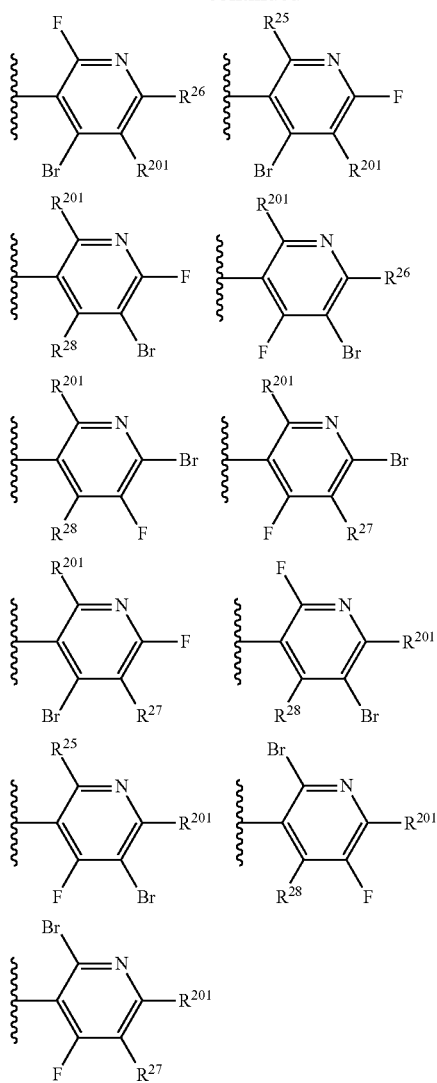
In one embodiment, B4 is selected from:
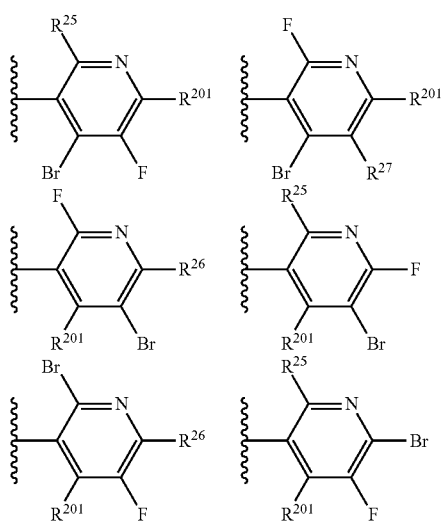
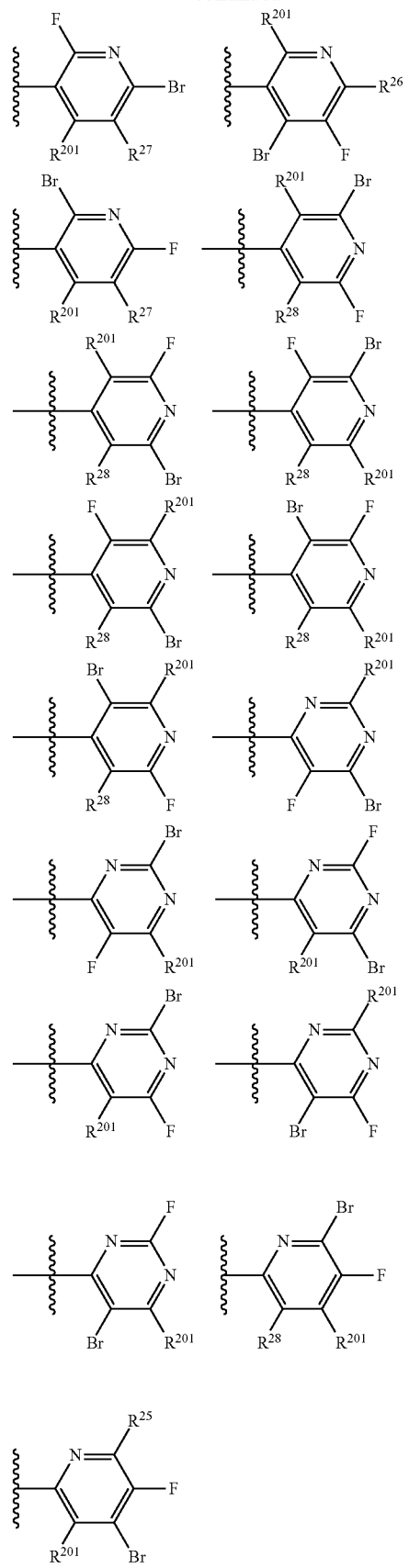

In one embodiment, B4 is selected from:
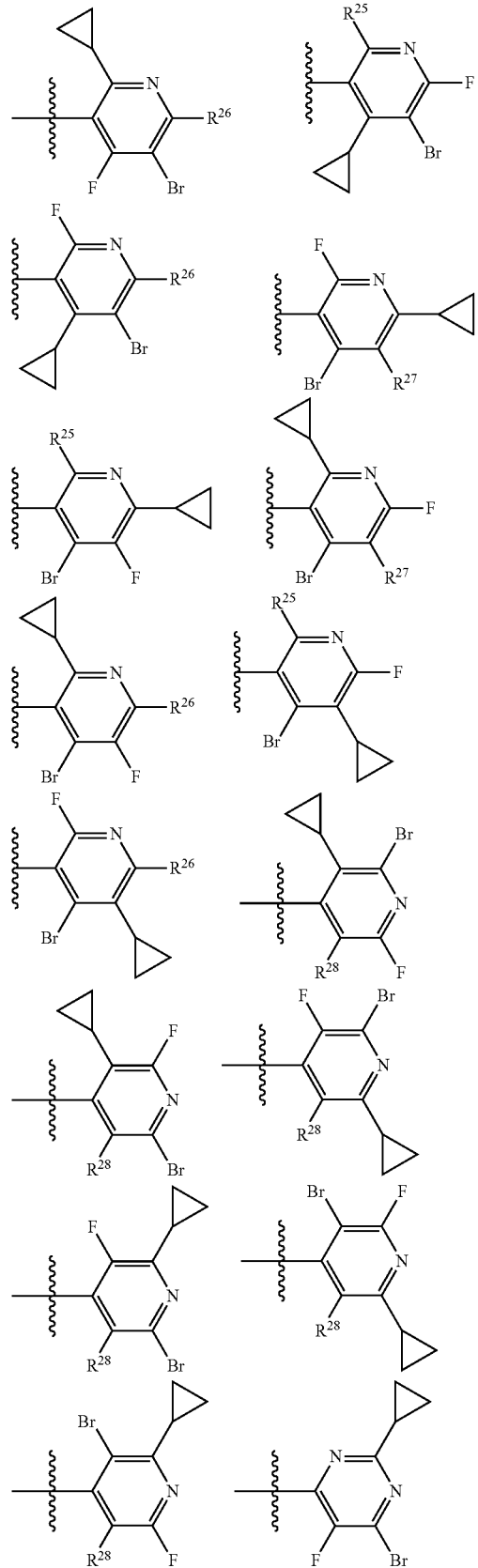
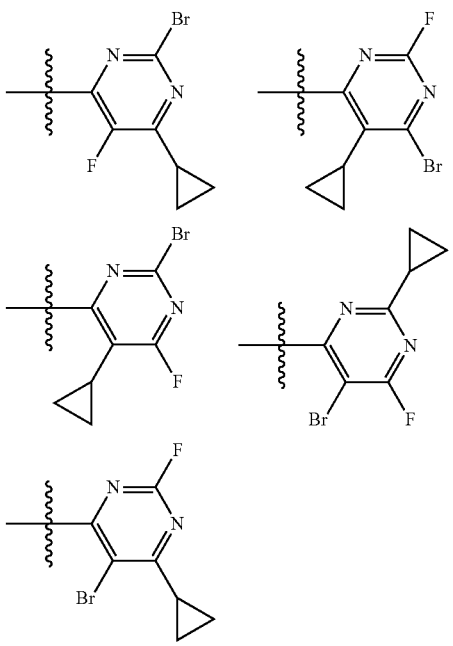
In one embodiment, B4 is selected from:
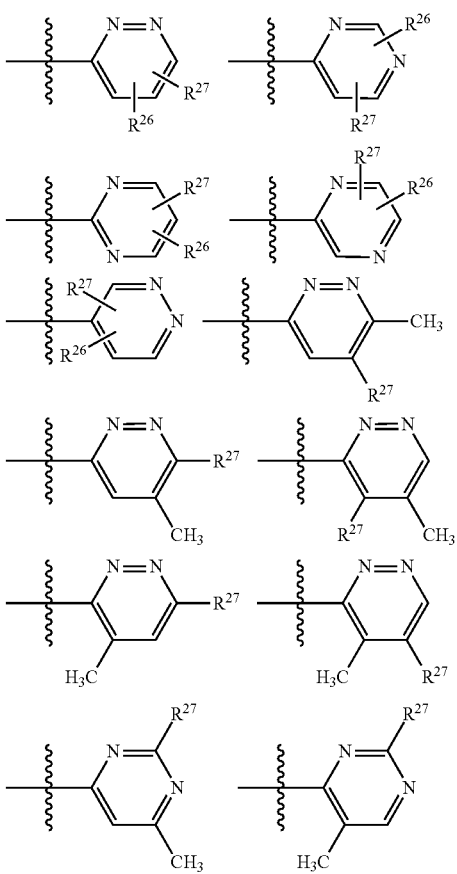

-continued
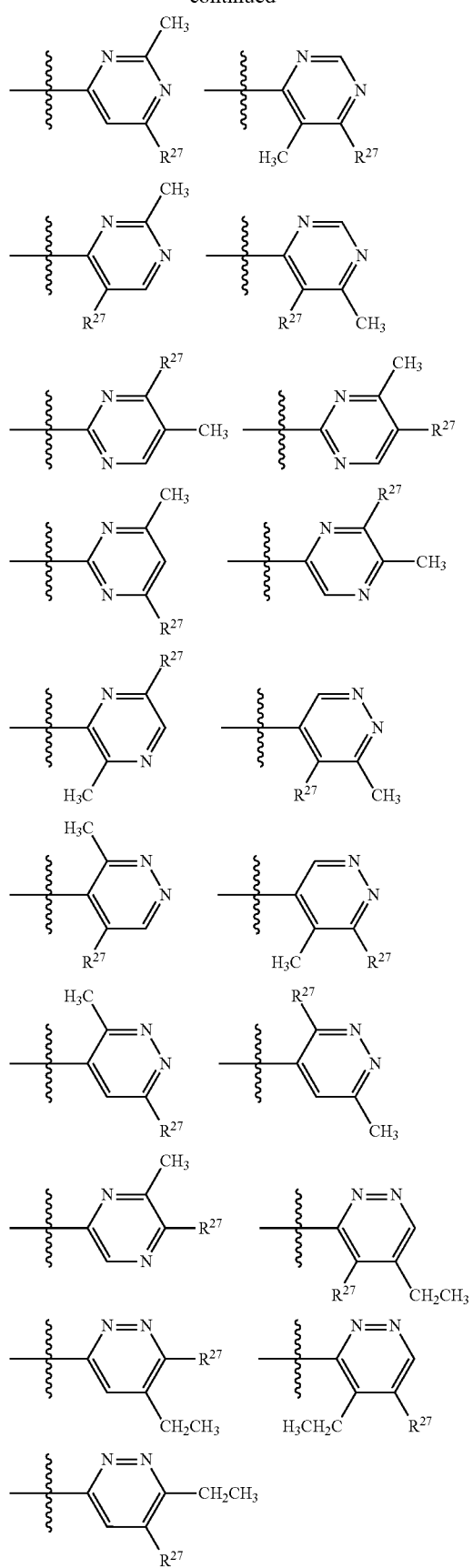
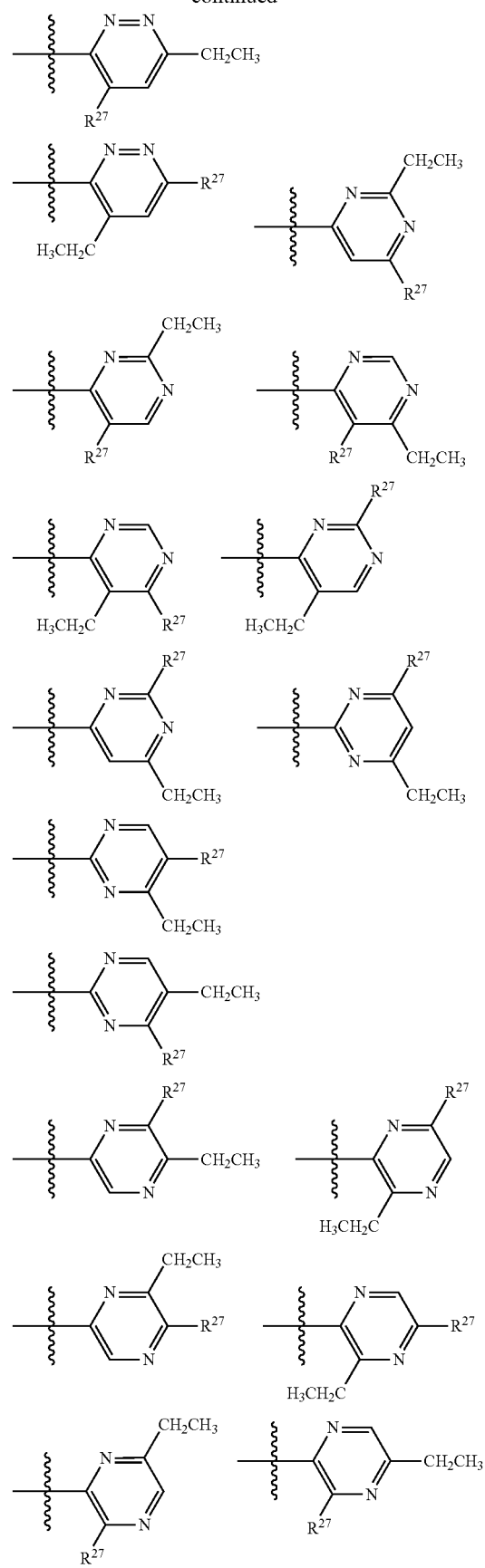

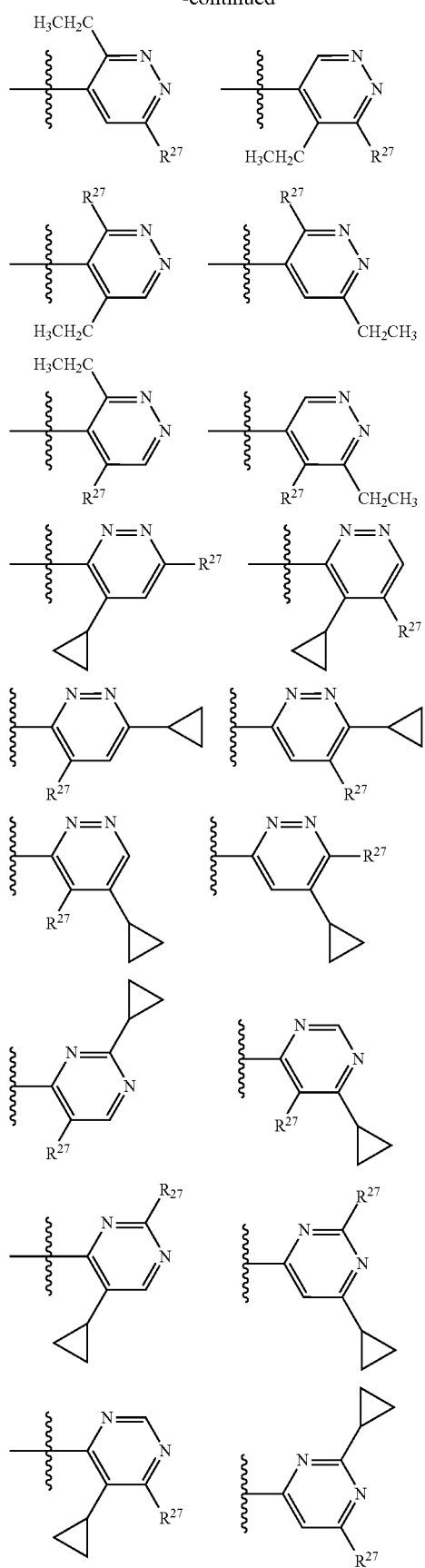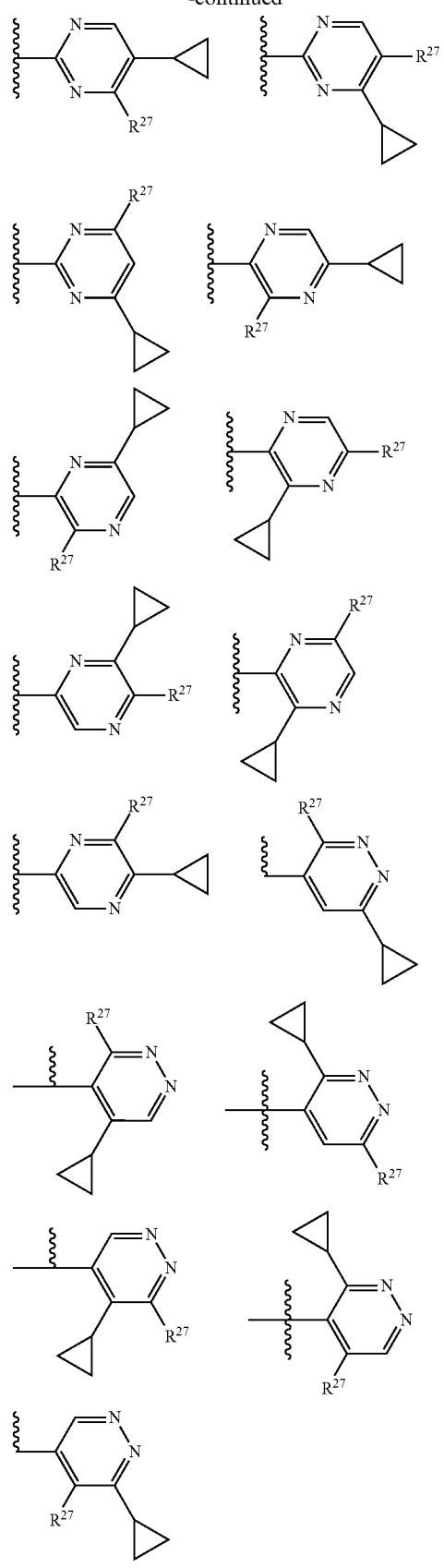

In one embodiment, B4 is selected from:
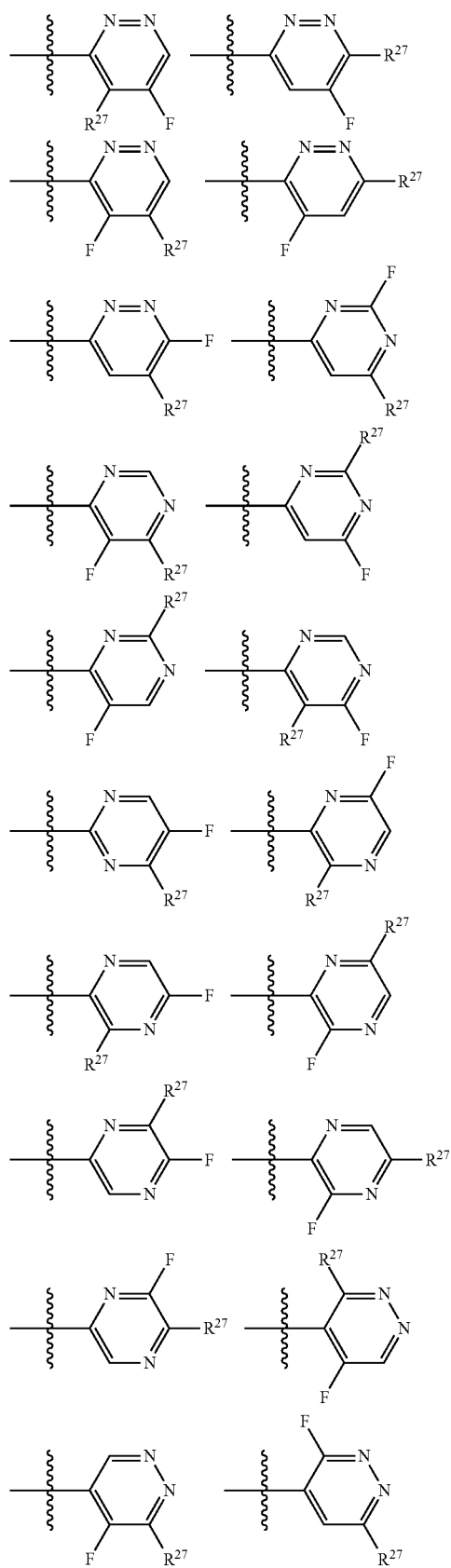
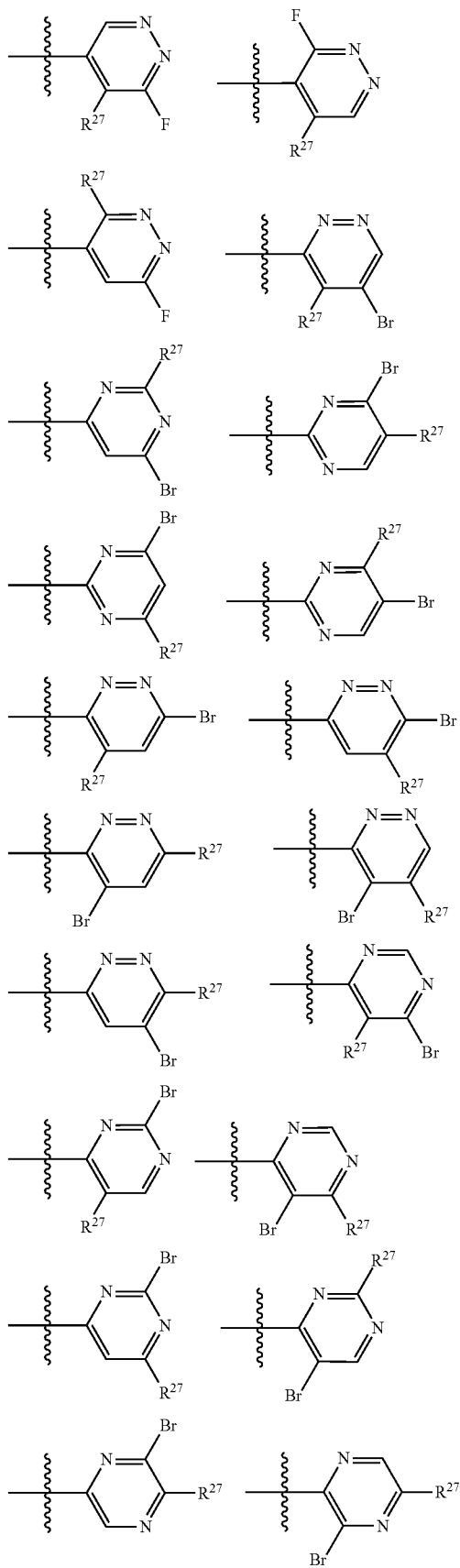

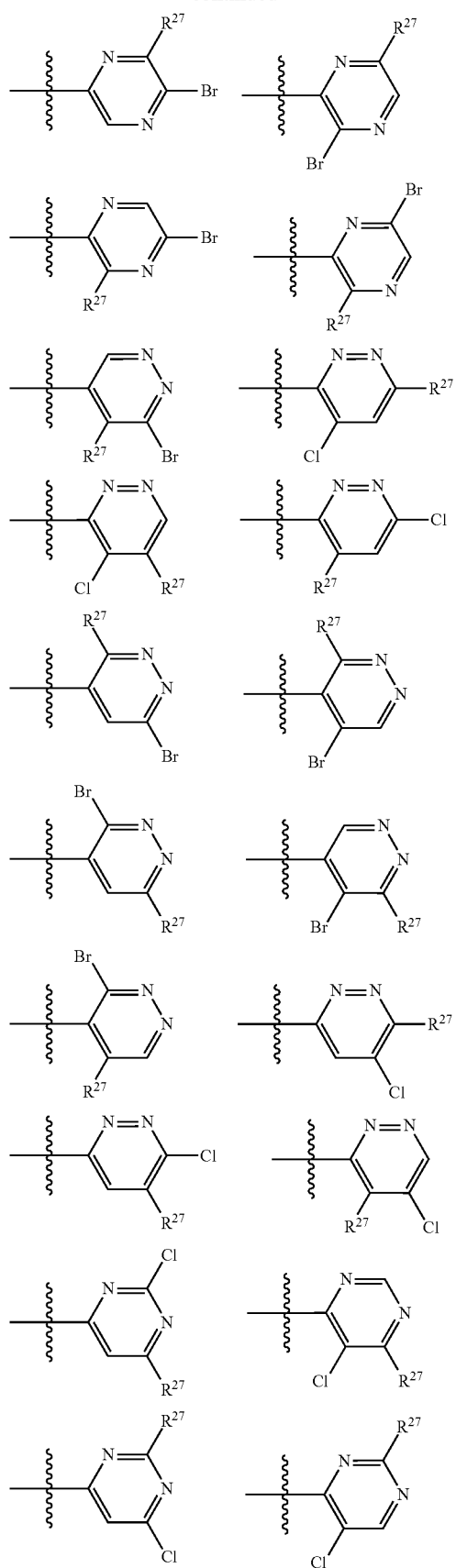
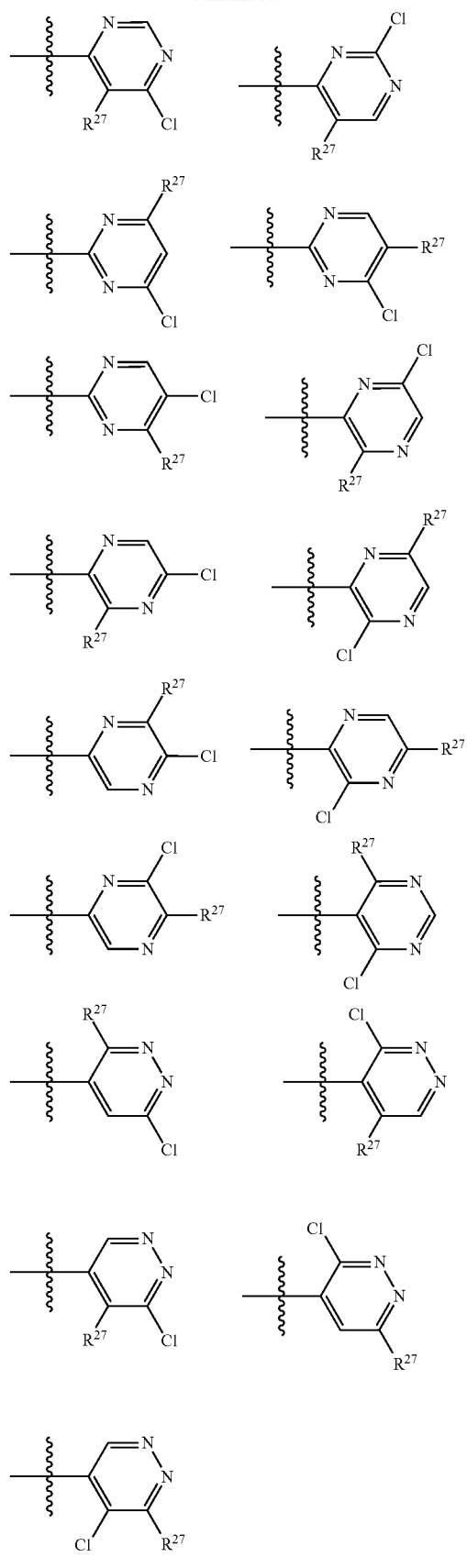

In one embodiment, B4 is selected from:
-continued
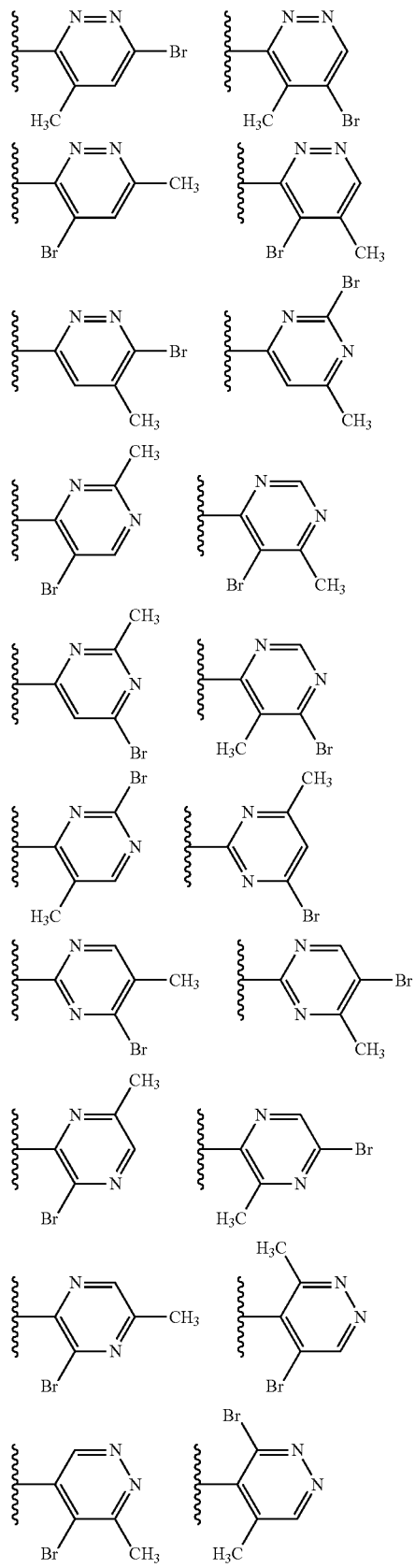
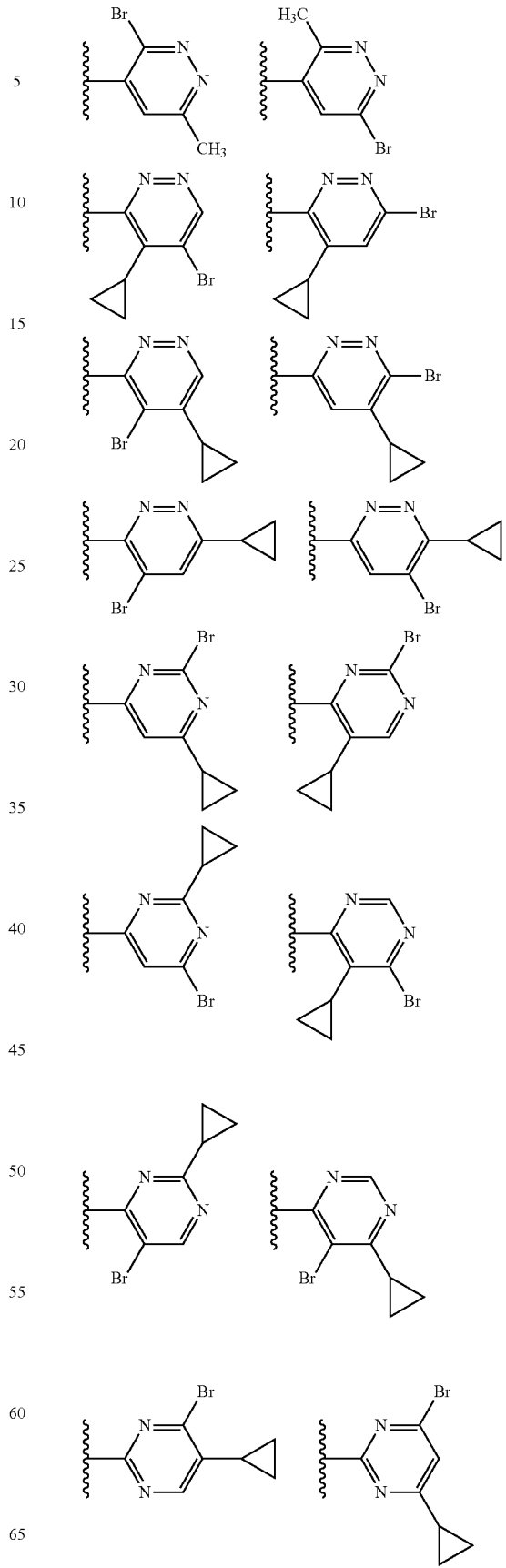

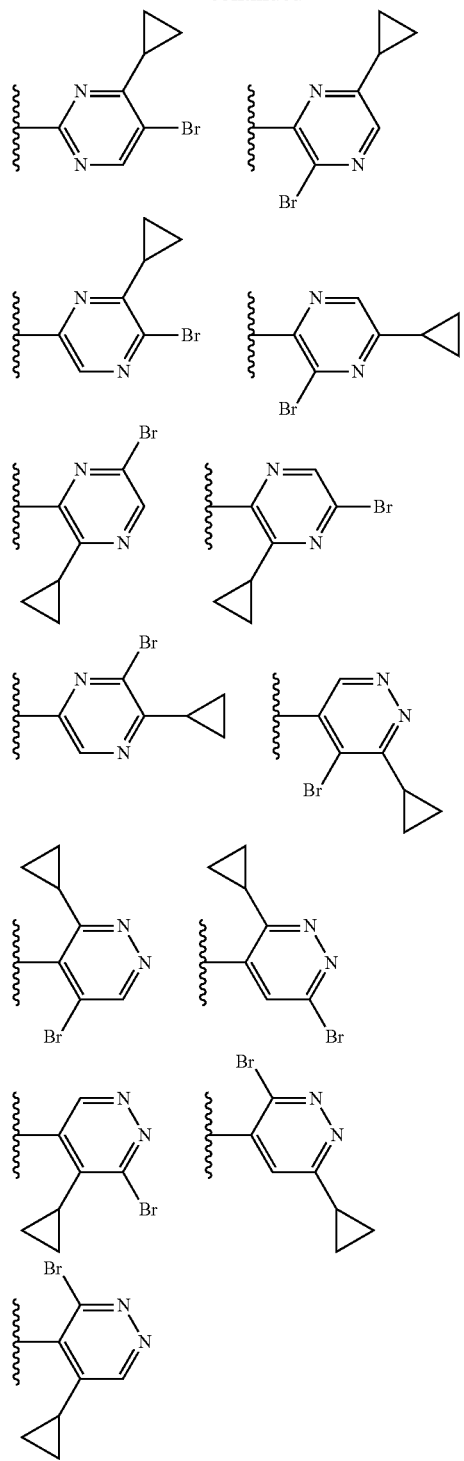
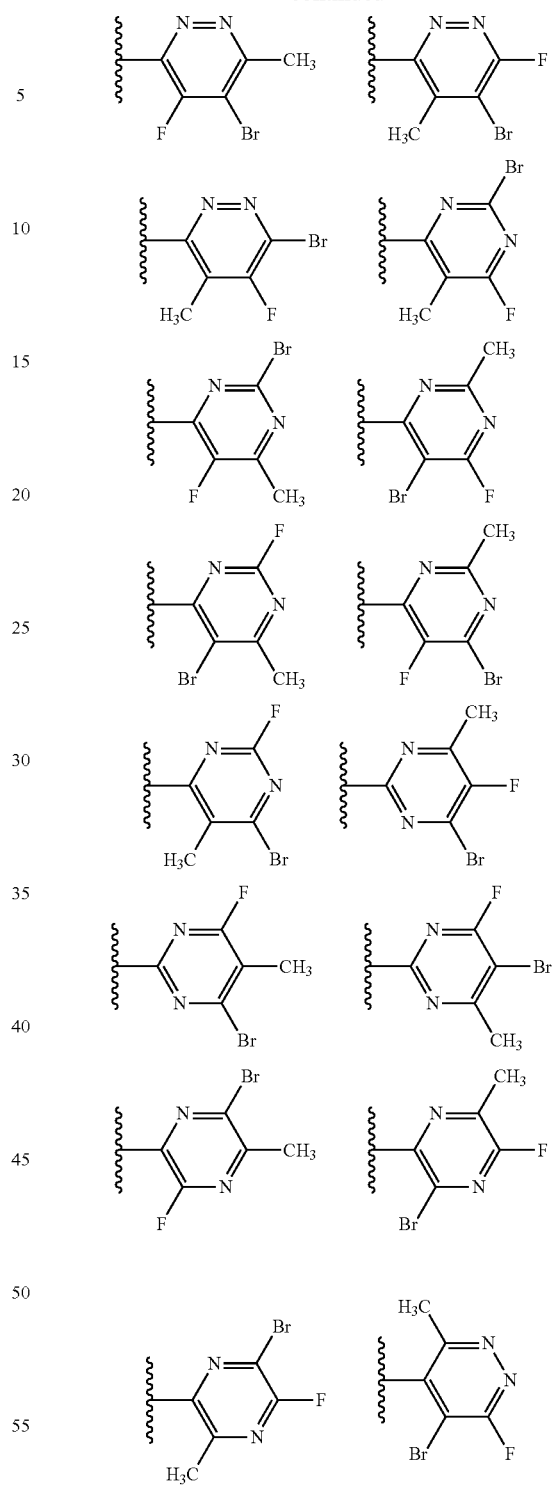
In one embodiment, B4 is selected from:
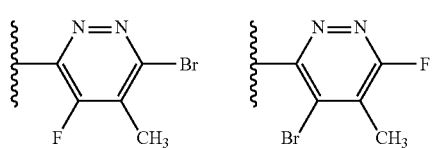
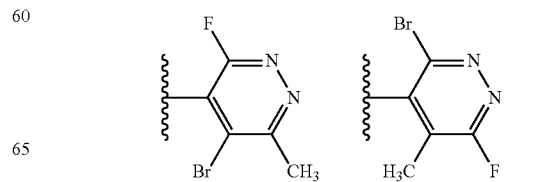

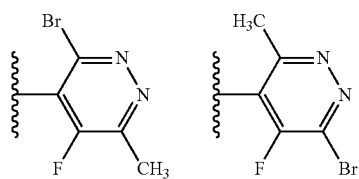
In one embodiment, B4 is selected from:
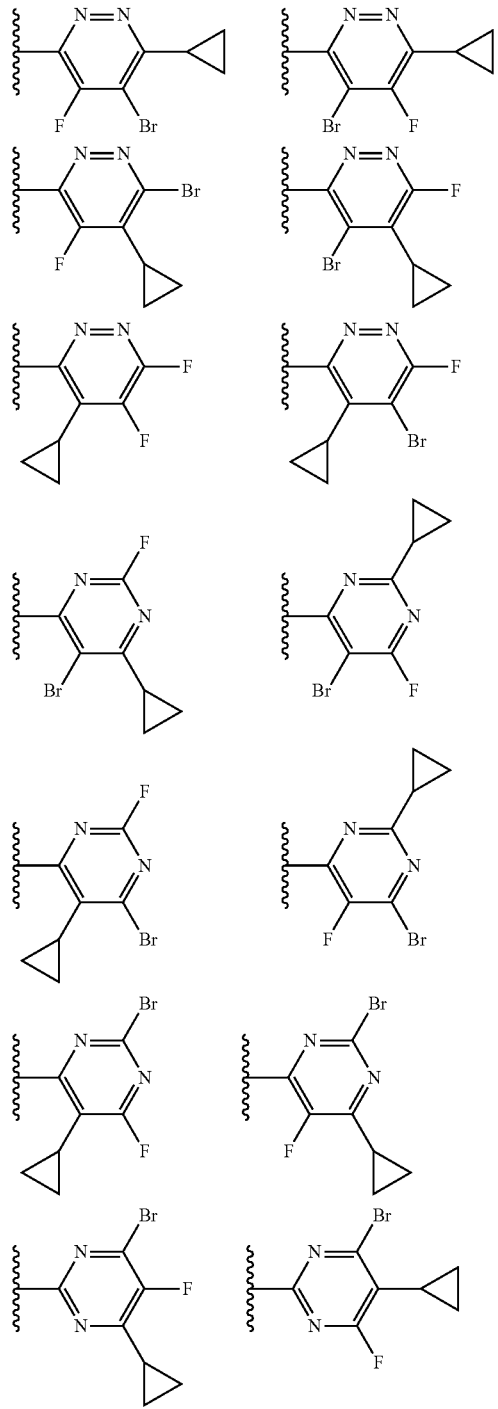
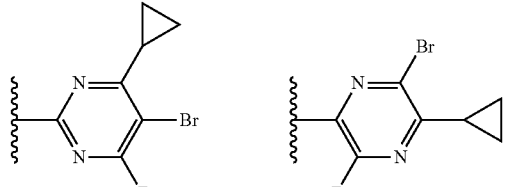
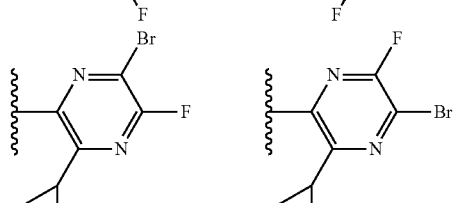
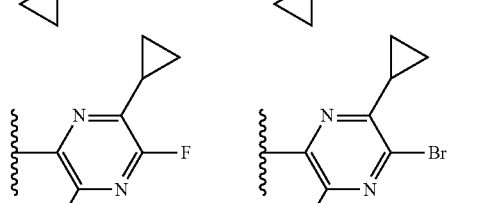
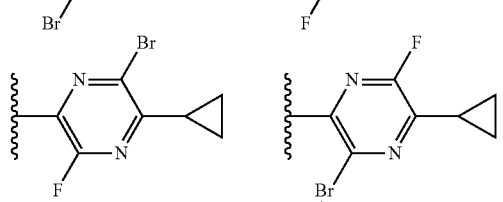
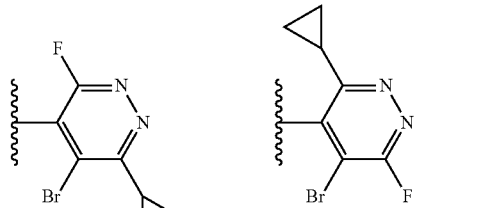
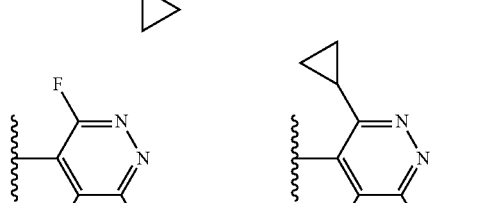
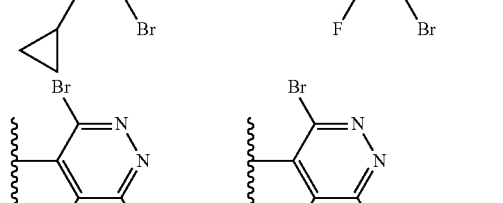
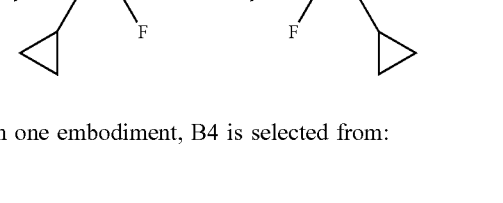
In one embodiment, B4 is selected from:
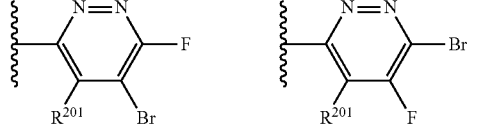

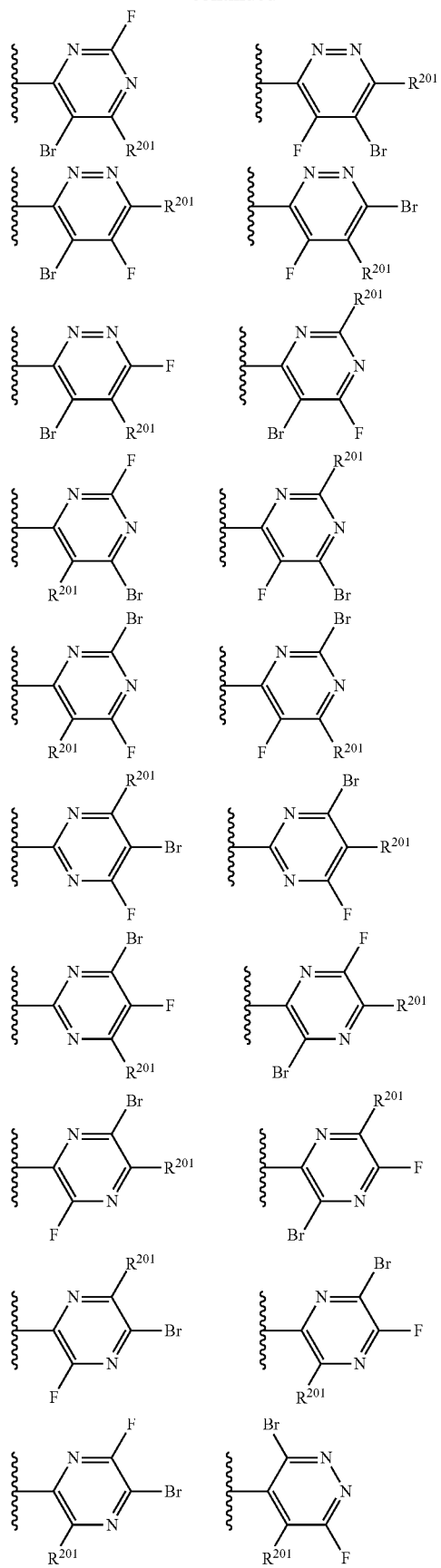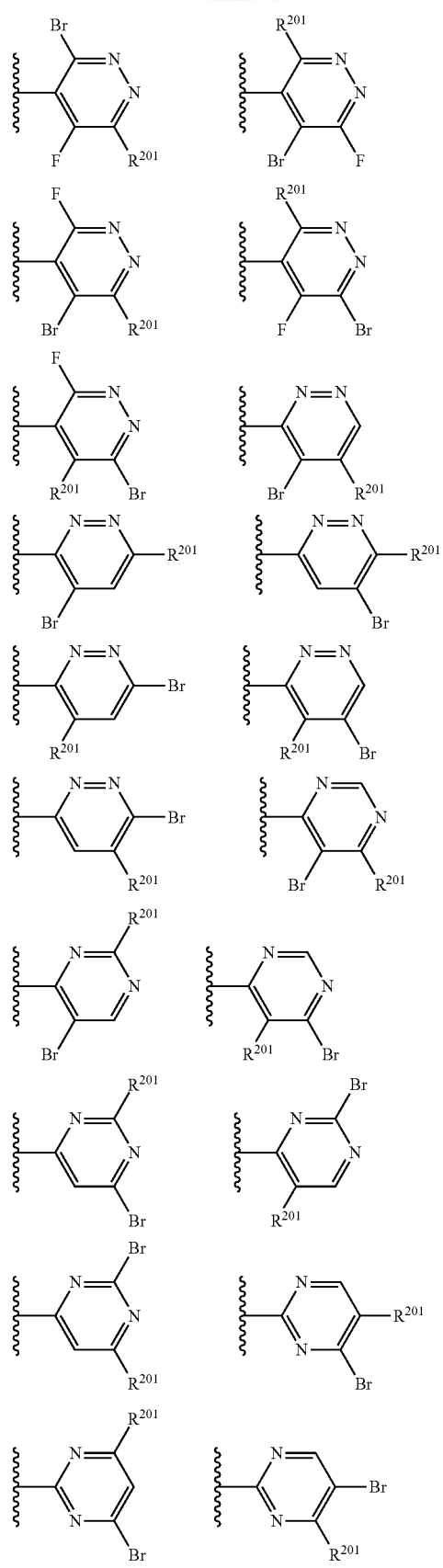

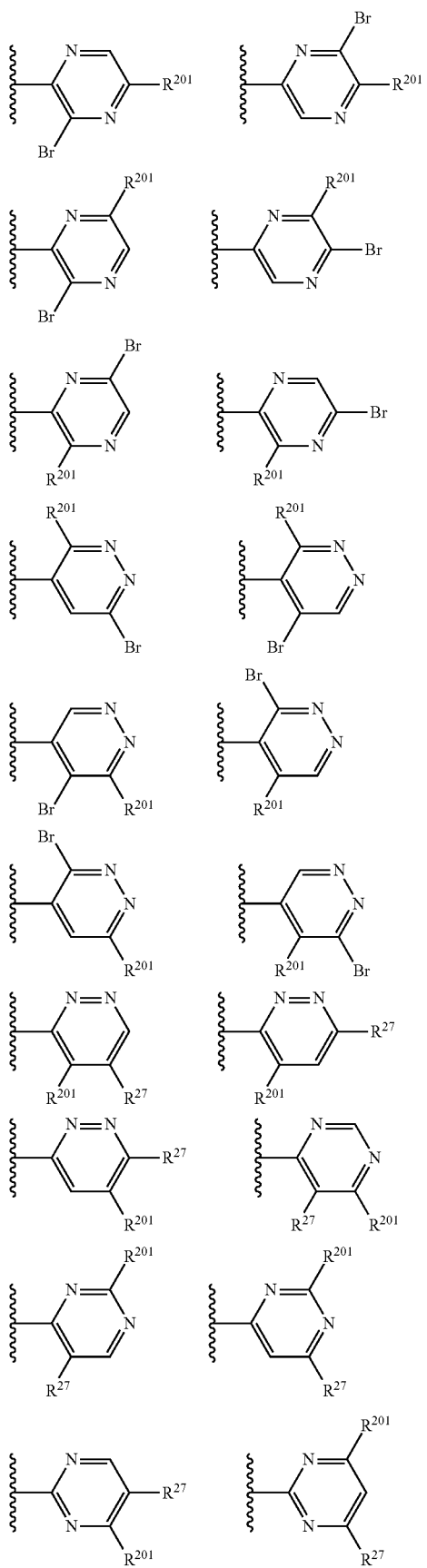
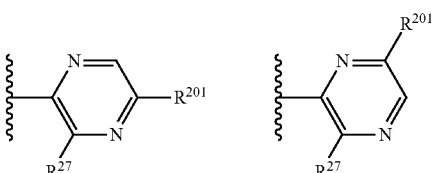
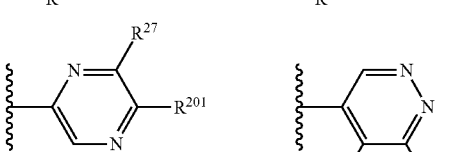
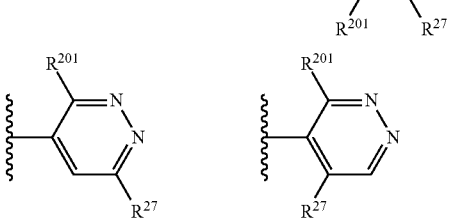
In one embodiment $R^{25}$, $R^{26}$, $R^{27}$, and $R^{28}$ are independently selected from hydrogen, halogen, and $C_1$-$C_6$alkyl.
In another embodiment, B4 is selected from:
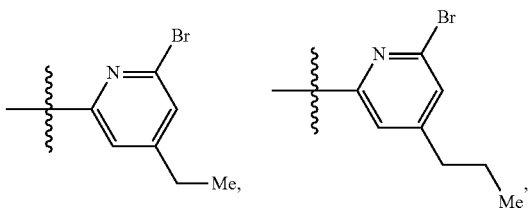
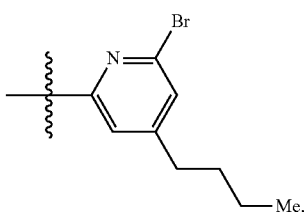
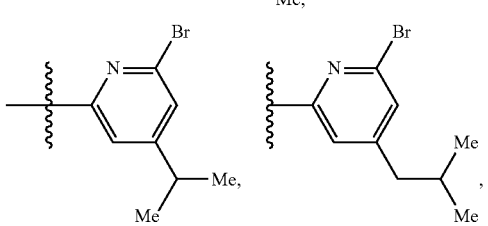
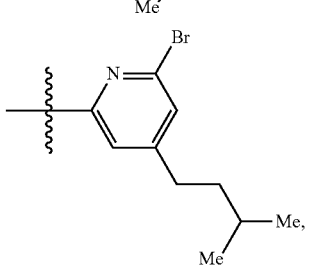

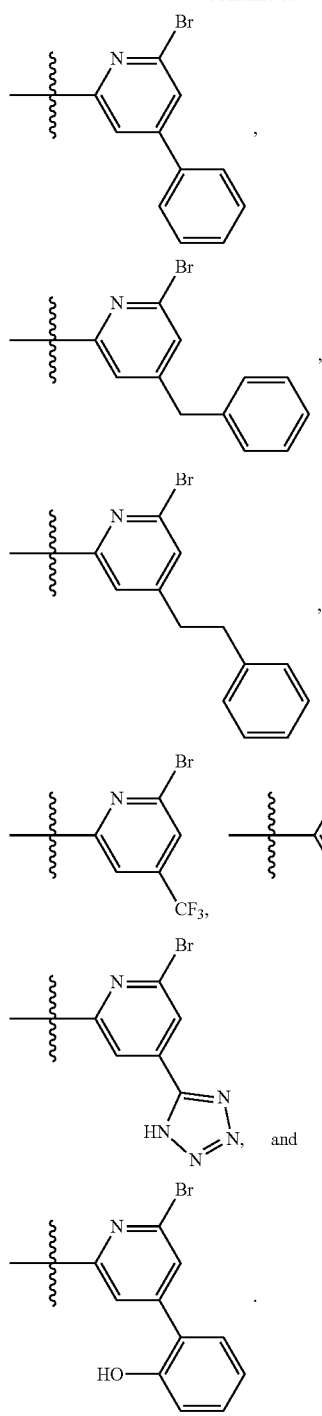
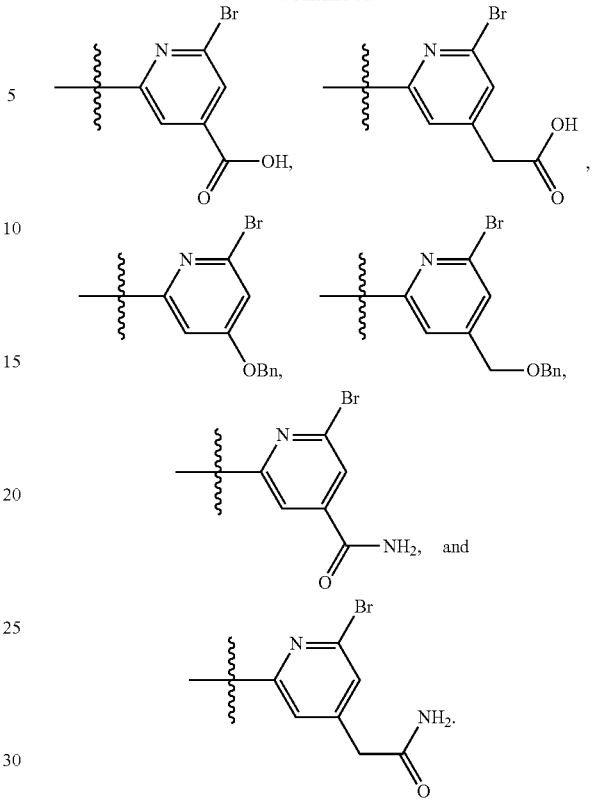
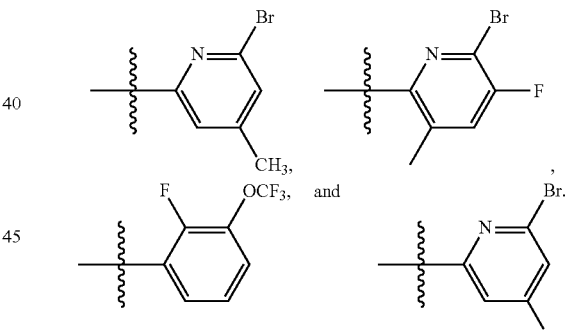
In another embodiment, B4 is selected from:
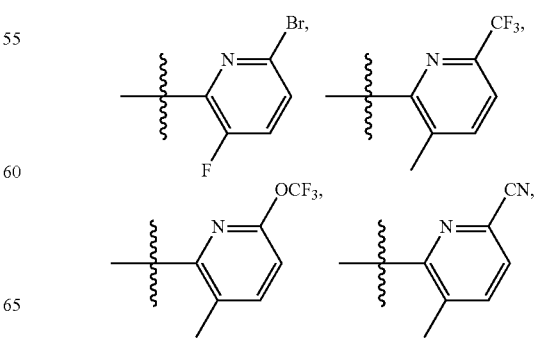
In another embodiment, B4 is selected from:
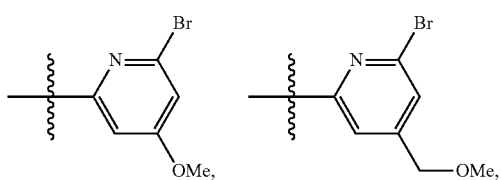

-continued
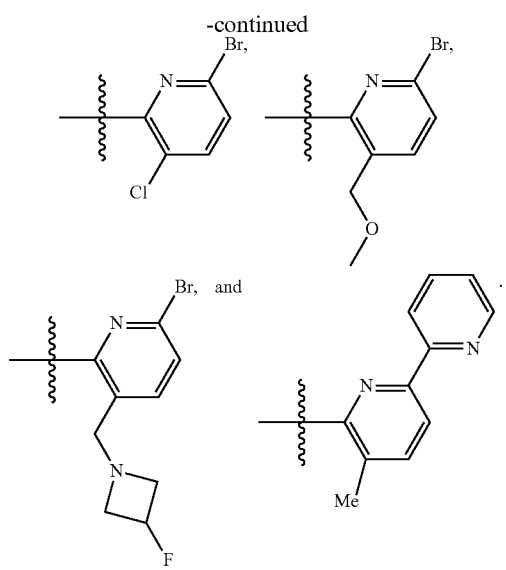
In another embodiment, B4 is selected from:
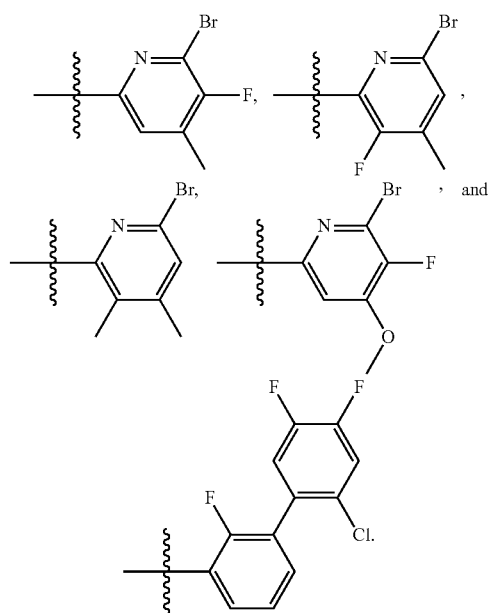
In another embodiment, B4 is selected from:
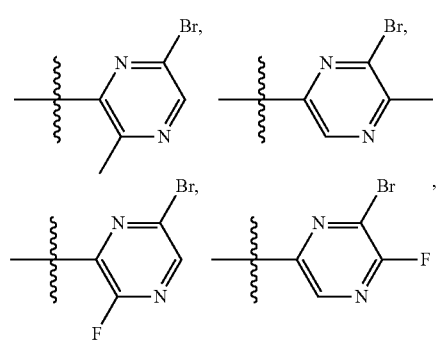
-continued
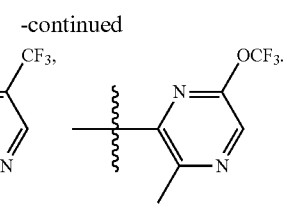
In an alternative embodiment, B4 is selected from:
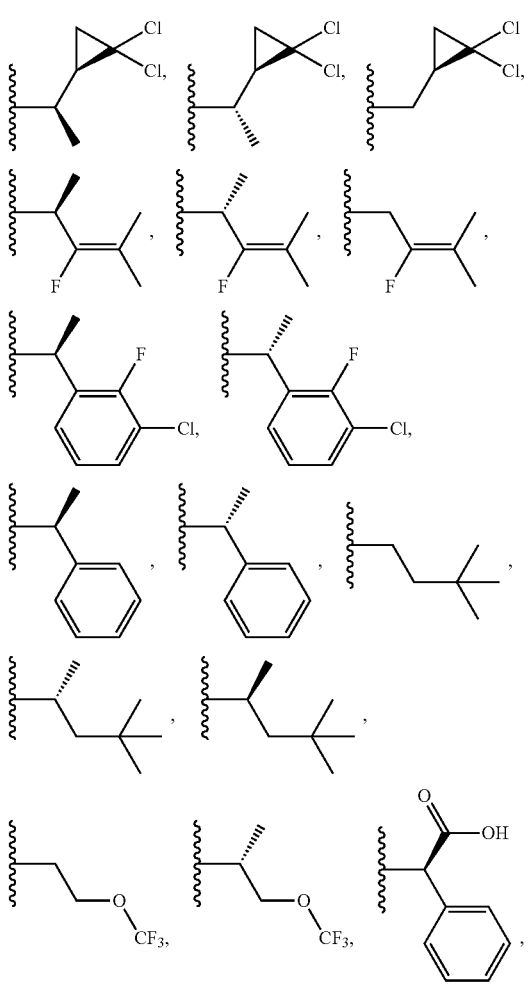
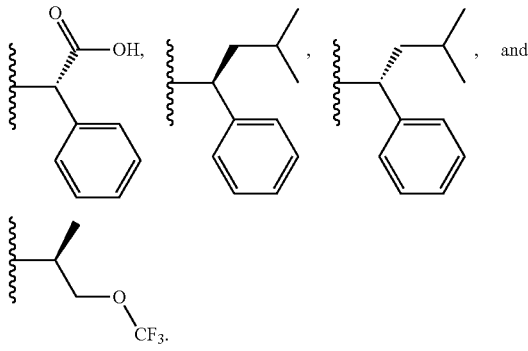

In an alternative embodiment, B4 is selected from:

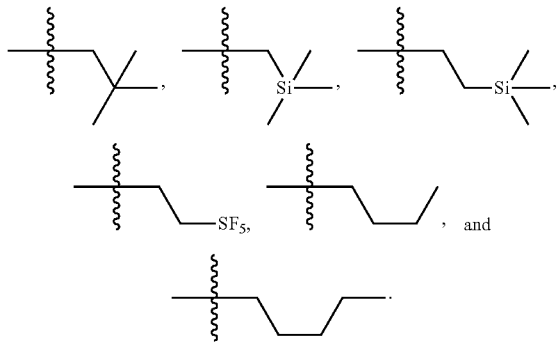

In an alternative embodiment, B4 is -alkyl-Si(alkyl)$_3$ or -alkyl-SF$_5$.

In an alternative embodiment, B4 is a B ring substituted with oxo. In this embodiment if the B ring is a nitrogen containing heteroaryl group then the nitrogen may also be substituted as defined herein. For example:

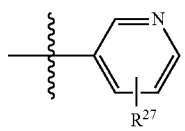

substituted with an oxo can be selected from the following compounds:

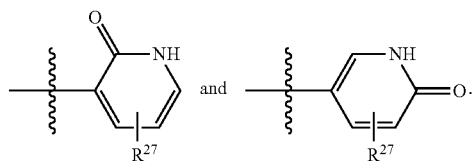

And examples of

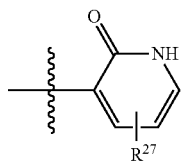

include:

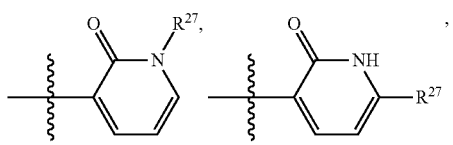

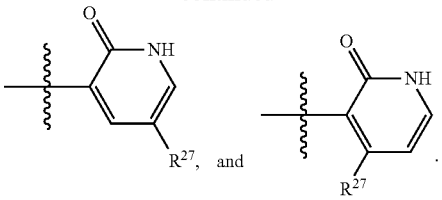

In another alternative embodiment, B4 is selected from:

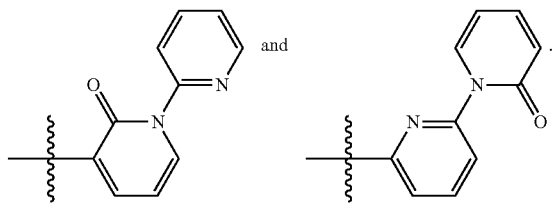

In another alternative embodiment, $R^{32}$ is a heteroaryl ring substituted with oxo as allowed by valence. In this embodiment if the $R^{32}$ ring is a nitrogen containing heteroaryl group then the nitrogen may also be substituted as defined herein. For example:

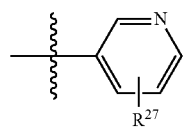

substituted with an oxo can be selected from the following compounds:

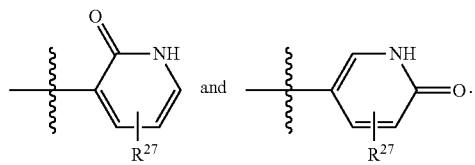

And examples of

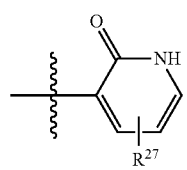

include:

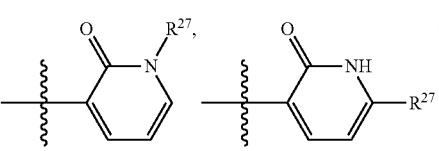

-continued

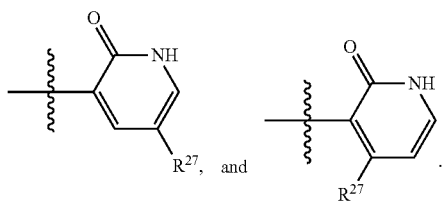

In another alternative embodiment, $R^{32}$ is selected from:

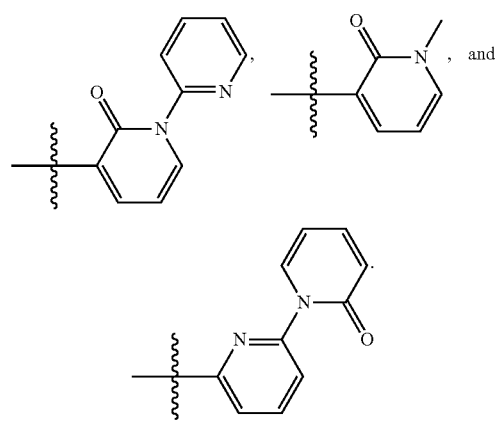

In another alternative embodiment, B4 is an alkyl group.

In another alternative embodiment, B4 is an alkenyl group.

In another embodiment, C4 is selected from:

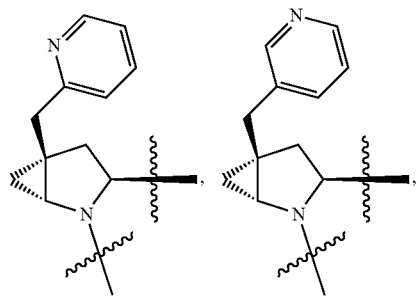

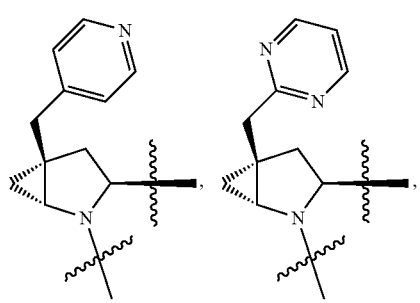

-continued

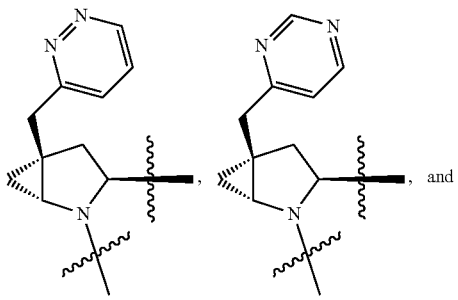

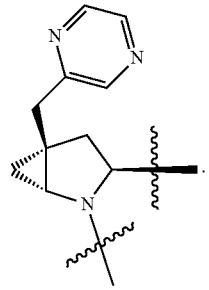

In one embodiment L2 is a spirocyclic linker attached to the C ring so that the resultant compound of Formula I is:

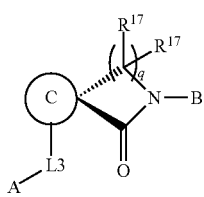

In one embodiment L2 is a spirocyclic linker attached to the C ring so that the resultant compound of Formula II is:

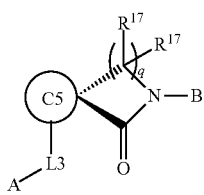

In one embodiment L2 is a spirocyclic linker attached to the C ring so that the resultant compound of Formula III is:

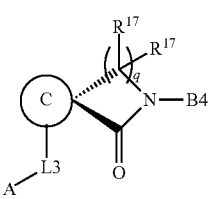

In one embodiment a compound of Formula

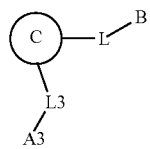

is provided.

In one embodiment $R^{32}$ is selected from:

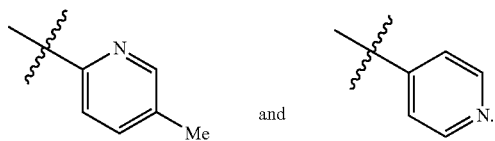 [SMILES: *c1ccc(C)cn1 ; *c1ccncc1]

In one embodiment $R^{32}$ is selected from:

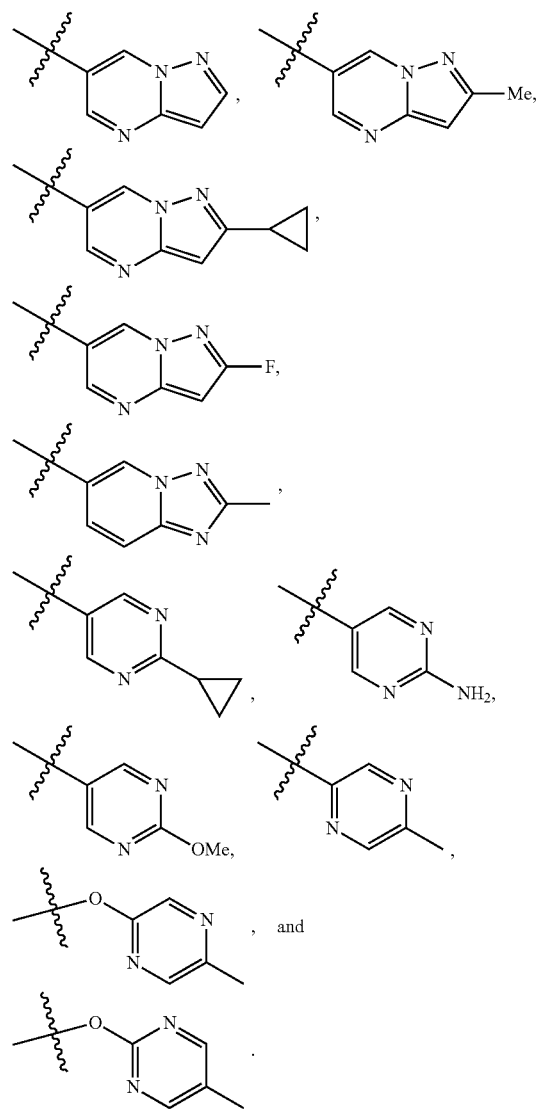

In an alternative embodiment $R^{32}$ is selected from:

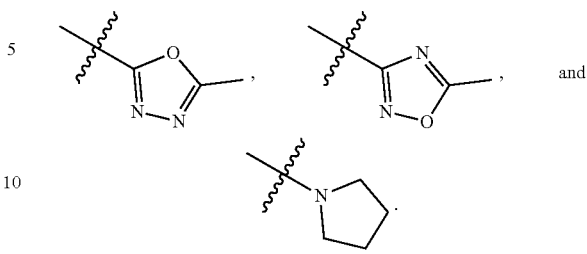

In an alternative embodiment $R^{11}$, $R^{12}$, $R^{13}$, $R^{14}$, or $R^{15}$ is -alkyl-$R^{32}$ or —O-alkyl-$R^{32}$.

In an alternative embodiment $R^{11}$, $R^{12}$, $R^{13}$, $R^{14}$, or $R^{15}$ is

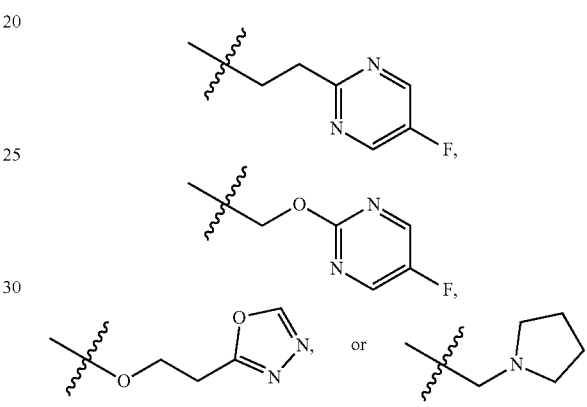

In one embodiment $R^{11}$, $R^{12}$, $R^{13}$, $R^{14}$, or $R^{15}$ is

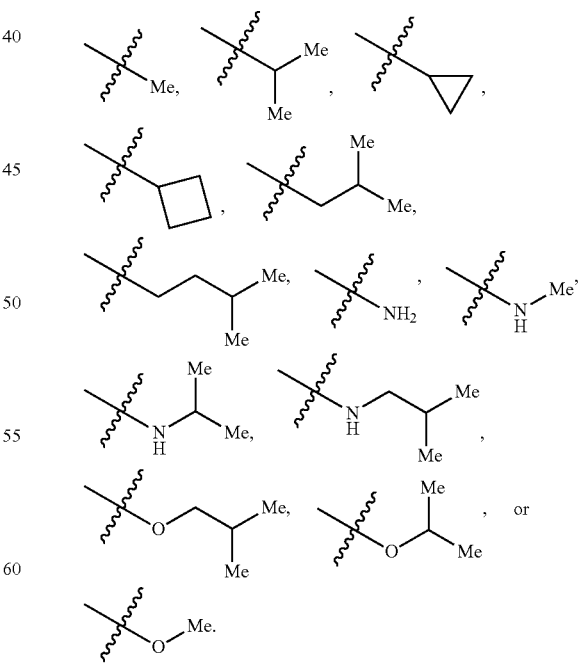

In one embodiment $X^{31}$ is selected from N and $CR^{54}$;
In another embodiment $X^{31}$ is $C(R^{54})_2$;
In one embodiment $X^{25}$ is O or S;

In one embodiment R⁴' is selected from -JCHO, -JCONH$_2$, -JCONR⁹R¹⁰, JC$_2$-C$_6$alkanoyl, -JSO$_2$NH$_2$, -JSO$_2$NR²¹R²², -JC(CH$_2$)$_2$F, -JCH(CF$_3$)NH$_2$, -J-haloalkyl-NH$_2$, -J-haloalkyl-NR⁹R¹⁰, alkyl including C$_1$-C$_6$alkyl, —C$_0$-C$_4$alkyl(C$_3$-C$_7$cycloalkyl), -JC(O)C$_0$-C$_2$alkyl(C$_3$-C$_7$cycloalkyl), -JNR⁹(C$_2$-C$_6$alkanoyl), -JNR⁹C(O)NR⁹R¹⁰,

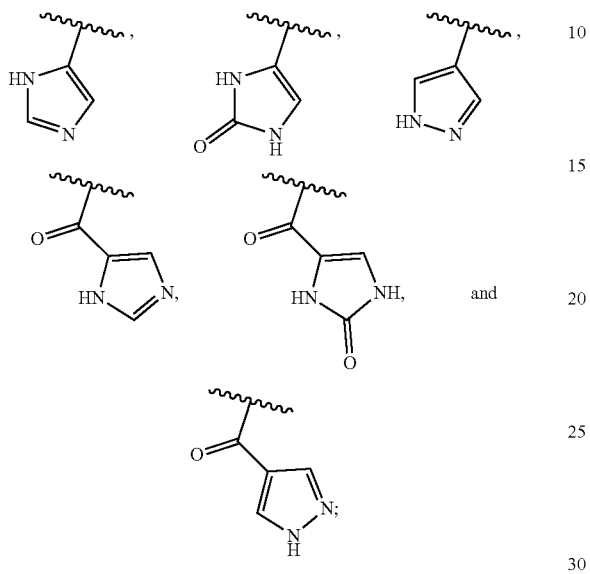

each of which R⁴' other than —CHO, is optionally substituted with one or more of amino, imino, halogen, hydroxyl, cyano, cyanoimino, alkyl including C$_1$-C$_6$alkyl, alkoxy including C$_1$-C$_6$alkoxy, —C$_0$-C$_2$alkyl(mono- and di-C$_1$-C$_6$alkylamino), haloalkyl including C$_1$-C$_6$haloalkyl, and haloalkoxy including C$_1$-C$_6$haloalkoxy.

Additional Embodiments of R³²

In one embodiment R³² is

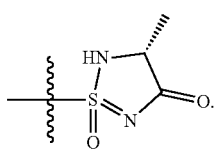 [SMILES: *S1(=O)=NC(=O)[C@@H](C)N1]

Embodiments of B

In one embodiment B is selected from:

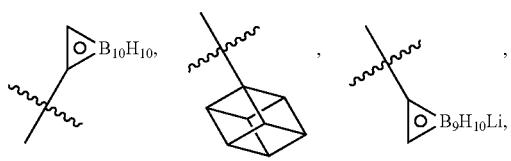

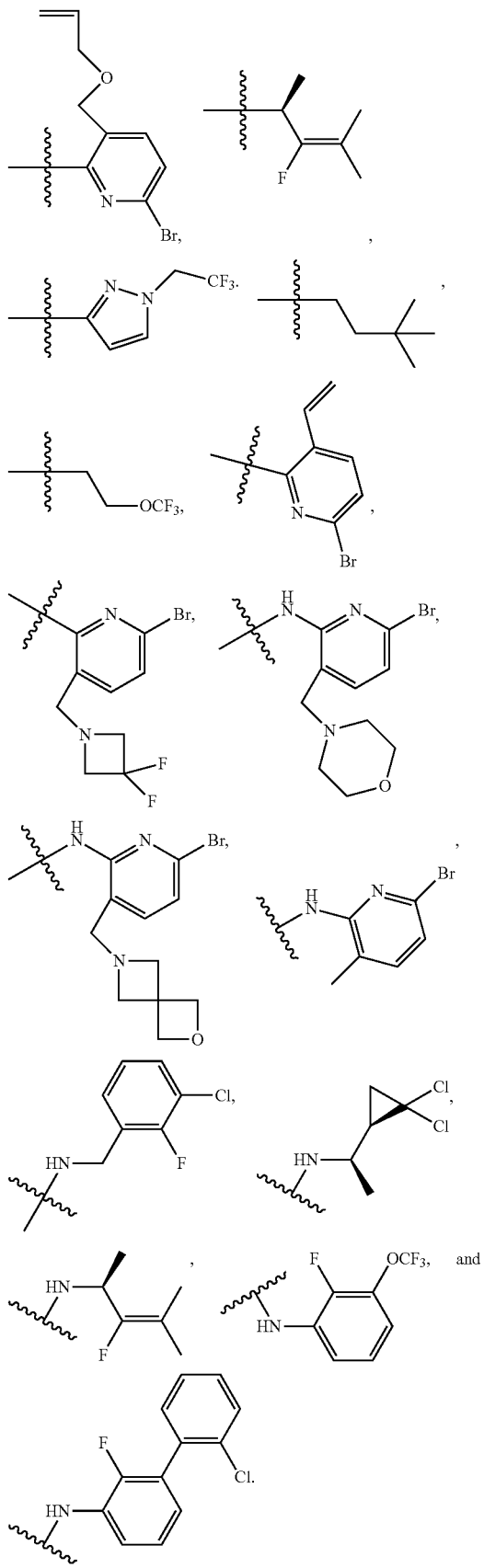

Embodiments of $R^{301}$

Examples of $R^{301}$ are provided below. In the compounds of the present invention, $R^{301}$ is monovalently attached to the molecule. The divalent species below are presented to illustrate that the $R^{301}$ can be linked at either point and the other is capped for example with H, alkyl, halogen, haloalkyl, aryl, heteroaryl, and heterocycle, each of which may be optionally substituted as described herein. In one embodiment $R^{301}$ is selected from:

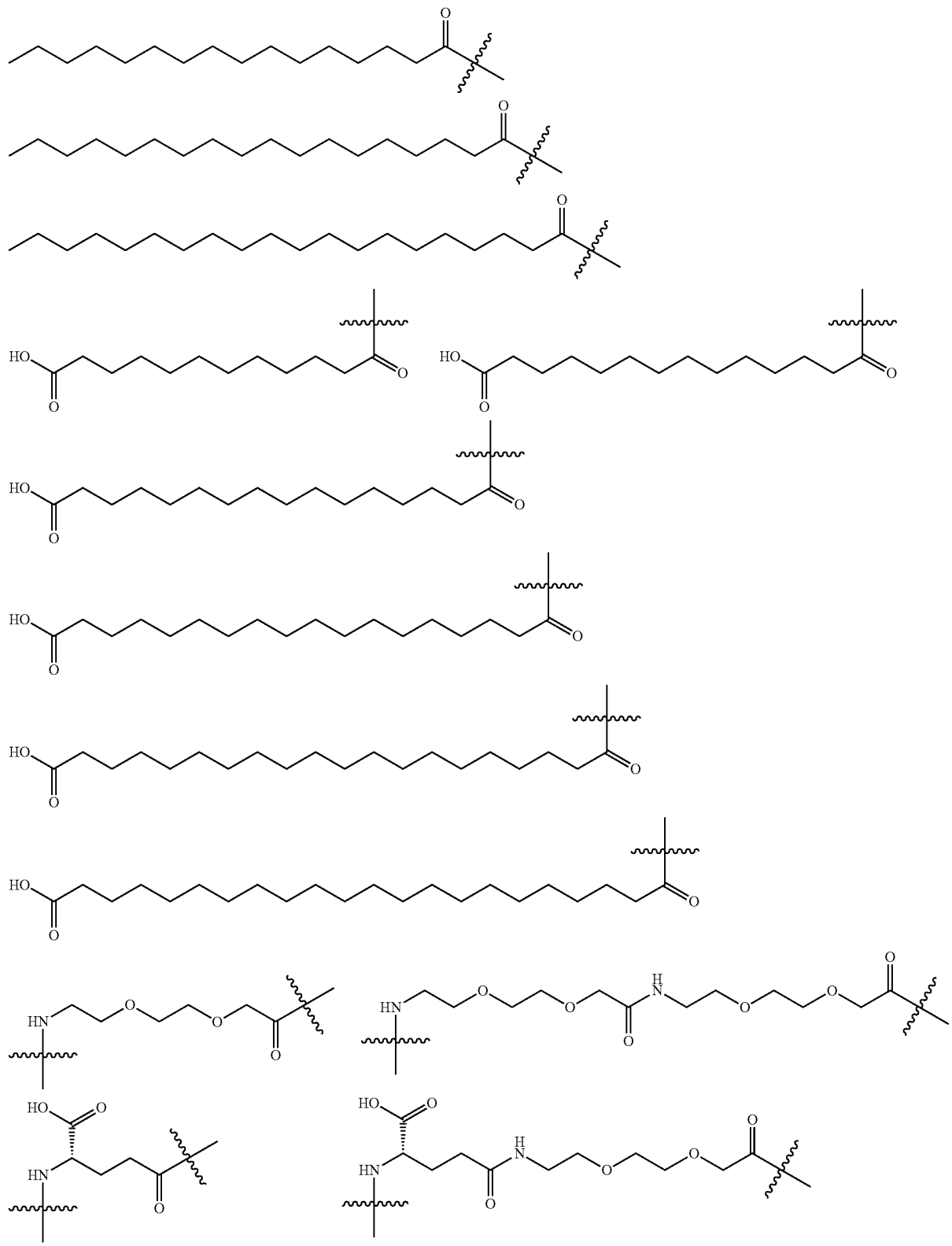

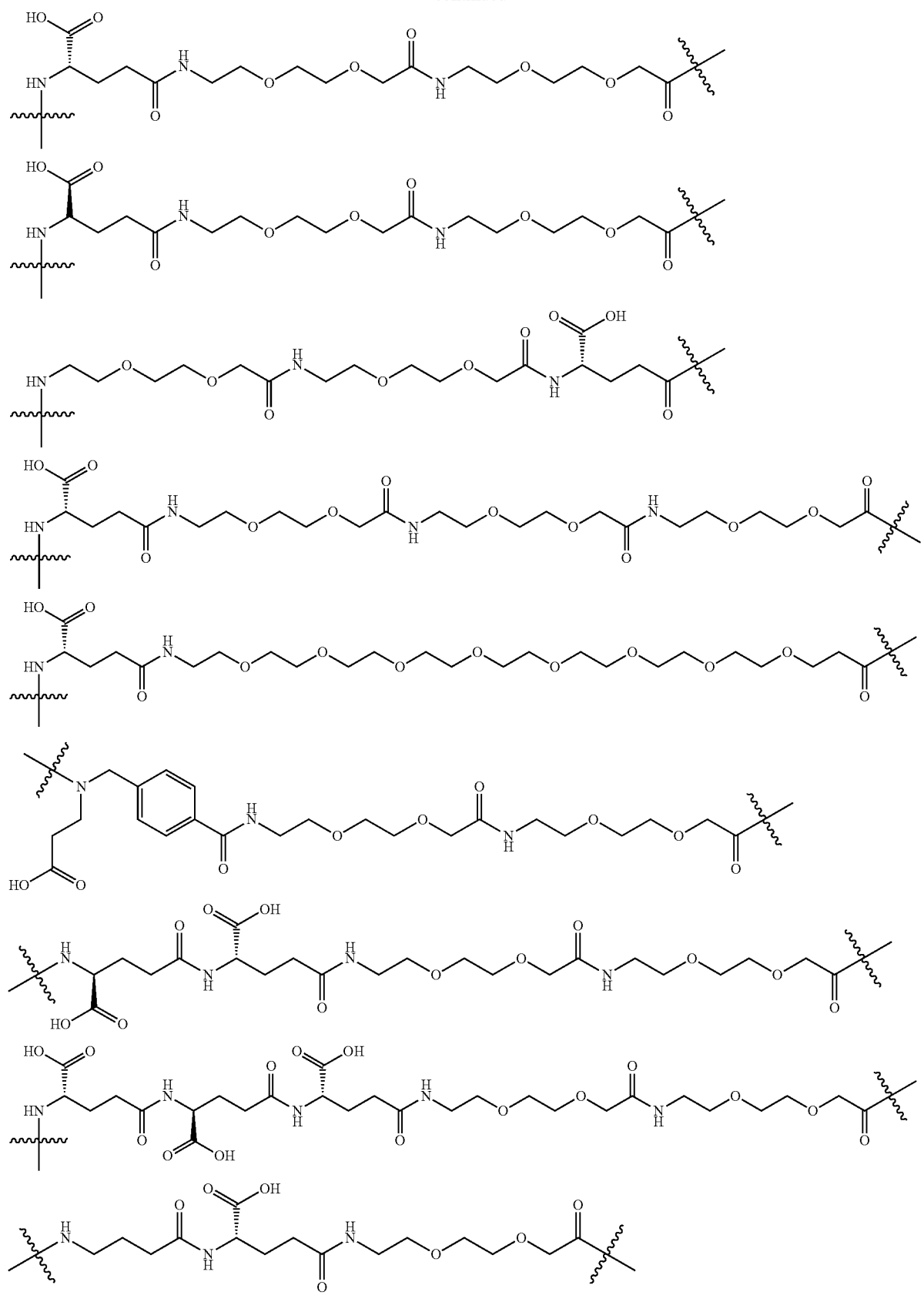

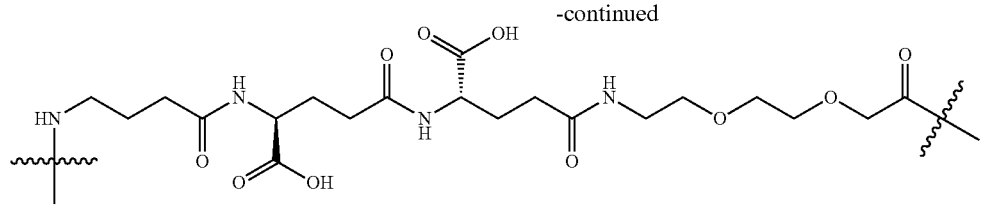

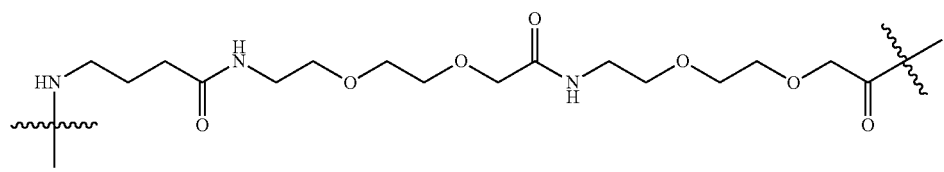

wherein if the moiety is shown as a divalent species, it can also be capped with hydrogen, methyl, alkyl, haloalkyl, aryl, heteroaryl, heterocyclic, other capping moiety of another bioactive moiety, or an additional prodrug moiety.

In one embodiment $R^{301}$ is selected from:

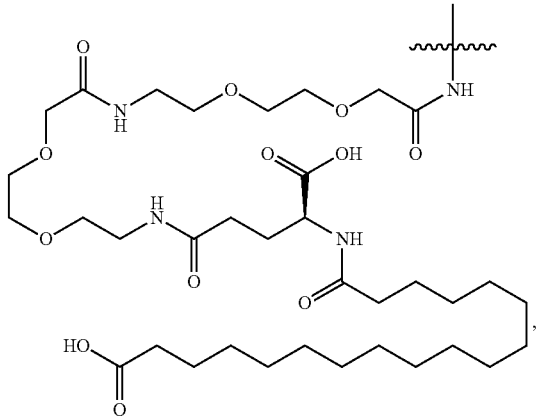

,

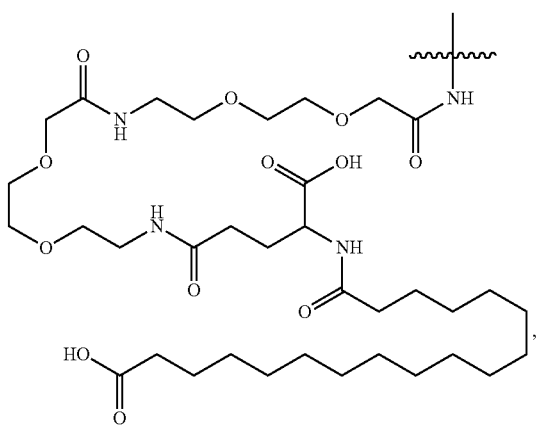

,

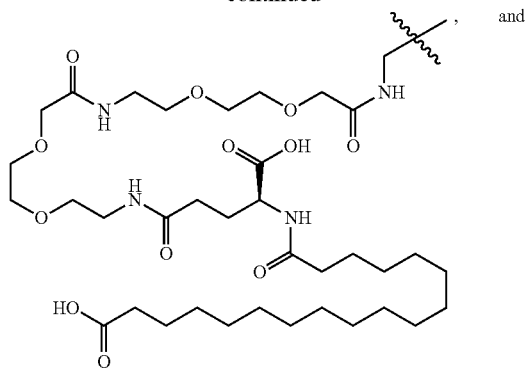

In one embodiment $R^{301}$ is

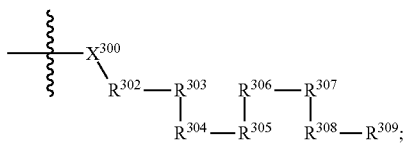

wherein $R^{302}$, $R^{303}$, $R^{304}$, $R^{305}$, $R^{306}$, $R^{307}$, and $R^{308}$ are selected from: bond, polyethylene glycol, a natural amino acid, an unnatural amino acid,

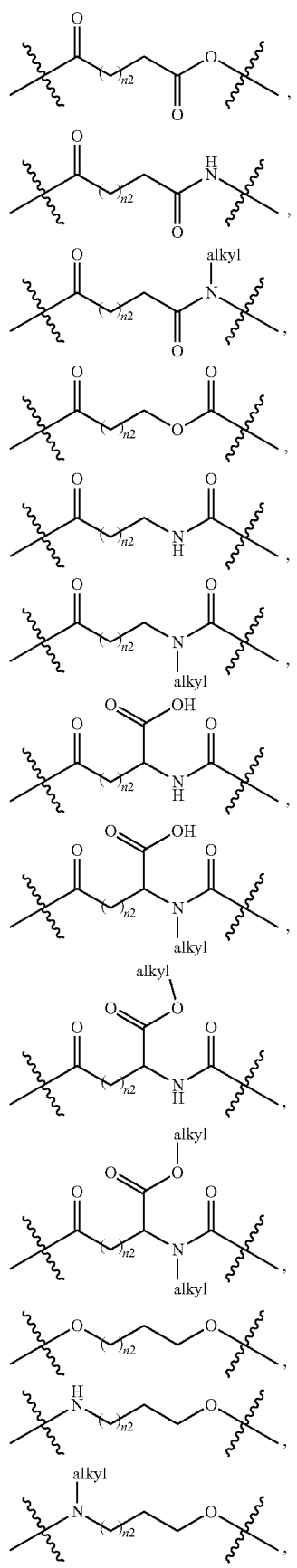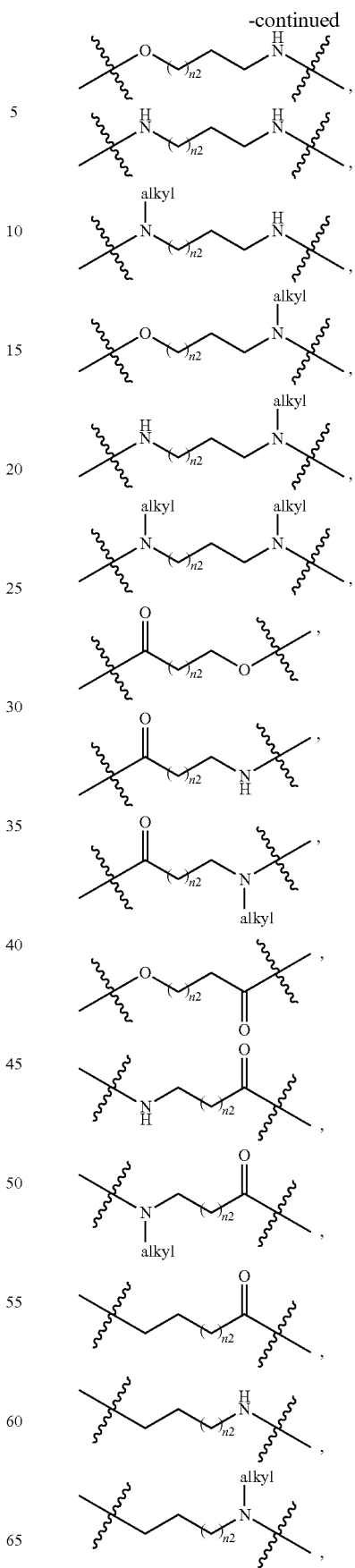

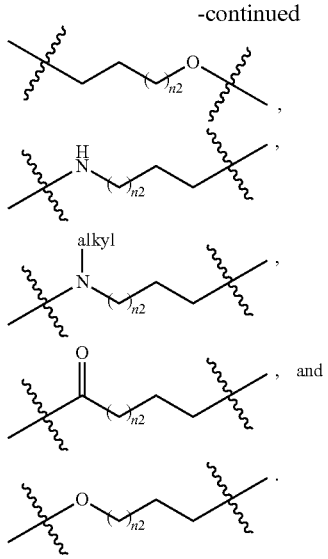

R³⁰⁹ is selected from: alkyl, hydrogen,

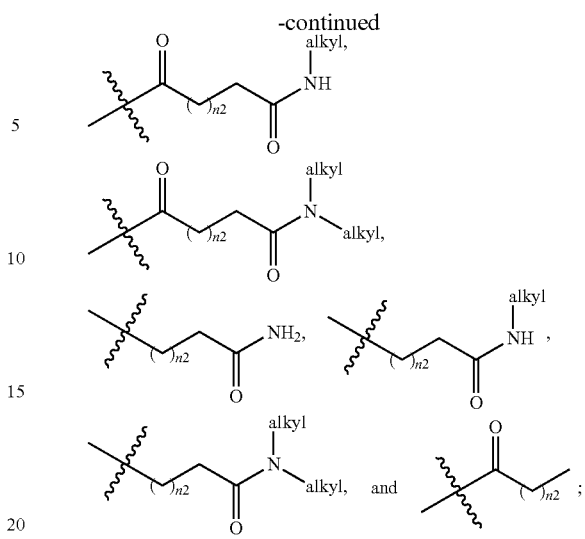

n2 is independently selected at each instance from 0, 1, 2, 3, 4, 5, 6, 7, 8, 9, 10, 11, 12, 13, 14, 15, 16, 17, 18, 19, and 20; and X³⁰⁰ is selected from bond, —NH—, —N(alkyl)-, O, —CH₂—O—, —CH₂—NH—, and —CH₂—N(alkyl).

In one embodiment only 1, 2, 3, 4, or 5 of R³⁰², R³⁰³, R³⁰, R³⁰⁵, R³⁰⁶, R³⁰⁷, and R³⁰⁸ are selected to be bond.

In one embodiment none of R³⁰², R³⁰³, R³⁰⁴, R³⁰⁵, R³⁰⁶, R³⁰⁷, and R³⁰⁸ are selected to be bond.

In one embodiment only 1 of R³⁰², R³⁰³, R³⁰⁴, R³⁰⁵, R³⁰⁶, R³⁰⁷, and R³⁰⁸ are selected to be bond.

In one embodiment only 2 of R³⁰², R³⁰³, R³⁰⁴, R³⁰⁵, R³⁰⁶, R³⁰⁷, and R³⁰⁸ are selected to be bond.

In one embodiment only 3 of R³⁰², R³⁰³, R³⁰⁴, R³⁰⁵, R³⁰⁶, R³⁰⁷, and R³⁰⁸ are selected to be bond.

In one embodiment only 4 of R³⁰², R³⁰³, R³⁰⁴, R³⁰⁵, R³⁰⁶, R³⁰⁷, and R³⁰⁸ are selected to be bond.

In one embodiment only 5 of R³⁰², R³⁰³, R³⁰⁴, R³⁰⁵, R³⁰⁶, R³⁰⁷, and R³⁰⁸ are selected to be bond.

Non-limiting examples of compounds of the present invention with a R³⁰¹ group include:

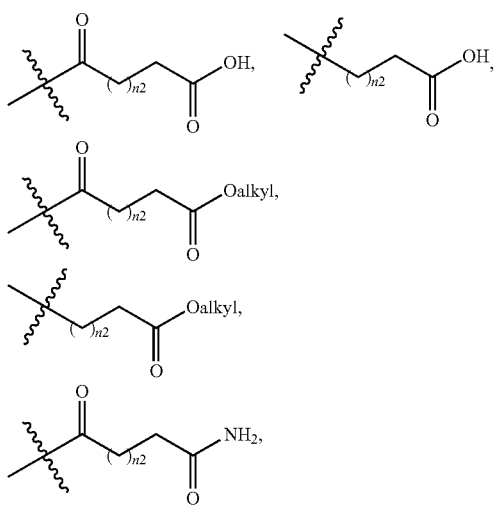

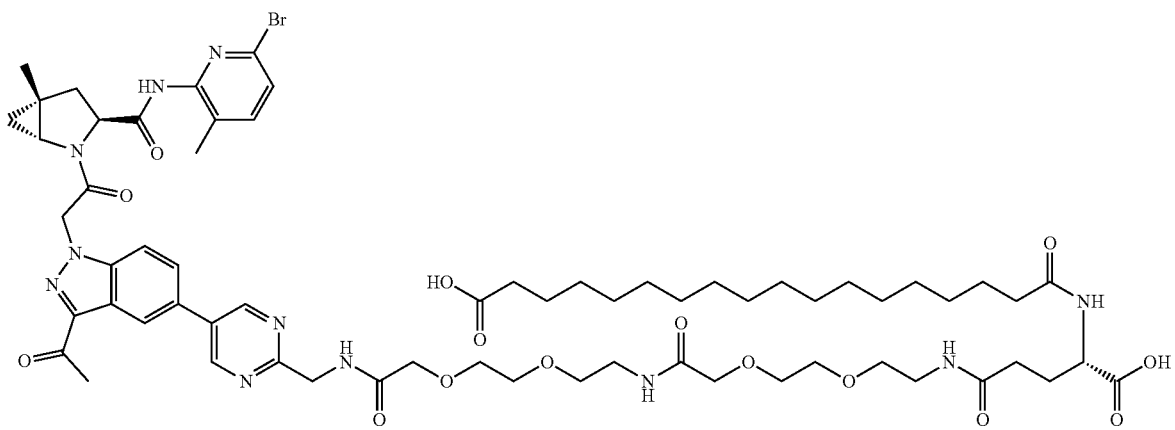

275 276
-continued
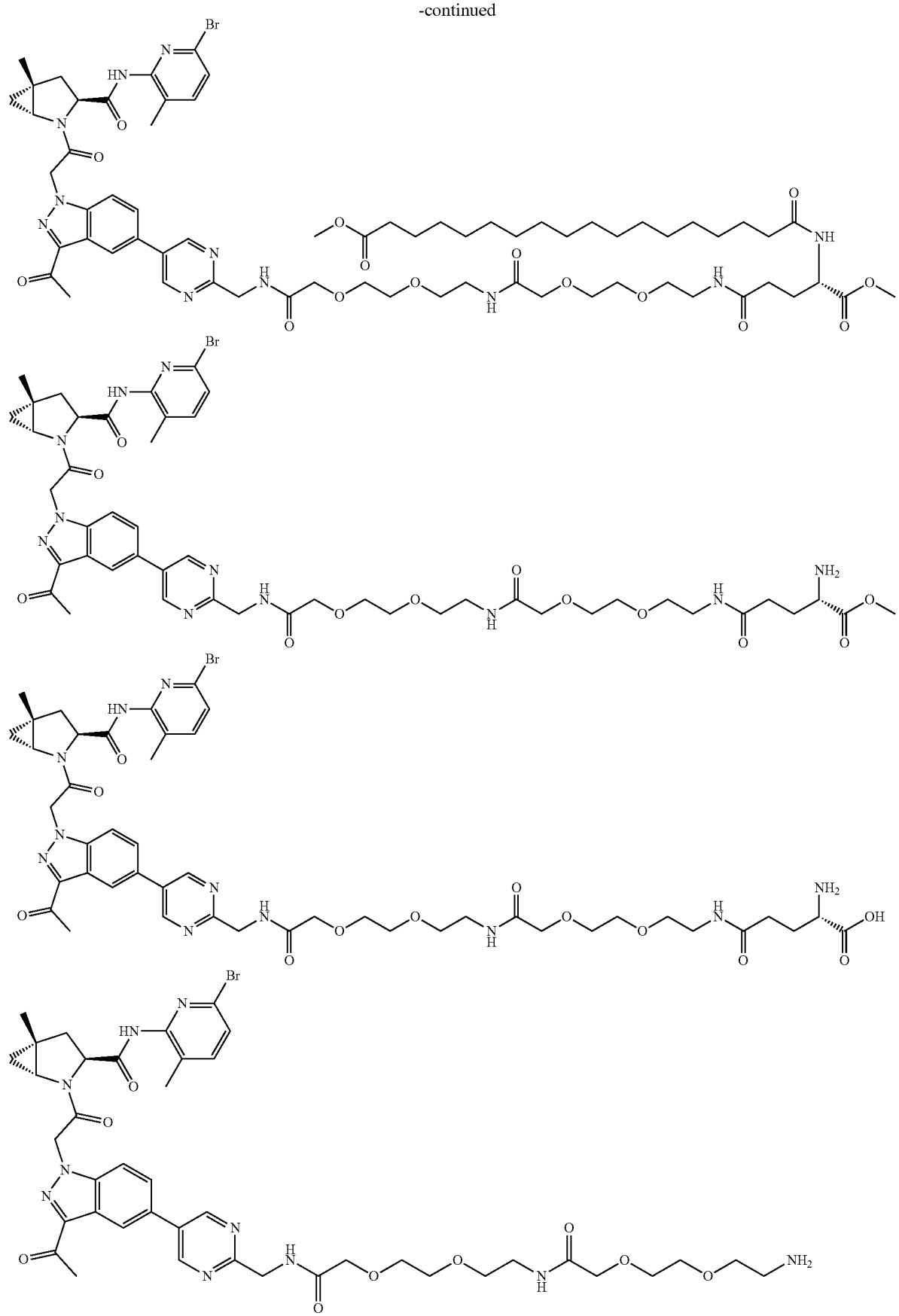

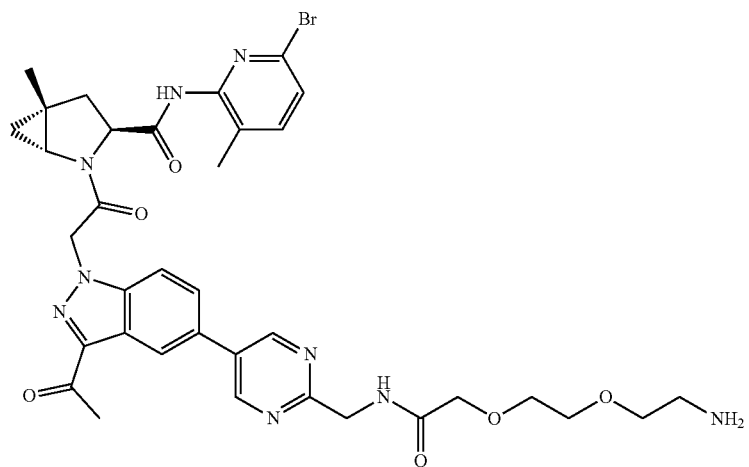
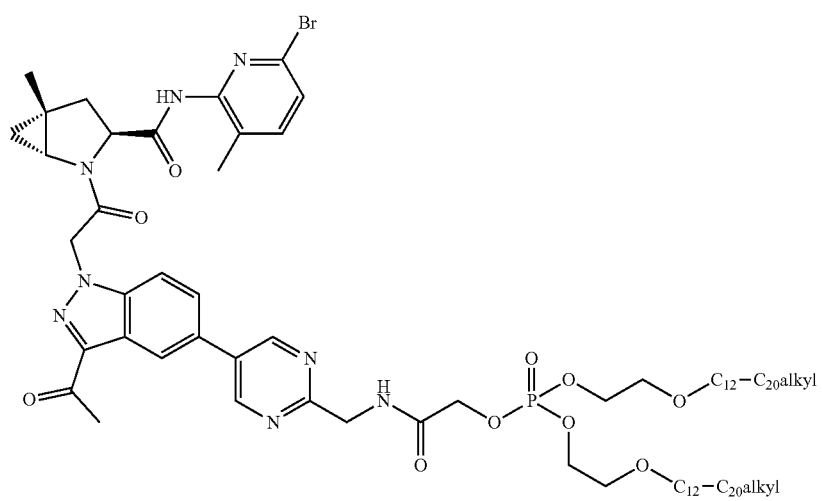
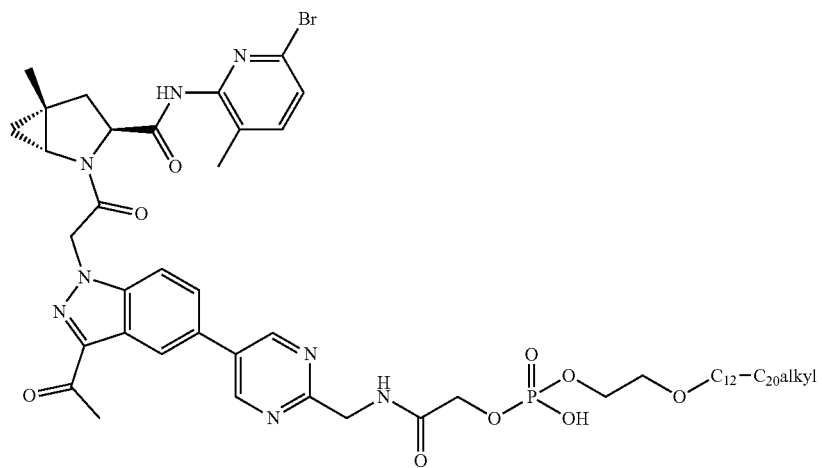

279
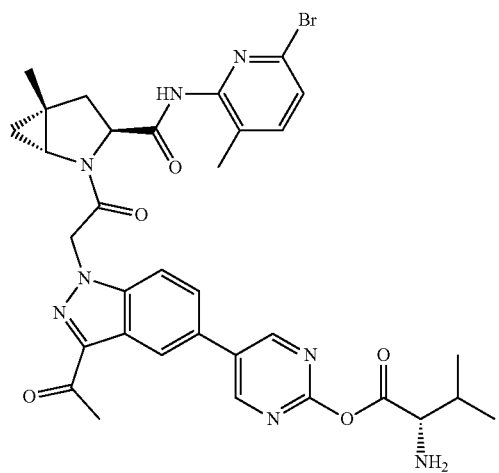 [SMILES: CC(=O)c1nn(CC(=O)N2[C@H](C(=O)Nc3nc(Br)ccc3C)C[C@@]3(C)C[C@@H]23)c2ccc(-c3cnc(OC(=O)[C@@H](N)C(C)C)nc3)cc12]
280
-continued
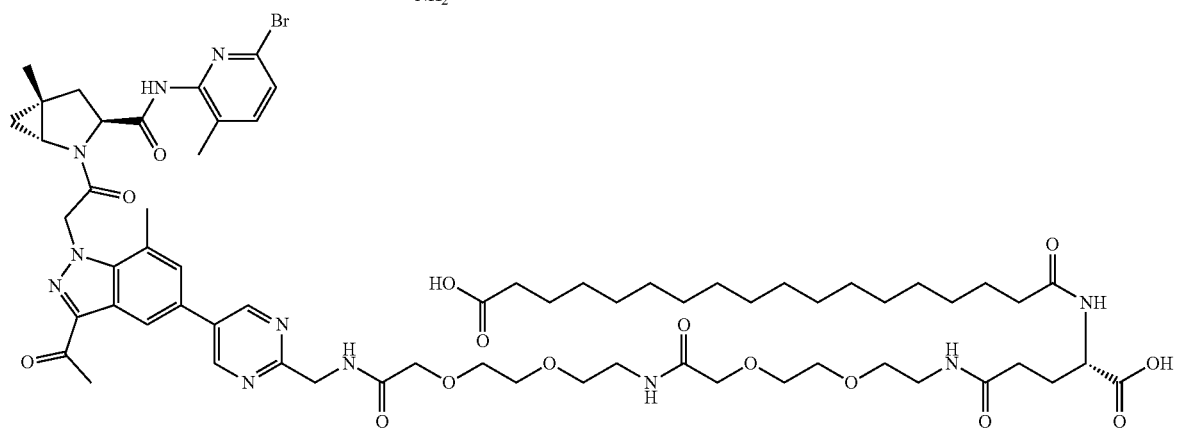
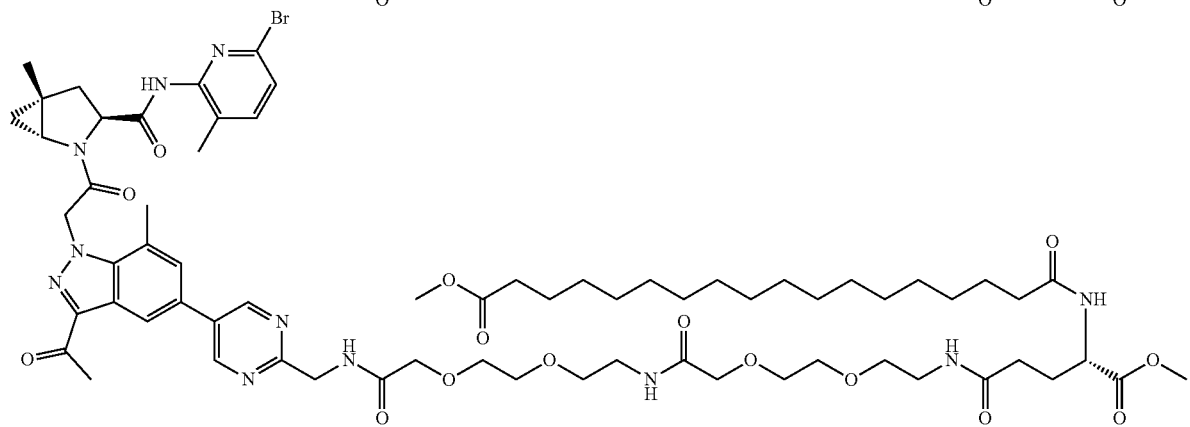
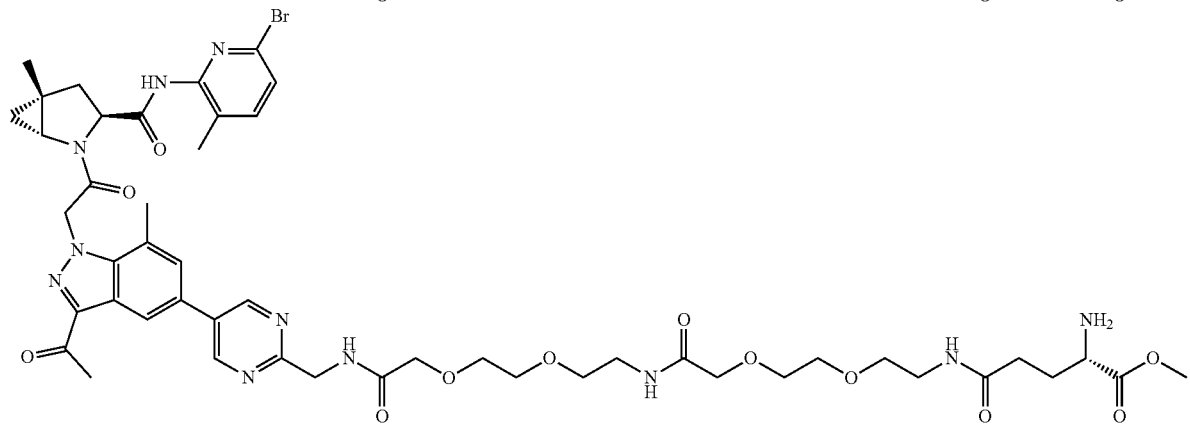

281
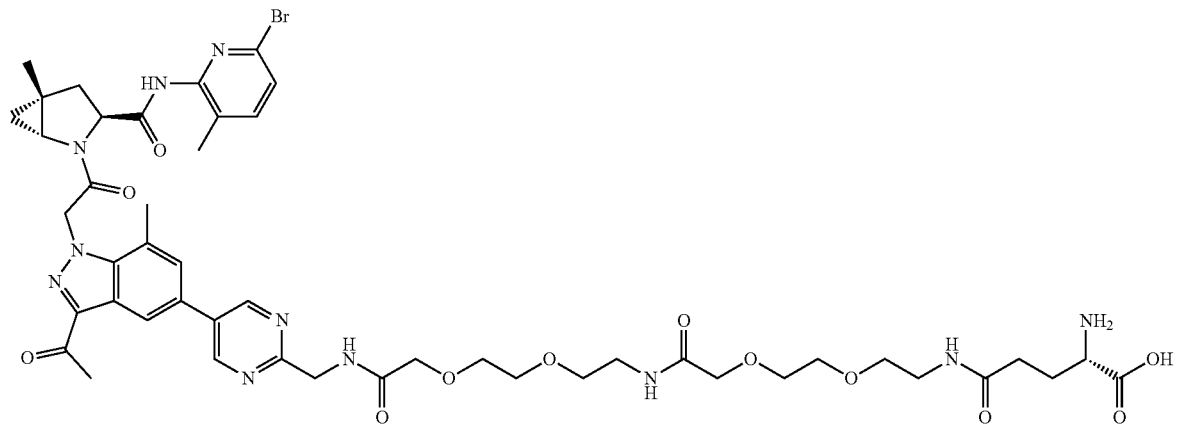
282
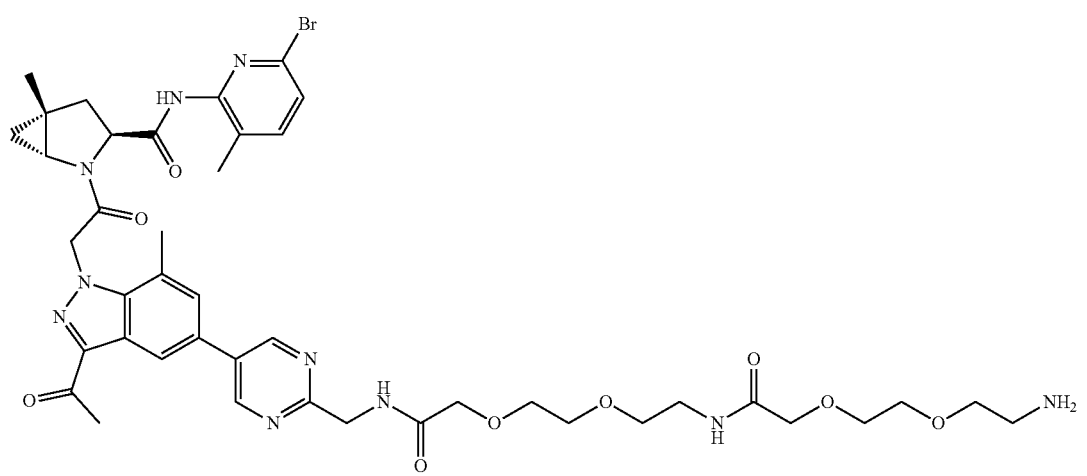
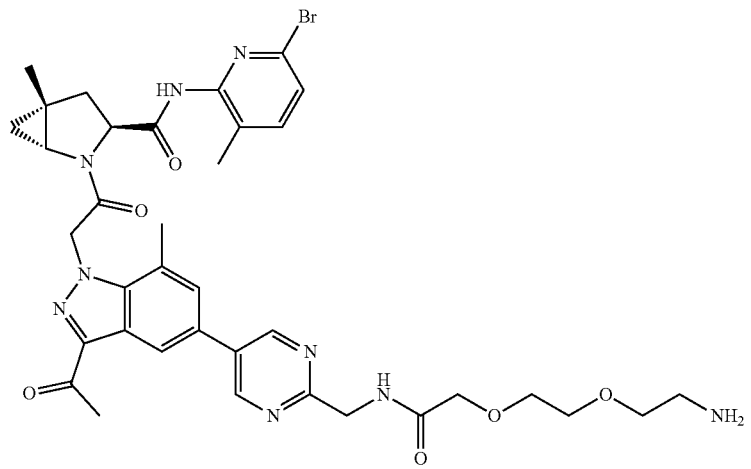

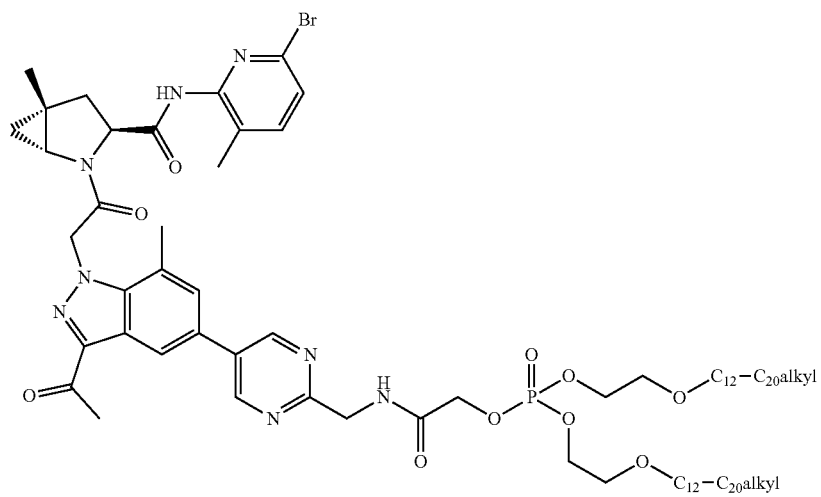
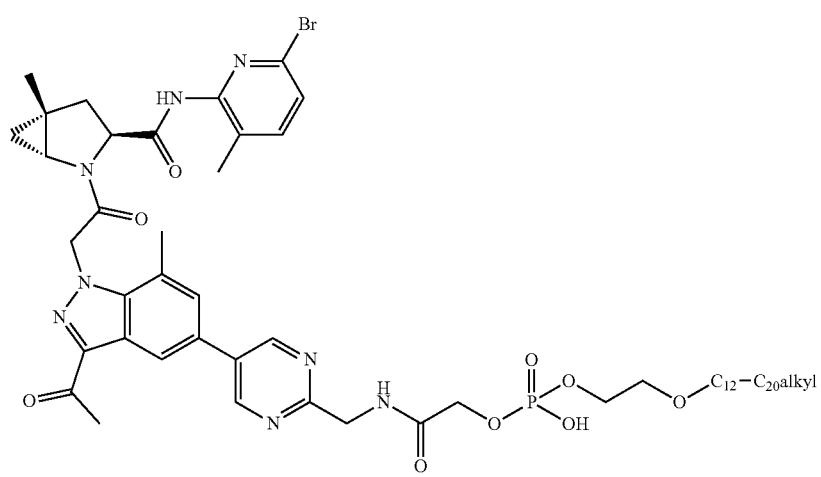
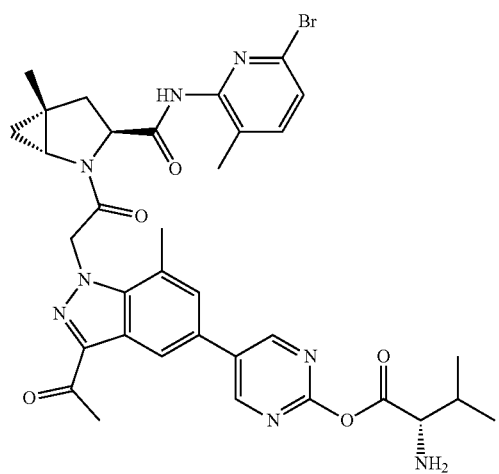 [SMILES: CC(=O)c1nn(CC(=O)N2[C@H](C(=O)Nc3nc(Br)ccc3C)C[C@@]3(C)C[C@@H]23)c2c(C)cc(-c3cnc(OC(=O)[C@@H](N)C(C)C)nc3)cc12]

285
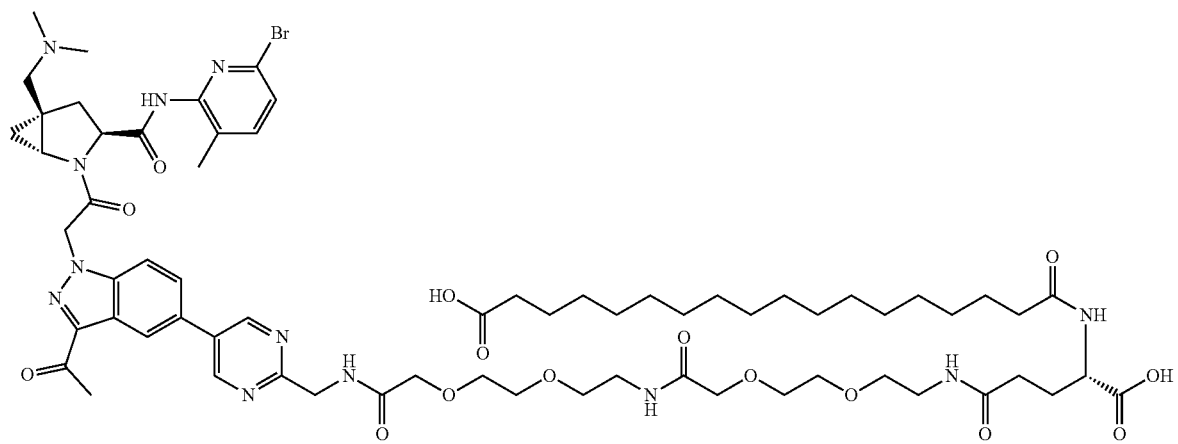
-continued
286
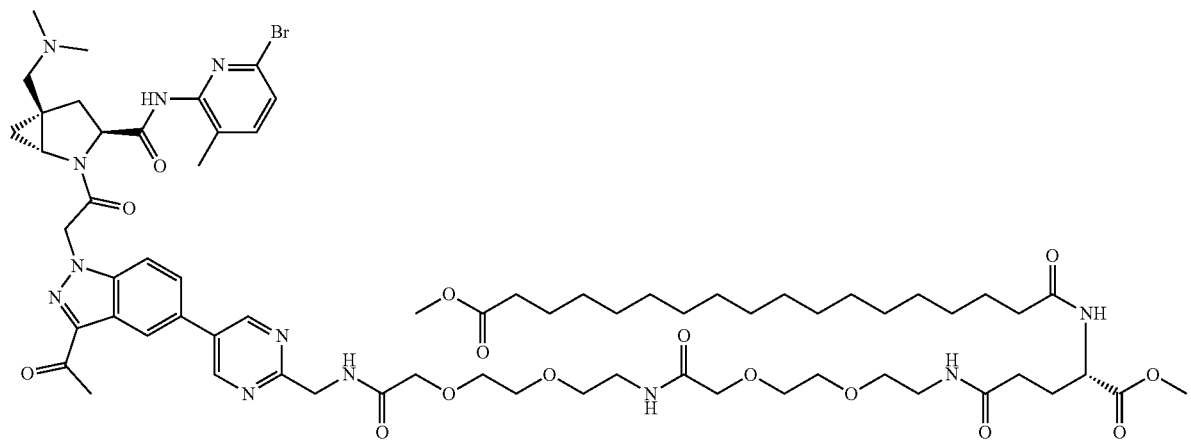
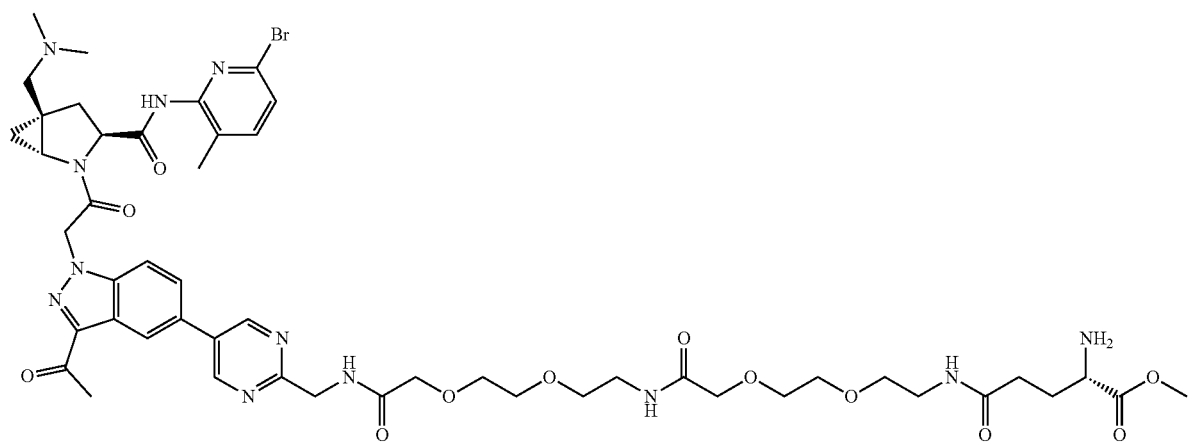

287
288
-continued
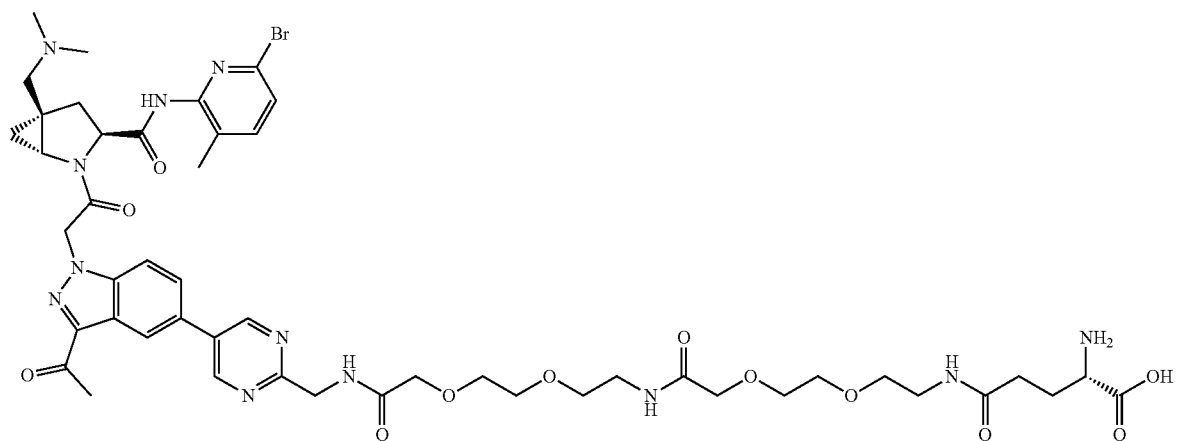
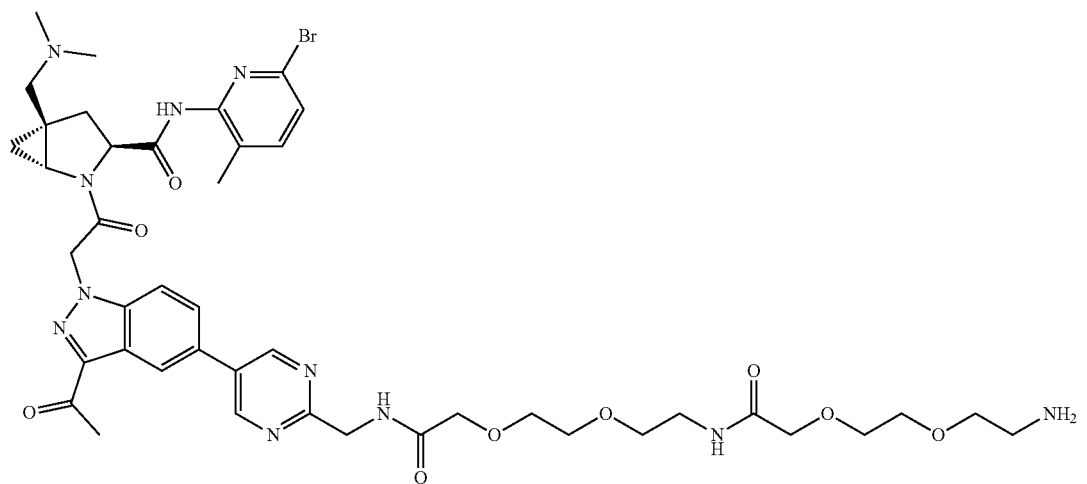
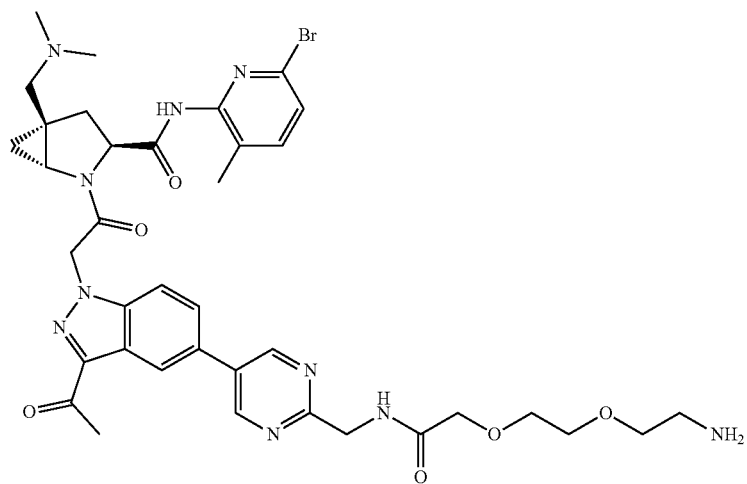

-continued
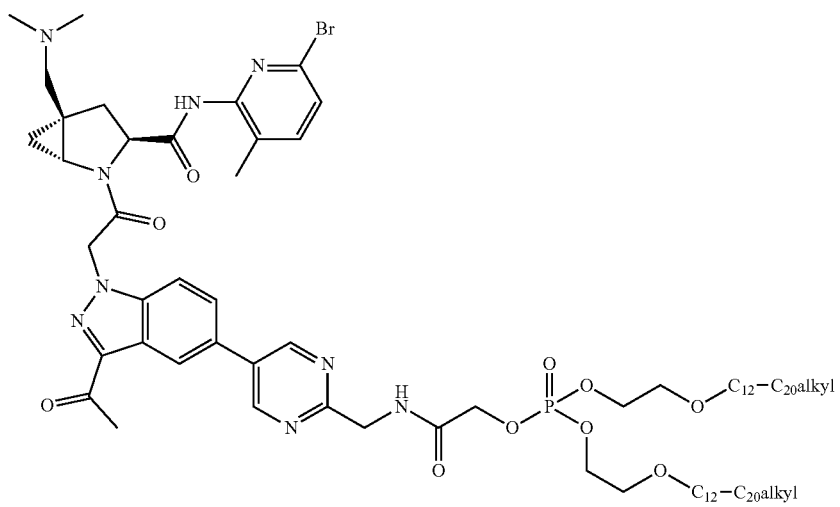
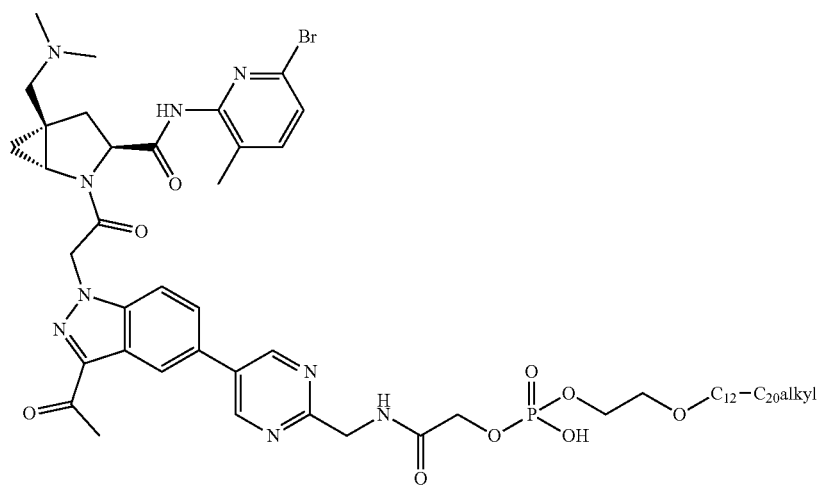
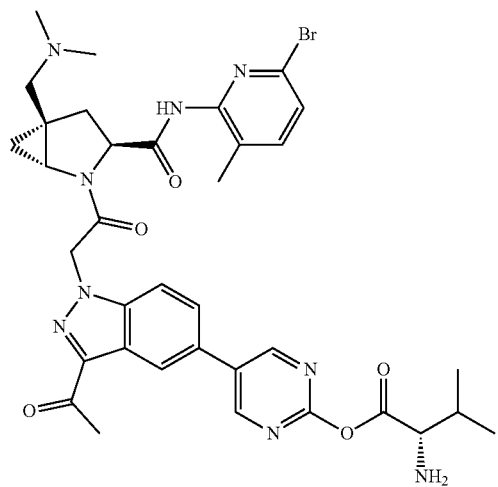 [SMILES: CC(=O)c1nn(CC(=O)N2[C@H](C(=O)Nc3nc(Br)ccc3C)C[C@@]3(CN(C)C)C[C@@H]23)c2ccc(-c3cnc(OC(=O)[C@@H](N)C(C)C)nc3)cc12]

291 292
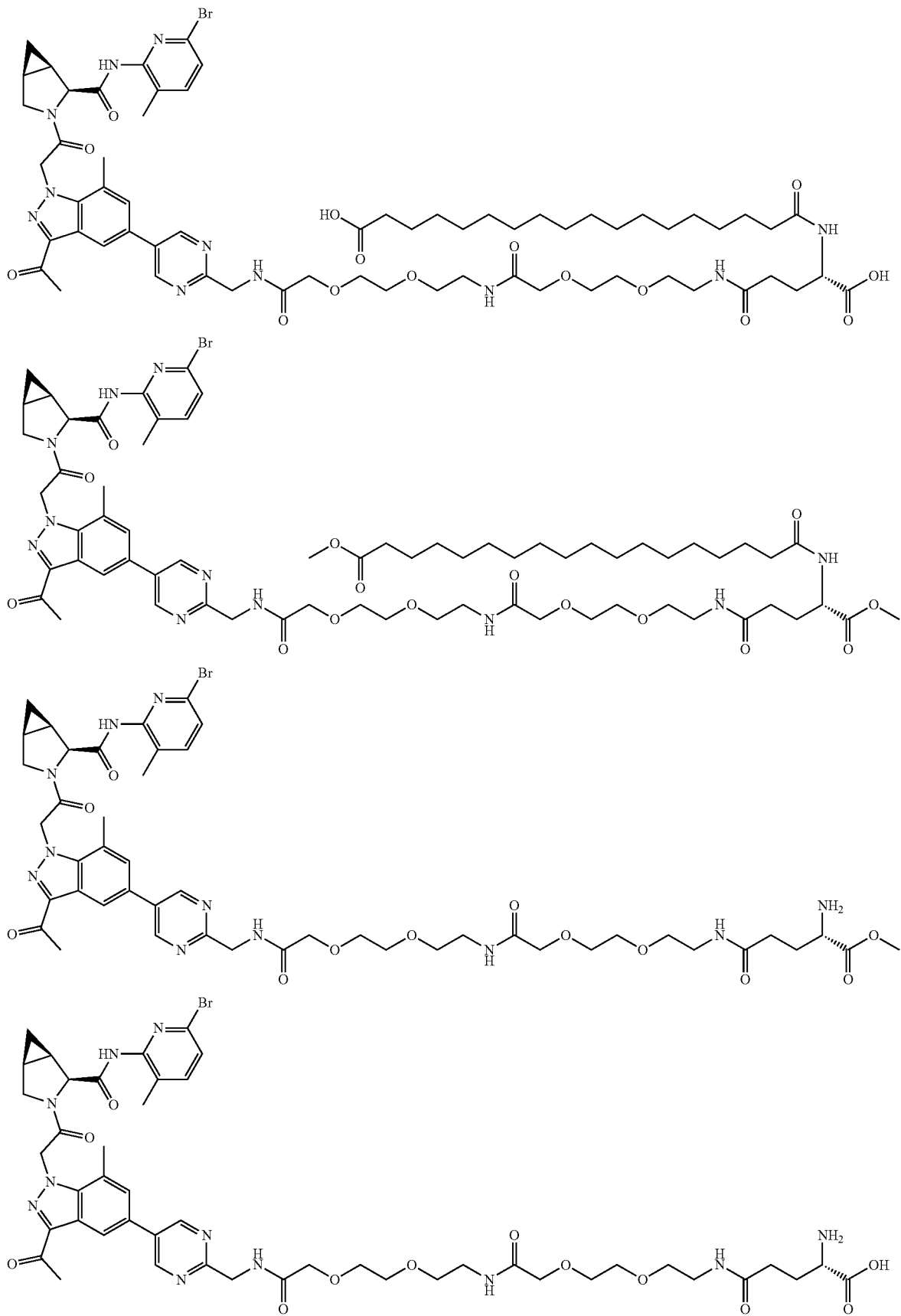

-continued
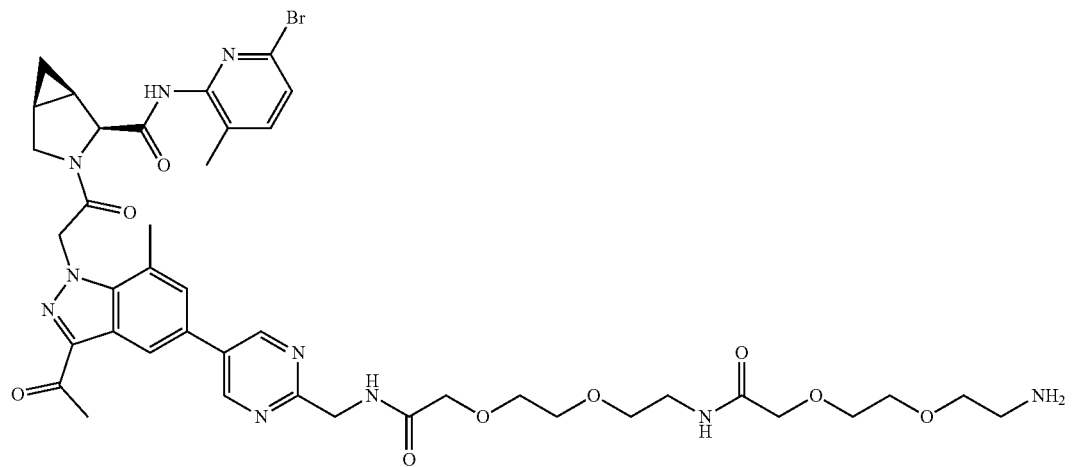
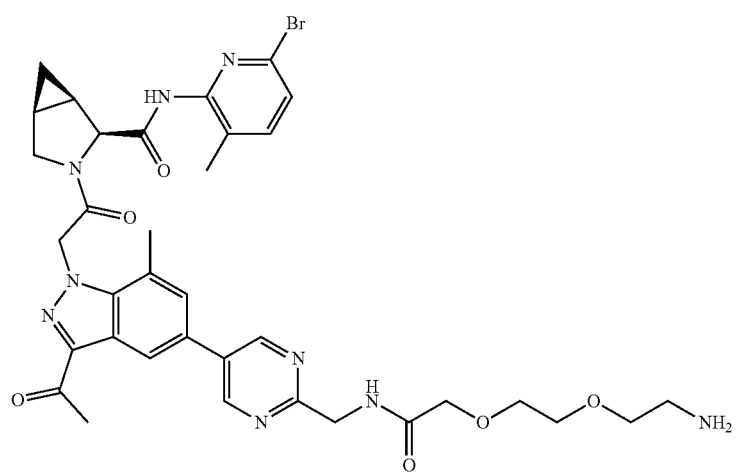
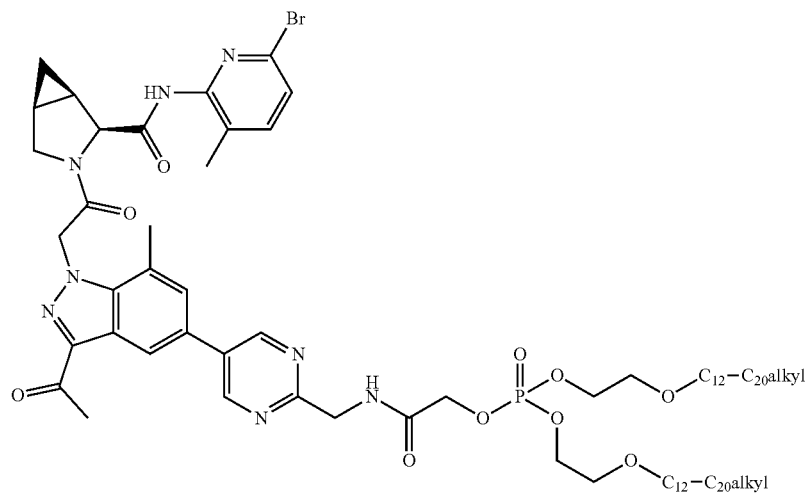

295
296
-continued
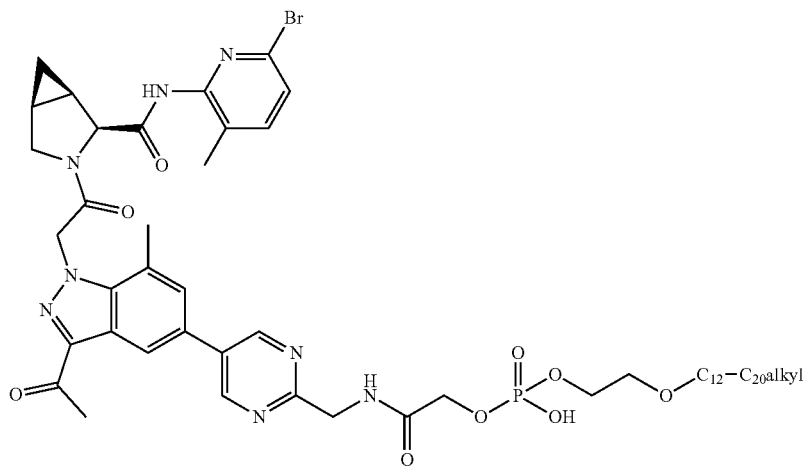
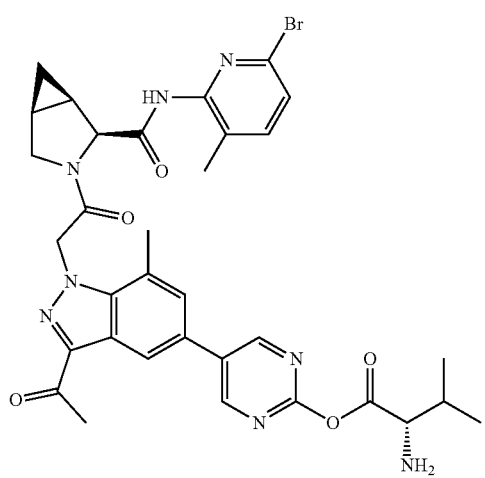 [SMILES: CC(=O)c1nn(CC(=O)N2C[C@H]3C[C@H]3[C@H]2C(=O)Nc2nc(Br)ccc2C)c2c(C)cc(-c3cnc(OC(=O)[C@@H](N)C(C)C)nc3)cc12]
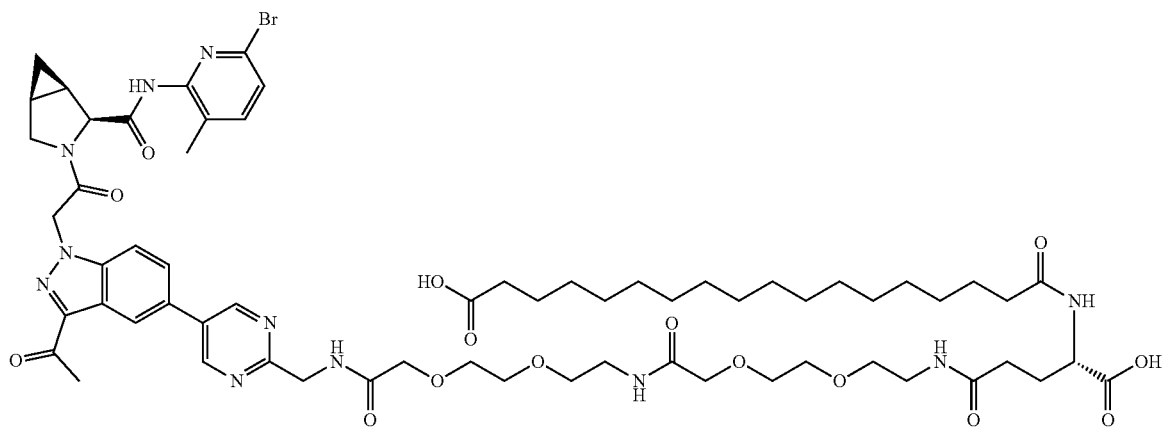

297
298
-continued
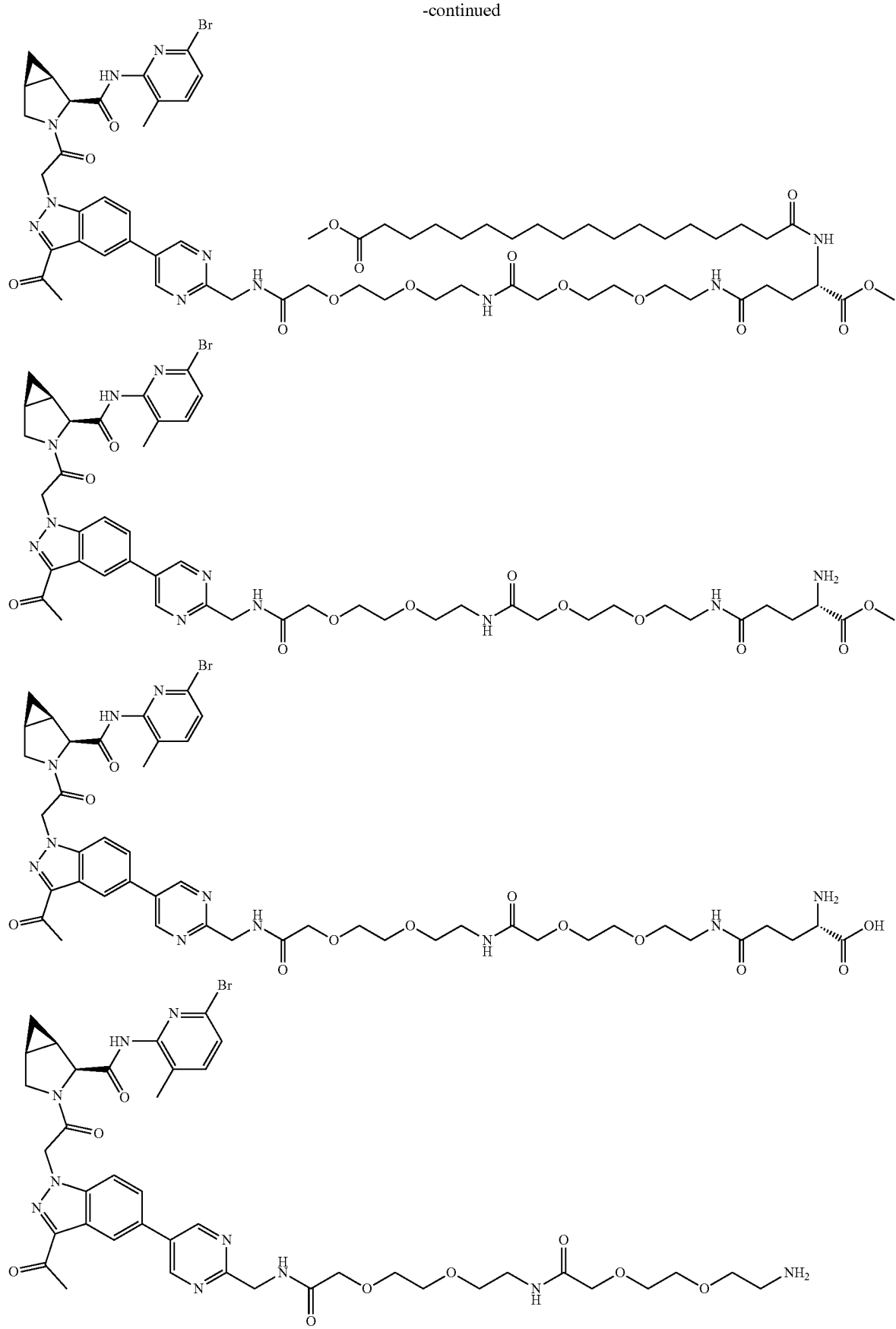

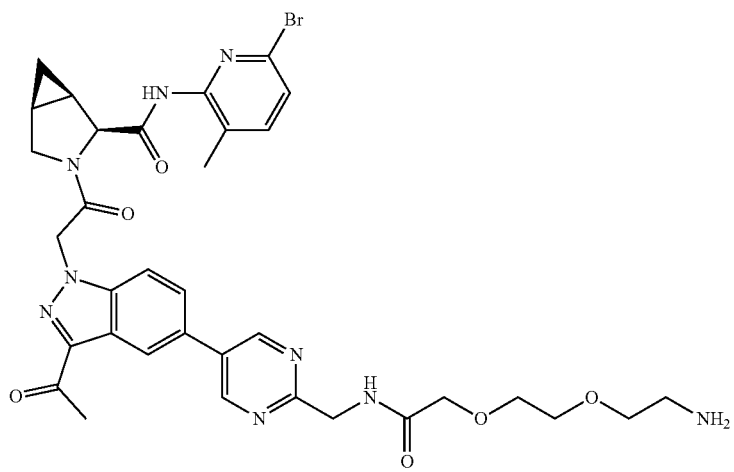
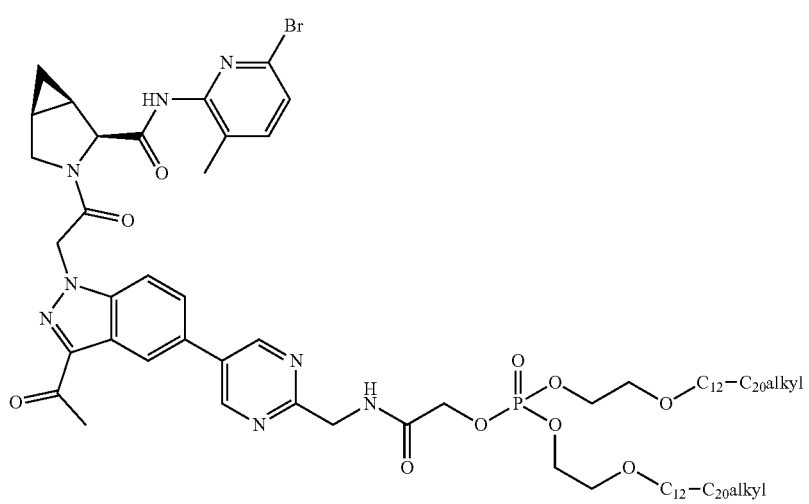
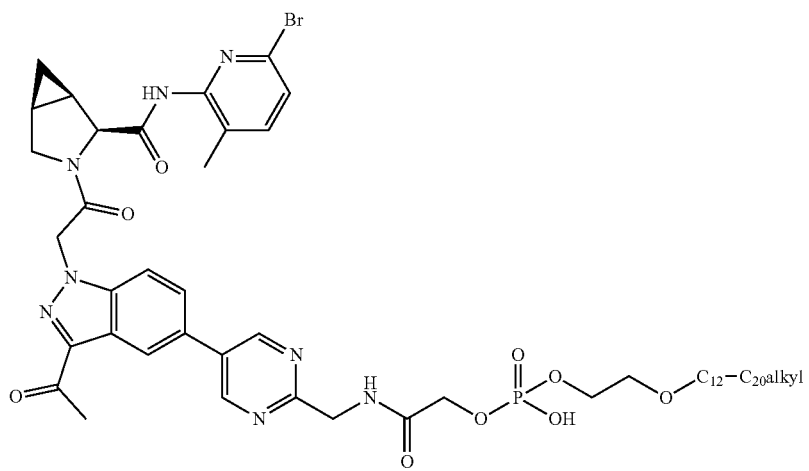

301
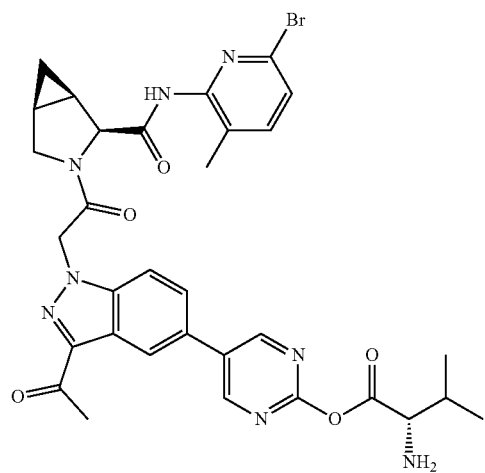 [SMILES: CC(=O)c1nn(CC(=O)N2C[C@H]3C[C@H]3[C@H]2C(=O)Nc2nc(Br)ccc2C)c2ccc(-c3cnc(OC(=O)[C@@H](N)C(C)C)nc3)cc12]
302
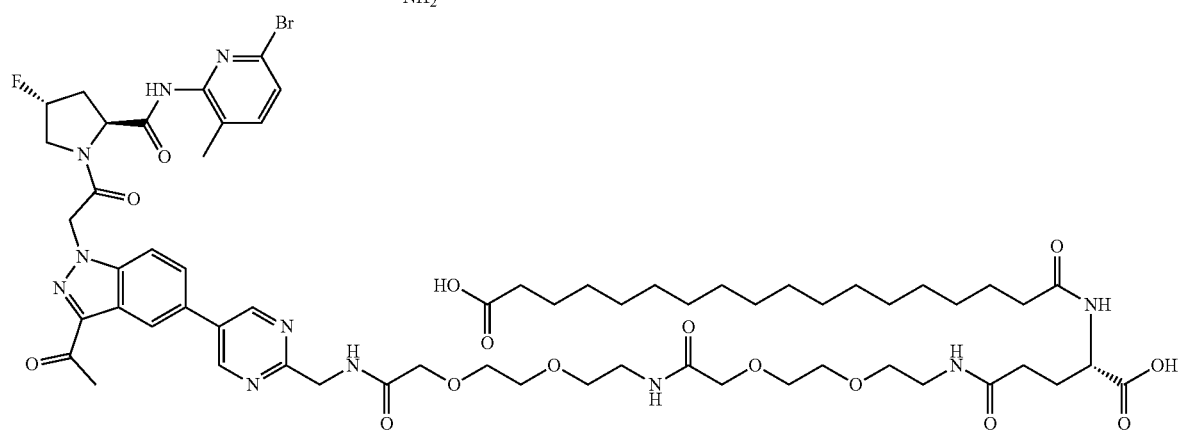
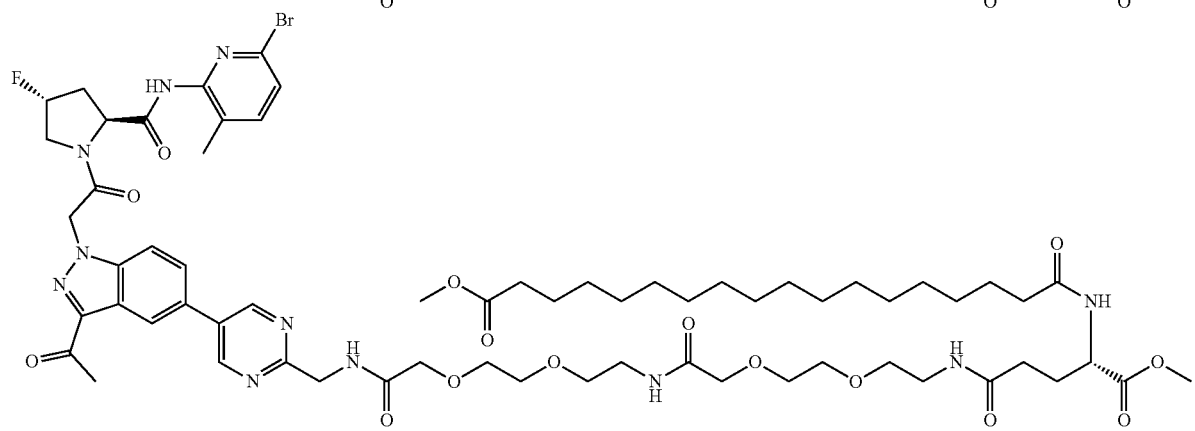
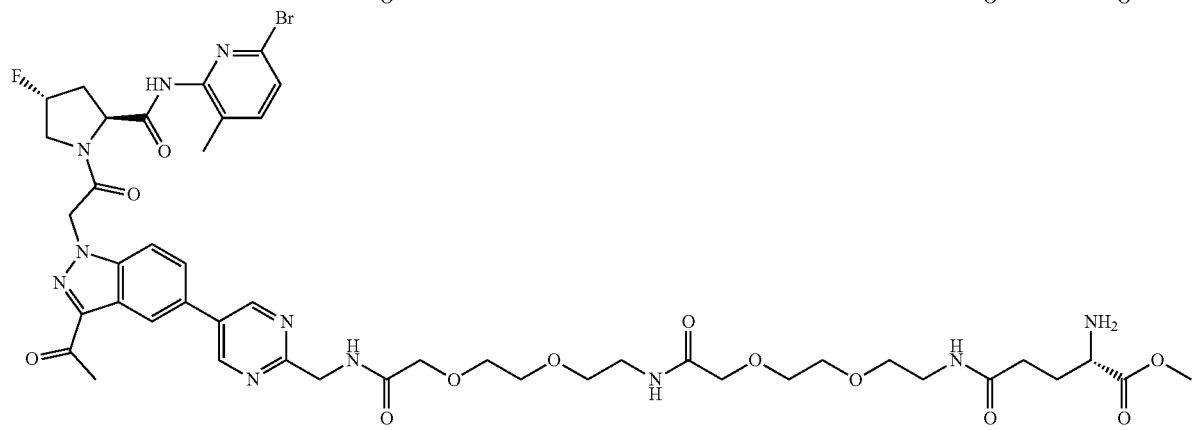

-continued
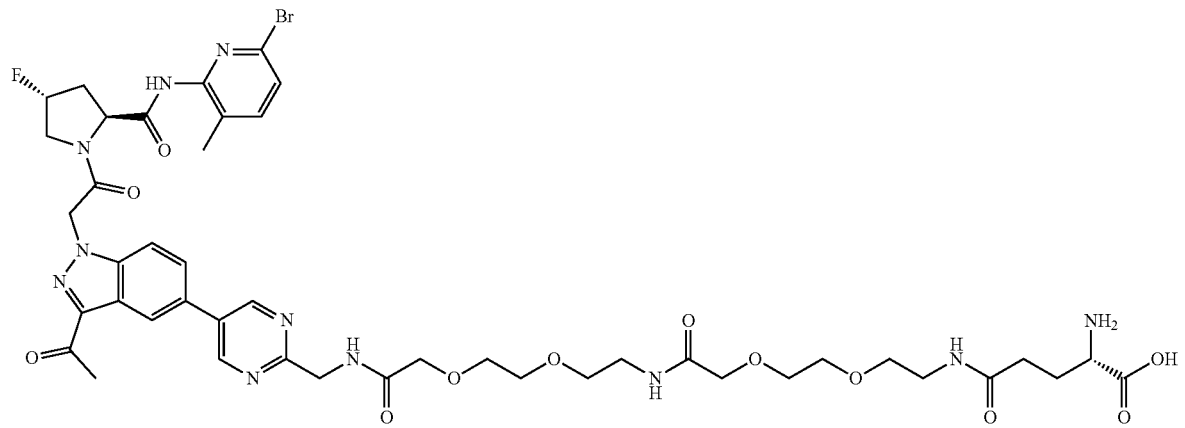
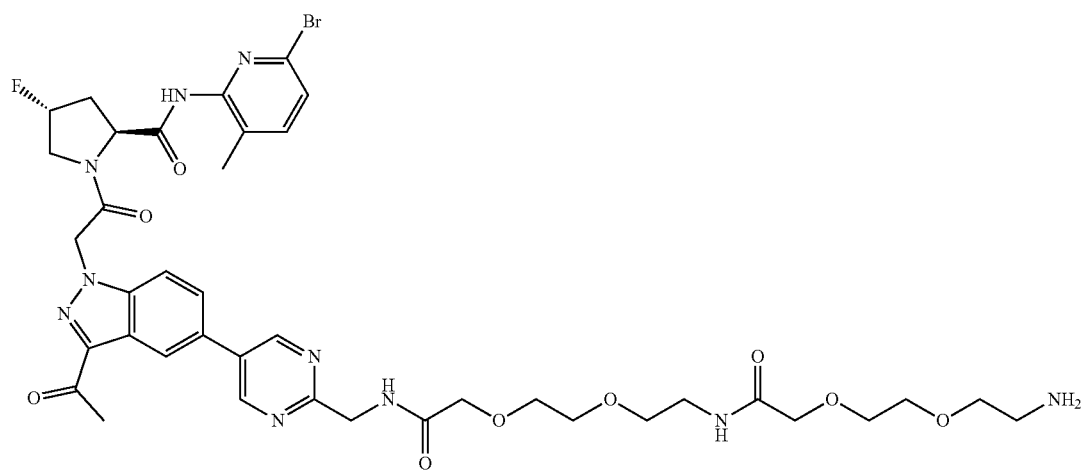
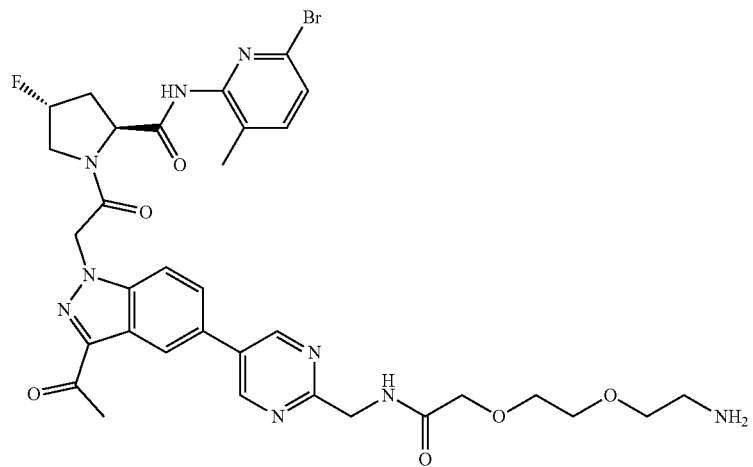

-continued
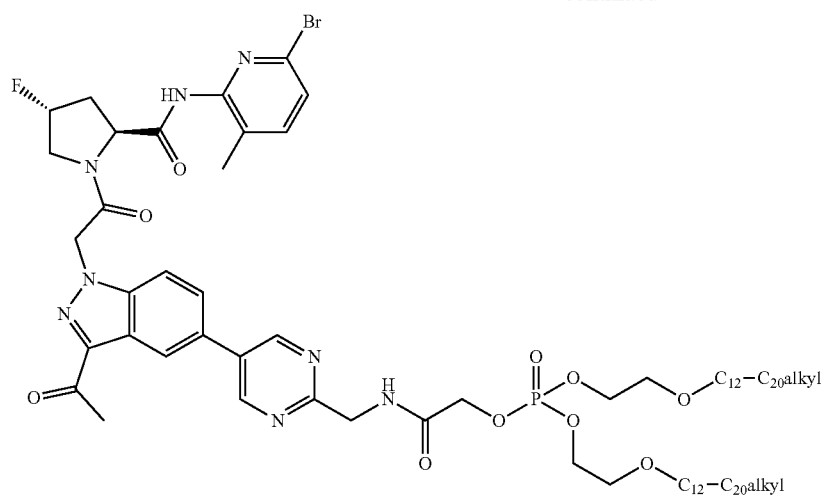
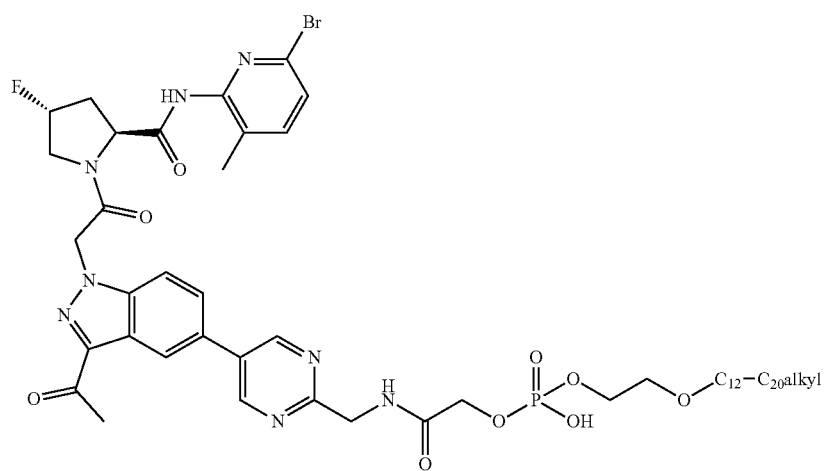
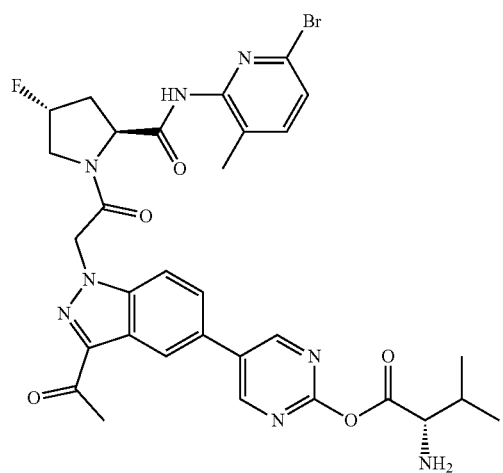 [SMILES: CC(=O)c1nn(CC(=O)N2C[C@H](F)C[C@H]2C(=O)Nc2nc(Br)ccc2C)c2ccc(-c3cnc(OC(=O)[C@@H](N)C(C)C)nc3)cc12]

307
308
-continued
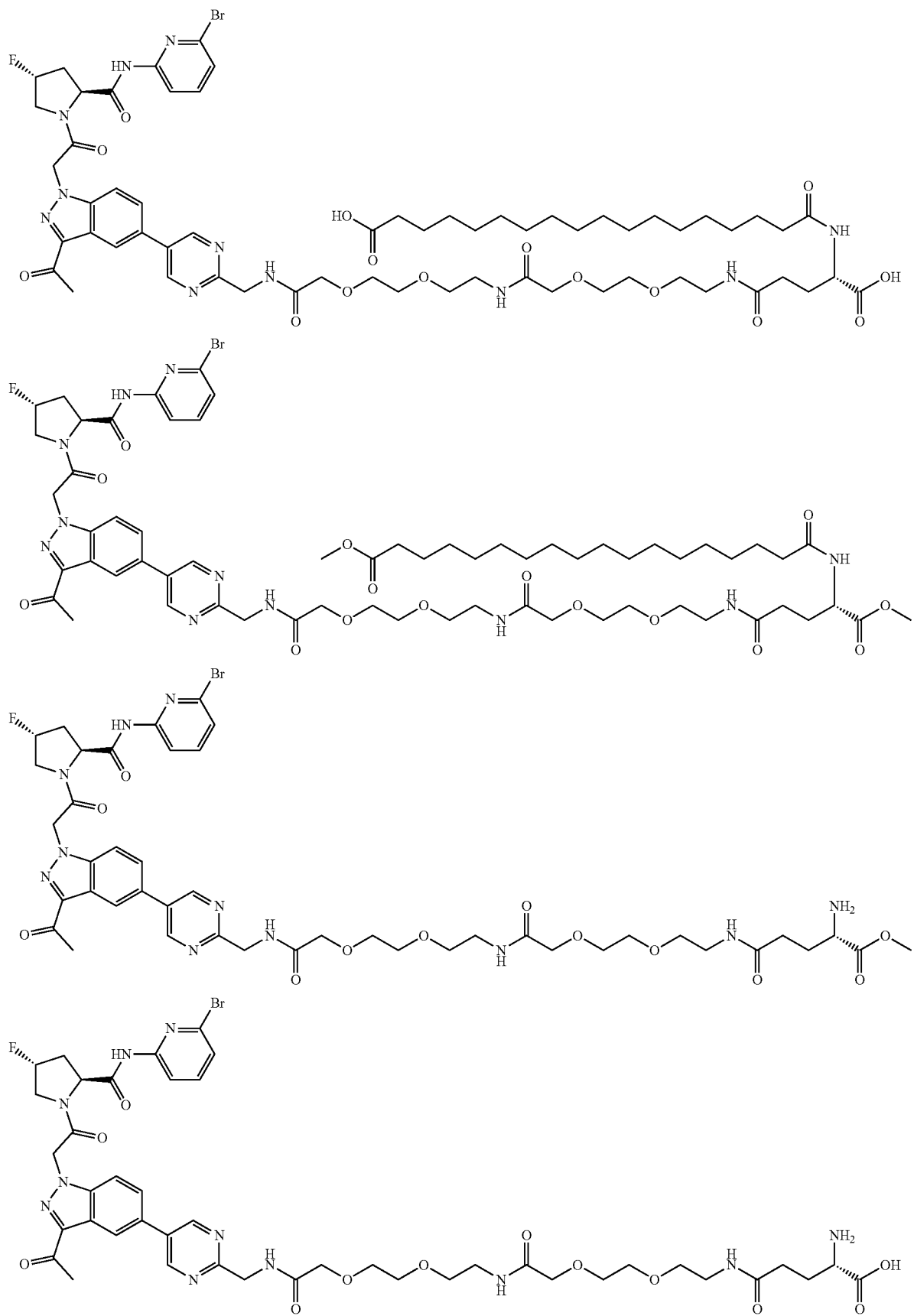

-continued
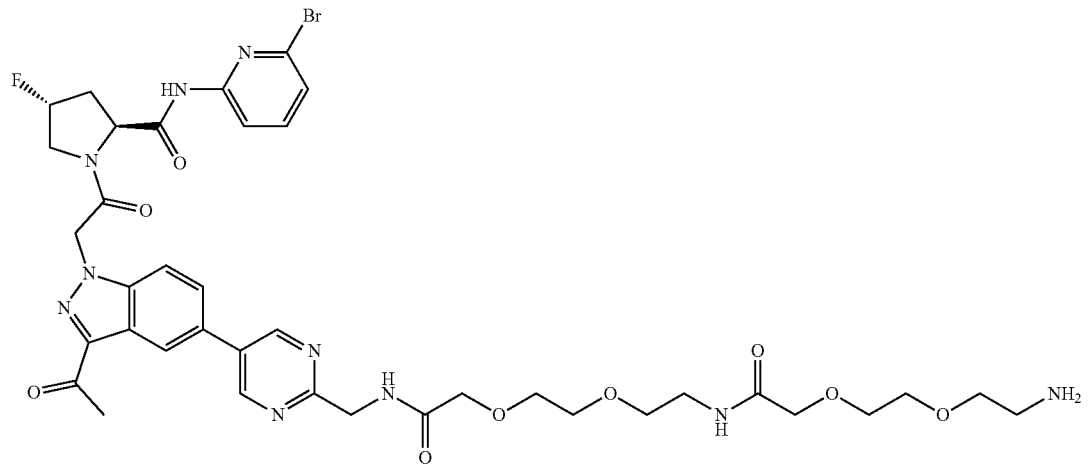
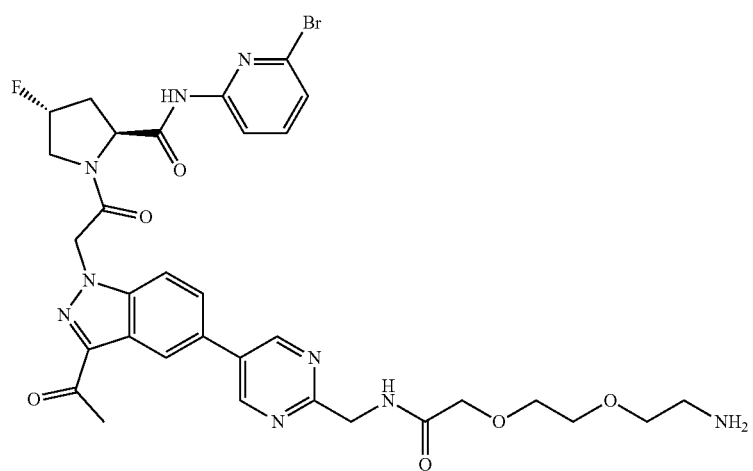
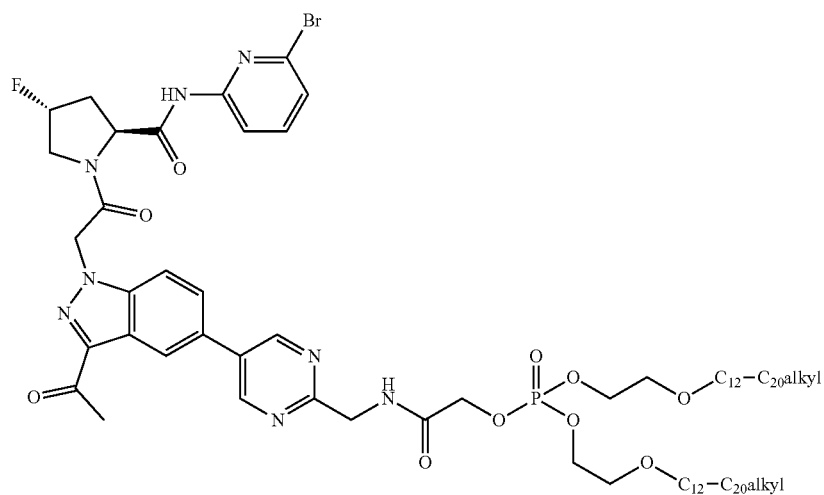

311
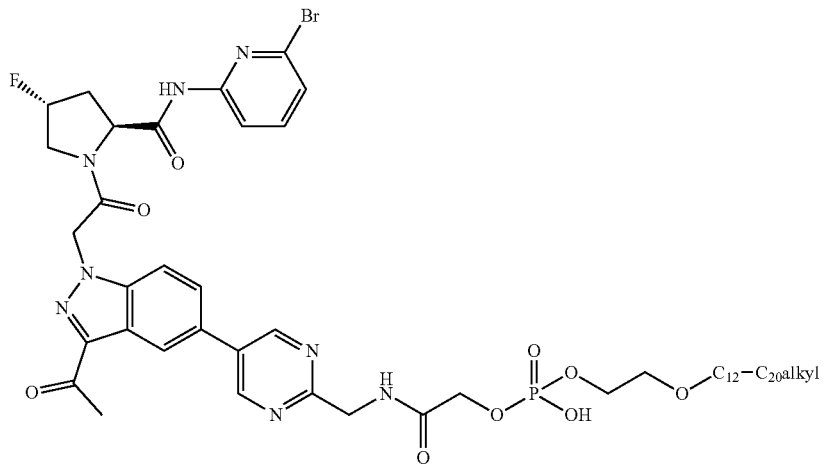
312
-continued
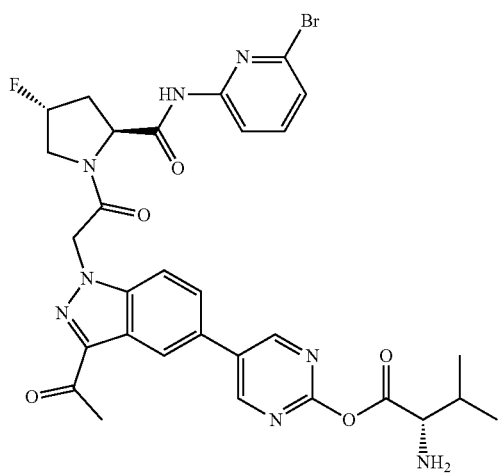 [SMILES: CC(=O)c1nn(CC(=O)N2C[C@H](F)C[C@H]2C(=O)Nc2cccc(Br)n2)c2ccc(-c3cnc(OC(=O)[C@@H](N)C(C)C)nc3)cc12]
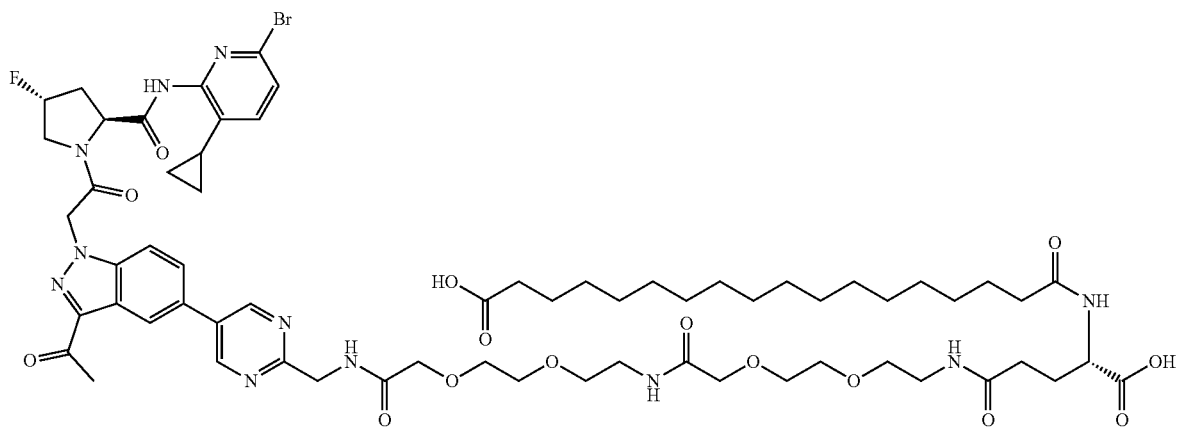

313 314
-continued
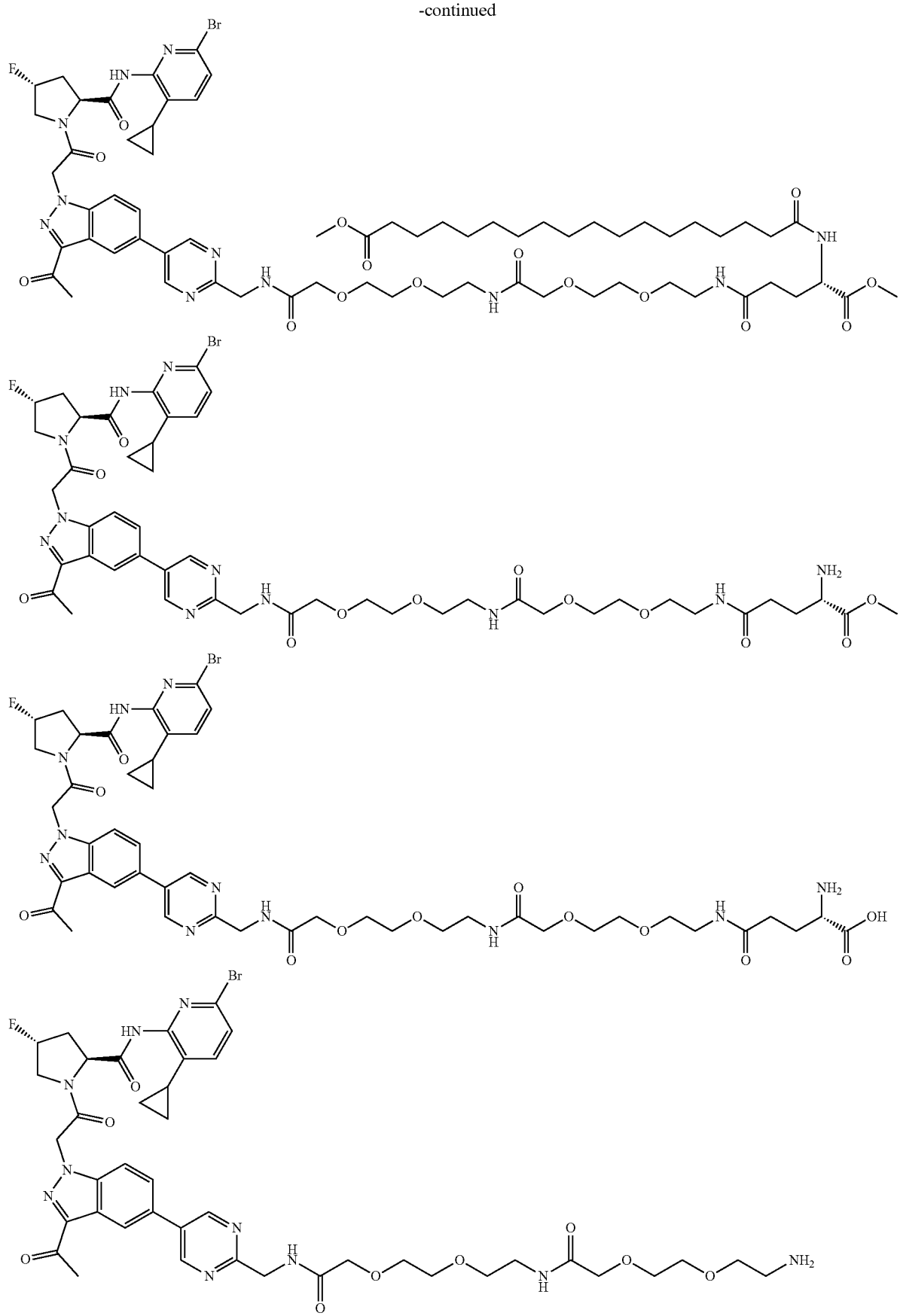

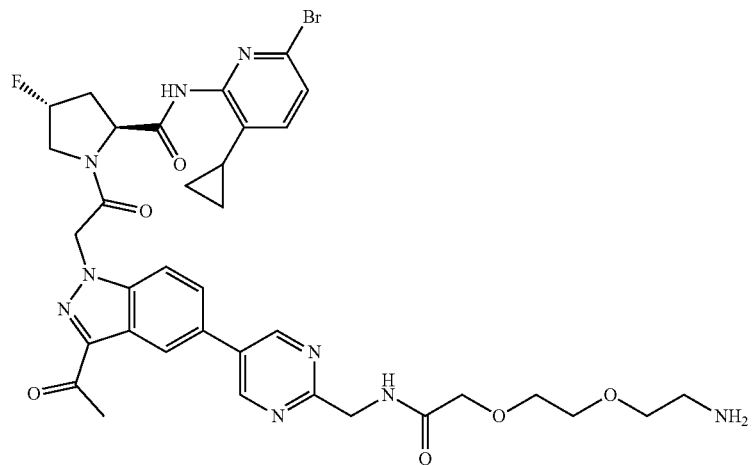
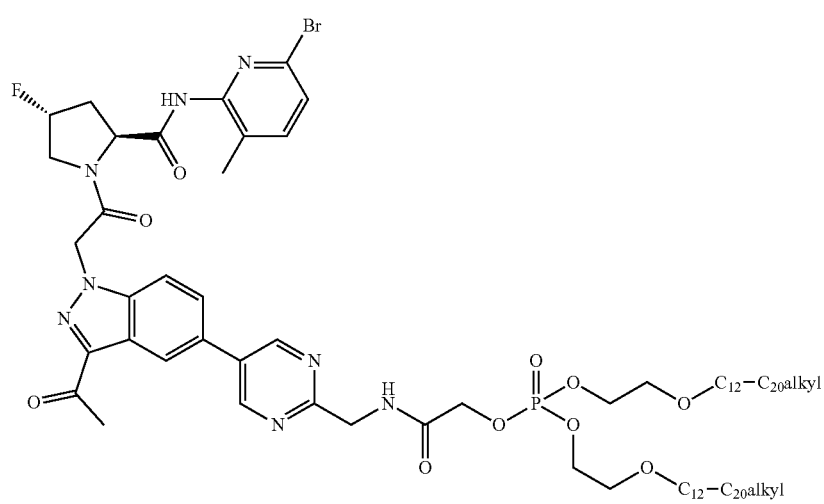
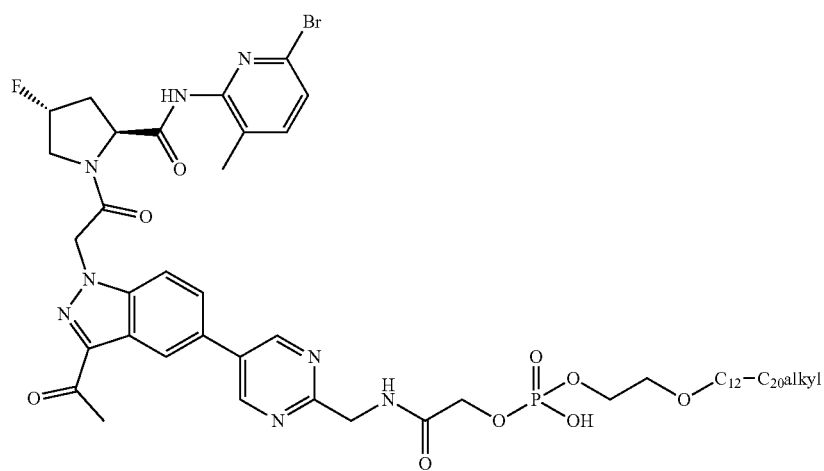

317
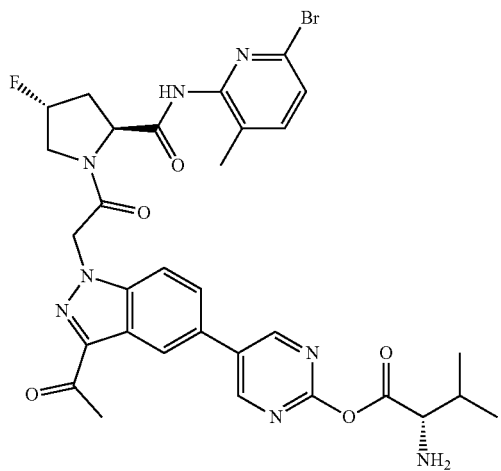 [SMILES: CC(=O)c1nn(CC(=O)N2C[C@H](F)C[C@H]2C(=O)Nc2nc(Br)ccc2C)c2ccc(-c3cnc(OC(=O)[C@@H](N)C(C)C)nc3)cc12]
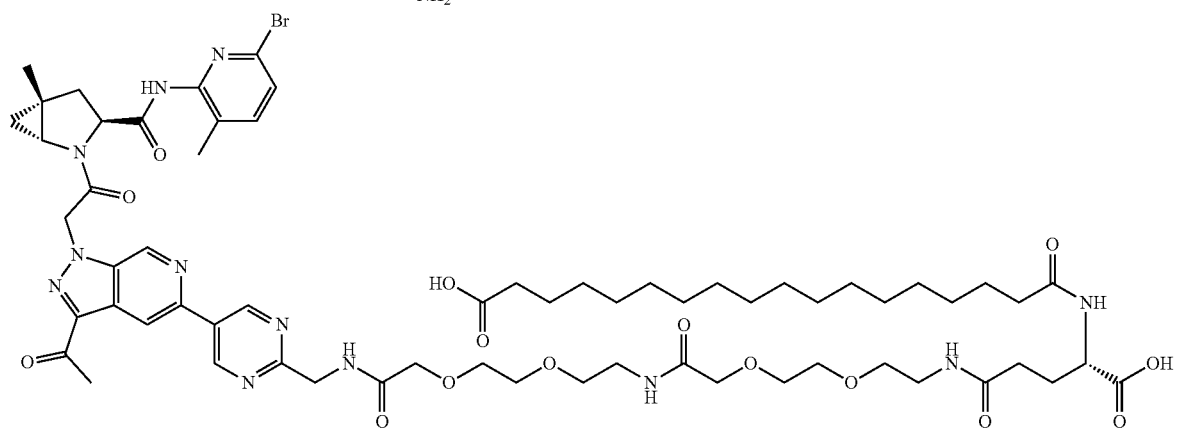
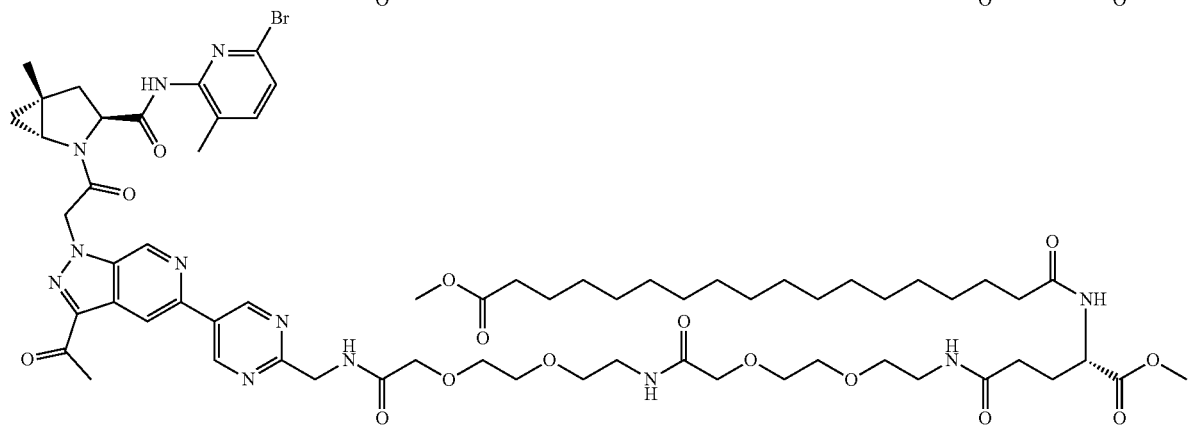
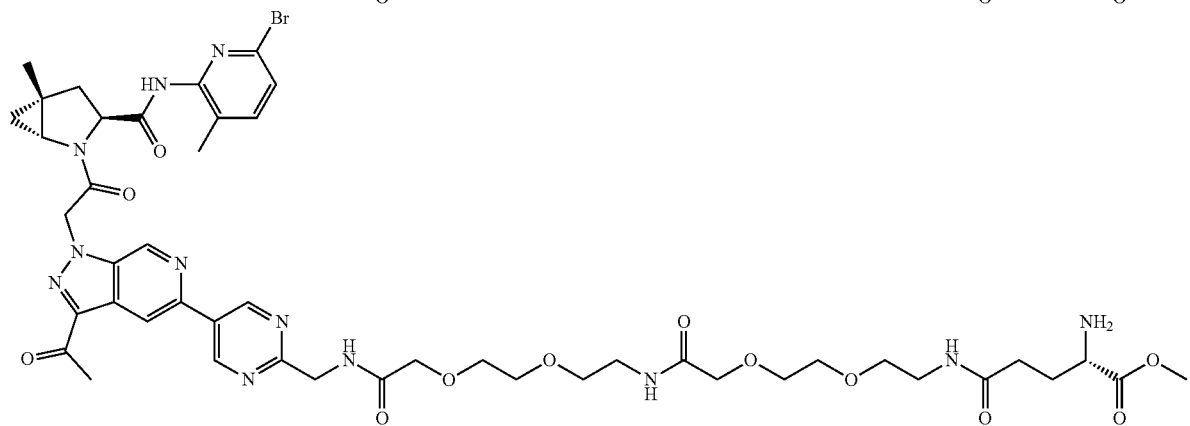

319
320
-continued
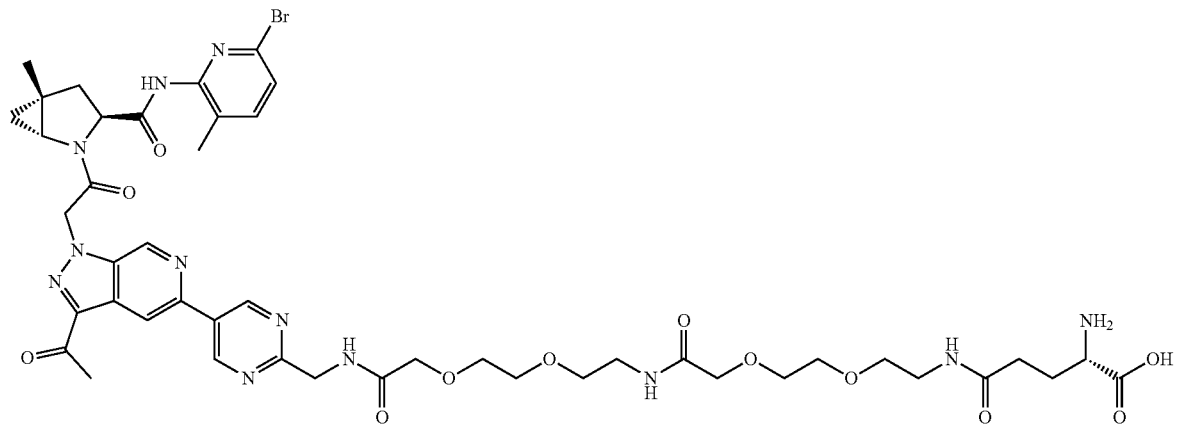
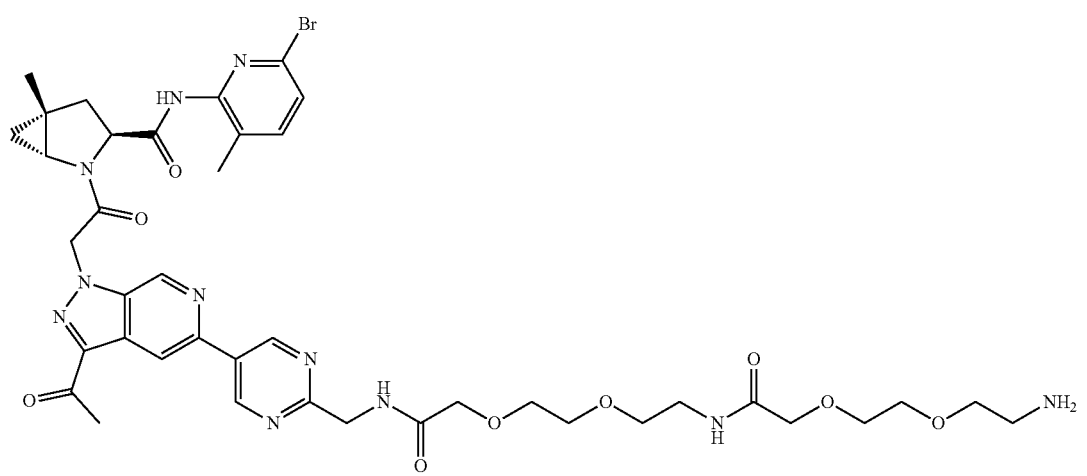
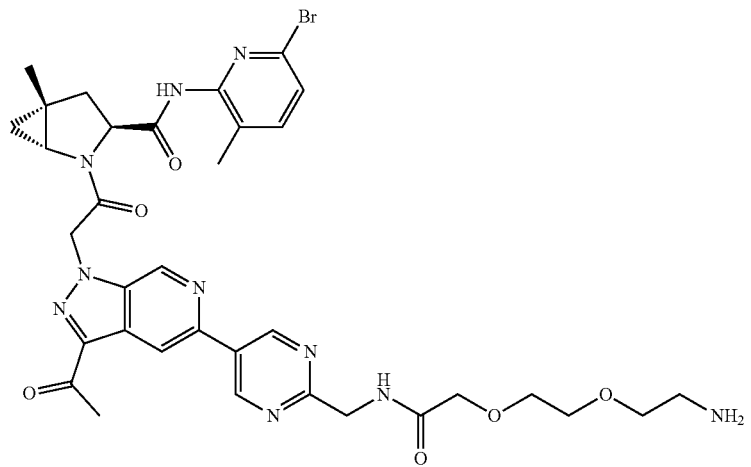

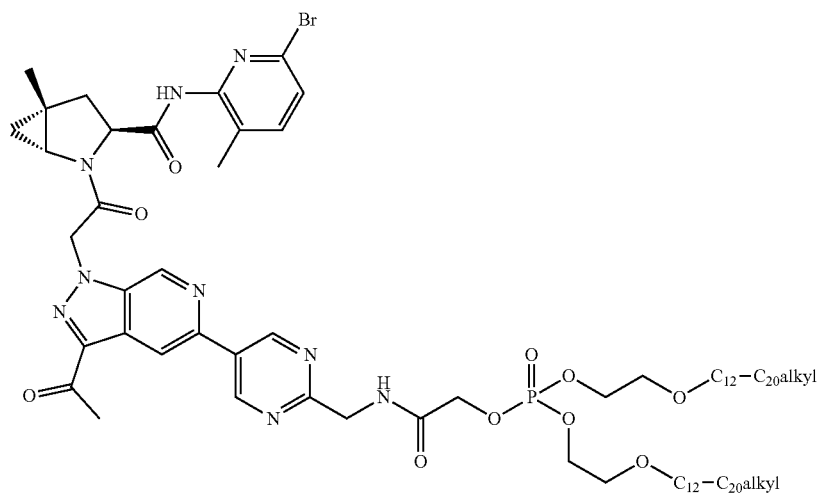
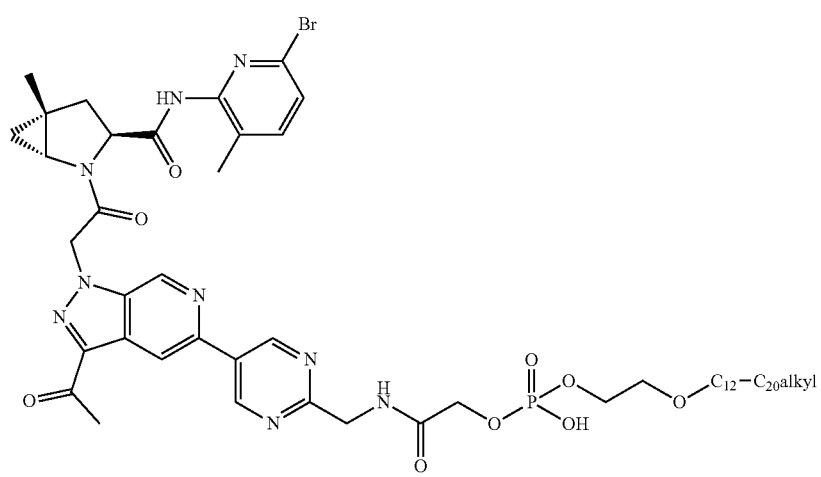
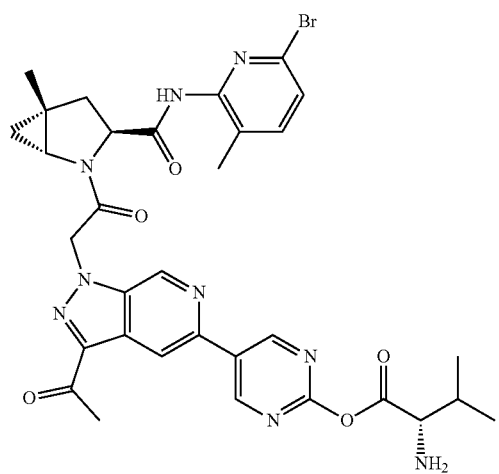 [SMILES: CC(=O)c1nn(CC(=O)N2[C@H](C(=O)Nc3nc(Br)ccc3C)C[C@@]3(C)C[C@@H]23)c2cnc(-c3cnc(OC(=O)[C@@H](N)C(C)C)nc3)cc12]

323 324
-continued
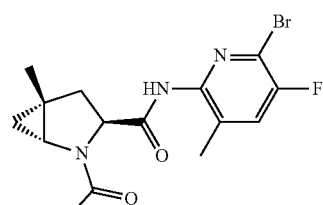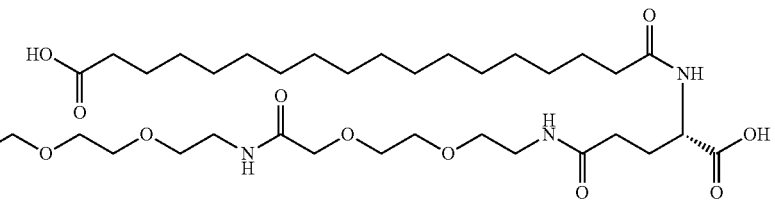
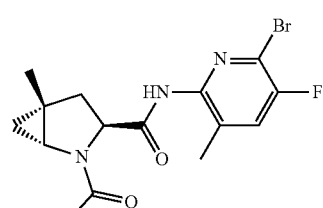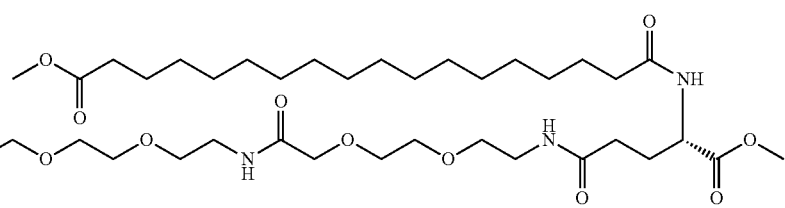
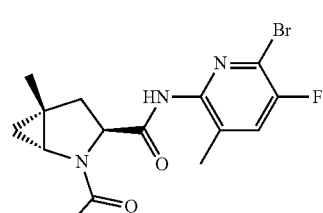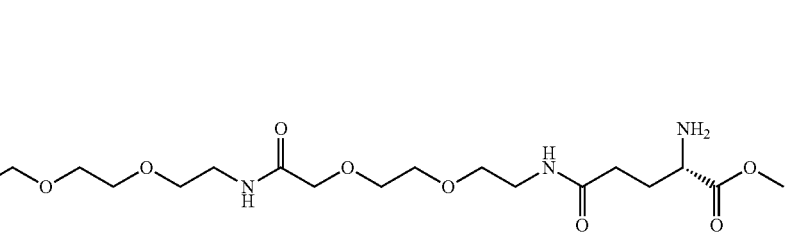
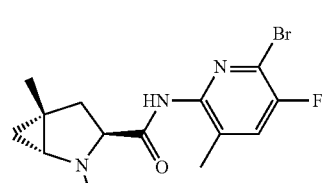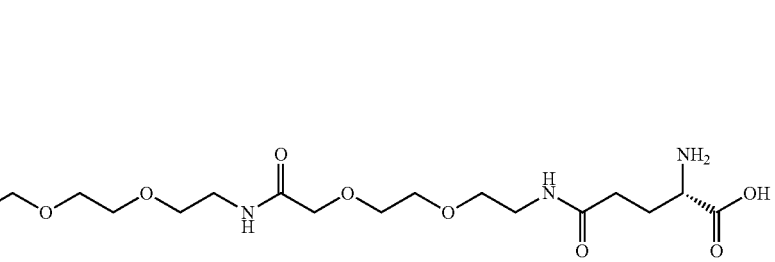

-continued
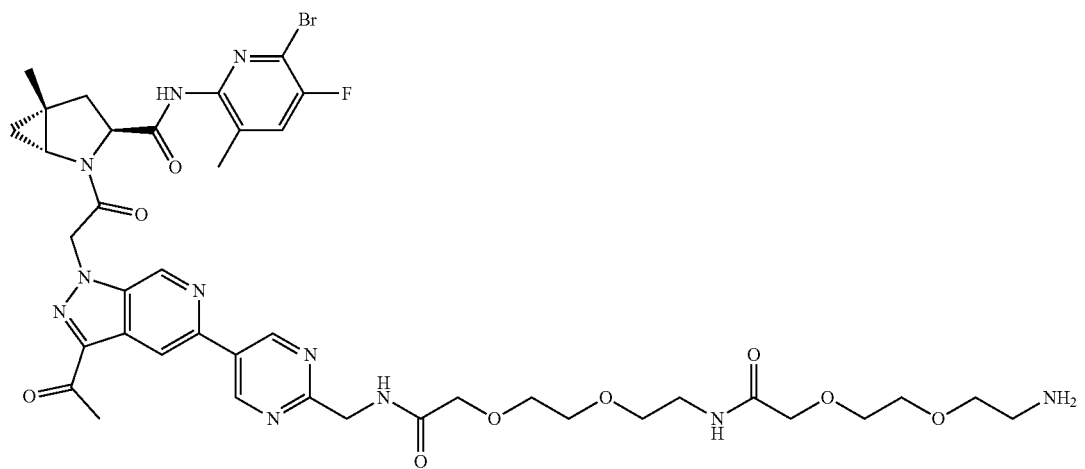
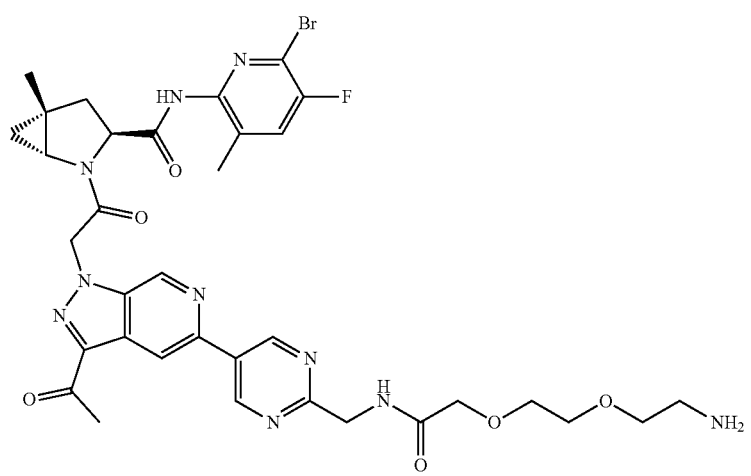
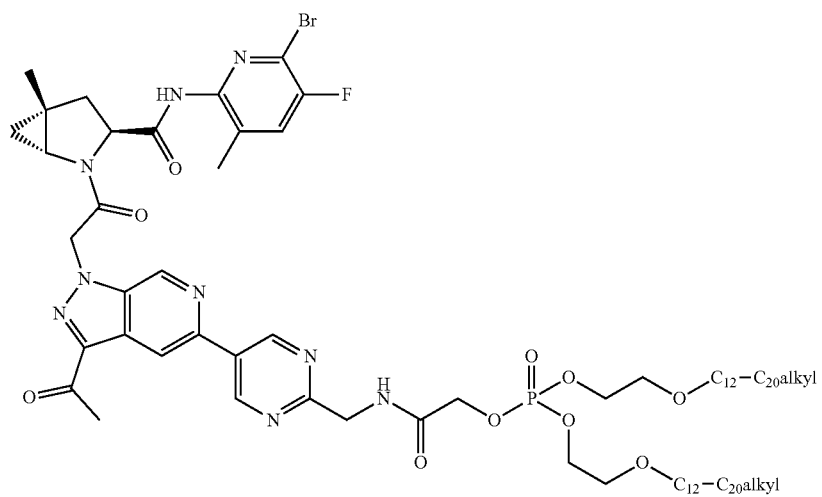

327
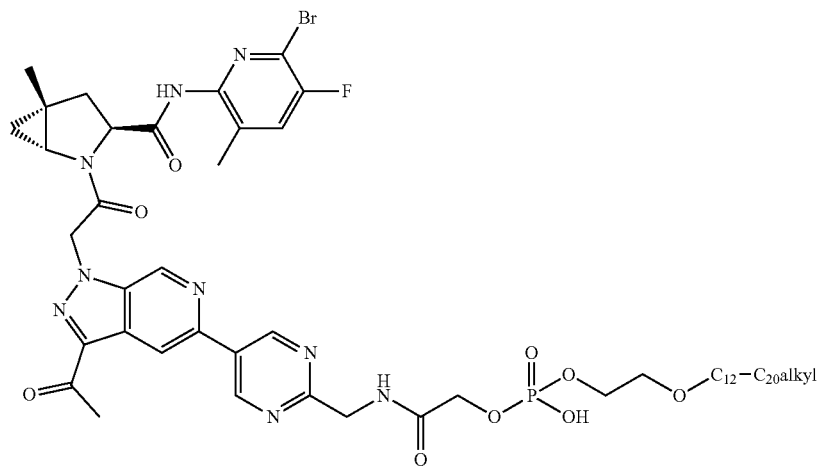
-continued
328
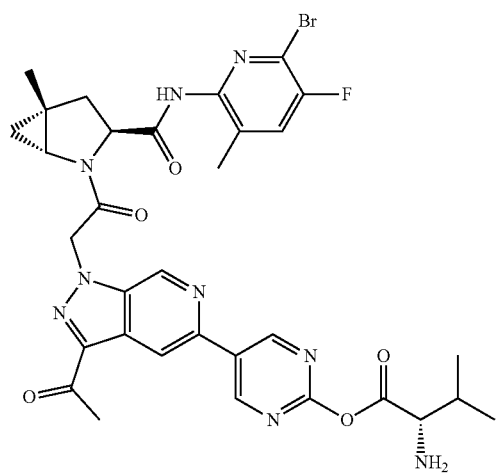 [SMILES: CC(=O)c1nn(CC(=O)N2[C@H](C(=O)Nc3nc(Br)c(F)cc3C)C[C@@]3(C)C[C@@H]23)c2cnc(-c3cnc(OC(=O)[C@@H](N)C(C)C)nc3)cc12]
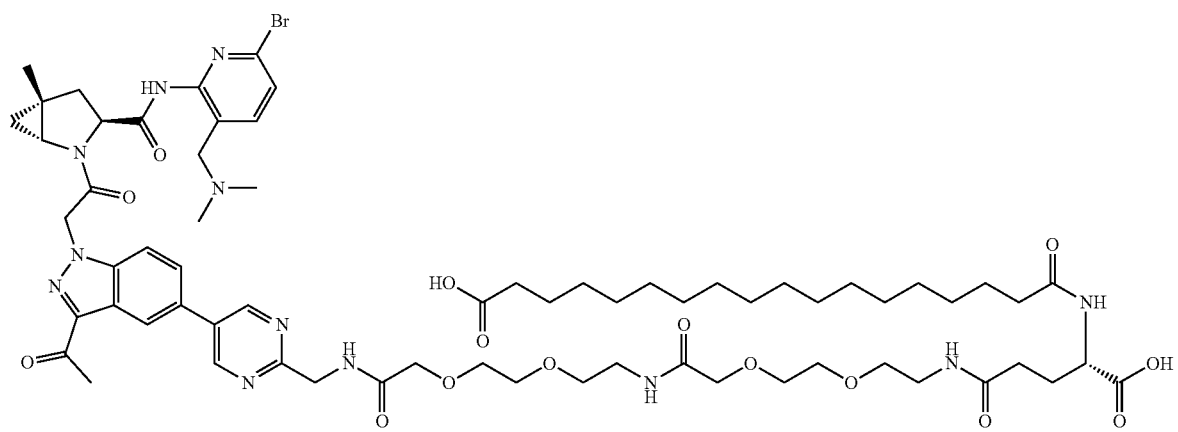

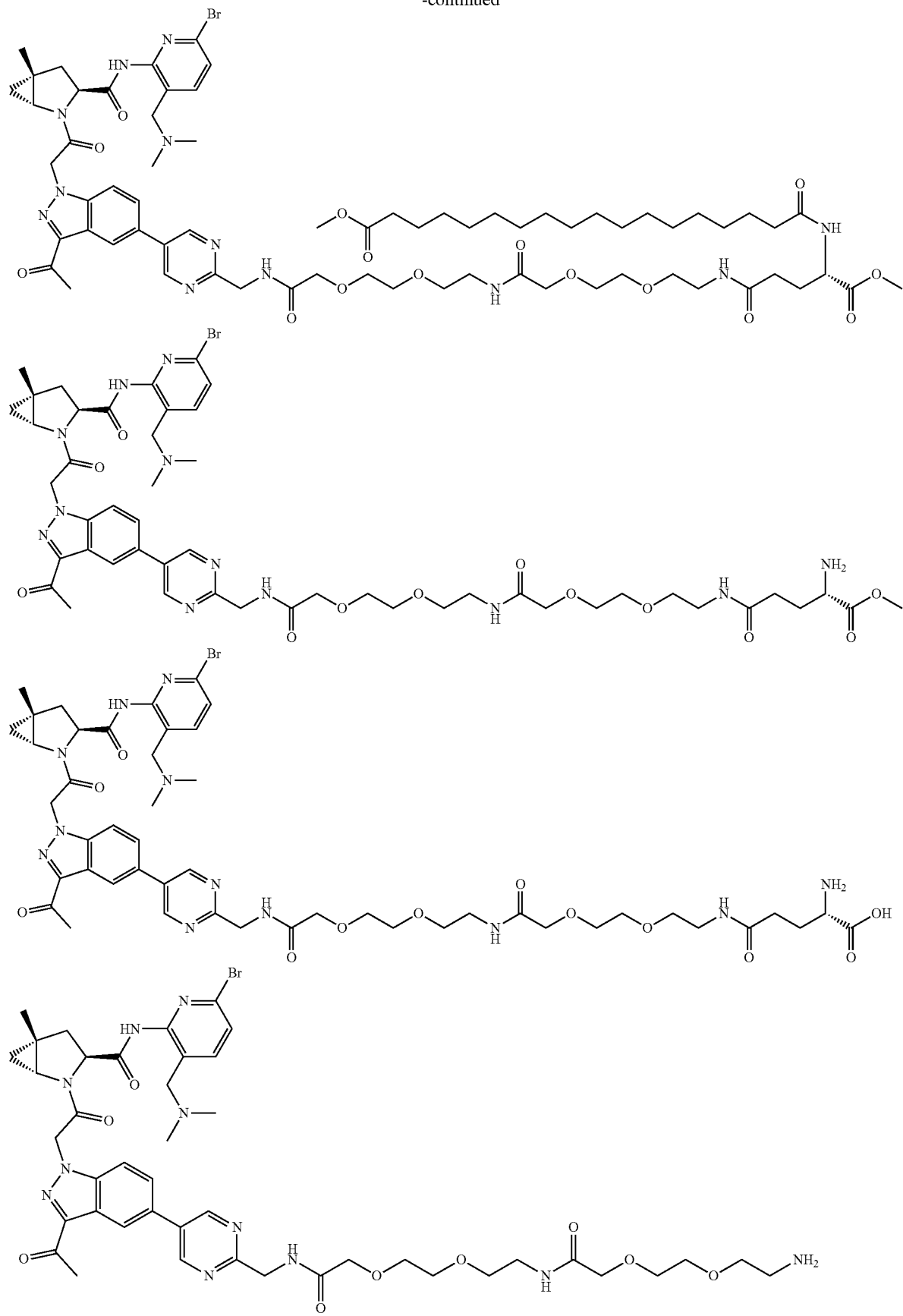

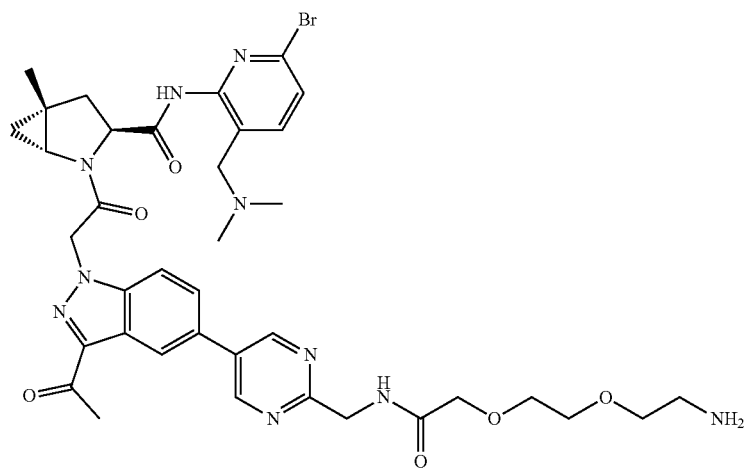
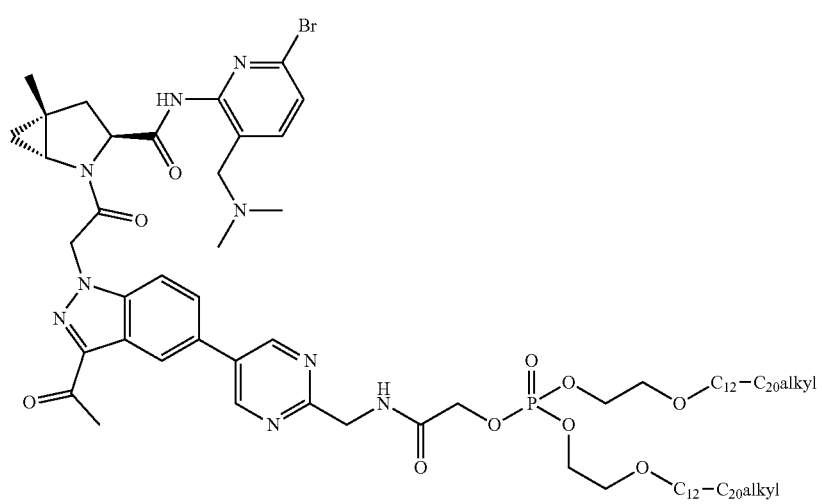
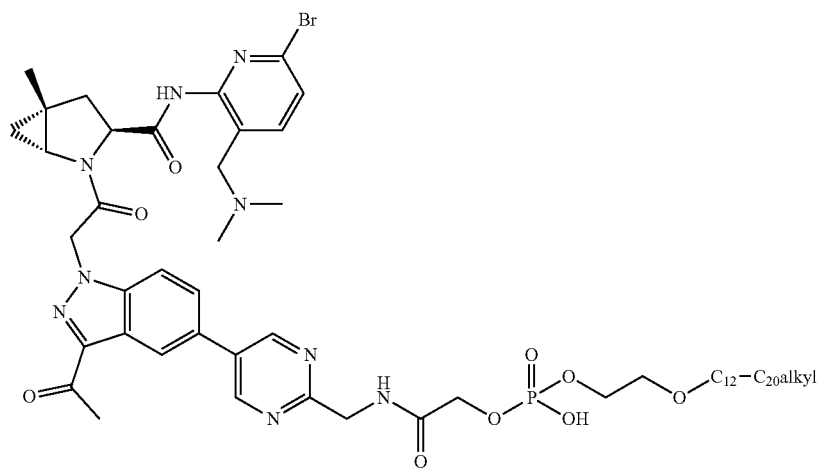

333 334
-continued
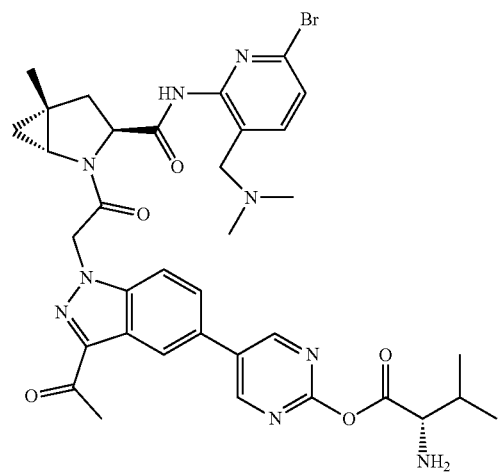
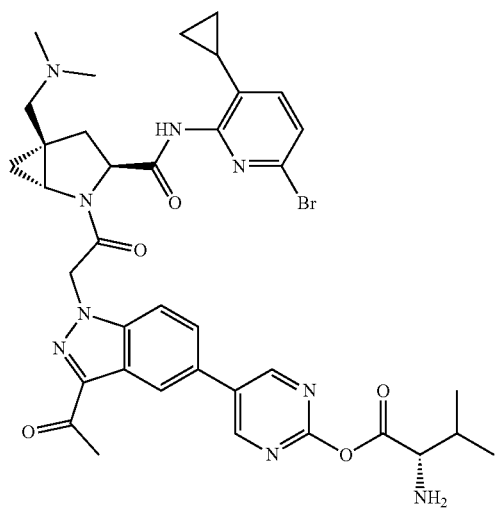
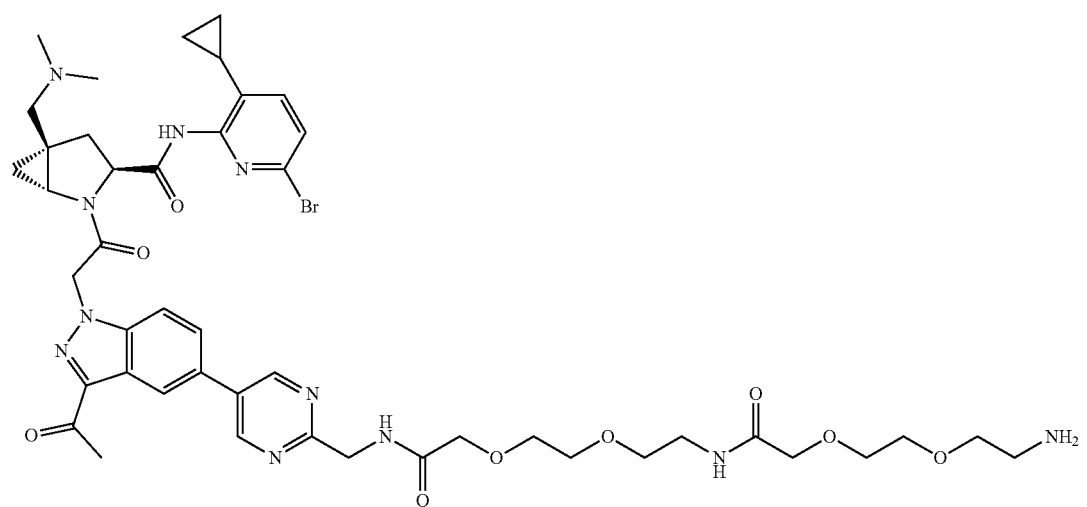
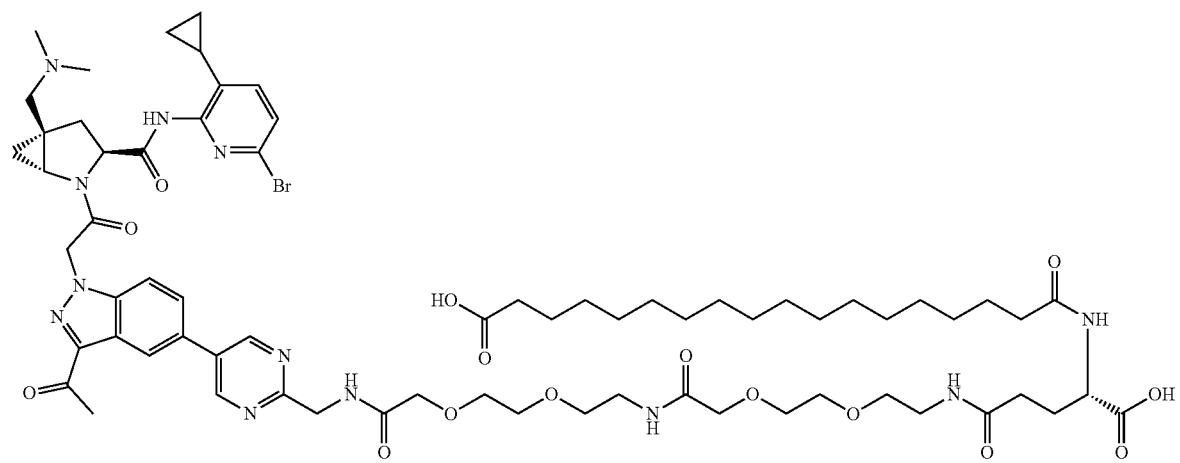

335
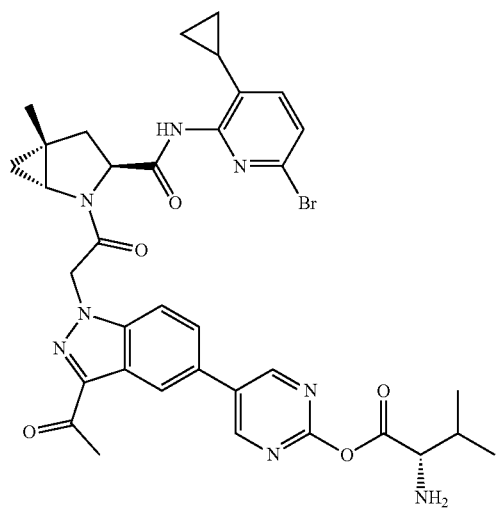
336
-continued
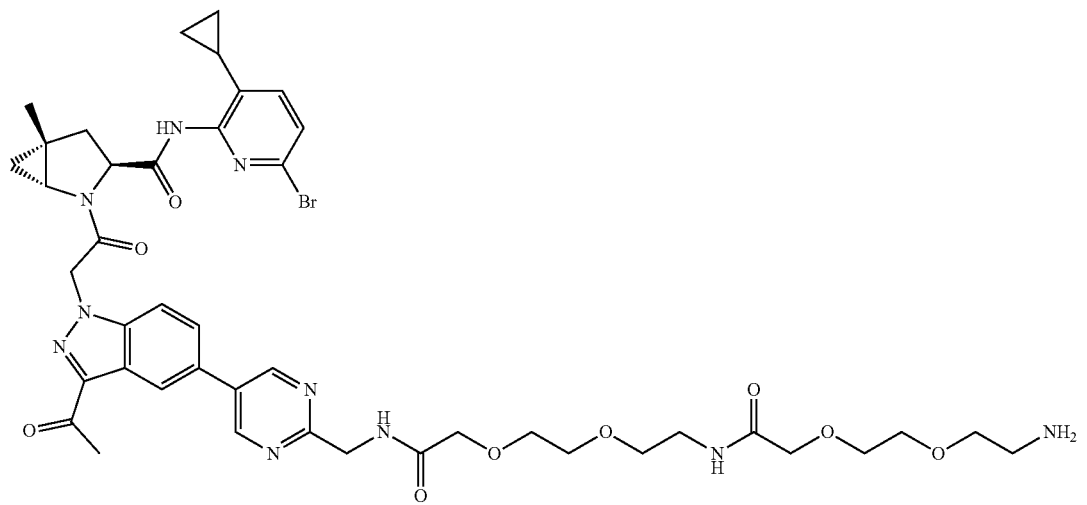
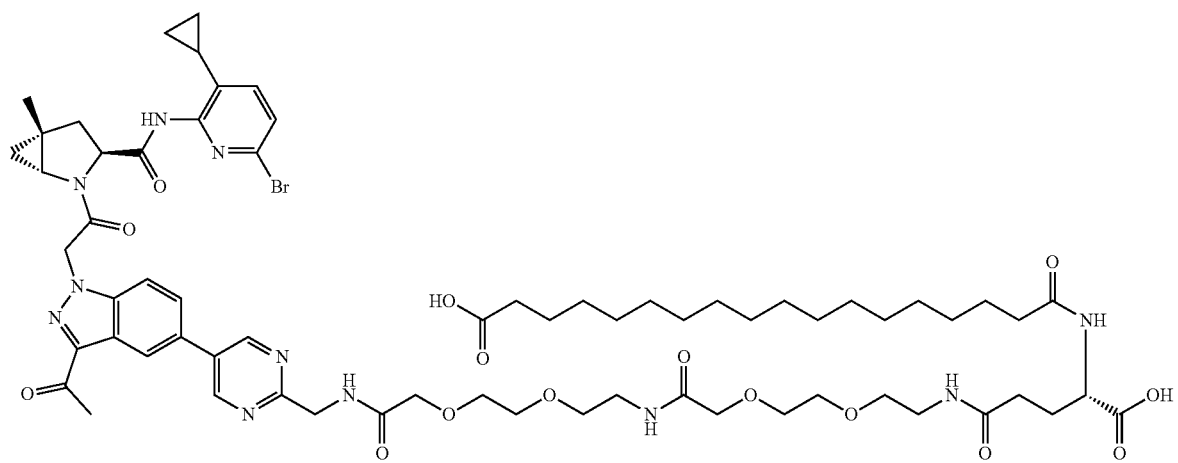

-continued
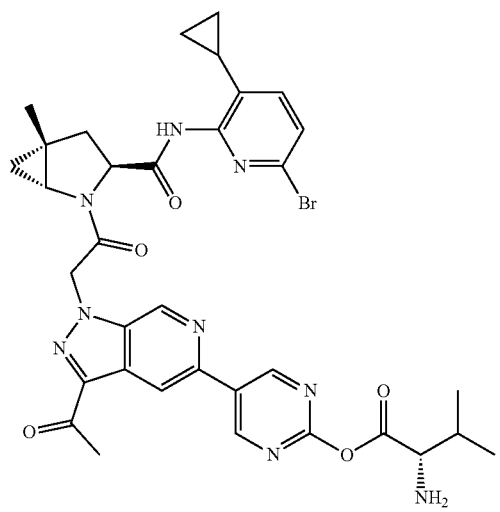
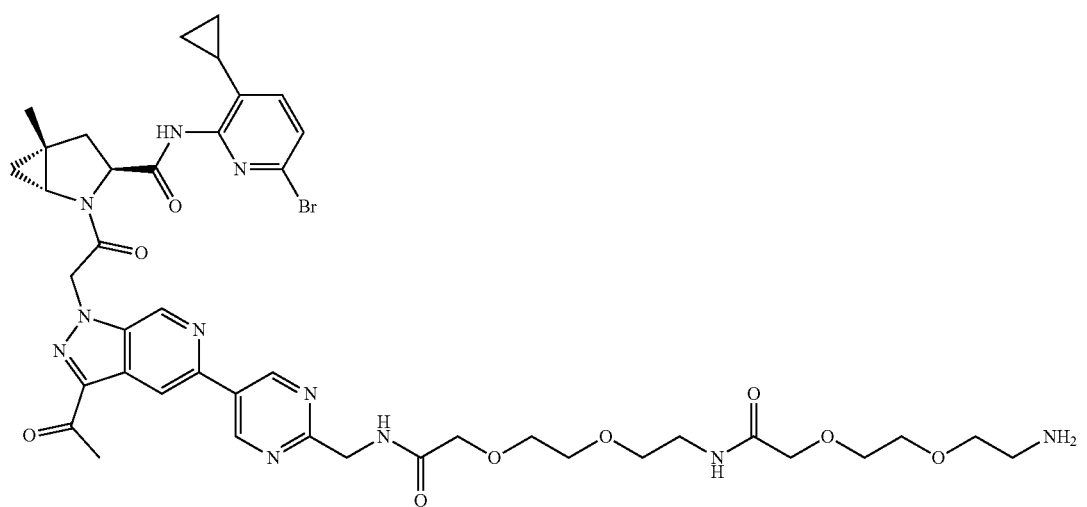
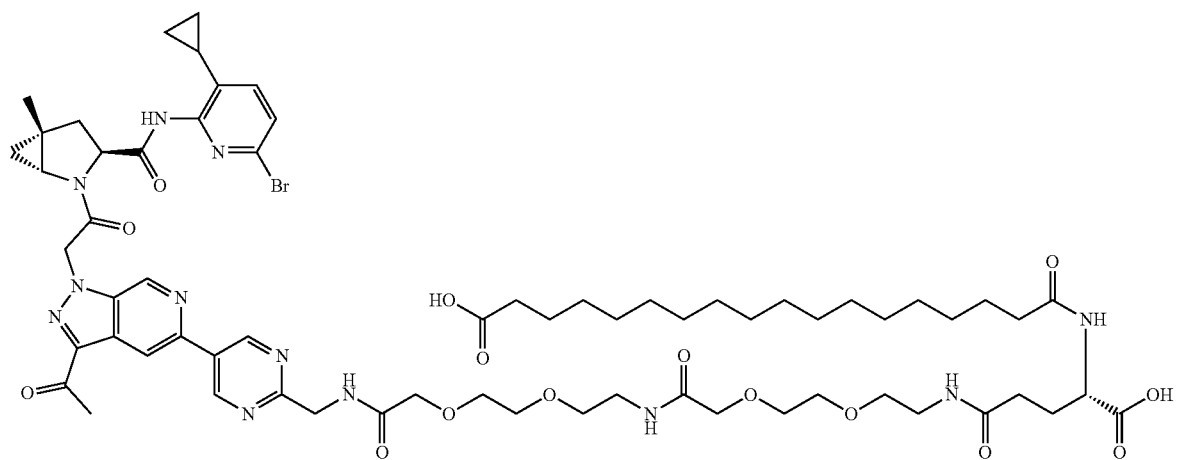

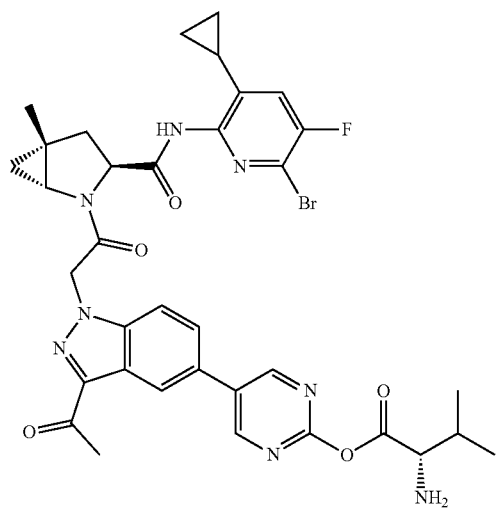
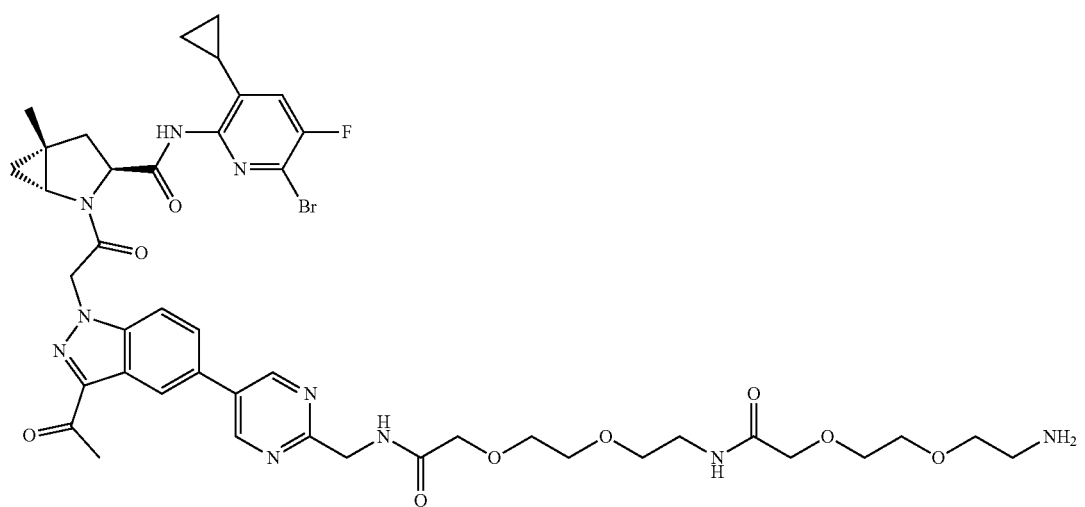
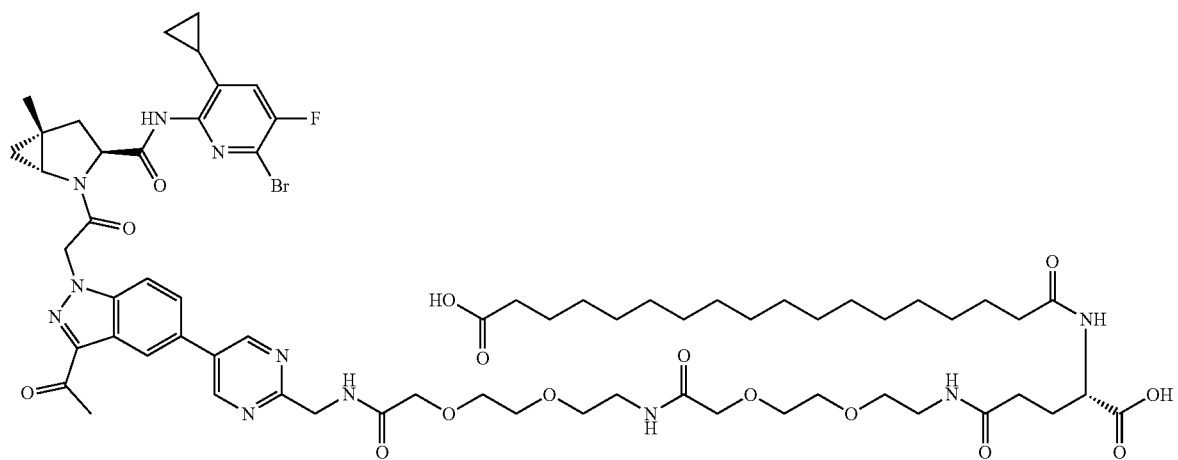

-continued
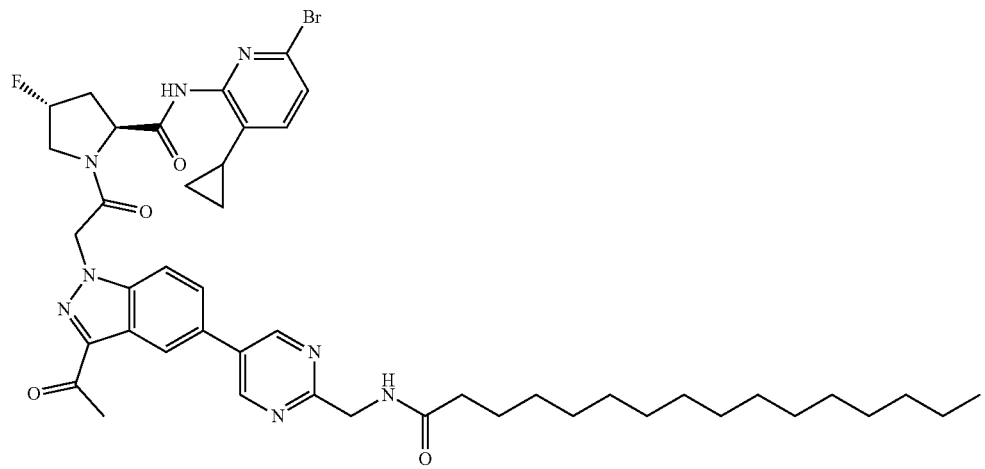
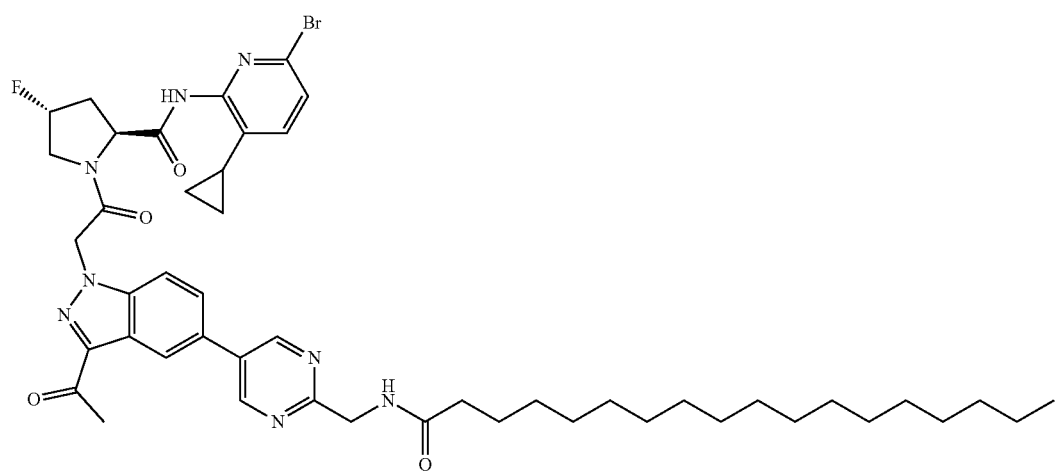
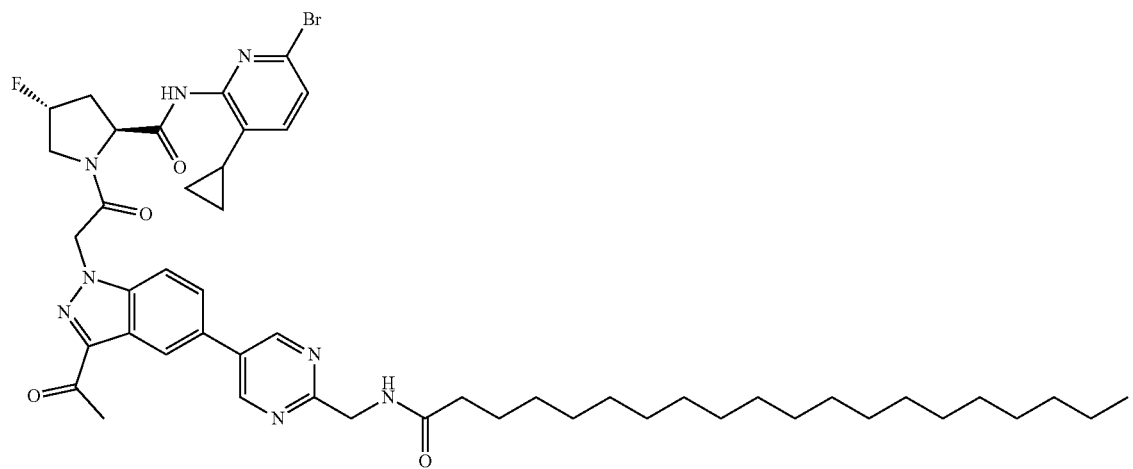

Non-limiting examples of compounds of the present invention with a $R^{301}$ group include:
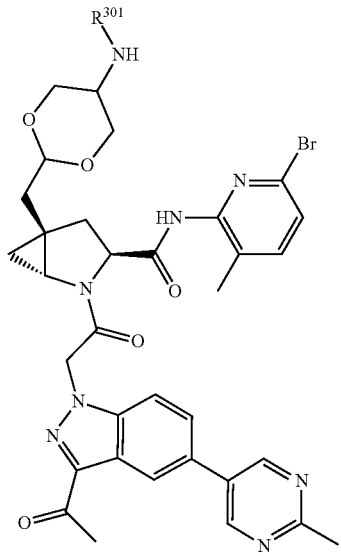
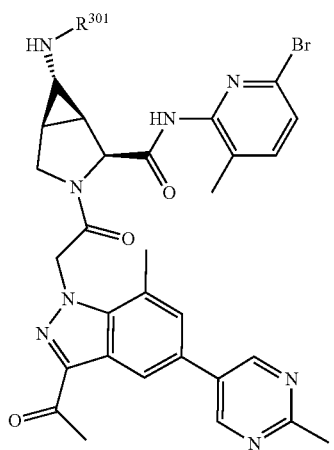
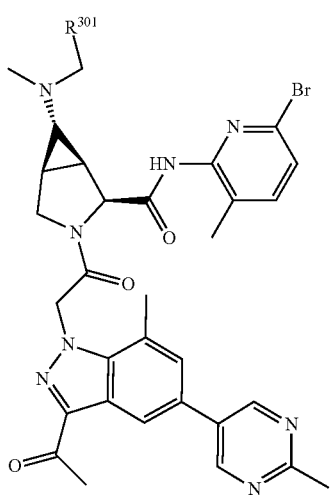
-continued
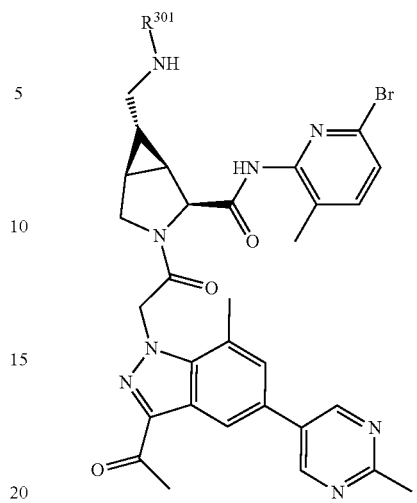
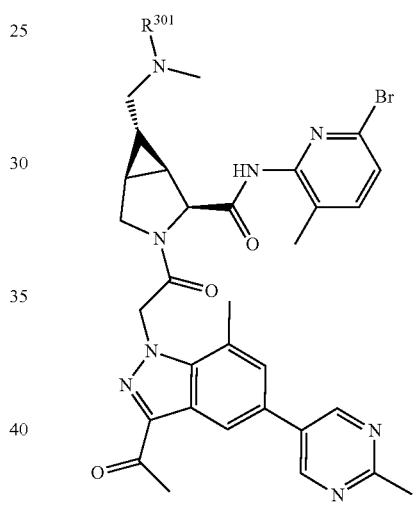
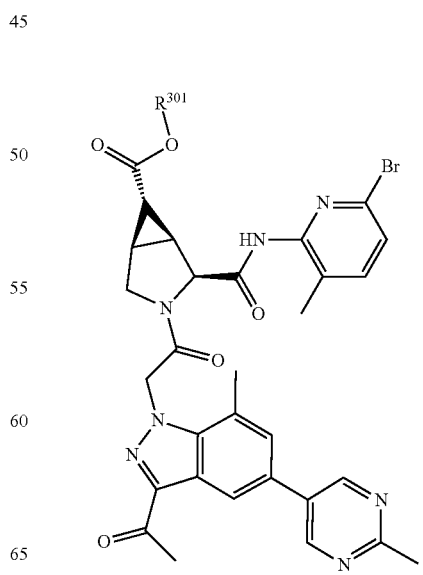

345
-continued
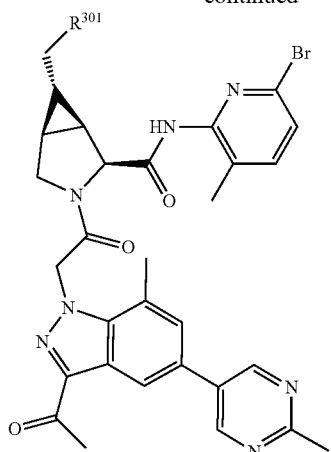
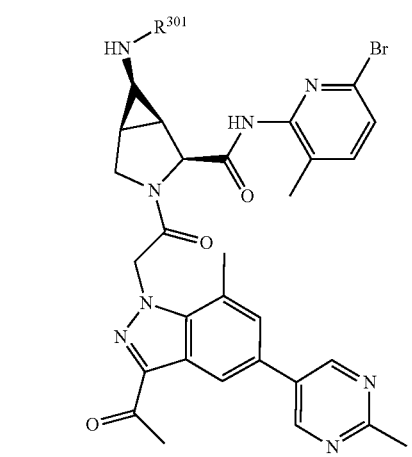
Non-limiting examples of compounds of the present invention with a R³⁰¹ group include:
346
-continued
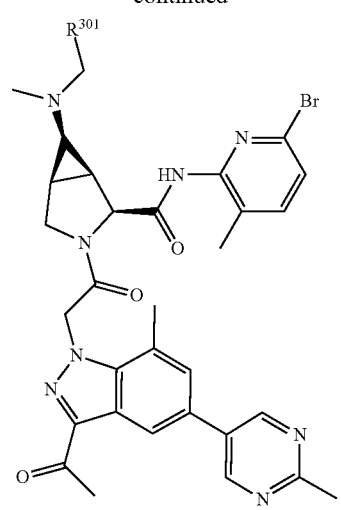
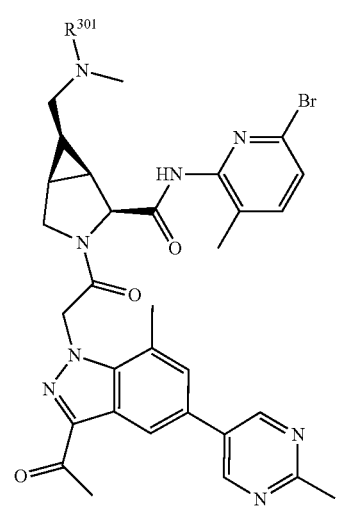

347
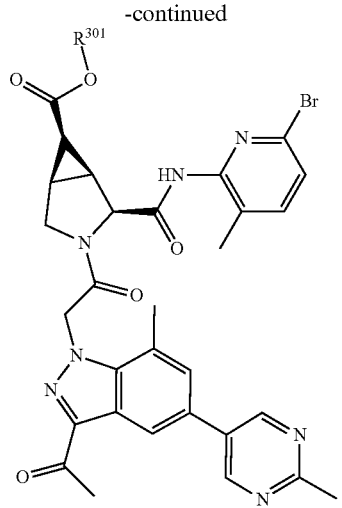
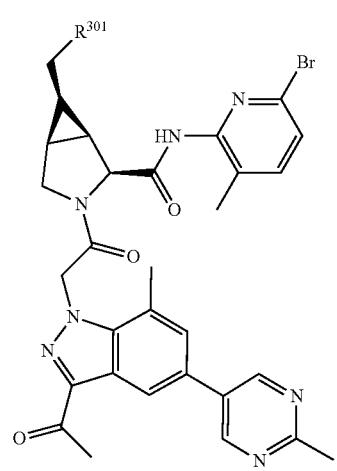
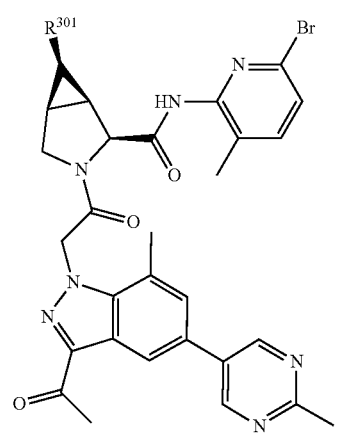
348
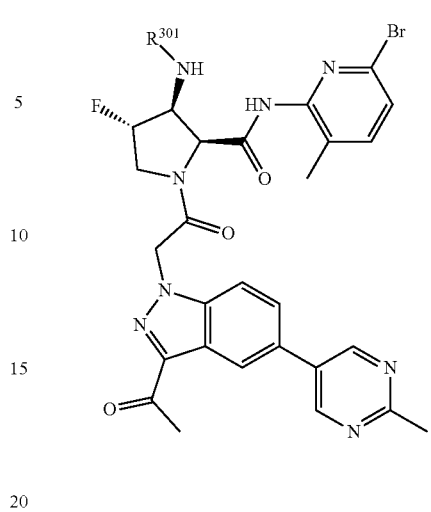
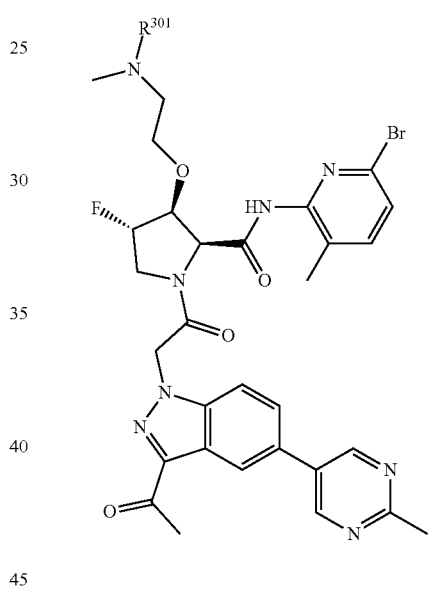
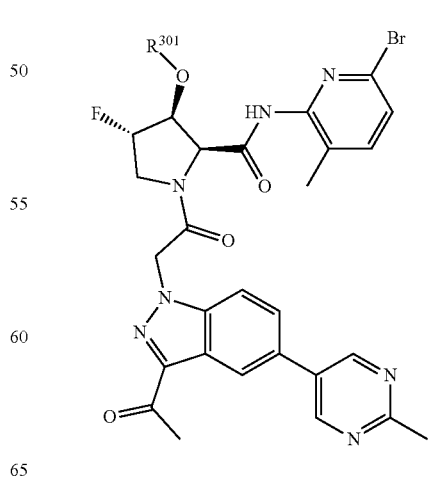
Non-limiting examples of compounds of the present invention with a $R^{301}$ group include:

349
-continued
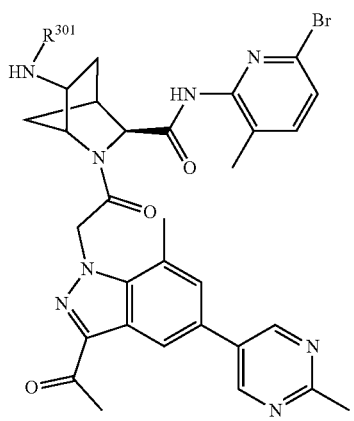
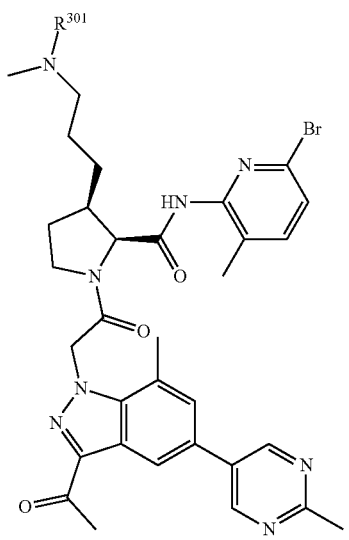
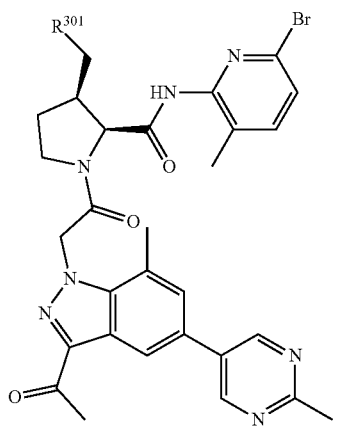
350
-continued
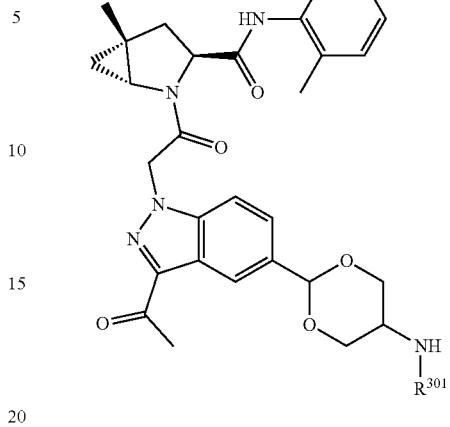
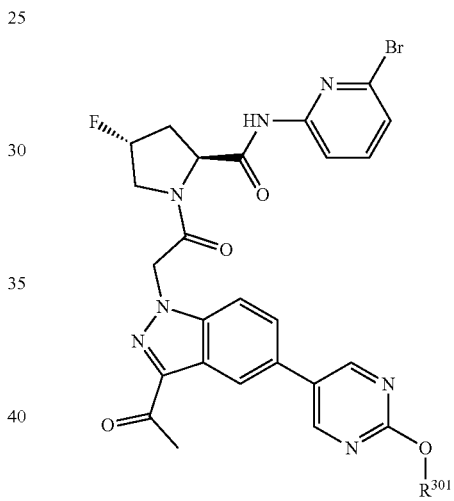
Non-limiting examples of compounds of the present invention with a $R^{301}$ group include:
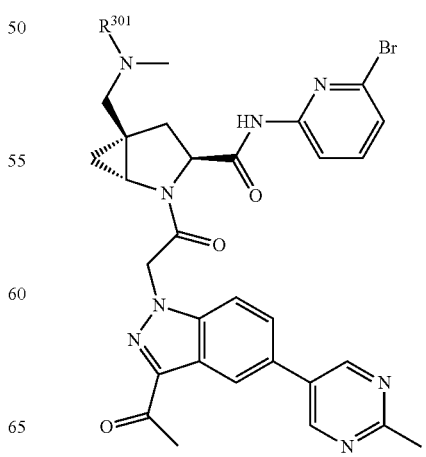

351
-continued
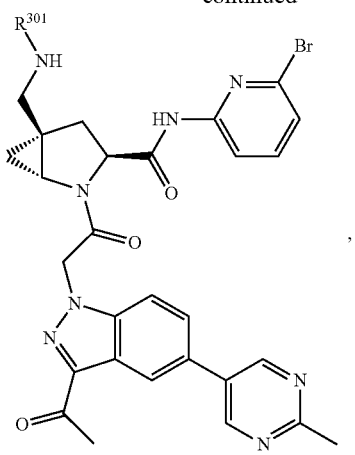
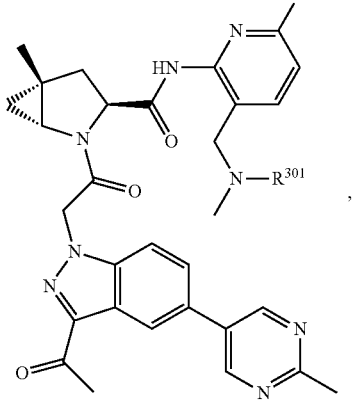
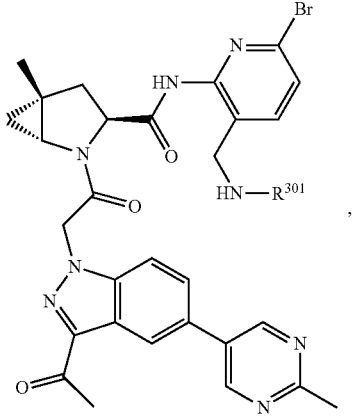
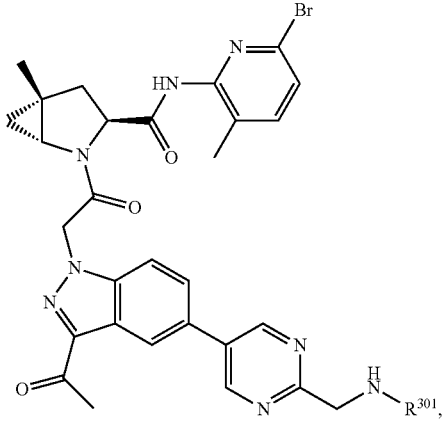
352
-continued
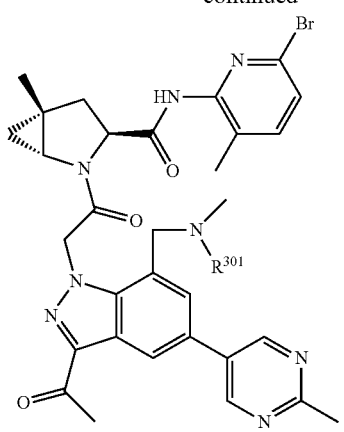
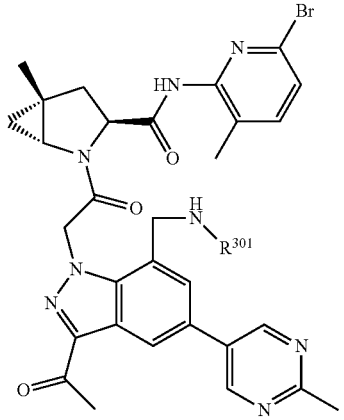
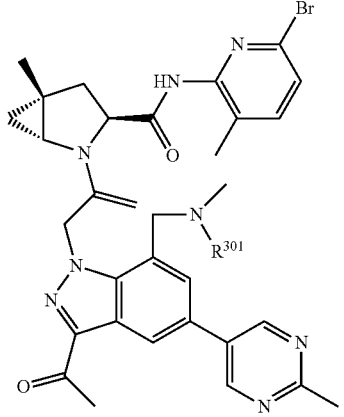
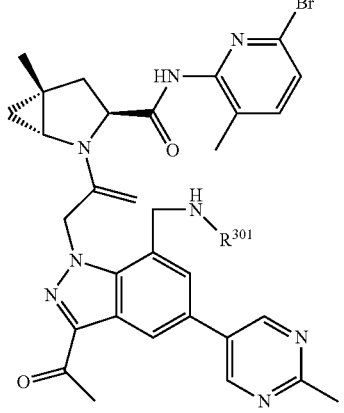
, and

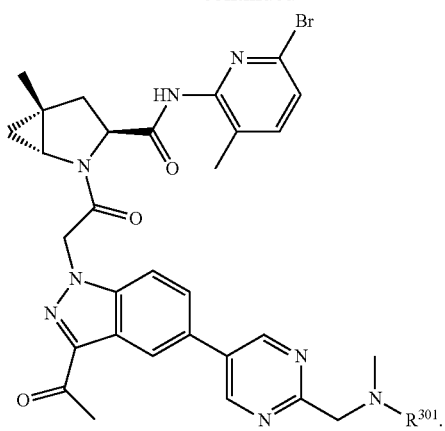
In one embodiment C is selected from:
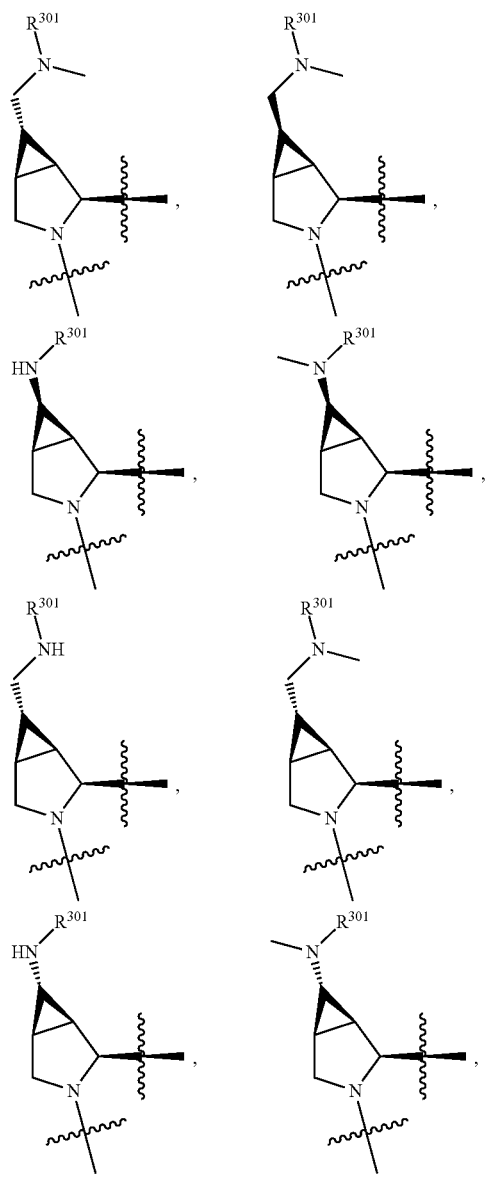
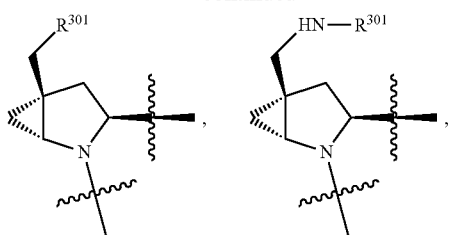
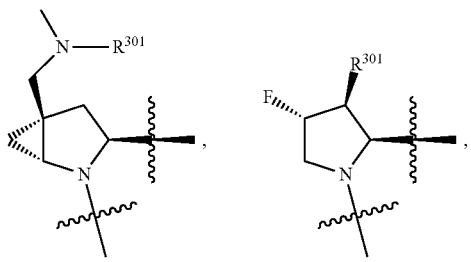
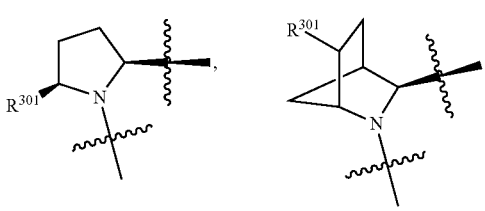
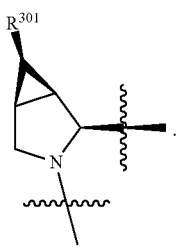
In one embodiment A is selected from:
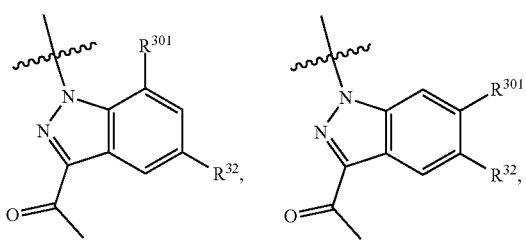
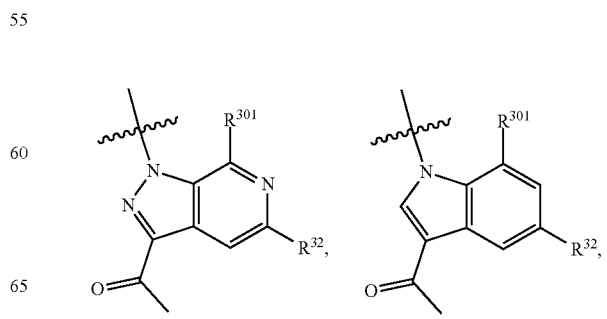

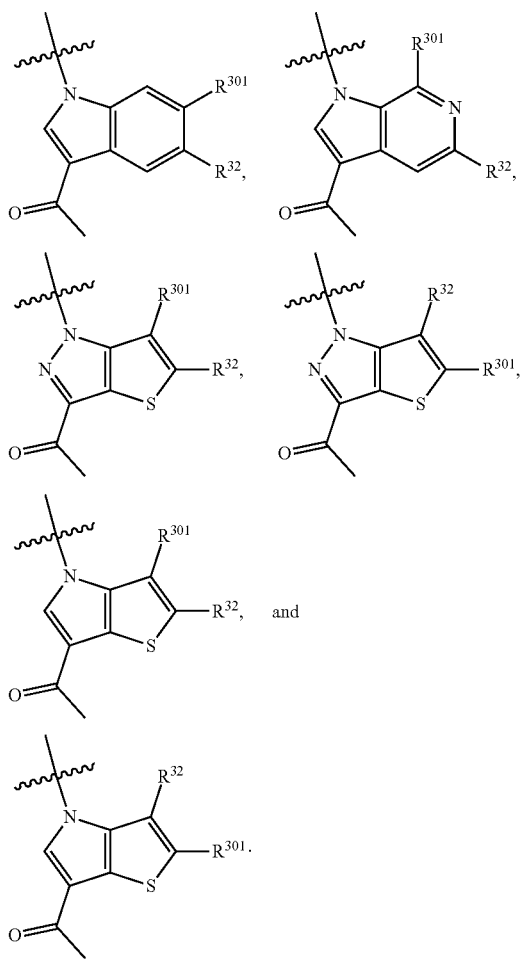

In one embodiment B is selected from:

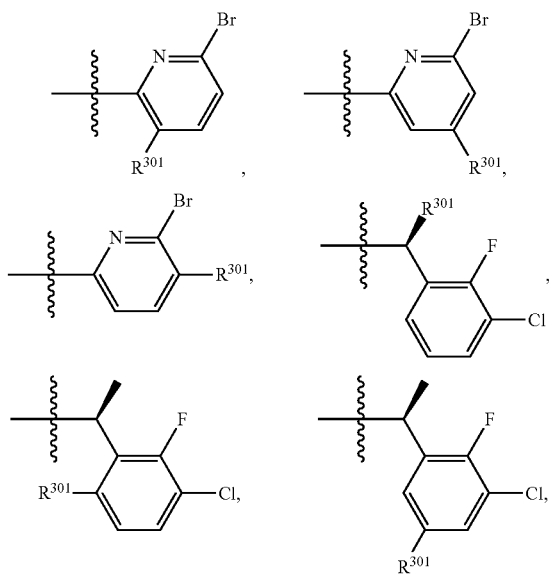

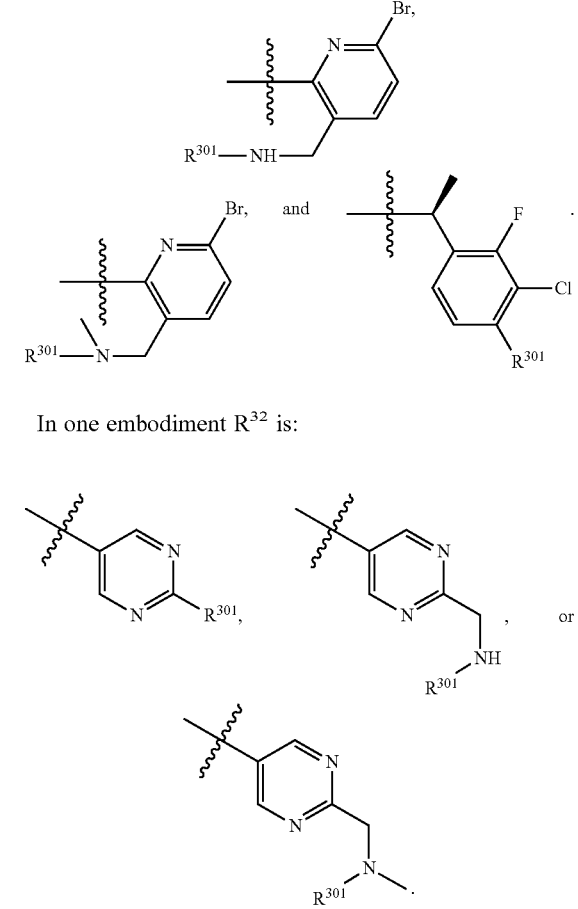

In one embodiment $R^{32}$ is:

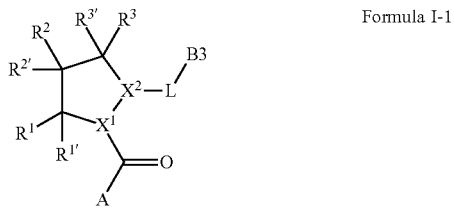

Additional Formulas

In one aspect, the disclosure includes compounds and salts of Formulas in Table 1 for any use and in any composition described in this application.

In some of the below Formulas for convenience and space purposes only, $R^{32}$ is illustrated as however each described or illustrated $R^{32}$ in this application is considered to be independently shown in each of these Formulas.

TABLE 1

Additional Exemplary Formulas within the Present Invention.

Formula I-1

TABLE 1-continued
Additional Exemplary Formulas within the Present Invention.
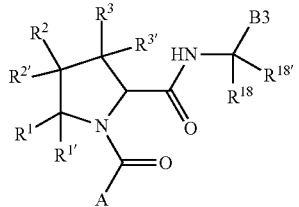 Formula I-2
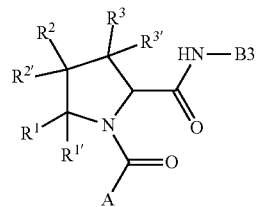 Formula I-3
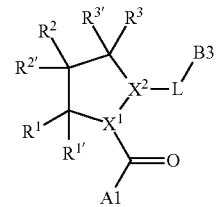 Formula I-4
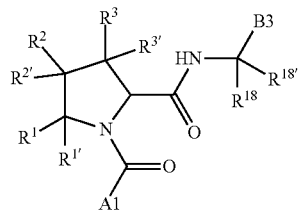 Formula I-5
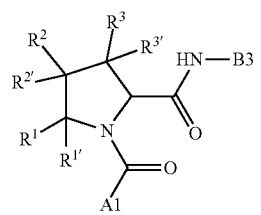 Formula I-6
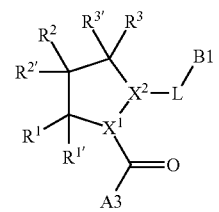 Formula I-7
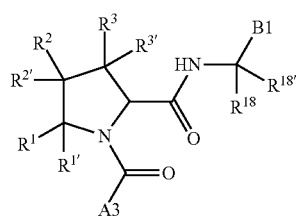 Formula I-8
TABLE 1-continued
Additional Exemplary Formulas within the Present Invention.
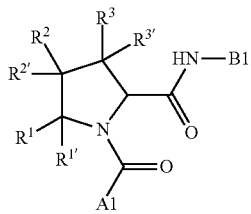 Formula I-9
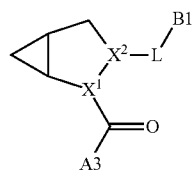 Formula I-10
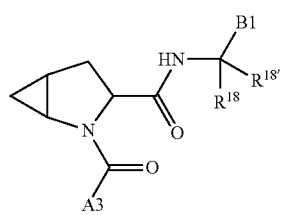 Formula I-11
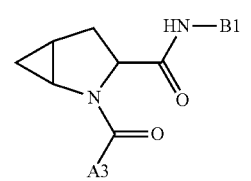 Formula I-12
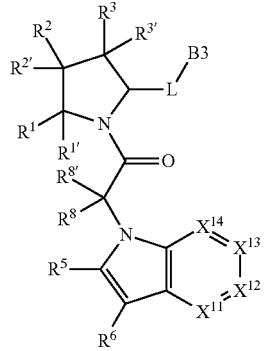 Formula I-13
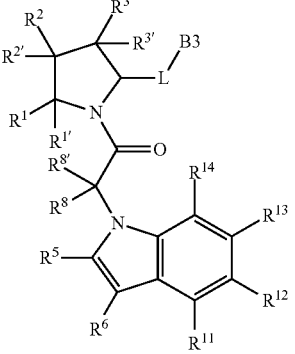 Formula I-14

TABLE 1-continued
Additional Exemplary Formulas within the Present Invention.
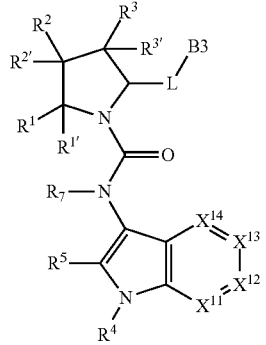
Formula I-15
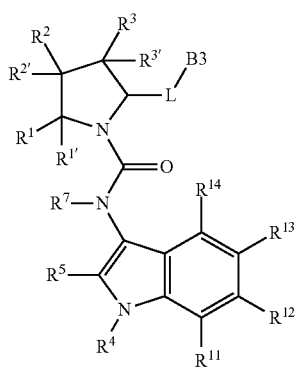
Formula I-16
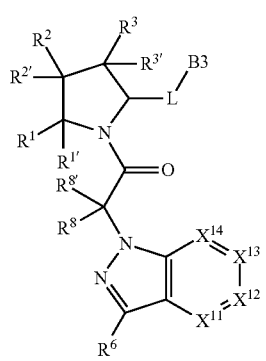
Formula I-17
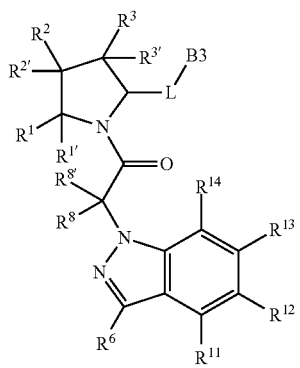
Formula I-18
TABLE 1-continued
Additional Exemplary Formulas within the Present Invention.
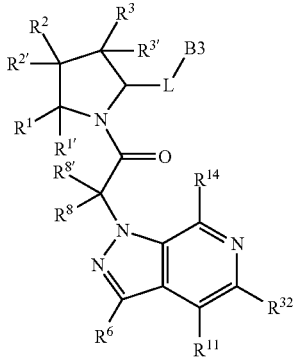
Formula I-19
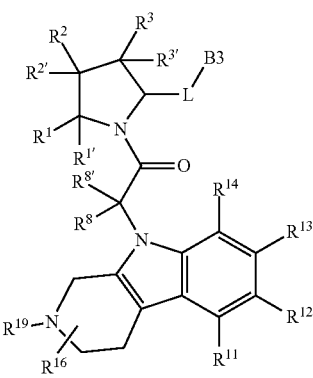
Formula I-20
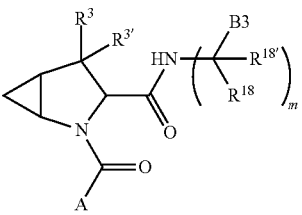
Formula I-21
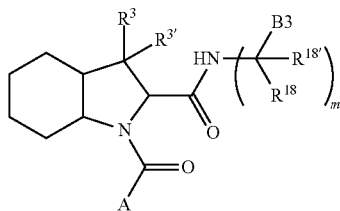
Formula I-22
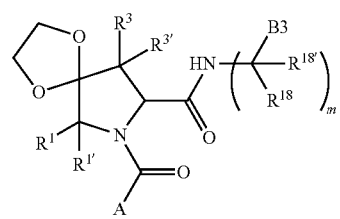
Formula I-23

TABLE 1-continued
Additional Exemplary Formulas within the Present Invention.
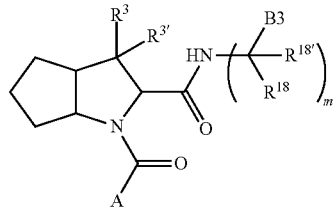
Formula I-24
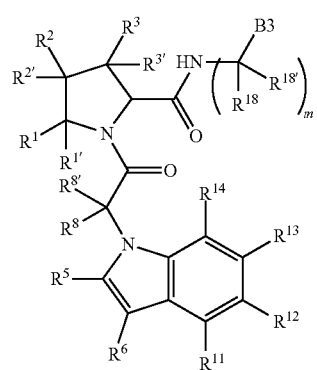
Formula I-25
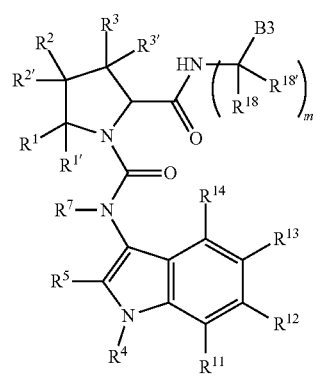
Formula I-26
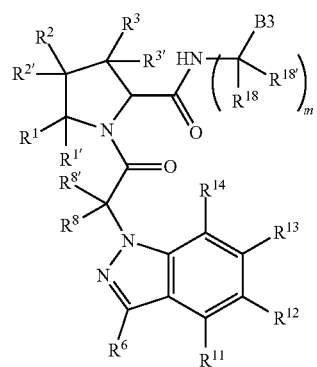
Formula I-27
TABLE 1-continued
Additional Exemplary Formulas within the Present Invention.
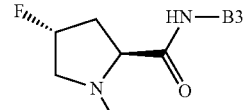
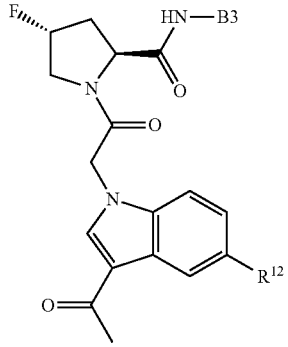
Formula I-28
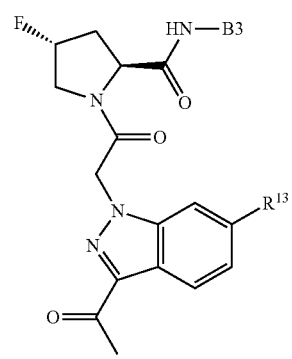
Formula I-29
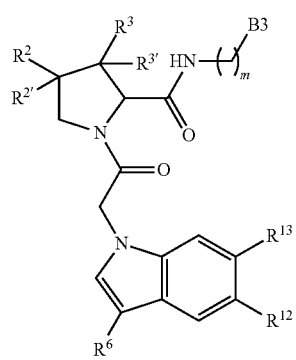
Formula I-30
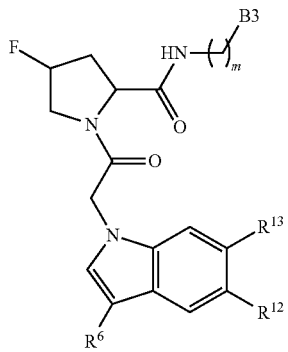
Formula I-31

TABLE 1-continued
Additional Exemplary Formulas within the Present Invention.
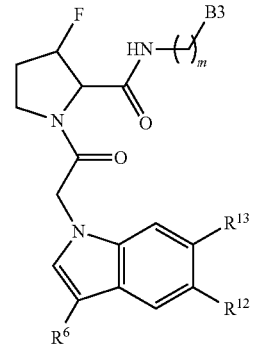 Formula I-32
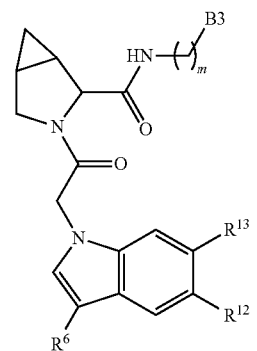 Formula I-33
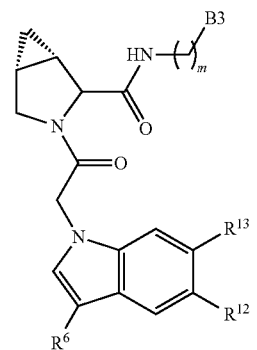 Formula I-34
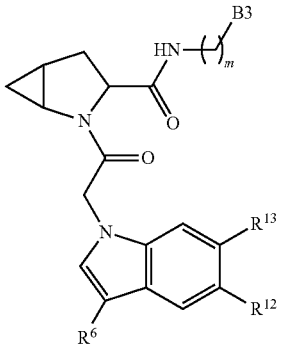 Formula I-35
TABLE 1-continued
Additional Exemplary Formulas within the Present Invention.
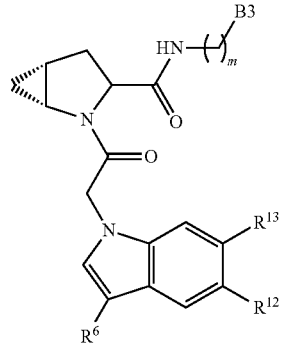 Formula I-36
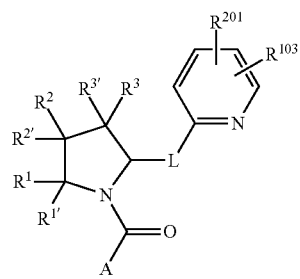 Formula I-37
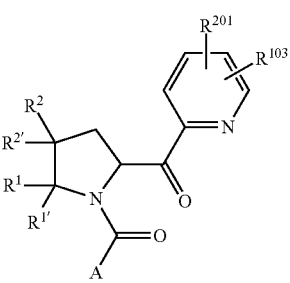 Formula I-38
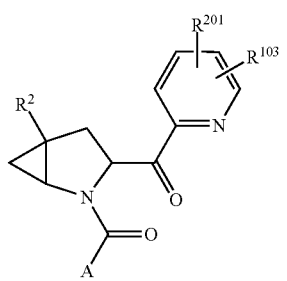 Formula I-39
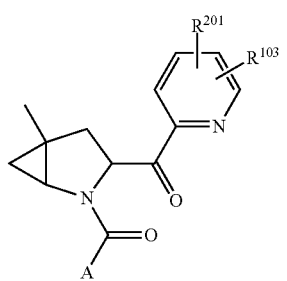 Formula I-40

TABLE 1-continued
Additional Exemplary Formulas within the Present Invention.
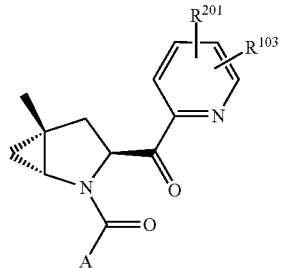 Formula I-41
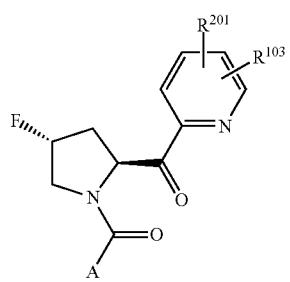 Formula I-42
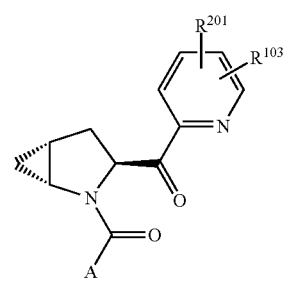 Formula I-43
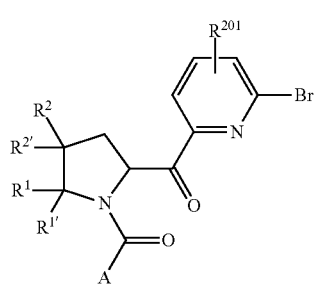 Formula I-44
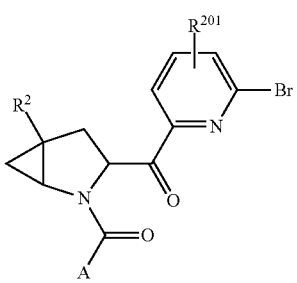 Formula I-45
TABLE 1-continued
Additional Exemplary Formulas within the Present Invention.
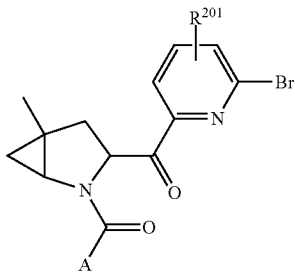 Formula I-46
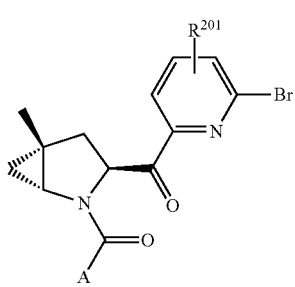 Formula I-47
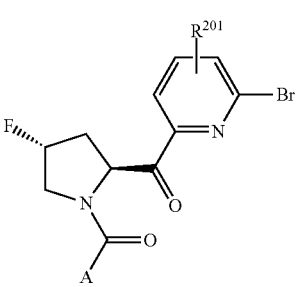 Formula I-48
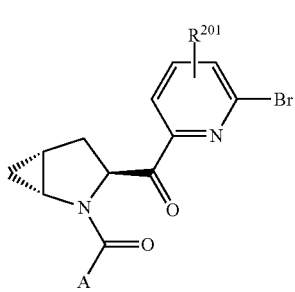 Formula I-49
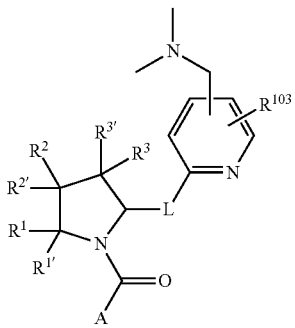 Formula I-50

TABLE 1-continued
Additional Exemplary Formulas within the Present Invention.
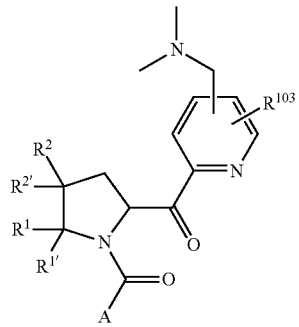
Formula I-51
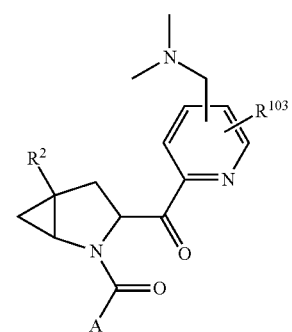
Formula I-52
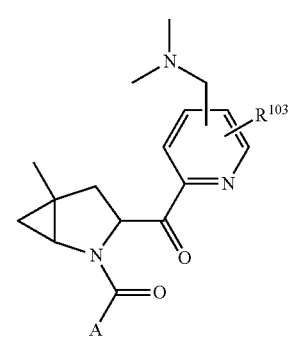
Formula I-53
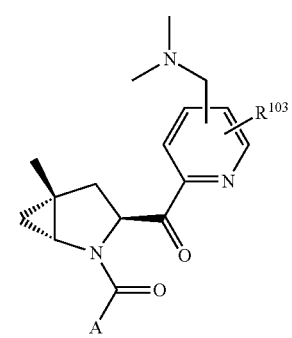
Formula I-54
TABLE 1-continued
Additional Exemplary Formulas within the Present Invention.
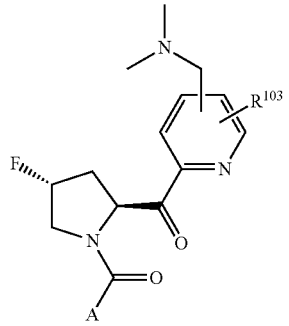
Formula I-55
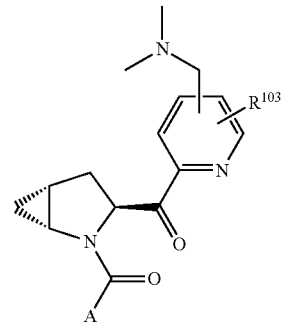
Formula I-56
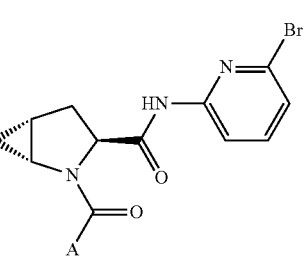
Formula I-57
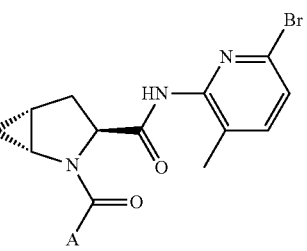
Formula I-58
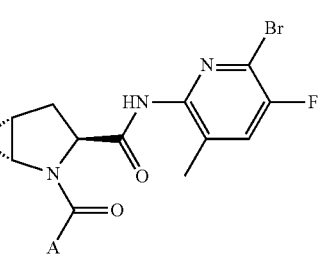
Formula I-59

TABLE 1-continued
Additional Exemplary Formulas within the Present Invention.
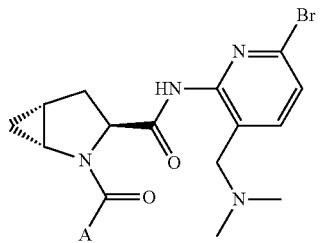 Formula I-60
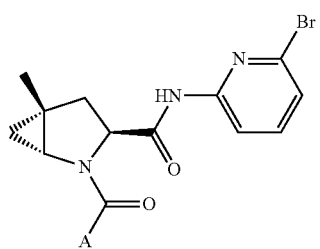 Formula I-61
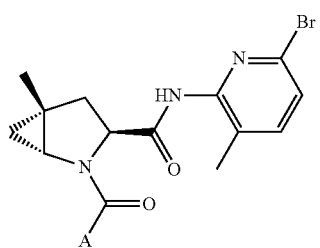 Formula I-62
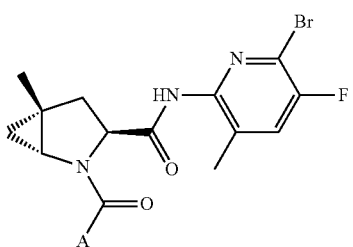 Formula I-63
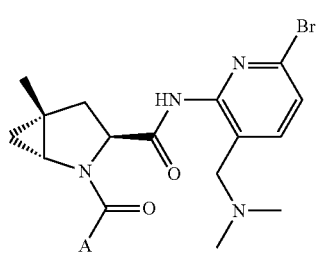 Formula I-64
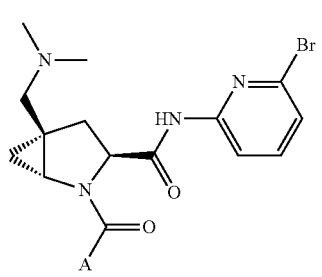 Formula I-65
TABLE 1-continued
Additional Exemplary Formulas within the Present Invention.
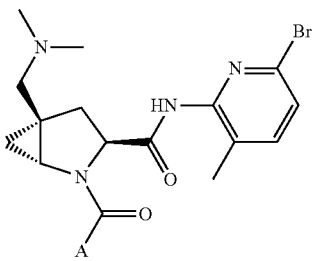 Formula I-66
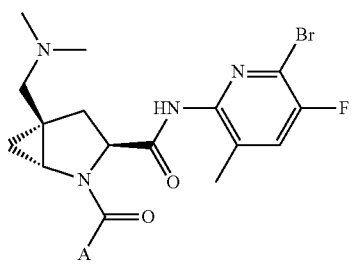 Formula I-67
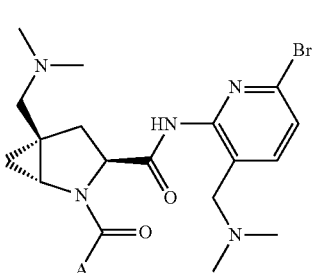 Formula I-68
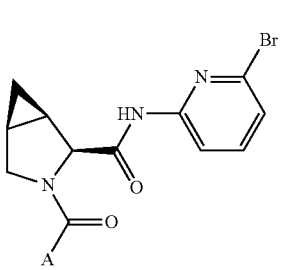 Formula I-69
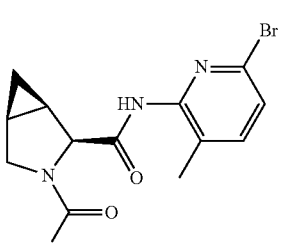 Formula I-70
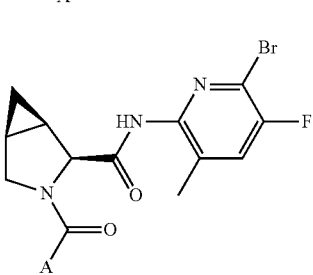 Formula I-71

TABLE 1-continued
Additional Exemplary Formulas within the Present Invention.
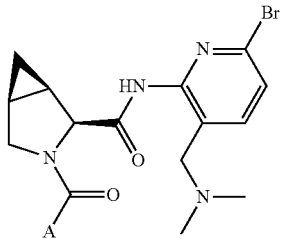
Formula I-72
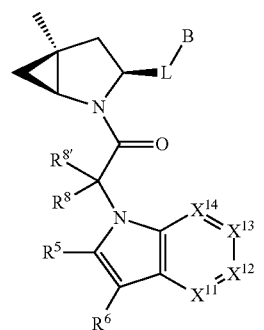
Formula I-73
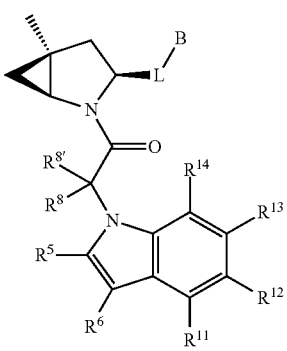
Formula I-74
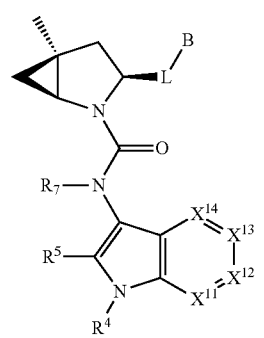
Formula I-75
TABLE 1-continued
Additional Exemplary Formulas within the Present Invention.
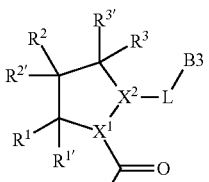
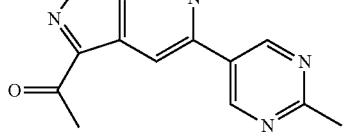
Formula I-76
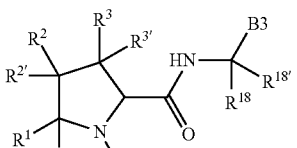
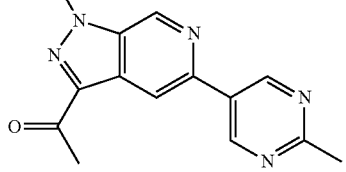
Formula I-77
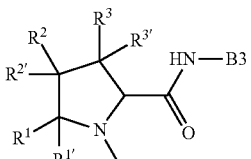
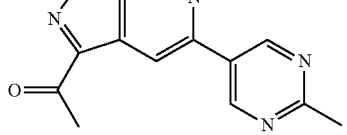
Formula I-78
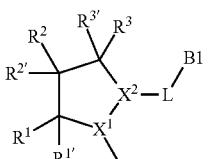
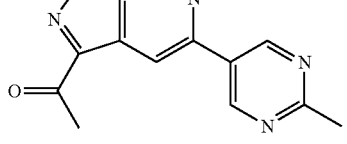
Formula I-79

TABLE 1-continued
Additional Exemplary Formulas within the Present Invention.
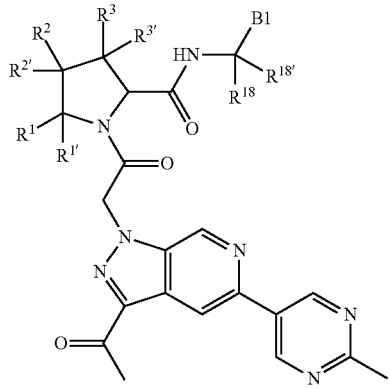
Formula I-80
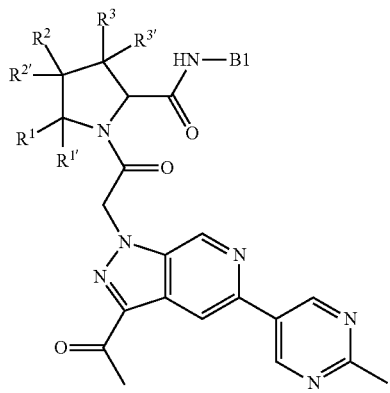
Formula I-81
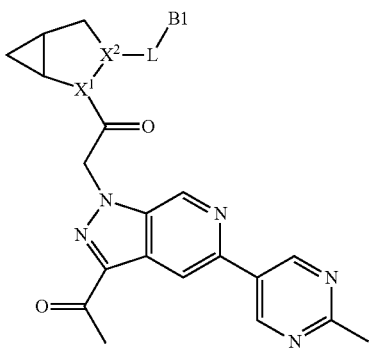
Formula I-82
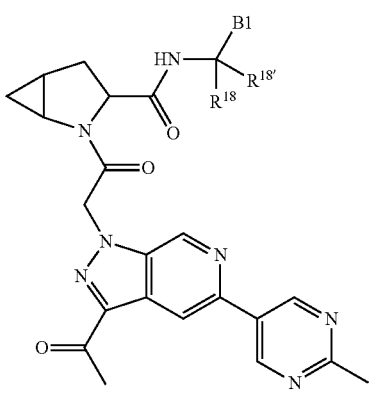
Formula I-83
TABLE 1-continued
Additional Exemplary Formulas within the Present Invention.
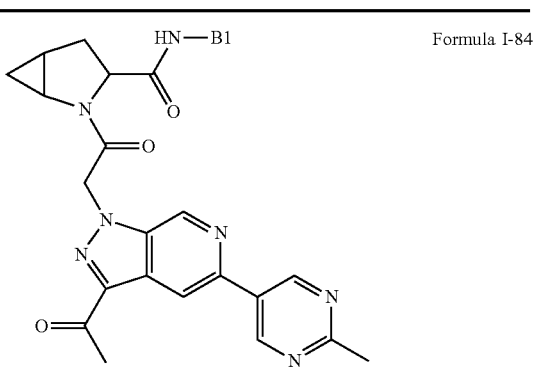
Formula I-84
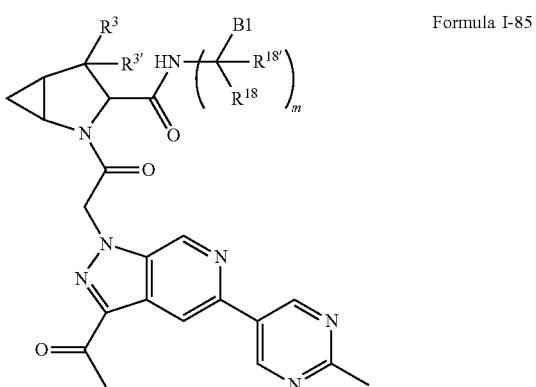
Formula I-85
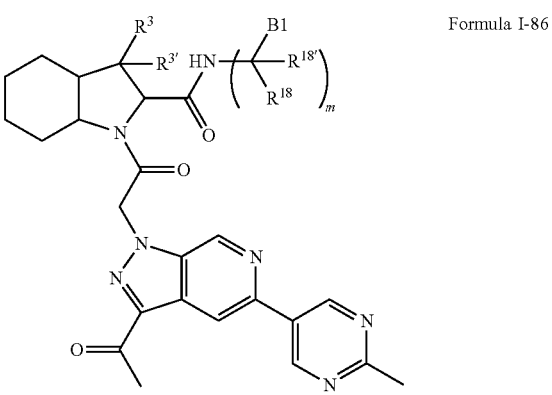
Formula I-86
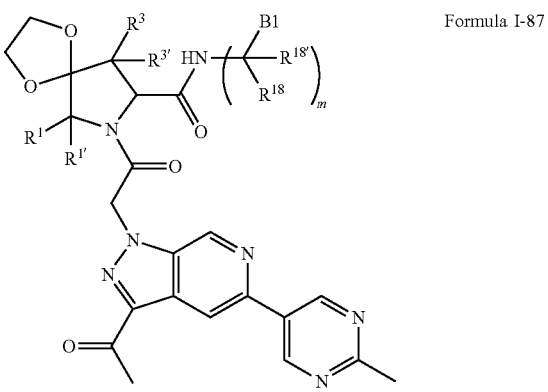
Formula I-87

TABLE 1-continued
Additional Exemplary Formulas within the Present Invention.
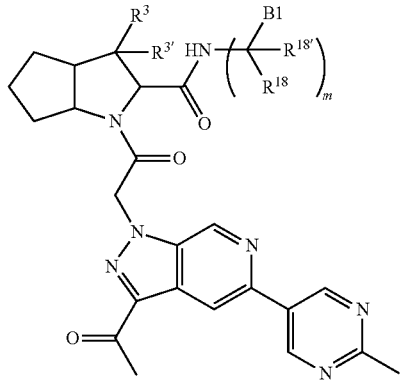
Formula I-88
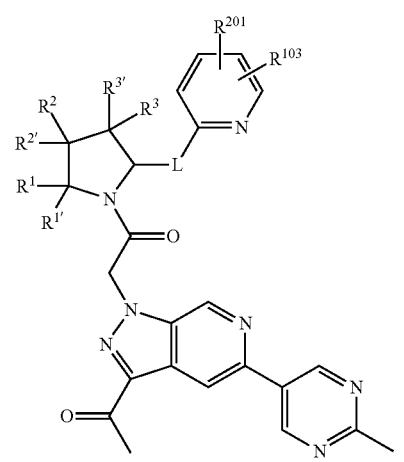
Formula I-89
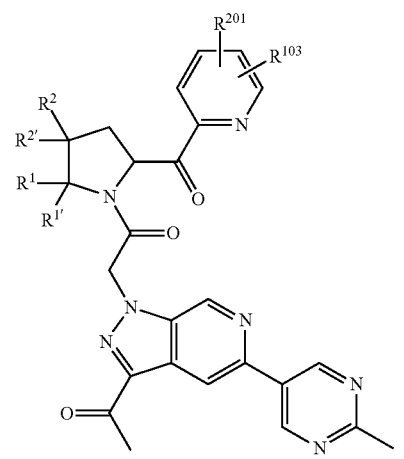
Formula I-90
TABLE 1-continued
Additional Exemplary Formulas within the Present Invention.
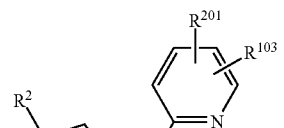
Formula I-91
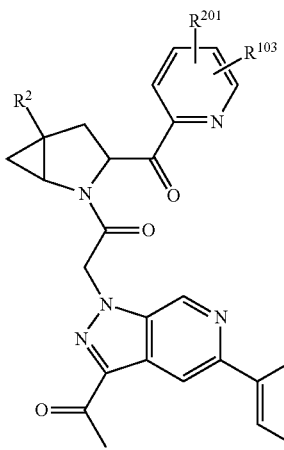
Formula I-92
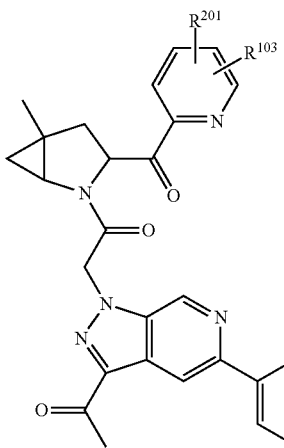
Formula I-93

TABLE 1-continued

Additional Exemplary Formulas within the Present Invention.

Formula I-94

Formula I-95

Formula I-96

TABLE 1-continued

Additional Exemplary Formulas within the Present Invention.

Formula I-97

Formula I-98

Formula I-99

TABLE 1-continued
Additional Exemplary Formulas within the Present Invention.
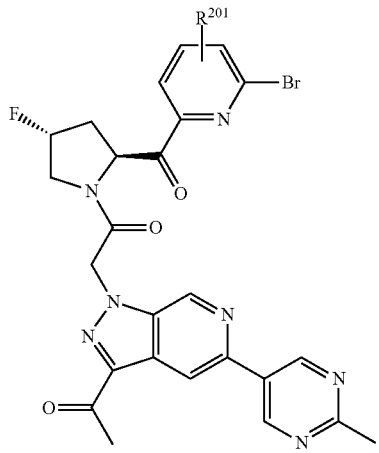
Formula I-100
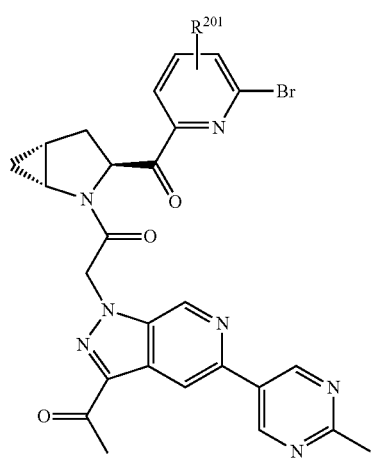
Formula I-101
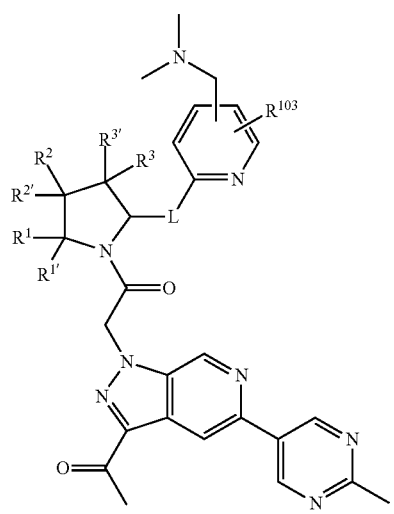
Formula I-102
TABLE 1-continued
Additional Exemplary Formulas within the Present Invention.
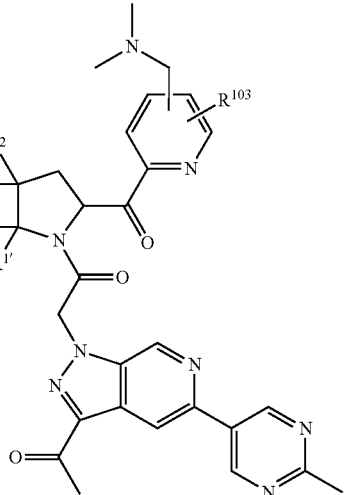
Formula I-103
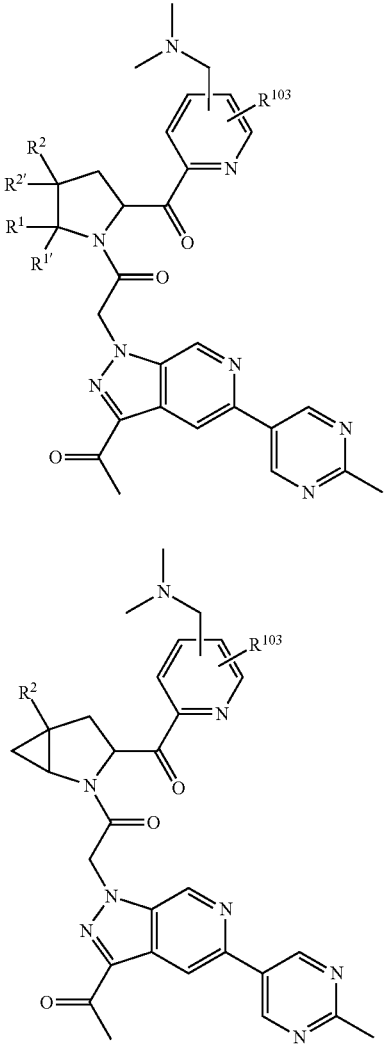
Formula I-104
Formula I-105
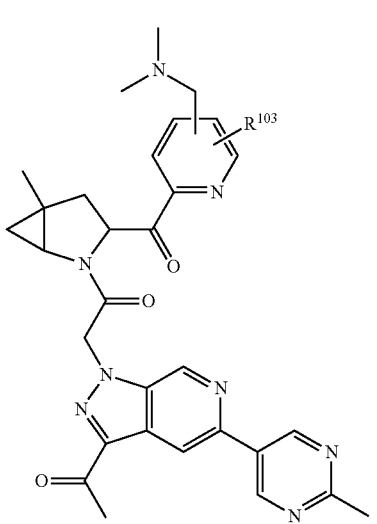

TABLE 1-continued
Additional Exemplary Formulas within the Present Invention.
Formula I-106
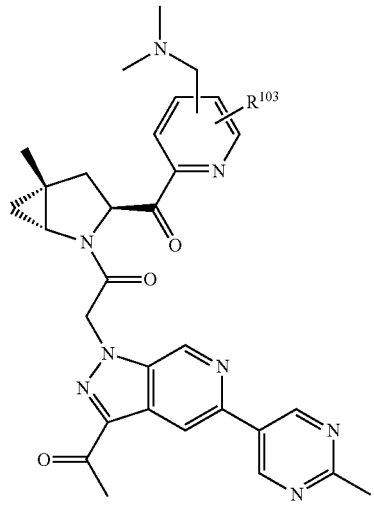
Formula I-107
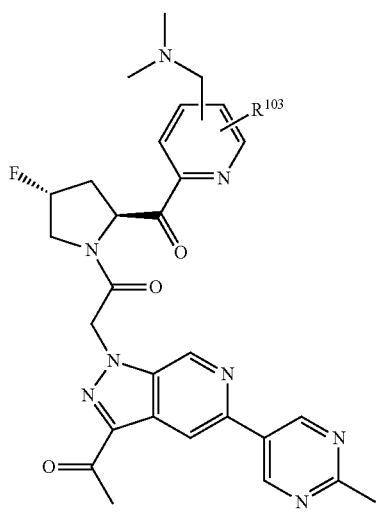
Formula I-108
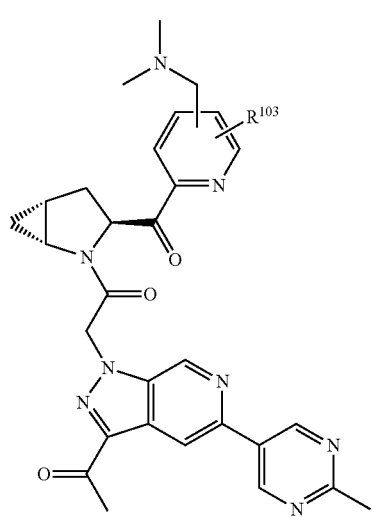
TABLE 1-continued
Additional Exemplary Formulas within the Present Invention.
Formula I-109
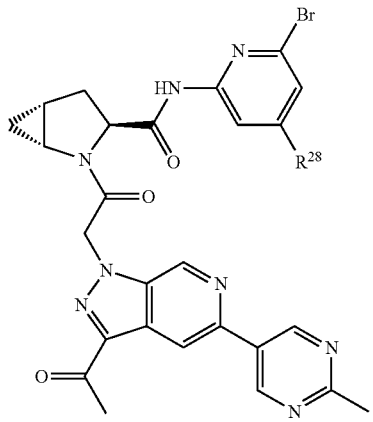
Formula I-110
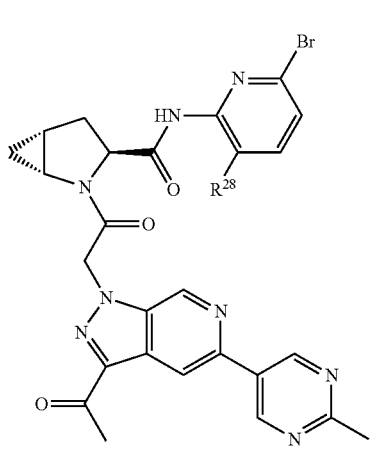
Formula I-111
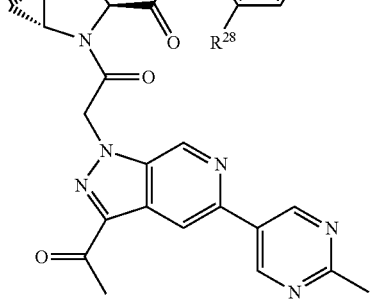

TABLE 1-continued
Additional Exemplary Formulas within the Present Invention.
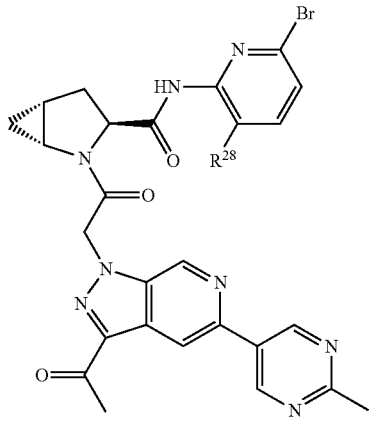
Formula I-112
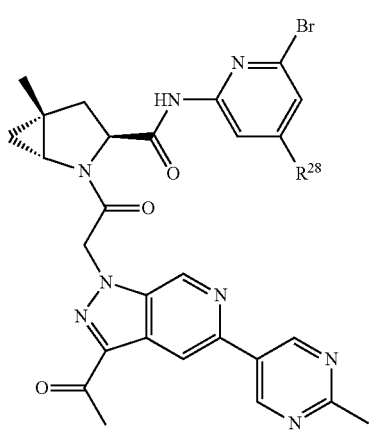
Formula I-113
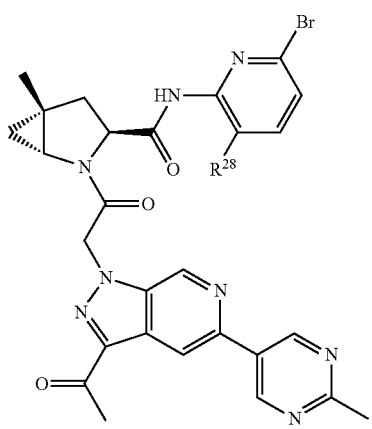
Formula I-114
TABLE 1-continued
Additional Exemplary Formulas within the Present Invention.
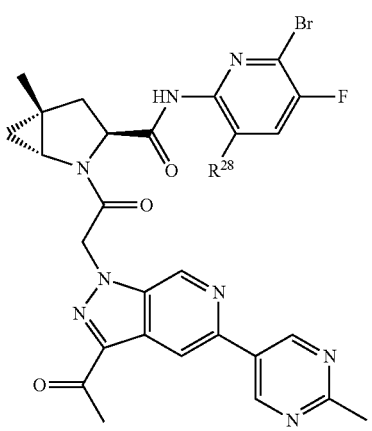
Formula I-115
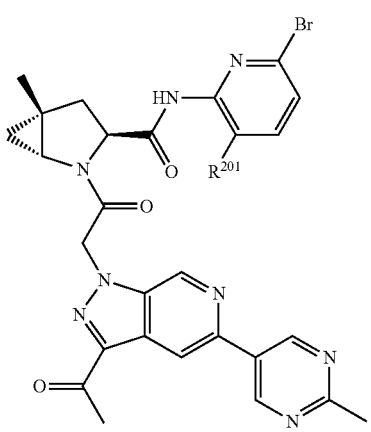
Formula I-116
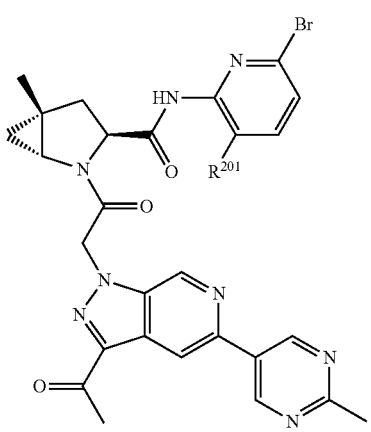
Formula I-117

TABLE 1-continued
Additional Exemplary Formulas within the Present Invention.
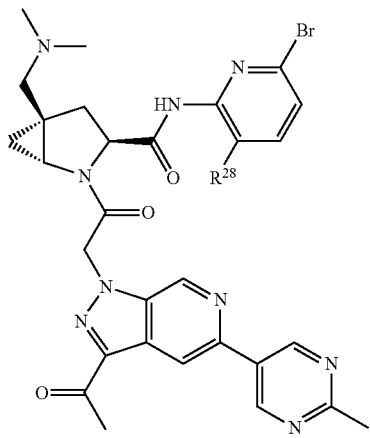
Formula I-118
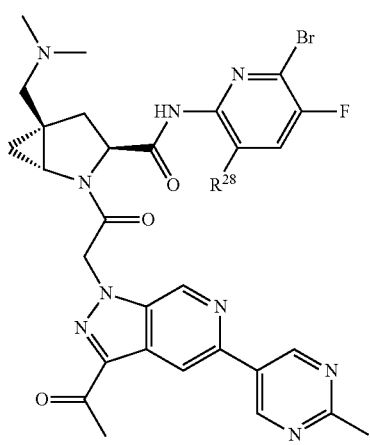
Formula I-119
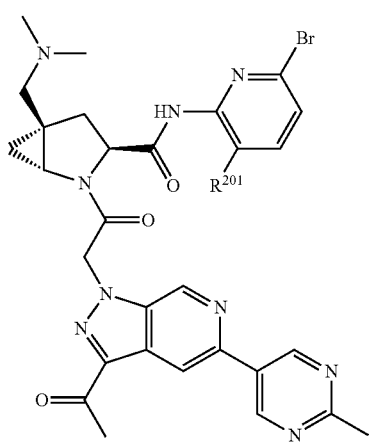
Formula I-120
TABLE 1-continued
Additional Exemplary Formulas within the Present Invention.
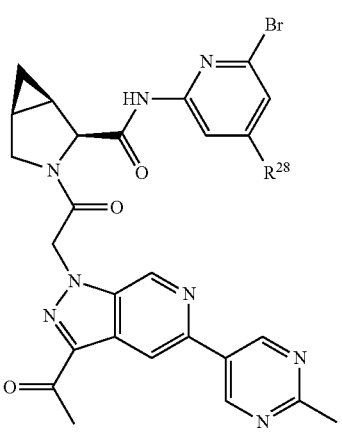
Formula I-121
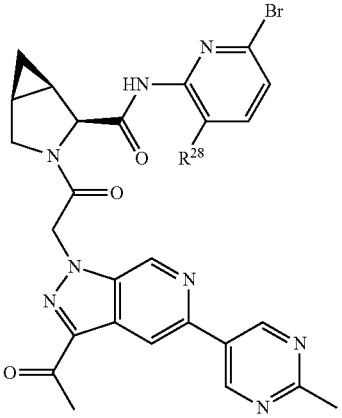
Formula I-122
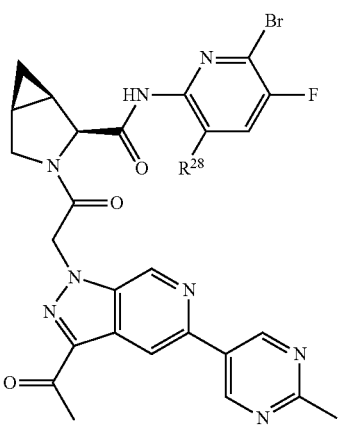
Formula I-123

TABLE 1-continued
Additional Exemplary Formulas within the Present Invention.
Formula I-124
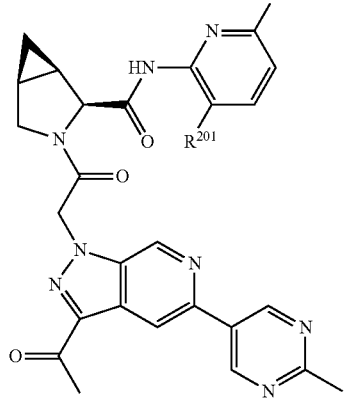
Formula I-125
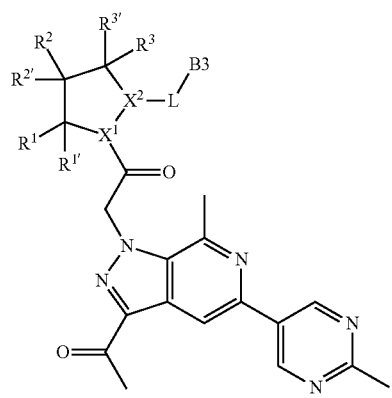
Formula I-126
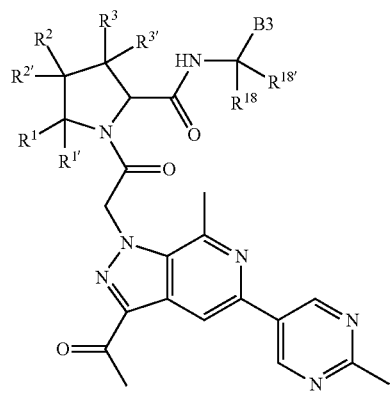
TABLE 1-continued
Additional Exemplary Formulas within the Present Invention.
Formula I-127
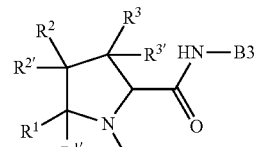
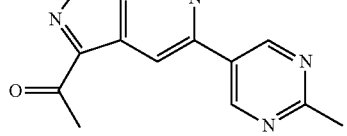
Formula I-128
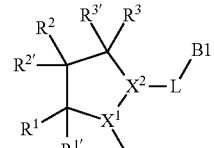
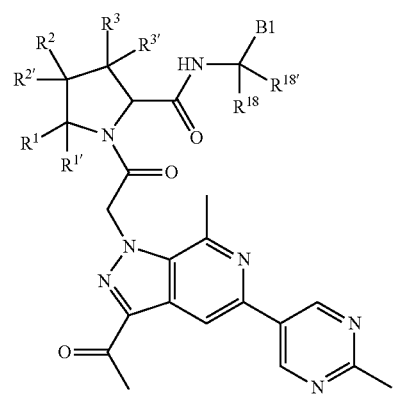
Formula I-129
Formula I-130
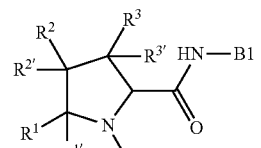

TABLE 1-continued
Additional Exemplary Formulas within the Present Invention.
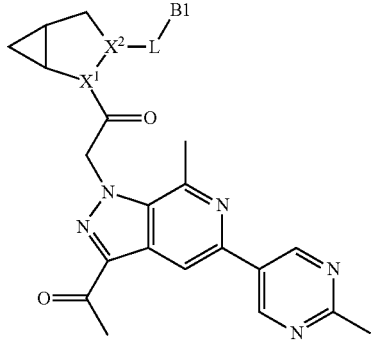
Formula I-131
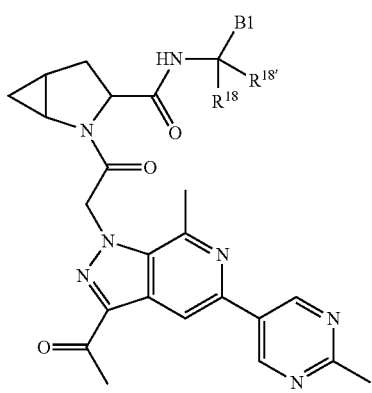
Formula I-132
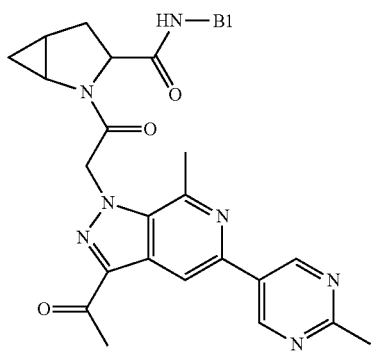
Formula I-133
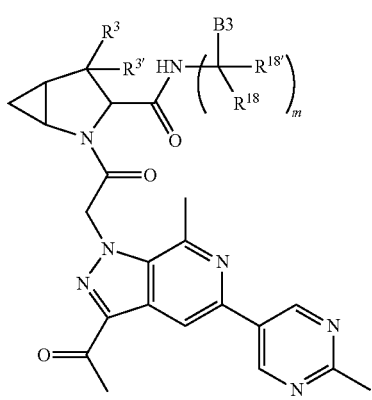
Formula I-134
TABLE 1-continued
Additional Exemplary Formulas within the Present Invention.
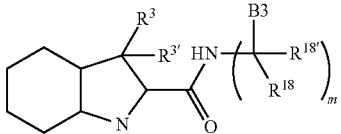
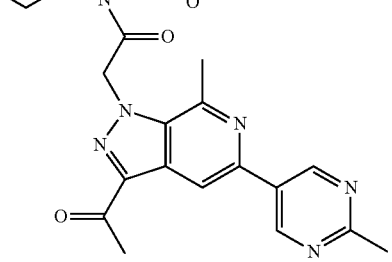
Formula I-135
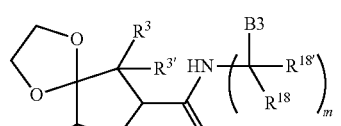
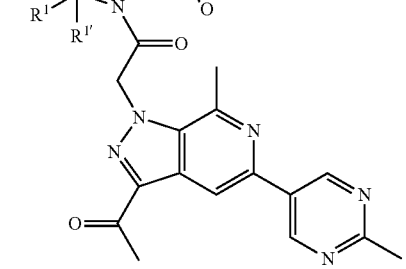
Formula I-136
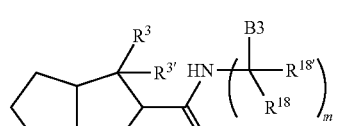
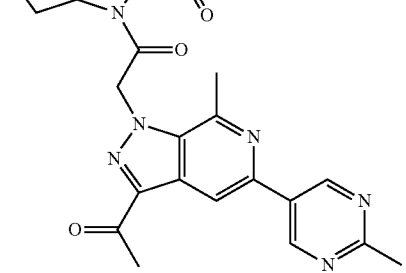
Formula I-137

TABLE 1-continued
Additional Exemplary Formulas within the Present Invention.
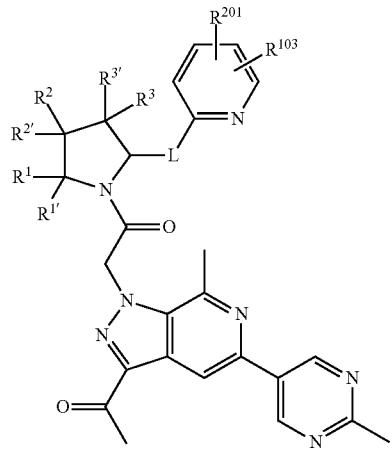
Formula I-138
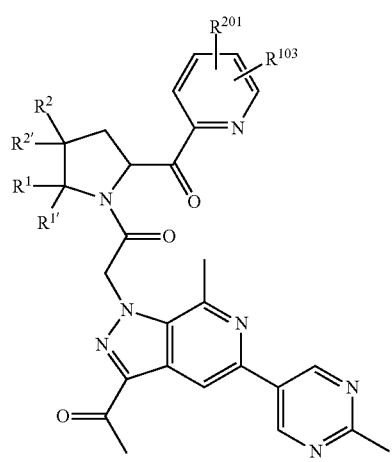
Formula I-139
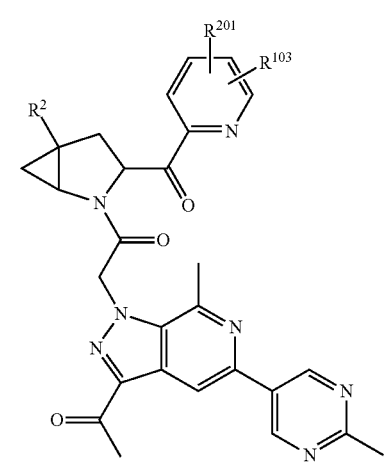
Formula I-140
TABLE 1-continued
Additional Exemplary Formulas within the Present Invention.
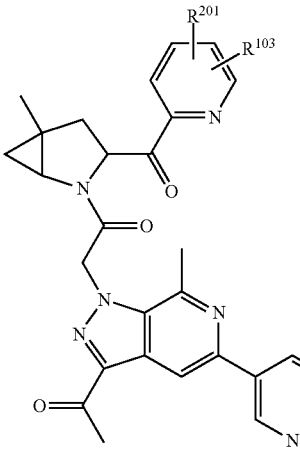
Formula I-141
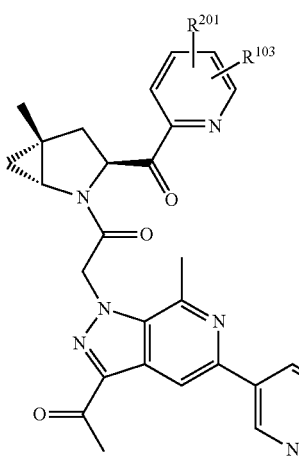
Formula I-142
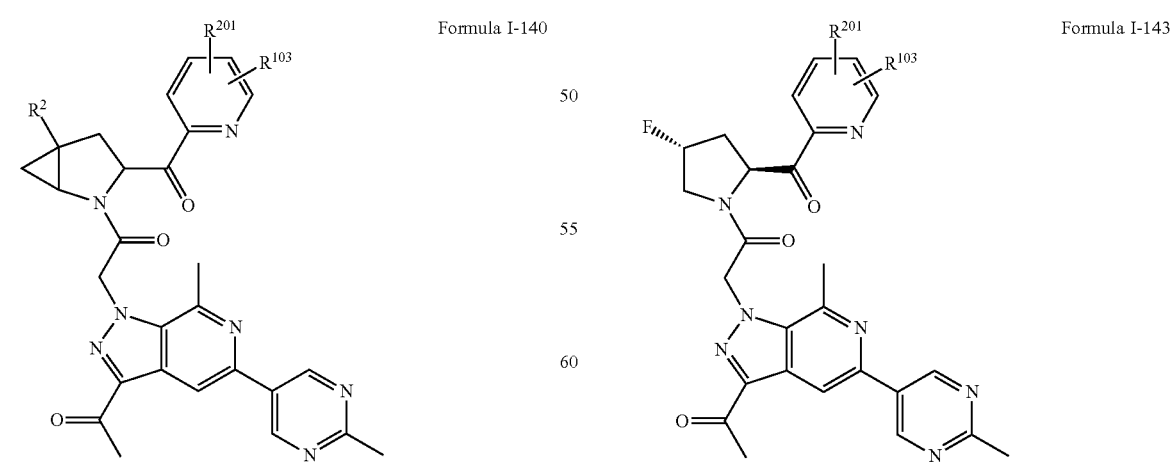
Formula I-143

TABLE 1-continued
Additional Exemplary Formulas within the Present Invention.
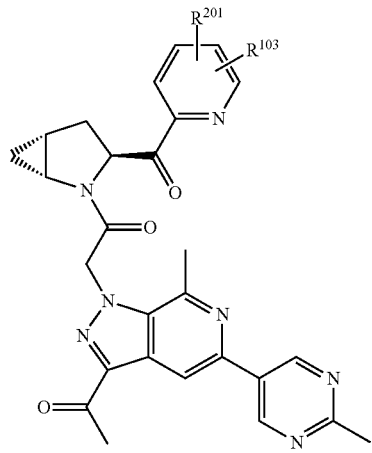
Formula I-144
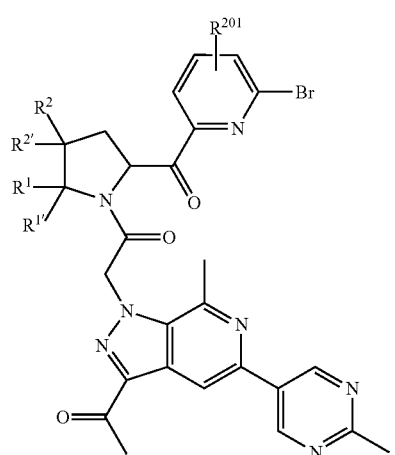
Formula I-145
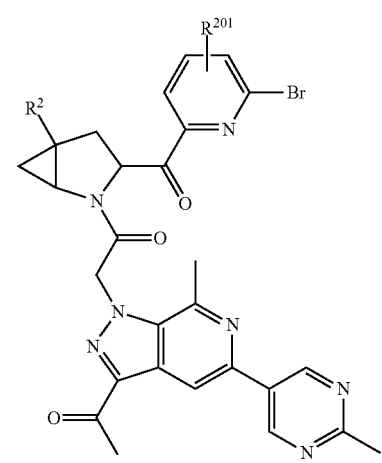
Formula I-146
TABLE 1-continued
Additional Exemplary Formulas within the Present Invention.
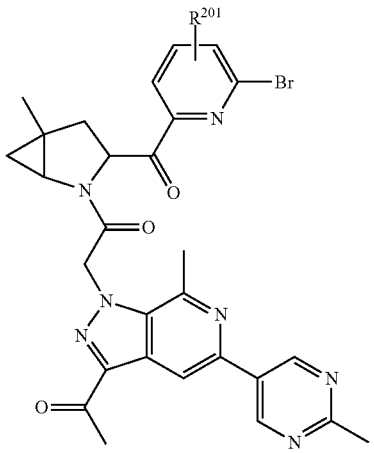
Formula I-147
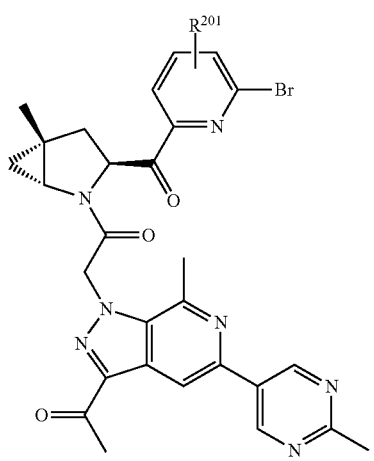
Formula I-148
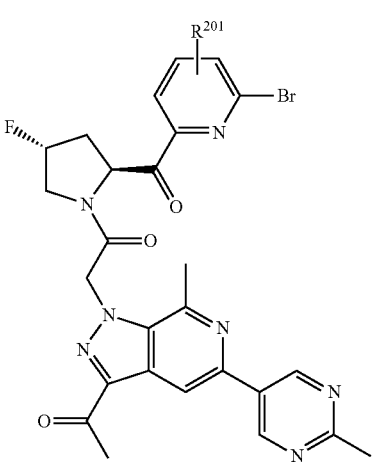
Formula I-149

TABLE 1-continued
Additional Exemplary Formulas within the Present Invention.
Formula I-150
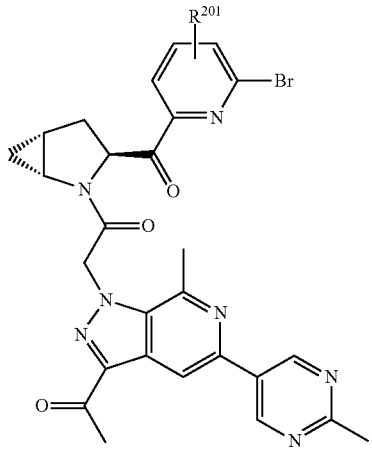
Formula I-151
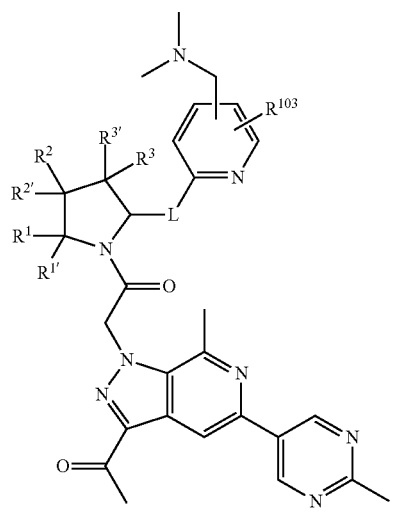
Formula I-152
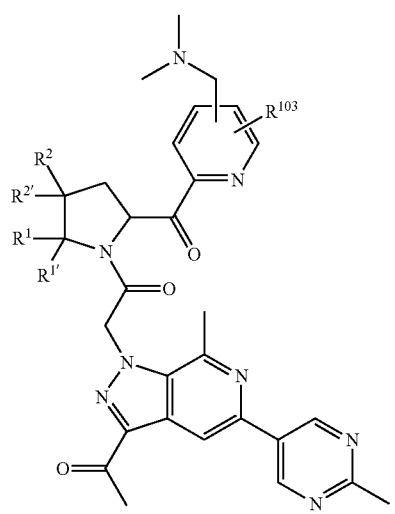
TABLE 1-continued
Additional Exemplary Formulas within the Present Invention.
Formula I-153
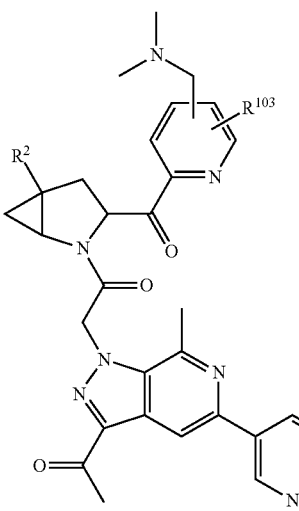
Formula I-154
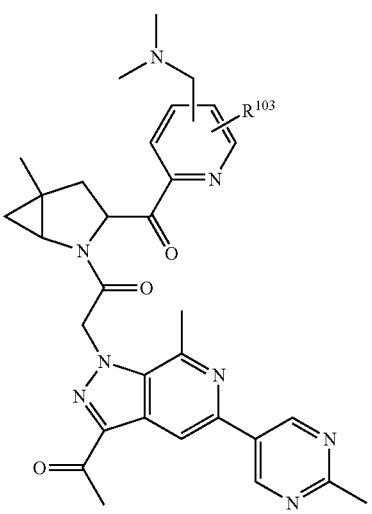
Formula I-155
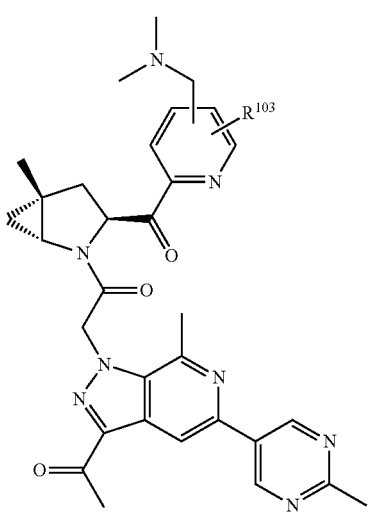

TABLE 1-continued
Additional Exemplary Formulas within the Present Invention.
Formula I-156
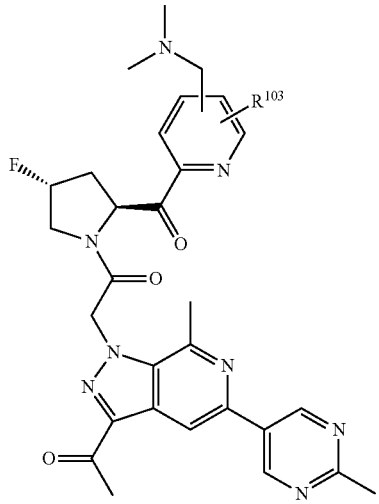
Formula I-157
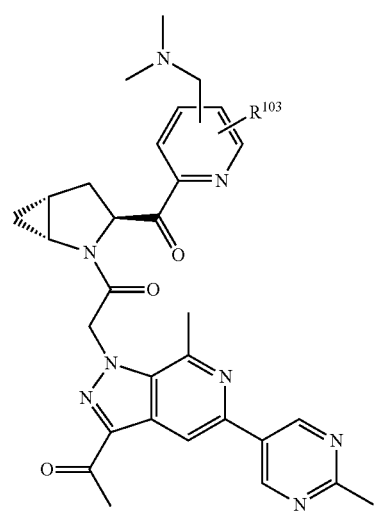
Formula I-158
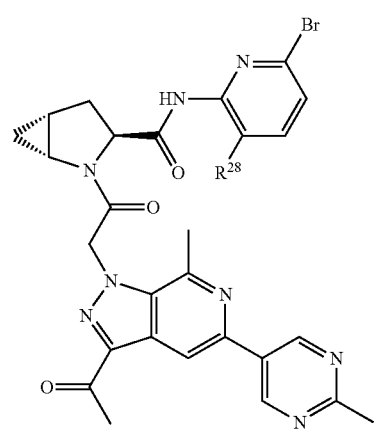
TABLE 1-continued
Additional Exemplary Formulas within the Present Invention.
Formula I-159
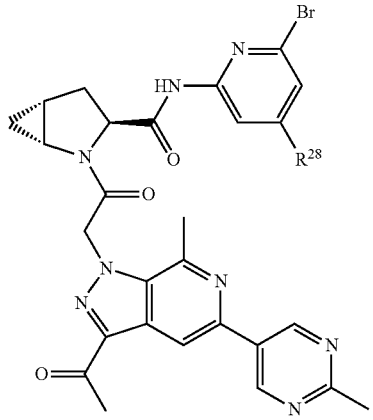
Formula I-160
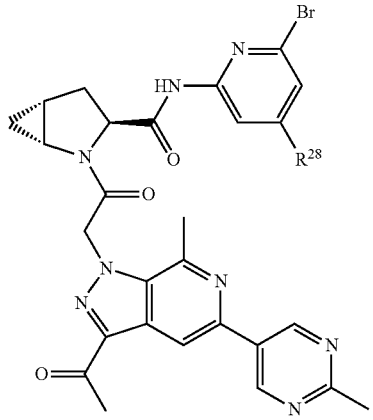
Formula I-161
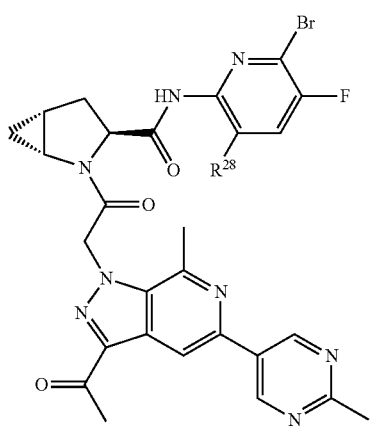

TABLE 1-continued
Additional Exemplary Formulas within the Present Invention.
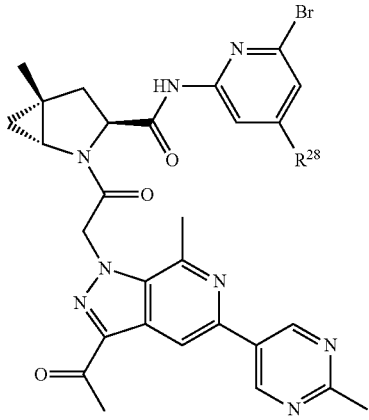
Formula I-162
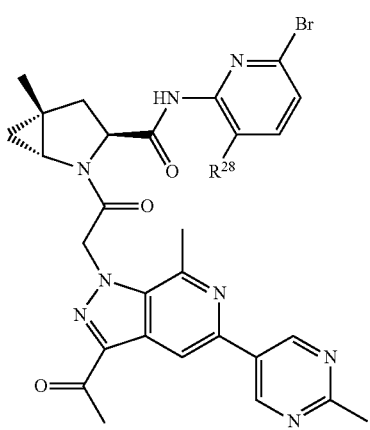
Formula I-163
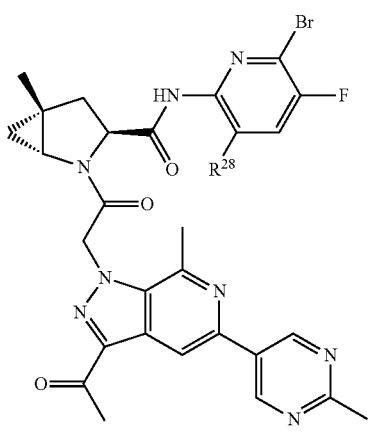
Formula I-164
TABLE 1-continued
Additional Exemplary Formulas within the Present Invention.
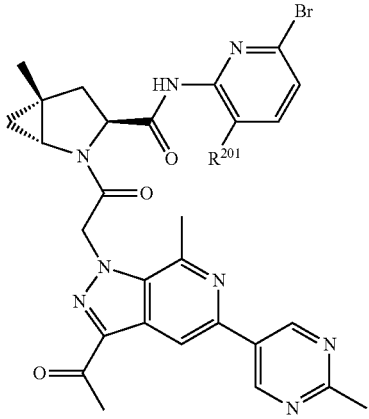
Formula I-165
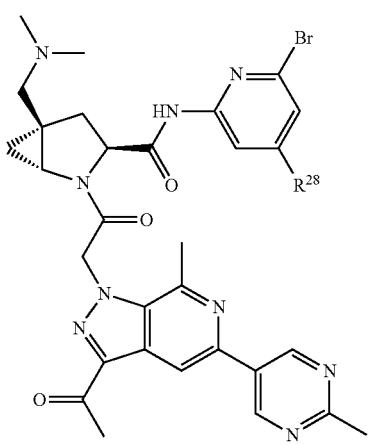
Formula I-166
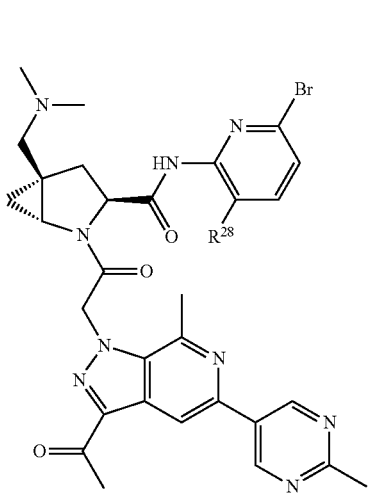
Formula I-167

TABLE 1-continued
Additional Exemplary Formulas within the Present Invention.
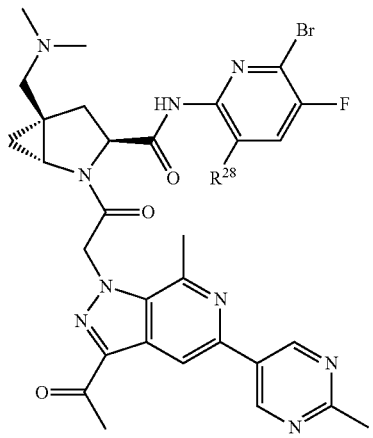
Formula I-168
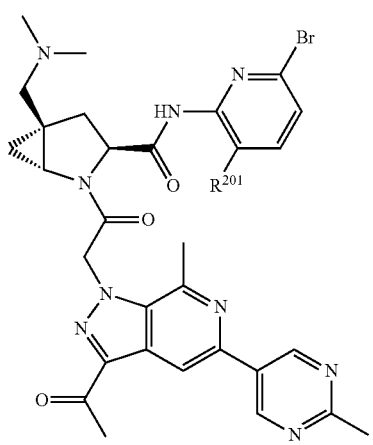
Formula I-169
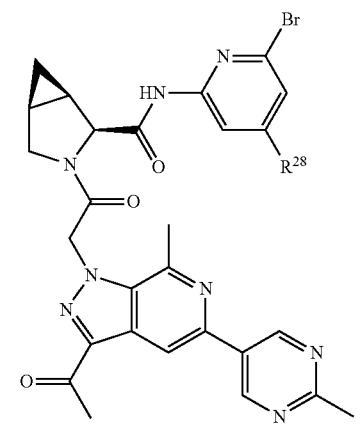
Formula I-170
TABLE 1-continued
Additional Exemplary Formulas within the Present Invention.
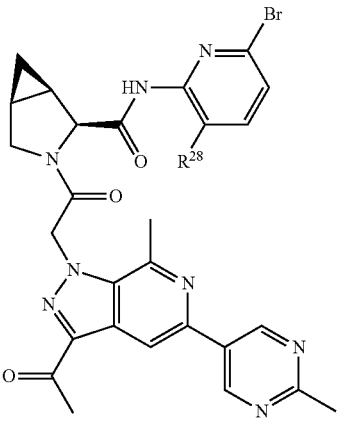
Formula I-171
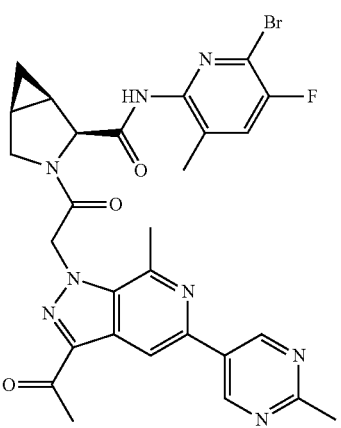 [SMILES: CC(=O)c1nn(CC(=O)N2C[C@H]3C[C@H]3[C@H]2C(=O)Nc2nc(Br)c(F)cc2C)c2c(C)nc(-c3cnc(C)nc3)cc12]
Formula I-172
Formula I-173

TABLE 1-continued
Additional Exemplary Formulas within the Present Invention.
Formula I-174
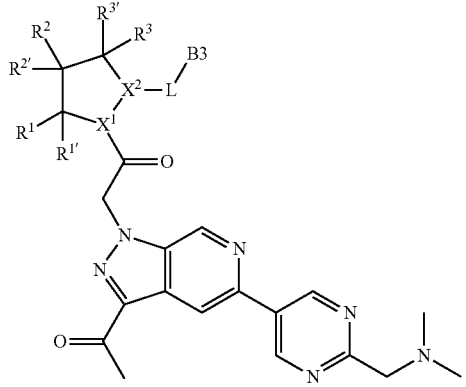
Formula I-175
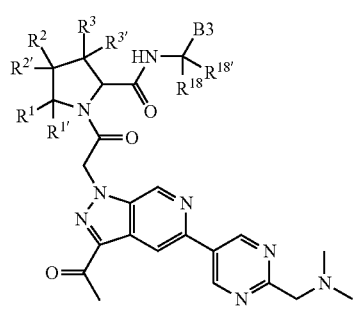
Formula I-176
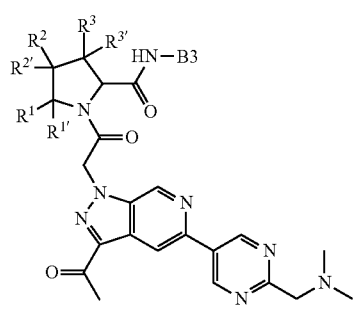
Formula I-177
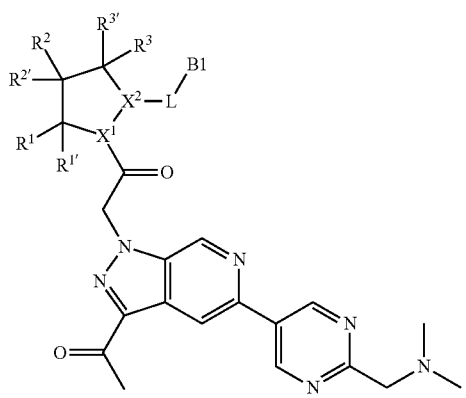
TABLE 1-continued
Additional Exemplary Formulas within the Present Invention.
Formula I-178
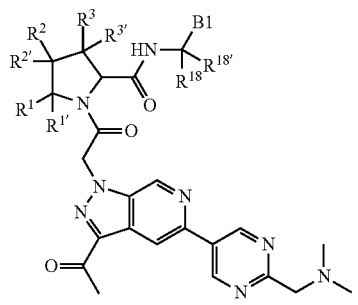
Formula I-179
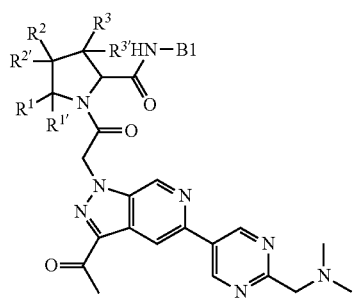
Formula I-180
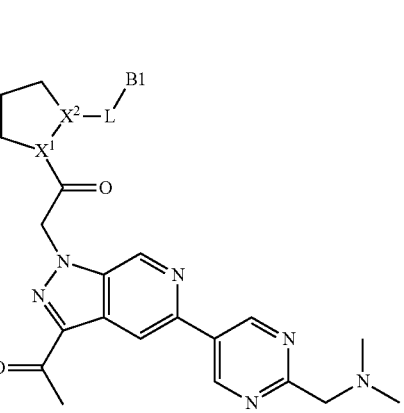
Formula I-181
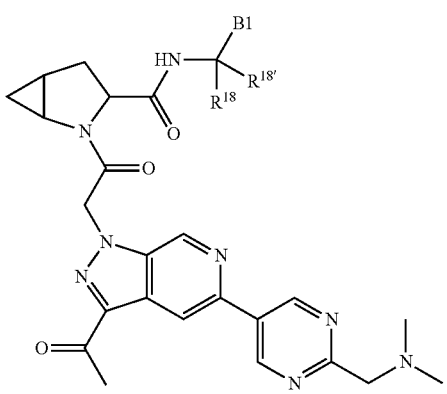

TABLE 1-continued
Additional Exemplary Formulas within the Present Invention.
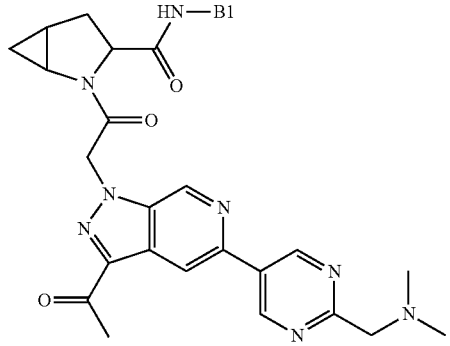 Formula I-182
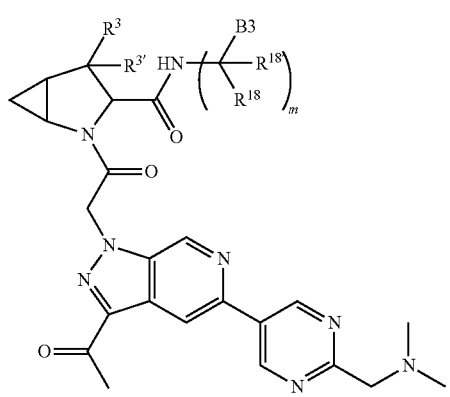 Formula I-183
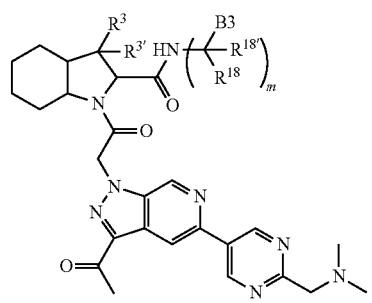 Formula I-184
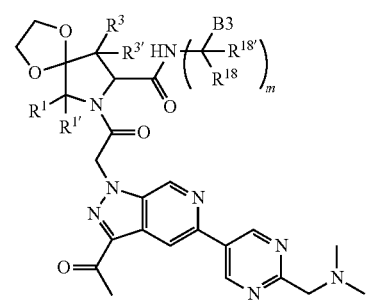 Formula I-185
TABLE 1-continued
Additional Exemplary Formulas within the Present Invention.
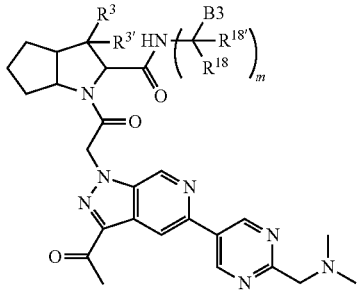 Formula I-186
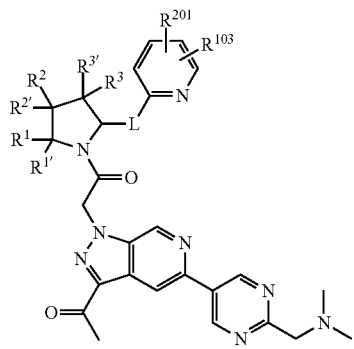 Formula I-187
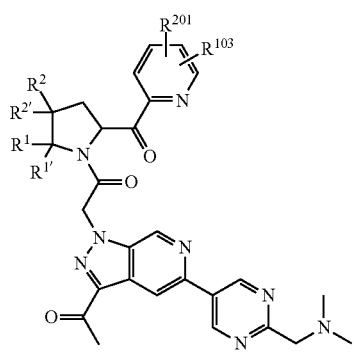 Formula I-188
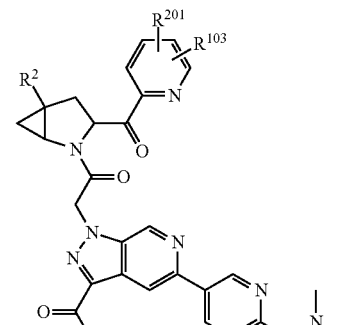 Formula I-189

TABLE 1-continued
Additional Exemplary Formulas within the Present Invention.
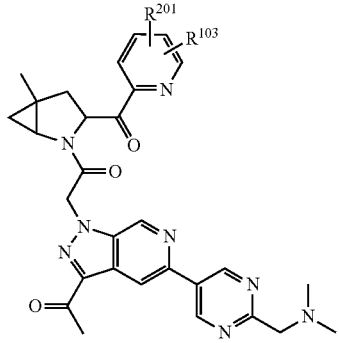
Formula I-190
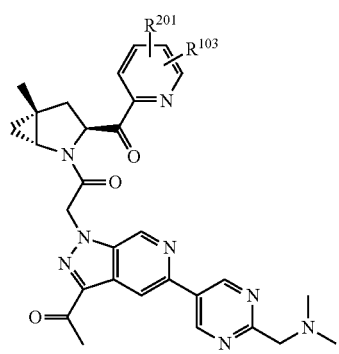
Formula I-191
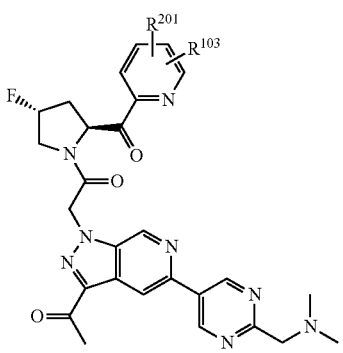
Formula I-192
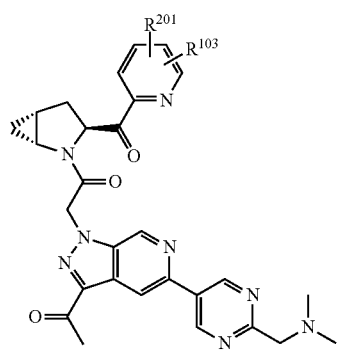
Formula I-193
TABLE 1-continued
Additional Exemplary Formulas within the Present Invention.
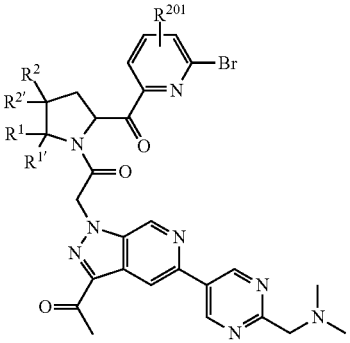
Formula I-194
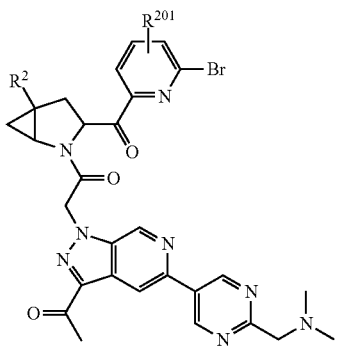
Formula I-195
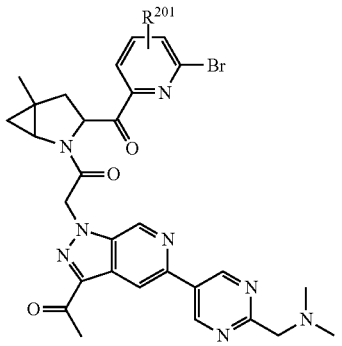
Formula I-196
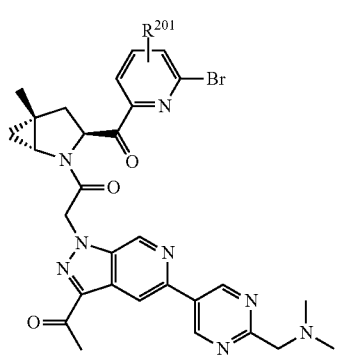
Formula I-197

TABLE 1-continued
Additional Exemplary Formulas within the Present Invention.
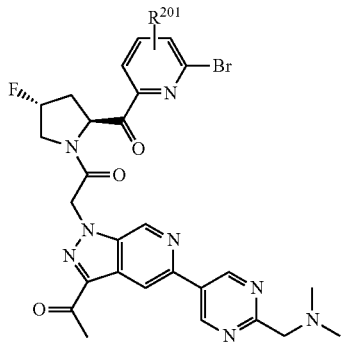
Formula I-198
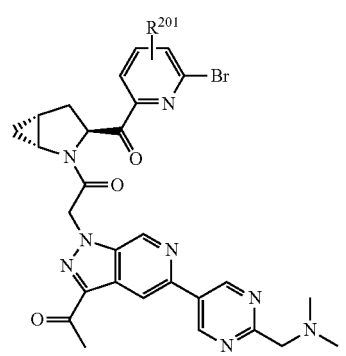
Formula I-199
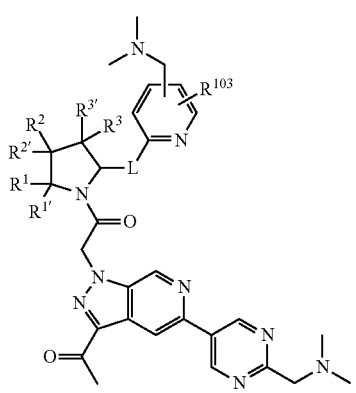
Formula I-200
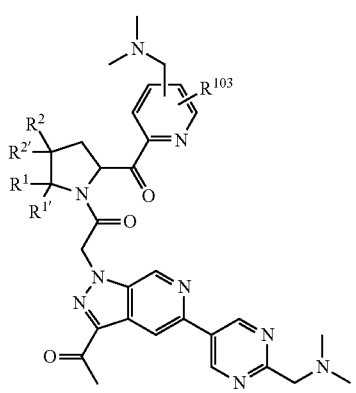
Formula I-201
TABLE 1-continued
Additional Exemplary Formulas within the Present Invention.
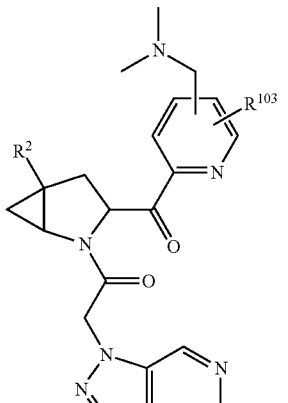
Formula I-202
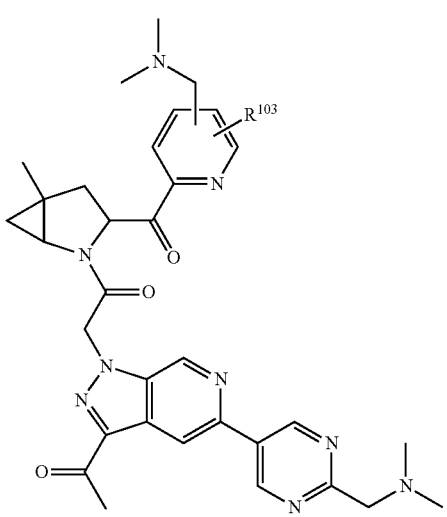
Formula I-203
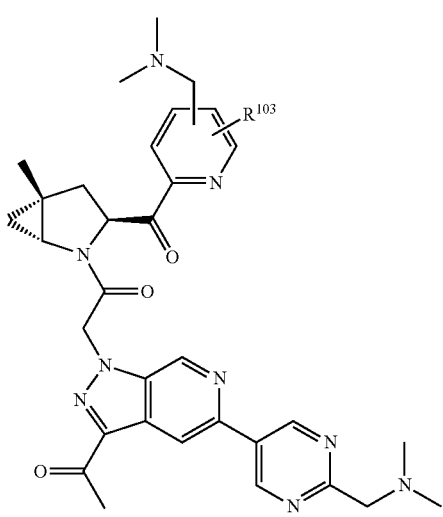
Formula I-204

TABLE 1-continued
Additional Exemplary Formulas within the Present Invention.
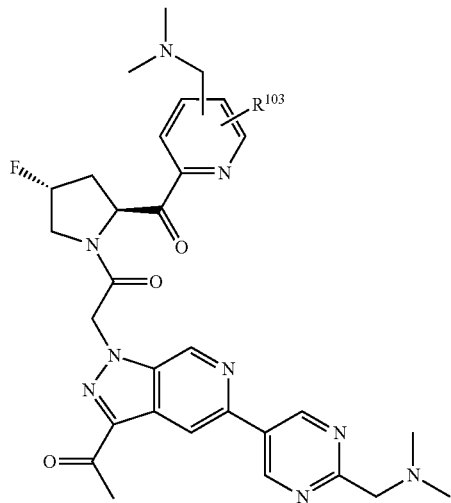
Formula I-205
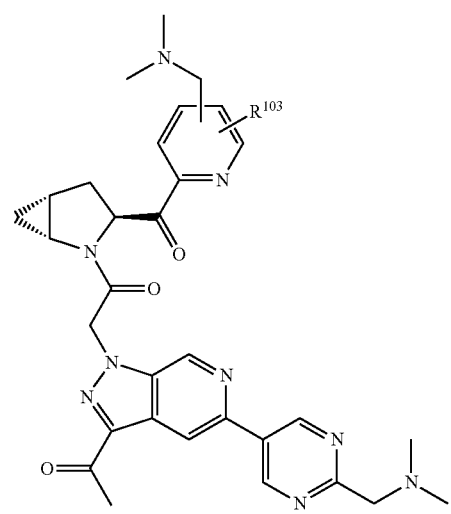
Formula I-206
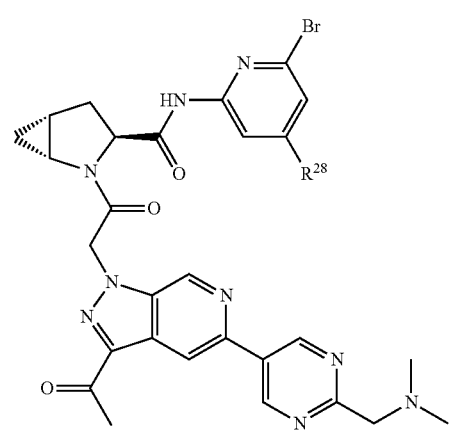
Formula I-207
TABLE 1-continued
Additional Exemplary Formulas within the Present Invention.
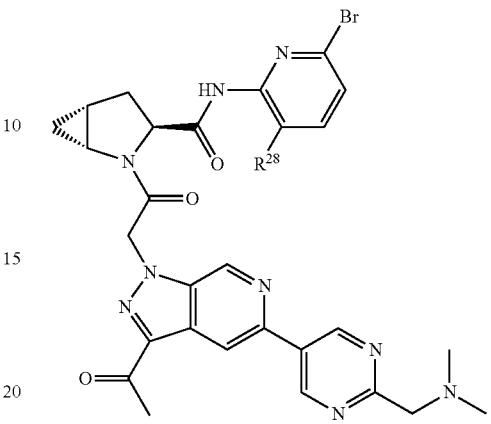
Formula I-208
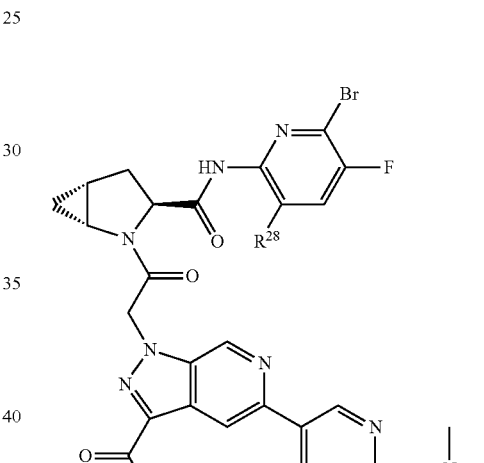
Formula I-209
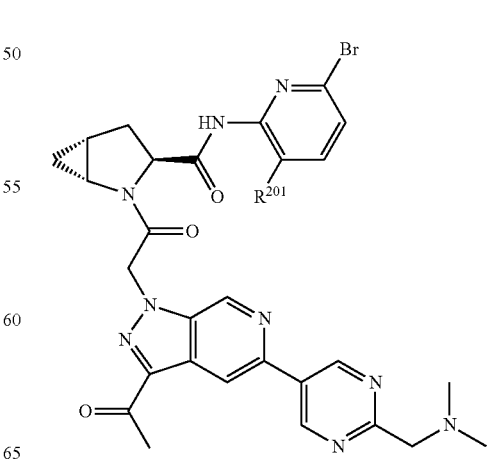
Formula I-210

TABLE 1-continued
Additional Exemplary Formulas within the Present Invention.
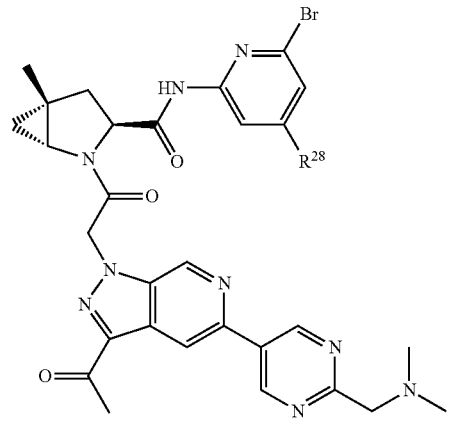
Formula I-211
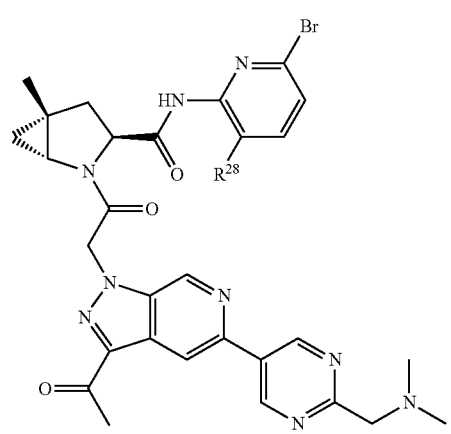
Formula I-212
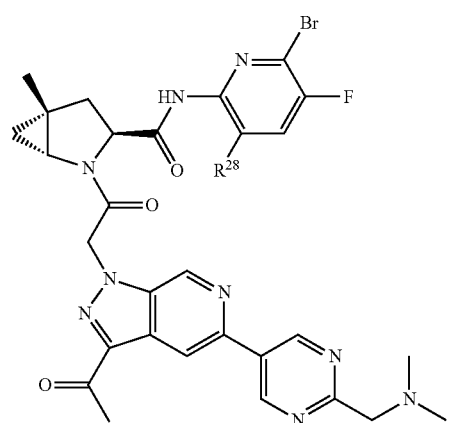
Formula I-213
TABLE 1-continued
Additional Exemplary Formulas within the Present Invention.
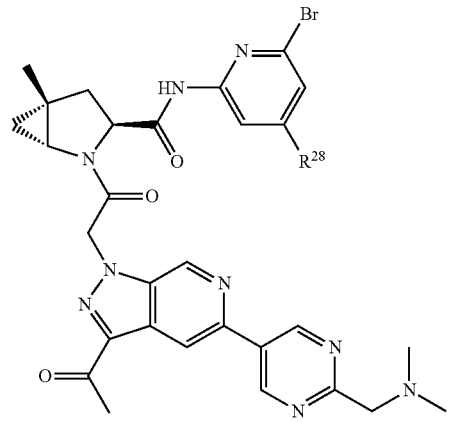
Formula I-214
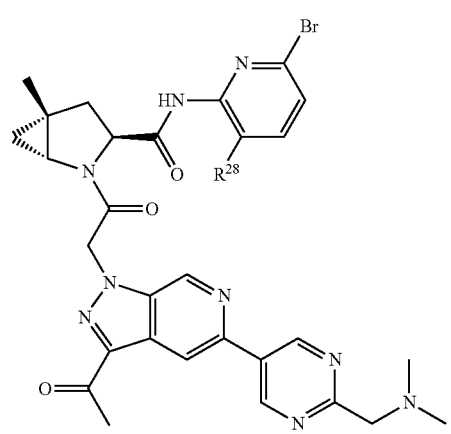
Formula I-215
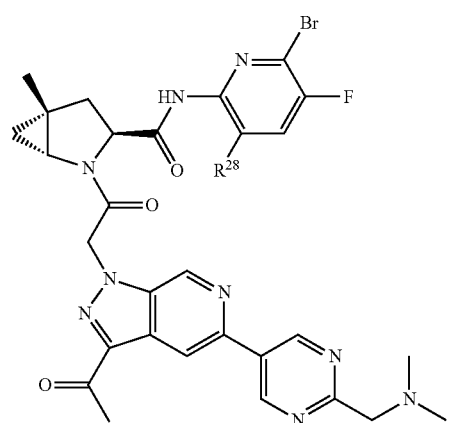
Formula I-216

TABLE 1-continued
Additional Exemplary Formulas within the Present Invention.
Formula I-217
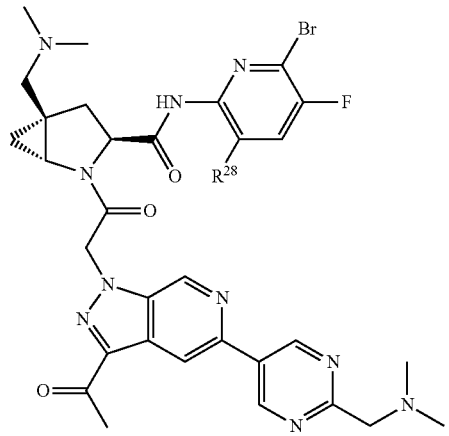
Formula I-218
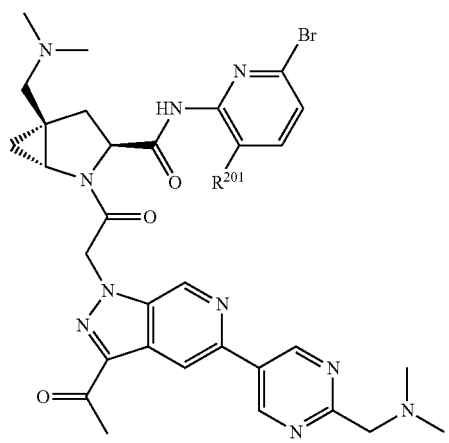
Formula I-219
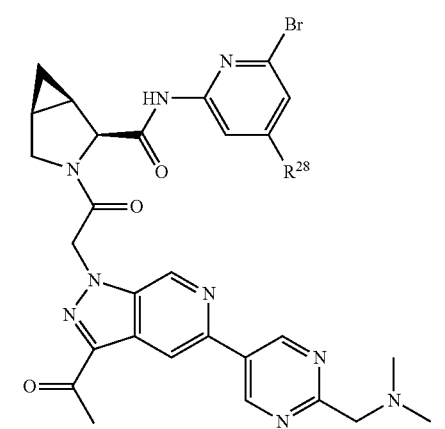
TABLE 1-continued
Additional Exemplary Formulas within the Present Invention.
Formula I-220
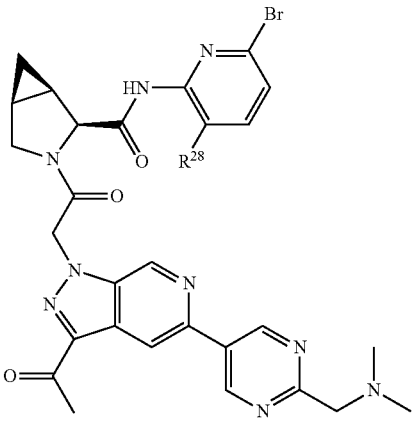
Formula I-221
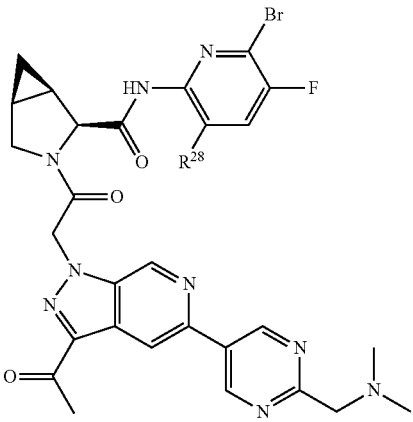
Formula I-222
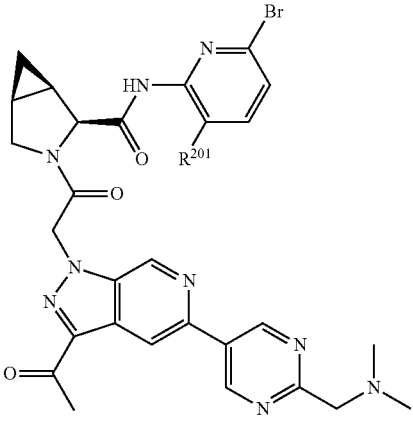

TABLE 1-continued
Additional Exemplary Formulas within the Present Invention.
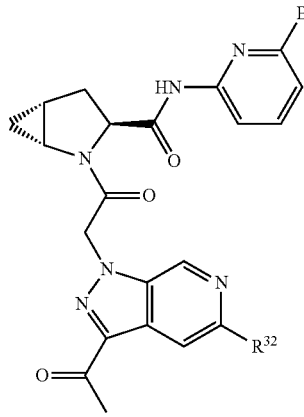
Formula I-223
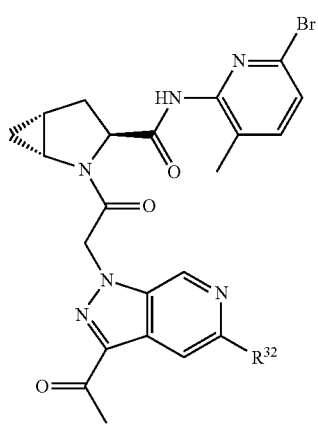
Formula I-224
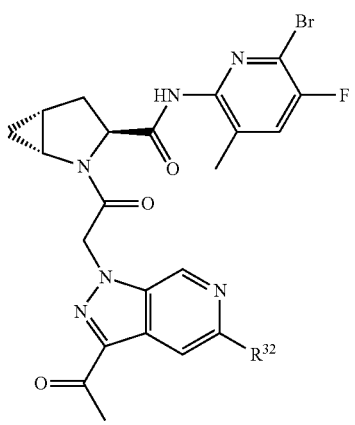
Formula I-225
TABLE 1-continued
Additional Exemplary Formulas within the Present Invention.
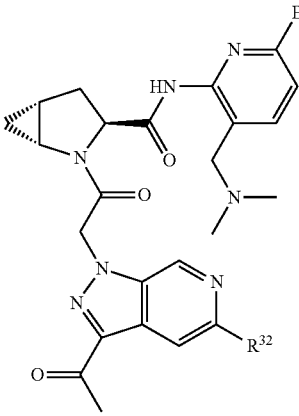
Formula I-226
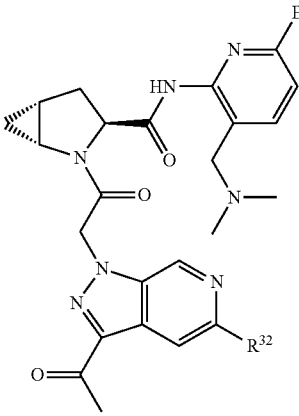
Formula I-227
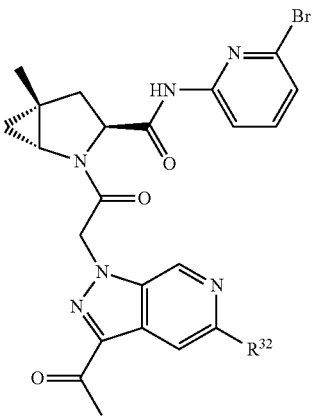
Formula I-228

TABLE 1-continued
Additional Exemplary Formulas within the Present Invention.
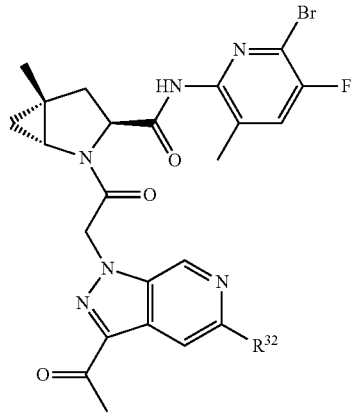 Formula I-229
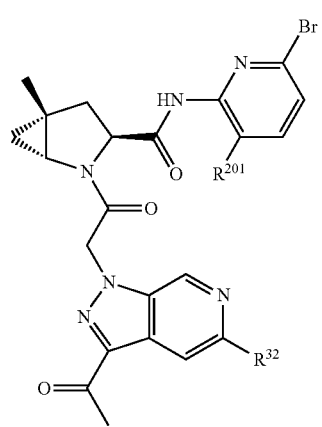 Formula I-230
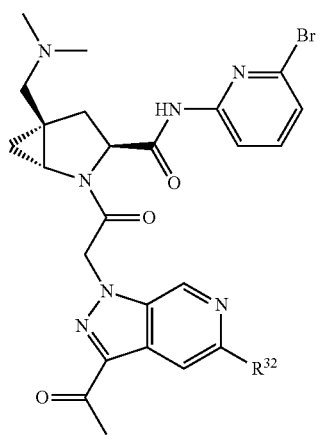 Formula I-232
TABLE 1-continued
Additional Exemplary Formulas within the Present Invention.
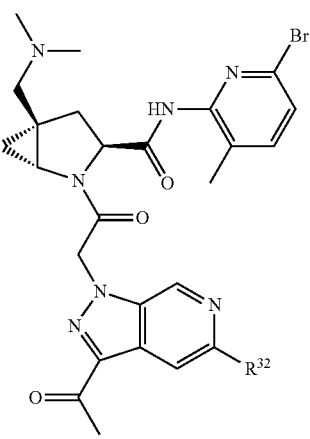 Formula I-233
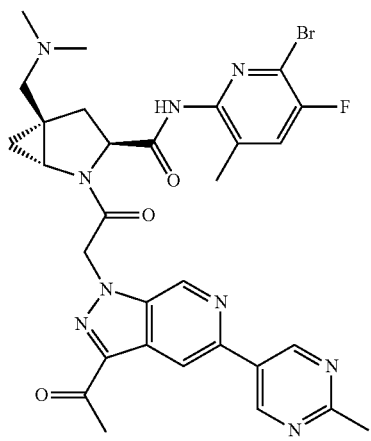 [SMILES: CC(=O)c1nn(CC(=O)N2[C@H](C(=O)Nc3nc(Br)c(F)cc3C)C[C@@]3(CN(C)C)C[C@@H]23)c2cnc(-c3cnc(C)nc3)cc12] Formula I-234
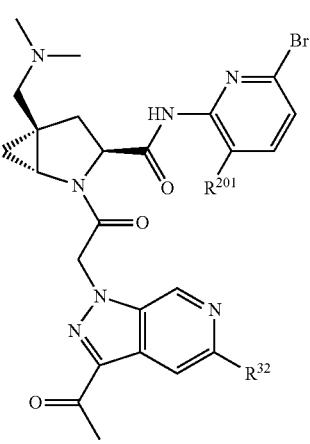 Formula I-235

TABLE 1-continued
Additional Exemplary Formulas within the Present Invention.
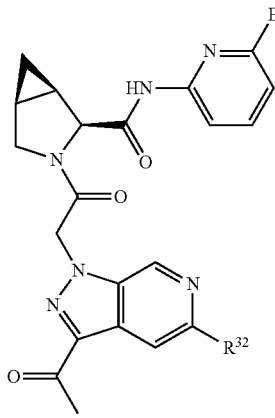
Formula I-236
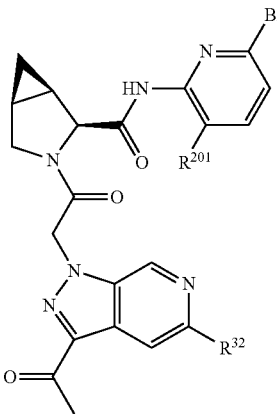
Formula I-239
wherein $R^{103}$ is $C_1$-$C_4$ alkyl, $C_3$-$C_6$ cycloalkyl, fluorine, chlorine, or bromine.
TABLE 2
Additional Exemplary Formulas within the Present Invention.
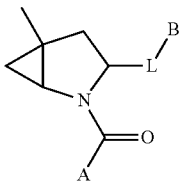
Formula II-1
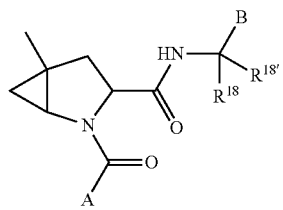
Formula II-2
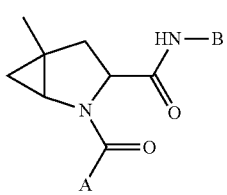
Formula II-3
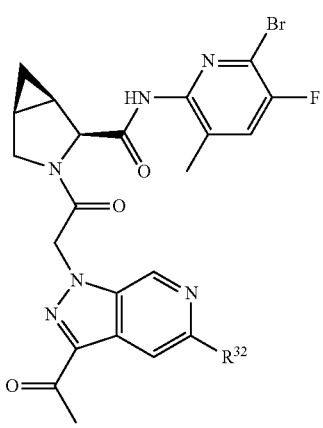
Formula I-237
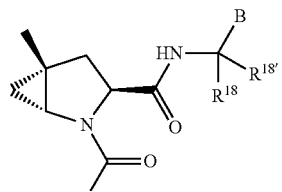
Formula II-4
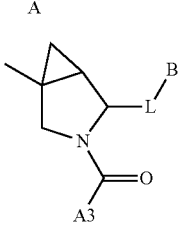
Formula II-5
Formula I-238

TABLE 2-continued
Additional Exemplary Formulas within the Present Invention.
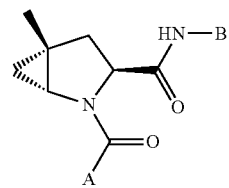
Formula II-6
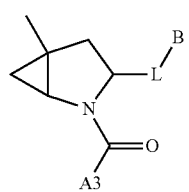
Formula II-7
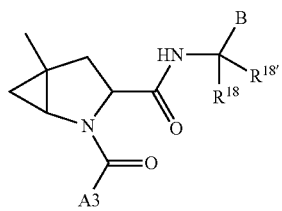
Formula II-8
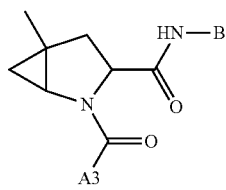
Formula II-9
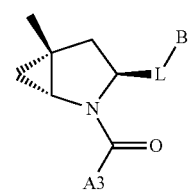
Formula II-10
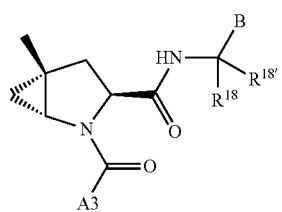
Formula II-11
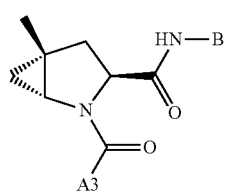
Formula II-12
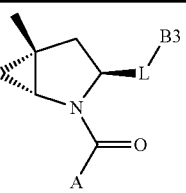
Formula II-13
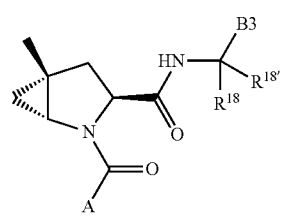
Formula II-14
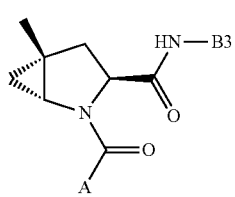
Formula II-15
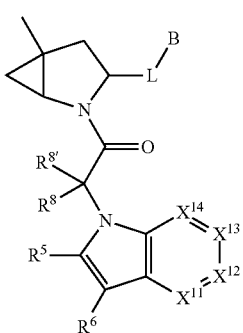
Formula II-16
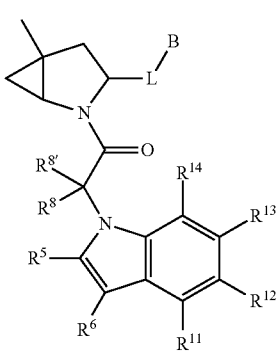
Formula II-17
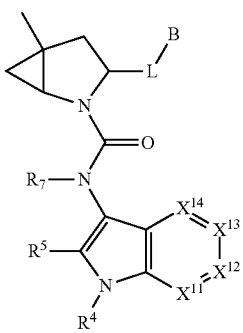
Formula II-18

TABLE 2-continued
Additional Exemplary Formulas within the Present Invention.
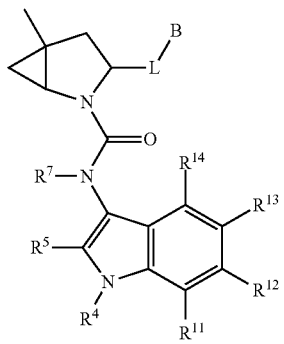
Formula II-19
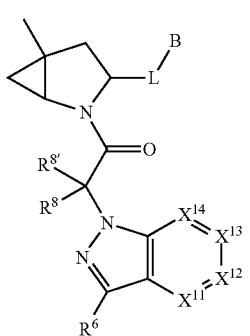
Formula II-20
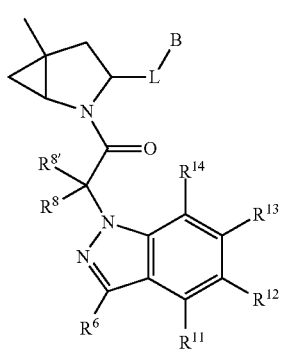
Formula II-21
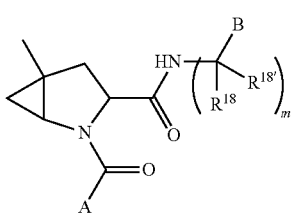
Formula II-22
TABLE 2-continued
Additional Exemplary Formulas within the Present Invention.
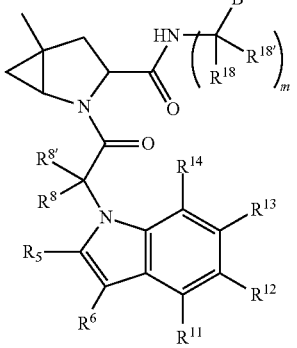
Formula II-23
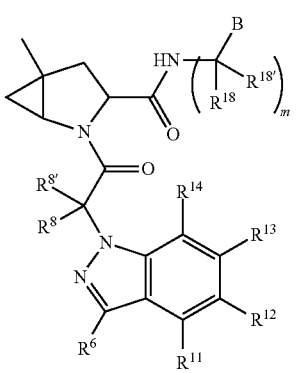
Formula II-24
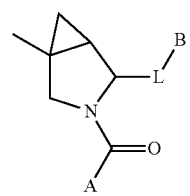
Formula II-25
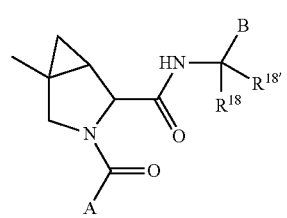
Formula II-26
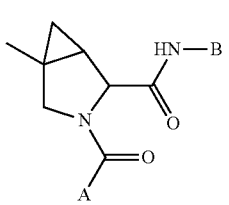
Formula II-27

TABLE 2-continued
Additional Exemplary Formulas within the Present Invention.
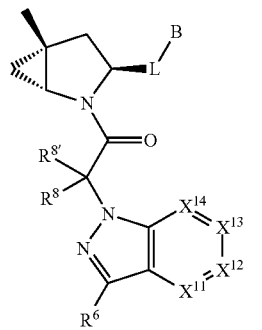
Formula II-28
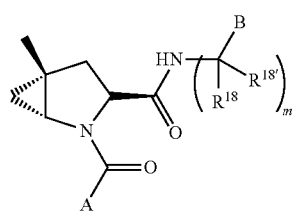
Formula II-29
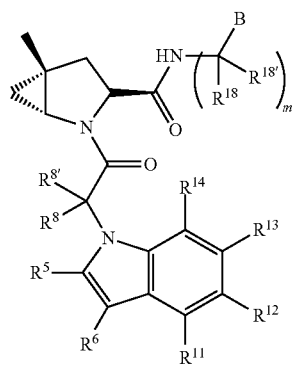
Formula II-30
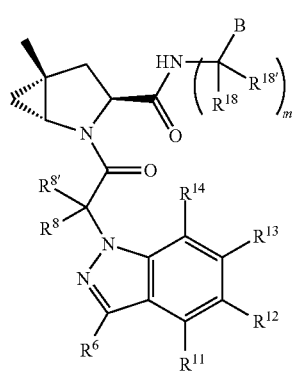
Formula II-31
TABLE 2-continued
Additional Exemplary Formulas within the Present Invention.
Formula II-32
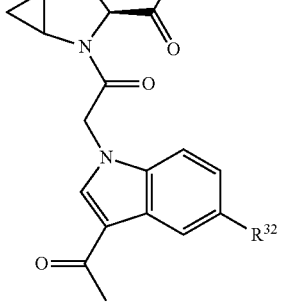
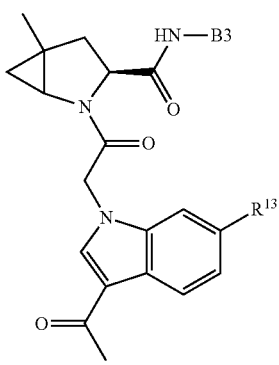
Formula II-33
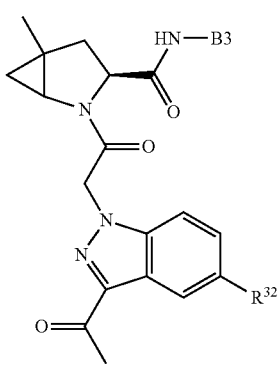
Formula II-34
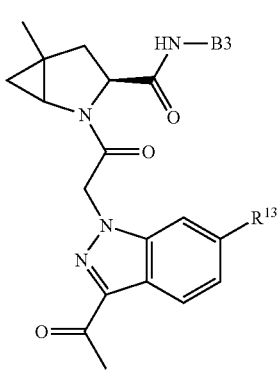
Formula II-35

TABLE 2-continued
Additional Exemplary Formulas within the Present Invention.
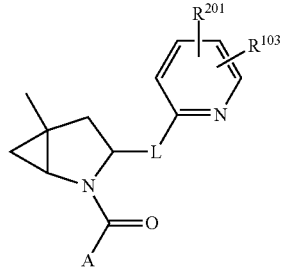
Formula II-36
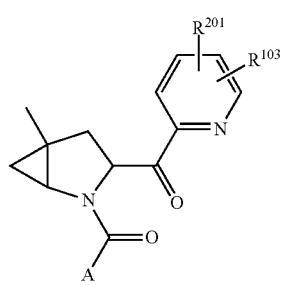
Formula II-37
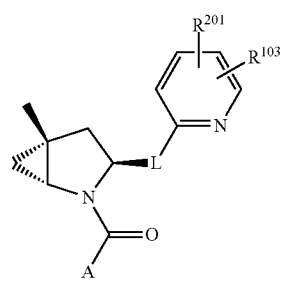
Formula II-38
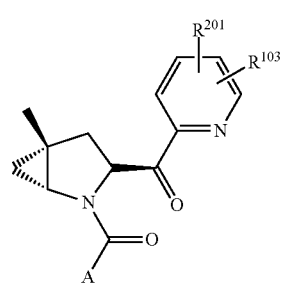
Formula II-39
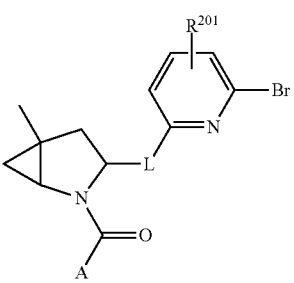
Formula II-40
TABLE 2-continued
Additional Exemplary Formulas within the Present Invention.
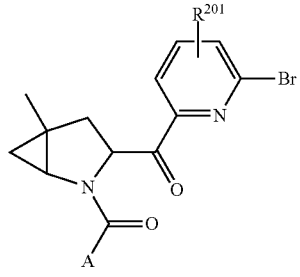
Formula II-41
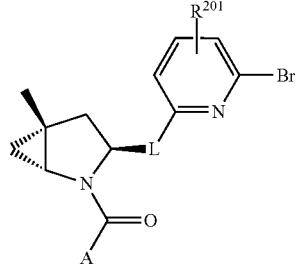
Formula II-42
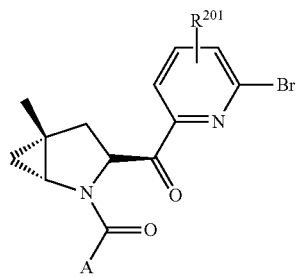
Formula II-43
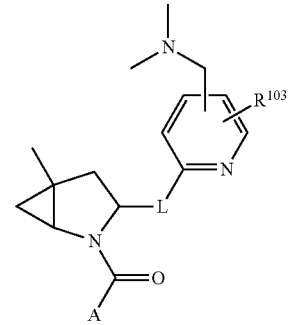
Formula II-44
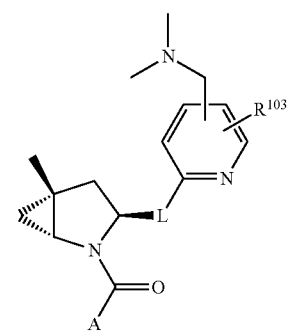
Formula II-45

TABLE 2-continued
Additional Exemplary Formulas within the Present Invention.
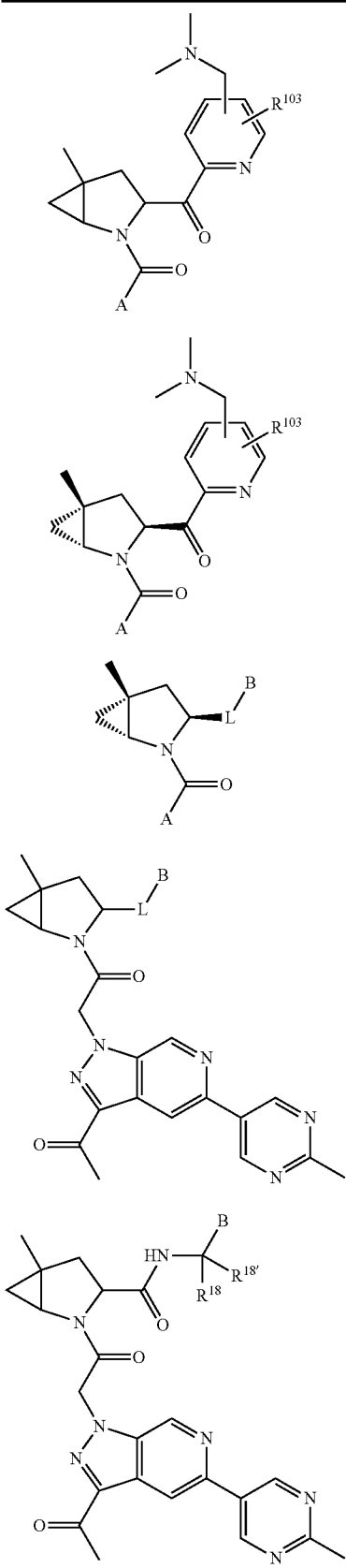
Formula II-46
Formula II-47
Formula II-48
Formula II-49
Formula II-50
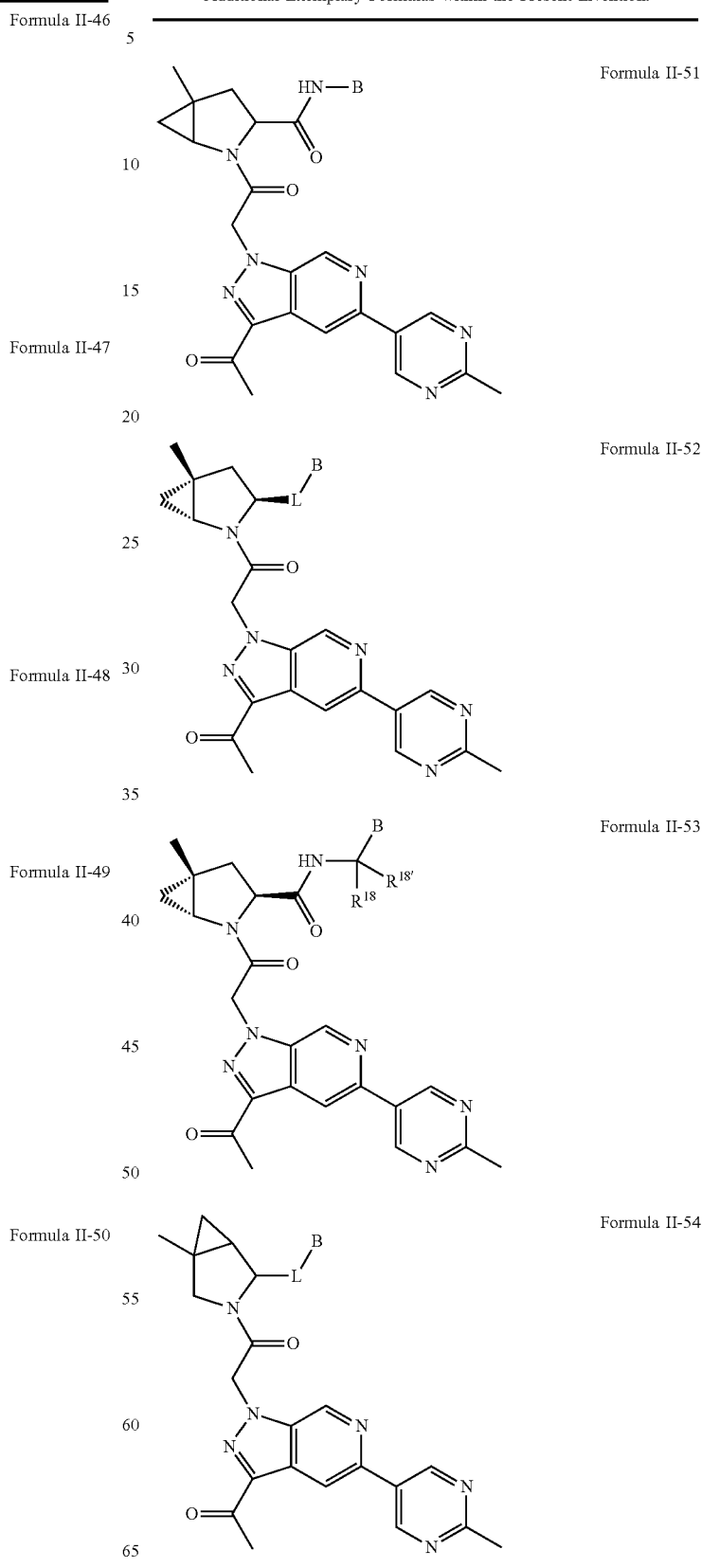
Formula II-51
Formula II-52
Formula II-53
Formula II-54

TABLE 2-continued
Additional Exemplary Formulas within the Present Invention.
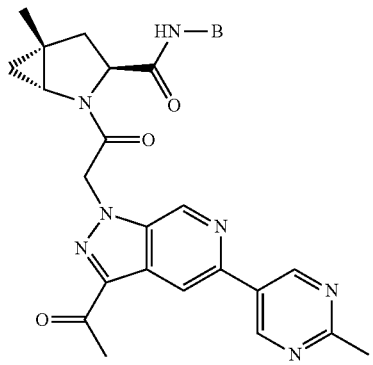
Formula II-55
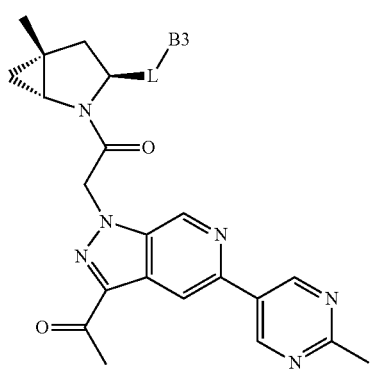
Formula II-56
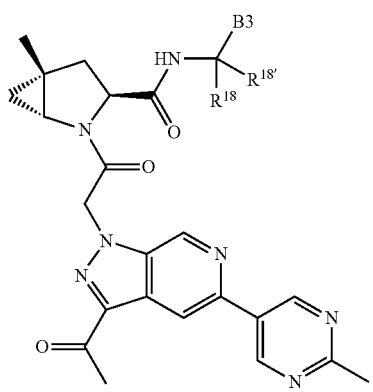
Formula II-57
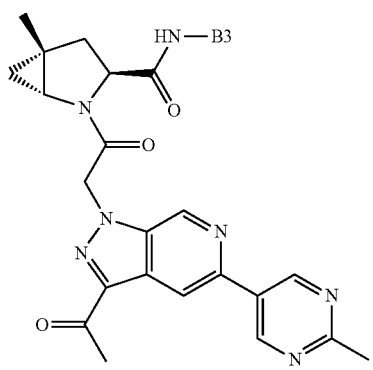
Formula II-58
TABLE 2-continued
Additional Exemplary Formulas within the Present Invention.
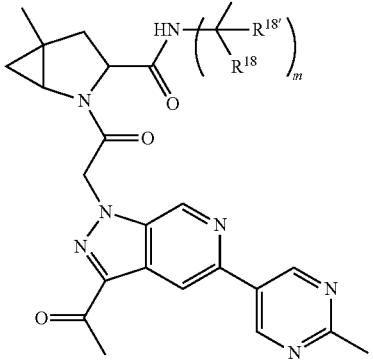
Formula II-59
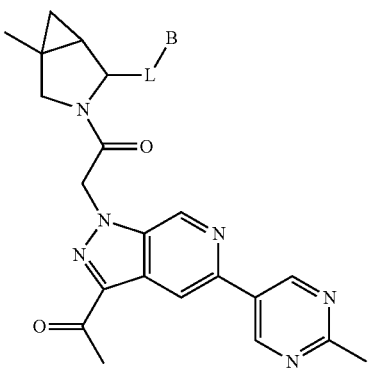
Formula II-60
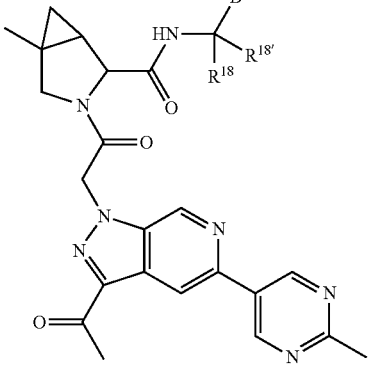
Formula II-61
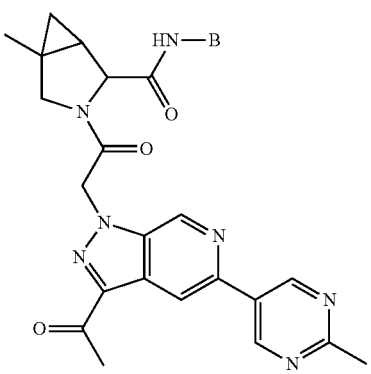
Formula II-62

TABLE 2-continued
Additional Exemplary Formulas within the Present Invention.
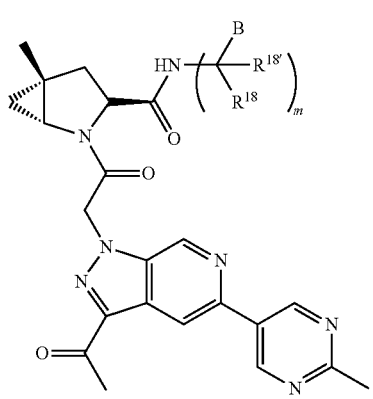
Formula II-63
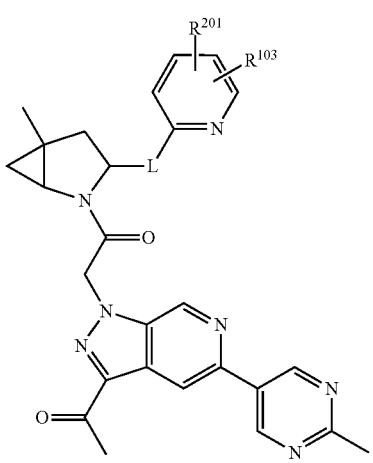
Formula II-64
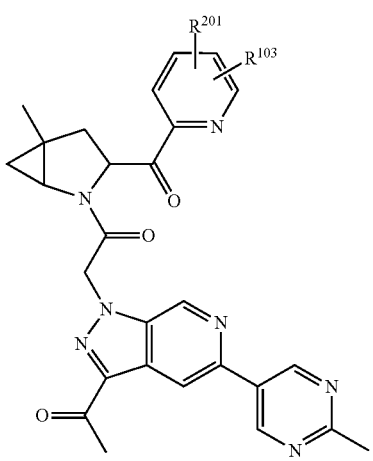
Formula II-65
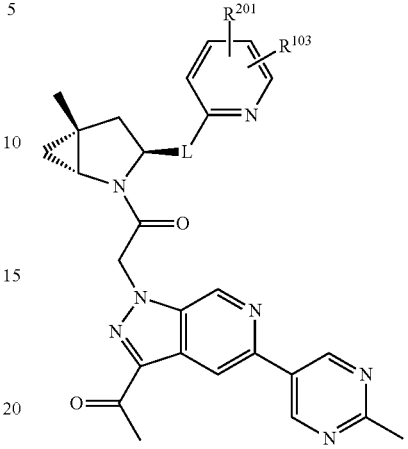
Formula II-66
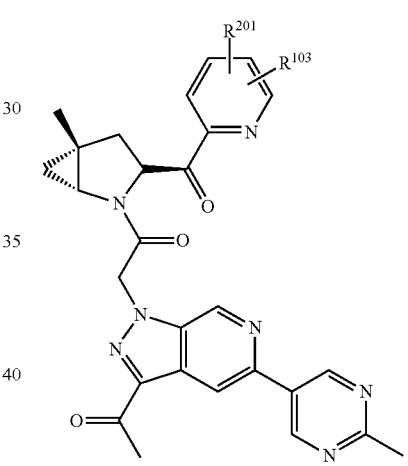
Formula II-67
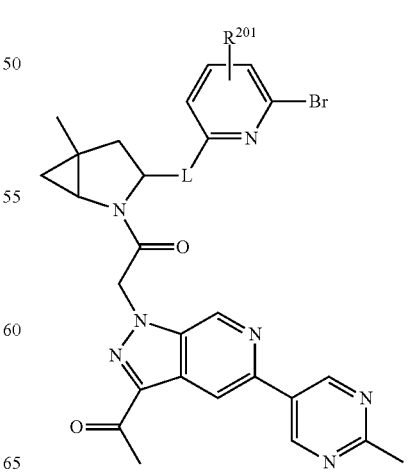
Formula II-68

TABLE 2-continued
Additional Exemplary Formulas within the Present Invention.
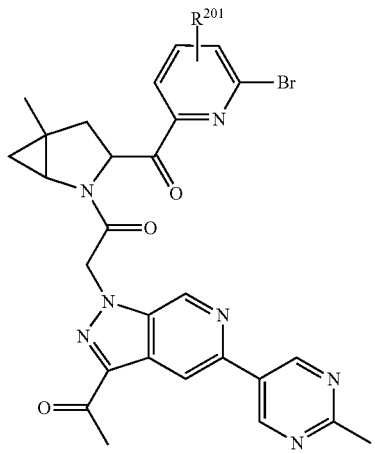
Formula II-69
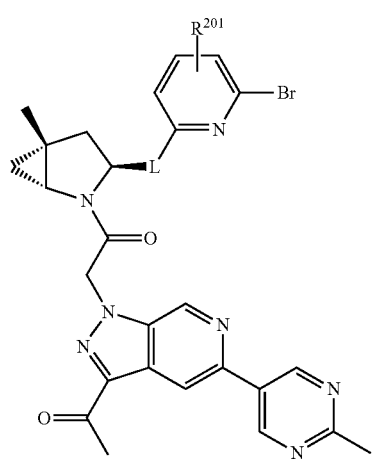
Formula II-70
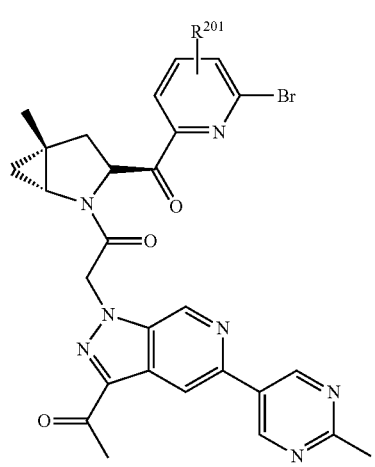
Formula II-71
TABLE 2-continued
Additional Exemplary Formulas within the Present Invention.
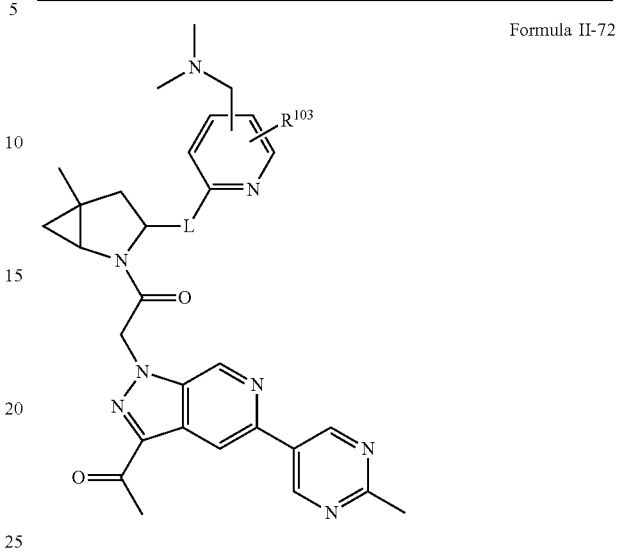
Formula II-72
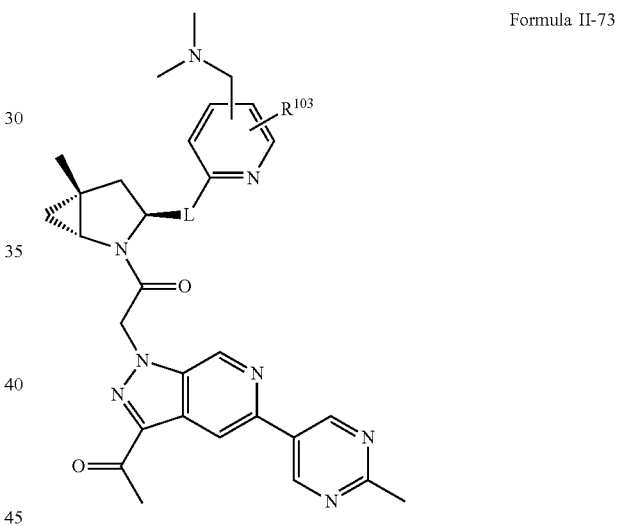
Formula II-73
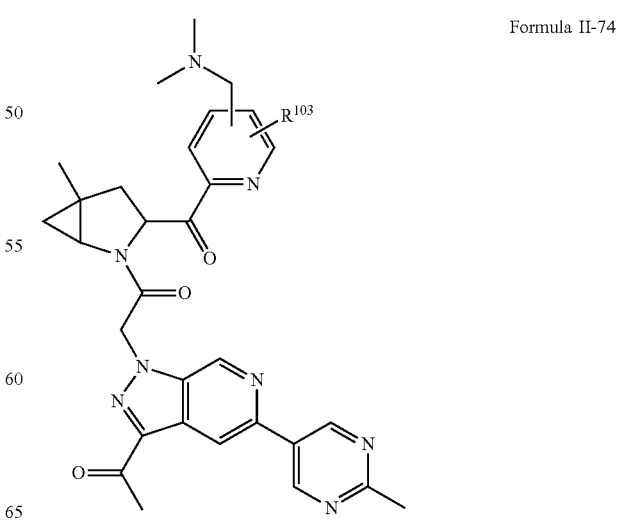
Formula II-74

TABLE 2-continued
Additional Exemplary Formulas within the Present Invention.
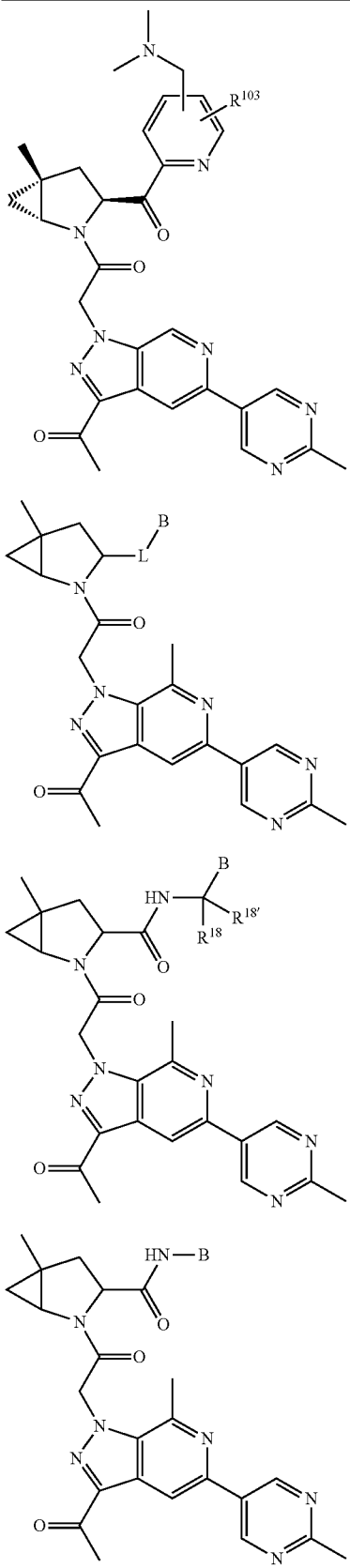
Formula II-75
Formula II-76
Formula II-77
Formula II-78
TABLE 2-continued
Additional Exemplary Formulas within the Present Invention.
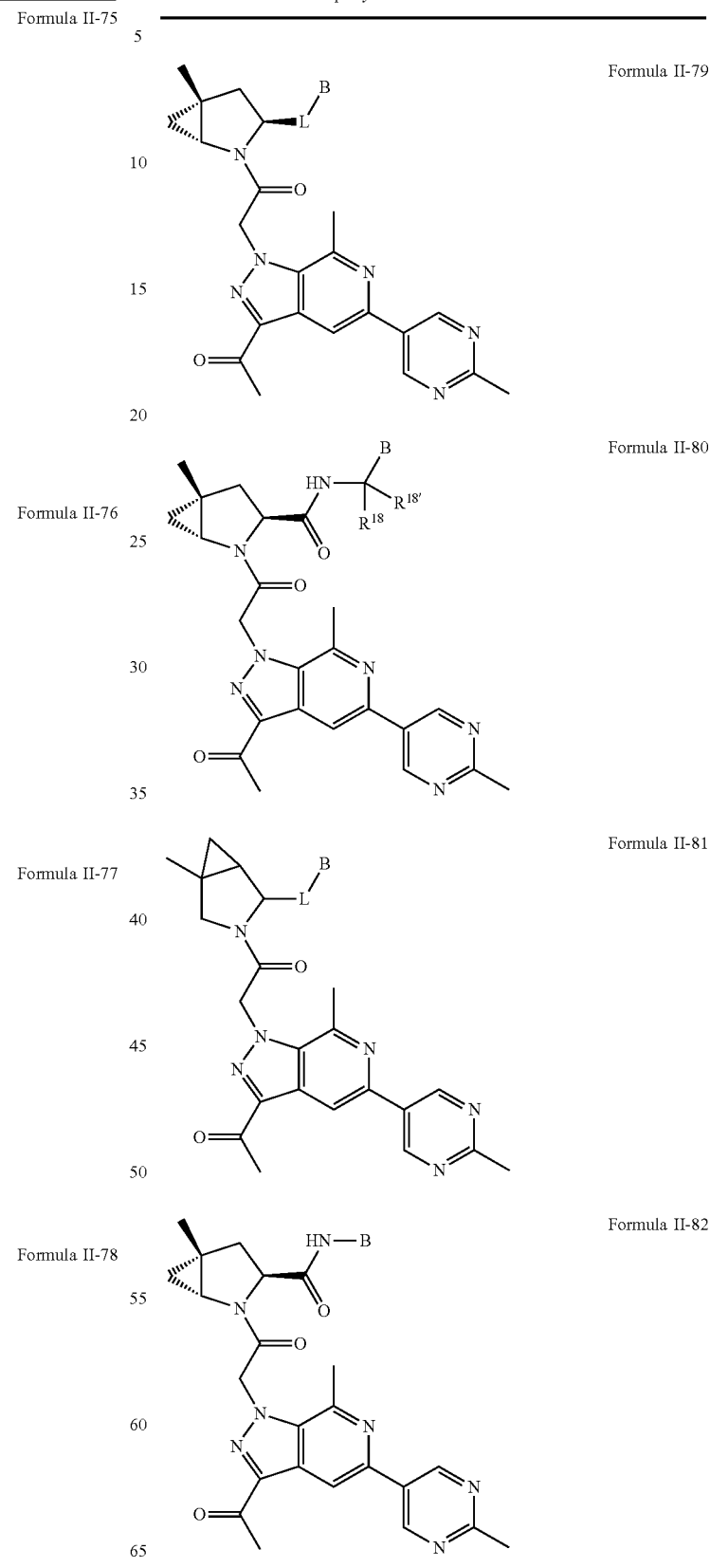
Formula II-79
Formula II-80
Formula II-81
Formula II-82

TABLE 2-continued
Additional Exemplary Formulas within the Present Invention.
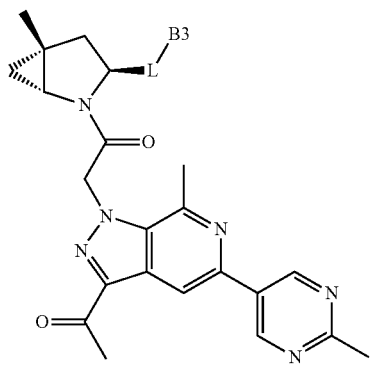
Formula II-83
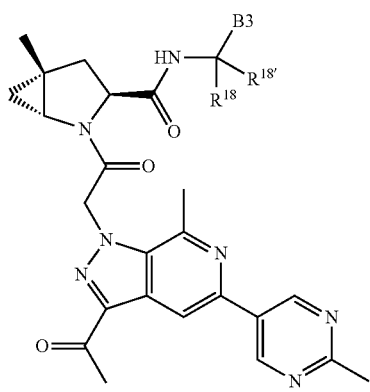
Formula II-84
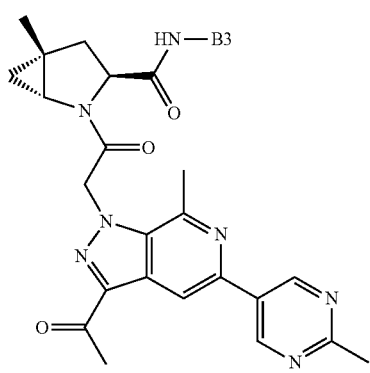
Formula II-85
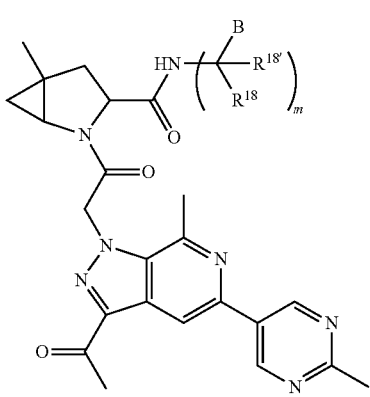
Formula II-86
TABLE 2-continued
Additional Exemplary Formulas within the Present Invention.
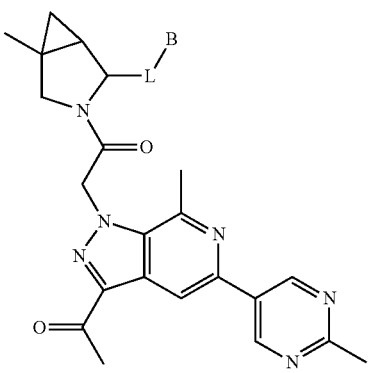
Formula II-87
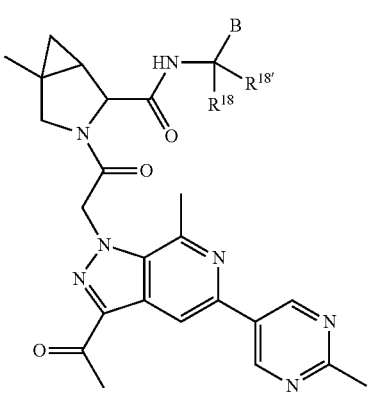
Formula II-88
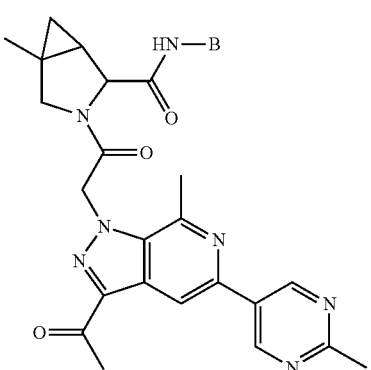
Formula II-89
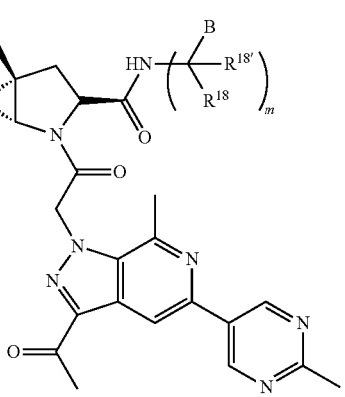
Formula II-90

TABLE 2-continued
Additional Exemplary Formulas within the Present Invention.
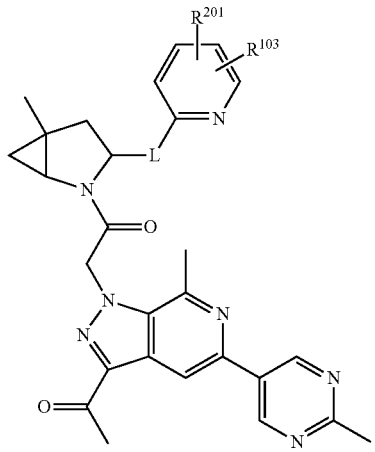
Formula II-91
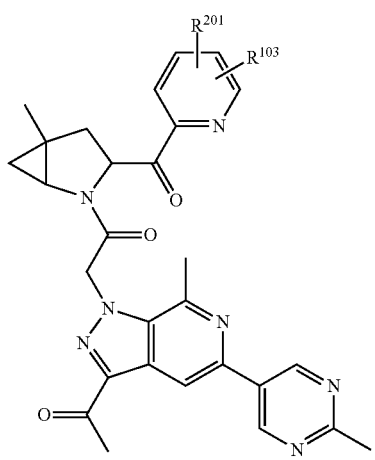
Formula II-92
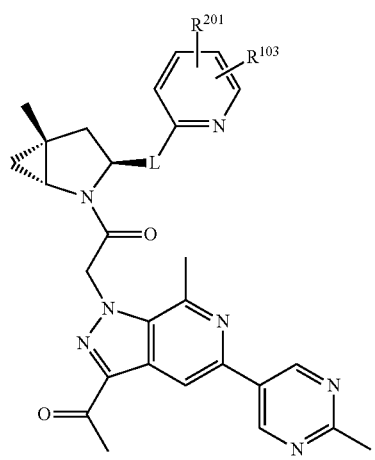
Formula II-93
TABLE 2-continued
Additional Exemplary Formulas within the Present Invention.
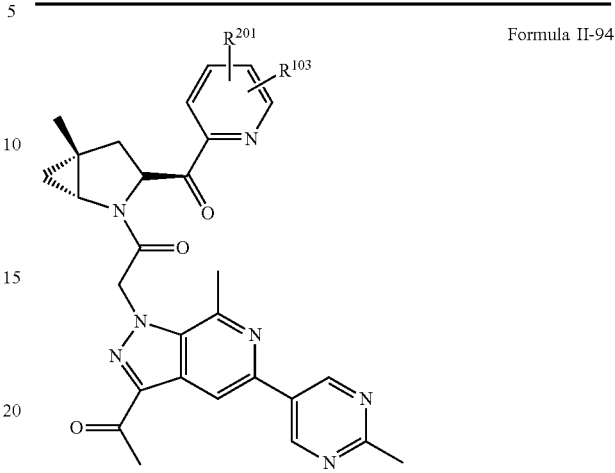
Formula II-94
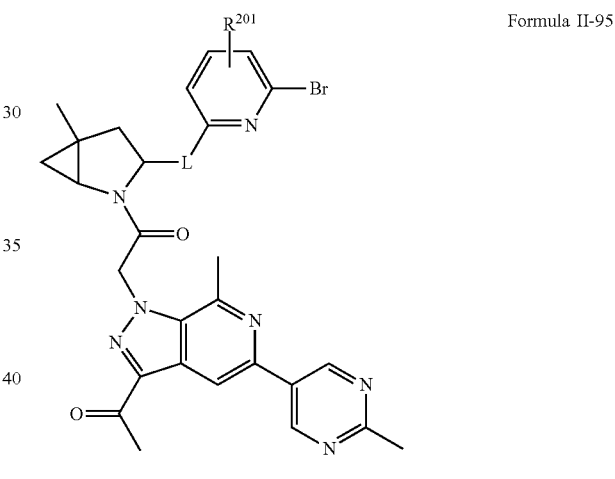
Formula II-95
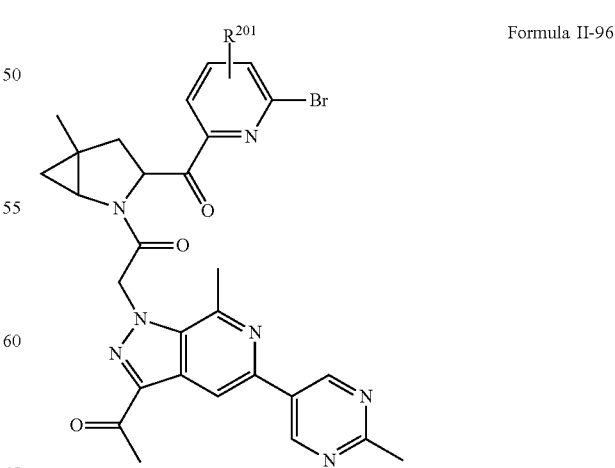
Formula II-96

TABLE 2-continued
Additional Exemplary Formulas within the Present Invention.
Formula II-97
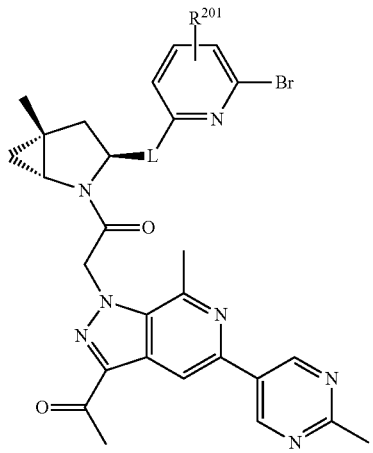
Formula II-98
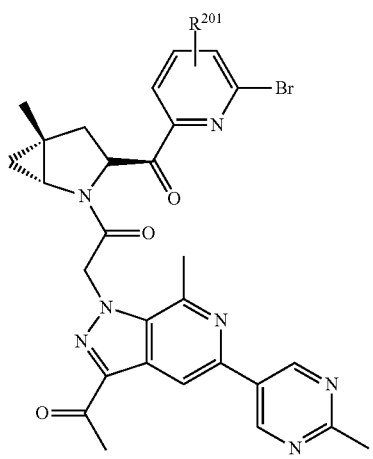
Formula II-99
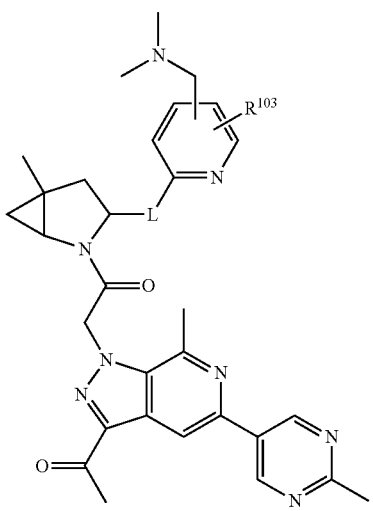
TABLE 2-continued
Additional Exemplary Formulas within the Present Invention.
Formula II-100
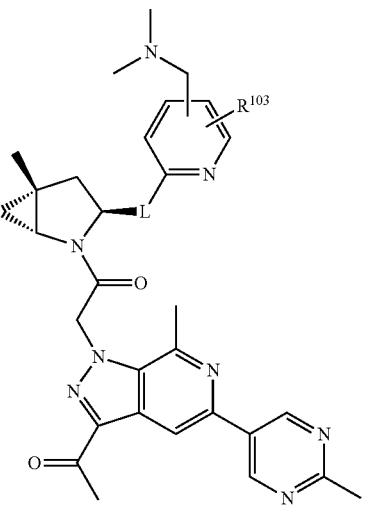
Formula II-101
Formula II-102
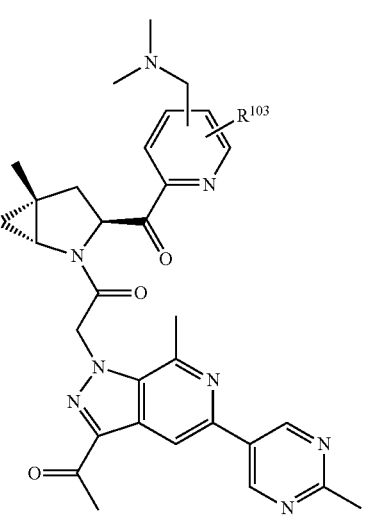

TABLE 2-continued
Additional Exemplary Formulas within the Present Invention.
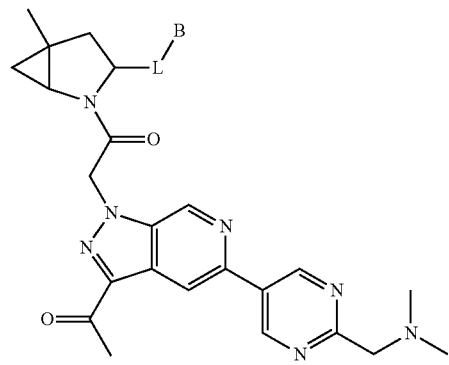
Formula II-103
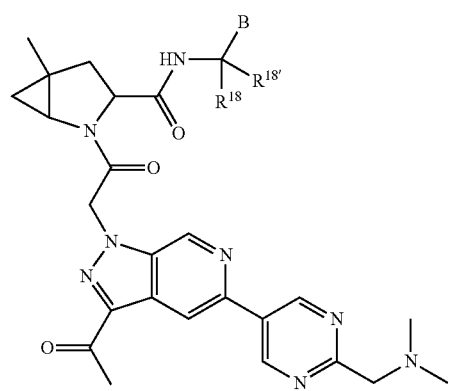
Formula II-104
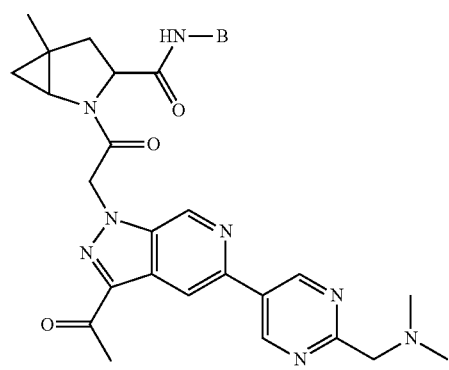
Formula II-105
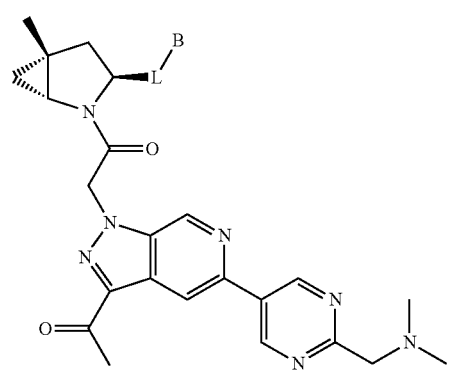
Formula II-106
TABLE 2-continued
Additional Exemplary Formulas within the Present Invention.
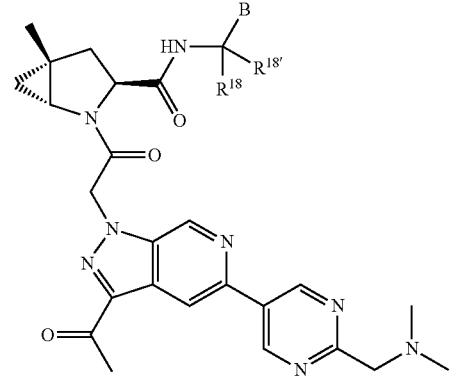
Formula II-107
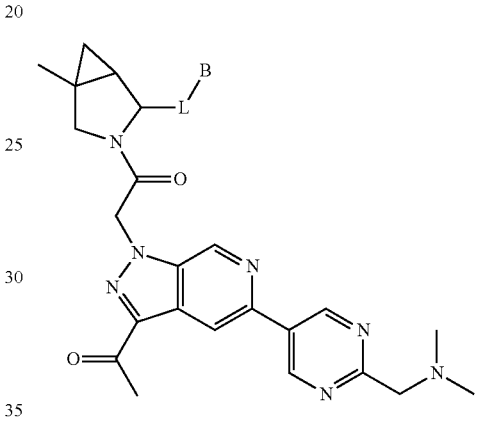
Formula II-108
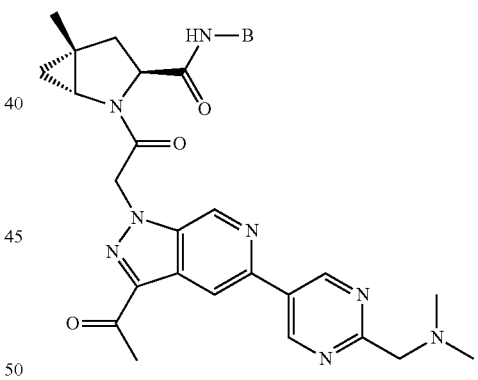
Formula II-109
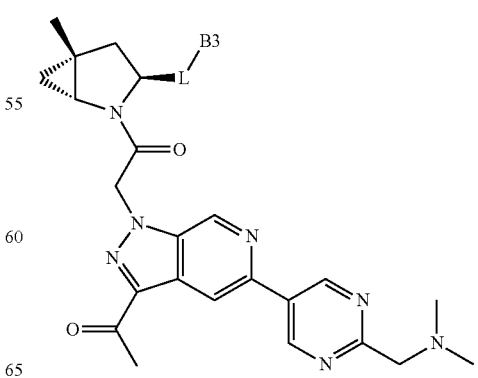
Formula II-110

TABLE 2-continued
Additional Exemplary Formulas within the Present Invention.
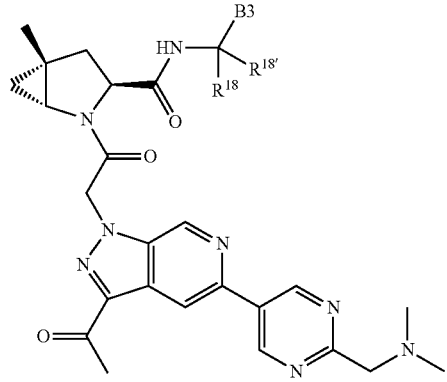
Formula II-111
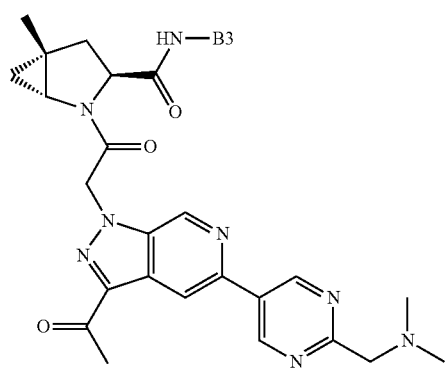
Formula II-112
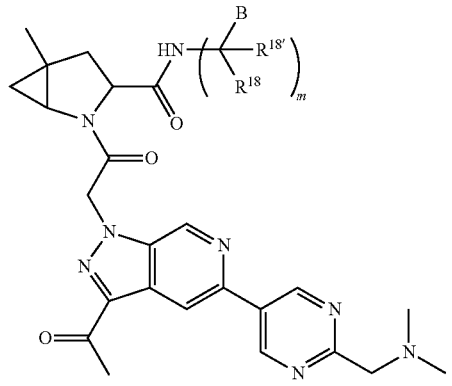
Formula II-113
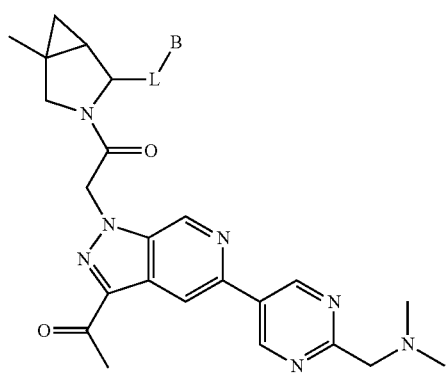
Formula II-114
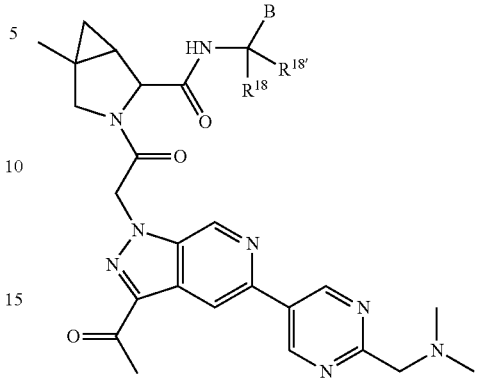
Formula II-115
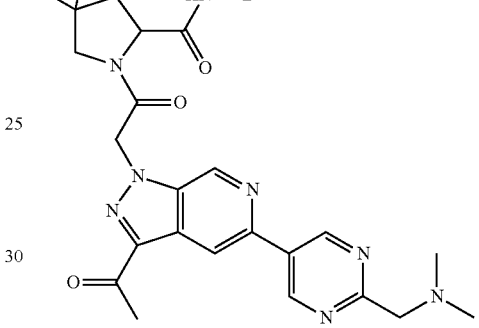
Formula II-116
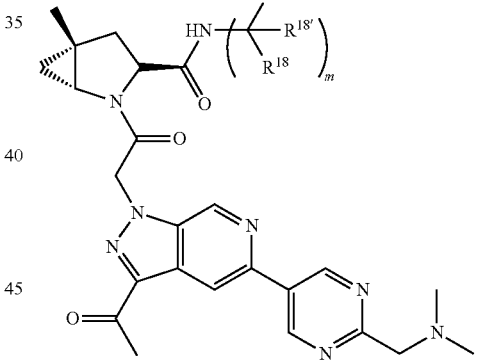
Formula II-117
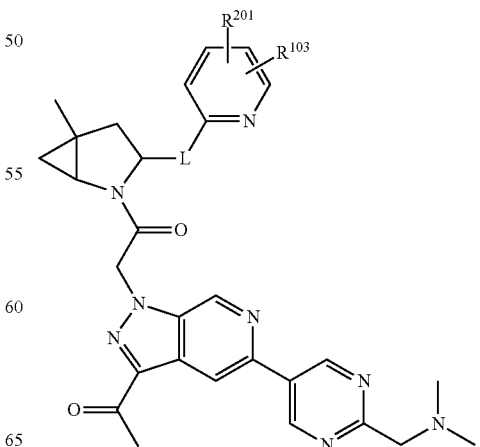
Formula II-118

TABLE 2-continued
Additional Exemplary Formulas within the Present Invention.
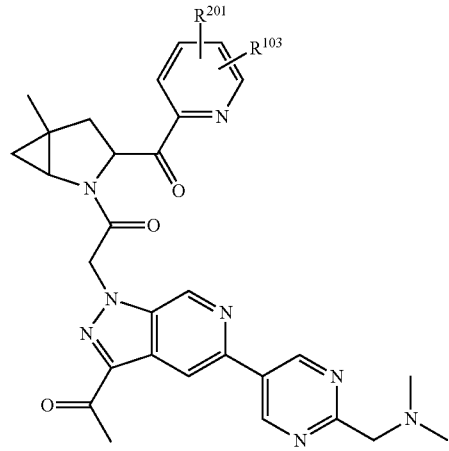
Formula II-119
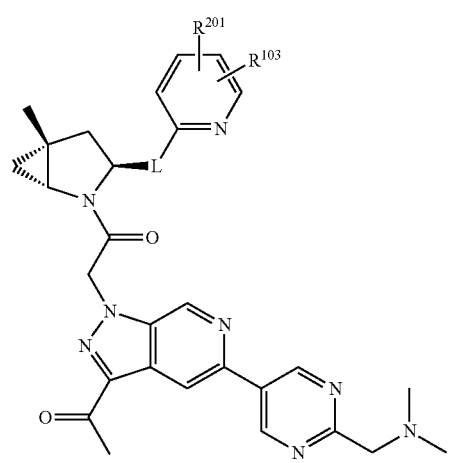
Formula II-120
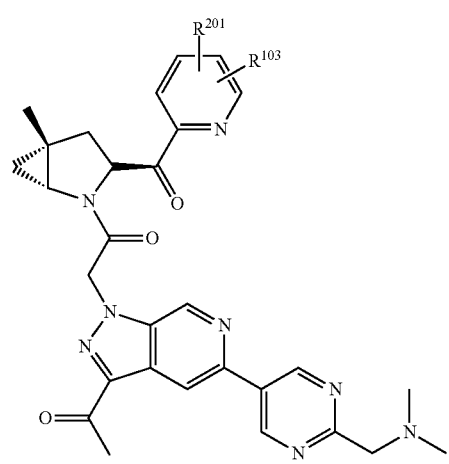
Formula II-121
TABLE 2-continued
Additional Exemplary Formulas within the Present Invention.
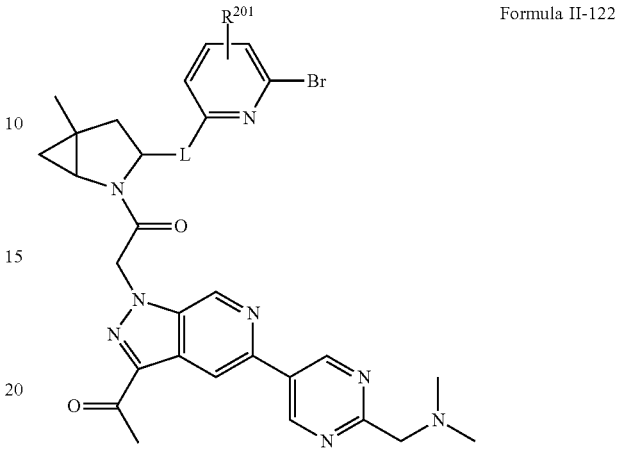
Formula II-122
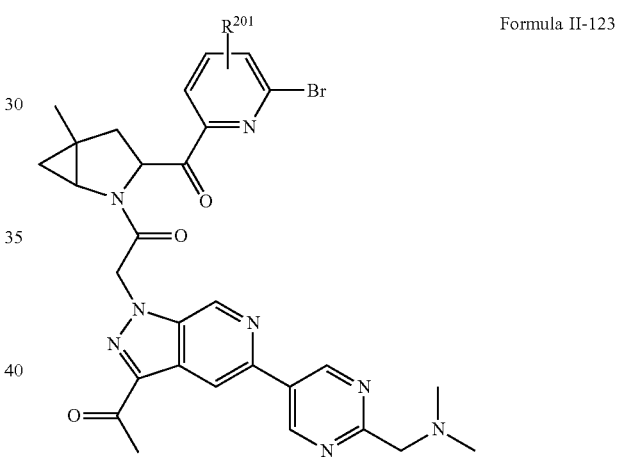
Formula II-123
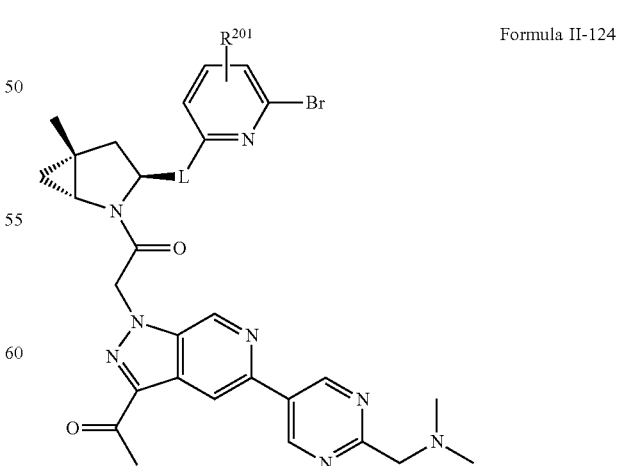
Formula II-124

TABLE 2-continued

Additional Exemplary Formulas within the Present Invention.

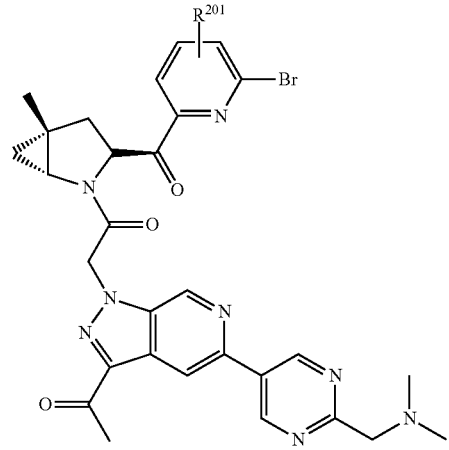

Formula II-125

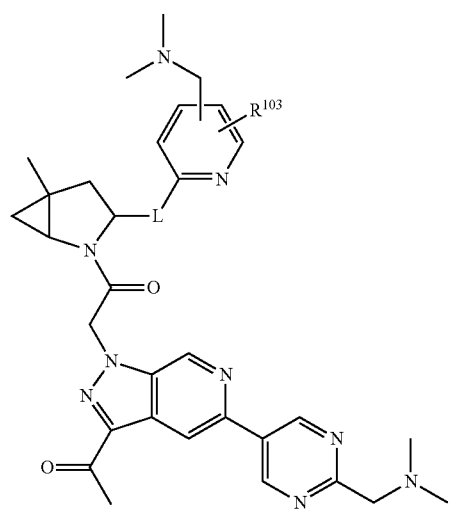

Formula II-126

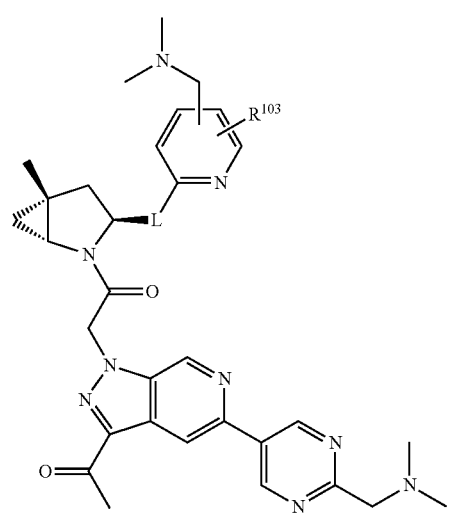

Formula II-127

TABLE 2-continued

Additional Exemplary Formulas within the Present Invention.

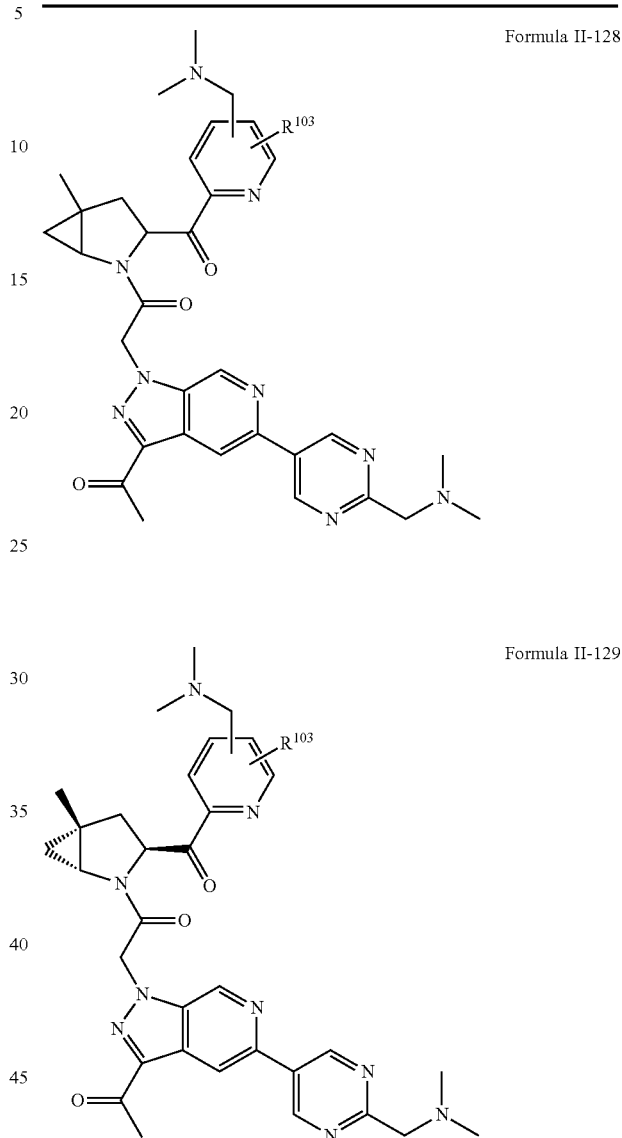

Formula II-128

Formula II-129 wherein $R^{103}$ is $C_1$-$C_4$ alkyl, $C_3$-$C_6$ cycloalkyl, fluorine, chlorine, or bromine.

TABLE 3

Additional Exemplary Formulas within the Present Invention.

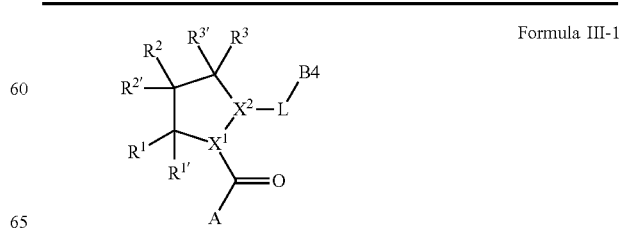

Formula III-1

TABLE 3-continued
Additional Exemplary Formulas within the Present Invention.
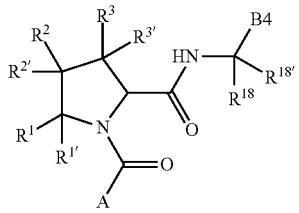 Formula III-2
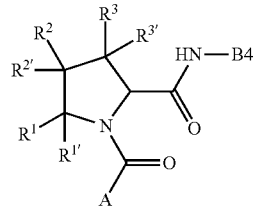 Formula III-3
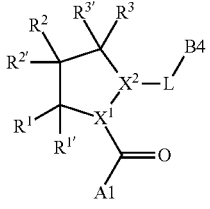 Formula III-4
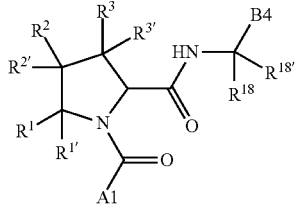 Formula III-5
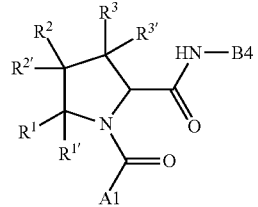 Formula III-6
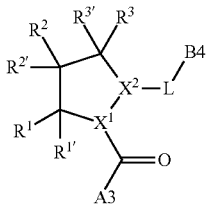 Formula III-7
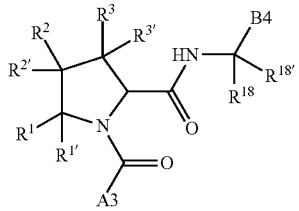 Formula III-8
TABLE 3-continued
Additional Exemplary Formulas within the Present Invention.
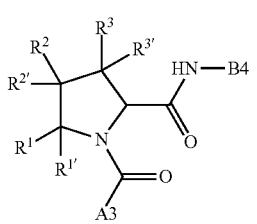 Formula III-9
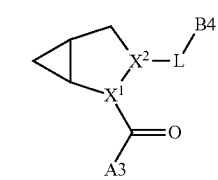 Formula III-10
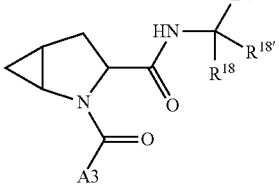 Formula III-11
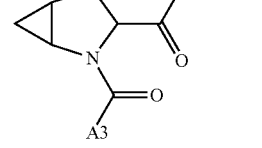 Formula III-12
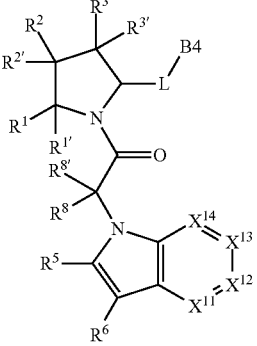 Formula III-13
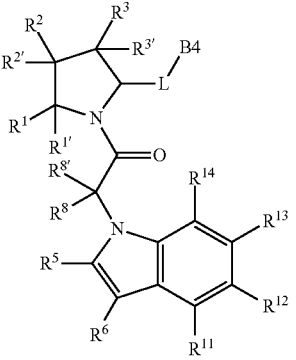 Formula III-14

TABLE 3-continued
Additional Exemplary Formulas within the Present Invention.
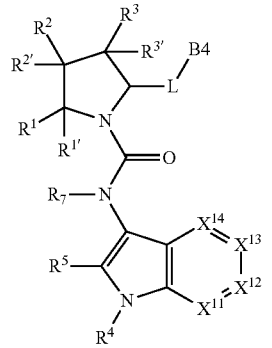
Formula III-15
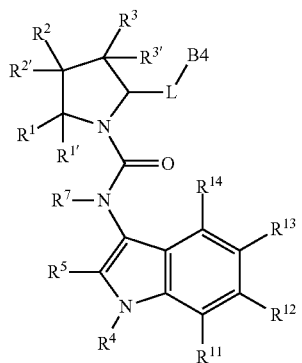
Formula III-16
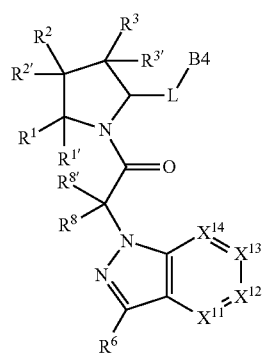
Formula III-17
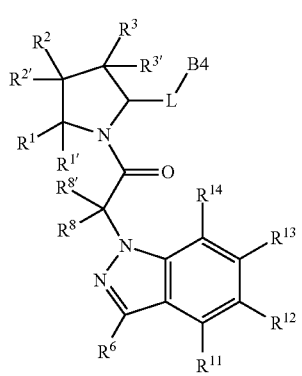
Formula III-18
TABLE 3-continued
Additional Exemplary Formulas within the Present Invention.
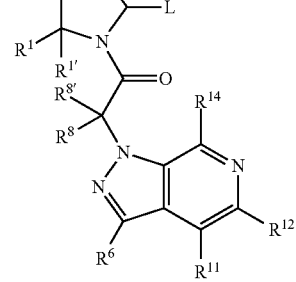
Formula III-19
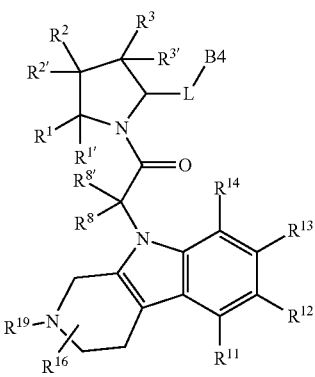
Formula III-20
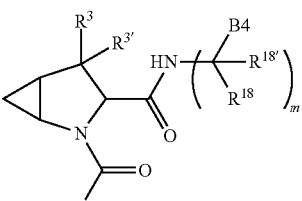
Formula III-21
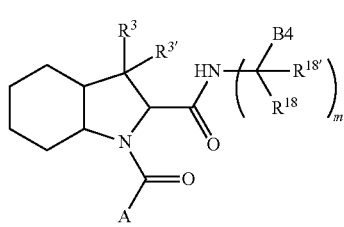
Formula III-22
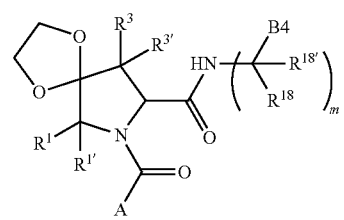
Formula III-23

TABLE 3-continued
Additional Exemplary Formulas within the Present Invention.
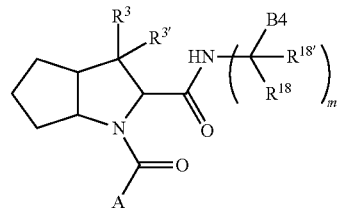
Formula III-24
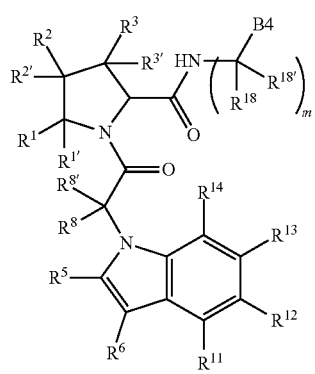
Formula III-25
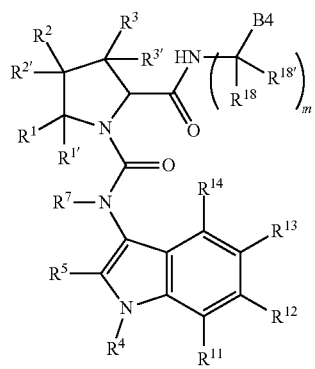
Formula III-26
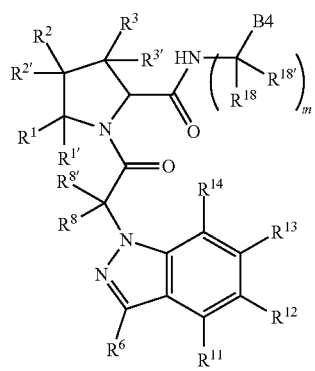
Formula III-27
TABLE 3-continued
Additional Exemplary Formulas within the Present Invention.
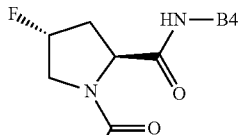
Formula III-28
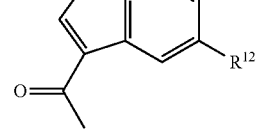
Formula III-29
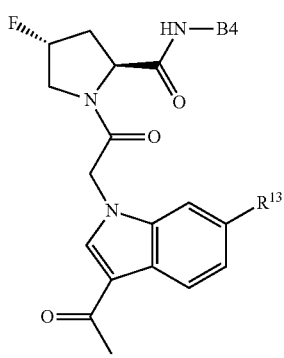
Formula III-30
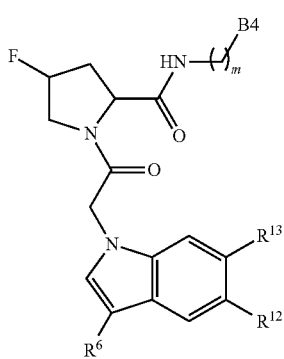
Formula III-31

TABLE 3-continued
Additional Exemplary Formulas within the Present Invention.
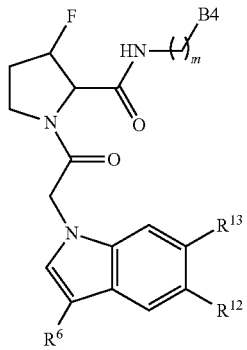
Formula III-32
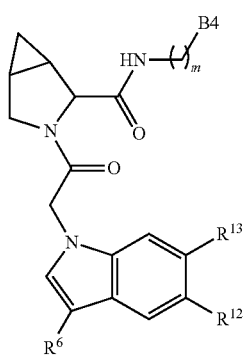
Formula III-33
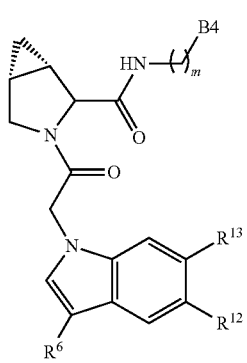
Formula III-34
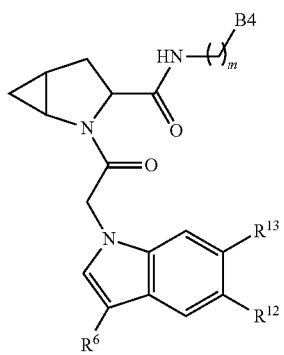
Formula III-35
TABLE 3-continued
Additional Exemplary Formulas within the Present Invention.
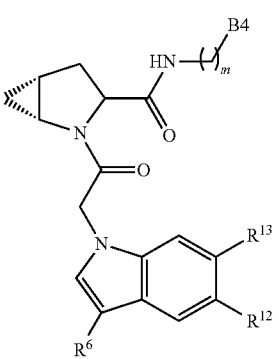
Formula III-36
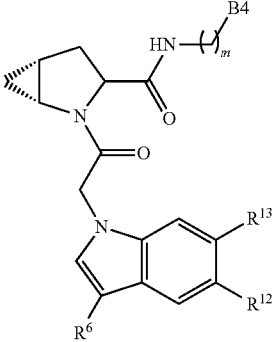
Formula III-37
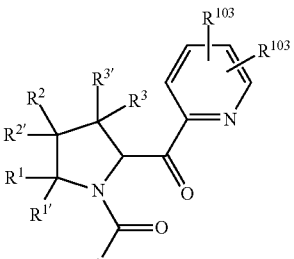
Formula III-38
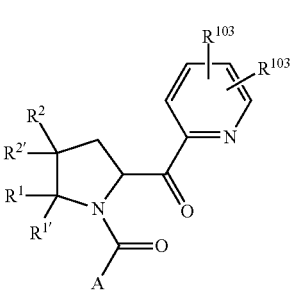
Formula III-39
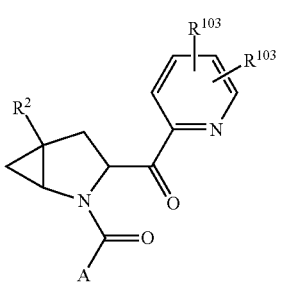
Formula III-40
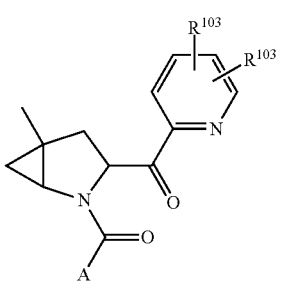

TABLE 3-continued

Additional Exemplary Formulas within the Present Invention.

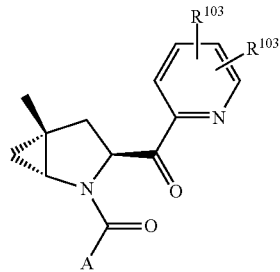

Formula III-41

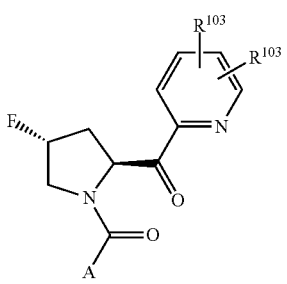

Formula III-42

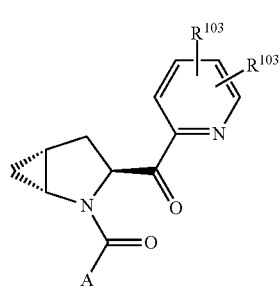

Formula III-43

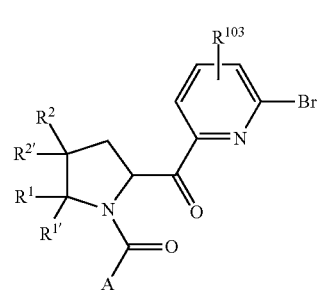

Formula III-44

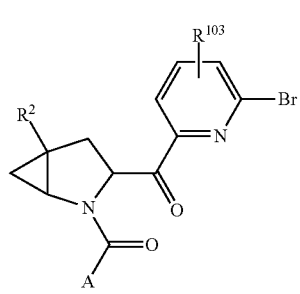

Formula III-45

TABLE 3-continued

Additional Exemplary Formulas within the Present Invention.

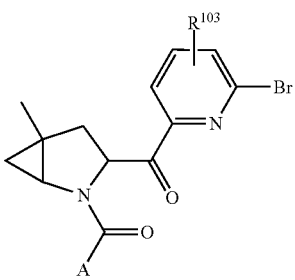

Formula III-46

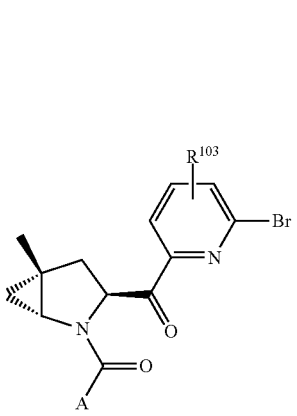

Formula III-47


Formula III-48

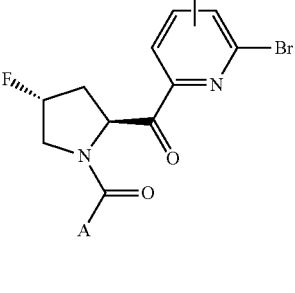

Formula III-49

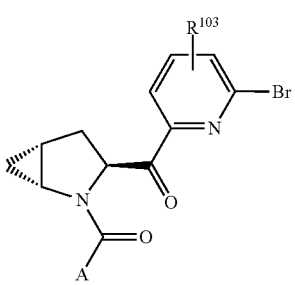

wherein $R^{103}$ is independently $C_1$-$C_4$ alkyl, $C_3$-$C_6$ cycloalkyl, fluorine, chlorine, or bromine.

TABLE 4
Additional Exemplary Formulas within the Present Invention.
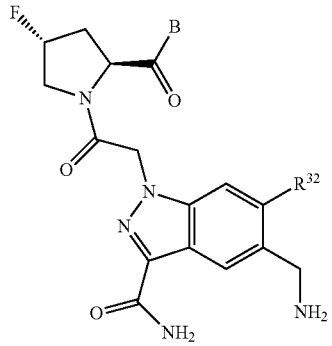
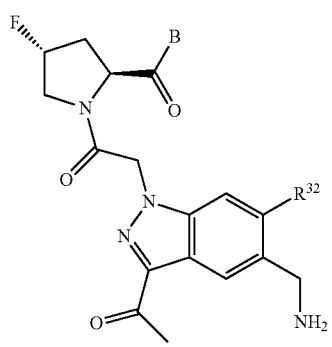
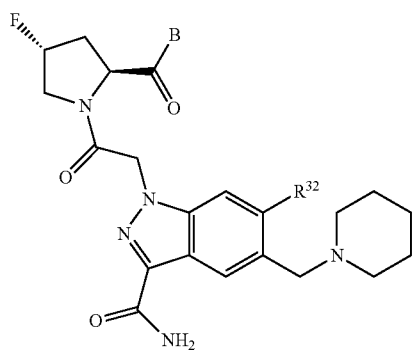
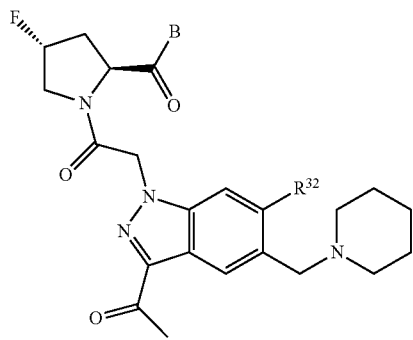
TABLE 4-continued
Additional Exemplary Formulas within the Present Invention.
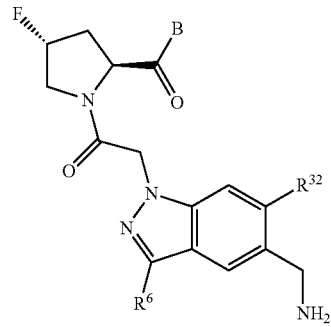
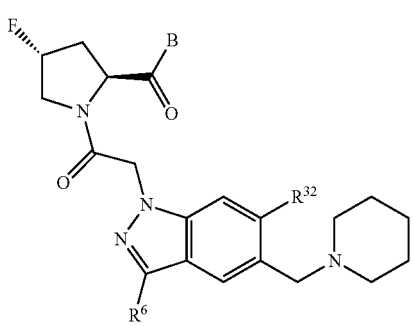
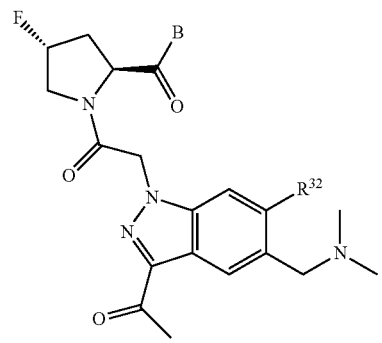
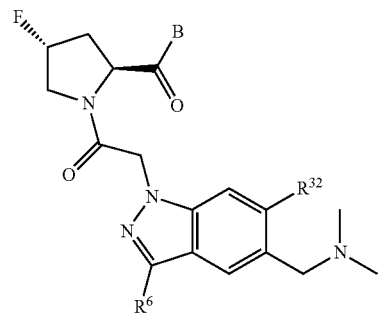

TABLE 4-continued
Additional Exemplary Formulas within the Present Invention.
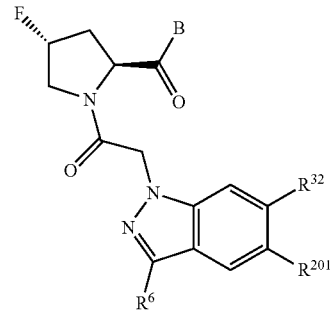
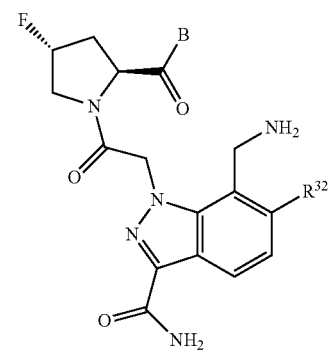
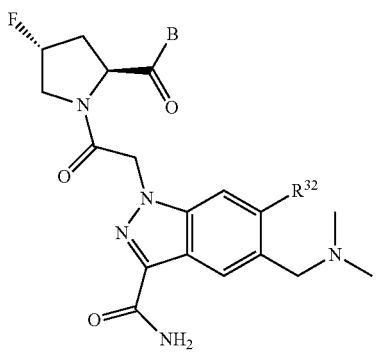
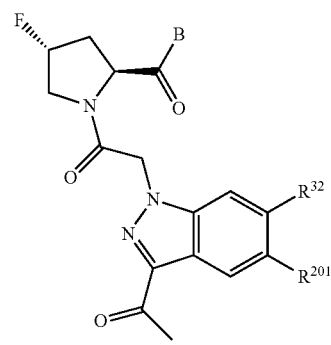
TABLE 4-continued
Additional Exemplary Formulas within the Present Invention.
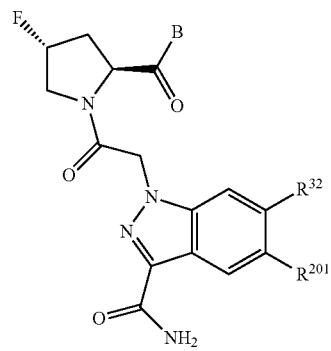
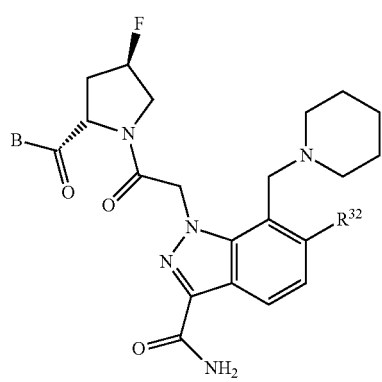
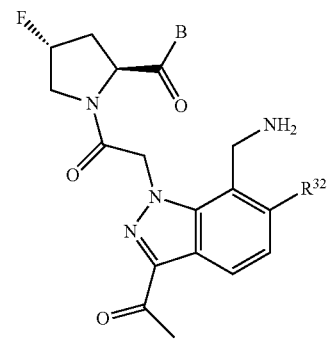
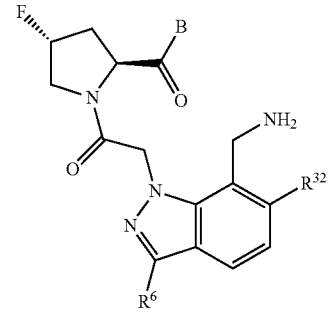

TABLE 4-continued
Additional Exemplary Formulas within the Present Invention.
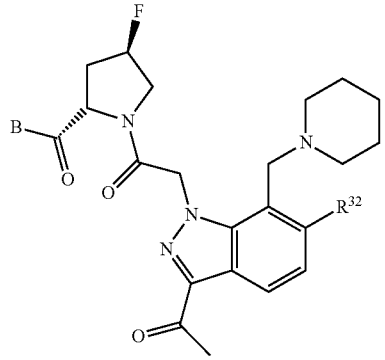
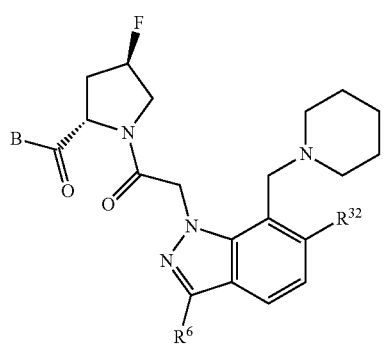
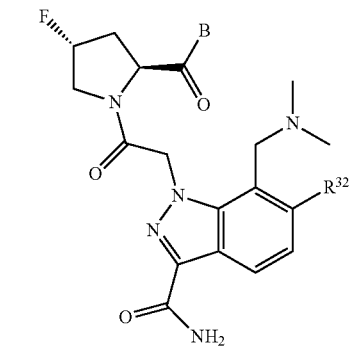
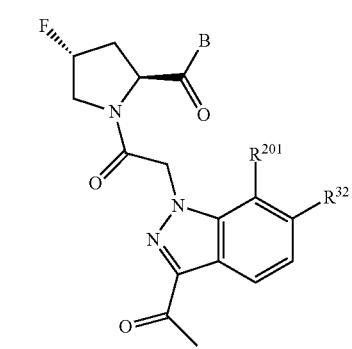
TABLE 4-continued
Additional Exemplary Formulas within the Present Invention.
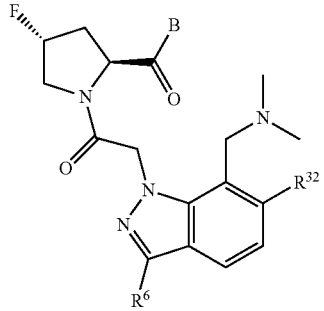
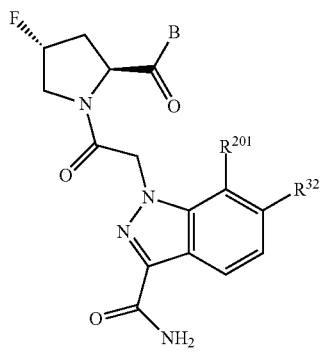
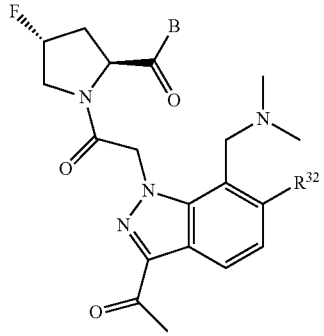
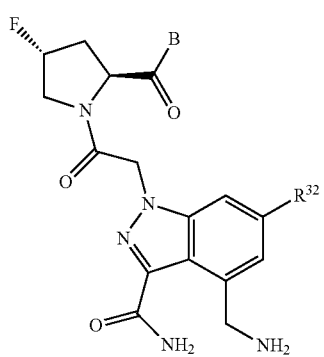

TABLE 4-continued
Additional Exemplary Formulas within the Present Invention.
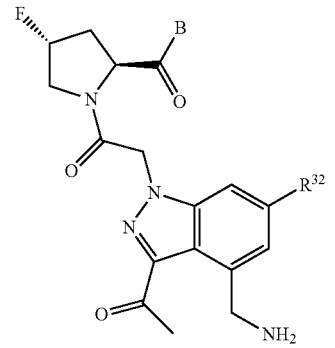
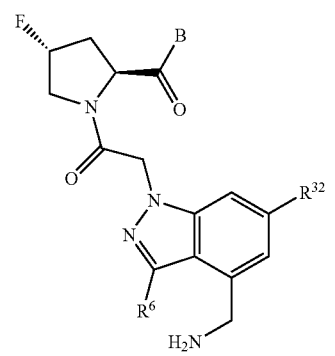
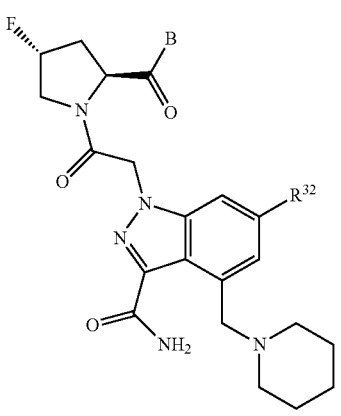
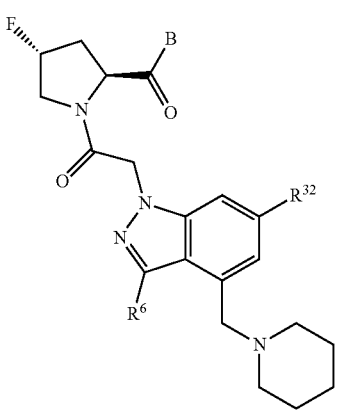
TABLE 4-continued
Additional Exemplary Formulas within the Present Invention.
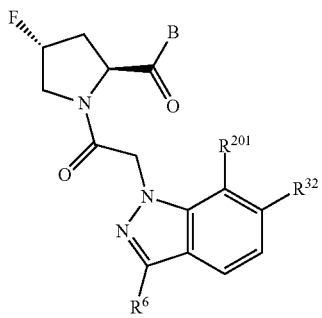
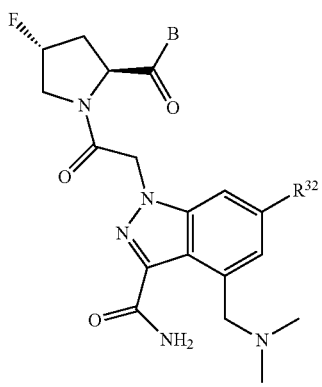
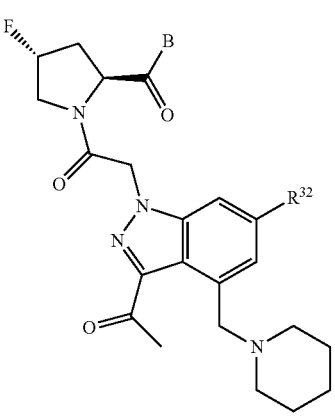
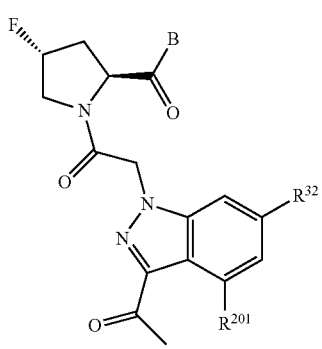

TABLE 4-continued
Additional Exemplary Formulas within the Present Invention.
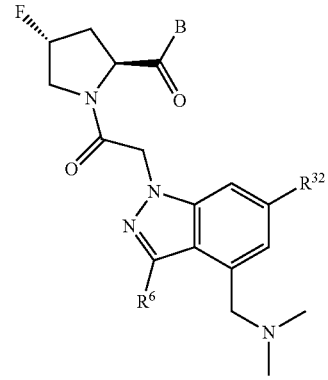
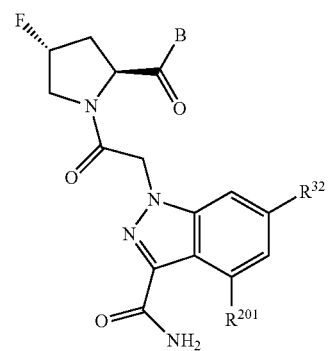
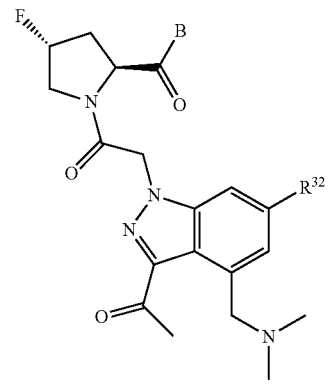
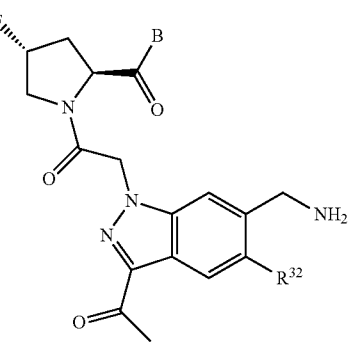
TABLE 4-continued
Additional Exemplary Formulas within the Present Invention.
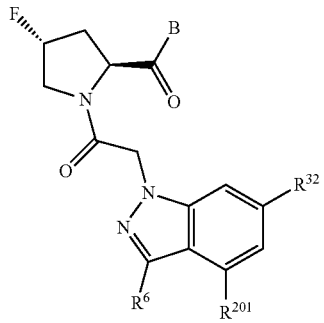
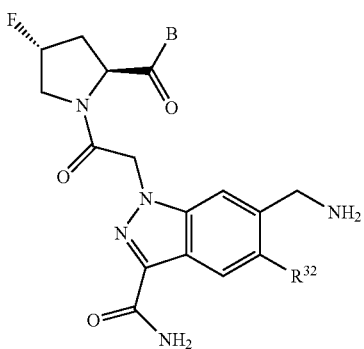
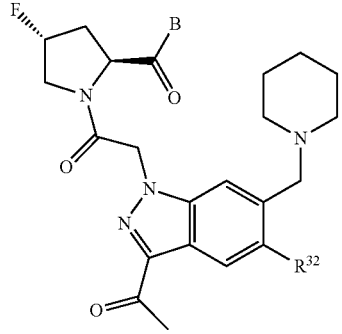
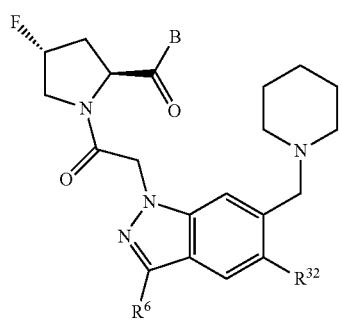

475
TABLE 4-continued
Additional Exemplary Formulas within the Present Invention.
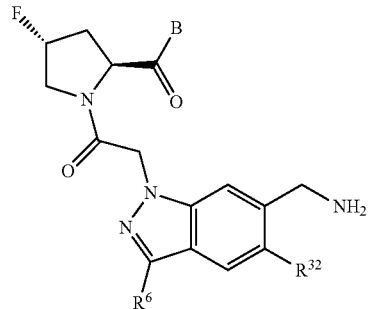
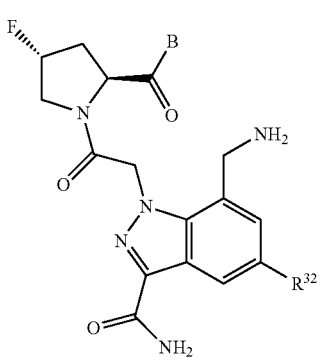
476
TABLE 4-continued
Additional Exemplary Formulas within the Present Invention.
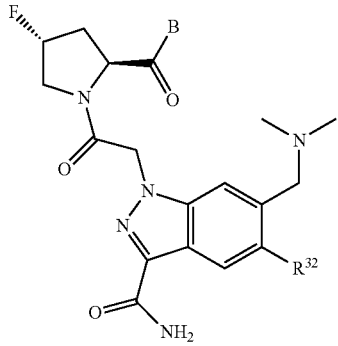
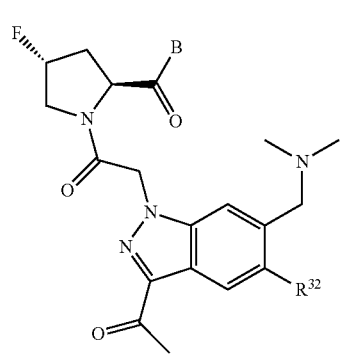
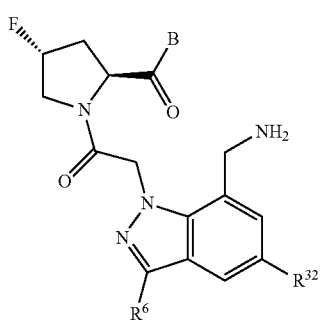
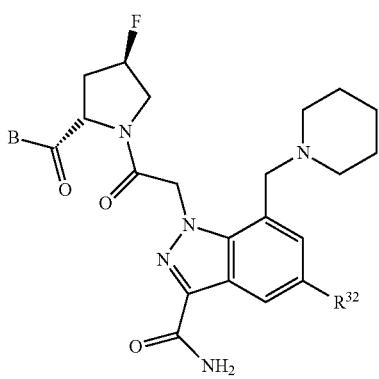

TABLE 4-continued
Additional Exemplary Formulas within the Present Invention.
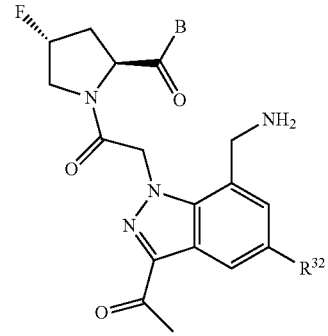
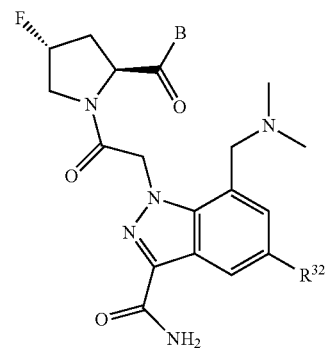
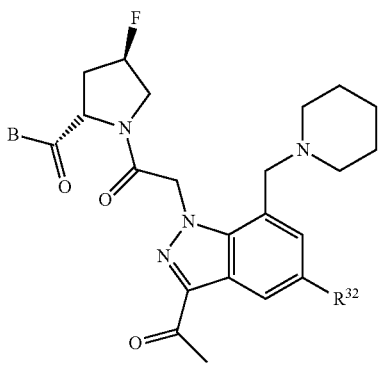
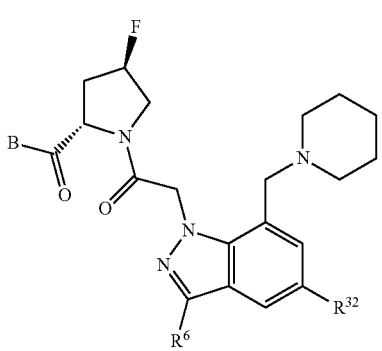
TABLE 4-continued
Additional Exemplary Formulas within the Present Invention.
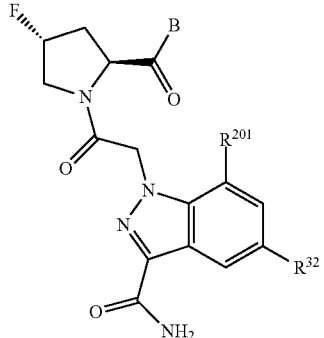
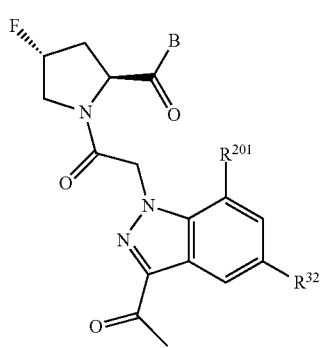
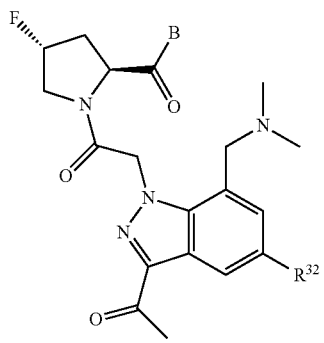
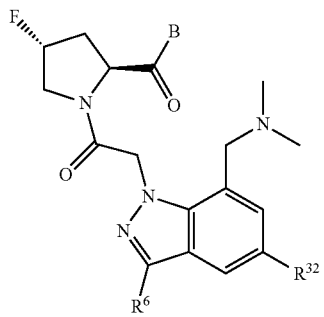

TABLE 4-continued
Additional Exemplary Formulas within the Present Invention.
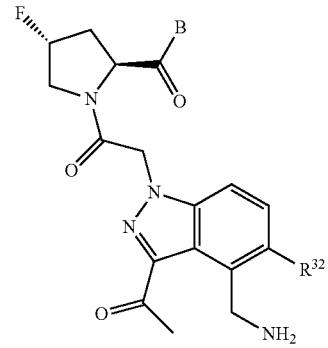
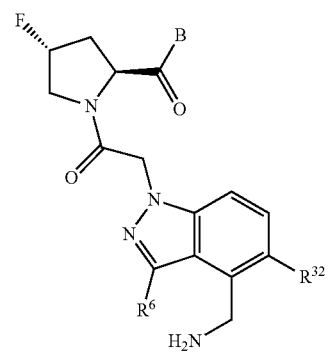
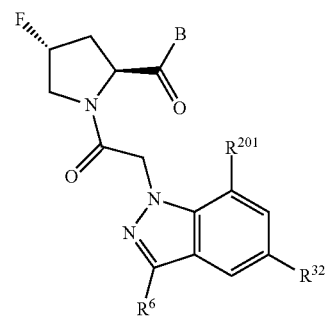
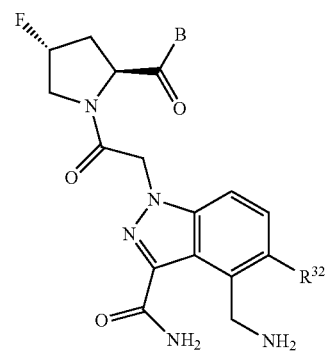
TABLE 4-continued
Additional Exemplary Formulas within the Present Invention.
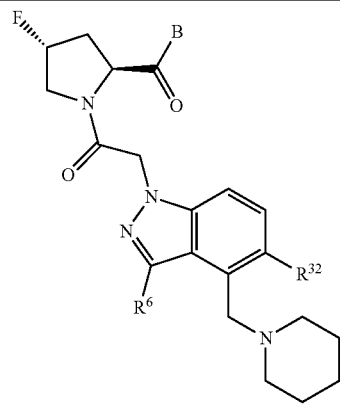
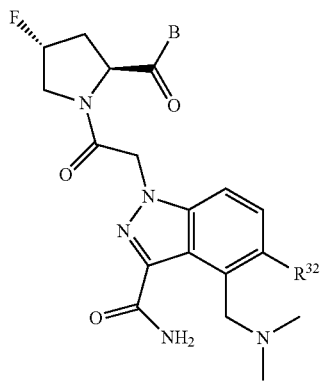
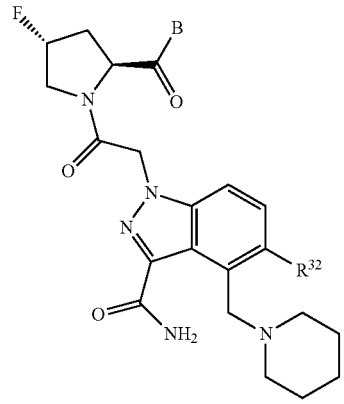
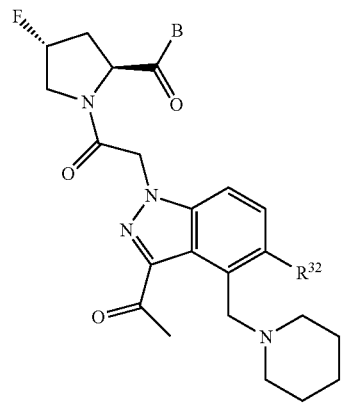

TABLE 4-continued
Additional Exemplary Formulas within the Present Invention.
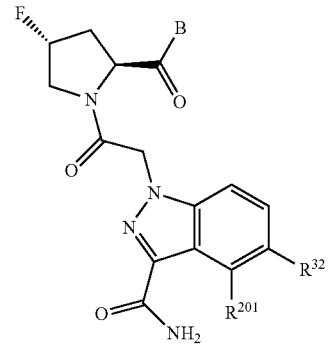
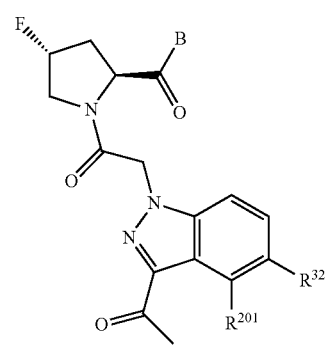
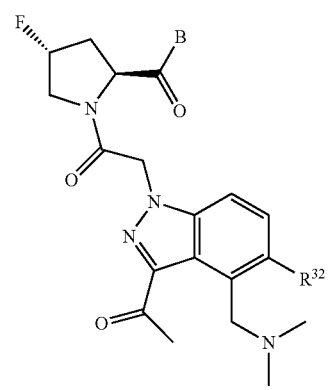
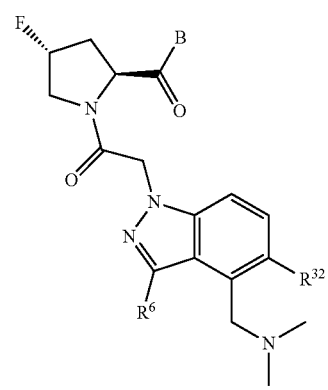
TABLE 4-continued
Additional Exemplary Formulas within the Present Invention.
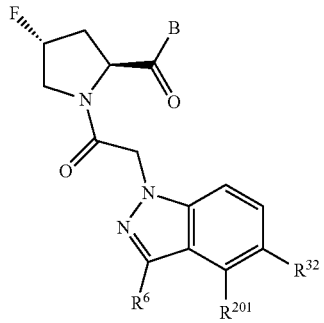
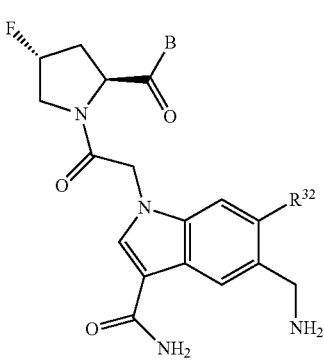
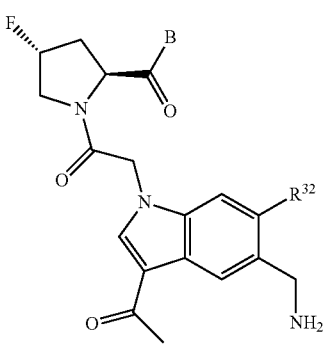
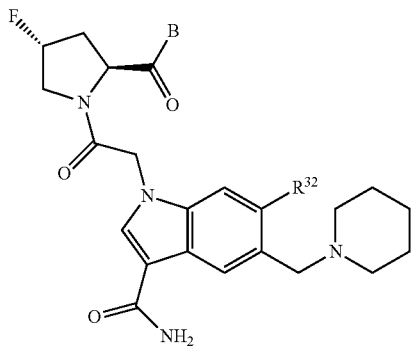

TABLE 4-continued
Additional Exemplary Formulas within the Present Invention.
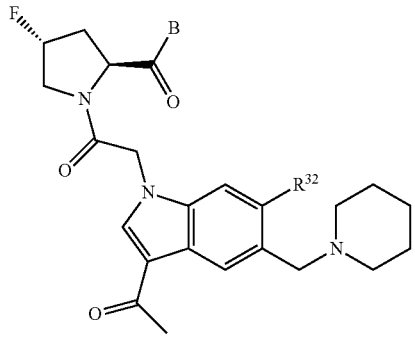
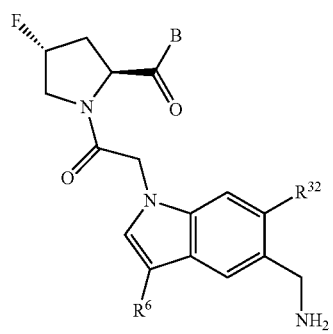
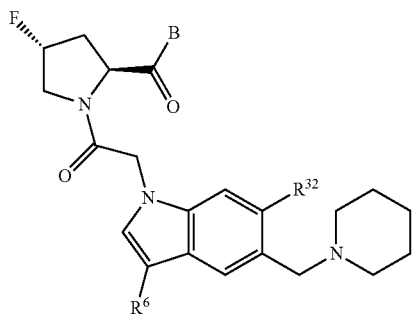
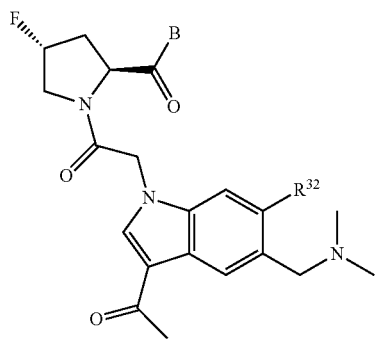
TABLE 4-continued
Additional Exemplary Formulas within the Present Invention.
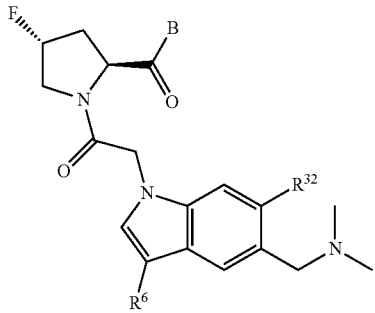
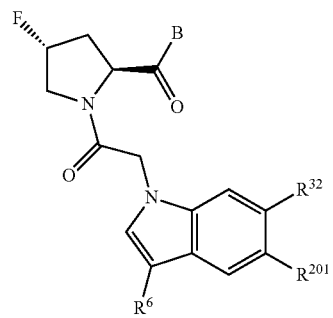
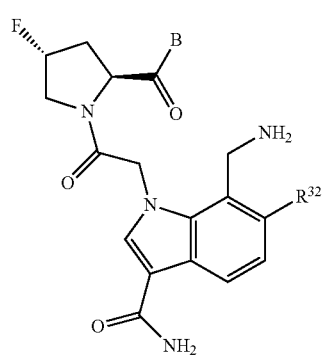
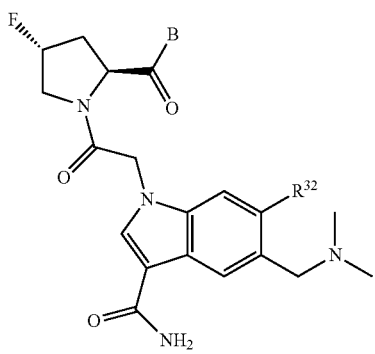

TABLE 4-continued
Additional Exemplary Formulas within the Present Invention.
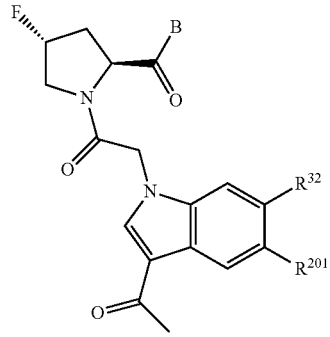
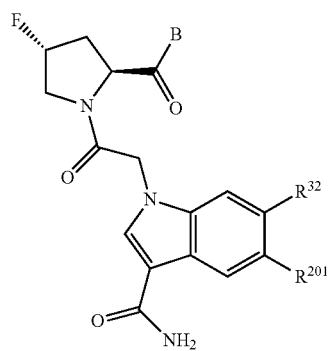
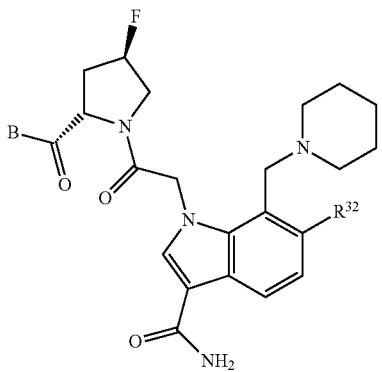
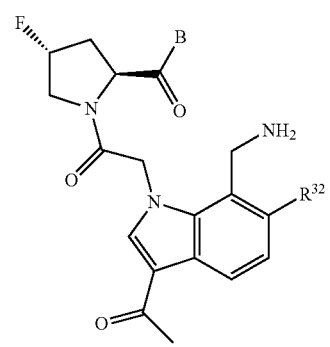
TABLE 4-continued
Additional Exemplary Formulas within the Present Invention.
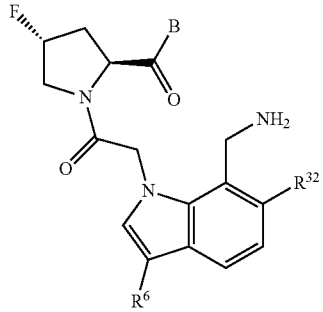
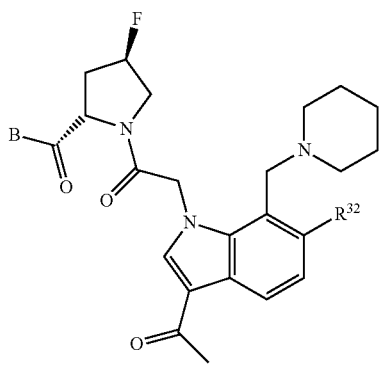
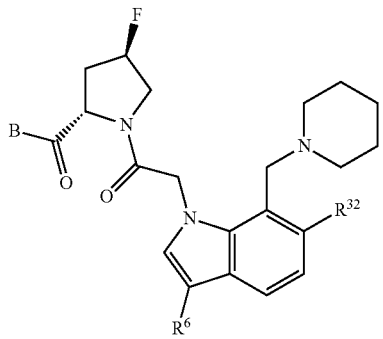
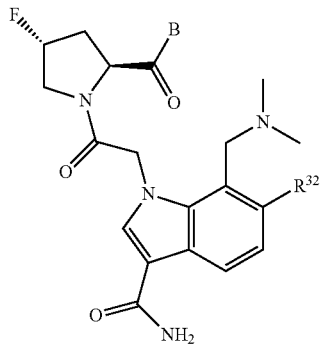

TABLE 4-continued
Additional Exemplary Formulas within the Present Invention.
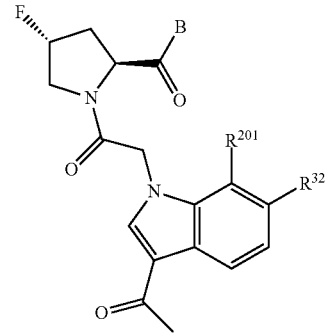
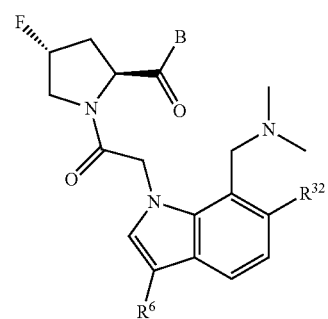
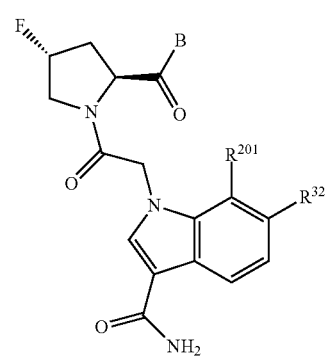
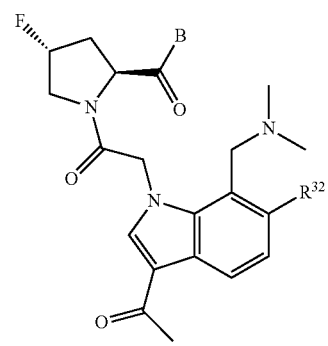
TABLE 4-continued
Additional Exemplary Formulas within the Present Invention.
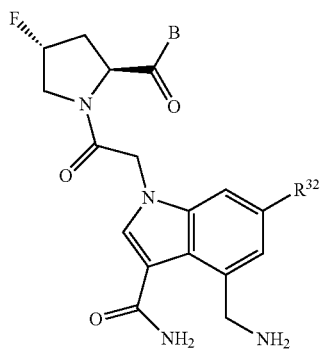
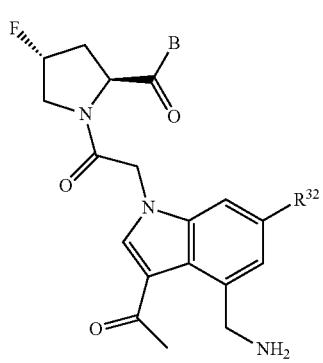
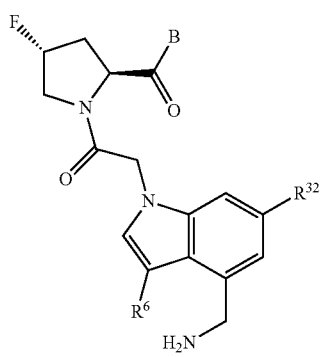
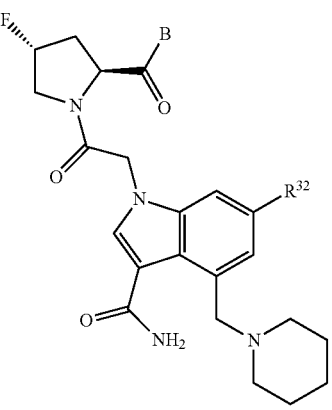

TABLE 4-continued
Additional Exemplary Formulas within the Present Invention.
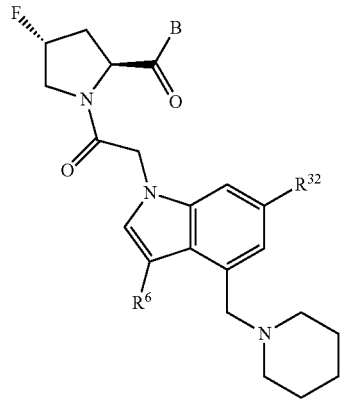
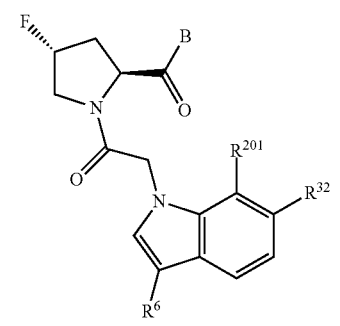
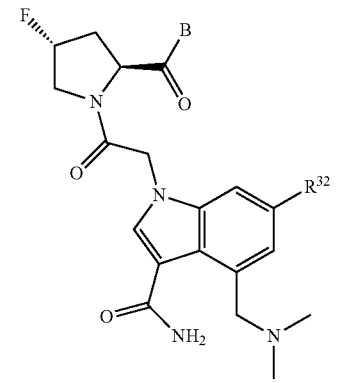
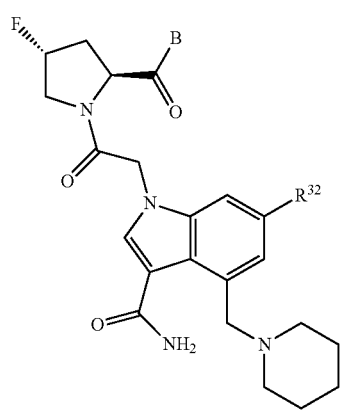
TABLE 4-continued
Additional Exemplary Formulas within the Present Invention.
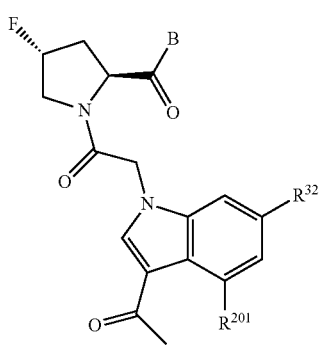
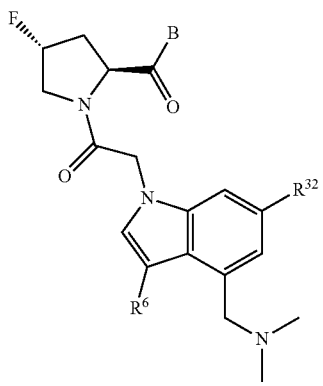
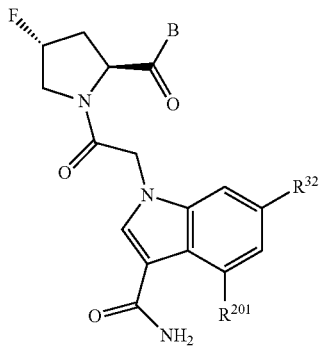
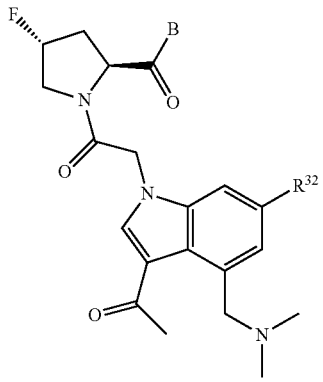

TABLE 4-continued
Additional Exemplary Formulas within the Present Invention.
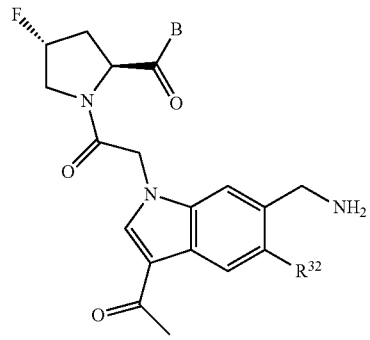
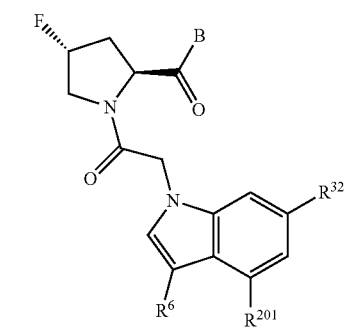
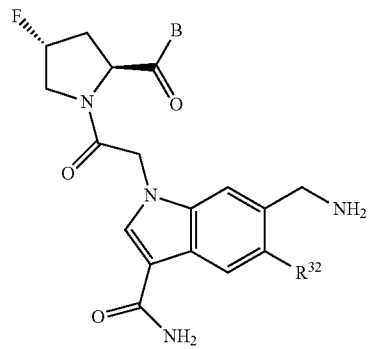
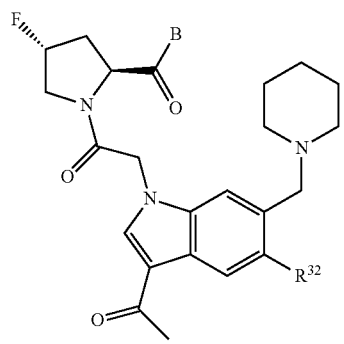
TABLE 4-continued
Additional Exemplary Formulas within the Present Invention.
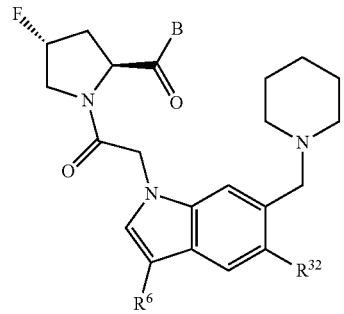
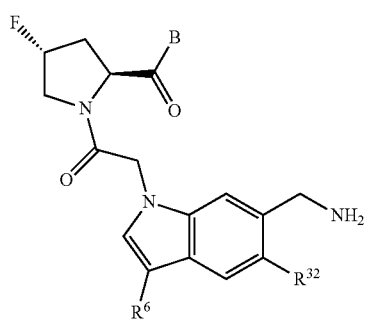
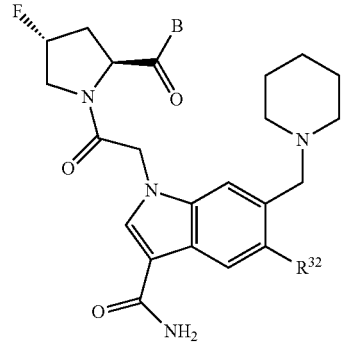

TABLE 4-continued
Additional Exemplary Formulas within the Present Invention.
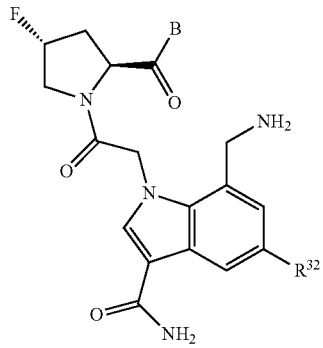
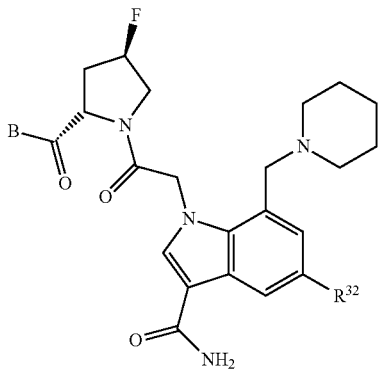
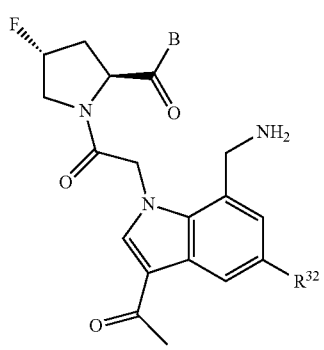
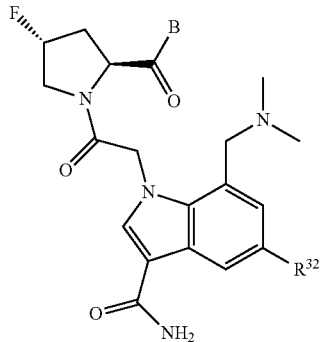
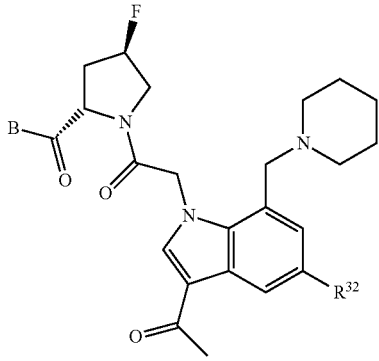

TABLE 4-continued
Additional Exemplary Formulas within the Present Invention.
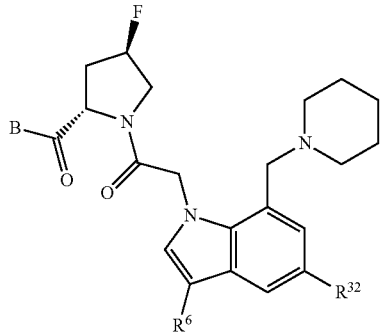
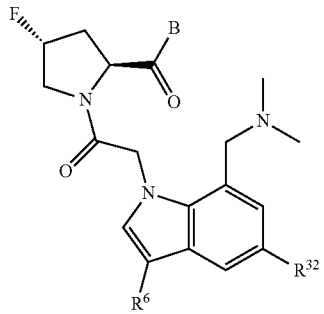
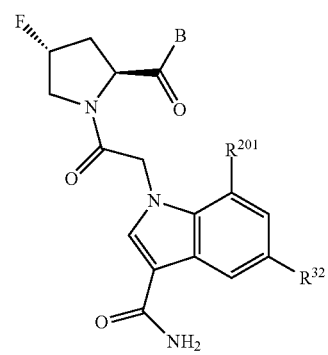
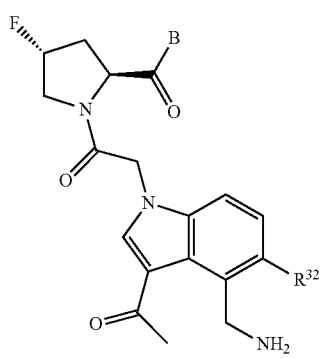
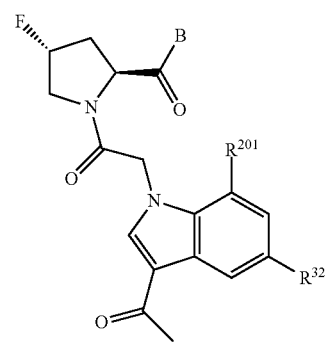
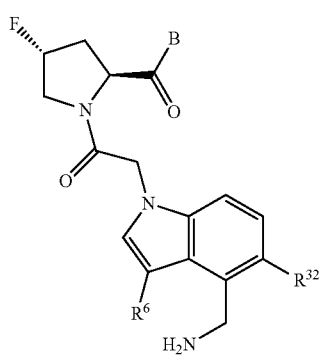
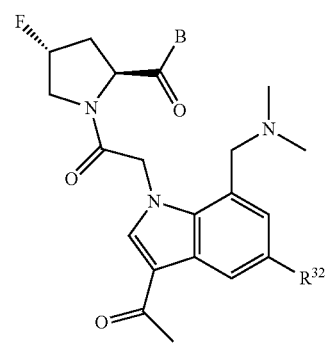
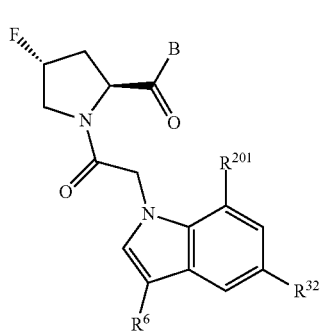

TABLE 4-continued
Additional Exemplary Formulas within the Present Invention.
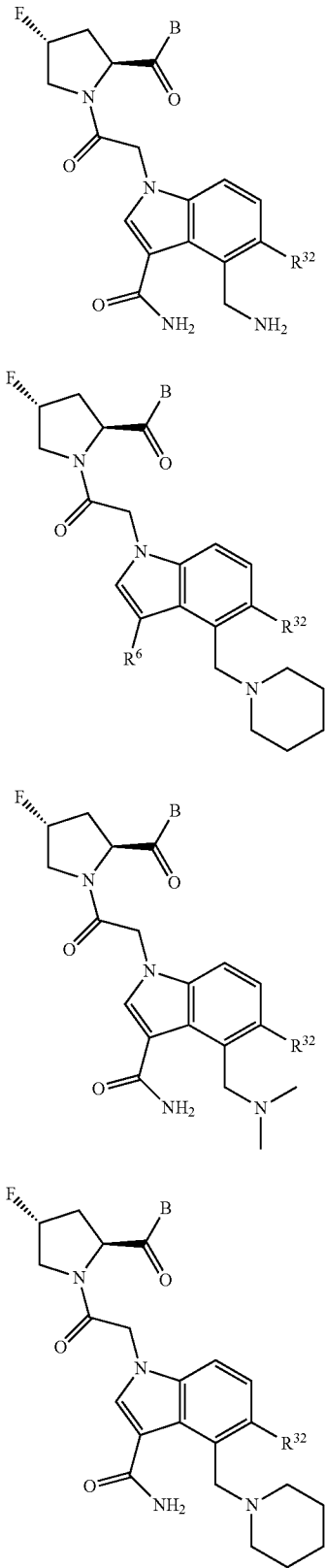
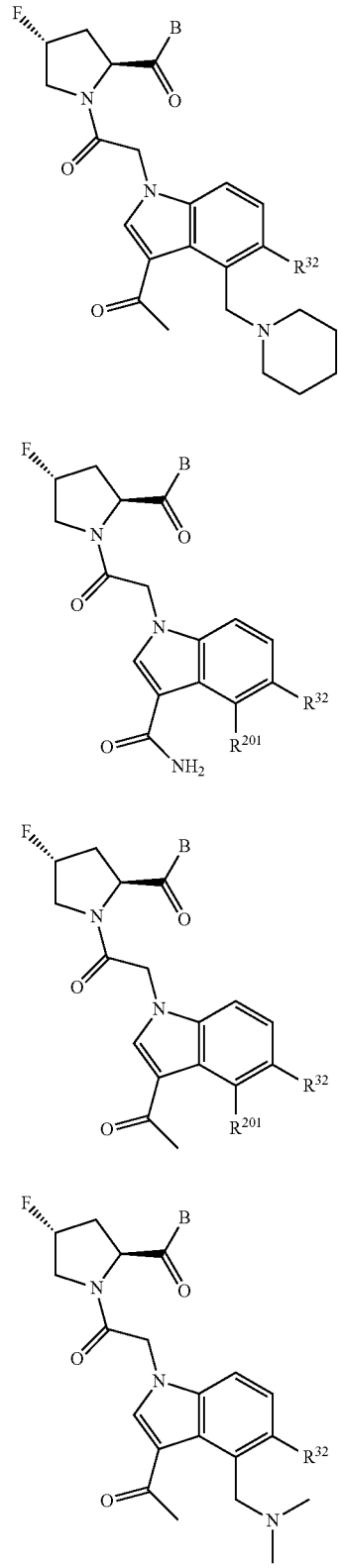

TABLE 4-continued
Additional Exemplary Formulas within the Present Invention.
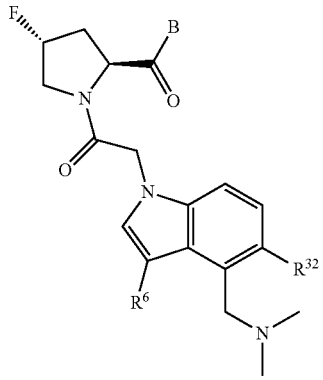
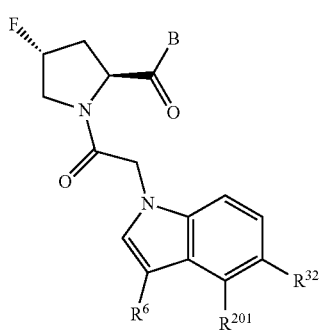
TABLE 5
Additional Exemplary Formulas within the Present Invention.
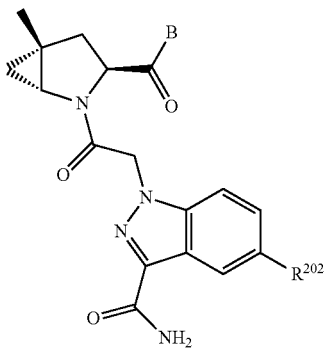
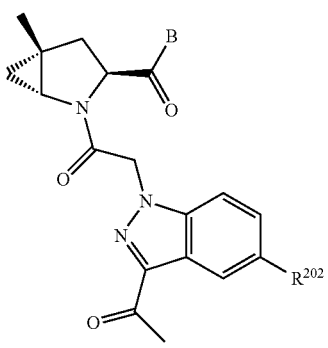
TABLE 5-continued
Additional Exemplary Formulas within the Present Invention.
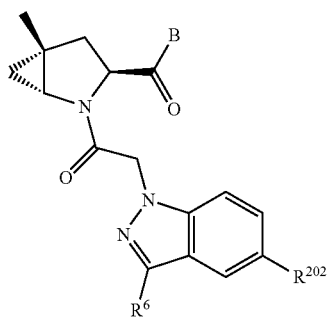
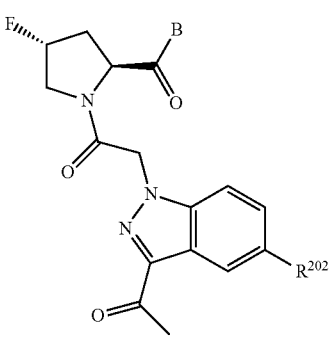
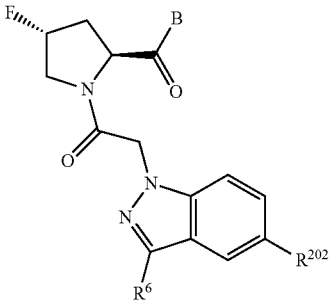
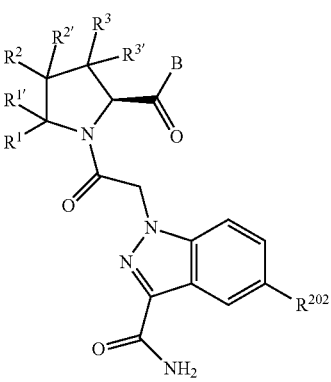

TABLE 5-continued
Additional Exemplary Formulas within the Present Invention.
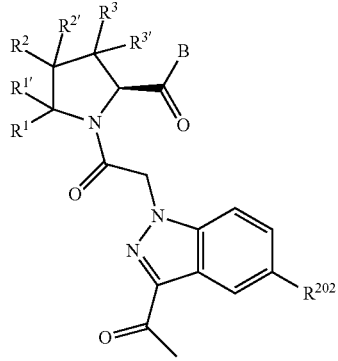
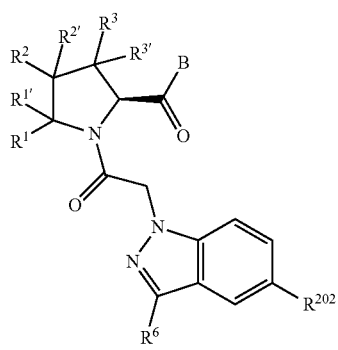
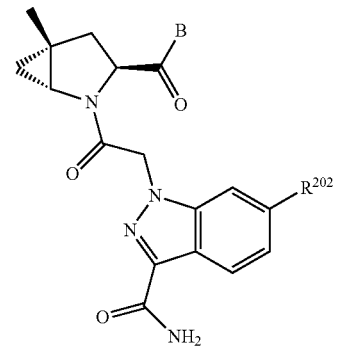
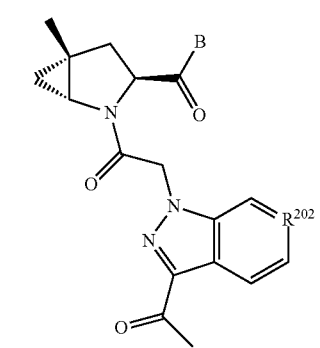
TABLE 5-continued
Additional Exemplary Formulas within the Present Invention.
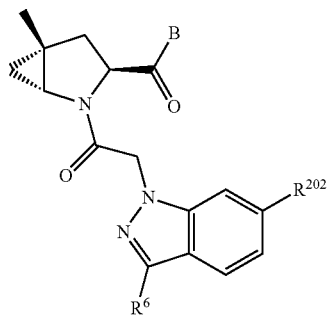
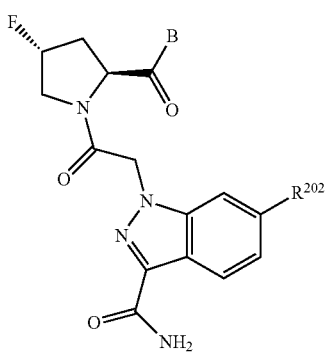
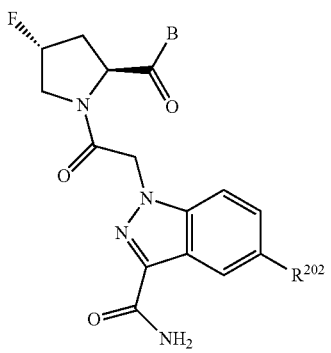
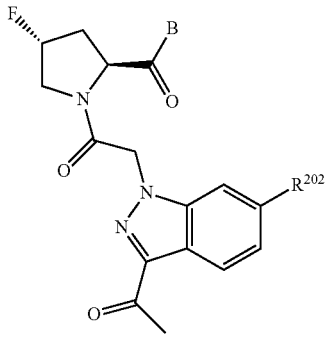

TABLE 5-continued
Additional Exemplary Formulas within the Present Invention.
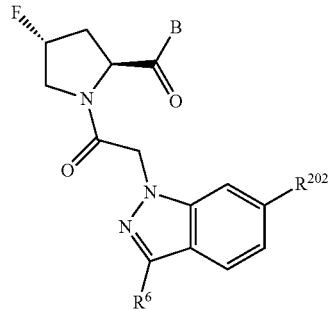
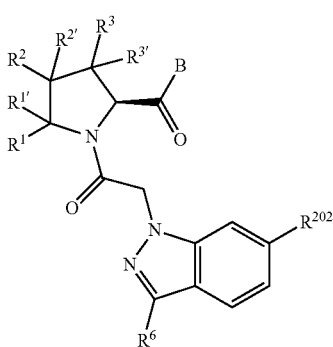
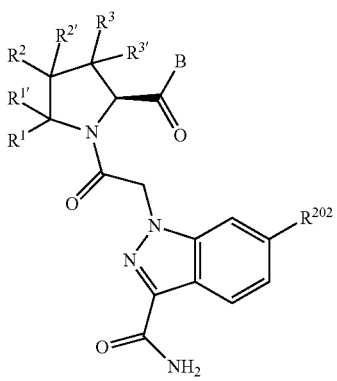
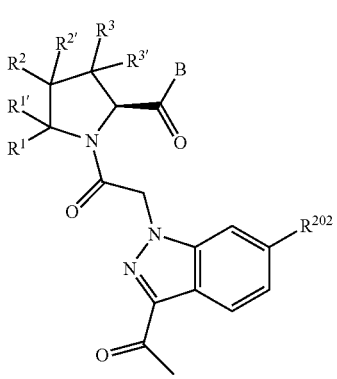
TABLE 5-continued
Additional Exemplary Formulas within the Present Invention.
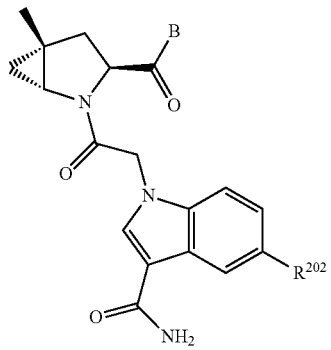
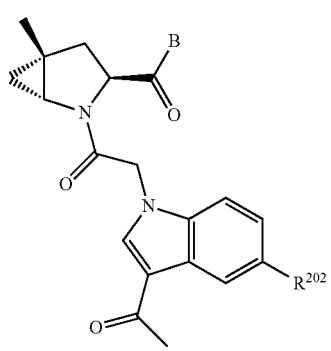
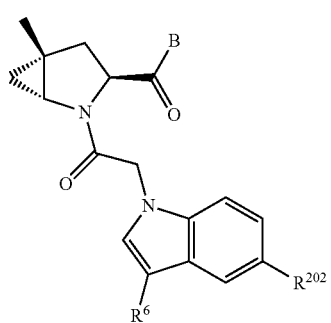
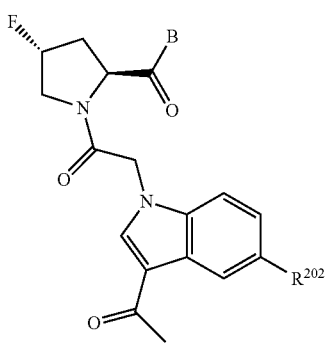

TABLE 5-continued
Additional Exemplary Formulas within the Present Invention.
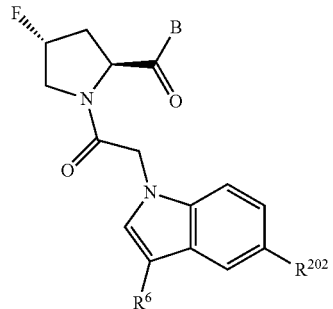
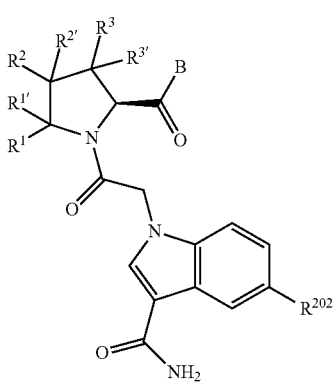
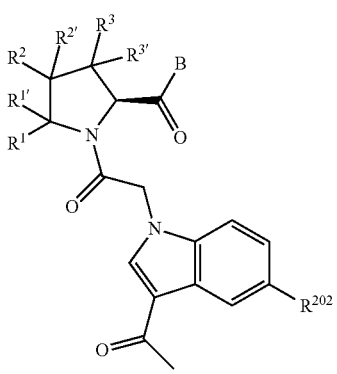
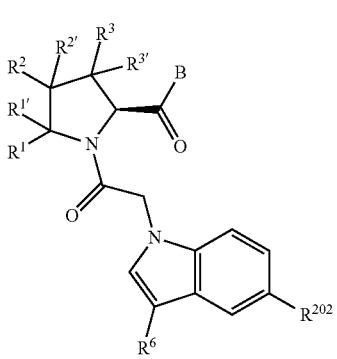
TABLE 5-continued
Additional Exemplary Formulas within the Present Invention.
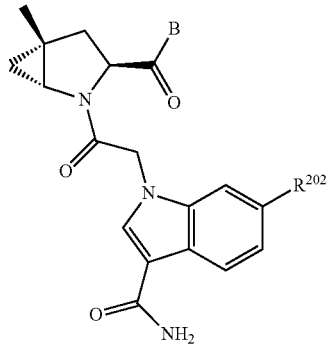
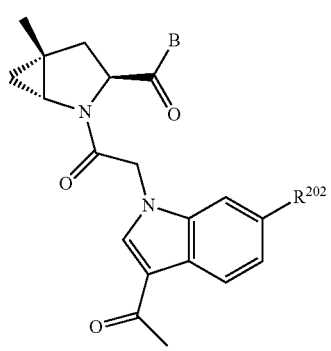
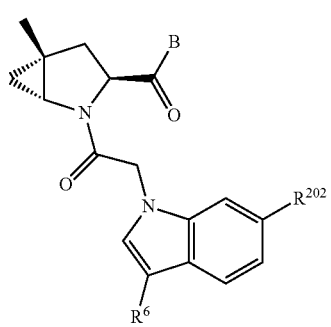
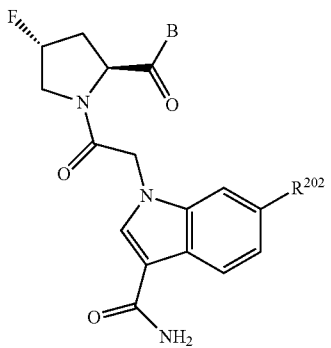

TABLE 5-continued

Additional Exemplary Formulas within the Present Invention.

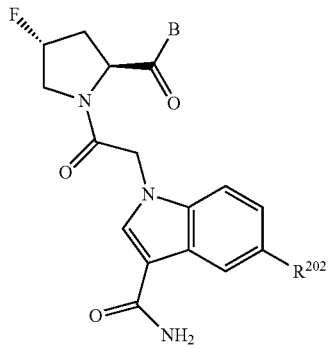

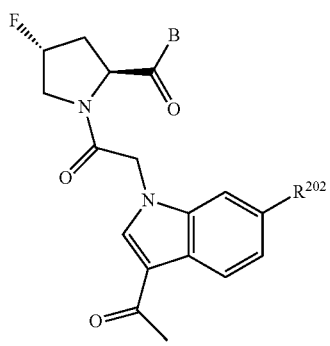

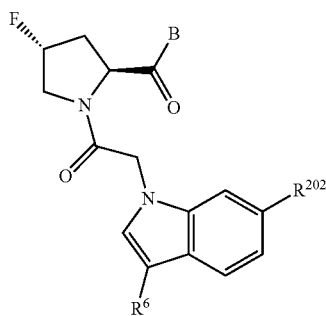

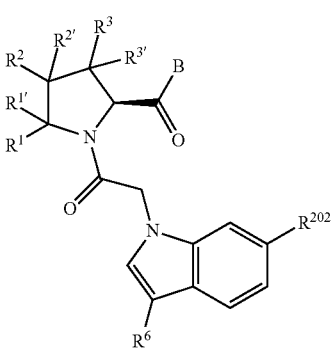

TABLE 5-continued

Additional Exemplary Formulas within the Present Invention.

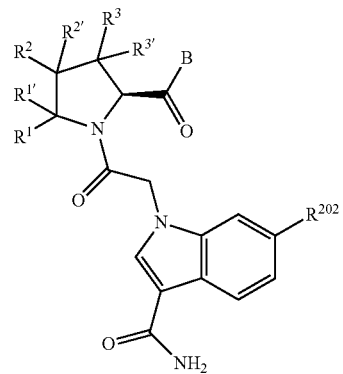

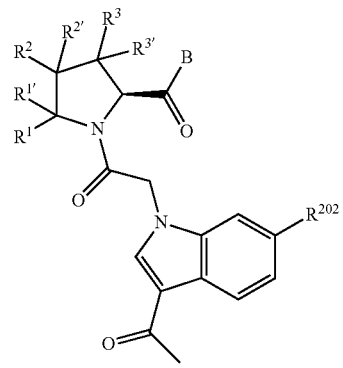

The $R^{12}$ and $R^{13}$ Heteroaryl, and Heterocycle Substituents

The invention includes a compound of Formula I, Formula II, Formula III, Formula IV, or Formula V a pharmaceutically acceptable salt, prodrug, isotopic analog, N-oxide, or isolated isomer thereof, optionally in a pharmaceutically acceptable composition, wherein at least one of $R^{12}$ or $R^{13}$ on the A group is an heteroaryl, or heterocycle for example, $R^{32}$.

One of $R^{12}$ and $R^{13}$ is selected from $R^{31}$ and the other of $R^{12}$ and $R^{13}$ is selected from $R^{32}$. In another embodiment, each of $R^{12}$ and $R^{13}$ can be independently selected from $R^{32}$.

$R^{31}$ is selected from hydrogen, halogen, hydroxyl, nitro, cyano, amino, —COOH, haloalkyl including $C_1$-$C_6$haloalkyl, haloalkoxy including $C_1$-$C_6$haloalkoxy, alkyl including $C_1$-$C_6$alkyl, —$C_0$-$C_4$alkyl($C_3$-$C_7$cycloalkyl), alkenyl including $C_2$-$C_6$alkenyl, alkanoyl including $C_2$-$C_6$alkanoyl, alkoxy including $C_1$-$C_6$alkoxy, alkenyloxy including $C_2$-$C_6$alkenyloxy, —C(O)OR$^9$, thioalkyl including $C_1$-$C_6$thioalkyl, —$C_0$-$C_4$alkylNR$^9$R$^{10}$, —C(O)NR$^9$R$^{10}$, —SO$_2$R$^9$, —SO$_2$NR$^9$R$^{10}$, —OC(O)R$^9$, and —C(NR$^9$)NR$^9$R$^{10}$, each of which $R^{31}$ other than hydrogen, halogen, hydroxyl, nitro, cyano, haloalkyl including $C_1$-$C_6$haloalkyl, and haloalkoxy including $C_1$-$C_6$haloalkoxy is unsubstituted or substituted with one or more substituents independently selected from halogen, hydroxyl, nitro, cyano, amino, —COOH, —CONH$_2$, haloalkyl including $C_1$-$C_6$haloalkyl, and haloalkoxy including $C_1$-$C_6$haloalkoxy, and each of which $R^{31}$ is also optionally substituted with one substituent selected from phenyl and 4- to 7-membered heterocycle containing 1, 2, or 3 heteroatoms independently selected from N, O, and S; which phenyl or 4- to 7-membered heterocycle is unsubstituted or substituted with one or more substituents independently selected from halogen, hydroxyl, nitro, cyano, alkyl including $C_1$-$C_6$alkyl, alkenyl including $C_2$-$C_6$alkenyl, alkanoyl including $C_2$-$C_6$alkanoyl, alkoxy including $C_1$-$C_6$alkoxy, (mono- and di-$C_1$-$C_6$alkylamino)$C_0$-$C_4$alkyl, $C_1$-$C_6$alkylester, —$C_0$-$C_4$alkyl) ($C_3$-$C_7$cycloalkyl), haloalkyl including $C_1$-$C_6$haloalkyl, and haloalkoxy including $C_1$-$C_6$haloalkoxy;

$R^{32}$ is selected from heteroaryl; saturated heterocycle or partially unsaturated heterocycle; wherein the heteroaryl; saturated heterocycle or partially unsaturated heterocycle ring can be optionally substituted.

Non-Limiting $R^{12}/R^{13}$ Embodiments

In one embodiment, $R^{12}$ is $R^{32}$.
In one embodiment, $R^{13}$ is $R^{32}$.
In one embodiment, $R^{12}$ is an optionally substituted heteroaryl.
In one embodiment, $R^{13}$ is an optionally substituted heteroaryl.
In one embodiment, $R^{12}$ is $R^{32}$.
In one embodiment, $R^{12}$ is $R^{32}$, which is (4- to 7-membered heterocycloalkyl) having 1, 2, or 3 heteroatoms independently selected from N, O, and S.
In one embodiment, the disclosure provides compounds of Formula I, wherein;
one of $R^{12}$ and $R^{13}$ is H and the other of $R^{12}$ and $R^{13}$ is $R^{32}$, where
$R^{32}$ is selected from heteroaryl; saturated heterocycle or partially unsaturated heterocycle; wherein the heteroaryl; saturated heterocycle or partially unsaturated heterocycle ring can be optionally substituted.

In another embodiment, the disclosure provides compounds of Formula I, Formula II, Formula III, Formula IV, or Formula V wherein;
$R^1$, $R^{1'}$, $R^2$, and $R^{3'}$ are all hydrogen;
$R^2$ is fluoro and $R^3$ is hydrogen, —$C_0$-$C_4$alkyl($C_3$-$C_7$cycloalkyl), or —O—$C_0$-$C_4$alkyl($C_3$-$C_7$cycloalkyl);
$R^5$ is hydrogen, halogen, or $C_1$-$C_6$alkyl;
$R^{11}$, $R^{13}$, $R^{14}$, and $R^{15}$ if present, are independently selected at each occurrence from hydrogen, halogen, hydroxyl, amino, $C_1$-$C_4$alkyl, $C_1$-$C_4$alkoxy, —$C_0$-$C_2$alkyl (mono- and di-$C_1$-$C_6$alkylamino), trifluoromethyl, and trifluoromethoxy;
$X^{12}$ is $CR^{12}$; and
$R^{12}$ is selected from heteroaryl; saturated heterocycle or partially unsaturated heterocycle; wherein the heteroaryl; saturated heterocycle or partially unsaturated heterocycle ring can be optionally substituted.

In one embodiment, the disclosure provides compounds of Formula I, wherein;
m is 0 or 1;
$R^2$ is halogen, $R^{2'}$ is hydrogen or halogen, and $R^3$ is hydrogen, halogen, —$C_0$-$C_4$alkyl($C_3$-$C_7$cycloalkyl), or —O—$C_0$-$C_4$alkyl($C_3$-$C_7$cycloalkyl);
$R^6$ is —C(O)$C_1$-$C_4$alkyl, —C(O)$NH_2$, —C(O)$CF_3$, —C(O)($C_3$-$C_7$cycloalkyl), or -ethyl(cyanoimino);
one of $R^{12}$ and $R^{13}$ is selected from hydrogen, halogen, $C_1$-$C_4$alkyl, $C_1$-$C_4$alkoxy, trifluoromethyl, and trifluoromethoxy; the other of $R^{12}$ and $R^{13}$ is $R^{32}$, where
$R^{32}$ is selected from aryl, heteroaryl; saturated or unsaturated heterocycle; wherein the aryl, heteroaryl, saturated or unsaturated heterocycle ring can be optionally substituted.

In one embodiment, the disclosure provides compounds of Formula I, Formula II, Formula III, Formula IV, or Formula V, wherein one of $R^{12}$ and $R^{13}$ is hydrogen, hydroxyl, halogen, methyl, or methoxy; and the other of $R^{12}$ and $R^{13}$ is $R^{32}$, where $R^{32}$ is selected from heteroaryl; saturated heterocycle or partially unsaturated heterocycle; wherein the heteroaryl; saturated heterocycle or partially unsaturated heterocycle ring, can be optionally substituted.

In one embodiment, $R^{32}$ may be unsubstituted or substituted with one or more substituents independently selected from halogen, hydroxyl, nitro, cyano, amino, oxo, —B(OH)$_2$, —Si(CH$_3$)$_3$, —COOH, —CONH$_2$, —P(O)(OH)$_2$, $C_1$-$C_6$alkyl, alkoxy including $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, haloalkyl including $C_1$-$C_6$haloalkyl, and haloalkoxy including $C_1$-$C_6$haloalkoxy.

In one embodiment, $R^{31}$ is hydrogen and $R^{32}$ is pyrimidinyl.

In another embodiment, $R^{31}$ is hydrogen and $R^{32}$ is pyrimidine substituted with a methyl group.

Non-Limiting Central Core Embodiments

In certain embodiments, $R^1$ and $R^{1'}$ or $R^3$ and $R^{3'}$ may be taken together to form a 3- to 6-membered carbocyclic spiro ring or a 3- to 6-membered heterocyclic spiro ring containing 1 or 2 heteroatoms independently selected from N, O, or S; $R^2$ and $R^{2'}$ may be taken together to form a 3- to 6-membered carbocyclic spiro ring; or $R^2$ and $R^{2'}$ may be taken together to form a 3- to 6-membered heterocyclic spiro ring; each of which ring may be unsubstituted or substituted with 1 or more substituents independently selected from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), haloalkyl including $C_1$-$C_6$haloalkyl, and haloalkoxy including $C_1$-$C_6$haloalkoxy.

In other embodiments, $R^1$ and $R^2$ may be taken together to form a 3-membered carbocyclic ring; $R^1$ and $R^2$ may be taken together to form a 4, 5 or 6-membered carbocyclic or an aryl ring or a 4, 5 to 6-membered heterocyclic or heteroaryl ring containing 1 or 2 heteroatoms independently selected from N, O, and S; or $R^2$ and $R^3$, if bound to adjacent carbon atoms, may be taken together to form a 3- to 6-membered carbocyclic or aryl ring or a 3- to 6-membered heterocyclic or heteroaryl ring;
each of which ring may be unsubstituted or substituted with 1 or more substituents independently selected from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), haloalkyl including $C_1$-$C_6$haloalkyl, and haloalkoxy including $C_1$-$C_6$haloalkoxy.

In one embodiment, the central core moiety is proline.
In one embodiment, the central core moiety is 4-fluoroproline.
In one embodiment, $R^1$, $R^{1'}$, $R^{2'}$, $R^3$, and $R^{3'}$, if present, are all hydrogen; and $R^2$ is fluoro.
In one embodiment, $R^1$, $R^{1'}$, $R^{2'}$, and $R^{3'}$, if present, are all hydrogen; and $R^2$ is fluoro and $R^3$ is —$C_0$-$C_4$alkyl($C_3$-$C_7$cycloalkyl) or —O—$C_0$-$C_4$alkyl($C_3$-$C_7$cycloalkyl).
In one embodiment, $R^1$ and $R^2$ are taken together to form a 3- to 6-membered cycloalkyl group, and $R^{1'}$, $R^{2'}$, $R^3$, and $R^{3'}$, where present, are all hydrogen. In one embodiment, the bicycle is fused in a cis fashion. In one embodiment, the bicyclic ring is fused in a trans fashion.

In one embodiment, $R^1$ and $R^2$ are taken together to form a 3- to 6-membered cycloalkyl group that is cis with respect to the carboxyl group of L-proline as shown below:

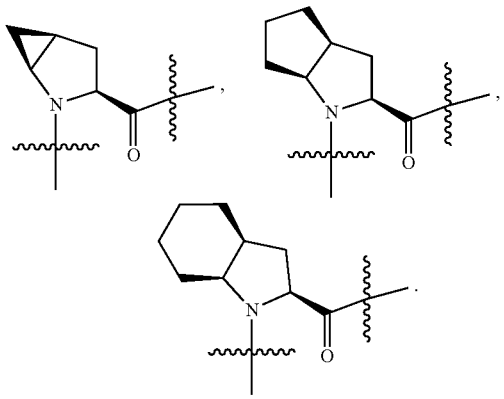

In one embodiment, $R^1$ and $R^2$ are taken together to form a 3- to 6-membered cycloalkyl group that is trans with respect to the carboxyl group of L-proline as shown below:

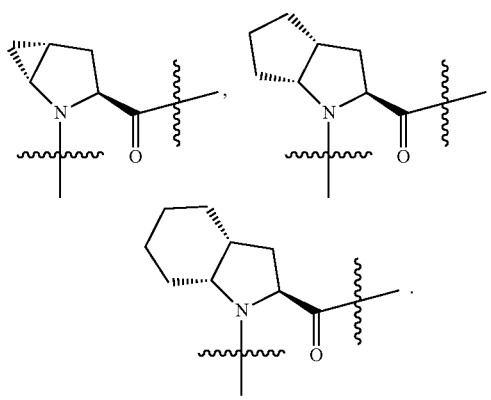

In one embodiment, $R^1$, $R^{1'}$, $R^3$, and $R^{3'}$, if present, are all hydrogen, and $R^2$ and $R^{2'}$ are taken together to form a 5- or 6-membered heterocycloalkyl group having 1 or 2 oxygen atoms.

In one embodiment, $R^1$ is hydrogen and $R^2$ is fluoro.

In one embodiment, $R^1$ and $R^2$ are joined to form a 3 membered ring.

In one embodiment, $R^1$ and $R^2$ are taken together to form a 3-membered cycloalkyl group that is cis with respect to the carboxyl group of L-proline as shown below:

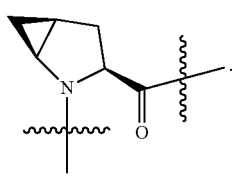 [SMILES: *C(=O)[C@@H]1C[C@@H]2C[C@@H]2N1*]

In one embodiment, $R^1$ and $R^2$ are taken together to form a 3-membered cycloalkyl group that is trans with respect to the carboxyl group of L-proline as shown below:

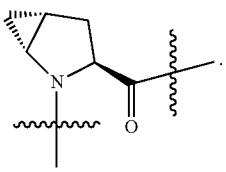 [SMILES: *C(=O)[C@@H]1C[C@H]2C[C@H]2N1*]

In one embodiment, $R^2$ and $R^3$ are taken together to form a 3- to 6-membered cycloalkyl group, and $R^1$, $R^{1'}$, $R^{2'}$ and $R^{3'}$, where present, are selected from hydrogen, $C_1$-$C_3$ alkyl or $C_1$-$C_3$ alkoxy.

In one embodiment, $R^2$ and $R^3$ are taken together to form a 3- to 6-membered cycloalkyl group that is cis with respect to the carboxyl group of L-proline as shown below:

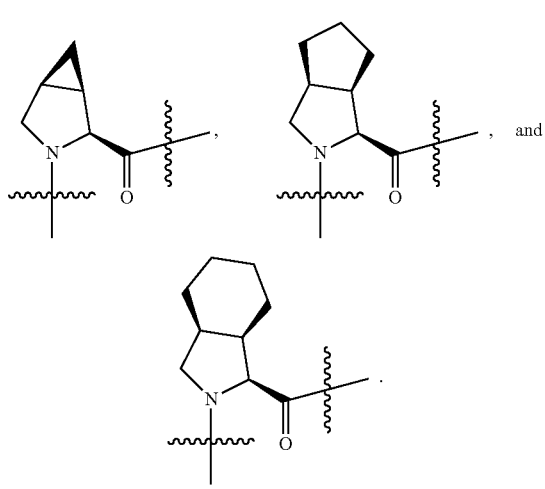

In one embodiment, $R^2$ and $R^3$ are taken together to form a 3- to 6-membered cycloalkyl group that is trans with respect to the carboxyl group of L-proline as shown below:

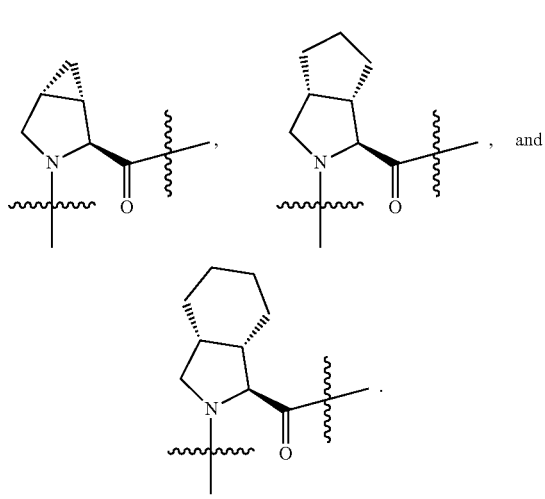

In one embodiment, $R^2$ and $R^3$ are taken together to form a 3-membered cycloalkyl group that is cis with respect to the carboxyl group of L-proline as shown below:

513

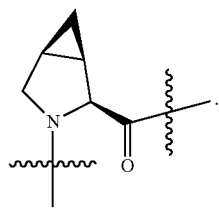 [SMILES: *C(=O)[C@@H]1[C@@H]2C[C@@H]2CN1*]

In one embodiment, $R^2$ and $R^3$ are taken together to form a 3-membered cycloalkyl group that is trans with respect to the carboxyl group of L-proline as shown below:

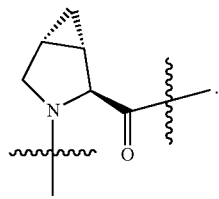 [SMILES: *C(=O)[C@@H]1[C@H]2C[C@H]2CN1*]

In one embodiment, $R^1$, $R^{1'}$, $R^3$, and $R^{3'}$, if present, are all hydrogen, and $R^2$ and $R^{2'}$ are taken together to form a 5- or 6-membered heterocycloalkyl group having 1 or 2 oxygen atoms.

In one embodiment, $R^1$ is hydrogen and $R^2$ is fluoro.

In one embodiment, $R^1$ and $R^2$ are joined to form a 3 membered ring.

Central Core L-B Substituents

Illustrative core L substituents and B substituents in Formula I are described below:

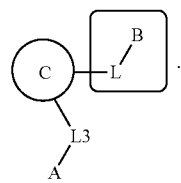

L is a bond or is selected from the formulas:

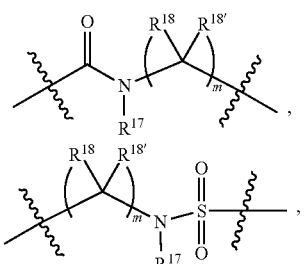

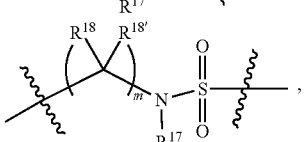

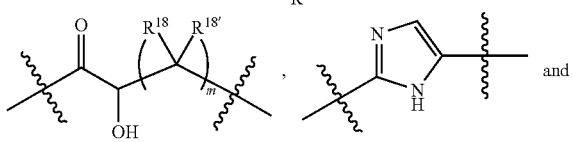
and

514

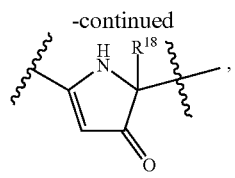

where $R^{17}$ is hydrogen, $C_1$-$C_6$alkyl, or —$C_0$-$C_4$alkyl($C_3$-$C_7$cycloalkyl) and $R^{18}$ and $R^{18'}$ are independently selected from hydrogen, halogen, hydroxymethyl, and methyl; and m is 0, 1, 2, or 3.

Non-Limiting L-B Embodiments

In one embodiment, -L1-B1- is:

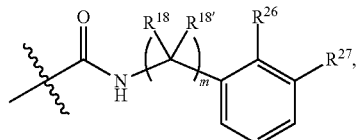

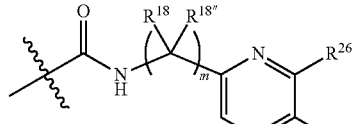

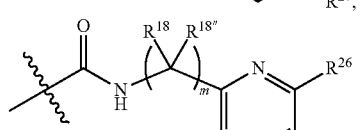

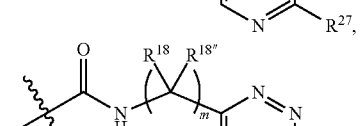

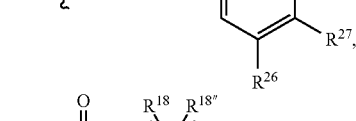

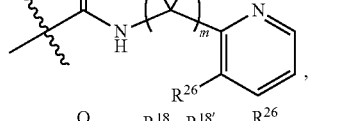

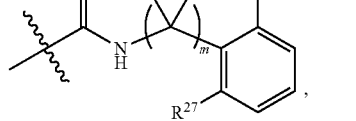

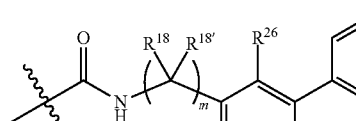

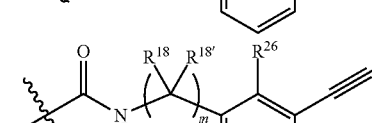

-continued

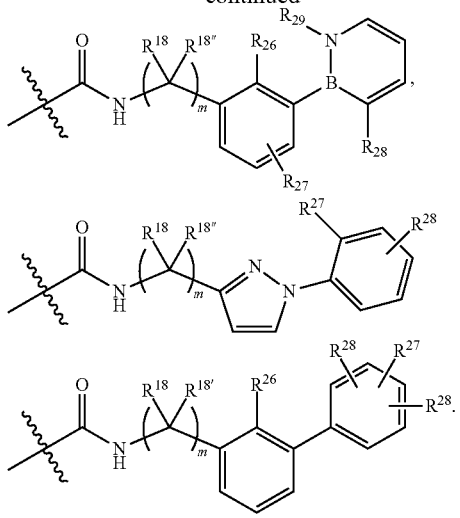

wherein
$R^{18}$ and $R^{18'}$ are independently selected from hydrogen, halogen, hydroxymethyl, and methyl; and m is 0 or 1; and
$R^{26}$, $R^{27}$, and $R^{28}$ are independently selected from hydrogen, halogen, hydroxyl, nitro, cyano, alkyl including $C_1$-$C_6$alkyl, alkenyl including $C_2$-$C_6$alkenyl, alkanoyl including $C_2$-$C_6$alkanoyl, alkoxy including $C_1$-$C_6$alkoxy, thioalkyl including $C_1$-$C_6$thioalkyl, (mono- and di-$C_1$-$C_6$alkylamino)$C_0$-$C_4$alkyl, ($C_3$-$C_7$cycloalkyl)$C_0$-$C_4$alkyl, (aryl)$C_0$-$C_4$alkyl-, (heteroaryl)$C_0$-$C_4$alkyl-, and —$C_0$-$C_4$alkoxy($C_3$-$C_7$cycloalkyl); each of which $R^{26}$, $R^{27}$, and $R^{28}$ other than hydrogen, halogen, hydroxyl, nitro, cyano, is unsubstituted or substituted with one or more substituents independently selected from halogen, hydroxyl, amino, alkoxy including $C_1$-$C_6$alkoxy, haloalkyl including $C_1$-$C_6$haloalkyl, ($C_3$-$C_7$cycloalkyl)$C_0$-$C_4$alkyl-, and haloalkoxy including $C_1$-$C_6$haloalkoxy; and
$R^{29}$ is hydrogen, alkyl including $C_1$-$C_6$alkyl, $C_1C_2$haloalkyl or —$Si(CH_3)_2C(CH_3)_3$.
In one embodiment, -L-B1- moiety is selected:

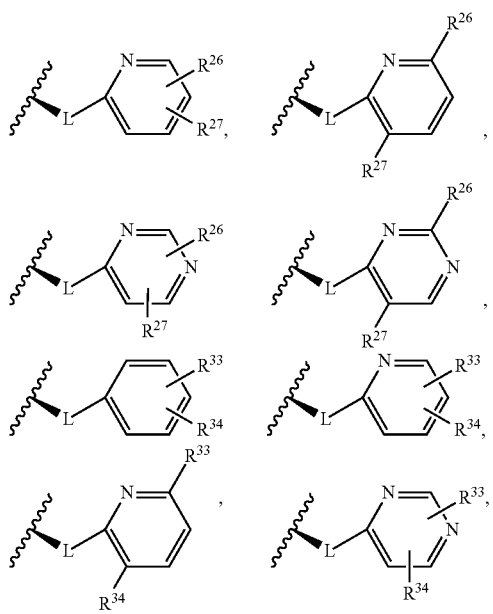

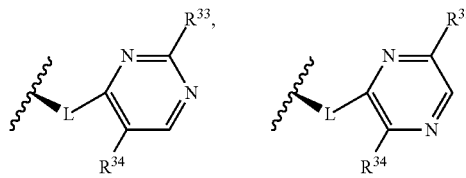

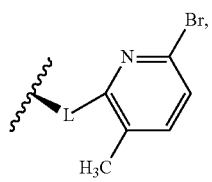

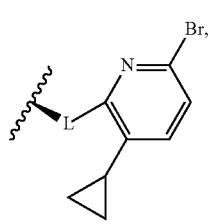

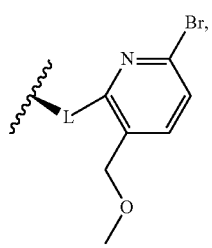

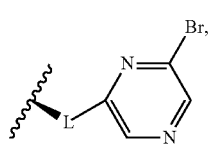 and 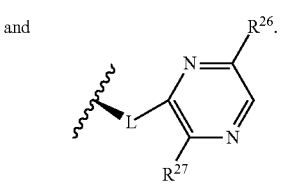

In one embodiment, -L1-B1- moiety is selected:

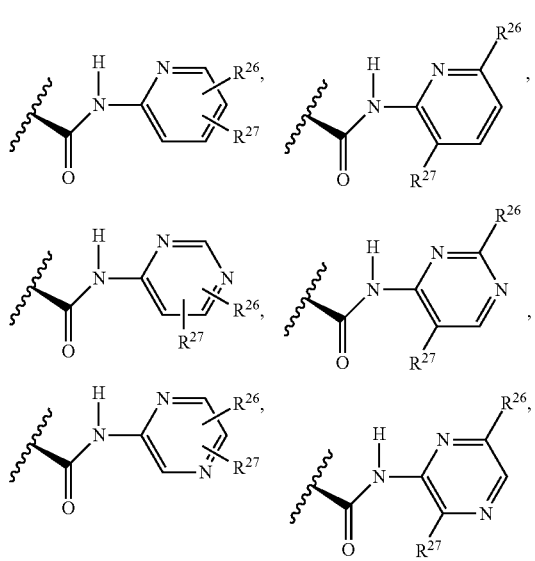

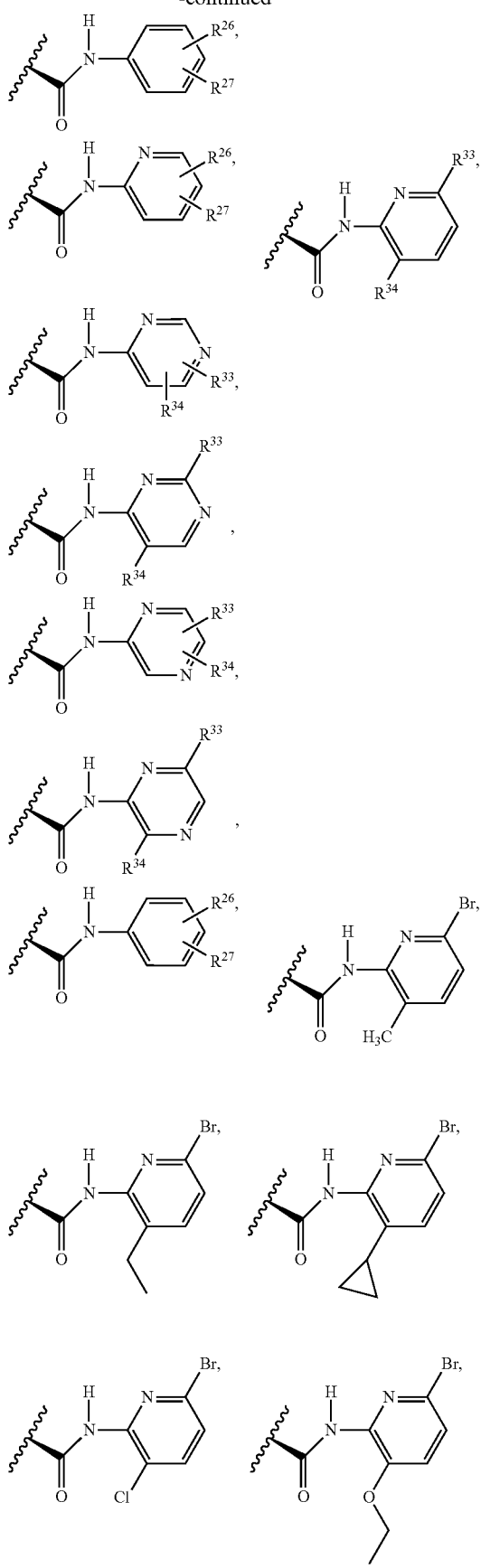
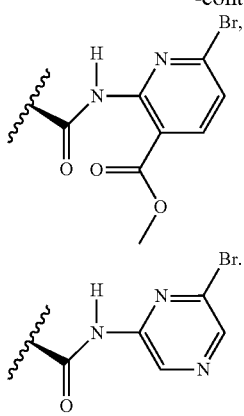
In one embodiment, -L2-B1- moiety is selected:
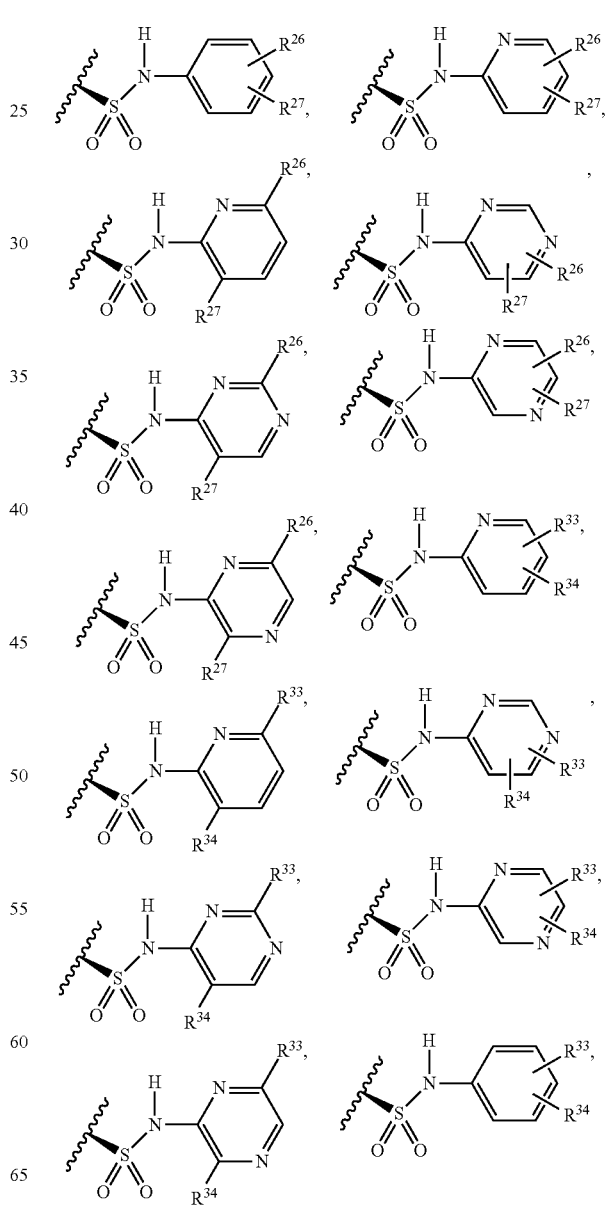

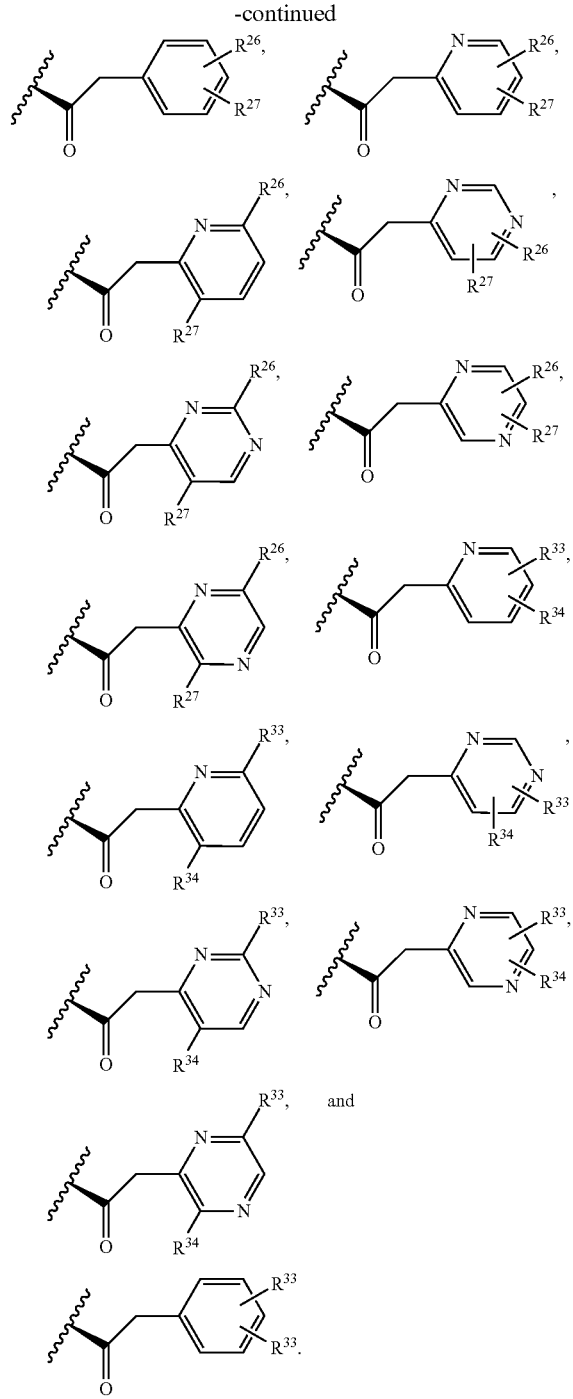

In one embodiment, -L2-B1- moiety is selected:

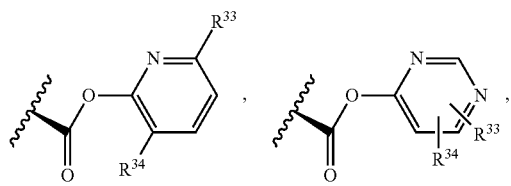

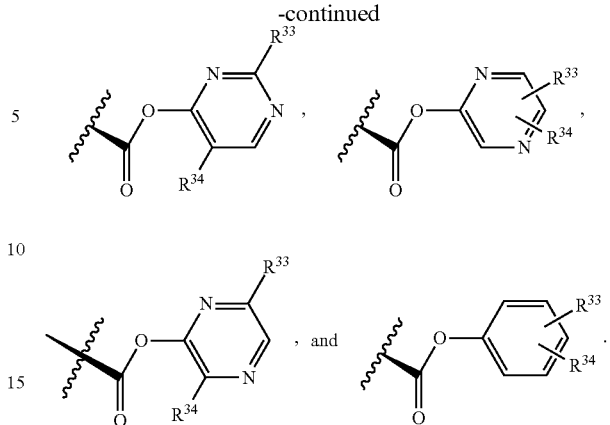

In one embodiment, m is 0.

In one embodiment, the disclosure further includes compounds and salts of Formula I in which B1 is 2-fluoro-3-chlorophenyl. In another embodiment, another carbocyclic, aryl, heterocyclic, or heteroaryl group such as 2-bromo-pyridin-6-yl, 1-(2,2,2-trifluoroethyl)-1H-pyrazol-3-yl, 2,2-dichlorocyclopropylmethyl, or 2-fluoro-3-trimethylsilylphenyl is used.

In another embodiment, B1 is phenyl, pyridyl, or indanyl each of which is unsubstituted or substituted with one or more substituents independently selected from hydrogen, halogen, hydroxyl, nitro, cyano, alkyl including $C_1$-$C_6$alkyl, alkenyl including $C_2$-$C_6$alkenyl, alkanoyl including $C_2$-$C_6$alkanoyl, alkoxy including $C_1$-$C_6$alkoxy, thioalkyl including $C_1$-$C_6$thioalkyl, (mono- and di-$C_1$-$C_6$alkylamino)$C_0$-$C_4$alkyl, ($C_3$-$C_7$cycloalkyl)$C_0$-$C_4$alkyl, —$C_0$-$C_4$alkoxy($C_3$-$C_7$cycloalkyl), (phenyl)$C_0$-$C_2$alkyl, (pyridyl)$C_0$-$C_2$alkyl; each of which substituents other than hydrogen, halogen, hydroxyl, nitro, cyano, is unsubstituted or substituted with one or more substituents independently selected from halogen, hydroxyl, amino, alkyl including $C_1$-$C_6$alkyl, alkoxy including $C_1$-$C_6$alkoxy, —OSi(CH$_3$)$_2$C(CH$_3$)$_3$, —Si(CH$_3$)$_2$C(CH$_3$)$_3$, haloalkyl including $C_1$-$C_6$haloalkyl, and haloalkoxy including $C_1$-$C_6$haloalkoxy.

In another embodiment, B1 is phenyl or pyridyl substituted with 1, 2, or 3 substituents selected from chloro, bromo, hydroxyl, —SCF$_3$, $C_1$-$C_6$alkyl, $C_1$-$C_6$alkoxy, trifluoromethyl, phenyl and trifluoromethoxy each of which substituents other than chloro, bromo, hydroxyl, —SCF$_3$, can be optionally substituted.

In certain embodiments, B1 is a 2-fluoro-3-chlorophenyl or a 2-fluoro-3-trifluoromethoxyphenyl group.

In one embodiment, B1 is pyridyl, optionally substituted with halogen, $C_1$-$C_6$alkoxy, and trifluoromethyl.

In one embodiment, B1 is phenyl, substituted with 1, 2, or 3 substituents independently selected from halogen, $C_1$-$C_6$alkyl, $C_1$-$C_6$alkoxy, trifluoromethyl, and optionally substituted phenyl.

In one embodiment, $R^{23}$ is independently selected at each occurrence from ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S.

In one embodiment, L1-B3 is:

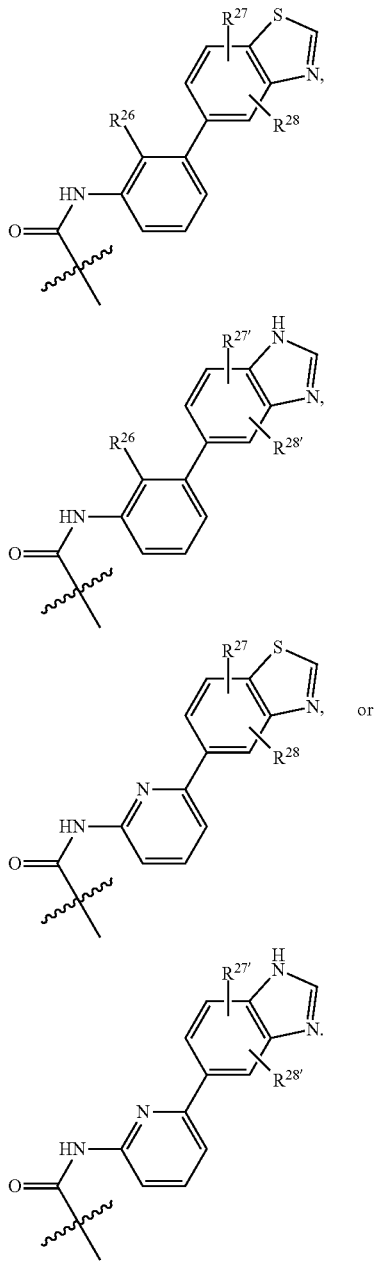

$R^{27'}$, and $R^{28'}$ are independently selected from hydrogen, fluoro, bromo, iodo, hydroxyl, nitro, cyano, alkyl including $C_1$-$C_6$alkyl, alkenyl including $C_2$-$C_6$alkenyl, alkanoyl including $C_2$-$C_6$alkanoyl, $C_2$-$C_6$alkoxy, $C_2$-$C_6$thioalkyl, (mono- and di-$C_1$-$C_6$alkylamino)$C_0$-$C_4$alkyl, ($C_3$-$C_7$cycloalkyl)$C_0$-$C_4$alkyl, (aryl)$C_0$-$C_4$alkyl-, (heteroaryl)$C_0$-$C_4$alkyl-, and —$C_0$-$C_4$alkoxy($C_3$-$C_7$cycloalkyl); each of which $R^{27'}$, and $R^{28'}$ other than hydrogen, fluoro, bromo, iodo, hydroxyl, nitro, and cyano, is unsubstituted or substituted with one or more substituents independently selected from halogen, hydroxyl, amino, alkoxy including $C_1$-$C_6$alkoxy, haloalkyl including $C_1$-$C_6$haloalkyl, ($C_3$-$C_7$cycloalkyl)$C_0$-$C_4$alkyl-, and haloalkoxy including $C_1$-$C_6$haloalkoxy.

Central Core (L3)-A Substituent

The central core (L3)-A substituent in Formula I is illustrated below:

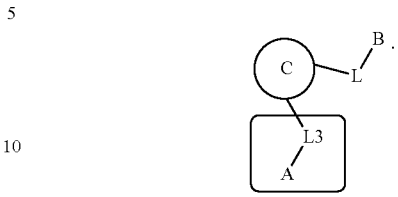

In one embodiment, $R^5$ and $R^6$ are independently selected from —CHO, —C(O)NH$_2$, —C(O)NH(CH$_3$), $C_2$-$C_6$alkanoyl, and hydrogen.

In one embodiment, each $R^5$ and $R^6$ other than hydrogen, hydroxyl, cyano, and —COOH is unsubstituted or substituted with one or more substituents independently selected from halogen, hydroxyl, amino, imino, cyano, cyanoimino, alkyl including $C_1$-$C_6$alkyl, $C_1$-$C_4$alkoxy, —$C_0$-$C_2$alkyl (mono- and di-$C_1$-$C_4$alkylamino), haloalkyl including $C_1$-$C_6$haloalkyl, and haloalkoxy including $C_1$-$C_6$haloalkoxy.

In one embodiment, $R^8$ and $R^{8'}$ are independently hydrogen or methyl.

In one embodiment, $R^8$ and $R^{8'}$ are hydrogen.

In one embodiment, $R^7$ is hydrogen or methyl.

In one embodiment, $R^7$ is hydrogen.

Additional Compounds of the Present Invention

In one embodiment the compound of the present invention is selected from:

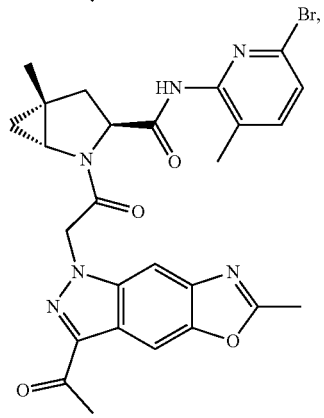

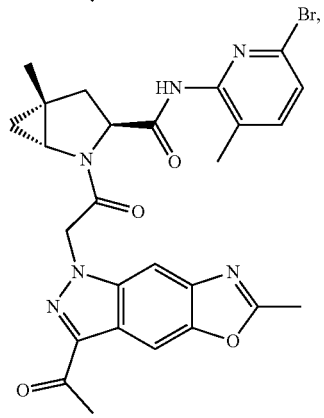

-continued
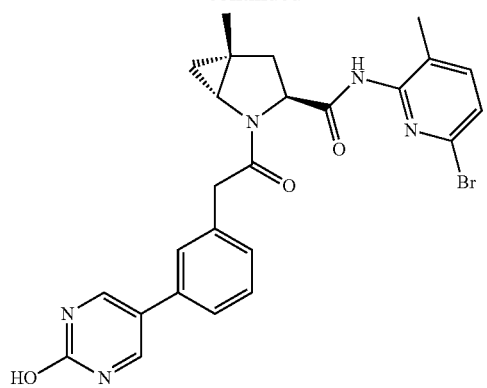
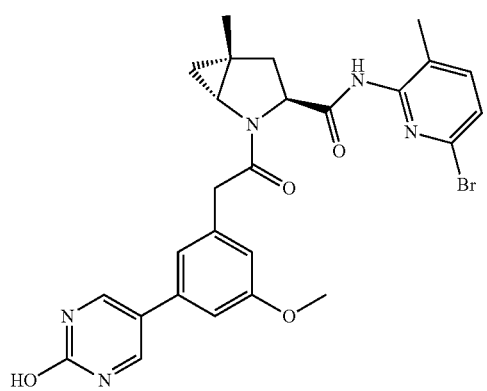
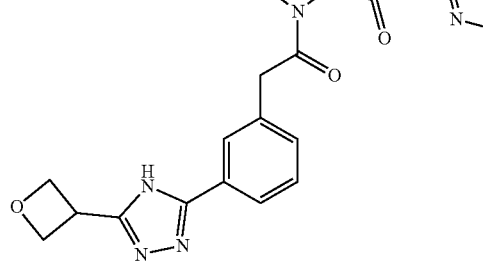
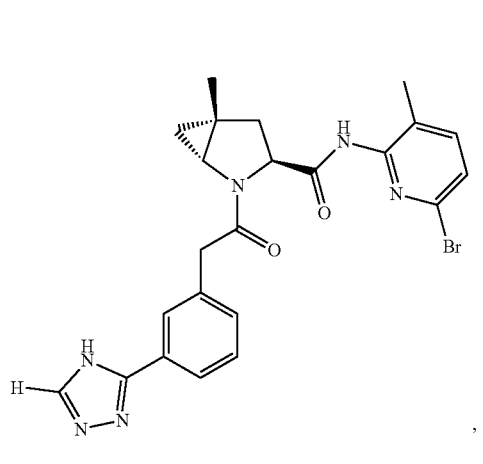
-continued
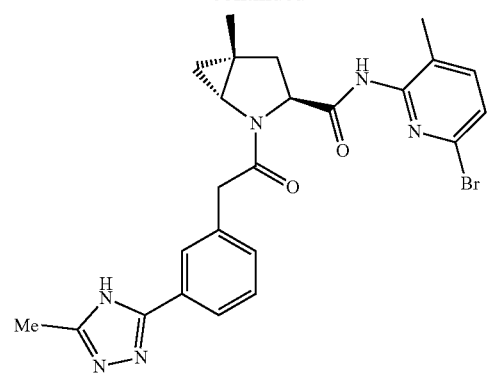
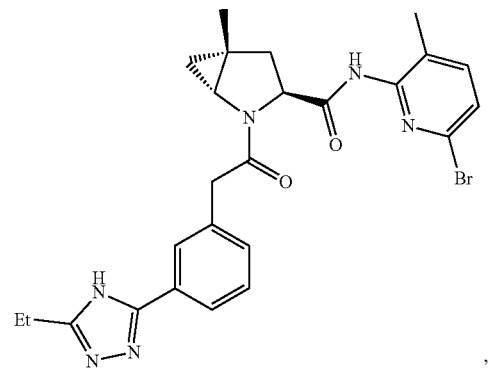
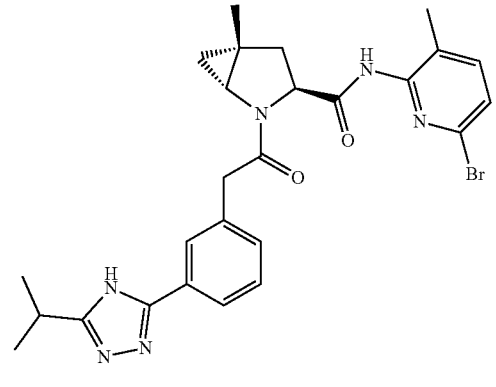
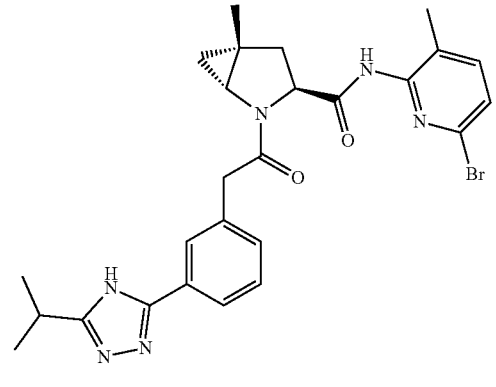

525
-continued
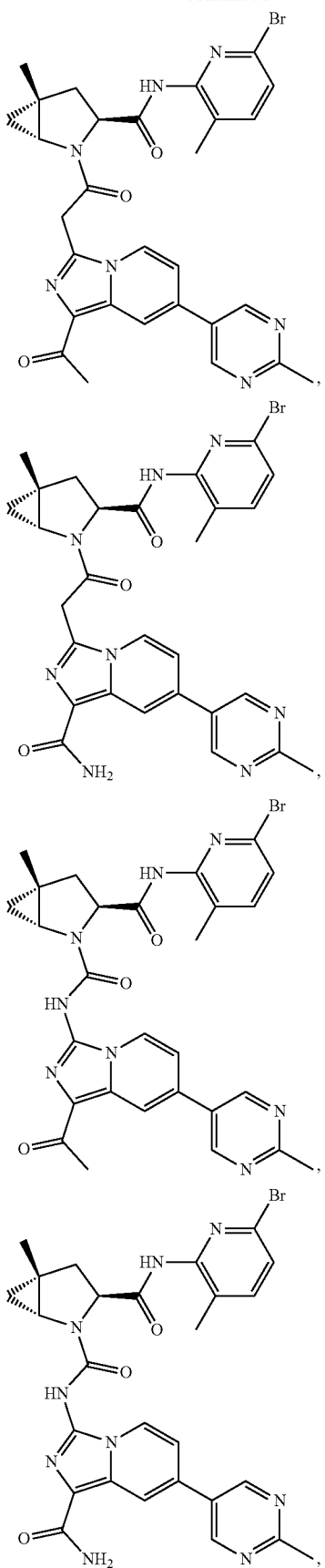
526
-continued
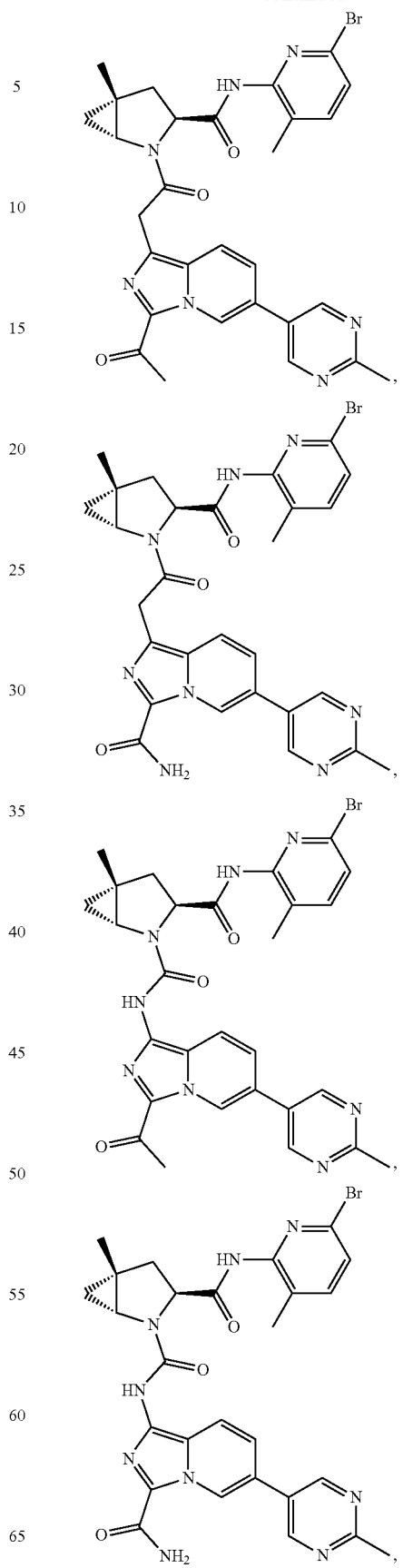

-continued
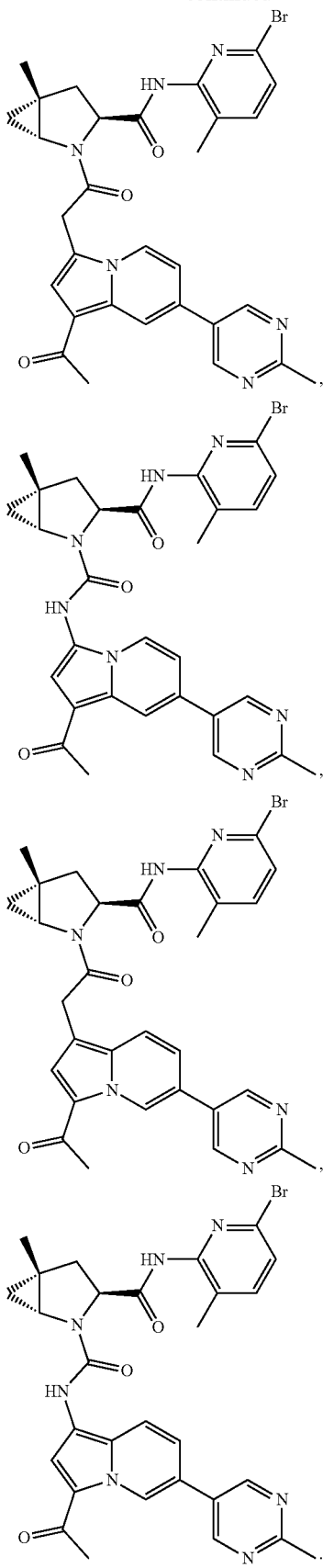
In one embodiment the compound of the present invention is selected from:
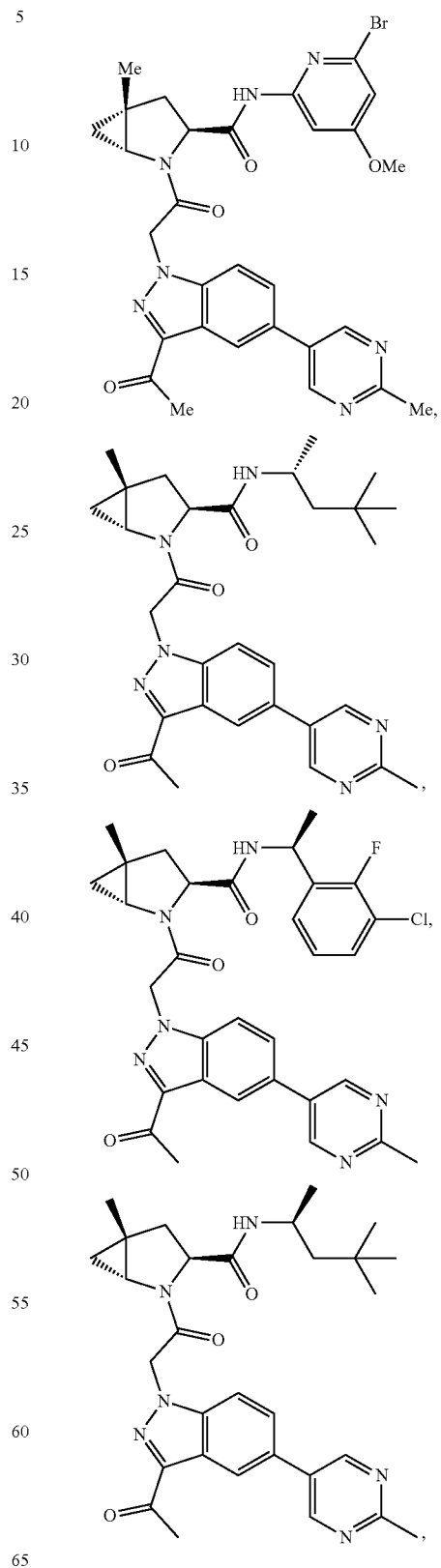

529
-continued
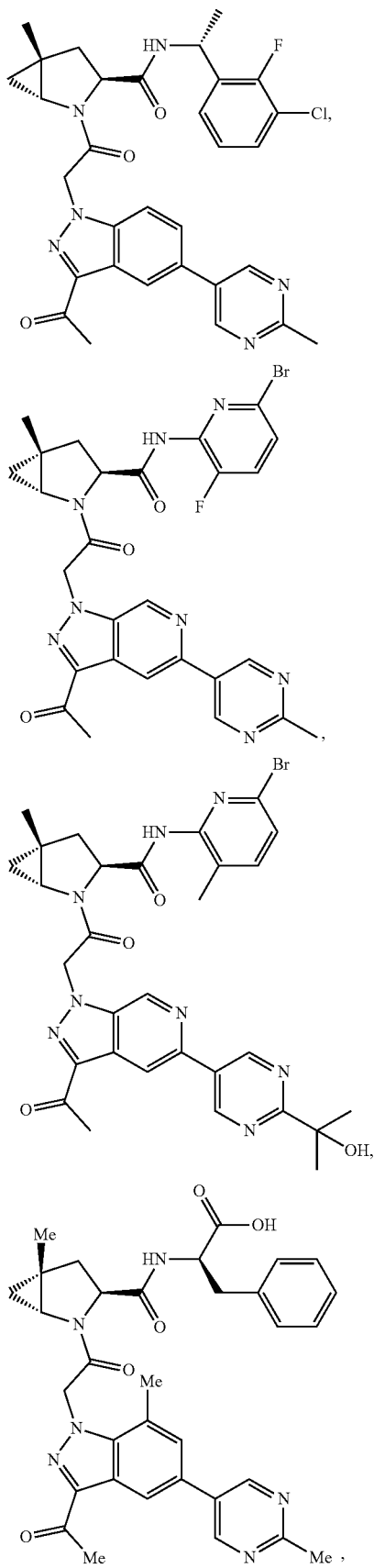
530
-continued
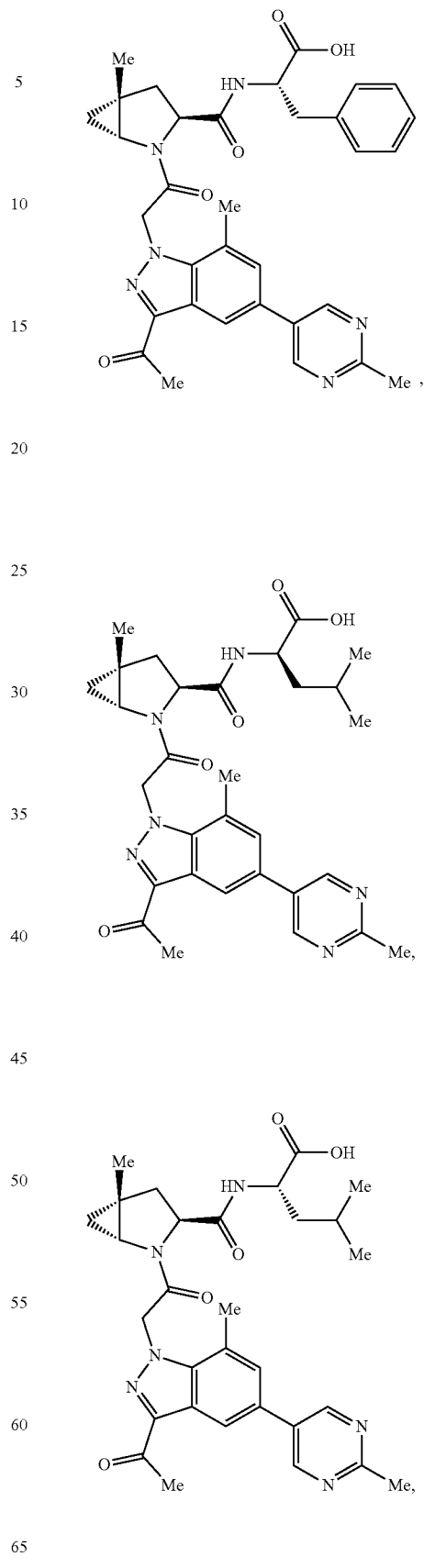

531
-continued
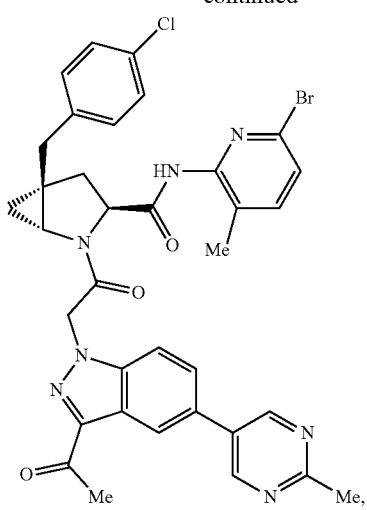
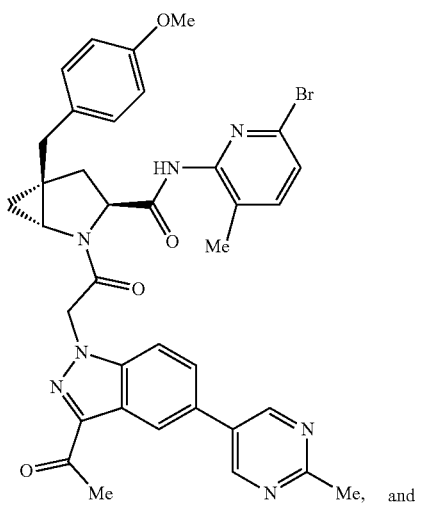
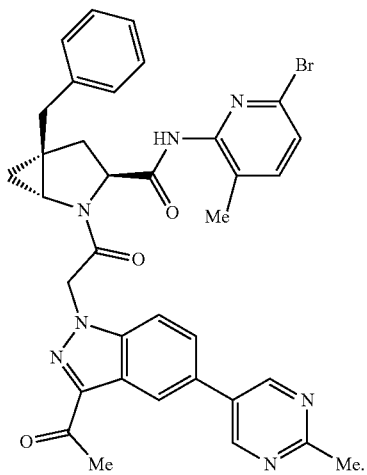
532
In one embodiment the compound of the present invention is selected from:
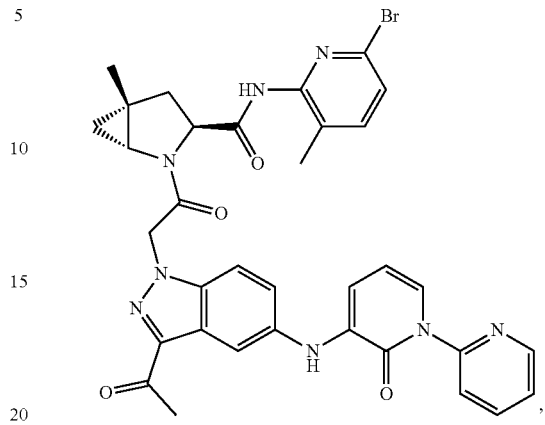
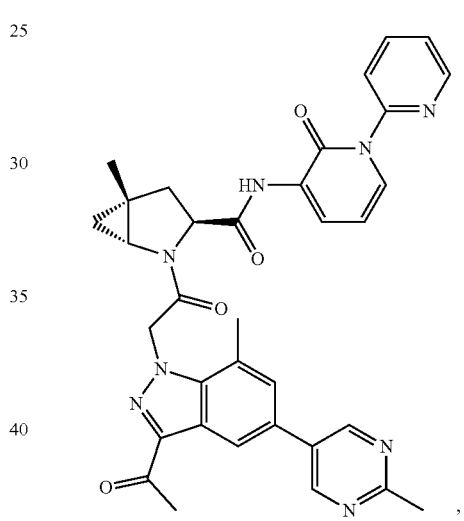
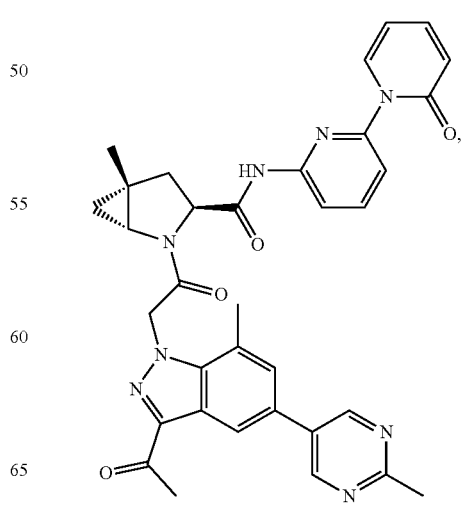

533
-continued
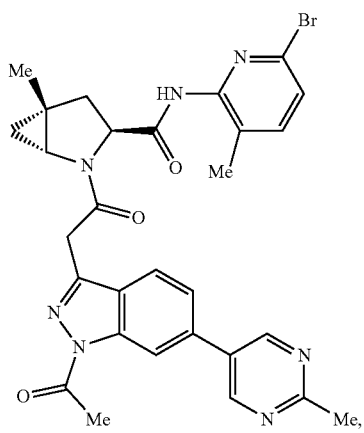
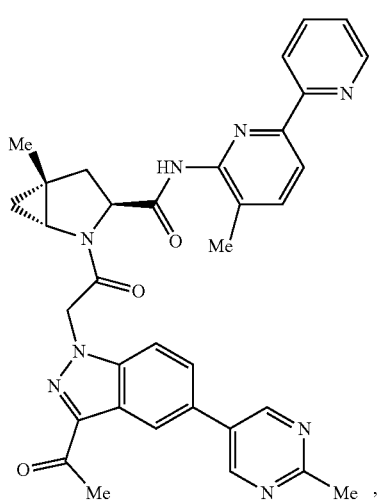
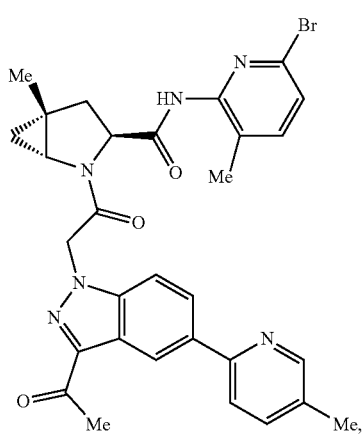
534
-continued
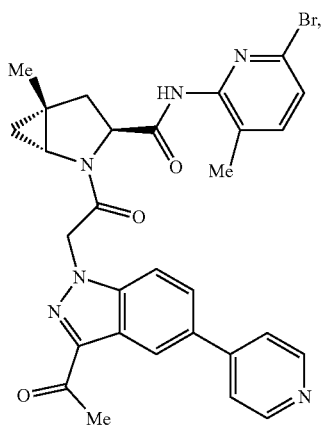
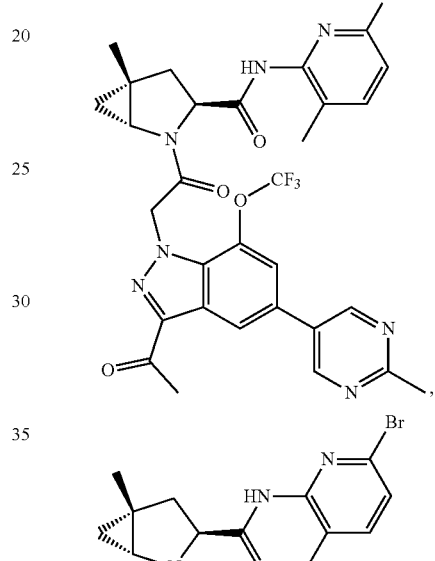
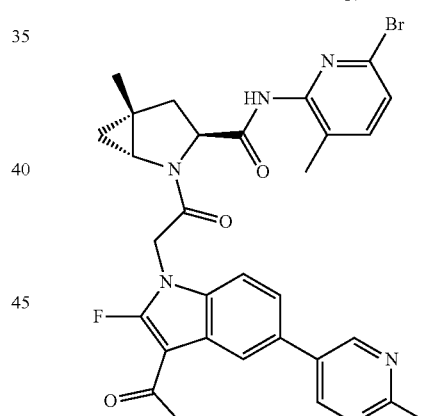
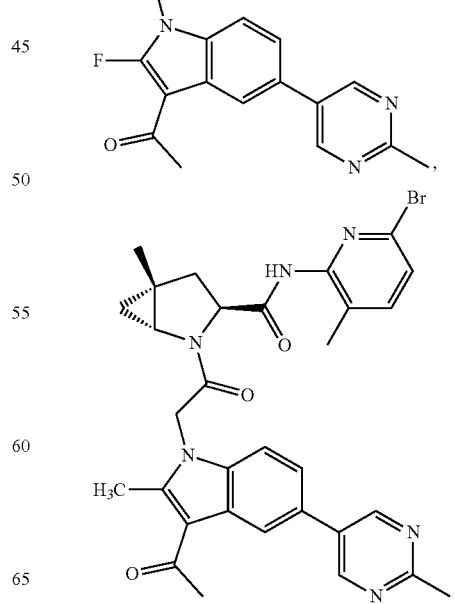

535
-continued
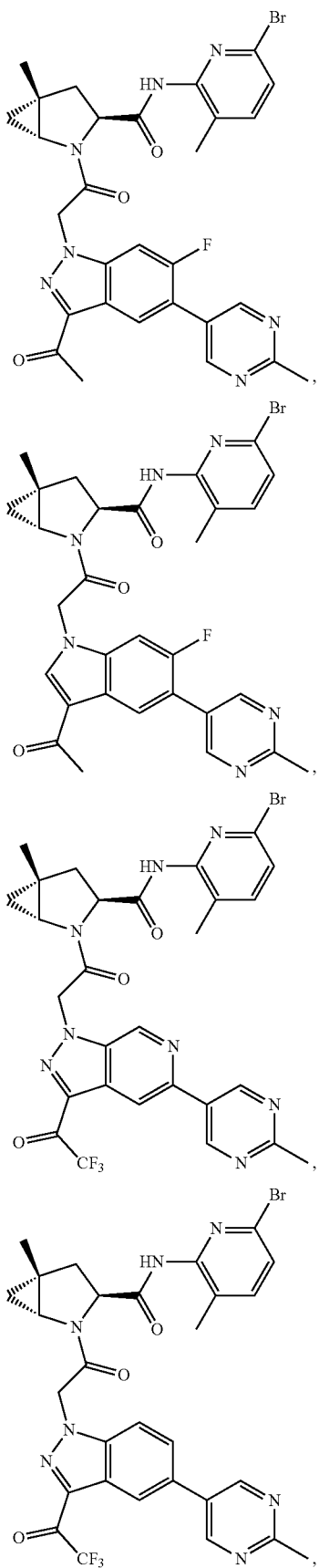
536
-continued
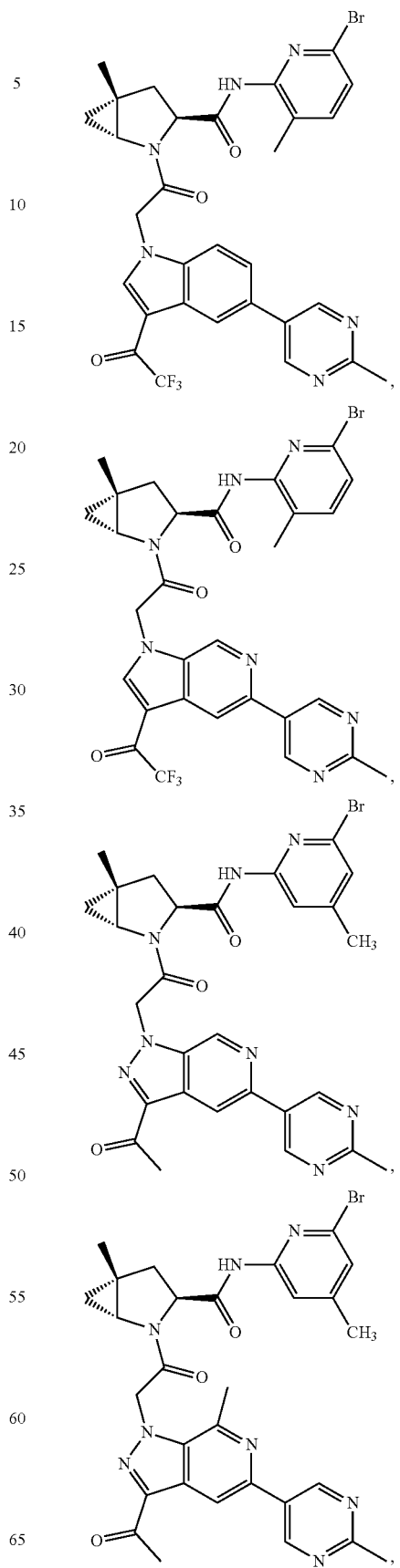

537
-continued
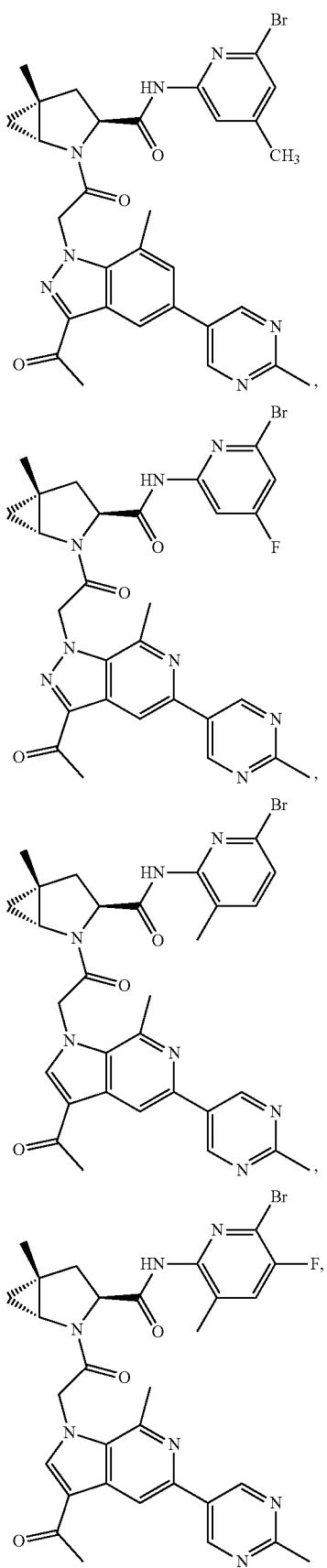
538
-continued
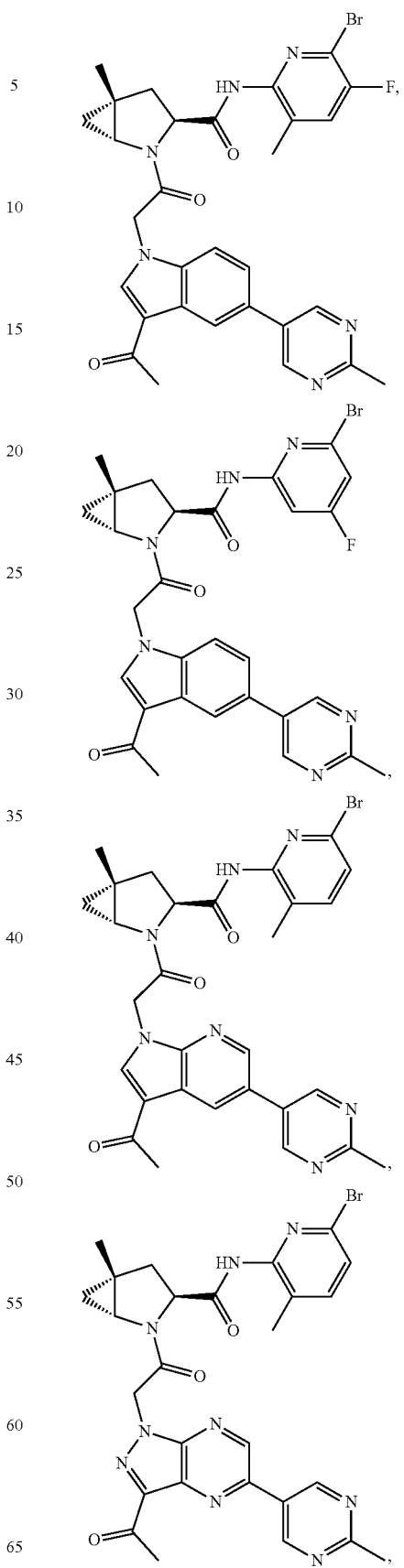

539
-continued
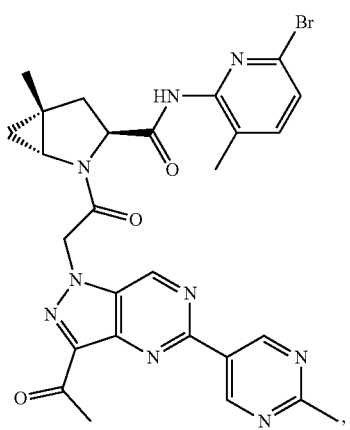
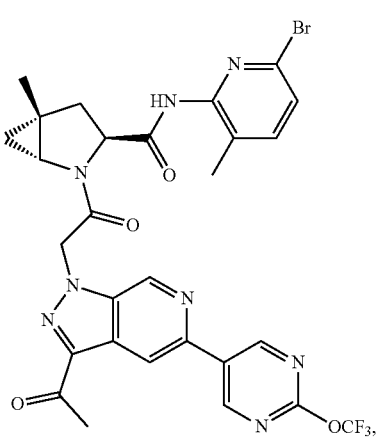
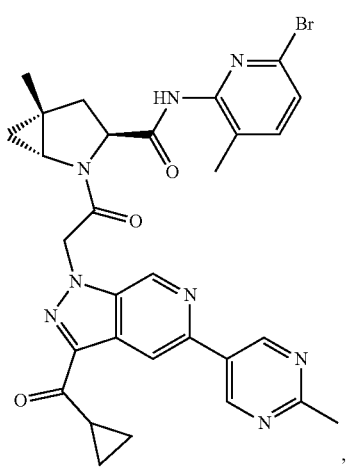
540
-continued
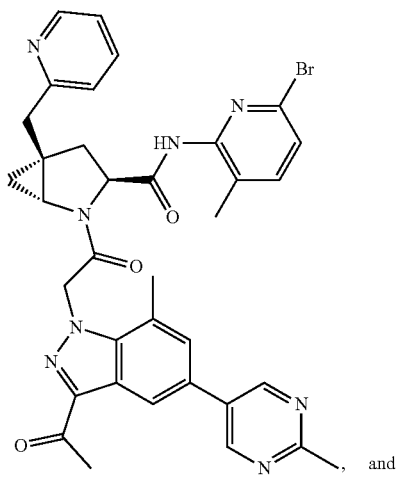
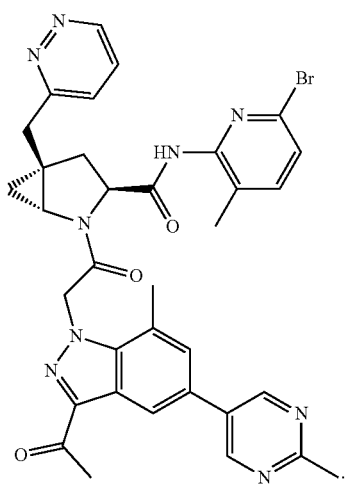 [SMILES: CC(=O)c1nn(CC(=O)N2[C@H](C(=O)Nc3nc(Br)ccc3C)C[C@@]3(Cc4cccnn4)C[C@@H]23)c2c(C)cc(-c3cnc(C)nc3)cc12]
In one embodiment the compound of the present invention is selected from:
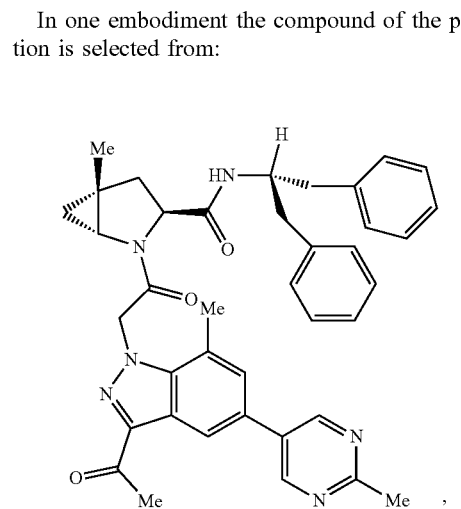

541
-continued

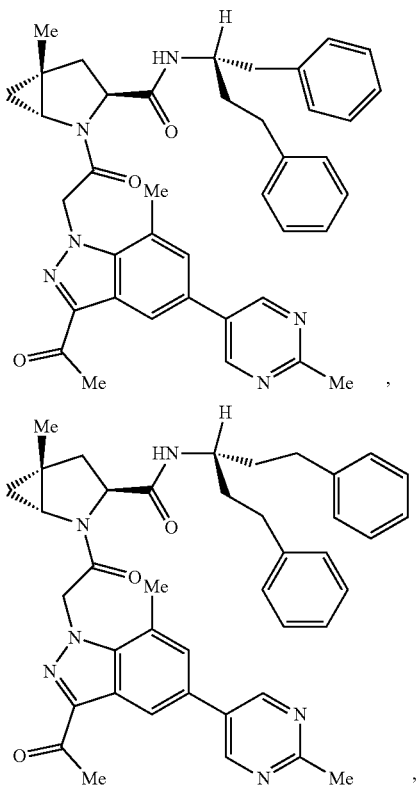

542
-continued

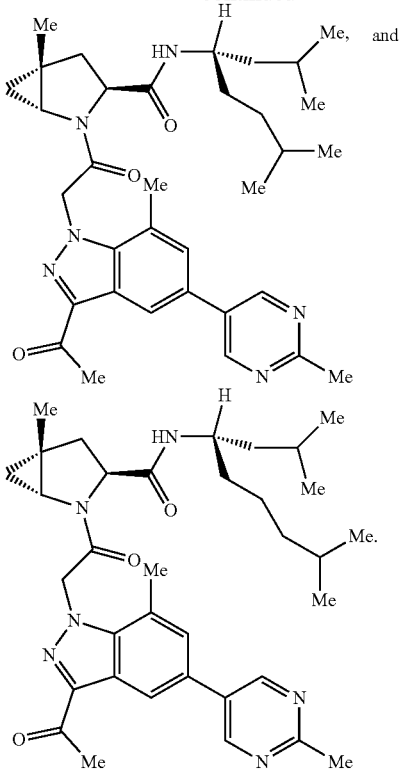

Pharmaceutical Preparations

Active compounds described herein can be administered to a host in need thereof as the neat chemical, but are more typically administered as a pharmaceutical composition that includes an effective amount for a host, typically a human, in need of such treatment of an active compound as described herein or its pharmaceutically acceptable salt, prodrug, isotopic analog, N-oxide, or isolated isomer thereof. Thus, in one embodiment, the disclosure provides pharmaceutical compositions comprising an effective amount of compound or pharmaceutically acceptable salt, prodrug, isotopic analog, N-oxide, or isolated isomer thereof together with at least one pharmaceutically acceptable carrier for any of the uses described herein. The pharmaceutical composition may contain a compound or salt as the only active agent, or, in an alternative embodiment, the compound and at least one additional active agent.

An effective amount of an active compound as described herein, or the active compound described herein in combination or alternation with, or preceded by, concomitant with or followed by another active agent, can be used in an amount sufficient to (a) inhibit the progression of a disorder mediated by the complement pathway, including an inflammatory, immune, including an autoimmune, disorder or complement Factor D related disorder; (b) cause a regression of an inflammatory, immune, including an autoimmune, disorder or complement Factor D related disorder; (c) cause a cure of an inflammatory, immune, including an autoimmune, disorder or complement Factor D related disorder; or inhibit or prevent the development of an inflammatory, immune, including an autoimmune, disorder or complement Factor D related disorder.

Accordingly, an effective amount of an active compound or its salt or composition described herein will provide a sufficient amount of the active agent when administered to a patient to provide a clinical benefit.

The exact amount of the active compound or pharmaceutical composition described herein to be delivered to the host, typically a human, in need thereof, will be determined by the health care provider to achieve the desired clinical benefit.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least about 0.5, 1, 1.5, 2, 2.5, 3, 3.5, 4, 4.5, 5, 10, 15, 20, 25, 50, 75, 100, 150, 200, 250, 300, 350, 400, 450, 500, 550, 600, 650, 700, 750, 800, 900, 1000, 1100, 1200, 1250, 1300, 1400, 1500, or 1600 mg of active compound, or its salt or prodrug. In one embodiment, the dosage form has at least about 1 mg, 5 mg, 10 mg, 25 mg, 50 mg, 75 mg, 100 mg, 200 mg, 400 mg, 500 mg, 600 mg, 1000 mg, 1200 mg, or 1600 mg of active compound, or its salt. The amount of active compound in the dosage form is calculated without reference to the salt. The dosage form can be administered, for example, once a day (q.d.), twice a day (b.i.d.), three times a day (t.i.d.), four times a day (q.i.d.), once every other day (Q2d), once every third day (Q3d), as needed, or any dosage schedule that provides treatment of a disorder described herein.

The pharmaceutical composition may for example include a molar ratio of the active compound and an additional active agent that achieves the desired result. For example, the pharmaceutical composition may contain a molar ratio of about 0.5:1, about 1:1, about 2:1, about 3:1 or from about 1.5:1 to about 4:1 of an additional active agent in combination with the active compound (additional active agent: active compound), or its salt, described herein. In one embodiment, the additional active agent is an anti-inflammatory or immunosuppressing agent.

Compounds disclosed herein or used as described herein may be administered orally, topically, parenterally, by inhalation or spray, sublingually, via implant, including ocular implant, transdermally, via buccal administration, rectally, as an ophthalmic solution, injection, including ocular injection, intravenous, intra-aortal, intracranial, subdermal, intraperitoneal, subcutaneous, transnasal, sublingual, intrathecal, or rectal or by other means, in dosage unit formulations containing conventional pharmaceutically acceptable carriers. For ocular delivery, the compound can be administered, as desired, for example, as a solution, suspension, or other formulation via intravitreal, intrastromal, intracameral, sub-tenon, sub-retinal, retro-bulbar, peribulbar, suprachoroidal, subchoroidal, choroidal, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device, injection, or topically administered formulation, for example a solution or suspension provided as an eye drop.

The pharmaceutical composition may be formulated as any pharmaceutically useful form, e.g., as an aerosol, a cream, a gel, a gel cap, a pill, a microparticle, a nanoparticle, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution or suspension. Some dosage forms, such as tablets and capsules, are subdivided into suitably sized unit doses containing appropriate quantities of the active components, e.g., an effective amount to achieve the desired purpose.

Pharmaceutical compositions, and methods of manufacturing such compositions, suitable for administration as contemplated herein are known in the art. Examples of known techniques include, for example, U.S. Pat. Nos. 4,983,593, 5,013,557, 5,456,923, 5,576,025, 5,723,269, 5,858,411, 6,254,889, 6,303,148, 6,395,302, 6,497,903, 7,060,296, 7,078,057, 7,404,828, 8,202,912, 8,257,741, 8,263,128, 8,337,899, 8,431,159, 9,028,870, 9,060,938, 9,211,261, 9,265,731, 9,358,478, and 9,387,252, incorporated by reference herein.

The pharmaceutical compositions contemplated here can optionally include a carrier. Carriers must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound. Classes of carriers include, but are not limited to binders, buffering agents, coloring agents, diluents, disintegrants, emulsifiers, fillers, flavorants, glidents, lubricants, pH modifiers, preservatives, stabilizers, surfactants, solubilizers, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Examples of other matrix materials, fillers, or diluents include lactose, mannitol, xylitol, microcrystalline cellulose, calcium diphosphate, and starch. Examples of surface active agents include sodium lauryl sulfate and polysorbate 80. Examples of drug complexing agents or solubilizers include the polyethylene glycols, caffeine, xanthene, gentisic acid and cylodextrins. Examples of disintegrants include sodium starch glycolate, sodium alginate, carboxymethyl cellulose sodium, methyl cellulose, colloidal silicon dioxide, and croscarmellose sodium. Examples of binders include methyl cellulose, microcrystalline cellulose, starch, and gums such as guar gum, and tragacanth. Examples of lubricants include magnesium stearate and calcium stearate. Examples of pH modifiers include acids such as citric acid, acetic acid, ascorbic acid, lactic acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids. Optional other active agents may be included in a pharmaceutical composition, which do not substantially interfere with the activity of the compound of the present invention.

In certain embodiments, the pharmaceutical composition for administration further includes a compound or salt of Formula I, II, or III and optionally comprises one or more of a phosphoglyceride; phosphatidylcholine; dipalmitoyl phosphatidylcholine (DPPC); dioleoylphosphatidyl ethanolamine (DOPE); dioleoyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohol such as polyethylene glycol (PEG); polyoxyethylene-9-lauryl ether; a surface active fatty acid, such as palmitic acid or oleic acid; fatty acid; fatty acid monoglyceride; fatty acid diglyceride; fatty acid amide; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebroside; dicetylphosphate; dipalmitoylphosphatidylglycerol; stearylamine; dodecylamine; hexadecyl-amine; acetyl palmitate; glycerol ricinoleate; hexadecyl stearate; isopropyl myristate; tyloxapol; poly(ethylene glycol)5000-phosphatidylethanolamine; poly(ethylene glycol)400-monostearate; phospholipid; synthetic and/or natural detergent having high surfactant properties; deoxycholate; cyclodextrin; chaotropic salt; ion pairing agent; glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid; pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan, mannitol, sorbitol, xylitol, erythritol, maltitol, and lactitol, a pluronic polymer, polyethylene, polycarbonate (e.g. poly(1,3-dioxan-2one)), polyanhydride (e.g. poly(sebacic anhydride)), polypropylfumerate, polyamide (e.g. polycaprolactam), polyacetal, polyether, polyester (e.g., polylactide, polyglycolide, polylactide-co-glycolide, polycaprolactone, polyhydroxyacid (e.g. poly((β-hydroxyalkanoate))), poly(orthoester), polycyanoacrylate, polyvinyl alcohol, polyurethane, polyphosphazene, polyacrylate, polymethacrylate, polyurea, polystyrene, and polyamine, polylysine, polylysine-PEG copolymer, and poly(ethyleneimine), poly(ethylene imine)-PEG copolymer, glycerol monocaprylocaprate, propylene glycol, Vitamin E TPGS (also known as d-α-Tocopheryl polyethylene glycol 1000 succinate), gelatin, titanium dioxide, polyvinylpyrrolidone (PVP), hydroxypropyl methyl cellulose (HPMC), hydroxypropyl cellulose (HPC), methyl cellulose (MC), block copolymers of ethylene oxide and propylene oxide (PEO/PPO), polyethyleneglycol (PEG), sodium carboxymethylcellulose (NaCMC), hydroxypropylmethyl cellulose acetate succinate (HPMCAS).

In some embodiments, the pharmaceutical preparation may include polymers for controlled delivery of the described compounds, including, but not limited to pluronic polymers, polyesters (e.g., polylactic acid, poly(lactic-co-glycolic acid), polycaprolactone, polyvalerolactone, poly(1, 3-dioxan-2one)); polyanhydrides (e.g., poly(sebacic anhydride)); polyethers (e.g., polyethylene glycol); polyurethanes; polymethacrylates; polyacrylates; and polycyanoacrylates. In some embodiments, polymers may be modified with polyethylene glycol (PEG), with a carbohydrate, and/or with acyclic polyacetals derived from polysaccharides. See, e.g., Papisov, 2001, ACS Symposium Series, 786:301, incorporated by reference herein.

The compounds of the present invention can be formulated as particles. In one embodiment the particles are or include microparticles. In an alternative embodiment the particles are or include nanoparticles.

In an additional alternative embodiment, common techniques for preparing particles include, but are not limited to, solvent evaporation, solvent removal, spray drying, phase inversion, coacervation, and low temperature casting. Suitable methods of particle formulation are briefly described below. Pharmaceutically acceptable excipients, including pH modifying agents, disintegrants, preservatives, and antioxidants, can optionally be incorporated into the particles during particle formation.

In one embodiment, the particles are derived through a solvent evaporation method. In this method, a compound described herein (or polymer matrix and one or more compounds described herein) is dissolved in a volatile organic solvent, such as methylene chloride. The organic solution containing a compound described herein is then suspended in an aqueous solution that contains a surface active agent such as poly(vinyl alcohol). The resulting emulsion is stirred until most of the organic solvent evaporated, leaving solid nanoparticles or microparticles. The resulting nanoparticles or microparticles are washed with water and dried overnight in a lyophilizer. Nanoparticles with different sizes and morphologies can be obtained by this method.

Pharmaceutical compositions which contain labile polymers, such as certain polyanhydrides, may degrade during the fabrication process due to the presence of water. For these polymers, methods which are performed in completely or substantially anhydrous organic solvents can be used to make the particles.

Solvent removal can also be used to prepare particles from a compound that is hydrolytically unstable. In this method, the compound (or polymer matrix and one or more compounds) is dispersed or dissolved in a volatile organic solvent such as methylene chloride. This mixture is then suspended by stirring in an organic oil (such as silicon oil) to form an emulsion. Solid particles form from the emulsion, which can subsequently be isolated from the supernatant. The external morphology of spheres produced with this technique is highly dependent on the identity of the drug.

In one embodiment an active compound as described herein is administered to a patient in need thereof as particles formed by solvent removal. In another embodiment the present invention provides particles formed by solvent removal comprising a compound of the present invention and one or more pharmaceutically acceptable excipients as defined herein. In another embodiment the particles formed by solvent removal comprise a compound of the present invention and an additional therapeutic agent. In a further embodiment the particles formed by solvent removal comprise a compound of the present invention, an additional therapeutic agent, and one or more pharmaceutically acceptable excipients. In another embodiment any of the described particles formed by solvent removal can be formulated into a tablet and then coated to form a coated tablet. In an alternative embodiment the particles formed by solvent removal are formulated into a tablet but the tablet is uncoated.

In one embodiment, the particles are derived by spray drying. In this method, a compound (or polymer matrix and one or more compounds) is dissolved in an organic solvent such as methylene chloride. The solution is pumped through a micronizing nozzle driven by a flow of compressed gas, and the resulting aerosol is suspended in a heated cyclone of air, allowing the solvent to evaporate from the micro droplets, forming particles. Microparticles and nanoparticles can be obtained using this method.

In one embodiment an active compound as described herein is administered to a patient in need thereof as a spray dried dispersion (SDD). In another embodiment the present invention provides a spray dried dispersion (SDD) comprising a compound of the present invention and one or more pharmaceutically acceptable excipients as defined herein. In another embodiment the SDD comprises a compound of the present invention and an additional therapeutic agent. In a further embodiment the SDD comprises a compound of the present invention, an additional therapeutic agent, and one or more pharmaceutically acceptable excipients. In another embodiment any of the described spray dried dispersions can be coated to form a coated tablet. In an alternative embodiment the spray dried dispersion is formulated into a tablet but is uncoated. Particles can be formed from the active compound as described herein using a phase inversion method. In this method, the compound (or polymer matrix and one or more active compounds) is dissolved in a suitable solvent, and the solution is poured into a strong non-solvent for the compound to spontaneously produce, under favorable conditions, microparticles or nanoparticles. The method can be used to produce nanoparticles in a wide range of sizes, including, for example, from nanoparticles to microparticles, typically possessing a narrow particle size distribution.

In one embodiment, an active compound as described herein is administered to a patient in need thereof as particles formed by phase inversion. In another embodiment the present invention provides particles formed by phase inversion comprising a compound of the present invention and one or more pharmaceutically acceptable excipients as defined herein. In another embodiment the particles formed by phase inversion comprise a compound of the present invention and an additional therapeutic agent. In a further embodiment the particles formed by phase inversion comprise a compound of the present invention, an additional therapeutic agent, and one or more pharmaceutically acceptable excipients. In another embodiment any of the described particles formed by phase inversion can be formulated into a tablet and then coated to form a coated tablet. In an alternative embodiment the particles formed by phase inversion are formulated into a tablet but the tablet is uncoated.

Techniques for particle formation using coacervation are known in the art, for example, as described in GB-B-929 406; GB-B-929 401; and U.S. Pat. Nos. 3,266,987, 4,794,000, and 4,460,563. Coacervation involves the separation of a compound (or polymer matrix and one or more compounds) solution into two immiscible liquid phases. One phase is a dense coacervate phase, which contains a high concentration of the compound, while the second phase contains a low concentration of the compound. Within the dense coacervate phase, the compound forms nanoscale or microscale droplets, which harden into particles. Coacervation may be induced by a temperature change, addition of a non-solvent or addition of a micro-salt (simple coacervation), or by the addition of another polymer thereby forming an interpolymer complex (complex coacervation).

In one embodiment an active compound as described herein is administered to a patient in need thereof as particles formed by coacervation. In another embodiment the present invention provides particles formed by coacervation comprising a compound of the present invention and one or more pharmaceutically acceptable excipients as defined herein. In another embodiment the particles formed by coacervation comprise a compound of the present invention and an additional therapeutic agent. In a further embodiment the particles formed by coacervation comprise a compound of the present invention, an additional therapeutic agent, and one or more pharmaceutically acceptable excipients. In another embodiment any of the described particles formed by coacervation can be formulated into a tablet and then coated to form a coated tablet. In an alternative embodiment the particles formed by coacervation are formulated into a tablet but the tablet is uncoated.

Methods for very low temperature casting of controlled release microspheres are described in U.S. Pat. No. 5,019,400 to Gombotz et al. In this method, the compound is dissolved in a solvent. The mixture is then atomized into a vessel containing a liquid non-solvent at a temperature below the freezing point of the drug solution which freezes the compound droplets. As the droplets and non-solvent for the compound are warmed, the solvent in the droplets thaws and is extracted into the non-solvent, hardening the microspheres.

In one embodiment, a compound of the present invention is administered to a patient in need thereof as particles formed by low temperature casting. In another embodiment the present invention provides particles formed by low temperature casting comprising a compound of the present invention and one or more pharmaceutically acceptable excipients as defined herein. In another embodiment the particles formed by low temperature casting comprise a compound of the present invention and an additional therapeutic agent. In a further embodiment the particles formed by low temperature casting comprise a compound of the present invention, an additional therapeutic agent, and one or more pharmaceutically acceptable excipients. In another embodiment any of the described particles formed by low temperature casting can be formulated into a tablet and then coated to form a coated tablet. In an alternative embodiment the particles formed by low temperature casting are formulated into a tablet but the tablet is uncoated.

In one aspect of the present invention, an effective amount of an active compound as described herein is incorporated into a nanoparticle, e.g. for convenience of delivery and/or extended release delivery. The use of materials in nanoscale provides one the ability to modify fundamental physical properties such as solubility, diffusivity, blood circulation half-life, drug release characteristics, and/or immunogenicity. A number of nanoparticle-based therapeutic and diagnostic agents have been developed for the treatment of cancer, diabetes, pain, asthma, allergy, and infections. These nanoscale agents may provide more effective and/or more convenient routes of administration, lower therapeutic toxicity, extend the product life cycle, and ultimately reduce health-care costs. As therapeutic delivery systems, nanoparticles can allow targeted delivery and controlled release.

In addition, nanoparticle-based compound delivery can be used to release compounds at a sustained rate and thus lower the frequency of administration, deliver drugs in a targeted manner to minimize systemic side effects, or deliver two or more drugs simultaneously for combination therapy to generate a synergistic effect and suppress drug resistance. A number of nanotechnology-based therapeutic products have been approved for clinical use. Among these products, liposomal drugs and polymer-based conjugates account for a large proportion of the products. See, Zhang, L., et al., Nanoparticles in Medicine: Therapeutic Applications and Developments, Clin. Pharm. and Ther., 83(5):761-769, 2008.

Methods for producing nanoparticles are known in the art. For example, see Muller, R. H., et al., Solid lipid nanoparticles (SLN) for controlled drug delivery—a review of the state of the art, Eur. H. Pharm. Biopharm., 50:161-177, 2000; U.S. Pat. No. 8,691,750 to Consien et al.; WO 2012/145801 to Kanwar. U.S. Pat. No. 8,580,311 to Armes, S. et al.; Petros, R. A. and DeSimone, J. M., Strategies in the design of nanoparticles for therapeutic applications, Nature Reviews/Drug Discovery, vol. 9:615-627, 2010; U.S. Pat. Nos. 8,465,775; 8,444,899; 8,420,124; 8,263,129; 8,158,728; 8,268,446; Pellegrino et al., 2005, Small, 1:48; Murray et al., 2000, Ann. Rev. Mat. Sci., 30:545; and Trindade et al., 2001, Chem. Mat., 13:3843; all incorporated herein by reference. Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6):843-853 (2010)), U.S. Pat. No. 5,543,158 to Gref et al., or WO publication WO2009/051837 by Von Andrian et al. Zauner et al., 1998, Adv. Drug Del. Rev., 30:97; and Kabanov et al., 1995, Bioconjugate Chem., 6:7; (PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372; Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester)(Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633; U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181; Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732; C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6):843-853 (2010); U.S. Pat. No. 6,632,671 to Unger Oct. 14, 2003, all incorporated herein by reference.

In one embodiment, the polymeric particle is between about 0.1 nm to about 10000 nm, between about 1 nm to about 1000 nm, between about 10 nm and 1000 nm, between about 1 and 100 nm, between about 1 and 10 nm, between about 1 and 50 nm, between about 100 nm and 800 nm, between about 400 nm and 600 nm, or about 500 nm. In one embodiment, the micro-particles are no more than about 0.1 nm, 0.5 nm, 1.0 nm, 5.0 nm, 10 nm, 25 nm, 50 nm, 75 nm, 100 nm, 150 nm, 200 nm, 250 nm, 300 nm, 400 nm, 450 nm, 500 nm, 550 nm, 600 nm, 650 nm, 700 nm, 750 nm, 800 nm, 850 nm, 900 nm, 950 nm, 1000 nm, 1250 nm, 1500 nm, 1750 nm, or 2000 nm. In some embodiments, a compound described herein may be covalently coupled to a polymer used in the nanoparticle, for example a polystyrene particle, PLGA particle, PLA particle, or other nanoparticle.

The pharmaceutical compositions can be formulated for oral administration. These compositions can contain any amount of active compound that achieves the desired result, for example between 0.1 and 99 weight % (wt. %) of the compound and usually at least about 5 wt. % of the compound. Some embodiments contain at least about 10%, 15%, 20%, 25 wt. % to about 50 wt. % or from about 5 wt. % to about 75 wt. % of the compound.

Pharmaceutical compositions suitable for rectal administration are typically presented as unit dose suppositories. These may be prepared by admixing the active compound with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Pharmaceutical compositions suitable for transdermal administration may be presented as discrete patches adapted to remain in intimate contact with the epidermis of the recipient for a prolonged period of time. Pharmaceutical compositions suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Pharmaceutical compositions suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Additional non-limiting examples of inhalation drug delivery devices and methods include, for example, U.S. Pat. No. 7,383,837 titled "Inhalation device" (SmithKline Beecham Corporation); WO/2006/033584 titled "Powder inhaler" (Glaxo SmithKline Pharmaceuticals SA); WO/2005/044186 titled "Inhalable pharmaceutical formulations employing desiccating agents and methods of administering the same" (Glaxo Group Ltd and SmithKline Beecham Corporation); U.S. Pat. No. 9,095,670 titled "Inhalation device and method of dispensing medicament", U.S. Pat. No. 8,205,611 titled "Dry powder inhaler" (Astrazeneca AB); WO/2013/038170 titled "Inhaler" (Astrazeneca AB and Astrazeneca UK Ltd.); US/2014/0352690 titled "Inhalation Device with Feedback System", U.S. Pat. No. 8,910,625 and US/2015/0165137 titled "Inhalation Device for Use in Aerosol Therapy" (Vectura GmbH); U.S. Pat. No. 6,948,496 titled "Inhalers", US/2005/0152849 titled "Powders comprising anti-adherent materials for use in dry powder inhalers", U.S. Pat. Nos. 6,582,678, 8,137,657, US/2003/0202944, and US/2010/0330188 titled "Carrier particles for use in dry powder inhalers", U.S. Pat. No. 6,221,338 titled "Method of producing particles for use in dry powder inhalers", U.S. Pat. No. 6,989,155 titled "Powders", US/2007/0043030 titled "Pharmaceutical compositions for treating premature ejaculation by pulmonary inhalation", U.S. Pat. No. 7,845,349 titled "Inhaler", US/2012/0114709 and U.S. Pat. No. 8,101,160 titled "Formulations for Use in Inhaler Devices", US/2013/0287854 titled "Compositions and Uses", US/2014/0037737 and U.S. Pat. No. 8,580,306 titled "Particles for Use in a Pharmaceutical Composition", US/2015/0174343 titled "Mixing Channel for an Inhalation Device", U.S. Pat. No. 7,744,855 and US/2010/0285142 titled "Method of making particles for use in a pharmaceutical composition", U.S. Pat. No. 7,541,022, US/2009/0269412, and US/2015/0050350 titled "Pharmaceutical formulations for dry powder inhalers" (Vectura Limited).

Many methods and devices for drug delivery to the eye are known in the art. Non-limiting examples are described in the following patents and patent applications (fully incorporated herein by reference). Examples are U.S. Pat. No. 8,192,408 titled "Ocular trocar assembly" (Psivida Us, Inc.); U.S. Pat. No. 7,585,517 titled "Transcleral delivery" (Macusight, Inc.); U.S. Pat. Nos. 5,710,182 and 5,795,913 titled "Ophthalmic composition" (Santen OY); U.S. Pat. No. 8,663,639 titled "Formulations for treating ocular diseases and conditions", U.S. Pat. No. 8,486,960 titled "Formulations and methods for vascular permeability-related diseases or conditions", U.S. Pat. Nos. 8,367,097 and 8,927,005 titled "Liquid formulations for treatment of diseases or conditions", U.S. Pat. No. 7,455,855 titled "Delivering substance and drug delivery system using the same" (Santen Pharmaceutical Co., Ltd.); WO/2011/050365 titled "Conformable Therapeutic Shield For Vision and Pain" and WO/2009/145842 titled "Therapeutic Device for Pain Management and Vision" (Forsight Labs, LLC); U.S. Pat. Nos. 9,066,779 and 8,623,395 titled "Implantable therapeutic device", WO/2014/160884 titled "Ophthalmic Implant for Delivering Therapeutic Substances", U.S. Pat. Nos. 8,399,006, 8,277, 830, 8,795,712, 8,808,727, 8,298,578, and WO/2010/088548 titled "Posterior segment drug delivery", WO/2014/152959 and US20140276482 titled "Systems for Sustained Intraocular Delivery of Low Solubility Compounds from a Port Delivery System Implant", U.S. Pat. Nos. 8,905,963 and 9,033,911 titled "Injector apparatus and method for drug delivery", WO/2015/057554 titled "Formulations and Methods for Increasing or Reducing Mucus", U.S. Pat. Nos. 8,715,712 and 8,939,948 titled "Ocular insert apparatus and methods", WO/2013/116061 titled "Insertion and Removal Methods and Apparatus for Therapeutic Devices", WO/2014/066775 titled "Ophthalmic System for Sustained Release of Drug to the Eye", WO/2015/085234 and WO/2012/019176 titled "Implantable Therapeutic Device", WO/2012/065006 titled "Methods and Apparatus to determine Porous Structures for Drug Delivery", WO/2010/141729 titled "Anterior Segment Drug Delivery", WO/2011/050327 titled "Corneal Denervation for Treatment of Ocular Pain", WO/2013/022801 titled "Small Molecule Delivery with Implantable Therapeutic Device", WO/2012/019047 titled "Subconjunctival Implant for Posterior Segment Drug Delivery", WO/2012/068549 titled "Therapeutic Agent Formulations for Implanted Devices", WO/2012/019139 titled "Combined Delivery Methods and Apparatus", WO/2013/040426 titled "Ocular Insert Apparatus and Methods", WO/2012/019136 titled "Injector Apparatus and Method for Drug Delivery", WO/2013/040247 titled "Fluid Exchange Apparatus and Methods" (ForSight Vision4, Inc.).

Additional non-limiting examples of how to deliver the active compounds are provided in WO/2015/085251 titled "Intracameral Implant for Treatment of an Ocular Condition" (Envisia Therapeutics, Inc.); WO/2011/008737 titled "Engineered Aerosol Particles, and Associated Methods", WO/2013/082111 titled "Geometrically Engineered Particles and Methods for Modulating Macrophage or Immune Responses", WO/2009/132265 titled "Degradable compounds and methods of use thereof, particularly with particle replication in non-wetting templates", WO/2010/099321 titled "Interventional drug delivery system and associated methods", WO/2008/100304 titled "Polymer particle composite having high fidelity order, size, and shape particles", WO/2007/024323 titled "Nanoparticle fabrication methods, systems, and materials" (Liquidia Technologies, Inc. and the University of North Carolina at Chapel Hill); WO/2010/009087 titled "Iontophoretic Delivery of a Controlled-Release Formulation in the Eye", (Liquidia Technologies, Inc. and Eyegate Pharmaceuticals, Inc.) and WO/2009/132206 titled "Compositions and Methods for Intracellular Delivery and Release of Cargo", WO/2007/133808 titled "Nanoparticles for cosmetic applications", WO/2007/056561 titled "Medical device, materials, and methods", WO/2010/065748 titled "Method for producing patterned materials", WO/2007/081876 titled "Nanostructured surfaces for biomedical/biomaterial applications and processes thereof" (Liquidia Technologies, Inc.).

Additional non-limiting examples of methods and devices for drug delivery to the eye include, for example, WO2011/106702 and U.S. Pat. No. 8,889,193 titled "Sustained delivery of therapeutic agents to an eye compartment", WO2013/138343 and U.S. Pat. No. 8,962,577 titled "Controlled release formulations for the delivery of HIF-1 inhibitors", WO/2013/138346 and US2013/0272994 titled "Non-Linear Multiblock Copolymer-Drug Conjugates for the Delivery of Active Agents", WO2005/072710 and U.S. Pat. No. 8,957, 034 titled "Drug and Gene Carrier Particles that Rapidly Move Through Mucus Barriers", WO2008/030557, US2010/0215580, US2013/0164343 titled "Compositions and Methods for Enhancing Transport Through Mucous", WO2012/061703, US2012/0121718, and US2013/0236556 titled "Compositions and Methods Relating to Reduced Mucoadhesion", WO2012/039979 and US2013/0183244 titled "Rapid Diffusion of Large Polymeric Nanoparticles in the Mammalian Brain", WO2012/109363 and US2013/0323313 titled "Mucus Penetrating Gene Carriers", WO 2013/090804 and US2014/0329913 titled "Nanoparticles with enhanced mucosal penetration or decreased inflammation", WO2013/110028 titled "Nanoparticle formulations with enhanced mucosal penetration", WO2013/166498 and US2015/0086484 titled "Lipid-based drug carriers for rapid penetration through mucus linings" (The Johns Hopkins University); WO2013/166385 titled "Pharmaceutical Nanoparticles Showing Improved Mucosal Transport", US2013/0323179 titled "Nanocrystals, Compositions, And Methods that Aid Particle Transport in Mucus" (The Johns Hopkins University and Kala Pharmaceuticals, Inc.); WO/2015/066444 titled "Compositions and methods for ophthalmic and/or other applications", WO/2014/020210 and WO/2013/

166408 titled "Pharmaceutical nanoparticles showing improved mucosal transport" (Kala Pharmaceuticals, Inc.); U.S. Pat. No. 9,022,970 titled "Ophthalmic injection device including dosage control device", WO/2011/153349 titled "Ophthalmic compositions comprising pbo-peo-pbo block copolymers", WO/2011/140203 titled "Stabilized ophthalmic galactomannan formulations", WO/2011/068955 titled "Ophthalmic emulsion", WO/2011/037908 titled "Injectable aqueous ophthalmic composition and method of use therefor", US2007/0149593 titled "Pharmaceutical Formulation for Delivery of Receptor Tyrosine Kinase Inhibiting (RTKi) Compounds to the Eye", U.S. Pat. No. 8,632,809 titled "Water insoluble polymer matrix for drug delivery" (Alcon, Inc.).

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drugloading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilichydrophobic multiblock copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

Uses of Active Compounds for Treatment of Selected Disorders

In one aspect, an effective amount of an active compound or its salt or composition as described herein is used to treat a medical disorder which is an inflammatory or immune condition, a disorder mediated by the complement cascade (including a dysfunctional cascade) including a complement factor D-related disorder or alternative complement pathway-related disorder, a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration.

In one embodiment, the disorder is selected from fatty liver and conditions stemming from fatty liver, such as nonalcoholic steatohepatitis (NASH), liver inflammation, cirrhosis and liver failure. In one embodiment of the present invention, a method is provided for treating fatty liver disease in a host by administering an effective amount of an active compound or its salt or composition as described herein.

In another embodiment, an active compound or its salt or composition as described herein is used to modulate an immune response prior to or during surgery or other medical procedure. One non-limiting example is use in connection with acute or chronic graft versus host disease, which is a common complication as a result of allogeneic tissue transplant, and can also occur as a result of a blood transfusion.

In one embodiment, the present invention provides a method of treating or preventing dermatomyositis by administering to a subject in need thereof an effective amount of an active compound or its salt or composition as described herein.

In one embodiment, the present invention provides a method of treating or preventing amyotrophic lateral sclerosis by administering to a subject in need thereof an effective amount of an active compound or its salt or composition as described herein.

In one embodiment, the present invention provides a method of treating or preventing abdominal aortic aneurysm, hemodialysis complications, hemolytic anemia, or hemodialysis by administering to a subject in need thereof an effective amount of an active compound or its salt or composition as described herein.

In another embodiment, a method is provided for the treatment or prevention of cytokine or inflammatory reactions in response to the administration of pharmaceutical or biotherapeutic (e.g. CAR T-cell therapy or monoclonal antibody therapy) in a host by administering an effective amount of an active compound or its salt or composition as described herein. Various types of cytokine or inflammatory reactions may occur in response to a number of factors, such as the administrations of biotherapeutics. In one embodiment, the cytokine or inflammatory reaction is cytokine release syndrome. In one embodiment, the cytokine or inflammatory reaction is tumor lysis syndrome (which also leads to cytokine release). Symptoms of cytokine release syndrome range from fever, headache, and skin rashes to bronchospasm, hypotension and even cardiac arrest. Severe cytokine release syndrome is described as cytokine storm, and can be fatal.

Fatal cytokine storms have been observed in response to infusion with several monoclonal antibody therapeutics. See, Abramowicz D, et al. "Release of tumor necrosis factor, interleukin-2, and gamma-interferon in serum after injection of OKT3 monoclonal antibody in kidney transplant recipients" *Transplantation* (1989) 47(4):606-8; Chatenoud L, et al. "In vivo cell activation following OKT3 administration. Systemic cytokine release and modulation by corticosteroids" *Transplantation* (1990) 49(4):697-702; and Lim L C, Koh L P, and Tan P. "Fatal cytokine release syndrome with chimeric anti-CD20 monoclonal antibody rituximab in a 71-year-old patient with chronic lymphocytic leukemia" *J. Clin Oncol.* (1999) 17(6):1962-3.

Also contemplated herein, is the use of an active compound or its salt or composition as described herein to mediate an adverse immune response in patients receiving bi-specific T-cell engagers (BiTE). A bi-specific T-cell engager directs T-cells to target and bind with a specific antigen on the surface of a cancer cell. For example, Blinatumomab (Amgen), a BiTE has recently been approved as a second line therapy in Philadelphia chromosome-negative relapsed or refractory acute lymphoblastic leukemia. Blinatumomab is given by continuous intravenous infusion in 4-week cycles. The use of BiTE agents has been associated with adverse immune responses, including cytokine release syndrome. The most significantly elevated cytokines in the CRS associated with ACT include IL-10, IL-6, and IFN-γ (Klinger et al., Immunopharmacologic response of patients with B-lineage acute lymphoblastic leukemia to continuous infusion of T cell-engaging CD19/CD3-bispecific BiTE antibody blinatumomab. Blood (2012) 119:6226-6233).

In another embodiment, the disorder is episcleritis, idiopathic episcleritis, anterior episcleritis, or posterior episcleritis. In one embodiment, the disorder is idiopathic anterior uveitis, HLA-B27 related uveitis, herpetic keratouveitis, Posner Schlossman syndrome, Fuch's heterochromic iridocyclitis, or cytomegalovirus anterior uveitis.

In one embodiment, the present invention provides a method of treating or preventing a C3 glomurenopathy by administering to a subject in need thereof an effective amount of an active compound or its salt or composition as described herein. In one embodiment, the disorder is selected from dense deposit disease (DDD) and C3 glomerulonephritis (C3GN).

In one embodiment, the present invention provides a method of treating or preventing a IC-MPGN by administering to a subject in need thereof an effective amount of an active compound or its salt or composition as described herein.

In one embodiment, the present invention provides a method of treating or preventing a paroxysmal nocturnal hemoglobinuria (PNH) by administering to a subject in need thereof an effective amount of an active compound or its salt or composition as described herein.

In one embodiment, the present invention provides a method of treating or preventing age-related macular degeneration (AMD) by administering to a subject in need thereof an effective amount of an active compound or its salt or composition as described herein.

In one embodiment, the present invention provides a method of treating or preventing rheumatoid arthritis by administering to a subject in need thereof an effective amount of an active compound or its salt or composition as described herein.

In one embodiment, the present invention provides a method of treating or preventing multiple sclerosis by administering to a subject in need thereof an effective amount of an active compound or its salt or composition as described herein.

In one embodiment, the present invention provides a method of treating or preventing myasthenia gravis by administering to a subject in need thereof an effective amount of an active compound or its salt or composition as described herein.

In one embodiment, the present invention provides a method of treating or preventing atypical hemolytic uremic syndrome (aHUS) by administering to a subject in need thereof an effective amount of an active compound or its salt or composition as described herein.

In one embodiment, the present invention provides a method of treating or preventing neuromyelitis optica (NMO) by administering to a subject in need thereof an effective amount of an active compound or its salt or composition as described herein.

In yet another embodiment, the present invention provides a method of treating or preventing a disorder as described below by administering to a subject in need thereof an effective amount of an active compound or its salt or composition as described herein, including:
vitritis, sarcoidosis, syphilis, tuberculosis, or Lyme disease; retinal vasculitis, Eales disease, tuberculosis, syphilis, or toxoplasmosis; neuroretinitis, viral retinitis, or acute retinal necrosis; varicella zoster virus, herpes simplex virus, cytomegalovirus, Epstein-Barr virus, lichen planus, or Dengue-associated disease (e.g., hemorraghic Dengue Fever); Masquerade syndrome, contact dermatitis, trauma induced inflammation, UVB induced inflammation, eczema, granuloma annulare, or acne.

In an additional embodiment, the disorder is selected from: acute myocardial infarction, aneurysm, cardiopulmonary bypass, dilated cardiomyopathy, complement activation during cardiopulmonary bypass operations, coronary artery disease, restenosis following stent placement, or percutaneous transluminal coronary angioplasty (PTCA); antibody-mediated transplant rejection, anaphylactic shock, anaphylaxis, allogenic transplant, humoral and vascular transplant rejection, graft dysfunction, graft-versus-host disease, Graves' disease, adverse drug reactions, or chronic graft vasculopathy; allergic bronchopulmonary aspergillosis, allergic neuritis, drug allergy, radiation-induced lung injury, eosinophilic pneumonia, radiographic contrast media allergy, bronchiolitis obliterans, or interstitial pneumonia; parkinsonism-dementia complex, sporadic frontotemporal dementia, frontotemporal dementia with Parkinsonism linked to chromosome 17, frontotemporal lobar degeneration, tangle only dementia, cerebral amyloid angiopathy, cerebrovascular disorder, certain forms of frontotemporal dementia, chronic traumatic encephalopathy (CTE), PD with dementia (PDD), argyrophilic grain dementia, dementia pugilistica, dementia with Lewy Bodies (DLB), or multi-infarct dementia; Creutzfeldt-Jakob disease, Huntington's disease, multifocal motor neuropathy (MMN), prion protein cerebral amyloid angiopathy, polymyositis, postencephalitic parkinsonism, subacute sclerosing panencephalitis, non-Guamanian motor neuron disease with neurofibrillary tangles, neural regeneration, or diffuse neurofibrillary tangles with calcification.

In one embodiment, the disorder is selected from: atopic dermatitis, dermatitis, dermatomyositis bullous pemphigoid, scleroderma, sclerodermatomyositis, psoriatic arthritis, pemphigus vulgaris, Discoid lupus erythematosus, cutaneous lupus, chilblain lupus erythematosus, or lupus erythematosus-lichen planus overlap syndrome; cryoglobulinemic vasculitis, mesenteric/enteric vascular disorder, peripheral vascular disorder, antineutrophil cytoplasm antibody (ANCA)-associated vasculitis (AAV), IL-2 induced vascular leakage syndrome, or immune complex vasculitis; angioedema, low platelets (HELLP) syndrome, sickle cell disease, platelet refractoriness, red cell casts, or typical or infectious hemolytic uremic syndrome (tHUS); hematuria, hemorrhagic shock, drug-induced thrombocytopenia, autoimmune hemolytic anemia (AIHA), azotemia, blood vessel and/or lymph vessel inflammation, rotational atherectomy, or delayed hemolytic transfusion reaction; British type amyloid angiopathy, Buerger's disease, bullous pemphigoid, C1q nephropathy, cancer, or catastrophic antiphospholipid syndrome.

In another embodiment, the disorder is selected from: wet (exudative) AMD, dry (non-exudative) AMD, chorioretinal degeneration, choroidal neovascularization (CNV), choroiditis, loss of RPE function, loss of vision (including loss of visual acuity or visual field), loss of vision from AMD, retinal damage in response to light exposure, retinal degeneration, retinal detachment, retinal dysfunction, retinal neovascularization (RNV), retinopathy of prematurity, pathological myopia, or RPE degeneration; pseudophakic bullous keratopathy, symptomatic macular degeneration related disorder, optic nerve degeneration, photoreceptor degeneration, cone degeneration, loss of photoreceptor cells, pars planitis, scleritis, proliferative vitreoretinopathy, or formation of ocular drusen; chronic urticaria, Churg-Strauss syndrome, cold agglutinin disease (CAD), corticobasal degeneration (CBD), cryoglobulinemia, cyclitis, damage of the Bruch's membrane, Degos disease, diabetic angiopathy, elevated liver enzymes, endotoxemia, epidermolysis bullosa, or epidermolysis bullosa acquisita; essential mixed cryoglobulinemia, excessive blood urea nitrogen-BUN, focal segmental glomerulosclerosis, Gerstmann-Straussler-Scheinker disease, giant cell arteritis, gout, Hallervorden-Spatz disease, Hashimoto's thyroiditis, Henoch-Schonlein purpura nephritis, or abnormal urinary sediments; hepatitis, hepatitis A, hepatitis B, hepatitis C or human immunodeficiency virus (HIV), a viral infection more generally, for example selected from Flaviviridae, Retroviruses, Coronaviridae, Poxviridae, Adenoviridae, Herpesviridae, Caliciviridae, Reoviridae, Picornaviridae, Togaviridae, Orthomyxoviridae, Rhabdoviridae, or Hepadnaviridae; *Neisseria meningitidis*, shiga toxin *E. coli*-related hemolytic uremic syndrome (STEC-HUS), hemolytic uremic syndrome (HUS); *Streptococcus*, or poststreptococcal glomerulonephritis.

In a further embodiment, the disorder is selected from: hyperlipidemia, hypertension, hypoalbuminemia, hypobolemic shock, hypocomplementemic urticarial vasculitis syndrome, hypophosphastasis, hypovolemic shock, idiopathic pneumonia syndrome, or idiopathic pulmonary fibrosis; inclusion body myositis, intestinal ischemia, iridocyclitis, iritis, juvenile chronic arthritis, Kawasaki's disease (arteritis), or lipiduria; membranoproliferative glomerulonephritis (MPGN) I, microscopic polyangiitis, mixed cryoglobulinemia, molybdenum cofactor deficiency (MoCD) type A, pancreatitis, panniculitis, Pick's disease, polyarteritis nodosa (PAN), progressive subcortical gliosis, proteinuria, reduced glomerular filtration rate (GFR), or renovascular disorder; multiple organ failure, multiple system atrophy (MSA), myotonic dystrophy, Niemann-Pick disease type C, chronic demyelinating diseases, or progressive supranuclear palsy; spinal cord injury, spinal muscular atrophy, spondyloarthropathies, Reiter's syndrome, spontaneous fetal loss, recurrent fetal loss, pre-eclampsia, synucleinopathy, Takayasu's arteritis, post-partum thryoiditis, thyroiditis, Type I cryoglobulinemia, Type II mixed cryoglobulinemia, Type III mixed cryoglobulinemia, ulcerative colitis, uremia, urticaria, venous gas embolus (VGE), or Wegener's granulomatosis; von Hippel-Lindau disease, histoplasmosis of the eye, hard drusen, soft drusen, pigment clumping, or photoreceptor and/or retinal pigmented epithelia (RPE) loss.

In one embodiment, an active compound or its salt or composition as described herein is useful for treating or preventing a disorder selected from autoimmune oophoritis, endometriosis, autoimmune orchitis, Ord's thyroiditis, autoimmune enteropathy, coeliac disease, Hashimoto's encephalopathy, antiphospholipid syndrome (APLS) (Hughes syndrome), aplastic anemia, autoimmune lymphoproliferative syndrome (Canale-Smith syndrome), autoimmune neutropenia, Evans syndrome, pernicious anemia, pure red cell aplasia, thrombocytopenia, adipose dolorosa (Dercum's disease), adult onset Still's disease, ankylosing spondylitis, CREST syndrome, drug-induced lupus, eosinophilic fasciitis (Shulman's syndrome), Felty syndrome, IgG4-related disease, mixed connective tissue disease (MCTD), palindromic rheumatism (Hench-Rosenberg syndrome), Parry-Romberg syndrome, Parsonage-Turner syndrome, relapsing polychondritis (Meyenburg-Altherr-Uehlinger syndrome), retroperitonial fibrosis, rheumatic fever, Schnitzler syndrome, fibromyalgia, neuromyotonia (Isaac's disease), paraneoplastic degeneration, autoimmune inner ear disease, Meniere's disease, interstitial cystitis, autoimmune pancreatitis, zika virus-related disorders, chikungunya virus-related disorders, subacute bacterial endocarditis (SBE), IgA nephropathy, IgA vasculitis, polymyalgia rheumatic, rheumatoid vasculitis, alopecia areata, autoimmune progesterone dermatitis, dermatitis herpetiformis, erythema nodosum, gestational pemphigoid, hidradenitis suppurativa, lichen sclerosus, linear IgA disease (LAD), morphea, myositis, pityriasis lichenoides et varioliformis acuta, vitiligo post-myocardial infarction syndrome (Dressler's syndrome), post-pericardiotomy syndrome, autoimmune retinopathy, Cogan syndrome, Graves opthalmopathy, ligneous conjunctivitis, Mooren's ulcer, opsoclonus myoclonus syndrome, optic neuritis, retinocochleocerebral vasculopathy (Susac's syndrome), sympathetic opthalmia, Tolosa-Hunt syndrome, interstitial lung disease, antisynthetase syndrome, Addison's disease, autoimmune polyendocrine syndrome (APS) type I, autoimmune polyendocrine syndrome (APS) type II, autoimmune polyendocrine syndrome (APS) type III, disseminated sclerosis (multiple sclerosis, pattern II), rapidly progressing glomerulonephritis (RPGN), juvenile rheumatoid arthritis, enthesitis-related arthritis, reactive arthritis (Reiter's syndrome), autoimmune hepatitis or lupoid hepatitis, primary biliary cirrhosis (PBS), primary sclerosing cholangitis, microscopic colitis, latent lupus (undifferentiated connective tissue disease (UCTD)), acute disseminated encephalomyelitis (ADEM), acute motor axonal neuropathy, anti-n-methyl-D-aspartate receptor encephalitis, Balo concentric sclerosis (Schilders disease), Bickerstaff's encephalitis, chronic inflammatory demyelinating polyneuropathy, idiopathic inflammatory demyelinating disease, Lambert-Eaton mysathenic syndrome, Oshtoran syndrome, pediatric autoimmune neuropsychiatric disorder associated with *Streptococcus* (PANDAS), progressive inflammatory neuropathy, restless leg syndrome, stiff person syndrome, Sydenhem syndrome, transverse myelitis, lupus vasculitis, leukocytoclastic vasculitis, Microscopic Polyangiitis, polymyositis or ischemic-reperfusion injury of the eye.

Examples of eye disorders that may be treated according to the compositions and methods disclosed herein include amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, Sjogren's syndrome, Stevens-Johnson syndrome, autoimmune dry eye diseases, environmental dry eye diseases, corneal neovascularization diseases, post-corneal transplant rejection prophylaxis and treatment, autoimmune uveitis, infectious uveitis, posterior uveitis (including toxoplasmosis), pan-uveitis, an inflammatory disease of the vitreous or retina, endophthalmitis prophylaxis and treatment, macular edema, macular degeneration, age related macular degeneration, proliferative and non-proliferative diabetic retinopathy, hypertensive retinopathy, an autoimmune disease of the retina, primary and metastatic intraocular melanoma, other intraocular metastatic tumors, open angle glaucoma, closed angle glaucoma, pigmentary glaucoma and combinations thereof.

In a further embodiment, the disorder is selected from glaucoma, diabetic retinopathy, blistering cutaneous diseases (including bullous pemphigoid, pemphigus, and epidermolysis bullosa), ocular cicatrical pemphigoid, uveitis, adult macular degeneration, diabetic retinopa retinitis pigmentosa, macular edema, diabetic macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, and retinal vein occlusion, or central retinal vein occlusion (CVRO).

In some embodiments, complement mediated diseases include ophthalmic diseases (including early or neovascular age-related macular degeneration and geographic atrophy), autoimmune diseases (including arthritis, rheumatoid arthritis), respiratory diseases, cardiovascular diseases. In other embodiments, the compounds of the invention are suitable for use in the treatment of diseases and disorders associated with fatty acid metabolism, including obesity and other metabolic disorders.

Disorders that may be treated or prevented by an active compound or its salt or composition as described herein also include, but are not limited to: hereditary angioedema, capillary leak syndrome, hemolytic uremic syndrome (HUS), neurological disorders, Guillain Barre Syndrome, diseases of the central nervous system and other neurodegenerative conditions, glomerulonephritis (including membrane proliferative glomerulonephritis), SLE nephritis, proliferative nephritis, liver fibrosis, tissue regeneration and neural regeneration, or Barraquer-Simons Syndrome; inflammatory effects of sepsis, systemic inflammatory response syndrome (SIRS), disorders of inappropriate or undesirable complement activation, interleukin-2 induced toxicity during IL-2 therapy, inflammatory disorders, inflammation of autoimmune diseases, system lupus erythematosus (SLE), lupus nephritides, arthritis, immune complex disorders and autoimmune diseases, systemic lupus, or lupus erythematosus; ischemia/reperfusion injury (I/R injury), myocardial infarction, myocarditis, post-ischemic reperfusion conditions, balloon angioplasty, atherosclerosis, post-pump syndrome in cardiopulmonary bypass or renal bypass, renal ischemia, mesenteric artery reperfusion after aortic reconstruction, antiphospholipid syndrome, autoimmune heart disease, ischemia-reperfusion injuries, obesity, or diabetes; Alzheimer's dementia, stroke, schizophrenia, traumatic brain injury, trauma, Parkinson's disease, epilepsy, transplant rejection, prevention of fetal loss, biomaterial reactions (e.g. in hemodialysis, in plants), hyperacute allograft rejection, xenograft rejection, transplantation, psoriasis, burn injury, thermal injury including burns or frostbite, or crush injury; asthma, allergy, acute respiratory distress syndrome (ARDS), cystic fibrosis, adult respiratory distress syndrome, dyspnea, hemoptysis, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), bronchoconstriction, hypersensitivity pneumonitis, parasitic diseases, Goodpasture's Syndrome (anti-glomerular basement membrane nephritis), pulmonary vasculitis, Pauci-immune vasculitis, or immune complex-associated inflammation.

In one embodiment, a method for the treatment of sickle cell in a host is provided that includes the administration of an effective amount of an active compound or its salt or composition as described herein. In one embodiment, a method for the treatment of immunothrombocytopenic purpura (ITP), thrombotic thrombocytopenic purpura (TTP), or idiopathic thrombocytopenic purpura (ITP) in a host is provided that includes the administration of an effective amount of an active compound or its salt or composition as described herein. In one embodiment, a method for the treatment of ANCA-vasculitis in a host is provided that includes the administration of an effective amount of an active compound or its salt or composition as described herein. In one embodiment, a method for the treatment of IgA nephropathy in a host is provided that includes the administration of an effective amount of an active compound or its salt or composition as described herein. In one embodiment, a method for the treatment of rapidly progressing glomerulonephritis (RPGN), in a host is provided that includes the administration of an effective amount of an active compound or its salt or composition as described herein. In one embodiment, a method for the treatment of lupus nephritis, in a host is provided that includes the administration of an effective amount of an active compound or its salt or composition as described herein. In one embodiment, a method for the treatment of hemorraghic dengue fever, in a host is provided that includes the administration of an effective amount of an active compound or its salt or composition as described herein.

In an additional alternative embodiment, an active compound or its salt or composition as described herein is used in the treatment of an autoimmune disorder.

The complement pathway enhances the ability of antibodies and phagocytic cells to clear microbes and damaged cells from the body. It is part of the innate immune system and in healthy individuals is an essential process. Inhibiting the complement pathway will decrease the body's immune system response. Therefore, it is an object of the present invention to treat autoimmune disorders by administering an effective does of an active compound or its salt or composition as described herein to a subject in need thereof.

In one embodiment the autoimmune disorder is caused by activity of the complement system. In one embodiment the autoimmune disorder is caused by activity of the alternative complement pathway. In one embodiment the autoimmune disorder is caused by activity of the classical complement pathway. In another embodiment the autoimmune disorder is caused by a mechanism of action that is not directly related to the complement system, such as the over-proliferation of T-lymphocytes or the over-production of cytokines.

Non-limiting examples of autoimmune disorders include: lupus, allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, regional enteritis, granulomatous enteritis, distal ileitis, regional ileitis, and terminal ileitis), diabetes, multiple sclerosis, pernicious anemia, psoriasis, rheumatoid arthritis, sarcoidosis, and scleroderma.

In one embodiment, an active compound or its salt or composition as described herein is used in the treatment of lupus. Non-limiting examples of lupus include lupus erythematosus, cutaneous lupus, discoid lupus erythematosus, chilblain lupus erythematosus, or lupus erythematosus-lichen planus overlap syndrome.

Lupus erythematosus is a general category of disease that includes both systemic and cutaneous disorders. The systemic form of the disease can have cutaneous as well as systemic manifestations. However, there are also forms of the disease that are only cutaneous without systemic involvement. For example, SLE is an inflammatory disorder of unknown etiology that occurs predominantly in women, and is characterized by articular symptoms, butterfly erythema, recurrent pleurisy, pericarditis, generalized adenopathy, splenomegaly, as well as CNS involvement and progressive renal failure. The sera of most patients (over 98%) contain antinuclear antibodies, including anti-DNA antibodies. High titers of anti-DNA antibodies are essentially specific for SLE. Conventional treatment for this disease has been the administration of corticosteroids or immunosuppressants.

There are three forms of cutaneous lupus: chronic cutaneous lupus (also known as discoid lupus erythematosus or DLE), subacute cutaneous lupus, and acute cutaneous lupus. DLE is a disfiguring chronic disorder primarily affecting the skin with sharply circumscribed macules and plaques that display erythema, follicular plugging, scales, telangiectasia and atrophy. The condition is often precipitated by sun exposure, and the early lesions are erythematous, round scaling papules that are 5 to 10 mm in diameter and display follicular plugging. DLE lesions appear most commonly on the cheeks, nose, scalp, and ears, but they may also be generalized over the upper portion of the trunk, extensor surfaces of the extremities, and on the mucous membranes of the mouth. If left untreated, the central lesion atrophies and leaves a scar. Unlike SLE, antibodies against double-stranded DNA (e.g., DNA-binding test) are almost invariably absent in DLE.

Multiple Sclerosis is an autoimmune demyelinating disorder that is believed to be T lymphocyte dependent. MS generally exhibits a relapsing-remitting course or a chronic progressive course. The etiology of MS is unknown, however, viral infections, genetic predisposition, environment, and autoimmunity all appear to contribute to the disorder. Lesions in MS patients contain infiltrates of predominantly T lymphocyte mediated microglial cells and infiltrating macrophages. CD4+ T lymphocytes are the predominant cell type present at these lesions. The hallmark of the MS lesion is plaque, an area of demyelination sharply demarcated from the usual white matter seen in MRI scans. Histological appearance of MS plaques varies with different stages of the disease. In active lesions, the blood-brain barrier is damaged, thereby permitting extravasation of serum proteins into extracellular spaces. Inflammatory cells can be seen in perivascular cuffs and throughout white matter. CD4+ T-cells, especially Th1, accumulate around postcapillary venules at the edge of the plaque and are also scattered in the white matter. In active lesions, up-regulation of adhesion molecules and markers of lymphocyte and monocyte activation, such as IL2-R and CD26 have also been observed. Demyelination in active lesions is not accompanied by destruction of oligodendrocytes. In contrast, during chronic phases of the disease, lesions are characterized by a loss of oligodendrocytes and hence, the presence of myelin oligodendrocyte glycoprotein (MOG) antibodies in the blood.

Diabetes can refer to either type 1 or type 2 diabetes. In one embodiment an active compound or its salt or composition as described herein is provided at an effective dose to treat a patient with type 1 diabetes. In one embodiment an active compound or its salt or composition as described herein is provided at an effective dose to treat a patient with type 2 diabetes. Type 1 diabetes is an autoimmune disease. An autoimmune disease results when the body's system for fighting infection (the immune system) attacks a part of the body. In the case of diabetes type 1, the pancreas then produces little or no insulin.

Combination Therapy

In one embodiment an active compound or its salt or composition as described herein may be provided in combination or alternation with or preceded by, concomitant with or followed by, an effective amount of at least one additional therapeutic agent, for example, for treatment of a disorder listed herein. Non-limiting examples of second active agents for such combination therapy are provided below.

In one embodiment, an active compound or its salt or composition as described herein may be provided in combination or alternation with at least one additional inhibitor of the complement system or a second active compound with a different biological mechanism of action. In the description below and herein generally, whenever any of the terms referring to an active compound or its salt or composition as described herein are used, it should be understood that pharmaceutically acceptable salts, prodrugs or compositions are considered included, unless otherwise stated or inconsistent with the text.

In non-limiting embodiments, an active compound or its salt or composition as described herein may be provided together with a protease inhibitor, a soluble complement regulator, a therapeutic antibody (monoclonal or polyclonal), complement component inhibitor, receptor agonist, or siRNA.

In other embodiments, an active compound described herein is administered in combination or alternation with an antibody against tumor necrosis factor (TNF), including but not limited to infliximab (Remicade), adalimumab, certolizumab, golimumab, or a receptor fusion protein such as etanercept (Embrel).

In another embodiment, an active compound as described herein can be administered in combination or alternation with an anti-CD20 antibody, including but not limited to rituximab (Rituxan), adalimumab (Humira), ofatumumab (Arzerra), tositumomab (Bexxar), obinutuzumab (Gazyva), or ibritumomab (Zevalin).

In an alternative embodiment, an active compound as described herein can be administered in combination or alternation with an anti-IL6 antibody, including but not limited to tocilizumab (Actemra) and siltuximab (Sylvant).

In an alternative embodiment, an active compound as described herein can be administered in combination or alternation with an IL17 inhibitor, including but not limited to secukibumab (Cosentyx).

In an alternative embodiment, an active compound as described herein can be administered in combination or alternation with a p40 (IL12/IL23) inhibitor, including but not limited to ustekinumab (Stelara).

In an alternative embodiment, an active compound as described herein can be administered in combination or alteration with an IL23 inhibitor, including but not limited to risankizumab.

In an alternative embodiment, an active compound as described herein can be administered in combination or alteration with an anti-interferon α antibody, for example but not limited to sifalimumab.

In an alternative embodiment, an active compound as described herein can be administered in combination or alteration with a kinase inhibitor, for example but not limited to a JAK1/JAK3 inhibitor, for example but not limited to tofacitinib (Xelianz). In an alternative embodiment, an active compound as described herein can be administered in combination or alteration with a JAK1/JAK2 inhibitor, for example but not limited to baracitibib.

In an alternative embodiment, an active compound as described herein can be administered in combination or alteration with an anti-VEGF agent, for example but not limited to: aflibercept (Eylea®; Regeneron Pharmaceuticals); ranibizumab (Lucentis®: Genentech and Novartis); pegaptanib (Macugen®; OSI Pharmaceuticals and Pfizer); bevacizumab (Avastin; Genentech/Roche); lapatinib (Tykerb); sunitinib (Sutent); axitinib (Inlyta); pazopanib; sorafenib (Nexavar); ponatinib (Inclusig); regorafenib (Stivarga); cabozantinib (Abometyx; Cometriq); vendetanib (Caprelsa); ramucirumab (Cyramza); lenvatinib (Lenvima); ziv-aflibercept (Zaltrap); cediranib (Recentin); anecortane acetate, squalamine lactate, and corticosteroids.

In another embodiment, an active compound as described herein can be administered in combination or alternation with an immune checkpoint inhibitor. Non-limiting examples of checkpoint inhibitors include anti-PD-1 or anti-PDL1 antibodies, for example, nivolumab (Opdivo), pembrolizumab (Keytruda), pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.), atezolizumab, durvalumab, and KN035, or anti-CTLA4 antibodies, for example Ipilimumab, Tremelimumab, AGEN1884 and AGEN2041 (Agenus).

Non-limiting examples of active agents that can be used in combination with active compounds described herein are:

Protease inhibitors: plasma-derived C1-INH concentrates, for example Cetor® (Sanquin), Berinert-P® (CSL Behring, Lev Pharma), and Cinryze®; recombinant human C1-inhibitors, for example Rhucin®; ritonavir (Norvir®, Abbvie, Inc.);

Soluble complement regulators: Soluble complement receptor 1 (TP10) (Avant Immunotherapeutics); sCR1-sLe$^{x}$/TP-20 (Avant Immunotherapeutics); MLN-2222/CAB-2 (Millenium Pharmaceuticals); Mirococept (Inflazyme Pharmaceuticals);

Therapeutic antibodies: Eculizumab/Soliris (Alexion Pharmaceuticals); Pexelizumab (Alexion Pharmaceuticals); Ofatumumab (Genmab A/S); TNX-234 (Tanox); TNX-558 (Tanox); TA106 (Taligen Therapeutics); Neutrazumab (G2 Therapies); Anti-properdin (Novelmed Therapeutics); HuMax-CD38 (Genmab A/S);

Complement component inhibitors: Compstatin/POT-4 (Potentia Pharmaceuticals); ARC1905 (Archemix); 4(1MEW)APL-1, APL-2 (Appelis); CP40/AMY-101, PEG-Cp40 (Amyndas);

PDGF inhibitors: Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil;

Anti-factor H or anti-factor B agents: Anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas);

Complement C3 or CAP C3 Convertase targeting molecules: TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH; Anti-CR3, anti-MASP2, anti C1s, and anti-C1n molecules: Cynryze (ViroPharma/Baxter); TNT003 (True North); OMS721 (Omeros); OMS906 (Omeros); and Imprime PGG (Biothera);

Receptor agonists: PMX-53 (Peptech Ltd.); JPE-137 (Jerini); JSM-7717 (Jerini);

Others: Recombinant human MBL (rhMBL; Enzon Pharmaceuticals); Imides and glutarimide derivatives such as thalidomide, lenalidomide, pomalidomide; Additional non-limiting examples that can be used in combination or alternation with an active compound or its salt or composition as described herein include the following.

| Non-limiting examples of potential therapeutics for combination therapy | | | |
|---|---|---|---|
| Name | Target | Company | Class of Molecule |
| LFG316 | C5 | Novartis/Morphosys | Monoclonal antibody |
| 4(1MEW)APL-1, APL-2 | C3/C3b | Apellis | Compstatin Family |
| 4(1MeW)POT-4 | C3/C3b | Potentia | Compstatin Family |
| Anti-C5 siRNA | C5 | Alnylam | Si-RNA |
| Anti-FB siRNA | CFB | Alnylam | SiRNA |
| ARC1005 | C5 | Novo Nordisk | Aptamers |
| ATA | C5 | N.A. | Chemical |
| Coversin | C5 | Volution Immuno-Pharmaceuticals | Small animal protein |
| CP40/AMY-101, PEG-Cp40 | C3/C3b | Amyndas | Compstatin Family |
| CRIg/CFH | CAP C3 convertase | NA | CFH-based protein |
| Cynryze | C1n/C1s | ViroPharma/Baxter | Human purified protein |

-continued

| Non-limiting examples of potential therapeutics for combination therapy | | | |
|---|---|---|---|
| Name | Target | Company | Class of Molecule |
| FCFD4514S | CFD | Genentech/Roche | Monoclonal antibody |
| H17 | C3 (C3b/iC3b) | EluSys Therapeutics | Monoclonal antibody |
| Mini-CFH | CAP C3 convertase | Amyndas | CFH-based protein |
| Mirococept (APT070) | CAP and CCP C3 | NA | CR1-based protein |
| Mubodine | C5 | Adienne | Monoclonal antibody |
| RA101348 | C5 | Rapharma | Small molecule |
| sCR1 (CDX-1135) | CAP and CP C3 | Celldex | CR1-based protein |
| SOBI002 | C5 | Swedish Orphan Biovitrum | Affibody |
| SOMAmers | C5 | SomaLogic | Aptamers |
| SOMAmers | CFB and CFD | SomaLogic | Aptamers (SELEX) |
| TA106 | CFB | Alexion Pharmaceuticals | Monoclonal antibody |
| TNT003 | C1s | True North | Monoclonal antibody |
| TT30 (CR2/CFH) | CAP C3 convertase | Alexion | CFH-based protein |
| TT32 (CR2/CR1) | CAP and CCP C3 | Alexion Pharmaceuticals | CR1-based protein |
| Nafamostat (FUT-175, Futhan) | C1s, CFD, other proteases | Torri Pharmaceuticals | Small molecule |
| OMS721 | MASP-2 | Omeros | Monoclonal antibody |
| OMS906 | MASP-2 | Omeros | Monoclonal antibody |
| Bikaciomab, NM9308 | CFB | Novelmed | Monoclonal antibody |
| NM9401 | Properdin | Novelmed | Monoclonal antibody |
| CVF, HC-1496 | C3 | InCode | Recombinant peptide |
| ALXN1102/ALXN1103 (TT30) | C3-conv, C3b | Alexion Pharmaceuticals | Regulator |
| rFH | C3-conv, C3b | Optherion | Regulator |
| 5C6, AMY-301 | CFH | Amyndas | Regulator |
| Erdigna | C5 | Adienne Pharma | Antibody |
| ARC1905 | C5 | Opthotech | Monoclonal Antibody |
| MEDI7814 | C5/C5a | MedImmune | Monoclonal Antibody |
| NOX-D19 | C5a | Noxxon | Aptamer (Spiegelmer) |
| IFX-1, CaCP29 | C5a | InflaRx | Monoclonal Antibody |
| PMX53, PMX205 | C5aR | Cephalon, Teva | Peptidomimetic |
| CCX168 | C5aR | ChemoCentryx | Small molecule |
| ADC-1004 | C5aR | Alligator Bioscience | Small molecule |
| Anti-C5aR-151, NN8209; Anti-C5aR-215, NN8210 | C5aR | Novo Nordisk | Monoclonal Antibody |
| Imprime PGG | CR3 | Biothera | Soluble beta-glucan |
| ANX005; ANX007 | C1q | Annexon | Monoclonal Antibody |
| Lampalizumab | fD | Roche | Monoclonal Antibody |
| avacincaptad pegol | C5 | Opthotech | Aptamer |
| regenemab | C6 | Regenesance | Monoclonal Antibody |
| BIVV020 | C1s | Bioverativ | Monoclonal Antibody |
| PRO-02 | C2 | Broteio/Argen-x | Monoclonal Antibody |
| 5C6, compsorbin | fH | Amyndas | Peptide |
| SOBI005 | C5 | Sobi | Protein |
| ISU305 | C5 | ISU ABXIS | Monoclonal Antibody |
| Mubodina | C5 | Adienne | Monoclonal Antibody |
| IFX-2, IFX-3 | C5a | InflaRx | Monoclonal Antibody |
| ALS-205 | C5aR1 | Alsonex | Peptide |
| DF2593A | C5aR1 | Dompé | Small Molecule |
| IPH5401 | C5aR1 | Innate Pharma | Monoclonal Antibody |
| C6-LNA | C6 | Regenesance | Oligonucleotide |
| SKY59 | C5 | Roche | Monoclonal Antibody |
| REGN3918 | C5 | Regeneron | Monoclonal Antibody |
| Aptamers to Factor D | fD | Vitrisa Therapeutics | Aptamer |
| CLG561 | Properdin | Novartis | Monoclonal Antibody |
| Tesidolumab; LFG316 | C5 | Novartis and MorphoSys | Monoclonal Antibody |

In one embodiment, an active compound or its salt or composition as described herein may be provided together with a compound that inhibits an enzyme that metabolizes an administered protease inhibitor. In one embodiment, a compound or salt may be provided together with ritonavir.

In one embodiment, an active compound or its salt or composition as described herein may be provided in combination with a complement C5 inhibitor or C5 convertase inhibitor. In another embodiment, an active compound or its salt or composition as described herein may be provided in combination with eculizumab, a monoclonal antibody directed to the complement factor C5 and manufactured and marketed by Alexion Pharmaceuticals under the tradename Soliris. Eculizumab has been approved by the U.S. FDA for the treatment of PNH and aHUS.

In one embodiment, an active compound or its salt or composition as described herein may be provided together with a compound that inhibits Complement Factor D. In one embodiment of the invention, an active compound or its salt or composition as described herein as described herein can be used in combination or alternation with a compound described in Biocryst Pharmaceuticals U.S. Pat. No. 6,653,340 titled "Compounds useful in the complement, coagulate and kallikrein pathways and method for their preparation" describes fused bicyclic ring compounds that are potent inhibitors of Factor D; Novartis PCT patent publication WO2012/093101 titled "Indole compounds or analogues thereof useful for the treatment of age-related macular degeneration" describes certain Factor D inhibitors; Novartis PCT patent publications WO2013/164802, WO2013/192345, WO2014/002051, WO2014/002052, WO2014/002053, WO2014/002054, WO2014/002057, WO2014/002058, WO2014/002059, WO2014/005150, WO2014/009833, WO2014/143638, WO2015/009616, WO2015/009977, WO2015/066241, Bristol-Myers Squibb PCT patent publication WO2004/045518 titled "Open chain pro-lyl urea-related modulators of androgen receptor function"; Japan Tobacco Inc. PCT patent publication WO1999/048492 titled "Amide derivatives and nociceptin antagonists"; Ferring B. V. and Yamanouchi Pharmaceutical Co. LTD. PCT patent publication WO1993/020099 titled "CCK and/or gastrin receptor ligands"; Alexion Pharmaceuticals PCT patent publication WO1995/029697 titled "Methods and compositions for the treatment of glomerulonephritis and other inflammatory diseases"; or Achillion Pharmaceuticals filed PCT Patent Application No. PCT/US2015/017523 and U.S. patent application Ser. No. 14/631,090 titled "Alkyne Compounds for Treatment of Complement Mediated Disorders"; PCT Patent Application No. PCT/US2015/017538 and U.S. patent application Ser. No. 14/631,233 titled "Amide Compounds for Treatment of Complement Mediated Disorders"; PCT Patent Application No. PCT/US2015/017554 and U.S. patent application Ser. No. 14/631,312 titled "Amino Compounds for Treatment of Complement Mediated Disorders"; PCT Patent Application No. PCT/US2015/017583 and U.S. patent application Ser. No. 14/631,440 titled "Carbamate, Ester, and Ketone Compounds for Treatment of Complement Mediated Disorders"; PCT Patent Application No. PCT/US2015/017593 and U.S. patent application Ser. No. 14/631,625 titled "Aryl, Heteroaryl, and Heterocyclic Compounds for Treatment of Complement Mediated Disorders"; PCT Patent Application No. PCT/US2015/017597 and U.S. patent application Ser. No. 14/631,683 titled "Ether Compounds for Treatment of Complement Mediated Disorders"; PCT Patent Application No. PCT/US2015/017600 and U.S. patent application Ser. No. 14/631,785 titled "Phosphonate Compounds for Treatment of Complement Mediated Disorders"; and PCT Patent Application No. PCT/US2015/017609 and U.S. patent application Ser. No. 14/631,828 titled "Compounds for Treatment of Complement Mediated Disorders."

In one embodiment, an active compound or its salt or composition as described herein is administered in combination with an anti-inflammatory drug, antimicrobial agent, anti-angiogenesis agent, immunosuppressant, antibody, steroid, ocular antihypertensive drug or combinations thereof. Examples of such agents include amikacin, anecortane acetate, anthracenedione, anthracycline, an azole, amphotericin B, bevacizumab, camptothecin, cefuroxime, chloramphenicol, chlorhexidine, chlorhexidine digluconate, clortrimazole, a clotrimazole cephalosporin, corticosteroids, dexamethasone, desamethazone, econazole, eftazidime, epipodophyllotoxin, fluconazole, flucytosine, fluoropyrimidines, fluoroquinolines, gatifloxacin, glycopeptides, imidazoles, itraconazole, ivermectin, ketoconazole, levofloxacin, macrolides, miconazole, miconazole nitrate, moxifloxacin, natamycin, neomycin, nystatin, ofloxacin, polyhexamethylene biguanide, prednisolone, prednisolone acetate, pegaptanib, platinum analogues, polymicin B, propamidine isethionate, pyrimidine nucleoside, ranibizumab, squalamine lactate, sulfonamides, triamcinolone, triamcinolone acetonide, triazoles, vancomycin, anti-vascular endothelial growth factor (VEGF) agents, VEGF antibodies, VEGF antibody fragments, vinca alkaloid, timolol, betaxolol, travoprost, latanoprost, bimatoprost, brimonidine, dorzolamide, acetazolamide, pilocarpine, ciprofloxacin, azithromycin, gentamycin, tobramycin, cefazolin, voriconazole, gancyclovir, cidofovir, foscarnet, diclofenac, nepafenac, ketorolac, ibuprofen, indomethacin, fluoromethalone, rimexolone, anecortave, cyclosporine, methotrexate, tacrolimus, anti-PDGFR molecule, and combinations thereof.

In one embodiment of the present invention, an active compound or its salt or composition as described herein can be administered in combination or alternation with at least one immunosuppressive agent. The immunosuppressive agent as non-limiting examples, may be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, tocilizumab (Actemra), siltuximab (Sylvant), secukibumab (Cosentyx), ustekinumab (Stelara), risankizumab, sifalimumab, aspirin and ibuprofen.

Examples of anti-inflammatory agents include methotrexate, dexamethasone, dexamethasone alcohol, dexamethasone sodium phosphate, fluromethalone acetate, fluromethalone alcohol, lotoprendol etabonate, medrysone, prednisolone acetate, prednisolone sodium phosphate, difluprednate, rimexolone, hydrocortisone, hydrocortisone acetate, lodoxamide tromethamine, aspirin, ibuprofen, suprofen, piroxicam, meloxicam, flubiprofen, naproxan, ketoprofen, tenoxicam, diclofenac sodium, ketotifen fumarate, diclofenac sodium, nepafenac, bromfenac, flurbiprofen sodium, suprofen, celecoxib, naproxen, rofecoxib, glucocorticoids, diclofenac, and any combination thereof. In one embodiment, an active compound or its salt or composition as described herein is combined with one or more non-steroidal anti-inflammatory drugs (NSAIDs) selected from naproxen sodium (Anaprox), celecoxib (Celebrex), sulindac (Clinoril), oxaprozin (Daypro), salsalate (Disalcid), diflunisal (Dolobid), piroxicam (Feldene), indomethacin (Indocin), etodolac (Lodine), meloxicam (Mobic), naproxen (Naprosyn), nabumetone (Relafen), ketorolac tromethamine (Toradol), naproxen/esomeprazole (Vimovo), and diclofenac (Voltaren), and combinations thereof.

In one embodiment, an active compound or its salt or composition as described herein is administered in combination or alteration with an omega-3 fatty acid or a peroxisome proliferator-activated receptor (PPARs) agonist. Omega-3 fatty acids are known to reduce serum triglycerides by inhibiting DGAT and by stimulating peroxisomal and mitochondrial beta oxidation. Two omega-3 fatty acids, eicosapentaenoic acid (EPA) and docosahexaenoic acid (DHA), have been found to have high affinity for both PPAR-alpha and PPAR-gamma. Marine oils, e.g., fish oils, are a good source of EPA and DHA, which have been found to regulate lipid metabolism. Omega-3 fatty acids have been found to have beneficial effects on the risk factors for cardiovascular diseases, especially mild hypertension, hypertriglyceridemia and on the coagulation factor VII phospholipid complex activity. Omega-3 fatty acids lower serum triglycerides, increase serum HDL-cholesterol, lower systolic and diastolic blood pressure and the pulse rate, and lower the activity of the blood coagulation factor VII-phospholipid complex. Further, omega-3 fatty acids seem to be well tolerated, without giving rise to any severe side effects. One such form of omega-3 fatty acid is a concentrate of omega-3, long chain, polyunsaturated fatty acids from fish oil containing DHA and EPA and is sold under the trademark Omacor®. Such a form of omega-3 fatty acid is described, for example, in U.S. Pat. Nos. 5,502,077, 5,656,667 and 5,698,594, the disclosures of which are incorporated herein by reference.

Peroxisome proliferator-activated receptors (PPARs) are members of the nuclear hormone receptor superfamily ligand-activated transcription factors that are related to retinoid, steroid and thyroid hormone receptors. There are three distinct PPAR subtypes that are the products of different genes and are commonly designated PPAR-alpha, PPAR-beta/delta (or merely, delta) and PPAR-gamma. General classes of pharmacological agents that stimulate peroxisomal activity are known as PPAR agonists, e.g., PPAR-alpha agonists, PPAR-gamma agonists and PPAR-delta agonists. Some pharmacological agents are combinations of PPAR agonists, such as alpha/gamma agonists, etc., and some other pharmacological agents have dual agonist/antagonist activity. Fibrates such as fenofibrate, bezafibrate, clofibrate and gemfibrozil, are PPAR-alpha agonists and are used in patients to decrease lipoproteins rich in triglycerides, to increase HDL and to decrease atherogenic-dense LDL. Fibrates are typically orally administered to such patients. Fenofibrate or 2-[4-(4-chlorobenzoyl)phenoxy]-2-methylpropanoic acid, 1-methylethyl ester, has been known for many years as a medicinally active principle because of its efficacy in lowering blood triglyceride and cholesterol levels.

In one embodiment, the present invention provides a method of treating or preventing age-related macular degeneration (AMD) by administering to a subject in need thereof an effective amount of an active compound or its salt or composition as described herein in combination with an anti-VEGF agent. Non-limiting examples of anti-VEGF agents include, but are not limited to, aflibercept (Eylea®; Regeneron Pharmaceuticals); ranibizumab (Lucentis®: Genentech and Novartis); pegaptanib (Macugen®; OSI Pharmaceuticals and Pfizer); bevacizumab (Avastin; Genentech/Roche); lapatinib (Tykerb); sunitinib (Sutent); axitinib (Inlyta); pazopanib; sorafenib (Nexavar); ponatinib (Inclusig); regorafenib (Stivarga); Cabozantinib (Abometyx; Cometriq); vendetanib (Caprelsa); ramucirumab (Cyramza); lenvatinib (Lenvima); ziv-aflibercept (Zaltrap); cediranib (Recentin); anecortane acetate, squalamine lactate, and corticosteroids, including, but not limited to, triamcinolone acetonide.

In one embodiment, the present invention provides a method of treating or preventing age-related macular degeneration (AMD) by administering to a subject in need thereof an effective amount of an active compound or its salt or composition as described herein in combination with a complement C5 inhibitor, for example, a complement C5 inhibitor described herein and in the table above titled Non-limiting examples of potential therapeutics for combination therapy, including, but not limited to, eculizumab; LFG316 (Novartis/Morphosys); Anti-C5 siRNA (Alnylam); ARC1005 (Novo Nordisk); Coversin (Volution Immuno-Pharmaceuticals); Mubodine (Adienne Pharma); RA101348 (Ra Pharma); SOBI002 (Swedish Orphan Biovitrum); SOMAmers (SomaLogic); Erdigna (Adienne Pharma); ARC1905 (Opthotech); MED17814 (MedImmune); NOX-D19 (Noxxon); IFX-1, CaCP29 (InflaRx); PMX53, PMX205 (Cephalon, Teva); CCX168 (ChemoCentryx); ADC-1004 (Alligator Bioscience); and Anti-C5aR-151, NN8209; Anti-C5aR-215, NN8210 (Novo Nordisk).

In one embodiment, the present invention provides a method of treating or preventing age-related macular degeneration (AMD) by administering to a subject in need thereof an effective amount of an active compound or its salt or composition as described herein in combination with anti-properidin agent, for example, an anti-properidin agent as described above, including but not limited to NM9401 (Novelmed).

In one embodiment, the present invention provides a method of treating or preventing age-related macular degeneration (AMD) by administering to a subject in need thereof an effective amount of an active compound or its salt or composition as described herein in combination with a complement C3 inhibitor for example, a complement C3 inhibitor described above, including, but not limited to, a compstatin or compstatin analogue, for example Compstatin/POT-4 (Potentia Pharmaceuticals); ARC1905 (Archemix); 4(1MEW)APL-1, APL-2 (Appelis); CP40/AMY-101, PEG-Cp40 (Amyndas) Complement C3 or CAP C3 Convertase targeting molecules: TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30)(Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); and CRIg/CFH.

In one embodiment, the present invention provides a method of treating or preventing age-related macular degeneration (AMD) by administering to a subject in need thereof an effective amount of an active compound or its salt or composition as described herein in combination with an anti-factor H or anti-factor B agent selected from Anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas).

In one embodiment, the present invention provides a method of treating or preventing age-related macular degeneration (AMD) by administering to a subject in need thereof an effective amount of an active compound or its salt or composition as described herein in combination with an anti-MASP2, anti-C1s or anti-CR3 molecules, for example, but not limited to: Cynryze (ViroPharma/Baxter); TNT003 (True North); OMS721 (Omeros); OMS906 (Omeros); and Imprime PGG (Biothera).

In one embodiment, the present invention provides a method of treating or preventing age-related macular degeneration (AMD) by administering to a subject in need thereof an effective amount of an active compound or its salt or composition as described herein in combination with an PDGF inhibitor, for example as described herein including but not limited to Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil.

In one embodiment, the present invention provides a method of treating or preventing paroxysmal nocturnal hemoglobinuria (PNH) by administering to a subject in need thereof an effective amount of an active compound or its salt or composition as described herein with an additional inhibitor of the complement system or another active compound with a different biological mechanism of action. In another embodiment, the present invention provides a method of treating or preventing paroxysmal nocturnal hemoglobinuria (PNH) by administering to a subject in need thereof an effective amount of an active compound or its salt or composition as described herein in combination or alternation with eculizumab. In another embodiment, the present invention provides a method of treating or preventing paroxysmal nocturnal hemoglobinuria (PNH) by administering to a subject in need thereof an effective amount of an active compound or its salt or composition as described herein in combination or alternation with CP40. In one embodiment, the additional agent is PEGylated-CP40. CP40 is a peptide inhibitor that shows a strong binding affinity for C3b and inhibits hemolysis of paroxysmal nocturnal hemoglobinuria (PNH) erythrocytes. In one embodiment, the additional agent is a complement component inhibitor, for example but not limited to Compstatin/POT-4 (Potentia Pharmaceuticals); ARC1905 (Archemix); 4(1MEW)APL-1, APL-2 (Appelis); CP40/AMY-101, PEG-Cp40 (Amyndas); a PDGF inhibitor, for example, but not limited to Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil; an anti-factor H or anti-factor B agent, for example anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas); a complement C3 or CAP C3 convertase targeting molecule, for example but not limited to TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH, an anti-CR3, anti-MASP2, anti C1s, or anti-C1n molecule, for example but not limited to Cynryze (ViroPharma/Baxter); TNT003 (True North); OMS721 (Omeros); OMS906 (Omeros); and Imprime PGG (Biothera)

In one embodiment, the present invention provides a method of treating or preventing rheumatoid arthritis by administering to a subject in need thereof an effective amount of a composition comprising an active compound or its salt or composition as described herein in combination or alternation with an additional inhibitor of the complement system, or an active agent that functions through a different mechanism of action. In another embodiment, the present invention provides a method of treating or preventing rheumatoid arthritis by administering to a subject in need thereof an effective amount of an active compound or its salt or composition as described herein in combination or alternation with methotrexate. In certain embodiments, an active compound or its salt or composition as described herein is administered in combination or alternation with at least one additional therapeutic agent selected from: salicylates including aspirin (Anacin, Ascriptin, Bayer Aspirin, Ecotrin) and salsalate (Mono-Gesic, Salgesic); nonsteroidal anti-inflammatory drugs (NSAIDs); nonselective inhibitors of the cyclo-oxygenase (COX-1 and COX-2) enzymes, including diclofenac (Cataflam, Voltaren), ibuprofen (Advil, Motrin), ketoprofen (Orudis), naproxen (Aleve, Naprosyn), piroxicam (Feldene), etodolac (Lodine), indomethacin, oxaprozin (Daypro), nabumetone (Relafen), and meloxicam (Mobic); selective cyclo-oxygenase-2 (COX-2) inhibitors including Celecoxib (Celebrex); disease-modifying anti-rheumatic drugs (DMARDs), including azathioprine (Imuran), cyclosporine (Sandimmune, Neoral), gold salts (Ridaura, Solganal, Aurolate, Myochrysine), hydroxychloroquine (Plaquenil), leflunomide (Arava), methotrexate (Rheumatrex), penicillamine (Cuprimine), and sulfasalazine (Azulfidine); biologic drugs including abatacept (Orencia), etanercept (Enbrel), infliximab (Remicade), adalimumab (Humira), and anakinra (Kineret); corticosteroids including betamethasone (Celestone Soluspan), cortisone (Cortone), dexamethasone (Decadron), methylprednisolone (SoluMedrol, DepoMedrol), prednisolone (Delta-Cortef), prednisone (Deltasone, Orasone), and triamcinolone (Aristocort); gold salts, including Auranofin (Ridaura); Aurothioglucose (Solganal); Aurolate; Myochrysine; or any combination thereof.

In one embodiment, the present invention provides a method of treating or preventing multiple sclerosis by administering to a subject in need thereof an effective amount of an active compound or its salt or composition as described herein in combination or alternation with an additional inhibitor of the complement system, or an active agent that functions through a different mechanism of action. In another embodiment, the present invention provides a method of treating or preventing multiple sclerosis by administering to a subject in need thereof an effective amount of an active compound or its salt or composition as described herein in combination or alternation with a corticosteroid. Examples of corticosteroids include, but are not limited to, prednisone, dexamethasone, solumedrol, and methylprednisolone. In one embodiment, an active compound or its salt or composition as described herein is combined with at least one anti-multiple sclerosis drug, for example, selected from: Aubagio (teriflunomide), Avonex (interferon beta-1a), Betaseron (interferon beta-1b), Copaxone (glatiramer acetate), Extavia (interferon beta-1b), Gilenya (fingolimod), Lemtrada (alemtuzumab), Novantrone (mitoxantrone), Plegridy (peginterferon beta-1a), Rebif (interferon beta-1a), Tecfidera (dimethyl fumarate), Tysabri (natalizumab), Solu-Medrol (methylprednisolone), High-dose oral Deltasone (prednisone), H.P. Acthar Gel (ACTH), or a combination thereof.

In one embodiment, an active compound or its salt or composition as described herein is useful in a combination with another pharmaceutical agent to ameliorate or reduce a side effect of the agent. For example, in one embodiment, an active compound or its salt or composition as described herein may be used in combination with adoptive cell transfer therapies to reduce an associated inflammatory response associated with such therapies, for example, a cytokine mediated response such as cytokine release syndrome. In one embodiment, the adoptive cell transfer therapy includes the use of a chimeric antigen receptor T-Cell (CAR T). In one embodiment, the adoptive cell transfer therapy includes the use of a chimeric antigen receptor T-Cell (CAR T) or a dendritic cell to treat a hematologic or solid tumor, for example, a B-cell related hematologic cancer. In one embodiment, the hematologic or solid tumor is acute lymphoblastic leukemia (ALL), acute myeloid leukemia (AML), non-Hodgkin's lymphoma, chronic lymphocytic leukemia (CLL), pancreatic cancer, glioblastoma, or a cancer that expresses CD19.

In an additional alternative embodiment, an active compound or its salt or composition as described herein may be provided in combination with eculizumab for the treatment of PNH, aHUSs, STEC-HUS, ANCA-vasculitis, AMD, CAD, C3 glomerulopathy, for example DDD or C3GN, chronic hemolysis, neuromyelitis optica, or transplantation rejection. In one embodiment, an active compound or its salt or composition as described herein may be provided in combination with compstatin or a compstatin derivative for the treatment of PNH, aHUSs, STEC-HUS, ANCA-vasculitis, AMD, CAD, C3 glomerulopathy, for example DDD or C3GN, chronic hemolysis, neuromyelitis optica, or transplantation rejection. In one embodiment, the additional agent is a complement component inhibitor, for example but not limited to Compstatin/POT-4 (Potentia Pharmaceuticals); ARC1905 (Archemix); 4(1MEW)APL-1, APL-2 (Appelis); CP40/AMY-101, PEG-Cp40 (Amyndas); a PDGF inhibitor, for example, but not limited to Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil; an anti-factor H or anti-factor B agent, for example anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas); a complement C3 or CAP C3 convertase targeting molecule, for example but not limited to TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH, an anti-CR3, anti-MASP2, anti C1s, or anti-C1n molecule, for example but not limited to Cynryze (ViroPharma/Baxter); TNT003 (True North); OMS721 (Omeros); OMS906 (Omeros); and Imprime PGG (Biothera).

In one embodiment, an active compound or its salt or composition as described herein may be provided in combination with rituxan for the treatment of a complement mediated disorder. In one embodiment, the complement mediated disorder is, for example, rheumatoid arthritis, Granulomatosis with Polyangiitis (GPA) (Wegener's Granulomatosis), and Microscopic Polyangiitis (MPA). In one embodiment, the disorder is Lupus.

In one embodiment, an active compound or its salt or composition as described herein may be provided in combination with cyclophosphamide for the treatment of a complement mediated disorder. In one embodiment, the disorder is an autoimmune disease. In one embodiment, the complement mediated disorder is, for example, rheumatoid arthritis, Granulomatosis with Polyangiitis (GPA) (Wegener's Granulomatosis), and Microscopic Polyangiitis (MPA). In one embodiment, the disorder is Lupus.

In one embodiment, an active compound or its salt or composition as described herein is dosed in combination with a conventional DLE treatment for the treatment of lupus to a subject in need thereof.

Examples of conventional DLE treatments include topical corticosteroid ointments or creams, such as triamcinolone acetonide, fluocinolone, flurandrenolide, betamethasone valerate, or betamethasone dipropionate. Resistant plaques can be injected with an intradermal corticosteroid. Other potential DLE treatments include calcineurin inhibitors such as pimecrolimus cream or tacrolimus ointment. Particularly resistant cases can be treated with systemic antimalarial drugs, such as hydroxychloroquine (PLAQUENIL).

In one embodiment, an active compound or its salt or composition as described herein may be provided in combination with methotrexate for the treatment of Lupus.

In one embodiment, an active compound or its salt or composition as described herein may be provided in combination with azathioprine for the treatment of Lupus.

In one embodiment, an active compound or its salt or composition as described herein may be provided in combination with a non-steroidal anti-inflammatory drug for the treatment of Lupus.

In one embodiment, an active compound or its salt or composition as described herein may be provided in combination with a corticosteroid for the treatment of Lupus.

In one embodiment, an active compound or its salt or composition as described herein may be provided in combination with a belimumab (Benlysta) for the treatment of Lupus.

In one embodiment, an active compound or its salt or composition as described herein may be provided in combination with hydroxychloroquine (Plaquenil) for the treatment of Lupus.

In one embodiment, an active compound or its salt or composition as described herein may be provided in combination with sifalimumab for the treatment of Lupus.

In one embodiment, an active compound or its salt or composition as described herein may be provided in combination with OMS721 (Omeros) for the treatment of a complement mediated disorder. In one embodiment, an active compound or its salt or composition as described herein may be provided in combination with OMS906 (Omeros) for the treatment of a complement mediated disorder. In one embodiment, the complement mediated disorder is, for example, thrombotic thrombocytopenic purpura (TTP) or aHUS.

In one embodiment, an active compound or its salt or composition as described herein may be provided in combination with an anti-inflammatory agent, immunosuppressive agent, or anti-cytokine agent for the treatment or prevention of cytokine or inflammatory reactions in response to the administration of pharmaceuticals or biotherapeutics (e.g. adoptive T-cell therapy (ACT) such as CAR T-cell therapy, or monoclonal antibody therapy). In one embodiment, an active compound or its salt or composition as described herein may be provided in combination with a corticosteroid, for example prednisone, dexamethasone, solumedrol, and methylprednisolone, and/or anti-cytokine compounds targeting, e.g., IL-4, IL-10, IL-11, IL-13 and TGFβ. In one embodiment, an active compound or its salt or composition as described herein may be provided in combination with an anti-cytokine inhibitor including, but are not limited to, adalimumab, infliximab, etanercept, protopic, efalizumab, alefacept, anakinra, siltuximab, secukibumab, ustekinumab, golimumab, and tocilizumab, or a combination thereof. Additional anti-inflammatory agents that can be used in combination with an active compound or its salt or composition as described herein include, but are not limited to, non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline); DAB 486-IL-2 and/or DAB 389-IL-2 (IL-2 fusion proteins; Seragen); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-IRA (IL-1 receptor antagonist; Synergen/Amgen); anakinra (Kineret®/Amgen); TNF-bp/s-TNF (soluble TNF binding protein); R973401 (phosphodiesterase Type IV inhibitor); MK-966 (COX-2 Inhibitor); Iloprost, leflunomide (anti-inflammatory and cytokine inhibition); tranexamic acid (inhibitor of plasminogen activation); T-614 (cytokine inhibitor); prostaglandin E1; Tenidap (non-steroidal anti-inflammatory drug); Naproxen (non-steroidal anti-inflammatory drug); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine; Azathioprine; ICE inhibitor (inhibitor of the enzyme interleukin-1β converting enzyme); zap-70 and/or lck inhibitor (inhibitor of the tyrosine kinase zap-70 or lck); TNF-convertase inhibitors; anti-IL-12 antibodies; anti-IL-18 antibodies; interleukin-11; interleukin-13; interleukin-17 inhibitors; gold; penicillamine; chloroquine; chlorambucil; hydroxychloroquine; cyclosporine; cyclophosphamide; anti-thymocyte globulin; anti-CD4 antibodies; CD5-toxins; orally-administered peptides and collagen; lobenzarit disodium; Cytokine Regulating Agents (CRAB) HP228 and HP466 (Houghten Pharmaceuticals, Inc.); ICAM-1 antisense phosphorothioate oligo-deoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine).

In a specific embodiment, an active compound or its salt or composition as described herein may be provided in combination with a corticosteroid for the treatment or prevention of cytokine or inflammatory reactions in response to the administration of pharmaceuticals or biotherapeutics. In another embodiment, an active compound or its salt or composition as described herein may be provided in combination with etanercept for the treatment or prevention of cytokine or inflammatory reactions in response to the administration of pharmaceuticals or biotherapeutics. In another embodiment, an active compound or its salt or composition as described herein may be provided in combination with tocilizumab for the treatment or prevention of cytokine or inflammatory reactions in response to the administration of pharmaceuticals or biotherapeutics. In another embodiment, an active compound or its salt or composition as described herein may be provided in combination with etanercept and tocilizumab for the treatment or prevention of cytokine or inflammatory reactions in response to the administration of pharmaceuticals or biotherapeutics. In another embodiment, an active compound or its salt or composition as described herein may be provided in combination with infliximab for the treatment or prevention of cytokine or inflammatory reactions in response to the administration of pharmaceuticals or biotherapeutics. In another embodiment, an active compound or its salt or composition as described herein may be provided in combination with golimumab for the treatment or prevention of cytokine or inflammatory reactions in response to the administration of pharmaceuticals or biotherapeutics.

Combinations for Prophylactic or Concommitant Anti-Bacterial Therapy

In one aspect of the present invention, a method is provided for treating a host in need thereof that comprises administering an effective amount of a prophylactic anti-bacterial vaccine prior to administration of an active compound or its salt or composition for any of the disorders described herein. In another aspect of the present invention, a method is provided for treating a host in need thereof that comprises administering an effective amount of a prophylactic anti-bacterial drug, such as a pharmaceutical drug, prior to administration of an active compound or its salt or composition for any of the disorders described herein. In one aspect of the present invention, a method is provided for treating a host in need thereof that comprises administering an effective amount of an anti-bacterial vaccine after administration of an active compound or its salt or composition for any of the disorders described herein. In another aspect of the present invention, a method is provided for treating a host in need thereof that comprises administering an effective amount of an anti-bacterial drug, such as a pharmaceutical drug, after administration of an active compound or its salt or composition for any of the disorders described herein. In one embodiment, the disorder is PNH, C3G, or aHUS. In one embodiment, the host has received an organ or other tissue or biological fluid transplant. In one embodiment, the host is also administered eculizumab.

In one aspect of the present invention, an active compound or its salt or composition as described herein is administered to a host concomitantly to a subject following the prophylactic administration of a vaccine against a bacterial infection. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, an active compound or its salt or composition as described herein is administered to a subject concomitantly with the prophylactic administration of a vaccine against a bacterial infection. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, an active compound or its salt or composition as described herein is administered to a subject and, during the administration period of the compound or salt, a vaccine against a bacterial infection is administered to the subject. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, the subject is administered an active compound or its salt or composition as described herein in combination with an antibiotic compound for the duration of Factor D inhibitor administration. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, an active compound or its salt or composition as described herein is administered to a subject following the prophylactic administration of a vaccine against a bacterial infection, and in combination with an antibiotic compound for the duration of Factor D inhibitor administration. In one embodiment, the complement mediated disorder is PNH or aHUS. In one embodiment, the subject has received an organ or other tissue or biological fluid transplant. In one embodiment, the subject is also administered eculizumab. In one embodiment, the subject, prior to receiving an active compound or its salt or composition as described herein, is vaccinated against a bacterial infection caused by the bacterium *Neisseria meningitidis*. In one embodiment, the subject is vaccinated against a bacterial infection caused by the bacterium *Haemophilus influenzae*. In one embodiment, the *Haemophilus influenzae* is *Haemophilus influenzae* serotype B (Hib). In one embodiment, the subject is vaccinated against a bacterial infection caused by *Streptococcus pneumoniae*. In one embodiment, the subject is vaccinated against a bacterial infection caused by the bacterium *Neisseria meningitidis, Haemophilus influenzae*, or *Streptococcus pneumoniae*, or a combination of one or more of *Neisseria meningitidis, Haemophilus influenzae*, or *Streptococcus pneumoniae*. In one embodiment, the subject is vaccinated against a bacterial infection caused by the bacterium *Neisseria meningitidis, Haemophilus influenzae*, and *Streptococcus pneumoniae*.

In other embodiments, the subject is vaccinated against a bacterial infection caused by a bacterium selected from a Gram-negative bacterium. In one embodiment, the subject is vaccinated against a bacterial infection caused by a bacterium selected from a Gram-positive bacterium. In one embodiment, the subject is vaccinated against a bacterial infection caused by the bacterium *Neisseria meningitidis, Haemophilus influenzae*, or *Streptococcus pneunemoniae*, or a combination of one or more of *Neisseria meningitidis, Haemophilus influenzae*, or *Streptococcus pneumoniae*, and one or more of, but not limited to, *Bacillus anthracis, Bordetella pertussis, Clostridium tetani, Corynebacterium diphtheria, Coxiella burnetii, Mycobacterium tuberculosis, Salmonella typhi, Vibrio cholerae, Anaplasma phagocytophilum, Ehrlichia ewingii, Ehrlichia chaffeensis, Ehrlichia canis, Neorickettsia sennetsu, Mycobacterium leprae, Borrelia burgdorferi, Borrelia mayonii, Borrelia afzelii, Borrelia garinii, Mycobacterium bovis, Staphylococcus aureus, Streptococcus pyogenes, Treponema pallidum, Francisella tularensis, Yersinia pestis*, In one embodiment, the subject is vaccinated with one or more vaccines selected from, but not limited to, typhoid vaccine, live (Vivotif Berna Vaccine, PaxVax), typhoid Vi polysaccharide vaccine (Typhim Vi, Sanofi), pneumococcal 23-polyvalent vaccine, PCV13 (Pneumovax 23, Merck), pneumococcal 7-valent vaccine, PCV7 (Prevnar, Pfizer), pneumococcal 13-valent vaccine, PCV13 (Prevnar 13, Pfizer), *Haemophilus* b conjugate (prp-t) vaccine (ActHIB, Sanofi; Hibrix, GSK), *Haemophilus* b conjugate (hboc) vaccine (HibTITER, Neuron Biotech), *Haemophilus* b conjugate (prp-omp) vaccine (PedvaxHIB, Merck), *Haemophilus* b conjugate (prp-t) vaccine/meningococcal conjugate vaccine (MenHibrix, GSK), *Haemophilus* b conjugate (prp-t) vaccine/meningococcal conjugate vaccine/Hepatitis B vaccine (Comvax, Merck), meningococcal polysaccharide vaccine (Menomune A/C/Y/W-135, Sanofi), meningococcal conjugate vaccine/diphtheria CRM197 conjugate (Menveo, GSK; Menactra, Sanofi), meningococcal group B vaccine (Bexsero, GSK; Trumenba, Pfizer), anthrax vaccine adsorbed (Biothrax, Emergent Biosolutions), tetanus toxoid (Te Anatoxal Berna, Hendricks Regional Health), *Bacillus* Calmette and Guérin, live, intravesical (TheraCys, Sanofi; Tice BCG, Organon), cholera vaccine, live, oral (Vachora, Sanofi; Dukoral, SBL Vaccines; ShanChol, Shantha Biotec; Micromedex, Truven Health), tetanus toxoids and diphtheria absorbed (Tdap; Decavac, Sanofi; Tenivac, Sanofi; td, Massachusetts Biological Labs), diphtheria and tetanus toxois and pertussis (DTap; Daptacel, Sanofi; Infanrix, GSK; Tripedia, Sanofi), diphtheria and tetanus toxois and pertussis/polio (Kinrix, GSK; Quadracel, Sanofi), diphtheria and tetanus toxois and pertussis tetanus/hepatitis B/polio (Pediarix, GSK), diphtheria and tetanus toxois and pertussis/polio, *Haemophilus* influenza tybe b (Pentacel, Sanofi), and/or diphtheria, and pertussis (Tdap; Boostrix, GSK; Adacel, Sanofi), or a combination thereof.

As described above, a subject receiving a compound of the present invention to treat a disorder is prophylactically administered an antibiotic compound in addition to a Factor D inhibitor described herein. In one embodiment, the subject is administered an antibiotic compound for the duration of administration of the active compound to reduce the development of a bacterial infection. Antibiotic compounds for concomitant administration with a Factor D inhibitor described herein can be any antibiotic useful in preventing or reducing the effect of a bacterial infection. Antibiotics are well known in the art and include, but are not limited to, amikacin (Amikin), gentamicin (Garamycin), kanamycin (Kantrex), neomycin (Neo-Fradin), netilmicin (Netromycin), tobramycin (Nebcin), paromomycin (Humatin), streptomycin, spectinomycin (Trobicin), geldanamycin, herbimycin, rifaximin (Xifaxan), loracarbef (Lorabid), ertapenem (Invanz), doripenem (Doribax), imipenem/cilastatin (Primaxin), meropenem (Merrem), cefadroxil (Duricef), cefazolin (Ancef), cefalotin/cefalothin (Keflin), cephalexin (Keflex), cefaclor (Distaclor), cefamandole (Mandol), cefoxitin (Mefoxin), cefprozil (Cefzil), cefuroxime (Ceftin, Zinnat), cefixime (Cefspan), cefdinir (Omnicef, Cefdiel), cefditoren (Spectracef, Meiact), cefoperazone (Cefobid), cefotaxime (Claforan), cefpodoxime (Vantin) ceftazidime (Fortaz), ceftibuten (Cedax), ceftizoxime (Cefizox), ceftriaxone (Rocephin), cefepime (Maxipime), ceftaroline fosamil (Teflaro), ceftobiprole (Zeftera), teicoplanin (Targocid), vancomycin (Vancocin), telavancin (Vibativ), dalbavancin (Dalvance), oritavancin (Orbactiv), clindamycin (Cleocin), lincomycin (Lincocin), daptomycin (Cubicin), azithromycin (Zithromax, Sumamed, Xithrone), clarithromycin (Biaxin), dirithromycin (Dynabac), erythromycin (Erythocin, Erythroped), roxithromycin, troleandomycin (Tao), telithromycin (Ketek), spiramycin (Rovamycine), aztreonam (Azactam), furazolidone (Furoxone), nitrofurantoin (Macrodantin, Macrobid), linezolid (Zyvox), posizolid, radezolid, torezolid, amoxicillin (Novamox, Amoxil), ampicillin (Principen), azlocillin, carbenicillin (Geocillin), cloxacillin (Tegopen), dicloxacillin (Dynapen), flucloxacillin (Floxapen), mezlocillin (Mezlin), methicillin (Staphcillin), nafcillin (Unipen), oxacillin (Prostaphlin), penicillin G (Pentids), penicillin V (Veetids (Pen-Vee-K), piperacillin (Pipracil), penicillin G (Pfizerpen), temocillin (Negaban), ticarcillin (Ticar), amoxicillin/clavulanate (Augmentin), ampicillin/sulbactam (Unasyn), piperacillin/tazobactam (Zosyn), ticarcillin/clavulanate (Timentin), bacitracin, colistin (Coly-Mycin-S), polymyxin B, ciprofloxacin (Cipro, Ciproxin, Ciprobay), enoxacin (Penetrex), gatifloxacin (Tequin), gemifloxacin (Factive), levofloxacin (Levaquin), lomefloxacin (Maxaquin), moxifloxacin (Avelox), nalidixic acid (NegGram), norfloxacin (Noroxin), ofloxacin (Floxin, Ocuflox), trovafloxacin (Trovan), grepafloxacin (Raxar), sparfloxacin (Zagam), temafloxacin (Omniflox), mafenide (Sulfamylon), sulfacetamide (Sulamyd, Bleph-10), sulfadiazine (Micro-Sulfon), silver sulfadiazine (Silvadene), sulfadimethoxine (Di-Methox, Albon), sulfamethizole (Thiosulfil Forte), sulfamethoxazole (Gantanol), sulfanilamide, sulfasalazine (Azulfidine), sulfisoxazole (Gantrisin), trimethoprim-sulfamethoxazole (Co-trimoxazole) (TMP-SMX) (Bactrim, Septra), sulfonamidochrysoidine (Prontosil), demeclocycline (Declomycin), doxycycline (Vibramycin), minocycline (Minocin), oxytetracycline (Terramycin), tetracycline (Sumycin, Achromycin V, Steclin), clofazimine (Lamprene), dapsone (Avlosulfon), capreomycin (Capastat), cycloserine (Seromycin), ethambutol (Myambutol), ethionamide (Trecator), isoniazid (I.N.H.), pyrazinamide (Aldinamide), rifampicin (Rifadin, Rimactane), rifabutin (Mycobutin), rifapentine (Priftin), streptomycin, arsphenamine (Salvarsan), chloramphenicol (Chloromycetin), fosfomycin (Monurol, Monuril), fusidic acid (Fucidin), metronidazole (Flagyl), mupirocin (Bactroban), platensimycin, quinupristin/dalfopristin (Synercid), thiamphenicol, tigecycline (Tigacyl), tinidazole (Tindamax Fasigyn), trimethoprim (Proloprim, Trimpex), and/or teixobactin, or a combination thereof.

In one embodiment, the subject is administered a prophylactic antibiotic selected from cephalosporin, for example, ceftriaxone or cefotaxime, ampicillin-sulbactam, Penicillin G, ampicillin, chloramphenicol, fluoroquinolone, aztreonam, levofloxacin, moxifloxacin, gemifloxacin, vancomycin, clindamycin, cefazolin, azithromycin, meropenem, ceftaroline, tigecycline, clarithromycin, moxifloxacin, trimethoprim/sulfamethoxazole, cefuroxime, axetil, ciprofloxacin, rifampin, minocycline, spiramycin, and cefixime, or a combination of two or more thereof.

Process of Preparation of Compounds of the Present Invention

Abbreviations

ACN Acetonitrile
Ac Acetyl
$Ac_2O$ Acetic anhydride
AcOEt, EtOAc ethyl acetate
AcOH Acetic acid
$Boc_2O$ di-tert-butyl dicarbonate
Bu Butyl
CAN Ceric ammonium nitrate
CBz Carboxybenzyl
CDI Carbonyldiimidazole
$CH_3OH$, MeOH Methanol
CsF Cesium fluoride
CuI Cuprous iodide
DCM, $CH_2Cl_2$ Dichloromethane
DIEA, DIPEA N,N-diisopropylethylamine
DMA N,N-dimethylacetamide
DMAP 4-Dimethylaminopyridine
DMF N,N-dimethylformamide
DMS Dimethyl sulfide
DMSO Dimethylsulfoxide
DPPA Diphenyl phosphoryl azide
EDCI 1-Ethyl-3-(3-dimethylaminopropyl)carbodiimide
EEDQ N-Ethoxycarbonyl-2-ethoxy-1,2-dihydroquinoline
Et Ethyl
$Et_3N$, TEA Triethylamine
EtOAc Ethylacetate
EtOH Ethanol
HATU 1-[Bis(dimethylamino)methylene]-1H-1,2,3-triazolo[4,5-b]pyridinium3-oxide hexafluorophosphate
HCl Hydrochloric acid
HOBT Hydroxybenzotriazole
iBu, i-Bu, isoBu Isobutyl
iPr, i-Pr, isoPr Isopropyl
$^iPr_2NEt$ N,N-diisopropylethylamine
$K_2CO_3$ Potassium carbonate
$K_2CO_3$ Potassium carbonate
LiOH Lithium hydroxide
Me Methyl
MeI Methyl iodide
Ms Mesyl
MsCl Mesylchloride
MTBE Methyl $^t$butylether
$Na_2SO_4$ Sodium sulfate
NaCl Sodium chloride
NaH Sodium hydride NaHCO$_3$ Sodium bicarbonate
NBS N-bromo succinimide
NCS N-chloro succinimide
NEt$_3$ Trimethylamine
NMP N-Methyl-2-pyrrolidone
PCC Pyridinium chlorochromate
Pd (OAc)$_2$ Palladium acetate
Pd(dppf)Cl$_2$ [1,1′-Bis(diphenylphosphino) ferrocene]dichloropalladium(II)
Pd(PPh$_3$)$_2$Cl$_2$ Bis(triphenylphosphine)palladium(II) dichloride
Pd(PPh$_3$)$_4$ Tetrakis(triphenylphosphine)palladium(0)
Pd/C Palladium on carbon
Pd$_2$ (dba)$_3$ Tris(dibenzylideneacetone)dipalladium(0)
PMB 4-Methoxybenzyl ether
PPh$_3$ Triphenylphosphine
Pr Propyl
Py, py Pyridine
RT Room temperature
T3P Propane phosphonic acid anhydride
TBAF Tetra-n-butylammonium fluoride
TBAT Tetrabutylammonium difluorotriphenylsilicate
tBu, t-Bu tertbutyl
tBuOK Potassium tert-butoxide
TEA Trimethylamine
Tf$_2$O Trifluoromethanesulfonic anhydride
TFA Trifluoroacetic acid
THF Tetrahydrofuran
TMS Trimethylsilane
TMSBr Bromotrimethylsilane
t$_R$ Retention time
Troc 2,2,2-Trichlorethoxycarbonyl chloride
Zn (CN)$_2$ Zinc cyanide General Methods All nonaqueous reactions were performed under an atmosphere of dry argon or nitrogen gas using anhydrous solvents. The progress of reactions and the purity of target compounds were determined using one of the two liquid chromatography (LC) methods listed below. The structure of starting materials, intermediates, and final products was confirmed by standard analytical techniques, including NMR spectroscopy and mass spectrometry.

LC Method A
Instrument: Waters Acquity Ultra Performance LC
Column: ACQUITY UPLC BEH C18 2.1×50 mm, 1.7 μm
Column Temperature: 40° C.
Mobile Phase: Solvent A: H$_2$O+0.05% FA; Solvent B: CH$_3$CN+0.05% FA
Flow Rate: 0.8 mL/min
Gradient: 0.24 min @ 15% B, 3.26 min gradient (15-85% B), then 0.5 min @ 85% B.
Detection: UV (PDA), ELS, and MS (SQ in EI mode)

LC Method B
Instrument: Shimadzu LC-2010A HT
Column: Athena, C18-WP, 50×4.6 mm, 5 μm
Column Temperature: 40° C.
Mobile Phase: Solvent A: H$_2$O/CH$_3$OH/FA=90/10/0.1; Solvent B: H$_2$O/CH$_3$OH/FA=10/90/0.1
Flow Rate: 3 mL/min
Gradient: 0.4 min @ 30% B, 3.4 min gradient (30-100% B), then 0.8 min @ 100% B
Detection: UV (220/254 nm)

LC Method C
Instrument: Agilent 1100/1200 series LC system with DAD detector
Column: Atlantis dC18 (250×4.6) mm, 5 μm
Column Temperature: Ambient
Mobile Phase A: 0.1% TFA in water, Mobile Phase B: Acetonitrile
Flow Rate: 1.0 m/min
Gradient:

| Time (min) | 0.0 | 15 | 20 | 23 | 30 |
|---|---|---|---|---|---|
| % B | 10 | 100 | 100 | 10 | 10 |

Detection: (210-400 nm)

LC Method D
Instrument: Shimadzu LC 20AD system with PDA detector
Column: Phenomenex Gemini NX C18 (150×4.6) mm, 5 μm
Column Temperature: Ambient
Mobile Phase A: 10 mM NH$_4$OAC in water, Mobile Phase B: Acetonitrile
Flow Rate: 1.0 m/min
Gradient:

| Time (min) | 0.0 | 15 | 20 | 23 | 30 |
|---|---|---|---|---|---|
| % B | 10 | 100 | 100 | 10 | 10 |

Detection: (210-400 nm)

Example 1. General Route of Synthesis

A compound of the present invention can be prepared, for example, from a central core. In one embodiment, for example, the central core Structure 1 is an N-protected aminoacid where $X^1$ is nitrogen and PG=protecting group. In one embodiment, the central core is coupled to an amine to generate an amide of Structure 2 (wherein L-B includes a C(O)N moiety). Structure 2 can then be deprotected to generate Structure 3. Structure 3 is coupled to Structure 4(A-COOH) to generate a second amide bond, forming a compound within Formula I. The chemistry is illustrated in Route 1.

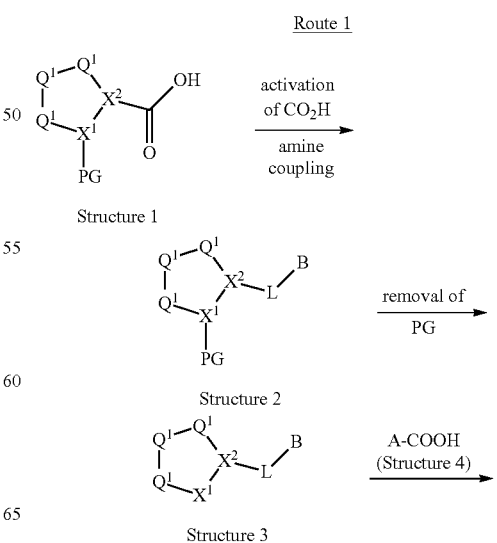

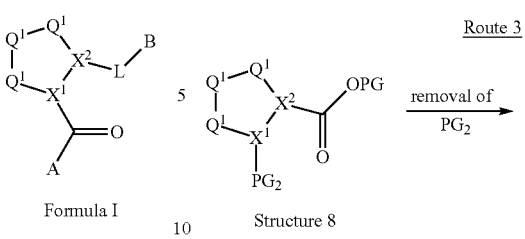

In an alternative embodiment, central core Structure 5 is reacted with a heterocyclic or heteroaryl compound to generate a compound of Structure 6. In one embodiment, Structure 6 is deprotected to generate a carboxylic acid, Structure 7. In one embodiment, Structure 7 is coupled to an amine to generate a compound of Formula I. This chemistry is illustrated in Route 2.

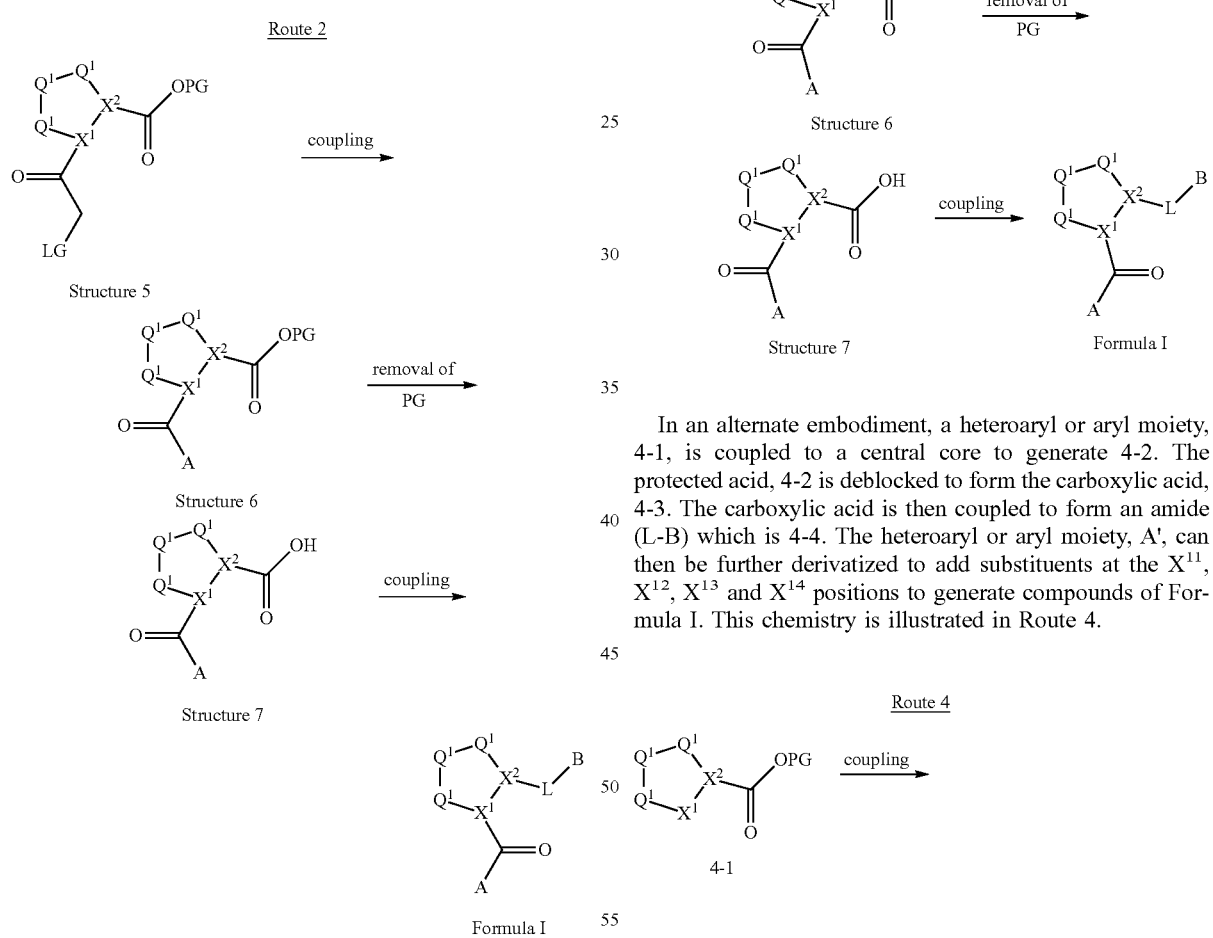

In an alternative embodiment, Structure 8 is deprotected to generate an amine which is Structure 9. Structure 9 is then coupled to generate an amide which is Structure 6. Structure 6 is then deprotected to generate a carboxylic acid which is Structure 7. Structure 7 is then coupled to form the amide which falls within Formula I. The chemistry is illustrated in Route 3.

In an alternate embodiment, a heteroaryl or aryl moiety, 4-1, is coupled to a central core to generate 4-2. The protected acid, 4-2 is deblocked to form the carboxylic acid, 4-3. The carboxylic acid is then coupled to form an amide (L-B) which is 4-4. The heteroaryl or aryl moiety, A', can then be further derivatized to add substituents at the $X^{11}$, $X^{12}$, $X^{13}$ and $X^{14}$ positions to generate compounds of Formula I. This chemistry is illustrated in Route 4.

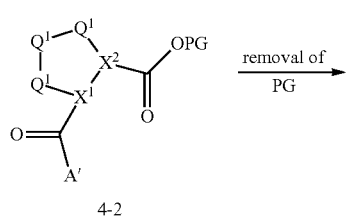

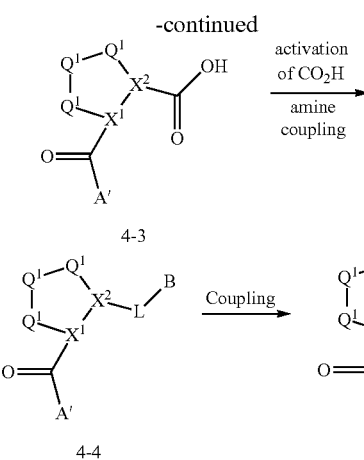

4-3

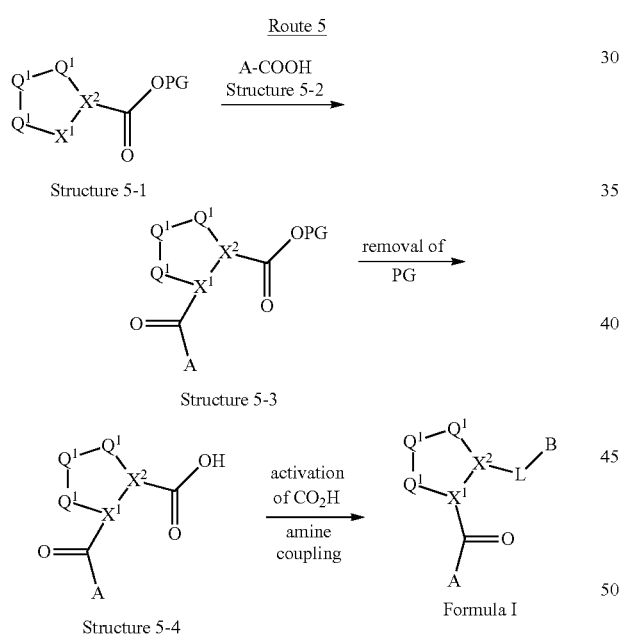

In an alternate embodiment, Structure 5-1 is coupled to an acid, Structure 5-2, to generate Structure 5-3. The carboxylic acid, Structure 5-3, is deblocked to generate a carboxylic acid which is Structure 5-4. Carboxylic acid Structure 5-4 is coupled to an amine to form the product amide (L-B) which is a compound within Formula I. This chemistry is illustrated in Route 5.

In an alternate embodiment, a heteroaryl compound of Structure 10 is acylated to generate a compound of Structure 11, wherein LG is a leaving group. As an example, the leaving group can be a halide, for example bromide. Structure 11 is coupled to Structure 12 to generate Structure 13. In some embodiments, $LG_1$ is a leaving group. In some embodiments, the $LG_1$ is a halide. Structure 13 is coupled to an aryl, heteroaryl or heterocyclic compound to generate Structure 14. In some embodiments, Structure 13 is treated with an aryl, heteroaryl or heterocylic boronic acid, an organometallic catalyst, a base and an organic solvent. In some embodiments, the organometallic catalyst is tetrakis (triphenylphosphine)palladium (0). In some embodiments, the base is cesium carbonate. In some embodiments, the organic solvent is DMF. Structure 14 is treated with an organic acid such as, but not limited to, trifluoroacetic acid to generate Structure 15. Structure 15 is coupled to Structure 3 from Route 1 to generate a compound within Formula I. This chemistry is illustrated in Route 6.

Route 6

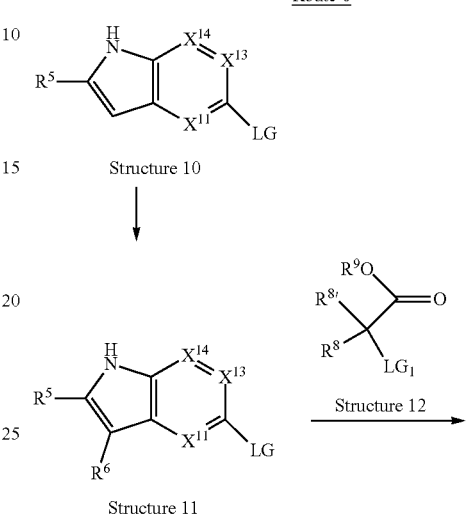

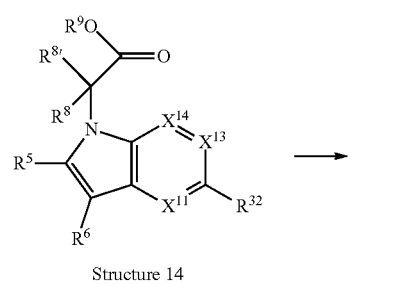

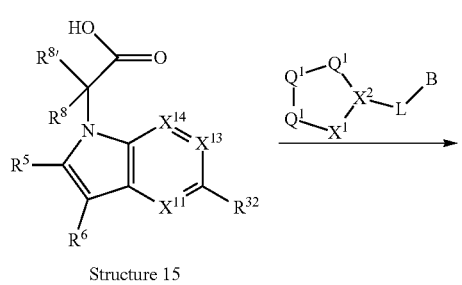

-continued

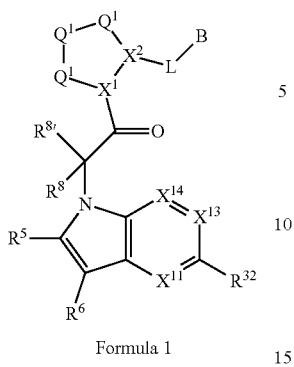

Formula 1

In an alternate embodiment, a heteroaryl compound of Structure 17 is acylated to generate a compound of Structure 18, wherein LG is a leaving group. As an example, the leaving group can be a halide, for example bromide. Structure 18 is coupled to an activated ester, Structure 12 from Route 6, wherein $LG_1$ can be a halogen to generate Structure 19.

Structure 19 is coupled to an aryl, heteroaryl or heterocylic compound to generate Structure 20. In some embodiments, Structure 19 is treated with an aryl, heteroaryl or heterocylic boronic acid, an organometallic catalyst, a base and an organic solvent. In some embodiments, the organometallic catalyst is tetrakis(triphenylphosphine)palladium (0). In some embodiments, the base is cesium carbonate. In some embodiments, the organic solvent is DMF. Structure 20 is treated with an organic acid such as, but not limited to, trifluoroacetic acid to generate Structure 21. Structure 21 is coupled to Structure 3 from Route 1 to generate a compound within Formula I. This chemistry is illustrated in Route 7.

Route 7

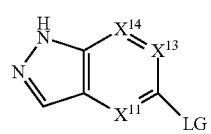

Structure 17

↓

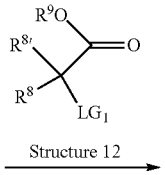

Structure 18

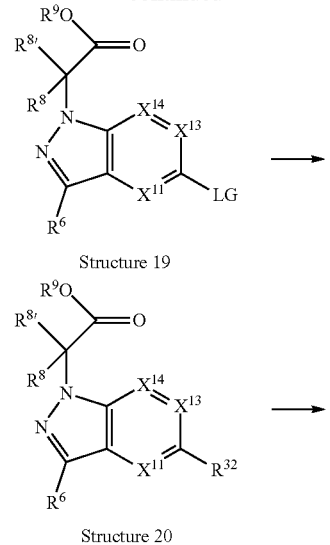

Structure 19

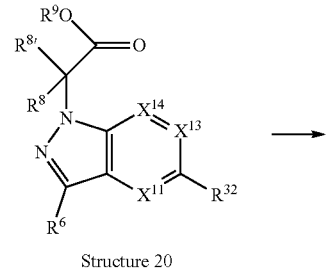

Structure 20

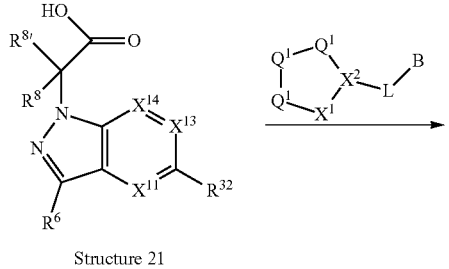

Structure 21

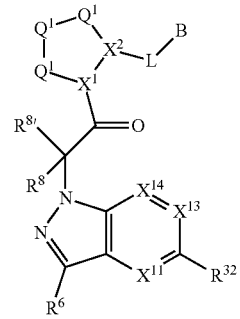

Formula 1

In an alternate embodiment, a heteroaryl compound of Structure 8-1 is acylated to generate a compound of Structure 8-2, wherein LG is a leaving group. As an example, the leaving group can be a halide, for example bromide. Structure 8-2 is coupled to Structure 8-3 to generate Structure 8-4. In some embodiments, $LG_1$ is a leaving group. In some embodiments, the $LG_1$ is a halide.

Structure 8-4 is coupled to an aryl, heteroaryl or heterocylic compound to generate Structure 8-5. In some embodiments, Structure 8-4 is treated with an aryl, heteroaryl or heterocylic boronic acid, an organometallic catalyst, a base and an organic solvent. In some embodiments, the organometallic catalyst is tetrakis(triphenylphosphine)palladium (0). In some embodiments, the base is cesium carbonate. In some embodiments, the organic solvent is DMF. Structure 8-5 is treated with an organic acid such as, but not limited to, trifluoroacetic acid to generate Structure 8-6. Structure 8-6 is coupled to Structure 3 from Route 1 to generate a compound within Formula I. This chemistry is illustrated in Route 8.

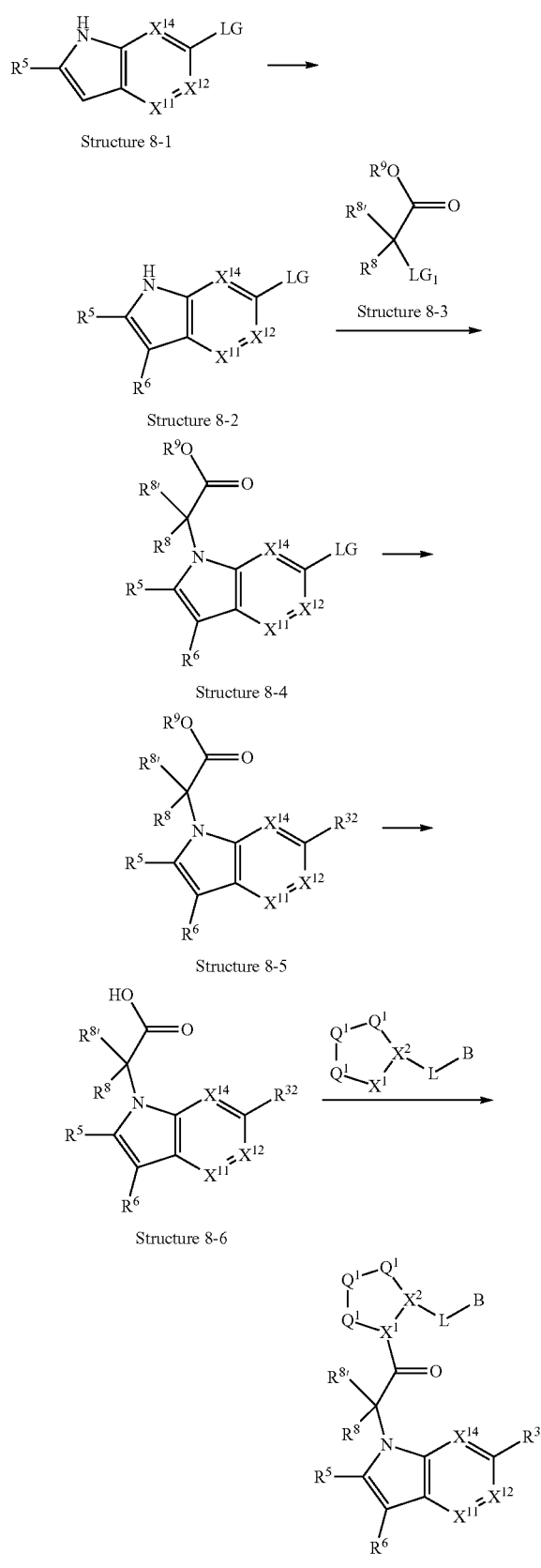

Route 8

In an alternate embodiment, a heteroaryl compound of Structure 9-1 is acylated to generate a compound of Structure 9-2, wherein LG is a leaving group. As an example, the leaving group can be a halide, for example bromide. Structure 9-2 is coupled to an activated ester, Structure 9-3, wherein $LG_1$ can be a halide to generate Structure 9-4. Structure 9-4 is coupled to an aryl, heteroaryl or heterocylic compound to generate Structure 9-5. In some embodiments, Structure 9-4 is treated with an aryl, heteroaryl or heterocylic boronic acid, an organometallic catalyst, a base and an organic solvent. In some embodiments, the organometallic catalyst is tetrakis(triphenylphosphine)palladium (0). In some embodiments, the base is cesium carbonate. In some embodiments, the organic solvent is DMF. Structure 9-5 is treated with an organic acid such as, but not limited to, trifluoroacetic acid to generate Structure 9-6. Structure 9-6 is coupled to Structure 3 from Route 1 to generate a compound within Formula I. This chemistry is illustrated in Route 9.

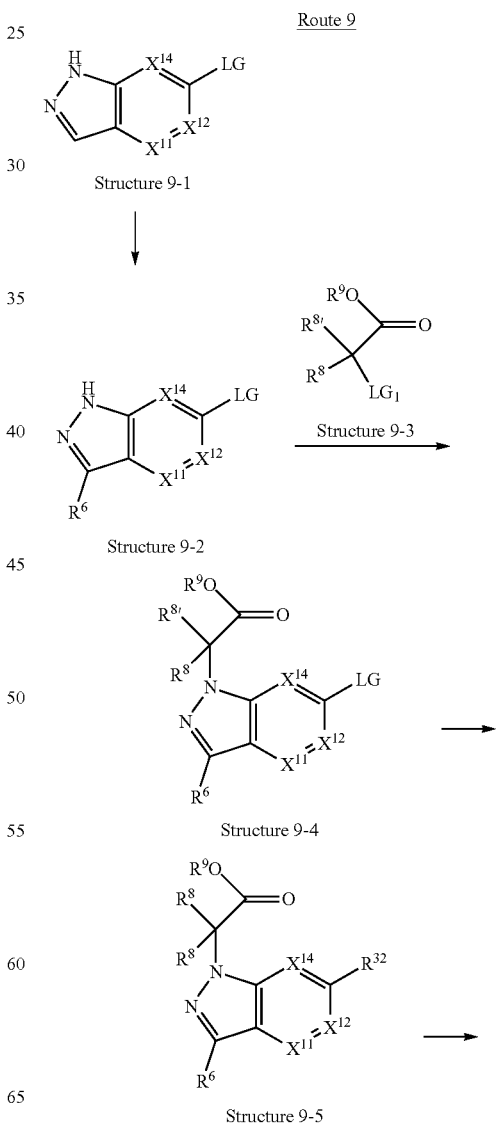

591
-continued
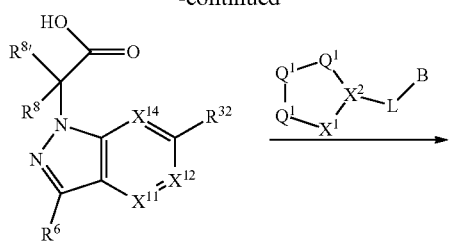
Structure 9-6
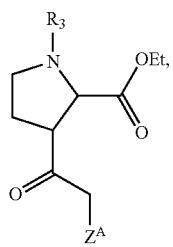
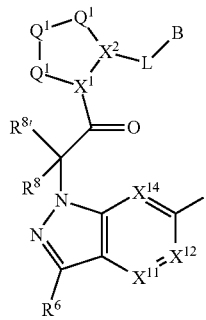
Formula 1
In an alternate embodiment, Structure 10-1 is coupled to an amine to generate an amide (L-B), and Structure 10-2. Structure 10-2, is coupled to an amine to generate compounds within Formula I. This chemistry is illustrated in Route 10.
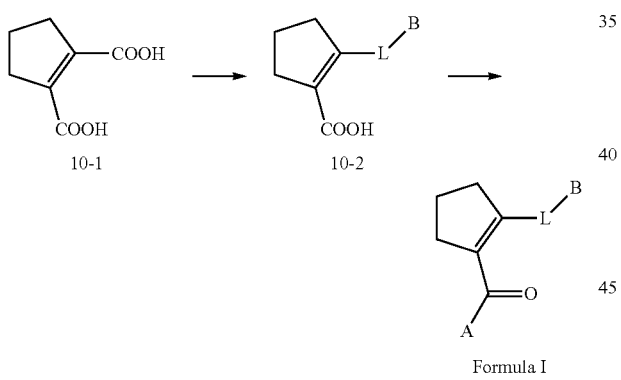
Formula I
Example 2. Examples of Central Synthons
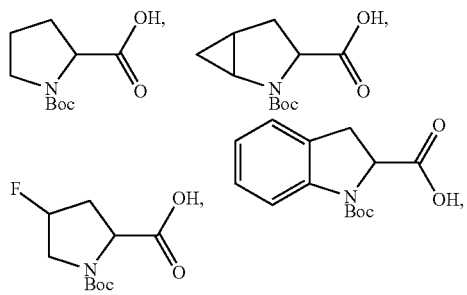
592
-continued
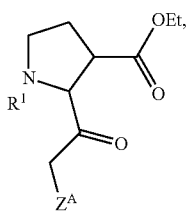
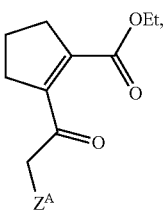
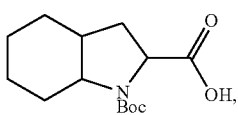
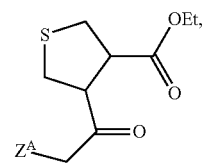
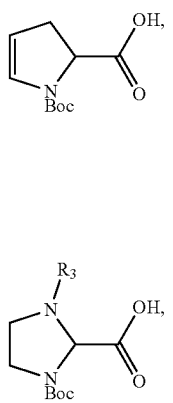
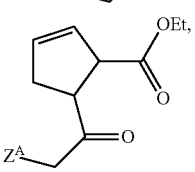
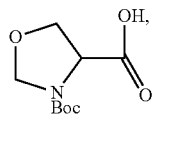
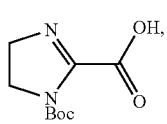
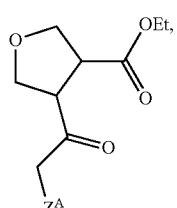
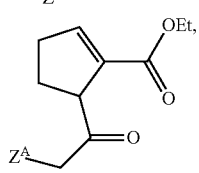
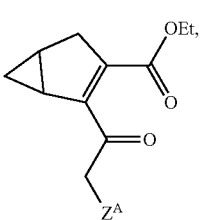
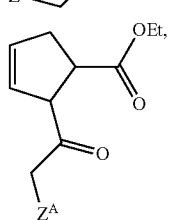
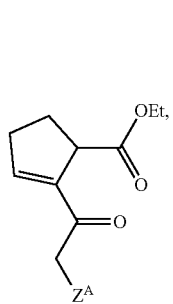

593
-continued
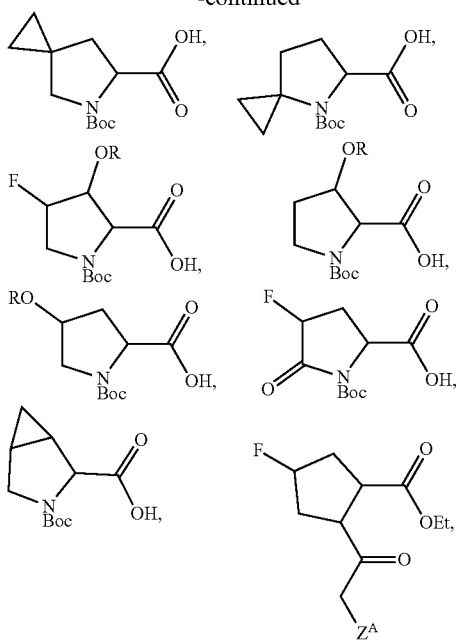
594
-continued
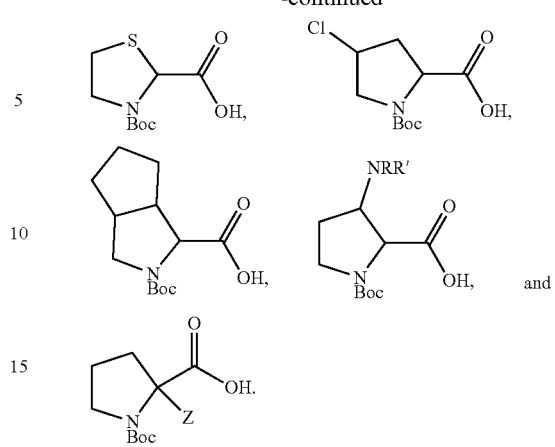
$Z^A$ is halogen.
In one embodiment, deuterated L-proline synthons are disclosed. Deuterated synthons include, but are not limited to, for example, the following compounds:
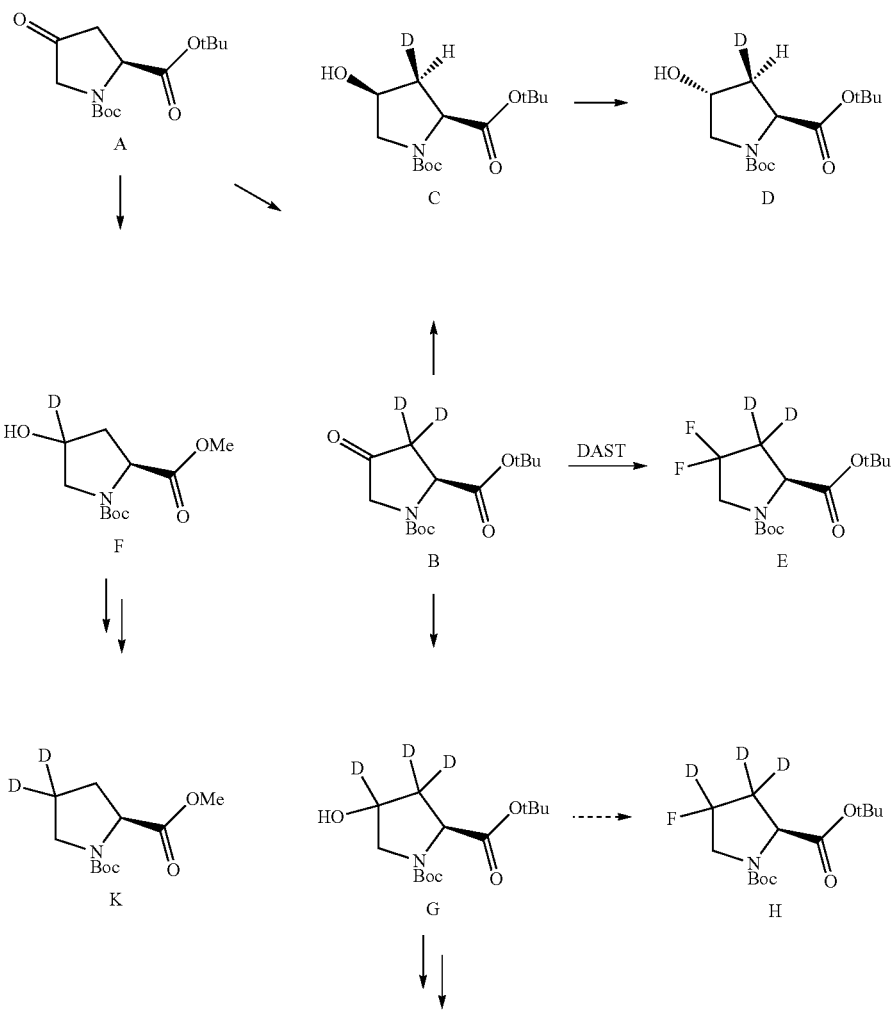

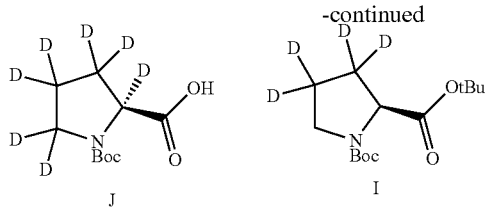

Structure A can be treated with deuterium oxide to generate Structure B. See, Barraclough, P. et al. Tetrahedron Lett. 2005, 46, 4653-4655; Barraclough, P. et al. Org. Biomol. Chem. 2006, 4, 1483-1491 and WO 2014/037480 (p. 103). Structure B can be reduced to generate Structure C. See, Barraclough, P. et al. Tetrahedron Lett. 2005, 46, 4653-4655; Barraclough, P. et al. Org. Biomol. Chem. 2006, 4, 1483-1491. Structure C can be treated with Mitsunobu reaction conditions to generate Structure D. Structure B can be treated with DAST to generate Structure E. See, WO 2014/037480. Structure A can be treated with sodium borodeuteride to generate Structure F. See, Dormoy, J.-R.; Castro, B. *Synthesis* 1986, 81-82. Compound F can be used to generate Structure K. See, Dormoy, J.-R.; Castro, B. *Synthesis* 1986, 81-82. Structure B can be treated with a deuterated reducing agent, for example sodium borodeuteride to generate Structure G. Structure G can be treated with DAST to generate Structure H. Structure F can be used to generate Structure K. See, Dormoy, J.-R.; Castro, B. *Synthesis* 1986, 81-82. Structure G can be used to generate Structure I. Structure J can be prepared according to Hruby, V. J. et al. *J. Am. Chem. Soc.* 1979, 101, 202-212. Structures A-J can be used to prepare compounds of Formula I.

Example 3. Preparation of Central-L-B Synthons

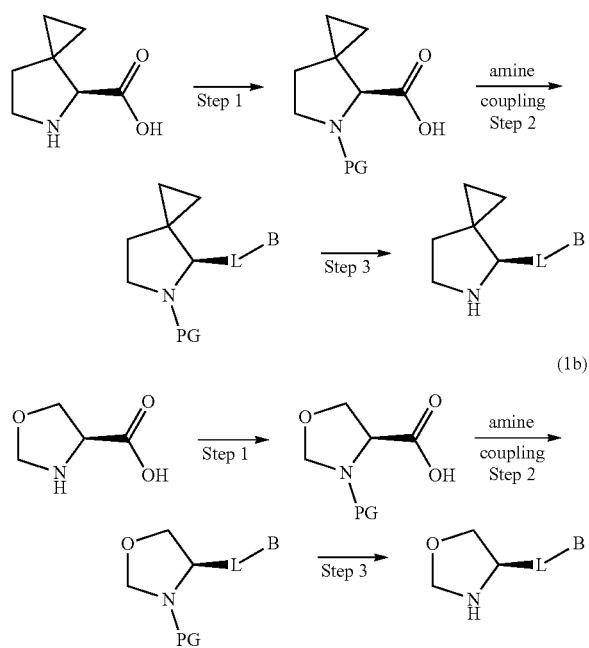

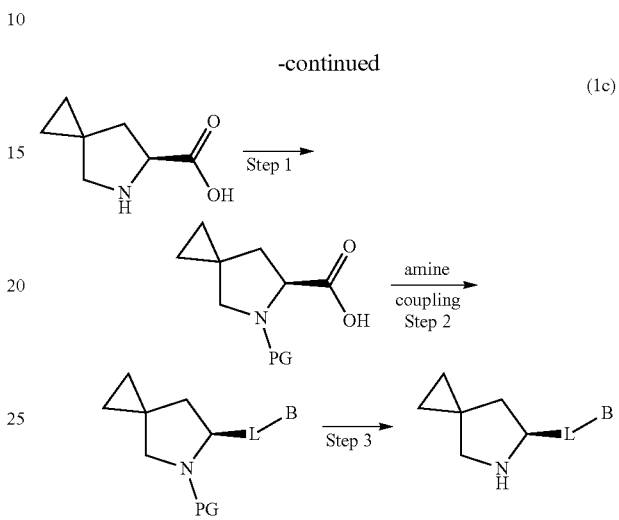

Routes 1a, 1b and 1c.

In Route 1a, 5-azaspiro[2.4]heptane-4,5-dicarboxylic acid, 5-(1,1-dimethylethyl) ester, (4S)—, CAS 209269-08-9, can be prepared as described in Tandon, M. et al. Bioorg. Med. Chem. Lett. 1998, 8, 1139-1144. In Step 2, the protected azaspiro[2.4]heptane is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

In Route 1b, (4S) 4-oxazolidinecarboxylic acid, hydrochloride is treated with an amine protecting reagent. In one embodiment, the amine protecting reagent is di-tert-butyl dicarbonate. In another embodiment, 3,4-oxazolidinedicarboxylic acid, 3-(1,1-dimethylethyl) ester, (4S)—, is commercially available from JPM2 Pharmaceuticals. In one embodiment the reaction is carried out in an organic solvent in the presence of a base. In one embodiment, the organic solvent is acetonitrile. In one embodiment, the base is 4-dimentylaminopyridine (DMAP). In Step 2, the protected 4-oxazolidinecarboxylic acid is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

In Route 1c, (S)-5-(tert-Butoxycarbonyl)-5-azaspiro[2.4]heptane-6-caboxylic acid, CAS 1129634-44-1, is commercially available from Ark Pharm. In Step 2, the carboxylic acid is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

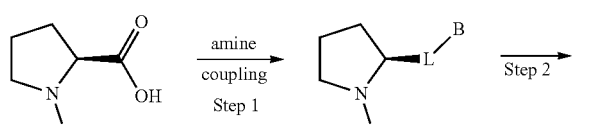

2a

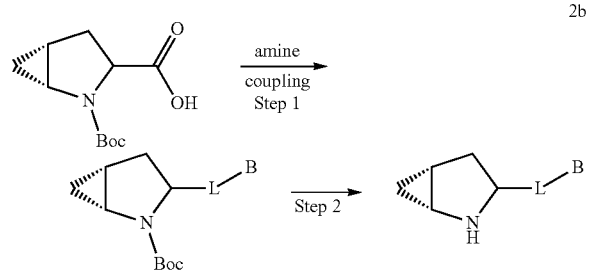

2b

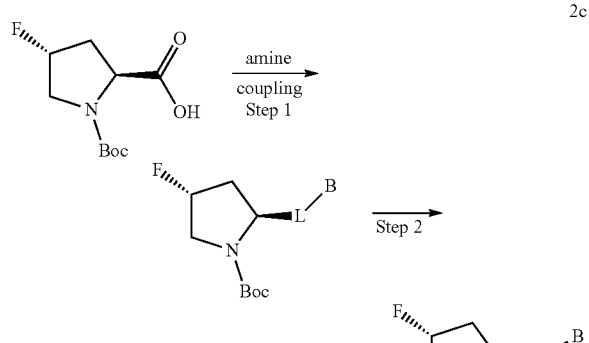

2c

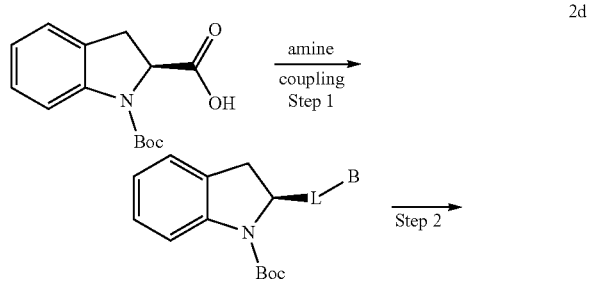

2d

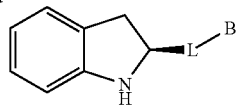

Routes 2a, 2b, 2c, and 2d.

In Route 2a, commercially available Boc-L-proline is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DWF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2b, commercially available (1R, 3S, 5R)-2-[(tert-butoxy)carbonyl]-2-azabicyclo[3.1.0]hexane-3-carboxylic acid, from Enamine, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DWF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2c, commercially available (2S,4R)-1-(tert-butoxycarbonyl)-4-fluoropyrrolidine-2-carboxylic acid, from Manchester Organics, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2d, commercially available (S)-1-(tert-butoxycarbonyl)indoline-2-carboxylic acid, from Chem-Impex, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane. This chemistry is illustrated in Scheme 2.

Additional starting materials that can readily be converted to Central-L-B-Synthons include, but are not limited to: (S)-1-(tert-butoxycarbonyl)-2,3-dihydro-1H-pyrrole-2-carboxylic acid, CAS 90104-21-5, available from Ark Pharm; cyclopent-1-ene-1,2-dicarboxylic acid, CAS 3128-15-2, purchased from Ark Pharm; imidazole, 1H-imidazole-1,2-dicarboxylic acid, 1-(1,1-dimethylethyl) 2-ethyl ester, CAS 553650-00-3, commercially available from FCH Group; Boc-L-octahydroindole-2-carboxylic acid can be purchased from Chem Impex. The compound,

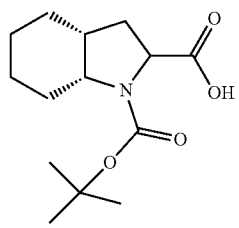 [SMILES: CC(C)(C)OC(=O)N1C(C(=O)O)C[C@H]2CCCC[C@H]21]

can be prepared according to the procedures disclosed in WO 2004/111041; (S)-Boc-5-oxopyrrolidine-2-carboxylic acid is available from the Aldrich Chemical Co.; (1S,2S, 5R)-3-(tert-butoxycarbonyl)-3-azabicyclo[3.3.0]hexane-2-carboxylic acid is available from Ark Pharm; (S)-3-Boc-thiazolidine-2-carboxylic acid is available from Alfa Aesar; (2S,4R)-1-(tert-butoxycarbonyl)-4-chloropyrrolidine-2-carboxylic acid is available from Arch Bioscience; (1S,3aR, 6aS)-2-(tert-butoxycarbonyl)octahydrocyclopenta[c]pyrrole-1-carboxylic acid is available from Ark Pharm; 1,2-pyrrolidinedicarboxylic acid, 3-[[(phenylmethoxy)carbonyl]amino]-, 1-(1,1-dimethylethyl) ester, (2S,3R) can be prepared as disclosed in WO 2004/007501. The Cbz group can be removed and the amino group can be alkylated to generate central core compounds of the present invention.

The compound

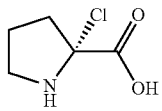

can be prepared as disclosed by Braun, J. V.; Heymons, Albrecht Berichte der Deutschen Chemischen Gesellschaft [Abteilung] B: Abhandlungen (1930) 63B, 502-7.

The compounds (2S,3S,4S)-4-fluoro-3-methoxy-pyrrolidine-1,2-dicarboxylic acid 1-tert-butyl ester and (2R,3R, 4R)-3-fluoro-4-methoxy-pyrrolidine-1,2-dicarboxylic acid 1-tert-butyl ester can be prepared as a mixture according to WO 2012/093101 to Novartis and the regioisomers can be ultimately separated once coupled to generate the central core-L-B synthons. The compound (S)-Boc-5-oxopyrrolidine-2-carboxylic acid is available from the Aldrich Chemical Co.

Example 4. Synthesis of L-B Moieties

Scheme 4-1

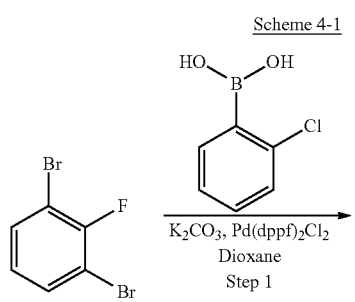

Scheme 4-1: In Step 1 the appropriately substituted dibromo species is coupled with an appropriate boronic acid as known in the art to form a mixture of biaryl and triaryl products from which the desired biaryl compound is isolated. In Step 2 the appropriately substituted biaryl species is converted to the Grignard reagent with activated magnesium. In Step 3 the appropriately substituted aldehyde is treated with the previously prepared Grignard reagent to form an alcohol. In Step 4 the appropriately substituted alcohol is converted to a bromide as known in the art with carbon tetrabromide and triphenyl phosphine. In Step 5 the appropriately substituted bromide is converted to the Grignard reagent with activated magnesium.

Example 5. Synthesis of C-L-B Moieties
Scheme 5-1
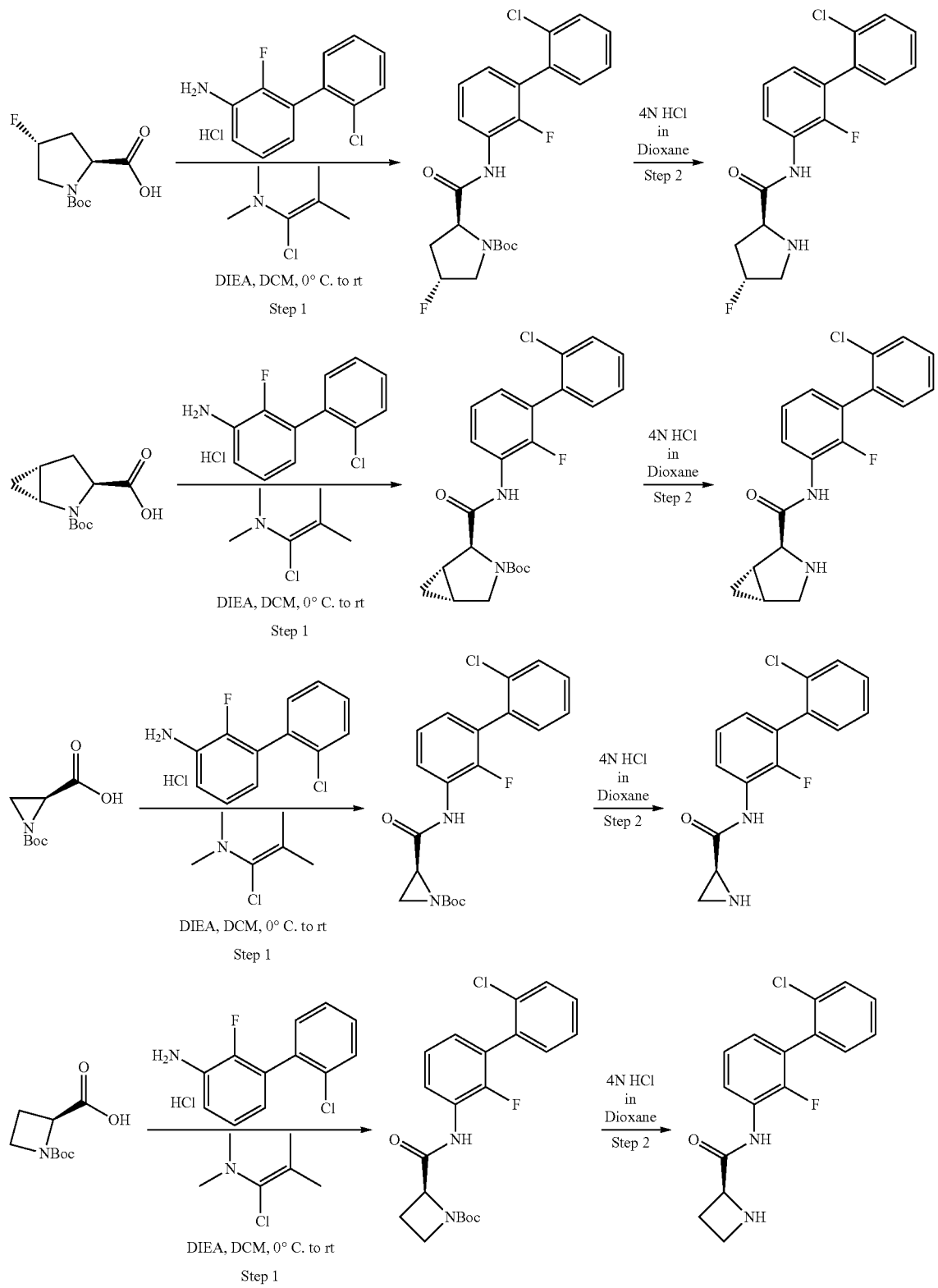

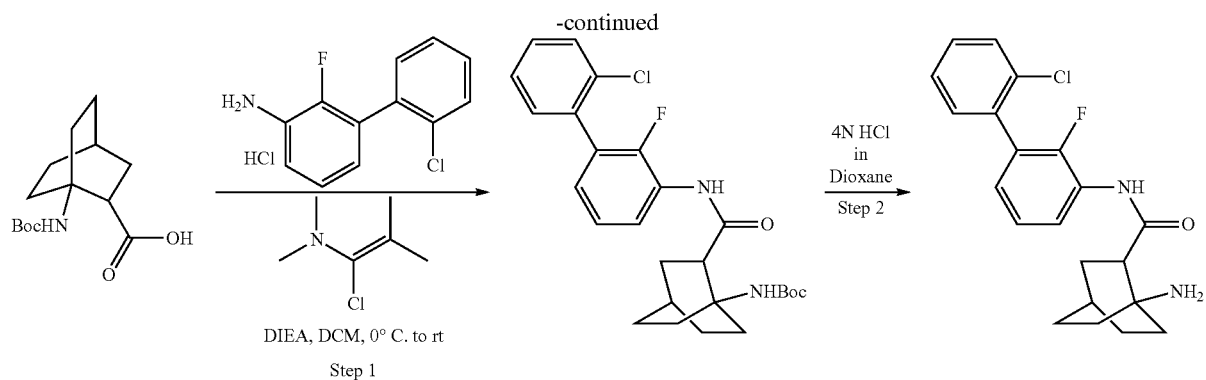

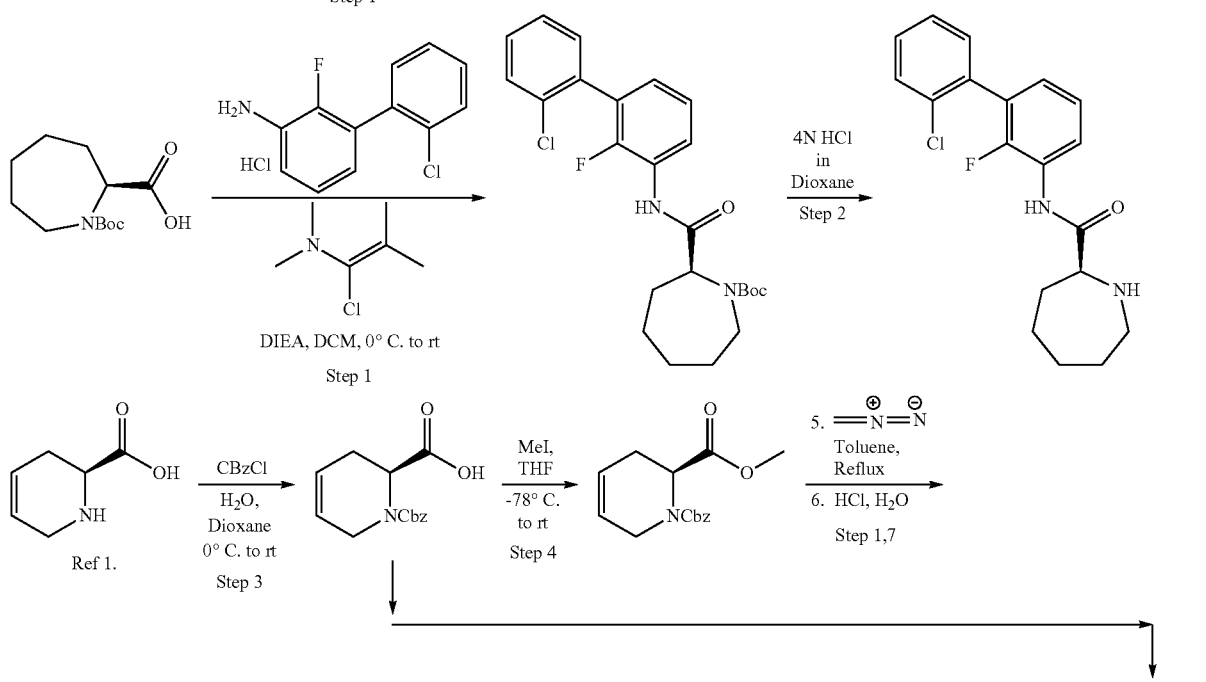

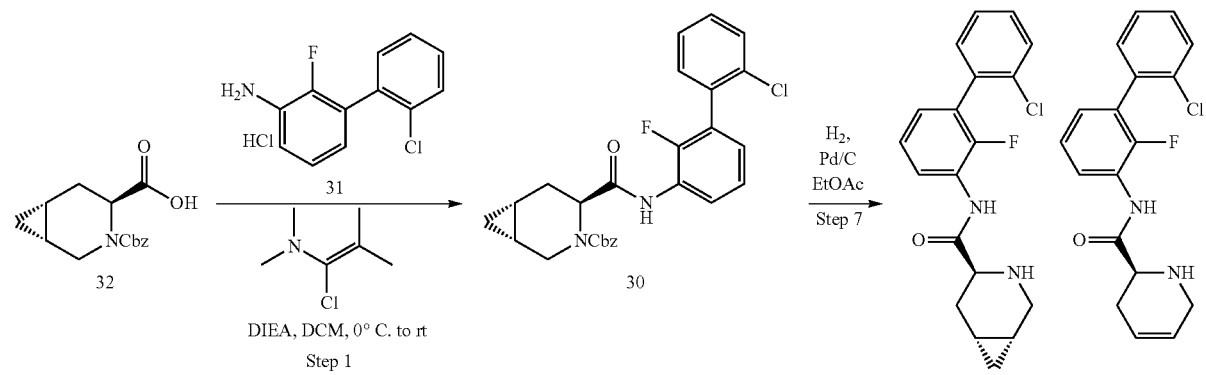

1. Herdeis, C., et al. (1994). Liebigs Ann. Chem.(11): 1117-1120.

Scheme 5-1: In Step 1 the appropriately substituted carboxylic acid is coupled to the appropriately substituted amine as known in the art to form an amide. In Step 2 the appropriately substituted Boc-protected species is deprotected with acid to liberate the free amine. In Step 3 the appropriately substituted amine is Cbz-protected as known in the art to form a protected carboxylic acid. In Step 4 the appropriately substituted carboxylic acid can be orthogonally protected as known in the art to form an ester. In Step 5 the appropriately substituted and protected alkene is subjected to a carbene to form a bicyclic ring. In Step 6 the appropriately substituted ester is saponified with acid to liberate the carboxylic acid. In Step 7 the appropriately substituted Cbz-protected species is deprotected with hydrogen to liberate the free amine.

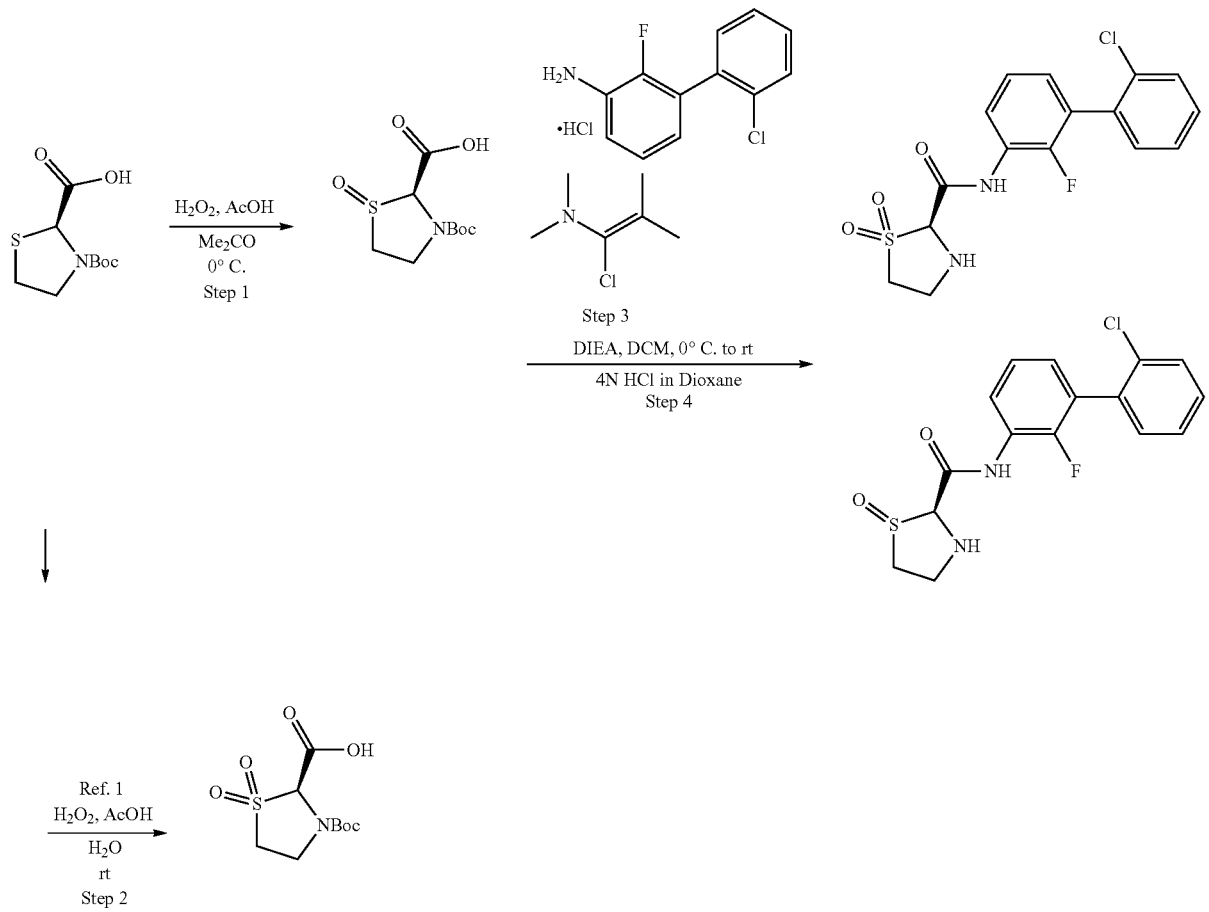

1. Vasil'eva, T.P. (2003). Russ. Chem. Bull. 52(4): 958-960.

Scheme 5-2: In Step 1 the appropriately substituted sulfide is oxidized to a sulfoxide as known in the art. Alternatively, in Step 2 the appropriately substituted sulfide is oxidized to a sulfone as known in the art. In Step 3 the appropriately substituted carboxylic acid is coupled to the appropriately substituted amine as known in the art to form an amide. In Step 4 the appropriately substituted Boc-protected species is deprotected with acid to liberate the free amine.

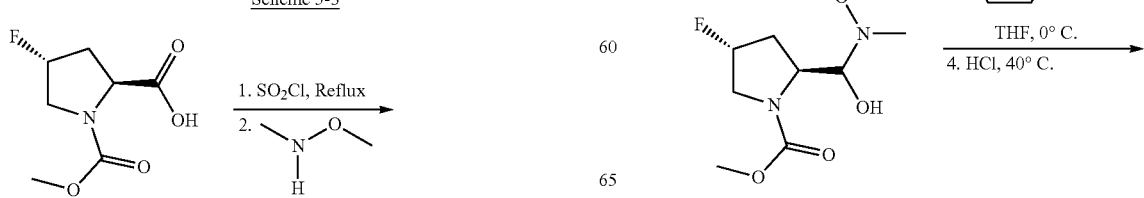

-continued

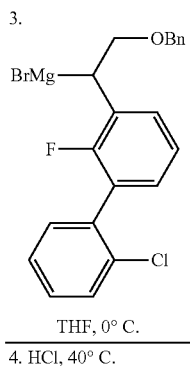

607
-continued

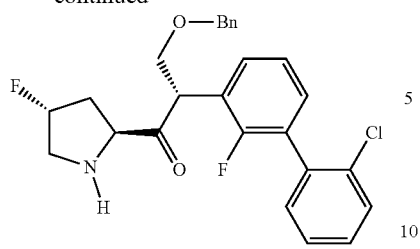

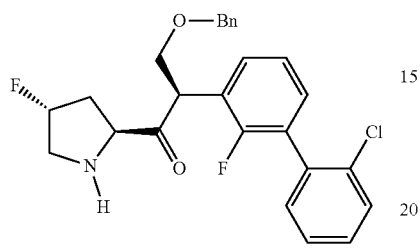

Scheme 5-3: In Step 1 the appropriately substituted carboxylic acid is converted to the acyl chloride as known in the art. In Step 2 the appropriately substituted acyl chloride is converted to the Weinreb amide as known in the art. In Step 3 the appropriately substituted Weinreb amide is reacted with a Grignard reagent to afford a ketone. The synthesis of complex Grignard reagents is described in Example 4. In Step 4 the appropriately substituted carbamate protected amine is deprotected to liberate the free amine.

Scheme 5-4

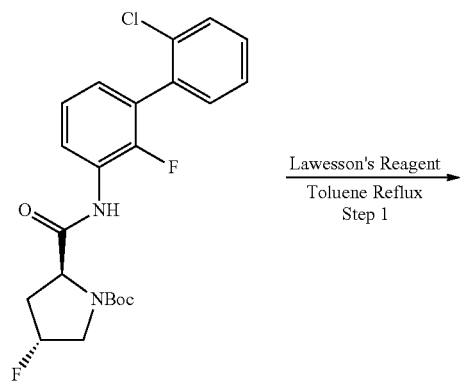

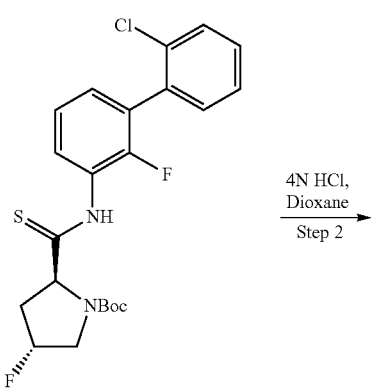

608
-continued

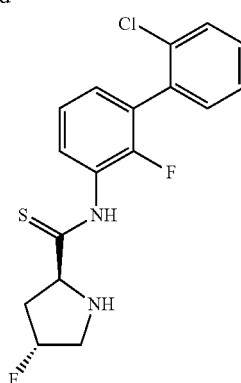

Scheme 5-4: In Step 1 the appropriately substituted amide is converted to a thioamide with Lawesson's reagent. In Step 2 the appropriately substituted Boc-protected amine is deprotected with acid to liberate the free amine.

Scheme 5-5

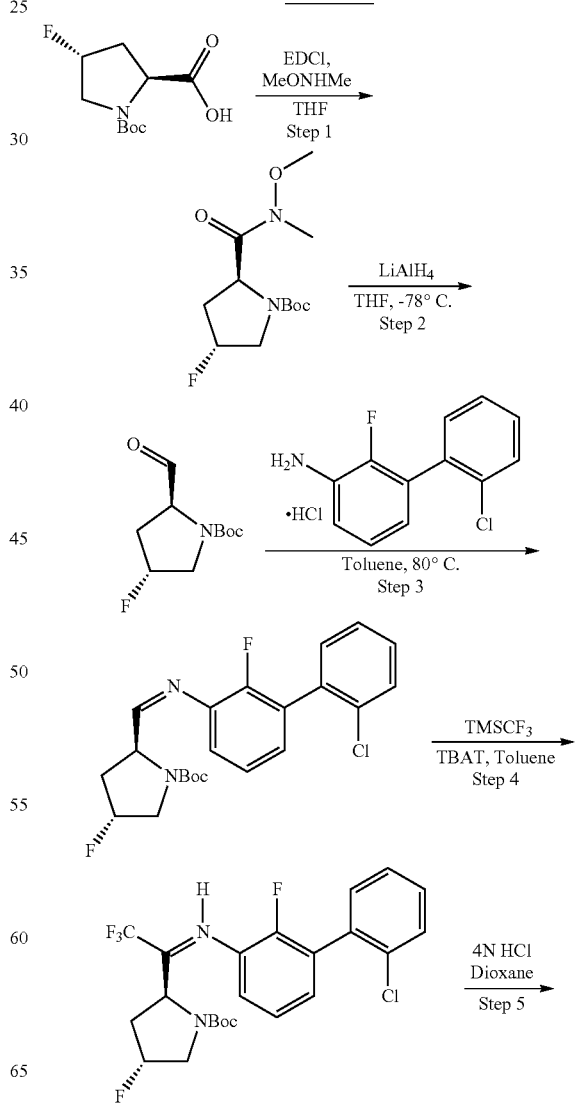

-continued

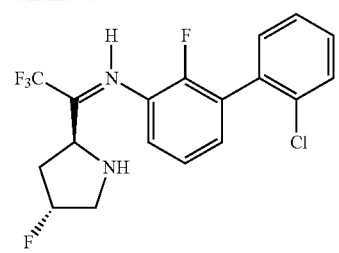

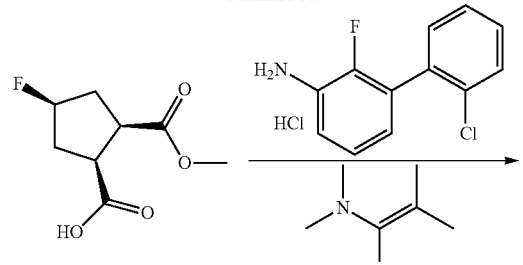

Scheme 5-5: In Step 1 the appropriately substituted carboxylic acid is converted to a Weinreb amide as known in the art. In Step 2 the appropriately substituted Weinreb amide is reduced as known in the art to afford an aldehyde. In Step 3 the appropriately substituted aldehyde is subjected to an amine to form a Schiff base which is subsequently quenched in Step 4. In Step 4 the appropriately substituted Schiff base is subjected to an appropriate nucleophile to form a complex amine. In Step 5 the appropriately substituted Boc-protected species is deprotected with acid to liberate the free amine.

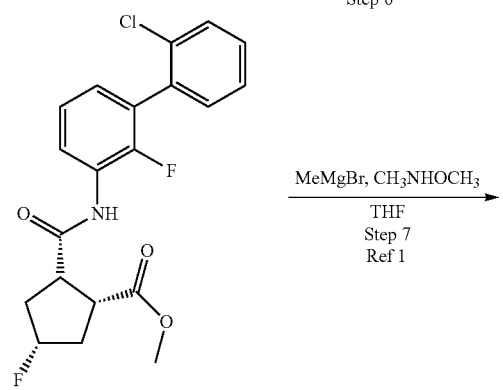

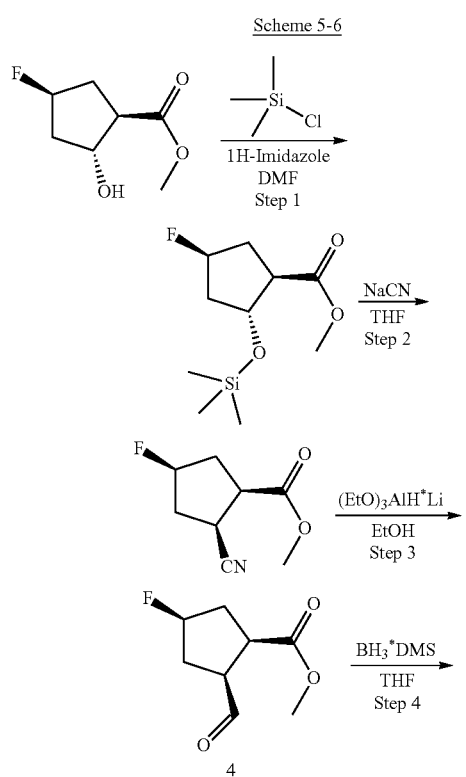

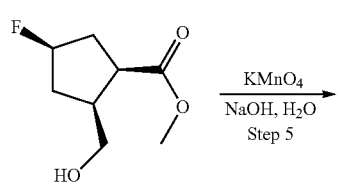

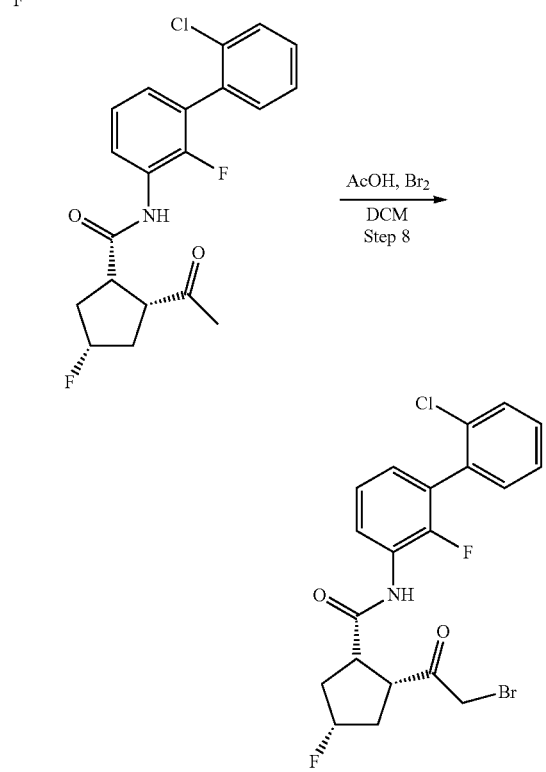

1. Posser, A. R. and D. C. Liotta (2015). Tetrahedron Lett. 56(23): 3005-3007.

Scheme 5-6: In Step 1 the appropriately substituted alcohol is subjected to TMS-Cl as known in the art to afford a silyl ether. In Step 2 the appropriately substituted silyl ether is subjected with sodium cyanide to afford a cyano species. In Step 3 the appropriately substituted cyano species is reduced as known in the art to afford an aldehyde. In Step 4 the appropriately substituted aldehyde is further reduced with borane to afford an alcohol. In Step 5 the appropriately substituted alcohol is oxidized as known in the art to afford a carboxylic acid. In Step 6 the appropriately substituted carboxylic acid is coupled to the appropriately substituted amine as known in the art to form an amide. In Step 7 the appropriately substituted ester is converted to a methyl ketone by insitu formation of the Weinreb amide with subsequent attack by the methyl Grignard reagent. In Step 8 the appropriately substituted methyl ketone is subjected to bromine to afford a bromide. By choice of the appropriate starting material all mixtures of chiral centers may be prepared as described.

Example 6. Synthesis of A Moieties

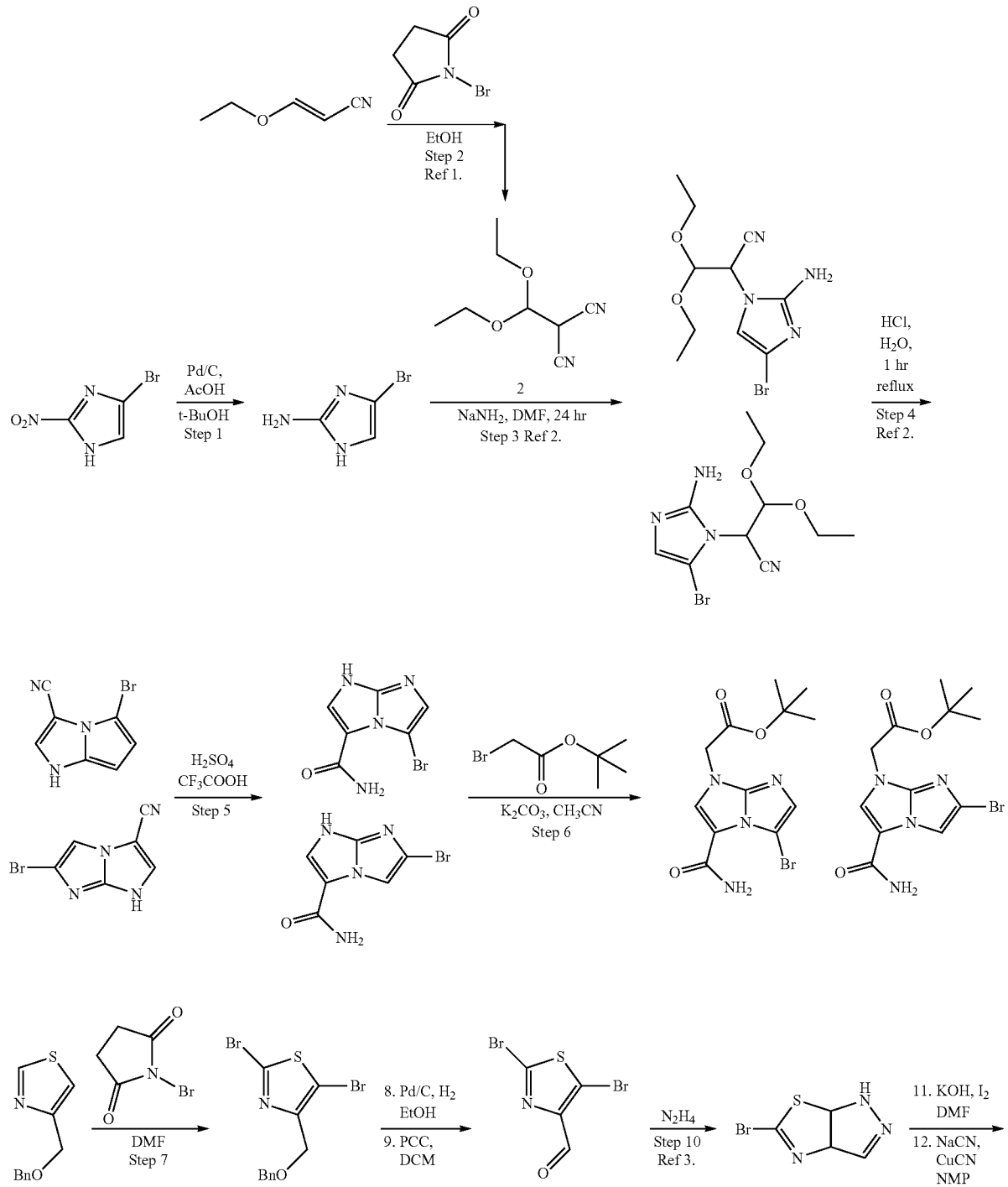

-continued

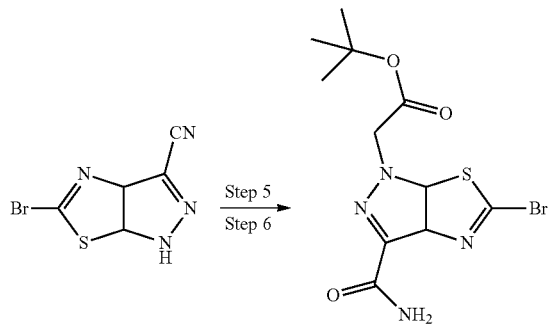

1. Babler, J. H. (1987). Synth. Commun. 17(1): 77-84.
2. Mas, T., et al. (2002). ARKIVOC (Gainesville, FL, U.S.)(5): 48-61.
3. Lebedev, A.Y., et al. (2005). J. Org. Chem. 70(2): 596-602.

Scheme 6-1: In Step 1 the appropriately substituted nitro species is reduced with palladium as known in the art to afford an amine. In Step 2 the appropriately substituted alkene species is brominated with concurrent addition of ethanol as known in the art to afford the bromide species. In Step 3 the appropriately substituted mixture of tautomers is subjected to the previously prepared bromide species as known in the art to afford the two isomers. The appropriately substituted isomers corresponding to each tautomer may either be separated or used as a mixture in the subsequent reactions with separation at a later step. In Step 4 the appropriately substituted ketal species is deprotected and subsequently cyclized in the presence of acid as known in the art. In Step 5 the appropriately substituted cyano species is subjected to strong acid to afford a primary amide. In Step 6 the appropriately substituted heterocycle is subjected to a bromide species of the appropriate linker to afford the appropriately protected species. Various 5-5 fused bicyclic systems can be appropriately prepared by slight modifications of this synthetic protocol, another non-limiting example is presented in Steps 5 through 12 with the same conditions for formation of a primary amide and installation of linker. In Step 7 the appropriately substituted aryl species is brominated as known in the art. In Step 8 the appropriately substituted ether species is deprotected with palladium as known in the art to afford an alcohol. In Step 9 the appropriately substituted alcohol is oxidized as known in the art to afford an aldehyde. In Step 10 the appropriately substituted aldehyde is subjected to hydrazine to first form a Schiff base and subsequently cyclize to afford a bicyclic system. In Step 11 the appropriately substituted bicyclic system is iodinated as known in the art. In Step 12 the appropriately substituted iodide is subjected to sodium cyanide to afford the cyano species.

Scheme 6-2

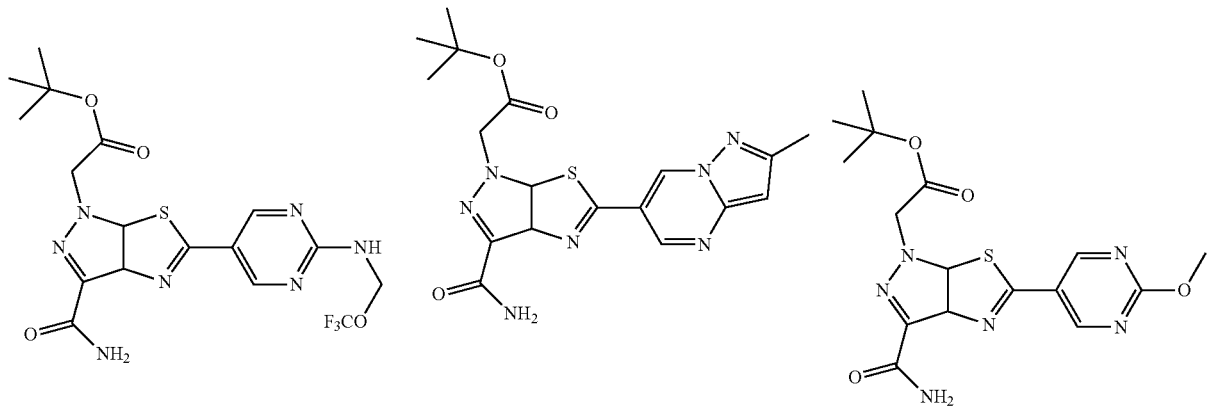

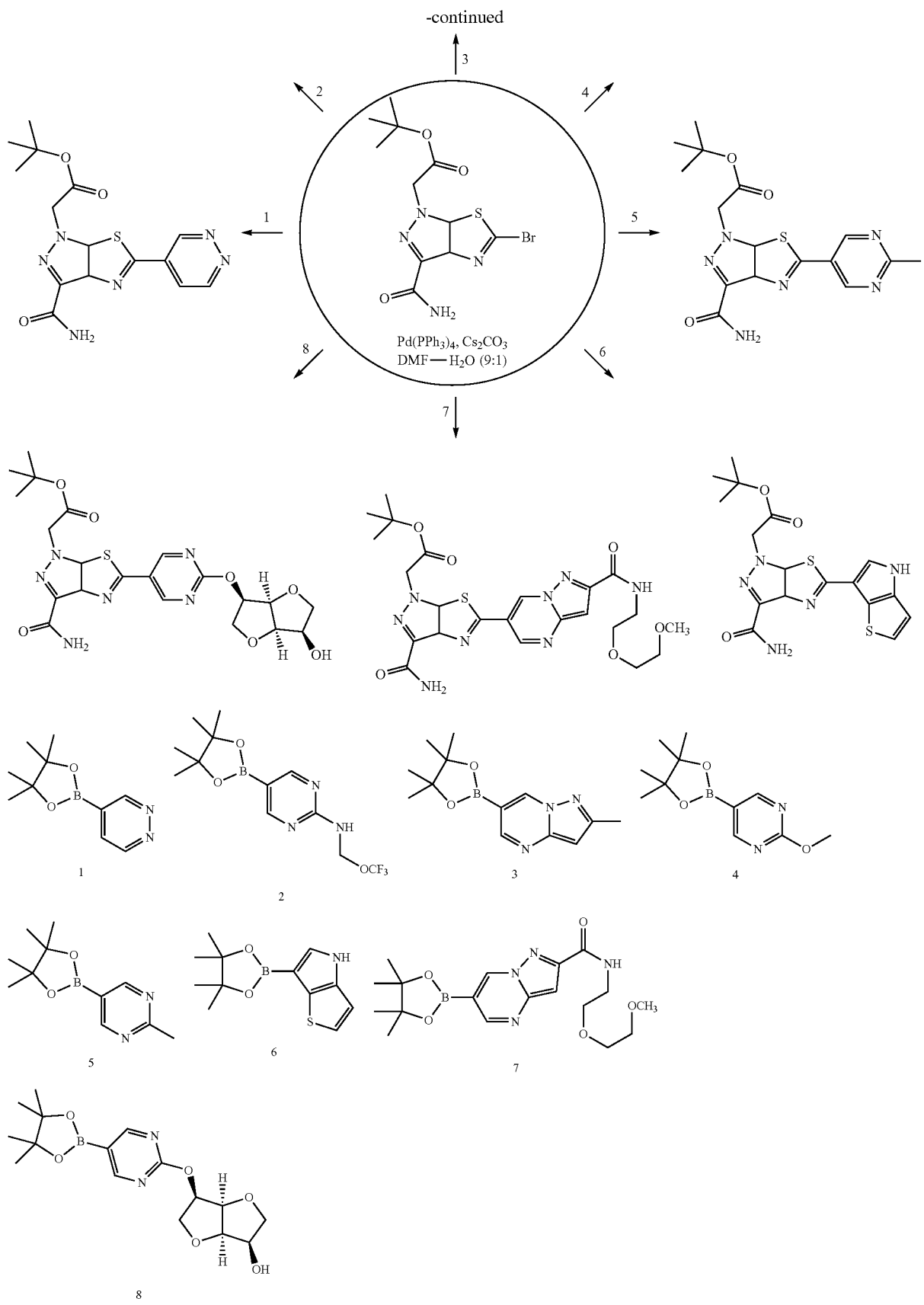

Scheme 6-2: Non-limiting examples of aryl substituents are provided demonstrating the robust nature of the synthetic protocol. Boronic acids 1-8 are subjected to an appropriately substituted aryl bromide to afford a biaryl system.

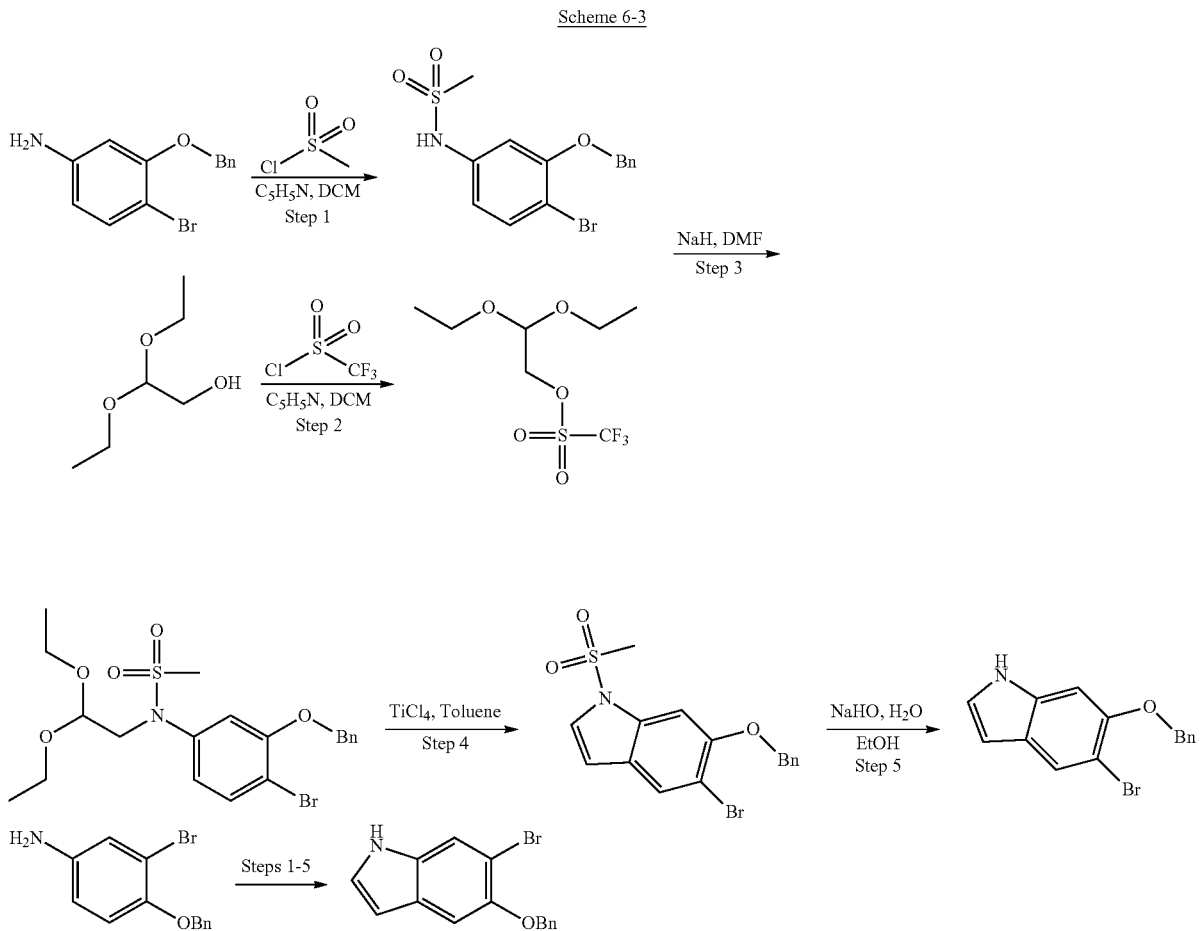

Scheme 6-3: In Step 1 the appropriately substituted and protected aniline is converted as known in the art to a sulfonamide. In Step 2 the appropriately substituted alcohol is converted as known in the art to a triflouro sulfonamide. In Step 3 the previously prepared reagents are subjected to sodium hydride to afford their adduct. In Step 4 the appropriately substituted ketal is subjected to a strong lewis acid to afford deprotection and subsequent cyclization to a biaryl species. In Step 5 the appropriately substituted sulfonamide is deprotected in the presence of base to afford a free amine. In an alternative embodiment this synthetic protocol can be applied to other aniline isomers to afford substituents on alternative positions.

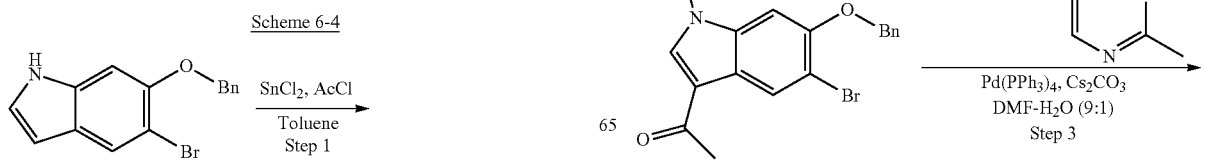

-continued

619
-continued

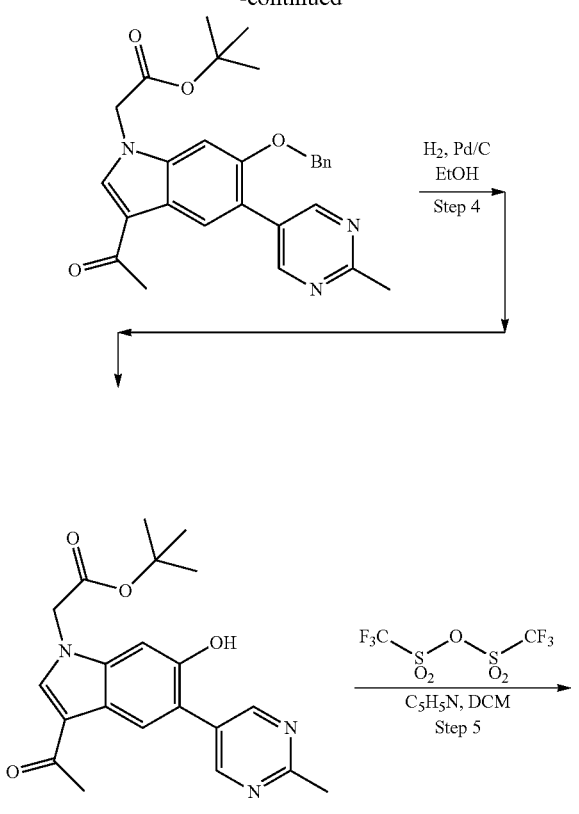

620
-continued

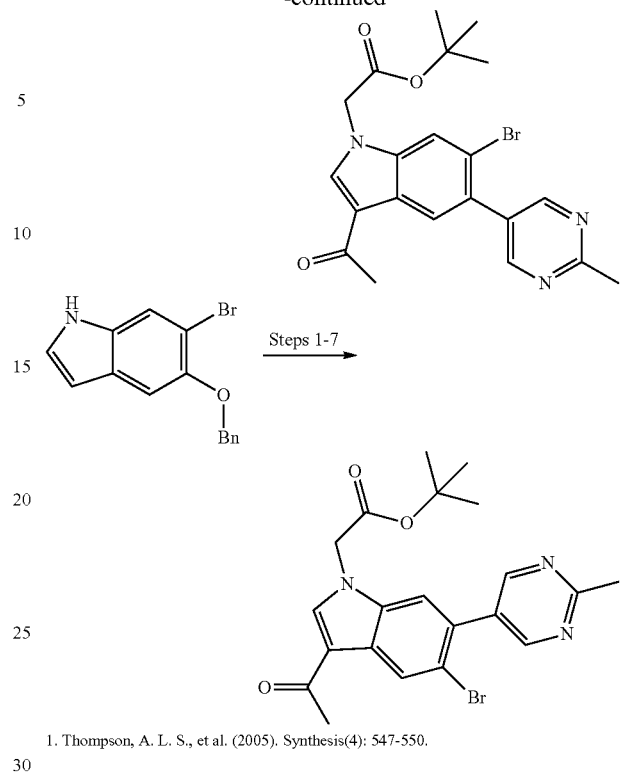

1. Thompson, A. L. S., et al. (2005). Synthesis(4): 547-550.

Scheme 6-4: In Step 1 the appropriately substituted indole is acylated as known in the art. In Step 2 the appropriately substituted heterocycle is subjected to a bromide species of the appropriate linker to afford the appropriately protected species. In Step 3 the appropriately substituted aryl bromide is subjected to a boronic acid to afford an aryl species. In Step 4 the appropriately substituted benzyl alcohol is deprotected in the presence of hydrogen gas and palladium to afford a free alcohol. In Step 5 the appropriately substituted phenol is subjected to a sulfonic anhydride to afford a leaving group. In Step 6 the appropriately substituted aryl species is converted to a boronic acid as known in the art. In Step 7 the appropriately substituted boronic acid is subjected to copper bromide to afford an aryl bromide species. In an alternative embodiment this synthetic protocol can simply be applied to other indole isomers to afford substituents on alternative positions.

Scheme 6-5

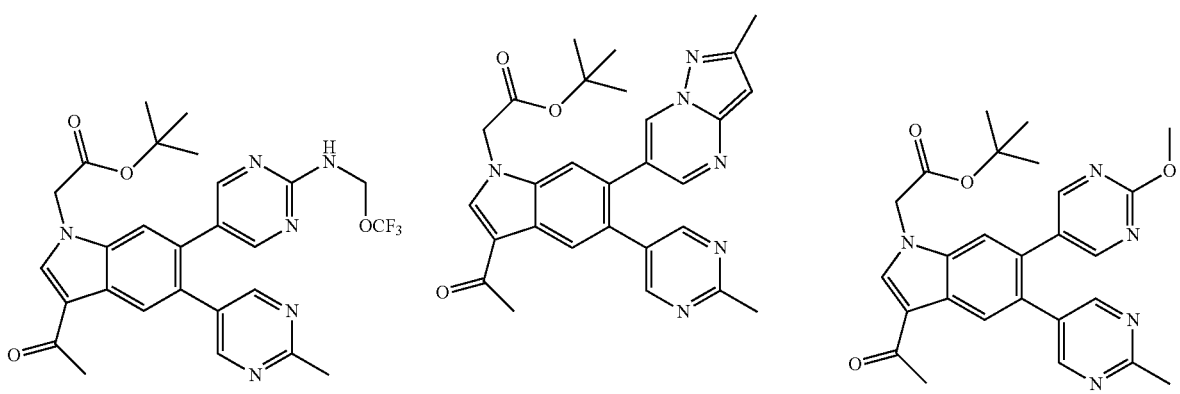

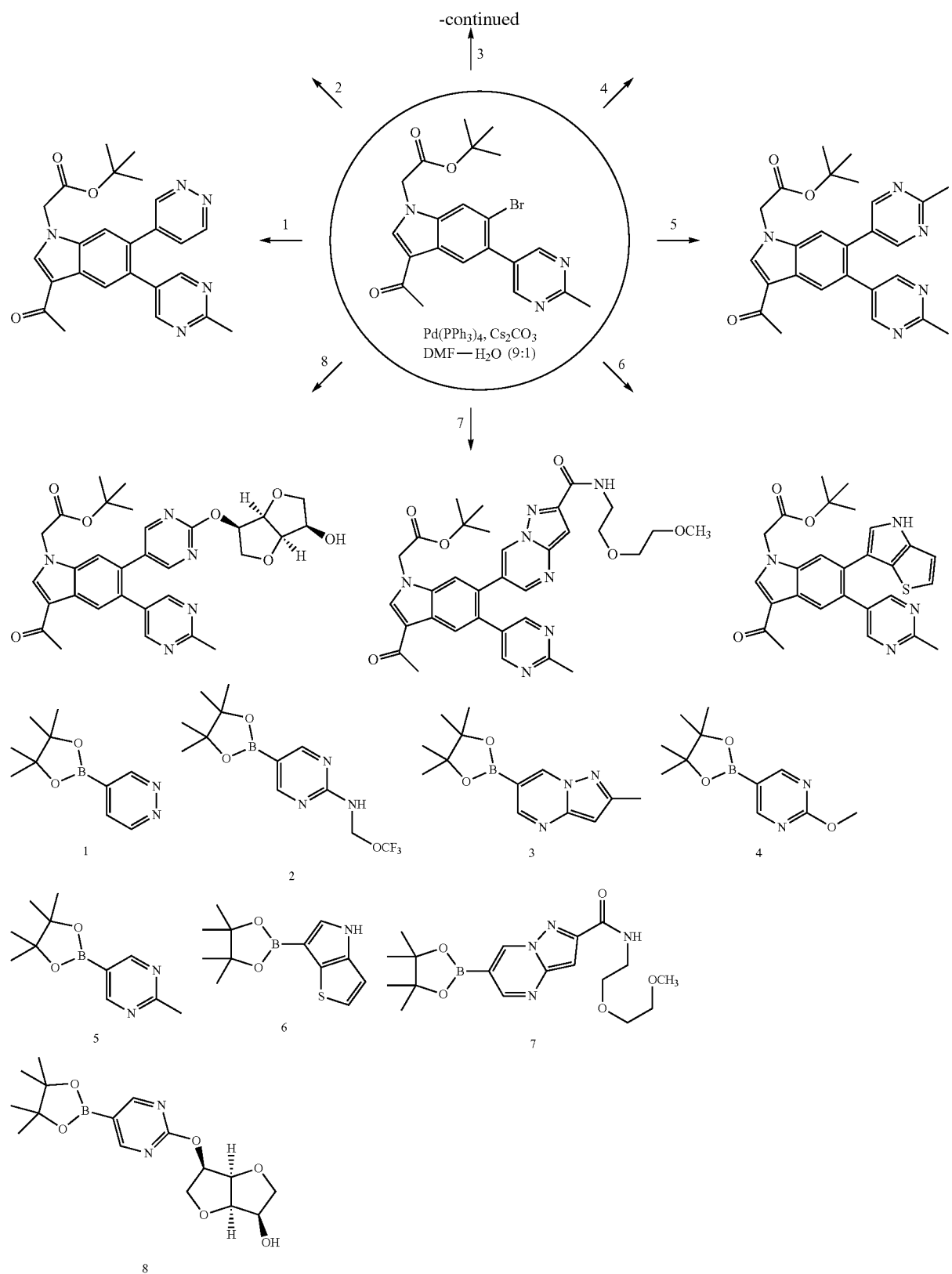
Scheme 6-5: Non-limiting examples of aryl substituents are provided demonstrating the robust nature of the synthetic protocol. Boronic acids 1-8 are subjected to an appropriately substituted aryl bromide to afford an aryl system.

623

Example 7. Synthesis of L3-A Moieties

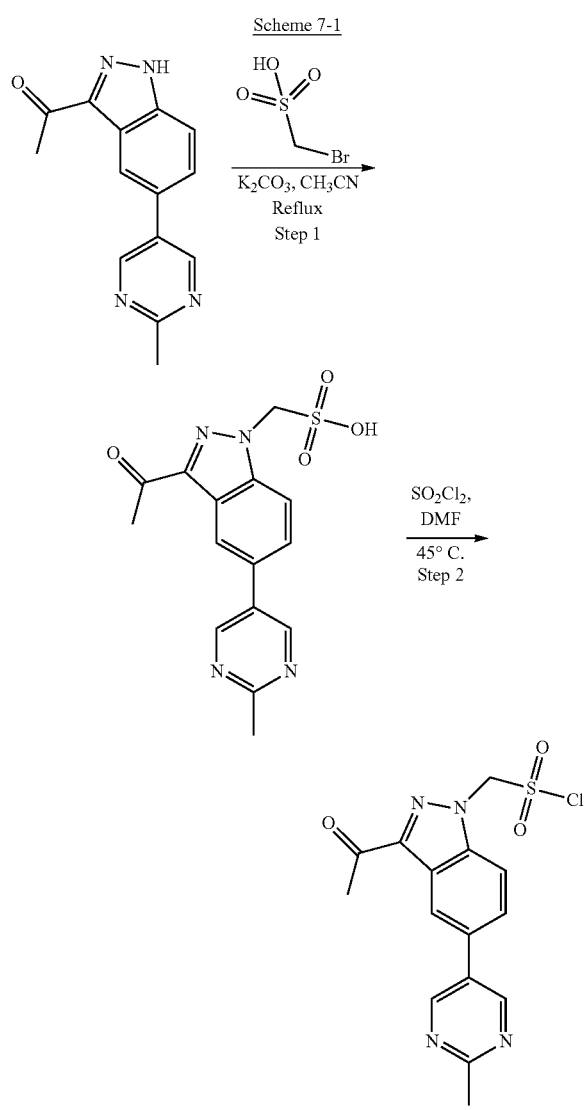 [SMILES: CC(=O)c1n[nH]c2ccc(-c3cnc(C)nc3)cc12 ; O=S(=O)(O)CBr ; CC(=O)c1nn(CS(=O)(=O)O)c2ccc(-c3cnc(C)nc3)cc12 ; CC(=O)c1nn(CS(=O)(=O)Cl)c2ccc(-c3cnc(C)nc3)cc12]

Scheme 7-1: In Step 1 the appropriately substituted aryl compound is subjected to a bromide to afford a sulfonic acid substituted species. In Step 2 the appropriately substituted sulfonic acid species is chlorinated as known in the art.

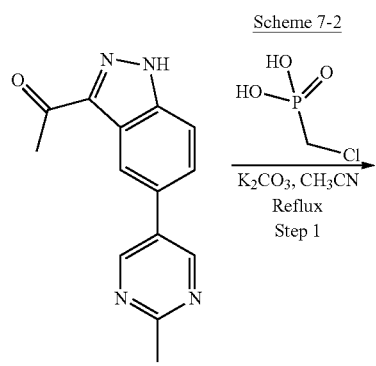

624

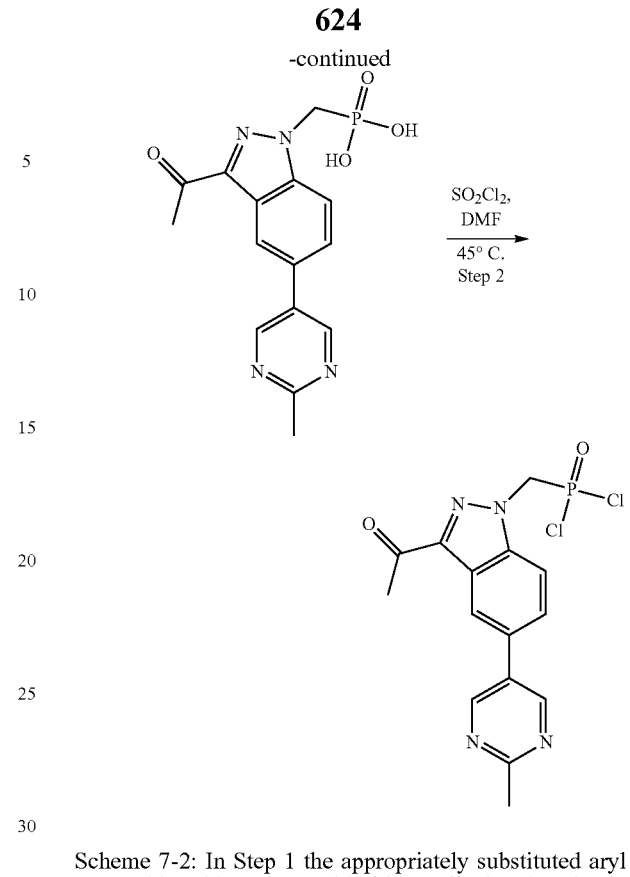

Scheme 7-2: In Step 1 the appropriately substituted aryl compound is subjected to a chloride to afford a phosphonic acid substituted species. In Step 2 the appropriately substituted phosphonic acid species is chlorinated as known in the art.

Example 8. Non-Limiting Synthetic Examples of Prodrug Compounds of the Present Invention Step 1: (((2S,4R)-1-(2-(3-Acetyl-5-(2-methylpyrimidin-5-yl)-1H-indazol-1-yl)acetyl)-4-fluoropyrrolidine-2-carbonyl)amino)methyl)-o-carborane (1)

To a solution of (((2S,4R)-4-fluoropyrrolidine-2-carbonyl)amino)methyl)-o-carborane hydrochloride (8-S1, 1 equiv) in DMF (10 vol) at 0° C. under nitrogen atmosphere was added 2-(3-acetyl-5-(2-methylpyrimidin-5-yl)-1H-indazol-1-yl)acetic acid (8-S2, 1.2 equiv), HATU (1.5 equiv) and DIPEA (3 equiv). The reaction mixture was stirred at room temperature for 16 hours. After completion of the reaction, the reaction mixture was quenched with water. The resulting mixture was extracted with DCM. The organic layer was separated, washed with brine, dried over anhydrous $Na_2SO_4$, filtered and then concentrated. The residue was purified by column chromatography on silica gel using DCM/MeOH to afford compound 1. $^1$H NMR (400 MHz, DMSO-d$_6$) δ: 9.04 (s, 2H), 8.86 (t, J=6.2 Hz, 1H), 8.43 (s, 1H), 7.88-7.81 (m, 2H), 5.86-5.82 (m, 1H), 5.61-5.47 (m, 2H), 4.68-4.67 (m, 1H), 4.38 (t, J=8.6 Hz, 1H), 4.25-4.16 (m, 1H), 3.92-3.77 (m, 4H), 2.69 (s, 3H), 2.65 (s, 3H), 2.30-1.30 (br, 10H).

Step 2: Lithium (2S,4R)-1-(2-(3-Acetyl-5-(2-methylpyrimidin-5-yl)-1H-indazol-1-yl)acetyl)-4-fluoropyrrolidine-2-carbonyl)amino)methyl)-nido-dodecahydroundecaborate (8)

To a solution of compound 1 (1 equiv) in EtOH (10 vol) at room temperature was added lithium hydroxide mono hydrate (0.9 equiv). The reaction mixture was stirred at 80° C. for 16 hours. After completion of the reaction, the reaction mixture was concentrated and the residue was purified by preparative HPLC to afford compound 8. ¹H NMR (400 MHz, D₂O) δ: 8.30 (s, 2H), 7.66-7.60 (m, 1H), 7.16-6.95 (m, 2H), 5.47-4.99 (m, 3H), 4.67-4.65 (m, 2H), 4.62-3.95 (m, 2H), 3.49-3.09 (m, 3H), 2.49 (s, 3H), 2.47 (s, 3H), 2.02-1.30 (br, 10H).

Scheme 2: Synthesis of (1S,3aS,6aR)-2-(2-(3-Acetyl-5-(2-methylpyrimidin-5-yl)-1H-indazol-1-yl) acetyl)-N-(6-bromopyridin-2-yl)octahydrocyclopenta[c]pyrrole-1-carboxamide (2)

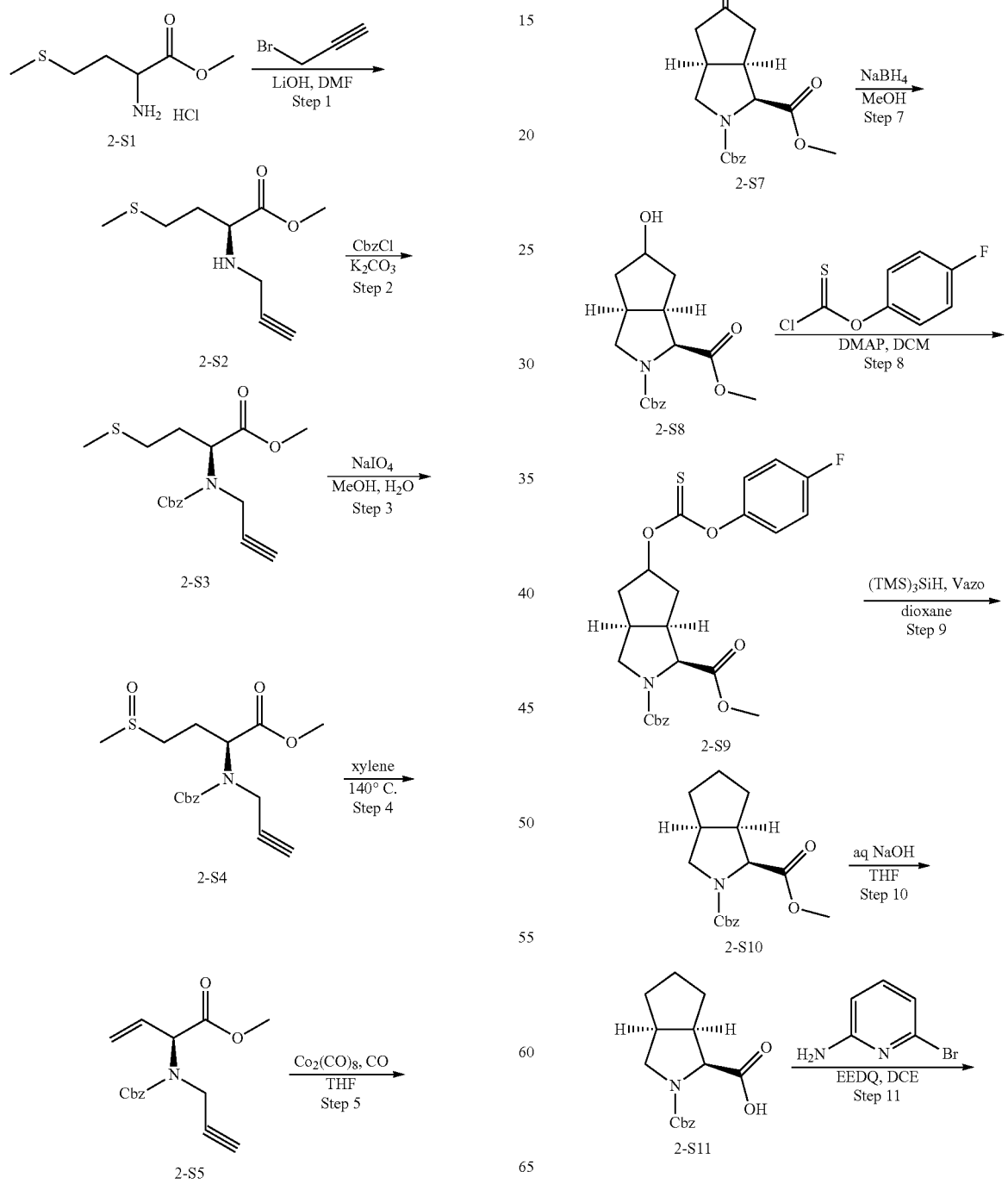

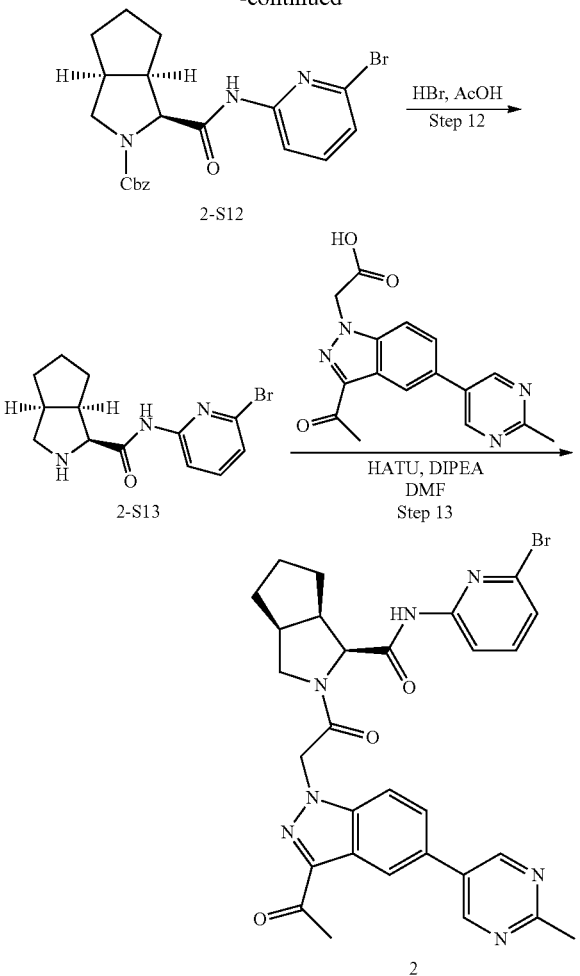

Step 1: (S)-Methyl 4-(methylthio)-2-(prop-2-yn-1-ylamino)butanoate (2-S2)

To a mixture of LiOH·H$_2$O (6.6 g, 157.7 mmol), 4 Å molecular sieves (39 g), and DMF (70 mL) that was stirred at 0° C. for 20 minutes was added L-methionine methyl ester hydrochloride (2-S1, 15.0 g, 75.1 mmol). The mixture was stirred for 45 minutes at 0° C. and then to this mixture was added 3-bromoprop-1-yne (10.6 g, 90.1). The resulting mixture was stirred at room temperature overnight and filtered. The filtrate was partitioned between EtOAc (100 mL) and water (200 mL). The organic layer was washed with brine, dried over Na$_2$SO$_4$, and concentrated to dryness. The remaining residue was purified by column chromatography on silica gel (eluted with PE/EtOAc=20:1 to 15:1) to afford 2-S2 (8.8 g, 58.6% yield) as light oil. LC/MS (ESI) m/z: 202 (M+H)$^+$.

Step 2: (S)-Methyl 2-(((benzyloxy)carbonyl)(prop-2-yn-1-yl)amino)-4-(methylthio)butanoate (2-S3)

To a mixture of (S)-methyl 4-(methylthio)-2-(prop-2-yn-1-ylamino)butanoate (2-S2, 8.8 g, 43.8 mmol), K$_2$CO$_3$ (18.1 g, 131.4 mmol), EtOAc (150 mL), and water (150 mL) was added CbzCl (11.2 g, 65.7 mmol) dropwise at 0° C. The reaction mixture was stirred at 0° C. overnight. The mixture was quenched by the addition of 10% aqueous HCl until pH ~3 at 0° C. The mixture was extracted with EtOAc (2×100 mL) and the combined organic layers were washed with brine, dried over Na$_2$SO$_4$, and concentrated under reduced pressure. The remaining residue was purified by column chromatography on silica gel (eluted with PE/EtOAc=10:1) to afford 2-S3 (12.9 g, 87.9% yield) as light oil. LC/MS (ESI) m/z: 336 (M+H)$^+$.

Step 3: (2S)-Methyl 2-(((benzyloxy)carbonyl)(prop-2-yn-1-yl)amino)-4-(methylsulfinyl)butanoate (2-S4)

To a solution of (S)-methyl 2-(((benzyloxy)carbonyl)(prop-2-yn-1-yl)amino)-4-(methylthio) butanoate (2-S3, 12.9 g, 38.5 mmol) in MeOH (100 mL) and water (100 mL) was added NaIO$_4$ (8.7 g, 40.4 mmol) in portions at 0° C. The mixture was stirred at this temperature for 4 hours. The mixture was extracted with EtOAc (2×50 mL) and the combined layers were washed with brine, dried over Na$_2$SO$_4$, and evaporated under reduced pressure to afford S4 (12 g, 88.8% yield) as a yellow oil. This crude product was carried forward in the next synthetic step without further purification. LC/MS (ESI) m/z: 352 (M+H)$^+$.

Step 4: (S)-Methyl 2-(((benzyloxy)carbonyl)(prop-2-yn-1-yl)amino)but-3-enoate (2-S5)

A solution of (2S)-methyl 2-(((benzyloxy)carbonyl)(prop-2-yn-1-yl)amino)-4-(methylsulfinyl) butanoate (2-S4, 2.0 g, 5.69 mmol) in xylene (8 mL) was stirred at 140° C. for 2 days. The mixture was evaporated under reduced pressure and the remaining residue was purified by column chromatography on silica gel (eluted with PE/EtOAc=25:1 to 20:1) to afford 2-S5 (480 mg, 23.5% yield) as a yellow oil. LC/MS (ESI) m/z: 288 (M+H)$^+$.

Step 5: (1S)-2-Benzyl 1-methyl 5-oxo-1,5,6,6a-tetrahydrocyclopenta[c]pyrrole-1,2 (3H)-dicarboxylate (2-S6)

To a solution of (S)-methyl 2-(((benzyloxy)carbonyl)(prop-2-yn-1-yl)amino)but-3-enoate (2-S5, 480 mg, 1.65 mmol) in THF (8 mL) was added Co$_2$(CO)$_8$ (81.4 mg, 0.24 mmol). The reaction mixture was pressurized with a CO atmosphere (50 psi) and mixed at 100° C. overnight. The mixture was filtered and the filtrate was evaporated under reduced pressure. The remaining residue was purified by column chromatography on silica gel (eluted with PE/EtOAc=4:1 to 2:1) to afford 2-S6 (130 mg, 18.8% yield) as a brown oil. LC/MS (ESI) m/z: 316 (M+H)$^+$.

Step 6: (1S,3aS,6aR)-2-Benzyl 1-methyl 5-oxo-hexahydrocyclopenta[c]pyrrole-1,2(1H)-dicarboxylate (2-S7)

To a solution of (1S)-2-benzyl 1-methyl 5-oxo-1,5,6,6a-tetrahydrocyclopenta[c]pyrrole-1,2 (3H)-dicarboxylate (2-S6, 130 mg, 0.41 mmol) in MeOH (1 mL) and THF (1 mL) was added Pd/C (13 mg) and the reaction mixture was stirred at 0° C. under an atmosphere of hydrogen (balloon) for 30 minutes. The mixture was filtered and the filtrate was evaporated under reduced pressure to afford 2-S7 (120 mg, 92.6% yield) as a yellow oil. This crude product was carried forward in the next synthetic step without further purification. LC/MS (ESI) m/z: 318 (M+H)$^+$.

Step 7: (1S,3aS,6aR)-2-Benzyl 1-methyl 5-hydroxyhexahydrocyclopenta[c]pyrrole-1,2(1H)-dicarboxylate (2-S8)

To a solution of (1S,3aS,6aR)-2-benzyl 1-methyl 5-oxohexahydrocyclopenta[c]pyrrole-1,2(1H)-dicarboxylate (2-S7, 120 mg, 0.38 mmol) in MeOH (3 mL) was added NaBH$_4$ (14.3 mg) at 0° C. under an atmosphere of nitrogen and the reaction mixture was stirred at 0° C. for 30 minutes. The mixture was quenched by the addition of aqueous NH$_4$Cl solution (15 mL) and extracted with EtOAc (2×10 mL). The combined organic layers were washed with brine, dried over Na$_2$SO$_4$, and evaporated under reduced pressure. The remaining residue was purified by column chromatography on silica gel (eluted with PE/EtOAc=3:1 to 2:1) to afford 2-S8 (90 mg, yield 74.4%) as a yellow oil. LC/MS (ESI) m/z: 320 (M+H)$^+$.

Step 8: (1S,3aS,6aR)-2-Benzyl 1-methyl 5-(((4-fluorophenoxy)carbonothioyl)oxy)hexahydrocyclopenta[c]pyrrole-1,2(1H)-dicarboxylate (2-S9)

To a solution of (1S,3aS,6aR)-2-benzyl 1-methyl 5-hydroxyhexahydrocyclopenta [c]pyrrole-1,2(1H)-dicarboxylate (2-S8, 143 mg, 0.45 mmol) in DCM (5 mL) were added 4-fluorophenylthionochloroformate (127.7 mg, 0.67 mmol) and DMAP (164.3 mg, 1.34 mmol). The reaction mixture was stirred at room temperature overnight. The mixture was diluted with DCM (20 mL), washed successively with 0.5 N aqueous HCl (10 mL), water (10 mL), and brine, dried over Na$_2$SO$_4$, filtered, and concentrated to dryness. The remaining residue was purified by column chromatography on silica gel (PE/EtOAc=20:1 to 4:1) to afford 2-S9 (110 mg, yield 51.6%) as a white solid. LC/MS (ESI) m/z: 496 (M+Na)$^+$.

Step 9: (1S,3aS,6aR)-2-Benzyl 1-methyl hexahydrocyclopenta[c]pyrrole-1,2(1H)-dicarboxylate (2-S10)

To a solution of (1S,3aS,6aR)-2-benzyl 1-methyl 5-(((4-fluorophenoxy)carbonothioyl)oxy)hexahydrocyclopenta[c]pyrrole-1,2(1H)-dicarboxylate (2-S9, 110 mg, 0.23 mmol) in 1,4-dioxane (3 mL) were added 1,1'-azobis(cyclohexanecarbonitrile) (Vazo, 18.9 mg, 0.12 mmol) and tris(trimethylsilyl)silane (86.8 mg, 0.35 mmol). The reaction mixture was stirred at 105° C. for 40 minutes. The reaction mixture was concentrated to dryness and the remaining residue was purified by column chromatography on silica gel (eluted with PE/EtOAc=40:1 to 10:1) to afford 2-S10 (68 mg, 97.5% yield) as light oil. LC/MS (ESI) m/z: 304 (M+H)$^+$.

Step 10: (1S,3aS,6aR)-2-((Benzyloxy)carbonyl)octahydrocyclopenta[c]pyrrole-1-carboxylic acid (2-S11)

To a solution of (1S,3aS,6aR)-2-benzyl 1-methyl hexahydrocyclopenta[c]pyrrole-1,2(1H)-dicarboxylate (2-S10, 68 mg, 0.22 mmol) in THF (3 mL) was added a 1 M aqueous NaOH solution (0.44 mL, 0.44 mmol) at 0° C. and the reaction mixture was stirred at room temperature for 2 hours. The mixture was diluted with water (15 mL) and concentrated under reduced pressure. The remaining residue was washed with Et$_2$O (2×10 mL). The aqueous layer was acidified with 2 N aqueous HCl until pH ~3 and extracted with EtOAc (2×15 mL). The combined organic layers were dried over Na$_2$SO$_4$ and concentrated under reduced pressure to afford 2-S11 (40 mg, 61.7% yield) as light oil. This crude product was carried forward without further purification. LC/MS (ESI) m/z: 290 (M+H)$^+$.

Step 11: (1S,3aS,6aR)-Benzyl 1-((6-bromopyridin-2-yl)carbamoyl)hexahydrocyclopenta[c] pyrrole-2(1H)-carboxylate (2-S12)

To a mixture of (1S,3aS,6aR)-2-((benzyloxy)carbonyl)octahydrocyclopenta[c]pyrrole-1-carboxylic acid (2-S11, 40 mg, 0.14 mmol), 6-bromopyridin-2-amine (25 mg, 0.14 mmol), and EEDQ (69.2 mg, 0.28 mmol) in DCE (4 mL) was added DIPEA (54.2 mg, 0.42 mmol) and the reaction mixture was stirred at 90° C. under an atmosphere of nitrogen overnight. The mixture was concentrated to dryness and the remaining residue was purified by column chromatography on silica gel (eluted with PE/EtOAc=20:1 to 10:1) to afford 2-S12 (30 mg, 48.4% yield) as a light oil. LC/MS (ESI) m/z: 444 (M+H)$^+$.

Step 12: (1S,3aS,6aR)—N-(6-Bromopyridin-2-yl)octahydrocyclopenta[c]pyrrole-1-carboxamide (2-S13)

To a solution of (1S,3aS,6aR)-benzyl 1-((6-bromopyridin-2-yl)carbamoyl)hexahydrocyclopenta[c] pyrrole-2(1H)-carboxylate (2-S12, 30 mg, 0.07 mmol) in AcOH (1.5 mL) was added a 30% HBr/AcOH solution (0.3 mL) at 0° C. and the reaction mixture was stirred at room temperature for 1 hour. The mixture was poured into ice-cooled aqueous NaHCO$_3$ solution and extracted with EtOAc (2×15 mL). The combined organic layers were dried over Na$_2$SO$_4$ and concentrated under reduced pressure to afford 2-S13 (25 mg, crude) as a brown oil. This crude product was used directly in the next reaction without further purification. LC/MS (ESI) m/z: 310 (M+H)$^+$.

Step 13: (1S,3aS,6aR)-2-(2-(3-Acetyl-5-(2-methylpyrimidin-5-yl)-1H-indazol-1-yl)acetyl)-N-(6-bromopyridin-2-yl)octahydrocyclopenta[c]pyrrole-1-carboxamide (2)

To a mixture of (1S,3aS,6aR)—N-(6-bromopyridin-2-yl)octahydrocyclopenta[c]pyrrole-1-carboxamide (2-S13, 25 mg, 0.08 mmol), 2-(3-acetyl-5-(2-methylpyrimidin-5-yl)-1H-indazol-1-yl) acetic acid (25 mg, 0.08 mmol), and HATU (45.6 mg, 0.12 mmol) in DMF (2 mL) was added DIPEA (31 mg, 0.24 mmol). The reaction mixture was stirred at room temperature overnight. The mixture was partitioned with EtOAc and water. The organic layer was washed with brine, dried over Na$_2$SO$_4$, and concentrated under reduced pressure. The remaining residue was purified by preparative HPLC to afford 2 (5 mg, 16.6% yield) as a white solid. $^1$H NMR (400 MHz, DMSO-d$_6$) δ 10.97 (s, 1H), 9.04 (s, 2H), 8.43 (s, 1H), 8.05 (d, J=8.2 Hz, 1H), 7.87-7.85 (m, 2H), 7.72 (t, J=8.0 Hz, 1H), 7.32 (d, J=7.7 Hz, 1H), 5.74 (d, J=17.3 Hz, 1H), 5.62 (d, J=17.2 Hz, 1H), 4.42 (d, J=2.8 Hz, 1H), 4.09-4.03 (m, 1H), 3.67-3.63 (m, 1H), 2.87-2.84 (m, 1H), 2.69 (s, 3H), 2.65 (s, 3H), 1.98-1.58 (m, 7H). LC/MS (ESI) m/z: 602 (M+H)+.

Scheme 3: Synthesis of (S)-2-(2-(3-Acetyl-5-(2-methylpyrimidin-5-yl)-1H-indazol-1-yl)acetyl)-N-(6-bromo-3-methylpyridin-2-yl)-2-azabicyclo[2.2.2]octane-3-carboxamide (3)

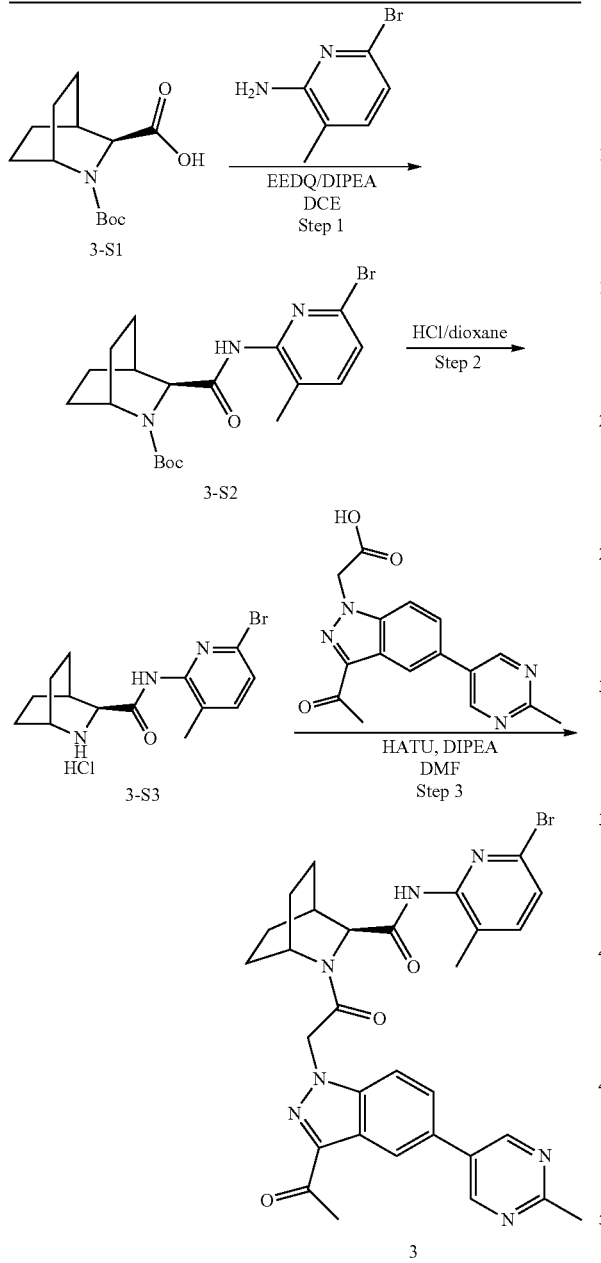

The above scheme and following detailed description depicts one non-limiting method for synthesizing compounds via the following steps: 1) the formation of an amide bond between the B-ring and the C-ring by utilizing a coupling reagent such as EEDQ ot HATU; 2) the removal of the Boc-group using an acid; and, 3) the formation of an amide bond between the C-ring (already linked to the B-ring) and A-ring utilizing HATU. The skilled artisan will recognize that the C- and B-ring synthetic intermediate can be replaced with other synthetic intermediates to afford additional compounds of the present invention. The skilled artisan will also recognize that the A-ring synthetic intermediate can be replaced with other synthetic intermediates to afford additional compounds of the present invention.

Step 1: (S)-tert-Butyl 3-(6-bromo-3-methylpyridin-2-ylcarbamoyl)-2-azabicyclo[2.2.2]octane-2-carboxylate (3-S2)

To a mixture of 3-S1 (230 mg, 0.902 mmol), 6-bromo-3-methylpyridin-2-amine (169 mg, 0.902 mmol), and EEDQ (446 mg, 1.80 mmol) in DCE (10 mL) was added DIPEA (0.6 mL, 3.61 mmol). The reaction mixture was stirred at 90° C. overnight. The mixture was then concentrated under reduced pressure and the remaining residue was purified by column chromatography on silica gel (eluted with PE/EtOAc=20:1 to 10:1) to afford 3-S2 (100 mg, 26.2% yield) as a yellow solid. LC/MS (ESI) m/z: 424 (M+H)$^+$.

Step 2: (S)—N-(6-Bromo-3-methylpyridin-2-yl)-2-azabicyclo[2.2.2]octane-3-carboxamide (3-S3)

To a solution of 3-S2 (100 mg, 0.236 mmol) in dioxane (2 mL) was added HCl/dioxane solution (1 mL, 2 M) at 0° C. and the reaction mixture was stirred at room temperature for 1 hour. The mixture was concentrated to dryness to afford 3-S3 (105 mg, 100% yield) as a brown solid, which was used in the next synthetic step without further purification. LC/MS (ESI) m/z: 324 (M+H)$^+$.

Step 3: (S)-2-(2-(3-Acetyl-5-(2-methylpyrimidin-5-yl)-1H-indazol-1-yl)acetyl)-N-(6-bromo-3-methylpyridin-2-yl)-2-azabicyclo[2.2.2]octane-3-carboxamide (3)

To a mixture of 2-(3-acetyl-5-(2-methylpyrimidin-5-yl)-1H-indazol-1-yl)acetic acid (24 mg, 0.078 mmol) in DMF were added DIPEA (0.03 mL, 0.195 mmol), HATU (37.0 mg, 0.097 mmol), and 3-S3 (21.0 mg, 0.065 mmol). The reaction mixture was stirred at room temperature overnight. The mixture was diluted with EtOAc, washed with water and brine, dried over Na$_2$SO$_4$, and concentrated under reduced pressure. The remaining residue was purified by preparative HPLC to afford 3 (2.5 mg, 6.27% yield) as a white solid. $^1$H NMR (400 MHz, CD$_3$OD) δ 9.01 (s, 2H), 8.54 (s, 1H), 7.79 (s, 2H), 7.54 (d, J=7.9 Hz, 1H), 7.36 (d, J=7.9 Hz, 1H), 5.63 (q, J=16.8 Hz, 2H), 4.50 (s, 1H), 4.22 (s, 1H), 2.75 (s, 3H), 2.71-2.66 (m, 3H), 2.41 (s, 1H), 2.30 (d, J=15.1 Hz, 1H), 2.09 (m, 3H), 1.88 (m, 5H), 1.69 (d, J=6.7 Hz, 1H), 1.34 (m, 1H). LC/MS (ESI) m/z: 616 (M+H)$^+$.

(1R,3S,5S)-2-(2-(3-Acetyl-5-(2-methylpyrimidin-5-yl)-1H-indazol-1-yl)acetyl)-N-(6-bromo-3-(methoxymethyl)pyridin-2-yl)-5-(methoxymethyl)-2-azabicyclo[3.1.0]hexane-3-carboxamide (49)

$^1$H NMR (400 MHz, CD$_3$OD) δ 9.01 (d, J=6.9 Hz, 2H), 8.54 (s, 1H), 8.04 (d, J=8.2 Hz, 1H), 7.80 (d, J=9.8 Hz, 2H), 7.27 (d, J=8.1 Hz, 1H), 5.81 (d, J=17.2 Hz, 1H), 5.66 (d, J=17.1 Hz, 1H), 4.76 (s, 1H), 4.46 (s, 2H), 3.79 (s, 1H), 3.74-3.69 (m, 1H), 3.63 (d, J=10.2 Hz, 1H), 3.51 (d, J=10.3 Hz, 1H), 3.43 (s, 3H), 3.40 (s, 3H), 2.75 (s, 3H), 2.70 (s, 3H), 2.59 (dd, J=16.6, 6.7 Hz, 2H), 2.19 (t, J=7.6 Hz, 1H), 1.16-1.11 (m, 1H), 0.90 (t, J=6.8 Hz, 1H). LC/MS (ESI) m/z: 662 (M+H)$^+$.

(1R,3S,5R)-2-(2-(3-Acetyl-7-methyl-5-(2-methylpyrimidin-5-yl)-1H-indazol-1-yl)acetyl)-N-(2-(3-chloro-2-fluorophenyl)propan-2-yl)-5-methyl-2-azabicyclo[3.1.0]hexane-3-carboxamide $^1$H NMR (400 MHz, Chloroform-d) δ 0.87 (dd, J=2.3, 5.4 Hz, 1H), 1.14 (t, J=5.5 Hz, 1H), 1.32 (s, 3H), 1.62 (s, 3H), 1.68 (s, 3H), 2.07 (dd, J=8.6, 13.3 Hz, 1H), 2.55 (dd, J=2.7, 13.3 Hz, 1H), 2.72 (s, 3H), 2.76 (s, 3H), 2.80 (s, 3H), 3.05 (dd, J=2.3, 5.5 Hz, 1H), 4.58 (dd, J=2.7, 8.7 Hz, 1H), 5.68 (s, 2H), 7.01 (t, J=8.0 Hz, 1H), 7.10 (s, 1H), 7.23-7.29 (m, 2H), 7.35 (s, 1H), 8.47 (d, J=1.6 Hz, 1H), 8.90 (s, 2H). $^{19}$F δ−115.9.

(S)-2-((1R,3S,5R)-2-(2-(3-Acetyl-7-methyl-5-(2-methylpyrimidin-5-yl)-1H-indazol-1-yl)acetyl)-5-methyl-2-azabicyclo[3.1.0]hexane-3-carboxamido)-4-methylpentanoic Acid $^1$H-NMR (400 MHz, CD$_3$OD) δ 8.99 (s, 2H), 8.41 (s, 1H), 7.53 (s, 1H), 5.90-5.94 (d, J=17.6 Hz, 1H), 5.73-5.78 (d, J=17.6 Hz, 1H), 4.43-4.35 (m, 2H), 3.46-3.44 (m, 1H), 2.72 (s, 6H), 2.68 (s, 3H), 2.48 (m, 1H), 2.17 (dd, J=13.2, 4.4 Hz, 1H), 1.65 (m, 1H), 1.62-1.53 (m, 2H), 1.35 (s, 3H), 1.09 (m, 1H), 0.90 (m, 1H), 0.85 (s, 3H), 0.84 (s, 3H). LC/MS (ESI) m/z: 561 (M+H)$^+$.

(S)-2-((1R,3R,5R)-2-(2-(3-Acetyl-7-methyl-5-(2-methylpyrimidin-5-yl)-1H-indazol-1-yl)acetyl)-5-methyl-2-azabicyclo[3.1.0]hexane-3-carboxamido)-3-phenylpropanoic Acid $^1$H-NMR (400 MHz, DMSO-d$_6$) δ 9.03 (s, 2H), 8.32 (t, J=4.8 Hz, 1H), 8.04 (d, J=8.0 Hz, 1H), 7.60 (d, J=8.0 Hz, 1H), 7.35-7.04 (m, 5H), 5.95-5.99 (d, J=18 Hz, 1H), 5.61-5.66 (d, J=17.6 Hz, 1H), 4.28-4.41 (m, 2H), 3.43-3.44 (m, 1H), 3.01 (dd, J=14, 5.2 Hz, 1H), 2.89 (dd, J=14.4, 6 Hz, 1H), 2.68 (s, 3H), 2.65 (s, 3H), 2.64 (s, 3H), 2.34 (dd, J=13.2, 9.6 Hz, 2H), 1.91 (m, 1H), 1.17 (s, 3H), 0.97-1.00 (m, 1H), 0.82-0.84 (m, 1H). LC/MS (ESI) m/z: 595 (M+H)$^+$.

(R)-2-((1R,3S,5R)-2-(2-(3-Acetyl-7-methyl-5-(2-methylpyrimidin-5-yl)-1H-indazol-1-yl)acetyl)-5-methyl-2-azabicyclo[3.1.0]hexane-3-carboxamido)-4-methylpentanoic Acid $^1$H-NMR (400 MHz, CD$_3$OD) δ 8.98 (s, 2H), 8.39 (s, 1H), 7.52 (s, 1H), 5.90 (d, J=17.6 Hz, 1H), 5.78 (d, J=18.0 Hz, 1H), 4.46-4.37 (m, 2H), 3.46-3.48 (m, 1H), 2.74 (s, 3H), 2.73 (s, 3H), 2.67 (s, 3H), 2.48-2.54 (m, 1H), 2.09-2.14 (m, 1H), 1.61-1.64 (m, 3H), 1.36 (s, 3H), 1.12-1.07 (m, 1H), 1.00 (m, 1H), 0.92-0.87 (m, 6H). LC/MS (ESI) m/z: 561 (M+H)$^+$.

(2R)-2-{[(1R,3S,5R)-2-{2-[3-Acetyl-7-methyl-5-(2-methylpyrimidin-5-yl)indazol-1-yl]acetyl}-5-methyl-2-azabicyclo[3.1.0]hexan-3-yl]formamido}-3-phenylpropanoic Acid $^1$H-NMR (400 MHz, CD$_3$OD) δ 8.99 (s, 2H), 8.41 (s, 1H), 7.52 (s, 1H), 7.30-7.16 (m, 5H), 5.88 (d, J=17.7 Hz, 1H), 5.75 (d, J=17.8 Hz, 1H), 4.72-4.68 (m, 1H), 4.37-4.32 (m, 1H), 3.38-3.36 (m, 1H), 3.25-3.20 (m, 1H), 2.97-2.91 (m, 1H), 2.81-2.65 (m, 9H), 2.34-2.28 (m, 1H), 1.75-1.70 (m, 1H), 1.22 (s, 3H), 1.07-1.02 (m, 1H), 0.87-0.83 (m, 1H). LC/MS (ESI) m/z: 595 (M+H)$^+$.

(1R,3S,5R)-2-(2-(3-Acetyl-7-methyl-5-(2-methylpyrimidin-5-yl)-1H-indazol-1-yl)acetyl)-N-(3-chloro-2-fluorobenzyl)-5-(((3-methyl-1,2,4-oxadiazol-5-yl)methyl)-2-azabicyclo[3.1.0]hexane-3-carboxamide $^1$H-NMR (400 MHz, CD$_3$OD) δ 8.99 (s, 2H), 8.41 (s, 1H), 7.52 (s, 1H), 7.29 (dd, J=11.0, 4.1 Hz, 1H), 7.21 (t, J=6.9 Hz, 1H), 6.97 (t, J=7.8 Hz, 1H), 5.93 (d, J=17.7 Hz, 1H), 5.79 (d, J=17.7 Hz, 1H), 4.57-4.35 (m, 3H), 3.79 (dd, J=5.7, 2.7 Hz, 1H), 3.12 (d, J=16.0 Hz, 1H), 2.75 (s, 3H), 2.69 (d, J=6.1 Hz, 3H), 2.65 (d, J=11.2 Hz, 3H), 2.62-2.55 (m, 1H), 2.37 (s, 3H), 2.29 (dd, J=13.8, 4.6 Hz, 1H), 1.36 (m, 1H), 1.13 (m, 1H). LC/MS (ESI) m/z: 671 [M+H]$^+$.

(1R,3S,5R)-2-(2-(3-Acetyl-7-methyl-5-(2-methylpyrimidin-5-yl)-1H-indazol-1-yl)acetyl)-N-(3-chloro-2-fluorobenzyl)-5-((5-methyl-1,3,4-oxadiazol-2-yl)methyl)-2-azabicyclo[3.1.0]hexane-3-carboxamide $^1$H-NMR (400 MHz, DMSO-d$_6$) δ 9.03 (s, 2H), 8.42-8.45 (t, 1H), 8.32 (s, 1H), 7.62 (s, 1H), 7.41-7.45 (t, 1H), 7.17-7.20 (t, 1H), 7.04-7.08 (t, 1H), 5.97-6.01 (d, J=17.6 Hz, 1H), 5.67-5.71 (d, J=17.6 Hz, 1H), 4.25-4.33 (m, 3H), 3.73-3.76 (m, 1H), 3.15-3.16 (d, J=16 Hz, 1H), 3.02-3.06 (d, J=16 Hz, 1H), 2.68 (s, 3H), 2.65 (s, 3H), 2.63 (s, 3H), 2.48 (s, 3H), 2.46-2.47 (m, 1H), 2.06-2.10 (m, 1H), 1.24-1.25 (m, 1H), 1.07-1.09 (m, 1H). LC/MS (ESI) m/z: 671 (M+H)$^+$.

(1R,2S,5S)-3-{2-[3-Acetyl-7-methyl-5-(2-methylpyrimidin-5-yl)indazol-1-yl]acetyl}-N-[(3-chloro-2-fluorophenyl)methyl]-3-azabicyclo[3.1.0]hexane-2-carboxamide $^1$H-NMR (400 MHz, CD$_3$OD) δ 8.99 (s, 2H), 8.41 (d, J=2.0 Hz, 1H), 7.53-7.50 (m, 1H), 7.31-7.24 (m, 2H), 6.94 (td, J=1.2, 1.2 Hz, 1H), 5.65 (s, 2H), 4.57 (d, J=6.0 Hz, 1H), 4.47 (d, J=15.2 Hz, 1H), 4.37 (d, J=15.6 Hz, 1H), 4.03 (dd, J=5.6, 5.6 Hz, 1H), 3.90 (d, J=10.0 Hz, 1H), 2.74 (s, 3H), 2.71 (s, 3H), 2.66 (s, 3H), 2.04-2.00 (m, 1H), 1.95-1.90 (m, 1H), 0.89 (q, J=4.6 Hz, 1H), 0.83-0.79 (m, 1H). LC/MS (ESI) m/z: 575 (M+H)$^+$.

(2S,4R)—N-(5'-Acetyl-2'-chloro-2-fluoro-[1,1'-biphenyl]-3-yl)-1-(2-(3-acetyl-5-(2-methylpyrimidin-5-yl)-1H-indazol-1-yl)acetyl)-4-fluoropyrrolidine-2-carboxamide $^1$H NMR (400 MHz, DMSO-d$_6$) δ 10.04 (s, 1H), 9.03 (s, 2H), 8.43 (s, 1H), 8.02-8.00 (m, 2H), 7.98 (s, 1H), 7.97-7.96 (m, 2H), 7.76-7.73 (m, 1H), 7.28-7.24 (m, 1H), 7.14-7.11 (m, 1H), 5.86 (d, J=17.2 Hz, 1H), 5.66 (d, J=17.2 Hz, 1H), 4.79-4.75 (m, 1H), 4.30-4.21 (m, 1H), 4.08-3.97 (m, 1H), 2.69 (s, 3H), 2.64 (s, 3H), 2.61-2.60 (m, 2H), 2.58 (s, 3H), 2.26-2.22 (m, 1H).

Scheme 4: Synthesis of (3S,5R)-2-(2-(3-Acetyl-5-(2-methylpyrimidin-5-yl)-1H-indazol-1-yl)acetyl)-N-(6-bromo-3-methylpyridin-2-yl)-5-piperidin-1-ylmethyl)-2-azabicyclo[3.1.0]hexane-3-carboxamide (4)

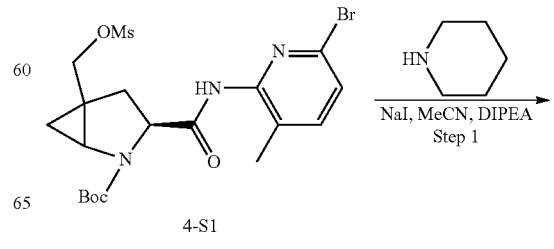

4-S1

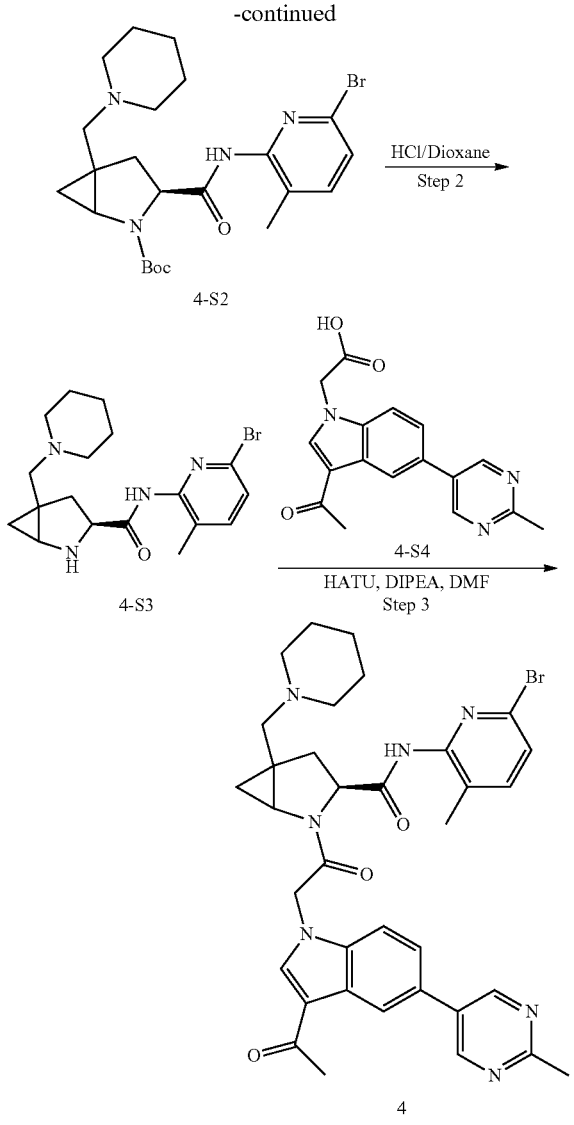

with DCM/MeOH=40:1 to 30:1) to afford the title compound (8 mg, 33.3% yield) as a yellow solid. LC/MS (ESI) m/z: 493 (M+H)$^+$.

Step 2: (3S)—N-(6-Bromo-3-methylpyridin-2-yl)-5-(piperidin-1-ylmethyl)-2-azabicyclo[3.1.0]hexane-3-carboxamide (4-S3)

To a solution of 4-S2 (8 mg, 0.016 mmol) in dioxane (1 mL) was added HCl/dioxane (1 mL) at 0° C. The reaction mixture was stirred at room temperature for 2 hours. The mixture was concentrated to dryness to afford the title compound (10 mg, 100% yield) as a brown solid. The crude material was carried forward in the next synthetic step without further purification. LC/MS (ESI) m/z: 393 (M+H)$^+$.

Step 3: (3S,5R)-2-(2-(3-Acetyl-5-(2-methylpyrimidin-5-yl)-1H-indazol-1-yl)acetyl)-N-(6-bromo-3-methylpyridin-2-yl)-5-(piperidin-1-ylmethyl)-2-azabicyclo[3.1.0]hexane-3-carboxamide (4)

To a solution of 4-S3 (10 mg, 0.025 mmol) and 4-S4 (7.75 mg, 0.025 mmol) in DMF (2 mL) was added HATU (17.1 mg, 0.045 mmol) and DIPEA (0.018 mL, 0.10 mmol) at 0° C. The reaction mixture was stirred at room temperature overnight. The mixture was diluted with EtOAc and washed with 10% aqueous LiCl solution and brine. The organic layer was dried over anhydrous Na$_2$SO$_4$ and concentrated to dryness. The remaining residue was purified by preparative HPLC to afford 4 (2.1 mg, 12.3% yield) as a white solid. $^1$H NMR (400 MHz, CD$_3$OD) δ 9.02 (s, 2H), 8.56 (s, 1H), 7.81 (s, 2H), 7.57 (d, J=7.9 Hz, 1H), 7.41 (d, J=7.9 Hz, 1H), 5.82 (d, J=17.2 Hz, 1H), 5.67 (d, J=17.2 Hz, 1H), 5.35-5.33 (m, 1H), 4.68 (t, J=7.2 Hz, 1H), 3.04 (d, J=7.3 Hz, 2H), 2.75 (s, 3H), 2.70 (d, J=2.0 Hz, 4H), 2.66 (d, J=8.4 Hz, 2H), 2.20 (t, J=7.2 Hz, 2H), 2.13 (s, 3H), 2.04 (s, 2H), 1.83 (s, 4H), 1.60 (s, 4H). LC/MS (ESI) m/z: 685 (M+H)$^+$.

(3S)-5-(6-Azaspiro[2.5]octan-6-ylmethyl)-2-(2-(3-acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide (5)

$^1$H NMR (400 MHz, CD$_3$OD) δ 9.01 (s, 2H), 8.57 (s, 1H), 7.80 (s, 2H), 7.59 (d, J=8.2 Hz, 1H), 7.42 (d, J=8.0 Hz, 1H), 5.82 (d, J=17.1 Hz, 1H), 5.67 (d, J=16.9 Hz, 1H), 2.75 (s, 3H), 2.70 (s, 3H), 2.67 (s, 1H), 2.13 (s, 3H), 1.48 (s, 2H), 1.33 (s, 2H), 1.29 (s, 6H), 0.90 (s, 3H), 0.51 (s, 3H). LC/MS (ESI) m/z: 711 (M+H)$^+$.

(3S)-2-(2-(3-Acetyl-5-(2-methylpyrimidin-5-yl)-1H-indazol-1-yl)acetyl)-5-(azetidin-1-ylmethyl)-N-(6-bromo-3-methylpyridin-2-yl)-2-azabicyclo[3.1.0]hexane-3-carboxamide (6)

$^1$H NMR (400 MHz, CD$_3$OD) δ 9.01 (s, 2H), 8.56 (s, 1H), 7.80 (s, 2H), 7.59 (d, J=7.9 Hz, 1H), 7.43 (d, J=8.0 Hz, 1H), 5.81 (d, J=17.2 Hz, 1H), 5.66 (d, J=17.1 Hz, 1H), 5.35 (d, J=5.0 Hz, 1H), 4.72-4.65 (m, 1H), 4.30 (s, 2H), 3.53 (d, J=13.3 Hz, 1H), 3.46 (t, J=6.8 Hz, 2H), 2.75 (s, 3H), 2.70 (s, 3H), 2.66-2.59 (m, 1H), 2.54-2.50 (m, 1H), 2.20 (dd, J=15.8, 8.3 Hz, 2H), 2.12 (s, 3H), 2.04 (s, 2H), 1.60 (s, 2H), 1.41 (d, J=6.2 Hz, 1H), 1.10-1.08 (m, 1H). LC/MS (ESI) m/z: 657 (M+H)$^+$.

The above scheme and following detailed description depicts one non-limiting method for synthesizing compounds with nucleophilic R$^{201}$ groups on the C-ring. The skilled artisan will recognize that piperidine can be replaced with other nucleophilic reagents to afford additional compounds of the present invention. Non-limiting examples of groups the skilled artisan can use instead of piperidine include azetidine, 6-azaspiro[2.5]octane, and 2-azaspiro[3.3]heptane.

Step 1: (3S)-tert-Butyl 3-((6-bromo-3-methylpyridin-2-yl)carbamoyl)-5-(piperidin-1-ylmethyl)-2-azabicyclo[3.1.0]hexane-2-carboxylate (4-S2)

To a mixture of 4-S1 (25 mg, 0.05 mmol) in MeCN (2 mL) were added DIPEA (0.035 mL, 0.2 mmol), piperidine (4 mg, 0.055 mmol), and NaI at 0° C. The reaction mixture was stirred at room temperature for 4 hours. The mixture was concentrated, diluted with DCM, and washed with water and brine. The organic layer was dried over anhydrous Na$_2$SO$_4$, filtered, and concentrated. The remaining residue was purified by column chromatography on silica gel (eluted

(3S)-5-(3-Azabicyclo[3.1.1]heptan-3-ylmethyl)-2-(2-(3-acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide (13)

$^1$H NMR (400 MHz, CD$_3$OD) δ 9.01 (s, 2H), 8.55 (s, 1H), 7.84-7.76 (m, 2H), 7.59 (d, J=8.2 Hz, 1H), 7.42 (d, J=8.0 Hz, 1H), 5.88 (d, J=17.2 Hz, 1H), 5.64 (d, J=17.2 Hz, 1H), 4.64 (dd, J=9.0, 4.2 Hz, 1H), 4.22 (s, 3H), 4.01 (d, J=3.2 Hz, 1H), 3.52-3.37 (m, 2H), 2.75 (s, 3H), 2.69 (s, 3H), 2.61 (d, J=9.2 Hz, 1H), 2.54 (d, J=3.8 Hz, 1H), 2.34 (s, 4H), 2.12 (s, 3H), 1.90 (t, J=7.6 Hz, 2H), 1.40 (s, 1H), 1.10-1.08 (m, 1H). LC/MS (ESI) m/z: 697 (M+H)$^+$.

(3S)-2-(2-(3-Acetyl-5-(2-methylpyrimidin-5-yl)-1H-indazol-1-yl)acetyl)-N-(6-bromo-3-methylpyridin-2-yl)-5-((4-methylpiperazin-1-yl)methyl)-2-azabicyclo[3.1.0]hexane-3-carboxamide (24)

$^1$H NMR (400 MHz, CD$_3$OD) δ 9.01 (s, 2H), 8.56 (s, 1H), 7.80 (d, J=1.2 Hz, 2H), 7.56 (d, J=7.8 Hz, 1H), 7.40 (d, J=7.9 Hz, 1H), 5.80 (d, J=17.2 Hz, 1H), 5.66 (d, J=17.2 Hz, 1H), 4.65-4.61 (m, 4.7 Hz, 1H), 3.66-3.64 (m, 1H), 3.28 (s, 3H), 2.99 (s, 4H), 2.75 (s, 4H), 2.72 (s, 1H), 2.69 (s, 4H), 2.65 (s, 3H), 2.54-2.44 (m, 2H), 2.12 (s, 3H), 1.20-1.02 (m, 2H). LC/MS (ESI) m/z: 700 (M+H)$^+$.

(1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-((4-methylpiperazin-1-yl)methyl)-2-azabicyclo[3.1.0]hexane-3-carboxamide (69)

$^1$H NMR (400 MHz, CD$_3$OD) δ 8.99 (s, 2H), 8.40 (s, 1H), 7.50-7.53 (m, 2H), 7.35 (d, J=8.0 Hz, 1H), 5.87 (s, 2H), 4.85-5.03 (m, 1H), 3.63-3.66 (m, 1H), 3.29-3.33 (m, 5H), 2.67-2.92 (m, 17H), 2.32-2.48 (m, 2H), 2.04 (s, 3H), 1.72-1.74 (m, 1H), 1.03-1.06 (m, 1H). LC/MS (ESI) m/z: 714/716 (M+H)$^+$.

Scheme 5: Sythesis of (3S)-2-(2-(3-Acetyl-5-(2-methylpyrimidin-5-yl)-1H-indazol-1-yl)acetyl)-5-(azetidin-1-ylmethyl)-N-(6-bromo-3-methylpyridin-2-yl)-2-azabicyclo[3.1.0]hexane-3-carboxamide (9)

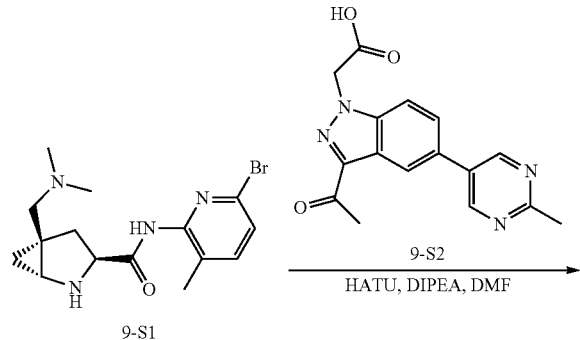

9-S1

HATU, DIPEA, DMF

9-S2

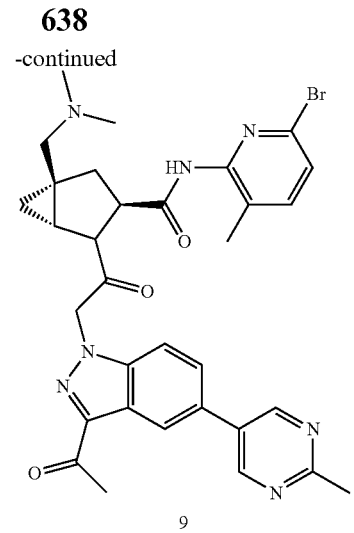

9

The above scheme and following detailed description depicts one non-limiting method for synthesizing compounds via the formation of an amide bond between the C-ring (already linked to the B-ring) and A-ring utilizing HATU or a different peptide coupling reagent, such as TBTU. The skilled artisan will recognize that the C- and B-ring synthetic intermediate can be replaced with other synthetic intermediates to afford additional compounds of the present invention. The skilled artisan will also recognize that the A-ring synthetic intermediate can be replaced with other synthetic intermediates to afford additional compounds of the present invention.

To a solution of 9-S1 (45 mg, 0.086 mmol) and 9-S2 (26.7 mg, 0.086 mmol) in DMF (2 mL) was added HATU (58.9 mg, 0.155 mmol) and DIPEA (0.06 mL, 0.344 mmol) at 0° C. The reaction mixture was stirred at room temperature overnight. The mixture was diluted with EtOAc and washed with 10% aqueous LiCl solution and brine. The organic layer was dried over anhydrous Na$_2$SO$_4$ and concentrated to dryness. The remaining residue was purified by preparative HPLC to afford 9 (23 mg, 41.5% yield) as a white solid. $^1$H NMR (400 MHz, DMSO-d$_6$) δ 10.35 (s, 1H), 9.51 (s, 1H), 9.05 (s, 2H), 8.45 (s, 1H), 7.87 (s, 2H), 7.63 (d, J=8.1 Hz, 1H), 7.45 (d, J=7.9 Hz, 1H), 5.94 (d, J=17.3 Hz, 1H), 5.62 (d, J=17.3 Hz, 1H), 4.47 (dd, J=9.0, 5.0 Hz, 1H), 2.82 (s, 2H), 2.69 (s, 3H), 2.66 (s, 3H), 2.66-2.64 (m, 1H), 2.51 (d, J=1.7 Hz, 6H), 2.42-2.31 (m, 2H), 2.04 (s, 3H), 2.00 (d, J=7.7 Hz, 1H), 1.34 (d, J=6.1 Hz, 1H). LC/MS (ESI) m/z: 645 (M+H)$^+$.

(2S,4R)-1-(2-(3-Acetyl-5-(2-methylpyrimidin-5-yl)-1H-indazol-1-yl)acetyl)-N-(cuban-1-ylmethyl)-4-fluoropyrrolidine-2-carboxamide (16)

$^1$H NMR (400 MHz, DMSO-d$_6$) δ: 9.05 (s, 2H), 8.44 (s, 1H), 8.02-8.01 (m, 1H), 7.89-7.82 (m, 2H), 5.82-5.78 (m, 1H), 5.61-5.43 (m, 2H), 4.39 (t, J=8.3 Hz, 1H), 4.22-3.80 (m, 4H), 3.73-3.72 (m, 3H), 3.51-3.36 (m, 2H), 3.17-3.10 (m, 3H), 2.69 (s, 3H), 2.64 (s, 3H), 2.11-1.98 (m, 1H).

(1R,3S,5R)-2-(2-(3-Acetyl-7-(fluoromethyl)-5-(2-methylpyrimidin-5-yl)-1H-indazol-1-yl)acetyl)-N-(6-bromopyridin-2-yl)-5-methyl-2-azabicyclo[3.1.0]hexane-3-carboxamide (30)

$^1$H NMR (400 MHz CD$_3$OD) δ 9.05 (s, 2H), 8.68 (t, J=1.9 Hz, 1H), 8.09 (d, J=8.2 Hz, 1H), 7.87 (dd, J=3.1, 1.7 Hz,

1H), 7.63 (t, J=8.0 Hz, 1H), 7.27 (d, J=7.7 Hz, 1H), 5.60-6.05 (m, 4H), 4.52 (dd, J=9.0, 5.8 Hz, 1H), 3.56 (dd, J=5.5, 2.4 Hz, 1H), 2.77 (s, 3H), 2.73 (s, 3H), 2.61 (dd, J=13.4, 9.3 Hz, 1H), 2.18-2.24 (m, 1H), 1.41 (s, 3H), 1.10-1.16 (m, 1H), 1.01-1.04 (m, 1H). LC/MS (ESI) m/z: 620/622 (M+H)$^+$.

(1R,3S,5R)-2-(2-(3-Acetyl-7-methyl-5-(2-methylpyrimidin-5-yl)-1H-indazol-1-yl)acetyl)-N-(2-fluoro-3-(trifluoromethoxy)phenyl)-5-methyl-2-azabicyclo[3.1.0]hexane-3-carboxamide (33)

$^1$H NMR (400 MHz, CD$_3$OD) δ: 9.01 (s, 2H), 8.42 (s, 1H), 7.92-7.89 (m, 1H), 7.54 (s, 1H), 7.21-7.19 (m, 2H), 5.98 (d, J=17.6 Hz, 1H), 5.82 (d, J=17.6 Hz, 1H), 4.60 (m, 1H), 3.57-3.55 (m, 1H), 2.76 (s, 3H), 2.74 (s, 3H), 2.71 (s, 3H), 2.63-2.57 (m, 1H), 2.28-2.23 (m, 1H), 1.42 (s, 3H), 1.15-1.13 (m, 1H), 1.00-0.99 (m, 1H).

(1R,3S,5R)-2-(2-(3-Acetyl-7-methyl-5-(2-methylpyrimidin-5-yl)-1H-indazol-1-yl)acetyl)-N—((S)-3-fluoro-4-methylpent-3-en-2-yl)-5-methyl-2-azabicyclo[3.1.0]hexane-3-carboxamide (34)

$^1$H NMR (400 MHz, CD$_3$OD) δ: 9.00 (s, 2H), 8.42 (s, 1H), 7.54 (s, 1H), 5.92 (d, J=17.6 Hz, 1H), 5.78 (d, J=17.6 Hz, 1H), 4.36-4.32 (m, 1H), 3.48-3.46 (m, 1H), 2.76 (s, 3H), 2.74 (s, 3H), 2.69 (s, 3H), 2.50-2.47 (m, 1H), 2.12-2.00 (m, 1H), 1.67 (s, 3H), 1.57 (s, 3H), 1.40 (s, 3H), 1.24 (s, 3H), 1.22-1.21 (m, 1H), 1.10-1.09 (m, 1H), 0.92-0.90 (m, 1H).

(1R,3S,5R)-2-(2-(3-Acetyl-7-methyl-5-(2-methylpyrimidin-5-yl)-1H-indazol-1-yl)acetyl)-5-methyl-N-(1-(2,2,2-trifluoroethyl)-1H-pyrazol-3-yl)-2-azabicyclo[3.1.0]hexane-3-carboxamide (35)

$^1$H NMR (400 MHz, CD$_3$OD) δ: 9.01 (s, 2H), 8.42 (s, 1H), 7.61 (s, 1H), 7.55 (s, 1H), 6.67 (s, 1H), 5.98 (d, J=18.0 Hz, 1H), 5.83 (d, J=18.0 Hz, 1H), 4.81-4.76 (m, 1H), 4.51-4.47 (m, 1H), 3.56-3.54 (m, 1H), 2.77 (s, 3H), 2.76 (s, 3H), 2.70 (s, 3H), 2.62-2.56 (m, 1H), 2.22-2.17 (m, 1H), 1.40 (s, 3H), 1.22-1.20 (m, 1H), 1.19-1.10 (m, 1H), 0.97-0.99 (m, 1H).

(1R,3S,5R)-2-(2-(3-Acetyl-7-methyl-5-(2-methylpyrimidin-5-yl)-1H-indazol-1-yl)acetyl)-5-methyl-N-(6-(trifluoromethyl)pyridin-2-yl)-2-azabicyclo[3.1.0]hexane-3-carboxamide (36)

$^1$H NMR (400 MHz, CD$_3$OD) δ: 9.01 (s, 2H), 8.42-8.36 (m, 2H), 7.99-7.95 (m, 1H), 7.54 (s, 1H), 7.48 (d, J=7.6 Hz, 1H), 6.01 (d, J=18.0 Hz, 1H), 5.81 (d, J=20.0 Hz, 1H), 4.54-4.52 (m, 1H), 3.59-3.58 (m, 1H), 2.78 (s, 3H), 2.75 (s, 3H), 2.68 (s, 3H), 2.61-2.59 (m, 1H), 2.23-2.19 (m, 1H), 1.40 (s, 3H), 1.14-1.11 (m, 1H), 1.00-0.98 (m, 1H).

(1R,3S,5R)-2-(2-(3-Acetyl-7-methyl-5-(2-methylpyrimidin-5-yl)-1H-indazol-1-yl)acetyl)-5-methyl-N-(6-(trifluoromethoxy)pyridin-2-yl)-2-azabicyclo[3.1.0]hexane-3-carboxamide (37)

$^1$H NMR (400 MHz, CD$_3$OD) δ: 9.05-9.02 (m, 2H), 8.43 (s, 1H), 8.11-8.09 (m, 1H), 7.91-7.87 (m, 1H), 7.54 (s, 1H), 6.83 (d, J=7.6 Hz, 1H), 6.00 (d, J=18.0 Hz, 1H), 5.80 (d, J=17.6 Hz, 1H), 4.55-4.54 (m, 1H), 3.74-3.58 (m, 1H), 3.57-3.56 (m, 1H), 2.77 (s, 3H), 2.75 (s, 3H), 2.74-2.73 (m, 2H), 2.61-2.57 (m, 1H), 2.21-2.16 (m, 1H), 1.40 (s, 3H), 1.14-1.11 (m, 1H), 0.98-0.97 (m, 1H).

(1R,3S,5R)-2-(2-(3-Acetyl-7-methyl-5-(2-methylpyrimidin-5-yl)-1H-indazol-1-yl)acetyl)-N-(2'-chloro-2-fluoro-[1,1'-biphenyl]-3-yl)-5-methyl-2-azabicyclo[3.1.0]hexane-3-carboxamide (38)

$^1$H NMR (400 MHz, DMSO-d$_6$) δ: 9.80 (s, 1H), 9.01 (s, 2H), 8.31 (s, 1H), 7.95-7.94 (m, 1H), 7.61-7.37 (m, 5H), 7.13-7.21 (m, 1H), 7.07-7.06 (m, 1H), 6.08 (d, J=18.0 Hz, 1H), 5.67 (d, J=18.0 Hz, 1H), 4.55-4.52 (m, 1H), 3.63-3.61 (m, 1H), 2.69 (s, 3H), 2.68 (s, 3H), 2.63 (s, 3H), 2.11-2.09 (m, 1H), 1.32 (s, 3H), 1.26-1.24 (m, 1H), 0.94-0.92 (m, 1H), 0.86-0.83 (m, 1H).

(1R,3S,5R)-2-(2-(3-Acetyl-5-(2-methylpyrimidin-5-yl)-1H-indazol-1-yl)acetyl)-N-(2'-chloro-2-fluoro-[1,1'-biphenyl]-3-yl)-5-methyl-2-azabicyclo[3.1.0]hexane-3-carboxamide (39)

$^1$H NMR (400 MHz, DMSO-d$_6$) δ: 9.77 (s, 1H), 9.03 (s, 2H), 8.43 (s, 1H), 7.91-7.80 (m, 3H), 7.57 (d, J=8.0 Hz, 1H), 7.45-7.37 (m, 3H), 7.25-7.21 (m, 1H), 7.08-7.06 (m, 1H), 5.95 (d, J=17.2 Hz, 1H), 5.58 (d, J=17.2 Hz, 1H), 4.58-4.56 (m, 1H), 3.62-3.60 (m, 1H), 2.69 (s, 3H), 2.64 (s, 3H), 2.47-2.46 (m, 1H), 2.11-2.09 (m, 1H), 1.32 (s, 3H), 1.01-1.00 (m, 1H), 0.86-0.83 (m, 1H).

1-(2-((1R,3S,5R)-3-((6-Bromo-3-methylpyridin-2-yl)carbamoyl)-5-methyl-2-azabicyclo[3.1.0]hexan-2-yl)-2-oxoethyl)-5-(2-methylpyrimidin-5-yl)-1H-indazole-3-carboxamide (55)

$^1$H NMR (400 MHz, DMSO-d$_6$) δ: 10.28 (s, 1H), 9.03 (s, 2H), 8.44 (s, 1H), 7.83-7.76 (m, 3H), 7.62 (d, J=8.0 Hz, 1H), 7.49-7.44 (m, 2H), 5.82 (d, J=17.6 Hz, 1H), 5.49 (d, J=17.2 Hz, 1H), 4.41-4.37 (m, 1H), 3.58-3.56 (m, 1H), 2.68 (s, 3H), 2.57-2.54 (m, 1H), 2.04 (s, 3H), 2.03-2.00 (m, 1H), 1.32 (s, 3H), 1.00-0.96 (m, 2H).

1-(2-((1R,2S,5S)-2-((6-Bromo-3-methylpyridin-2-yl)carbamoyl)-3-azabicyclo[3.1.0]hexan-3-yl)-2-oxoethyl)-5-(2-methylpyrimidin-5-yl)-1H-indazole-3-carboxamide (56)

$^1$H NMR (400 MHz, DMSO-d$_6$) δ: 10.31 (s, 1H), 9.03 (s, 2H), 8.42 (s, 1H), 7.79-7.74 (m, 2H), 7.69 (s, 1H), 7.59 (d, J=8.0 Hz, 1H), 7.47 (s, 1H), 7.41 (d, J=7.6 Hz, 1H), 5.58-5.47 (m, 2H), 4.58-4.57 (m, 1H), 4.01-4.00 (m, 1H), 3.88-3.81 (m, 1H), 2.77 (s, 3H), 2.03 (s, 3H), 2.02-2.01 (m, 1H), 1.89-1.82 (m, 1H), 0.92-0.69 (m, 2H).

(1R,3S,5R)-2-(2-(3-Acetyl-7-methyl-5-(2-methylpyrimidin-5-yl)-1H-indazol-1-yl)acetyl)-N—((R)-1-((R)-2,2-dichlorocyclopropyl)ethyl)-5-methyl-2-azabicyclo[3.1.0]hexane-3-carboxamide (52)

$^1$H NMR (400 MHz, DMSO-d$_6$) δ: 9.03 (s, 2H), 8.32 (s, 1H), 7.98 (d, J=8.0 Hz, 1H), 7.63 (s, 1H), 5.97 (d, J=18.0 Hz, 1H), 5.70 (d, J=18.0 Hz, 1H), 4.25-4.22 (m, 1H), 3.52-3.51 (m, 2H), 2.68 (s, 3H), 2.65 (s, 6H), 2.45-2.42 (m, 1H), 1.96-1.92 (m, 1H), 1.74-1.72 (m, 1H), 1.45-1.43 (m, 1H), 1.41-1.31 (m, 2H), 1.27-1.24 (m, 2H), 1.15-1.13 (m, 2H), 1.09-1.08 (m, 1H), 1.04-0.88 (m, 1H).

(1R,3S,5R)-2-(2-(3-Acetyl-7-methyl-5-(2-methylpyrimidin-5-yl)-1H-indazol-1-yl)acetyl)-N-(6-bromopyrazin-2-yl)-5-methyl-2-azabicyclo[3.1.0]hexane-3-carboxamide (53)

¹H NMR (400 MHz, DMSO-d₆) δ: 11.18 (s, 1H), 9.26 (s, 1H), 9.01 (s, 2H), 8.53 (s, 1H), 8.30 (s, 1H), 7.61 (s, 1H), 6.07 (d, J=18.0 Hz, 1H), 5.66 (d, J=18.0 Hz, 1H), 4.44 (t, J=14.0 Hz, 1H), 3.65-3.59 (m, 1H), 2.69 (s, 3H), 2.67 (s, 3H), 2.63 (s, 3H), 2.62-2.61 (m, 1H), 2.05-2.00 (m, 1H), 1.35 (s, 3H), 0.99-0.92 (m, 2H).

(1R,3S,5R)-2-(2-(3-Acetyl-7-methyl-5-(2-methylpyrimidin-5-yl)-1H-indazol-1-yl)acetyl)-N-(6-bromo-5-methylpyrazin-2-yl)-5-methyl-2-azabicyclo[3.1.0]hexane-3-carboxamide (54)

¹H NMR (400 MHz, DMSO-d₆) δ: 11.06 (s, 1H), 9.13 (s, 1H), 9.03 (s, 2H), 8.31 (s, 1H), 7.62 (s, 1H), 6.07 (d, J=18.0 Hz, 1H), 5.67 (d, J=18.0 Hz, 1H), 4.45-4.41 (m, 1H), 3.65-3.64 (m, 1H), 2.73 (s, 3H), 2.69 (s, 3H), 2.68 (s, 3H), 2.61 (s, 3H), 2.60-2.59 (m, 1H), 2.04-2.00 (m, 1H), 1.31 (s, 3H), 0.99-0.98 (m, 2H).

1-(2-((1R,3S,5R)-3-((6-Bromo-3-methylpyridin-2-yl)carbamoyl)-5-methyl-2-azabicyclo[3.1.0]hexan-2-yl)-2-oxoethyl)-7-methyl-5-(2-methylpyrimidin-5-yl)-1H-indazole-3-carboxamide (57)

¹H NMR (400 MHz, DMSO-d₆) δ: 10.33 (s, 1H), 9.02 (s, 2H), 8.32 (s, 1H), 7.73 (s, 1H), 7.62 (d, J=8.0 Hz, 1H), 7.56 (s, 1H), 7.46-7.42 (m, 2H), 5.94 (d, J=18.0 Hz, 1H), 5.59 (d, J=17.6 Hz, 1H), 4.41-4.37 (m, 1H), 3.60-3.58 (m, 1H), 2.68 (s, 3H), 2.66 (s, 3H), 2.66-2.53 (m, 1H), 2.01 (s, 3H), 2.00-1.99 (m, 1H), 1.32 (s, 3H), 1.03-1.00 (m, 1H), 0.89-0.88 (m, 1H).

1-(2-((1R,3S,5R)-3-((6-Bromopyridin-2-yl)carbamoyl)-5-methyl-2-azabicyclo[3.1.0]hexan-2-yl)-2-oxoethyl)-7-methyl-5-(2-methylpyrimidin-5-yl)-1H-indazole-3-carboxamide (58)

¹H NMR (400 MHz, DMSO-d₆) δ: 10.82 (s, 1H), 9.00 (s, 2H), 8.30 (s, 1H), 8.03 (d, J=8.0 Hz, 1H), 7.74-7.70 (m, 2H), 7.56 (s, 1H), 7.46 (s, 1H), 7.32 (d, J=7.6 Hz, 1H), 5.97 (d, J=18.0 Hz, 1H), 5.57 (d, J=18.0 Hz, 1H), 4.40 (t, J=14.8 Hz, 1H), 3.62 (t, J=8.8 Hz, 1H), 2.67 (s, 6H), 2.00-1.96 (m, 1H), 1.30 (s, 3H), 1.29-1.27 (m, 1H), 1.00-0.84 (m, 2H).

(2S,4R)-1-(2-(3-Acetyl-7-methyl-5-(2-methylpyrimidin-5-yl)-1H-indazol-1-yl)acetyl)-N-(6-bromo-3-methylpyridin-2-yl)-4-fluoro-4-(fluoromethyl)pyrrolidine-2-carboxamide (66)

¹H NMR (400 MHz, CD₃OD) δ 9.02 (s, 2H), 8.44 (s, 1H), 7.56 (d, J=7.8 Hz, 2H), 7.39 (d, J=8.0 Hz, 1H), 5.84 (d, J=17.6 Hz, 1H), 5.74 (d, J=17.5 Hz, 1H), 4.74-4.70 (m, 2H), 4.35-4.31 (m, 1H), 4.17-4.15 (m, 1H), 4.10-4.07 (m, 1H), 2.77 (s, 6H), 2.70 (s, 3H), 2.50-2.44 (m, 1H), 2.42-2.36 (m, 1H), 2.12 (s, 3H). LC/MS (ESI) m/z: 640 (M+H)⁺.

(1R,3S,5R)-2-(2-(3-Acetyl-7-methyl-5-(2-methylpyrimidin-5-yl)-1H-indazol-1-yl)acetyl)-N-(3,3-dimethylbutyl)-5-methyl-2-azabicyclo[3.1.0]hexane-3-carboxamide (80)

¹H NMR (400 MHz, DMSO-d₆) δ: 9.03 (s, 2H), 8.32 (s, 1H), 7.75-7.73 (m, 1H), 7.63 (s, 1H), 5.96 (d, J=17.2 Hz, 1H), 5.67 (d, J=17.2 Hz, 1H), 4.14-4.12 (m, 1H), 3.86-3.75 (m, 4H), 3.50-3.49 (m, 1H), 3.06-3.00 (m, 2H), 2.66 (s, 3H), 2.61 (s, 3H), 2.49-2.33 (m, 1H), 1.90-1.89 (m, 1H), 1.30-1.28 (s, 5H), 1.00-0.99 (m, 1H), 0.98 (s, 9H).

(1R,3S,5R)-2-(2-(3-Acetyl-7-methyl-5-(2-methylpyrimidin-5-yl)-1H-indazol-1-yl)acetyl)-5-methyl-N-(2-(trifluoromethoxy)ethyl)-2-azabicyclo[3.1.0]hexane-3-carboxamide (81)

¹H NMR (400 MHz, DMSO-d₆) δ: 9.03 (s, 2H), 8.31 (s, 1H), 8.15-8.12 (m, 1H), 7.62 (s, 1H), 5.96 (d, J=18 Hz, 1H), 5.67 (d, J=18 Hz, 1H), 4.22-4.02 (m, 4H), 3.51-3.49 (m, 1H), 3.36-3.24 (m, 2H), 2.68 (s, 3H), 2.64 (s, 3H), 2.49-2.33 (m, 3H), 1.89-1.85 (m, 1H), 1.26 (s, 3H), 1.00-0.99 (m, 1H), 0.88-0.87 (m, 1H).

(1R,3S,5R)-2-(2-(3-Acetyl-7-methyl-5-(2-methylpyrimidin-5-yl)-1H-indazol-1-yl)acetyl)-N-(6-methoxypyridin-2-yl)-5-methyl-2-azabicyclo[3.1.0]hexane-3-carboxamide (82)

¹H NMR (400 MHz, DMSO-d₆) δ: 10.20 (s, 1H), 9.01 (s, 2H), 8.30 (s, 1H), 7.67-7.61 (m, 3H), 6.49 (d, J=7.6 Hz, 1H), 6.08 (d, J=16 Hz, 1H), 5.65 (d, J=17.6 Hz, 1H), 4.51-4.48 (m, 1H), 3.78 (s, 3H), 3.63-3.62 (m, 1H), 2.67 (s, 3H), 2.61 (s, 3H), 2.55 (s, 3H), 2.02-1.97 (m, 1H), 1.31 (s, 3H), 0.88-0.86 (m, 3H).

(2S,4R)-1-(2-(3-Acetyl-5-(2-methylpyrimidin-5-yl)-1H-indazol-1-yl)acetyl)-4-fluoro-N-(6-hydroxypyridin-2-yl)pyrrolidine-2-carboxamide (83)

¹H NMR (400 MHz, DMSO-d₆) δ: 10.38 (s, 1H), 9.04 (s, 2H), 8.43 (s, 1H), 7.89-7.83 (m, 2H), 7.54-7.50 (m, 1H), 7.25-7.18 (m, 1H), 6.28 (d, J=8.0 Hz, 1H), 5.85 (d, J=17.2 Hz, 1H), 5.65 (d, J=17.2 Hz, 1H), 4.69-4.65 (m, 1H), 4.28-4.19 (m, 1H), 4.06-3.94 (m, 2H), 2.68 (s, 3H), 2.64 (s, 3H), 2.18-2.04 (m, 1H).

(1R,3S,5S)-2-(2-(3-Acetyl-7-methyl-5-(2-methylpyrimidin-5-yl)-1H-indazol-1-yl)acetyl)-N-(6-bromo-3-methylpyridin-2-yl)-5-(methoxymethyl)-2-azabicyclo[3.1.0]hexane-3-carboxamide (98)

¹H NMR (400 MHz CD₃OD) δ 9.00 (s, 2H), 8.42 (d, J=1.1 Hz, 1H), 7.57-7.51 (m, 2H), 7.39 (d, J=8.0 Hz, 1H), 5.98 (d, J=16.0 Hz, 1H), 5.82 (d, J=16.0 Hz, 1H), 4.64 (m, 1H), 3.73 (m, 1H), 3.58 (d, J=1.2 Hz, 1H), 3.43 (s, 3H), 2.76 (s, 6H), 2.70 (s, 3H), 2.62 (m, 1H), 2.54 (m, 1H), 2.14 (s, 3H), 1.34 (t, J=5.5 Hz, 1H), 1.09 (m, 1H). LC/MS (ESI) m/z: 646 (M+H)⁺.

(1R,3S,5R)-2-(2-(3-Acetyl-7-methyl-5-(2-methylpyrimidin-5-yl)-1H-indazol-1-yl)acetyl)-N-(6-hydroxypyridin-2-yl)-5-methyl-2-azabicyclo[3.1.0]hexane-3-carboxamide (105)

¹H NMR (400 MHz, DMSO-d₆) δ: 10.20 (s, 1H), 9.02 (s, 2H), 8.31 (s, 1H), 7.55 (s, 1H), 7.53-7.50 (m, 1H), 7.21-7.20 (m, 1H), 6.27-6.26 (m, 1H), 6.08 (d, J=20 Hz, 1H), 5.66 (d, J=20 Hz, 1H), 4.47-4.43 (m, 2H), 3.77-3.62 (m, 1H), 2.68 (s, 9H), 2.04-2.00 (m, 1H), 1.24 (s, 3H), 1.01-0.98 (m, 1H), 0.89-0.88 (m, 1H).

(1R,3S,5R)-2-(2-(3-Acetyl-5-(2-hydroxypyrimidin-5-yl)-1H-indazol-1-yl)acetyl)-N-(6-bromo-3-methylpyridin-2-yl)-5-methyl-2-azabicyclo[3.1.0]hexane-3-carboxamide (106)

¹H NMR (400 MHz, DMSO-d₆) δ: 10.29 (s, 1H), 8.66 (s, 2H), 8.30 (s, 1H), 7.90-7.72 (m, 2H), 7.63 (d, J=7.6 Hz, 1H), 7.45 (d, J=7.6 Hz, 1H), 5.90 (d, J=17.6 Hz, 1H), 5.55 (d, J=17.6 Hz, 1H), 4.42-4.38 (m, 1H), 3.59-3.58 (m, 1H), 2.64 (s, 3H), 2.04 (s, 3H), 1.32-1.24 (m, 5H), 1.03-1.00 (m, 2H).

(1R,3S,5R)-2-(2-(3-Acetyl-5-(2-methoxypyrimidin-5-yl)-1H-indazol-1-yl)acetyl)-N-(6-bromopyridin-2-yl)-5-methyl-2-azabicyclo[3.1.0]hexane-3-carboxamide (108)

¹H NMR (400 MHz, DMSO-d₆) δ: 10.77 (s, 1H), 8.94 (s, 1H), 8.37 (s, 1H), 8.07 (d, J=8.0 Hz, 1H), 7.85-7.79 (m, 2H), 7.72-7.70 (m, 1H), 7.31 (d, J=8.0 Hz, 1H), 5.94 (d, J=17.2 Hz, 1H), 5.55 (d, J=17.2 Hz, 1H), 4.43-4.39 (m, 1H), 3.97 (s, 3H), 3.67-3.61 (m, 1H), 2.68 (s, 3H), 2.00-1.96 (m, 1H), 1.29 (s, 3H), 0.95-0.83 (m, 3H).

(1R,3S,5R)-2-(2-(3-Acetyl-5-(2-hydroxypyrimidin-5-yl)-1H-indazol-1-yl)acetyl)-N-(6-bromopyridin-2-yl)-5-methyl-2-azabicyclo[3.1.0]hexane-3-carboxamide (109)

¹H NMR (400 MHz, DMSO-d₆) δ: 10.79 (s, 1H), 8.74 (s, 2H), 8.30 (s, 1H), 8.04 (d, J=8.4 Hz, 1H), 7.82-7.69 (m, 2H), 7.33 (d, J=8.0 Hz, 1H), 5.94 (d, J=17.2 Hz, 1H), 5.55 (d, J=17.2 Hz, 1H), 4.43-4.39 (m, 1H), 3.64-3.62 (m, 1H), 2.67 (s, 3H), 2.01-1.96 (m, 1H), 1.30 (s, 3H), 0.97-0.86 (m, 3H).

(1R,3S,5S)-2-(2-(3-Acetyl-7-(methoxymethyl)-5-(2-methylpyrimidin-5-yl)-1H-indazol-1-yl)acetyl)-N-(6-bromo-3-methylpyridin-2-yl)-5-(methoxymethyl)-2-azabicyclo[3.1.0]hexane-3-carboxamide (114)

¹H NMR (400 MHz, CD₃OD) δ 9.04 (s, 2H), 8.61 (d, J=2.0 Hz, 1H), 7.75 (d, J=2.0 Hz, 1H), 7.56 (d, J=8.0 Hz, 1H), 7.39 (d, J=8.0 Hz, 1H), 6.04 (d, J=16.0 Hz, 1H), 5.89 (d, J=16.0 Hz, 1H), 4.98 (d, J=12.0 Hz, 1H), 4.71 (d, J=12.0 Hz, 1H), 4.63 (m, 1H), 3.69 (m, 1H), 3.58 (m, 2H), 3.43 (s, 3H), 3.39 (s, 3H), 2.77 (s, 3H), 2.71 (s, 3H), 2.58 (m, 2H), 2.15 (s, 3H), 1.33 (m, 1H), 1.15 (m, 1H). LC/MS (ESI) m/z: 676 (M+H)⁺.

(1R,3S,5R)-2-(2-(3-Acetyl-5-(2-hydroxypyrimidin-5-yl)-7-methyl-1H-indazol-1-yl)acetyl)-N-(6-bromo-3-methylpyridin-2-yl)-5-methyl-2-azabicyclo[3.1.0]hexane-3-carboxamide (121)

¹H NMR (400 MHz, DMSO-d₆) δ: 10.32 (s, 1H), 8.72 (s, 2H), 8.19 (s, 1H), 7.62 (d, J=8.0 Hz, 1H), 7.49 (s, 1H), 7.44 (d, J=8.0 Hz, 1H), 6.01 (d, J=17.6 Hz, 1H), 5.66 (d, J=18.0 Hz, 1H), 4.42-4.38 (m, 1H), 2.67 (s, 3H), 2.64 (s, 3H), 2.63-2.58 (m, 1H), 2.04 (s, 3H), 2.01-1.99 (m, 1H), 1.32 (s, 3H), 1.01-0.94 (m, 2H).

(1R,3S,5R)-2-(2-(3-Acetyl-4-fluoro-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (130)

¹H NMR (400 MHz, CD₃OD) δ 8.92 (d, J=1.1 Hz, 2H), 7.60 (m, 3H), 7.38 (d, J=7.9 Hz, 1H), 5.80 (m, 1H), 5.65 (m, 1H), 4.53 (m, 1H), 3.53 (m, 1H), 2.76 (s, 3H), 2.71 (s, 3H), 2.63 (m, 1H), 2.31 (m, 1H), 2.12 (s, 3H), 1.40 (s, 3H), 1.10 (m, 1H), 1.00 (m, 1H). LC/MS (ESI) m/z: 620 (M+H)⁺.

(1R,3S,5R)-2-(2-(3-Acetyl-7-cyclopropyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (131)

¹H NMR (400 MHz, DMSO-d₆) δ 10.31 (s, 1H), 9.03 (S, 2H), 8.32 (d, J=1.2 Hz, 1H), 7.62 (d, J=7.6 Hz, 1H), 7.48 (s, 1H), 7.44 (d, J=7.6 Hz, 1H), 6.14 (d, J=17.6 Hz, 1H), 5.87 (d, J=17.6 Hz, 1H), 4.42-4.38 (m, 1H), 3.61-3.59 (m, 1H), 2.68 (s, 3H), 2.65 (s, 3H), 2.58-2.52 (m, 1H), 2.30 (m, 1H), 2.04 (m, 4H), 1.32 (m, 3H), 1.04-1.00 (m, 4H), 0.91-0.89 (m, 2H). LC/MS (ESI) m/z: 642 (M+H)⁺.

(1R,2S,5S)-3-(2-(3-Acetyl-5-(2-methylpyrimidin-5-yl)-1H-pyrazolo[3,4-c]pyridin-1-yl)acetyl)-N-(6-bromo-3-methylpyridin-2-yl)-3-azabicyclo[3.1.0]hexane-2-carboxamide (141)

¹H NMR (400 MHz, DMSO-d₆) δ 0.73-0.89 (m, 2H), 1.88-1.96 (m, 1H), 2.03 (s, 4H), 2.67 (s, 3H), 2.70 (s, 3H), 3.91 (d, J=9.6 Hz, 1H), 4.02-4.11 (m, 1H), 4.62 (d, J=5.4 Hz, 1H), 5.65-5.80 (m, 2H), 7.41 (d, J=7.9 Hz, 1H), 7.60 (d, J=8.0 Hz, 1H), 8.60 (s, 1H), 9.26 (d, J=1.3 Hz, 1H), 9.34 (s, 2H), 10.30 (s, 1H).

(1R,3S,5S)-2-(2-(3-Acetyl-5-(2-methylpyrimidin-5-yl)-1H-indazol-1-yl)acetyl)-N-(6-bromo-3-(methoxymethyl)pyridin-2-yl)-5-(methoxymethyl)-2-azabicyclo[3.1.0]hexane-3-carboxamide (152)

¹H NMR (400 MHz, CD₃OD) δ 8.99 (s, 2H), 8.53 (s, 1H), 7.78 (d, J=1.2 Hz, 2H), 7.75 (d, J=8.0 Hz, 1H), 7.46 (d, J=8.0 Hz, 1H), 5.81 (d, J=16.0 Hz, 1H), 5.66 (d, J=16.0 Hz, 1H), 4.58 (m, 1H), 4.28 (m, 2H), 3.73 (m, 1H), 3.55 (m, 2H), 3.42 (s, 3H), 3.17 (s, 3H), 2.75 (s, 3H), 2.69 (s, 3H), 2.63-2.50 (m, 2H), 1.32 (d, J=4.0 Hz, 1H), 1.11 (m, 1H). LC/MS (ESI) m/z: 662 (M+H)⁺.

(1R,3S,5R)-2-(2-(3-Acetyl-5-(2-methylpyrimidin-5-yl)-1H-indazol-1-yl)acetyl)-N-(6-bromo-3-methylpyridin-2-yl)-5-((2,2-difluorocyclopentanecarboxamido)methyl)-2-azabicyclo[3.1.0]hexane-3-carboxamide (159)

¹H NMR (400 MHz, CD₃OD) δ 8.93 (s, 2H), 8.47 (s, 1H), 7.71 (s, 2H), 7.47 (d, J=7.9 Hz, 1H), 7.31 (dd, J=7.9, 2.2 Hz, 1H), 5.69 (m, 1H), 5.57 (m, 1H), 4.54 (m, 1H), 3.67-3.29 (m, 3H), 3.05-2.88 (m, 1H), 2.66 (s, 3H), 2.61 (s, 3H), 2.18-1.88 (m, 6H), 1.94-1.73 (m, 2H), 1.65 (m, 1H), 1.21 (m, 1H), 1.06-0.93 (m, 1H). LC/MS (ESI) m/z: 749 (M+H)⁺.

(1R,2S,5S)-3-(2-(3-Acetyl-5-(2-methylpyrimidin-5-yl)-1H-pyrazolo[3,4-c]pyridin-1-yl)acetyl)-N-(6-bromo-5-fluoro-3-methylpyridin-2-yl)-3-azabicyclo[3.1.0]hexane-2-carboxamide (172)

¹H NMR (400 MHz, DMSO-d₆) δ 0.74-0.88 (m, 2H), 1.88-1.98 (m, 1H), 2.02-2.09 (m, 4H), 2.68 (s, 3H), 2.70 (s, 3H), 3.91 (d, J=9.6 Hz, 1H), 4.01-4.09 (m, 1H), 4.60 (d, J=5.4 Hz, 1H), 5.67-5.83 (m, 2H), 7.80 (d, J=8.4 Hz, 1H), 8.60 (d, J=1.3 Hz, 1H), 9.26 (s, 1H), 9.34 (s, 2H), 10.30 (s, 1H).

(1R,3S,5R)-2-(2-(3-Acetyl-5-(2-methylpyrimidin-5-yl)-1H-pyrazolo[3,4-b]pyridin-1-yl)acetyl)-N-(6-bromo-5-fluoro-3-methylpyridin-2-yl)-5-methyl-2-azabicyclo[3.1.0]hexane-3-carboxamide (182)

$^1$H NMR (400 MHz, DMSO-d$_6$) δ 0.94-0.98 (m, 1H), 1.02-1.08 (m, 1H), 1.33 (s, 3H), 1.97-2.14 (m, 4H), 2.54-2.60 (m, 1H), 2.68 (s, 3H), 2.71 (s, 3H), 3.59-3.66 (m, 1H), 4.40 (dd, J=5.1, 9.2 Hz, 1H), 5.62 (d, J=17.0 Hz, 1H), 5.91 (d, J=17.1 Hz, 1H), 7.83 (d, J=8.4 Hz, 1H), 8.84 (d, J=2.0 Hz, 1H), 9.02 (d, J=2.0 Hz, 1H), 9.14 (s, 2H), 10.27 (s, 1H).

(1R,2S,5S)-3-(2-(3-Acetyl-5-(2-methylpyrimidin-5-yl)-1H-pyrazolo[3,4-b]pyridin-1-yl)acetyl)-N-(6-bromo-3-methylpyridin-2-yl)-3-azabicyclo[3.1.0]hexane-2-carboxamide (183)

$^1$H NMR (400 MHz, DMSO-d$_6$) δ 0.73-0.81 (m, 1H), 0.82-0.92 (m, 2H), 1.89 (s, 1H), 2.04 (s, 3H), 2.66 (s, 3H), 2.71 (s, 3H), 3.93 (d, J=9.8 Hz, 1H), 4.05-4.13 (m, 1H), 4.60 (d, J=5.4 Hz, 1H), 5.59 (s, 2H), 7.40 (d, J=7.9 Hz, 1H), 7.59 (d, J=7.9 Hz, 1H), 8.82 (d, J=2.0 Hz, 1H), 8.99 (d, J=2.0 Hz, 1H), 9.13 (s, 2H), 10.27 (s, 1H).

(1R,3S,5R)-2-(2-(3-Acetyl-5-(2-methylpyrimidin-5-yl)-1H-pyrazolo[4,3-b]pyridin-1-yl)acetyl)-N-(6-bromo-5-fluoro-3-methylpyridin-2-yl)-5-methyl-2-azabicyclo[3.1.0]hexane-3-carboxamide (185)

$^1$H NMR (400 MHz, DMSO-d$_6$) δ 0.96-1.08 (m, 2H), 1.31-1.35 (m, 3H), 2.07 (s, 4H), 2.53-2.60 (m, 1H), 2.73 (s, 3H), 2.82 (s, 3H), 3.53-3.60 (m, 1H), 4.35-4.43 (m, 1H), 5.61 (d, J=17.2 Hz, 1H), 5.93 (d, J=17.2 Hz, 1H), 7.83 (d, J=8.4 Hz, 1H), 8.23 (d, J=9.0 Hz, 1H), 8.35 (d, J=8.9 Hz, 1H), 9.44 (s, 2H), 10.26 (s, 1H).

(1R,3S,5R)-2-(2-(3-Acetyl-5-(2-methylpyrimidin-5-yl)-1H-pyrazolo[3,4-c]pyridin-1-yl)acetyl)-N-(6-bromo-3-(morpholinomethyl)pyridin-2-yl)-5-methyl-2-azabicyclo[3.1.0]hexane-3-carboxamide (192)

$^1$H NMR (400 MHz, DMSO-d$_6$) δ 10.42 (s, 1H), 9.36 (s, 2H), 9.33 (s, 1H), 8.63 (s, 1H), 7.77 (d, 1H, J=8.4 Hz), 7.47 (d, 1H, J=8.4 Hz), 6.08 (d, 1H, J=17.7 Hz), 5.74 (d, 1H, J=17.7 Hz), 4.44-4.49 (m, 1H), 3.61-3.65 (m 1H), 3.42-3.46 (m, 4H), 3.28 (s, 2H), 2.70 (s, 3H), 2.69 (s, 3H), 2.54-2.59 (m, 1H), 2.07-2.18 (m, 5H), 1.35 (s, 3H), 0.99-1.13 (m, 2H).

(1R,3S,5R)-2-(2-(3-Acetyl-5-(2-aminopyrimidin-5-yl)-1H-pyrazolo[3,4-c]pyridin-1-yl)acetyl)-N-(6-bromo-5-fluoro-3-methylpyridin-2-yl)-5-methyl-2-azabicyclo[3.1.0]hexane-3-carboxamide (195)

$^1$H NMR (400 MHz, DMSO-d$_6$) δ 0.98-1.04 (m, 1H), 1.07-1.12 (m, 1H), 1.33 (s, 3H), 2.01-2.12 (m, 4H), 2.54-2.61 (m, 1H), 2.67 (s, 3H), 3.56-3.65 (m, 1H), 4.38-4.45 (m, 1H), 5.69 (d, J=17.2 Hz, 1H), 6.00 (d, J=17.2 Hz, 1H), 6.90 (s, 2H), 7.83 (d, J=8.4 Hz, 1H), 8.37 (s, 1H), 8.93 (s, 2H), 9.20 (s, 1H), 10.27 (s, 1H).

(1R,3S,5R)-2-(2-(3-Acetyl-5-(2-methoxypyrimidin-5-yl)-1H-pyrazolo[3,4-c]pyridin-1-yl)acetyl)-N-(6-bromo-5-fluoro-3-methylpyridin-2-yl)-5-methyl-2-azabicyclo[3.1.0]hexane-3-carboxamide (198)

$^1$H NMR (400 MHz, DMSO-d$_6$) δ 0.99-1.06 (m, 1H), 1.07-1.12 (m, 1H), 1.34 (s, 3H), 2.00-2.12 (m, 4H), 2.53-2.61 (m, 1H), 2.69 (s, 3H), 3.55-3.63 (m, 1H), 4.01 (s, 3H), 4.29-4.49 (m, 1H), 5.73 (d, J=17.2 Hz, 1H), 6.04 (d, J=17.3 Hz, 1H), 7.83 (d, J=8.4 Hz, 1H), 8.55 (d, J=1.3 Hz, 1H), 9.20-9.33 (m, 3H), 10.27 (s, 1H).

(1R,3S,5R)-2-(2-(3-Acetyl-7-methyl-5-(2-methylpyrimidin-5-yl)-1H-pyrrolo[2,3-c]pyridin-1-yl)acetyl)-N-(6-bromo-5-fluoro-3-methylpyridin-2-yl)-5-methyl-2-azabicyclo[3.1.0]hexane-3-carboxamide $^1$H-NMR (400 MHz, DMSO-d$_6$) δ 10.33 (s, 1H), 9.26 (s, 2H), 8.49 (d, J=6.0 Hz, 2H), 7.82 (d, J=8.3 Hz, 1H), 5.79 (d, J=17.9 Hz, 1H), 5.48 (d, J=17.8 Hz, 1H), 4.39 (m, 1H), 3.57 (m, 1H), 2.82 (s, 3H), 2.67 (s, 3H), 2.60-2.52 (m, 1H), 2.10-1.97 (m, 4H), 1.33 (s, 3H), 1.02 (m, 1H), 0.91 (m, 1H). LC/MS (ESI) m/z: 634/636 (M+H)$^+$.

(1R,3S,5R)-2-(2-(3-Acetyl-7-methyl-5-(2-methylpyrimidin-5-yl)-1H-indazol-1-yl)acetyl)-N-(6-bromo-4-methylpyridin-2-yl)-5-methyl-2-aza-bicyclo[3.1.0]hexane-3-carboxamide $^1$H-NMR (400 MHz, CD$_3$OD) δ 8.97 (s, 2H), 8.39 (s, 1H), 7.91 (s, 1H), 7.52 (s, 1H), 7.11 (s, 1H), 5.95-6.00 (d, J=18 Hz, 1H), 5.76-5.80 (d, J=18 Hz, 1H), 4.46-4.50 (m, 1H), 3.53-3.55 (m, 1H), 2.75 (s, 3H), 2.73 (s, 3H), 2.67 (s, 3H), 2.53-2.59 (m, 1H), 2.31 (s, 3H), 2.15-2.19 (m, 1H), 1.38 (s, 3H), 1.08-1.11 (m, 1H), 0.94-0.96 (m, 1H). LC/MS (ESI) m/z: 616/618 (M+H)$^+$.

(1R,3S,5R)-2-(2-(3-Acetyl-5-(2-methylpyrimidin-5-yl)-1H-pyrazolo[3,4-c]pyridin-1-yl)acetyl)-N-(6-bromo-4-methylpyridin-2-yl)-5-methyl-2-aza-bicyclo[3.1.0]hexane-3-carboxamide $^1$H-NMR (400 MHz, CD$_3$OD) δ 9.31 (s, 2H), 9.20 (s, 1H), 8.63 (s, 1H), 7.90 (s, 1H), 7.10 (s, 1H), 5.93-5.98 (d, J=17.6 Hz, 1H), 5.72-5.77 (d, J=17.2 Hz, 1H), 4.48-4.51 (m, 1H), 3.54-3.56 (m, 1H), 2.74 (s, 3H), 2.70 (s, 3H), 2.53-2.59 (m, 1H), 2.29 (s, 3H), 2.15-2.20 (m, 1H), 1.38 (s, 3H), 1.08-1.11 (m, 1H), 1.00-1.02 (m, 1H). LC/MS (ESI) m/z: 603/605 (M+H)$^+$.

(1R,3S,5R)-2-{2-[3-Acetyl-5-(2-methylpyrimidin-5-yl)indazol-1-yl] acetyl}-N-(6-bromo-4-methylpyridin-2-yl)-5-methyl-2-azabicyclo[3.1.0]hexane-3-carboxamide $^1$H-NMR (400 MHz, CD$_3$OD) δ 8.97 (d, J=7.1 Hz, 2H), 8.54-8.48 (m, 1H), 7.90 (s, 1H), 7.77 (d, J=1.2 Hz, 2H), 7.11 (s, 1H), 5.80 (d, J=17.2 Hz, 1H), 5.63 (d, J=17.2 Hz, 1H), 4.53-4.44 (m, 1H), 3.57-3.52 (m, 1H), 2.74 (s, 3H), 2.69 (s, 3H), 2.59-2.52 (m, 1H), 2.30 (s, 3H), 2.21-2.14 (m, 1H), 1.37 (s, 3H), 1.10-1.04 (m, 1H), 0.99-0.95 (m, 1H). LC/MS (ESI) m/z: 602/604 (M+H)$^+$.

(1R,3S,5R)-2-(2-(3-Acetyl-7-methyl-5-(2-methylpyrimidin-5-yl)-1H-pyrazolo[3,4-c]pyridin-1-yl)acetyl)-N-(6-bromo-4-fluoropyridin-2-yl)-5-methyl-2-aza-bicyclo[3.1.0]hexane-3-carboxamide $^1$H-NMR (400 MHz, DMSO-d$_6$) δ 11.14 (s, 1H), 9.32 (s, 2H), 8.48 (s, 1H), 7.84-7.87 (dd, J=11.2 Hz, 1.6 Hz, 1H), 7.41-7.43 (dd, J=7.6 Hz, 1.2 Hz, 1H), 6.16-6.20 (d, J=18.0 Hz, 1H) 5.75-5.79 (d, J=18.0 Hz, 1H), 4.35-4.45 (m, 1H), 3.66-3.67 (m, 1H), 2.92 (s, 3H), 2.68 (s, 3H), 2.67 (s, 3H), 2.64-2.65 (m, 1H), 2.02-2.03 (m, 1H), 1.31 (s, 3H), 0.99-1.01 (m, 1H), 0.92-0.94 (m, 1H). LC/MS (ESI) m/z: 621/623 (M+H)+.

(1R,3S,5R)-2-(2-(3-Acetyl-7-methyl-5-(2-methylpyrimidin-5-yl)-1H-pyrazolo[3,4-c]pyridin-1-yl)acetyl)-N-(6-bromo-5-fluoro-3-methylpyridin-2-yl)-5-((5-methyl-1,3,4-oxadiazol-2-yl)methyl)-2-azabicyclo[3.1.0]hexane-3-carboxamide 1H-NMR (400 MHz, DMSO-d6) δ 10.32 (s, 1H), 9.33 (s, 2H), 8.50 (s, 1H), 7.82 (d, J=8.4 Hz, 1H), 6.17 (d, J=18.0 Hz, 1H), 5.80 (d, J=18.0 Hz, 1H), 4.45 (m, 1H), 3.86 (m, 1H), 3.25 (d, J=16.0 Hz, 1H), 3.10 (d, J=16.0 Hz, 1H), 2.92 (s, 3H), 2.68 (s, 3H), 2.67 (s, 3H), 2.66-2.62 (m, 1H), 2.46 (s, 3H), 2.18 (m, 1H), 2.03 (s, 3H), 1.25 (m, 1H), 1.16 (m, 1H). LC/MS (ESI) m/z: 717/719 (M+H)+.

(2S,4R)-1-{2-[3-Acetyl-7-methyl-5-(2-methylpyrimidin-5-yl)pyrazolo[3,4-c]pyridin-1-yl]acetyl}-N-(6-bromo-3-methylpyridin-2-yl)-4-fluoro-4-methylpyrrolidine-2-carboxamide 1H-NMR (400 MHz, DMSO-d6) δ 10.51 (s, 1H), 9.33 (d, J=5.4 Hz, 2H), 8.49 (d, J=6.9 Hz, 1H), 7.60 (d, J=8.0 Hz, 1H), 7.42 (d, J=7.9 Hz, 1H), 6.01 (d, J=17.9 Hz, 1H), 5.82 (d, J=17.8 Hz, 1H), 4.68-4.62 (m, 1H), 4.30-4.22 (m, 1H), 3.94-3.83 (m, 1H), 2.89 (s, 3H), 2.68 (s, 3H), 2.67 (s, 3H), 2.24-2.16 (m, 1H), 2.13-2.04 (m, 1H), 1.99 (s, 3H), 1.64 (d, J=21.0 Hz, 3H). LC/MS (ESI) m/z: 623 (M+H)+.

(2S,4R)-1-(2-(3-Acetyl-7-methyl-5-(2-methylpyrimidin-5-yl)-1H-indazol-1-yl)acetyl)-N-(6-bromo-3-methylpyridin-2-yl)-4-fluoro-4-methylpyrrolidine-2-carboxamide 1H-NMR (400 MHz, DMSO-d6) δ 10.50 (s, 1H), 9.02 (d, J=6.8 Hz, 2H), 8.30 (d, J=1.1 Hz, 1H), 7.63-7.56 (m, 2H), 7.42 (d, J=7.9 Hz, 1H), 5.89 (d, J=17.9 Hz, 1H), 5.70 (d, J=17.8 Hz, 1H), 4.67-4.62 (m, 1H), 4.28-4.20 (m, 1H), 3.92-3.80 (m, 1H), 2.68 (s, 3H), 2.66 (s, 3H), 2.64 (s, 3H), 2.24-2.14 (m, 1H), 2.13-2.02 (m, 1H), 2.00 (s, 3H), 1.63 (d, J=21.0 Hz, 3H). LC/MS (ESI) m/z: 622 (M+H)+.

(1R,3S,5R)-2-(2-(3-Acetyl-7-methyl-5-(2-methylpyrimidin-5-yl)-1H-pyrazolo[3,4-c]pyridin-1-yl)acetyl)-N-(6-bromo-5-fluoro-3-methylpyridin-2-yl)-5-((3-methyl-1,2,4-oxadiazol-5-yl)methyl)-2-azabicyclo[3.1.0]hexane-3-carboxamide 1H-NMR (400 MHz, CD3OD) δ 8.98 (s, 2H), 8.40 (d, J=1.1 Hz, 1H), 7.58-7.48 (m, 2H), 5.98 (d, J=17.7 Hz, 1H), 5.80 (d, J=17.7 Hz, 1H), 4.59-4.56 (m, 1H), 3.85 (dd, J=5.7, 2.7 Hz, 1H), 3.37 (d, J=16.1 Hz, 1H), 3.16 (d, J=16.1 Hz, 1H), 2.73 (dd, J=11.1, 3.4 Hz, 7H), 2.67 (s, 3H), 2.48 (dd, J=13.7, 4.3 Hz, 1H), 2.36 (s, 3H), 2.12 (s, 3H), 1.37 (t, J=5.7 Hz, 1H), 1.29 (m, 1H), 1.18 (m, 1H). LC/MS (ESI) m/z: 717/719 [M+H]+.

(1R,3S,5R)-2-(2-(3-Acetyl-7-(fluoromethyl)-5-(2-methylpyrimidin-5-yl)-1H-indazol-1-yl)acetyl)-N-(6-bromo-3-methylpyridin-2-yl)-5-((5-methyl-1,3,4-oxadiazol-2-yl)methyl)-2-azabicyclo[3.1.0]hexane-3-carboxamide 1H-NMR (400 MHz, DMSO-d6) δ 10.31 (s, 1H), 9.07 (s, 2H), 8.58 (s, 1H), 8.01 (s, 1H), 7.62 (d, J=8.3 Hz, 1H), 7.44 (d, J=7.9 Hz, 1H), 5.72-5.97 (m, 3H), 5.62-5.70 (m, 1H), 4.45 (dd, J=9.3, 5.3 Hz, 1H), 3.82 (dd, J=5.6, 2.7 Hz, 1H), 3.09-3.23 (m, 2H), 2.69 (s, 3H), 2.68 (s, 3H), 2.51-2.52 (m, 1H), 2.45 (s, 3H), 2.14-2.21 (m, 1H), 1.99 (s, 3H), 1.22-1.26 (m, 1H), 1.13-1.20 (m, 1H). LC/MS (ESI) m/z: 716/718 (M+H)+.

(1R,3S,5R)—N-(6-Bromo-3-methylpyridin-2-yl)-2-{2-[3-carbamoyl-5-(2-methylpyrimidin-5-yl)pyrazolo[3,4-c]pyridin-1-yl]acetyl}-5-methyl-2-azabicyclo[3.1.0]hexane-3-carboxamide 1H-NMR (400 MHz, CD3OD) δ 9.34 (s, 2H), 9.21 (d, J=1.2 Hz, 1H), 8.69 (d, J=1.2 Hz, 1H), 7.55 (d, J=8.0 Hz, 1H), 7.38 (d, J=8.0 Hz, 1H), 5.90 (d, J=20.0 Hz, 1H), 5.75 (d, J=20.0 Hz, 1H), 4.54 (m, 1H), 3.54 (m, 1H), 2.76 (s, 3H), 2.63 (m, 1H), 2.31 (m, 1H), 2.11 (s, 3H), 1.41 (s, 3H), 1.10 (t, J=4.0 Hz, 1H), 1.00 (m, 1H). LC/MS (ESI) m/z: 604/606 (M+H)+.

(1R, 2S, 5S)-3-{2-[3-Acetyl-7-methyl-5-(2-methylpyrimidin-5-yl) pyrazolo [3, 4-c]pyridin-1-yl] acetyl}-N-[(3-chloro-2-fluorophenyl) methyl]-3-azabicyclo [3.1.0] hexane-2-carboxamide 1H-NMR (400 MHz, DMSO-d6) δ 9.33 (s, 2H), 8.49 (s, 1H), 8.43 (t, J=5.7 Hz, 1H), 7.40 (dd, J=14.7, 7.8 Hz, 1H), 7.23 (dd, J=14.0, 7.4 Hz, 1H), 7.00 (t, J=7.5 Hz, 1H), 5.87-5.70 (m, 2H), 4.47 (t, J=9.6 Hz, 1H), 4.35 (dd, J=15.6, 5.9 Hz, 1H), 4.24 (dd, J=15.6, 5.6 Hz, 1H), 4.00 (dd, J=9.7, 5.1 Hz, 1H), 3.85 (d, J=9.8 Hz, 1H), 2.88 (s, 3H), 2.66 (t, J=9.4 Hz, 6H), 1.93 (d, J=12.2 Hz, 1H), 1.84 (s, 1H), 0.81-0.67 (m, 2H). LC/MS (ESI) m/z: 576 (M+H)+.

(1R,2S,5S)-3-(2-(3-Acetyl-5-(2-methylpyrimidin-5-yl)-1H-indazol-1-yl)acetyl)-N-(3-chloro-2-fluorobenzyl)-3-azabicyclo[3.1.0]hexane-2-carboxamide 1H-NMR (400 MHz, CD3OD) δ 9.00 (s, 2H), 8.53 (s, 1H), 7.75 (s, 2H), 7.31-7.23 (m, 2H), 6.97-6.91 (m, 1H), 5.48 (t, J=13.4 Hz, 2H), 4.56 (d, J=5.6 Hz, 1H), 4.49 (d, J=15.6 Hz, 1H), 4.38 (d, J=15.6 Hz, 1H), 4.08-4.03 (m, 1H), 3.91 (d, J=9.7 Hz, 1H), 2.75 (s, 3H), 2.67 (s, 3H), 2.05-2.00 (m, 1H), 1.96-1.90 (m, 1H), 0.87-0.78 (m, 2H). LC/MS (ESI) m/z: 561 (M+H)+.

(2S)-1-{2-[3-Acetyl-7-methyl-5-(2-methylpyrimidin-5-yl)pyrazolo [3,4-c]pyridin-1-yl]acetyl}-N-(6-bromo-3-methylpyridin-2-yl)-4-fluoro-4-(fluoromethyl)pyrrolidine-2-carboxamide 1H-NMR (400 MHz, DMSO-d6) δ 10.56 (s, 1H), 9.32 (s, 2H), 8.48 (s, 1H), 7.60 (d, J=8.4 Hz, 1H), 7.42 (d, J=7.9 Hz, 1H), 6.06 (d, J=17.9 Hz, 1H), 5.88 (d, J=17.8 Hz, 1H), 4.96 (d, J=22.5 Hz, 1H), 4.84 (d, J=21.2 Hz, 1H), 4.72 (t, J=8.4 Hz, 1H), 4.41-4.31 (m, 1H), 4.14-4.03 (m, 1H), 2.90 (s, 3H), 2.69 (s, 3H), 2.67 (s, 3H), 2.37-2.15 (m, 2H), 1.99 (s, 3H). LC/MS (ESI) m/z: 641/643 (M+H)+.

2-{2-[3-Acetyl-7-(fluoromethyl)-5-(2-methylpyrimidin-5-yl) indazol-1-yl] acetyl}-N-(6-bromo-3-methylpyridin-2-yl)-5-[(3-methyl-1, 2, 4-oxadiazol-5-yl) methyl]-2-azabicyclo [3.1.0] hexane-3-carboxamide 1H-NMR (400 MHz, CD3OD) δ 9.04 (s, 2H), 8.67 (t, J=1.9 Hz, 1H), 7.85 (d, J=1.7 Hz, 1H), 7.54 (d, J=7.9 Hz, 1H), 7.41-7.33 (m, 1H), 5.98-5.64 (m, 4H), 4.59 (dd, J=9.2, 4.9 Hz, 1H), 3.84 (dd, J=5.7, 2.7 Hz, 1H), 3.39 (d, J=16.1 Hz, 1H), 3.16 (d, J=16.1 Hz, 1H), 2.85-2.62 (m, 6H), 2.52 (dd, J=13.5, 5.2 Hz, 1H), 2.33 (d, J=20.8 Hz, 3H), 2.13-1.98 (m, 3H), 1.60 (s, 1H), 1.42-1.37 (m, 1H), 1.22 (dd, J=5.9, 2.6 Hz, 1H). LC/MS (ESI) m/z: 716 (M+H)⁺.

(1R,3S,5R)—N-(6-Bromo-3-methylpyridin-2-yl)-2-(2-(3-cyano-7-methyl-5-(2-methylpyrimidin-5-yl)-1H-indazol-1-yl)acetyl)-5-methyl-2-azabicyclo[3.1.0]hexane-3-carboxamide 1H NMR (400 MHz, DMSO-d6) δ 10.32 (s, 1H), 9.13 (s, 2H), 8.13 (s, 1H), 7.73 (s, 1H), 7.61 (d, J=8.0 Hz, 1H), 7.43 (d, J=8.0 Hz, 1H), 7.24-7.22 (m, 1H), 7.17-7.10 (m, 1H), 6.05 (d, J=18.0 Hz, 1H), 5.70 (d, J=18.0 Hz, 1H), 4.40-4.37 (m, 1H), 3.57-3.56 (m, 1H), 2.68 (s, 3H), 2.67 (s, 3H), 2.66-2.65 (m, 1H), 2.02 (s, 3H), 2.01-2.02 (m, 1H), 1.31 (s, 3H), 1.01-0.98 (m, 1H), 0.93-0.92 (m, 1H).

Scheme 6: (1S,3S,5S)-2-(2-(3-Acetyl-5-(2-methylpyrimidin-5-yl)-1H-indazol-1-yl)acetyl)-N-(6-bromo-3-methylpyridin-2-yl)-5-((dimethylamino)methyl)-2-azabicyclo[3.1.0]hexane-3-carboxamide (10)

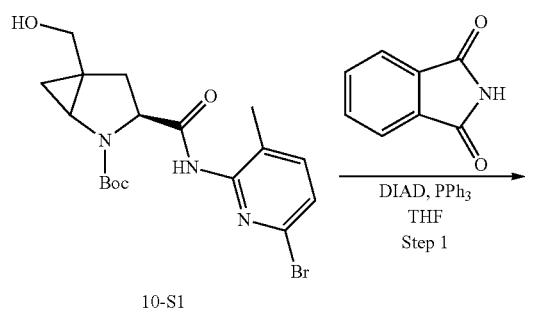

10-S1

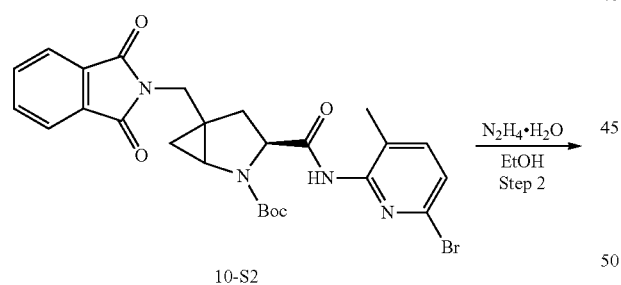

10-S2

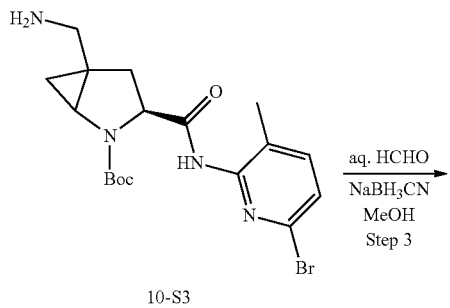

10-S3

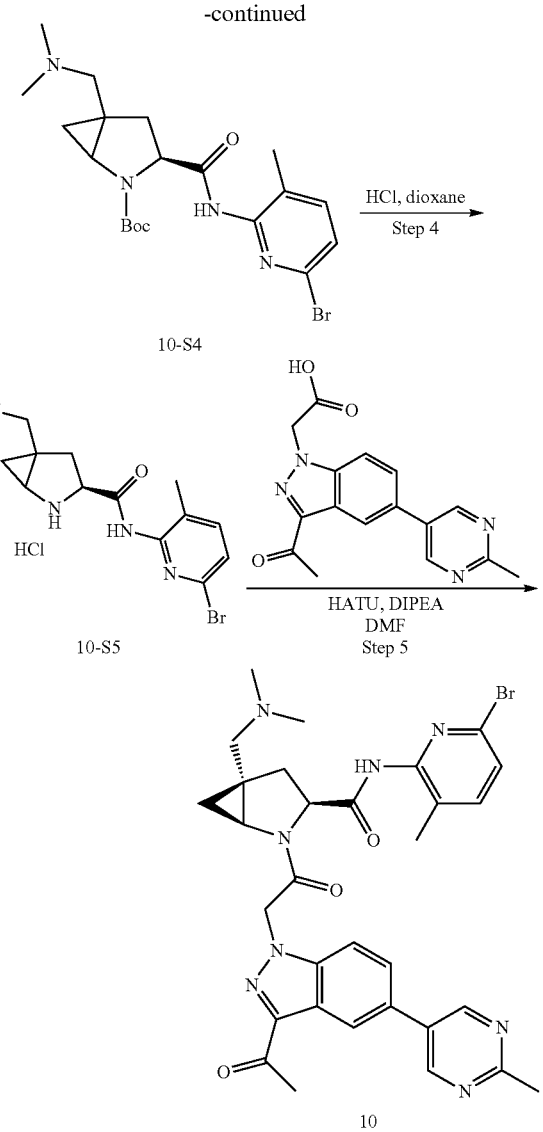

Step 1: (3S)-tert-Butyl 3-(6-bromo-3-methylpyridin-2-ylcarbamoyl)-5-((1,3-dioxoisoindolin-2-yl)methyl)-2-azabicyclo[3.1.0]hexane-2-carboxylate (10-S2)

To a solution of 10-S1 (1 g, 2.34 mmol), isoindoline-1,3-dione (517 mg, 3.52 mmol), and PPh₃ (1.22 g, 4.68 mmol) in THF (15 mL) was added DIAD (0.92 mL, 4.68 mmol) dropwise at 0° C. under an atmosphere of nitrogen. The reaction mixture was stirred at room temperature for 16 hours. The resulting mixture was partitioned with EtOAc and water. The organic layer was washed with brine, dried over anhydrous Na₂SO₄, and concentrated under reduced pressure. The remaining residue was purified by column chromatography on silica gel (eluted with PE/EtOAc=10:1 to 3:1) to afford the title compound (1.25 g, 96.1% yield) as a light yellow solid. LC/MS (ESI) m/z: 555/557 (M+H)⁺.

Step 2: (3S)-tert-Butyl 5-(aminomethyl)-3-(6-bromo-3-methylpyridin-2-ylcarbamoyl)-2-azabicyclo[3.1.0]hexane-2-carboxylate (10-S3)

To a solution of 10-S2 (1.2 g, 2.16 mmol) in EtOH (10 mL) was added hydrazine hydrate (1 mL, 85%). The reaction mixture was stirred at 60° C. for 3 hours and then cooled to room temperature. The mixture was filtered, the filtrate was concentrated to dryness, and the remaining crude product was purified by column chromatography on silica gel (eluted with DCM/MeOH=80:1 to 5:1) to afford 10-S3 (500 mg, 52.4% yield) as a light yellow oil. LC/MS (ESI) m/z: 425/427 (M+H)$^+$.

Step 3: (3S)-tert-Butyl 3-(6-bromo-3-methylpyridin-2-ylcarbamoyl)-5-((dimethylamino)methyl)-2-azabicyclo[3.1.0]hexane-2-carboxylate (10-S4)

To a solution of 10-S3 (500 mg, 1.18 mmol) in MeOH (5 mL) were added NaBH$_3$CN (148 mg, 2.36 mmol) and 15% aqueous formaldehyde solution (0.3 mL). The reaction mixture was stirred at room temperature for 1 hour and concentrated to dryness. The remaining residue was purified by column chromatography on silica gel (eluted with DCM/MeOH=30:1) followed by preparative HPLC to afford 10-S4 (90 mg, 16.8% yield) as a white solid. LC/MS (ESI) m/z: 453/455 (M+H)$^+$.

Step 4: (1R,3S,5R)—N-(6-Bromo-3-methylpyridin-2-yl)-5-((dimethylamino)methyl)-2-azabicyclo[3.1.0]hexane-3-carboxamide (10-S5)

To a solution of 10-S4 (90 mg, 0.21 mmol) in DCM (3 mL) was added TFA (1 mL). The reaction mixture was stirred at room temperature for 1.5 hours and then concentrated under reduced pressure to afford 10-S5 (65 mg, 94.6% yield) as a yellow solid. The crude material was carried forward in the next synthetic step without further purification. LC/MS (ESI) m/z: 353/355 (M+H)$^+$.

Step 5: (1S,3S,5S)-2-(2-(3-Acetyl-5-(2-methylpyrimidin-5-yl)-1H-indazol-1-yl)acetyl)-N-(6-bromo-3-methylpyridin-2-yl)-5-((dimethylamino)methyl)-2-azabicyclo[3.1.0]hexane-3-carboxamide (10)

To a solution of 10-S5 (90 mg, 0.20 mmol), 2-(3-acetyl-5-(2-methylpyrimidin-5-yl)-1H-indazol-1-yl)acetic acid (75 mg, 0.24 mmol), and HATU (152 mg, 0.40 mmol) in DMF (3 mL) was added DIPEA (0.13 mL, 0.80 mmol). The reaction mixture was stirred at room temperature for 16 hours. The mixture was partitioned with EtOAc and water. The organic layer was washed with brine, dried over anhydrous Na$_2$SO$_4$, and concentrated under reduced pressure. The crude product was purified by preparative TLC to afford 10 (35 mg, 27.3% yield) as a white solid. $^1$H NMR (400 MHz, CD$_3$OD) δ 8.99 (s, 2H), 8.52 (s, 1H), 7.75 (s, 2H), 7.53 (d, J=7.6 Hz, 1H), 7.37 (d, J=8.0 Hz, 1H), 5.78-5.82 (m, 1H), 5.62-5.67 (m, 1H), 5.10-5.12 (m, 1H), 3.82-3.85 (m, 1H), 3.42-3.48 (m, 1H), 2.73-2.86 (m, 10H), 2.69 (s, 3H), 2.47-2.52 (m, 1H), 2.06 (s, 3H), 1.79-1.81 (m, 1H), 0.89-0.92 (m, 2H). LC/MS (ESI) m/z: 645/647 (M+H)$^+$.

Scheme 7: Synthesis of (3S)-2-(2-(3-Acetyl-5-(2-methylpyrimidin-5-yl)-1H-indazol-1-yl)acetyl)-N-(6-bromo-1-methylpyridin-2-yl)-5-((hexahydrocyclopenta[c]pyrrol-2(1H)-yl)methyl)-2-azabicyclo[3.1.0]hexane-3-carboxamide (11)

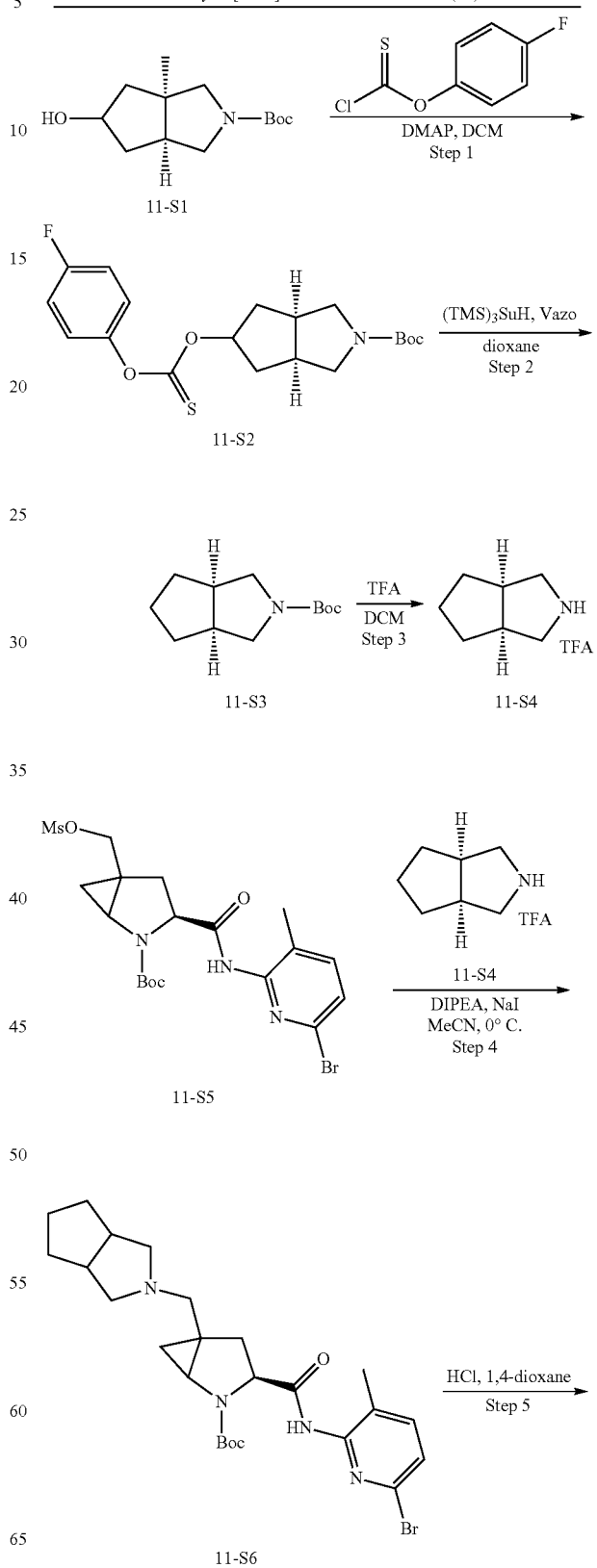

-continued

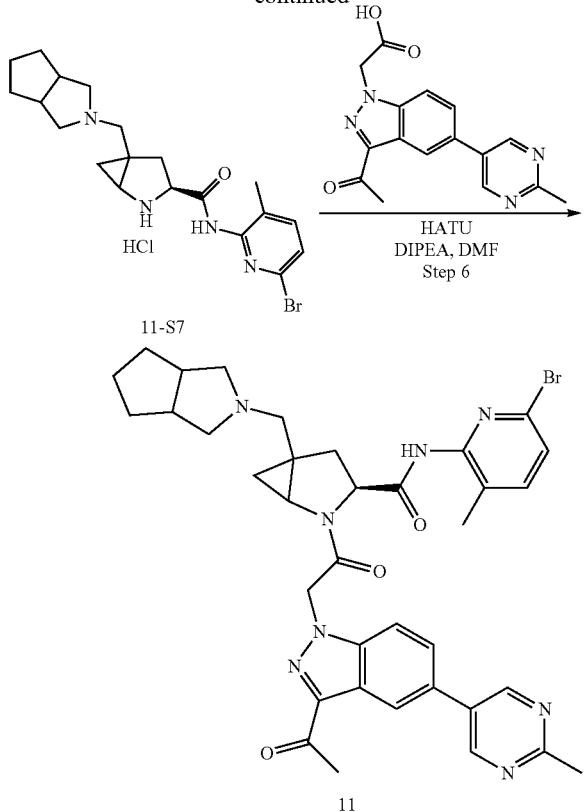

Step 1: (3aR,6aS)-tert-Butyl 5-(((4-fluorophenoxy)carbonothioyl)oxy)hexahydrocyclopenta[c] pyrrole-2(1H)-carboxylate (11-S2)

To a solution of (3aR,6aS)-tert-butyl 5-hydroxy-3a-methylhexahydrocyclopenta[c]pyrrole-2(1H)-carboxylate (11-S1, 300 mg, 0.94 mmol) in DCM (5 mL) were added 4-fluorophenylthionochloroformate (213.5 mg, 1.12 mmol) and DMAP (344.6 mg, 2.82 mmol). The reaction mixture was stirred at room temperature overnight. The mixture was diluted with DCM (20 mL), washed with 0.5 N aqueous HCl (10 mL), water (10 mL), and brine, dried over $Na_2SO_4$, filtered, and concentrated to dryness. The remaining residue was purified by column chromatography on silica gel (eluted with PE/EtOAc=20:1 to 10:1) to afford 11-S2 (338 mg, 94.3% yield) as a white solid. LC/MS (ESI) m/z: 404 $(M+Na)^+$.

Step 2: (3aR,6aS)-tert-Butyl hexahydrocyclopenta[c]pyrrole-2(1H)-carboxylate (11-S3)

To a solution of (3aR,6aS)-tert-butyl 5-(((4-fluorophenoxy)carbonothioyl)oxy)hexahydro cyclopenta[c]pyrrole-2(1H)-carboxylate (11-S2, 338 mg, 0.89 mmol) in 1,4-dioxane (3 mL) were added 1,1'-azobis(cyclohexanecarbonitrile) (Vazo, 73.0 mg, 0.45 mmol) and tris(trimethylsilyl)silane (330.9 mg, 1.33 mmol). The reaction mixture was stirred at 105° C. for 40 minutes at room temperature for 30 minutes. The mixture was concentrated to dryness to afford the crude product, which was purified by column chromatography on silica gel (eluted with PE/EtOAc=40:1 to 10:1) to afford 11-S3 (73 mg, 38.8% yield) as a yellow oil. LC/MS (ESI) m/z: 156 $(M+H-56)^+$.

Step 3: (3aR,6aS)-Octahydrocyclopenta[c]pyrrole (11-S4)

To a solution of (3aR,6aS)-tert-butyl hexahydrocyclopenta[c]pyrrole-2(1H)-carboxylate (11-S3, 73 mg, 0.14 mmol) in DCM (3 mL) was added TFA (1 mL) at 0° C. and the reaction mixture was stirred at room temperature for 1 hour. The mixture was evaporated under reduced pressure to afford 11-S4 (70 mg, 100% yield). This crude material was carried forward in the next synthetic step without further purification. LC/MS (ESI) m/z: 112 $(M+H)^+$.

Step 4: (3S)-tert-Butyl 3-((6-bromo-3-methylpyridin-2-yl)carbamoyl)-5-((hexahydrocyclopenta[c]pyrrol-2(1H)-yl)methyl)-2-azabicyclo[3.1.0]hexane-2-carboxylate (11-S6)

To a mixture of (3aR,6aS)-octahydrocyclopenta[c]pyrrole (11-S4, 35 mg, 0.3 mmol) and DIPEA (77.4 mmol, 0.6 mmol) in MeCN (3 mL) was added (3S)-tert-butyl 3-((6-bromo-3-methylpyridin-2-yl) carbamoyl)-5-(((methylsulfonyl)oxy)methyl)-2-azabicyclo[3.1.0]hexane-2-carboxylate (S5, 100 mg, 0.20 mmol) and NaI (32 mg, 0.2 mmol) at 0° C. After stirring at room temperature overnight, the mixture was evaporated under reduced pressure and the remaining residue was purified by column chromatography on silica gel (PE/EtOAc=5:1 to 1:1) to afford 11-S6 (30 mg, 28.9% yield) as a brown oil. LC/MS (ESI) m/z: 519 $(M+H)^+$.

Step 5: (3S)—N-(6-Bromo-3-methylpyridin-2-yl)-5-((hexahydrocyclopenta[c]pyrrol-2(1H)-yl)methyl)-2-azabicyclo[3.1.0]hexane-3-carboxamide (11-S7)

To a solution of (3S)-tert-butyl 3-((6-bromo-3-methylpyridin-2-yl)carbamoyl)-5-((hexahydrocyclopenta[c]pyrrol-2(1H)-yl)methyl)-2-azabicyclo[3.1.0]hexane-2-carboxylate (11-S6, 30 mg) in 1,4-dioxane (1 mL) was added a 4 N solution of HCl in 1,4-dioxane (1 mL) at 0° C. and the reaction mixture was stirred at room temperature for 1 hour. The mixture was concentrated to dryness to afford 11-S7 (30 mg, 100% yield), which was used in the next synthetic step without further purification.

Step 6: (3S)-2-(2-(3-Acetyl-5-(2-methylpyrimidin-5-yl)-1H-indazol-1-yl)acetyl)-N-(6-bromo-3-methylpyridin-2-yl)-5-((hexahydrocyclopenta[c]pyrrol-2(1H)-yl)methyl)-2-azabicyclo[3.1.0]hexane-3-carboxamide (11)

To a mixture of (3S)—N-(6-bromo-3-methylpyridin-2-yl)-5-((hexahydrocyclopenta[c]pyrrol-2(1H)-yl)methyl)-2-azabicyclo[3.1.0]hexane-3-carboxamide (11-S7, 20 mg, 0.05 mmol), 2-(3-acetyl-5-(2-methylpyrimidin-5-yl)-1H-indazol-1-yl) acetic acid (14.8 mg, 0.05 mmol), and HATU (28.5 mg, 0.08 mmol) in DMF (2 mL) was added DIPEA (19.3 mg, 0.15 mmol) and the mixture was stirred at room temperature overnight. The mixture was partitioned with EtOAc and water. The organic layer was washed with brine, dried over $Na_2SO_4$, and concentrated under reduced pressure. The remaining residue was purified by preparative TLC to afford 11 (1.1 mg, 3.1% yield) as a white solid. $^1$H NMR (400 MHz, $CD_3OD$) δ 9.01 (d, J=2.8 Hz, 2H), 8.56 (d, J=5.3 Hz, 1H), 7.79-7.76 (m, 2H), 7.58-7.54 (m, 1H), 7.44-7.39 (m, 1H), 5.83-5.79 (d, 1H), 5.69-5.64 (s, 1H), 3.93-3.86 (m, 2H), 3.49-3.46 (m, 1H), 2.97-2.93 (m, 2H), 2.75 (s, 3H), 2.70 (s, 3H), 2.10 (d, J=18.6 Hz, 3H), 1.40-1.26 (m, 13H). LC/MS (ESI) m/z: 711 $(M+H)^+$.

Scheme 8: Synthesis of (3S)-5-(3-Azabicyclo[3.1.1]heptan-3-ylmethyl)-2-(2-(3-acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide (12)
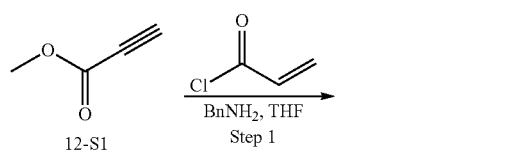
12-S1
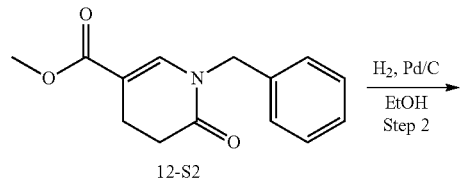
12-S2
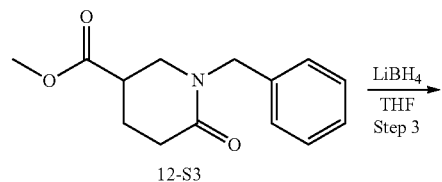
12-S3
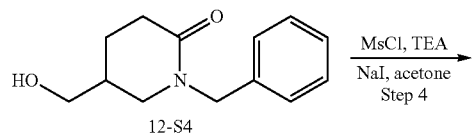
12-S4
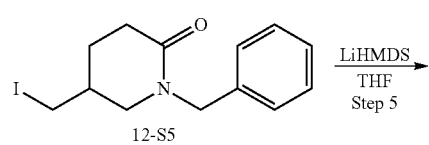
12-S5
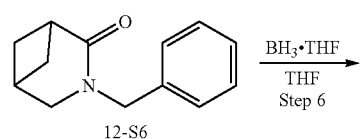
12-S6
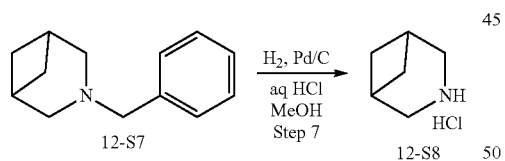
12-S7    12-S8
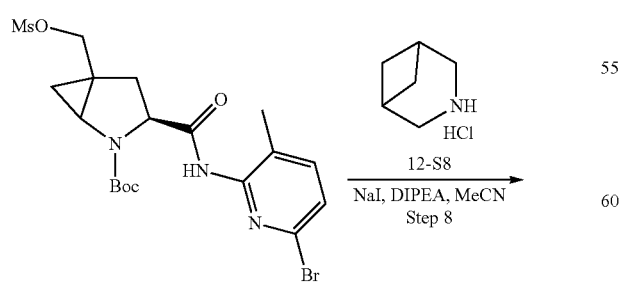
12-S9
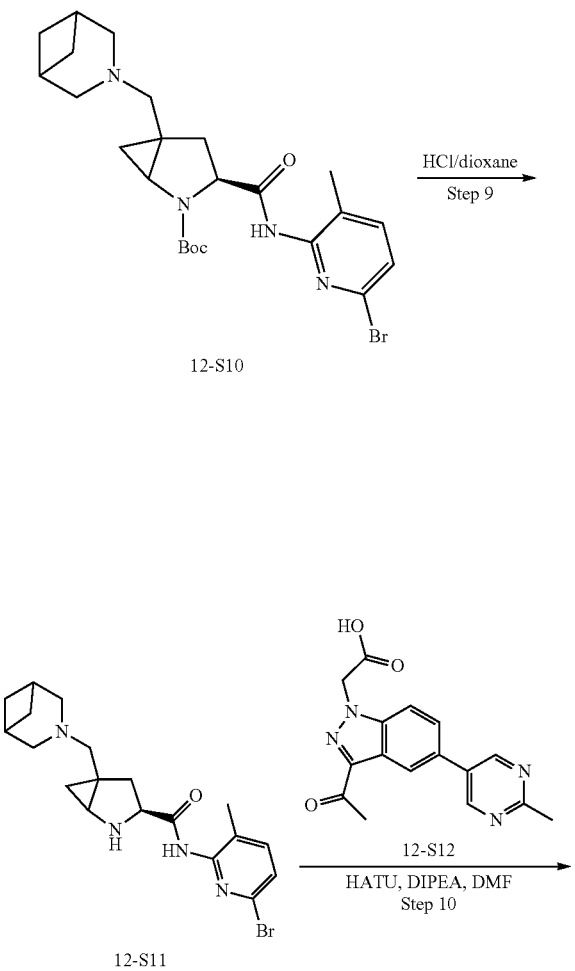
12-S10
12-S11

12-S12
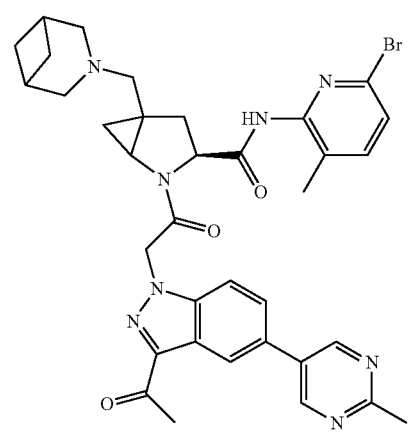
12

Scheme 1. Sythesis of (((2S,4R)-1-(2-(3-Acetyl-5-(2-methylpyrimidin-5-yl)-1H-indazol-1-yl)acetyl)-4-fluoropyrrolidine-2-carbonyl)amino)methyl)-o-carborane (1) & Lithium salt of (2S,4R)-1-(2-(3-acetyl-5-(2-methylpyrimidin-5-yl)-1H-indazol-1-yl)acetyl)-4-fluoropyrrolidine-2-carbonyl)amino)methyl-nido-dodecahydroundecaborate (8)

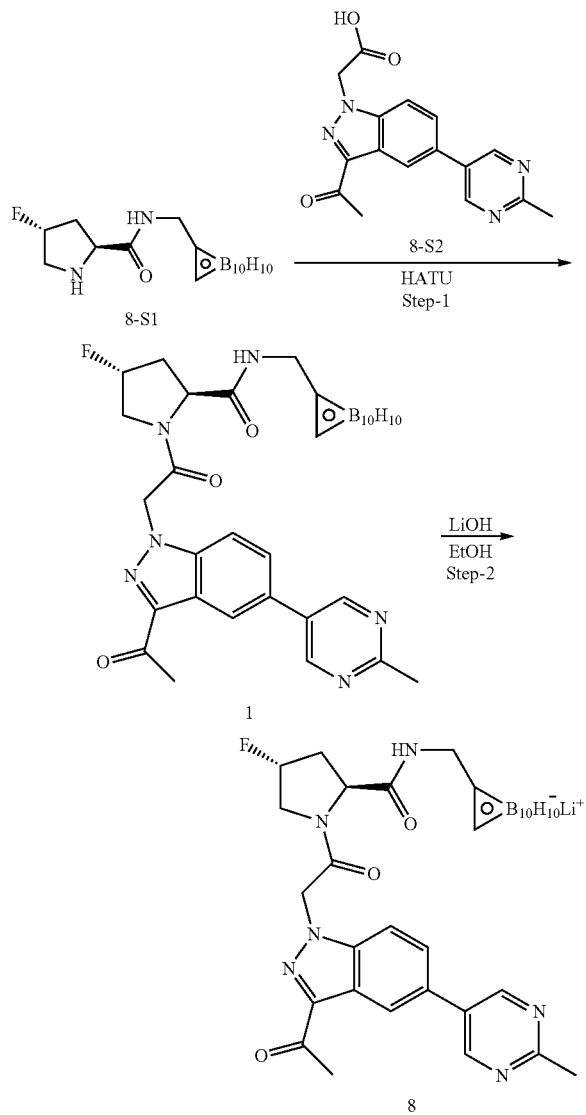

Step 1: Methyl 1-benzyl-6-oxo-1,4,5,6-tetrahydro-pyridine-3-carboxylate (12-S2)

To a solution of benzylamine (6 g, 56.1 mmol) in THF (50 mL) was added 12-S1 (4.55 g, 56.1 mmol) at 0° C. The reaction mixture was stirred at room temperature for 3 hours. The mixture was concentrated under reduced pressure and dissolved in THF (100 mL). Acryloyl chloride (5.55 g, 61.7 mmol) was added to the solution at 0° C. and the reaction mixture was stirred at room temperature overnight. The solution was diluted with EtOAc and washed with saturated aqueous NaHCO$_3$. The organic layer was dried over anhydrous Na$_2$SO$_4$ and concentrated under reduced pressure. The remaining residue was purified by column chromatography on silica gel (eluted with PE/EtOAc=5:1 to 3:1) to afford the title compound (3.5 g, 25.5% yield) as a yellow oil. LC/MS (ESI) m/z: 246 (M+H)$^+$.

Step 2: Methyl 1-benzyl-6-oxopiperidine-3-carboxylate (12-S3)

To a solution of 12-S2 (3.5 g, 14.3 mmol) in EtOH (30 mL) was added Pd/C (10% mol, 151 mg). The mixture was purged with nitrogen, purged with hydrogen, and stirred under an atmosphere of hydrogen (balloon) at room temperature for 1.5 hours. The mixture was filtered through a pad of Celite and washed with EtOH. The filtrate was concentrated to dryness to afford the title compound (3.2 g, 90.2% yield) as a colorless oil. LC/MS (ESI) m/z: 248 (M+H)$^+$.

Step 3: 1-Benzyl-5-(hydroxymethyl)piperidin-2-one (12-S4)

To a solution of 12-S3 (3.2 g, 13.0 mmol) in THF (45 mL) was added LiBH$_4$ (566 mg, 26.0 mmol) at 0° C. The reaction mixture was stirred under an atmosphere of nitrogen at room temperature overnight. The reaction mixture was quenched with water and extracted with EtOAc (50 mL). The organic phase was washed with brine, dried over anhydrous Na$_2$SO$_4$, and concentrated. The remaining residue was purified by column chromatography on silica gel (eluted with DCM/MeOH=50:1) to afford the title compound (2.2 g, 77.3% yield) as a yellow oil. LC/MS (ESI) m/z: 220 (M+H)$^+$.

Step 4: 1-Benzyl-5-(iodomethyl)piperidin-2-one (12-S5)

To a solution of 12-S4 (2.2 g, 10.0 mmol) in DCM (45 mL) under an atmosphere of nitrogen were added Et$_3$N (3.47 mL, 25.0 mmol) and MsCl (1.72 g, 15 mmol) at 0° C. The reaction mixture was stirred at room temperature overnight under an atmosphere of nitrogen. Ice water was added and the organic layer was separated, washed with brine, dried over anhydrous Na$_2$SO$_4$, and filtered. The filtrate was concentrated and diluted with acetone (25 mL). After NaI (4.50 g, 30.0 mmol) was added, the mixture was stirred at reflux for 24 hours. The mixture was cooled to room temperature and concentrated. The remaining residue was diluted with water and extracted with EtOAc. The combined organic phases were washed with brine, dried over anhydrous Na$_2$SO$_4$, and concentrated. The remaining residue was purified by column chromatography on silica gel (eluted with PE/EtOAc=5:1 to 3:1) to afford the title compound (1.5 g, 45.5% yield) as a yellow oil. LC/MS (ESI) m/z: 330 (M+H)$^+$.

Step 5: 3-Benzyl-3-azabicyclo[3.1.1]heptan-2-one (12-S6)

To a solution of 12-S5 (1.5 g, 4.56 mmol) in THF (45 mL) under an atmosphere of nitrogen was added LiHMDS (1 M solution in THF, 13.68 mL, 13.68 mmol) at -20° C. The reaction mixture was stirred at -20° C. for 1.5 hours under an atmosphere of nitrogen. The reaction mixture was quenched by addition of water and extracted with EtOAc (50 mL). The organic phase was washed with brine, dried with anhydrous Na$_2$SO$_4$, and concentrated. The remaining residue was purified by column chromatography on silica gel (eluted with PE/EtOAc=8:1) to afford the title compound (600 mg, 65.5% yield) as a colorless oil. LC/MS (ESI) m/z: 202 (M+H)$^+$.

Step 6: 3-Benzyl-3-azabicyclo[3.1.1]heptane (12-S7)

To a solution of 12-S6 (600 mg, 2.99 mmol) in THF (45 mL) under an atmosphere of nitrogen was added BH$_3$.THF (1 M solution in THF, 8.97 mL, 8.97 mmol) at 0° C. The reaction mixture was stirred at room temperature for 3 hours under an atmosphere of nitrogen. The reaction mixture was quenched with MeOH at 0° C. and concentrated. The remaining residue was diluted with EtOH (4.5 mL) and water (0.5 mL) and then stirred at 100° C. for 3 hours. The mixture was concentrated, diluted with EtOAc, and washed with water and brine. The organic phase was dried over anhydrous Na$_2$SO$_4$ and concentrated to dryness. The remaining residue was purified by column chromatography on silica gel (eluted with DCM/MeOH=50:1) to afford the title compound (300 mg, 53.7% yield) as a colorless oil. LC/MS (ESI) m/z: 188 (M+H)$^+$.

Step 7: 3-Benzyl-3-azabicyclo[3.1.1]heptane hydrochloride (12-S8)

To a solution of compound 12-S7 (300 mg, 1.6 mmol) and concentrated HCl (0.27 mL) in EtOH (35 mL) was added Pd/C (60 mg). The mixture was purged with nitrogen and stirred under an atmosphere of hydrogen (balloon) at room temperature for 2 hours. The mixture was filtered and filtrate was evaporated to afford the title compound (180 mg, 65.9% yield) as a light a brown solid. LC/MS (ESI) m/z: 98 (M+H)$^+$.

Step 8: (3S)-tert-Butyl 5-(azetidin-1-ylmethyl)-3-((6-bromo-3-methylpyridin-2-yl)carbamoyl)-2-azabicyclo[3.1.0]hexane-2-carboxylate (12-S10)

To a solution of 12-S9 (80 mg, 0.19 mmol) in MeCN (2 mL) were added DIPEA (0.13 mL, 0.76 mmol), 12-S8 (18.5 mg, 0.19 mmol), and NaI at 0° C. The reaction mixture was stirred at room temperature for 4 hours. The mixture was concentrated and the remaining residue was diluted with DCM and washed with water. The organic layer was dried over anhydrous Na$_2$SO$_4$, filtered, and concentrated to dryness. The remaining residue was purified by column chromatography on silica gel (eluted with DCM/MeOH=50:1) to afford the title compound (21 mg, 21.9% yield) as a yellow solid. LC/MS (ESI) m/z: 505 (M+H)$^+$.

Step 9: (3S)-5-(Azetidin-1-ylmethyl)-N-(6-bromo-3-methylpyridin-2-yl)-2-azabicyclo[3.1.0]hexane-3-carboxamide (12-S11)

To a solution of 12-S10 (21 mg, 0.042 mmol) in dioxane (1 mL) was added HCl/dioxane (1 mL) at 0° C. The reaction mixture was stirred at room temperature for 2 hours. The mixture was concentrated to dryness to afford the title compound (25 mg, 100% yield) as a brown solid. LC/MS (ESI) m/z: 405 (M+H)$^+$.

Step 10: (3S)-2-(2-(3-Acetyl-5-(2-methylpyrimidin-5-yl)-1H-indazol-1-yl)acetyl)-5-(azetidin-1-ylmethyl)-N-(6-bromo-3-methylpyridin-2-yl)-2-azabicyclo[3.1.0]hexane-3-carboxamide (12)

To a solution of 12-S11 (25 mg, 0.042 mmol) and 12-S12 (13.02 mg, 0.042 mmol) in DMF (2 mL) were added HATU (28.7 mg, 0.076 mmol) and DIPEA (0.029 mL, 0.168 mmol) at 0° C. The reaction mixture was stirred at room temperature overnight. The mixture was diluted with EtOAc and washed with 10% aqueous LiCl solution and brine. The organic layer was dried over anhydrous Na$_2$SO$_4$ and concentrated to dryness. The remaining residue was purified by preparative HPLC to afford 12 (2.1 mg, 7.2% yield) as a white solid. $^1$H NMR (400 MHz, CD$_3$OD) δ 9.01 (s, 2H), 8.56 (s, 1H), 7.80 (s, 2H), 7.58 (d, J=8.2 Hz, 1H), 7.41 (d, J=8.0 Hz, 1H), 5.82 (d, J=17.1 Hz, 1H), 5.67 (d, J=17.1 Hz, 1H), 5.34 (t, J=4.6 Hz, 1H), 4.70 (d, J=4.2 Hz, 1H), 2.75 (d, J=5.0 Hz, 4H), 2.70 (s, 3H), 2.57-2.47 (m, 4H), 2.38-2.27 (m, 4H), 2.22-2.17 (m, 2H), 2.12 (s, 3H), 2.02 (d, J=7.8 Hz, 2H), 1.49-1.46 (m, 1H), 1.39 (d, J=6.8 Hz, 1H), 1.10-1.08 (m, 1H). LC/MS (ESI) m/z: 697 (M+H)$^+$.

Scheme 9. Synthesis of (1R,3S,5R)-2-(2-(3-Acetyl-5-(2-methylpyrimidin-5-yl)-1H-indazol-1-yl)acetyl)-N-(6-bromo-3-isopropylpyridin-2-yl)-5-methyl-2-azabicyclo[3.1.0]hexane-3-carboxamide (14)

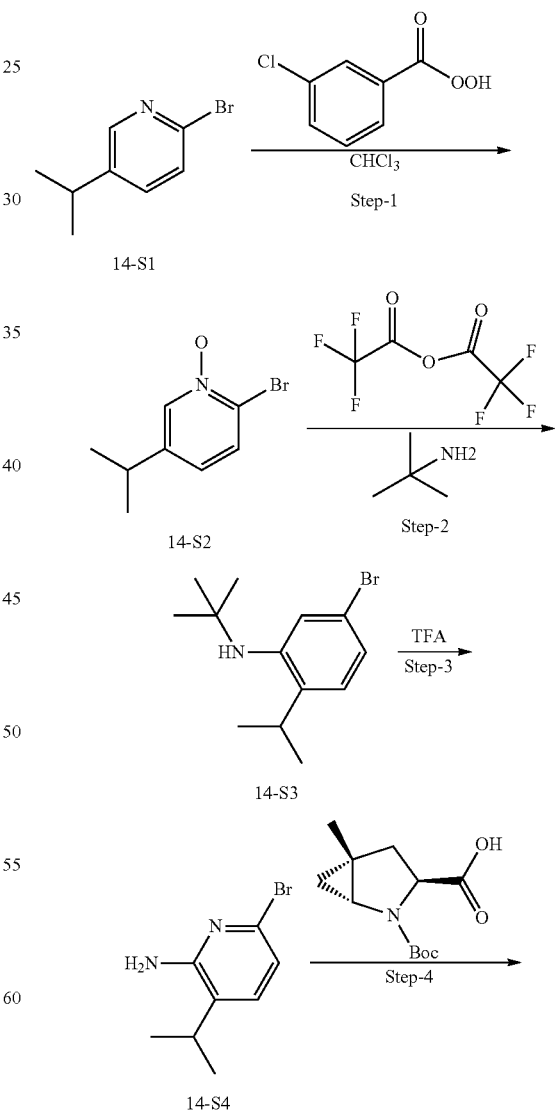

-continued

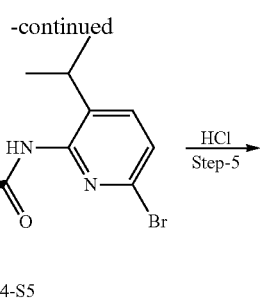

14-S5

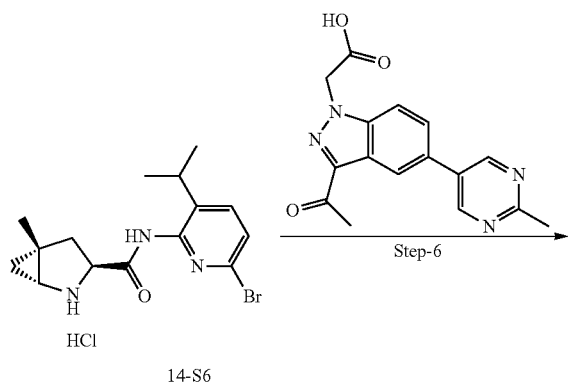

14-S6

14

Step 1: 2-Bromo-5-isopropyl-1-(oxidanyl)-pyridine (14-S2)

To a stirred solution of 2-bromo-5-isopropylpyridine (14-S1, 3 g, 1 equiv) in CHCl₃ (200 mL) was added 3-chlorobenzoperoxoic acid (10 g, 3 equiv). The reaction mixture was heated to 50° C. until completion. The reaction mixture was cooled and saturated aqueous NaHCO₃ solution (100 mL) was added. The organic and aqueous layers were separated and the organic layer was washed with saturated aqueous NaHCO₃ (100 mL×3). The combined organic layers were concentrated to dryness. The residue was purified by column chromatography on SiO₂ gel (eluted with 5% MeOH in DCM) to afford 14-S2 (2.6 g, 80%).

Step 2: 5-Bromo-N-(tert-butyl)-2-isopropylaniline (14-S3)

To a stirred solution of 14-S2 (812 mg, 1 equiv) and 2-methylpropan-2-amine (1.97 mL, 5 equiv) in DCM (100 mL), trifluoroacidic anhydride (0.7 mL, 1.1 equiv) was added dropwise at 0-5° C. under an atmosphere of argon. The reaction mixture was stirred at 0-5° C. for 1 hour and TFAA solution was added (0.7 mL in 5 mL DCM, I equiv)) followed by 2-methylpropan-2-amine (0.4 mL, 1 equiv). The reaction mixture was neutralized with aqueous saturated NaHCO₃ solution (50 mL). The organic layer was washed with brine (50 mL), dried over Na₂SO₄, and concentrated to dryness. The residue was purified by column chromatography on silica gel (eluted by hexanes/EtOAc=3:1 to afford 14-S3 (397 mg, 39%).

Step 3: 5-Bromo-N-(tert-butyl)-2-isopropylaniline (14-S4)

TFA (10 mL) was added to 14-S3 (397 mg) and the reaction mixture was heated at 70° C. The reaction mixture was concentrated to dryness and the residue was dissolved in DCM (15 mL), washed with aqueous saturated NaHCO₃ solution (15 mL). The organic layer was dried over Na₂SO₄ and concentrated to dryness to afford 14-S4 (316 mg, quantitative yield)

Step 4: tert-Butyl (1R,3S,5R)-3-((6-Bromo-3-isopropylpyridin-2-yl)carbamoyl)-5-methyl-2-azabicyclo[3.1.0]hexane-2-carboxylate (14-S5)

To a stirred solution of (1R, 3S, 5R)-2-(tert-butoxycarbonyl)-5-methyl-2-azabicyclo[3.1.0]hexane-3-carboxylic acid (99 mg, 1 equiv), 14-S4 (89 mg, 1 equiv) in DCM (8 mL) and pyridine (0.17 mL, 5 equiv) was added. POCl₃ was then added dropwise (0.04 mL, 2 equiv) at 0-5° C. under an atmosphere of argon. The reaction mixture was warmed to room temperature and stirred for 2 hours. The reaction was then diluted with DCM (10 mL), neutralized with aqueous saturated NaHCO₃ solution (10 mL), and the aqueous layer was extracted with DCM (1×10 mL). The combined organic layers were washed with brine (10 mL), dried over Na₂SO₄, and concentrated to dryness. The residue was purified by column chromatography on silica gel (eluted by 5% MeOH in DCM gradient) to afford 14-S5 (130 mg, 73%).

Step 5: (1R,3S,5R)—N-(6-Bromo-3-isopropylpyridin-2-yl)-5-methyl-2-azabicyclo[3.1.0]hexane-3-carboxamide Hydrochloride (14-S6)

To a solution of 14-S5 (130 mg) in DCM (5 mL) was added TFA (5 mL). The resulting solution was stirred at room temperature for 3 hours. The reaction mixture was concentrated to dryness to afford 14-S6 as TFA salt (135 mg, quantitative yield).

Step 6: (1R,3S,5R)-2-(2-(3-Acetyl-5-(2-methylpyrimidin-5-yl)-1H-indazol-1-yl)acetyl)-N-(6-bromo-3-isopropylpyridin-2-yl)-5-methyl-2-azabicyclo[3.1.0]hexane-3-carboxamide (14)

To a solution of 14-S6 (72 mg, 1 equiv), 2-(3-acetyl-5-(2-methylpyrimidin-5-yl)-1H-indazol-1-yl)acetic acid (50 mg, 1.2 equiv) in DMF (8 mL) and DIPEA (0.17 ml, 5 equiv) was added HATU (70 mg, 1.2 equiv) at 0° C. under an atmosphere of argon. The reaction mixture was stirred at room temperature for 3 hours before it was diluted with EtOAc (25 mL) and water (15 mL). The aqueous layer was extracted with EtOAc (15 mL) and the combined organic layers were washed with brine, dried over anhydrous Na₂SO₄, and concentrated to dryness. The residue was purified by column chromatography on silica gel (eluted by DCM/MeOH=10:1) to afford 14 (84 mg, 82%). $^1$H NMR (400 MHz, DMSO-d$_6$) δ 10.11 (s, 1H), 9.05 (s, 2H), 8.45 (s, 1H), 7.87 (s, 2H), 7.75 (d, 1H, J=8.3 Hz), 7.54 (d, 1H, J=8.3 Hz), 5.91 (d, 1H, J=17.5 Hz), 5.59 (d, 1H, J=17.5 Hz), 4.41-4.46 (m, 1H), 3.58 (t, 11H, J=5.4 Hz), 3.16-3.19 (m, 1H), 2.89-2.97 (m, 1H), 2.70 (s, 3H), 2.68 (s, 3H), 2.54-2.58 (m, 1H), 2.01-2.09 (m, 1H), 1.33 (s, 3H), 1.16-1.27 (m, 1H), 1.03-1.09 (m, 6H).

Scheme 10. Synthesis of (1R,3S,5R)-2-(2-(3-Acetyl-5-(2-methylpyrimidin-5-yl)-1H-pyrazolo[3,4-c]pyridin-1-yl)acetyl)-N-(6-bromo-3-methylpyridin-2-yl)-5-methyl-2-azabicyclo[3.1.0]hexane-3-carboxamide (15)

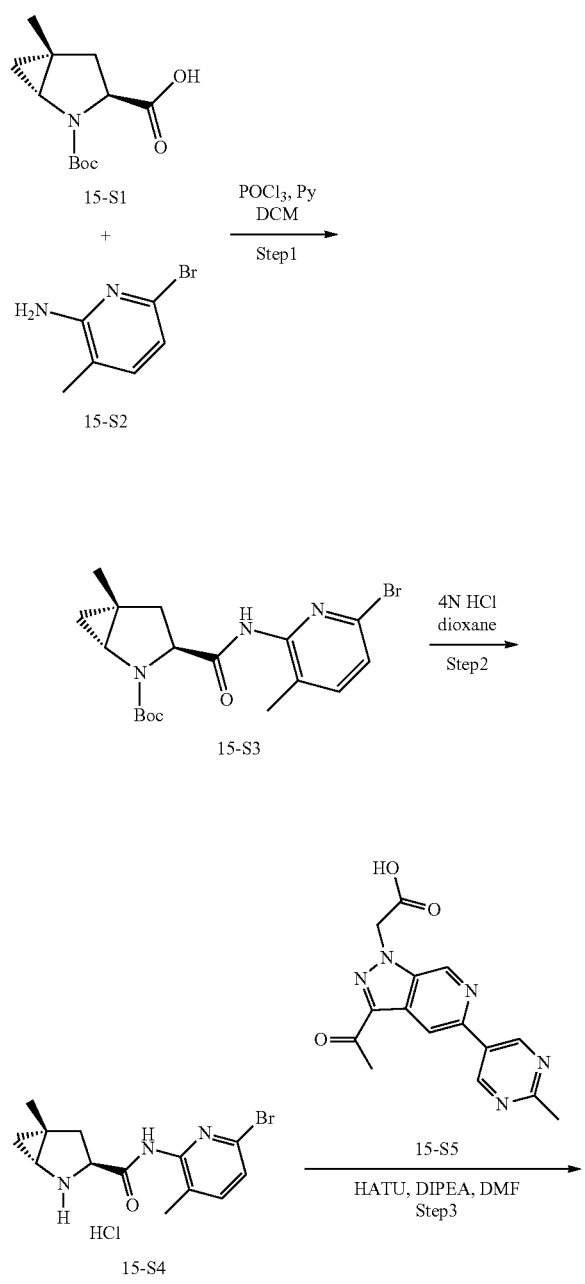

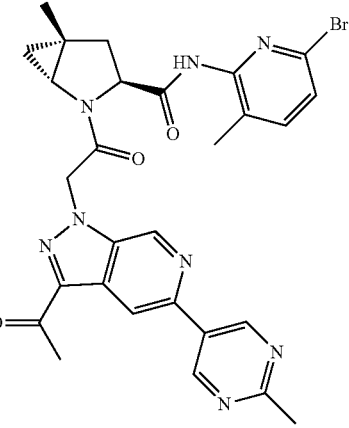

15

The above scheme and following detailed description depicts one non-limiting method for synthesizing compounds via the following steps: 1) the formation of an amide bond between the B-ring and the C-ring by first generating an acyl chloride B-ring with POCl$_3$; 2) the removal of the Boc-group using an acid; and, 3) the formation of an amide bond between the C-ring (already linked to the B-ring) and A-ring utilizing HATU. The skilled artisan will recognize that the C- and B-ring synthetic intermediate can be replaced with other synthetic intermediates to afford additional compounds of the present invention. The skilled artisan will also recognize that the A-ring synthetic intermediate can be replaced with other synthetic intermediates to afford additional compounds of the present invention. The skilled artisan will further recognize that the B-ring linked to the C-ring can be further functionalized prior to the HATU coupling. Additional functionalization includes a Stille cross-coupling and an Ullmann cross-coupling.

Step 1: tert-Butyl (1R,3S,5R)-3-((6-bromo-3-methylpyridin-2-yl)carbamoyl)-5-methyl-2-azabicyclo[3.1.0]hexane-2-carboxylate (15-S3)

(1R,3S,5R)-2-(tert-Butoxycarbonyl)-5-methyl-2-azabicyclo[3.1.0]hexane-3-carboxylic acid (15-S1, 483 mg, 2.0 mmol) and 6-bromo-3-methylpyridin-2-amine (15-S2, 374 mg, 2.0 mmol) were dissolved in anhydrous DCM (15 mL). The reaction was cooled in an ice bath and dry pyridine (0.5 mL, 6.0 mmol) was added in one portion, followed by POCl$_3$ (200 μL, 2.0 mmol). After completion of the addition, the mixture was stirred for 4 hours at 0° C., and the reaction was quenched with water (15 mL). The aqueous phase was extracted with DCM (15 mL×2) and the combined organic layers was washed with brine dried over MgSO$_4$. The solution was filtered and concentrated and the resulting residue was purified to afford 15-S3 (595 mg). $^1$H NMR (400 MHz, DMSO-d$_6$): (major rotamer) δ 0.61 (dd, J=2.4, 5.3 Hz, 1H), 0.68 (t, J=5.6 Hz, 1H), 1.20 (s, 3H), 1.38 (s, 9H), 1.88-1.98 (m, 1H), 2.11 (s, 3H), 2.37-2.45 (m, 1H), 3.12 (s, 1H), 4.06 (dd, J=6.6, 8.9 Hz, 1H), 7.44 (d, J=7.9 Hz, 1H), 7.63 (d, J=7.9 Hz, 1H), 10.17 (s, 1H) ppm.

Step 2: (1R,3S,5R)—N-(6-Bromo-3-methylpyridin-2-yl)-5-methyl-2-azabicyclo[3.1.0]hexane-3-carboxamide hydrochloride (15-S4)

tert-Butyl (1R,3S,5R)-3-((6-bromo-3-methylpyridin-2-yl)carbamoyl)-5-methyl-2-azabicyclo[3.1.0]hexane-2-carboxylate (15-S3, 595 mg) was taken up in 4N HCl dioxane (3.0 mL) and the resulting reaction mixture was stirred at room temperature for 2 hours. After completion of the reaction (as monitored by HPLC), the solvent was removed under reduced pressure. The remaining residue (15-S4) was carried forward without additional purification and used directly in the next step.

Step 3: (1R,3S,5R)-2-(2-(3-Acetyl-5-(2-methylpyrimidin-5-yl)-1H-pyrazolo[3,4-c]pyridin-1-yl)acetyl)-N-(6-bromo-3-methylpyridin-2-yl)-5-methyl-2-azabicyclo[3.1.0]hexane-3-carboxamide (15)

To the solution of (1R,3S,5R)—N-(6-bromo-3-methylpyridin-2-yl)-5-methyl-2-azabicyclo[3.1.0]hexane-3-carboxamide hydrochloride (15-S4, 87 mg, 0.25 mmol), 2-(3-acetyl-5-(2-methylpyrimidin-5-yl)-1H-pyrazolo[3,4-c]pyridin-1-yl)acetic acid (15-S5, 78 mg, 0.25 mmol) in DMF (2.0 mL), HATU (114 mg, 0.3 mmol) was added, followed by the dropwise addition of DIEA (4.0 eq) at room temperature. The mixture was stirred for 1 hour at room temperature before the volatiles were evaporated. The residue was diluted with 10% sodium carbonate (50 mL) and extracted with EtOAc. The combined organic solutions were successively washed with water, brine, and dried over MgSO$_4$. The solution was filtered and the solvent was removed. The residue was purified to afford 15 (136.1 mg). $^1$H NMR (400 MHz, DMSO-d$_6$): (major rotamer) δ 1.02 (t, J=5.4 Hz, 1H), 1.07-1.13 (m, 1H 1.33 (s, 3H), 2.04 (s, 3H), 2.05-2.11 (m, 1H), 2.56 (dd, J=9.2, 13.3 Hz, 1H), 2.69 (s, 3H), 2.70 (s, 3H), 3.54-3.62 (m, 1H), 4.35-4.48 (m, 1H), 5.72 (d, J=17.2 Hz, 1H), 6.04 (d, J=17.3 Hz, 1H), 7.44 (d, J=7.9 Hz, 1H), 7.62 (d, J=8.0 Hz, 1H), 8.60 (s, 1H), 9.30 (s, 1H), 9.34 (s, 2H), 10.27 (s, 1H) ppm. LC (method A): t$_R$=1.71 min. LC/MS (EI) m/z: [M+H]$^+$ 605.44.

(1R,3S,5R)-2-(2-(3-Acetyl-5-(2-methylpyrimidin-5-yl)-1H-indazol-1-yl)acetyl)-N-(3-bromoisoquinolin-1-yl)-5-methyl-2-azabicyclo[3.1.0]hexane-3-carboxamide (73)

$^1$H NMR (400 MHz, DMSO-d$_6$) δ 10.75 (s, 1H), 9.04 (s, 2H), 8.46 (s, 1H), 8.09 (s, 1H), 7.82-7.96 (m, 4H), 7.74-7.80 (m, 1H), 7.51 (t, 1H, J=7.7 Hz), 5.97 (d, 1H, J=17.5 Hz), 5.62 (d, 1H, J=17.5 Hz), 4.51-4.58 (m, 1H), 3.64-3.67 (m, 1H), 2.70 (s, 3H), 2.66 (s, 3H), 2.61-2.65 (m, 1H), 2.14-2.20 (m, 1H), 1.38 (s, 3H), 1.00-1.10 (m, 2H).

(1R,3S,5R)-2-(2-(3-Acetyl-7-methyl-5-(2-methylpyrimidin-5-yl)-1H-indol-1-yl)acetyl)-N-(6-bromo-3-methylpyridin-2-yl)-5-methyl-2-azabicyclo[3.1.0]hexane-3-carboxamide $^1$H NMR (400 MHz, Chloroform-d) δ 0.87 (dd, J=2.4, 5.4 Hz, 1H), 1.15 (t, J=5.4 Hz, 1H), 1.42 (s, 3H), 2.08 (s, 3H), 2.30-2.36 (m, 1H), 2.53 (s, 3H), 2.67 (d, J=14.8 Hz, 1H), 2.72 (s, 3H), 2.79 (s, 3H), 3.10 (d, J=2.8, 1H), 4.83 (d, J=8.3 Hz, 1H), 5.30 (d, J=17.7 Hz, 1H), 5.46 (d, J=17.7 Hz, 1H), 7.16-7.26 (m, 2H), 7.34 (d, J=7.9 Hz, 1H), 7.71 (s, 1H), 8.55 (s, 1H), 8.56 (brs, 1H), 8.89 (s, 2H).

(1R,3S,5R)-2-(2-(3-Acetyl-5-(2-methylpyrimidin-5-yl)-1H-indazol-1-yl)acetyl)-N-(6-bromo-5-fluoro-3-((methylthio)methyl)pyridin-2-yl)-5-methyl-2-azabicyclo[3.1.0]hexane-3-carboxamide $^1$H NMR (400 MHz, DMSO-d$_6$) δ 0.97-1.08 (m, 2H), 1.34 (s, 3H), 1.77 (s, 3H), 2.06 (m, 1H), 2.56 (m, 1H), 2.66 (s, 3H), 2.70 (s, 3H), 3.60 (m, 1H), 4.00-4.80 (m, 2H), 4.40 (m, 1H), 5.59 (m, 1H), 5.92 (m, 1H), 7.85-7.96 (m, 3H), 8.45 (s, 1H), 9.05 (s, 2H), 10.35 (s, 1H).

(2S,4R)-1-(2-(3-Acetyl-5-(2-methylpyrimidin-5-yl)-H-indazol-1-yl)acetyl)-4-fluoro-N-(6-iodopyridin-2-yl)pyrrolidine-2-carboxamide $^1$H-NMR (400 MHz, DMSO-d$_6$) δ 10.95 (s, 1H), 9.03 (s, 2H), 8.42 (s, 1H), 8.00-8.02 (d, J=7.2 Hz, 1H), 7.85-7.86 (m, 2H), 7.51-7.53 (d, J=7.2 Hz, 1H), 7.42-7.46 (t, 1H), 5.82-5.86 (d, J=13.2 Hz, 1H), 5.62-5.66 (d, J=13.2 Hz, 1H), 5.48-5.61 (m, 1H), 4.65-4.69 (m, 1H), 4.18-4.27 (m, 1H), 3.96-4.08 (m, 1H), 2.68 (s, 3H), 2.64 (s, 3H), 2.51-2.56 (m, 1H), 2.06-2.23 (m, 1H). LC/MS (ESI) m/z: 628 (M+H)$^+$.

(2S,4R)-2-(3-Acetyl-5-(2-methylpyrimidin-5-yl)-1-H-pyrazolo[3,4-c]pyridine-1-yl)acetyl)-4-fluoro-N-(pyridine-2-yl)pyrrolidine-2-carboxamide $^1$H-NMR (400 MHz, DMSO-d$_6$) δ 10.66 (s, 1H), 9.03 (s, 2H), 8.41 (s, 1H), 8.28-8.29 (m, 1H), 8.01-8.03 (d, J=8.4 Hz, 1H), 7.85 (m, 2H), 7.72-7.76 (m, 1H), 7.06-7.09 (m, 1H), 5.82-5.86 (d, J=17.2 Hz, 1H), 5.63-5.74 (d, J=17.2 Hz, 1H), 5.62 (m, 0.5H), 5.49 (m, 0.5H), 4.69-4.73 (m, 1H), 4.23-4.28 (m, 1H), 3.95-4.08 (m, 1H), 2.67 (s, 3H), 2.64 (s, 3H), 2.53-2.58 (m, 1H), 2.11-2.21 (m, 1H). LC/MS (ESI) m/z: 502 (M+H)$^+$.

(2S,4R)-1-(2-(3-Acetyl-5-(2-methylpyrimidin-5-yl)-1-H-pyrazolo[3,4-c]pyridine-1-yl)acetyl)-N-(6-bromopyridin-2-yl)4-fluoro-N-methylpyrrolidine-2-carboxamide $^1$H-NMR (400 MHz, DMSO-d$_6$) δ 10.12 (s, 2H), 8.43 (s, 1H), 7.77-7.92 (m, 3H), 7.53-7.55 (d, J=8.0 Hz, 1H), 7.45-7.47 (d, J=8.0 Hz, 1H), 5.76-5.81 (d, J=17.2 Hz, 1H), 5.58-5.62 (d, J=17.2 Hz, 1H), 5.49-5.51 (m, 1H), 4.60-4.63 (m, 1H), 4.18-4.27 (m, 1H), 3.92-4.05 (m, 1H), 3.23 (s, 3H), 2.72 (s, 1H), 2.71 (s, 1H), 2.63-2.69 (m, 1H), 2.20-2.33 (m, 1H). LC/MS (ESI) m/z: 595/597 (M+H)$^+$.

(1R,3S,5R)-2-(2-(3-Acetyl-7-methyl-5-(2-methylpyrimidin-5-yl)-1H-pyrazolo[3,4-c]pyridin-1-yl)acetyl)-N-(6-bromo-4-methylpyridin-2-yl)-5-methyl-2-aza-bicyclo[3.1.0]hexane-3-carboxamide $^1$H-NMR (400 MHz, CD$_3$OD) δ 8.54 (s, 2H), 7.91 (s, 1H), 7.11 (s, 1H), 6.04-6.08 (d, J=17.6 Hz, 1H), 5.84-5.88 (d, J=17.6 Hz, 1H), 4.48-4.49 (m, 1H), 3.56-3.58 (m, 1H), 2.97 (s, 3H), 2.74 (s, 3H), 2.69 (s, 3H), 2.55-2.60 (m, 1H), 2.31 (s, 3H), 2.16-2.21 (m, 1H), 1.39 (s, 3H), 1.10-1.13 (m, 1H), 0.97-0.99 (m, 1H). LC/MS (ESI) m/z: 617/619 (M+H)$^+$.

(1R,3S,5R)-2-(2-(3-Acetyl-5-(2-methylpyrimidin-5-yl)-1H-indazol-1-yl)acetyl)-5-methyl-N-(5-methyl-[2,2'-bipyridin]-6-yl)-2-azabicyclo[3.1.0]hexane-3-carboxamide $^1$H-NMR (400 MHz, CD$_3$OD) δ 8.96 (s, 2H), 8.58 (d, J=4.8 Hz, 1H), 8.52-8.49 (m, 1H), 8.25 (d, J=8.0 Hz, 1H), 8.09 (d, J=8.0 Hz, 1H), 7.82 (t, J=7.6 Hz, 1H), 7.77-7.69 (m, 3H), 7.36 (t, J=6.4 Hz, 1H), 5.79 (d, J=17.2 Hz, 1H), 5.63 (d, J=17.2 Hz, 1H), 4.67-4.55 (m, 2H), 3.56-3.52 (m, 1H), 2.74 (s, 3H), 2.69 (s, 3H), 2.35 (dd, J=13.6, 13.6 Hz, 1H), 2.23 (s, 3H), 1.42 (s, 3H), 1.11 (t, J=5.2 Hz, 1H), 1.03-0.99 (m, 1H). LC/MS (ESI) m/z: 601 (M+H)+.

(1R,3S,5R)-2-(2-(3-Acetyl-7-methyl-5-(2-methylpyrimidin-5-yl)-1H-indazol-1-yl)acetyl)-5-methyl-N-(6-(pyridin-2-yloxy)pyridin-2-yl)-2-azabicyclo[3.1.0]hexane-3-carboxamide $^1$H-NMR (400 MHz, DMSO-d$_6$) δ 10.42 (s, 1H), 9.01 (s, 2H), 8.30 (d, J=2.0 Hz, 1H), 8.18 (m, 1H), 7.91-7.82 (m, 3H), 7.60 (dd, J=1.6, 1.6 Hz, 1H), 7.16 (m, 1H), 7.07 (m, 1H), 6.81-6.77 (m, 1H), 6.07 (d, J=17.6 Hz, 1H), 5.64 (d, J=17.6 Hz, 1H), 4.41 (dd, J=9.2, 9.2 Hz, 1H), 3.62 (dd, J=5.6, 5.6 Hz, 1H), 2.72-2.62 (m, 9H), 2.43 (d, J=12.0 Hz, 1H), 1.96 (dd, J=13.2, 13.2 Hz, 1H), 1.29 (s, 3H), 0.98 (t, J=5.2 Hz, 1H), 0.86-0.82 (m, 1H). LC/MS (ESI) m/z: 617 (M+H)+.

(1R,3S,5R)-2-{2-[3-Acetyl-7-methyl-5-(2-methylpyrimidin-5-yl) indazol-1-yl]acetyl}-5-methyl-N-{2-oxo-[1,2'-bipyridine]-6'-yl}-2-azabicyclo[3.1.0]hexane-3-carboxamide $^1$H-NMR (400 MHz, DMSO-d$_6$) δ 10.70 (s, 1H), 9.01 (s, 2H), 8.30 (s, 1H), 8.09 (d, J=8.2 Hz, 1H), 7.98-7.93 (m, 1H), 7.77 (d, J=5.4 Hz, 1H), 7.61 (s, 1H), 7.52-7.47 (m, 1H), 7.38 (d, J=7.7 Hz, 1H), 6.47 (d, J=9.2 Hz, 1H), 6.33-6.28 (m, 1H), 6.09 (d, J=17.9 Hz, 1H), 5.66 (d, J=17.8 Hz, 1H), 4.48-4.43 (m, 1H), 3.64 (m, 1H), 2.70 (s, 3H), 2.67 (s, 3H), 2.64 (s, 3H), 2.05-1.99 (m, 1H), 1.81 (m, 1H), 1.31 (s, 3H), 1.02-0.97 (m, 1H), 0.90 (m, 1H). LC/MS (ESI) m/z: 617 (M+H)+.

(1R,3S,5R)-2-(2-(3-Acetyl-7-methyl-5-(2-methylpyrimidin-5-yl)-1H-indazol-1-yl)acetyl)-N-(6-bromo-5-fluoro-3-methylpyridin-2-yl)-5-((5-methyl-1,3,4-oxadiazol-2-yl)methyl)-2-azabicyclo[3.1.0]hexane-3-carboxamide $^1$H-NMR (400 MHz, DMSO-d$_6$) δ 10.32 (s, 1H), 9.33 (s, 2H), 8.50 (s, 1H), 7.82 (d, J=8.4 Hz, 1H), 6.17 (d, J=18.0 Hz, 1H), 5.80 (d, J=18.0 Hz, 1H), 4.45 (m, 1H), 3.86 (m, 1H), 3.25 (d, J=16.0 Hz, 1H), 3.10 (d, J=16.0 Hz, 1H), 2.92 (s, 3H), 2.68 (s, 3H), 2.67 (s, 3H), 2.66-2.62 (m, 1H), 2.46 (s, 3H), 2.18 (m, 1H), 2.03 (s, 3H), 1.25 (m, 1H), 1.16 (m, 1H). LC/MS (ESI) m/z: 717/719 (M+H)+.

(1R,3S,5R)-2-(2-(3-Acetyl-7-methyl-5-(2-methylpyrimidin-5-yl)-1H-indazol-1-yl)acetyl)-N-(6-bromo-3-chloropyridin-2-yl)-5-((5-methyl-1,3,4-oxadiazol-2-yl)methyl)-2-azabicyclo[3.1.0]hexane-3-carboxamide $^1$H-NMR (400 MHz, CD$_3$OD) δ 9.00 (s, 2H), 8.42 (s, 1H), 7.75 (d, J=8.3 Hz, 1H), 7.54 (s, 1H), 7.43 (d, J=8.3 Hz, 1H), 6.01 (d, J=17.7 Hz, 1H), 5.83 (d, J=17.8 Hz, 1H), 4.76 (m, 1H), 3.87-3.84 (m, 1H), 3.20 (s, 2H), 2.78 (s, 3H), 2.74 (s, 3H), 2.69 (s, 3H), 2.67 (d, J=4.3 Hz, 1H), 2.54 (s, 3H), 2.47 (d, J=10.3 Hz, 1H), 1.42 (m, 1H), 1.21 (m, 1H). LC/MS (ESI) m/z: 718/720 (M+H)+.

(1R,3S,5R)-2-(2-(3-Acetyl-7-methyl-5-(2-methylpyrimidin-5-yl)-1H-indazol-1-yl)acetyl)-N-(6-bromopyrazin-2-yl)-5-((3-methyl-1,2,4-oxadiazol-5-yl)methyl)-2-azabicyclo[3.1.0]hexane-3-carboxamide $^1$H-NMR (400 MHz, CD$_3$OD) δ: 9.27 (s, 1H), 8.98 (s, 2H), 8.42 (s, 1H), 8.40 (d, J=1.1 Hz, 1H), 7.53 (s, 1H), 6.01 (d, J=17.7 Hz, 1H), 5.80 (d, J=17.7 Hz, 1H), 4.68-4.49 (m, 2H), 3.87 (dd, J=5.8, 2.7 Hz, 1H), 3.23 (d, J=1.9 Hz, 2H), 2.77 (s, 3H), 2.73 (s, 3H), 2.68 (s, 3H), 2.67-2.62 (m, 1H), 2.45 (dd, J=13.8, 3.6 Hz, 1H), 2.31 (s, 3H), 1.40 (m, 1H), 1.20 (m, 1H). LC/MS (ESI) m/z: 685/687 [M+H]+.

(2S,4S)-1-{2-[3-Acetyl-5-(2-methylpyrimidin-5-yl)indazol-1-yl] acetyl}-N-(6-bromopyridin-2-yl)-4-fluoro-4-(1,2,3-triazol-1-ylmethyl)pyrrolidine-2-carboxamide $^1$H-NMR (400 MHz, CD$_3$OD) δ 9.01 (s, 2H), 8.54 (s, 1H), 8.13 (s, 1H), 7.85 (s, 1H), 7.82-7.79 (m, 2H), 7.55 (d, J=8.3 Hz, 1H), 7.38 (d, J=7.9 Hz, 1H), 5.67-5.55 (m, 2H), 5.11 (d, J=10.4 Hz, 1H), 5.05 (d, J=4.8 Hz, 1H), 5.01-4.97 (m, 1H), 4.38-4.28 (m, 1H), 4.16-4.08 (m, 1H), 2.76 (s, 3H), 2.70 (s, 3H), 2.67-2.50 (m, 2H), 2.10 (s, 3H). LC/MS (ESI) m/z: 675 (M+H)+.

(2S,4R)-1-{2-[3-Acetyl-5-(2-methylpyrimidin-5-yl)indazol-acetyl}-N-(6-bromo-3-methylpyridin-2-yl)-4-[(dimethylamino)methyl]-4-fluoropyrrolidine-2-carboxamide $^1$H-NMR (400 MHz, DMSO-d$_6$) δ 10.19 (s, 1H), 9.05 (s, 2H), 8.44 (s, 1H), 7.92-7.85 (m, 2H), 7.63 (d, J=8.0 Hz, 1H), 7.46 (d, J=7.9 Hz, 1H), 5.74 (d, J=16.4 Hz, 1H), 5.62 (d, J=17.2 Hz, 1H), 4.70 (d, J=9.6 Hz, 1H), 4.20-4.08 (m, 2H), 2.78-2.71 (m, 2H), 2.69 (s, 3H), 2.65 (s, 3H), 2.47-2.35 (m, 2H), 2.32 (s, 6H), 2.02 (s, 3H). LC/MS (ESI) m/z: 651 (M+H)+.

(2S,4R)-1-(2-(3-Acetyl-7-methyl-5-(2-methylpyrimidin-5-yl)-1H-pyrazolo[3,4-c]pyridin-1-yl)acetyl)-N-(6-bromo-5-fluoro-3-methylpyridin-2-yl)-4-fluoro-4-(fluoromethyl)pyrrolidine-2-carboxamide $^1$H-NMR (400 MHz, DMSO-d$_6$) δ 9.32 (s, 2H), 8.49 (s, 1H), 7.80 (d, J=8.8 Hz, 1H), 6.06 (d, J=18.0 Hz, 1H), 5.88 (d, J=17.8 Hz, 1H), 4.85-4.68 (m, 3H), 4.36 (dd, J=19.0, 12.3 Hz, 1H), 4.14-4.05 (m, 1H), 2.90 (s, 3H), 2.68 (d, J=6.5 Hz, 6H), 2.35-2.24 (m, 2H), 2.02 (s, 3H). LC/MS (ESI) m/z: 659 (M+H)+.

(2S,4R)-1-(2-(3-Acetyl-7-methyl-5-(2-methylpyrimidin-5-yl)-1H-pyrazolo[3,4-c]pyridin-1-yl)acetyl)-N-(6-bromopyrazin-2-yl)-4-fluoro-4-(fluoromethyl)pyrrolidine-2-carboxamide $^1$H-NMR (400 MHz, DMSO-d$_6$) δ 11.41 (s, 1H), 9.32 (s, 2H), 9.25 (s, 1H), 8.56-8.53 (m, 1H), 8.48 (s, 1H), 6.09 (d, J=18.0 Hz, 1H), 5.91 (d, J=17.9 Hz, 1H), 4.94-4.78 (m, 3H), 4.38 (dd, J=18.6, 12.2 Hz, 1H), 4.17-4.06 (m, 1H), 2.92 (s, 3H), 2.68 (s, 3H), 2.67 (s, 3H), 2.63-2.56 (m, 1H), 2.33-2.23 (m, 1H). LC/MS (ESI) m/z: 628 (M+H)+.

(2S,4S)-1-(2-(3-Acetyl-5-(2-methylpyrimidin-5-yl)-1H-indazol-1-yl)acetyl)-N-(6-bromo-3-methylpyridin-2-yl)-4-fluoro-4-(fluoromethyl)pyrrolidine-2-carboxamide $^1$H-NMR (400 MHz, DMSO-d$_6$) δ 10.28 (s, 1H), 9.05 (s, 2H), 8.44 (d, J=1.2 Hz, 1H), 7.64 (d, J=8.4 Hz, 1H), 7.47 (d, J=7.9 Hz, 1H), 5.75 (d, J=17.3 Hz, 1H), 5.63 (d, J=17.3 Hz, 1H), 4.88-4.72 (m, 3H), 4.30-4.16 (m, 2H), 2.69 (s, 3H), 2.65 (s, 3H), 2.63-2.53 (m, 1H), 2.43-2.34 (m, 1H), 2.03 (s, 3H). LC/MS (ESI) m/z: 626 (M+H)$^+$.

(1R,3S,5R)-2-(2-(3-Acetyl-7-methyl-5-(2-methylpyrimidin-5-yl)-1H-indazol-1-yl)acetyl)-N-(6-bromo-5-fluoro-3-methylpyridin-2-yl)-5-((3-methyl-1,2,4-oxadiazol-5-yl)methyl)-2-azabicyclo[3.1.0]hexane-3-carboxamide $^1$H-NMR (400 MHz, CD$_3$OD) δ 8.99 (d, J=5.2 Hz, 2H), 8.40 (d, J=1.1 Hz, 1H), 7.61-7.46 (m, 2H), 5.98 (d, J=17.7 Hz, 1H), 5.80 (d, J=17.7 Hz, 1H), 4.57 (dd, J=9.2, 5.0 Hz, 2H), 3.85 (dd, J=5.7, 2.7 Hz, 1H), 3.37 (d, J=16.1 Hz, 1H), 3.16 (d, J=16.1 Hz, 1H), 2.75 (s, 3H), 2.73 (d, J=7.8 Hz, 3H), 2.72-2.68 (m, 1H), 2.67 (s, 3H), 2.48 (dd, J=13.7, 4.3 Hz, 1H), 2.36 (s, 3H), 2.12 (s, 3H), 1.37 (m, 1H), 1.29 (m, 1H), 1.18 (m, 1H). LC/MS (ESI) m/z: 716/718 [M+H]$^+$.

(1R,3S,5R)-2-(2-(3-Acetyl-7-methyl-5-(2-methylpyrimidin-5-yl)-1H-indazol-1-yl)acetyl)-N-(6-bromo-3-chloropyridin-2-yl)-5-((3-methyl-1,2,4-oxadiazol-5-yl)methyl)-2-azabicyclo[3.1.0]hexane-3-carboxamide $^1$H-NMR (400 MHz, CD$_3$OD) δ 8.99 (s, 2H), 8.42 (s, 1H), 7.76 (d, J=8.3 Hz, 1H), 7.54 (s, 1H), 7.44 (d, J=8.3 Hz, 1H), 6.00 (d, J=17.6 Hz, 1H), 5.82 (d, J=17.8 Hz, 1H), 4.74 (d, J=8.2 Hz, 1H), 3.85 (d, J=3.1 Hz, 1H), 3.40 (s, 1H), 3.14 (d, J=15.9 Hz, 1H), 2.77 (s, 3H), 2.74 (s, 3H), 2.68 (s, 3H), 2.57-2.50 (m, 1H), 2.35 (s, 3H), 1.41 (t, J=5.5 Hz, 1H), 1.34-1.26 (m, 1H), 1.20 (m, 1H). LC/MS (ESI) m/z: 718/720 [M+H]$^+$.

(1R,3S,5R)-2-(2-(3-Acetyl-7-methyl-5-(2-methylpyrimidin-5-yl)-1H-indazol-1-yl)acetyl)-5-((3-methyl-1,2,4-oxadiazol-5-yl)methyl)-N-(3-methyl-6-(trifluoromethyl)pyridin-2-yl)-2-azabicyclo[3.1.0]hexane-3-carboxamide $^1$H-NMR (400 MHz, CD$_3$OD) δ 8.99 (s, 2H), 8.41 (s, 1H), 7.86 (d, J=7.8 Hz, 1H), 7.59 (d, J=7.8 Hz, 1H), 7.53 (s, 1H), 6.00 (M, 1H), 5.82 (M, 1H), 4.66-4.61 (m, 1H), 3.86 (m, 1H), 3.38 (m, 1H), 3.15 (m, 1H), 2.75 (m, 6H), 2.68 (s, 3H), 2.54-2.49 (m, 1H), 2.33 (s, 4H), 2.23 (s, 3H), 1.38 (m, 1H), 1.18 (m, 1H). LC/MS (ESI) m/z: 688 (M+H)$^+$.

(1R, 3S, 5R)-2-(2-(3-Acetyl-7-methyl-5-(2-methylpyrimidin-5-yl)-1H-indazol-1-yl) cetyl)-5-((5-methyl-1, 3, 4-oxadiazol-2-yl) methyl)-N-(3-methyl-6-(trifluoromethyl) pyridin-2-yl)-2-azabicyclo 13.1.01 hexane-3-carboxamide $^1$H-NMR (400 MHz, DMSO-d$_6$) δ 10.46 (s, 1H), 9.02 (s, 2H), 8.32 (d, J=0.9 Hz, 1H), 7.94 (d, J=7.6 Hz, 1H), 7.70 (d, J=7.6 Hz, 1H), 7.62 (s, 1H), 6.08 (d, J=17.6 Hz, 1H), 5.70 (d, J=18.0 Hz, 1H), 5.32 (t, J=4.4 Hz, 1H), 4.51 (dd, J=9.6, 5.2 Hz, 1H), 3.85 (dd, J=5.2, 2.4 Hz, 1H), 3.27-3.22 (m, 1H), 3.12-3.06 (m, 1H), 2.92-2.51 (m, 9H), 2.45 (s, 3H), 2.22-2.11 (m, 3H), 2.03-1.96 (m, 2H), 1.48-1.42 (m, 1H), 1.16-1.12 (m, 1H). LC/MS (ESI) m/z: 688 (M+H)$^+$.

(1R, 3S, 5R)-2-(2-(3-Acetyl-5-(2-methylpyrimidin-5-yl)-1H-pyrazolo [3, 4-c] pyridin-1-yl) acetyl)-N-(6-bromo-3-methylpyridin-2-yl)-5-(2-oxopropyl)-2-azabicyclo 13.1.01 hexane-3-carboxamide $^1$H-NMR (400 MHz, DMSO-d$_6$) δ 10.26 (s, 1H), 9.35 (s, 2H), 9.32 (d, J=1.2 Hz, 1H), 8.62 (d, J=1.2 Hz, 1H), 7.62 (d, J=8.0 Hz, 1H), 7.44 (d, J=8.0 Hz, 1H), 6.07 (d, J=17.2 Hz, 1H), 5.74 (d, J=17.2 Hz, 1H), 4.43 (dd, J=9.6, 5.2 Hz, 1H), 3.71 (dd, J=5.6, 2.4 Hz, 1H), 2.93 (d, J=16.8 Hz, 1H), 2.69 (d, J=3.2 Hz, 6H), 2.64-2.56 (m, 2H), 2.16 (s, 3H), 2.11-2.05 (m, 1H), 2.03 (s, 3H), 1.21-1.18 (m, 1H), 1.13-1.08 (m, 1H). LC/MS (ESI) m/z: 646 (M+H)$^+$.

(1R,2S,5S)-3-(2-(3-Acetyl-5-(2-methylpyrimidin-5-yl)-1H-indazol-1-yl)acetyl)-N-(6-bromo-3-methylpyridin-2-yl)-3-azabicyclo[3.1.0]hexane-2-carboxamide $^1$H NMR (400 MHz, DMSO-d$_6$) δ 10.87 (s, 1H), 9.03 (s, 2H), 8.41 (s, 1H), 7.86-7.85 (m, 2H), 7.59 (d, J=8.0 Hz, 1H), 7.40 (d, J=8.0 Hz, 1H), 5.63-5.53 (m, 2H), 4.59-4.58 (m, 1H), 4.05-4.01 (m, 1H), 3.89-3.87 (m, 1H), 2.67 (s, 3H), 2.63 (s, 3H), 2.00 (s, 3H), 1.92-1.91 (m, 1H), 1.90-1.85 (m, 1H), 0.86-0.75 (m, 2H).

(1R,3S,5R)-2-{2-[3-Acetyl-5-(2-methylpyrimidin-5-yl)indazol-1-yl]acetyl}-N-(6-bromo-3-methylpyridin-2-yl)-5-[(4-ethyl-1, 3-thiazol-2-yl)methyl]-2-azabicyclo[3.1.0]hexane-3-carboxamide $^1$H NMR (400 MHz, Chloroform-d) δ 8.89 (s, 2H), 8.83 (s, 1H), 8.56 (t, J=1.3 Hz, 1H), 7.61 (d, J=1.3 Hz, 2H), 7.42 (d, J=1.1 Hz, 1H), 7.33 (dd, J=0.8, 7.9 Hz, 1H), 7.20 (s, 0H), 5.58-5.44 (m, 2H), 4.78 (dd, J=3.5, 9.3 Hz, 1H), 3.54 (dd, J=2.7, 5.7 Hz, 1H), 3.41 (d, J=15.8 Hz, 1H), 3.24-3.11 (m, 2H), 2.80 (s, 4H), 2.68 (s, 3H), 2.41 (dd, J=9.0, 13.7 Hz, 1H), 1.33 (d, J=6.8 Hz, 6H), 0.99 (dd, J=2.7, 5.9 Hz, 1H). LC (method A): t$_R$=2.20 min. LC/MS (EI) m/z: [M+H]$^+$ 727.

(1R,3S,5R)-2-(2-(3-Acetyl-5-(2-methylpyrimidin-5-yl)-1H-pyrazolo[3,4-c]pyridin-1-yl)acetyl)-N-(6-bromo-3-fluoropyridin-2-yl)-5-methyl-2-azabicyclo[3.1.0]hexane-3-carboxamide $^1$H-NMR (400 MHz, DMSO-d$_6$) δ 10.55 (s, 1H), 9.35 (s, 2H), 9.32 (d, J=1.2 Hz, 1H), 8.62 (d, J=1.2 Hz, 1H), 7.81-7.75 (m, 1H), 7.57 (dd, J=8.4, 3.2 Hz, 1H), 6.06 (d, J=17.2 Hz, 1H), 5.74 (d, J=17.2 Hz, 1H), 4.45 (m, 1H), 3.59 (m, 1H), 2.71 (s, 3H), 2.69 (s, 3H), 2.53-2.60 (m, 1H), 2.03 (dd, J=13.2, 5.2 Hz, 1H), 1.31 (s, 3H), 1.11 (m, 1H), 1.02 (t, m, 1H). LC/MS (ESI) m/z: 607 (M+H)$^+$.

(1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-((diisopropylamino)methyl)-2-azabicyclo[3.1.0]hexane-3-carboxamide $^1$H-NMR (400 MHz, CD$_3$OD) δ 9.00 (s, 2H), 8.43 (s, 1H), 7.54 (d, J=7.4 Hz, 2H), 7.37 (d, J=8.0 Hz, 1H), 5.98 (d, J=17.7 Hz, 1H), 5.81 (d, J=17.7 Hz, 1H), 4.59-4.57 (m, 1H), 3.52 (dd, J=4.9, 2.0 Hz, 1H), 3.21-3.19 (m, 1H), 3.14-3.11 (m, 1H), 2.77 (s, 3H), 2.74 (s, 3H), 2.68 (s, 3H), 2.64-2.62 (m, 1H), 2.60-2.58 (m, 1H), 2.48-2.43 (m, 2H), 2.13 (s, 3H), 1.30-1.29 (m, 1H), 1.20-1.18 (m, 1H), 1.08-1.00 (m, 12H). LC/MS (ESI) m/z: 715 (M+H)$^+$.

Scheme 11. Synthesis of (1R,3S,5R)-2-(2-(3-Acetyl-7-methyl-5-(2-methylpyrimidin-5-yl)-1H-indazol-1-yl)acetyl)-n-((e)-2-fluoro-3-phenylbut-2-en-1-yl)-2-azabicyclo[3.1.0]hexane-3-carboxamide (17)

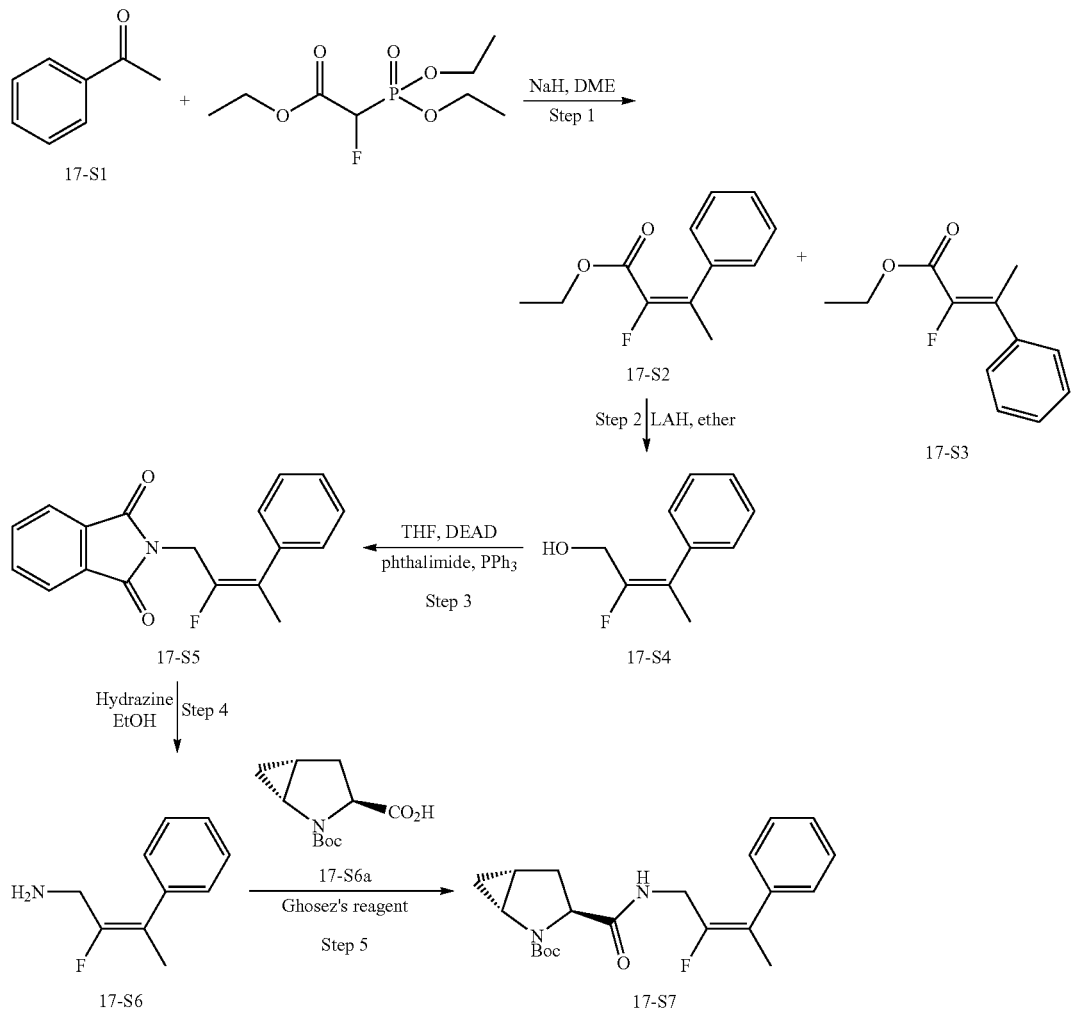

The three-part synthesis shown below and the accompanying detailed description depicts one non-limiting method for synthesizing compounds by first generating intermediate 17-S7 by using Ghosez's reagent to generate an amide bond. Intermediate 17-S7 is the coupled to the A-ring using a coupling reagent, such as HATU. The skilled artisan will recognize that the A-ring synthetic intermediate shown below can be replaced with other A-ring synthetic intermediates to afford additional compounds of the present invention.

Synthesis of tert-Butyl (1R,3S,5R)-3-(((E)-2-fluoro-3-phenylbut-2-en-1-yl)carbamoyl)-2-azabicyclo[3.1.0]hexane-2-carboxylate (Intermediate 17-S7)

Step 1: Ethyl (E)-2-fluoro-3-phenylbut-2-enoate (S2) and Ethyl (Z)-2-fluoro-3-phenylbut-2-enoate (17-S3)

Ethyl 2-(diethoxyphosphoryl)-2-fluoroacetate (5 g) was added dropwise to a stirred solution of NaH (0.9 g, 60% in mineral oil) in DME (50 mL) at 0° C. The cooling bath was removed and the reaction mixture was stirred at room temperature for 1 hour. Benzaldehyde (3.6 mL) was added at room temperature and the reaction mixture was stirred at 90° C. overnight. The reaction mixture was cooled to room temperature, diluted with ether, washed with water, dried ($Na_2SO_4$), and concentrated. The resultant residue was purified by silica gel flash column chromatography (eluent: 0-0.5% EtOAc in hexanes). Ethyl (Z)-2-fluoro-3-phenylbut-2-enoate (17-S3) eluted first as colorless liquid (0.37 g) and ethyl (E)-2-fluoro-3-phenylbut-2-enoate (17-S2) eluted second as light yellow liquid (1.3 g). (Ref. WO 2014/002052 and J. Org. Chem. 2009, 74, 4124-4131)

Step 2: (E)-2-Fluoro-3-phenylbut-2-en-1-ol (17-S4)

To a stirred solution of LAH (0.221 g) in ether (20 mL) at room temperature, ethyl (E)-2-fluoro-3-phenylbut-2-enoate (17-S2) (1.3 g) in ether (10 mL) was added dropwise. The reaction mixture was stirred at room temperature for 1 hour and quenched with the careful addition of saturated aqueous $NH_4Cl$ solution. The heterogeneous mixture was then extracted with ether, washed with water and brine, and dried with Na$_2$SO$_4$. Upon concentration of the organic layer, the residue was carried forward without additional purification and carried forward in the next step.

Step 3: (E)-2-(2-Fluoro-3-phenylbut-2-en-1-yl)isoindoline-1,3-dione (17-S5)

DEAD (1.52 mL) was added dropwise to a stirred solution of (E)-2-fluoro-3-phenylbut-2-en-1-ol (1 g), phthalimide (1.06 g) and triphenylphosphine (2.4 g) in THF (20 mL). After stirring for 16 hours at room temperature, the reaction mixture was concentrated under reduced pressure. The residue obtained was purified by silica gel flash column chromatography (eluent: 0-2.5% EtOAc in hexanes) to afford 1.5 g of 17-S5 as white solid.

Step 4: (E)-2-Fluoro-3-phenylbut-2-en-1-amine Hydrochloride (17-S6)

Hydrazine hydrate (0.74 mL) was added to heterogeneous solution of (E)-2-(2-fluoro-3-phenylbut-2-en-1-yl)isoindoline-1,3-dione (1.7 g) in EtOH (30 mL) and stirred at room temperature overnight. The precipitate was filtered off and the filtrate was concentrated. The residue was triturated with 4N HCl in dioxane (10 mL) and the volatiles were removed under reduced pressure. The resulting white solid was dried under high vacuum to afford 17-S6.

Step 5: tert-Butyl (1R,3S5R)-3-(((E)-2-fluoro-3-phenylbut-2-en-1-yl)carbamoyl)-2-azabicyclo[3.1.0]hexane-2-carboxylate (17-S7)

To an ice cold solution of (1R,3S,5R)-2-(tert-butoxycarbonyl)-2-azabicyclo[3.1.0]hexane-3-carboxylic acid (17-S6a) (0.25 g) in 6 mL of CH$_2$Cl$_2$, 1-chloro-N,N,2-trimethyl-1-propenylamine (0.16 mL, 1.1 equiv.) was added dropwise with stirring. After stirring for 3 hours at same temperature, solid (E)-2-fluoro-3-phenylbut-2-en-1-amine hydrochloride (17-S6) (0.2 g, 1.0 equiv.) was added followed by 0.7 mL of DIPEA (4 equiv.). The cooling bath was removed and the reaction mixture was stirred overnight at room temperature. The solvent was co-evaporated with MeOH (1 mL) and the crude product was purified by silica gel flash column chromatography (eluent: 0-0.5% MeOH in CH$_2$Cl$_2$) to afford 0.18 g of a colorless resin.

Synthesis of tert-Butyl 2-(3-acetyl-7-methyl-5-(2-methylpyrimidin-5-yl)-1H-indazol-1-yl)acetate (Intermediate 17-S12)

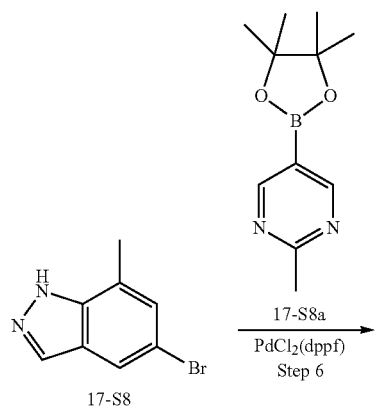

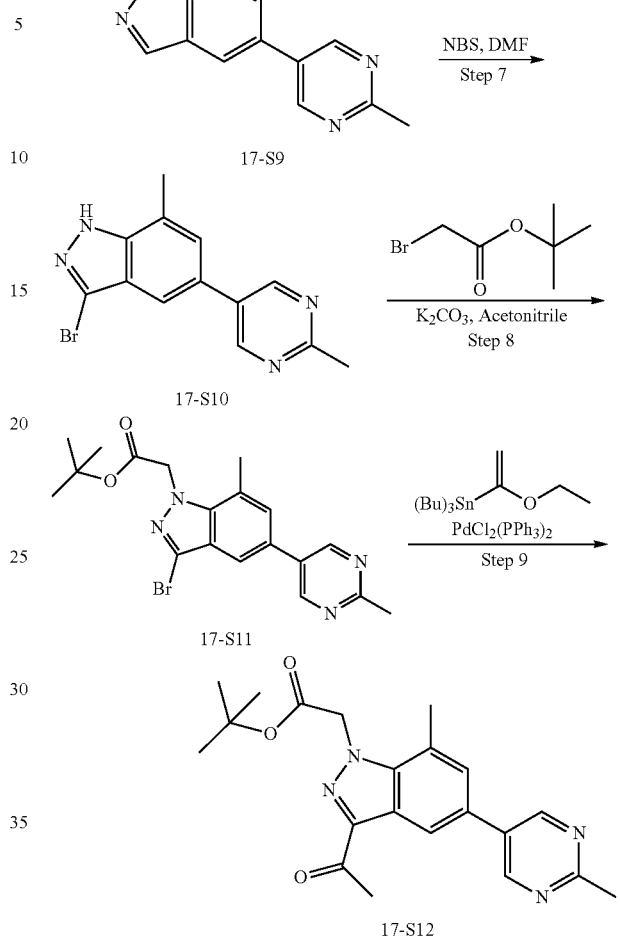

Step 6: 7-Methyl-5-(2-methylpyrimidin-5-yl)-1H-indazole (17-S9)

A mixture of 0.5 g of bromoindazole (1 equiv), 2-methyl-5-(4,4,5,5-tetramethyl-1,3,2-dioxaborolan-2-yl)pyrimidine (0.782 g, 1.5 equiv), cesium carbonate (2.315 g, 3 equiv) in dioxane (10 mL) and water (1.0 mL) was purged with argon in a pressure vessel for 5 minutes. Tetrakis(triphenylphosphine)palladium (0) (0.550 g, 0.2 equiv) was then added under argon and the pressure vessel was sealed and heated at 90° C. overnight. The reaction mixture was cooled to room temperature and the solvent was removed under reduced pressure. The crude product was purified by silica gel flash column chromatography (eluent: 0-3% MeOH in CH$_2$Cl$_2$) to afford 0.395 g of the product as a white solid.

Step 7: 3-Bromo-7-methyl-5-(2-methylpyrimidin-5-yl)-1H-indazole (17-S10)

To a stirred solution of indazole 17-S9 (1.75 g) in DMF (20 mL), NBS (1.05 g) was added. The reaction mixture was stirred at room temperature for 2 hours and additional NBS (0.209 g) was added followed by stirring for 30 minutes at room temperature. The reaction mixture was poured into water and the precipitate was isolated by filtration, dried and purified by silica gel flash column chromatography (eluent: 0-5% MeOH in CH$_2$Cl$_2$) to afford 17-S10 as a white solid.

Step 8: tert-Butyl 2-(3-bromo-7-methyl-5-(2-methylpyrimidin-5-yl)-1H-indazol-1-yl)acetate 17-(S11)

A mixture of 3-bromo-7-methyl-5-(2-methylpyrimidin-5-yl)-1H-indazole (0.215 g), tert-butyl bromoacetate (115 µL), and potassium carbonate (0.196 g) in anhydrous acetonitrile (10 mL) was refluxed for 4 hours. The reaction mixture was then cooled to room temperature and the solvent was removed under reduced pressure. The residue was purified by silica gel flash column chromatography (eluent: 0-1% MeOH in CH$_2$Cl$_2$) to afford the product as a white foam.

Step 9: tert-Butyl 2-(3-acetyl-7-methyl-5-(2-methylpyrimidin-5-yl)-1H-indazol-1-yl)acetate (17-S12)

A solution of tert-butyl 2-(3-bromo-7-methyl-5-(2-methylpyrimidin-5-yl)-1H-indazol-1-yl)acetate (17-S11) (0.170 g 1 equiv), tri-butyl(1-ethoxyvinyl)tin 0.249 g, 2 equiv) and PdCl$_2$(PPh$_3$)$_2$ (28 mg, 0.1 equiv) in DMF (3 mL) was heated at 80° C. overnight under argon atmosphere. The mixture was concentrated under reduced pressure, diluted with CH$_2$Cl$_2$, and washed with cold aqueous HCl (1N). The organic layer was dried (Na$_2$SO$_4$), filtered and concentrated. The residue was purified by silica gel flash column chromatography (eluent: 0-1% MeOH in CH$_2$Cl$_2$) to afford a yellow solid.

Synthesis of (1R,3S,5R)-2-(2-(3-Acetyl-7-methyl-5-(2-methylpyrimidin-5-yl)-1H-indazol-1-yl)acetyl)-N-((E)-2-fluoro-3-phenylbut-2-en-1-yl)-2-azabicyclo[3.1.0]hexane-3-carboxamide (17)

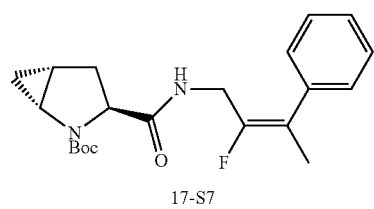

17-S7

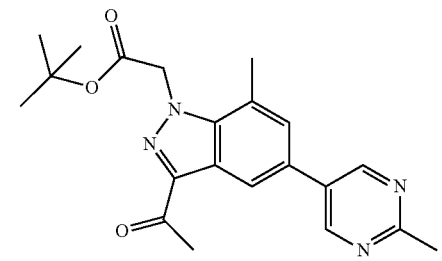

17-S12

TFA/CH$_2$Cl$_2$ | Step 10

TFA/CH$_2$Cl$_2$ | Step 11

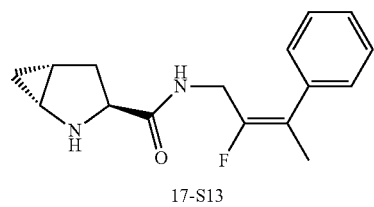

17-S13

+

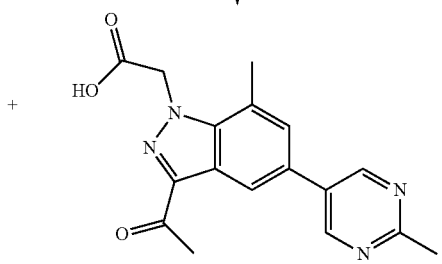

17-S14

HATU, DIEA
―――――
DMF
Step 12

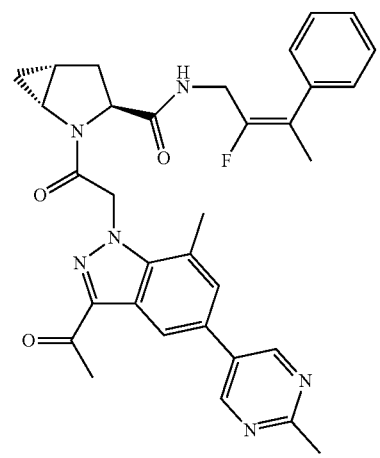

17

Step 10: (1R,3S,5R)—N-((E)-2-Fluoro-3-phenylbut-2-en-1-yl)-2-azabicyclo[3.1.0]hexane-3-carboxamide TFA Salt (17-S13)

tert-Butyl (1R,3S,5R)-3-(((E)-2-fluoro-3-phenylbut-2-en-1-yl)carbamoyl)-2-azabicyclo[3.1.0]hexane-2-carboxylate (0.1 g) was dissolved in CH₂Cl₂ (1 mL) and an equal volume of TFA was added. The mixture was stirred for 30 minutes at room temperature. Then the volatiles were removed under reduced pressure and the residue was carried forward without additional purification in the next step.

Step 11: 2-(3-Acetyl-7-methyl-5-(2-methylpyrimidin-5-yl)-1H-indazol-1-yl)acetic Acid (17-S14)

tert-Butyl 2-(3-acetyl-7-methyl-5-(2-methylpyrimidin-5-yl)-1H-indazol-1-yl)acetate (17-S12, 0.13 g) was stirred in CH₂Cl₂ (1 mL) and TFA (2 mL). After completion of the reaction (monitored by HPLC), the solvent was removed under reduced pressure and the remaining residue was used in the next synthetic step without purification.

Step 12: (1R,3S,5R)-2-(2-(3-Acetyl-7-methyl-5-(2-methylpyrimidin-5-yl)-1H-indazol-1-yl)acetyl)-N-((E)-2-fluoro-3-phenylbut-2-en-1-yl)-2-azabicyclo[3.1.0]hexane-3-carboxamide (17)

Compound 17-S14 was dissolved in DMF (1 mL) and iPr₂NEt (0.297 mL, 5 equiv) was added, followed by the addition 17-S13 at 5° C. HATU (0.156 g, 1.2 equiv) was then added slowly at 5° C. and the reaction mixture was stirred for 30 minutes at room temperature. The reaction mixture was poured into water and the precipitate was isolated by filtration. The solid was dried and purified by silica gel flash column chromatography (eluent: 0-2.5% MeOH in CH₂Cl₂) to afford 17 as a cream colored solid. $^1$H NMR (400 MHz, DMSO) δ 0.65-0.71 (m, 1H), 0.78 (s, 0H), 1.02-1.07 (m, 1H), 1.15-1.26 (m, 1H), 1.81-1.98 (m, 1H), 1.93 (d, J=3.2 Hz, 3H), 2.06-2.12 (m, 1H), 2.23-2.26 (m, 1H), 2.64 (s, 3H), 2.68 (s, 6H), 3.70-3.93 (m, 2H), 4.24 (dd, J=5.0, 9.1 Hz, 1H), 5.70 (d, J=17.7 Hz, 1H), 6.03 (d, J=17.8 Hz, 1H), 7.20-7.33 (m, 5H), 7.63 (s, 1H), 8.15 (t, J=5.3 Hz, 1H), 8.32 (d, J=1.6 Hz, 1H), 9.02 (s, 2H). $^{19}$F-NMR (DMSO-d₆): δ−113.2.

(1R,3S,5R)-2-(2-(3-Acetyl-5-(2-methylpyrimidin-5-yl)-1H-indazol-1-yl)acetyl)-N-((E)-2-fluoro-3-phenylbut-2-en-1-yl)-5-methyl-2-azabicyclo[3.1.0]hexane-3-carboxamide $^1$H NMR (400 MHz, Chloroform-d) δ 0.85 (dd, J=2.4, 5.4 Hz, 1H), 1.13 (t, J=5.3 Hz, 1H), 1.41 (s, 3H), 1.95 (d, J=3.7 Hz, 3H), 2.13 (dd, J=8.7, 13.4 Hz, 1H), 2.64-2.68 (m, 1H), 2.72 (s, 3H), 2.81 (s, 3H), 3.11 (dd, J=2.4, 5.5 Hz, 1H), 3.85-4.07 (m, 2H), 4.55 (dd, J=3.0, 8.7 Hz, 1H), 5.45 (d, J=2.7 Hz, 2H), 6.78 (t, J=5.2 Hz, 1H), 7.08-7.15 (m, 2H), 7.18-7.32 (m, 3H), 7.51 (d, J=8.7 Hz, 1H), 7.61 (dd, J=1.7, 8.7 Hz, 1H), 8.59 (s, 1H), 8.89 (s, 2H). $^{19}$F δ−115.9.

(1R,3S,5R)-2-(2-(3-Acetyl-5-(2-methylpyrimidin-5-yl)-1H-pyrrolo[2,3-C]pyridine-1-yl)acetyl)-N-((E)-2-fluoro-3-phenylbut-2-en-1-yl)-5-methyl-2-azabicyclo[3.1.0]hexane-3-carboxamide $^1$H NMR (400 MHz, DMSO-d₆) δ 0.94 (dd, J=2.4, 5.4 Hz, 1H), 1.00 (t, J=5.4 Hz, 1H), 1.28 (s, 3H), 1.84-1.97 (m, 1H), 1.94 (d, J=3.2 Hz, 3H), 2.39 (dd, J=9.1, 13.2 Hz, 1H), 2.53 (s, 3H), 2.68 (s, 3H), 3.48 (d, J=3.2 Hz, 1H), 3.84 (dd, J=5.3, 20.8 Hz, 2H), 4.21 (dd, J=4.9, 9.2 Hz, 1H), 5.36 (d, J=17.1 Hz, 1H), 5.63 (d, J=17.2 Hz, 1H), 7.20-7.35 (m, 5H), 8.17 (t, J=5.4 Hz, 1H), 8.52 (s, 1H), 8.58 (s, 1H), 8.98 (s, 1H), 9.29 (s, 2H). $^{19}$F δ−113.6.

(1R,3S,5R)-2-(2-(3-Acetyl-7-methyl-5-(2-methylpyrimidin-5-yl)-1H-indazol-1-yl)acetyl)-N-((E)-2-fluoro-3-phenylbut-2-en-1-yl)-5-methyl-2-azabicyclo[3.1.0]hexane-3-carboxamide $^1$H NMR (400 MHz, Chloroform-d) δ 0.87 (dd, J=2.4, 5.5 Hz, 1H), 1.15 (t, J=5.4 Hz, 1H), 1.42 (s, 3H), 1.94 (d, J=3.6 Hz, 3H), 2.14 (dd, J=8.7, 13.4 Hz, 1H), 2.68 (s, 3H), 2.71 (s, 3H), 2.80 (s, 3H), 3.08 (dd, J=2.4, 5.5 Hz, 1H), 3.96 (dd, J=5.3, 20.9 Hz, 2H), 4.55 (dd, J=3.0, 8.7 Hz, 1H), 5.64 (s, 2H), 6.81 (t, J=5.4 Hz, 1H), 7.07-7.14 (m, 2H), 7.18-7.31 (m, 4H), 7.32 (s, 1H), 8.47 (s, 1H), 8.88 (s, 2H). $^{19}$F δ−115.6.

Scheme 12: Synthesis of (2S,4R)-1-(2-(3-Acetyl-7-((dimethylamino)methyl)-5-(2-methylpyrimidin-5-yl)-1H-indazol-1-yl)acetyl)-N-(6-bromopyridin-2-yl)-4-fluoropyrrolidine-2-carboxamide (19)

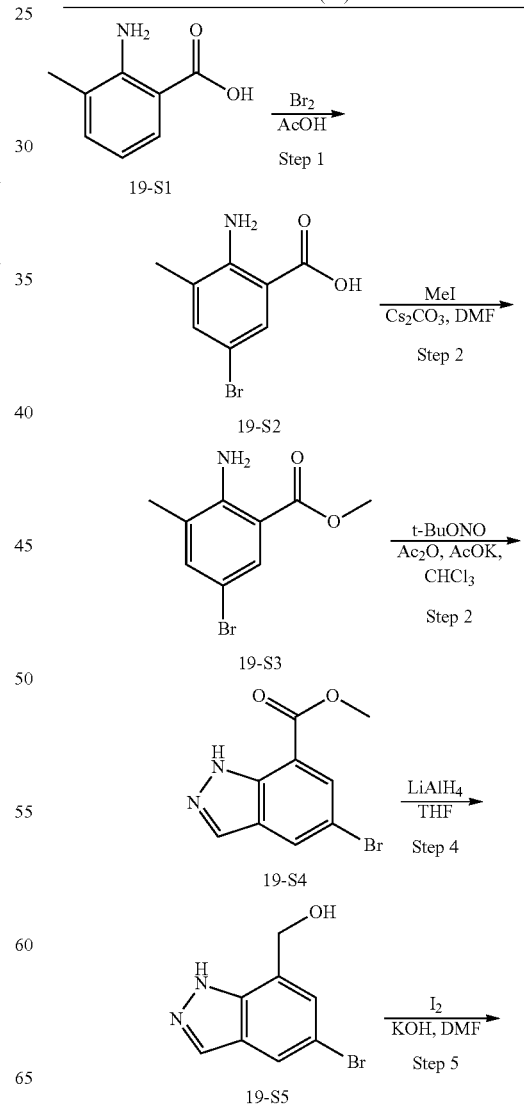

-continued

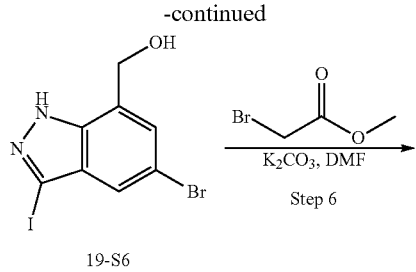

19-S6

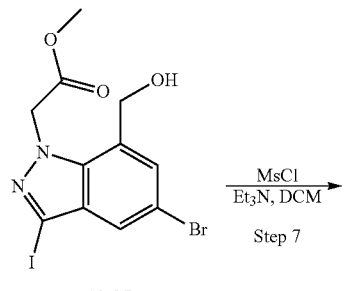

19-S7

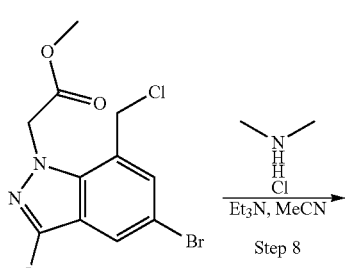

19-S8

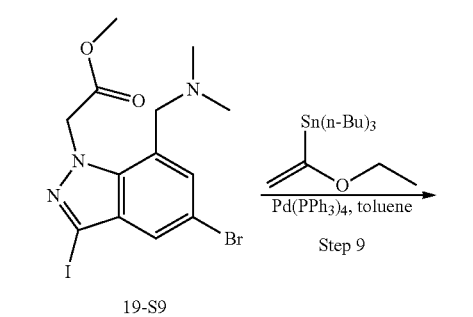

19-S9

-continued

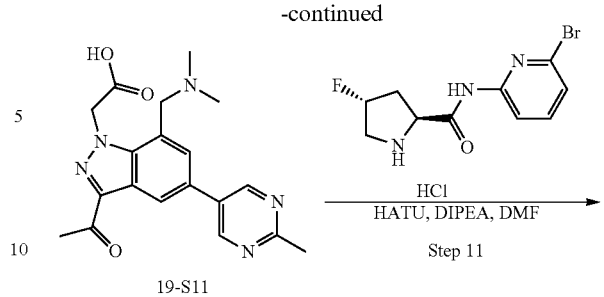

19-S11

19

Step 1: 2-Amino-5-bromo-3-methylbenzoic Acid (19-S2)

To a solution of 19-S1 (15 g, 0.1 mol) in AcOH (80 mL) was added Br$_2$ (5.1 mL, 0.1 mol) dropwise at 0° C. The reaction mixture was stirred at room temperature for 4 h. The mixture was diluted with EtOAc and basified with aqueous NaOH solution (4 N) to pH 7. The mixture was extracted with EtOAc, dried, and concentrated to afford the crude product, which was purified by column chromatography on silica gel (eluted with DCM/MeOH=100:0 to 50:1) to afford 19-S2 (12.0 g, 52.2% yield) as a white solid. LC/MS (ESI) m/z: 230 (M+H)$^+$.

Step 2: Methyl 2-amino-5-bromo-3-methylbenzoate (19-S3)

To a solution of 19-S2 (12 g, 52.2 mmol) in DMF (60 mL) was added Cs$_2$CO$_3$ (25.5 g, 78.3 mmol) and CH$_3$I (7.79 g, 54.8 mmol) at 0° C. The reaction mixture was stirred at room temperature for 16 hours. The mixture was then diluted with EtOAc, washed with 5% aqueous LiCl solution and brine, dried, and concentrated to afford the crude product, which was purified by column chromatography on silica gel (eluted with PE/EtOAc=50:1 to 20:1) to afford 19-S3 (11.0 g, 86.6% yield) as a white solid. LC/MS (ESI) m/z: 244 (M+H)$^+$.

Step 3: Methyl 5-bromo-1H-indazole-7-carboxylate (19-S4)

To a mixture of 19-S3 (10.9 g, 44.7 mmol) and AcOK (1.32 g, 13.41 mmol) in CHCl$_3$ (50 mL) was added Ac$_2$O (10.6 g, 103 mmol) at 0° C. slowly under an atmosphere of nitrogen. The reaction mixture was stirred at room temperature for 1 hour. The mixture was then heated to 60° C. and t-BuONO (10.2 g, 98.3 mmol) was added to the above mixture. The resulting mixture was stirred at 60° C. for 4 hours. After cooling, the mixture was quenched with saturated aqueous NaHCO$_3$ solution and extracted with EtOAc. The organic layer was separated, dried, and concentrated to afford the crude product, which was purified by column chromatography on silica gel (eluted with PE/EtOAc=100:0 to 10:1) to afford 19-S4 (8.0 g 70.5% yield) as a yellow solid. LC/MS (ESI) m/z: 255 (M+H)$^+$.

Step 4: (5-Bromo-1H-indazol-7-yl) methanol (19-S5)

To a solution of 19-S4 (5 g, 19.6 mmol) in anhydrous THF (50 mL) was added LiAlH$_4$ (1.49 g 39.2 mmol) in portions at 0° C. The reaction mixture was stirred at 0° C. for 30 minutes and at room temperature for 1 hour. The mixture was then quenched with water (1.5 mL), 10% aqueous NaOH solution (3 g), and water (4.5 mL). The mixture was filtered and the filter cake was washed with EtOAc. The filtrate was dried and concentrated to afford the crude product, which was purified by column chromatography on silica gel (eluted with DCM/MeOH=100:0 to 20:1) to afford 19-S5 (3.36 g, 76.1% yield) as a white solid. LC/MS (ESI) m/z: 227 (M+H)$^+$.

Step 5: (5-Bromo-3-iodo-1H-indazol-7-yl) methanol (19-S6)

To a solution of 19-S5 (2.27 g 10 mmol) in DMF (25 mL) were added KOH (1.26 g, 22.5 mmol) and I$_2$ (3.81 g. 15 mmol) at 0° C. The mixture was stirred at room temperature for 16 hours. The mixture was then quenched with 5% aqueous Na$_2$S$_2$O$_3$ solution and extracted with EtOAc. The organic layer was separated, dried, and concentrated to afford the crude product, which was recrystallized with EtOAc/PE (1:2) to afford 19-S6 (2.85 g. 81.0% yield) as a brown solid. LC/MS (ESI) m/z: 353 (M+H)$^+$.

Step 6: Methyl 2-(5-bromo-7-(hydroxymethyl)-3-iodo-1H-indazol-1-yl)acetate (19-S7)

To a solution of 19-S6 (1.98 g. 5.6 mmol) in DMF (20 mL) was added K$_2$CO$_3$ (1.38 g, 10 mmol) and methyl 2-bromoacetate (900 mg, 5.88 mmol). The reaction mixture was stirred at room temperature for 2.5 hours. The mixture was diluted with EtOAc, washed with 10% aqueous LiCl solution, dried, and concentrated to afford the crude product, which was purified by column chromatography on silica gel (eluted with PE/EtOAc=10:1 to 3:1) to afford 19-S7 (1.34 g, 56.4% yield) as colorless oil. LC/MS (ESI) m/z: 425 (M+H)$^+$.

Step 7: Methyl 2-(5-bromo-7-(chloromethyl)-3-iodo-1H-indazol-1-yl)acetate (19-S8)

To a mixture of 19-S7 (424 mg, 1 mol) in dry DCM (10 mL) was added Et$_3$N (250 mg, 2.5 mmol) followed by dropwise addition of MsCl (173 mg, 1.5 mmol) at 0° C. The reaction mixture was stirred at room temperature for 16 hours. The mixture was quenched with saturated aqueous NaHCO$_3$ solution and extracted with EtOAc. The organic layer was separated, dried, and concentrated to afford the crude product, which was purified by column chromatography on silica gel (eluted with PE/EtOAc=100:0 to 15:1) to afford 19-S8 (360 mg, 81.1% yield) as a brown solid. LC/MS (ESI) m/z: 443 (M+H)$^+$.

Step 8: Methyl 2-(5-bromo-7-((dimethylamino)methyl)-3-iodo-1H-indazol-1-yl)acetate (19-S9)

To a solution of 19-S8 (360 mg, 0.82 mol) in MeCN (10 mL) were added Et$_3$N (249 mg, 2.46 mmol) and dimethylamine hydrochloride (133 mg, 1.64 mmol) at 0° C. The reaction mixture was stirred at room temperature for 3 hours. The mixture was quenched with saturated aqueous NaHCO$_3$ solution and extracted with EtOAc. The organic layer was separated, dried, and concentrated to afford the crude product, which was purified by column chromatography on silica gel (eluted with PE/EtOAc=20:1 to 10:1) to afford 19-S9 (328 mg, 88.5% yield) as a brown solid. LC/MS (ESI) m/z: 452 (M+H)$^+$.

Step 9: 2-(3-Acetyl-5-bromo-7-((dimethylamino)methyl)-1H-indazol-1-yl)acetic Acid (19-S10)

To a mixture of 19-S9 (68 mg, 0.15 mol) in dry toluene (10 mL) were added tributyl(1-ethoxyvinyl)stannane (82 mg, 0.226 mmol) and Pd(PPh$_3$)$_4$ (14 mg, 0.012 mmol). The reaction mixture was stirred at 95° C. for 16 hours under an atmosphere of nitrogen. After cooling, the mixture was quenched with 1 N aqueous HCl solution and the mixture was stirred at room temperature for 15 minutes. The mixture was extracted with DCM/MeOH (20:1), dried over anhydrous Na$_2$SO$_4$, filtered, and concentrated to afford the crude product, which was purified by preparative TLC (DCM/MeOH=20:1) to afford 19-S10 (38 mg, 71.7% yield) as colorless oil. LC/MS (ESI) m/z: 354 (M+H)$^+$.

Step 10: 2-(3-Acetyl-7-((dimethylamino)methyl)-5-(2-methylpyrimidin-5-yl)-1H-indazol-1-yl)acetic Acid (19-S11)

To a solution of 19-S10 (38 mg, 0.11 mol) in 1,4-dioxane/H$_2$O (7 mL, 6:1) were added 2-methylpyrimidin-5-ylboronic acid (23 mg, 0.162 mmol), K$_2$CO$_3$ (46 mg, 0.33 mmol), and Pd(PPh$_3$)$_4$ (12 mg, 0.011 mmol). The reaction mixture was stirred at 90° C. for 16 hours under an atmosphere of nitrogen. After cooling, the mixture was acidified with 10% aqueous HCl solution and extracted with DCM/MeOH (10:1). The organic layer was separated, dried, and concentrated to afford the crude product, which was purified by preparative TLC (DCM/MeOH=5:1) to afford 19-S11 (21 mg, 52.0% yield) as a yellow solid. LC/MS (ESI) m/z: 368 (M+H)$^+$.

Step 11: (2S,4R)-1-(2-(3-Acetyl-7-((dimethylamino)methyl)-5-(2-methylpyrimidin-5-yl)-1H-indazol-1-yl)acetyl)-N-(6-bromopyridin-2-yl)-4-fluoropyrrolidine-2-carboxamide (19)

To a mixture of 19-S11 (21 mg, 0.057 mmol) and (2S,4R)—N-(6-bromopyridin-2-yl)-4-fluoropyrrolidine-2-carboxamide hydrochloride (19 mg, 0.057 mmol) in DMF (1 mL) were added DIPEA (23 mg, 0.171 mmol) followed by HATU (43 mg, 0.114 mmol) at 0° C. The reaction mixture was stirred at room temperature for 1 h. The mixture was diluted with EtOAc, washed with 10% aqueous LiCl solution and brine, dried, and concentrated to afford the crude product, which was purified by preparative HPLC to afford 19 (6 mg, 16.7% yield) as a white solid. $^1$H NMR (400 MHz, DMSO-d$_6$) δ 11.12 (s, 1H), 9.10 (s, 2H), 8.50 (d, J=1.7 Hz, 1H), 8.09 (d, J=8.3 Hz, 1H), 7.73-7.83 (m, 2H), 7.39 (d, J=7.7 Hz, 1H), 6.31 (d, J=17.4 Hz, 1H), 6.09 (d, J=17.3 Hz, 1H), 5.55-5.68 (m, 1H), 4.80 (t, J=8.7 Hz, 1H), 4.30-4.39

(m, 1H), 3.86-3.99 (m, 2H), 3.43-3.48 (m, 1H), 2.73 (s, 3H), 2.68 (s, 3H), 2.57-2.66 (m, 1H), 2.29 (s, 6H), 2.13-2.19 (m, 1H). LC/MS (ESI) m/z: 637 (M+H)$^+$.

Scheme 13: Synthesis of (2S,4R)-1-(2-(3-Acetyl-7-(fluoromethyl)-5-(2-methylpyrimidin-5-yl)-1H-indazol-1-yl)acetyl)-N-(6-bromopyridin-2-yl)-4-fluoropyrrolidine-2-carboxamide (20)

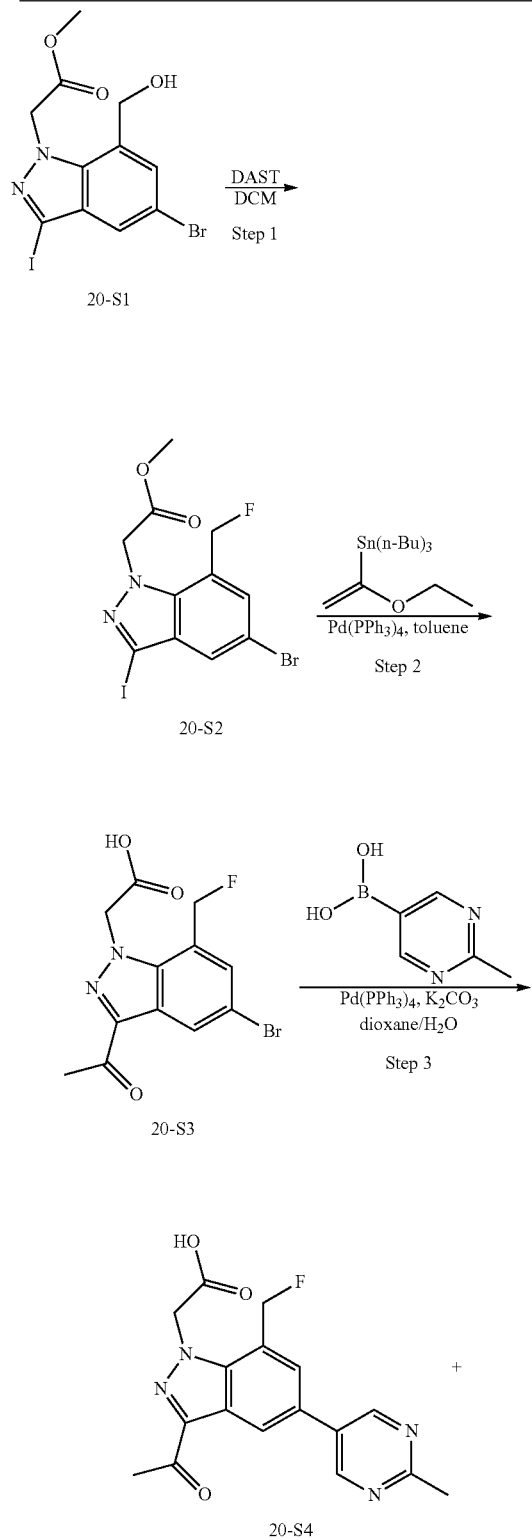

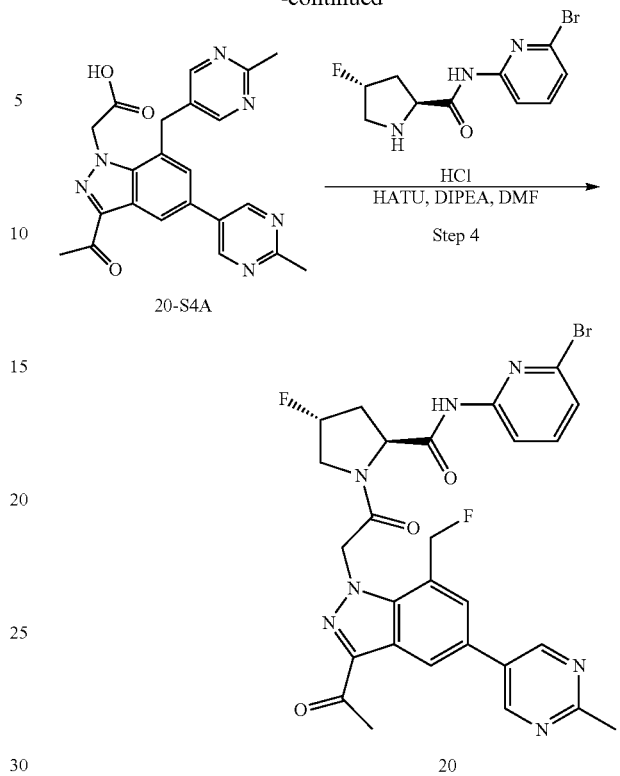

The above scheme and following detailed description depicts one non-limiting method for synthesizing compounds by 1) a Stille carbonylative cross-coupling using tributyl(1-ethoxyvinyl)stannane to functionalize the R$^6$ position of the A-ring; 2) a Suzuki cross-coupling to functionalize the R$^{32}$ of the A-ring; and, 3) the formation of an amide bond between the C-ring (already linked to the B-ring) and A-ring utilizing HATU. The skilled artisan will recognize that the C- and B-ring synthetic intermediate can be replaced with other synthetic intermediates to afford additional compounds of the present invention. The skilled artisan will also recognize that the A-ring synthetic intermediate can be replaced with other synthetic intermediates to afford additional compounds of the present invention.

Step 1: Methyl 2-(5-bromo-7-(fluoromethyl)-3-iodo-1H-indazol-1-yl)acetate (20-S2)

To a solution of 20-S1 (85 mg, 0.2 mmol) in dry DCM (6 mL) was added DAST (64 mg, 0.4 mmol) dropwise at −30° C. The resulting mixture was stirred from −30° C. to room temperature for 1 hour. The mixture was then quenched with saturated aqueous NaHCO$_3$ solution and extracted with EtOAc. The organic layer was separated, dried, and concentrated to dryness. The remaining residue was purified by column chromatography on silica gel (eluted with PE/EtOAc=20:1 to 10:1) to afford 20-S2 (73 mg, 85.7% yield) as a yellow oil. LC/MS (ESI) m/z: 427 (M+H)$^+$.

Step 2: 2-(3-Acetyl-5-bromo-7-(fluoromethyl)-1H-indazol-1-yl)acetic Acid (20-S3)

To a mixture of 20-S2 (73 mg, 0.171 mol) in dry toluene (8 mL) were added tributyl(1-ethoxyvinyl)stannane (87 mg, 0.24 mmol) and Pd(PPh$_3$)$_4$ (16 mg, 0.0137 mmol). The reaction mixture was stirred at 95° C. for 16 hours under an atmosphere of nitrogen. After cooling, the mixture was quenched with 1 N aqueous HCl solution and the mixture was stirred at room temperature for 15 minutes. The mixture was then extracted with DCM/MeOH (15:1), the organic layer was separated, dried, and concentrated to afford the crude product, which was purified by preparative TLC (DCM/MeOH=15:1) to afford 20-S3 (50 mg, 88.8% yield) as colorless oil. LC/MS (ESI) m/z: 329 (M+H)+.

Step 3: 2-(3-Acetyl-7-(fluoromethyl)-5-(2-methylpyrimidin-5-yl)-1H-indazol-1-yl)acetic Acid (2-S4) and 2-(3-acetyl-5-(2-methylpyrimidin-5-yl)-7-((2-methylpyrimidin-5-yl)methyl)-1H-indazol-1-yl)acetic Acid (20-S4A)

To a mixture of 20-S3 (50 mg, 0.152 mol) in 1,4-dioxane/H$_2$O (7 mL, 6:1) was added 2-methylpyrimidin-5-ylboronic acid (26 mg, 0.182 mmol), K$_2$CO$_3$ (63 mg, 0.456 mmol), and Pd(PPh$_3$)$_4$ (18 mg, 0.0152 mmol). The reaction mixture was stirred at 90° C. for 16 hours under an atmosphere of nitrogen. After cooling, the mixture was acidified with 10% aqueous HCl solution and extracted with DCM/MeOH (10:1). The organic layer was separated, dried, and concentrated to afford the crude product, which was purified by preparative TLC (DCM/MeOH=5:1) to afford 20-S4 (30 mg, 57.5% yield) and 20-S4A (25 mg, 39.4% yield) as colorless oils. LC/MS (ESI) m/z: 343 (M+H)+, 417 (M+H)+.

Step 4: (2S,4R)-1-(2-(3-Acetyl-7-(fluoromethyl)-5-(2-methylpyrimidin-5-yl)-1H-indazol-1-yl)acetyl)-N-(6-bromopyridin-2-yl)-4-fluoropyrrolidine-2-carboxamide (20)

To a mixture of 20-S4 (30 mg, 0.088 mmol) and (2S,4R)—N-(6-bromopyridin-2-yl)-4-fluoropyrrolidine-2-carboxamide hydrochloride (30 mg, 0.088 mmol) in DMF (1 mL) was added DIPEA (36 mg, 0.264 mmol) followed by HATU (52 mg, 0.132 mmol) at 0° C. The reaction mixture was stirred at room temperature overnight. The mixture was diluted with EtOAc, washed with 10% aqueous LiCl solution and brine, dried, and concentrated to afford the crude product, which was purified by preparative HPLC to afford 20 (6 mg, 11.1% yield) as a white solid. $^1$H NMR (400 MHz, DMSO-d$_6$) δ 11.07 (s, 1H), 9.06 (s, 2H), 8.55 (s, 1H), 8.06-7.94 (m, 2H), 7.72 (t, J=8.0 Hz, 1H), 7.33 (d, J=7.3 Hz, 1H), 5.94 (d, J=18.0 Hz, 1H), 5.78-5.88 (m, 1H), 5.47-5.71 (m, 3H), 4.68-4.74 (m, 1H), 4.24-4.33 (m, 1H), 3.86-4.02 (m, 1H), 2.69 (s, 3H), 2.67 (s, 3H), 2.18-2.27 (m, 1H), 2.07-2.16 (m, 1H). LC/MS (ESI) m/z: 612 (M+H)+.

3-Acetyl-1-(2-((3S)-3-(6-bromo-3-methylpyridin-2-ylcarbamoyl)-5-((dimethylamino)methyl)-2-azabicyclo[3.1.0]hexan-2-yl)-2-oxoethyl)-5-(2-methylpyrimidin-5-yl)-1H-indazole-7-carboxylic Acid (63)

$^1$H NMR (400 MHz, DMSO-d$_6$) δ 10.53 (s, 1H), 8.99 (s, 2H), 8.46 (d, J=1.6 Hz, 1H), 7.96 (s, 1H), 7.58 (d, J=8.0 Hz, 1H), 7.40 (d, J=7.9 Hz, 1H), 6.08 (d, J=16.8 Hz, 1H), 5.93 (d, J=16.8 Hz, 1H), 5.82-5.85 (m, 1H), 4.33-4.40 (m, 1H), 3.62-3.66 (m, 1H), 3.57-3.61 (m, 1H), 2.68 (s, 3H), 2.66 (s, 3H), 2.40-2.44 (m, 1H), 2.37 (s, 3H), 2.33 (s, 3H), 2.17-2.22 (m, 1H), 2.01 (s, 3H), 1.21-1.25 (m, 1H), 1.10-1.15 (m, 1H). LC/MS (ESI) m/z: 689/691 (M+H)+.

(1R,3S,5R)-2-(2-(3-Acetyl-4-fluoro-5-(2-methylpyrimidin-5-yl)-1H-indazol-1-yl)acetyl)-N-(6-bromo-3-methylpyridin-2-yl)-5-((dimethylamino)methyl)-2-azabicyclo[3.1.0]hexane-3-carboxamide (155)

$^1$H NMR (400 MHz, CD$_3$OD) δ 8.84 (s, 2H), 7.61-7.44 (m, 3H), 7.30 (d, J=7.9 Hz, 1H), 5.73 (d, J=17.3 Hz, 1H), 5.58 (d, J=17.5 Hz, 1H), 4.55 (m, 1H), 3.63 (m, 1H), 2.96 (m, 1H), 2.67 (s, 3H), 2.62 (s, 3H), 2.59-2.47 (m, 3H), 2.44 (m, 6H), 2.04 (s, 3H), 1.20 (d, J=19.2 Hz, 2H). LC/MS (ESI) m/z: 662 (M+H)+.

(1S,3S,5S)-2-(2-(3-Acetyl-4-fluoro-5-(2-methylpyrimidin-5-yl)-1H-indazol-1-yl)acetyl)-N-(6-bromo-3-methylpyridin-2-yl)-5-((dimethylamino)methyl)-2-azabicyclo[3.1.0]hexane-3-carboxamide (156)

$^1$H NMR (400 MHz, CD$_3$OD) δ 8.83 (s, 2H), 7.57-7.44 (m, 3H), 7.28 (d, J=7.9 Hz, 1H), 5.74 (d, J=17.0 Hz, 1H), 5.55 (d, J=17.1 Hz, 1H), 4.99 (d, J=9.5 Hz, 1H), 3.59 (s, 1H), 2.81 (s, 1H), 2.67 (s, 3H), 2.62 (s, 3H), 2.33 (m, 9H), 1.99 (m, 3H), 1.60 (m, 1H), 1.01 (m, 1H). LC/MS (ESI) m/z: 662 (M+H)+.

(1R,3S,5R)-2-(2-(3-Acetyl-5-(2-methylpyrimidin-5-yl)-1H-pyrazolo[3,4-b]pyridin-1-yl)acetyl)-N-(6-bromo-3-methylpyridin-2-yl)-5-methyl-2-azabicyclo[3.1.0]hexane-3-carboxamide (181)

$^1$H NMR (400 MHz, DMSO-d$_6$) δ 0.93-0.99 (m, 1H), 1.02-1.08 (m, 1H), 1.33 (s, 3H), 2.07 (s, 4H), 2.52-2.61 (m, 1H), 2.68 (s, 3H), 2.71 (s, 3H), 3.62 (dd, J=2.4, 5.7 Hz, 1H), 4.42 (dd, J=5.0, 9.3 Hz, 1H), 5.62 (d, J=17.0 Hz, 1H), 5.91 (d, J=17.0 Hz, 1H), 7.45 (d, J=7.9 Hz, 1H), 7.63 (d, J=7.9 Hz, 1H), 8.84 (d, J=2.2 Hz, 1H), 9.02 (d, J=2.1 Hz, 1H), 9.14 (s, 2H), 10.26 (s, 1H).

(1R,3S,5R)-2-(2-(3-Acetyl-5-(2-methylpyrimidin-5-yl)-1H-pyrazolo[4,3-b]pyridin-1-yl)acetyl)-N-(6-bromo-3-methylpyridin-2-yl)-5-methyl-2-azabicyclo[3.1.0]hexane-3-carboxamide (184)

$^1$H NMR (400 MHz, DMSO-d$_6$) δ 0.97-1.07 (m, 2H), 1.33 (s, 3H), 2.00-2.10 (m, 4H), 2.53-2.59 (m, 1H), 2.72 (s, 3H), 2.82 (s, 3H), 3.54-3.63 (m, 1H), 4.37-4.50 (m, 1H), 5.61 (d, J=17.2 Hz, 1H), 5.94 (d, J=17.2 Hz, 1H), 7.45 (d, J=7.9 Hz, 1H), 7.63 (d, J=7.9 Hz, 1H), 8.23 (d, J=9.0 Hz, 1H), 8.34 (d, J=8.9 Hz, 1H), 9.44 (s, 2H), 10.26 (s, 1H).

(2S,4R)—N-(6-bromopyridin-2-yl)-1-(2-(3-ethyl-5-(2-methylpyrimidin-5-yl)-1H-indazol-1-yl)acetyl)-4-fluoropyrrolidine-2-carboxamide $^1$H-NMR (400 MHz, DMSO-d$_6$) δ 10.98 (s, 1H), 9.05 (s, 2H), 8.15 (s, 1H), 8.02-8.04 (d, J=8.4 Hz, 1H), 7.68-7.75 (m, 2H), 7.59-7.62 (d, J=8.8 Hz, 1H), 7.31-7.33 (d, J=7.6 Hz, 1H), 5.45-5.58 (m, 1H), 5.50-5.54 (m, J=17.2 Hz, 1H), 5.30-5.34 (d, J=17.2 Hz, 1H), 4.61-4.65 (m, 1H), 4.13-4.22 (m, 1H), 3.88-3.98 (m, 1H), 2.94-2.97 (m, 2H), 2.66 (s, 3H), 2.07-2.17 (m, 1H), 1.29-1.35 (t, 3H). LC/MS (ESI) m/z: 566/568 (M+H)+.

(1R,3S,5R)-2-(2-(3-Acetyl-6-fluoro-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide ¹H-NMR (400 MHz, DMSO-d₆) δ 10.27 (s, 1H), 8.91 (s, 2H), 8.30 (d, J=8 Hz, 1H), 7.84 (d, J=12 Hz, 1H), 7.64 (d, J=8 Hz, 1H), 7.45 (d, J=8 Hz, 1H), 5.92 (d, J=20 Hz, 1H), 5.56 (d, J=20 Hz, 1H), 4.40 (t, J=4 Hz, 1H), 3.57 (t, J=3.2 Hz, 1H), 2.70 (S, 3H), 2.64 (S, 3H), 2.04 (S, 3H), 1.32 (S, 3H), 1.08-1.05 (m, 2H). LC/MS (ESI) m/z: 620 (M+H)⁺.

(1R,3S,5R)-2-(2-(3-Acetyl-7-chloro-5-(2-methylpyrimidin-5-yl)-1H-indazol-1-yl)acetyl)-N-(6-bromo-3-((dimethylamino)methyl)pyridin-2-yl)-5-methyl-2-azabicyclo[3.1.0]hexane-3-carboxamide ¹H-NMR (400 MHz, DMSO-d₆) δ 10.57 (s, 1H), 9.06 (s, 2H), 8.44 (d, J=1.6 Hz, 1H), 8.00 (d, J=1.6 Hz, 1H), 7.71 (d, J=7.2 Hz, 1H), 7.43 (d, J=6.8 Hz, 1H), 6.02 (d, J=17.6 Hz, 1H), 5.87 (d, J=17.6 Hz, 1H), 5.32 (t, J=4.8 Hz, 1H), 4.47-4.34 (m, 1H), 3.64-3.56 (m, 1H), 3.41-3.37 (m, 1H), 3.04-2.52 (m, 6H), 2.08 (s, 3H), 2.04-1.87 (m, 2H), 1.23 (s, 3H), 1.10-1.00 (m, 1H), 0.99-0.88 (m, 1H). LC/MS (ESI) m/z: 679 (M+H)⁺.

(1R,3S,5R)-2-{2-[3-Acetyl-6-chloro-5-(2-methylpyrimidin-5-yl) indazol-1-yl]acetyl}-N-{6-bromo-3-[(dimethylamino)methyl]pyridin-2-yl}-5-methyl-2-azabicyclo[3.1.0]hexane-3-carboxamide ¹H-NMR (400 MHz, DMSO-d₆) δ 10.61 (s, 1H), 8.81 (d, J=5.5 Hz, 2H), 8.19 (s, 1H), 8.17 (s, 1H), 7.71 (d, J=8.0 Hz, 1H), 7.43 (d, J=7.9 Hz, 1H), 5.95 (d, J=17.3 Hz, 1H), 5.60 (d, J=17.2 Hz, 1H), 4.43 (s, 1H), 3.61-3.59 (m, 1H), 3.23-3.19 (m, 1H), 2.71 (s, 3H), 2.62 (s, 3H), 2.59-2.55 (m, 1H), 2.12-2.09 (m, 1H), 2.06 (s, 6H), 1.34 (s, 3H), 1.23 (m, 1H), 1.11-1.08 (m, 1H), 1.00 (t, J=5.3 Hz, 1H). LC/MS (ESI) m/z: 681 (M+H)⁺.

Scheme 14: Synthesis of (2S,4R)-1-(2-(3-Acetyl-7-((5-methylpyrimidin-2-yl)methyl)-5-(2-methylpyrimidin-5-yl)-1H-indazol-1-yl)acetyl)-N-(6-bromopyridin-2-yl)-4-fluoropyrrolidine-2-carboxamide (21)

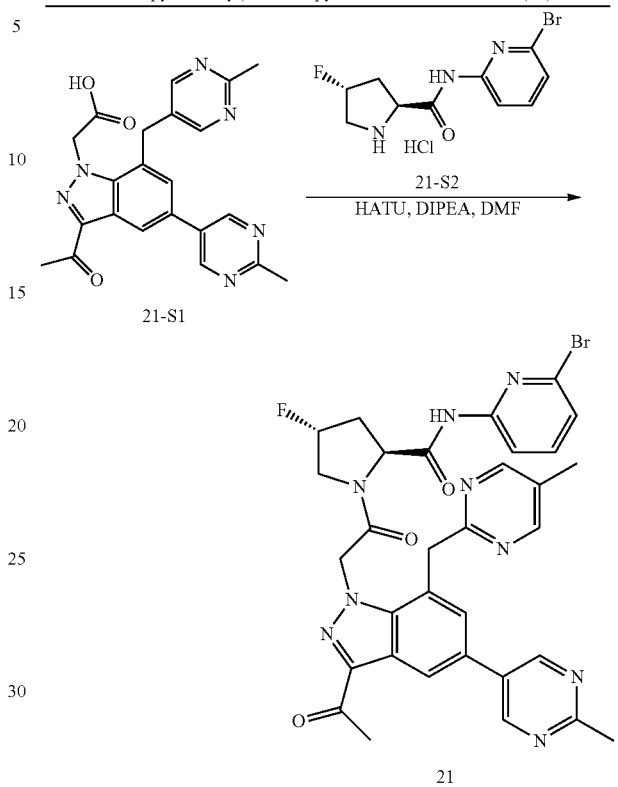

The title compound (21) was prepared according to the procedure described in Step 4 of Scheme 13 using appropriate starting materials. ¹H NMR (400 MHz, DMSO-d₆) δ 11.11 (s, 1H), 8.94 (s, 2H), 8.55 (s, 2H), 8.37-8.44 (m, 1H), 8.01 (d, J=8.0 Hz, 1H), 7.73 (t, J=8.0 Hz, 1H), 7.35 (d, J=7.3 Hz, 1H), 7.24 (s, 1H), 5.92 (d, J=18.1 Hz, 1H), 5.45-5.61 (m, 2H), 4.67-4.76 (m, 1H), 4.51 (d, J=16.9 Hz, 1H), 4.34 (d, J=16.7 Hz, 1H), 4.23 (dd, J=20.8, 13.0 Hz, 1H), 3.84-3.94 (m, 1H), 2.68 (s, 3H), 2.62 (s, 3H), 2.52 (s, 3H), 2.18-2.26 (m, 1H), 2.06-2.15 (m, 1H). LC/MS (ESI) m/z: 686 (M+H)⁺.

Scheme 15: (3S)-2-(2-(3-Acetyl-5-(2-methylpyrimidin-5-yl)-1H-indazol-1-yl)acetyl)-N-(6-bromo-3-methylpyridin-2-yl)-5-(piperazin-1-ylmethyl)-2-azabicyclo[3.1.0]hexane-3-carboxamide. (22)

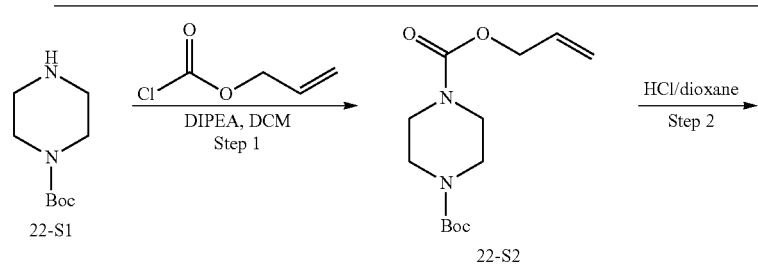

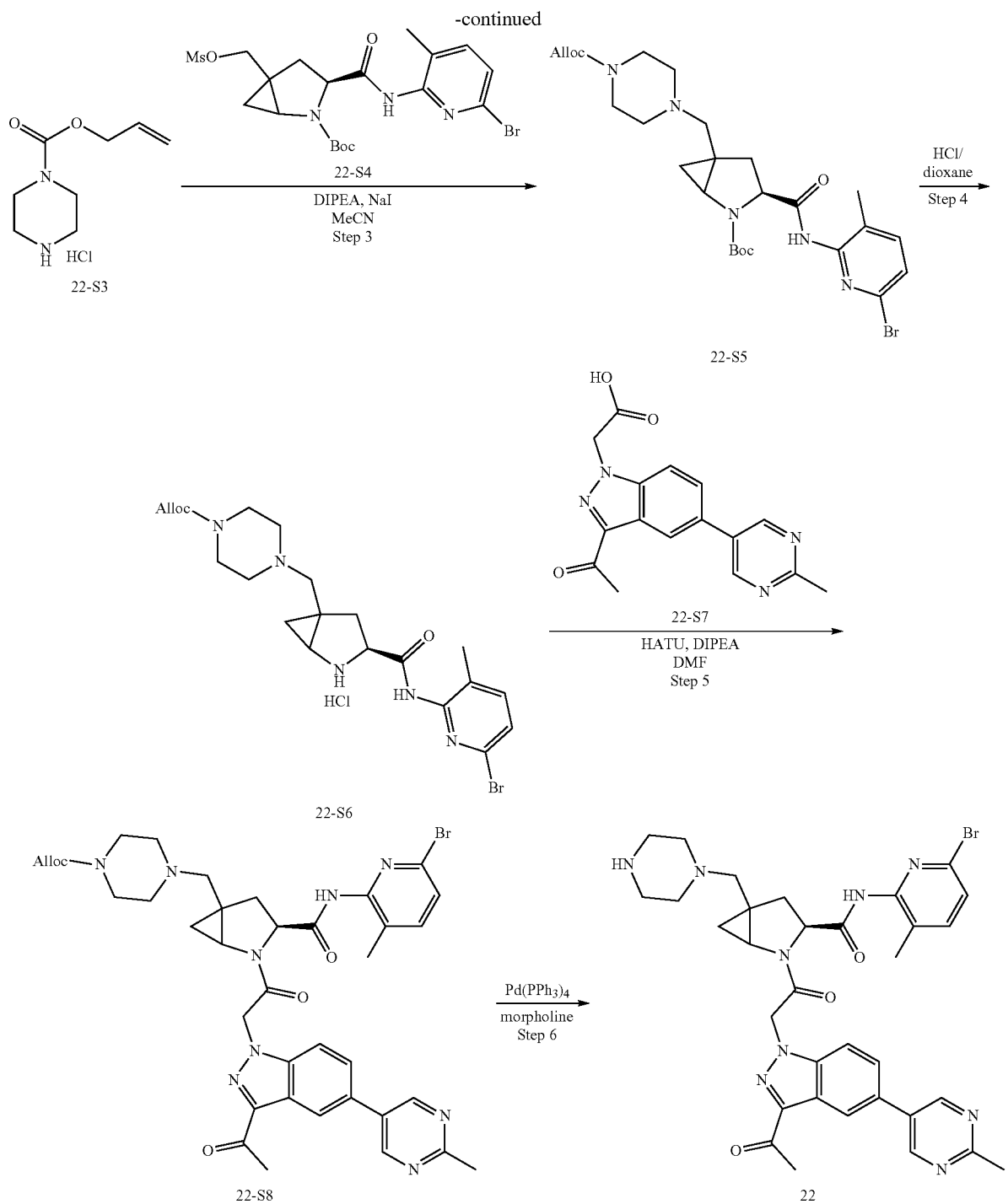

Step 1: 1-Allyl 4-tert-butyl piperazine-1,4-dicarboxylate (22-S2)

To a solution of 22-S1 (375 mg, 2.02 mmol) in DCM (10 mL) were added DIPEA (0.032 mL, 10.10 mmol) and allyl chloroformate (727 mg, 6.06 mmol) at 0° C. The reaction mixture was stirred at room temperature overnight. The mixture was washed with water and brine. The organic phase was dried over anhydrous $Na_2SO_4$, filtered, and concentrated to dryness. The remaining residue was purified by column chromatography on silica gel (eluted with PE/EtOAc=30:1 to 20:1) to afford the title compound (400 mg, 73.4% yield) as a yellow oil. LC/MS (ESI) m/z: 271 $(M+H)^+$.

Step 2: Allyl piperazine-1-carboxylate Hydrochloride (22-S3)

To a solution of 22-S2 (400 mg, 1.48 mmol) in dioxane (1 mL) was added HCl/dioxane (1 mL) at 0° C. The reaction mixture was stirred at room temperature for 2 hours. The mixture was concentrated to dryness to afford the title compound (450 mg, 100% yield) as a brown oil. LC/MS (ESI) m/z: 171 (M+H)⁺.

Step 3: (3S)-tert-Butyl 5-((4-((allyloxy)carbonyl)piperazin-1-yl)methyl)-3-((6-bromo-3-methylpyridin-2-yl)carbamoyl)-2-azabicyclo[3.1.0]hexane-2-carboxylate (22-S5)

To a solution of 22-S4 (280 mg, 0.66 mmol) in MeCN (5 mL) were added DIPEA (0.45 mL, 2.64 mmol), 22-S3 (179 mg, 0.66 mmol), and NaI at 0° C. The reaction mixture was stirred at room temperature overnight. The mixture was concentrated, diluted with DCM, and washed with water. The organic layer was dried over anhydrous Na$_2$SO$_4$, filtered, and concentrated. The remaining residue was purified by column chromatography on silica gel (eluted with DCM/MeOH=20:1) to afford the title compound (45 mg, 11.8% yield) as a yellow solid. LC/MS (ESI) m/z: 578 (M+H)⁺.

Step 4: Allyl 4-(((3S)-3-((6-bromo-3-methylpyridin-2-yl)carbamoyl)-2-azabicyclo[3.1.0]hexan-5-yl)methyl)piperazine-1-carboxylate (22-S6)

To a solution of 22-S5 (45 mg, 0.078 mmol) in dioxane (2 mL) was added HCl/dioxane (2 mL) at 0° C. The reaction mixture was stirred at room temperature for 2 hours. The mixture was concentrated to dryness to afford the title compound (65 mg, 100% yield) as a brown oil. LC/MS (ESI) m/z: 477 (M+H)⁺.

Step 5: Allyl 4-(((3S)-2-(2-(3-acetyl-5-(2-methylpyrimidin-5-yl)-1H-indazol-1-yl)acetyl)-3-((6-bromo-3-methylpyridin-2-yl)carbamoyl)-2-azabicyclo[3.1.0]hexan-5-yl)methyl)piperazine-1-carboxylate (22-S8)

To a solution of 22-S6 (65 mg, 0.078 mmol) and 22-S7 (24.18 mg, 0.078 mmol) in DMF (3 mL) were added HATU (53.4 mg, 0.14 mmol) and DIPEA (0.054 mL, 0.312 mmol) at 0° C. The reaction mixture was stirred at room temperature overnight. The mixture was diluted with water and extracted with EtOAc. The organic layer was washed with brine, dried over anhydrous Na$_2$SO$_4$, and concentrated to dryness. The remaining residue was purified by column chromatography on silica gel (eluted with DCM/MeOH=20:1) to afford the title compound (30 mg, 50.0% yield) as a white solid. LC/MS (ESI) m/z: 697 (M+H)⁺.

Step 6: (3S)-2-(2-(3-Acetyl-5-(2-methylpyrimidin-5-yl)-1H-indazol-1-yl)acetyl)-N-(6-bromo-3-methylpyridin-2-yl)-5-(piperazin-1-ylmethyl)-2-azabicyclo[3.1.0]hexane-3-carboxamide (22)

To a solution of 22-S8 (30 mg, 0.039 mmol) in dry THF (5 mL) were added morpholine (33.93 mg, 0.39 mmol) and Pd(PPh$_3$)$_4$ (2.3 mg, 0.0020 mmol) under an atmosphere of nitrogen at 0° C. The reaction mixture continued to stir at room temperature overnight. The mixture was diluted with EtOAc and washed with 10% aqueous LiCl solution and brine. The organic layer was dried over anhydrous Na$_2$SO$_4$ and concentrated to dryness. The remaining residue was purified by preparative HPLC to afford 22 (3.5 mg, 13.1% yield) as a white solid. ¹H NMR (400 MHz, CD$_3$OD) δ 9.01 (s, 2H), 8.56 (s, 1H), 7.80 (d, J=1.2 Hz, 2H), 7.55 (d, J=8.0 Hz, 1H), 7.38 (d, J=7.9 Hz, 1H), 5.80 (d, J=17.2 Hz, 1H), 5.66 (d, J=17.1 Hz, 1H), 4.65-4.62 (m, 1H), 3.64-3.66 m, 1H), 2.93 (t, J=4.9 Hz, 4H), 2.75 (s, 3H), 2.72-2.61 (m, 6H), 2.56 (d, J=6.9 Hz, 5H), 2.14 (d, J=8.2 Hz, 3H), 1.15 (t, J=5.6 Hz, 1H), 1.10-1.08 (m, 1H). LC/MS (ESI) m/z: 686 (M+H)⁺.

Scheme 16. Synthesis of (2S,4R)-1-(2-(3-Acetyl-5-(2-methylprimidin-5-yl)-1H-indazol-1-yl)acetyl)-N-(6-bromo-3-(cyanmethyl)pyridin-2-yl)-4-fluoropyrrolidine-2-carboxamide (23)

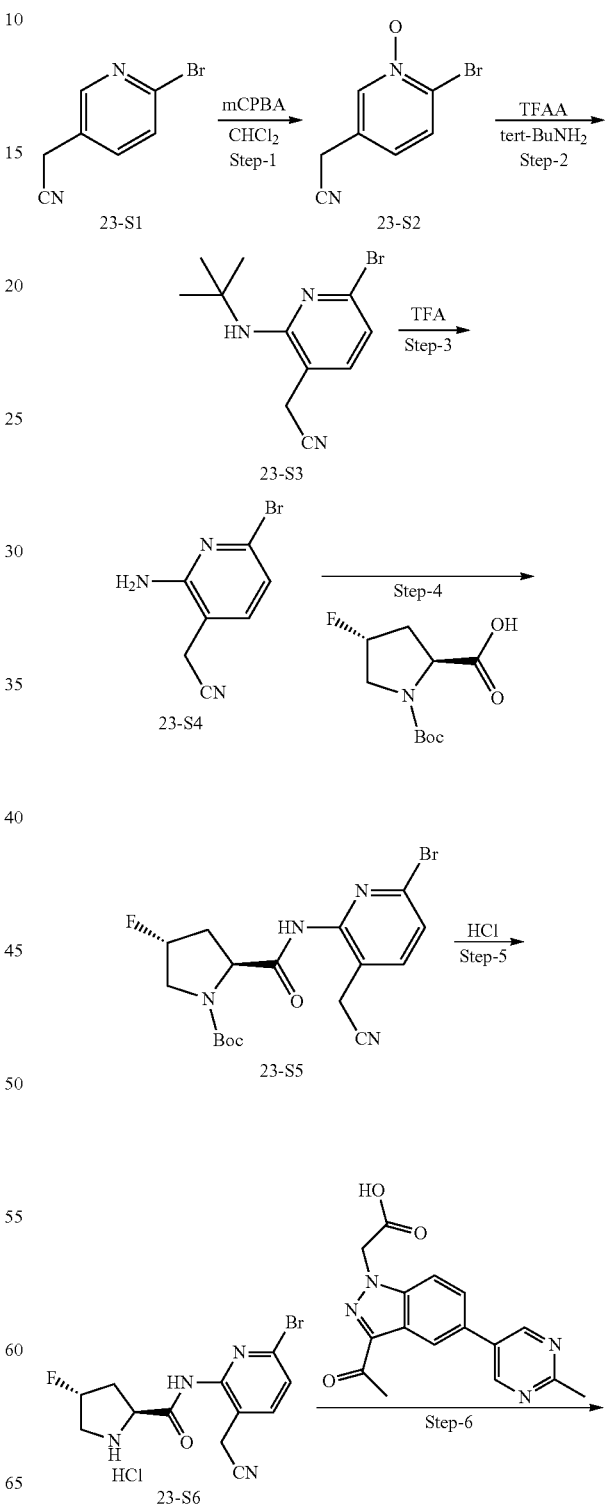

693

-continued

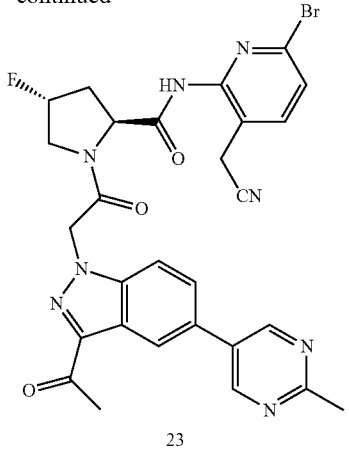

23

Step 1: 2-(6-Bromo-1-(1-oxidanyl)-pyridin-3-yl)acetonitrile (23-S2)

To a stirred solution of 2-(6-bromopyridin-3-yl) acetonitrile (23-S1, 1 g, 1 equiv) in CHCl₃ (100 mL) was added 3-chlorobenzoperoxoic acid (1.72 g, 77%, 1.5 equiv). The reaction mixture was heated to 50° C. The reaction mixture was cooled and neutralized with saturated aqueous NaHCO₃ solution (100 mL). The organic layer was washed with brine, dried over Na₂SO₄, and concentrated to dryness. The residue was purified by chromatography on silica gel (5% CH₃OH in DCM, gradient) to afford 23-S2 (99 mg, 10%).

Step 2: 2-(6-Bromo-2-(tert-butylamino)pyridin-3-yl)acetonitrile (23-S3)

To a stirred solution of 23-S2 (99 mg, 1 equiv) and 2-methylpropan-2-amine (0.24 mL, 5 equiv) in DCM (8 mL) was added trifluoroacidic anhydride (0.08 mL, 1.1 equiv) solution in DCM (3 mL) dropwise at 0-5° C. under an atmosphere of argon. The reaction mixture was stirred at 0-5° C. for 1 hour and TFAA (0.07 mL, 1 equiv) was added followed by 2-methylpropan-2-amine (0.02 mL, 1 equiv). The reaction mixture was diluted with DCM (25 mL) and neutralized with aqeuous saturated NaHCO₃ solution (10 mL). The organic layers were washed with brine (10 mL), dried over Na₂SO₄ and concentrated to dryness. The residue was purified by column chromatography on silica gel (eluted by hexanes/EtOAc=3/1) to afford 23-S3 (80 mg, 30%)

Step 3: 2-(2-Amino-6-bromopyridin-3-yl)acetonitrile (23-S4)

TFA (10 mL) was added to solid 23-S3 (80 mg) and the reaction mixture was heated at 70° C. The reaction mixture was concentrated to dryness. The residue was dissolved in DCM (15 mL) and washed with an aqueous saturated solution of NaHCO₃ (8 mL). The organic layer was dried over Na₂SO₄ and concentrated to dryness to afford 23-S4 (63 mg, quantitative yield)

Step 4: tert-Butyl (2S,4R)-2-((6-bromo-3-(cyanomethyl)pyridin-2-yl)carbamoyl)-4-fluoropyrrolidine-1-carboxylate (23-S5)

To a stirred solution of (2S, 4R)-1-(tert-butoxycarbonyl)-4-fluoropyrrolidine-2-carboxylic acid (69 mg, 1 equiv) and

694

23-S4 (63 mg, 1 equiv) in DCM (10 mL), was added pyridine (0.12 mL, 5 equiv). The reaction was cooled to 0-5° C. and POCl₃ was added dropwise (0.024 mL, 2 equiv) under an atmosphere of argon. The reaction mixture was warmed to room temperature, diluted with DCM (10 mL) and neutralized with aqueous saturated NaHCO₃ solution (10 mL). The aqueous layer was extracted with DCM (1×10 mL) and the combined organic layers were washed with brine (10 mL), dried over Na₂SO₄ and concentrated to dryness. The residue was purified by column chromatography on silica gel (eluted by 5% MeOH in DCM gradient) to afford 23-S5 (56 mg, 26%).

Step 5: (2S,4R)—N-(6-Bromo-3-(cyanomethyl)pyridin-2-yl)-4-fluoropyrrolidine-2-carboxamide Hydrochloride (23-S6)

To a solution of 23-S5 was added 4N HCl in dioxane (10 mL). The resulting solution was stirred at room temperature for 6 hours and then concentrated to dryness to afford 23-S6 (61 mg).

Step 6: (2S,4R)-1-(2-(3-Acetyl-5-(2-methylpyrimidin-5-yl)-1H-indazol-1-yl)acetyl)-N-(6-bromo-3-(cyanomethyl)pyridin-2-yl)-4-fluoropyrrolidine-2-carboxamide (23)

To a solution of 23-S6 (61 mg, 1 equiv), 2-(3-acetyl-5-(2-methylpyrimidin-5-yl)-1H-indazol-1-yl)acetic acid (50 mg, 1.2 equiv) in DMF (8 ml) and DIPEA (0.12 mL, 5 equiv) was added HATU (63 mg, 1.2 equiv) at 0° C. under an atmosphere of argon. The reaction mixture was stirred at room temperature for 3 hours before it was diluted with EtOAc (25 mL) and water (15 mL). The aqueous layer was extracted with EtOAc (15 mL) and the combined organic layers were washed with brine (15 mL×3), dried over anhydrous Na₂SO₄ and concentrated to dryness. The residue was purified by column chromatography on silica gel (eluted by DCM/MeOH=10:1) to afford 23. ¹H NMR (400 MHz, DMSO-d₆) δ 10.93 (s, 1H), 9.04 (s, 2H), 8.45 (s, 1H), 7.77-7.90 (m, 3H), 7.63 (d, 1H, J=8.2 Hz), 5.52-5.89 (m, 3H), 4.57-4.64 (m, 1H), 4.19-4.31 (m, 1H), 3.95-4.13 (m, 1H), 3.61-3.74 (m, 2H), 2.70 (s, 3H), 2.66 (s, 3H), 2.65-2.68 (m, 1H), 2.24-2.33 (m, 1H), 0.84-0.90 (m, 2H); ¹⁹F NMR (376 MHz, DMSO-d₆) δ −176.02 (s, 1F).

Scheme 17. Synthesis of Methyl 3-acetyl-1-(2-((2S,4R)-2-((6-bromopyridin-2-yl)carbamoyl)-4-fluoropyrrolidin-1-yl)-2-oxoethyl)-5-(2-methylpyrimidin-5-yl)-1H-indazole-7-carboxylate (25)

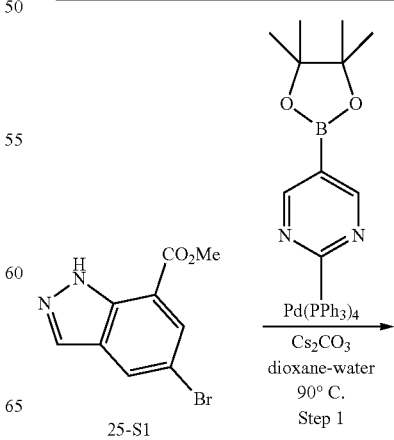

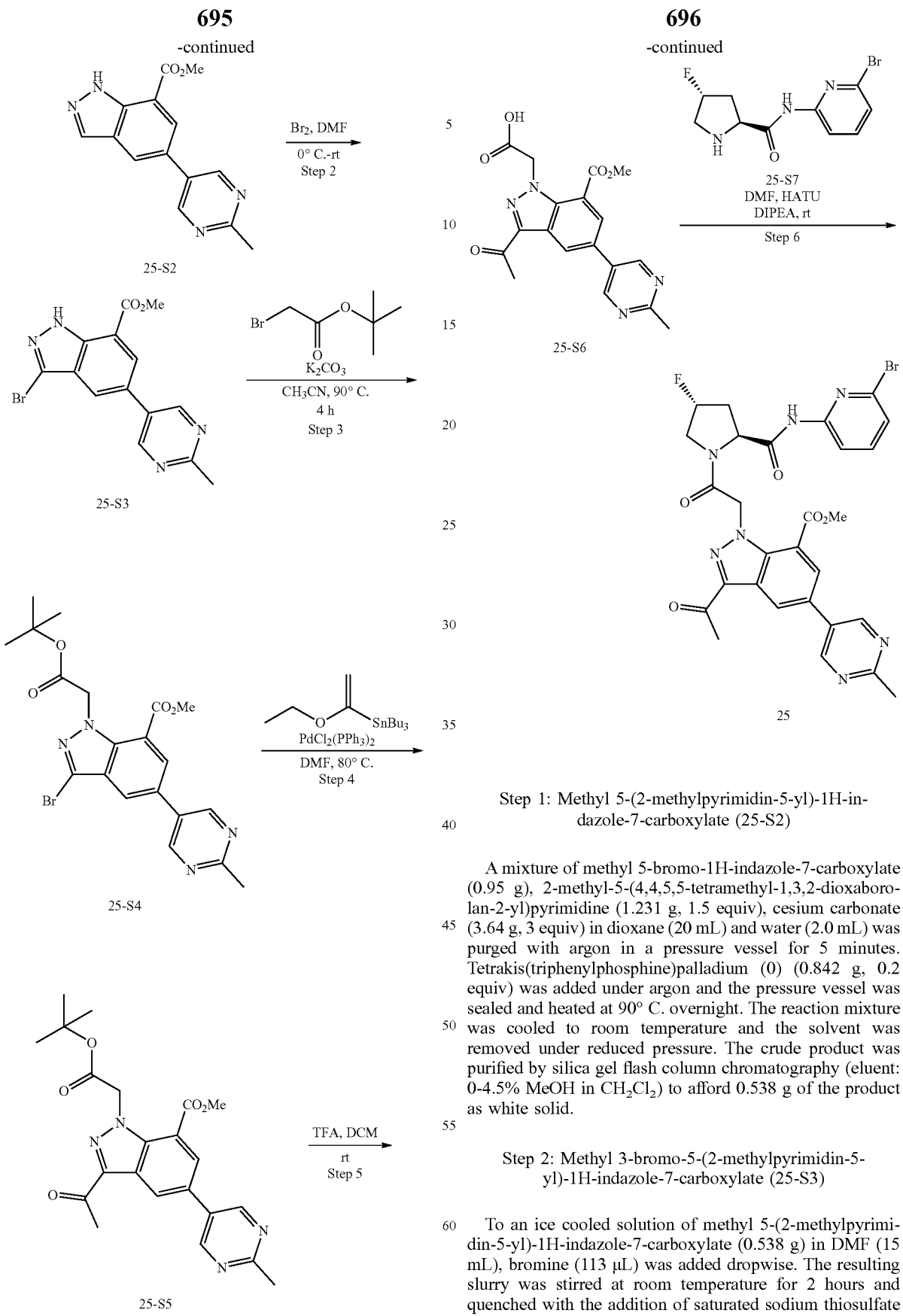

Step 1: Methyl 5-(2-methylpyrimidin-5-yl)-1H-indazole-7-carboxylate (25-S2)

A mixture of methyl 5-bromo-1H-indazole-7-carboxylate (0.95 g), 2-methyl-5-(4,4,5,5-tetramethyl-1,3,2-dioxaborolan-2-yl)pyrimidine (1.231 g, 1.5 equiv), cesium carbonate (3.64 g, 3 equiv) in dioxane (20 mL) and water (2.0 mL) was purged with argon in a pressure vessel for 5 minutes. Tetrakis(triphenylphosphine)palladium (0) (0.842 g, 0.2 equiv) was added under argon and the pressure vessel was sealed and heated at 90° C. overnight. The reaction mixture was cooled to room temperature and the solvent was removed under reduced pressure. The crude product was purified by silica gel flash column chromatography (eluent: 0-4.5% MeOH in $CH_2Cl_2$) to afford 0.538 g of the product as white solid.

Step 2: Methyl 3-bromo-5-(2-methylpyrimidin-5-yl)-1H-indazole-7-carboxylate (25-S3)

To an ice cooled solution of methyl 5-(2-methylpyrimidin-5-yl)-1H-indazole-7-carboxylate (0.538 g) in DMF (15 mL), bromine (113 μL) was added dropwise. The resulting slurry was stirred at room temperature for 2 hours and quenched with the addition of saturated sodium thiosulfate solution. The solid was isolated by filtration, washed with water, and dried. The material was carried forward in the next step without additional purification.

Step 3: Methyl 3-bromo-1-(2-(tert-butoxy)-2-oxo-ethyl)-5-(2-methylpyrimidin-5-yl)-1H-indazole-7-carboxylate (25-S4)

A mixture of methyl 3-bromo-5-(2-methylpyrimidin-5-yl)-1H-indazole-7-carboxylate (0.150 g), tert-butyl bromo-acetate (67 μL) and potassium carbonate (0.090 g) in anhydrous acetonitrile (10 mL) and DMF (1 mL) was refluxed for 4 hours. The reaction mixture was then cooled to room temperature and the solvent was removed under reduced pressure. The residue was triturated with water, filtered and dried. The material was carried forward in the next step without additional purification.

Step 4: Methyl 3-acetyl-1-(2-(tert-butoxy)-2-oxo-ethyl)-5-(2-methylpyrimidin-5-yl)-1H-indazole-7-carboxylate (25-S5)

A solution of methyl 3-bromo-1-(2-(tert-butoxy)-2-oxoethyl)-5-(2-methylpyrimidin-5-yl)-1H-indazole-7-carboxylate (0.100 g 1 equiv), tri-butyl(1-ethoxyvinyl)tin 0.15 mL, 2 equiv) and $PdCl_2(PPh_3)_2$ (15 mg, 0.1 equiv) in DMF (2 mL) was heated at 80° C. overnight under argon atmosphere. The reaction was then concentrated under reduced pressure and diluted with $CH_2Cl_2$ and washed with cold aqueous HCl (1N). The organic layer was dried ($Na_2SO_4$), filtered, concentrated, and the residue was purified by silica gel flash column chromatography (eluent: 0-1.5% MeOH in $CH_2Cl_2$) to afford a yellow solid.

Step 5: 2-(3-Acetyl-7-(methoxycarbonyl)-5-(2-methylpyrimidin-5-yl)-1H-indazol-1-yl)acetic Acid (25-S6)

Methyl 3-acetyl-1-(2-(tert-butoxy)-2-oxoethyl)-5-(2-methylpyrimidin-5-yl)-1H-indazole-7-carboxylate (25-S5) (0.08 g) was stirred in $CH_2Cl_2$ (1 mL) and TFA (2 mL). After completion of the reaction (monitored by HPLC), the solvent was removed under reduced pressure and the remaining residue was used directly in the next synthetic step without purification.

Step 6: Methyl 3-acetyl-1-(2-((2S,4R)-2-((6-bromopyridin-2-yl)carbamoyl)-4-fluoropyrrolidin-1-yl)-2-oxoethyl)-5-(2-methylpyrimidin-5-yl)-1H-indazole-7-carboxylate (25)

Compound 25-S6 from above was dissolved in DMF (1 mL) and $iPr_2NEt$ (0.164 mL, 5 equiv) was added, followed by the addition of 25-S7 at 5° C. HATU (86 mg, 1.2 equiv) was then added slowly at 5° C. and the reaction mixture was stirred for 30 minutes at room temperature. The reaction mixture was poured into water and the precipitate was isolated by filtration. The solid was dried and purified by silica gel flash column chromatography (eluent: 0-2.0% MeOH in $CH_2Cl_2$) to afford 25 as white solid. $^1H$ NMR (400 MHz, DMSO) δ 2.05-2.23 (m, 1H), 2.50-2.59 (m, 1H), 2.68 (s, 3H), 2.69 (s, 3H), 3.88-4.03 (m, 1H), 3.94 (s, 3H), 4.19 (dd, J=12.4, 21.8 Hz, 1H), 4.64 (t, J=8.4 Hz, 1H), 5.54 (d, J=52 Hz, 1H), 5.76 (d, J=17.4 Hz, 1H), 5.95 (d, J=17.4 Hz, 1H), 7.31 (d, J=7.7 Hz, 1H), 7.70 (t, J=8.0 Hz, 1H), 8.00 (d, J=8.2 Hz, 1H), 8.22 (d, J=2 Hz, 1H), 8.70 (d, J=1.8 Hz, 1H), 9.06 (s, 2H), 10.95 (s, 1H). $^{19}F$ NMR (DMSO-$d_6$): δ−176.1.

Scheme 18: Synthesis of (3S)-2-(2-(3-Acetyl-5-(2-methylpyrimidin-5-yl)-1H-indazol-1-yl)acetyl)-5-(aminoethyl)-N-(6-bromo-3-methylpyridin-2-yl)-2-azabicyclo[3.1.0]hexane-3-carboxamide (26)

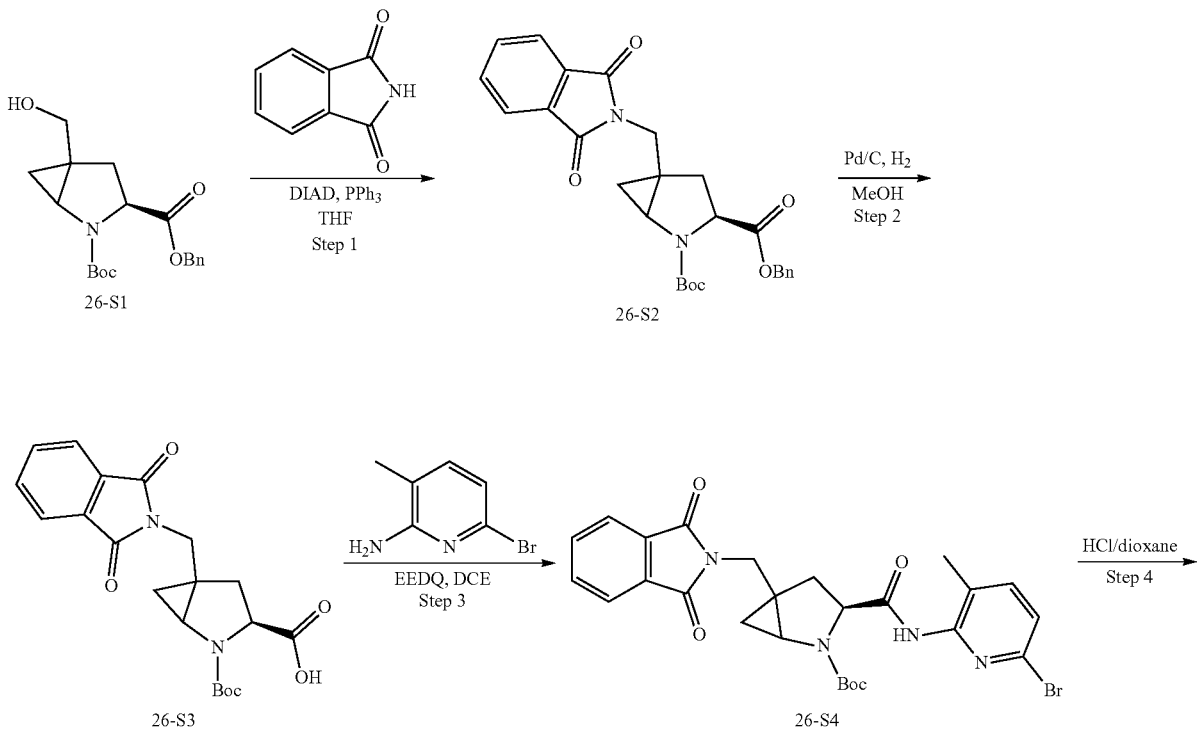

-continued

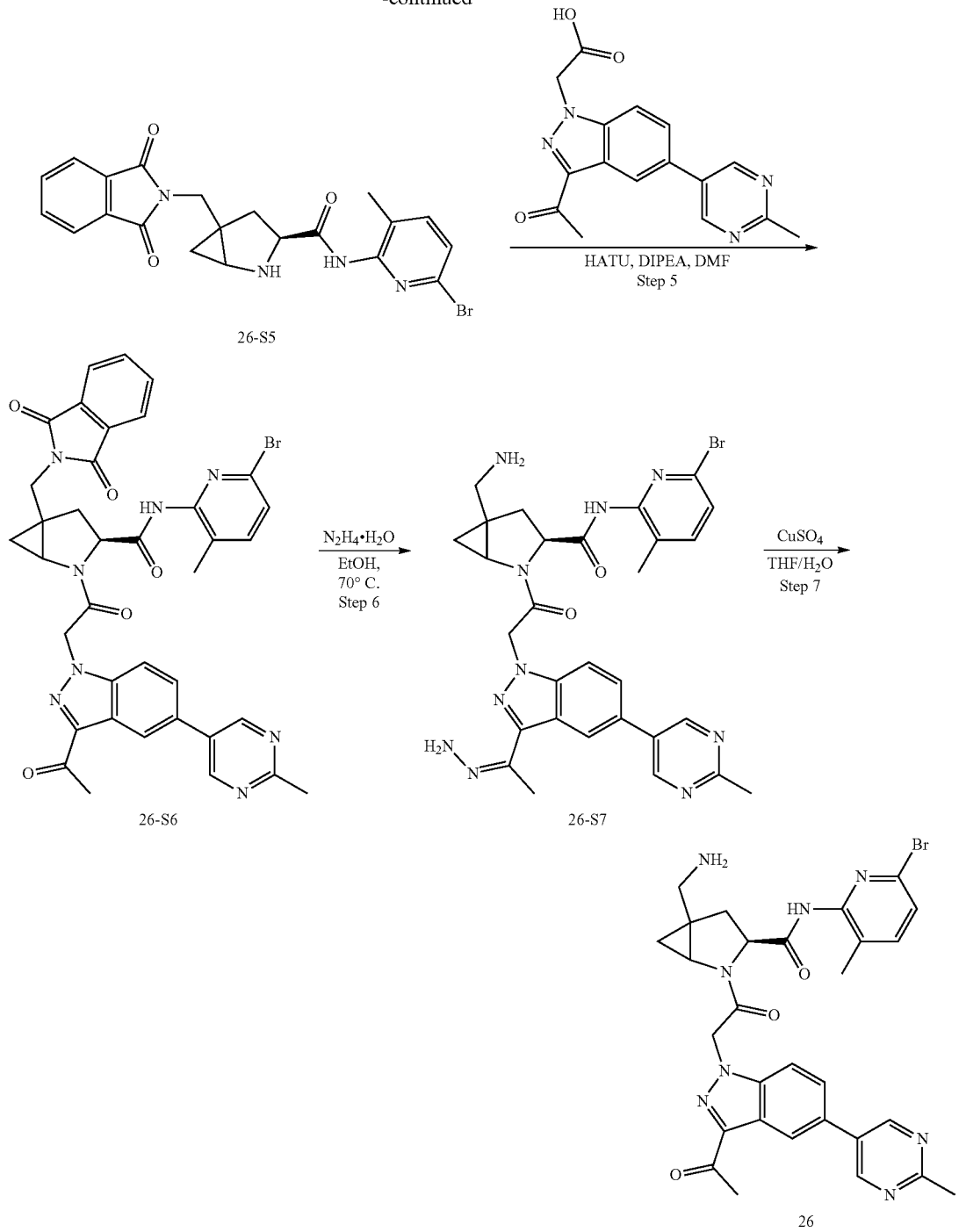

Step 1: (3S)-3-Benzyl 2-tert-butyl 5-((1,3-dioxoisoindolin-2-yl)methyl)-2-azabicyclo[3.1.0]hexane-2,3-dicarboxylate (26-S2)

To a solution of 26-S1 (300 mg, 0.86 mmol), isoindoline-1,3-dione (190 mg, 1.29 mmol), and PPh₃ (452 mg, 1.72 mmol) in THF (6 mL) was added DIAD (0.34 mL, 1.72 mmol) dropwise at 0° C. under an atmosphere of nitrogen. The reaction mixture was stirred at room temperature for 16 hours. The resulting mixture was partitioned with EtOAc and water. The organic layer was washed with brine, dried over anhydrous Na₂SO₄, and concentrated under reduced pressure. The remaining residue was purified by column chromatography on silica gel (eluted with PE/EtOAc=6:1) to afford 26-S2 (400 mg, 97.1% yield) as a light yellow viscous oil. LC/MS (ESI) m/z: 377 (M+H−100)⁺.

Step 2: (3S)-2-(tert-Butoxycarbonyl)-5-((1,3-dioxoisoindolin-2-yl)methyl)-2-azabicyclo[3.1.0]hexane-3-carboxylic Acid (26-S3)

A solution of 26-S2 (400 mg, 0.83 mmol) in MeOH (10 mL) was purged with nitrogen and Pd/C (60 mg, 5% wt) was added. The mixture was then purged with hydrogen and stirred under an atmosphere of hydrogen (balloon) at room temperature for 12 h. The reaction mixture was filtered through Celite, and the filtrate was concentrated. The remaining residue was purified by column chromatography on silica gel (eluted with DCM/MeOH=40:1) to afford 26-S3 (170 mg, 32.3% yield) as a light yellow oil. LC/MS (ESI) m/z: 287 (M+H−100)+.

Step 3: (3S)-tert-Butyl 3-(6-bromo-3-methylpyridin-2-ylcarbamoyl)-5-((1,3-dioxoisoindolin-2-yl)methyl)-2-azabicyclo[3.1.0]hexane-2-carboxylate (26-S4)

To a solution of 26-S3 (170 mg, 0.44 mmol) and 6-methylpyridin-2-amine (90 mg, 0.48 mmol) in DCE (5 mL) were added DIPEA (0.29 mL, 1.76 mmol) and EEDQ (217 mg, 0.88 mmol). The reaction mixture was stirred at 90° C. overnight and concentrated under high vacuum. The remaining residue was purified by column chromatography on silica gel (eluted with PE/EtOAc=4:1) to afford 26-S4 (103 mg, 41% yield) as a yellow solid. LC/MS (ESI) m/z: 555/557 (M+H)+.

Step 4: (3S)—N-(6-Bromo-3-methylpyridin-2-yl)-5-((1,3-dioxoisoindolin-2-yl)methyl)-2-azabicyclo[3.1.0]hexane-3-carboxamide (26-S5)

To a solution of 26-S4 (100 mg, 0.18 mmol) in dioxane (1 mL) was added HCl/dioxane (4 M, 1 mL). The reaction mixture was stirred at room temperature for 1 hour and concentrated to afford 26-S5 (82 mg, 100% yield) as a white solid. The crude material was carried forward in the next synthetic step without purification.

Step 5: (3S)-2-(2-(3-Acetyl-5-(2-methylpyrimidin-5-yl)-1H-indazol-1-yl)acetyl)-N-(6-bromo-3-methylpyridin-2-yl)-5-((1,3-dioxoisoindolin-2-yl)methyl)-2-azabicyclo[3.1.0]hexane-3-carboxamide (26-S6)

To a solution of 26-S5 (82 mg, 0.18 mmol), 2-(3-acetyl-5-(2-methylpyrimidin-5-yl)-1H-indazol-1-yl)acetic acid (67 mg, 0.21 mmol), and HATU (136 mg, 0.36 mmol) in DMF (2 mL) was added DIPEA (0.12 mL, 0.72 mmol). The reaction mixture was stirred at room temperature for 16 hours. The mixture was partitioned with EtOAc and water. The organic layer was washed with brine, dried over anhydrous Na2SO4, and concentrated under reduced pressure. The crude product was purified by column chromatography on silica gel (eluted with DCM/MeOH=30:1) to afford 26-S6 (60 mg, 44.7% yield) as an off-white solid.

Step 6: (3S)-5-(Aminomethyl)-N-(6-bromo-3-methylpyridin-2-yl)-2-(2-(3-((Z)-1-hydrazonoethyl)-5-(2-methylpyrimidin-5-yl)-1H-indazol-1-yl)acetyl)-2-azabicyclo[3.1.0]hexane-3-carboxamide (26-S7)

To a solution of 26-S6 (60 mg, 0.08 mmol) in EtOH (3 mL) was added hydrazine hydrate (0.1 mL, 85%). The reaction mixture was stirred at 50° C. for 12 hours and then cooled to room temperature. The mixture was filtered, the filtrate was concentrated to dryness, and the remaining crude product was purified by column chromatography on silica gel (eluted with DCM/MeOH=20:1) to afford 26-S7 (30 mg, 60.1% yield) as a yellow oil.

Step 7: (3S)-2-(2-(3-Acetyl-5-(2-methylpyrimidin-5-yl)-1H-indazol-1-yl)acetyl)-5-(aminomethyl)-N-(6-bromo-3-methylpyridin-2-yl)-2-azabicyclo[3.1.0]hexane-3-carboxamide (26)

To a solution of 26-S7 (30 mg, 0.047 mmol) in THF/H2O (1 mL/1 mL) was added copper(II) sulfate (38 mg, 0.24 mmol). The reaction mixture was stirred at 50° C. for 12 hours and then cooled to room temperature. The mixture was filtered, the filtrate was concentrated to dryness, and the remaining crude product was purified by preparative TLC to afford 26 (3.6 mg, 12.4% yield) as a yellow solid. 1H NMR (400 MHz, CD3OD) δ 9.01 (s, 2H), 8.55 (s, 1H), 7.78 (s, 2H), 7.54 (d, J=8.0 Hz, 1H), 7.38 (d, J=8.0 Hz, 1H), 5.65-5.79 (m, 2H), 5.14-5.19 (m, 1H), 3.90-3.94 (m, 1H), 3.40-3.43 (m, 1H), 3.01-3.05 (m, 1H), 2.75 (s, 3H), 2.70 (s, 3H), 2.47-2.51 (m, 1H), 2.29-2.39 (m, 1H), 2.08 (s, 3H), 0.83-0.90 (m, 2H). LC/MS (ESI) ml/z: 617 (M+H)+.

Scheme 19. Synthesis of (1R,3S,5R)-2-(2-(3-Acetyl-7-methyl-5-(2-methylpyrimidin-5-yl)-1H-indazol-1-yl)acetyl)-N-(6-bromo-5-fluoro-3-methylpyridin-2-yl)-5-methyl-2-azabicyclo[3.1.0]hexane-3-carboxamide (27)

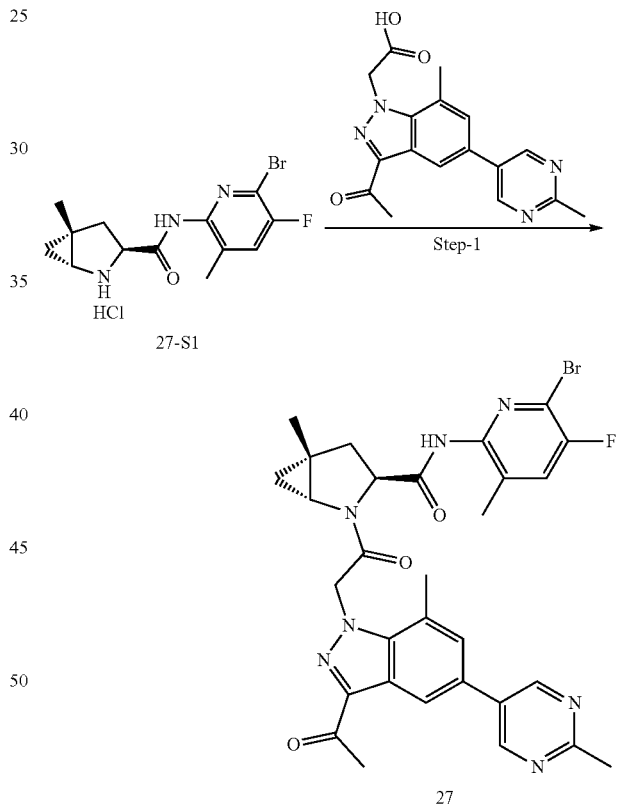

HATU (128 mg, 1.2 equiv) was added at 0° C. under an atmosphere of argon to a solution of 27-S6 (102 mg, 1 equiv), 2-(3-acetyl-7-methyl-5-(2-methylpyrimidin-5-yl)-1H-indazol-1-yl)acetic acid (92 mg, 1.2 equiv), and DIPEA (0.24 mL, 5 equiv) in DMF (8 mL). The reaction mixture was stirred at room temperature for 3 hours before it was diluted with EtOAc (30 mL) and water (15 mL). The organic layer was washed with brine, dried over anhydrous Na2SO4, and concentrated to dryness. The residue was purified by column chromatography on silica gel (eluted with DCM/MeOH=10:1) to afford 27 (70 mg, 39%). 1H NMR (400

MHz, DMSO-d$_6$) δ 10.31 (s, 1H), 9.03 (s, 2H), 8.35 (s, 1H), 7.82 (d, 1H, J=8.4 Hz), 7.62 (s, 1H), 6.03 (d, 1H, J=18.0 Hz), 5.69 (d, 1H, J=18.0 Hz), 4.37-4.43 (m, 1H), 3.59-3.62 (m, 1H), 2.69 (s, 6H), 2.65 (s, 3H), 2.53-2.60 (m, 1H), 2.08 (s, 3H), 2.02-2.10 (m, 1H), 1.33 (s, 3H), 0.93-1.05 (m, 2H). $^{19}$F NMR (376 MHz, DMSO-d$_6$): δ−119.12 (s, 1F).

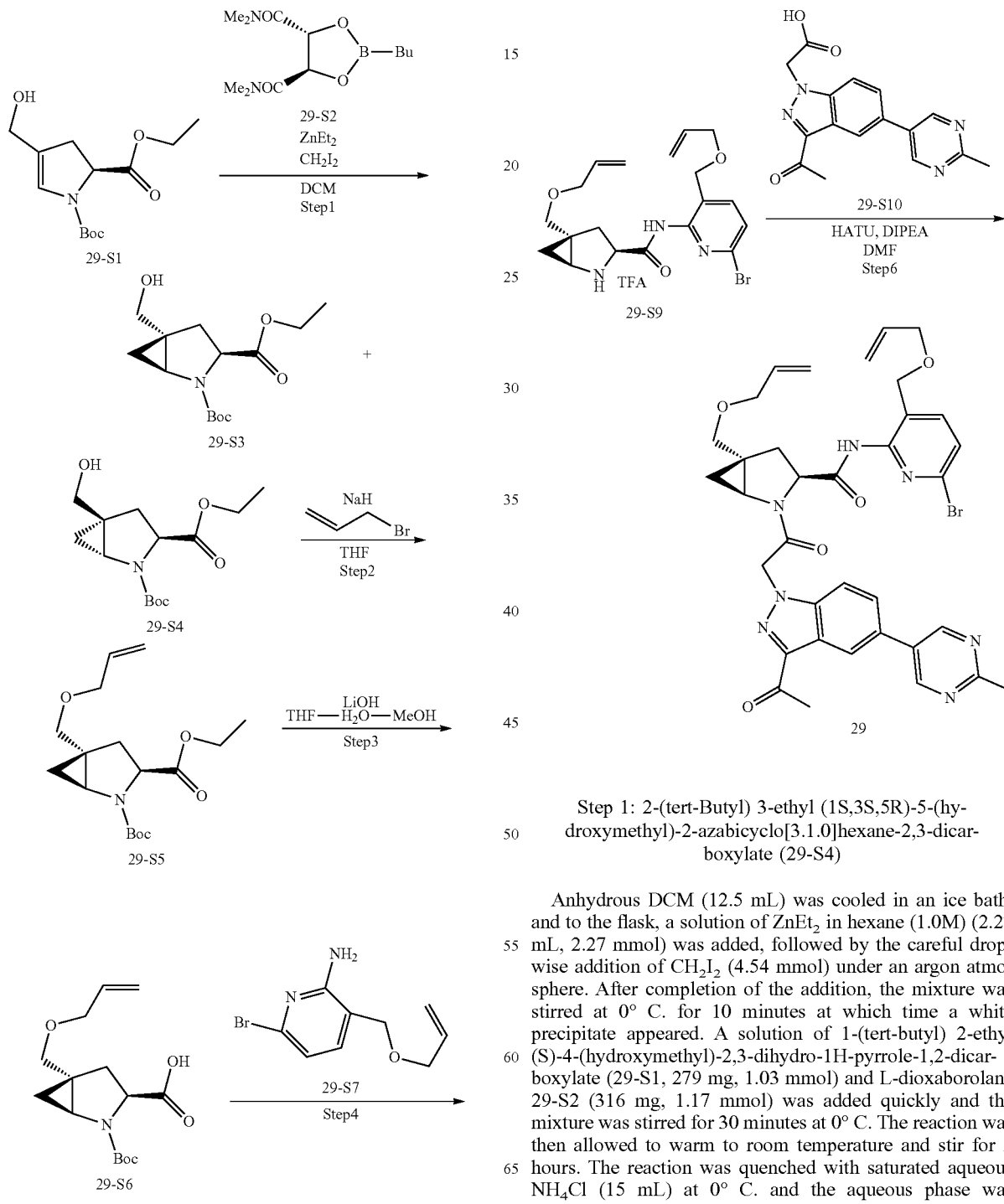

Scheme 20. Synthesis of (1S,3S,5R)-2-(2-(3-Acetyl-5-(2-methylpyrimidin-5-yl)-1H-indazol-1-yl)acetyl)-5-((allyloxy)methyl)-N-(3-((allyloxy)methyl)-6-bromopyridin-2-yl)-2-azabicyclo[3.1.0]hexane-3-carboxamide (29)

Step 1: 2-(tert-Butyl) 3-ethyl (1S,3S,5R)-5-(hydroxymethyl)-2-azabicyclo[3.1.0]hexane-2,3-dicarboxylate (29-S4)

Anhydrous DCM (12.5 mL) was cooled in an ice bath, and to the flask, a solution of ZnEt$_2$ in hexane (1.0M) (2.27 mL, 2.27 mmol) was added, followed by the careful dropwise addition of CH$_2$I$_2$ (4.54 mmol) under an argon atmosphere. After completion of the addition, the mixture was stirred at 0° C. for 10 minutes at which time a white precipitate appeared. A solution of 1-(tert-butyl) 2-ethyl (S)-4-(hydroxymethyl)-2,3-dihydro-1H-pyrrole-1,2-dicarboxylate (29-S1, 279 mg, 1.03 mmol) and L-dioxaborolane 29-S2 (316 mg, 1.17 mmol) was added quickly and the mixture was stirred for 30 minutes at 0° C. The reaction was then allowed to warm to room temperature and stir for 2 hours. The reaction was quenched with saturated aqueous NH$_4$Cl (15 mL) at 0° C. and the aqueous phase was extracted with DCM (15 mL×2). The combined DCM solutions were washed with brine and dried over MgSO$_4$. The solution was filtered and concentrated and the resulting residue was purified to afford 29-S4 (153 mg).

Step 2: 2-(tert-Butyl) 3-ethyl (1S,3S,5R)-5-((allyloxy)methyl)-2-azabicyclo[3.1.0]hexane-2,3-dicarboxylate (29-S5)

To the solution of 2-(tert-butyl) 3-ethyl (1S,3S,5R)-5-(hydroxymethyl)-2-azabicyclo[3.1.0]hexane-2,3-dicarboxylate (29-S4, 153 mg, 0.53 mmol) in THF at 0° C., NaH (60%, 2.65 mmol) was added under argon. The mixture was stirred for 30 minutes, allyl bromide (3.0 mmol) was added, and the reaction was warmed to 40° C. for 4 hours. The reaction was cooled in an ice bath and quenched carefully with aqueous NH$_4$Cl. The mixture was extracted with ethyl acetate (15 mL×3) and the combined organic layers were washed with water, brine, and dried over MgSO$_4$. The solution was concentrated and the residue was purified to afford 29-S5 (137 mg). $^1$H NMR (400 MHz, DMSO-d$_6$, 300 K): δ 0.77-0.85 (m, 1H), 1.18-1.94 (m, 1H), 1.27 (t, J=7.2 Hz, 3H), 1.41 (s, 9H), 2.09-2.14 (m, 1H), 2.57-2.71 (m, 1H), 3.33-3.45 (m, 3H), 3.97 (d, J=5.2 Hz, 2H), 4.10-4.20 (m, 2H), 4.52-4.64 (m, 1H), 5.18 (d, J=10.4 hz, 1H), 5.26 (d, J=17.2 Hz, 1H), 5.84-5.93 (m, 1H) ppm.

Step 3: (1S,3S,5R)-5-((Allyloxy)methyl)-2-(tert-butoxycarbonyl)-2-azabicyclo[3.1.0]hexane-3-carboxylic Acid (29-S6)

Compound 29-S5 (137 mg, 0.42 mmol) was dissolved in a mixture of CH$_3$OH-THF—H$_2$O (2 mL-2 mL-2 mL) and treated with LiOH (40 mg, 1.67 mmol). The reaction mixture was stirred overnight at room temperature before the volatiles were evaporated under reduced pressure and the remaining residue was acidified with 10% citric acid (10 mL). The mixture was extracted with ethyl acetate (15 mL×3) and the combined organic layers were washed with water, brine and dried over MgSO$_4$. The solution was concentrated and the residue 29-S6 (108 mg) was dried and carried forward without additional purification. LC (method A): t$_R$=1.66 min. LC/MS (EI) m/z: [M+H]$^+$ 298.4

Step 4: tert-Butyl (1S,3S,5R)-5-((allyloxy)methyl)-3-((3-((allyloxy)methyl)-6-bromopyridin-2-yl)carbamoyl)-2-azabicyclo[3.1.0]hexane-2-carboxylate (29-S8)

(1S,3S,5R)-5-((Allyloxy)methyl)-2-(tert-butoxycarbonyl)-2-azabicyclo[3.1.0]hexane-3-carboxylic acid (29-S6, 108 mg, 0.36 mmol), 3-((allyloxy)methyl)-6-bromopyridin-2-amine (29-S7, 97 mg, 0.40 mmol) were dissolved in anhydrous DCM (5 mL) in a pre-dried flask. The flask was cooled using an ice bath and dry pyridine (0.25 mL) was added in one portion, followed by POCl$_3$ (100 μL, 1.0 mmol). After completion of the addition, the mixture was stirred for 4 hours at 0° C. and the reaction was quenched with water (15 mL). The DCM layer was collected and the aqueous phase was extracted with DCM (15 mL×2). The combined DCM solutions were washed with brine and dried over MgSO$_4$. The solution was filtered and concentrated and the resulting residue was purified to afford 29-S8 (126 mg). $^1$H NMR (400 MHz, Chloroform-d) δ 0.75-0.92 (m, 1H), 1.02-1.17 (m, 1H), 1.51 (s, 9H), 2.35-2.80 (m, 2H), 3.42 (d, J=10.4 Hz, 1H), 3.52-3.63 (m, 2H), 3.90-4.11 (m, 4H), 4.36-4.44 (m, 2H), 4.74-4.87 (br, 1H), 5.18-5.31 (m, 4H), 5.85-5.92 (m, 2H), 7.29 (d, J=8.0 Hz, 1H), 7.62 (d, J=7.9 Hz, 1H), 9.16 (s, 1H) ppm. LC (method A): t$_R$=2.68 min. LC/MS (EI) m/z: [M+H]$^+$ 524.44

Step 5: (1S,3S,5R)-5-((Allyloxy)methyl)-N-(3-((allyloxy)methyl)-6-bromopyridin-2-yl)-2-azabicyclo[3.1.0]hexane-3-carboxamide TFA Salt (29-S9)

tert-Butyl (1S,3S,5R)-5-((allyloxy)methyl)-3-((3-((allyloxy)methyl)-6-bromopyridin-2-yl)carbamoyl)-2-azabicyclo[3.1.0]hexane-2-carboxylate (29-S8, 104 mg) was dissolved in DCM (4 mL) and treated with TFA (1 mL). The mixture was stirred overnight at room temperature. The volatiles were evaporated under reduced pressure. The remaining material was co-evaporated with toluene twice and the residue (29-S9) was carried forward in the next step without additional purification.

Step 6: (1S,3S,5R)-2-(2-(3-Acetyl-5-(2-methylpyrimidin-5-yl)-1H-indazol-1-yl)acetyl)-5-((allyloxy)methyl)-N-(3-((allyloxy)methyl)-6-bromopyridin-2-yl)-2-azabicyclo[3.1.0]hexane-3-carboxamide (29)

To the solution of (1S,3S,5R)-5-((allyloxy)methyl)-N-(3-((allyloxy)methyl)-6-bromopyridin-2-yl)-2-azabicyclo[3.1.0]hexane-3-carboxamide TFA salt (29-S9, 0.2 mmol), 2-(3-acetyl-5-(2-methylpyrimidin-5-yl)-1H-pyrazolo[3,4-c]pyridin-1-yl)acetic acid (29-S10, 62 mg, 0.2 mmol) in DMF (2.0 mL), HATU (114 mg, 0.3 mmol) was added, followed by the dropwise addition of DIEA (5.0 eq) at room temperature. The mixture was stirred for 1 hour at room temperature and the volatiles were evaporated. The residue was diluted with 10% sodium carbonate (50 mL) and extracted with ethyl acetate. The combined organic solution was successively washed with water and brine and dried over MgSO$_4$. The solution was filtered and the solvent was removed. The residue was purified to afford 29 (31.1 mg). $^1$H NMR (400 MHz, DMSO-d$_6$): (major rotamer) δ 1.05 (t, J=5.7 Hz, 1H), 1.44-1.46 (m, 1H), 2.07 (dd, J=13.5, 3.6 Hz, 1H), 2.64 (s, 3H), 2.68 (s, 4H), 3.41-3.76 (m, 4H), 3.79 (dd, J=6.0, 2.6 Hz, 1H), 4.03 (d, J=5.5 Hz, 2H), 4.16 (s, 2H), 4.91 (dd, J=11.4, 3.6 Hz, 1H), 4.96-5.13 (m, 2H), 5.20-5.36 (m, 2H), 5.58 (d, J=17.2 Hz, 1H), 5.69-5.74 (m 1H), 5.91-5.98 (m, 2H), 7.52 (d, J=8.0 Hz, 1H), 7.75-7.88 (m, 3H), 8.43 (s, 1H), 9.03 (s, 2H), 10.55 (s, 1H) ppm. LC (method A): t$_R$=2.28 min. LC/MS (EI) m/z: [M+H]$^+$ 714.44, 716.47.

Scheme 21: Synthesis of 1R,3S,5R)-2-(2-(3-Acetyl-7-(fluoromethyl)-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (31)

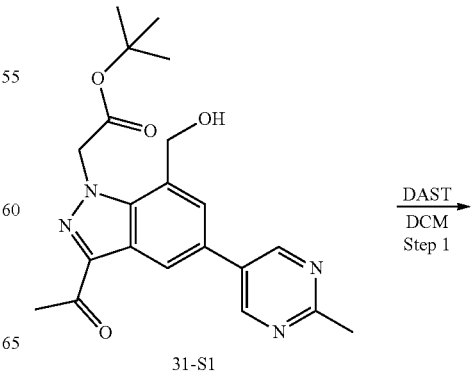

31-S1

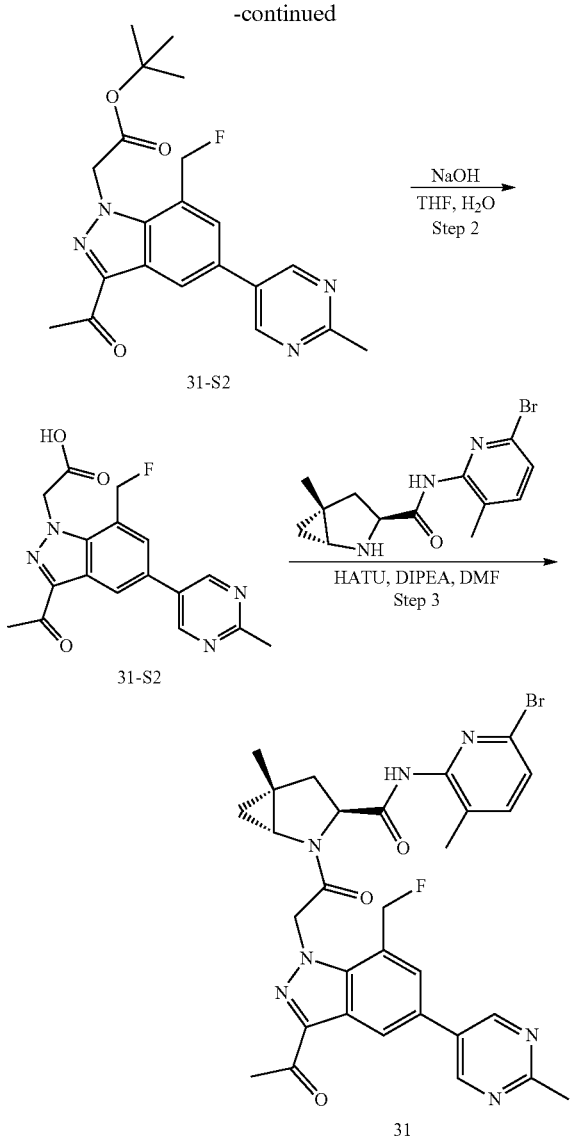

31-S2

31-S2

31

Step 1: tert-Butyl 2-(3-acetyl-7-(fluoromethyl)-5-(2-methylpyrimidin-5-yl)-1H-indazol-1-yl)acetate (31-S2)

To a mixture of 31-S1 (163 mg, 0.38 mmol) in dry DCM (10 mL) was added DAST (124 mg, 0.76 mmol) at −30° C. under an atmosphere of nitrogen. The reaction mixture was stirred at room temperature for 1 hour. The reaction mixture was quenched with saturated aqueous NaHCO$_3$ solution and extracted with DCM twice. The combined organic layers were washed with brine, dried over anhydrous Na$_2$SO$_4$, and concentrated under reduced pressure to afford 31-S2 (140 mg, 92% yield) as a white solid, which was used in the next synthetic step without further purification. LC/MS (ESI) m/z: 399 (M+H)$^+$.

Step 2: 2-(3-Acetyl-7-(fluoromethyl)-5-(2-methylpyrimidin-5-yl)-1H-indazol-1-yl)acetic Acid (31-S3)

To a solution of 31-S2 (65 mg, 0.16 mmol) in THF/H$_2$O (3:1 v/v, 4 mL) was added NaOH (14 mg, 0.32 mmol). The reaction mixture was stirred at room temperature for 1 hour. The mixture was diluted with water and washed with diethyl ether twice. The aqueous layer was adjusted to pH 5 with 10% aqueous HCl solution and extracted with DCM twice. The organic layer was dried over Na$_2$SO$_4$ and concentrated to afford 31-S3 (35 mg, 63.8% yield) as a white solid, which was used in the next synthetic step without further purification. LC/MS (ESI) m/z: 343 (M+H)$^+$.

Step 3: (1R,3S,5R)-2-(2-(3-Acetyl-7-(fluoromethyl)-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (31)

To a solution of 31-S3 (35 mg, 0.1 mmol), (1R,3S,5R)—N-(6-bromo-3-methylpyridin-2-yl)-5-methyl-2-azabicyclo[3.1.0]hexane-3-carboxamide (46 mg, 0.13 mmol), and HATU (57 mg, 0.15 mmol) in DMF (3 mL) was added DIPEA (39 mg, 0.3 mmol). The reaction mixture was stirred at room temperature for 16 hours. The mixture was diluted with EtOAc, washed successively with 10% aqueous LiCl solution and brine, dried over anhydrous Na$_2$SO$_4$, and concentrated under reduced pressure. The remaining residue was purified by preparative HPLC (eluted with MeCN/water) to afford 31 (8 mg, 12.6% yield) as a white solid. $^1$H NMR (400 MHz, DMSO-d$_6$) δ 10.34 (s, 1H), 9.08 (s, 2H), 8.58 (s, 1H), 8.01 (s, 1H), 7.63 (d, J=8.1 Hz, 1H), 7.45 (d, J=7.9 Hz, 1H), 5.95 (t, J=5.7 Hz, 1H), 5.81-5.91 (m, 1H), 5.72-5.78 (m, 1H), 5.61-5.69 (m, 1H), 4.38-4.44 (m, 1H), 3.58 (d, J=2.9 Hz, 1H), 2.69 (s, 3H), 2.66 (s, 3H), 2.55-2.62 (m, 1H), 1.98-2.13 (m, 4H), 1.33 (s, 3H), 0.97-1.06 (m, 2H). LC/MS (ESI) m/z: 634 (M+H)$^+$.

Scheme 22. Synthesis of (1R,3S,5S)-2-(2-(3-Acetyl-7-(methoxymethyl)-5-(2-methylpyrimidin-5-yl)-1H-indazol-1-yl)acetyl)-N-(6-bromopyridin-2-yl)-5-(methoxymethyl)-2-azabicyclo[3.1.0]hexane-3-carboxamide (32)

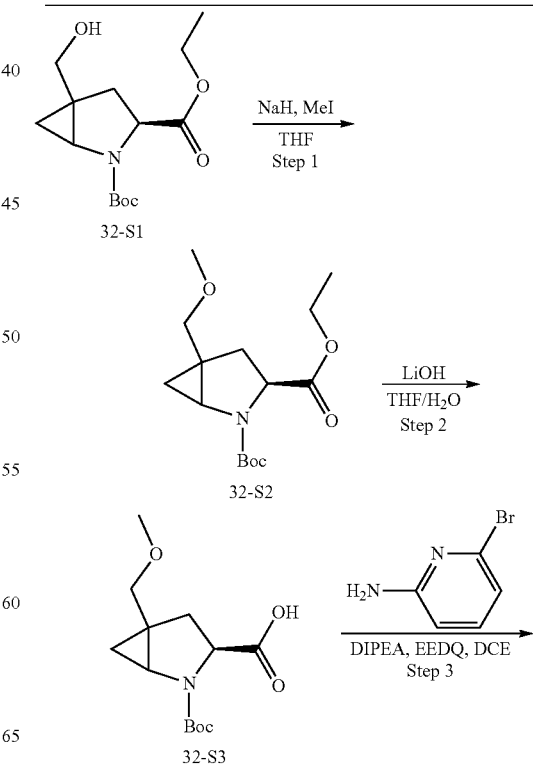

32-S1

32-S2

32-S3

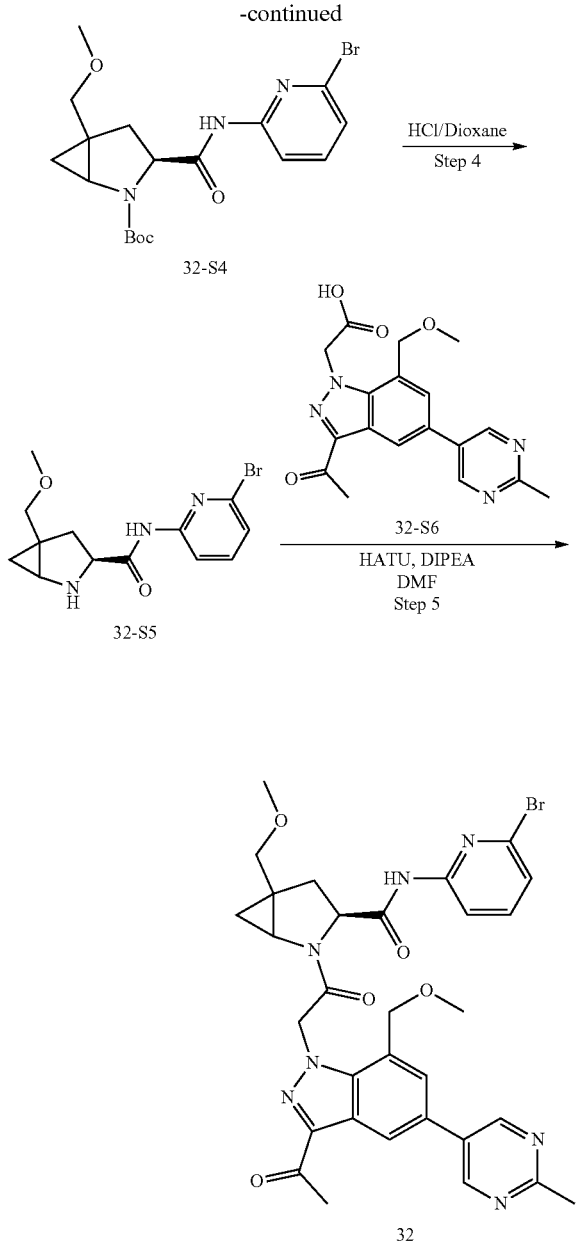

Step 2: (3S)-2-(tert-Butoxycarbonyl)-5-(methoxymethyl)-2-azabicyclo[3.1.0]hexane-3-carboxylic Acid (32-S3)

To a mixture of 32-S2 (160 mg, 0.5 mmol) in THF (2 mL) and water (2 mL) was added LiOH (62.7 mg, 1.5 mmol) at 0° C. The reaction mixture was stirred at room temperature for 3 hours. The mixture was concentrated to half volume and washed with EtOAc twice. The mixture was acidified by 2 N aqueous HCl and extracted with DCM twice. The combined organic layers were concentrated to dryness to afford 32-S3 (120 mg, 88.9% yield) as a colorless oil. LC/MS (ESI) m/z: 272 (M+H)+.

Step 3: tert-Butyl (3S)-3-((6-bromopyridin-2-yl)carbamoyl)-5-(methoxymethyl)-2-azabicyclo[3.1.0]hexane-2-carboxylate (32-S4)

To a mixture of 32-S3 (100 mg, 0.37 mmol) and 6-bromopyridin-2-amine (24.6 mg, 0.37 mmol) in DCE (5 mL) were added DIPEA (0.25 mL, 1.48 mmol) and EEDQ (183 mg, 0.74 mmol) at 0° C. The reaction mixture was stirred at 90° C. overnight. The mixture was concentrated to dryness and the remaining residue was purified by column chromatography on silica gel (eluted with PE/EtOAc=1:1) to afford 32-S4 (110 mg, 69.8% yield) as a yellow solid. LC/MS (ESI) m/z: 426 (M+H)+.

Step 4: (3S)—N-(6-Bromopyridin-2-yl)-5-(methoxymethyl)-2-azabicyclo[3.1.0]hexane-3-carboxamide (32-S5)

To a solution of 32-S4 (95 mg, 0.223 mmol) in dioxane (2 mL) was added HCl/dioxane (2 mL, 2 M) at 0° C. The reaction mixture was stirred at room temperature for 2 hours. The mixture was concentrated to dryness to afford 32-S5 (114 mg, 100% yield) as a brown syrup, which was used in the next synthetic step without purification. LC/MS (ESI) m/z: 326 (M+H)+.

Step 5: (3S)-2-(2-(3-Acetyl-7-(methoxymethyl)-5-(2-methylpyrimidin-5-yl)-1H-indazol-1-yl)acetyl)-N-(6-bromopyridin-2-yl)-5-(methoxymethyl)-2-azabicyclo[3.1.0]hexane-3-carboxamide (32)

To a mixture of 32-S5 (57 mg, 0.11 mmol), 2-(3-acetyl-7-(methoxymethyl)-5-(2-methylpyrimidin-5-yl)-1H-indazol-1-yl)acetic acid (39 mg, 0.078 mmol), and HATU (75 mg, 0.198 mmol) in DMF (3 mL) was added DIPEA (0.076 mL, 0.44 mmol) at 0° C. The reaction mixture was stirred at room temperature overnight. The mixture was diluted with EtOAc, washed with 10% aqueous LiCl solution and brine, dried over Na$_2$SO$_4$, and concentrated to dryness. The remaining residue was purified by preparative HPLC to afford 32 (19 mg, 50.4% yield) as a white solid. $^1$H NMR (400 MHz, CD$_3$OD) δ 9.02 (s, 2H), 8.59 (d, J=1.7 Hz, 1H), 8.08 (d, J=7.9 Hz, 1H), 7.73 (d, J=1.7 Hz, 1H), 7.61 (t, J=8.0 Hz, 1H), 7.25 (d, J=7.3 Hz, 1H), 6.04 (d, J=17.5 Hz, 1H), 5.86 (d, J=17.4 Hz, 1H), 4.99 (s, 1H), 4.72 (d, J=12.6 Hz, 1H), 4.56 (d, J=9.0 Hz, 1H), 3.69 (dd, J=5.7, 2.6 Hz, 1H), 3.53 (q, J=10.3 Hz, 2H), 3.39 (d, J=3.1 Hz, 6H), 2.75 (s, 3H), 2.70 (d, J=2.5 Hz, 3H), 2.53 (dd, J=13.5, 9.2 Hz, 1H), 2.41 (dd, J=12.8, 5.1 Hz, 1H), 1.15-1.11 (m, 1H), 0.90 (t, J=6.8 Hz, 1H). LC/MS (ESI) m/z: 662 (M+H)+.

Step 1: 2-(tert-Butyl) 3-ethyl (3S)-5-(methoxymethyl)-2-azabicyclo[3.1.0]hexane-2,3-dicarboxylate (32-S2)

To a solution of 32-S1 (500 mg, 1.75 mmol) in THF (5 mL) was added NaH (105.4 mg, 4.39 mmol) at 0° C. under an atmosphere of nitrogen and the mixture was stirred at 0° C. for 20 minutes. Iodomethane (740 mg, 5.25 mmol) was added and the resulting mixture was stirred at 0° C. under an atmosphere of nitrogen for 3 hours. The reaction mixture was quenched by aqueous NH$_4$Cl solution and diluted with EtOAc. The mixture was washed with water and brine, dried over Na$_2$SO$_4$, filtered, and concentrated to dryness. The remaining residue was purified by column chromatography on silica gel (eluted with PE/EtOAc=5:1) to afford 32-S2 (160 mg, 30.5% yield) as a colorless oil. LC/MS (ESI) m/z: 300 (M+H)+.

Scheme 23. Synthesis of 3-Acetyl-1-(2-((2S,4R)-2-((6-bromopyridin-2-yl)carbamoyl)-4-fluoropyrrolidin-1-yl)-2-oxoethyl)-5-(2-methylpyrimidin-5-yl)-1h-indazole-7-carboxylic acid (41)

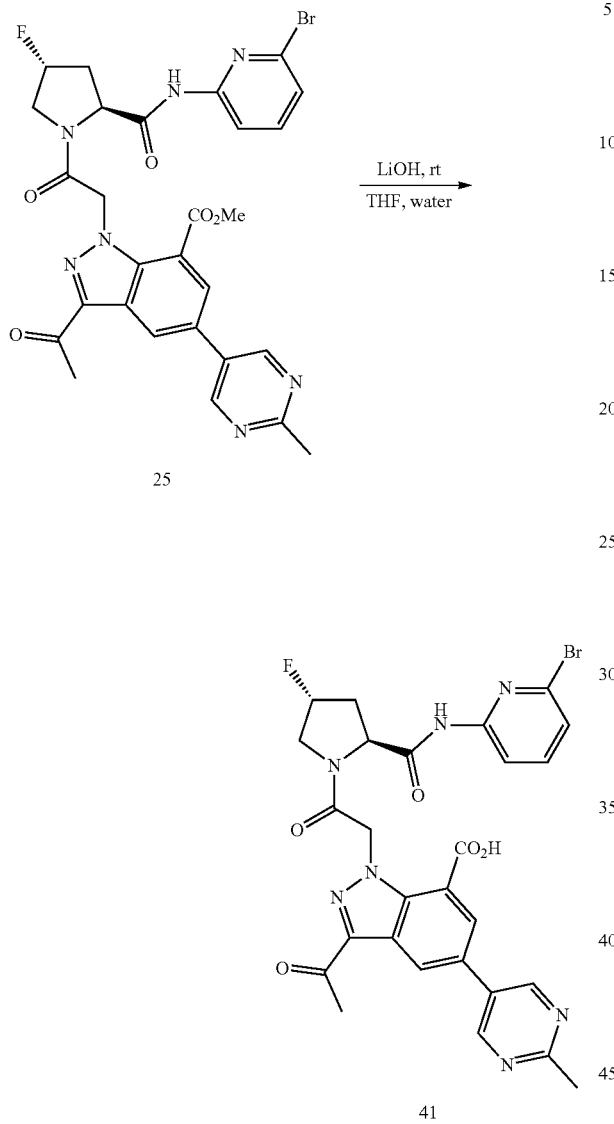

Scheme 24. Synthesis of (3S)-2-(2-(3-Acetyl-5-(2-methylpyrimidin-5-yl)-1H-indazol-1-yl)acetyl)-N-(6-bromo-3-methylpyridin-2-yl)-5-((methylamino)methyl)-2-azabicyclo[3.1.0]hexane-3-carboxamide (42)

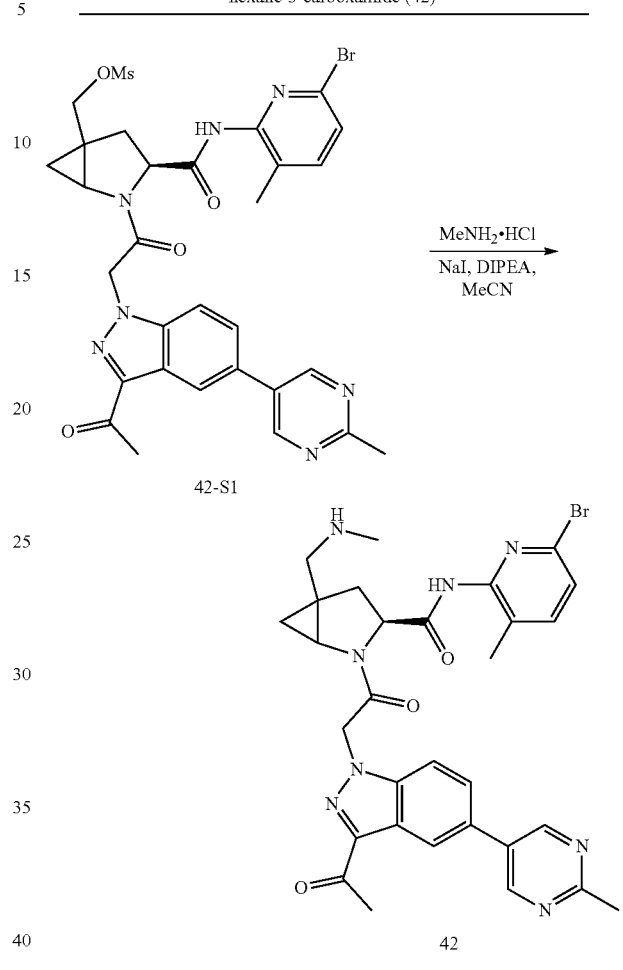

To a suspension of methyl 3-acetyl-1-(2-((2S,4R)-2-((6-bromopyridin-2-yl)carbamoyl)-4-fluoropyrrolidin-1-yl)-2-oxoethyl)-5-(2-methylpyrimidin-5-yl)-1H-indazole-7-carboxylate (25, 0.13 g) in THF (3 mL) was added a solution of LiOH (25 mg) in water (1 mL). The resulting homogeneous solution was stirred overnight at room temperature. The organic solvent was removed and the residue was diluted with water (2 mL). The white solid obtained by the acidification of the aqueous solution with 2N aqueous HCl was isolated and purified by reverse phase HPLC to afford 41. $^1$H NMR (400 MHz, DMSO) δ 2.03-2.25 (m, 1H), 2.50-2.58 (m, 1H), 2.68 (s, 3H), 2.69 (s, 3H), 3.56-3.68 (m, 1H), 3.91-4.13 (m, 2H), 4.64 (t, J=8.4 Hz, 1H), 5.53 (d, J=52.4 Hz, 1H), 5.74 (d, J=17.1 Hz, 1H), 6.10 (d, J=17.1 Hz, 1H), 7.30 (d, J=7.7 Hz, 1H), 7.68 (t, J=8.0 Hz, 1H), 7.99 (d, J=8.3 Hz, 1H), 8.26 (d, J=1.8 Hz, 1H), 8.69 (d, J=1.8 Hz, 1H), 9.05 (s, 2H), 10.96 (s, 1H), 13.72 (s, 1H). $^{19}$F-NMR (DMSO-d$_6$): δ−175.2.

The above scheme and following detailed description depicts one non-limiting method for synthesizing compounds with nucleophilic R$^{201}$ groups on the C-ring. The skilled artisan will recognize that MeNH$_2$ can be replaced with other nucleophilic reagents to afford additional compounds of the present invention. Non-limiting examples of groups the skilled artisan can use instead of MeNH$_2$ include ethanamine, 2-fluoroethan-1-amine, 2,2,2-trifluoroethanamine, N-ethylpropan-1-amine, cyclopropanamine, piperazine, azetidine, azetidin-3-ol, 3,3-difluoroazetidine, 2-azaspiro[3.3]heptane, 2-azaspiro[3.4]octane, (3aR,6aS)-octahydrocyclopenta[c]pyrrole, 2-oxa-6-azaspiro[3.3]heptane, 2-azaspiro[3.4]octane, phenylmethanamine, (2-fluorophenyl)methanamine, and sodium cyanide To a solution of 42-S1 (84 mg, 0.12 mmol) in MeCN (3 mL) were added DIPEA (0.04 mL, 0.24 mmol), NaI (18 mg, 0.12 mmol), and MeNH$_2$·HCl (16 mg, 0.24 mmol). The reaction mixture was stirred at 30° C. overnight. The mixture was partitioned with EtOAc and water. The organic layer was washed with brine, dried over anhydrous Na$_2$SO$_4$, and concentrated under reduced pressure. The remaining residue was purified by column chromatography on silica gel (eluted with DCM/MeOH=10:1) and further purified by preparative HPLC to afford 42 (1.5 mg, 3.3% yield) as a white solid. $^1$H NMR (400 MHz, CD$_3$OD) δ 9.01 (s, 2H), 8.57 (s, 1H), 7.76-7.83 (m, 2H), 7.58 (d, J=8.0 Hz, 1H), 7.42 (d, J=8.0 Hz, 1H), 5.65-5.79 (m, 2H), 4.72-4.75 (m, 1H), 3.85-3.87 (m, 1H), 2.61-2.79 (m, 11H), 2.59-2.60 (m, 2H), 2.12 (s, 3H), 1.28-1.45 (m, 2H). LC/MS (ESI) m/z: 631/633 (M+H)+.

(1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-(piperazin-1-ylmethyl)-2-azabicyclo[3.1.0]hexane-3-carboxamide (88)

¹H NMR (400 MHz, CD₃OD) δ 9.02 (s, 2H), 8.55 (s, 1H), 8.45 (s, 1H), 7.58 (d, J=8.5 Hz, 2H), 7.41 (d, J=7.9 Hz, 1H), 6.00 (m, 1H), 5.83 (m, 1H), 4.66 (m, 1H), 3.68 (m, 1H), 3.25 (m, 4H), 2.91 (m, 2H), 2.77 (d, J=4.9 Hz, 6H), 2.74 (d, J=3.9 Hz, 2H), 2.70 (s, 3H), 2.68 (s, 2H), 2.51 (m, 2H), 2.14 (s, 3H), 1.20 (m, 1H), 1.10 (m, 1H). LC/MS (ESI) m/z: 700 (M+H)+.

(1R,3S,5R)-5-(2-Azaspiro[3.3]heptan-2-ylmethyl)-2-(2-(3-acetyl-7-methyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide (89)

¹H NMR (400 MHz, CD₃OD) δ 9.02 (s, 2H), 8.45 (s, 1H), 7.64-7.52 (m, 2H), 7.42 (d, J=7.9 Hz, 1H), 5.99 (m, 1H), 5.82 (m, 1H), 4.64 (m, 1H), 3.79 (m, 4H), 3.16-3.06 (m, 1H), 2.77 (d, J=2.9 Hz, 6H), 2.70 (s, 3H), 2.66 (s, 2H), 2.63-2.49 (m, 2H), 2.26 (m, 4H), 2.15 (s, 3H), 1.93-1.85 (m, 2H), 1.35 (m, 1H), 1.16 (m, 1H). LC/MS (ESI) m/z: 711 (M+H)+.

(1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-((methylamino)methyl)-2-azabicyclo[3.1.0]hexane-3-carboxamide (94)

¹H NMR (400 MHz, CD₃OD) δ 9.02 (s, 2H), 8.45 (d, J=6.7 Hz, 1H), 7.67-7.45 (m, 2H), 7.40 (m, 1H), 6.03-5.77 (m, 2H), 3.84 (s, 1H), 3.15 (m, 1H), 2.93 (m, 1H), 2.79 (d, J=10.8 Hz, 2H), 2.75 (m, 4H), 2.77-2.68 (m, 4H), 2.70-2.63 (m, 2H), 2.66-2.56 (m, 1H), 2.47 (dd, J=13.8, 3.5 Hz, 1H), 2.10 (m, 3H), 1.79 (m, 1H), 1.30 (m, 2H). LC/MS (ESI) m/z: 645 (M+H)+.

(1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-((2-fluoroethylamino)methyl)-2-azabicyclo[3.1.0]hexane-3-carboxamide (113)

¹H NMR (400 MHz CD₃OD) δ 9.01 (s, 2H), 8.43 (s, 1H), 7.66-7.47 (m, 3H), 7.41 (d, J=7.9 Hz, 2H), 5.99 (m, 1H), 5.82 (m, 1H), 4.71 (m, 1H), 4.66 (m, 1H), 4.60 (m, 1H), 3.77 (m, 1H), 3.19 (m, 1H), 3.15-3.09 (m, 2H), 3.00 (d, J=12.9 Hz, 1H), 2.76 (s, 6H), 2.70 (s, 3H), 2.63 (m, 2H), 2.14 (s, 3H), 1.18 (m, 1H), 0.92 (m, 1H). LC/MS (ESI) m/z: 677 (M+H)+.

(1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-((diethylamino)methyl)-2-azabicyclo[3.1.0]hexane-3-carboxamide (118)

¹H NMR (400 MHz, CD₃OD) δ 8.89 (s, 2H), 8.33 (s, 1H), 7.51-7.42 (m, 2H), 7.30 (d, J=7.9 Hz, 1H), 5.80 (dd, J=18.0, 18.0 Hz, 2H), 4.59 (dd, J=8.9, 4.5 Hz, 1H), 3.76 (d, J=3.2 Hz, 1H), 3.36 (d, J=14.6 Hz, 1H), 3.10 (s, 5H), 2.65 (d, J=5.3 Hz, 6H), 2.57 (d, J=7.6 Hz, 4H), 2.48 (dd, J=13.3, 4.3 Hz, 1H), 2.06 (s, 6H), 2.02 (s, 3H), 1.40-1.36 (m, 1H), 0.82-0.78 (m, 1H). LC/MS (ESI) m/z: 687 (M+H)+.

(1R,3S,5R)-2-(2-(3-Acetyl-5-(2-methylpyrimidin-5-yl)-1H-indazol-1-yl)acetyl)-N-(6-bromo-3-methylpyridin-2-yl)-5-(((3aR,6aS)-hexahydrocyclopenta[c]pyrrol-2(1H)-yl)methyl)-2-azabicyclo[3.1.0]hexane-3-carboxamide (119)

¹H NMR (400 MHz, CD₃OD) δ 8.92 (s, 2H), 8.47 (s, 1H), 7.72 (s, 2H), 7.49 (d, J=8.2 Hz, 1H), 7.32 (d, J=8.0 Hz, 1H), 5.74 (d, J=16.7 Hz, 1H), 5.57 (d, J=17.2 Hz, 1H), (dd, J=8.9, 4.5 Hz, 1H), 3.80 (d, J=5.2 Hz, 1H), 3.63 (s, 2H), 3.54 (s, 2H), 3.40-3.38 (m, 1H), 3.04-3.03 (m, 1H), 2.80 (s, 3H), 2.66 (s, 4H), 2.62-2.55 (m, 6H), 2.04 (s, 3H), 1.64 (s, 4H), 1.50 (s, 2H), 1.36-1.31 (m, 1H), 1.21-1.18 (s, 1H). LC/MS (ESI) m/z: 711 (M+H)+.

(1R,3S,5R)-5-(2-Oxa-6-azaspiro[3.3]heptan-6-ylmethyl)-2-(2-(3-acetyl-7-methyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide (127)

¹H NMR (400 MHz, CD₃OD) δ 8.98 (s, 2H), 8.41 (s, 1H), 7.57 (d, J=8.0 Hz, 1H), 7.53 (s, 1H), 7.40 (d, J=8.0 Hz, 1H), 5.94-5.99 (m, 1H), 5.76-5.81 (m, 1H), 4.80 (s, 4H), 4.63-4.65 (m, 1H), 4.08-4.15 (m, 4H), 3.81-3.83 (m, 1H), 3.13 (s, 2H), 2.74 (s, 6H), 2.65 (s, 3H), 2.49-2.59 (m, 2H), 2.12 (s, 3H), 1.30-1.33 (m, 1H), 0.95-0.98 (m, 1H). LC/MS (ESI) m/z: 713 (M+H)+.

(1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-(((3aR,6aS)-hexahydrocyclopenta[c]pyrrol-2(1H)-yl)methyl)-2-azabicyclo[3.1.0]hexane-3-carboxamide (128)

¹H NMR (400 MHz, CD₃OD) δ 8.98 (s, 2H), 8.41 (s, 1H), 7.53-7.58 (m, 2H), 7.40 (d, J=8.0 Hz, 1H), 5.96-6.01 (m, 2H), 5.77-5.81 (m, 1H), 4.66-4.70 (m, 1H), 3.86-3.89 (m, 3H), 2.63-2.89 (m, 17H), 2.12 (s, 3H), 1.59-1.76 (m, 6H), 1.43-1.46 (m, 1H), 1.27-1.30 (m, 1H). LC/MS (ESI) m/z: 725 (M+H)+.

(1R,3S,5R)-5-(2-Azaspiro[3.4]octan-2-ylmethyl)-2-(2-(3-acetyl-7-methyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide (129)

¹H NMR (400 MHz, CD₃OD) δ 8.98 (s, 2H), 8.41 (s, 1H), 7.58 (d, J=8.0 Hz, 1H), 7.52 (s, 1H), 7.41 (d, J=8.0 Hz, 1H), 5.97 (m, 1H), 5.79 (m, 1H), 4.67 (m, 1H), 4.07-4.04 (m, 1H), 4.03-3.90 (m, 1H), 3.44 (q, J=13.6 Hz, 2H), 2.74 (m, 6H), 2.67 (s, 3H), 2.61-2.55 (m, 1H), 2.12 (s, 3H), 1.94 (m, 4H), 1.66 (m, 5H), 1.45 (m, 1H), 1.29-1.20 (m, 1H). LC/MS (ESI) m/z: 725 (M+H)+.

(1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-((ethylamino)methyl)-2-azabicyclo[3.1.0]hexane-3-carboxamide (132)

¹H NMR (400 MHz, CD₃OD) δ 9.00 (s, 2H), 8.44 (s, 1H), 7.60-7.44 (m, 2H), 7.43 (d, J=7.9 Hz, 1H), 5.98 (d, J=17.6

Hz, 1H), 5.83 (d, J=17.6 Hz, 1H), 4.74 (dd, J=8.3, 4.4 Hz, 1H), 3.91 (dd, J=5.8, 2.8 Hz, 1H), 3.28-3.07 (m, 3H), 2.77 (s, 6H), 2.70 (s, 3H), 2.68-2.59 (m, 2H), 2.14 (s, 3H), 1.50 (d, J=5.9 Hz, 1H), 1.39 (t, J=7.3 Hz, 3H), 1.35 (dd, J=5.9, 2.8 Hz, 1H). LC/MS (ESI) m/z: 658 (M+H)+.

(1R,3S,5R)-5-(2-Azaspiro[3.4]octan-2-ylmethyl)-2-(2-(3-acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide (142)

¹H NMR (400 MHz, CD₃OD) δ 8.99 (s, 2H), 8.53 (s, 1H), 7.77 (s, 2H), 7.57 (d, J=8.0 Hz, 1H), 7.41 (d, J=8.0 Hz, 1H), 5.77-5.81 (m, 1H), 5.62-5.66 (m, 1H), 4.65-4.68 (m, 1H), 3.99-4.07 (m, 4H), 3.88-3.90 (m, 1H), 3.36 (s, 2H), 2.75 (s, 3H), 2.68 (s, 3H), 2.57-2.60 (m, 2H), 2.12 (s, 3H), 1.91-1.95 (m, 4H), 1.63-1.67 (m, 4H), 1.37-1.39 (m, 1H), 1.23-1.25 (m, 1H). LC/MS (ESI) m/z: 711 (M+H)+.

(1R,3S,5R)-2-(2-(3-Acetyl-7-methyl-5-(2-methylpyrimidin-5-yl)-1H-indazol-1-yl)acetyl)-5-(azetidin-1-ylmethyl)-N-(6-bromo-3-methylpyridin-2-yl)-2-azabicyclo[3.1.0]hexane-3-carboxamide (149)

¹H NMR (400 MHz, CD₃OD) δ 9.00 (s, 2H), 8.42 (s, 1H), 7.58 (d, J=8.0 Hz, 1H), 7.55 (s, 1H), 7.42 (d, J=8.0 Hz, 1H), 5.96-6.01 (m, 1H), 5.78-5.83 (m, 1H), 4.64-4.68 (m, 1H), 4.04-4.09 (m, 4H), 3.86-3.88 (m, 1H), 3.32-3.34 (m, 1H), 3.18-3.21 (m, 1H), 2.76 (s, 6H), 2.71 (s, 4H), 2.44-2.53 (m, 3H), 2.13 (s, 3H), 1.39-1.42 (m, 1H), 1.21-1.23 (m, 1H). LC/MS (ESI) m/z: 671 (M+H)+.

(1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-((3,3-difluoroazetidin-1-yl)methyl)-2-azabicyclo[3.1.0]hexane-3-carboxamide (150)

¹H NMR (400 MHz, CD₃OD) δ 9.01 (s, 2H), 8.43 (s, 1H), 7.55-7.57 (m, 2H), 7.38 (d, J=8.0 Hz, 1H), 5.97-6.02 (m, 1H), 5.78-5.83 (m, 1H), 4.59-4.63 (m, 1H), 3.67-3.82 (m, 5H), 2.70-2.81 (m, 11H), 2.58-2.60 (m, 2H), 2.16 (s, 3H), 1.24-1.27 (m, 1H), 1.03-1.05 (m, 1H). LC/MS (ESI) m/z: 707 (M+H)+.

(1R,3S,5R)-2-(2-(3-Acetyl-5-(2-methylpyrimidin-5-yl)-1H-indazol-1-yl)acetyl)-N-(6-bromo-3-methylpyridin-2-yl)-5-((cyclopropylamino)methyl)-2-azabicyclo[3.1.0]hexane-3-carboxamide (151)

¹H NMR (400 MHz, CD₃OD) δ 9.03 (s, 2H), 8.58 (s, 1H), 7.81 (s, 2H), 7.58 (d, J=8.0 Hz, 1H), 7.41 (d, J=7.9 Hz, 1H), 5.82 (d, J=17.2 Hz, 1H), 5.68 (d, J=17.1 Hz, 1H), 4.68-4.57 (m, 1H), 3.69 (s, 1H), 3.16-3.01 (m, 1H), 2.84 (d, J=12.7 Hz, 1H), 2.77 (s, 3H), 2.72 (s, 3H), 2.66-2.56 (m, 2H), 2.35 (s, 1H), 1.30 (s, 1H), 1.13 (s, 1H), 0.58 (d, J=5.5 Hz, 2H), 0.47 (s, 2H). LC/MS (ESI) m/z: 657 (M+H)+.

(1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-(((2,2,2-trifluoroethyl)amino)methyl)-2-azabicyclo[3.1.0]hexane-3-carboxamide (160)

¹H NMR (400 MHz, CD₃OD) δ 9.01 (s, 2H), 8.44 (s, 1H), 7.56-7.58 (m, 2H), 7.40 (d, J=8.0 Hz, 1H), 5.97-6.02 (m, 1H), 5.80-5.85 (m, 1H), 4.61-4.64 (m, 1H), 3.66-3.69 (m, 1H), 3.32-3.34 (m, 2H), 2.94-2.96 (m, 2H), 2.78 (s, 6H), 2.76 (s, 3H), 2.59-2.61 (m, 2H), 2.15 (s, 3H), 1.29-1.32 (m, 1H), 1.05-1.08 (m, 1H). LC/MS (ESI) m/z: 713 (M+H)+.

(1R,3S,5R)-2-(2-(3-Acetyl-7-methyl-5-(2-methylpyrimidin-5-yl)-1H-indazol-1-yl)acetyl)-5-((benzylamino)methyl)-N-(6-bromo-3-methylpyridin-2-yl)-2-azabicyclo[3.1.0]hexane-3-carboxamide (161)

¹H NMR (400 MHz, CD₃OD) δ 8.85 (s, 2H), 8.27 (s, 1H), 7.28-7.46 (m, 8H), 5.81-5.86 (m, 1H), 5.64-5.69 (m, 1H), 4.56-4.58 (m, 1H), 4.01-4.11 (m, 2H), 3.71-3.74 (m, 1H), 3.01 (s, 2H), 2.63 (s, 6H), 2.56 (s, 3H), 2.50-2.54 (m, 2H), 1.99 (s, 3H), 1.29-1.31 (m, 1H), 1.14-1.17 (m, 1H). LC/MS (ESI) m/z: 721 (M+H)+.

(1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-(cyanomethyl)-2-azabicyclo[3.1.0]hexane-3-carboxamide (162)

¹H NMR (400 MHz, CD₃OD) δ 8.99 (s, 2H), 8.41 (s, 1H), 7.53-7.56 (m, 2H), 7.39 (d, J=8.0 Hz, 1H), 5.96-6.00 (m, 1H), 5.77-5.82 (m, 1H), 4.62-4.66 (m, 1H), 3.82-3.84 (m, 1H), 3.04-3.08 (m, 1H), 2.87-2.91 (m, 1H), 2.69-2.78 (m, 10H), 2.46-2.50 (m, 1H), 2.14 (s, 3H), 1.40-1.43 (m, 1H), 1.22-1.25 (m, 1H). LC/MS (ESI) m/z: 641 (M+H)+.

(1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-((3-hydroxyazetidin-1-yl)methyl)-2-azabicyclo[3.1.0]hexane-3-carboxamide (164)

¹H NMR (400 MHz, CD₃OD) δ 9.01 (s, 2H), 8.44 (s, 1H), 7.63-7.53 (m, 2H), 7.42 (d, J=7.9 Hz, 1H), 6.00 (d, J=17.7 Hz, 1H), 5.82 (d, J=17.7 Hz, 1H), 4.70-4.48 (m, 2H), 4.15 (d, J=26.0 Hz, 2H), 3.81 (s, 1H), 3.50 (s, 2H), 3.24-3.12 (m, 1H), 3.03 (d, J=13.0 Hz, 1H), 2.77 (d, J=2.9 Hz, 6H), 2.70 (s, 3H), 2.61 (d, J=8.8 Hz, 1H), 2.53 (dd, J=13.5, 4.8 Hz, 1H), 2.14 (s, 3H), 1.34 (d, J=22.4 Hz, 2H), 1.17 (s, 1H). LC/MS (ESI) m/z: 687 (M+H)+.

(1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-(((2-fluorobenzyl)amino)methyl)-2-azabicyclo[3.1.0]hexane-3-carboxamide (170)

¹H NMR (400 MHz, CD₃OD) δ 8.99 (s, 2H), 8.43 (s, 1H), 7.59-7.54 (m, 3H), 7.48-7.41 (m, 2H), 7.29-7.22 (m, 2H), 5.96 (d, J=12.8 Hz, 1H), 5.81 (d, J=9 Hz, 1H), 4.70 (s, 1H), 4.26 (d, J=3 Hz, 2H), 3.86-3.84 (m, 1H), 3.24 (d, J=2.4 Hz, 2H), 2.76 (d, J=2.8 Hz, 6H), 2.69 (s, 3H), 2.66-2.63 (m, 2), 2.12 (s, 3H), 1.45 (s, 1H), 1.28-1.26 (m, 1H). LC/MS (ESI) m/z: 739 (M+H)+.

(1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-(((1-(2,2,2-trifluoroethyl)-1H-pyrazol-3-yl)amino)methyl)-2-azabicyclo[3.1.0]hexane-3-carboxamide ¹H-NMR (400 MHz, CD₃OD) δ 8.99 (s, 2H), 8.41 (s, 1H), 7.53 (d, J=7.4 Hz, 2H), 7.42 (d, J=2.5 Hz, 1H), 7.37 (d, J=7.9 Hz, 1H), 5.95 (d, J=17.8 Hz, 1H), 5.80 (d, J=17.7 Hz, 1H), 5.72 (d, J=2.5 Hz, 1H), 4.71-4.58 (m, 3H), 3.74-3.65 (m, 1H), 3.48 (d, J=13.6 Hz, 1H), 3.34 (s, 1H), 2.75 (d, J=4.4 Hz, 6H), 2.68 (s, 3H), 2.63-2.49 (m, 2H), 2.11 (s, 3H), 1.38-1.35 (m, 1H), 1.10-1.01 (m, 1H). LC/MS (ESI) m/z: 779 (M+H)+.

Scheme 25. Synthesis of (1S,3S,5S)-5-(Acetamidomethyl)-2-(2-(3-acetyl-5-(2-methylpyrimidin-5-yl)-1H-indazol-1-yl)acetyl)-N-(6-bromopyridin-2-yl)-2-azabicyclo[3.1.0]hexane-3-carboxamide (43) and (1R,3S,5R)-5-(Acetamidomethyl)-2-(2-(3-acetyl-5-(2-methylpyrimidin-5-yl)-1H-indazol-1-yl)acetyl)-N-(6-bromopyridin-2-yl)-2-azabicyclo[3.1.0]hexane-3-carboxamide (44)
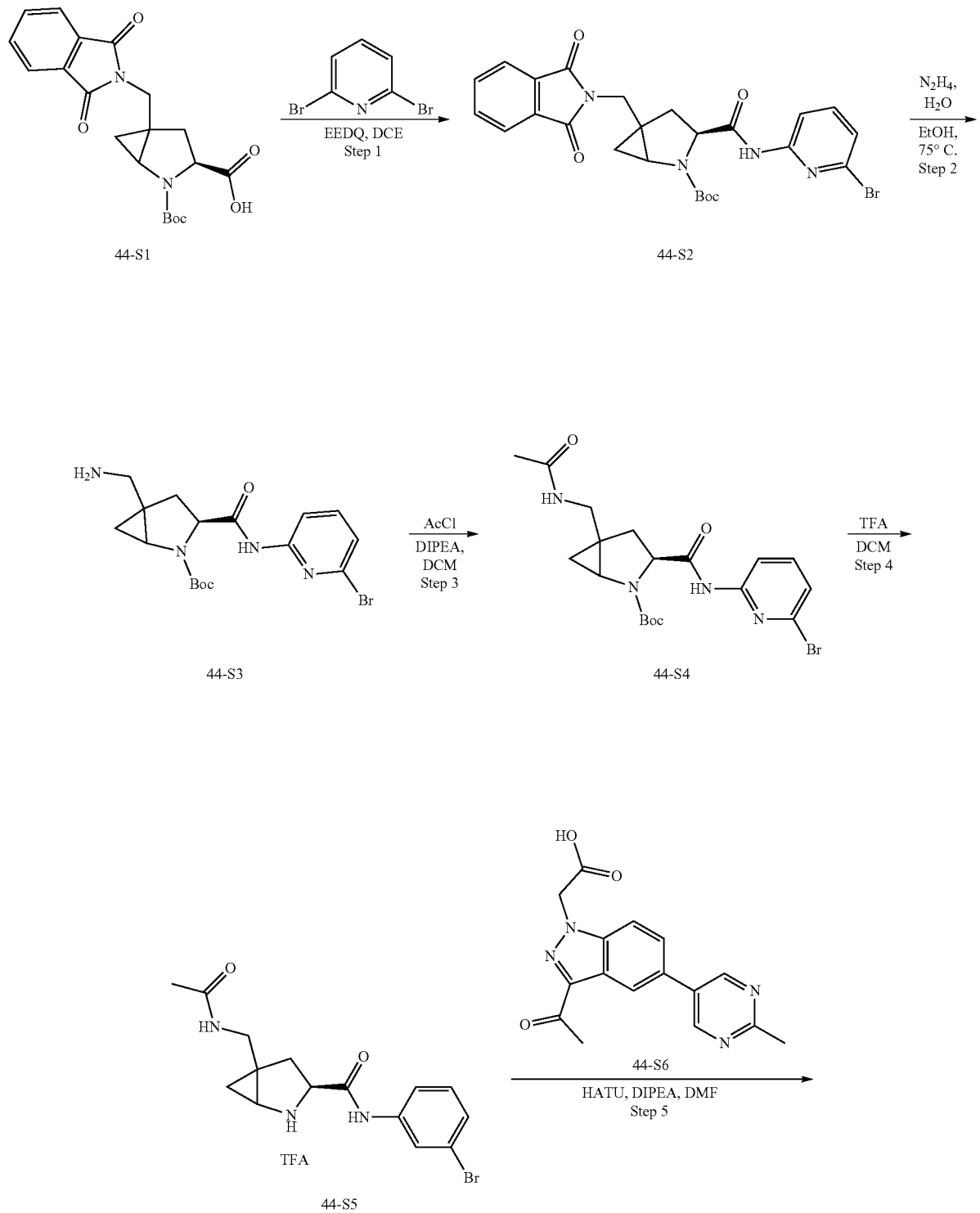

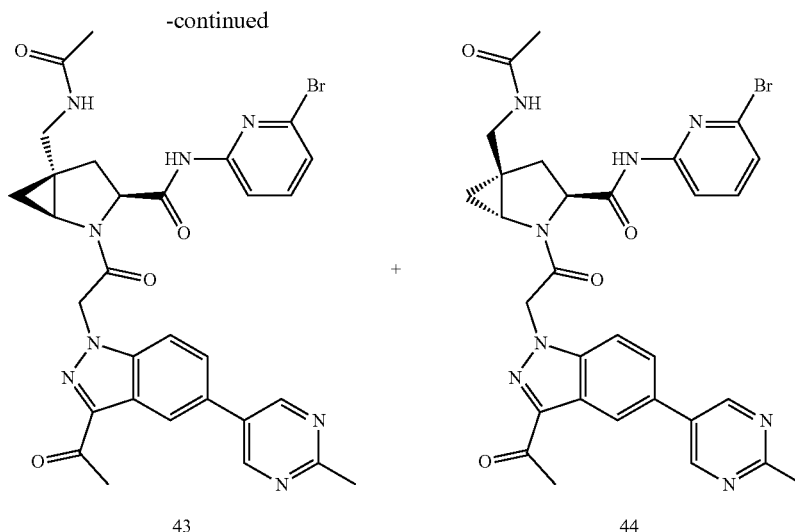

43

44

Step 1: (3S)-tert-Butyl 3-(6-bromopyridin-2-ylcarbamoyl)-5-((1,3-dioxoisoindolin-2-yl)methyl)-2-azabicyclo[3.1.0]hexane-2-carboxylate (44-S2)

To a solution of 44-S1 (250 mg, 0.64 mmol) and 6-bromopyridin-2-amine (123 mg, 0.71 mmol) in DCE (5 mL) were added DIPEA (0.43 mL, 2.58 mmol) and EEDQ (319 mg, 1.29 mmol). The reaction mixture was stirred at 90° C. overnight and concentrated under vacuum. The remaining residue was purified by column chromatography on silica gel (eluted with PE/EtOAc=4:1) to afford 44-S2 (300 mg, 85.9% yield) as a white solid. LC/MS (ESI) m/z: 541/543 (M+H)$^+$.

Step 2: (3S)-tert-Butyl 5-(aminomethyl)-3-(6-bromopyridin-2-ylcarbamoyl)-2-azabicyclo[3.1.0]hexane-2-carboxylate (44-S3)

To a solution of 44-S2 (300 mg, 0.55 mmol) in EtOH (6 mL) was added hydrazine hydrate (0.3 mL, 85% w/w). The reaction mixture was stirred at 75° C. for 2 hours and then cooled to room temperature. The mixture was filtered, the filtrate was concentrated to dryness, and the remaining crude product was purified by column chromatography on silica gel (eluted with DCM/MeOH=10:1) to afford 44-S3 (210 mg, 92.5% yield) as light a yellow oil. LC/MS (ESI) m/z: 411/413 (M+H)$^+$.

Step 3: (3S)-tert-Butyl 5-(Acetamidomethyl)-3-(6-bromopyridin-2-ylcarbamoyl)-2-azabicyclo[3.1.0]hexane-2-carboxylate (44-S4)

To a mixture of 44-S3 (100 mg, 0.24 mmol) in dry DCM (3 mL) were added DIPEA (0.08 mL, 0.48 mmol) and acetyl chloride (0.02 mL, 0.28 mmol) at 0° C. The reaction mixture was stirred at room temperature for 1 hour. The mixture was then diluted with water (20 mL) and extracted with DCM (4 mL×2). The combined organic phases were washed with brine, dried over anhydrous Na$_2$SO$_4$, filtered, and concentrated. The remaining crude product was purified by column chromatography on silica gel (eluted with DCM/MeOH=30:1) to afford 44-S4 (94 mg, 85.4% yield) as a white solid. LC/MS (ESI) m/z: 453/455 (M+H)$^+$.

Step 4: (3S)-5-(Acetamidomethyl)-N-(6-bromopyridin-2-yl)-2-azabicyclo[3.1.0]hexane-3-carboxamide (44-S5)

To a solution of 44-S4 (90 mg, 0.2 mmol) in DCM (2.5 mL) was added TFA (1 mL). The reaction mixture was stirred at room temperature for 1.5 hours and then concentrated under reduced pressure to afford 44-S5 (80 mg, 100.0% yield) as a yellow solid, which was carried forward in the next synthetic step without further purification. LC/MS (ESI) m/z: 353/355 (M+H)$^+$.

Step 5: (1S,3S,5S)-5-(Acetamidomethyl)-2-(2-(3-acetyl-5-(2-methylpyrimidin-5-yl)-1H-indazol-1-yl)acetyl)-N-(6-bromopyridin-2-yl)-2-azabicyclo[3.1.0]hexane-3-carboxamide (43) and (1R,3S,5R)-5-(Acetamidomethyl)-2-(2-(3-acetyl-5-(2-methylpyrimidin-5-yl)-1H-indazol-1-yl)acetyl)-N-(6-bromopyridin-2-yl)-2-azabicyclo[3.1.0]hexane-3-carboxamide (44)

To a solution of 44-S5 (35 mg, 0.078 mmol), 2-(3-acetyl-5-(2-methylpyrimidin-5-yl)-1H-indazol-1-yl)acetic acid (44-S6, 29 mg, 0.093 mmol), and HATU (59 mg, 0.155 mmol) in DMF (2 mL) was added DIPEA (0.065 mL, 0.40 mmol). The reaction mixture was stirred at room temperature for 16 hours. The mixture was partitioned with EtOAc and water. The organic layer was washed with brine, dried over anhydrous Na$_2$SO$_4$, and concentrated under reduced pressure. The crude product was purified by preparative HPLC to afford 43 (25 mg, 49.8% yield) and 44 (2 mg, 3.98% yield) as white solids.

(1S,3S,5S)-5-(acetamidomethyl)-2-(2-(3-acetyl-5-(2-methylpyrimidin-5-yl)-1H-indazol-1-yl)acetyl)-N-(6-bromopyridin-2-yl)-2-azabicyclo[3.1.0]hexane-3-carboxamide (43)

$^1$H NMR (400 MHz, DMSO-d$_6$) δ 10.91 (s, 1H), 9.04 (s, 2H), 8.48 (s, 1H), 8.02-8.05 (m, 2H), 7.83-7.89 (m, 2H), 7.70 (t, J=8.0 Hz, 1H), 7.31 (d, J=7.6 Hz, 1H), 5.86-5.90 (m, 1H), 5.58-5.63 (m, 1H), 4.92-4.95 (m, 1H), 3.72-3.74 (m, 1H), 3.37-3.40 (m, 2H), 2.62-2.68 (m, 6H), 2.01-2.05 (m, 1H), 1.86 (s, 3H), 1.40-1.42 (m, 1H), 0.89-1.01 (m, 2H). LC/MS (ESI) m/z: 645/647 (M+H)$^+$.

(1R,3S,5R)-5-(acetamidomethyl)-2-(2-(3-acetyl-5-(2-methylpyrimidin-5-yl)-1H-indazol-1-yl)acetyl)-N-(6-bromopyridin-2-yl)-2-azabicyclo[3.1.0]hexane-3-carboxamide (44)

$^1$H NMR (400 MHz, CD$_3$OD) δ 9.00 (s, 2H), 8.54 (s, 1H), 8.08-8.10 (m, 1H), 7.79 (s, 2H), 7.62 (t, J=8.0 Hz, 1H), 7.26 (d, J=7.6 Hz, 1H), 5.77-5.82 (m, 1H), 5.63-5.68 (m, 1H), 4.57-4.62 (m, 1H), 3.70-3.72 (m, 1H), 3.46-3.50 (m, 1H), 3.20-3.23 (m, 1H), 2.73-2.75 (m, 6H), 2.30-2.52 (m, 2H), 1.92 (s, 3H), 1.26-1.29 (m, 1H), 1.06-1.08 (m, 1H). LC/MS (ESI) m/z: 645/647 (M+H)$^+$.

Scheme 26. Synthesis of Methyl (2S)-1-(((3S)-2-(2-(3-acetyl-5-(2-methylpyrimidin-5-yl)-1H-indazol-1-yl)acetyl)-3-(6-bromopyridin-2-ylcarbamoyl)-2-azabicyclo[3.1.0]hexan-5-yl)methylamino)-3-methyl-1-oxobutan-2-ylcarbamate (45)

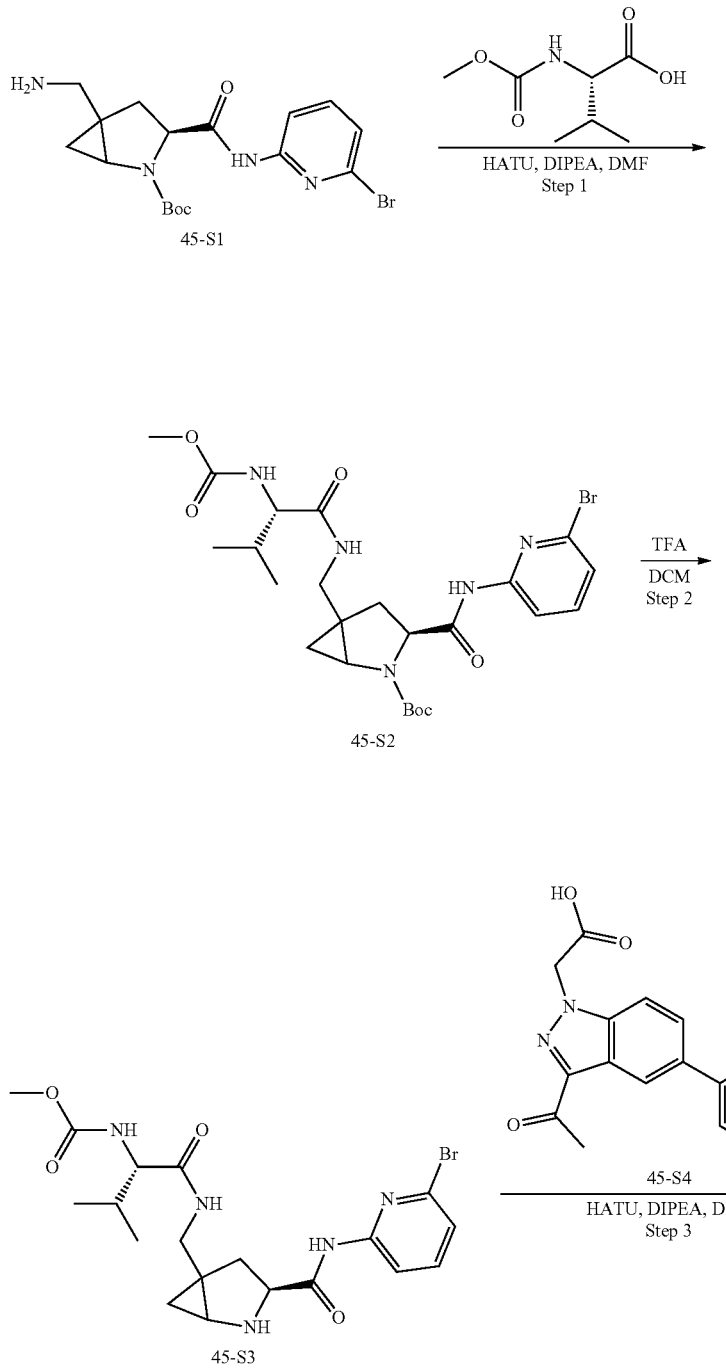

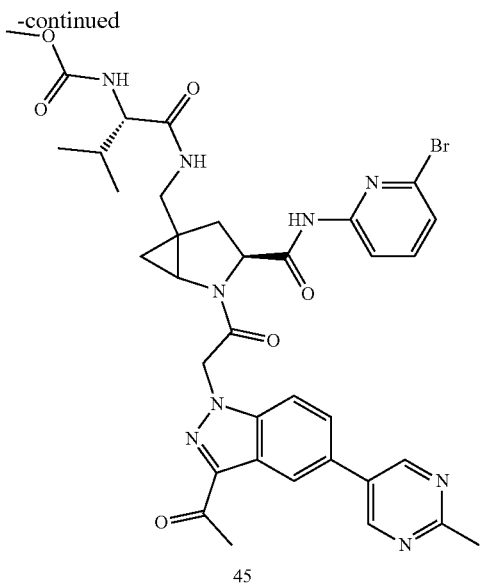

45

Step 1: (3S)-tert-Butyl 3-(6-bromopyridin-2-ylcarbamoyl)-5-(((S)-2-(methoxycarbonylamino)-3-methylbutanamido)methyl)-2-azabicyclo[3.1.0]hexane-2-carboxylate (45-S2)

To a mixture of 45-S1 (100 mg, 0.24 mmol), (S)-2-(methoxycarbonylamino)-3-methylbutanoic acid (51 mg, 0.29 mmol), and HATU (182 mg, 0.48 mmol) in DMF (2 mL) was added DIPEA (0.16 mL, 0.96 mmol). The reaction mixture was stirred at room temperature for 16 hours. The mixture was partitioned with EtOAc and water. The organic layer was washed with brine, dried over anhydrous $Na_2SO_4$, and concentrated under reduced pressure. The remaining residue product was purified by column chromatography on silica gel (eluted with DCM/MeOH=30:1) to afford 45-S2 (105 mg, 76.0% yield) as a white solid. LC/MS (ESI) m/z: 568/570 (M+H)$^+$.

Step 2: Methyl (2S)-1-(((3S)-3-(6-Bromopyridin-2-ylcarbamoyl)-2-azabicyclo[3.1.0]hexan-5-yl)methylamino)-3-methyl-1-oxobutan-2-ylcarbamate (S3)

To a solution of 45-S2 (105 mg, 0.18 mmol) in DCM (2.5 mL) was added TFA (1 mL). The reaction mixture was stirred at room temperature for 1.5 hours and then concentrated under reduced pressure to afford 45-S3 (85 mg, 100.0% yield) as a yellow solid, which was carried forward in the next synthetic step without further purification. LC/MS (ESI) m/z: 468/470 (M+H)$^+$.

Step 3: Methyl (2S)-1-(((3S)-2-(2-(3-acetyl-5-(2-methylpyrimidin-5-yl)-1H-indazol-1-yl)acetyl)-3-(6-bromopyridin-2-ylcarbamoyl)-2-azabicyclo[3.1.0]hexan-5-yl)methylamino)-3-methyl-1-oxobutan-2-ylcarbamate (45)

To a solution of 45-S3 (35 mg, 0.074 mmol), 2-(3-acetyl-5-(2-methylpyrimidin-5-yl)-1H-indazol-1-yl)acetic acid (45-S4, 28 mg, 0.089 mmol) and HATU (57 mg, 0.15 mmol) in DMF (2 mL) was added DIPEA (0.05 mL, 0.29 mmol). The reaction mixture was stirred at room temperature for 16 hours. The mixture was partitioned with EtOAc and water. The organic layer was washed with brine, dried over anhydrous $Na_2SO_4$, and concentrated under reduced pressure. The remaining residue was purified by preparative HPLC (eluted with MeCN/water) to afford 45 (39 mg, 68.6% yield) as a white solid. $^1$H NMR (400 MHz, DMSO-$d_6$) δ 10.9 (s, 1H), 9.04 (s, 2H), 8.47 (s, 1H), 8.01-8.25 (m, 2H), 7.70-7.89 (m, 3H), 7.30-7.33 (m, 1H), 7.11-7.24 (m, 1H), 5.84-5.91 (m, 1H), 5.57-5.64 (m, 1H), 4.92-4.95 (m, 1H), 3.71-3.79 (m, 2H), 3.49 (s, 4H), 3.29-3.33 (m, 1H), 2.65-2.68 (m, 7H), 1.97-2.02 (m, 2H), 1.05-1.36 (m, 2H), 0.87-0.95 (m, 6H). LC/MS (ESI) m/z: 760/762 (M+H)$^+$.

Scheme 27. Synthesis of (1R,3S,5R)-2-(2-(3-Acetyl-7-ethyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (47)

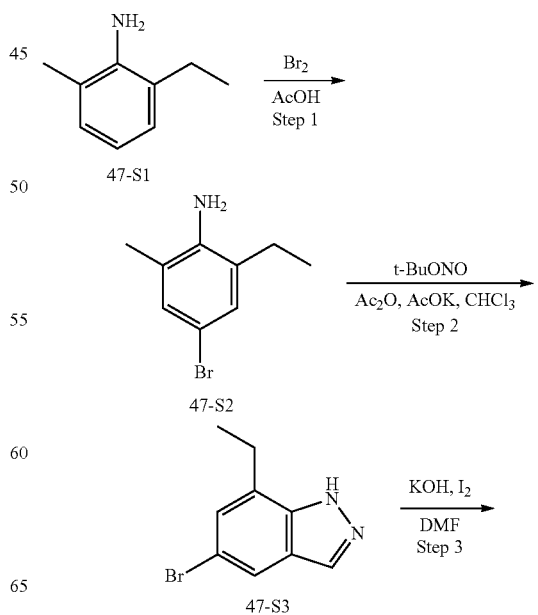

-continued

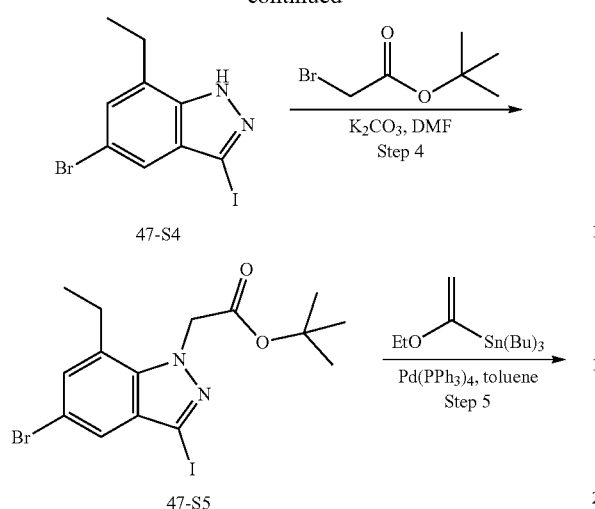

-continued

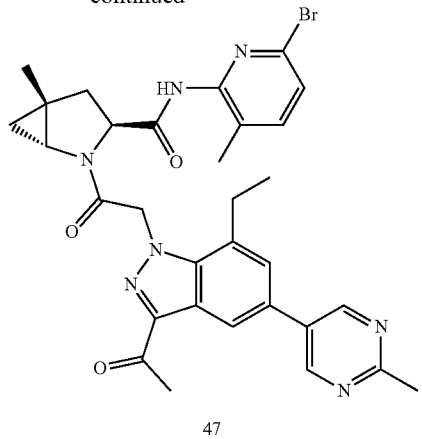

Step 1: 4-Bromo-2-ethyl-6-methylaniline (47-S2)

To a solution of 47-S1 (12 g, 88.7 mmol) in AcOH (250 mL) was added dropwise $Br_2$ (5.1 mL) at 0° C. The reaction mixture was stirred at room temperature for 2 hours. The mixture was filtered and the filter cake was washed with diethyl ether. The solid was suspended in water and neutralized with saturated aqueous $K_2CO_3$ solution. The mixture was extracted with EtOAc twice and the combined organic layers were dried over anhydrous $Na_2SO_4$ and concentrated to dryness to afford 47-S2 (12.2 g, 57.0% yield) as a purple oil. LC/MS (ESI) m/z: 214 $(M+H)^+$.

Step 2: 5-Bromo-7-ethyl-1H-indazole (47-S3)

To a solution of 47-S2 (6 g, 28.2 mmol) and KOAc (3.3 g 33.8 mmol) in $CHCl_3$ (60 mL) was added dropwise acetic anhydride (8.6 g, 86.4 mmol) at 0° C. under an atmosphere of nitrogen and the resulting mixture was stirred at room temperature for 1 hour. The reaction mixture was heated to 60° C. and tert-butyl nitrite (5.8 g, 56.4 mmol) was added. The resulting mixture was stirred at 60° C. overnight. The mixture was diluted with DCM and washed with water and brine. The organic layer was dried over anhydrous $Na_2SO_4$ and concentrated. The remaining residue was dissolved in MeOH and 6 N aqueous HCl (20 mL) and the mixture was stirred at room temperature for 4 hours. The reaction mixture was basified with 2 N aqueous NaOH solution and extracted with DCM twice. The combined organic layers were washed with brine, dried over anhydrous $Na_2SO_4$, and concentrated to afford 47-S3 (5.0 g, 79.2% yield) as a light a yellow solid. LC/MS (ESI) m/z: 225 $(M+H)^+$.

Step 3: 5-Bromo-7-ethyl-3-iodo-1H-indazole (47-S4)

To a solution of 47-S3 (4.5 g, 20.1 mmol) in DMF (50 mL) were added KOH (2.53 g, 45.23 mmol) and iodine (7.65 g, 30.15 mmol) at 0° C. The reaction mixture was stirred at 0° C. for 30 minutes. The reaction mixture was quenched by addition of saturated aqueous $Na_2S_2O_3$ solution (15 mL). The mixture was diluted with DCM and washed with 10% aqueous LiCl solution and brine. The organic layer was dried over anhydrous $Na_2SO_4$ and concentrated to dryness to afford 47-S4 (6.56 g, 93.2% yield) as a white solid. LC/MS (ESI) m/z: 351 $(M+H)^+$.

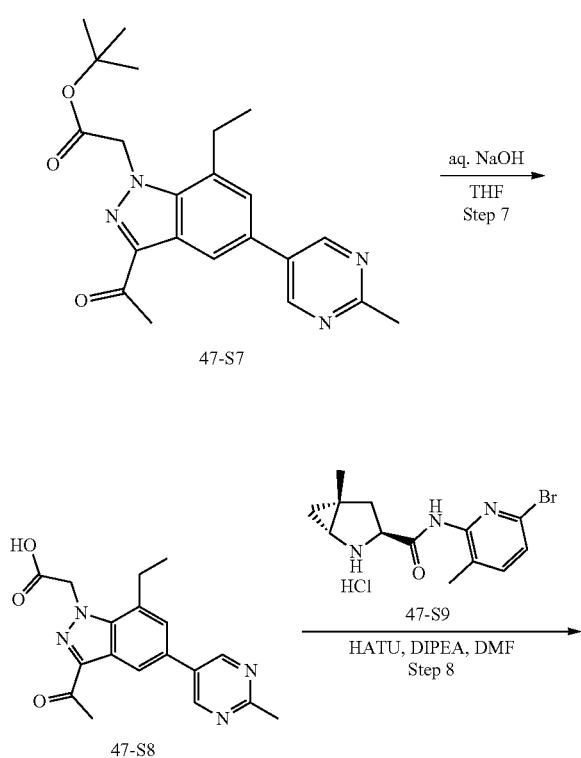

Step 4: tert-Butyl 2-(5-bromo-7-ethyl-3-iodo-H-indazol-1-yl)acetate (47-S5)

To a solution of 47-S4 (6.56 g, 18.75 mmol) in DMF (70 mL) were added $K_2CO_3$ (7.76 g, 56.2 mmol) and tert-butyl 2-bromoacetate (2.73 mL, 18.75 mmol). The reaction mixture was stirred at room temperature overnight. The mixture was diluted with EtOAc and washed with 10% aqueous LiCl solution and brine. The organic layer was dried over anhydrous $Na_2SO_4$ and concentrated to dryness. The remaining residue was purified by column chromatography on silica gel (eluted with PE/EtOAc=10:1) to afford 47-S5 (3.5 g, 40.2% yield) as a yellow solid. LC/MS (ESI) m/z: 465 $(M+H)^+$.

Step 5: tert-Butyl 2-(3-acetyl-5-bromo-7-ethyl-1H-indazol-1-yl)acetate (47-S6)

To a solution of 47-S5 (1.5 g, 3.23 mmol) in toluene (15 mL) were added tributyl(1-ethoxyvinyl)stannane (1.75 g, 4.85 mmol) and $Pd(PPh_3)_4$ (373 mg, 0.32 mmol). The mixture was stirred at 100° C. under an atmosphere of nitrogen overnight. The mixture was cooled to room temperature and 0.5 M aqueous HCl was added. The resulting mixture was stirred for another 30 minutes, diluted with EtOAc, and washed with brine. The organic layer was dried over anhydrous $Na_2SO_4$ and concentrated to dryness. The remaining residue was purified by column chromatography on silica gel (eluted with PE/EtOAc=60:1) to afford 47-S6 (976 mg, 79.5% yield) as a brown solid. LC/MS (ESI) m/z: 381 $(M+H)^+$.

Step 6: tert-Butyl 2-(3-acetyl-7-ethyl-5-(2-methylpyrimidin-5-yl)-1H-indazol-1-yl)acetate (47-S7)

To a solution of 47-S6 (500 mg, 1.32 mmol) and (2-methylpyrimidin-5-yl)boronic acid (182 mg, 1.32 mmol) in dioxane (6 mL) and water (0.6 mL) were added $K_2CO_3$ (455 mg, 3.3 mmol) and $Pd(PPh_3)_4$. The reaction mixture was stirred at 90° C. under an atmosphere of nitrogen overnight. The mixture was diluted with EtOAc, washed with water and brine, dried over $Na_2SO_4$ and concentrated to afford 47-S7 (210 mg, 40.4% yield) as a white solid. LC/MS (ESI) m/z: 395 $(M+H)^+$.

Step 7: 2-(3-Acetyl-7-ethyl-5-(2-methylpyrimidin-5-yl)-1H-indazol-1-yl)acetic Acid (47-S8)

To a solution of 47-S7 (170 mg, 0.43 mmol) in THF (3 mL) was added 1 M aqueous NaOH solution (0.86 mL, 0.86 mmol) and the reaction mixture was stirred at room temperature overnight. The mixture was concentrated to dryness, diluted with water, and washed with diethyl ether twice. The aqueous layer was acidified by addition of 1 N aqueous HCl and extracted with DCM twice. The combined organic layers were washed with brine, dried over anhydrous $Na_2SO_4$, and concentrated to dryness to afford 47-S8 (106 mg, 72.9% yield) as a white solid. LC/MS (ESI) m/z: 339 $(M+H)^+$.

Step 8: (1R,3S,5R)-2-(2-(3-Acetyl-7-ethyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (47)

To a solution of 47-S8 (30 mg, 0.089 mmol), 47-S9 (32 mg, 0.093 mmol), and HATU (50.0 mg, 0.133 mmol) in DMF (3 mL) was added DIPEA (34 mg, 0.267 mmol) and the reaction mixture was stirred at room temperature under an atmosphere of nitrogen for 2 hours. The mixture was diluted with EtOAc and washed with 10% aqueous LiCl solution and brine. The organic layer was dried over anhydrous $Na_2SO_4$ and concentrated to dryness. The remaining residue was purified by preparative HPLC to afford 47 (8 mg, 10.7% yield) as a white solid. $^1$H NMR (400 MHz, DMSO-$d_6$) δ 10.32 (s, 1H), 9.04 (s, 2H), 8.35 (d, J=1.5 Hz, 1H), 7.64-7.60 (m, 2H), 7.45 (d, J=8.0 Hz, 1H), 5.96 (d, J=16.0 Hz, 1H), 5.68 (d, J=20.0 Hz, 1H), 4.40 (m, 1H), 3.60 (m, 2H), 3.03-2.97 (m, 2H), 2.69 (s, 3H), 2.65 (s, 3H), 2.58 (m, 2H), 2.04 (s, 4H), 1.33 (d, J=8.0 Hz, 6H), 1.06 (t, J=5.3 Hz, 1H), 0.93 (m, 1H). LC/MS (ESI) m/z: 630 $(M+H)^+$.

Scheme 28. Synthesis of Methyl 5-(3-acetyl-1-(2-((1R,3S,5R)-3-(6-bromo-3-methylpyridin-2-ylcarbamoyl)-5-methyl-2-azabicyclo[3.1.0]hexan-2-yl)-2-oxoethyl)-7-methyl-1H-indazol-5-yl)-2-methylpyrimidine 1-oxide (50)

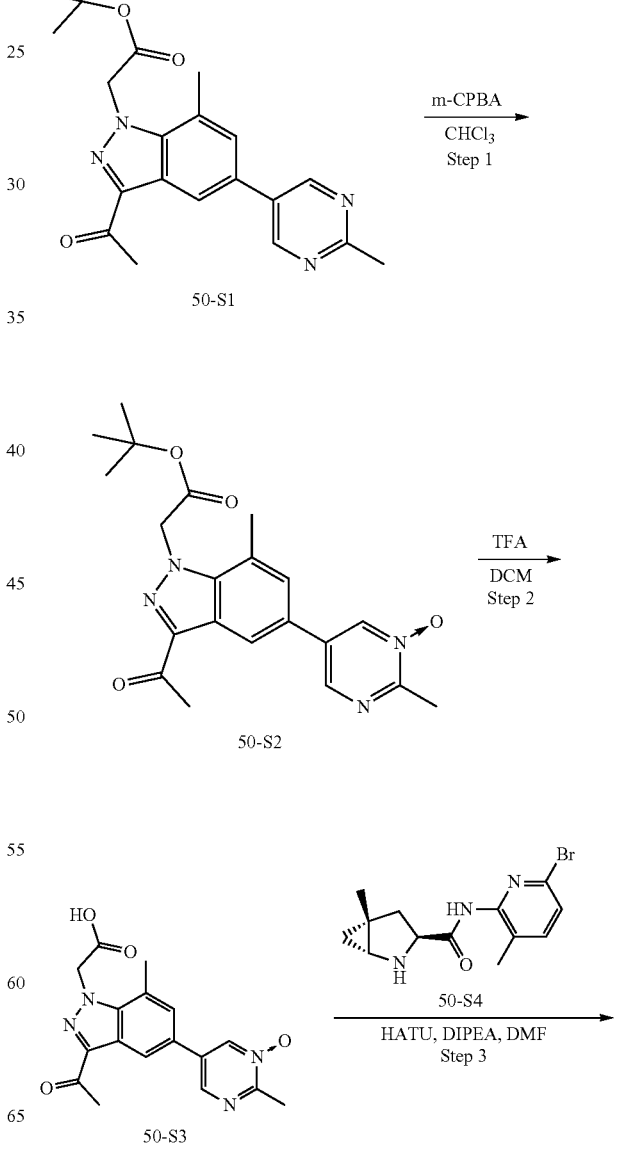

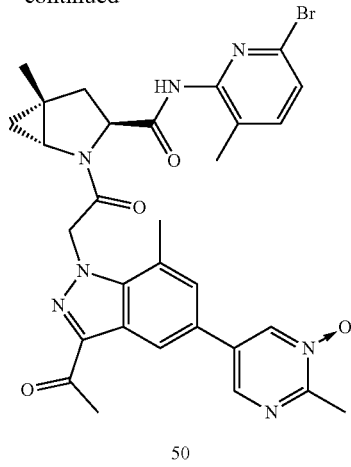

50

Step 1: 5-(3-Acetyl-1-(2-tert-butoxy-2-oxoethyl)-7-methyl-1H-indazol-5-yl)-2-methylpyrimidine 1-oxide (50-S2)

To a mixture of 50-S1 (130 mg, 0.39 mmol) in CHCl$_3$ (10 mL) was added m-CPBA (67 mg, 0.39 mmol). The reaction mixture was stirred at room temperature for 16 hours. The mixture was adjusted to pH 10 with aqueous NaHCO$_3$. The mixture was partitioned with DCM/MeOH (20:1) and water. The organic layer was washed with brine, dried over anhydrous Na$_2$SO$_4$, and concentrated under reduced pressure. The remaining residue was purified by column chromatography on silica gel (eluted with DCM/MeOH=120:1) to afford the title product (77 mg, 49.2% yield) as a white solid. LC/MS (ESI) m/z: 397 (M+H)$^+$.

Step 2: 5-(3-Acetyl-1-(carboxymethyl)-7-methyl-1H-indazol-5-yl)-2-methylpyrimidine 1-oxide (50-S3)

To a solution of 50-S2 (77 mg, 0.18 mmol) in DCM (2 mL) was added TFA (2 mL). The reaction mixture was stirred at room temperature for 1.5 hours and then concentrated under reduced pressure to afford the title product (60 mg, 88.4% yield) as a yellow solid, which was carried forward in the next synthetic step without further purification. LC/MS (ESI) m/z: 341 (M+H)$^+$.

Step 3: 5-(3-Acetyl-1-(2-((1R,3S,5R)-3-(6-bromo-3-methylpyridin-2-ylcarbamoyl)-5-methyl-2-azabicyclo[3.1.0]hexan-2-yl)-2-oxoethyl)-7-methyl-1H-indazol-5-yl)-2-methylpyrimidine 1-oxide (50)

To a solution of 50-S3 (60 mg, 0.145 mmol), (1R,3S,5R)—N-(6-bromo-3-methylpyridin-2-yl)-5-methyl-2-azabicyclo[3.1.0]hexane-3-carboxamide (50 mg, 0.145 mmol), and HATU (84 mg, 0.22 mmol) in DMF (3 mL) was added DIPEA (57 mg, 0.43 mmol). The reaction mixture was stirred at room temperature for 1 hour. The mixture was partitioned with DCM/MeOH (20:1) and water. The organic layer was washed with brine, dried over anhydrous Na$_2$SO$_4$, and concentrated under reduced pressure. The remaining residue was purified by preparative HPLC (eluted with MeCN/water) to afford 50 (2.2 mg, 1.6% yield) as a white solid. $^1$H NMR (400 MHz, DMSO-d$_6$) δ 10.32 (s, 1H), 8.95 (d, J=1.9 Hz, 1H), 8.57 (d, J=1.9 Hz, 1H), 8.35 (s, 1H), 7.62 (d, J=8.0 Hz, 2H), 7.44 (d, J=7.9 Hz, 1H), 6.03 (d, J=17.9 Hz, 1H), 5.69 (d, J=17.8 Hz, 1H), 4.41 (dd, J=9.1, 5.5 Hz, 1H), 3.56-3.61 (m, 1H), 2.67 (s, 3H), 2.65 (s, 3H), 2.61 (s, 3H), 2.53-2.59 (m, 1H), 2.04 (s, 3H), 1.97-2.03 (m, 1H), 1.33 (s, 3H), 1.00-1.05 (m, 1H), 0.91-0.97 (m, 1H). LC/MS (ESI) m/z: 632/634 (M+H)$^+$.

Scheme 29. Synthesis of (3S)-2-(2-(3-Acetyl-7-methyl-5-(2-methylpyrimidin-5-yl)-1H-indazol-1-yl) acetyl)-N-(6-bromo-3-methylpyridin-2-yl)-5-((dimethylamino) methyl)-2-azabicyclo[3.1.0] hexane-3-carboxamide (51)

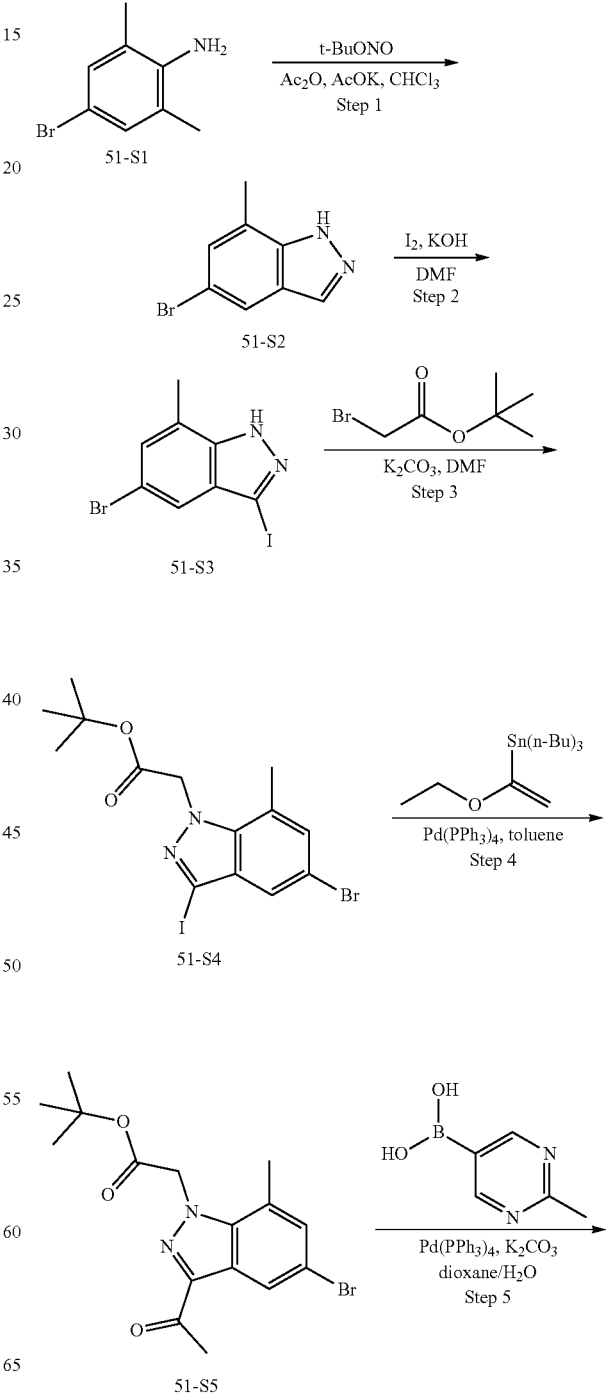

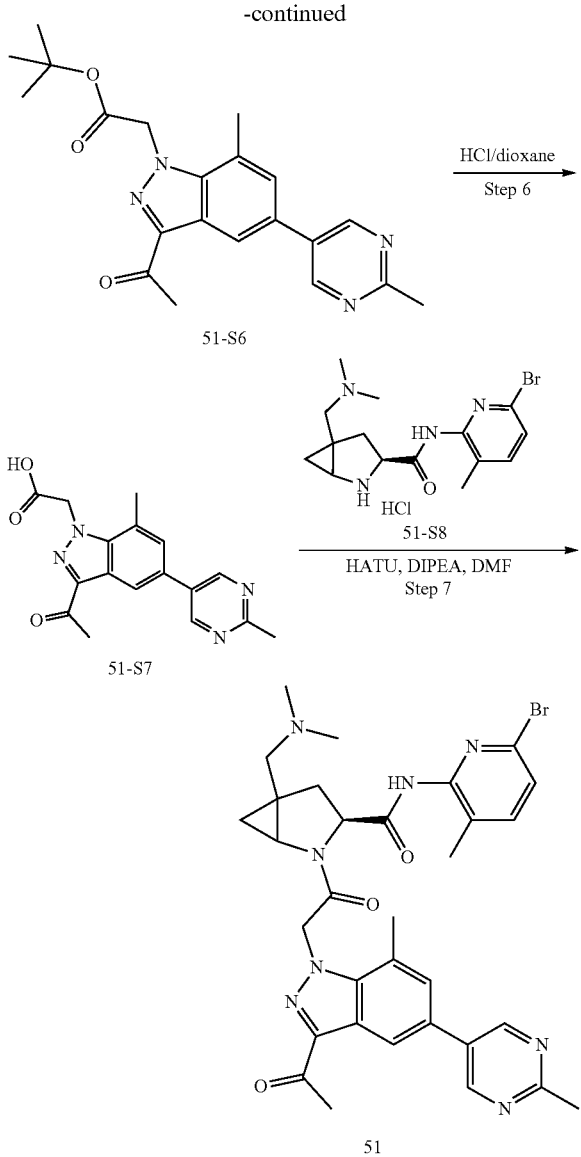

Step 2: 5-Bromo-3-iodo-7-methyl-1H-indazole (51-S3)

To a solution of 51-S2 (10 g, 0.047 mol) in DMF (50 mL) was added KOH (6.63 g, 0.18 mol) followed by I$_2$ (18.06 g, 0.071 mol) at 0° C. The mixture was stirred at room temperature for 1.5 hour. The reaction mixture was quenched by aqueous Na$_2$S$_2$O$_3$ and diluted with EtOAc. The mixture was washed with water and brine, dried over anhydrous Na$_2$SO$_4$, and concentrated to dryness. The remaining residue was washed with a mixture of PE/EtOAc (50 mL, 5:1) and dried under vacuum to afford 51-S3 (15.1 g, 94.6% yield) as light a yellow solid. LC/MS (ESI) m/z: 338 (M+H)$^+$.

Step 3: tert-Butyl 2-(5-bromo-3-iodo-7-methyl-1H-indazol-1-yl) acetate (51-S4)

To a solution of 51-S3 (6.9 g, 0.02 mol) in DMF (20 mL) were added K$_2$CO$_3$ (8.48 g, 0.06 mol) and tert-butyl 2-bromoacetate (3.97 g, 0.02 mol) and the resulting mixture was stirred at room temperature overnight. The mixture was diluted with EtOAc, washed with water and brine, dried over anhydrous Na$_2$SO$_4$, and concentrated to dryness. The remaining crude product was purified by column chromatography on silica gel (eluted with PE/EtOAc=200:1 to 70:1) to afford 51-S4 (5.66 g, 61.3% yield) as light a yellow solid. LC/MS (ESI) m/z: 452 (M+H)$^+$.

Step 4: tert-Butyl 2-(3-acetyl-5-bromo-7-methyl-1H-indazol-1-yl) acetate (51-S5)

To a solution of 51-S4 (4.63 g, 10.27 mmol) in dry toluene (25 mL) were added tributyl(1-ethoxyvinyl)stannane (5.19 g, 14.38 mmol) and Pd(PPh$_3$)$_4$ (0.83 g, 0.72 mmol). The reaction mixture was degassed with nitrogen and stirred at 100° C. under an atmosphere of nitrogen overnight. The mixture was cooled to room temperature, 0.5 M aqueous HCl (20 mL) was added, and then stirred at room temperature for 20 minutes. The reaction mixture was diluted with H$_2$O and extracted with EtOAc twice. The combined organic layers were washed by brine, dried over anhydrous Na$_2$SO$_4$, and concentrated. The remaining crude product was purified by column chromatography on silica gel (eluted with PE/EtOAc=150:1 to 60:1) to afford 51-S5 (2.63 g, 70.0% yield) as milky a white solid. LC/MS (ESI) m/z: 367 (M+H)$^+$.

Step 5: tert-Butyl 2-(3-acetyl-7-methyl-5-(2-methylpyrimidin-5-yl)-1H-indazol-1-yl) acetate (51-S6)

A round-bottom flask was charged with 51-S5 (2.63 g, 7.18 mmol), 2-methylpyrimidin-5-ylboronic acid (0.99 g, 7.18 mmol), K$_2$CO$_3$ (2.48 g, 17.96 mmol), and dioxane/H$_2$O (20 mL, v/v=9:1) under an atmosphere of nitrogen. To this mixture was added tetrakis(triphenylphosphine) palladium (0) (0.42 g, 0.36 mmol) and the resulting mixture was stirred at 90° C. overnight under an atmosphere of nitrogen. The mixture was diluted with EtOAc and filtered. The filtrate was diluted with EtOAc, washed with brine, dried over anhydrous Na$_2$SO$_4$, and concentrated to dryness. The remaining crude product was purified by column chromatography on silica gel (eluted with PE/EtOAc=100:1 to 3:1) to afford 51-S6 (1.93 g, 70.7% yield) as light a yellow solid. LC/MS (ESI) m/z: 381 (M+H)$^+$.

Step 1: 5-Bromo-7-methyl-1H-indazole (51-S2)

To a solution of 4-bromo-2,6-dimethylaniline (51-S1, 10 g, 0.05 mol) and potassium acetate (5.88 g, 0.06 mol) in CHCl$_3$ (120 mL) was added acetic anhydride (15.3 g, 0.15 mol) dropwise at 0° C. under an atmosphere of nitrogen and the resulting mixture was stirred at room temperature for 1 hour. The reaction mixture was heated to 60° C. and tert-butyl nitrite (10.3 g, 0.1 mol) was added dropwise. The resulting mixture was stirred overnight at 60° C. The mixture was cooled to room temperature, diluted with H$_2$O, and extracted with DCM twice. The combined organic layers were washed by brine, dried over anhydrous Na$_2$SO$_4$, and concentrated to dryness. The remaining residue was dissolved in MeOH and 6 N aqueous HCl (50 mL, v/v=1:1) and the resulting mixture was stirred at room temperature for 4 hour. The reaction mixture was basified with 10 N aqueous NaOH and extracted with DCM. The organic layer was washed by brine, dried over anhydrous Na$_2$SO$_4$, and concentrated to afford 51-S2 (10.1 g, 95.7% yield) as light a yellow solid. LC/MS (ESI) m/z: 212 (M+H)$^+$.

Step 6: 2-(3-Acetyl-7-methyl-5-(2-methylpyrimidin-5-yl)-1H-indazol-1-yl) acetic Acid (51-S7)

Compound 51-S6 (1.45 g, 3.81 mmol) was treated with HCl/dioxane (9 mL) and stirred at room temperature for 2 hours. The reaction mixture was concentrated to dryness and the remaining residue was washed with ether and dried under vacuum to afford 51-S7 (1.23 g, 99.8% yield) as light a yellow solid. LC/MS (ESI) m/z: 324 (M+H)$^+$.

Step 7: (3S)-2-(2-(3-Acetyl-7-methyl-5-(2-methylpyrimidin-5-yl)-1H-indazol-1-yl) acetyl)-N-(6-bromo-3-methylpyridin-2-yl)-5-((dimethylamino)methyl)-2-azabicyclo [3.1.0] hexane-3-carboxamide (51)

To a mixture of 51-S7 (30 mg, 0.093 mmol) and 51-S8 (33 mg, 0.093 mmol) in DMF (1 mL) was added DIPEA (60 mg, 0.46 mmol) followed by HATU (77 mg, 0.20 mmol). The reaction mixture was stirred at room temperature for 1 hour. The mixture was diluted with EtOAc, washed with 10% aqueous LiCl solution and brine, dried, and concentrated to afford the crude product, which was purified by preparative HPLC to afford 51 (2 mg, 3.28% yield) as a white solid. $^1$H NMR (400 MHz, CD$_3$OD) δ 9.02 (s, 2H), 8.46 (s, 1H), 7.64-7.55 (m, 2H), 7.43 (d, J=8.0 Hz, 1H), 6.01 (d, J=17.6 Hz, 1H), 5.83 (d, J=17.6 Hz, 1H), 4.72 (dd, J=8.8, 4.4 Hz, 1H), 3.95 (dd, J=5.6, 2.8 Hz, 1H), 3.59 (d, J=14.0 Hz, 1H), 3.24 (d, J=13.6 Hz, 1H), 2.98 (s, 6H), 2.78 (s, 3H), 2.77 (s, 3H), 2.75-2.73 (m, 1H), 2.70 (s, 3H), 2.59 (dd, J=13.6, 4.0 Hz, 1H), 2.14 (s, 3H), 1.52 (t, J=5.6 Hz, 1H), 1.42-1.39 (m, 1H). LC/MS (ESI) m/z: 660 (M+H)$^+$.

Scheme 30. Synthesis of (2S,4R)-1-(2-(3-Acetyl-5-(2-hydroxypyrimidin-5-yl)-1H-indazol-1-yl)acetyl)-N-(6-bromo-3-methylpyridin-2-yl)-4-fluoropyrrolidine-2-carboxamide (59)

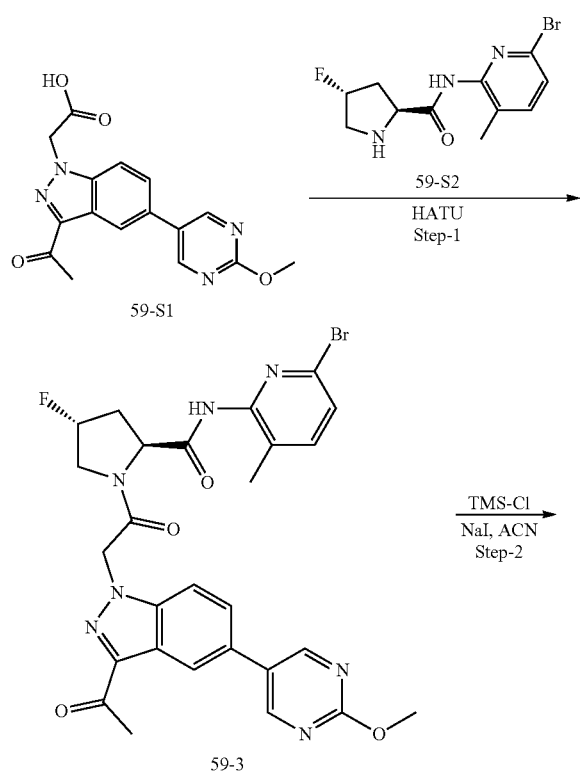

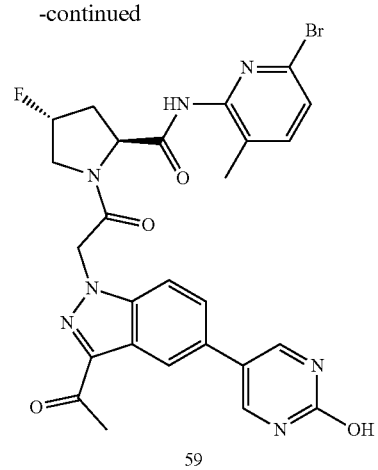

Step 1: (2S,4R)-1-(2-(3-Acetyl-5-(2-methoxypyrimidin-5-yl)-1H-indazol-1-yl)acetyl)-N-(6-bromo-3-methylpyridin-2-yl)-4-fluoropyrrolidine-2-carboxamide (59-S3)

To a solution of 2-(3-acetyl-5-(2-methoxypyrimidin-5-yl)-1H-indazol-1-yl)acetic acid (59-S1, 1 equiv) in DMF (10 vol) at 0° C. under nitrogen atmosphere was added (2S,4R)—N-(6-bromo-3-methylpyridin-2-yl)-4-fluoropyrrolidine-2-carboxamide (59-S2, 1.2 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous Na$_2$SO$_4$, filtered and concentrated. The residue was purified by column chromatography on silica gel using DCM/MeOH to afford compound 59-S3. $^1$H NMR (400 MHz, DMSO-d$_6$) δ: 10.47 (s, 1H), 8.95 (s, 2H), 8.38 (s, 1H), 7.81 (s, 2H), 7.71 (d, J=8.0 Hz, 1H), 7.43 (d, J=8.0 Hz, 1H), 5.85 (d, J=17.2 Hz, 1H), 5.62 (d, J=16.8 Hz, 1H), 5.50 (s, 1H), 4.60 (t, J=16.8 Hz, 1H), 4.29-4.21 (m, 1H), 4.08-4.05 (m, 1H), 3.98 (s, 3H), 2.67 (s, 3H), 2.66-2.65 (m, 1H), 2.25-2.14 (m, 1H), 2.00 (s, 3H).

Step 2: (2S,4R)-1-(2-(3-Acetyl-5-(2-hydroxypyrimidin-5-yl)-1H-indazol-1-yl)acetyl)-N-(6-bromo-3-methylpyridin-2-yl)-4-fluoropyrrolidine-2-carboxamide (59)

To a solution of compound 59-S3 (1 equiv) in ACN (10 vol) at 0° C. under nitrogen atmosphere was added TMSCl (2.5 equiv) and NaI (2 equiv). The reaction mixture was stirred at room temperature for 16 hours. After completion of the reaction, the reaction mixture was concentrated and quenched with water. The resulting solid was filtered and dried to afford compound 59. $^1$H NMR (400 MHz, DMSO-d$_6$) δ: 10.47 (s, 1H), 8.65 (s, 2H), 8.29 (s, 1H), 7.75 (s, 2H), 7.61 (d, J=8.4 Hz, 1H), 7.43 (d, J=8.0 Hz, 1H), 5.82 (d, J=17.2 Hz, 1H), 5.62 (d, J=16.8 Hz, 1H), 5.50 (s, 1H), 4.59 (t, J=16.8 Hz, 1H), 4.28-4.20 (m, 1H), 4.07-4.04 (m, 1H), 2.55-2.54 (m, 1H), 2.53 (s, 3H), 2.33-2.21 (m, 1H), 2.00 (s, 3H).

Scheme 31. Synthesis of (1R,3S,5R)-2-(2-(3-Acetyl-5-(2-methylpyrimidin-5-yl)-1H-indazol-1-yl)acetyl)-5-((allyl(methyl)amino)methyl)-N-(3-((allyloxy)methyl)-6-bromopyridin-2-yl)-2-azabicyclo[3.1.0]hexane-3-carboxamide (70)

step 3

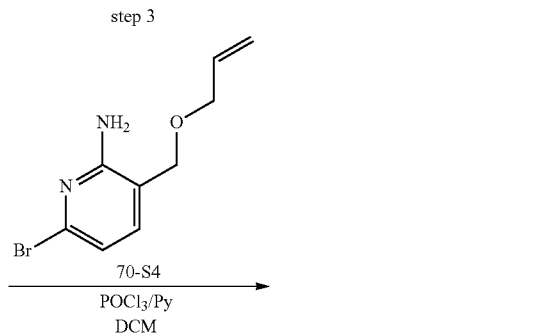

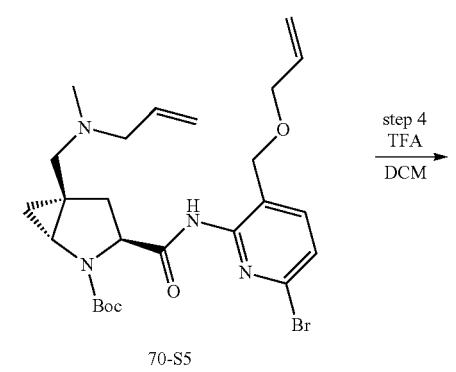

step 5

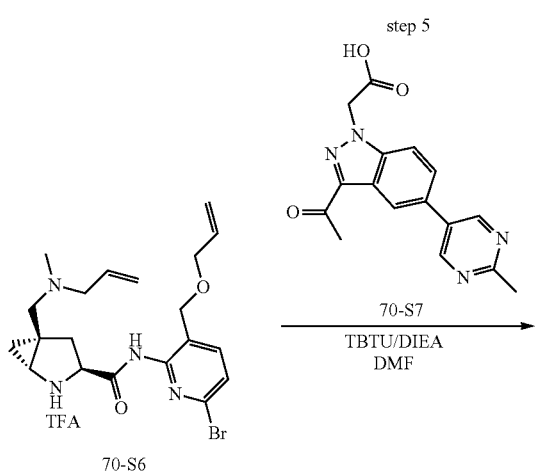

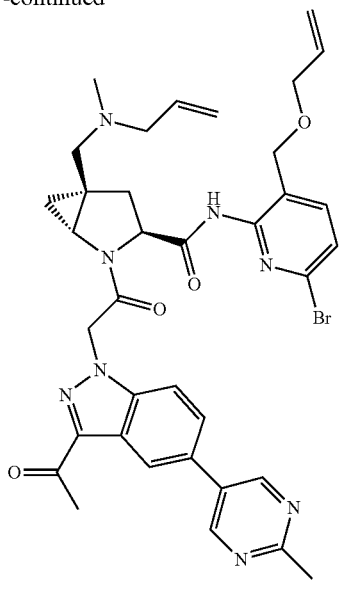

Step 1: 2-(tert-Butyl) 3-ethyl (1R,3S,5R)-5-((allyl(methyl)amino)methyl)-2-azabicyclo[3.1.0]hexane-2,3-dicarboxylate (70-S2)

K$_2$CO$_3$ (1 g) was added to a mixture of 2-(tert-butyl) 3-ethyl (1R,3S,5S)-5-(((methylsulfonyl)oxy)methyl)-2-azabicyclo[3.1.0]hexane-2,3-dicarboxylate (70-S1, 0.77 mmol) and N-methylprop-2-en-1-amine (0.663 mL, 6.93 mmol) in ACN (8 mL) and the reaction was heated at 40° C. under argon for 4 hours. EtOAc was added and the diluted reaction mixture was filtered through Celite to remove any solids. Solvents were removed under reduced pressure and the residue was purified by column chromatography on silica gel with MeOH in DCM (0-10%) as the eluent to afford 2-(tert-butyl) 3-ethyl (1R,3S,5R)-5-((allyl(methyl)amino)methyl)-2-azabicyclo[3.1.0]hexane-2,3-dicarboxylate 70-S2 (0.211 g) as yellow amorphous solid.

Step 2: (1R,3S,5R)-5-((Allyl(methyl)amino)methyl)-2-(tert-butoxycarbonyl)-2-azabicyclo[3.1.0]hexane-3-carboxylic Acid (70-S3)

2-(tert-Butyl) 3-ethyl (1R,3S,5R)-5-((allyl(methyl)amino)methyl)-2-azabicyclo[3.1.0]hexane-2,3-dicarboxylate (70-S2, 0.211 g, 0.624 mmol) was dissolved in a mixture of THF-EtOH-water (3 mL-0.75 mL-0.7 mL) and treated with LiOH monohydrate (32 mg, 0.75 mmol). The reaction stirred at room temperature for 6 hours before Amberlite (weakly acidic cation exchanger H form, 1 g) was added. After stirring for 20 minutes, the reaction was filtered and the resulting resin was washed with MeOH. The combined filtrates were concentrated under reduced pressure and the residue was purified by column chromatography on silica gel with MeOH in DCM (0-10%) as an eluent to afford (1R,3S,5R)-5-((allyl(methyl)amino)methyl)-2-(tert-butoxycarbonyl)-2-azabicyclo[3.1.0]hexane-3-carboxylic acid 70-S3 (0.188 g) as colorless amorphous solid.

Step 3: tert-Butyl (1R,3S,5R)-5-((allyl(methyl)amino)methyl)-3-((3-((allyloxy)methyl)-6-bromopyridin-2-yl)carbamoyl)-2-azabicyclo[3.1.0]hexane-2-carboxylate (70-S5)

To a mixture of 70-S3 (188 mg, 0.61 mmol) and 70-S4 (148 mg, 0.61 mmol) in DCM (10 mL), pyridine (0.246 mL, 3.05 mmol) was added followed by POCl₃ (0.057 mL, 0.61 mmol) at 0° C. under argon. The reaction mixture was stirred at room temperature for 2 hours before NaHCO₃ aqueous solution was added and the mixture was extracted with DCM. After washing with brine, the organic layer was dried over anhydrous Na₂SO₄. The solution was filtered and the solvent was removed under reduced pressure. The remaining residue was purified by column chromatography on silica gel with MeOH in DCM (0-10%) as eluent to afford tert-butyl (1R,3S,5R)-5-((allyl(methyl)amino)methyl)-3-((3-((allyloxy)methyl)-6-bromopyridin-2-yl)carbamoyl)-2-azabicyclo[3.1.0]hexane-2-carboxylate (70-S5, 173.5 mg).

Step 4: (1R,3S,5R)-5-((Allyl(methyl)amino)methyl)-N-(3-((allyloxy)methyl)-6-bromopyridin-2-yl)-2-azabicyclo[3.1.0]hexane-3-carboxamide TFA Salt (70-S6)

tert-Butyl (1R,3S,5R)-5-((allyl(methyl)amino)methyl)-3-((3-((allyloxy)methyl)-6-bromopyridin-2-yl)carbamoyl)-2-azabicyclo[3.1.0]hexane-2-carboxylate (70-S5, 29.5 mg) in DCM (2 mL) was treated with TFA (2 mL) at room temperature for 1 hour. The volatiles were removed under reduced pressure and the residue was co-evaporated with toluene (5 mL) twice to afford (1R,3S,5R)-5-((allyl(methyl)amino)methyl)-N-(3-((allyloxy)methyl)-6-bromopyridin-2-yl)-2-azabicyclo[3.1.0]hexane-3-carboxamide TFA salt 70-S6. The material was carried forward without additional purification.

Step 5: (1R,3S,5R)-2-(2-(3-Acetyl-5-(2-methylpyrimidin-5-yl)-1H-indazol-1-yl)acetyl)-5-((allyl(methyl)amino)methyl)-N-(3-((allyloxy)methyl)-6-bromopyridin-2-yl)-2-azabicyclo[3.1.0]hexane-3-carboxamide (70)

To a mixture of (1R,3S,5R)-5-((allyl(methyl)amino)methyl)-N-(3-((allyloxy)methyl)-6-bromopyridin-2-yl)-2-azabicyclo[3.1.0]hexane-3-carboxamide TFA salt 70-S6 and 2-(3-acetyl-5-(2-methylpyrimidin-5-yl)-1H-indazol-1-yl)acetic acid (70-S7, 17 mg, 0.055 mmol) in DMF (1 mL), TBTU (26.5 mg) was added at room temperature followed by the addition of DIEA (0.096 mL) with stirring. After the reaction was complete, NaHCO₃ aqueous solution (10 mL) was added to form a precipitation that was collected by filtration and purified by column chromatography on silica gel with MeOH in DCM (0-10%) as the eluent to afford 70 (29 mg) as an off-white solid. ¹H NMR (400 MHz, Chloroform-d) δ 8.89 (s, 3H), 8.56 (dd, J=1.7, 0.9 Hz, 1H), 7.61 (qd, J=8.7, 1.3 Hz, 2H), 7.48 (d, J=8.0 Hz, 1H), 7.23 (d, J=7.8 Hz, 1H), 5.91-5.76 (m, 2H), 5.50 (d, J=2.7 Hz, 2H), 5.25-5.11 (m, 4H), 4.95 (s, 1H), 4.41-4.26 (m, 2H), 3.88 (d, J=5.7 Hz, 2H), 3.29 (dd, J=5.5, 2.5 Hz, 1H), 3.06 (dt, J=6.4, 1.4 Hz, 2H), 2.80 (m, 6H), 2.72 (s, 3H), 1.21 (t, J=5.6 Hz, 1H), 0.99 (dd, J=5.5, 2.5 Hz, 1H). LC (method A): $t_R$=1.35 min. LC/MS (EI) m/z: [M+H]⁺ 727.

Scheme 32. Synthesis of (1R,3S,5R)-2-(2-(3-Acetyl-7-(fluoromethyl)-5-(2-methylpyrimidin-5-yl)-1H-indazol-1-yl)acetyl)-N-(6-bromo-3-methylpyridin-2-yl)-5-((dimethylamino)methyl)-2-azabicyclo[3.1.0]hexane-3-carboxamide (74) and (1S,3S,5S)-2-(2-(3-Acetyl-7-(fluoromethyl)-5-(2-methylpyrimidin-5-yl)-1H-indazol-1-yl)acetyl)-N-(6-bromo-3-methylpyridin-2-yl)-5-((dimethylamino)methyl)-2-azabicyclo[3.1.0]hexane-3-carboxamide (75)

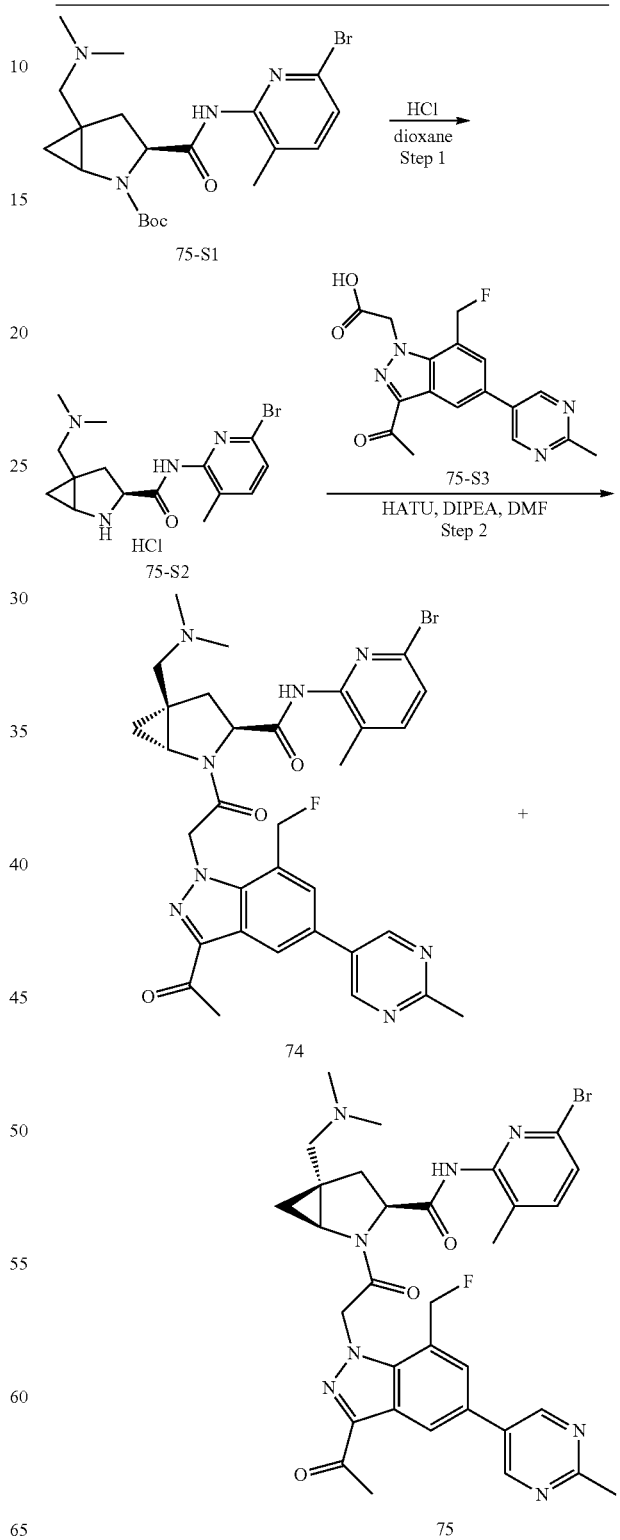

Step 1: (3S)—N-(6-Bromo-3-methylpyridin-2-yl)-5-((dimethylamino)methyl)-2-azabicyclo[3.1.0]hexane-3-carboxamide (75-S2)

To a solution of 75-S1 (150 mg, 0.33 mmol) in dioxane (1.5 mL) was added HCl/dioxane (1.5 mL, 2 M). The reaction mixture was stirred at room temperature for 30 minutes. The mixture was concentrated to dryness, diluted with DCM, washed with aqueous NaHCO$_3$ solution, dried over anhydrous Na$_2$SO$_4$, and concentrated to dryness. The remaining residue was purified by column chromatography on silica gel (DCM/MeOH=60:1) to afford 75-S2 (100 mg, 86.2% yield) as a yellow oil. LC/MS (ESI) m/z: 352 (M+H)$^+$.

Step 2: (1R,3S,5R)-2-(2-(3-Acetyl-7-(fluoromethyl)-5-(2-methylpyrimidin-5-yl)-1H-indazol-1-yl)acetyl)-N-(6-bromo-3-methylpyridin-2-yl)-5-((dimethylamino)methyl)-2-azabicyclo[3.1.0]hexane-3-carboxamide (74) and (1S,3S,5S)-2-(2-(3-Acetyl-7-(fluoromethyl)-5-(2-methylpyrimidin-5-yl)-1H-indazol-1-yl)acetyl)-N-(6-bromo-3-methylpyridin-2-yl)-5-((dimethylamino)methyl)-2-azabicyclo[3.1.0]hexane-3-carboxamide (75)

To a solution of 75-S2 (40 mg, 0.105 mmol), 75-S3 (30 mg, 0.087 mmol), and HATU (50.0 mg, 0.13 mmol) in DMF (3 mL) was added DIPEA (34 mg, 0.26 mmol). The reaction mixture was stirred at room temperature under an atmosphere of nitrogen for 2 hours. The mixture was diluted with EtOAc, washed with 10% aqueous LiCl solution and brine, dried over anhydrous Na$_2$SO$_4$, and concentrated to dryness. The remaining residue was purified by preparative HPLC to afford 74 (2.0 mg, 3.4% yield) and 75 (2.2 mg, 3.8% yield) as white solids.

Compound 74

$^1$H NMR (400 MHz, DMSO-d$_6$) δ 10.34 (s, 1H), 9.07 (s, 2H), 8.58 (s, 1H), 8.01 (s, 1H), 7.63 (d, J=8.0 Hz, 1H), 7.45 (d, J=8.0 Hz, 1H), 5.97-5.93 (m, 1H), 5.85-5.76 (m, 1H), 5.75-5.62 (m, 2H), 4.46 (m, 1H), 3.63 (m, 1H), 2.69 (d, J=8.0 Hz, 6H), 2.46-2.31 (m, 4H), 2.24 (s, 6H), 2.05 (s, 3H), 1.09-1.02 (m, 2H).

Compound 75

$^1$H NMR (400 MHz, DMSO-d$_6$) δ 10.46 (s, 1H), 9.05 (s, 2H), 8.56 (s, 1H), 7.98 (s, 1H), 7.60 (d, J=8.0 Hz, 1H), 7.42 (d, J=8.0 Hz, 1H), 6.09 (d, J=20.0 Hz, 1H), 5.96 (m, 1H), 5.78-5.65 (m, 1H), 5.64-5.59 (m, 1H), 4.92 (d, J=8.0 Hz, 1H), 3.73-3.68 (m, 1H), 2.77 (t, J=12.0 Hz, 1H), 2.68 (d, J=4.0 Hz, 6H), 2.38 (s, 2H), 2.23 (s, 6H), 2.00 (m, 1H), 1.96 (s, 3H), 1.46 (d, J=4.0 Hz, 1H), 0.93 (m, 1H).

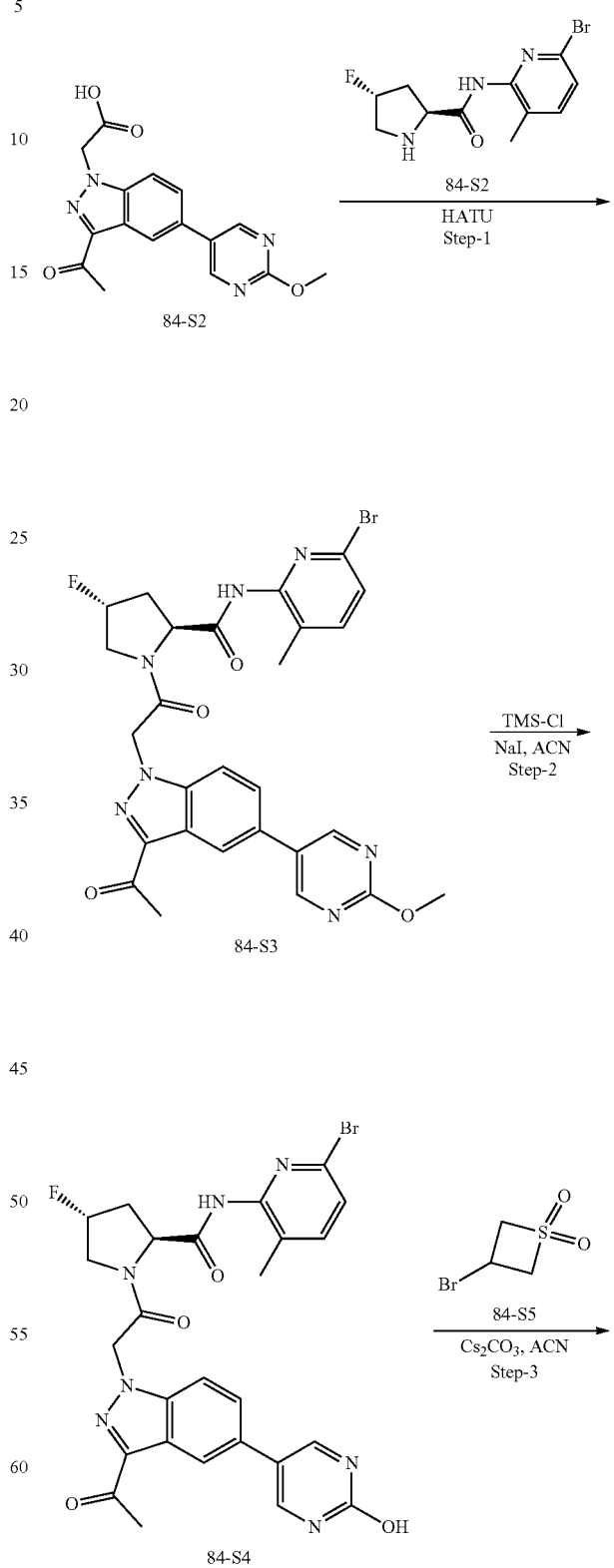

Scheme 33. Synthesis of (2S,4R)-1-(2-(3-Acetyl-5-(2-((1,1-dioxidothietan-3-yl)oxy)pyrimidin-5-yl)-1H-indazol-1-yl)acetyl)-N-(6-bromo-3-methylpyridin-2-yl)-4-fluoropyrrolidine-2-carboxamide (84)

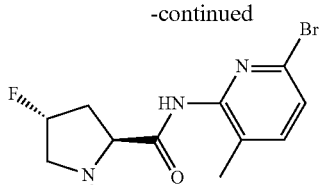

Step 1: (2S,4R)-1-(2-(3-Acetyl-5-(2-methoxypyrimidin-5-yl)-1H-indazol-1-yl)acetyl)-N-(6-bromo-3-methylpyridin-2-yl)-4-fluoropyrrolidine-2-carboxamide (84-S3)

To a solution of 2-(3-acetyl-5-(2-methoxypyrimidin-5-yl)-1H-indazol-1-yl)acetic acid (84-S1, 1 equiv) in DMF (10 vol) at 0° C. under nitrogen atmosphere was added (2S,4R)—N-(6-bromo-3-methylpyridin-2-yl)-4-fluoropyrrolidine-2-carboxamide (84-S2, 1.2 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and concentrated. The residue was purified by column chromatography on silica gel using DCM/MeOH to afford compound 84-S3.

Step 2: (2S,4R)-1-(2-(3-Acetyl-5-(2-hydroxypyrimidin-5-yl)-1H-indazol-1-yl)acetyl)-N-(6-bromo-3-methylpyridin-2-yl)-4-fluoropyrrolidine-2-carboxamide (84-S4)

To a solution of compound 84-S3 (1 equiv) in ACN (10 vol) at 0° C. under nitrogen atmosphere was added TMSCl (2.5 equiv) and NaI (2 equiv). The reaction mixture was stirred at room temperature for 16 hours. After completion of the reaction, the reaction mixture was concentrated and quenched with water. The resulting solid was filtered and dried to afford compound 84-54.

Step 3: (2S,4R)-1-(2-(3-Acetyl-5-(2-((1,1-dioxidothietan-3-yl)oxy)pyrimidin-5-yl)-1H-indazol-1-yl)acetyl)-N-(6-bromo-3-methylpyridin-2-yl)-4-fluoropyrrolidine-2-carboxamide (84)

To a solution of compound 84-S4 (1 equiv) in ACN (10 vol) was added cesium carbonate (3 equiv) and 3-bromothietane 1,1-dioxide (84-S5, 2 equiv). The reaction mixture was stirred at room temperature for 16 hours. After completion of the reaction, the reaction mixture was concentrated and quenched with water. The resulting solid was filtered, dried and then purified by preparative purification to afford compound 84. $^1$H NMR (400 MHz, DMSO-$d_6$) δ: 10.84 (s, 1H), 9.02 (s, 1H), 8.59 (s, 1H), 8.36 (s, 1H), 7.78-7.72 (m, 2H), 7.61 (d, J=8.0 Hz, 1H), 7.43 (d, J=7.6 Hz, 1H), 5.83 (d, J=17.2 Hz, 1H), 5.62 (d, J=17.2 Hz, 1H), 5.58-5.50 (m, 1H), 5.30-5.28 (m, 1H), 5.02-4.96 (m, 2H), 4.61-4.55 (m, 3H), 4.28-3.88 (m, 2H), 2.63 (s, 3H), 2.30-2.12 (m, 1H), 2.00 (s, 3H), 0.98-0.95 (m, 1H).

Scheme 34. Synthesis of (1R,3S,5S)-2-(2-(3-Acetyl-5-(2-methylpyrimidin-5-yl)-1H-indazol-1-yl)acetyl)-5-((allyloxy)methyl)-N-(6-bromo-3-vinylpyridin-2-yl)-2-azabicyclo[3.1.0]hexane-3-carboxamide (93)

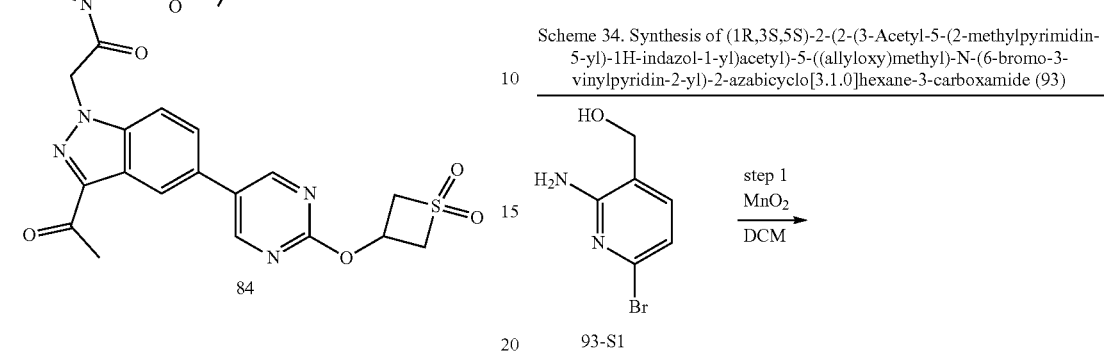

-continued

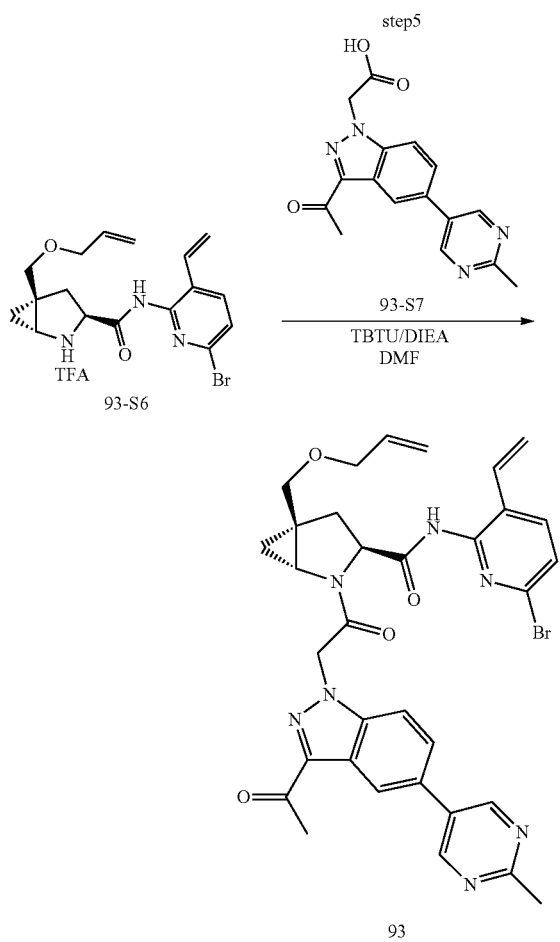

Step 1: 2-Amino-6-bromonicotinaldehyde (93-S2)

(2-Amino-6-bromopyridin-3-yl)methanol (93-S1, 1.0 g, 4.93 mmol) was treated with activated $MnO_2$ (4.29 g, 49.3 mmol) in DCM (50 mL) at room temperature overnight. The mixture was filtered through Celite and the solvent was removed under reduced pressure to afford 2-amino-6-bromonicotinaldehyde 93-S2 (0.9 g) as a yellow solid.

Step 2: 6-Bromo-3-vinylpyridin-2-amine (93-S3)

Into a suspension of methyltriphenylphosphonium bromide (1.28 g, 3.6 mmol) in THF (10 mL), n-BuLi (1.6M in hexane, 2.25 mL, 3.6 mmol) was added with stirring at 0° C. under argon. After 1 hour, 2-amino-6-bromonicotinaldehyde (93-S2, 0.18 g, 0.9 mmol) in THF (5 mL) was added and the mixture was stirred at room temperature for 2 hours. The reaction was cooled in an ice bath and saturated $NH_4Cl$ aqueous solution (10 mL) was added. The mixture was extracted with EtOAc and the organic layer was washed with water and brine, and dried over anhydrous $Na_2SO_4$. Solvent was removed under reduced pressure and the residue was purified by column chromatography on silica gel with MeOH in DCM (0-10%) as the eluent to afford 6-bromo-3-vinylpyridin-2-amine 93-S3 (0.13 g) as a white solid.

Step 3: tert-Butyl (1R,3S,5S)-5-((Allyloxy)methyl)-3-((6-bromo-3-vinylpyridin-2-yl)carbamoyl)-2-azabicyclo[3.1.0]hexane-2-carboxylate (93-S5)

To a mixture of 93-S4 (97 mg, 0.33 mmol) and 93-S3 (65 mg, 0.33 mmol) in DCM (4 mL), pyridine (0.133 mL) was added followed by $POCl_3$ (0.031 mL, 0.33 mmol) at 0° C. under argon. The reaction mixture was stirred overnight at room temperature. Water was added and the mixture was extracted with AcOEt. After washing with brine, the organic layer was dried over anhydrous $Na_2SO_4$. The solution was filtered and the solvent was removed under reduced pressure. The remaining residue was purified by column chromatography on silica gel with EtOAc in hexane (0-50%) as the eluent to afford tert-butyl (1R,3S,5S)-5-((allyloxy) methyl)-3-((6-bromo-3-vinylpyridin-2-yl)carbamoyl)-2-azabicyclo[3.1.0]hexane-2-carboxylate 93-S5 (88 mg) as colorless oil.

Step 4: (1R,3S,5S)-5-((Allyloxy)methyl)-N-(6-bromo-3-vinylpyridin-2-yl)-2-azabicyclo[3.1.0] hexane-3-carboxamide TFA Salt (93-S6)

tert-Butyl (1R,3S,5S)-5-((allyloxy)methyl)-3-((6-bromo-3-vinylpyridin-2-yl)carbamoyl)-2-azabicyclo[3.1.0]hexane-2-carboxylate (93-S5, 23 mg, 0.048 mmol) was dissolved in DCM (2 mL) and treated with TFA (1 mL) at room temperature. The reaction was stirred for 1 hour and the volatiles were removed under reduced pressure. The residue was co-evaporated with toluene (5 mL) twice to afford (1R,3S, 5S)-5-((allyloxy)methyl)-N-(6-bromo-3-vinylpyridin-2-yl)-2-azabicyclo[3.1.0]hexane-3-carboxamide TFA salt 93-S6. The crude material was carried forward in the next step without additional purification.

Step 5: (1R,3S,5S)-2-(2-(3-Acetyl-5-(2-methylpyrimidin-5-yl)-1H-indazol-1-yl)acetyl)-5-((allyloxy) methyl)-N-(6-bromo-3-vinylpyridin-2-yl)-2-azabicyclo[3.1.0]hexane-3-carboxamide (93)

To a mixture of (1R,3S,5S)-5-((allyloxy)methyl)-N-(6-bromo-3-vinylpyridin-2-yl)-2-azabicyclo[3.1.0]hexane-3-carboxamide TFA salt 93-S6 and 2-(3-acetyl-5-(2-methylpyrimidin-5-yl)-1H-indazol-1-yl)acetic acid (S7 15.5 mg, 0.05 mmol) in DMF (1 mL), TBTU (32.1 mg, 0.1 mmol) followed by DIEA (0.0435 mL) was added at room temperature with stirring. After 1 h, $NaHCO_3$ aqueous solution (10 mL) was added to form precipitation. Solid was collected by filtration and purified by column chromatography on silica gel with MeOH in DCM (0-10%) as eluent to afford 93 (21 mg). $^1H$ NMR (400 MHz, Chloroform-d) δ 8.90 (s, 2H), 8.75 (s, 1H), 8.58 (dd, J=1.7, 0.9 Hz, 1H), 7.71-7.58 (m, 3H), 7.30 (d, J=8.1 Hz, 1H), 6.45 (dd, J=17.4, 11.0 Hz, 1H), 5.89 (ddt, J=17.3, 10.4, 5.7 Hz, 1H), 5.65 (dd, J=17.5, 0.8 Hz, 1H), 5.52 (s, 2H), 5.32-5.15 (m, 3H), 4.91 (dd, J=8.8, 2.9 Hz, 1H), 4.01 (dq, J=5.7, 1.5 Hz, 2H), 3.73 (d, J=9.8 Hz, 1H), 3.56 (d, J=9.8 Hz, 1H), 3.42 (dd, J=5.6, 2.6 Hz, 1H), 2.80 (s, 3H), 2.72 (s, 3H), 2.29 (dd, J=13.8, 8.8 Hz, 1H), 1.46 (t, J=5.5 Hz, 1H), 0.99 (dd, J=5.5, 2.7 Hz, 1H). LC (method A): $t_R$=2.01 min. LC/MS (EI) m/z: $[M+H]^+$ 670.

Scheme 35: Synthesis of (1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-((2-fluorocyclopent-1-enecarboxamido)methyl)-2-azabicyclo[3.1.0]hexane-3-carboxamide (95)

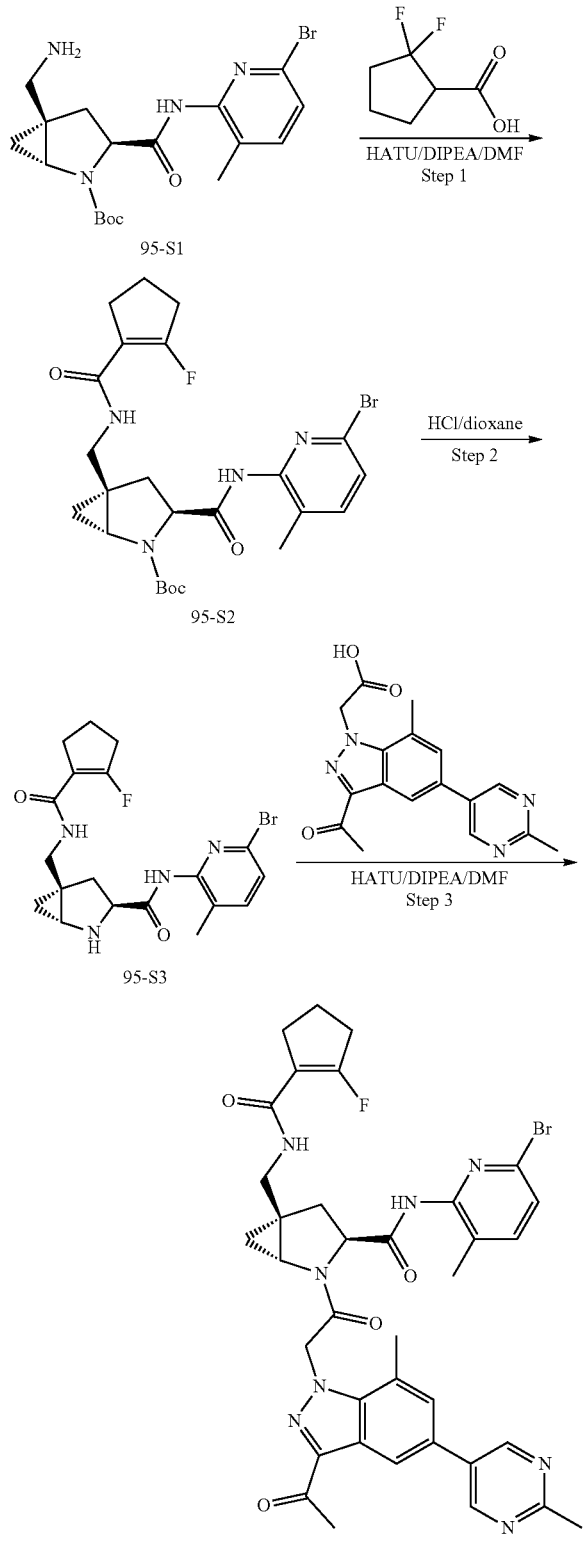

Step 1: (1R,3S,5R)-tert-Butyl 3-(6-bromo-3-methylpyridin-2-ylcarbamoyl)-5-((2-fluorocyclopent-1-enecarboxamido)methyl)-2-azabicyclo[3.1.0]hexane-2-carboxylate (95-S2)

To a mixture of 95-S1 (30 mg, 0.07 mmol), 2,2-difluorocyclopentanecarboxylic acid (11 mg, 0.07 mmol), and HATU (40 mg, 0.48 mmol) in DMF (2 mL) was added DIPEA (0.03 mL, 0.21 mmol). The reaction mixture was stirred at room temperature for 16 hours. The mixture was partitioned with EtOAc and water. The organic layer was washed with brine, dried over anhydrous $Na_2SO_4$, and concentrated under reduced pressure. The remaining residue was purified by column chromatography on silica gel (eluted with DCM/MeOH=80:1) to afford 95-S2 (15 mg, 40.0% yield) as a white solid. LC/MS (ESI) m/z: 537 (M+H)$^+$.

Step 2: (1R,3S,5R)—N-(6-Bromo-3-methylpyridin-2-yl)-5-((2-fluorocyclopent-1-enecarboxamido)methyl)-2-azabicyclo[3.1.0]hexane-3-carboxamide (95-S3)

To a solution of 95-S2 (15 mg, 0.03 mmol) in dioxane (0.5 mL) was added HCl/dioxane (2 M, 2 mL). The reaction mixture was stirred at room temperature for 1 hour. The reaction mixture was concentrated under reduced pressure to afford 95-S3 (15 mg, 100% yield) as a white solid, which was carried forward in the next synthetic step without purification. LC/MS (ESI) m/z: 437 (M+H)$^+$.

Step 3: (1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-((2-fluorocyclopent-1-enecarboxamido)methyl)-2-azabicyclo[3.1.0]hexane-3-carboxamide (95)

To a mixture of 95-S3 (15 mg, 0.03 mmol), 2-(3-acetyl-7-methyl-5-(2-methylpyrimidin-5-yl)-1H-indazol-1-yl)acetic acid (19 mg, 0.05 mmol), and HATU (27 mg, 0.07 mmol) in DMF (3 mL) was added DIPEA (0.02 mL, 0.11 mmol). The reaction mixture was stirred at room temperature for 16 hours. The mixture was partitioned with EtOAc and water. The organic layer was washed with brine, dried over anhydrous $Na_2SO_4$, and concentrated under reduced pressure. The remaining residue was purified by column chromatography on silica gel (eluted with DCM/MeOH=30:1) and further purified by preparative HPLC to afford 95 (4.0 mg, 15.0% yield) as a white solid. $^1$H NMR (400 MHz, $CD_3OD$) δ 8.91 (s, 2H), 8.33 (d, J=1.1 Hz, 1H), 7.46 (d, J=8.0 Hz, 2H), 7.29 (d, J=7.9 Hz, 1H), 5.88 (m, 1H), 5.72 (m, 1H), 4.54 (m, 1H), 3.68-3.53 (m, 2H), 2.67 (m, 6H), 2.60 (s, 3H), 2.53-2.34 (m, 6H), 2.03 (s, 3H), 1.80 (dt, J=15.4, 7.9 Hz, 2H), 1.24 (m, 2H), 0.98 (m, 1H). LC/MS (ESI) m/z: 743 (M+H)$^+$.

Scheme 36. Synthesis of (1R,3S,5R)-5-(Acetamidomethyl)-2-(2-(3-acetyl-7-methyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide (96)

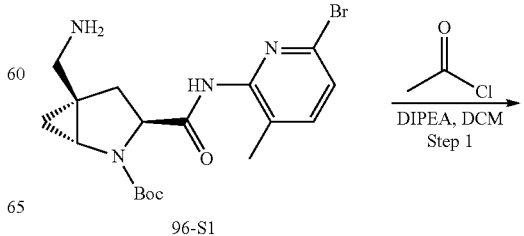

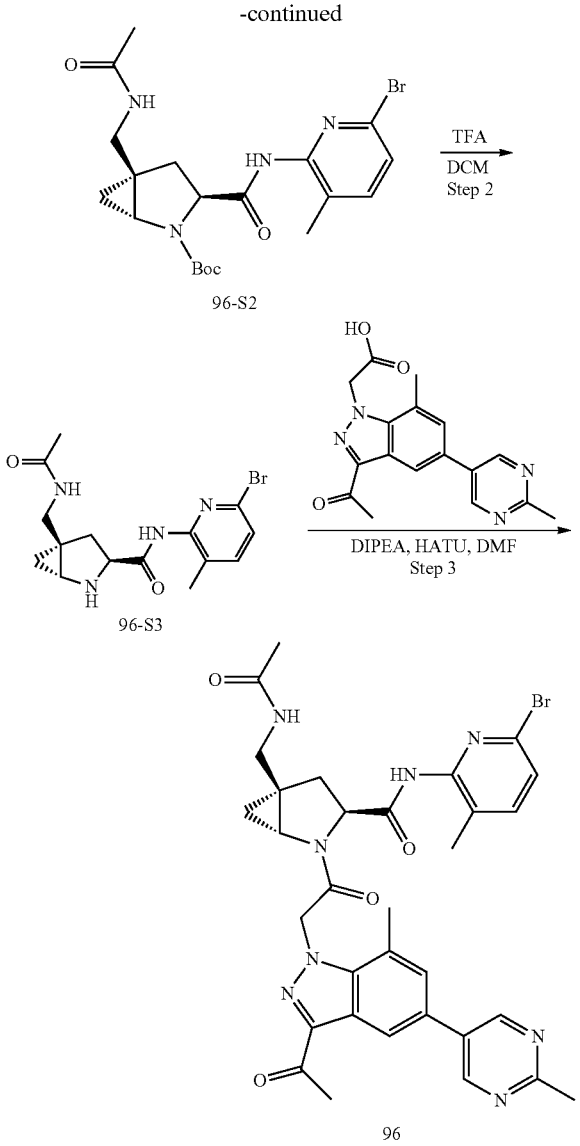

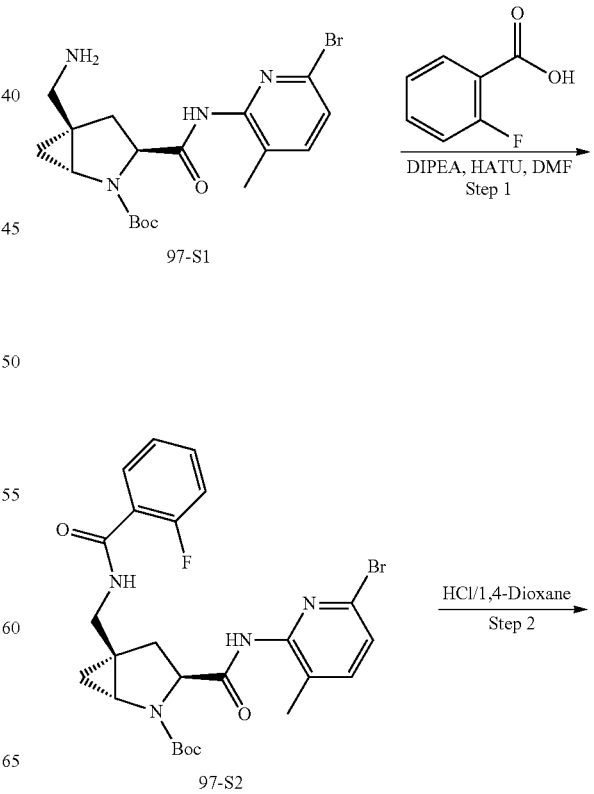

stirred at room temperature for 1.5 hours and then concentrated under reduced pressure to afford 96-S3 (24 mg, 100.0% yield) as light a yellow solid, which was carried forward in the next synthetic step without further purification. LC/MS (ESI) m/z: 367 (M+H)$^+$.

Step 3: (1R,3S,5R)-5-(Acetamidomethyl)-2-(2-(3-acetyl-7-methyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide (96)

To a solution of 96-S3 (24 mg, 0.066 mmol), 2-(3-acetyl-7-methyl-5-(2-methylpyrimidin-5-yl)-1H-indazol-1-yl)acetic acid (23 mg, 0.071 mmol), and HATU (50 mg, 0.13 mmol) in DMF (2 mL) was added DIPEA (25 mg, 0.20 mmol) at 0° C. The reaction mixture was stirred at room temperature overnight. The mixture was diluted with EtOAc, washed with 10% aqueous LiCl solution and brine, dried over Na$_2$SO$_4$, and concentrated to dryness. The remaining residue was purified by preparative HPLC to afford 96 (5.5 mg, 12.5% yield) as a white solid. $^1$H NMR (400 MHz, CD$_3$OD) δ 8.89 (d, J=3.3 Hz, 2H), 8.32 (s, 1H), 7.53-7.57 (m, 2H), 7.29 (d, J=8 Hz, 1H), 5.86 (d, J=17.6 Hz, 1H), 5.71 (d, J=17.6 Hz, 1H), 4.53 (m, 1H), 3.61 (m, 1H), 3.45 (d, J=14.2 Hz, 1H), 3.18-3.05 (m, 1H), 2.66 (s, 3H), 2.65 (s, 3H), 2.58 (s, 3H), 2.42 (m, 2H), 2.02 (s, 3H), 1.90 (s, 3H), 1.22 (m, 1H), 0.98 (m, 1H). LC/MS (ESI) m/z: 673 (M+H)$^+$.

Scheme 37. Synthesis of (1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-((2-fluorobenzamido)methyl)-2-azabicyclo[3.1.0]hexane-3-carboxamide (97)

Step 1: (1R,3S,5R)-tert-Butyl 5-(acetamidomethyl)-3-(6-bromo-3-methylpyridin-2-ylcarbamoyl)-2-azabicyclo[3.1.0]hexane-2-carboxylate (96-S2)

To a solution of 96-S1 (30 mg, 0.071 mmol) in DCM (2 mL) was added DIPEA (18 mg, 0.14 mmol) followed by acetyl chloride (7 mg, 0.089 mmol) at 0° C. The reaction mixture was stirred at room temperature for 1 hour. The mixture was diluted with DCM, washed with water and brine, dried over Na$_2$SO$_4$, and concentrated to dryness. The remaining residue was purified by column chromatography on silica gel (eluted with DCM/MeOH=30:1) to afford 96-S2 (31 mg, 93.9% yield) as a white solid. LC/MS (ESI) m/z: 467 (M+H)$^+$.

Step 2: (1R,3S,5R)-5-(Acetamidomethyl)-N-(6-bromo-3-methylpyridin-2-yl)-2-azabicyclo[3.1.0]hexane-3-carboxamide (96-S3)

To a solution of 96-S2 (31 mg, 0.067 mmol) in DCM (2.5 mL) was added TFA (1 mL). The reaction mixture was -continued

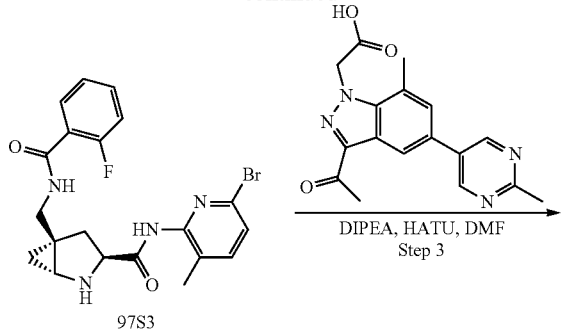

Step 3

Step 3: (1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-((2-fluorobenzamido)methyl)-2-azabicyclo[3.1.0]hexane-3-carboxamide (97)

To a solution of 97-S3 (25 mg, 0.056 mmol), 2-(3-acetyl-7-methyl-5-(2-methylpyrimidin-5-yl)-1H-indazol-1-yl)acetic acid (20 mg, 0.062 mmol), and HATU (32 mg, 0.084 mmol) in DMF (2 mL) was added DIPEA (15 mg, 0.12 mmol) at 0° C. The reaction mixture was stirred at room temperature overnight. The mixture was diluted with EtOAc, washed with 10% aqueous LiCl solution and brine, dried over $Na_2SO_4$, and concentrated to dryness. The remaining residue was purified by preparative HPLC to afford 97 (4.2 mg, 10.00 yield) as a white solid. $^1$H NMR (400 MHz, $CD_3OD$) δ 9.01 (s, 2H), 8.44 (s, 1H), 7.72 (td, J=7.5, 1.7 Hz, 1H), 7.52 (m, 3H), 7.38 (d, J=7.9 Hz, 1H), 7.27-7.15 (m, 2H), 6.00 (d, J=18 Hz, 1H), 5.84 (d, J=18 Hz, 1H), 4.64 (m, 1H), 3.85-3.75 (m, 2H), 3.58-3.49 (m, 1H), 2.78 (s, 3H), 2.76 (s, 3H), 2.70 (s, 3H), 2.67-2.54 (m, 2H), 2.09 (s, 3H), 1.42 (m, 1H), 1.13 (m, 1H). LC/MS (ESI) m/z: 753 $(M+H)^+$.

Scheme 38: Synthesis of (1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-(methylsulfonamidomethyl)-2-azabicyclo[3.1.0]hexane-3-carboxamide (101)

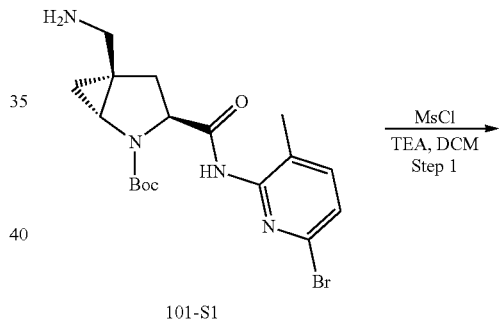

101-S1

MsCl
TEA, DCM
Step 1

Step 1: (1R,3S,5R)-tert-Butyl 3-(6-bromo-3-methylpyridin-2-ylcarbamoyl)-5-((2-fluorobenzamido)methyl)-2-azabicyclo[3.1.0]hexane-2-carboxylate (97-S2)

To a mixture of 97-S1 (30 mg, 0.071 mmol), 2-fluorobenzoic acid (12 mg, 0.086 mmol), and HATU (54 mg, 0.14 mmol) in DMF (2 mL) was added DIPEA (27 mg, 0.21 mmol) at 0° C. The reaction mixture was stirred at room temperature overnight. The mixture was diluted with EtOAc, washed with 10% aqueous LiCl solution and brine, dried over $Na_2SO_4$, and concentrated to dryness. The remaining residue was purified by column chromatography on silica gel (eluted with DCM/MeOH=20:1) to afford 97-S2 (31 mg, 80.3% yield) as a white solid. LC/MS (ESI) m/z: 547 $(M+H)^+$.

Step 2: (1R,3S,5R)—N-(6-Bromo-3-methylpyridin-2-yl)-5-((2-fluorobenzamido)methyl)-2-azabicyclo[3.1.0]hexane-3-carboxamide (97-S3)

To a solution of 97-S2 (31 mg, 0.057 mmol) in dioxane (2 mL) was added HCl/dioxane (2 mL, 2 M) at 0° C. The reaction mixture was stirred at room temperature for 2 hours. The mixture was concentrated to dryness to afford 97-S3 (25 mg, 100% yield) as a brown oil, which was carried forward in the next synthetic step without purification. LC/MS (ESI) m/z: 447 $(M+H)^+$.

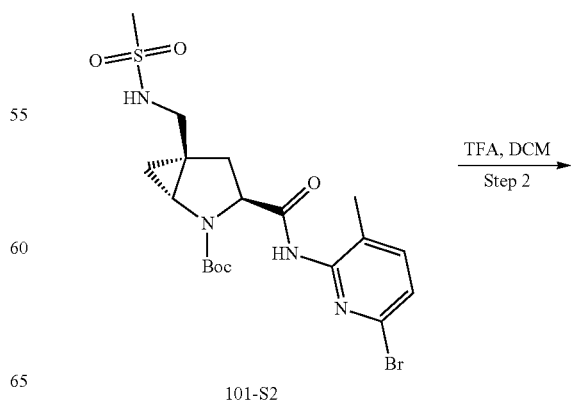

101-S2

TFA, DCM
Step 2

-continued

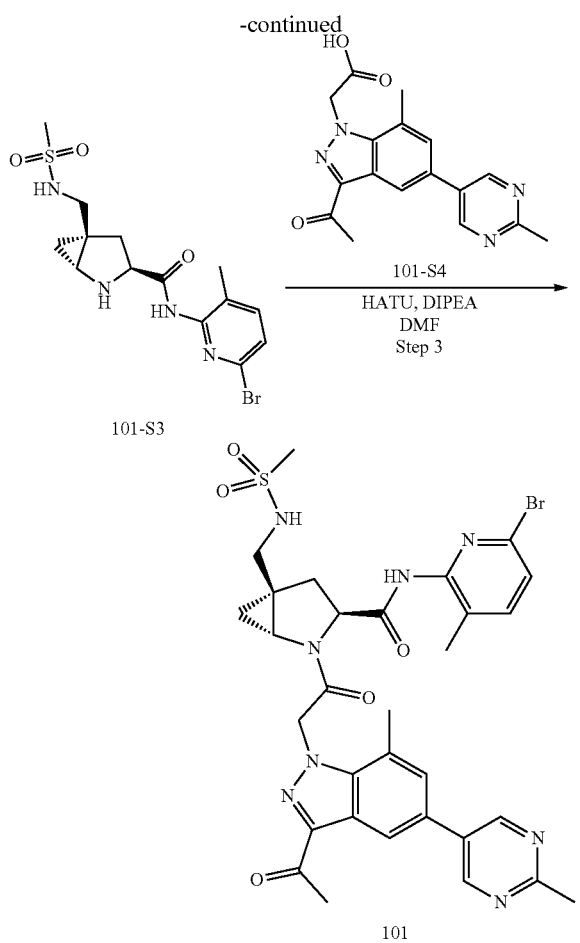

Step 1: (1R,3S,5R)-tert-Butyl 3-((6-bromo-3-methylpyridin-2-yl)carbamoyl)-5-(methylsulfonamidomethyl)-2-azabicyclo[3.1.0]hexane-2-carboxylate (101-S2)

To a solution of 101-S1 (40 mg, 0.09 mmol) in dry DCM (3 mL) was added Et$_3$N (0.03 mL, 0.18 mmol) followed by methanesulfonyl chloride (0.01 mL, 0.11 mmol) at 0° C. The reaction mixture was stirred at 0° C. for 1 hour. The mixture was then diluted with water (4 mL) and extracted with DCM (3 mL×2). The combined organic phases were washed with brine, dried over anhydrous Na$_2$SO$_4$, filtered, and concentrated. The crude product was purified by column chromatography on silica gel (eluted with DCM/MeOH=60:1) to afford 101-S2 (30 mg, 62.5% yield) as a light a yellow oil. LC/MS (ESI) m/z: 503 (M+H)$^+$.

Step 2: (1R,3S,5R)—N-(6-Bromo-3-methylpyridin-2-yl)-5-(methylsulfonamidomethyl)-2-azabicyclo[3.1.0]hexane-3-carboxamide (101-S3)

To a solution of 101-S2 (30 mg, 0.06 mmol) in DCM (0.5 mL) was added TFA (0.2 mL). The reaction mixture was stirred at room temperature for 1.5 hours and then concentrated under reduced pressure to afford 101-S3 (24 mg, 100.0% yield) as a yellow oil, which was carried forward in the next synthetic step without further purification. LC/MS (ESI) m/z: 403 (M+H)$^+$.

Step 3: (1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-(methylsulfonamidomethyl)-2-azabicyclo[3.1.0]hexane-3-carboxamide (101)

To a solution of 101-S3 (24 mg, 0.06 mmol), 2-(3-acetyl-7-methyl-5-(2-methylpyrimidin-5-yl)-1H-indazol-1-yl)acetic acid (101-S4, 23 mg, 0.07 mmol), and HATU (45 mg, 0.12 mmol) in DMF (2 mL) was added DIPEA (0.04 mL, 0.24 mmol). The reaction mixture was stirred at room temperature for 2 hours. The mixture was partitioned with EtOAc and water. The organic layer was washed with brine, dried over anhydrous Na$_2$SO$_4$, and concentrated under reduced pressure. The remaining residue was purified by preparative HPLC (eluted with MeCN/water) to afford 101 (5.3 mg, 12.6% yield) as a white solid. $^1$H NMR (400 MHz, CD$_3$OD) δ 8.99 (s, 2H), 8.41 (s, 1H), 7.52-7.56 (m, 2H), 7.38 (d, J=8.0 Hz, 1H), 5.94-5.99 (m, 1H), 5.78-5.83 (m, 1H), 4.63-4.65 (m, 1H), 3.72-3.75 (m, 1H), 3.35-3.43 (m, 2H), 3.01 (s, 3H), 2.76 (s, 6H), 2.69 (s, 3H), 2.53-2.59 (m, 2H), 2.15 (s, 3H), 1.36-1.39 (m, 1H), 1.11-1.13 (m, 1H). LC/MS (ESI) m/z: 709 (M+H)$^+$.

Scheme 39: Synthesis of (1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-((3,3,3-trifluoropropanamido)methyl)-2-azabicyclo[3.1.0]hexane-3-carboxamide (102)

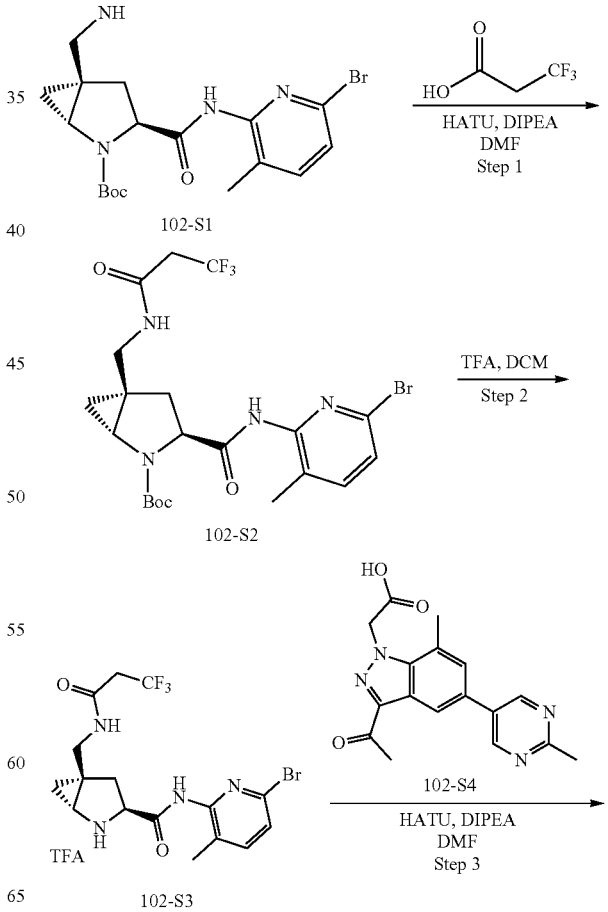

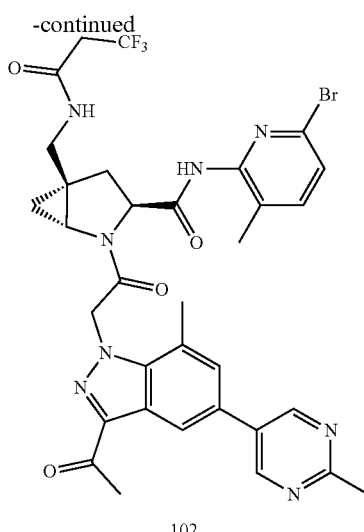

102

Step 1: (MS)-tert-Butyl 3-(6-bromopyridin-2-ylcarbamoyl)-5-(((S)-2-(methoxycarbonylamino)-3-methylbutanamido)methyl)-2-azabicyclo[3.1.0]hexane-2-carboxylate (102-S2)

To a mixture of 102-S1 (70 mg, 0.16 mmol), 3,3,3-trifluoropropanoic acid (25 mg, 0.19 mmol), and HATU (122 mg, 0.32 mmol) in DMF (2 mL) was added DIPEA (0.05 mL, 0.32 mmol). The reaction mixture was stirred at room temperature for 16 hours. The mixture was partitioned with EtOAc and water. The organic layer was washed with brine, dried over anhydrous $Na_2SO_4$, and concentrated under reduced pressure. The remaining residue product was purified by column chromatography on silica gel (eluted with DCM/MeOH=80:1) to afford 102-S2 (75 mg, 85.2% yield) as a white solid. LC/MS (ESI) m/z: 535 (M+H)$^+$.

Step 2: (1R,3S,5R)—N-(6-Bromo-3-methylpyridin-2-yl)-5-((3,3,3-trifluoropropanamido)methyl)-2-azabicyclo[3.1.0]hexane-3-carboxamide (102-S3)

To a solution of 102-S2 (75 mg, 0.14 mmol) in DCM (2.5 mL) was added TFA (1 mL). The reaction mixture was stirred at room temperature for 1.5 hours and then concentrated under reduced pressure to afford 102-S3 (61 mg, 100.0% yield) as a yellow oil, which was carried forward in the next synthetic step without further purification. LC/MS (ESI) m/z: 435 (M+H)$^+$.

Step 3: (1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-((3,3,3-trifluoropropanamido)methyl)-2-azabicyclo[3.1.0]hexane-3-carboxamide (102)

To a solution of 102-S3 (30 mg, 0.07 mmol), 2-(3-acetyl-7-methyl-5-(2-methylpyrimidin-5-yl)-1H-indazol-1-yl)acetic acid (102-S4, 27 mg, 0.08 mmol), and HATU (53 mg, 0.14 mmol) in DMF (2 mL) was added DIPEA (0.06 mL, 0.35 mmol). The reaction mixture was stirred at room temperature for 2 hours. The mixture was partitioned with EtOAc and water. The organic layer was washed with brine, dried over anhydrous $Na_2SO_4$, and concentrated under reduced pressure. The remaining residue was purified by preparative HPLC (eluted with MeCN/water) to afford 102 (4.5 mg, 12.8% yield) as a white solid. $^1$H NMR (400 MHz, $CD_3OD$) δ 9.01 (s, 2H), 8.36 (s, 1H), 7.45-7.47 (m, 2H), 7.29 (d, J=8.0 Hz, 1H), 5.85-5.89 (m, 1H), 5.69-5.73 (m, 1H), 4.75-4.79 (m, 1H), 3.62-3.64 (m, 1H), 3.24-3.46 (m, 4H), 2.69 (s, 3H), 2.63 (s, 3H), 2.58 (s, 3H), 2.39-2.47 (m, 2H), 1.23-1.25 (m, 1H), 1.00-1.02 (m, 1H). LC/MS (ESI) m/z: 741 (M+H)$^+$ Scheme 40. Synthesis of (1R,3S,5R)-2-(2-(3-Acetyl-5-(2-((dimethylamino)methyl)pyrimidin-5-yl)-1H-indazol-1-yl)acetyl)-N-(6-bromo-3-methylpyridin-2-yl)-5-methyl-2-azabicyclo[3.1.0]hexane-3-carboxamide (103)

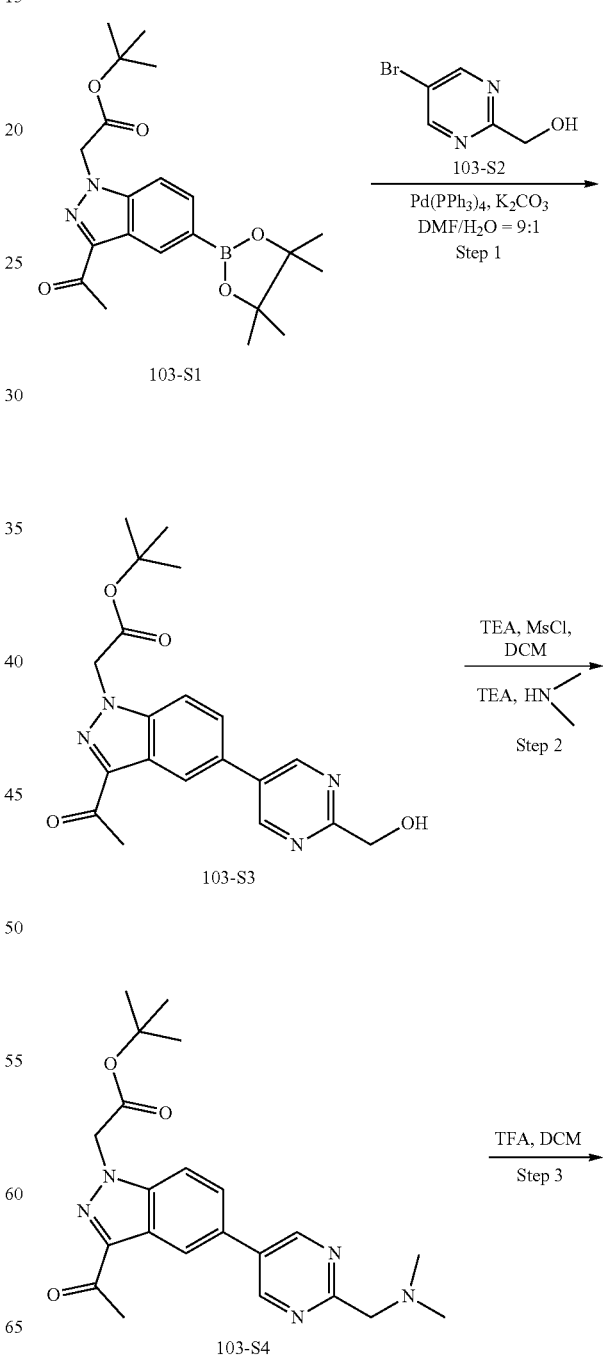

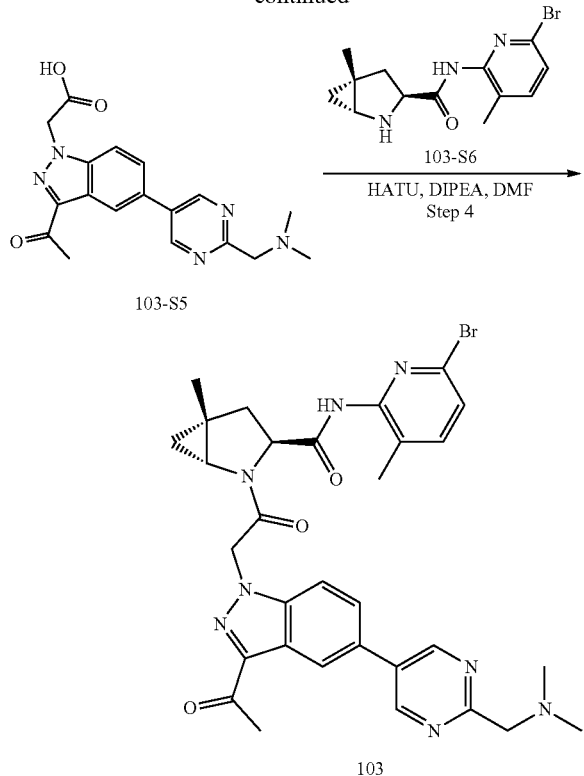

The reaction mixture was stirred at room temperature for 3 hours and concentrated to dryness. The remaining material was used directly in the next synthetic step.

Step 4: (1R,3S,5R)-2-(2-(3-Acetyl-5-(2-((dimethylamino)methyl)pyrimidin-5-yl)-1H-indazol-1-yl)acetyl)-N-(6-bromo-3-methylpyridin-2-yl)-5-methyl-2-azabicyclo[3.1.0]hexane-3-carboxamide (103)

To a solution of compound 103-S5 (1 equiv) in DMF (10 vol) at 0° C. under an atmosphere of argon were added (1R,3S,5R)—N-(6-bromo-3-methylpyridin-2-yl)-5-methyl-2-azabicyclo[3.1.0]hexane-3-carboxamide (1 equiv), HATU (2.1 equiv), and DIPEA (5 equiv). The reaction mixture was stirred at room temperature for 3 hours and then quenched with water (30 vol). The resulting mixture was extracted with DCM. The organic layer was washed with brine, dried over anhydrous Na$_2$SO$_4$, filtered, and concentrated to dryness. The remaining residue was purified by column chromatography on silica gel (eluted with DCM/MeOH) to afford compound 103. $^1$H NMR (400 MHz, DMSO-d$_6$) δ 1.05-1.13 (m, 2H), 1.39 (s, 3H), 2.07-2.16 (m, 4H), 2.54-2.60 (m, 1H), 2.73 (s, 3H), 3.01 (s, 6H), 3.64-3.74 (m, 1H), 4.47 (dd, J=5.2, 9.3 Hz, 1H), 4.78 (s, 2H), 5.66 (d, J=17.2 Hz, 1H), 6.02 (d, J=17.3 Hz, 1H), 7.52 (d, J=7.9 Hz, 1H), 7.69 (d, J=7.9 Hz, 1H), 7.99 (q, J=8.8 Hz, 2H), 8.60 (s, 1H), 9.36 (s, 2H), 10.36 (s, 1H).

Scheme 41. Synthesis of (1R,3S,5R)-2-(2-(3-Acetyl-5-(2-methylpyrimidin-5-yl)-1H-pyrazolo[3,4-c]pyridin-1-yl)acetyl)-N-(6-bromo-5-fluoro-3-methylpyridin-2-yl)-5-methyl-2-azabicyclo[3.1.0]hexane-3-carboxamide (104)

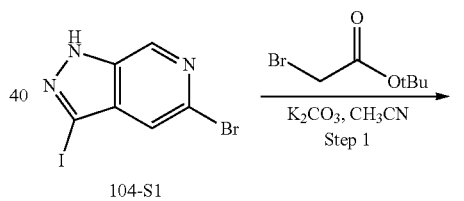

Step 1: tert-Butyl 2-(3-acetyl-5-(2-(hydroxymethyl)pyrimidin-5-yl)-1H-indazol-1-yl)acetate (103-S3)

To a solution of (5-bromopyrimidin-2-yl)methanol (103-S2, 1 equiv) in DMF/H$_2$O (9:1, 10 vol) was added compound 103-S1 (1 equiv), K$_2$CO$_3$ (2 equiv) and tetrakis(triphenylphosphine)palladium (0.1 equiv). The reaction mixture was stirred at 90° C. for 5 hours and concentrated under reduced pressure. The remaining residue was purified by column chromatography on silica gel to afford compound 103-S3.

Step 2: tert-Butyl 2-(3-acetyl-5-(2-((dimethylamino)methyl)pyrimidin-5-yl)-1H-indazol-1-yl)acetate (103-S4)

To a mixture of compound 103-S3 (1 equiv) in dry DCM (10 vol) was added Et$_3$N (1 equiv) followed by the dropwise addition of MsCl (1.5 equiv) at 0° C. and the reaction mixture was stirred for 2 hours at same temperature. Dimethylamine hydrochloride (1.1 equiv) at 0° C. was added and the reaction mixture was stirred at room temperature for 3 hours. The reaction mixture was quenched with saturated aqueous NaHCO$_3$ solution and extracted with DCM. The combined organic layers were separated, dried, and concentrated to afford crude product, which was purified by silica gel column (eluted with DCM/EtOAc) to afford compound 103-S4.

Step 3: 2-(3-Acetyl-5-(2-((dimethylamino)methyl)pyrimidin-5-yl)-1H-indazol-1-yl)acetic Acid (103-S5)

To a solution of compound 103-S4 (1 equiv) under an atmosphere of argon was added 4N dioxane HCl (10 vol).

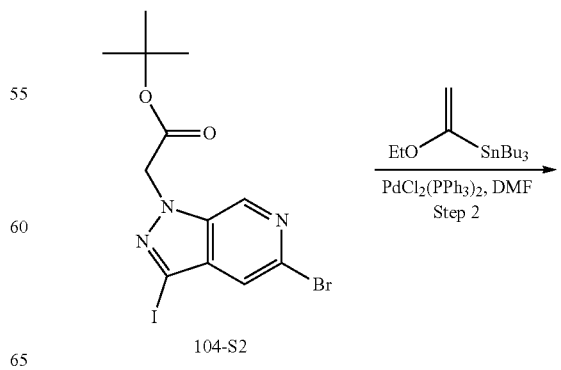

-continued

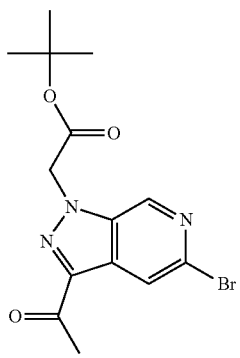

104-S3

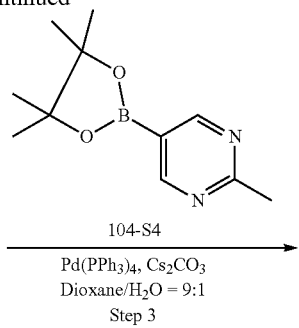

104-S4

Pd(PPh₃)₄, Cs₂CO₃
Dioxane/H₂O = 9:1
Step 3

TFA/DCM
3-4 h, rt
Step 4

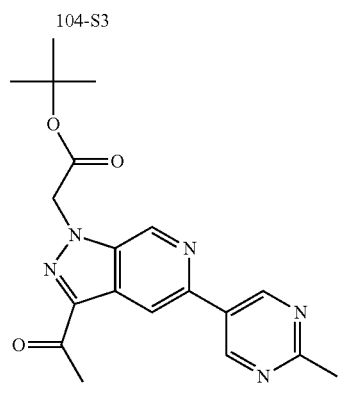

104-S5

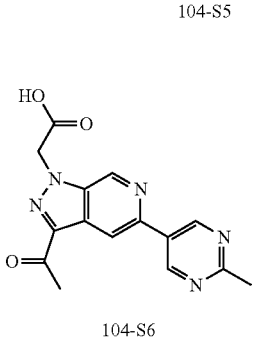

104-S6

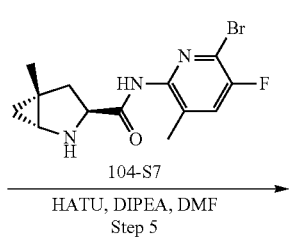

104-S7

HATU, DIPEA, DMF
Step 5

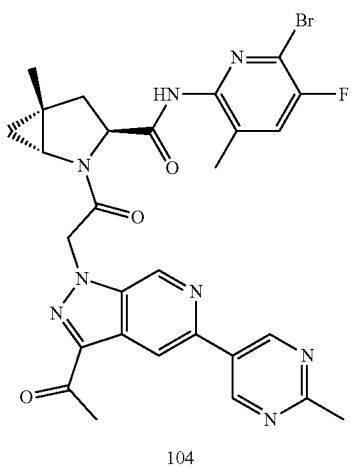

104

Step 1: tert-Butyl 2-(5-bromo-3-iodo-1H-pyrazolo[3,4-c]pyridin-1-yl)acetate (104-S2)

To a solution of 5-bromo-3-iodo-1H-pyrazolo[3,4-c]pyridine (1 equiv) in CH₃CN (10 vol) was added tert-butyl 2-bromoacetate (1.1 equiv) and potassium carbonate (1.1 equiv). The mixture was refluxed overnight under an atmosphere of argon. After cooling the reaction mixture to room temperature, the mixture was filtered through Celite and washed with CH₃CN. The filtrate was concentrated under reduced pressure and the remaining residue was purified by column chromatography on silica gel (eluted with DCM/MeOH) to afford compound 104-S2.

Step 2: tert-Butyl 2-(3-acetyl-5-bromo-1H-pyrazolo[3,4-c]pyridin-1-yl)acetate (104-S3)

To a solution of tert-butyl 2-(5-bromo-3-iodo-1H-pyrazolo[3,4-c]pyridin-1-yl)acetate (1 equiv) in dry DMF (10 vol) were added tributyl (1-ethoxyvinyl) stannane (1.5 equiv) and PdCl₂(PPh₃)₂ (0.05 equiv) and the resulting mixture was stirred at 80° C. under argon atmosphere overnight and concentrated to dryness. The remaining residue was diluted with DCM and washed with 2N aqueous HCl. The organic layer was separated, dried over anhydrous Na₂SO₄, and concentrated to dryness. The obtained crude product was purified by column chromatography on silica gel (eluted with DCM/MeOH) to afford compound 104-S3.

Step 3: tert-Butyl 2-(3-acetyl-5-(2-methylpyrimidin-5-yl)-1H-pyrazolo[3,4-c]pyridin-1-yl)acetate (104-S5)

To a solution of 2-methyl-5-(4,4,5,5-tetramethyl-1,3,2-dioxaborolan-2-yl)pyrimidine (104-S4, 1 equiv) in dioxane/H₂O (9:1, 10 vol) was added compound 104-S3 (1 equiv), Cs₂CO₃ (2 equiv), and tetrakis(triphenylphosphine)palladium (0.1 equiv). The reaction mixture was stirred at 90° C. for 5 hours and concentrated to dryness. The remaining residue was purified by column chromatography on silica gel (eluted with DCM/MeOH) to afford compound 104-S5.

Step 4: 2-(3-Acetyl-5-(2-methylpyrimidin-5-yl)-1H-pyrazolo[3,4-c]pyridin-1-yl)acetic Acid (104-S6)

To a solution of compound 104-S5 (1 equiv) in DCM (10 vol) at 0° C. under an atmosphere of argon was added TFA (5 vol). The reaction mixture was stirred at room temperature for 3 hours and concentrated to dryness. The remaining material was carried forward without additional purification and used directly in the next synthetic step.

Step 5: (1R,3S,5R)-2-(2-(3-Acetyl-5-(2-methylpyrimidin-5-yl)-1H-pyrazolo[3,4-c]pyridin-1-yl)acetyl)-N-(6-bromo-5-fluoro-3-methylpyridin-2-yl)-5-methyl-2-azabicyclo[3.1.0]hexane-3-carboxamide (104)

To a solution of compound 104-S6 (1 equiv) in DMF (10 vol) at 0° C. under an atmosphere of argon were added (1R,3S,5R)-N-(6-bromo-5-fluoro-3-methylpyridin-2-yl)-5-methyl-2-azabicyclo[3.1.0]hexane-3-carboxamide (S7, 1 equiv), HATU (2.1 equiv), and DIPEA (5 equiv). The reaction mixture was stirred at room temperature for 3 hours and then quenched with water (30 vol). The resulting mixture was extracted with DCM. The organic layer was washed with brine, dried over anhydrous Na₂SO₄, filtered, and then concentrated to dryness. The remaining residue was purified by column chromatography on silica gel (eluted with DCM/MeOH) to afford compound 104. $^1$H NMR (400 MHz, DMSO-$d_6$) δ 0.90-0.97 (m, 1H), 1.00-1.05 (m, 1H), 1.26 (s, 3H), 2.00 (s, 4H), 2.45-2.52 (m, 1H), 2.62 (d, J=4.3 Hz, 6H), 3.47-3.56 (m, 1H), 4.27-4.39 (m, 1H), 5.66 (d, J=17.2 Hz, 1H), 5.97 (d, J=17.3 Hz, 1H), 7.75 (d, J=8.4 Hz, 1H), 8.51-8.57 (m, 1H), 9.23 (d, J=1.4 Hz, 1H), 9.27 (s, 2H), 10.20 (s, 1H).

Scheme 42. Synthesis of (1R,3S,5R)-2-(2-(3-Acetyl-5-(2-((1,1-dioxidothietan-3-yl)oxy)pyrimidin-5-yl)-1H-indazol-1-yl)acetyl)-N-(6-bromo-3-methylpyridin-2-yl)-5-methyl-2-azabicyclo[3.1.0]hexane-3-carboxamide (107)

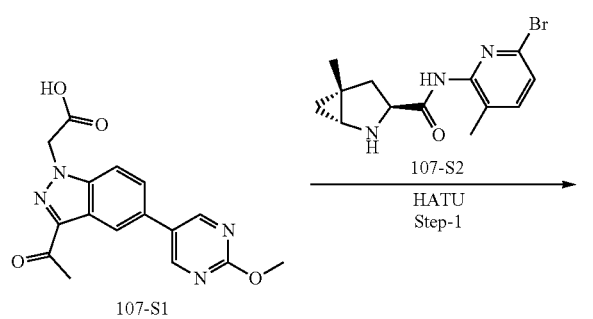

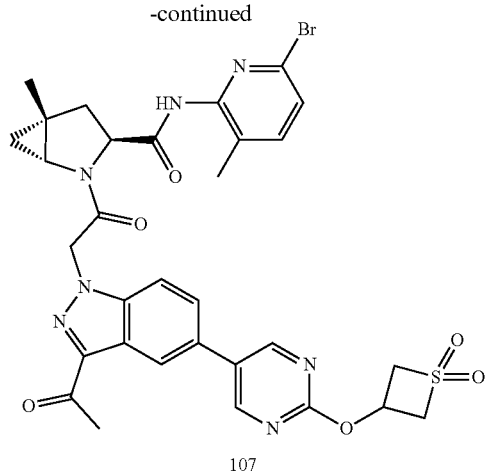

Step 1: (1R,3S,5R)-2-(2-(3-Acetyl-5-(2-methoxypyrimidin-5-yl)-1H-indazol-1-yl)acetyl)-N-(6-bromo-3-methylpyridin-2-yl)-5-methyl-2-azabicyclo[3.1.0] hexane-3-carboxamide (107-S3)

To a solution of 2-(3-acetyl-5-(2-methoxypyrimidin-5-yl)-1H-indazol-1-yl)acetic acid (107-S1, 1 equiv) in DMF (10 vol) at 0° C. under nitrogen atmosphere was added (1R,3S,5R)—N-(6-bromo-3-methylpyridin-2-yl)-5-methyl-2-azabicyclo[3.1.0]hexane-3-carboxamide (107-S2, 1.2 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to afford compound 107-S3.

Step 2: (1R,3S,5R)-2-(2-(3-Acetyl-5-(2-hydroxypyrimidin-5-yl)-1H-indazol-1-yl)acetyl)-N-(6-bromo-3-methylpyridin-2-yl)-5-methyl-2-azabicyclo[3.1.0] hexane-3-carboxamide (107-S4)

To a solution of compound 107-S3 (1 equiv) in ACN (10 vol) at 0° C. under nitrogen atmosphere was added TMSCl (2.5 equiv) and NaI (2 equiv). The reaction mixture was stirred at room temperature for 16 hours. After completion of the reaction, the reaction mixture was concentrated and quenched with water. The resulting solid was filtered and dried to afford compound 107-S4.

Step 3: (1R,3S,5R)-2-(2-(3-Acetyl-5-(2-((1,1-dioxidothietan-3-yl)oxy)pyrimidin-5-yl)-1H-indazol-1-yl) acetyl)-N-(6-bromo-3-methylpyridin-2-yl)-5-methyl-2-azabicyclo[3.1.0]hexane-3-carboxamide (107)

To a solution of compound 107-S4 (1 equiv) in ACN (10 vol) was added cesium carbonate (3 equiv) and 3-bromothietane 1,1-dioxide (107-S5, 2 equiv). The reaction mixture was stirred at room temperature for 16 hours. After completion of the reaction, the reaction mixture was concentrated and quenched with water. The resulting solid was filtered, dried and purified by preparative purification to afford compound 107. $^1$H NMR (400 MHz, DMSO-$d_6$) δ: 10.29 (s, 1H), 9.03 (s, 1H), 8.60 (s, 1H), 8.37 (s, 1H), 7.82-7.14 (m, 2H), 7.63 (d, J=8.0 Hz, 1H), 7.46 (d, J=8.0 Hz, 1H), 5.91 (d, J=17.6 Hz, 1H), 5.56 (d, J=17.6 Hz, 1H), 5.29-5.27 (m, 1H), 5.02-4.97 (m, 2H), 4.62-4.56 (m, 2H), 4.42-4.38 (m, 1H), 2.67 (s, 3H), 2.05 (s, 3H), 1.32 (s, 3H), 1.04-1.00 (m, 2H), 0.99-0.85 (m, 2H).

Scheme 43: Synthesis of (1R,3S,5R)-2-(2-(3-Acetyl-5-(2-methylpyrimidin-5-yl)-1H-indazol-1-yl)acetyl)-N-(6-bromo-3-cyclopropylpyridin-2-yl)-5-((dimethylamino)methyl)-2-azabicyclo[3.1.0]hexane-3-carboxamide (112)

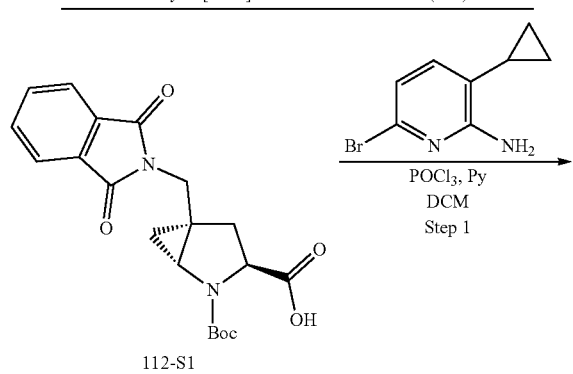

Step 1: (1R,3S,5R)-tert-Butyl 3-((6-bromo-3-cyclopropylpyridin-2-yl)carbamoyl)-5-((1,3-dioxoisoindolin-2-yl)methyl)-2-azabicyclo[3.1.0]hexane-2-carboxylate (112-S2)

To a mixture of 112-S1 (100 mg, 0.26 mmol) and 6-bromo-3-cyclopropylpyridin-2-amine (55.1 mg, 0.26 mmol) in dry DCM (3 mL) was added pyridine (0.1 mL, 1.30 mmol) followed by POCl₃ (39.8 mg, 0.26 mmol) at 0° C. The reaction mixture was stirred at room temperature for 30 minutes. The mixture was poured into ice water and extracted with DCM twice. The organic layers were washed with brine, dried over Na₂SO₄, and concentrated under reduced pressure. The remaining residue was purified by silica gel chromatography (PE/EtOAc=6:1 to 2:1) to afford 112-S2 (127 mg, 84.2% yield) as a white solid. LC/MS (ESI) m/z: 581 (M+H)⁺.

Step 2: (1R,3S,5R)-tert-Butyl 5-(aminomethyl)-3-((6-bromo-3-cyclopropylpyridin-2-yl)carbamoyl)-2-azabicyclo[3.1.0]hexane-2-carboxylate (112-S3)

To a solution of 112-S2 (127 mg, 0.22 mmol) in EtOH (3 mL) was added hydrazine hydrate (21.9 mg, 0.44 mmol). The reaction mixture was stirred at 75° C. for 2 hours and then cooled to room temperature. The mixture was filtered and the filtrate was concentrated under reduced pressure. The remaining residue was purified by column chromatography on silica gel (eluted with DCM/MeOH=5:1) to afford 112-S3 (79 mg, 79.8% yield) as a white solid. LC/MS (ESI) m/z: 451 (M+H)⁺.

Step 3: (1R,3S,5R)-tert-Butyl 3-((6-bromo-3-cyclopropylpyridin-2-yl)carbamoyl)-5-((dimethylamino)methyl)-2-azabicyclo[3.1.0]hexane-2-carboxylate (112-S4)

To a solution of 112-S3 (79 mg, 0.18 mmol) in MeOH (3 mL) was added aqueous HCHO solution (42.6 mg, 0.53 mmol, ~37% wt) and NaBH$_3$CN (22 mg, 0.35 mmol) at 0° C. The reaction mixture was stirred at room temperature for 1 hour. The mixture was then diluted with water (20 mL) and extracted with DCM (5 mL×2). The combined organic phases were washed with brine, dried over anhydrous Na$_2$SO$_4$, filtered, and concentrated. The remaining crude product was purified by column chromatography on silica gel (eluted with DCM/MeOH=10:1) to afford 112-S4 (55 mg, 63.9% yield) as a light oil. LC/MS (ESI) m/z: 479 (M+H)$^+$.

Step 4: (1R,3S,5R)—N-(6-Bromo-3-cyclopropylpyridin-2-yl)-5-((dimethylamino)methyl)-2-azabicyclo[3.1.0]hexane-3-carboxamide (112-S5)

To a solution of 112-S4 (55 mg, 0.12 mmol) in DCM (2 mL) was added TFA (1 mL). The reaction mixture was stirred at room temperature for 1.5 hours and then concentrated under reduced pressure to afford 112-S5 (43 mg) as a yellow solid, which was carried forward in the next synthetic step without further purification. LC/MS (ESI) m/z: 379 (M+H)$^+$.

Step 5: (1R,3S,5R)-2-(2-(3-Acetyl-5-(2-methylpyrimidin-5-yl)-1H-indazol-1-yl)acetyl)-N-(6-bromo-3-cyclopropylpyridin-2-yl)-5-((dimethylamino)methyl)-2-azabicyclo[3.1.0]hexane-3-carboxamide (112)

To a mixture of 112-S5 (43 mg, 0.113 mmol), 2-(3-acetyl-5-(2-methylpyrimidin-5-yl)-1H-indazol-1-yl)acetic acid (112-S6, 36.6 mg, 0.118 mmol), and HATU (64.6 mg, 0.17 mmol) in DMF (2 mL) was added DIPEA (0.06 mL, 0.339 mmol). The reaction mixture was stirred at room temperature for 16 hours. The mixture was partitioned with EtOAc and water. The organic layer was washed with brine, dried over anhydrous Na$_2$SO$_4$, and concentrated under reduced pressure. The crude product was purified by preparative HPLC to afford 112 (6.5 mg, 8.57% yield) as a white solid. $^1$H NMR (400 MHz, CD$_3$OD) δ 9.02 (s, 2H), 8.56 (s, 1H), 7.80 (d, J=1.2 Hz, 2H), 7.38 (d, J=8.1 Hz, 1H), 7.30 (d, J=8.1 Hz, 1H), 5.82 (d, J=17.2 Hz, 1H), 5.67 (d, J=17.1 Hz, 1H), 4.71 (t, J=7.0 Hz, 1H), 3.68-3.66 (m, 1H), 2.95-2.90 (m, 1H), 2.77 (s, 3H), 2.71 (s, 3H), 2.66-2.60 (m, 2H), 2.40 (s, 6H), 2.35-2.30 (m, 1H), 1.87-1.84 (m, 1H), 1.28-1.25 (m, 1H), 1.22-1.20 (m, 1H), 0.87-0.84 (m, 2H), 0.60-0.568 (m, 2H). LC/MS (ESI) m/z: 671 (M+H)$^+$.

Scheme 44. Synthesis of (1R,3S,5R)-2-(2-(3-Acetyl-7-methyl-5-(2-methylpyrimidin-5-yl)-1H-indazol-1-yl)acetyl)-N-(6-bromo-4-fluoropyridin-2-yl)-5-methyl-2-azabicyclo[3.1.0]hexane-3-carboxamide (116)

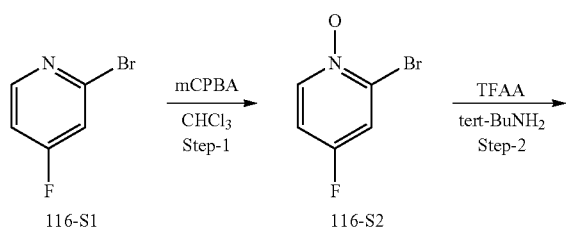

Step 1: 2-Bromo-4-fluoro-1-oxidanylpyridine (116-S2)

To a stirred solution of 2-bromo-4-fluoropyridine (116-S1, 2 g, 1 equiv) in CHCl$_3$ (130 mL) was added 3-chlorobenzoperoxoic acid (5 g, 2 equiv). The reaction mixture was heated to 50° C. The reaction was cooled and neutralized with saturated aqueous NaHCO$_3$ solution (100 mL).

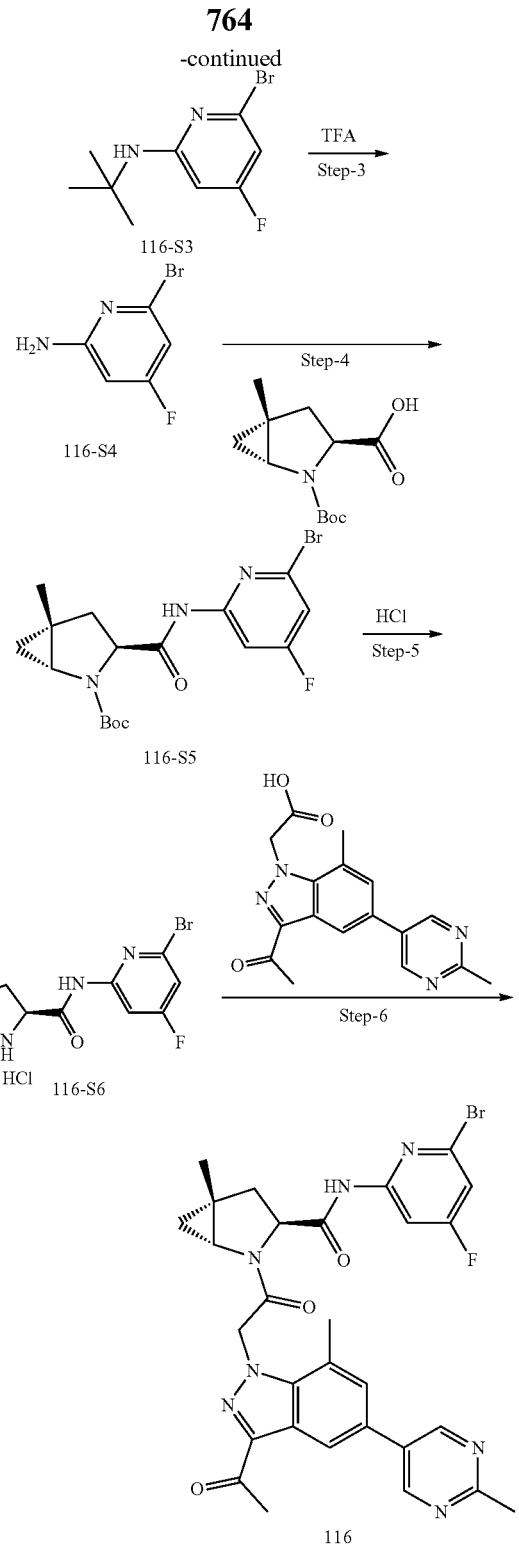

The organic layer was washed with saturated aqueous NaHCO$_3$ (50 mL×2) and the combined organic layers were washed with brine, dried over Na$_2$SO$_4$, and concentrated to dryness. The residue was purified by column chromatography on silica gel (eluted by 5% CH$_3$OH in DCM, gradient) to afford 116-S2 (622 mg, 31%).

Step 2: 6-Bromo-N-(tert-butyl)-4-fluoropyridin-2-amine (116-S3)

To a stirred solution of 116-S2 (622 mg, 1 equiv), 2-methylpropan-2-amine (1.7 mL, 5 equiv) in DCM (100 mL) was added trifluoroacidic anhydride solution (1.1 mL, 1.1 equiv) in DCM (10 mL) dropwise at 0-5° C. under an atmosphere of argon. The reaction mixture was stirred at 0-5° C. for 1 hour before TFA solution (1 mL, 1 equiv) in DCM (10 mL) was added followed by 2-methylpropan-2-amine (0.4 mL, 1.1 equiv). The reaction mixture was neutralized with aqueous saturated NaHCO$_3$ solution (20 mL) and the organic layer was washed with brine, dried over Na$_2$SO$_4$, and concentrated to dryness. The residue was purified by column chromatography on silica gel (eluted by 30% EtOAc in hexanes) to afford 116-S3 (81 mg, 10%).

Step 3: 6-Bromo-4-fluoropyridin-2-amine (116-S4)

TFA (6 mL) was added to solid 116-S3 and the reaction mixture was heated at 70° C. until completion. The reaction mixture was concentrated to dryness and the residue was dissolved in DCM (15 mL) and washed with aqueous saturated NaHCO$_3$ solution (10 mL). The organic layer was washed with brine, dried over Na$_2$SO$_4$ and concentrated to dryness to afford 116-S4 (63 mg).

Step 4: tert-Butyl (1R,3S,5R)-3-((6-bromo-4-fluoropyridin-2-yl)carbamoyl)-5-methyl-2-azabicyclo[3.1.0]hexane-2-carboxylate (116-S5)

POCl$_3$ (0.04 mL, 2 equiv) was added dropwise at 0-5° C. under an atmosphere of argon to a stirred solution of (1R,3S,5R)-2-(tert-butoxycarbonyl)-5-methyl-2-azabicyclo[3.1.0]hexane-3-carboxylic acid (79 mg, 1 equiv) and 116-S4 (63 mg, 1 equiv) in DCM (15 mL) and pyridine (0.13 mL, 5 equiv). The reaction mixture was stirred at room temperature for 2 hours before the reaction was diluted with DCM (10 mL) and neutralized with aqueous saturated NaHCO$_3$ solution (10 mL). The aqueous layer was extracted with DCM (1×10 mL) and the combined organic layers were washed with brine (10 mL), dried over Na$_2$SO$_4$, and concentrated to dryness. The residue was purified by column chromatography on silica gel (eluted by 5% MeOH in DCM gradient) to afford 116-S5 (97 mg, 71%).

Step 5: (1R,3S,5R)—N-(6-Bromo-4-fluoropyridin-2-yl)-5-methyl-2-azabicyclo[3.1.0]hexane-3-carboxamide Hydrochloride (116-S6)

To a solution of 116-S5 (97 mg) was added 4N HCl in dioxane (10 mL) and the resulting solution was stirred at room temperature for 6 hours. The reaction mixture was concentrated to dryness to afford 116-S6 (75 mg).

Step 6: (1R,3S,5R)-2-(2-(3-Acetyl-7-methyl-5-(2-methylpyrimidin-5-yl)-1H-indazol-1-yl)acetyl)-N-(6-bromo-4-fluoropyridin-2-yl)-5-methyl-2-azabicyclo[3.1.0]hexane-3-carboxamide (116)

HATU (109 mg, 1.2 equiv) was added at 0° C. under an atmosphere of argon to a solution of 116-S6 (75 mg, 1 equiv), 2-(3-acetyl-7-methyl-5-(2-methylpyrimidin-5-yl)-1H-indazol-1-yl)acetic acid (78 mg, 1.1 equiv), and DIPEA (0.21 mL, 5 equiv) in DMF (8 mL). The reaction mixture was stirred at room temperature for 3 hours before it was diluted with EtOAc (35 mL) and water (15 mL). The aqueous layer was extracted with EtOAc (15 mL) and the combined organic layers were washed with brine, dried over anhydrous Na$_2$SO$_4$, filtered and concentrated. The residue was purified by column chromatography on silica gel (eluted by DCM/MeOH=10:1) to afford 116 (87 mg, 53%). $^1$H NMR (400 MHz, DMSO-d$_6$) δ 11.11 (s, 1H), 9.02 (s, 2H), 8.31 (s, 1H), 7.86 (d, 1H, J=10.6 Hz), 7.63 (s, 1H), 7.43 (d, 1H, J=7.6 Hz), 6.08 (d, 1H, J=17.6 Hz), 5.67 (d, 1H, J=17.6 Hz), 4.39-4.45 (m, 1H), 3.62-3.66 (m, 1H), 2.70 (s, 3H), 2.69 (s, 3H), 2.65 (s, 3H), 2.08 (s, 3H), 1.98-2.03 (m, 1H), 1.31 (s, 3H), 1.17-1.21 (m, 1H), 0.86-1.03 (m, 2H); $^{19}$F NMR (376 MHz, DMSO-d$_6$) δ−98.11 (s, 1F).

Scheme 45. Synthesis of Methyl 2-(2-((2S,4R)-1-(2-(3-Acetyl-5-(2-methylpyrimidin-5-yl)-1H-indazol-1-yl)acetyl)-4-fluoropyrrolidine-2-carboxamido)-6-bromopyridin-3-yl)acetate (61) and 2-(2-((2S,4R)-1-(2-(3-acetyl-5-(2-methylpyrimidin-5-yl)-1H-indazol-1-yl)acetyl)-4-fluoropyrrolidine-2-carboxamido)-6-bromopyridin-3-yl)acetic acid (62) and (2S,4R)-1-(2-(3-Acetyl-5-(2-Methylpyrimidin-5-yl)-1H-indazol-1-yl)acetyl)-N-(6-bromo-3-(2-(dimethylamino)-2-oxoethyl)pyridin-2-yl)-4-fluoropyrrolidine-2-carboxamide (117)

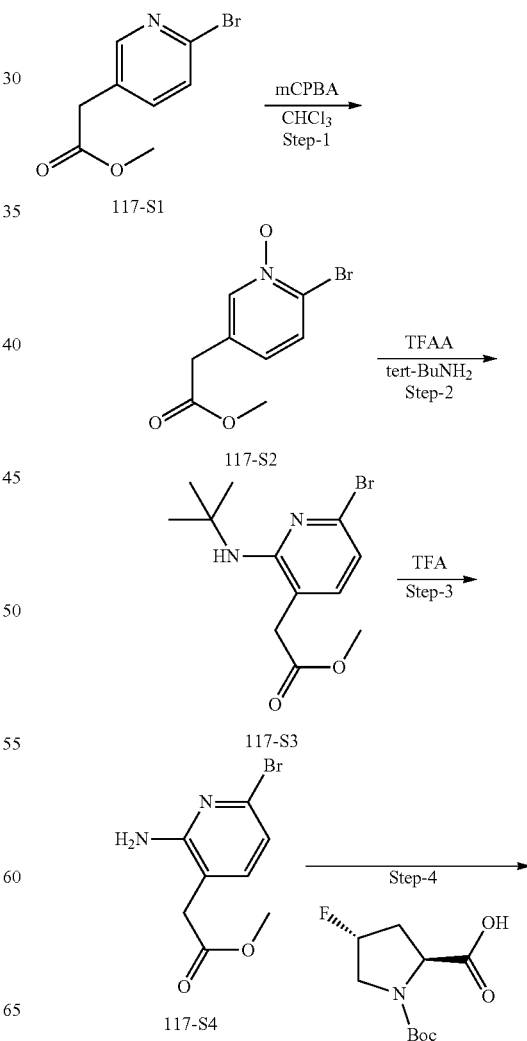

767

-continued

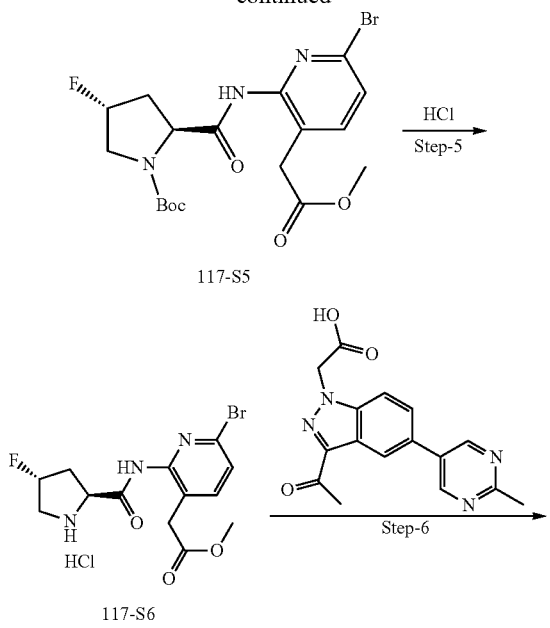

117-S5

117-S6

61

62

768

-continued

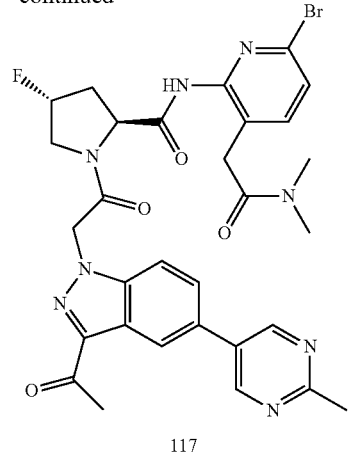

117

Step 1: Methyl 2-(6-bromo-1-oxidanyl)-pyridin-3-yl)acetate (117-S2)

To a stirred solution of methyl 2-(6-bromopyridin-3-yl)acetate (117-S1, 1 g, 1 equiv) in CHCl$_3$ (100 mL) was added 3-chlorobenzoperoxoic acid (1.93 g, 2 equiv). The reaction mixture was heated to 50° C. until it was complete. The reaction was cooled and neutralized with saturated aqueous NaHCO$_3$ solution (50 mL). The organic layer was washed with brine, dried over Na$_2$SO$_4$ and concentrated to dryness. The residue was purified by column chromatography on silica gel (5% CH$_3$OH in DCM, gradient) to afford 117-S2 (848 mg, 80%).

Step 2: Methyl 2-(6-bromo-2-(tert-butylamino)pyridin-3-yl)acetate (117-S3)

To a stirred solution of 117-S2 (848 mg, 1 equiv) and 2-methylpropan-2-amine (1.8 mL, 5 equiv) in DCM (90 mL) was added trifluoroacidic anhydride solution (0.87 mL, 1.5 equiv) in DCM (10 mL) at 0-5° C. dropwise under an atmosphere of argon. The reaction mixture was stirred at 0-5° C. for 2 hours before it was neutralized with a solution of aqueous saturated NaHCO$_3$ (20 mL). The organic layer was washed with aqueous saturated NaHCO$_3$ (40 mL) and brine (40 mL), dried over Na$_2$SO$_4$, and concentrated to dryness. The residue was purified by column chromatography on silica gel (eluted by 30% EtOAc in hexanes, gradient) to afford 117-S3 (104 mg, 10%).

Step 3: Methyl 2-(2-amino-6-bromopyridin-3-yl)acetate (117-S4)

TFA (10 mL) was added to solid 117-S3 (104 mg) and the reaction mixture was heated at 70° C. The reaction was concentrated to dryness and the residue was dissolved in DCM (25 mL) and neutralized with aqueous saturated NaHCO$_3$ (20 mL). The organic layer was washed with brine, dried over Na$_2$SO$_4$ and concentrated to dryness to afford 117-S4 (96 mg).

Step-4: tert-Butyl (2S,4R)-2-((6-bromo-3-(2-methoxy-2-oxoethyl)pyridin-2-yl)carbamoyl)-4-fluoropyrrolidine-1-carboxylate (117-S5)

POCl$_3$ (0.08 mL, 2 equiv) was added dropwise at 0-5° C. under an atmosphere of argon to a solution of (2S,4R)-1-

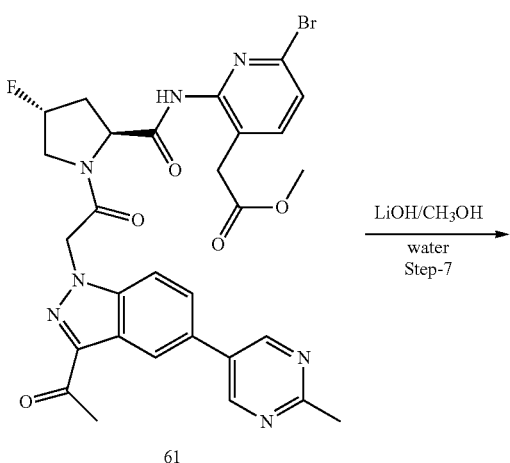

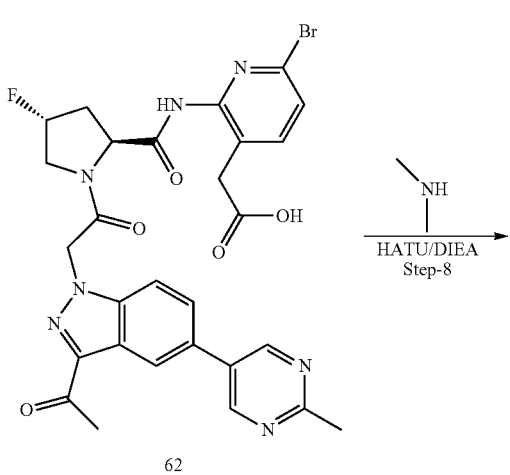

(tert-butoxycarbonyl)-4-fluoropyrrolidine-2-carboxylic acid (91 mg, 1 equiv) and 117-S4 (96 mg, 1 equiv) in DCM (10 mL) and pyridine (0.16 mL, 5 equiv). The reaction mixture was warmed to room temperature and stirred until complete. The reaction was diluted with DCM (10 mL) and neutralized with aqueous saturated NaHCO$_3$ solution (10 mL). The aqueous layer was extracted with DCM (1×10 mL) and the combined organic layers were washed with brine (10 mL), dried over Na$_2$SO$_4$, and concentrated to dryness. The residue was purified by column chromatography on silica gel (eluted by 5% MeOH in DCM gradient) to afford 117-S5 (146 mg, 82%).

Step 5: Methyl 2-(6-bromo-2-((2S,4R)-4-fluoropyr-rolidine-2-carboxamido)pyridin-3-yl)acetate Hydro-chloride (117-S6)

To a solution of 117-S5 (146 mg) was added 4N HCl in Dioxane (10 mL). The resulting solution was stirred at room temperature for 6 hours. The reaction mixture was concentrated to dryness to afford 117-S6 (117 mg).

Step 6: Methyl 2-(2-((2S,4R)-1-(2-(3-acetyl-5-(2-methylpyrimidin-5-yl)-1H-indazol-1-yl)acetyl)-4-fluoropyrrolidine-2-carboxamido)-6-bromopyridin-3-yl)acetate (61)

To a solution of 117-S6 (117 mg, 1 equiv), 2-(3-acetyl-5-(2-methylpyrimidin-5-yl)-1H-indazol-1-yl)acetic acid (92 mg, 1 equiv) and DIPEA (0.25 mL, 5 equiv) in DMF (15 mL) was added HATU (137 mg, 1.2 equiv) at 0° C. under an atmosphere of argon. The reaction mixture was stirred at room temperature for 3 hours before the reaction mixture was diluted with EtOAc (35 mL) and water (15 mL). The aqueous layer was extracted with EtOAc (15 mL). The combined organic layers were washed with brine, dried over anhydrous Na$_2$SO$_4$ and concentrated to dryness. The residue was purified by column chromatography on silica gel (eluted by DCM/MeOH=10:1) to afford 61 (99 mg, 50%). $^1$H NMR (400 MHz, DMSO-d$_6$) δ 10.58 (s, 1H), 9.04 (s, 2H), 8.40 (s, 1H), 7.79-7.90 (m, 2H), 7.68 (d, 1H, J=8.1 Hz), 7.52 (d, 1H, J=8.1 Hz), 5.49-5.88 (m, 3H), 4.56-4.62 (m, 1H), 4.19-4.29 (m, 1H), 3.94-4.30 (m, 1H), 3.55 (s, 2H), 3.44 (s, 3H), 2.70 (s, 3H), 2.65 (s, 3H), 2.07-2.34 (m, 1H), 0.85-0.92 (m, 1H); $^{19}$F NMR (376 MHz, DMSO-d$_6$) δ−176.07 (s, 1F).

Step 7: 2-(2-((2S,4R)-1-(2-(3-Acetyl-5-(2-methylpyrimidin-5-yl)-1H-indazol-1-yl)acetyl)-4-fluoropyrrolidine-2-carboxamido)-6-bromopyridin-3-yl)acetic Acid (62)

To a solution of 61 (45 mg, 1 equiv) in methanol (6 mL) was added aqueous LiOH solution in water (3 mL, 1M, 1.2 equiv) and the reaction mixture was stirred at room temperature. After completion of the reaction, the reaction mixture was acidified with HCl (1N) and extracted with DCM (10 mL). The organic layer was washed with brine, dried over anhydrous Na$_2$SO$_4$, filtered, and concentrated to dryness to afford 62 (15 mg, 34%). $^1$H NMR (400 MHz, DMSO-d$_6$) δ 10.48 (s, 1H), 8.98 (s, 2H), 8.36 (s, 1H), 7.69-7.82 (m, 2H), 7.60 (d, 1H, J=8.2 Hz), 7.44 (d, 1H, J=8.2 Hz), 5.42-5.77 (m, 3H), 4.52-4.58 (m, 1H), 4.11-4.23 (m, 1H), 3.86-4.01 (m, 1H), 3.41 (s, 2H), 2.62 (s, 3H), 2.58 (s, 3H), 2.46-2.56 (m, 1H), 2.01-2.21 (m, 1H); $^{19}$F NMR (376 MHz, DMSO-d$_6$) δ−176.12 (s, 1F).

Step-8: (2S,4R)-1-(2-(3-Acetyl-5-(2-methylpyrimidin-5-yl)-1H-indazol-1-yl)acetyl)-N-(6-bromo-3-(2-(dimethylamino)-2-oxoethyl)pyridin-2-yl)-4-fluoro-pyrrolidine-2-carboxamide (117)

To a solution of 62 (44 mg, 1.2 equiv), dimethyl amine hydrochloride (33 mg, 1.0 equiv), and DIPEA (0.08 mL, 5 equiv) in DMF (10 mL) was added HATU (32 mg, 1.2 equiv) at 0° C. under an atmosphere of argon. The reaction mixture was stirred at room temperature for 3 hours before the reaction mixture was diluted with EtOAc (20 mL) and water (10 mL). The aqueous layer was extracted with EtOAC (15 mL) and the combined organic layers were washed with brine, dried over anhydrous Na$_2$SO$_4$, filtered and concentrated to dryness. The residue was purified by column chromatography on silica gel (eluted by DCM/MeOH=10:1) to afford 117 (32 mg, 50%). $^1$H NMR (400 MHz, DMSO-d$_6$) δ 10.46 (s, 1H), 8.98 (s, 2H), 8.38 (s, 1H), 7.70-7.84 (m, 1H), 7.78 (s, 1H), 7.48 (d, 1H, J=8.0 Hz), 7.40 (d, 1H, J=8.0 Hz), 5.42-5.81 (m, 3H), 4.46-4.52 (m, 1H), 4.11-4.21 (m, 1H), 3.89-4.04 (m, 1H), 2.57 (s, 2H), 2.61 (s, 3H), 2.58 (s, 3H), 2.51 (s, 3H), 2.36 (s, 3H), 1.96-2.15 (m, 2H); $^{19}$F NMR (376 MHz, DMSO-d$_6$) δ−175.89 (s, 1F).

Scheme 46. Synthesis of (1R,3S,5R)-2-(2-(3-Acetyl-5-(2-(methylamino)pyrimidin-5-yl)-1H-indazol-1-yl)acetyl)-N-(6-bromo-3-methylpyridin-2-yl)-5-methyl-2-azabicyclo[3.1.0] hexane-3-carbxamide (120)

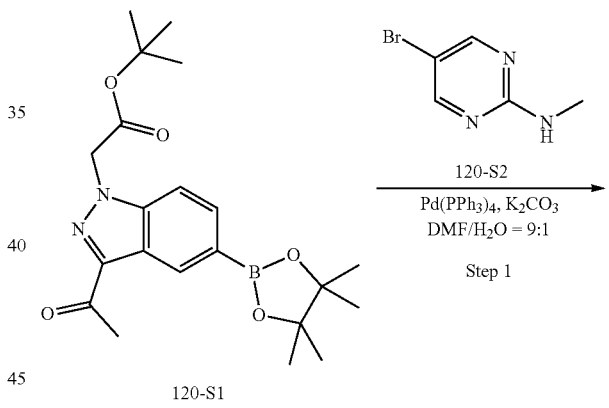

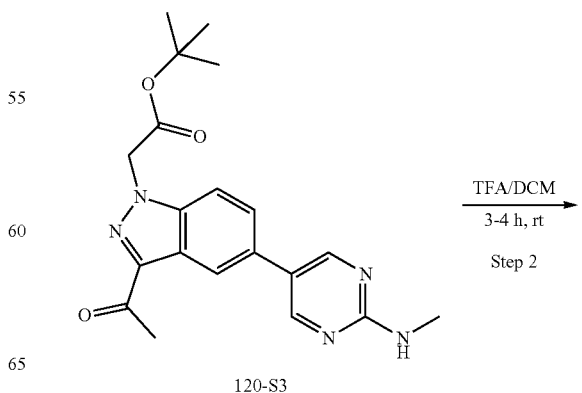

Step 3: (1R,3S,5R)-2-(2-(3-Acetyl-5-(2-(methyl-amino)pyrimidin-5-yl)-1H-indazol-1-yl)acetyl)-N-(6-bromo-3-methylpyridin-2-yl)-5-methyl-2-azabi-cyclo[3.1.0]hexane-3-carboxamide (120)

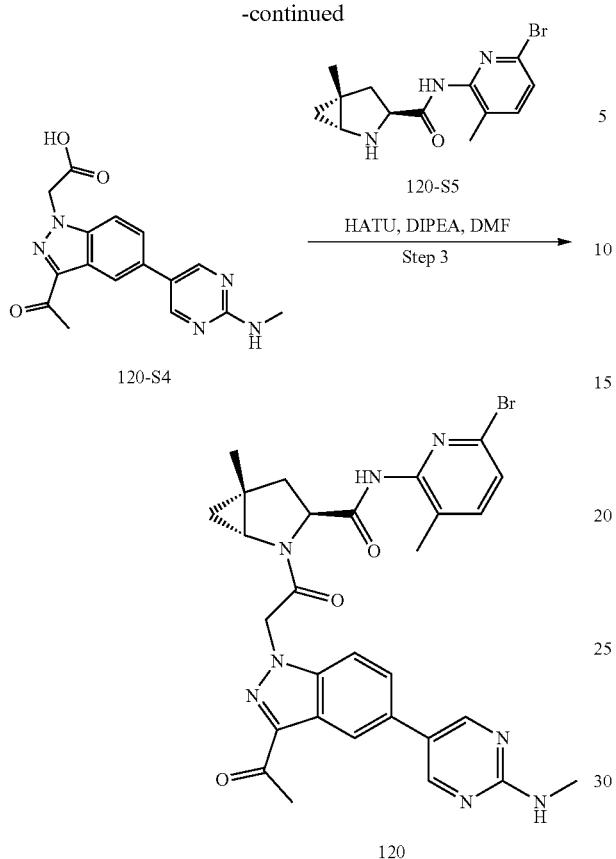

To a solution of compound 120-S4 (1 equiv) in DMF (10 vol) at 0° C. under an atmosphere of argon were added (1R,3S,5R)—N-(6-bromo-3-methylpyridin-2-yl)-5-methyl-2-azabicyclo[3.1.0]hexane-3-carboxamide (1 equiv), HATU (2.1 equiv), and DIPEA (5 equiv). The reaction mixture was stirred at room temperature for 3 hours and then quenched with water (30 vol). The resulting mixture was extracted with DCM. The organic layer was washed with brine, dried over anhydrous $Na_2SO_4$, filtered, and concentrated to dryness. The remaining residue was purified by column chromatography on silica gel (eluted with DCM/MeOH) to afford compound 120. $^1$H NMR (400 MHz, DMSO-$d_6$) δ 0.97-1.06 (m, 2H), 1.33 (s, 3H), 2.05 (s, 4H), 2.53-2.58 (m, 1H), 2.65 (s, 3H), 2.87 (d, J=4.5 Hz, 3H), 3.55-3.64 (m, 1H), 4.33-4.47 (m, 1H), 5.55 (d, J=17.2 Hz, 1H), 5.88 (d, J=17.3 Hz, 1H), 7.26 (q, J=4.9 Hz, 1H), 7.45 (d, J=7.9 Hz, 1H), 7.63 (d, J=8.0 Hz, 1H), 7.69-7.80 (m, 2H), 8.29 (s, 1H), 8.64 (s, 2H), 10.26 (s, 1H).

The above scheme and following detailed description depicts one non-limiting method for synthesizing compounds with a substituted pyrimidine in the $R^{32}$ position via a Suzuki cross-coupling reaction where the A-ring is functionalized with a boronic ester. The skilled artisan will recognize that the aryl halide 5-bromo-N-methylpyrimidin-2-amine shown above can be replaced with other aryl halides to afford additional compounds of the present invention. Non-limiting examples of aryl halides that the skilled artisan can use include 5-bromo-2-methylpyrimide.

Step 1: tert-Butyl 2-(3-acetyl-5-(2-(methylamino)pyrimidin-5-yl)-1H-indazol-1-yl)acetate (120-S3)

To a solution of 5-bromo-N-methylpyrimidin-2-amine (120-S2, 1 equiv) in DMF/$H_2O$ (9:1, 10 vol) was added compound 120-S1 (1 equiv), $K_2CO_3$ (2 equiv) and tetrakis(triphenylphosphine)palladium (0.1 equiv). The reaction mixture was stirred at 90° C. for 5 hours and concentrated under reduced pressure. The remaining residue was purified by column chromatography on silica gel (eluted with DCM/MeOH) to afford compound 120-S3.

Step 2: 2-(3-Acetyl-5-(2-(methylamino)pyrimidin-5-yl)-1H-indazol-1-yl)acetic Acid (120-S4)

To a solution of compound 120-S3 (1 equiv) in DCM (10 vol) at 0° C. under an atmosphere of argon was added TFA (5 vol). The reaction mixture was stirred at room temperature for 3 hours and concentrated to dryness. The remaining material was used directly in the next synthetic step.

(1R,3S,5R)-2-(2-(3-Acetyl-5-(2-methylpyrimidin-5-yl)-1H-indol-1-yl)acetyl)-N-(6-bromo-3-methylpyridin-2-yl)-5-methyl-2-azabicyclo[3.1.0]hexane-3-carboxamide $^1$H-NMR (400 MHz, CDCl$_3$): δ 0.86-0.88 (m, 1H), 1.16 (t, J=5.2 Hz, 1H), 1.41 (s, 3H), 2.08 (s, 3H), 2.33 (t, J=8.8 Hz, 1H) 2.55 (s, 3H), 2.67 (d, J=13.2 Hz, 1H), 2.81 (s, 3H), 3.14 (d, J=2.8 Hz, 1H), 4.83 (d, J=6.4 Hz, 1H), 5.18 (s, 2H), 7.23 (d, J=8 Hz, 1H), 7.35 (d, J=8 Hz, 1H), 7.39 (d, J=8.4 Hz, 1H), 7.49 (dd, J=8.4, 1.2 Hz, 1H), 7.88 (s, 1H), 8.57 (brs, 1H), 8.65 (s, 1H), 8.94 (s, 2H).

(1R,3S,5R)-2-(2-(3-Acetyl-5-(pyridin-4-yl)-1H-indazol-1-yl)acetyl)-N-(6-bromo-3-methylpyridin-2-yl)-5-methyl-2-azabicyclo[3.1.0]hexane-3-carboxamide $^1$H-NMR (400 MHz, DMSO-$d_6$) δ 10.28 (s, 1H), 8.66 (dd, J=4.5, 1.6 Hz, 2H), 8.52 (d, J=0.8 Hz, 1H), 7.91 (dd, J=8.9, 1.7 Hz, 1H), 7.85 (d, J=8.6 Hz, 1H), 7.76 (dd, J=4.5, 1.6 Hz, 2H), 7.63 (d, J=8.1 Hz, 1H), 7.45 (d, J=7.9 Hz, 1H), 5.92 (d, J=17.3 Hz, 1H), 5.58 (d, J=17.2 Hz, 1H), 4.41 (m, 1H), 3.59 (m, 1H), 2.66 (s, 3H), 2.60-2.52 (m, 1H), 2.11-1.99 (m, 4H), 1.32 (s, 3H), 1.07-0.96 (m, 2H). LC/MS (ESI) m/z: 587/589 (M+H)$^+$.

(1R,3S,5R)-2-(2-(3-Acetyl-5-(5-methylpyridin-2-yl)-1H-indazol-1-yl)acetyl)-N-(6-bromo-3-methylpyridin-2-yl)-5-methyl-2-azabicyclo[3.1.0]hexane-3-carboxamide $^1$H-NMR (400 MHz, DMSO-$d_6$) δ 10.28 (s, 1H), 8.86 (s, 1H), 8.54 (s, 1H), 8.19 (dd, J=8.9, 1.6 Hz, 1H), 7.92 (d, J=8.2 Hz, 1H), 7.75 (dd, J=16.9, 8.5 Hz, 2H), 7.62 (d, J=7.9 Hz, 1H), 7.45 (d, J=7.9 Hz, 1H), 5.89 (d, J=17.3 Hz, 1H), 5.55 (d, J=17.1 Hz, 1H), 4.41 (dd, J=9.3, 5.1 Hz, 1H), 3.59 (dd, J=5.3, 2.4 Hz, 1H), 2.64 (d, J=6.6 Hz, 3H), 2.58-2.51 (m, 1H), 2.35 (s, 3H), 2.04 (s, 3H), 1.32 (s, 3H), 1.18-1.14 (m, 1H), 1.04-1.00 (m, 1H). LC/MS (ESI) m/z: 601/603 (M+H)$^+$.

773

Scheme 47. Synthesis of (1R,3S,5R)-2-(2-(3-Acetyl-5-(2-methylpyrimidin-5-yl)-1H-indazol-1-yl)acetyl)-N-(6-bromo-3-vinylpyridin-2-yl)-5-((hex-5-en-1-yl(methyl)amino)methyl)-2-azabicylco[3.1.0]hexane-3-carboxamide (123)

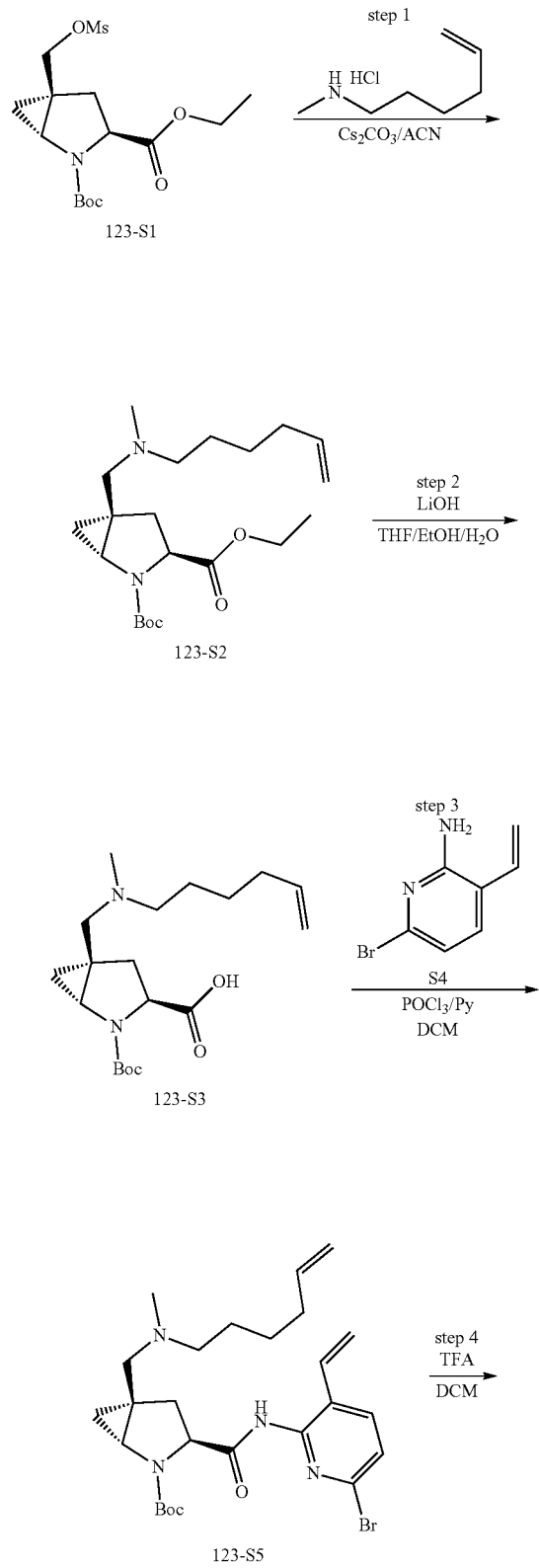

774

-continued

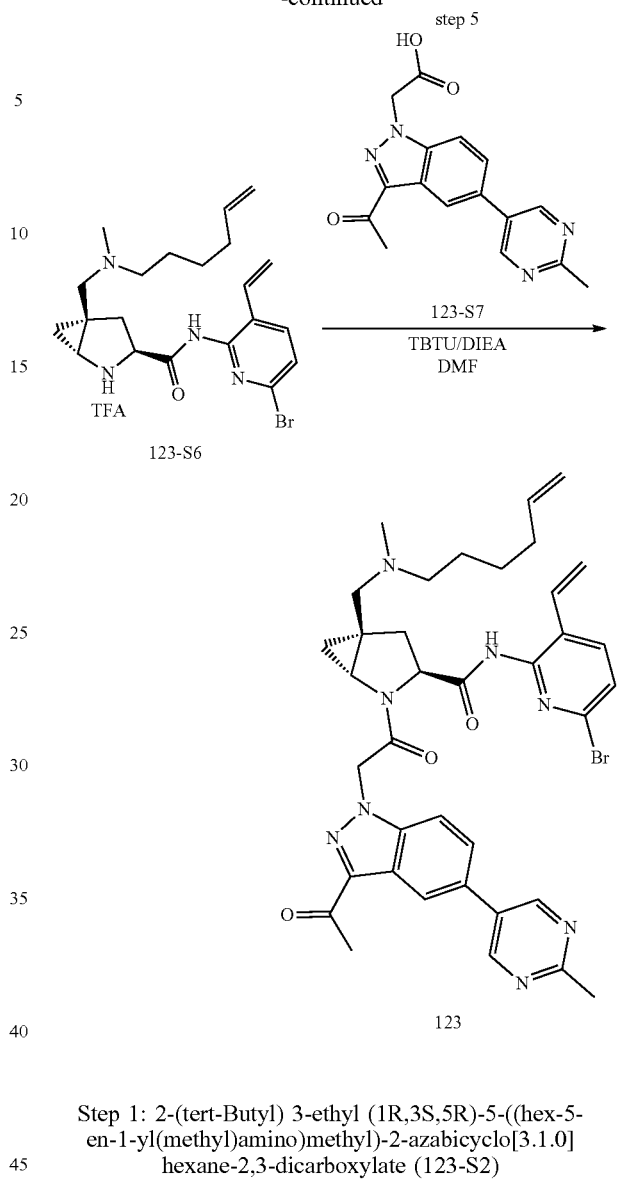

Step 1: 2-(tert-Butyl) 3-ethyl (1R,3S,5R)-5-((hex-5-en-1-yl(methyl)amino)methyl)-2-azabicyclo[3.1.0]hexane-2,3-dicarboxylate (123-S2)

$Cs_2CO_3$ (0.8 g) was added to a mixture of 2-(tert-butyl) 3-ethyl (1R,3S,5S)-5-(((methylsulfonyl)oxy)methyl)-2-azabicyclo[3.1.0]hexane-2,3-dicarboxylate (123-S1, 0.807 mmol) and N-methylhex-5-en-1-amine HCl salt (0.145 g, 0.968 mmol) in ACN (10 mL). The reaction was heated and stirred in the presence at 50° C. under argon overnight. EtOAC was added and the diluted reaction mixture was filtered through Celite to remove solids. Solvents were removed under reduced pressure and the residue was purified by column chromatography on silica gel with MeOH in DCM (0-10%) as the eluent to afford 2-(tert-butyl) 3-ethyl (1R,3S,5R)-5-((hex-5-en-1-yl(methyl)amino)methyl)-2-azabicyclo[3.1.0]hexane-2,3-dicarboxylate 123-S2 (0.193 g) as a yellowish oil.

Step 2: (1R,3S,5R)-5-((Hex-5-en-1-yl(methyl)amino)methyl)-2-(tert-butoxycarbonyl)-2-azabicyclo[3.1.0]hexane-3-carboxylic acid (123-S3)

2-(tert-Butyl) 3-ethyl (1R,3S,5R)-5-((hex-5-en-1-yl(methyl)amino)methyl)-2-azabicyclo[3.1.0]hexane-2,3-dicarboxylate (123-S2, 0.193 g, 0.508 mmol) was dissolved in a mixture of THF-EtOH-water (3 mL-0.5 mL-0.5 mL) and treated with LiOH monohydrate (25.6 mg, 0.609 mmol). The reaction was stirred at room temperature for 24 hours before Amberlite (the weakly acidic cation exchanger H form, 1 g) was added. After stirred for 5 minutes, the reaction was filtered and the resulting resin was washed with MeOH. The combined filtrates were concentrated under reduced pressure to afford (1R,3S,5R)-5-((hex-5-en-1-yl (methyl)amino)methyl)-2-(tert-butoxycarbonyl)-2-azabicyclo[3.1.0]hexane-3-carboxylic acid 123-S3 (0.171 g) as a colorless amorphous solid.

Step 3: tert-Butyl (1R,3S,5R)-3-((6-bromo-3-vinylpyridin-2-yl)carbamoyl)-5-((hex-5-en-1-yl (methyl)amino)methyl)-2-azabicyclo[3.1.0]hexane-2-carboxylate (123-S5)

To a mixture of 123-S3 (171 mg, 0.486 mmol) and 123-S4 (77 mg, 0.389 mmol) in DCM (10 mL), pyridine (0.196 mL, 2.43 mmol) was added followed by POCl$_3$ (0.045 mL, 0.486 mmol) at 0° C. under argon. The reaction mixture was stirred at room temperature for 2 hours. NaHCO$_3$ aqueous solution was added and the mixture was extracted with DCM. After washing with brine, the organic layer was dried over anhydrous Na$_2$SO$_4$. The solution was filtered and the solvent was removed under reduced pressure. The remaining residue was purified by column chromatography on silica gel with MeOH in DCM (0-10%) as the eluent to afford tert-butyl (1R,3S,5R)-3-((6-bromo-3-vinylpyridin-2-yl)carbamoyl)-5-((hex-5-en-1-yl(methyl)amino)methyl)-2-azabicyclo[3.1.0] hexane-2-carboxylate 123-S5 (99 mg).

Step 4: (1R,3S,5R)—N-(6-Bromo-3-vinylpyridin-2-yl)-5-((hex-5-en-1-yl(methyl)amino)methyl)-2-azabicyclo[3.1.0]hexane-3-carboxamide TFA Salt (123-S6)

tert-Butyl (1R,3S,5R)-3-((6-bromo-3-vinylpyridin-2-yl)carbamoyl)-5-((hex-5-en-1-yl(methyl)amino)methyl)-2-azabicyclo[3.1.0]hexane-2-carboxylate (123-S5, 5.7 mg) in DCM (1 mL) was treated with TFA (1 mL) at room temperature. The reaction stirred for 1 hour before the volatiles were removed under reduced pressure and the residue was co-evaporated with toluene (5 mL) twice to afford (1R,3S, 5R)—N-(6-bromo-3-vinylpyridin-2-yl)-5-((hex-5-en-1-yl (methyl)amino)methyl)-2-azabicyclo[3.1.0]hexane-3-carboxamide TFA salt 123-S6. The material was carried forward without additional purification.

Step 5: (1R,3S,5R)-2-(2-(3-Acetyl-5-(2-methylpyrimidin-5-yl)-1H-indazol-1-yl)acetyl)-N-(6-bromo-3-vinylpyridin-2-yl)-5-((hex-5-en-1-yl(methyl) amino)methyl)-2-azabicyclo[3.1.0]hexane-3-carboxamide (123)

To a mixture of (1R,3S,5R)—N-(6-bromo-3-vinylpyridin-2-yl)-5-((hex-5-en-1-yl(methyl)amino)methyl)-2-azabicyclo[3.1.0]hexane-3-carboxamide TFA salt 123-S6 and 2-(3-acetyl-5-(2-methylpyrimidin-5-yl)-1H-indazol-1-yl) acetic acid (123-S7, 3.4 mg, 0.011 mmol) in DMF (0.5 mL), TBTU (7.1 mg) was added followed by DIEA (0.0096 mL) with stirring. After the reaction was complete, NaHCO$_3$ aqueous solution (10 mL) was added to form a precipitate that was collected by filtration and purified by column chromatography on silica gel with MeOH in DCM (0-10%) as the eluent to afford (1R,3S,5R)-2-(2-(3-acetyl-5-(2-methylpyrimidin-5-yl)-1H-indazol-1-yl)acetyl)-N-(6-bromo-3-vinylpyridin-2-yl)-5-((hex-5-en-1-yl(methyl)amino) methyl)-2-azabicyclo[3.1.0]hexane-3-carboxamide (123) (6.2 mg) as an off-white solid. $^1$H NMR (400 MHz, Chloroform-d) δ 8.90 (s, 2H), 8.67 (s, 1H), 8.58 (dd, J=0.9, 1.6 Hz, 1H), 7.69-7.59 (m, 4H), 7.30 (d, J=8.1 Hz, 1H), 6.46 (dd, J=11.0, 17.4 Hz, 1H), 5.80 (ddt, J=6.7, 10.2, 16.9 Hz, 1H), 5.66 (dd, J=0.8, 17.4 Hz, 1H), 5.51 (d, J=1.1 Hz, 2H), 5.27 (d, J=11.1 Hz, 1H), 5.05-4.91 (m, 2H), 4.88 (d, J=8.6 Hz, 1H), 3.25 (dd, J=2.5, 5.8 Hz, 1H), 2.91 (t, J=14.1 Hz, 2H), 2.80 (s, 3H), 2.72 (s, 3H), 2.41 (tt, J=5.7, 13.0 Hz, 1H), 2.28 (s, 4H), 2.11-2.01 (m, 2H), 1.54-1.34 (m, 4H), 1.30 (s, 0H), 1.02 (dt, J=2.1, 4.1 Hz, 1H), 0.93-0.76 (m, 1H). LC (method A): t$_R$=1.48 min. LC/MS (EI) m/z: [M+H]$^+$ 725.

Scheme 48. Synthesis of (1R,3S,5R)-2-(2-(3-Acetyl-7-cyano-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (124)

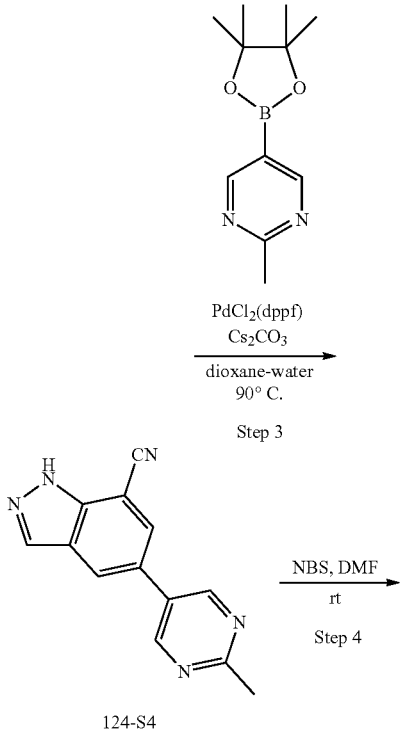

124-S4

-continued

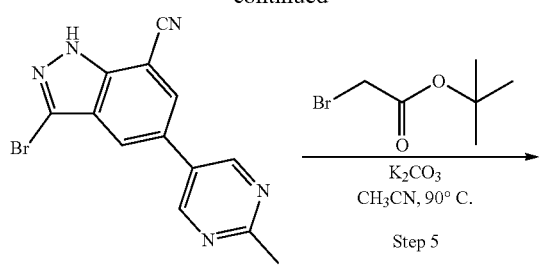

124-S5

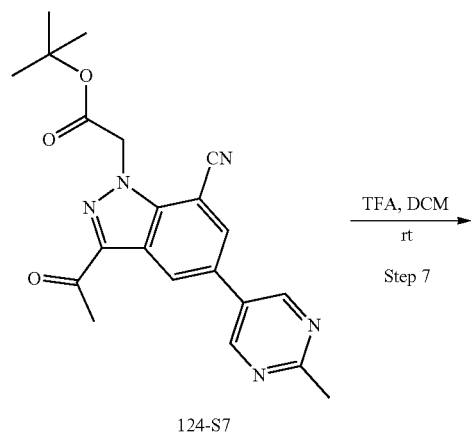

124-S6

124-S7

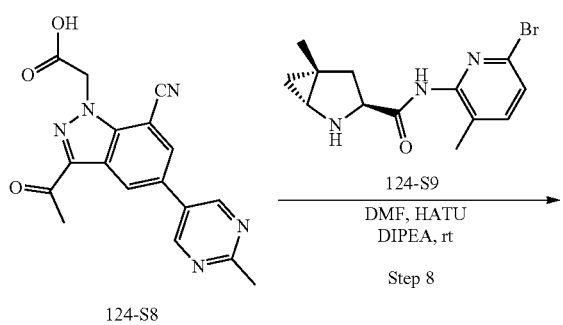

124-S8

-continued

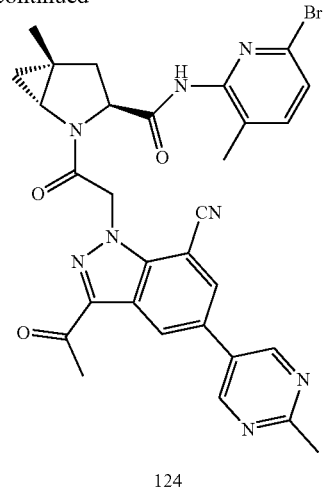

124

Step 1: 5-Bromo-1H-indazole-7-carboxamide (124-S2)

5-Bromo-1H-indazole-7-carboxylic acid (1 g) was dissolved in DMF (10 mL) and iPr$_2$NEt (3.42 mL, 5 equiv) was added, followed by the addition of NH$_4$Cl (1.2 g) at 5° C. HATU (1.8 g, 1.2 equiv) was added slowly at 5° C. and the reaction mixture was stirred overnight at room temperature. Then the reaction mixture was poured into water and the precipitate was isolated by filtration. The white solid was dried and carried forward without additional purification in the next step.

Step 2: 5-Bromo-1H-indazole-7-carbonitrile (124-S3)

To a heterogeneous mixture of 5-bromo-1H-indazole-7-carboxamide (0.6 g) in CH$_2$Cl$_2$ (6 mL) and pyridine (6 mL), TFAA (0.87 mL) was added dropwise. The resulting homogeneous solution was stirred for 10 minutes at room temperature. The volatiles were removed and the residue was poured into water (60 mL). The precipitated white product was isolated by filtration, washed with water, and dried in vacuo. The solid carried forward without additional purification in the next step.

Step 3: 5-(2-Methylpyrimidin-5-yl)-1H-indazole-7-carbonitrile (124-S4)

A mixture of 5-bromo-1H-indazole-7-carbonitrile (0.32 g equiv), 2-methyl-5-(4,4,5,5-tetramethyl-1,3,2-dioxaborolan-2-yl)pyrimidine (0.708 g), cesium carbonate (1.4 g) in dioxane (12 mL) and water (3.0 mL) was purged with argon in a pressure vessel for 5 minutes. PdCl$_2$(dppf) (0.4 g) was added under argon and the pressure vessel was sealed and heated at 90° C. overnight. The reaction mixture was cooled to room temperature and the solvent was removed under reduced pressure. The crude product was purified by silica gel flash column chromatography (eluent: 0-30% MeOH in CH$_2$Cl$_2$) to afford 0.24 g of 124-S4 as white solid.

Step 4: 3-Bromo-5-(2-methylpyrimidin-5-yl)-1H-indazole-7-carbonitrile (124-S5)

To a stirred solution of 5-(2-methylpyrimidin-5-yl)-1H-indazole-7-carbonitrile (0.24 g) in DMF (4 mL), NBS (0.2 g) was added. The reaction mixture was stirred at room temperature for 30 minutes. The reaction mixture was then poured into water and the precipitate was isolated by filtration, washed with water, and dried. The solid carried forward without additional purification in the next step.

Step 5: tert-Butyl 2-(3-bromo-7-cyano-5-(2-methylpyrimidin-5-yl)-1H-indazol-1-yl)acetate (124-S6)

A mixture of 3-bromo-5-(2-methylpyrimidin-5-yl)-1H-indazole-7-carbonitrile (0.3 g), tert-butyl bromoacetate (148 μl) and potassium carbonate (0.264 g) in anhydrous acetonitrile (5 mL) was refluxed for 2 hours. The reaction mixture was then cooled to room temperature and the solvent was removed under reduced pressure. The residue was purified by silica gel flash column chromatography (eluent: 0-1.5% MeOH in $CH_2Cl_2$) to afford 124-S6 as white foam.

Step 6: tert-Butyl 2-(3-acetyl-7-cyano-5-(2-methylpyrimidin-5-yl)-1H-indazol-1-yl)acetate (124-S7)

A solution of tert-butyl 2-(3-bromo-7-cyano-5-(2-methylpyrimidin-5-yl)-1H-indazol-1-yl)acetate (0.06 g 1 equiv), tri-butyl(1-ethoxyvinyl)tin (0.101 g, 2 equiv) and $PdCl_2(PPh_3)_2$ (10 mg, 0.1 equiv) in DMF (5 mL) was heated at 80° C. overnight under an argon atmosphere. The reaction mixture was concentrated under reduced pressure, diluted with $CH_2Cl_2$, and washed with cold aqueous HCl (1N). The organic layer was dried ($Na_2SO_4$), filtered and concentrated. The residue was purified by silica gel flash column chromatography (eluent: 0-1.5% MeOH in $CH_2Cl_2$) to afford the title compound.

Step 7: 2-(3-Acetyl-7-cyano-5-(2-methylpyrimidin-5-yl)-1H-indazol-1-yl)acetic Acid (124-S8)

tert-Butyl 2-(3-acetyl-7-cyano-5-(2-methylpyrimidin-5-yl)-1H-indazol-1-yl)acetate (124-S7, 45 mg) was stirred in $CH_2Cl_2$ (0.5 mL) and TFA (1 mL). After completion of the reaction (monitored by HPLC), the solvent was removed under reduced pressure and the remaining residue was carried forward without additional purification in the next synthetic step.

Step 8: (1R,3S,5R)-2-(2-(3-Acetyl-7-cyano-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (124)

Compound 124-S8 was dissolved in DMF (1 mL) and iPr$_2$NEt (60 μL, 3 equiv) was added, followed by the addition of the TFA salt of (1R,3S,5R)—N-(6-bromopyridin-2-yl)-5-methyl-2-azabicyclo[3.1.0]hexane-3-carboxamide (124-S9, obtained by stirring 47 mg of tert-butyl (1R,3S,5R)-3-((6-bromopyridin-2-yl)carbamoyl)-5-methyl-2-azabicyclo[3.1.0]hexane-2-carboxylate in 0.5 mL of TFA and 0.5 mL of $CH_2Cl_2$ for 15 minutes at room temperature and evaporating the volatiles) at 5° C. HATU (48 mg, 1.2 equiv) was then added slowly at this same temperature and the reaction mixture was stirred for 30 minutes at room temperature. The reaction mixture was poured into water and the precipitate was isolated by filtration. The solid was dried and purified by silica gel flash column chromatography (eluent: 0-2.0% MeOH in $CH_2Cl_2$) to afford 124 as a white solid. $^1$H NMR (400 MHz, DMSO-d$_6$) δ 1.01-1.06 (m, 2H), 1.32 (s, 3H), 2.05 (s, 3H), 2.07 (t, J=5.6 Hz, 1H), 2.51-2.56 (m, 1H), 2.69 (s, 3H), 2.70 (s, 3H), 3.59 (t, J=3.8 Hz, 1H), 4.41 (dd, J=5.3, 9.1 Hz, 1H), 5.88 (d, J=17.9 Hz, 1H), 6.09 (d, J=17.9 Hz, 1H), 7.43 (d, J=7.8 Hz, 1H), 7.62 (d, J=7.9 Hz, 1H), 8.52 (s, 1H), 8.78 (s, 1H), 9.12 (s, 2H), 10.26 (s, 1H).

Scheme 49. Synthesis of (1R,3S,5R)-2-(2-(3-Acetyl-5-(2-(dimethylamino)pyrimidin-5-yl)-1H-indazol-1-yl)acetyl)-N-(6-bromo-3-methylpyridin-2-yl)-5-methyl-2-azabicyclo[3.1.0]hexane-3-carbxamide (125)

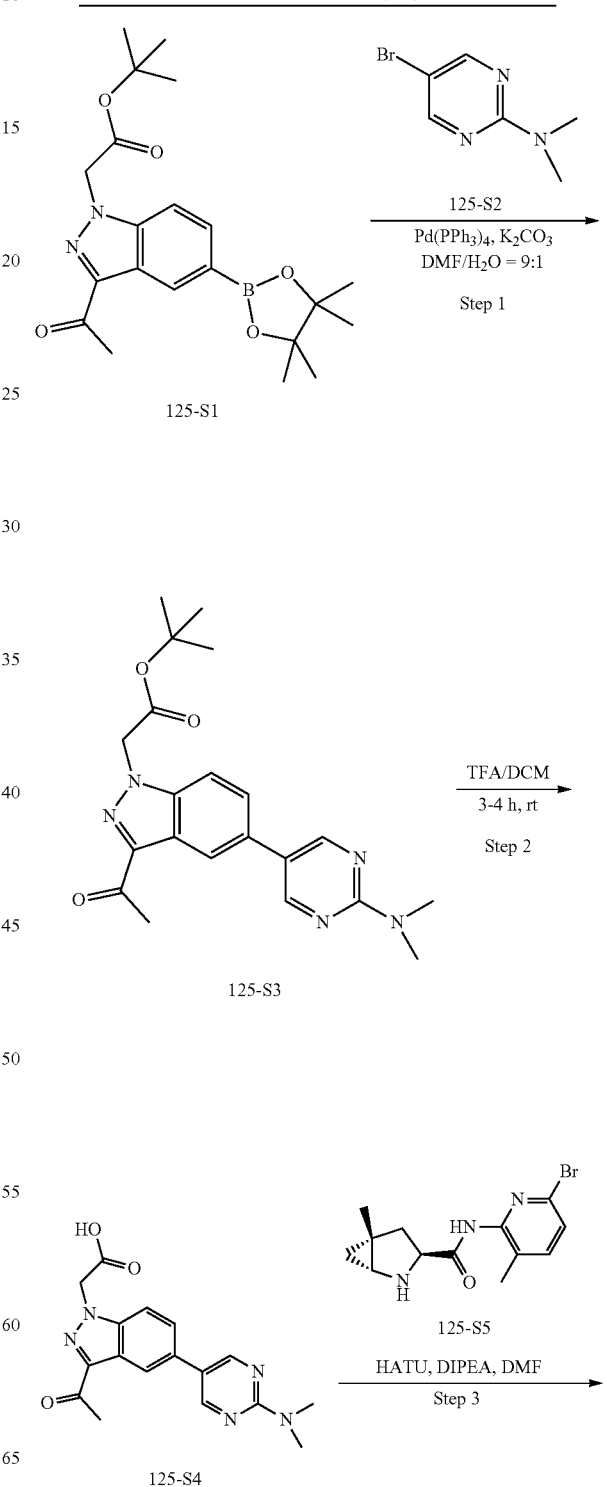

-continued

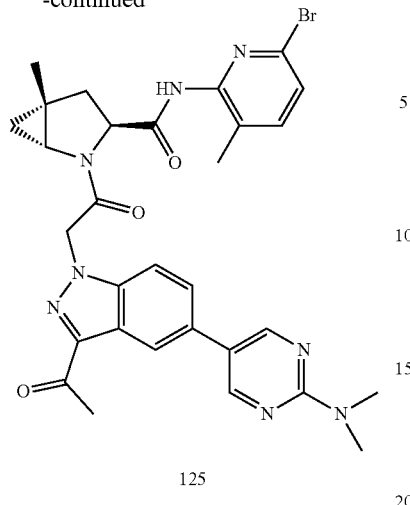

125

Step 1: tert-Butyl 2-(3-acetyl-5-(2-(dimethylamino)pyrimidin-5-yl)-1H-indazol-1-yl)acetate (125-S3)

To a solution of 5-bromo-N,N-dimethylpyrimidin-2-amine (125-S2, 1 equiv) in DMF/H$_2$O (9:1, 10 vol) was added compound (125-S1, 1 equiv), K$_2$CO$_3$ (2 equiv) and tetrakis(triphenylphosphine)palladium (0.1 equiv). The reaction mixture was stirred at 90° C. for 5 hours and concentrated under reduced pressure. The remaining residue was purified by column chromatography on silica gel (eluted with DCM/MeOH) to afford compound 125-S3.

Step 2: 2-(3-Acetyl-5-(2-(dimethylamino)pyrimidin-5-yl)-1H-indazol-1-yl)acetic Acid (125-S4)

To a solution of compound 125-S3 (1 equiv) in DCM (10 vol) at 0° C. under an atmosphere of argon was added TFA (5 vol). The reaction mixture was stirred at room temperature for 3 hours and concentrated to dryness. The remaining material was carried forward without additional purification and used directly in the next synthetic step.

Step 3: (1R,3S,5R)-2-(2-(3-Acetyl-5-(2-(dimethylamino)pyrimidin-5-yl)-1H-indazol-1-yl)acetyl)-N-(6-bromo-3-methylpyridin-2-yl)-5-methyl-2-azabicyclo[3.1.0]hexane-3-carboxamide (125)

To a solution of compound 125-S4 (1 equiv) in DMF (10 vol) at 0° C. under an atmosphere of argon was added (1R,3S,5R)—N-(6-bromo-3-methylpyridin-2-yl)-5-methyl-2-azabicyclo[3.1.0]hexane-3-carboxamide (1 equiv), HATU (2.1 equiv), and DIPEA (5 equiv). The reaction mixture was stirred at room temperature for 3 hours and then quenched with water (30 vol). The resulting mixture was extracted with DCM. The organic layer was washed with brine, dried over anhydrous Na$_2$SO$_4$, filtered, and concentrated to dryness. The remaining residue was purified by column chromatography on silica gel (eluted with DCM/MeOH) to afford compound 125. $^1$H NMR (400 MHz, DMSO-d$_6$) δ 0.97-1.05 (m, 2H), 1.33 (s, 3H), 2.05 (s, 4H), 2.53-2.58 (m, 1H), 2.65 (s, 3H), 3.19 (s, 6H), 3.54-3.62 (m, 1H), 4.41 (dd, J=5.1, 9.3 Hz, 1H), 5.55 (d, J=17.2 Hz, 1H), 5.88 (d, J=17.3 Hz, 1H), 7.45 (d, J=7.9 Hz, 1H), 7.63 (d, J=7.9 Hz, 1H), 7.71-7.81 (m, 2H), 8.30 (s, 1H), 8.71 (s, 2H), 10.26 (s, 1H).

Scheme 50: Synthesis of (1R,3S,5R)-2-(2-(3-Acetyl-5-(2-(methylpyrimidin-5-yl)-7-(trifluoromethyl)-1H-indazol-1-yl)acetyl)-N-(6-bromo-3-methylpyridin-2-yl)-5-methyl-2-azabicyclo[3.1.0]hexane-3-carbxamide (133)

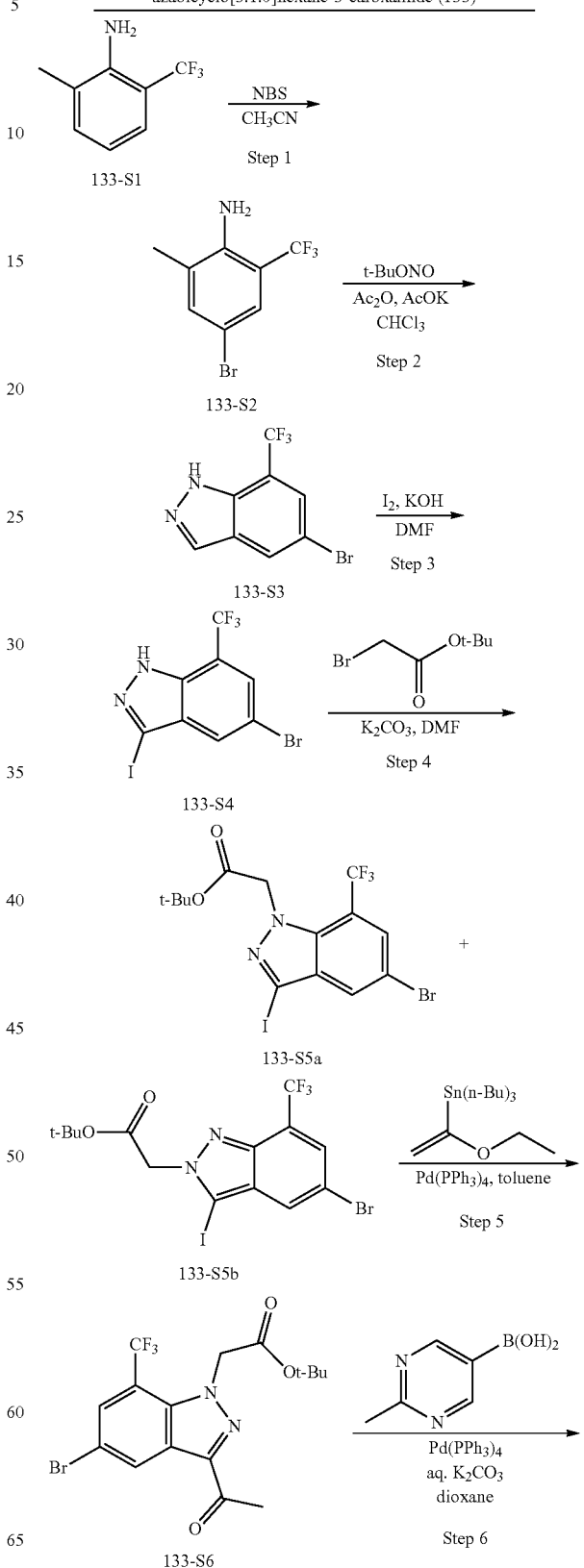

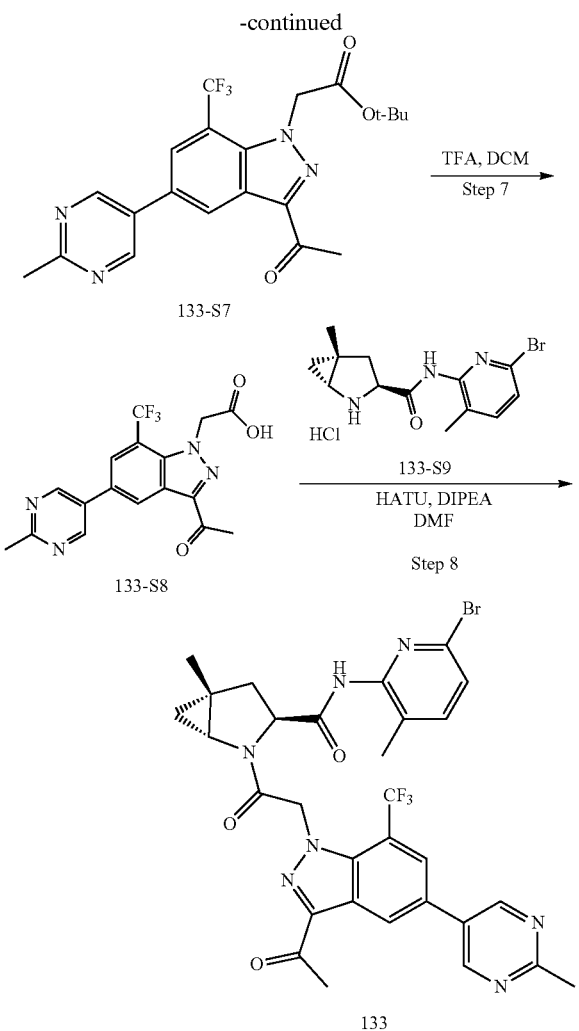

Step 1: 4-Bromo-2-methyl-6-(trifluoromethyl)aniline (133-S2)

To a solution of 133-S1 (1.0 g, 5.7 mmol) in MeCN (15 mL) was added N-bromosuccinimide (1.0 g, 5.7 mmol) in portions at 0° C. The reaction mixture was allowed to stir for 1 hour at room temperature. The reaction mixture was poured into water and extracted with EtOAc twice. The combined organics were washed with brine, dried over $Na_2SO_4$, filtered, and concentrated. The remaining residue was purified by chromatography on silica gel (eluted with PE) to afford 133-S2 (1.3 g, 90.3% yield) as a brown oil. LC/MS (ESI) m/z: 254 (M+H)$^+$.

Step 2: 5-Bromo-7-(trifluoromethyl)-1H-indazole (133-S3)

To a mixture of 133-S2 (700 mg, 2.77 mmol) and potassium acetate (325.8 mg, 3.32 mmol) in $CHCl_3$ (20 mL) was added dropwise acetic anhydride (846.6 mg, 8.30 mmol) at 0° C. The resulting mixture was stirred at room temperature for 1 hour. The reaction mixture was heated to 60° C. and tert-butyl nitrite (570.6 mg, 5.54 mmol) was added. After stirring overnight at 60° C., the mixture was diluted with water and extracted with DCM twice. The combined organic layers were washed with brine, dried over anhydrous $Na_2SO_4$, and concentrated under reduced pressure. The remaining residue was dissolved in MeOH (5 mL) and 6 N HCl (5 mL). The mixture was stirred at room temperature for 4 hours, basified with 10 N aqueous NaOH solution, and extracted with DCM twice. The combined organic layers were washed with brine, dried over anhydrous $Na_2SO_4$, and concentrated under reduced pressure. The remaining residue was purified by column chromatography on silica gel (PE/EtOAc=10:1 to 3:1) to afford 133-S3 (420 mg, 57.5% yield) as a yellow oil. LC/MS (ESI) m/z: 265 (M+H)$^+$.

Step 3: 5-Bromo-3-iodo-7-(trifluoromethyl)-1H-indazole (133-S4)

To a solution of 133-S3 (420 mg, 1.6 mmol) in DMF (6 mL) was added KOH (201.6 mg, 3.6 mmol) followed by $I_2$ (605.7 mg, 2.4 mmol) in portions at 0° C. The resulting mixture was stirred at room temperature for 1 hour. The mixture was diluted with water and extracted with EtOAc twice. The combined organic layers were washed with 5% aqueous $Na_2S_2O_3$ solution and brine, dried over anhydrous $Na_2SO_4$, and concentrated to afford 133-S4 (610 mg, 97.7% yield) as a yellow solid, which was carried forward without further purification. LC/MS (ESI) m/z: 391 (M+H)$^+$.

Step 4: tert-Butyl 2-(5-bromo-3-iodo-7-(trifluoromethyl)-1H-indazol-1-yl)acetate (133-S5a) and tert-butyl 2-(5-bromo-3-iodo-7-(trifluoromethyl)-2H-indazol-2-yl)acetate (133-S5b)

To a solution of 133-S4 (610 mg, 1.57 mmol) in DMF (8 mL) was added $K_2CO_3$ (541.7 mg, 3.93 mmol) followed by tert-butyl 2-bromoacetate (399.8 mg, 2.05 mmol). The resulting mixture was stirred at room temperature overnight, diluted with water, and extracted with EtOAc twice. The combined organic layers were washed with brine, dried over anhydrous $Na_2SO_4$, and concentrated under reduced pressure. The remaining residue was purified by chromatography on silica gel (PE/EtOAc=1:0 to 50:1 to 30:1) to afford 133-S5a (173 mg, 21.8% yield) and 133-S5b (433 mg, 54.7% yield) as light yellow solids. LC/MS (ESI) m/z: 505 (M+H)$^+$.

Step 5: tert-Butyl 2-(3-acetyl-5-bromo-7-(trifluoromethyl)-1H-indazol-1-yl)acetate (133-S6)

To a solution of 133-S5a (144 mg, 0.28 mmol) in dry toluene (9 mL) were added tributyl(1-ethoxyvinyl)stannane (155 mg, 0.43 mmol) and $Pd(PPh_3)_4$ (33 mg, 0.028 mmol). The resulting mixture was stirred at 100° C. under an atmosphere of nitrogen overnight. The cooled reaction mixture was diluted with $H_2O$ and extracted with EtOAc twice. The combined organic layers were washed with brine, dried over anhydrous $Na_2SO_4$, and concentrated. The remaining crude product was dissolved in THF (0.5 mL) and 0.5 M HCl (5 mL) and stirred for 1.5 hours at room temperature. The reaction mixture was basified with 2 N aqueous NaOH solution and extracted with EtOAc twice. The combined organic layers were washed with brine, dried over anhydrous $Na_2SO_4$, and concentrated under reduced pressure. The remaining residue was purified by chromatography on silica gel (PE/EtOAc=50:1 to 30:1) to afford 133-S6 (86 mg, 71.4% yield) as a brown solid. LC/MS (ESI) m/z: 421 (M+H)$^+$.

Step 6: tert-Butyl 2-(3-acetyl-5-(2-methylpyrimidin-5-yl)-7-(trifluoromethyl)-1H-indazol-1-yl)acetate (133-S7)

To a mixture of 133-S6 (86 mg, 0.2 mmol), (2-methylpyrimidin-5-yl)boronic acid (42 mg, 0.31 mmol), and K₂CO₃ (70 mg, 0.51 mmol) in 1,4-dioxane (5 mL) and H₂O (1 mL) was added Pd(PPh₃)₄ (23 mg, 0.02 mmol). The reaction mixture was stirred at 90° C. under an atmosphere of nitrogen overnight. The mixture was filtered and the filtrate was diluted with water and extracted with EtOAc twice. The combined organic layers were washed with brine, dried over anhydrous Na₂SO₄, and concentrated under reduced pressure. The remaining residue was purified by chromatography on silica gel (PE/EtOAc=3:1 to 1:1) to afford 133-S7 (67 mg, 75.5% yield) as a yellow solid. LC/MS (ESI) m/z: 435 (M+H)⁺.

Step 7: 2-(3-Acetyl-5-(2-methylpyrimidin-5-yl)-7-(trifluoromethyl)-1H-indazol-1-yl)acetic Acid (133-S8)

To a solution of 133-S7 (35 mg, 0.08 mmol) in DCM (2 mL) was added TFA (1 mL). The reaction mixture was stirred at room temperature for 1.5 hours and then concentrated under reduced pressure to afford 133-S8 (31 mg, 100% yield) as a yellow solid, which was carried forward in the next synthetic step without further purification. LC/MS (ESI) m/z: 335 (M+H)⁺.

Step 8: (1R,3S,5R)-2-(2-(3-Acetyl-5-(2-methylpyrimidin-5-yl)-7-(trifluoromethyl)-1H-indazol-1-yl)acetyl)-N-(6-bromo-3-methylpyridin-2-yl)-5-methyl-2-azabicyclo[3.1.0]hexane-3-carboxamide (133)

To a mixture of 133-S8 (26 mg, 0.07 mmol) and 133-S9 (23 mg, 0.07 mmol) in DMF (2 mL) was added DIPEA (0.04 mL, 0.22 mmol) followed by HATU (41.8 mg, 0.11 mmol) and the reaction mixture was stirred at room temperature for 1 hour. The mixture was diluted with EtOAc, washed with 10% aqueous LiCl solution and brine, dried, and concentrated to afford the crude product, which was purified by preparative HPLC to afford 133 (11.0 mg, 3.28% yield) as a white solid. ¹H NMR (400 MHz, DMSO-d₆) δ 10.27 (s, 1H), 9.13 (s, 2H), 8.82 (s, 1H), 8.28 (s, 1H), 7.63 (d, J=8.0 Hz, 1H), 7.44 (d, J=7.9 Hz, 1H), 5.99 (d, J=18.1 Hz, 1H), 5.59 (d, J=17.9 Hz, 1H), 4.34-4.31 (m, 1H), 3.59-3.55 (m, 1H), 2.71 (d, J=2.1 Hz, 6H), 2.59-2.53 (m, 1H), 2.09-2.07 (m, 1H), 2.05 (s, 3H), 1.33 (s, 3H), 1.09-1.06 (m, 1H), 0.85-0.83 (m, 1H). LC/MS (ESI) m/z: 670 (M+H)⁺.

Scheme 51. Synthesis of (1R,3S,5R)-2-(2-(3-Acetyl-5-(2-methylpyrimidin-5-yl)-1H-indazol-1-yl)acetyl)-N-(3-((allyloxy)methyl)-6-bromopyridin-2-yl)-5-vinyl-2-azabicyclo[3.1.0]hexane-3-carboxamide (134)

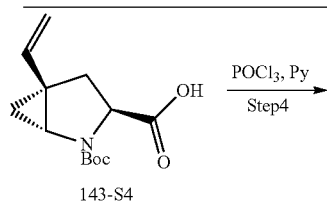

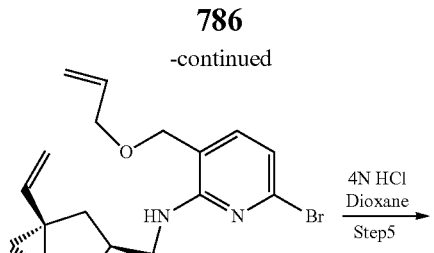

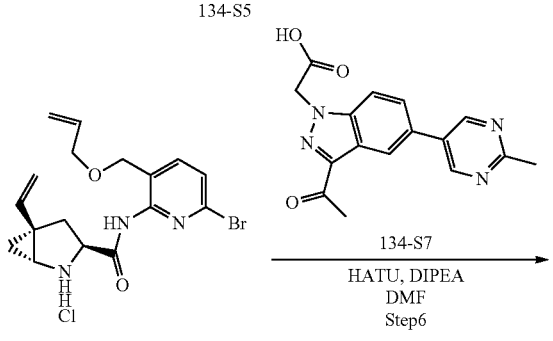

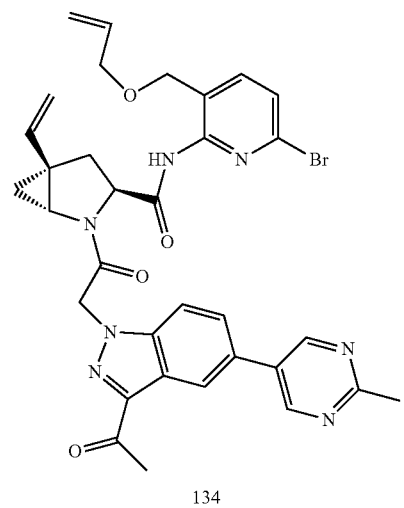 [SMILES: C=CCOCc1ccc(Br)nc1NC(=O)[C@@H]1C[C@@]2(C=C)C[C@H]2N1C(=O)Cn1nc(C(C)=O)c2cc(-c3cnc(C)nc3)ccc21]

Step 1: 2-(tert-Butyl) 3-ethyl (1R,3S,5S)-5-formyl-2-azabicyclo[3.1.0]hexane-2,3-dicarboxylate (134-S2)

To the solution of 2-(tert-butyl) 3-ethyl (1R,3S,5S)-5-(hydroxymethyl)-2-azabicyclo[3.1.0]hexane-2,3-dicarboxylate (134-S1, 67 mg, 0.23 mmol) in DCM (4 mL), Dess-Martin reagent (0.31 mmol) was added at 0° C. under argon. The mixture was stirred for an additional 3 hours, the reaction was diluted with DCM (20 mL), and quenched with aqueous NaHCO₃ (10%, 15 mL). The DCM layer was collected and the aqueous phase was extracted with DCM (15 mL×2). The DCM phase was combined, washed with brine, and dried over magnesium sulfate. The solution was filtered and concentrated to afford crude product 134-S2 (62 mg) that was carried forward without additional purification.

Step 2: 2-(tert-Butyl) 3-ethyl (1R,3S,5R)-5-vinyl-2-azabicyclo[3.1.0]hexane-2,3-dicarboxylate (134-S3)

To the suspension of methyltriphenylphosphonium bromide (111 mg, 0.31 mmol) in 5 mL of dry THF, BuLi (0.31 mmol) was added dropwise at 0° C. under argon. The mixture was stirred for 1 hour and a solution of aldehyde 134-S2 (62 mg) in THF (2 mL) was added dropwise. The mixture was warmed to room temperature and stirred overnight. The reaction was quenched with water (10 ml) and extracted with EtOAc (15 mL×3). The organic phases were combined, washed with brine and dried over magnesium sulfate. The solution was filtered, concentrated and purified to afford 134-S3 (31 mg). $^1$H NMR (400 MHz, CDCl$_3$) δ 0.89-0.94 (m, 1H), 1.04-1.08 (m, 1H), 1.28 (t, J=7.2 Hz, 3H), 1.44 (s, 9H), 2.32 (dd, J=13.2, 7.0 Hz, 1H), 2.43 (dd, J=13.1, 8.8 Hz, 1H), 3.43 (s, 1H), 3.97-4.09 (m, 1H), 4.16-4.26 (m, 2H), 4.99 (d, J=7.8 Hz, 1H), 5.02 (s, 1H), 5.70 (dd, J=17.0, 10.7 Hz, 1H) ppm.

Step 3: (1R,3S,5R)-2-(tert-Butoxycarbonyl)-5-vinyl-2-azabicyclo[3.1.0]hexane-3-carboxylic Acid (134-S4)

Compound 134-S3 (31 mg, 0.11 mmol) was dissolved in a mixture of CH$_3$OH—THF—H$_2$O (2 mL-2 mL-2 mL) and treated with LiOH (24 mg). The reaction mixture was stirred overnight at room temperature. The volatiles were evaporated under reduced pressure and the remaining residue was acidified with 10% citric acid (10 mL). The mixture was extracted with EtOAc (15 mL×3) and the combined organic layers were washed with water and brine and dried over MgSO$_4$. The solution was concentrated and the residue (134-S4, 26 mg) was dried and carried forward without additional purification.

Step 4: tert-Butyl (1R,3S,5R)-3-((3-((allyloxy)methyl)-6-bromopyridin-2-yl)carbamoyl)-5-vinyl-2-azabicyclo[3.1.0]hexane-2-carboxylate (134-S5)

(1R,3S,5R)-2-(tert-Butoxycarbonyl)-5-vinyl-2-azabicyclo[3.1.0]hexane-3-carboxylic Acid (134-S4, 26 mg, 0.10 mmol) and 3-((allyloxy)methyl)-6-bromopyridin-2-amine (27 mg, 0.11 mmol) were dissolved in anhydrous DCM (5 mL) in a pre-dried flask. The flask was cooled in an ice bath and dry pyridine (0.25 mL, 3.0 mmol) was added in one portion, followed by POCl$_3$ (100 μL, 1.0 mmol). After completion of the addition, the mixture was stirred for 4 hours at 0° C., and the reaction was quenched with water (15 mL). The DCM layer was collected and the aqueous phase was extracted with DCM (15 mL×2). The combined DCM solutions were washed with brine, and dried over MgSO$_4$. The solution was filtered and concentrated and the resulting residue was purified to afford 134-S5 (35 mg).

Step 5: (1R,3S,5R)—N-(3-((Allyloxy)methyl)-6-bromopyridin-2-yl)-5-vinyl-2-azabicyclo[3.1.0] hexane-3-carboxamide hydrochloride (134-S6)

tert-Butyl (1R,3S,5R)-3-((3-((allyloxy)methyl)-6-bromopyridin-2-yl)carbamoyl)-5-vinyl-2-azabicyclo[3.1.0]hexane-2-carboxylate (134-S5, 28 mg, 0.058 mmol) was taken up in 4N HCl dioxane (2.0 mL) and the resulting reaction mixture was stirred at room temperature for 2 hours. After completion of the reaction (as monitored by HPLC), the solvent was removed under reduced pressure. The remaining residue 134-S6 was used carried forward without additional purification.

Step 6: (1R,3S,5R)-2-(2-(3-Acetyl-5-(2-methylpyrimidin-5-yl)-1H-indazol-1-yl)acetyl)-N-(3-((allyloxy)methyl)-6-bromopyridin-2-yl)-5-vinyl-2-azabicyclo[3.1.0]hexane-3-carboxamide (134)

To the solution of (1R,3S,5R)—N-(3-((allyloxy)methyl)-6-bromopyridin-2-yl)-5-vinyl-2-azabicyclo[3.1.0]hexane-3-carboxamide hydrochloride (134-S6, 0.058 mmol) and 2-(3-acetyl-5-(2-methylpyrimidin-5-yl)-1H-pyrazolo[3,4-c]pyridin-1-yl)acetic acid (134-S7, 18 mg, 0.058 mmol) in DMF (2.0 mL), HATU (33 mg, 0.087 mmol) was added, followed by the dropwise addition of DIEA (5.0 eq) at room temperature. The mixture was stirred for 1 hour at room temperature and then the volatiles were evaporated. The residue was diluted with 10% sodium carbonate (50 mL) and extracted with ethyl acetate. The combined organic solutions were successively washed with water and brine and dried over MgSO$_4$. The solution was filtered and the solvent was removed. The residue was purified to afford 134 (8.1 mg). $^1$H NMR (400 MHz, DMSO-d$_6$): (major rotamer) δ 1.21-1.25 (m, 1H), 1.35-1.41 (m, 1H), 2.37-2.44 (m, 1H), 2.52-2.57 (m, 1H), 2.65 (s, 3H), 2.69 (s, 3H), 3.62-3.79 (m, 2H), 3.87-3.93 (m, 1H), 4.20 (d, J=3.2 Hz, 2H), 4.42-4.46 (m, 1H), 4.96-5.23 (m, 4H), 5.60 (d, J=17.3 Hz, 1H), 5.65-5.79 (m, 1H), 5.84 (dd, J=17.3, 10.6 Hz, 1H), 5.95 (d, J=17.3 Hz, 1H), 7.54 (d, J=8.1 Hz, 1H), 7.78 (d, J=8.1 Hz, 1H), 7.86 (s, 2H), 8.44 (s, 1H), 9.03 (s, 2H), 10.48 (s, 1H) ppm. LC (method A): t$_R$=2.15 min. LC/MS (EI) m/z: [M+H]$^+$ 670.20, 672.16

Scheme 52. Synthesis of (1R,3S,5R)-2-(2-(3-Acetyl-5-(2-methylpyrimidin-5-yl)-1H-indazol-1-yl)acetyl)-N-(3-bromoisoquinolin-1-yl)-5-methyl-2-azabicyclo[3.1.0]hexane-3-carboxamide (91) and (1R,3S,5R)-2-(2-(3-Acetyl-5-(2-methylpyrimidin-5-yl)-1H-indazol-1-yl)acetyl)-N-(6-chloro-3-((dimethylamino)methyl)pyridin-2-yl)-5-methyl-2-azabicyclo[3.1.0]hexane-3-carboxamide (135)

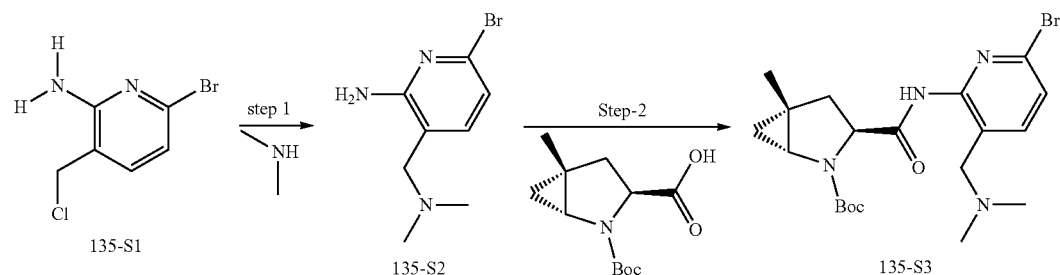

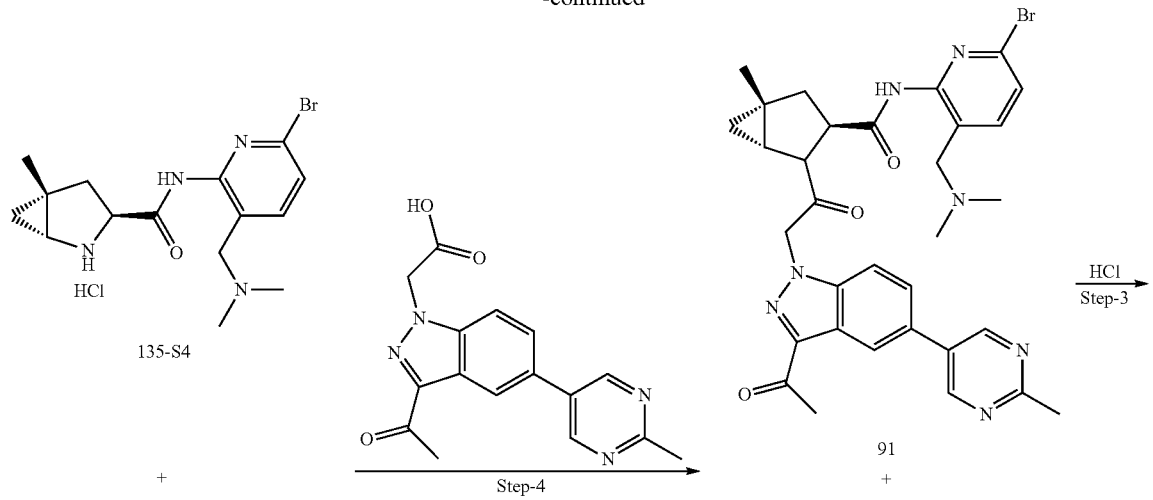

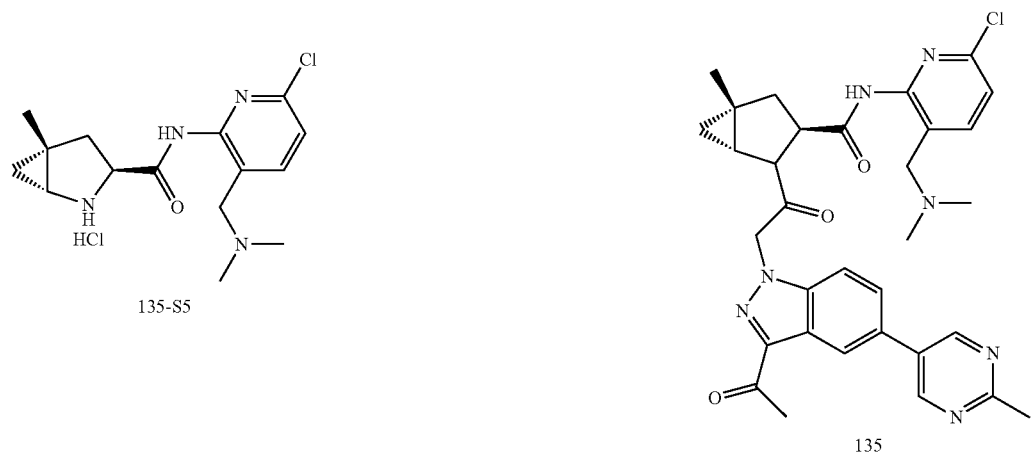

Step 1: 6-Bromo-3-((dimethylamino)methyl)pyridin-2-amine (135-S2)

To a stirred solution 6-bromo-3-(chloromethyl)pyridin-2-amine (133 mg, 1 equiv) in acetonitrile (10 mL) was added triethyl amine (0.3 mL, 3 equiv) and dimethyl amine hydrochloride (84 mg, 2 equiv) at 0-5° C. under an atmosphere of argon. The reaction mixture was stirred at room temperature before the reaction was diluted with DCM (10 mL) and basified with aqueous saturated NaHCO$_3$ solution (10 mL). The aqueous layer was extracted with DCM (2×10 mL) and the combined organic layers were washed with brine (10 mL), dried over Na$_2$SO$_4$ and concentrated to dryness to afford 135-S2 (100 mg, 99%).

Step 2: tert-Butyl (1R,3S,5R)-3-((6-bromo-3-((dimethylamino)methyl)pyridin-2-yl)carbamoyl)-5-methyl-2-azabicyclo[3.1.0]hexane-2-carboxylate (135-S3)

POCl$_3$ was added dropwise (0.08 mL, 2 equiv) at 0-5° C. under an atmosphere of argon to a stirred solution of (1R,3S,5R)-2-(tert-butoxycarbonyl)-5-methyl-2-azabicyclo[3.1.0]hexane-3-carboxylic acid (106 mg, 1 equiv) and 135-S2 (100 mg, 1 equiv) in DCM (20 mL) and pyridine (0.18 mL, 5 equiv). The reaction mixture was stirred at room temperature until completion before it was diluted with DCM (10 mL) and neutralized with aqueous saturated NaHCO$_3$ solution (10 mL). The aqueous layer was extracted with DCM (1×10 mL) and the combined organic layers were washed with brine (10 mL), dried over Na$_2$SO$_4$, and concentrated to dryness. The residue was purified by column chromatography on silica gel (eluted by 5% MeOH in DCM gradient) to afford 135-S3 (169 mg, 85%).

Step 3: (1R,3S,5R)—N-(6-Bromo-3-((dimethylamino)methyl)pyridin-2-yl)-5-methyl-2-azabicyclo[3.1.0]hexane-3-carboxamide hydrochloride (135-S4) and (1R,3S,5R)—N-(6-Chloro-3-((dimethylamino)methyl)pyridin-2-yl)-5-methyl-2-azabicyclo[3.1.0]hexane-3-carboxamide Hydrochloride (136-S5)

To a solution of 135-S3 (169 mg) was added 4N HCl in dioxane (15 mL) and the resulting solution was stirred at room temperature for 6 hours. The reaction mixture was concentrated to dryness to afford 135-S4 (133 mg).

Step 4: (1R,3S,5R)-2-(2-(3-Acetyl-5-(2-methylpyrimidin-5-yl)-1H-indazol-1-yl)acetyl)-N-(3-bromoisoquinolin-1-yl)-5-methyl-2-azabicyclo[3.1.0]hexane-3-carboxamide (91) and (1R,3S,5R)-2-(2-(3-Acetyl-5-(2-methylpyrimidin-5-yl)-1H-indazol-1-yl)acetyl)-N-(6-chloro-3-((dimethylamino)methyl)pyridin-2-yl)-5-methyl-2-azabicyclo[3.1.0]hexane-3-carboxamide (135)

HATU (233 mg, 1.2 equiv) was added at 0° C. under an atmosphere of argon to a solution of 135-S4 and 135-S5 (133 mg, 1 equiv), 2-(3-acetyl-5-(2-methylpyrimidin-5-yl)-1H-indazol-1-yl)acetic acid (158 mg, 1.2 equiv), and DIPEA (0.53 mL, 5 equiv) in DMF (10 mL). The reaction mixture was stirred at room temperature for 3 hours before it was diluted with EtOAc (30 mL) and water (15 mL). The aqueous layer was extracted with EtOAc (20 mL) and the combined organic layers were washed with brine (3×25 mL), dried over anhydrous $Na_2SO_4$, filtered and concentrated. The residue was purified by reverse phase chromatography on C18 (YMC pack, eluted with acetonitrile and water to afford 91 (60 mg, 24%) and 135 (15 mg).

Compound 91

$^1$H NMR (400 MHz, DMSO-$d_6$) δ 10.86 (s, 1H), 9.07 (s, 2H), 8.46 (s, 1H), 7.86-7.91 (m, 3H), 7.72 (d, 1H, J=8.3 Hz), 6.01 (d, 1H, J=17.1 Hz), 5.65 (d, 1H, J=17.1 Hz), 4.27 (t, 1H, J=8.5 Hz), 3.92-4.02 (m, 2H), 3.70-3.74 (m 1H), 2.71 (s, 3H), 2.66 (s, 3H), 2.54-2.61 (m, 1H), 2.32 (s, 3H), 2.16 (s, 3H), 1.98-2.05 (m, 1H), 1.35 (s, 3H), 0.96-1.07 (m, 2H).

Compound 135

$^1$H NMR (400 MHz, DMSO-$d_6$) δ 10.81 (s, 1H), 9.09 (s, 2H), 8.48 (s, 1H), 8.00 (d, 1H, J=8.4 Hz), 7.87-7.95 (m, 2H), 7.60 (d, 1H, J=8.4 Hz), 6.02 (d, 1H, J=16.8 Hz), 5.65 (d, 1H, J=16.8 Hz), 4.27 (t, 1H, J=8.2 Hz), 3.94-4.04 (m, 2H), 3.69-3.74 (m, 1H), 2.70 (s, 3H), 2.67 (s, 3H), 2.54-2.61 (m, 1H), 2.31 (s, 3H), 2.16 (s, 3H), 1.98-2.05 (m, 1H), 1.35 (s, 3H), 0.95-1.07 (m, 2H).

Scheme 53. Synthesis of (1R,3S,5R)-2-(2-(3-Acetyl-7-methyl-5-(2methylpyrimidin-5-yl)-1H-indazol-1-yl)acetyl)-N-(6-bromo-3-((dimethylamino)methyl)pyridin-2-yl)-5-methyl-2-azabicyclo[3.1.0]hexane-3-carboxamide (136) and (1R,3S,5R)-2-(2-(3-Acetyl-7-methyl-5-(2-methylpyrimidin-5-yl)-1H-indazol-1-yl)acetyl)-N-(6-chloro-3-((dimethylamino)methyl)pyridin-2-yl)-5-methyl-2-azabicyclo[3.1.0]hexane-3-carboxamide (137)

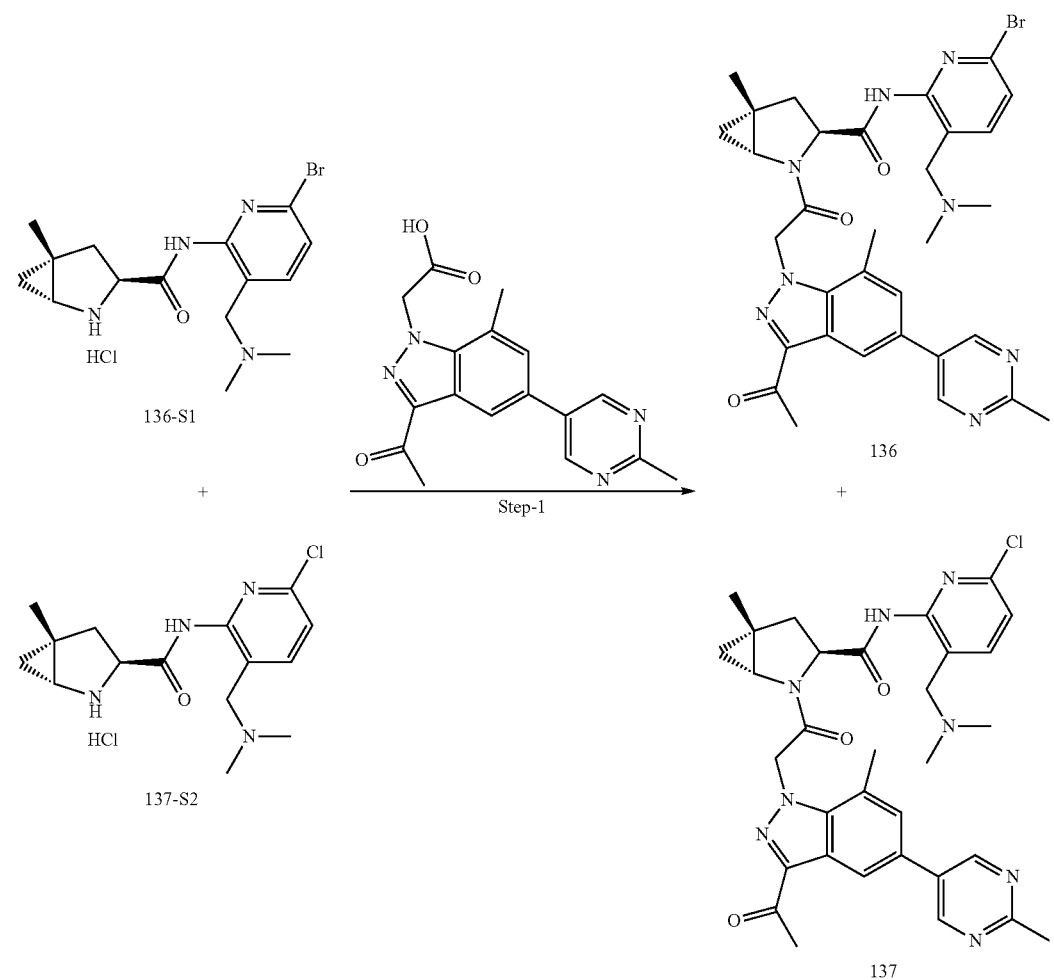

Step 1: (1R,3S,5R)-2-(2-(3-Acetyl-7-methyl-5-(2-methylpyrimidin-5-yl)-1H-indazol-1-yl)acetyl)-N-(6-bromo-3-((dimethylamino)methyl)pyridin-2-yl)-5-methyl-2-azabicyclo[3.1.0]hexane-3-carboxamide (136) and (1R,3S,5R)-2-(2-(3-Acetyl-7-methyl-5-(2-methylpyrimidin-5-yl)-1H-indazol-1-yl)acetyl)-N-(6-chloro-3-((dimethylamino)methyl)pyridin-2-yl)-5-methyl-2-azabicyclo[3.1.0]hexane-3-carboxamide (137)

HATU (100 mg, 1.2 equiv) was added at 0° C. under an atmosphere of argon to a solution of 136-S1 and 137-S2 (84 mg, 1 equiv), 2-(3-acetyl-7-methyl-5-(2-methylpyrimidin-5-yl)-1H-indazol-1-yl)acetic acid (71 mg, 1 equiv), DIPEA (0.2 mL, 5 equiv) in DMF (10 mL). The reaction mixture was stirred at room temperature for 3 hours before the reaction mixture was diluted with EtOAc (30 mL) and water (15 mL). The aqueous layer was extracted with EtOAc (15 mL) and the combined organic layers were washed with brine, dried over anhydrous $Na_2SO_4$, filtered and concentrated. The residue was purified by C18 HPLC column chromatography (eluted by ACN/water/TFA=20:80:0.1) to afford 136 (48 mg) and 137 (32 mg).

Compound 136

$^1$H NMR (400 MHz, DMSO-$d_6$) δ 10.89 (s, 1H), 9.06 (s, 2H), 8.33 (s, 1H), 7.95 (d, 1H, J=8.5 Hz), 7.72 (d, 11H, J=8.5 Hz), 7.65 (s, 1H), 6.13 (d, 11H, J=18.1 Hz), 5.73 (d, 1H, J=18.1 Hz), 4.26-4.31 (m, 1H), 3.91-4.03 (m, 3H), 2.73 (s, 3H), 2.70 (s, 3H), 2.65 (s, 3H), 2.54-2.61 (m, 1H), 2.27 (s, 3H), 2.14 (s, 3H), 1.97-2.00 (m, 1H), 1.35 (s, 3H), 0.96-1.00 (m, 2H).

Compound 137

$^1$H NMR (400 MHz, DMSO-$d_6$): δ 10.85 (s, 1H), 9.05 (s, 2H), 8.34 (s, 1H), 7.99 (d, 1H, J=8.0 Hz), 7.65 (s, 1H), 7.59 (d, 1H, J=8.0 Hz), 6.13 (d, 1H, J=17.9 Hz), 5.72 (d, 1H, J=17.9 Hz), 4.25-4.31 (m, 1H), 3.94-4.03 (m, 3H), 2.73 (s, 3H), 2.70 (s, 3H), 2.66 (s, 3H), 2.55-2.60 (m, 1H), 2.28 (s, 3H), 2.15 (s, 3H), 1.96-2.06 (m, 1H), 1.35 (s, 3H), 0.97-1.03 (m, 2H).

Scheme 54. Synthesis of (1R,3S,5R)-2-(2-(3-Acetyl-5-(2-methylpyrimidin-5-yl)-1H-indazol-1-yl)acetyl)-N-(6-bromo-3-(morpholinomethyl)pyridin-2-yl)5-methyl-2-azabicyclo[3.1.0]hexane-3-carboxamide (138) and (1R,3S,5R)-2-(2-(3-Acetyl-5-(2-methylpyrimidin-5-yl)-1H-indazol-1-yl)acetyl)-N-(6-chloro-3-(morpholinomethyl)pyridin-2-yl)-5-methyl-2-azabicyclo[3.1.0]hexane-3-carboxamide (139)

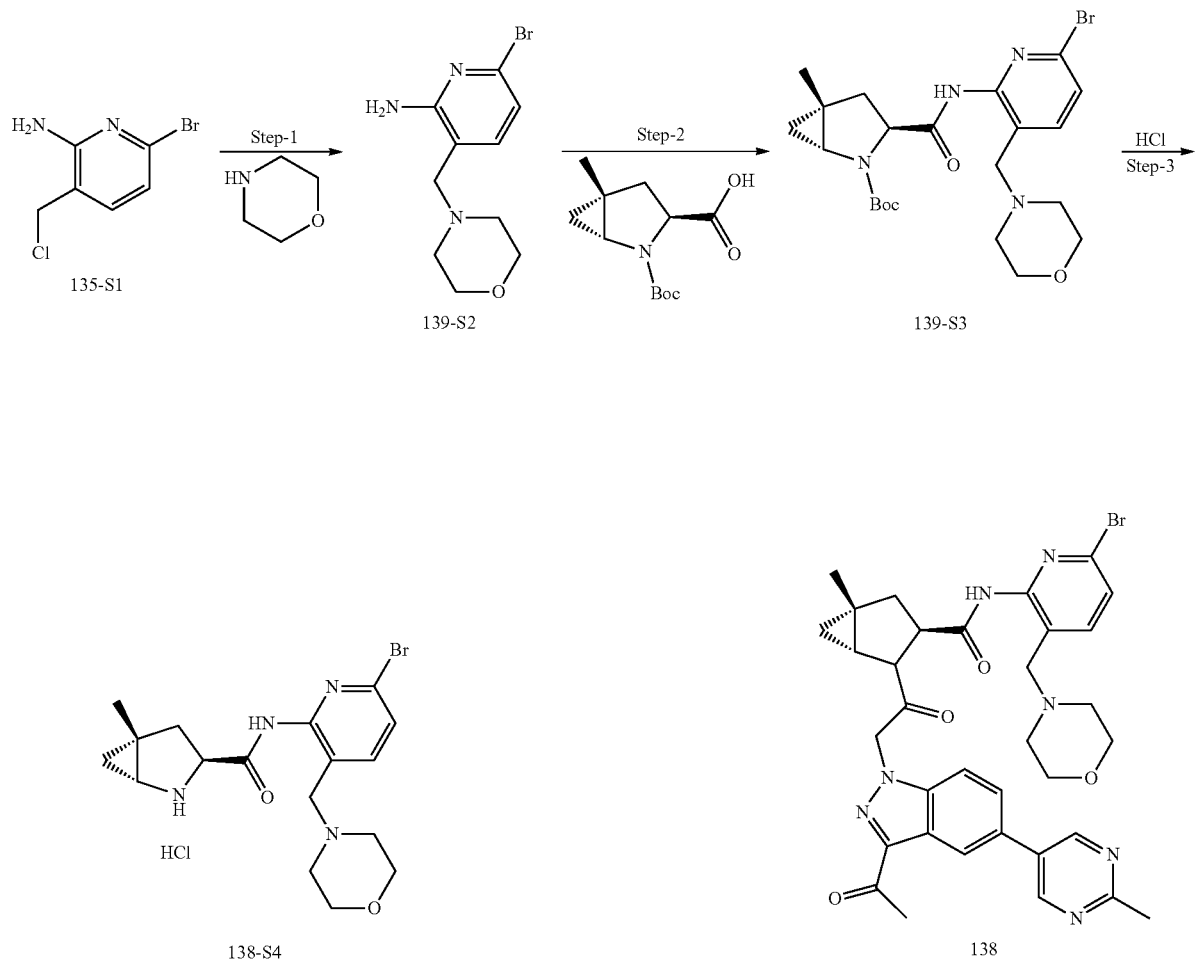

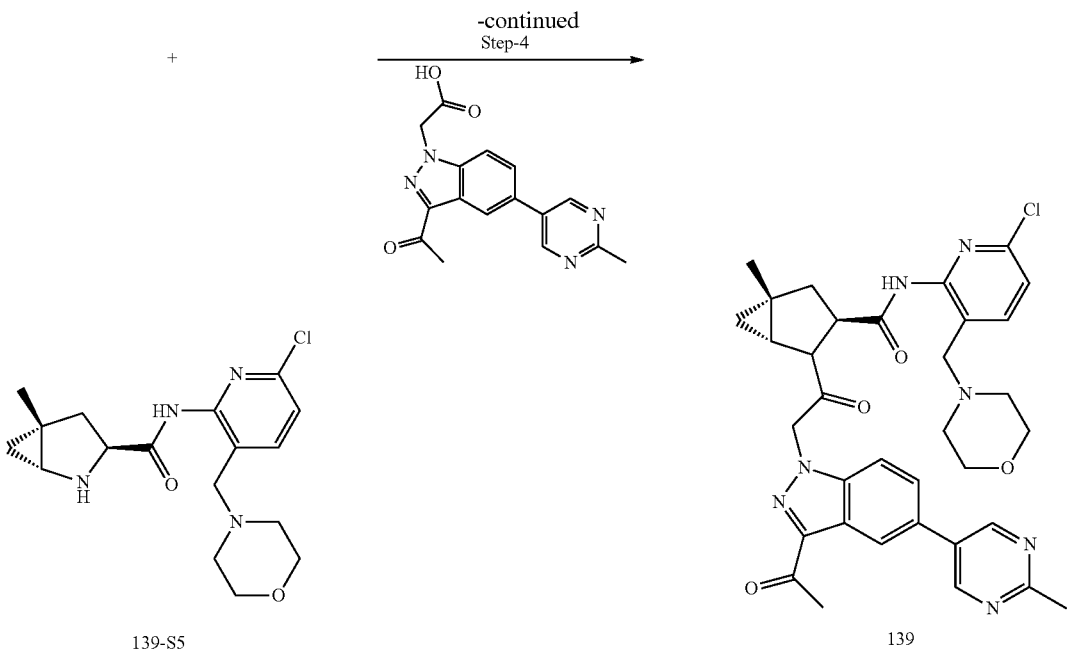

Step 1: 6-Bromo-3-(morpholinomethyl)pyridin-2-amine (139-S2)

To a stirred solution 6-bromo-3-(chloromethyl)pyridin-2-amine (241 mg, 1 equiv) and triethyl amine (0.48 mL, 3 equiv) in acetonitrile (20 mL) was added morpholine (162 mg, 2 equiv) at 0-5° C. under an atmosphere of argon. The reaction mixture was stirred at room temperature until completion. The reaction was diluted with DCM (25 mL) and basified with aqueous saturated NaHCO$_3$ solution (10 mL). The aqueous layer was extracted with DCM (2×10 mL) and the combined organic layers were washed with brine, dried over Na$_2$SO$_4$ and concentrated to dryness. The residue was purified by column chromatography on silica gel (eluted by 5% MeOH in DCM gradient) to afford 139-S2 (215 mg, 85%).

Step 2: tert-Butyl (1R,3S,5R)-3-((6-bromo-3-(morpholinomethyl)pyridin-2-yl)carbamoyl)-5-methyl-2-azabicyclo[3.1.0]hexane-2-carboxylate (139-S3)

POCl$_3$ was added dropwise (0.03 mL, 2 equiv) at 0-5° C. under an atmosphere of argon to a stirred solution of (1R,3S,5R)-2-(tert-butoxycarbonyl)-5-methyl-2-azabicyclo[3.1.0]hexane-3-carboxylic acid (69 mg, 1 equiv) and 139-S2 (78 mg, 1 equiv) in DCM (10 mL) and pyridine (0.12 mL, 5 equiv). The reaction mixture was stirred at room temperature until completion. The reaction mixture was diluted with DCM (10 mL) and neutralized with aqueous saturated NaHCO$_3$ solution (10 mL). The aqueous layer was extracted with DCM (1×10 mL) and the combined organic layers were washed with brine, dried over Na$_2$SO$_4$ and concentrated to dryness. The residue was purified by column chromatography on silica gel (eluted by 5% MeOH in DCM gradient) to afford 139-S3 (87 mg, 70%).

Step 3: (1R,3S,5R)—N-(6-Bromo-3-(morpholinomethyl)pyridin-2-yl)-5-methyl-2-azabicyclo[3.1.0]hexane-3-carboxamide hydrochloride (138-S4) and (1R,3S,5R)—N-(6-Chloro-3-(morpholinomethyl)pyridin-2-yl)-5-methyl-2-azabicyclo[3.1.0]hexane-3-carboxamide Hydrochloride (139-S5)

To a solution of 139-S3 (87 mg) was added 4N HCl in dioxane (10 mL) and the resulting solution was stirred at room temperature for 6 hours. The reaction mixture was concentrated to dryness to afford 138-S4 and 139-S5.

Step 4: (1R,3S,5R)-2-(2-(3-Acetyl-5-(2-methylpyrimidin-5-yl)-1H-indazol-1-yl)acetyl)-N-(6-bromo-3-(morpholinomethyl)pyridin-2-yl)-5-methyl-2-azabicyclo[3.1.0]hexane-3-carboxamide (138) and (1R,3S,5R)-2-(2-(3-Acetyl-5-(2-methylpyrimidin-5-yl)-1H-indazol-1-yl)acetyl)-N-(6-chloro-3-(morpholinomethyl)pyridin-2-yl)-5-methyl-2-azabicyclo[3.1.0]hexane-3-carboxamide (139)

HATU (68 mg, 1.2 equiv) was added at 0° C. under an atmosphere of argon to a solution of 138-S4 and 139-S5 (65 mg, 1 equiv), 2-(3-acetyl-5-(2-methylpyrimidin-5-yl)-1H-indazol-1-yl)acetic acid (47 mg, 1.05 equiv), and DIPEA (0.13 mL, 5 equiv) in DMF (10 mL). The reaction mixture was stirred at room temperature for 3 hours before the reaction mixture was diluted with EtOAc (35 mL) and water (15 mL). The aqueous layer was extracted with EtOAc (20 mL) and the combined organic layers were washed with brine, dried over anhydrous Na$_2$SO$_4$, filtered and concentrated. The residue was purified by HPLC column chromatography on C18 (eluted with ACN/water/TFA=20/80/0.1) to afford 138 (30 mg) and 139 (12 mg).

Compound 138

$^1$H NMR (400 MHz, DMSO-d$_6$): δ 10.72 (s, 1H), 8.97 (s, 2H), 8.39 (s, 1H), 7.70-7.89 (m, 3H), 7.57 (s, 1H), 5.98 (d, 1H, J=17.5 Hz), 5.55 (d, 1H, J=17.5 Hz), 4.13-4.27 (m, 1H), 3.86-4.02 (m, 4H), 3.63-3.73 (m, 1H), 2.62 (s, 3H), 2.59 (s, 3H), 2.46-2.52 (m, 1H), 2.33 (s, 2H), 2.11-2.24 (m, 4H), 1.89-2.09 (m, 1H), 1.26 (s, 3H), 0.87-0.99 (m, 2H).

Compound 139

$^1$H NMR (400 MHz, DMSO-d$_6$): δ 10.69 (s, 1H), 8.98 (s, 2H), 9.33 (s, 1H), 8.38 (s, 1H), 7.79-7.93 (m, 3H), 7.46 (s, 1H), 5.96 (d, 1H, J=17.2 Hz), 5.55 (d, 1H, J=17.2 Hz), 4.14-4.32 (m, 1H), 3.80-4.02 (m 1H), 3.57-3.69 (m, 4H), 3.06 (s, 2H), 2.62 (s, 3H), 2.59 (s, 3H), 2.47-2.52 (m, 1H), 1.92-2.13 (m, 5H), 1.28 (s, 3H), 0.89-0.99 (m, 2H).

Scheme 55: Synthesis of (1R,3S,5R)-2-(2-(3-Acetyl-7-cyano-5-(2-methylpyrimidin-5-yl)-1H-indazol-1-yl)acetyl)-N-(6-bromo-3-methylpyridin-2-yl)-5-((dimethylamino)methyl)-2-zabicyclo[3.1.0]hexane-3-carboxamide (143) and (1S,3S)-2-(2-(3-Acetyl-7-cyano-5-(2-methylpyrimidin-5-yl)-1H-indazol-1-yl)aceteyl)-N-(6-bromo-3-methylpyridin-2-yl)-5-((dimethylamino)methyl)-2-azabicyclo[3.1.0]hexane-3-carboxamide (144)

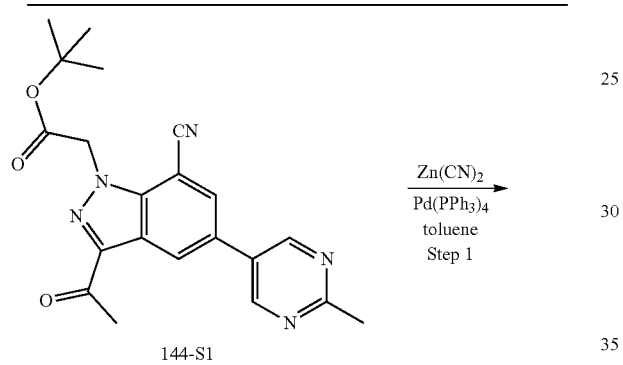

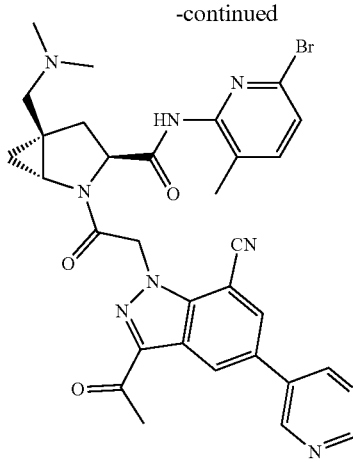

143

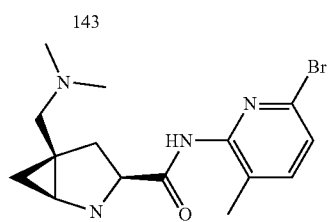

144

Step 1: tert-Butyl 2-(3-acetyl-7-cyano-5-(2-methylpyrimidin-5-yl)-1H-indazol-1-yl)acetate (144-S2)

A sealable vial was charged with 144-S1 (50 mg, 0.112 mmol), Zn(CN)$_2$ (53 mg, 0.449 mmol), Pd(PPh$_3$)$_4$ (7 mg, 0.056 mmol), and toluene (3 mL) under an atmosphere of nitrogen. The vial was sealed and irradiated in the microwave reactor at 150° C. for 2 hours. The mixture was diluted with EtOAc and filtered. The filtrate was concentrated and the remaining residue was purified by preparative TLC to afford 144-S2 (42 mg, 95.9% yield) as a white solid. LC/MS (ESI) m/z: 392 (M+H)$^+$.

Step 2: 2-(3-Acetyl-7-cyano-5-(2-methylpyrimidin-5-yl)-1H-indazol-1-yl)acetic Acid (144-S3)

To a solution of 144-S2 (42 mg, 0.102 mmol) in DCM (1 mL) was added TFA (1 mL). The resulting mixture was stirred at room temperature for 2 hours and concentrated to afford 144-S3 (36 mg, 100% yield) as a white solid, which was carried forward in the next synthetic step without purification. LC/MS (ESI) m/z: 336 (M+H)$^+$.

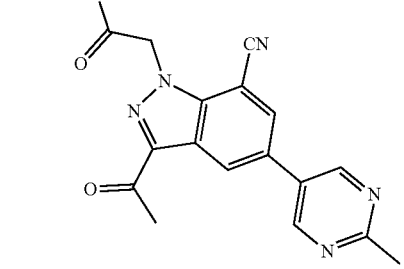

Step 3: (1R,3S,5R)-2-(2-(3-Acetyl-7-cyano-5-(2-methylpyrimidin-5-yl)-1H-indazol-1-yl)acetyl)-N-(6-bromo-3-methylpyridin-2-yl)-5-((dimethylamino)methyl)-2-azabicyclo[3.1.0]hexane-3-carboxamide (143) and (1S,3S)-2-(2-(3-acetyl-7-cyano-5-(2-methylpyrimidin-5-yl)-1H-indazol-1-yl)acetyl)-N-(6-bromo-3-methylpyridin-2-yl)-5-((dimethylamino)methyl)-2-azabicyclo[3.1.0]hexane-3-carboxamide (144)

To a solution of 144-S3 (35 mg, 0.093 mmol), 144-S4 (37 mg, 0.093 mmol), and DIPEA (40 mg, 0.279 mmol) in DMF (1 mL) at room temperature was added HATU (79 mg, 0.186 mmol). The resulting mixture was stirred at room temperature overnight. The mixture was diluted with EtOAc, washed with 5% aqueous LiCl solution and brine, dried over $Na_2SO_4$, filtered, and concentrated to dryness. The remaining residue was purified by preparative HPLC to afford 143 (3 mg, yield 4.8% yield) and 144 (1 mg, 1.6% yield) as white solids.

Compound 143

$^1$H NMR (400 MHz, $CD_3OD$) δ 9.06 (s, 2H), 8.89 (d, J=1.6 Hz, 1H), 8.32 (d, J=1.6 Hz, 1H), 7.59 (d, J=8.1 Hz, 1H), 7.43 (d, J=7.9 Hz, 1H), 6.08 (d, J=17.8 Hz, 1H), 6.00 (d, J=17.8 Hz, 1H), 4.73 (m, 1H), 3.89-3.84 (m, 1H), 3.50 (m, 2H), 3.13 (d, J=14.0 Hz, 1H), 2.90 (s, 6H), 2.79 (s, 3H), 2.73 (s, 3H), 2.62 (m, 1H), 2.15 (s, 3H), 1.58 (d, J=3.1 Hz, 1H), 1.50 (m, 1H). LC/MS (ESI) m/z: 670 (M+H)$^+$.

Compound 144

$^1$H NMR (400 MHz, $CD_3OD$) δ 9.07 (s, 2H), 8.90 (d, J=1.6 Hz, 1H), 8.34 (d, J=1.6 Hz, 1H), 7.57 (d, J=8.1 Hz, 1H), 7.41 (d, J=7.9 Hz, 1H), 6.18 (d, J=17.7 Hz, 1H), 5.90 (d, J=17.6 Hz, 1H), 5.19 (m, 1H), 4.00 (m, 1H), 3.70 m, 1H), 3.50 (m, 1H), 3.21-3.15 (m, 1H), 2.98 (s, 6H), 2.79 (s, 3H), 2.73 (s, 3H), 2.62 (m, 1H), 2.19-2.08 (m, 3H), 1.90 (s, 1H), 1.42 (m, 1H). LC/MS (ESI) m/z: 670 (M+H)$^+$.

Scheme 56: Synthesis of 1-(2-((1R,3S,5R)-3-((6-Bromo-3-methylpyridin-2-yl)carbamoyl)-5-methyl-2-azabicyclo[3.1.0]hexan-2-yl)-2-oxoethyl)-4-fluoro-5-(2-methylpyrimidin-5-yl)-1H-indazole-3-carboxamide (145)

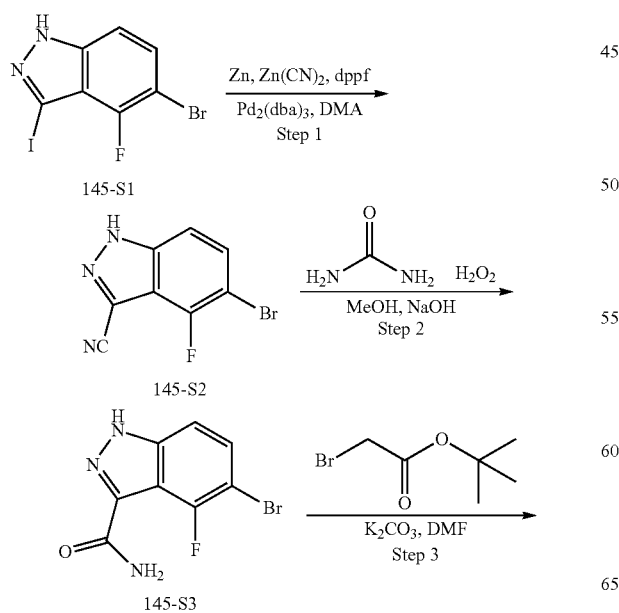

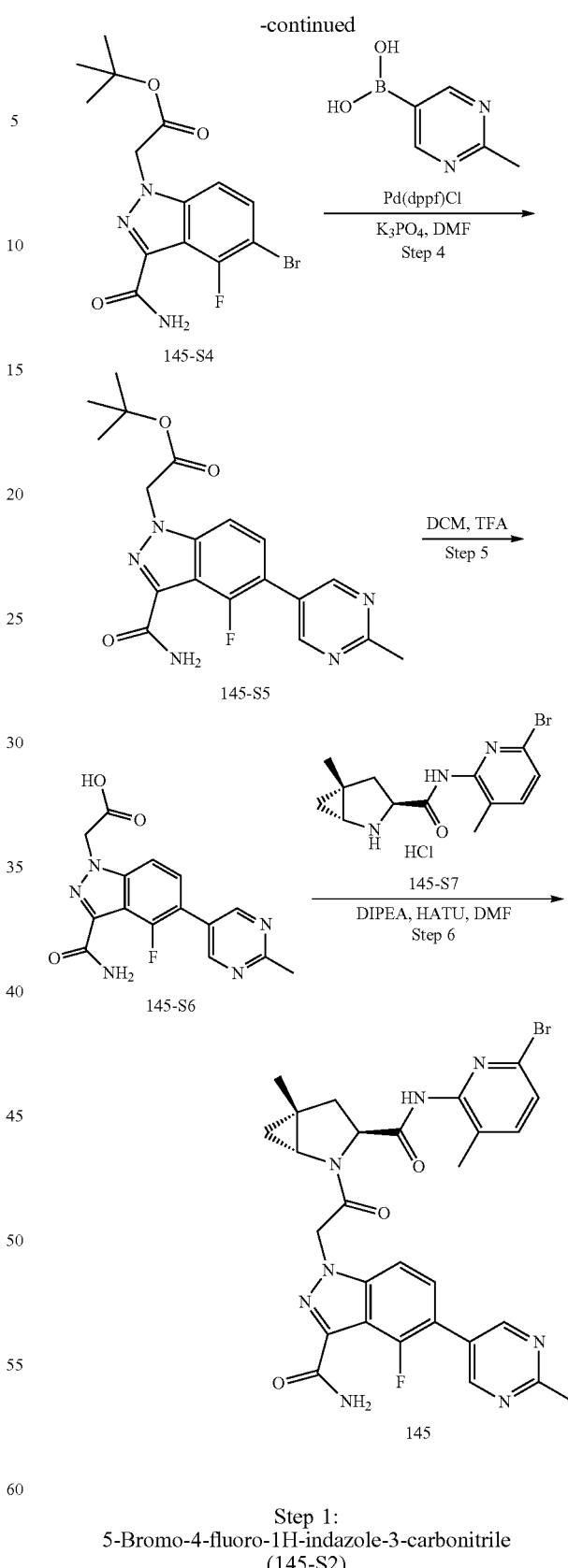

Step 1:
5-Bromo-4-fluoro-1H-indazole-3-carbonitrile (145-S2)

To a solution of 145-S1 (800 mg, 2.346 mmol) in DMA (8 mL) was added Zn powder (18 mg, 0.28200 mmol), $Zn(CN)_2$ (138 mg, 1.173 mmol), dppf (52 mg, 0.094 mmol), Pd₂(dba)₃ (43 mg, 0.0469 mmol) and the mixture was purged with nitrogen. The reaction mixture was heated at 100° C. overnight under an atmosphere of nitrogen. The solution was cooled to room temperature and partitioned between EtOAc and 0.5 N aqueous HCl. The organic phase was washed twice with 0.5 N aqueous HCl and brine, and dried over Na₂SO₄. The mixture was filtered and concentrated to dryness. The remaining residue was purified by column chromatography on silica gel (eluted with PE/EtOAc=5:1) to afford 145-S2 (469 mg, 83.3% yield) as a white solid. LC/MS (ESI) m/z: 240 (M+H)⁺.

Step 2: 5-Bromo-4-fluoro-1H-indazole-3-carboxamide (145-S3)

To a solution of 145-S2 (469 mg, 1.95 mmol) in MeOH (25 mL) at 0° C. was added an ice-cooled solution of urea hydrogen peroxide (1.8 g, 19.54 mmol) in 1 N aqueous NaOH solution (25 mL, 19.54 mmol) and the reaction mixture was stirred at room temperature overnight. The mixture was concentrated to half volume and extracted with EtOAc twice. The combined organic layers were washed with brine, dried over Na₂SO₄, filtered, and concentrated to dryness to afford 145-S3 (270 mg, 54% yield) as a white solid. LC/MS (ESI) m/z: 258 (M+H)⁺.

Step 3: tert-Butyl 2-(5-bromo-3-carbamoyl-4-fluoro-1H-indazol-1-yl)acetate (145-S4)

To a solution of 145-S3 (270 mg, 1.05 mmol) in DMF (2 mL) were added tert-butyl 2-bromoacetate (0.18 mL, 1.26 mmol) and K₂CO₃ (363 mg, 2.625 mmol). The mixture was stirred at room temperature overnight. The mixture was diluted water, extracted with EtOAc, washed with 10% aqueous LiCl solution and brine, and dried over Na₂SO₄. The mixture was filtered and concentrated to dryness. The remaining residue was purified by column chromatography on silica gel (eluted with PE/EtOAc=1:1) to afford 145-S4 (210 mg, 53.7% yield) as a white solid. LC/MS (ESI) m/z: 372 (M+H)⁺.

Step 4: tert-Butyl 2-(3-carbamoyl-4-fluoro-5-(2-methylpyrimidin-5-yl)-1H-indazol-1-yl)acetate (145-S5)

To a solution of 145-S4 (41 mg, 0.11 mmol) and 2-methylpyrimidin-5-ylboronic acid (18 mg, 0.13 mmol) in DMF (2 mL) was added K₃PO₄ (0.17 mL, 2 N, 0.33 mmol) and Pd(dppf)Cl₂ (4 mg, 0.005 mmol) under an atmosphere of nitrogen. The reaction mixture was further purged with nitrogen and stirred at 100° C. for 3 hours. The mixture was poured into ice water and extracted with EtOAc, washed with 10% aqueous LiCl solution and brine, and dried over Na₂SO₄. The mixture was filtered and concentrated to dryness. The remaining residue was purified by column chromatography on silica gel (eluted with DCM/MeOH=50:1) to afford 145-S5 (32 mg, 76% yield) as a white solid. LC/MS (ESI) m/z: 386 (M+H)⁺.

Step 5: 2-(3-Carbamoyl-4-fluoro-5-(2-methylpyrimidin-5-yl)-1H-indazol-1-yl)acetic Acid (145-S6)

To a solution of 145-S5 in DCM (2 mL) was added TFA (1 mL) at 0° C. and the reaction mixture was stirred at room temperature for 3 hours. The mixture was concentrated to dryness under reduced pressure to afford 145-S6 (32 mg, 100% yield), which was carried forward in the next synthetic step without further purification LC/MS (ESI) m/z: 330 (M+H)⁺.

Step 6: 1-(2-(((1R,3S,5R)-3-((6-Bromo-3-methylpyridin-2-yl)carbamoyl)-5-methyl-2-azabicyclo[3.1.0]hexan-2-yl)-2-oxoethyl)-4-fluoro-5-(2-methylpyrimidin-5-yl)-1H-indazole-3-carboxamide (145)

To a mixture of 145-S6 (32 mg, 0.097 mmol), 145-S7 (52 mg, 0.126 mmol), and HATU (74 mg, 0.194 mmol) in DMF (1 mLl) was added DIPEA (0.1 mL, 0.582 mmol) and the reaction mixture was stirred at room temperature for 2 hours. The mixture was diluted with EtOAc, washed with 10% aqueous LiCl solution and brine, dried over Na₂SO₄, filtered, and concentrated under reduced pressure. The remaining residue was purified by preparative HPLC to afford 145 (7 mg, 12% yield) as a light a yellow solid. ¹H NMR (400 MHz, CD₃OD) δ 8.93 (s, 2H), 7.64-7.53 (m, 3H), 7.38 (d, J=8 Hz, 1H), 5.76-5.59 (m, 2H), 4.54-4.50 (m, 1H), 3.53-5.50 (m, 1H), 2.73 (s, 3H), 2.65-2.58 (m, 1H), 2.32-2.27 (m, 1H), 2.12 (s, 3H), 1.40 (s, 3H), 1.07 (t, J=5.6 Hz, 1H), 0.97-0.95 (m, 1H). LC/MS (ESI) m/z: 621 (M+H)⁺.

Scheme 57: Synthesis of (1R,3S,5R)-2-(2-(3-Acetyl-7-(difluoromethyl)-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (146)

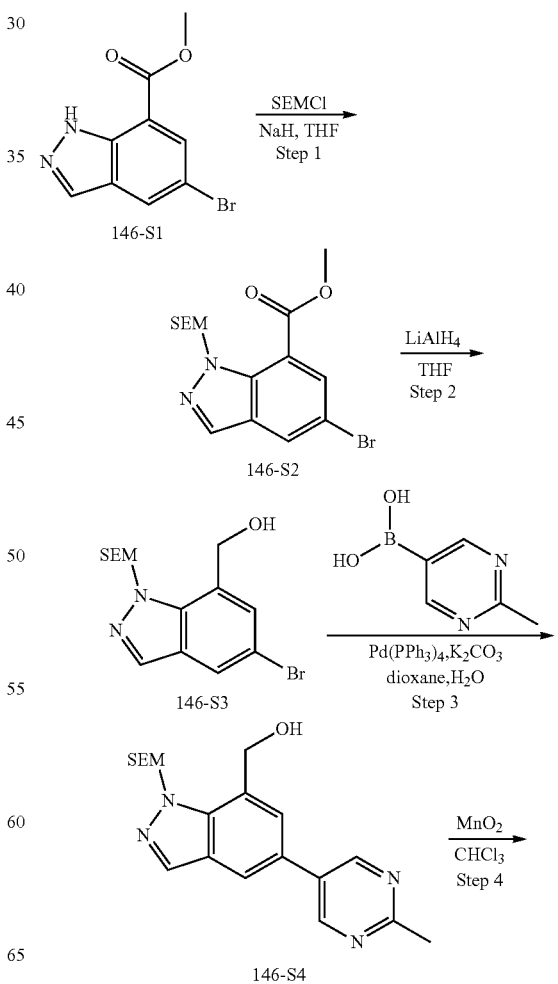

803
-continued

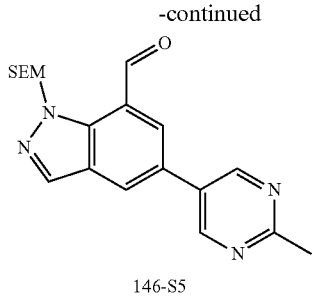
146-S5

DAST
DCM
Step 5

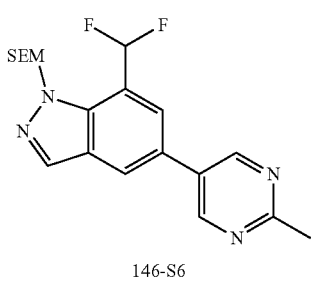
146-S6

TFA
DCM
Step 6

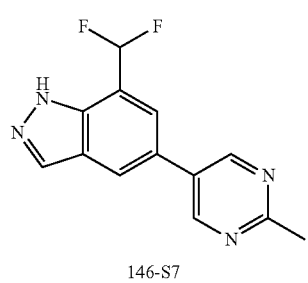
146-S7

I₂
KOH,DMF
Step 7

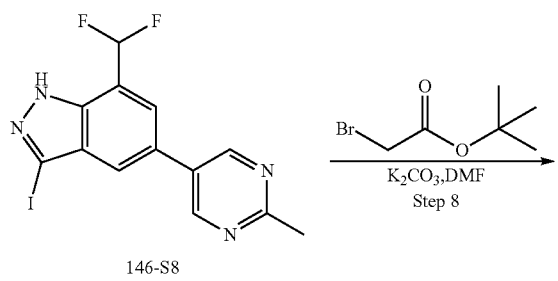
146-S8

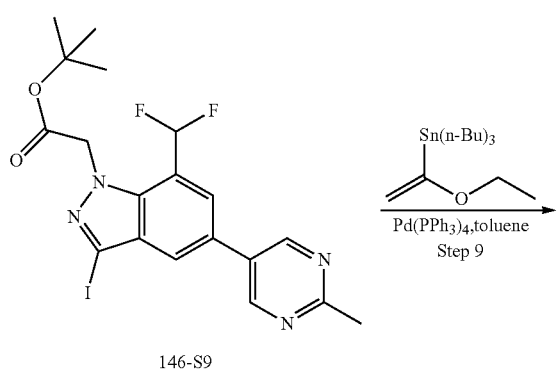
146-S9

Sn(n-Bu)₃
Pd(PPh₃)₄,toluene
Step 9

804
-continued

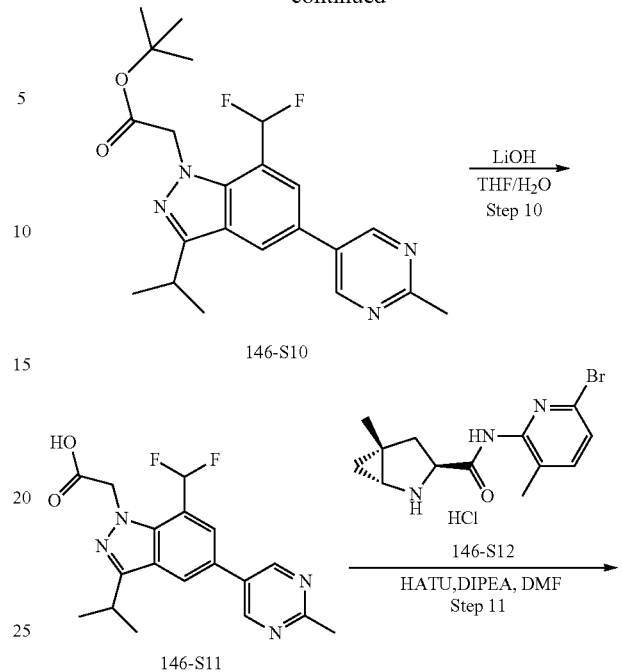
146-S10

LiOH
THF/H₂O
Step 10

146-S11

146-S12

HATU,DIPEA, DMF
Step 11

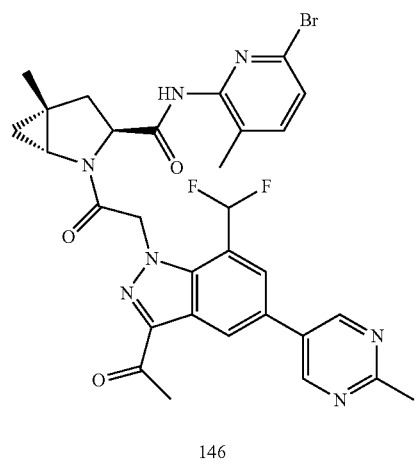 [SMILES: CC(=O)c1nn(CC(=O)N2[C@H](C(=O)Nc3nc(Br)ccc3C)C[C@@]3(C)C[C@@H]23)c2c(C(F)F)cc(-c3cnc(C)nc3)cc12]
146

Step 1: Methyl 5-bromo-1-((2-(trimethylsilyl)ethoxy)methyl)-1H-indazole-7-carboxylate (146-S2)

To a solution of 146-S1 (765 mg, 3 mmol) in dry THF (2 mL) was added NaH (144 mg, 3.6 mmol, 60% dispersion in mineral oil) at 0° C. The reaction mixture was stirred at 0° C. for 30 minutes, SEMCl (648 mg, 3.9 mmol) was added into the above mixture, and the resulting mixture was stirred at room temperature for 2 hours. The mixture was then quenched with saturated NH₄Cl solution and extracted with EtOAc. The organic layer was separated, dried over Na₂SO₄, and concentrated to afford the crude product, which was purified by column chromatography on silica gel (eluted with PE/EtOAc=100:0 to 7:1) to afford 146-S2 (750 mg, 65.1% yield) as a white solid. LC/MS (ESI) m/z: 385 (M+H)⁺.

Step 2: (5-Bromo-1-((2-(trimethylsilyl)ethoxy)methyl)-1H-indazol-7-yl)methanol (146-S3)

To a solution of 146-S2 (750 mg, 1.95 mmol) in dry THF (20 mL) was added LiAlH₄ (148 mg, 3.5 mmol) at 0° C. in small portions. The reaction mixture was stirred at 0° C. for 30 minutes and then warmed to room temperature for 1 hour. The mixture was then quenched slowly with water (0.75 mL), 10% aqueous NaOH solution (1.5 mL), and water (2.25 mL). The resulting mixture was filtered and the filtrate was diluted with EtOAc, dried over $Na_2SO_4$, and concentrated to afford the crude product, which was purified by column chromatography on silica gel (eluted with PE/EA=100:1 to 5:1) to afford 146-S3 (494 mg, 71.1% yield) as a colorless oil. LC/MS (ESI) m/z: 357 (M+H)+.

Step 3: (5-(2-Methylpyrimidin-5-yl)-1-((2-(trimethylsilyl)ethoxy)methyl)-1H-indazol-7-yl)methanol (146-S4)

To a solution of 146-S3 (494 mg, 1.384 mol) in 1,4-dioxane/$H_2O$ (28 mL, 6:1) was added 2-methylpyrimidin-5-ylboronic acid (210 mg, 1.52 mmol), $K_2CO_3$ (573 mg, 4.152 mmol), and Pd(PPh$_3$)$_4$ (128 mg, 0.111 mmol). The reaction mixture was stirred at 95° C. for 16 hours under an atmosphere of nitrogen. After cooling, the mixture was diluted with water and extracted with DCM/MeOH (20:1). The organic layer was separated, dried, and concentrated to afford the crude product, which was purified by column chromatography on silica gel (eluted with DCM/MeOH=100:0 to 50:1) to afford 146-S4 (288 mg, 56.2% yield) as a colorless oil. LC/MS (ESI) m/z: 371 (M+H)+.

Step 4: 5-(2-Methylpyrimidin-5-yl)-1-((2-(trimethylsilyl)ethoxy)methyl)-1H-indazole-7-carbaldehyde (146-S5)

To a solution of 146-S4 (240 mg, 0.65 mmol) in CHCl$_3$ (12 mL) was added MnO$_2$ (565 mg, 6.5 mmol). The reaction mixture was stirred at room temperature for 3 hours. The mixture was then filtered and the filtrate was concentrated to afford the crude product, which was purified by column chromatography on silica gel (eluted with DCM/EtOAc=100:1 to 8:1) to afford 146-S5 (150 mg, 62.7% yield) as a colorless oil. LC/MS (ESI) m/z: 369 (M+H)+.

Step 5: 7-(Difluoromethyl)-5-(2-methylpyrimidin-5-yl)-1-((2-(trimethylsilyl)ethoxy)methyl)-1H-indazole (146-S6)

To a solution of 146-S5 (150 mg, 0.41 mmol) in dry DCM (10 mL) was added DAST (198 mg, 1.23 mmol) at 0° C. slowly under an atmosphere of nitrogen. The resulting mixture was stirred from 0° C. to room temperature for 1 hour and then heated to 40° C. for 24 hours. The mixture was then quenched with saturated aqueous NaHCO$_3$ solution and extracted with EtOAc. The organic layer was separated, dried, and concentrated to dryness. The remaining residue was purified by preparative TLC (eluted with DCM/MeOH=20:1) to afford 146-S6 (92 mg, 58.2% yield) as a colorless oil. LC/MS (ESI) m/z: 391 (M+H)+.

Step 6: 7-(Difluoromethyl)-5-(2-methylpyrimidin-5-yl)-1H-indazole (146-S7)

To a solution of 146-S6 (92 mg, 0.24 mmol) in dry DCM (2 mL) was added TFA (2 mL) at room temperature under an atmosphere of nitrogen. The resulting mixture was stirred at room temperature for 2 hours. The mixture was then concentrated to afford 146-S7 (62 mg, 68.8% yield) as a colorless oil. LC/MS (ESI) m/z: 261 (M+H)+.

Step 7: 7-(Difluoromethyl)-3-iodo-5-(2-methylpyrimidin-5-yl)-1H-indazole (146-S8)

To a solution of 146-S7 (62 mg, 0.24 mmol) in DMF (5 mL) were added KOH (41 mg, 0.72 mmol) and I$_2$ (92 mg, 0.36 mmol) at 0° C. The mixture was stirred at room temperature for 16 hours. The mixture was then quenched with 5% aqueous Na$_2$S$_2$O$_3$ solution and extracted with EtOAc. The organic layer was separated, dried, and concentrated to afford 146-S8 (85 mg, 91.7% yield) as a colorless oil. LC/MS (ESI) m/z: 387 (M+H)+.

Step 8: tert-Butyl 2-(7-(difluoromethyl)-3-iodo-5-(2-methylpyrimidin-5-yl)-1H-indazol-1-yl)acetate (146-S9)

To a solution of 146-S8 (85 mg, 0.22 mmol) in DMF (6 mL) were added K$_2$CO$_3$ (61 mg, 0.44 mmol) and tert-butyl 2-bromoacetate (65 mg, 0.33 mmol). The reaction mixture was stirred at room temperature for 16 hours. The mixture was diluted with EtOAc, washed with 10% aqueous LiCl solution, dried, and concentrated to afford the crude product, which was purified by column chromatography on silica gel (eluted with PE/EtOAc=100:0 to 4:1) to afford 146-S9 (66 mg, 60.0% yield) as a colorless oil. LC/MS (ESI) m/z: 501 (M+H)+.

Step 9: tert-Butyl 2-(3-acetyl-7-(difluoromethyl)-5-(2-methylpyrimidin-5-yl)-1H-indazol-1-yl)acetate (146-S10)

To a mixture of 146-S9 (66 mg, 0.132 mmol) in dry toluene (8 mL) were added tributyl(1-ethoxyvinyl)stannane (67 mg, 0.185 mmol) and Pd(PPh$_3$)$_4$ (13 mg, 0.01 mmol). The reaction mixture was stirred at 100° C. for 16 hours under an atmosphere of nitrogen. After cooling, the mixture was quenched with 1 N aqueous HCl solution and the mixture was stirred at room temperature for 15 minutes. The mixture was extracted with EtOAc and the organic layer was washed with brine, dried over Na$_2$SO$_4$, filtered, and concentrated to afford the crude product, which was purified by column chromatography on silica gel (eluted with DCM/MeOH=100:0 to 50:1) to afford 146-S10 (52 mg, 92.8% yield) as a colorless oil. LC/MS (ESI) m/z: 417 (M+H)+.

Step 10: 2-(3-Acetyl-7-(difluoromethyl)-5-(2-methylpyrimidin-5-yl)-1H-indazol-1-yl)acetic Acid (146-S11)

To a mixture of 146-S10 (52 mg, 0.13 mmol) in THF/H$_2$O (8 mL, 3:1, v/v) was added LiOH·H$_2$O (12 mg, 0.26 mmol). The reaction mixture was stirred at room temperature for 20 hours. The mixture was diluted with water, washed with ether, and the aqueous layer was acidified with aqueous HCl solution (1 N) to pH 5. The resulting mixture was extracted with DCM/MeOH (5 mL×2, 10:1 v/v). The combined organic phases were washed with brine, dried over anhydrous Na$_2$SO$_4$, filtered, and concentrated to afford 146-S11 (36 mg, yield 76.9%) as a white solid. LC/MS (ESI) m/z: 361 (M+H)+.

Step 11: (1R,3S,5R)-2-(2-(3-Acetyl-7-(difluoromethyl)-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (146)

To a solution of 146-S11 (36 mg, 0.1 mmol), 146-S12 (45 mg, 0.13 mmol), and HATU (57 mg, 0.15 mmol) in DMF (2 mL) was added DIPEA (40 mg, 0.3 mmol). The reaction mixture was stirred at room temperature for 16 hours. The mixture was then diluted with EtOAc, washed with 10% aqueous LiCl solution and brine, dried, and concentrated to afford the crude product, which was purified via preparative HPLC to afford 146 (15 mg, 23.0% yield) as a white solid. $^1$H NMR (400 MHz, DMSO-$d_6$) δ 10.29 (s, 1H), 9.10 (s, 2H), 8.72 (s, 1H), 8.17 (s, 1H), 7.63 (d, J=7.9 Hz, 1H), 7.27-7.55 (m, 2H), 5.95 (d, J=18.0 Hz, 1H), 5.72 (d, J=17.7 Hz, 1H), 4.35 (dd, J=9.1, 5.2 Hz, 1H), 3.53-3.58 (m, 1H), 2.71 (s, 3H), 2.69 (s, 3H), 2.53-2.59 (m, 1H), 2.05 (s, 3H), 1.96-2.03 (m, 1H), 1.33 (s, 3H), 1.02-1.07 (m, 1H), 0.87-0.94 (m, 1H). LC/MS (ESI) m/z: 652 (M+H)$^+$.

Scheme 58.
Synthesis of (1R,3S,5R)-2-(2-(3-Acetyl-7-fluoro-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (147)

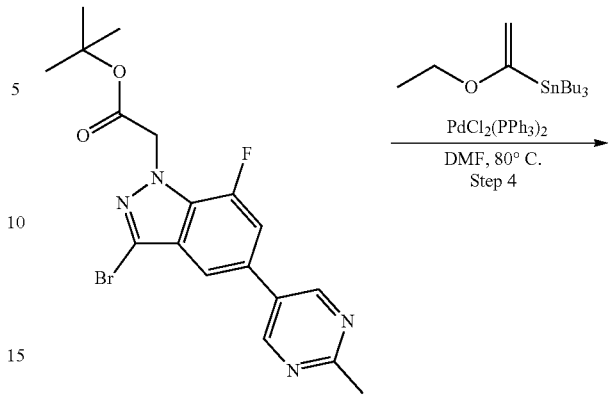

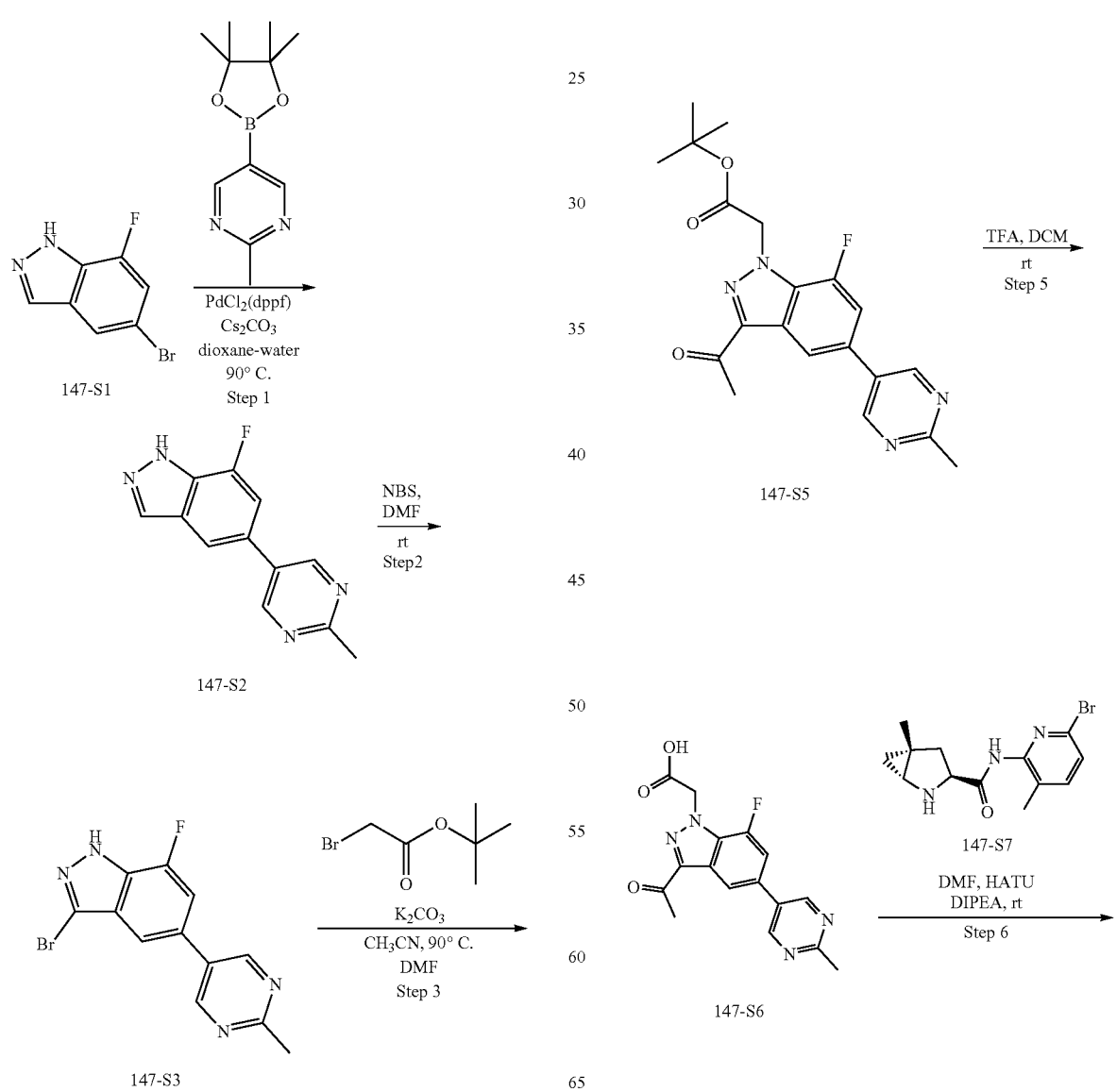

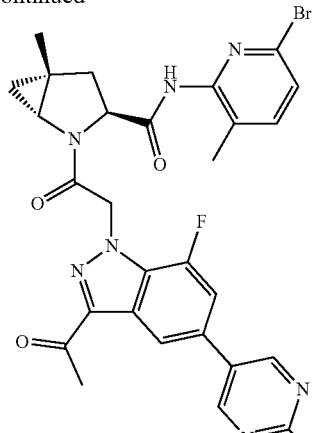

147

Step 1: 7-Fluoro-5-(2-methylpyrimidin-5-yl)-1H-indazole (147-S2)

A mixture of 5-bromo-7-fluoro-1H-indazole (0.32 g equiv), 2-methyl-5-(4,4,5,5-tetramethyl-1,3,2-dioxaborolan-2-yl)pyrimidine (0.384 g), cesium carbonate (1.14 g) in dioxane (8 mL) and water (2.0 mL) was purged with argon in a pressure vessel for 5 minutes. $PdCl_2(dppf)$ (0.190 g) was added under argon and the pressure vessel was sealed and heated at 90° C. overnight. The reaction mixture was cooled to room temperature and poured into water. The precipitated product was isolated by filtration, washed with water, and dried. The material was carried forward without additional purification and used directly in the next step.

Step 2: 3-Bromo-7-fluoro-5-(2-methylpyrimidin-5-yl)-1H-indazole (147-S3)

To a stirred solution of 7-fluoro-5-(2-methylpyrimidin-5-yl)-1H-indazole (0.39 g) in DMF (5 mL), NBS (0.335 g) was added. The reaction mixture was stirred at room temperature for 1 hour. The reaction mixture was poured into water and the precipitate was isolated by filtration, washed with water, and dried. The material was carried forward without additional purification and used directly in the next step.

Step 3: tert-Butyl 2-(3-bromo-7-fluoro-5-(2-methylpyrimidin-5-yl)-1H-indazol-1-yl)acetate (147-S4)

A mixture of 3-bromo-7-fluoro-5-(2-methylpyrimidin-5-yl)-1H-indazole (0.36 g), tert-butyl bromoacetate (181 μL), and potassium carbonate (0.323 g) in anhydrous acetonitrile (5 mL) and DMF (2 mL) was refluxed for 1 hour. The reaction mixture was then cooled to room temperature and the solvent was removed under reduced pressure. The residue was purified by silica gel flash column chromatography (eluent: 0-1.5% MeOH in $CH_2Cl_2$) to afford 147-S4 as white solid.

Step 4: tert-Butyl 2-(3-acetyl-7-fluoro-5-(2-methylpyrimidin-5-yl)-1H-indazol-1-yl)acetate (147-S5)

A solution of tert-butyl 2-(3-bromo-7-fluoro-5-(2-methylpyrimidin-5-yl)-1H-indazol-1-yl)acetate (0.25 g 1 equiv), tri-butyl(1-ethoxyvinyl)tin 0.429 g, 2 equiv) and $PdCl_2$ $(PPh_3)_2$ (42 mg, 0.1 equiv) in DMF (3 mL) was heated at 80° C. overnight under argon atmosphere. Then concentrated under reduced pressure and diluted with $CH_2Cl_2$ and washed with cold aqueous HCl (1N). The organic layer was dried ($Na_2SO_4$), filtered, and concentrated. The residue was purified by silica gel flash column chromatography (eluent: 0-1.5% MeOH in $CH_2Cl_2$) to afford 147-S5.

Step 6: (1R,3S,5R)-2-(2-(3-Acetyl-7-fluoro-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (147)

tert-Butyl 2-(3-acetyl-7-fluoro-5-(2-methylpyrimidin-5-yl)-1H-indazol-1-yl)acetate (70 mg) was stirred in $CH_2Cl_2$ (0.5 mL) and TFA (1.5 mL). After completion of the reaction (monitored by HPLC), the solvent was removed under reduced pressure. The remaining residue was dissolved in DMF (1 mL) and $iPr_2NEt$ (95 μL, 3 equiv) was added, followed by the addition of the TFA salt of (1R,3S,5R)—N-(6-bromopyridin-2-yl)-5-methyl-2-azabicyclo[3.1.0]hexane-3-carboxamide TFA salt (obtained by stirring 74 mg of tert-butyl (1R,3S,5R)-3-((6-bromopyridin-2-yl)carbamoyl)-5-methyl-2-azabicyclo[3.1.0]hexane-2-carboxylate in 1 mL of TFA and 1 mL of $CH_2Cl_2$ for 15 minutes at room temperature and evaporating the volatiles) at 5° C. HATU (76 mg, 1.2 equiv) was added slowly at this same temperature and the reaction mixture was stirred for 30 minutes at room temperature. Then the reaction mixture was poured into water and the precipitate was isolated by filtration. The solid was dried and purified by silica gel flash column chromatography (eluent: 0-2.5% MeOH in $CH_2Cl_2$) to afford 147 as a light yellow solid. $^1H$ NMR (400 MHz, DMSO-$d_6$) δ 0.84-0.91 (m, 1H), 1.05 (t, J=5.4 Hz, 1H), 1.32 (s, 3H), 2.05 (s, 3H), 2.03-2.07 (m, 1H), 2.52-2.58 (m, 1H), 2.67 (s, 3H), 2.69 (s, 3H), 3.56 (d, J=4 Hz, 1H), 4.41 (dd, J=5.2, 9.2 Hz, 1H), 5.65 (d, J=17.4 Hz, 1H), 5.90 (d, J=17.4 Hz, 1H), 7.44 (d, J=7.9 Hz, 1H), 7.62 (d, J=7.9 Hz, 1H), 7.79 (d, J=12.7 Hz, 1H), 8.28 (s, 1H), 9.06 (s, 2H), 10.26 (s, 1H). $^{19}F$ NMR (DMSO-$d_6$): δ −131.6.

Scheme 59.
Synthesis of (1R,3S,5R)-2-(2-(3-Acetyl-5-(2-(2-(dimethylamino)-2-oxoethyl)pyrimidin-5-yl)-1H-indazol-1-yl)acetyl)-N-(6-bromo-3-methylpyridin-2-yl)-5-methyl-2-azabicyclo[3.1.0]hexane-3-carboxamide (148)

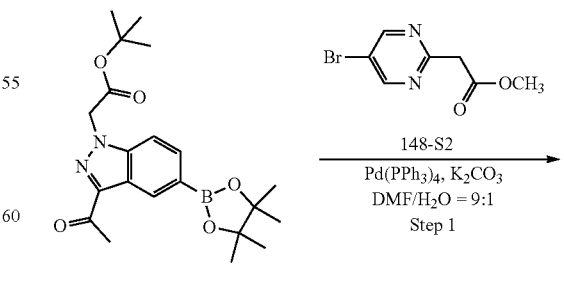

148-S1

148-S2

Pd(PPh$_3$)$_4$, K$_2$CO$_3$
DMF/H$_2$O = 9:1
Step 1

811
-continued

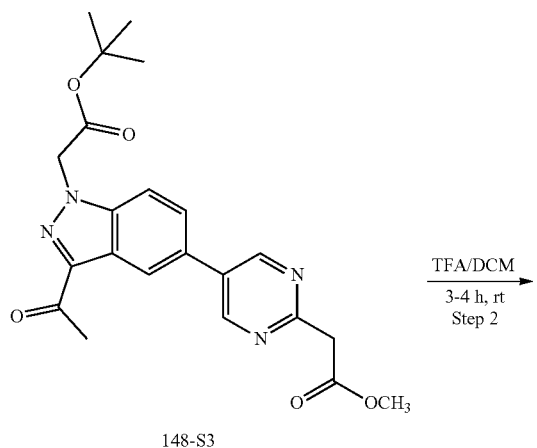

148-S3

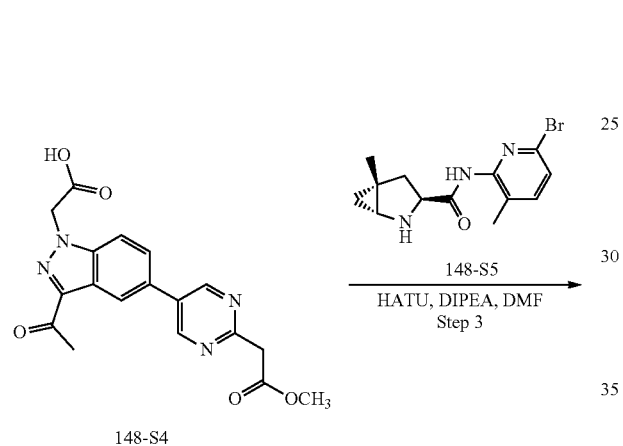

148-S4

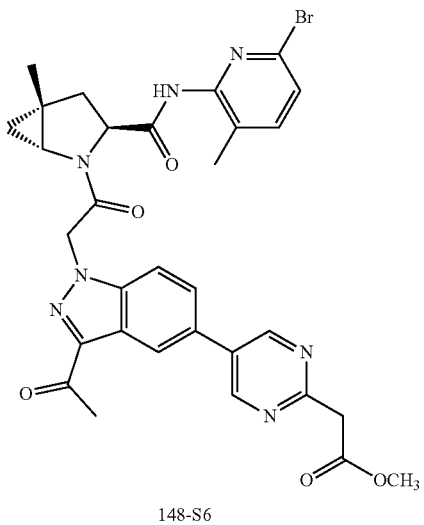

148-S6

812
-continued

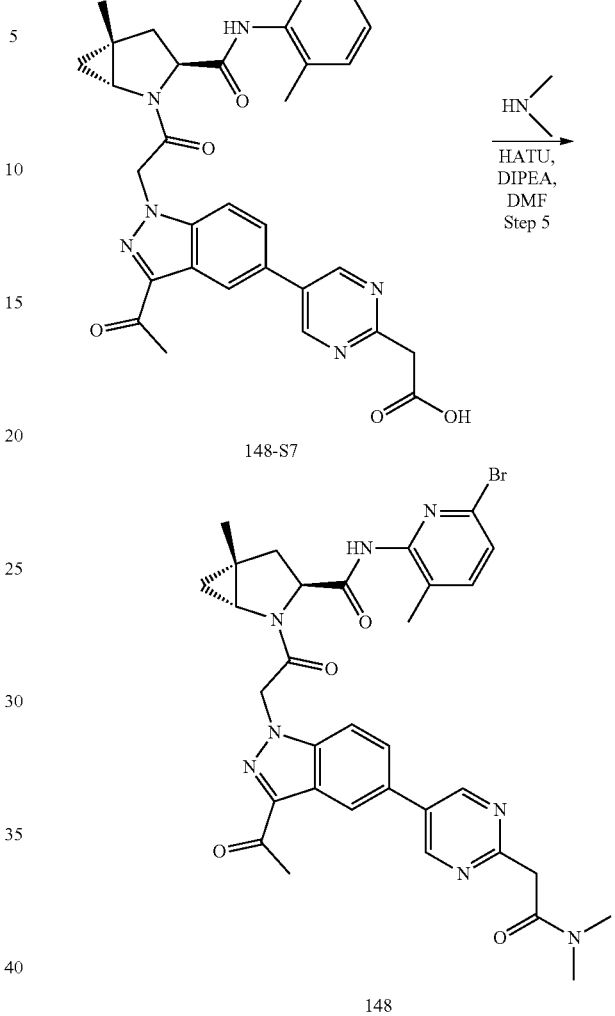

Step 1: tert-Butyl 2-(3-acetyl-5-(2-(2-methoxy-2-oxoethyl)pyrimidin-5-yl)-1H-indazol-1-yl)acetate (148-S3)

To a solution of methyl 2-(5-bromopyrimidin-2-yl)acetate (148-S2, 1 equiv) in DMF/H₂O (9:1, 10 vol) was added compound 148-S1 (1 equiv), K₂CO₃ (2 equiv) and tetrakis (triphenylphosphine)palladium (0.1 equiv). The reaction mixture was stirred at 90° C. for 5 hours and concentrated under reduced pressure. The remaining residue was purified by column chromatography on silica gel (eluted with DCM/MeOH) to afford compound 148-S3.

Step 2: 2-(3-Acetyl-5-(2-(2-methoxy-2-oxoethyl)pyrimidin-5-yl)-1H-indazol-1-yl)acetic Acid (148-S4)

To a solution of compound 148-S3 (1 equiv) in DCM (10 vol) at 0° C. under an atmosphere of argon was added TFA (5 vol). The reaction mixture was stirred at room temperature for 3 hours and concentrated to dryness. The remaining material was carried forward without further purification and used directly in the next synthetic step.

Step 3: Methyl 2-(5-(3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-indazol-5-yl)pyrimidin-2-yl)acetate (148-S6)

To a solution of compound 148-S4 (1 equiv) in DMF (10 vol) at 0° C. under an atmosphere of argon was added (1R,3S,5R)—N-(6-bromo-3-methylpyridin-2-yl)-5-methyl-2-azabicyclo[3.1.0]hexane-3-carboxamide (148-S5, 1 equiv), HATU (2.1 equiv), and DIPEA (5 equiv). The reaction mixture was stirred at room temperature for 3 hours and quenched with water (30 vol). The resulting mixture was extracted with DCM. The organic layer was washed with brine, dried over anhydrous $Na_2SO_4$, filtered, and concentrated to dryness. The remaining residue was purified by column chromatography on silica gel (eluted with DCM/MeOH) to afford compound 148-S6.

Step 4: 2-(5-(3-Acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-indazol-5-yl)pyrimidin-2-yl)acetic Acid (148-S7)

To a solution of methyl 2-(5-(3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-indazol-5-yl)pyrimidin-2-yl)acetate (148-S6, 1 equiv) in $THF/H_2O$ (3:1, 10 vol) was added LiOH (2.1 equiv). The reaction mixture was stirred at room temperature for 5 hours and concentrated under reduced pressure. The remaining residue was neutralized using 2N HCl and the precipitated solid was filtered, dried, and directly used in the next synthetic step.

Step 5: (1R,3S,5R)-2-(2-(3-Acetyl-5-(2-(2-(dimethylamino)-2-oxoethyl)pyrimidin-5-yl)-1H-indazol-1-yl)acetyl)-N-(6-bromo-3-methylpyridin-2-yl)-5-methyl-2-azabicyclo[3.1.0]hexane-3-carboxamide (148)

To a solution of compound 148-S7 (1 equiv) in DMF (10 vol) at 0° C. under an atmosphere of argon was added dimethylamine hydrochloride (1.2 equiv), HATU (2.1 equiv), and DIPEA (5 equiv). The reaction mixture was stirred at room temperature for 3 hours and quenched with water (30 vol). The resulting mixture was extracted with DCM. The organic layer was washed with brine, dried over anhydrous $Na_2SO_4$, filtered, and concentrated to dryness. The remaining residue was purified by column chromatography on silica gel (eluted with DCM/MeOH) to afford compound 148. $^1$H NMR (400 MHz, DMSO-$d_6$) δ 0.98-1.06 (m, 2H), 1.33 (s, 3H), 2.05 (s, 4H), 2.53-2.59 (m, 1H), 2.67 (s, 3H), 2.88 (s, 3H), 3.07 (s, 3H), 3.55-3.68 (m, 1H), 4.08 (s, 2H), 4.37-4.47 (m, 1H), 5.59 (d, J=17.2 Hz, 1H), 5.92 (d, J=17.2 Hz, 1H), 7.45 (d, J=7.9 Hz, 1H), 7.63 (d, J=7.9 Hz, 1H), 7.87 (t, J=6.5 Hz, 2H), 8.47 (s, 1H), 9.10 (s, 2H), 10.26 (s, 1H).

Scheme 60:
Synthesis of Methyl ((S)-1-(((((1R,3S,5R)-2-(2-(3-acetyl-5-(2-methylpyrimidin-5-yl)-1H-indazol-1-yl)acetyl)-3-((6-bromo-3-(methoxymethyl)pyridin-2-yl)carbamoyl)-2-azabicyclo[3.1.0]hexan-5-yl)methyl)amino)-3-methyl-1-oxobutan-2-yl)carbamate (153)

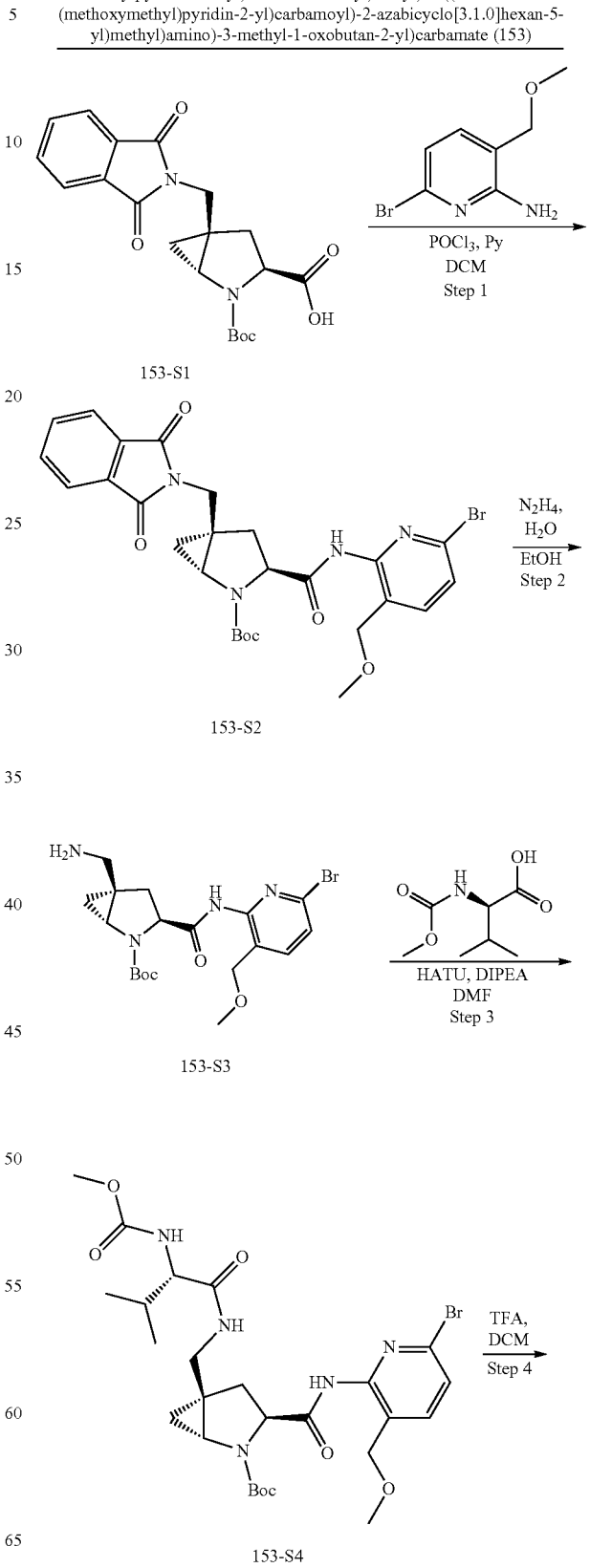

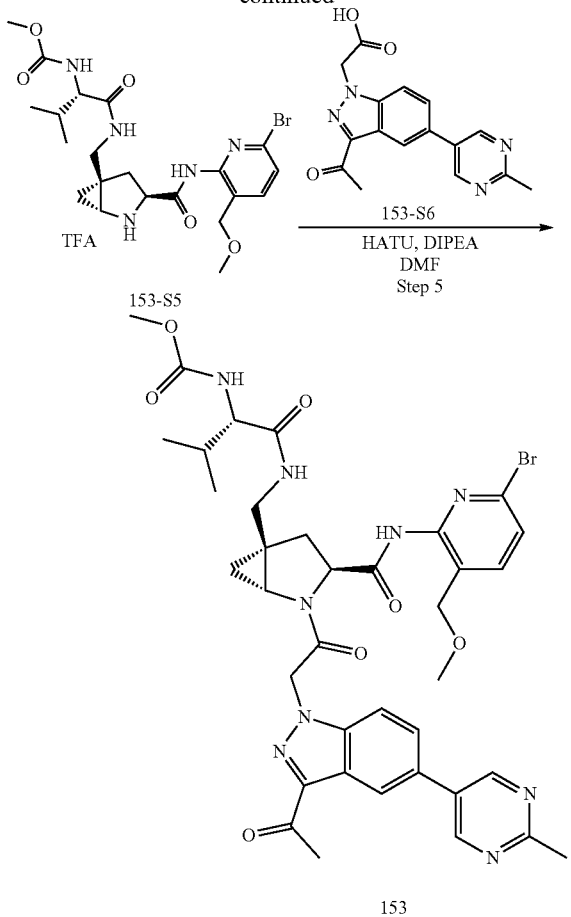

raphy on silica gel (eluted with DCM/MeOH=5:1) to afford 153-S3 (130 mg, 92.2% yield) as a white solid. LC/MS (ESI) m/z: 455/(M+H)$^+$.

Step 3: (1R,3S,5R)-tert-Butyl 3-((6-bromo-3-(methoxymethyl)pyridin-2-yl)carbamoyl)-5-(((S)-2-((methoxycarbonyl)amino)-3-methylbutanamido)methyl)-2-azabicyclo[3.1.0]hexane-2-carboxylate (153-S4)

To a mixture of 153-S3 (30 mg, 0.066 mmol), (S)-2-(methoxycarbonylamino)-3-methylbutanoic acid (13.9 mg, 0.079 mmol), and HATU (37.6 mg, 0.099 mmol) in DMF (2 mL) was added DIPEA (0.04 mL, 0.198 mmol). The reaction mixture was stirred at room temperature for 16 hours. The mixture was partitioned with EtOAc and water. The organic layer was washed with brine, dried over anhydrous $Na_2SO_4$, and concentrated under reduced pressure. The remaining residue was purified by column chromatography on silica gel (PE/EtOAc=2:1 to 0:1) to afford 153-S4 (29 mg, 72.0% yield) as a light oil. LC/MS (ESI) m/z: 612 (M+H)$^+$.

Step 4: Methyl ((S)-1-((((1R,3S,5R)-3-((6-bromo-3-(methoxymethyl)pyridin-2-yl)carbamoyl)-2-azabicyclo[3.1.0]hexan-5-yl)methyl)amino)-3-methyl-1-oxobutan-2-yl)carbamate (153-S5)

To a solution of 153-S4 (29 mg, 0.05 mmol) in DCM (2 mL) was added TFA (1 mL). The reaction mixture was stirred at room temperature for 1.5 hours and then concentrated under reduced pressure to afford 153-S5 (25.6 mg, 100% yield) as a yellow solid, which was carried forward in the next synthetic step without further purification. LC/MS (ESI) m/z: 512 (M+H)$^+$.

Step 5: Methyl ((S)-1-((((1R,3S,5R)-2-(2-(3-acetyl-5-(2-methylpyrimidin-5-yl)-1H-indazol-1-yl)acetyl)-3-((6-bromo-3-(methoxymethyl)pyridin-2-yl)carbamoyl)-2-azabicyclo[3.1.0]hexan-5-yl)methyl)amino)-3-methyl-1-oxobutan-2-yl)carbamate (153)

To a mixture of 153-S5 (25.6 mg, 0.05 mmol), 2-(3-acetyl-5-(2-methylpyrimidin-5-yl)-1H-indazol-1-yl)acetic acid (153-S6, 16.1 mg, 0.05 mmol), and HATU (29.6 mg, 0.08 mmol) in DMF (2 mL) was added DIPEA (0.03 mL, 0.14 mmol). The reaction mixture was stirred at room temperature for 16 hours. The mixture was partitioned with EtOAc and water. The organic layer was washed with brine, dried over anhydrous $Na_2SO_4$, and concentrated under reduced pressure. The crude product was purified by preparative HPLC to afford 153 (5.2 mg, 12.9% yield) as a white solid. $^1$H NMR (400 MHz, DMSO-$d_6$) δ 10.43 (s, 1H), 9.04 (s, 2H), 8.44 (s, 1H), 8.16 (s, 1H), 7.87 (d, J=1.1 Hz, 2H), 7.77 (d, J=8.1 Hz, 1H), 7.55 (d, J=8.0 Hz, 1H), 7.12 (d, J=9.1 Hz, 1H), 5.88 (d, J=17.2 Hz, 1H), 5.61 (d, J=17.1 Hz, 1H), 4.44-4.39 (m, 1H), 4.17 (s, 1H), 3.85-3.79 (m, 1H), 3.76-3.73 (m, 1H), 3.65-3.63 (m, 1H), 3.54 (s, 3H), 3.08 (s, 3H), 3.07-3.05 (m, 1H), 2.69 (s, 3H), 2.68-2.67 (m, 1H), 2.66 (s, 3H), 2.20-2.17 (m, 1H), 1.97-1.94 (m, 1H), 1.24 (s, 1H), 1.17 (t, J=5.6 Hz, 1H), 1.08 (s, 1H), 0.94-0.81 (m, 6H). LC/MS (ESI) m/z: 804 (M+H)$^+$.

Step 1: (5R,3S,5R)-tert-Butyl 3-((6-bromo-3-(methoxymethyl)pyridin-2-yl)carbamoyl)-5-((1,3-dioxoisoindolin-2-yl)methyl)-2-azabicyclo[3.1.0]hexane-2-carboxylate (153-S2)

To a mixture of 153-S1 (290 mg, 0.75 mmol) and 6-bromo-3-(methoxymethyl)pyridin-2-amine (162 mg, 0.75 mmol) in dry DCM (3 mL) was added pyridine (0.3 mL, 3.75 mmol) followed by POCl$_3$ (114.7 mg, 0.75 mmol) at 0° C. The reaction mixture was stirred at room temperature for 30 minutes. The mixture was poured into ice water and extracted with DCM twice. The organic layers were washed with brine, dried over $Na_2SO_4$, and concentrated under reduced pressure. The remaining residue was purified by silica gel chromatography (PE/EtOAc=6:1 to 2:1) to afford 153-S2 (180 mg, 41.0% yield) as a white solid. LC/MS (ESI) m/z: 585 (M+H)$^+$.

Step 2: (1R,3S,5R)-tert-Butyl 5-(aminomethyl)-3-((6-bromo-3-(methoxymethyl)pyridin-2-yl)carbamoyl)-2-azabicyclo[3.1.0]hexane-2-carboxylate (153-S3)

To a solution of 153-S2 (180 mg, 0.31 mmol) in EtOH (3 mL) was added hydrazine hydrate (72.5 mg, 1.24 mmol). The reaction mixture was stirred at 75° C. for 2 hours and then cooled to room temperature. The mixture was filtered and the filtrate was concentrated under reduced pressure. The remaining residue was purified by column chromatog- Scheme 61: Synthesis of (1R,3S,5S)-2-(2-(3-Acetyl-7-methyl-5-(2-methylpyrimidin-5-yl)-1H-indazol-1-yl)acetyl)-N-(6-bromo-3-methylpyridin-2-yl)-5-((2-(dimethylamino)ethoxy)methyl)-2-azabicyclo[3.1.0]hexane-3-carboxamide (157)

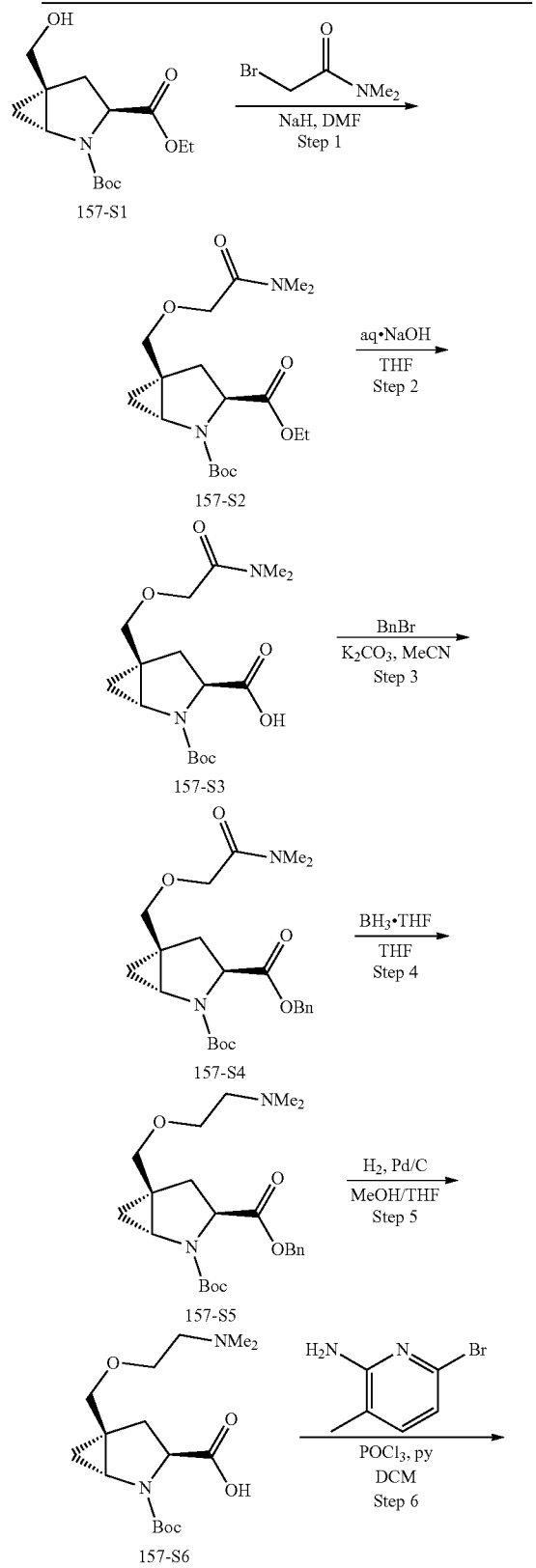

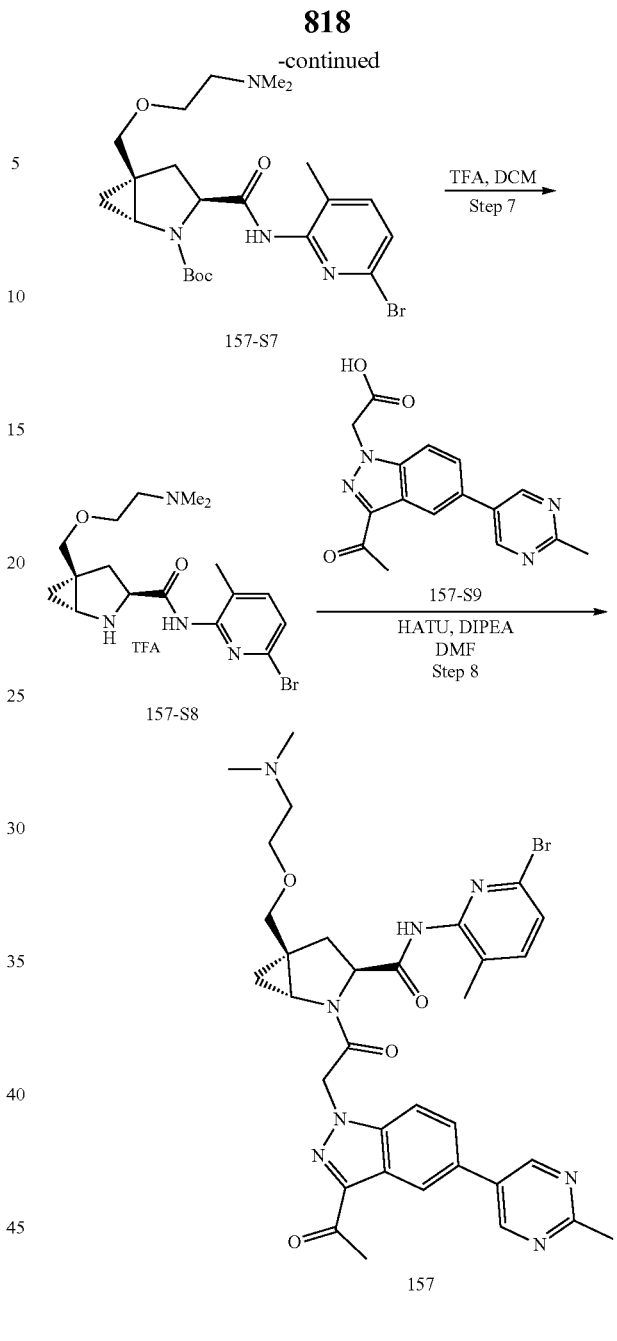

Step 1: (1R,3S,5S)-2-tert-Butyl 3-ethyl 5-((2-(dimethylamino)-2-oxoethoxy)methyl)-2-azabicyclo[3.1.0]hexane-2,3-dicarboxylate (157-S2)

To a solution of 157-S1 (200 mg, 0.70 mmol) in DMF (3 mL) was added NaH (56 mg, 60% dispersion in mineral oil, 1.40 mmol) at 0° C., and after 5 minutes, 2-bromo-N,N-dimethylacetamide (232 mg, 1.40 mmol) was added. The reaction mixture was stirred at room temperature for 3 hours. The mixture was partitioned with ice water and EtOAc. The organic layer was washed with brine, dried over anhydrous $Na_2SO_4$, and concentrated under reduced pressure to afford 157-S2 (110 mg, 42.5% yield) as a yellow oil. LC/MS (ESI) m/z: 371 (M+H)$^+$.

Step 2: (1R,3S,5S)-2-(tert-Butoxycarbonyl)-5-((2-(dimethylamino)-2-oxoethoxy)methyl)-2-azabicyclo[3.1.0]hexane-3-carboxylic acid (157-S3)

To a solution of 157-S2 (110 mg, 0.30 mmol) in THF (3 mL) and water (3 mL) was added NaOH (36 mg, 0.90 mmol) at 0° C. The reaction mixture was stirred at room temperature for 2 hours. The mixture was concentrated to half volume and washed with EtOAc twice. The mixture was acidified with 2 N aqueous HCl to pH 4 and extracted with DCM three times. The combined organic layers were concentrated to dryness to afford 157-S3 (85 mg, 83.3% yield) as a colorless oil. LC/MS (ESI) m/z: 343 (M+H)$^+$.

Step 3: (1R,3S,5S)-3-Benzyl 2-tert-butyl 5-((2-(dimethylamino)-2-oxoethoxy)methyl)-2-azabicyclo[3.1.0]hexane-2,3-dicarboxylate (157-S4)

To a solution of 157-S3 (85 mg, 0.25 mmol) in MeCN (2 mL) were added K$_2$CO$_3$ (69 mg, 0.50 mmol) and BnBr (58 mg, 0.34 mmol). The reaction mixture was stirred at room temperature for 16 hours and concentrated under reduced pressure. The remaining residue was purified by column chromatography on silica gel (eluted with PE/EtOAc=2:1) to afford 157-S4 (95 mg, 88.0% yield) as a colorless oil. LC/MS (ESI) m/z: 433 (M+H)$^+$.

Step 4: (1R,3S,5S)-3-Benzyl 2-tert-butyl 5-((2-(dimethylamino)ethoxy)methyl)-2-azabicyclo[3.1.0]hexane-2,3-dicarboxylate (157-S5)

To a solution of 157-S4 (95 mg, 0.22 mmol) in THF (5 mL) was added BH$_3$.THF (0.66 mL, 0.66 mmol, 1 M). The reaction mixture was stirred at reflux for 16 hours. The reaction mixture was quenched with MeOH and concentrated to dryness. The remaining residue was diluted with EtOH (8 mL) and H$_2$O (1 mL) and the mixture was stirred at reflux for 4 hours. The mixture was concentrated to dryness and the remaining residue was purified by column chromatography on silica gel (eluted with DCM/MeOH=30:1) to afford 157-S5 (90 mg, 97.8% yield) as a white solid. LC/MS (ESI) m/z: 419 (M+H)$^+$.

Step 5: (1R,3S,5S)-2-(tert-Butoxycarbonyl)-5-((2-(dimethylamino)ethoxy)methyl)-2-azabicyclo[3.1.0]hexane-3-carboxylic Acid (157-S6)

To a solution of 157-S5 (90 mg, 0.21 mmol) in MeOH (5 mL) was added Pd/C (10 mg, 10% wt). The reaction mixture was stirred at room temperature for 1 hour. The mixture was filtered and concentrated to dryness to afford 157-S6 (65 mg, 94.3% yield) as a white solid. LC/MS (ESI) m/z: 329 (M+H)$^+$.

Step 6: (1R,3S,5S)-tert-Butyl 3-(6-bromo-3-methylpyridin-2-ylcarbamoyl)-5-((2-(dimethylamino)ethoxy)methyl)-2-azabicyclo[3.1.0]hexane-2-carboxylate (157-S7)

To a solution of 157-S6 (65 mg, 0.20 mmol) and 6-bromo-3-methylpyridin-2-amine (23 mg, 0.24 mmol) in DCM (5 mL) was added pyridine (24 mg, 1.22 mmol) at 0° C. followed by dropwise addition of POCl$_3$ (0.02 mL, 0.20 mmol). The reaction mixture was stirred at 0° C. for 30 minutes. The reaction mixture was quenched with ice-cooled water and extracted with DCM twice. The combined organic phases were washed with brine, dried over anhydrous Na$_2$SO$_4$, filtered, and concentrated to dryness. The remaining residue was purified by column chromatography on silica gel (eluted with DCM/MeOH=50:1) to afford 157-S7 (80 mg, 67.2% yield) as a white solid. LC/MS (ESI) m/z: 497 (M+H)$^+$.

Step 7: (1R,3S,5S)—N-(6-Bromo-3-methylpyridin-2-yl)-5-((2-(dimethylamino)ethoxy)methyl)-2-azabicyclo[3.1.0]hexane-3-carboxamide (157-S8)

To a solution of 157-S7 (80 mg, 0.14 mmol) in DCM (2.5 mL) was added TFA (1 mL). The reaction mixture was stirred at room temperature for 1.5 hours and then concentrated under reduced pressure to afford 157-S8 (80 mg, 100.0% yield) as a yellow solid, which was carried forward in the next synthetic step without further purification. LC/MS (ESI) m/z: 397 (M+H)$^+$.

Step 8: (1R,3S,5S)-2-(2-(3-Acetyl-7-methyl-5-(2-methylpyrimidin-5-yl)-1H-indazol-1-yl)acetyl)-N-(6-bromo-3-methylpyridin-2-yl)-5-((2-(dimethylamino)ethoxy)methyl)-2-azabicyclo[3.1.0]hexane-3-carboxamide (157)

To a solution of 157-S8 (30 mg, 0.08 mmol), 2-(3-acetyl-5-(2-methylpyrimidin-5-yl)-1H-indazol-1-yl)acetic acid (157-S9, 28 mg, 0.089 mmol) and HATU (46 mg, 0.12 mmol) in DMF (2 mL) was added DIPEA (0.04 mL, 0.24 mmol). The reaction mixture was stirred at room temperature for 16 hours. The mixture was partitioned with EtOAc and water. The organic layer was washed with brine, dried over anhydrous Na$_2$SO$_4$, and concentrated under reduced pressure. The remaining residue was purified by preparative HPLC to afford 157 (2.9 mg, 5.3% yield) as a white solid. $^1$H NMR (400 MHz, CD$_3$OD) δ 9.04 (s, 2H), 8.59 (s, 1H), 7.85-7.77 (m, 2H), 7.61 (d, J=7.5 Hz, 1H), 7.44 (d, J=7.9 Hz, 1H), 5.82 (m, 1H), 5.71 (m, 1H), 5.36 (m, 1H), 4.72 (m, 1H), 3.98-3.89 (m, 2H), 3.87-3.76 (m, 2H), 3.41 (m, 2H), 2.94 (s, 6H), 2.78 (s, 3H), 2.67 (m, 1H), 2.59 (m, 1H), 2.14 (s, 3H), 1.20 (m, 1H), 0.91 (m, 1H). LC/MS (ESI) m/z: 689 (M+H)$^+$.

Scheme 62: Synthesis of (1R,3S,5S)-2-(2-(3-Acetyl-7-methyl-5-(2-methylpyrimidin-5-yl)-1H-indazol-1-yl)acetyl)-N-(6-bromo-3-methylpyridin-2-yl)-5-((2,2-difluorocyclopentanecarboxamido)methyl)-2-azabicyclo[3.1.0]hexane-3-carboxamide (158)

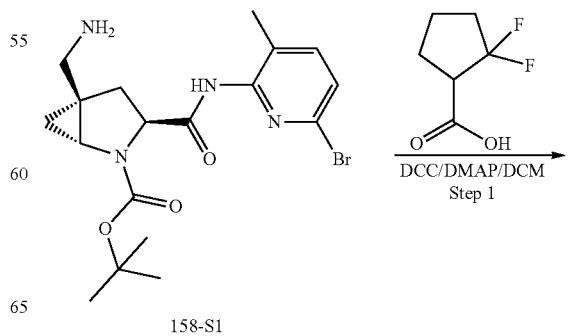

158-S1

-continued

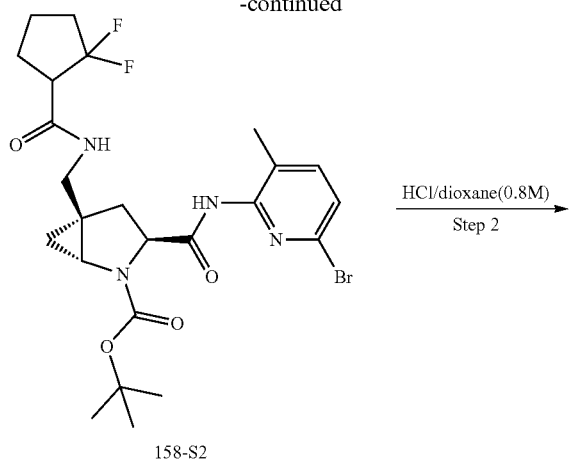

158-S2

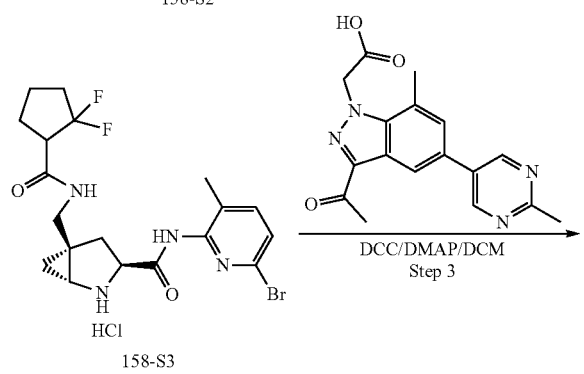

158-S3

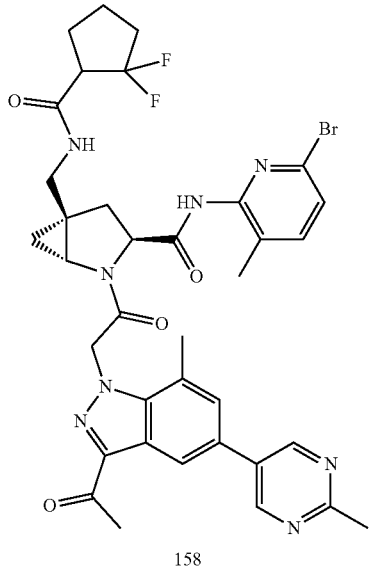

158

Step 1: (1R,3S,5R)-tert-Butyl 3-(6-bromo-3-methylpyridin-2-ylcarbamoyl)-5-((2,2-difluorocyclopentanecarboxamido)methyl)-2-azabicyclo[3.1.0]hexane-2-carboxylate (158-S2)

To a solution of 158-S1 (50 mg, 0.12 mmol) and 2,2-difluorocyclopentanecarboxylic acid (18 mg, 0.12 mmol) in DCM (3 mL) was added DCC (36 mg, 0.18 mmol) at 0° C. followed by DMAP (2 mg, 0.01 mmol). The reaction mixture was stirred at room temperature for 1 hour. The mixture was concentrated under vacuum and the remaining residue was purified by silica gel chromatography (DCM/MeOH=80:1) to afford 158-S2 (60 mg, 89.8% yield) as a white solid. LC/MS (ESI) m/z: 557 (M+H)+.

Step 2: (1R,3S,5R)—N-(6-Bromo-3-methylpyridin-2-yl)-5-((2,2-difluorocyclopentanecarboxamido)methyl)-2-azabicyclo[3.1.0]hexane-3-carboxamide (158-S3)

To a solution of 158-S2 (60 mg, 0.11 mmol) in dioxane (1.5 mL) was added HCl/dioxane (2 M, 0.4 mL). The reaction mixture was stirred at room temperature for 1 hour. The reaction mixture was concentrated to afford 158-S3 (60 mg, 100% yield) as a white solid, which was carried forward in the next synthetic step without purification. LC/MS (ESI) m/z: 457 (M+H)+.

Step 3: (1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-((2,2-difluorocyclopentanecarboxamido)methyl)-2-azabicyclo[3.1.0]hexane-3-carboxamide (158)

To a solution of 158-S3 (30 mg, 0.08 mmol) and 2-(3-acetyl-7-methyl-5-(2-methylpyrimidin-5-yl)-1H-indazol-1-yl)acetic acid (27 mg, 0.08 mmol) in DCM (3 mL) was added DCC (25 mg, 0.12 mmol) at 0° C. followed by DMAP (2 mg, 0.01 mmol). The reaction mixture was stirred at room temperature for 1 hour. The mixture was concentrated to dryness and the remaining residue was purified by preparative HPLC to afford 158 (10.1 mg, 16.6% yield) as a white solid. $^1$H NMR (400 MHz, CD$_3$OD) δ 8.99 (s, 2H), 8.40 (s, 1H), 7.61-7.48 (m, 2H), 7.39 (d, J=8.1 Hz, 1H), 5.96 (m, 1H), 5.80 (m, 1H), 4.65 (m, 1H), 3.58 (m, 3H), 3.13-3.00 (m, 1H), 2.76 (s, 6H), 2.69 (s, 3H), 2.62-2.41 (m, 2H), 2.21-2.06 (m, 6H), 1.99-1.86 (m, 2H), 1.73 (m, 1H), 1.34 (m, 1H), 1.10 (m, 1H). LC/MS (ESI) m/z: 763 (M+H)+.

Scheme 63: Synthesis of (1R,3S,5S)-2-(2-(3-Acetyl-7-methyl-5-(2-methylpyrimidin-5-yl)-1H-indazol-1-yl)acetyl)-N-(6-bromo-3-methylpyridin-2-yl)-5-(fluoromethyl)-2-azabicyclo[3.1.0]hexane-3-carboxamide (163)

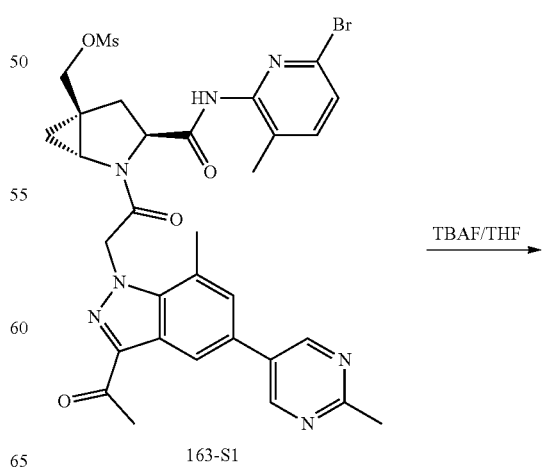

163-S1

823

-continued

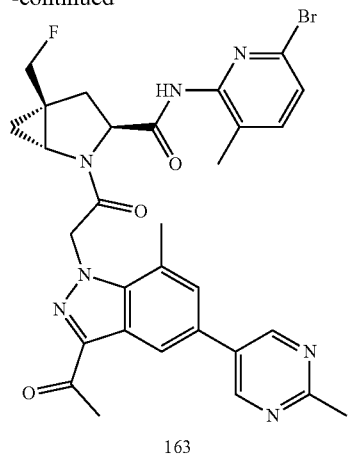

163

A solution of 163-S1 (40 mg, 0.056 mmol) in TBAF/THF (3 mL, 1 M) was stirred at 60° C. for 1 hour. The mixture was partitioned with EtOAc and water. The organic layer was washed with brine, dried over anhydrous $Na_2SO_4$, and concentrated under reduced pressure. The remaining residue product was purified by preparative HPLC to afford 163 (5 mg, 13.8% yield) as a white solid. $^1H$ NMR (400 MHz, $CD_3OD$) δ 8.98 (s, 2H), 8.40 (s, 1H), 7.52-7.55 (m, 2H), 7.37 (d, J=8.0 Hz, 1H), 5.94-5.99 (m, 1H), 5.78-5.83 (m, 1H), 4.64-4.68 (m, 1H), 4.59 (s, 1H), 4.47 (s, 1H), 3.81-3.83 (m, 1H), 2.74 (s, 6H), 2.69 (s, 4H), 2.56-2.59 (m, 1H), 2.12 (s, 3H), 1.38-1.42 (m, 1H), 1.18-1.20 (m, 1H). LC/MS (ESI) m/z: 634 (M+H)$^+$.

Scheme 64: Synthesis of (1R,3S,5R)-5-(Acetamidomethyl)-2-(2-(3-acetyl-5-(2-methylpyrimidin-5-yl)-1H-indazol-1-yl)acetyl)-N-(6-bromo-3-(methoxymethyl)pyridin-2-yl)-2-azabicyclo[3.1.0]hexane-3-carboxamide (165)

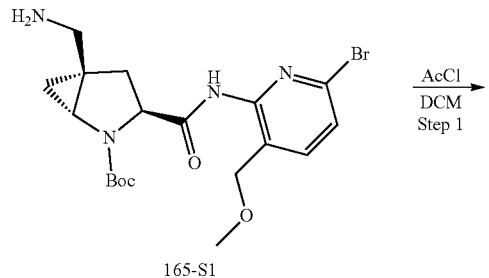

165-S1

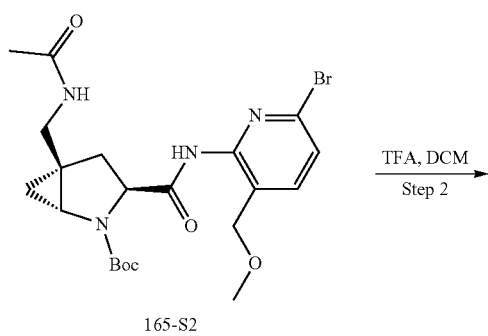

165-S2

824

-continued

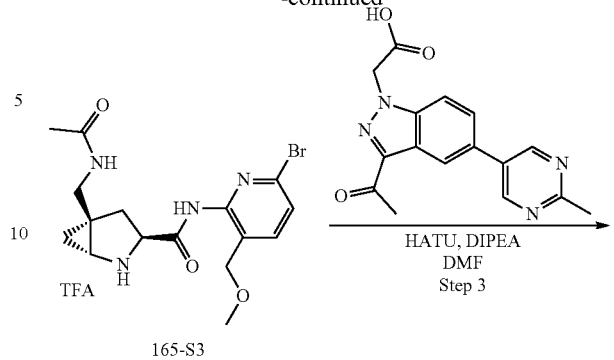

165-S3

165

Step 1: (1R,3S,5R)-tert-Butyl 5-(acetamidomethyl)-3-((6-bromo-3-(methoxymethyl)pyridin-2-yl)carbamoyl)-2-azabicyclo[3.1.0]hexane-2-carboxylate (165-S2)

To a mixture of 165-S1 (40 mg, 0.088 mmol) in dry DCM (3 mL) was added DIPEA (0.03 mL, 0.176 mmol) followed by a solution of acetyl chloride (8.3 mg, 0.106 mmol) in DCM (0.5 mL) at 0° C. The reaction mixture was stirred at room temperature for 1 hour. The mixture was then diluted with water (20 mL) and extracted with DCM (4 mL×2). The combined organic phases were washed with brine, dried over anhydrous $Na_2SO_4$, filtered, and concentrated. The crude was purified by column chromatography on silica gel (eluted with DCM/MeOH=240:1) to afford 165-S2 (40 mg, 91.7% yield) as a white solid. LC/MS (ESI) m/z: 497 (M+H)$^+$.

Step 2: (1R,3S,5R)-5-(Acetamidomethyl)-N-(6-bromo-3-(methoxymethyl)pyridin-2-yl)-2-azabicyclo[3.1.0]hexane-3-carboxamide (165-S3)

To a solution of 165-S2 (40 mg, 0.08 mmol) in DCM (2 mL) was added TFA (1 mL). The reaction mixture was stirred at room temperature for 1.5 hours and then concentrated under reduced pressure to afford 165-S3 (35.6 mg, 100% yield) as a yellow solid, which was carried forward in the next synthetic step without further purification. LC/MS (ESI) m/z: 397 (M+H)$^+$.

Step 3: (1R,3S,5R)-5-(Acetamidomethyl)-2-(2-(3-acetyl-5-(2-methylpyrimidin-5-yl)-1H-indazol-1-yl)acetyl)-N-(6-bromo-3-(methoxymethyl)pyridin-2-yl)-2-azabicyclo[3.1.0]hexane-3-carboxamide (165)

To a mixture of 165-S3 (35.6 mg, 0.09 mmol), 2-(3-acetyl-5-(2-methylpyrimidin-5-yl)-1H-indazol-1-yl)acetic acid (26.9 mg, 0.09 mmol), and HATU (49.6 mg, 0.13 mmol) in DMF (2 mL) was added DIPEA (0.04 mL, 0.26 mmol). The reaction mixture was stirred at room temperature for 16 hours. The mixture was partitioned with EtOAc and water. The organic layer was washed with brine, dried over anhydrous $Na_2SO_4$, and concentrated under reduced pressure. The crude product was purified by preparative HPLC to afford 165 (15.5 mg, 25.0% yield) as a white solid. $^1$H NMR (400 MHz, DMSO-$d_6$) δ 10.39 (s, 1H), 9.04 (s, 2H), 8.44 (s, 1H), 8.03 (t, J=5.9 Hz, 1H), 7.87 (d, J=1.6 Hz, 2H), 7.77 (d, J=8.1 Hz, 1H), 7.55 (d, J=8.0 Hz, 1H), 5.88 (d, J=17.3 Hz, 1H), 5.61 (d, J=17.2 Hz, 1H), 4.44-4.41 (m, 1H), 4.21-4.12 (m, 2H), 3.71-3.69 (m, 1H), 3.34-3.32 (m, 1H), 3.25-3.23 (m, 1H), 3.10 (s, 3H), 2.69 (s, 3H), 2.65 (s, 3H), 2.47-2.43 (m, 1H), 2.24-2.21 (m, 1H), 1.86 (s, 3H), 1.16-1.14 (m, 1H), 1.09-1.07 (m, 1H). LC/MS (ESI) m/z: 689 (M+H)$^+$.

Scheme 65:
Synthesis of (1R,3S,5R)-2-(2-(3-Acetyl-5-(2-methylpyrimidin-5-yl)-1H-indazol-1-yl)acetyl)-N-(6-bromo-3-(methoxymethyl)pyridin-2-yl)-5-((dimethylamino)methyl)-2-azabicyclo[3.1.0]hexane-3-carboxamide (166)

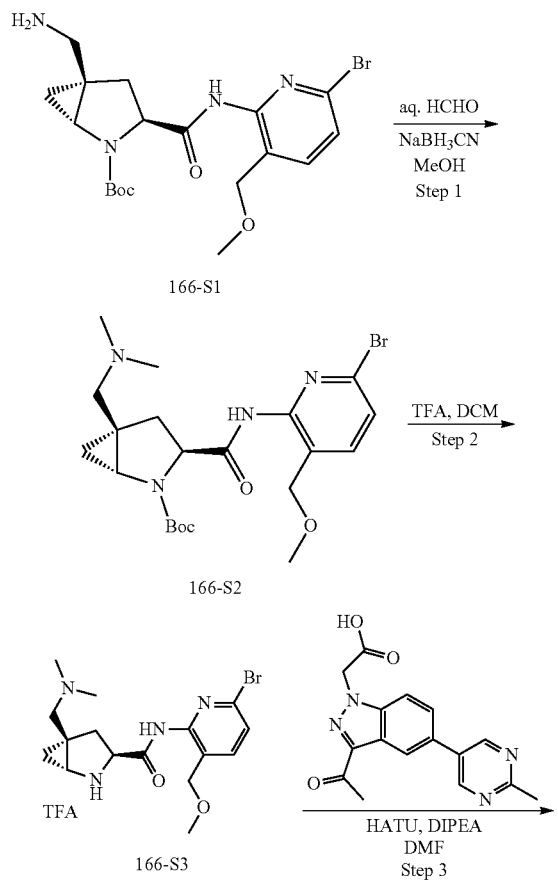

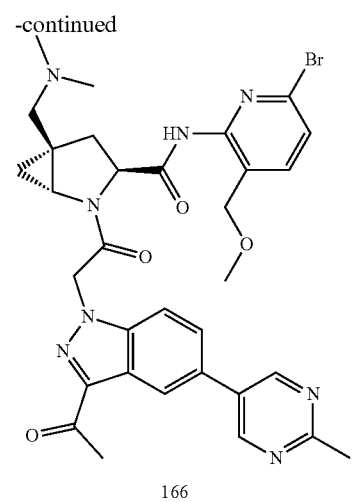

Step 1: (1R,3S,5R)-tert-Butyl 3-((6-bromo-3-(methoxymethyl)pyridin-2-yl)carbamoyl)-5-((dimethylamino)methyl)-2-azabicyclo[3.1.0]hexane-2-carboxylate (166-S2)

To a solution of 166-S1 (67 mg, 0.147 mmol) in MeOH (3 mL) were added aqueous HCHO solution (13.3 mg, 0.443 mmol) and NaBH$_3$CN (18.5 mg, 0.294 mmol) at 0° C. The reaction mixture was stirred at room temperature overnight. The mixture was then diluted with water (20 mL) and extracted with DCM (5 mL×2). The combined organic phases were washed with brine, dried over anhydrous $Na_2SO_4$, filtered, and concentrated. The remaining residue was purified by column chromatography on silica gel (eluted with DCM/MeOH=20:1) to afford 166-S2 (60 mg, 84.6% yield) as a white solid. LC/MS (ESI) m/z: 483 (M+H)$^+$.

Step 2: (1R,3S,5R)—N-(6-Bromo-3-(methoxymethyl)pyridin-2-yl)-5-((dimethylamino)methyl)-2-azabicyclo[3.1.0]hexane-3-carboxamide (166-S3)

To a solution of 166-S2 (38.5 mg, 0.08 mmol) in DCM (2 mL) was added TFA (1 mL). The reaction mixture was stirred at room temperature for 1.5 hours and then concentrated under reduced pressure to afford 166-S3 (38 mg, 100% yield) as a yellow solid, which was carried forward in the next synthetic step without further purification. LC/MS (ESI) m/z: 383 (M+H)$^+$.

Step 3: (1R,3S,5R)-2-(2-(3-Acetyl-5-(2-methylpyrimidin-5-yl)-1H-indazol-1-yl)acetyl)-N-(6-bromo-3-(methoxymethyl)pyridin-2-yl)-5-((dimethylamino)methyl)-2-azabicyclo[3.1.0]hexane-3-carbonamide (166)

To a mixture of 166-S3 (30.5 mg, 0.08 mmol), 2-(3-acetyl-5-(2-methylpyrimidin-5-yl)-1H-indazol-1-yl)acetic acid (25.3 mg, 0.08 mmol), and HATU (44.3 mg, 0.12 mmol) in DMF (2 mL) was added DIPEA (0.04 mL, 0.24 mmol). The reaction mixture was stirred at room temperature for 2 hours. The mixture was partitioned with EtOAc and water. The organic layer was washed with brine, dried over anhydrous $Na_2SO_4$, and concentrated under reduced pressure. The crude product was purified by preparative HPLC to afford 166 (6.5 mg, 12.1% yield) as a white solid.

¹H NMR (400 MHz, CD₃OD) δ 8.99 (s, 2H), 8.53 (s, 1H), 7.78 (s, 2H), 7.75 (d, J=8.1 Hz, 1H), 7.48 (d, J=8.0 Hz, 1H), 5.82 (d, J=17.2 Hz, 1H), 5.66 (d, J=17.1 Hz, 1H), 4.67 (d, J=4.0 Hz, 1H), 4.30-4.22 (m, 2H), 3.87 (d, J=2.9 Hz, 1H), 3.46 (d, J=13.2 Hz, 1H), 3.14 (s, 3H), 3.03 (d, J=13.3 Hz, 1H), 2.83 (s, 6H), 2.76 (s, 3H), 2.70 (s, 3H), 2.67 (s, 1H), 2.59-2.55 (m, 1H), 1.46-1.43 (m, 1H), 1.37-1.35 (m, 1H). LC/MS (ESI) m/z: 675 (M+H)⁺.

Scheme 66:
Synthesis of (1R,3S,5R)-2-(2-(3-Acetyl-7-((dimethylamino)methyl)-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (167)

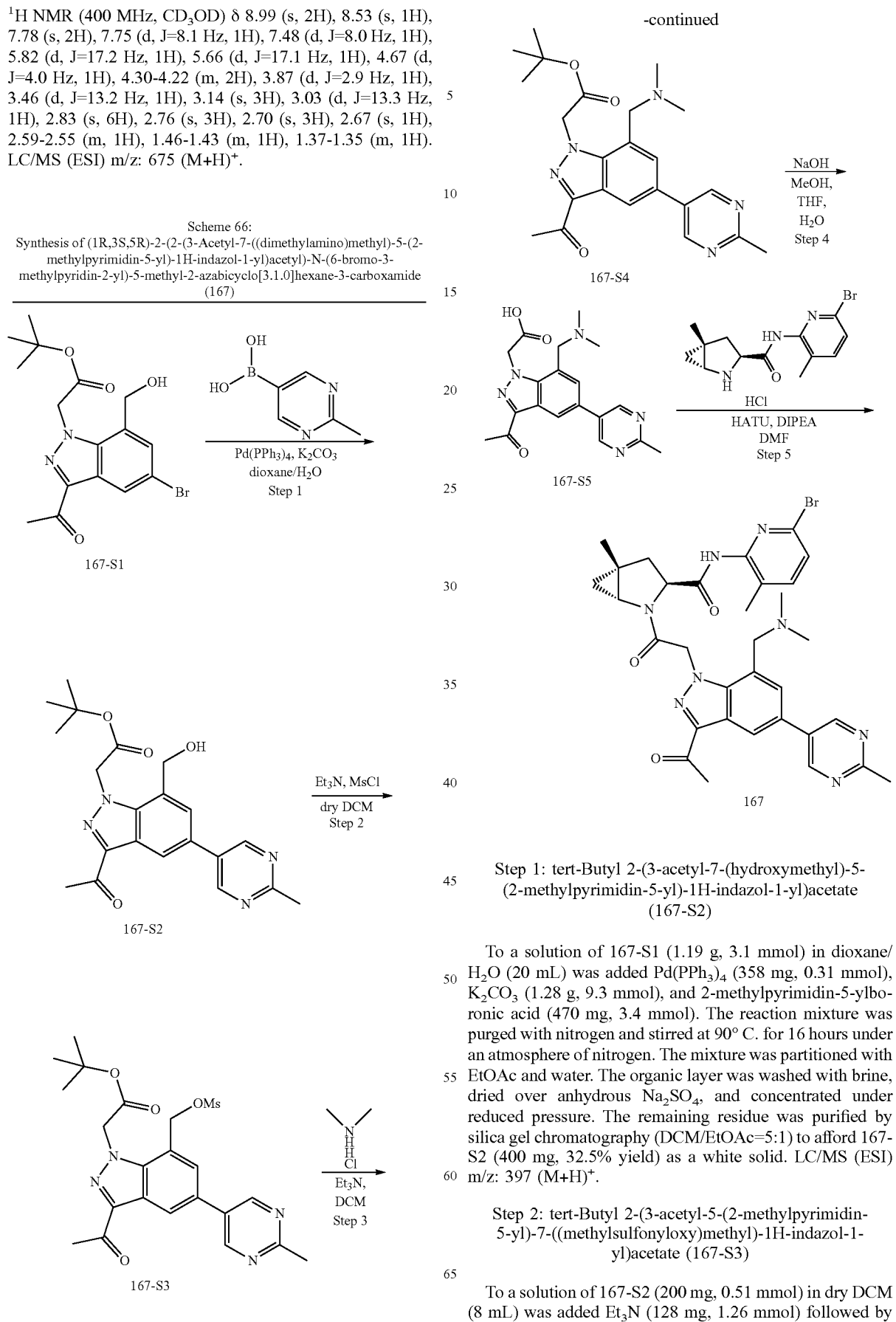

Step 1: tert-Butyl 2-(3-acetyl-7-(hydroxymethyl)-5-(2-methylpyrimidin-5-yl)-1H-indazol-1-yl)acetate (167-S2)

To a solution of 167-S1 (1.19 g, 3.1 mmol) in dioxane/H₂O (20 mL) was added Pd(PPh₃)₄ (358 mg, 0.31 mmol), K₂CO₃ (1.28 g, 9.3 mmol), and 2-methylpyrimidin-5-ylboronic acid (470 mg, 3.4 mmol). The reaction mixture was purged with nitrogen and stirred at 90° C. for 16 hours under an atmosphere of nitrogen. The mixture was partitioned with EtOAc and water. The organic layer was washed with brine, dried over anhydrous Na₂SO₄, and concentrated under reduced pressure. The remaining residue was purified by silica gel chromatography (DCM/EtOAc=5:1) to afford 167-S2 (400 mg, 32.5% yield) as a white solid. LC/MS (ESI) m/z: 397 (M+H)⁺.

Step 2: tert-Butyl 2-(3-acetyl-5-(2-methylpyrimidin-5-yl)-7-((methylsulfonyloxy)methyl)-1H-indazol-1-yl)acetate (167-S3)

To a solution of 167-S2 (200 mg, 0.51 mmol) in dry DCM (8 mL) was added Et₃N (128 mg, 1.26 mmol) followed by dropwise addition of MsCl (88 mg, 0.77 mmol) at 0° C. The reaction mixture was stirred at room temperature for 1 hour under an atmosphere of nitrogen. The mixture was diluted with DCM, washed with saturated aqueous NaHCO$_3$ solution and brine, dried over anhydrous Na$_2$SO$_4$, and concentrated under reduced pressure to afford 167-S3 (220 mg, 90.8% yield) as a white solid, which was used in the next synthetic step without further purification. LC/MS (ESI) m/z: 475 (M+H)$^+$.

Step 3: tert-Butyl 2-(3-acetyl-7-((dimethylamino)methyl)-5-(2-methylpyrimidin-5-yl)-1H-indazol-1-yl)acetate (167-S4)

To a solution of 167-S3 (110 mg, 0.3 mmol) in dry DCM (8 mL) were added Et$_3$N (90 mg, 0.9 mmol) and dimethylamine hydrochloride (60 mg, 0.54 mmol) at 0° C. The reaction mixture was stirred at room temperature for 16 hours under an atmosphere of nitrogen. The mixture was partitioned with DCM and NaHCO$_3$. The organic layer was washed with brine, dried over anhydrous Na$_2$SO$_4$ and concentrated under reduced pressure. The remaining residue was purified by column chromatography on silica gel (eluted with PE/EtOAc=5:1) to afford 167-S4 (62 mg, 48.7% yield) as a white solid. LC/MS (ESI) m/z: 424 (M+H)$^+$.

Step 4: 2-(3-Acetyl-7-(methoxycarbonyl)-5-(2-methylpyrimidin-5-yl)-1H-indazol-1-yl)acetic Acid (167-S5)

To a solution of 167-S4 (62 mg, 0.15 mmol) in MeOH/THF/H$_2$O (2:1:1, 4 mL) was added NaOH (18 mg, 0.45 mmol). The reaction mixture was stirred at room temperature for 1 hour. The mixture was diluted with water and washed with diethyl ether twice. The aqueous layer was adjusted to pH 5 with 10% aqueous HCl solution and extracted with DCM twice. The combined organic layers were dried over Na$_2$SO$_4$ and concentrated to afford 167-S5 (50 mg, 90.6% yield) as a white solid, which was carried forward in the next synthetic step without further purification. LC/MS (ESI) m/z: 368 (M+H)$^+$.

Step 5: (1R,3S,5R)-2-(2-(3-Acetyl-7-((dimethylamino)methyl)-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (167)

To a solution of 167-S5 (30 mg, 0.08 mmol) and (1R,3S,5R)—N-(6-bromo-3-methylpyridin-2-yl)-5-methyl-2-azabicyclo[3.1.0]hexane-3-carboxamide hydrochloride (28 mg, 0.08 mmol) in DMF (3 mL) were added DIPEA (42 mg, 0.32 mmol) and HATU (61 mg, 0.16 mmol). The reaction mixture was stirred at room temperature for 16 hours. The mixture was diluted with EtOAc, washed with 10% aqueous LiCl solution and brine successively, dried over anhydrous Na$_2$SO$_4$, and concentrated under reduced pressure. The remaining residue was purified by preparative HPLC (eluted with MeCN/water) to afford 167 (10 mg, 18.9% yield) as a white solid. $^1$H NMR (400 MHz, DMSO-d$_6$) δ 10.34 (s, 1H), 9.05 (s, 2H), 8.46 (d, J=1.6 Hz, 1H), 7.72 (s, 1H), 7.62 (d, J=8.0 Hz, 1H), 7.43 (d, J=7.9 Hz, 1H), 6.49 (d, J=17.3 Hz, 1H), 5.82 (d, J=17.1 Hz, 1H), 4.43 (dd, J=9.0, 5.5 Hz, 1H), 3.79 (d, J=12.8 Hz, 1H), 3.46-3.54 (m, 2H), 2.69 (s, 3H), 2.65 (s, 3H), 2.54-2.58 (m, 1H), 2.23 (s, 6H), 2.04 (s, 3H), 1.97-2.02 (m, 1H), 1.32 (s, 3H), 0.96-1.04 (m, 2H). LC/MS (ESI) m/z: 661 (M+H)$^+$.

Scheme 67:
Synthesis of (1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-((2,2,2-trifluoroacetamido)methyl)-2-azabicyclo[3.1.0]hexane-3-carboxamide (168)

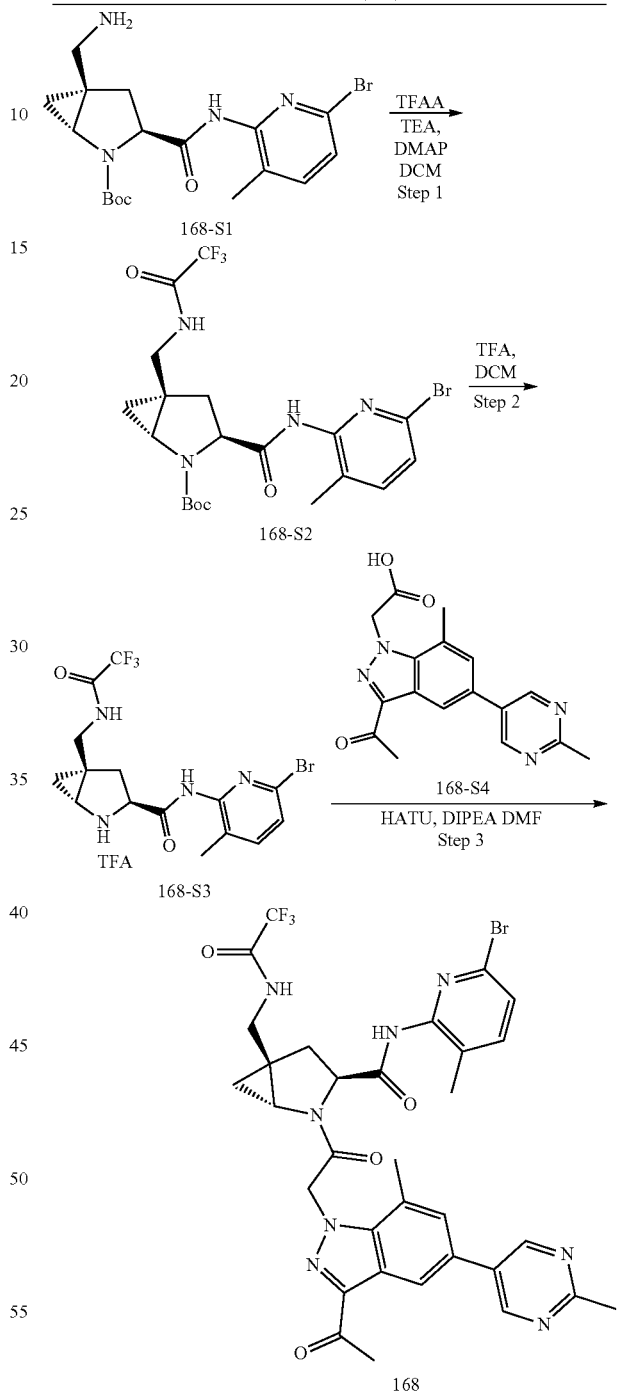

Step 1: (1R,3S,5R)-tert-Butyl 3-((6-bromo-3-methylpyridin-2-yl)carbamoyl)-5-((2,2,2-trifluoroacetamido)methyl)-2-azabicyclo[3.1.0]hexane-2-carboxylate (168-S2)

To a mixture of 169-S1 (40 mg, 0.094 mmol), Et$_3$N (23 mg, 0.24 mmol), and DMAP (1 mg, cat. amount) in dry DCM (2 mL) was added 2,2,2-trifluoroacetic anhydride (40 mg, 0.19 mmol) at 0° C. under an atmosphere of nitrogen. The reaction mixture was stirred at 0° C. for 2 hours. The mixture was diluted with DCM, washed with brine, dried, and concentrated to afford the crude product, which was purified by chromatography on silica gel (PE/EtOAc=10:1 to 5:1 to 4:1) to afford 168-S2 (35 mg, 71.5% yield) as a light oil. LC/MS (ESI) m/z: 521 (M+H)$^+$.

Step 2: 3-(6-Bromo-3-methyl-pyridin-2-ylcarbamoyl)-5-[(2,2,2-trifluoro-acetylamino)-methyl]-2-aza-bicyclo[3.1.0]hexane-2-carboxylic Acid Tert-Butyl Ester (168-S3)

To a solution of 168-S2 (35 mg, 0.067 mmol) in DCM (2 mL) was added TFA (1 mL) at 0° C. The reaction mixture was stirred at room temperature for 1 hour. The mixture was concentrated under reduced pressure to afford 168-S3 (28 mg, 99.5% yield) as a light oil, which was carried forward in the next synthetic step without further purification. LC/MS (ESI) m/z: 421 (M+H)$^+$.

Step 3: 2-{2-[3-Acetyl-7-methyl-5-(2-methyl-pyrimidin-5-yl)-indazol-1-yl]-acetyl}-5-[(2,2,2-trifluoro-acetylamino)-methyl]-2-aza-bicyclo[3.1.0]hexane-3-carboxylic Acid (6-bromo-3-methyl-pyridin-2-yl)-amide (168)

To a mixture of 168-S3 (28 mg, 0.067 mmol), 165-S4 (22 mg, 0.067 mmol), and HATU (38 mg, 0.10 mmol) in DMF (3 mL) was added DIPEA (26 mg, 0.20 mmol). The reaction mixture was stirred at room temperature for 2 hours. The mixture was diluted with EtOAc, washed with 10% aqueous LiCl solution and brine, dried, and concentrated to afford the crude product, which was purified with preparative HPLC to afford 168 (5.5 mg, 11.3% yield) as a white solid. $^1$H NMR (400 MHz, DMSO-d$_6$) δ 10.34 (s, 1H), 9.68 (s, 1H), 9.03 (s, 2H), 8.32 (s, 1H), 7.63 (d, J=8.0 Hz, 2H), 7.44 (d, J=8.0 Hz, 1H), 6.00 (d, J=20.0 Hz, 1H), 5.71 (d, J=20.0 Hz, 1H), 4.47 (m, 1H), 3.79 (m, 1H), 3.51 (m, 1H), 2.68 (s, 6H), 2.64 (d, J=8.0 Hz, 3H), 2.54 (d, J=8.0 Hz, 1H), 2.24 (m, 1H), 2.07 (d, J=12.0 Hz, 3H), 1.27-1.04 (m, 3H). LC/MS (ESI) m/z: 727 (M+H)$^+$.

Scheme 68: Synthesis of 2-{2-[3-Acetyl-7-methoxymethyl-5-(2-methyl-pyrimidin-5-yl)-indazol-1-yl]-acetyl}-5-methyl-2-aza-bicyclo[3.1.0]hexane-3-carboxylic acid (6-bromo-3-methoxymethyl-pyridin-2-yl)-amide (169)

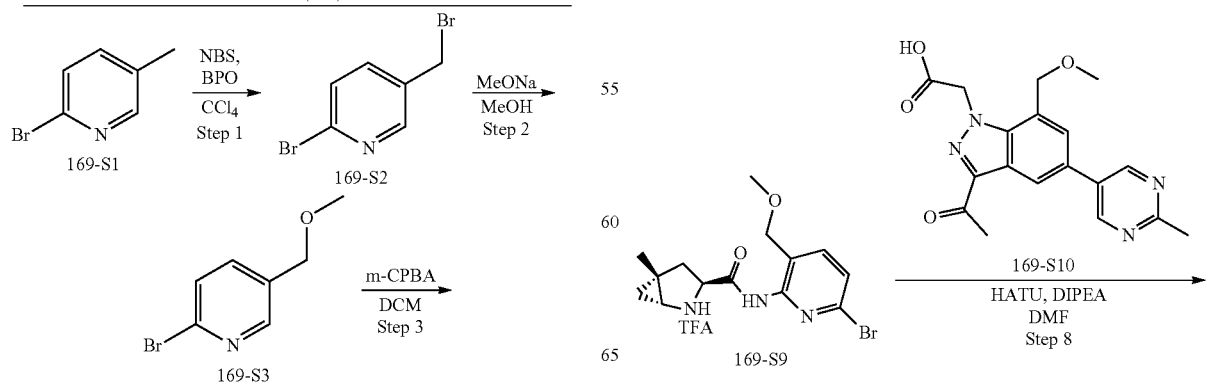

-continued

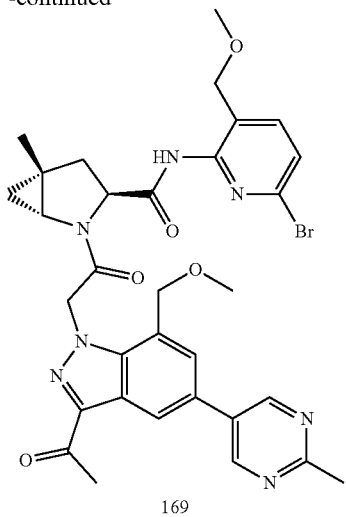

169

Step 1: 2-Bromo-5-bromomethyl-pyridine (169-S2)

To a solution of 169-S1 (5.0 g, 29.1 mmol) in CCl₄ (40 mL) was added NBS (5.22 g, 29.1 mmol) and BPO (350 mg, 1.4 mmol). The reaction mixture was stirred at 80° C. under an atmosphere of nitrogen for 2 hours. The mixture was diluted with DCM, washed with water and brine, dried, and concentrated to dryness. The remaining residue was purified by column chromatography on silica gel (eluted with PE/EtOAc=120:1) to afford 169-S2 (3.81 g, 52.6% yield) as a yellow oil. LC/MS (ESI) m/z: 250 (M+H)⁺.

Step 2: 2-Bromo-5-methoxymethyl-pyridine (169-S3)

To a solution of 169-S2 (3.81 g, 15.3 mmol) in MeOH (38 mL) was added MeONa (4.1 mL, 30% wt in MeOH) at 0° C. The reaction mixture was stirred at room temperature for 3 hours and concentrated to dryness. The remaining material was diluted with EtOAc, washed with water and brine, dried over Na₂SO₄, and concentrated to dryness. The remaining residue was purified by column chromatography on silica gel (eluted with PE/EtOAc=100:1) to afford 169-S3 (2.7 g, 87.8% yield) as a yellow oil. LC/MS (ESI) m/z: 202 (M+H)⁺.

Step 3: 2-Bromo-5-methoxymethyl-pyridine 1-oxide (169-S4)

To a solution of 169-S3 (2.7 g, 13.4 mmol) in DCM (23 mL) was added m-CPBA (3.47 g, 20.1 mmol). The reaction mixture was stirred at room temperature overnight. The mixture was filtered and the filtrate was diluted with DCM, washed with 1 N aqueous NaOH solution and brine, dried over Na₂SO₄, and concentrated to dryness. The remaining residue was purified by column chromatography on silica gel (eluted with DCM/MeOH=40:1) to afford 169-S4 (2.5 g, 86.2% yield) as a yellow oil. LC/MS (ESI) m/z: 218 (M+H)⁺.

Step 4: (6-Bromo-3-methoxymethyl-pyridin-2-yl)-tert-butyl-amine (169-S5)

To a solution of 169-S4 (1.0 g, 4.6 mmol) in DCM/toluene (20 mL, v/v=5/2) was added tert-butylamine (2.42 g, 33.2 mmol) followed by dropwise addition of a solution of p-toluenesulfonic anhydride (4.96 g, 15.2 mmol) in DCM/toluene (240 mL, v/v=5/2) for 4 h at −15° C. The reaction mixture was stirred at room temperature overnight, washed with aqueous NaHCO₃ solution and brine, dried, and concentrated to dryness. The remaining residue was purified by column chromatography on silica gel (eluted with PE/EtOAc=400:1) to afford 169-S5 (425 mg, 34.0% yield) as a yellow oil. LC/MS (ESI) m/z: 273 (M+H)⁺.

Step 5: 6-Bromo-3-methoxymethyl-pyridin-2-ylamine (169-S6)

To a solution of 169-S5 (214 mg, 0.78 mmol) in chloroform (3 mL) was added TFA (3 mL). The mixture was stirred at 90° C. for 20 minutes in a microwave reactor. The mixture was concentrated to dryness and diluted with DCM. The mixture was washed with aqueous NaHCO₃ solution and brine, dried, and concentrated to dryness. The remaining residue was purified by column chromatography on silica gel (eluted with PE/EtOAc=6:1) to afford 169-S6 (65 mg, 38.4% yield) as a white solid. LC/MS (ESI) m/z: 217 (M+H)⁺.

Step 6: 3-(6-Bromo-3-methoxymethyl-pyridin-2-ylcarbamoyl)-5-methyl-2-aza-bicyclo[3.1.0]hexane-2-carboxylic Acid Tert-Butyl Ester (169-S8)

To a mixture of 169-S6 (40 mg, 0.18 mmol) and 169-S7 (45 mg, 0.186 mmol) in DCM (3 mL) was added pyridine (0.08 mL, 0.93 mmol) and POCl₃ (0.02 mL, 0.186 mmol) under an atmosphere of nitrogen at 0° C. The mixture was stirred at room temperature for 30 minutes. The mixture was diluted with DCM, washed with aqueous NaHCO₃ solution and brine, dried, and concentrated to dryness. The remaining residue was purified by column chromatography on silica gel (eluted with PE/EtOAc=3:1) to afford 169-S8 (38 mg, 46.9% yield) as a white solid. LC/MS (ESI) m/z: 440 (M+H)⁺.

Step 7: 5-Methyl-2-aza-bicyclo[3.1.0]hexane-3-carboxylic Acid (6-bromo-3-methoxymethyl-pyridin-2-yl)-amide (169-S9)

To a solution of 169-S8 (38 mg, 0.086 mmol) in DCM (2 mL) was added TFA (1 mL) at 0° C. The reaction mixture was stirred at room temperature for 1 hour. The mixture was concentrated under reduced pressure to afford 169-S9 (29 mg, 99.5% yield) as a light oil, which was carried forward in the next synthetic step without further purification. LC/MS (ESI) m/z: 340 (M+H)⁺.

Step 8: 2-{2-[3-Acetyl-7-methoxymethyl-5-(2-methyl-pyrimidin-5-yl)-indazol-1-yl]-acetyl}-5-methyl-2-aza-bicyclo[3.1.0]hexane-3-carboxylic Acid (6-bromo-3-methoxymethyl-pyridin-2-yl)-amide (169)

To a mixture of 169-S9 (29 mg, 0.086 mmol), 169-S10 (40 mg, 0.11 mmol), and HATU (49 mg, 0.13 mmol) in DMF (3 mL) was added DIPEA (33 mg, 0.26 mmol). The reaction mixture was stirred at room temperature overnight. The mixture was diluted with EtOAc, washed with 10% aqueous LiCl solution and brine, dried, and concentrated to afford the crude product, which was purified with preparative HPLC to afford 169 (5.3 mg, 9.1% yield) as a white solid. $^1$H NMR (400 MHz, DMSO-d$_6$) δ 10.48 (s, 1H), 9.05 (s, 2H), 8.49 (d, J=2.0 Hz, 1H), 7.86 (d, J=1.5 Hz, 1H), 7.76 (d, J=8.0 Hz, 1H), 7.54 (d, J=12.0 Hz, 1H), 6.00 (d, J=16.0 Hz, 1H), 5.73 (d, J=20.0 Hz, 1H), 4.84 (d, J=12.0 Hz, 1H), 4.66 (d, J=12.0 Hz, 1H), 4.39 (m, 1H), 4.15 (d, J=4.0 Hz, 2H), 3.56 (m, 1H), 3.34-3.33 (m, 3H), 3.08 (s, 3H), 2.69 (s, 3H), 2.66 (s, 3H), 2.58-2.53 (m, 1H), 2.04 (m, 1H), 1.34 (s, 3H), 1.04-0.99 (m, 2H). LC/MS (ESI) m/z: 676 (M+H)$^+$.

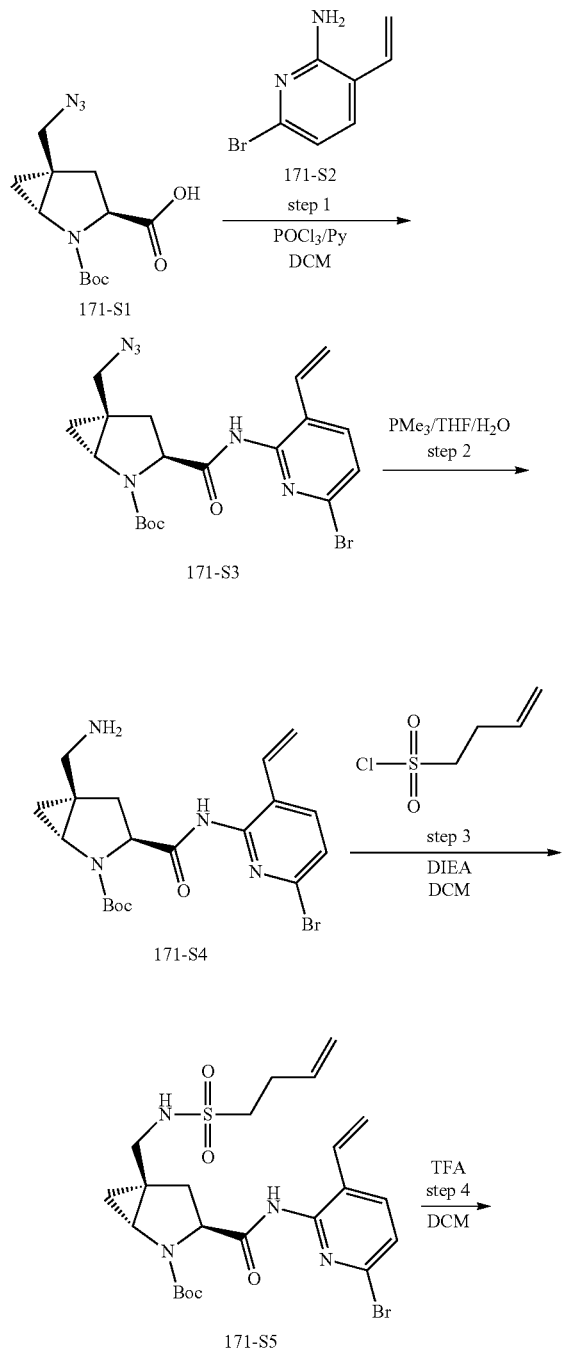

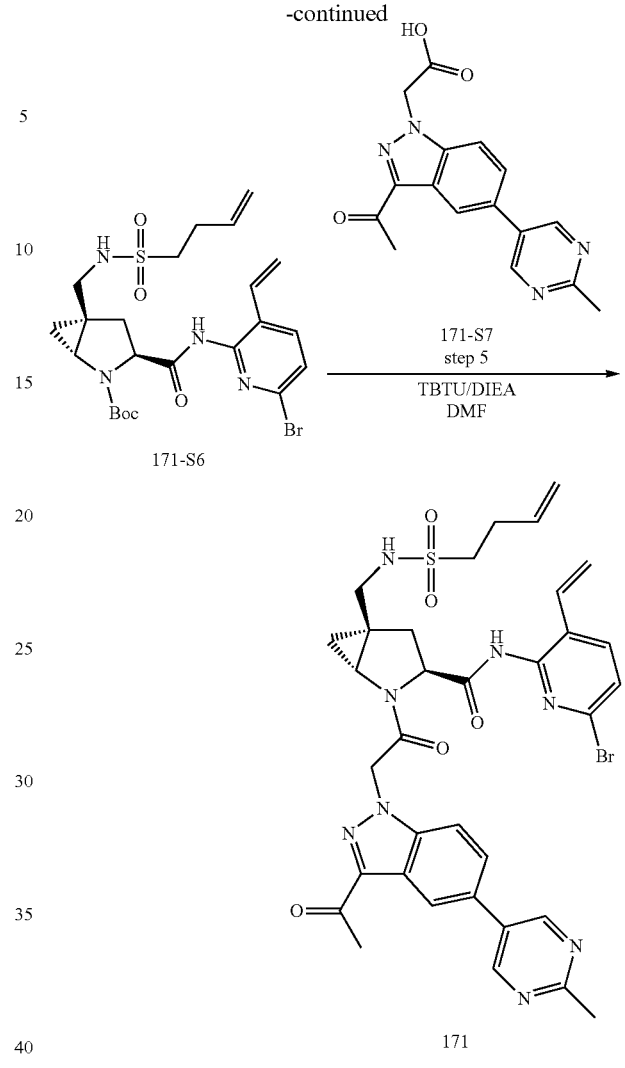

Step 1: tert-Butyl (1R,3S,5R)-5-(azidomethyl)-3-((6-bromo-3-vinylpyridin-2-yl)carbamoyl)-2-azabicyclo[3.1.0]hexane-2-carboxylate (171-S3)

To a mixture of 171-S1 (135 mg, 0.479 mmol) and 171-S2 (95.3 mg, 0.479 mmol) in DCM (5 mL), pyridine (0.193 mL, 2.4 mmol) was added followed by POCl$_3$ (0.045 mL, 0.48 mmol) at 0° C. under argon. The reaction mixture was stirred at room temperature for 2 hours. NaHCO$_3$ aqueous solution was added and the mixture was extracted with DCM. After washing with brine, the organic layer was dried over anhydrous Na$_2$SO$_4$. The solution was filtered and the solvent was removed under reduced pressure to afford tert-butyl (1R,3S,5R)-5-(azidomethyl)-3-((6-bromo-3-vinylpyridin-2-yl)carbamoyl)-2-azabicyclo[3.1.0]hexane-2-carboxylate 171-S3 (0.23 g) as a foam. The material was carried forward without additional purification.

Step 2: tert-Butyl (1R,3S,5R)-5-(aminomethyl)-3-((6-bromo-3-vinylpyridin-2-yl)carbamoyl)-2-azabicyclo[3.1.0]hexane-2-carboxylate (171-S4)

tert-Butyl (1R,3S,5R)-5-(azidomethyl)-3-((6-bromo-3-vinylpyridin-2-yl)carbamoyl)-2-azabicyclo[3.1.0]hexane-2- carboxylate (171-S3, 0.23 g) was treated with trimethylphosphane (1.0 M in THF, 0.958 mL, 0.958 mmol) in THF (10 mL) in the presence of water (0.017 mL, 0.958 mmol) at room temperature overnight. The mixture was extracted with EtOAc and the organic layer was washed with aqueous NaHCO$_3$ and brine, and dried over anhydrous Na$_2$SO$_4$. The solvent was removed under reduced pressure to afford tert-butyl (1R,3S,5R)-5-(aminomethyl)-3-((6-bromo-3-vinylpyridin-2-yl)carbamoyl)-2-azabicyclo[3.1.0]hexane-2-carboxylate 171-S4 (0.221 g) as pale yellow syrup. The material was carried forward in the next step without additional purification.

Step 3: tert-Butyl (1R,3S,5R)-3-((6-bromo-3-vinylpyridin-2-yl)carbamoyl)-5-((but-3-en-1-ylsulfonamido)methyl)-2-azabicyclo[3.1.0]hexane-2-carboxylate (171-S5)

tert-Butyl (1R,3S,5R)-5-(aminomethyl)-3-((6-bromo-3-vinylpyridin-2-yl)carbamoyl)-2-azabicyclo[3.1.0]hexane-2-carboxylate (171-S4, 0.221 g) was treated with but-3-ene-1-sulfonyl chloride (46.5 mg, 0.30 mmol) in DCM (5 mL) in the presence of DIEA (0.066 mL, 0.378 mmol). The reaction was stirred at room temperature for 30 minutes before NaHCO$_3$ aqueous was added and organic layer was washed with brine and dried over anhydrous Na$_2$SO$_4$. The solvent was removed under reduced pressure to afford tert-butyl (1R,3S,5R)-3-((6-bromo-3-vinylpyridin-2-yl)carbamoyl)-5-((but-3-en-1-ylsulfonamido)methyl)-2-azabicyclo[3.1.0]hexane-2-carboxylate 171-S5 (0.158 g) as a pale yellow syrup. The material was carried forward in the next step without additional purification.

Step 4: (1R,3S,5R)—N-(6-Bromo-3-vinylpyridin-2-yl)-5-((but-3-en-1-ylsulfonamido)methyl)-2-azabicyclo[3.1.0]hexane-3-carboxamide TFA Salt (171-S6)

tert-Butyl (1R,3S,5R)-3-((6-bromo-3-vinylpyridin-2-yl)carbamoyl)-5-((but-3-en-1-ylsulfonamido)methyl)-2-azabicyclo[3.1.0]hexane-2-carboxylate (171-S5, 19.8 mg) in DCM (1 mL) was treated with TFA (1 mL). The reaction was stirred at room temperature for 1 hour before the volatiles were removed under reduced pressure and the residue was co-evaporated with toluene (5 mL) twice to afford (1R,3S,5R)—N-(6-bromo-3-vinylpyridin-2-yl)-5-((but-3-en-1-ylsulfonamido)methyl)-2-azabicyclo[3.1.0]hexane-3-carboxamide TFA salt 171-S6. for the next step. The material was carried forward in the next step without additional purification.

Step 5: (1R,3S5R)-2-(2-(3-Acetyl-5-(2-methylpyrimidin-5-yl)-1H-indazol-1-yl)acetyl)-N-(6-bromo-3-vinylpyridin-2-yl)-5-((but-3-en-1-ylsulfonamido)methyl)-2-azabicyclo[3.1.0]hexane-3-carboxamide (171)

To a mixture of (1R,3S,5R)—N-(6-bromo-3-vinylpyridin-2-yl)-5-((but-3-en-1-ylsulfonamido)methyl)-2-azabicyclo[3.1.0]hexane-3-carboxamide TFA salt (171-S6, 0.0356 mmol) and 2-(3-acetyl-5-(2-methylpyrimidin-5-yl)-1H-indazol-1-yl)acetic acid (171-S7, 11 mg) in DMF (1.0 mL), TBTU (23 mg) was added followed by DIEA (0.031 mL) with stirring. After the reaction was complete, NaHCO$_3$ aqueous solution (10 mL) was added to form a precipitate that was collected by filtration and purified by column chromatography on silica gel with MeOH in DCM (0-10%) as the eluent to afford (1R,3S,5R)-2-(2-(3-acetyl-5-(2-methylpyrimidin-5-yl)-1H-indazol-1-yl)acetyl)-N-(6-bromo-3-vinylpyridin-2-yl)-5-((but-3-en-1-ylsulfonamido)methyl)-2-azabicyclo[3.1.0]hexane-3-carboxamide (171) (17 mg) as a pale yellow solid. $^1$H NMR (400 MHz, Chloroform-d) δ 8.90 (s, 2H), 8.83 (s, 1H), 8.58 (t, J=1.2 Hz, 1H), 7.69-7.58 (m, 3H), 7.30 (d, J=8.2 Hz, 1H), 6.44 (dd, J=11.0, 17.4 Hz, 1H), 5.81 (ddt, J=6.5, 10.2, 16.8 Hz, 1H), 5.74 (s, 1H), 5.64 (d, J=17.4 Hz, 1H), 5.51 (d, J=3.1 Hz, 2H), 5.28 (d, J=11.1 Hz, 1H), 5.18-5.06 (m, 2H), 4.94 (d, J=8.3 Hz, 1H), 3.58 (dd, J=4.6, 13.7 Hz, 1H), 3.52 (dd, J=2.8, 5.7 Hz, 1H), 3.16-3.08 (m, 3H), 2.80 (s, 4H), 2.72 (s, 3H), 2.56 (q, J=7.0 Hz, 2H), 2.27 (dd, J=8.4, 13.9 Hz, 1H), 1.44 (t, J=5.8 Hz, 1H), 1.12 (dd, J=2.8, 5.9 Hz, 1H). LC (method A): t$_R$=1.85 min. LC/MS (EI) m/z: [M+H]$^+$ 747.

Scheme 70.
Synthesis of (1R,3S,5R)-2-(2-(3-Acetyl-5-(2-Methylpyrimidin-5-yl)-1H-indazol-1-yl)acetyl)-N-(6-bromo-3-((3,3-difluoroazetidin-1-yl)methyl)pyridin-2-yl)-5-methyl-2-azabicyclo[3.1.0]hexane-3-carboxamide (177)

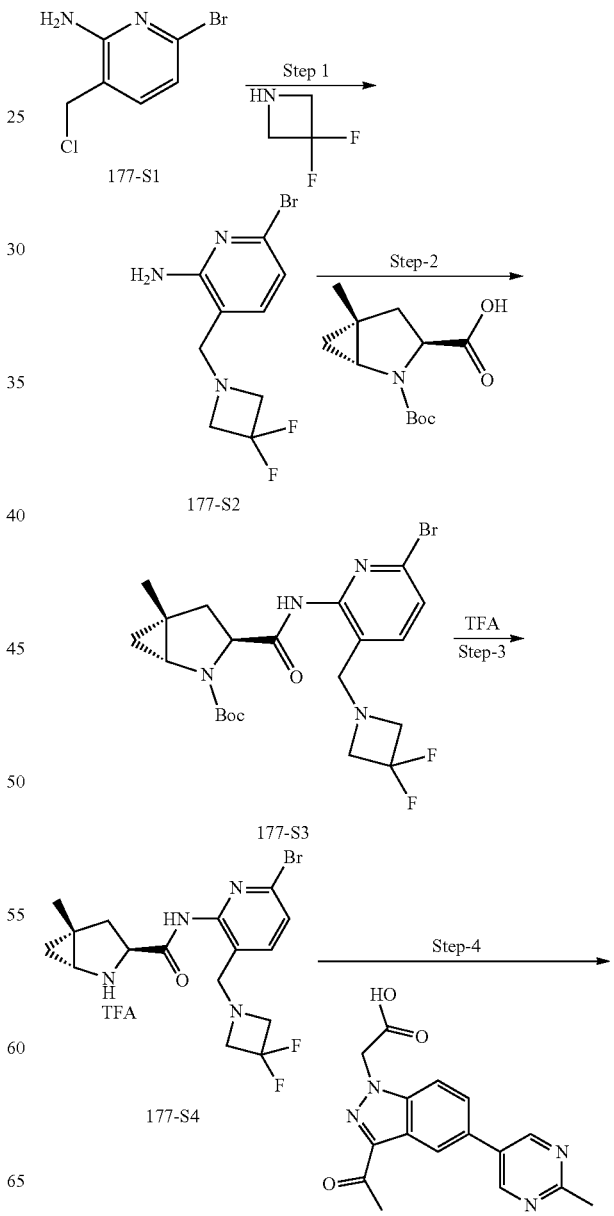

839

-continued

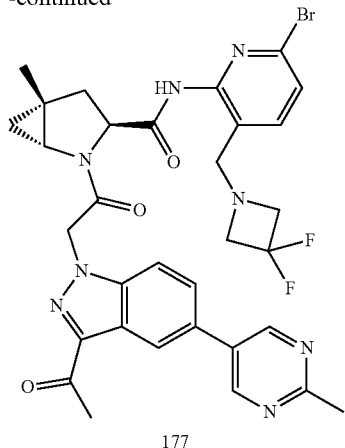

177

Step 1: 6-Bromo-3-((3,3-difluoroazetidin-1-yl)methyl)pyridin-2-amine (177-S2)

To a stirred solution 6-bromo-3-(chloromethyl)pyridin-2-amine (204 mg, 1 equiv) and triethyl amine (0.4, 3 equiv) in acetonitrile (20 mL) was added 3,3-difluoroazetidine hydrochloride (230 mg, 2 equiv) at 0-5° C. under an atmosphere of argon. The reaction mixture was stirred at room temperature until completion. The reaction was diluted with DCM (25 mL) and basified with aqueous saturated NaHCO$_3$ solution (20 mL). The aqueous layer was extracted with DCM (2×10 mL) and the combined organic layers were washed with brine (25 mL), dried over Na$_2$SO$_4$ and concentrated to dryness to afford 177-S2 (96 mg, 40%).

Step 2: tert-Butyl (1R,3S,5R)-3-((6-bromo-3-((3,3-difluoroazetidin-1-yl)methyl)pyridin-2-yl)carbamoyl)-5-methyl-2-azabicyclo[3.1.0]hexane-2-carboxylate (177-S3)

POCl$_3$ (0.04 mL, 2 equiv) was added dropwise at 0-5° C. under an atmosphere of argon to a stirred solution of (1R,3S,5R)-2-(tert-butoxycarbonyl)-5-methyl-2-azabicyclo[3.1.0]hexane-3-carboxylic acid (83 mg, 1 equiv) and 177-S2 (96 mg, 1 equiv) in DCM (10 mL) and pyridine (0.1 mL, 5 equiv). The reaction mixture was stirred at room temperature until completion. The reaction was diluted with DCM (15 mL) and basified with aqueous saturated NaHCO$_3$ solution (10 mL). The aqueous layer was extracted with DCM (1×15 mL) and the combined organic layers were washed with brine (20 mL), dried over Na$_2$SO$_4$ and concentrated to dryness. The residue was purified by column chromatography on silica gel (eluted by 5% MeOH in DCM gradient) to afford 177-S3 (147 mg, 85%).

Step 3: (1R,3S,5R)—N-(6-Bromo-3-((3,3-difluoroazetidin-1-yl)methyl)pyridin-2-yl)-5-methyl-2-azabicyclo[3.1.0]hexane-3-carboxamide (TFA Salt) (177-S4)

To a solution of 177-S3 (147 mg) in DCM (5 mL) was added TFA (5 mL). The resulting solution was stirred at room temperature for 2 hours. The reaction mixture was concentrated to dryness to afford 177-S4.

840

Step 4: (1R,3S,5R)-2-(2-(3-Acetyl-5-(2-methylpyrimidin-5-yl)-1H-indazol-1-yl)acetyl)-N-(6-bromo-3-((3,3-difluoroazetidin-1-yl)methyl)pyridin-2-yl)-5-methyl-2-azabicyclo[3.1.0]hexane-3-carboxamide (177)

To a solution of 177-S4 (135 mg, 1 equiv), 2-(3-acetyl-5-(2-methylpyrimidin-5-yl)-1H-indazol-1-yl)acetic acid (100 mg, 1.05 equiv), and DIPEA (0.26, 5 equiv) in DMF (10 mL) was added HATU (146 mg, 1.2 equiv) at 0° C. under an atmosphere of argon. The reaction mixture was stirred at room temperature for 3 hours. The reaction was diluted with EtOAc (40 mL) and water (20 mL). The aqueous layer was extracted with EtOAc (25 mL) and the combined organic layers were washed with brine, dried over anhydrous Na$_2$SO$_4$, filtered and concentrated. The residue was purified by column chromatography on silica gel (eluted by DCM/MeOH=10:1) to afford 177 (25 mg, 12%). $^1$H NMR (400 MHz, DMSO-d$_6$) δ 10.30 (s, 1H), 8.96 (s, 2H), 8.37 (s, 1H), 7.80 (m, 2H), 7.67 (d, 1H, J=8.2 Hz), 7.42 (d, 1H, J=8.2 Hz), 5.87 (d, 1H, J=17.5 Hz), 5.52 (d, 1H, J=17.5 Hz), 4.29-4.36 (m, 1H), 3.22-3.56 (m, 1H), 3.37-3.45 (m, 2H), 3.25-3.33 (m, 3H), 2.62 (s, 3H), 2.58 (s, 3H), 2.26 (s, 1H), 1.99-2.04 (m, 1H), 1.27 (s, 3H), 0.91-0.99 (m, 3H); $^{19}$F NMR (376 MHz, DMSO-d$_6$) δ −97.89 (2F).

Scheme 71.
Synthesis of (1R,3S,5R)-2-(2-(3-Acetyl-5-(2-methylpyrimidin-5-yl)-1H-indazol-1-yl)acetyl)-N-(6-bromo-5-fluoro-3-methylpyridin-2-yl)-5-methyl-2-azabicyclo[3.1.0]hexane-3-carboxamide (178)

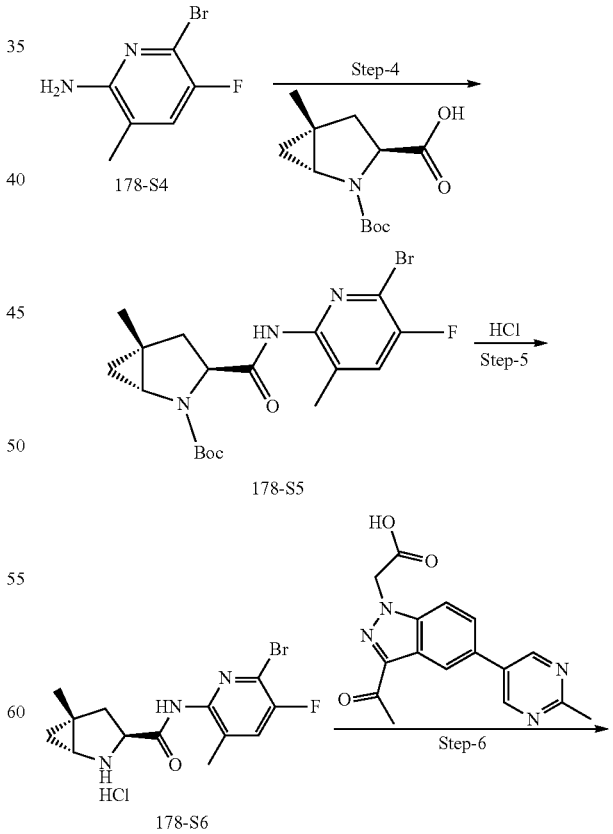

841

-continued

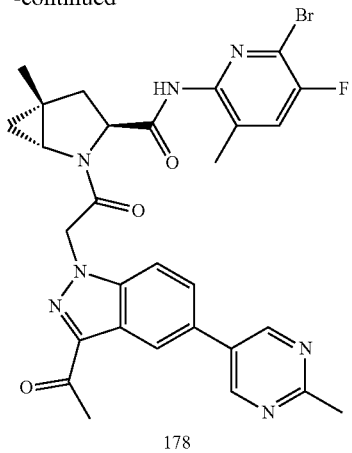

178

Step 1: 2-Bromo-3-fluoro-5-methyl-(1-oxidanyl)-pyridine (178-S2)

To a stirred solution of 2-bromo-3-fluoro-5-methylpyridine (175-S1, 10 g, 1 equiv) in $CHCl_3$ (200 mL) was added 3-chlorobenzoperoxoic acid (24 g, 2 equiv). The reaction mixture was heated to 50° C. The reaction was cooled and neutralized with saturated aqueous $NaHCO_3$ ((100 mL). The organic layer was washed with brine, dried over $Na_2SO_4$ and concentrated to dryness. The residue was purified by column chromatography silica gel (5% $CH_3OH$ in DCM, gradient) to afford 178-S2 (9.4 g, 87%).

Step 2: 6-Bromo-N-(tert-butyl)-5-fluoro-3-methylpyridin-2-amine (178-S3)

To a stirred solution of 178-S2 (3.2 g, 1 equiv) and 2-methylpropan-2-amine (8.1 mL, 5 equiv) in DCM (100 mL) at 0-5° C. was slowly added trifluoroacetic anhydride (TFAA, 2.7 mL, 1.1 equiv) solution in DCM (20 mL) dropwise using an additional funnel over 40 minutes under an atmosphere of argon at 0-5° C. The reaction mixture was stirred at 0-5° C. for 1 hour and monitored by LC/MS. (If the reaction was not complete after 1 hour, TFAA ((2.5 mL, 1 equiv) solution in DCM (20 mL, added over 15 to 20 minutes) and 2-methylpropan-2-amine (1.6 mL, 1 equiv, added once) were added). The reaction was diluted with DCM (60 mL) and neutralized with aqueous saturated $NaHCO_3$ (80 mL). The organic layer was washed with brine (80 mL), dried over $Na_2SO_4$ and concentrated to dryness. The residue was purified by column chromatography on silica gel (eluted by hexanes/EtOAc=3:1) to afford 178-S3.

Step 3: 6-Bromo-5-fluoro-3-methylpyridin-2-amine (178-S4)

TFA (20 mL) was added to solid 178-S3 and the reaction mixture was heated at 70° C. until completion. The reaction was concentrated to dryness and the residue was dissolved in DCM (35 mL), washed with aqueous saturated $NaHCO_3$ solution (15 mL×2) and brine, dried over $Na_2SO_4$, and concentrated to afford 178-S4 (838 mg, 26%).

Step 4: (1R,3S,5R)—N-(6-Bromo-5-fluoro-3-methylpyridin-2-yl)-5-methyl-2-azabicyclo[3.1.0]hexane-3-carboxamide Hydrochloride (178-S5)

$POCl_3$ (0.1 mL, 2 equiv) was added dropwise to a solution of (1R,3S,5R)-2-(tert-butoxycarbonyl)-5-methyl-2-azabicyclo[3.1.0]hexane-3-carboxylic acid (121 mg, 1 equiv) and 178-S4 (101 mg, 1 equiv) in DCM (8 mL) and pyridine (0.2 mL, 5 equiv) cooled at 0-5° C. under an atmosphere of argon. The reaction mixture was stirred at room temperature until completion. The reaction was diluted with DCM (10 mL) and neutralized with aqueous saturated $NaHCO_3$ solution (10 mL). The aqueous layer was extracted with DCM (1× mL) and the combined organic layers were washed with brine (10 mL), dried over $Na_2SO_4$, and concentrated to dryness. The residue was purified by column chromatography on silica gel (eluted by 5% MeOH in DCM gradient) to afford 178-S5 (131 mg, 62%)

Step 5: (1R,3S,5R)—N-(6-Bromo-5-fluoro-3-methylpyridin-2-yl)-5-methyl-2-azabicyclo[3.1.0]hexane-3-carboxamide Hydrochloride (178-S6)

To a solution of 178-S5 (131 mg) was added 4N HCl in dioxane (8 mL). The resulting solution was stirred at room temperature for 6 hours. The reaction mixture was concentrated to dryness to afford 178-S6.

Step 6: (1R,3S,5R)-2-(2-(3-Acetyl-5-(2-methylpyrimidin-5-yl)-1H-indazol-1-yl)acetyl)-N-(6-bromo-5-fluoro-3-methylpyridin-2-yl)-5-methyl-2-azabicyclo[3.1.0]hexane-3-carboxamide (178)

To a solution of 178-S6 (137 mg, 1 equiv), 2-(3-acetyl-5-(2-methylpyrimidin-5-yl)-1H-indazol-1-yl)acetic acid (115 mg, 1.2 equiv) and DIPEA (0.3 mL, 5 equiv) in DMF (10 mL) was added HATU (141 mg, 1.2 equiv) at 0° C. under an atmosphere of argon. The reaction mixture was stirred at room temperature for 3 hours before it was diluted with EtOAc (30 mL) and water (15 mL). The organic layer was washed with brine, dried over anhydrous $Na_2SO_4$ and concentrated to dryness. The residue was purified by column chromatography on silica gel (eluted by DCM/MeOH=10:1) to afford 178 (79 mg, 41%). $^1$H NMR (400 MHz, DMSO-$d_6$) δ 10.11 (s, 1H), 9.06 (s, 2H), 8.46 (s, 1H), 7.87 (s, 1H), 7.81-7.87 (m, 2H), 5.92 (d, 1H, J=17.4 Hz), 5.59 (d, 1H, J=17.4 Hz), 4.37-4.42 (m, 1H), 3.58 (d, 1H, J=5.4 Hz), 2.70 (s, 3H), 2.67 (s, 3H), 2.54-2.59 (m, 1H), 2.08 (s, 3H), 2.02-2.07 (m, 1H), 1.33 (s, 3H), 0.99-1.06 (m, 2H). $^{19}$F NMR (376 MHz, DMSO-$d_6$) δ-118.95 (s, 1F).

Scheme 72. Synthesis of (1R,3S,5R)-2-(2-(3-Acetyl-5-(2-methylpyrazolo[1,5-a]pyrimidin-6-yl)-1H-indazol-1-yl)acetyl)-N-(6-bromo-3-methylpyridin-2-yl)-5-methyl-2-azabicyclo[3.1.0]hexane-3-carboxamide (180)

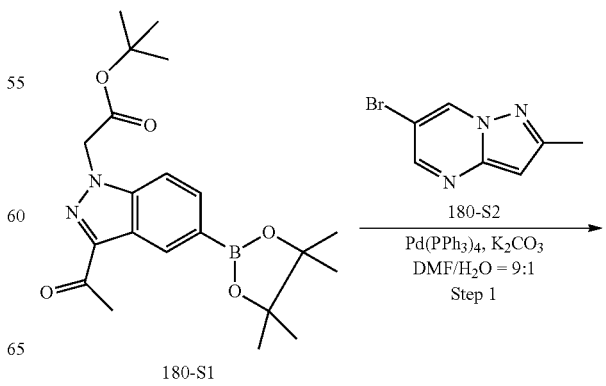

843
-continued

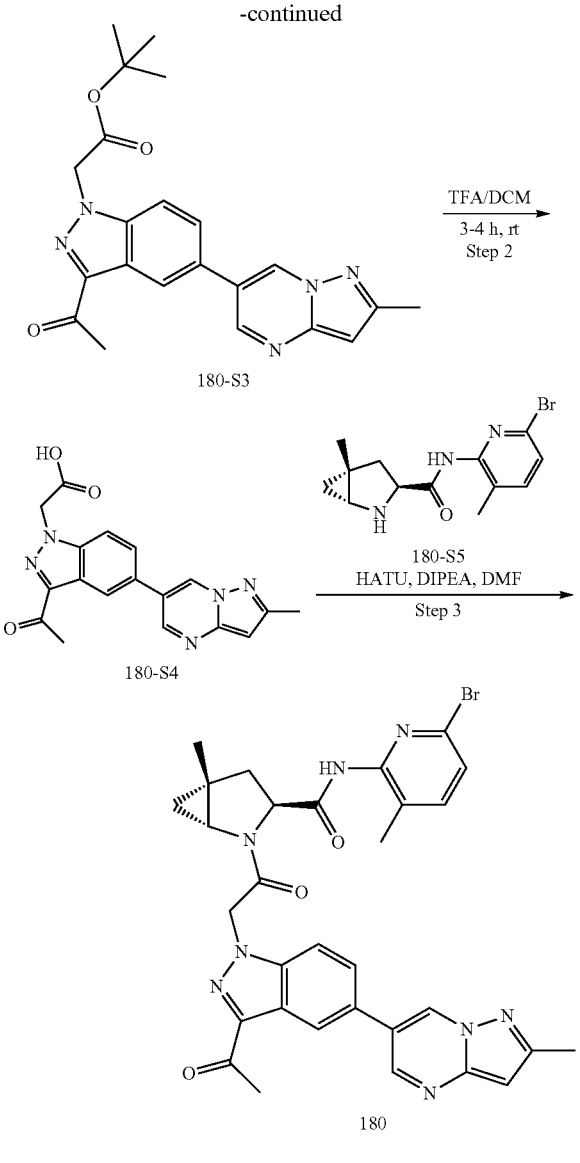

Step 1: tert-butyl 2-(3-Acetyl-5-(2-methylpyrazolo[1,5-a]pyrimidin-6-yl)-1H-indazol-1-yl)acetate (180-S3)

To a solution of 6-bromo-2-methylpyrazolo[1,5-a]pyrimidine (180-S2, 1 equiv) in DMF/H$_2$O (9:1, 10 vol) was added compound 180-S1 (1 equiv), K$_2$CO$_3$ (2 equiv) and tetrakis(triphenylphosphine)palladium (0.1 equiv). The reaction mixture was stirred at 90° C. for 5 hours and concentrated under reduced pressure. The remaining residue was purified by column chromatography on silica gel (eluted with DCM/MeOH) to afford compound 180-S3.

Step 2: 2-(3-Acetyl-5-(2-methylpyrazolo[1,5-a]pyrimidin-6-yl)-1H-indazol-1-yl)acetic Acid (180-S4)

To a solution of compound 180-S3 (1 equiv) in DCM (10 vol) at 0° C. under an atmosphere of argon was added TFA (5 vol). The reaction mixture was stirred at room temperature for 3 hours and concentrated to dryness. The remaining material was used directly in the next synthetic step.

844

Step 3: (1R,3S,5R)-2-(2-(3-Acetyl-5-(2-methylpyrazolo[1,5-a]pyrimidin-6-yl)-1H-indazol-1-yl)acetyl)-N-(6-bromo-3-methylpyridin-2-yl)-5-methyl-2-azabicyclo[3.1.0]hexane-3-carboxamide (180)

To a solution of compound 180-S4 (1 equiv) in DMF (10 vol) at 0° C. under an atmosphere of argon was added (1R,3S,5R)—N-(6-bromo-3-methylpyridin-2-yl)-5-methyl-2-azabicyclo[3.1.0]hexane-3-carboxamide (1 equiv), HATU (2.1 equiv), and DIPEA (5 equiv). The reaction mixture was stirred at room temperature for 3 hours and quenched with water (30 vol). The resulting mixture was extracted with DCM. The organic layer was washed with brine, dried over anhydrous Na$_2$SO$_4$, filtered, and concentrated to dryness. The remaining residue was purified by column chromatography on silica gel (eluted with DCM/MeOH) to afford compound 180. $^1$H NMR (400 MHz, DMSO-d$_6$) δ 0.98-1.09 (m, 2H), 1.33 (s, 3H), 2.06 (s, 4H), 2.47 (s, 3H), 2.52-2.59 (m, 1H), 2.67 (s, 3H), 3.56-3.63 (m, 1H), 4.42 (dd, J=5.1, 9.3 Hz, 1H), 5.58 (d, J=17.2 Hz, 1H), 5.92 (d, J=17.3 Hz, 1H), 6.58 (s, 1H), 7.45 (d, J=7.9 Hz, 1H), 7.63 (d, J=7.9 Hz, 1H), 7.84 (d, J=8.8 Hz, 1H), 7.90 (d, J=8.8 Hz, 1H), 8.48 (s, 1H), 8.86 (d, J=2.2 Hz, 1H), 9.35 (d, J=2.2 Hz, 1H), 10.26 (s, 1H).

Scheme 73.
Synthesis of (1R,3S,5R)-2-(2-(3-Acetyl-5-(2-methylpyrimidin-5-yl)-1H-indazol-1-yl)acetyl)-N-(6-bromo-3-(difluoromethyl)-4-methylpyridin-2-yl)-5-methyl-2-azabicyclo[3.1.0]hexane-3-carboxamide (187)

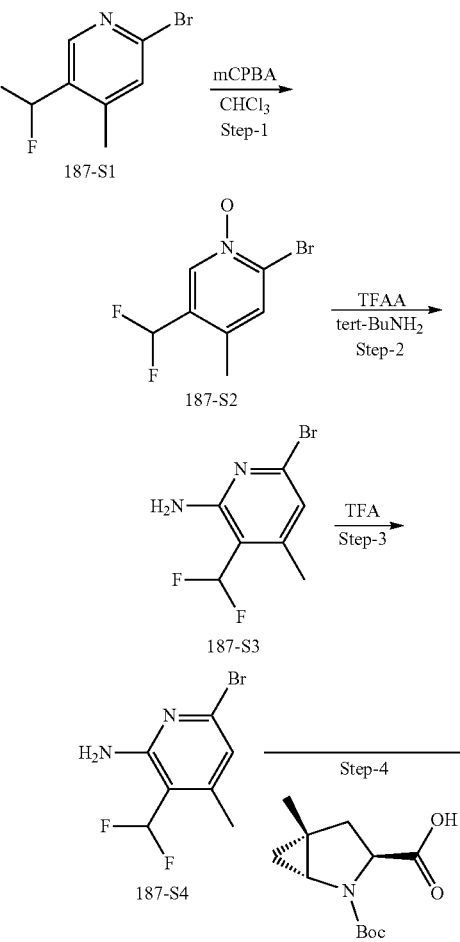

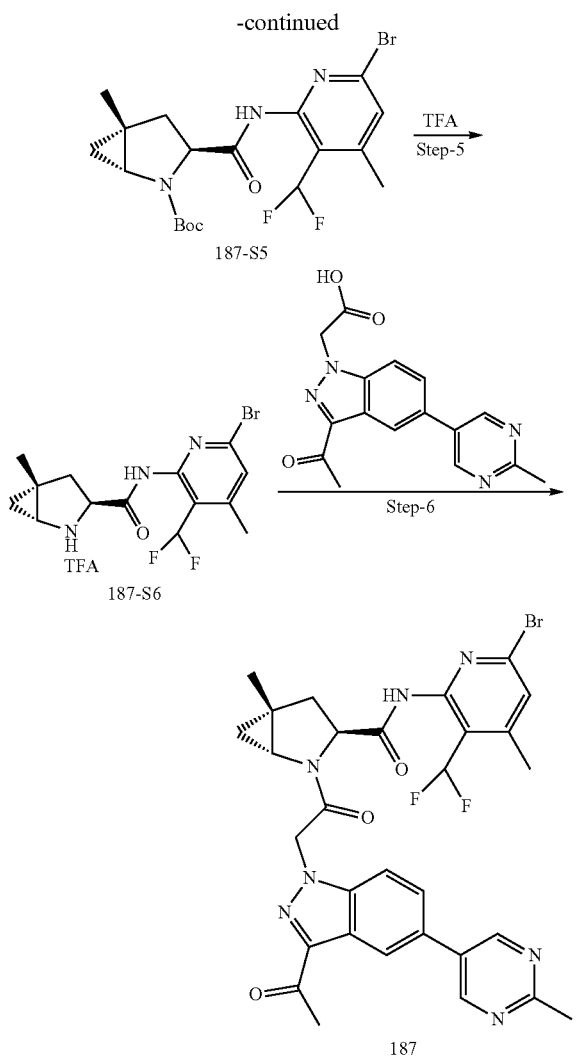

Step 1: 2-Bromo-5-(difluoromethyl)-4-methyl-1-oxidanyl)pyridine (187-S2)

To a stirred solution of 2-bromo-5-(difluoromethyl)-4-methylpyridine (187-S1, 1 g, 1 equiv) in CHCl₃ (150 mL) was added 3-chlorobenzoperoxoic acid (2.1 g, 2 equiv). The reaction mixture was heated to 50° C. until completion. The reaction was cooled and neutralized with saturated aqueous NaHCO₃ solution (60 mL). The organic layer was washed with brine, dried over Na₂SO₄ and concentrated to dryness. The residue was purified by column chromatography on silica gel (eluted by 5% CH₃OH in DCM, gradient) to afford 187-S2 (851 mg, 80%).

Step 2: 6-Bromo-N-(tert-butyl)-3-(difluoromethyl)-4-methylpyridin-2-amine (187-S3)

To a stirred solution of 187-S2 (222 mg, 1 equiv) and 2-methylpropan-2-amine (0.49 mL, 5 equiv) in DCM (100 mL) was added trifluoroacidic anhydride (0.3 mL, 2 equiv) solution in DCM (5 mL) at 0-5° C. dropwise under an atmosphere of argon. The reaction mixture was stirred at 0-5° C. for 2 hours before the reaction was neutralized with aqueous saturated NaHCO₃ solution (15 mL). The organic layer was washed with brine (15 mL), dried over Na₂SO₄ and concentrated. The crude was purified by column chromatography on silica gel (eluted by 30% EtOAc in hexanes) to afford 187-S3 (130 mg, 48%)

Step 3: 6-Bromo-3-(difluoromethyl)-4-methylpyridin-2-amine (187-S4)

TFA (8 mL) was added to solid 187-S3 (130 mg) and the reaction mixture was heated at 70° C. until completion. The reaction mixture was concentrated to dryness and the residue was dissolved in DCM (15 mL) and neutralized with aqueous saturated NaHCO₃ solution (15 mL). The organic layer was washed with brine, dried over Na₂SO₄ and concentrated to dryness to afford 187-S4 (92 mg, 87%).

Step 4: tert-Butyl (1R,3S,5R)-3-((6-bromo-3-(difluoromethyl)-4-methylpyridin-2-yl)carbamoyl)-5-methyl-2-azabicyclo[3.1.0]hexane-2-carboxylate (187-S5)

POCl₃ was added dropwise (0.05 mL, 2 equiv) at 0-5° C. under an atmosphere of argon to a stirred solution of (1R,3S,5R)-2-(tert-butoxycarbonyl)-5-methyl-2-azabicyclo [3.1.0]hexane-3-carboxylic acid (94 mg, 1 equiv) and 187-S4 (92 mg, 1 equiv) in DCM (10 mL) and pyridine (0.1 mL, 5 equiv). The reaction mixture was stirred at room temperature until completion. The reaction was diluted with DCM (20 mL) and neutralized with aqueous saturated NaHCO₃ solution (15 mL). The aqueous layer was extracted with DCM (1×10 mL) and the combined organic layers were washed with brine (10 mL), dried over Na₂SO₄, and concentrated to dryness. The residue was purified by column chromatography on silica gel (eluted by 5% MeOH in DCM gradient) to afford 187-S5 (109 mg, 61%).

Step 5: (1R,3S,5R)—N-(6-Bromo-3-(difluoromethyl)-4-methylpyridin-2-yl)-5-methyl-2-azabicyclo [3.1.0]hexane-3-carboxamide (TFA Salt) (187-S6)

To a solution of S5 (109 mg) in DCM (5 mL) was added TFA (5 mL). The resulting solution was stirred at room temperature for 1 hour. The reaction mixture was concentrated to dryness to afford 187-S6 (65 mg).

Step 6: (1R,3S,5R)-2-(2-(3-Acetyl-5-(2-methylpyrimidin-5-yl)-1H-indazol-1-yl)acetyl)-N-(6-bromo-3-(difluoromethyl)-4-methylpyridin-2-yl)-5-methyl-2-azabicyclo[3.1.0]hexane-3-carboxamide (187)

To a solution of 187-S6 (65 mg, 1 equiv), 2-(3-acetyl-5-(2-methylpyrimidin-5-yl)-1H-indazol-1-yl)acetic acid (44 mg, 1.05 equiv), and DIPEA (0.12 mL, 5 equiv) in DMF (8 mL) was added HATU (64 mg, 1.2 equiv) at 0° C. under an atmosphere of argon. The reaction mixture was stirred at room temperature for 3 hours. The reaction mixture was diluted with EtOAc (40 mL) and water (20 mL). The aqueous layer was extracted with EtOAc (20 mL) and the combined organic layers were washed with brine (3×20 mL), dried over anhydrous Na₂SO₄, filtered and concentrated. The residue was purified by column chromatography on silica gel (eluted by DCM/MeOH=10:1) to afford 187 (67 mg, 27%). ¹H NMR (400 MHz, DMSO-d₆) δ 10.70 (s, 1H), 9.04 (s, 2H), 8.46 (s, 1H), 7.87 (S, br, 2H), 7.64 (s, 1H), 6.66 (m, 1H), 5.93 (d, 1H, J=18.2 Hz), 5.61 (d, 1H, J=18.2 Hz), 4.28-4.34 (m, 1H), 3.62-3.66 (m, 1H), 2.69 (s, 3H), 2.66 (s, 3H), 2.46 (s, 3H), 2.53-2.58 (m, 1H), 1.99-2.06 (M, 1H), 1.33 (s, 3H), 0.93-1.05 (m, 2H); $^{19}$F NMR (376 MHz, DMSO-d$_6$) δ −112.35 (1F), −113.24 (1F).

Scheme 74. Synthesis of (1R,3S,5R)-2-(2-(3-Acetyl-5-(2-methylpyrimidin-5-yl)-1H-indazol-1-yl)acetyl)-N-(6-bromo-3-vinylpyridin-2-yl)-5-((N-methylbut-3-en-1-ylsulfonamido)methyl)-2-azabicyclo[3.1.0]hexane-3-carboxamide (188)

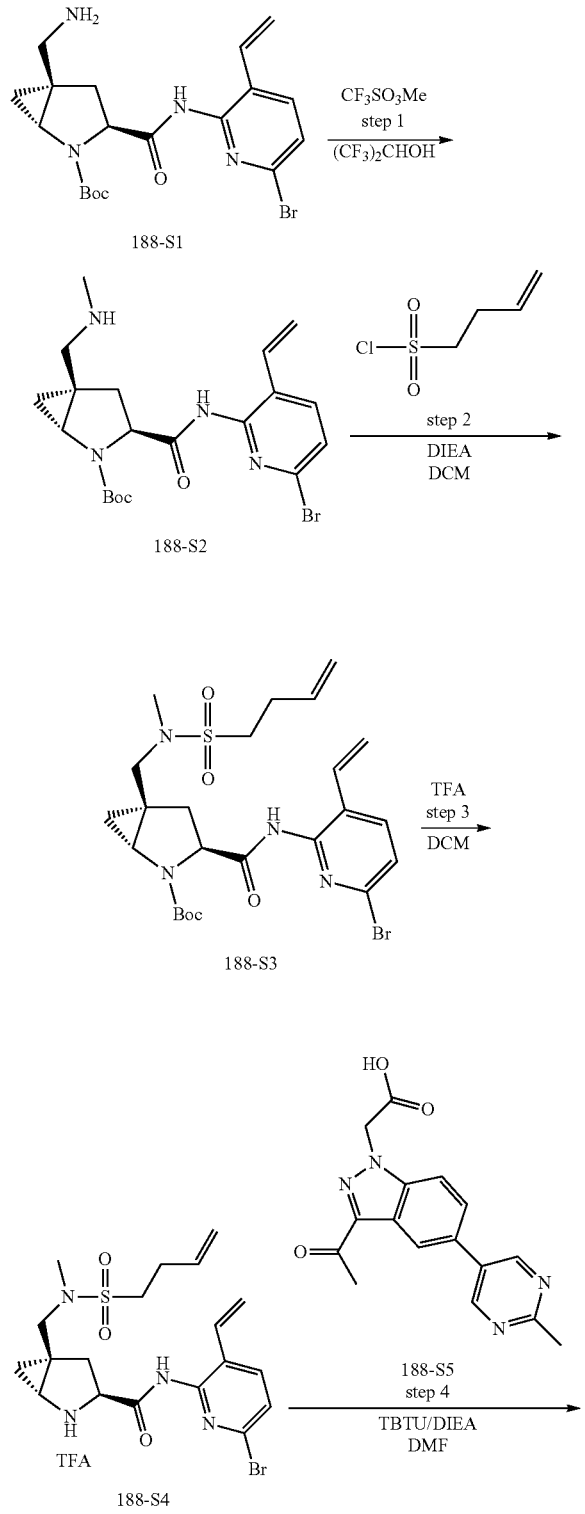

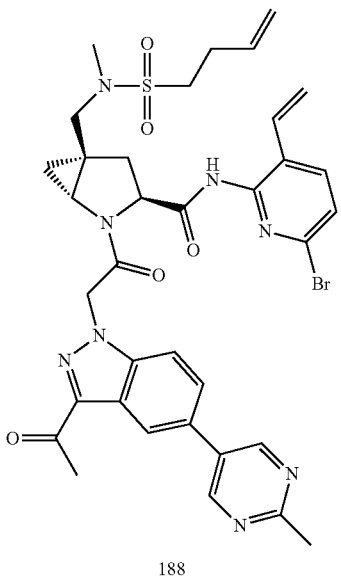 [SMILES: C=CCCS(=O)(=O)N(C)C[C@@]12C[C@@H](C(=O)Nc3nc(Br)ccc3C=C)N(C(=O)Cn3nc(C(C)=O)c4cc(-c5cnc(C)nc5)ccc43)[C@@H]1C2]

Step 1: tert-Butyl (1R,3S,5R)-3-((6-bromo-3-vinylpyridin-2-yl)carbamoyl)-5-((methylamino)methyl)-2-azabicyclo[3.1.0]hexane-2-carboxylate (188-S2)

tert-Butyl (1R,3S,5R)-5-(aminomethyl)-3-((6-bromo-3-vinylpyridin-2-yl)carbamoyl)-2-azabicyclo[3.1.0]hexane-2-carboxylate (188-S1, 0.104 g, 0.238 mmol) was treated with methyl triflate (0.032 mL, 0.286 mmol) in 1,1,1,3,3,3-hexafluoro-2-propanol at room temperature. The reaction stirred at room temperature for 3 hours before EtOAc was added to dilute the reaction. The mixture was washed with NaHCO$_3$ and brine and dried over anhydrous Na$_2$SO$_4$. The solvent was removed to afford tert-butyl (1R,3S,5R)-3-((6-bromo-3-vinylpyridin-2-yl)carbamoyl)-5-((methylamino)methyl)-2-azabicyclo[3.1.0]hexane-2-carboxylate 188-S2. The material was carried forward in the next step without additional purification.

Step 2: tert-Butyl (1R,3S,5R)-3-((6-bromo-3-vinylpyridin-2-yl)carbamoyl)-5-((N-methylbut-3-en-1-ylsulfonamido)methyl)-2-azabicyclo[3.1.0]hexane-2-carboxylate (188-S3)

tert-Butyl (1R,3S,5R)-5-((methylamino)aminomethyl)-3-((6-bromo-3-vinylpyridin-2-yl)carbamoyl)-2-azabicyclo[3.1.0]hexane-2-carboxylate 188-S2 was treated with but-3-ene-1-sulfonyl chloride (44 mg, 0.286 mmol) in DCM (5 mL) in the presence of DIEA (0.062 mL, 0.357 mmol). The reaction stirred at room temperature for 30 minutes before NaHCO$_3$ aqueous was added. The organic layer was washed with brine and dried over anhydrous Na$_2$SO$_4$. The solvent was removed under reduced pressure to afford a mixture containing tert-butyl (1R,3S,5R)-3-((6-bromo-3-vinylpyridin-2-yl)carbamoyl)-5-((N-methylbut-3-en-1-ylsulfonamido)methyl)-2-azabicyclo[3.1.0]hexane-2-carboxylate 188-S3. The material was carried forward in the next step without additional purification.

Step 3: (1R,3S,5R)—N-(6-Bromo-3-vinylpyridin-2-yl)-5-((N-methylbut-3-en-1-ylsulfonamido)methyl)-2-azabicyclo[3.1.0]hexane-3-carboxamide TFA Salt (188-S4)

tert-Butyl (1R,3S,5R)-3-((6-bromo-3-vinylpyridin-2-yl)carbamoyl)-5-((N-methylbut-3-en-1-ylsulfonamido)methyl)-2-azabicyclo[3.1.0]hexane-2-carboxylate 188-S3 in DCM (3 mL) was treated with TFA (3 mL) at room temperature for 1 hour. The volatiles were removed under reduced pressure and the residue was co-evaporated with toluene (5 mL) twice to afford a mixture (1R,3S,5R)—N-(6-bromo-3-vinylpyridin-2-yl)-5-((N-methylbut-3-en-1-ylsulfonamido)methyl)-2-azabicyclo[3.1.0]hexane-3-carboxamide TFA salt 188-S4. The material was carried forward in the next step without additional purification.

Step 4: (1R,3S,5R)-2-(2-(3-Acetyl-5-(2-methylpyrimidin-5-yl)-1H-indazol-1-yl)acetyl)-N-(6-bromo-3-vinylpyridin-2-yl)-5-((N-methylbut-3-en-1-ylsulfonamido)methyl)-2-azabicyclo[3.1.0]hexane-3-carboxamide (188)

To a mixture of (1R,3S,5R)—N-(6-bromo-3-vinylpyridin-2-yl)-5-((N-methylbut-3-en-1-ylsulfonamido)methyl)-2-azabicyclo[3.1.0]hexane-3-carboxamide TFA salt 188-S4 and 2-(3-acetyl-5-(2-methylpyrimidin-5-yl)-1H-indazol-1-yl)acetic acid (188-S5, 74 mg) in DMF (3.0 mL), TBTU (115 mg) was added followed by DIEA (0.414 mL) with stirring. After the reaction was complete, the mixture was purified by HPLC to afford (1R,3S,5R)-2-(2-(3-acetyl-5-(2-methylpyrimidin-5-yl)-1H-indazol-1-yl)acetyl)-N-(6-bromo-3-vinylpyridin-2-yl)-5-((N-methylbut-3-en-1-ylsulfonamido)methyl)-2-azabicyclo[3.1.0]hexane-3-carboxamide (188, 25.5 mg) as a white powder. $^1$H NMR (400 MHz, Chloroform-d) δ 8.90 (s, 2H), 8.74 (s, 1H), 8.58 (s, 1H), 7.71-7.55 (m, 3H), 7.30 (d, J=8.1 Hz, 1H), 6.44 (dd, J=11.0, 17.4 Hz, 1H), 5.91-5.70 (m, 1H), 5.65 (d, J=17.4 Hz, 1H), 5.51 (s, 2H), 5.27 (d, J=11.0 Hz, 1H), 5.19-5.02 (m, 2H), 4.93 (d, J=8.4 Hz, 1H), 3.48 (dd, J=6.8, 13.0 Hz, 3H), 3.01 (d, J=18.8 Hz, 5H), 2.80 (s, 4H), 2.72 (s, 3H), 2.54 (q, J=7.3 Hz, 2H), 2.31 (t, J=11.4 Hz, 1H), 1.48 (t, J=5.9 Hz, 1H), 1.06 (dd, J=2.7, 6.0 Hz, 1H). LC (method A): $t_R$=2.01 min. LC/MS (EI) m/z: [M+H]$^+$ 761.

Scheme 75. Synthesis of (1R,3S,5R)-2-(2-(3-Acetyl-5-(2-methoxypyrimidin-5-yl)-1H-pyrazolo[3,4-c]pyridin-1-yl)acetyl)-N-(6-bromo-3-methylpyridin-2-yl)-5-methyl-2-azabicyclo[3.1.0]hexane-3-carboxamide (193)

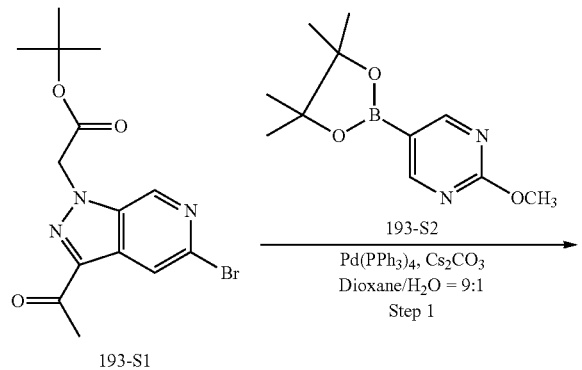

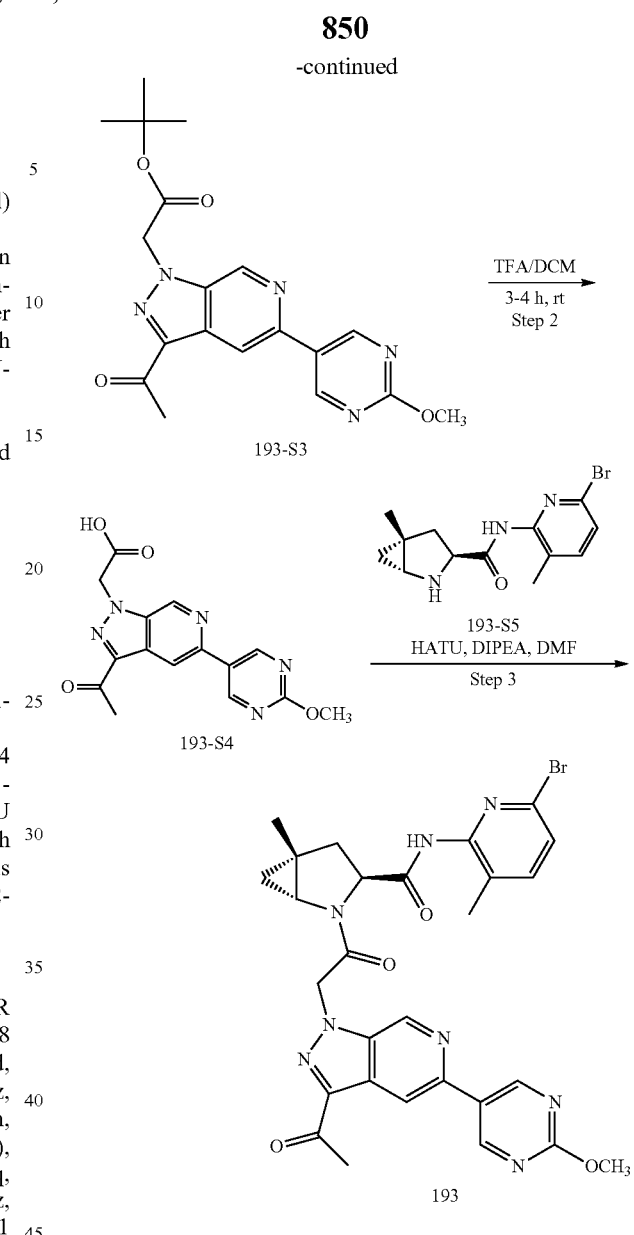

The above scheme and following detailed description depicts one non-limiting method for synthesizing compounds with a substituted pyrimidine in the R$^{32}$ position utilizing a boronic ester in a Suzuki cross-coupling. The skilled artisan will recognize that the boronic ester shown above can be replaced with other boronic esters or boronic acids to afford additional compounds of the present invention. The skilled artisan will also recognize that the A-ring shown can be replaced with other A-rings to afford additional compounds of the present invention. Non-limiting examples of boronic esters that the skilled artisan can use include 5-(4,4,5,5-tetramethyl-1,3,2-dioxaborolan-2-yl)pyrimidin-2-amine and 2-methyl-5-(4,4,5,5-tetramethyl-1,3,2-dioxaborolan-2-yl)pyrimidine.

Step 1: tert-Butyl 2-(3-acetyl-5-(2-methoxypyrimidin-5-yl)-1H-pyrazolo[3,4-c]pyridin-1-yl)acetate (193-S3)

To a solution of 2-methoxy-5-(4,4,5,5-tetramethyl-1,3,2-dioxaborolan-2-yl)pyrimidine (193-S2, 1 equiv) in dioxane/

H₂O (9:1, 10 vol) was added compound 193-S1 (1 equiv), Cs₂CO₃ (2 equiv), and tetrakis(triphenylphosphine)palladium (0.1 equiv). The reaction mixture was stirred at 90° C. for 5 hours and concentrated to dryness. The remaining residue was purified by column chromatography on silica gel (eluted with DCM/MeOH) to afford compound 193-S3.

Step 2: 2-(3-Acetyl-5-(2-methoxypyrimidin-5-yl)-1H-pyrazolo[3,4-c]pyridin-1-yl)acetic Acid (193-S4)

To a solution of compound 193-S3 (1 equiv) in DCM (10 vol) at 0° C. under an atmosphere of argon was added TFA (5 vol). The reaction mixture was stirred at room temperature for 3 hours and concentrated to dryness. The remaining material was carried forward without additional purification and used directly in the next synthetic step.

Step 3: (1R,3S,5R)-2-(2-(3-Acetyl-5-(2-methoxypyrimidin-5-yl)-1H-pyrazolo[3,4-c]pyridin-1-yl)acetyl)-N-(6-bromo-3-methylpyridin-2-yl)-5-methyl-2-azabicyclo[3.1.0]hexane-3-carboxamide (193)

To a solution of compound 193-S4 (1 equiv) in DMF (10 vol) at 0° C. under an atmosphere of argon was added (1R,3S,5R)—N-(6-bromo-3-methylpyridin-2-yl)-5-methyl-2-azabicyclo[3.1.0]hexane-3-carboxamide (193-S5, 1 equiv), HATU (2.1 equiv), and DIPEA (5 equiv). The reaction mixture was stirred at room temperature for 3 hours and quenched with water (30 vol). The resulting mixture was extracted with DCM. The organic layer was washed with brine, dried over anhydrous Na₂SO₄, filtered, and then concentrated to dryness. The remaining residue was purified by column chromatography on silica gel (eluted with DCM/MeOH) to afford compound 193. $^1$H NMR (400 MHz, DMSO-d₆) δ 1.02 (t, J=5.5 Hz, 1H), 1.10 (dd, J=2.4, 5.3 Hz, 1H), 1.34 (s, 3H), 2.01-2.10 (m, 4H), 2.56 (dd, J=9.3, 13.3 Hz, 1H), 2.69 (s, 3H), 3.58-3.65 (m, 1H), 4.01 (s, 3H), 4.35-4.52 (m, 1H), 5.72 (d, J=17.2 Hz, 1H), 6.04 (d, J=17.3 Hz, 1H), 7.45 (d, J=7.9 Hz, 1H), 7.63 (d, J=7.9 Hz, 1H), 8.55 (d, J=1.3 Hz, 1H), 9.22-9.30 (m, 3H), 10.27 (s, 1H).

(1R,3S,5R)-2-(2-(3-Acetyl-5-(2-aminopyrimidin-5-yl)-1H-pyrazolo[3,4-c]pyridin-1-yl)acetyl)-N-(6-bromo-3-methylpyridin-2-yl)-5-methyl-2-azabicyclo[3.1.0]hexane-3-carboxamide (194)

$^1$H NMR (400 MHz, DMSO-d₆) δ 0.98-1.04 (m, 1H), 1.06-1.11 (m, 1H), 1.33 (s, 3H), 1.98-2.09 (m, 4H), 2.54-2.61 (m, 1H), 2.67 (s, 3H), 3.55-3.65 (m, 1H), 4.38-4.46 (m, 1H), 5.69 (d, J=17.2 Hz, 1H), 6.01 (d, J=17.3 Hz, 1H), 6.90 (s, 2H), 7.45 (d, J=7.9 Hz, 1H), 7.63 (d, J=7.9 Hz, 1H), 8.37 (s, 1H), 8.93 (s, 2H), 9.20 (s, 1H), 10.27 (s, 1H).

1-(2-((1R,3S,5R)-3-((6-Bromo-5-fluoro-3-methylpyridin-2-yl)carbamoyl)-5-methyl-2-azabicyclo[3.1.0]hexan-2-yl)-2-oxoethyl)-5-(2-methylpyrimidin-5-yl)-1H-pyrazolo[3,4-c]pyridine-3-carboxamide (199)

$^1$H NMR (400 MHz, DMSO-d₆) δ 0.89-0.98 (m, 2H), 1.26 (s, 3H), 1.93-2.02 (m, 4H), 2.47-2.51 (m, 1H), 2.62 (s, 3H), 3.47-3.54 (m, 1H), 4.27-4.40 (m, 1H), 5.57 (d, J=17.3 Hz, 1H), 5.87 (d, J=17.3 Hz, 1H), 7.55 (d, 1H), 7.75 (d, J=8.4 Hz, 1H), 7.81 (s, 1H), 8.53 (s, 1H), 9.18 (s, 1H), 9.26 (s, 2H), 10.19 (s, 1H).

(1R,3S,5R)-2-(2-(3-Acetyl-5-(2-methylpyrimidin-5-yl)-1H-pyrazolo[3,4-c]pyridin-1-yl)acetyl)-N-(6-bromo-3-methylpyridin-2-yl)-5-methyl-2-azabicyclo[3.1.0]hexane-3-carboxamide $^1$H-NMR (400 MHz, CDCl₃): δ 0.91-0.93 (m, 1H), 1.20 (t, J=5.6 Hz, 1H), 1.43 (s, 3H), 2.11 (s, 3H), 2.39 (t, J=8.4 Hz, 1H), 2.58 (s, 3H), 2.66 (d, J=11.6 Hz, 1H), 2.81 (s, 3H), 3.18 (d, J=4 Hz, 1H), 4.84 (d, J=7.6 Hz, 1H), 5.21 (d, J=16.8 Hz, 1H), 5.32 (d, J=17.2 Hz, 1H), 7.23 (d, J=8 Hz, 1H), 7.36 (d, J=7.6 Hz, 1H), 7.98 (s, 1H), 8.41 (brs, 1H), 8.71 (s, 1H), 8.81 (s, 1H), 9.29 (s, 2H).

((2S,4R)—N-(6-Bromopyridin-2-yl)-4-fluoro-1-(2-(5-(2-methylpyrimidin-5-yl)-1H-indazol-1-yl)acetyl)pyrrolidine-2-carboxamide $^1$H-NMR (400 MHz, CDCl₃) δ 9.22 (s, 1H), 8.58 (s, 2H), 8.14 (s, 1H), 8.00 (d, J=8 Hz, 1H), 7.84 (s, 1H), 7.54-7.43 (m, 3H), 7.14 (d, J=8 Hz, 1H), 5.29-5.16 (dd, J=16 Hz, 2H), 4.81 (t, J=8 Hz, 1H), 4.03-3.95 (q, J=12 Hz, 1H), 3.52-3.39 (m, 1H), 2.8 (s, 3H), 2.51-2.45 (m, 3H). LC/MS (ESI) m/z: 537 (M+H)⁺.

(1R,3S,5R)—N-(6-Bromo-3-methylpyridin-2-yl)-5-methyl-2-(2-(5-(2-methylpyrimidin-5-yl)-3-(2,2,2-trifluoroacetyl)-1H-indol-1-yl)acetyl)-2-azabicyclo[3.1.0]hexane-3-carboxamide $^1$H-NMR (400 MHz, DMSO-d₆) δ 10.29 (s, 1H), 9.02 (s, 2H), 8.66 (s, 1H), 8.45 (s, 1H), 7.73-7.79 (m, 2H), 7.61-7.63 (d, J=8 Hz, 1H), 7.43-7.45 (d, J=7.2 Hz, 1H), 5.67-5.71 (d, J=16.8 Hz, 1H), 5.44-5.48 (d, J=17.2 Hz, 1H), 4.37-4.41 (m, 1H), 3.57-3.58 (m, 1H), 2.68 (s, 3H), 2.02 (s, 3H), 1.95-2.07 (m, 2H), 1.33 (s, 3H), 0.98-1.05 (m, 2H). LC/MS (ESI) m/z: 657 (M+H)⁺.

(1R,3S,5R)-2-(2-(3-Acetyl-5-(2-methylpyrimidin-5-yl)-1H-indol-1-yl)acetyl)-N-(6-bromo-5-fluoro-3-methylpyridin-2-yl)-5-methyl-2-azabicyclo[3.1.0]hexane-3-carboxamide $^1$H-NMR (400 MHz, CD₃OD) δ 8.97 (s, 2H), 8.55 (s, 1H), 8.25 (s, 1H), 7.55-7.58 (m, 3H), 5.45-5.48 (d, J=17.2 Hz, 1H), 5.34-5.39 (d, J=17.2 Hz, 1H), 4.48-4.51 (m, 1H), 3.51-3.53 (m, 1H), 2.73 (s, 3H), 2.60-2.64 (m, 1H), 2.54 (s, 3H), 2.28-2.29 (m, 1H), 2.14 (s, 3H), 1.40 (s, 3H), 1.08-1.11 (m, 1H), 0.97-0.099 (m, 2H). LC/MS (ESI) m/z: 619/621 (M+H)⁺.

(1R,3S,5R)—N-(6-Bromo-3-methylpyridin-2-yl)-5-methyl-2-(2-(5-(2-methylpyrimidin-5-yl)-3-(2,2,2-trifluoroacetyl)-1H-pyrrolo[2,3-c]pyridin-1-yl)acetyl)-2-azabicyclo[3.1.0]hexane-3-carboxamide $^1$H-NMR (400 MHz, DMSO-d₆) δ 10.29 (s, 1H), 9.32 (s, 2H), 9.09 (s, 1H), 8.81 (d, J=1.5 Hz, 1H), 8.62 (s, 1H), 7.63 (d, J=8.0 Hz, 1H), 7.45 (d, J=7.9 Hz, 1H), 5.81 (d, J=17.2 Hz, 1H), 5.57 (d, J=17.1 Hz, 1H), 4.41-4.42 (m, 1H), 3.55 (t, J=3.9 Hz, 1H), 2.69 (s, 3H), 2.52-2.54 (m, 1H), 2.03-2.04 (m, 1H), 2.02 (s, 3H), 1.33 (s, 3H), 1.04 (m, 2H). LC/MS (ESI) m/z: 656 (M+H)⁺.

(1R, 3S, 5R)-2-(2-(3-Acetyl-2-methyl-5-(2-methylpyrimidin-5-yl)-1H-indol-1-yl)acetyl)-N-(6-bromo-3-methylpyridin-2-yl)-5-methyl-2-azabicyclo[3.1.0]hexane-3-carboxamide $^1$H-NMR (400 MHz, DMSO-d₆) δ 10.26 (s, 1H), 9.03 (s, 2H), 8.28 (s, 1H), 7.67-7.41 (m, 4H), 5.54 (d, J=17.8 Hz, 1H), 5.23 (d, J=17.8 Hz, 1H), 4.39 (m, 1H), 3.66 (m, 1H), 2.67 (s, 3H), 2.65 (s, 3H), 2.64 (s, 3H), 2.33 (m, 1H), 2.04-2.05 (m, 1H), 2.02 (s, 3H), 1.33 (s, 3H), 1.02 (m, 2H). LC/MS (ESI) m/z: 615/617 (M+H)$^+$.

(1R,3S,5R)-2-(2-(3-Acetyl-5-(2-methylpyrimidin-5-yl)-1H-pyrrolo[2,3-b]pyridin-1-yl)acetyl)-N-(6-bromo-3-methylpyridin-2-yl)-5-methyl-2-azabicyclo[3.1.0]hexane-3-carboxamide $^1$H-NMR (400 MHz, DMSO-d$_6$) δ 10.27 (s, 1H), 9.07 (s, 2H), 8.73 (d, J=2.2 Hz, 1H), 8.69 (d, J=2.2 Hz, 1H), 8.56 (s, 1H), 7.62 (d, J=8.1 Hz, 1H), 7.44 (d, J=7.9 Hz, 1H), 5.56 (d, J=17.1 Hz, 1H), 5.36 (d, J=16.9 Hz, 1H), 4.41 (m, 1H), 3.59-3.55 (m, 1H), 2.67 (s, 3H), 2.53-2.55 (m, 1H), 2.51 (s, 3H), 2.07 (s, 3H), 2.02-2.05 (m, 1H), 1.32 (s, 3H), 1.06 (m, 1H), 0.95 (m, 1H). LC/MS (ESI) m/z: 602/604 (M+H)$^+$.

(1R,3S,5R)-2-(2-(3-Acetyl-6-fluoro-5-(2-methylpyrimidin-5-yl)-1H-indol-1-yl)acetyl)-N-(6-bromo-3-methylpyridin-2-yl)-5-methyl-2-azabicyclo[3.1.0]hexane-3-carboxamide $^1$H-NMR (400 MHz, DMSO-d$_6$) δ 10.27 (s, 1H), 8.87 (s, 2H), 8.39 (s, 1H), 8.25-8.27 (d, J=7.8 Hz, 1H), 7.61 (dd, J=17.8, 9.7 Hz, 2H), 7.45 (d, J=7.9 Hz, 1H), 5.55 (d, J=17.2 Hz, 1H), 5.27 (d, J=17.2 Hz, 1H), 4.39 (m, 1H), 3.56-3.57 (m, 1H), 2.69 (s, 3H), 2.51 (s, 3H), 2.33-2.35 (m, 1H), 2.07-2.10 (m, 1H), 2.03 (s, 3H), 1.33 (s, 3H), 1.05-0.95 (m, 2H). LC/MS (ESI) m/z: 619/621 (M+H)$^+$.

(1R,3S,5R)-2-{2-[1-Acetyl-6-(2-methylpyrimidin-5-yl)indazol-3-yl] acetyl}-N-(6-bromo-3-methylpyridin-2-yl)-5-methyl-2-azabicyclo[3.1.0]hexane-3-carboxamide $^1$H-NMR (400 MHz, CD$_3$OD) δ 8.99 (d, J=4.9 Hz, 2H), 8.61 (s, 1H), 7.97-7.92 (m, 1H), 7.69-7.64 (m, 1H), 7.54 (d, J=8.0 Hz, 1H), 7.37 (d, J=7.9 Hz, 1H), 4.54-4.48 (m, 1H), 4.42-4.27 (m, 2H), 3.56-3.51 (m, 1H), 2.75 (s, 3H), 2.74 (s, 3H), 2.63-2.55 (m, 1H), 2.32-2.25 (m, 1H), 2.14 (s, 3H), 1.36 (s, 3H), 1.02-0.97 (m, 1H), 0.88-0.83 (m, 1H). LC/MS (ESI) m/z: 602/604 (M+H)$^+$.

(1R,3S,5R)-2-{2-[3-Acetyl-5-({2-oxo-[1,2'-bipyridine]-3-yl}amino) indazol-1-yl]acetyl}-N-(6-bromo-3-methylpyridin-2-yl)-5-methyl-2-azabicyclo[3.1.0]hexane-3-carboxamide $^1$H-NMR (400 MHz, CD$_3$OD) δ 8.64-8.60 (m, 1H), 8.10 (d, J=1.6 Hz, 1H), 8.05-8.01 (m, 1H), 7.80 (d, J=8.1 Hz, 1H), 7.59-7.50 (m, 3H), 7.39-7.33 (m, 2H), 7.28-7.25 (m, 1H), 7.24-7.21 (m, 1H), 6.44-6.40 (m, 1H), 5.71 (d, J=17.2 Hz, 1H), 5.58 (d, J=17.1 Hz, 1H), 4.60-4.51 (m, 2H), 3.52-3.49 (m, 1H), 2.66 (s, 3H), 2.64-2.58 (m, 1H), 2.33-2.28 (m, 1H), 2.12 (s, 3H), 1.39 (s, 3H), 1.08-1.04 (m, 1H), 0.98-0.95 (m, 1H). LC/MS (ESI) m/z: 695 (M+H)$^+$.

Scheme 76.
Synthesis of (1R,3S,5R)-2-(2-(3-Acetyl-5-(2-methylpyrimidin-5-yl)-1H-indazol-1-yl)acetyl)-5-methyl-N-(3-methyl-6-(trifluoromethoxy)pyridin-2-yl)-2-azabicyclo[3.1.0]hexane-3-carboxamide (196)

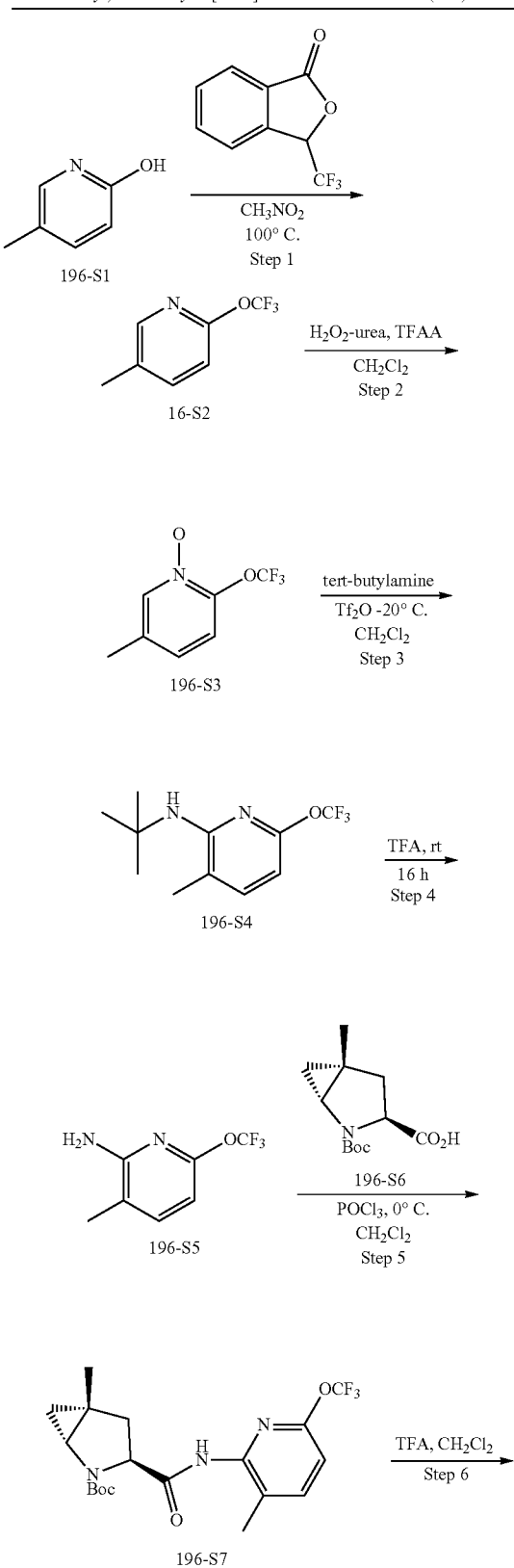

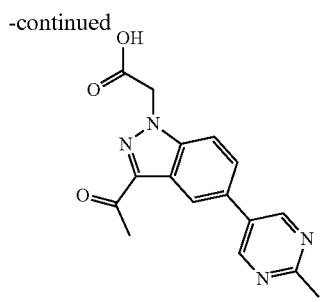
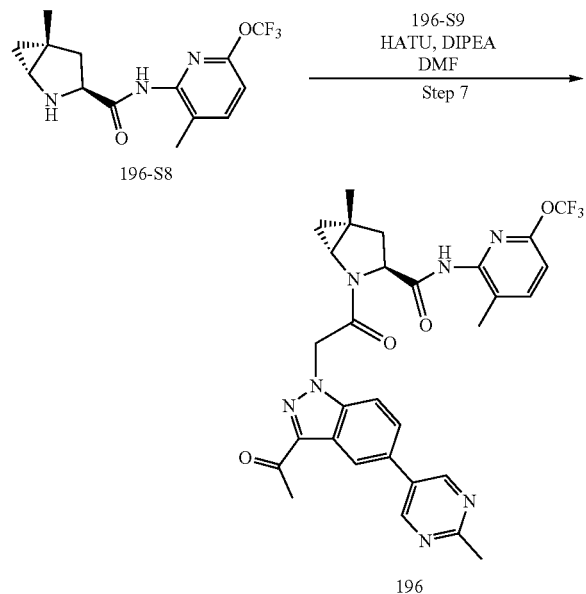

The above scheme and following detailed description depicts one non-limiting method for synthesizing compounds with a trifluromethyl group on the B-ring by utilizing Togni reagent to generate the B-ring synthetic intermediate. The skilled artisan will recognize that other B-rings with trifluromethyl functionality can be prepared to afford additional compounds of the present invention. The skilled artisan will also recognize that other A-rings can be coupled with the C- and B-ring shown above to afford compounds of the present invention.

Step 1: 5-Methyl-2-(trifluoromethoxy)pyridine (196-S2)

A dried glass was charged with 5-methyl-pyridin-2-ol (0.518 g) and Togni reagent (0.5 g) in nitromethane (10 mL). The reaction mixture was stirred at 100° C. for 5 hours in presence of air. After cooling the reaction mixture to room temperature, the reaction was diluted with water and extracted repeatedly with $CH_2Cl_2$. The combined organic layer was dried ($Na_2SO_4$) and concentrated to afford 196-S2, which was carried forward without additional purification in the next synthetic step without purification.

Step 2: 2-Trifluoromethoxy-2-methyl-pyridine-N-oxide (196-S3)

Crude 5-methyl-2-(trifluoromethoxy)pyridine (196-S2) in $CH_2Cl_2$ was cooled in an ice bath and solid hydrogen peroxide urea complex (0.688 g) was added followed by the dropwise addition of TFAA (1.7 mL). After the addition was complete, the cooling bath was removed and the reaction mixture was stirred overnight at room temperature. Additional hydrogen peroxide urea complex (0.688 g) and TFAA (1.7 mL) was added and the reaction mixture was stirred for 24 hours. The reaction mixture was diluted with $CH_2Cl_2$. The organic layer was washed with water, saturated aqueous sodium metabisulfite solution, and dried ($Na_2SO_4$). The organic layer was filtered and concentrated to afford 196-S3, which was carried forward without additional purification and used as such for the next step.

Step 3. N-(tert-Butyl)-3-methyl-6-(trifluoromethoxy)pyridin-2-amine (196-S4)

To a solution of 196-S3 (0.46 g) at −20° C. in $CH_2Cl_2$ (10 mL), tert-butylamine (1.25 mL) was added, followed by the dropwise addition of trifluoromethanesulfonic anhydride (1.2 mL). After stirring for 1 hour at −20° C., the reaction mixture was quenched with the addition of water. The layers were separated and the organic layer was washed with saturated $K_2CO_3$ solution, dried, and concentrated. The residue was purified by silica gel column chromatography (eluent: hexanes) to afford 196-S4 as colorless liquid.

Step 4. 3-Methyl-6-(trifluoromethoxy)pyridin-2-amine TFA Salt (196-S5)

A solution of 196-S4 (50 mg) in TFA (1.0 mL) was stirred at room temperature for 24 hours. Then the volatiles were removed under reduced pressure and the residue was carried forward without additional purification in the next step (196-S5).

Step 5: tert-Butyl (1R,3S,5R)-5-methyl-3-((3-methyl-6-(trifluoromethoxy)pyridin-2-yl)carbamoyl)-2-azabicyclo[3.1.0]hexane-2-carboxylate (196-S7)

To an ice cooled solution of 196-S5 (50 mg) and (1R,2S,5S)-3-(tert-butoxycarbonyl)-3-azabicyclo[3.1.0]hexane-2-carboxylic acid (196-S6, 53 mg) in $CH_2Cl_2$ (1.5 ml) pyridine (82 μL) was added, followed by the slow dropwise addition of $POCl_3$ (20 μL) at 5° C. and the reaction mixture was stirred for 3 hours. Then saturated aqueous $NaHCO_3$ solution was added and stirred for 1 h at room temperature. The organic layer was separated and the aqueous layer was extracted with $CH_2Cl_2$ (10 mL). The combined organic layers were dried ($Na_2SO_4$), filtered, and concentrated. The residue was purified by silica gel flash column chromatography (eluent: 0-2% EtOAc in hexanes) to afford 196-S7.

Step 6: (1R,3S,5R)-5-Methyl-N-(3-methyl-6-(trifluoromethoxy)pyridin-2-yl)-2-azabicyclo[3.1.0] hexane-3-carboxamide TFA Salt (196-S8)

Compound 196-S7 (11 mg) was stirred in TFA (0.25 mL) and $CH_2Cl_2$ (0.25 mL) for 30 minutes at room temperature. The reaction mixture was evaporated to dryness under reduced pressure and the remaining residue was carried forward without additional purification in the next synthetic step.

Step 7: (1R,3S,5R)-2-(2-(3-Acetyl-5-(2-methylpyrimidin-5-yl)-1H-indazol-1-yl)acetyl)-5-methyl-N-(3-methyl-6-(trifluoromethoxy)pyridin-2-yl)-2-azabicyclo[3.1.0]hexane-3-carboxamide (196)

To a solution of 2-(3-acetyl-5-(2-methylpyrimidin-5-yl)-1H-indazol-1-yl)acetic acid (12 mg) in DMF (0.5 mL), iPr₂NEt (35 μL, 5 equiv) was added, followed by the addition of 196-S7 (from above) at 5° C. HATU (16 mg, 1.1 equiv) was added slowly at this same temperature and the reaction mixture was stirred for 30 minutes at room temperature. The reaction mixture was taken to dryness and the residue was dissolved in CH₂Cl₂. The organic layer was washed with 1% aq. LiOH solution and water and dried (Na₂SO₄). After the filtration, the filtrate was concentrated under reduced pressure and the residue was purified by silica gel flash column chromatography (eluent: 0-2.5% MeOH in CH₂Cl₂) to afford 196 as white solid. ¹H NMR (400 MHz, Chloroform-d) δ 0.77-0.96 (m, 2H), 1.42 (s, 3H), 2.09 (s, 3H), 2.29 (dd, J=8.8, 13.6 Hz, 1H), 2.71 (s, 3H), 2.66-2.77 (m, 1H), 2.81 (s, 3H), 3.20 (dd, J=2.4, 5.4 Hz, 1H), 4.88 (d, J=7.7 Hz, 1H), 5.50 (s, 2H), 6.80 (d, J=8.1 Hz, 1H), 7.53-7.66 (m, 3H), 8.58 (s, 1H), 8.68 (s, 1H), 8.90 (s, 2H). ¹⁹F-NMR (Chloroform-d): δ−56.6.

(1R,3S,5R)-2-(2-(3-Acetyl-7-methyl-5-(2-methylpyrimidin-5-yl)-1H-indol-1-yl)acetyl)-5-methyl-N-(3-methyl-6-(trifluoromethoxy)pyridin-2-yl)-2-azabicyclo[3.1.0]hexane-3-carboxamide ¹H-NMR (400 MHz, CDCl3): δ 0.84-0.90 (m, 1H), 1.16 (t, J=5.4 Hz, 1H), 1.43 (s, 3H), 2.12 (s, 3H), 2.35 (t, J=8.4 Hz, 1H), 2.53 (s, 3H), 2.66 (brs, 1H), 2.69 (s, 3H), 2.79 (s, 3H), 3.11 (d, J=4.4 Hz, 1H), 4.93 (s, 1H), 5.35 (d, J=17.6 Hz, 1H), 5.42 (d, J=17.7 Hz, 1H), 6.79 (d, J=8.1 Hz, 1H), 7.17 (s, 1H), 7.57 (d, J=8.1 Hz, 1H), 7.69 (s, 1H), 8.49 (brs, 1H), 8.55 (s, 1H), 8.89 (s, 2H). ¹⁹F (CDCl3): δ−56.5.

(1R,3S,5R)-2-(2-(3-Acetyl-7-methyl-5-(2-methylpyrimidin-5-yl)-1H-indol-1-yl)acetyl)-5-methyl-N-(3-methyl-6-(trifluoromethyl)pyridin-2-yl)-2-azabicyclo[3.1.0]hexane-3-carboxamide ¹H NMR (400 MHz, Chloroform-d) δ 0.88 (dd, J=2.4, 5.5 Hz, 1H), 1.16 (t, J=5.4 Hz, 1H), 1.43 (s, 3H), 2.22 (s, 3H), 2.36-2.42 (m, 1H), 2.53 (s, 3H), 2.67 (d, J=14 Hz, 1H), 2.72 (s, 3H), 2.79 (s, 3H), 3.13 (d, J=4.0 Hz, 1H), 4.65 (d, J=5.2 Hz, 1H), 5.31 (d, J=17.6 Hz, 1H), 5.48 (d, J=17.5 Hz, 1H), 7.19 (s, 1H), 7.42 (d, J=7.7 Hz, 1H), 7.65 (d, J=8 Hz, 1H), 7.69 (s, 1H), 8.55 (s, 1H), 8.57 (brs, 1H), 8.89 (s, 2H). ¹⁹F: δ−67.6.

Scheme 77.
Synthesis of (1R,3S,5S)-2-(2-(3-Acetyl-5-(2-methylpyrimidin-5-yl)-1H-indazol-1-yl)acetyl)-N-(6-bromo-3-methylpyridin-2-yl)-5-(oxazol-5-yl)-2-azabicyclo[3.1.0]hexane-3-carboxamide (197)

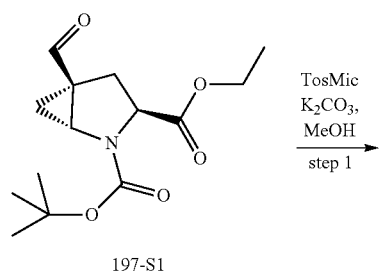

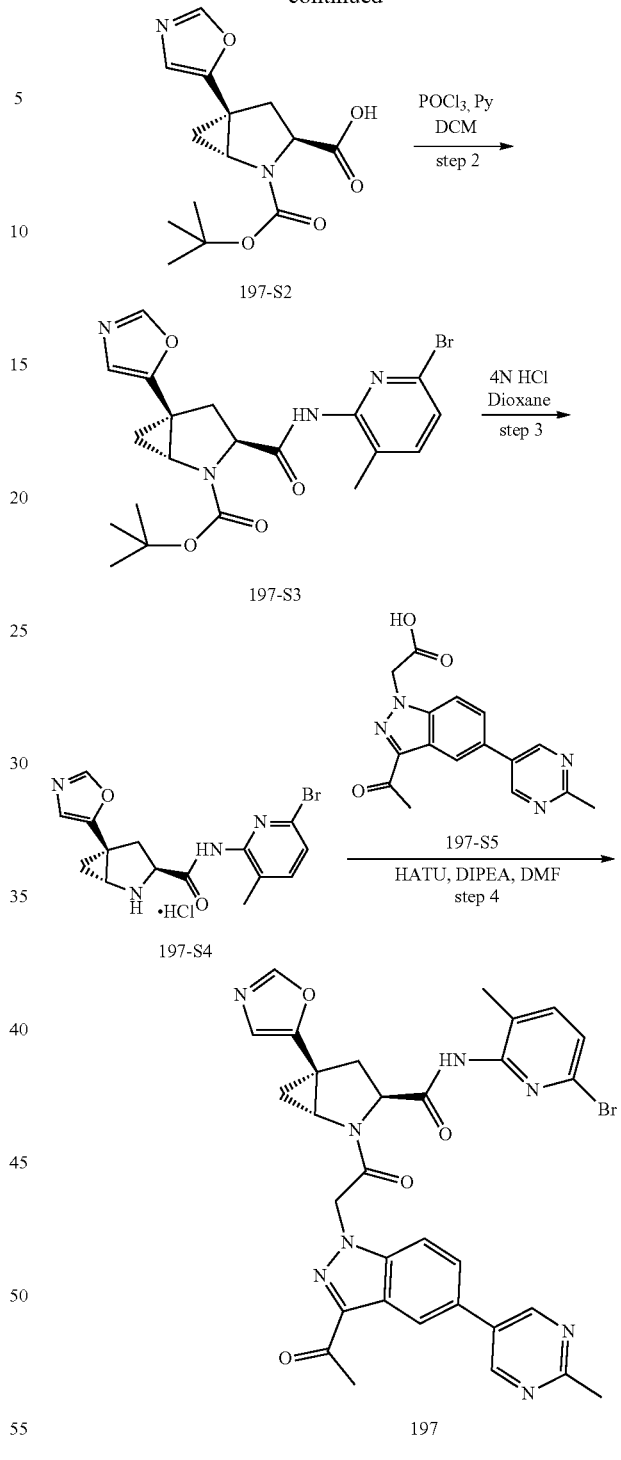

Step 1: (1R,3S,5S)-2-(tert-Butoxycarbonyl)-5-(oxazol-5-yl)-2-azabicyclo[3.1.0]hexane-3-carboxylic Acid (197-S2)

To the solution of 2-(tert-butyl) 3-ethyl (1R,3S,5S)-5-formyl-2-azabicyclo[3.1.0]hexane-2,3-dicarboxylate (197-S1, 142 mg, 0.50 mmol) and p-toluenesulfonylmethyl isocyanide (146.4 mg, 0.75 mmol) in MeOH (15 mL), solid K₂CO₃ (1.50 mmol) was added. The mixture was refluxed overnight under argon. The reaction was cooled to room temperature and the volatiles were evaporated. The residue was loaded on a pad of silica gel and purified to afford 197-S2 (72 mg).

Step 2: tert-Butyl (1R,3S,5S)-3-((6-Bromo-3-methylpyridin-2-yl)carbamoyl)-5-(oxazol-5-yl)-2-azabicyclo[3.1.0]hexane-2-carboxylate (197-S3)

(1R,3S,5S)-2-(tert-Butoxycarbonyl)-5-(oxazol-5-yl)-2-azabicyclo[3.1.0]hexane-3-carboxylic acid (197-S1, 72 mg, 0.24 mmol) and 6-bromo-3-methylpyridin-2-amine (197-S2, 46 mg, 0.24 mmol) were dissolved in anhydrous DCM (6.0 mL) in a pre-dried flask. The flask was cooled in an ice bath and dry pyridine (0.25 mL, 3.0 mmol) was added in one portion, followed by $POCl_3$ (100 μL, 1.0 mmol). After completion of the addition, the mixture was stirred for 4 hours at 0° C., and then the reaction was quenched with water (15 mL). The DCM layer was collected and the aqueous phase was extracted with DCM (15 mL×2). The combined DCM solution was washed with brine and dried over $MgSO_4$. The solution was filtered and concentrated and the resulting residue was purified to afford 197-S3 (59.3 mg).

Step 3: (1R,3S,5S)—N-(6-Bromo-3-methylpyridin-2-yl)-5-(oxazol-5-yl)-2-azabicyclo[3.1.0]hexane-3-carboxamide Hydrochloride (197-S4)

tert-Butyl (1R,3S,5S)-3-((6-bromo-3-methylpyridin-2-yl)carbamoyl)-5-(oxazol-5-yl)-2-azabicyclo[3.1.0]hexane-2-carboxylate (197-S3, 59.3 mg, 0.13 mmol) was taken up in 4N HCl dioxane (2.0 mL) and the resulting reaction mixture was stirred at room temperature for 2 hours. After completion of the reaction (as monitored by HPLC), the solvent was removed under reduced pressure. The remaining residue 197-S4 was carried forward without additional purification.

Step 4: (1R,3S,5S)-2-(2-(3-Acetyl-5-(2-methylpyrimidin-5-yl)-1H-indazol-1-yl)acetyl)-N-(6-bromo-3-methylpyridin-2-yl)-5-(oxazol-5-yl)-2-azabicyclo[3.1.0]hexane-3-carboxamide (197)

To the solution of (1R,3S,5S)—N-(6-bromo-3-methylpyridin-2-yl)-5-(oxazol-5-yl)-2-azabicyclo[3.1.0]hexane-3-carboxamide hydrochloride (197-S4, 0.13 mmol) and 2-(3-acetyl-5-(2-methylpyrimidin-5-yl)-1H-pyrazolo[3,4-c]pyridin-1-yl)acetic acid (197-S5, 40 mg, 0.13 mmol) in DMF (2.0 mL), HATU (1.5 equiv, 0.20 mmol) was added, followed by the dropwise addition of DIEA (5.0 equiv) at room temperature. The mixture was stirred for 1 hour at room temperature and then the volatiles were evaporated. The residue was diluted with 10% sodium carbonate (50 mL) and extracted with ethyl acetate. The combined organic solutions were successively washed with water and brine and dried over $MgSO_4$. The solution was filtered and the solvent was removed. The residue was purified to afford 197 (29.2 mg). $^1$H NMR (400 MHz, DMSO-$d_6$): (major rotamer) δ 1.71 (d, J=4.6 Hz, 2H), 2.03 (s, 3H), 2.59 (dd, J=13.5, 4.8 Hz, 1H), 2.66 (s, 3H), 2.69 (s, 3H), 2.82 (dd, J=13.5, 9.2 Hz, 1H), 4.20 (t, J=4.6 Hz, 1H), 4.60 (dd, J=9.2, 4.7 Hz, 1H), 5.65 (d, J=17.3 Hz, 1H), 5.97 (d, J=17.3 Hz, 1H), 7.15 (s, 1H), 7.44 (d, J=7.9 Hz, 1H), 7.62 (d, J=7.9 Hz, 1H), 7.87 (s, 2H), 8.31 (s, 1H), 8.45 (s, 1H), 9.04 (s, 2H), 10.38 (s, 1H) ppm. LC (method A): $t_R$=1.55 min. LC/MS (EI) m/z: [M+H]$^+$ 655.07, 657.16

Scheme 78.
Synthesis of (1R,3S,5R)-2-(2-(3-Acetyl-7-methyl-5-(2-(oxetan-3-yloxy)pyrimidin-5-yl)-1H-indazol-1-yl)acetyl)-N-(6-bromo-3-methylpyridin-2-yl)-5-methyl-2-azabicyclo[3.1.0]hexane-3-carboxamide (208)

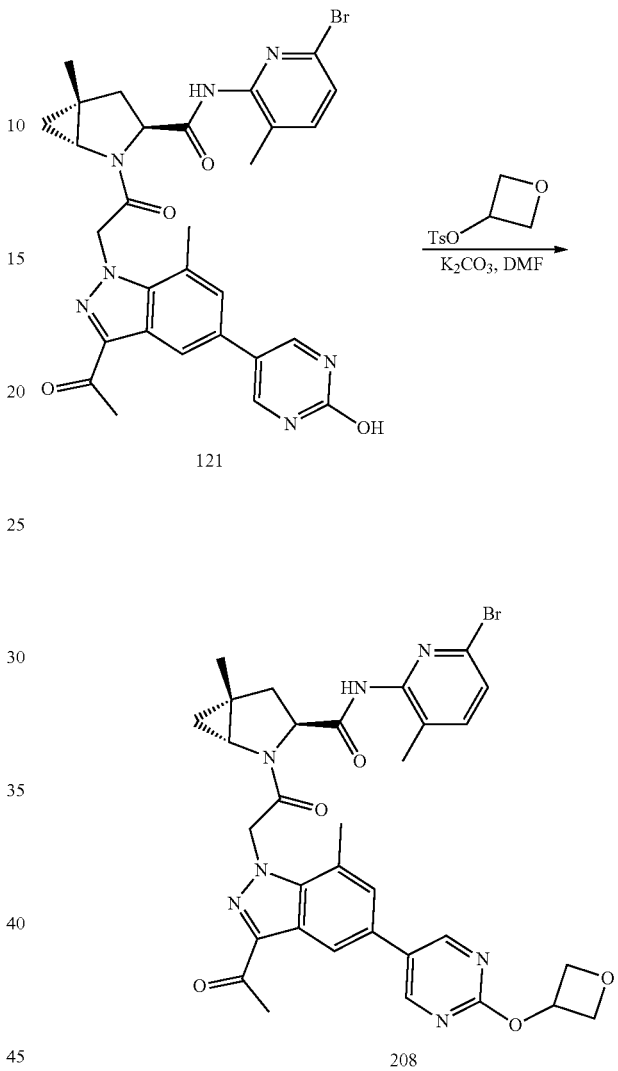

To a solution of 121 (1 equiv) in DMF (10 vol) was added potassium carbonate (3 equiv) and oxetan-3-yl 4-methylbenzenesulfonate (2 equiv). The reaction mixture was heated to 100° C. for 12 hours. The reaction mixture was quenched with water and the resulting mixture was extracted with EtOAc. The organic layer was washed with brine, dried over anhydrous $Na_2SO_4$, filtered and concentrated. The residue was purified by preparative purification to afford 208. $^1$H NMR (400 MHz, DMSO-$d_6$) δ 10.33 (s, 1H), 8.94 (d, J=2.6 Hz, 1H), 8.42 (d, J=2.3 Hz, 1H), 8.21 (s, 1H), 7.62 (d, J=8.0 Hz, 1H), 7.51 (s, 1H), 7.44 (d, J=8.0 Hz, 1H), 6.02 (d, J=17.3 Hz, 1H), 5.65 (d, J=18.0 Hz, 1H), 5.41-5.38 (m, 1H), 4.93-4.84 (m, 4H), 4.34-4.32 (m, 1H), 3.59-3.58 (m, 1H), 2.65 (s, 3H), 2.64-2.63 (m, 1H), 2.58 (s, 3H), 2.04 (s, 3H), 2.01-1.98 (m, 1H), 1.32 (s, 3H), 1.01-0.94 (m, 2H).

Scheme 79.
Synthesis of 1-(2-((2S,4R)-2-((6-Bromopyridin-2-yl)carbamoyl)-4-fluoropyrrolidin-1-yl)-2-oxoethyl)-5-(pyridin-3-yl)-1H-pyrazole-3-carboxamide (211)

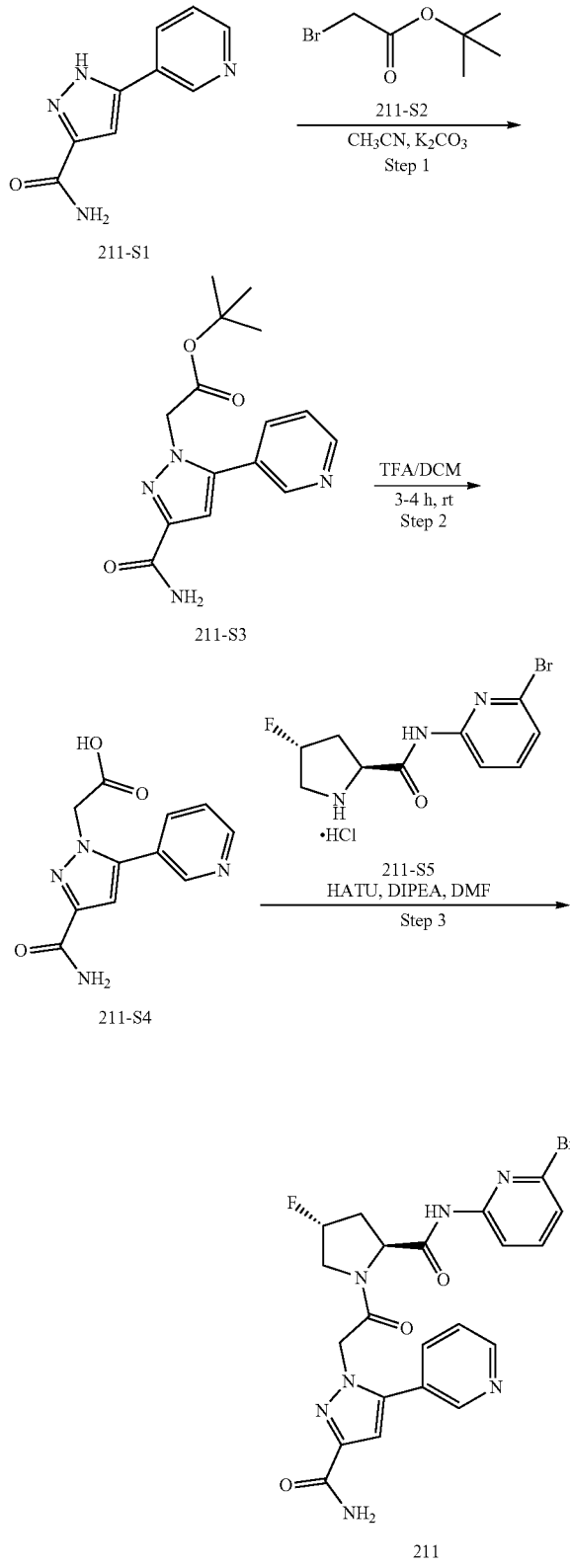

Step 1: tert-Butyl 2-(3-carbamoyl-5-(pyridin-3-yl)-1H-pyrazol-1-yl)acetate (211-S3)

To a solution of 5-(pyridin-3-yl)-1H-pyrazole-3-carboxamide (211-S1, 1 equiv) in $CH_3CN$ (10 vol) was added tert-butyl 2-bromoacetate (211-S2, 1.1 equiv) and potassium carbonate (1.1 equiv). The mixture was refluxed overnight under an atmosphere of argon. After cooling the reaction mixture to room temperature, the mixture was filtered through Celite and washed with $CH_3CN$. The filtrate was concentrated under reduced pressure and the remaining residue was purified by column chromatography on silica gel (eluted with DCM/EtOAc) to afford compound 211-S3.

Step 2: 2-(3-Carbamoyl-5-(pyridin-3-yl)-1H-pyrazol-1-yl)acetic Acid (211-S4)

To a solution of compound 211-S3 (1 equiv) in DCM (10 vol) at 0° C. under an atmosphere of argon was added TFA (5 vol). The reaction mixture was stirred at room temperature for 3 hours and concentrated to dryness. The remaining material (211-S4) was carried forward in the next synthetic step without additional purification.

Step 3: 1-(2-((2S,4R)-2-((6-Bromopyridin-2-yl)carbamoyl)-4-fluoropyrrolidin-1-yl)-2-oxoethyl)-5-(pyridin-3-yl)-1H-pyrazole-3-carboxamide (211)

To a solution of compound 211-S4 (1 equiv) in DMF (10 vol) at 0° C. under an atmosphere of argon was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 hours and then quenched with water (30 vol). The resulting mixture was extracted with DCM. The organic layer was washed with brine, dried over anhydrous $Na_2SO_4$, filtered, and concentrated to dryness. The remaining residue was purified by column chromatography on silica gel (eluted with DCM/MeOH) to afford compound 211. $^1$H NMR (400 MHz, DMSO-$d_6$) δ 2.02-2.24 (m, 1H), 2.54-2.61 (m, 1H), 3.73-3.89 (m, 1H), 4.00-4.17 (dd, J=12.9, 21.3 Hz, 1H), 4.62-4.71 (t, J=8.3 Hz, 1H), 5.03-5.13 (d, J=17.4 Hz, 1H), 5.34-5.58 (m, 2H), 6.81-6.92 (d, J=2.7 Hz, 1H), 7.26-7.31 (s, 1H), 7.33-7.37 (d, J=7.7 Hz, 1H), 7.46-7.57 (m, 2H), 7.71-7.78 (t, J=8.0 Hz, 1H), 7.84-7.89 (m, 1H), 8.03-8.12 (d, J=8.2 Hz, 1H), 8.57-8.75 (m, 2H), 10.18-11.70 (s, 1H).

Scheme 80.
Synthesis of (1R,3S,5R)-N-(6-Bromo-3-methylpyridin-2-yl)-2-(2-(3-carbamoyl-5-(furan-2-yl)-1H-pyrazol-1-yl)acetyl)-5-methyl-2-azabicyclo[3.1.0]hexane-3-carboxamide (212) and (1R,3S,5R)-N-(6-Bromo-3-methylpyridin-2-yl)-2-(2-(5-carbamoyl-3-(furan-2-yl)-1H-pyrazol-1-yl)acetyl)-5-methyl-2-azabicyclo[3.1.0]hexane-3-carboxamide (213)

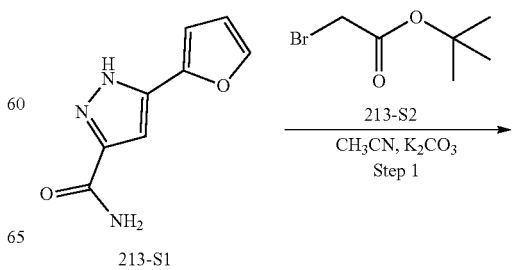

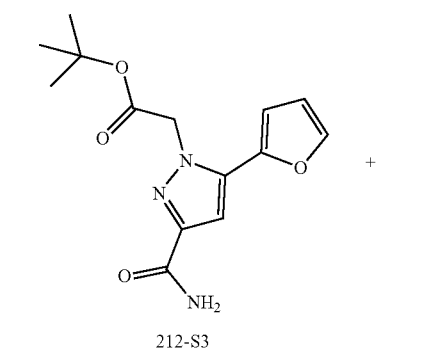

212-S3

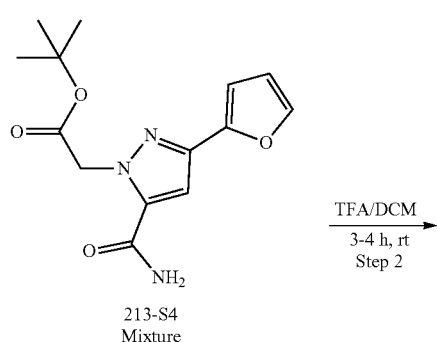

213-S4
Mixture

TFA/DCM
3-4 h, rt
Step 2
→

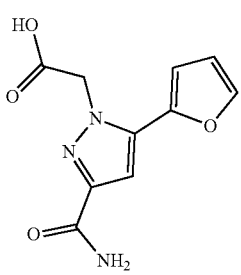

212-S5

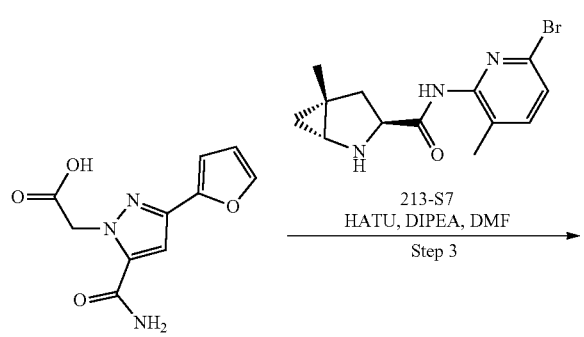

213-S6
Mixture

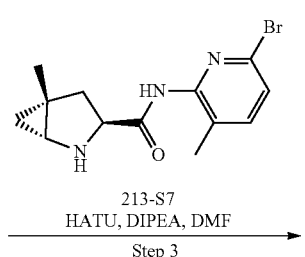

213-S7

HATU, DIPEA, DMF
Step 3
→

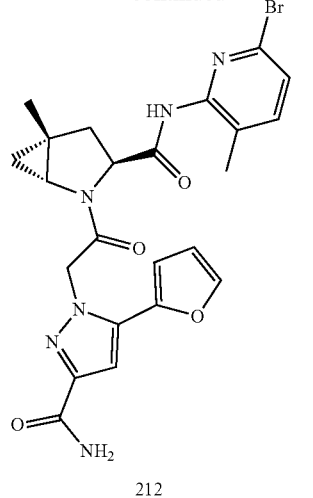

212

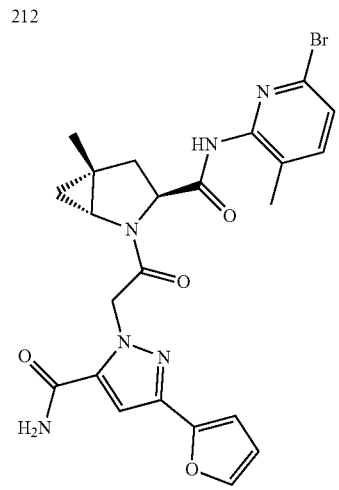

213

Step 1: tert-Butyl 2-(3-carbamoyl-5-(furan-2-yl)-1H-pyrazol-1-yl)acetate and tert-butyl 2-(5-carbamoyl-3-(furan-2-yl)-1H-pyrazol-1-yl)acetate (212-S3 and 213-S4)

To a solution of 5-(furan-2-yl)-1H-pyrazole-3-carboxamide (213-S1, 1 equiv) in CH$_3$CN (10 vol) was added tert-butyl 2-bromoacetate (213-S2, 1.1 equiv) and potassium carbonate (1.1 equiv). The mixture was refluxed overnight under an atmosphere of argon. After cooling the reaction mixture to room temperature, the mixture was filtered through Celite and washed with CH$_3$CN. The filtrate was concentrated under reduced pressure and the remaining residue was purified by column chromatography on silica gel (eluted with EtOAc/DCM) to afford a mixture of compounds 212-S3 and 213-S4. This mixture was carried forward as mixture without additional purification.

Step 2: 2-(3-Carbamoyl-5-(furan-2-yl)-1H-pyrazol-1-yl)acetic Acid and 2-(5-carbamoyl-3-(furan-2-yl)-1H-pyrazol-1-yl)acetic Acid (212-S5 and 213-S6)

To a solution of compound 212-S3 and 213-S4 (1 equiv, Mixture) in DCM (10 vol) at 0° C. under an atmosphere of argon was added TFA (5 vol). The reaction mixture was stirred at room temperature for 3 hours and concentrated to dryness. The remaining material (a mixture of 212-S5 and 213-S6) was carried forward as mixture without additional purification.

Step 3: (1R,3S,5R)—N-(6-Bromo-3-methylpyridin-2-yl)-2-(2-(3-carbamoyl-5-(furan-2-yl)-1H-pyrazol-1-yl)acetyl)-5-methyl-2-azabicyclo[3.1.0]hexane-3-carboxamide (212) and (1R,3S,5R)—N-(6-Bromo-3-methylpyridin-2-yl)-2-(2-(5-carbamoyl-3-(furan-2-yl)-1H-pyrazol-1-yl)acetyl)-5-methyl-2-azabicyclo [3.1.0]hexane-3-carboxamide (213)

To a solution of compound 212-S5 and 213-S6 (1 equiv) in DMF (10 vol) at 0° C. under an atmosphere of argon was added (1R,3S,5R)—N-(6-bromo-3-methylpyridin-2-yl)-5-methyl-2-azabicyclo[3.1.0]hexane-3-carboxamide (213-S7, 1 equiv), HATU (2.1 equiv), and DIPEA (5 equiv). The reaction mixture was stirred at room temperature for 3 hours and quenched with water (30 vol). The resulting mixture was extracted with DCM. The organic layer was washed with brine, dried over anhydrous $Na_2SO_4$, filtered, and concentrated to dryness. The remaining residue was purified by column chromatography on silica gel (eluted with DCM/MeOH) to afford compounds 212 and 213.

(1R,3S,5R)—N-(6-Bromo-3-methylpyridin-2-yl)-2-(2-(3-carbamoyl-5-(furan-2-yl)-1H-pyrazol-1-yl)acetyl)-5-methyl-2-azabicyclo[3.1.0]hexane-3-carboxamide (212)

$^1$H NMR (400 MHz, DMSO-$d_6$) δ 0.87 (dd, J=2.4, 5.4 Hz, 1H), 0.99 (t, J=5.5 Hz, 1H), 1.21-1.34 (m, 4H), 1.94-2.08 (m, 4H), 3.51 (dd, J=2.4, 5.6 Hz, 1H), 4.36 (dd, J=5.5, 9.2 Hz, 1H), 5.38 (d, J=17.4 Hz, 1H), 5.52 (d, J=17.3 Hz, 1H), 6.60 (dd, J=1.8, 3.5 Hz, 1H), 6.79 (d, J=3.4 Hz, 1H), 6.96 (s, 1H), 7.28 (s, 1H), 7.45 (d, J=7.9 Hz, 1H), 7.52 (s, 1H), 7.62 (d, J=7.9 Hz, 1H), 7.79 (d, J=1.7 Hz, 1H), 10.28 (s, 1H).

(1R,3S,5R)—N-(6-Bromo-3-methylpyridin-2-yl)-2-(2-(5-carbamoyl-3-(furan-2-yl)-1H-pyrazol-1-yl)acetyl)-5-methyl-2-azabicyclo[3.1.0]hexane-3-carboxamide (213)

$^1$H NMR (400 MHz, DMSO-$d_6$) δ 0.83-0.93 (m, 1H), 0.99 (t, J=5.4 Hz, 1H), 1.20-1.32 (m, 4H), 1.98-2.10 (m, 4H), 3.37-3.43 (m, 1H), 4.35 (dd, J=5.0, 9.2 Hz, 1H), 5.51 (d, J=16.4 Hz, 1H), 5.69 (d, J=16.3 Hz, 1H), 6.58 (dd, J=1.7, 3.4 Hz, 1H), 6.69 (t, J=3.9 Hz, 1H), 7.19 (s, 1H), 7.42-7.50 (m, 2H), 7.63 (d, J=7.9 Hz, 1H), 7.73 (d, J=1.7 Hz, 1H), 8.02 (s, 1H), 10.18 (s, 1H).

Scheme 81. Synthesis of (1R,3S,5R)-N-(6-Bromo-3-methylpyridin-2-yl)-2-(2-(3-carbamoyl-5-(thiophen-2-yl)-1H-pyrazol-1-yl)acetyl)-5-methyl-2-azabicyclo[3.1.0]hexane-3-carboxamide (214)

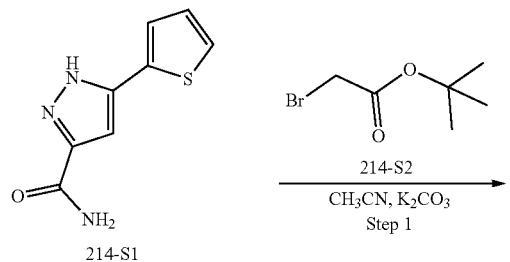

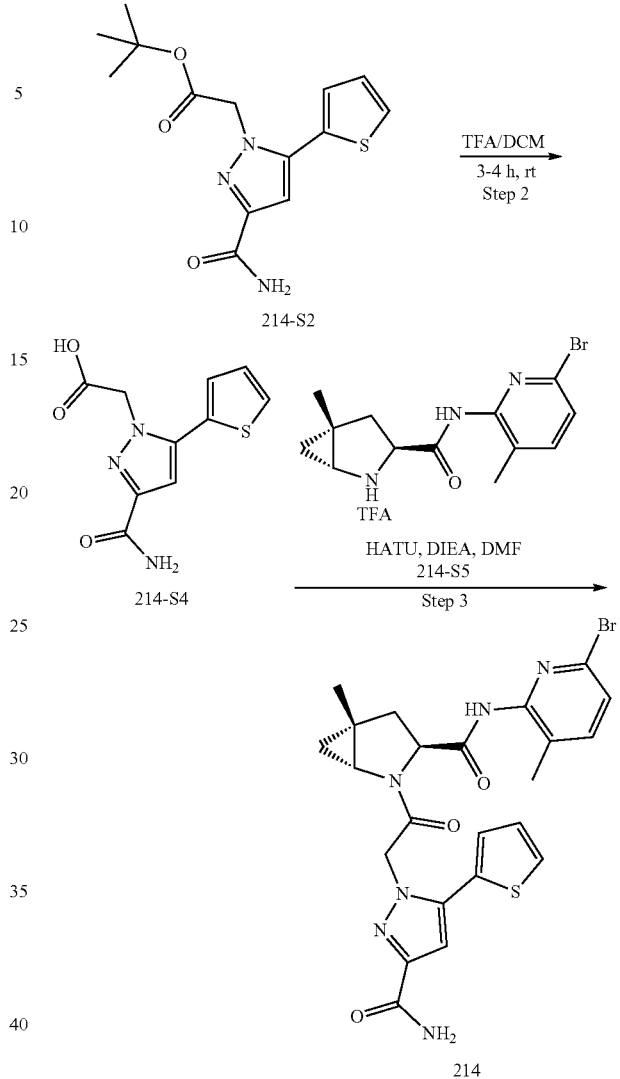

Step 1: tert-Butyl 2-(3-carbamoyl-5-(thiophen-2-yl)-1H-pyrazol-1-yl)acetate (214-S3)

To a solution of 5-(thiophen-2-yl)-1H-pyrazole-3-carboxamide (214-S1, 1 equiv) in $CH_3CN$ (10 vol) was added tert-butyl 2-bromoacetate (214-S2, 1.1 equiv) and potassium carbonate (1.1 equiv). The mixture was refluxed overnight under an atmosphere of argon. After cooling the reaction mixture to room temperature, the mixture was filtered through Celite and washed with $CH_3CN$. The filtrate was concentrated under reduced pressure and the remaining residue was purified by column chromatography on silica gel (eluted with DCM/EtOAc) to afford compound 214-S3.

Step 2: 2-(3-Carbamoyl-5-(thiophen-2-yl)-1H-pyrazol-1-yl)acetic acid (214-S4)

To a solution of compound 214-S3 (1 equiv) in DCM (10 vol) at 0° C. under an atmosphere of argon was added TFA (5 vol). The reaction mixture was stirred at room temperature for 3 hours and concentrated to dryness. The remaining material (214-S4) was used directly in the next synthetic step without additional purification.

Step 3: (1R,3S,5R)—N-(6-Bromo-3-methylpyridin-2-yl)-2-(2-(3-carbamoyl-5-(thiophen-2-yl)-1H-pyrazol-1-yl)acetyl)-5-methyl-2-azabicyclo[3.1.0]hexane-3-carboxamide (214)

To a solution of compound 214-S4 (1 equiv) in DMF (10 vol) at 0° C. under an atmosphere of argon was added (1R,3S,5R)—N-(6-bromo-3-methylpyridin-2-yl)-5-methyl-2-azabicyclo[3.1.0]hexane-3-carboxamide (214-S5, 1 equiv), HATU (2.1 equiv), and DIPEA (5 equiv). The reaction mixture was stirred at room temperature for 3 hours and quenched with water (30 vol). The resulting mixture was extracted with DCM. The organic layer was washed with brine, dried over anhydrous Na$_2$SO$_4$, filtered, and concentrated to dryness. The remaining residue was purified by column chromatography on silica gel (eluted with DCM/MeOH) to afford compound 214. $^1$H NMR (400 MHz, DMSO-d$_6$) δ 0.77 (dd, J=2.3, 5.3 Hz, 1H), 0.93 (t, J=5.4 Hz, 1H), 1.09-1.32 (m, 4H), 1.98-2.05 (m, 1H), 2.07 (s, 3H), 3.47 (dd, J=2.3, 5.6 Hz, 1H), 4.38 (dd, J=5.5, 9.2 Hz, 1H), 5.24 (d, J=17.4 Hz, 1H), 5.44 (d, J=17.4 Hz, 1H), 6.86 (s, 1H), 7.13 (dd, J=3.7, 5.1 Hz, 1H), 7.24-7.33 (m, 2H), 7.46 (d, J=7.9 Hz, 1H), 7.53 (s, 1H), 7.64 (d, J=7.9 Hz, 1H), 7.70 (dd, J=1.1, 5.1 Hz, 1H), 10.30 (s, 1H)

Scheme 82. Synthesis of 1-(2-((2S,4R)-2-((6-Bromopyridin-2-yl)carbamoyl)-4-fluoropyrrolidin-1-yl)-2-oxoethyl)-5(2-methylpyrimidin-5-yl)-1H-pyrazole-3-carboxamide (215)

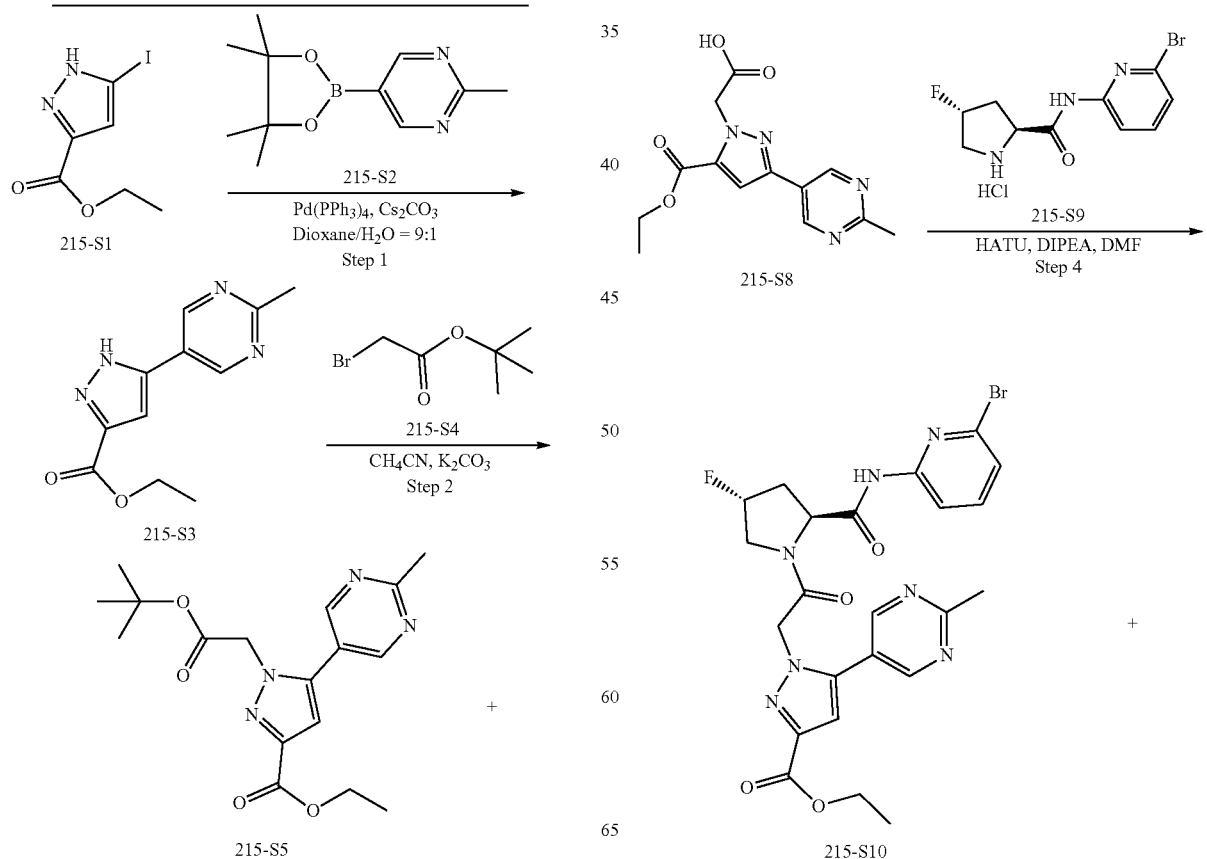

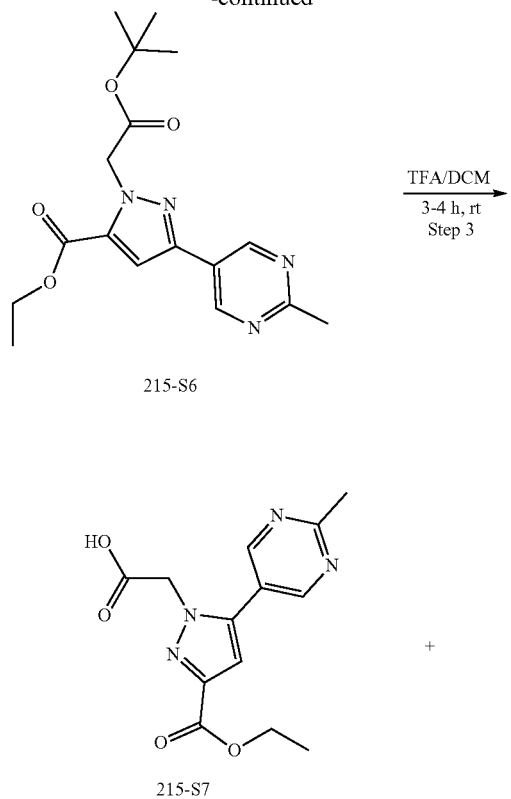

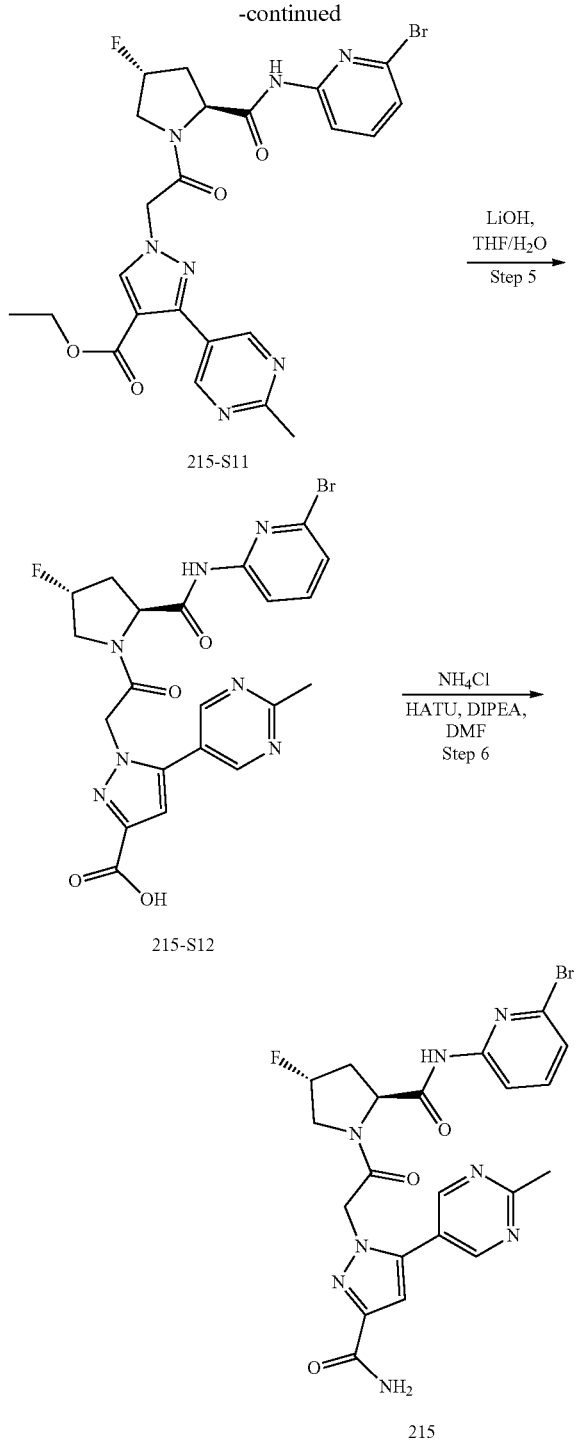

by column chromatography on silica gel (eluted with DCM/MeOH) to afford compound 215-S3.

Step 2: tert-Butyl 2-(3-carbamoyl-5-(2-methylpyrimidin-5-yl)-1H-pyrazol-1-yl)acetate and ethyl 1-(2-(tert-Butoxy)-2-oxoethyl)-3-(2-methylpyrimidin-5-yl)-1H-pyrazole-5-carboxylate (215-S5 and 215-S6)

To a solution of ethyl 5-(2-methylpyrimidin-5-yl)-1H-pyrazole-3-carboxylate (215-S3, 1 equiv) in $CH_3CN$ (10 vol) was added tert-butyl 2-bromoacetate (215-S2, 1.1 equiv) and potassium carbonate (1.1 equiv). The mixture was refluxed overnight under an atmosphere of argon. After cooling the reaction mixture to room temperature, the mixture was filtered through Celite and washed with $CH_3CN$. The filtrate was concentrated under reduced pressure and the remaining residue was purified by column chromatography on silica gel (elute with DCM/EtOAc) to afford a mixture of compounds 215-S5 and 215-S6. The mixture was carried forward without additional purification.

Step 3: 2-(3-(Ethoxycarbonyl)-5-(2-methylpyrimidin-5-yl)-1H-pyrazol-1-yl)acetic Acid and 2-(5-(ethoxycarbonyl)-3-(2-methylpyrimidin-5-yl)-1H-pyrazol-1-yl)acetic Acid (215-S7 and 215-S8)

To a solution of compounds 215-S5 and 215-S6 (1 equiv, Mixture) in DCM (10 vol) at 0° C. under an atmosphere of argon was added TFA (5 vol). The reaction mixture was stirred at room temperature for 3 hours and concentrated to dryness. The remaining material (a mixture of 215-S7 and 215-S8) was carried forward without additional purification.

Step 4: Ethyl 1-(2-((2S,4R)-2-((6-bromopyridin-2-yl)carbamoyl)-4-fluoropyrrolidin-1-yl)-2-oxoethyl)-5-(2-methylpyrimidin-5-yl)-1H-pyrazole-3-carboxylate (215-S10) and Ethyl 1-(2-((2S,4R)-2-((6-bromopyridin-2-yl)carbamoyl)-4-fluoropyrrolidin-1-yl)-2-oxoethyl)-3-(2-methylpyrimidin-5-yl)-1H-pyrazole-4-carboxylate (215-S11)

To a solution of compounds 215-S7 and 215-S8 (1 equiv) in DMF (10 vol) at 0° C. under an atmosphere of argon was added (2S,4R)—N-(6-bromopyridin-2-yl)-4-fluoropyrrolidine-2-carboxamide hydrochloride (215-S9, 1 equiv), HATU (2.1 equiv), and DIPEA (5 equiv). The reaction mixture was stirred at room temperature for 3 hours and quenched with water (30 vol). The resulting mixture was extracted with DCM. The organic layer was washed with brine, dried over anhydrous $Na_2SO_4$, filtered, and concentrated to dryness. The remaining residue was purified by column chromatography on silica gel (eluted with DCM/MeOH) to afford separate pure compounds 215-S10 and 215-S11.

Step 5: 1-(2-((2S,4R)-2-((6-Bromopyridin-2-yl)carbamoyl)-4-fluoropyrrolidin-1-yl)-2-oxoethyl)-5-(2-methylpyrimidin-5-yl)-1H-pyrazole-3-carboxylic Acid (215-S12)

To a solution of ethyl 1-(2-((2S,4R)-2-((6-bromopyridin-2-yl)carbamoyl)-4-fluoropyrrolidin-1-yl)-2-oxoethyl)-5-(2-methylpyrimidin-5-yl)-1H-pyrazole-3-carboxylate (215-S10, 1 equiv) in $THF/H_2O$ (3:1, 10 vol) was added LiOH (2.1 equiv). The reaction mixture was stirred at room temperature for 5 hours and concentrated under reduced pres- Step 1: Ethyl 5-(2-methylpyrimidin-5-yl)-1H-pyrazole-3-carboxylate (215-S3)

To a solution of ethyl 5-iodo-1H-pyrazole-3-carboxylate (215-S1, 1 equiv) in dioxane/$H_2O$ (9:1, 10 vol) was added compound 215-S2 (1 equiv), $Cs_2CO_3$ (3 equiv), and tetrakis(triphenylphosphine)palladium (0.1 equiv). The reaction mixture was stirred at 90° C. for 5 hours and concentrated under reduced pressure. The remaining residue was purified sure to remove the volatiles. The remaining water was neutralized using 2N HCl before the solid was filtered and purified by column chromatography on silica gel (eluted with DCM/MeOH) to afford compound 215-S12.

Step 6: 1-(2-((2S,4R)-2-((6-Bromopyridin-2-yl)carbamoyl)-4-fluoropyrrolidin-1-yl)-2-oxoethyl)-5-(2-methylpyrimidin-5-yl)-1H-pyrazole-3-carboxamide (215)

To a solution of compound 215-S12 (1 equiv) in DMF (10 vol) at 0° C. under an atmosphere of argon was added NH$_4$Cl (3 equiv), HATU (2.1 equiv), and DIPEA (5 equiv). The reaction mixture was stirred at room temperature for 3 hours and quenched with water (30 vol). The resulting mixture was extracted with DCM. The organic layer was washed with brine, dried over anhydrous Na$_2$SO$_4$, filtered, and concentrated to dryness. The remaining residue was purified by column chromatography on silica gel (eluted with DCM/MeOH) to afford compound 215. $^1$H NMR (400 MHz, DMSO-d$_6$) δ 2.03-2.23 (m, 1H), 2.52-2.58 (m, 1H), 2.66 (s, 3H), 3.81-3.98 (m, 1H), 4.10 (dd, J=12.5, 21.9 Hz, 1H), 4.66 (t, J=8.4 Hz, 1H), 5.36 (d, J=16.5 Hz, 1H), 5.41-5.57 (m, 1H), 5.73 (d, J=16.5 Hz, 1H), 7.33 (d, J=7.7 Hz, 1H), 7.43 (s, 1H), 7.54 (s, 1H), 7.71 (t, J=8.0 Hz, 1H), 7.97-8.06 (m, 2H), 9.00 (d, J=3.7 Hz, 2H), 10.98 (s, 1H).

Scheme 83. Synthesis of 1-(2-((2S,4R)-2-((6-Bromopyridin-2-yl)carbamoyl)-4-fluoropyrrolidin-1-yl)-2-oxoethyl)-3-(2-methylpyrimidin-5-yl)-1H-pyrazole-4-carboxamide (216)

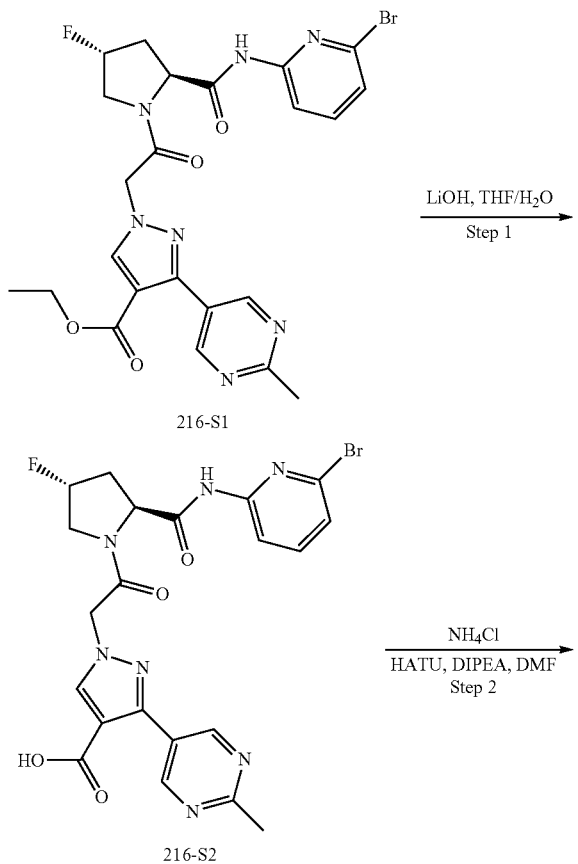

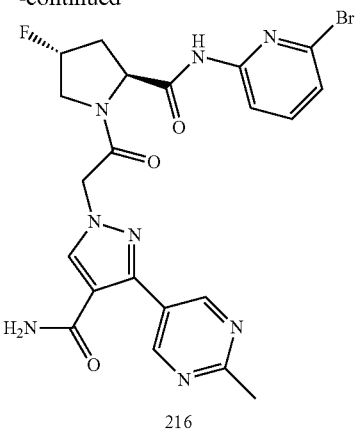

Step 1: 1-(2-((2S,4R)-2-((6-Bromopyridin-2-yl)carbamoyl)-4-fluoropyrrolidin-1-yl)-2-oxoethyl)-3-(2-methylpyrimidin-5-yl)-1H-pyrazole-4-carboxylic Acid (216-S2)

To a solution of ethyl 1-(2-((2S,4R)-2-((6-bromopyridin-2-yl)carbamoyl)-4-fluoropyrrolidin-1-yl)-2-oxoethyl)-3-(2-methylpyrimidin-5-yl)-1H-pyrazole-4-carboxylate (216-S1, 1 equiv) in THF/H$_2$O (3:1, 10 vol) was added LiOH (2.1 equiv). The reaction mixture was stirred at room temperature for 5 hours and concentrated under reduced pressure to remove the volatiles. The remaining water was neutralized using 2N HCl before the solid was filtered and purified by column chromatography on silica gel (eluted with DCM/MeOH) to afford compound 216-S2.

Step 2: 1-(2-((2S,4R)-2-((6-Bromopyridin-2-yl)carbamoyl)-4-fluoropyrrolidin-1-yl)-2-oxoethyl)-3-(2-methylpyrimidin-5-yl)-1H-pyrazole-4-carboxamide (216)

To a solution of compound 216-S2 (1 equiv) in DMF (10 vol) at 0° C. under an atmosphere of argon was added NH$_4$Cl (3 equiv), HATU (2.1 equiv), and DIPEA (5 equiv). The reaction mixture was stirred at room temperature for 3 hours and quenched with water (30 vol). The resulting mixture was extracted with DCM. The organic layer was washed with brine, dried over anhydrous Na$_2$SO$_4$, filtered, and concentrated to dryness. The remaining residue was purified by column chromatography on silica gel (eluted with DCM/MeOH) to afford compound 216. $^1$H NMR (400 MHz, DMSO-d$_6$) δ 1.92-2.12 (m, 1H), 2.45-2.50 (m, 1H), 2.61 (d, J=3.1 Hz, 3H), 3.64-3.83 (m, 1H), 3.94-4.08 (m, 1H), 4.57 (t, J=8.5 Hz, 1H), 5.10 (d, J=17.5 Hz, 1H), 5.31-5.50 (m, 2H), 6.89 (s, 1H), 7.19-7.29 (m, 2H), 7.44 (s, 1H), 7.62-7.71 (m, 1H), 7.95 (d, J=8.2 Hz, 1H), 8.69 (s, 2H), 10.94 (s, 1H).

Scheme 84: Synthesis of (1R, 3S, 5R)-2-(2-(3-Acetyl-7-(1-fluoroethyl)-5-(2-methylpyrimidin-5-yl)-1H-indazol-1-yl)acetyl)-N-(6-bromo-3-methylpyridin-2-yl)-5-methyl-2-azabicyclo [3.1.0] hexane-3-carboxamide (220)

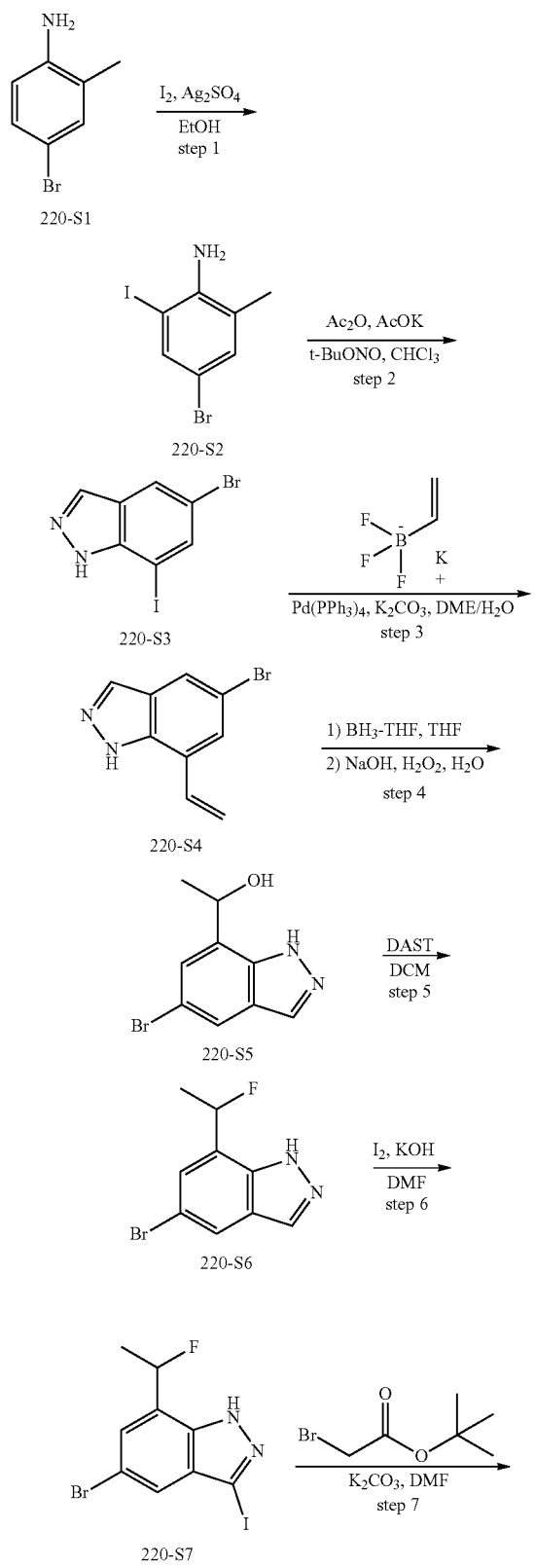

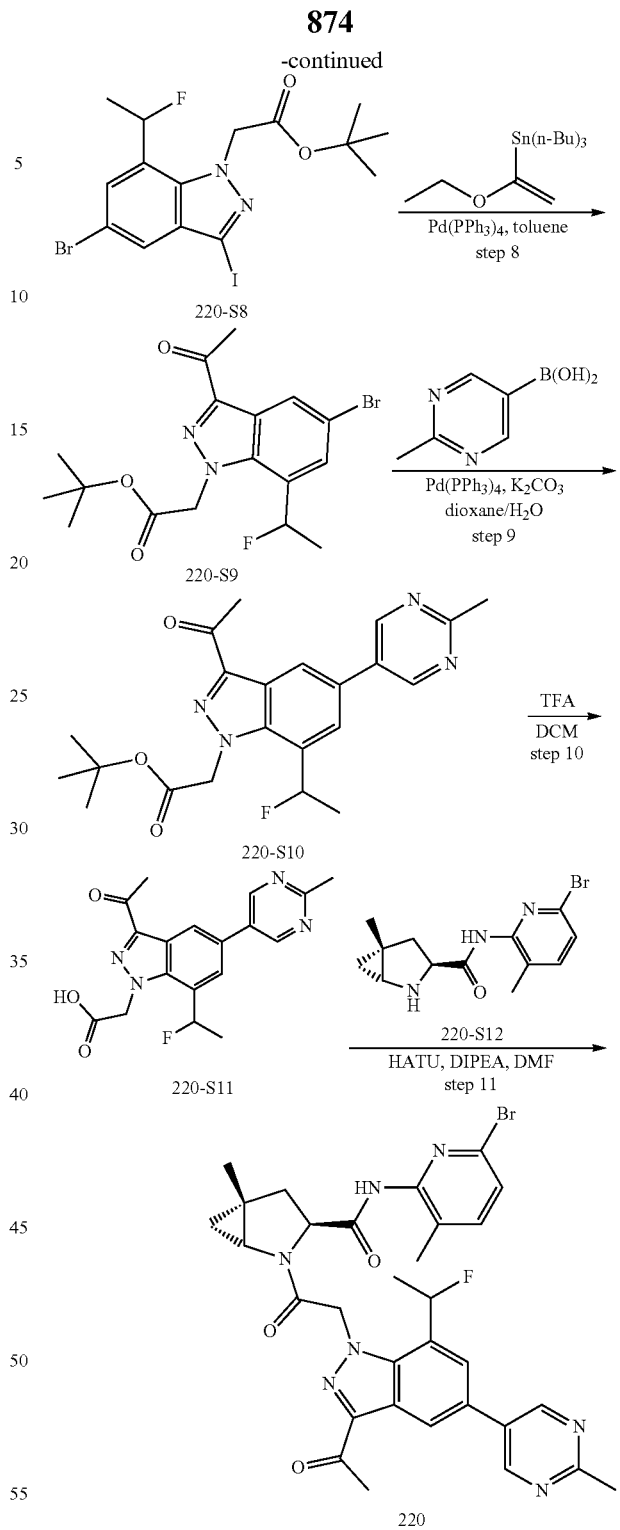

Step 1: 4-Bromo-2-iodo-6-methylaniline (220-S2)

To a solution of compound 220-S1 (5 g, 26.88 mmol) in EtOH (100 mL) was added $I_2$ (6.828 g, 26.88 mmol) and $Ag_2SO_4$ (8.382 g, 26.88 mmol). The mixture was stirred at room temperature overnight. The mixture was quenched with aqueous $Na_2S_2O_3$ solution and extracted with EtOAc (2×). The combined organic layers were washed with brine, dried over anhydrous Na$_2$SO$_4$, and concentrated. The residue was purified by column chromatography on silica gel eluted with petroleum ether to afford compound 220-S2 (6.31 g, 75.5%) as a light brown solid. LC/MS (ESI) m/z: 312 (M+H)$^+$.

Step 2: 5-Bromo-7-iodo-1H-indazole (220-3)

To a solution of compound 220-S2 (6.31 g, 20.29 mmol) and potassium acetate (2.386 g, 24.35 mmol) in CHCl$_3$ (100 mL) was added acetic anhydride (6.209 g, 60.87 mmol) dropwise at 0° C. under N$_2$ atmosphere and the mixture was stirred at room temperature for 1 hour. The reaction mixture was heated to 60° C. and tert-butyl nitrite (10.3 g, 0.1 mol) was added and the reaction was stirred at 60° C. overnight. The mixture was diluted with water and extracted with DCM (2×). The combined organic layers were washed with brine, dried over anhydrous Na$_2$SO$_4$, and concentrated. The residue was dissolved in MeOH and 6 N HCl (v/v=1:1), and the mixture was stirred at room temperature for 5 hours. The mixture was basified with 10 N aqueous NaOH solution and extracted with DCM twice. The combined organic layers were washed with brine, dried over anhydrous Na$_2$SO$_4$, and concentrated. The residue was purified by column chromatography on silica gel eluted with petroleum ether/EtOAc (100:1 to 8:1) to afford compound 220-S3 (3.73 g, 57.1%) as a light yellow solid. LC/MS (ESI) m/z: 323 (M+H)$^+$.

Step 3: 5-Bromo-7-vinyl-1H-indazole (220-S4)

To a solution of compound 220-S3 (1.9 g, 5.92 mmol) in DME/H$_2$O (40 mL, v/v=3/1) was added potassium trifluoro(vinyl)borate (0.793 g, 5.92 mmol), K$_2$CO$_3$ (0.980 g, 7.10 mmol) and Pd(PPh$_3$)$_4$ (0.684 g, 0.59 mmol). The mixture was degassed under N$_2$ atmosphere three times and stirred at 85° C. under N$_2$ atmosphere overnight. The mixture was diluted with EtOAc and washed with water and brine, dried over anhydrous Na$_2$SO$_4$, and concentrated. The residue was purified by column chromatography on silica gel eluted with petroleum ether/EtOAc (100:1 to 8:1) to afford compound 220-S4 (0.78 g, 59.4%) as a light yellow solid. LC/MS (ESI) m/z: 223 (M+H)$^+$.

Step 4: 1-(5-Bromo-1H-indazol-7-yl) ethanol (220-S5)

To a solution of compound 220-S4 (0.78 g, 3.51 mmol) in anhydrous THF (20 mL) was added BH$_3$-THF (1.13 mL, 1 M in THF) dropwise at 0° C. under N$_2$ atmosphere and the mixture was stirred at reflux overnight. The mixture was cooled to 0° C. and 3 N aqueous NaOH solution was added followed by 30% H$_2$O$_2$. The mixture was stirred at room temperature for 1 hour. The solvent was removed and the residue was dissolved in DCM. The mixture was washed with brine, dried over anhydrous Na$_2$SO$_4$, and concentrated. The residue was purified by column chromatography on silica gel eluted with petroleum ether/EtOAc (100:1 to 6:1) to afford compound 220-S5 (170 mg, 20.1%) as a light brown solid. LC/MS (ESI) m/z: 242 (M+H)$^+$.

Step 5: 5-Bromo-7-(1-fluoroethyl)-1H-indazole (220-S6)

To a solution of compound 220-S5 (0.16 g, 0.66 mmol) in anhydrous DCM (5 mL) was added DAST (0.22 g, 1.33 mmol) dropwise at −70° C. under N$_2$ atmosphere. The reaction mixture was allowed to warm to room temperature and was stirred for 2 hours. The reaction was quenched with aqueous NaHCO$_3$ solution at 0° C. and diluted with DCM. The layers were separated and the organic layer was washed with brine, dried over anhydrous Na$_2$SO$_4$, and concentrated. The residue was purified by column chromatography on silica gel eluted with petroleum ether/EtOAc (100:1 to 6:1) to afford compound 220-S6 (70 mg, 43.5% yield) as a light white solid. LC/MS (ESI) m/z: 244 (M+H)$^+$.

Step 6: 5-Bromo-7-(1-fluoroethyl)-3-iodo-1H-indazole (220-S7)

To a solution of compound 220-S6 (70 mg, 0.29 mmol) in DMF (2 mL) was added KOH (40 mg, 0.72 mmol) followed by I$_2$ (110 mg, 0.43 mmol) at 0° C. and the mixture was stirred at room temperature for 2 hours. The reaction was quenched with aqueous Na$_2$S$_2$O$_3$ solution, diluted with water, and extracted with EtOAc twice. The combined organic layers were washed with brine, dried over anhydrous Na$_2$SO$_4$, and concentrated. The residue was purified by column chromatography on silica gel eluted with petroleum ether/EtOAc (80:1 to 6:1) to afford compound 220-S7 (80 mg, 75.5% yield) as a light yellow solid. LC/MS (ESI) m/z: 370 (M+H)$^+$.

Step 7: tert-Butyl 2-(5-bromo-7-(1-fluoroethyl)-3-iodo-1H-indazol-1-yl) acetate (220-S8)

To a solution of compound 220-S7 (80 mg, 0.22 mmol) in DMF (2 mL) was added K$_2$CO$_3$ (75 mg, 0.54 mmol) and tert-butyl 2-bromoacetate (46 mg, 0.24 mmol). The mixture was stirred at room temperature overnight and then diluted with H$_2$O and extracted with EtOAc twice. The combined organic layers were washed with brine, dried over anhydrous Na$_2$SO$_4$, and concentrated. The obtained crude product was purified by column chromatography on silica gel eluted with petroleum ether/EtOAc (100:1 to 20:1) to afford compound 220-S8 (50 mg, 47.7% yield) as a light yellow solid. LC/MS (ESI) m/z: 485 (M+H)$^+$.

Step 8: tert-Butyl 2-(3-acetyl-5-bromo-7-(1-fluoroethyl)-1H-indazol-1-yl) acetate (220-S9)

To a solution of compound 220-S8 (50 mg, 0.10 mmol) in dry toluene (3 mL) was added tributyl(1-ethoxyvinyl)stannane (45 mg, 0.12 mmol) and Pd(PPh$_3$)$_4$ (12 mg, 0.01 mmol). The mixture was stirred at 100° C. under N$_2$ atmosphere overnight. The mixture was cooled to room temperature, 0.5 M aqueous HCl was added, and the mixture was stirred at room temperature for 30 minutes. The reaction mixture was diluted with EtOAc and washed with water and brine, dried over anhydrous Na$_2$SO$_4$, and concentrated. The obtained crude product is purified by column chromatography on silica gel eluted with petroleum ether/EtOAc (80:1 to 8:1) to afford compound 220-S9 (30 mg, 73.2% yield) as a milky white solid. LC/MS (ESI) m/z: 399 (M+H)$^+$.

Step 9: tert-Butyl 2-(3-acetyl-7-(1-fluoroethyl)-5-(2-methylpyrimidin-5-yl)-1H-indazol-1-yl) acetate (220-S10)

A round-bottom flask was charged with compound 220-S9 (30 mg, 0.075 mmol), 2-methylpyrimidin-5-ylboronic acid (11 mg, 0.083 mmol), K$_2$CO$_3$ (26 mg, 0.19 mmol) in dioxane/H$_2$O (2 mL, v/v=5:1). Tetrakis(triphenylphosphine) palladium(0) (9 mg, 0.008 mmol) was added to the mixture under N$_2$ atmosphere and the reaction was stirred at 90° C.

overnight under N₂ atmosphere. The mixture was diluted with EtOAc and washed with brine, dried over anhydrous Na₂SO₄, and concentrated to dryness. The residue was purified by column chromatography on silica gel eluted with petroleum ether/EtOAc (50:1 to 3:1) to afford compound 220-S10 (18 mg, 58.1% yield) as a light yellow solid. LC/MS (ESI) m/z: 413 (M+H)⁺.

Step 10: 2-(3-Acetyl-7-(1-fluoroethyl)-5-(2-methylpyrimidin-5-yl)-1H-indazol-1-yl) acetic Acid (220-S11)

To a solution of compound 220-S10 (18 mg, 0.044 mol) in DCM (1 mL) was added TFA (0.5 mL) and the mixture was stirred at room temperature for 1.5 hours. The solvent was removed and the residue was washed with ether and dried under vacuum to afford compound 220-S11 (10 mg, 64.3% yield) as a light yellow solid. LC/MS (ESI) m/z: 357 (M+H)⁺.

Step 11: (1R, 3S, 5R)-2-(2-(3-Acetyl-7-(1-fluoroethyl)-5-(2-methylpyrimidin-5-yl)-1H-indazol-1-yl)acetyl)-N-(6-bromo-3-methylpyridin-2-yl)-5-methyl-2-azabicyclo 13.1.01 hexane-3-carboxamide (220)

To a mixture of compound 220-S11 (9 mg, 0.025 mmol) and compound 220-S12 (10 mg, 0.032 mmol) in DMF (1 mL) was added DIPEA (15 mg, 0.12 mmol) followed by HATU (24 mg, 0.064 mmol). The reaction was stirred at room temperature for 2 hours. The mixture was diluted with EtOAc and washed with 10% aqueous LiCl solution and brine, dried, and concentrated to afford crude product, which was purified by prep-HPLC to afford 220 (2 mg, 12.5%) as a white solid. ¹H NMR (400 MHz, CD₃OD) δ 9.03 (s, 2H), 8.68-8.62 (m, 1H), 7.83 (s, 1H), 7.54 (d, J=8.0 Hz, 1H), 7.38 (d, J=8.0 Hz, 1H), 6.44-6.05 (m, 1H), 6.03-5.78 (m, 2H), 4.58-4.46 (m, 1H), 3.52 (dd, J=5.6, 2.4 Hz, 1H), 2.76 (s, 3H), 2.70 (d, J=1.6 Hz, 3H), 2.63 (dd, J=13.2, 9.2 Hz, 1H), 2.35-2.26 (m, 1H), 2.11 (s, 3H), 1.96-1.82 (m, 3H), 1.42 (s, 3H), 1.16-1.10 (m, 1H), 1.03-0.97 (m, 1H). LC/MS (ESI) m/z: 648 (M+H)⁺.

Scheme 85: Synthesis of (1R,3S,5S)-2-(2-(3-Acetyl-7-methyl-5-(2-methylpyrimidin-5-yl)-1H-indazol-1-yl)acetyl)-N3-(6-bromo-3-methylpridin-2-yl)-2-azabicyclo[3.1.0]hexane-3,5-dicarboxamide (221) and (1R,3S,5S)-2-(2-(3-Acetyl-7-methyl-5-(2-methylpyrimidin-5-yl)-1H-indazol-1-yl)acetyl-N-(6-bromo-3-methylpridin-2-yl)-5-cyano-2-azabicyclo[3.1.0]hexane-3-carboxamide (222)

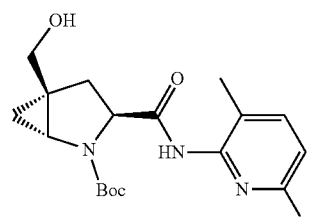

222-S1

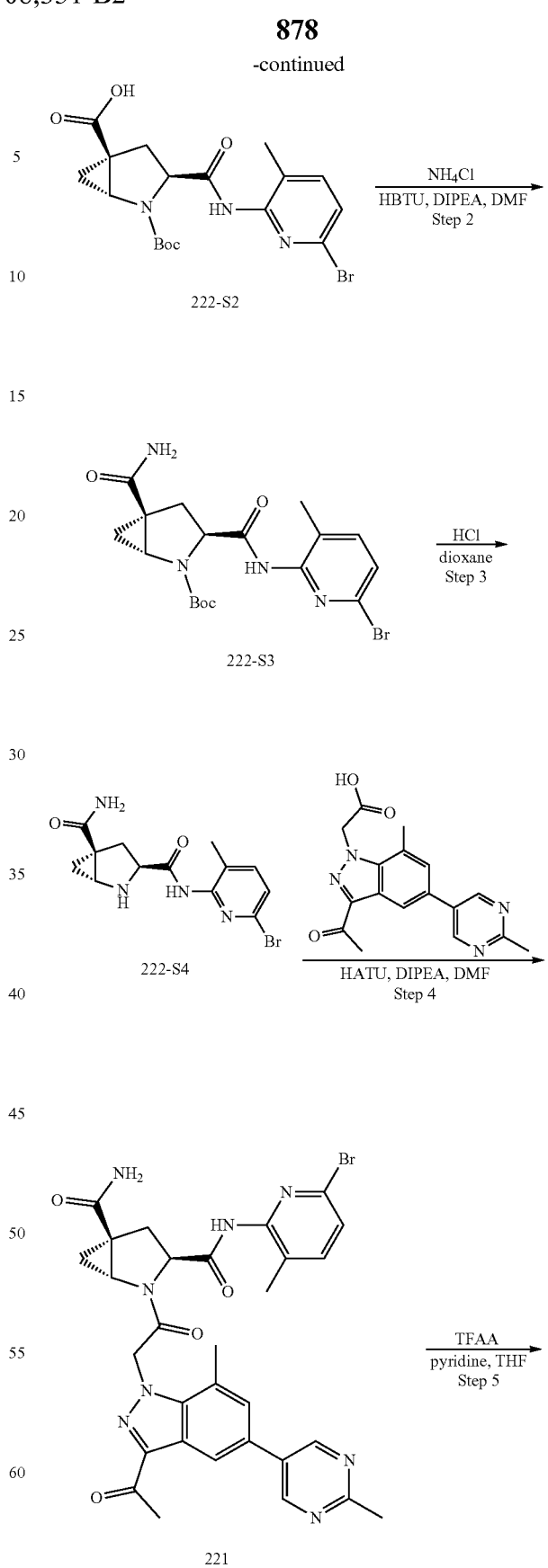

-continued

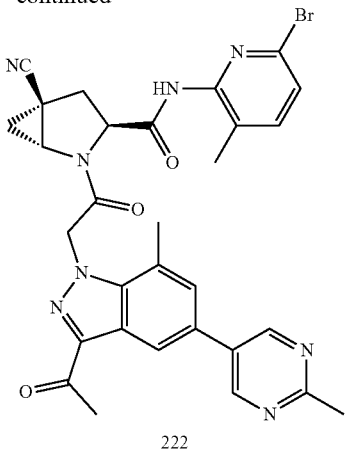

222

Step 1: (1R,3S,5S)-3-((6-Bromo-3-methylpyridin-2-yl)carbamoyl)-2-(tert-butoxycarbonyl)-2-azabicyclo[3.1.0]hexane-5-carboxylic Acid (222-S2)

To a mixture of compound 222-S1 (380 mg, 0.89 mmol) in t-BuOH (10 mL) was added aqueous NaOH (3.12 mL, 1M, 3.12 mmol), followed by potassium permanganate (281 mg, 1.78 mmol) dissolved in water (20 mL) at 0° C. The reaction was stirred at 30° C. overnight and the solvent was removed under vacuum. The residue was acidified by 2N aqueous HCl and extracted with DCM/i-PrOH (3/1, v/v) twice. The combined organic layers were dried over anhydrous $Na_2SO_4$ and concentrated. The crude product was purified by silica gel column (eluted with DCM/MeOH=50/1) to afford compound 222-S2 (220 mg, 57.8% yield) as a white solid. LC/MS (ESI) m/z: 440/442 (M+H)⁺.

Step 2: (1R,3S,5S)-tert-Butyl 3-((6-bromo-3-methylpyridin-2-yl)carbamoyl)-5-carbamoyl-2-azabicyclo[3.1.0]hexane-2-carboxylate (222-S3)

To a mixture of the compound 222-S2 (220 mg, 0.50 mmol) and ammonium chloride (53 mg, 2.50 mmol) in DMF (4 mL) was added HBTU (379 mg, 1.0 mmol) and DIPEA (0.16 mL, 1.0 mmol) at 0° C. The reaction was stirred at room temperature for 16 hours. The mixture was partitioned with EtOAc and water. The organic layer was washed with brine, dried over anhydrous $Na_2SO_4$, and concentrated under reduced pressure. The crude product was purified by silica gel column (eluted with DCM/MeOH=60/1) to afford compound 222-S3 (200 mg, 90.1% yield) as a white solid. LC/MS (ESI) m/z: 439/441 (M+H)⁺.

Step 3: (1R,3S,5S)—N³-(6-Bromo-3-methylpyridin-2-yl)-2-azabicyclo[3.1.0]hexane-3,5-dicarboxamide (222-4)

To a solution of compound 222-S3 (80 mg, 0.18 mmol) in dioxane (1 mL) was added HCl/dioxane (4 M, 1 mL). The reaction mixture was stirred at room temperature for 1 hour. The reaction solution was concentrated to afford compound 222-S4 (80 mg, 100% yield) as a white solid, which was directly used to the next reaction without additional purification. LC/MS (ESI) m/z: 339/341 (M+H)⁺

Step 4: (1R,3S,5S)-2-(2-(3-Acetyl-7-methyl-5-(2-methylpyrimidin-5-yl)-1H-indazol-1-yl)acetyl)-N³-(6-bromo-3-methylpyridin-2-yl)-2-azabicyclo[3.1.0]hexane-3,5-dicarboxamide (221)

To a solution of the compound 222-S4 (80 mg, 0.18 mmol), 2-(3-acetyl-7-methyl-5-(2-methylpyrimidin-5-yl)-1H-indazol-1-yl)acetic acid (59 mg, 0.18 mmol) and HATU (138 mg, 0.36 mmol) in DMF (2 mL) was added DIPEA (0.12 mL, 0.73 mmol). The reaction was stirred at room temperature for 2 hours. The mixture was partitioned with EtOAc and water. The organic layer was washed with brine, dried over anhydrous $Na_2SO_4$, and concentrated under reduced pressure. The residue was purified by silica gel column (eluted with DCM/MeOH=60/1) to afford 221 (30 mg, 25.6% yield) as a white solid. ¹H-NMR (400 MHz, $CD_3OD$) δ 9.04 (s, 2H), 8.43 (s, 1H), 7.65 (d, J=7.4 Hz, 1H), 7.57 (s, 1H), 7.44 (d, J=7.4 Hz, 1H), 5.82 (m, 1H), 5.71 (m, 1H), 5.36 (m, 1H), 4.72 (m, 1H), 3.29-3.31 (m, 2H), 2.67-2.80 (m, 10H), 2.26 (s, 3H), 0.85-0.89 (m, 2H). LC/MS (ESI) m/z: 645/647 (M+H)⁺.

Step 5: (1R,3S,5S)-2-(2-(3-Acetyl-7-methyl-5-(2-methylpyrimidin-5-yl)-1H-indazol-1-yl)acetyl)-N-(6-bromo-3-methylpyridin-2-yl)-5-cyano-2-azabicyclo[3.1.0]hexane-3-carboxamide (222)

To a solution of 221 (20 mg, 0.03 mmol) and pyridine (4.9 mg, 0.06 mmol) in dry THF (3 mL) was added TFAA (31.5 mg, 0.25 mmol). The reaction was stirred at 60° C. for 12 hours and then concentrated under reduced pressure. The residue product was purified by prep-TLC to afford 222 (3.5 mg, 17.5% yield) as a white solid. ¹H-NMR (400 MHz, $CD_3OD$) δ 9.04 (s, 2H), 8.43 (s, 1H), 7.65 (d, J=7.4 Hz, 1H), 7.57 (s, 1H), 7.44 (d, J=7.4 Hz, 1H), 5.82 (m, 1H), 5.71 (m, 1H), 5.36 (m, 1H), 4.72 (m, 1H), 3.46-3.51 (m, 1H), 2.67-2.80 (m, 9H), 2.01-2.11 (m, 1H), 2.24 (s, 3H), 0.85-0.89 (m, 2H). LC/MS (ESI) m/z:627/629 (M+H)⁺.

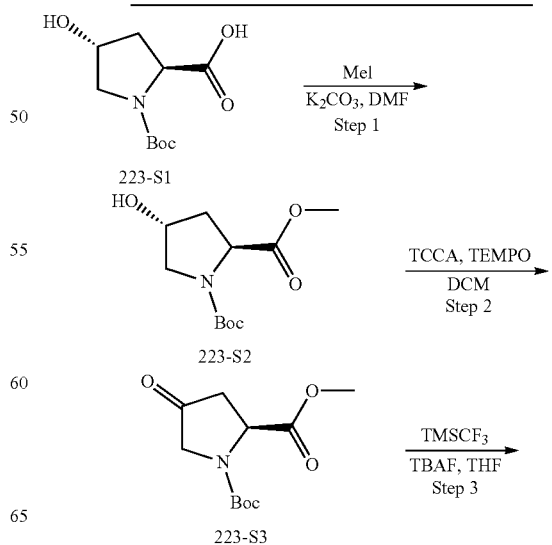

Scheme 86: Synthesis of (2S,4S)-1-(2-(3-Acetyl-7-methyl-5-(2-methylpyrimidin-5-yl)-1H-indazol-1-yl)acetyl)-N-(6-bromo-3-methylpyridine-2-yl)-4-(trifluoromethyl)pyrrolidine-2-carboxamide (223)

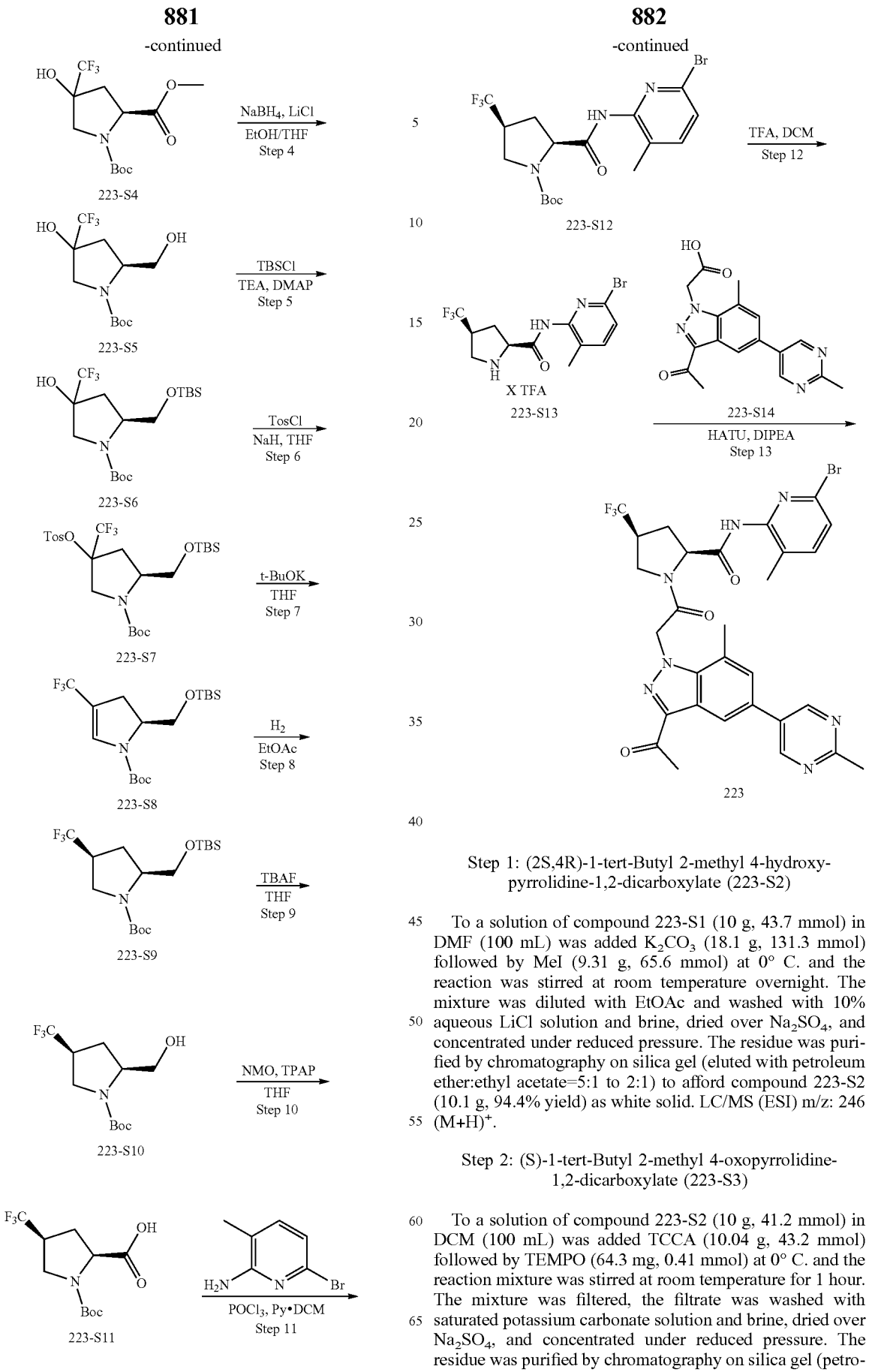

Step 1: (2S,4R)-1-tert-Butyl 2-methyl 4-hydroxy-pyrrolidine-1,2-dicarboxylate (223-S2)

To a solution of compound 223-S1 (10 g, 43.7 mmol) in DMF (100 mL) was added $K_2CO_3$ (18.1 g, 131.3 mmol) followed by MeI (9.31 g, 65.6 mmol) at 0° C. and the reaction was stirred at room temperature overnight. The mixture was diluted with EtOAc and washed with 10% aqueous LiCl solution and brine, dried over $Na_2SO_4$, and concentrated under reduced pressure. The residue was purified by chromatography on silica gel (eluted with petroleum ether:ethyl acetate=5:1 to 2:1) to afford compound 223-S2 (10.1 g, 94.4% yield) as white solid. LC/MS (ESI) m/z: 246 (M+H)$^+$.

Step 2: (S)-1-tert-Butyl 2-methyl 4-oxopyrrolidine-1,2-dicarboxylate (223-S3)

To a solution of compound 223-S2 (10 g, 41.2 mmol) in DCM (100 mL) was added TCCA (10.04 g, 43.2 mmol) followed by TEMPO (64.3 mg, 0.41 mmol) at 0° C. and the reaction mixture was stirred at room temperature for 1 hour. The mixture was filtered, the filtrate was washed with saturated potassium carbonate solution and brine, dried over $Na_2SO_4$, and concentrated under reduced pressure. The residue was purified by chromatography on silica gel (petroleum ether:ethyl acetate=10:1) to afford compound 223-S3 (8 g, 80.7% yield) as a white solid. LC/MS (ESI) m/z: 244 (M+H)+.

Step 3: (2S)-1-tert-Butyl 2-methyl 4-hydroxy-4-(trifluoromethyl)pyrrolidine-1,2-dicarboxylate (223-S4)

To a solution of compound 223-S3 (6 g, 24.7 mmol) in THF (100 mL) was added TMSCF$_3$ (5.26 g, 37.0 mmol) followed by TBAF (0.15 mL, 0.15 mmol, 1 mol/L in THF) at 0° C. and the reaction was stirred at room temperature overnight. The reaction was quenched with aqueous NH$_4$Cl solution and extracted with EtOAc twice. The combined organic layers were washed with water and brine, dried over Na$_2$SO$_4$, and concentrated under reduced pressure. The residue was purified by chromatography on silica gel (petroleum ether:ethyl acetate=20:1) to afford compound 223-S4 (4.4 g, 56.8% yield) as a yellow oil. LC/MS (ESI) m/z: 314 (M+H)+.

Step 4: (2S)-tert-Butyl 4-hydroxy-2-(hydroxymethyl)-4-(trifluoromethyl)pyrrolidine-1-carboxylate (223-S5)

To a solution of compound 223-S4 (4.4 g, 14.1 mmol) in THF (56 mL) was added LiCl (1.31 g, 30.91 mmol) and NaBH4 (1.33 g, 35.1 mmol) followed by the dropwise addition of EtOH (112 mL) at 0° C. The reaction mixture was stirred at 0° C. for 1 hour and was allowed to warm to room temperature and stir overnight. The mixture was cooled at 0° C. and acidified to pH=4 with 10% aqueous citric acid solution. The mixture was extracted with DCM and washed with water and brine, dried over Na$_2$SO$_4$, and concentrated under reduced pressure. The residue was purified by chromatography on silica gel (petroleum ether:ethyl acetate=15:1) to afford compound 223-S5 (3.4 g, 85.0% yield) as a yellow oil. LC/MS (ESI) m/z: 286 (M+H)+.

Step 5: (2S)-tert-Butyl 2-(((tert-butyldimethylsilyl)oxy)methyl)-4-hydroxy-4-(trifluoromethyl)pyrrolidine-1-carboxylate (223-S6)

To a solution of compound 223-S5 (3.4 g, 11.9 mmol) in DCM (50 mL) was added TEA (1.2 g, 11.9 mmol) and TBDMSCl (2.15 g, 14.28 mmol) at 0° C. and the reaction was stirred at room temperature overnight under N$_2$ atmosphere. The reaction mixture was diluted with DCM, washed with saturated aqueous NH$_4$Cl solution and brine, dried over Na$_2$SO$_4$, and concentrated under reduced pressure to remove the volatiles. The residue was purified by chromatography on silica gel (petroleum ether:ethyl acetate=60:1) to afford compound 223-S6 (4.2 g, 88.3% yield) as yellow oil. LC/MS (ESI) m/z: 400 (M+H)+.

Step 6: (2S)-tert-Butyl 2-(((tert-butyldimethylsilyl)oxy)methyl)-4-(tosyloxy)-4 (trifluoromethyl)pyrrolidine-1-carboxylate (223-S7)

To a solution of compound 223-S6 (4 g, 10.0 mmol) in THF (40 mL) was added NaH (802 mg, 20.0 mmol) at 0° C. The mixture was stirred at room temperature for 30 minutes and tosyl chloride (3.82 g, 20.0 mmol) was added in portions at 0° C. The reaction mixture was stirred at room temperature overnight under N$_2$ atmosphere. The reaction was quenched with saturated aqueous NH$_4$Cl solution and the mixture was diluted with EtOAc, washed with water and brine, dried over Na$_2$SO$_4$, and concentrated under reduced pressure. The residue was purified by chromatography on silica gel (petroleum ether:ethyl acetate=80:1) to afford compound 223-S7 (4.9 g, 88.5%) as yellow oil. LC/MS (ESI) m/z: 554 (M+H)+.

Step 7: (S)-tert-Butyl 2-(((tert-butyldimethylsilyl)oxy)methyl)-4-(trifluoromethyl)-2,3-dihydro-1H-pyrrole-1-carboxylate (223-S8)

To a solution of compound 223-S7 (4.2 g, 7.59 mmol) in THF (40 mL) was added t-BuOK (1.70 g, 15.19 mmol) at −78° C. and the reaction was stirred at room temperature for 2 hours under N$_2$ atmosphere. The reaction was quenched with cooled water and the mixture was diluted with EtOAc, washed with water and brine, dried over Na$_2$SO$_4$, and concentrated under reduced pressure. The residue was purified by chromatography on silica gel (petroleum ether:ethyl acetate=80:1) to afford compound 223-S8 (1.6 g, 55.3% yield) as a yellow oil. LC/MS (ESI) m/z: 382 (M+H)+.

Step 8: (2S,4S)-tert-Butyl 2-(((tert-butyldimethylsilyl)oxy)methyl)-4-(trifluoromethyl)pyrrolidine-1-carboxylate (223-S9)

To a solution of compound 223-S8 (300 mg, 0.78 mmol) in EtOAc (5 ml) was added Pd/C (15 mg, 10% wt). The reaction mixture was stirred under a H$_2$ balloon at room temperature for 2 hours. The mixture was filtered and concentrated to dryness to afford compound 223-S9 (280 mg, 93.3%) as a brown oil. LC/MS (ESI) m/z: 384 (M+H)+.

Step 9: (2S,4S)-tert-Butyl 2-(hydroxymethyl)-4-(trifluoromethyl)pyrrolidine-1-carboxylate (223-S10)

To a solution of compound 223-S9 (280 mg, 0.73 mmol) in THF (5 ml) was added TBAF (1 mol/L in THF)(3.65 mL, 3.65 mmol) at 0° C. The reaction mixture was stirred at room temperature for 1 hour under a nitrogen atmosphere. The reaction mixture was diluted with EtOAc, washed with saturated NH$_4$Cl and brine, dried over Na$_2$SO$_4$, and concentrated under reduced pressure. The residue was purified by chromatography on silica gel (petroleum ether:ethyl acetate=20:1) to afford compound 223-S10 (200 mg, 96.6% yield) as a yellow oil. LC/MS (ESI) m/z: 270 (M+H)+.

Step 10: (2S,4S)-1-(tert-Butoxycarbonyl)-4-(trifluoromethyl)pyrrolidine-2-carboxylic Acid (223-S11)

To a solution of compound 223-S10 (200 mg, 0.72 mmol) in THF (5 ml) was added NMO (842 mg, 7.20 mmol) and TPAP (25.2 mg, 0.073 mmol). The reaction mixture was stirred at room temperature for 2 hours under a nitrogen atmosphere. The reaction mixture was diluted with EtOAc, washed with water and brine, dried over Na$_2$SO$_4$, and concentrated under reduced pressure. The residue was purified by chromatography on silica gel (DCM:CH+OH=50:1) to afford compound 223-S11 (150 mg, 71.4%) as a yellow oil. LC/MS (ESI) m/z: 284 (M+H)+.

Step 11: (2S,4S)-tert-Butyl 2-((6-bromo-3-methylpyridin-2-yl)carbamoyl)-4-(trifluoromethyl)pyrrolidine-1-carboxylate (223-S12)

To a solution of compound 223-S11 (50 mg, 0.18 mmol) and 6-bromo-3-methylpyridin-2-amine (33.3 mg, 0.18 mmol) in DCM (3 mL) was added pyridine (71.1 mg, 0.90 mmol) at 0° C. followed by the dropwise addition of POCl₃ (27.54 mg, 0.18 mmol). The reaction mixture was stirred at 0° C. for 30 minutes. The reaction mixture was quenched with ice-cooled water and extracted with DCM twice. The combined organic phases were washed with brine, dried over anhydrous Na₂SO₄, filtered, and concentrated to dryness. The residue was purified by silica gel column (eluted with DCM/MeOH=50/1) to afford compound 223-S12 (45 mg, 57.0%) as a white solid. LC/MS (ESI) m/z: 452/454 (M+H)⁺.

Step 12: (2S,4S)—N-(6-Bromo-3-methylpyridin-2-yl)-4-(trifluoromethyl)pyrrolidine-2-carboxamide TFA Salt (223-S13)

To a solution of compound 223-S12 (45 mg, 0.10 mmol) in DCM (2.5 mL) was added TFA (1 mL). The reaction was stirred at room temperature for 1.5 hours and then concentrated under reduced pressure to afford compound 223-S13 (50 mg, 100.0% yield) as a yellow solid, which was directly carried forward in the next step without additional purification. LC/MS (ESI) m/z: 352/354 (M+H)⁺.

Step 13: (2S,4S)-1-(2-(3-Acetyl-7-methyl-5-(2-methylpyrimidin-5-yl)-1H-indazol-1-yl)acetyl)-N-(6-bromo-3-methylpyridin-2-yl)-4-(trifluoromethyl) pyrrolidine-2-carboxamide (223)

To a solution of the compound 223-S13 (50 mg, 0.10 mmol), compound 223-S14 (32.4 mg, 0.10 mmol) and HATU (76.0 mg, 0.20 mmol) in DMF (2 mL) was added DIPEA (0.07 mL, 0.40 mmol) at 0° C. The reaction was stirred at room temperature overnight. The mixture was diluted with EtOAc and washed with 10% aqueous LiCl solution and brine, dried over Na₂SO₄, and concentrated to dryness. The residue was purified by prep-HPLC to afford 233 (5.2 mg, 7.9% yield) as a white solid. ¹H NMR (400 MHz, CD₃OD) δ 8.99 (d, J=3.4 Hz, 2H), 8.41 (s, 1H), 7.53 (d, J=8.4 Hz, 2H), 7.37 (d, J=7.9 Hz, 1H), 5.78 (s, 2H), 4.72 (t, J=8.3 Hz, 1H), 4.37-4.29 (m, 1H), 3.87 (t, J=10.4 Hz, 1H), 3.48 (s, 1H), 2.74 (s, 7H), 2.67 (s, 3H), 2.28 (d, J=5.8 Hz, 1H), 2.08 (s, 3H). LC/MS (ESI) m/z:658/660 (M+H)⁺.

Scheme 87: Synthesis of (1R,3S,5R)-2-(2-(3-Acetyl-7-methyl-5-(2-methylpyrimidin-5-yl)-1H-indazol-1-yl)acetyl)-5-((bis(2-fluoroethyl)amino)methyl)-N-(6-bromo-3-methylpyridin-2-yl)-2-azabicyclo[3.1.0]hexane-3-carboxamide (227)

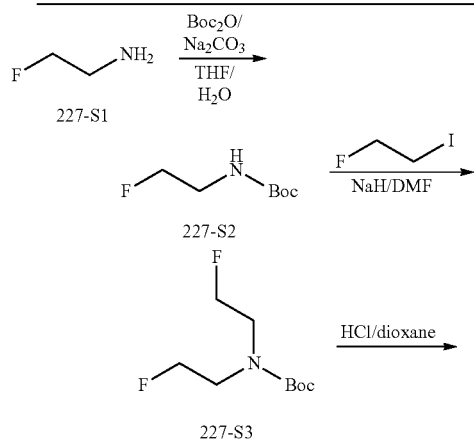

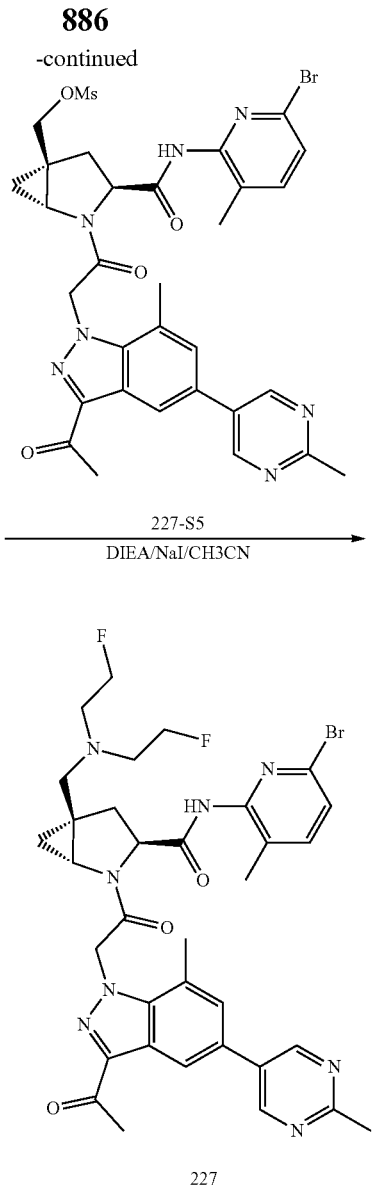

Step 1: tert-Butyl 2-fluoroethylcarbamate (227-S2)

To a solution of 227-S1 (500 mg, 5.03 mmol) in THF (5 mL)/H₂O (5 mL) was added NaHCO₃ (1.69 g, 20.1 mmol) and Boc₂O (1.31 g, 6.03 mmol) at 0° C. The reaction mixture was stirred at room temperature overnight. The mixture was diluted with EtOAc and washed with H₂O solution and brine, dried over Na₂SO₄, and concentrated to dryness. The residue was purified by silica gel column (eluted with PE:EtOAc=20:1 to 10:1) to afford compound 227-S2 (400 mg, 48.8%) as a white solid. LC/MS (ESI) m/z: 108 (M−56+H)⁺.

Step 2: tert-Butyl bis(2-fluoroethyl)carbamate (227-S3)

To a solution of 227-S2 (200 mg, 1.23 mmol) in DMF (5 mL) was added NaH (59 mg, 1.47 mmol) at 0° C. After stirring at room temperature for 30 minutes, 1-fluoro-2-iodoethane (235 mg, 1.35 mmol) was added. The reaction mixture was stirred at room temperature for 2 hours. The mixture was diluted with H$_2$O at 0° C., extracted with EtOAc, washed with water and brine, dried over Na$_2$SO$_4$, and concentrated to dryness. The residue was purified by silica gel column (eluted with PE:EtOAc=30:1 to 20:1) to afford compound 227-S3 (130 mg, 50.6%) as a white solid. LC/MS (ESI) m/z: 154 (M−56+H)$^+$.

Step 3: Bis(2-fluoroethyl)amine (227-S4)

To a solution of compound 227-S3 (130 mg, 0.62 mmol) in dioxane (1 mL) was added HCl/dioxane (1 mL, 4 M) and the reaction mixture was stirred at room temperature for 2 hours. The mixture was concentrated to dryness to afford compound 227-S4 (120 mg, 100%) as a white solid, which was directly used in the next reaction without further purification. LC/MS (ESI) m/z: 110 (M+H)$^+$.

Step 4: (1R,3S,5R)-2-(2-(3-Acetyl-7-methyl-5-(2-methylpyrimidin-5-yl)-1H-indazol-1-yl)acetyl)-5-((bis(2-fluoroethyl)amino)methyl)-N-(6-bromo-3-methylpyridin-2-yl)-2-azabicyclo[3.1.0]hexane-3-carboxamide (227)

To a solution of compound 227-S5 (30 mg, 0.05 mmol) in MeCN (3 mL) was added DIPEA (0.03 mL, 0.21 mmol), NaI (8 mg, 0.05 mmol) and compound 227-S4 (120 mg, 0.62 mmol). The reaction mixture was stirred at 60° C. overnight. The mixture was partitioned with EtOAc and water. The organic layer was washed with brine, dried over anhydrous Na$_2$SO$_4$, and concentrated under reduced pressure. The residue was purified by silica gel column (eluted with DCM/MeOH=20/1) and further purified by prep-HPLC to afford 227 (1.3 mg, 3.6%) as a white solid. $^1$H NMR (400 MHz, CD$_3$OD) δ 8.97 (s, 2H), 8.39 (d, J=1.0 Hz, 1H), 7.58-7.46 (m, 2H), 7.36 (d, J=7.9 Hz, 1H), 5.95 (m, 1H), 5.77 (m, 1H), 4.62 (m, 3H), 4.50 (m, 2H), 3.61 (m, 1H), 3.10-2.87 (m, 5H), 2.74 (s, 7H), 2.67 (s, 3H), 2.64-2.48 (m, 2H), 2.12 (s, 3H), 1.06 (m, 1H), 0.90 (m, 1H). LC/MS (ESI) m/z:723/725 (M+H)$^+$.

Scheme 88: Synthesis of 5-(3-Acetyl-1-(2-((1R,3S,5R)-3-(6-bromo-3-methylpyridin-2-ylcarbamoyl)-5-methyl-2-azabicyclo[3.1.0]hexan-2-yl)-2-oxoethyl)-1H-pyrazolo[3,4-c]pyridin-5-yl)-2-methylpyrimidine 1-oxide (228)

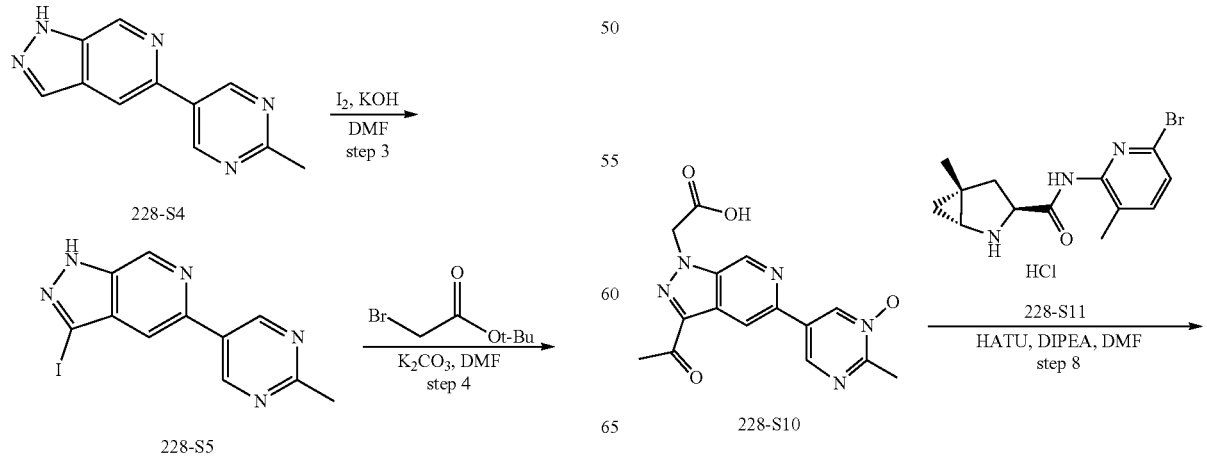

-continued

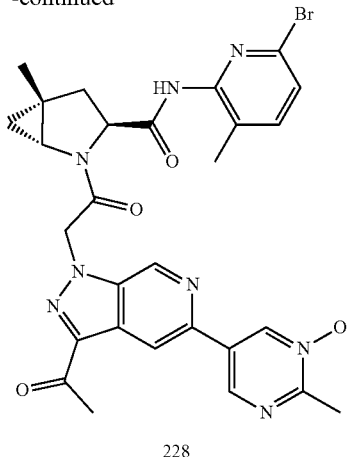

228

Step 1: 4-Methyl-6-(2-methylpyrimidin-5-yl)pyridin-3-amine (229-S3)

To a mixture of compound 229-S1 (1.6 g, 8.6 mmol), (2-methylpyrimidin-5-yl) boronic acid (2.14 g, 15.5 mmol) and potassium carbonate (3.0 g, 21.5 mmol) in dioxane (18 mL) and water (2 mL) was added Pd(PPh$_3$)$_4$ (0.99 g, 0.86 mmol) and the mixture was stirred at 80° C. for 16 hours under N$_2$ atmosphere. The mixture was cooled and filtered and the filtrate was diluted with water (20 mL) and extracted with EtOAc (50 mL×3). The organic layer was dried with Na$_2$SO$_4$ and concentrated to afford crude product, which was re-crystallized from EtOAc to afford compound 229-S3 (750 mg, 43.6%) as a white solid. LC/MS (ESI) m/z: 201 (M+H)$^+$.

Step 2: 5-(2-Methylpyrimidin-5-yl)-1H-pyrazolo[3,4-c]pyridine (229-S4)

To a mixture of compound 229-S3 (750 mg, 3.55 mmol) and potassium acetate (107 mg, 1.09 mmol) in CHCl$_3$ (15 mL) was added acetic anhydride (869 mg, 8.51 mmol) at 0° C. The mixture was stirred at 25° C. for 1 hour and then heated to 60° C. tert-Butyl nitrite (831 mg, 8.05 mmol) was added dropwise and the mixture was stirred at 60° C. for 16 hours. The mixture was cooled and extracted with EtOAc (20 mL×3). The combined organic layers were dried with Na$_2$SO$_4$ and concentrated to afford crude product, which was re-crystallized from EtOAc to afford compound 228-S4 (300 mg, 40.1%) as a white solid. LC/MS (ESI) m/z: 212 (M+H)$^+$.

Step 3: 3-Iodo-5-(2-methylpyrimidin-5-yl)-1H-pyrazolo[3,4-c]pyridine (228-S5)

To a mixture of compound 228-S4 (300 mg, 1.42 mmol) in DMF was added KOH (179 mg, 3.20 mmol) and I$_2$ (541 mg, 2.13 mmol) at 0° C. The mixture was stirred at room temperature for 1.5 hours. The mixture was quenched with 5% aqueous Na$_2$S$_2$O$_3$ solution (10 mL) and extracted with EtOAc (20 mL×3). The combined organic layers were dried with Na$_2$SO$_4$ and concentrated to afford compound 228-S5 (350 mg, 73.1%) as a yellow solid. LC/MS (ESI) m/z: 338 (M+H)$^+$.

Step 4: tert-Butyl 2-(3-iodo-5-(2-methylpyrimidin-5-yl)-1H-pyrazolo[3,4-c]pyridin-1-yl)acetate (228-S6)

To a mixture of compound 228-S5 (350 mg, 1.04 mmol), tert-butyl 2-bromoacetate (304 mg, 1.56 mmol) in DMF (6 mL) was added K$_2$CO$_3$ (287 mg, 2.08 mmol) and the mixture was stirred at room temperature overnight. The reaction mixture was diluted with water and extracted with ethyl acetate twice. The combined organic layers were washed with brine, dried with Na$_2$SO$_4$, and concentrated to dryness. The residue was purified with silica gel column (eluted with petroleum ether:ethyl acetate=5:1 to 1:1) to afford compound 228-S6 (350 mg, 82.2%) as a white solid. LC/MS (ESI) m/z: 452 (M+H)$^+$.

Step 5: tert-Butyl 2-(3-iodo-5-(2-methylpyrimidin-5-yl)-1H-pyrazolo[3,4-c]pyridin-1-yl)acetate (228-S8)

To a mixture of compound 228-S6 (350 mg, 0.78 mmol) in toluene (15 mL) was added Pd(PPh$_3$)$_4$ (72 mg, 0.062 mmol) and tributyl(1-ethoxyvinyl)stannane (336 mg, 0.93 mmol). The mixture was stirred at 100° C. for 16 hours under nitrogen atmosphere. The reaction mixture was quenched with 0.5 N hydrochloride (10 mL) and stirred at room temperature for 1 hour. The mixture was extracted with ethyl acetate twice and the combined organic layer were washed with brine, dried with Na$_2$SO$_4$, and concentrated to dryness. The residue was purified with silica gel column (eluted with petroleum ether:ethyl acetate=5:1 to 1:1) to afford compound 228-S8 (270 mg, 94.3%) as a white solid. LC/MS (ESI) m/z: 368 (M+H)$^+$.

Step 6: 5-(3-Acetyl-1-(2-tert-butoxy-2-oxoethyl)-1H-pyrazolo[3,4-c]pyridin-5-yl)-2-methylpyrimidine 1-oxide (228-S9)

To a solution of compound 228-S8 (270 mg, 0.73 mmol) was added m-CPBA (165 mg, 0.96 mmol). The mixture was stirred at room temperature for 16 hours and then quenched with a 5% Na$_2$S$_2$O$_3$ solution and extracted with DCM. The organic layer was separated, dried, and concentrated to afford crude product, which was purified by silica gel column (eluted with DCM:MeOH=100:0 to 80:1) to afford compound 228-S9 (110 mg, 39.3%) as a white solid. LC/MS (ESI) m/z: 384 (M+H)$^+$.

Step 7: 5-(3-Acetyl-1-(carboxymethyl)-1H-pyrazolo[3,4-c]pyridin-5-yl)-2-methylpyrimidine 1-oxide (228-S10)

A solution of NaOH (34 mg, 0.86 mmol) in 1 mL of water was added into a solution of compound 228-S9 (110 mg, 0.29 mmol) in methanol (1 mL) and THF (1 mL). The mixture was stirred at room temperature for 16 hours. The solvent was removed under vacuum and the residue was taken up in ether (20 mL) and additional water (10 mL). The organic phase was separated and the aqueous phase was diluted with EtOAc and then acidified with 1 N HCl to pH of approximately 5. The organic phase was washed with brine and dried, concentrated to afford compound 228-S10 (80 mg, 84.2%) as a white solid. LC/MS (ESI) m/z: 328 (M+H)$^+$.

Step 8: 5-(3-Acetyl-1-(2-((1R,3S,5R)-3-(6-bromo-3-methylpyridin-2-ylcarbamoyl)-5-methyl-2-azabicyclo[3.1.0]hexan-2-yl)-2-oxoethyl)-1H-pyrazolo[3,4-c]pyridin-5-yl)-2-methylpyrimidine 1-oxide (228)

To a solution of the compound 228-S10 (80 mg, 0.244 mmol), compound 228-S11 (75 mg, 0.244 mmol) and HATU (139 mg, 0.366 mmol) in DMF (3 mL) was added DIPEA (127 mg, 0.976 mmol). The reaction was stirred at room temperature for 16 hours. The reaction was diluted with EtOAc, washed with 10% aqueous LiCl solution and brine, dried, and concentrated to afford crude product, which was purified via pre-HPCL to afford compound 228 (14 mg, 9.3%) as a white solid. $^1$H-NMR (400 MHz, DMSO-d$_6$) δ 10.30 (s, 1H), 9.32 (d, J=1.2 Hz, 1H), 9.17 (d, J=1.8 Hz, 1H), 8.91 (d, J=1.9 Hz, 1H), 8.69 (d, J=1.2 Hz, 1H), 7.63 (d, J=8.2 Hz, 1H), 7.45 (d, J=7.9 Hz, 1H), 6.07 (d, J=17.3 Hz, 1H), 5.75 (d, J=17.2 Hz, 1H), 4.43 (dd, J=9.2, 5.1 Hz, 1H), 3.60 (dd, J=5.5, 2.3 Hz, 1H), 2.69 (s, 3H), 2.63 (s, 3H), 2.53-2.57 (m, 1H), 2.05-2.11 (m, 1H), 2.04 (s, 3H), 1.33 (s, 3H), 1.07-1.13 (m, 1H), 0.98-1.04 (m, 1H). LC/MS (ESI) m/z: 619/621 (M+H)$^+$.

Scheme 89: Synthesis of (1R,3S,5S)-2-(2-(3-Acetyl-7-allyl-5-(2-methylpyrimidin-5-yl)-1H-indazol-1-yl)acetyl)-5-(allyloxymethyl)-N-(6-bromo-3-methylpyridin-2-yl)-2-azabicyclo[3.1.0]hexane-3-carboxamide (229)

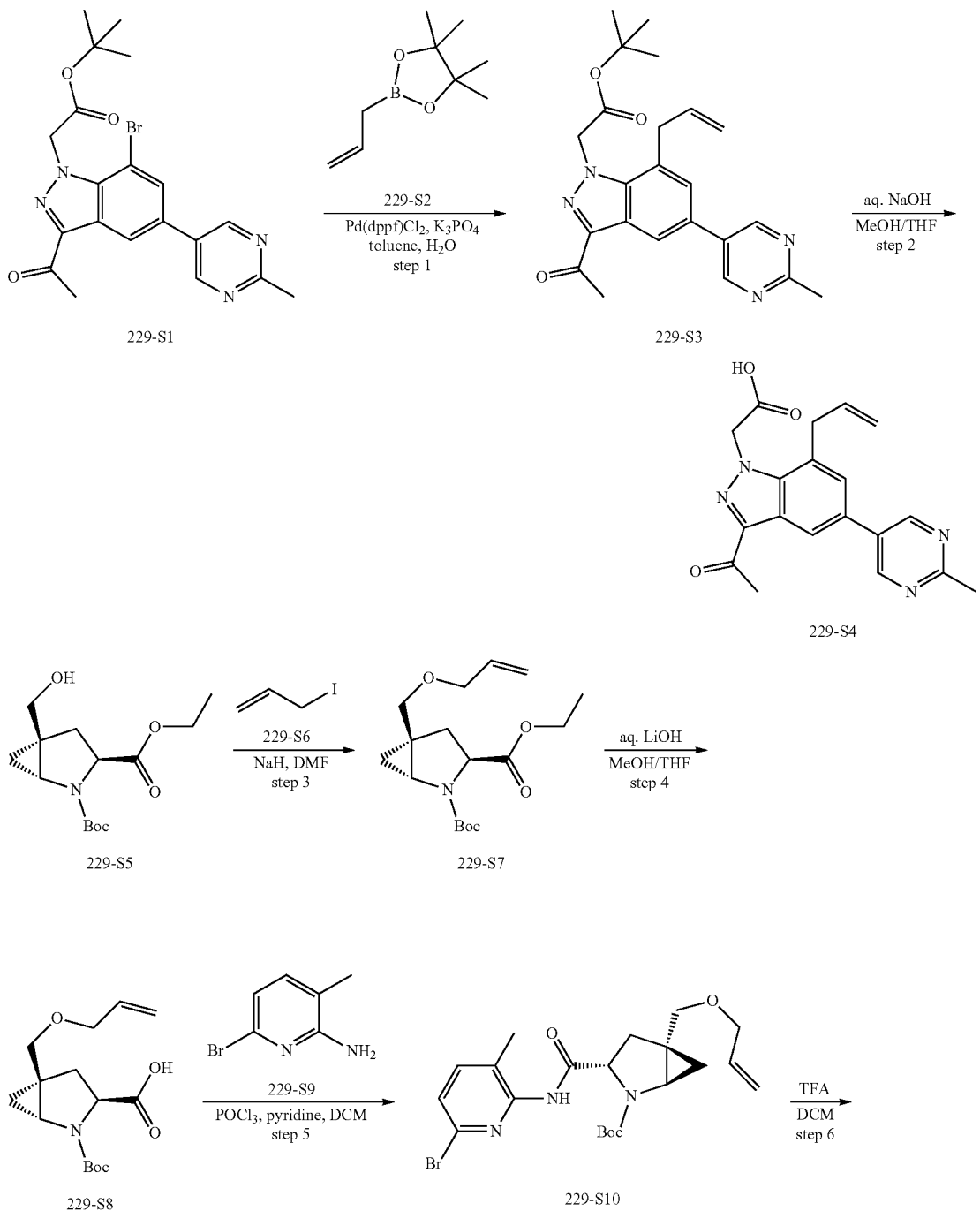

-continued

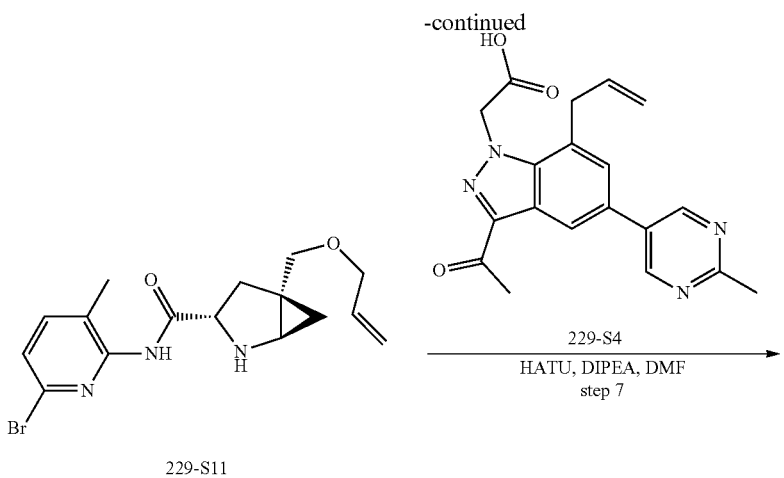

229-S11

HATU, DIPEA, DMF
step 7
229-S4

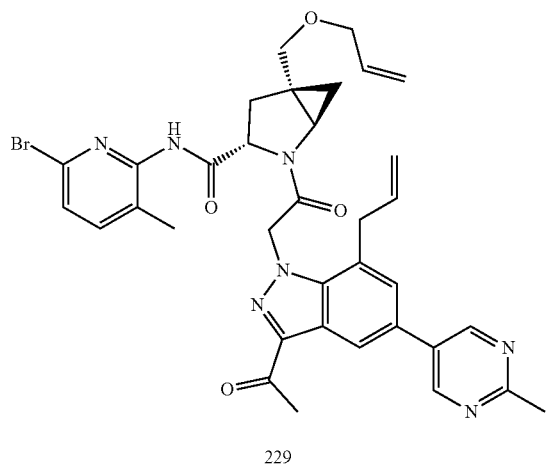

229

Step 1: tert-Butyl 2-(3-acetyl-7-allyl-5-(2-methylpyrimidin-5-yl)-1H-indazol-1-yl)acetate (229-3)

To a mixture of compound 229-S1 (267 mg, 0.6 mmol) and compound 229-S2 (222 mg, 1.32 mmol) in toluene (10 mL) and H$_2$O (2 mL) was added K$_3$PO$_4$ (382 mg, 1.8 mmol) followed by the addition of Pd(dppf)Cl$_2$ (44 mg, 0.06 mmol). The reaction was stirred at 100° C. for 16 hours under N$_2$ atmosphere. The mixture was cooled, diluted with EtOAc, and washed with water and brine. The organic layer was separated, dried and concentrated to afford crude product, which was purified by silica gel column (eluted with PE:EtOAc=20:1 to 2:1) to afford compound 229-S3 (194 mg, 79.5%) as a white solid. LC/MS (ESI) m/z: 407 (M+H)$^+$.

Step 2: 2-(3-Acetyl-7-allyl-5-(2-methylpyrimidin-5-yl)-1H-indazol-1-yl)acetic Acid (229-S4)

To a mixture of compound 229-S3 (130 mg, 0.32 mmol) in MeOH/THF (4 mL, 1:1) was added aqueous NaOH solution (39 mg, 0.96 mmol in 2 mL of water). The mixture was stirred at room temperature for 4 hours and then diluted with water (3 mL) and extracted with ether. The aqueous layer was collected and acidified with aqueous HCl solution (1 N) to a pH of approximately 5. The resulting mixture was extracted with DCM/MeOH (20 mL×2, 10:1, V/V) and the combined organic phases were washed with brine, dried over anhydrous Na$_2$SO$_4$, filtered and concentrated to afford compound 229-S4 (73 mg, 65.2%) as a white solid. LC/MS (ESI) m/z: 351 (M+H)$^+$.

Step 3: (1R,3S,5S)-2-tert-Butyl 3-ethyl 5-(allyloxymethyl)-2-azabicyclo[3.1.0]hexane-2,3-dicarboxylate (229-S7)

To a mixture of compound 229-S5 (1.37 g, 4.8 mmol) in dry DMF (20 mL) was added NaH (384 mg, 9.6 mmol) at 0° C. under N$_2$ atmosphere and the mixture was stirred at room temperature for 40 minutes before compound 229-S6 (3.24 g, 19.2 mmol) was added at 0° C. in portions. The mixture was stirred at room temperature for 2 hours and the mixture was quenched with saturated aqueous NH$_4$Cl solution. The reaction was extracted with DCM and the organic layer was dried and concentrated to afford crude compound 229-S7 (1.56 g, 99.9% yield) as a colorless oil, which was carried forward without additional purification. LC/MS (ESI) m/z: 348 (M+Na)$^+$.

Step 4: (1R,3S,5S)-5-(Allyloxymethyl)-2-(tert-butoxycarbonyl)-2-azabicyclo[3.1.0]hexane-3-carboxylic Acid (229-S8)

To a mixture of compound 229-S7 (1.56 g, 4.8 mmol) in MeOH/THF (20 mL, 1:1) was added aqueous NaOH solution (384 mg, 9.6 mmol in 10 mL of water). The mixture was stirred at room temperature for 4 hours and then diluted with water (20 mL). The reaction was extracted with ether and the aqueous layer was collected and acidified with aqueous HCl solution (1 N) to a pH of approximately 5. The mixture was extracted with DCM/MeOH (20 mL×2, 10:1, V/V) and the combined organic phases were washed with brine, dried over anhydrous $Na_2SO_4$, filtered and concentrated to afford compound 229-S8 (630 mg, 44.0%) as a colorless oil. LC/MS (ESI) m/z: 320 (M+Na)$^+$.

Step 5: (1R,3S,5S)-tert-Butyl 5-(allyloxymethyl)-3-(6-bromo-3-methylpyridin-2-ylcarbamoyl)-2-azabi-cyclo[3.1.0]hexane-2-carboxylate (229-S10)

To a solution of compound 229-S8 (210 mg, 0.71 mmol) and 6-bromo-3-methylpyridin-2-amine (133 mg, 0.71 mmol) in dry DCM (6 mL) was added pyridine (280 mg, 3.55 mmol) at 0° C. followed by the dropwise addition of $POCl_3$ (120 mg, 0.78 mmol). The reaction mixture was stirred at room temperature for 30 minutes and then quenched with ice-cooled water and extracted with DCM twice. The combined organic phases were washed with brine, dried over anhydrous $Na_2SO_4$, filtered and concentrated to dryness. The residue was purified by silica gel column (eluted with PE:EtOAc=12:1) to afford compound 229-S10 (150 mg, 67.2%) as a colorless oil. LC/MS (ESI) m/z: 466/468 (M+H)$^+$.

Step 6: (1R,3S,5S)-5-(Allyloxymethyl)-N-(6-bromo-3-methylpyridin-2-yl)-2-azabicyclo[3.1.0]hexane-3-carboxamide (229-S11)

To a solution of compound 229-S10 (150 mg, 0.32 mmol) in DCM (2 mL) was added TFA (2 mL) at room temperature under $N_2$ atmosphere. The resulting mixture was stirred at room temperature for 2 hours and the mixture was concentrated to afford compound 229-S11 (100 mg, 85.5%) as a colorless oil, which was directly used in the next reaction without additional purification. LC/MS (ESI) m/z: 366 (M+H)$^+$.

Step 7: (1R,3S,5S)-2-(2-(3-Acetyl-7-allyl-5-(2-methylpyrimidin-5-yl)-1H-indazol-1-yl)acetyl)-5-(allyloxymethyl)-N-(6-bromo-3-methylpyridin-2-yl)-2-azabicyclo[3.1.0]hexane-3-carboxamide (229)

To a solution of the compound 229-S11 (100 mg, 0.21 mmol), compound 229-S4 (73 mg, 0.21 mmol) and HATU (160 mg, 0.42 mmol) in DMF (2 mL) was added DIPEA (110 mg, 0.84 mmol). The reaction was stirred at room temperature for 16 hours. The mixture was diluted with EtOAc and washed with 10% aqueous LiCl solution and brine, dried, and concentrated to afford crude product, which was purified by silica gel column chromatography (eluted with DCM:MeOH=100:0 to 80:1) to afford compound 229 (130 mg, 88.4%) as a white solid. $^1$H-NMR (400 MHz, DMSO-$d_6$) δ 10.32 (s, 1H), 9.03 (s, 2H), 8.40 (d, J=1.7 Hz, 1H), 7.56-7.66 (m, 2H), 7.45 (d, J=7.9 Hz, 1H), 6.17-6.26 (m, 1H), 5.86-5.97 (m, 2H), 5.65 (d, J=17.5 Hz, 1H), 5.29 (dd, J=17.3, 1.9 Hz, 1H), 5.18 (t, J=9.9 Hz, 2H), 4.91 (d, J=17.1 Hz, 1H), 4.48 (dd, J=9.4, 5.1 Hz, 1H), 4.07 (dd, J=13.2, 5.4 Hz, 1H), 3.99 (dd, J=13.2, 5.3 Hz, 1H), 3.78-3.86 (m, 1H), 3.67-3.75 (m, 2H), 3.58 (d, J=10.6 Hz, 1H), 3.47 (d, J=10.7 Hz, 1H), 2.69 (s, 3H), 2.66 (s, 3H), 2.24-2.35 (m, 2H), 2.05 (s, 3H), 1.17-1.21 (m, 1H), 1.03-1.08 (m, 1H). LC/MS (ESI) m/z: 698/700 (M+H)$^+$.

Scheme 90: Synthesis of (2S,4R)-1-(2-(3-Acetyl-5-(2-((3-methyloxetan-3-yl)methylsulfonyl)ethoxy)-1H-indazol-1-yl)acetyl)-N-(6-bromo-3-methylpyridin-2-yl)-4-fluoropyrrolidine-2-carboxamide (230)

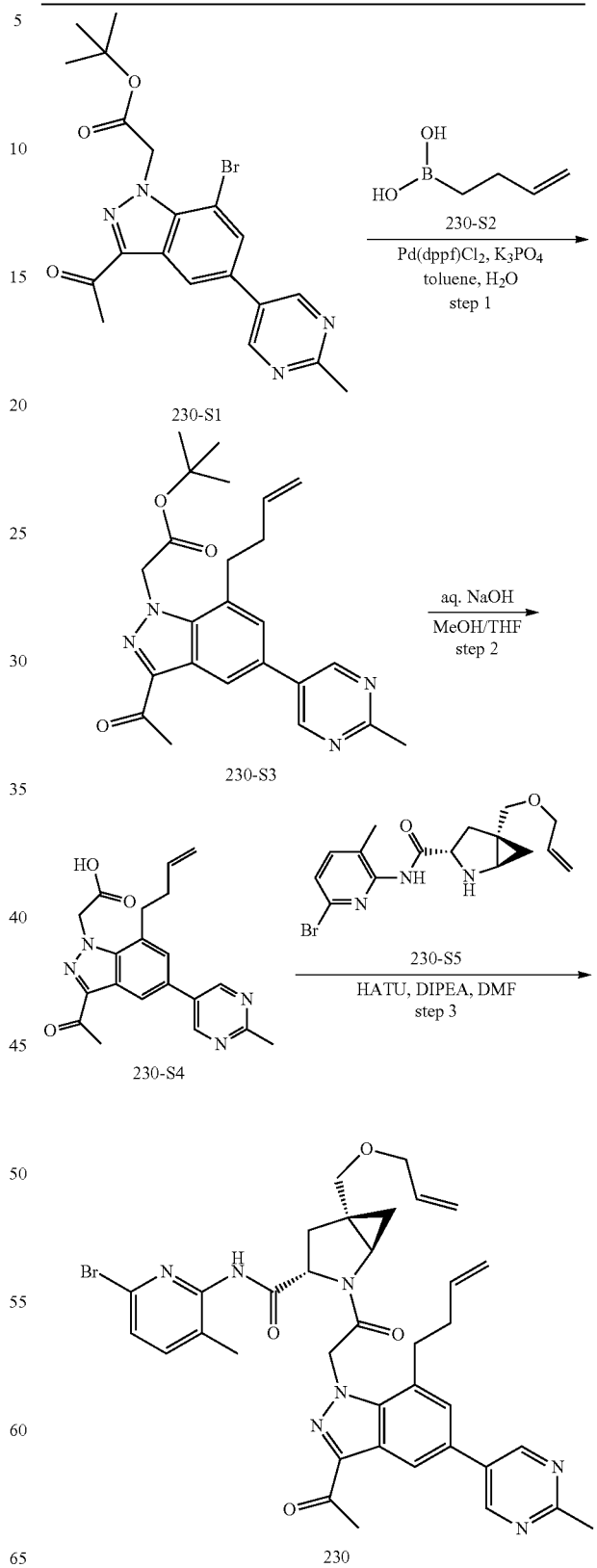

Step 1: tert-Butyl 2-(3-acetyl-7-(but-3-enyl)-5-(2-methylpyrimidin-5-yl)-1H-indazol-1-yl)acetate (230-3)

To a mixture of compound 230-S1 (444 mg, 1 mmol) and compound 230-S2 (200 ms, 2 mmol) in toluene (15 mL) and H$_2$O (3 mL) was added K$_3$PO$_4$ (637 mg, 3 mmol) followed by the addition of Pd(dppf)Cl$_2$ (74 mg, 0.1 mmol). The reaction was stirred at 100° C. for 16 hours under N$_2$ atmosphere before the mixture was cooled, diluted with EtOAc, and washed with water and brine. The organic layer was separated, dried and concentrated to afford crude product, which was purified by silica gel column (eluted with PE:acetone=20:1 to 12:1) to afford compound 230-S3 (354 mg, 84.1%) as a white solid. LC/MS (ESI) m/z: 421 (M+H)$^+$.

Step 2: 2-(3-Acetyl-7-allyl-5-(2-methylpyrimidin-5-yl)-1H-indazol-1-yl)acetic Acid (230-S4)

To a mixture of compound 230-S3 (354 mg, 0.843 mmol) in MeOH/THF (12 mL, 1:1) was added 3 mL of aqueous NaOH solution (101 mg, 2.53 mmol). The mixture was stirred at room temperature for 4 hours before the mixture was diluted with water (15 mL) and extracted with ether. The aqueous layer was collected and acidified with aqueous HCl solution (1 N) to a pH of approximately 5. The resulting mixture was extracted with DCM/MeOH (20 mL×2, 10:1, V/V). The combined organic phases were washed with brine, dried over anhydrous Na$_2$SO$_4$, filtered and concentrated to afford compound 230-S4 (280 mg, 90.9%) as a white solid. LC/MS (ESI) m/z: 365 (M+H)$^+$.

Step 3: (1R,3S,5S)-2-(2-(3-Acetyl-7-(but-3-enyl)-5-(2-methylpyrimidin-5-yl)-1H-indazol-1-yl)acetyl)-5-(allyloxymethyl)-N-(6-bromo-3-methylpyridin-2-yl)-2-azabicyclo[3.1.0]hexane-3-carboxamide (230)

To a solution of the compound 230-S4 (210 mg, 0.44 mmol), compound 230-S5 (160 mg, 0.44 mmol) and HATU (334 mg, 0.88 mmol) in DMF (4 mL) was added DIPEA (286 mg, 2.2 mmol). The reaction was stirred at room temperature for 16 hours. The mixture was diluted with EtOAc and washed with 10% aqueous LiCl solution and brine, dried, and concentrated to afford crude product, which was purified by silica gel column (eluted with DCM:MeOH=100:0 to 80:1) to afford compound 230 (250 mg, 79.9%) as a white solid. 1H-NMR (400 MHz, DMSO-d$_6$) δ 10.32 (d, J=8.1 Hz, 1H), 8.95-9.10 (m, 2H), 8.36-8.40 (m, 1H), 7.56-7.64 (m, 2H), 7.45 (d, J=7.9 Hz, 1H), 6.19-6.32 (m, 1H), 5.84-6.00 (m, 2H), 5.63-5.75 (m, 1H), 5.26-5.35 (m, 1H), 5.06-5.18 (m, 2H), 4.87-4.98 (m, 1H), 4.44-4.51 (m, 1H), 3.93-4.06 (m, 3H), 3.72-3.81 (m, 2H), 3.59 (d, J=10.5 Hz, 1H), 3.46-3.51 (m, 1H), 2.71 (s, 3H), 2.65 (s, 3H), 2.19-2.36 (m, 2H), 2.05 (s, 3H), 1.63-1.70 (m, 1H), 1.41-1.50 (m, 1H), 1.16-1.25 (m, 1H), 0.92-1.06 (m, 1H). LC/MS (ESI) m/z: 712/714 (M+H)$^+$.

Scheme 91. Synthesis of Methyl 1-{2-[(1R,3S,5R)-3-[(6-bromo-3-methylpyridin-2-yl)carbamoyl]-5-methyl-2-azabicyclo[3.1.0]hexan-2-yl]-2-oxoethyl}-5-(2-methylpyrimidin-5-yl)indazole-3-carboxylate (467), 1-{2-[(1R,3S,5R)-3-[(6-bromo-3-methylpyridin-2-yl)carbamoyl]-5-methyl-2-azabicyclo[3.1.0]hexan-2-yl]-2-oxoethyl}-5-(2-methylpyrimidin-5-yl)indazole-3-carboxylic acid (469), and Methyl 1-{2-[(1R,3S,5R)-3-[(6-bromo-3-methylpyridin-2-yl)carbamoyl]-5-methyl-2-azabicyclo[3.1.0]hexan-2-yl]-2-oxoethyl}-5-(2-methylpyrimidin-5-yl)indazole-3-carboxylate (474)

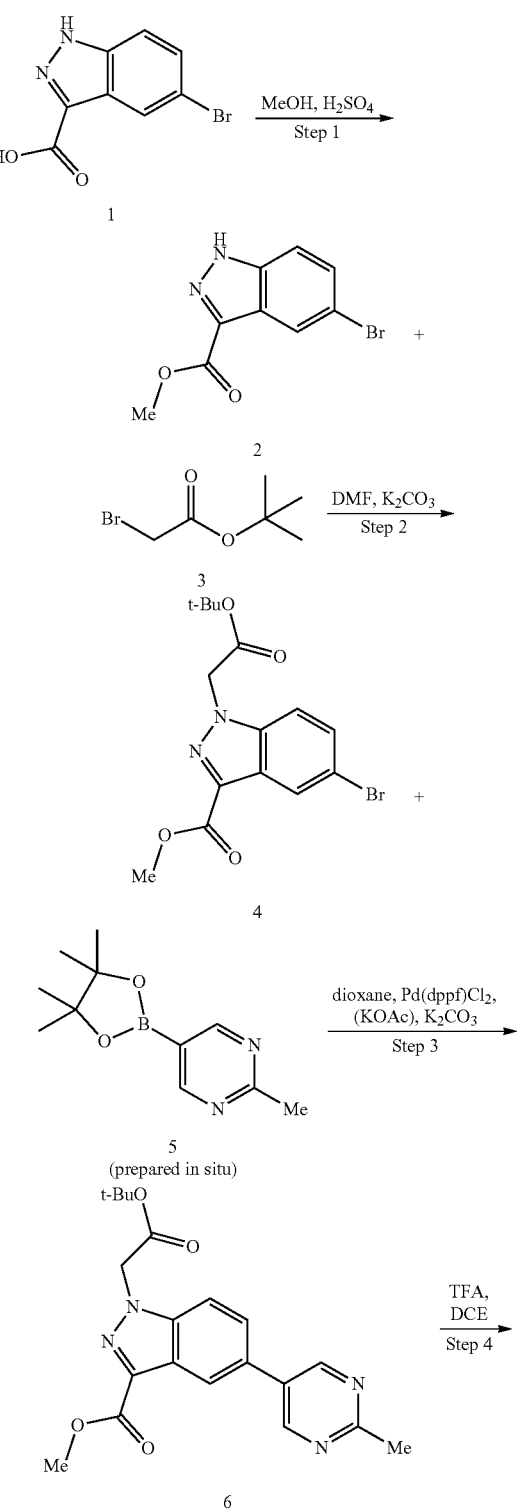

899
-continued

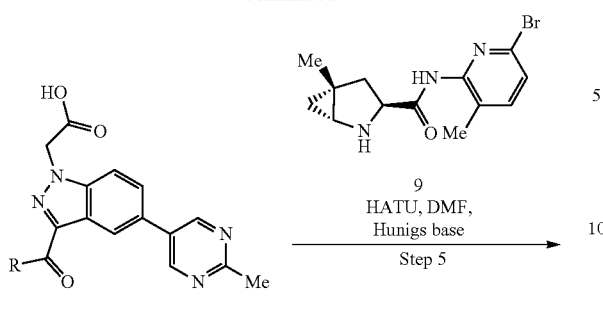

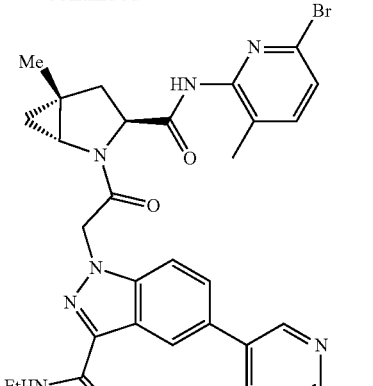

900
-continued

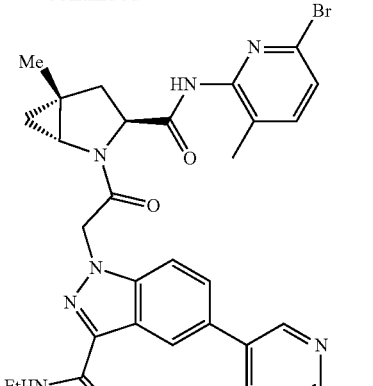

The above scheme and following detailed description depicts one non-limiting method for synthesizing compounds where the carboxylic acid in the $R^6$ position is functionalized via a coupling with an amine using HATU. The skilled artisan will recognize that ethylamine can be replaced with other amines to afford additional compounds of the present invention. Non-limiting examples of amines include methylamine, 2,2,2-trifluoroethylamine, isobutylamine, propylamine, butylamine, pentylamine, cyclopropylmethanamine, cyclobutylmethanamine, 2,2-dimethyl-1-propylamine, ethylenediamine, $N^1$-methylethane-1,2-diamine, (2-aminoethyl)dimethylamine, aminocyclopropane, isopropylamine, allylamine, propargylamine, 1-cyclopropylethanamine, 2-cyclopropylpropan-2-amine, 2-methylpent-3-yn-2-amine, and but-3-yn-2-amine.

Step 1: Methyl 5-bromo-1H-indazole-3-carboxylate (2)

To a stirring suspension of 5-bromo-1H-indazole-3-carboxylic acid (5.0 g, 21 mmol, 1 equiv.) in methanol (84 mL, 2.0 mol, 100 equiv.) was added sulfuric acid (10 g, 100 mmol, 5 equiv.). The mixture was heated to 60° C. and stirred overnight at which point the LCMS showed quantitative conversion to the desired product. The mixture was then concentrated to a residue that was taken up in EtOAc (20 mL) and washed with water (20 mL). The aqueous layer was neutralized with saturated sodium bicarbonate and then extracted with EtOAc (2×20 mL). The combined organic extracts were washed with saturated aqueous bicarbonate solution, brine, dried over NasSO4, filtered and concentrated to afford the desired product 2 as a tan solid which was used in the next step without purification.

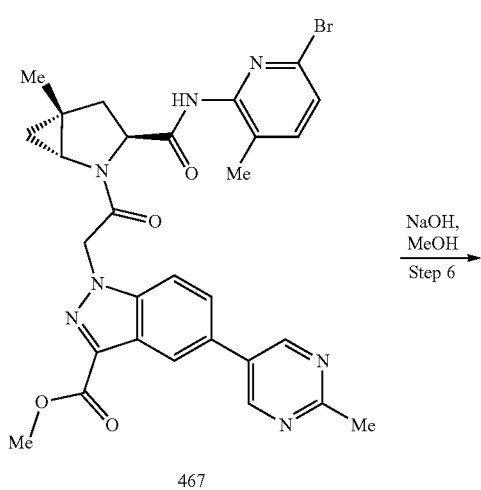

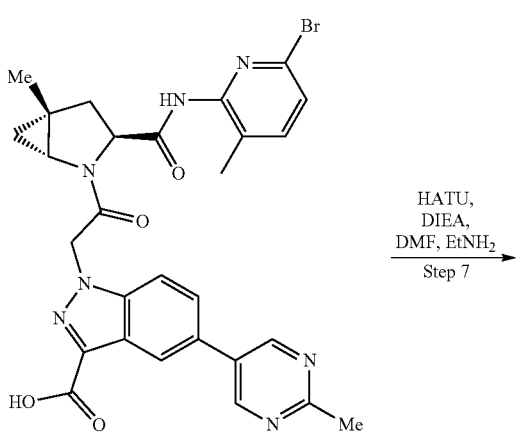

Step 2: Methyl 5-bromo-1-[2-(tert-butoxy)-2-oxo-ethyl]indazole-3-carboxylate (4)

To a solution of methyl 5-bromo-1H-indazole-3-carboxylate (0.60 g, 2.4 mmol, 1 equiv.) in dimethyl-formamide (23 mL, 0.1 M, 39 Vols) at room temperature were added tert-butyl 2-bromoacetate (0.51 g, 0.38 mL, 2.6 mmol, 1.1 equiv.) and potassium carbonate (0.36 g, 2.6 mmol, 1.1 equiv.). The mixture was stirred overnight at room temperature under an atmosphere of argon. The mixture was then concentrated, diluted with DCM, filtered through a pad of Celite and then purified by column chromatography on silica gel (eluted with a 0-100% EtOAc in hexanes gradient) to afford 4.

Step 3: Methyl 1-[2-(tert-butoxy)-2-oxoethyl]-5-(2-methylpyrimidin-5-yl)indazole-3-carboxylate (6)

5-Bromo-2-methylpyrimidine (250 mg, 1.44 mmol, 1 equiv.), bis(pinacolato)diboron (0.385 g, 1.52 mmol, 1.05 equiv.), potassium acetate (0.425 g, 4.34 mmol, 3 equiv.), and 1,1'-bis(diphenylphosphino)ferrocene-dichloropalladium (1:1) (0.106 g, 0.144 mmol, 0.1 equiv.) were combined in a sealed reaction vessel, evacuated and charged with Ar gas. The mixture was then diluted with 1,4-dioxane (5.0 mL, 0.29 M, 20 Vols) and heated to 90° C. for 3 hours at which point the LCMS showed conversion to the desired boronate. To this mixture was added potassium carbonate (0.665 g, 4.81 mmol, 3 equiv.) followed by methyl 5-bromo-1-[2-(tert-butoxy)-2-oxoethyl]indazole-3-carboxylate (0.592 g, 1.60 mmol, 1 equiv.) and water (0.3 mL). The orange mixture was allowed to stir at 100° C. for 2 hours at which point the LCMS showed conversion to a peak with a mass corresponding to the desired product. The mixture was diluted with EtOAc (20 mL) and washed with water. The aqueous layer was extracted once with EtOAc (20 mL). The organic extracts were washed with brine, dried over $Na_2SO_4$, filtered and concentrated to afford an orange solid. This solid was then purified on silica gel chromatography eluting with a 0-100% EtOAc in hexanes gradient over 15 CVs to afford 6 as a colorless solid.

Step 4: [3-(Methoxycarbonyl)-5-(2-methylpyrimidin-5-yl)indazol-1-yl]acetic Acid (7)

To a stirring solution of methyl 1-[2-(tert-butoxy)-2-oxoethyl]-5-(2-methylpyrimidin-5-yl)indazole-3-carboxylate (250 mg, 0.654 mmol, 1 equiv.) in 1,2-dichloroethane (6.54 mL, 0.1 M, 26 Vols) at room temperature was added trifluoroacetic acid (1.00 mL, 13.1 mmol, 20 equiv.). The solution was stirred at room temperature for 24 hours. The mixture was concentrated in vacuo azeotroping with toluene (2×15 mL) and DCM (2×15 mL) to afford 7 as a yellow solid. This material was carried on without further purification.

Alternatively, [3-(methoxycarbonyl)-5-(2-methylpyrimidin-5-yl)indazol-1-yl]acetic acid (7) was formed in the following manner: molecular iodine (14 g, 56 mmol, 3.5 equiv.) was taken up in methanol (160 mL, 0.1 M, 32 Vols) and [3-acetyl-5-(2-methylpyrimidin-5-yl)indazol-1-yl]acetic acid (5.0 g, 16 mmol, 1 equiv.) was added. Next, sodium methoxide (5.0 g, 97 mmol, 6 equiv.) was added as a solution in MeOH (30 mL). The resulting slurry was vigorously stirred at room temperature for 1 hour. The mixture was concentrated and then taken up in a 3:1 mixture of acetonitrile and 2-propanol (100 mL). The mixture was acidified with 1M HCl and the layers were separated. The aqueous layer was extracted with a 3:1 mixture of acetonitrile and 2-propanol (2×30 mL). The combined organic extracts were washed with water, brine, dried over $Na_2SO_4$, filtered and concentrated to afford the desired product 7 as a tan solid. This material was carried on without further purification.

Step 5: Methyl 1-{2-[(1R,3S,5R)-3-[(6-bromo-3-methylpyridin-2-yl)carbamoyl]-5-methyl-2-azabicyclo[3.1.0]hexan-2-yl]-2-oxoethyl}-5-(2-methylpyrimidin-5-yl)indazole-3-carboxylate (467)

To a stirring solution of [3-(methoxycarbonyl)-5-(2-methylpyrimidin-5-yl)indazol-1-yl]acetic acid (0.019 g, 0.058 mmol, 1 equiv.) and (1R,3S,5R)—N-(6-bromo-3-methylpyridin-2-yl)-5-methyl-2-azabicyclo[3.1.0]hexane-3-carboxamide (0.022 g, 0.070 mmol, 1.2 equiv.) in dimethylformamide (0.58 mL, 0.1 M, 30 Vols) was added successively (2-(7-aza-1H-benzotriazol-1-yl)-1,1,3,3-tetramethyluronium hexafluorophosphate) (0.055 g, 0.15 mmol, 2.5 equiv.) followed by diisopropylethylamine (0.023 g, 0.18 mmol, 3 equiv.). The mixture was stirred at room temperature for 30 minutes at which point LCMS showed quantitative conversion to a peak corresponding to the desired product. The reaction solution was purified directly via reverse phase HPLC and concentrated to afford methyl 1-{2-[(1R,3S,5R)-3-[(6-bromo-3-methylpyridin-2-yl)carbamoyl]-5-methyl-2-azabicyclo[3.1.0]hexan-2-yl]-2-oxoethyl}-5-(2-methylpyrimidin-5-yl)indazole-3-carboxylate (467) as a white film. $^1$H NMR (400 MHz, DMSO-$d_6$) δ 10.25 (s, 1H), 9.06 (s, 2H), 8.35 (s, 1H), 7.86 (s, 2H), 7.62 (d, J=7.9 Hz, 1H), 7.44 (d, J=7.9 Hz, 1H), 5.89 (d, J=17.2 Hz, 1H), 5.57 (d, J=17.2 Hz, 1H), 4.40 (dd, J=9.3, 5.1 Hz, 1H), 3.96 (s, 3H), 3.56 (t, J=4.0 Hz, 1H), 2.69 (s, 3H), 2.09-1.99 (m, 1H), 2.04 (s, 3H), 1.32 (s, 3H), 1.30-1.22 (m, 1H), 1.00 (d, J=4.6 Hz, 2H).

Step 6: 1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-5-(2-methylpyrimidin-5-yl)indazole-3-carboxylic Acid (469)

Sodium hydroxide (0.23 mL, 0.23 mmol, 10 equiv.) (1M aq) was added to a stirring suspension of methyl 1-{2-[(1R,3S,5R)-3-[(6-bromo-3-methylpyridin-2-yl)carbamoyl]-5-methyl-2-azabicyclo[3.1.0]hexan-2-yl]-2-oxoethyl}-5-(2-methylpyrimidin-5-yl)indazole-3-carboxylate (15 mg, 0.023 mmol, 1 equiv.) in methanol (1.0 mL, 0.023 M, 69 Vols) at room temperature. The mixture was stirred at room temperature for 2 hours, after which time the mixture had become a solution and LCMS showed no starting material. The solution was directly purified by reverse phase HPLC to afford 1-{2-[(1R,3S,5R)-3-[(6-bromo-3-methylpyridin-2-yl)carbamoyl]-5-methyl-2-azabicyclo[3.1.0]hexan-2-yl]-2-oxoethyl}-5-(2-methylpyrimidin-5-yl)indazole-3-carboxylic acid (469) as a white solid. $^1$H NMR (400 MHz, DMSO-$d_6$) δ 13.18 (s, 1H), 10.26 (s, 1H), 9.05 (s, 2H), 8.34 (d, J=1.2 Hz, 1H), 7.84 (s, 2H), 7.63 (d, J=8.0 Hz, 1H), 7.45 (d, J=7.9 Hz, 1H), 5.88 (d, J=17.2 Hz, 1H), 5.55 (d, J=17.2 Hz, 1H), 4.41 (dd, J=9.2, 5.1 Hz, 1H), 3.57 (t, J=4.0 Hz, 1H), 2.69 (s, 3H), 2.60-2.51 (m, 1H), 2.05 (dd, J=17.6, 4.2 Hz, 1H), 2.05 (s, 3H), 1.33 (s, 3H), 1.01 (d, J=4.1 Hz, 2H).

Step 7: 1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-N-ethyl-5-(2-methylpyrimidin-5-yl)indazole-3-carboxamide (474)

To a stirring solution of 1-{2-[(1R,3S,5R)-3-[(6-bromo-3-methylpyridin-2-yl)carbamoyl]-5-methyl-2-azabicyclo[3.1.0]hexan-2-yl]-2-oxoethyl}-5-(2-methylpyrimidin-5-yl)indazole-3-carboxylic acid (21 mg, 0.035 mmol) in dimethyl-formamide (1.5 mL) was added 1-[bis(dimethylamino)methylene]-1H-1,2,3-triazolo[4,5-b]pyridinium 3-oxid hexafluorophosphate N-oxide (0.026 g, 0.069 mmol) and diisopropylethylamine (0.024 mL, 0.139 mmol). The mixture was stirred at room temperature for 15 minutes and then ethylamine (0.17 mL, 0.35 mmol) was added. The mixture was stirred at room temperature for an additional 2 hours at which point the LCMS showed conversion to a peak with the desired mass. The solution was filtered and directly purified via reverse phase HPLC to afford 1-{2-[(1R,3S,5R)-3-[(6-bromo-3-methylpyridin-2-yl)carbamoyl]-5-methyl-2-azabicyclo[3.1.0]hexan-2-yl]-2-oxoethyl}-N-ethyl-5-(2-methylpyrimidin-5-yl)indazole-3-carboxamide (10 mg, 0.016 mmol, yield 46%) as a white solid. $^1$H NMR (400 MHz, Methanol-d4) δ 9.04 (s, 2H), 8.56 (s, 1H), 7.84-7.73 (m, 2H), 7.57 (d, J=8.0 Hz, 1H), 7.40 (d, J=8.0 Hz, 1H), 5.73 (d, J=17.2 Hz, 1H), 5.63 (d, J=17.1 Hz, 1H), 4.55 (dd, J=9.3, 5.3 Hz, 1H), 3.51 (dt, J=14.4, 6.3 Hz, 3H), 2.77 (s, 3H), 2.67 (s, 1H), 2.67-2.57 (m, 1H), 2.33 (dd, J=13.4, 5.1 Hz, 1H), 2.16 (d, J=13.7 Hz, 3H), 1.42 (s, 3H), 1.28 (t, J=7.2 Hz, 3H), 1.07 (t, J=5.5 Hz, 1H), 0.95 (dd, J=5.5, 2.5 Hz, 1H).

1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-N-methyl-5-(2-methylpyrimidin-5-yl)indazole-3-carboxamide $^1$H NMR (400 MHz, Methanol-d4) δ 9.04 (s, 2H), 8.57 (s, 1H), 8.47 (s, 3H), 7.79 (q, J=8.7 Hz, 2H), 7.57 (d, J=8.0 Hz, 1H), 7.41 (d, J=7.9 Hz, 1H), 5.72 (d, J=17.1 Hz, 1H), 5.63 (d, J=17.1 Hz, 1H), 4.55 (s, 1H), 3.53 (s, 1H), 3.00 (s, 3H), 2.77 (s, 3H), 2.37-2.29 (m, 1H), 2.14 (s, 3H), 1.41 (s, 3H), 1.25 (m, 1H), 1.07 (s, 1H), 0.94 (s, 1H).

1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-N-methyl-5-(2-methylpyrimidin-5-yl)indazole-3-carboxamide $^1$H NMR (400 MHz, Methanol-d4) δ 9.04 (s, 2H), 8.56 (s, 1H), 7.86-7.75 (m, 2H), 7.56 (d, J=7.9 Hz, 1H), 7.40 (d, J=8.0 Hz, 1H), 5.76 (d, J=17.0 Hz, 1H), 5.66 (d, J=17.1 Hz, 1H), 4.55 (t, J=7.2 Hz, 1H), 4.14 (dd, J=13.7, 6.1 Hz, 2H), 3.54 (s, 1H), 2.77 (s, 3H), 2.70-2.54 (m, 2H), 2.38-2.28 (m, 1H), 2.14 (s, 3H), 1.42 (s, 3H), 1.07 (t, J=5.7 Hz, 1H), 0.96 (s, 1H).

1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-N-(2-methylpropyl)-5-(2-methylpyrimidin-5-yl)indazole-3-carboxamide $^1$H NMR (400 MHz, Methanol-d4) δ 9.03 (s, 2H), 8.55 (d, J=1.4 Hz, 1H), 8.41 (t, J=6.3 Hz, 1H), 7.82-7.72 (m, 2H), 7.56 (d, J=7.9 Hz, 1H), 7.39 (d, J=7.9 Hz, 1H), 5.73 (d, J=17.1 Hz, 1H), 5.62 (d, J=17.2 Hz, 1H), 4.55 (dd, J=9.3, 5.2 Hz, 1H), 3.53 (dd, J=5.6, 2.4 Hz, 1H), 3.29 (t, J=6.4 Hz, 2H), 2.77 (s, 3H), 2.70-2.57 (m, 1H), 2.32 (dd, J=13.5, 5.2 Hz, 1H), 2.13 (s, 3H), 1.97 (hept, J=6.7 Hz, 1H), 1.41 (s, 3H), 1.11-0.98 (m, 7H), 0.95 (dd, J=5.5, 2.4 Hz, 1H).

1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-5-(2-methylpyrimidin-5-yl)-N-propylindazole-3-carboxamide $^1$H NMR (400 MHz, Methanol-d4) δ 9.04 (s, 2H), 8.56 (s, 1H), 8.45 (d, J=5.9 Hz, 1H), 8.30 (s, 1H), 7.84-7.73 (m, 2H), 7.57 (d, J=8.0 Hz, 1H), 7.41 (d, J=7.9 Hz, 1H), 5.73 (d, J=17.1 Hz, 1H), 5.63 (d, J=17.1 Hz, 1H), 4.55 (dd, J=9.2, 5.3 Hz, 1H), 3.57-3.50 (m, 1H), 3.48-3.34 (m, 2H), 2.77 (s, 3H), 2.70-2.57 (m, 2H), 2.33 (dd, J=13.7, 5.1 Hz, 1H), 2.14 (s, 3H), 1.70 (h, J=7.3 Hz, 2H), 1.41 (s, 3H), 1.11-0.92 (m, 5H).

1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-N-butyl-5-(2-methylpyrimidin-5-yl)indazole-3-carboxamide $^1$H NMR (400 MHz, Methanol-d4) δ 9.04 (s, 2H), 8.56 (s, 1H), 8.41 (t, J=5.9 Hz, 1H), 8.24 (s, 1H), 7.84-7.73 (m, 2H), 7.57 (d, J=7.9 Hz, 1H), 7.40 (d, J=7.9 Hz, 1H), 5.73 (d, J=17.1 Hz, 1H), 5.63 (d, J=17.1 Hz, 1H), 4.55 (dd, J=9.3, 5.2 Hz, 1H), 3.57-3.42 (m, 3H), 3.23 (dt, J=34.7, 6.7 Hz, 1H), 2.77 (s, 3H), 2.74-2.57 (m, 2H), 2.38-2.28 (m, 1H), 2.14 (s, 3H), 1.66 (p, J=7.3 Hz, 2H), 1.60-1.49 (m, 1H), 1.41 (m, 3H), 1.11-0.90 (m, 6H).

1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-5-(2-methylpyrimidin-5-yl)-N-pentylindazole-3-carboxamide $^1$H NMR (400 MHz, Methanol-d4) δ 9.04 (s, 2H), 8.56 (s, 1H), 8.42 (s, 1H), 8.28 (s, 1H), 7.84-7.73 (m, 2H), 7.57 (d, J=8.0 Hz, 1H), 7.40 (d, J=8.0 Hz, 1H), 5.73 (d, J=17.1 Hz, 1H), 5.63 (d, J=17.1 Hz, 1H), 4.55 (dd, J=9.3, 5.2 Hz, 1H), 3.56-3.50 (m, 1H), 3.46 (q, J=6.5 Hz, 2H), 2.77 (s, 3H), 2.70-2.57 (m, 2H), 2.33 (dd, J=13.8, 5.2 Hz, 1H), 2.14 (s, 3H), 1.68 (s, 2H), 1.42 (d, J=5.2 Hz, 2H), 1.41 (s, 3H), 1.35 (s, 1H), 1.07 (t, J=5.6 Hz, 1H), 1.00-0.92 (m, 4H).

1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-N-(cyclopropylmethyl)-5-(2-methylpyrimidin-5-yl)indazole-3-carboxamide $^1$H NMR (400 MHz, Methanol-d4) δ 9.04 (s, 2H), 8.56 (s, 1H), 8.46 (t, J=6.0 Hz, 1H), 8.23 (s, 1H), 7.84-7.73 (m, 2H), 7.56 (d, J=8.0 Hz, 1H), 7.40 (d, J=7.9 Hz, 1H), 5.74 (d, J=17.2 Hz, 1H), 5.63 (d, J=17.1 Hz, 1H), 4.56 (dd, J=9.4, 5.2 Hz, 1H), 3.54 (dd, J=5.7, 2.4 Hz, 1H), 3.36 (d, J=5.7 Hz, 1H), 2.77 (s, 3H), 2.70-2.57 (m, 2H), 2.33 (dd, J=13.6, 5.2 Hz, 1H), 2.14 (s, 3H), 1.42 (s, 3H), 1.15 (q, J=6.4, 5.4 Hz, 1H), 1.08 (t, J=5.6 Hz, 1H), 0.96 (dd, J=5.6, 2.4 Hz, 1H), 0.61-0.51 (m, 2H), 0.34 (q, J=5.1 Hz, 2H).

1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-N-(cyclobutylmethyl)-5-(2-methylpyrimidin-5-yl)indazole-3-carboxamide $^1$H NMR (400 MHz, Methanol-d4) δ 9.04 (s, 2H), 8.55 (d, J=1.5 Hz, 1H), 8.37 (dd, J=12.1, 6.1 Hz, 1H), 7.83-7.72 (m, 2H), 7.56 (d, J=8.0 Hz, 1H), 7.40 (d, J=8.0 Hz, 1H), 5.73 (d, J=17.1 Hz, 1H), 5.62 (d, J=17.1 Hz, 1H), 4.55 (dd, J=9.2, 5.2 Hz, 1H), 3.57-3.45 (m, 3H), 2.77 (s, 3H), 2.74-2.57 (m, 2H), 2.32 (dd, J=13.6, 5.2 Hz, 1H), 2.13 (s, 3H), 2.19-2.06 (m, 2H), 2.02-1.78 (m, 4H), 1.41 (s, 3H), 1.07 (t, J=5.7 Hz, 1H), 0.95 (dd, J=5.6, 2.4 Hz, 1H).

1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-N-(2,2-dimethylpropyl)-5-(2-methylpyrimidin-5-yl)indazole-3-carboxamide $^1$H NMR (400 MHz, Methanol-d4) δ 9.04 (s, 2H), 8.58-8.48 (m, 1H), 8.23 (t, J=6.6 Hz, 1H), 7.84-7.73 (m, 2H), 7.56 (d, J=8.0 Hz, 1H), 7.40 (d, J=7.9 Hz, 1H), 5.75 (d, J=17.2 Hz, 1H), 5.64 (d, J=17.2 Hz, 1H), 4.56 (dd, J=9.3, 5.3 Hz, 1H), 3.54 (dd, J=5.6, 2.4 Hz, 1H), 3.30 (d, J=5.5 Hz, 2H), 2.77 (s, 3H), 2.70-2.57 (m, 1H), 2.33 (dd, J=13.7, 5.3 Hz, 1H), 2.13 (s, 3H), 1.41 (s, 3H), 1.38 (s, 1H), 1.02 (s, 8H), 1.00-0.90 (m, 2H).

N-(2-aminoethyl)-1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-5-(2-methylpyrimidin-5-yl)indazole-3-carboxamide $^1$H NMR (400 MHz, Methanol-d4) δ 9.04 (s, 2H), 8.58 (s, 1H), 8.49 (s, 2H), 7.88-7.76 (m, 2H), 7.57 (d, J=7.9 Hz, 1H), 7.40 (d, J=7.9 Hz, 1H), 5.77 (d, J=17.3 Hz, 1H), 5.64 (d, J=17.2 Hz, 1H), 4.60-4.51 (m, 1H), 3.74 (t, J=5.6 Hz, 2H), 3.59-3.52 (m, 1H), 3.22 (t, J=5.8 Hz, 2H), 2.78 (s, 3H), 2.74-2.59 (m, 4H), 2.32 (dd, J=13.4, 5.4 Hz, 1H), 2.15 (s, 3H), 1.43 (s, 3H), 1.12 (t, J=5.5 Hz, 1H), 1.00-0.91 (m, 1H).

1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-N-[2-(methylamino)ethyl]-5-(2-methylpyrimidin-5-yl)indazole-3-carboxamide $^1$H NMR (400 MHz, Methanol-d4) δ 9.03 (s, 2H), 8.57 (s, 1H), 8.43 (s, 2H), 7.87-7.76 (m, 2H), 7.57 (d, J=7.9 Hz, 1H), 7.40 (d, J=7.9 Hz, 1H), 5.77 (d, J=17.2 Hz, 1H), 5.64 (d, J=17.2 Hz, 1H), 4.55 (dd, J=9.1, 5.3 Hz, 1H), 3.77 (t, J=5.5 Hz, 2H), 3.59-3.52 (m, 1H), 3.29 (t, J=5.5 Hz, 2H), 2.78 (d, J=4.1 Hz, 6H), 2.74-2.57 (m, 2H), 2.32 (dd, J=13.5, 5.4 Hz, 1H), 2.15 (s, 3H), 1.42 (s, 3H), 1.12 (t, J=5.6 Hz, 1H), 0.97 (dd, J=5.6, 2.4 Hz, 1H).

1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-N-[2-(dimethylamino)ethyl]-5-(2-methylpyrimidin-5-yl)indazole-3-carboxamide $^1$H NMR (400 MHz, Methanol-d4) δ 9.04 (s, 2H), 8.57 (s, 1H), 8.44 (s, 2H), 7.86-7.75 (m, 2H), 7.57 (d, J=7.9 Hz, 1H), 7.40 (d, J=8.0 Hz, 1H), 5.77 (d, J=17.2 Hz, 1H), 5.64 (d, J=17.2 Hz, 1H), 4.55 (dd, J=9.1, 5.2 Hz, 1H), 3.81 (t, J=5.9 Hz, 2H), 3.55 (dd, J=5.8, 2.3 Hz, 1H), 3.30 (d, J=5.7 Hz, 2H), 2.92 (s, 6H), 2.78 (s, 3H), 2.74-2.59 (m, 2H), 2.32 (dd, J=13.6, 5.2 Hz, 1H), 2.15 (s, 3H), 1.42 (s, 3H), 1.11 (t, J=5.5 Hz, 1H), 0.97 (dd, J=5.5, 2.4 Hz, 1H).

1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-N-cyclopropyl-5-(2-methylpyrimidin-5-yl)indazole-3-carboxamide $^1$H NMR (400 MHz, DMSO-d$_6$) δ 10.24 (s, 1H), 9.03 (s, 2H), 8.45 (d, J=4.6 Hz, 2H), 7.86-7.73 (m, 2H), 7.62 (d, J=7.9 Hz, 1H), 7.44 (d, J=7.9 Hz, 1H), 5.80 (d, J=17.4 Hz, 1H), 5.75 (s, 1H), 5.47 (d, J=17.4 Hz, 1H), 4.38 (dd, J=9.2, 5.3 Hz, 1H), 3.55 (dd, J=5.5, 2.4 Hz, 1H), 2.91 (td, J=11.2, 4.4 Hz, 1H), 2.69 (s, 3H), 2.54 (dd, J=9.6, 3.7 Hz, 1H), 2.05 (d, J=13.6 Hz, 4H), 1.32 (s, 3H), 1.04-0.91 (m, 2H), 0.68 (tt, J=7.1, 2.2 Hz, 4H).

1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-N-isopropyl-5-(2-methylpyrimidin-5-yl)indazole-3-carboxamide $^1$H NMR (400 MHz, DMSO-d$_6$) δ 10.25 (s, 1H), 9.04 (s, 2H), 8.46 (d, J=1.5 Hz, 1H), 8.10 (d, J=8.3 Hz, 1H), 7.89-7.75 (m, 2H), 7.63 (d, J=7.9 Hz, 1H), 7.45 (d, J=7.9 Hz, 1H), 5.83 (d, J=17.4 Hz, 1H), 5.76 (s, 0H), 5.50 (d, J=17.3 Hz, 1H), 4.40 (dd, J=9.3, 5.2 Hz, 1H), 4.19 (dt, J=13.5, 6.7 Hz, 1H), 3.56 (dd, J=5.6, 2.4 Hz, 1H), 2.69 (s, 3H), 2.60-2.51 (m, 1H), 2.06 (d, J=12.4 Hz, 4H), 1.33 (s, 3H), 1.22 (dd, J=6.6, 1.4 Hz, 6H), 1.06-0.94 (m, 2H).

1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-5-(2-methylpyrimidin-5-yl)-N-(prop-2-en-1-yl)indazole-3-carboxamide $^1$H NMR (400 MHz, DMSO-d$_6$) δ 10.25 (s, 1H), 9.04 (s, 2H), 8.56 (t, J=6.0 Hz, 1H), 8.46 (d, J=1.5 Hz, 1H), 7.89-7.76 (m, 2H), 7.63 (d, J=7.9 Hz, 1H), 7.45 (d, J=7.9 Hz, 1H), 6.00-5.73 (m, 2H), 5.51 (d, J=17.3 Hz, 1H), 5.19 (dt, J=17.2, 1.8 Hz, 1H), 5.09 (dd, J=10.2, 1.7 Hz, 1H), 4.41 (dd, J=9.2, 5.1 Hz, 1H), 3.99-3.91 (m, 2H), 3.57 (dd, J=5.5, 2.4 Hz, 1H), 2.69 (s, 3H), 2.55 (dd, J=9.2, 4.3 Hz, 1H), 2.05 (s, 3H), 1.33 (s, 3H), 1.05-0.93 (m, 2H).

1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-5-(2-methylpyrimidin-5-yl)-N-(prop-2-yn-1-yl)indazole-3-carboxamide $^1$H NMR (400 MHz, DMSO-d$_6$) δ 10.25 (s, 1H), 9.05 (s, 2H), 8.81 (t, J=6.0 Hz, 1H), 8.46 (d, J=1.5 Hz, 1H), 7.89-7.77 (m, 2H), 7.63 (d, J=8.0 Hz, 1H), 7.45 (d, J=7.9 Hz, 1H), 5.84 (d, J=17.3 Hz, 1H), 5.51 (d, J=17.2 Hz, 1H), 4.41 (dd, J=9.2, 5.2 Hz, 1H), 4.08 (dt, J=5.5, 2.5 Hz, 2H), 3.58 (dd, J=5.5, 2.4 Hz, 1H), 3.08 (t, J=2.5 Hz, 1H), 2.69 (s, 3H), 2.60-2.51 (m, 1H), 2.05 (s, 3H), 2.10-1.96 (m, 1H), 1.33 (s, 3H), 1.05-0.93 (m, 2H).

1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-N-(1-cyclopropylethyl)-5-(2-methylpyrimidin-5-yl)indazole-3-carboxamide $^1$H NMR (400 MHz, DMSO-d$_6$) δ 10.26 (s, 1H), 9.05 (s, 2H), 8.47 (d, J=1.4 Hz, 1H), 8.23 (dd, J=8.7, 2.0 Hz, 1H), 7.88-7.75 (m, 2H), 7.64 (d, J=8.0 Hz, 1H), 7.46 (d, J=7.9 Hz, 1H), 5.86 (dd, J=17.5, 3.7 Hz, 1H), 5.77 (s, 0H), 5.52 (dd, J=17.3, 3.9 Hz, 1H), 4.42 (dd, J=9.3, 5.2 Hz, 1H), 3.58 (dd, J=5.6, 2.4 Hz, 1H), 3.50 (q, J=8.1 Hz, 1H), 2.70 (s, 3H), 2.61-2.53 (m, 1H), 2.08 (s, 3H), 2.01 (m, 1H), 1.31, (s, 3H), 1.32-1.25 (m, 3H), 1.26-1.08 (m, 1H), 1.08-0.96 (m, 2H), 0.49 (m, 1H), 0.41 (m, 1H), 0.29 (ddt, J=29.4, 9.4, 4.5 Hz, 2H).

1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-N-(2-methylbut-3-yn-2-yl)-5-(2-methylpyrimidin-5-yl)indazole-3-carboxamide $^1$H NMR (400 MHz, DMSO-d$_6$) δ 10.25 (s, 1H), 9.06 (s, 2H), 8.46 (d, J=1.5 Hz, 1H), 7.92 (s, 1H), 7.89-7.75 (m, 2H), 7.63 (d, J=8.0 Hz, 1H), 7.45 (d, J=7.9 Hz, 1H), 5.85 (d, J=17.3 Hz, 1H), 5.51 (d, J=17.2 Hz, 1H), 4.40 (dd, J=9.2, 5.1 Hz, 1H), 3.57 (dd, J=5.3, 2.6 Hz, 1H), 3.19 (s, 1H), 2.70 (s, 3H), 2.60-2.51 (m, 1H), 2.05 (s, 3H), 2.00 (m, 1H), 1.68 (s, 6H), 1.33 (s, 3H), 1.06-0.96 (m, 2H).

1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-N-(2-cyclopropylpropan-2-yl)-5-(2-methylpyrimidin-5-yl)indazole-3-carboxamide $^1$H NMR (400 MHz, DMSO-d$_6$) δ 10.26 (s, 1H), 9.05 (s, 2H), 8.46 (d, J=1.5 Hz, 1H), 7.87-7.76 (m, 2H), 7.63 (d, J=7.9 Hz, 1H), 7.45 (d, J=7.9 Hz, 1H), 7.25 (s, 1H), 5.84 (d, J=17.3 Hz, 1H), 5.51 (d, J=17.3 Hz, 1H), 4.40 (dd, J=9.2, 5.1 Hz, 1H), 3.58 (t, J=4.0 Hz, 1H), 3.18 (d, J=4.7 Hz, 1H), 2.69 (s, 3H), 2.60-2.51 (m, 1H), 2.06 (m, 1H), 2.05 (s, 3H), 1.46 (dq, J=10.8, 6.2 Hz, 1H), 1.36 (s, 3H), 1.34 (s, 3H), 1.02 (d, J=4.0 Hz, 2H), 0.45-0.37 (m, 4H).

1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-5-(2-methylpyrimidin-5-yl)-N-(sec-butyl)indazole-3-carboxamide $^1$H NMR (400 MHz, DMSO-d$_6$) δ 10.25 (s, 1H), 9.04 (s, 2H), 8.46 (t, J=1.2 Hz, 1H), 8.05 (d, J=8.8 Hz, 1H), 7.87-7.75 (m, 2H), 7.63 (d, J=8.0 Hz, 1H), 7.45 (d, J=7.9 Hz, 1H), 5.84 (d, J=17.4 Hz, 1H), 5.50 (d, J=17.3 Hz, 1H), 4.40 (dd, J=9.3, 5.2 Hz, 1H), 4.01 (p, J=7.1 Hz, 1H), 3.57 (d, J=5.0 Hz, 1H), 2.69 (s, 3H), 2.60-2.51 (m, 1H), 2.06 (m, 1H), 2.05 (s, 3H), 1.33 (s, 3H), 1.32-1.21 (m, 1H), 1.19 (dd, J=6.7, 1.7 Hz, 3H), 1.06-0.95 (m, 2H), 0.89 (td, J=7.4, 2.2 Hz, 3H).

1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-N-tert-butyl-5-(2-methylpyrimidin-5-yl)indazole-3-carboxamide $^1$H NMR (400 MHz, DMSO-d$_6$) δ 10.25 (s, 1H), 9.05 (s, 2H), 8.46 (t, J=1.2 Hz, 1H), 7.87-7.75 (m, 2H), 7.63 (d, J=8.0 Hz, 1H), 7.45 (d, J=7.9 Hz, 1H), 7.39 (s, 1H), 5.83 (d, J=17.4 Hz, 1H), 5.50 (d, J=17.3 Hz, 1H), 4.40 (dd, J=9.3, 5.1 Hz, 1H), 3.61-3.54 (m, 1H), 2.69 (s, 3H), 2.60-2.51 (m, 1H), 2.06 (m, 1H), 2.05 (s, 3H), 1.45 (s, 9H), 1.33 (s, 3H), 1.05-0.98 (m, 2H).

1-{2-[(1R,3S,5R)-3-[(6-Bromo-3-methylpyridin-2-yl)carbamoyl]-5-methyl-2-azabicyclo[3.1.0]hexan-2-yl]-2-oxoethyl}-N-(but-3-yn-2-yl)-5-(2-methylpyrimidin-5-yl)indazole-3-carboxamide $^1$H NMR (400 MHz, DMSO-d$_6$) δ 10.25 (s, 1H), 9.04 (s, 2H), 8.73 (d, J=8.3 Hz, 1H), 8.45 (s, 1H), 7.89-7.77 (m, 2H), 7.63 (d, J=7.9 Hz, 1H), 7.45 (d, J=7.9 Hz, 1H), 5.85 (d, J=17.7 Hz, 1H), 5.52 (d, J=17.7 Hz, 1H), 4.92 (t, J=7.6 Hz, 1H), 4.45-4.36 (m, 1H), 3.57 (dd, J=5.4, 2.4 Hz, 1H), 3.21-3.13 (m, 1H), 2.69 (s, 3H), 2.60-2.51 (m, 1H), 2.06 (m, 1H), 2.05 (s, 3H), 1.46 (dd, J=7.0, 2.4 Hz, 3H), 1.33 (s, 3H), 1.06-0.95 (m, 2H).

Scheme 92. Synthesis of (1R,3S,5R)-2-{2-[3-Acetyl-7-methyl-5-(2-methylpyrimidin-5-yl)indazol-1-yl]acetyl}-N-ethyl-5-methyl-2-azabicyclo[3.1.0]hexane-3-carboxamide (506)

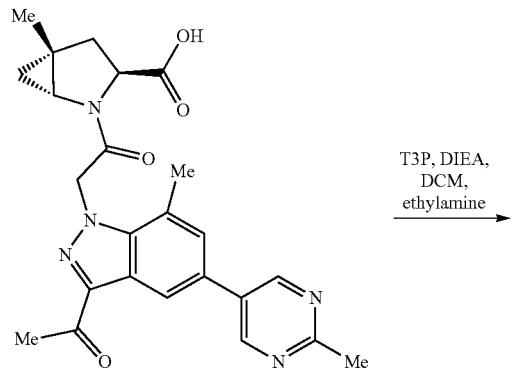

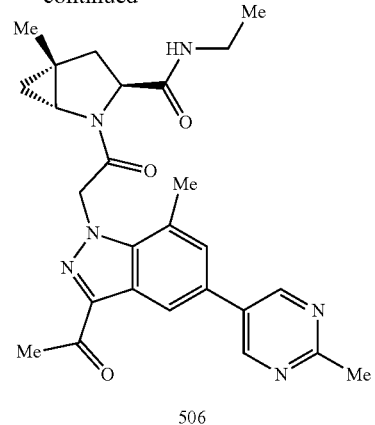

The above scheme and following detailed description depicts one non-limiting method for synthesizing compounds where the carboxylic acid on the C-ring is functionalized via a coupling with an amine using propane phosphonic acid anhydride (T3P). The skilled artisan will recognize that ethylamine can be replaced with other amines to afford additional compounds of the present invention. Non-limiting examples of amines include propylamine, butylamine, arylamine, cyclopropylmethanamine, 2,2-dimethyl-1-propylamine, isobutylamine, methylamine, 1,3-propanediamine, dimethylaminopropylamine, amylamine, benzyl amine, hexylamine, heptylamine, octylamine, and 2-phenylethylamine.

To a stirring solution of 1 (1 equiv) in DCM (10 vol) at 0° C. under nitrogen atmosphere was added N,N-diisopropylethylamine (DIEA) (3 equiv) and propane phosphonic acid anhydride (T3P) (1.5 equiv). The reaction mixture was stirred at 0° C. for 10 minutes. Ethylamine was added to the reaction mixture at 0° C. and the mixture was stirred at room temperature for 16 hours. After completion of the reaction, the reaction mixture was concentrated and purified directly by reverse phase HPLC to afford Compound 506. $^1$H NMR (400 MHz, DMSO-d$_6$) δ 9.03 (s, 2H), 8.33 (d, J=1.6 Hz, 1H), 7.80 (t, J=5.6 Hz, 1H), 7.63 (s, 1H), 5.97 (d, J=17.8 Hz, 1H), 5.67 (d, J=17.8 Hz, 1H), 4.16 (dd, J=9.1, 5.0 Hz, 1H), 3.51 (dd, J=5.7, 2.3 Hz, 1H), 3.11-2.99 (m, 2H), 2.69 (s, 3H), 2.68 (s, 3H), 2.65 (s, 3H), 2.38 (dd, J=13.1, 9.1 Hz, 1H), 1.90 (dd, J=13.1, 5.0 Hz, 1H), 1.28 (s, 3H), 1.01 (m, 1H), 0.98 (t, J=7.2 Hz, 3H), 0.85 (dd, J=5.4, 2.4 Hz, 1H).

(1R,3S,5R)-2-{2-[3-Acetyl-7-methyl-5-(2-methylpyrimidin-5-yl)indazol-1-yl]acetyl}-5-methyl-N-propyl-2-azabicyclo[3.1.0]hexane-3-carboxamide $^1$H NMR (400 MHz, DMSO-d$_6$) δ 9.03 (s, 2H), 8.33 (d, J=1.6 Hz, 1H), 7.79 (t, J=5.8 Hz, 1H), 7.63 (s, 1H), 5.97 (d, J=17.8 Hz, 1H), 5.67 (d, J=17.8 Hz, 1H), 4.18 (dd, J=9.1, 5.0 Hz, 1H), 3.51 (dd, J=5.6, 2.4 Hz, 1H), 3.00 (q, J=6.6 Hz, 2H), 2.69 (s, 3H), 2.68 (s, 3H), 2.65 (s, 3H), 2.40 (dd, J=13.1, 9.1 Hz, 1H), 1.90 (dd, J=13.0, 5.0 Hz, 1H), 1.38 (h, J=7.2 Hz, 2H), 1.28 (s, 3H), 1.01 (t, J=5.4 Hz, 1H), 0.86 (m, 1H), 0.81 (t, J=7.2 Hz, 3H).

(1R,3S,5R)-2-{2-[3-Acetyl-7-methyl-5-(2-methylpyrimidin-5-yl)indazol-1-yl]acetyl}-N-butyl-5-methyl-2-azabicyclo[3.1.0]hexane-3-carboxamide $^1$H NMR (400 MHz, DMSO-d$_6$) δ 9.03 (s, 2H), 8.33 (d, J=1.6 Hz, 1H), 7.76 (t, J=5.7 Hz, 1H), 7.63 (s, 1H), 5.97 (d, J=17.8 Hz, 1H), 5.67 (d, J=17.7 Hz, 1H), 4.17 (dd, J=9.1, 4.9 Hz, 1H), 3.50 (dd, J=5.6, 2.4 Hz, 1H), 3.03 (q, J=6.7 Hz, 2H), 2.69 (s, 3H), 2.68 (s, 3H), 2.65 (s, 3H), 2.39 (dd, J=13.2, 9.1 Hz, 1H), 1.90 (dd, J=13.2, 4.9 Hz, 1H), 1.41-1.29 (m, 2H), 1.28 (s, 3H), 1.27-1.17 (m, 2H), 1.01 (t, J=5.4 Hz, 1H), 0.84 (t, J=7.2 Hz, 4H).

(1R,3S,5R)-2-{2-[3-Acetyl-7-methyl-5-(2-methylpyrimidin-5-yl)indazol-1-yl]acetyl}-5-methyl-N-pentyl-2-azabicyclo[3.1.0]hexane-3-carboxamide $^1$H NMR (400 MHz, DMSO-d$_6$) δ 9.03 (s, 2H), 8.32 (d, J=1.6 Hz, 1H), 7.77 (t, J=5.7 Hz, 1H), 7.63 (s, 1H), 5.97 (d, J=17.8 Hz, 1H), 5.67 (d, J=17.7 Hz, 1H), 4.17 (dd, J=9.1, 4.9 Hz, 1H), 3.50 (dd, J=5.6, 2.4 Hz, 1H), 3.02 (q, J=6.6 Hz, 2H), 2.69 (s, 3H), 2.68 (s, 3H), 2.65 (s, 3H), 2.39 (dd, J=13.1, 9.1 Hz, 1H), 1.90 (dd, J=13.2, 4.9 Hz, 1H), 1.37 (p, J=6.9 Hz, 2H), 1.31-1.14 (m, 7H), 1.01 (t, J=5.3 Hz, 1H), 0.89-0.78 (m, 4H).

(1R,3S,5R)-2-{2-[3-Acetyl-7-methyl-5-(2-methylpyrimidin-5-yl)indazol-1-yl]acetyl}-N-(cyclopropylmethyl)-5-methyl-2-azabicyclo[3.1.0]hexane-3-carboxamide $^1$H NMR (400 MHz, DMSO-d$_6$) δ 9.06 (s, 2H), 8.35 (d, J=1.6 Hz, 1H), 7.87 (t, J=5.8 Hz, 1H), 7.66 (s, 1H), 6.01 (d, J=17.8 Hz, 1H), 5.70 (d, J=17.7 Hz, 1H), 4.23 (dd, J=9.1, 4.9 Hz, 1H), 3.54 (dd, J=5.6, 2.3 Hz, 1H), 2.98 (t, J=6.1 Hz, 2H), 2.74-2.63 (m, 9H), 2.43 (dd, J=13.1, 9.1 Hz, 1H), 1.94 (dd, J=13.3, 4.9 Hz, 1H), 1.32 (s, 3H), 1.04 (t, J=5.5 Hz, 1H), 0.89 (dq, J=6.2, 3.7 Hz, 2H), 0.38 (dt, J=8.6, 2.8 Hz, 2H), 0.16 (p, J=3.9, 3.3 Hz, 2H).

(1R,3S,5R)-2-{2-[3-Acetyl-7-methyl-5-(2-methylpyrimidin-5-yl)indazol-1-yl]acetyl}-N-(2,2-dimethylpropyl)-5-methyl-2-azabicyclo[3.1.0]hexane-3-carboxamide $^1$H NMR (400 MHz, DMSO-d$_6$) δ 9.03 (s, 2H), 8.32 (d, J=1.6 Hz, 1H), 7.71 (t, J=6.4 Hz, 1H), 7.63 (s, 1H), 6.00 (d, J=17.8 Hz, 1H), 5.66 (d, J=17.7 Hz, 1H), 4.27 (dd, J=9.1, 5.0 Hz, 1H), 3.53 (dd, J=5.6, 2.3 Hz, 1H), 2.93 (dd, J=13.1, 6.7 Hz, 1H), 2.79 (dd, J=13.0, 6.0 Hz, 1H), 2.72-2.59 (m, 9H), 2.42 (dd, J=13.1, 9.1 Hz, 1H), 1.92 (dd, J=13.1, 4.9 Hz, 1H), 1.29 (s, 3H), 1.01 (t, J=5.4 Hz, 1H), 0.94-0.72 (m, 2H), 0.80 (s, 8H).

(1R,3S,5R)-2-{2-[3-Acetyl-7-methyl-5-(2-methylpyrimidin-5-yl)indazol-1-yl]acetyl}-5-methyl-N-(2-methylpropyl)-2-azabicyclo[3.1.0]hexane-3-carboxamide $^1$H NMR (400 MHz, DMSO-d$_6$) δ 9.03 (s, 2H), 8.33 (d, J=1.6 Hz, 1H), 7.80 (t, J=5.9 Hz, 1H), 7.63 (s, 1H), 5.98 (d, J=17.8 Hz, 1H), 5.67 (d, J=17.7 Hz, 1H), 4.21 (dd, J=9.1, 4.9 Hz, 1H), 3.51 (dd, J=5.6, 2.3 Hz, 1H), 2.86 (h, J=6.6 Hz, 2H), 2.72-2.60 (m, 9H), 2.41 (dd, J=13.2, 9.1 Hz, 1H), 1.91 (dd, J=13.1, 5.0 Hz, 1H), 1.66 (hept, J=6.7 Hz, 1H), 1.28 (s, 3H), 1.01 (t, J=5.4 Hz, 1H), 0.94-0.77 (m, 7H).

(1R,3S,5R)-2-{2-[3-Acetyl-7-methyl-5-(2-methylpyrimidin-5-yl)indazol-1-yl]acetyl}-N,5-dimethyl-2-azabicyclo[3.1.0]hexane-3-carboxamide $^1$H NMR (400 MHz, Methanol-d4) δ 8.97 (s, 2H), 8.41-8.35 (m, 1H), 7.52 (s, 1H), 5.89 (d, J=17.7 Hz, 1H), 5.78 (d, J=17.7 Hz, 1H), 4.30 (dd, J=9.2, 5.3 Hz, 1H), 3.46 (dd, J=5.6, 2.4 Hz, 1H), 2.78-2.65 (m, 12H), 2.51 (dd, J=13.4, 9.2 Hz, 1H), 2.09 (dd, J=13.3, 5.4 Hz, 1H), 1.38 (s, 3H), 1.10 (t, J=5.5 Hz, 1H), 0.91 (dd, J=5.5, 2.4 Hz, 1H).

(1R,3S,5R)-2-{2-[3-Acetyl-5-(2-methylpyrimidin-5-yl)indazol-1-yl]acetyl}-N-(3-aminopropyl)-5-methyl-2-azabicyclo[3.1.0]hexane-3-carboxamide $^1$H NMR (400 MHz, DMSO-d$_6$) δ 9.06 (s, 2H), 8.45 (s, 1H), 8.39 (s, 1H), 8.12 (t, J=5.9 Hz, 1H), 7.88 (d, J=7.6 Hz, 2H), 5.88 (dd, J=17.2, 12.1 Hz, 1H), 5.54 (d, J=17.2 Hz, 1H), 4.17 (dd, J=9.3, 4.8 Hz, 1H), 3.51 (m, 1H), 3.31 (m, 1H) 3.11 (m, 2H), 2.91 (d, J=6.6 Hz, 1H), 2.68 (d, J=14.6 Hz, 7H), 2.40 (dt, J=16.3, 8.3 Hz, 1H), 1.91 (dd, J=12.8, 5.2 Hz, 1H), 1.62 (t, J=6.9 Hz, 1H), 1.53-1.45 (m, 1H), 1.28 (s, 3H), 0.99 (p, J=5.1 Hz, 2H).

(1R,3S,5R)-2-{2-[3-Acetyl-5-(2-methylpyrimidin-5-yl)indazol-1-yl]acetyl}-5-methyl-N-[3-(methylamino)propyl]-2-azabicyclo[3.1.0]hexane-3-carboxamide $^1$H NMR (400 MHz, DMSO-d$_6$) δ 9.05 (s, 2H), 8.35 (s, 1H), 8.05 (t, J=5.8 Hz, 1H), 7.88 (s, 2H), 5.89 (d, J=17.2 Hz, 1H), 5.54 (d, J=17.2 Hz, 1H), 4.16 (dd, J=9.2, 4.9 Hz, 1H), 3.51 (t, J=3.9 Hz, 1H), 3.11 (q, J=6.6 Hz, 2H), 2.70 (s, 3H), 2.66 (s, 3H), 2.58-2.61 (m, 3H), 2.28 (s, 3H), 1.92 (dd, J=13.1, 4.9 Hz, 1H), 1.60 (p, J=6.9 Hz, 1H), 1.28 (s, 3H), 0.98 (s, 2H).

(1R,3S,5R)-2-{2-[3-Acetyl-5-(2-methylpyrimidin-5-yl)indazol-1-yl]acetyl}-N-[3-(dimethylamino)propyl]-5-methyl-2-azabicyclo[3.1.0]hexane-3-carboxamide $^1$H NMR (400 MHz, DMSO-d$_6$) δ 9.05 (s, 2H), 8.23 (s, 1H), 7.87 (s, 2H), 5.87 (d, J=17.2 Hz, 1H), 5.54 (d, J=17.2 Hz, 1H), 4.17 (dd, J=9.2, 4.7 Hz, 1H), 3.49 (dd, J=5.4, 2.7 Hz, 1H), 3.07 (q, J=6.5 Hz, 2H), 2.70 (d, J=15.4 Hz, 3H), 2.66 (d, J=15.4 Hz, 3H), 2.38 (dd, J=13.2, 9.1 Hz, 1H), 2.20 (t, J=7.2 Hz, 2H), 2.09 (s, 6H), 1.92 (dd, J=13.1, 4.7 Hz, 1H), 1.51 (p, J=7.0 Hz, 2H), 1.28 (s, 3H), 1.03-0.94 (m, 2H).

(1R,3S,5R)-2-{2-[3-Acetyl-5-(2-methylpyrimidin-5-yl)indazol-1-yl]acetyl}-5-methyl-N-propyl-2-azabicyclo[3.1.0]hexane-3-carboxamide $^1$H NMR (400 MHz, DMSO-d$_6$) δ 9.05 (s, 2H), 8.45 (s, 1H), 7.87 (m, 2H), 7.82 (m, 1H), 5.87 (d, J=17.2 Hz, 1H), 5.53 (d, J=17.2 Hz, 1H), 4.18 (dd, J=9.2, 4.6 Hz, 1H), 3.48 (dd, J=5.5, 2.5 Hz, 1H), 3.01 (q, J=6.5 Hz, 2H), 2.70 (s, 3H), 2.66 (s, 3H), 2.38 (dd, J=13.2, 9.1 Hz, 1H), 1.92 (dd, J=13.2, 4.6 Hz, 1H), 1.39 (h, J=7.2 Hz, 2H), 1.28 (s, 3H), 1.03-0.85 (m, 2H), 0.81 (t, J=7.4 Hz, 3H).

(1R,3S,5R)-2-{2-[3-Acetyl-5-(2-methylpyrimidin-5-yl)indazol-1-yl]acetyl}-N-butyl-5-methyl-2-azabicyclo[3.1.0]hexane-3-carboxamide $^1$H NMR (400 MHz, DMSO-d$_6$) δ 9.05 (s, 2H), 8.45 (s, 1H), 7.87 (s, 2H), 7.80 (t, J=5.8 Hz, 1H), 5.87 (d, J=17.2 Hz, 1H), 5.53 (d, J=17.2 Hz, 1H), 4.18 (dd, J=9.2, 4.5 Hz, 1H), 3.48 (dd, J=5.5, 2.5 Hz, 1H), 3.05 (q, J=6.7 Hz, 2H), 2.68 (d, J=14.0 Hz, 6H), 2.38 (dd, J=13.2, 9.2 Hz, 1H), 1.91 (dd, J=13.2, 4.6 Hz, 1H), 1.36 (p, J=7.0 Hz, 2H), 1.30-1.18 (m, 5H), 0.98 (dt, J=7.6, 5.0 Hz, 2H), 0.83 (t, J=7.3 Hz, 3H).

(1R,3S,5R)-2-{2-[3-Acetyl-5-(2-methylpyrimidin-5-yl)indazol-1-yl]acetyl}-5-methyl-N-pentyl-2-azabicyclo[3.1.0]hexane-3-carboxamide ¹H NMR (400 MHz, DMSO-d₆) δ 9.05 (s, 2H), 8.45 (s, 1H), 7.87 (s, 2H), 7.80 (t, J=5.8 Hz, 1H), 5.87 (d, J=17.2 Hz, 1H), 5.53 (d, J=17.2 Hz, 1H), 4.18 (dd, J=9.2, 4.5 Hz, 1H), 3.48 (dd, J=5.5, 2.5 Hz, 1H), 3.04 (q, J=6.6 Hz, 2H), 2.70 (s, 3H), 2.66 (s, 3H), 2.38 (dd, J=13.2, 9.2 Hz, 1H), 1.91 (dd, J=13.1, 4.5 Hz, 1H), 1.37 (td, J=13.0, 11.7, 6.0 Hz, 2H), 1.33-1.16 (m, 7H), 1.06-0.93 (m, 2H), 0.81 (t, J=6.8 Hz, 3H).

(1R,3S,5R)-2-{2-[3-Acetyl-5-(2-methylpyrimidin-5-yl)indazol-1-yl]acetyl}-N-(2,2-dimethylpropyl)-5-methyl-2-azabicyclo[3.1.0]hexane-3-carboxamide ¹H NMR (400 MHz, DMSO-d₆) δ 9.05 (s, 2H), 8.44 (d, J=6.1 Hz, 1H), 7.86 (s, 2H), 7.69 (t, J=6.4 Hz, 1H), 5.90 (d, J=17.2 Hz, 1H), 5.54 (d, J=17.1 Hz, 1H), 4.27 (dd, J=9.2, 4.6 Hz, 1H), 3.51 (dd, J=5.6, 2.4 Hz, 1H), 2.94 (dd, J=13.0, 6.8 Hz, 1H), 2.81 (dd, J=13.0, 6.0 Hz, 1H), 2.70 (s, 3H), 2.66 (s, 3H), 2.40 (dd, J=13.2, 9.2 Hz, 1H), 1.95 (dd, J=13.2, 4.6 Hz, 1H), 1.28 (s, 2H), 1.03-0.88 (m, 2H), 0.80 (s, 9H).

(1R,3S,5R)-2-{2-[3-Acetyl-5-(2-methylpyrimidin-5-yl)indazol-1-yl]acetyl}-N-benzyl-5-methyl-2-azabicyclo[3.1.0]hexane-3-carboxamide ¹H NMR (400 MHz, DMSO-d₆) δ 9.06 (s, 2H), 8.48-8.39 (m, 2H), 7.86 (s, 2H), 7.39-7.16 (m, 5H), 5.88 (d, J=17.2 Hz, 1H), 5.56 (d, J=17.2 Hz, 1H), 4.29 (m, 3H), 3.51 (t, J=4.1 Hz, 1H), 2.70 (s, 3H), 2.66 (s, 3H), 2.44 (dd, J=13.2, 9.2 Hz, 1H), 1.97 (dd, J=13.2, 4.5 Hz, 1H), 1.28 (s, 3H), 1.01 (d, J=3.9 Hz, 2H).

(1R,3S,5R)-2-{2-[3-Acetyl-7-methyl-5-(2-methylpyrimidin-5-yl)indazol-1-yl]acetyl}-N-hexyl-5-methyl-2-azabicyclo[3.1.0]hexane-3-carboxamide ¹H NMR (400 MHz, DMSO-d₆) δ 9.03 (s, 2H), 8.32 (d, J=1.6 Hz, 1H), 7.76 (t, J=5.7 Hz, 1H), 7.63 (s, 1H), 5.97 (d, J=17.8 Hz, 1H), 5.67 (d, J=17.8 Hz, 1H), 4.17 (dd, J=9.1, 4.9 Hz, 1H), 3.50 (dd, J=5.6, 2.3 Hz, 1H), 3.02 (q, J=6.5 Hz, 2H), 2.69 (s, 3H), 2.68 (s, 3H), 2.65 (s, 3H), 2.39 (dd, J=13.1, 9.1 Hz, 1H), 1.89 (dd, J=13.1, 4.9 Hz, 1H), 1.36 (m, 2H), 1.28 (s, 3H), 1.29-1.21 (m, 6H), 1.01 (t, J=5.4 Hz, 1H), 0.88-0.77 (m, 4H).

(1R,3S,5R)-2-{2-[3-Acetyl-7-methyl-5-(2-methylpyrimidin-5-yl)indazol-1-yl]acetyl}-N-heptyl-5-methyl-2-azabicyclo[3.1.0]hexane-3-carboxamide ¹H NMR (400 MHz, DMSO-d₆) δ 9.03 (s, 2H), 8.32 (d, J=1.6 Hz, 1H), 7.76 (t, J=5.7 Hz, 1H), 7.63 (s, 1H), 5.97 (d, J=17.8 Hz, 1H), 5.66 (d, J=17.7 Hz, 1H), 4.17 (dd, J=9.0, 4.9 Hz, 1H), 3.50 (dd, J=5.7, 2.3 Hz, 1H), 3.02 (q, J=6.5 Hz, 2H), 2.69 (s, 3H), 2.68 (s, 3H), 2.65 (s, 3H), 2.39 (dd, J=13.2, 9.1 Hz, 1H), 1.89 (dd, J=13.2, 5.0 Hz, 1H), 1.36 (q, J=7.0 Hz, 2H), 1.28 (s, 3H), 1.21 (m, 8H), 1.01 (t, J=5.4 Hz, 1H), 0.88-0.77 (m, 4H).

(1R,3S,5R)-2-{2-[3-Acetyl-7-methyl-5-(2-methylpyrimidin-5-yl)indazol-1-yl]acetyl}-5-methyl-N-octyl-2-azabicyclo[3.1.0]hexane-3-carboxamide ¹H NMR (400 MHz, DMSO-d₆) δ 9.03 (s, 2H), 8.33 (s, 1H), 7.76 (t, J=5.7 Hz, 1H), 7.62 (s, 1H), 5.97 (d, J=17.8 Hz, 1H), 5.66 (d, J=17.8 Hz, 1H), 4.17 (dd, J=9.2, 5.0 Hz, 1H), 3.50 (dd, J=5.9, 2.3 Hz, 1H), 3.02 (q, J=6.6 Hz, 2H), 2.69 (s, 3H), 2.68 (s, 3H), 2.65 (s, 3H) 2.39 (dd, J=13.1, 9.1 Hz, 1H), 1.89 (dd, J=13.0, 4.9 Hz, 1H), 1.35 (s, 2H), 1.28 (s, 3H), 1.20 (m, 10H), 1.01 (t, J=5.5 Hz, 1H), 0.83 (dt, J=13.1, 5.9 Hz, 4H).

(1R,3S,5R)-2-{2-[3-Acetyl-7-methyl-5-(2-methylpyrimidin-5-yl)indazol-1-yl]acetyl}-5-methyl-N-nonyl-2-azabicyclo[3.1.0]hexane-3-carboxamide ¹H NMR (400 MHz, DMSO-d₆) δ 9.03 (s, 2H), 8.32 (d, J=1.6 Hz, 1H), 7.76 (t, J=5.8 Hz, 1H), 7.62 (s, 1H), 5.97 (d, J=17.8 Hz, 1H), 5.66 (d, J=17.8 Hz, 1H), 4.17 (dd, J=9.1, 4.9 Hz, 1H), 3.50 (dd, J=5.7, 2.3 Hz, 1H), 3.02 (q, J=6.6 Hz, 2H), 2.69 (s, 3H), 2.68 (s, 3H), 2.65 (s, 3H), 2.39 (dd, J=13.1, 9.1 Hz, 1H), 1.89 (dd, J=13.2, 4.9 Hz, 1H), 1.35 (t, J=6.9 Hz, 2H), 1.28 (s, 3H), 1.28-1.16 (m, 12H), 1.01 (t, J=5.4 Hz, 1H), 0.83 (q, J=7.8, 7.0 Hz, 4H).

(1R,3S,5R)-2-{2-[3-Acetyl-7-methyl-5-(2-methylpyrimidin-5-yl)indazol-1-yl]acetyl}-N-decyl-5-methyl-2-azabicyclo[3.1.0]hexane-3-carboxamide ¹H NMR (400 MHz, DMSO-d₆) δ 9.03 (s, 2H), 8.32 (d, J=1.6 Hz, 1H), 7.76 (t, J=5.8 Hz, 1H), 7.62 (s, 1H), 5.97 (d, J=17.8 Hz, 1H), 5.66 (d, J=17.8 Hz, 1H), 4.17 (dd, J=9.1, 4.9 Hz, 1H), 3.50 (dd, J=5.7, 2.3 Hz, 1H), 3.02 (q, J=6.6 Hz, 2H), 2.69 (s, 3H), 2.68 (s, 3H), 2.65 (s, 3H), 2.39 (dd, J=13.1, 9.1 Hz, 1H), 1.89 (dd, J=13.2, 4.9 Hz, 1H), 1.35 (t, J=6.9 Hz, 2H), 1.28 (s, 3H), 1.28-1.16 (m, 14H), 1.01 (t, J=5.4 Hz, 1H), 0.83 (q, J=7.8, 7.0 Hz, 4H).

(1R,3S,5R)-2-{2-[3-Acetyl-7-methyl-5-(2-methylpyrimidin-5-yl)indazol-1-yl]acetyl}-5-methyl-N-(2-phenylethyl)-2-azabicyclo[3.1.0]hexane-3-carboxamide ¹H NMR (400 MHz, DMSO-d₆) δ 9.03 (s, 2H), 8.33 (s, 1H), 7.89 (t, J=5.8 Hz, 1H), 7.63 (s, 1H), 7.22 (dd, J=25.8, 7.1 Hz, 5H), 5.96 (d, J=17.7 Hz, 1H), 5.67 (d, J=17.7 Hz, 1H), 4.17 (dd, J=9.2, 4.9 Hz, 1H), 3.48 (dd, J=5.6, 2.3 Hz, 1H), 3.24 (m, 2H), 2.73-2.63 (m, 11H), 2.35 (dd, J=13.2, 9.1 Hz, 1H), 1.81 (dd, J=13.2, 4.9 Hz, 1H), 1.24 (s, 3H), 0.99 (t, J=5.4 Hz, 1H), 0.84 (dd, J=5.1, 2.3 Hz, 1H).

(1R,3S,5R)-2-{2-[3-Acetyl-7-methyl-5-(2-methylpyrimidin-5-yl)indazol-1-yl]acetyl}-5-methyl-N-(3-phenylpropyl)-2-azabicyclo[3.1.0]hexane-3-carboxamide ¹H NMR (400 MHz, DMSO-d₆) δ 9.01 (s, 2H), 8.32 (s, 1H), 7.86 (t, J=5.5 Hz, 1H), 7.60 (s, 1H), 7.16 (m, 5H), 5.98 (d, J=17.8 Hz, 1H), 5.68 (d, J=17.7 Hz, 1H), 4.18 (dd, J=9.2, 5.1 Hz, 1H), 3.52 (dd, J=5.6, 2.3 Hz, 1H), 3.05 (q, J=6.5 Hz, 2H), 2.74-2.57 (m, 11H), 2.41 (dd, J=13.2, 9.1 Hz, 1H), 1.92 (dd, J=13.2, 5.2 Hz, 1H), 1.64 (dt, J=13.6, 6.7 Hz, 2H), 1.29 (s, 3H), 1.00 (t, J=5.5 Hz, 1H), 0.86 (dd, J=5.3, 2.4 Hz, 1H).

(1R,3S,5R)-2-{2-[3-Acetyl-7-methyl-5-(2-methylpyrimidin-5-yl)indazol-1-yl]acetyl}-5-methyl-N-(4-phenylbutyl)-2-azabicyclo[3.1.0]hexane-3-carboxamide $^1$H NMR (400 MHz, DMSO-d$_6$) δ 9.01 (s, 2H), 8.32 (d, J=1.6 Hz, 1H), 7.79 (t, J=5.8 Hz, 1H), 7.61 (s, 1H), 7.23-7.09 (m, 5H), 5.97 (d, J=17.8 Hz, 1H), 5.66 (d, J=17.7 Hz, 1H), 4.16 (dd, J=9.1, 5.0 Hz, 1H), 3.50 (dd, J=5.6, 2.3 Hz, 1H), 3.06 (q, J=6.5 Hz, 2H), 2.71-2.57 (m, 11H), 2.38 (dd, J=13.2, 9.1 Hz, 1H), 1.88 (dd, J=13.1, 5.0 Hz, 1H), 1.52 (tt, J=8.4, 4.7 Hz, 2H), 1.39 (p, J=7.2 Hz, 2H), 1.27 (s, 3H), 1.00 (t, J=5.4 Hz, 1H), 0.85 (dd, J=5.2, 2.4 Hz, 1H).

(1R,3S,5R)-2-{2-[3-Acetyl-7-methyl-5-(2-methylpyrimidin-5-yl)indazol-1-yl]acetyl}-5-methyl-N-(5-phenylpentyl)-2-azabicyclo[3.1.0]hexane-3-carboxamide $^1$H NMR (400 MHz, DMSO-d$_6$) δ 9.01 (s, 2H), 8.32 (s, 1H), 7.77 (t, J=5.9 Hz, 1H), 7.61 (s, 1H), 7.30-7.09 (m, 5H), 5.97 (d, J=17.8 Hz, 1H), 5.66 (d, J=17.8 Hz, 1H), 4.16 (dd, J=9.1, 5.0 Hz, 1H), 3.50 (dd, J=5.6, 2.3 Hz, 1H), 3.02 (q, J=6.5 Hz, 2H), 2.71-2.53 (m, 11H), 2.37 (dd, J=13.2, 9.2 Hz, 1H), 1.87 (dd, J=13.1, 5.0 Hz, 1H), 1.52 (p, J=7.7 Hz, 2H), 1.40 (p, J=7.1 Hz, 2H), 1.26 (m, 5H), 1.00 (t, J=5.4 Hz, 1H), 0.85 (dd, J=5.5, 2.3 Hz, 1H).

(1R,3S,5R)-2-{2-[3-Acetyl-7-methyl-5-(2-methylpyrimidin-5-yl)indazol-1-yl]acetyl}-5-methyl-N-(6-phenylhexyl)-2-azabicyclo[3.1.0]hexane-3-carboxamide $^1$H NMR (400 MHz, DMSO-d$_6$) δ 9.02 (s, 2H), 8.32 (s, 1H), 7.76 (t, J=5.7 Hz, 1H), 7.61 (s, 1H), 7.31-7.19 (m, 2H), 7.13 (m, 3H), 5.97 (d, J=17.8 Hz, 1H), 5.66 (d, J=17.7 Hz, 1H), 4.17 (dd, J=9.1, 4.9 Hz, 1H), 3.53-3.46 (m, 1H), 3.01 (q, J=6.5 Hz, 2H), 2.71-2.54 (m, 11H), 2.38 (dd, J=13.2, 9.1 Hz, 1H), 1.89 (dd, J=13.2, 4.9 Hz, 1H), 1.50 (t, J=7.5 Hz, 2H), 1.35 (s, 2H), 1.36-1.18 (m, 7H), 1.00 (t, J=5.5 Hz, 1H), 0.85 (dd, J=5.0, 2.4 Hz, 1H).

(1R,3S,5R)-2-{2-[3-Acetyl-7-methyl-5-(2-methylpyrimidin-5-yl)indazol-1-yl]acetyl}-N-benzyl-5-methyl-2-azabicyclo[3.1.0]hexane-3-carboxamide $^1$H NMR (400 MHz, DMSO-d$_6$) δ 9.04 (d, J=1.7 Hz, 2H), 8.42-8.31 (m, 2H), 7.63 (s, 1H), 7.32-7.19 (m, 5H), 5.98 (d, J=17.7 Hz, 1H), 5.78-5.65 (m, 1H), 4.28 (m, 3H), 3.55-3.49 (m, 1H), 2.69 (s, 3H), 2.67 (s, 3H), 2.65 (s, 3H), 2.50-2.42 (m, 1H), 1.94 (dd, J=13.3, 4.8 Hz, 1H), 1.29 (s, 3H), 1.02 (d, J=5.5 Hz, 1H), 0.91-0.85 (m, 1H).

(1R,3S,5R)-2-{2-[3-Acetyl-7-methyl-5-(2-methylpyrimidin-5-yl)indazol-1-yl]acetyl}-N-[(2-methoxyphenyl)methyl]-5-methyl-2-azabicyclo[3.1.0]hexane-3-carboxamide $^1$H NMR (400 MHz, DMSO-d$_6$) δ 9.04 (s, 2H), 8.34 (d, J=1.6 Hz, 1H), 8.19 (t, J=6.0 Hz, 1H), 7.63 (s, 1H), 7.30-6.86 (m, 4H), 6.81 (t, J=7.4 Hz, 1H), 5.99 (d, J=17.8 Hz, 1H), 5.70 (d, J=17.8 Hz, 1H), 4.31 (dd, J=9.2, 4.9 Hz, 1H), 4.29-4.15 (m, 2H), 3.78 (s, 3H), 3.56-3.49 (m, 1H), 3.18 (s, 1H), 2.72-2.61 (m, 9H), 2.44 (dd, J=13.2, 9.1 Hz, 1H), 2.08 (s, 1H), 1.97 (dd, J=13.3, 4.8 Hz, 1H), 1.30 (s, 3H), 1.03 (t, J=5.4 Hz, 1H), 0.88 (dd, J=5.2, 2.4 Hz, 1H).

(1R,3S,5R)-2-{2-[3-Acetyl-7-methyl-5-(2-methylpyrimidin-5-yl)indazol-1-yl]acetyl}-N-[(3-methoxyphenyl)methyl]-5-methyl-2-azabicyclo[3.1.0]hexane-3-carboxamide $^1$H NMR (400 MHz, DMSO-d$_6$) δ 9.04 (s, 2H), 8.43-8.31 (m, 2H), 7.62 (s, 1H), 7.16 (t, J=7.8 Hz, 1H), 6.81-6.70 (m, 3H), 5.99 (d, J=17.8 Hz, 1H), 5.70 (d, J=17.8 Hz, 1H), 4.39-4.17 (m, 3H), 3.54 (dd, J=5.6, 2.3 Hz, 1H), 3.52 (s, 3H), 3.18 (s, 1H), 2.69 (s, 3H), 2.67 (s, 3H), 2.65 (s, 3H), 2.45 (dd, J=13.1, 9.1 Hz, 1H), 1.94 (dd, J=13.2, 5.2 Hz, 1H), 1.29 (s, 3H), 1.02 (t, J=5.3 Hz, 1H), 0.88 (dd, J=5.4, 2.4 Hz, 1H).

(1R,3S,5R)-2-{2-[3-Acetyl-7-methyl-5-(2-methylpyrimidin-5-yl)indazol-1-yl]acetyl}-N-[(4-methoxyphenyl)methyl]-5-methyl-2-azabicyclo[3.1.0]hexane-3-carboxamide $^1$H NMR (400 MHz, DMSO-d$_6$) δ 9.04 (s, 2H), 8.36-8.25 (m, 2H), 7.63 (s, 1H), 7.13 (d, J=8.5 Hz, 2H), 6.81 (d, J=8.5 Hz, 2H), 5.98 (d, J=17.9 Hz, 1H), 5.68 (d, J=17.7 Hz, 1H), 4.83 (s, 6H), 4.23 (dd, J=22.3, 5.1 Hz, 3H), 3.69 (s, 3H), 3.52 (dd, J=5.7, 2.5 Hz, 1H), 3.18 (s, 1H), 2.72-2.61 (m, 9H), 2.43 (dd, J=13.2, 9.2 Hz, 1H), 2.08 (s, 2H), 1.93 (dd, J=13.1, 4.9 Hz, 1H), 1.28 (s, 3H), 1.22 (d, J=18.3 Hz, 0H), 1.01 (t, J=5.4 Hz, 1H), 0.87 (dd, J=5.3, 2.4 Hz, 1H).

(1R,3S,5R)-2-{2-[3-Acetyl-7-methyl-5-(2-methylpyrimidin-5-yl)indazol-1-yl]acetyl}-5-methyl-N-[(1S)-1-phenylethyl]-2-azabicyclo[3.1.0]hexane-3-carboxamide $^1$H NMR (400 MHz, DMSO-d$_6$) δ 9.04 (s, 2H), 8.33 (d, J=1.7 Hz, 1H), 8.22 (d, J=8.0 Hz, 1H), 7.64 (t, J=1.5 Hz, 1H), 7.41-7.17 (m, 5H), 6.02 (d, J=17.9 Hz, 1H), 5.65 (d, J=17.8 Hz, 1H), 4.87 (p, J=7.1 Hz, 1H), 4.25 (dd, J=9.0, 5.4 Hz, 1H), 3.53 (dd, J=5.6, 2.3 Hz, 1H), 2.69 (s, 3H), 2.69 (s, 3H), 2.65 (s, 3H), 2.41 (dd, J=13.1, 9.0 Hz, 1H), 1.83 (dd, J=13.0, 5.4 Hz, 1H), 1.30 (d, J=7.0 Hz, 3H), 1.23 (s, 3H), 0.99 (t, J=5.4 Hz, 1H), 0.86 (dd, J=5.3, 2.4 Hz, 1H).

(1R,3S,5R)-2-{2-[3-Acetyl-7-methyl-5-(2-methylpyrimidin-5-yl)indazol-1-yl]acetyl}-5-methyl-N-[(1R)-1-phenylethyl]-2-azabicyclo[3.1.0]hexane-3-carboxamide $^1$H NMR (400 MHz, DMSO-d$_6$) δ 9.03 (s, 2H), 8.33 (d, J=1.7 Hz, 1H), 8.18 (d, J=8.2 Hz, 1H), 7.62 (d, J=1.7 Hz, 1H), 7.32-7.18 (m, 4H), 7.22-7.13 (m, 1H), 5.99 (d, J=17.8 Hz, 1H), 5.66 (d, J=17.8 Hz, 1H), 4.91 (p, J=7.0 Hz, 1H), 4.29 (dd, J=9.1, 4.9 Hz, 1H), 3.54 (dd, J=5.5, 2.4 Hz, 1H), 2.69 (s, 3H), 2.66 (s, 3H), 2.65 (s, 3H), 2.42 (dd, J=13.2, 9.2 Hz, 1H), 1.92 (dd, J=13.2, 4.8 Hz, 1H), 1.40-1.14 (m, 6H), 1.02 (t, J=5.4 Hz, 1H), 0.87 (dd, J=5.3, 2.4 Hz, 1H).

(1R,3S,5R)-2-{2-[3-Acetyl-7-methyl-5-(2-methylpyrimidin-5-yl)indazol-1-yl]acetyl}-N-[(2-fluorophenyl)methyl]-5-methyl-2-azabicyclo[3.1.0]hexane-3-carboxamide $^1$H NMR (400 MHz, DMSO-d$_6$) δ 9.04 (s, 2H), 8.42-8.31 (m, 2H), 7.63 (s, 1H), 7.27 (q, J=7.2 Hz, 2H), 7.24-7.12 (m, 1H), 7.15-7.02 (m, 1H), 5.98 (d, J=17.8 Hz, 1H), 5.70 (d, J=17.8 Hz, 1H) 4.39-4.24 (m, 3H), 3.53 (dd, J=5.5, 2.3 Hz, 1H), 2.70 (s, 3H), 2.67 (s, 3H), 2.65 (s, 3H), 2.45 (dd, J=13.2, 9.1 Hz, 1H), 1.93 (dd, J=13.3, 5.0 Hz, 1H), 1.28 (s, 3H), 1.02 (t, J=5.4 Hz, 1H), 0.89 (dd, J=5.4, 2.3 Hz, 1H).

(1R,3S,5R)-2-{2-[3-Acetyl-7-methyl-5-(2-methylpyrimidin-5-yl)indazol-1-yl]acetyl}-N-[(3-fluorophenyl)methyl]-5-methyl-2-azabicyclo[3.1.0]hexane-3-carboxamide $^1$H NMR (400 MHz, DMSO-d$_6$) δ 9.04 (s, 2H), 8.46 (t, J=6.0 Hz, 1H), 8.33 (d, J=1.7 Hz, 1H), 7.63 (s, 1H), 7.31 (td, J=8.5, 6.3 Hz, 1H), 7.10-6.98 (m, 3H), 5.98 (d, J=17.8 Hz, 1H), 5.71 (d, J=17.8 Hz, 1H), 4.33-4.24 (m, 3H), 3.53 (dd, J=5.7, 2.4 Hz, 1H), 2.70 (s, 3H), 2.67 (s, 3H), 2.65 (s, 3H), 2.49-2.41 (m, 1H), 1.94 (dd, J=13.2, 5.0 Hz, 1H), 1.29 (s, 3H), 1.03 (t, J=5.4 Hz, 1H), 0.89 (dd, J=5.3, 2.4 Hz, 1H).

(1R,3S,5R)-2-{2-[3-Acetyl-7-methyl-5-(2-methylpyrimidin-5-yl)indazol-1-yl]acetyl}-N-[(4-fluorophenyl)methyl]-5-methyl-2-azabicyclo[3.1.0]hexane-3-carboxamide $^1$H NMR (400 MHz, DMSO-d$_6$) δ 9.04 (s, 2H), 8.44-8.31 (m, 2H), 7.63 (s, 1H), 7.29-7.20 (m, 2H), 7.12-7.02 (m, 2H), 5.98 (d, J=17.8 Hz, 1H), 5.68 (d, J=17.8 Hz, 1H), 4.26 (dd, J=7.9, 5.4 Hz, 3H), 3.52 (dd, J=5.5, 2.4 Hz, 1H), 2.70 (s, 3H), 2.66 (s, 3H), 2.65 (s, 3H), 2.44 (dd, J=13.2, 9.1 Hz, 1H), 1.93 (dd, J=13.2, 4.9 Hz, 1H), 1.28 (s, 3H), 1.02 (t, J=5.3 Hz, 1H), 0.88 (dd, J=5.3, 2.4 Hz, 1H).

(1R,3S,5R)-2-{2-[3-Acetyl-7-methyl-5-(2-methylpyrimidin-5-yl)indazol-1-yl]acetyl}-5-methyl-N-[(2-methylphenyl)methyl]-2-azabicyclo[3.1.0]hexane-3-carboxamide $^1$H NMR (400 MHz, DMSO-d$_6$) δ 9.04 (s, 2H), 8.34 (d, J=1.7 Hz, 1H), 8.24 (t, J=5.8 Hz, 1H), 7.63 (s, 1H), 7.19-7.02 (m, 4H), 5.99 (d, J=17.8 Hz, 1H), 5.69 (d, J=17.8 Hz, 1H), 4.34-4.16 (m, 3H), 3.53 (dd, J=5.7, 2.4 Hz, 1H), 2.70 (s, 3H), 2.67 (s, 3H), 2.65 (s, 3H), 2.45 (dd, J=13.1, 9.2 Hz, 1H), 2.23 (s, 3H), 1.95 (dd, J=13.1, 5.0 Hz, 1H), 1.30 (s, 3H), 1.02 (t, J=5.4 Hz, 1H), 0.88 (dd, J=5.3, 2.4 Hz, 1H).

(1R,3S,5R)-2-{2-[3-Acetyl-7-methyl-5-(2-methylpyrimidin-5-yl)indazol-1-yl]acetyl}-5-methyl-N-[(3-methylphenyl)methyl]-2-azabicyclo[3.1.0]hexane-3-carboxamide $^1$H NMR (400 MHz, DMSO-d$_6$) δ 9.04 (s, 2H), 8.39-8.31 (m, 2H), 7.63 (s, 1H), 7.15 (t, J=7.5 Hz, 1H), 7.01 (dd, J=13.2, 7.6 Hz, 3H), 5.98 (d, J=17.8 Hz, 1H), 5.70 (d, J=17.8 Hz, 1H), 4.32-4.16 (m, 3H), 3.53 (dd, J=5.6, 2.4 Hz, 1H), 2.70 (s, 3H), 2.67 (s, 3H), 2.65 (s, 3H), 2.45 (dd, J=13.2, 9.1 Hz, 1H), 2.18 (s, 3H), 1.95 (dd, J=13.2, 4.9 Hz, 1H), 1.30 (s, 3H), 1.03 (t, J=5.5 Hz, 1H), 0.88 (dd, J=5.2, 2.5 Hz, 1H).

(1R,3S,5R)-2-{2-[3-Acetyl-7-methyl-5-(2-methylpyrimidin-5-yl)indazol-1-yl]acetyl}-5-methyl-N-[(4-methylphenyl)methyl]-2-azabicyclo[3.1.0]hexane-3-carboxamide $^1$H NMR (400 MHz, DMSO-d$_6$) δ 9.04 (s, 2H), 8.36-8.29 (m, 2H), 7.63 (d, J=1.7 Hz, 1H), 7.08 (q, J=8.0 Hz, 4H), 5.98 (d, J=17.8 Hz, 1H), 5.70 (d, J=17.8 Hz, 1H), 4.25 (m, 3H), 3.52 (dd, J=5.5, 2.5 Hz, 1H), 2.70 (s, 3H), 2.67 (s, 3H), 2.65 (s, 3H), 2.44 (dd, J=13.2, 9.2 Hz, 1H), 2.24 (s, 3H), 1.94 (dd, J=13.2, 4.9 Hz, 1H), 1.29 (s, 3H), 1.02 (t, J=5.4 Hz, 1H), 0.88 (dd, J=5.4, 2.4 Hz, 1H).

(1R,3S,5R)-2-{2-[3-Acetyl-7-methyl-5-(2-methylpyrimidin-5-yl)indazol-1-yl]acetyl}-5-methyl-N-(pyrimidin-2-ylmethyl)-2-azabicyclo[3.1.0]hexane-3-carboxamide $^1$H NMR (400 MHz, DMSO-d$_6$) δ 9.04 (s, 2H), 8.79-8.69 (m, 2H), 8.41-8.30 (m, 2H), 7.63 (s, 1H), 7.42-7.36 (m, 1H), 5.99 (d, J=17.8 Hz, 1H), 5.69 (d, J=17.7 Hz, 1H), 4.49-4.42 (m, 2H), 4.37 (dd, J=9.1, 4.5 Hz, 1H), 3.51 (dd, J=5.5, 2.4 Hz, 1H), 2.69 (s, 3H), 2.68 (s, 3H), 2.65 (s, 3H), 2.43 (dd, J=13.2, 9.1 Hz, 1H), 2.15-2.08 (m, 1H), 1.31 (s, 3H), 1.04 (t, J=5.2 Hz, 1H), 0.93-0.82 (m, 1H).

(1R,3S,5R)-2-{2-[3-Acetyl-7-methyl-5-(2-methylpyrimidin-5-yl)indazol-1-yl]acetyl}-5-methyl-N-(pyrimidin-4-ylmethyl)-2-azabicyclo[3.1.0]hexane-3-carboxamide $^1$H NMR (400 MHz, DMSO-d$_6$) δ 9.06 (m, 3H), 8.59 (m, 2H), 8.34 (s, 1H), 7.64 (m, 1H), 7.31 (d, J=5.3 Hz, 1H), 5.99 (d, J=17.8 Hz, 1H), 5.71 (d, J=17.8 Hz, 1H), 4.33 (m, 3H), 3.56-3.50 (m, 1H), 2.77-2.63 (m, 9H), 2.43-2.39 (m, 1H), 2.04-1.96 (m, 1H), 1.28 (s, 3H), 1.02 (t, J=5.6 Hz, 1H), 0.93-0.91 (m, 1H).

(1R,3S,5R)-2-{2-[3-Acetyl-7-methyl-5-(2-methylpyrimidin-5-yl)indazol-1-yl]acetyl}-5-methyl-N-(pyrimidin-5-ylmethyl)-2-azabicyclo[3.1.0]hexane-3-carboxamide $^1$H NMR (400 MHz, DMSO-d$_6$) δ 9.04 (d, J=2.9 Hz, 3H), 8.64 (s, 2H), 8.53 (t, J=5.9 Hz, 1H), 8.33 (d, J=1.6 Hz, 1H), 7.62 (s, 1H), 5.97 (d, J=17.8 Hz, 1H), 5.70 (d, J=17.8 Hz, 1H), 4.32 (d, J=5.9 Hz, 2H), 4.25 (dd, J=9.1, 5.3 Hz, 1H), 3.53 (dd, J=5.6, 2.3 Hz, 1H), 2.70 (s, 3H), 2.65 (s, 3H), 2.65 (s, 3H), 2.45 (dd, J=13.1, 9.1 Hz, 1H), 1.92 (dd, J=13.3, 5.4 Hz, 1H), 1.28 (s, 3H), 1.01 (t, J=5.4 Hz, 1H), 0.90 (dd, J=5.3, 2.4 Hz, 1H).

(1R,3S,5R)-2-{2-[3-Acetyl-7-methyl-5-(2-methylpyrimidin-5-yl)indazol-1-yl]acetyl}-5-methyl-N-(pyridin-2-ylmethyl)-2-azabicyclo[3.1.0]hexane-3-carboxamide $^1$H NMR (400 MHz, DMSO-d$_6$) δ 9.04 (s, 2H), 8.60-8.51 (m, 2H), 8.34 (d, J=1.7 Hz, 1H), 7.80 (t, J=7.9 Hz, 1H), 7.63 (s, 1H), 7.41-7.31 (m, 2H), 5.99 (d, J=17.8 Hz, 1H), 5.70 (d, J=17.8 Hz, 1H), 4.41 (d, J=5.9 Hz, 2H), 4.31 (dd, J=9.2, 5.2 Hz, 1H), 3.54 (dd, J=5.6, 2.4 Hz, 1H), 2.70 (s, 3H), 2.66 (s, 3H), 2.65 (s, 3H), 2.50-2.42 (m, 1H), 1.99 (dd, J=13.2, 5.2 Hz, 1H), 1.30 (s, 3H), 1.02 (t, J=5.5 Hz, 1H), 0.91 (dd, J=5.2, 2.4 Hz, 1H).

(1R,3S,5R)-2-{2-[3-Acetyl-7-methyl-5-(2-methylpyrimidin-5-yl)indazol-1-yl]acetyl}-5-methyl-N-(pyridin-3-ylmethyl)-2-azabicyclo[3.1.0]hexane-3-carboxamide $^1$H NMR (400 MHz, DMSO-d$_6$) δ 9.04 (s, 2H), 8.56 (dd, J=6.6, 4.0 Hz, 3H), 8.34 (d, J=1.6 Hz, 1H), 7.93 (d, J=7.9 Hz, 1H), 7.63 (s, 1H), 7.55 (dd, J=7.9, 5.2 Hz, 1H), 5.97 (d, J=17.8 Hz, 1H), 5.70 (d, J=17.8 Hz, 1H), 4.38 (d, J=5.9 Hz, 2H), 4.26 (dd, J=9.1, 5.4 Hz, 1H), 3.53 (dd, J=5.5, 2.4 Hz, 1H), 2.70 (s, 3H), 2.65 (s, 3H), 2.64 (s, 3H), 2.50-2.41 (m, 1H), 1.93 (dd, J=13.0, 5.4 Hz, 1H), 1.29 (s, 3H), 1.01 (t, J=5.4 Hz, 1H), 0.90 (dd, J=5.2, 2.4 Hz, 1H).

(1R,3S,5R)-2-{2-[3-Acetyl-7-methyl-5-(2-methylpyrimidin-5-yl)indazol-1-yl]acetyl}-5-methyl-N-(pyridin-4-ylmethyl)-2-azabicyclo[3.1.0]hexane-3-carboxamide ¹H NMR (400 MHz, DMSO-d₆) δ 9.05 (s, 2H), 8.74-8.59 (m, 3H), 8.35 (d, J=1.6 Hz, 1H), 7.65-7.58 (m, 3H), 5.99 (d, J=17.8 Hz, 1H), 5.70 (d, J=17.8 Hz, 1H), 4.47 (d, J=5.9 Hz, 2H), 4.30 (dd, J=9.2, 5.5 Hz, 1H), 3.55 (dd, J=5.6, 2.4 Hz, 1H), 3.18 (s, 2H), 2.72-2.62 (m, 9H), 2.48 (s, 0H), 1.97 (dd, J=13.2, 5.5 Hz, 1H), 1.31 (s, 3H), 1.02 (t, J=5.4 Hz, 1H), 0.93 (dd, J=5.4, 2.4 Hz, 1H).

(1R,3S,5R)-2-{2-[3-Acetyl-7-methyl-5-(2-methylpyrimidin-5-yl)indazol-1-yl]acetyl}-5-methyl-N-(pyridazin-3-ylmethyl)-2-azabicyclo[3.1.0]hexane-3-carboxamide ¹H NMR (400 MHz, DMSO-d₆) δ 9.10 (dd, J=4.9, 1.6 Hz, 1H), 9.05 (s, 2H), 8.65 (t, J=6.0 Hz, 1H), 8.34 (d, J=1.7 Hz, 1H), 7.63 (s, 1H), 7.54 (dd, J=8.5, 4.8 Hz, 1H), 7.47 (dd, J=8.6, 1.7 Hz, 1H), 5.98 (d, J=17.8 Hz, 1H), 5.70 (d, J=17.8 Hz, 1H), 4.57 (d, J=5.9 Hz, 2H), 4.29 (dd, J=9.2, 5.3 Hz, 1H), 3.53 (dd, J=5.7, 2.4 Hz, 1H), 2.70 (s, 3H), 2.65 (s, 3H), 2.56 (s, 3H), 2.50-2.42 (m, 1H), 1.97 (dd, J=13.3, 5.2 Hz, 1H), 1.29 (s, 3H), 1.01 (t, J=5.5 Hz, 1H), 0.90 (dd, J=5.2, 2.5 Hz, 1H).

(1R,3S,5R)-2-(2-(3-Acetyl-5-(2-methylpyrimidin-5-yl)-1H-indazol-1-yl)acetyl)-N-isopentyl-5-methyl-2-azabicyclo[3.1.0]hexane-3-carboxamide ¹H-NMR (400 MHz, DMSO-d₆): δ 9.06 (s, 2H), 8.45 (s, 1H), 7.87 (s, 2H), 7.81 (t, J=5.56 Hz, 1H), 5.87 (d, J=17.36 Hz, 1H), 5.53 (d, J=17.08 Hz, 1H), 4.16 (q, J=4.76 Hz, 1H), 3.07-3.05 (m, 2H), 2.68 (s, 3H), 2.66 (s, 3H), 2.40-2.34 (m, 2H), 1.92-1.87 (m, 1H), 1.55-1.48 (m, 1H), 1.30-1.24 (m, 5H), 0.99-0.98 (m, 2H), 0.88-0.82 (m, 6H).

(1R,3S,5R)-2-(2-(3-Acetyl-5-(2-methylpyrimidin-5-yl)-1H-indazol-1-yl)acetyl)-5-methyl-N—((S)-3-methylbutan-2-yl)-2-azabicyclo[3.1.0]hexane-3-carboxamide ¹H-NMR (400 MHz, DMSO-d₆): δ 9.07 (s, 2H), 8.45 (s, 1H), 7.87 (s, 2H), 7.51 (d, J=8.04 Hz, 1H), 5.91 (d, J=17.36 Hz, 1H), 5.53 (d, J=17.24 Hz, 1H), 4.19-4.16 (m, 1H), 3.57-3.53 (m, 2H), 2.70 (s, 3H), 2.66 (s, 3H), 2.41-2.33 (m, 1H), 1.90-1.87 (m, 1H), 1.60-1.57 (m, 1H), 1.27 (s, 3H), 0.97-0.91 (m, 5H), 0.80 (t, J=3.76 Hz, 6H).

(1R,3S,5R)-2-(2-(3-Acetyl-5-(2-methylpyrimidin-5-yl)-1H-indazol-1-yl)acetyl)-N—((S)-3,3-dimethylbutan-2-yl)-5-methyl-2-azabicyclo[3.1.0]hexane-3-carboxamide ¹H-NMR (400 MHz, DMSO-d₆): δ 9.06 (s, 2H), 8.45 (s, 1H), 7.87 (s, 2H), 7.38 (d, J=9.60 Hz, 1H), 5.93 (d, J=17.32 Hz, 1H), 5.53 (d, J=17.12 Hz, 1H), 4.23 (q, J=5.20 Hz, 1H), 3.64 (q, J=6.56 Hz, 1H), 3.55-3.54 (m, 1H), 2.70 (s, 3H), 2.66 (s, 3H), 2.38-2.33 (m, 2H), 1.90 (d, J=4.80 Hz, 1H), 1.27 (s, 3H), 0.93-0.92 (m, 4H), 0.79 (s, 9H).

(1R,3S,5R)-2-(2-(3-Acetyl-5-(2-methylpyrimidin-5-yl)-1H-indazol-1-yl)acetyl)-5-methyl-N—((S)-pentan-2-yl)-2-azabicyclo[3.1.0]hexane-3-carboxamide ¹H-NMR (400 MHz, DMSO-d₆): δ 9.06 (s, 2H), 8.45 (s, 1H), 7.87 (s, 2H), 7.52 (d, J=8.44 Hz, 1H), 5.90 (d, J=17.16 Hz, 1H), 5.52 (d, J=17.12 Hz, 1H), 4.13 (q, J=5.00 Hz, 2H), 3.73 (q, J=6.52 Hz, 1H), 3.52-3.51 (m, 1H), 2.70 (s, 3H), 2.66 (s, 3H), 2.39-2.33 (m, 2H), 1.87 (d, J=4.76 Hz, 1H), 1.50-1.47 (m, 1H), 1.35-1.33 (m, 1H), 1.27 (s, 3H), 1.27-1.20 (m, 1H), 1.17-0.97 (m, 4H), 0.80 (t, J=7.16 Hz, 3H).

(1R,3S,5R)-2-(2-(3-Acetyl-5-(2-methylpyrimidin-5-yl)-1H-indazol-1-yl)acetyl)-N—((S)-hexan-2-yl)-5-methyl-2-azabicyclo[3.1.0]hexane-3-carboxamide ¹H-NMR (400 MHz, DMSO-d₆): δ 9.05 (s, 2H), 8.45 (s, 1H), 7.87 (s, 2H), 7.52 (d, J=8.44 Hz, 1H), 5.90 (d, J=17.20 Hz, 1H), 5.52 (d, J=17.20 Hz, 1H), 4.14 (q, J=4.80 Hz, 1H), 3.73-3.69 (m, 1H), 3.52-3.51 (m, 1H), 2.70 (s, 3H), 2.66 (s, 3H), 2.41-2.34 (m, 1H), 1.87 (d, J=5.40 Hz, 1H), 1.37-1.32 (m, 3H), 1.27 (s, 3H), 1.25-1.21 (m, 4H), 1.19-0.99 (m, 4H), 0.77 (t, J=7.04 Hz, 3H).

(1R,3S,5R)-2-(2-(3-Acetyl-5-(2-methylpyrimidin-5-yl)-1H-indazol-1-yl)acetyl)-N—((S)-heptan-2-yl)-5-methyl-2-azabicyclo[3.1.0]hexane-3-carboxamide ¹H-NMR (400 MHz, DMSO-d₆): δ 9.05 (s, 2H), 8.45 (s, 1H), 7.87 (s, 2H), 7.52 (d, J=8.44 Hz, 1H), 5.90 (d, J=17.36 Hz, 1H), 5.52 (d, J=16.88 Hz, 1H), 4.14 (q, J=4.84 Hz, 1H), 3.73-3.69 (m, 1H), 3.56-3.48 (m, 1H), 2.69 (s, 3H), 2.66 (s, 3H), 2.41-2.34 (m, 2H), 1.87 (d, J=4.56 Hz, 1H), 1.34-1.33 (m, 2H), 1.27 (s, 3H), 1.24-1.10 (m, 6H), 1.00-0.96 (m, 4H), 0.77 (t, J=6.48 Hz, 3H).

(1R,3S,5R)-2-(2-(3-Acetyl-5-(2-methylpyrimidin-5-yl)-1H-indazol-1-yl)acetyl)-N—((S)-1-(4-fluorophenyl)ethyl)-5-methyl-2-azabicyclo[3.1.0]hexane-3-carboxamide ¹H-NMR (400 MHz, DMSO-d₆): δ 9.06 (s, 2H), 8.46 (s, 1H), 8.23 (d, J=8.04 Hz, 1H), 7.87 (s, 2H), 7.30-7.27 (m, 2H), 7.06 (t, J=8.84 Hz, 2H), 5.92 (d, J=17.24 Hz, 1H), 5.54 (d, J=17.16 Hz, 1H), 4.89 (t, J=7.36 Hz, 1H), 4.21 (q, J=5.24 Hz, 1H), 3.53 (t, J=3.96 Hz, 1H), 2.70 (s, 3H), 2.66 (s, 3H), 2.42-2.34 (m, 1H), 1.84 (d, J=5.32 Hz, 1H), 1.32 (d, J=7.00 Hz, 3H), 1.24 (s, 3H), 0.97-0.96 (m, 2H).

(1R,3S,5R)-2-(2-(3-Acetyl-5-(2-methylpyrimidin-5-yl)-1H-indazol-1-yl)acetyl)-N—((S)-1-(2,3-dimethylphenyl)ethyl)-5-methyl-2-azabicyclo[3.1.0]hexane-3-carboxamide ¹H-NMR (400 MHz, DMSO-d₆): δ 9.07 (s, 2H), 8.46 (s, 1H), 8.20 (d, J=7.64 Hz, 1H), 7.87 (s, 2H), 7.12-7.10 (m, 1H), 7.01-6.99 (m, 2H), 5.92 (d, J=17.28 Hz, 1H), 5.53 (d, J=17.04 Hz, 1H), 5.07 (t, J=7.16 Hz, 1H), 4.22 (q, J=5.52 Hz, 1H), 3.52-3.52 (m, 1H), 2.70 (s, 3H), 2.66 (s, 3H), 2.40-2.33 (m, 2H), 2.21 (s, 3H), 2.14 (s, 3H), 1.82 (d, J=5.00 Hz, 1H), 1.26-1.23 (m, 4H), 1.17-1.14 (m, 1H), 0.97-0.88 (m, 2H).

Scheme 93: Synthesis of (1R,3S,5R)-2-(2-(3-Acetyl-5-(2-methylpyrimidin-5-yl)-1H-indazol-1-yl)acetyl)-N-(6-bromo-4-carbamoylpyridin-2-yl)-5-methyl-2-azabicyclo[3.1.0]hexane-3-carboxamide (503)

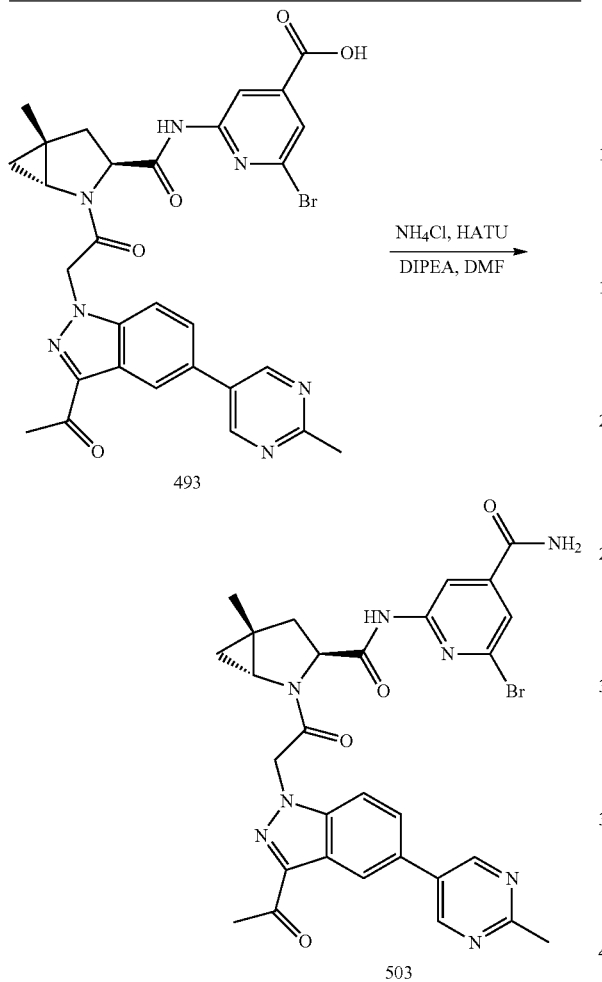

The above scheme and following detailed description depicts one non-limiting method for synthesizing compounds where the carboxylic acid on the C-ring is functionalized utilizing HATU and ammonium chloride. The skilled artisan will recognize that the A-ring can be replaced with other A-rings to afford additional compounds of the present invention. The skilled artisan will also recognize that the C-ring can be functionalized utilizing coupling reagents other than HATU.

To a mixture of Compound 493 (20 mg, 0.032 mmol) and NH₄Cl (2 mg, 0.041 mmol) in DMF (2 mL) was added HATU (0.016 g, 0.041 mmol) and DIPEA (0.012 g, 0.095 mmol) and the mixture was stirred at 25° C. for 12 hrs. The mixture was diluted with EtOAc and washed with water and brine, dried over Na₂SO₄, filtered and concentrated to dryness. The residue was purified by prep-HPLC to afford Compound 503 (6.5 mg, yield 32.5%) as white solid. ¹H-NMR (400 MHz, CDCl₃) δ 9.52 (s, 1H), 8.93 (s, 2H), 8.42 (s, 1H), 8.31 (s, 1H), 7.52-7.20 (m, 3H), 6.82 (s, 1H), 6.32 (s, 1H), 5.43 (dd, J=38.5, 16.2 Hz, 2H), 4.73 (m, 1H), 3.20 (m, 1H), 2.86 (s, 3H), 2.64 (s, 3H), 2.33 (m, 2H), 1.31 (s, 3H), 1.04 (m, 1H), 0.91 (m, 1H). LC/MS (ESI) m/z: 631/633 (M+H)⁺.

(1R,3S,5R)-2-(2-(3-Acetyl-5-(2-methylpyrimidin-5-yl)-1H-indazol-1-yl)acetyl)-N-(4-(2-amino-2-oxoethyl)-6-bromopyridin-2-yl)-5-methyl-2-azabicyclo[3.1.0]hexane-3-carboxamide ¹H-NMR (400 MHz, CD₃OD) δ 9.01 (s, 2H), 8.54 (s, 1H), 8.06 (s, 1H), 7.80 (m, 2H), 7.24 (m, 1H), 5.82 (d, J=17.4 Hz, 1H), 5.64 (d, J=17.2 Hz, 1H), 4.48 (m, 1H), 3.55 (m, 1H), 3.51 (m, 2H), 2.75 (s, 3H), 2.70 (s, 3H), 2.63-2.49 (m, 1H), 2.20-2.16 (m, 1H), 1.37 (s, 3H), 1.07 (m, 1H), 0.99 (m, 1H). LC/MS (ESI) m/z: 645/647 (M+H)⁺.

(1R,3S,5R)-2-(2-(3-Acetyl-5-(2-methylpyrimidin-5-yl)-1H-indazol-1-yl)acetyl)-5-methyl-N—((S)-1-(p-tolyl)ethyl)-2-azabicyclo[3.1.0]hexane-3-carboxamide ¹H-NMR (400 MHz, CD₃OD): δ 9.07 (s, 2H), 8.57 (s, 1H), 7.80 (s, 2H), 7.16 (d, J=8.00 Hz, 2H), 7.10 (d, J=8.40 Hz, 2H), 5.78 (d, J=17.20 Hz, 1H), 5.61 (d, J=17.20 Hz, 1H), 4.95-4.94 (m, 1H), 4.37-4.33 (m, 1H), 3.49-3.47 (m, 1H), 2.79 (s, 3H), 2.71 (s, 3H), 2.51-2.46 (m, 1H), 2.30 (s, 3H), 2.01-1.96 (m, 1H), 1.39 (d, J=6.80 Hz, 3H), 1.31 (s, 3H), 1.05 (t, J=5.60 Hz, 1H), 0.95-0.93 (m, 1H).

(1R,3S,5R)-2-(2-(3-Acetyl-5-(2-methylpyrimidin-5-yl)-1H-indazol-1-yl)acetyl)-N—((S)-1-(3-chlorophenyl)ethyl)-5-methyl-2-azabicyclo[3.1.0]hexane-3-carboxamide ¹H-NMR (400 MHz, CD₃OD): δ 9.07 (s, 2H), 8.58 (s, 1H), 7.84-7.79 (m, 2H), 7.31-7.27 (m, 2H), 7.25-7.22 (m, 2H), 5.79 (d, J=17.20 Hz, 1H), 5.64 (d, J=17.20 Hz, 1H), 4.95-4.85 (m, 1H), 4.37-4.34 (m, 1H), 3.50-3.48 (m, 1H), 2.79 (s, 3H), 2.72 (s, 3H), 2.54-2.49 (m, 1H), 1.99 (d, J=5.60 Hz, 1H), 1.42 (d, J=7.20 Hz, 3H), 1.32 (s, 3H), 1.08-1.05 (m, 1H), 0.97-0.96 (m, 1H).

(1R,3S,5R)-2-(2-(3-Acetyl-5-(2-methylpyrimidin-5-yl)-1H-indazol-1-yl)acetyl)-N—((S)-1-(2-fluorophenyl)ethyl)-5-methyl-2-azabicyclo[3.1.0]hexane-3-carboxamide ¹H-NMR (400 MHz, DMSO-d₆): δ 9.07 (s, 2H), 8.46 (s, 1H), 8.31 (d, J=7.52 Hz, 1H), 7.90 (s, 2H), 7.32-7.22 (m, 2H), 7.12-7.04 (m, 2H), 5.94 (d, J=17.12 Hz, 1H), 5.54 (d, J=17.20 Hz, 1H), 5.08 (t, J=6.92 Hz, 1H), 4.22 (q, J=4.72 Hz, 1H), 3.53-3.43 (m, 1H), 2.70 (s, 3H), 2.66 (s, 3H), 2.43-2.33 (m, 1H), 1.85-1.81 (m, 1H), 1.32 (d, J=6.96 Hz, 3H), 1.13 (s, 3H), 0.96 (d, J=3.40 Hz, 2H).

(1R,3S,5R)-2-(2-(3-Acetyl-5-(2-methylpyrimidin-5-yl)-1H-indazol-1-yl)acetyl)-5-methyl-N—((S)-1-phenylethyl)-2-azabicyclo[3.1.0]hexane-3-carboxamide ¹H-NMR (400 MHz, CD₃OD): δ 9.06 (s, 2H), 8.57 (s, 1H), 7.81 (s, 2H), 7.30-7.30 (m, 4H), 7.29-7.18 (m, 1H), 5.79 (d, J=17.20 Hz, 1H), 5.63 (d, J=17.20 Hz, 1H), 5.12-5.06 (m, 1H), 4.38-4.34 (m, 1H), 3.49-3.48 (m, 1H), 2.79 (s, 3H), 2.72 (s, 3H), 2.50 (q, J=9.20 Hz, 1H), 1.99 (q, J=5.20 Hz, 1H), 1.42 (d, J=6.80 Hz, 3H), 1.32 (s, 3H), 1.07-1.04 (m, 1H), 0.95-0.93 (m, 1H).

(1R,3S,5R)-2-(2-(3-Acetyl-5-(2-methylpyrimidin-5-yl)-1H-indazol-1-yl)acetyl)-5-methyl-N—((R)-1-phenylethyl)-2-azabicyclo[3.1.0]hexane-3-carboxamide ¹H-NMR (400 MHz, DMSO-d₆): δ 9.06 (s, 2H), 8.45 (s, 1H), 8.20 (d, J=8.24 Hz, 1H), 7.87 (s, 2H), 7.30-7.19 (m, 5H), 5.90 (d, J=17.24 Hz, 1H), 5.54 (d, J=17.20 Hz, 1H), 4.92 (t, J=7.88 Hz, 1H), 4.27 (q, J=4.76 Hz, 1H), 2.69 (s, 3H), 2.63 (s, 3H), 2.44-2.33 (m, 2H), 1.92 (d, J=4.72 Hz, 1H), 1.36-1.24 (m, 6H), 1.00-0.98 (m, 2H).

(1R,3S,5R)-2-(2-(3-Acetyl-5-(2-methylpyrimidin-5-yl)-1H-indazol-1-yl)acetyl)-N-(3,3-dimethylbutyl)-5-methyl-2-azabicyclo[3.1.0]hexane-3-carboxamide $^1$H-NMR (400 MHz, DMSO-d$_6$): δ 9.06 (s, 2H), 8.45 (d, J=0.92 Hz, 1H), 7.87 (s, 2H), 7.79 (t, J=5.64 Hz, 1H), 5.87 (d, J=17.32 Hz, 1H), 5.53 (d, J=17.12 Hz, 1H), 4.17-4.13 (m, 1H), 3.47 (s, 1H), 3.05 (q, J=7.92 Hz, 2H), 2.70 (s, 3H), 2.66 (s, 3H), 2.39-2.33 (m, 1H), 2.09-2.08 (m, 1H), 1.31-1.26 (m, 4H), 0.99-0.97 (m, 2H), 0.96 (s, 1H), 0.87 (s, 9H).

Scheme 94. Synthesis of (1R,3S,5R)-5-((1H-Pyrazol-1-yl)methyl)-2-(2-(3-acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide (310)

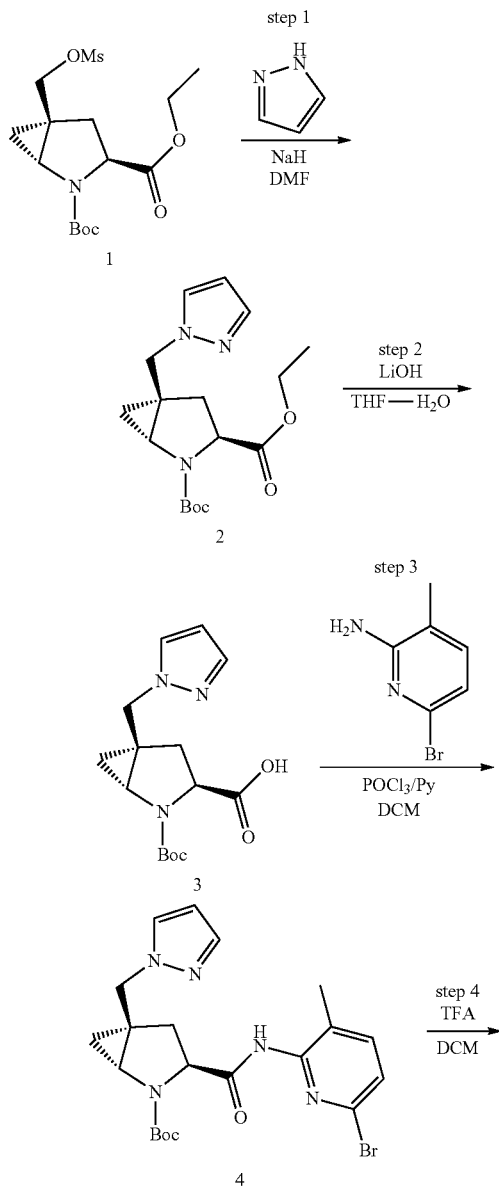

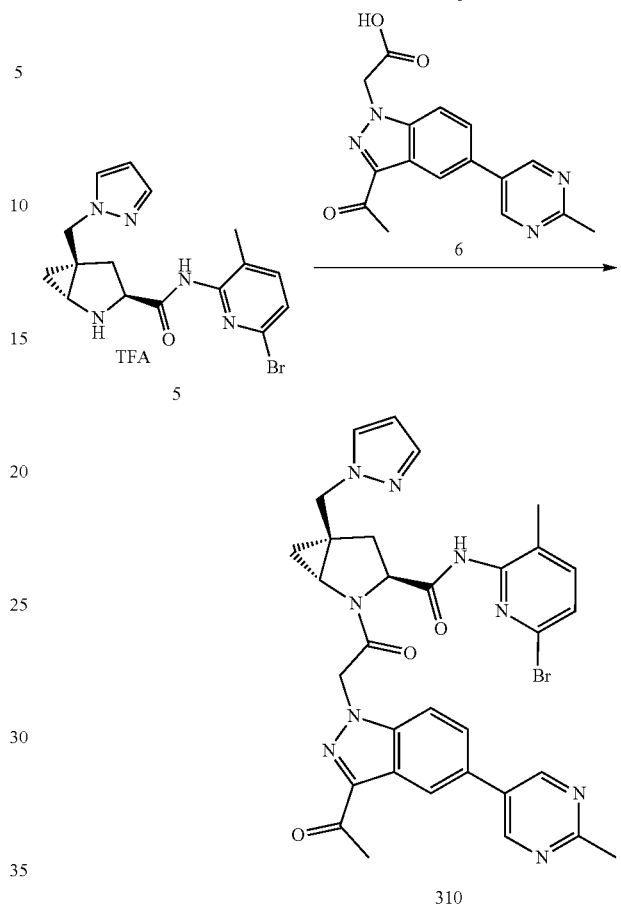

The above scheme and following detailed description depicts one non-limiting method for synthesizing compounds with nucleophilic R$^{201}$ groups on the C-Ring. The skilled artisan will recognize that pyrazole can be replaced with other nucleophilic reagents to afford additional compounds of the present invention. Non-limiting examples of groups the skilled artisan can use instead of pyrazole include: triazole, imidazole, azetidine, or the like.

Step 1: 2-(tert-butyl) 3-ethyl (1R,3S,5R)-5-((1H-pyrazol-1-yl)methyl)-2-azabicyclo[3.1.0]hexane-2,3-dicarboxylate (2)

Into pyrazole (0.035 g, 0.51 mmol) in DMF 0.5 ml, sodium hydride (0.02 g, 0.51 mmol) was added with stirring. After 20 minutes at room temperature, 2-tert-butyl 3-ethyl (1R,3S,5S)-5-[(methanesulfonyloxy)methyl]-2-azabicyclo[3.1.0]hexane-2,3-dicarboxylate 1 (0.124 g, 0.34 mmol) in DMF (2 mL) was added. The mixture was stirred at 60° C. for 3 hours to afford a racemic mixture. The resulting solid was removed by filtration and the filtrate was purified by HPLC to afford 2-tert-butyl 2-(tert-butyl) 3-ethyl (1R,3S,5R)-5-((1H-pyrazol-1-yl)methyl)-2-azabicyclo[3.1.0]hexane-2,3-dicarboxylate 2 (24 mg).

Step 2: (1R,3S,5R)-5-((1H-Pyrazol-1-yl)methyl)-2-(tert-butoxycarbonyl)-2-azabicyclo[3.1.0]hexane-3-carboxylic Acid (3)

2-(tert-Butyl) 3-ethyl (1R,3S,5R)-5-((1H-pyrazol-1-yl)methyl) (24 mg, 0.072 mmol) was treated with lithium hydroxide (1.5 N, 0.072 mL, 0.107 mmol) in THF (1 mL) and ethanol (0.1 mL) at room temperature overnight. After the reaction was completed, Amberlite CG-50 (0.1 g) was added and the mixture was stirred for 30 minutes. Resin was removed by filtration and washed with MeOH. Solvent was removed under reduced pressure to afford (1R,3S,5R)-5-((1H-pyrazol-1-yl) methyl)-2-(tert-butoxycarbonyl)-2-azabicyclo[3.1.0] hexane-3-carboxylic acid 3 (25 mg).

Step 3: tert-Butyl (1R,3S,5R)-5-((1H-pyrazol-1-yl) methyl)-3-((6-bromo-3-methylpyridin-2-yl)carbamoyl)-2-azabicyclo[3.1.0]hexane-2-carboxylate (4)

Into mixture of (1R,3S,5R)-5-((1H-pyrazol-1-yl)methyl)-2-(tert-butoxycarbonyl)-2-azabicyclo[3.1.0]hexane-3-carboxylic acid 3 (25 mg) and 6-bromo-3-methylpyridin-2-amine (15.2 mg) in DCM (1.5 mL), pyridine (0.033 mL, 0.407 mmol) followed by phosphoryl chloride (7.6 µL, 0.081 mmol) was added with stirring. After 2 hours, NaHCO$_3$ aqueous solution was added. The mixture was extracted with DCM. Solvent was removed under reduced pressure and the residue was purified by column chromatography on silica gel (MeOH in DCM 0-10%) to afford tert-butyl (1R,3S,5R)-5-((1H-pyrazol-1-yl)methyl)-3-((6-bromo-3-methylpyridin-2-yl)carbamoyl)-2-azabicyclo [3.1.0]hexane-2-carboxylate S4 (23 mg).

Step 4: (1R,3S,5R)-5-((1H-pyrazol-1-yl)methyl)-N-(6-bromo-3-methylpyridin-2-yl)-2-azabicyclo[3.1.0] hexane-3-carboxamide TFA Salt (5)

tert-Butyl (1R,3S,5R)-5-((1H-pyrazol-1-yl)methyl)-3-((6-bromo-3-methylpyridin-2-yl)carbamoyl)-2-azabicyclo [3.1.0]hexane-2-carboxylate 4 (23 mg, 0.048 mmol) was treated with TFA (1.0 mL) in DCM (1 mL) at room temperature for 2 hours. Solvent was removed under reduced pressure and the residue was co-evaporated with toluene (5 ml×2) to afford (1R,3S,5R)-5-((1H-pyrazol-1-yl)methyl)-N-(6-bromo-3-methylpyridin-2-yl)-2-azabicyclo[3.1.0] hexane-3-carboxamide TFA salt 5 for next step.

Step 5: (1R,3S,5R)-5-((1H-Pyrazol-1-yl)methyl)-2-(2-(3-acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide (310)

Into mixture of (1R,3S,5R)—N-(6-bromo-3-methylpyridin-2-yl)-5-(pyrazol-1-ylmethyl)-2-azabicyclo[3.1.0] hexane-3-carboxamide TFA salt 5 (0.048 mmol) and [3-acetyl-5-(2-methylpyrimidin-5-yl)indazol-1-yl]acetic acid 6 (0.015 g, 0.048 mmol) in DMF (1 mL), TBTU (0.023 g, 0.072 mmol) followed by N,N-diisopropylethylamine (0.062 g, 0.084 mL, 0.48 mmol) was added with stirring. After reaction was complete, NaHCO$_3$ aqueous solution was added. The mixture was extracted with EtOAc and solvent was removed under reduced pressure. The residue was purified by column chromatography on silica gel (MeOH in DCM 0-10%) to afford (1R,3S,5R)-5-((1H-pyrazol-1-yl)methyl)-2-(2-(3-acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide (310) (25 mg). $^1$H NMR (400 MHz, Chloroform-d) δ 8.93-8.86 (m, 2H), 8.74 (s, 1H), 8.59-8.52 (m, 1H), 7.70-7.59 (m, 1H), 7.55-7.51 (m, 1H), 7.45 (q, J=2.1 Hz, 1H), 7.34 (dd, J=3.5, 8.3 Hz, 1H), 7.23 (dd, J=4.0, 7.9 Hz, 1H), 6.27 (p, J=2.2 Hz, 1H), 5.57-5.42 (m, 2H), 4.88 (s, 1H), 4.53 (dd, J=7.2, 14.1 Hz, 1H), 4.35 (dt, J=2.2, 14.3 Hz, 1H), 3.49 (dd, J=2.8, 5.8 Hz, 1H), 2.80 (d, J=2.3 Hz, 3H), 2.70 (dd, J=1.5, 2.6 Hz, 3H), 2.26 (dd, J=8.7, 13.7 Hz, 1H), 1.26 (q, J=6.3 Hz, 1H), 1.03 (dd, J=3.5, 6.0 Hz, 1H). LC (method A): t$_R$=1.62 min. LC/MS (EI) m/z: [M+H]$^+$ 668.

(1R,3S,5R)-2-(2-(3-Acetyl-5-(2-methylpyrimidin-5-yl)-1H-indazol-1-yl)acetyl)-N-(6-bromo-3-methylpyridin-2-yl)-5-((3-(tert-butyl)-1H-pyrazol-1-yl) methyl)-2-azabicyclo[3.1.0]hexane-3-carboxamide $^1$H NMR (400 MHz, Chloroform-d) δ 8.90 (s, 2H), 8.70 (d, J=14.2 Hz, 1H), 8.57 (dd, J=0.8, 1.7 Hz, 1H), 7.70-7.56 (m, 2H), 7.39-7.19 (m, 4H), 6.09 (d, J=2.3 Hz, 1H), 5.48 (s, 2H), 4.89 (d, J=7.9 Hz, 1H), 4.53 (d, J=14.4 Hz, 1H), 4.34 (d, J=14.3 Hz, 1H), 4.12 (q, J=7.1 Hz, 1H), 3.39 (dd, J=2.7, 5.8 Hz, 1H), 2.81 (s, 4H), 2.70 (s, 4H), 2.28 (t, J=11.3 Hz, 1H), 2.05 (d, J=3.5 Hz, 4H), 1.99 (s, 2H), 1.28 (s, 9H), 1.20-1.15 (m, 1H), 0.96 (dd, J=2.7, 5.9 Hz, 1H). LC (method A): t$_R$=2.22 min. LC/MS (EI) m/z: [M+H]$^+$ 724.

(1R,3S,5R)-5-((1H-1,2,4-Triazol-1-yl)methyl)-2-(2-(3-acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide $^1$H NMR (400 MHz, Chloroform-d) δ 8.90 (d, J=2.6 Hz, 2H), 8.81 (s, 1H), 8.56 (t, J=2.2 Hz, 1H), 8.20 (s, 1H), 7.98 (d, J=2.0 Hz, 1H), 7.67-7.55 (m, 2H), 7.38-7.30 (m, 1H), 7.23 (d, J=8.0 Hz, 1H), 5.61-5.41 (m, 2H), 4.91 (d, J=8.2 Hz, 1H), 4.62 (d, J=14.0 Hz, 1H), 4.30 (d, J=14.4 Hz, 1H), 3.58 (dd, J=5.9, 2.8 Hz, 1H), 2.80 (d, J=2.0 Hz, 3H), 2.71 (d, J=2.1 Hz, 3H), 2.21 (q, J=15.8, 13.0 Hz, 2H), 2.03 (d, J=2.5 Hz, 3H), 1.38 (t, J=5.8 Hz, 1H), 1.12 (dd, J=6.1, 2.9 Hz, 1H). LC (method A): t$_R$=1.36 min. LC/MS (EI) m/z: [M+H]$^+$ 669.

(1R,3S,5R)-5-((1H-1,2,4-Triazol-1-yl)methyl)-2-(2-(3-acetyl-5-(2-methylpyrimidin-5-yl)-1H-pyrazolo [3,4-c]pyridin-1-yl)acetyl)-N-(6-bromo-3-methylpyridin-2-yl)-2-azabicyclo[3.1.0]hexane-3-carboxamide $^1$H NMR (400 MHz, Chloroform-d) δ 9.28 (s, 2H), 9.10 (d, J=1.3 Hz, 1H), 8.72 (s, 1H), 8.62 (d, J=1.3 Hz, 1H), 8.21 (s, 1H), 7.99 (s, 1H), 7.34 (dd, J=0.8, 7.9 Hz, 1H), 7.22 (d, J=7.9 Hz, 1H), 5.73-5.50 (m, 2H), 4.92 (d, J=8.4 Hz, 1H), 4.62 (d, J=14.4 Hz, 1H), 4.34 (d, J=14.4 Hz, 1H), 3.64 (dd, J=2.8, 5.9 Hz, 1H), 2.81 (s, 3H), 2.76 (s, 1H), 2.72 (s, 3H), 2.32 (s, 1H), 2.04 (s, 3H), 1.43 (t, J=6.0 Hz, 1H), 1.18 (dd, J=2.9, 6.1 Hz, 1H). LC (method A): t$_R$=1.27 min. LC/MS (EI) m/z: [M+H]$^+$ 670.

Scheme 95. Synthesis of (1R,3S,5R)-2-(2-(3-Acetyl-5-(2-methylpyrimidin-5-yl)-1H-indazol-1-yl)acetyl)-N-(6-bromo-3-methylpyridin-2-yl)-5-((4-methyl-1H-imidazol-1-yl)methyl)-2-azabicyclo[3.1.0]hexane-3-carboxamide (314) and (1R,3S,5R)-5-((1H-1,2,4-Triazol-1-yl)methyl)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-2-azabicyclo[3.1.0]hexane-3-carboxamide (315)

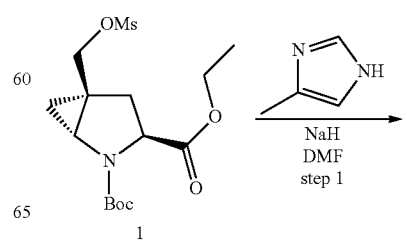

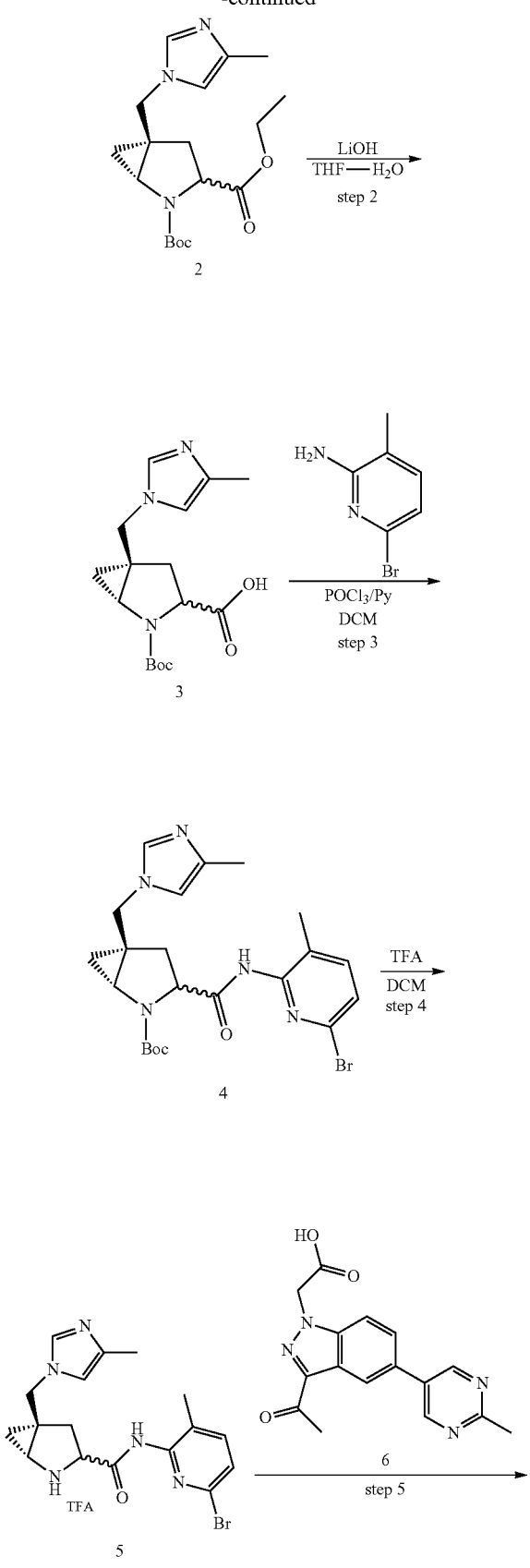

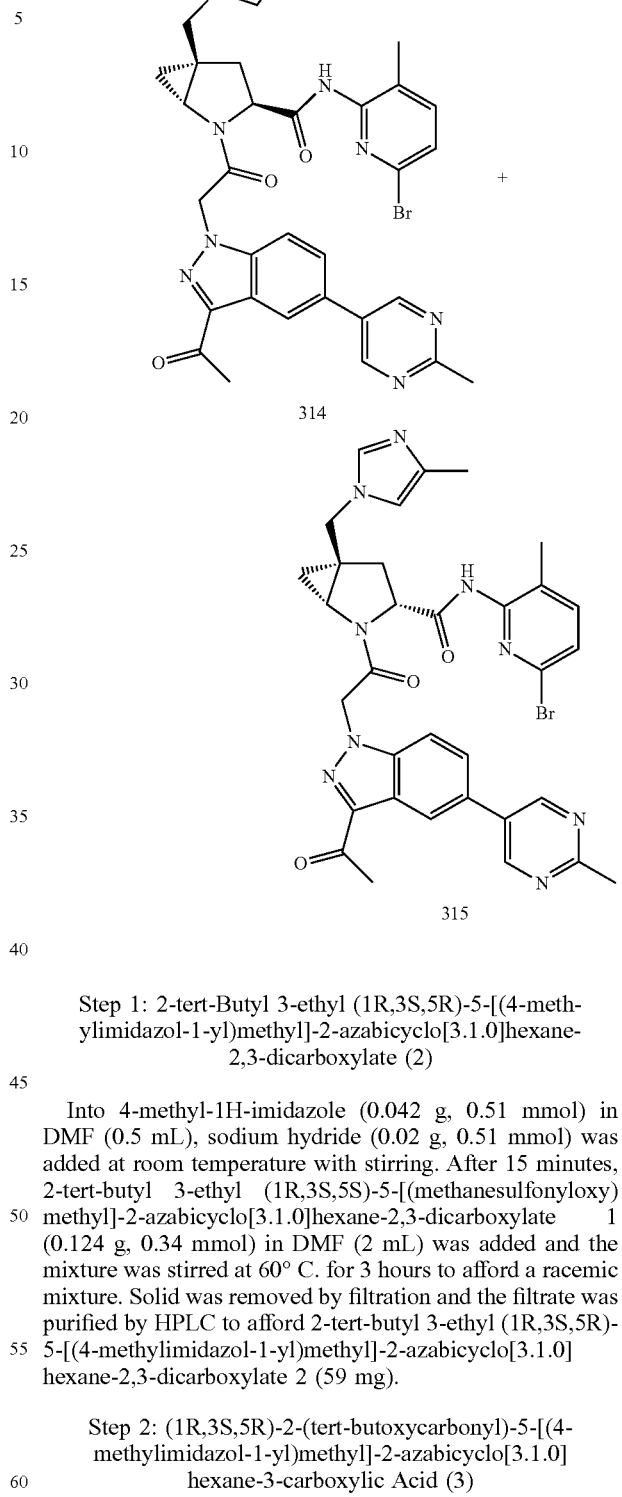

Step 1: 2-tert-Butyl 3-ethyl (1R,3S,5R)-5-[(4-methylimidazol-1-yl)methyl]-2-azabicyclo[3.1.0]hexane-2,3-dicarboxylate (2)

Into 4-methyl-1H-imidazole (0.042 g, 0.51 mmol) in DMF (0.5 mL), sodium hydride (0.02 g, 0.51 mmol) was added at room temperature with stirring. After 15 minutes, 2-tert-butyl 3-ethyl (1R,3S,5S)-5-[(methanesulfonyloxy)methyl]-2-azabicyclo[3.1.0]hexane-2,3-dicarboxylate 1 (0.124 g, 0.34 mmol) in DMF (2 mL) was added and the mixture was stirred at 60° C. for 3 hours to afford a racemic mixture. Solid was removed by filtration and the filtrate was purified by HPLC to afford 2-tert-butyl 3-ethyl (1R,3S,5R)-5-[(4-methylimidazol-1-yl)methyl]-2-azabicyclo[3.1.0]hexane-2,3-dicarboxylate 2 (59 mg).

Step 2: (1R,3S,5R)-2-(tert-butoxycarbonyl)-5-[(4-methylimidazol-1-yl)methyl]-2-azabicyclo[3.1.0]hexane-3-carboxylic Acid (3)

2-tert-Butyl 3-ethyl (1R,3S,5R)-5-[(4-methylimidazol-1-yl)methyl]-2-azabicyclo[3.1.0]hexane-2,3-dicarboxylate S2 (57.4 mg) was treated with lithium hydroxide (10 mg) in THF (2 mL), ethanol (0.15 mL), and water (0.15 mL) at room temperature for 4 days. Amberlite CG-50 (0.2 g) was added and the mixture was stirred for 30 minutes. Resin was removed by filtration and washed with MeOH. Solvent was removed under reduced pressure to afford (1R,3S,5R)-2-(tert-butoxycarbonyl)-5-[(4-methylimidazol-1-yl)methyl]-2-azabicyclo[3.1.0]hexane-3-carboxylic acid 3 (59 mg).

Step 3: tert-butyl (1R,3S,5R)-3-[(6-bromo-3-methylpyridin-2-yl)carbamoyl]-5-[(4-methylimidazol-1-yl)methyl]-2-azabicyclo[3.1.0]hexane-2-carboxylate (4)

Into the mixture of (1R,3S,5R)-2-(tert-butoxycarbonyl)-5-[(4-methylimidazol-1-yl)methyl]-2-azabicyclo[3.1.0]hexane-3-carboxylic acid S3 (53 mg, 0.164 mmol) and 6-bromo-3-methylpyridin-2-amine (34 mg, 0.18 mmol) in DCM (3.0 mL), pyridine (0.066 mL, 0.82 mmol) followed by phosphoryl chloride (15 µL, 0.16 mmol) was added at 0° C. with stirring. After 2 hours at room temperature, NaHCO₃ aqueous solution was added. The mixture was extracted with DCM. Solvent was removed under reduced pressure and the residue was purified by column chromatography on silica gel (MeOH in DCM 0-10%) to afford tert-butyl (1R,3S,5R)-3-[(6-bromo-3-methylpyridin-2-yl)carbamoyl]-5-[(4-methylimidazol-1-yl)methyl]-2-azabicyclo[3.1.0]hexane-2-carboxylate 4 (35 mg) as white solid.

Step 4: (1R,3S,5R)—N-(6-bromo-3-methylpyridin-2-yl)-5-[(4-methylimidazol-1-yl)methyl]-2-azabicyclo[3.1.0]hexane-3-carboxamide TFA Salt (5)

tert-Butyl (1R,3S,5R)-3-[(6-bromo-3-methylpyridin-2-yl)carbamoyl]-5-[(4-methylimidazol-1-yl)methyl]-2-azabicyclo[3.1.0]hexane-2-carboxylate 4 (35 mg, 0.065 mmol) was treated with TFA (2.0 mL) in DCM (2 mL) at room temperature for 2 hours. Solvent was removed under reduced pressure and the residue was co-evaporated with toluene (5 ml×2) to afford (1R,3S,5R)—N-(6-bromo-3-methylpyridin-2-yl)-5-[(4-methylimidazol-1-yl)methyl]-2-azabicyclo[3.1.0]hexane-3-carboxamide TFA salt S5 for next step.

Step 5: (1R,3S,5R)-2-(2-(3-Acetyl-5-(2-methylpyrimidin-5-yl)-1H-indazol-1-yl)acetyl)-N-(6-bromo-3-methylpyridin-2-yl)-5-((4-methyl-1H-imidazol-1-yl)methyl)-2-azabicyclo[3.1.0]hexane-3-carboxamide (314) and (1R,3R,5R)-5-((1H-1,2,4-Triazol-1-yl)methyl)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-2-azabicyclo[3.1.0]hexane-3-carboxamide (315)

Into a mixture of (1R,3S,5R)—N-(6-bromo-3-methylpyridin-2-yl)-5-[(4-methylimidazol-1-yl)methyl]-2-azabicyclo[3.1.0]hexane-3-carboxamide TFA salt S5 (0.065 mmol) and [3-acetyl-5-(2-methylpyrimidin-5-yl)indazol-1-yl]acetic acid S6 (0.020 g, 0.065 mmol) in DMF (1 mL), TBTU (0.04 g, 0.098 mmol) followed by N,N-diisopropylethylamine (0.091 mL, 0.52 mmol) was added with stirring. After the reaction was complete, the mixture was purified with HPLC to afford (1R,3S,5R)-2-(2-(3-acetyl-5-(2-methylpyrimidin-5-yl)-1H-indazol-1-yl)acetyl)-N-(6-bromo-3-methylpyridin-2-yl)-5-((4-methyl-1H-imidazol-1-yl)methyl)-2-azabicyclo[3.1.0]hexane-3-carboxamide (314) (17 mg) and (315) (18 mg).

(1R,3S,5R)-2-(2-(3-Acetyl-5-(2-methylpyrimidin-5-yl)-1H-indazol-1-yl)acetyl)-N-(6-bromo-3-methylpyridin-2-yl)-5-((4-methyl-1H-imidazol-1-yl)methyl)-2-azabicyclo[3.1.0]hexane-3-carboxamide (314)

¹H NMR (400 MHz, Chloroform-d) δ 8.90 (s, 2H), 8.80 (s, 1H), 8.57 (dt, J=0.8, 1.6 Hz, 1H), 7.71-7.56 (m, 2H), 7.53-7.33 (m, 2H), 7.28-7.20 (m, 2H), 6.84-6.64 (m, 1H), 5.59-5.38 (m, 2H), 4.96 (d, J=8.1 Hz, 1H), 4.44 (t, J=15.5 Hz, 1H), 4.00 (dd, J=14.5, 37.2 Hz, 1H), 3.41-3.25 (m, 1H), 2.81 (s, 3H), 2.71 (d, J=2.0 Hz, 3H), 2.22 (dd, J=0.9, 2.1 Hz, 3H), 2.05 (d, J=1.5 Hz, 3H), 2.04-1.97 (m, 4H), 1.28 (dd, J=5.4, 11.4 Hz, 1H), 1.13 (td, J=2.7, 6.0, 6.7 Hz, 1H). LC (method A): $t_R$=1.12 min. LC/MS (EI) m/z: [M+H]⁺ 682.

(1R,3R,5R)-2-(2-(3-Acetyl-5-(2-methylpyrimidin-5-yl)-1H-indazol-1-yl)acetyl)-N-(6-bromo-3-methylpyridin-2-yl)-5-((4-methyl-1H-imidazol-1-yl)methyl)-2-azabicyclo[3.1.0]hexane-3-carboxamide (315)

¹H NMR (400 MHz, Chloroform-d) δ 8.89 (s, 3H), 8.56 (dd, J=0.9, 1.8 Hz, 1H), 7.69-7.53 (m, 3H), 7.53-7.37 (m, 1H), 7.33 (d, J=7.9 Hz, 1H), 7.21 (d, J=7.9 Hz, 1H), 6.72 (d, J=74.9 Hz, 1H), 5.63-5.37 (m, 3H), 5.14 (t, J=19.5 Hz, 2H), 4.04 (d, J=6.7 Hz, 3H), 3.54 (ddd, J=2.7, 6.4, 16.7 Hz, 1H), 2.80 (s, 4H), 2.72 (d, J=1.3 Hz, 4H), 2.49 (d, J=13.5 Hz, 1H), 2.21 (s, 4H), 2.02 (d, J=6.5 Hz, 9H), 0.95 (t, J=6.4 Hz, 1H), 0.87 (t, J=6.2 Hz, 0H). LC (method A): $t_R$=1.19 min. LC/MS (EI) m/z: [M+H]⁺ 682.

Scheme 96. Synthesis of (1R,3S,5R)-2-{2-[3-Acetyl-5-(2-methylpyrimidin-5-yl)indazol-1-yl]acetyl}-N-(6-bromo-3-methylpyridin-2-yl)-5-[(4-tert-butyl-1,3-thiazol-2-yl)methyl]-2-azabicyclo[3.1.0]hexane-3-carboxamide (338)

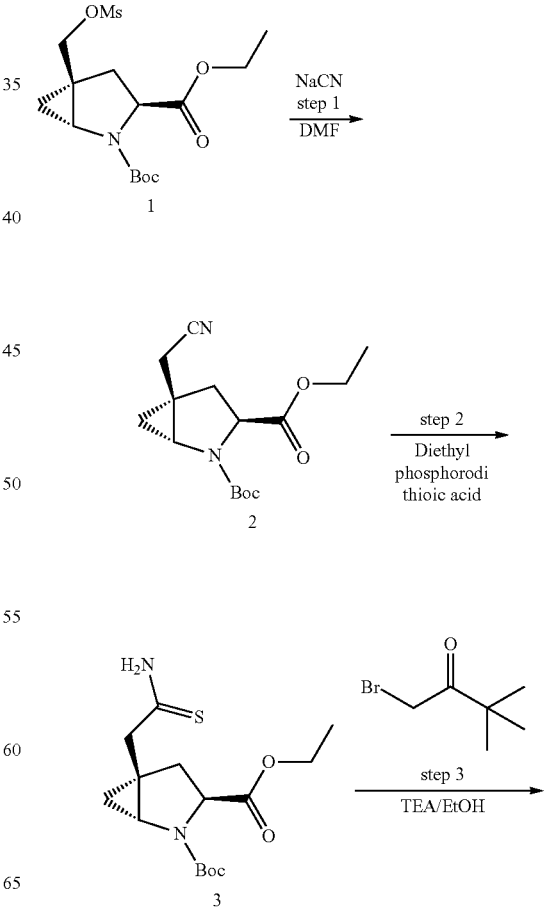

929

-continued

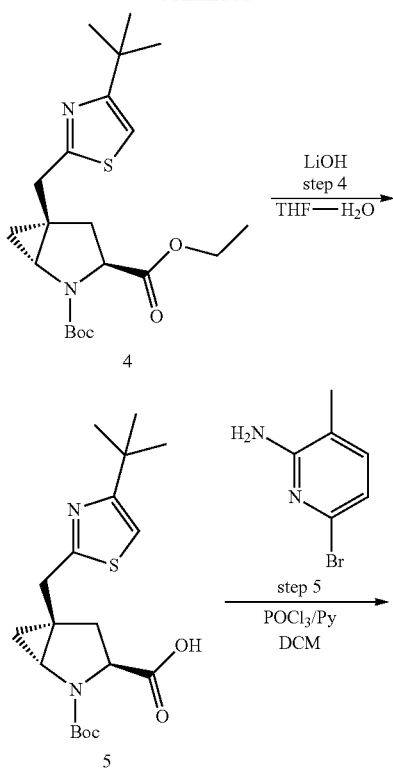

930

-continued

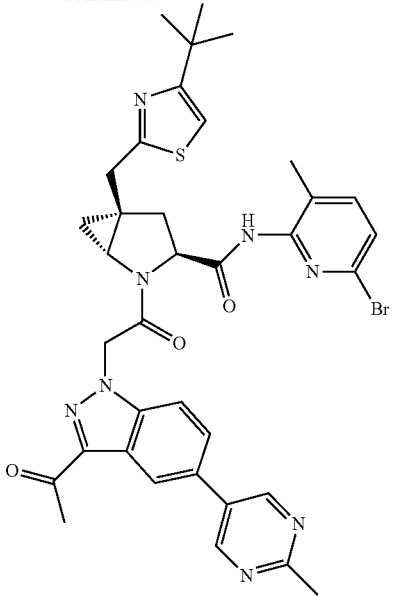

338

Step 1: 2-tert-butyl 3-ethyl (1R,3S,5R)-5-(cyanomethyl)-2-azabicyclo[3.1.0]hexane-2,3-dicarboxylate (2)

Into 2-tert-Butyl 3-ethyl (1R,3S,5S)-5-[(methanesulfonyloxy)methyl]-2-azabicyclo[3.1.0]hexane-2,3-dicarboxylate 1 (0.124 g, 0.34 mmol) in DMF (2.5 ml), sodium cyanide (0.083 g, 1.7 mmol) was added with stirring. The mixture was stirred at 60° C. for 3 hours. Solid was removed by filtration. Filtrate was diluted with water and extracted with EtOAc. Organic layer was washed with water, brine, and dried over anhydrous $Na_2SO_4$. Solvent was removed under reduced pressure, and the residue was purified by column chromatography on silica gel (EtOAc in Hex 0-50%) to afford 2-tert-butyl 3-ethyl (1R,3S,5R)-5-(cyanomethyl)-2-azabicyclo[3.1.0]hexane-2,3-dicarboxylate 2 (81 mg) as colorless oil.

Step 2: 2-tert-Butyl 3-ethyl (1R,3S,5R)-5-(carbamothioylmethyl)-2-azabicyclo[3.1.0]hexane-2,3-dicarboxylate (3)

2-tert-Butyl 3-ethyl (1R,3S,5R)-5-(cyanomethyl)-2-azabicyclo[3.1.0]hexane-2,3-dicarboxylate (40 mg, 0.136 mmol) was dissolved in hydrochloric acid 4N in dioxane (0.34 mL, 1.36 mmol) and treated with diethyl phosphorodithioic acid (0.034 mL, 0.204 mmol) at room temperature for 1 day. Water (10 mL) was added followed by 1N NaOH aqueous solution to adjust the pH to approximately 9. Into the mixture, di-tert-butyl dicarbonate (0.297 g, 1.36 mmol) in EtOAc (10 mL) was added with vigorous stirring for 15 minutes. The EtOAc layer was separated and washed with brine. Solvent was removed under reduced pressure and the residue was purified by column chromatography on silica gel (EtOAc in Hex, 0-50%) to afford 2-tert-butyl 3-ethyl (1R,3S,5R)-5-(carbamothioylmethyl)-2-azabicyclo[3.1.0]hexane-2,3-dicarboxylate 3 (24 mg).

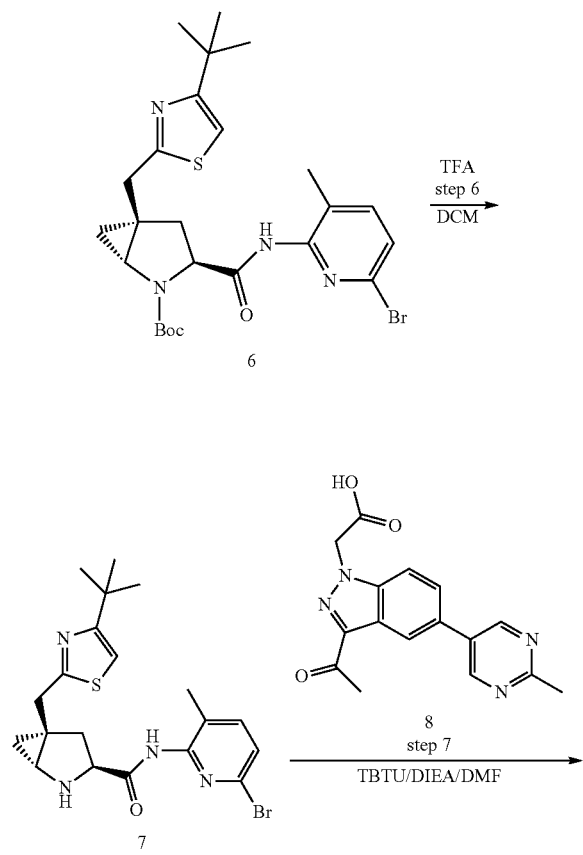

Step 3: 2-tert-Butyl 3-ethyl (1R,3S,5R)-5-[(4-tert-butyl-1,3-thiazol-2-yl)methyl]-2-azabicyclo[3.1.0]hexane-2,3-dicarboxylate (4)

A mixture of 2-tert-butyl 3-ethyl (1R,3S,5R)-5-(carbamothioylmethyl)-2-azabicyclo[3.1.0]hexane-2,3-dicarboxylate (24 mg, 0.073 mmol), 1-bromopinacolone (0.015 g, 0.08 mmol), and triethylamine (0.011 mL, 0.08 mmol) was refluxed in ethanol (5 mL) under Ar for 1 hour. Solvent was removed under reduced pressure and residue was purified with column chromatography on silica gel to afford intermediate. The hydrate intermediate was refluxed in toluene (5 mL) for an additional 2 hours. Solvent was removed under reduced pressure to afford 2-tert-butyl 3-ethyl (1R,3S,5R)-5-[(4-tert-butyl-1,3-thiazol-2-yl)methyl]-2-azabicyclo[3.1.0]hexane-2,3-dicarboxylate 4 (23 mg).

Step 4: (1R,3S,5R)-2-(tert-Butoxycarbonyl)-5-[(4-tert-butyl-1,3-thiazol-2-yl)methyl]-2-azabicyclo[3.1.0]hexane-3-carboxylic Acid (5)

2-tert-Butyl 3-ethyl (1R,3S,5R)-5-[(4-tert-butyl-1,3-thiazol-2-yl)methyl]-2-azabicyclo[3.1.0]hexane-2,3-dicarboxylate (23 mg, 0.056 mmol) in tetrahydrofuran (0.5 mL) and ethanol 0.05 mL) was treated with lithium hydroxide (1.5 N, 0.056 mL, 0.084 mmol) at room temperature overnight. After the reaction was completed, Amberlite CG-50 (0.1 g, 1 equiv.) was added and stirred for 10 minutes. Resin was removed by filtration and washed with MeOH. Filtrate was concentrated and the residue was co-evaporated with toluene to afford (1R,3S,5R)-2-(tert-butoxycarbonyl)-5-[(4-tert-butyl-1,3-thiazol-2-yl)methyl]-2-azabicyclo[3.1.0]hexane-3-carboxylic acid 5 (21 mg) for next step.

Step 5: tert-Butyl (1R,3S,5R)-3-[(6-bromo-3-methylpyridin-2-yl)carbamoyl]-5-[(4-tert-butyl-1,3-thiazol-2-yl)methyl]-2-azabicyclo[3.1.0]hexane-2-carboxylate (6)

A mixture of (1R,3S,5R)-2-(tert-butoxycarbonyl)-5-[(4-tert-butyl-1,3-thiazol-2-yl)methyl]-2-azabicyclo[3.1.0]hexane-3-carboxylic acid (21 mg, 0.055 mmol) and 6-bromo-3-methylpyridin-2-amine (0.011 g, 0.058 mmol) in dichloromethane (2 mL) was treated with pyridine (0.022 mL, 0.276 mmol) followed by phosphoryl chloride (0.005 mL, 0.055 mmol) at 0° C. After the reaction was stirred at room temperature for 2 hours, NaHCO$_3$ aqueous was added. The mixture was extracted with EtOAc. The organic layer was washed with brine and dried over anhydrous Na$_2$SO$_4$. Solvent was removed under reduced pressure and the residue was purified by column chromatography on silica gel to afford tert-butyl (1R,3S,5R)-3-[(6-bromo-3-methylpyridin-2-yl)carbamoyl]-5-[(4-tert-butyl-1,3-thiazol-2-yl)methyl]-2-azabicyclo[3.1.0]hexane-2-carboxylate 6 (8.5 mg).

Step 6: (1R,3S,5R)—N-(6-bromo-3-methylpyridin-2-yl)-5-[(4-tert-butyl-1,3-thiazol-2-yl)methyl]-2-azabicyclo[3.1.0]hexane-3-carboxamide (7)

tert-Butyl (1R,3S,5R)-3-[(6-bromo-3-methylpyridin-2-yl)carbamoyl]-5-[(4-tert-butyl-1,3-thiazol-2-yl)methyl]-2-azabicyclo[3.1.0]hexane-2-carboxylate (8.5 mg, 0.015 mmol) was treated with trifluoroacetic acid (1 mL) in dichloromethane (1 mL) at room temperature for 90 minutes. Solvent was removed under reduced pressure and the residue was coevaporated with toluene to afford (1R,3S,5R)—N-(6-bromo-3-methylpyridin-2-yl)-5-[(4-tert-butyl-1,3-thiazol-2-yl)methyl]-2-azabicyclo[3.1.0]hexane-3-carboxamide 7 as TFA salt for next step.

Step 7: (1R,3S,5R)-2-{2-[3-Acetyl-5-(2-methylpyrimidin-5-yl)indazol-1-yl]acetyl}-N-(6-bromo-3-methylpyridin-2-yl)-5-[(4-tert-butyl-1,3-thiazol-2-yl)methyl]-2-azabicyclo[3.1.0]hexane-3-carboxamide (338)

Into a mixture of (1R,3S,5R)—N-(6-bromo-3-methylpyridin-2-yl)-5-[(4-tert-butyl-1,3-thiazol-2-yl)methyl]-2-azabicyclo[3.1.0]hexane-3-carboxamide TFA salt 7 (0.015 mmol) and [3-acetyl-5-(2-methylpyrimidin-5-yl)indazol-1-yl]acetic acid 8 (4.6 mg, 0.015 mmol) in N,N-dimethylformamide (1 mL), 0-(benzotriazol-1-yl)-N,N,N,N-tetramethyluronium tetrafluoroborate (0.007 g, 0.023 mmol) followed by N,N-diisopropylethylamine (0.019 g, 0.026 mL, 0.15 mmol) was added with stirring. After the reaction was complete, NaHCO$_3$ aqueous solution was added and the mixture was extracted with EtOAc. Solvent was removed under reduced pressure and the residue was purified by column chromatography on silica gel (MeOH in DCM 0-10%) to afford (1R,3S,5R)-2-{2-[3-acetyl-5-(2-methylpyrimidin-5-yl)indazol-1-yl]acetyl}-N-(6-bromo-3-methylpyridin-2-yl)-5-[(4-tert-butyl-1,3-thiazol-2-yl)methyl]-2-azabicyclo[3.1.0]hexane-3-carboxamide (338) (8.2 mg). $^1$H $^1$H NMR (400 MHz, Chloroform-d) δ 8.91 (s, 2H), 8.65 (s, 1H), 8.58 (dd, J=0.9, 1.7 Hz, 1H), 7.71-7.55 (m, 2H), 7.39-7.30 (m, 1H), 7.23 (d, J=7.9 Hz, 1H), 6.78 (s, 1H), 5.50 (s, 2H), 4.88 (d, J=8.4 Hz, 1H), 3.64 (d, J=15.2 Hz, 1H), 3.46 (dd, J=2.6, 5.6 Hz, 1H), 3.14 (d, J=15.3 Hz, 1H), 2.88 (d, J=13.7 Hz, 1H), 2.81 (s, 3H), 2.71 (s, 3H), 2.40 (t, J=11.4 Hz, 1H), 1.33 (s, 10H), 1.00 (dd, J=2.6, 5.8 Hz, 1H), 0.92-0.79 (m, 1H). LC (method A): $t_R$=2.40 min. LC/MS (EI) m/z: [M+H]$^+$ 741.

Scheme 97: (1R,3S,5R)-2-(2-(3-Acetyl-7-(hydroxymethyl)-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (526):

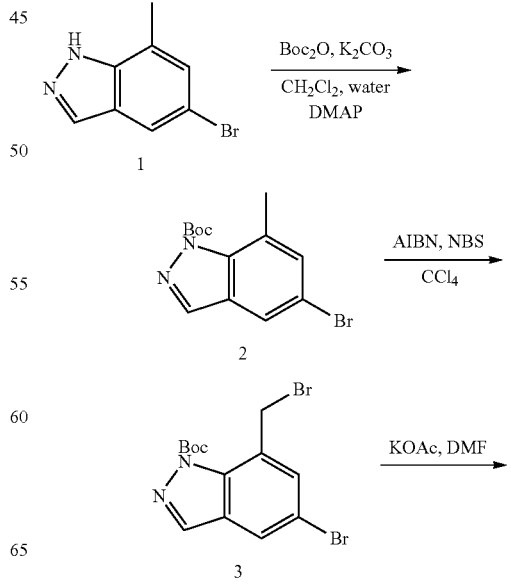

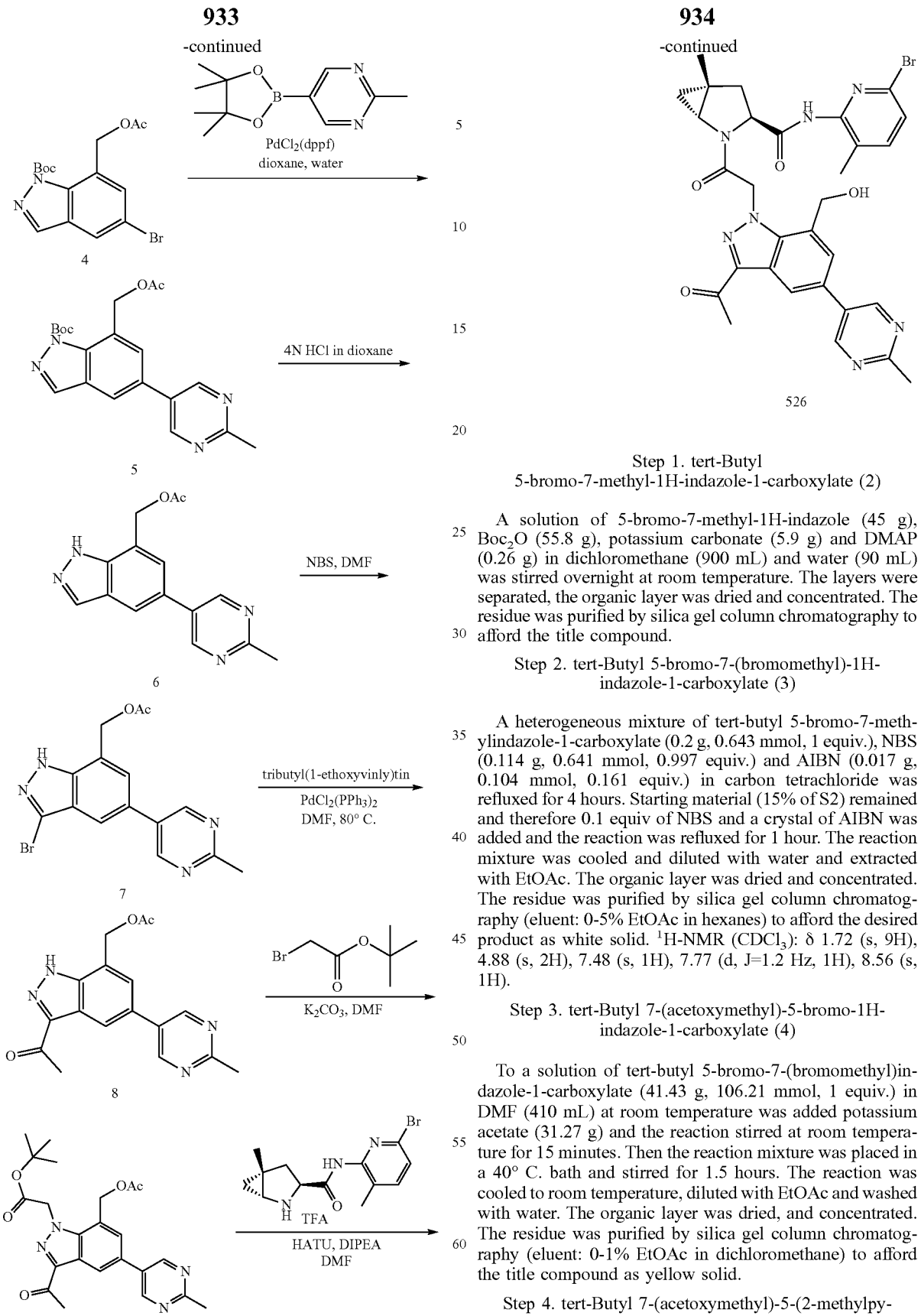

Step 1. tert-Butyl 5-bromo-7-methyl-1H-indazole-1-carboxylate (2)

A solution of 5-bromo-7-methyl-1H-indazole (45 g), Boc₂O (55.8 g), potassium carbonate (5.9 g) and DMAP (0.26 g) in dichloromethane (900 mL) and water (90 mL) was stirred overnight at room temperature. The layers were separated, the organic layer was dried and concentrated. The residue was purified by silica gel column chromatography to afford the title compound.

Step 2. tert-Butyl 5-bromo-7-(bromomethyl)-1H-indazole-1-carboxylate (3)

A heterogeneous mixture of tert-butyl 5-bromo-7-methylindazole-1-carboxylate (0.2 g, 0.643 mmol, 1 equiv.), NBS (0.114 g, 0.641 mmol, 0.997 equiv.) and AIBN (0.017 g, 0.104 mmol, 0.161 equiv.) in carbon tetrachloride was refluxed for 4 hours. Starting material (15% of S2) remained and therefore 0.1 equiv of NBS and a crystal of AIBN was added and the reaction was refluxed for 1 hour. The reaction mixture was cooled and diluted with water and extracted with EtOAc. The organic layer was dried and concentrated. The residue was purified by silica gel column chromatography (eluent: 0-5% EtOAc in hexanes) to afford the desired product as white solid. ¹H-NMR (CDCl₃): δ 1.72 (s, 9H), 4.88 (s, 2H), 7.48 (s, 1H), 7.77 (d, J=1.2 Hz, 1H), 8.56 (s, 1H).

Step 3. tert-Butyl 7-(acetoxymethyl)-5-bromo-1H-indazole-1-carboxylate (4)

To a solution of tert-butyl 5-bromo-7-(bromomethyl)indazole-1-carboxylate (41.43 g, 106.21 mmol, 1 equiv.) in DMF (410 mL) at room temperature was added potassium acetate (31.27 g) and the reaction stirred at room temperature for 15 minutes. Then the reaction mixture was placed in a 40° C. bath and stirred for 1.5 hours. The reaction was cooled to room temperature, diluted with EtOAc and washed with water. The organic layer was dried, and concentrated. The residue was purified by silica gel column chromatography (eluent: 0-1% EtOAc in dichloromethane) to afford the title compound as yellow solid.

Step 4. tert-Butyl 7-(acetoxymethyl)-5-(2-methylpyrimidin-5-yl)-1H-indazole-1-carboxylate (5)

A heterogeneous mixture of 5-bromo-2-methylpyrimidine (23.91 g, 138.198 mmol, 1.501 equiv.), bis(pinacolato)diboron (38.47 g, 152.031 mmol, 1.651 equiv.), potassium acetate (27.13 g, 276.414 mmol, 3.002 equiv.), and dichloro 1,1'-bis(diphenylphosphino) palladium (II) dichloromethane adduct (5.64 g, 6.906 mmol, 0.075 equiv.) in dioxane was degassed with argon and heated at 100° C. overnight. The reaction mixture was cooled to room temperature and charged with tert-butyl 7-[(acetyloxy)methyl]-5-bromoindazole-1-carboxylate (34 g, 92.087 mmol, 1 equiv.), potassium carbonate (38.2 g, 276.391 mmol, 3.001 equiv.) and water. The reaction mixture was again degassed and heated at 100° C. for 1.5 hours. Then the solvent was removed under reduced pressure and the residue was partitioned between dichloromethane and water. The organic layer was separated and washed with water. The combined aqueous layer was extracted with dichloromethane. The combined organic layer was dried and concentrated. The residue was purified by silica gel column chromatography (eluent: 0-5% MeOH in dichloromethane) to afford the title compound as a cream colored solid.

Step 5. (5-(2-Methylpyrimidin-5-yl)-1H-indazol-7-yl)methyl acetate (6)

A finely powdered tert-Butyl 7-[(acetyloxy)methyl]-5-(2-methylpyrimidin-5-yl)indazole-1-carboxylate (20.8 g, 54.39 mmol, 1 equiv.) was suspended in 4N HCl in dioxane (210 mL, 54.39 mmol, 1 equiv.) and stirred at room temperature for 1 hour with frequent sonication. After the reaction was complete, the solid was isolated by filtration. The solid was partitioned between chloroform (1 L) and saturated aqueous sodium bicarbonate. The organic layer was separated, dried and concentrated to afford the title compound as cream colored solid.

Step 6. (3-Bromo-5-(2-methylpyrimidin-5-yl)-1H-indazol-7-yl)methyl acetate (7)

[5-(2-Methylpyrimidin-5-yl)-1H-indazol-7-yl]methyl acetate (20 g, 70.846 mmol, 1 equiv.) was suspended in DMF (200 mL) and the mixture was warmed till the solution was homogeneous. This solution was then allowed to come to room temperature with stirring. Once the solution was cooled to room temperature, NBS (13.88 g) was added portion-wise at room temperature. The reaction mixture was stirred at room temperature for 30 minutes and then poured into 2 L of water with stirring. The solid was isolated by filtration, washed with 100 mL of saturated aqueous sodium bicarbonate solution and water and dried to afford the title compound as cream colored solid. $^1$H-NMR (DMSO-$d_6$): δ 2.10 (s, 3H), 2.68 (s, 3H), 5.38 (s, 2H), 7.89 (s, 1H), 7.95 (s, 1H), 9.09 (s, 2H), 13.75 (s, 1H).

Step 7. (3-Acetyl-5-(2-methylpyrimidin-5-yl)-1H-indazol-7-yl)methyl acetate (8)

A solution of [3-bromo-5-(2-methylpyrimidin-5-yl)-1H-indazol-7-yl]methyl acetate (10 g, 27.686 mmol, 1 equiv.) and trans-dichlorobis(triphenylphosphine)palladium (II) (1.94 g, 2.764 mmol, 0.1 equiv.) in DMF (200 mL) was purged with argon, and tributyl(1-ethoxyvinyl)tin (14.99 g, 14.03 mL, 41.506 mmol, 1.499 equiv.) was added while continuing to purge with argon for 5 additional minutes. Then the reaction mixture was heated at 80° C. overnight. The solvent was removed under reduced pressure. Chloroform (200 mL) and cold 2N aqeuous HCl (50 mL) was added to the reaction mixture and the mixture was stirred for 10 minutes in an ice bath. Then the reaction mixture was made basic by the careful addition of saturated aqueous NaHCO$_3$ solution. The organic layer was separated and the aqueous layer was extracted with chloroform. The combined organic layer was taken to dryness. The residue was used as such for the next step.

Step 8. tert-Butyl 2-(7-(acetoxymethyl)-3-acetyl-5-(2-methylpyrimidin-5-yl)-1H-indazol-1-yl)acetate (9)

[3-Acetyl-5-(2-methylpyrimidin-5-yl)-1H-indazol-7-yl] methyl acetate (from above) was taken in DMF (150 mL) and potassium carbonate (7.65 g, 55.351 mmol, 2 equiv.) was added followed by tert-butyl bromoacetate (6.5 g, 4.921 mL, 33.325 mmol, 1.204 equiv.). The reaction mixture was stirred at room temperature for 1 hour. The reaction mixture was filtered through a fritted funnel and the filtrate was concentrated under reduced pressure. The residue was purified by silica gel column chromatography (0-5% MeOH in dichloromethane) to afford title compound as cream colored solid.

Step 9. (1R,3S,5R)-2-(2-(3-Acetyl-7-(hydroxymethyl)-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (526)

A solution of {3-acetyl-1-[2-(tert-butoxy)-2-oxoethyl]-5-(2-methylpyrimidin-5-yl}indazol-7-yl)methyl acetate (S9, 0.05 g, 0.115 mmol, 1 equiv.) in dichloromethane (1 mL) and TFA (1 mL) was stirred at room temperature for 3 hours and the volatiles were removed under reduced pressure. Separately, tert-butyl (1R,3S,5R)-3-[(6-bromo-3-methylpyridin-2-yl)carbamoyl]-5-methyl-2-azabicyclo[3.1.0] hexane-2-carboxylate (0.047 g, 0.115 mmol, 1 equiv.) S10, 1 mL of TFA, and 1 mL of dichloromethane in DCM (1 mL) was stirred at room temperature for 30 minutes. Upon evaporation of the solvents, the S10 mixture was mixed with the S9 reside. The reaction mixture was cooled in an ice-bath and DIPEA (0.1 mL) and HATU (0.048 g, 0.126 mmol, 1.102 equiv.) were added successively before the reaction mixture was stirred at room temperature for 30 minutes. The reaction mixture was then poured into 10 mL of 1% aqueous LiOH and extracted with chloroform. The organic layer was dried, concentrated and the residue was purified by silica gel column chromatography (eluent: 0-4% MeOH in dichloromethane) to afford Compound 526 as a white solid. $^1$H-NMR (Chloroform-d) δ 0.97 (d, J=5.2 Hz, 1H), 1.17 (t, J=5.5 Hz, 1H), 1.39 (s, 3H), 2.08-2.15 (m, 1H), 2.15 (s, 3H), 2.72-2.75 (m, 1H), 2.75 (s, 3H), 2.81 (s, 3H), 3.18 (d, J=3.7 Hz, 1H), 4.86 (d, J=8.1 Hz, 1H), 5.14-5.24 (m, 2H), 5.51 (d, J=16.9 Hz, 1H), 6.07 (d, J=17.0 Hz, 1H), 7.29 (d, J=8 Hz, 1H), 7.43 (d, J=8.0 Hz, 1H), 7.49 (s, 1H), 8.59 (s, 1H), 8.91 (s, 2H), 9.19 (s, 1H).

(3-Acetyl-1-(2-((1R,3S,5R)-3-((6-bromo-3-methylpyridin-2-yl)carbamoyl-5-methyl-2-azabicyclo [3.1.0]hexan-2-yl)-2-oxoethyl)-5-(2-methylpyrimidin-5-yl)-1H-indazol-7-yl)methyl Acetate (529)

Compound 529 was prepared in a similar manner to Compound 526 with the exception of Step 8: A solution of {3-acetyl-1-[2-(tert-butoxy)-2-oxoethyl]-5-(2-methylpyrimidin-5-yl)indazol-7-yl}methyl acetate (S9, 0.05 g, 0.114 mmol, 1 equiv.) in TFA (1 mL) and dichloromethane (1 mL) was stirred at room temperature for 3 hours. Then the volatiles were removed under reduced pressure. To the residue was added (1R,3S,5R)—N-(6-bromo-3-methylpyridin-2-yl)-5-methyl-2-azabicyclo[3.1.0]hexane-3-carboxamide (0.035 g, 0.114 mmol, 1 equiv.) and DMF (1 mL). The solution was cooled in an ice-bath. DIPEA (0.1 mL) was added to this cooled solution, followed by TBTU (0.04 g). The reaction mixture was stirred at room temperature for 30 minutes. Then the solvent was removed under reduced pressure and the residue was partitioned between chloroform and saturated aqueous sodium bicarbonate solution. The organic layer was separated and washed with water. The organic layer was dried, concentrated and the residue was purified by silica gel column chromatography (0-2.5% MeOH in dichloromethane) to afford compound 529 as white solid. ¹H NMR (400 MHz, Chloroform-d) δ 0.99 (dd, J=2.3, 5.4 Hz, 1H), 1.19 (t, J=5.2 Hz, 1H), 1.44 (s, 3H), 2.08 (s, 3H), 2.10 (s, 3H), 2.34 (t, J=11.4 Hz, 1H), 2.70-2.72 (m, 1H), 2.72 (s, 3H), 2.81 (s, 3H), 3.21 (d, J=3.6 Hz, 1H), 4.83 (d, J=8.3 Hz, 1H), 5.46-5.60 (m, 2H), 5.70 (d, J=17.4 Hz, 1H), 5.87 (d, J=17.4 Hz, 1H), 7.23 (d, J=8 Hz, 1H), 7.35 (d, J=7.9 Hz, 1H), 7.69 (s, 1H), 8.63 (s, 1H), 8.69 (s, 1H), 8.91 (s, 2H).

Scheme 98: Synthesis of (1R,3S,5R)-2-(2-(3-acetyl-7-methyl-5-(2-methylpyrimidin-5-yl)-1H-pyrrolo[2,3-c]pyridin-1-yl)acetyl)-N-(6-bromo-3-methylpyridin-2-yl)-5-methyl-2-azabicyclo[3.1.0]hexane-3-carboxamide (472)

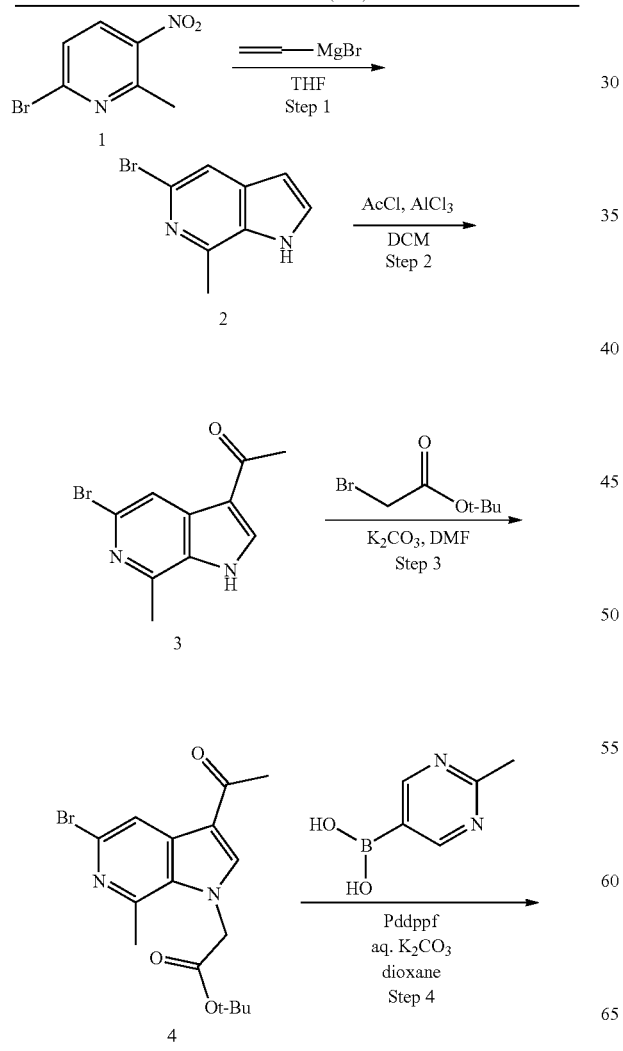

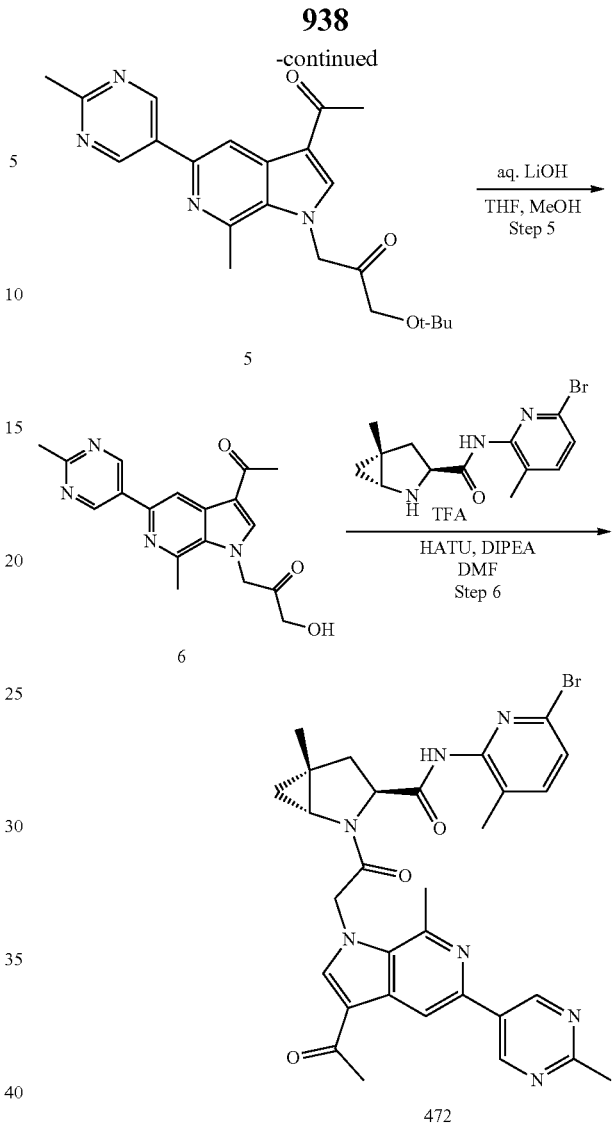

Step 1: 5-Bromo-7-methyl-1H-pyrrolo[2,3-c]pyridine (2)

A stirred solution of compound 1 (1.5 g 6.91 mmol) in THF (30 mL) under N₂ atmosphere at -78° C. was treated with bromo(ethenyl)magnesium (20.7 mL, 20.7 mmol, 1M) and the mixture was stirred at -40° C. for 2 hours. The reaction mixture was quenched with saturated aqueous NH₄Cl solution and diluted with EtOAc. The layers were separated and the organic phase was dried over Na₂SO₄ and concentrated to dryness. The residue was purified by column chromatography on silica gel (eluted with PE:EtOAc=1:0 to 1:1) to afford compound 2 (0.45 g, yield 30.85%) as orange oil. LC/MS (ESI) m/z: 211/213 (M+H)⁺.

Step 2: 1-(5-Bromo-7-methyl-1H-pyrrolo[2,3-c]pyridin-3-yl)ethanone (3)

To a solution of compound 2 (464 mg, 2.2 mmol) in DCM (20 mL) was added acetyl chloride (0.345 g, 4.4 mmol) and AlCl₃ (0.59 g, 4.4 mmol) and the reaction mixture was stirred at ambient temperature for 3 hours. The mixture was poured into ice-water and extracted with DCM twice. The combined organic layers were dried over anhydrous Na₂SO₄, filtered and concentrated under reduced pressure to dryness. The residue was purified by silica gel chromatography (eluted with PE:EtOAc=4:1) to give compound 3 (0.22 g, yield 39.5%) as yellow oil. LC/MS (ESI) m/z: 253/255 (M+H)⁺.

Step 3: tert-Butyl 2-(3-acetyl-5-bromo-7-methyl-1H-pyrrolo[2,3-c]pyridin-1-yl)acetate (4)

To a solution of compound 3 (220 mg, 0.869 mmol) in DMF (5 mL) was added K₂CO₃ (0.24 g, 1.74 mmol) followed by tert-butyl 2-bromoacetate (0.203 g, 1.04 mmol) and the mixture was stirred at room temperature for 2 hours. The mixture was diluted with EtOAc and washed with water and brine, dried over anhydrous Na₂SO₄, filtered and concentrated under vacuum to afford compound 4 (0.21 g, yield 65.8%) as white solid. LC/MS (ESI) m/z: 367/369 (M+H)⁺.

Step 4: tert-Butyl 2-(3-acetyl-7-methyl-5-(2-methylpyrimidin-5-yl)-1H-pyrrolo[2,3-c]pyridin-1-yl)acetate (5)

To the stirred solution of compound 4 (210 mg, 0.57 mmol) in 1,4-dioxane (2 mL) and water (0.5 mL) was added 2-methylpyrimidin-5-ylboronic acid (95 mg, 0.69 mmol) and K₂CO₃ (0.158 g, 1.144 mmol). The mixture was degassed under N₂ atmosphere for three times, Pd(dppf)Cl₂ (0.042 g, 0.057 mmol) was added, and the reaction was stirred at 100° C. under N₂ atmosphere for 16 hours. The reaction mixture was diluted with water and extracted with EtOAc twice. The combined organic layers were washed with brine, dried over anhydrous Na₂SO₄ and concentrated under reduced pressure. The obtained residue was purified by silica gel chromatography (eluted with PE:EtOAc=1:0 to 1:1) to afford compound 5 (0.15 g, yield 68.9%) as white solid. LC/MS (ESI) m/z: 381/383 (M+H)⁺.

Step 5: 2-(3-acetyl-7-methyl-5-(2-methylpyrimidin-5-yl)-1H-pyrrolo[2,3-c]pyridin-1-yl)acetic Acid (6)

To a solution of compound 5 (150 mg, 0.39 mmol) in THF (3 mL) and water (1 mL) was added lithium hydroxide (0.019 g, 0.79 mmol) and the reaction mixture was stirred at 25° C. for 2 hours. The mixture was diluted with water and washed with ether twice. The aqueous layer was acidified with 1N aqueous HCl to pH of approximately 3 and extracted with DCM twice. The combined organic layers were washed with brine, dried over anhydrous Na₂SO₄, filtered and concentrated to dryness to afford compound 6 (75 mg, yield 58.6%) as white solid. LC/MS (ESI) m/z: 325 (M+H)⁺.

Step 6: (1R,3S,5R)-2-(2-(3-Acetyl-7-methyl-5-(2-methylpyrimidin-5-yl)-1H-pyrrolo[2,3-c]pyridin-1-yl)acetyl)-N-(6-bromo-3-methylpyridin-2-yl)-5-methyl-2-azabicyclo[3.1.0]hexane-3-carboxamide (472)

To a stirred solution of compound 6 (20 mg, 0.062 mmol) and (1R,3S,5R)—N-(6-bromo-3-methylpyridin-2-yl)-5-methyl-2-azabicyclo[3.1.0]hexane-3-carboxamide TFA salt (25.6 mg, 0.062 mmol) in DMF (3 mL) was added HATU (23 mg, 0.062 mmol) and DIPEA (23.2 mg, 0.18 mmol) and the reaction mixture was stirred at ambient temperature for 4 hours. The mixture was diluted with EtOAc and washed with water and brine, dried over anhydrous Na₂SO₄, filtered and concentrated to dryness. The residue was purified by prep-HPLC to afford 472 (4.5 mg, yield 11.8%) as an off-white solid. ¹H-NMR (400 MHz, DMSO-d₆) δ 10.33 (s, 1H), 9.26 (s, 2H), 8.48 (t, J=11.9 Hz, 2H), 7.61 (d, J=8.0 Hz, 1H), 7.43 (d, J=7.9 Hz, 1H), 5.80 (d, J=17.9 Hz, 1H), 5.48 (d, J=17.8 Hz, 1H), 4.41 (m, 1H), 3.58-3.55 (m, 1H), 2.55 (m, 1H), 2.49 (s, 3H), 2.09-1.96 (m, 4H), 1.33 (s, 3H), 1.02 (m, 1H), 0.91 (m, 1H). LC/MS (ESI) m/z: 616/618 (M+H)⁺.

Scheme 99: Synthesis of 2-((1R,3S,5R)-2-(2-(3-acetyl-5-(2-methylpyrimidin-5-yl)-1H-indazol-1-yl)acetyl)-5-methyl-2-azabicyclo[3.1.0]hexane-3-carboxamido)-6-bromoisonicotinic acid (493)

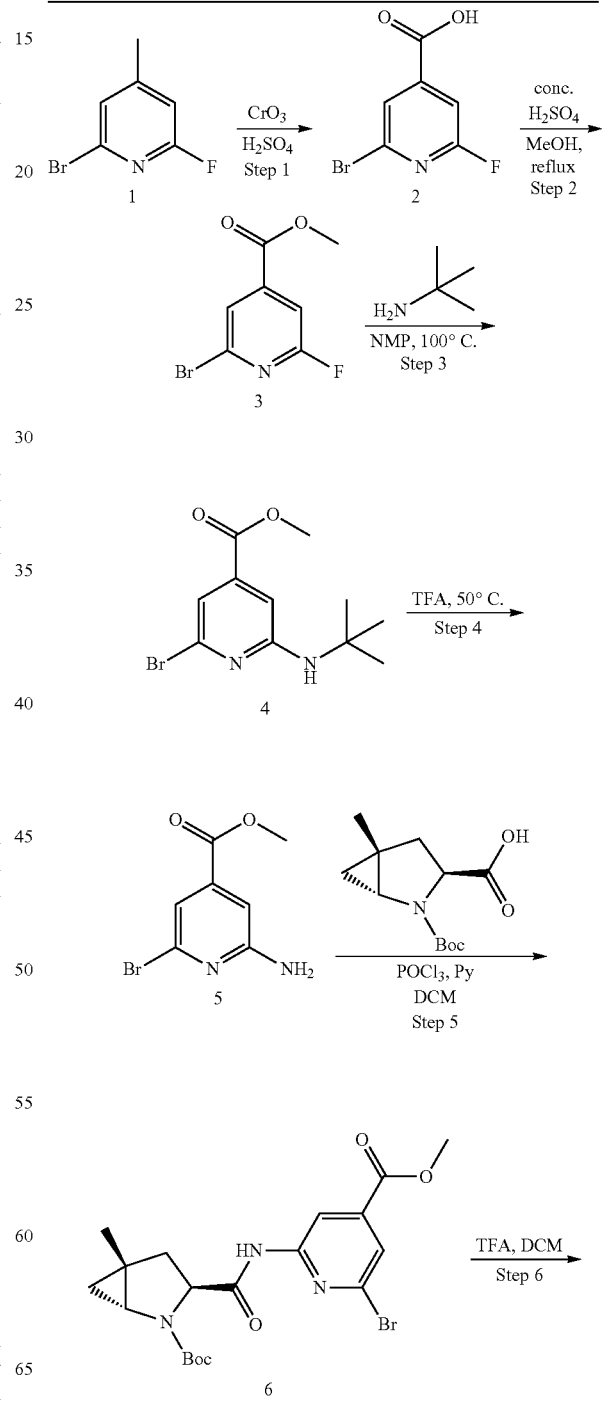

-continued

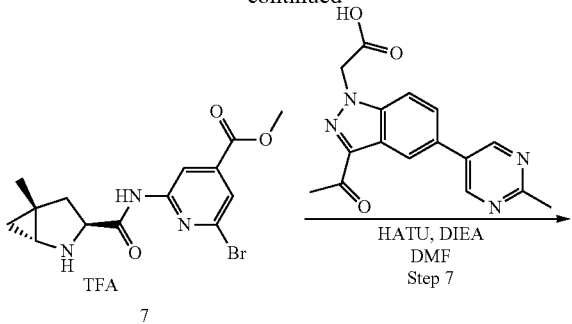

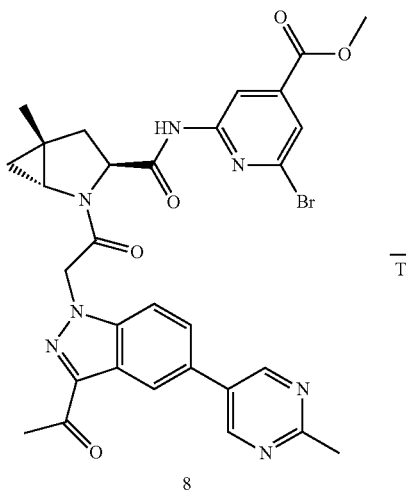

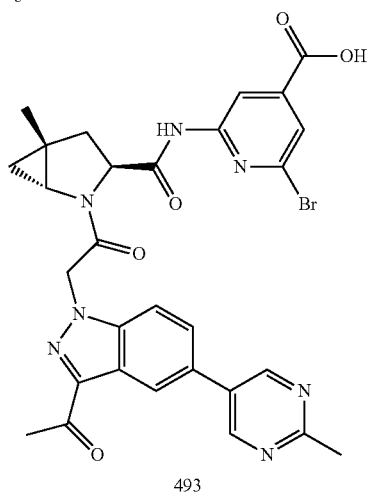

Step 1: 2-Bromo-6-fluoroisonicotinic Acid (2)

To a stirred solution of compound 1 (400 mg, 2.105 mmol) in sulfuric acid (3 mL) was added chromium trioxide (0.631 g, 6.315 mmol) portion-wise in a water bath while the temperature was maintained between 20-50° C. and the mixture was stirred at room temperature for 16 hours. The reaction mixture was poured slowly into ice-water and the mixture was stirred at room temperature for 1 hour. The mixture was filtered and the filter cake was washed with water, dried under vacuum to afford compound 2 (400 mg, yield 86.4%) as white solid. LC/MS (ESI) m/z: 220/222 (M+H)+.

Step 2: Methyl 2-bromo-6-fluoropyridine-4-carboxylate (3)

To a solution of compound 2 (400 mg, 1.82 mmol) in methanol (10 mL) was added sulfuric acid (0.5 mL) at 0° C. and the mixture was heated to 60° C. overnight. The mixture was then concentrated to dryness and the residue was partitioned between water and EtOAc. The layers were separated and the organic layer was dried over Na$_2$SO$_4$, filtered and concentrated under vacuum to afford compound 3 (380 mg, yield 89.2%) as white solid. LC/MS (ESI) m/z: 234/236 (M+H)+.

Step 3: Methyl 2-bromo-6-(tert-butylamino)pyridine-4-carboxylate (4)

Compound 3 (200 mg, 0.855 mmol) and erbumine (0.63 g, 8.55 mmol) were dissolved in NMP (3 mL) and the reaction mixture was stirred at 100° C. for 4 hours in a sealed tube. The mixture was diluted with EtOAc and washed with water and brine, dried over anhydrous Na$_2$SO$_4$, filtered and concentrated to dryness. The residue was purified by silica gel chromatography (eluted with PE:EtOAc=5:1) to afford compound 4 (150 mg, yield 61.8%) as white solid. LC/MS (ESI) m/z: 287/289 (M+H)+.

Step 4: Methyl 2-amino-6-bromopyridine-4-carboxylate (5)

A solution of compound 4 (150 mg, 0.522 mmol) in TFA (3 mL) was stirred at 70° C. under N$_2$ atmosphere for 16 hours. The mixture was concentrated to dryness and the residue was poured into saturated aqueous NaHCO$_3$ solution and extracted with EtOAc twice. The combined organic layers were washed with brine, dried and concentrated to dryness. The residue was purified by silica gel column chromatography (eluted with PE:EtOAc=9:1 to 5:1) to afford compound 5 (81 mg, yield 67.1%) as white solid. LC/MS (ESI) m/z: 231/233 (M+H)+.

Step 5: tert-Butyl (1R,3S,5R)-3-{[6-bromo-4-(methoxycarbonyl)pyridin-2-yl]carbamoyl}-5-methyl-2-azabicyclo[3.1.0]hexane-2-carboxylate (6)

To a mixture of compound 5 (71 mg, 0.307 mmol), pyridine (0.146 g, 1.844 mmol) and (2S,4S)-1-(tert-butoxycarbonyl)-4-methylpyrrolidine-2-carboxylic acid (74 mg, 0.307 mmol) in DCM (5 mL) was added POCl$_3$ (0.061 g, 0.399 mmol) drop-wise at 0° C. and the mixture was stirred at 20° C. for 5 hours under N$_2$ atmosphere. The mixture was diluted with DCM and washed with 0.5 N aqueous HCl and brine, dried over Na$_2$SO$_4$, filtered and concentrated to dryness. The residue was purified by silica gel column chromatography (eluted with PE:EtOAc=9:1 to 5:1) to afford compound 6 (100 mg, yield 71.6%) as white solid. LC/MS (ESI) m/z: 454/456 (M+H)+.

Step 6: Methyl 2-bromo-6-[(1R,3S,5R)-5-methyl-2-azabicyclo[3.1.0]hexane-3-amido]pyridine-4-carboxylate (7)

To a solution of compound 6 (100 mg, 0.22 mmol) in DCM (2 mL) was added TFA (1 mL) and the mixture was stirred at room temperature for 2 hours. The mixture was concentrated to dryness and the residue was washed with ether and dried under vacuum to afford compound 7 (95 mg, yield 100/a) as a yellow oil. LC/MS (ESI) m/z: 354/356 (M+H)⁺.

Step 7: Methyl 2-[(1R,3S,5R)-2-{2-[3-acetyl-5-(2-methylpyrimidin-5-yl)indazol-1-yl]acetyl}-5-methyl-2-azabicyclo[3.1.0]hexane-3-amido]-6-bromopyridine-4-carboxylate (8)

To a mixture of compound 7 (95 mg, 0.22 mmol) and [3-acetyl-5-(2-methylpyrimidin-5-yl)indazol-1-yl]acetic acid (75 mg, 0.242 mmol) in DMF (4 mL) was added HATU (0.167 g 0.44 mmol) and DIPEA (0.114 g, 0.881 mmol). The reaction mixture was stirred at ambient temperature for 4 hours. The mixture was diluted with EtOAc and washed with saturated aqueous NH₄Cl solution and brine, dried over Na₂SO₄, filtered and concentrated to dryness. The residue was purified by silica gel column chromatography (eluted with PE:EtOAc=10:1 to 5:1) to afford compound 8 (110 mg, yield 77.3%) as white solid. LC/MS (ESI) m/z: 646/648 (M+H)⁺.

Step 8: 2-[(1R,3S,5R)-2-{2-[3-Acetyl-5-(2-methylpyrimidin-5-yl)indazol-1-yl]acetyl}-5-methyl-2-azabicyclo[3.1.0]hexane-3-amido]-6-bromopyridine-4-carboxylic Acid (493)

A solution of compound 8 (110 mg, 0.17 mmol) in THF (2 mL) and water (1 mL) was added lithiumol (16 mg, 0.68 mmol) and the mixture was stirred at room temperature for 2 hours. The mixture was acidified by adding 1N aqueous HCl and extracted with EtOAc twice. The combined organic layers were washed with brine, dried over Na₂SO₄, filtered, and concentrated to dryness. The residue was purified by prep-HPLC to afford Compound 493 (80 mg, yield 74.34%) as white solid. ¹H-NMR (400 MHz, DMSO-d₆) δ 11.00 (s, 1H), 9.03 (s, 2H), 8.49 (s, 1H), 8.42 (s, 1H), 7.87 (m, 2H), 7.61 (m, 1H), 5.97 (d, J=17.3 Hz, 1H), 5.57 (d, J=17.2 Hz, 1H), 4.42 (m, 1H), 3.66-3.62 (m, 1H), 2.68 (s, 3H), 2.65 (s, 3H), 2.48 (m, 1H), 2.01 (m, 1H), 1.30 (s, 3H), 0.98 (m, 2H). LC/MS (ESI) m/z: 632/634 (M+H)⁺.

Scheme 100: Synthesis of 2-(2-((1R,3S,5R)-2-(2-(3-acetyl-5-(2-methylpyrimidin-5-yl)-1H-indazol-1-yl)acetyl)-5-methyl-2-azabicyclo[3.1.0]hexane-3-carboxamido)-6-bromopyridin-4-yl)acetic acid (514)

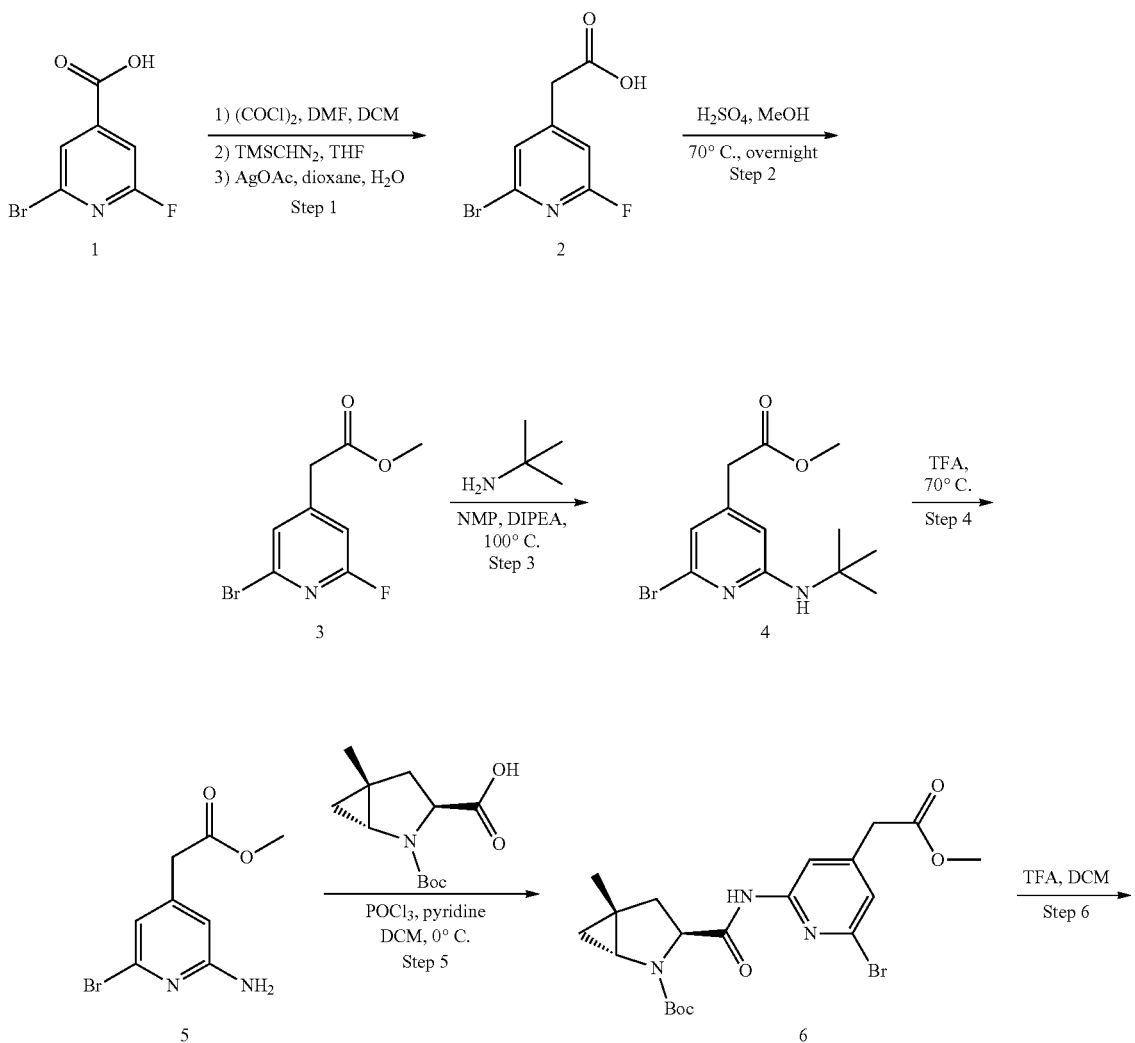

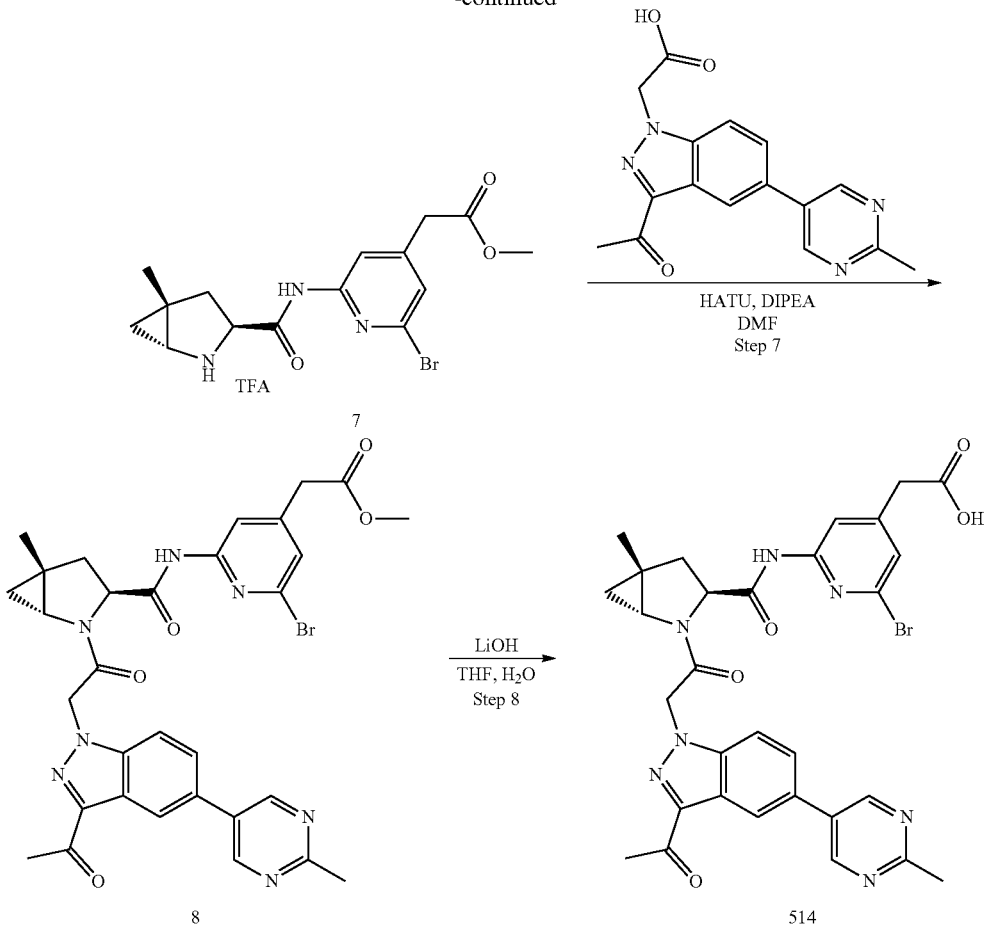

Step 1: 2-(2-Bromo-6-fluoropyridin-4-yl)acetic Acid (2)

To a solution of compound 1 (200 mg, 0.91 mmol) in DCM (5 mL) was added oxalyl chloride (0.231 g, 1.82 mmol) followed by DMF (0.1 mL) at 0° C. The mixture was stirred at room temperature for 2 hours and concentrated to dryness. The residue was dissolved in THF (5 mL) and TMSCHN$_2$ (0.114 g, 1 mmol) was added at 0° C. The mixture was stirred at 0° C. for 3 hours and allowed to warm to room temperature. The reaction was quenched with acetic acid at 0° C., diluted with EtOAc, washed with water and brine, dried over anhydrous Na$_2$SO$_4$, filtered, and concentrated to dryness. The residue was dissolved in 1,4-dioxane (3 mL) and water (3 mL), and AgOAc (0.015 g, 0.091 mmol) was added. The reaction mixture was stirred at 100° C. for 12 hours. The mixture was diluted with EtOAc, washed with water and brine, dried over anhydrous Na$_2$SO$_4$ and concentrated dryness to afford compound 2 (150 mg, yield 70.5%) as a white solid. LC/MS (ESI) m/z: 234/236 (M+H)$^+$.

Step 2: methyl 2-(2-Bromo-6-fluoropyridin-4-yl)acetate (3)

To a solution of compound 2 (150 mg, 0.64 mmol) in MeOH (4 mL) was added H$_2$SO$_4$ (1 mL) at 0° C. and the mixture was stirred at 60° C. overnight. The mixture was diluted with EtOAc, washed with saturated aqueous NaHCO$_3$ solution and brine, dried over Na$_2$SO$_4$, filtered, and concentrated under vacuum to afford compound 3 (130 mg, yield 81.8%) as a white solid. LC/MS (ESI) m/z: 248/250 (M+H)$^+$.

Step 3: methyl 2-(2-bromo-6-(tert-butylamino)pyridin-4-yl)acetate (4)

Compound 3 (130 mg, 0.524 mmol) and erbumine (0.46 g, 6.29 mmol) was dissolved in NMP (4 mL) and the reaction mixture was stirred at 100° C. for 24 hours in a sealed tube. The mixture was diluted with EtOAc, washed with water and brine, dried over Na$_2$SO$_4$, filtered and concentrated to dryness. The residue was purified by silica gel chromatography (eluted with PE:EtOAc=5:1) to afford compound 4 (48 mg, yield 30.4%) as yellow solid. LC/MS (ESI) m/z: 301/303 (M+H)$^+$.

Step 4: methyl 2-(2-amino-6-bromopyridin-4-yl)acetate (5)

A solution of compound 4 (48 mg, 0.159 mmol) in TFA (3 mL) was heated to 70° C. under N$_2$ for 2 hours. The mixture was concentrated to dryness, saturated aqueous NaHCO$_3$ solution was added, and the oranganic layer was extracted with EtOAc twice. The combined organic layers were washed with brine, dried and concentrated to dryness. The residue was purified by silica gel column chromatography (eluted with: PE:EtOAc=9:1-5:1) to afford compound 5 (30 mg, yield 76.7%) as white solid. LC/MS (ESI) m/z: 245/247 (M+H)⁺.

Step 5: (1R,3S,5R)-tert-Butyl 3-((6-bromo-4-(2-methoxy-2-oxoethyl)pyridin-2-yl)carbamoyl)-5-methyl-2-azabicyclo[3.1.0]hexane-2-carboxylate (6)

To a solution of compound 5 (40 mg, 0.163 mmol), pyridine (77 mg, 0.979 mmol) and (1R,3S,5R)-2-(tert-butoxycarbonyl)-5-methyl-2-azabicyclo[3.1.0]hexane-3-carboxylic acid (39 mg, 0.163 mmol) in DCM (5 mL) was added POCl₃ (38 mg, 0.245 mmol) drop-wise at 0° C. The mixture was stirred at 20° C. for 5 hours. The mixture was diluted with EtOAc and washed with water and brine, dried, and concentrated to dryness. The residue was purified by silica gel chromatography (eluted with PE:EtOAc=3:1) to afford compound 6 (26 mg, yield 34.0%) as white solid. LC/MS (ESI) m/z: 468/470 (M+H)⁺.

Step 6: Methyl 2-(2-bromo-6-((1R,3S,5R)-5-methyl-2-azabicyclo[3.1.0]hexane-3-carboxamido) pyridin-4-yl)acetate (7)

To a solution of compound 6 (26 mg, 0.055 mmol) in DCM (1 mL) was added TFA (0.5 mL) and the mixture was stirred at room temperature for 2 hours. The mixture was concentrated to dryness and the residue was washed with ether and dried under vacuum to afford compound 7 (25 mg, yield 100%) as a yellow solid. LC/MS (ESI) m/z: 368/370 (M+H)⁺.

Step 7: methyl 2-(2-((1R,3S,5R)-2-(2-(3-acetyl-5-(2-methylpyrimidin-5-yl)-1H-indazol-1-yl)acetyl)-5-methyl-2-azabicyclo[3.1.0]hexane-3-carboxamido)-6-bromopyridin-4-yl)acetate (8)

To a solution of compound 7 (25 mg, 0.055 mmol) and [3-acetyl-5-(2-methylpyrimidin-5-yl)indazol-1-yl]acetic acid (21 mg, 0.068 mmol) in DMF (4 mL) was added HATU (0.043 g, 0.114 mmol) and DIPEA (0.029 g, 0.228 mmol) and the reaction mixture was stirred at ambient temperature for 4 hours. The mixture was diluted with EtOAc, washed with water and brine, dried over anhydrous Na₂SO₄, filtered, and concentrated to dryness. The residue was purified by silica gel chromatography (eluted with PE:EtOAc=3:1 to 1:1) to afford compound 8 (25 mg, yield 66.4%) as white solid. LC/MS (ESI) m/z: 660/662 (M+H)⁺.

Step 8: 2-(2-((1R,3S,5R)-2-(2-(3-acetyl-5-(2-methylpyrimidin-5-yl)-1H-indazol-1-yl)acetyl)-5-methyl-2-azabicyclo[3.1.0]hexane-3-carboxamido)-6-bromopyridin-4-yl)acetic Acid (514)

To a solution of compound 8 (25 mg, 0.038 mmol) in THF (1 mL) and water (0.5 mL) was added lithiumol (3 mg, 0.114 mmol) and the mixture was stirred at room temperature for 2 hours. The mixture was acidified by adding 1N aqueous HCl and the organic layer was extracted with EtOAc twice. The combined organic layers were washed with brine, dried and concentrated to dryness. The residue was purified by prep-HPLC to afford Compound 514 (20 mg, yield 81.7%) as a white solid. ¹H-NMR (400 MHz, CD₃OD) δ 8.99 (s, 2H), 8.52 (s, 1H), 8.02 (s, 1H), 7.78 (m, 2H), 7.22 (m, 1H), 5.81 (d, J=18.0 Hz, 1H), 5.63 (d, J=16.9 Hz, 1H), 5.33 (m, 1H), 4.47 (m, 1H), 3.54 (m, 1H), 3.47 (m, 2H), 2.74 (s, 3H), 2.69 (s, 3H), 2.55 (m, 1H), 2.17-2.12 (m, 1H), 1.37 (s, 3H), 1.07 (m, 1H), 0.98 (m, 1H). LC/MS (ESI) m/z: 646/648 (M+H)⁺.

Scheme 101: Synthesis of (1R,3S,5R)-2-{2-[3-Acetyl-7-methyl-5-(2-methylpyrimidin-5-yl)indazol-1-yl)acetyl}-5-methyl-N-{2-oxo-[1,2'-bipyridine]-3-yl}-2-azabicyclo[3.1.0]hexane-3-carboxamide (460)

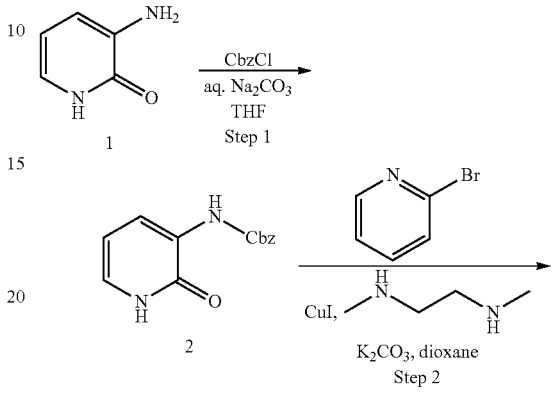

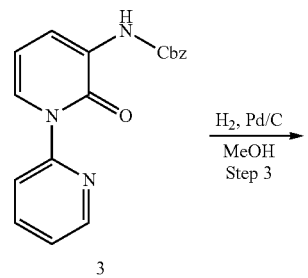

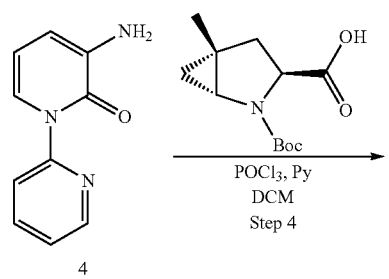

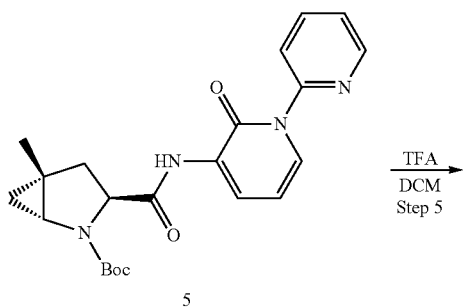

-continued

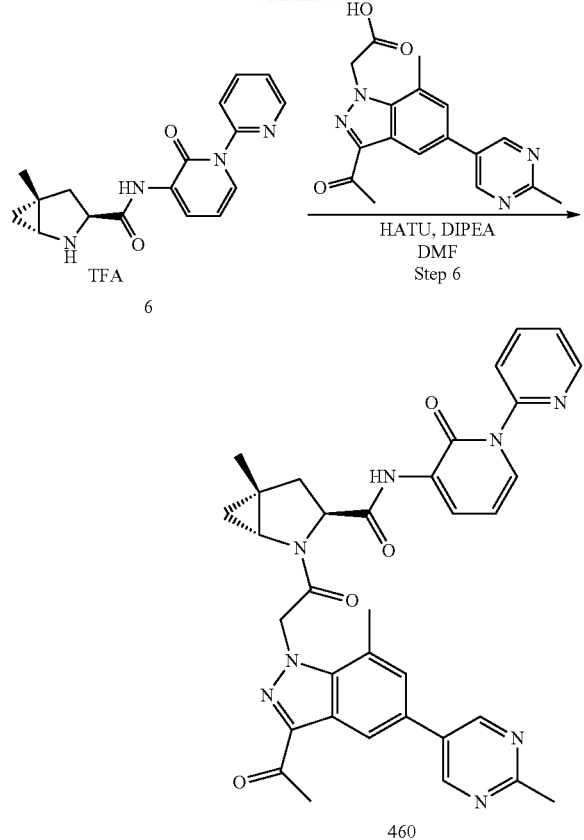

Step 1: Benzyl N-(2-hydroxypyridin-3-yl)carbamate (2)

To a solution of 3-amino-1,2-dihydropyridin-2-ol (4.97 g, 44.32 mmol) in THF (125 mL) was added a solution of sodium carbonate (5.16 g, 48.75 mmol) in water (60 mL) followed by the drop-wise addition of CbzCl (8.31 g, 48.75 mmol) at 0° C. The mixture was stirred at room temperature for 16 hours. The mixture was poured into ice-water and the resulting slurry was filtered. The filter cake was washed with water and dried under vacuum to afford benzyl N-(2-hydroxypyridin-3-yl)carbamate (6.51 g, yield 60.13%) as white solid. LC/MS (ESI) m/z: 245 (M+H)$^+$.

Step 2: Benzyl N-{2-oxo-[1,2'-bipyridine]-3-yl}carbamate (3)

To a solution of benzyl N-(2-hydroxypyridin-3-yl)carbamate (0.51 g, 2.08 mmol) in 1,4-Dioxane (10 mL) was added 2-bromopyridine (0.42 g, 2.71 mmol), 1,2-dimethylethylenediamine (0.074 g, 0.83 mmol), copper iodide (0.08 g, 0.41 mmol) and K$_2$CO$_3$ (0.57 g, 4.17 mmol), and the mixture was degassed under N$_2$ three times. The reaction was stirred at 115° C. for 16 hours in a sealed tube. The mixture was diluted with EtOAc and filtered. The filtrate was washed with water and brine, dried over anhydrous Na$_2$SO$_4$, and concentrated to dryness. The residue was purified by column chromatography on silica gel (eluted with PE:EtOAc=3:1) to afford benzyl N-{2-oxo-[1,2'-bipyridine]-3-yl}carbamate (0.19 g, yield 28.3%) as white solid. LC/MS (ESI) m/z: 322 (M+H)$^+$.

Step 3: 3-Amino-[1,2'-bipyridine]-2-one (4)

To a solution of benzyl N-{2-oxo-[1,2'-bipyridine]-3-yl} carbamate (0.19 g, 0.59 mmol) in methanol (6 mL) and THF (2 mL) was added Pd/C (20 mg, 10% wt), and the mixture was degassed under N$_2$ three times. The reaction was stirred under a H$_2$ balloon at room temperature for 2 hours. The mixture was filtered and the filtrate was concentrated to dryness to afford 3-amino-[1,2'-bipyridine]-2-one (0.11 g, yield 99.4%) as a yellow solid. LC/MS (ESI) m/z: 188 (M+H)$^+$.

Step 4: tert-Butyl (1R,3S,5R)-5-methyl-3-({2-oxo-[1,2'-bipyridine]-3-yl}carbamoyl)-2-azabicyclo[3.1.0]hexane-2-carboxylate (5)

To a mixture of 3-amino-[1,2'-bipyridine]-2-one (0.051 g, 0.27 mmol) and (1R,3S,5R)-2-(tert-butoxycarbonyl)-5-methyl-2-azabicyclo[3.1.0]hexane-3-carboxylic acid (0.066 g, 0.27 mmol) in DCM (3 mL) was added pyridine (0.11 g, 1.36 mmol) followed by POCl$_3$ (0.063 g, 0.41 mmol) at 0° C. The mixture was stirred at room temperature for 30 minutes and then diluted with DCM and washed with 0.5 N aqueous HCl and brine, dried over Na$_2$SO$_4$, filtered, and concentrated to afford tert-butyl (1R,3S,5R)-5-methyl-3-({2-oxo-[1,2'-bipyridine]-3-yl}carbamoyl)-2-azabicyclo[3.1.0]hexane-2-carboxylate (0.11 g, yield 98.4%) as a light yellow solid that was used directly in the next step. LC/MS (ESI) m/z: 411 (M+H)$^+$.

Step 5: (1R,3S,5R)-5-Methyl-N-{2-oxo-[1,2'-bipyridine]-3-yl}-2-azabicyclo[3.1.0]hexane-3-carboxamide TFA Salt (6)

To a solution of tert-butyl (1R,3S,5R)-5-methyl-3-({2-oxo-[1,2'-bipyridine]-3-yl} carbamoyl)-2-azabicyclo[3.1.0]hexane-2-carboxylate (0.11 g, 0.25 mmol) in DCM (3 mL) was added TFA (1.5 mL) at 0° C. and the mixture was stirred at room temperature for 2 hours. The reaction mixture was concentrated to dryness and co-evaporated with DCM twice and dried under vacuum to afford (1R,3S,5R)-5-methyl-N-{2-oxo-[1,2'-bipyridine]-3-yl}-2-azabicyclo[3.1.0]hexane-3-carboxamide TFA salt (105 mg, yield 100%) as yellow oil that was used directly in the next step. LC/MS (ESI) m/z: 311 (M+H)$^+$.

Step 6: (1R,3S,5R)-2-{2-[3-Acetyl-7-methyl-5-(2-methylpyrimidin-5-yl)indazol-1-yl]acetyl}-5-methyl-N-{2-oxo-[1,2'-bipyridine]-3-yl}-2-azabicyclo[3.1.0]hexane-3-carboxamide (460)

To a mixture of (1R,3S,5R)-5-methyl-N-{2-oxo-[1,2'-bipyridine]-3-yl}-2-azabicyclo [3.1.0]hexane-3-carboxamide (40 mg, 0.12 mmol) and [3-acetyl-7-methyl-5-(2-methylpyrimidin-5-yl)indazol-1-yl]acetic acid (42 mg, 0.12 mmol) in DMF (3 mL) was added HATU (74 mg, 0.19 mmol) and DIPEA (84 mg, 0.64 mmol) and the mixture was stirred at room temperature for 1 hour. The reaction mixture was diluted with EtOAc and washed with saturated aqueous NH$_4$Cl solution and brine, dried over anhydrous Na$_2$SO$_4$, filtered, and concentrated to dryness. The residue was purified by prep.HPLC to afford 460 (31 mg, yield 38.8%) as white solid. $^1$H-NMR (400 MHz, CD$_3$OD) δ 8.95 (s, 2H), 8.59-8.54 (m, 1H), 8.42-8.35 (m, 2H), 7.98-7.93 (m, 1H), 7.72 (d, J=8.1 Hz, 1H), 7.57-7.53 (m, 1H), 7.51-7.44 (m, 2H), 6.47-6.42 (m, 1H), 5.98 (d, J=17.8 Hz, 1H), 5.77 (d, J=17.7 Hz, 1H), 4.68-4.53 (m, 2H), 3.55-3.51 (m, 1H), 2.73

(d, J=4.9 Hz, 6H), 2.66 (s, 3H), 2.57-2.51 (m, 1H), 2.30-2.25 (m, 1H), 1.39 (s, 3H), 1.14-1.08 (m, 1H), 1.00-0.96 (m, 1H). LC/MS (ESI) m/z: 617 (M+H)+.

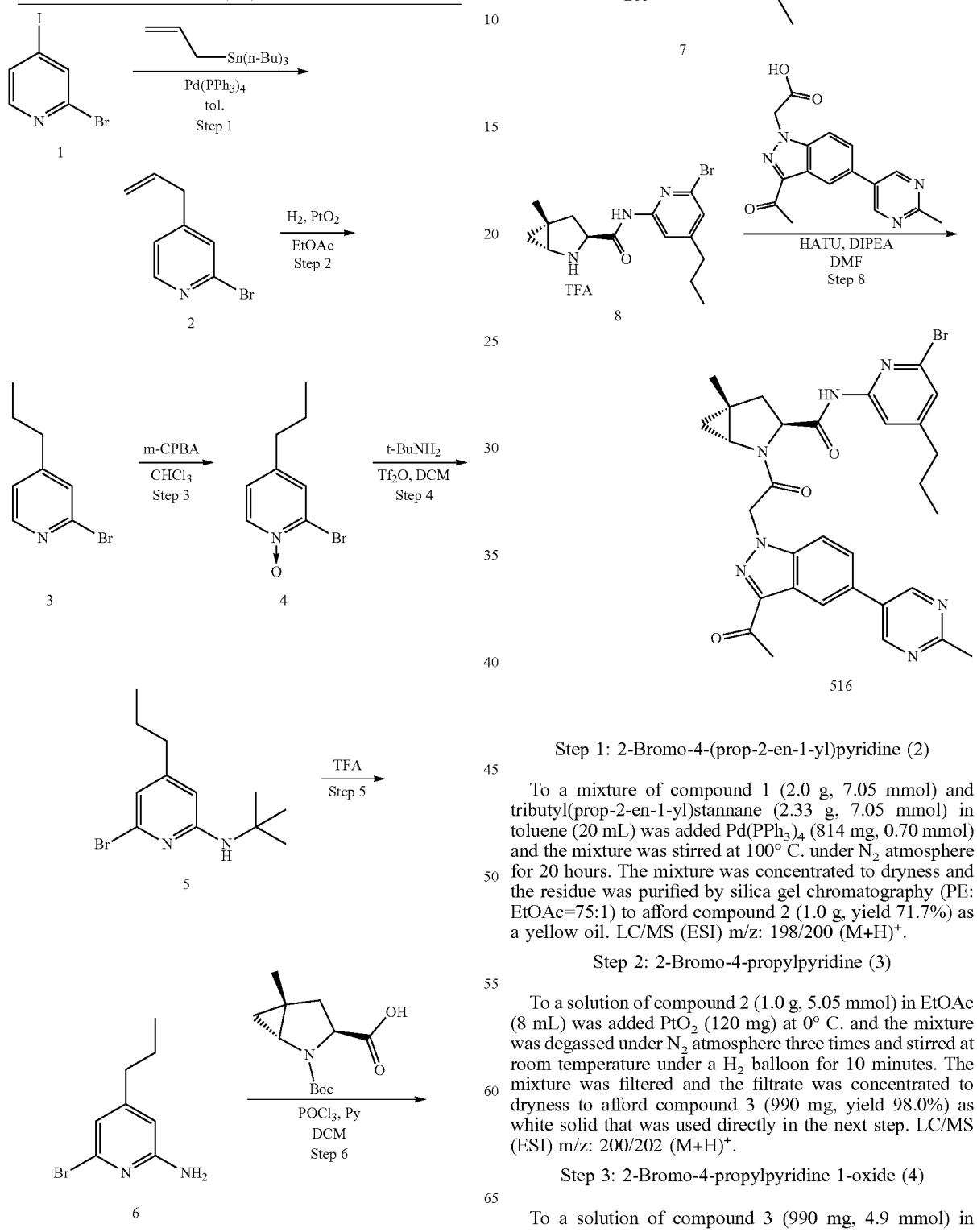

Step 1: 2-Bromo-4-(prop-2-en-1-yl)pyridine (2)

To a mixture of compound 1 (2.0 g, 7.05 mmol) and tributyl(prop-2-en-1-yl)stannane (2.33 g, 7.05 mmol) in toluene (20 mL) was added Pd(PPh$_3$)$_4$ (814 mg, 0.70 mmol) and the mixture was stirred at 100° C. under N$_2$ atmosphere for 20 hours. The mixture was concentrated to dryness and the residue was purified by silica gel chromatography (PE: EtOAc=75:1) to afford compound 2 (1.0 g, yield 71.7%) as a yellow oil. LC/MS (ESI) m/z: 198/200 (M+H)+.

Step 2: 2-Bromo-4-propylpyridine (3)

To a solution of compound 2 (1.0 g, 5.05 mmol) in EtOAc (8 mL) was added PtO$_2$ (120 mg) at 0° C. and the mixture was degassed under N$_2$ atmosphere three times and stirred at room temperature under a H$_2$ balloon for 10 minutes. The mixture was filtered and the filtrate was concentrated to dryness to afford compound 3 (990 mg, yield 98.0%) as white solid that was used directly in the next step. LC/MS (ESI) m/z: 200/202 (M+H)+.

Step 3: 2-Bromo-4-propylpyridine 1-oxide (4)

To a solution of compound 3 (990 mg, 4.9 mmol) in chloroform (10 mL) was added m-CPBA (1.37 g, 7.9 mmol)

and the mixture was stirred at room temperature overnight under $N_2$ atmosphere. The mixture was washed with saturated aqueous $NaHCO_3$ solution and extracted with DCM twice. The combined organic layers were washed with brine, dried over $Na_2SO_4$, filtered, and concentrated to dryness. The residue was purified by column chromatography on silica gel (DCM:MeOH=20:1) to afford compound 4 (800 mg, yield 74.1%) as yellow oil. LC/MS (ESI) m/z: 216/218 $(M+H)^+$.

Step 4:
6-Bromo-N-tert-butyl-4-propylpyridin-2-amine (5)

To a solution of compound 4 (800 mg, 3.7 mmol) in DCM (10 mL) was added 2-methylpropan-2-amine (1.34 g, 18.3 mmoL) followed by the drop-wise addition of trifluoromethanesulfonic anhydride (1.55 g, 5.5 mmol) at 0° C. The mixture was stirred at 0° C. for 30 minutes under a $N_2$ atmosphere. The mixture was washed with aqueous $NaHCO_3$ solution and brine, dried, and concentrated to dryness. The residue was purified by column chromatography on silica gel (PE:EtOAc=20:1) to afford compound 5 (800 mg, yield 80.4%) as yellow oil. LC/MS (ESI) m/z: 271/273 $(M+H)^+$.

Step 5: 6-Bromo-4-propylpyridin-2-amine (6)

A solution of compound 5 (800 mg, 2.95 mmol) in TFA (8 mL) was stirred at 70° C. for 16 hours. The mixture was concentrated to dryness and the residue was poured into an ice-cooled saturated aqueous $NaHCO_3$ solution and extracted with DCM twice. The combined organic phases were washed with brine, dried over anhydrous $Na_2SO_4$, filtered and concentrated to dryness. The residue was purified by column chromatography on silica gel (eluted with PE:EtOAc=10:1) to afford compound 6 (144 mg, yield 22.7%) as a light yellow oil. LC/MS (ESI) m/z: 215/217 $(M+H)^+$.

Step 6: tert-Butyl (1R,3S,5R)-3-[(6-Bromo-4-propylpyridin-2-yl)carbamoyl]-5-methyl-2-azabicyclo[3.1.0]hexane-2-carboxylate (7)

To a solution of compound 6 (68 mg, 0.32 mmol) and (1R,3S,5R)-2-(tert-butoxycarbonyl)-5-methyl-2-azabicyclo[3.1.0]hexane-3-carboxylic acid (76 mg, 0.32 mmol) in DCM (5 mL) was added pyridine (125 mg, 1.6 mmol) followed by the drop-wise addition of $POCl_3$ (53 mg, 0.35 mmol) at 0° C. The mixture was stirred at room temperature for 1 hour. The mixture was diluted with DCM and washed with 0.5 N aqueous HCl and brine, dried over $Na_2SO_4$, filtered, and concentrated to dryness to afford compound 7 (139 mg, yield 100.0%) as a yellow solid that was used directly in the next step. LC/MS (ESI) m/z: 438/440 $(M+H)^+$.

Step 7: (1R,3S,5R)—N-(6-Bromo-4-propylpyridin-2-yl)-5-methyl-2-azabicyclo[3.1.0]hexane-3-carboxamide (8)

To a solution of compound 7 (139 mg, 0.32 mmol) in DCM (4 mL) was added TFA (2 mL) at 0° C. and the reaction was stirred at room temperature for 2 hours. The mixture was concentrated to dryness and washed with ether and dried under vacuum to afford compound 8 (130 mg, yield 100%) as a brown syrup that was directly used to the next reaction without purification. LC/MS (ESI) m/z: 338/340 $(M+H)^+$.

Step 8: (1R,3S,5R)-2-(2-(3-Acetyl-5-(2-methylpyrimidin-5-yl)-1H-indazol-1-yl)acetyl)-N-(6-bromo-4-propylpyridin-2-yl)-5-methyl-2-azabicyclo[3.1.0]hexane-3-carboxamide (516)

To a mixture of compound 8 (65 mg, 0.15 mmol) and [3-acetyl-5-(2-methylpyrimidin-5-yl)indazol-1-yl]acetic acid (46 mg, 0.15 mmol) in DMF (5 mL) was added DIPEA (96 mg, 0.74 mmol) and HATU (84 mg, 0.22 mmol) at 0° C. and the mixture was stirred at room temperature for 1 hour. The mixture was diluted with EtOAc and washed with 10% aqueous LiCl solution and brine, dried over $Na_2SO_4$ and concentrated to dryness. The residue was purified by prep-HPLC to afford Compound 516 (12 mg, yield 12.9%) as white solid. $^1$H-NMR (400 MHz, DMSO-$d_6$) δ 10.73 (s, 1H), 9.04 (t, J=2.6 Hz, 2H), 8.43 (d, J=3.2 Hz, 1H), 7.91 (d, J=3.6 Hz, 1H), 7.88 (t, J=2.4 Hz, 2H), 7.21 (t, J=2.4 Hz, 1H), 5.96 (d, J=17.6 Hz, 1H), 5.57 (d, J=17.6 Hz, 1H), 4.40 (d, J=8.8 Hz, 1H), 3.63 (d, J=4.4 Hz, 1H), 2.69 (s, 3H), 2.66 (s, 3H), 2.63-2.52 (m, 2H), 2.46 (d, J=14.4 Hz, 1H), 2.02-1.95 (m, 1H), 1.57 (q, J=8.4 Hz, 2H), 1.30 (t, J=2.7 Hz, 3H), 0.98 (d, J=4.4 Hz, 2H), 0.90-0.84 (m, 3H). LC/MS (ESI) m/z: 630/632 $(M+H)^+$.

Scheme 103: Synthesis of (2S,4R)-1-{2-[3-Acetyl-5-(2-methylpyrimidin-5-y)indazol-1-yl]acetyl}-N-(6-bromo-3-methylpyridin-2-yl)-4-fluoro-4-methylpyrrolidine-2-carboxamide (430)

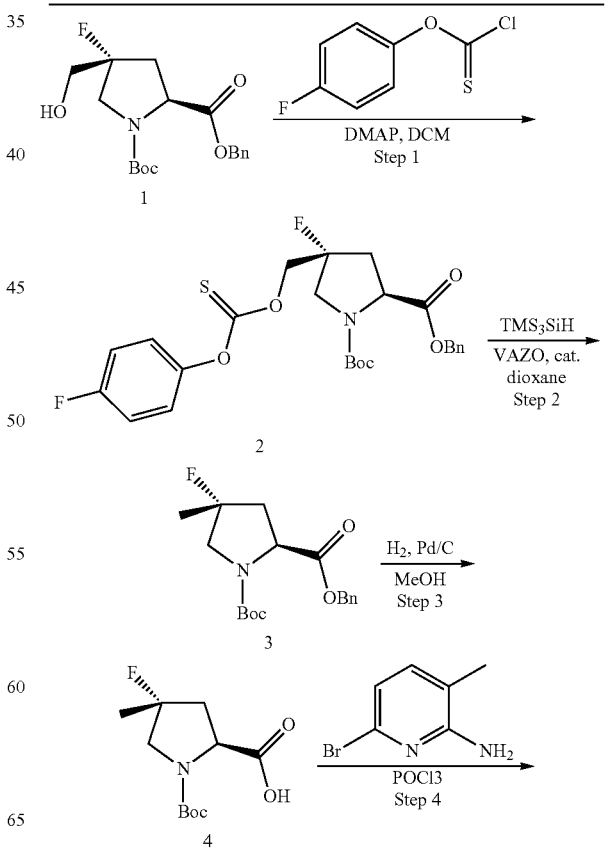

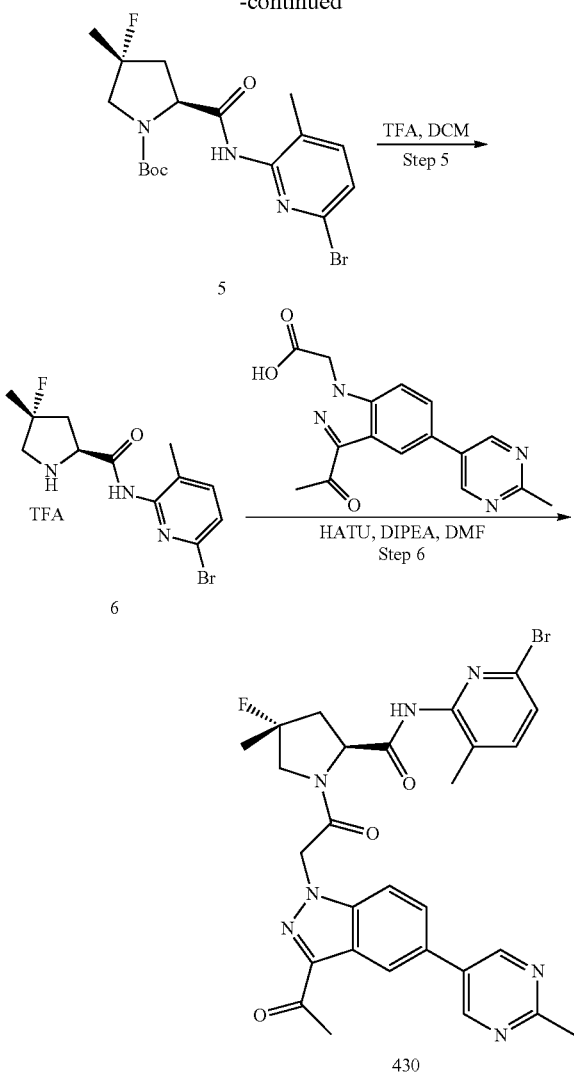

Step 1: 2-Benzyl 1-tert-butyl (2S,4R)-4-fluoro-4-{[(4-fluorophenoxymethanethioyl)oxy]methyl}pyrrolidine-1,2-dicarboxylate (2)

To a mixture of compound 1 (0.41 g, 1.15 mmol) and 4-fluorophenyl chloromethanethioate (0.33 g, 1.73 mmol) in DCM (10 mL) was added DMAP (0.42 g, 3.39 mmol) and the mixture was stirred at 25° C. for 1 day. The mixture was diluted with DCM and washed with 0.5 N HCl and brine, dried and concentrated to dryness. The residue was purified by chromatography on silica gel (eluted with PE:EtOAc=30:1 to 20:1) to afford compound 2 (0.19 g yield 32%) as yellow oil. LC/MS (ESI) m/z: 452 (M+H)$^+$.

Step 2: 2-Benzyl 1-tert-butyl (2S,4R)-4-fluoro-4-methylpyrrolidine-1,2-dicarboxylate (3)

To a solution of compound 2 (0.19 g, 0.37 mmol) in 1,4-dioxane (5 mL) was added tris(trimethylsilyl)silane (0.14 g 0.55 mmol) and VAZO (0.03 g, 0.18 mmol) and the mixture was stirred at 105° C. for 1.5 hours. The reaction mixture was concentrated to dryness and the residue was purified by column chromatographed on silica gel (PE: EtOAc=100:1) to afford compound 3 (84 mg, yield 94.60%) as light yellow oil that was used directly in the next step. LC/MS (ESI) m/z: 338 (M+H)$^+$.

Step 3: (2S,4R)-1-(tert-Butoxycarbonyl)-4-fluoro-4-methylpyrrolidine-2-carboxylic Acid (4)

To a solution of compound 3 (84 mg, 0.25 mmol) in MeOH (3 mL) was added Pd/C (17 mg, 10% wt), and the mixture was degassed under N$_2$ three times and stirred under a H$_2$ balloon at room temperature for 2 hours. The mixture was filtered and the filtrate was concentrated to dryness to afford compound 4 (60 mg, yield 97.46%) as light oil. LC/MS (ESI) m/z: 248 (M+H)$^+$.

Step 4: tert-Butyl (2S,4R)-2-[(6-bromo-3-methylpyridin-2-yl)carbamoyl]-4-fluoro-4-methylpyrrolidine-1-carboxylate (5)

To a mixture of compound 4 (60 mg, 0.24 mmol) and 6-bromo-3-methylpyridin-2-amine (0.045 g, 0.24 mmol) in DCM (3 mL) was added pyridine (0.096 g, 1.21 mmol) followed by POCl$_3$ (0.041 g, 0.27 mmol) at 0° C. The mixture was stirred at room temperature for 30 minutes. The mixture was quenched by ice water and extracted with DCM. The combined organic layers were washed with 0.5 N HCl and brine, dried with anhydrous Na$_2$SO$_4$ and concentrated to dryness to afford compound 5 (87 mg, yield 86.13%) as a yellow solid. LC/MS (ESI) m/z: 416 (M+H)$^+$.

Step 5: (2S,4R)—N-(6-Bromo-3-methylpyridin-2-yl)-4-fluoro-4-methylpyrrolidine-2-carboxamide TFA Salt (6)

To a solution of compound 5 (87 mg, 0.21 mmol) in DCM (2 mL) was added TFA (1 mL) at 0° C., and the mixture was stirred at 25° C. for 2 hours. The mixture was concentrated to dryness and washed with ether to afford compound 6 (90 mg, yield 100%) as a yellow solid that was used directly in the next step. LC/MS (ESI) m/z: 316 (M+H)$^+$.

Step 6: (2S,4R)-1-{2-[3-Acetyl-5-(2-methylpyrimidin-5-yl)indazol-1-yl]acetyl}-N-(6-bromo-3-methylpyridin-2-yl)-4-fluoro-4-methylpyrrolidine-2-carboxamide (430)

To a mixture of compound 6 (30 mg, 0.07 mmol) and [3-acetyl-5-(2-methylpyrimidin-5-yl)indazol-1-yl] acetic acid (25 mg, 0.079 mmol) in DMF (3 mL) was added HATU (45 mg, 0.12 mmol) and DIPEA (0.031 g, 0.24 mmol) at 0° C., and the mixture was stirred at room temperature for 1 hour. The reaction mixture diluted with EtOAc and washed with saturated aqueous NH$_4$Cl solution and brine, dried over anhydrous Na$_2$SO$_4$, filtered and concentrated to dryness. The residue was purified by prep-HPLC to afford 430 (8 mg, yield 17.04%) as white solid. $^1$H-NMR (400 MHz, DMSO-d$_6$) δ 10.46 (s, 1H), 9.04 (d, J=2.2 Hz, 2H), 8.43 (s, 1H), 7.87-7.78 (m, 2H), 7.60 (d, J=8.1 Hz, 1H), 7.42 (d, J=7.9 Hz, 1H), 5.82 (d, J=17.2 Hz, 1H), 5.57 (d, J=17.2 Hz, 1H), 4.64-4.59 (m, 1H), 4.27-4.20 (m, 1H), 3.94-3.86 (m, 1H), 2.68 (s, 3H), 2.64 (s, 3H), 2.20-2.04 (m, 2H), 2.00 (s, 3H), 1.64 (d, J=21.0 Hz, 3H). LC/MS (ESI) m/z: 607 (M+H)$^+$.

Scheme 104: Synthesis of (1R,3S,5R)-2-(2-(3-acetyl-6-fluoro-5-(2-methylpyrimidin-5-yl)-1H-indol-1-yl)acetyl)-N-(6-bromo-3-methylpyridin-2-yl)-5-methyl-2-azabicyclo[3.1.0]hexane-3-carboxamide (505)

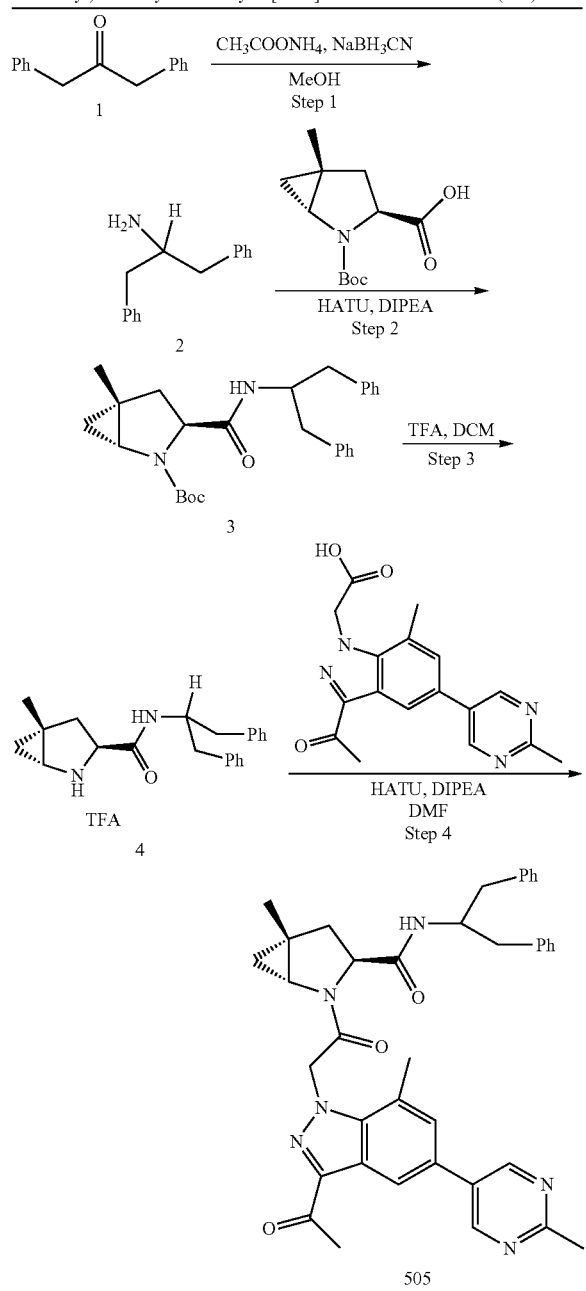

Step 1: 1,3-Diphenylpropan-2-amine (2)

To a solution of dibenzyl ketone (500 mg, 2.38 mmol) in MeOH (10 mL) was added ammonium acetate (1.83 g, 23.78 mmol) and NaBH₃CN (300 mg, 4.76 mmol) at 0° C. and the mixture was stirred at 25° C. for 3 hours. The reaction mixture was quenched with 1N aqueous NaOH solution and extracted with EtOAc twice. The combined organic layers were washed with brine, dried over Na₂SO₄, filtered and concentrated to dryness. The residue was purified by column chromatography via silica gel (eluted with DCM: MeOH=200:1 to 20:1) to afford compound 2 (340 mg, yield 67.7%) as colorless oil. LC/MS (ESI) m/z: 212 (M+H)⁺.

Step 2: tert-Butyl(1R,3S,5R)-3-((1,3-diphenylpropan-2-yl)carbamoyl)-5-methyl-2-azabicyclo[3.1.0]hexane-2-carboxylate (3)

To a mixture of 2 (70 mg, 0.33 mmol) and (1R,3S,5R)-2-(tert-butoxycarbonyl)-5-methyl-2-azabicyclo[3.1.0]hexane-3-carboxylic acid (88 mg, 0.36 mmol) in DMF (3 mL) was added DIPEA (86 mg, 0.66 mmol) and HATU (252 mg, 0.66 mmol) at 0° C. and the mixture was stirred at 25° C. for 2 hours. The mixture was diluted with ethyl acetate, washed with water and brine, dried over Na₂SO₄, filtered and concentrated to dryness. The residue was purified by column chromatography via silica gel (eluted with petroleum ether:EtOAc=50:1 to 1:1) to afford compound 3 (110 mg, yield 76.4%) as colorless oil. LC/MS (ESI) m/z: 435 (M+H)⁺.

Step 3: (1R,3S,5R)—N-(1,3-Diphenylpropan-2-yl)-5-methyl-2-azabicyclo[3.1.0]hexane-3-carboxamide (4)

To a solution of compound 3 (50 mg, 0.115 mmol) in DCM (3 mL) was added TFA (1 mL) at 0° C., and the mixture was stirred at 25° C. for 4 hours. The mixture was concentrated to dryness and the residue was co-evaporated with DCM twice and dried under vacuum to afford 4 (55 mg, yield 100%) as a brown oil that was directly used in the next step without further purification. LC/MS (ESI) m/z: 335 (M+H)⁺.

Step 4: (1R,3S,5R)-2-(2-(3-Acetyl-7-methyl-5-(2-methylpyrimidin-5-yl)-1H-indazol-1-yl)acetyl)-N-(1,3-diphenylpropan-2-yl)-5-methyl-2-azabicyclo[3.1.0]hexane-3-carboxamide (505)

To a mixture of compound 4 (20 mg, 0.06 mmol) and 2-(3-acetyl-7-methyl-5-(2-methylpyrimidin-5-yl)-1H-indazol-1-yl)acetic acid (16.5 mg, 0.05 mmol) in DMF (1 mL) was added DIPEA (23 mg, 0.18 mmol) and HATU (45 mg, 0.12 mmol) at 0° C. and the mixture was stirred at room temperature for 2 hrs. The mixture was diluted with ethyl acetate, washed with water and brine, dried over Na₂SO₄, filtered and concentrated to dryness. The residue was purified by prep-HPLC to afford 505 (1.9 mg, yield 6.44%) as white solid. ¹H-NMR (400 MHz, DMSO-d₆) δ 9.04 (s, 2H), 8.34 (s, 1H), 7.58-7.73 (m, 2H), 7.13-7.30 (m, 10H), 5.92-5.96 (d, J=17.9 Hz, 1H), 5.63-5.67 (d, J=17.8 Hz, 1H), 4.10-4.17 (m, 2H), 3.10-3.11 (m, 1H), 2.63-2.72 (m, 13H), 21.3-2.23 (m, 1H), 1.08 (s, 3H), 0.93-0.95 (m, 1H), 0.76-0.78 (m, 1H). LC/MS (ESI) m/z: 641 (M+H)⁺.

Scheme 105: Synthesis of (2S,4S)-1-(2-(3-Acetyl-5-(2-methylpyrimidin-5-yl)-1H-indazol-1-yl)acetyl)-N-(6-bromo-3-methylpyridin-2-yl)-4-fluoro-4-(methoxymethyl)pyrrolidine-2-carboxamide (421)

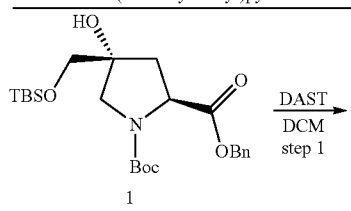

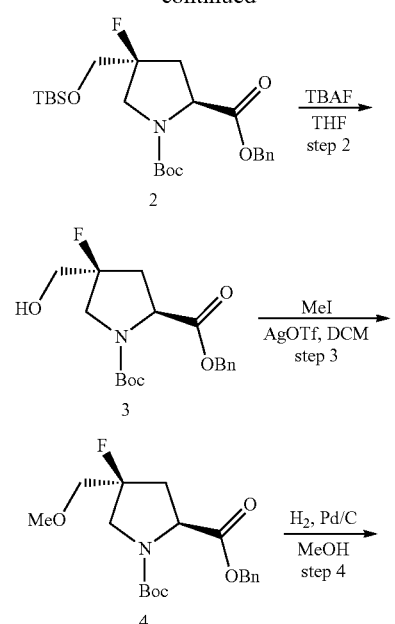

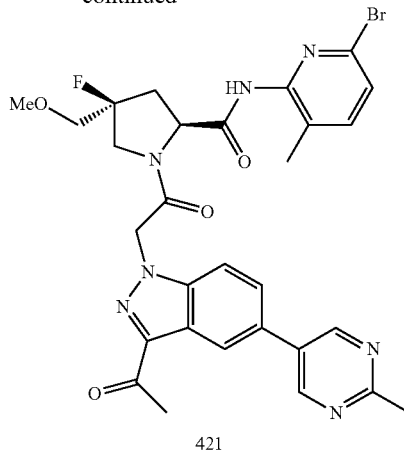

421

Step 1: (2S,4S)-2-Benzyl 1-tert-butyl 4-(((tert-butyldimethylsilyl)oxy)methyl)-4-fluoropyrrolidine-1,2-dicarboxylate (2)

To a solution of compound 1 (1.8 g, 3.87 mmol) in anhydrous DCM (30 mL) was added DAST (0.78 mL, 5.81 mmol) at −65° C. under $N_2$ atmosphere and the reaction mixture was stirred at room temperature for 2 hours. Then the mixture was poured into ice-cooled saturated $NaHCO_3$ solution and extracted with DCM twice. The combined organic layers was washed with brine, dried over anhydrous $Na_2SO_4$ and concentrated to dryness to afford compound 2 (1.6 g, crude) as yellow oil that was directly used to the next reaction without further purification. LC/MS (ESI) m/z: 468 (M+H)$^+$.

Step 2: (2S,4S)-2-Benzyl 1-tert-butyl 4-fluoro-4-(hydroxymethyl)pyrrolidine-1,2-dicarboxylate (3)

To a solution of compound 2 (1.6 g, 34.2 mmol) in THF (15 mL) was added TBAF (4.3 mL, 4.28 mmol, 1M in THF) at 0° C. and the reaction mixture was stirred at room temperature for 30 minutes. Then the mixture was poured into ice water and extracted with EtOAc twice. The combined organic layers were washed with brine, dried over anhydrous $Na_2SO_4$ and concentrated under reduced pressure. The residue was purified by chromatography on silica gel (eluted with petroleum ether:ethyl acetate=6:1 to 2:1) to afford compound 3 (700 mg, yield 57.9%) as light yellow oil. LC-MS: m/z 354 (M+H)$^+$.

Step 3: (2S,4S)-2-Benzyl 1-tert-butyl 4-fluoro-4-(methoxymethyl)pyrrolidine-1,2-dicarboxylate (4)

To a solution of compound 3 (100 mg, 0.283 mmol) in anhydrous DCM (4 mL) was added AgOTf (116.4 mg, 0.453 mmol) followed by 2, 6-di-tert-butylpyridine (0.13 mL, 0.566 mmol). Then the reaction mixture was cooled to 0° C. (external temperature, ice bath) and MeI (0.04 mL, 0.567 mmol) was added drop wise. The resulting slurry was stirred at 0° C. for 1.5 hours at room temperature overnight. The mixture was filtered and the filtrate was evaporated under reduced pressure. The residue was purified by chromatography on silica gel (eluted with petroleum ether:ethyl acetate=15:1 to 5:1) to afford compound 4 (30 mg, yield 28.9%) as a light oil. LC-MS: m/z 368 (M+H)$^+$.

Step 5: (2S,4S)-1-(tert-Butoxycarbonyl)-4-fluoro-4-(methoxymethyl)pyrrolidine-2-carboxylic Acid (5)

To a solution of compound 4 (30 mg, 0.082 mmol) in methanol (2 mL) was added Pd/C (5 mg, 10% wt) and the reaction mixture was stirred at room temperature under a $H_2$ balloon for 1 hour. The mixture was filtered and the filtrate was concentrated to dryness to afford compound 5 (22 mg, yield 97.2%) as a light oil. LC-MS: m/z 278 (M+H)$^+$.

Step 6: (2S,4S)-tert-Butyl 2-((6-bromo-3-methylpyridin-2-yl)carbamoyl)-4-fluoro-4-(methoxymethyl)pyrrolidine-1-carboxylate (7)

To a mixture of compound 5 (22 mg, 0.079 mmol) and compound 6 (14.7 mg, 0.079 mmol) in anhydrous DCM (3 mL) was added pyridine (31.2 mg, 0.395 mmol) followed by POCl$_3$ (13.3 mg, 0.087 mmol) at 0° C. under N$_2$ atmosphere and the reaction mixture was stirred at room temperature for 30 minutes. The mixture was poured into ice water and extracted with DCM twice. The combined organic layers were washed with brine, dried over anhydrous Na$_2$SO$_4$ and concentrated to dryness to afford compound 7 (30 mg, crude) as a light yellow solid that was directly used to the next reaction without further purification. LC/MS (ESI) m/z: 446 (M+H)$^+$.

Step 7: (2S,4S)—N-(6-Bromo-3-methylpyridin-2-yl)-4-fluoro-4-(methoxymethyl)pyrrolidine-2-carboxamide (8)

To a solution of compound 7 (30 mg) in DCM (2 mL) was added TFA (1 mL) at 0° C. and the reaction mixture was stirred at room temperature for 1 hour. The mixture was evaporated to dryness to afford compound 8 (30 mg, crude) as a yellow oil that was directly used to the next reaction without further purification. LC/MS (ESI) m/z: 346 (M+H)$^+$.

Step 8: (2S,4R)-1-(2-(3-Acetyl-5-(2-methylpyrimidin-5-yl)-1H-indazol-1-yl)acetyl)-N-(6-bromo-3-methylpyridin-2-yl)-4-fluoro-4-(methoxymethyl)pyrrolidine-2-carboxamide (421)

To a mixture of compound 8 (30 mg, 0.09 mmol) and compound 9 (28 mg, 0.09 mmol) in DMF (2 mL) was added DIPEA (35 mg, 0.27 mmol) followed by HATU (32 mg, 0.135 mmol) and the reaction mixture was stirred at room temperature for 1 hour. The mixture was poured into ice water and extracted with EtOAc twice. The organic layers were washed with brine, dried over anhydrous Na$_2$SO$_4$ and concentrated under reduced pressure. The residue was purified by prep-HPLC to afford Compound 421 (8 mg, yield 14.48%) as white solid. $^1$H-NMR (400 MHz, DMSO-d$_6$) δ 10.22 (s, 1H), 9.05 (s, 2H), 8.44 (s, 1H), 7.91-7.86 (m, 2H), 7.63 (d, J=8.3 Hz, 1H), 7.46 (d, J=7.9 Hz, 1H), 5.73 (d, J=17.3 Hz, 1H), 5.62 (d, J=17.2 Hz, 1H), 4.72 (d, J=10.3 Hz, 1H), 4.15 (d, J=27.8 Hz, 2H), 3.75-3.64 (m, 3H), 3.41 (s, 3H), 2.69 (s, 3H), 2.65 (s, 3H), 2.36-2.31 (m, 1H), 2.02 (s, 3H). LC/MS (ESI) m/z: 638 (M+H)$^+$.

Scheme 106: Synthesis of (1R,3S,5R)-5-((1,3,4-oxadiazol-2-yl)methyl)-2-(2-(3-acetyl-7-methyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide (359)

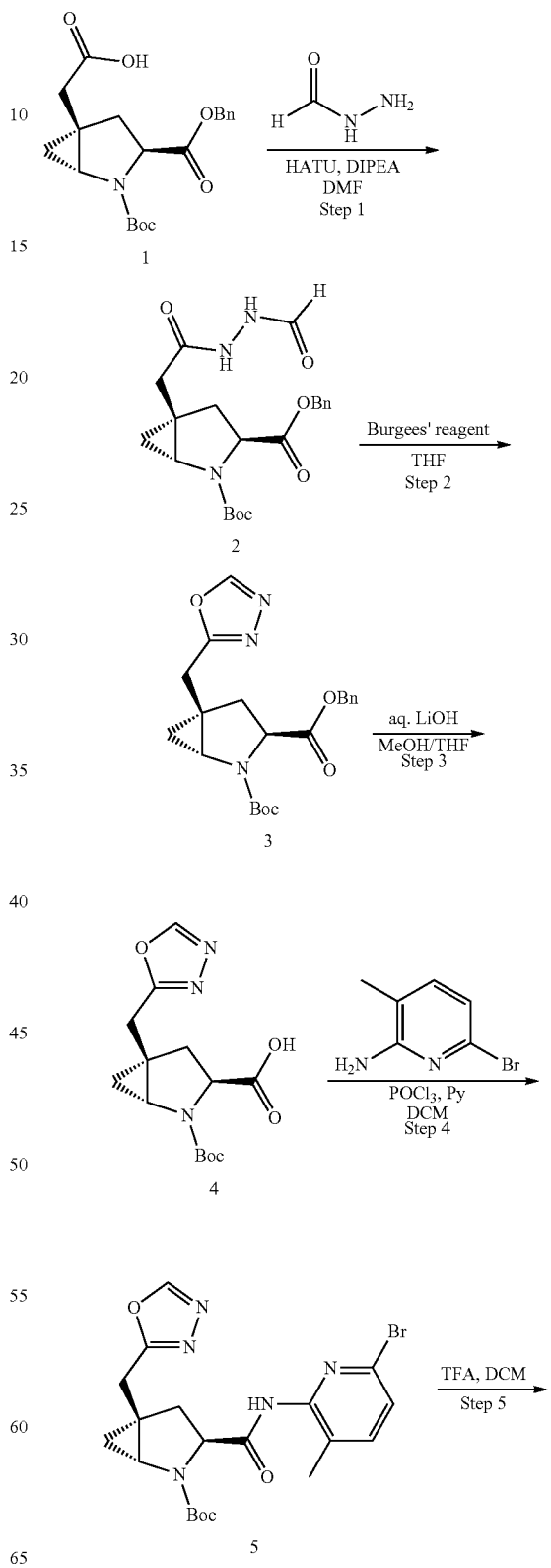

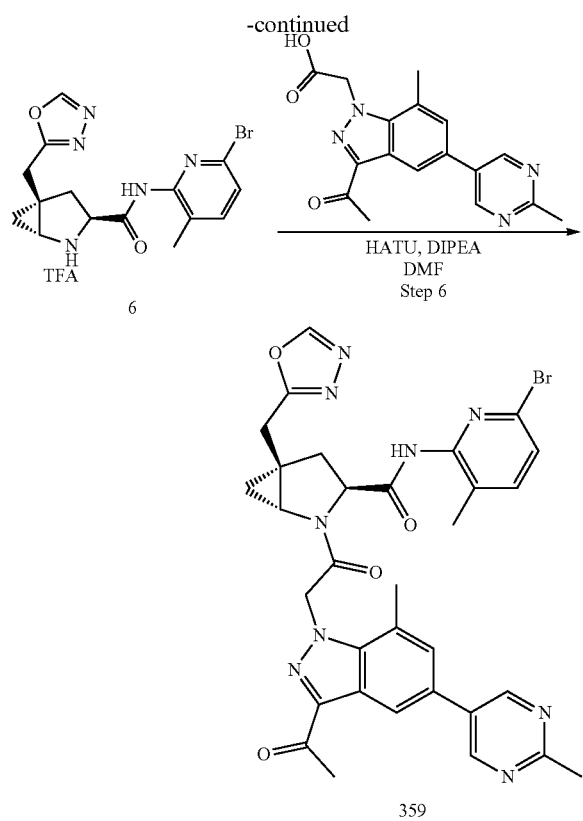

The above scheme and following detailed description depicts one non-limiting method for synthesizing compounds with a —CH$_2$-oxadiazole in the R$^{201}$ position. The skilled artisan will recognize that formohydrazide can be replaced with other hydrazide reagents to afford additional compounds of the present invention. For example, acetohydrazine could be utilized instead of formohydrazide to generate a substituted —CH2-oxadiazole in the R$^{201}$ position.

Step 1: (1R,3S,5R)-3-Benzyl 2-tert-butyl 5-(2-(2-formylhydrazinyl)-2-oxoethyl)-2-azabicyclo[3.1.0]hexane-2,3-dicarboxylate (2)

To a mixture of compound 1 (0.2 g, 0.53 mmol) and N-formylhydrazine (0.064 g, 1.06 mmol) in 1,4-dioxane (4 mL) was added EDCI (0.124 g, 0.8 mmol) and HOBt (0.108 g, 0.8 mmol) followed by DIPEA (0.37 mL, 2.13 mmol) at 0° C., and the mixture was stirred at 25° C. for 16 hours. The mixture was diluted with EtOAc and washed with saturated aqueous NH$_4$Cl solution three times. The organic layer was dried over Na$_2$SO$_4$, filtered, and concentrated to dryness. The residue was purified by silica gel chromatography (eluted with DCM:MeOH=20:1 to 10:1) to afford compound 2 (0.12 g, yield 53.9%) as light yellow solid. LC/MS (ESI) m/z: 440 (M+Na)$^+$.

Step 2: (1R,3S,5R)-3-Benzyl 2-tert-butyl 5-((1,3,4-oxadiazol-2-yl)methyl)-2-azabicyclo[3.1.0]hexane-2,3-dicarboxylate (3)

To a solution of compound 2 (0.12 g, 0.29 mmol) in tetrahydrofuran (5 mL) was added (A1) Burgess reagent (0.082 g, 0.34 mmol) in one portion under N$_2$ atmosphere and the reaction was stirred at 75° C. under N$_2$ atmosphere for 4 hours at which TLC (DCM:MeOH=20:1) showed about 30% conversion. Additional Burgess reagent (0.089 g, 0.37 mmol) was added and the reaction mixture was stirred under N$_2$ atmosphere for 16 hours. The mixture was diluted with EtOAc, washed with water and brine, dried and concentrated to dryness. The residue was purified by silica gel chromatography (eluted with DCM:MeOH=30:1 to 15:1) to afford compound 3 (0.089 g, yield 62%) as a light yellow oil. LC/MS (ESI) m/z: 422 (M+Na)$^+$.

Step 3: (1R,3S,5R)-5-((1,3,4-Oxadiazol-2-yl)methyl)-2-(tert-butoxycarbonyl)-2-azabicyclo[3.1.0]hexane-3-carboxylic Acid (4)

To a solution of compound 3 (0.08 g, 0.16 mmol) in THF (2 mL), MeOH (2 mL) and water (1 mL) was added lithiumol (0.012 g, 0.481 mmol) at 0° C. and the reaction mixture was stirred at 0° C. for 3 hours. The mixture was concentrated to dryness and diluted with water. The mixture was washed with EtOAc twice and the aqueous layer was acidified by adding 0.5 N HCl to pH of approximately 3. The mixture was extracted with DCM twice and the combined organic layers were dried over anhydrous Na$_2$SO$_4$, filtered, and concentrated to afford compound 4 (0.035 g, Yield 70.6%) as a yellow solid. LC/MS (ESI) m/z: 332 (M+Na)$^+$.

Step 4: (1R,3S,5R)-tert-Butyl 5-((1,3,4-oxadiazol-2-yl)methyl)-3-((6-bromo-3-methylpyridin-2-yl)carbamoyl)-2-azabicyclo[3.1.0]hexane-2-carboxylate (5)

To a mixture of compound 4 (0.035 g, 0.113 mmol) and 6-bromo-3-methylpyridin-2-amine (0.021 g, 0.113 mmol) in DCM (2 mL) was added pyridine (0.054 g, 0.679 mmol) and the mixture was cooled to 0° C. POCl$_3$ (0.035 g, 0.226 mmol) was added to the mixture drop-wise at 0° C. and the reaction mixture was stirred at 0° C. for 3 hours. The mixture was diluted with DCM and washed with ice-cool 0.5 N aqueous HCl and brine, dried over Na$_2$SO$_4$, filtered, and concentrated to dryness to afford compound 5 (0.033 g, Yield 61%) as a light yellow solid that was directly used to the next reaction without purification. LC/MS (ESI) m/z: 480 (M+H)$^+$.

Step 5: (1R,3S,5R)-5-((1,3,4-Oxadiazol-2-yl)methyl)-N-(6-bromo-3-methylpyridin-2-yl)-2-azabicyclo[3.1.0]hexane-3-carboxamide TFA Salt (6)

To a solution of compound 5 (0.033 g, 0.069 mmol) in DCM (1 mL) was added TFA (0.4 mL) at 0° C. and the mixture was stirred at 0° C. for 2 hours. The mixture was concentrated to dryness to afford compound 6 (0.04 g, yield 95.6%) as a yellow syrup that was directly used in the next reaction without purification. LC/MS (ESI) m/z: 380 (M+H)$^+$.

Step 6: (1R,3S,5R)-5-((1,3,4-Oxadiazol-2-yl)methyl)-2-(2-(3-acetyl-7-methyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide (359)

To a mixture of compound 6 (0.04 g, 0.081 mmol) and [3-acetyl-7-methyl-5-(2-methylpyrimidin-5-yl)indazol-1-yl]acetic acid (0.029 g, 0.089 mmol) in DMF (2 mL) was added DIPEA (0.053 g, 0.41 mmol) at 0° C. followed by HATU (0.046 g, 0.12 mmol) and the mixture was stirred at 25° C. for 4 hours. The mixture was diluted with EtOAc and washed with saturated aqueous NH₄Cl solution and brine successively, dried over Na₂SO₄, filtered and concentrated to afford crude product that was purified by preparatory TLC (eluted with DCM:MeOH=15:1) to afford Compound 359 (6 mg, yield 10.8%) as white solid. ¹H-NMR (400 MHz, CD₃OD) δ 8.97 (s, 2H), 8.93 (s, 1H), 8.39 (s, 1H), 7.51-7.53 (d, J=8.0 Hz, 1H), 7.51 (s, 1H), 7.35-7.37 (d, J=8.0 Hz, 1H), 5.95-6.00 (d, J=18.0 Hz, 1H), 5.78-5.82 (d, J=18.0 Hz, 1H), 4.59-4.63 (m, 1H), 3.84-3.86 (m, 1H), 3.37-3.41 (d, J=16.0 Hz, 1H), 3.18-3.22 (d, J=16.0 Hz, 1H), 2.73 (s, 3H), 2.74 (s, 3H), 2.69-2.72 (m, 1H), 2.67 (s, 3H), 2.44-2.49 (m, 1H), 2.08 (s, 3H), 1.28-1.30 (m, 1H), 1.18-1.20 (m, 1H). LC/MS (ESI) m/z: 684/686 (M+H)⁺.

(1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-((5-methyl-1,3,4-oxadiazol-2-yl)methyl)-2-azabicyclo[3.1.0]hexane-3-carboxamide ¹H-NMR (400 MHz, CD₃OD) δ 8.97 (s, 2H), 8.99 (s, 1H), 8.41 (s, 1H), 7.52-7.54 (d, J=8.0 Hz, 1H), 7.53 (s, 1H), 5.97-6.01 (d, J=17.6 Hz, 1H), 5.79-5.84 (d, J=17.6 Hz, 1H), 4.60-4.62 (m, 1H), 3.83-3.85 (m, 1H), 3.23-3.27 (d, J=15.6 Hz, 1H), 3.14-3.18 (d, J=15.6 Hz, 1H), 2.76 (s, 3H), 2.74 (s, 3H), 2.70-2.72 (m, 1H), 2.71 (s, 3H), 2.51 (s, 3H), 2.43-2.48 (m, 1H), 2.08 (s, 3H), 1.28-1.30 (m, 1H), 1.17-1.19 (m, 1H). LC/MS (ESI) m/z: 698/700 (M+H)⁺.

Scheme 107: Synthesis of (1R,3S,5R)-N-(3-((2H-Tetrazol-5-yl)methyl)-6-bromopyridin-2-yl)-2-(2-(3-acetyl-5-(2-methylpyrimidin-5-yl)-1H-pyrazolo[3,4-c]pyridin-1-yl)acetyl)-5-methyl-2-azabicyclo[3.1.0]hexane-3-carboxamide (397)

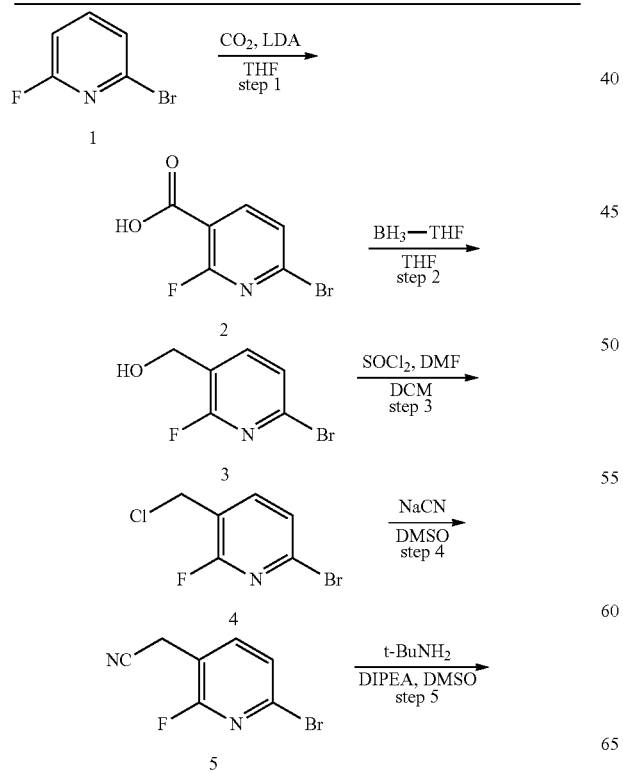

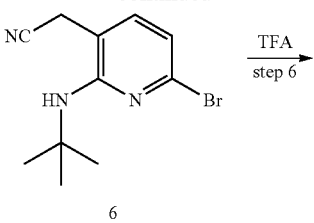

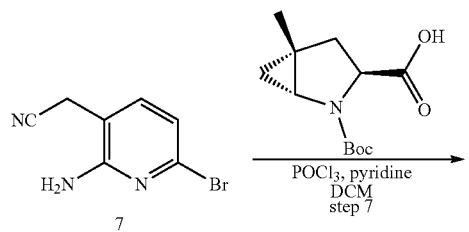

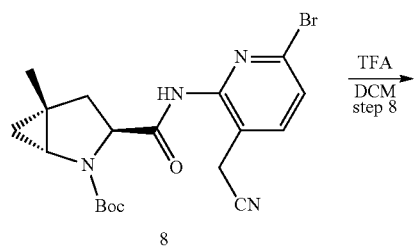

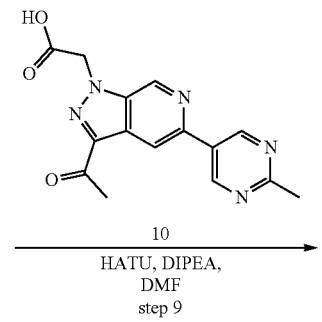

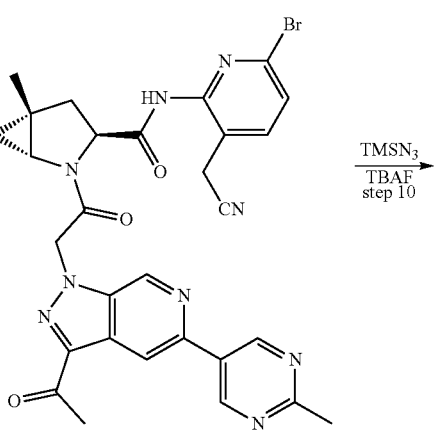

-continued

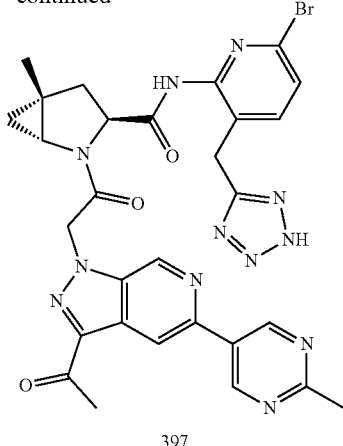

397

Step 1: 6-Bromo-2-fluoronicotinic Acid (2)

To a solution of compound 1 (5 g, 28.41 mmol) in tetrahydrofuran (80 mL) was added LDA (15.6 mL, 31.2 mmol, 2M in THF) drop-wise at −78° C. under $N_2$ atmosphere and the mixture was stirred at −78° C. for 3 hours. A steam of dry $CO_2$ was passed through the solution and the mixture was stirred at −78° C. for an additional 30 minutes. The reaction was quenched with water and washed with EtOAc. The aqueous layer was acidified with 1 N aqueous HCl and extracted with EtOAc twice. The combined organic layers were washed with brine, dried with anhydrous $Na_2SO_4$ and concentrated to afford compound 2 (2.85 g, yield 45.60%) as a yellow solid that was used directly in the next step. LC/MS (ESI) m/z: 221 (M+H)$^+$.

Step 2: (6-Bromo-2-fluoropyridin-3-yl) methanol (3)

To a solution of compound 2 (2.85 g, 12.96 mmol) in tetrahydrofuran (20 mL) was added borane-tetrahydrofuran complex (32.3 mL, 32.3 mmol, 1M in THF) drop-wise at 0° C. and the mixture was stirred at room temperature under $N_2$ atmosphere overnight. After cooling to 0° C., the reaction mixture was basified with saturated aqueous $K_2CO_3$ solution and the solvent was removed. The residue was extracted with EtOAc twice and the combined organic layers were washed with brine, dried over anhydrous $Na_2SO_4$ and concentrated. The residue was purified by column chromatography on silica gel (eluted with PE:EtOAc=30:1 to 10:1) to afford compound 3 (1 g, yield 37.47%) as a white solid. LC/MS (ESI) m/z: 206 (M+H)$^+$.

Step 3: 6-Bromo-3-(chloromethyl)-2-fluoropyridine (4)

To a solution of compound 3 (53 mg, 0.26 mmol) in thionyl chloride (8 mL) was added DMF (0.02 mL) at 0° C. under a $N_2$ atmosphere and the mixture was stirred at room temperature for 5 hours under $N_2$ atmosphere. The mixture was concentrated to dryness and the residue was dissolved in DCM. The mixture was basified by adding saturated aqueous $NaHCO_3$ solution and the layers were separated. The organic layers were washed with brine, dried with anhydrous $Na_2SO_4$, filtered and concentrated to dryness to afford compound 4 (52 mg, yield 90.07%) as a yellow oil that was used directly in the next step. LC/MS (ESI) m/z: 224 (M+H)$^+$.

Step 4: 2-(6-Bromo-2-fluoropyridin-3-yl) acetonitrile (5)

Powered sodium cyanide (0.22 g, 4.46 mmol) was added to DMSO (5 mL) and the mixture was stirred at room temperature for 20 minutes. A solution of compound 4 (0.5 g, 2.23 mmol) in DMSO (5 mL) was added to the above mixture drop-wise for 10 minutes. The resulting mixture was stirred at room temperature for 1 hour. The mixture was cooled to 0° C. and water was added slowly to the mixture. The resulting mixture was extracted with DCM twice and the combined organic layers were washed with brine, dried over anhydrous $Na_2SO_4$, filtered and concentrated to dryness. The residue was purified by column chromatography on silica gel (eluted with PE:EtOAc=50:1 to 40:1) to afford compound 5 (0.17 g, yield 34.66%) as a light yellow solid. LC/MS (ESI) m/z: 216 (M+H)$^+$.

Step 5: 2-(6-Bromo-2-(tert-butylamino) pyridin-3-yl) acetonitrile (6)

To a mixture of compound 5 (0.17 g, 0.77 mmol) and DIPEA (0.3 g, 2.32 mmol) in DMSO (4 mL) was added erbumine (0.28 g, 3.86 mmol) and the mixture was stirred at 40° C. in a sealed tube overnight. The mixture was diluted with $H_2O$ and extracted with EtOAc twice. The combined organic layers were washed with brine, dried with anhydrous $Na_2SO_4$ and concentrated to dryness. The residue was purified by chromatography on silica gel (PE:EtOAc=100:1 to 60:1) to afford compound 6 (0.11 g, yield 53.13%) as a yellow oil. LC/MS (ESI) m/z: 268 (M+H)$^+$.

Step 6: 2-(2-Amino-6-bromopyridin-3-yl) acetonitrile (7)

A round-bottom flask was charged with compound 6 (0.11 g, 0.41 mmol) and trifluoroacetic acid (2 mL) and the mixture was stirred at 70° C. for 0.5 hour. The reaction mixture was concentrated to dryness and the residue was basified with saturated aqueous $NaHCO_3$ solution and extracted with EtOAc twice. The combined organic layers were washed with brine, dried with anhydrous $Na_2SO_4$ and concentrated to dryness. The residue was purified by chromatography on silica gel (PE:EtOAc=50:1 to 8:1) to afford compound 7 (69 mg, yield 79.31%) as white solid. LC/MS (ESI) m/z: 214 (M+H)$^+$.

Step 7: (1R, 3S, 5R)-tert-Butyl 3-(6-bromo-3-(cyanomethyl) pyridin-2-ylcarbamoyl)-5-methyl-2-azabicyclo [3.1.0] hexane-2-carboxylate (8)

To a mixture of compound 7 (65 mg, 0.31 mmol) and (1R, 3S, 5R)-2-(tert-butoxycarbonyl)-5-methyl-2-azabicyclo [3.1.0] hexane-3-carboxylic acid (81 mg, 0.34 mmol) in dichloromethane (5 mL) was added pyridine (121 mg 1.53 mmol) followed by phosphoryl chloride (52 mg, 0.34 mmol) at 0° C. and the mixture was stirred at room temperature for 0.5 hour under $N_2$ atmosphere. The mixture was poured into iced-water and extracted with DCM twice. The combined organic layers were washed with brine, dried with anhydrous $Na_2SO_4$ and concentrated to dryness. The residue was purified by chromatography on silica gel (PE:EtOAc=30:1 to 8:1) to afford compound 8 (45 mg, yield 33.72%) as a yellow solid. LC/MS (ESI) m/z: 436 (M+H)⁺.

Step 8: (1R, 3S, 5R)—N-(6-Bromo-3-(cyanomethyl) pyridin-2-yl)-5-methyl-2-azabicyclo [3.1.0] hexane-3-carboxamide (9)

To a solution of compound 8 (45 mg, 0.10 mmol) in dichloromethane (3 mL) was added trifluoroacetic acid (1 mL) at 0° C., and the mixture was stirred at room temperature for 1 hour. The reaction mixture was concentrated to dryness and the residue was washed with ether and dried under vacuum to afford compound 9 (30 mg, yield 86.58%) as a yellow solid that was used directly in the next step. LC/MS (ESI) m/z: 336 (M+H)⁺.

Step 9: (1R, 3S, 5R)-2-(2-(3-Acetyl-5-(2-methylpyrimidin-5-yl)-1H-pyrazolo [3, 4-c]pyridin-1-yl) acetyl)-N-(6-bromo-3-(cyanomethyl) pyridin-2-yl)-5-methyl-2-azabicyclo [3.1.0] hexane-3-carboxamide (11)

To a mixture of compound 9 (30 mg, 0.089 mmol) and compound 10 (28 mg, 0.089 mmol) in DMF (1.5 mL) was added DIPEA (58 mg, 0.45 mmol) followed by HATU (68 mg, 0.18 mmol) at 0° C. The reaction mixture was stirred at room temperature for 1 hour. The mixture was diluted with H₂O and extracted with EtOAc twice. The combined organic layers were washed with 10% aqueous LiCl solution and brine, dried with anhydrous Na₂SO₄, and concentrated. The residue was purified by chromatography on silica gel (DCM: MeOH=100:1 to 50:1) to afford compound 11 (38 mg, yield 67.56%) as a dark green solid. LC/MS (ESI) m/z: 628 (M+H)⁺.

Step 10: (1R, 3S, 5R)—N-(3-((2H-Tetrazol-5-yl) methyl)-6-bromopyridin-2-yl)-2-(2-(3-acetyl-5-(2-methylpyrimidin-5-yl)-1H-pyrazolo [3, 4-c] pyridin-1-yl) acetyl)-5-methyl-2-azabicyclo [3.1.0] hexane-3-carboxamide (397)

A sealed tube was charged with compound 11 (34 mg, 0.054 mmol), TBAF (0.1 mL, 1 M in THF) and azidotrimethylsilane (1 mL), and the reaction mixture was stirred at 85° C. overnight. The mixture was concentrated to dryness and the residue was purified by pre-HPLC to afford Compound 397 (5 mg, yield 27.5%) as white solid. ¹H-NMR (400 MHz, DMSO-d₆) δ 11.21 (s, 1H), 9.33 (s, 2H), 9.26 (d, J=1.2 Hz, 1H), 8.60 (d, J=1.2 Hz, 1H), 7.63 (d, J=8.0 Hz, 1H), 7.45 (d, J=8.0 Hz, 1H), 6.23 (d, J=17.2 Hz, 1H), 5.74 (d, J=16.8 Hz, 1H), 4.44 (dd, J=9.6, 4.8 Hz, 1H), 4.05 (d, J=15.6 Hz, 2H), 3.53-3.50 (m, 1H), 2.68 (d, J=5.6 Hz, 6H), 2.16-1.96 (m, 2H), 1.28 (s, 3H), 1.10-1.05 (m, 1H), 1.05-1.00 (m, 1H). LC/MS (ESI) m/z: 671 (M+H)⁺.

Scheme 108: Synthesis of (1R,3S,5R)-2-(2-(3-acetyl-5-(2-methylpyrimidin-5-yl)-1H-pyrazolo[3,4-c]pyridin-1-yl)acetyl)-N-(6-bromo-3-(3-morpholinopropyl)pyridin-2-yl)-5-methyl-2-azabicyclo[3.1.0]hexane-3-carboxamide (400)

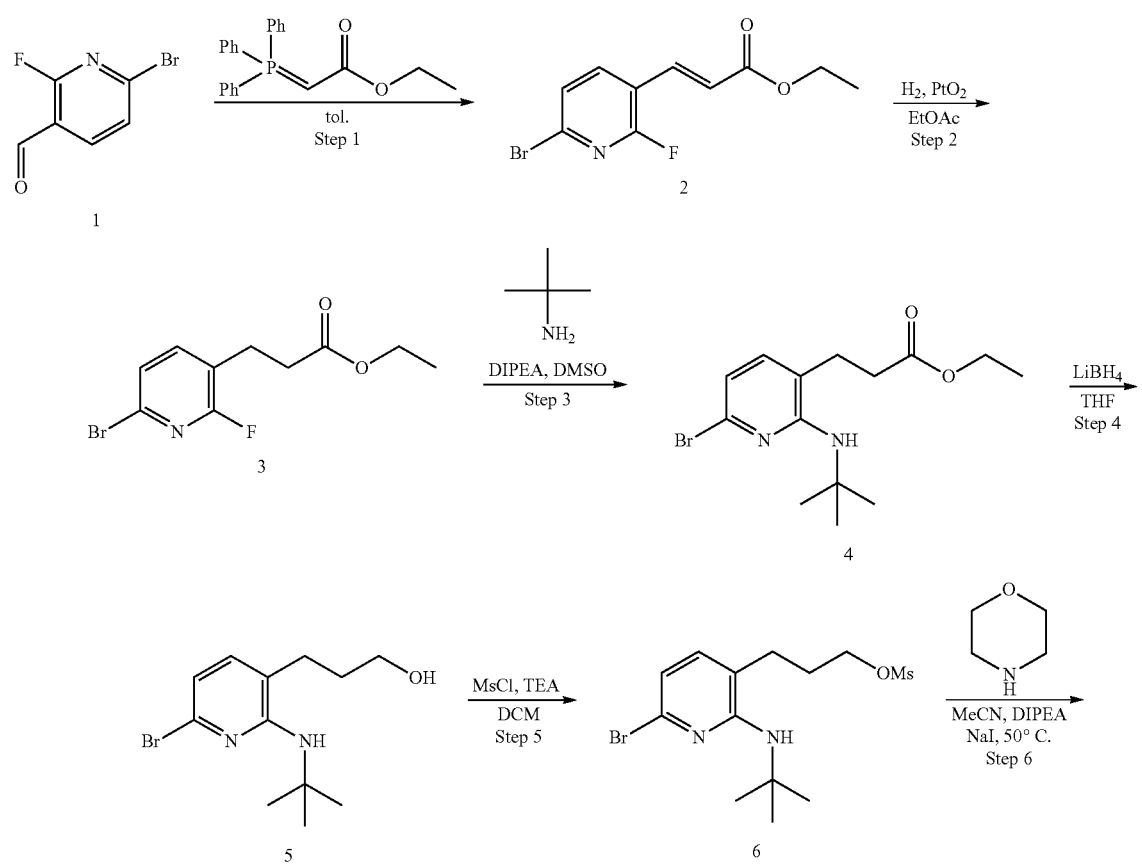

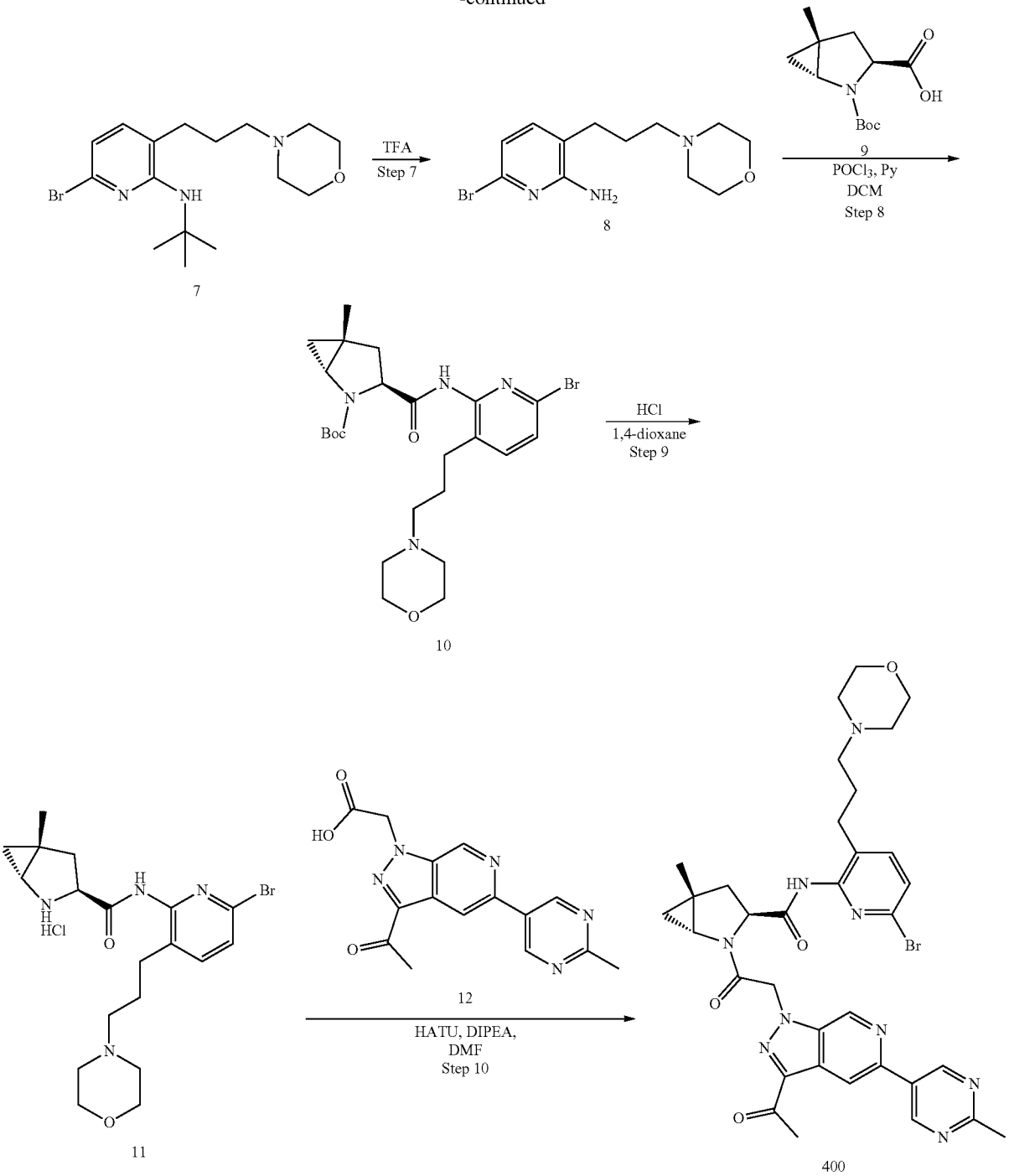

Step 1: (E)-Ethyl 3-(6-bromo-2-fluoropyridin-3-yl) acrylate (2)

To a solution of compound 1 (500 mg, 2.45 mmol) in toluene (6 mL) was added ethyl 2-(triphenylphosphoranylidene)acetate (937.9 mg, 2.70 mmol) at 0° C. and the reaction mixture was stirred at 50° C. overnight. The mixture was evaporated under reduced pressure and the residue was purified by chromatography on silica gel (petroleum ether: ethyl acetate=20:1 to 10:1) to afford compound 2 (523 mg, yield 78.4%) as white solid. LC/MS (ESI) m/z: 274 (M+H)$^+$.

Step 2: Ethyl 3-(6-bromo-2-fluoropyridin-3-yl)propanoate (3)

To a solution of compound 2 (523 mg, 1.92 mmol) in EtOAc (6 mL) was added PtO$_2$ (53 mg) and the mixture was degassed under N$_2$ atmosphere three times and stirred under a H$_2$ balloon at room temperature for 2 hours. The mixture was filtered and the filtrate was evaporated under reduced

Step 3: Ethyl 3-(6-bromo-2-(tert-butylamino)pyridin-3-yl)propanoate (4)

To a mixture of compound 3 (500 mg, 1.82 mmol) and 2-methylpropan-2-amine (664 mg, 9.09 mmol) in DMSO (5 mL) was added DIPEA (704 mg, 5.45 mmol) and the reaction mixture was stirred at 75° C. in a sealed tube for 48 hours. The mixture was poured into ice water and extracted with EtOAc twice. The combined organic layers were washed with brine, dried over anhydrous $Na_2SO_4$ and evaporated under reduced pressure. The residue was purified by chromatography on silica gel (eluted with petroleum ether:ethyl acetate=1:0 to 100:1) to afford compound 4 (104 mg, yield 17.4%) as a light oil. LC/MS (ESI) m/z: 329 (M+H)$^+$.

Step 4: 3-(6-Bromo-2-(tert-butylamino)pyridin-3-yl)propan-1-ol (5)

To a solution of compound 4 (104 mg, 0.32 mmol) in anhydrous THF (3 mL) was added 1 M $LiBH_4$ THF solution (0.64 mL, 0.64 mmol) at 0° C. under $N_2$ atmosphere and the reaction mixture was stirred at 40° C. for 2 hours. The mixture was poured into ice water and extracted with EtOAc twice. The combined organic layers were washed with brine, dried over anhydrous $Na_2SO_4$ and concentrated under reduced pressure to afford compound 5 (70 mg, yield 76.5%) as a yellow oil that was used in the next reaction without further purification. LC/MS (ESI) m/z: 287 (M+H)$^+$.

Step 5: 3-(6-Bromo-2-(tert-butylamino)pyridin-3-yl)propyl methanesulfonate (6)

To a solution of compound 5 (69 mg, 0.24 mmol) in anhydrous DCM (3 mL) was added TEA (0.07 mL, 0.48 mmol) followed by a solution of MsCl (41.5 mg, 0.36 mmol) in DCM (0.5 mL) at 0° C. under $N_2$ atmosphere. The reaction mixture was stirred at 0° C. for 1 hour. The mixture was poured into ice water and extracted with DCM twice. The combined organic layers were dried over anhydrous $Na_2SO_4$ and concentrated under reduced pressure to afford compound 6 (85 mg, yield 97.2%) as a yellow oil that was directly used in the next reaction without further purification. LC/MS (ESI) m/z: 365 (M+H)$^+$.

Step 6: 6-Bromo-N-(tert-butyl)-3-(3-morpholinopropyl)pyridin-2-amine (7)

To a mixture of compound 6 (85 mg, 0.24 mmol) and 2-methylpropan-2-amine (0.1 mL, 1.21 mmol) in MeCN (2 mL) was added DIPEA (0.12 mL, 0.72 mmol) followed by NaI (26.4 mg, 0.24 mmol) and the reaction mixture was stirred at 50° C. overnight. The mixture was poured into ice water and extracted with EtOAc twice. The combined organic layers were washed with brine, dried over anhydrous $Na_2SO_4$ and evaporated under reduced pressure to afford compound 7 (75 mg, crude) as a yellow oil that was directly used to the next reaction without further purification. LC/MS (ESI) m/z: 329 (M+H)$^+$.

Step 7: 6-Bromo-3-(3-morpholinopropyl)pyridin-2-amine (8)

A solution of compound 7 (75 mg, 0.24 mmol) in TFA (2 mL) was stirred at 70° C. for 30 minutes. The mixture was evaporated under reduced pressure and the residue was portioned with EtOAc and saturated aqueous $NaHCO_3$ solution. The organic layer was washed with brine, dried over anhydrous $Na_2SO_4$ and evaporated under reduced pressure. The residue was purified by chromatography on silica gel (eluted with petroleum ether:ethyl acetate=1:1 to 0:1) to afford compound 8 (44 mg, yield 61.3%) as a light brown solid. LC/MS (ESI) m/z: 300 (M+H)$^+$.

Step 8: (1R,3S,5R)-tert-Butyl 3-((6-bromo-3-(3-morpholinopropyl)pyridin-2-yl)carbamoyl)-5-methyl-2-azabicyclo[3.1.0]hexane-2-carboxylate (10)

To a mixture of compound 8 (44 mg, 0.15 mmol) and compound 9 (35.5 mg, 0.147 mmol) in anhydrous DCM (3 mL) was added pyridine (0.06 mL, 0.735 mmol) followed by $POCl_3$ (0.02 mL, 0.162 mmol) at 0° C., and the reaction mixture was stirred at room temperature for 30 minutes. The mixture was poured into ice water and extracted with DCM twice. The organic layers were washed with brine, dried over $Na_2SO_4$ and concentrated under reduced pressure. The residue was purified by chromatography on silica gel (eluted with petroleum ether:ethyl acetate=1:1 to 0:1) to afford compound 10 (27 mg, yield 34.6%) as light yellow solid. LC/MS (ESI) m/z: 523 (M+H)$^+$.

Step 9: (1R,3S,5R)-tert-Butyl 3-((6-bromo-3-(3-morpholinopropyl)pyridin-2-yl)carbamoyl)-5-methyl-2-azabicyclo[3.1.0]hexane-2-carboxylate (11)

A solution of 4 N HCl/dioxane solution (2 mL) was added to compound 10 (27 mg, 0.05 mmol) at 0° C. under $N_2$ atmosphere and the mixture was stirred at room temperature for 1 hour. The mixture was concentrated to dryness to afford compound 11 (20 mg, yield 100%) as a brown solid that was directly used in the next reaction without further purification. LC/MS (ESI) m/z: 423 (M+H)$^+$.

Step 10: (1R,3S,5R)-2-(2-(3-Acetyl-5-(2-methylpyrimidin-5-yl)-1H-pyrazolo[3,4-c]pyridin-1-yl)acetyl)-N-(6-bromo-3-(3-morpholinopropyl)pyridin-2-yl)-5-methyl-2-azabicyclo[3.1.0]hexane-3-carboxamide (400)

To a mixture of compound 11 (20 mg, 0.052 mmol) and compound 12 (17.7 mg, 0.057 mmol) in DMF (2 mL) was added HATU (29.6 mg, 0.078 mmol) followed by DIPEA (0.04 mL, 0.156 mmol) at 0° C. and the reaction mixture was stirred at room temperature for 1.5 hours. The mixture was poured into ice water and extracted with EtOAc twice. The organic layers were washed with brine, dried over anhydrous $Na_2SO_4$ and concentrated under reduced pressure. The residue was purified by prep-HPLC to afford 400 (7 mg, yield 18.9%) as white solid. $^1$H-NMR (400 MHz, DMSO-$d_6$) δ 10.22 (s, 1H), 9.35 (s, 2H), 9.31 (d, J=1.2 Hz, 1H), 8.62 (d, J=1.2 Hz, 1H), 7.65 (d, J=8.0 Hz, 1H), 7.47 (d, J=8.0 Hz, 1H), 6.07 (d, J=17.4 Hz, 1H), 5.72 (d, J=17.2 Hz, 1H), 4.40 (dd, J=9.2, 5.4 Hz, 1H), 3.61 (dd, J=5.5, 2.3 Hz, 1H), 3.40-3.37 (m, 4H), 2.69 (d, J=3.8 Hz, 6H), 2.60-2.52 (m, 2H), 2.41-2.33 (m, 2H), 2.03 (d, J=12.5 Hz, 4H), 1.94 (t, J=7.1 Hz, 2H), 1.54-1.46 (m, 2H), 1.34 (s, 3H), 1.09 (dd, J=5.3, 2.2 Hz, 1H), 1.01 (t, J=5.4 Hz, 1H). LC/MS (ESI) m/z: 716 (M+H)$^+$.

Scheme 109: Synthesis of (1R,3S,5R)-2-(2-(3-Acetyl-5-(2-methylpyrimidin-5-yl)-1H-pyrazolo[3,4-c]pyridin-1-yl)acetyl)-N-(6-bromo-3-methylpyridin-2-yl)-5-(((difluoromethoxy)methyl)-2-azabicyclo[3.1.0]hexane-3-carboxamide (384)

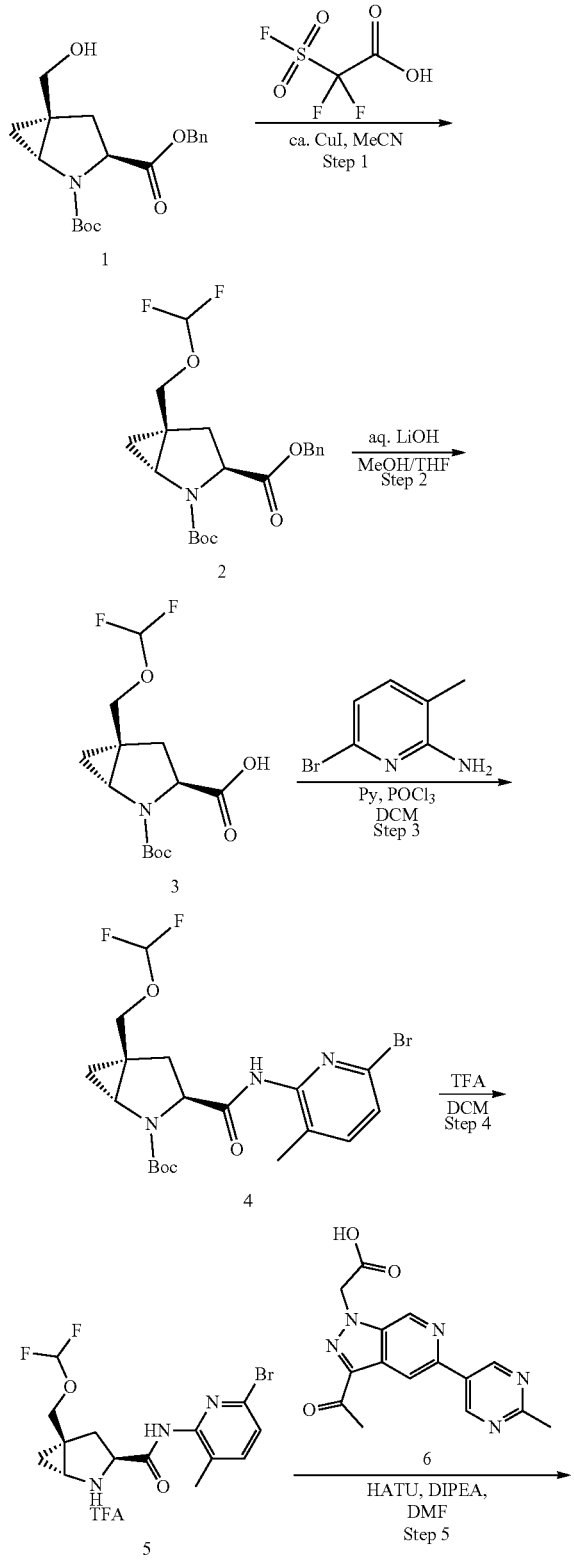

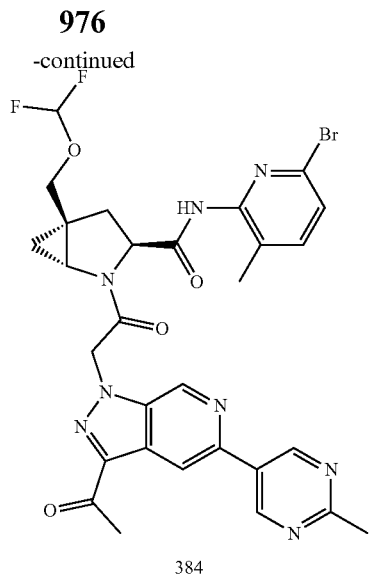

384

Step 1: (1R,3S,5S)-2-tert-Butyl 3-ethyl 5-((difluoromethoxy)methyl)-2-azabicyclo[3.1.0]hexane-2,3-dicarboxylate (2)

To a mixture of compound 1 (500 mg, 1.44 mmol) and CuI (55 mg, 0.288 mmol) in anhydrous MeCN (25 mL) was added 2,2-difluoro-2-(fluorosulfonyl)acetic acid (513 mg, 2.88 mmol) at room temperature under $N_2$ atmosphere and the resulting mixture was stirred at 45° C. under $N_2$ atmosphere for 1 hour. The mixture was diluted with EtOAc and filtered, and the filtrate was washed with saturated aqueous $NaHCO_3$ solution and brine, dried over anhydrous $Na_2SO_4$, filtered, and concentrated to afford crude product. The residue was purified by silica gel column (eluted with PE:EtOAc=15:1) to afford compound 2 (350 mg, yield 61.4%) as colorless oil. LC/MS (ESI) m/z: 420 (M+Na)$^+$.

Step 2: (1R,3S,5S)-2-(tert-Butoxycarbonyl)-5-((difluoromethoxy)methyl)-2-azabicyclo[3.1.0]hexane-3-carboxylic Acid (3)

To a solution of compound 2 (350 mg, 0.88 mmol) in MeOH (12 mL) was added 4 mL of aqueous LiOH solution (4 mmol, 1 M) and the mixture was stirred at room temperature for 4 hours. The mixture was diluted with water (20 mL) and extracted with ether and the aqueous layer was collected and acidified with aqueous HCl solution (1 N) to pH of 5. The mixture was extracted with DCM/MeOH (20 mL×2, 15:1, v/v) and the combined organic layers were washed with brine, dried over anhydrous $Na_2SO_4$, filtered and concentrated to afford compound 3 (240 mg, yield 88.9%) as a colorless oil. LC/MS (ESI) m/z: 330 (M+Na)$^+$.

Step 3: (1R,3S,5S)-tert-Butyl 3-((6-bromo-3-methylpyridin-2-yl)carbamoyl)-5-((difluoromethoxy)methyl)-2-azabicyclo[3.1.0]hexane-2-carboxylate (4)

To a solution of compound 3 (138 mg, 0.45 mmol) and 6-bromo-3-methylpyridin-2-amine (85 mg, 0.45 mmol) in anhydrous DCM (10 mL) was added pyridine (178 mg, 2.25 mmol) followed by the drop-wise addition of $POCl_3$ (77 mg, 0.5 mmol) at 0° C. The reaction mixture was stirred at room temperature for 1 hour. The reaction mixture was quenched with ice-cool water and extracted with DCM twice. The combined organic phases were washed with brine, dried over anhydrous Na₂SO₄, filtered and concentrated to dryness. The residue was purified by silica gel column (eluted with PE:EtOAc=6:1) to afford compound 4 (131 mg, yield 61.2%) as colorless oil. LC/MS (ESI) m/z: 476/478 (M+H)⁺.

Step 4: (1R,3S,5S)—N-(6-Bromo-3-methylpyridin-2-yl)-5-((difluoromethoxy)methyl)-2-azabicyclo[3.1.0]hexane-3-carboxamide TFA Salt (5)

To a solution of compound 4 (55 mg, 0.116 mmol) in DCM (2 mL) was added TFA (1 mL) drop-wise at 0° C. under a N₂ atmosphere and the mixture was stirred at room temperature for 1 hour. The mixture was concentrated to dryness to afford compound 5 (60 mg, yield 95.9%) as a dark-brown oil that was directly used in the next reaction without further purification. LC/MS (ESI) m/z: 376/378 (M+H)⁺.

Step 5: (1R,3S,5S)-2-(2-(3-Acetyl-5-(2-methylpyrimidin-5-yl)-1H-pyrazolo[3,4-c]pyridin-1-yl)acetyl)-N-(6-bromo-3-methylpyridin-2-yl)-5-((difluoromethoxy)methyl)-2-azabicyclo[3.1.0]hexane-3-carboxamide (384)

To a mixture of compound 5 (60 mg, 0.116 mmol), compound 6 (36 mg, 0.116 mmol) and HATU (80 mg, 0.21 mmol) in DMF (3 mL) was added DIPEA (76 mg, 0.58 mmol) at 0° C. and the reaction mixture was stirred at room temperature for 1 hour. The mixture was diluted with EtOAc and washed with 10% aqueous LiCl solution and brine, dried over anhydrous Na₂SO₄, filtered and concentrated to dryness. The residue was purified via pre-HPLC to afford Compound 384 (25 mg, yield 32.3%) as white solid. ¹H-NMR (400 MHz, DMSO-d₆) δ 10.30 (s, 1H), 9.25-9.42 (m, 3H), 8.62 (d, J=1.1 Hz, 1H), 7.63 (d, J=8.1 Hz, 1H), 7.45 (d, J=7.9 Hz, 1H), 6.94 (s, 1H), 6.75 (s, 1H), 6.56 (s, 1H), 6.07 (d, J=17.3 Hz, 1H), 5.76 (d, J=17.2 Hz, 1H), 4.51 (dd, J=9.4, 4.7 Hz, 1H), 3.98 (dd, J=25.7, 10.9 Hz, 2H), 3.85 (dd, J=5.7, 2.7 Hz, 1H), 2.70 (s, 3H), 2.69 (s, 3H), 2.53-2.60 (m, 1H), 2.25-2.32 (m, 1H), 2.04 (s, 3H), 1.31-1.37 (m, 1H), 1.28 (t, J=5.6 Hz, 1H). LC/MS (ESI) m/z: 669/671 (M+H)⁺.

Scheme 110: Synthesis of (1R,3S,5R)-2-(2-(3-(1H-Imidazole-2-carbonyl)-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (389)

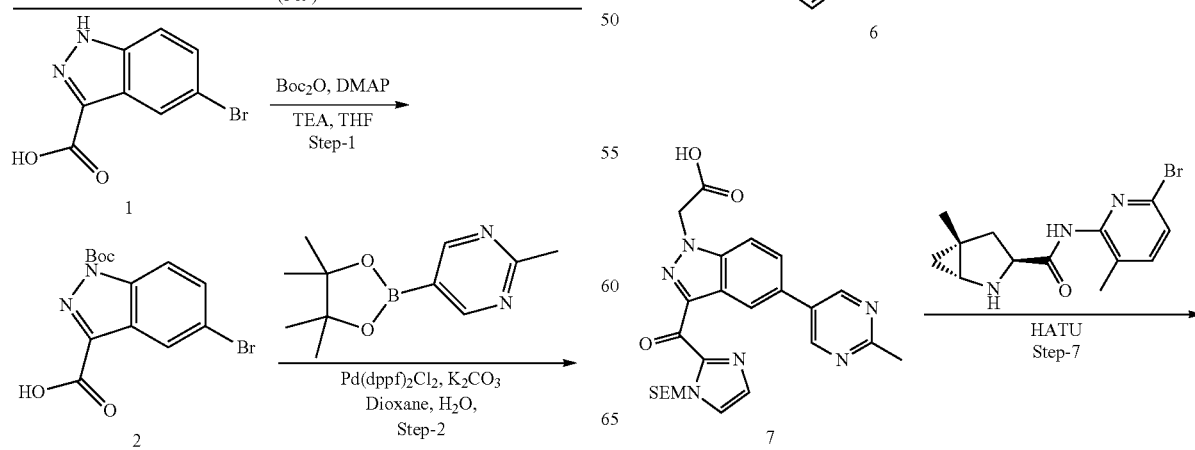

-continued

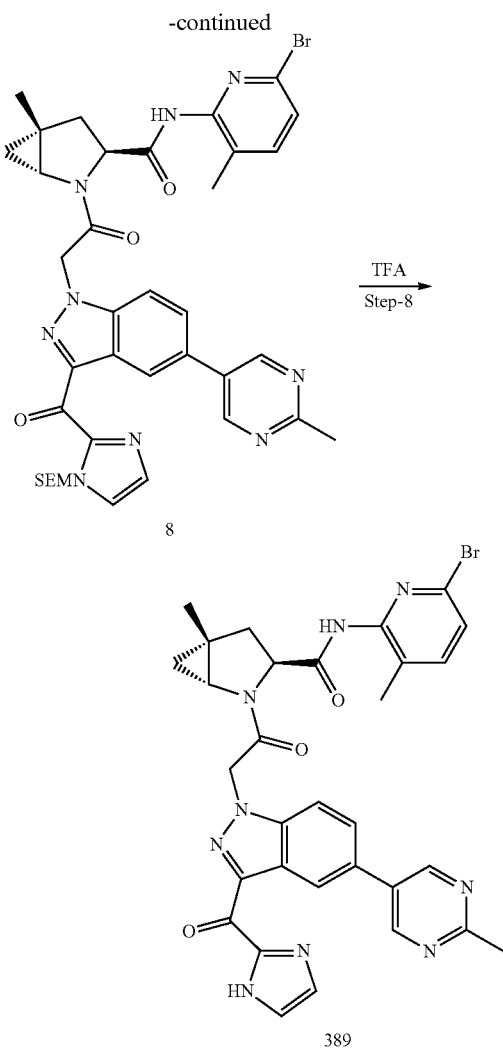

Step 1: 5-Bromo-1-(tert-butoxycarbonyl)-1H-indazole-3-carboxylic Acid (2)

To a solution of 5-bromo-1H-indazole-3-carboxylic acid (1 equiv) in THF (10 vol) at 0° C. under nitrogen atmosphere was added DMAP (0.1 equiv) and triethylamine (3 equiv). Boc anhydride (1 equiv) was added and the reaction mixture was stirred at room temperature for 16 hours. After completion of the reaction, water was added and the resulting mixture was extracted with ethyl acetate. The organic layer was separated, dried over anhydrous $Na_2SO_4$, filtered and concentrated to afford compound 2 that was used as such for the next step.

Step 2: 5-(2-Methylpyrimidin-5-yl)-1H-indazole-3-carboxylic Acid (3)

To a solution of compound 2 (1 equiv) in 1,4-dioxane (20 vol) and water (2 vol) at 0° C. under nitrogen atmosphere was added 2-methyl-5-(4,4,5,5-tetramethyl-1,3,2-dioxaborolan-2-yl)pyrimidine (1.5 equiv), potassium carbonate (3 equiv). After degassing with nitrogen, $PdCl_2$(dppf) (0.1 equiv) was added to the reaction mixture. The reaction mixture was sealed and kept in microwave at 100° C. for 1 hour. After completion of the reaction, the reaction mixture was concentrated to afford compound 3 and the resulting residue was used as such for the next step.

Step 3: N-Methoxy-N-methyl-5-(2-methylpyrimidin-5-yl)-1H-indazole-3-carboxamide (4)

To a solution of compound 3 (1 equiv) in DMF (10 vol) at 0° C. under nitrogen atmosphere was added N,O-dimethylhydroxylamine hydrochloride (1.5 equiv), EDCI-HCl (1.5 equiv) and DMAP (1.2 equiv). The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and concentrated to afford compound 4 and the resulting residue was used as such for the next step.

Step 4: (5-(2-Methylpyrimidin-5-yl)-1H-indazol-3-yl)(1-((2-(trimethylsilyl)ethoxy)methyl)-1H-imidazol-2-yl)methanone (5)

To a solution of compound 4 (1 equiv) in THF (10 vol) at −40° C. under nitrogen atmosphere was added n-BuLi (5 equiv). The reaction mixture was stirred at −40° C. for 1 hour. 1-((2-(Trimethylsilyl)ethoxy)methyl)-1H-imidazole (5 equiv) was added to the reaction mixture and stirred at −40° C. for 3 hours. After completion of the reaction, the reaction mixture was quenched with ice water. The resulting mixture was extracted with DCM. The organic layer was washed with brine, dried over anhydrous $Na_2SO_4$, filtered and concentrated. The residue was purified by preparative purification to afford compound 5.

Step 5: Methyl 2-(5-(2-methylpyrimidin-5-yl)-3-(1-((2-(trimethylsilyl)ethoxy)methyl)-1H-imidazole-2-carbonyl)-1H-indazol-1-yl)acetate (6)

To a solution of compound 5 (1 equiv) in DMF (10 vol) was added potassium carbonate (1.5 equiv) and methyl 2-bromoacetate (1.1 equiv). The reaction mixture was stirred at 50° C. for 3 hours and then quenched with water. The resulting solid was filtered, taken in MTBE, stirred for 30 minutes, filtered, and dried to afford compound 6.

Step 6: 2-(5-(2-Methylpyrimidin-5-yl)-3-(1-((2-(trimethylsilyl)ethoxy)methyl)-1H-imidazole-2-carbonyl)-1H-indazol-1-yl)acetic Acid (7)

To a solution of compound 6 (1 equiv) in THF/water (10 vol/2 vol) was added LiOH (3 equiv). The reaction mixture was stirred at room temperature for 4 hours and concentrated. Water was added to the residue and washed with ethyl acetate (3 times). The aqueous layer was acidified with 1.5 N HCl and then extracted with ethyl acetate. The organic layer was separated, dried over anhydrous $Na_2SO_4$, filtered, and concentrated to afford compound 7.

Step 7: (1R,3S,5R)—N-(6-Bromo-3-methylpyridin-2-yl)-5-methyl-2-(2-(5-(2-methylpyrimidin-5-yl)-3-(1-((2-(trimethylsilyl)ethoxy)methyl)-1H-imidazole-2-carbonyl)-1H-indazol-1-yl)acetyl)-2-azabicyclo[3.1.0]hexane-3-carboxamide (8)

To a solution of compound 7 (1 equiv) in DMF (10 vol) at 0° C. under nitrogen atmosphere was added (1R,3S,5R)—N-(6-bromo-3-methylpyridin-2-yl)-5-methyl-2-azabicyclo[3.1.0]hexane-3-carboxamide (1 equiv), HATU (1.5 equiv)

and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered, and concentrated. The residue was purified by preparative purification to afford compound 8.

Step 8: (1R,3S,5R)-2-(2-(3-(1H-Imidazole-2-carbonyl)-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (389)

A solution of compound 8 (1 equiv) in TFA (5 vol) was stirred at room temperature for 4 hours and concentrated. The residue was purified by preparative purification to afford Compound 389. $^1$H NMR (400 MHz, CD3OD) δ 9.08 (s, 2H), 8.68 (s, 1H), 7.97 (s, 2H), 7.85 (s, 2H), 7.55 (d, J=8.0 Hz, 1H), 7.40 (d, J=8.0 Hz, 1H), 6.01 (d, J=18.0 Hz, 1H), 5.96 (d, J=18.0 Hz, 1H), 3.75-3.69 (m, 2H), 3.61-3.59 (m, 2H), 3.80 (s, 3H), 2.13 (s, 3H), 1.45 (s, 3H), 1.21-1.28 (m, 1H), 1.11-1.10 (m, 1H).

Scheme 111: Synthesis of (1R,3S,5R)-N-(6-bromo-3-methylpyridin-2-yl)-5-methyl-2-(2-(7-methyl-5-(2-methylpyrimidin-5-yl)-3-(2-azaspiro[3.3]heptane-2-carbonyl)-1H-indazol-1-yl)acetyl)-2-azabicyclo[3.1.0]hexane-3-carboxamide (390)

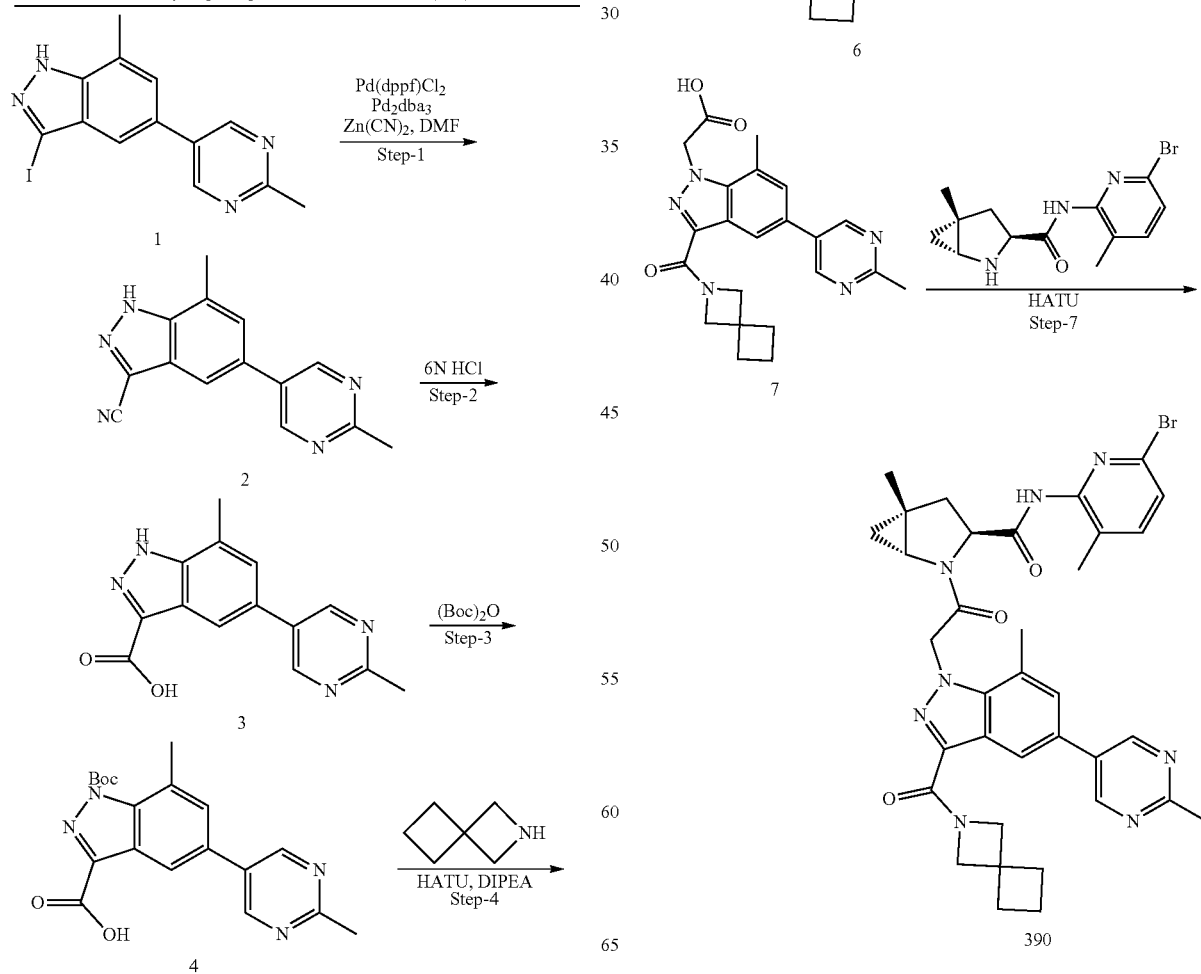

Step 1: 7-Methyl-5-(2-methylpyrimidin-5-yl)-1H-indazole-3-carbonitrile (2)

To a solution of 3-iodo-7-methyl-5-(2-methylpyrimidin-5-yl)-1H-indazole (1 equiv) in DMF (10 vol) and water (1 vol) at room temperature was added Zn(CN)$_2$ (1.1 equiv). After degassing with nitrogen, Pd(dppf)Cl$_2$ (0.1 equiv) and Pd$_2$(dba)$_3$ (0.1 equiv) were added and the mixture was stirred at 90° C. for 5 hours. The reaction mixture was cooled to room temperature. Water was added and the mixture was extracted with ethyl acetate. The organic layer was separated, dried over anhydrous Na$_2$SO$_4$, filtered, and concentrated. The residue was purified by column chromatography on silica gel using hexane/EtOAc to afford compound 2.

Step 2: 7-Methyl-5-(2-methylpyrimidin-5-yl)-1H-indazole-3-carboxylic Acid (3)

To a solution of compound 2 (1 equiv) in dioxane (5 vol) at 0° C. was added 6N HCl (20 vol). The reaction mixture was stirred at 90° C. for 3 hours in a sealed tube and then concentrated. 10% NaHCO$_3$ was added and the resulting mixture was extracted with EtOAc. The organic layer was separated, dried over anhydrous Na$_2$SO$_4$, filtered, and concentrated to afford compound 3.

Step 3: 1-(tert-Butoxycarbonyl)-7-methyl-5-(2-methylpyrimidin-5-yl)-1H-indazole-3-carboxylic Acid (4)

To a solution of compound 3 (1 equiv) in dioxane (10 vol) and water (3 vol) at 0° C. was added 2M NaOH (3 equiv). Boc anhydride (1.5 equiv) was added and the mixture was stirred at room temperature for 16 hours. After completion of the reaction, water was added and the resulting mixture was acidified with 1M citric acid solution before being extracted with EtOAc. The organic layer was washed with brine, dried over anhydrous Na$_2$SO$_4$, filtered and concentrated. The residue was purified by column chromatography on silica gel using DCM/MeOH to afford compound 4.

Step 4: tert-Butyl 7-methyl-5-(2-methylpyrimidin-5-yl)-3-(2-azaspiro[3.3]heptane-2-carbonyl)-1H-indazole-1-carboxylate (5)

To a solution of compound 4 (1 equiv) in DMF (10 vol) at 0° C. under nitrogen atmosphere was added 2-azaspiro[3.3]heptane (1 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous Na$_2$SO$_4$, filtered and concentrated. The residue was purified by column chromatography on silica gel using DCM/MeOH to afford compound 5.

Step 5: tert-Butyl 2-(7-methyl-5-(2-methylpyrimidin-5-yl)-3-(2-azaspiro[3.3]heptane-2-carbonyl)-1H-indazol-1-yl)acetate (6)

To a solution of compound 5 (1 equiv) in 1,4-dioxane (3 vol) at 0° C. under nitrogen atmosphere was added 4 N HCl in 1,4-dioxane (10 vol) and the mixture was stirred at room temperature for 3 hours. The volatiles were removed under reduced pressure and the resulting residue was used as such for the next step.

To a solution of above residue in DMF (10 vol) was added potassium carbonate (3 equiv) and tert-butyl 2-bromoacetate (1.5 equiv). The reaction mixture was stirred at 50° C. for 3 hours. After completion of the reaction, the mixture was quenched with water. The resulting mixture was extracted with EtOAc. The organic layer was washed with brine, dried over anhydrous Na$_2$SO$_4$, filtered and concentrated. The residue was purified by column chromatography on silica gel using DCM/MeOH to afford compound 6.

Step 6: 2-(7-Methyl-5-(2-methylpyrimidin-5-yl)-3-(2-azaspiro[3.3]heptane-2-carbonyl)-1H-indazol-1-yl)acetic Acid (7)

To a solution of compound 6 (1 equiv) in DCM (10 vol) at 0° C. was added TFA (5 vol). The reaction mixture was stirred at 50° C. for 2 hours. The volatiles were removed under reduced pressure to afford compound 7 and the resulting residue was used as such for the next step.

Step 7: (1R,3S,5R)—N-(6-Bromo-3-methylpyridin-2-yl)-5-methyl-2-(2-(7-methyl-5-(2-methylpyrimidin-5-yl)-3-(2-azaspiro[3.3]heptane-2-carbonyl)-1H-indazol-1-yl)acetyl)-2-azabicyclo[3.1.0]hexane-3-carboxamide (390)

To a solution of compound 7 (1 equiv) in DMF (10 vol) at 0° C. under nitrogen atmosphere was added (1R,3S,5R)—N-(6-bromo-3-methylpyridin-2-yl)-5-methyl-2-azabicyclo[3.1.0]hexane-3-carboxamide (1.2 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous Na$_2$SO$_4$, filtered and concentrated. The residue was purified by preparative purification to afford Compound 390. $^1$H NMR (400 MHz, CD3OD) δ 9.01 (s, 2H), 8.41 (s, 1H), 7.57-7.54 (m, 2H), 7.40 (d, J=8.0 Hz, 1H), 5.92 (d, J=18.0 Hz, 1H), 5.78 (d, J=18.0 Hz, 1H), 4.65-4.64 (m, 1H), 4.19-4.17 (m, 2H), 3.65-3.64 (m, 1H), 3.56-3.55 (m, 1H), 2.76 (s, 3H), 2.33 (s, 3H), 2.27-2.13 (m, 2H), 1.92-1.91 (m, 2H), 1.43-1.42 (m, 2H), 1.30 (s, 3H), 1.29 (s, 3H), 0.97-0.91 (m, 2H).

Scheme 112: Synthesis of (1R,5R)-2-(2-(3-Acetyl-5-(2-methylpyrimidin-5-yl)-1H-indazol-1-yl)acetyl)-N-(6-bromo-5-fluoro-3-((methylthio)methyl)pyridin-2-yl)-5-methyl-2-azabicyclo[3.1.0]hexane-3-carboxamide (438)

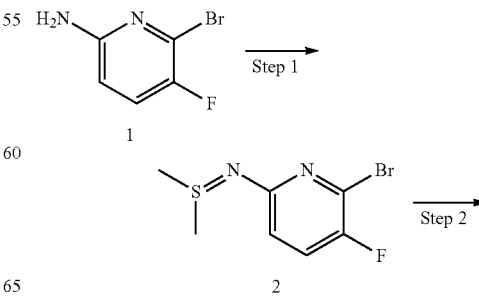

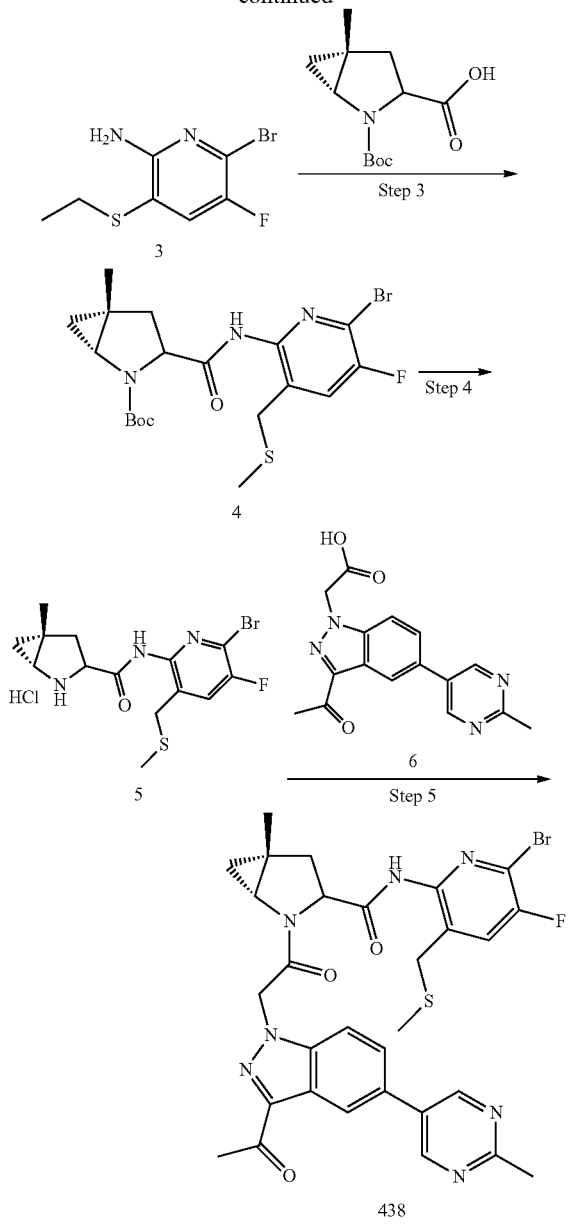

Step 2: 6-Bromo-5-fluoro-3-((methylthio)methyl)pyridin-2-amine (3)

To N-(6-bromo-5-fluoropyridin-2-yl)-S,S-dimethyl-λ⁴-sulfanimine (0.98 g, 3.903 mmol), potassium tert-butoxide (4 mmol) in tert-butyl alcohol (10 mL) was added and the reaction was refluxed for 16 hours. Solvent was removed and the residue was purified by SiO$_2$ chromatography to afford 6-bromo-5-fluoro-3-((methylthio)methyl)pyridin-2-amine (0.5 g, 1.99 mmol, yield 51%).

Step 3: tert-Butyl (1R,3S,5R)-3-((6-bromo-5-fluoro-3-((methylthio)methyl)pyridin-2-yl)carbamoyl)-5-methyl-2-azabicyclo[3.1.0]hexane-2-carboxylate (4)

(1R,3S,5R)-2-(tert-Butoxycarbonyl)-5-methyl-2-azabicyclo[3.1.0]hexane-3-carboxylic acid (0.05 g, 0.209 mmol, 1.05 equiv.) and 6-bromo-5-fluoro-3-[(methylsulfanyl)methyl]pyridin-2-amine (0.05 g, 0.199 mmol, 1 equiv.) were dissolved in dichloromethane (5 ml) and pyridine (0.079 g, 0.08 mL, 0.996 mmol, 5 equiv.) was added followed by phosphoryl chloride (0.031 g, 0.019 mL, 0.199 mmol, 1 equiv.) at 0° C. The reaction mixture was stirred for 1 hour at 0° C. and water was added followed by K$_2$CO$_3$ to basify the reaction. The organic layer was separated and solvent was removed. The crude material was purified by SiO$_2$ chromatography to afford tert-butyl (1R,3S,5R)-3-({6-bromo-5-fluoro-3-[(methylsulfanyl)methyl]pyridin-2-yl}carbamoyl)-5-methyl-2-azabicyclo[3.1.0]hexane-2-carboxylate (0.09 g, 0.19 mmol, yield 95.284%)

Step 4: (1R,3S,5R)—N-(6-Bromo-5-fluoro-3-((methylthio)methyl)pyridin-2-yl)-5-methyl-2-azabicyclo[3.1.0]hexane-3-carboxamide Hydrochloride (5)

To tert-butyl (1R,3S,5R)-3-({6-bromo-5-fluoro-3-[(methylsulfanyl)methyl]pyridin-2-yl}carbamoyl)-5-methyl-2-azabicyclo[3.1.0]hexane-2-carboxylate (0.09 g, 0.19 mmol, 1 equiv.), 4N hydrochloric acid in dioxane (5 mL) was added and the reaction was stirred for 1 hour at room temperature. Solvent was removed and the residue was used in the next step.

Step 5: (1R,3S,5R)-2-(2-(3-Acetyl-5-(2-methylpyrimidin-5-yl)-1H-indazol-1-yl)acetyl)-N-(6-bromo-5-fluoro-3-((methylthio)methyl)pyridin-2-yl)-5-methyl-2-azabicyclo[3.1.0]hexane-3-carboxamide (438)

To a solution of (1R,3S,5R)—N-{6-bromo-5-fluoro-3-[(methylsulfanyl)methyl]pyridin-2-yl}-5-methyl-2-azabicyclo[3.1.0]hexane-3-carboxamide hydrochloride (0.078 g, 0.19 mmol, 1 equiv.) and [3-acetyl-5-(2-methylpyrimidin-5-yl)indazol-1-yl]acetic acid (0.062 g, 0.199 mmol, 1.05 equiv.) in N,N-dimethylformamide (1.56 mL, 0.122 M, 20 Vols), was added Hunig's Base (0.123 g, 0.165 mL, 0.95 mmol, 5 equiv.) and the reaction was cooled to 0° C. N,N,N',N'-Tetramethyl-O-(benzotriazol-1-yl)uronium tetrafluoroborate (0.067 g, 0.209 mmol, 1.1 equiv.) was added and the reaction was stirred for 1 hour. Excess solvent was removed and the residue was purified by SiO$_2$ chromatography to afford (1R,3S,5R)-2-{2-[3-acetyl-5-(2-methylpyrimidin-5-yl)indazol-1-yl]acetyl}-N-{6-bromo-5-fluoro-3-[(methylsulfanyl)methyl]pyridin-2-yl}-5-methyl-2-azabicyclo[3.1.0]hexane-3-carboxamide 438 (0.05 g, 0.064 mmol, yield 33.729%) ¹H NMR (400 MHz, DMSO-d$_6$) δ

Step 1: N-(6-Bromo-5-fluoropyridin-2-yl)-1,1-dimethyl-14-sulfanimine (2)

6-Bromo-5-fluoropyridin-2-amine (0.97 g, 5.078 mmol, 1 equiv.) in dichloromethane (5 mL, 1.016 M, 5.155 Vols) was cooled to −60° C. N-Chlorosuccinimide (0.712 g, 0.432 mL, 5.332 mmol, 1.05 equiv.) in dichloromethane (10 mL) was slowly added at −60° C. The reaction mixture was stirred for 30 minutes before methyl sulfide (0.947 g, 1.119 mL, 15.235 mmol, 3 equiv.) was slowly added and the reaction was stirred for 1 hour. Sodium methoxide (0.329 g, 12.188 mL, 6.094 mmol, 1.2 equiv.) was slowly at −60° C. and the reaction was stirred for 1 hour at −60° C. before the reaction was allowed to warm to room temperature. Upon evaporation of the solvent, crude material was purified by SiO$_2$ chromatography to afford N-(6-bromo-5-fluoropyridin-2-yl)-S,S-dimethyl-λ⁴-sulfanimine (0.98 g, 3.903 mmol, yield 76.845%).

0.97-1.08 (m, 2H), 1.34 (s, 3H), 1.77 (s, 3H), 2.06 (m, 1H), 2.56 (m, 1H), 2.66 (s, 3H), 2.70 (s, 3H), 3.60 (m, 1H), 4.00-4.80 (m, 2H), 4.40 (m, 1H), 5.59 (m, 1H), 5.92 (m, 1H), 7.85-7.96 (m, 3H), 8.45 (s, 1H), 9.05 (s, 2H), 10.35 (s, 1H).

Scheme 11: Synthesis of (S)-1-{5-(3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-indazol-5-yl)pyrimidin-2-yl)-24-carboxy-3,12,21,26-tetraoxo-5,8,14,17-tetraoxa-2,11,20,25-tetraazatritetracontan-43-oic acid (233)
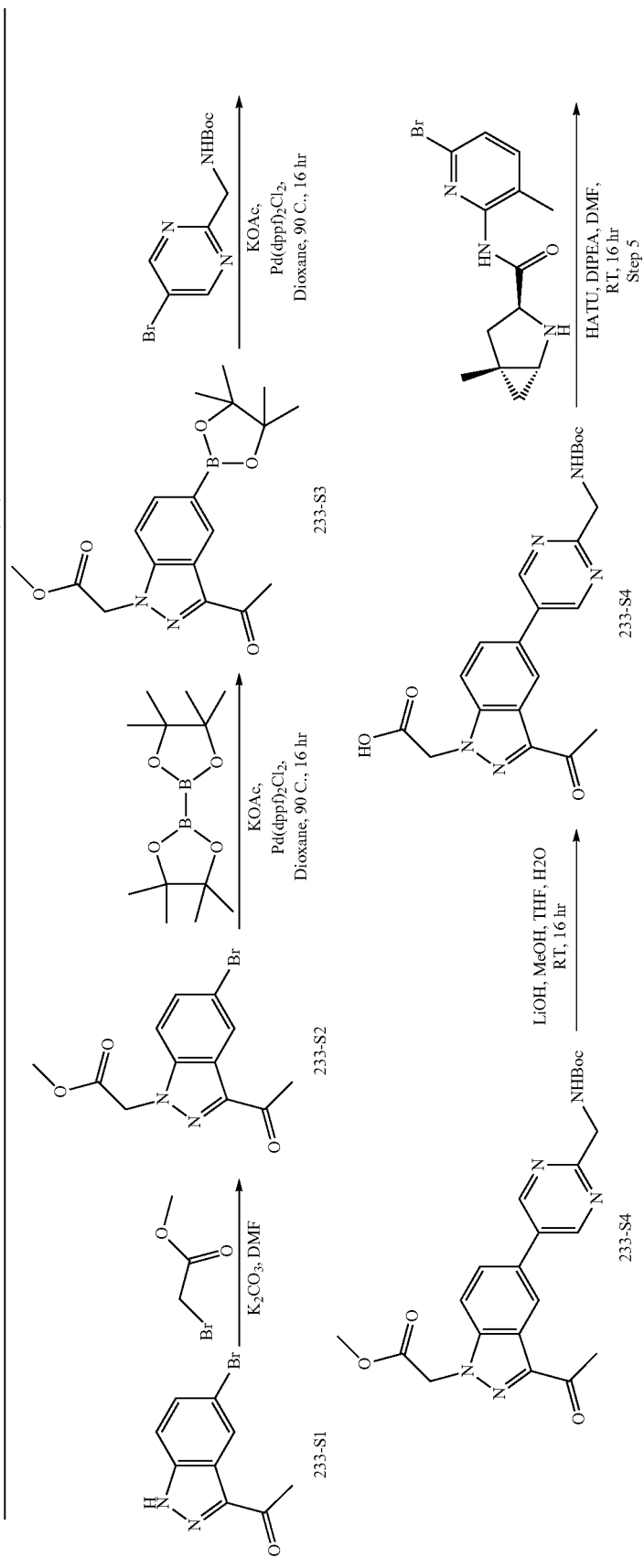

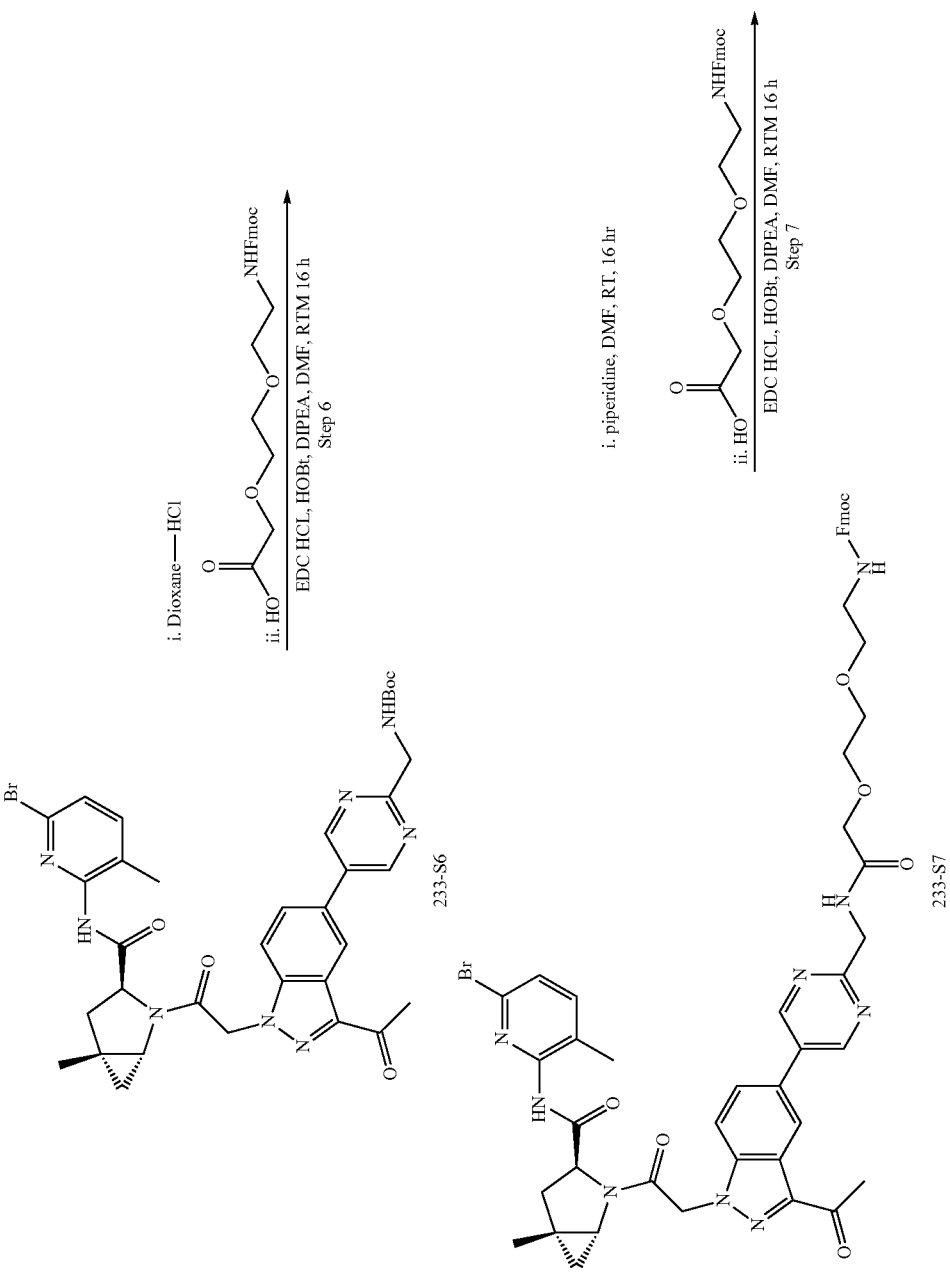

-continued
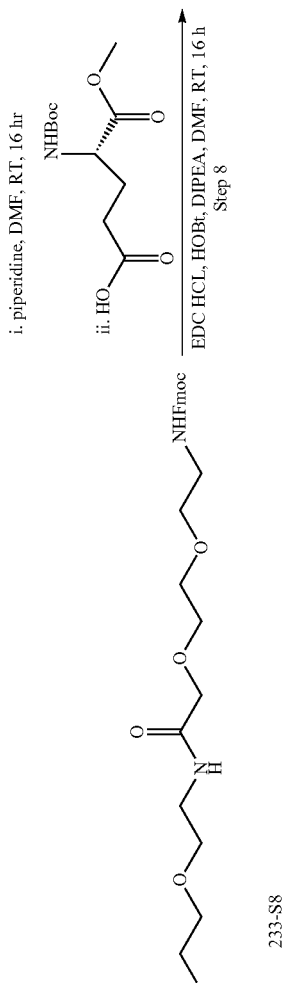
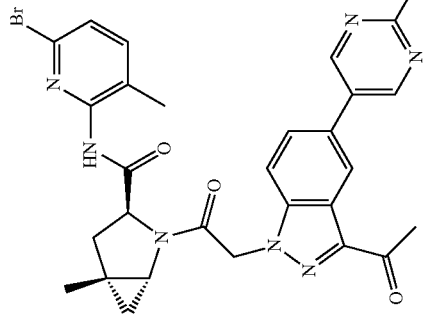
233-S8
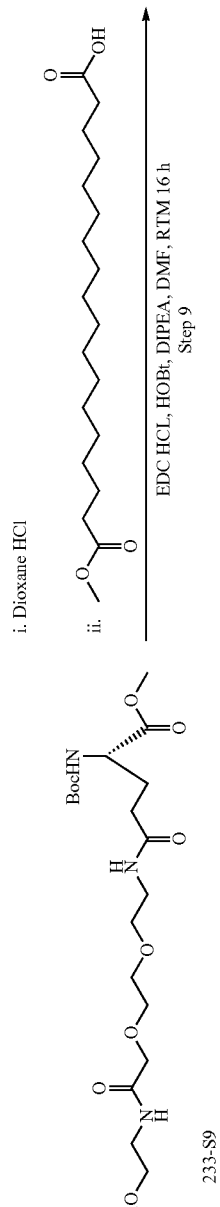
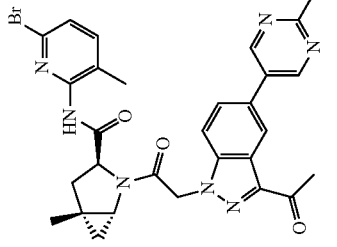
233-S9

995 996
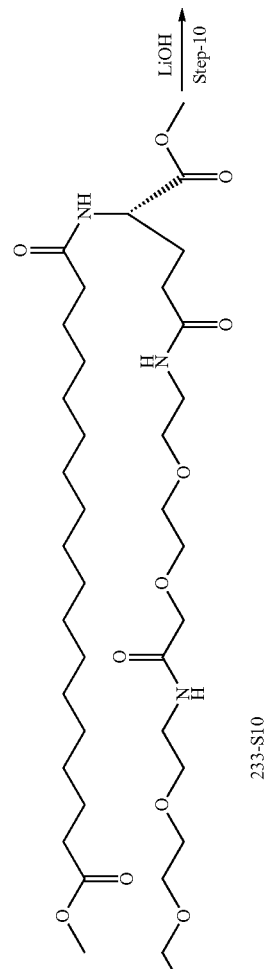
233-S10
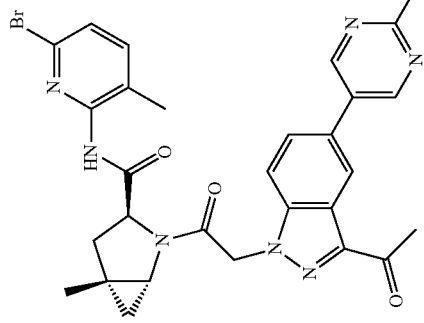
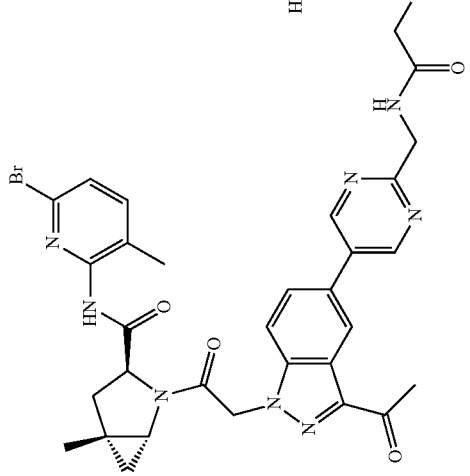
233

The above scheme and following detailed description depicts one non-limiting method for synthesizing compounds with a fatty acid in the $R^{32}$ position via the formation of an amide bond utilizing the coupling reagent HATU. The skilled artisan will recognize that the A-ring shown above can be replaced with other A-rings to afford additional compounds of the present invention. The skilled artisan will also recognize that the fatty acid in the $R^{32}$ shown above can be replaced with other fatty acids.

Step 1: Methyl 2-(3-acetyl-5-bromo-1H-indazol-1-yl)acetate (233-S2)

To a solution of 1-(5-bromo-1H-indazol-3-yl)ethan-1-one (1 equiv) in DMF (10 vol) was added potassium carbonate (2.5 equiv) and methyl bromoacetate (1.1 equiv). The reaction mixture was stirred at room temperature for 3 hours and quenched with water. The resulting solid was filtered, taken up in MTBE, stirred for 30 minutes, filtered, and dried to afford compound 233-S2.

Step-2: Methyl 2-(3-acetyl-5-(4,4,5,5-tetramethyl-1,3,2-dioxaborolan-2-yl)-1H-indazol-1-yl)acetate (233-S3)

To a solution of compound 233-S32 (1 equiv) in 1,4-dioxane (10 vol) at 0° C. under nitrogen atmosphere was added 4,4,4',4',5,5,5',5'-octamethyl-2,2'-bi(1,3,2-dioxaborolane (1.5 equiv), potassium acetate (3 equiv) and $PdCl_2$(dppf) (0.1 equiv). The reaction mixture was stirred at 90° C. for 12 hours. After completion of the reaction, the reaction mixture was quenched with water. The resulting mixture was extracted with DCM and the organic layer was washed with brine, dried over anhydrous $Na_2SO_4$, filtered and concentrated. The residue was purified by column chromatography on silica gel using hexane/EtOAc to afford compound 233-S3.

Step-3: Methyl 2-(3-acetyl-5-(2-(((tert-butoxycarbonyl)amino)methyl)pyrimidin-5-yl)-1H-indazol-1-yl)acetate (233-S4)

To a solution of compound 233-S3 (1.2 equiv) in 1,4-dioxane (10 vol) at 0° C. under nitrogen atmosphere was added tert-butyl ((5-bromopyrimidin-2-yl)methyl)carbamate (1 equiv), potassium acetate (3 equiv) and $PdCl_2$(dppf) (0.1 equiv). The reaction mixture was stirred at 90° C. for 12 hours and concentrated. The residue was purified by column chromatography on silica gel using hexane/EtOAc to afford compound 233-S4.

Step 4: 2-(3-Acetyl-5-(2-(((tert-butoxycarbonyl)amino)methyl)pyrimidin-5-yl)-1H-indazol-1-yl)acetic Acid (233-S5)

To a solution of compound 233-S4 (1 equiv) in THF/MeOH/water (2:1:1) was added LiOH (1.5 equiv). The reaction mixture was stirred at room temperature for 12 hours and concentrated. Water was added to the residue and the solution was washed with ethyl acetate (3 times). The aqueous layer was acidified with 1.5 N HCl and extracted with ethyl acetate. The organic layer was separated, dried over anhydrous $Na_2SO_4$, filtered and concentrated to afford compound 233-S5.

Step 5: tert-Butyl ((5-(3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-indazol-5-yl)pyrimidin-2-yl)methyl)carbamate (6)

To a solution of compound 233-S5 (1 equiv) in DMF (10 vol) at 0° C. under nitrogen atmosphere was added (1R,3S,5R)—N-(6-bromo-3-methylpyridin-2-yl)-5-methyl-2-azabicyclo[3.1.0]hexane-3-carboxamide (1 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and concentrated. The residue was purified by column chromatography on silica gel using DCM/MeOH to afford compound 233-S6.

Step 6: (9H-Fluoren-9-yl)methyl (2-(2-(2-(((5-(3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-indazol-5-yl)pyrimidin-2-yl)methyl)amino)-2-oxoethoxy)ethoxy)ethyl)carbamate (233-S7)

To a solution of compound 233-S6 (1 equiv) in 1,4-dioxane (2 vol) at 0° C. under nitrogen atmosphere was added 4 N HCl in 1,4-dioxane (10 vol) and the reaction was stirred at room temperature for 3 hours. The reaction mixture was concentrated and dissolved in DMF (10 vol). 1-(9H-Fluoren-9-yl)-3-oxo-2,7,10-trioxa-4-azadodecan-12-oic acid (1.2 equiv), EDCI-HCl (1.5 equiv), HOBt (1.2 equiv) and DIPEA (5 equiv) were added at 0° C. under nitrogen atmosphere. The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and concentrated. The residue was purified by column chromatography on silica gel using DCM/MeOH to afford compound 233-S7.

Step 7: (9H-Fluoren-9-yl)methyl (1-(5-(3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-indazol-5-yl)pyrimidin-2-yl)-3,12-dioxo-5,8,14,17-tetraoxa-2,11-diazanonadecan-19-yl)carbamate (233-S8)

A solution of compound 233-S7 (1 equiv) in 20% piperidine in DMF (20 vol) was stirred at room temperature for 16 hours. The reaction mixture was concentrated and dissolved in DMF (10 vol). 1-(9H-Fluoren-9-yl)-3-oxo-2,7,10-trioxa-4-azadodecan-12-oic acid (1.2 equiv), EDCI-HCl (1.5 equiv), HOBt (1.2 equiv) and DIPEA (5 equiv) were added at 0° C. under nitrogen atmosphere. The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and concentrated. The residue was purified by column chromatography on silica gel using DCM/MeOH to afford compound 233-S8.

Step 8: Methyl (S)-1-(5-(3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-indazol-5-yl)pyrimidin-2-yl)-24-((tert-butoxycarbonyl)amino)-3,12,21-trioxo-5,8,14,17-tetraoxa-2,11,20-triazapentacosan-25-oate (233-S9)

A solution of compound 233-S8 (1 equiv) in 20% piperidine in DMF (20 vol) was stirred at room temperature for 16 hours. The reaction mixture was concentrated and dissolved in DMF (10 vol) at 0° C. (S)-4-((tert-Butoxycarbonyl)amino)-5-methoxy-5-oxopentanoic acid (6 equiv), EDCI-HCl (6 equiv), HOBt (1.2 equiv) and DIPEA (7.5 equiv) were added under nitrogen atmosphere. The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and concentrated. The residue was purified by column chromatography on silica gel using DCM/MeOH to afford compound 233-S9.

Step 9: (9H-Fluoren-9-yl)methyl (2-(2-(2-(((5-(3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-indazol-5-yl)pyrimidin-2-yl)methyl)amino)-2-oxoethoxy)ethoxy)ethyl)carbamate (233-S7)

To a solution of compound 233-S9 (1 equiv) in 1,4-dioxane (2 vol) at 0° C. under a nitrogen atmosphere 4 N HCl in 1,4-dioxane (10 vol) was added and the reaction stirred at room temperature for 3 hours. The reaction mixture was concentrated and dissolved in DMF (10 vol) at 0° C. 18-Methoxy-18-oxooctadecanoic acid (1.2 equiv), EDCI-HCl (1.5 equiv), HOBt (1.2 equiv) and DIPEA (5 equiv) were added under nitrogen atmosphere. The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and concentrated. The residue was purified by column chromatography on silica gel using DCM/MeOH to afford compound 233-S10.

Step 10: (S)-1-(5-(3-Acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-indazol-5-yl)pyrimidin-2-yl)-24-carboxy-3,12,21,26-tetraoxo-5,8,14,17-tetraoxa-2,11,20,25-tetraazatritetracontan-43-oic Acid (233)

To a solution of compound 233-S10 (1 equiv) in THF/water (8:2) was added LiOH (4 equiv). The reaction mixture was stirred at room temperature for 4 hours and then quenched with 1 M citric acid. The resulting mixture was extracted with ethyl acetate. The organic layer was separated, dried over anhydrous $Na_2SO_4$, filtered and concentrated to afford 233. $^1$H NMR (400 MHz, $CD_3OD$) δ 9.10 (s, 1H), 8.07-8.05 (m, 1H), 7.99 (s, 1H), 7.83-7.81 (m, 1H), 7.65-7.56 (m, 1H), 7.52-7.45 (m, 1H), 7.42-7.35 (m, 1H), 5.83 (d, J=17.2 Hz, 1H), 5.68 (d, J=17.2 Hz, 1H), 5.37-5.35 (m, 1H), 4.78-4.77 (m, 1H), 4.60-4.48 (m, 1H), 4.38-4.25 (m, 1H), 4.15-4.11 (m, 2H), 4.00-3.89 (m, 1H), 3.82-3.75 (m, 1H), 3.73-3.71 (m, 1H), 3.67-3.53 (m, 4H), 3.52-3.48 (m, 2H), 3.01-2.95 (m, 4H), 2.88 (s, 3H), 2.82-2.78 (m, 1H), 2.65-2.62 (m, 2H), 2.35-2.20 (m, 4H), 2.15-2.13 (m, 1H), 2.11-2.09 (m, 1H), 2.00-1.96 (m, 1H), 1.94 (s, 3H), 1.70-1.58 (m, 3H), 1.50-1.48 (m, 4H), 1.40 (s, 3H), 1.39-1.24 (m, 23H), 0.93-0.92 (m, 2H), 0.90-0.87 (m, 3H), 0.85-0.81 (m, 1H).

Methyl (S)-1-(5-(3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-7-methyl-1H-indazol-5-yl)pyrimidin-2-yl)-24-(methoxycarbonyl)-3,12,21,26-tetraoxo-5,8,14,17-tetraoxa-2,11,20,25-tetraazatritetracontan-43-oate $^1$H NMR (400 MHz, $CD_3OD$) δ 9.08 (s, 2H), 8.44 (s, 1H), 7.56-7.55 (m, 2H), 7.51 (d, J=8.0 Hz, 1H), 5.95 (d, J=18.0 Hz, 1H), 5.87 (d, J=18.0 Hz, 1H), 4.75-4.74 (m, 1H), 4.55-4.54 (m, 1H), 4.34-4.33 (m, 2H), 4.19 (s, 2H), 3.95 (s, 2H), 3.85-3.43 (m, 25H), 2.82-2.79 (m, 2H), 2.32-1.85 (m, 15H), 1.55-1.53 (m, 4H), 1.42 (s, 3H), 1.28-1.19 (m, 28H), 1.11-0.98 (m, 2H).

(S)-1-(5-(3-Acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-7-methyl-1H-indazol-5-yl)pyrimidin-2-yl)-24-carboxy-3,12,21,26-tetraoxo-5,8,14,17-tetraoxa-2,11,20,25-tetraazatritetracontan-43-oic Acid $^1$H NMR (400 MHz, $CD_3OD$) δ 9.08 (s, 2H), 8.45 (s, 1H), 7.57-7.55 (m, 2H), 7.39 (d, J=7.2 Hz, 1H), 5.97 (d, J=18.0 Hz, 1H), 5.87 (d, J=18.0 Hz, 1H), 4.75 (m, 2H), 4.57-4.55 (m, 1H), 4.32-4.31 (m, 1H), 4.17 (s, 2H), 3.98 (s, 2H), 3.82-3.41 (m, 13H), 2.81-2.80 (m, 2H), 2.75-2.73 (m, 4H), 2.41-1.99 (m, 10H), 1.61-1.60 (m, 4H), 1.42 (s, 3H), 1.35-1.31 (m, 29H), 1.11-1.10 (m, 2H).

Methyl (S)-1-(5-(3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-pyrazolo[3,4-c]pyridin-5-yl)pyrimidin-2-yl)-24-(methoxycarbonyl)-3,12,21,26-tetraoxo-5,8,14,17-tetraoxa-2,11,20,25-tetraazatritetracontan-43-oate $^1$H NMR (400 MHz, $CD_3OD$) δ 9.41 (s, 2H), 9.23 (s, 1H), 8.72 (s, 1H), 7.55 (d, J=7.2 Hz, 1H), 7.39 (d, J=7.2 Hz, 1H), 5.97 (d, J=18.0 Hz, 1H), 5.85 (d, J=18.0 Hz, 1H), 4.77-4.75 (m, 2H), 4.56-4.55 (m, 1H), 4.35-4.34 (m, 1H), 4.13 (s, 2H), 3.98 (s, 2H), 3.82-3.41 (m, 25H), 2.71 (s, 3H), 2.33-2.22 (m, 7H), 2.15 (s, 3H), 2.13-2.11 (m, 2H), 1.51-1.49 (m, 4H), 1.26-1.23 (m, 26H), 1.11-1.10 (m, 2H).

(S)-1-(5-(3-Acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-pyrazolo[3,4-c]pyridin-5-yl)pyrimidin-2-yl)-24-carboxy-3,12,21,26-tetraoxo-5,8,14,17-tetraoxa-2,11,20,25-tetraazatritetracontan-43-oic Acid $^1$H NMR (400 MHz, $CD_3OD$) δ 9.44 (s, 2H), 9.26 (s, 1H), 8.74 (s, 1H), 7.56 (d, J=7.2 Hz, 1H), 7.41 (d, J=7.2 Hz, 1H), 6.00 (d, J=18.0 Hz, 1H), 5.85 (d, J=18.0 Hz, 1H), 4.85 (s, 2H), 4.55-4.54 (m, 1H), 4.31-4.30 (m, 1H), 4.18 (s, 2H), 3.98 (s, 2H), 3.82-3.21 (m, 18H), 2.74 (s, 3H), 2.73-2.72 (m, 1H), 2.33-2.12 (m, 10H), 2.02-1.98 (m, 1H), 1.61-1.60 (m, 8H), 1.42-1.28 (m, 22H), 1.11-1.10 (m, 1H), 0.98-0.97 (m, 1H).

Synthesis 114: Synthesis of Methyl (S)-1-((1R,3S,5R)-2-(2-(3-acetyl-7-methyl-5-(2-methylpyrimidin-5-yl)-1H-indazol-1-yl)acetyl)-3-((6-bromo-3-methylpyridin-2-yl)carbamoyl)-2-azabicyclo[3.1.0]hexan-5-yl)-24-(methoxycarbonyl)-3,12,21,26-tetraoxo-5,8,14,17-tetraoxa-2,11,20,25-tetraazatritetracontan-43-oate (391) & (S)-1-((1R,3S,5R)-2-(2-(3-Acetyl-7-methyl-5-(2-methylpyrimidin-5-yl)-1H-indazol-1-yl)acetyl)-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-2,11,14,17-tetraoxa-2,11,20,25-tetraazatritetracontan-43-oic acid (392)

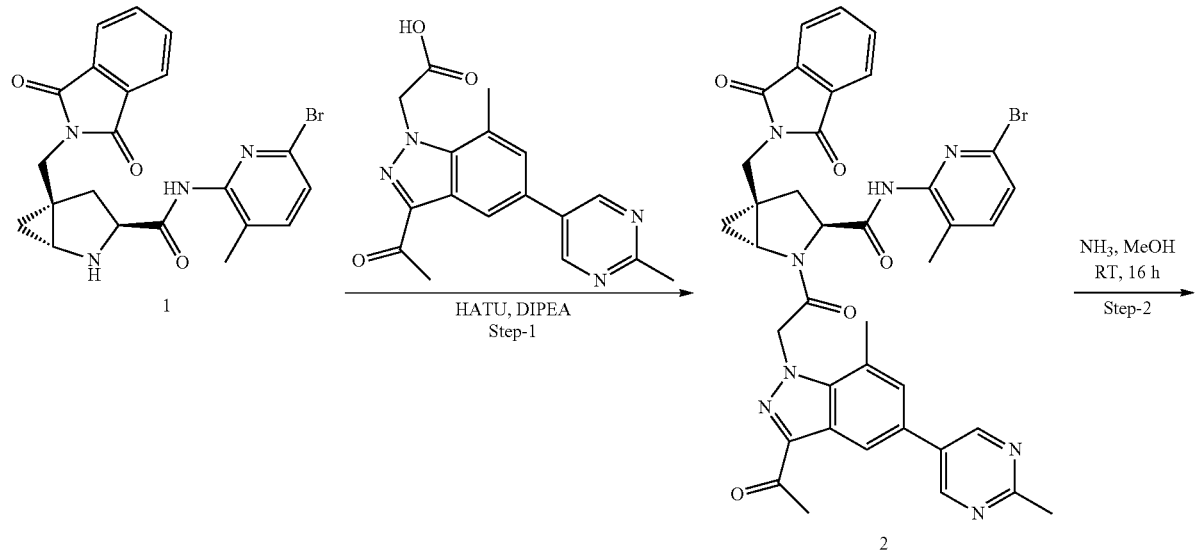

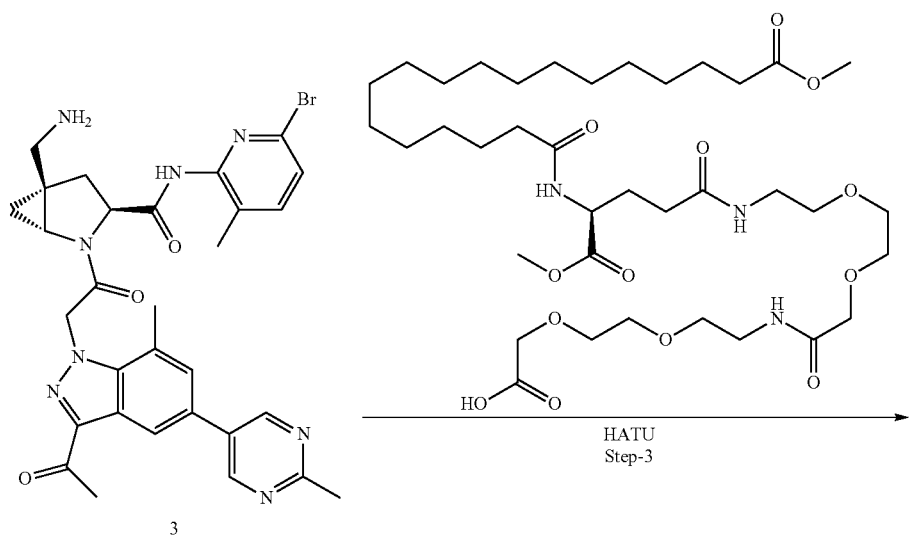

-continued

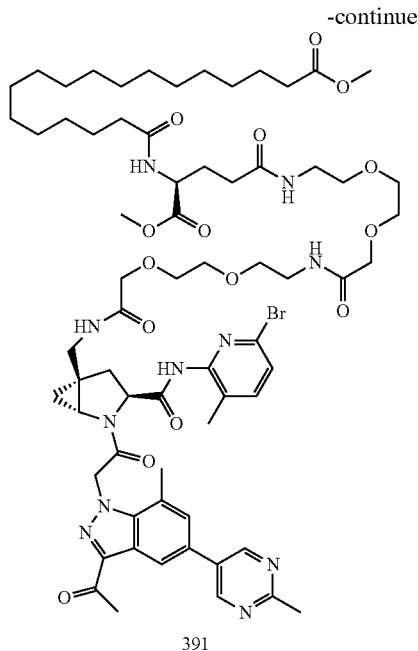

391

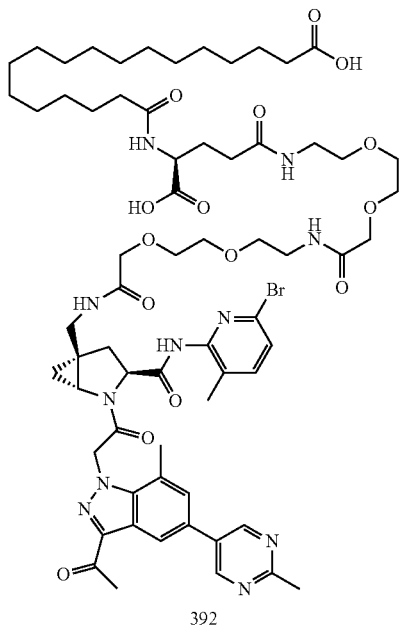

392

The above scheme and following detailed description depicts one non-limiting method for synthesizing compounds with a fatty acid in the $R^{301}$ position via the formation of an amide bond utilizing HATU. The skilled artisan will recognize that the A-ring shown above can be replaced with other A-rings to afford additional compounds of the present invention.

Step 1: (1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-((1,3-dioxoisoindolin-2-yl)methyl)-2-azabicyclo[3.1.0]hexane-3-carboxamide (2)

To a solution of (1R,3S,5R)—N-(6-bromo-3-methylpyridin-2-yl)-5-((1,3-dioxoisoindolin-2-yl)methyl)-2-azabicyclo[3.1.0]hexane-3-carboxamide hydrochloride (1.2 equiv) in DMF (10 vol) at 0° C. under nitrogen atmosphere was added 2-(3-acetyl-7-methyl-5-(2-methylpyrimidin-5-yl)-1H-indazol-1-yl)acetic acid (1 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and concentrated. The residue was purified by column chromatography on silica gel using DCM/MeOH to afford compound 2.

Step 2: (1R,3S,5R)-2-(2-(3-Acetyl-7-methyl-5-(2-methylpyrimidin-5-yl)-1H-indazol-1-yl)acetyl)-5-(aminomethyl)-N-(6-bromo-3-methylpyridin-2-yl)-2-azabicyclo[3.1.0]hexane-3-carboxamide (3)

To a solution of compound 2 (1 equiv) in MeOH (10 vol) at −30° C. was added saturated methanolic ammonia solution (50 vol). The reaction mixture was stirred at room temperature for 48 hours. After completion of the reaction, solvent was removed under reduced pressure and the residue was purified by preparative purification to afford compound 3.

Step 3: Methyl (S)-1-((1R,3S,5R)-2-(2-(3-acetyl-7-methyl-5-(2-methylpyrimidin-5-yl)-1H-indazol-1-yl)acetyl)-3-((6-bromo-3-methylpyridin-2-yl)carbamoyl)-2-azabicyclo[3.1.0]hexan-5-yl)-24-(methoxycarbonyl)-3,12,21,26-tetraoxo-5,8,14,17-tetraoxa-2,11,20,25-tetraazatritetracontan-43-oate (391)

To a solution of compound 3 (1 equiv) in DMF (10 vol) at 0° C. under nitrogen atmosphere was added (S)-22-(methoxycarbonyl)-3,20,25,34-tetraoxo-2,29,32,38,41-pentaoxa-21,26,35-triazatritetracontan-43-oic acid (1.1 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and concentrated. The residue was purified by preparative purification to afford Compound 391: $^1$H NMR (400 MHz, $CD_3OD$) δ 9.00 (s, 2H), 8.42 (s, 1H), 7.54-7.51 (m, 2H), 7.39 (d, J=7.2 Hz, 1H), 5.97 (d, J=18.0 Hz, 1H), 5.85 (d, J=18.0 Hz, 1H), 4.63-4.62 (m, 1H), 4.44-4.43 (m, 1H), 4.08-4.01 (m, 4H), 3.89-3.45 (m, 17H), 3.31-3.29 (m, 4H), 2.85 (s, 3H), 2.83 (s, 3H), 2.56-2.55 (m, 3H), 2.32-2.12 (m, 8H), 2.55-2.53 (m, 4H), 1.32-1.21 (m, 33H), 1.11-1.10 (m, 2H).

Step 4: (S)-1-((1R,3S,5R)-2-(2-(3-Acetyl-7-methyl-5-(2-methylpyrimidin-5-yl)-1H-indazol-1-yl)acetyl)-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-2,11,20,25-tetraazatritetracontan-43-oic Acid (392)

To a solution of Compound 391 (1 equiv) in THF/water (8:2) was added CsOH (2 equiv). The reaction mixture was stirred at room temperature for 2 hours and then quenched with 1 M citric acid. The resulting mixture was extracted with ethyl acetate. The organic layer was separated, dried over anhydrous $Na_2SO_4$, filtered and concentrated. The residue is purified by preparative purification to afford Compound 392: $^1$H NMR (400 MHz, $CD_3OD$) δ 9.03 (s, 2H), 8.45 (s, 1H), 7.57-7.56 (m, 2H), 7.40 (d, J=8.0 Hz, 1H), 5.99 (d, J=17.0 Hz, 1H), 5.85 (d, J=17.0 Hz, 1H), 4.65-4.63 (m, 3H), 4.12-4.00 (m, 4H), 3.81-3.53 (m, 13H), 2.81 (s, 3H), 2.79 (s, 3H), 2.56-2.55 (m, 3H), 2.32-2.29 (m, 6H), 2.12 (s, 3H), 1.61-1.59 (m, 4H), 1.42-1.39 (m, 33H), 0.89-0.85 (m, 2H).

Methyl (S)-1-((1R,3S,5R)-2-(2-(3-acetyl-5-(2-methylpyrimidin-5-yl)-1H-pyrazolo[3,4-c]pyridin-1-yl)acetyl)-3-((6-bromo-3-methylpyridin-2-yl)carbamoyl)-2-azabicyclo[3.1.0]hexan-5-yl)-24-(methoxycarbonyl)-3,12,21,26-tetraoxo-5,8,14,17-tetraoxa-2,11,20,25-tetraazatritetracontan-43-oate $^1$H NMR (400 MHz, $CD_3OD$) δ 9.36 (s, 2H), 9.25 (s, 1H), 8.71 (s, 1H), 7.55 (d, J=7.2 Hz, 1H), 7.43 (d, J=7.2 Hz, 1H), 6.00 (d, J=18.0 Hz, 1H), 5.82 (d, J=18.0 Hz, 1H), 4.65-4.64 (m, 1H), 4.45-4.44 (m, 1H), 4.12-4.11 (m, 4H), 3.85-3.41 (m, 19H), 2.85 (s, 3H), 2.82 (s, 3H), 2.55-2.54 (m, 2H), 2.32-2.22 (m, 6H), 2.12 (s, 3H), 1.61-1.59 (m, 5H), 1.29-1.27 (m, 31H), 1.11-0.98 (m, 2H).

Scheme 115: (4S,7S,10S,13S,16S,19S,22S)-22-acetamido-4-(((((1R,3S,5R)-2-(2-(3-acetyl-7-methyl-5-(2-methylpyrimidin-5-yl)-1H-indazol-1-yl)acetyl)-3-((6-bromo-3-methylpyridin-2-yl)carbamoyl)-2-azabicyclo[3.1.0]hexan-5-yl)methyl)carbamoyl)-10,16-bis(2-carboxyethyl)-7,19-bis(4-hydroxybenzyl)-6,9,12,15,18,21-hexaoxo-13-(4-palmitamidobutyl)-5,8,11,14,17,20-hexaazapentacosanedioic acid (443)

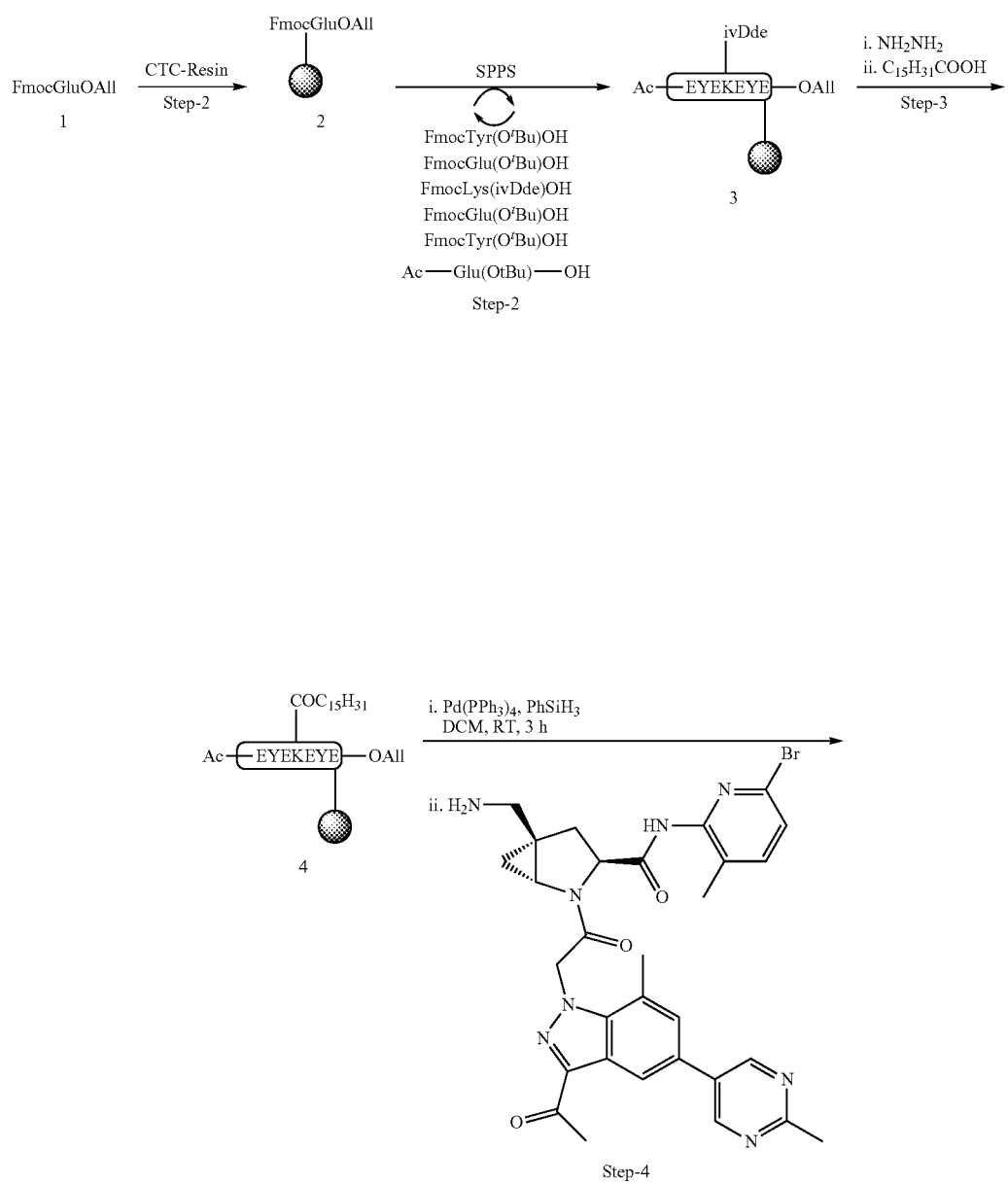

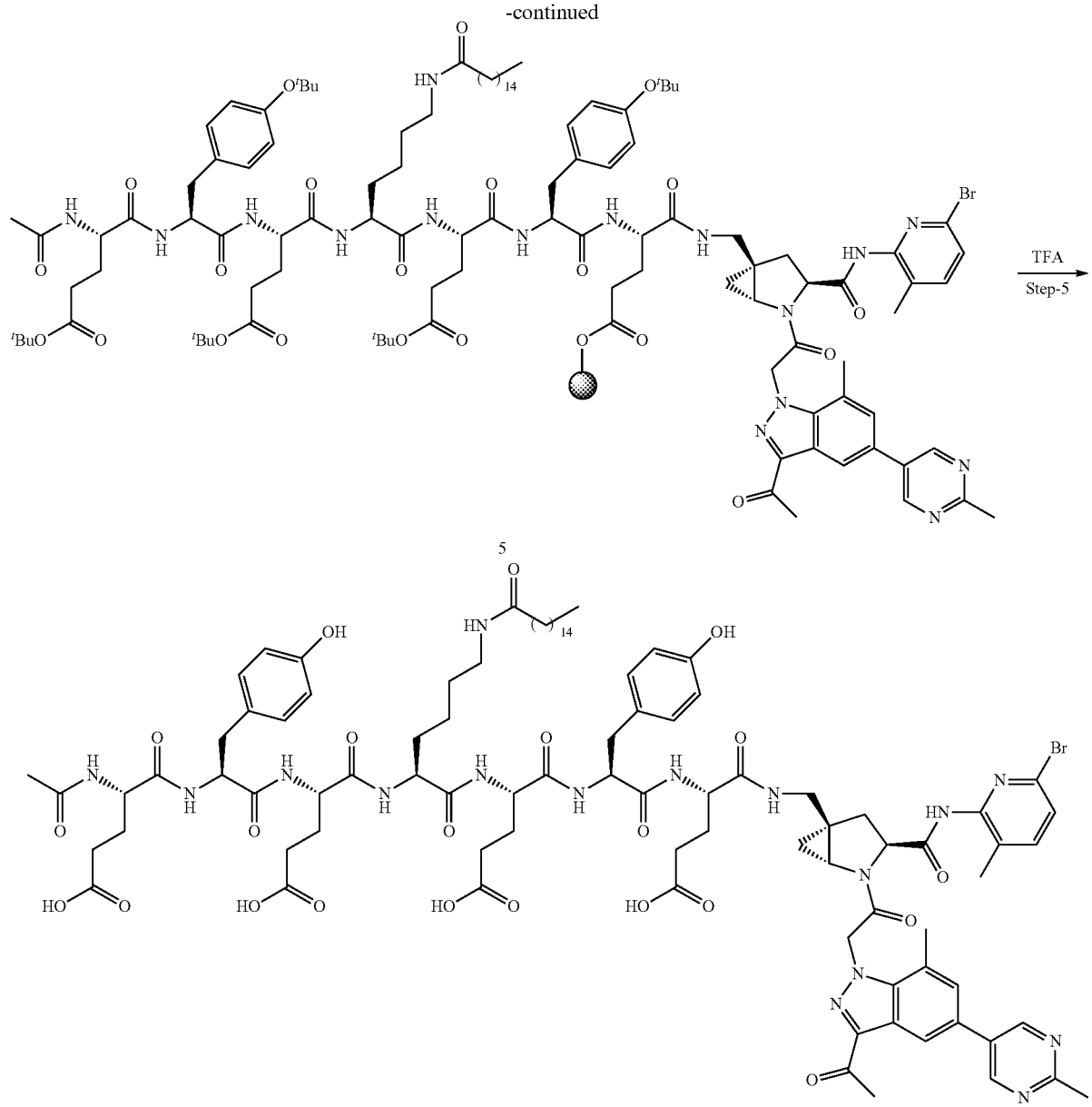

Step-1: Loading 2-chlorotrityl Chloride

A solution of 2-chlorotrityl chloride (1 equiv) in DCM (10 vol) was swelled in a closed syringe filter for 15 minutes and then filtered. A mixture of FmocGluOAll (1.5 equiv) in DCM (10 vol) and DIPEA (4 equiv) was added to the resin. The resulting mixture was shook for 16 hours and filtered. The resin was washed with DMF (5 times), DCM (5 times) and DMF (5 times) again. The resulting resin was dried for 15 minutes.

Capping: Capping solution (DCM, MeOH and DIPEA; 17:2:1) was added to the above resin and the mixture was shook for 1 hour at room temperature. The capping solution was pushed out=with nitrogen and the resin with washed with DMF (5 times), DCM (5 times) and DMF (5 times) again. The resulting resin was dried for 15 minutes to afford compound 2.

Step-2: Deprotection of Fmoc

Resin (2) was treated with 20% piperidine solution in DMF (5 vol) and shook for 15 minutes. The piperidine solution was pushed out with nitrogen and the process was repeated once again. The resin was washed with DMF (5 times), DCM (5 times) and DMF (5 times) again. The resulting resin was dried for 15 minutes.

Manual coupling of amino acids: To a mixture of Fmoc-Tyr(O'Bu)OH (3 equiv), DMF (10 vol), HATU (3 equiv) and DIPEA (5 equiv) was added to the above resin and shook for 6 hours at room temperature. The reaction mixture was pushed out with nitrogen and the resin was washed with DMF (5 times), DCM (5 times) and DMF (5 times) again. The resulting resin was dried for 15 minutes. The same process was repeated for all Fmoc-deprotections and amino acid couplings (FmocGlu(OtBu)OH, FmocLys(ivDde)OH, FmocGlu(OtBu)OH, FmocTyr(OtBu)OH and Ac-Glu(OtBu)-OH) to afford compound 3.

Step-3: Deprotection of ivDde

Resin was treated with 5% hydrazine in DMF (5 vol) and shook for 15 minutes. The hydrazine solution was pushed out with nitrogen and the process was repeated once again. The resin was washed with DMF (5 times), DCM (5 times) and DMF (5 times) again. The resulting resin was dried for 15 minutes.

Palmitic acid coupling: A mixture of palmitic acid (3 equiv), DMF (10 vol), HATU (3 equiv) and DIPEA (5 equiv) was added to the above resin and shook for 6 hours at room temperature. The reaction mixture was pushed out with nitrogen and the resin was washed with DMF (5 times), DCM (5 times) and DMF (5 times) again. The resulting resin was dried for 15 minutes to afford compound 4.

Step-4: Deprotection of Alloc

To a solution of resin compound 4 in DCM (10 vol), tetrakis (0.5 equiv) and phenylsilane (20 equiv) were added and the mixture was shook for 15 minutes and degassed with nitrogen. The reaction mixture was pushed out with nitrogen and the process was repeated once again. The resin was washed with DMF (5 times), DCM (5 times) and DMF (5 times) again. The resulting resin was dried for 15 minutes.

API coupling: To a mixture of (1R,3S,5R)-2-(2-(3-acetyl-7-methyl-5-(2-methylpyrimidin-5-yl)-1H-indazol-1-yl)acetyl)-5-(aminomethyl)-N-(6-bromo-3-methylpyridin-2-yl)-2-azabicyclo[3.1.0]hexane-3-carboxamide (3 equiv), DMF (10 vol), DIPC (3 equiv) and HOBt (3 equiv) were added and the resin was shook for 6 hours at room temperature. The reaction mixture was pushed out with nitrogen and the resin was washed with DMF (5 times), DCM (5 times) and DMF (5 times) again. The resulting resin was dried for 15 minutes to afford compound 5.

Step-5: Cleavage of Resin

Resin (compound 5) was treated with scavenger solution (TFA:TIPS:H$_2$O; 9.5:0.25:0.25, 10 vol) and shook for 4 hours. the scavenger solution was filtered and the resin was washed with TFA (2 vol) and concentrated. The crude product was purified by preparative purification to afford Compound 443. $^1$H NMR (400 MHz, DMSO-d$_6$) δ 12.08 (s, 2H), 10.31 (s, 1H), 9.21-9.20 (m, 1H), 9.00 (s, 2H), 8.12-8.00 (m, 4H), 7.98-7.96 (m, 2H), 7.56-7.55 (m, 2H), 7.42-7.41 (m, 2H), 7.00-6.98 (m, 3H), 6.55-6.54 (m, 3H), 6.00 (d, J=18.0 Hz, 1H), 5.65 (d, J=18.0 Hz, 1H), 4.44-4.43 (m, 2H), 4.21-4.20 (m, 4H), 3.63-3.62 (m, 1H), 3.00-2.98 (m, 4H), 2.81-2.80 (m, 10H), 2.32-2.31 (m, 10H), 1.98-1.97 (m, 10H), 1.56-1.55 (m, 12H), 1.21-1.10 (m, 37H), 1.11-1.10 (m, 1H), 0.98-0.97 (m, 1H).

Scheme 116: Synthesis of (4S,7S,10S,13S,16S,19S,22S)-22-acetamido-4-((1-((1R,3S,5R)-2-(2-(3-acetyl-7-methyl-5-(2-methylpyrimidin-5-yl)-1H-indazol-1-yl)acetyl)-3-((6-bromo-3-methylpyridin-2-yl)carbamoyl)-2-azabicyclo[3.1.0]hexan-5-yl)-3-oxo-6,9,12,15,18,21,24,27,30,33,36,39,42,45,48,51,54,57,60,63,66,69,72,75-tetracosaoxa-2-azaheptaheptacontan-77-yl)carbamoyl)-10,16-bis(2-carboxyethyl)-7,19-bis(4-hydroxybenzyl)-6,9,12,15,18,21-hexaoxo-13(4-palmitamidobutyl)-5,8,11,14,17,20-hexaazapentacosanedioic acid (535)

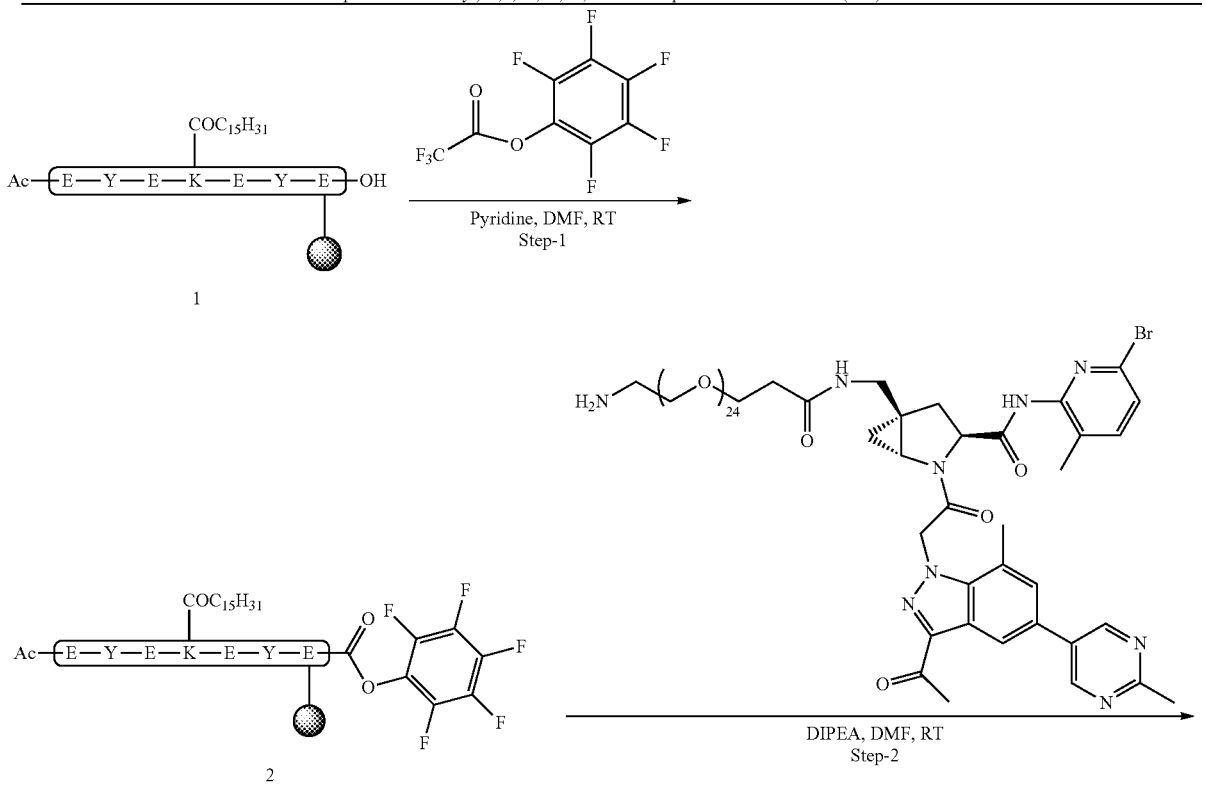

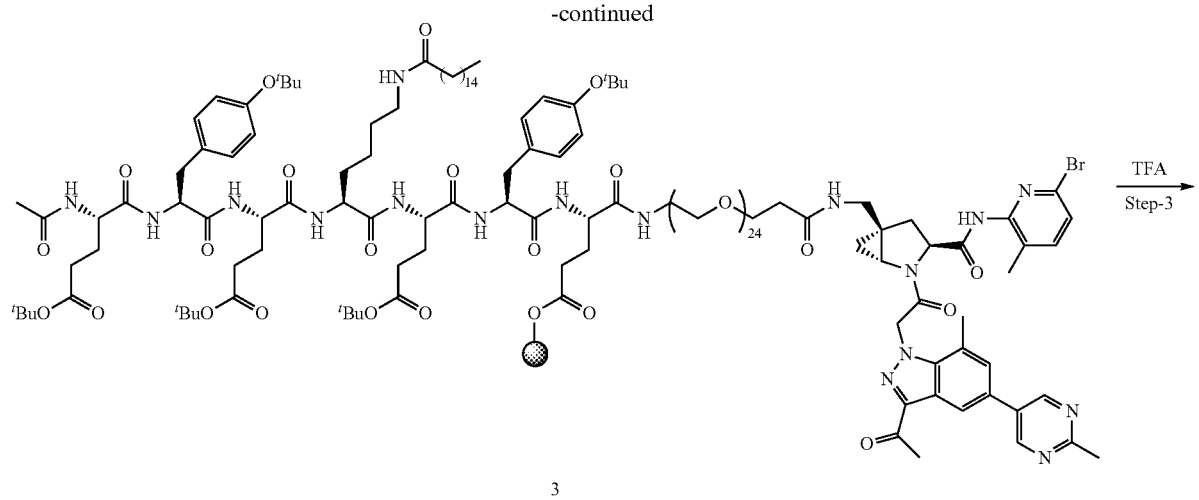

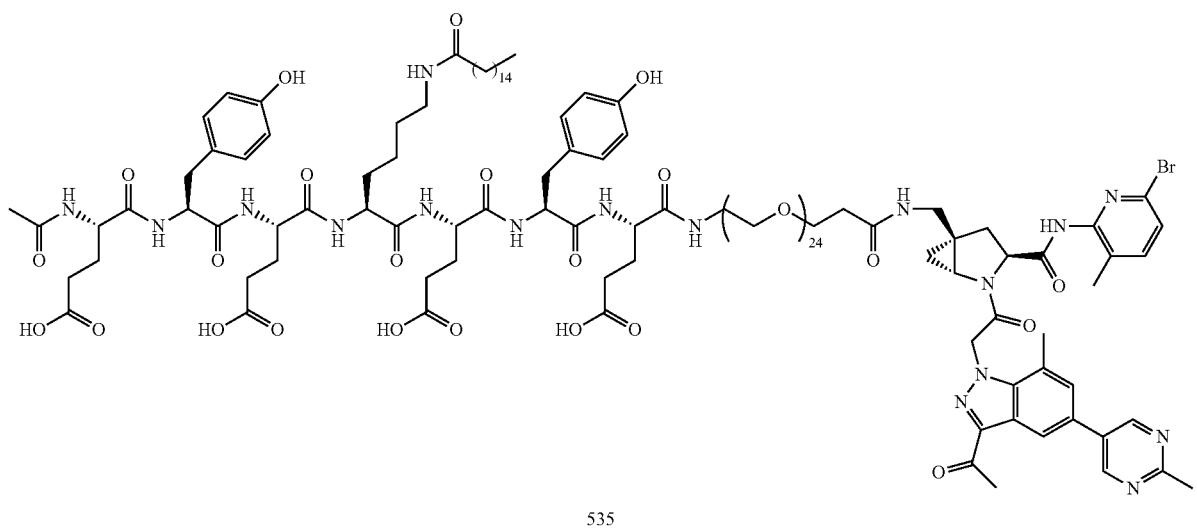

Step-1: Perfluorophenyl 2,2,2-trifluoroacetate Coupling

To a mixture of compound 1 (1 equiv), DMF (10 vol), pyridine (5 equiv), and perfluorophenyl 2,2,2-trifluoroacetate (1.2 equiv) were added and the resin was shook for 16 hours at room temperature. The reaction mixture was pushed out with nitrogen and the resin was washed with DMF (5 times), DCM (5 times) and DMF (5 times). The resulting resin was dried for 15 minutes to afford compound 2.

Step-2: API Coupling

A mixture of (1R,3S,5R)-2-(2-(3-acetyl-7-methyl-5-(2-methylpyrimidin-5-yl)-1H-indazol-1-yl)acetyl)-5-(77-amino-3-oxo-6,9,12,15,18,21,24,27,30,33,36,39,42,45,48,51,54,57,60,63,66,69,72,75-tetracosaoxa-2-azaheptaheptacontyl)-N-(6-bromo-3-methylpyridin-2-yl)-2-azabicyclo[3.1.0]hexane-3-carboxamide hydrochloride (1.2 equiv), DMF (10 vol) and DIPEA (5 equiv) were added to the above resin (compound 2) and the resin was shook for 16 hours at room temperature. The reaction mixture was pushed out with nitrogen and the resin was washed with DMF (5 times), DCM (5 times) and DMF (5 times). The resulting resin was dried for 15 minutes to afford compound 3.

Step-3: Cleavage of Resin

Resin (compound 3) was treated with scavenger solution (TFA:TIPS:$H_2O$; 9.5:0.25:0.25, 10 vol) and shook for 4 hours. The scavenger solution was filtered and the resin was washed with TFA (2 vol) and concentrated. The crude product was purified by preparative purification to afford Compound 535.

Example 9. Non-Limiting Examples of Compounds of the Present Invention I

Table 6, Table 7, and Table 8 show illustrative Factor D inhibitors with characterizing data. The assay of Example 10 was used to determine the $IC_{50}$'s of the compounds. Other standard factor D inhibition assays are also available. Three *s are used to denote compounds with an $IC_{50}$ less than 1 micromolar; two s indicate compound with an $IC_{50}$ between 1 micromolar and 10 micromolar, and one * denotes compounds with an $IC_{50}$ greater than 10 micromolar.

TABLE 6

Non-limiting Examples of Compounds of the Present Invention

| Cmp No. | Structure | Name | IC$_{50}$ | RT min (Method A, B, C or D) | MS (M + 1) |
|---|---|---|---|---|---|
| 1 | 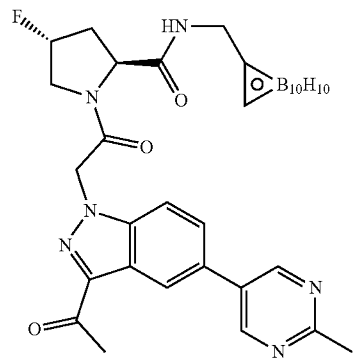 | | *** | 12.55 (D) | 580 (M − 1) |
| 2 | 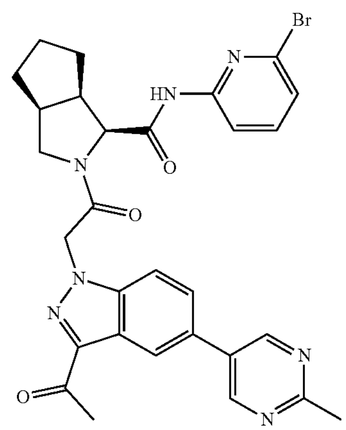 [SMILES: CC(=O)c1nn(CC(=O)N2C[C@H]3CCC[C@H]3[C@H]2C(=O)Nc2cccc(Br)n2)c2ccc(-c3cnc(C)nc3)cc12] | (1S,3aS,6aR)-2-(2-(3-acetyl-5-(2-methylpyrimidin-5-yl)-1H-indazol-1-yl)acetyl)-N-(6-bromopyridin-2-yl)octahydro-cyclopenta[c]pyrrole-1-carboxamide | ** | 3.52 (B) | 602 |
| 3 | 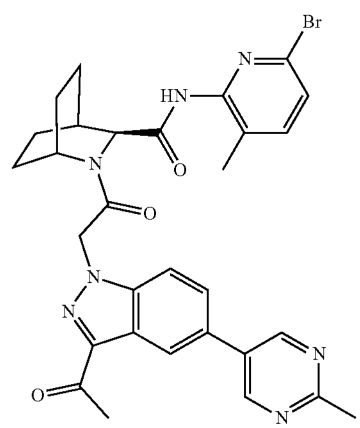 [SMILES: CC(=O)c1nn(CC(=O)N2C3CCC(CC3)[C@H]2C(=O)Nc2nc(Br)ccc2C)c2ccc(-c3cnc(C)nc3)cc12] | (1s,4s)-2-(2-(3-acetyl-5-(2-methylpyrimidin-5-yl)-1H-indazol-1-yl)acetyl)-N-(6-bromo-3-methylpyridin-2-yl)-2-azabicyclo[2.2.2]octane-3-carboxamide | *** | 3.07 (B) | 616 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 4 | 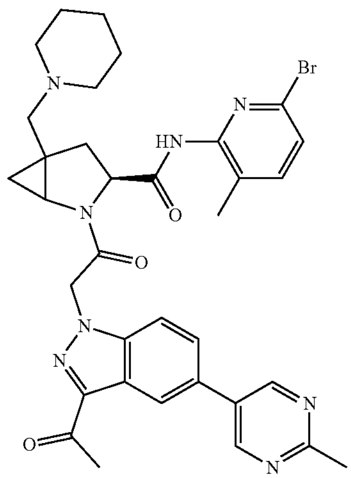 [SMILES: CC(=O)c1nn(CC(=O)N2C3CC3(CN3CCCCC3)C[C@H]2C(=O)Nc2nc(Br)ccc2C)c2ccc(-c3cnc(C)nc3)cc12] | (3S)-2-(2-(3-acetyl-5-(2-methylpyrimidin-5-yl)-1H-indazol-1-yl)acetyl)-N-(6-bromo-3-methylpyridin-2-yl)-5-(piperidin-1-ylmethyl)-2-azabicyclo[3.1.0]hexane-3-carboxamide | *** | 3.66 (B) | 685 |
| 5 | 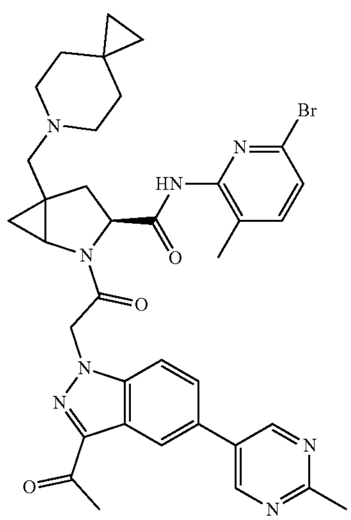 [SMILES: CC(=O)c1nn(CC(=O)N2C3CC3(CN3CCC4(CC3)CC4)C[C@H]2C(=O)Nc2nc(Br)ccc2C)c2ccc(-c3cnc(C)nc3)cc12] | (3S)-5-(6-azaspiro[2.5]octan-6-ylmethyl)-2-(2-(3-acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide | *** | 3.82 (B) | 711 |
| 6 | 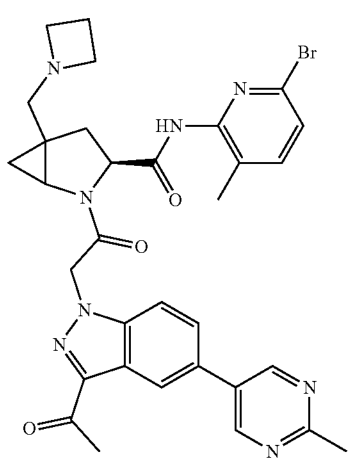 [SMILES: CC(=O)c1nn(CC(=O)N2C3CC3(CN3CCC3)C[C@H]2C(=O)Nc2nc(Br)ccc2C)c2ccc(-c3cnc(C)nc3)cc12] | (3S)-2-(2-(3-acetyl-5-(2-methylpyrimidin-5-yl)-1H-indazol-1-yl)acetyl)-5-(azetidin-1-ylmethyl)-N-(6-bromo-3-methylpyridin-2-yl)-2-azabicyclo[3.1.0]hexane-3-carboxamide | *** | 3.57 (B) | 657 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 7 | 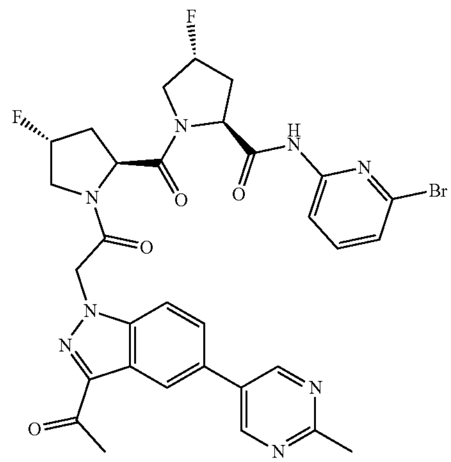 [SMILES: CC(=O)c1nn(CC(=O)N2C[C@H](F)C[C@H]2C(=O)N2C[C@H](F)C[C@H]2C(=O)Nc2cccc(Br)n2)c2ccc(-c3cnc(C)nc3)cc12] | (2S,4R)-1-((2S,4R)-1-(2-(3-acetyl-5-(2-methylpyrimidin-5-yl)-1H-indazol-1-yl)acetyl)-4-fluoropyrrolidine-2-carbonyl)-N-(6-bromopyridin-2-yl)-4-fluoropyrrolidine-2-carboxamide | ** | 1.68 (A) | 695 |
| 8 | 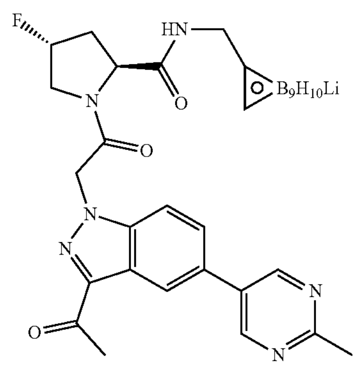 | | *** | 13.19 (C) | 570 |
| 9 | 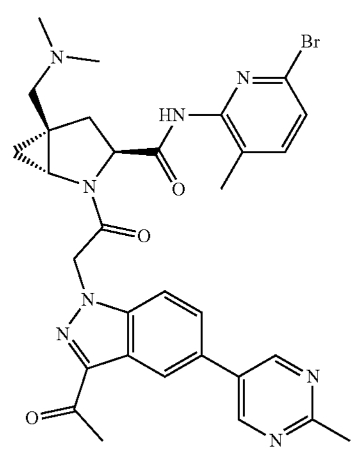 | (1R,3S,5R)-2-(2-(3-acetyl-5-(2-methylpyrimidin-5-yl)-1H-indazol-1-yl)acetyl)-N-(6-bromo-3-methylpyridin-2-yl)-5-((dimethylamino)methyl)-2-azabicyclo[3.1.0]hexane-3-carboxamide | *** | 1.17 (B) | 645 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 10 | 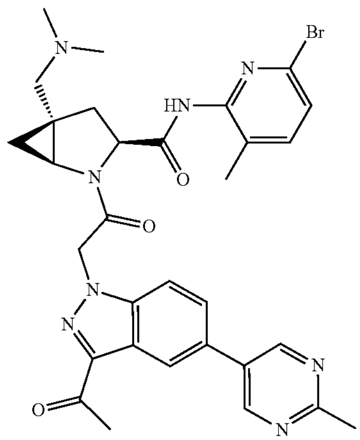 [SMILES: CC(=O)c1nn(CC(=O)N2[C@H]3C[C@@]3(CN(C)C)C[C@H]2C(=O)Nc2nc(Br)ccc2C)c2ccc(-c3cnc(C)nc3)cc12] | (1S,3S,5S)-2-(2-(3-acetyl-5-(2-methylpyrimidin-5-yl)-1H-indazol-1-yl)acetyl)-N-(6-bromo-3-methylpyridin-2-yl)-5-((dimethyl-amino)methyl)-2-azabicyclo[3.1.0]hexane-3-carboxamide | ** | 2.35 (B) | 645 |
| 11 | 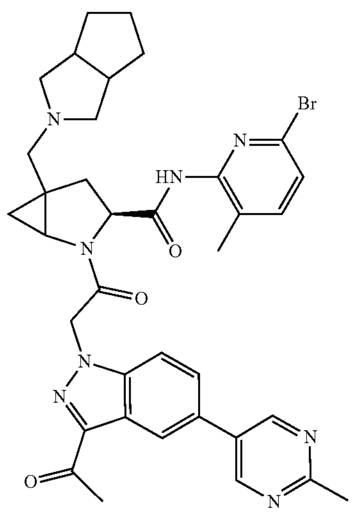 [SMILES: CC(=O)c1nn(CC(=O)N2C3CC3(CN3CC4CCCC4C3)C[C@H]2C(=O)Nc2nc(Br)ccc2C)c2ccc(-c3cnc(C)nc3)cc12] | (3S)-2-(2-(3-acetyl-5-(2-methylpyrimidin-5-yl)-1H-indazol-1-yl)acetyl)-N-(6-bromo-3-methylpyridin-2-yl)-5-((hexahydro-cyclopenta[c]pyrrol-2(1H)-yl)methyl)-2-azabicyclo[3.1.0]hexane-3-carboxamide | *** | 0.36 (B) | 711 |
| 12 | 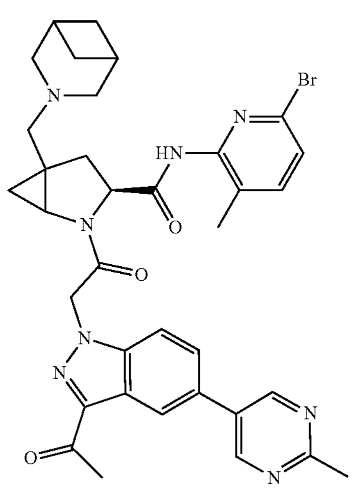 [SMILES: CC(=O)c1nn(CC(=O)N2C3CC3(CN3CC4CC(C4)C3)C[C@H]2C(=O)Nc2nc(Br)ccc2C)c2ccc(-c3cnc(C)nc3)cc12] | (3S)-5-(3-azabicyclo[3.1.1]heptan-3-ylmethyl)-2-(2-(3-acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide | *** | 3.63 (B) | 697 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 13 | 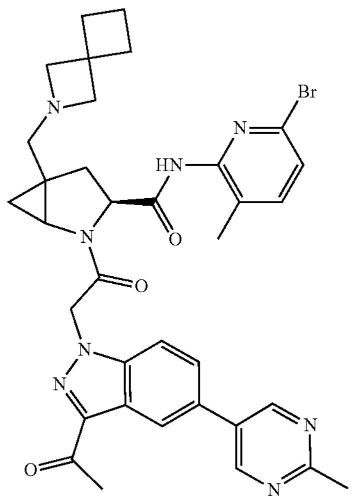 [SMILES: CC(=O)c1nn(CC(=O)N2C3CC3(CN3CC4(CCC4)C3)C[C@H]2C(=O)Nc2nc(Br)ccc2C)c2ccc(-c3cnc(C)nc3)cc12] | (3S)-5-(2-azaspiro[3.3]heptan-2-ylmethyl)-2-(2-(3-acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide | *** | 3.58 (B) | 697 |
| 14 | 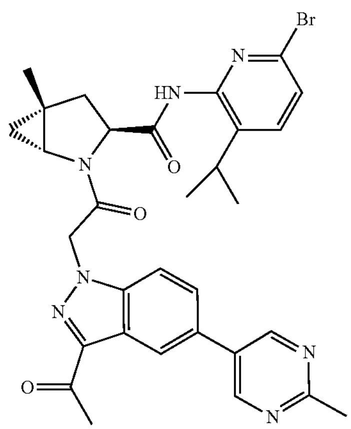 [SMILES: CC(=O)c1nn(CC(=O)N2[C@H](C(=O)Nc3nc(Br)ccc3C(C)C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-isopropylpyridin-2-yl)-5-methyl-2-azabicyclo[3.1.0]hexane-3-carboxamide | *** | 2.06 (A) | 630 |
| 15 | 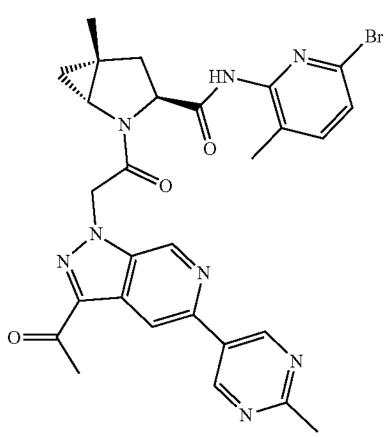 [SMILES: CC(=O)c1nn(CC(=O)N2[C@H](C(=O)Nc3nc(Br)ccc3C)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-methyl-2-azabicyclo[3.1.0]hexane-3-carboxamide | *** | 1.71 (A) | 605 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 16 | 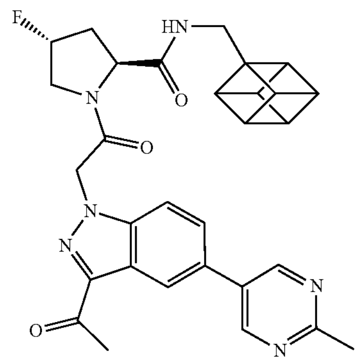 [SMILES: CC(=O)c1nn(CC(=O)N2C[C@H](F)C[C@H]2C(=O)NCC23C4C5C6C4C2C6C53)c2ccc(-c3cnc(C)nc3)cc12] | (2S,4R)-1-(2-(3-acetyl-5-(2-methylpyrimidin-5-yl)-1H-indazol-1-yl)acetyl)-N-(cuban-1-ylmethyl)-4-fluoropyrrolidine-2-carboxamide | ** | 10.52 (D) | 541 |
| 17 | 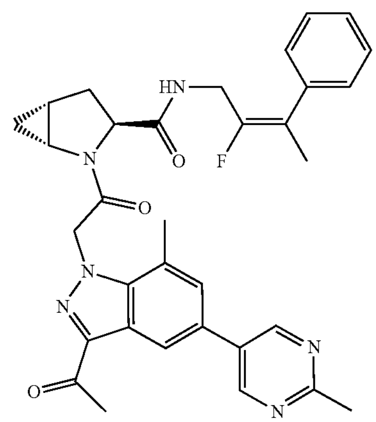 [SMILES: CC(=O)c1nn(CC(=O)N2[C@@H]3C[C@@H]3C[C@H]2C(=O)NC/C(F)=C(/C)c2ccccc2)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-((E)-2-fluoro-3-phenylbut-2-en-1-yl)-2-azabicyclo[3.1.0]hexane-3-carboxamide | *** | 2.08 (A) | 581 |
| 18 | 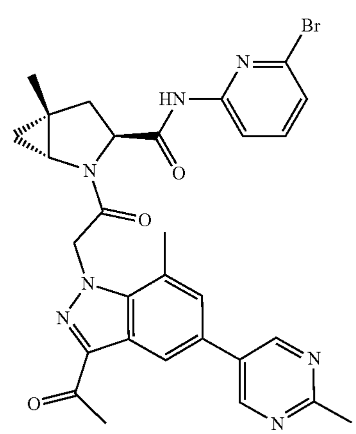 [SMILES: CC(=O)c1nn(CC(=O)N2[C@H](C(=O)Nc3cccc(Br)n3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromopyridin-2-yl)-5-methyl-2-azabicyclo[3.1.0]hexane-3-carboxamide | *** | 12.76 (C) | 605 (M + 2) |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 19 | 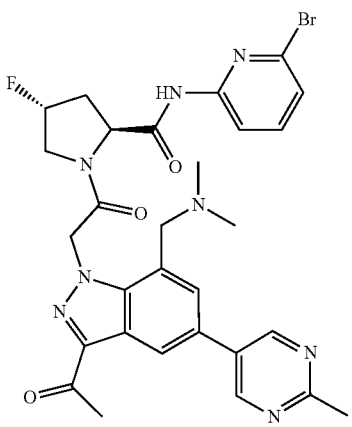 [SMILES: CC(=O)c1nn(CC(=O)N2C[C@H](F)C[C@H]2C(=O)Nc2cccc(Br)n2)c2c(CN(C)C)cc(-c3cnc(C)nc3)cc12] | (2S,4R)-1-(2-(3-acetyl-7-((dimethyl-amino)methyl)-5-(2-methylpyrimidin-5-yl)-1H-indazol-1-yl)acetyl)-N-(6-bromopyridin-2-yl)-4-fluoropyrrolidine-2-carboxamide | *** | 2.31 (B) | 637 |
| 20 | 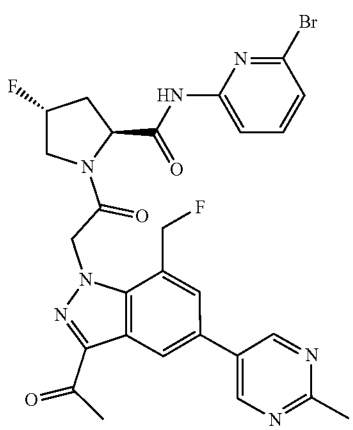 [SMILES: CC(=O)c1nn(CC(=O)N2C[C@H](F)C[C@H]2C(=O)Nc2cccc(Br)n2)c2c(CF)cc(-c3cnc(C)nc3)cc12] | (2S,4R)-1-(2-(3-acetyl-7-(fluoromethyl)-5-(2-methylpyrimidin-5-yl)-1H-indazol-1-yl)acetyl)-N-(6-bromopyridin-2-yl)-4-fluoropyrrolidine-2-carboxamide | *** | 3.29 (B) | 612 |
| 21 | 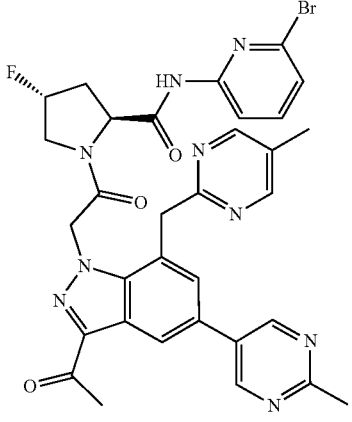 [SMILES: CC(=O)c1nn(CC(=O)N2C[C@H](F)C[C@H]2C(=O)Nc2cccc(Br)n2)c2c(Cc3ncc(C)cn3)cc(-c3cnc(C)nc3)cc12] | (2S,4R)-1-(2-(3-acetyl-7-((5-methylpyrimidin-2-yl)methyl)-5-(2-methylpyrimidin-5-yl)-1H-indazol-1-yl)acetyl)-N-(6-bromopyridin-2-yl)-4-fluoropyrrolidine-2-carboxamide | *** | 3.18 (B) | 686 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 22 | 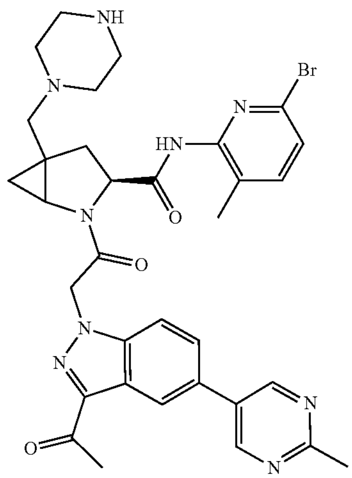 [SMILES: CC(=O)c1nn(CC(=O)N2C3CC3(CN3CCNCC3)C[C@H]2C(=O)Nc2nc(Br)ccc2C)c2ccc(-c3cnc(C)nc3)cc12] | (3S)-2-(2-(3-acetyl-5-(2-methylpyrimidin-5-yl)-1H-indazol-1-yl)acetyl)-N-(6-bromo-3-methylpyridin-2-yl)-5-(piperazin-1-ylmethyl)-2-azabicyclo[3.1.0]hexane-3-carboxamide | *** | 3.77 (B) | 686 |
| 23 | 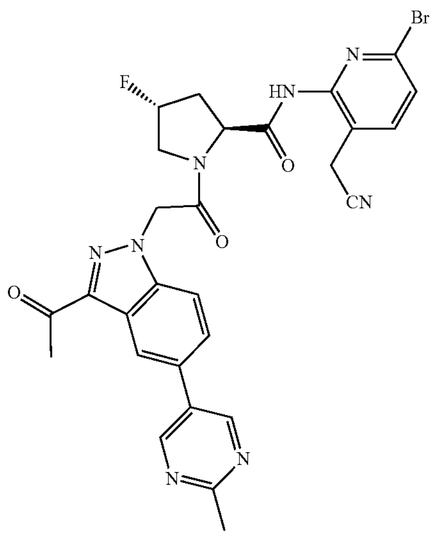 [SMILES: CC(=O)c1nn(CC(=O)N2C[C@H](F)C[C@H]2C(=O)Nc2nc(Br)ccc2CC#N)c2ccc(-c3cnc(C)nc3)cc12] | (2S,4R)-1-(2-(3-acetyl-5-(2-methylpyrimidin-5-yl)-1H-indazol-1-yl)acetyl)-N-(6-bromo-3-(cyanomethyl)-pyridin-2-yl)-4-fluoropyrrolidine-2-carboxamide | *** | 1.50 (A) | 619 |
| 24 | 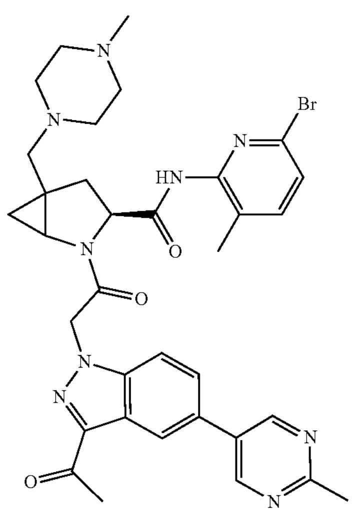 [SMILES: CC(=O)c1nn(CC(=O)N2C3CC3(CN3CCN(C)CC3)C[C@H]2C(=O)Nc2nc(Br)ccc2C)c2ccc(-c3cnc(C)nc3)cc12] | (3S)-2-(2-(3-acetyl-5-(2-methylpyrimidin-5-yl)-1H-indazol-1-yl)acetyl)-N-(6-bromo-3-methylpyridin-2-yl)-5-((4-methylpiperazin-1-yl)methyl)-2-azabicyclo[3.1.0]hexane-3-carboxamide | *** | 3.70 (B) | 700 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 25 | 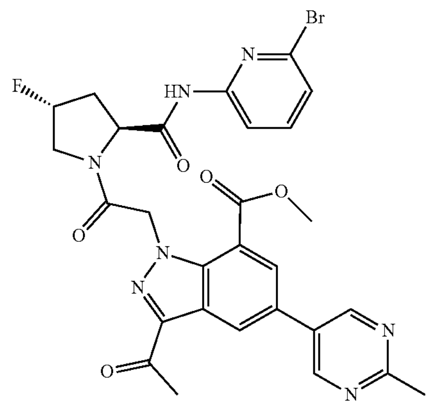 [SMILES: COC(=O)c1cc(-c2cnc(C)nc2)cc2c(C(C)=O)nn(CC(=O)N3C[C@H](F)C[C@H]3C(=O)Nc3cccc(Br)n3)c12] | methyl 3-acetyl-1-(2-((2S,4R)-2-((6-bromopyridin-2-yl)carbamoyl)-4-fluoropyrrolidin-1-yl)-2-oxoethyl)-5-(2-methylpyrimidin-5-yl)-1H-indazole-7-carboxylate | *** | 1.94 (A) | 638 |
| 26 | 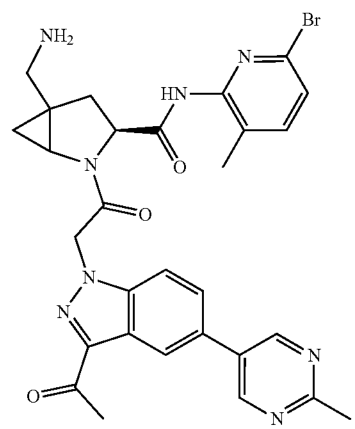 [SMILES: CC(=O)c1nn(CC(=O)N2C3CC3(CN)C[C@H]2C(=O)Nc2nc(Br)ccc2C)c2ccc(-c3cnc(C)nc3)cc12] | (3S)-2-(2-(3-acetyl-5-(2-methylpyrimidin-5-yl)-1H-indazol-1-yl)acetyl)-5-(aminomethyl)-N-(6-bromo-3-methylpyridin-2-yl)-2-azabicyclo[3.1.0]hexane-3-carboxamide | ** | 2.49 (B) | 617 |
| 27 | 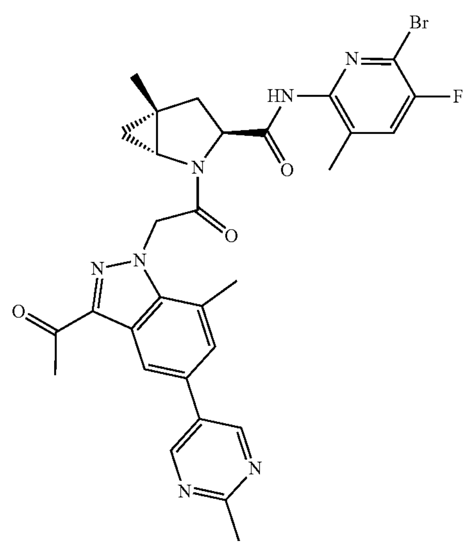 [SMILES: CC(=O)c1nn(CC(=O)N2[C@H](C(=O)Nc3nc(Br)c(F)cc3C)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-5-fluoro-3-methylpyridin-2-yl)-5-methyl-2-azabicyclo[3.1.0]hexane-3-carboxamide | *** | 2.01 (A) | 634 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 28 | 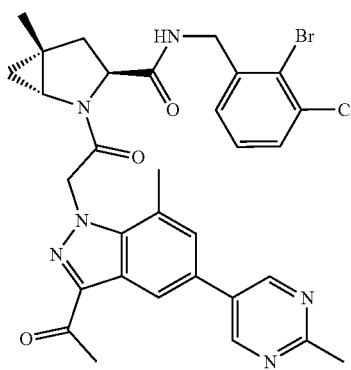 | (1R,3S,5R)-2-(2-(3-acetyl-7-methyl-5-(2-methylpyrimidin-5-yl)-1H-indazol-1-yl)acetyl)-N-(3-chloro-2-fluorobenzyl)-5-methyl-2-azabicyclo[3.1.0]hexane-3-carboxamide | *** | 11.61 (C) | 590 |
| 29 | 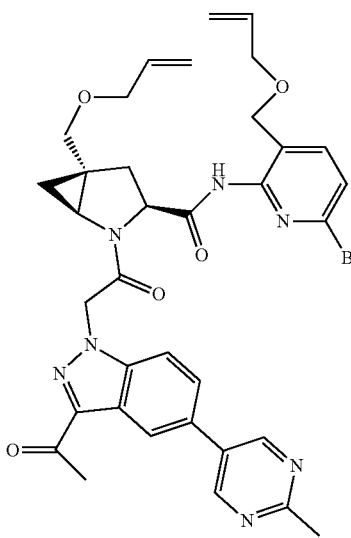 | (1S,3S,5R)-2-(2-methylpyrimidin-5-yl)-1H-indazol-1-yl)acetyl)-5-((allyloxy)-methyl)-N-(3-((allyloxy)-methyl)-6-bromopyridin-2-yl)-2-azabicyclo[3.1.0]hexane-3-carboxamide | *** | 2.28 (A) | 714 |
| 30 | 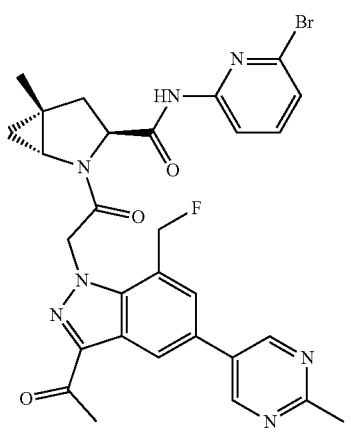 [SMILES: CC(=O)c1nn(CC(=O)N2[C@H](C(=O)Nc3cccc(Br)n3)C[C@@]3(C)C[C@@H]23)c2c(CF)cc(-c3cnc(C)nc3)cc12] | (1R,3S,5R)-2-(2-(3-acetyl-7-(fluoromethyl)-5-(2-methylpyrimidin-5-yl)-1H-indazol-1-yl)acetyl)-N-(6-bromopyridin-2-yl)-5-methyl-2-azabicyclo[3.1.0]hexane-3-carboxamide | | 3.69 (B) | 620 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 31 | 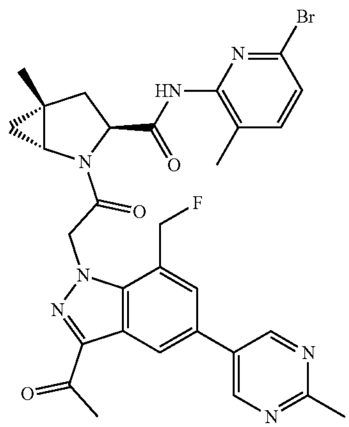 [SMILES: CC(=O)c1nn(CC(=O)N2[C@H](C(=O)Nc3nc(Br)ccc3C)C[C@@]3(C)C[C@@H]23)c2c(CF)cc(-c3cnc(C)nc3)cc12] | (1R,3S,5R)-2-(2-(3-acetyl-7-(fluoromethyl)-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 3.48 (B) | 634 |
| 32 | 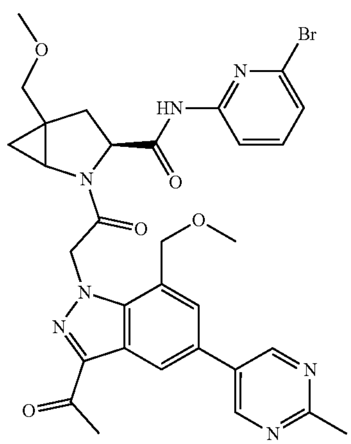 [SMILES: COCc1cc(-c2cnc(C)nc2)cc2c(C(C)=O)nn(CC(=O)N3C4CC4(COC)C[C@H]3C(=O)Nc3cccc(Br)n3)c12] | (3S)-2-(2-(3-acetyl-7-(methoxymethyl)-5-(2-methylpyrimidin-5-yl)-1H-indazol-1-yl)acetyl)-N-(6-bromopyridin-2-yl)-5-(methoxymethyl)-2-azabicyclo[3.1.0]hexane-3-carboxamide | *** | 3.47 (B) | 662 |
| 33 | 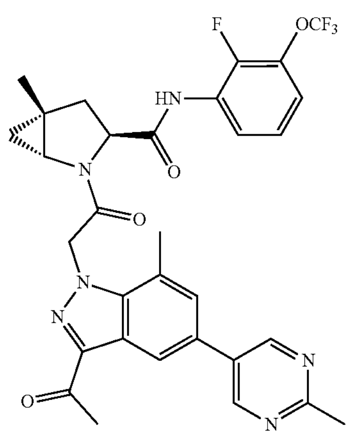 [SMILES: CC(=O)c1nn(CC(=O)N2[C@H](C(=O)Nc3cccc(OC(F)(F)F)c3F)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(2-fluoro-3-(trifluoromethoxy)phenyl)-5-methyl-2-azabicyclo[3.1.0]hexane-3-carboxamide | *** | 13.96 (C) | 625 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 34 | 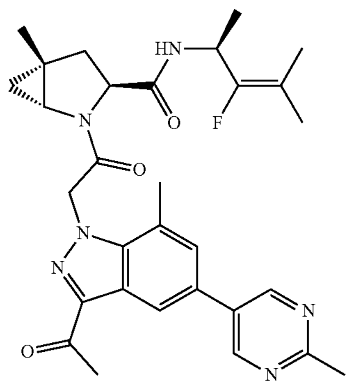 [SMILES: CC(=O)c1nn(CC(=O)N2[C@H](C(=O)N[C@@H](C)C(F)=C(C)C)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-((S)-3-fluoro-4-methylpent-3-en-2-yl)-5-methyl-2-azabicyclo[3.1.0]hexane-3-carboxamide | *** | 10.92 (D) | 547 |
| 35 | 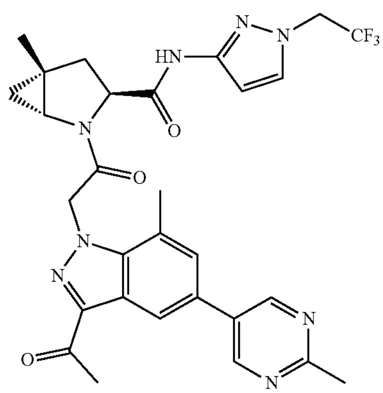 [SMILES: CC(=O)c1nn(CC(=O)N2[C@H](C(=O)Nc3ccn(CC(F)(F)F)n3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-methyl-N-(1-(2,2,2-trifluoroethyl)-1H-pyrazol-3-yl)-2-azabicyclo[3.1.0]hexane-3-carboxamide | *** | 10.92 (D) | 595 |
| 36 | 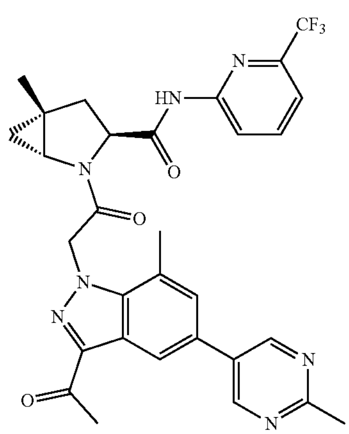 [SMILES: CC(=O)c1nn(CC(=O)N2[C@H](C(=O)Nc3cccc(C(F)(F)F)n3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-methyl-N-(6-(trifluoromethyl)pyridin-2-yl)-2-azabicyclo[3.1.0]hexane-3-carboxamide | *** | 12.55 (D) | 592 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 37 | 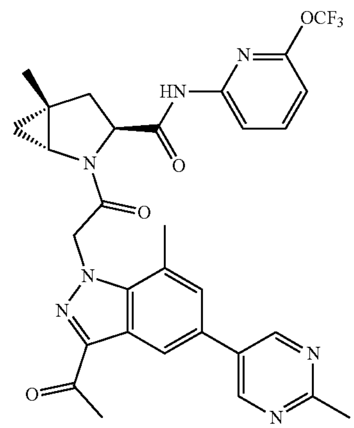 [SMILES: CC(=O)c1nn(CC(=O)N2[C@H](C(=O)Nc3cccc(OC(F)(F)F)n3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-methyl-N-(6-(trifluoromethoxy)pyridin-2-yl)-2-azabicyclo[3.1.0]hexane-3-carboxamide | *** | 14.96 (C) | 608 |
| 38 | 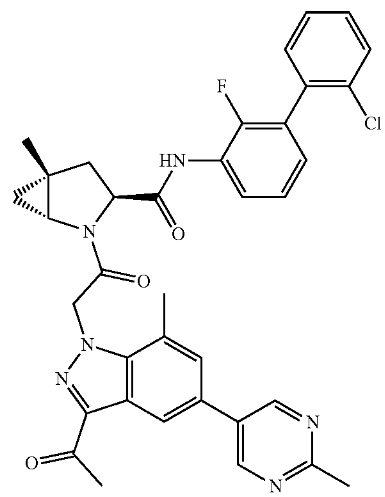 [SMILES: CC(=O)c1nn(CC(=O)N2[C@H](C(=O)Nc3cccc(-c4ccccc4Cl)c3F)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(2'-chloro-2-fluoro-[1,1'-biphenyl]-3-yl)-5-methyl-2-azabicyclo[3.1.0]hexane-3-carboxamide | *** | 15.94 (C) | 652 |
| 39 | 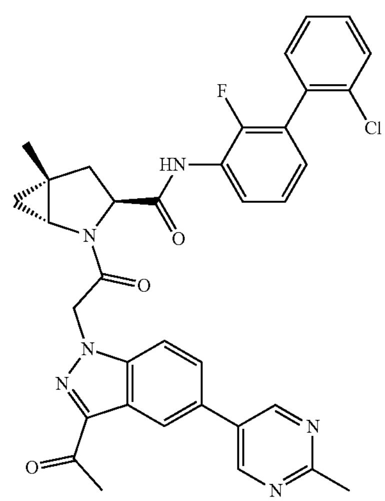 [SMILES: CC(=O)c1nn(CC(=O)N2[C@H](C(=O)Nc3cccc(-c4ccccc4Cl)c3F)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(2'-chloro-2-fluoro-[1,1'-biphenyl]-3-yl)-5-methyl-2-azabicyclo[3.1.0]hexane-3-carboxamide | *** | 12.84 (D) | 636 (M − 1) |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 40 | 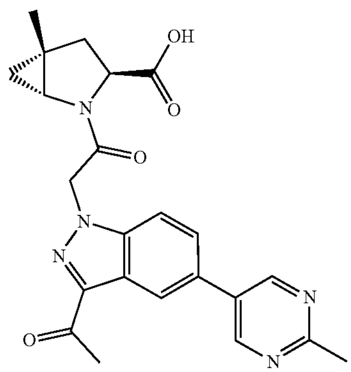 [SMILES: CC(=O)c1nn(CC(=O)N2[C@H](C(=O)O)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-5-methyl-2-azabicyclo[3.1.0]hexane-3-carboxylic acid | * | 1.31 (A) | 434 |
| 41 | 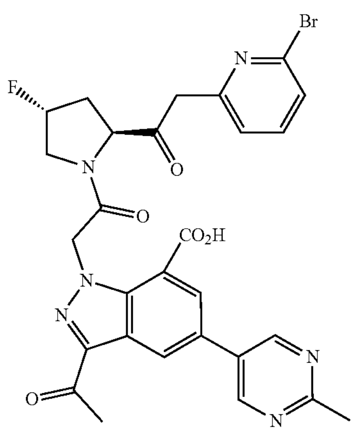 [SMILES: CC(=O)c1nn(CC(=O)N2C[C@H](F)C[C@H]2C(=O)Cc2cccc(Br)n2)c2c(C(=O)O)cc(-c3cnc(C)nc3)cc12] | 3-acetyl-1-(2-((2S,4R)-2-((6-bromopyridin-2-yl)carbamoyl)-4-fluoropyrrolidin-1-yl)-2-oxoethyl)-5-(2-methylpyrimidin-5-yl)-1H-indazole-7-carboxylic acid | *** | | 624 |
| 42 | 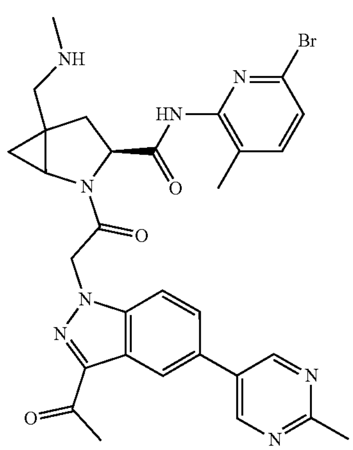 [SMILES: CNCC12CC1N(C(=O)Cn1nc(C(C)=O)c3cc(-c4cnc(C)nc4)ccc31)[C@H](C(=O)Nc1nc(Br)ccc1C)C2] | (3S)-2-(2-(3-acetyl-5-(2-methylpyrimidin-5-yl)-1H-indazol-1-yl)acetyl)-N-(6-bromo-3-methylpyridin-2-yl)-5-((methylamino)methyl)-2-azabicyclo[3.1.0]hexane-3-carboxamide | *** | 4.42 (B) | 631 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 43 | 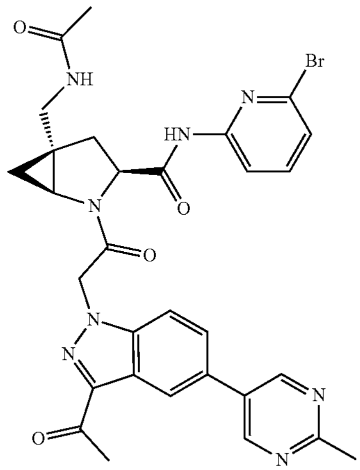 [SMILES: CC(=O)NC[C@@]12C[C@@H]1N(C(=O)Cn1nc(C(C)=O)c3cc(-c4cnc(C)nc4)ccc31)[C@H](C(=O)Nc1cccc(Br)n1)C2] | (1S,3S,5S)-5-(acetamidomethyl)-2-(2-(3-acetyl-5-(2-methylpyrimidin-5-yl)-1H-indazol-1-yl)acetyl)-N-(6-bromopyridin-2-yl)-2-azabicyclo[3.1.0]hexane-3-carboxamide | ** | 3.00 (B) | 645 |
| 44 | 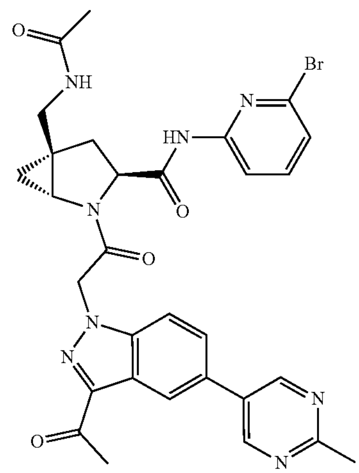 [SMILES: CC(=O)NC[C@@]12C[C@@H](C(=O)Nc3cccc(Br)n3)N(C(=O)Cn3nc(C(C)=O)c4cc(-c5cnc(C)nc5)ccc43)[C@@H]1C2] | (1R,3S,5R)-5-(acetamidomethyl)-2-(2-(3-acetyl-5-(2-methylpyrimidin-5-yl)-1H-indazol-1-yl)acetyl)-N-(6-bromopyridin-2-yl)-2-azabicyclo[3.1.0]hexane-3-carboxamide | *** | 3.08 (B) | 645 |
| 45 | 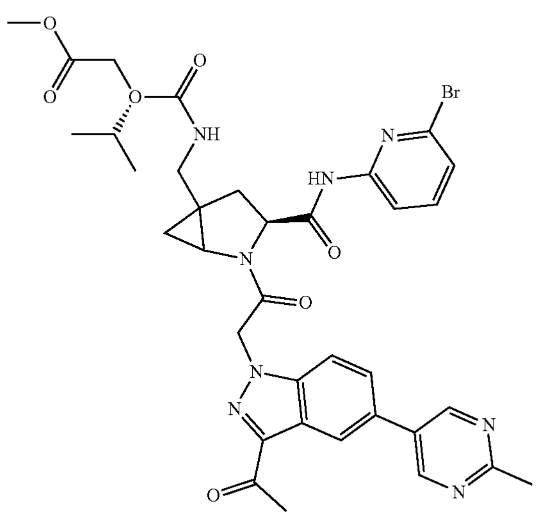 | methyl ((2S)-1-((((3S)-2-(2-(3-acetyl-5-(2-methylpyrimidin-5-yl)-1H-indazol-1-yl)acetyl)-3-((6-bromopyridin-2-yl)carbamoyl)-2-azabicyclo[3.1.0]hexan-5-yl)methyl)amino)-3-methyl-1-oxobutan-2-yl)carbamate | *** | 3.32 (B) | 760 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 46 | 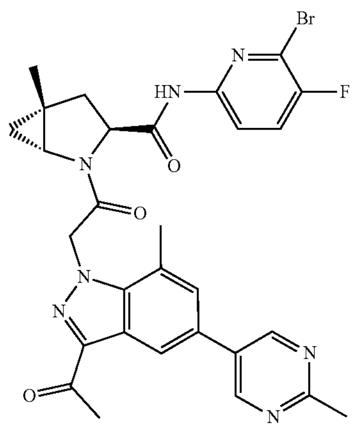 [SMILES: CC(=O)c1nn(CC(=O)N2[C@H](C(=O)Nc3ccc(F)c(Br)n3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-5-fluoropyridin-2-yl)-5-methyl-2-azabicyclo[3.1.0]hexane-3-carboxamide | *** | 3.77 (B) | 620 |
| 47 | 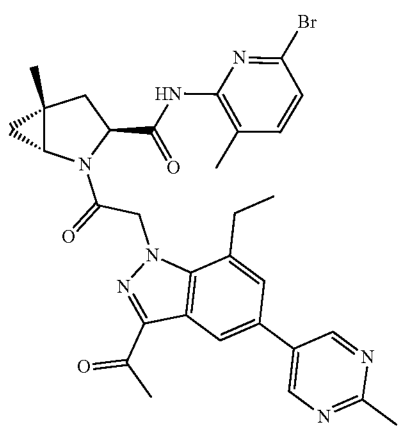 [SMILES: CCc1cc(-c2cnc(C)nc2)cc2c(C(C)=O)nn(CC(=O)N3[C@H](C(=O)Nc4nc(Br)ccc4C)C[C@@]4(C)C[C@@H]34)c12] | (1R,3S,5R)-2-(2-(3-acetyl-7-ethyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 3.59 (B) | 630 |
| 48 | 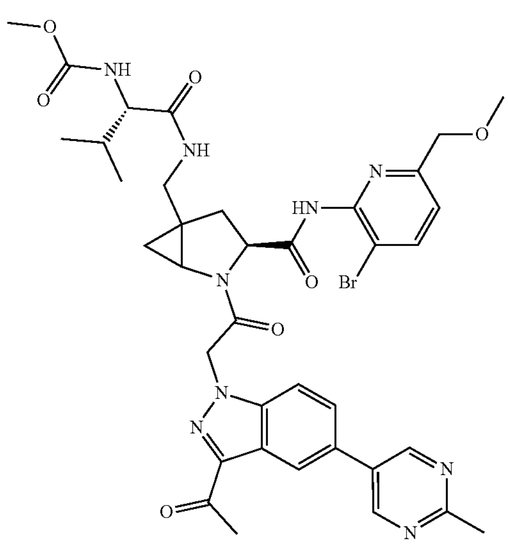 | methyl ((2S)-1-((((3S)-2-(2-(3-acetyl-5-(2-methylpyrimidin-5-yl)-1H-indazol-1-yl)acetyl)-3-((3-bromo-6-(methoxymethyl)pyridin-2-yl)carbamoyl)-2-azabicyclo[3.1.0]hexan-5-yl)methyl)amino)-3-methyl-1-oxobutan-2-yl)carbamate | * | 3.20 (B) | 804 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 49 | 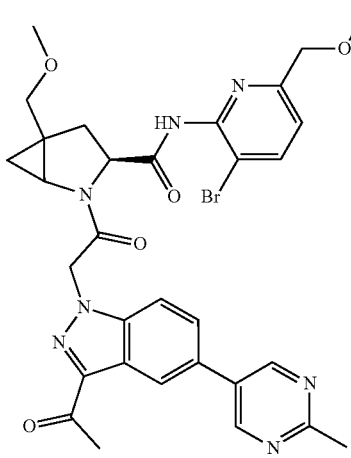 | (3S)-2-(2-(3-acetyl-5-(2-methylpyrimidin-5-yl)-1H-indazol-1-yl)acetyl)-N-(3-bromo-6-(methoxymethyl)pyridin-2-yl)-5-(methoxymethyl)-2-azabicyclo[3.1.0]hexane-3-carboxamide | *** | 3.07 (B) | 662 |
| 50 | 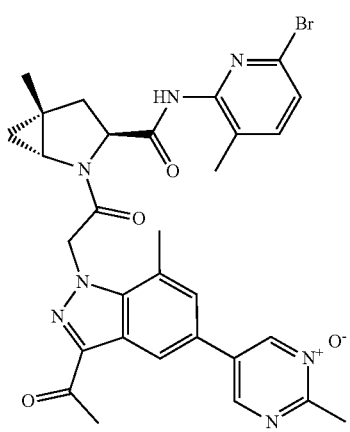 | 5-(3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-7-methyl-1H-indazol-5-yl)-2-methylpyrimidine-1-oxide | *** | 3.15 (B) | 632 |
| 51 | 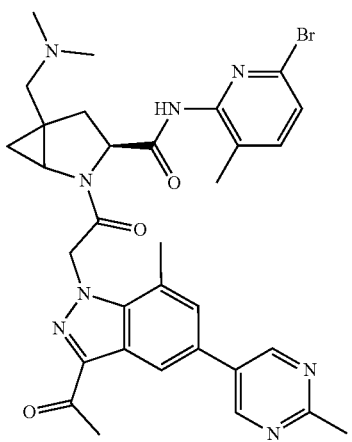 [SMILES: CC(=O)c1nn(CC(=O)N2C3CC3(CN(C)C)C[C@H]2C(=O)Nc2nc(Br)ccc2C)c2c(C)cc(-c3cnc(C)nc3)cc12] | (3S)-2-(2-(3-acetyl-7-methyl-5-(2-methylpyrimidin-5-yl)-1H-indazol-1-yl)acetyl)-N-(6-bromo-3-methylpyridin-2-yl)-5-((dimethylamino)methyl)-2-azabicyclo[3.1.0]hexane-3-carboxamide | | 2.08 (B) | 659 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 52 | 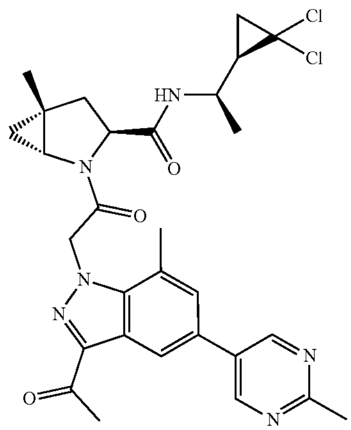 [SMILES: CC(=O)c1nn(CC(=O)N2[C@H](C(=O)N[C@H](C)[C@H]3CC3(Cl)Cl)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-((R)-1-((R)-2,2-dichlorocyclopropyl)ethyl)-5-methyl-2-azabicyclo[3.1.0]hexane-3-carboxamide | *** | 11.25 (D) | 584 |
| 53 | 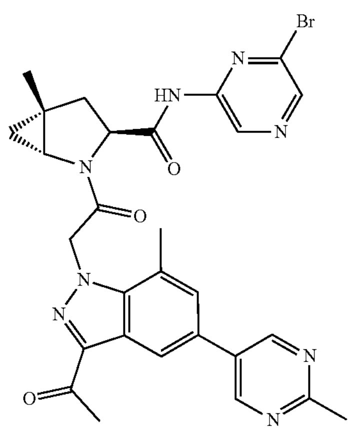 [SMILES: CC(=O)c1nn(CC(=O)N2[C@H](C(=O)Nc3cncc(Br)n3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromopyrazin-2-yl)-5-methyl-2-azabicyclo[3.1.0]hexane-3-carboxamide | | 11.10 (C) | 604 |
| 54 | 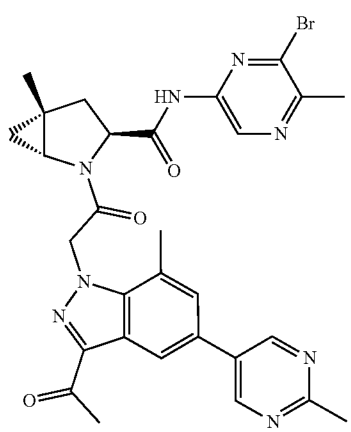 [SMILES: CC(=O)c1nn(CC(=O)N2[C@H](C(=O)Nc3cnc(C)c(Br)n3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-5-methylpyrazin-2-yl)-5-methyl-2-azabicyclo[3.1.0]hexane-3-carboxamide | *** | 14.12 (C) | 615 (M − 2) |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 55 | 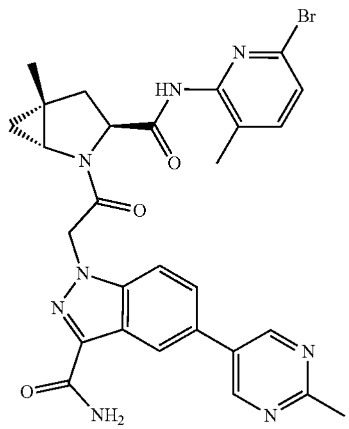 [SMILES: Cc1ncc(-c2ccc3c(c2)c(C(N)=O)nn3CC(=O)N2[C@H](C(=O)Nc3nc(Br)ccc3C)C[C@@]3(C)C[C@@H]23)cn1] | 1-(2-((1R,3S,5R)-3-((6-bromo-3-methylpyridin-2-yl)carbamoyl)-5-methyl-2-azabicyclo[3.1.0]hexan-2-yl)-2-oxoethyl)-5-(2-methylpyrimidin-5-yl)-1H-indazole-3-carboxamide | *** | 8.30 (C) | 601 (M − 2) |
| 56 | 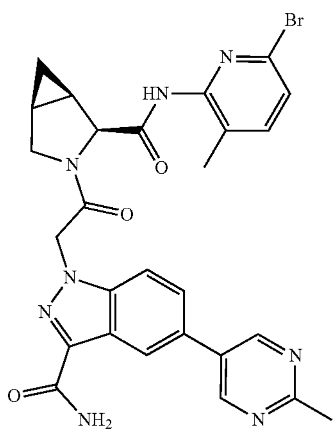 [SMILES: Cc1ncc(-c2ccc3c(c2)c(C(N)=O)nn3CC(=O)N2C[C@H]3C[C@H]3[C@H]2C(=O)Nc2nc(Br)ccc2C)cn1] | 1-(2-((1R,2S,5S)-2-((6-bromo-3-methylpyridin-2-yl)carbamoyl)-3-azabicyclo[3.1.0]hexan-3-yl)-2-oxoethyl)-5-(2-methylpyrimidin-5-yl)-1H-indazole-3-carboxamide | *** | 8.30 (D) | 591 (M + 2) |
| 57 | 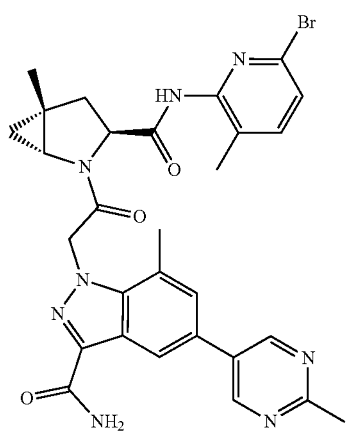 [SMILES: Cc1ncc(-c2cc(C)c3c(c2)c(C(N)=O)nn3CC(=O)N2[C@H](C(=O)Nc3nc(Br)ccc3C)C[C@@]3(C)C[C@@H]23)cn1] | 1-(2-((1R,3S,5R)-3-((6-bromo-3-methylpyridin-2-yl)carbamoyl)-5-methyl-2-azabicyclo[3.1.0]hexan-2-yl)-2-oxoethyl)-7-methyl-5-(2-methylpyrimidin-5-yl)-1H-indazole-3-carboxamide | *** | 8.84 (C) | 619 (M + 2) |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 58 | 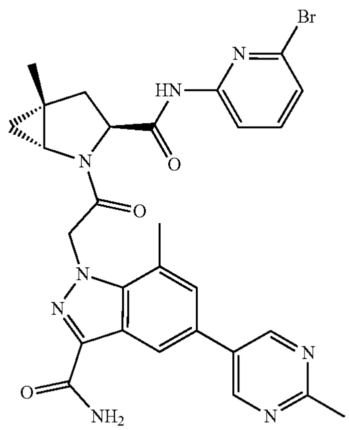 | 1-(2-((1R,3S,5R)-3-((6-bromopyridin-2-yl)carbamoyl)-5-methyl-2-azabicyclo[3.1.0]hexan-2-yl)-2-oxoethyl)-7-methyl-5-(2-methylpyrimidin-5-yl)-1H-indazole-3-carboxamide | *** | 12.45 (C) | 605 (M + 2) |
| 59 | 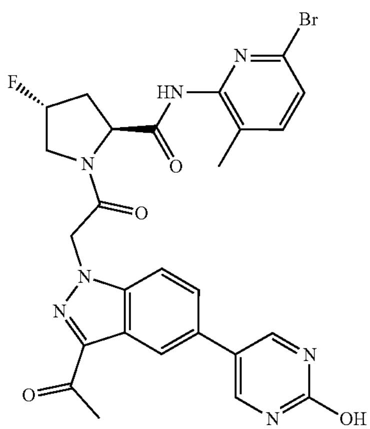 [SMILES: CC(=O)c1nn(CC(=O)N2C[C@H](F)C[C@H]2C(=O)Nc2nc(Br)ccc2C)c2ccc(-c3cnc(O)nc3)cc12] | (2S,4R)-1-(2-(3-acetyl-5-(2-hydroxypyrimidin-5-yl)-1H-indazol-1-yl)acetyl)-N-(6-bromo-3-methylpyridin-2-yl)-4-fluoropyrrolidine-2-carboxamide | | 7.92 (D) | 597 |
| 60 | 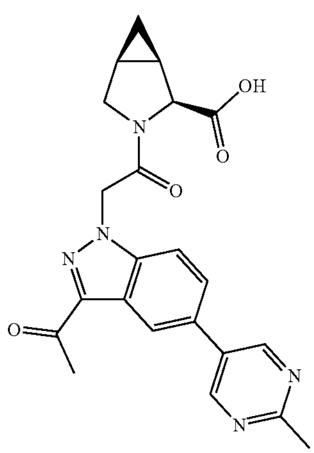 [SMILES: CC(=O)c1nn(CC(=O)N2C[C@H]3C[C@H]3[C@H]2C(=O)O)c2ccc(-c3cnc(C)nc3)cc12] | (1R,2S,5S)-3-(2-(3-acetyl-5-(2-methylpyrimidin-5-yl)-1H-indazol-1-yl)acetyl)-3-azabicyclo[3.1.0]hexane-2-carboxylic acid | | 1.10 (A) | 420 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 61 | 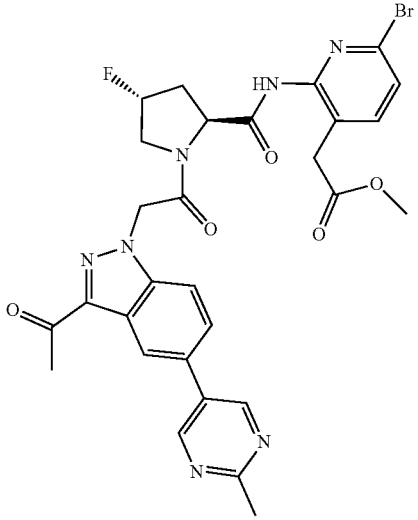 [SMILES: COC(=O)Cc1ccc(Br)nc1NC(=O)[C@@H]1C[C@@H](F)CN1C(=O)Cn1nc(C(C)=O)c2cc(-c3cnc(C)nc3)ccc21] | methyl 2-(2-((2S,4R)-1-(2-(3-acetyl-5-(2-methylpyrimidin-5-yl)-1H-indazol-1-yl)acetyl)-4-fluoropyrrolidine-2-carboxamido)-6-bromopyridin-3-yl)acetate | *** | 1.50 (A) | 651 |
| 62 | 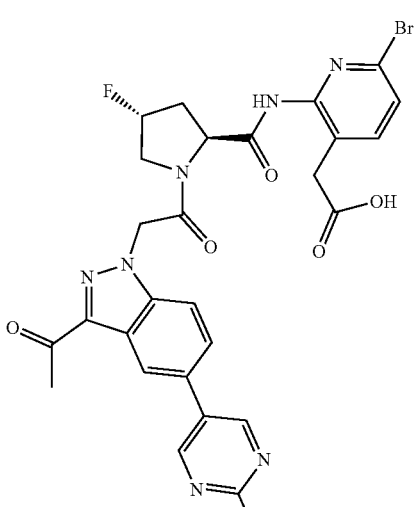 | 2-(2-((2S,4R)-1-(2-(3-acetyl-5-(2-methylpyrimidin-5-yl)-1H-indazol-1-yl)acetyl)-4-fluoropyrrolidine-2-carboxamido)-6-bromopyridin-3-yl)acetic acid | *** | 1.27 (A) | 638 |
| 63 | 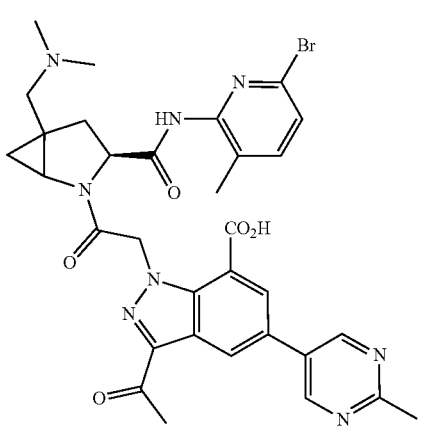 [SMILES: CC(=O)c1nn(CC(=O)N2C3CC3(CN(C)C)C[C@H]2C(=O)Nc2nc(Br)ccc2C)c2c(C(=O)O)cc(-c3cnc(C)nc3)cc12] | 3-acetyl-1-(2-((3S)-3-((6-bromo-3-methylpyridin-2-yl)carbamoyl)-5-((dimethylamino)methyl)-2-azabicyclo[3.1.0]hexan-2-yl)-2-oxoethyl)-5-(2-methylpyrimidin-5-yl)-1H-indazole-7-carboxylic acid | | 2.07 (B) | 689 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 64 | 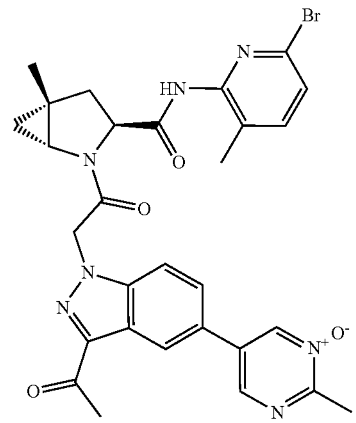 | 5-(3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-indazol-5-yl)-2-methylpyrimidine-1-oxide | *** | 3.06 (B) | 618 |
| 65 | 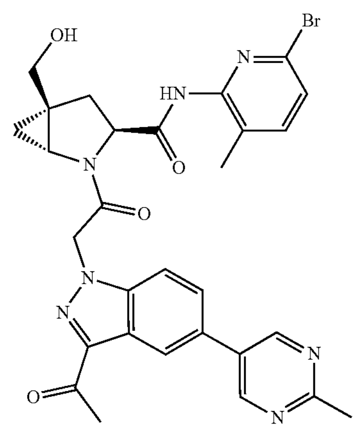 [SMILES: CC(=O)c1nn(CC(=O)N2[C@H](C(=O)Nc3nc(Br)ccc3C)C[C@@]3(CO)C[C@@H]23)c2ccc(-c3cnc(C)nc3)cc12] | (1R,3S,5S)-2-(2-(3-acetyl-5-(2-methylpyrimidin-5-yl)-1H-indazol-1-yl)acetyl)-N-(6-bromo-3-methylpyridin-2-yl)-5-(hydroxymethyl)-2-azabicyclo[3.1.0]hexane-3-carboxamide | *** | 2.46 (B) | 618 |
| 66 | 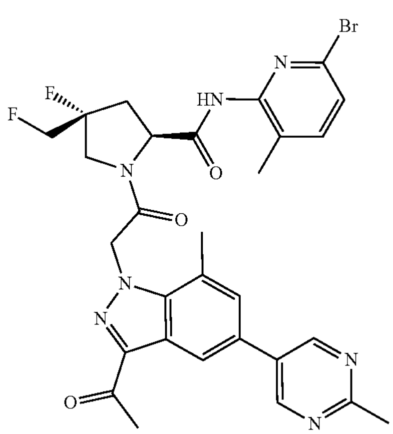 [SMILES: CC(=O)c1nn(CC(=O)N2C[C@@](F)(CF)C[C@H]2C(=O)Nc2nc(Br)ccc2C)c2c(C)cc(-c3cnc(C)nc3)cc12] | (2S,4R)-1-(2-(3-acetyl-7-methyl-5-(2-methylpyrimidin-5-yl)-1H-indazol-1-yl)acetyl)-N-(6-bromo-3-methylpyridin-2-yl)-4-fluoro-4-(fluoromethyl)-pyrrolidine-2-carboxamide | *** | 2.88 (B) | 640 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 67 | 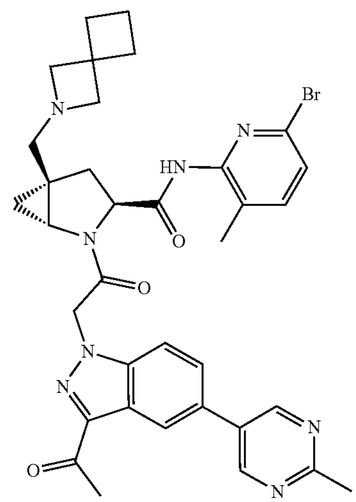 [SMILES: CC(=O)c1nn(CC(=O)N2[C@H](C(=O)Nc3nc(Br)ccc3C)C[C@@]3(CN4CC5(CCC5)C4)C[C@@H]23)c2ccc(-c3cnc(C)nc3)cc12] | (1R,3S,5R)-5-(2-azaspiro[3.3]heptan-2-ylmethyl)-2-(2-(3-acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide | *** | 2.78 (B) | 697 |
| 68 | 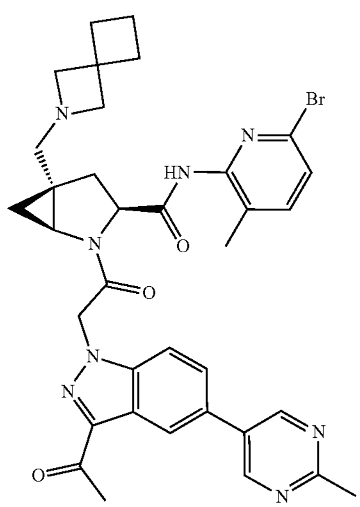 [SMILES: CC(=O)c1nn(CC(=O)N2[C@H]3C[C@@]3(CN3CC4(CCC4)C3)C[C@H]2C(=O)Nc2nc(Br)ccc2C)c2ccc(-c3cnc(C)nc3)cc12] | (1S,3S,5S)-5-(2-azaspiro[3.3]heptan-2-ylmethyl)-2-(2-(3-acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide | *** | 2.71 (B) | 697 |
| 69 | 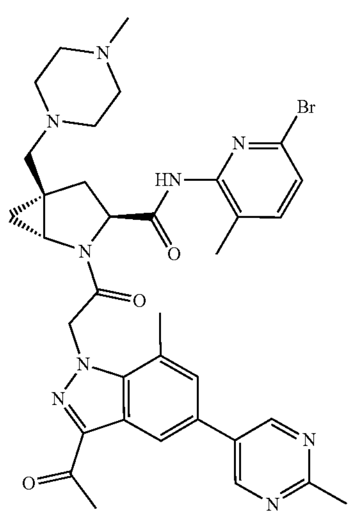 [SMILES: CC(=O)c1nn(CC(=O)N2[C@H](C(=O)Nc3nc(Br)ccc3C)C[C@@]3(CN4CCN(C)CC4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-((4-methylpiperazin-1-yl)methyl)-2-azabicyclo[3.1.0]hexane-3-carboxamide | *** | 2.56 (B) | 714 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 70 | 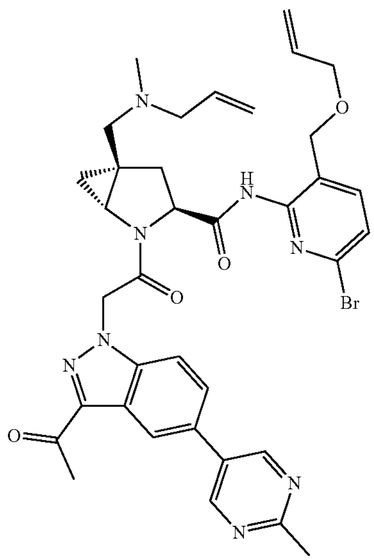 [SMILES: C=CCOCc1ccc(Br)nc1NC(=O)[C@@H]1C[C@@]2(CN(C)CC=C)C[C@H]2N1C(=O)Cn1nc(C(C)=O)c2cc(-c3cnc(C)nc3)ccc21] | (1R,3S,5R)-2-(2-(3-acetyl-5-(2-methylpyrimidin-5-yl)-1H-indazol-1-yl)acetyl)-5-((allyl(methyl)-amino)methyl)-N-(3-((allyloxy)-methyl)-6-bromopyridin-2-yl)-2-azabicyclo[3.1.0]hexane-3-carboxamide | *** | 1.35 (A) | 727 |
| 71 | 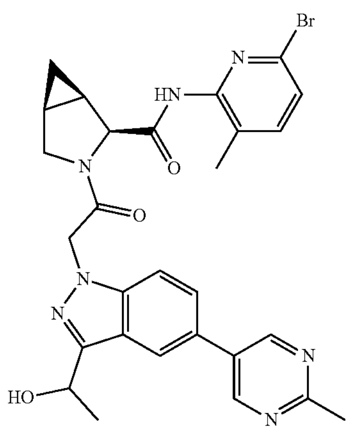 [SMILES: Cc1ncc(-c2ccc3c(c2)c(C(C)O)nn3CC(=O)N2C[C@H]3C[C@H]3[C@H]2C(=O)Nc2nc(Br)ccc2C)cn1] | (1R,2S,5S)-N-(6-bromo-3-methylpyridin-2-yl)-3-(2-(3-(1-hydroxyethyl)-5-(2-methylpyrimidin-5-yl)-1H-indazol-1-yl)acetyl)-3-azabicyclo[3.1.0]hexane-2-carboxamide | ** | 1.33 (A) | 592 |
| 72 | 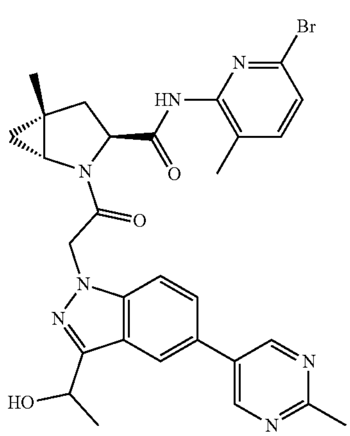 | (1R,3S,5R)-N-(6-bromo-3-methylpyridin-2-yl)-2-(2-(3-(1-hydroxyethyl)-5-(2-methylpyrimidin-5-yl)-1H-indazol-1-yl)acetyl)-5-methyl-2-azabicyclo[3.1.0]hexane-3-carboxamide | ** | 1.52 (A) | 604 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 73 | 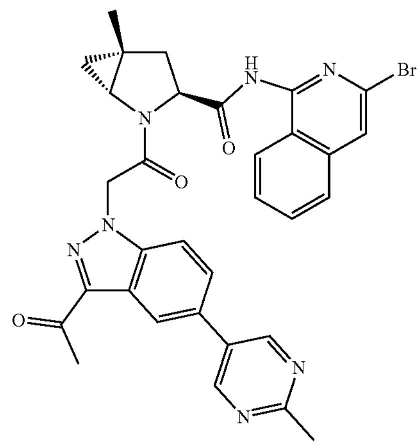 [SMILES: CC(=O)c1nn(CC(=O)N2[C@H](C(=O)Nc3nc(Br)cc4ccccc34)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(3-bromoisoquinolin-1-yl)-5-methyl-2-azabicyclo[3.1.0]hexane-3-carboxamide | *** | 2.04 (A) | 638 |
| 74 | 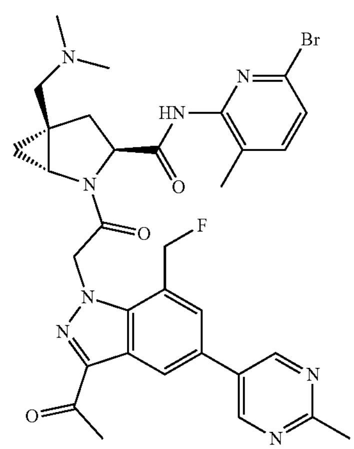 [SMILES: CC(=O)c1nn(CC(=O)N2[C@H](C(=O)Nc3nc(Br)ccc3C)C[C@@]3(CN(C)C)C[C@@H]23)c2c(CF)cc(-c3cnc(C)nc3)cc12] | (1R,3S,5R)-2-(2-(3-acetyl-7-(fluoromethyl)-5-(2-methylpyrimidin-5-yl)-1H-indazol-1-yl)acetyl)-N-(6-bromo-3-methylpyridin-2-yl)-5-((dimethylamino)-methyl)-2-azabicyclo[3.1.0]hexane-3-carboxamide | *** | 2.19 (B) | 677 |
| 75 | 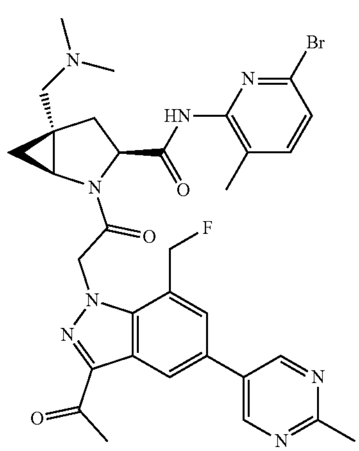 [SMILES: CC(=O)c1nn(CC(=O)N2[C@H]3C[C@@]3(CN(C)C)C[C@H]2C(=O)Nc2nc(Br)ccc2C)c2c(CF)cc(-c3cnc(C)nc3)cc12] | (1S,3S,5S)-2-(2-(3-acetyl-7-(fluoromethyl)-5-(2-methylpyrimidin-5-yl)-1H-indazol-1-yl)acetyl)-N-(6-bromo-3-methylpyridin-2-yl)-5-((dimethylamino)-methyl)-2-azabicyclo[3.1.0]hexane-3-carboxamide | *** | 2.28 (B) | 677 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 76 | 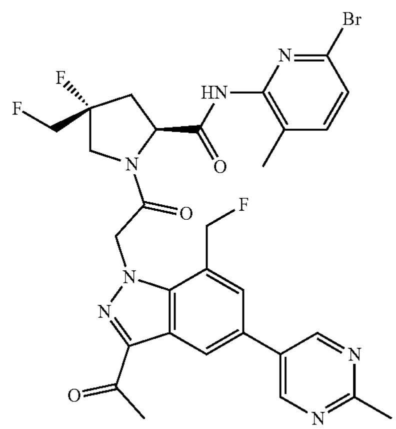 [SMILES: CC(=O)c1nn(CC(=O)N2C[C@@](F)(CF)C[C@H]2C(=O)Nc2nc(Br)ccc2C)c2c(CF)cc(-c3cnc(C)nc3)cc12] | (2S,4R)-1-(2-(3-acetyl-7-(fluoromethyl)-5-(2-methylpyrimidin-5-yl)-1H-indazol-1-yl)acetyl)-N-(6-bromo-3-methylpyridin-2-yl)-4-fluoro-4-(fluoromethyl)-pyrrolidine-2-carboxamide | *** | 3.22 (B) | 658 |
| 77 | 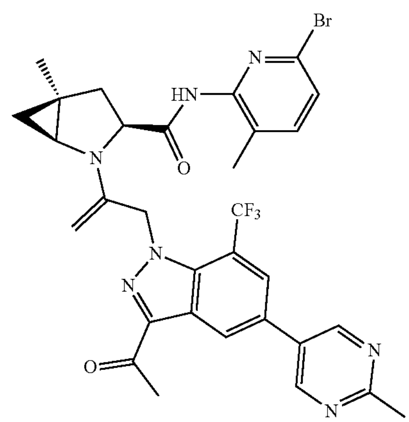 [SMILES: C=C(Cn1nc(C(C)=O)c2cc(-c3cnc(C)nc3)cc(C(F)(F)F)c21)N1[C@H]2C[C@@]2(C)C[C@H]1C(=O)Nc1nc(Br)ccc1C] | (1S,3S,5S)-2-(2-(3-acetyl-5-(2-methylpyrimidin-5-yl)-7-(trifluoromethyl)-1H-indazol-1-yl)acetyl)-N-(6-bromo-3-methylpyridin-2-yl)-5-methyl-2-azabicyclo[3.1.0]hexane-3-carboxamide | * | 3.66 (B) | 670 |
| 78 | 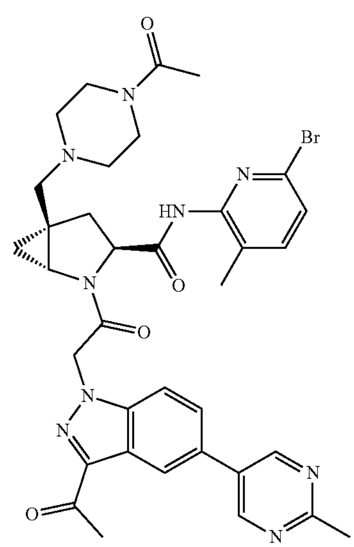 [SMILES: CC(=O)c1nn(CC(=O)N2[C@H](C(=O)Nc3nc(Br)ccc3C)C[C@@]3(CN4CCN(C(C)=O)CC4)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-5-((4-acetylpiperazin-1-yl)methyl)-N-(6-bromo-3-methylpyridin-2-yl)-2-azabicyclo[3.1.0]hexane-3-carboxamide | *** | 3.69 (B) | 728 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 79 | 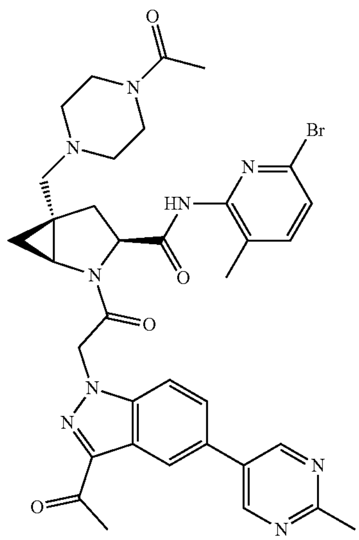 [SMILES: CC(=O)c1nn(CC(=O)N2[C@H]3C[C@@]3(CN3CCN(C(C)=O)CC3)C[C@H]2C(=O)Nc2nc(Br)ccc2C)c2ccc(-c3cnc(C)nc3)cc12] | (1S,3S,5S)-2-(2-(3-acetyl-5-(2-methylpyrimidin-5-yl)-1H-indazol-1-yl)acetyl)-5-((4-acetylpiperazin-1-yl)methyl)-N-(6-bromo-3-methylpyridin-2-yl)-2-azabicyclo[3.1.0]hexane-3-carboxamide | ** | 3.74 (B) | 728 |
| 80 | 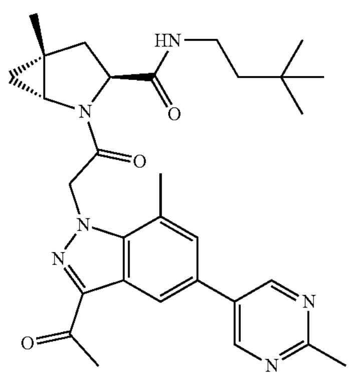 [SMILES: CC(=O)c1nn(CC(=O)N2[C@H](C(=O)NCCC(C)(C)C)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(3,3-dimethylbutyl)-5-methyl-2-azabicyclo[3.1.0]hexane-3-carboxamide | *** | 11.05 (D) | 531 |
| 81 | 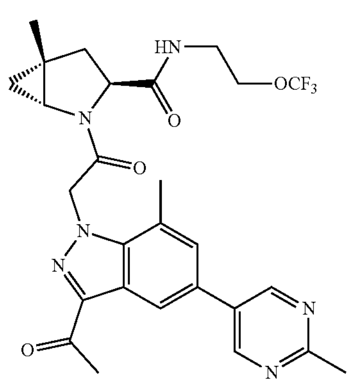 [SMILES: CC(=O)c1nn(CC(=O)N2[C@H](C(=O)NCCOC(F)(F)F)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-methyl-N-(2-(trifluoromethoxy)ethyl)-2-azabicyclo[3.1.0]hexane-3-carboxamide | *** | 10.79 (D) | 559 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 82 | 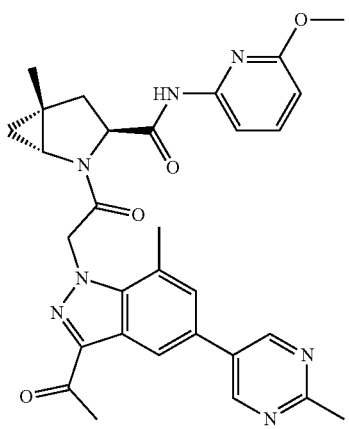 [SMILES: COc1cccc(NC(=O)[C@@H]2C[C@@]3(C)C[C@H]3N2C(=O)Cn2nc(C(C)=O)c3cc(-c4cnc(C)nc4)cc(C)c32)n1] | (1R,3S,5R)-2-(2-(3-acetyl-7-methyl-5-(2-methylpyrimidin-5-yl)-1H-indazol-1-yl)acetyl)-N-(6-methoxypyridin-2-yl)-5-methyl-2-azabicyclo[3.1.0]hexane-3-carboxamide | *** | 11.79 (D) | 554 |
| 83 | 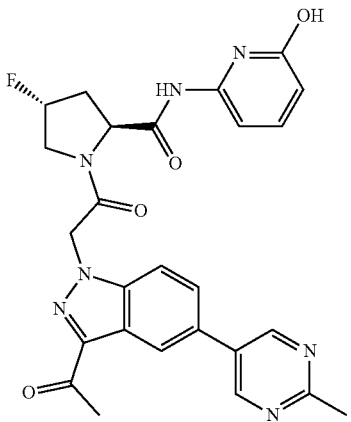 [SMILES: CC(=O)c1nn(CC(=O)N2C[C@H](F)C[C@H]2C(=O)Nc2cccc(O)n2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(6-hydroxypyridin-2-yl)pyrrolidine-2-carboxamide | ** | 6.71 (C) | 518 |
| 84 | 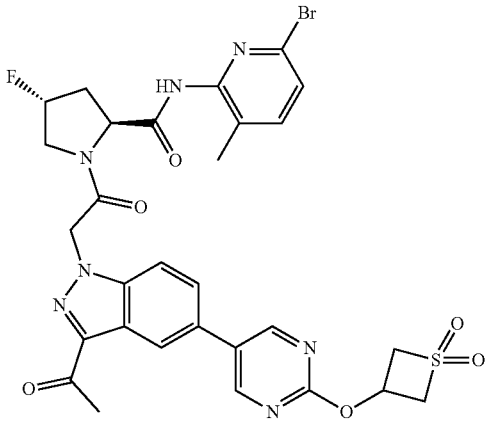 [SMILES: CC(=O)c1nn(CC(=O)N2C[C@H](F)C[C@H]2C(=O)Nc2nc(Br)ccc2C)c2ccc(-c3cnc(OC4CS(=O)(=O)C4)nc3)cc12] | (2S,4R)-1-(2-(3-acetyl-5-(2-((1,1-dioxidothietan-3-yl)oxy)pyrimidin-5-yl)-1H-indazol-1-yl)acetyl)-N-(6-bromo-3-methylpyridin-2-yl)-4-fluoropyrrolidine-2-carboxamide | *** | 8.16 (C) | 698 (M − 2) |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 86 | 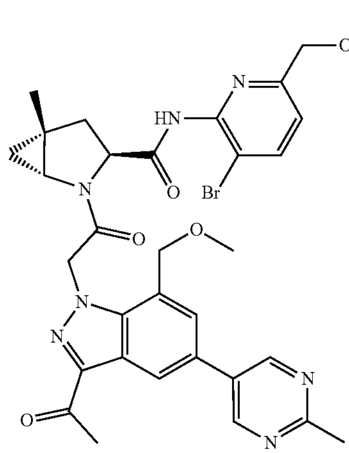 | (1R,3S,5R)-2-(2-(3-acetyl-7-(methoxymethyl)-5-(2-methylpyrimidin-5-yl)-1H-indazol-1-yl)acetyl)-N-(3-bromo-6-(methoxymethyl)pyridin-2-yl)-5-methyl-2-azabicyclo[3.1.0]hexane-3-carboxamide | * | 3.24 (B) | 676 |
| 88 | 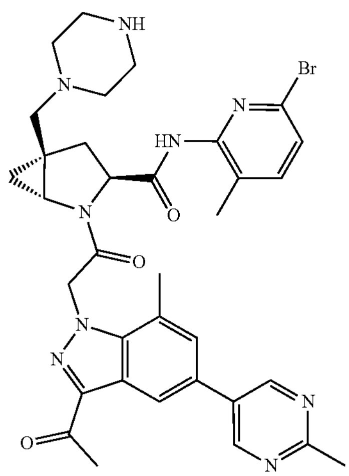 [SMILES: CC(=O)c1nn(CC(=O)N2[C@H](C(=O)Nc3nc(Br)ccc3C)C[C@@]3(CN4CCNCC4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-(piperazin-1-ylmethyl)-2-azabicyclo[3.1.0]hexane-3-carboxamide | *** | 2.03 (B) | 700 |
| 89 | 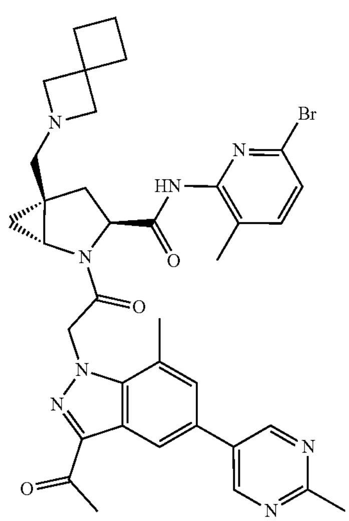 [SMILES: CC(=O)c1nn(CC(=O)N2[C@H](C(=O)Nc3nc(Br)ccc3C)C[C@@]3(CN4CC5(CCC5)C4)C[C@@H]23)c2c(C)cc(-c3cnc(C)nc3)cc12] | (1R,3S,5R)-5-(2-azaspiro[3.3]heptan-2-ylmethyl)-2-(2-(3-acetyl-7-methyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide | *** | 2.55 (B) | 711 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 90 | 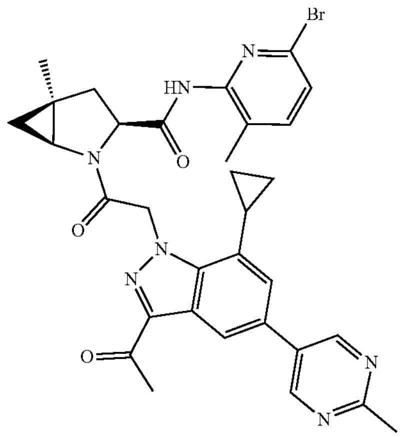 [SMILES: CC(=O)c1nn(CC(=O)N2[C@H]3C[C@@]3(C)C[C@H]2C(=O)Nc2nc(Br)ccc2C)c2c(C3CC3)cc(-c3cnc(C)nc3)cc12] | (1S,3S,5S)-2-(2-(3-acetyl-7-cyclopropyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 3.81 (B) | 642 |
| 91 | 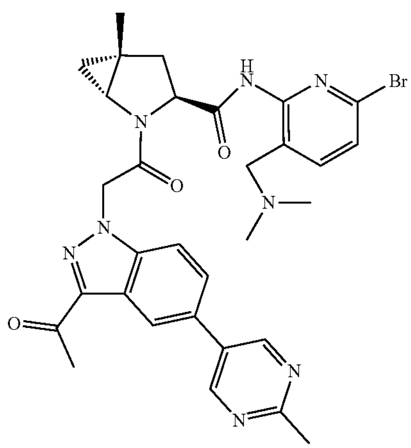 [SMILES: CC(=O)c1nn(CC(=O)N2[C@H](C(=O)Nc3nc(Br)ccc3CN(C)C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-((dimethylamino)methyl)pyridin-2-yl)-5-methyl-2-azabicyclo[3.1.0]hexane-3-carboxamide | *** | 1.15 (A) | 645 |
| 92 | 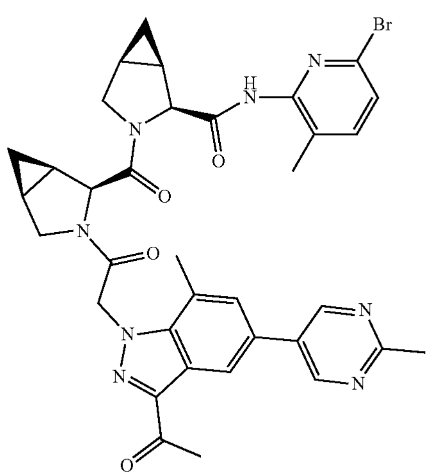 [SMILES: CC(=O)c1nn(CC(=O)N2C[C@H]3C[C@H]3[C@H]2C(=O)N2C[C@H]3C[C@H]3[C@H]2C(=O)Nc2nc(Br)ccc2C)c2c(C)cc(-c3cnc(C)nc3)cc12] | (1R,2S,5S)-3-((1R,2S,5S)-3-(2-(3-acetyl-7-methyl-5-(2-methylpyrimidin-5-yl)-1H-indazol-1-yl)acetyl)-3-azabicyclo[3.1.0]hexane-2-carbonyl)-N-(6-bromo-3-methylpyridin-2-yl)-3-azabicyclo[3.1.0]hexane-2-carboxamide | ** | 1.77 (A) | 713 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 93 | 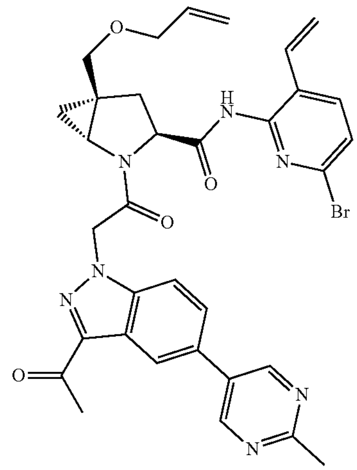 [SMILES: C=CCOC[C@@]12C[C@@H](C(=O)Nc3nc(Br)ccc3C=C)N(C(=O)Cn3nc(C(C)=O)c4cc(-c5cnc(C)nc5)ccc43)[C@@H]1C2] | (1R,3S,5S)-2-(2-(3-acetyl-5-(2-methylpyrimidin-5-yl)-1H-indazol-1-yl)acetyl)-5-((allyloxy)-methyl)-N-(6-bromo-3-vinylpyridin-2-yl)-2-azabicyclo[3.1.0]hexane-3-carboxamide | *** | 2.01 (A) | 670 |
| 94 | 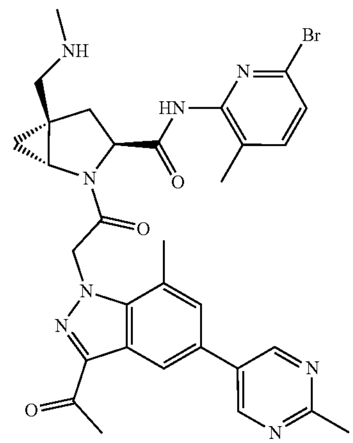 [SMILES: CNC[C@@]12C[C@@H](C(=O)Nc3nc(Br)ccc3C)N(C(=O)Cn3nc(C(C)=O)c4cc(-c5cnc(C)nc5)cc(C)c43)[C@@H]1C2] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-((methylamino)methyl)-2-azabicyclo[3.1.0]hexane-3-carboxamide | *** | 3.06 (B) | 645 |
| 95 | 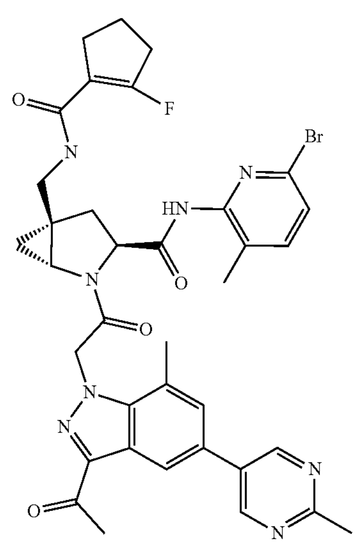 [SMILES: CC(=O)c1nn(CC(=O)N2[C@H](C(=O)Nc3nc(Br)ccc3C)C[C@@]3(CNC(=O)C4=C(F)CCC4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-((2-fluorocyclopent-1-ene-1-carboxamido)-methyl)-2-azabicyclo[3.1.0]hexane-3-carboxamide | *** | 3.47 (B) | 743 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 96 | 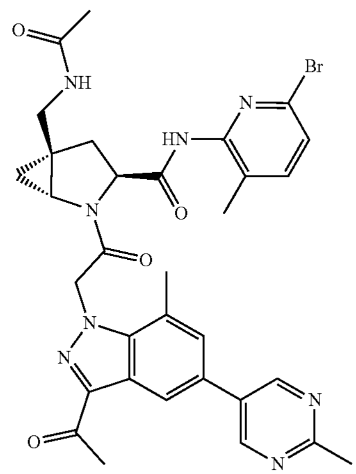 [SMILES: CC(=O)NC[C@@]12C[C@@H](C(=O)Nc3nc(Br)ccc3C)N(C(=O)Cn3nc(C(C)=O)c4cc(-c5cnc(C)nc5)cc(C)c43)[C@@H]1C2] | (1R,3S,5R)-5-(acetamidomethyl)-2-(2-(3-acetyl-7-methyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide | *** | 2.96 (B) | 673 |
| 97 | 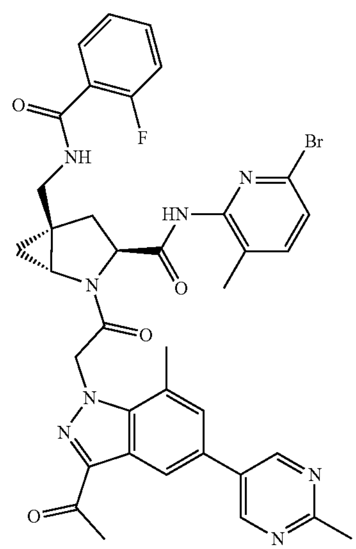 [SMILES: CC(=O)c1nn(CC(=O)N2[C@H](C(=O)Nc3nc(Br)ccc3C)C[C@@]3(CNC(=O)c4ccccc4F)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-((2-fluorobenzamido)-methyl)-2-azabicyclo[3.1.0]hexane-3-carboxamide | *** | 3.52 (B) | 753 |
| 98 | 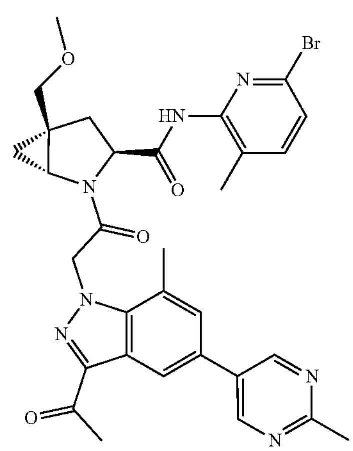 [SMILES: COC[C@@]12C[C@@H](C(=O)Nc3nc(Br)ccc3C)N(C(=O)Cn3nc(C(C)=O)c4cc(-c5cnc(C)nc5)cc(C)c43)[C@@H]1C2] | (1R,3S,5S)-2-(2-(3-acetyl-7-methyl-5-(2-methylpyrimidin-5-yl)-1H-indazol-1-yl)acetyl)-N-(6-bromo-3-methylpyridin-2-yl)-5-(methoxymethyl)-2-azabicyclo[3.1.0]hexane-3-carboxamide | *** | 3.26 (B) | 646 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 99 | 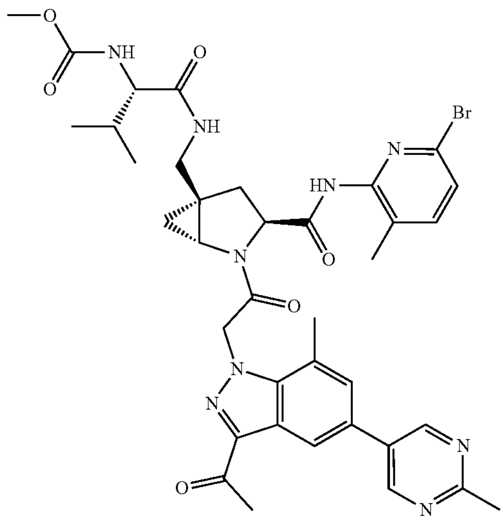 | methyl ((S)-1-(((((1R,3S,5R)-2-(2-(3-acetyl-7-methyl-5-(2-methylpyrimidin-5-yl)-1H-indazol-1-yl)acetyl)-3-((6-bromo-3-methylpyridin-2-yl)carbamoyl)-2-azabicyclo[3.1.0]hexan-5-yl)methyl)amino)-3-methyl-1-oxobutan-2-yl)carbamate | *** | 3.36 (B) | 788 |
| 100 | 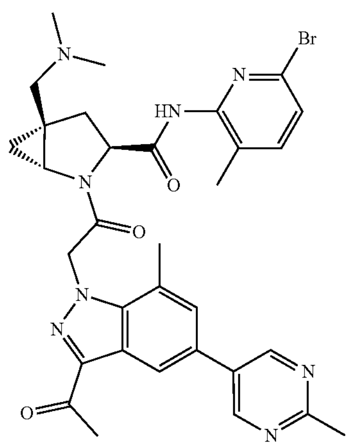 | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-((dimethylamino)-methyl)-2-azabicyclo[3.1.0]hexane-3-carboxamide | *** | 2.55 (B) | 659 |
| 101 | 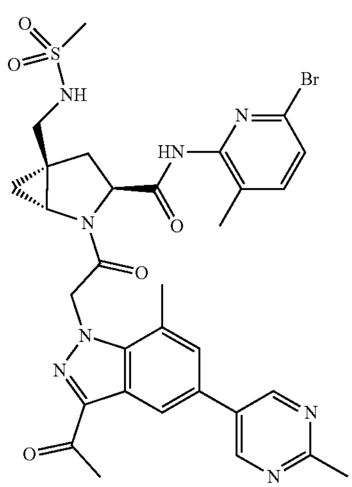 [SMILES: CC(=O)c1nn(CC(=O)N2[C@H](C(=O)Nc3nc(Br)ccc3C)C[C@@]3(CNS(C)(=O)=O)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-(methylsulfon-amidomethyl)-2-azabicyclo[3.1.0]hexane-3-carboxamide | *** | 2.47 (B) | 709 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 102 | 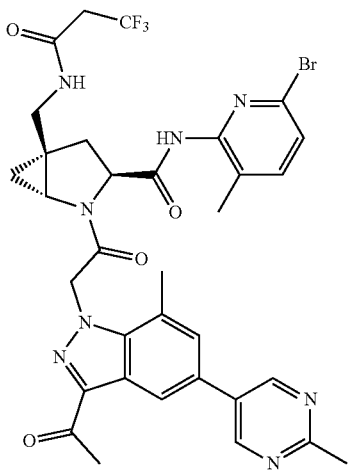 [SMILES: CC(=O)c1nn(CC(=O)N2[C@H](C(=O)Nc3nc(Br)ccc3C)C[C@@]3(CNC(=O)CC(F)(F)F)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-((3,3,3-trifluoropropanamido)-methyl)-2-azabicyclo[3.1.0]hexane-3-carboxamide | *** | 3.45 (B) | 741 |
| 103 | 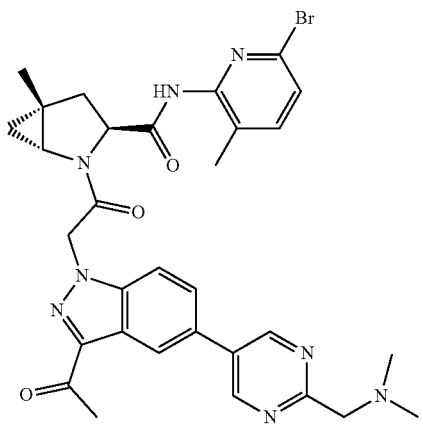 [SMILES: CC(=O)c1nn(CC(=O)N2[C@H](C(=O)Nc3nc(Br)ccc3C)C[C@@]3(C)C[C@@H]23)c2ccc(-c3cnc(CN(C)C)nc3)cc12] | (1R,3S,5R)-2-(2-(3-acetyl-5-(2-((dimethylamino)-methyl)pyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 1.28 (A) | 645 |
| 104 | 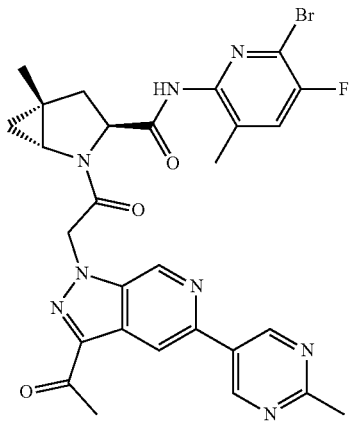 [SMILES: CC(=O)c1nn(CC(=O)N2[C@H](C(=O)Nc3nc(Br)c(F)cc3C)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-5-fluoro-3-methylpyridin-2-yl)-5-methyl-2-azabicyclo[3.1.0]hexane-3-carboxamide | *** | 1.76 (A) | 621 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 105 | 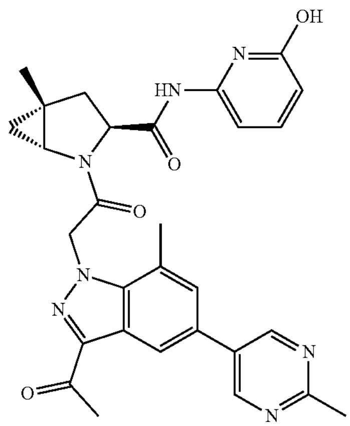 [SMILES: CC(=O)c1nn(CC(=O)N2[C@H](C(=O)Nc3cccc(O)n3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-hydroxypyridin-2-yl)-5-methyl-2-azabicyclo[3.1.0]hexane-3-carboxamide | *** | 8.61 (D) | 540 |
| 106 | 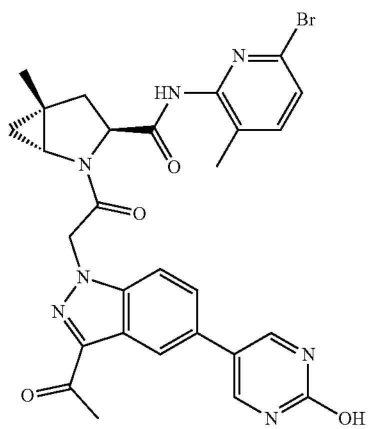 [SMILES: CC(=O)c1nn(CC(=O)N2[C@H](C(=O)Nc3nc(Br)ccc3C)C[C@@]3(C)C[C@@H]23)c2ccc(-c3cnc(O)nc3)cc12] | (1R,3S,5R)-2-(2-(3-acetyl-5-(2-hydroxypyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 8.16 (C) | 603 (M − 1) |
| 107 | 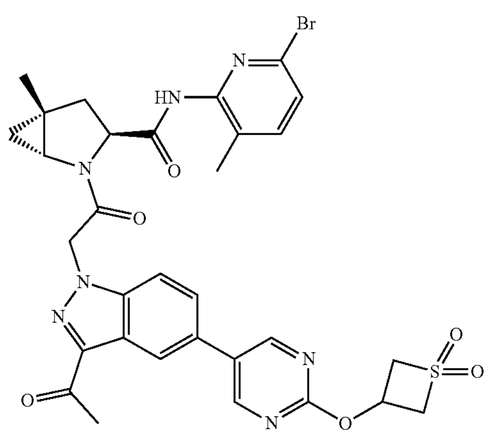 [SMILES: CC(=O)c1nn(CC(=O)N2[C@H](C(=O)Nc3nc(Br)ccc3C)C[C@@]3(C)C[C@@H]23)c2ccc(-c3cnc(OC4CS(=O)(=O)C4)nc3)cc12] | (1R,3S,5R)-2-(2-(3-acetyl-5-(2-((1,1-dioxidothietan-3-yl)oxy)pyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 9.30 (C) | 706 (M − 2) |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 108 | 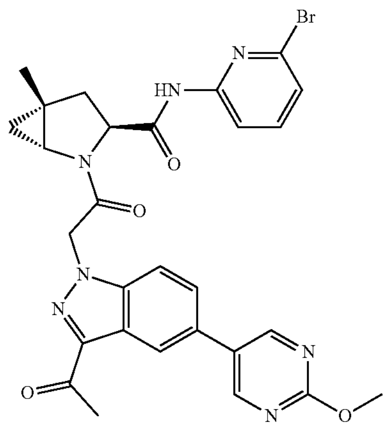 [SMILES: COc1ncc(-c2ccc3c(c2)c(C(C)=O)nn3CC(=O)N2[C@H](C(=O)Nc3cccc(Br)n3)C[C@@]3(C)C[C@@H]23)cn1] | (1R,3S,5R)-2-(2-(3-acetyl-5-(2-methoxypyrimidin-5-yl)-1H-indazol-1-yl)acetyl)-N-(6-bromopyridin-2-yl)-5-methyl-2-azabicyclo[3.1.0]hexane-3-carboxamide | *** | 12.23 (D) | 606 (M + 2) |
| 109 | 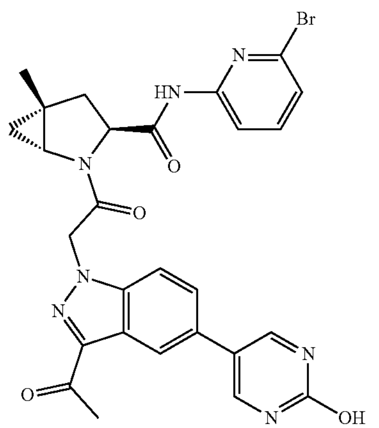 [SMILES: CC(=O)c1nn(CC(=O)N2[C@H](C(=O)Nc3cccc(Br)n3)C[C@@]3(C)C[C@@H]23)c2ccc(-c3cnc(O)nc3)cc12] | (1R,3S,5R)-2-(2-(3-acetyl-5-(2-hydroxypyrimidin-5-yl)-1H-indazol-1-yl)acetyl)-N-(6-bromopyridin-2-yl)-5-methyl-2-azabicyclo[3.1.0]hexane-3-carboxamide | *** | 9.82 (D) | 588 (M − 2) |
| 110 | 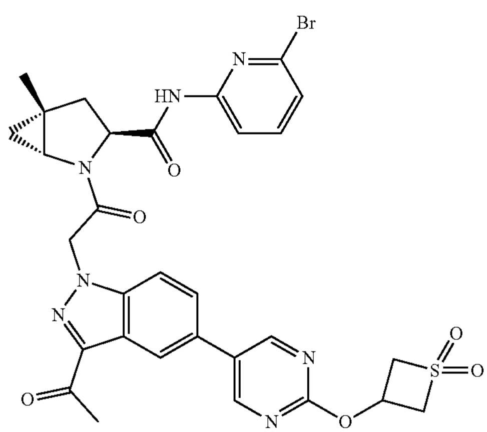 | (1R,3S,5R)-2-(2-(3-acetyl-5-(2-(((1,1-dioxidothietan-3-yl)oxy)pyrimidin-5-yl)-1H-indazol-1-yl)acetyl)-N-(6-bromopyridin-2-yl)-5-methyl-2-azabicyclo[3.1.0]hexane-3-carboxamide | *** | 10.49 (C) | 692 (M − 2) |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 111 | 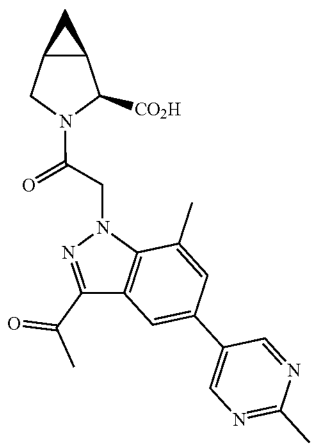 [SMILES: CC(=O)c1nn(CC(=O)N2C[C@H]3C[C@H]3[C@H]2C(=O)O)c2c(C)cc(-c3cnc(C)nc3)cc12] | (1R,2S,5S)-3-(2-(3-acetyl-7-methyl-5-(2-methylpyrimidin-5-yl)-1H-indazol-1-yl)acetyl)-3-azabicyclo[3.1.0]hexane-2-carboxylic acid | * | 1.23 (A) | 434 |
| 112 | 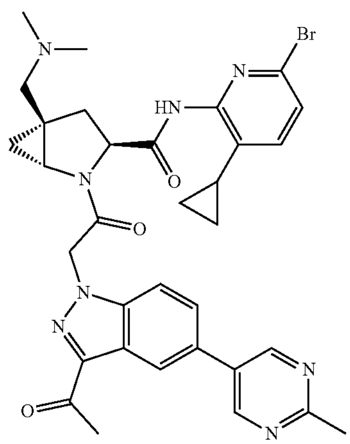 [SMILES: CC(=O)c1nn(CC(=O)N2[C@H](C(=O)Nc3nc(Br)ccc3C3CC3)C[C@@]3(CN(C)C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-cyclopropyl-pyridin-2-yl)-5-((dimethylamino)methyl)-2-azabicyclo[3.1.0]hexane-3-carboxamide hexane-3-carboxamide | *** | 2.37 (B) | 671 |
| 113 | 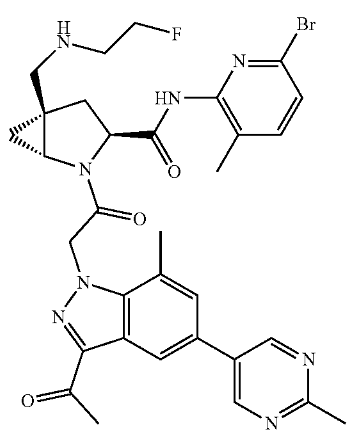 [SMILES: CC(=O)c1nn(CC(=O)N2[C@H](C(=O)Nc3nc(Br)ccc3C)C[C@@]3(CNCCF)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-(((2-fluoroethyl)amino)methyl)-2-azabicyclo[3.1.0]hexane-3-carboxamide | *** | 2.21 (B) | 677 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 114 | 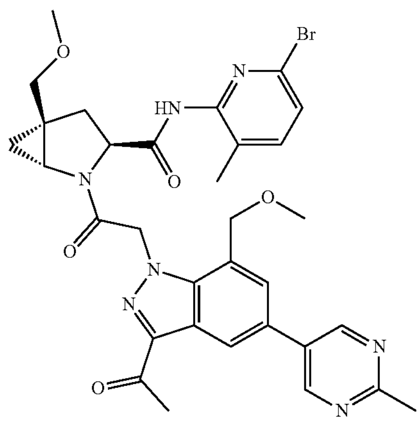 [SMILES: COCc1cc(-c2cnc(C)nc2)cc2c(C(C)=O)nn(CC(=O)N3[C@H](C(=O)Nc4nc(Br)ccc4C)C[C@@]4(COC)C[C@@H]34)c12] | (1R,3S,5S)-2-(2-(3-acetyl-7-(methoxymethyl)-5-(2-methylpyrimidin-5-yl)-1H-indazol-1-yl)acetyl)-N-(6-bromo-3-methylpyridin-2-yl)-5-(methoxymethyl)-2-azabicyclo[3.1.0]hexane-3-carboxamide | *** | 2.36 (B) | 676 |
| 115 | 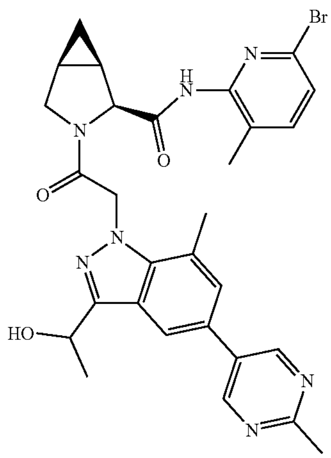 [SMILES: Cc1ncc(-c2cc(C)c3c(c2)c(C(C)O)nn3CC(=O)N2C[C@H]3C[C@H]3[C@H]2C(=O)Nc2nc(Br)ccc2C)cn1] | (1R,2S,5S)-N-(6-bromo-3-methylpyridin-2-yl)-3-(2-(3-(1-hydroxyethyl)-7-methyl-5-(2-methylpyrimidin-5-yl)-1H-indazol-1-yl)acetyl)-3-azabicyclo[3.1.0]hexane-2-carboxamide | ** | 1.47 (A) | 604 |
| 116 | 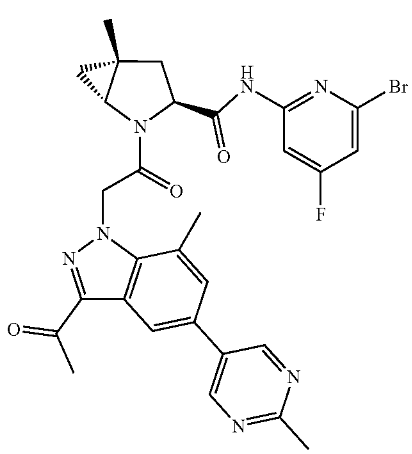 [SMILES: CC(=O)c1nn(CC(=O)N2[C@H](C(=O)Nc3cc(F)cc(Br)n3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-4-fluoropyridin-2-yl)-5-methyl-2-azabicyclo[3.1.0]hexane-3-carboxamide | *** | 2.31 (A) | 620 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 117 | 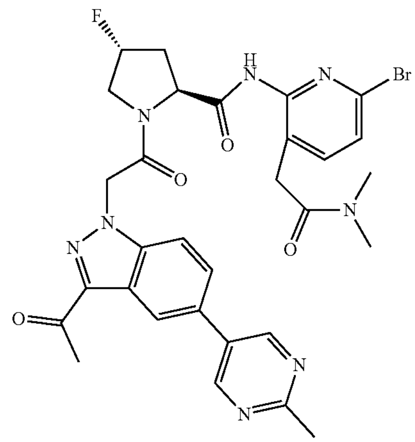 [SMILES: CC(=O)c1nn(CC(=O)N2C[C@H](F)C[C@H]2C(=O)Nc2nc(Br)ccc2CC(=O)N(C)C)c2ccc(-c3cnc(C)nc3)cc12] | (2S,4R)-1-(2-(3-acetyl-5-(2-methylpyrimidin-5-yl)-1H-indazol-1-yl)acetyl)-N-(6-bromo-3-(2-(dimethylamino)-2-oxoethyl)-pyridin-2-yl)-4-fluoropyrrolidine-2-carboxamide | *** | 1.33 (A) | 665 |
| 118 | 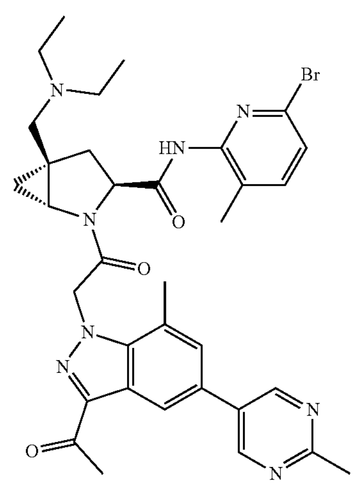 [SMILES: CCN(CC)C[C@@]12C[C@@H](C(=O)Nc3nc(Br)ccc3C)N(C(=O)Cn3nc(C(C)=O)c4cc(-c5cnc(C)nc5)cc(C)c43)[C@@H]1C2] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-((diethylamino)methyl)-2-azabicyclo[3.1.0]hexane-3-carboxamide | *** | 3.76 (B) | 687 |
| 119 | 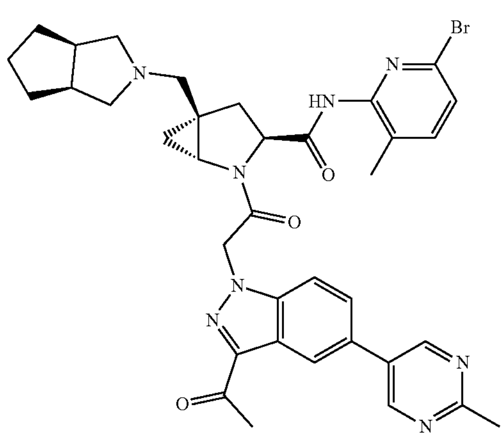 [SMILES: CC(=O)c1nn(CC(=O)N2[C@H](C(=O)Nc3nc(Br)ccc3C)C[C@@]3(CN4C[C@H]5CCC[C@H]5C4)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-methylpyridin-2-yl)-5-(((3aR,6aS)-hexahydrocyclopenta[c]pyrrol-2(1H)-yl)methyl)-2-azabicyclo[3.1.0]hexane-3-carboxamide | *** | 2.82 (B) | 711 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 120 | 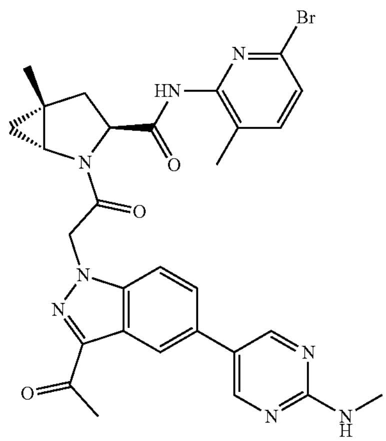 [SMILES: CNc1ncc(-c2ccc3c(c2)c(C(C)=O)nn3CC(=O)N2[C@H](C(=O)Nc3nc(Br)ccc3C)C[C@@]3(C)C[C@@H]23)cn1] | (1R,3S,5R)-2-(2-(3-acetyl-5-(2-(methylamino)-pyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 1.77(A) | 617 |
| 121 | 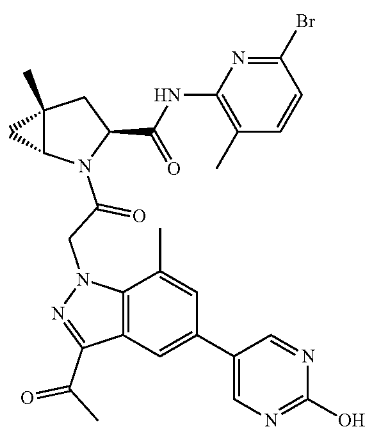 [SMILES: CC(=O)c1nn(CC(=O)N2[C@H](C(=O)Nc3nc(Br)ccc3C)C[C@@]3(C)C[C@@H]23)c2c(C)cc(-c3cnc(O)nc3)cc12] | (1R,3S,5R)-2-(2-(3-acetyl-5-(2-hydroxypyrimidin-5-yl)-7-methyl-1H-indazol-1-yl)acetyl)-N-(6-bromo-3-methylpyridin-2-yl)-5-methyl-2-azabicyclo[3.1.0]hexane-3-carboxamide | *** | 1.52 (A) | 617 |
| 122 | 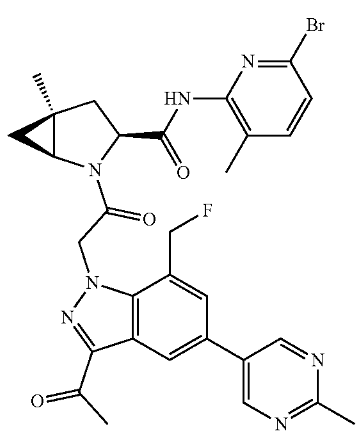 [SMILES: CC(=O)c1nn(CC(=O)N2[C@H]3C[C@@]3(C)C[C@H]2C(=O)Nc2nc(Br)ccc2C)c2c(CF)cc(-c3cnc(C)nc3)cc12] | (1S,3S,5S)-2-(2-(3-acetyl-7-(fluoromethyl)-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | | 2.06 (A) | 633 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 123 | 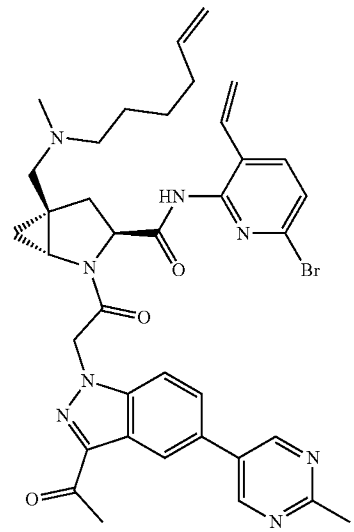 [SMILES: C=CCCCCN(C)C[C@@]12C[C@@H](C(=O)Nc3nc(Br)ccc3C=C)N(C(=O)Cn3nc(C(C)=O)c4cc(-c5cnc(C)nc5)ccc43)[C@@H]1C2] | (1R,3S,5R)-2-(2-(3-acetyl-5-(2-methylpyrimidin-5-yl)-1H-indazol-1-yl)acetyl)-N-(6-bromo-3-vinylpyridin-2-yl)-5-((hex-5-en-1-yl(methyl)amino)-methyl)-2-azabicyclo[3.1.0]hexane-3-carboxamide | *** | 1.47 (A) | 725 |
| 124 | 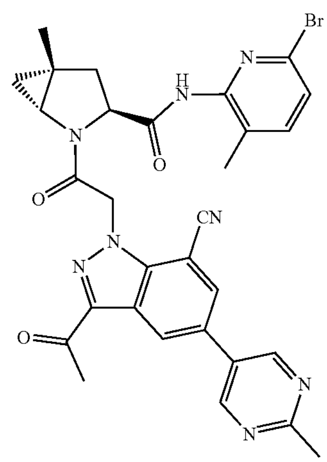 [SMILES: CC(=O)c1nn(CC(=O)N2[C@H](C(=O)Nc3nc(Br)ccc3C)C[C@@]3(C)C[C@@H]23)c2c(C#N)cc(-c3cnc(C)nc3)cc12] | (1R,3S,5R)-2-(2-(3-acetyl-7-cyano-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 1.94 (A) | 629 |
| 125 | 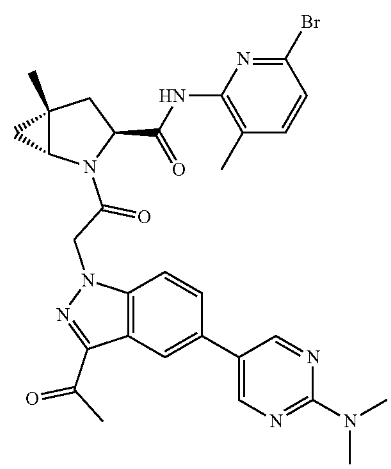 [SMILES: CC(=O)c1nn(CC(=O)N2[C@H](C(=O)Nc3nc(Br)ccc3C)C[C@@]3(C)C[C@@H]23)c2ccc(-c3cnc(N(C)C)nc3)cc12] | (1R,3S,5R)-2-(2-(3-acetyl-5-(2-(dimethylamino)pyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 2.13 (A) | 631 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 126 | 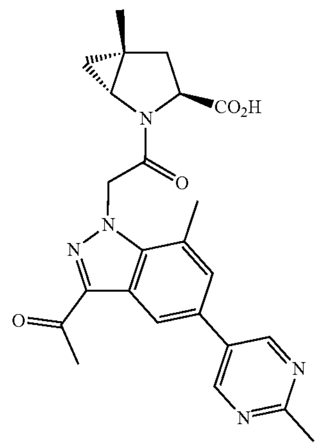 | (1R,3S,5R)-2-(2-(3-acetyl-7-methyl-5-(2-methylpyrimidin-5-yl)-1H-indazol-1-yl)acetyl)-5-methyl-2-azabicyclo[3.1.0]hexane-3-carboxylic acid | * | 1.42 (A) | 448 |
| 127 | 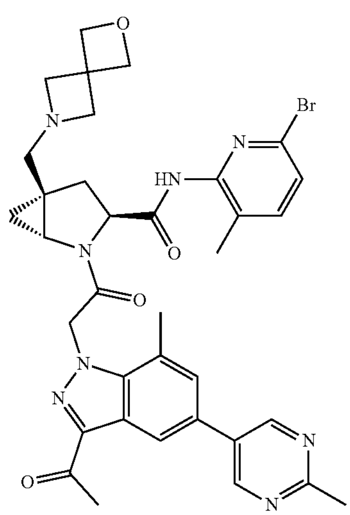 [SMILES: CC(=O)c1nn(CC(=O)N2[C@H](C(=O)Nc3nc(Br)ccc3C)C[C@@]3(CN4CC5(COC5)C4)C[C@@H]23)c2c(C)cc(-c3cnc(C)nc3)cc12] | (1R,3S,5R)-5-(2-oxa-6-azaspiro[3.3]heptan-6-ylmethyl)-2-(2-(3-acetyl-7-methyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide | *** | 2.35 (B) | 713 |
| 128 | 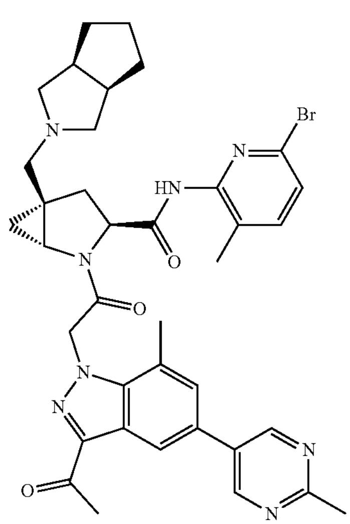 [SMILES: CC(=O)c1nn(CC(=O)N2[C@H](C(=O)Nc3nc(Br)ccc3C)C[C@@]3(CN4C[C@H]5CCC[C@H]5C4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-(((3aR,6aS)-hexahydrocyclopenta[c]pyrrol-2(1H)-yl)methyl)-2-azabicyclo[3.1.0]hexane-3-carboxamide | *** | 2.90 (B) | 725 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 129 | 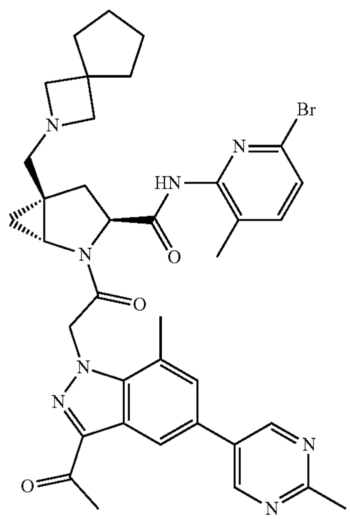 [SMILES: CC(=O)c1nn(CC(=O)N2[C@H](C(=O)Nc3nc(Br)ccc3C)C[C@@]3(CN4CC5(CCCC5)C4)C[C@@H]23)c2c(C)cc(-c3cnc(C)nc3)cc12] | (1R,3S,5R)-5-(2-azaspiro[3.4]-octan-2-ylmethyl)-2-(2-(3-acetyl-7-methyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide | *** | 2.78 (B) | 725 |
| 130 | 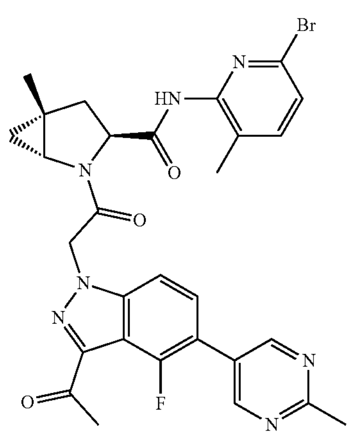 [SMILES: CC(=O)c1nn(CC(=O)N2[C@H](C(=O)Nc3nc(Br)ccc3C)C[C@@]3(C)C[C@@H]23)c2ccc(-c3cnc(C)nc3)c(F)c12] | (1R,3S,5R)-2-(2-(3-acetyl-4-fluoro-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 3.41 (B) | 620 |
| 131 | 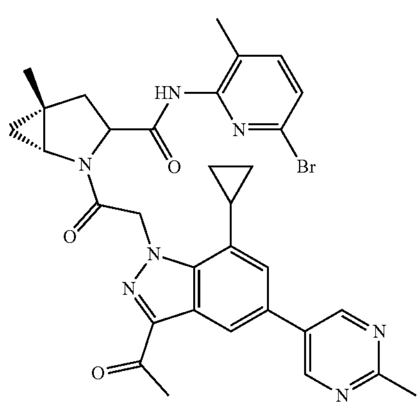 [SMILES: CC(=O)c1nn(CC(=O)N2C(C(=O)Nc3nc(Br)ccc3C)C[C@@]3(C)C[C@@H]23)c2c(C3CC3)cc(-c3cnc(C)nc3)cc12] | (1R,5R)-2-(2-(3-acetyl-7-cyclopropyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 3.66 (B) | 642 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 132 | 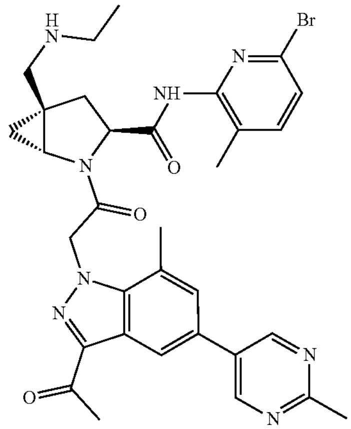 | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-((ethylamino)-methyl)-2-azabicyclo[3.1.0]hexane-3-carboxamide | *** | 2.31 (B) | 659 |
| 133 | 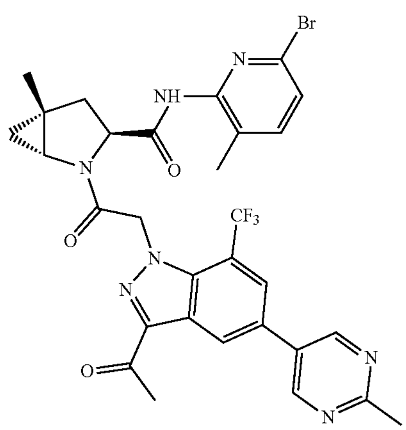 [SMILES: CC(=O)c1nn(CC(=O)N2[C@H](C(=O)Nc3nc(Br)ccc3C)C[C@@]3(C)C[C@@H]23)c2c(C(F)(F)F)cc(-c3cnc(C)nc3)cc12] | (1R,3S,5R)-2-(2-(3-acetyl-5-(2-methylpyrimidin-5-yl)-7-(trifluoromethyl)-1H-indazol-1-yl)acetyl)-N-(6-bromo-3-methylpyridin-2-yl)-5-methyl-2-azabicyclo[3.1.0]hexane-3-carboxamide | *** | 3.72 (B) | 670 |
| 134 | 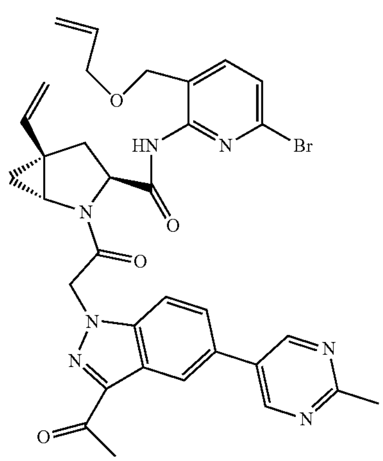 [SMILES: C=CCOCc1ccc(Br)nc1NC(=O)[C@@H]1C[C@@]2(C=C)C[C@H]2N1C(=O)Cn1nc(C(C)=O)c2cc(-c3cnc(C)nc3)ccc21] | (1R,3S,5R)-2-(2-(3-acetyl-5-(2-methylpyrimidin-5-yl)-1H-indazol-1-yl)acetyl)-N-(3-((allyloxy)-methyl)-6-bromopyridin-2-yl)-5-vinyl-2-azabicyclo[3.1.0]hexane-3-carboxamide | *** | 2.15 (A) | 670 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 135 | 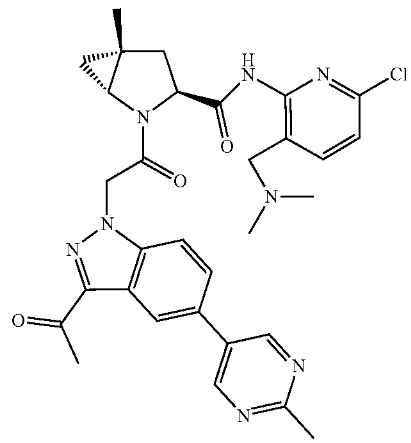 [SMILES: CC(=O)c1nn(CC(=O)N2[C@H](C(=O)Nc3nc(Cl)ccc3CN(C)C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-chloro-3-((dimethylamino)-methyl)pyridin-2-yl)-5-methyl-2-azabicyclo[3.1.0]hexane-3-carboxamide | *** | 1.12 (A) | 601 |
| 136 | 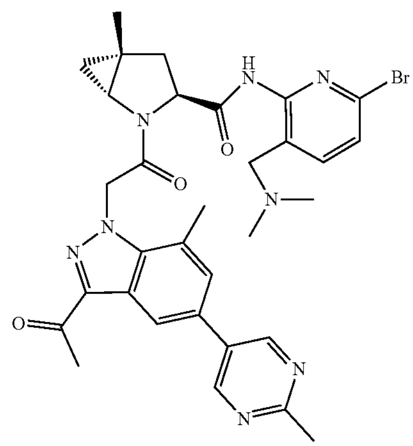 [SMILES: CC(=O)c1nn(CC(=O)N2[C@H](C(=O)Nc3nc(Br)ccc3CN(C)C)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-((dimethylamino)-methyl)pyridin-2-yl)-5-methyl-2-azabicyclo[3.1.0]hexane-3-carboxamide | *** | 1.24 (A) | 659 |
| 137 | 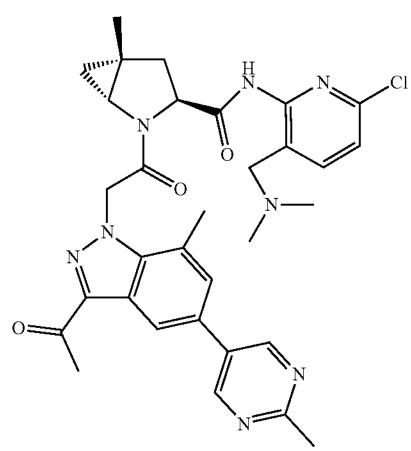 | (1R,3S,5R)-2-(2-(3-acetyl-7-methyl-5-(2-methylpyrimidin-5-yl)-1H-indazol-1-yl)acetyl)-N-(6-chloro-3-((dimethylamino)-methyl)pyridin-2-yl)-5-methyl-2-azabicyclo[3.1.0]hexane-3-carboxamide | *** | 1.21 (A) | 615 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 138 | 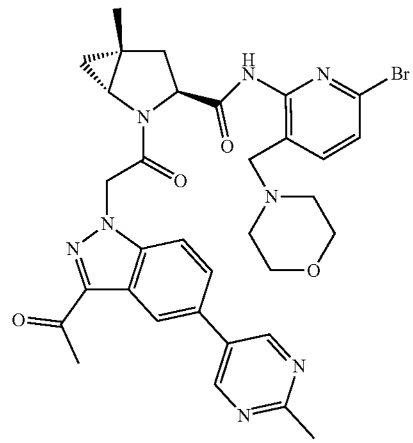 [SMILES: CC(=O)c1nn(CC(=O)N2[C@H](C(=O)Nc3nc(Br)ccc3CN3CCOCC3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-(morpholino-methyl)pyridin-2-yl)-5-methyl-2-azabicyclo[3.1.0]hexane-3-carboxamide | *** | 1.21 (A) | 687 |
| 139 | 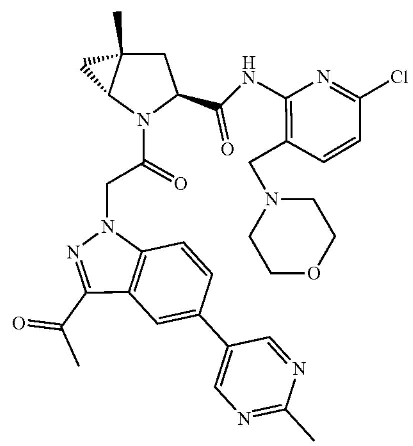 [SMILES: CC(=O)c1nn(CC(=O)N2[C@H](C(=O)Nc3nc(Cl)ccc3CN3CCOCC3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-chloro-3-(morpholino-methyl)pyridin-2-yl)-5-methyl-2-azabicyclo[3.1.0]hexane-3-carboxamide | *** | 1.19 (A) | 643 |
| 140 | 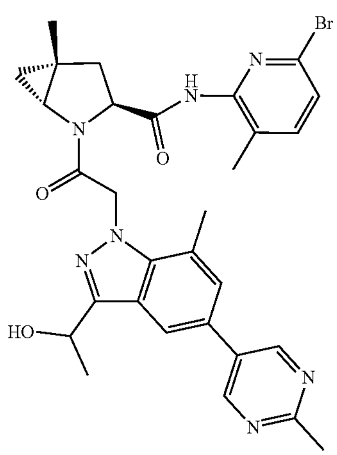 [SMILES: Cc1ncc(-c2cc(C)c3c(c2)c(C(C)O)nn3CC(=O)N2[C@H](C(=O)Nc3nc(Br)ccc3C)C[C@@]3(C)C[C@@H]23)cn1] | (1R,3S,5R)-N-(6-bromo-3-methylpyridin-2-yl)-2-(2-(3-(1-hydroxyethyl)-7-methyl-5-(2-methylpyrimidin-5-yl)-1H-indazol-1-yl)acetyl)-5-methyl-2-azabicyclo[3.1.0]hexane-3-carboxamide | *** | 1.63 (A) | 618 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 141 | 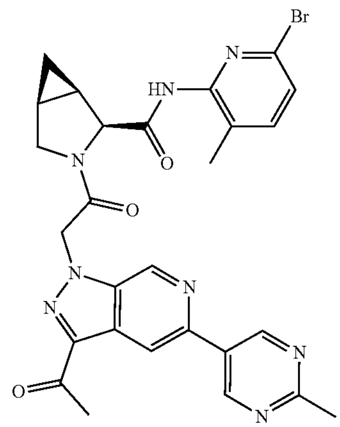 [SMILES: CC(=O)c1nn(CC(=O)N2C[C@H]3C[C@H]3[C@H]2C(=O)Nc2nc(Br)ccc2C)c2cnc(-c3cnc(C)nc3)cc12] | (1R,2S,5S)-3-(2-(3-acetyl-5-(2-methylpyrimidin-5-yl)-1H-pyrazolo[3,4-c]pyridin-1-yl)acetyl)-N-(6-bromo-3-methylpyridin-2-yl)-3-azabicyclo[3.1.0]hexane-2-carboxamide | *** | 1.46 (A) | 589 |
| 142 | 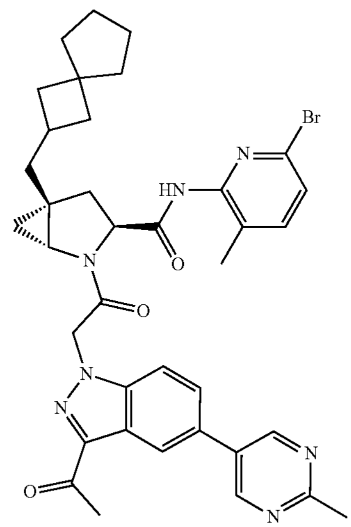 [SMILES: CC(=O)c1nn(CC(=O)N2[C@H](C(=O)Nc3nc(Br)ccc3C)C[C@@]3(CC4CC5(CCCC5)C4)C[C@@H]23)c2ccc(-c3cnc(C)nc3)cc12] | (1R,3S,5R)-5-(2-azaspiro[3.4]octan-2-ylmethyl)-2-(2-(3-acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide | *** | 2.49 (B) | 711 |
| 143 | 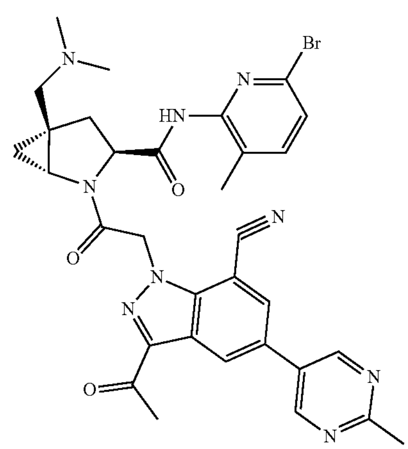 [SMILES: CC(=O)c1nn(CC(=O)N2[C@H](C(=O)Nc3nc(Br)ccc3C)C[C@@]3(CN(C)C)C[C@@H]23)c2c(C#N)cc(-c3cnc(C)nc3)cc12] | (1R,3S,5R)-2-(2-(3-acetyl-7-cyano-5-(2-methylpyrimidin-5-yl)-1H-indazol-1-yl)acetyl)-N-(6-bromo-3-methylpyridin-2-yl)-5-((dimethylamino)-methyl)-2-azabicyclo[3.1.0]hexane-3-carboxamide | *** | 2.59 (B) | 670 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 144 | 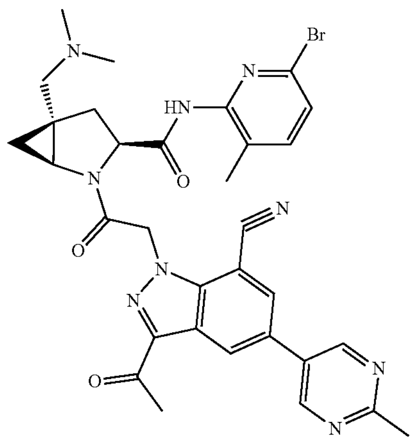 [SMILES: CC(=O)c1nn(CC(=O)N2[C@H]3C[C@@]3(CN(C)C)C[C@H]2C(=O)Nc2nc(Br)ccc2C)c2c(C#N)cc(-c3cnc(C)nc3)cc12] | (1S,3S,5S)-2-(2-(3-acetyl-7-cyano-5-(2-methylpyrimidin-5-yl)-1H-indazol-1-yl)acetyl)-N-(6-bromo-3-methylpyridin-2-yl)-5-((dimethylamino)-methyl)-2-azabicyclo[3.1.0]hexane-3-carboxamide | ** | 2.65 (B) | 670 |
| 145 | 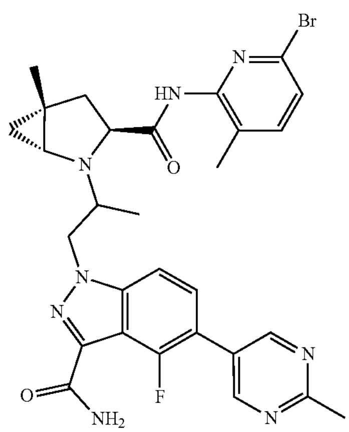 [SMILES: Cc1ncc(-c2ccc3c(c(C(N)=O)nn3CC(C)N3[C@H](C(=O)Nc4nc(Br)ccc4C)C[C@@]4(C)C[C@@H]34)c2F)cn1] | 1-(2-((1R,3S,5R)-3-((6-bromo-3-methylpyridin-2-yl)carbamoyl)-5-methyl-2-azabicyclo[3.1.0]hexan-2-yl)-2-oxoethyl)-4-fluoro-5-(2-methylpyrimidin-5-yl)-1H-indazole-3-carboxamide | *** | 2.40 (B) | 621 |
| 146 | 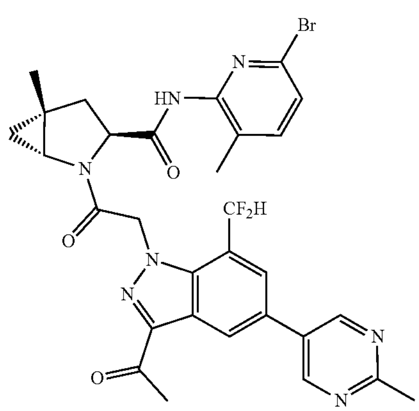 [SMILES: CC(=O)c1nn(CC(=O)N2[C@H](C(=O)Nc3nc(Br)ccc3C)C[C@@]3(C)C[C@@H]23)c2c(C(F)F)cc(-c3cnc(C)nc3)cc12] | (1R,3S,5R)-2-(2-(3-acetyl-7-(difluoromethyl)-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 3.72 (B) | 652 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 147 | 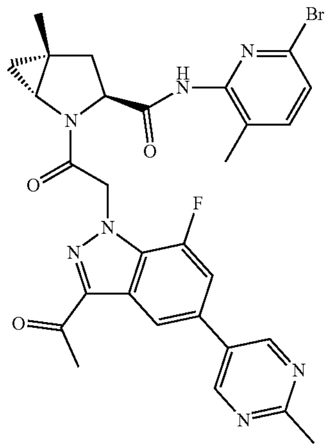 [SMILES: CC(=O)c1nn(CC(=O)N2[C@H](C(=O)Nc3nc(Br)ccc3C)C[C@@]3(C)C[C@@H]23)c2c(F)cc(-c3cnc(C)nc3)cc12] | (1R,3S,5R)-2-(2-(3-acetyl-7-fluoro-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 1.92 (A) | 620 |
| 148 | 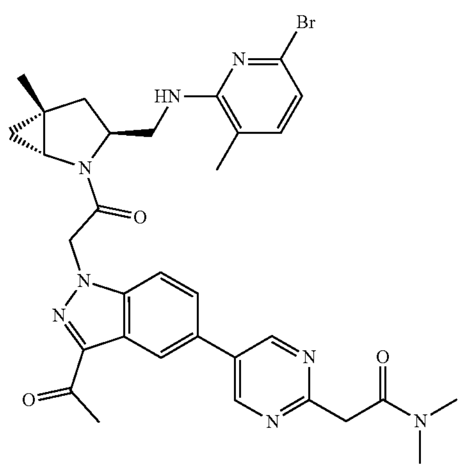 [SMILES: CC(=O)c1nn(CC(=O)N2[C@H](CNc3nc(Br)ccc3C)C[C@@]3(C)C[C@@H]23)c2ccc(-c3cnc(CC(=O)N(C)C)nc3)cc12] | (1R,3S,5R)-2-(2-(3-acetyl-5-(2-(2-(dimethylamino)-2-oxoethyl)pyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 1.66 (A) | 673 |
| 149 | 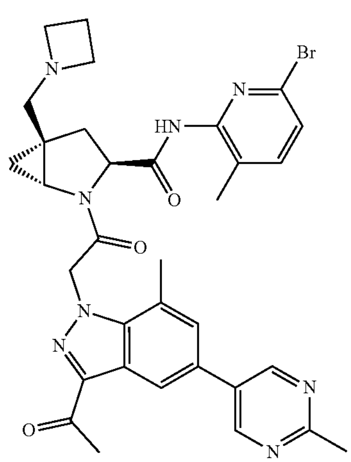 [SMILES: CC(=O)c1nn(CC(=O)N2[C@H](C(=O)Nc3nc(Br)ccc3C)C[C@@]3(CN4CCC4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-(azetidin-1-ylmethyl)-N-(6-bromo-3-methylpyridin-2-yl)-2-azabicyclo[3.1.0]hexane-3-carboxamide | *** | 2.34 (B) | 671 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 150 | 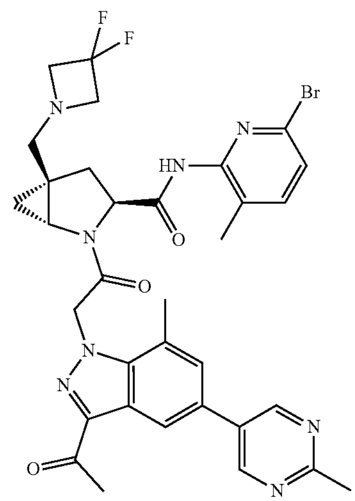 [SMILES: CC(=O)c1nn(CC(=O)N2[C@H](C(=O)Nc3nc(Br)ccc3C)C[C@@]3(CN4CC(F)(F)C4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-((3,3-difluoroazetidin-1-yl)methyl)-2-azabicyclo[3.1.0]hexane-3-carboxamide | *** | 2.46 (B) | 707 |
| 151 | 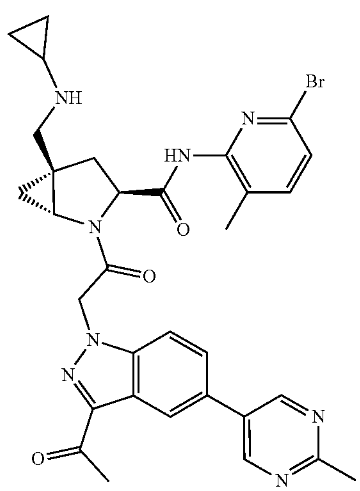 [SMILES: CC(=O)c1nn(CC(=O)N2[C@H](C(=O)Nc3nc(Br)ccc3C)C[C@@]3(CNC4CC4)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-methylpyridin-2-yl)-5-((cyclopropylamino)methyl)-2-azabicyclo[3.1.0]hexane-3-carboxamide | *** | 3.82 (B) | 657 |
| 152 | 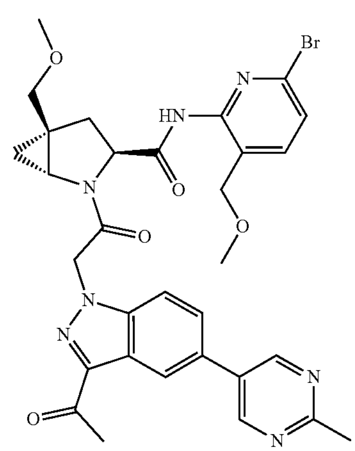 [SMILES: COCc1ccc(Br)nc1NC(=O)[C@@H]1C[C@@]2(COC)C[C@H]2N1C(=O)Cn1nc(C(C)=O)c2cc(-c3cnc(C)nc3)ccc21] | (1R,3S,5S)-2-(2-(3-acetyl-5-(2-methylpyrimidin-5-yl)-1H-indazol-1-yl)acetyl)-N-(6-bromo-3-(methoxymethyl)pyridin-2-yl)-5-(methoxymethyl)-2-azabicyclo[3.1.0]hexane-3-carboxamide | *** | 3.33 (B) | 662 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 153 | 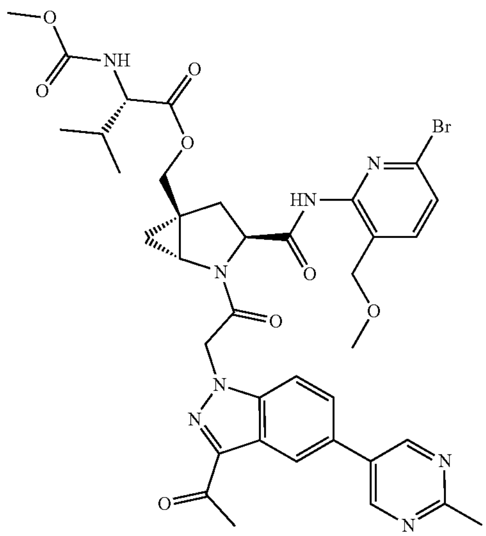 | methyl ((S)-1-((((1R,3S,5R)-2-(2-(3-acetyl-5-(2-methylpyrimidin-5-yl)-1H-indazol-1-yl)acetyl)-3-((6-bromo-3-(methoxymethyl)pyridin-2-yl)carbamoyl)-2-azabicyclo[3.1.0]hexan-5-yl)methyl)amino)-3-methyl-1-oxobutan-2-yl)carbamate | *** | 2.95 (B) | 804 |
| 154 | 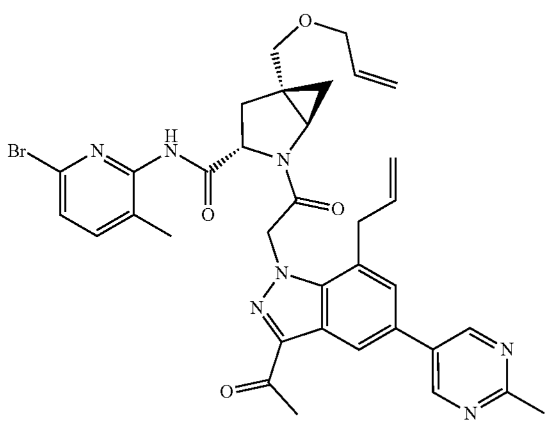 [SMILES: C=CCOC[C@@]12C[C@@H](C(=O)Nc3nc(Br)ccc3C)N(C(=O)Cn3nc(C(C)=O)c4cc(-c5cnc(C)nc5)cc(CC=C)c43)[C@@H]1C2] | (1R,3S,5S)-2-(2-(3-acetyl-7-allyl-5-(2-methylpyrimidin-5-yl)-1H-indazol-1-yl)acetyl)-5-((allyloxy)methyl)-N-(6-bromo-3-methylpyridin-2-yl)-2-azabicyclo[3.1.0]hexane-3-carboxamide | *** | 3.71 (B) | 698 |
| 155 | 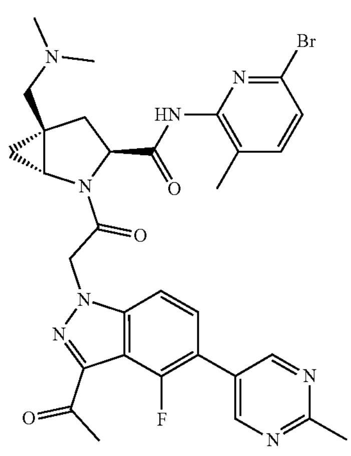 [SMILES: CC(=O)c1nn(CC(=O)N2[C@H](C(=O)Nc3nc(Br)ccc3C)C[C@@]3(CN(C)C)C[C@@H]23)c2ccc(-c3cnc(C)nc3)c(F)c12] | (1R,3S,5R)-2-(2-(3-acetyl-4-fluoro-5-(2-methylpyrimidin-5-yl)-1H-indazol-1-yl)acetyl)-N-(6-bromo-3-methylpyridin-2-yl)-5-((dimethylamino)methyl)-2-azabicyclo[3.1.0]hexane-3-carboxamide | *** | 2.33 (B) | 663 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 156 | 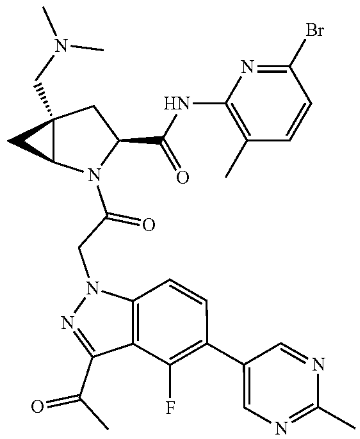 [SMILES: CC(=O)c1nn(CC(=O)N2[C@H]3C[C@@]3(CN(C)C)C[C@H]2C(=O)Nc2nc(Br)ccc2C)c2ccc(-c3cnc(C)nc3)c(F)c12] | (1S,3S,5S)-2-(2-(3-acetyl-4-fluoro-5-(2-methylpyrimidin-5-yl)-1H-indazol-1-yl)acetyl)-N-(6-bromo-3-methylpyridin-2-yl)-5-((dimethylamino)-methyl)-2-azabicyclo[3.1.0]hexane-3-carboxamide | * | 2.51 (B) | 663 |
| 157 | 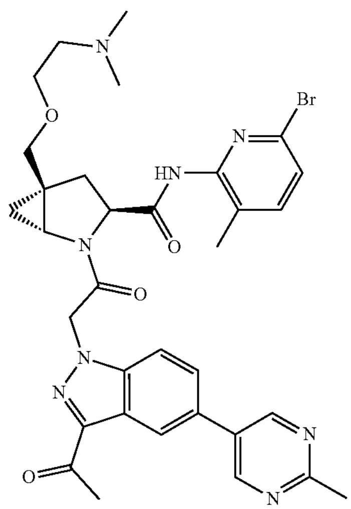 [SMILES: CC(=O)c1nn(CC(=O)N2[C@H](C(=O)Nc3nc(Br)ccc3C)C[C@@]3(COCCN(C)C)C[C@@H]23)c2ccc(-c3cnc(C)nc3)cc12] | (1R,3S,5S)-2-(2-(3-acetyl-5-(2-methylpyrimidin-5-yl)-1H-indazol-1-yl)acetyl)-N-(6-bromo-3-methylpyridin-2-yl)-5-((2-(dimethylamino)ethoxy)methyl)-2-azabicyclo[3.1.0]hexane-3-carboxamide | *** | 1.08 (A) | 688 |
| 158 | 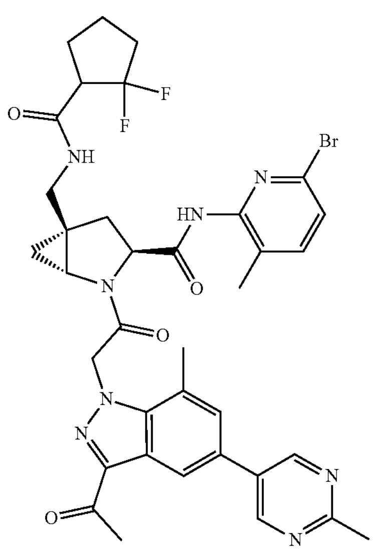 [SMILES: CC(=O)c1nn(CC(=O)N2[C@H](C(=O)Nc3nc(Br)ccc3C)C[C@@]3(CNC(=O)C4CCCC4(F)F)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-((2,2-difluorocyclo-pentane-1-carboxamido)-methyl)-2-azabicyclo[3.1.0]hexane-3-carboxamide | *** | 1.87 (A) | 762 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 159 | 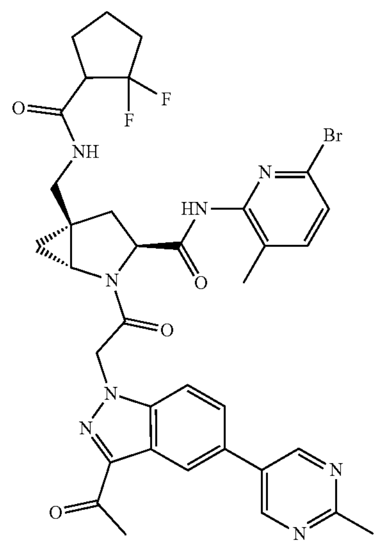 [SMILES: CC(=O)c1nn(CC(=O)N2[C@H](C(=O)Nc3nc(Br)ccc3C)C[C@@]3(CNC(=O)C4CCCC4(F)F)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-methylpyridin-2-yl)-5-((2,2-difluorocyclo-pentane-1-carboxamido)-methyl)-2-azabicyclo[3.1.0]hexane-3-carboxamide | *** | 1.79 (A) | 748 |
| 160 | 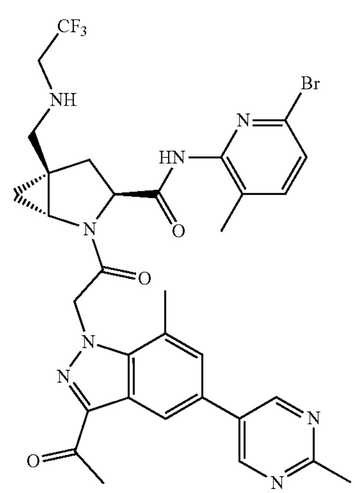 [SMILES: CC(=O)c1nn(CC(=O)N2[C@H](C(=O)Nc3nc(Br)ccc3C)C[C@@]3(CNCC(F)(F)F)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-(((2,2,2-trifluoroethyl)-amino)methyl)-2-azabicyclo[3.1.0]hexane-3-carboxamide | *** | 1.70 (A) | 712 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 161 | 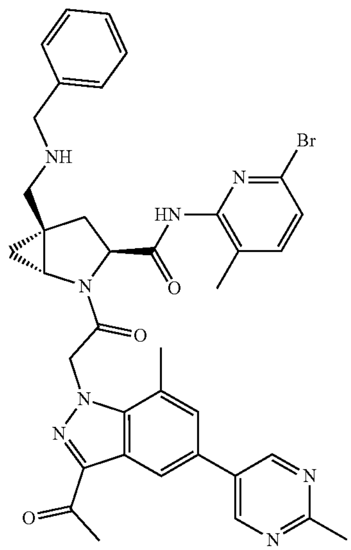 [SMILES: CC(=O)c1nn(CC(=O)N2[C@H](C(=O)Nc3nc(Br)ccc3C)C[C@@]3(CNCc4ccccc4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-((benzylamino)-methyl)-N-(6-bromo-3-methylpyridin-2-yl)-2-azabicyclo[3.1.0]hexane-3-carboxamide | *** | 1.36 (A) | 720 |
| 162 | 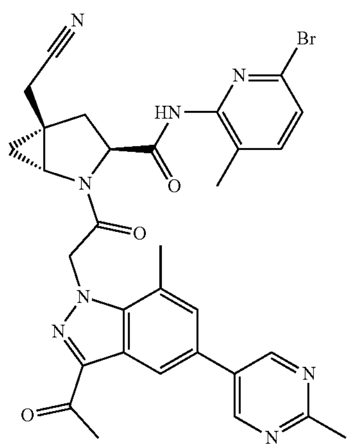 [SMILES: CC(=O)c1nn(CC(=O)N2[C@H](C(=O)Nc3nc(Br)ccc3C)C[C@@]3(CC#N)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-(cyanomethyl)-2-azabicyclo[3.1.0]hexane-3-carboxamide | *** | 1.65 (A) | 640 |
| 163 | 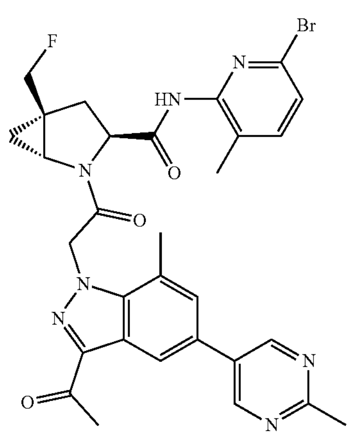 [SMILES: CC(=O)c1nn(CC(=O)N2[C@H](C(=O)Nc3nc(Br)ccc3C)C[C@@]3(CF)C[C@@H]23)c2c(C)cc(-c3cnc(C)nc3)cc12] | (1R,3S,5S)-2-(2-(3-acetyl-7-methyl-5-(2-methylpyrimidin-5-yl)-1H-indazol-1-yl)acetyl)-N-(6-bromo-3-methylpyridin-2-yl)-5-(fluoromethyl)-2-azabicyclo[3.1.0]hexane-3-carboxamide | *** | 1.77 (A) | 633 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 164 | 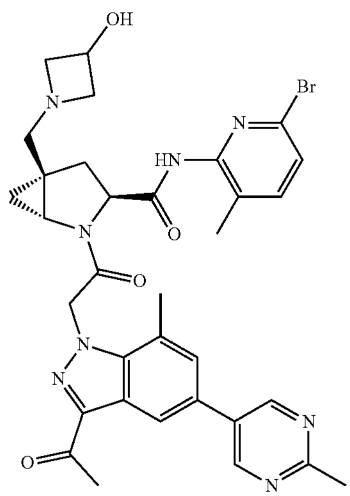 [SMILES: CC(=O)c1nn(CC(=O)N2[C@H](C(=O)Nc3nc(Br)ccc3C)C[C@@]3(CN4CC(O)C4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-((3-hydroxyazetidin-1-yl)methyl)-2-azabicyclo[3.1.0]hexane-3-carboxamide | *** | 1.05 (A) | 686 |
| 165 | 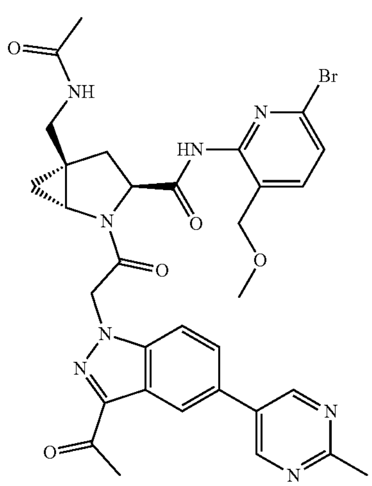 [SMILES: COCc1ccc(Br)nc1NC(=O)[C@@H]1C[C@@]2(CNC(C)=O)C[C@H]2N1C(=O)Cn1nc(C(C)=O)c2cc(-c3cnc(C)nc3)ccc21] | (1R,3S,5R)-5-(acetamidomethyl)-2-(2-(3-acetyl-5-(2-methylpyrimidin-5-yl)-1H-indazol-1-yl)acetyl)-N-(6-bromo-3-(methoxymethyl)pyridin-2-yl)-2-azabicyclo[3.1.0]hexane-3-carboxamide | *** | 1.36 (A) | 688 |
| 166 | 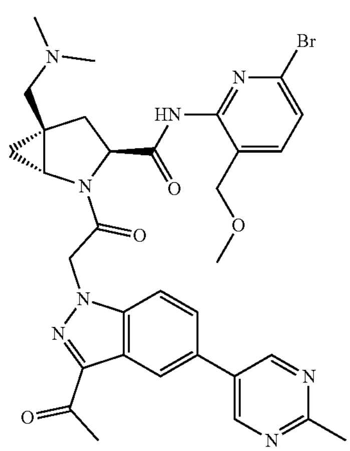 [SMILES: COCc1ccc(Br)nc1NC(=O)[C@@H]1C[C@@]2(CN(C)C)C[C@H]2N1C(=O)Cn1nc(C(C)=O)c2cc(-c3cnc(C)nc3)ccc21] | (1R,3S,5R)-2-(2-(3-acetyl-5-(2-methylpyrimidin-5-yl)-1H-indazol-1-yl)acetyl)-N-(6-bromo-3-(methoxymethyl)pyridin-2-yl)-5-((dimethylamino)methyl)-2-azabicyclo[3.1.0]hexane-3-carboxamide | *** | 1.02 (A) | 674 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 167 | 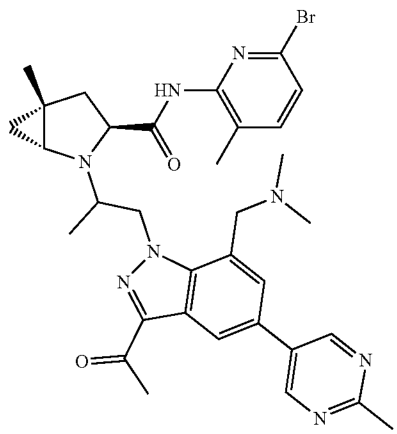 [SMILES: CC(=O)c1nn(CC(C)N2[C@H](C(=O)Nc3nc(Br)ccc3C)C[C@@]3(C)C[C@@H]23)c2c(CN(C)C)cc(-c3cnc(C)nc3)cc12] | (1R,3S,5R)-2-(2-(3-acetyl-7-((dimethylamino)-methyl)-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 1.27 (A) | 658 |
| 168 | 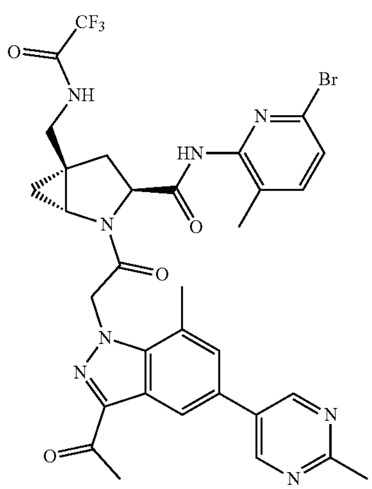 [SMILES: CC(=O)c1nn(CC(=O)N2[C@H](C(=O)Nc3nc(Br)ccc3C)C[C@@]3(CNC(=O)C(F)(F)F)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-((2,2,2-trifluoro-acetamido)-methyl)-2-azabicyclo[3.1.0]hexane-3-carboxamide | *** | 1.89 (A) | 726 |
| 169 | 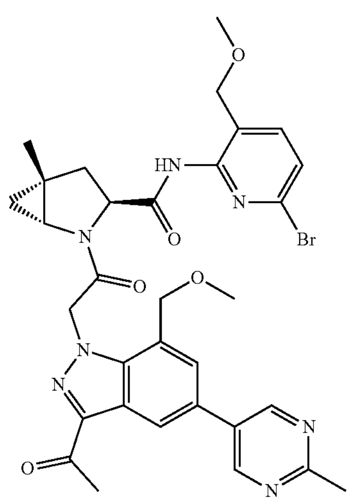 [SMILES: COCc1ccc(Br)nc1NC(=O)[C@@H]1C[C@@]2(C)C[C@H]2N1C(=O)Cn1nc(C(C)=O)c2cc(-c3cnc(C)nc3)cc(COC)c21] | (1R,3S,5R)-2-(2-(3-acetyl-7-(methoxymethyl)-5-(2-methylpyrimidin-5-yl)-1H-indazol-1-yl)acetyl)-N-(6-bromo-3-(methoxymethyl)pyridin-2-yl)-5-methyl-2-azabicyclo[3.1.0]hexane-3-carboxamide | *** | 2.01 (A) | 675 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 170 | 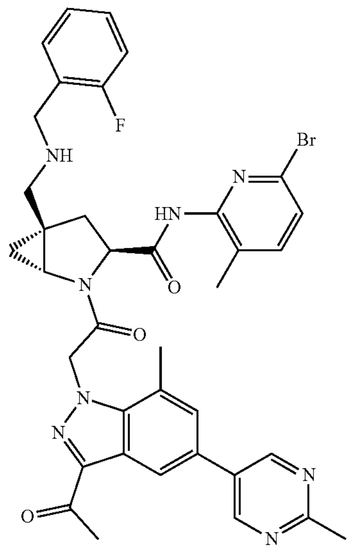 [SMILES: CC(=O)c1nn(CC(=O)N2[C@H](C(=O)Nc3nc(Br)ccc3C)C[C@@]3(CNCc4ccccc4F)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-(((2-fluorobenzyl)-amino)methyl)-2-azabicyclo[3.1.0]hexane-3-carboxamide | *** | 1.35 (A) | 738 |
| 171 | 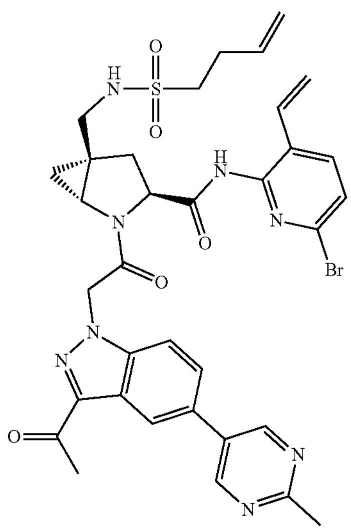 | (1R,3S,5R)-2-(2-(3-acetyl-5-(2-methylpyrimidin-5-yl)-1H-indazol-1-yl)acetyl)-N-(6-bromo-3-vinylpyridin-2-yl)-5-((but-3-en-1-ylsulfonamido)-methyl)-2-azabicyclo[3.1.0]hexane-3-carboxamide | *** | 1.85 (A) | 748 |
| 172 | 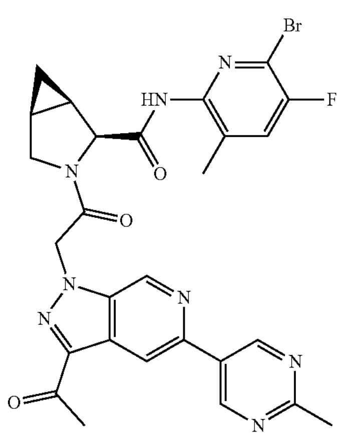 [SMILES: CC(=O)c1nn(CC(=O)N2C[C@H]3C[C@H]3[C@H]2C(=O)Nc2nc(Br)c(F)cc2C)c2cnc(-c3cnc(C)nc3)cc12] | (1R,2S,5S)-3-(2-(3-acetyl-5-(2-methylpyrimidin-5-yl)-1H-pyrazolo[3,4-c]pyridin-1-yl)acetyl)-N-(6-bromo-5-fluoro-3-methylpyridin-2-yl)-3-azabicyclo[3.1.0]hexane-2-carboxamide | *** | 1.55 (A) | 607 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 173 | 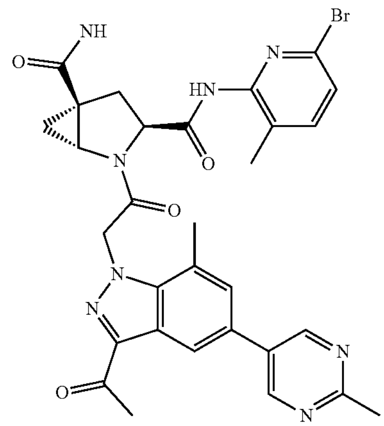 [SMILES: CC(=O)c1nn(CC(=O)N2[C@H](C(=O)Nc3nc(Br)ccc3C)C[C@@]3(C(N)=O)C[C@@H]23)c2c(C)cc(-c3cnc(C)nc3)cc12] | (1R,3S,5S)-2-(2-(3-acetyl-7-methyl-5-(2-methylpyrimidin-5-yl)-1H-indazol-1-yl)acetyl)-N3-(6-bromo-3-methylpyridin-2-yl)-2-azabicyclo[3.1.0]hexane-3,5-dicarboxamide | * | 3.02 (B) | 645 |
| 174 | 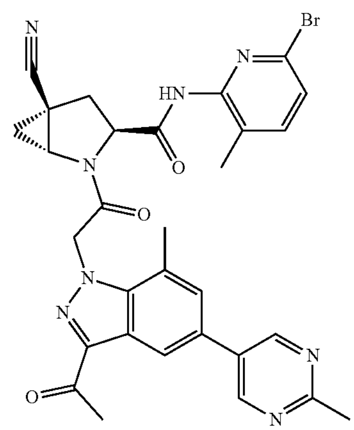 [SMILES: CC(=O)c1nn(CC(=O)N2[C@H](C(=O)Nc3nc(Br)ccc3C)C[C@@]3(C#N)C[C@@H]23)c2c(C)cc(-c3cnc(C)nc3)cc12] | (1R,3S,5S)-2-(2-(3-acetyl-7-methyl-5-(2-methylpyrimidin-5-yl)-1H-indazol-1-yl)acetyl)-N-(6-bromo-3-methylpyridin-2-yl)-5-cyano-2-azabicyclo[3.1.0]hexane-3-carboxamide | * | 3.35 (B) | 627 |
| 175 | 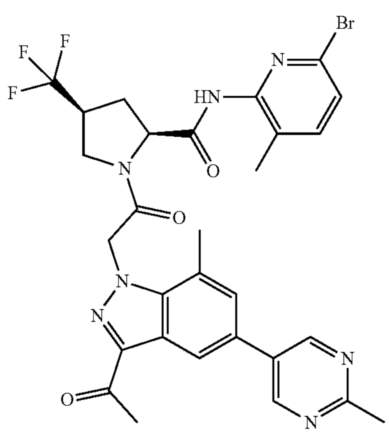 [SMILES: CC(=O)c1nn(CC(=O)N2C[C@@H](C(F)(F)F)C[C@H]2C(=O)Nc2nc(Br)ccc2C)c2c(C)cc(-c3cnc(C)nc3)cc12] | (2S,4S)-1-(2-(3-acetyl-7-methyl-5-(2-methylpyrimidin-5-yl)-1H-indazol-1-yl)acetyl)-N-(6-bromo-3-methylpyridin-2-yl)-4-(trifluoromethyl)pyrrolidine-2-carboxamide | *** | 3.36 (B) | 658 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 176 | 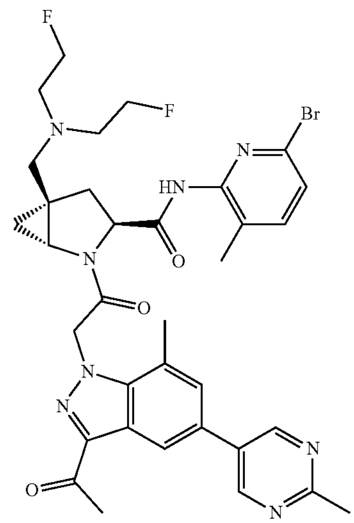 [SMILES: CC(=O)c1nn(CC(=O)N2[C@H](C(=O)Nc3nc(Br)ccc3C)C[C@@]3(CN(CCF)CCF)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-((bis(2-fluoroethyl)-amino)methyl)-N-(6-bromo-3-methylpyridin-2-yl)-2-azabicyclo[3.1.0]hexane-3-carboxamide | *** | 2.48 (B) | 723 |
| 177 | 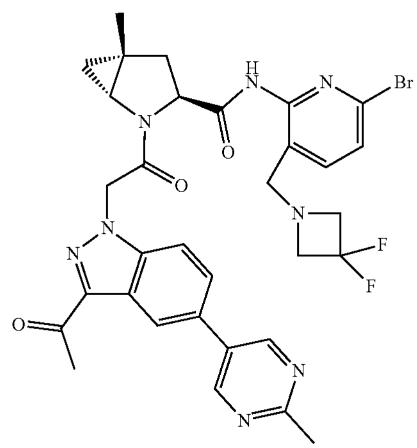 [SMILES: CC(=O)c1nn(CC(=O)N2[C@H](C(=O)Nc3nc(Br)ccc3CN3CC(F)(F)C3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-((3,3-difluoroazetidin-1-yl)methyl)pyridin-2-yl)-5-methyl-2-azabicyclo[3.1.0]hexane-3-carboxamide | *** | 1.83 (A) | 693 |
| 178 | 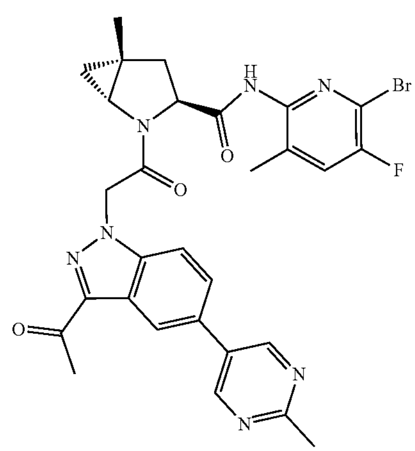 [SMILES: CC(=O)c1nn(CC(=O)N2[C@H](C(=O)Nc3nc(Br)c(F)cc3C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-5-fluoro-3-methylpyridin-2-yl)-5-methyl-2-azabicyclo[3.1.0]hexane-3-carboxamide | *** | 1.87 (A) | 620 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 179 | 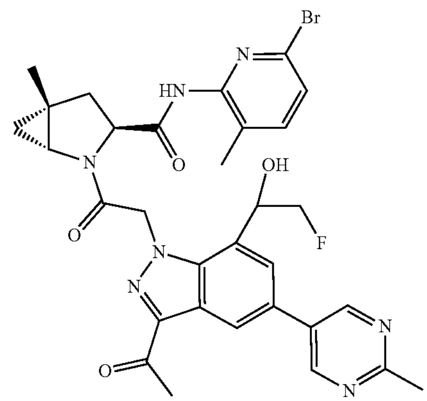 [SMILES: CC(=O)c1nn(CC(=O)N2[C@H](C(=O)Nc3nc(Br)ccc3C)C[C@@]3(C)C[C@@H]23)c2c(C(O)CF)cc(-c3cnc(C)nc3)cc12] | (1R,3S,5R)-2-(2-(3-acetyl-7-(2-fluoro-1-hydroxyethyl)-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 2.70 (B) | 604 |
| 180 | 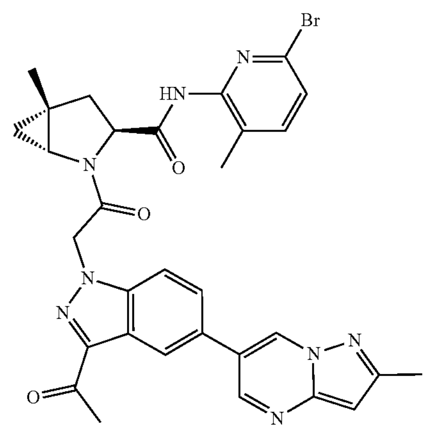 [SMILES: CC(=O)c1nn(CC(=O)N2[C@H](C(=O)Nc3nc(Br)ccc3C)C[C@@]3(C)C[C@@H]23)c2ccc(-c3cnc4cc(C)nn4c3)cc12] | (1R,3S,5R)-2-(2-(3-acetyl-5-(2-methylpyrazolo[1,5-a]pyrimidin-6-yl)-1H-indazol-1-yl)acetyl)-N-(6-bromo-3-methylpyridin-2-yl)-5-methyl-2-azabicyclo[3.1.0]hexane-3-carboxamide | *** | 2.04 (A) | 641 |
| 181 | 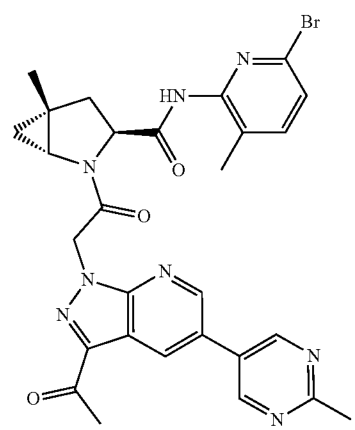 [SMILES: CC(=O)c1nn(CC(=O)N2[C@H](C(=O)Nc3nc(Br)ccc3C)C[C@@]3(C)C[C@@H]23)c2ncc(-c3cnc(C)nc3)cc12] | (1R,3S,5R)-2-(2-(3-acetyl-5-(2-methylpyrimidin-5-yl)-1H-pyrazolo[3,4-b]pyridin-1-yl)acetyl)-N-(6-bromo-3-methylpyridin-2-yl)-5-methyl-2-azabicyclo[3.1.0]hexane-3-carboxamide | | 1.70 (A) | 603 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 182 | 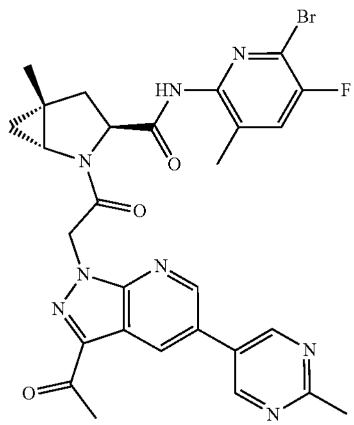 [SMILES: CC(=O)c1nn(CC(=O)N2[C@H](C(=O)Nc3nc(Br)c(F)cc3C)C[C@@]3(C)C[C@@H]23)c2ncc(-c3cnc(C)nc3)cc12] | (1R,3S,5R)-2-(2-(3-acetyl-5-(2-methylpyrimidin-5-yl)-1H-pyrazolo[3,4-b]pyridin-1-yl)acetyl)-N-(6-bromo-5-fluoro-3-methylpyridin-2-yl)-5-methyl-2-azabicyclo[3.1.0]hexane-3-carboxamide | *** | 1.79 (A) | 621 |
| 183 | 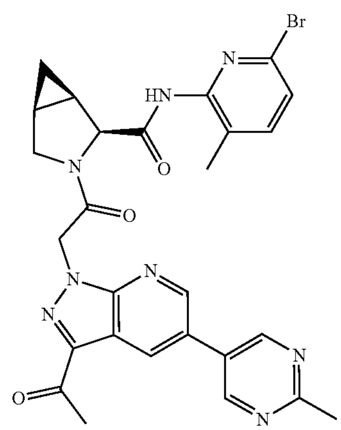 [SMILES: CC(=O)c1nn(CC(=O)N2C[C@H]3C[C@H]3[C@H]2C(=O)Nc2nc(Br)ccc2C)c2ncc(-c3cnc(C)nc3)cc12] | (1R,2S,5S)-3-(2-(3-acetyl-5-(2-methylpyrimidin-5-yl)-1H-pyrazolo[3,4-b]pyridin-1-yl)acetyl)-N-(6-bromo-3-methylpyridin-2-yl)-3-azabicyclo[3.1.0]hexane-2-carboxamide | *** | 1.47 (A) | 589 |
| 184 | 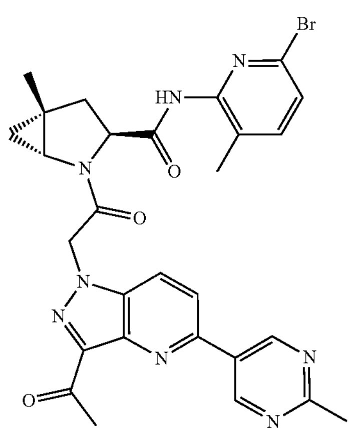 [SMILES: CC(=O)c1nn(CC(=O)N2[C@H](C(=O)Nc3nc(Br)ccc3C)C[C@@]3(C)C[C@@H]23)c2ccc(-c3cnc(C)nc3)nc12] | (1R,3S,5R)-2-(2-(3-acetyl-5-(2-methylpyrimidin-5-yl)-1H-pyrazolo[4,3-b]pyridin-1-yl)acetyl)-N-(6-bromo-3-methylpyridin-2-yl)-5-methyl-2-azabicyclo[3.1.0]hexane-3-carboxamide | ** | 1.55 (A) | 603 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 185 | 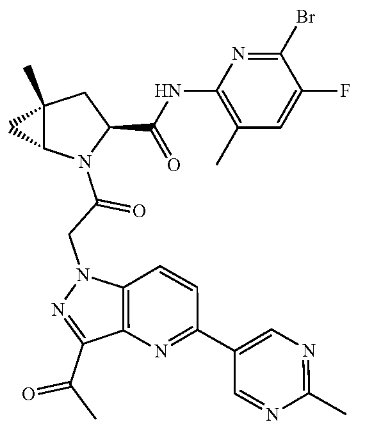 [SMILES: CC(=O)c1nn(CC(=O)N2[C@H](C(=O)Nc3nc(Br)c(F)cc3C)C[C@@]3(C)C[C@@H]23)c2ccc(-c3cnc(C)nc3)nc12] | (1R,3S,5R)-2-(2-(3-acetyl-5-(2-methylpyrimidin-5-yl)-1H-pyrazolo[4,3-b]pyridin-1-yl)acetyl)-N-(6-bromo-5-fluoro-3-methylpyridin-2-yl)-5-methyl-2-azabicyclo[3.1.0]hexane-3-carboxamide | ** | 1.64 (A) | 621 |
| 187 | 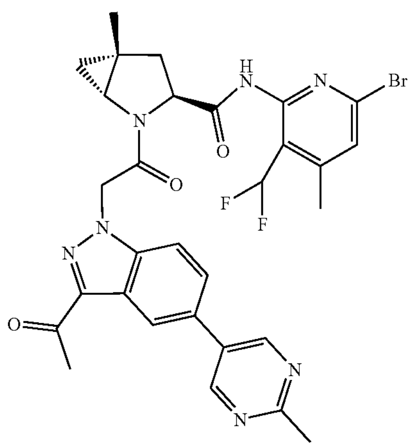 [SMILES: CC(=O)c1nn(CC(=O)N2[C@H](C(=O)Nc3nc(Br)cc(C)c3C(F)F)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-(difluoromethyl)-4-methylpyridin-2-yl)-5-methyl-2-azabicyclo[3.1.0]hexane-3-carboxamide | *** | 2.04 (A) | 652 |
| 188 | 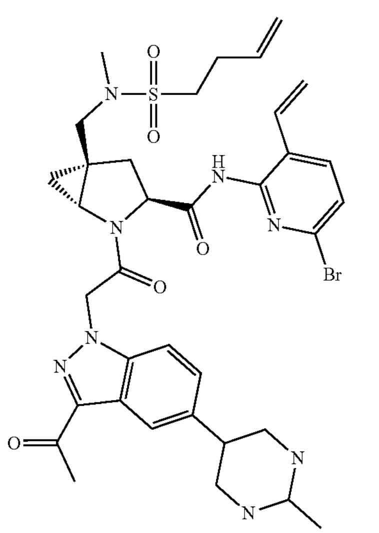 [SMILES: C=CCCS(=O)(=O)N(C)C[C@@]12C[C@@H](C(=O)Nc3nc(Br)ccc3C=C)N(C(=O)Cn3nc(C(C)=O)c4cc(C5CNC(C)NC5)ccc43)[C@@H]1C2] | (1R,3S,5R)-2-(2-(3-acetyl-5-(2-methylpyrimidin-5-yl)-1H-indazol-1-yl)acetyl)-N-(6-bromo-3-vinylpyridin-2-yl)-5-(((N-methylbut-3-en-1-yl)sulfonamido)methyl)-2-azabicyclo[3.1.0]hexane-3-carboxamide | *** | 2.01 (A) | 761 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 189 | 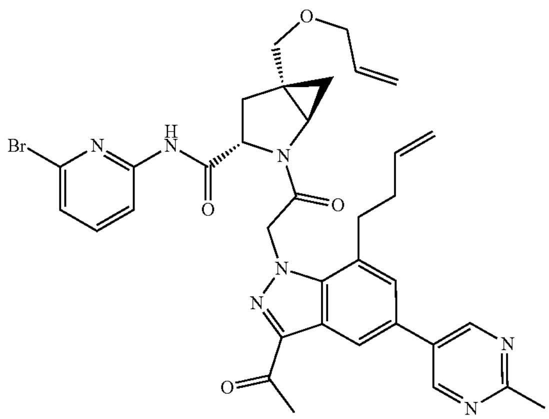 [SMILES: C=CCCc1cc(-c2cnc(C)nc2)cc2c(C(C)=O)nn(CC(=O)N3[C@H](C(=O)Nc4cccc(Br)n4)C[C@@]4(COCC=C)C[C@@H]34)c12] | (1R,3S,5S)-2-(2-(3-acetyl-7-(but-3-en-1-yl)-5-(2-methylpyrimidin-5-yl)-1H-indazol-1-yl)acetyl)-5-((allyloxy)methyl)-N-(6-bromo-3-methylpyridin-2-yl)-2-azabicyclo[3.1.0]hexane-3-carboxamide | *** | 2.36 (A) | 711 |
| 190 | 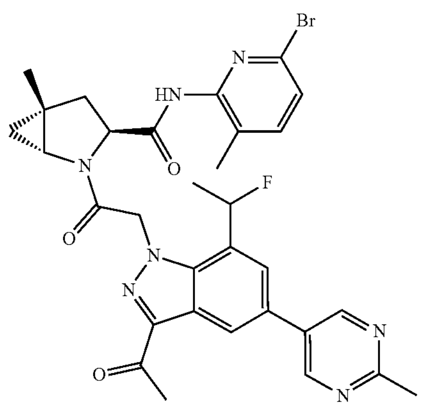 [SMILES: CC(=O)c1nn(CC(=O)N2[C@H](C(=O)Nc3nc(Br)ccc3C)C[C@@]3(C)C[C@@H]23)c2c(C(C)F)cc(-c3cnc(C)nc3)cc12] | (1R,3S,5R)-2-(2-(3-acetyl-7-(1-fluoroethyl)-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 2.05 (A) | 647 |
| 191 | 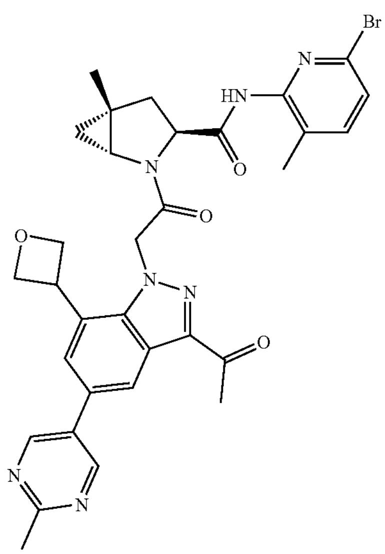 [SMILES: CC(=O)c1nn(CC(=O)N2[C@H](C(=O)Nc3nc(Br)ccc3C)C[C@@]3(C)C[C@@H]23)c2c(C3COC3)cc(-c3cnc(C)nc3)cc12] | (1R,3S,5R)-2-(2-(3-acetyl-5-(2-methylpyrimidin-5-yl)-7-(oxetan-3-yl)-1H-indazol-1-yl)acetyl)-N-(6-bromo-3-methylpyridin-2-yl)-5-methyl-2-azabicyclo[3.1.0]hexane-3-carboxamide | | | |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 192 | 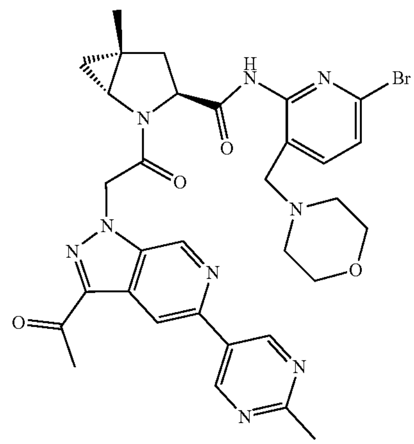 [SMILES: CC(=O)c1nn(CC(=O)N2[C@H](C(=O)Nc3nc(Br)ccc3CN3CCOCC3)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-(morpholinomethyl)pyridin-2-yl)-5-methyl-2-azabicyclo[3.1.0]hexane-3-carboxamide | *** | 1.10 (A) | 688 |
| 193 | 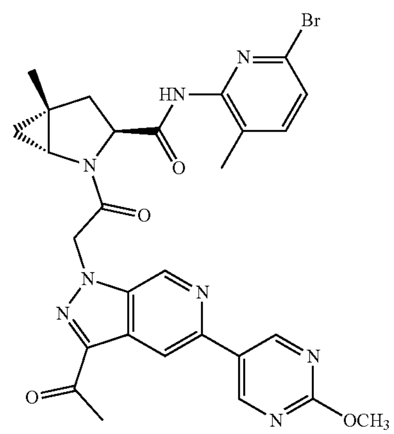 [SMILES: COc1ncc(-c2cc3c(C(C)=O)nn(CC(=O)N4[C@H](C(=O)Nc5nc(Br)ccc5C)C[C@@]5(C)C[C@@H]45)c3cn2)cn1] | (1R,3S,5R)-2-(2-(3-acetyl-5-(2-methoxypyrimidin-5-yl)-1H-pyrazolo[3,4-c]pyridin-1-yl)acetyl)-N-(6-bromo-3-methylpyridin-2-yl)-5-methyl-2-azabicyclo[3.1.0]hexane-3-carboxamide | *** | 1.84 (A) | 619 |
| 194 | 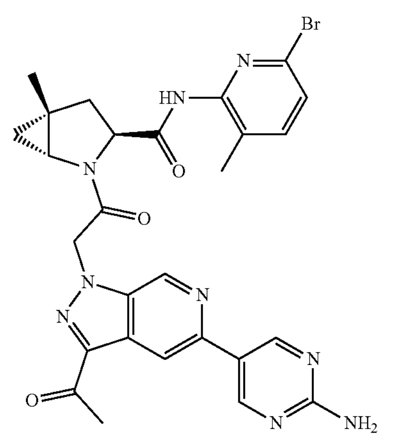 [SMILES: CC(=O)c1nn(CC(=O)N2[C@H](C(=O)Nc3nc(Br)ccc3C)C[C@@]3(C)C[C@@H]23)c2cnc(-c3cnc(N)nc3)cc12] | (1R,3S,5R)-2-(2-(3-acetyl-5-(2-aminopyrimidin-5-yl)-1H-pyrazolo[3,4-c]pyridin-1-yl)acetyl)-N-(6-bromo-3-methylpyridin-2-yl)-5-methyl-2-azabicyclo[3.1.0]hexane-3-carboxamide | *** | 1.49 (A) | 604 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 195 | 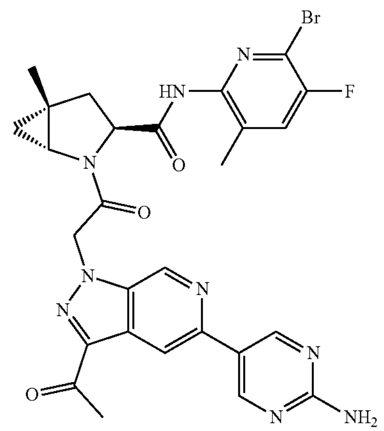 [SMILES: CC(=O)c1nn(CC(=O)N2[C@H](C(=O)Nc3nc(Br)c(F)cc3C)C[C@@]3(C)C[C@@H]23)c2cnc(-c3cnc(N)nc3)cc12] | (1R,3S,5R)-2-(2-(3-acetyl-5-(2-aminopyrimidin-5-yl)-1H-pyrazolo[3,4-c]pyridin-1-yl)acetyl)-N-(6-bromo-5-fluoro-3-methylpyridin-2-yl)-5-methyl-2-azabicyclo[3.1.0]hexane-3-carboxamide | *** | 1.58 (A) | 622 |
| 196 | 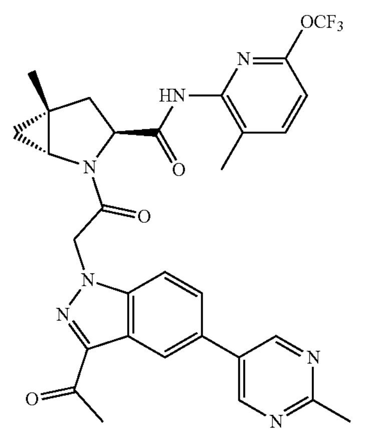 [SMILES: CC(=O)c1nn(CC(=O)N2[C@H](C(=O)Nc3nc(OC(F)(F)F)ccc3C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-5-methyl-N-(3-methyl-6-(trifluoromethoxy)-pyridin-2-yl)-2-azabicyclo[3.1.0]hexane-3-carboxamide | *** | 2.04 (A) | 608 |
| 197 | 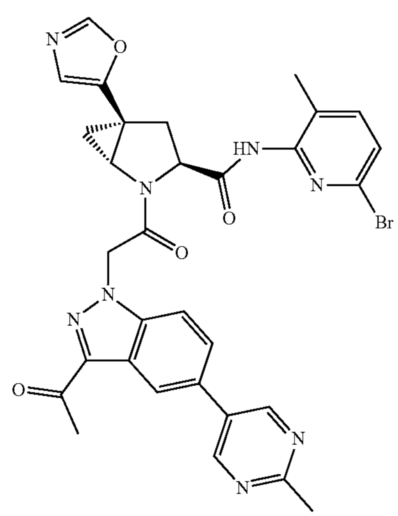 [SMILES: CC(=O)c1nn(CC(=O)N2[C@H](C(=O)Nc3nc(Br)ccc3C)C[C@@]3(c4cnco4)C[C@@H]23)c2ccc(-c3cnc(C)nc3)cc12] | (1R,3S,5S)-2-(2-(3-acetyl-5-(2-methylpyrimidin-5-yl)-1H-indazol-1-yl)acetyl)-N-(6-bromo-3-methylpyridin-2-yl)-5-(oxazol-5-yl)-2-azabicyclo[3.1.0]hexane-3-carboxamide | *** | 1.55 (A) | 655 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 198 | 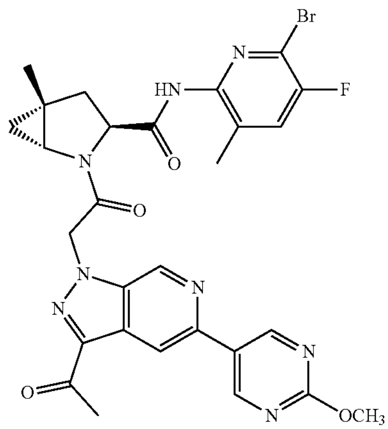 | (1R,3S,5R)-2-(2-(3-acetyl-5-(2-methoxypyrimidin-5-yl)-1H-pyrazolo[3,4-c]pyridin-1-yl)acetyl)-N-(6-bromo-5-fluoro-3-methylpyridin-2-yl)-5-methyl-2-azabicyclo[3.1.0]hexane-3-carboxamide | *** | 1.92 (A) | 637 |
| 199 | 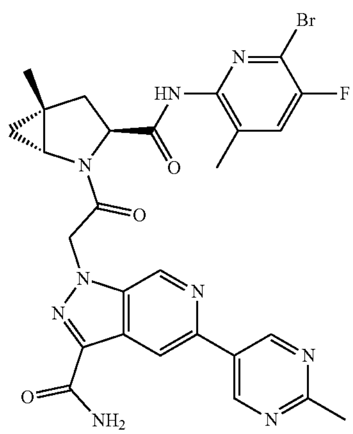 [SMILES: Cc1ncc(-c2cc3c(C(N)=O)nn(CC(=O)N4[C@H](C(=O)Nc5nc(Br)c(F)cc5C)C[C@@]5(C)C[C@@H]45)c3cn2)cn1] | 1-(2-((1R,3S,5R)-3-((6-bromo-5-fluoro-3-methylpyridin-2-yl)carbamoyl)-5-methyl-2-azabicyclo[3.1.0]hexan-2-yl)-2-oxoethyl)-5-(2-methylpyrimidin-5-yl)-1H-pyrazolo[3,4-c]pyridine-3-carboxamide | *** | 1.39 (A) | 623 |
| 200 | 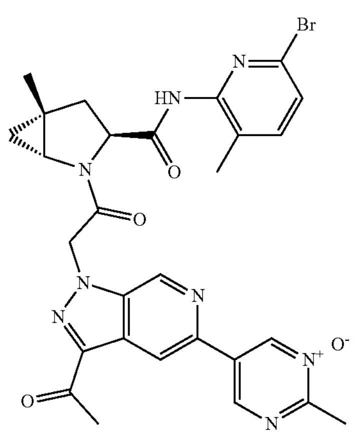 | 5-(3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-pyrazolo[3,4-c]pyridin-5-yl)-2-methylpyrimidine 1-oxide | *** | 2.97 (B) | 619 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 201 | 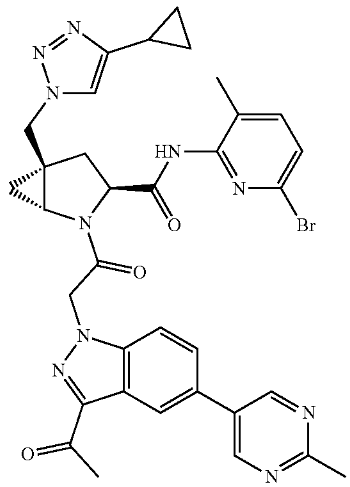 [SMILES: CC(=O)c1nn(CC(=O)N2[C@H](C(=O)Nc3nc(Br)ccc3C)C[C@@]3(Cn4cc(C5CC5)nn4)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-methylpyridin-2-yl)-5-((4-cyclopropyl-1H-1,2,3-triazol-1-yl)methyl)-2-azabicyclo[3.1.0]hexane-3-carboxamide | *** | 1.65 (A) | 709 |
| 202 | 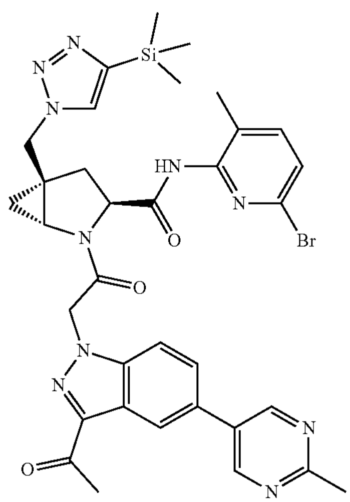 [SMILES: CC(=O)c1nn(CC(=O)N2[C@H](C(=O)Nc3nc(Br)ccc3C)C[C@@]3(Cn4cc([Si](C)(C)C)nn4)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-methylpyridin-2-yl)-5-((4-(trimethylsilyl)-1H-1,2,3-triazol-1-yl)methyl)-2-azabicyclo[3.1.0]hexane-3-carboxamide | *** | 1.99 (A) | 741 |
| 203 | 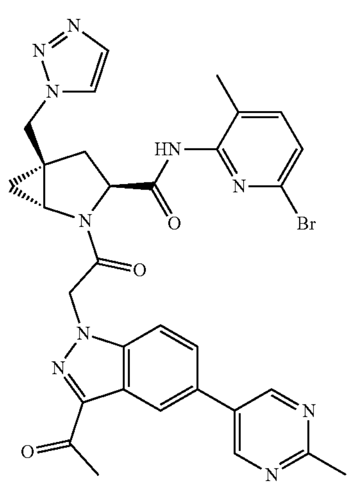 [SMILES: CC(=O)c1nn(CC(=O)N2[C@H](C(=O)Nc3nc(Br)ccc3C)C[C@@]3(Cn4ccnn4)C[C@@H]23)c2ccc(-c3cnc(C)nc3)cc12] | (1R,3S,5R)-5-((1H-1,2,3-triazol-1-yl)methyl)-2-(2-(3-acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide | *** | 1.41 (A) | 669 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 204 | 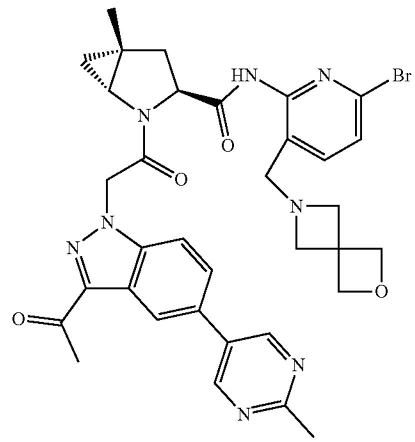 [SMILES: CC(=O)c1nn(CC(=O)N2[C@H](C(=O)Nc3nc(Br)ccc3CN3CC4(COC4)C3)C[C@@]3(C)C[C@@H]23)c2ccc(-c3cnc(C)nc3)cc12] | (1R,3S,5R)-N-(3-(2-oxa-6-azaspiro[3.3]heptan-6-ylmethyl)-6-bromopyridin-2-yl)-2-(2-(3-acetyl-5-(2-methylpyrimidin-5-yl)-1H-indazol-1-yl)acetyl)-5-methyl-2-azabicyclo[3.1.0]hexane-3-carboxamide | *** | 1.16 (A) | 699 |
| 205 | 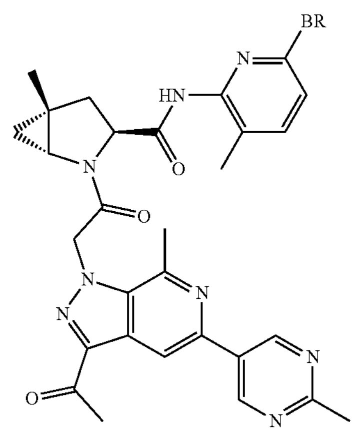 | (1R,3S,5R)-2-(2-(3-acetyl-7-methyl-5-(2-methylpyrimidin-5-yl)-1H-pyrazolo[3,4-c]pyridin-1-yl)acetyl)-N-(6-bromo-3-methylpyridin-2-yl)-5-methyl-2-azabicyclo[3.1.0] | *** | 1.78 (A) | 617 |
| 206 | 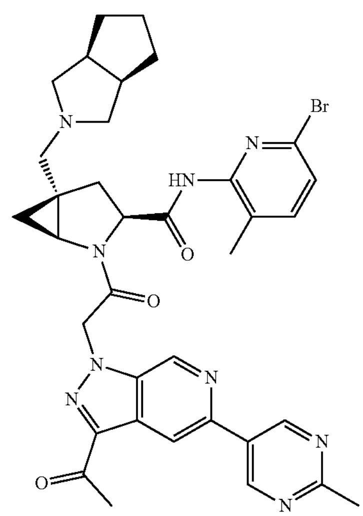 [SMILES: CC(=O)c1nn(CC(=O)N2[C@H]3C[C@@]3(CN3C[C@H]4CCC[C@H]4C3)C[C@H]2C(=O)Nc2nc(Br)ccc2C)c2cnc(-c3cnc(C)nc3)cc12] | (1S,3S,5S)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-(((3aR,6aS)-hexahydrocyclopenta[c]pyrrol-2(1H)-yl)methyl)-2-azabicyclo[3.1.0]hexane-3-carboxamide | *** | 2.15 (B) | 712 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 207 | 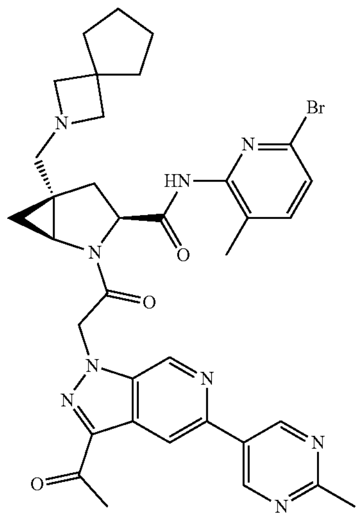 [SMILES: CC(=O)c1nn(CC(=O)N2[C@H]3C[C@@]3(CN3CC4(CCCC4)C3)C[C@H]2C(=O)Nc2nc(Br)ccc2C)c2cnc(-c3cnc(C)nc3)cc12] | (1S,3S,5S)-5-((2-azaspiro[3.4]octan-2-yl)methyl)-2-(2-(3-acetyl-5-(2-met-hylpyrimidin-5-yl)-1H-pyrazolo[3,4-c]pyridin-1-yl)acetyl)-N-(6-bromo-3-methylpyridin-2-yl)-2-azabicyclo[3.1.0]hexane-3-carboxamide | *** | 2.16 (B) | 712 |
| 208 | 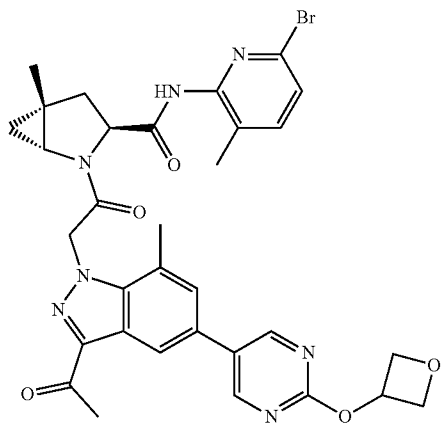 [SMILES: CC(=O)c1nn(CC(=O)N2[C@H](C(=O)Nc3nc(Br)ccc3C)C[C@@]3(C)C[C@@H]23)c2c(C)cc(-c3cnc(OC4COC4)nc3)cc12] | (1R,3S,5R)-2-(2-(3-acetyl-7-methyl-5-(2-(oxetan-3-yloxy)pyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 9.30 (D) | 676 (M + 2) |
| 209 | 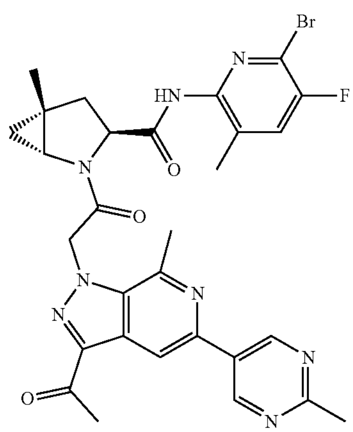 [SMILES: CC(=O)c1nn(CC(=O)N2[C@H](C(=O)Nc3nc(Br)c(F)cc3C)C[C@@]3(C)C[C@@H]23)c2c(C)nc(-c3cnc(C)nc3)cc12] | (1R,3S,5R)-2-(2-(3-acetyl-7-methyl-5-(2-methylpyrimidin-5-yl)-1H-pyrazolo[3,4-c]pyridin-1-yl)acetyl)-N-(6-bromo-5-fluoro-3-methylpyridin-2-yl)-5-methyl-2-azabicyclo[3.1.0]hexane-3-carboxamide | *** | 1.86 (A) | 635 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 210 | 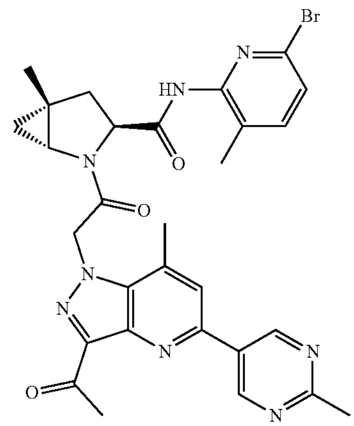 [SMILES: CC(=O)c1nn(CC(=O)N2[C@H](C(=O)Nc3nc(Br)ccc3C)C[C@@]3(C)C[C@@H]23)c2c(C)cc(-c3cnc(C)nc3)nc12] | (1R,3S,5R)-2-(2-(3-acetyl-7-methyl-5-(2-methylpyrimidin-5-yl)-1H-pyrazolo[4,3-b]pyridin-1-yl)acetyl)-N-(6-bromo-3-methylpyridin-2-yl)-5-methyl-2-azabicyclo[3.1.0]hexane-3-carboxamide | * | 1.80 (A) | 617 |
| 211 | 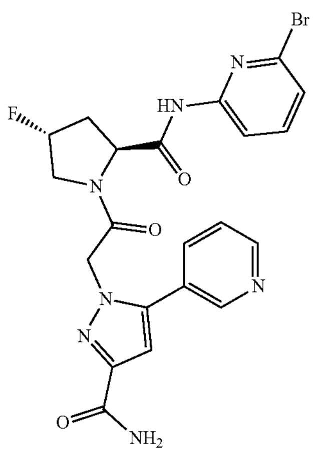 [SMILES: NC(=O)c1cc(-c2cccnc2)n(CC(=O)N2C[C@H](F)C[C@H]2C(=O)Nc2cccc(Br)n2)n1] | 1-(2-((2S,4R)-2-((6-bromopyridin-2-yl)carbamoyl)-4-fluoropyrrolidin-1-yl)-2-oxoethyl)-5-(pyridin-3-yl)-1H-pyrazole-3-carboxamide | *** | 0.97 (A) | 516 |
| 212 | 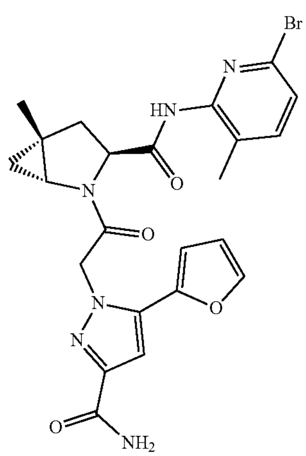 [SMILES: Cc1ccc(Br)nc1NC(=O)[C@@H]1C[C@@]2(C)C[C@H]2N1C(=O)Cn1nc(C(N)=O)cc1-c1ccco1] | (1R,3S,5R)-N-(6-bromo-3-methylpyridin-2-yl)-2-(2-(3-carbamoyl-5-(furan-2-yl)-1H-pyrazol-1-yl)acetyl)-5-methyl-2-azabicyclo[3.1.0]hexane-3-carboxamide | *** | 1.56 (A) | 527 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 213 | 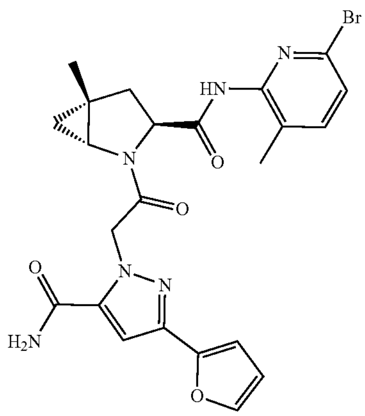 [SMILES: Cc1ccc(Br)nc1NC(=O)[C@@H]1C[C@@]2(C)C[C@H]2N1C(=O)Cn1nc(-c2ccco2)cc1C(N)=O] | (1R,3S,5R)-N-(6-bromo-3-methylpyridin-2-yl)-2-(2-(5-carbamoyl-3-(furan-2-yl)-1H-pyrazol-1-yl)acetyl)-5-methyl-2-azabicyclo[3.1.0]hexane-3-carboxamide | ** | 1.67(A) | 527 |
| 214 | 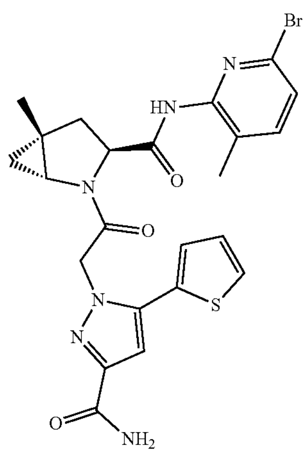 | (1R,3S,5R)-N-(6-bromo-3-methylpyridin-2-yl)-2-(2-(3-carbamoyl-5-(thiophen-2-yl)-1H-pyrazol-1-yl)acetyl)-5-methyl-2-azabicyclo[3.1.0]hexane-3-carboxamide | *** | 1.65 (A) | 543 |
| 215 | 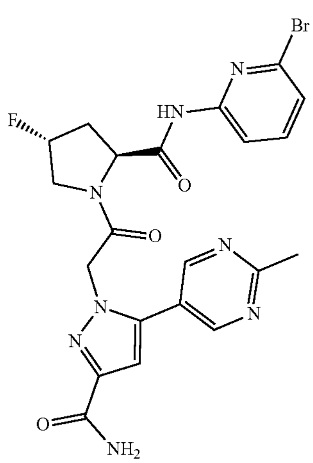 [SMILES: Cc1ncc(-c2cc(C(N)=O)nn2CC(=O)N2C[C@H](F)C[C@H]2C(=O)Nc2cccc(Br)n2)cn1] | 1-(2-((2S,4R)-2-((6-broyl)carbamoyl)-4-mopyridin-2-fluoropyrrolidin-1-yl)-2-oxoethyl)-5-(2-methylpyrimidin-5-yl)-1H-pyrazole-3-carboxamide | * | 1.15 (A) | 531 |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 216 | 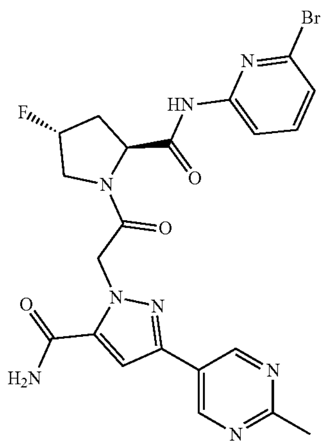 [SMILES: Cc1ncc(-c2cc(C(N)=O)n(CC(=O)N3C[C@H](F)C[C@H]3C(=O)Nc3cccc(Br)n3)n2)cn1] | 1-(2-((2S,4R)-2-((6-bromopyridin-2-yl)carbamoyl)-4-fluoropyrrolidin-1-yl)-2-oxoethyl)-3-(2-methylpyrimidin-5-yl)-1H-pyrazole-5-carboxamide | ** | 1.04 (A) | 531 |
| 217 | 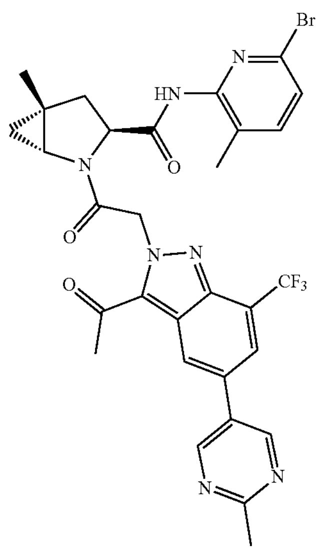 [SMILES: CC(=O)c1c2cc(-c3cnc(C)nc3)cc(C(F)(F)F)c2nn1CC(=O)N1[C@H](C(=O)Nc2nc(Br)ccc2C)C[C@@]2(C)C[C@@H]12] | (1R,3S,5R)-2-(2-(3-acetyl-5-(2-methylpyrimidin-5-yl)-7-(trifluoromethyl)-2H-indazol-2-yl)acetyl)-N-(6-bromo-3-methylpyridin-2-yl)-5-methyl-2-azabicyclo[3.1.0]hexane-3-carboxamide | * | 3.62 (B) | 670 |
| 218 | 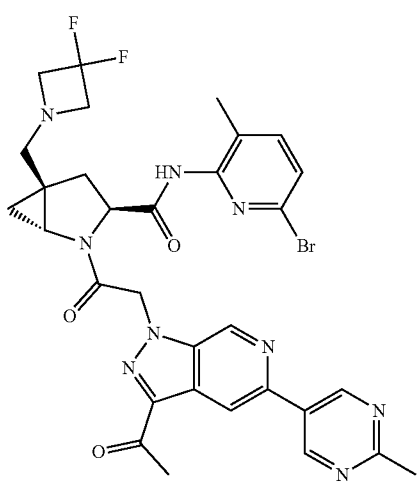 [SMILES: CC(=O)c1nn(CC(=O)N2[C@H](C(=O)Nc3nc(Br)ccc3C)C[C@@]3(CN4CC(F)(F)C4)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-((3,3-difluoroazetidin-1-yl)methyl)-2-azabicyclo[3.1.0]hexane-3-carboxamide | | | |

TABLE 6-continued

Non-limiting Examples of Compounds of the Present Invention

| Cmp No. | Structure | Name | IC$_{50}$ | RT min (Method A, B, C or D) | MS (M + 1) |
|---|---|---|---|---|---|
| 219 | 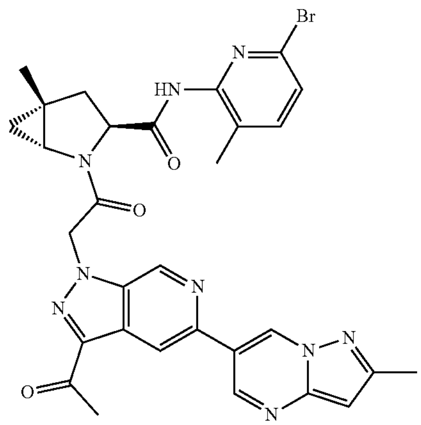 [SMILES: CC(=O)c1nn(CC(=O)N2[C@H](C(=O)Nc3nc(Br)ccc3C)C[C@@]3(C)C[C@@H]23)c2cnc(-c3cnc4cc(C)nn4c3)cc12] | (1R,3S,5R)-2-(2-(3-acetyl-5-(2-methyl-pyrazolo[1,5-a]pyrimidin-6-yl)-1H-pyrazolo[3,4-c]pyridin-1-yl)acetyl)-N-(6-bromo-3-methylpyridin-2-yl)-5-methyl-2-azabicyclo[3.1.0]hexane-3-carboxamide | *** | 1.94 (A) | 642 |
| 231 | 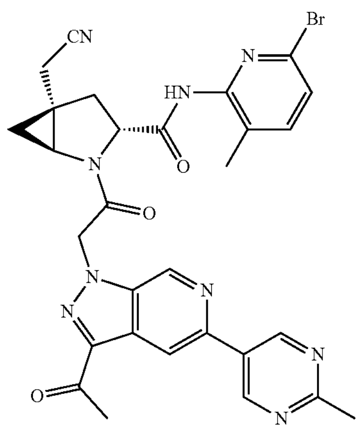 [SMILES: CC(=O)c1nn(CC(=O)N2[C@@H](C(=O)Nc3nc(Br)ccc3C)C[C@]3(CC#N)C[C@H]23)c2cnc(-c3cnc(C)nc3)cc12] | (1S,3S,5S)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-(cyanomethyl)-2-azabicyclo[3.1.0]hexane-3-carboxamide | | 2.45 (B) | 628 |
| 232 | 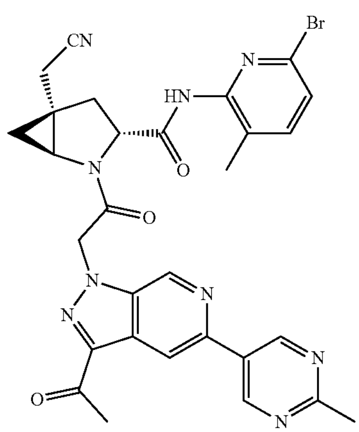 [SMILES: CC(=O)c1nn(CC(=O)N2[C@@H](C(=O)Nc3nc(Br)ccc3C)C[C@]3(CC#N)C[C@H]23)c2cnc(-c3cnc(C)nc3)cc12] | (1S,3R,5S)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-(cyanomethyl)-2-azabicyclo[3.1.0]hexane-3-carboxamide | | 2.34 (B) | 628 |

TABLE 6-continued

Non-limiting Examples of Compounds of the Present Invention

| Cmp No. | Structure | Name | $IC_{50}$ | RT min (Method A, B, C or D) | MS (M + 1) |
|---|---|---|---|---|---|
| 233 | 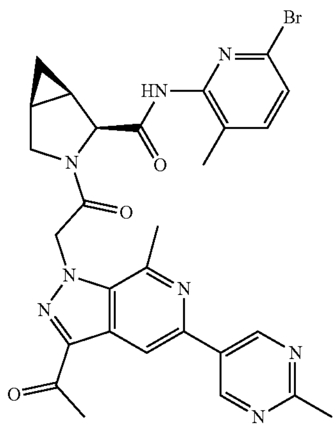 [SMILES: CC(=O)c1nn(CC(=O)N2C[C@H]3C[C@H]3[C@H]2C(=O)Nc2nc(Br)ccc2C)c2c(C)nc(-c3cnc(C)nc3)cc12] | (1R,2S,5S)-3-(2-(3-acetyl-7-methyl-5-(2-methylpyrimidin-5-yl)-1H-pyrazolo[3,4-c]pyridin-1-yl)acetyl)-N-(6-bromo-3-methylpyridin-2-yl)-3-azabicyclo[3.1.0]hexane-2-carboxamide | | 1.58 (A) | 603 |

TABLE 7

Additional Non-limiting Examples of Compounds of the Present Invention

| Cmp No. | Structure | Name | $IC_5$ (Stars) | RT min (A, B, C or D) | MS (M + 1) |
|---|---|---|---|---|---|
| 234 | 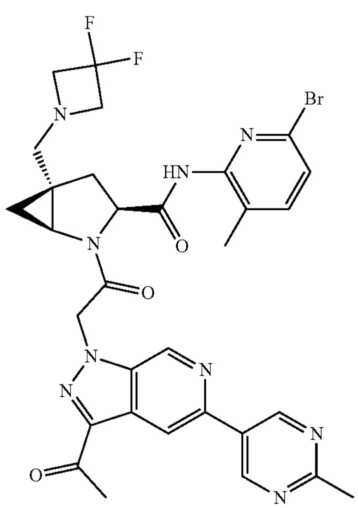 [SMILES: CC(=O)c1nn(CC(=O)N2[C@H]3C[C@@]3(CN3CC(F)(F)C3)C[C@H]2C(=O)Nc2nc(Br)ccc2C)c2cnc(-c3cnc(C)nc3)cc12] | (1S,3S,5S)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-((3,3-difluoroazetidin-1-yl)methyl)-2-azabicyclo[3.1.0]hexane-3-carboxamide | | | |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 235 | 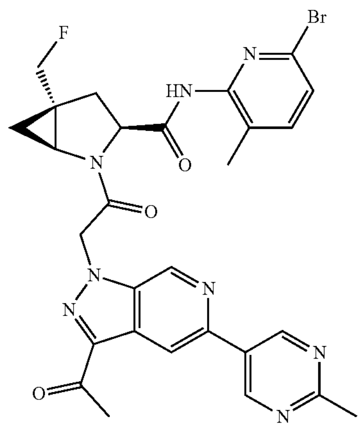 | (1S,3S,5R)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-(fluoromethyl)-2-azabicyclo[3.1.0]hexane-3-carboxamide | *** | 3.06 (B) | 621 |
| 237 | 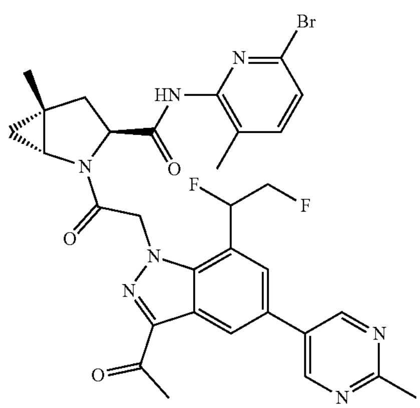 [SMILES: CC(=O)c1nn(CC(=O)N2[C@H](C(=O)Nc3nc(Br)ccc3C)C[C@@]3(C)C[C@@H]23)c2c(C(F)CF)cc(-c3cnc(C)nc3)cc12] | (1R,3S,5R)-2-(2-(3-acetyl-7-(1,2-difluoroethyl)-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 3.12 (B) | 666 |
| 238 | 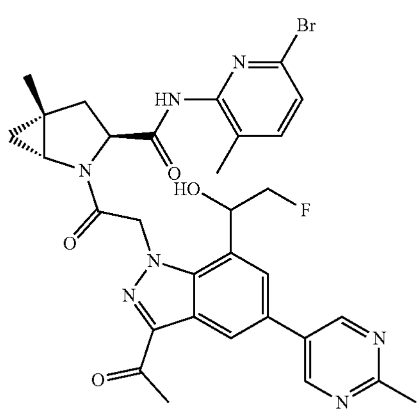 [SMILES: CC(=O)c1nn(CC(=O)N2[C@H](C(=O)Nc3nc(Br)ccc3C)C[C@@]3(C)C[C@@H]23)c2c(C(O)CF)cc(-c3cnc(C)nc3)cc12] | (1R,3S,5R)-2-(2-(3-acetyl-7-(2-fluoro-1-hydroxyethyl)-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 2.70 (B) | 664 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 239 | 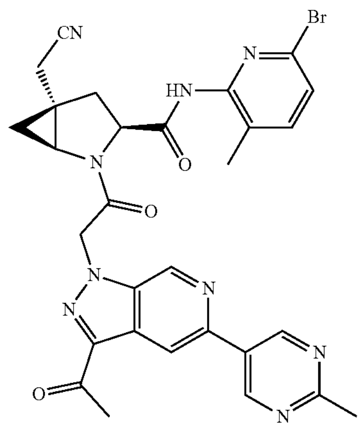 [SMILES: CC(=O)c1nn(CC(=O)N2[C@H]3C[C@@]3(CC#N)C[C@H]2C(=O)Nc2nc(Br)ccc2C)c2cnc(-c3cnc(C)nc3)cc12] | (1S,3S,5S)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-(cyanomethyl)-2-azabicyclo[3.1.0]hexane-3-carboxamide | ** | 2.45 (B) | 628 |
| 240 | 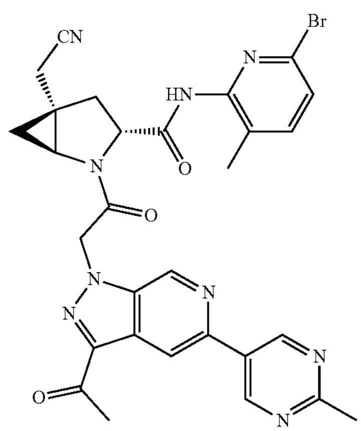 [SMILES: CC(=O)c1nn(CC(=O)N2[C@@H](C(=O)Nc3nc(Br)ccc3C)C[C@]3(CC#N)C[C@H]23)c2cnc(-c3cnc(C)nc3)cc12] | (1S,3R,5S)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-(cyanomethyl)-2-azabicyclo[3.1.0]hexane-3-carboxamide | ** | 2.34 (B) | 628 |
| 241 | 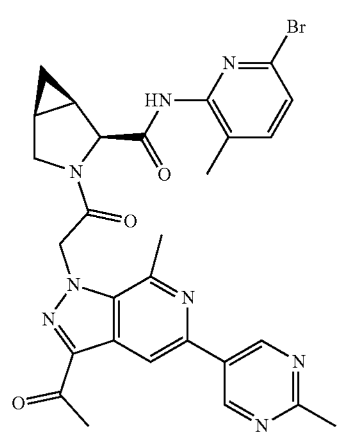 [SMILES: CC(=O)c1nn(CC(=O)N2C[C@H]3C[C@H]3[C@H]2C(=O)Nc2nc(Br)ccc2C)c2c(C)nc(-c3cnc(C)nc3)cc12] | (1R,2S,5S)-3-(2-(3-acetyl-7-methyl-5-(2-methylpyrimidin-5-yl)-1H-pyrazolo[3,4-c]pyridin-1-yl)acetyl)-N-(6-bromo-3-methylpyridin-2-yl)-3-azabicyclo[3.1.0]hexane-2-carboxamide | *** | 1.58 (A) | 603 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 245 | 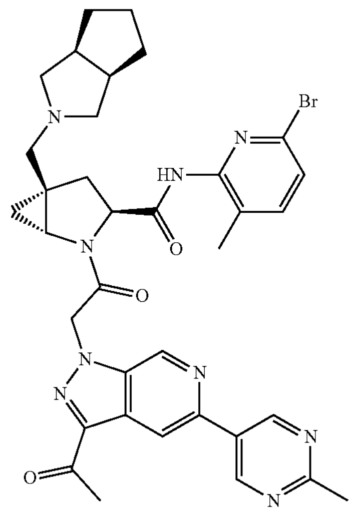 [SMILES: CC(=O)c1nn(CC(=O)N2[C@H](C(=O)Nc3nc(Br)ccc3C)C[C@@]3(CN4C[C@H]5CCC[C@H]5C4)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-(((3aR,6aS)-hexahydrocyclopenta[c]pyrrol-2(1H)-yl)methyl)-2-azabicyclo[3.1.0]hexane-3-carboxamide | *** | 2.44 (B) | 712 |
| 246 | 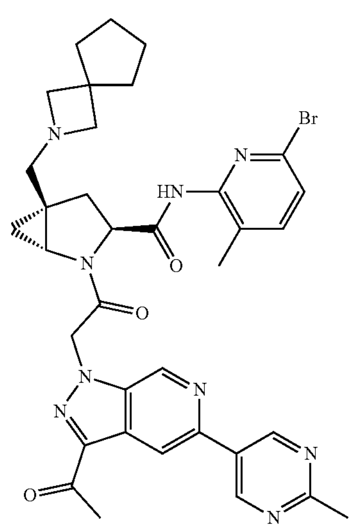 [SMILES: CC(=O)c1nn(CC(=O)N2[C@H](C(=O)Nc3nc(Br)ccc3C)C[C@@]3(CN4CC5(CCCC5)C4)C[C@@H]23)c2cnc(-c3cnc(C)nc3)cc12] | (1R,3S,5R)-5-(2-azaspiro[3.4]octan-2-ylmethyl)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-2-azabicyclo[3.1.0]hexane-3-carboxamide | *** | 2.49 (B) | 712 |

TABLE 7-continued

Additional Non-limiting Examples of Compounds of the Present Invention

| Cmp No. | Structure | Name | IC₅ (Stars) | RT min (A, B, C or D) | MS (M + 1) |
|---|---|---|---|---|---|
| 247 | 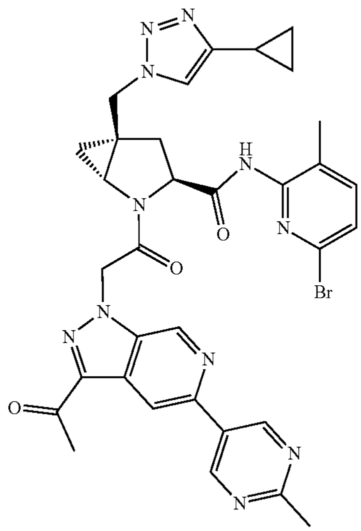 [SMILES: CC(=O)c1nn(CC(=O)N2[C@H](C(=O)Nc3nc(Br)ccc3C)C[C@@]3(Cn4cc(C5CC5)nn4)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-((4-cyclopropyl-1H-1,2,3-triazol-1-yl)methyl)-2-azabicyclo[3.1.0]hexane-3-carboxamide | *** | 1.56 (A) | 710 |
| 248 | 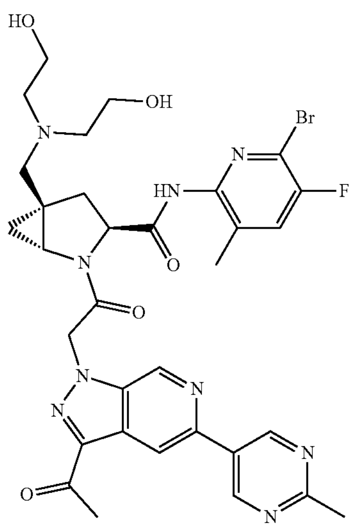 [SMILES: CC(=O)c1nn(CC(=O)N2[C@H](C(=O)Nc3nc(Br)c(F)cc3C)C[C@@]3(CN(CCO)CCO)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-5-((bis(2-hydroxyethyl)amino)methyl)-N-(6-bromo-5-fluoro-3-methylpyridin-2-yl)-2-azabicyclo[3.1.0]hexane-3-carboxamide | *** | 2.11 (B) | 724 |
| 249 | 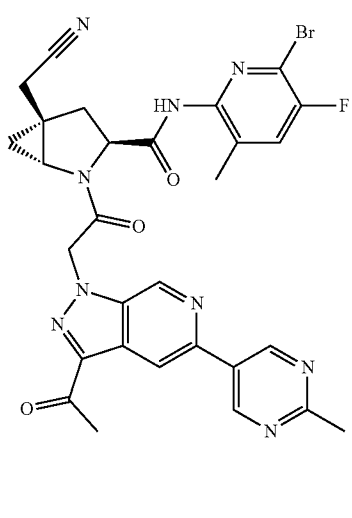 [SMILES: CC(=O)c1nn(CC(=O)N2[C@H](C(=O)Nc3nc(Br)c(F)cc3C)C[C@@]3(CC#N)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-5-fluoro-3-methylpyridin-2-yl)-5-(cyanomethyl)-2-azabicyclo[3.1.0]hexane-3-carboxamide | *** | 3.04 (B) | 646 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 250 | 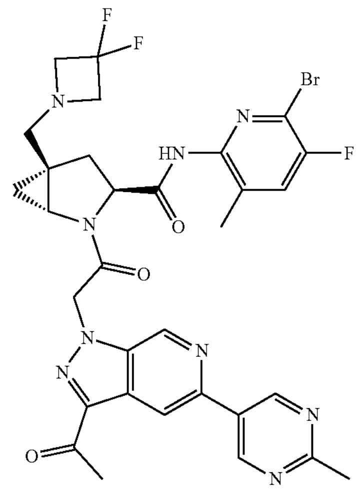 [SMILES: CC(=O)c1nn(CC(=O)N2[C@H](C(=O)Nc3nc(Br)c(F)cc3C)C[C@@]3(CN4CC(F)(F)C4)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-5-fluoro-3-methylpyridin-2-yl)-5-((3,3-difluoroazetidin-1-yl)methyl)-2-azabicyclo[3.1.0]hexane-3-carboxamide | *** | 2.07 (B) | 712 |
| 251 | 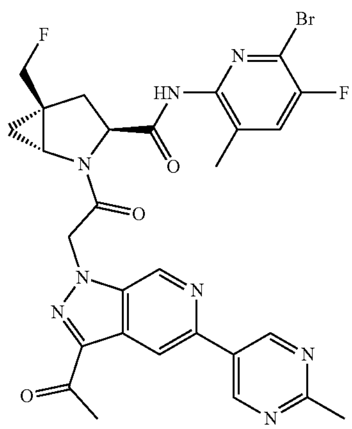 [SMILES: CC(=O)c1nn(CC(=O)N2[C@H](C(=O)Nc3nc(Br)c(F)cc3C)C[C@@]3(CF)C[C@@H]23)c2cnc(-c3cnc(C)nc3)cc12] | (1R,3S,5S)-2-(2-(3-acetyl-5-(2-methylpyrimidin-5-yl)-1H-pyrazolo[3,4-c]pyridin-1-yl)acetyl)-N-(6-bromo-5-fluoro-3-methylpyridin-2-yl)-5-(fluoromethyl)-2-azabicyclo[3.1.0]hexane-3-carboxamide | *** | 2.88 (B) | 639 |
| 252 | 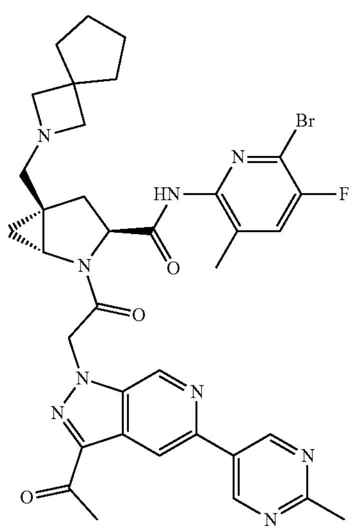 [SMILES: CC(=O)c1nn(CC(=O)N2[C@H](C(=O)Nc3nc(Br)c(F)cc3C)C[C@@]3(CN4CC5(CCCC5)C4)C[C@@H]23)c2cnc(-c3cnc(C)nc3)cc12] | (1R,3S,5R)-5-(2-azaspiro[3.4]octan-2-ylmethyl)-2-(2-(3-acetyl-5-(2-methylpyrimidin-5-yl)-1H-pyrazolo[3,4-c]pyridin-1-yl)acetyl)-N-(6-bromo-5-fluoro-3-methylpyridin-2-yl)-2-azabicyclo[3.1.0]hexane-3-carboxamide | *** | 2.32 (B) | 730 |

TABLE 7-continued

Additional Non-limiting Examples of Compounds of the Present Invention

| Cmp No. | Structure | Name | IC₅ (Stars) | RT min (A, B, C or D) | MS (M + 1) |
|---|---|---|---|---|---|
| 253 | 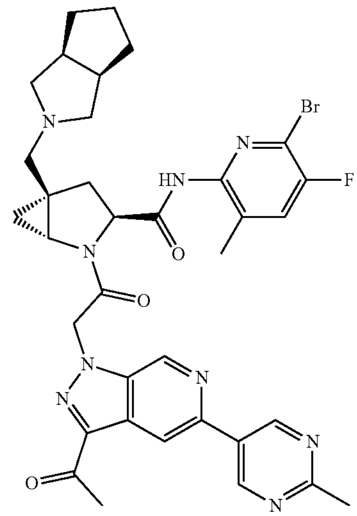 [SMILES: CC(=O)c1nn(CC(=O)N2[C@H](C(=O)Nc3nc(Br)c(F)cc3C)C[C@@]3(CN4C[C@H]5CCC[C@H]5C4)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-5-fluoro-3-methylpyridin-2-yl)-5-(((3aR,6aS)-hexahydrocyclopenta[c]pyrrol-2(1H)-yl)methyl)-2-azabicyclo[3.1.0]hexane-3-carboxamide | *** | 2.26 (B) | 730 |
| 254 | 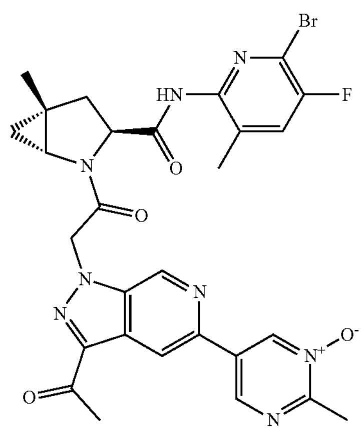 [SMILES: CC(=O)c1nn(CC(=O)N2[C@H](C(=O)Nc3nc(Br)c(F)cc3C)C[C@@]3(C)C[C@@H]23)c2cnc(-c3cnc(C)[n+]([O-])c3)cc12] | 5-(3-acetyl-1-(2-(((1R,3S,5R)-3-((6-bromo-5-fluoro-3-methylpyridin-2-yl)carbamoyl)-5-methyl-2-azabicyclo[3.1.0]hexan-2-yl)-2-oxoethyl)-1H-pyrazolo[3,4-c]pyridin-5-yl)-2-methylpyrimidine 1-oxide | *** | 2.50 (B) | 637 |
| 255 | 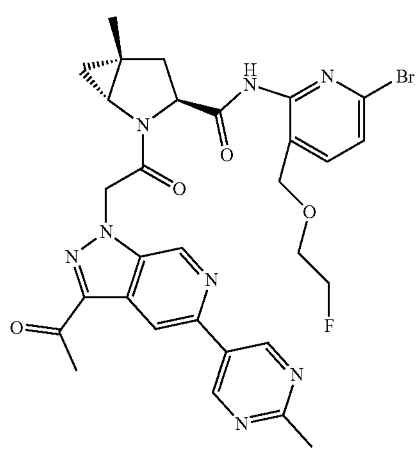 [SMILES: CC(=O)c1nn(CC(=O)N2[C@H](C(=O)Nc3nc(Br)ccc3COCCF)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-((2-fluoroethoxy)methyl)pyridin-2-yl)-5-methyl-2-azabicyclo[3.1.0]hexane-3-carboxamide | *** | 1.77 (A) | 666 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 256 | 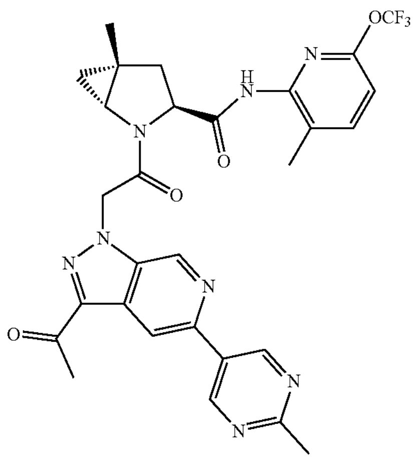 [SMILES: CC(=O)c1nn(CC(=O)N2[C@H](C(=O)Nc3nc(OC(F)(F)F)ccc3C)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-5-methyl-N-(3-methyl-6-(trifluoromethoxy)pyridin-2-yl)-2-azabicyclo[3.1.0]hexane-3-carboxamide | *** | 1.93 (A) | 609 |
| 257 | 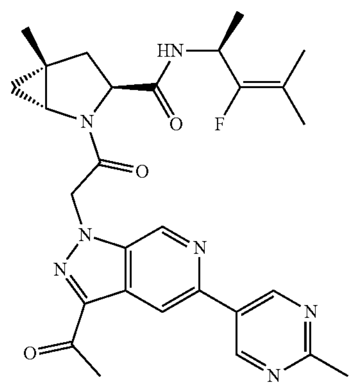 [SMILES: CC(=O)c1nn(CC(=O)N2[C@H](C(=O)N[C@@H](C)C(F)=C(C)C)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-((S)-3-fluoro-4-methylpent-3-en-2-yl)-5-methyl-2-azabicyclo[3.1.0]hexane-3-carboxamide | *** | 2.16 (A) | 533 |
| 258 | 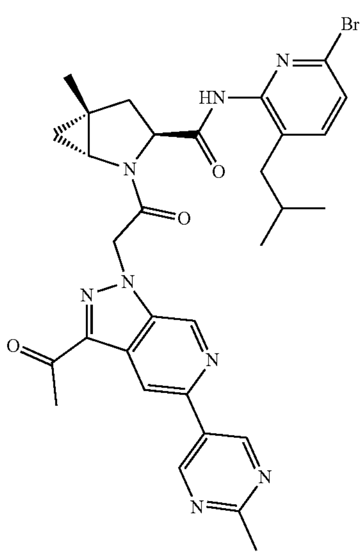 [SMILES: CC(=O)c1nn(CC(=O)N2[C@H](C(=O)Nc3nc(Br)ccc3CC(C)C)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-isobutylpyridin-2-yl)-5-methyl-2-azabicyclo[3.1.0]hexane-3-carboxamide | *** | 2.05 (A) | 645 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 259 | 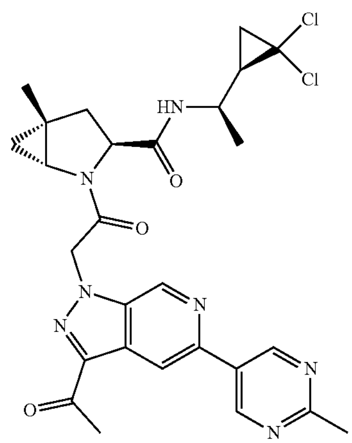 [SMILES: CC(=O)c1nn(CC(=O)N2[C@H](C(=O)N[C@H](C)[C@H]3CC3(Cl)Cl)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-((R)-1-((R)-2,2-dichlorocyclopropyl)ethyl)-5-methyl-2-azabicyclo[3.1.0]hexane-3-carboxamide | *** | 2.11 (A) | 569 |
| 260 | 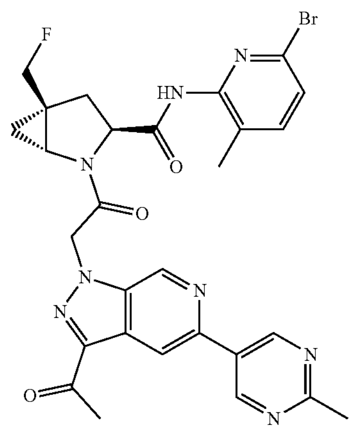 [SMILES: CC(=O)c1nn(CC(=O)N2[C@H](C(=O)Nc3nc(Br)ccc3C)C[C@@]3(CF)C[C@@H]23)c2cnc(-c3cnc(C)nc3)cc12] | (1R,3S,5S)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-(fluoromethyl)-2-azabicyclo[3.1.0]hexane-3-carboxamide | *** | 2.95 (B) | 621 |
| 261 | 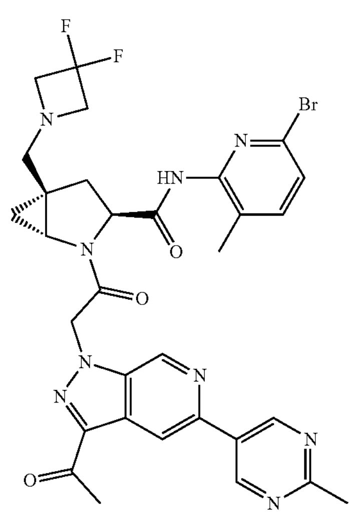 [SMILES: CC(=O)c1nn(CC(=O)N2[C@H](C(=O)Nc3nc(Br)ccc3C)C[C@@]3(CN4CC(F)(F)C4)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-((3,3-difluoroazetidin-1-yl)methyl)-2-azabicyclo[3.1.0]hexane-3-carboxamide | *** | 2.47 (B) | 694 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 262 | 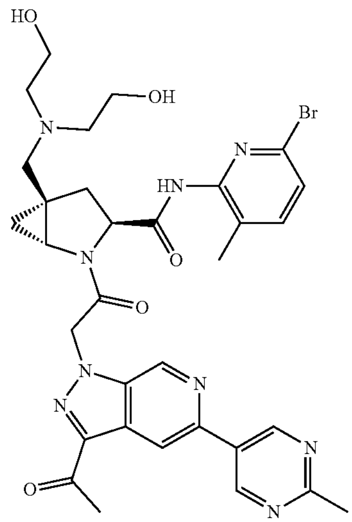 [SMILES: CC(=O)c1nn(CC(=O)N2[C@H](C(=O)Nc3nc(Br)ccc3C)C[C@@]3(CN(CCO)CCO)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-5-((bis(2-hydroxy-ethyl)amino)methyl)-N-(6-bromo-3-methylpyridin-2-yl)-2-azabicyclo[3.1.0]hexane-3-carboxamide | *** | 2.34 (B) | 706 |
| 263 | 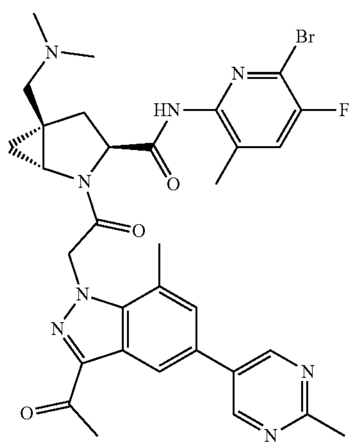 [SMILES: CC(=O)c1nn(CC(=O)N2[C@H](C(=O)Nc3nc(Br)c(F)cc3C)C[C@@]3(CN(C)C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-5-fluoro-3-methylpyridin-2-yl)-5-((dimethylamino)methyl)-2-azabicyclo[3.1.0]hexane-3-carboxamide | *** | 2.56 (B) | 677 |
| 264 | 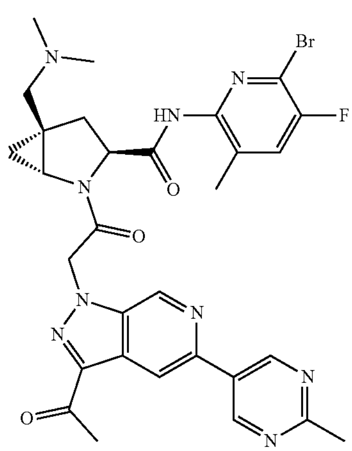 [SMILES: CC(=O)c1nn(CC(=O)N2[C@H](C(=O)Nc3nc(Br)c(F)cc3C)C[C@@]3(CN(C)C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-5-fluoro-3-methylpyridin-2-yl)-5-((dimethylamino)methyl)-2-azabicyclo[3.1.0]hexane-3-carboxamide | *** | 2.33 (B) | 664 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 265 | 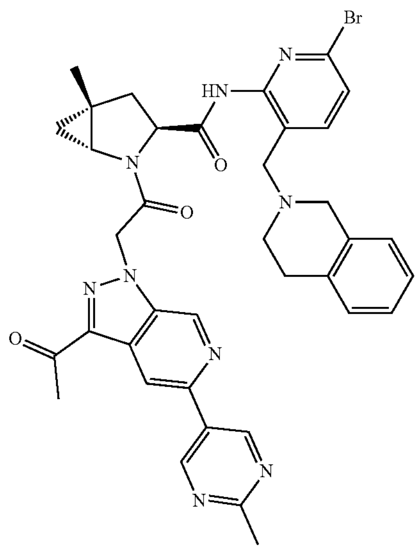 [SMILES: CC(=O)c1nn(CC(=O)N2[C@H](C(=O)Nc3nc(Br)ccc3CN3CCc4ccccc4C3)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-((3,4-dihydroisoquinolin-2(1H)-yl)methyl)pyridin-2-yl)-5-methyl-2-azabicyclo[3.1.0]hexane-3-carboxamide | *** | 1.46 (A) | 734 |
| 269 | 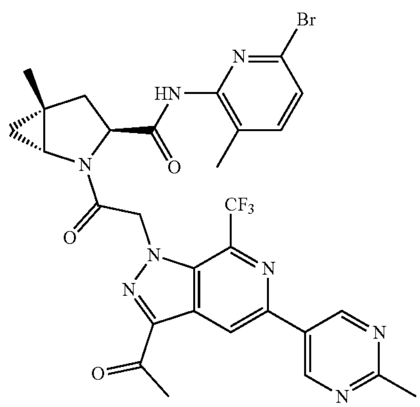 [SMILES: CC(=O)c1nn(CC(=O)N2[C@H](C(=O)Nc3nc(Br)ccc3C)C[C@@]3(C)C[C@@H]23)c2c(C(F)(F)F)nc(-c3cnc(C)nc3)cc12] | (1R,3S,5R)-2-(2-(3-acetyl-5-(2-methylpyrimidin-5-yl)-7-(trifluoromethyl)-1H-pyrazolo[3,4-c]pyridin-1-yl)acetyl)-N-(6-bromo-3-methylpyridin-2-yl)-5-methyl-2-azabicyclo[3.1.0]hexane-3-carboxamide | *** | 3.54 (B) | 671 |
| 270 | 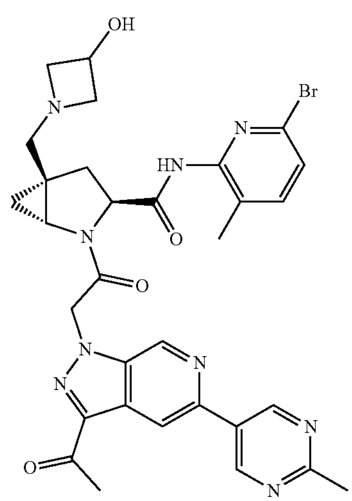 [SMILES: CC(=O)c1nn(CC(=O)N2[C@H](C(=O)Nc3nc(Br)ccc3C)C[C@@]3(CN4CC(O)C4)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-((3-hydroxyazetidin-1-yl)methyl)-2-azabicyclo[3.1.0]hexane-3-carboxamide | *** | 1.84 (B) | 674 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 271 | 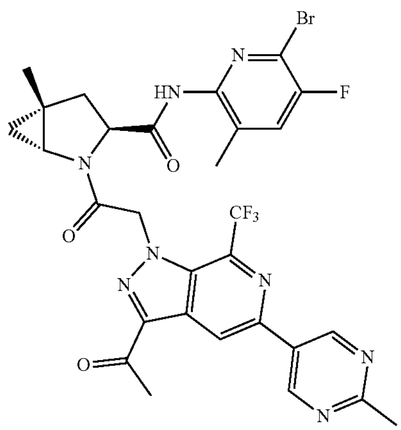 [SMILES: CC(=O)c1nn(CC(=O)N2[C@H](C(=O)Nc3nc(Br)c(F)cc3C)C[C@@]3(C)C[C@@H]23)c2c(C(F)(F)F)nc(-c3cnc(C)nc3)cc12] | (1R,3S,5R)-2-(2-(3-acetyl-5-(2-methylpyrimidin-5-yl)-7-(trifluoromethyl)-1H-pyrazolo[3,4-c]pyridin-1-yl)acetyl)-N-(6-bromo-5-fluoro-3-methylpyridin-2-yl)-5-methyl-2-azabicyclo[3.1.0]hexane-3-carboxamide | *** | 3.68 (B) | 689 |
| 272 | 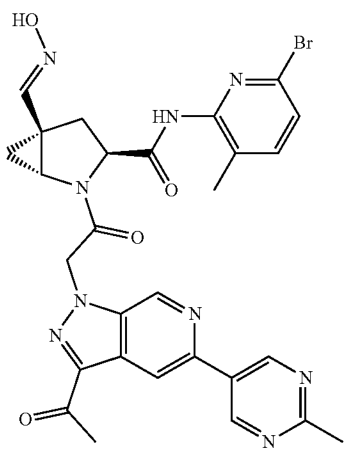 [SMILES: CC(=O)c1nn(CC(=O)N2[C@H](C(=O)Nc3nc(Br)ccc3C)C[C@@]3(/C=N/O)C[C@@H]23)c2cnc(-c3cnc(C)nc3)cc12] | (1R,3S,5S)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-((E)-(hydroxyimino)methyl)-2-azabicyclo[3.1.0]hexane-3-carboxamide | *** | 2.37 (B) | 632 |
| 273 | 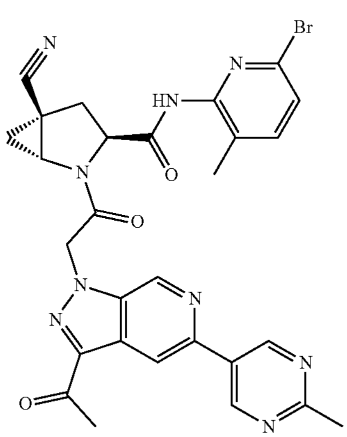 [SMILES: CC(=O)c1nn(CC(=O)N2[C@H](C(=O)Nc3nc(Br)ccc3C)C[C@@]3(C#N)C[C@@H]23)c2cnc(-c3cnc(C)nc3)cc12] | (1R,3S,5S)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-cyano-2-azabicyclo[3.1.0]hexane-3-carboxamide | *** | 2.87 (B) | 614 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 274 | 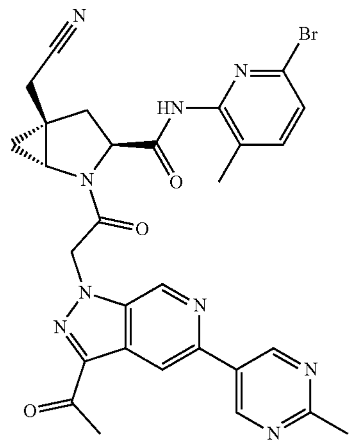 [SMILES: CC(=O)c1nn(CC(=O)N2[C@H](C(=O)Nc3nc(Br)ccc3C)C[C@@]3(CC#N)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-(cyanomethyl)-2-azabicyclo[3.1.0]hexane-3-carboxamide | *** | 2.43 (B) | 628 |
| 275 | 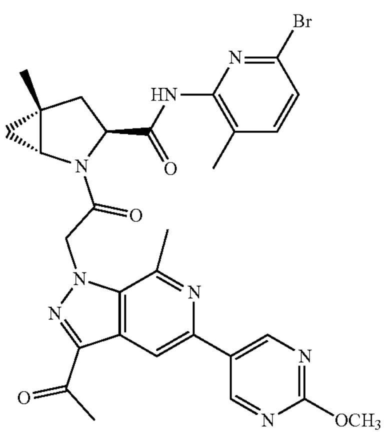 [SMILES: COc1ncc(-c2cc3c(C(C)=O)nn(CC(=O)N4[C@H](C(=O)Nc5nc(Br)ccc5C)C[C@@]5(C)C[C@@H]45)c3c(C)n2)cn1] | (1R,3S,5R)-2-(2-(3-acetyl-5-(2-methoxypyrimidin-5-yl)-7-methyl-1H-pyrazolo[3,4-c]pyridin-1-yl)acetyl)-N-(6-bromo-3-methylpyridin-2-yl)-5-methyl-2-azabicyclo[3.1.0]hexane-3-carboxamide | *** | 1.96 (A) | 633 |
| 277 | 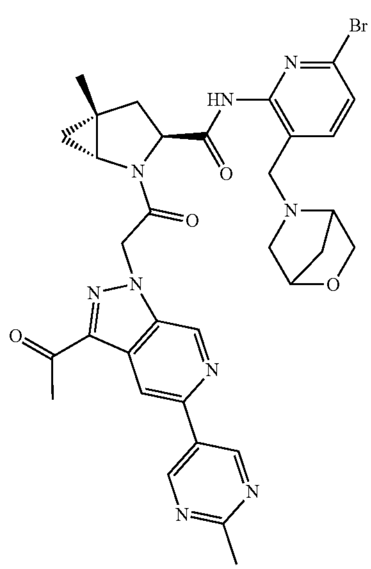 [SMILES: CC(=O)c1nn(CC(=O)N2[C@H](C(=O)Nc3nc(Br)ccc3CN3CC4CC3CO4)C[C@@]3(C)C[C@@H]23)c2cnc(-c3cnc(C)nc3)cc12] | (1R,3S,5R)-N-(3-(2-oxa-5-azabicyclo[2.2.1]heptan-5-ylmethyl)-6-bromopyridin-2-yl)-2-(2-(3-acetyl-5-(2-methylpyrimidin-5-yl)-1H-pyrazolo[3,4-c]pyridin-1-yl)acetyl)-5-methyl-2-azabicyclo[3.1.0]hexane-3-carboxamide | *** | 1.14 (A) | 700 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 278 | 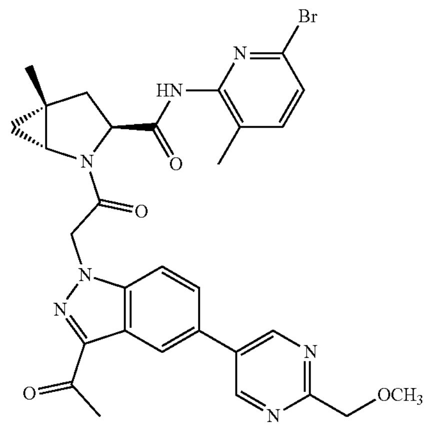 [SMILES: COCc1ncc(-c2ccc3c(c2)c(C(C)=O)nn3CC(=O)N2[C@H](C(=O)Nc3nc(Br)ccc3C)C[C@@]3(C)C[C@@H]23)cn1] | (1R,3S,5R)-2-(2-(3-acetyl-5-(2-(methoxymethyl)pyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 1.77 (A) | 632 |
| 279 | 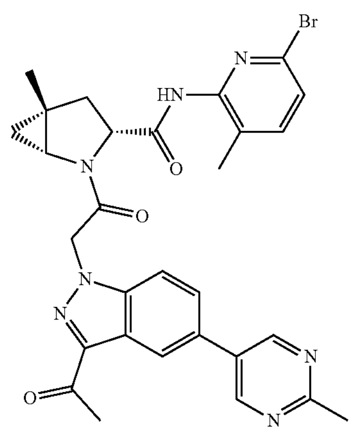 [SMILES: CC(=O)c1nn(CC(=O)N2[C@@H](C(=O)Nc3nc(Br)ccc3C)C[C@@]3(C)C[C@@H]23)c2ccc(-c3cnc(C)nc3)cc12] | (1R,3R,5R)-2-(2-(3-acetyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | * | 2.23 (A) | 601 |
| 280 | 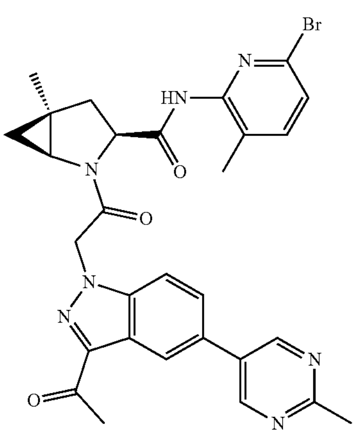 [SMILES: CC(=O)c1nn(CC(=O)N2[C@H]3C[C@@]3(C)C[C@H]2C(=O)Nc2nc(Br)ccc2C)c2ccc(-c3cnc(C)nc3)cc12] | (1S,3S,5S)-2-(2-(3-acetyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 2.22 (A) | 601 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 281 | 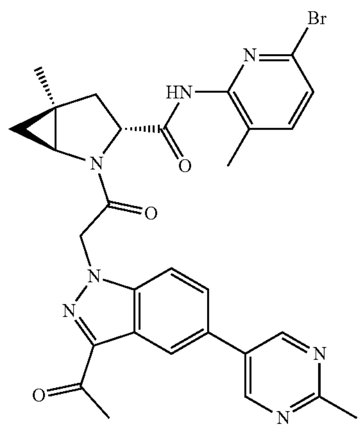 [SMILES: CC(=O)c1nn(CC(=O)N2[C@@H](C(=O)Nc3nc(Br)ccc3C)C[C@]3(C)C[C@H]23)c2ccc(-c3cnc(C)nc3)cc12] | (1S,3R,5S)-2-(2-(3-acetyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | * | 2.14 (A) | 601 |
| 282 | 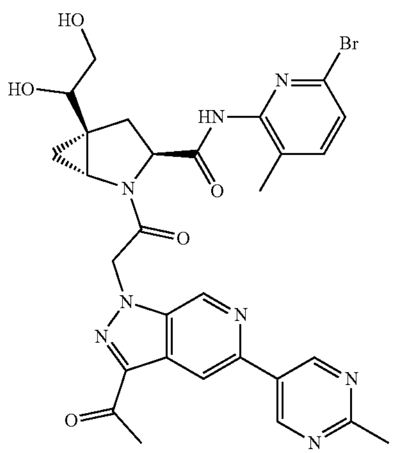 [SMILES: CC(=O)c1nn(CC(=O)N2[C@H](C(=O)Nc3nc(Br)ccc3C)C[C@@]3(C(O)CO)C[C@@H]23)c2cnc(-c3cnc(C)nc3)cc12] | (1R,3S,5S)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-((S)-1,2-dihydroxyethyl)-2-azabicyclo[3.1.0]hexane-3-carboxamide | *** | 2.77 (B) | 649 |
| 283 | 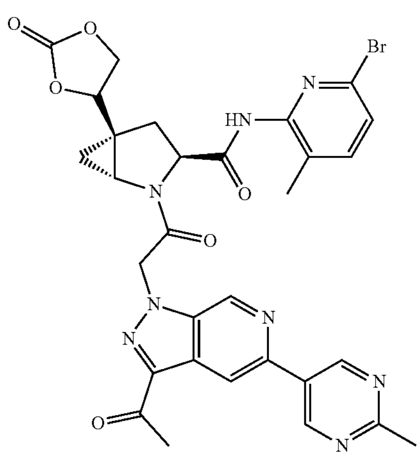 [SMILES: CC(=O)c1nn(CC(=O)N2[C@H](C(=O)Nc3nc(Br)ccc3C)C[C@@]3(C4COC(=O)O4)C[C@@H]23)c2cnc(-c3cnc(C)nc3)cc12] | (1R,3S,5S)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-((S)-2-oxo-1,3-dioxolan-4-yl)-2-azabicyclo[3.1.0]hexane-3-carboxamide | | 2.45 (B) | 675 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 284 | 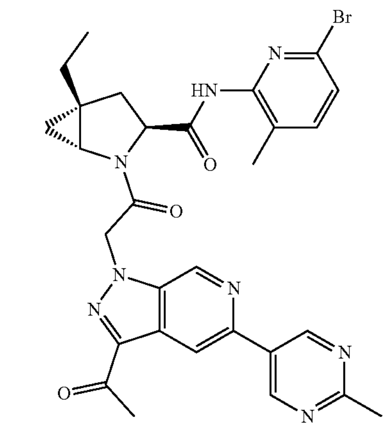 [SMILES: CC[C@@]12C[C@@H](C(=O)Nc3nc(Br)ccc3C)N(C(=O)Cn3nc(C(C)=O)c4cc(-c5cnc(C)nc5)ncc43)[C@@H]1C2] | (1R,3S,5R)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-ethyl-2-azabicyclo[3.1.0]hexane-3-carboxamide | *** | 3.28 (B) | 617 |
| 285 | 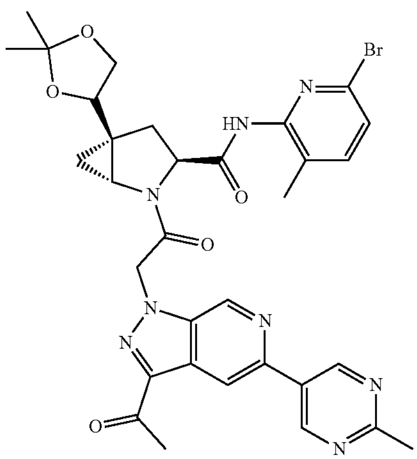 | (1R,3S,5S)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-((S)-2,2-dimethyl-1,3-dioxolan-4-yl)-2-azabicyclo[3.1.0]hexane-3-carboxamide | *** | 3.38 (B) | 689 |
| 286 | 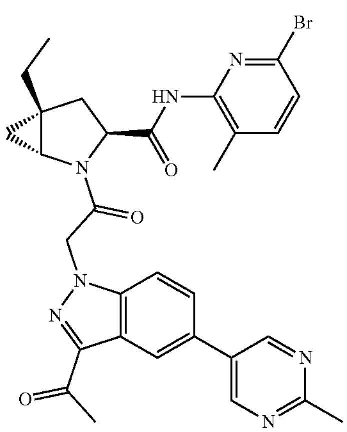 | (1R,3S,5R)-2-(2-(3-acetyl-5-(2-methylpyrimidin-5-yl)-1H-indazol-1-yl)acetyl)-N-(6-bromo-3-methylpyridin-2-yl)-5-ethyl-2-azabicyclo[3.1.0]hexane-3-carboxamide | *** | 3.22 (B) | 616 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 287 | 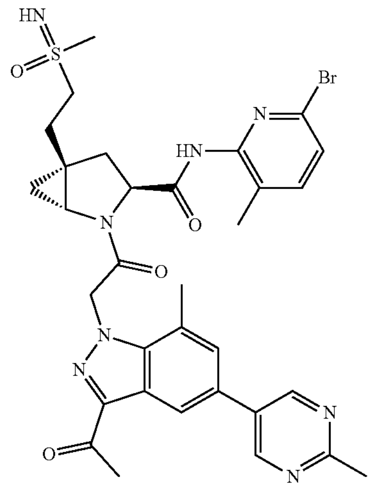 | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-(2-(S-methyl-sulfonimidoyl)ethyl)-2-azabicyclo[3.1.0]hexane-3-carboxamide | *** | 2.56 (B) | 707 |
| 288 | 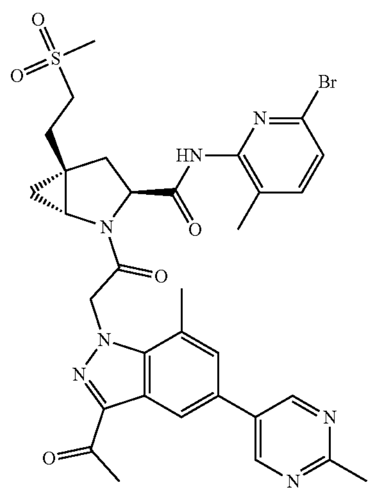 [SMILES: CC(=O)c1nn(CC(=O)N2[C@H](C(=O)Nc3nc(Br)ccc3C)C[C@@]3(CCS(C)(=O)=O)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-(2-(methylsulfonyl)ethyl)-2-azabicyclo[3.1.0]hexane-3-carboxamide | *** | 2.96 (B) | 708 |
| 289 | 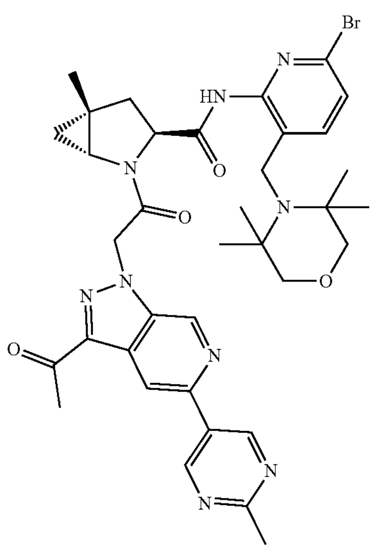 [SMILES: CC(=O)c1nn(CC(=O)N2[C@H](C(=O)Nc3nc(Br)ccc3CN3C(C)(C)COCC3(C)C)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-((3,3,5,5-tetramethylmorpholino)methyl)pyridin-2-yl)-5-methyl-2-azabicyclo[3.1.0]hexane-3-carboxamide | *** | 1.91 (A) | 744 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 290 | 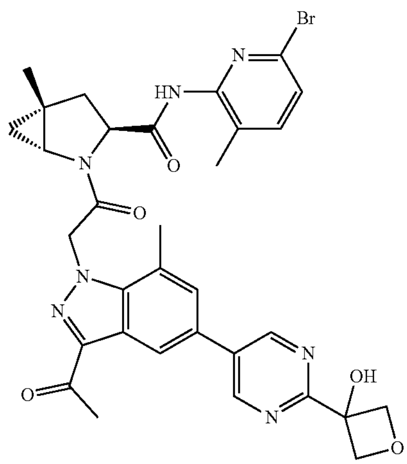 [SMILES: CC(=O)c1nn(CC(=O)N2[C@H](C(=O)Nc3nc(Br)ccc3C)C[C@@]3(C)C[C@@H]23)c2c(C)cc(-c3cnc(C4(O)COC4)nc3)cc12] | (1R,3S,5R)-2-(2-(3-acetyl-5-(2-(3-hydroxyoxetan-3-yl)pyrimidin-5-yl)-7-methyl-1H-indazol-1-yl)acetyl)-N-(6-bromo-3-methylpyridin-2-yl)-5-methyl-2-azabicyclo[3.1.0]hexane-3-carboxamide | *** | 2.15 (A) | 673 |
| 291 | 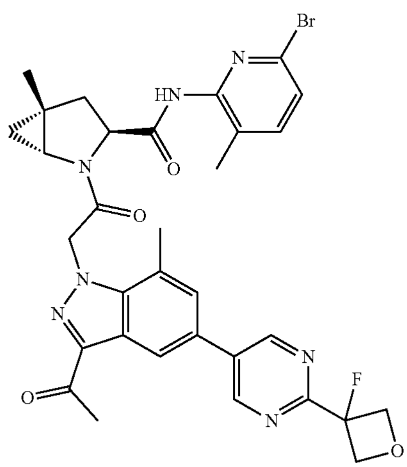 [SMILES: CC(=O)c1nn(CC(=O)N2[C@H](C(=O)Nc3nc(Br)ccc3C)C[C@@]3(C)C[C@@H]23)c2c(C)cc(-c3cnc(C4(F)COC4)nc3)cc12] | (1R,3S,5R)-2-(2-(3-acetyl-5-(2-(3-fluorooxetan-3-yl)pyrimidin-5-yl)-7-methyl-1H-indazol-1-yl)acetyl)-N-(6-bromo-3-methylpyridin-2-yl)-5-methyl-2-azabicyclo[3.1.0]hexane-3-carboxamide | *** | 2.41 (A) | 675 |
| 292 | 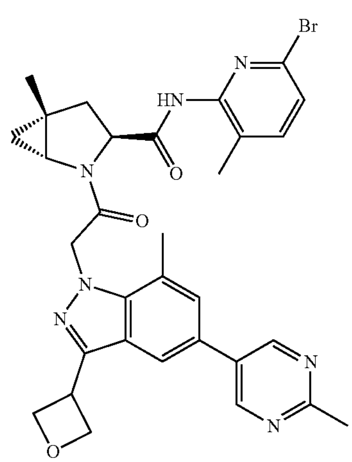 [SMILES: Cc1ncc(-c2cc(C)c3c(c2)c(C2COC2)nn3CC(=O)N2[C@H](C(=O)Nc3nc(Br)ccc3C)C[C@@]3(C)C[C@@H]23)cn1] | (1R,3S,5R)-N-(6-bromo-3-methylpyridin-2-yl)-5-methyl-2-(2-(7-methyl-5-(2-methylpyrimidin-5-yl)-3-(oxetan-3-yl)-1H-indazol-1-yl)acetyl)-2-azabicyclo[3.1.0]hexane-3-carboxamide | *** | 2.07 (A) | 629 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 293 | 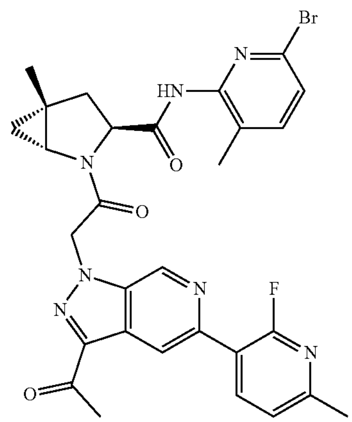 [SMILES: CC(=O)c1nn(CC(=O)N2[C@H](C(=O)Nc3nc(Br)ccc3C)C[C@@]3(C)C[C@@H]23)c2cnc(-c3ccc(C)nc3F)cc12] | (1R,3S,5R)-2-(2-(3-acetyl-5-(2-fluoro-6-methylpyridin-3-yl)-1H-pyrazolo[3,4-c]pyridin-1-yl)acetyl)-N-(6-bromo-3-methylpyridin-2-yl)-5-methyl-2-azabicyclo[3.1.0]hexane-3-carboxamide | *** | 2.09 (A) | 620 |
| 294 | 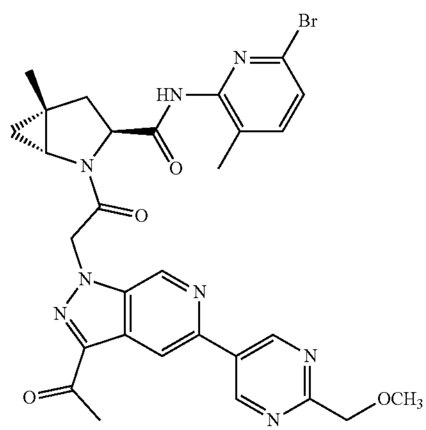 [SMILES: COCc1ncc(-c2cc3c(C(C)=O)nn(CC(=O)N4[C@H](C(=O)Nc5nc(Br)ccc5C)C[C@@]5(C)C[C@@H]45)c3cn2)cn1] | (1R,3S,5R)-2-(2-(3-acetyl-5-(2-(methoxymethyl)pyrimidin-5-yl)-1H-pyrazolo[3,4-c]pyridin-1-yl)acetyl)-N-(6-bromo-3-methylpyridin-2-yl)-5-methyl-2-azabicyclo[3.1.0]hexane-3-carboxamide | *** | 1.66 (A) | 633 |
| 295 | 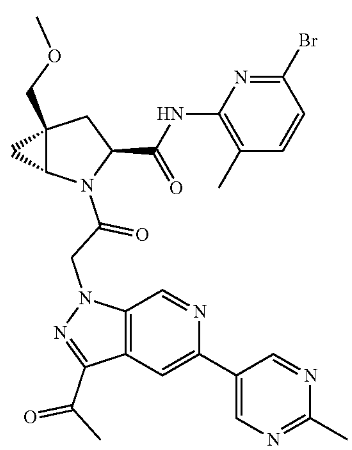 [SMILES: COC[C@@]12C[C@@H](C(=O)Nc3nc(Br)ccc3C)N(C(=O)Cn3nc(C(C)=O)c4cc(-c5cnc(C)nc5)ncc43)[C@@H]1C2] | (1R,3S,5S)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-(methoxymethyl)-2-azabicyclo[3.1.0]hexane-3-carboxamide | *** | 3.04 (B) | 633 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 296 | 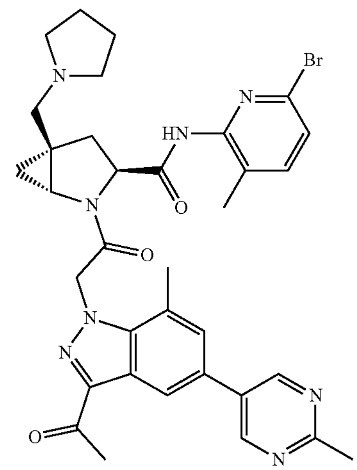 [SMILES: CC(=O)c1nn(CC(=O)N2[C@H](C(=O)Nc3nc(Br)ccc3C)C[C@@]3(CN4CCCC4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-(pyrrolidin-1-ylmethyl)-2-azabicyclo[3.1.0]hexane-3-carboxamide | *** | 2.23 (B) | 685 |
| 297 | 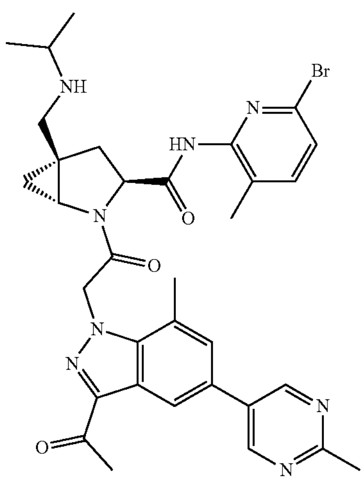 [SMILES: CC(=O)c1nn(CC(=O)N2[C@H](C(=O)Nc3nc(Br)ccc3C)C[C@@]3(CNC(C)C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-((isopropylamino)methyl)-2-azabicyclo[3.1.0]hexane-3-carboxamide | *** | 2.91 (B) | 673 |
| 298 | 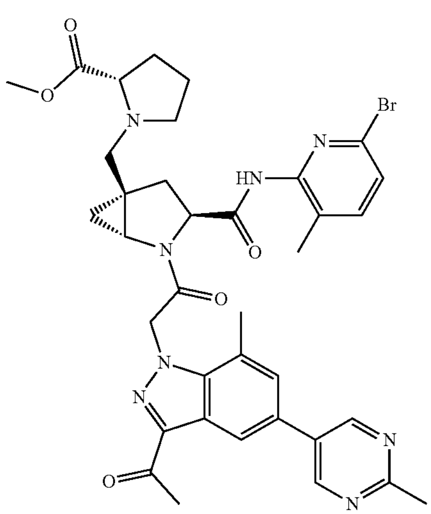 | methyl (((1R,3S,5R)-2-(2-(3-acetyl-7-methyl-5-(2-methylpyrimidin-5-yl)-1H-indazol-1-yl)acetyl)-3-((6-bromo-3-methylpyridin-2-yl)carbamoyl)-2-azabicyclo[3.1.0]hexan-5-yl)methyl)-L-prolinate | *** | 2.92 (B) | 743 |

TABLE 7-continued

Additional Non-limiting Examples of Compounds of the Present Invention

| Cmp No. | Structure | Name | IC₅ (Stars) | RT min (A, B, C or D) | MS (M + 1) |
|---|---|---|---|---|---|
| 299 | 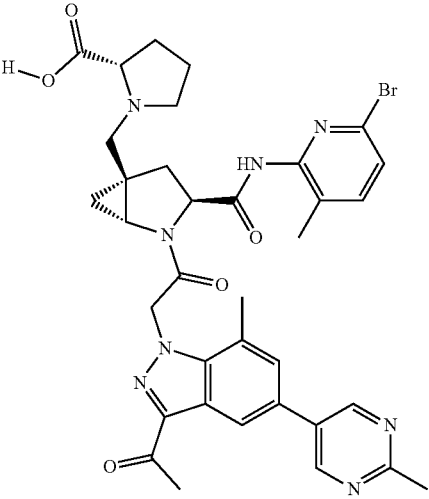 [SMILES: CC(=O)c1nn(CC(=O)N2[C@H](C(=O)Nc3nc(Br)ccc3C)C[C@@]3(CN4CCC[C@H]4C(=O)O)C[C@@H]23)c2c(C)cc(-c3cnc(C)nc3)cc12] | (((1R,3S,5R)-2-(2-(3-acetyl-7-methyl-5-(2-methylpyrimidin-5-yl)-1H-indazol-1-yl)acetyl)-3-((6-bromo-3-methylpyridin-2-yl)carbamoyl)-2-azabicyclo[3.1.0]hexan-5-yl)methyl)-L-proline | *** | 2.85 (B) | 729 |
| 300 | 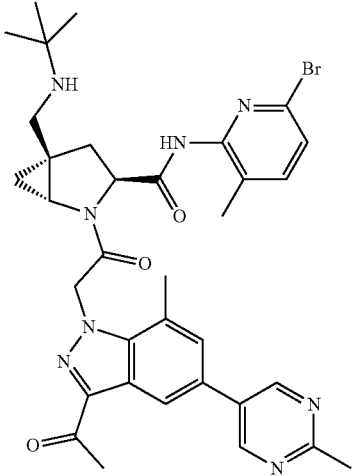 [SMILES: CC(=O)c1nn(CC(=O)N2[C@H](C(=O)Nc3nc(Br)ccc3C)C[C@@]3(CNC(C)(C)C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-((tert-butylamino)methyl)-2-azabicyclo[3.1.0]hexane-3-carboxamide | *** | 2.16 (B) | 687 |
| 301 | 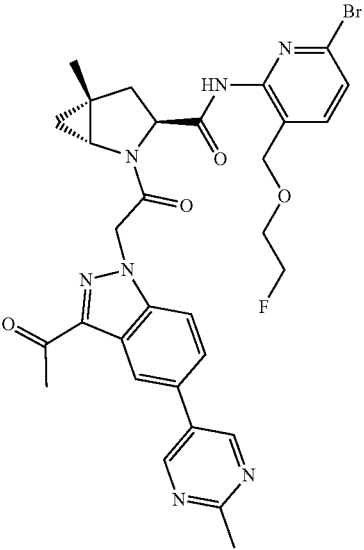 [SMILES: CC(=O)c1nn(CC(=O)N2[C@H](C(=O)Nc3nc(Br)ccc3COCCF)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-((2-fluoro-ethoxy)methyl)pyridin-2-yl)-5-methyl-2-azabicyclo[3.1.0]hexane-3-carboxamide | *** | 1.89 (A) | 664 |

TABLE 7-continued

Additional Non-limiting Examples of Compounds of the Present Invention

| Cmp No. | Structure | Name | IC₅ (Stars) | RT min (A, B, C or D) | MS (M + 1) |
|---|---|---|---|---|---|
| 302 | 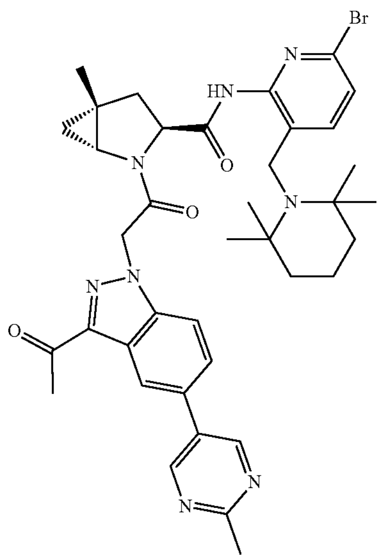 [SMILES: CC(=O)c1nn(CC(=O)N2[C@H](C(=O)Nc3nc(Br)ccc3CN3C(C)(C)CCCC3(C)C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-((2,2,6,6-tetramethylpiperidin-1-yl)methyl)pyridin-2-yl)-5-methyl-2-azabicyclo[3.1.0]hexane-3-carboxamide | *** | | |
| 303 | 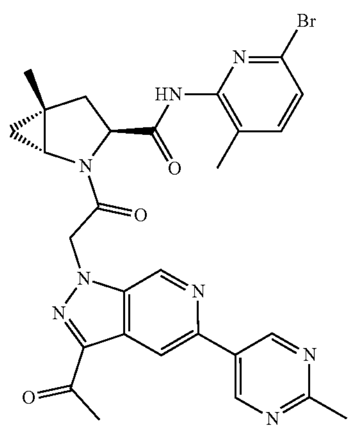 [SMILES: CC(=O)c1nn(CC(=O)N2[C@H](C(=O)Nc3nc(Br)ccc3C)C[C@@]3(C)C[C@@H]23)c2cnc(-c3cnc(C)nc3)cc12] | (1R,3S,5R)-2-(2-(3-acetyl-5-(5-methylpyrazin-2-yl)-1H-pyrazolo[3,4-c]pyridin-1-yl)acetyl)-N-(6-bromo-3-methylpyridin-2-yl)-5-methyl-2-azabicyclo[3.1.0]hexane-3-carboxamide | *** | 1.91 (A) | 603 |
| 304 | 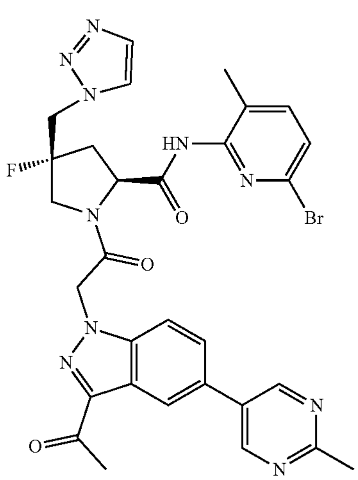 [SMILES: CC(=O)c1nn(CC(=O)N2C[C@@](F)(Cn3ccnn3)C[C@H]2C(=O)Nc2nc(Br)ccc2C)c2ccc(-c3cnc(C)nc3)cc12] | (2S,4R)-4-((1H-1,2,3-triazol-1-yl)methyl)-1-(2-(3-acetyl-5-(2-methylpyrimidin-5-yl)-1H-indazol-1-yl)acetyl)-N-(6-bromo-3-methylpyridin-2-yl)-4-fluoropyrrolidine-2-carboxamide | *** | 3.03 (B) | 675 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 305 | 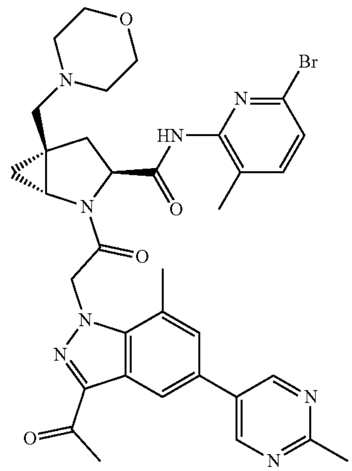 [SMILES: CC(=O)c1nn(CC(=O)N2[C@H](C(=O)Nc3nc(Br)ccc3C)C[C@@]3(CN4CCOCC4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-(morpholinomethyl)-2-azabicyclo[3.1.0]hexane-3-carboxamide | *** | 2.03 (B) | 703 |
| 306 | 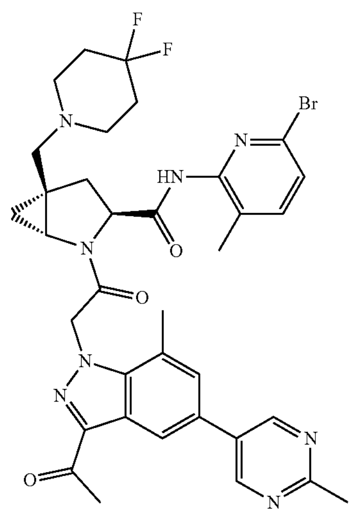 [SMILES: CC(=O)c1nn(CC(=O)N2[C@H](C(=O)Nc3nc(Br)ccc3C)C[C@@]3(CN4CCC(F)(F)CC4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-(4,4-difluoropiperidin-1-yl)methyl)-2-azabicyclo[3.1.0]hexane-3-carboxamide | *** | 2.95 (B) | 737 |
| 307 | 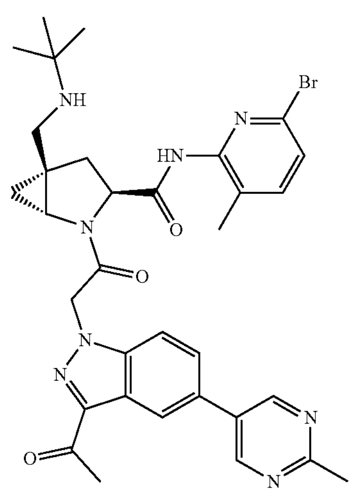 [SMILES: CC(=O)c1nn(CC(=O)N2[C@H](C(=O)Nc3nc(Br)ccc3C)C[C@@]3(CNC(C)(C)C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-methylpyridin-2-yl)-5-((tert-butylamino)methyl)-2-azabicyclo[3.1.0]hexane-3-carboxamide | *** | 2.26 (B) | 675 |

TABLE 7-continued

Additional Non-limiting Examples of Compounds of the Present Invention

| Cmp No. | Structure | Name | IC₅ (Stars) | RT min (A, B, C or D) | MS (M + 1) |
|---|---|---|---|---|---|
| 308 | 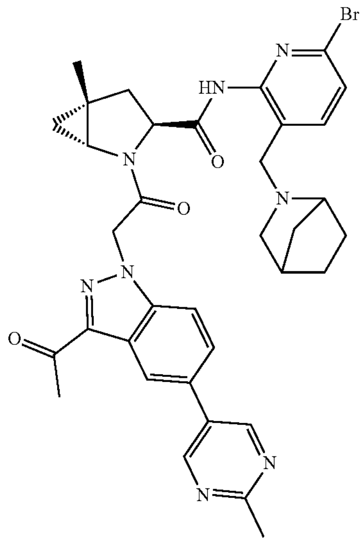 [SMILES: CC(=O)c1nn(CC(=O)N2[C@H](C(=O)Nc3nc(Br)ccc3CN3CC4CCC3C4)C[C@@]3(C)C[C@@H]23)c2ccc(-c3cnc(C)nc3)cc12] | (1R,3S,5R)-N-(3-(2-azabicyclo[2.2.1]heptan-2-ylmethyl)-6-bromopyridin-2-yl)-2-(2-(3-acetyl-5-(2-methylpyrimidin-5-yl)-1H-indazol-1-yl)acetyl)-5-methyl-2-azabicyclo[3.1.0]hexane-3-carboxamide | *** | | |
| 309 | 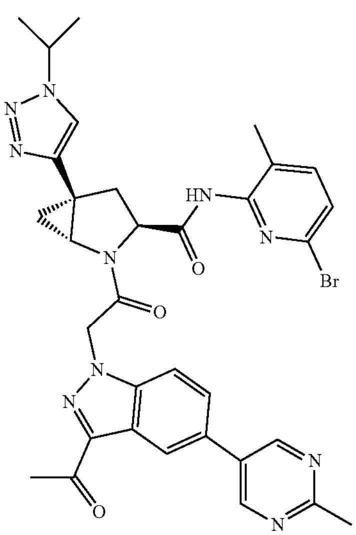 [SMILES: CC(=O)c1nn(CC(=O)N2[C@H](C(=O)Nc3nc(Br)ccc3C)C[C@@]3(c4cn(C(C)C)nn4)C[C@@H]23)c2ccc(-c3cnc(C)nc3)cc12] | (1R,3S,5S)-2-(2-(3-acetyl-5-(2-methylpyrimidin-5-yl)-1H-indazol-1-yl)acetyl)-N-(6-bromo-3-methylpyridin-2-yl)-5-(1-isopropyl-1H-1,2,3-triazol-4-yl)-2-azabicyclo[3.1.0]hexane-3-carboxamide | *** | 1.71 (A) | 699 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 310 | 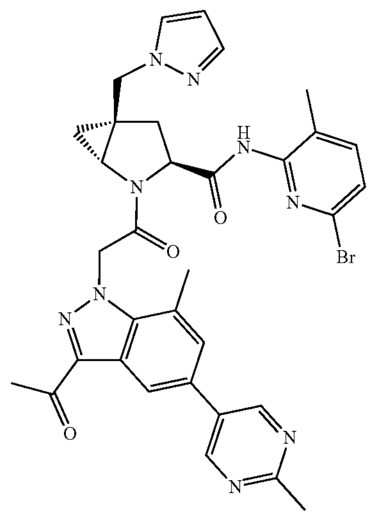 [SMILES: CC(=O)c1nn(CC(=O)N2[C@H](C(=O)Nc3nc(Br)ccc3C)C[C@@]3(Cn4cccn4)C[C@@H]23)c2c(C)cc(-c3cnc(C)nc3)cc12] | (1R,3S,5R)-5-((1H-pyrazol-1-yl)methyl)-2-(2-(3-acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide | *** | 1.62 (A) | 670 |
| 311 | 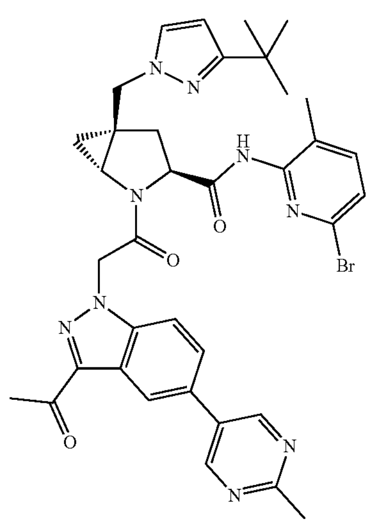 [SMILES: CC(=O)c1nn(CC(=O)N2[C@H](C(=O)Nc3nc(Br)ccc3C)C[C@@]3(Cn4ccc(C(C)(C)C)n4)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-methylpyridin-2-yl)-5-((3-(tert-butyl)-1H-pyrazol-1-yl)methyl)-2-azabicyclo[3.1.0]hexane-3-carboxamide | *** | 2.22 (A) | 726 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 312 | 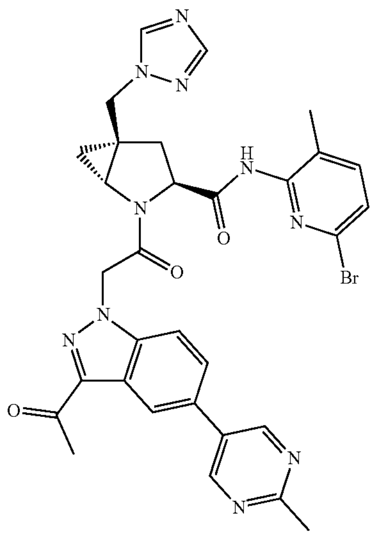 [SMILES: CC(=O)c1nn(CC(=O)N2[C@H](C(=O)Nc3nc(Br)ccc3C)C[C@@]3(Cn4cncn4)C[C@@H]23)c2ccc(-c3cnc(C)nc3)cc12] | (1R,3S,5R)-5-((1H-1,2,4-triazol-1-yl)methyl)-2-(2-(3-acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide | *** | 1.36 (A) | 671 |
| 313 | 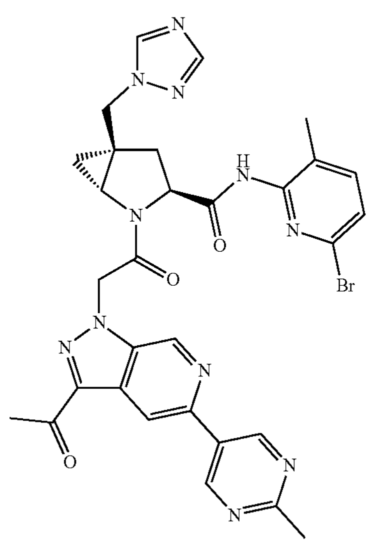 [SMILES: CC(=O)c1nn(CC(=O)N2[C@H](C(=O)Nc3nc(Br)ccc3C)C[C@@]3(Cn4cncn4)C[C@@H]23)c2cnc(-c3cnc(C)nc3)cc12] | (1R,3S,5R)-5-((1H-1,2,4-triazol-1-yl)methyl)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-2-azabicyclo[3.1.0]hexane-3-carboxamide | *** | 1.27 (A) | 672 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 314 | 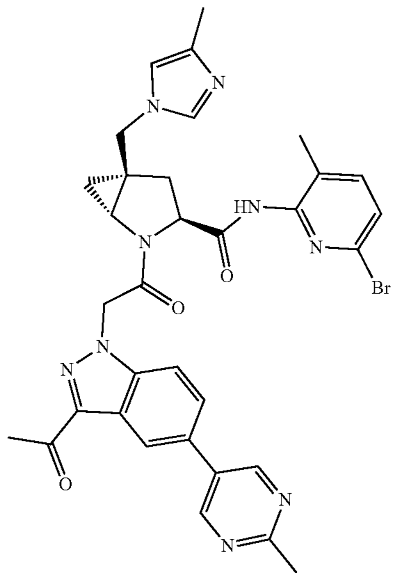 [SMILES: CC(=O)c1nn(CC(=O)N2[C@H](C(=O)Nc3nc(Br)ccc3C)C[C@@]3(Cn4cnc(C)c4)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-methylpyridin-2-yl)-5-((4-methyl-1H-imidazol-1-yl)methyl)-2-azabicyclo[3.1.0]hexane-3-carboxamide | *** | 1.12 (A) | 684 |
| 315 | 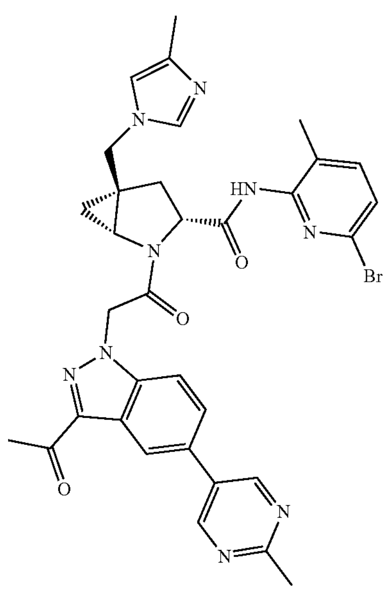 [SMILES: CC(=O)c1nn(CC(=O)N2[C@@H](C(=O)Nc3nc(Br)ccc3C)C[C@@]3(Cn4cnc(C)c4)C[C@@H]23)c2ccc(-c3cnc(C)nc3)cc12] | (1R,3R,5R)-2-(2-(3-acetyl-5-(2-methylpyrimidin-5-yl)-1H-indazol-1-yl)acetyl)-N-(6-bromo-3-methylpyridin-2-yl)-5-((4-methyl-1H-imidazol-1-yl)methyl)-2-azabicyclo[3.1.0]hexane-3-carboxamide | ** | 1.19 (A) | 684 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 316 | 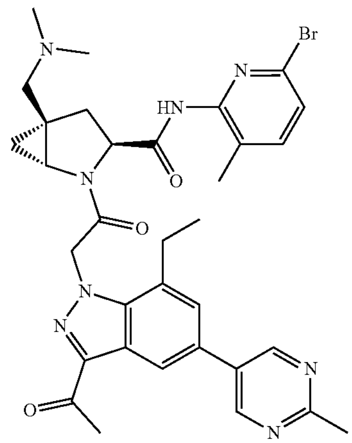 [SMILES: CCc1cc(-c2cnc(C)nc2)cc2c(C(C)=O)nn(CC(=O)N3[C@H](C(=O)Nc4nc(Br)ccc4C)C[C@@]4(CN(C)C)C[C@@H]34)c12] | (1R,3S,5R)-2-(2-(3-acetyl-7-ethyl-5-(2-methylpyrimidin-5-yl)-1H-indazol-1-yl)acetyl)-N-(6-bromo-3-methylpyridin-2-yl)-5-((dimethylamino)methyl)-2-azabicyclo[3.1.0]hexane-3-carboxamide | *** | 2.17 (B) | 675 |
| 319 | 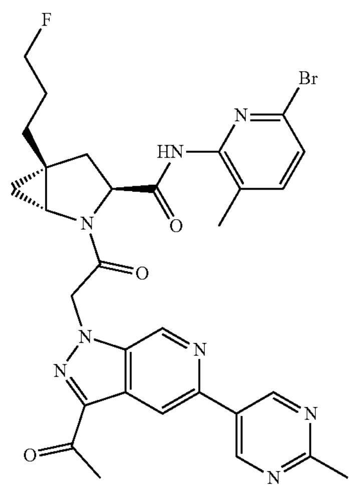 [SMILES: CC(=O)c1nn(CC(=O)N2[C@H](C(=O)Nc3nc(Br)ccc3C)C[C@@]3(CCCF)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-(3-fluoropropyl)-2-azabicyclo[3.1.0]hexane-3-carboxamide | *** | 3.05 (B) | 651 |
| 320 | 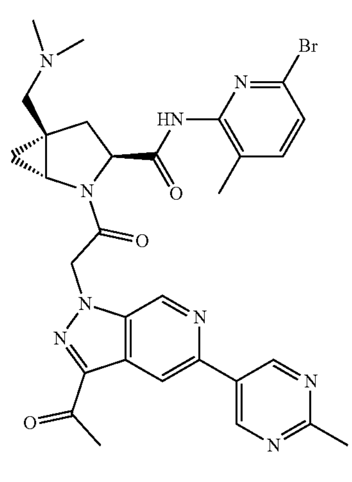 [SMILES: CC(=O)c1nn(CC(=O)N2[C@H](C(=O)Nc3nc(Br)ccc3C)C[C@@]3(CN(C)C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-((dimethylamino)methyl)-2-azabicyclo[3.1.0]hexane-3-carboxamide | *** | 2.23 (B) | 648 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 321 | 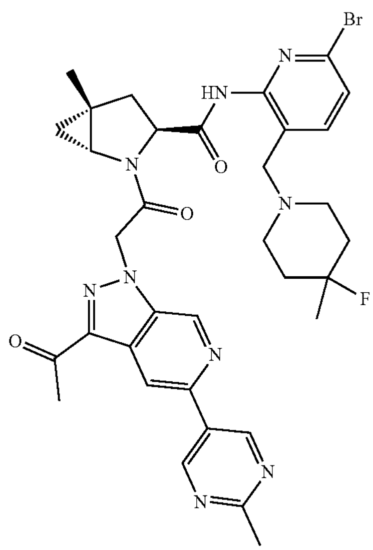 [SMILES: CC(=O)c1nn(CC(=O)N2[C@H](C(=O)Nc3nc(Br)ccc3CN3CCC(C)(F)CC3)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-((4-fluoro-4-methylpiperidin-1-yl)methyl)pyridin-2-yl)-5-methyl-2-azabicyclo[3.1.0]hexane-3-carboxamide | *** | 1.26 (A) | 718 |
| 322 | 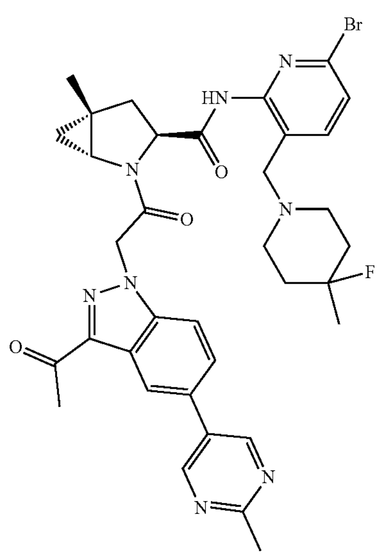 [SMILES: CC(=O)c1nn(CC(=O)N2[C@H](C(=O)Nc3nc(Br)ccc3CN3CCC(C)(F)CC3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-((4-fluoro-4-methylpiperidin-1-yl)methyl)pyridin-2-yl)-5-methyl-2-azabicyclo[3.1.0]hexane-3-carboxamide | *** | | |

TABLE 7-continued

Additional Non-limiting Examples of Compounds of the Present Invention

| Cmp No. | Structure | Name | IC₅ (Stars) | RT min (A, B, C or D) | MS (M + 1) |
|---|---|---|---|---|---|
| 323 | 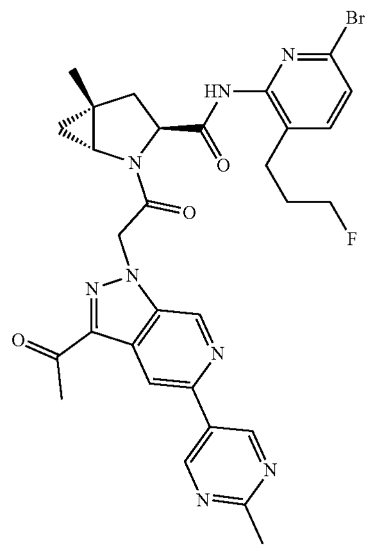 [SMILES: CC(=O)c1nn(CC(=O)N2[C@H](C(=O)Nc3nc(Br)ccc3CCCF)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-(3-fluoropropyl)pyridin-2-yl)-5-methyl-2-azabicyclo[3.1.0]hexane-3-carboxamide | *** | | |
| 324 | 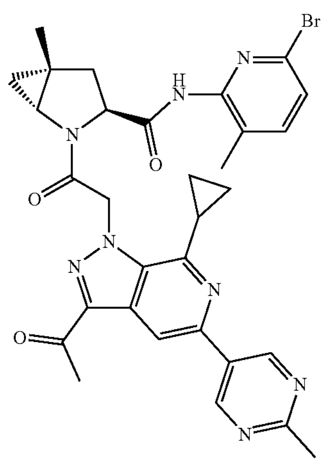 [SMILES: CC(=O)c1nn(CC(=O)N2[C@H](C(=O)Nc3nc(Br)ccc3C)C[C@@]3(C)C[C@@H]23)c2c(C3CC3)nc(-c3cnc(C)nc3)cc12] | (1R,3S,5R)-2-(2-(3-acetyl-7-cyclopropyl-5-(2-methylpyrimidin-5-yl)-1H-pyrazolo[3,4-c]pyridin-1-yl)acetyl)-N-(6-bromo-3-methylpyridin-2-yl)-5-methyl-2-azabicyclo[3.1.0]hexane-3-carboxamide | *** | 2.07 (A) | 643 |
| 325 | 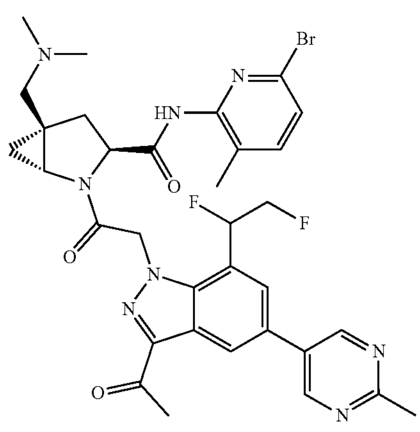 [SMILES: CC(=O)c1nn(CC(=O)N2[C@H](C(=O)Nc3nc(Br)ccc3C)C[C@@]3(CN(C)C)C[C@@H]23)c2c(C(F)CF)cc(-c3cnc(C)nc3)cc12] | (1R,3S,5R)-2-(2-(3-acetyl-7-(1,2-difluoroethyl)-5-(2-methylpyrimidin-5-yl)-1H-indazol-1-yl)acetyl)-N-(6-bromo-3-methylpyridin-2-yl)-5-((dimethylamino)methyl)-2-azabicyclo[3.1.0]hexane-3-carboxamide | *** | 2.09 (B) | 709 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 326 | 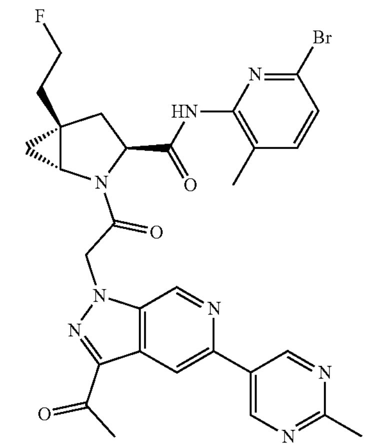 [SMILES: CC(=O)c1nn(CC(=O)N2[C@H](C(=O)Nc3nc(Br)ccc3C)C[C@@]3(CCF)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-(2-fluoroethyl)-2-azabicyclo[3.1.0]hexane-3-carboxamide | *** | 3.31 (B) | 635 |
| 327 | 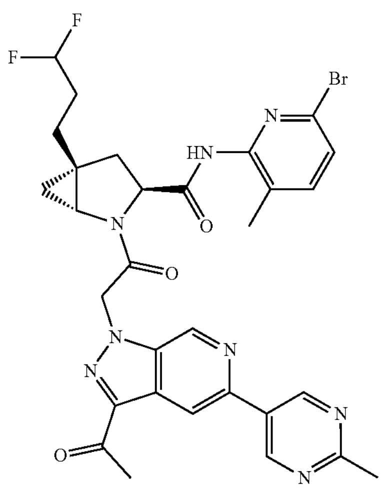 [SMILES: CC(=O)c1nn(CC(=O)N2[C@H](C(=O)Nc3nc(Br)ccc3C)C[C@@]3(CCC(F)F)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-(3,3-difluoropropyl)-2-azabicyclo[3.1.0]hexane-3-carboxamide | *** | 3.56 (B) | 667 |
| 328 | 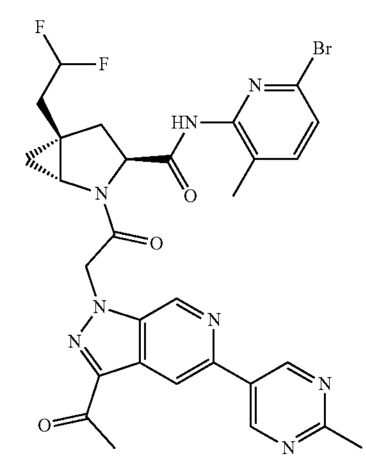 [SMILES: CC(=O)c1nn(CC(=O)N2[C@H](C(=O)Nc3nc(Br)ccc3C)C[C@@]3(CC(F)F)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-(2,2-difluoroethyl)-2-azabicyclo[3.1.0]hexane-3-carboxamide | *** | 3.37 (B) | 653 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 330 | 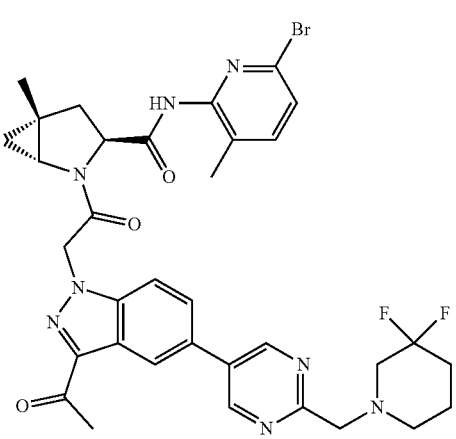 [SMILES: CC(=O)c1nn(CC(=O)N2[C@H](C(=O)Nc3nc(Br)ccc3C)C[C@@]3(C)C[C@@H]23)c2ccc(-c3cnc(CN4CCCC(F)(F)C4)nc3)cc12] | (1R,3S,5R)-2-(2-(3-acetyl-5-(2-((3,3-difluoropiperidin-1-yl)methyl)pyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 1.65 (A) | 722 |
| 331 | 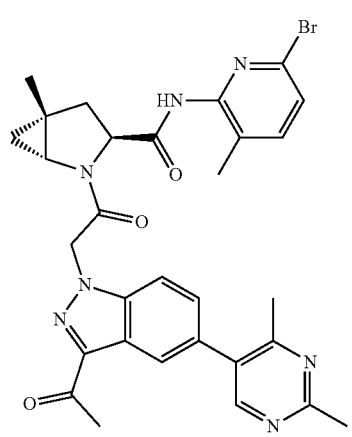 [SMILES: CC(=O)c1nn(CC(=O)N2[C@H](C(=O)Nc3nc(Br)ccc3C)C[C@@]3(C)C[C@@H]23)c2ccc(-c3cnc(C)nc3C)cc12] | (1R,3S,5R)-2-(2-(3-acetyl-5-(2,4-dimethylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 1.81 (A) | 618 |
| 332 | 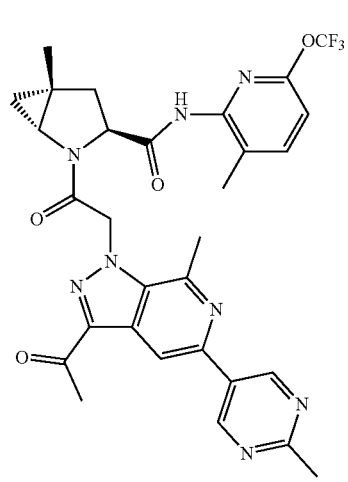 | (1R,3S,5R)-2-(2-(3-acetyl-7-methyl-5-(2-methylpyrimidin-5-yl)-1H-pyrazolo[3,4-c]pyridin-1-yl)acetyl)-5-methyl-N-(3-methyl-6-(trifluoromethoxy)pyridin-2-yl)-2-azabicyclo[3.1.0]hexane-3-carboxamide | *** | 2.03 (A) | 623 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 333 | 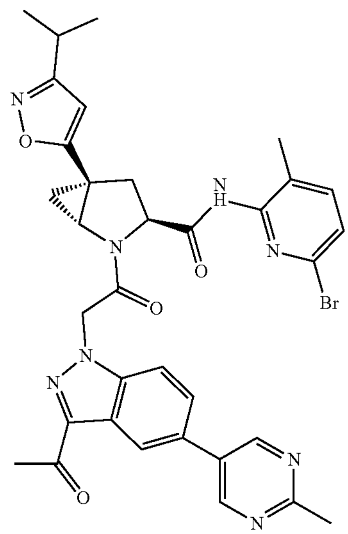 [SMILES: CC(=O)c1nn(CC(=O)N2[C@H](C(=O)Nc3nc(Br)ccc3C)C[C@@]3(c4cc(C(C)C)no4)C[C@@H]23)c2ccc(-c3cnc(C)nc3)cc12] | (1R,3S,5S)-2-(2-(3-acetyl-5-(2-methylpyrimidin-5-yl)-1H-indazol-1-yl)acetyl)-N-(6-bromo-3-methylpyridin-2-yl)-5-(3-isopropylisoxazol-5-yl)-2-azabicyclo[3.1.0]hexane-3-carboxamide | *** | 2.13 (A) | 699 |
| 334 | 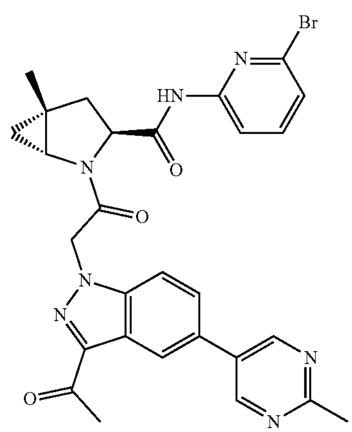 [SMILES: CC(=O)c1nn(CC(=O)N2[C@H](C(=O)Nc3cccc(Br)n3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromopyridin-2-yl)-5-methyl-2-azabicyclo[3.1.0]hexane-3-carboxamide | *** | 1.91 (A) | 589 |
| 335 | 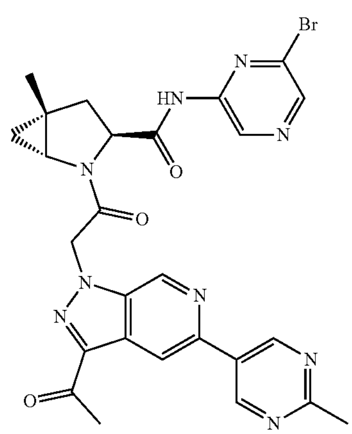 [SMILES: CC(=O)c1nn(CC(=O)N2[C@H](C(=O)Nc3cncc(Br)n3)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromopyrazin-2-yl)-5-methyl-2-azabicyclo[3.1.0]hexane-3-carboxamide | *** | 1.71 (A) | 592 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 336 | 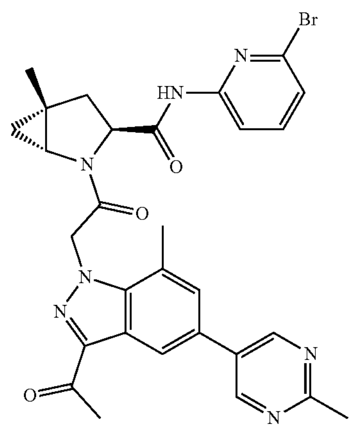 [SMILES: CC(=O)c1nn(CC(=O)N2[C@H](C(=O)Nc3cccc(Br)n3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-pyrazolo[3,4-c]pyridin-1-yl)acetyl)-N-(6-bromopyridin-2-yl)-5-methyl-2-azabicyclo[3.1.0]hexane-3-carboxamide | *** | 2.02 (A) | 603 |
| 337 | 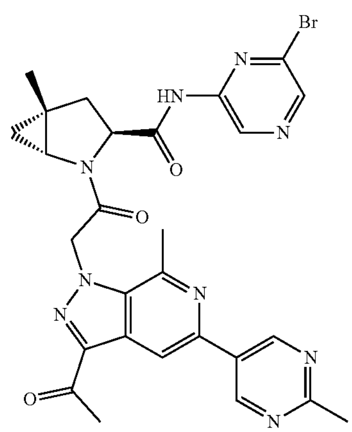 [SMILES: CC(=O)c1nn(CC(=O)N2[C@H](C(=O)Nc3cncc(Br)n3)C[C@@]3(C)C[C@@H]23)c2c(C)nc(-c3cnc(C)nc3)cc12] | (1R,3S,5R)-2-(2-(3-acetyl-7-methyl-5-(2-methylpyrimidin-5-yl)-1H-pyrazolo[3,4-c]pyridin-1-yl)acetyl)-N-(6-bromopyrazin-2-yl)-5-methyl-2-azabicyclo[3.1.0]hexane-3-carboxamide | *** | 1.82 (A) | 604 |
| 338 | 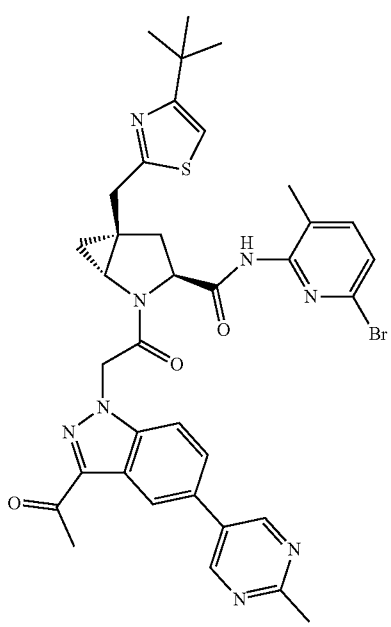 | (1R,3S,5R)-2-(2-(3-acetyl-5-(2-methylpyrimidin-5-yl)-1H-indazol-1-yl)acetyl)-N-(6-bromo-3-methylpyridin-2-yl)-5-((4-(tert-butyl)thiazol-2-yl)methyl)-2-azabicyclo[3.1.0]hexane-3-carboxamide | *** | 2.40 (A) | 741 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 339 | 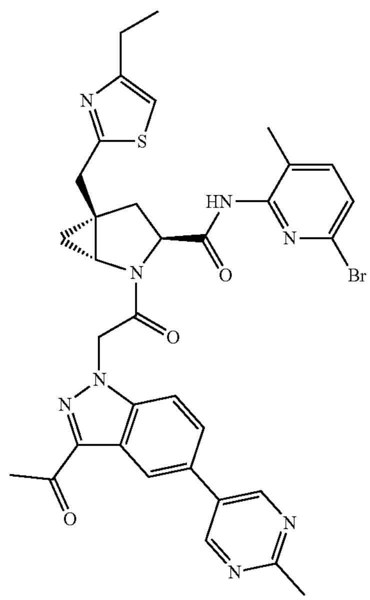 [SMILES: CCc1csc(C[C@@]23C[C@@H](C(=O)Nc4nc(Br)ccc4C)N(C(=O)Cn4nc(C(C)=O)c5cc(-c6cnc(C)nc6)ccc54)[C@@H]2C3)n1] | (1R,3S,5R)-2-(2-(3-acetyl-5-(2-methylpyrimidin-5-yl)-1H-indazol-1-yl)acetyl)-N-(6-bromo-3-methylpyridin-2-yl)-5-((4-ethylthiazol-2-yl)methyl)-2-azabicyclo[3.1.0]hexane-3-carboxamide | *** | 1.99 (A) | 713 |
| 340 | 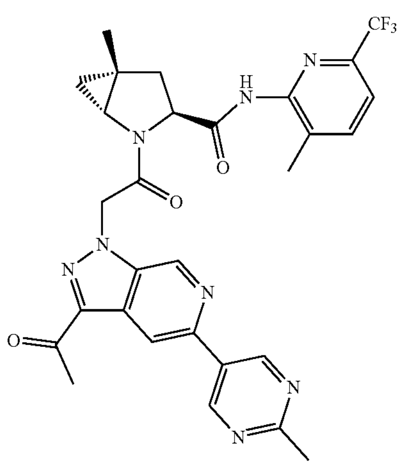 | (1R,3S,5R)-2-(2-(3-acetyl-5-(2-methylpyrimidin-5-yl)-1H-pyrazolo[3,4-c]pyridin-1-yl)acetyl)-5-methyl-N-(3-methyl-6-(trifluoromethyl)pyridin-2-yl)-2-azabicyclo[3.1.0]hexane-3-carboxamide | *** | 1.82 (A) | 593 |
| 341 | 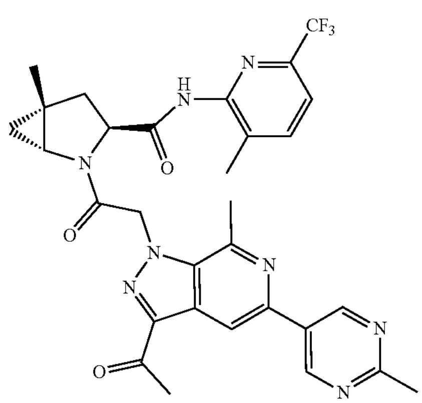 | (1R,3S,5R)-2-(2-(3-acetyl-7-methyl-5-(2-methylpyrimidin-5-yl)-1H-pyrazolo[3,4-c]pyridin-1-yl)acetyl)-5-methyl-N-(3-methyl-6-(trifluoromethyl)pyridin-2-yl)-2-azabicyclo[3.1.0]hexane-3-carboxamide | *** | 1.92 (A) | 607 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 342 | 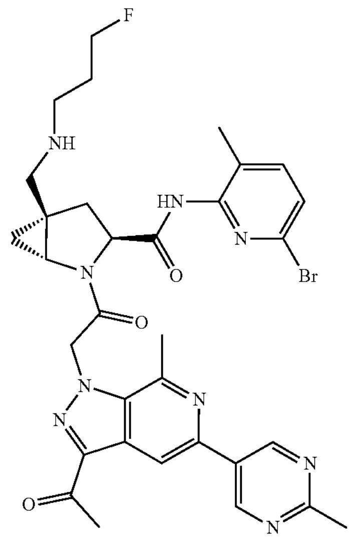 [SMILES: CC(=O)c1nn(CC(=O)N2[C@H](C(=O)Nc3nc(Br)ccc3C)C[C@@]3(CNCCCF)C[C@@H]23)c2c(C)nc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-(((3-fluoropropyl)amino)methyl)-2-azabicyclo[3.1.0]hexane-3-carboxamide | *** | 3.62 (B) | 691 |
| 344 | 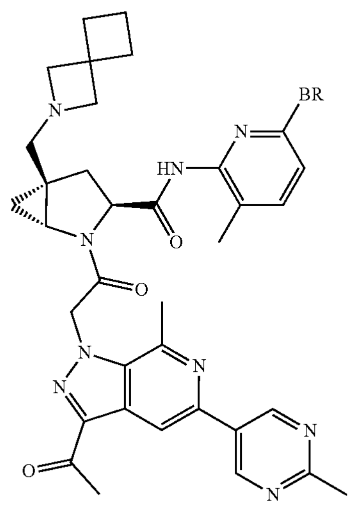 | (1R,3S,5R)-5-(2-azaspiro[3.3]heptan-2-ylmethyl)-2-(2-(3-acetyl-7-methyl-5-(2-methylpyrimidin-5-yl)-1H-pyrazolo[3,4-c]pyridin-1-yl)acetyl)-N-(6-bromo-3-methylpyridin-2-yl)-2-azabicyclo[3.1.0]hexane-3-carboxamide | *** | 2.71 (B) | 712 |
| 345 | 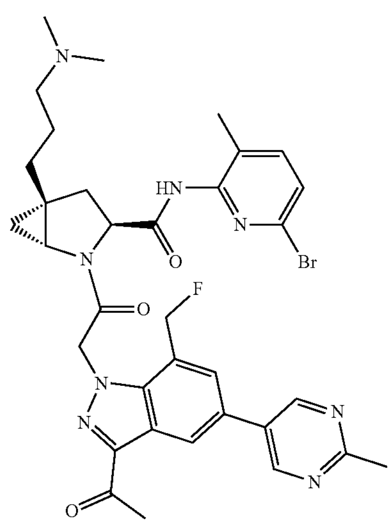 [SMILES: CC(=O)c1nn(CC(=O)N2[C@H](C(=O)Nc3nc(Br)ccc3C)C[C@@]3(CCCN(C)C)C[C@@H]23)c2c(CF)cc(-c3cnc(C)nc3)cc12] | (1R,3S,5R)-2-(2-(3-acetyl-7-(fluoromethyl)-5-(2-methylpyrimidin-5-yl)-1H-indazol-1-yl)acetyl)-N-(6-bromo-3-methylpyridin-2-yl)-5-(3-(dimethylamino)propyl)-2-azabicyclo[3.1.0]hexane-3-carboxamide | *** | 2.61 (B) | 705 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 346 | 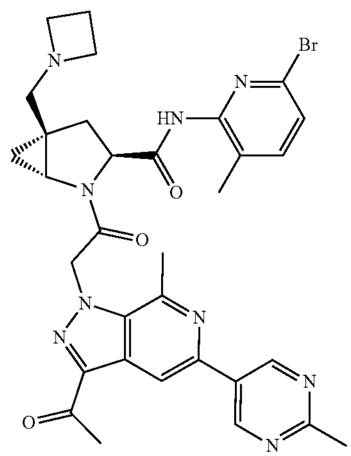 [SMILES: CC(=O)c1nn(CC(=O)N2[C@H](C(=O)Nc3nc(Br)ccc3C)C[C@@]3(CN4CCC4)C[C@@H]23)c2c(C)nc(-c3cnc(C)nc3)cc12] | (1R,3S,5R)-2-(2-(3-acetyl-7-methyl-5-(2-methylpyrimidin-5-yl)-1H-pyrazolo[3,4-c]pyridin-1-yl)acetyl)-5-(azetidin-1-ylmethyl)-N-(6-bromo-3-methylpyridin-2-yl)-2-azabicyclo[3.1.0]hexane-3-carboxamide | *** | 2.31 (B) | 672 |
| 347 | 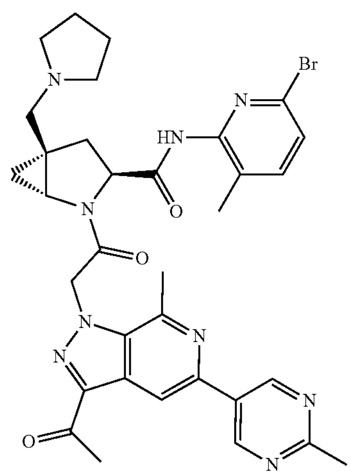 [SMILES: CC(=O)c1nn(CC(=O)N2[C@H](C(=O)Nc3nc(Br)ccc3C)C[C@@]3(CN4CCCC4)C[C@@H]23)c2c(C)nc(-c3cnc(C)nc3)cc12] | (1R,3S,5R)-2-(2-(3-acetyl-7-methyl-5-(2-methylpyrimidin-5-yl)-1H-pyrazolo[3,4-c]pyridin-1-yl)acetyl)-N-(6-bromo-3-methylpyridin-2-yl)-5-(pyrrolidin-1-ylmethyl)-2-azabicyclo[3.1.0]hexane-3-carboxamide | *** | 3.29 (B) | 686 |
| 348 | 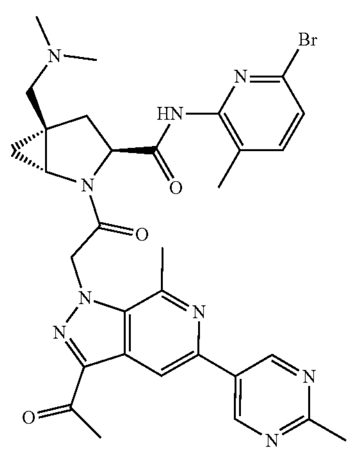 [SMILES: CC(=O)c1nn(CC(=O)N2[C@H](C(=O)Nc3nc(Br)ccc3C)C[C@@]3(CN(C)C)C[C@@H]23)c2c(C)nc(-c3cnc(C)nc3)cc12] | (1R,3S,5R)-2-(2-(3-acetyl-7-methyl-5-(2-methylpyrimidin-5-yl)-1H-pyrazolo[3,4-c]pyridin-1-yl)acetyl)-N-(6-bromo-3-methylpyridin-2-yl)-5-((dimethylamino)methyl)-2-azabicyclo[3.1.0]hexane-3-carboxamide | *** | 2.56 (B) | 660 |

… TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 349 | 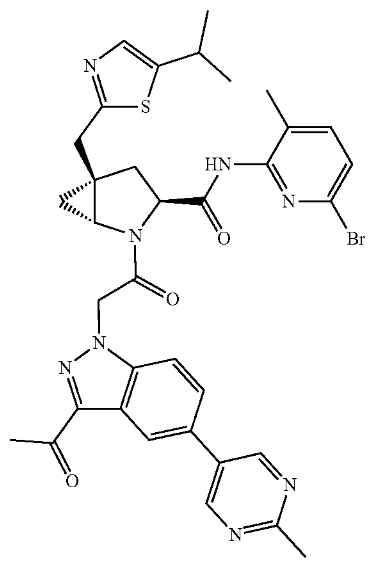 [SMILES: CC(=O)c1nn(CC(=O)N2[C@H](C(=O)Nc3nc(Br)ccc3C)C[C@@]3(Cc4ncc(C(C)C)s4)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-methylpyridin-2-yl)-5-((5-isopropylthiazol-2-yl)methyl)-2-azabicyclo[3.1.0]hexane-3-carboxamide | *** | 2.20 (A) | 729 |
| 350 | 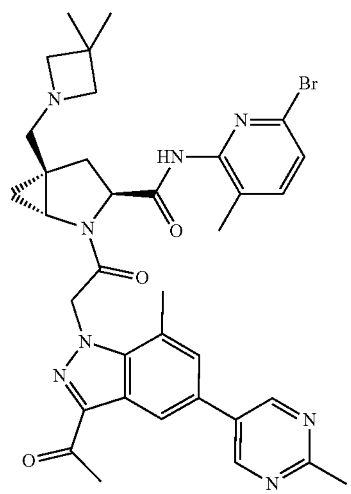 [SMILES: CC(=O)c1nn(CC(=O)N2[C@H](C(=O)Nc3nc(Br)ccc3C)C[C@@]3(CN4CC(C)(C)C4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-((3,3-dimethylazetidin-1-yl)methyl)-2-azabicyclo[3.1.0]hexane-3-carboxamide | *** | 2.47 (B) | 699 |
| 351 | 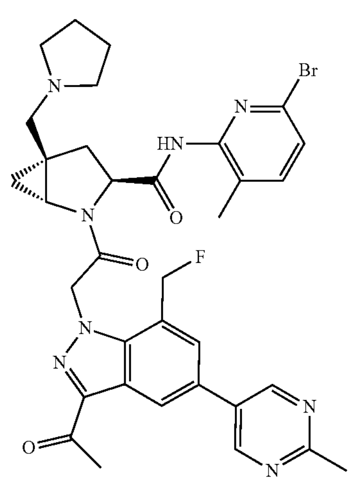 [SMILES: CC(=O)c1nn(CC(=O)N2[C@H](C(=O)Nc3nc(Br)ccc3C)C[C@@]3(CN4CCCC4)C[C@@H]23)c2c(CF)cc(-c3cnc(C)nc3)cc12] | (1R,3S,5R)-2-(2-(3-acetyl-7-(fluoromethyl)-5-(2-methylpyrimidin-5-yl)-1H-indazol-1-yl)acetyl)-N-(6-bromo-3-methylpyridin-2-yl)-5-(pyrrolidin-1-ylmethyl)-2-azabicyclo[3.1.0]hexane-3-carboxamide | *** | 4.28 (B) | 703 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 352 | 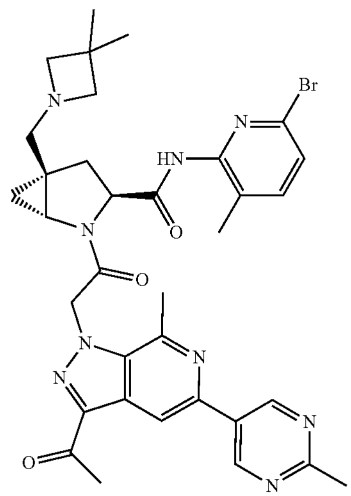 [SMILES: CC(=O)c1nn(CC(=O)N2[C@H](C(=O)Nc3nc(Br)ccc3C)C[C@@]3(CN4CC(C)(C)C4)C[C@@H]23)c2c(C)nc(-c3cnc(C)nc3)cc12] | (1R,3S,5R)-2-(2-(3-acetyl-7-methyl-5-(2-methylpyrimidin-5-yl)-1H-pyrazolo[3,4-c]pyridin-1-yl)acetyl)-N-(6-bromo-3-methylpyridin-2-yl)-5-((3,3-dimethylazetidin-1-yl)methyl)-2-azabicyclo[3.1.0]hexane-3-carboxamide | *** | 4.25 (B) | 700 |
| 353 | 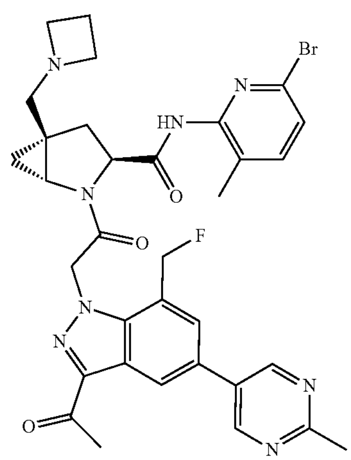 [SMILES: CC(=O)c1nn(CC(=O)N2[C@H](C(=O)Nc3nc(Br)ccc3C)C[C@@]3(CN4CCC4)C[C@@H]23)c2c(CF)cc(-c3cnc(C)nc3)cc12] | (1R,3S,5R)-2-(2-(3-acetyl-7-(fluoromethyl)-5-(2-methylpyrimidin-5-yl)-1H-indazol-1-yl)acetyl)-5-(azetidin-1-ylmethyl)-N-(6-bromo-3-methylpyridin-2-yl)-2-azabicyclo[3.1.0]hexane-3-carboxamide | *** | 4.46 (B) | 689 |
| 354 | 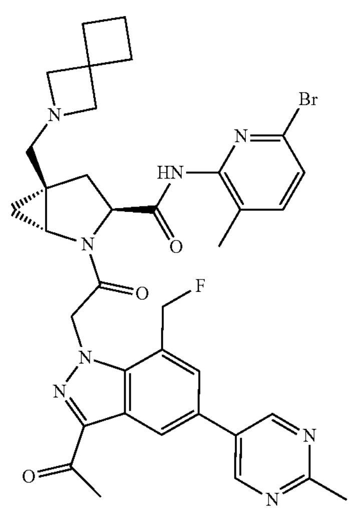 [SMILES: CC(=O)c1nn(CC(=O)N2[C@H](C(=O)Nc3nc(Br)ccc3C)C[C@@]3(CN4CC5(CCC5)C4)C[C@@H]23)c2c(CF)cc(-c3cnc(C)nc3)cc12] | (1R,3S,5R)-5-(2-azaspiro[3.3]heptan-2-ylmethyl)-2-(2-(3-acetyl-7-(fluoromethyl)-5-(2-methylpyrimidin-5-yl)-1H-indazol-1-yl)acetyl)-N-(6-bromo-3-methylpyridin-2-yl)-2-azabicyclo[3.1.0]hexane-3-carboxamide | *** | 2.26 (B) | 729 |

TABLE 7-continued

Additional Non-limiting Examples of Compounds of the Present Invention

| Cmp No. | Structure | Name | IC₅ (Stars) | RT min (A, B, C or D) | MS (M + 1) |
|---|---|---|---|---|---|
| 355 | 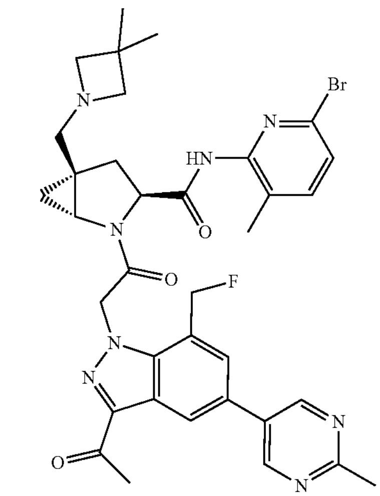 [SMILES: CC(=O)c1nn(CC(=O)N2[C@H](C(=O)Nc3nc(Br)ccc3C)C[C@@]3(CN4CC(C)(C)C4)C[C@@H]23)c2c(CF)cc(-c3cnc(C)nc3)cc12] | (1R,3S,5R)-2-(2-(3-acetyl-7-(fluoromethyl)-5-(2-methylpyrimidin-5-yl)-1H-indazol-1-yl)acetyl)-N-(6-bromo-3-methylpyridin-2-yl)-5-((3,3-dimethylazetidin-1-yl)methyl)-2-azabicyclo[3.1.0]hexane-3-carboxamide | *** | 2.95 (B) | 717 |
| 356 | 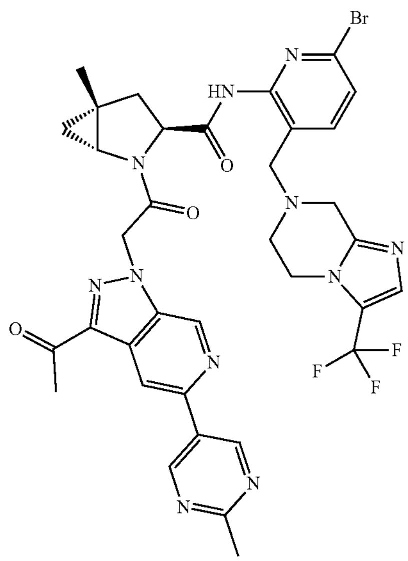 [SMILES: CC(=O)c1nn(CC(=O)N2[C@H](C(=O)Nc3nc(Br)ccc3CN3CCn4c(C(F)(F)F)cnc4C3)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-((3-(trifluoromethyl)-5,6-dihydro-[1,2,4]triazolo[4,3-a]pyrazin-7(8H)-yl)methyl)pyridin-2-yl)-5-methyl-2-azabicyclo[3.1.0]hexane-3-carboxamide | *** | | |
| 357 | 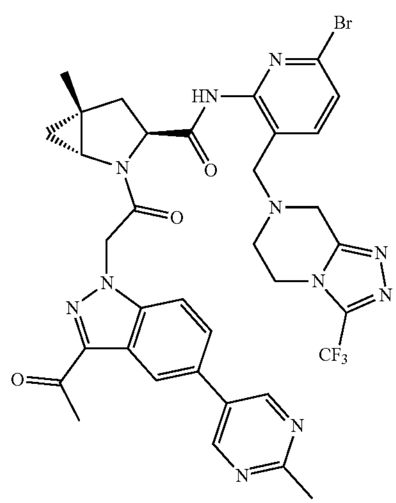 [SMILES: CC(=O)c1nn(CC(=O)N2[C@H](C(=O)Nc3nc(Br)ccc3CN3CCn4c(nnc4C(F)(F)F)C3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-((3-(trifluoromethyl)-5,6-dihydro-[1,2,4]triazolo[4,3-a]pyrazin-7(8H)-yl)methyl)pyridin-2-yl)-5-methyl-2-azabicyclo[3.1.0]hexane-3-carboxamide | *** | | |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 359 | 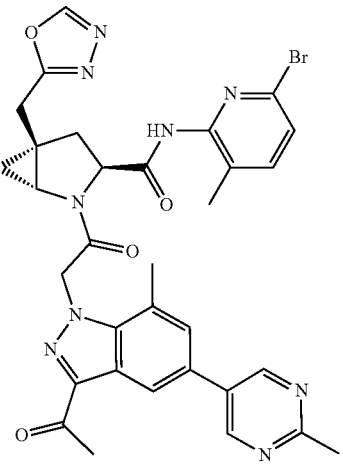 [SMILES: CC(=O)c1nn(CC(=O)N2[C@H](C(=O)Nc3nc(Br)ccc3C)C[C@@]3(Cc4nnco4)C[C@@H]23)c2c(C)cc(-c3cnc(C)nc3)cc12] | (1R,3S,5R)-5-((1,3,4-oxadiazol-2-yl)methyl)-2-(2-(3-acetyl-7-methyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide | *** | 2.87 (B) | 684 |
| 360 | 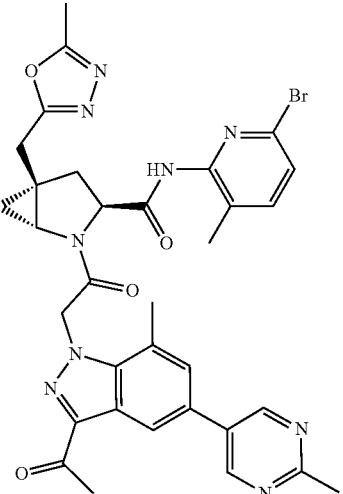 | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-((5-methyl-1,3,4-oxadiazol-2-yl)methyl)-2-azabicyclo[3.1.0]hexane-3-carboxamide | *** | 2.98 (B) | 698 |
| 361 | 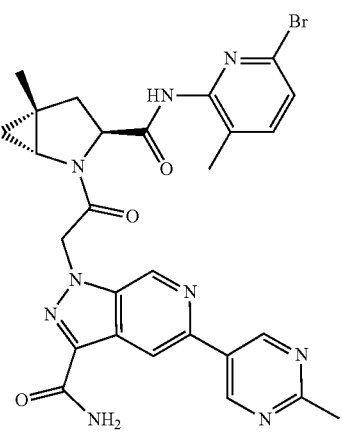 [SMILES: Cc1ncc(-c2cc3c(C(N)=O)nn(CC(=O)N4[C@H](C(=O)Nc5nc(Br)ccc5C)C[C@@]5(C)C[C@@H]45)c3cn2)cn1] | 1-(2-((1R,3S,5R)-3-((6-bromo-3-methylpyridin-2-yl)carbamoyl)-5-methyl-2-azabicyclo[3.1.0]hexan-2-yl)-2-oxoethyl)-5-(2-methylpyrimidin-5-yl)-1H-pyrazolo[3,4-c]pyridine-3-carboxamide | *** | 2.50 (B) | 604 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 362 | 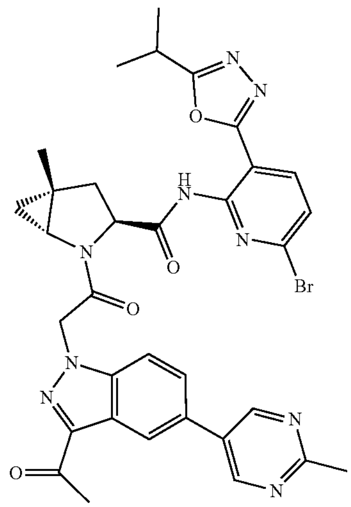 [SMILES: CC(=O)c1nn(CC(=O)N2[C@H](C(=O)Nc3nc(Br)ccc3-c3nnc(C(C)C)o3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-(5-isopropyl-1,3,4-oxadiazol-2-yl)pyridin-2-yl)-5-methyl-2-azabicyclo[3.1.0]hexane-3-carboxamide | ** | 1.93 (A) | 700 |
| 363 | 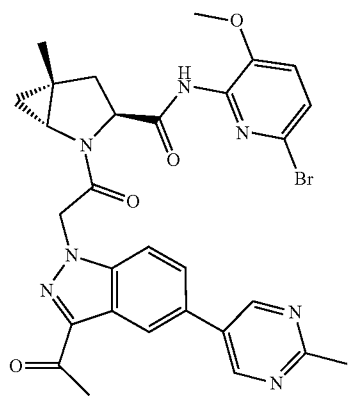 [SMILES: COc1ccc(Br)nc1NC(=O)[C@@H]1C[C@@]2(C)C[C@H]2N1C(=O)Cn1nc(C(C)=O)c2cc(-c3cnc(C)nc3)ccc21] | (1R,3S,5R)-2-(2-(3-acetyl-5-(2-methylpyrimidin-5-yl)-1H-indazol-1-yl)acetyl)-N-(6-bromo-3-methoxypyridin-2-yl)-5-methyl-2-azabicyclo[3.1.0]hexane-3-carboxamide | *** | 1.80 (A) | 620 |
| 364 | 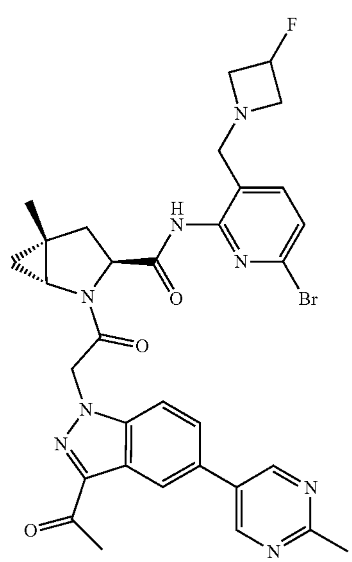 | (1R,3S,5R)-2-(2-(3-acetyl-5-(2-methylpyrimidin-5-yl)-1H-indazol-1-yl)acetyl)-N-(6-bromo-3-((3-fluoroazetidin-1-yl)methyl)pyridin-2-yl)-5-methyl-2-azabicyclo[3.1.0]hexane-3-carboxamide | *** | 2.74 (B) | 675 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 365 | 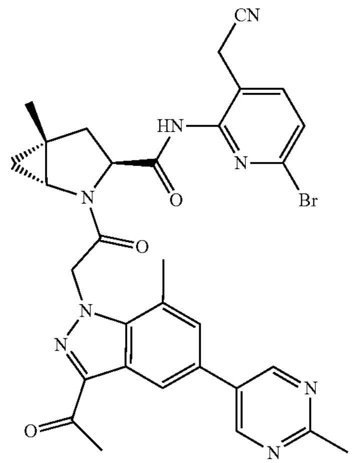 [SMILES: CC(=O)c1nn(CC(=O)N2[C@H](C(=O)Nc3nc(Br)ccc3CC#N)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-(cyanomethyl)pyridin-2-yl)-5-methyl-2-azabicyclo[3.1.0]hexane-3-carboxamide | *** | 3.39 (B) | 641 |
| 366 | 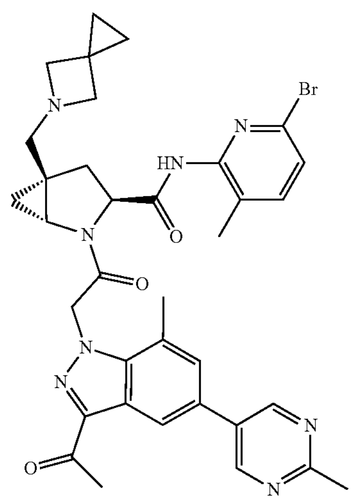 [SMILES: CC(=O)c1nn(CC(=O)N2[C@H](C(=O)Nc3nc(Br)ccc3C)C[C@@]3(CN4CC5(CC5)C4)C[C@@H]23)c2c(C)cc(-c3cnc(C)nc3)cc12] | (1R,3S,5R)-5-(5-azaspiro[2.3]hexan-5-ylmethyl)-2-(2-(3-acetyl-7-methyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide | *** | 2.74 (B) | 697 |
| 367 | 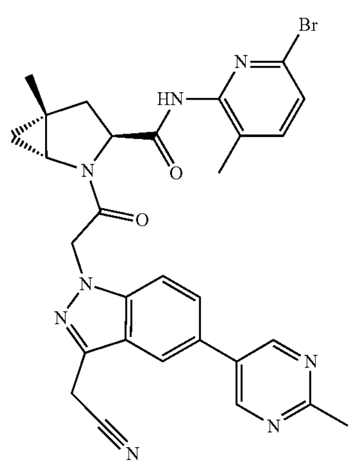 [SMILES: Cc1ncc(-c2ccc3c(c2)c(CC#N)nn3CC(=O)N2[C@H](C(=O)Nc3nc(Br)ccc3C)C[C@@]3(C)C[C@@H]23)cn1] | (1R,3S,5R)-N-(6-bromo-3-methylpyridin-2-yl)-2-(2-(3-(cyanomethyl)-5-(2-methylpyrimidin-5-yl)-1H-indazol-1-yl)acetyl)-5-methyl-2-azabicyclo[3.1.0]hexane-3-carboxamide | * | 3.05 (B) | 599 |

TABLE 7-continued

Additional Non-limiting Examples of Compounds of the Present Invention

| Cmp No. | Structure | Name | IC₅ (Stars) | RT min (A, B, C or D) | MS (M + 1) |
|---|---|---|---|---|---|
| 368 | 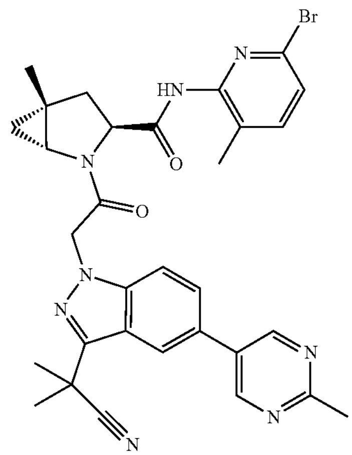 [SMILES: Cc1ncc(-c2ccc3c(c2)c(C(C)(C)C#N)nn3CC(=O)N2[C@H](C(=O)Nc3nc(Br)ccc3C)C[C@@]3(C)C[C@@H]23)cn1] | (1R,3S,5R)-N-(6-bromo-3-methylpyridin-2-yl)-2-(2-(3-(2-cyanopropan-2-yl)-5-(2-methylpyrimidin-5-yl)-1H-indazol-1-yl)acetyl)-5-methyl-2-azabicyclo[3.1.0]hexane-3-carboxamide | * | 3.74 (B) | 627 |
| 369 | 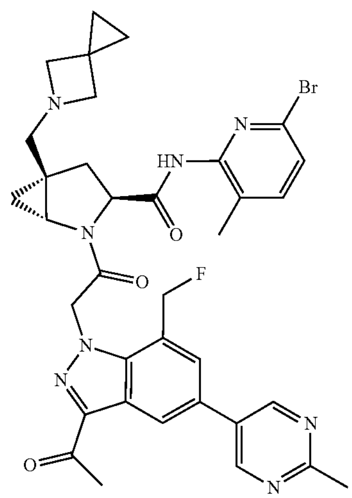 [SMILES: CC(=O)c1nn(CC(=O)N2[C@H](C(=O)Nc3nc(Br)ccc3C)C[C@@]3(CN4CC5(CC5)C4)C[C@@H]23)c2c(CF)cc(-c3cnc(C)nc3)cc12] | (1R,3S,5R)-5-(5-azaspiro[2.3]hexan-5-ylmethyl)-2-(2-(3-acetyl-7-(fluoromethyl)-5-(2-methylpyrimidin-5-yl)-1H-indazol-1-yl)acetyl)-N-(6-bromo-3-methylpyridin-2-yl)-2-azabicyclo[3.1.0]hexane-3-carboxamide | *** | 2.65 (B) | 715 |
| 370 | 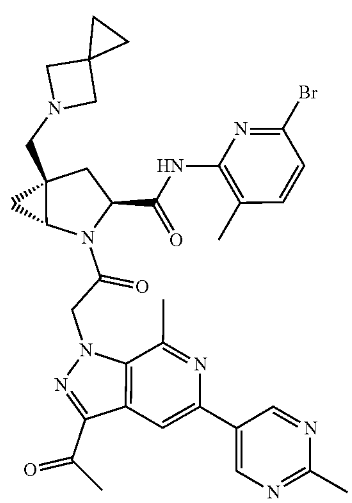 [SMILES: CC(=O)c1nn(CC(=O)N2[C@H](C(=O)Nc3nc(Br)ccc3C)C[C@@]3(CN4CC5(CC5)C4)C[C@@H]23)c2c(C)nc(-c3cnc(C)nc3)cc12] | (1R,3S,5R)-5-(5-azaspiro[2.3]hexan-5-ylmethyl)-2-(2-(3-acetyl-7-methyl-5-(2-methylpyrimidin-5-yl)-1H-pyrazolo[3,4-c]pyridin-1-yl)acetyl)-N-(6-bromo-3-methylpyridin-2-yl)-2-azabicyclo[3.1.0]hexane-3-carboxamide | *** | 2.67 (B) | 698 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 371 | 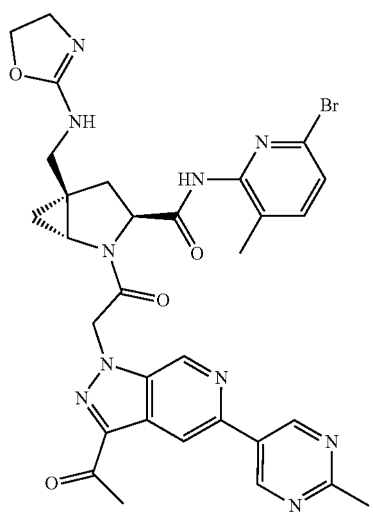 [SMILES: CC(=O)c1nn(CC(=O)N2[C@H](C(=O)Nc3nc(Br)ccc3C)C[C@@]3(CNC4=NCCO4)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-(((4,5-dihydrooxazol-2-yl)amino)methyl)-2-azabicyclo[3.1.0]hexane-3-carboxamide | *** | 2.53 (B) | 687 |
| 372 | 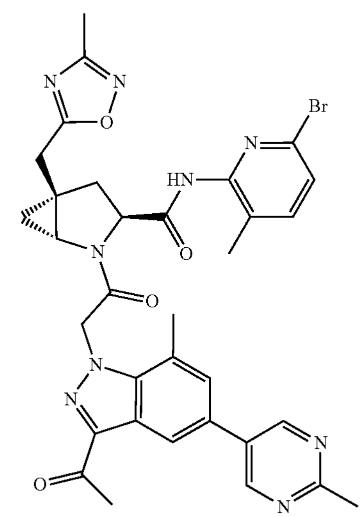 [SMILES: CC(=O)c1nn(CC(=O)N2[C@H](C(=O)Nc3nc(Br)ccc3C)C[C@@]3(Cc4nc(C)no4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-((3-methyl-1,2,4-oxadiazol-5-yl)methyl)-2-azabicyclo[3.1.0]hexane-3-carboxamide | *** | 3.00 (B) | 698 |
| 373 | 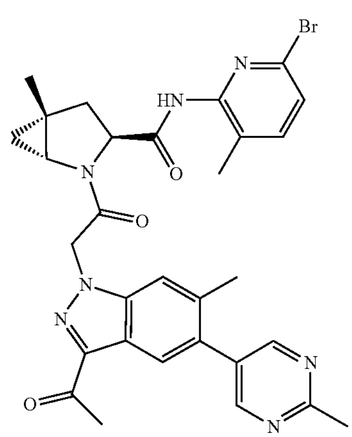 [SMILES: CC(=O)c1nn(CC(=O)N2[C@H](C(=O)Nc3nc(Br)ccc3C)C[C@@]3(C)C[C@@H]23)c2cc(C)c(-c3cnc(C)nc3)cc12] | (1R,3S,5R)-2-(2-(3-acetyl-6-methyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 1.89 (A) | 616 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 374 | 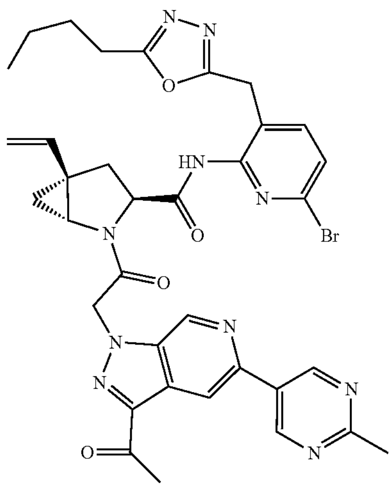 [SMILES: C=C[C@@]12C[C@@H](C(=O)Nc3nc(Br)ccc3Cc3nnc(CCCC)o3)N(C(=O)Cn3nc(C(C)=O)c4cc(-c5cnc(C)nc5)ncc43)[C@@H]1C2] | (1R,3S,5R)-2-(2-(3-acetyl-5-(2-methylpyrimidin-5-yl)-1H-pyrazolo[3,4-c]pyridin-1-yl)acetyl)-N-(6-bromo-3-((5-butyl-1,3,4-oxadiazol-2-yl)methyl)pyridin-2-yl)-5-vinyl-2-azabicyclo[3.1.0]hexane-3-carboxamide | *** | 2.04 (A) | 741 |
| 375 | 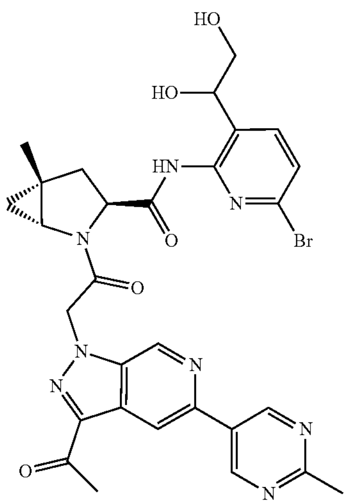 [SMILES: CC(=O)c1nn(CC(=O)N2[C@H](C(=O)Nc3nc(Br)ccc3C(O)CO)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-(1,2-dihydroxyethyl)pyridin-2-yl)-5-methyl-2-azabicyclo[3.1.0]hexane-3-carboxamide | *** | 2.19 (B) | 649 |
| 376 | 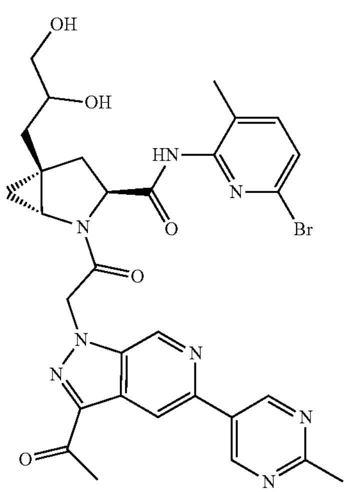 [SMILES: CC(=O)c1nn(CC(=O)N2[C@H](C(=O)Nc3nc(Br)ccc3C)C[C@@]3(CC(O)CO)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-(2,3-dihydroxypropyl)-2-azabicyclo[3.1.0]hexane-3-carboxamide | *** | 2.44 (B) | 663 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 377 | 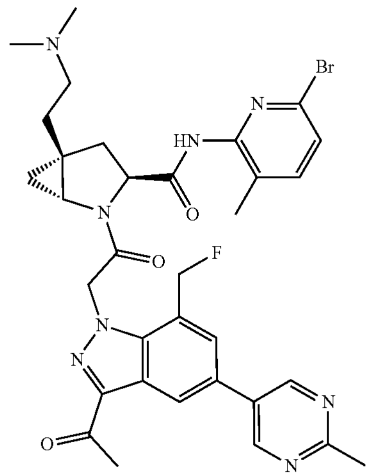 | (1R,3S,5R)-2-(2-(3-acetyl-7-(fluoromethyl)-5-(2-methylpyrimidin-5-yl)-1H-indazol-1-yl)acetyl)-N-(6-bromo-3-methylpyridin-2-yl)-5-(2-(dimethylamino)ethyl)-2-azabicyclo[3.1.0]hexane-3-carboxamide | *** | 2.42 (B) | 691 |
| 378 | 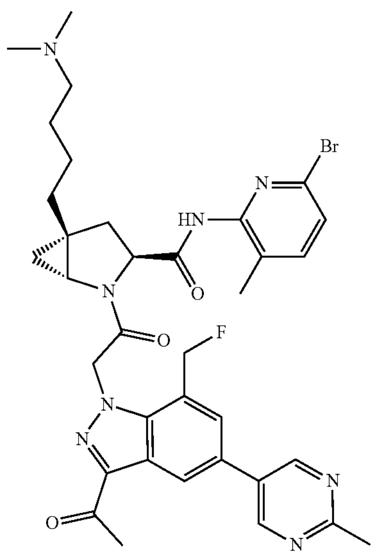 | (1R,3S,5R)-2-(2-(3-acetyl-7-(fluoromethyl)-5-(2-methylpyrimidin-5-yl)-1H-indazol-1-yl)acetyl)-N-(6-bromo-3-methylpyridin-2-yl)-5-(4-(dimethylamino)butyl)-2-azabicyclo[3.1.0]hexane-3-carboxamide | *** | 2.24 (B) | 719 |
| 380 | 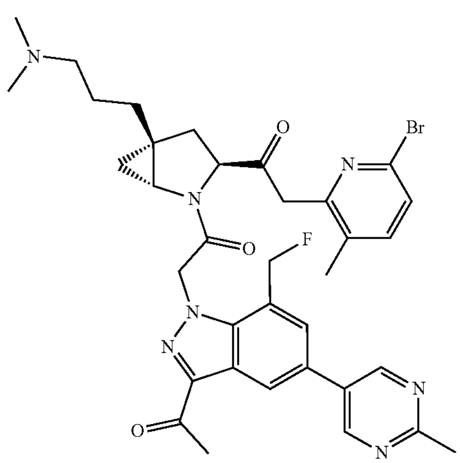 | (1R,3S,5R)-2-(2-(3-acetyl-7-(fluoromethyl)-5-(2-methylpyrimidin-5-yl)-1H-indazol-1-yl)acetyl)-5-(3-(dimethylamino)propyl)-N-(3-methyl-6-(trifluoromethyl)pyridin-2-yl)-2-azabicyclo[3.1.0]hexane-3-carboxamide | *** | 2.95 (B) | 695 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 381 | 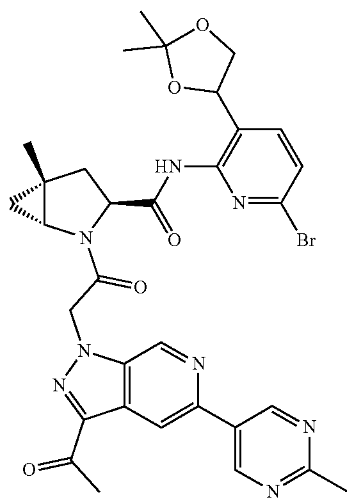 [SMILES: CC(=O)c1nn(CC(=O)N2[C@H](C(=O)Nc3nc(Br)ccc3C3COC(C)(C)O3)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-(2,2-dimethyl-1,3-dioxolan-4-yl)pyridin-2-yl)-5-methyl-2-azabicyclo[3.1.0]hexane-3-carboxamide | *** | 3.29 (B) | 689 |
| 382 | 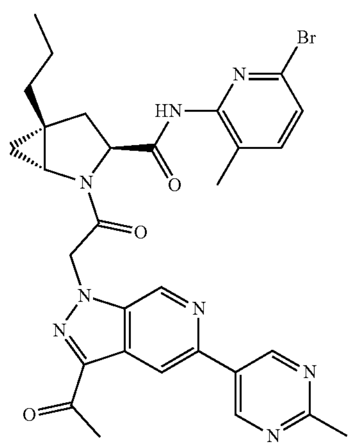 [SMILES: CCC[C@@]12C[C@@H](C(=O)Nc3nc(Br)ccc3C)N(C(=O)Cn3nc(C(C)=O)c4cc(-c5cnc(C)nc5)ncc43)[C@@H]1C2] | (1R,3S,5R)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-propyl-2-azabicyclo[3.1.0]hexane-3-carboxamide | *** | 3.40 (B) | 631 |
| 383 | 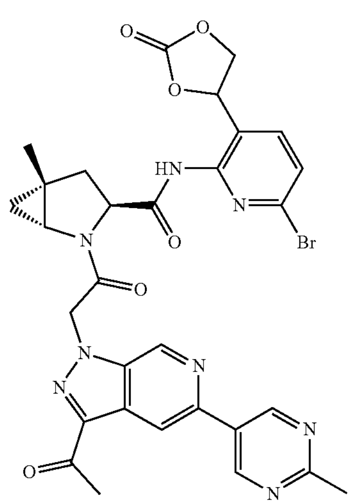 [SMILES: CC(=O)c1nn(CC(=O)N2[C@H](C(=O)Nc3nc(Br)ccc3C3COC(=O)O3)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-(2-oxo-1,3-dioxolan-4-yl)pyridin-2-yl)-5-methyl-2-azabicyclo[3.1.0]hexane-3-carboxamide | *** | 2.70 (B) | 675 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 384 | 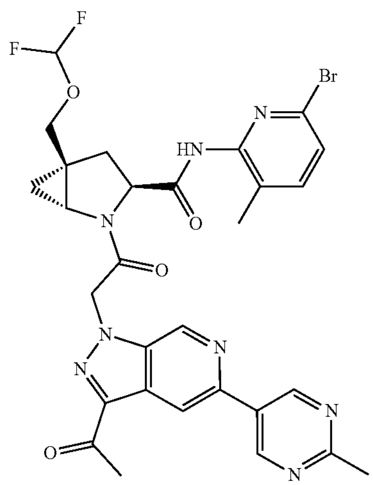 [SMILES: CC(=O)c1nn(CC(=O)N2[C@H](C(=O)Nc3nc(Br)ccc3C)C[C@@]3(COC(F)F)C[C@@H]23)c2cnc(-c3cnc(C)nc3)cc12] | (1R,3S,5S)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-((difluoromethoxy)methyl)-2-azabicyclo[3.1.0]hexane-3-carboxamide | *** | 2.86 (B) | 669 |
| 385 | 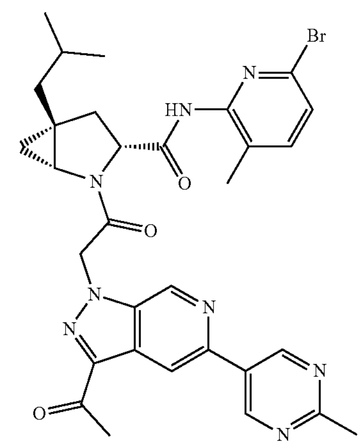 [SMILES: CC(=O)c1nn(CC(=O)N2[C@@H](C(=O)Nc3nc(Br)ccc3C)C[C@@]3(CC(C)C)C[C@@H]23)c2cnc(-c3cnc(C)nc3)cc12] | (1R,3R,5R)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-isobutyl-2-azabicyclo[3.1.0]hexane-3-carboxamide | * | 3.55 (B) | 645 |
| 386 | 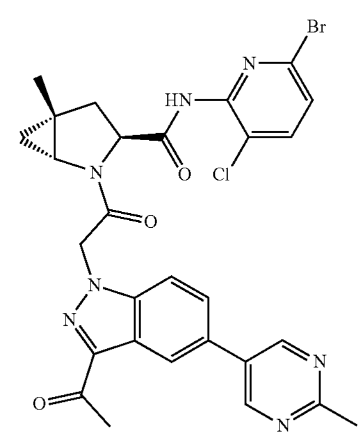 [SMILES: CC(=O)c1nn(CC(=O)N2[C@H](C(=O)Nc3nc(Br)ccc3Cl)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-chloropyridin-2-yl)-5-methyl-2-azabicyclo[3.1.0]hexane-3-carboxamide | *** | 3.35 (B) | 622 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 387 | 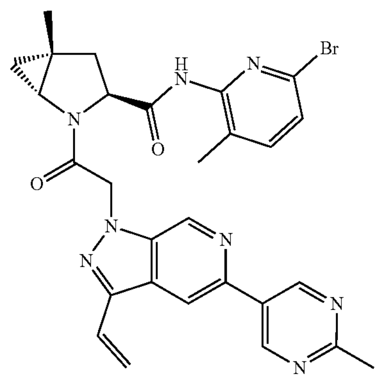 [SMILES: C=Cc1nn(CC(=O)N2[C@H](C(=O)Nc3nc(Br)ccc3C)C[C@@]3(C)C[C@@H]23)c2cnc(-c3cnc(C)nc3)cc12] | (1R,3S,5R)-N-(6-bromo-3-methylpyridin-2-yl)-5-methyl-2-(2-(5-(2-methylpyrimidin-5-yl)-3-vinyl-1H-pyrazolo[3,4-c]pyridin-1-yl)acetyl)-2-azabicyclo[3.1.0]hexane-3-carboxamide | *** | 1.78 (A) | 586 |
| 388 | 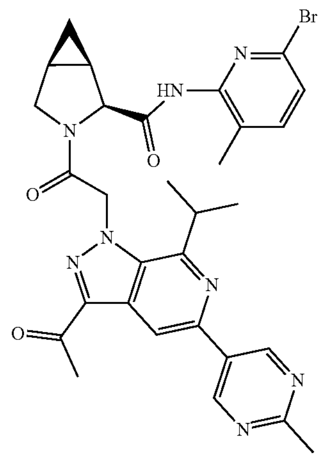 [SMILES: CC(=O)c1nn(CC(=O)N2C[C@H]3C[C@H]3[C@H]2C(=O)Nc2nc(Br)ccc2C)c2c(C(C)C)nc(-c3cnc(C)nc3)cc12] | (1R,2S,5S)-3-(2-(3-acetyl-7-isopropyl-5-(2-methylpyrimidin-5-yl)-1H-pyrazolo[3,4-c]pyridin-1-yl)acetyl)-N-(6-bromo-3-methylpyridin-2-yl)-3-azabicyclo[3.1.0]hexane-2-carboxamide | *** | 2.01 (A) | 633 |
| 389 | 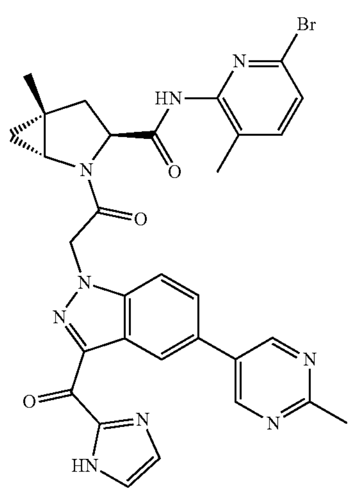 [SMILES: Cc1ncc(-c2ccc3c(c2)c(C(=O)c2ncc[nH]2)nn3CC(=O)N2[C@H](C(=O)Nc3nc(Br)ccc3C)C[C@@]3(C)C[C@@H]23)cn1] | (1R,3S,5R)-2-(2-(3-(1H-imidazole-2-carbonyl)-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | * | 8.79 (D) | 656 (M + 2) |

TABLE 7-continued

Additional Non-limiting Examples of Compounds of the Present Invention

| Cmp No. | Structure | Name | IC₅ (Stars) | RT min (A, B, C or D) | MS (M + 1) |
|---|---|---|---|---|---|
| 390 | 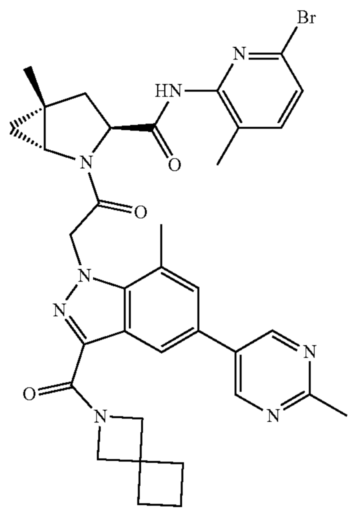 [SMILES: Cc1ncc(-c2cc(C)c3c(c2)c(C(=O)N2CC4(CCC4)C2)nn3CC(=O)N2[C@H](C(=O)Nc3nc(Br)ccc3C)C[C@@]3(C)C[C@@H]23)cn1] | (1R,3S,5R)-N-(6-bromo-3-methylpyridin-2-yl)-5-methyl-2-(2-(7-methyl-5-(2-methylpyrimidin-5-yl)-3-(2-azaspiro[3.3]heptane-2-carbonyl)-1H-indazol-1-yl)acetyl)-2-azabicyclo[3.1.0]hexane-3-carboxamide | * | 11.51 (D) | 695 (M − 2) |
| 393 | 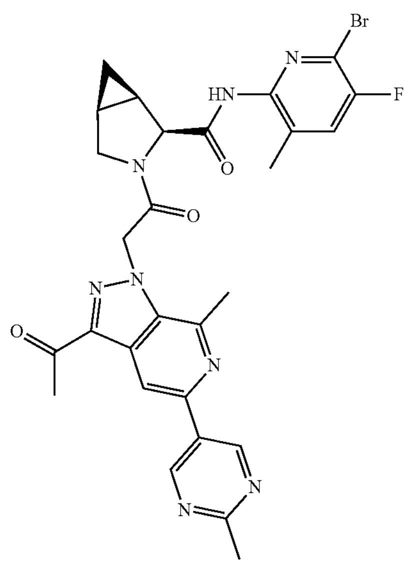 [SMILES: CC(=O)c1nn(CC(=O)N2C[C@H]3C[C@H]3[C@H]2C(=O)Nc2nc(Br)c(F)cc2C)c2c(C)nc(-c3cnc(C)nc3)cc12] | (1R,2S,5S)-3-(2-(3-acetyl-7-methyl-5-(2-methylpyrimidin-5-yl)-1H-pyrazolo[3,4-c]pyridin-1-yl)acetyl)-N-(6-bromo-5-fluoro-3-methylpyridin-2-yl)-3-azabicyclo[3.1.0]hexane-2-carboxamide | *** | 1.73 (A) | 623 |
| 394 | 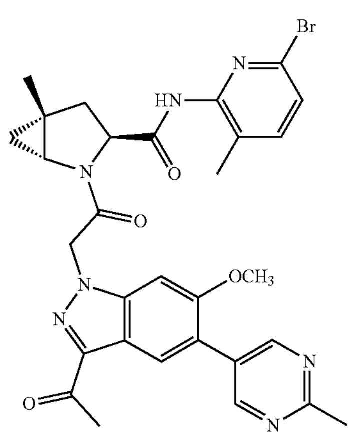 [SMILES: COc1cc2c(cc1-c1cnc(C)nc1)c(C(C)=O)nn2CC(=O)N1[C@H](C(=O)Nc2nc(Br)ccc2C)C[C@@]2(C)C[C@@H]12] | (1R,3S,5R)-2-(2-(3-acetyl-6-methoxy-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 1.88 (A) | 632 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 395 | 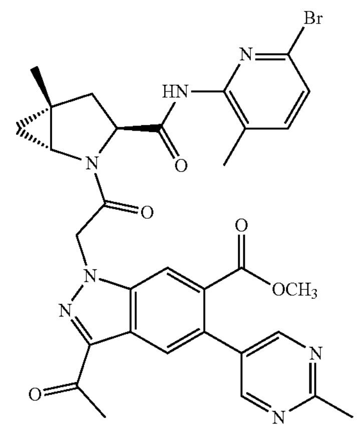 [SMILES: COC(=O)c1cc2c(cc1-c1cnc(C)nc1)c(C(C)=O)nn2CC(=O)N1[C@H](C(=O)Nc2nc(Br)ccc2C)C[C@@]2(C)C[C@@H]12] | methyl 3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-5-(2-methylpyrimidin-5-yl)-1H-indazole-6-carboxylate | *** | 1.87 (A) | 660 |
| 396 | 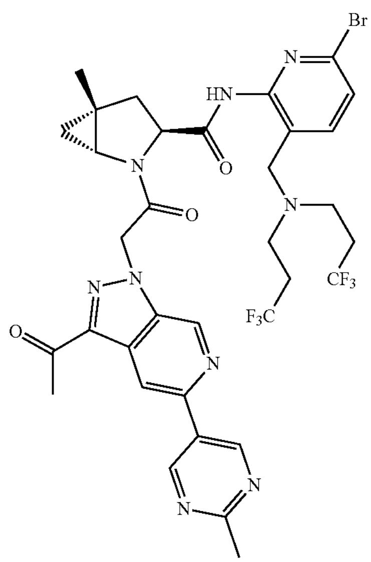 [SMILES: CC(=O)c1nn(CC(=O)N2[C@H](C(=O)Nc3nc(Br)ccc3CN(CCC(F)(F)F)CCC(F)(F)F)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(3-((bis(3,3,3-trifluoropropyl)amino)methyl)-6-bromopyridin-2-yl)-5-methyl-2-azabicyclo[3.1.0]hexane-3-carboxamide | *** | 2.62 (A) | 810 |
| 397 | 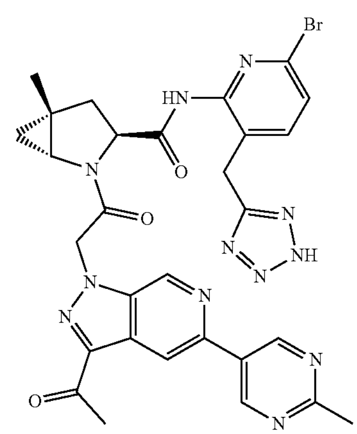 [SMILES: CC(=O)c1nn(CC(=O)N2[C@H](C(=O)Nc3nc(Br)ccc3Cc3nn[nH]n3)C[C@@]3(C)C[C@@H]23)c2cnc(-c3cnc(C)nc3)cc12] | (1R,3S,5R)-N-(3-((2H-tetrazol-5-yl)methyl)-6-bromopyridin-2-yl)-2-(2-(3-acetyl-5-(2-methylpyrimidin-5-yl)-1H-pyrazolo[3,4-c]pyridin-1-yl)acetyl)-5-methyl-2-azabicyclo[3.1.0]hexane-3-carboxamide | *** | 2.94 (B) | 671 |

TABLE 7-continued

*Additional Non-limiting Examples of Compounds of the Present Invention*

| Cmp No. | Structure | Name | IC$_5$ (Stars) | RT min (A, B, C or D) | MS (M + 1) |
|---|---|---|---|---|---|
| 398 | 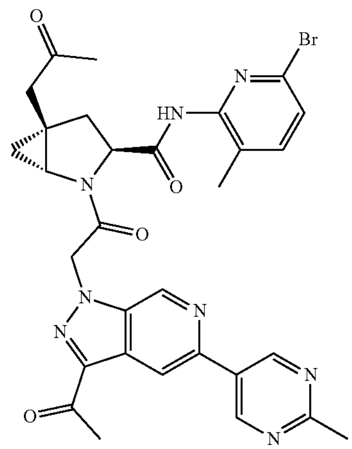 [SMILES: CC(=O)C[C@@]12C[C@@H](C(=O)Nc3nc(Br)ccc3C)N(C(=O)Cn3nc(C(C)=O)c4cc(-c5cnc(C)nc5)ncc43)[C@@H]1C2] | (1R,3S,5R)-2-(2-(3-acetyl-5-(2-methylpyrimidin-5-yl)-1H-pyrazolo[3,4-c]pyridin-1-yl)acetyl)-N-(6-bromo-3-methylpyridin-2-yl)-5-(2-oxopropyl)-2-azabicyclo[3.1.0]hexane-3-carboxamide | *** | 2.77 (B) | 645 |
| 399 | 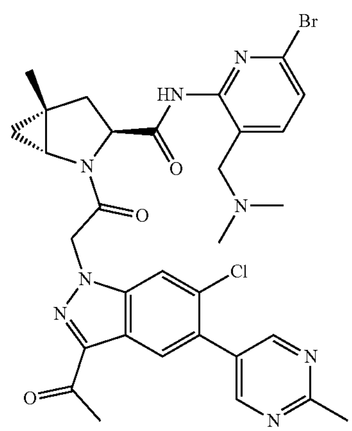 [SMILES: CC(=O)c1nn(CC(=O)N2[C@H](C(=O)Nc3nc(Br)ccc3CN(C)C)C[C@@]3(C)C[C@@H]23)c2cc(Cl)c(-c3cnc(C)nc3)cc12] | (1R,3S,5R)-2-(2-(3-acetyl-6-chloro-5-(2-methylpyrimidin-5-yl)-1H-indazol-1-yl)acetyl)-N-(6-bromo-3-((dimethylamino)methyl)pyridin-2-yl)-5-methyl-2-azabicyclo[3.1.0]hexane-3-carboxamide | *** | 2.77 (B) | 679 |
| 400 | 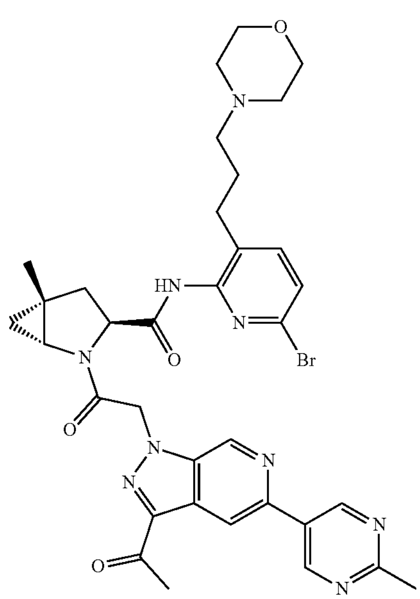 [SMILES: CC(=O)c1nn(CC(=O)N2[C@H](C(=O)Nc3nc(Br)ccc3CCCN3CCOCC3)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-(3-morpholinopropyl)pyridin-2-yl)-5-methyl-2-azabicyclo[3.1.0]hexane-3-carboxamide | *** | 2.48 (B) | 716 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 401 | 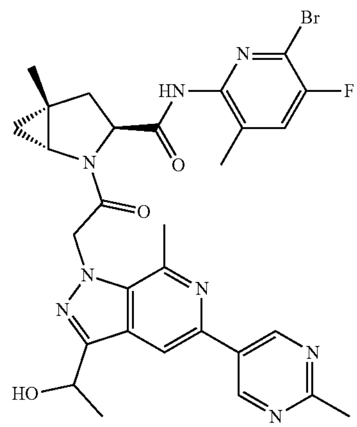 [SMILES: Cc1ncc(-c2cc3c(C(C)O)nn(CC(=O)N4[C@H](C(=O)Nc5nc(Br)c(F)cc5C)C[C@@]5(C)C[C@@H]45)c3c(C)n2)cn1] | (1R,3S,5R)-N-(6-bromo-5-fluoro-3-methylpyridin-2-yl)-2-(2-(3-(1-hydroxyethyl)-7-methyl-5-(2-methylpyrimidin-5-yl)-1H-pyrazolo[3,4-c]pyridin-1-yl)acetyl)-5-methyl-2-azabicyclo[3.1.0]hexane-3-carboxamide | *** | 1.62 (A) | 636 |
| 402 | 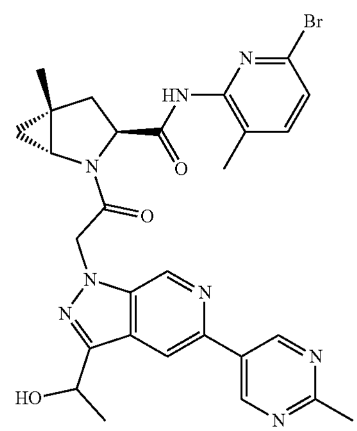 [SMILES: Cc1ncc(-c2cc3c(C(C)O)nn(CC(=O)N4[C@H](C(=O)Nc5nc(Br)ccc5C)C[C@@]5(C)C[C@@H]45)c3cn2)cn1] | (1R,3S,5R)-N-(6-bromo-3-methylpyridin-2-yl)-2-(2-(3-(1-hydroxyethyl)-5-(2-methylpyrimidin-5-yl)-1H-pyrazolo[3,4-c]pyridin-1-yl)acetyl)-5-methyl-2-azabicyclo[3.1.0]hexane-3-carboxamide | ** | 1.42 (A) | 607 |
| 407 | 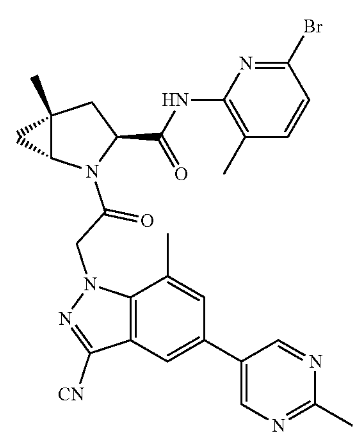 | (1R,3S,5R)-N-(6-bromo-3-methylpyridin-2-yl)-2-(2-(3-cyano-7-methyl-5-(2-methylpyrimidin-5-yl)-1H-indazol-1-yl)acetyl)-5-methyl-2-azabicyclo[3.1.0]hexane-3-carboxamide | *** | 11.21 (D) | 601 (M + 2) |

TABLE 7-continued

Additional Non-limiting Examples of Compounds of the Present Invention

| Cmp No. | Structure | Name | IC₅₀ (Stars) | RT min (A, B, C or D) | MS (M + 1) |
|---|---|---|---|---|---|
| 408 | 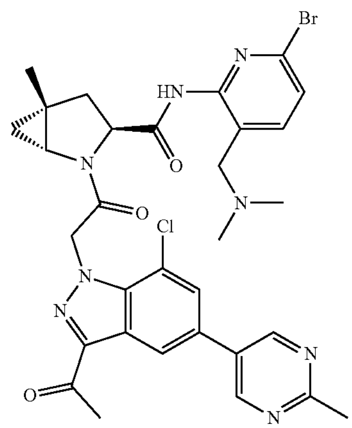 [SMILES: CC(=O)c1nn(CC(=O)N2[C@H](C(=O)Nc3nc(Br)ccc3CN(C)C)C[C@@]3(C)C[C@@H]23)c2c(Cl)cc(-c3cnc(C)nc3)cc12] | (1R,3S,5R)-2-(2-(3-acetyl-7-chloro-5-(2-methylpyrimidin-5-yl)-1H-indazol-1-yl)acetyl)-N-(6-bromo-3-((dimethyl-amino)methyl)pyridin-2-yl)-5-methyl-2-azabicyclo[3.1.0]hexane-3-carboxamide | *** | 3.00 (B) | 679 |
| 409 | 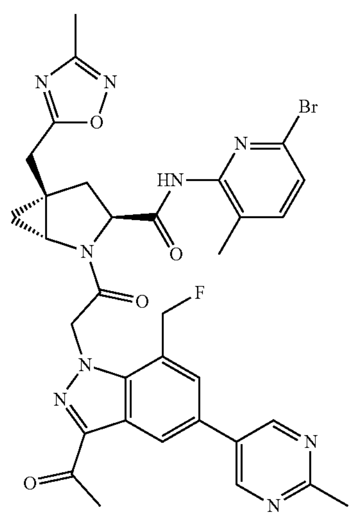 [SMILES: CC(=O)c1nn(CC(=O)N2[C@H](C(=O)Nc3nc(Br)ccc3C)C[C@@]3(Cc4nc(C)no4)C[C@@H]23)c2c(CF)cc(-c3cnc(C)nc3)cc12] | (1R,3S,5R)-2-(2-(3-acetyl-7-(fluoromethyl)-5-(2-methylpyrimidin-5-yl)-1H-indazol-1-yl)acetyl)-N-(6-bromo-3-methylpyridin-2-yl)-5-((3-methyl-1,2,4-oxadiazol-5-yl)methyl)-2-azabicyclo[3.1.0]hexane-3-carboxamide | *** | 2.92 (B) | 716 |
| 410 | 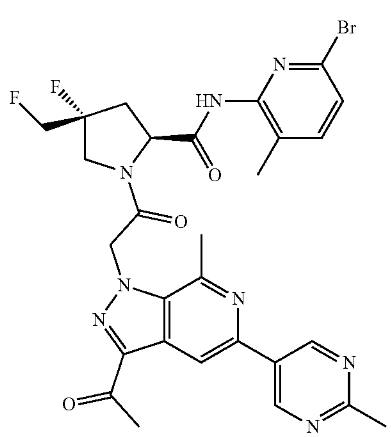 [SMILES: CC(=O)c1nn(CC(=O)N2C[C@@](F)(CF)C[C@H]2C(=O)Nc2nc(Br)ccc2C)c2c(C)nc(-c3cnc(C)nc3)cc12] | (2S,4R)-1-(2-(3-acetyl-7-methyl-5-(2-methylpyrimidin-5-yl)-1H-pyrazolo[3,4-c]pyridin-1-yl)acetyl)-N-(6-bromo-3-methylpyridin-2-yl)-4-fluoro-4-(fluoro-methyl)pyrrolidine-2-carboxamide | *** | 3.02 (B) | 641 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 411 | 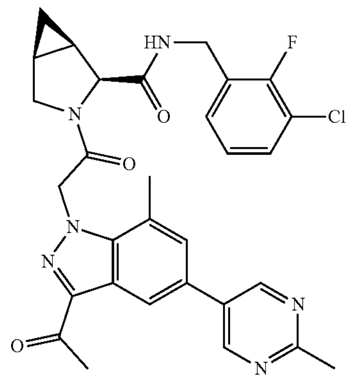 [SMILES: CC(=O)c1nn(CC(=O)N2C[C@H]3C[C@H]3[C@H]2C(=O)NCc2cccc(Cl)c2F)c2c(C)cc(-c3cnc(C)nc3)cc12] | (1R,2S,5S)-3-(2-(3-acetyl-7-methyl-5-(2-methylpyrimidin-5-yl)-1H-pyrazolo[3,4-c]pyridin-1-yl)acetyl)-N-(3-chloro-2-fluorobenzyl)-3-azabicyclo[3.1.0]hexane-2-carboxamide | *** | 3.29 (B) | 576 |
| 412 | 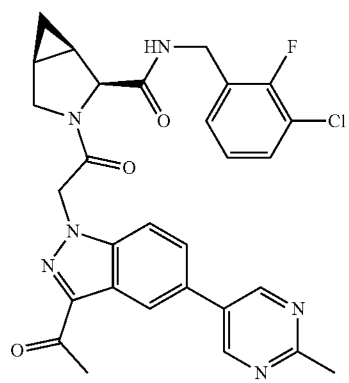 [SMILES: CC(=O)c1nn(CC(=O)N2C[C@H]3C[C@H]3[C@H]2C(=O)NCc2cccc(Cl)c2F)c2ccc(-c3cnc(C)nc3)cc12] | (1R,2S,5S)-3-(2-(3-acetyl-5-(2-methylpyrimidin-5-yl)-1H-indazol-1-yl)acetyl)-N-(3-chloro-2-fluorobenzyl)-3-azabicyclo[3.1.0]hexane-2-carboxamide | *** | 3.28 (B) | 561 |
| 413 | 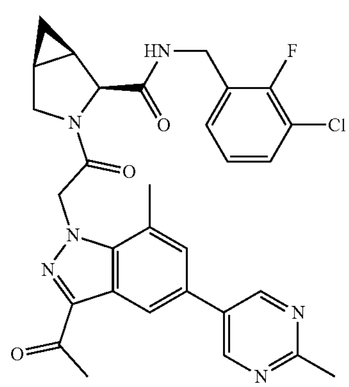 [SMILES: CC(=O)c1nn(CC(=O)N2C[C@H]3C[C@H]3[C@H]2C(=O)NCc2cccc(Cl)c2F)c2c(C)cc(-c3cnc(C)nc3)cc12] | (1R,2S,5S)-3-(2-(3-acetyl-7-methyl-5-(2-methylpyrimidin-5-yl)-1H-indazol-1-yl)acetyl)-N-(3-chloro-2-fluorobenzyl)-3-azabicyclo[3.1.0]hexane-2-carboxamide | *** | 3.41 (B) | 575 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 415 | 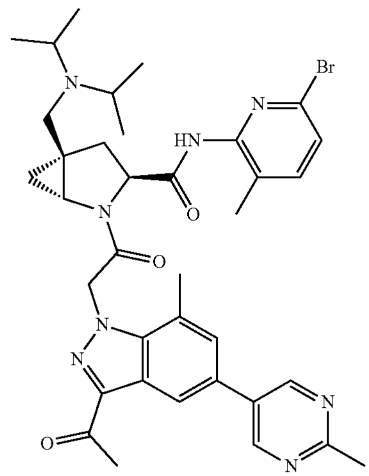 [SMILES: CC(=O)c1nn(CC(=O)N2[C@H](C(=O)Nc3nc(Br)ccc3C)C[C@@]3(CN(C(C)C)C(C)C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-((diisopropylamino)methyl)-2-azabicyclo[3.1.0]hexane-3-carboxamide | *** | 2.81 (B) | 715 |
| 416 | 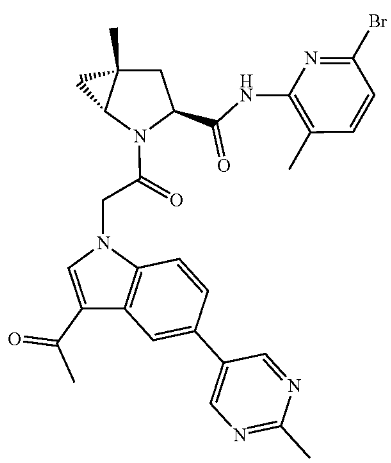 [SMILES: CC(=O)c1cn(CC(=O)N2[C@H](C(=O)Nc3nc(Br)ccc3C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indol-1-yl)acetyl)-N-(6-bromo-3-methylpyridin-2-yl)-5-methyl-2-azabicyclo[3.1.0]hexane-3-carboxamide | *** | 1.70 (A) | 603 |
| 417 | 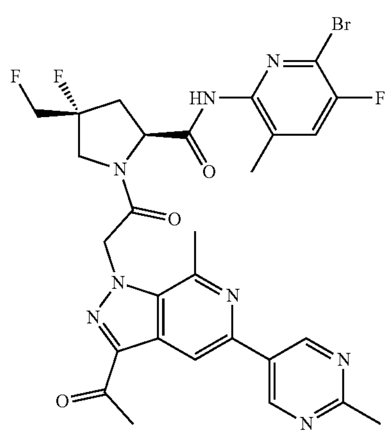 [SMILES: CC(=O)c1nn(CC(=O)N2C[C@@](F)(CF)C[C@H]2C(=O)Nc2nc(Br)c(F)cc2C)c2c(C)nc(-c3cnc(C)nc3)cc12] | (2S,4R)-1-(2-(3-acetyl-7-methyl-5-(2-methylpyrimidin-5-yl)-1H-pyrazolo[3,4-c]pyridin-1-yl)acetyl)-N-(6-bromo-5-fluoro-3-methylpyridin-2-yl)-4-fluoro-4-(fluoromethyl)pyrrolidine-2-carboxamide | *** | 3.11 (B) | 659 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 418 | 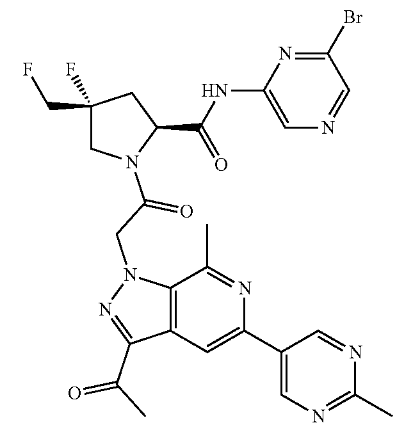 [SMILES: CC(=O)c1nn(CC(=O)N2C[C@@](F)(CF)C[C@H]2C(=O)Nc2cncc(Br)n2)c2c(C)nc(-c3cnc(C)nc3)cc12] | (2S,4R)-1-(2-(3-acetyl-7-methyl-5-(2-methylpyrimidin-5-yl)-1H-pyrazolo[3,4-c]pyridin-1-yl)acetyl)-N-(6-bromopyrazin-2-yl)-4-fluoro-4-(fluoromethyl)pyrrolidine-2-carboxamide | *** | 3.13 (B) | 628 |
| 419 | 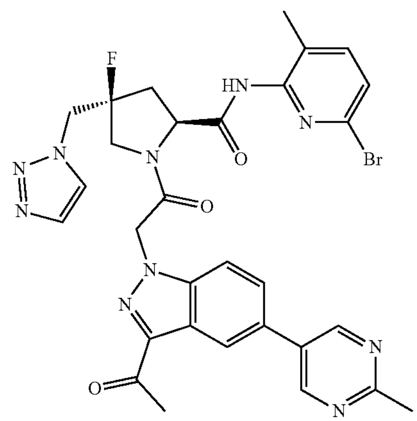 [SMILES: CC(=O)c1nn(CC(=O)N2C[C@](F)(Cn3ccnn3)C[C@H]2C(=O)Nc2nc(Br)ccc2C)c2ccc(-c3cnc(C)nc3)cc12] | (2S,4S)-4-((1H-1,2,3-triazol-1-yl)methyl)-1-(2-(3-acetyl-5-(2-methylpyrimidin-5-yl)-1H-indazol-1-yl)acetyl)-N-(6-bromo-3-methylpyridin-2-yl)-4-fluoropyrrolidine-2-carboxamide | *** | 2.97 (B) | 675 |
| 420 | 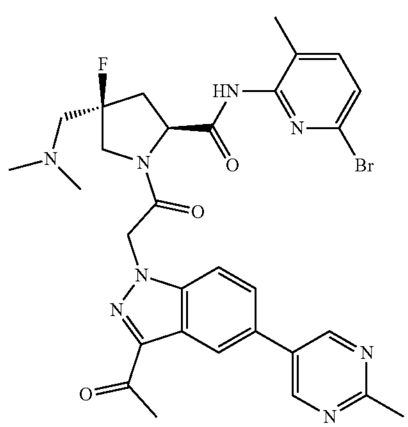 | (2S,4R)-1-(2-(3-acetyl-5-(2-methylpyrimidin-5-yl)-1H-indazol-1-yl)acetyl)-N-(6-bromo-3-methylpyridin-2-yl)-4-((dimethylamino)methyl)-4-fluoropyrrolidine-2-carboxamide | ** | 2.16 (B) | 651 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 421 | 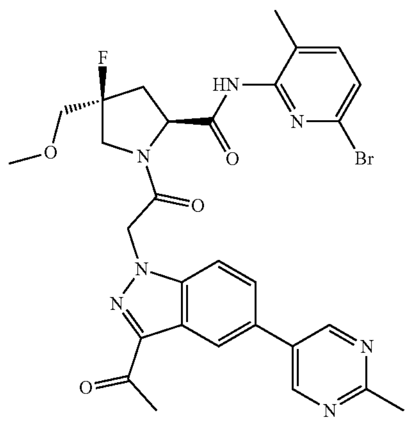 | (2S,4S)-1-(2-(3-acetyl-5-(2-methylpyrimidin-5-yl)-1H-indazol-1-yl)acetyl)-N-(6-bromo-3-methylpyridin-2-yl)-4-fluoro-4-(methoxymethyl)pyrrolidine-2-carboxamide | *** | 3.22 (B) | 638 |
| 422 | 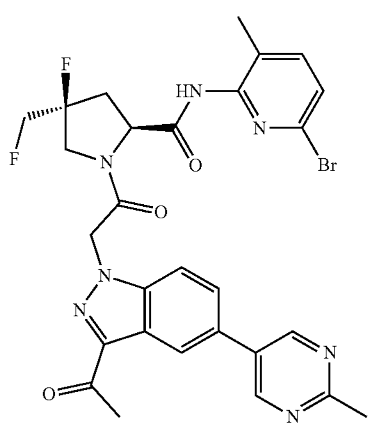 [SMILES: CC(=O)c1nn(CC(=O)N2C[C@](F)(CF)C[C@H]2C(=O)Nc2nc(Br)ccc2C)c2ccc(-c3cnc(C)nc3)cc12] | (2S,4S)-1-(2-(3-acetyl-5-(2-methylpyrimidin-5-yl)-1H-indazol-1-yl)acetyl)-N-(6-bromo-3-methylpyridin-2-yl)-4-fluoro-4-(fluoromethyl)pyrrolidine-2-carboxamide | *** | 2.67 (B) | 626 |
| 423 | 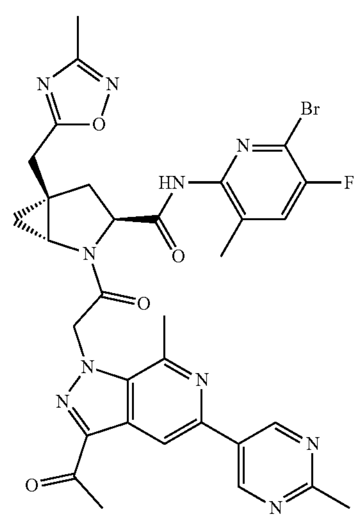 [SMILES: CC(=O)c1nn(CC(=O)N2[C@H](C(=O)Nc3nc(Br)c(F)cc3C)C[C@@]3(Cc4nc(C)no4)C[C@@H]23)c2c(C)nc(-c3cnc(C)nc3)cc12] | (1R,3S,5R)-2-(2-(3-acetyl-7-methyl-5-(2-methylpyrimidin-5-yl)-1H-pyrazolo[3,4-c]pyridin-1-yl)acetyl)-N-(6-bromo-5-fluoro-3-methylpyridin-2-yl)-5-((3-methyl-1,2,4-oxadiazol-5-yl)methyl)-2-azabicyclo[3.1.0]hexane-3-carboxamide | *** | 3.44 (B) | 717 |

TABLE 7-continued

Additional Non-limiting Examples of Compounds of the Present Invention

| Cmp No. | Structure | Name | IC₅ (Stars) | RT min (A, B, C or D) | MS (M + 1) |
|---|---|---|---|---|---|
| 424 | 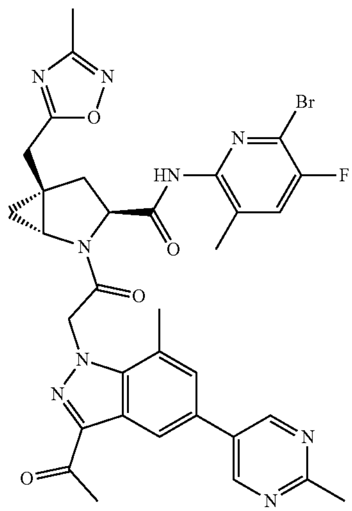 [SMILES: CC(=O)c1nn(CC(=O)N2[C@H](C(=O)Nc3nc(Br)c(F)cc3C)C[C@@]3(Cc4nc(C)no4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-5-fluoro-3-methylpyridin-2-yl)-5-((3-methyl-1,2,4-oxadiazol-5-yl)methyl)-2-azabicyclo[3.1.0]hexane-3-carboxamide | *** | 3.54 (B) | 716 |
| 425 | 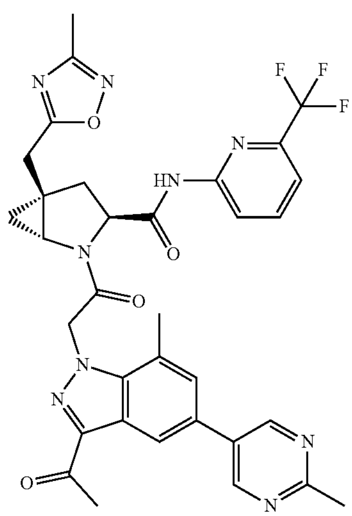 [SMILES: CC(=O)c1nn(CC(=O)N2[C@H](C(=O)Nc3cccc(C(F)(F)F)n3)C[C@@]3(Cc4nc(C)no4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-((3-methyl-1,2,4-oxadiazol-5-yl)methyl)-N-(3-methyl-6-(trifluoromethyl)pyridin-2-yl)-2-azabicyclo[3.1.0]hexane-3-carboxamide | *** | 3.66 (B) | 688 |
| 426 | 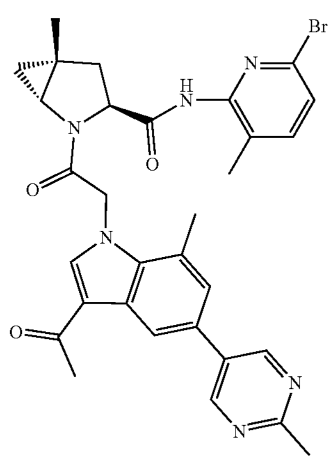 [SMILES: CC(=O)c1cn(CC(=O)N2[C@H](C(=O)Nc3nc(Br)ccc3C)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indol-1-yl)acetyl)-N-(6-bromo-3-methylpyridin-2-yl)-5-methyl-2-azabicyclo[3.1.0]hexane-3-carboxamide | *** | 1.78 (A) | 615 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 427 | 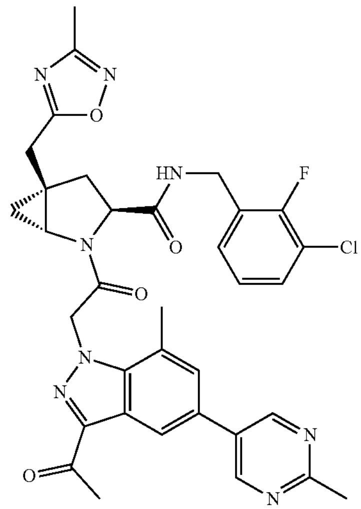 [SMILES: CC(=O)c1nn(CC(=O)N2[C@H](C(=O)NCc3cccc(Cl)c3F)C[C@@]3(Cc4nc(C)no4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(3-chloro-2-fluorobenzyl)-5-((3-methyl-1,2,4-oxadiazol-5-yl)methyl)-2-azabicyclo[3.1.0]hexane-3-carboxamide | *** | 3.62 (B) | 671 |
| 428 | 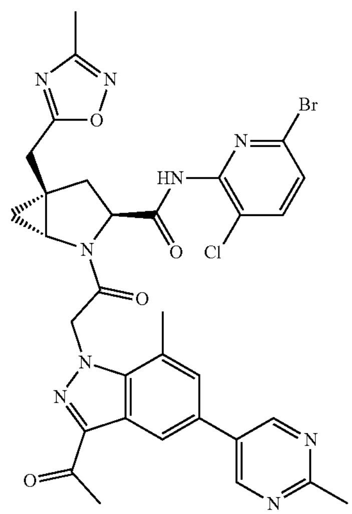 [SMILES: CC(=O)c1nn(CC(=O)N2[C@H](C(=O)Nc3nc(Br)ccc3Cl)C[C@@]3(Cc4nc(C)no4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-chloropyridin-2-yl)-5-((3-methyl-1,2,4-oxadiazol-5-yl)methyl)-2-azabicyclo[3.1.0]hexane-3-carboxamide | *** | 3.35 (B) | 720 |
| 429 | 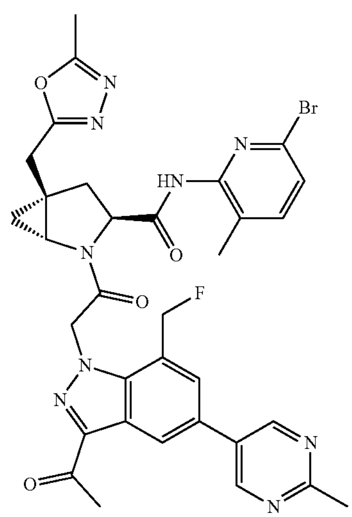 [SMILES: CC(=O)c1nn(CC(=O)N2[C@H](C(=O)Nc3nc(Br)ccc3C)C[C@@]3(Cc4nnc(C)o4)C[C@@H]23)c2c(CF)cc(-c3cnc(C)nc3)cc12] | (1R,3S,5R)-2-(2-(3-acetyl-7-(fluoromethyl)-5-(2-methylpyrimidin-5-yl)-1H-indazol-1-yl)acetyl)-N-(6-bromo-3-methylpyridin-2-yl)-5-((5-methyl-1,3,4-oxadiazol-2-yl)methyl)-2-azabicyclo[3.1.0]hexane-3-carboxamide | *** | 3.22 (B) | 716 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 430 | 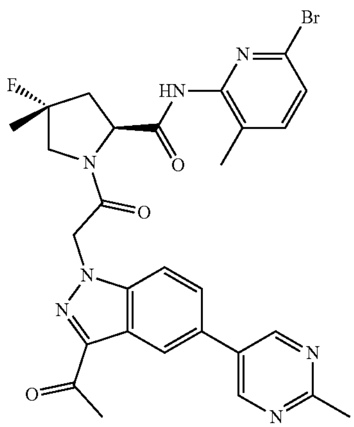 | (2S,4R)-1-(2-(3-acetyl-5-(2-methylpyrimidin-5-yl)-1H-indazol-1-yl)acetyl)-N-(6-bromo-3-methylpyridin-2-yl)-4-fluoro-4-methylpyrrolidine-2-carboxamide | *** | 3.18 (B) | 608 |
| 431 | 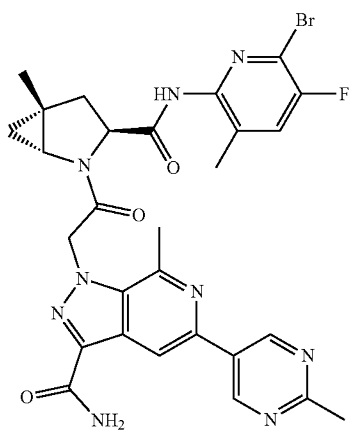 [SMILES: Cc1ncc(-c2cc3c(C(N)=O)nn(CC(=O)N4[C@H](C(=O)Nc5nc(Br)c(F)cc5C)C[C@@]5(C)C[C@@H]45)c3c(C)n2)cn1] | 1-(2-((1R,3S,5R)-3-((6-bromo-5-fluoro-3-methylpyridin-2-yl)carbamoyl)-5-methyl-2-azabicyclo[3.1.0]hexan-2-yl)-2-oxoethyl)-7-methyl-5-(2-methylpyrimidin-5-yl)-1H-pyrazolo[3,4-c]pyridine-3-carboxamide | *** | 1.55 (A) | 636 |
| 432 | 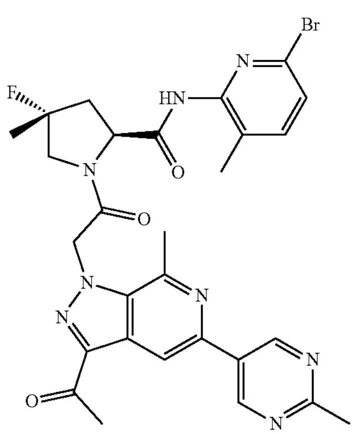 | (2S,4R)-1-(2-(3-acetyl-7-methyl-5-(2-methylpyrimidin-5-yl)-1H-pyrazolo[3,4-c]pyridin-1-yl)acetyl)-N-(6-bromo-3-methylpyridin-2-yl)-4-fluoro-4-methylpyrrolidine-2-carboxamide | *** | 2.84 (B) | 623 |

TABLE 7-continued

Additional Non-limiting Examples of Compounds of the Present Invention

| Cmp No. | Structure | Name | IC₅ (Stars) | RT min (A, B, C or D) | MS (M + 1) |
|---|---|---|---|---|---|
| 433 | 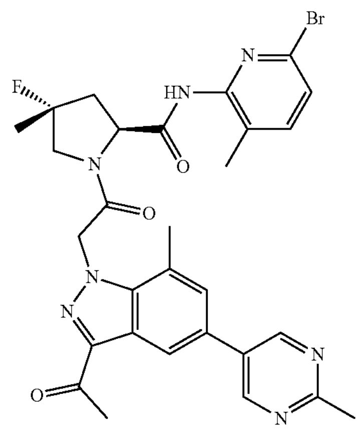 | (2S,4R)-1-(2-(3-acetyl-7-methyl-5-(2-methylpyrimidin-5-yl)-1H-indazol-1-yl)acetyl)-N-(6-bromo-3-methylpyridin-2-yl)-4-fluoro-4-methylpyrrolidine-2-carboxamide | *** | 2.96 (B) | 622 |
| 434 | 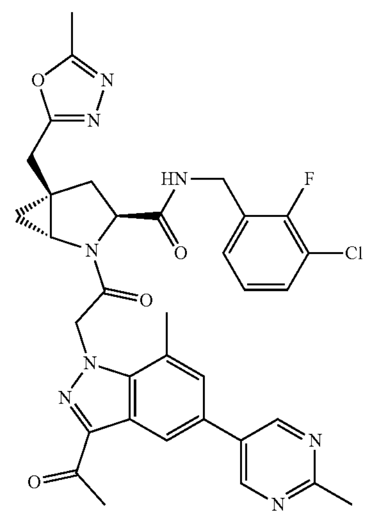 [SMILES: CC(=O)c1nn(CC(=O)N2[C@H](C(=O)NCc3cccc(Cl)c3F)C[C@@]3(Cc4nnc(C)o4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(3-chloro-2-fluorobenzyl)-5-((5-methyl-1,3,4-oxadiazol-2-yl)methyl)-2-azabicyclo[3.1.0]hexane-3-carboxamide | *** | 3.15 (B) | 671 |
| 435 | 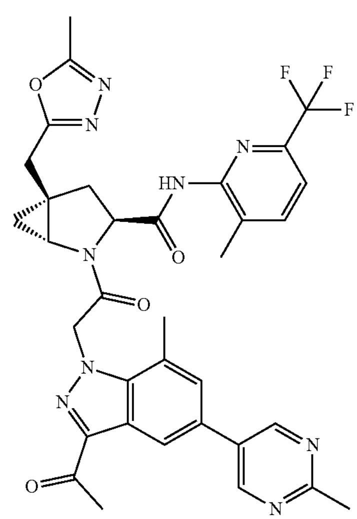 [SMILES: CC(=O)c1nn(CC(=O)N2[C@H](C(=O)Nc3nc(C(F)(F)F)ccc3C)C[C@@]3(Cc4nnc(C)o4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-((5-methyl-1,3,4-oxadiazol-2-yl)methyl)-N-(3-methyl-6-(trifluoromethyl)pyridin-2-yl)-2-azabicyclo[3.1.0]hexane-3-carboxamide | *** | 3.27 (B) | 688 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 436 | 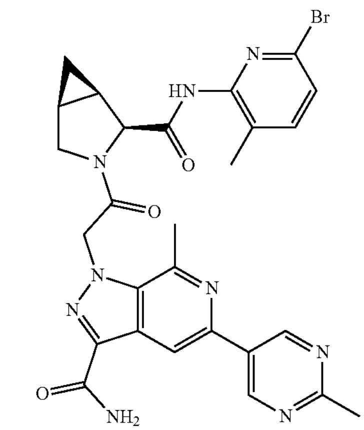 [SMILES: Cc1ncc(-c2cc3c(C(N)=O)nn(CC(=O)N4C[C@H]5C[C@H]5[C@H]4C(=O)Nc4nc(Br)ccc4C)c3c(C)n2)cn1] | 1-(2-((1R,2S,5S)-2-((6-bromo-3-methylpyridin-2-yl)carbamoyl)-3-azabicyclo[3.1.0]hexan-3-yl)-2-oxoethyl)-7-methyl-5-(2-methylpyrimidin-5-yl)-1H-pyrazolo[3,4-c]pyridine-3-carboxamide | *** | 1.30 (A) | 604 |
| 437 | 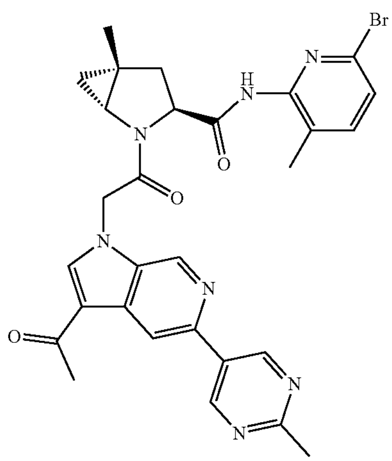 [SMILES: CC(=O)c1cn(CC(=O)N2[C@H](C(=O)Nc3nc(Br)ccc3C)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrrolo[2,3-c]pyridin-1-yl)acetyl)-N-(6-bromo-3-methylpyridin-2-yl)-5-methyl-2-azabicyclo[3.1.0]hexane-3-carboxamide | *** | 1.46 (A) | 602 |
| 438 | 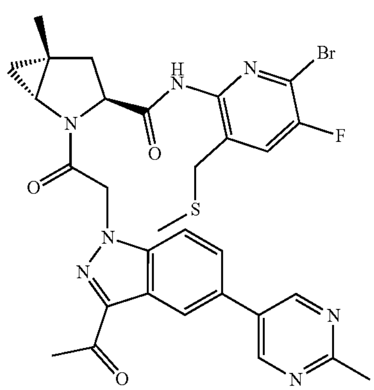 [SMILES: CSCc1cc(F)c(Br)nc1NC(=O)[C@@H]1C[C@@]2(C)C[C@H]2N1C(=O)Cn1nc(C(C)=O)c2cc(-c3cnc(C)nc3)ccc21] | (1R,3S,5R)-2-(2-(3-acetyl-5-(2-methylpyrimidin-5-yl)-1H-indazol-1-yl)acetyl)-N-(6-bromo-5-fluoro-3-((methylthio)methyl)pyridin-2-yl)-5-methyl-2-azabicyclo[3.1.0]hexane-3-carboxamide | *** | | |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 439 | 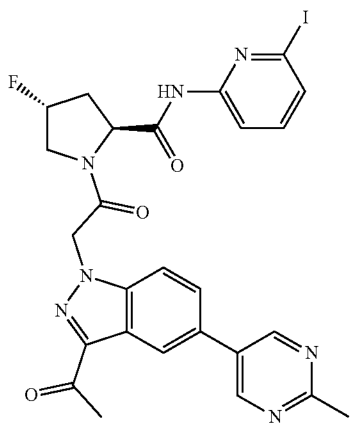 [SMILES: CC(=O)c1nn(CC(=O)N2C[C@H](F)C[C@H]2C(=O)Nc2cccc(I)n2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(6-iodopyridin-2-yl)pyrrolidine-2-carboxamide | *** | 2.93 (B) | 628 |
| 440 | 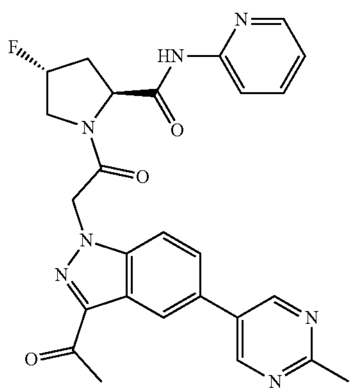 [SMILES: CC(=O)c1nn(CC(=O)N2C[C@H](F)C[C@H]2C(=O)Nc2ccccn2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(pyridin-2-yl)pyrrolidine-2-carboxamide | *** | 1.63 (B) | 502 |
| 441 | 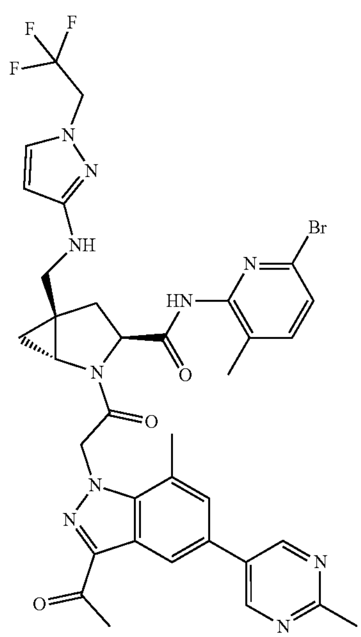 [SMILES: CC(=O)c1nn(CC(=O)N2[C@H](C(=O)Nc3nc(Br)ccc3C)C[C@@]3(CNc4ccn(CC(F)(F)F)n4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-(((1-(2,2,2-trifluoroethyl)-1H-pyrazol-3-yl)amino)methyl)-2-azabicyclo[3.1.0]hexane-3-carboxamide | *** | 3.23 (B) | 779 |

TABLE 7-continued

Additional Non-limiting Examples of Compounds of the Present Invention

| Cmp No. | Structure | Name | IC₅ (Stars) | RT min (A, B, C or D) | MS (M + 1) |
|---|---|---|---|---|---|
| 444 | 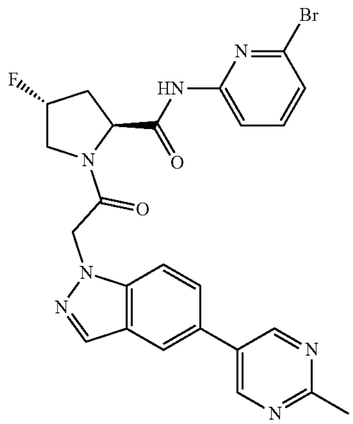 [SMILES: Cc1ncc(-c2ccc3c(cnn3CC(=O)N3C[C@H](F)C[C@H]3C(=O)Nc3cccc(Br)n3)c2)cn1] | (2S,4R)-N-(6-bromopyridin-2-yl)-4-fluoro-1-(2-(5-(2-methylpyrimidin-5-yl)-1H-indazol-1-yl)acetyl)pyrrolidine-2-carboxamide | ** | 2.68 (B) | 538 |
| 445 | 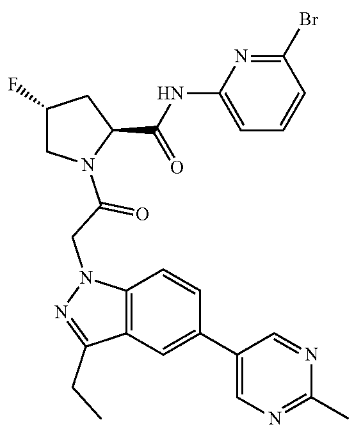 [SMILES: CCc1nn(CC(=O)N2C[C@H](F)C[C@H]2C(=O)Nc2cccc(Br)n2)c2ccc(-c3cnc(C)nc3)cc12] | (2S,4R)-N-(6-bromopyridin-2-yl)-1-(2-(3-ethyl-5-(2-methylpyrimidin-5-yl)-1H-indazol-1-yl)acetyl)-4-fluoropyrrolidine-2-carboxamide | ** | 3.18 (B) | 566 |
| 446 | 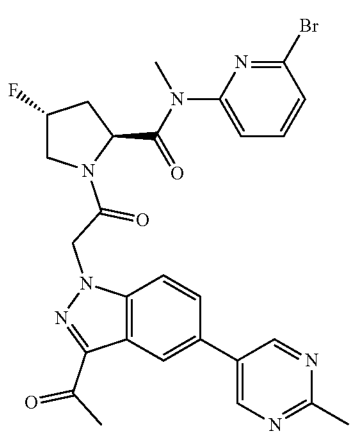 [SMILES: CC(=O)c1nn(CC(=O)N2C[C@H](F)C[C@H]2C(=O)N(C)c2cccc(Br)n2)c2ccc(-c3cnc(C)nc3)cc12] | (2S,4R)-1-(2-(3-acetyl-5-(2-methylpyrimidin-5-yl)-1H-indazol-1-yl)acetyl)-N-(6-bromopyridin-2-yl)-4-fluoro-N-methylpyrrolidine-2-carboxamide | * | 3.05 (B) | 594 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 447 | 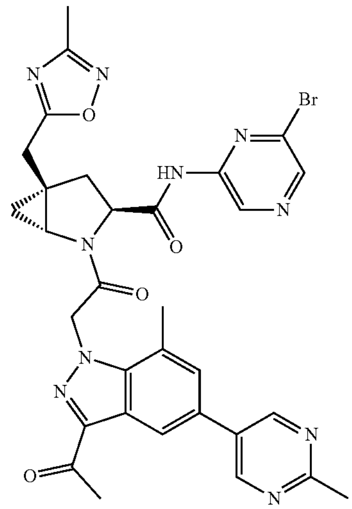 [SMILES: CC(=O)c1nn(CC(=O)N2[C@H](C(=O)Nc3cncc(Br)n3)C[C@@]3(Cc4nc(C)no4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromopyrazin-2-yl)-5-((3-methyl-1,2,4-oxadiazol-5-yl)methyl)-2-azabicyclo[3.1.0]hexane-3-carboxamide | *** | 3.33 (B) | 685 |
| 448 | 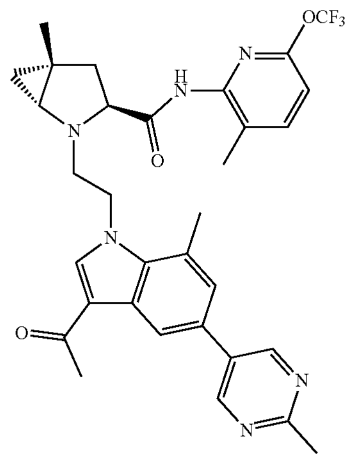 [SMILES: CC(=O)c1cn(CCN2[C@H](C(=O)Nc3nc(OC(F)(F)F)ccc3C)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indol-1-yl)acetyl)-5-methyl-N-(3-methyl-6-(trifluoromethoxy)pyridin-2-yl)-2-azabicyclo[3.1.0]hexane-3-carboxamide | *** | 2.04 (A) | 621 |
| 449 | 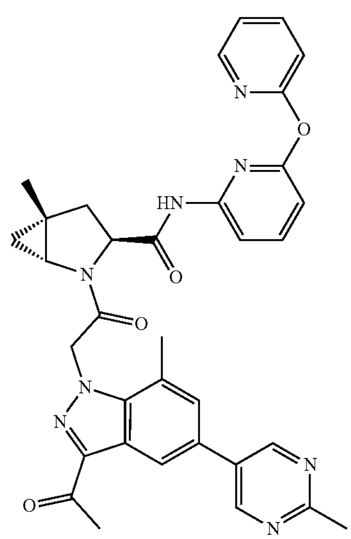 [SMILES: CC(=O)c1nn(CC(=O)N2[C@H](C(=O)Nc3cccc(Oc4ccccn4)n3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-methyl-N-(6-(pyridin-2-yloxy)pyridin-2-yl)-2-azabicyclo[3.1.0]hexane-3-carboxamide | *** | 3.16 (B) | 617 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 450 | 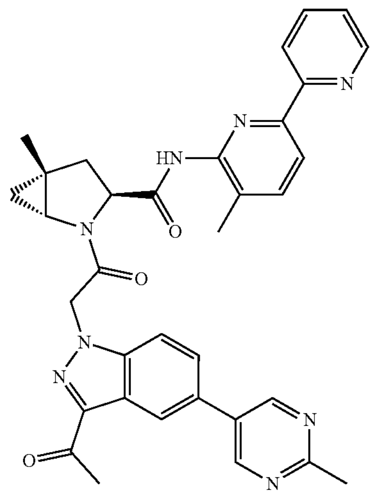 [SMILES: CC(=O)c1nn(CC(=O)N2[C@H](C(=O)Nc3nc(-c4ccccn4)ccc3C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-5-methyl-N-(5-methyl-[2,2'-bipyridin]-6-yl)-2-azabicyclo[3.1.0]hexane-3-carboxamide | ** | 2.31 (B) | 601 |
| 451 | 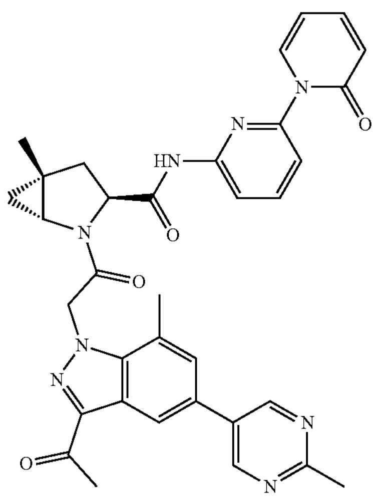 [SMILES: CC(=O)c1nn(CC(=O)N2[C@H](C(=O)Nc3cccc(-n4ccccc4=O)n3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-methyl-N-(2-oxo-2H-[1,2'-bipyridin]-6'-yl)-2-azabicyclo[3.1.0]hexane-3-carboxamide | *** | 3.00 (B) | 617 |
| 452 | 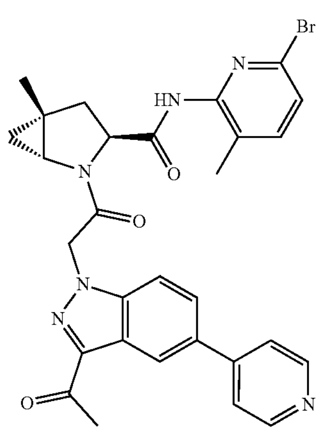 [SMILES: CC(=O)c1nn(CC(=O)N2[C@H](C(=O)Nc3nc(Br)ccc3C)C[C@@]3(C)C[C@@H]23)c2ccc(-c3ccncc3)cc12] | (1R,3S,5R)-2-(2-(3-acetyl-5-(pyridin-4-yl)-1H-indazol-1-yl)acetyl)-N-(6-bromo-3-methylpyridin-2-yl)-5-methyl-2-azabicyclo[3.1.0]hexane-3-carboxamide | *** | 2.26 (B) | 587 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 453 | 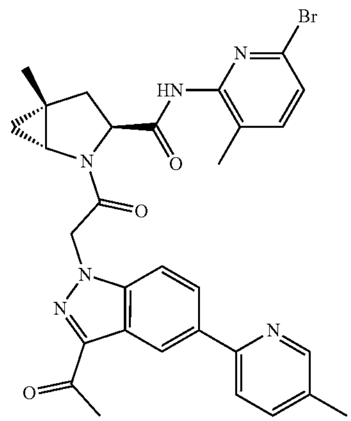 [SMILES: CC(=O)c1nn(CC(=O)N2[C@H](C(=O)Nc3nc(Br)ccc3C)C[C@@]3(C)C[C@@H]23)c2ccc(-c3ccc(C)cn3)cc12] | (1R,3S,5R)-2-(2-(3-acetyl-5-(5-methylpyridin-2-yl)-1H-indazol-1-yl)acetyl)-N-(6-bromo-3-methylpyridin-2-yl)-5-methyl-2-azabicyclo[3.1.0]hexane-3-carboxamide | *** | 2.20 (B) | 601 |
| 454 | 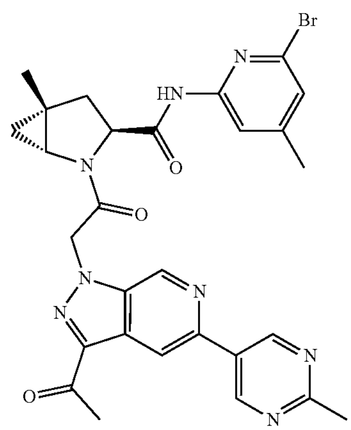 [SMILES: CC(=O)c1nn(CC(=O)N2[C@H](C(=O)Nc3cc(C)cc(Br)n3)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-4-methylpyridin-2-yl)-5-methyl-2-azabicyclo[3.1.0]hexane-3-carboxamide | | 3.36 (B) | 603 |
| 455 | 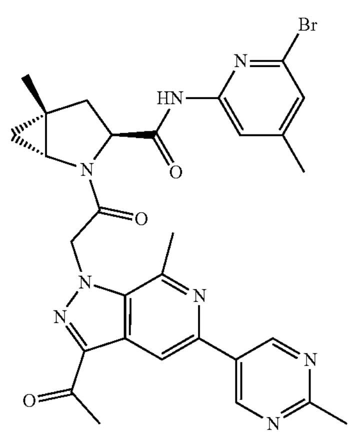 [SMILES: CC(=O)c1nn(CC(=O)N2[C@H](C(=O)Nc3cc(C)cc(Br)n3)C[C@@]3(C)C[C@@H]23)c2c(C)nc(-c3cnc(C)nc3)cc12] | (1R,3S,5R)-2-(2-(3-acetyl-7-methyl-5-(2-methylpyrimidin-5-yl)-1H-pyrazolo[3,4-c]pyridin-1-yl)acetyl)-N-(6-bromo-4-methylpyridin-2-yl)-5-methyl-2-azabicyclo[3.1.0]hexane-3-carboxamide | *** | 3.48 (B) | 617 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 456 | 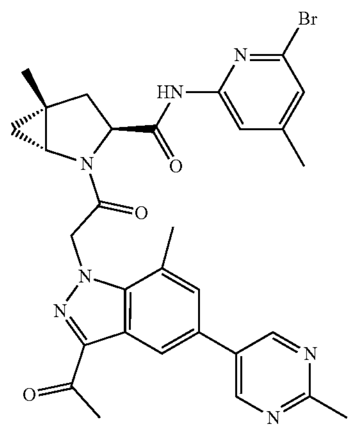 [SMILES: CC(=O)c1nn(CC(=O)N2[C@H](C(=O)Nc3cc(C)cc(Br)n3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-4-methylpyridin-2-yl)-5-methyl-2-azabicyclo[3.1.0]hexane-3-carboxamide | *** | 3.50 (B) | 616 |
| 457 | 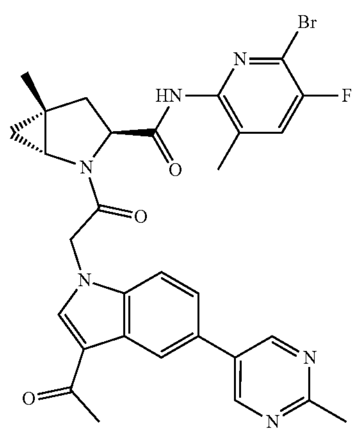 [SMILES: CC(=O)c1cn(CC(=O)N2[C@H](C(=O)Nc3nc(Br)c(F)cc3C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indol-1-yl)acetyl)-N-(6-bromo-5-fluoro-3-methylpyridin-2-yl)-5-methyl-2-azabicyclo[3.1.0]hexane-3-carboxamide | *** | 2.89 (B) | 619 |
| 458 | 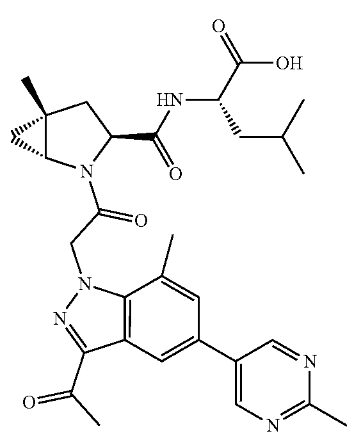 [SMILES: CC(=O)c1nn(CC(=O)N2[C@H](C(=O)N[C@@H](CC(C)C)C(=O)O)C[C@@]3(C)C[C@@H]23)c2c(C)cc(-c3cnc(C)nc3)cc12] | ((1R,3S,5R)-2-(2-(3-acetyl-7-methyl-5-(2-methylpyrimidin-5-yl)-1H-indazol-1-yl)acetyl)-5-methyl-2-azabicyclo[3.1.0]hexane-3-carbonyl)-L-leucine | *** | 2.98 (B) | 561 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 459 | 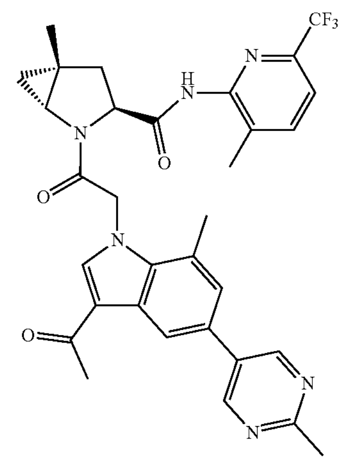 [SMILES: CC(=O)c1cn(CC(=O)N2[C@H](C(=O)Nc3nc(C(F)(F)F)ccc3C)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indol-1-yl)acetyl)-5-methyl-N-(3-methyl-6-(trifluoromethyl)pyridin-2-yl)-2-azabicyclo[3.1.0]hexane-3-carboxamide | *** | 1.92 (A) | 605 |
| 460 | 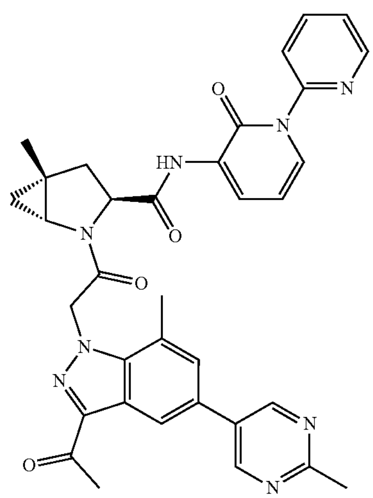 [SMILES: CC(=O)c1nn(CC(=O)N2[C@H](C(=O)Nc3cccn(-c4ccccn4)c3=O)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-methyl-N-(2-oxo-2H-[1,2'-bipyridin]-3-yl)-2-azabicyclo[3.1.0]hexane-3-carboxamide | *** | 3.35 (B) | 617 |
| 461 | 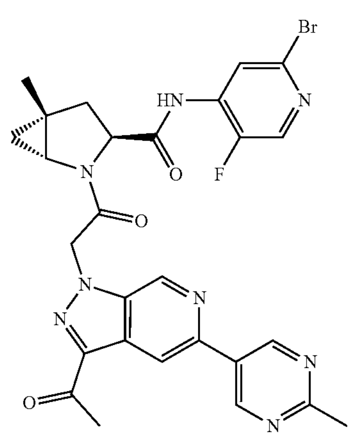 [SMILES: CC(=O)c1nn(CC(=O)N2[C@H](C(=O)Nc3cc(Br)ncc3F)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(2-bromo-5-fluoropyridin-4-yl)-5-methyl-2-azabicyclo[3.1.0]hexane-3-carboxamide | ** | 3.48 (B) | 607 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 462 | 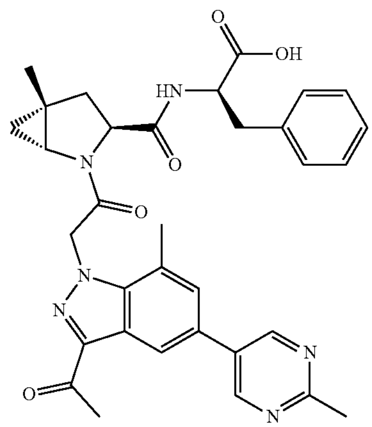 [SMILES: CC(=O)c1nn(CC(=O)N2[C@H](C(=O)N[C@H](Cc3ccccc3)C(=O)O)C[C@@]3(C)C[C@@H]23)c2c(C)cc(-c3cnc(C)nc3)cc12] | ((1R,3S,5R)-2-(2-(3-acetyl-7-methyl-5-(2-methylpyrimidin-5-yl)-1H-indazol-1-yl)acetyl)-5-methyl-2-azabicyclo[3.1.0]hexane-3-carbonyl)-D-phenylalanine | ** | 3.50 (B) | 595 |
| 463 | 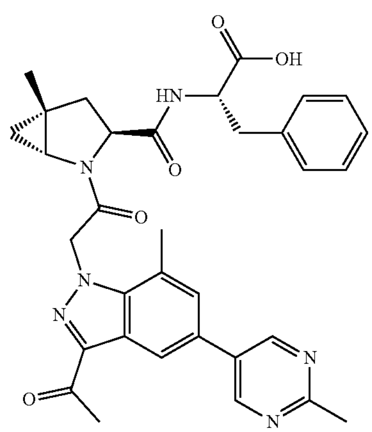 [SMILES: CC(=O)c1nn(CC(=O)N2[C@H](C(=O)N[C@@H](Cc3ccccc3)C(=O)O)C[C@@]3(C)C[C@@H]23)c2c(C)cc(-c3cnc(C)nc3)cc12] | ((1R,3S,5R)-2-(2-(3-acetyl-7-methyl-5-(2-methylpyrimidin-5-yl)-1H-indazol-1-yl)acetyl)-5-methyl-2-azabicyclo[3.1.0]hexane-3-carbonyl)-L-phenylalanine | | 3.48 (B) | 595 |
| 464 | 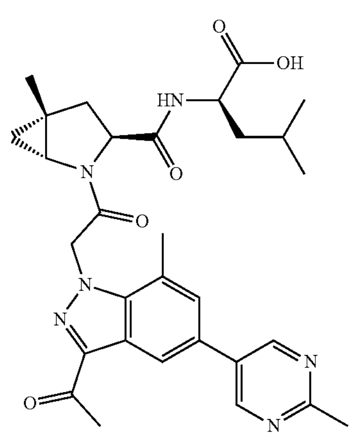 [SMILES: CC(=O)c1nn(CC(=O)N2[C@H](C(=O)N[C@H](CC(C)C)C(=O)O)C[C@@]3(C)C[C@@H]23)c2c(C)cc(-c3cnc(C)nc3)cc12] | ((1R,3S,5R)-2-(2-(3-acetyl-7-methyl-5-(2-methylpyrimidin-5-yl)-1H-indazol-1-yl)acetyl)-5-methyl-2-azabicyclo[3.1.0]hexane-3-carbonyl)-D-leucine | ** | 3.30 (B) | 561 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 465 | 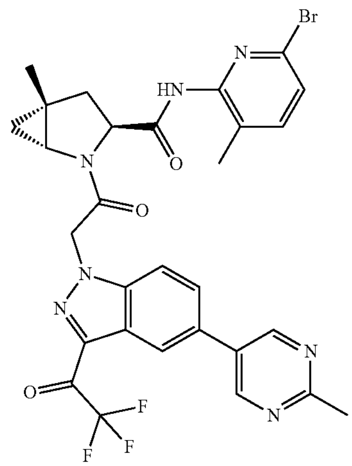 [SMILES: Cc1ncc(-c2ccc3c(c2)c(C(=O)C(F)(F)F)nn3CC(=O)N2[C@H](C(=O)Nc3nc(Br)ccc3C)C[C@@]3(C)C[C@@H]23)cn1] | (1R,3S,5R)-N-(6-bromo-3-methylpyridin-2-yl)-5-methyl-2-(2-(5-(2-methylpyrimidin-5-yl)-3-(2,2,2-trifluoroacetyl)-1H-indol-1-yl)acetyl)-2-azabicyclo[3.1.0]hexane-3-carboxamide | *** | 3.51 (B) | 655 |
| 466 | 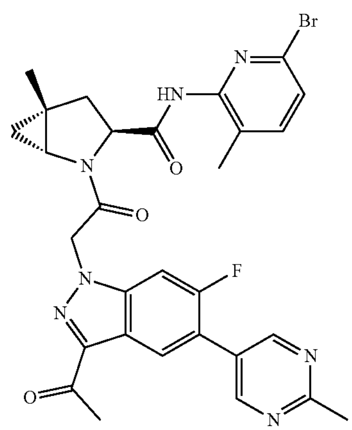 [SMILES: CC(=O)c1nn(CC(=O)N2[C@H](C(=O)Nc3nc(Br)ccc3C)C[C@@]3(C)C[C@@H]23)c2cc(F)c(-c3cnc(C)nc3)cc12] | (1R,3S,5R)-2-(2-(3-acetyl-6-fluoro-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 3.28 (B) | 620 |
| 467 | 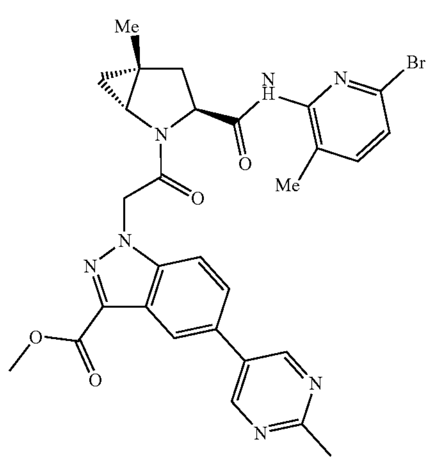 [SMILES: COC(=O)c1nn(CC(=O)N2[C@H](C(=O)Nc3nc(Br)ccc3C)C[C@@]3(C)C[C@@H]23)c2ccc(-c3cnc(C)nc3)cc12] | methyl 1-(2-((1R,3S,5R)-3-((6-bromo-3-methylpyridin-2-yl)carbamoyl)-5-methyl-2-azabicyclo[3.1.0]hexan-2-yl)-2-oxoethyl)-5-(2-methylpyrimidin-5-yl)-1H-indazole-3-carboxylate | *** | | |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 468 | 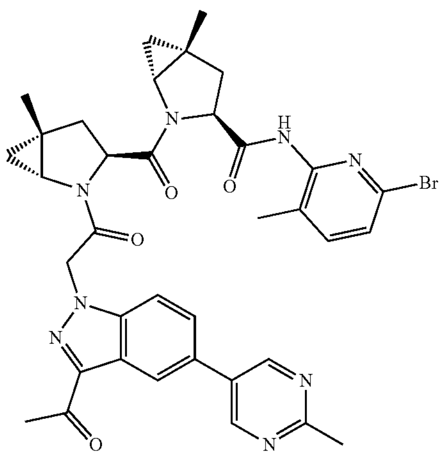 [SMILES: CC(=O)c1nn(CC(=O)N2[C@H](C(=O)N3[C@H](C(=O)Nc4nc(Br)ccc4C)C[C@@]4(C)C[C@@H]34)C[C@@]3(C)C[C@@H]23)c2ccc(-c3cnc(C)nc3)cc12] | (1R,3S,5R)-2-((1R,3S,5R)-2-(2-(3-acetyl-5-(2-methylpyrimidin-5-yl)-1H-indazol-1-yl)acetyl)-5-methyl-2-azabicyclo[3.1.0]hexane-3-carbonyl)-N-(6-bromo-3-methylpyridin-2-yl)-5-methyl-2-azabicyclo[3.1.0]hexane-3-carboxamide | | | |
| 469 | 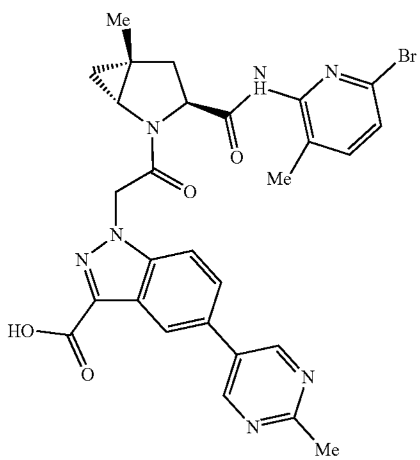 [SMILES: Cc1ncc(-c2ccc3c(c2)c(C(=O)O)nn3CC(=O)N2[C@H](C(=O)Nc3nc(Br)ccc3C)C[C@@]3(C)C[C@@H]23)cn1] | 1-(2-((1R,3S,5R)-3-((6-bromo-3-methylpyridin-2-yl)carbamoyl)-5-methyl-2-azabicyclo[3.1.0]hexan-2-yl)-2-oxoethyl)-5-(2-methylpyrimidin-5-yl)-1H-indazole-3-carboxylic acid | * | 1.52 (A) | 604 |
| 470 | 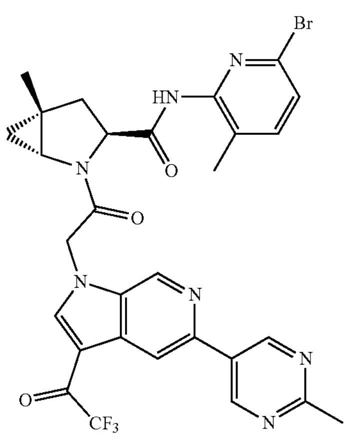 | (1R,3S,5R)-N-(6-bromo-3-methylpyridin-2-yl)-5-methyl-2-(2-(5-(2-methylpyrimidin-5-yl)-3-(2,2,2-trifluoroacetyl)-1H-pyrrolo[2,3-c]pyridin-1-yl)acetyl)-2-azabicyclo[3.1.0]hexane-3-carboxamide | *** | 2.67 (B) | 656 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 471 | 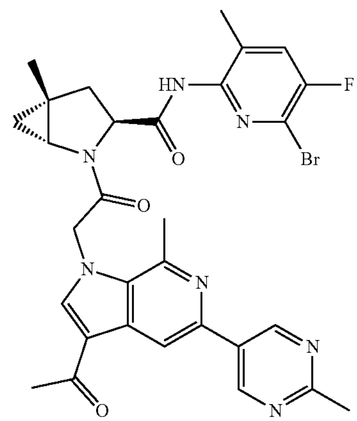 [SMILES: CC(=O)c1cn(CC(=O)N2[C@H](C(=O)Nc3nc(Br)c(F)cc3C)C[C@@]3(C)C[C@@H]23)c2c(C)nc(-c3cnc(C)nc3)cc12] | (1R,3S,5R)-2-(2-(3-acetyl-7-methyl-5-(2-methylpyrimidin-5-yl)-1H-pyrrolo[2,3-c]pyridin-1-yl)acetyl)-N-(6-bromo-5-fluoro-3-methylpyridin-2-yl)-5-methyl-2-azabicyclo[3.1.0]hexane-3-carboxamide | *** | 1.95 (B) | 634 |
| 472 | 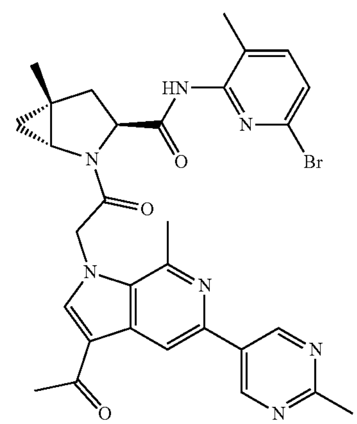 [SMILES: CC(=O)c1cn(CC(=O)N2[C@H](C(=O)Nc3nc(Br)ccc3C)C[C@@]3(C)C[C@@H]23)c2c(C)nc(-c3cnc(C)nc3)cc12] | (1R,3S,5R)-2-(2-(3-acetyl-7-methyl-5-(2-methylpyrimidin-5-yl)-1H-pyrrolo[2,3-c]pyridin-1-yl)acetyl)-N-(6-bromo-3-methylpyridin-2-yl)-5-methyl-2-azabicyclo[3.1.0]hexane-3-carboxamide | *** | 1.88 (B) | 616 |
| 473 | 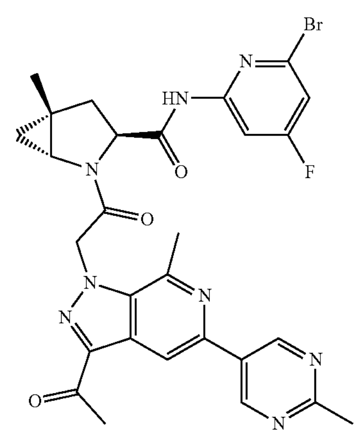 [SMILES: CC(=O)c1nn(CC(=O)N2[C@H](C(=O)Nc3cc(F)cc(Br)n3)C[C@@]3(C)C[C@@H]23)c2c(C)nc(-c3cnc(C)nc3)cc12] | (1R,3S,5R)-2-(2-(3-acetyl-7-methyl-5-(2-methylpyrimidin-5-yl)-1H-pyrazolo[3,4-c]pyridin-1-yl)acetyl)-N-(6-bromo-4-fluoropyridin-2-yl)-5-methyl-2-azabicyclo[3.1.0]hexane-3-carboxamide | *** | 3.68 (B) | 621 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 474 | 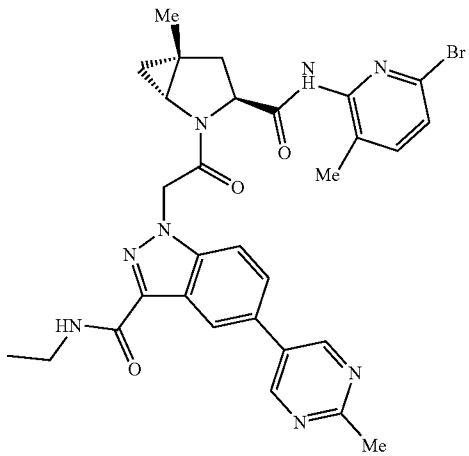 [SMILES: CCNC(=O)c1nn(CC(=O)N2[C@H](C(=O)Nc3nc(Br)ccc3C)C[C@@]3(C)C[C@@H]23)c2ccc(-c3cnc(C)nc3)cc12] | 1-(2-((1R,3S,5R)-3-((6-bromo-3-methylpyridin-2-yl)carbamoyl)-5-methyl-2-azabicyclo[3.1.0]hexan-2-yl)-2-oxoethyl)-N-ethyl-5-(2-methylpyrimidin-5-yl)-1H-indazole-3-carboxamide | *** | 1.71 (A) | 631 |
| 481 | 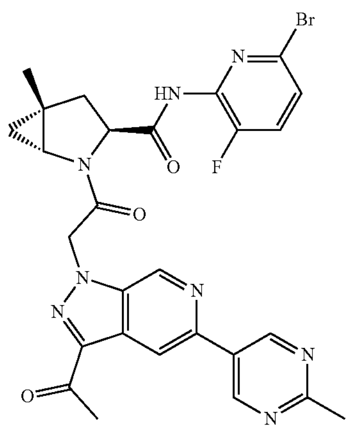 [SMILES: CC(=O)c1nn(CC(=O)N2[C@H](C(=O)Nc3nc(Br)ccc3F)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrazolo[3,4-c]pyridin-1-yl)acetyl)-N-(6-bromo-3-fluoropyridin-2-yl)-5-methyl-2-azabicyclo[3.1.0]hexane-3-carboxamide | *** | 3.03 (B) | 607 |
| 482 | 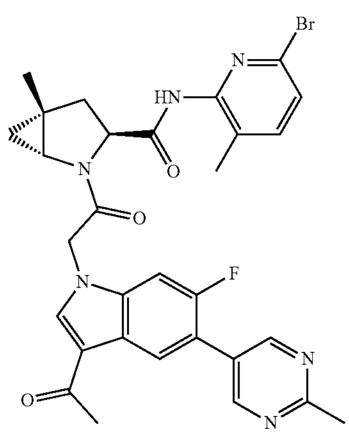 [SMILES: CC(=O)c1cn(CC(=O)N2[C@H](C(=O)Nc3nc(Br)ccc3C)C[C@@]3(C)C[C@@H]23)c2cc(F)c(-c3cnc(C)nc3)cc12] | (1R,3S,5R)-2-(2-(3-acetyl-6-fluoro-5-(2-methylpyrimidin-5-yl)-1H-indol-1-yl)acetyl)-N-(6-bromo-3-methylpyridin-2-yl)-5-methyl-2-azabicyclo[3.1.0]hexane-3-carboxamide | *** | 3.34 (B) | 619 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 483 | 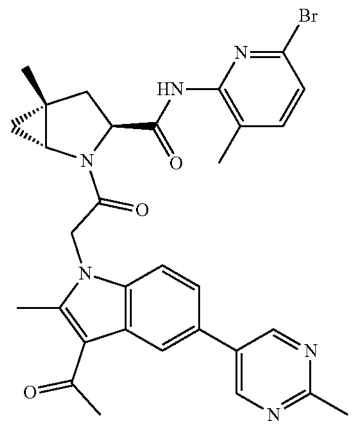 [SMILES: CC(=O)c1c(C)n(CC(=O)N2[C@H](C(=O)Nc3nc(Br)ccc3C)C[C@@]3(C)C[C@@H]23)c2ccc(-c3cnc(C)nc3)cc12] | (1R,3S,5R)-2-(2-(3-acetyl-2-methyl-5-(2-methylpyrimidin-5-yl)-1H-indol-1-yl)acetyl)-N-(6-bromo-3-methylpyridin-2-yl)-5-methyl-2-azabicyclo[3.1.0]hexane-3-carboxamide | *** | 3.29 (B) | 615 |
| 484 | 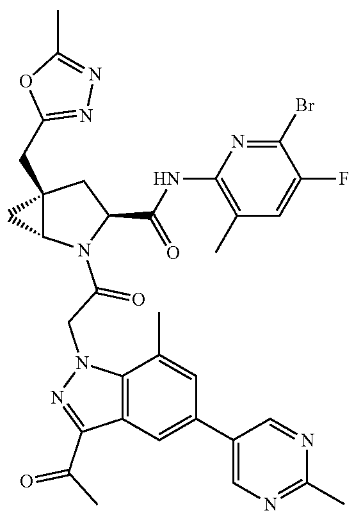 [SMILES: CC(=O)c1nn(CC(=O)N2[C@H](C(=O)Nc3nc(Br)c(F)cc3C)C[C@@]3(Cc4nnc(C)o4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-5-fluoro-3-methylpyridin-2-yl)-5-((5-methyl-1,3,4-oxadiazol-2-yl)methyl)-2-azabicyclo[3.1.0]hexane-3-carboxamide | *** | 3.04 (B) | 716 |
| 485 | 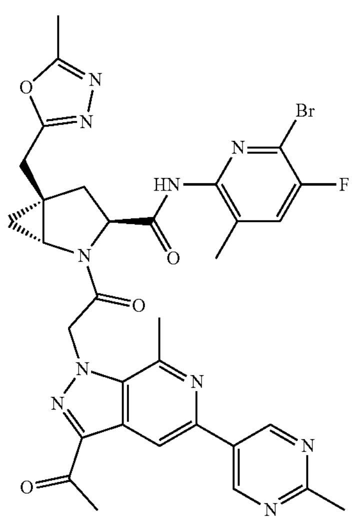 [SMILES: CC(=O)c1nn(CC(=O)N2[C@H](C(=O)Nc3nc(Br)c(F)cc3C)C[C@@]3(Cc4nnc(C)o4)C[C@@H]23)c2c(C)nc(-c3cnc(C)nc3)cc12] | (1R,3S,5R)-2-(2-(3-acetyl-7-methyl-5-(2-methylpyrimidin-5-yl)-1H-pyrazolo[3,4-c]pyridin-1-yl)acetyl)-N-(6-bromo-5-fluoro-3-methylpyridin-2-yl)-5-((5-methyl-1,3,4-oxadiazol-2-yl)methyl)-2-azabicyclo[3.1.0]hexane-3-carboxamide | *** | 2.97 (B) | 717 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 486 | 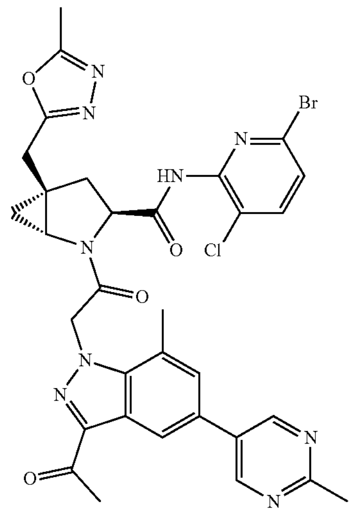 [SMILES: CC(=O)c1nn(CC(=O)N2[C@H](C(=O)Nc3nc(Br)ccc3Cl)C[C@@]3(Cc4nnc(C)o4)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-chloropyridin-2-yl)-5-((5-methyl-1,3,4-oxadiazol-2-yl)methyl)-2-azabicyclo[3.1.0]hexane-3-carboxamide | *** | 2.92 (B) | 720 |
| 487 | 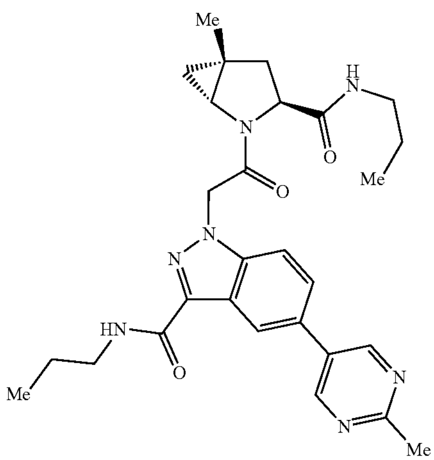 [SMILES: CCCNC(=O)c1nn(CC(=O)N2[C@H](C(=O)NCCC)C[C@@]3(C)C[C@@H]23)c2ccc(-c3cnc(C)nc3)cc12] | 1-(2-((1R,3S,5R)-5-methyl-3-(propylcarbamoyl)-2-azabicyclo[3.1.0]hexan-2-yl)-2-oxoethyl)-5-(2-methylpyrimidin-5-yl)-N-propyl-1H-indazole-3-carboxamide | ** | 1.57 (A) | 518 |
| 488 | 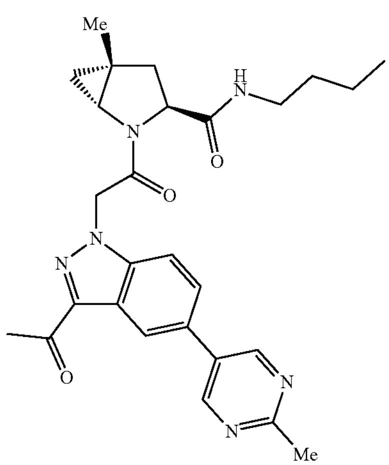 [SMILES: CCCCNC(=O)[C@@H]1C[C@@]2(C)C[C@H]2N1C(=O)Cn1nc(C(C)=O)c2cc(-c3cnc(C)nc3)ccc21] | (1R,3S,5R)-2-(2-(3-acetyl-5-(2-methylpyrimidin-5-yl)-1H-indazol-1-yl)acetyl)-N-butyl-5-methyl-2-azabicyclo[3.1.0]hexane-3-carboxamide | *** | 1.67 (A) | 489 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 492 | 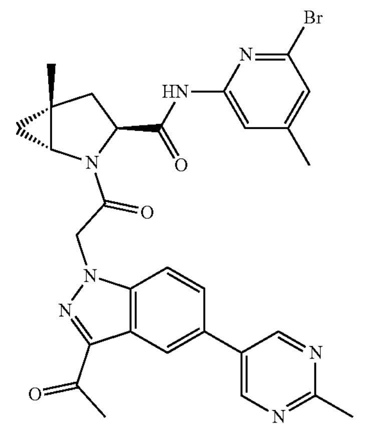 [SMILES: CC(=O)c1nn(CC(=O)N2[C@H](C(=O)Nc3cc(C)cc(Br)n3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-4-methylpyridin-2-yl)-5-methyl-2-azabicyclo[3.1.0]hexane-3-carboxamide | *** | 3.49 (B) | 602 |
| 493 | 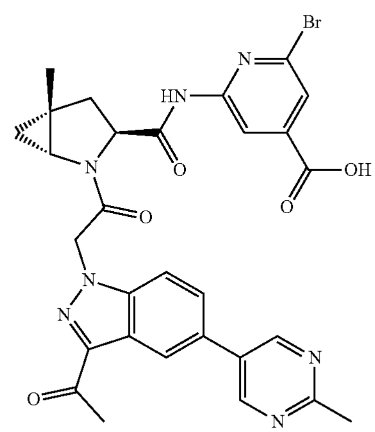 [SMILES: CC(=O)c1nn(CC(=O)N2[C@H](C(=O)Nc3cc(C(=O)O)cc(Br)n3)C[C@@]3(C)C[C@@H]23)c2ccc(-c3cnc(C)nc3)cc12] | 2-((1R,3S,5R)-2-(2-(3-acetyl-5-(2-methylpyrimidin-5-yl)-1H-indazol-1-yl)acetyl)-5-methyl-2-azabicyclo[3.1.0]hexane-3-carboxamido)-6-bromoisonicotinic acid | *** | 3.37 (B) | 632 |
| 494 | 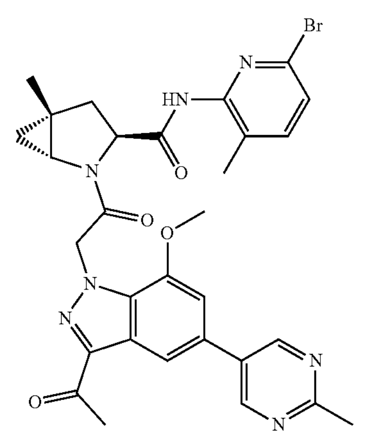 [SMILES: COc1cc(-c2cnc(C)nc2)cc2c(C(C)=O)nn(CC(=O)N3[C@H](C(=O)Nc4nc(Br)ccc4C)C[C@@]4(C)C[C@@H]34)c12] | (1R,3S,5R)-2-(2-(3-acetyl-7-methoxy-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 3.39 (B) | 632 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 495 | 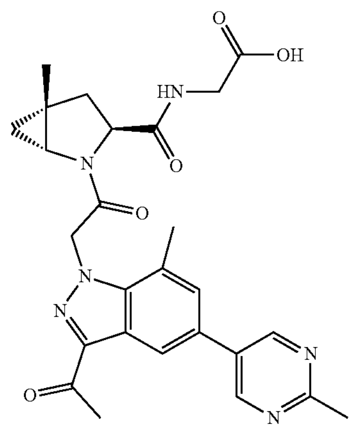 [SMILES: CC(=O)c1nn(CC(=O)N2[C@H](C(=O)NCC(=O)O)C[C@@]3(C)C[C@@H]23)c2c(C)cc(-c3cnc(C)nc3)cc12] | ((1R,3S,5R)-2-(2-(3-acetyl-7-methyl-5-(2-methylpyrimidin-5-yl)-1H-indazol-1-yl)acetyl)-5-methyl-2-azabicyclo[3.1.0]hexane-3-carbonyl)glycine | ** | 2.88 (B) | 505 |
| 496 | 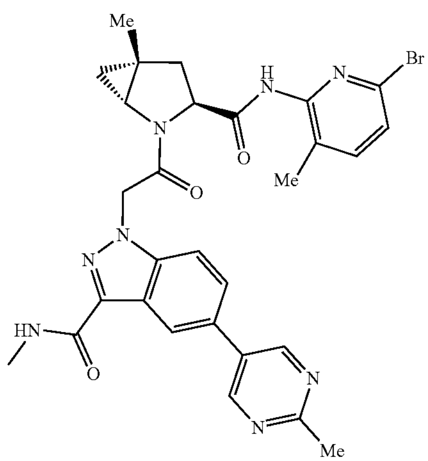 [SMILES: CNC(=O)c1nn(CC(=O)N2[C@H](C(=O)Nc3nc(Br)ccc3C)C[C@@]3(C)C[C@@H]23)c2ccc(-c3cnc(C)nc3)cc12] | 1-(2-((1R,3S,5R)-3-((6-bromo-3-methylpyridin-2-yl)carbamoyl)-5-methyl-2-azabicyclo[3.1.0]hexan-2-yl)-2-oxoethyl)-N-methyl-5-(2-methylpyrimidin-5-yl)-1H-indazole-3-carboxamide | *** | 1.31 (A) | 461 |
| 497 | 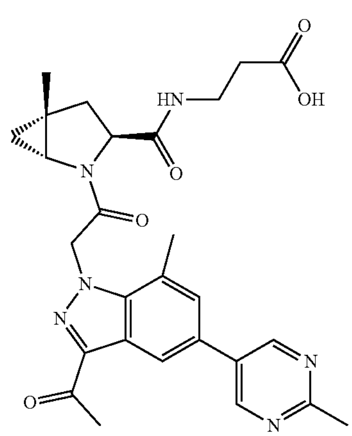 [SMILES: CC(=O)c1nn(CC(=O)N2[C@H](C(=O)NCCC(=O)O)C[C@@]3(C)C[C@@H]23)c2c(C)cc(-c3cnc(C)nc3)cc12] | 3-((1R,3S,5R)-2-(2-(3-acetyl-7-methyl-5-(2-methylpyrimidin-5-yl)-1H-indazol-1-yl)acetyl)-5-methyl-2-azabicyclo[3.1.0]hexane-3-carboxamido)propanoic acid | *** | 2.92 (B) | 519 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 498 | 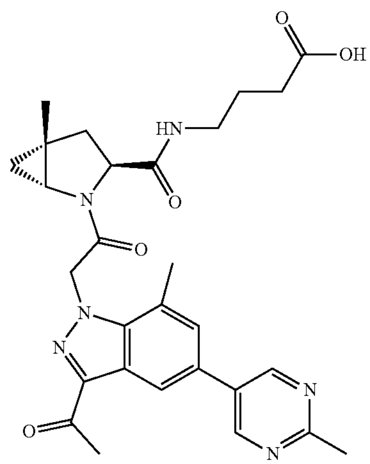 [SMILES: CC(=O)c1nn(CC(=O)N2[C@H](C(=O)NCCCC(=O)O)C[C@@]3(C)C[C@@H]23)c2c(C)cc(-c3cnc(C)nc3)cc12] | 4-((1R,3S,5R)-2-(2-(3-acetyl-7-methyl-5-(2-methylpyrimidin-5-yl)-1H-indazol-1-yl)acetyl)-5-methyl-2-azabicyclo[3.1.0]hexane-3-carboxamido)butanoic acid | *** | 3.09 (B) | 533 |
| 501 | 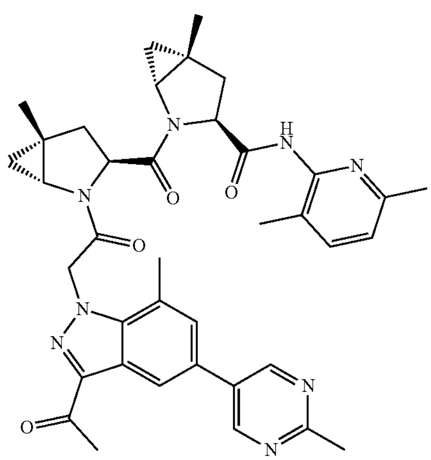 [SMILES: CC(=O)c1nn(CC(=O)N2[C@H](C(=O)N3[C@H](C(=O)Nc4nc(C)ccc4C)C[C@@]4(C)C[C@@H]34)C[C@@]3(C)C[C@@H]23)c2c(C)cc(-c3cnc(C)nc3)cc12] | (1R,3S,5R)-2-((1R,3S,5R)-2-(2-(3-acetyl-7-methyl-5-(2-methylpyrimidin-5-yl)-1H-indazol-1-yl)acetyl)-5-methyl-2-azabicyclo[3.1.0]hexane-3-carbonyl)-N-(3,6-dimethylpyridin-2-yl)-5-methyl-2-azabicyclo[3.1.0]hexane-3-carboxamide | | | |
| 502 | 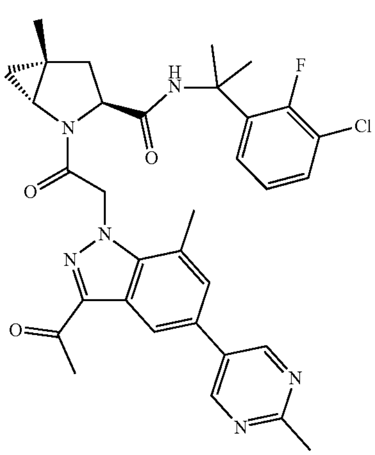 [SMILES: CC(=O)c1nn(CC(=O)N2[C@H](C(=O)NC(C)(C)c3cccc(Cl)c3F)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(2-(3-chloro-2-fluorophenyl)propan-2-yl)-5-methyl-2-azabicyclo[3.1.0]hexane-3-carboxamide | *** | 2.31 (A) | 617 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 503 | 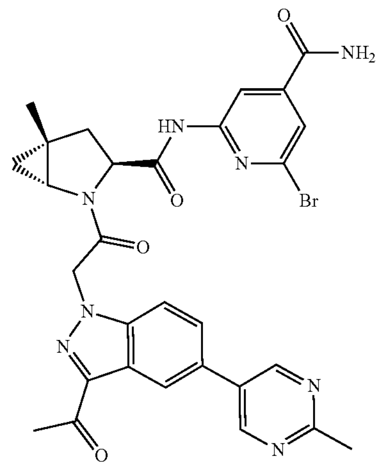 [SMILES: CC(=O)c1nn(CC(=O)N2[C@H](C(=O)Nc3cc(C(N)=O)cc(Br)n3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-4-carbamoylpyridin-2-yl)-5-methyl-2-azabicyclo[3.1.0]hexane-3-carboxamide | *** | 2.80 (B) | 631 |
| 504 | 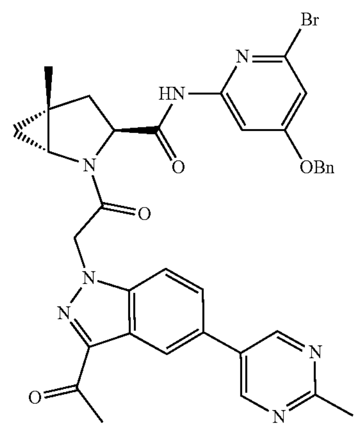 [SMILES: CC(=O)c1nn(CC(=O)N2[C@H](C(=O)Nc3cc(OCc4ccccc4)cc(Br)n3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(4-(benzyloxy)-6-bromopyridin-2-yl)-5-methyl-2-azabicyclo[3.1.0]hexane-3-carboxamide | *** | 4.42 (B) | 694 |
| 505 | 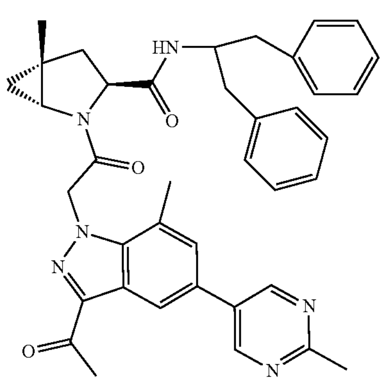 [SMILES: CC(=O)c1nn(CC(=O)N2[C@H](C(=O)NC(Cc3ccccc3)Cc3ccccc3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(1,3-diphenylpropan-2-yl)-5-methyl-2-azabicyclo[3.1.0]hexane-3-carboxamide | ** | 3.87 (B) | 641 |

TABLE 7-continued

Additional Non-limiting Examples of Compounds of the Present Invention

| Cmp No. | Structure | Name | IC₅ (Stars) | RT min (A, B, C or D) | MS (M + 1) |
|---|---|---|---|---|---|
| 506 | 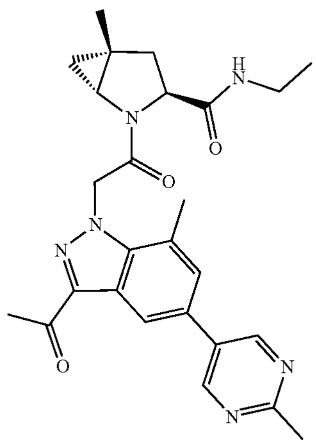 [SMILES: CCNC(=O)[C@@H]1C[C@@]2(C)C[C@H]2N1C(=O)Cn1nc(C(C)=O)c2cc(-c3cnc(C)nc3)cc(C)c21] | (1R,3S,5R)-2-(2-(3-acetyl-7-methyl-5-(2-methylpyrimidin-5-yl)-1H-indazol-1-yl)acetyl)-N-ethyl-5-methyl-2-azabicyclo[3.1.0]hexane-3-carboxamide | *** | 1.42 (A) | 474 |
| 507 | 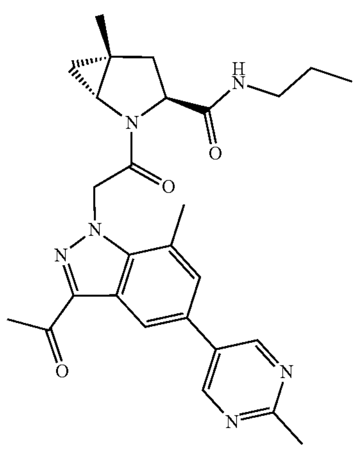 [SMILES: CCCNC(=O)[C@@H]1C[C@@]2(C)C[C@H]2N1C(=O)Cn1nc(C(C)=O)c2cc(-c3cnc(C)nc3)cc(C)c21] | (1R,3S,5R)-2-(2-(3-acetyl-7-methyl-5-(2-methylpyrimidin-5-yl)-1H-indazol-1-yl)acetyl)-5-methyl-N-propyl-2-azabicyclo[3.1.0]hexane-3-carboxamide | *** | 1.58 (A) | 488 |
| 508 | 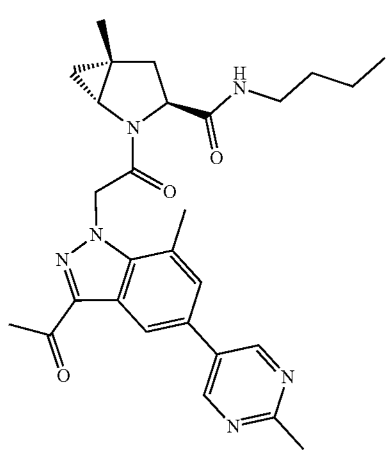 [SMILES: CCCCNC(=O)[C@@H]1C[C@@]2(C)C[C@H]2N1C(=O)Cn1nc(C(C)=O)c2cc(-c3cnc(C)nc3)cc(C)c21] | (1R,3S,5R)-2-(2-(3-acetyl-7-methyl-5-(2-methylpyrimidin-5-yl)-1H-indazol-1-yl)acetyl)-N-butyl-5-methyl-2-azabicyclo[3.1.0]hexane-3-carboxamide | *** | 1.77 (A) | 502 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 509 | 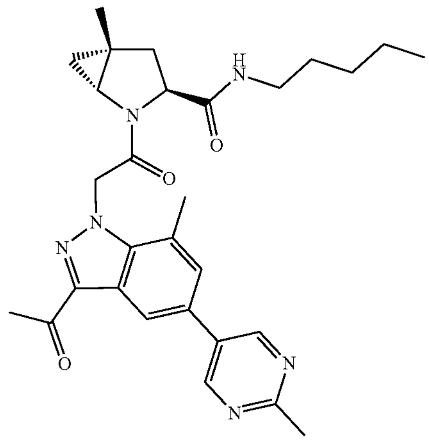 [SMILES: CCCCCNC(=O)[C@@H]1C[C@@]2(C)C[C@H]2N1C(=O)Cn1nc(C(C)=O)c2cc(-c3cnc(C)nc3)cc(C)c21] | (1R,3S,5R)-2-(2-(3-acetyl-7-methyl-5-(2-methylpyrimidin-5-yl)-1H-indazol-1-yl)acetyl)-5-methyl-N-pentyl-2-azabicyclo[3.1.0]hexane-3-carboxamide | *** | 1.94 (A) | 516 |
| 510 | 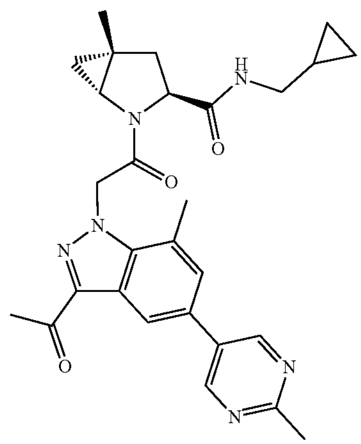 [SMILES: CC(=O)c1nn(CC(=O)N2[C@H](C(=O)NCC3CC3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(cyclopropylmethyl)-5-methyl-2-azabicyclo[3.1.0]hexane-3-carboxamide | *** | 1.64 (A) | 500 |
| 511 | 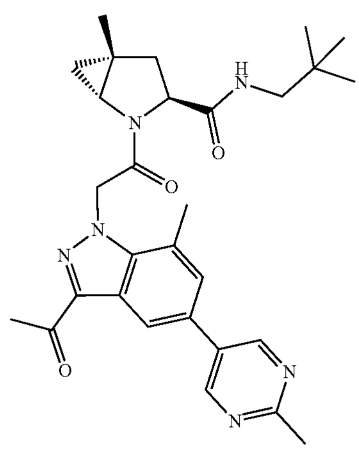 [SMILES: CC(=O)c1nn(CC(=O)N2[C@H](C(=O)NCC(C)(C)C)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-methyl-N-neopentyl-2-azabicyclo[3.1.0]hexane-3-carboxamide | | 1.92 (A) | 516 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 512 | 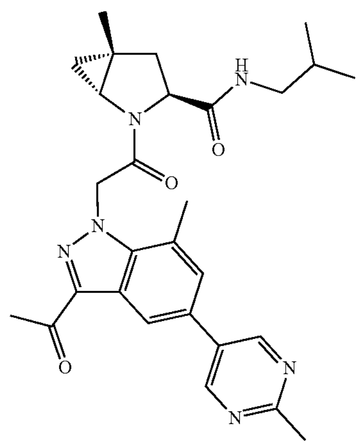 [SMILES: CC(=O)c1nn(CC(=O)N2[C@H](C(=O)NCC(C)C)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-isobutyl-5-methyl-2-azabicyclo[3.1.0]hexane-3-carboxamide | *** | 1.75 (A) | 502 |
| 513 | 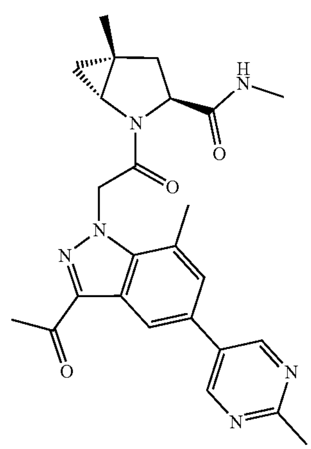 [SMILES: CNC(=O)[C@@H]1C[C@@]2(C)C[C@H]2N1C(=O)Cn1nc(C(C)=O)c2cc(-c3cnc(C)nc3)cc(C)c21] | (1R,3S,5R)-2-(2-(3-acetyl-7-methyl-5-(2-methylpyrimidin-5-yl)-1H-indazol-1-yl)acetyl)-N,5-dimethyl-2-azabicyclo[3.1.0]hexane-3-carboxamide | *** | | |
| 514 | 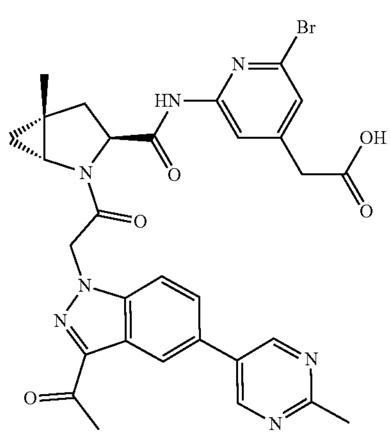 [SMILES: CC(=O)c1nn(CC(=O)N2[C@H](C(=O)Nc3cc(CC(=O)O)cc(Br)n3)C[C@@]3(C)C[C@@H]23)c2ccc(-c3cnc(C)nc3)cc12] | 2-(2-((1R,3S,5R)-2-(2-(3-acetyl-5-(2-methylpyrimidin-5-yl)-1H-indazol-1-yl)acetyl)-5-methyl-2-azabicyclo[3.1.0]hexane-3-carboxamido)-6-bromopyridin-4-yl)acetic acid | *** | 3.23 (B) | 646 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 516 | 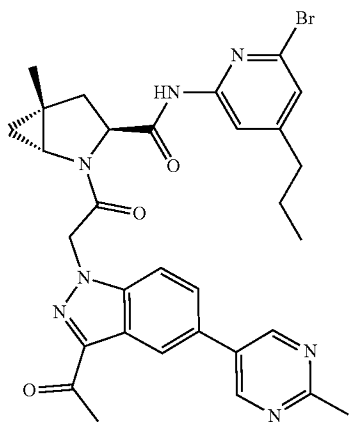 [SMILES: CCCc1cc(Br)nc(NC(=O)[C@@H]2C[C@@]3(C)C[C@H]3N2C(=O)Cn2nc(C(C)=O)c3cc(-c4cnc(C)nc4)ccc32)c1] | (1R,3S,5R)-2-(2-(3-acetyl-5-(2-methylpyrimidin-5-yl)-1H-indazol-1-yl)acetyl)-N-(6-bromo-4-propylpyridin-2-yl)-5-methyl-2-azabicyclo[3.1.0]hexane-3-carboxamide | ** | 4.10 (B) | 630 |
| 517 | 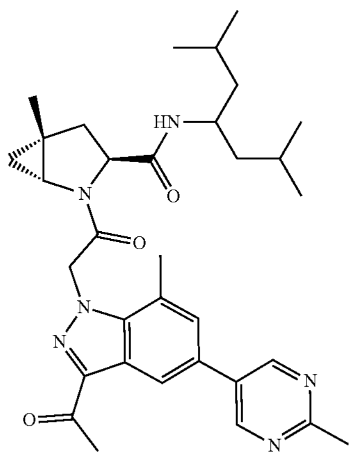 [SMILES: CC(=O)c1nn(CC(=O)N2[C@H](C(=O)NC(CC(C)C)CC(C)C)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(2,6-dimethylheptan-4-yl)-5-methyl-2-azabicyclo[3.1.0]hexane-3-carboxamide | *** | 4.30 (B) | 573 |
| 518 | 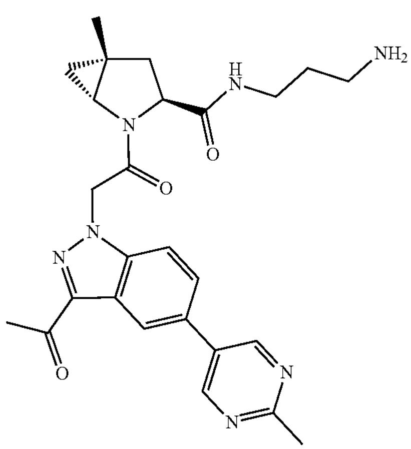 [SMILES: CC(=O)c1nn(CC(=O)N2[C@H](C(=O)NCCCN)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(3-aminopropyl)-5-methyl-2-azabicyclo[3.1.0]hexane-3-carboxamide | * | 0.89 (A) | 489 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 519 | 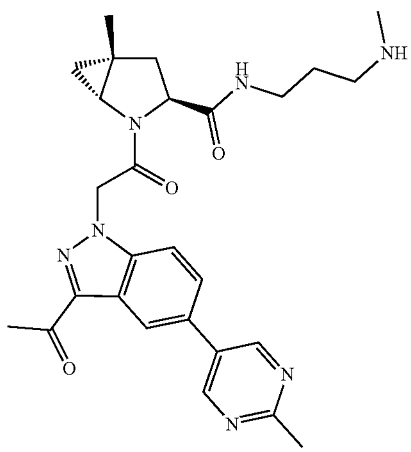 [SMILES: CNCCCNC(=O)[C@@H]1C[C@@]2(C)C[C@H]2N1C(=O)Cn1nc(C(C)=O)c2cc(-c3cnc(C)nc3)ccc21] | (1R,3S,5R)-2-(2-(3-acetyl-5-(2-methylpyrimidin-5-yl)-1H-indazol-1-yl)acetyl)-5-methyl-N-(3-(methylamino)propyl)-2-azabicyclo[3.1.0]hexane-3-carboxamide | ** | 0.91 (A) | 503 |
| 520 | 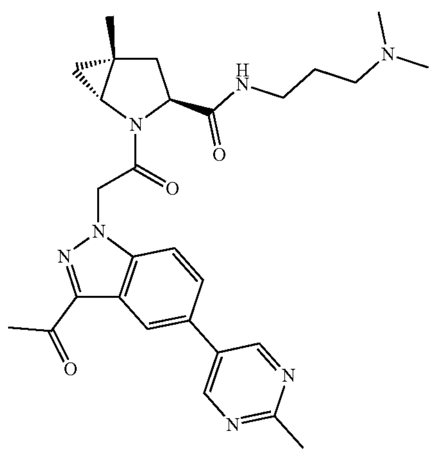 [SMILES: CC(=O)c1nn(CC(=O)N2[C@H](C(=O)NCCCN(C)C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(3-(dimethylamino)propyl)-5-methyl-2-azabicyclo[3.1.0]hexane-3-carboxamide | ** | 0.93 (A) | 517 |
| 521 | 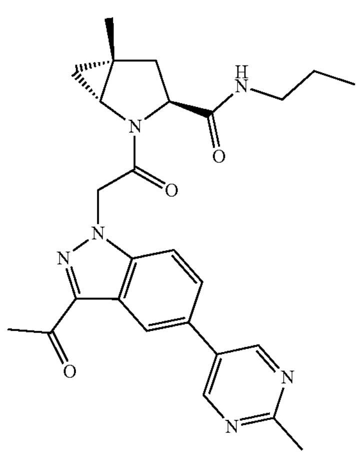 [SMILES: CCCNC(=O)[C@@H]1C[C@@]2(C)C[C@H]2N1C(=O)Cn1nc(C(C)=O)c2cc(-c3cnc(C)nc3)ccc21] | (1R,3S,5R)-2-(2-(3-acetyl-5-(2-methylpyrimidin-5-yl)-1H-indazol-1-yl)acetyl)-5-methyl-N-propyl-2-azabicyclo[3.1.0]hexane-3-carboxamide | *** | 1.48 (A) | 474 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 522 | 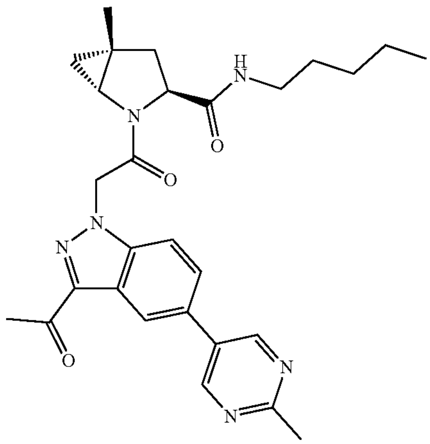 [SMILES: CCCCCNC(=O)[C@@H]1C[C@@]2(C)C[C@H]2N1C(=O)Cn1nc(C(C)=O)c2cc(-c3cnc(C)nc3)ccc21] | (1R,3S,5R)-2-(2-(3-acetyl-5-(2-methylpyrimidin-5-yl)-1H-indazol-1-yl)acetyl)-5-methyl-N-pentyl-2-azabicyclo[3.1.0]hexane-3-carboxamide | *** | 1.86 (A) | 502 |
| 523 | 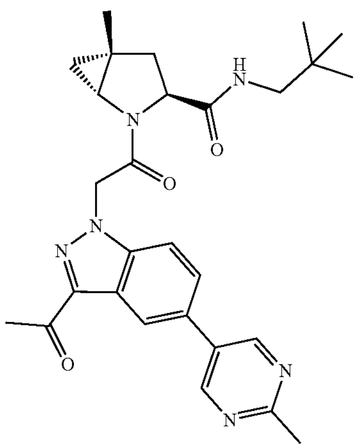 [SMILES: CC(=O)c1nn(CC(=O)N2[C@H](C(=O)NCC(C)(C)C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-5-methyl-N-neopentyl-2-azabicyclo[3.1.0]hexane-3-carboxamide | *** | 1.81 (A) | 502 |
| 524 | 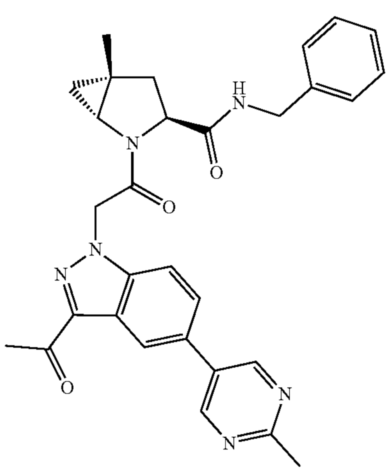 [SMILES: CC(=O)c1nn(CC(=O)N2[C@H](C(=O)NCc3ccccc3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-benzyl-5-methyl-2-azabicyclo[3.1.0]hexane-3-carboxamide | *** | 1.74 (A) | 522 |

TABLE 7-continued

Additional Non-limiting Examples of Compounds of the Present Invention

| Cmp No. | Structure | Name | IC₅ (Stars) | RT min (A, B, C or D) | MS (M + 1) |
|---|---|---|---|---|---|
| 525 | 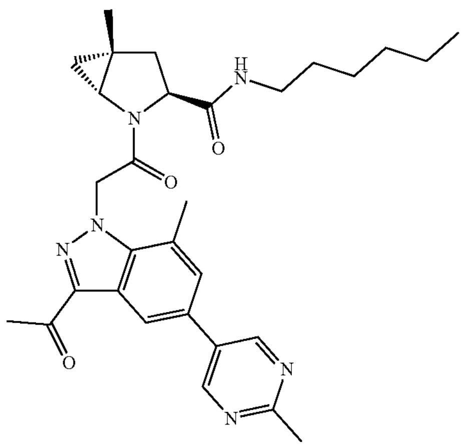 [SMILES: CCCCCCNC(=O)[C@@H]1C[C@@]2(C)C[C@H]2N1C(=O)Cn1nc(C(C)=O)c2cc(-c3cnc(C)nc3)cc(C)c21] | (1R,3S,5R)-2-(2-(3-acetyl-7-methyl-5-(2-methylpyrimidin-5-yl)-1H-indazol-1-yl)acetyl)-N-hexyl-5-methyl-2-azabicyclo[3.1.0]hexane-3-carboxamide | *** | 2.12 (A) | 530 |
| 526 | 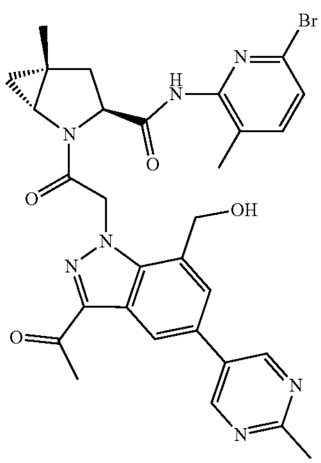 [SMILES: CC(=O)c1nn(CC(=O)N2[C@H](C(=O)Nc3nc(Br)ccc3C)C[C@@]3(C)C[C@@H]23)c2c(CO)cc(-c3cnc(C)nc3)cc12] | (1R,3S,5R)-2-(2-(3-acetyl-7-(hydroxymethyl)-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 1.68 (A) | 632 |
| 529 | 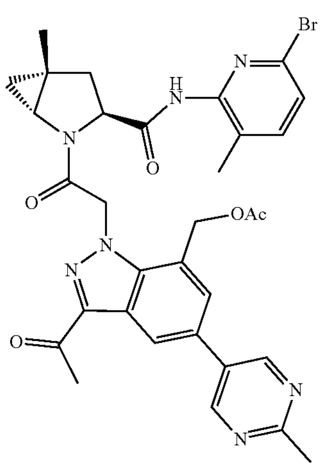 [SMILES: CC(=O)OCc1cc(-c2cnc(C)nc2)cc2c(C(C)=O)nn(CC(=O)N3[C@H](C(=O)Nc4nc(Br)ccc4C)C[C@@]4(C)C[C@@H]34)c12] | (3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-5-(2-methylpyrimidin-5-yl)-1H-indazol-7-yl)methyl acetate | *** | 1.95 (A) | 674 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 532 | 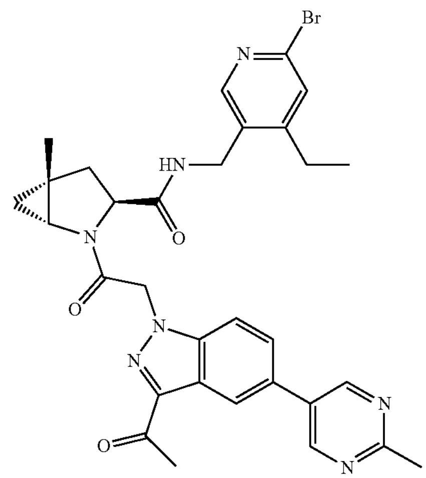 [SMILES: CCc1cc(Br)ncc1CNC(=O)[C@@H]1C[C@@]2(C)C[C@H]2N1C(=O)Cn1nc(C(C)=O)c2cc(-c3cnc(C)nc3)ccc21] | (1R,3S,5R)-2-(2-(3-acetyl-5-(2-methylpyrimidin-5-yl)-1H-indazol-1-yl)acetyl)-N-(6-bromo-4-ethylpyridin-2-yl)-5-methyl-2-azabicyclo[3.1.0]hexane-3-carboxamide | *** | 3.71 (B) | 616 |
| 533 | 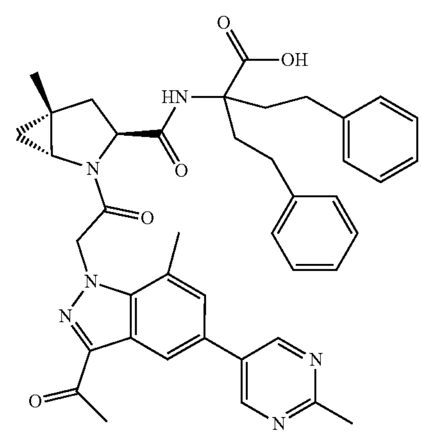 [SMILES: CC(=O)c1nn(CC(=O)N2[C@H](C(=O)NC(CCc3ccccc3)(CCc3ccccc3)C(=O)O)C[C@@]3(C)C[C@@H]23)c2c(C)cc(-c3cnc(C)nc3)cc12] | 2-((1R,3S,5R)-2-(2-(3-acetyl-7-methyl-5-(2-methylpyrimidin-5-yl)-1H-indazol-1-yl)acetyl)-5-methyl-2-azabicyclo[3.1.0]hexane-3-carboxamido)-2-phenethyl-4-phenylbutanoic acid | * | 3.96 (B) | 713 |
| 534 | 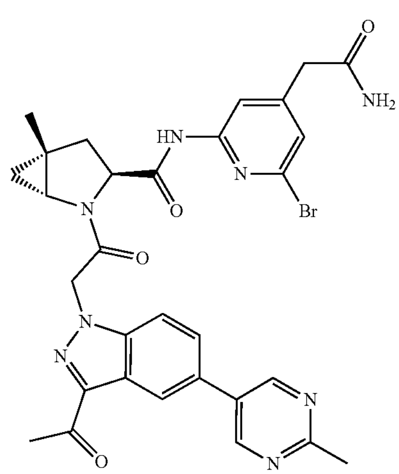 [SMILES: CC(=O)c1nn(CC(=O)N2[C@H](C(=O)Nc3cc(CC(N)=O)cc(Br)n3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(4-(2-amino-2-oxoethyl)-6-bromopyridin-2-yl)-5-methyl-2-azabicyclo[3.1.0]hexane-3-carboxamide | *** | 2.81 (B) | 645 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 536 | 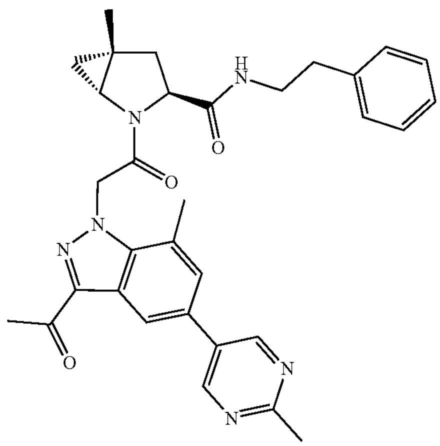 [SMILES: CC(=O)c1nn(CC(=O)N2[C@H](C(=O)NCCc3ccccc3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-methyl-N-phenethyl-2-azabicyclo[3.1.0]hexane-3-carboxamide | *** | 1.94 (A) | 550 |
| 537 | 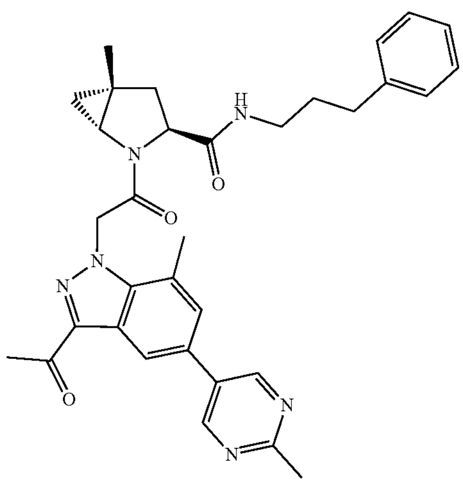 [SMILES: CC(=O)c1nn(CC(=O)N2[C@H](C(=O)NCCCc3ccccc3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-methyl-N-(3-phenylpropyl)-2-azabicyclo[3.1.0]hexane-3-carboxamide | *** | 2.03 (A) | 564 |
| 541 | 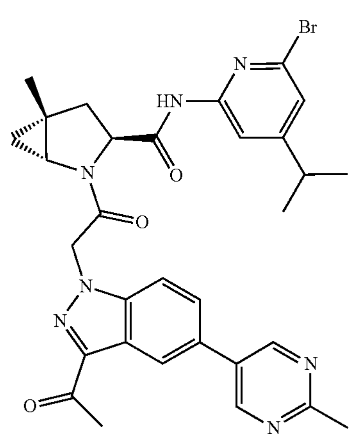 [SMILES: CC(=O)c1nn(CC(=O)N2[C@H](C(=O)Nc3cc(C(C)C)cc(Br)n3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-4-isopropylpyridin-2-yl)-5-methyl-2-azabicyclo[3.1.0]hexane-3-carboxamide | *** | 3.93 (B) | 630 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 542 | 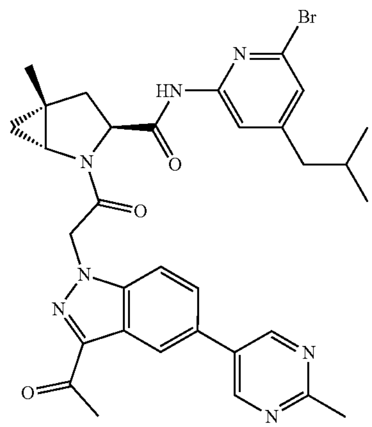 [SMILES: CC(=O)c1nn(CC(=O)N2[C@H](C(=O)Nc3cc(CC(C)C)cc(Br)n3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-4-isobutylpyridin-2-yl)-5-methyl-2-azabicyclo[3.1.0]hexane-3-carboxamide | *** | 4.45 (B) | 644 |
| 543 | 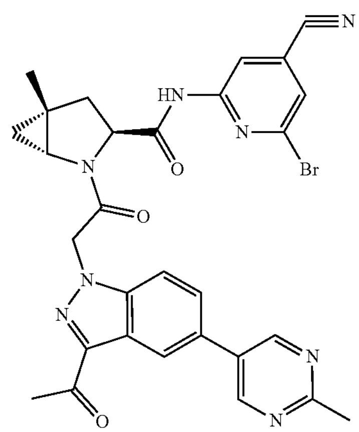 [SMILES: CC(=O)c1nn(CC(=O)N2[C@H](C(=O)Nc3cc(C#N)cc(Br)n3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-4-cyanopyridin-2-yl)-5-methyl-2-azabicyclo[3.1.0]hexane-3-carboxamide | *** | 1.95 (B) | 613 |
| 544 | 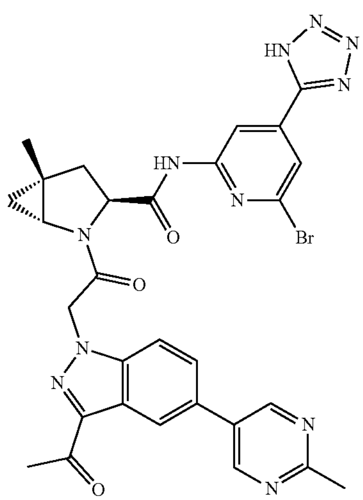 [SMILES: CC(=O)c1nn(CC(=O)N2[C@H](C(=O)Nc3cc(-c4nnn[nH]4)cc(Br)n3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-4-(1H-tetrazol-5-yl)pyridin-2-yl)-5-methyl-2-azabicyclo[3.1.0]hexane-3-carboxamide | *** | 3.65 (B) | 656 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 545 | 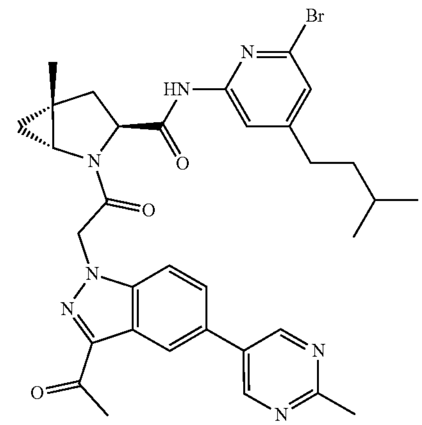 [SMILES: CC(=O)c1nn(CC(=O)N2[C@H](C(=O)Nc3cc(CCC(C)C)cc(Br)n3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-4-isopentylpyridin-2-yl)-5-methyl-2-azabicyclo[3.1.0]hexane-3-carboxamide | *** | 4.65 (B) | 658 |
| 546 | 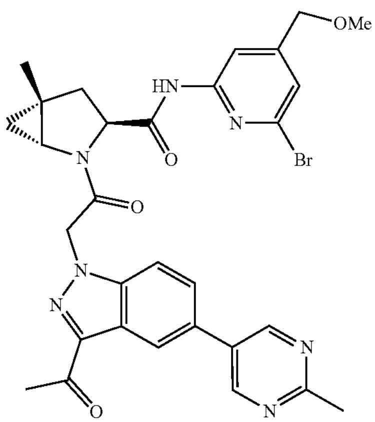 [SMILES: COCc1cc(Br)nc(NC(=O)[C@@H]2C[C@@]3(C)C[C@H]3N2C(=O)Cn2nc(C(C)=O)c3cc(-c4cnc(C)nc4)ccc32)c1] | (1R,3S,5R)-2-(2-(3-acetyl-5-(2-methylpyrimidin-5-yl)-1H-indazol-1-yl)acetyl)-N-(6-bromo-4-(methoxymethyl)pyridin-2-yl)-5-methyl-2-azabicyclo[3.1.0]hexane-3-carboxamide | *** | 3.68 (B) | 632 |
| 547 | 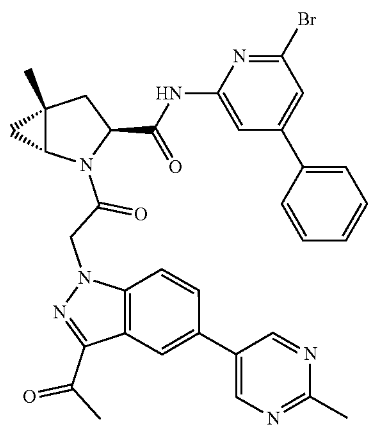 [SMILES: CC(=O)c1nn(CC(=O)N2[C@H](C(=O)Nc3cc(-c4ccccc4)cc(Br)n3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-4-phenylpyridin-2-yl)-5-methyl-2-azabicyclo[3.1.0]hexane-3-carboxamide | *** | 4.45 (B) | 664 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 548 | 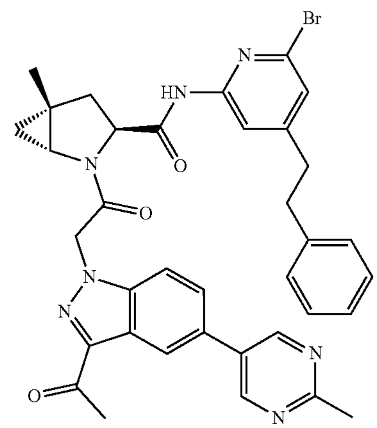 [SMILES: CC(=O)c1nn(CC(=O)N2[C@H](C(=O)Nc3cc(CCc4ccccc4)cc(Br)n3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-4-phenethylpyridin-2-yl)-5-methyl-2-azabicyclo[3.1.0]hexane-3-carboxamide | *** | 4.45 (B) | 692 |
| 549 | 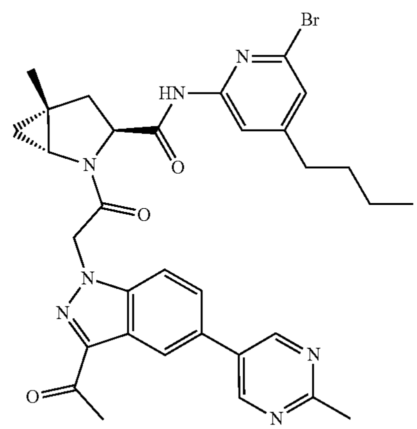 [SMILES: CCCCc1cc(Br)nc(NC(=O)[C@@H]2C[C@@]3(C)C[C@H]3N2C(=O)Cn2nc(C(C)=O)c3cc(-c4cnc(C)nc4)ccc32)c1] | (1R,3S,5R)-2-(2-(3-acetyl-5-(2-methylpyrimidin-5-yl)-1H-indazol-1-yl)acetyl)-N-(6-bromo-4-butylpyridin-2-yl)-5-methyl-2-azabicyclo[3.1.0]hexane-3-carboxamide | *** | 4.53 (B) | 644 |
| 550 | 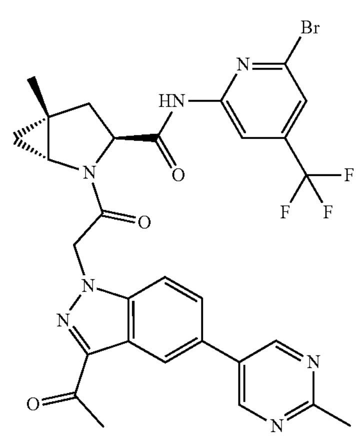 [SMILES: CC(=O)c1nn(CC(=O)N2[C@H](C(=O)Nc3cc(C(F)(F)F)cc(Br)n3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-4-(trifluoromethyl)pyridin-2-yl)-5-methyl-2-azabicyclo[3.1.0]hexane-3-carboxamide | *** | | |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 551 | 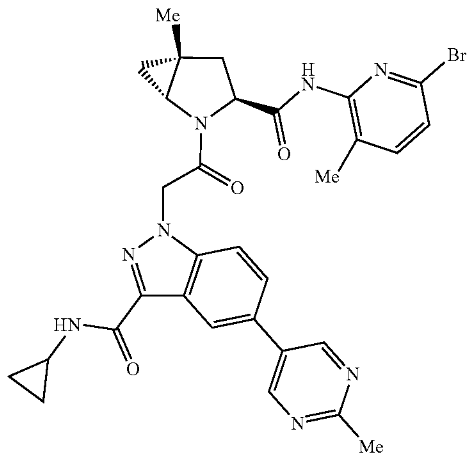 [SMILES: Cc1ncc(-c2ccc3c(c2)c(C(=O)NC2CC2)nn3CC(=O)N2[C@H](C(=O)Nc3nc(Br)ccc3C)C[C@@]3(C)C[C@@H]23)cn1] | 1-(2-((1R,3S,5R)-3-((6-bromo-3-methylpyridin-2-yl)carbamoyl)-5-methyl-2-azabicyclo[3.1.0]hexan-2-yl)-2-oxoethyl)-N-cyclopropyl-5-(2-methylpyrimidin-5-yl)-1H-indazole-3-carboxamide | *** | 1.73 (A) | 642 |
| 552 | 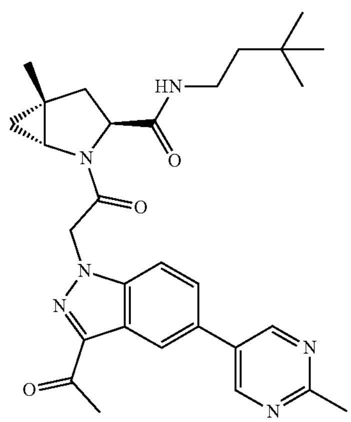 [SMILES: CC(=O)c1nn(CC(=O)N2[C@H](C(=O)NCCC(C)(C)C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(3,3-dimethylbutyl)-5-methyl-2-azabicyclo[3.1.0]hexane-3-carboxamide | *** | | |
| 553 | 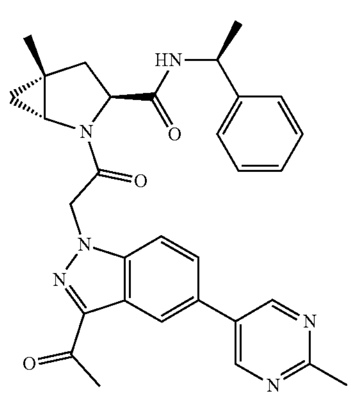 [SMILES: CC(=O)c1nn(CC(=O)N2[C@H](C(=O)N[C@@H](C)c3ccccc3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-5-methyl-N-((S)-1-phenylethyl)-2-azabicyclo[3.1.0]hexane-3-carboxamide | *** | | |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 554 | 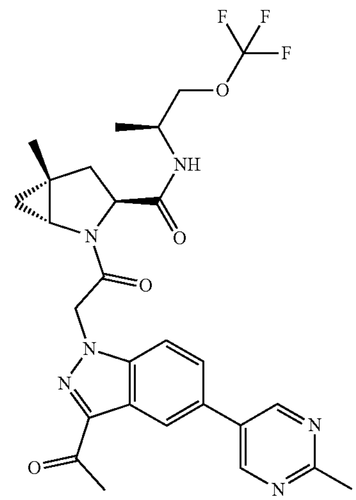 [SMILES: CC(=O)c1nn(CC(=O)N2[C@H](C(=O)N[C@@H](C)COC(F)(F)F)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-5-methyl-N-((S)-1-(trifluoromethoxy)propan-2-yl)-2-azabicyclo[3.1.0]hexane-3-carboxamide | *** | | |
| 555 | 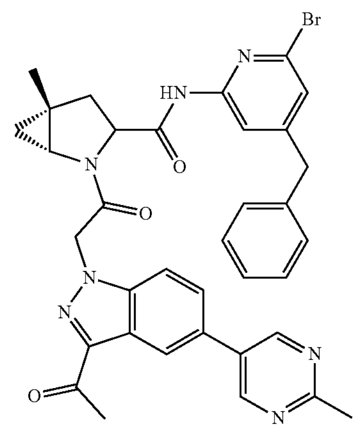 [SMILES: CC(=O)c1nn(CC(=O)N2C(C(=O)Nc3cc(Cc4ccccc4)cc(Br)n3)C[C@@]3(C)C[C@@H]23)c2ccc(-c3cnc(C)nc3)cc12] | (1R,5R)-2-(2-(3-acetyl-5-(2-methylpyrimidin-5-yl)-1H-indazol-1-yl)acetyl)-N-(4-benzyl-6-bromopyridin-2-yl)-5-methyl-2-azabicyclo[3.1.0]hexane-3-carboxamide | *** | | |
| 556 | 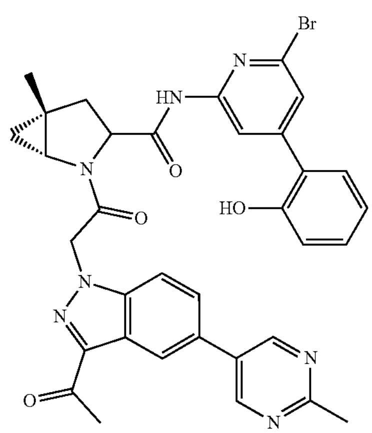 [SMILES: CC(=O)c1nn(CC(=O)N2C(C(=O)Nc3cc(-c4ccccc4O)cc(Br)n3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-4-(2-hydroxyphenyl)pyridin-2-yl)-5-methyl-2-azabicyclo[3.1.0]hexane-3-carboxamide | *** | | |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 557 | 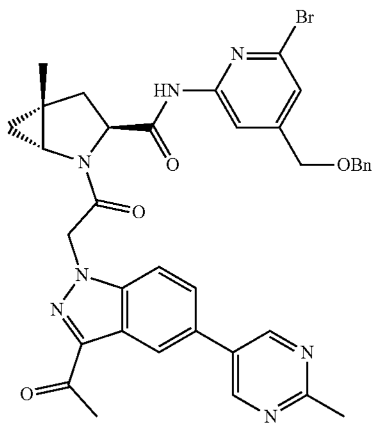 [SMILES: CC(=O)c1nn(CC(=O)N2[C@H](C(=O)Nc3cc(COCc4ccccc4)cc(Br)n3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(4-((benzyloxy)methyl)-6-bromopyridin-2-yl)-5-methyl-2-azabicyclo[3.1.0]hexane-3-carboxamide | *** | | |
| 558 | 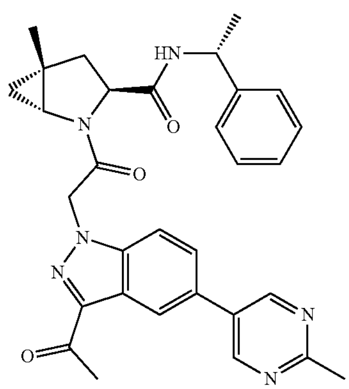 [SMILES: CC(=O)c1nn(CC(=O)N2[C@H](C(=O)N[C@H](C)c3ccccc3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-5-methyl-N-((R)-1-phenylethyl)-2-azabicyclo[3.1.0]hexane-3-carboxamide | *** | | |
| 559 | 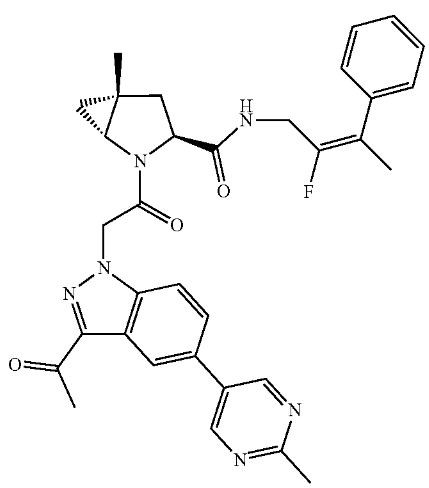 [SMILES: CC(=O)c1nn(CC(=O)N2[C@H](C(=O)NC/C(F)=C(/C)c3ccccc3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((E)-2-fluoro-3-phenylbut-2-en-1-yl)-5-methyl-2-azabicyclo[3.1.0]hexane-3-carboxamide | *** | 2.14 (A) | 581 |

TABLE 7-continued

Additional Non-limiting Examples of Compounds of the Present Invention

| Cmp No. | Structure | Name | IC₅ (Stars) | RT min (A, B, C or D) | MS (M + 1) |
|---|---|---|---|---|---|
| 560 | 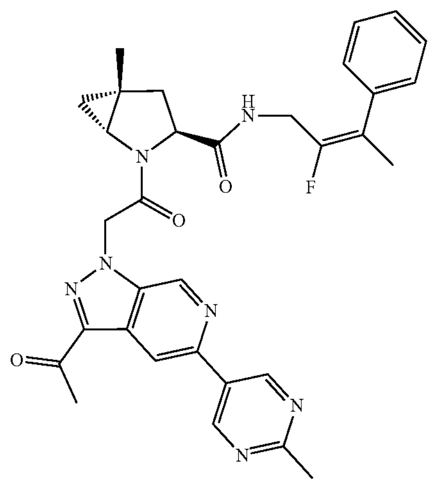 [SMILES: CC(=O)c1nn(CC(=O)N2[C@H](C(=O)NC/C(F)=C(/C)c3ccccc3)C[C@@]3(C)C[C@@H]23)c2cnc(-c3cnc(C)nc3)cc12] | (1R,3S,5R)-2-(2-(3-acetyl-5-(2-methylpyrimidin-5-yl)-1H-pyrrolo[2,3-c]pyridin-1-yl)acetyl)-N-((E)-2-fluoro-3-phenylbut-2-en-1-yl)-5-methyl-2-azabicyclo[3.1.0]hexane-3-carboxamide | *** | 1.85 (A) | 581 |
| 561 | 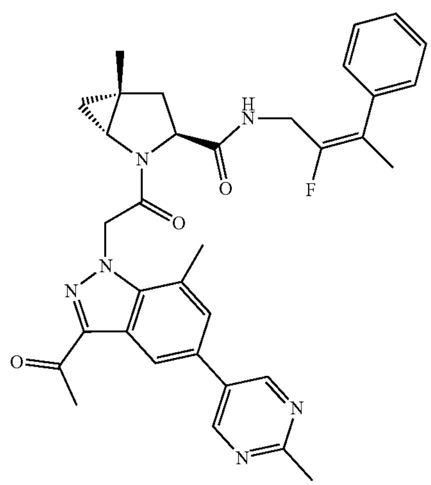 [SMILES: CC(=O)c1nn(CC(=O)N2[C@H](C(=O)NC/C(F)=C(/C)c3ccccc3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-((E)-2-fluoro-3-phenylbut-2-en-1-yl)-5-methyl-2-azabicyclo[3.1.0]hexane-3-carboxamide | *** | 2.23 (A) | 595 |
| 562 | 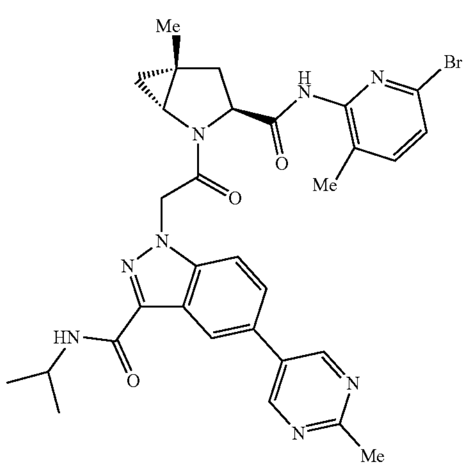 [SMILES: Cc1ncc(-c2ccc3c(c2)c(C(=O)NC(C)C)nn3CC(=O)N2[C@H](C(=O)Nc3nc(Br)ccc3C)C[C@@]3(C)C[C@@H]23)cn1] | 1-(2-((1R,3S,5R)-3-((6-bromo-3-methylpyridin-2-yl)carbamoyl)-5-methyl-2-azabicyclo[3.1.0]hexan-2-yl)-2-oxoethyl)-N-isopropyl-5-(2-methylpyrimidin-5-yl)-1H-indazole-3-carboxamide | ** | 1.87 (A) | 644 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 563 | 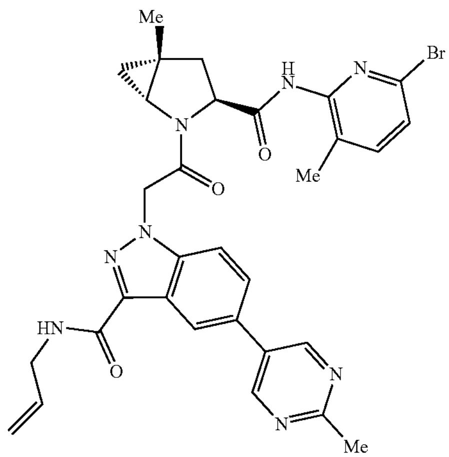 [SMILES: C=CCNC(=O)c1nn(CC(=O)N2[C@H](C(=O)Nc3nc(Br)ccc3C)C[C@@]3(C)C[C@@H]23)c2ccc(-c3cnc(C)nc3)cc12] | N-allyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-5-(2-methylpyrimidin-5-yl)-1H-indazole-3-carboxamide | *** | 1.80 (A) | 642 |
| 564 | 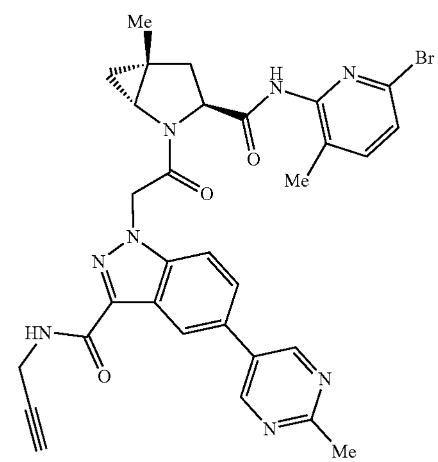 [SMILES: C#CCNC(=O)c1nn(CC(=O)N2[C@H](C(=O)Nc3nc(Br)ccc3C)C[C@@]3(C)C[C@@H]23)c2ccc(-c3cnc(C)nc3)cc12] | 1-(2-((1R,3S,5R)-3-((6-bromo-3-methylpyridin-2-yl)carbamoyl)-5-methyl-2-azabicyclo[3.1.0]hexan-2-yl)-2-oxoethyl)-5-(2-methylpyrimidin-5-yl)-N-(prop-2-yn-1-yl)-1H-indazole-3-carboxamide | *** | 1.73 (A) | 640 |
| 565 | 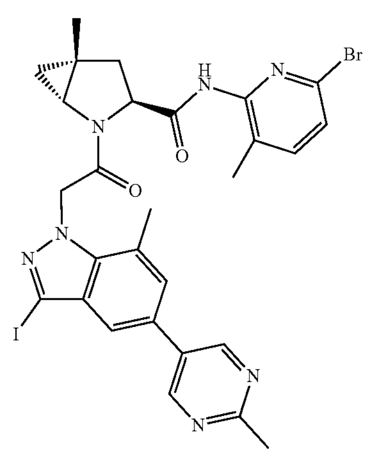 [SMILES: Cc1ncc(-c2cc(C)c3c(c2)c(I)nn3CC(=O)N2[C@H](C(=O)Nc3nc(Br)ccc3C)C[C@@]3(C)C[C@@H]23)cn1] | (1R,3S,5R)-N-(6-bromo-3-methylpyridin-2-yl)-2-(2-(3-iodo-7-methyl-5-(2-methylpyrimidin-5-yl)-1H-indazol-1-yl)acetyl)-5-methyl-2-azabicyclo[3.1.0]hexane-3-carboxamide | *** | 2.15 (A) | 699 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 566 | 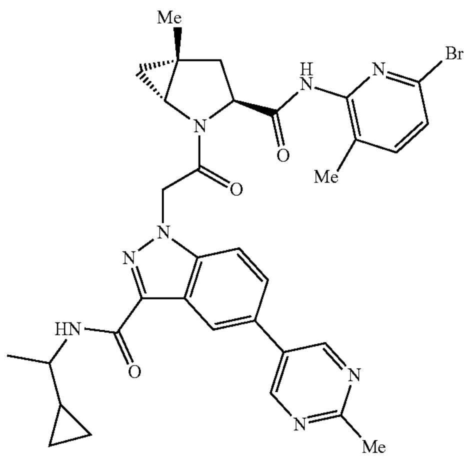 [SMILES: Cc1ncc(-c2ccc3c(c2)c(C(=O)NC(C)C2CC2)nn3CC(=O)N2[C@H](C(=O)Nc3nc(Br)ccc3C)C[C@@]3(C)C[C@@H]23)cn1] | 1-(2-(((1R,3S,5R)-3-((6-bromo-3-methylpyridin-2-yl)carbamoyl)-5-methyl-2-azabicyclo[3.1.0]hexan-2-yl)-2-oxoethyl)-N-(1-cyclopropylethyl)-5-(2-methylpyrimidin-5-yl)-1H-indazole-3-carboxamide | *** | 2.07 (A) | 670 |
| 567 | 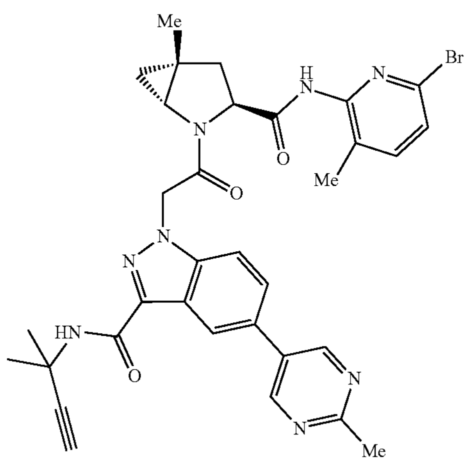 [SMILES: C#CC(C)(C)NC(=O)c1nn(CC(=O)N2[C@H](C(=O)Nc3nc(Br)ccc3C)C[C@@]3(C)C[C@@H]23)c2ccc(-c3cnc(C)nc3)cc12] | 1-(2-(((1R,3S,5R)-3-((6-bromo-3-methylpyridin-2-yl)carbamoyl)-5-methyl-2-azabicyclo[3.1.0]hexan-2-yl)-2-oxoethyl)-N-(2-methylbut-3-yn-2-yl)-5-(2-methylpyrimidin-5-yl)-1H-indazole-3-carboxamide | * | 1.99 (A) | 668 |
| 568 | 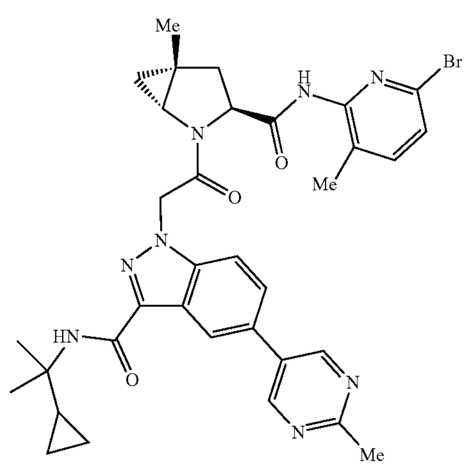 [SMILES: Cc1ncc(-c2ccc3c(c2)c(C(=O)NC(C)(C)C2CC2)nn3CC(=O)N2[C@H](C(=O)Nc3nc(Br)ccc3C)C[C@@]3(C)C[C@@H]23)cn1] | 1-(2-(((1R,3S,5R)-3-((6-bromo-3-methylpyridin-2-yl)carbamoyl)-5-methyl-2-azabicyclo[3.1.0]hexan-2-yl)-2-oxoethyl)-N-(2-cyclopropylpropan-2-yl)-5-(2-methylpyrimidin-5-yl)-1H-indazole-3-carboxamide | * | 2.30 (A) | 684 |

TABLE 7-continued

Additional Non-limiting Examples of Compounds of the Present Invention

| Cmp No. | Structure | Name | IC₅ (Stars) | RT min (A, B, C or D) | MS (M + 1) |
|---|---|---|---|---|---|
| 570 | 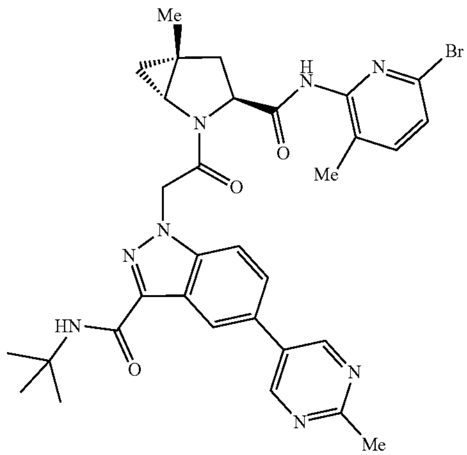 [SMILES: Cc1ncc(-c2ccc3c(c2)c(C(=O)NC(C)(C)C)nn3CC(=O)N2[C@H](C(=O)Nc3nc(Br)ccc3C)C[C@@]3(C)C[C@@H]23)cn1] | 1-(2-((1R,3S,5R)-3-((6-bromo-3-methylpyridin-2-yl)carbamoyl)-5-methyl-2-azabicyclo[3.1.0]hexan-2-yl)-2-oxoethyl)-N-(tert-butyl)-5-(2-methylpyrimidin-5-yl)-1H-indazole-3-carboxamide | * | 2.14 (A) | 658 |
| 571 | 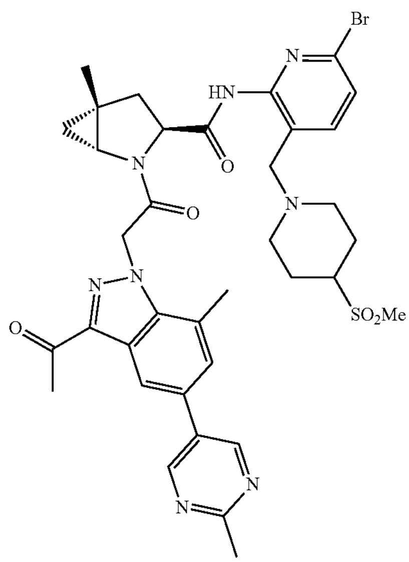 [SMILES: CC(=O)c1nn(CC(=O)N2[C@H](C(=O)Nc3nc(Br)ccc3CN3CCC(S(C)(=O)=O)CC3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-((4-(methylsulfonyl)piperidin-1-yl)methyl)pyridin-2-yl)-5-methyl-2-azabicyclo[3.1.0]hexane-3-carboxamide | *** | 1.28 (A) | 776 |
| 572 | 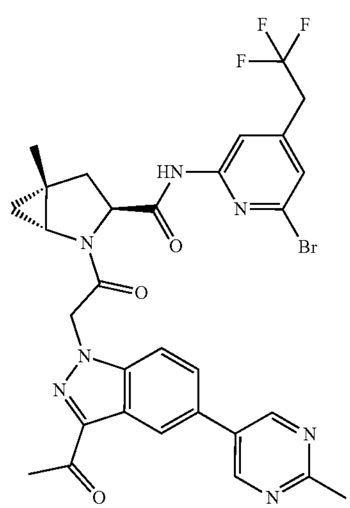 [SMILES: CC(=O)c1nn(CC(=O)N2[C@H](C(=O)Nc3cc(CC(F)(F)F)cc(Br)n3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-4-(2,2,2-trifluoroethyl)pyridin-2-yl)-5-methyl-2-azabicyclo[3.1.0]hexane-3-carboxamide | *** | | |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 573 | 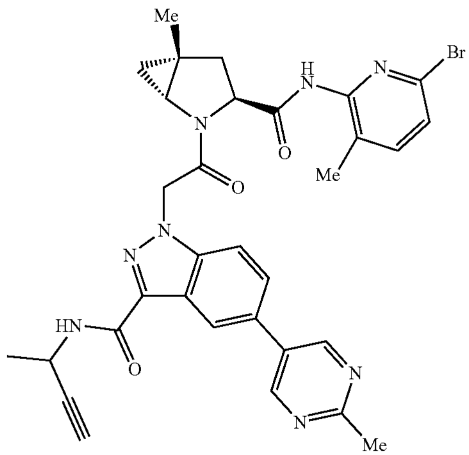 [SMILES: C#CC(C)NC(=O)c1nn(CC(=O)N2[C@H](C(=O)Nc3nc(Br)ccc3C)C[C@@]3(C)C[C@@H]23)c2ccc(-c3cnc(C)nc3)cc12] | 1-(2-((1R,3S,5R)-3-((6-bromo-3-methylpyridin-2-yl)carbamoyl)-5-methyl-2-azabicyclo[3.1.0]hexan-2-yl)-2-oxoethyl)-N-(but-3-yn-2-yl)-5-(2-methylpyrimidin-5-yl)-1H-indazole-3-carboxamide | *** | 1.87 (A) | 654 |
| 574 | 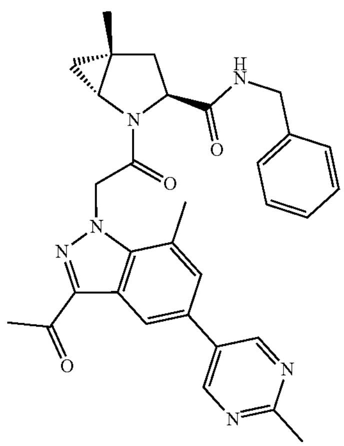 | (1R,3S,5R)-2-(2-(3-acetyl-7-methyl-5-(2-methylpyrimidin-5-yl)-1H-indazol-1-yl)acetyl)-N-benzyl-5-methyl-2-azabicyclo[3.1.0]hexane-3-carboxamide | *** | 1.88 (A) | 536 |
| 575 | 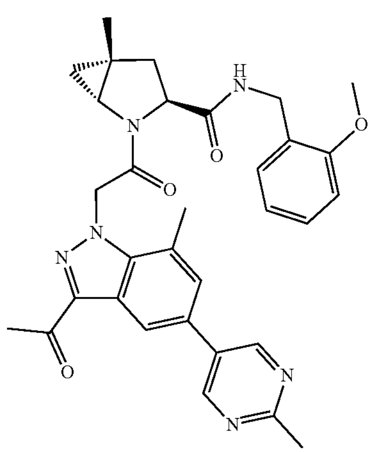 [SMILES: COc1ccccc1CNC(=O)[C@@H]1C[C@@]2(C)C[C@H]2N1C(=O)Cn1nc(C(C)=O)c2cc(-c3cnc(C)nc3)cc(C)c21] | (1R,3S,5R)-2-(2-(3-acetyl-7-methyl-5-(2-methylpyrimidin-5-yl)-1H-indazol-1-yl)acetyl)-N-(2-methoxybenzyl)-5-methyl-2-azabicyclo[3.1.0]hexane-3-carboxamide | *** | 1.94 (A) | 566 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 576 | 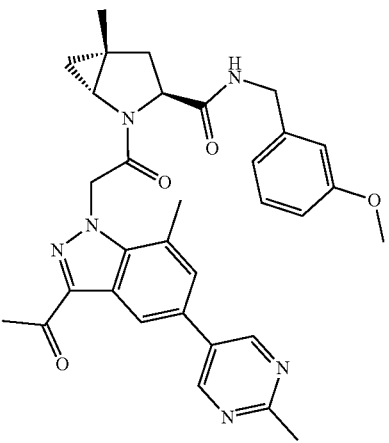 [SMILES: COc1cccc(CNC(=O)[C@@H]2C[C@@]3(C)C[C@H]3N2C(=O)Cn2nc(C(C)=O)c3cc(-c4cnc(C)nc4)cc(C)c32)c1] | (1R,3S,5R)-2-(2-(3-acetyl-7-methyl-5-(2-methylpyrimidin-5-yl)-1H-indazol-1-yl)acetyl)-N-(3-methoxybenzyl)-5-methyl-2-azabicyclo[3.1.0]hexane-3-carboxamide | *** | 1.86 (A) | 566 |
| 577 | 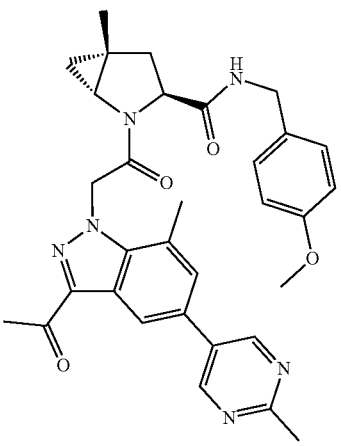 [SMILES: COc1ccc(CNC(=O)[C@@H]2C[C@@]3(C)C[C@H]3N2C(=O)Cn2nc(C(C)=O)c3cc(-c4cnc(C)nc4)cc(C)c32)cc1] | (1R,3S,5R)-2-(2-(3-acetyl-7-methyl-5-(2-methylpyrimidin-5-yl)-1H-indazol-1-yl)acetyl)-N-(4-methoxybenzyl)-5-methyl-2-azabicyclo[3.1.0]hexane-3-carboxamide | *** | 1.90 (A) | 566 |
| 578 | 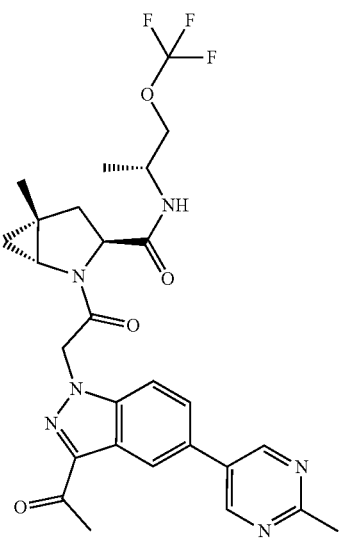 [SMILES: CC(=O)c1nn(CC(=O)N2[C@H](C(=O)N[C@H](C)COC(F)(F)F)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-5-methyl-N-((R)-1-(trifluoromethoxy)propan-2-yl)-2-azabicyclo[3.1.0]hexane-3-carboxamide | | | |

TABLE 7-continued

Additional Non-limiting Examples of Compounds of the Present Invention

| Cmp No. | Structure | Name | IC₅ (Stars) | RT min (A, B, C or D) | MS (M + 1) |
|---|---|---|---|---|---|
| 579 | 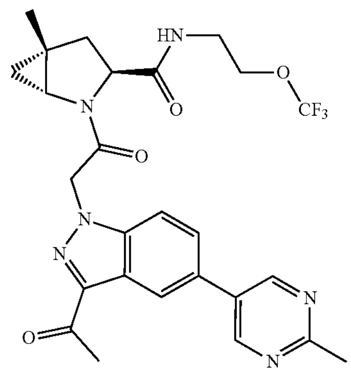 [SMILES: CC(=O)c1nn(CC(=O)N2[C@H](C(=O)NCCOC(F)(F)F)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-5-methyl-N-(2-(trifluoromethoxy)ethyl)-2-azabicyclo[3.1.0]hexane-3-carboxamide | *** | | |
| 580 | 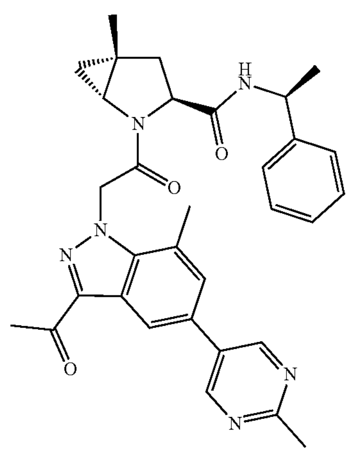 [SMILES: CC(=O)c1nn(CC(=O)N2[C@H](C(=O)N[C@@H](C)c3ccccc3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-methyl-N-((S)-1-phenylethyl)-2-azabicyclo[3.1.0]hexane-3-carboxamide | *** | 1.93 (A) | 550 |
| 581 | 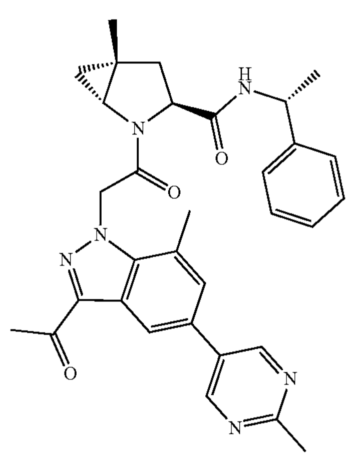 [SMILES: CC(=O)c1nn(CC(=O)N2[C@H](C(=O)N[C@H](C)c3ccccc3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-methyl-N-((R)-1-phenylethyl)-2-azabicyclo[3.1.0]hexane-3-carboxamide | *** | 1.92 (A) | 550 |

TABLE 7-continued

Additional Non-limiting Examples of Compounds of the Present Invention

| Cmp No. | Structure | Name | IC₅ (Stars) | RT min (A, B, C or D) | MS (M + 1) |
|---|---|---|---|---|---|
| 582 | 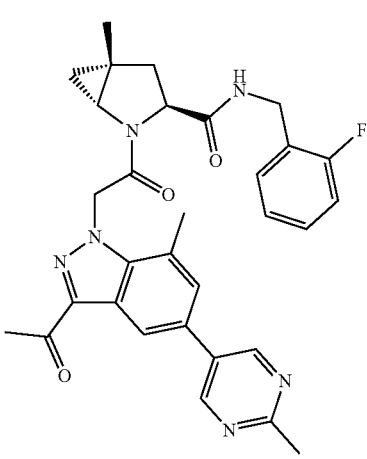 [SMILES: CC(=O)c1nn(CC(=O)N2[C@H](C(=O)NCc3ccccc3F)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(2-fluorobenzyl)-5-methyl-2-azabicyclo[3.1.0]hexane-3-carboxamide | *** | 1.87 (A) | 554 |
| 583 | 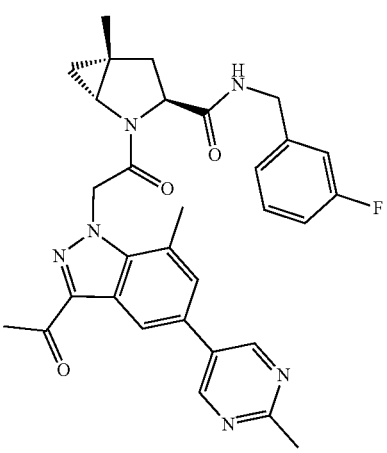 [SMILES: CC(=O)c1nn(CC(=O)N2[C@H](C(=O)NCc3cccc(F)c3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(3-fluorobenzyl)-5-methyl-2-azabicyclo[3.1.0]hexane-3-carboxamide | *** | 1.86 (A) | 554 |
| 584 | 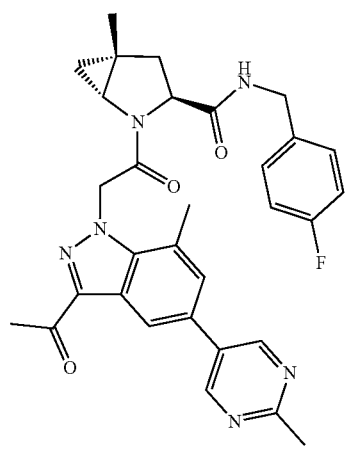 | (1R,3S,5R)-2-(2-(3-acetyl-7-methyl-5-(2-methylpyrimidin-5-yl)-1H-indazol-1-yl)acetyl)-N-(4-fluorobenzyl)-5-methyl-2-azabicyclo[3.1.0]hexane-3-carboxamide | *** | 1.88 (A) | 554 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 585 | 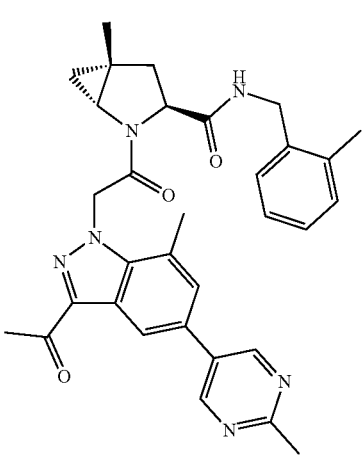 [SMILES: CC(=O)c1nn(CC(=O)N2[C@H](C(=O)NCc3ccccc3C)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-methyl-N-(2-methylbenzyl)-2-azabicyclo[3.1.0]hexane-3-carboxamide | *** | 1.95 (A) | 550 |
| 586 | 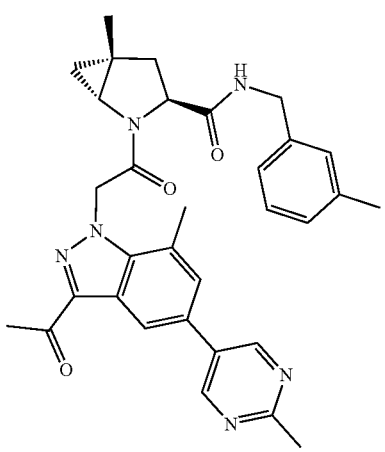 [SMILES: CC(=O)c1nn(CC(=O)N2[C@H](C(=O)NCc3cccc(C)c3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-methyl-N-(3-methylbenzyl)-2-azabicyclo[3.1.0]hexane-3-carboxamide | *** | 1.96 (A) | 550 |
| 587 | 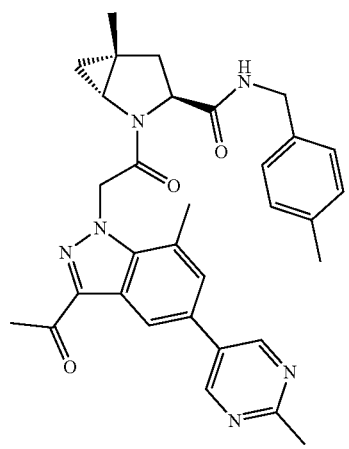 [SMILES: CC(=O)c1nn(CC(=O)N2[C@H](C(=O)NCc3ccc(C)cc3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-methyl-N-(4-methylbenzyl)-2-azabicyclo[3.1.0]hexane-3-carboxamide | *** | 1.96 (A) | 550 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 588 | 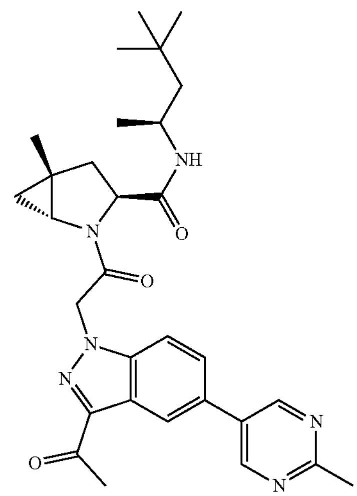 [SMILES: CC(=O)c1nn(CC(=O)N2[C@H](C(=O)N[C@@H](C)CC(C)(C)C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((S)-4,4-dimethylpentan-2-yl)-5-methyl-2-azabicyclo[3.1.0]hexane-3-carboxamide | ** | | |
| 589 | 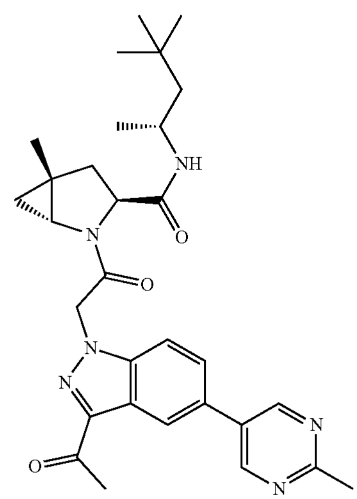 [SMILES: CC(=O)c1nn(CC(=O)N2[C@H](C(=O)N[C@H](C)CC(C)(C)C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((R)-4,4-dimethylpentan-2-yl)-5-methyl-2-azabicyclo[3.1.0]hexane-3-carboxamide | *** | | |
| 590 | 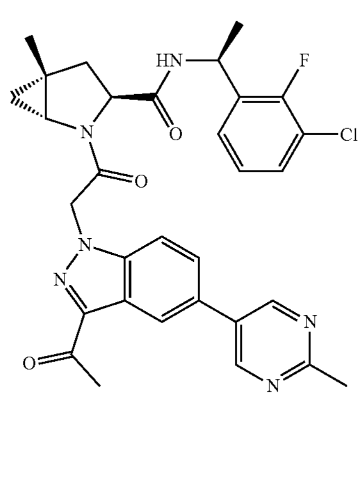 [SMILES: CC(=O)c1nn(CC(=O)N2[C@H](C(=O)N[C@@H](C)c3cccc(Cl)c3F)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((S)-1-(3-chloro-2-fluorophenyl)ethyl)-5-methyl-2-azabicyclo[3.1.0]hexane-3-carboxamide | *** | | |

TABLE 7-continued

Additional Non-limiting Examples of Compounds of the Present Invention

| Cmp No. | Structure | Name | IC₅ (Stars) | RT min (A, B, C or D) | MS (M + 1) |
|---|---|---|---|---|---|
| 591 | 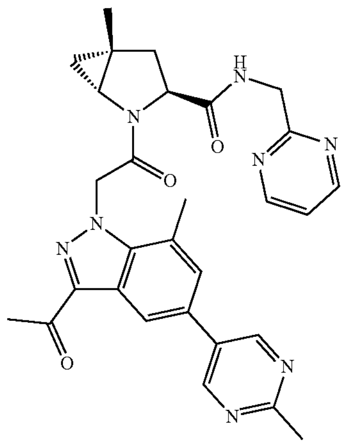 [SMILES: CC(=O)c1nn(CC(=O)N2[C@H](C(=O)NCc3ncccn3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-methyl-N-(pyrimidin-2-ylmethyl)-2-azabicyclo[3.1.0]hexane-3-carboxamide | *** | 1.37 (A) | 538 |
| 592 | 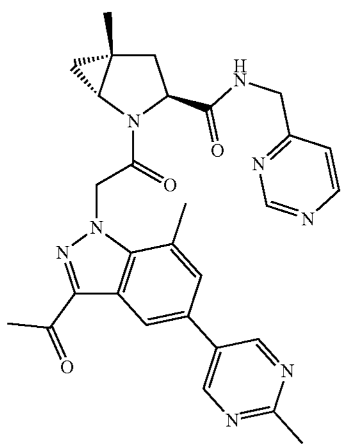 | (1R,3S,5R)-2-(2-(3-acetyl-7-methyl-5-(2-methylpyrimidin-5-yl)-1H-indazol-1-yl)acetyl)-5-methyl-N-(pyrimidin-4-ylmethyl)-2-azabicyclo[3.1.0]hexane-3-carboxamide | ** | 1.32 (A) | 538 |
| 593 | 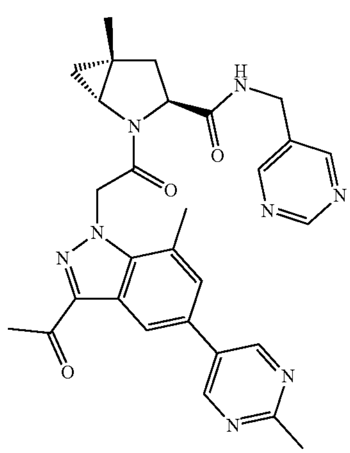 [SMILES: CC(=O)c1nn(CC(=O)N2[C@H](C(=O)NCc3cncnc3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-methyl-N-(pyrimidin-5-ylmethyl)-2-azabicyclo[3.1.0]hexane-3-carboxamide | *** | 1.31 (A) | 538 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 594 | 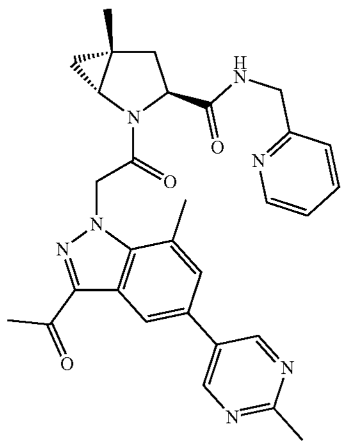 [SMILES: CC(=O)c1nn(CC(=O)N2[C@H](C(=O)NCc3ccccn3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-methyl-N-(pyridin-2-ylmethyl)-2-azabicyclo[3.1.0]hexane-3-carboxamide | *** | 1.24 (A) | 537 |
| 595 | 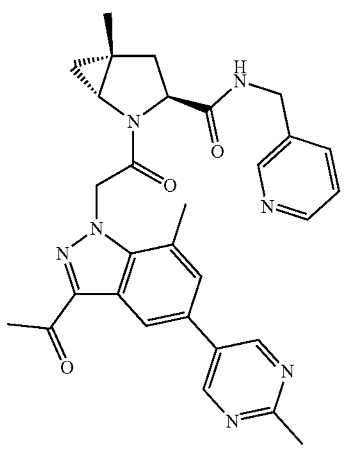 [SMILES: CC(=O)c1nn(CC(=O)N2[C@H](C(=O)NCc3cccnc3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-methyl-N-(pyridin-3-ylmethyl)-2-azabicyclo[3.1.0]hexane-3-carboxamide | *** | 1.15 (A) | 537 |
| 596 | 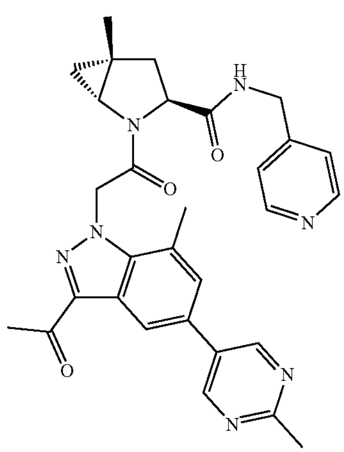 [SMILES: CC(=O)c1nn(CC(=O)N2[C@H](C(=O)NCc3ccncc3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-methyl-N-(pyridin-4-ylmethyl)-2-azabicyclo[3.1.0]hexane-3-carboxamide | *** | 1.13 (A) | 537 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 597 | 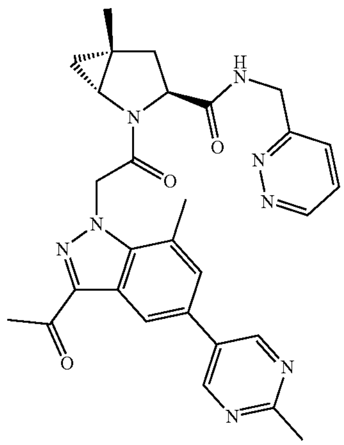 | (1R,3S,5R)-2-(2-(3-acetyl-7-methyl-5-(2-methylpyrimidin-5-yl)-1H-indazol-1-yl)acetyl)-5-methyl-N-(pyridazin-3-ylmethyl)-2-azabicyclo[3.1.0]hexane-3-carboxamide | *** | 1.26 (A) | 538 |
| 598 | 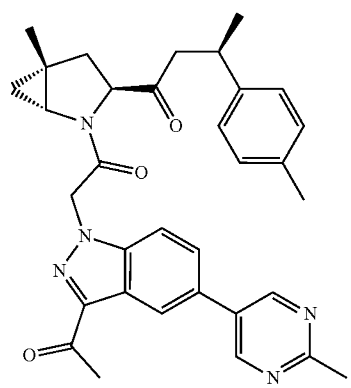 [SMILES: CC(=O)c1nn(CC(=O)N2[C@H](C(=O)C[C@@H](C)c3ccc(C)cc3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-5-methyl-N-((S)-1-(p-tolyl)ethyl)-2-azabicyclo[3.1.0]hexane-3-carboxamide | ** | | |
| 599 | 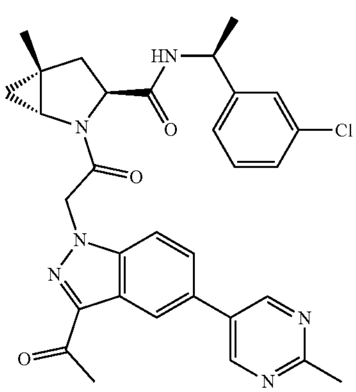 [SMILES: CC(=O)c1nn(CC(=O)N2[C@H](C(=O)N[C@@H](C)c3cccc(Cl)c3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((S)-1-(3-chlorophenyl)ethyl)-5-methyl-2-azabicyclo[3.1.0]hexane-3-carboxamide | *** | | |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 600 | 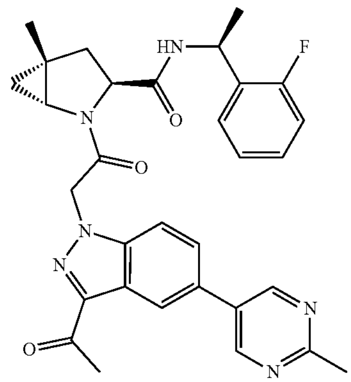 [SMILES: CC(=O)c1nn(CC(=O)N2[C@H](C(=O)N[C@@H](C)c3ccccc3F)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((S)-1-(2-fluorophenyl)ethyl)-5-methyl-2-azabicyclo[3.1.0]hexane-3-carboxamide | *** | | |
| 601 | 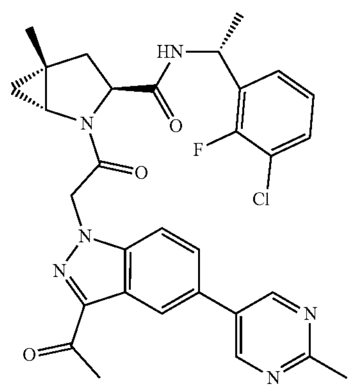 [SMILES: CC(=O)c1nn(CC(=O)N2[C@H](C(=O)N[C@H](C)c3cccc(Cl)c3F)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((R)-1-(3-chloro-2-fluorophenyl)ethyl)-5-methyl-2-azabicyclo[3.1.0]hexane-3-carboxamide | *** | | |
| 602 | 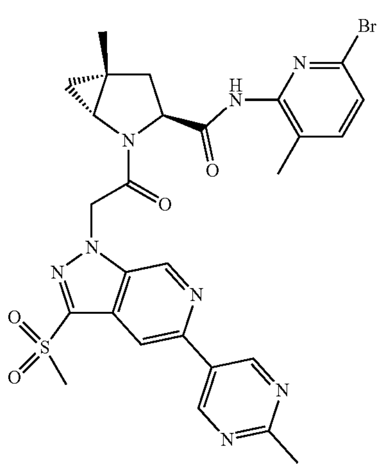 [SMILES: Cc1ncc(-c2cc3c(S(C)(=O)=O)nn(CC(=O)N4[C@H](C(=O)Nc5nc(Br)ccc5C)C[C@@]5(C)C[C@@H]45)c3cn2)cn1] | (1R,3S,5R)-N-(6-bromo-3-methylpyridin-2-yl)-5-methyl-2-(2-(5-(2-methylpyrimidin-5-yl)-3-(methylsulfonyl)-1H-pyrazolo[3,4-c]pyridin-1-yl)acetyl)-2-azabicyclo[3.1.0]hexane-3-carboxamide | | 1.53 (A) | 640 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 603 | 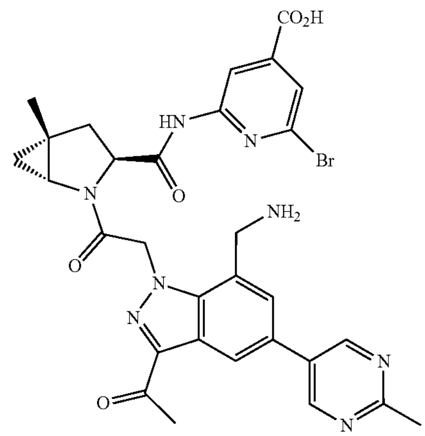 [SMILES: CC(=O)c1nn(CC(=O)N2[C@H](C(=O)Nc3cc(C(=O)O)cc(Br)n3)C[C@@]3(C)C[C@@H]23)c2c(CN)cc(-c3cnc(C)nc3)cc12] | 2-((1R,3S,5R)-2-(2-(3-acetyl-7-(aminomethyl)-5-(2-methylpyrimidin-5-yl)-1H-indazol-1-yl)acetyl)-5-methyl-2-azabicyclo[3.1.0]hexane-3-carboxamido)-6-bromoisonicotinic acid | *** | 1.39 (A) | 660 |
| 604 | 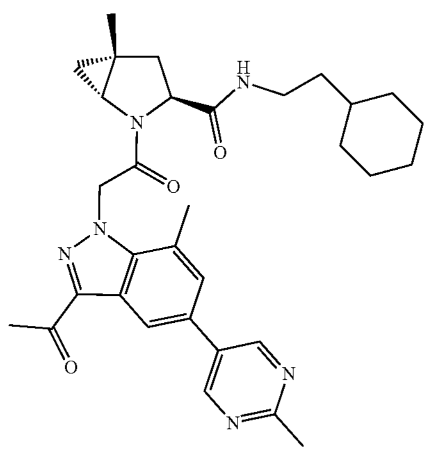 [SMILES: CC(=O)c1nn(CC(=O)N2[C@H](C(=O)NCCC3CCCCC3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(2-cyclohexylethyl)-5-methyl-2-azabicyclo[3.1.0]hexane-3-carboxamide | *** | 2.29 (A) | 556 |
| 605 | 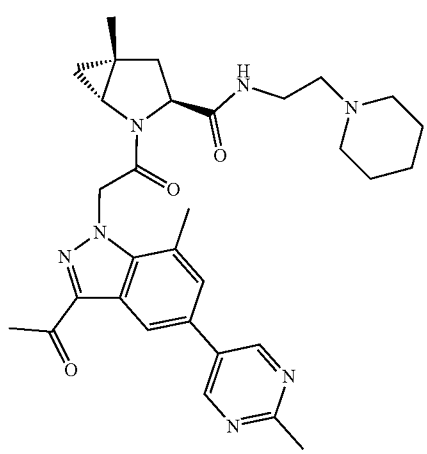 | (1R,3S,5R)-2-(2-(3-acetyl-7-methyl-5-(2-methylpyrimidin-5-yl)-1H-indazol-1-yl)acetyl)-5-methyl-N-(2-(piperidin-1-yl)ethyl)-2-azabicyclo[3.1.0]hexane-3-carboxamide | * | 1.23 (A) | 557 |

TABLE 7-continued

Additional Non-limiting Examples of Compounds of the Present Invention

| Cmp No. | Structure | Name | IC₅ (Stars) | RT min (A, B, C or D) | MS (M + 1) |
|---|---|---|---|---|---|
| 606 | 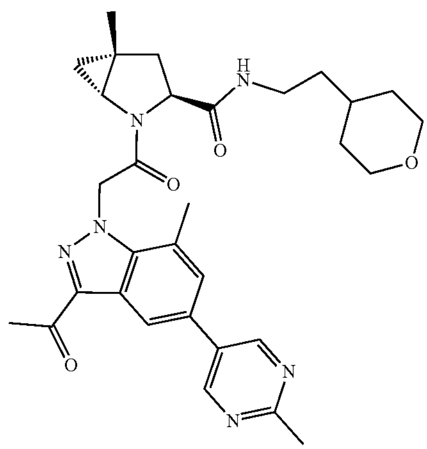 | (1R,3S,5R)-2-(2-(3-acetyl-7-methyl-5-(2-methylpyrimidin-5-yl)-1H-indazol-1-yl)acetyl)-5-methyl-N-(2-(tetrahydro-2H-pyran-4-yl)ethyl)-2-azabicyclo[3.1.0]hexane-3-carboxamide | ** | 1.55 (A) | 558 |
| 607 | 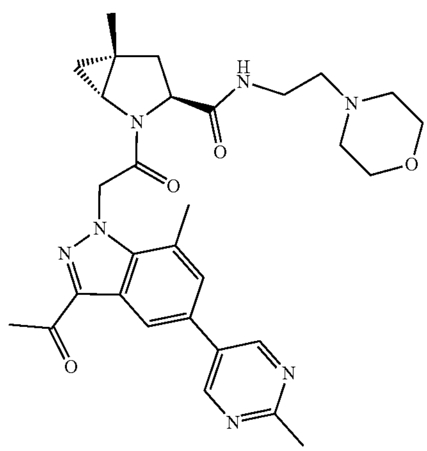 [SMILES: CC(=O)c1nn(CC(=O)N2[C@H](C(=O)NCCN3CCOCC3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-5-methyl-N-(2-morpholinoethyl)-2-azabicyclo[3.1.0]hexane-3-carboxamide | ** | 1.14 (A) | 559 |
| 608 | 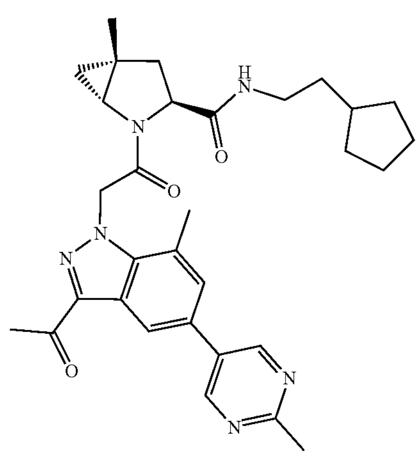 [SMILES: CC(=O)c1nn(CC(=O)N2[C@H](C(=O)NCCC3CCCC3)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(2-cyclopentylethyl)-5-methyl-2-azabicyclo[3.1.0]hexane-3-carboxamide | | 2.14 (A) | 542 |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 609 | 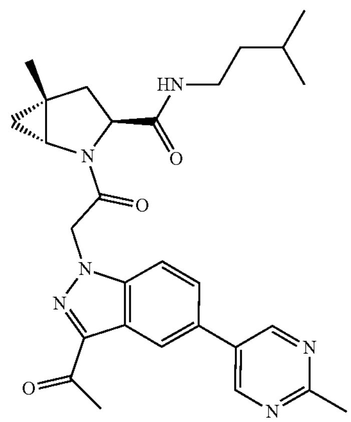 [SMILES: CC(=O)c1nn(CC(=O)N2[C@H](C(=O)NCCC(C)C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-isopentyl-5-methyl-2-azabicyclo[3.1.0]hexane-3-carboxamide | | | |
| 610 | 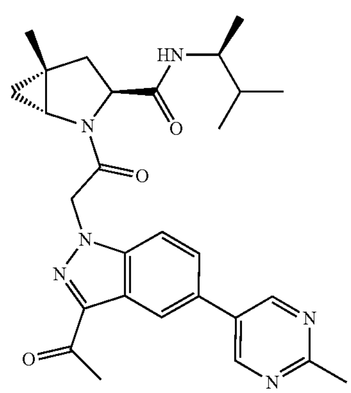 [SMILES: CC(=O)c1nn(CC(=O)N2[C@H](C(=O)N[C@@H](C)C(C)C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-5-methyl-N-((S)-3-methylbutan-2-yl)-2-azabicyclo[3.1.0]hexane-3-carboxamide | | | |
| 611 | 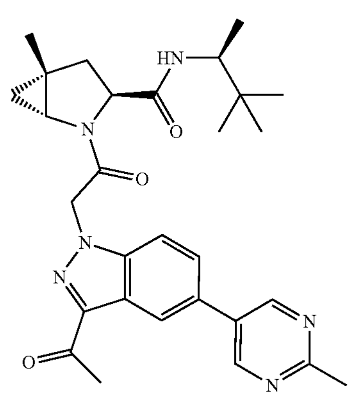 [SMILES: CC(=O)c1nn(CC(=O)N2[C@H](C(=O)N[C@@H](C)C(C)(C)C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((S)-3,3-dimethylbutan-2-yl)-5-methyl-2-azabicyclo[3.1.0]hexane-3-carboxamide | | | |

TABLE 7-continued

Additional Non-limiting Examples of Compounds of the Present Invention

| Cmp No. | Structure | Name | IC$_5$ (Stars) | RT min (A, B, C or D) | MS (M + 1) |
|---|---|---|---|---|---|
| 612 | 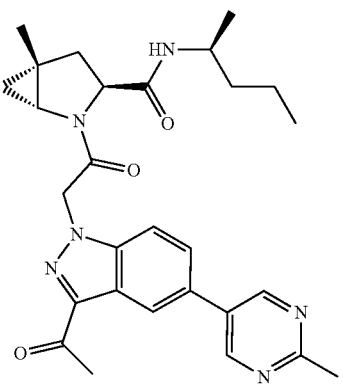 | (1R,3S,5R)-2-(2-(3-acetyl-5-(2-methylpyrimidin-5-yl)-1H-indazol-1-yl)acetyl)-5-methyl-N-((S)-pentan-2-yl)-2-azabicyclo[3.1.0]hexane-3-carboxamide | | | |
| 613 | 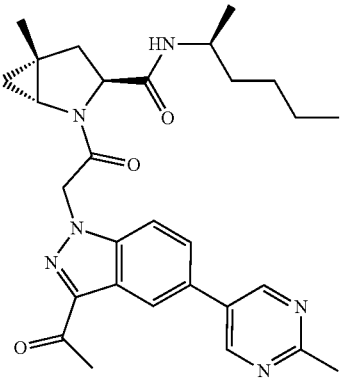 [SMILES: CCCC[C@H](C)NC(=O)[C@@H]1C[C@@]2(C)C[C@H]2N1C(=O)Cn1nc(C(C)=O)c2cc(-c3cnc(C)nc3)ccc21] | (1R,3S,5R)-2-(2-(3-acetyl-5-(2-methylpyrimidin-5-yl)-1H-indazol-1-yl)acetyl)-N-((S)-hexan-2-yl)-5-methyl-2-azabicyclo[3.1.0]hexane-3-carboxamide | | | |
| 614 | 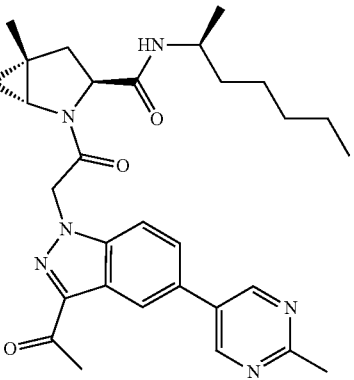 | (1R,3S,5R)-2-(2-(3-acetyl-5-(2-methylpyrimidin-5-yl)-1H-indazol-1-yl)acetyl)-N-((S)-heptan-2-yl)-5-methyl-2-azabicyclo[3.1.0]hexane-3-carboxamide | | | |

TABLE 7-continued

Additional Non-limiting Examples of Compounds of the Present Invention

| Cmp No. | Structure | Name | IC₅ (Stars) | RT min (A, B, C or D) | MS (M + 1) |
|---|---|---|---|---|---|
| 615 | 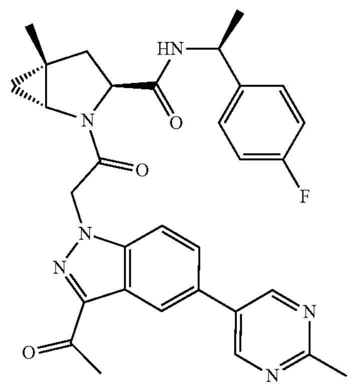 [SMILES: CC(=O)c1nn(CC(=O)N2[C@H](C(=O)N[C@@H](C)c3ccc(F)cc3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((S)-1-(4-fluorophenyl)ethyl)-5-methyl-2-azabicyclo[3.1.0]hexane-3-carboxamide | | | |
| 616 | 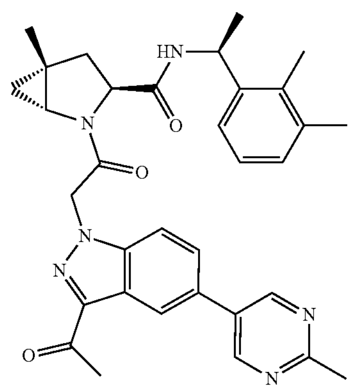 [SMILES: CC(=O)c1nn(CC(=O)N2[C@H](C(=O)N[C@@H](C)c3cccc(C)c3C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((S)-1-(2,3-dimethylphenyl)ethyl)-5-methyl-2-azabicyclo[3.1.0]hexane-3-carboxamide | | | |
| 617 | 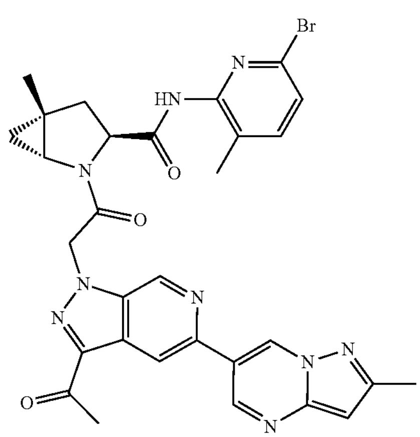 [SMILES: CC(=O)c1nn(CC(=O)N2[C@H](C(=O)Nc3nc(Br)ccc3C)C[C@@]3(C)C[C@@H]23)c2cnc(-c3cnc4cc(C)nn4c3)cc12] | (1R,3S,5R)-2-(2-(3-acetyl-5-(2-methylpyrazolo[1,5-a]pyrimidin-6-yl)-1H-pyrazolo[3,4-c]pyridin-1-yl)acetyl)-N-(6-bromo-3-methylpyridin-2-yl)-5-methyl-2-azabicyclo[3.1.0]hexane-3-carboxamide | *** | 1.94 (A) | 642 |

TABLE 8

Additional Non-limiting Examples of Compounds of the Present Invention

| Cmp No. | Structure and Name | IC$_{50}$ | RT min (A, B, C or D) | MS (M + 1) |
|---|---|---|---|---|
| 236 | 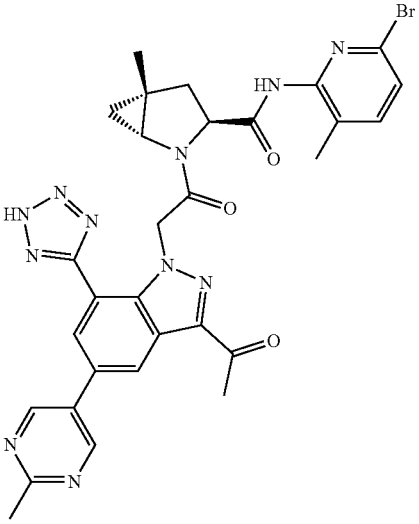 [SMILES: CC(=O)c1nn(CC(=O)N2[C@H](C(=O)Nc3nc(Br)ccc3C)C[C@@]3(C)C[C@@H]23)c2c(-c3nn[nH]n3)cc(-c3cnc(C)nc3)cc12]<br>(1R,3S,5R)-2-(2-(3-acetyl-5-(2-methylpyrimidin-5-yl)-7-(2H-tetrazol-5-yl)-1H-indazol-1-yl)acetyl)-N-(6-bromo-3-methylpyridin-2-yl)-5-methyl-2-azabicyclo[3.1.0]hexane-3-carboxamide | *** | 3.34 (B) | 670 |
| 242 | 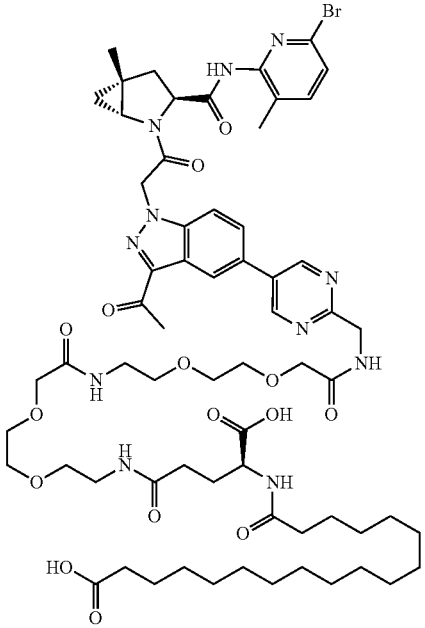 [SMILES: CC(=O)c1nn(CC(=O)N2[C@H](C(=O)Nc3nc(Br)ccc3C)C[C@@]3(C)C[C@@H]23)c2ccc(-c3cnc(CNC(=O)COCCOCCNC(=O)COCCOCCNC(=O)CC[C@H](NC(=O)CCCCCCCCCCCCCCCCC(=O)O)C(=O)O)nc3)cc12]<br>(S)-1-(5-(3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-indazol-5-yl)pyrimidin-2-yl)-24-carboxy-3,12,21,26-tetraoxo-5,8,14,17-tetraoxa-2,11,20,25-tetraazatritetracontan-43-oic acid | *** | 15.30 (C) | 1334 |

TABLE 8-continued

Additional Non-limiting Examples of Compounds of the Present Invention

| Cmp No. | Structure and Name | IC$_{50}$ | RT min (A, B, C or D) | MS (M + 1) |
|---|---|---|---|---|
| 243 | 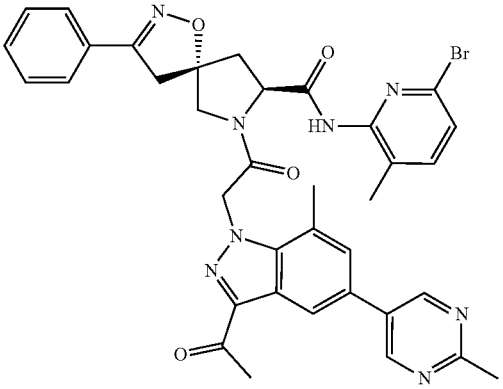 [SMILES: CC(=O)c1nn(CC(=O)N2C[C@@]3(CC(c4ccccc4)=NO3)C[C@H]2C(=O)Nc2nc(Br)ccc2C)c2c(C)cc(-c3cnc(C)nc3)cc12]<br>(5S,8S)-7-(2-(3-acetyl-7-methyl-5-(2-methylpyrimidin-5-yl)-1H-indazol-1-yl)acetyl)-N-(6-bromo-3-methylpyridin-2-yl)-3-phenyl-1-oxa-2,7-diazaspiro[4.4]non-2-ene-8-carboxamide | ** | 3.73 (B) | 721 |
| 244 | 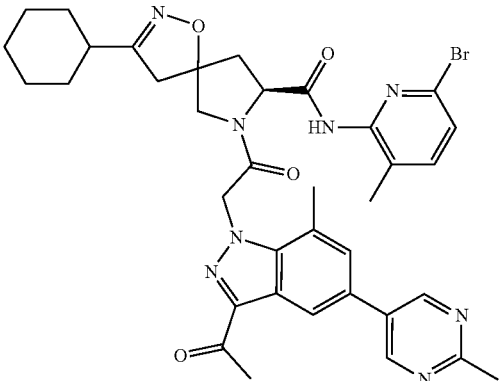<br>(8S)-7-(2-(3-acetyl-7-methyl-5-(2-methylpyrimidin-5-yl)-1H-indazol-1-yl)acetyl)-N-(6-bromo-3-methylpyridin-2-yl)-3-cyclohexyl-1-oxa-2,7-diazaspiro[4.4]non-2-ene-8-carboxamide | *** | 3.82 (B) | 727 |
| 266 | 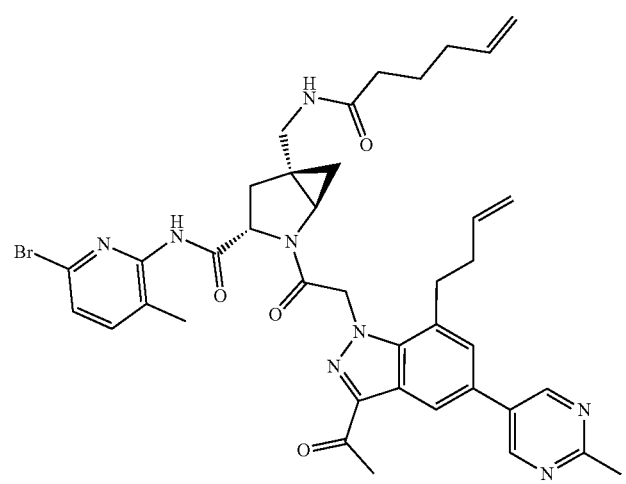 [SMILES: C=CCCCC(=O)NC[C@@]12C[C@@H](C(=O)Nc3nc(Br)ccc3C)N(C(=O)Cn3nc(C(C)=O)c4cc(-c5cnc(C)nc5)cc(CCC=C)c43)[C@@H]1C2]<br>(1R,3S,5R)-2-(2-(3-acetyl-7-(but-3-en-1-yl)-5-(2-methylpyrimidin-5-yl)-1H-indazol-1-yl)acetyl)-N-(6-bromo-3-methylpyridin-2-yl)-5-(hex-5-enamidomethyl)-2-azabicyclo[3.1.0]hexane-3-carboxamide | *** | 3.73 (B) | 767 |

TABLE 8-continued

Additional Non-limiting Examples of Compounds of the Present Invention

| Cmp No. | Structure and Name | IC$_{50}$ | RT min (A, B, C or D) | MS (M + 1) |
|---|---|---|---|---|
| 317 | 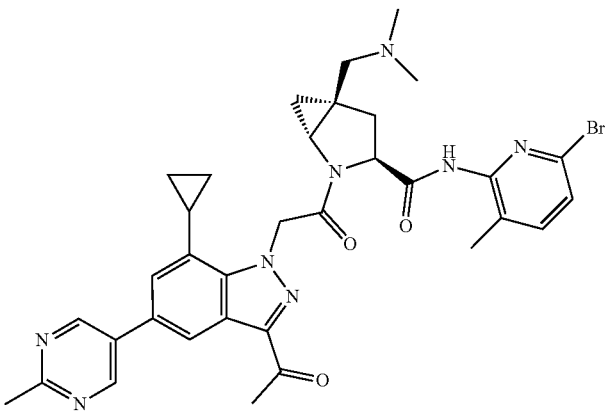 [SMILES: CC(=O)c1nn(CC(=O)N2[C@H](C(=O)Nc3nc(Br)ccc3C)C[C@@]3(CN(C)C)C[C@@H]23)c2c(C3CC3)cc(-c3cnc(C)nc3)cc12] (1R,3S,5R)-2-(2-(3-acetyl-7-cyclopropyl-5-(2-methylpyrimidin-5-yl)-1H-indazol-1-yl)acetyl)-N-(6-bromo-3-methylpyridin-2-yl)-5-((dimethylamino)methyl)-2-azabicyclo[3.1.0]hexane-3-carboxamide | *** | 2.18 (B) | 687 |
| 318 | 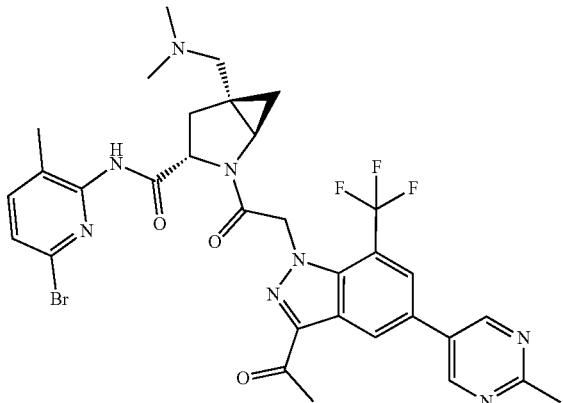 (1R,3S,5R)-2-(2-(3-acetyl-5-(2-methylpyrimidin-5-yl)-7-(trifluoromethyl)-1H-indazol-1-yl)acetyl)-N-(6-bromo-3-methylpyridin-2-yl)-5-((dimethylamino)methyl)-2-azabicyclo[3.1.0]hexane-3-carboxamide | *** | 2.39 (B) | 715 |

TABLE 8-continued

Additional Non-limiting Examples of Compounds of the Present Invention

| Cmp No. | Structure and Name | IC$_{50}$ | RT min (A, B, C or D) | MS (M + 1) |
|---|---|---|---|---|
| 329 | (S)-methyl 1-(5-(3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-indazol-5-yl)pyrimidin-2-yl)-24-(methoxycarbonyl)-3,12,21,26-tetraoxo-5,8,14,17-tetraoxa-2,11,20,25-tetraazatritetracontan-43-oate | *** | 14.33 (D) | 1363 (M + 2) |
| 343 | (1R,3S,5R)-2-(2-(3-acetyl-5-(2-methylpyrimidin-5-yl)-7-(oct-7-en-1-yl)-1H-indazol-1-yl)acetyl)-N-(3-allyl-6-bromopyridin-2-yl)-5-methyl-2-azabicyclo[3.1.0]hexane-3-carboxamide | *** | 4.43 (B) | 738 |

TABLE 8-continued

Additional Non-limiting Examples of Compounds of the Present Invention

| Cmp No. | Structure and Name | IC$_{50}$ | RT min (A, B, C or D) | MS (M + 1) |
|---|---|---|---|---|
| 358 | (S)-methyl 1-((1R,3S,5R)-2-(2-(3-acetyl-5-(2-methylpyrimidin-5-yl)-1H-indazol-1-yl)acetyl)-3-((6-bromo-3-methylpyridin-2-yl)carbamoyl)-2-azabicyclo[3.1.0]hexan-5-yl)-24-(methoxycarbonyl)-3,12,21,26-tetraoxo-5,8,14,17-tetraoxa-2,11,20,25-tetraazatritetracontan-43-oate | * | 14.18 (D) | 1363 (M + 2) |
| 379 | (S)-1-((1R,3S,5R)-2-(2-(3-acetyl-5-(2-methylpyrimidin-5-yl)-1H-indazol-1-yl)acetyl)-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid | *** | 2.41 (A) | 1332 |

TABLE 8-continued

Additional Non-limiting Examples of Compounds of the Present Invention

| Cmp No. | Structure and Name | IC$_{50}$ | RT min (A, B, C or D) | MS (M + 1) |
|---|---|---|---|---|
| 391 | (S)-methyl 1-((1R,3S,5R)-2-(2-(3-acetyl-7-methyl-5-(2-methylpyrimidin-5-yl)-1H-indazol-1-yl)acetyl)-3-((6-bromo-3-methylpyridin-2-yl)carbamoyl)-2-azabicyclo[3.1.0]hexan-5-yl)-24-(methoxycarbonyl)-3,12,21,26-tetraoxo-5,8,14,17-tetraoxa-2,11,20,25-tetraazatritetracontan-43-oate | *** | 13.74 (D) | 1377 (M + 2) |
| 392 | (S)-1-((1R,3S,5R)-2-(2-(3-acetyl-7-methyl-5-(2-methylpyrimidin-5-yl)-1H-indazol-1-yl)acetyl)-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid | *** | 12.83 (C) | 1345 (M − 2) |

TABLE 8-continued

Additional Non-limiting Examples of Compounds of the Present Invention

| Cmp No. | Structure and Name | IC$_{50}$ | RT min (A, B, C or D) | MS (M + 1) |
|---|---|---|---|---|
| 403 | 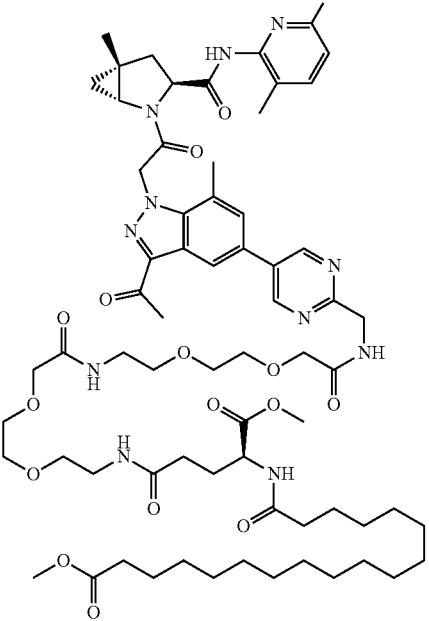<br>(S)-methyl 1-(5-(3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-7-methyl-1H-indazol-5-yl)pyrimidin-2-yl)-24-(methoxycarbonyl)-3,12,21,26-tetraoxo-5,8,14,17-tetraoxa-2,11,20,25-tetraazatritetracontan-43-oate | *** | 13.95 (D) | 1377 (M + 2) |
| 404 | 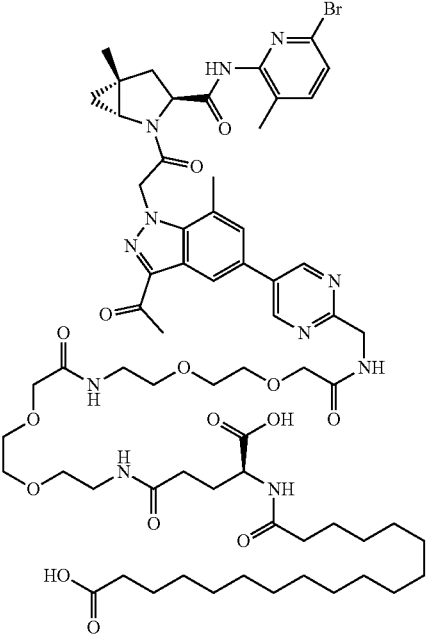 [SMILES: CC(=O)c1nn(CC(=O)N2[C@H](C(=O)Nc3nc(Br)ccc3C)C[C@@]3(C)C[C@@H]23)c2c(C)cc(-c3cnc(CNC(=O)COCCOCCNC(=O)COCCOCCNC(=O)CC[C@H](NC(=O)CCCCCCCCCCCCCCCCC(=O)O)C(=O)O)nc3)cc12]<br>(S)-1-(5-(3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-7-methyl-1H-indazol-5-yl)pyrimidin-2-yl)-24-carboxy-3,12,21,26-tetraoxo-5,8,14,17-tetraoxa-2,11,20,25-tetraazatritetracontan-43-oic acid | *** | 13.32 (C) | 1349 (M + 2) |

TABLE 8-continued

Additional Non-limiting Examples of Compounds of the Present Invention

| Cmp No. | Structure and Name | IC$_{50}$ | RT min (A, B, C or D) | MS (M + 1) |
|---|---|---|---|---|
| 405 | 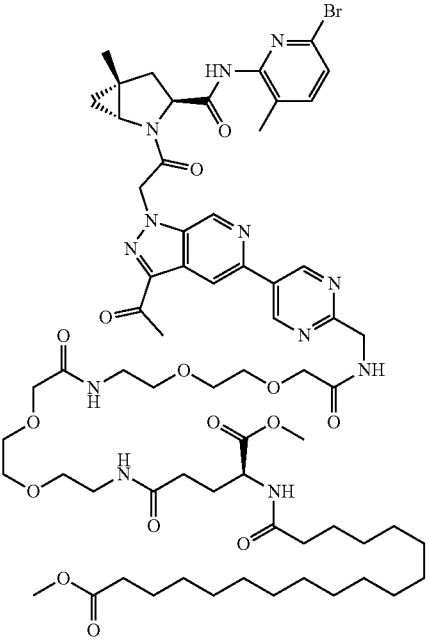 [SMILES: COC(=O)CCCCCCCCCCCCCCCCC(=O)N[C@@H](CCC(=O)NCCOCCOCC(=O)NCCOCCOCC(=O)NCc1ncc(-c2cc3c(C(C)=O)nn(CC(=O)N4[C@H](C(=O)Nc5nc(Br)ccc5C)C[C@@]5(C)C[C@@H]45)c3cn2)cn1)C(=O)OC]<br>(S)-methyl 1-(5-(3-acetyl-1-(2-(((1R,3S,5R)-3-((6-bromo-3-methylpyridin-2-yl)carbamoyl)-5-methyl-2-azabicyclo[3.1.0]hexan-2-yl)-2-oxoethyl)-1H-pyrazolo[3,4-c]pyridin-5-yl)pyrimidin-2-yl)-24-(methoxycarbonyl)-3,12,21,26-tetraoxo-5,8,14,17-tetraoxa-2,11,20,25-tetraazatritetracontan-43-oate | *** | 14.41 (D) | 1364 (M + 2) |
| 406 | 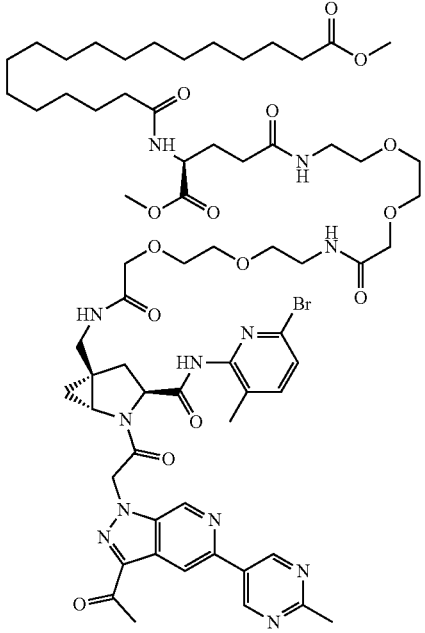 [SMILES: COC(=O)CCCCCCCCCCCCCCCCC(=O)N[C@@H](CCC(=O)NCCOCCOCC(=O)NCCOCCOCC(=O)NC[C@@]12C[C@@H](C(=O)Nc3nc(Br)ccc3C)N(C(=O)Cn3nc(C(C)=O)c4cc(-c5cnc(C)nc5)ncc43)[C@@H]1C2)C(=O)OC]<br>(S)-methyl 1-((1R,3S,5R)-2-(2-(3-acetyl-5-(2-methylpyrimidin-5-yl)-1H-pyrazolo[3,4-c]pyridin-1-yl)acetyl)-3-((6-bromo-3-methylpyridin-2-yl)carbamoyl)-2-azabicyclo[3.1.0]hexan-5-yl)-24-(methoxycarbonyl)-3,12,21,26-tetraoxo-5,8,14,17-tetraoxa-2,11,20,25-tetraazatritetracontan-43-oate | *** | 13.42 (D) | 1364 (M + 2) |

TABLE 8-continued

Additional Non-limiting Examples of Compounds of the Present Invention

| Cmp No. | Structure and Name | IC$_{50}$ | RT min (A, B, C or D) | MS (M + 1) |
|---|---|---|---|---|
| 414 | 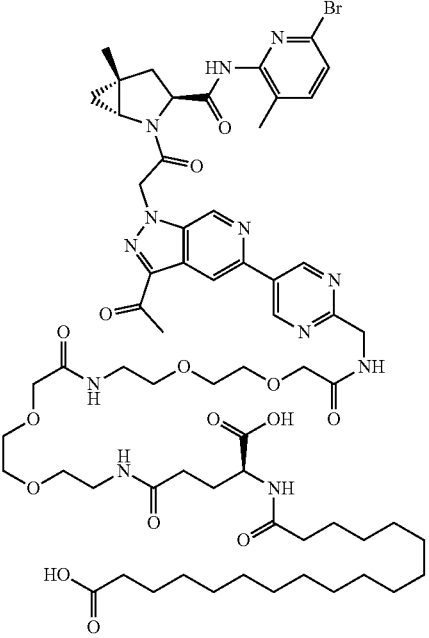 [SMILES: CC(=O)c1nn(CC(=O)N2[C@H](C(=O)Nc3nc(Br)ccc3C)C[C@@]3(C)C[C@@H]23)c2cnc(-c3cnc(CNC(=O)COCCOCCNC(=O)COCCOCCNC(=O)CC[C@H](NC(=O)CCCCCCCCCCCCCCCCC(=O)O)C(=O)O)nc3)cc12] (S)-1-(5-(3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-pyrazolo[3,4-c]pyridin-5-yl)pyrimidin-2-yl)-24-carboxy-3,12,21,26-tetraoxo-5,8,14,17-tetraoxa-2,11,20,25-tetraazatritetracontan-43-oic acid | *** | 9.04 (D) | 1336 (M + 2) |
| 442 | 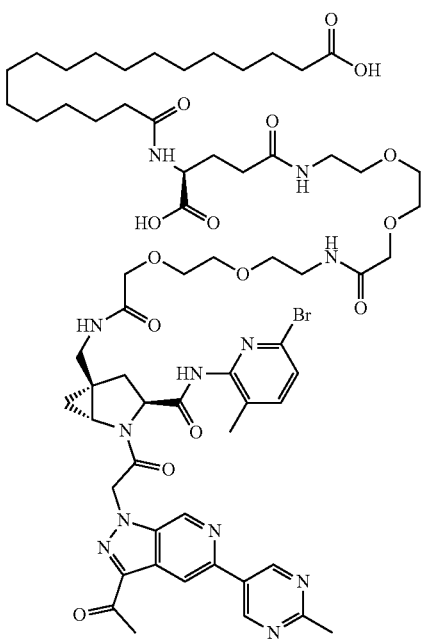 [SMILES: CC(=O)c1nn(CC(=O)N2[C@H](C(=O)Nc3nc(Br)ccc3C)C[C@@]3(CNC(=O)COCCOCCNC(=O)COCCOCCNC(=O)CC[C@H](NC(=O)CCCCCCCCCCCCCCCCC(=O)O)C(=O)O)C[C@@H]23)c2cnc(-c3cnc(C)nc3)cc12] (S)-1-((1R,3S,5R)-2-(2-(3-acetyl-5-(2-methylpyrimidin-5-yl)-1H-pyrazolo[3,4-c]pyridin-1-yl)acetyl)-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid | *** | 4.92 (D) | 1336 (M + 2) |

TABLE 8-continued

Additional Non-limiting Examples of Compounds of the Present Invention

| Cmp No. | Structure and Name | IC$_{50}$ | RT min (A, B, C or D) | MS (M + 1) |
|---|---|---|---|---|
| 443 | (Structure is shown below) (4S,7S,10S,13S,16S,19S,22S)-22-acetamido-4-((((1R,3S,5R)-2-(2-(3-acetyl-7-methyl-5-(2-methylpyrimidin-5-yl)-1H-indazol-1-yl)acetyl)-3-((6-bromo-3-methylpyridin-2-yl)carbamoyl)-2-azabicyclo[3.1.0]hexan-5-yl)methyl)carbamoyl)-10,16-bis(2-carboxyethyl)-7,19-bis(4-hydroxybenzyl)-6,9,12,15,18,21-hexaoxo-13-(4-palmitamidobutyl)-5,8,11,14,17,20-hexaazapentacosanedioic acid | ** | 14.70 (C) | 1884 (M + 2) |
| 475 | 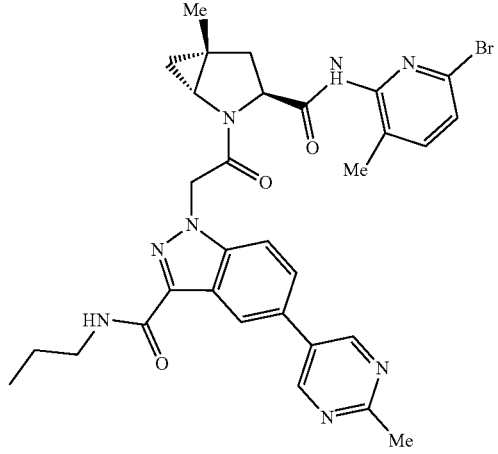 [SMILES: CCCNC(=O)c1nn(CC(=O)N2[C@H](C(=O)Nc3nc(Br)ccc3C)C[C@@]3(C)C[C@@H]23)c2ccc(-c3cnc(C)nc3)cc12] 1-(2-((1R,3S,5R)-3-((6-bromo-3-methylpyridin-2-yl)carbamoyl)-5-methyl-2-azabicyclo[3.1.0]hexan-2-yl)-2-oxoethyl)-5-(2-methylpyrimidin-5-yl)-N-propyl-1H-indazole-3-carboxamide | *** | 1.89 (A) | 645 |
| 476 | 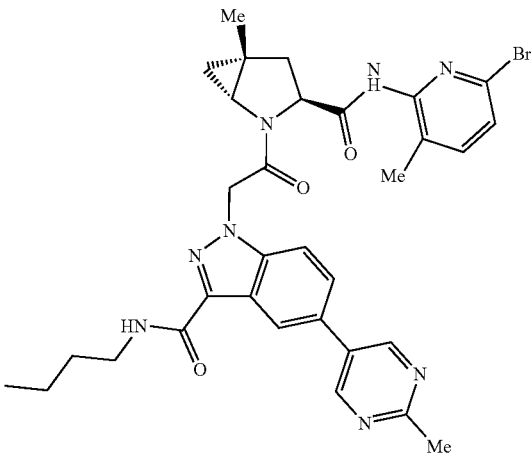 [SMILES: CCCCNC(=O)c1nn(CC(=O)N2[C@H](C(=O)Nc3nc(Br)ccc3C)C[C@@]3(C)C[C@@H]23)c2ccc(-c3cnc(C)nc3)cc12] 1-(2-((1R,3S,5R)-3-((6-bromo-3-methylpyridin-2-yl)carbamoyl)-5-methyl-2-azabicyclo[3.1.0]hexan-2-yl)-2-oxoethyl)-N-butyl-5-(2-methylpyrimidin-5-yl)-1H-indazole-3-carboxamide | *** | | |

TABLE 8-continued

Additional Non-limiting Examples of Compounds of the Present Invention

| Cmp No. | Structure and Name | IC$_{50}$ | RT min (A, B, C or D) | MS (M + 1) |
|---|---|---|---|---|
| 477 | 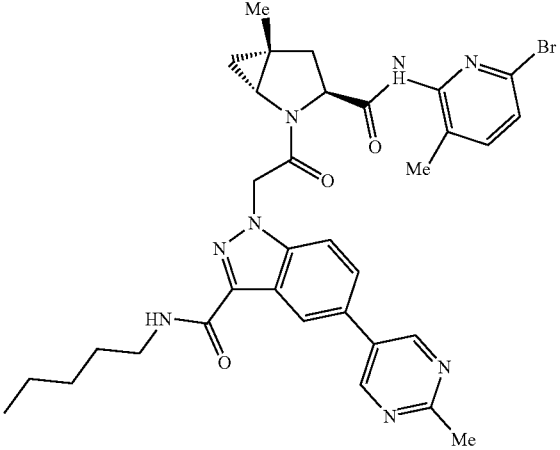 [SMILES: CCCCCNC(=O)c1nn(CC(=O)N2[C@H](C(=O)Nc3nc(Br)ccc3C)C[C@@]3(C)C[C@@H]23)c2ccc(-c3cnc(C)nc3)cc12]  1-(2-((1R,3S,5R)-3-((6-bromo-3-methylpyridin-2-yl)carbamoyl)-5-methyl-2-azabicyclo[3.1.0]hexan-2-yl)-2-oxoethyl)-5-(2-methylpyrimidin-5-yl)-N-pentyl-1H-indazole-3-carboxamide | * | 2.26 (A) | 673 |
| 478 | 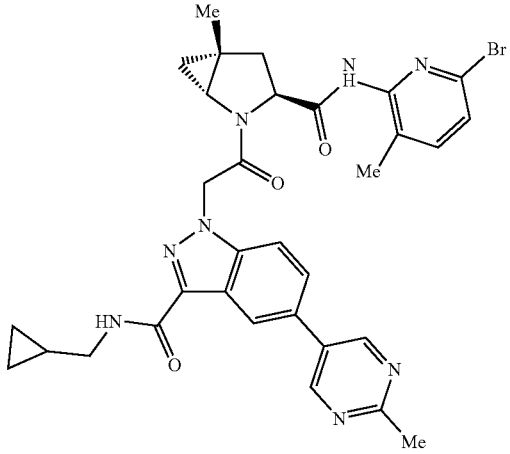 [SMILES: Cc1ncc(-c2ccc3c(c2)c(C(=O)NCC2CC2)nn3CC(=O)N2[C@H](C(=O)Nc3nc(Br)ccc3C)C[C@@]3(C)C[C@@H]23)cn1]  1-(2-((1R,3S,5R)-3-((6-bromo-3-methylpyridin-2-yl)carbamoyl)-5-methyl-2-azabicyclo[3.1.0]hexan-2-yl)-2-oxoethyl)-N-(cyclopropylmethyl)-5-(2-methylpyrimidin-5-yl)-1H-indazole-3-carboxamide | *** | 1.95 (A) | 657 |

TABLE 8-continued

Additional Non-limiting Examples of Compounds of the Present Invention

| Cmp No. | Structure and Name | IC$_{50}$ | RT min (A, B, C or D) | MS (M + 1) |
|---|---|---|---|---|
| 479 | 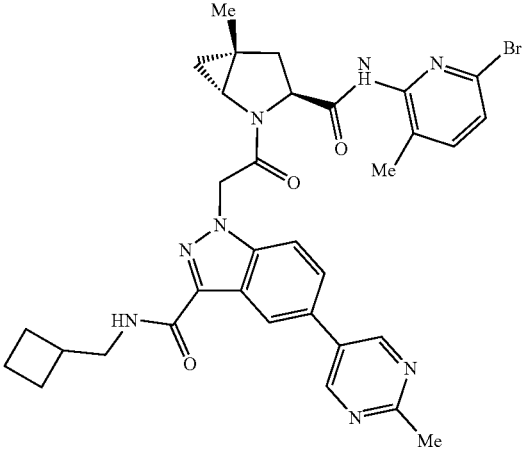 [SMILES: Cc1ncc(-c2ccc3c(c2)c(C(=O)NCC2CCC2)nn3CC(=O)N2[C@H](C(=O)Nc3nc(Br)ccc3C)C[C@@]3(C)C[C@@H]23)cn1] 1-(2-((1R,3S,5R)-3-((6-bromo-3-methylpyridin-2-yl)carbamoyl)-5-methyl-2-azabicyclo[3.1.0]hexan-2-yl)-2-oxoethyl)-N-(cyclobutylmethyl)-5-(2-methylpyrimidin-5-yl)-1H-indazole-3-carboxamide | ** | 2.14 (A) | 671 |
| 480 | 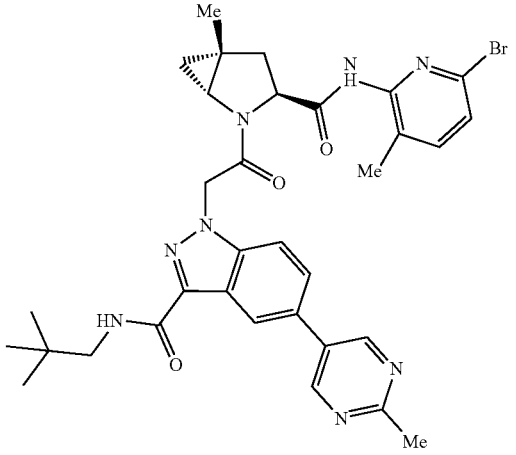 [SMILES: Cc1ncc(-c2ccc3c(c2)c(C(=O)NCC(C)(C)C)nn3CC(=O)N2[C@H](C(=O)Nc3nc(Br)ccc3C)C[C@@]3(C)C[C@@H]23)cn1] 1-(2-((1R,3S,5R)-3-((6-bromo-3-methylpyridin-2-yl)carbamoyl)-5-methyl-2-azabicyclo[3.1.0]hexan-2-yl)-2-oxoethyl)-5-(2-methylpyrimidin-5-yl)-N-neopentyl-1H-indazole-3-carboxamide | * | 2.21 (A) | 673 |

TABLE 8-continued

Additional Non-limiting Examples of Compounds of the Present Invention

| Cmp No. | Structure and Name | IC$_{50}$ | RT min (A, B, C or D) | MS (M + 1) |
|---|---|---|---|---|
| 489 | 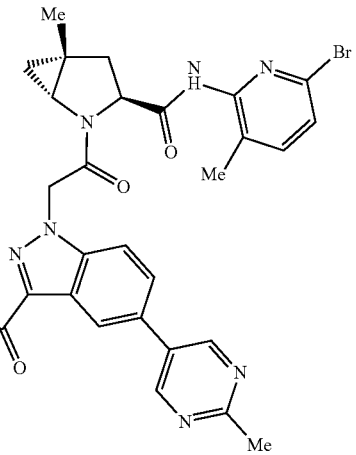 N-(2-aminoethyl)-1-(2-((1R,3S,5R)-3-((6-bromo-3-methylpyridin-2-yl)carbamoyl)-5-methyl-2-azabicyclo[3.1.0]hexan-2-yl)-2-oxoethyl)-5-(2-methylpyrimidin-5-yl)-1H-indazole-3-carboxamide | ** | 1.29 (A) | 646 |
| 490 | 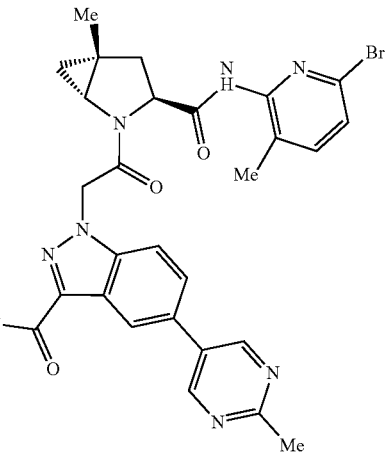 1-(2-((1R,3S,5R)-3-((6-bromo-3-methylpyridin-2-yl)carbamoyl)-5-methyl-2-azabicyclo[3.1.0]hexan-2-yl)-2-oxoethyl)-N-(2-(methylamino)ethyl)-5-(2-methylpyrimidin-5-yl)-1H-indazole-3-carboxamide | ** | 1.31 (A) | 660 |

TABLE 8-continued

Additional Non-limiting Examples of Compounds of the Present Invention

| Cmp No. | Structure and Name | IC$_{50}$ | RT min (A, B, C or D) | MS (M + 1) |
|---|---|---|---|---|
| 491 | 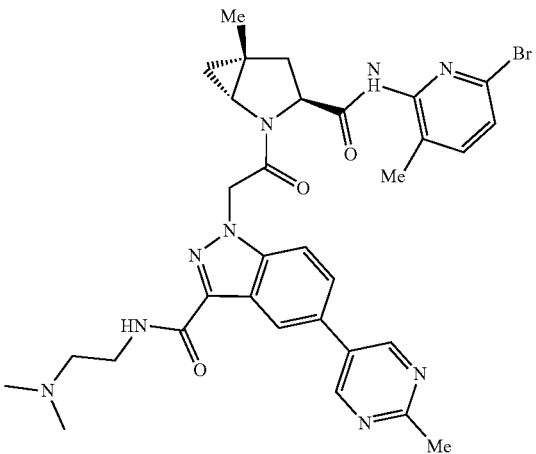 [SMILES: Cc1ncc(-c2ccc3c(c2)c(C(=O)NCCN(C)C)nn3CC(=O)N2[C@H](C(=O)Nc3nc(Br)ccc3C)C[C@@]3(C)C[C@@H]23)cn1] 1-(2-((1R,3S,5R)-3-((6-bromo-3-methylpyridin-2-yl)carbamoyl)-5-methyl-2-azabicyclo[3.1.0]hexan-2-yl)-2-oxoethyl)-N-(2-(dimethylamino)ethyl)-5-(2-methylpyrimidin-5-yl)-1H-indazole-3-carboxamide | * | 1.33 (A) | 674 |
| 499 | 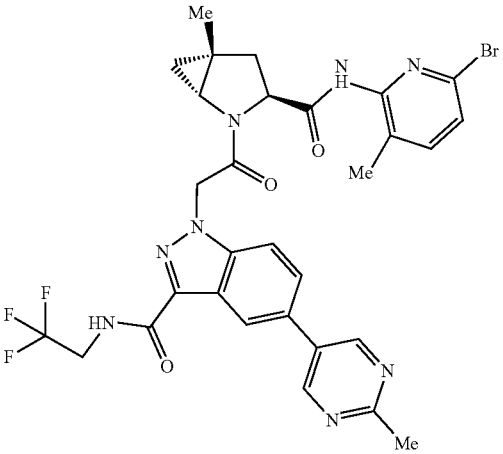 [SMILES: Cc1ncc(-c2ccc3c(c2)c(C(=O)NCC(F)(F)F)nn3CC(=O)N2[C@H](C(=O)Nc3nc(Br)ccc3C)C[C@@]3(C)C[C@@H]23)cn1] 1-(2-((1R,3S,5R)-3-((6-bromo-3-methylpyridin-2-yl)carbamoyl)-5-methyl-2-azabicyclo[3.1.0]hexan-2-yl)-2-oxoethyl)-5-(2-methylpyrimidin-5-yl)-N-(2,2,2-trifluoroethyl)-1H-indazole-3-carboxamide | *** | | |

TABLE 8-continued

Additional Non-limiting Examples of Compounds of the Present Invention

| Cmp No. | Structure and Name | IC$_{50}$ | RT min (A, B, C or D) | MS (M + 1) |
|---|---|---|---|---|
| 500 | 1-(2-((1R,3S,5R)-3-((6-bromo-3-methylpyridin-2-yl)carbamoyl)-5-methyl-2-azabicyclo[3.1.0]hexan-2-yl)-2-oxoethyl)-N-isobutyl-5-(2-methylpyrimidin-5-yl)-1H-indazole-3-carboxamide | *** | | |
| 515 | 1-(2-((1R,3S,5R)-3-((6-bromo-3-methylpyridin-2-yl)carbamoyl)-5-methyl-2-azabicyclo[3.1.0]hexan-2-yl)-2-oxoethyl)-7-cyano-5-(2-methylpyrimidin-5-yl)-1H-indazole-3-carboxamide | *** | 3.15 (B) | 628 |
| 527 | (1R,3S,5R)-2-(2-(3-acetyl-7-methyl-5-(2-methylpyrimidin-5-yl)-1H-indazol-1-yl)acetyl)-N-heptyl-5-methyl-2-azabicyclo[3.1.0]hexane-3-carboxamide | *** | | |

TABLE 8-continued

Additional Non-limiting Examples of Compounds of the Present Invention

| Cmp No. | Structure and Name | IC$_{50}$ | RT min (A, B, C or D) | MS (M + 1) |
|---|---|---|---|---|
| 528 | (1R,3S,5R)-2-(2-(3-acetyl-7-methyl-5-(2-methylpyrimidin-5-yl)-1H-indazol-1-yl)acetyl)-5-methyl-N-octyl-2-azabicyclo[3.1.0]hexane-3-carboxamide | ** | 2.50 (A) | 558 |
| 530 | (1R,3S,5R)-2-(2-(3-acetyl-7-methyl-5-(2-methylpyrimidin-5-yl)-1H-indazol-1-yl)acetyl)-5-methyl-N-nonyl-2-azabicyclo[3.1.0]hexane-3-carboxamide | ** | 2.68 (A) | 572 |
| 531 | (1R,3S,5R)-2-(2-(3-acetyl-7-methyl-5-(2-methylpyrimidin-5-yl)-1H-indazol-1-yl)acetyl)-N-decyl-5-methyl-2-azabicyclo[3.1.0]hexane-3-carboxamide | * | 2.87 (A) | 586 |

TABLE 8-continued

Additional Non-limiting Examples of Compounds of the Present Invention

| Cmp No. | Structure and Name | IC$_{50}$ | RT min (A, B, C or D) | MS (M + 1) |
|---|---|---|---|---|
| 535 | (Structure is shown below) (4S,7S,10S,13S,16S,19S,22S)-22-acetamido-4-((1-((1R,3S,5R)-2-(2-(3-acetyl-7-methyl-5-(2-methylpyrimidin-5-yl)-1H-indazol-1-yl)acetyl)-3-((6-bromo-3-methylpyridin-2-yl)carbamoyl)-2-azabicyclo[3.1.0]hexan-5-yl)-3-oxo-6,9,12,15,18,21,24,27,30,33,36,39,42,45,48,51,54,57,60,63,66,69,72,75-tetracosaoxa-2-azaheptaheptacontan-77-yl)carbamoyl)-10,16-bis(2-carboxyethyl)-7,19-bis(4-hydroxybenzyl)-6,9,12,15,18,21-hexaoxo-13-(4-palmitamidobutyl)-5,8,11,14,17,20-hexaazapentacosanedioic acid | ** | 1.51 ( ) | 1506 ((M + 2)/2) |
| 538 | (1R,3S,5R)-2-(2-(3-acetyl-7-methyl-5-(2-methylpyrimidin-5-yl)-1H-indazol-1-yl)acetyl)-5-methyl-N-(4-phenylbutyl)-2-azabicyclo[3.1.0]hexane-3-carboxamide | *** | 2.18 (A) | 578 |
| 539 | (1R,3S,5R)-2-(2-(3-acetyl-7-methyl-5-(2-methylpyrimidin-5-yl)-1H-indazol-1-yl)acetyl)-5-methyl-N-(5-phenylpentyl)-2-azabicyclo[3.1.0]hexane-3-carboxamide | *** | 2.34 (A) | 592 |

TABLE 8-continued

Additional Non-limiting Examples of Compounds of the Present Invention

| Cmp No. | Structure and Name | IC$_{50}$ | RT min (A, B, C or D) | MS (M + 1) |
|---|---|---|---|---|
| 540 | 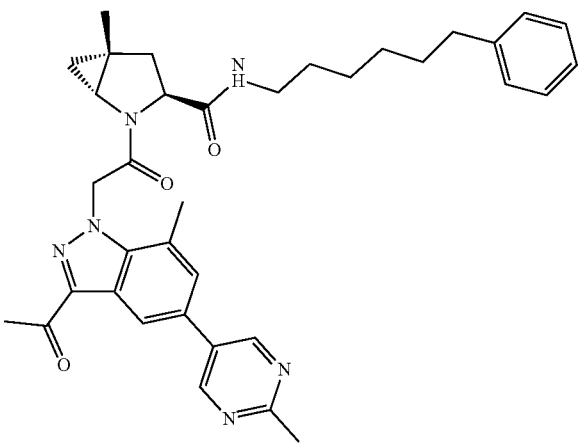 [SMILES: CC(=O)c1nn(CC(=O)N2[C@H](C(=O)NCCCCCCc3ccccc3)C[C@@]3(C)C[C@@H]23)c2c(C)cc(-c3cnc(C)nc3)cc12]<br>(1R,3S,5R)-2-(2-(3-acetyl-7-methyl-5-(2-methylpyrimidin-5-yl)-1H-indazol-1-yl)acetyl)-5-methyl-N-(6-phenylhexyl)-2-azabicyclo[3.1.0]hexane-3-carboxamide | ** | 2.49 (A) | 606 |
| 569 | 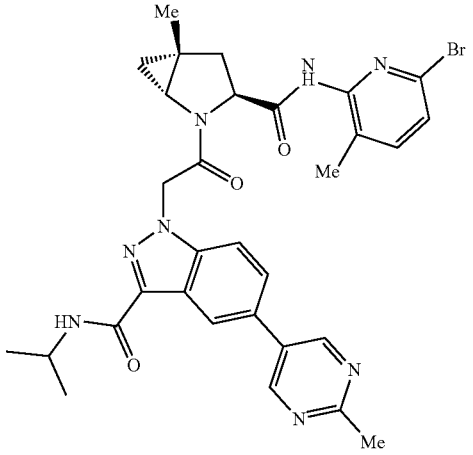 [SMILES: Cc1ncc(-c2ccc3c(c2)c(C(=O)NC(C)C)nn3CC(=O)N2[C@H](C(=O)Nc3nc(Br)ccc3C)C[C@@]3(C)C[C@@H]23)cn1]<br>1-(2-((1R,3S,5R)-3-((6-bromo-3-methylpyridin-2-yl)carbamoyl)-5-methyl-2-azabicyclo[3.1.0]hexan-2-yl)-2-oxoethyl)-N-(sec-butyl)-5-(2-methylpyrimidin-5-yl)-1H-indazole-3-carboxamide | ** | 2.05 (A) | 658 |

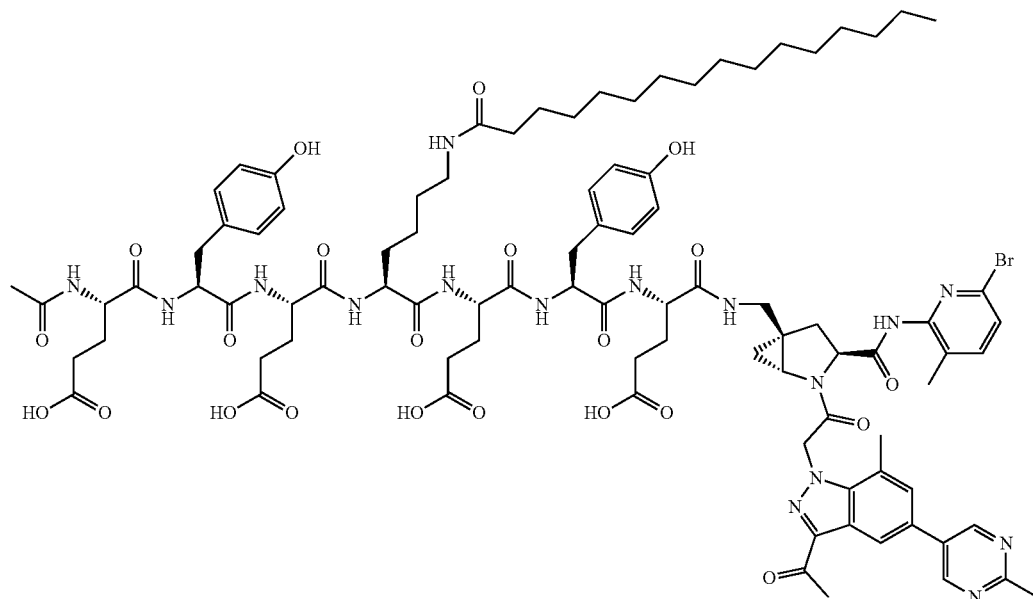

Compound 443

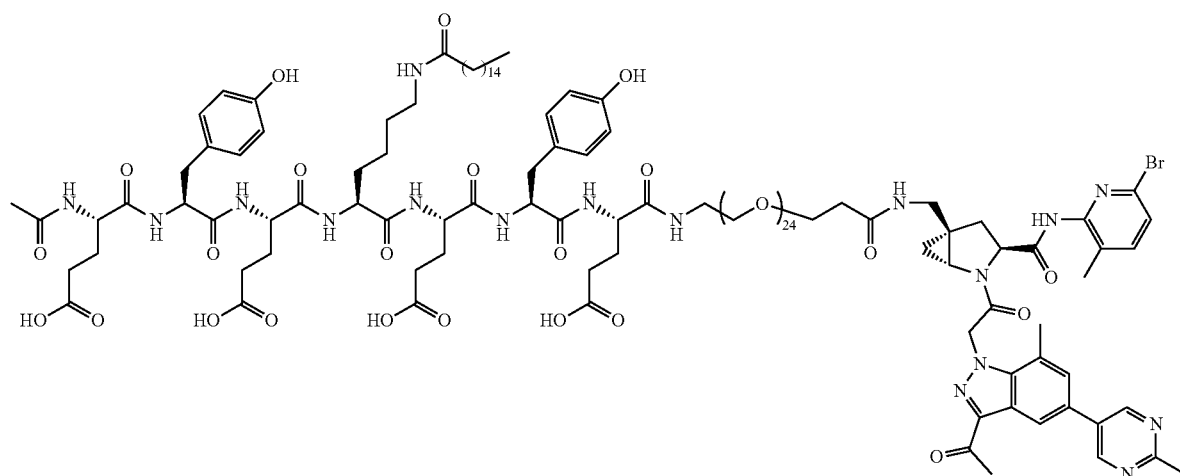

Compound 535

Example 10. Human Factor D Assay

Human Factor D (purified from human serum, Complement Technology, Inc.) at 80 nM final concentration is incubated with test compound at various concentrations for 5 min at room temperature in 50 mM Tris, 1M NaCl, pH 7.5. A synthetic substrate Z-L-Lys-SBzl and DTNB (Ellman's reagent) are added to final concentrations of 100 µM each. Absorbance at 405 nm ($A_{405}$) is recorded at 30 second intervals for 30 min using a microplate spectrophotometer. $IC_{50}$ values are calculated by nonlinear regression of complement Factor D reaction rates as a function of test compound concentration.

Example 11. Hemolysis Assay

The hemolysis assay was previously described by G. Ruiz-Gomez, et al., J. Med. Chem. (2009) 52: 6042-6052. Prior to the assay, the optimum concentration of Normal Human Serum (NHS) needed to achieve 100% lysis of rabbit erythrocytes (RE) is determined by titration. In the assay, NHS (Complement Technology) is diluted in $GVB^0$ Buffer (0.1% gelatin, 5 mM Veronal, 145 mM NaCl, 0.025% $NaN_3$, pH 7.3, Complement Technology) plus 10 mM Mg-EGTA and incubated with test compound at various concentrations for 15 min at 37° C. RE (Complement Technology) freshly suspended in $GVB^0$ plus 10 mM Mg-EGTA are added to a final concentration of $1\times10^8$ cells/mL and reactions are incubated for 30 min at 37° C. Positive control reactions (100% lysis) consist of $GVB^0$ plus 10 mM Mg-EGTA with NHS and RE but without test compound; negative control reactions (0% lysis) consist of $GVB^0$ plus 10 mM Mg-EGTA with RE only. Samples are centrifuged at 2000 g for 3 min and supernatants collected. Absorbance at 405 nm ($A_{405}$) is recorded using a microplate spectrophotometer. $IC_{50}$ values are calculated by nonlinear regression from the percentage of hemolysis as a function of test compound concentration.

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

What is claimed is:

1. A method of treating a disorder mediated by complement cascade Factor D, the method comprising administering to a subject ion need thereof an effective amount of a compound selected from:

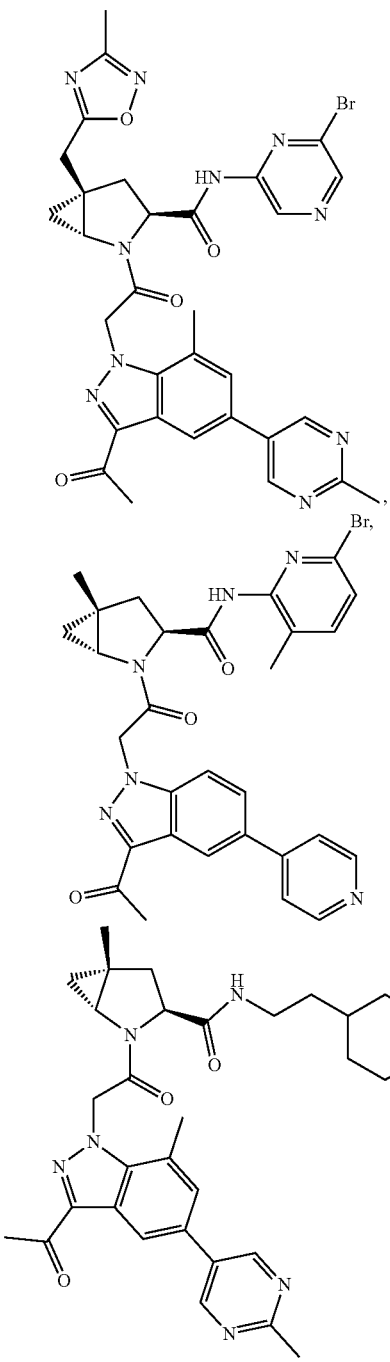

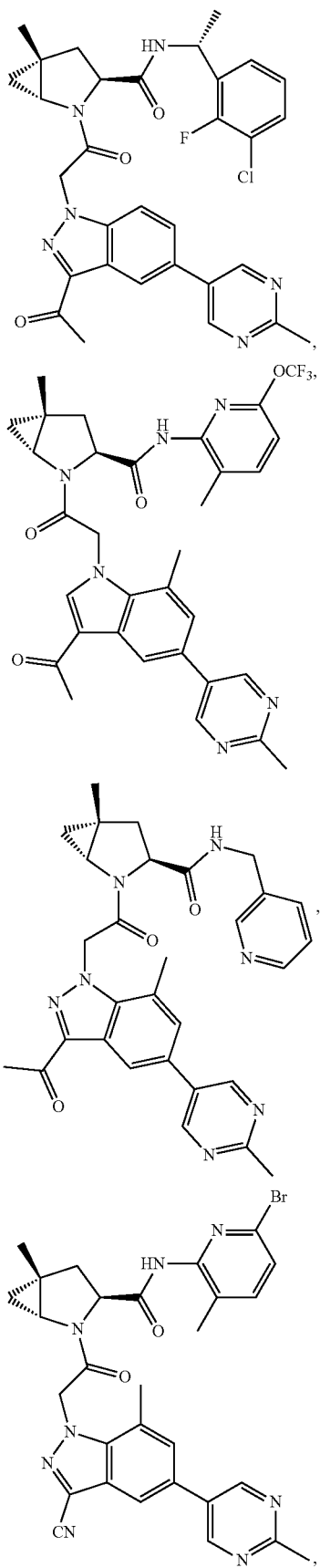

-continued

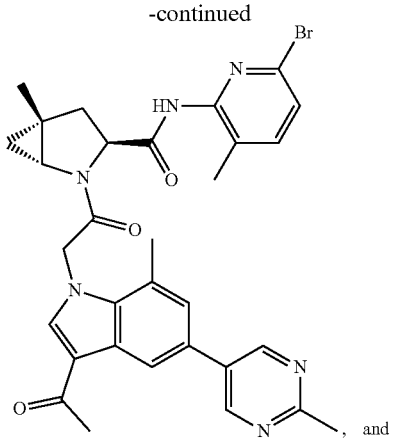

, and

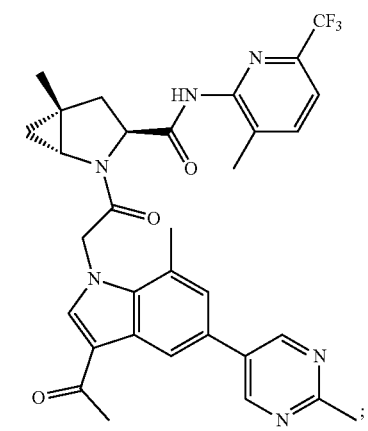

or a pharmaceutically acceptable salt thereof.

2. The method of claim 1, wherein the compound is

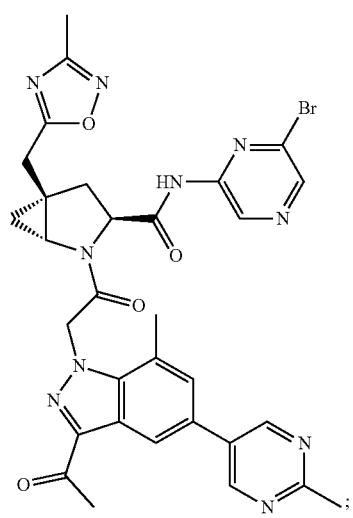 [SMILES: CC(=O)c1nn(CC(=O)N2[C@H](C(=O)Nc3cncc(Br)n3)C[C@@]3(Cc4nc(C)no4)C[C@@H]23)c2c(C)cc(-c3cnc(C)nc3)cc12]

or a pharmaceutically acceptable salt thereof.

3. The method of claim 1, wherein the compound is

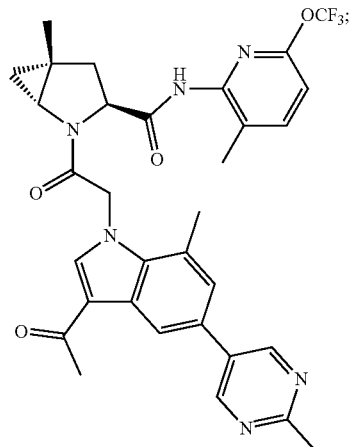

or a pharmaceutically acceptable salt thereof.

4. The method of claim 1, wherein the compound is

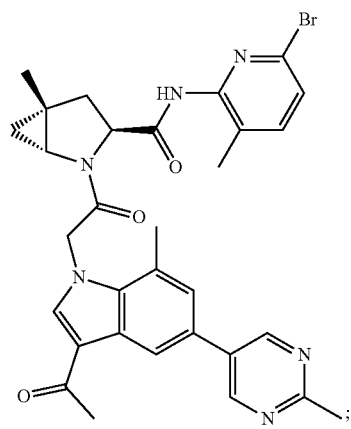 [SMILES: CC(=O)c1cn(CC(=O)N2[C@H](C(=O)Nc3nc(Br)ccc3C)C[C@@]3(C)C[C@@H]23)c2c(C)cc(-c3cnc(C)nc3)cc12]

or a pharmaceutically acceptable salt thereof.

5. The method of claim 1, wherein the compound is

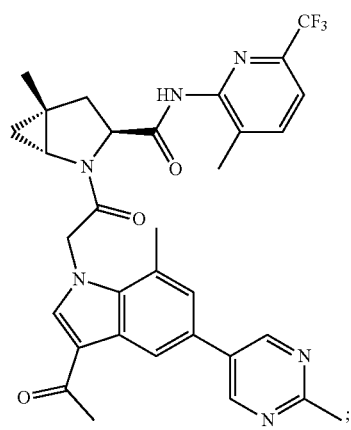 [SMILES: CC(=O)c1cn(CC(=O)N2[C@H](C(=O)Nc3nc(C(F)(F)F)ccc3C)C[C@@]3(C)C[C@@H]23)c2c(C)cc(-c3cnc(C)nc3)cc12]

or a pharmaceutically acceptable salt thereof.

6. The method of claim 1, wherein the compound is

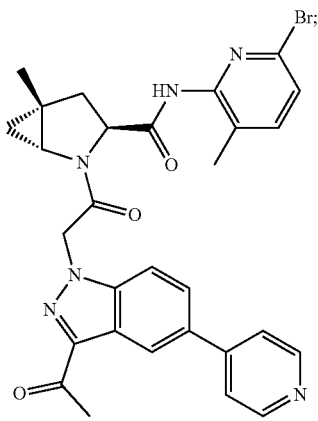 [SMILES: CC(=O)c1nn(CC(=O)N2[C@H](C(=O)Nc3nc(Br)ccc3C)C[C@@]3(C)C[C@@H]23)c2ccc(-c3ccncc3)cc12]

or a pharmaceutically acceptable salt thereof.

7. The method of claim 1, wherein the subject is a human.

8. The method of claim 1, wherein the disorder is selected from acute respiratory distress syndrome, age-related macular degeneration, arthritis, asthma, Alzheimer's dementia, amyotrophic lateral sclerosis, antibody-mediated transplant rejection, antineutrophil cytoplasm antibody-associated vasculitis, antiphospholipid syndrome, atypical or typical hemolytic uremic syndrome, a cardiovascular disease, cold agglutinin disease, chronic obstructive pulmonary disease, cirrhosis, Crohn's disease, C3 glomerulonephritis, diabetic retinopathy, dense deposit disease, dermatomyositis, dermatitis, epidermolysis bullosa acquisita, fatty liver, focal segmental glomerulosclerosis, geographic atrophy, glomerulonephritis, graft versus host disease, Guillain Barre syndrome, hemolytic anemia, hidradenitis suppurativa, IgA nephropathy, ischemia/reperfusion injury, liver failure, liver inflammation, lupus nephritis, membrane proliferative glomerulonephritis, multifocal motor neuropathy, multiple sclerosis, myasthenia gravis, neuromyelitis optica, nonalcoholic steatohepatitis (NASH), an ophthalmic disease, pancreatitis, paroxysmal nocturnal hemoglobinuria, pemphigoid, pemphigus vulgaris, pre-eclampsia, reduced glomerular filtration rate, a renovascular disorder, a respiratory disease, retinal detachment, rheumatoid arthritis, scleroderma, sepsis, shiga toxin *E. coli*-related hemolytic uremic syndrome, spinal cord injury, sickle cell disease, traumatic brain injury, and ulcerative colitis.

9. The method of claim 8, wherein the disorder is IgA nephropathy.

10. The method of claim 8, wherein the disorder is geographic atrophy.

11. The method of claim 8, wherein the disorder is lupus nephritis.

12. The method of claim 8, wherein the disorder is myasthenia gravis.

13. The method of claim 8, wherein the disorder is reduced glomerular filtration rate.

14. The method of claim 8, wherein the disorder is renovascular disorder.

15. The method of claim 8, wherein the disorder is sickle cell disease.

16. The method of claim 8, wherein the disorder is C3 glomerulonephritis.

17. The method of claim 8, wherein the disorder is dense deposit disease.

* * * * *